US008734812B1

(12) United States Patent
Galeotti et al.

(10) Patent No.: US 8,734,812 B1
(45) Date of Patent: May 27, 2014

(54) NEISSERIAL ANTIGENIC PEPTIDES

(75) Inventors: Cesira Galeotti, Montegriggioni (IT); Guido Grandi, Siena (IT); Vega Masignani, Siena (IT); Mariarosa Mora, Siena (IT); Mariagrazia Pizza, Siena (IT); Rino Rappuoli, Siena (IT); Guilio Ratti, Siena (IT); Vincenzo Scarlato, Siena (IT); Maria Scarselli, Siena (IT)

(73) Assignee: Novartis AG, Basel (CH)

( * ) Notice: Subject to any disclaimer, the term of this patent is extended or adjusted under 35 U.S.C. 154(b) by 1816 days.

(21) Appl. No.: 10/111,983

(22) PCT Filed: Oct. 30, 2000

(86) PCT No.: PCT/IB00/01661
§ 371 (c)(1),
(2), (4) Date: Feb. 26, 2003

(87) PCT Pub. No.: WO01/31019
PCT Pub. Date: May 3, 2001

Related U.S. Application Data

(60) Provisional application No. 60/162,616, filed on Oct. 29, 1999.

(51) Int. Cl.
*A61K 39/095* (2006.01)
*A61K 39/02* (2006.01)
*A61K 39/00* (2006.01)
*A61K 38/00* (2006.01)

(52) U.S. Cl.
USPC ............ 424/250.1; 424/234.1; 424/190.1; 424/184.1; 514/1.1; 530/300; 530/825

(58) Field of Classification Search
USPC ............ 530/300, 350, 825; 514/2; 424/190.1, 424/250.1, 234.1, 184.1
See application file for complete search history.

(56) References Cited

U.S. PATENT DOCUMENTS

| | | | |
|---|---|---|---|
| 6,197,312 B1* | 3/2001 | Peak et al. .................. | 424/250.1 |
| 6,696,062 B1 | 2/2004 | Thonnard | |
| 7,018,636 B1* | 3/2006 | Bhattacharjee et al. . | 424/197.11 |
| 7,348,006 B2 | 3/2008 | Contorni et al. | |
| 7,576,176 B1* | 8/2009 | Fraser et al. .................. | 530/350 |
| 7,785,608 B2* | 8/2010 | Zlotnick et al. ............ | 424/249.1 |
| 7,862,827 B2 | 1/2011 | Giuliani et al. | |
| 8,273,360 B2 | 9/2012 | Pizza et al. | |
| 8,398,988 B2 | 3/2013 | Contorni et al. | |
| 8,563,007 B1 | 10/2013 | Zlotnick et al. | |
| 2004/0092711 A1 | 5/2004 | Arico et al. | |
| 2004/0110670 A1 | 6/2004 | Arico et al. | |
| 2004/0167068 A1 | 8/2004 | Zlotnick et al. | |
| 2005/0222385 A1 | 10/2005 | Pizza | |
| 2006/0029621 A1 | 2/2006 | Granoff et al. | |
| 2006/0051840 A1 | 3/2006 | Arico et al. | |
| 2006/0171957 A1 | 8/2006 | Pizza | |
| 2006/0240045 A1 | 10/2006 | Berthet et al. | |
| 2006/0251670 A1 | 11/2006 | Comanducci et al. | |
| 2007/0026021 A1 | 2/2007 | Fraser et al. | |
| 2007/0082014 A1 | 4/2007 | Costantino | |
| 2008/0241180 A1 | 10/2008 | Contorni | |
| 2009/0232820 A1 | 9/2009 | Fraser et al. | |
| 2009/0285845 A1 | 11/2009 | Masignani et al. | |
| 2010/0267931 A1 | 10/2010 | Arico et al. | |

FOREIGN PATENT DOCUMENTS

| | | |
|---|---|---|
| EP | 0467714 | 1/1992 |
| EP | 1645631 A2 | 4/2006 |
| EP | 1790660 A2 | 5/2007 |
| EP | 2042512 A2 | 4/2009 |
| EP | 2351767 A2 | 8/2011 |
| WO | WO 93/18150 * | 9/1993 |
| WO | WO-95/09232 A2 | 4/1995 |
| WO | WO 96/12020 A2 | 4/1996 |
| WO | WO-9612020 | 4/1996 |
| WO | WO-9629412 | 9/1996 |
| WO | WO-9817805 | 4/1998 |
| WO | WO 98/18810 A1 | 5/1998 |
| WO | WO 98/49288 A1 | 11/1998 |
| WO | WO 98/55495 A2 | 12/1998 |
| WO | WO-98/55604 A1 | 12/1998 |
| WO | WO-99/55872 A1 | 11/1999 |
| WO | WO 99/57280 A2 | 11/1999 |
| WO | WO 99/58683 A2 | 11/1999 |
| WO | WO-9957280 | 11/1999 |
| WO | WO-0022430 | 4/2000 |

(Continued)

OTHER PUBLICATIONS

Tettelin et al. Science 287: 1809-1815, 2000.*
Harlow et al. In: Antibodies: A Laboratory Manual. Cold Spring Harbor Laboratory, New York, p. 76, 1988.*
Forster et al. Nucleic Acid Res. 16: 291-303, 1988.*
Gomez et al. Vaccine 14: 1340-1346, 1996.*
Malorny et al. J. Bacteriol. 180: 1323-1330, 1998.*
Teerlink et al. J. Exp. Med. 166: 63-76, abstract, 1987.*
Ala'Aldeen et al. Vaccine 12: 535-541, 1994.*

(Continued)

*Primary Examiner* — Gary Nickol
(74) *Attorney, Agent, or Firm* — Morrison & Foerster LLP

(57) ABSTRACT

This invention provides, among other things, proteins, polypeptides, and fragments thereof, derived from the bacteria *Neisseria meningitidis* B. Also provided are nucleic acids encoding for such proteins, polypeptides, and/or fragments, as well as nucleic acids complementary thereto (e.g., antisense nucleic acids). Additionally, this invention provides antibodies which bind to the proteins, polypeptides, and/or fragments. This invention further provides expression vectors useful for making the proteins, polypeptides, and/or fragments, as well as host cells transformed with such vectors. This invention also provides compositions of the proteins, polypeptides, fragments, and/or nucleic acids, for use as vaccines, diagnostic reagents, immunogenic compositions, and the like. Methods of making the compositions and methods of treatment with the compositions are also provided. This invention also provides methods of detecting the proteins, polypeptides, fragments, and/or nucleic acids.

16 Claims, No Drawings

(56) References Cited

FOREIGN PATENT DOCUMENTS

| WO | WO-00/42192 A1 | 7/2000 |
| --- | --- | --- |
| WO | WO-00/44890 A1 | 8/2000 |
| WO | WO-0066791 | 11/2000 |
| WO | WO-01031019 | 5/2001 |
| WO | WO-0152885 | 7/2001 |
| WO | WO 0164920 * | 9/2001 |
| WO | WO-0164922 | 9/2001 |
| WO | WO-03/009869 A1 | 2/2003 |
| WO | WO-03020756 | 3/2003 |
| WO | WO-03/063766 | 8/2003 |
| WO | WO-2004032958 | 4/2004 |
| WO | WO-2004048404 | 6/2004 |
| WO | WO-2006024954 | 3/2006 |
| WO | WO-2006/081259 | 8/2006 |
| WO | WO-2007/060548 A2 | 5/2007 |
| WO | WO-2009/104097 A2 | 8/2009 |
| WO | WO-2010/046715 A1 | 4/2010 |
| WO | WO-00/43518 A1 | 7/2013 |

OTHER PUBLICATIONS

Cruse et al., Illustrated Dictionary of Immunology, 2nd Edn., CRC Press, pp. 46, 166 and 382, 2003.*

McGuiness et al. Mol. Microbiol. 7: 505-514, Feb. 1993.*

Greenspan et al., Nature Biotechnology 17:936-937, 1999.*

Fletcher et al. Infect. Immun. 72: 2088-2100, 2004.*

Dillard et al., "A peptidoglycan hydrolase similar to bacteriophage endolysins acts as an autolysin in Neisseria gonorrhoeae," Molecular Microbiology 25(5):893-901, 1997.

Fussenegger et al., "Tetrapac(tpc), a novel genotype of Neisseria gonorrhoeae affecting epithelial cell invasion, natural transformation competence and cell separation," Mol. Microbiol. 19:1357-1372, 1996.

Hopp et al., "Prediction of protein antigenic determinants from amino acid sequences," Proc. Natl. Acad. Sci. USA 78(6): 3824-3828, 1981.

Lommatzsch et al., "Outer membrane localization of murein hydrolases: MltA, a third lipoprotein lytic transglycosylase in Escherichia coli," Journal of Bacteriology 179(17):5465-5470, 1997.

Millan et al., "CpG DNA can induce strong Th1 humoral and cell-mediated immune responses against hepatitis B surface antigen in young mice," Proc. Natl. Acad. Sci. USA 95(26): 15553-15558, 1998.

Rokbi et al. "Evaluation of Recombinant Transferrin-Binding Protein B Variants from Neisseria meningitidis for Their Ability to Induce Cross-Reactive and Bactericidal Antibodies against a Genetically Diverse Collection of Serogroup B Strains," Infection and Immunity, 65(1):55-63, 1997.

Sun et al., "DNA as an adjuvant: capacity of insect DNA and synthetic oligodeoxynucleotides to augment T cell responses to specific antigen," J. Experimental Medicine 187(7):1145-1150, 1998.

Tabata, "Membrane bound lytic transglycosylase A MltA synechocystis sp strain PCC 6803," Database EMBL EBI Acc No. Q55666, 1996.

European Search Report and Examination Report mailed Jun. 18, 2007, for European Application No. 07075161.5 filed Oct. 30, 2000, 10 pages.

Delvig, A. A. et al. (Jul. 1997). "Vaccine-Induced IgG Antibodies to the Linear Epitope on the PorB Outer Membrane Protein Promote Opsonophagocytosis of Neisseria meningitides by Human Neutrophils," Clinical Immunology and Immunopathology 84(1):27-35.

Parkhill, J. et al. (Mar. 2000). "Complete DNA Sequence of a Serogroup A Strain of Neisseria meningitides Z2491," Nature 404:502-505.

Pizza, M. et al. (Mar. 2000). "Identification of Vaccine Candidates Against Serogroup B Meningococcus by Whole-Genome Sequencing," Science 287:1816-1820.

Database accession No. NMB1994.Tettelin at al. (Mar. 2, 2010).

Koeberling at al. (2007). "Improved immunogenicity of a H44/76 group B outer membrane vesicle vaccine with over-expressed genome-derived Neisserial antigen 1870," Vaccine 25(10):1912-1920.

The printed output from the NCBI open reading frame finder (12 pages).

United States Office Action mailed on Feb. 11, 2009, for U.S. Appl. No. 10/181,600, filed Jan. 17, 2001, 5 pages.

United States Office Action mailed on Jul. 24, 2008, for U.S. Appl. No. 10/181,600, filed Jan. 17, 2001, 23 pages.

United States Office Action mailed on Jul. 7, 2009, for U.S. Appl. No. 10/181,600, filed Jan. 17, 2001, 23 pages.

1997-11-17-NM_shotgun.dbs and 1997-12-15-NM.dbs, located at <ftp://ftp.sanger.ac.uk/pub/pathogens/nm/old data/>.

Aasel et al. (1998). Abstract from the 11th International Pathogenic Neisseria Conference, Nice France, Nov. 1-6, 1998. pp. 37-38.

Bernfield L. et al. (Sep. 2002). "Identification of a novel vaccine candidate for group B Neisseria meningitidis," Thirteenth International Pathogenic Neisseria Conference, Norwegian Institute of Public Health, Oslo, Norway, pp. 116.

Boslego et al. (1991). "Gonorrhea Vaccines," Chapter 17 In Vaccines and Immunotherapy, Cryz S.J. (Ed.), Pergamon Press: New York, NY, pp. 211-223.

Cannon (1989). "Conserved Lipoproteins of Pathogenic Neisseria Species Bearing the H.8 Epitope: Lipid-Modified Azurin and H.8 Outer Membrane Protein," Clinical Microbiology Reviews, vol. 2, Suppl., S1-S4.

Cantini et al. (Mar. 2006). "Solution Structure of the Immunodominant Domain of Protective Antigen GNA 1870 of Neisseria meningitidis," Journal of Biological Chemistry 281(11): 7220-7227.

Declaration by Dr. Julian Parkhill dated Jun. 12, 2008. 2 pages.

Farley J. et al. (Sep. 2002). "Characterization, cloning and expression of different subfamilies of the ORF 2086 gene from Neisseria meningitidis," Thirteenth International Pathogenic Neisseria Conference, Norwegian Institute of Public Health, Oslo, Norway, p. 124.

Feavers et al. (2009). "Meningococcal protein antigens and vaccines," Vaccine 275:B42-B50.

Fleischmann et al. (1995). "Whole-Genome Random Sequencing and Assembly of Haemophilus influenzae Rd," Science 269:496-501.

Fontana et al. (2002). "A genomic approach to identify vaccine candidates against gonococcus." Abstract from the 13th International Pathogenic Neisseria Conference, Oslo, Norway, Sep. 1-6, 2002. p. 248.

Giuliani et al. (2006). "A universal vaccine for serogroup B meningococcus," PNAS 103(29):10834-10839.

Giuliani et al. (Feb. 2005). "The Region Comprising Amino Acids 100 to 255 of Neisseria meningitidis Lipoprotein GNA 1870 Elicits Bactericidal Antibodies," Infection and Immunity 73(2): 1151-1160.

Masignani V. (Mar. 17. 2003). "Vaccination against Neisseria meningitidis using three variants of the lipoprotein GNA1870," J. Exp. Med. 197(6):789-799.

Morley, S. et al. (Dec. 12, 2001). "Vaccine prevention of meningococcal disease, coming soon?" Vaccine 20(5-6):666-687.

Nassif (2000). "A Furtive Pathogen Revealed," Science 287: 1767-1768.

Phase II clinical results for Novartis vaccine, Oct. 9, 2008.

Post by Dr. Parkhill on BIOSCI/Bionet of May 8, 1998.

Response to Communication, filed in EP Application No. 07075161. 5. Oct. 28, 2009.

Rinaudo et al. (2009). "Vaccinology in the genome era", The Journal of Clinical Investigation, 119(9):2515-2525.

Romero et al. (1994). "Current status of Meningococcal group B vaccine candidates: capsular or noncapsular?" Clin. Microbiol. Rev. 7(4):559-575.

Sanger Centre's "Projects" website as of Dec. 10, 1997 as retrievable via http://web.archive.org.

Sequence for "Putative Lipoprotein [Neisseria Meningitidis Z2491]," NCBI Reference Sequence: YP_002342062.1, Mar. 30, 2000.

Serruto et al. (2009). "Genome-based approaches to develop vaccines against bacterial pathogens," Vaccine 27:3245-3250.

(56) References Cited

OTHER PUBLICATIONS

Supplementary Declaration by Dr. Julian Parkhill, dated May 10, 2010.
Telford et al. (2003). "Genomic and Proteomics in Vaccine Design," in New Bacterial Vaccines, edited by Ellis et al. Kleweur Academic/Plenum Publishers, USA. pp. 1-11 (2 pages).
U.S. Appl. No. 60/098,685, "*Neisseria* Spp, Polypeptide, Gene Sequence and Uses Thereof," filed Sep. 1, 1998.
Welsch et al. (2004). "Protective Activity of Monoclonal Antibodies to Genome-Derived Neisserial Antigen 1870, a *Neisseria meningitidis* Candidate Vaccine," The Journal of Immunology 172: 5606-5615.
Zollinger (1997). "New and Improved Vaccines Against Meningococcal Disease" in New Generation Vaccines, 2nd Ed., edited by Levine et al., Marcel Dekker, New York. pp. 469-488.
Supplemental Submission in Opposition against European Patent EP 1645631, granted on Oct. 24, 2007. Opposition filed on May 25, 2010. 28 pages.
Hou et al. (2005). "Protective Antibody Responses Elicited by a Meningococcal Outer Membrane Vesicle Vaccine with Overexpressed Genome-Derived Neisserial Antigen 1870," J Infect Dis 192(4):580-90.
Zhu et al. (2005). "Evaluation of Recombinant Lipidated P2086 Protein as a Vaccine Candidate for Group B *Neisseria meningitidis* in a Murine Nasal Challenge Model," Infect Immun 73(10):6838-45. Norway, Sep. 1-6, 2002. p. 248.
JCVI-CMR website showing Z2491 Sanger sequence (http://cmr.jcvi.org/tigr-scripts/CMR/shared/Genomes.cgi and links).
Progress through the Sanger Institute FTP server. FTP root at ftp.sanger.ac.uk.
PSORT analysis of 200 of the sequences disclosed in PCT/US99/09346 (i.e., the original application underlying the Patent; published as W099/057280).
PSORT analysis of SEQ ID Nos. 4 and 6, and of 'Contig295' 300mer.
PSORT prediction result for SEQ ID No. 2.
Sutcliffe and Russell (1995). "Lipoproteins of gram-positive bacteria," J Bacteriol 177(5):11231128.
Appendix I to Statement of Grounds of Appeal filed by df-mp on Sep. 28, 2012, in relation to EP1645631, 1 pages.
Appendix II to Statement of Grounds of Appeal filed by df-mp on Sep. 28, 2012, in relation to EP1645631, 2 pages.
Beernick (Jul. 2010) "Impaired immungenicity of a meningococcal factor H-binding protein vaccine engineered to eliminate factor h binding," Clin Vac Immunol 17(7):1074-1078.
Beernink et al (Jul. 2006). "Rapid Genetic Grouping of Factor H-Binding Protein (Genome-Derived Neisserial Antigen 1870), a Promising Group B Meningococcal Vaccine Candidate," Clinical and Vaccine Immunology 13(7):758-763.
Beernink et al. (Jun. 2008). "Bactericidal antibody responses, induced by meningococcal recombinant chimeric factor H-binding protein vaccines," Infection and Immunity 76(6):25682575.
Beernink et al. (Sep. 2008). "Fine antigenic specificity and cooperative bactericidal activity of monoclonal antibodies directed at the meningococcal vaccine candidate factor h-binding protein," Infection and Immunity 76(9):4232-4240.
Cordis, "Preparation of meningococcal antigens," posted online on Feb. 2, 2005, 2 pages.
Declaration by Dr. Ellen Murphy, Ph.D., dated Sep. 14, 2011, submitted in opposition proceedings for EP1645631, 4 pages.
Declaration by E. Richard Moxon dated Feb. 16, 2013, submitted in opposition proceedings for EP1645631, 5 pages.
Declaration by Emilio A. Emini, Ph.D., dated Nov. 2, 2011, submitted in opposition proceedings for EP1645631, 5 pages.
Declaration by Isabel Delany, dated Feb. 18, 2013, submitted in opposition proceedings for EP1645631, 5 pages.
Declaration by Prof. Paul Dunman, Ph.D., dated Sep. 25, 2012, submitted in opposition proceedings for EP1645631, 14 pages.
Declaration by Rino Rappuoli, dated Oct. 13, 2011, submitted in opposition proceedings for EP1645631, 5 pages.
Declaration by Vega Masignani dated Feb. 18, 2013, submitted in opposition proceedings for EP1645631, 4 pages.
Facts and Submissions dated May 21, 2012, in relation to EP1645631, 30 pages.
GenPept accession No. AAF42204, "hypothetical protein NMB1870 [*Neisseria meningitidis* MC58]," retrieved on Sep. 26, 2012, 2 pages.
Granoff, DM. (2009). Relative importance of complement-mediated bactericidal and opsonic activity for protection against meningococcal disease. Vaccine 27(Supplement 2): B117-B125.
Jacobsson et al. (2009). "Prevalence and sequence variations of the genes encoding the five antigens included in the novel 5CVMB vaccine covering group B meningococcal disease" Vaccine. 27:1579-1584.
Jiang et al., (2010) "Broad vaccine coverage predicted for a bivalent recombinant factor H binding protein based vaccine to prevent serogroup B meningococcal disease" Vaccine 28:6086-6093.
Lucidarme et al., (Sep. 16, 2009) "Characterization of fHbp, nhba (gna2132), nadA, porA, sequence type (St), and genomic presence of IS1301 in group B meningococcal ST269 clonal complex isolates from England and Wales" Journal of Clinical Microbiology, 47(11):3577-85.
Lucidarme et al., 2010 "Characterization of fHbp, nhba (gna2132), nadA, porA, and sequence type in group B meningococcal case isolates collected in England and Wales during Jan. 2008 and potential coverage of an investigational group B meningococcal vaccine" Clinical and Vaccine Immunology 17(6):919-929.
Murphy et al., (2009) "Sequence diversity of the factor H binding protein vaccine candidate in epidemiologically relevant strains of serogroup B Neisseria meningitidis" J Infect Dis 200:379-389.
Notice of Opposition against European Patent EP 1645631, granted on Oct. 24, 2007. Opposition filed on Jul. 23, 2008. 20 pages.
Novartis (Jan. 22, 2013) "Novartis receives Eu approval for Bexsero®, first vaccine to prevent the leading cause of life-threatening meningitis across Europe," Media Release, 3 pages.
Pajon et al. (2010). "Frequency of factor H-binding protein modular groups and susceptibility to cross-reactive bactericidal activity in invasive meningococcal isolates" Vaccine 28:2122-2129.
Patentees' Response to Opposition against European Patent EP 1645631, granted on Oct. 24, 2007. 13 pages.
Pizza et al. (2008) "Factor H-binding protein, a unique meningococcal vaccine antigen" Vaccine 26S:146-8.
Prosite, "ScanProsite Results Viewer: USERSEQ1 (280aa)," retrieved on Jun. 21, 2012, 1 page.
Response to Appeal filed by Carpmaels & Ransford on Feb. 18, 2013, in relation to EP1645631, 21 pages.
Response to Appeal filed by df-mp on Feb. 18, 2013, in relation to EP1645631, 28 pages.
Scarselli et al. (Feb. 13, 2009). "Epitope Mapping of a Bactericidal Monoclonal Antibody against the Factor H Binding Protein of Neisseria meningitides," Journal of Molecular Biology 386(1):97-108.
Schneider et al. (Apr. 16, 2009) "Neisseria meningitidis recruits factor H using protein mimicry of host carbohydrates," Nature 458(7240):890-893.
Statement of Grounds of Appeal filed by Carpmaels & Ransford on Oct. 4, 2012, in relation to EP1645631, 9 pages.
Statement of Grounds of Appeal filed by df-mp on Sep. 28, 2012, in relation to EP1645631, 54 pages.
Supplementary declaration by Ellen Murphy dated Sep. 26, 2012, submitted in opposition proceedings for EP1645631, 3 pages.
Supplementary declaration by Prof. Paul Dunman, Ph.D., dated Sep. 25, 2012, submitted in opposition proceedings for EP1645631, 14 pages.
Tigr website as of 1998, 8 pages.
Welsch et al. (2007) "A novel mechanism for complement-mediated killing of encapsulated Neisseria meningitidis elicited by monoclonal antibodies to factor H-binding protein (genome-derived Neisserial antigen 1870)" Molecular Immunology 44(1-3):256.
Welsch et al. (Apr. 1, 2008). "Complement-dependent synergistic bactericidal activity of antibodies against factor H-binding protein, a sparsely distributed meningococcal vaccine antigen," J Infect Dis 197(7):1053-1061.

(56) References Cited

OTHER PUBLICATIONS

Bouvier et al. (1991). "A gene for a new lipoprotein in the dapA-purC interval of the Escherichia coli chromosome," J Bacteriol 173(17):5523-5531.

Chen, et al. (1994). "Determination of the optimal aligned spacing between the Shine-Dalgarno sequence and the translation initiation codon of *Escherichia coli* mRNAs," Nucleic Acids Res. 22(23):4953-4957.

Delgado et al. (2007). "Lipoprotein NMB0928 from Neisseria meningitidis serogroup B as a novel vaccine candidate," Vaccine 25:8420-8431.

Dinthilhac and Claverys (1997). "The adc locus, which affects competence for genetic transformation in Streptococcus pneumoniae, encodes an ABC transporter with a putative lipoprotein homologous to a family of streptococcal adhesins," Res Bicrobiol 148:119-131.

Fraser et al. (1997). "Genomic sequence of a lyme disease spirochaete, *Borrelia burgdorferi*," Nature 390:580-586.

Fraser et al. (1998). "Complete genome sequence of Treponema pallidum, the syphilis spirochete," Science 281:375-388.

Gold and Stormo (1987). "Translation Initiation", in *Escherichia con and Salmonella typhimurium*, Cellular and Molecular Biology, Ed. Neidhardt, pp. 1302-1307.

Grandi (2005). "Reverse vaccinology: a critical analysis," in *Encyclopedia of Genetics, Genomics, Proteomics and Bioinformatics*, pp. 1322-1326.

Hayashi and Wu, "Identification and characterization of lipid-modified proteins in bacteria," Chapter 10 in *Lipid Modifications of Proteins: a Practical Approach*, Hooper and Turner (eds.), published in 1992, 27 pages.

Hung et al. (2011). "The Neisseria meningitidis macrophage infectivity potentiator protein induces cross-strain serum bactericidal sctivity and is a potential serogroup B vaccine candidate," Infect Immun 79(9):3784-3791.

Johnson et al. (1999). "Analysis of the human Ig isotype response to lactoferrin binding protein a from *Neisseria meningitidis*," FEMS Immun. Med. Microbial. 25(4): 349-354.

Juncker et al. (2003). "Prediction of lipoprotein signal peptides in gram-negative bacteria," Protein Sci 12:1652-1662.

Liebl et al. (1997). "Properties and gene structure of the Thermotoga maritima alpha-amylase AmyA, a putative lipoprotein of a hyperthermophilic bacterium," J Bacteriol 179(3):941-948.

Milagres et al. (1998). "Specificity of bactericidal antibody response to serogroup B meningococcal strains in Brazilian children after immunization with an outer membrane vaccine," Infection and Immun. 66(10): 4755-4781.

Moxon (1997). "Applications of molecular microbiology to vaccinology," Lancet 350(9086):1240-1244.

Munkley, et al. (1991). "Blocking of bactericidal killing of Neisseria meningitidis by antibodies directed against slacc 4 outer membrane proteins," Microbial Pathogenesis 11: 447-452.

Pettersson, et al. (2006). "Vaccine potential of the Neisseria meningitidis lactoferrin-binding proteins LbpA and LbpB," Vaccine 24(17):3545-3557.

Pugsley (1993). "The complete general secretory pathway in gram-negative bacteria," Microbiological Rev 5(1):50-108.

Shevchik et al. (1996). "Characterization of pectin methylesterase B, an outer membrane lipoprotein of Erwinia chrysanthemi 3937," Mole Microbiol 19(3):455-466.

Sutcliffe and Russell (1995). "Lipoproteins of gram-positive bacteria," J Bacteriol 177(5):1123-1128.

von Heijne (1989). "The structure of signal peptides from bacterial lipoproteins," Protein Engineering 2(7):531-534.

Woods, et al. (1987). "Resistance to meningococcemia apparently conferred by anti-H.8 monoclonal antibody is due to contaminating endotoxin and not to specific immunoprotection," Infection and Immunity 55(8):1927-1928.

Wu et al. (1996). "A protein class database organized with ProSite protein groups and PIR superfamilies," J Comp Biol 3(4):547-561.

* cited by examiner

NEISSERIAL ANTIGENIC PEPTIDES

RELATED APPLICATIONS

This application is the National Stage of International Application No. PCT/IB00/01661, filed Oct. 30, 2000, which claims the benefit of U.S. Provisional App. No. 60/162,616, filed Oct. 29, 1999, all of which are incorporated by reference herein in their entireties.

All documents cited herein are incorporated by reference in their entirety.

REFERENCE TO SEQUENCE LISTING

This specification incorporates by reference the compact discs submitted in lieu of a paper copy of the Sequence Listing. Two (2) copies of CD-R compact discs, labeled Copy 1 and Copy 2, of the Sequence Listing were submitted. The two compact discs are identical. Also submitted is one (1) CD-R containing the computer readable form (CRF) of the Sequence Listing in accordance with 37 CFR 1.824. The compact discs were formatted on an IBM-PC and are compatible with MS-Windows. The compact discs contain the following file: Seqlist223002100000.txt, which is 6.24 MB. This file was created on Mar. 21, 2007.

TECHNICAL FIELD

This invention relates to antigenic peptide sequences from the bacteria *Neisseria meningitidis* and *Neisseria gonorrhoea*.

BACKGROUND ART

*N. meningitidis* is a non-motile, Gram-negative *diplococcus* that is pathogenic in humans.

Based on the organism's capsular polysaccharide, 12 serogroups of *N. meningitidis* have been identified. Group A is the pathogen most often implicated in epidemic disease in sub-Saharan Africa. Serogroups B and C are responsible for the vast majority of cases in the United States and in most developed countries. Serogroups W135 and Y are responsible for the rest of the cases in the United States and developed countries.

The meningococcal vaccine currently in use is a tetravalent polysaccharide vaccine composed of serogroups A, C, Y and W135. Meningococcus B remains a problem, however. The polysaccharide approach cannot be used because the menB capsular polysaccharide is a polymer of □(2-8)-linked N-acetyl neuraminic acid that is also present in mammalian tissue. One approach to a menB vaccine uses mixtures of outer membrane proteins (OMPs). To overcome the antigenic variability, multivalent vaccines containing up to nine different porins have been constructed [e.g., Poolman J T (1992) Development of a meningococcal vaccine. *Infect. Agents Dis.* 4:13-28]. Additional proteins to be used in outer membrane vaccines have been the opa and opc proteins, but none of these approaches have been able to overcome the antigenic variability [e.g., Ala'Aldeen & Borriello (1996)]. The meningococcal transferrin-binding proteins 1 and 2 are both surface exposed and generate bactericidal antibodies capable of killing homologous and heterologous strains. [*Vaccine* 14(1):49-53].

DISCLOSURE OF THE INVENTION

The invention provides fragments of the proteins disclosed in international patent applications WO99/57280 and WO00/22430 (the "International Applications"), wherein the fragments comprise at least one antigenic determinant.

Thus, if the length of any particular protein sequence disclosed in the International Applications is x amino acids, the present invention provides fragments of at most x-1 amino acids of that protein. The fragment may be shorter than this (e.g., x-2, x-3, x-4, . . . ), and is preferably 100 amino acids or less (e.g., 90 amino acids, 80 amino acids etc.). The fragment may be as short as 3 amino acids, but is preferably longer (e.g., up to 5, 6, 7, 8, 9, 10, 12, 15, 20, 25, 30, 35, 40, 50, 75, or 100 amino acids).

Preferred fragments comprise the meningococcal peptide sequences disclosed in Table 1, or sub-sequences thereof. The fragments may be longer than those given in Table 1 e.g., where a fragment in Table 1 runs from amino acid residue p to residue q of a protein, the invention also relates to fragments from residue (p-1), (p-2), or (p-3) to residue (q+1), (q+2), or (q+3).

The invention also provides polypeptides that are homologous (i.e., have sequence identity) to these fragments. Depending on the particular fragment, the degree of sequence identity is preferably greater than 50% (e.g., 60%, 70%, 80%, 90%, 95%, 99% or more). These homologous polypeptides include mutants and allelic variants of the fragments. Identity between the two sequences is preferably determined by the Smith-Waterman homology search algorithm as implemented in the MPSRCH program (Oxford Molecular), using an affine gap search with parameters gap open penalty=12 and gap extension penally 1.

The invention also provides proteins comprising one or more of the above-defined fragments.

The invention is subject to the proviso that it does not include within its scope proteins limited to any of the full length protein sequences disclosed in the International Applications (i.e., the even SEQ IDs: 2-3020 of WO99/57280 and the odd SEQ IDs: 963-1045 of WO00/22430).

The proteins of the invention can, of course, be prepared by various means (e.g., recombinant expression, purification from cell culture, chemical synthesis etc.) and in various forms (e.g., native, C-terminal and/or N-terminal fusions etc.). They are preferably prepared in substantially pure form (i.e., substantially free from other Neisserial or host cell proteins). Short proteins are preferably produced using chemical peptide synthesis.

According to a further aspect, the invention provides antibodies which recognise the fragments of the invention, with the proviso that the invention does not include within its scope antibodies which recognise any of the complete protein sequences in the International Applications. The antibodies may be polyclonal or monoclonal, and may be produced by any suitable means.

The invention also provides proteins comprising peptide sequences recognised by these antibodies. These peptide sequences will, of course, include fragments of the meningococcal proteins in the International Applications, but will also include peptides that mimic the antigenic structure of the meningococcal peptides when bound to immunoglobulin.

According to a further aspect, the invention provides nucleic acid encoding the fragments and proteins of the invention, with the proviso that the invention does not include within its scope nucleic acid encoding any of the full length protein sequences in the International Applications. The nucleic acids may be as short as 10 nucleotides, but are preferably longer (e.g., up to 10, 12, 15, 18, 20, 25, 30, 35, 40, 50, 75, or 100 nucleotides).

In addition, the invention provides nucleic acid comprising sequences homologous (i.e., having sequence identity) to these sequences. The degree of sequence identity is preferably greater than 50% (e.g., 60%, 70%, 80%, 90%, 95%, 99% or more). Furthermore, the invention provides nucleic acid which can hybridise to these sequences, preferably under "high stringency" conditions (e.g., 65° C. in a 0.1×SSC, 0.5% SDS solution).

It should also be appreciated that the invention provides nucleic acid comprising sequences complementary to those described above (e.g., for antisense or probing purposes).

Nucleic acid according to the invention can, of course, be prepared in many ways (e.g., by chemical synthesis, from genomic or cDNA libraries, from the organism itself etc.) and can take various forms (e.g., single stranded, double stranded, vectors, probes etc.). In addition, the term "nucleic acid" includes DNA and RNA, and also their analogues, such as those containing modified backbones, and also peptide nucleic acids (PNA), etc.

According to a further aspect, the invention provides vectors comprising nucleotide sequences of the invention (e.g., expression vectors) and host cells transformed with such vectors.

According to a further aspect, the invention provides compositions comprising protein, antibody, and/or nucleic acid according to the invention. These compositions may be suitable as vaccines, for instance, or as diagnostic reagents, or as immunogenic compositions.

The invention also provides nucleic acid, protein, or antibody according to the invention for use as medicaments (e.g., as vaccines or as immunogenic compositions) or as diagnostic reagents. It also provides the use of nucleic acid, protein, or antibody according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. Said Neisserial bacteria may be any species or strain (such as *N. gonorrhoeae*) but are preferably *N. meningitidis*, especially strain A or strain B.

The invention also provides a method of treating a patient, comprising administering to the patient a therapeutically effective amount of nucleic acid, protein, and/or antibody according to the invention.

According to further aspects, the invention provides various processes, for example:
A process for producing proteins of the invention is provided, comprising the step of culturing a host cell according to the invention under conditions which induce protein expression;
A process for producing protein or nucleic acid of the invention is provided, wherein the protein or nucleic acid is synthesised in part or in whole using chemical means;
A process for detecting polynucleotides of the invention is provided, comprising the steps of: (a) contacting a nucleic probe according to the invention with a biological sample under hybridizing conditions to form duplexes; and (b) detecting said duplexes; and
A process for detecting proteins of the invention is provided, comprising the steps of: (a) contacting an antibody according to the invention with a biological sample under conditions suitable for the formation of an antibody-antigen complexes; and (b) detecting said complexes.

A summary of standard techniques and procedures which may be employed in order to perform the invention (e.g., to utilise the disclosed sequences for vaccination or diagnostic purposes) follows. This summary is not a limitation on the invention but, rather, gives examples which may be used, but which are not required.

General

The practice of the present invention will employ, unless otherwise indicated, conventional techniques of molecular biology, microbiology, recombinant DNA, and immunology, which are within the skill of the art. Such techniques are explained fully in the literature e.g., Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

All publications, patents, and patent applications cited herein are incorporated in full by reference.

DEFINITIONS

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g., a composition "comprising" X may consist exclusively of X or may include something additional to X, such as X+Y.

The term "antigenic determinant" includes B-cell epitopes and T-cell epitopes.

The term "heterologous" refers to two biological, components that are not found together in nature. The components may be host cells, genes, or regulatory regions, such as promoters. Although the heterologous components are not found together in nature, they can function together, as when a promoter heterologous to a gene is operably linked to the gene. Another example is where a meningococcal sequence is heterologous to a mouse host cell. A further example would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

Expression Systems

The meningococcal nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (e.g., structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed]*.

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell,* 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual]*.

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and Methods for baculovirus/insect cell expression systems are commercially available in kit form from, inter alia, INVITROGEN, Carlsbab Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (e.g., plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g., structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human □-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 □m in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda*, and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, e.g., Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, e.g., HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, e.g., proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659, 122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology, Malcolm B. Wilkins, ed.,* 1984 Pitman Publishing Limited, London, pp. 21-52. References that describe other metabolically-regulated genes: Sheen, *Plant Cell,* 2:1027-1038 (1990); Maas et al., *EMBO J.* 9:3447-3452 (1990); Benkel and Hickey, *Proc. Natl. Acad. Sci.* 84:1337-1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr*, 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet*, 202:179-185, 1985. The genetic material may also be transferred into the plant cell by using polyethylene glycol, Krens, et al., *Nature*, 296, 72-74, 1982. Another method of introduction of nucleic acid segments is high velocity ballistic penetration by small particles with the nucleic acid either within the matrix of small beads or particles, or on the surface, Klein, et al., *Nature*, 327, 70-73, 1987 and Knudsen and Muller, 1991, *Planta*, 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA*, 79, 1859-1863, 1982.

The vector may also be introduced into the plant cells by electroporation. (Fromm et al., *Proc. Natl. Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Herocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (e.g., structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Nall. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) J. Biotechnol. 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g., ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, KANAMYCIN (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541*], Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907*], Streptococcus cremoris* [Powell et al. (1988) *Appl. Environ. Microbiol.* 54:655*]; Streptococcus lividans* [Powell et al. (1988) *Appl. Environ. Microbiol.* 54:655*], Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteria* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus* lactis by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (e.g., structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g., EP-A-0 196 056. Another example is a ubiquitin fusion protein. Such a fusion protein is made with the ubiquitin region that preferably retains a site for a processing enzyme (e.g., ubiquitin-specific processing protease) to cleave the ubiquitin from the foreign protein. Through this method, therefore, native foreign protein can be isolated (e.g., WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (e.g., see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17-24], pCl/1 [Brake et al. (1984) *PNAS USA* 81:4642-4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Either a high or low copy number vector may be selected, depending upon the effect of the vector and the foreign protein on the host. See e.g., Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141], *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See e.g., [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula*]; [Das et al. (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying meningococcal proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 □g/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (e.g., 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g., see WO98/20734), needles, and gene guns or hyposprays. Dosage treatment may be a single dose schedule or a multiple dose schedule.

Vaccines

Vaccines according to the invention may either be prophylactic (i.e., to prevent infection) or therapeutic (i.e., to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% TWEEN 80, and 0.5% SPAN 85 (optionally containing various amounts of MTP-PE (see below), although not required) formulated into submicron particles using a microfluidizer such as Model 110Y MICROFLUIDIZER (Microfluidics, Newton, Mass.), (b) SAF, containing 10% Squalane, 0.4% TWEEN 80, 5% PLURONIC blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% TWEEN 80, and one or more bacterial cell wall components from the group consisting of monophosphorylipid A (MPL), trehalose dimycolate (TDM), and cell wall skeleton (CWS), preferably MPL+ CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g., IL-1, IL-2, IL-4, IL-5, IL-6, IL-7, IL-12, etc.), interferons (e.g., gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (e.g., the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g., nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g., by injection, either subcutaneously, intramuscularly, or transdermally/transcutaneously (e.g., WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be employed [e.g., Robinson & Torres (1997) *Seminars in Immunology* 9:271-283; Donnelly et al. (1997) *Annu Rev Immunol* 15:617-648; see later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) *Cancer Gene Therapy* 1:51-64; Kimura (1994) *Human Gene Therapy* 5:845-852; Connelly (1995) *Human Gene Therapy* 6:185-193; and Kaplitt (1994) *Nature Genetics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses e.g., MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (e.g., HT1080 cells) or mink parent cell lines, which eliminates inactivation in human serum.

Preferred retroviruses for the construction of retroviral gene therapy vectors include Avian Leukosis Virus, Bovine Leukemia Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J Virol* 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in P.O. Box 1549 Manassas, Va. 20108 USA or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405, 712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Nall Acad Sci* 81:6349; and Miller (1990) *Human Gene Therapy* 1.

Human adenoviral gene therapy vectors are also known in the art and employable in this invention. See, for example, Berkner (1988) *Biolechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e., there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in P.O. Box 1549 Manassas, Va. 20108 USA or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, Nature 339 (1989) 385 and Sabin (1973) *J. Biol. Standardization* 1:115; rhinovirus, for example ATCC VR-1110 and those described in Arnold (1990) *J Cell Biochem* L401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569: 86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Nall Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochem Biophys*

*Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprise therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (e.g., see WO98/20734), needles, and gene guns or hyposprays. Dosage treatment may be a single dose schedule or a multiple dose schedule.

Methods for the ex vivo delivery and reimplantation of transformed cells into a subject are known in the art and described in e.g., WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta.* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Feigner (1987) *Proc. Natl. Acad. Sci. USA* 84:7413-7416); mRNA (Malone (1989) *Proc. Natl. Acad. Sci. USA* 86:6077-6081); and purified transcription factors (Debs (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark LIPOFECTIN, from GIBCO BRL, Grand Island, N.Y. (See, also, Feigner supra). Other commercially available liposomes include transfectace (DDAB/DOPE) and DOTAP/DOPE (Boerhinger). Other cationic liposomes can be prepared from readily available materials using techniques well known in the art. See, e.g., Szoka (1978) *Proc. Natl. Acad. Sci. USA* 75:4194-4198; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Alabaster, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See e.g., Straubinger (1983) *Meth. Immunol.* 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77; Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acid of these apoproteins are known and are described in, for example, Breslow (1985) Annu Rev. Biochem 54:699; Law (1986) Adv. Exp Med. Biol. 151:162; Chen (1986) J Biol Chem 261:12918; Kane (1980) Proc Natl Acad Sci USA 77:2465; and Utermann (1984) Hum Genet. 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J. Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Technologies, Inc., Stoughton, Mass., USA. Further description of lipoproteins can be found in Zuckermann et al. WO98/06437.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, POLYBRENE. Lipofectin™, and lipofectAMINE™ are monomers that form polycationic complexes when combined with polynucleotides/polypeptides.

Immunodiagnostic Assays

Meningogoccal antigens of the invention can be used in immunoassays to detect antibody levels (or, conversely, anti-meningococcal antibodies can be used to detect antigen levels). Immunoassays based on well defined, recombinant antigens can be developed to replace invasive diagnostics methods. Antibodies to meningococcal proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10}Ci)+0.4[\%(G+C)]-0.6(\% \text{ formamide})-600/n-1.5(\% \text{ mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex, which is stable enough to be detected.

The nucleic acid probes will hybridize to the meningococcal nucleotide sequences of the invention (including both sense and antisense strands). Though many different nucleotide sequences will encode the amino acid sequence, the native meningococcal sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to the meningococcal sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional meningococcal sequence may also be helpful as a label to detect the formed duplex. For example, a non-complementary nucleotide sequence may be attached to the 5' end of the probe, with the remainder of the probe sequence being complementary to a meningococcal sequence. Alternatively, non-complementary bases or longer sequences can be interspersed into the probe, provided that the probe sequence has sufficient complementarity with the a meningococcal sequence in order to hybridize therewith and thereby form a duplex which can be detected.

The exact length and sequence of the probe will depend on the hybridization conditions, such as temperature, salt condition and the like. For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*Proc. Natl. Acad. Sci. USA* (1983) 80: 7461], or using commercially available automated oligonucleotide synthesizers.

The chemical nature of the probe can be selected according to preference. For certain applications, DNA or RNA are appropriate. For other applications, modifications may be incorporated e.g., backbone modifications, such as phosphorothioates or methylphosphonates, can be used to increase in vivo half-life, alter RNA affinity, increase nuclease resistance etc. [e.g., see Agrawal & Iyer (1995) *Curr Opin Biotechnol* 6:12-19; Agrawal (1996) *TIBTECH* 14:376-387]; analogues such as peptide nucleic acids may also be used [e.g., see Corey (1997) *TIBTECH* 15:224-229; Buchardt et al. (1993) *TIBTECH* 11:384-386].

Alternatively, the polymerase chain reaction (PCR) is another well-known means for detecting small amounts of target nucleic acids. The assay is described in: Mullis et al. [*Meth. Enzymol.* (1987) 155: 335-350]; U.S. Pat. Nos. 4,683,195 and 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired meningococcal sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the meningococcal sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

MODES FOR CARRYING OUT THE INVENTION

Preferred Fragments

The protein sequences disclosed in the International Applications have been, inter alia, subjected to computer analysis to predict antigenic peptide fragments within the full-length proteins. Three algorithms have been used in this analysis:
AMPHI This program has been used to predict T-cell epitopes [Gao et al. (1989) *J. Immunol.* 143:3007; Roberts et al. (1996) *AIDS Res Hum Retrovir* 12:593; Quakyi et al. (1992) *Scand J Immunol* suppl. 11:9] and is available in the Protean package of DNASTAR, Inc. (1228 South Park Street, Madison, Wis. 53715 USA).
ANTIGENIC INDEX as disclosed by Jameson & Wolf (1988) The antigenic index: a novel algorithm for predicting antigenic determinants. CABIOS, 4:181:186
HYDROPHILICITY as disclosed by Hopp & Woods (1981) Prediction of protein antigenic determinants from amino acid sequences. PNAS, 78:3824-3828

The three algorithms often identify the same fragments. Such multiply-identified fragments are particularly preferred. The algorithms often identify overlapping fragments (e.g., for antigen "013", AMPHI identifies aa 42-46, and Antigenic. Index identifies aa 39-45). The invention explicitly includes fragments resulting from a combination of these overlapping fragments (e.g., the fragment from residue 39 to residue 46, in the case of "013"). Fragments separated by a single amino acid are also often identified (e.g., for "018-2", antigenic index identifies aa 19-23 and 25-41). The invention also includes fragments spanning the two extremes of such "adjacent" fragments (e.g., 19-41 for "081-2"). The Example provides preferred antigenic fragments of the proteins disclosed in the International Applications.

EXAMPLE 1

Preferred Antigenic Protein Fragments

The following amino acid sequences in Table 1 are identified by titles indicating the number assigned to the particular open reading frame (ORF), consistent with those designated in the International Applications. The titles are of the following form: [no prefix, g, or a] [#], where "no prefix" means a sequence from *N. meningitidis* serotype B, "a" means a sequence from *N. meningitidis* serotype A, and "g" means a sequence from *N. gonorrhoeae*; and "#" means the number assigned to that open reading frame (ORF). For example, "127" refers to an *N. meningitidis* B amino acid sequence, ORF number 127. The presence of a suffix "-1" or "-2" to these titles indicates an additional sequence found for that particular ORF. Thus, for example, "a12-2" refers to an *N. meningitidis* A amino acid sequence, ORF number 12, which is another sequence found for ORF 12 in addition to the originally designated ORF 12 and ORF 12-1. Each amino acid sequence is preceded by the beginning amino acid position number and followed by the ending amino acid position number.

TABLE 1

012-1
AMPHI Regions - AMPHI
SEQ. ID. NO. 1    19-LysLeuLeuGluGlnLeuMetArgPheLeuGlnPheLeuSerGluPheLeuPheAlaLeuPheArgIle-41
SEQ. ID. NO. 2    48-ArgAlaLeuLysPheAlaArgArg-55
SEQ. ID. NO. 3    90-AsnPheIleArgHisThr-95
SEQ. ID. NO. 4    133-HisAlaAlaArgThrPhe-138
SEQ. ID. NO. 5    160-GlnGlyPheTyrGlyVal-165
SEQ. ID. NO. 6    179-GlyPheLeuArgPheGlyArgPheLeuProThrLeuLeuGlnThrLeu-194
Antigenic Index - Jameson-Wolf
SEQ. ID. NO. 7    42-PheThrHisLysSerAsnArgAlaLeuLysPheAlaArgArgHisHis-57
SEQ. ID. NO. 8    77-HisThrHisArgThrAspAsnArgLysArgSerGlySerAsnPhe-91
SEQ. ID. NO. 9    93-ArgHisThrArgHis-97
SEQ. ID. NO. 10   101-AlaAlaArgArgHisLeuIleAspGlyAspGlyGlnArgAsn-114
SEQ. ID. NO. 11   120-ThrXxxLysLeuArgSerArgGlnThr-128
SEQ. ID. NO. 12   137-ThrPheGlnSerGluGlnAsnLeu-144
SEQ. ID. NO. 13   147-ArgLeuGlyAsnGlnLysHisArgArgAsnLeuMetThrGln-160
SEQ. ID. NO. 14   173-IleGlnHisLysLysAlaGly-179
Hydrophilic Regions - Hopp-Woods
SEQ. ID. NO. 15   45-LysSerAsnArgAlaLeuLysPheAlaArgArgHisHis-57
SEQ. ID. NO. 16   77-HisThrHisArgThrAspAsnArgLysArgSerGly-88
SEQ. ID. NO. 17   101-AlaAlaArgArgHisLeuIleAspGlyAspGlyGlnArg-113
SEQ. ID. NO. 18   121-XxxLysLeuArgSerArgGln-127
SEQ. ID. NO. 19   149-GlyAsnGlnLysHisArgArgAsnLeu-157
SEQ. ID. NO. 20   173-IleGlnHisLysLysAlaGly-179
013
AMPHI Regions - AMPHI
SEQ. ID. NO. 21   42-AspSerTyrThrPhe-46
Antigenic Index - Jameson-Wolf
SEQ. ID. NO. 22   17-LysSerGluArgXxxSerGlyGlyAsnMetValProArgProSerProPheLeuPro-35
SEQ. ID. NO. 23   39-ThrGlnLeuAspSerTyrThr-45
SEQ. ID. NO. 24   58-GluAlaAlaAlaGlnLysGlnProLysThrArgAlaValGly-71
SEQ. ID. NO. 25   91-ArgSerGlyXxxLysIle-96
Hydrophilic Regions - Hopp-Woods
SEQ. ID. NO. 26   17-LysSerGluArgXxxSerGly-23

TABLE 1-continued

| | |
|---|---|
| SEQ. ID. NO. 27 | 58-GluAlaAlaAlaGlnLysGlnProLysThrArgAlaValGly-71 |
| 015-2 | |
| AMPHI Regions - AMPHI | |
| SEQ. ID. NO. 28 | 33-GluLysProLeuAlaGlyPheTrpLysAlaLeuProHis-45 |
| SEQ. ID. NO. 29 | 107-MetCysCysValAlaCysIleVal-114 |
| Antigenic Index - Jameson-Wolf | |
| SEQ. ID. NO. 30 | 29-TrpLysAsnProGluLysProLeu-36 |
| SEQ. ID. NO. 31 | 90-MetArgAlaArgProArgSerThrLys-98 |
| Hydrophilic Regions - Hopp-Woods | |
| SEQ. ID. NO. 32 | 31-AsnProGluLysProLeu-36 |
| SEQ. ID. NO. 33 | 90-MetArgAlaArgProArgSerThrLys-98 |
| 018-2 | |
| AMPHI Regions - AMPHI | |
| SEQ. ID. NO. 34 | 6-IleGlnHisLeuArg-10 |
| SEQ. ID. NO. 35 | 180-HisGlyCysGlnHisIlePhe-186 |
| Antigenic Index - Jameson-Wolf | |
| SEQ. ID. NO. 36 | 1-MetValGluArgHisIleGln-7 |
| SEQ. ID. NO. 37 | 9-LeuArgAsnGlyHis-13 |
| SEQ. ID. NO. 38 | 19-ProSerGlnGlnVal-23 |
| SEQ. ID. NO. 39 | 25-GlnMetPheGlyGlyArgAlaTyrAspPheArgAlaAspLysAlaAlaGly-41 |
| SEQ. ID. NO. 40 | 67-TyrPheAlaAspAspLysPhe-73 |
| SEQ. ID. NO. 41 | 78-LeuArgGlyAsnLeuArg-83 |
| SEQ. ID. NO. 42 | 85-PheGlnThrAspLysAlaAspLeuArgThrGlyLysHisHisAlaAspGlyAlaAlaPro-104 |
| SEQ. ID. NO. 43 | 106-ThrAlaAlaAspIleArgValAlaAla-114 |
| SEQ. ID. NO. 44 | 129-GlnGlnArgGlnLeuVal-134 |
| SEQ. ID. NO. 45 | 137-IleAlaCysAspGluAspMetArgAsnThrGlyLeuHis-149 |
| SEQ. ID. NO. 46 | 151-GlnArgValGlyAsnArgTyrAla-158 |
| Hydrophilic Regions - Hopp-Woods | |
| SEQ. ID. NO. 47 | 1-MetValGluArgHisIleGln-7 |
| SEQ. ID. NO. 48 | 30-ArgAlaTyrAspPheArgAlaAspLysAlaAla-40 |
| SEQ. ID. NO. 49 | 67-TyrPheAlaAspAspLysPhe-73 |
| SEQ. ID. NO. 50 | 85-PheGlnThrAspLysAlaAspLeuArgThrGlyLysHisHisAlaAspGlyAlaAla-103 |
| SEQ. ID. NO. 51 | 106-ThrAlaAlaAspIleArgValAlaAla-114 |
| SEQ. ID. NO. 52 | 137-IleAlaCysAspGluAspMetArgAsn-145 |
| 019-2 | |
| AMPHI Regions - AMPHI | |
| SEQ. ID. NO. 53 | 33-ProAlaAspAsnIleGlu-38 |
| SEQ. ID. NO. 54 | 60-AspTyrGlyGlyTyrProSerAlaLeuAspAla-70 |
| SEQ. ID. NO. 55 | 80-AlaAlaTyrLeuGluAsnAlaGlyAsp-88 |
| SEQ. ID. NO. 56 | 90-AlaMetAlaGluAsnValArgAsnGluTrpLeuLysSer-102 |
| SEQ. ID. NO. 57 | 142-AlaAlaGluLeuValLysAsnThrGlyLysLeuProSerGlyCysThrLysLeuLeuGluGlnAlaAlaAlaSer-166 |
| SEQ. ID. NO. 58 | 173-AspAlaTrpArgArgValArg-179 |
| SEQ. ID. NO. 59 | 193-LeuAlaAlaAlaLeuGlySerProPheAspGlyGlyThrGlnGly-207 |
| SEQ. ID. NO. 60 | 215-AsnValIleGlyLysGluAlaArgLysSer-224 |
| SEQ. ID. NO. 61 | 229-AlaLeuLeuSerGluMet-234 |
| SEQ. ID. NO. 62 | 259-AsnValProAlaAlaLeuAspTyrTyrGly-268 |
| SEQ. ID. NO. 63 | 292-ArgArgTrpAspGluLeuAlaSerValIleSerHisMetProGluLysLeuGlnLys-310 |
| SEQ. ID. NO. 64 | 329-GlnGluAlaGluLysLeuTyrLysGlnAla-338 |
| SEQ. ID. NO. 65 | 367-AlaGlyLysAsnSerValArgArgMetAlaGlu-377 |
| SEQ. ID. NO. 66 | 451-ArgTyrIleSerPro-455 |
| SEQ. ID. NO. 67 | 495-GlnGlyLeuMetGlnValMet-501 |
| SEQ. ID. NO. 68 | 582-ArgAspTyrValLysLysValMet-589 |
| Antigenic Index - Jameson-Wolf | |
| SEQ. ID. NO. 69 | 22-SerSerThrAsnThr-26 |
| SEQ. ID. NO. 70 | 28-ProAlaGlyLysThrProAlaAspAsnIleGluThrAlaAspLeuSerAlaSerValProThrArgProAlaGluProGluArgLysThrLeuAlaAspTyrGlyGlyTyrProSerAla-67 |
| SEQ. ID. NO. 71 | 69-AspAlaValLysGlnLysAsnAspAla-77 |
| SEQ. ID. NO. 72 | 85-AsnAlaGlyAspSerAlaMet-91 |
| SEQ. ID. NO. 73 | 103-LeuGlyAlaArgArgGln-108 |
| SEQ. ID. NO. 74 | 115-GluTyrAlaLysLeuGluProAlaGlyArgAlaGlnGluValGluCysTyrAlaAspSerSerArgAsnAspTyrThrArgAlaAlaGluLeuValLysAsnThrGlyLysLeuProSerGlyCys-156 |
| SEQ. ID. NO. 75 | 167-GlyLeuLeuAspGlyAsnAspAlaTrpArgArgValArgGly-180 |
| SEQ. ID. NO. 76 | 182-LeuAlaGlyArgGlnThrThrArgAspAlaArgAsn-192 |
| SEQ. ID. NO. 77 | 199-SerProPheAspGlyGlyThrGlnGlySerArgGluTyr-211 |
| SEQ. ID. NO. 78 | 217-IleGlyLysGluAlaArgLysSerProAsnAla-227 |
| SEQ. ID. NO. 79 | 232-SerGluMetGluSerGlyLeuSerLeuGluGlnArgSer-244 |
| SEQ. ID. NO. 80 | 254-GlnSerGlnAsnLeu-258 |
| SEQ. ID. NO. 81 | 266-TyrTyrGlyLysValAlaAspArgArgGlnLeuThrAspAspGlnIle-281 |
| SEQ. ID. NO. 82 | 287-AlaAlaLeuArgAlaArgArgTrpAspGlu-296 |
| SEQ. ID. NO. 83 | 304-MetProGluLysLeuGlnLysSerProThr-313 |
| SEQ. ID. NO. 84 | 320-ArgSerArgAlaAlaThrGlyAsnThrGlnGluAlaGluLysLeuTyrLys-336 |
| SEQ. ID. NO. 85 | 339-AlaAlaThrGlyArgAsn-344 |
| SEQ. ID. NO. 86 | 350-AlaGlyGluGluLeuGlyArgLysIleAspThrArgAsnAsnValProAspAlaGlyLysAsnSerValArgArgMetAlaGluAspGlyAlaValLysArg-383 |
| SEQ. ID. NO. 87 | 389-GlnAsnSerGlnAsnSerAlaGlyAspAlaLysMetArgArgGlnAlaGlnAla-405 |
| SEQ. ID. NO. 88 | 409-PheAlaThrArgGlyPheAspGluAspLysLeuLeu-420 |
| SEQ. ID. NO. 89 | 438-SerAlaGluArgThrAspArgLysLeuAsnTyr-448 |
| SEQ. ID. NO. 90 | 454-SerProPheLysAspThrValIle-461 |
| SEQ. ID. NO. 91 | 464-AlaGlnAsnValAsnValAspProAla-472 |
| SEQ. ID. NO. 92 | 478-IleArgGlnGluSerArgPhe-484 |

TABLE 1-continued

| | |
|---|---|
| SEQ. ID. NO. 93 | 488-AlaGlnSerArgValGlyAla-494 |
| SEQ. ID. NO. 94 | 504-ThrAlaArgGluIleAlaGly-510 |
| SEQ. ID. NO. 95 | 520-TyrThrAlaAspGlyAsnIleArgMetGly-529 |
| SEQ. ID. NO. 96 | 535-AspThrLysArgArgLeuGlnAsnAsnGluVal-545 |
| SEQ. ID. NO. 97 | 550-GlyTyrAsnAlaGlyProGlyArgAlaArgArgTrpGlnAlaAspThrProLeuGlu-568 |
| SEQ. ID. NO. 98 | 579-SerGluThrArgAspTyrValLys-586 |
| SEQ. ID. NO. 99 | 606-LeuLysGlnArgMet-610 |
| Hydrophilic Regions - Hopp-Woods | |
| SEQ. ID. NO. 100 | 30-GlyLysThrProAlaAspAsnIleGluThrAlaAspLeu-42 |
| SEQ. ID. NO. 101 | 46-ValProThrArgProAlaGluProGluArgLysThrLeuAla-59 |
| SEQ. ID. NO. 102 | 69-AspAlaValLysGlnLysAsnAspAla-77 |
| SEQ. ID. NO. 103 | 85-AsnAlaGlyAspSerAlaMet-91 |
| SEQ. ID. NO. 104 | 103-LeuGlyAlaArgArgGln-108 |
| SEQ. ID. NO. 105 | 115-GluTyrAlaLysLeuGluProAlaGlyArgAlaGlnGluValGluCysTyrAla AspSerSerArgAsnAspTyrThrArgAlaAlaGluLeuValLysAsnThrGlyLysLeuProSerGlyCys-156 |
| SEQ. ID. NO. 106 | 170-AspGlyAsnAspAlaTrpArgArgValArgGly-180 |
| SEQ. ID. NO. 107 | 185-ArgGlnThrThrAspAlaArgAsn-192 |
| SEQ. ID. NO. 108 | 201-PheAspGlyGlyThrGlnGlySerArgGlu-210 |
| SEQ. ID. NO. 109 | 217-IleGlyLysGluAlaArgLysSerProAsn-226 |
| SEQ. ID. NO. 110 | 232-SerGluMetGluSer-236 |
| SEQ. ID. NO. 111 | 238-LeuSerLeuGluGlnArgSer-244 |
| SEQ. ID. NO. 112 | 270-ValAlaAspArgArgGlnLeuThrAspAspGlnIle-281 |
| SEQ. ID. NO. 113 | 287-AlaAlaLeuArgAlaArgArgTrpAspGlu-296 |
| SEQ. ID. NO. 114 | 304-MetProGluLysLeuGlnLys-310 |
| SEQ. ID. NO. 115 | 320-ArgSerArgAlaAlaThr-325 |
| SEQ. ID. NO. 116 | 327-AsnThrGlnGluAlaGluLysLeuTyrLys-336 |
| SEQ. ID. NO. 117 | 350-AlaGlyGluGluLeuGlyArgLysIleAspThrArgAsnAsnValProAspAla GlyLysAsnSerValArgArgMetAlaGluAspGlyAlaValLysArg-383 |
| SEQ. ID. NO. 118 | 392-GlnSerAlaGlyAspAlaLysMetArgArgGlnAlaGlnAla-405 |
| SEQ. ID. NO. 119 | 411-ThrArgGlyPheAspGluAspLysLeuLeu-420 |
| SEQ. ID. NO. 120 | 438-SerAlaGluArgThrAspArgLysLeu-446 |
| SEQ. ID. NO. 121 | 478-IleArgGlnGluSerArgPhe-484 |
| SEQ. ID. NO. 122 | 504-ThrAlaArgGluIleAlaGly-510 |
| SEQ. ID. NO. 123 | 535-AspThrLysArgArgLeuGlnAsn-542 |
| SEQ. ID. NO. 124 | 554-GlyProGlyArgAlaArgArgTrpGlnAla-563 |
| SEQ. ID. NO. 125 | 579-SerGluThrArgAspTyrValLys-586 |
| SEQ. ID. NO. 126 | 606-LeuLysGlnArgMet-610 |
| 023 | |
| AMPHI Regions - AMPHI | |
| SEQ. ID. NO. 127 | 42-LysGluTyrSerAlaTrpGlnAlaPhePheSerGlnThrTrpValLysValPhePhrGlnValSerPheIleAlaValPheLeuHisAlaTrpValGly-74 |
| SEQ. ID. NO. 128 | 77-AspLeuTrpMetAspTyrIleLys-84 |
| Antigenic Index - Jameson-Wolf | |
| SEQ. ID. NO. 129 | 1-MetValGluArgLysLeuThr-7 |
| SEQ. ID. NO. 130 | 40-LeuProLysGluTyrSer-45 |
| Hydrophilic Regions - Hopp-Woods | |
| SEQ. ID. NO. 131 | 1-MetValGluArgLysLeuThr-7 |
| 025-2 | |
| AMPHI Regions - AMPHI | |
| SEQ. ID. NO. 132 | 9-AlaAlaCysThrAlaValAlaAlaLeuLeuGlyGlyCysAla-22 |
| SEQ. ID. NO. 133 | 36-MetGlnAspAlaProSerSerAlaValTyrAsnAsnProTyrGlyAla-51 |
| SEQ. ID. NO. 134 | 126-AspPheArgAlaTrpAsnGlyMetThrAsp-135 |
| SEQ. ID. NO. 135 | 140-IleGlyGlnIleValLysVal-146 |
| SEQ. ID. NO. 136 | 206-AspPheArgAlaTrpAsnGlyMetThrAspAsnMet-217 |
| SEQ. ID. NO. 137 | 219-SerIleGlyGlnIleValLysVal-226 |
| SEQ. ID. NO. 138 | 248-AlaValGlnThrProValLysProAlaAla-257 |
| SEQ. ID. NO. 139 | 261-ValGlnSerAlaProGlnPro-267 |
| SEQ. ID. NO. 140 | 290-SerGlyThrArgSer-294 |
| SEQ. ID. NO. 141 | 307-LysValValAlaAspPhe-312 |
| SEQ. ID. NO. 142 | 343-GlyLeuArgGlyTyrGlyAsn-349 |
| Antigenic Index - Jameson-Wolf | |
| SEQ. ID. NO. 143 | 22-AlaThrGlnGlnPro-26 |
| SEQ. ID. NO. 144 | 33-AsnSerGlyMetGlnSerGlyAlaProSerSer-42 |
| SEQ. ID. NO. 145 | 52-ThrProTyrSerProAlaProAlaGlyAspAlaProTyr-64 |
| SEQ. ID. NO. 146 | 108-ValArgGlyAspThr-112 |
| SEQ. ID. NO. 147 | 115-AsnIleSerLysArgTyrHisIleSerGlnAspAspPheArgAla-129 |
| SEQ. ID. NO. 148 | 131-AsnGlyMetThrAspAsnThrLeu-138 |
| SEQ. ID. NO. 149 | 144-ValLysValLysProAlaGly-150 |
| SEQ. ID. NO. 150 | 157-AlaAlaValLysSerArgProAlaVal-165 |
| SEQ. ID. NO. 151 | 170-GlnProProValGln-174 |
| SEQ. ID. NO. 152 | 188-ValArgGlyAspThr-192 |
| SEQ. ID. NO. 153 | 195-AsnIleSerLysArgTyrHisIleSerGlnAspAspPheArgAla-209 |
| SEQ. ID. NO. 154 | 211-AsnGlyMetThrAspAsnMetLeu-218 |
| SEQ. ID. NO. 155 | 224-ValLysValLysProAlaGly-230 |
| SEQ. ID. NO. 156 | 232-AlaAlaProLysThrAlaAlaValGluSerArgProAlaValPro-246 |
| SEQ. ID. NO. 157 | 252-ProValLysProAlaAlaAlaGlnProProValGlnSerAlaProGlnPro-267 |
| SEQ. ID. NO. 158 | 270-ProAlaAlaGluAsnLysAlaValPro-278 |
| SEQ. ID. NO. 159 | 280-ProAlaProGlnSerProAlaAlaSerProSerGlyThrArgSerValGly-296 |
| SEQ. ID. NO. 160 | 302-ArgProThrGlnGlyLysValValAlaAspPheGlyGlyAsnAsnLysGlyValAsp-320 |
| SEQ. ID. NO. 161 | 333-AlaAspGlyLysVal-337 |
| SEQ. ID. NO. 162 | 342-SerGlyLeuArgGlyTyrGly-348 |

TABLE 1-continued

| | |
|---|---|
| SEQ. ID. NO. 163 | 363-TyrGlyHisAsnGln-367 |
| SEQ. ID. NO. 164 | 370-LeuValGlyGluGlyGlnGlnValLysArgGlyGlnGln-382 |
| SEQ. ID. NO. 165 | 387-GlyAsnThrAspAlaSerArgThrGlnLeu-396 |
| SEQ. ID. NO. 166 | 398-PheGluValArgGlnAsnGlyLysProValAsnProAsnSer-411 |
| Hydrophilic Regions - Hopp-Woods | |
| SEQ. ID. NO. 167 | 35-GlyMetGlnAspAlaProSer-41 |
| SEQ. ID. NO. 168 | 108-ValArgGlyAspThr-112 |
| SEQ. ID. NO. 169 | 120-TyrHisIleSerGlnAspAspPheArg-128 |
| SEQ. ID. NO. 170 | 144-ValLysValLysPro-148 |
| SEQ. ID. NO. 171 | 157-AlaAlaValLysSerArgProAlaVal-165 |
| SEQ. ID. NO. 172 | 188-ValArgGlyAspThr-192 |
| SEQ. ID. NO. 173 | 200-TyrHisIleSerGlnAspAspPheArg-208 |
| SEQ. ID. NO. 174 | 224-ValLysValLysPro-228 |
| SEQ. ID. NO. 175 | 237-AlaAlaValGluSerArgProAlaVal-245 |
| SEQ. ID. NO. 176 | 253-ValLysProAlaAla-257 |
| SEQ. ID. NO. 177 | 270-ProAlaAlaGluAsnLysAlaValPro-278 |
| SEQ. ID. NO. 178 | 290-SerGlyThrArgSer-294 |
| SEQ. ID. NO. 179 | 313-GlyGlyAsnAsnLysGlyValAsp-320 |
| SEQ. ID. NO. 180 | 333-AlaAspGlyLysVal-337 |
| SEQ. ID. NO. 181 | 373-GluGlyGlnGlnValLysArgGlyGln-381 |
| SEQ. ID. NO. 182 | 389-ThrAspAlaSerArgThr-394 |
| SEQ. ID. NO. 183 | 400-ValArgGlnAsnGlyLysProValAsn-408 |
| 031 | |
| AMPHI Regions - AMPHI | |
| SEQ. ID. NO. 184 | 11-TyrSerAlaIleArgLeuPheThrGlnAlaValIleGluPheProGlnThrAlaGluHisCysArgArgThrArgAsp-36 |
| SEQ. ID. NO. 185 | 48-ArgArgProValGln-52 |
| Antigenic Index - Jameson-Wolf | |
| SEQ. ID. NO. 186 | 1-ArgLeuLysHisGlyVal-6 |
| SEQ. ID. NO. 187 | 25-ProGlnThrAlaGluHisCysArgArgThrArgAspGlnHisGlnGluArgArgAsnArgGlnGlyPheArgArgProValGlnHisValGlyArgArgAsnGlnGlnGlnArgHisSerGlnThrCysGlyGlnSerGlyArgAsnHisAlaGlnLysGlnGlnCysAlaThrArgGln-84 |
| Hydrophilic Regions - Hopp-Woods | |
| SEQ. ID. NO. 188 | 28-AlaGluHisCysArgArgThrArgAspGlnHisGlnGluArgArgAsnArgGlnGlyPheArgArgProVal-51 |
| SEQ. ID. NO. 189 | 54-ValGlyArgArgAsnGlnGlnGlnArgHisSerGln-65 |
| SEQ. ID. NO. 190 | 69-GlnSerGlyArgAsnHisAlaGlnLysGlnGlnCysAlaThrArgGln-84 |
| 032-2 | |
| AMPHI Regions - AMPHI | |
| SEQ. ID. NO. 191 | 11-LeuArgArgProLeuArgGln-17 |
| SEQ. ID. NO. 192 | 67-ProPheAlaAspAsnValTyrPro-74 |
| SEQ. ID. NO. 193 | 94-ThrAlaAlaValHisGlnPheGluGln-102 |
| SEQ. ID. NO. 194 | 114-ValHisGlyGlnIleGlnHisProValGlnProPheLeuArg-127 |
| SEQ. ID. NO. 195 | 134-LeuGlyLeuLeuArgArgPheAspVal-142 |
| Antigenic Index - Jameson-Wolf | |
| SEQ. ID. NO. 196 | 1-MetArgArgAsnVal-5 |
| SEQ. ID. NO. 197 | 10-ValLeuArgArgProLeuArg-16 |
| SEQ. ID. NO. 198 | 28-ArgAlaValProAlaGlyLysGlnGlyPhe-37 |
| SEQ. ID. NO. 199 | 41-CysArgLeuThrGlnArgGln-47 |
| SEQ. ID. NO. 200 | 57-AlaAspGlnArgHis-61 |
| SEQ. ID. NO. 201 | 107-HisArgGlnArgVal-111 |
| SEQ. ID. NO. 202 | 138-ArgArgPheAspValGlyGlyArgVal-146 |
| SEQ. ID. NO. 203 | 160-LeuProProArgArgLysLeuAlaSerGlnArgProPheProGln-174 |
| Hydrophilic Regions - Hopp-Woods | |
| SEQ. ID. NO. 204 | 1-MetArgArgAsnVal-5 |
| SEQ. ID. NO. 205 | 10-ValLeuArgArgProLeuArg-16 |
| SEQ. ID. NO. 206 | 28-ArgAlaValProAlaGlyLys-34 |
| SEQ. ID. NO. 207 | 41-CysArgLeuThrGln-45 |
| SEQ. ID. NO. 208 | 57-AlaAspGlnArgHis-61 |
| SEQ. ID. NO. 209 | 107-HisArgGlnArgVal-111 |
| SEQ. ID. NO. 210 | 138-ArgArgPheAspValGlyGly-144 |
| SEQ. ID. NO. 211 | 161-ProProArgArgLysLeuAlaSer-168 |
| 033-2 | |
| AMPHI Regions - AMPHI | |
| SEQ. ID. NO. 212 | 6-GlnTyrGlyGlyLeuAlaGlyPheProLysArgCysGluSerGlu-20 |
| SEQ. ID. NO. 213 | 64-GlyGlnAlaPheGluAlaLeuAsnCys-72 |
| SEQ. ID. NO. 214 | 95-ValGlyAlaLeuProLysTyrLeuAlaSerAsnValValArgAspMetHisGlyLeuLeuSerThrVal-117 |
| SEQ. ID. NO. 215 | 120-GlnThrGlyLysValLeuAspLysIleProGlyAlaMetGlu-133 |
| SEQ. ID. NO. 216 | 142-IleLysThrLeuAlaGlu-147 |
| SEQ. ID. NO. 217 | 157-SerLeuPheGluAsnPhe-162 |
| SEQ. ID. NO. 218 | 168-GlyProValAspGlyHisAsnValGluAsnLeuValAspValLeuLysAspLeuArgSerArg-188 |
| SEQ. ID. NO. 219 | 207-AlaGluAsnAspPro-211 |
| SEQ. ID. NO. 220 | 213-LysTyrHisAlaValAlaAlaAsnLeuProLysGluSerAlaAla-226 |
| SEQ. ID. NO. 221 | 242-TyrThrGlnValPheGlyLys-248 |
| SEQ. ID. NO. 222 | 280-PheProAspArgTyrPheAspVal-287 |
| SEQ. ID. NO. 223 | 307-LysProValValAlaIleTyrSer-314 |
| SEQ. ID. NO. 224 | 316-PheLeuGlnArgAlaTyrAspGlnLeu-324 |
| SEQ. ID. NO. 225 | 363-CysValProAsnMet-367 |
| SEQ. ID. NO. 226 | 390-AlaProAlaAlaValArgTyrProArgGlyThr-400 |

TABLE 1-continued

| | |
|---|---|
| SEQ. ID. NO. 227 | 406-ValSerAspGlyMetGluThrValGlu-414 |
| SEQ. ID. NO. 228 | 419-IleIleArgArgGlu-423 |
| SEQ. ID. NO. 229 | 432-PheGlySerMetValAla-437 |
| SEQ. ID. NO. 230 | 453-MetArgPheValLysProIleAspGluGlu-462 |
| SEQ. ID. NO. 231 | 469-ArgSerHisAspArgIle-474 |
| SEQ. ID. NO. 232 | 489-AlaValLeuGluValLeu-494 |
| SEQ. ID. NO. 233 | 510-AspThrValThrGlyHisGly-516 |
| SEQ. ID. NO. 234 | 518-ProLysLysLeuLeu-522 |
| Antigenic Index - Jameson-Wolf | |
| SEQ. ID. NO. 235 | 11-AlaGlyPheProLysArgCysGluSerGluTyrAspAla-23 |
| SEQ. ID. NO. 236 | 28-HisSerSerThrSerIle-33 |
| SEQ. ID. NO. 237 | 41-AlaAlaAspLysLeuLeuGlySerAspArgArgSerVal-53 |
| SEQ. ID. NO. 238 | 57-GlyAspGlyAlaMetThr-62 |
| SEQ. ID. NO. 239 | 72-CysAlaGlyAspMetAspVal-78 |
| SEQ. ID. NO. 240 | 85-AsnAspAsnGluMetSerIle-91 |
| SEQ. ID. NO. 241 | 105-AsnValValArgAspMetHisGly-112 |
| SEQ. ID. NO. 242 | 117-ValLysAlaGlnThrGlyLysValLeuAspLysIleProGly-130 |
| SEQ. ID. NO. 243 | 134-PheAlaGlnLysValGluHisLysIleLysThrLeuAlaGluGluAlaGluHisAlaLysGln-154 |
| SEQ. ID. NO. 244 | 166-TyrThrGlyProValAspGlyHisAsn-174 |
| SEQ. ID. NO. 245 | 181-ValLeuLysAspLeuArgSerArgLysGlyProGln-192 |
| SEQ. ID. NO. 246 | 198-ThrLysLysGlyAsnGlyTyrLysLeuAlaGluAsnAspProValLys-213 |
| SEQ. ID. NO. 247 | 220-LeuProLysGluSerAlaAla-226 |
| SEQ. ID. NO. 248 | 228-MetProSerGluLysGluProLysProAlaAlaLysProThrTyr-242 |
| SEQ. ID. NO. 249 | 253-ArgAlaAlaAlaAspSerArgLeu-260 |
| SEQ. ID. NO. 250 | 266-AlaMetArgGluGlySerGlyLeuValGluPheGluGlnArgPheProAspArgTyrPhe-285 |
| SEQ. ID. NO. 251 | 345-ValGlyAlaAspGlyProThrHis-352 |
| SEQ. ID. NO. 252 | 370-AlaAlaProSerAspGluAsnGluCysArg-379 |
| SEQ. ID. NO. 253 | 395-ArgTyrProArgGlyThrGlyThrGlyAlaProValSerAspGlyMetGluThr<br>ValGluIleGlyLysGlyIleIleArgArgGluGlyGluLysThrAla-428 |
| SEQ. ID. NO. 254 | 457-LysProIleAspGluGluLeuIle-464 |
| SEQ. ID. NO. 255 | 467-LeuAlaAlaArgSerHisAspArgIleValThrLeuGluGluAsnAlaGluGlnGlyGlyAlaGlyGly-488 |
| SEQ. ID. NO. 256 | 512-ValThrGlyHisGlyAspProLysLysLeuLeuAspAspLeuGlyLeu-527 |
| SEQ. ID. NO. 257 | 530-GluAlaValGluArgArgValArg-537 |
| SEQ. ID. NO. 258 | 540-LeuSerAspArgAspAlaAlaAsn-547 |
| Hydrophilic Regions - Hopp-Woods | |
| SEQ. ID. NO. 259 | 13-PheProLysArgCysGluSerGluTyrAsp-22 |
| SEQ. ID. NO. 260 | 41-AlaAlaAspLysLeuLeuGlySerAspArgArgSerVal-53 |
| SEQ. ID. NO. 261 | 74-GlyAspMetAspVal-78 |
| SEQ. ID. NO. 262 | 85-AsnAspAsnGluMetSerIle-91 |
| SEQ. ID. NO. 263 | 106-ValValArgAspMetHis-111 |
| SEQ. ID. NO. 264 | 123-LysValLeuAspLysIleProGly-130 |
| SEQ. ID. NO. 265 | 134-PheAlaGlnLysValGluHisLysIleLysThrLeuAlaGluGluAlaGluHisAlaLysGln-154 |
| SEQ. ID. NO. 266 | 181-ValLeuLysAspLeuArgSerArgLysGlyPro-191 |
| SEQ. ID. NO. 267 | 198-ThrLysLysGlyAsnGly-203 |
| SEQ. ID. NO. 268 | 205-LysLeuAlaGluAsnAspProValLys-213 |
| SEQ. ID. NO. 269 | 220-LeuProLysGluSerAlaAla-226 |
| SEQ. ID. NO. 270 | 228-MetProSerGluLysGluProLysProAlaAla-238 |
| SEQ. ID. NO. 271 | 253-ArgAlaAlaAlaAspSerArgLeu-260 |
| SEQ. ID. NO. 272 | 266-AlaMetArgGluGlySerGly-272 |
| SEQ. ID. NO. 273 | 274-ValGluPheGluGlnArgPheProAspArgTyrPhe-285 |
| SEQ. ID. NO. 274 | 372-ProSerAspGluAsnGluCys-378 |
| SEQ. ID. NO. 275 | 405-ProValSerAspGlyMetGluThrValGluIleGlyLysGlyIleIleArgArgGluGlyGluLysThrAla-428 |
| SEQ. ID. NO. 276 | 457-LysProIleAspGluGluLeuIle-464 |
| SEQ. ID. NO. 277 | 467-LeuAlaAlaArgSerHisAspArgIleValThrLeuGluGluAsnAlaGluGlnGlyGly-485 |
| SEQ. ID. NO. 278 | 513-ThrGlyHisGlyAspProLysLysLeuLeuAsp-523 |
| SEQ. ID. NO. 279 | 530-GluAlaValGluArgArgValArg-537 |
| SEQ. ID. NO. 280 | 540-LeuSerAspArgAspAlaAlaAsn-547 |
| 034-2 | |
| AMPHI Regions - AMPHI | |
| SEQ. ID. NO. 281 | 35-LeuAspHisAlaAla-39 |
| SEQ. ID. NO. 282 | 52-AsnLeuGluGlnMetArgAlaIleMetGluAlaAlaAspGln-65 |
| SEQ. ID. NO. 283 | 94-AlaValGluGluPheProHisIlePro-102 |
| SEQ. ID. NO. 284 | 152-ThrValValAsnPheSer-157 |
| SEQ. ID. NO. 285 | 168-IleGlyValLeuGlyAsnLeuGluThrGly-177 |
| SEQ. ID. NO. 286 | 186-GlyAlaValGlyLysLeuSer-192 |
| SEQ. ID. NO. 287 | 226-TyrLysPheThrArgProProThrGly-234 |
| SEQ. ID. NO. 288 | 236-ValLeuArgIleAspArgIleLysGluIleHisGlnAlaLeu-249 |
| SEQ. ID. NO. 289 | 261-SerValProGlnGluTrpLeuLysValIleAsnGluTyrGlyGlyAsnIleGly<br>GluThrTyrGlyValProValGluGluIleValGluGlyIleLysHisGly-295 |
| SEQ. ID. NO. 290 | 314-ArgArgTyrLeuAlaGluAsn-320 |
| SEQ. ID. NO. 291 | 330-LeuSerLysThrIleGluAlaMetLys-338 |
| Antigenic Index - Jameson-Wolf | |
| SEQ. ID. NO. 292 | 20-LeuProLysGluThrGln-25 |
| SEQ. ID. NO. 293 | 37-HisAlaAlaGluAsnSerTyrGly-44 |
| SEQ. ID. NO. 294 | 54-GluGlnMetArgAlaIleMetGluAlaAlaAspGlnValAsp-67 |
| SEQ. ID. NO. 295 | 75-SerAlaGlyAlaArgLysTyrAla-82 |
| SEQ. ID. NO. 296 | 106-HisGlnAspHisGlyAlaSerProAspValCysGlnArgSerIle-120 |
| SEQ. ID. NO. 297 | 129-MetAspGlySerLeuMetGluAspGlyLysThrProSerSerTyrGluTyr-145 |
| SEQ. ID. NO. 298 | 164-ValGluGlyGluIle-168 |
| SEQ. ID. NO. 299 | 173-AsnLeuGluThrGlyGluAlaGlyGluGluAspGlyVal-185 |

TABLE 1-continued

| | |
|---|---|
| SEQ. ID. NO. 300 | 191-LeuSerHisAspGln-195 |
| SEQ. ID. NO. 301 | 208-LysAspThrGlyVal-212 |
| SEQ. ID. NO. 302 | 221-ThrSerHisGlyAla-225 |
| SEQ. ID. NO. 303 | 227-LysPheThrArgProProThrGlyAspValLeuArgIleAspArgIleLysGluIleHis-246 |
| SEQ. ID. NO. 304 | 258-GlySerSerSerValPro-263 |
| SEQ. ID. NO. 305 | 271-AsnGluTyrGlyGlyAsnIleGlyGlu-279 |
| SEQ. ID. NO. 306 | 287-GluIleValGluGlyIleLysHisGlyValArgLysValAsnIleAspThrAspLeuArgLeuAlaSerThrGlyAlaVal-313 |
| SEQ. ID. NO. 307 | 316-TyrLeuAlaGluAsnProSerAspPheAspProArgLysTyrLeuSer-331 |
| SEQ. ID. NO. 308 | 333-ThrIleGluAlaMetLys-338 |
| SEQ. ID. NO. 309 | 350-CysGluGlyGlnAlaGlyLysIleLysProValSerLeuGluLysMetAlaSerArgTyrAlaLysGlyGluLeu-374 |
| Hydrophilic Regions - Hopp-Woods | |
| SEQ. ID. NO. 310 | 54-GluGlnMetArgAlaIleMetGluAlaAlaAspGlnValAsp-67 |
| SEQ. ID. NO. 311 | 76-AlaGlyAlaArgLysTyrAla-82 |
| SEQ. ID. NO. 312 | 108-AspHisGlyAlaSerProAspValCysGln-117 |
| SEQ. ID. NO. 313 | 132-SerLeuMetGluAspGlyLysThrProSer-141 |
| SEQ. ID. NO. 314 | 164-ValGluGlyGluIle-168 |
| SEQ. ID. NO. 315 | 175-GluThrGlyGluAlaGlyGluAspGlyVal-185 |
| SEQ. ID. NO. 316 | 208-LysAspThrGlyVal-212 |
| SEQ. ID. NO. 317 | 235-AspValLeuArgIleAspArgIleLysGluIleHis-246 |
| SEQ. ID. NO. 318 | 287-GluIleValGluGlyIleLysHisGlyValArgLysValAsnIleAspThrAspLeuArgLeu-307 |
| SEQ. ID. NO. 319 | 320-AsnProSerAspPheAspProArgLysTyrLeu-330 |
| SEQ. ID. NO. 320 | 333-ThrIleGluAlaMetLys-338 |
| SEQ. ID. NO. 321 | 352-GlyGlnAlaGlyLysIleLysProValSerLeuGluLysMetAlaSerArgTyrAlaLysGlyGluLeu-374 |
| 036-1 | |
| AMPHI Regions - AMPHI | |
| SEQ. ID. NO. 322 | 6-AlaValTyrSerAlaCysAlaAla-13 |
| SEQ. ID. NO. 323 | 29-GlyArgCysValAsnGlnTyr-35 |
| SEQ. ID. NO. 324 | 59-SerSerGlyArgPheCysGlnThrIleLys-68 |
| SEQ. ID. NO. 325 | 106-AlaAlaSerSerSerGlnSer-112 |
| SEQ. ID. NO. 326 | 142-AlaAsnArgArgVal-146 |
| Antigenic Index - Jameson-Wolf | |
| SEQ. ID. NO. 327 | 16-ProAlaArgThrSerSerSerArgArgCysValSerSerGlyArgCysValAsnGlnTyrSerSerArgAlaAspAla-41 |
| SEQ. ID. NO. 328 | 43-ProTrpArgArgHisSerGlyAla-50 |
| SEQ. ID. NO. 329 | 55-CysSerSerAspSerSerGlyArgPhe-63 |
| SEQ. ID. NO. 330 | 73-ProSerPheSerAlaArgLysThrCysSerAspGlyGluThrSerAlaAspSerAsnTrpArg-93 |
| SEQ. ID. NO. 331 | 96-HisAlaAspGlyLeuGlnThrAlaSerSerAlaAlaSerSerSerGlnSerAlaGlnThrAlaArgArgMetPhe-120 |
| SEQ. ID. NO. 332 | 133-SerGlyArgPheCysCysGlyArgArgAlaAsnArgArgValArgHisGlyArgGlnAspAsnArgPro-155 |
| SEQ. ID. NO. 333 | 158-ProMetArgGluSerArgArgGlnSerAla-167 |
| SEQ. ID. NO. 334 | 178-LeuProAlaArgThrArgCys-184 |
| SEQ. ID. NO. 335 | 186-CysArgLeuLysArgArgIleProProAla-195 |
| SEQ. ID. NO. 336 | 200-ProProAlaArgProAspAsnArgSerAsnGlyGlySerSerAlaTyrArgThrMetHisLysThrLeuArgProTyrGluArgPro-228 |
| Hydrophilic Regions - Hopp-Woods | |
| SEQ. ID. NO. 337 | 18-ArgThrSerSerSerArgArgCysValSerSer-28 |
| SEQ. ID. NO. 338 | 35-TyrSerSerArgAlaAsp-40 |
| SEQ. ID. NO. 339 | 45-ArgArgHisSerGly-49 |
| SEQ. ID. NO. 340 | 55-CysSerSerAspSerSerGlyArg-62 |
| SEQ. ID. NO. 341 | 75-PheSerAlaArgLysThrCysSerAspGlyGluThrSerAla-88 |
| SEQ. ID. NO. 342 | 107-AlaSerSerSerGlnSer-112 |
| SEQ. ID. NO. 343 | 114-GlnThrAlaArgArgMetPhe-120 |
| SEQ. ID. NO. 344 | 137-CysCysGlyArgArgAlaAsnArgArgValArgHisGlyArgGlnAspAsnArgPro-155 |
| SEQ. ID. NO. 345 | 160-ArgGluSerArgArgGlnSer-166 |
| SEQ. ID. NO. 346 | 178-LeuProAlaArgThrArgCys-184 |
| SEQ. ID. NO. 347 | 186-CysArgLeuLysArgArgIleProPro-194 |
| SEQ. ID. NO. 348 | 202-AlaArgProAspAsnArgSerAsnGlyGly-211 |
| SEQ. ID. NO. 349 | 217-ThrMetHisLysThrLeuArgProTyrGluArgPro-228 |
| 038 | |
| AMPHI Regions - AMPHI | |
| SEQ. ID. NO. 350 | 100-GluAlaLysAspHis-104 |
| SEQ. ID. NO. 351 | 134-GluSerIleLys-137 |
| SEQ. ID. NO. 352 | 157-GluLysGlyThrGlyGluLeuSerAlaValGlnGluValGluLys-171 |
| SEQ. ID. NO. 353 | 178-AlaProIleAlaSerLeuAsn-184 |
| SEQ. ID. NO. 354 | 195-GluPheGlyGlnPheLeuGluProValArgAlaTyrArgArgGlnTyrGlyVal-212 |
| Antigenic Index - Jameson-Wolf | |
| SEQ. ID. NO. 355 | 2-ThrAspPheArgGlnAspPhe-8 |
| SEQ. ID. NO. 356 | 22-GluPheThrThrLysAlaGlyArgArgSerPro-32 |
| SEQ. ID. NO. 357 | 38-GlyLeuPheAsnAspGlyLeu-44 |
| SEQ. ID. NO. 358 | 58-IleGluSerGlyIleArg-63 |
| SEQ. ID. NO. 359 | 85-LeuAlaGluLysGlyVal-90 |
| SEQ. ID. NO. 360 | 96-TyrAsnArgLysGluAlaLysAspHisGlyGluGlyGly-108 |
| SEQ. ID. NO. 361 | 125-ValIleSerAlaGlyThrSerValArgGluSerIleLysLeuIleGluAlaGluGlyAlaThrLeuAspArgMetGluLysGlyThrGlyGlu-162 |
| SEQ. ID. NO. 362 | 167-GlnGluValGluLysGlnTyrGlyLeu-175 |
| SEQ. ID. NO. 363 | 191-GlnAsnAsnProGluPheGlyGln-198 |
| SEQ. ID. NO. 364 | 203-ValArgAlaTyrArgArgGlnTyrGlyValGlu-213 |
| Hydrophilic Regions - Hopp-Woods | |
| SEQ. ID. NO. 365 | 2-ThrAspPheArgGlnAspPhe-8 |
| SEQ. ID. NO. 366 | 22-GluPheThrThrLysAlaGlyArgArgSer-31 |
| SEQ. ID. NO. 367 | 85-LeuAlaGluLysGlyVal-90 |

TABLE 1-continued

| | |
|---|---|
| SEQ. ID. NO. 368 | 96-TyrAsnArgLysGluAlaLysAspHisGlyGlu-106 |
| SEQ. ID. NO. 369 | 130-ThrSerValArgGluSerIleLysLeuIleGluAlaGluGlyAlaThr-145 |
| SEQ. ID. NO. 370 | 153-LeuAspArgMetGluLysGlyThrGlyGlu-162 |
| SEQ. ID. NO. 371 | 167-GlnGluValGluLysGlnTyr-173 |
| SEQ. ID. NO. 372 | 204-ArgAlaTyrArgArgGlnTyrGly-211 |
| 040-2 | |
| AMPHI Regions - AMPHI | |
| SEQ. ID. NO. 373 | 8-ValAlaHisPheArgGluAlaValProTyrIleArg-19 |
| SEQ. ID. NO. 374 | 28-AlaGlyIleAspAsp-32 |
| SEQ. ID. NO. 375 | 38-AspThrLeuAsnLysLeu-43 |
| SEQ. ID. NO. 376 | 78-ProHisTyrCysArgGlyLeuArgValThrAspGlu-89 |
| SEQ. ID. NO. 377 | 92-LeuGluGlnAlaGlnGlnPheAlaGly-100 |
| SEQ. ID. NO. 378 | 113-SerValSerGlyPheAlaArgAlaPro-121 |
| SEQ. ID. NO. 379 | 134-ArgProIleGlyValIleAspGly-141 |
| SEQ. ID. NO. 380 | 146-TyrAlaGlyValIleArg-151 |
| SEQ. ID. NO. 381 | 187-LeuGlnThrAlaAla-191 |
| SEQ. ID. NO. 382 | 207-LeuSerAspGlyIleSerArgProAspGlyThrLeuAlaGlu-220 |
| SEQ. ID. NO. 383 | 223-SerAlaGlnGluAlaGlnSerLeuAlaGluHisAla-234 |
| SEQ. ID. NO. 384 | 244-SerAlaValAlaAlaLeuGluGly-251 |
| SEQ. ID. NO. 385 | 277-IleGlyThrSerIle-281 |
| SEQ. ID. NO. 386 | 289-IleArgGlnAlaHisSerGlyAspIleProHisIleAlaAlaLeuIleArgProLeuGlu-308 |
| SEQ. ID. NO. 387 | 320-TyrLeuGluAsnHisIleSerGluPheSerIle-330 |
| SEQ. ID. NO. 388 | 338-TyrGlyCysAlaAlaLeuLysThrPheAlaGluAlaAsp-350 |
| SEQ. ID. NO. 389 | 371-ArgLeuLeuAlaHisIle-376 |
| SEQ. ID. NO. 390 | 386-SerArgLeuPheAla-390 |
| Antigenic Index - Jameson-Wolf | |
| SEQ. ID. NO. 391 | 19-ArgGlnMetArgGlyLysThrLeu-26 |
| SEQ. ID. NO. 392 | 29-GlyIleAspAspArgLeuLeuGluGlyAspThrLeuAsn-41 |
| SEQ. ID. NO. 393 | 65-HisPheLeuAspArgHisAlaAlaAlaGlnGlyArgThrProHisTyrCysArgGlyLeuArgValThrAspGluThrSerLeuGluGlnAlaGln-96 |
| SEQ. ID. NO. 394 | 101-ThrValArgSerArgPheGlu-107 |
| SEQ. ID. NO. 395 | 119-ArgAlaProSerVal-123 |
| SEQ. ID. NO. 396 | 140-AspGlyThrAspMetGluTyr-146 |
| SEQ. ID. NO. 397 | 150-IleArgLysThrAspThrAlaAla-157 |
| SEQ. ID. NO. 398 | 173-LeuGlyHisSerTyrSerGlyLysThrPhe-182 |
| SEQ. ID. NO. 399 | 208-SerAspGlyIleSerArgProAspGlyThrLeuAla-219 |
| SEQ. ID. NO. 400 | 222-LeuSerAlaGlnGluAlaGlnSerLeuAlaGluHisAlaGlyGlyGluThrArgArgLeuIle-242 |
| SEQ. ID. NO. 401 | 249-LeuGluGlyGlyVal-253 |
| SEQ. ID. NO. 402 | 261-GlyAlaAlaAspGlySerLeuLeu-268 |
| SEQ. ID. NO. 403 | 272-PheThrArgAsnGlyIleGlyThrSerIleAlaLysGluAlaPheVal-287 |
| SEQ. ID. NO. 404 | 289-IleArgGlnAlaHisSerGlyAspIle-297 |
| SEQ. ID. NO. 405 | 305-ArgProLeuGluGluGlnGly-311 |
| SEQ. ID. NO. 406 | 313-LeuLeuHisArgSerArgGluTyrLeu-321 |
| SEQ. ID. NO. 407 | 331-LeuGluHisAspGlyAsnLeuTyr-338 |
| SEQ. ID. NO. 408 | 345-ThrPheAlaGluAlaAspCysGlyGlu-353 |
| SEQ. ID. NO. 409 | 361-ProGlnAlaGlnAspGlyGlyTyrGlyGluArgLeu-372 |
| SEQ. ID. NO. 410 | 377-IleAspLysAlaArgGly-382 |
| SEQ. ID. NO. 411 | 393-ThrAsnThrGlyGlu-397 |
| SEQ. ID. NO. 412 | 402-ArgGlyPheGlnThrAlaSerGluAspGluLeuProGluThrArgArgLysAspTyrArgSerAsnGlyArgAsnSerHisIleLeu-430 |
| Hydrophilic Regions - Hopp-Woods | |
| SEQ. ID. NO. 413 | 19-ArgGlnMetArgGlyLysThr-25 |
| SEQ. ID. NO. 414 | 29-GlyIleAspAspArgLeuLeuGluGlyAspThrLeuAsn-41 |
| SEQ. ID. NO. 415 | 65-HisPheLeuAspArgHisAlaAlaAlaGlnGlyArgThr-77 |
| SEQ. ID. NO. 416 | 84-LeuArgValThrAspGluThrSerLeuGluGln-94 |
| SEQ. ID. NO. 417 | 102-ValArgSerArgPheGlu-107 |
| SEQ. ID. NO. 418 | 140-AspGlyThrAspMetGluTyr-146 |
| SEQ. ID. NO. 419 | 150-IleArgLysThrAspThrAlaAla-157 |
| SEQ. ID. NO. 420 | 210-GlyIleSerArgProAspGlyThrLeu-218 |
| SEQ. ID. NO. 421 | 222-LeuSerAlaGlnGluAlaGlnSerLeuAlaGlu-232 |
| SEQ. ID. NO. 422 | 234-AlaGlyGlyGluThrArgArgLeuIle-242 |
| SEQ. ID. NO. 423 | 291-GlnAlaHisSerGlyAsp-296 |
| SEQ. ID. NO. 424 | 305-ArgProLeuGluGluGlnGly-311 |
| SEQ. ID. NO. 425 | 315-HisArgSerArgGluTyrLeu-321 |
| SEQ. ID. NO. 426 | 345-ThrPheAlaGluAlaAspCysGlyGlu-353 |
| SEQ. ID. NO. 427 | 362-GlnAlaGlnAspGlyGlyTyrGlyGlu-370 |
| SEQ. ID. NO. 428 | 377-IleAspLysAlaArgGly-382 |
| SEQ. ID. NO. 429 | 402-ArgGlyPheGlnThrAlaSerGluAspGluLeuProGluThrArgArgLysAspTyrArgSerAsnGlyArgAsn-426 |
| 041-1 | |
| AMPHI Regions - AMPHI | |
| SEQ. ID. NO. 430 | 6-AspProTyrArgHisPheGluAsnLeuAspSerAlaGluThr-19 |
| SEQ. ID. NO. 431 | 45-AspGlyIleLeuAla-49 |
| SEQ. ID. NO. 432 | 78-LysGlyValTyrArgValCysThrAlaAla-87 |
| SEQ. ID. NO. 433 | 102-ValAlaAspPheAspGluLeuLeu-109 |
| SEQ. ID. NO. 434 | 117-GlyValSerHisLeuValGluGlnProAsn-126 |
| SEQ. ID. NO. 435 | 219-ValAsnAlaTrpArgTyrLeuAsp-226 |
| SEQ. ID. NO. 436 | 232-IleAspLeuIleGluAlaSer-238 |
| SEQ. ID. NO. 437 | 258-LeuAsnLeuProAsnAspCysAspValValGlyTyrLeu-270 |
| SEQ. ID. NO. 438 | 282-TrpAsnArgAlaAsnGln-287 |
| SEQ. ID. NO. 439 | 317-GlnAlaLeuGluSerValGluThr-324 |
| SEQ. ID. NO. 440 | 331-AlaSerLeuLeuGluAsnValGlnGlyArg-340 |

TABLE 1-continued

| | |
|---|---|
| SEQ. ID. NO. 441 | 382-AspPheThrThrProLeu-387 |
| SEQ. ID. NO. 442 | 405-GlnProGlnGlnPhe-409 |
| SEQ. ID. NO. 443 | 451-GlyPheGlyIleProGluLeuProHisTyrLeuGlySerIleGlyLys-466 |
| SEQ. ID. NO. 444 | 493-AlaAlaGlnGlyIleSerLysHisLysSerValAspAspLeuLeuAlaValValArgAspLeuSerGluArg-516 |
| SEQ. ID. NO. 445 | 519-SerSerProGluHis-523 |
| SEQ. ID. NO. 446 | 541-ValArgGluProGlnSer-546 |
| SEQ. ID. NO. 447 | 556-LeuThrAspMetIleArgTyr-562 |
| SEQ. ID. NO. 448 | 571-TrpThrAspGluTyrGlyAsnProGlnLysTyrGlu-582 |
| SEQ. ID. NO. 449 | 591-LeuSerProTyrHisAsnLeuSerAspGlyIleAspTyrProPro-605 |
| SEQ. ID. NO. 450 | 620-AlaHisAlaLeuLys-624 |
| SEQ. ID. NO. 451 | 626-TyrAlaLysLeuArg-630 |
| SEQ. ID. NO. 452 | 645-GlyHisThrGlyAsn-649 |
| SEQ. ID. NO. 453 | 651-ThrGlnArgGluSer-655 |
| AntigenicIndex - Jameson-Wolf | |
| SEQ. ID. NO. 454 | 1-MetLysSerTyrProAspProTyrArgHisPheGluAsnLeuAspSerAlaGluThrGln-20 |
| SEQ. ID. NO. 455 | 26-AlaAsnAlaGluThrArgAlaArgPheLeuGluAsnAspLysAlaArgAlaLeuSerAspGly-46 |
| SEQ. ID. NO. 456 | 51-LeuGlnAspThrArgGlnIleProPhe-59 |
| SEQ. ID. NO. 457 | 61-GlnGluHisArgAlaArg-66 |
| SEQ. ID. NO. 458 | 72-GlnAspAlaGluTyrProLysGlyVal-80 |
| SEQ. ID. NO. 459 | 89-TyrArgSerGlyTyrProGluTrp-96 |
| SEQ. ID. NO. 460 | 104-AspPheAspGluLeuLeuGlyAspAspValTyr-114 |
| SEQ. ID. NO. 461 | 123-GluGlnProAsnArg-127 |
| SEQ. ID. NO. 462 | 133-SerLysLeuGlySerAspThrAlaTyr-141 |
| SEQ. ID. NO. 463 | 145-ValAspLeuGluAlaGlyGluLeuValGlu-154 |
| SEQ. ID. NO. 464 | 161-AlaGlyLysAsnHisValSerTrpArgAspGluAsnSerVal-174 |
| SEQ. ID. NO. 465 | 178-ProAlaTrpAsnGluArgGlnLeuThrGlnSerGlyTyrProArgGluValTrpLeuValGluArgGlyLysSerPheGluGluSerLeu-207 |
| SEQ. ID. NO. 466 | 212-IleGlyGluAspGlyMet-217 |
| SEQ. ID. NO. 467 | 223-ArgTyrLeuAspProGlnGlySerProIleAspLeuIleGluAlaSerAspGlyPheTyr-242 |
| SEQ. ID. NO. 468 | 249-ValSerAlaGluGlyGluAlaLysProLeuAsnLeuProAsnAspCysAspVal-266 |
| SEQ. ID. NO. 469 | 277-ThrLeuArgLysAspTrpAsnArgAlaAsnGlnSerTyrProSer-291 |
| SEQ. ID. NO. 470 | 298-LysLeuAsnArgGlyGluLeuGly-305 |
| SEQ. ID. NO. 471 | 313-ProAspGluThrGlnAla-318 |
| SEQ. ID. NO. 472 | 320-GluSerValGluThrThrLys-326 |
| SEQ. ID. NO. 473 | 337-ValGlnGlyArgLeuLysAla-343 |
| SEQ. ID. NO. 474 | 345-ArgPheAlaAspGlyLysTrpGlnGluValGluLeuProArgLeuProSerGly-362 |
| SEQ. ID. NO. 475 | 365-GluMetThrAspGlnProTrpGlyGly-373 |
| SEQ. ID. NO. 476 | 401-ValMetArgArgGlnProGlnGlnPheAspSerAspGlyIleAsn-415 |
| SEQ. ID. NO. 477 | 422-ThrSerAlaAspGlyGluArgIle-429 |
| SEQ. ID. NO. 478 | 435-GlyLysAsnAlaAlaProAspMet-442 |
| SEQ. ID. NO. 479 | 479-AsnIleArgGlyGlyGlyGluPheGlyProArgTrpHis-491 |
| SEQ. ID. NO. 480 | 496-GlyIleSerLysHisLysSerValAspAsp-505 |
| SEQ. ID. NO. 481 | 511-ArgAspLeuSerGluArgGlyIleSerSerProGluHisIle-524 |
| SEQ. ID. NO. 482 | G528-lyGlySerAsnGly-532 |
| SEQ. ID. NO. 483 | 540-PheValArgGluProGlnSerIleGlyAla-549 |
| SEQ. ID. NO. 484 | 568-GlySerSerTrpThrAspGluTyrGlyAsnProGlnLysTyrGluValCysLysArgArgLeuGlyGluLeuSerProTyr-594 |
| SEQ. ID. NO. 485 | 596-AsnLeuSerAspGlyIleAspTyrPro-604 |
| SEQ. ID. NO. 486 | 610-ThrSerLeuAspAspArgValHis-618 |
| SEQ. ID. NO. 487 | 627-AlaLysLeuArgGluThrSerAla-634 |
| SEQ. ID. NO. 488 | 639-TyrSerProAspGlyGlyGlyHisThrGlyAsnGlyThrGlnArgGluSerAlaAspGluLeu-659 |
| Hydrophilic Regions - Hopp-Woods | |
| SEQ. ID. NO. 489 | 3-SerTyrProAspProTyrArgHis-10 |
| SEQ. ID. NO. 490 | 12-GluAsnLeuAspSerAlaGluThr-19 |
| SEQ. ID. NO. 491 | 26-AlaAsnAlaGluThrArgAlaArgPheLeuGluAsnAspLysAlaArgAlaLeuSer-44 |
| SEQ. ID. NO. 492 | 52-GlnAspThrArgGln-56 |
| SEQ. ID. NO. 493 | 61-GlnGluHisArgAlaArg-66 |
| SEQ. ID. NO. 494 | 72-GlnAspAlaGluTyrPro-77 |
| SEQ. ID. NO. 495 | 104-AspPheAspGluLeuLeuGly-110 |
| SEQ. ID. NO. 496 | 145-ValAspLeuGluAlaGlyGluLeuValGlu-154 |
| SEQ. ID. NO. 497 | 166-ValSerTrpArgAspGluAsnSer-173 |
| SEQ. ID. NO. 498 | 180-TrpAsnGluArgGlnLeuThr-186 |
| SEQ. ID. NO. 499 | 198-GluArgGlyLysSerPheGluGluSerLeu-207 |
| SEQ. ID. NO. 500 | 212-IleGlyGluAspGlyMet-217 |
| SEQ. ID. NO. 501 | 233-AspLeuIleGluAlaSerAsp-239 |
| SEQ. ID. NO. 502 | 249-ValSerAlaGluGlyGluAlaLysPro-257 |
| SEQ. ID. NO. 503 | 278-LeuArgLysAspTrpAsnArg-284 |
| SEQ. ID. NO. 504 | 298-LysLeuAsnArgGlyGluLeuGly-305 |
| SEQ. ID. NO. 505 | 313-ProAspGluThrGlnAla-318 |
| SEQ. ID. NO. 506 | 320-GluSerValGluThrThrLys-326 |
| SEQ. ID. NO. 507 | 337-ValGlnGlyArgLeuLysAla-343 |
| SEQ. ID. NO. 508 | 401-ValMetArgArgGlnProGlnGlnPheAspSerAspGlyIleAsn-415 |
| SEQ. ID. NO. 509 | 424-AlaAspGlyGluArg-428 |
| SEQ. ID. NO. 510 | 436-LysAsnAlaAlaProAsp-441 |
| SEQ. ID. NO. 511 | 481-ArgGlyGlyGlyGluPheGly-487 |
| SEQ. ID. NO. 512 | 496-GlyIleSerLysHisLysSerValAspAsp-505 |
| SEQ. ID. NO. 513 | 511-ArgAspLeuSerGluArgGlyIleSerSer-520 |
| SEQ. ID. NO. 514 | 540-PheValArgGluProGlnSer-546 |
| SEQ. ID. NO. 515 | 571-TrpThrAspGluTyrGlyAsn-577 |
| SEQ. ID. NO. 516 | 579-GlnLysTyrGluValCysLysArgArgLeuGlyGlu-590 |
| SEQ. ID. NO. 517 | 612-LeuSerAspAspArgValHis-618 |
| SEQ. ID. NO. 518 | 627-AlaLysLeuArgGluThrSer-633 |

TABLE 1-continued

SEQ. ID. NO. 519    650-GlyThrGlnArgGluSerAlaAspGluLeu-659
042-1
AMPHI Regions - AMPHI
SEQ. ID. NO. 520    17-AlaLeuSerAsnThrSerThr-23
SEQ. ID. NO. 521    33-AlaValArgSerMetMetLysIle-40
SEQ. ID. NO. 522    138-SerProLeuValArgIleLeuProLeuSer-147
SEQ. ID. NO. 523    151-SerMetValValAlaPhePheAlaAsn-159
Antigenic Index - Jameson-Wolf
SEQ. ID. NO. 524    14-ArgThrSerAlaLeuSerAsnThrSerThrAlaAlaGlyProSerCys-29
SEQ. ID. NO. 525    49-TyrSerLysGluThrGlyCysProCysProSerLeuArgLysAspSerSerThrGlyGlyArgProMetSerProCys-74
SEQ. ID. NO. 526    77-LeuAlaAsnArgAspCysValProLysAlaAspThr-88
SEQ. ID. NO. 527    93-ThrAspSerThrSerProArgProLeu-101
SEQ. ID. NO. 528    122-AlaArgAlaSerLeuProLysIleArgAlaLysVal-133
SEQ. ID. NO. 529    160-CysSerTyrAlaSerAlaProGlyPro-168
Hydrophilic Regions - Hopp-Woods
SEQ. ID. NO. 530    49-TyrSerLysGluThrGlyCys-55
SEQ. ID. NO. 531    59-SerLeuArgLysAspSerSerThrGlyGlyArgProMet-71
SEQ. ID. NO. 532    78-AlaAsnArgAspCysValProLysAlaAspThr-88
SEQ. ID. NO. 533    94-AspSerThrSerProArg-99
SEQ. ID. NO. 534    125-SerLeuProLysIleArgAlaLysVal-133
043-2
AMPHI Regions - AMPHI
SEQ. ID. NO. 535    24-ValGluProSerArg-28
SEQ. ID. NO. 536    36-HisGlyGlyLeuAspGlyAlaAlaGlyPheAspGluGlyGluArg-50
SEQ. ID. NO. 537    59-AlaSerGlyAspGlyPhe-64
SEQ. ID. NO. 538    83-AlaGlyAspPheGlyAspGlyGlnArg-91
Antigenic Index - Jameson-Wolf
SEQ. ID. NO. 539    1-MetProProAlaPro-5
SEQ. ID. NO. 540    11-IleArgArgGlnLysSerValMetProSerGluArgPheValGluProSerArg-28
SEQ. ID. NO. 541    35-ValHisGlyGlyLeuAspGlyAlaAlaGlyPheAspGluGlyGluArgValPhe-52
SEQ. ID. NO. 542    56-AlaAlaGlnAlaSerGlyAspGlyPheAla-65
SEQ. ID. NO. 543    79-GlnSerAspAlaAlaGlyAspPheGlyAspGlyGlnArgThrGlyGlu-94
SEQ. ID. NO. 544    96-ValLeuGlnAspValGlyGly-102
SEQ. ID. NO. 545    116-AlaGluGlyGluAlaGln-121
Hydrophilic Regions - Hopp-Woods
SEQ. ID. NO. 546    11-IleArgArgGlnLysSerValMetProSerGluArgPheValGluProSerArg-28
SEQ. ID. NO. 547    43-AlaGlyPheAspGluGlyGluArgValPhe-52
SEQ. ID. NO. 548    81-AspAlaAlaGlyAspPheGlyAspGlyGlnArgThrGly-93
SEQ. ID. NO. 549    116-AlaGluGlyGluAlaGln-121
046-2
AMPHI Regions - AMPHI
SEQ. ID. NO. 550    6-ArgProThrSerSerPro-11
SEQ. ID. NO. 551    46-ThrSerCysSerGlyLeuMetValSer-54
SEQ. ID. NO. 552    64-PheSerLeuPheSerSer-69
SEQ. ID. NO. 553    113-LysSerAlaSerSer-117
SEQ. ID. NO. 554    143-SerCysAsnAlaPheSerSer-149
SEQ. ID. NO. 555    155-ThrSerLeuLeuGlyMetAlaAlaArgPheCysAlaThrVal-168
Antigenic Index - Jameson-Wolf
SEQ. ID. NO. 556    6-ArgProThrSerSerProProArgArgAlaCys-16
SEQ. ID. NO. 557    20-IleArgThrArgSerSerAlaLysArgLysThrCysAsnAlaProGlyGlnSerIleArgProAlaSerCysSer-44
SEQ. ID. NO. 558    57-ProAsnMetGluArgLeuPro-63
SEQ. ID. NO. 559    75-SerArgTyrSerLeuGluArgThrArgAlaMetArgProGlyMetLeuAsnArgSerAlaAla-95
SEQ. ID. NO. 560    105-SerLeuArgGluSerAlaSerSerLysSerAlaSerSerAlaProAlaArgSerAsnValLysGlyAspAlaProLeuProLysThrValTrp
                    ThrSerArgArgLeuProVal-142
SEQ. ID. NO. 561    169-GluProThrCysProLeuProLys-176
Hydrophilic Regions - Hopp-Woods
SEQ. ID. NO. 562    7-ProThrSerSerProProArgArgAlaCys-16
SEQ. ID. NO. 563    20-IleArgThrArgSerSerAlaLysArgLysThrCysAsn-32
SEQ. ID. NO. 564    36-GlnSerIleArgProAlaSer-42
SEQ. ID. NO. 565    58-AsnMetGluArgLeuPro-63
SEQ. ID. NO. 566    75-SerArgTyrSerLeuGluArgThrArgAlaMetArg-86
SEQ. ID. NO. 567    105-SerLeuArgGluSerAlaSerSerLysSerAlaSer-116
SEQ. ID. NO. 568    118-AlaProAlaArgSerAsnValLysGlyAspAlaProLeu-130
047-2
AMPHI Regions - AMPHI
SEQ. ID. NO. 569    17-IleAlaAspIleAlaGlnAspLeuProAspGlyAla-28
SEQ. ID. NO. 570    62-AlaGluAsnIleGlyAlaVal-68
SEQ. ID. NO. 571    93-ArgLeuAlaLysGlnLeuGlu-99
SEQ. ID. NO. 572    141-TyrIleAspGluIleAspValPhe-148
SEQ. ID. NO. 573    161-SerAlaLeuLeuAla-165
SEQ. ID. NO. 574    185-LeuLeuGluGlyAsn-189
SEQ. ID. NO. 575    202-IleGlySerIleLeuAla-207
SEQ. ID. NO. 576    247-SerGlyIleLysTrpProGluGlyCys-255
SEQ. ID. NO. 577    257-IleAlaAlaValValArgAlaGlyThrGly-266
SEQ. ID. NO. 578    293-IleLeuAsnGluLeuGluLysLeuIle-301
Antigenic Index - Jameson-Wolf
SEQ. ID. NO. 579    5-GlnAlaArgArgGlyGlyLeuLeu-12
SEQ. ID. NO. 580    20-IleAlaGlnAspLeuProAspGlyAlaAsp-29
SEQ. ID. NO. 581    36-TyrArgAsnAsnArgLeu-41
SEQ. ID. NO. 582    51-IleGluGlyAspGlu-55

TABLE 1-continued

| | |
|---|---|
| SEQ. ID. NO. 583 | 70-ProGluLeuArgProLysGluThrSerThrArgArgIleMet-83 |
| SEQ. ID. NO. 584 | 86-GlyGlyGlyAsnIle-90 |
| SEQ. ID. NO. 585 | 96-LysGlnLeuGluHis-100 |
| SEQ. ID. NO. 586 | 106-IleIleGluCysArgProArgArgAlaGluTrpIle-117 |
| SEQ. ID. NO. 587 | 119-GluAsnLeuAspAsnThrLeu-125 |
| SEQ. ID. NO. 588 | 130-SerAlaThrAspGluThrLeuLeuAspAsnGluTyrIleAspGluIleAsp-146 |
| SEQ. ID. NO. 589 | 152-ThrAsnAspAspGluSerAsnIle-159 |
| SEQ. ID. NO. 590 | 168-LeuGlyAlaLysArgVal-173 |
| SEQ. ID. NO. 591 | 178-AsnArgSerSerTyr-182 |
| SEQ. ID. NO. 592 | 186-LeuGluGlyAsnLysIle-191 |
| SEQ. ID. NO. 593 | 208-HisIleArgArgGlyAspIleVal-215 |
| SEQ. ID. NO. 594 | 219-ProIleArgArgGlyThrAlaGluAlaIleGlu-229 |
| SEQ. ID. NO. 595 | 232-AlaHisGlyAspLysLysThrSer-239 |
| SEQ. ID. NO. 596 | 242-IleGlyArgArgIleSerGlyIleLysTrpProGluGlyCysHis-256 |
| SEQ. ID. NO. 597 | 262-ArgAlaGlyThrGlyGluThr-268 |
| SEQ. ID. NO. 598 | 277-ValIleGlnAspGlyAspHis-283 |
| SEQ. ID. NO. 599 | 288-ValSerArgArgArgIleLeuAsnGluLeuGluLys-299 |
| Hydrophilic Regions - Hopp-Woods | |
| SEQ. ID. NO. 600 | 5-GlnAlaArgArgGlyGly-10 |
| SEQ. ID. NO. 601 | 20-IleAlaGlnAspLeuProAspGlyAlaAsp-29 |
| SEQ. ID. NO. 602 | 51-IleGluGlyAspGlu-55 |
| SEQ. ID. NO. 603 | 70-ProGluLeuArgProLysGluThrSerThrArgArgIleMet-83 |
| SEQ. ID. NO. 604 | 106-IleIleGluCysArgProArgArgAlaGluTrpIle-117 |
| SEQ. ID. NO. 605 | 130-SerAlaThrAspGluThrLeuLeu-137 |
| SEQ. ID. NO. 606 | 140-GluTyrIleAspGluIleAsp-146 |
| SEQ. ID. NO. 607 | 152-ThrAsnAspAspGluSerAsnIle-159 |
| SEQ. ID. NO. 608 | 168-LeuGlyAlaLysArgVal-173 |
| SEQ. ID. NO. 609 | 186-LeuGluGlyAsnLysIle-191 |
| SEQ. ID. NO. 610 | 209-IleArgArgGlyAspIle-214 |
| SEQ. ID. NO. 611 | 219-ProIleArgArgGlyThrAlaGluAlaIleGlu-229 |
| SEQ. ID. NO. 612 | 232-AlaHisGlyAspLysLysThrSer-239 |
| SEQ. ID. NO. 613 | 242-IleGlyArgArgIleSer-247 |
| SEQ. ID. NO. 614 | 277-ValIleGlnAspGlyAsp-282 |
| SEQ. ID. NO. 615 | 289-SerArgArgArgIleLeuAsnGluLeuGluLys-299 |
| 049-2 | |
| AMPHI Regions - AMPHI | |
| SEQ. ID. NO. 616 | 15-GlnHisLeuLeuGlu-19 |
| SEQ. ID. NO. 617 | 34-AspAspAlaValAspGlyIleGlyGlnMet-43 |
| SEQ. ID. NO. 618 | 50-GlnProPheGlyGln-54 |
| SEQ. ID. NO. 619 | 61-GluHisPheAlaProValAspGlyPheArg-70 |
| SEQ. ID. NO. 620 | 79-HisGlnArgPhePheArgIle-85 |
| SEQ. ID. NO. 621 | 202-ArgGlyAlaGlyGlnArgArgValSerArgHisCys-213 |
| SEQ. ID. NO. 622 | 217-AlaArgLeuThrGlnValPheGlnThrPhePhe-227 |
| Antigenic Index - Jameson-Wolf | |
| SEQ. ID. NO. 623 | 6-PheAspTyrArgProArgLeuLeu-13 |
| SEQ. ID. NO. 624 | 21-IleGlyGluAsnArgHis-26 |
| SEQ. ID. NO. 625 | 28-LeuLeuHisArgArgSerAspAspAlaValAspGlyIleGly-41 |
| SEQ. ID. NO. 626 | 49-AspGlnProPheGly-53 |
| SEQ. ID. NO. 627 | 64-AlaProValAspGlyPheArgValGlnAspIleAspLeuAspGlyHisGlnArgPhe-82 |
| SEQ. ID. NO. 628 | 89-ValPheArgAsnArgArgLeuIle-96 |
| SEQ. ID. NO. 629 | 111-LeuSerGlyPheLys-115 |
| SEQ. ID. NO. 630 | 122-GlyIleLysProAspSerProProArgPhe-131 |
| SEQ. ID. NO. 631 | 135-PheArgAsnArgHisLeuGlnGlySerLeuArgVal-146 |
| SEQ. ID. NO. 632 | 150-PheLeuLysAspAspHisArgValGly-158 |
| SEQ. ID. NO. 633 | 182-GlnHisThrGlySer-186 |
| SEQ. ID. NO. 634 | 193-ArgHisArgArgValArgSerGlyPheArgGlyAlaGlyGlnArgArgValSerArgHisCys-213 |
| SEQ. ID. NO. 635 | 246-LysGlnThrAsnProArgProLysArgGlyLeu-256 |
| Hydrophilic Regions - Hopp-Woods | |
| SEQ. ID. NO. 636 | 21-IleGlyGluAsnArgHis-26 |
| SEQ. ID. NO. 637 | 30-HisArgArgSerAspAspAlaValAsp-38 |
| SEQ. ID. NO. 638 | 67-AspGlyPheArgValGlnAspIleAspLeuAspGlyHisGlnArg-81 |
| SEQ. ID. NO. 639 | 91-ArgAsnArgArgLeuIle-96 |
| SEQ. ID. NO. 640 | 124-LysProAspSerProProArg-130 |
| SEQ. ID. NO. 641 | 150-PheLeuLysAspAspHisArgVal-157 |
| SEQ. ID. NO. 642 | 193-ArgHisArgArgValArgSerGlyPheArgGlyAlaGlyGlnArgArgValSerArg-211 |
| SEQ. ID. NO. 643 | 246-LysGlnThrAsnProArgProLysArgGlyLeu-256 |
| 050-1 | |
| AMPHI Regions - AMPHI | |
| SEQ. ID. NO. 644 | 10-IleGlnSerIleCysAspAlaPheGlnPheIleSerTyrTyr-23 |
| SEQ. ID. NO. 645 | 25-ProLysAspTyrIleAspAlaLeuTyrLysAlaTrpGlnLys-38 |
| SEQ. ID. NO. 646 | 94-ValAsnGlyGlyVal-98 |
| SEQ. ID. NO. 647 | 163-AsnProSerAspAsnIleValAspTrpValLeuLys-174 |
| SEQ. ID. NO. 648 | 177-ProThrMetGlyAla-181 |
| SEQ. ID. NO. 649 | 235-LeuGluLeuPheGluLysValAsnAla-243 |
| SEQ. ID. NO. 650 | 250-GlyLeuGlyGlyLeuThrThr-256 |
| SEQ. ID. NO. 651 | 275-AlaMetIleProAsn-279 |
| SEQ. ID. NO. 652 | 302-ArgValGluAspTrpProAspLeuThr-310 |
| SEQ. ID. NO. 653 | 315-AsnGlyLysArgValAspValAsp-322 |
| SEQ. ID. NO. 654 | 353-LysArgLeuValAspMetLeuAsnLys-361 |
| SEQ. ID. NO. 655 | 367-ValAspPheThrAsnArgLeu-373 |

TABLE 1-continued

| | |
|---|---|
| SEQ. ID. NO. 656 | 379-ProValAspProValGlyAspGlu-386 |
| SEQ. ID. NO. 657 | 396-AlaThrArgMetAspLysPheThrArgGlnMet-406 |
| SEQ. ID. NO. 658 | 410-ThrAspLeuLeuGlyMet-415 |
| SEQ. ID. NO. 659 | 422-GlyValAlaThrCysGluAlaIleAla-430 |
| SEQ. ID. NO. 660 | 452-LysSerSerLysValLeuAlaPhe-459 |
| SEQ. ID. NO. 661 | 490-AlaThrAlaProArgLysTrp-496 |
| Antigenic Index - Jameson-Wolf | |
| SEQ. ID. NO. 662 | 4-IleLysGlnGluAspPheIle-10 |
| SEQ. ID. NO. 663 | 23-TyrHisProLysAspTyrIleAspAlaLeu-32 |
| SEQ. ID. NO. 664 | 36-TrpGlnLysGluGluAsnProAlaAlaLysAspAlaMet-48 |
| SEQ. ID. NO. 665 | 55-SerArgMetCysAlaGluAsnAsnArgProIleCysGlnAspThrGly-70 |
| SEQ. ID. NO. 666 | 88-MetSerValGluGluMetValAsnGluGlyValArgArgAlaTyrThrTrpGluGlyAsnThrLeuArgAlaSerVal-113 |
| SEQ. ID. NO. 667 | 116-AspProAlaGlyLysArgGlnAsnThrLysAspAsnThr-128 |
| SEQ. ID. NO. 668 | 138-ProGlyGlyLysValGluVal-144 |
| SEQ. ID. NO. 669 | 148-AlaLysGlyGlyGlySerGluAsnLysSerLysLeu-159 |
| SEQ. ID. NO. 670 | 163-AsnProSerAspAsnIle-168 |
| SEQ. ID. NO. 671 | 192-GlyIleGlyGlyThrProGluLysAlaValLeuMetAlaLysGluSerLeu-208 |
| SEQ. ID. NO. 672 | 213-AspIleGlnGluLeuGlnGluLysAlaAlaSerGlyAlaGluLeuSerThr-229 |
| SEQ. ID. NO. 673 | 284-ArgHisValGluPheGluLeuAspGlySerGlyProValGluLeuThrProProArgValGluAspTrpProAspLeuThrTyrSerProAspAsn GlyLysArgValAspValAspLysLeuThrLysGluGluValAlaSer-331 |
| SEQ. ID. NO. 674 | 345-LeuThrGlyArgAspAlaAlaHisLysArgLeuVal-356 |
| SEQ. ID. NO. 675 | 359-LeuAsnLysGlyGluGluLeuPro-366 |
| SEQ. ID. NO. 676 | 379-ProValAspProValGlyAspGluValValGlyProAlaGlyProThrThrAlaThrArgMetAspLysPheThrArgGlnMetLeuGluGln ThrAsp-411 |
| SEQ. ID. NO. 677 | 417-GlyLysSerGluArgGlyValAlaThr-425 |
| SEQ. ID. NO. 678 | 428-AlaIleAlaAspAsnLysAla-434 |
| SEQ. ID. NO. 679 | 450-AlaIleLysSerSerLys-455 |
| SEQ. ID. NO. 680 | 470-PheGluValLysAspMetPro-476 |
| SEQ. ID. NO. 681 | 481-ValAspSerLysGlyGluSerIle-488 |
| SEQ. ID. NO. 682 | 492-AlaProArgLysTrpGlnAla-498 |
| Hydrophilic Regions - Hopp-Woods | |
| SEQ. ID. NO. 683 | 4-IleLysGlnGluAspPheIle-10 |
| SEQ. ID. NO. 684 | 36-TrpGlnLysGluGluAsnProAlaAlaLysAspAlaMet-48 |
| SEQ. ID. NO. 685 | 57-MetCysAlaGluAsnAsnArgProIleCys-66 |
| SEQ. ID. NO. 686 | 88-MetSerValGluGluMetValAsnGluGlyValArgArg-100 |
| SEQ. ID. NO. 687 | 117-ProAlaGlyLysArgGlnAsnThrLysAspAsnThr-128 |
| SEQ. ID. NO. 688 | 140-GlyLysValGluVal-144 |
| SEQ. ID. NO. 689 | 148-AlaLysGlyGlyGlySerGluAsnLysSerLysLeu-159 |
| SEQ. ID. NO. 690 | 195-GlyThrProGluLysAlaValLeuMetAlaLysGluSerLeu-208 |
| SEQ. ID. NO. 691 | 213-AspIleGlnGluLeuGlnGluLysAlaAlaSer-223 |
| SEQ. ID. NO. 692 | 225-AlaGluLeuSerThr-229 |
| SEQ. ID. NO. 693 | 284-ArgHisValGluPheGluLeuAspGly-292 |
| SEQ. ID. NO. 694 | 299-ThrProProArgValGluAspTrpPro-307 |
| SEQ. ID. NO. 695 | 313-ProAspAsnGlyLysArgValAspValAspLysLeuThrLysGluGluValAlaSer-331 |
| SEQ. ID. NO. 696 | 345-LeuThrGlyArgAspAlaAlaHisLysArgLeuVal-356 |
| SEQ. ID. NO. 697 | 359-LeuAsnLysGlyGluGluLeuPro-366 |
| SEQ. ID. NO. 698 | 382-ProValGlyAspGluValVal-388 |
| SEQ. ID. NO. 699 | 397-ThrArgMetAspLysPheThrArgGlnMetLeuGluGlnThrAsp-411 |
| SEQ. ID. NO. 700 | 417-GlyLysSerGluArgGlyValAla-424 |
| SEQ. ID. NO. 701 | 428-AlaIleAlaAspAsnLysAla-434 |
| SEQ. ID. NO. 702 | 450-AlaIleLysSerSerLys-455 |
| SEQ. ID. NO. 703 | 470-PheGluValLysAspMetPro-476 |
| SEQ. ID. NO. 704 | 481-ValAspSerLysGlyGluSerIle-488 |
| SEQ. ID. NO. 705 | 492-AlaProArgLysTrpGlnAla-498 |
| 052 | |
| AMPHI Regions - AMPHI | |
| SEQ. ID. NO. 706 | 12-AlaProCysPheLysGlyCysGluProThrGlyAsp-23 |
| SEQ. ID. NO. 707 | 41-AlaLysAlaSerLysSerAlaThrSerProLysGlyLeuAspGlyValSerLys-58 |
| SEQ. ID. NO. 708 | 67-ThrAlaAlaPheHisSerPheIleSer-75 |
| SEQ. ID. NO. 709 | 84-MetProAsnLeuValThrMetLeu-91 |
| Antigenic Index - Jameson-Wolf | |
| SEQ. ID. NO. 710 | 4-ValAlaGluGluThrGluIle-10 |
| SEQ. ID. NO. 711 | 14-CysPheLysGlyCysGluProThrGlyAspSerArgLeuLeuSerThrThrLysSerAlaPro-34 |
| SEQ. ID. NO. 712 | 37-CysAlaAsnSerAlaLysAlaSerLysSerAlaThrSerProLysGlyLeuAspGlyValSerLysAsnSerSer-61 |
| SEQ. ID. NO. 713 | 75-SerValGlyAspThrArgLeuThrProMet-84 |
| SEQ. ID. NO. 714 | 97-ValValProAsnArgLeuArgLeuGluThrThrTrpSerProAlaCysArgLysValLysAsnAlaAla-119 |
| Hydrophilic Regions - Hopp-Woods | |
| SEQ. ID. NO. 715 | 4-ValAlaGluGluThrGluIle-10 |
| SEQ. ID. NO. 716 | 16-LysGlyCysGluProThrGlyAspSerArgLeu-26 |
| SEQ. ID. NO. 717 | 30-ThrLysSerAlaPro-34 |
| SEQ. ID. NO. 718 | 39-AsnSerAlaLysAlaSerLysSerAlaThrSerProLysGlyLeuAspGlyValSerLysAsnSer-60 |
| SEQ. ID. NO. 719 | 77-GlyAspThrArgLeu-81 |
| SEQ. ID. NO. 720 | 100-AsnArgLeuArgLeu-104 |
| SEQ. ID. NO. 721 | 111-AlaCysArgLysValLysAsnAlaAla-119 |
| 075 | |
| AMPHI Regions - AMPHI | |
| SEQ. ID. NO. 722 | 15-LysSerAlaAlaLysMetProThrThrIleGlnProAlaSerIleProSer-31 |
| SEQ. ID. NO. 723 | 65-AlaProTyrLeuArgGlnValLeu-72 |
| SEQ. ID. NO. 724 | 80-PheLysLysCysLeuAla-85 |

TABLE 1-continued

| | |
|---|---|
| SEQ. ID. NO. 725 | 116-AspPhePheGlnThrCysValAsnArgPhePheGluValValGluIleIleGlyIleGly-135 |
| Antigenic Index - Jameson-Wolf | |
| SEQ. ID. NO. 726 | 12-GluAsnThrLysSerAlaAlaLysMetPro-21 |
| SEQ. ID. NO. 727 | 52-AlaLysAlaArgGly-56 |
| SEQ. ID. NO. 728 | 91-PhePheArgArgProProAsnIleArgLysSerValPheGlnLysSerGluTyrAspLys-110 |
| Hydrophilic Regions - Hopp-Woods | |
| SEQ. ID. NO. 729 | 12-GluAsnThrLysSerAlaAlaLys-19 |
| SEQ. ID. NO. 730 | 52-AlaLysAlaArgGly-56 |
| SEQ. ID. NO. 731 | 91-PhePheArgArgProProAsnIleArgLysSerValPheGlnLysSerGluTyrAspLys-110 |
| 080 | |
| AMPHI Regions - AMPHI | |
| SEQ. ID. NO. 732 | 6-GluAlaMetGluArgLeuThrArg-13 |
| SEQ. ID. NO. 733 | 95-PheProAspThrValGlu-100 |
| SEQ. ID. NO. 734 | 108-ProValAlaArgTrpGlyAspHis-115 |
| SEQ. ID. NO. 735 | 144-SerAlaGluMetLeuArgArgTyrAspGluPheSerThrValLeu-158 |
| SEQ. ID. NO. 736 | 195-LysArgLeuArgLeuPheThrGluAlaTrpGlnHis-206 |
| Antigenic Index - Jameson-Wolf | |
| SEQ. ID. NO. 737 | 1-MetTrpAspAsnAlaGluAlaMetGluArgLeuThr-12 |
| SEQ. ID. NO. 738 | 33-AsnSerAsnHisLeuPro-38 |
| SEQ. ID. NO. 739 | 42-ValSerLeuLysGly-46 |
| SEQ. ID. NO. 740 | 48-LeuValTyrSerAspLysLysThrLeu-56 |
| SEQ. ID. NO. 741 | 67-AsnIleLeuArgThrAspIleAsnGlyAlaGlnGluAlaTyrArg-81 |
| SEQ. ID. NO. 742 | 90-MetValArgArgArgPheProAspThrValGlu-100 |
| SEQ. ID. NO. 743 | 103-LeuThrGluArgLysProValAlaArgTrpGly-113 |
| SEQ. ID. NO. 744 | 116-AlaLeuValAspGlyGluGlyAsnValPhe-125 |
| SEQ. ID. NO. 745 | 127-AlaArgLeuAspArgProGlyMetPro-135 |
| SEQ. ID. NO. 746 | 138-ArgGlyAlaGluGlyThrSer-144 |
| SEQ. ID. NO. 747 | 146-GluMetLeuArgArgTyrAspGlu-153 |
| SEQ. ID. NO. 748 | 163-LeuGlyIleLysGlu-167 |
| SEQ. ID. NO. 749 | 187-ArgLeuGlyArgGluAsnGluMetLysArgLeuArgLeu-199 |
| SEQ. ID. NO. 750 | 207-LeuLeuArgLysAsnLysAsnArgLeuSer-216 |
| SEQ. ID. NO. 751 | 220-MetArgTyrLysAspGlyPheSer-227 |
| SEQ. ID. NO. 752 | 230-TyrAlaSerAspGlyLeuProGluLysGluSerGluGlu-242 |
| Hydrophilic Regions - Hopp-Woods | |
| SEQ. ID. NO. 753 | 3-AspAsnAlaGluAlaMetGluArgLeuThr-12 |
| SEQ. ID. NO. 754 | 50-TyrSerAspLysLysThrLeu-56 |
| SEQ. ID. NO. 755 | 69-LeuArgThrAspIleAsnGlyAlaGlnGluAlaTyrArg-81 |
| SEQ. ID. NO. 756 | 90-MetValArgArgArgPheProAspThrVal-99 |
| SEQ. ID. NO. 757 | 103-LeuThrGluArgLysProValAlaArgTrpGly-113 |
| SEQ. ID. NO. 758 | 116-AlaLeuValAspGlyGluGlyAsnValPhe-125 |
| SEQ. ID. NO. 759 | 127-AlaArgLeuAspArgProGly-133 |
| SEQ. ID. NO. 760 | 138-ArgGlyAlaGluGlyThrSer-144 |
| SEQ. ID. NO. 761 | 146-GluMetLeuArgArgTyrAspGlu153153 |
| SEQ. ID. NO. 762 | 163-LeuGlyIleLysGlu-167 |
| SEQ. ID. NO. 763 | 187-ArgLeuGlyArgGluAsnGluMetLysArgLeuArgLeu-199 |
| SEQ. ID. NO. 764 | 208-LeuArgLysAsnLysAsnArgLeuSer-216 |
| SEQ. ID. NO. 765 | 220-MetArgTyrLysAspGlyPheSer-227 |
| SEQ. ID. NO. 766 | 234-GlyLeuProGluLysGluSerGluGlu-242 |
| 081 | |
| AMPHI Regions - AMPHI | |
| SEQ. ID. NO. 767 | 22-LysProValSerArgIleValThrAspSer-31 |
| SEQ. ID. NO. 768 | 85-LeuAlaAlaLeuGlnThrLeuAlaLysAlaTrpArgGluAsn-98 |
| SEQ. ID. NO. 769 | 116-LysGluMetLeuAlaAlaValLeuArg-124 |
| SEQ. ID. NO. 770 | 135-ThrAlaGlyAsnPhe-139 |
| SEQ. ID. NO. 771 | 165-MetAsnHisPheGlyGluLeuAlaValLeuThrXxxIleAlaLys-179 |
| SEQ. ID. NO. 772 | 185-ValAsnAsnAlaMetArg-190 |
| SEQ. ID. NO. 773 | 198-AspGlyValGlyAspIleAlaLysAla-206 |
| SEQ. ID. NO. 774 | 303-LeuAsnAspValAlaGluGlyLeuLysGlyPheSerAsnIle-316 |
| SEQ. ID. NO. 775 | 345-AlaAlaIleAspValLeuAlaArgMetPro-354 |
| SEQ. ID. NO. 776 | 360-ValMetGlyAspMetGlyGluLeuGlyGluLeuGlyGlu-372 |
| SEQ. ID. NO. 777 | 402-ValGluAlaAlaGlu-406 |
| Antigenic Index - Jameson-Wolf | |
| SEQ. ID. NO. 778 | 16-ProMetProSerGluSerLysProValSer-25 |
| SEQ. ID. NO. 779 | 27-IleValThrAspSerArgAspIleArgAlaGlyAsp-38 |
| SEQ. ID. NO. 780 | 44-AlaGlyGluArgPheAspAla-50 |
| SEQ. ID. NO. 781 | 67-ValSerArgGluAspCysAlaAla-74 |
| SEQ. ID. NO. 782 | 77-GlyAlaLeuLysValAspAspThrLeu-85 |
| SEQ. ID. NO. 783 | 94-AlaTrpArgGluAsnValAsnProPhe-102 |
| SEQ. ID. NO. 784 | 108-GlySerGlyGlyLysThrThrValLysGluMetLeu-119 |
| SEQ. ID. NO. 785 | 123-LeuArgArgArgPheGlyAspAspAlaVal-132 |
| SEQ. ID. NO. 786 | 138-AsnPheAsnAsnHisIle-143 |
| SEQ. ID. NO. 787 | 151-LysLeuAsnGluLysHisArg-157 |
| SEQ. ID. NO. 788 | 178-AlaLysProAsnAla-182 |
| SEQ. ID. NO. 789 | 194-GlyCysGlyPheAspGlyValGlyAspIleAlaLysAlaLysSerGluIle-210 |
| SEQ. ID. NO. 790 | 212-GlnGlyLeuCysSerAspGly-218 |
| SEQ. ID. NO. 791 | 223-ProGlnGluAspAlaAsn-228 |
| SEQ. ID. NO. 792 | 239-LeuAsnThrArgThrPheGlyIleAspSerGlyAspValHisAla-253 |
| SEQ. ID. NO. 793 | 269-CysGlyAspGluArgAlaAla-275 |
| SEQ. ID. NO. 794 | 280-ValProGlyArgHisAsnVal-286 |
| SEQ. ID. NO. 795 | 305-AspValAlaGluGlyLeuLys-311 |

TABLE 1-continued

| | |
|---|---|
| SEQ. ID. NO. 796 | 313-PheSerAsnIleLysGlyArgLeuAsnValLysSerGlyIleLysGly-328 |
| SEQ. ID. NO. 797 | 330-ThrLeuIleAspAspThrTyrAsnAlaAsnProAspSerMetLysAlaAla-346 |
| SEQ. ID. NO. 798 | 363-AspMetGlyGluLeuGlyGluLeuGlyGluAspGluAlaAla-376 |
| SEQ. ID. NO. 799 | 384-AlaTyrAlaArgAspGlnGlyIle-391 |
| SEQ. ID. NO. 800 | 398-GlyAspAsnSerValGluAlaAlaGluLysPheGlyAla-410 |
| SEQ. ID. NO. 801 | 425-LeuArgHisAspLeuProGluArgAlaThrVal-435 |
| SEQ. ID. NO. 802 | 437-ValLysGlySerArg-441 |
| SEQ. ID. NO. 803 | 446-GluGluValValGluAlaLeuGluAspLys-455 |
| Hydrophilic Regions - Hopp-Woods | |
| SEQ. ID. NO. 804 | 17-MetProSerGluSerLysProValSer-25 |
| SEQ. ID. NO. 805 | 27-IleValThrAspSerArgAspIleArgAla-36 |
| SEQ. ID. NO. 806 | 44-AlaGlyGluArgPheAspAla-50 |
| SEQ. ID. NO. 807 | 67-ValSerArgGluAspCysAlaAla-74 |
| SEQ. ID. NO. 808 | 77-GlyAlaLeuLysValAspAspThrLeu-85 |
| SEQ. ID. NO. 809 | 94-AlaTrpArgGluAsnVal-99 |
| SEQ. ID. NO. 810 | 109-SerGlyGlyLysThrThrValLysGluMetLeu-119 |
| SEQ. ID. NO. 811 | 123-LeuArgArgArgPheGlyAsp-129 |
| SEQ. ID. NO. 812 | 151-LysLeuAsnGluLysHisArg-157 |
| SEQ. ID. NO. 813 | 199-GlyValGlyAspIleAlaLysAlaLysSerGluIle-210 |
| SEQ. ID. NO. 814 | 223-ProGlnGluAspAlaAsn-228 |
| SEQ. ID. NO. 815 | 247-AspSerGlyAspValHisAla-253 |
| SEQ. ID. NO. 816 | 269-CysGlyAspGluArgAlaAla-275 |
| SEQ. ID. NO. 817 | 305-AspValAlaGluGlyLeuLys-311 |
| SEQ. ID. NO. 818 | 316-IleLysGlyArgLeuAsnVal-322 |
| SEQ. ID. NO. 819 | 335-ThrTyrAsnAlaAsnProAspSerMetLysAlaAla-346 |
| SEQ. ID. NO. 820 | 363-AspMetGlyGluLeuGlyGluLeuGlyGluAspGluAlaAla-376 |
| SEQ. ID. NO. 821 | 384-AlaTyrAlaArgAspGlnGlyIle-391 |
| SEQ. ID. NO. 822 | 400-AsnSerValGluAlaAlaGluLysPheGlyAla-410 |
| SEQ. ID. NO. 823 | 425-LeuArgHisAspLeuProGluArgAlaThrVal-435 |
| SEQ. ID. NO. 824 | 446-GluGluValValGluAlaLeuGluAspLys-455 |
| 084-2 | |
| AMPHI Regions - AMPHI | |
| SEQ. ID. NO. 825 | 6-ArgIleLysAsnMetAsnGlnThrLeuLysAsnThrLeuGly-19 |
| SEQ. ID. NO. 826 | 21-CysAlaLeuLeuAla-25 |
| SEQ. ID. NO. 827 | 48-AlaValGlyAlaLeuAla-53 |
| SEQ. ID. NO. 828 | 65-PheProArgValSer-69 |
| SEQ. ID. NO. 829 | 96-GlnIleValGlySerIleLeuGluSer-104 |
| SEQ. ID. NO. 830 | 111-GluPheValGlyAsnLeuProGly-118 |
| Antigenic Index - Jameson-Wolf | |
| SEQ. ID. NO. 831 | 1-MetLysGlnSerAlaArgIleLysAsnMetAsnGlnThrLeuLysAsnThr-17 |
| SEQ. ID. NO. 832 | 40-TyrGluTyrGlyTyrArgTyrSer-47 |
| SEQ. ID. NO. 833 | 102-LeuGluSerAsnProAlaGluAlaArgGluPheValGly-114 |
| SEQ. ID. NO. 834 | 139-ValSerGlyGlyGly-143 |
| Hydrophilic Regions - Hopp-Woods | |
| SEQ. ID. NO. 835 | 1-MetLysGlnSerAlaArgIleLysAsnMetAsnGlnThrLeu-14 |
| SEQ. ID. NO. 836 | 105-AsnProAlaGluAlaArgGluPheVal-113 |
| 085-2 | |
| AMPHI Regions - AMPHI | |
| SEQ. ID. NO. 837 | 41-GluArgValSerGlnIleGlyLysMetPheAspGlyLeu-53 |
| SEQ. ID. NO. 838 | 60-LeuLysAspAlaLeuAspAsnGlyPheAsp-69 |
| SEQ. ID. NO. 839 | 90-AsnGlyGlyArgValLeuGlyAspIleGluLeuLeuAlaAsp-103 |
| SEQ. ID. NO. 840 | 125-ThrSerLeuValGlyTyr-130 |
| SEQ. ID. NO. 841 | 141-IleAlaGlyAsnIleGlyThr-147 |
| SEQ. ID. NO. 842 | 174-GluAsnThrGluSerLeu-179 |
| SEQ. ID. NO. 843 | 193-HisLeuAspArgTyrAspAspLeuLeuAspTyr-203 |
| SEQ. ID. NO. 844 | 212-ArgGlyAspGlyValGln-217 |
| SEQ. ID. NO. 845 | 225-PheCysArgAlaMetLysArgAla-232 |
| SEQ. ID. NO. 846 | 275-HisAsnAlaAlaAsnValMetAlaAlaValAlaLeuCysGluAla-289 |
| SEQ. ID. NO. 847 | 300-HisValLysThrPheGlnGlyLeuProHisArgValGluLysIleGly-315 |
| SEQ. ID. NO. 848 | 336-AlaAlaIleAlaGlyLeu-341 |
| SEQ. ID. NO. 849 | 353-GlyLysGlyGlnAspPheThr-359 |
| SEQ. ID. NO. 850 | 395-AspCysAlaThrLeuGlyGluAlaValGlnThr-405 |
| SEQ. ID. NO. 851 | 424-SerPheAspMetPheLysGlyTyr-431 |
| Antigenic Index - Jameson-Wolf | |
| SEQ. ID. NO. 852 | 4-GlnAsnLysLysIleLeu-9 |
| SEQ. ID. NO. 853 | 23-TyrLeuArgLysAsnGlyAlaGluValAlaAlaTyrAspAlaGluLeuLysProGluArgValSerGlnIleGlyLysMetPheAsp-51 |
| SEQ. ID. NO. 854 | 58-GlyArgLeuLysAspAlaLeuAspAsnGlyPhe-68 |
| SEQ. ID. NO. 855 | 74-SerProGlyIleSerGluArgGlnProAspIleGluAlaPheLysGlnAsnGlyGlyArgValLeuGly-96 |
| SEQ. ID. NO. 856 | 104-IleValAsnArgArgAspAspLysValIle-113 |
| SEQ. ID. NO. 857 | 116-ThrGlySerAsnGlyLysThrThr-123 |
| SEQ. ID. NO. 858 | 153-GluTrpGlnArgGlyLysLysAlaAsp-162 |
| SEQ. ID. NO. 859 | 169-SerSerPheGlnLeuGluAsnThrGluSerLeuArgProThrAla-183 |
| SEQ. ID. NO. 860 | 189-IleSerGluAspHisLeuAspArgTyrAspAspLeuLeu-201 |
| SEQ. ID. NO. 861 | 204-AlaHisThrLysAlaLysIlePheArgGlyAspGlyVal-216 |
| SEQ. ID. NO. 862 | 220-AsnAlaAspAspAlaPheCysArgAlaMetLysArgAlaGlyArgGluValLys-237 |
| SEQ. ID. NO. 863 | 247-PheTrpLeuGluArgGluThrGlyArgLeuLysGlnGlyAsnGluAspLeuIleVal-265 |
| SEQ. ID. NO. 864 | 291-GlyLeuSerArgGluAlaLeu-297 |
| SEQ. ID. NO. 865 | 307-LeuProHisArgValGluLysIleGlyGluLysAsnGly-319 |
| SEQ. ID. NO. 866 | 322-PheIleAspAspSerLysGlyThrAsnVal-331 |
| SEQ. ID. NO. 867 | 351-GlyMetGlyLysGlyGlnAspPheThrProLeuArgAspAlaLeuValGlyLysAlaLys-370 |

TABLE 1-continued

| | |
|---|---|
| SEQ. ID. NO. 868 | 378-AspAlaProGlnIleArgArgAspLeuAspGlyCysGly-390 |
| SEQ. ID. NO. 869 | 431-TyrAlaHisArgSer-435 |

Hydrophilic Regions - Hopp-Woods

| | |
|---|---|
| SEQ. ID. NO. 870 | 4-GlnAsnLysLysIleLeu-9 |
| SEQ. ID. NO. 871 | 25-ArgLysAsnGlyAlaGlu-30 |
| SEQ. ID. NO. 872 | 32-AlaAlaTyrAspAlaGluLeuLysProGluArgValSerGln-45 |
| SEQ. ID. NO. 873 | 59-ArgLeuLysAspAlaLeuAspAsnGlyPhe-68 |
| SEQ. ID. NO. 874 | 76-GlyIleSerGluArgGlnProAspIleGluAlaPheLysGlnAsnGlyGly-92 |
| SEQ. ID. NO. 875 | 104-IleValAsnArgArgAspAspLysVal-112 |
| SEQ. ID. NO. 876 | 118-SerAsnGlyLysThrThr-123 |
| SEQ. ID. NO. 877 | 153-GluTrpGlnArgGluGlyLysLysAlaAsp-162 |
| SEQ. ID. NO. 878 | 174-GluAsnThrGluSerLeuArgPro-181 |
| SEQ. ID. NO. 879 | 189-IleSerGluAspHisLeuAspArgTyrAspAspLeuLeu-201 |
| SEQ. ID. NO. 880 | 204-AlaHisThrLysAlaLysIlePheArgGlyAspGly-215 |
| SEQ. ID. NO. 881 | 220-AsnAlaAspAspAlaPheCysArgAlaMetLysArgAlaGlyArgGluValLys-237 |
| SEQ. ID. NO. 882 | 247-PheTrpLeuGluArgGluThrGlyArgLeuLysGlnGlyAsnGluAspLeuIleVal-265 |
| SEQ. ID. NO. 883 | 291-GlyLeuSerArgGluAlaLeu-297 |
| SEQ. ID. NO. 884 | 309-HisArgValGluLysIleGlyGluLysAsnGly-319 |
| SEQ. ID. NO. 885 | 324-AspAspSerLysGlyThrAsn-330 |
| SEQ. ID. NO. 886 | 353-GlyLysGlyGlnAsp-357 |
| SEQ. ID. NO. 887 | 359-ThrProLeuArgAspAlaLeuValGlyLysAlaLys-370 |
| SEQ. ID. NO. 888 | 380-ProGlnIleArgArgAspLeuAspGly-388 |
| SEQ. ID. NO. 889 | 431-TyrAlaHisArgSer-435 |

086-2
AMPHI Regions - AMPHI

| | |
|---|---|
| SEQ. ID. NO. 890 | 55-MetArgThrTrpArgArgLeuValPro-63 |
| SEQ. ID. NO. 891 | 83-IleAsnGlyAlaThrArg-88 |
| SEQ. ID. NO. 892 | 99-ProThrGluLeuPheLysLeuAlaVal-107 |
| SEQ. ID. NO. 893 | 120-GluValLeuArgSerMetGluSerLeuGlyTrpGlnSerIleTrpArgGlyThrAlaAsn-139 |
| SEQ. ID. NO. 894 | 155-GluMetTyrGlyArgPhe-160 |
| SEQ. ID. NO. 895 | 185-SerPheValValIle-189 |
| SEQ. ID. NO. 896 | 228-ArgValGlnArgValValAlaPheLeuAspProTrpLysAspProGln-243 |
| SEQ. ID. NO. 897 | 293-GlyPhePheGlyMetCys-298 |
| SEQ. ID. NO. 898 | 336-TrpIleGlyIleGlnSerPhe-342 |

Antigenic Index - Jameson-Wolf

| | |
|---|---|
| SEQ. ID. NO. 899 | 20-LeuAlaSerLysGluGlyGlyAsp-27 |
| SEQ. ID. NO. 900 | 55-MetArgThrTrpArgArg-60 |
| SEQ. ID. NO. 901 | 79-AlaGlyArgGluIleAsnGlyAlaThr-87 |
| SEQ. ID. NO. 902 | 115-PheThrArgArgGluGluValLeuArgSerMetGlu-126 |
| SEQ. ID. NO. 903 | 134-TrpArgGlyThrAla-138 |
| SEQ. ID. NO. 904 | 144-AlaThrAsnProGlnAlaArgArgGluThrLeuGluMet-156 |
| SEQ. ID. NO. 905 | 225-AlaProTyrArgVal-229 |
| SEQ. ID. NO. 906 | 236-LeuAspProTrpLysAspProGlnGlyAla-245 |
| SEQ. ID. NO. 907 | 265-GlyLeuGlyAlaSerLeuSerLysArgGlyPheLeu-276 |
| SEQ. ID. NO. 908 | 313-SerIleGlyLysGlnSerArgAspLeuGly-322 |
| SEQ. ID. NO. 909 | 352-LeuProThrLysGlyLeu-357 |
| SEQ. ID. NO. 910 | 382-IleAspTyrGluAsnArgArgLysMetArgGlyTyrArgValGlu-396 |

Hydrophilic Regions - Hopp-Woods

| | |
|---|---|
| SEQ. ID. NO. 911 | 21-AlaSerLysGluGlyGlyAsp-27 |
| SEQ. ID. NO. 912 | 79-AlaGlyArgGluIleAsnGly-85 |
| SEQ. ID. NO. 913 | 115-PheThrArgArgGluGluValLeuArgSerMetGlu-126 |
| SEQ. ID. NO. 914 | 147-ProGlnAlaArgArgGluThrLeuGluMet-156 |
| SEQ. ID. NO. 915 | 238-ProTrpLysAspProGlnGly-244 |
| SEQ. ID. NO. 916 | 270-LeuSerLysArgGlyPheLeu-276 |
| SEQ. ID. NO. 917 | 316-LysGlnSerArgAspLeu-321 |
| SEQ. ID. NO. 918 | 382-IleAspTyrGluAsnArgArgLysMetArgGlyTyrArgValGlu-396 |

087-2
AMPHI Regions - AMPHI

| | |
|---|---|
| SEQ. ID. NO. 919 | 23-ValAlaAspSerLeuArg-28 |
| SEQ. ID. NO. 920 | 80-GlnThrValArgGluAlaGlnArgIleIle-89 |
| SEQ. ID. NO. 921 | 99-GlyPheGlyGlyPheValThrPheProGlyGlyLeuAlaAlaLysLeuLeu-115 |
| SEQ. ID. NO. 922 | 129-GlyLeuSerAsnArgHisLeuSerArgTrpAlaLysArgValLeuTyrAlaPheProLys-148 |
| SEQ. ID. NO. 923 | 157-ValGlyAsnProValArg-162 |
| SEQ. ID. NO. 924 | 192-GlyAlaAspValLeuAsnLysThrVal-200 |
| SEQ. ID. NO. 925 | 241-ValGluPheIleThrAspMetValSerAlaTyr-251 |
| SEQ. ID. NO. 926 | 313-GluLysLeuAlaGluIleLeuGly-320 |
| SEQ. ID. NO. 927 | 330-TrpAlaGluAsnAla-334 |

Antigenic Index - Jameson-Wolf

| | |
|---|---|
| SEQ. ID. NO. 928 | 25-AspSerLeuArgAlaArgGly-31 |
| SEQ. ID. NO. 929 | 37-LeuGlySerLysAspSerMetGluGluArgIleValProGlnTyrGlyIle-53 |
| SEQ. ID. NO. 930 | 61-LysGlyValArgGlyAsnGlyIleLysArgLysLeu-72 |
| SEQ. ID. NO. 931 | 81-ThrValArgGluAlaGlnArgIleIleArgLysHisArgVal-94 |
| SEQ. ID. NO. 932 | 130-LeuSerAsnArgHisLeuSerArgTrpAlaLys-140 |
| SEQ. ID. NO. 933 | 150-PheSerHisGluGlyGlyLeu-156 |
| SEQ. ID. NO. 934 | 159-AsnProValArgAlaAspIleSer-166 |
| SEQ. ID. NO. 935 | 171-ProAlaGluArgPheGlnGlyArgGluGlyArgLeu-182 |
| SEQ. ID. NO. 936 | 195-ValLeuAsnLysThrVal-200 |
| SEQ. ID. NO. 937 | 207-LeuProAspAsnAlaArgProGlnMetTyrHisGlnSerGlyArgGlyLysLeuGly-225 |
| SEQ. ID. NO. 938 | 229-AlaAspTyrAspAla-233 |
| SEQ. ID. NO. 939 | 235-GlyValLysAlaGluCys-240 |

TABLE 1-continued

| | |
|---|---|
| SEQ. ID. NO. 940 | 249-SerAlaTyrArgAspAlaAsp-255 |
| SEQ. ID. NO. 941 | 284-AlaValAspAspHisGlnThrAla-291 |
| SEQ. ID. NO. 942 | 309-GlnLeuThrAlaGluLysLeuAlaGlu-317 |
| SEQ. ID. NO. 943 | 321-GlyLeuAsnArgGluLysCysLeuLys-329 |
| SEQ. ID. NO. 944 | 331-AlaGluAsnAlaArgThr-336 |
| SEQ. ID. NO. 945 | 341-HisSerAlaAspAspValAlaGlu-348 |
| Hydrophilic Regions - Hopp-Woods | |
| SEQ. ID. NO. 946 | 25-AspSerLeuArgAlaArgGly-31 |
| SEQ. ID. NO. 947 | 39-SerLysAspSerMetGluGluArgIleVal-48 |
| SEQ. ID. NO. 948 | 66-AsnGlyIleLysArgLysLeu-72 |
| SEQ. ID. NO. 949 | 81-ThrValArgGluAlaGlnArgIleIleArgLysHisArgVal-94 |
| SEQ. ID. NO. 950 | 134-HisLeuSerArgTrpAlaLys-140 |
| SEQ. ID. NO. 951 | 161-ValArgAlaAspIle-165 |
| SEQ. ID. NO. 952 | 171-ProAlaGluArgPheGlnGlyArgGluGlyArgLeu-182 |
| SEQ. ID. NO. 953 | 219-SerGlyArgGlyLysLeu-224 |
| SEQ. ID. NO. 954 | 235-GlyValLysAlaGluCys-240 |
| SEQ. ID. NO. 955 | 249-SerAlaTyrArgAspAlaAsp-255 |
| SEQ. ID. NO. 956 | 284-AlaValAspAspHisGlnThrAla-291 |
| SEQ. ID. NO. 957 | 310-LeuThrAlaGluLysLeuAlaGlu-317 |
| SEQ. ID. NO. 958 | 322-LeuAsnArgGluLysCysLeuLys-329 |
| SEQ. ID. NO. 959 | 331-AlaGluAsnAlaArg-335 |
| SEQ. ID. NO. 960 | 341-HisSerAlaAspAspValAlaGlu-348 |
| 088-2 | |
| AMPHI Regions - AMPHI | |
| SEQ. ID. NO. 961 | 7-HisPheSerAsnTrpLeuThrGlyLeuAsnIlePheGlnTyrThrThr-22 |
| SEQ. ID. NO. 962 | 24-ArgAlaValMetAlaAlaLeu-30 |
| SEQ. ID. NO. 963 | 43-ThrIleArgArgLeuThrAlaLeuLysCysGlyGln-54 |
| SEQ. ID. NO. 964 | 88-LeuTrpGlyAsnTrpAlaAsn-94 |
| SEQ. ID. NO. 965 | 111-GlyPheTyrAspAspTrpArgLysValValTyr-121 |
| SEQ. ID. NO. 966 | 140-AlaIleIleAlaSerLeuAlaLeu-147 |
| SEQ. ID. NO. 967 | 175-GlyPheLeuValLeuSerTyrLeuThrIle-184 |
| SEQ. ID. NO. 968 | 187-ThrSerAsnAlaValAsnLeuThrAspGlyLeuAspGlyLeuAlaThr-202 |
| SEQ. ID. NO. 969 | 221-HisSerGlnPheAlaGlnTyrLeuGlnLeuProTyr-232 |
| SEQ. ID. NO. 970 | 245-AlaMetCysGlyAlaCysLeuGlyPhe-253 |
| Antigenic Index - Jameson-Wolf | |
| SEQ. ID. NO. 971 | 48-ThrAlaLeuLysCysGlyGlnAlaValArgThrAspGlyProGln-62 |
| SEQ. ID. NO. 972 | 66-ValLysAsnGlyThrProThrMet-73 |
| SEQ. ID. NO. 973 | 114-AspAspTrpArgLysValValTyrLysAspProAsnGlyValSerAlaLysPhe-131 |
| SEQ. ID. NO. 974 | 193-LeuThrAspGlyLeuAsp-198 |
| SEQ. ID. NO. 975 | 312-LysLysThrLysLysArgIle-318 |
| SEQ. ID. NO. 976 | 328-TyrGluGlnLysGlyTrpLysGluThrGlnVal-338 |
| Hydrophilic Regions - Hopp-Woods | |
| SEQ. ID. NO. 977 | 56-ValArgThrAspGlyProGln-62 |
| SEQ. ID. NO. 978 | 114-AspAspTrpArgLysValValTyrLysAspProAsnGlyVal-127 |
| SEQ. ID. NO. 979 | 312-LysLysThrLysLysArgIle-318 |
| SEQ. ID. NO. 980 | 331-LysGlyTrpLysGlu-335 |
| 089-2 | |
| AMPHI Regions - AMPHI | |
| SEQ. ID. NO. 981 | 40-PheSerThrArgCysGlyArgProTrpLysValLeu-51 |
| SEQ. ID. NO. 982 | 74-LeuAlaAlaLeuCysArgProCysAsnGlyMetSerCys-86 |
| SEQ. ID. NO. 983 | 118-SerArgProAlaArgPhe-123 |
| Antigenic Index - Jameson-Wolf | |
| SEQ. ID. NO. 984 | 1-MetProProLysIleThrLysSerGlyPhe-10 |
| SEQ. ID. NO. 985 | 40-PheSerThrArgCysGlyArgProTrpLys-49 |
| SEQ. ID. NO. 986 | 54-SerSerAsnAlaSerArgAspLysProMetAlaSerHisLysAla-68 |
| SEQ. ID. NO. 987 | 79-ArgProCysAsnGlyMetSerCys-86 |
| SEQ. ID. NO. 988 | 95-CysPheArgArgProValSerArgSerAsnGlnLysSerAlaSerCysSerAsnGluAsnHisPheThrSerArgProAlaArgPheIleAlaArgGlnAsnAlaSerSerAlaPheLysThrCysThrProSerProArgLysIleLeu-144 |
| Hydrophilic Regions - Hopp-Woods | |
| SEQ. ID. NO. 989 | 43-ArgCysGlyArgPro-47 |
| SEQ. ID. NO. 990 | 56-AsnAlaSerArgAspLysProMetAlaSerHisLysAla-68 |
| SEQ. ID. NO. 991 | 95-CysPheArgArgProValSerArgSerAsnGlnLysSerAlaSerCysSerAsn-112 |
| SEQ. ID. NO. 992 | 119-ArgProAlaArgPheIleAla-125 |
| SEQ. ID. NO. 993 | 137-ThrProSerProArgLysIle-143 |
| 090-1 | |
| AMPHI Regions - AMPHI | |
| SEQ. ID. NO. 994 | 10-SerGlnSerLeuLysArgPheAspLysHisPheArg-21 |
| SEQ. ID. NO. 995 | 56-SerGlnSerGlyAlaValGlyHisIle-64 |
| SEQ. ID. NO. 996 | 141-AlaAspPhePheHisAlaValArgGlnAla-150 |
| SEQ. ID. NO. 997 | 152-GluGlyPheAspValPheGluGlnCysPheAla-162 |
| SEQ. ID. NO. 998 | 164-GlnThrAspGlyLeuThrGln-170 |
| SEQ. ID. NO. 999 | 177-ValSerGlyValValGlnThrLeuGlnArg-186 |
| SEQ. ID. NO. 1000 | 226-LeuHisArgAlaAlaGluArgIleValArgIleGlnAsnLeuHisAlaVal-242 |
| SEQ. ID. NO. 1001 | 387-IleGluThrValValGlnArgIlePheGlnThrAla-398 |
| SEQ. ID. NO. 1002 | 404-ProValLysHisLeuThrAspLeuArg-412 |
| SEQ. ID. NO. 1003 | 425-AsnLeuArgAlaValPheAlaGlnValGlyAsnHisGlyAsnThrArgThrAlaGluSer-444 |
| Antigenic Index - Jameson-Wolf | |
| SEQ. ID. NO. 1004 | 9-AlaSerGlnSerLeuLysArgPheAspLysHisPheArg-21 |
| SEQ. ID. NO. 1005 | 29-HisIleLysAlaArgAlaGlyGlyAlaGluGlnHis-40 |
| SEQ. ID. NO. 1006 | 53-AsnGlyPheSerGlnSerGly-59 |

TABLE 1-continued

| | |
|---|---|
| SEQ. ID. NO. 1007 | 73-AlaAspLeuArgArgIleAspThrAsnGlnGlu-83 |
| SEQ. ID. NO. 1008 | 94-AlaGlnGlyArgGluVal-99 |
| SEQ. ID. NO. 1009 | 107-GlnAsnHisGluGluArgIleLeuGlnThrGlyAsnArgGlyGlySerArgAlaAspIleArg-127 |
| SEQ. ID. NO. 1010 | 149-GlnAlaLeuGluGly-153 |
| SEQ. ID. NO. 1011 | 161-PheAlaArgGlnThrAspGlyLeuThrGlnSerHisGlySerHisAspValSerGly-179 |
| SEQ. ID. NO. 1012 | 187-AsnValLeuArgAspAsnGln-193 |
| SEQ. ID. NO. 1013 | 214-PheGlnArgLysProPheTyr-220 |
| SEQ. ID. NO. 1014 | 228-ArgAlaAlaGluArgIleValArg-235 |
| SEQ. ID. NO. 1015 | 269-GlnHisArgArgArgSerArgThrGlnAla-278 |
| SEQ. ID. NO. 1016 | 285-GluAlaGlyLysLeuGln-290 |
| SEQ. ID. NO. 1017 | 304-ArgLeuGlnAsnArgArgAlaAspIleAlaArgAspAsnGlyIle-318 |
| SEQ. ID. NO. 1018 | 320-ProAlaLeuAspThrGluIleAlaAspGlnAlaArgTyrArgGly-334 |
| SEQ. ID. NO. 1019 | 339-AlaGlyAsnArgAsnTyr-344 |
| SEQ. ID. NO. 1020 | 353-ValArgGlnGlnPhe-357 |
| SEQ. ID. NO. 1021 | 379-AspAlaGlyThrGluSerGlnAsnIle-387 |
| SEQ. ID. NO. 1022 | 398-AlaArgValLysHisGlnProValLysHisLeuThrAspLeuArgHis-413 |
| SEQ. ID. NO. 1023 | 421-IleIleArgSerAsnLeuArg-427 |
| SEQ. ID. NO. 1024 | 434-GlyAsnHisGlyAsnThrArgThrAlaGluSerGlyAspGluAspPhePhe-450 |
| Hydrophilic Regions - Hopp-Woods | |
| SEQ. ID. NO. 1025 | 11-GlnSerLeuLysArgPheAspLysHisPheArg-21 |
| SEQ. ID. NO. 1026 | 29-HisIleLysAlaArgAlaGlyGlyAlaGluGlnHis-40 |
| SEQ. ID. NO. 1027 | 73-AlaAspLeuArgArgIleAspThrAsnGln-82 |
| SEQ. ID. NO. 1028 | 94-AlaGlnGlyArgGluVal-99 |
| SEQ. ID. NO. 1029 | 107-GlnAsnHisGluGluArgIleLeu-114 |
| SEQ. ID. NO. 1030 | 117-GlyAsnArgGlyGlySerArgAlaAspIleArg-127 |
| SEQ. ID. NO. 1031 | 163-ArgGlnThrAspGlyLeuThr-169 |
| SEQ. ID. NO. 1032 | 173-GlySerHisAspVal-177 |
| SEQ. ID. NO. 1033 | 187-AsnValLeuArgAspAsnGln-193 |
| SEQ. ID. NO. 1034 | 228-ArgAlaAlaGluArgIleValArg-235 |
| SEQ. ID. NO. 1035 | 269-GlnHisArgArgArgSerArgThrGln-277 |
| SEQ. ID. NO. 1036 | 285-GluAlaGlyLysLeuGln-290 |
| SEQ. ID. NO. 1037 | 305-LeuGlnAsnArgArgAlaAspIleAlaArgAspAsnGlyIle-318 |
| SEQ. ID. NO. 1038 | 322-LeuAspThrGluIleAlaAspGlnAlaArgTyrArg-333 |
| SEQ. ID. NO. 1039 | 380-AlaGlyThrGluSerGlnAsnIle-387 |
| SEQ. ID. NO. 1040 | 398-AlaArgValLysHisGlnPro-404 |
| SEQ. ID. NO. 1041 | 407-HisLeuThrAspLeuArgHis-413 |
| SEQ. ID. NO. 1042 | 421-IleIleArgSerAsnLeu-426 |
| SEQ. ID. NO. 1043 | 437-GlyAsnThrArgThrAlaGluSerGlyAspGluAspPhePhe-450 |
| 091-2 | |
| AMPHI Regions - AMPHI | |
| SEQ. ID. NO. 1044 | 11-ProLeuSerAspGlyIleAlaSerCys-19 |
| SEQ. ID. NO. 1045 | 21-IleThrArgLeuGlnAlaLeuVal-28 |
| SEQ. ID. NO. 1046 | 33-ValLeuValSerValLeuThrSerLeuAlaLys-43 |
| Antigenic Index - Jameson-Wolf | |
| SEQ. ID. NO. 1047 | 1-LeuSerArgArgCysProProLeuProLysProLeuSerAspGlyIleAla-17 |
| SEQ. ID. NO. 1048 | 73-LeuArgCysArgLeuProLysProSerAspArgPheAsp-85 |
| SEQ. ID. NO. 1049 | 105-LeuAspAsnProLeuArgCysArgLeuProIleProSerAspArgPheGly-121 |
| Hydrophilic Regions - Hopp-Woods | |
| SEQ. ID. NO. 1050 | 1-LeuSerArgArgCysProProLeu-8 |
| SEQ. ID. NO. 1051 | 75-CysArgLeuProLysProSerAspArgPheAsp-85 |
| SEQ. ID. NO. 1052 | 107-AsnProLeuArgCys-111 |
| SEQ. ID. NO. 1053 | 115-IleProSerAspArgPhe-120 |
| 092 | |
| AMPHI Regions - AMPHI | |
| SEQ. ID. NO. 1054 | 55-GlyMetSerGlyIleAlaGluValLeuHis-64 |
| SEQ. ID. NO. 1055 | 76-AlaArgAsnAlaAlaThrGluHisLeu-84 |
| SEQ. ID. NO. 1056 | 95-HisThrAlaGluHisValAsnGly-102 |
| SEQ. ID. NO. 1057 | 120-ValAlaAlaLeuGlu-124 |
| SEQ. ID. NO. 1058 | 137-AlaGluLeuMetArgPheArgAsp-144 |
| SEQ. ID. NO. 1059 | 209-LeuThrProIleMetSerValValThrAsnIleAsp-220 |
| SEQ. ID. NO. 1060 | 226-ThrTyrGlyHisSerValGluLysLeuHisGlnAlaPheIleAspPheHisArg-244 |
| SEQ. ID. NO. 1061 | 259-HisValArgAlaIleLeuProLysValSerLysProTyr-271 |
| SEQ. ID. NO. 1062 | 273-ThrTyrGlyLeuAspAspThrAla-280 |
| SEQ. ID. NO. 1063 | 321-AsnValLeuAsnAlaLeuAlaAlaIle-329 |
| SEQ. ID. NO. 1064 | 339-ValGluAlaIleGlnLysGly-345 |
| SEQ. ID. NO. 1065 | 353-GlyArgArgPheGlnLysTyrGlyAspIleLys-363 |
| SEQ. ID. NO. 1066 | 407-ArgTyrThrArgThrArgAspLeuPheGluAspPheThrLysValLeuAsnThrValAspAlaLeu-428 |
| SEQ. ID. NO. 1067 | 449-LeuAlaArgAlaIleArgValLeuGlyLysLeu-459 |
| SEQ. ID. NO. 1068 | 464-CysGluAsnValAlaAspLeuProGluMetLeuLeuAsn-476 |
| Antigenic Index - Jameson-Wolf | |
| SEQ. ID. NO. 1069 | 14-LeuTrpArgAlaAsnGlyGlnProPheLys-23 |
| SEQ. ID. NO. 1070 | 25-ThrProLeuArgIleGluAsnProProGluArgAsnIleMetMetLysAsnArgVal-43 |
| SEQ. ID. NO. 1071 | 70-ValSerGlySerAspGlnAlaArgAsnAlaAla-80 |
| SEQ. ID. NO. 1072 | 111-AlaValLysLysGluAsnProGluVal-119 |
| SEQ. ID. NO. 1073 | 140-MetArgPheArgAspGlyIle-146 |
| SEQ. ID. NO. 1074 | 150-GlyThrHisGlyLysThrThrThr-157 |
| SEQ. ID. NO. 1075 | 184-GlyThrAsnAlaArgLeuGlyLysGlyGluTyr-194 |
| SEQ. ID. NO. 1076 | 198-GluAlaAspGluSerAspAla-204 |
| SEQ. ID. NO. 1077 | 218-AsnIleAspGluAspHisMetAspThrTyrGly-228 |
| SEQ. ID. NO. 1078 | 230-SerValGluLysLeuHis-235 |

TABLE 1-continued

| | |
|---|---|
| SEQ. ID. NO. 1079 | 255-IleAspSerGluHisVal-260 |
| SEQ. ID. NO. 1080 | 263-IleLeuProLysValSerLysProTyrAla-272 |
| SEQ. ID. NO. 1081 | 275-GlyLeuAspAspThrAlaAsp-281 |
| SEQ. ID. NO. 1082 | 286-AspIleGluAsnValGlyAla-292 |
| SEQ. ID. NO. 1083 | 302-MetLysGlyHisGluGlnGlySerPhe-310 |
| SEQ. ID. NO. 1084 | 351-GlyValGlyArgArgPheGlnLysTyrGlyAspIleLysLeuProAsnGlyGly-368 |
| SEQ. ID. NO. 1085 | 374-AspAspTyrGlyHisHisPro-380 |
| SEQ. ID. NO. 1086 | 393-AlaTyrLeuGluLysArgLeu-399 |
| SEQ. ID. NO. 1087 | 404-GlnProHisArgTyrThrArgThrArgAspLeuPheGluAspPheThrLys-420 |
| SEQ. ID. NO. 1088 | 435-AlaAlaGlyGluGluProIleAlaAlaAlaAspSerArgAlaLeuAlaArg-451 |
| SEQ. ID. NO. 1089 | 466-AsnValAlaAspLeuPro-471 |
| SEQ. ID. NO. 1090 | 478-LeuGlnAspGlyAspIle-483 |
| SEQ. ID. NO. 1091 | 488-GlyAlaGlySerIleAsn-493 |
| Hydrophilic Regions - Hopp-Woods | |
| SEQ. ID. NO. 1092 | 26-ProLeuArgIleGluAsnProProGluArgAsnIleMetMetLysAsnArgVal-43 |
| SEQ. ID. NO. 1093 | 71-SerGlySerAspGlnAlaArgAsnAlaAla-80 |
| SEQ. ID. NO. 1094 | 111-AlaValLysLysGluAsnProGlu-118 |
| SEQ. ID. NO. 1095 | 140-MetArgPheArgAsp-144 |
| SEQ. ID. NO. 1096 | 152-HisGlyLysThrThr-156 |
| SEQ. ID. NO. 1097 | 187-AlaArgLeuGlyLysGlyGlu-193 |
| SEQ. ID. NO. 1098 | 198-GluAlaAspGluSerAspAla-204 |
| SEQ. ID. NO. 1099 | 218-AsnIleAspGluAspHisMetAsp-225 |
| SEQ. ID. NO. 1100 | 230-SerValGluLysLeuHis-235 |
| SEQ. ID. NO. 1101 | 256-AspSerGluHisVal-260 |
| SEQ. ID. NO. 1102 | 275-GlyLeuAspAspThrAlaAsp-281 |
| SEQ. ID. NO. 1103 | 303-LysGlyHisGluGlnGlySer-309 |
| SEQ. ID. NO. 1104 | 351-GlyValGlyArgArgPheGlnLys-358 |
| SEQ. ID. NO. 1105 | 360-GlyAspIleLysLeu-364 |
| SEQ. ID. NO. 1106 | 393-AlaTyrLeuGluLysArgLeu-399 |
| SEQ. ID. NO. 1107 | 407-ArgTyrThrArgThrArgAspLeuPheGluAspPheThrLys-420 |
| SEQ. ID. NO. 1108 | 435-AlaAlaGlyGluGluProIleAlaAlaAlaAspSerArgAlaLeuAlaArg-451 |
| SEQ. ID. NO. 1109 | 466-AsnValAlaAspLeuPro-471 |
| SEQ. ID. NO. 1110 | 479-GlnAspGlyAspIle-483 |
| 093-2 | |
| AMPHI Regions - AMPHI | |
| SEQ. ID. NO. 1111 | 26-ThrAlaIleLeuAsn-30 |
| SEQ. ID. NO. 1112 | 59-ThrAlaPheAsnIleLeuHisGly-66 |
| SEQ. ID. NO. 1113 | 159-LysSerValTyrGluGluLeuLysHisLeu-168 |
| SEQ. ID. NO. 1114 | 196-IleHisIleIleProAlaThrGluPhe-204 |
| SEQ. ID. NO. 1115 | 254-PheLeuLysAspThr-258 |
| SEQ. ID. NO. 1116 | 267-IleAsnThrLeuProGlyMetThrSer-275 |
| Antigenic Index - Jameson-Wolf | |
| SEQ. ID. NO. 1117 | 12-GlyGlyPheSerSerGluArgGluIleSerLeuAspSerGlyThr-26 |
| SEQ. ID. NO. 1118 | 32-LeuLysSerLysGlyIleAsp-38 |
| SEQ. ID. NO. 1119 | 41-AlaPheAspProLysGluThrProLeuSerGluLeuLysAlaGlnGly-56 |
| SEQ. ID. NO. 1120 | 66-GlyThrTyrGlyGluAspGlyAlaVal-74 |
| SEQ. ID. NO. 1121 | 96-GlyMetAspLysTyrArgCys-102 |
| SEQ. ID. NO. 1122 | 120-HisAspAspThrAspPheAspAlaValGluGluLysLeuGly-133 |
| SEQ. ID. NO. 1123 | 140-ProAlaAlaGluGlySerSer-146 |
| SEQ. ID. NO. 1124 | 151-LysValLysGlyLysGlyArgLeuLysSerValTyrGluGluLeuLysHisLeuGln-169 |
| SEQ. ID. NO. 1125 | 176-ArgPheIleGlyGlyGlyGluTyrSer-184 |
| SEQ. ID. NO. 1126 | 189-AsnGlyLysGlyLeuPro-194 |
| SEQ. ID. NO. 1127 | 203-GluPheTyrAspTyrGluAlaLysTyrAsnArgAspAspThrIleTyrGlnCysProSerGluAspLeuThrGluAlaGluGluSerLeuMetArg-234 |
| SEQ. ID. NO. 1128 | 245-GlyAlaGluGlyCysVal-250 |
| SEQ. ID. NO. 1129 | 253-AspPheLeuLysAspThrAspGly-260 |
| SEQ. ID. NO. 1130 | 270-LeuProGlyMetThr-274 |
| SEQ. ID. NO. 1131 | 279-ValProLysSerAlaAla-284 |
| Hydrophilic Regions - Hopp-Woods | |
| SEQ. ID. NO. 1132 | 15-SerSerGluArgGluIleSerLeu-22 |
| SEQ. ID. NO. 1133 | 32-LeuLysSerLysGlyIleAsp-38 |
| SEQ. ID. NO. 1134 | 41-AlaPheAspProLysGluThrProLeuSerGluLeuLysAla-54 |
| SEQ. ID. NO. 1135 | 68-TyrGlyGluAspGlyAlaVal-74 |
| SEQ. ID. NO. 1136 | 96-GlyMetAspLysTyrArgCys-102 |
| SEQ. ID. NO. 1137 | 120-HisAspAspThrAspPheAspAlaValGluGluLysLeuGly-133 |
| SEQ. ID. NO. 1138 | 140-ProAlaAlaGluGlySerSer-146 |
| SEQ. ID. NO. 1139 | 151-LysValLysGlyLysGlyArgLeuLysSerValTyrGluGluLeuLysHisLeuGln-169 |
| SEQ. ID. NO. 1140 | 205-TyrAspTyrGluAlaLysTyrAsnArgAspAspThrIle-217 |
| SEQ. ID. NO. 1141 | 221-ProSerGluAspLeuThrGluAlaGluGluSerLeuMetArg-234 |
| SEQ. ID. NO. 1142 | 253-AspPheLeuLysAspThrAspGly-260 |
| 094 | |
| AMPHI Regions - AMPHI | |
| SEQ. ID. NO. 1143 | 17-LeuProProIleThrLysValGlySer-25 |
| SEQ. ID. NO. 1144 | 80-PheSerPheLeuThrAlaVal-86 |
| Antigenic Index - Jameson-Wolf | |
| SEQ. ID. NO. 1145 | 3-SerProLeuProLysArgAlaLeu-10 |
| SEQ. ID. NO. 1146 | 24-GlySerSerProAlaAlaProArgMetGluAla-34 |
| SEQ. ID. NO. 1147 | 50-MetProSerArgLysArgIleAsnSerAlaAsnIleArgAlaArgGlyIleThr-67 |
| Hydrophilic Regions - Hopp-Woods | |
| SEQ. ID. NO. 1148 | 5-LeuProLysArgAlaLeu-10 |
| SEQ. ID. NO. 1149 | 28-AlaAlaProArgMetGluAla-34 |

TABLE 1-continued

| | |
|---|---|
| SEQ. ID. NO. 1150 | 51-ProSerArgLysArgIleAsn-57 |
| SEQ. ID. NO. 1151 | 60-AsnIleArgAlaArgGly-65 |
| 095-2 | |
| AMPHI Regions - AMPHI | |
| SEQ. ID. NO. 1152 | 9-CysAlaSerAsnLeuPheArgGlnCysGlnGlnArgGlyGlyAspAlaValAsp-26 |
| SEQ. ID. NO. 1153 | 38-ValLeuGlnAsnValGlnGlnHisPheGlyGlnIleGlyAsnValPheAlaVal-55 |
| SEQ. ID. NO. 1154 | 86-PheGlyGlnHisGlnArgValAsnGlyIleGluAspPheGlyLysValPheLysGlnIleAlaArg-107 |
| SEQ. ID. NO. 1155 | 132-GlyArgGlyArgHisPheAspGlyValValSer-141 |
| SEQ. ID. NO. 1156 | 174-PheLeuAspArgPheAsnArgCysAlaAspPheGlnArgHisAlaAspGlyCysGlnCysValGlnHisVal-197 |
| SEQ. ID. NO. 1157 | 204-GlnHisAspPheLys-208 |
| SEQ. ID. NO. 1158 | 236-AspValGlyGlyIleValGlnThrValSerSerIle-247 |
| SEQ. ID. NO. 1159 | 274-ThrValAspGluIleAspLysArgLeuMetGlnPhePheAspAlaVal-289 |
| SEQ. ID. NO. 1160 | 313-GlyCysIleArgLeuValGly-319 |
| SEQ. ID. NO. 1161 | 370-AsnGlyAspAlaValThrGluAlaHisGlnLeuArgGlnHisGlnGlyAla-386 |
| SEQ. ID. NO. 1162 | 412-AspAspIleArgThrValAsnValPheGlyGlyMet-423 |
| SEQ. ID. NO. 1163 | 435-MetLeuGlySerGlyIleSerArgLeuIleArgThrGly-447 |
| SEQ. ID. NO. 1164 | 451-AlaGlnIleValGlnAspPheGlyAspAlaAlaHisAla-463 |
| Antigenic Index - Jameson-Wolf | |
| SEQ. ID. NO. 1165 | 6-SerGlyGlyCysAlaSerAsnLeu-13 |
| SEQ. ID. NO. 1166 | 16-GlnCysGlnGlnArgGlyGlyAspAlaValAspAlaSerArgAlaHisIle-32 |
| SEQ. ID. NO. 1167 | 62-GlnHisAlaAspGlyAlaGlyLysSerAlaGlyIleGlyGlyAlaAsnArgLeuPhe-80 |
| SEQ. ID. NO. 1168 | 88-GlnHisGlnArgValAsnGlyIleGluAspPheGlyLys-100 |
| SEQ. ID. NO. 1169 | 112-ValArgLeuGluGlyGluTyr-118 |
| SEQ. ID. NO. 1170 | 127-AlaCysGlyGlyLysGlyArgArgHisPheAspGly-138 |
| SEQ. ID. NO. 1171 | 144-ValHisGlnGluArgGlyProAla-151 |
| SEQ. ID. NO. 1172 | 163-AlaAlaAlaAspAlaPheLysAlaGluGlnAlaPhe-174 |
| SEQ. ID. NO. 1173 | 176-AspArgPheAsnArgCysAlaAspPheGlnArgHisAlaAspGlyCysGln-192 |
| SEQ. ID. NO. 1174 | 205-HisAspPheLysArg-209 |
| SEQ. ID. NO. 1175 | 253-GlyGlnAsnArgAlaAspVal-259 |
| SEQ. ID. NO. 1176 | 263-AsnThrGlnLysGlyPheAlaVal-270 |
| SEQ. ID. NO. 1177 | 273-HisThrValAspGluIleAspLysArgLeu-282 |
| SEQ. ID. NO. 1178 | 300-IleGlyAsnAspGlyHisAsnArgCysGlnValGlnLysGlyCys-314 |
| SEQ. ID. NO. 1179 | 339-PheAlaAlaAspAsnGluSerArgValLysSerCysArgAlaGluAspGlyGlyGlyGlnAlaGlyGlyArg GlyPheAlaValArgAlaGlyAsnGlyAspAlaValThr-375 |
| SEQ. ID. NO. 1180 | 378-HisGlnLeuArgGlnHisGlnGlyAlaArgAsnAsnGlyAsn-391 |
| SEQ. ID. NO. 1181 | 394-LeuGlnArgSerAspAsnPheGly-401 |
| SEQ. ID. NO. 1182 | 405-PheAspGlyGlyArgGlyAsnAspAspIleArgThr-416 |
| SEQ. ID. NO. 1183 | 442-ArgLeuIleArgThrGlyAsnPheLys-450 |
| SEQ. ID. NO. 1184 | 461-AlaHisAlaAspAlaAlaAspThrAspLysMetAspValGlyAsn-475 |
| Hydrophilic Regions - Hopp-Woods | |
| SEQ. ID. NO. 1185 | 17-CysGlnGlnArgGlyGlyAspAlaValAspAlaSerArgAlaHisIle-32 |
| SEQ. ID. NO. 1186 | 64-AlaAspGlyAlaGlyLysSerAlaGly-72 |
| SEQ. ID. NO. 1187 | 93-AsnGlyIleGluAspPheGlyLys-100 |
| SEQ. ID. NO. 1188 | 112-ValArgLeuGluGlyGluTyr-118 |
| SEQ. ID. NO. 1189 | 128-CysGlyGlyLysGlyArgArgHisPhe-136 |
| SEQ. ID. NO. 1190 | 145-HisGlnGluArgGlyPro-150 |
| SEQ. ID. NO. 1191 | 163-AlaAlaAlaAspAlaPheLysAlaGluGlnAlaPhe-174 |
| SEQ. ID. NO. 1192 | 182-AlaAspPheGlnArgHisAlaAspGly-190 |
| SEQ. ID. NO. 1193 | 205-HisAspPheLysArg-209 |
| SEQ. ID. NO. 1194 | 273-HisThrValAspGluIleAspLysArgLeu-282 |
| SEQ. ID. NO. 1195 | 300-IleGlyAsnAspGlyHisAsnArgCysGlnVal-310 |
| SEQ. ID. NO. 1196 | 339-PheAlaAlaAspAsnGluSerArgValLysSerCysArgAlaGluAspGlyGlyGly-357 |
| SEQ. ID. NO. 1197 | 368-AlaGlyAsnGlyAspAlaValThr-375 |
| SEQ. ID. NO. 1198 | 378-HisGlnLeuArgGlnHisGlnGlyAlaArgAsnAsnGly-390 |
| SEQ. ID. NO. 1199 | 395-GlnArgSerAspAsn-399 |
| SEQ. ID. NO. 1200 | 407-GlyGlyArgGlyAsnAspAspIleArgThr-416 |
| SEQ. ID. NO. 1201 | 461-AlaHisAlaAspAlaAlaAspThrAspLysMetAspVal-473 |
| 096-2 | |
| AMPHI Regions - AMPHI | |
| SEQ. ID. NO. 1202 | 19-GlyIlePheGluGluIleAspAlaHis-27 |
| SEQ. ID. NO. 1203 | 37-AlaAlaAsnArgGln-41 |
| SEQ. ID. NO. 1204 | 61-GlyValValAlaVal-65 |
| SEQ. ID. NO. 1205 | 112-GlnPhePheValAsnAlaPheGln-119 |
| SEQ. ID. NO. 1206 | 129-AlaTyrAlaAlaAlaPheGlyArg-136 |
| SEQ. ID. NO. 1207 | 172-AsnGlnPheAlaAla-176 |
| SEQ. ID. NO. 1208 | 187-AspThrAlaAlaGlyIleGlyAsnAlaGln-196 |
| SEQ. ID. NO. 1209 | 228-GlnTrpGlyPhePhe-232 |
| Antigenic Index - Jameson-Wolf | |
| SEQ. ID. NO. 1210 | 1-MetAlaArgHisThrGlyGlnGlyVal-9 |
| SEQ. ID. NO. 1211 | 22-GluGluIleAspAla-26 |
| SEQ. ID. NO. 1212 | 30-PheArgThrAspCysLeuArgAlaAlaAsn-39 |
| SEQ. ID. NO. 1213 | 75-GlyCysGlyAsnAspValTyrAla-82 |
| SEQ. ID. NO. 1214 | 88-ValGlnAspGlyAla-92 |
| SEQ. ID. NO. 1215 | 97-AlaAlaAspLysThrPheGlyAsn-104 |
| SEQ. ID. NO. 1216 | 137-ArgPheHisLysHisArgGln-143 |
| SEQ. ID. NO. 1217 | 157-ValGlnAspGlyGluLeuGlyAsnGlyGlnSerGlnCysLeu-170 |
| SEQ. ID. NO. 1218 | 181-AlaAspGlyGlyCysGlyAspThr-188 |
| SEQ. ID. NO. 1219 | 211-ThrValLysAspValGluCysArgLeu-219 |
| Hydrophilic Regions - Hopp-Woods | |
| SEQ. ID. NO. 1220 | 1-MetAlaArgHisThrGlyGln-7 |

TABLE 1-continued

| | |
|---|---|
| SEQ. ID. NO. 1221 | 22-GluGluIleAspAla-26 |
| SEQ. ID. NO. 1222 | 33-AspCysLeuArgAlaAlaAsn-39 |
| SEQ. ID. NO. 1223 | 97-AlaAlaAspLysThrPheGly-103 |
| SEQ. ID. NO. 1224 | 137-ArgPheHisLysHisArgGln-143 |
| SEQ. ID. NO. 1225 | 158-GlnAspGlyGluLeuGlyAsn-164 |
| SEQ. ID. NO. 1226 | 183-GlyGlyCysGlyAspThr-188 |
| SEQ. ID. NO. 1227 | 211-ThrValLysAspValGluCysArgLeu-219 |

097-2
AMPHI Regions - AMPHI

| | |
|---|---|
| SEQ. ID. NO. 1228 | 28-AlaGlyLeuThrThrPheLeuThrMetCysTyrIleVal-40 |
| SEQ. ID. NO. 1229 | 72-MetGlyPheValGly-76 |
| SEQ. ID. NO. 1230 | 166-AlaThrLeuValGlyLeuGlyAspIleHisGlnProSerAlaLeuLeuAlaLeuPheGly-185 |
| SEQ. ID. NO. 1231 | 207-ThrIleThrValIleAlaSerLeuMetGlyLeuAsnGluPheHisGlyIleIleGlyGluValProSerIle-230 |
| SEQ. ID. NO. 1232 | 242-LeuPheThrValSer-246 |
| SEQ. ID. NO. 1233 | 260-PheAspSerThrGlyThrLeu-266 |
| SEQ. ID. NO. 1234 | 342-LeuAlaLysSerValProAlaPheAlaThr-351 |
| SEQ. ID. NO. 1235 | 362-MetLeuArgSerAlaArgAspIle-369 |

Antigenic Index - Jameson-Wolf

| | |
|---|---|
| SEQ. ID. NO. 1236 | 1-MetAspThrSerLysGlnThrLeu-8 |
| SEQ. ID. NO. 1237 | 13-PheLysLeuLysAlaAsnGlyThrThrValArgThrGluLeu-26 |
| SEQ. ID. NO. 1238 | 125-LysValArgGluMetLeu-130 |
| SEQ. ID. NO. 1239 | 260-PheAspSerThrGly-264 |
| SEQ. ID. NO. 1240 | 277-ValAspGlyLysLeuProArgLeuLysArg-286 |
| SEQ. ID. NO. 1241 | 317-SerAlaGlyGlyArgThrGly-323 |
| SEQ. ID. NO. 1242 | 364-ArgSerAlaArgAspIleAspTrpAspAspMetThrGlu-376 |
| SEQ. ID. NO. 1243 | 410-LeuCysArgArgThrLysAspValProPro-419 |

Hydrophilic Regions - Hopp-Woods

| | |
|---|---|
| SEQ. ID. NO. 1244 | 1-MetAspThrSerLys-5 |
| SEQ. ID. NO. 1245 | 16-LysAlaAsnGlyThrThrValArgThrGluLeu-26 |
| SEQ. ID. NO. 1246 | 125-LysValArgGluMetLeu-130 |
| SEQ. ID. NO. 1247 | 279-GlyLysLeuProArgLeuLysArg-286 |
| SEQ. ID. NO. 1248 | 318-AlaGlyGlyArgThr-322 |
| SEQ. ID. NO. 1249 | 364-ArgSerAlaArgAspIleAspTrpAspAspMetThrGlu-376 |
| SEQ. ID. NO. 1250 | 410-LeuCysArgArgThrLysAspValPro-418 |

098-2
AMPHI Regions - AMPHI

| | |
|---|---|
| SEQ. ID. NO. 1251 | 29-AlaGluAlaGlyAspGlnPheValGlyAsp-38 |
| SEQ. ID. NO. 1252 | 110-ValGlyAspPhePheLysLeuAlaPhe-118 |
| SEQ. ID. NO. 1253 | 120-CysGlnIleGlnAsnValValThrAlaIleAlaGlnIleValAla-134 |
| SEQ. ID. NO. 1254 | 163-LeuSerSerPheSerHisGly-169 |

Antigenic Index - Jameson-Wolf

| | |
|---|---|
| SEQ. ID. NO. 1255 | 24-ValGlnGluAspAlaAlaGluAlaGlyAspGlnPheVal-36 |
| SEQ. ID. NO. 1256 | 68-MetGlyMetCysArg-72 |
| SEQ. ID. NO. 1257 | 78-PheAsnHisThrAspArgGlnAlaAla-86 |
| SEQ. ID. NO. 1258 | 136-ThrAlaAsnGlyThrGlnSerGlyIleThrGlyArgAsnAlaArgLysArgAsnGlyPhe-155 |
| SEQ. ID. NO. 1259 | 158-PheGluGlyArgGlyLeuSerSerPheSerHisGlyIle-170 |
| SEQ. ID. NO. 1260 | 180-ValPheArgArgProMetArgIleCys-188 |

Hydrophilic Regions - Hopp-Woods

| | |
|---|---|
| SEQ. ID. NO. 1261 | 24-ValGlnGluAspAlaAlaGluAlaGlyAsp-33 |
| SEQ. ID. NO. 1262 | 79-AsnHisThrAspArgGlnAla-85 |
| SEQ. ID. NO. 1263 | 144-IleThrGlyArgAsnAlaArgLysArgAsnGly-154 |
| SEQ. ID. NO. 1264 | 158-PheGluGlyArgGly-162 |
| SEQ. ID. NO. 1265 | 180-ValPheArgArgProMetArg-186 |

099 (delete this one--mistaken sequence)
AMPHI Regions - AMPHI

| | |
|---|---|
| SEQ. ID. NO. 1266 | 6-SerMetMetArgLeuProAspIle-13 |
| SEQ. ID. NO. 1267 | 47-AlaPheValGluPhePheGlyGluGly-55 |
| SEQ. ID. NO. 1268 | 102-LysLeuValGluThrTyrAlaLysThr-110 |
| SEQ. ID. NO. 1269 | 114-TrpAlaAspAlaLeuLysThrAla-121 |
| SEQ. ID. NO. 1270 | 135-ThrArgAsnMetAlaGlyProSerAsn-143 |
| SEQ. ID. NO. 1271 | 154-AlaAlaLysGlyLeuAlaLysProTyrGluGluProSerAspGly-168 |
| SEQ. ID. NO. 1272 | 178-AlaAlaIleThrSerCysThrAsnThrSerAsnProArgAsnVal-192 |
| SEQ. ID. NO. 1273 | 251-ThrCysAsnGlyMetSer-256 |
| SEQ. ID. NO. 1274 | 341-IleAspAlaValValAlaGluTyrValLysProGlnGlnPheArgAspValTyrVal-359 |
| SEQ. ID. NO. 1275 | 371-ProSerProLeuTyrAspTrpArg-378 |
| SEQ. ID. NO. 1276 | 381-SerThrTyrIleArg-385 |
| SEQ. ID. NO. 1277 | 398-ArgThrLeuArgGlyMetArgProLeu-406 |
| SEQ. ID. NO. 1278 | 443-AspPheAsnSerTyrAlaThr-449 |
| SEQ. ID. NO. 1279 | 468-PheAsnGluMetValLys-473 |
| SEQ. ID. NO. 1280 | 494-MetArgMetTrpGluAlaIleGluThrTyrMet-504 |
| SEQ. ID. NO. 1281 | 532-ArgLeuAlaGlyVal-536 |
| SEQ. ID. NO. 1282 | 539-IleValAlaGluGlyPheGluArgIleHisArgThrAsn-551 |
| SEQ. ID. NO. 1283 | 575-GlyThrGluThrTyr-579 |

Antigenic Index - Jameson-Wolf

| | |
|---|---|
| SEQ. ID. NO. 1284 | 17-GluLeuAsnGlyLysArgGlnAlaGly-25 |
| SEQ. ID. NO. 1285 | 38-PheLeuArgLysGluArgValVal-45 |
| SEQ. ID. NO. 1286 | 53-GlyGluGlyAlaArgSer-58 |
| SEQ. ID. NO. 1287 | 60-SerIleGlyAspArgAlaThr-66 |
| SEQ. ID. NO. 1288 | 70-MetThrProGluPhe-74 |
| SEQ. ID. NO. 1289 | 83-IleAspGluGlnThr-87 |

TABLE 1-continued

| SEQ. ID. NO. 1290 | 94-ThrGlyArgAspAspAlaGlnValLysLeu-103 |
| SEQ. ID. NO. 1291 | 133-SerValThrArgAsnMetAlaGlyProSerAsnProHis-145 |
| SEQ. ID. NO. 1292 | 157-GlyLeuAlaLysProTyrGluGluProSerAspGlyGlnMetProAspGly-173 |
| SEQ. ID. NO. 1293 | 183-CysThrAsnThrSerAsnProArgAsnVal-192 |
| SEQ. ID. NO. 1294 | 201-AsnAlaAsnArgLeuGlyLeuLysArgLysProTrpVal-213 |
| SEQ. ID. NO. 1295 | 216-SerPheAlaProGlySerLysValAla-224 |
| SEQ. ID. NO. 1296 | 235-ProGluMetGluLysLeu-240 |
| SEQ. ID. NO. 1297 | 251-ThrCysAsnGlyMetSerGlyAlaLeuAspProLysIleGlnLysGluIleIleAspArgAspLeuTyr-273 |
| SEQ. ID. NO. 1298 | 279-SerGlyAsnArgAsnPheAspGlyArgIleHisProTyrAlaLys-293 |
| SEQ. ID. NO. 1299 | 312-IleArgPheAspIleGluAsnAspVal-320 |
| SEQ. ID. NO. 1300 | 322-GlyValAlaAspGlyLysGluIleArgLeuLysAsp-333 |
| SEQ. ID. NO. 1301 | 335-TrpProAlaAspGluGluIleAspAlaVal-344 |
| SEQ. ID. NO. 1302 | 348-TyrValLysProGlnGlnPheArgAspVal-357 |
| SEQ. ID. NO. 1303 | 363-AspThrGlyThrAlaGlnLysAlaProSerProLeuTyrAspTrpArgProMetSerThrTyrIleArgArgProProTyrTrp-390 |
| SEQ. ID. NO. 1304 | 394-LeuAlaGlyGluArgThrLeuArgGlyMetArg-404 |
| SEQ. ID. NO. 1305 | 409-LeuProAspAsnIleThrThrAspHisLeuSerProSerAsn-422 |
| SEQ. ID. NO. 1306 | 438-GlyLeuProGluGluAspPheAsnSerTyrAlaThrHisArgGlyAspHisLeuThr-456 |
| SEQ. ID. NO. 1307 | 463-AlaAsnProLysLeuPhe-468 |
| SEQ. ID. NO. 1308 | 471-MetValLysAsnGluAspGlySerValArgGlnGlySerPheAlaArgValGluProGluGlyGluThr-493 |
| SEQ. ID. NO. 1309 | 503-TyrMetAsnArgLysGlnPro-509 |
| SEQ. ID. NO. 1310 | 516-AlaAspTyrGlyGlnGlySerSerArgAspTrpAlaAlaLysGlyValArg-532 |
| SEQ. ID. NO. 1311 | 543-GlyPheGluArgIleHisArgThrAsnLeu-552 |
| SEQ. ID. NO. 1312 | 562-PheLysProAspThrAsnArgHis-569 |
| SEQ. ID. NO. 1313 | 571-LeuGlnLeuAspGlyThrGluThrTyrAspValValGlyGluArgThrProArgCysAspLeu-591 |
| SEQ. ID. NO. 1314 | 595-IleHisArgLysAsnGlyGluThrValGlu-604 |
| SEQ. ID. NO. 1315 | 612-AspThrAlaGluGlu-616 |
| Hydrophilic Regions - Hopp-Woods | |
| SEQ. ID. NO. 1316 | 18-LeuAsnGlyLysArgGlnAlaGly-25 |
| SEQ. ID. NO. 1317 | 38-PheLeuArgGlyLysGluArgValVal-45 |
| SEQ. ID. NO. 1318 | 53-GlyGluGlyAlaArg-57 |
| SEQ. ID. NO. 1319 | 60-SerIleGlyAspArgAlaThr-66 |
| SEQ. ID. NO. 1320 | 83-IleAspGluGlnThr-87 |
| SEQ. ID. NO. 1321 | 94-ThrGlyArgAspAspAlaGlnValLysLeu-103 |
| SEQ. ID. NO. 1322 | 157-GlyLeuAlaLysProTyrGluGluProSerAspGlyGlnMetProAsp-172 |
| SEQ. ID. NO. 1323 | 205-LeuGlyLeuLysArgLysProTrpVal-213 |
| SEQ. ID. NO. 1324 | 235-ProGluMetGluLysLeu-240 |
| SEQ. ID. NO. 1325 | 259-LeuAspProLysIleGlnLysGluIleIleAspArgAspLeuTyr-273 |
| SEQ. ID. NO. 1326 | 282-ArgAsnPheAspGlyArgIle-288 |
| SEQ. ID. NO. 1327 | 312-IleArgPheAspIleGluAsnAspVal-320 |
| SEQ. ID. NO. 1328 | 324-AlaAspGlyLysGluIleArgLeuLysAsp-333 |
| SEQ. ID. NO. 1329 | 335-TrpProAlaAspGluGluIleAspAlaVal-344 |
| SEQ. ID. NO. 1330 | 366-ThrAlaGlnLysAlaPro-371 |
| SEQ. ID. NO. 1331 | 394-LeuAlaGlyGluArgThrLeuArgGlyMetArg-404 |
| SEQ. ID. NO. 1332 | 438-GlyLeuProGluGluAspPheAsn-445 |
| SEQ. ID. NO. 1333 | 450-HisArgGlyAspHis-454 |
| SEQ. ID. NO. 1334 | 471-MetValLysAsnGluAspGlySerValArg-480 |
| SEQ. ID. NO. 1335 | 485-AlaArgValGluProGluGlyGluThr-493 |
| SEQ. ID. NO. 1336 | 503-TyrMetAsnArgLysGlnPro-509 |
| SEQ. ID. NO. 1337 | 518-TyrGlyGlnGlySerSerArgAspTrpAlaAlaLysGlyValArg-532 |
| SEQ. ID. NO. 1338 | 543-GlyPheGluArgIleHisArg-549 |
| SEQ. ID. NO. 1339 | 562-PheLysProAspThrAsnArgHis-569 |
| SEQ. ID. NO. 1340 | 574-AspGlyThrGluThr-578 |
| SEQ. ID. NO. 1341 | 580-AspValValGlyGluArgThrProArgCysAsp-590 |
| SEQ. ID. NO. 1342 | 596-HisArgLysAsnGlyGluThrValGlu-604 |
| SEQ. ID. NO. 1343 | 612-AspThrAlaGluGlu-616 |
| 099-2 | |
| AMPHI Regions - AMPHI | |
| SEQ. ID. NO. 1344 | 30-ProGlySerTyrAspLysLeuPro-37 |
| SEQ. ID. NO. 1345 | 57-ProThrLeuGlnSerTrpLeuGlyGln-65 |
| SEQ. ID. NO. 1346 | 91-ThrAlaLeuValAspLeuAlaGlyLeuArgAsp-101 |
| SEQ. ID. NO. 1347 | 106-LysGlyGlyAspProAlaLysValAsn-114 |
| SEQ. ID. NO. 1348 | 138-AlaPheArgLysAsn-142 |
| SEQ. ID. NO. 1349 | 212-AspSerLeuGlyVal-216 |
| SEQ. ID. NO. 1350 | 234-AlaSerMetMetArgLeuProAspIle-242 |
| SEQ. ID. NO. 1351 | 276-AlaPheValGluPhePheGlyGluGly-284 |
| SEQ. ID. NO. 1352 | 331-LysLeuValGluThrTyrAlaLysThr-339 |
| SEQ. ID. NO. 1353 | 343-TrpAlaAspAlaLeuLysThrAla-350 |
| SEQ. ID. NO. 1354 | 364-ThrArgAsnMetAlaGlyProSerAsn-372 |
| SEQ. ID. NO. 1355 | 383-AlaAlaLysGlyLeuAlaLysProTyrGluGluProSerAspGly-397 |
| SEQ. ID. NO. 1356 | 407-AlaAlaIleThrSerCysThrAsnThrSerAsnProArgAsnVal-421 |
| SEQ. ID. NO. 1357 | 480-ThrCysAsnGlyMetSer-485 |
| SEQ. ID. NO. 1358 | 570-IleAspAlaValValAlaGluTyrValLysProGlnGlnPheArgAspValTyrVal-588 |
| SEQ. ID. NO. 1359 | 600-ProSerProLeuTyrAspTrpArg-607 |
| SEQ. ID. NO. 1360 | 610-SerThrTyrIleArg-614 |
| SEQ. ID. NO. 1361 | 627-ArgThrLeuArgGlyMetArgProLeu-635 |
| SEQ. ID. NO. 1362 | 672-AspPheAsnSerTyrAlaThr-678 |
| SEQ. ID. NO. 1363 | 697-PheAsnGluMetValLys-702 |
| SEQ. ID. NO. 1364 | 723-MetArgMetTrpGluAlaIleGluThrTyrMet-733 |
| SEQ. ID. NO. 1365 | 761-ArgLeuAlaGlyVal-765 |
| SEQ. ID. NO. 1366 | 768-IleValAlaGluGlyPheGluArgIleHisArgThrAsn-780 |

TABLE 1-continued

| | |
|---|---|
| SEQ. ID. NO. 1367 | 804-GlyThrGluThrTyr-808 |
| Antigenic Index - Jameson-Wolf | |
| SEQ. ID. NO. 1368 | 3-AlaAsnGlnArgTyrArgLysProLeuProGlyThrAspLeuGluTyrTyrAsp-20 |
| SEQ. ID. NO. 1369 | 22-ArgAlaAlaCysGluAspIleLysProGlySerTyrAspLysLeuProTyr-38 |
| SEQ. ID. NO. 1370 | 47-LeuValAsnArgAlaAspLysValAspLeuPro-57 |
| SEQ. ID. NO. 1371 | 67-IleGluGlyLysGlnGluIle-73 |
| SEQ. ID. NO. 1372 | 97-AlaGlyLeuArgAspAlaIleAlaGluLysGlyGlyAspProAlaLys-112 |
| SEQ. ID. NO. 1373 | 131-CysGlyGlyTyrAspProAspAlaPheArgLysAsnArgGluIleGluAspArgArgAsnGluAspArgPhe-154 |
| SEQ. ID. NO. 1374 | 162-ThrAlaPheGluAsn-166 |
| SEQ. ID. NO. 1375 | 181-AsnLeuGluLysMetSer-186 |
| SEQ. ID. NO. 1376 | 200-ThrCysValGlyThrAspSerHisThrProHisValAspSer-213 |
| SEQ. ID. NO. 1377 | 222-GlyGlyLeuGluAlaGluThr-228 |
| SEQ. ID. NO. 1378 | 246-GluLeuAsnGlyLysArgGlnAlaGly-254 |
| SEQ. ID. NO. 1379 | 267-PheLeuArgLysGluArgValVal-274 |
| SEQ. ID. NO. 1380 | 282-GlyGluGlyAlaArgSer-287 |
| SEQ. ID. NO. 1381 | 289-SerIleGlyAspArgAlaThr-295 |
| SEQ. ID. NO. 1382 | 299-MetThrProGluPhe-303 |
| SEQ. ID. NO. 1383 | 312-IleAspGluGlnThr-316 |
| SEQ. ID. NO. 1384 | 323-ThrGlyArgAspAspAlaGlnValLysLeu-332 |
| SEQ. ID. NO. 1385 | 362-SerValThrArgAsnMetAlaGlyProSerAsnProHis-374 |
| SEQ. ID. NO. 1386 | 386-GlyLeuAlaLysProTyrGluGluProSerAspGlyGlnMetProAspGly-402 |
| SEQ. ID. NO. 1387 | 412-CysThrAsnThrSerAsnProArgAsnVal-421 |
| SEQ. ID. NO. 1388 | 430-AsnAlaAsnArgLeuGlyLeuLysArgLysProTrpVal-442 |
| SEQ. ID. NO. 1389 | 445-SerPheAlaProGlySerLysValAla-453 |
| SEQ. ID. NO. 1390 | 464-ProGluMetGluLysLeu-469 |
| SEQ. ID. NO. 1391 | 480-ThrCysAsnGlyMetSerGlyAlaLeuAspProLysIleGlnLysGluIleIleAspArgAspLeuTyr-502 |
| SEQ. ID. NO. 1392 | 508-SerGlyAsnArgAsnPheAspGlyArgIleHisProTyrAlaLys-522 |
| SEQ. ID. NO. 1393 | 541-IleArgPheAspIleGluAsnAspVal-549 |
| SEQ. ID. NO. 1394 | 551-GlyValAlaAspGlyLysGluIleArgLeuLysAsp-562 |
| SEQ. ID. NO. 1395 | 564-TrpProAlaAspGluGluIleAspAlaVal-573 |
| SEQ. ID. NO. 1396 | 577-TyrValLysProGlnGlnPheArgAspVal-586 |
| SEQ. ID. NO. 1397 | 592-AspThrGlyThrAlaGlnLysAlaProSerProLeuTyrAspTrpArgProMetSerThrTyrIleArgArgProProTyrTrp-619 |
| SEQ. ID. NO. 1398 | 623-LeuAlaGlyGluArgThrLeuArgGlyMetArg-633 |
| SEQ. ID. NO. 1399 | 638-LeuProAspAsnIleThrThrAspHisLeuSerProSerAsn-651 |
| SEQ. ID. NO. 1400 | 667-GlyLeuProGluGluAspPheAsnSerTyrAlaThrHisArgGlyAspHisLeuThr-685 |
| SEQ. ID. NO. 1401 | 692-AlaAsnProLysLeuPhe-697 |
| SEQ. ID. NO. 1402 | 700-MetValLysAsnGluAspGlySerValArgGlnGlySerPheAlaArgValGluProGluGlyGluThr-722 |
| SEQ. ID. NO. 1403 | 732-TyrMetAsnArgLysGlnPro-738 |
| SEQ. ID. NO. 1404 | 745-AlaAspTyrGlyGlnGlySerSerArgAspTrpAlaAlaLysGlyValArg-761 |
| SEQ. ID. NO. 1405 | 772-GlyPheGluArgIleHisArgThrAsnLeu-781 |
| SEQ. ID. NO. 1406 | 791-PheLysProAspThrAsnArgHis-798 |
| SEQ. ID. NO. 1407 | 800-LeuGlnLeuAspGlyThrGluThrTyrAspValValGlyGluArgThrProArgCysAspLeu-820 |
| SEQ. ID. NO. 1408 | 824-IleHisArgLysAsnGlyGluThrValGlu-833 |
| SEQ. ID. NO. 1409 | 841-AspThrAlaGluGlu-845 |
| Hydrophilic Regions - Hopp-Woods | |
| SEQ. ID. NO. 1410 | 5-GlnArgTyrArgLysProLeuPro-12 |
| SEQ. ID. NO. 1411 | 22-ArgAlaAlaCysGluAspIleLysProGlySerTyrAsp-34 |
| SEQ. ID. NO. 1412 | 47-LeuValAsnArgAlaAspLysValAspLeu-56 |
| SEQ. ID. NO. 1413 | 67-IleGluGlyLysGlnGluIle-73 |
| SEQ. ID. NO. 1414 | 97-AlaGlyLeuArgAspAlaIleAlaGluLysGlyGlyAspProAlaLys-112 |
| SEQ. ID. NO. 1415 | 132-GlyGlyTyrAspProAspAlaPheArgLysAsnArgGluIleGluAspArgArgAsnGluAspArgPhe-154 |
| SEQ. ID. NO. 1416 | 181-AsnLeuGluLysMetSer-186 |
| SEQ. ID. NO. 1417 | 205-AspSerHisThrProHis-210 |
| SEQ. ID. NO. 1418 | 224-LeuGluAlaGluThr-228 |
| SEQ. ID. NO. 1419 | 247-LeuAsnGlyLysArgGlnAlaGly-254 |
| SEQ. ID. NO. 1420 | 267-PheLeuArgLysGluArgValVal-274 |
| SEQ. ID. NO. 1421 | 282-GlyGluGlyAlaArg-286 |
| SEQ. ID. NO. 1422 | 289-SerIleGlyAspArgAlaThr-295 |
| SEQ. ID. NO. 1423 | 312-IleAspGluGlnThr-316 |
| SEQ. ID. NO. 1424 | 323-ThrGlyArgAspAspAlaGlnValLysLeu-332 |
| SEQ. ID. NO. 1425 | 386-GlyLeuAlaLysProTyrGluGluProSerAspGlyGlnMetProAsp-401 |
| SEQ. ID. NO. 1426 | 434-LeuGlyLeuLysArgLysProTrpVal-442 |
| SEQ. ID. NO. 1427 | 464-ProGluMetGluLysLeu-469 |
| SEQ. ID. NO. 1428 | 488-LeuAspProLysIleGlnLysGluIleIleAspArgAspLeuTyr-502 |
| SEQ. ID. NO. 1429 | 511-ArgAsnPheAspGlyArgIle-517 |
| SEQ. ID. NO. 1430 | 541-IleArgPheAspIleGluAsnAspVal-549 |
| SEQ. ID. NO. 1431 | 553-AlaAspGlyLysGluIleArgLeuLysAsp-562 |
| SEQ. ID. NO. 1432 | 564-TrpProAlaAspGluGluIleAspAlaVal-573 |
| SEQ. ID. NO. 1433 | 595-ThrAlaGlnLysAlaPro-600 |
| SEQ. ID. NO. 1434 | 623-LeuAlaGlyGluArgThrLeuArgGlyMetArg-633 |
| SEQ. ID. NO. 1435 | 667-GlyLeuProGluGluAspPheAsn-674 |
| SEQ. ID. NO. 1436 | 679-HisArgGlyAspHisLeuThr-685 |
| SEQ. ID. NO. 1437 | 700-MetValLysAsnGluAspGlySerValArg-709 |
| SEQ. ID. NO. 1438 | 714-AlaArgValGluProGluGlyGluThr-722 |
| SEQ. ID. NO. 1439 | 732-TyrMetAsnArgLysGlnPro-738 |
| SEQ. ID. NO. 1440 | 747-TyrGlyGlnGlySerSerArgAspTrpAlaAlaLysGlyValArg-761 |
| SEQ. ID. NO. 1441 | 772-GlyPheGluArgIleHisArg-778 |
| SEQ. ID. NO. 1442 | 791-PheLysProAspThrAsnArgHis-798 |
| SEQ. ID. NO. 1443 | 803-AspGlyThrGluThr-807 |
| SEQ. ID. NO. 1444 | 809-AspValValGlyGluArgThrProArgCysAsp-819 |

TABLE 1-continued

| | |
|---|---|
| SEQ. ID. NO. 1445 | 824-IleHisArgLysAsnGlyGluThrValGlu-833 |
| SEQ. ID. NO. 1446 | 841-AspThrAlaGluGlu-845 |
| 102 | |
| AMPHI Regions - AMPHI | |
| SEQ. ID. NO. 1447 | 42-ValLeuLeuTyrThrTrpPheSerMetLeu-51 |
| SEQ. ID. NO. 1448 | 67-GlyAlaSerPheAspThrMetValLysAspLeuLeuGlyArgGlyTrpAsnIleIleAsnGlyIleAla-89 |
| SEQ. ID. NO. 1449 | 109-ThrAlaLysGlyLeuGlySerAlaAla-117 |
| SEQ. ID. NO. 1450 | 128-LeuValPhePheGlyIleLeuAlaPheCys-137 |
| SEQ. ID. NO. 1451 | 144-LeuValAspArgPheThrGlyValLeu-152 |
| SEQ. ID. NO. 1452 | 155-GlyMetValLeuThr-159 |
| SEQ. ID. NO. 1453 | 207-AsnValSerSerLeuLeuLysTyrPheLys-216 |
| SEQ. ID. NO. 1454 | 221-LysValAlaLysSerIle-226 |
| SEQ. ID. NO. 1455 | 265-ValLeuIleGluThrLeuSerLysPheAlaGlnThrGlyAsnMetAspLysIleLeuSerLeuPheSerTyrMetAla-290 |
| SEQ. ID. NO. 1456 | 303-PheAspTyrIleAlaAspIlePheLysTrpAsnAsp-314 |
| SEQ. ID. NO. 1457 | 341-PheValThrAlaIleGlyTyr-347 |
| SEQ. ID. NO. 1458 | 352-AlaThrValTrpThrGlyIleIlePro-360 |
| SEQ. ID. NO. 1459 | 374-GlyLysThrTyrLysVal-379 |
| Antigenic Index - Jameson-Wolf | |
| SEQ. ID. NO. 1460 | 1-MetProAsnLysThrProSer-7 |
| SEQ. ID. NO. 1461 | 64-TyrProHisGlyAla-68 |
| SEQ. ID. NO. 1462 | 77-LeuLeuGlyArgGly-81 |
| SEQ. ID. NO. 1463 | 107-AspLeuThrAlaLysGlyLeuGlySerAlaAlaGlyGly-119 |
| SEQ. ID. NO. 1464 | 169-AlaAspAlaLysProSerVal-175 |
| SEQ. ID. NO. 1465 | 179-ThrGlnAlaProAlaGlyThr-185 |
| SEQ. ID. NO. 1466 | 214-TyrPheLysGlyAspAlaProLysValAla-223 |
| SEQ. ID. NO. 1467 | 246-GlyAsnLeuProArgAsnGluPhe-253 |
| SEQ. ID. NO. 1468 | 274-AlaGlnThrGlyAsnMetAspLysIle-282 |
| SEQ. ID. NO. 1469 | 311-LysTrpAsnAspSerIleSerGlyArgThrLysThr-322 |
| SEQ. ID. NO. 1470 | 364-LeuTyrArgSerArgLysLysPheGlyAlaGlyLysThrTyrLysVal-379 |
| Hydrophilic Regions - Hopp-Woods | |
| SEQ. ID. NO. 1471 | 1-MetProAsnLysThr-5 |
| SEQ. ID. NO. 1472 | 169-AlaAspAlaLysPro-173 |
| SEQ. ID. NO. 1473 | 215-PheLysGlyAspAlaProLysValAla-223 |
| SEQ. ID. NO. 1474 | 248-LeuProArgAsnGluPhe-253 |
| SEQ. ID. NO. 1475 | 277-GlyAsnMetAspLys-281 |
| SEQ. ID. NO. 1476 | 316-IleSerGlyArgThrLysThr-322 |
| SEQ. ID. NO. 1477 | 366-ArgSerArgLysLysPheGlyAla-373 |
| 105-2 | |
| AMPHI Regions - AMPHI | |
| SEQ. ID. NO. 1478 | 11-TrpIleGlyLeuGly-15 |
| SEQ. ID. NO. 1479 | 22-ValThrArgLeuLeuAsp-27 |
| SEQ. ID. NO. 1480 | 51-LysValTyrGlyAsnThrAlaGluLeu-59 |
| SEQ. ID. NO. 1481 | 74-AlaAlaValCysAspIleLeuAsnGlyValArgAspGlyLeu-87 |
| SEQ. ID. NO. 1482 | 97-ThrIleSerProThr-101 |
| SEQ. ID. NO. 1483 | 110-ValGluAlaAlaGlyGlyGlnPheAlaGluAlaProVal-122 |
| SEQ. ID. NO. 1484 | 143-AlaValLeuAsnProLeuGlnLysIlePheSer-153 |
| SEQ. ID. NO. 1485 | 162-PheGlyAspValGlyLysGlySer-169 |
| SEQ. ID. NO. 1486 | 176-AsnSerLeuLeuGlyIlePheGlyGluAlaTyr-186 |
| SEQ. ID. NO. 1487 | 203-IleValGluAlaIleGlyXxxSerAla-211 |
| SEQ. ID. NO. 1488 | 249-LeuGluGlnAlaGlyAsnThrLeuProAlaValGlu-260 |
| SEQ. ID. NO. 1489 | 263-AlaAlaSerTyrArgLysAlaValGluAla-272 |
| Antigenic Index - Jameson-Wolf | |
| SEQ. ID. NO. 1490 | 25-LeuLeuAspGlyGlyIleGlu-31 |
| SEQ. ID. NO. 1491 | 34-ValTyrAsnArgSerProAspLysThrAlaProIleSerAlaLysGlyAlaLysValTyrGlyAsnThr-56 |
| SEQ. ID. NO. 1492 | 81-AsnGlyValArgAspGlyLeuAla-88 |
| SEQ. ID. NO. 1493 | 96-SerThrIleSerProThrGluAsnLeuAla-105 |
| SEQ. ID. NO. 1494 | 121-ProValSerGlySerValGlyProAlaThr-130 |
| SEQ. ID. NO. 1495 | 139-GlyGlySerGluAla-143 |
| SEQ. ID. NO. 1496 | 155-ValGlyLysLysThrPheHisPheGlyAspValGlyLysGlySerGly-170 |
| SEQ. ID. NO. 1497 | 196-PheGlyIleAspThrAspThrIleVal-204 |
| SEQ. ID. NO. 1498 | 211-AlaMetAspSerProMetPheGlnThrLysLysSerLeuTrpAlaAsnArgGluPheProPro-231 |
| SEQ. ID. NO. 1499 | 237-HisAlaSerLysAspLeuAsnLeuAlaValLysGluLeuGluGlnAlaGlyAsnThrLeuPro-257 |
| SEQ. ID. NO. 1500 | 264-AlaSerTyrArgLysAlaValGluAlaGlyTyrGlyGluGlnAspValSerGly-281 |
| Hydrophilic Regions - Hopp-Woods | |
| SEQ. ID. NO. 1501 | 25-LeuLeuAspGlyGlyIle-30 |
| SEQ. ID. NO. 1502 | 37-ArgSerProAspLysThrAlaProIleSerAlaLysGlyAlaLys-51 |
| SEQ. ID. NO. 1503 | 81-AsnGlyValArgAspGlyLeuAla-88 |
| SEQ. ID. NO. 1504 | 164-AspValGlyLysGlySerGly-170 |
| SEQ. ID. NO. 1505 | 196-PheGlyIleAspThrAspThrIle-203 |
| SEQ. ID. NO. 1506 | 218-GlnThrLysLysSerLeuTrpAla-225 |
| SEQ. ID. NO. 1507 | 237-HisAlaSerLysAspLeuAsnLeuAlaValLysGluLeuGluGlnAlaGly-253 |
| SEQ. ID. NO. 1508 | 265-SerTyrArgLysAlaValGlu-271 |
| SEQ. ID. NO. 1509 | 273-GlyTyrGlyGluGlnAspVal-279 |
| 109-2 | |
| AMPHI Regions - AMPHI | |
| SEQ. ID. NO. 1510 | 6-GlyThrTyrArgAspLeuHisArgProAlaSerGlu-17 |
| SEQ. ID. NO. 1511 | 53-LeuIleProAlaMetAlaGlyThrIleGly-62 |
| SEQ. ID. NO. 1512 | 69-AlaValAlaAlaAlaPhe-74 |
| SEQ. ID. NO. 1513 | 145-GlyLeuLeuMetAla-149 |
| SEQ. ID. NO. 1514 | 156-IleMetAlaLysLeuThrSer-162 |

TABLE 1-continued

| | |
|---|---|
| SEQ. ID. NO. 1515 | 177-GlyThrThrGlyGlnValLysLysLeuPheSerTrpAlaGly-190 |
| SEQ. ID. NO. 1516 | 207-ValMetTyrAlaLeuLeuGluHisTrpLysLysArgTrpLeu-220 |
| SEQ. ID. NO. 1517 | 222-ValProLeuGlyCysLeuIleAla-229 |
| SEQ. ID. NO. 1518 | 294-HisGlnValPheGlnLysIle-300 |
| SEQ. ID. NO. 1519 | 326-ValGlySerIleLeuGly-331 |
| SEQ. ID. NO. 1520 | 336-ThrSerSerTrpGlyThr-341 |
| SEQ. ID. NO. 1521 | 471-AlaValGlyMetLeuProGlyIleProProPheLeuGluHisPheLysSerLeu-488 |
| Antigenic Index - Jameson-Wolf | |
| SEQ. ID. NO. 1522 | 1-MetGluLysHisAsnGlyThrTyrArgAspLeuHisArgProAlaSer-16 |
| SEQ. ID. NO. 1523 | 18-PheAlaThrArgAspGluTyrLeuGlu-26 |
| SEQ. ID. NO. 1524 | 32-MetGlnProLysArgTrpArgProAsnLeuProPheArgAspTyrArgPheGluTrp-50 |
| SEQ. ID. NO. 1525 | 78-LeuGlyLeuProAsp-82 |
| SEQ. ID. NO. 1526 | 109-ProGlyAlaAsnLeuProGlyThrHis-117 |
| SEQ. ID. NO. 1527 | 160-LeuThrSerAsnGlyVal-165 |
| SEQ. ID. NO. 1528 | 179-ThrGlyGlnValLysLys-184 |
| SEQ. ID. NO. 1529 | 259-GluAsnSerGlyTrp-263 |
| SEQ. ID. NO. 1530 | 301-SerTyrProGluLysThrAspLysVal-309 |
| SEQ. ID. NO. 1531 | 312-AsnIleAspAspThrMetThr-318 |
| SEQ. ID. NO. 1532 | 348-IleAlaLysArgProIleProGlyGly-356 |
| SEQ. ID. NO. 1533 | 398-AlaGlyMetGluMetThrArgLysGlyLysThrThrGln-410 |
| SEQ. ID. NO. 1534 | 441-GlyCysLysGluArgSerAla-447 |
| Hydrophilic Regions - Hopp-Woods | |
| SEQ. ID. NO. 1535 | 1-MetGluLysHisAsnGlyThrTyrArgAspLeuHisArgProAlaSer-16 |
| SEQ. ID. NO. 1536 | 18-PheAlaThrArgAspGluTyrLeuGlu-26 |
| SEQ. ID. NO. 1537 | 35-LysArgTrpArgPro-39 |
| SEQ. ID. NO. 1538 | 44-ArgAspTyrArgPheGluTrp-50 |
| SEQ. ID. NO. 1539 | 180-GlyGlnValLysLys-184 |
| SEQ. ID. NO. 1540 | 301-SerTyrProGluLysThrAspLysVal-309 |
| SEQ. ID. NO. 1541 | 313-IleAspAspThrMetThr-318 |
| SEQ. ID. NO. 1542 | 348-IleAlaLysArgProIlePro-354 |
| SEQ. ID. NO. 1543 | 398-AlaGlyMetGluMetThrArgLysGlyLysThrThrGln-410 |
| SEQ. ID. NO. 1544 | 441-GlyCysLysGluArgSerAla-447 |
| 111-2 | |
| AMPHI Regions - AMPHI | |
| SEQ. ID. NO. 1545 | 6-ArgLeuProAsnPheIleArgVal-13 |
| SEQ. ID. NO. 1546 | 27-SerGluGlnThrTyrThrValLys-48 |
| SEQ. ID. NO. 1547 | 58-ProSerProAlaGluIleGlnLysArgIleAspAspAlaLeuLysGluValAsnArgGlnMetSerPheAsnGlnHisThrAlaGlyLeuArgIleSer-102 |
| SEQ. ID. NO. 1548 | 128-GlyProLeuValAsnLeuTrp-134 |
| SEQ. ID. NO. 1549 | 151-IleLysGlnAlaAlaSerTyrThrGlyAspTyrAlaSerLeu-174 |
| SEQ. ID. NO. 1550 | 183-LeuAspLeuSerSerIleAlaLys-190 |
| SEQ. ID. NO. 1551 | 198-AlaGlyGluTyrLeuValGluIleGlyGly-215 |
| SEQ. ID. NO. 1552 | 237-AsnIleValGlnLeuSerHisIle-276 |
| SEQ. ID. NO. 1553 | 314-GluThrGluAlaLeu-318 |
| Antigenic Index - Jameson-Wolf | |
| SEQ. ID. NO. 1554 | 1-MetProSerGluThrArgLeuProAsnPhe-10 |
| SEQ. ID. NO. 1555 | CysSerGluGlnThrAla-31 |
| SEQ. ID. NO. 1556 | 37-GlnGlyGluThrMetGlyTyr-45 |
| SEQ. ID. NO. 1557 | 49-TyrLeuSerAsnAsnArgAspLysLeuProSerProAlaGluIleGlnLysArgIleAspAspAlaLeuLysGluValAsnArgGlnMetSerThrTyrGln<br>ProAspSerGluIleSerArgPheAsnGlnHisThrAlaGlyLysProLeuArgIleSerSerAspPhe-105 |
| SEQ. ID. NO. 1558 | 111-GluAlaValArgLeuAsnArg-117 |
| SEQ. ID. NO. 1559 | GlyPheGlyProAspLysSerValThrArgGluProSerProGluGlnIleLysGlnThrGly-159 |
| SEQ. ID. NO. 1560 | 163-IleIleLeuLysGlnGlyLysAspTyrAlaSerLeuSerLysThrHisProLysAla-181 |
| SEQ. ID. NO. 1561 | 187-SerPheGlyValAspLysValAlaGlyGluLeuGluLysTyrGly-205 |
| SEQ. ID. NO. 1562 | 213-IleGlyGlyGluLeuHisGlyLysGlyLysAsnAlaArgGlyProTrpArgIleGlyIleGluGlnProAsnIle-238 |
| SEQ. ID. NO. 1563 | 240-GlnGlyGlyAsnLeuAsnAsnArgSerLeuAlaThrSerGlyAspTyrArg-262 |
| SEQ. ID. NO. 1564 | 264-PheHisValAspLysAsnGlyLysArgLeuSerIleAsnProAsnAsnLysArgProIleSerAlaMetThrAlaAspGlyLeuSer-306 |
| SEQ. ID. NO. 1565 | 314-GluThrGluAlaLeuLysLeuAlaGluArgGluLysLeu-326 |
| SEQ. ID. NO. 1566 | 332-ValArgAspLysGlyGlyTyrArgMetSerSerGluPheGluLysLeuLeuArg-351 |
| Hydrophilic Regions - Hopp-Woods | |
| SEQ. ID. NO. 1567 | 1-MetProSerGluThrArgLeu-7 |
| SEQ. ID. NO. 1568 | 26-CysSerGluGlnThrAlaThrMet-41 |
| SEQ. ID. NO. 1569 | 51-SerAsnAsnArgAspLysLeuProSer-59 |
| SEQ. ID. NO. 1570 | 61-AlaGluIleGlnLysArgIleAspAspAlaLeuLysGluValAsnArgGlnGlnProAspSerGluIleSerArg-89 |
| SEQ. ID. NO. 1571 | 97-LysProLeuArgIleSerSer-103 |
| SEQ. ID. NO. 1572 | 111-GluAlaValArgLeuAsnArg-117 |
| SEQ. ID. NO. 1573 | 137-GlyProAspLysSerValThrArgGluProSerProGluGlnIleLysGln-153 |
| SEQ. ID. NO. 1574 | 163-IleIleLeuLysGlnGlyLysAspTyrAlaSer-173 |
| SEQ. ID. NO. 1575 | 175-SerLysThrHisPro-179 |
| SEQ. ID. NO. 1576 | 196-LysValAlaGlyGluLeuGluLysTyrGly-205 |
| SEQ. ID. NO. 1577 | 217-LeuHisGlyLysGlyLysAsnAlaArgGlyGluProTrp-229 |
| SEQ. ID. NO. 1578 | 267-AspLysAsnGlyLysArgLeuSerProAsnAsnLysArgProIle-285 |
| SEQ. ID. NO. 1579 | 299-AlaMetThrGlyLeuGluThrGluAlaLeuLysLeuAlaGluArgGluLysLeu-326 |
| SEQ. ID. NO. 1580 | 332-ValArgAspLysGlyGlyTyr-338 |
| SEQ. ID. NO. 1581 | 344-SerGluPheGluLysLeuLeuArg-351 |
| 117-1 | |
| AMPHI Regions - AMPHI | |
| SEQ. ID. NO. 1582 | 6-ProIleGlnAspThrGlnSerAla-13 |
| SEQ. ID. NO. 1583 | 15-LeuGlnGluLeuArgGluTrpPheAspSerTyrCysAlaThrPro-55 |
| SEQ. ID. NO. 1584 | 57-GlyGluProLeuProAspHisHisGluLeuAspLeuLeu-77 |
| SEQ. ID. NO. 1585 | 79-AspAlaValAlaAlaThrLeuLeuAlaAspIleGlyArgTyr-92 |

TABLE 1-continued

| | |
|---|---|
| SEQ. ID. NO. 1586 | 94-ProAspTrpLeuValSerCysAsnSerThrValAlaGluLeuValLysGlyValAspGluValGlnLysLeuThrHisPheAlaArgValAspSerLeuGlnAlaGluThrLysMetLeuLeuAlaMet-150 |
| SEQ. ID. NO. 1587 | 170-PheLeuSerAsnAlaProAspSerProGluLysAspIlePhe-191 |
| SEQ. ID. NO. 1588 | 216-LysProGluLysTyrArgArgLeuGluTyrIleGluAsnPheLeuAsnIleLeuArg-246 |
| SEQ. ID. NO. 1589 | 260-GlyArgProLysHisIleTyrSerIleTyrLys-270 |
| SEQ. ID. NO. 1590 | 282-LeuPheAspIleArg-286 |
| SEQ. ID. NO. 1591 | 290-IleLeuValAspThrValProGluCysTyrThrThrLeuGlyIleValHisSerLeuTrpGlnProIleProGlyGluPheAspAspTyrIleAla-321 |
| SEQ. ID. NO. 1592 | 327-GlyTyrLysSerLeuHisThr-333 |
| SEQ. ID. NO. 1593 | 351-AspMetHisGlnPheAsnGluPheGlyValAla-361 |
| SEQ. ID. NO. 1594 | 385-GlnLeuLeuAspTrp-389 |
| SEQ. ID. NO. 1595 | 412-AspThrHisGlyLysValHisSerSerIleGlyAspArgLeuGluAsn-465 |
| SEQ. ID. NO. 1596 | 485-TyrGluLysAlaIleGlyLysIleArgAlaTyrGlnGlnAsnAlaAsp-508 |
| SEQ. ID. NO. 1597 | 510-ValArgGluGlnLeuAlaLysLeuGlnGluLeuAlaGluGlyTyrLysLysProGluAspLeuTyrThrAsnArgAlaIleGlnLysAlaCysGlyThrLeuAsnGluProPro-571 |
| SEQ. ID. NO. 1598 | 585-LysIleLysLysGlyGlyMetThrThrLeuAlaLysCysCysLysProAlaAspAspIleIleGly-620 |
| SEQ. ID. NO. 1599 | 636-ProSerPheGlnHisLeuAlaGluHisAlaProGluLysValLeuAspAlaLeuGlnGlu-659 |
| SEQ. ID. NO. 1600 | 679-ArgAspValSerAspAla-684 |
| SEQ. ID. NO. 1601 | 714-GlnValAsnAspLeuProArgValLeuAlaSerLeuGlyAspValLysGlyValLeuSerValThrArg-736 |
| Antigenic Index - Jameson-Wolf | |
| SEQ. ID. NO. 1602 | 5-SerProIleGlnAspThrGlnSerAlaThr-14 |
| SEQ. ID. NO. 1603 | 16-GlnGluLeuArgGluTrpPheAspSerTyrCysAlaAlaLeuProAspAsnAspLysAsnLeuHisTyrProAla-50 |
| SEQ. ID. NO. 1604 | 52-AlaAlaThrProTyrGlyGluProLeuProAspHisPhe-64 |
| SEQ. ID. NO. 1605 | 72-HisAspLeuLeuPro-78 |
| SEQ. ID. NO. 1606 | 88-AspIleGlyArgTyrValProAspTrp-96 |
| SEQ. ID. NO. 1607 | 100-ValSerGluArgCysAsnSerThrVal-108 |
| SEQ. ID. NO. 1608 | 110-GluLeuValLysGlyValAspGluValGlnLysHis-123 |
| SEQ. ID. NO. 1609 | 125-AlaArgValAspSerLeuAlaThrProGluGluArgAlaGlnGlnAlaGluThrMetArg-144 |
| SEQ. ID. NO. 1610 | 162-AlaMetArgThrArgThr-167 |
| SEQ. ID. NO. 1611 | 173-AsnAlaProAspSerProGluLysArgAlaValAlaLysGluThrLeu-188 |
| SEQ. ID. NO. 1612 | 209-AspLeuGlyPheArgHisGlnLysProGluLysTyrArgGluLeuAspGluLysArgThrGluArgLeuGluTyr-237 |
| SEQ. ID. NO. 1613 | 245-LeuArgGlyGluLeuLysLysTyrAsnValAlaGlyArgProLysHisLysMetValLysLysLysLeuSerPhe-279 |
| SEQ. ID. NO. 1614 | 283-PheArgAlaThrValProGluCysTyr-299 |
| SEQ. ID. NO. 1615 | 311-ProIleProGlyGluPheAspAspTyrIleAlaAsnProLysGlyAsnGlyTyrLysSerIleValGlyProGluAspLysGlyValGluValGlnIleArgThr-349 |
| SEQ. ID. NO. 1616 | 356-AsnGlyTrpArgTyrLysGluGlyGlyLysGlyAspSerAlaTyrGluGlnLys-379 |
| SEQ. ID. NO. 1617 | 387-LeuAspTrpArgGluAsnMetAlaGluSerGlyLysGluAspLeuAlaAla-403 |
| SEQ. ID. NO. 1618 | 418-ThrProHisGlyLysProThrGly-429 |
| SEQ. ID. NO. 1619 | 440-HisSerSerIleGlyAspArgCysArgGlyAlaLysValGluGlyThrProLeuGluAsnGlyGlnArgValGluIleIleThrAlaLysGluGlyHisProSerValAsnGlyTrpValLysSerAsnLysAlaIleGlyLysAla-500 |
| SEQ. ID. NO. 1620 | 502-IleArgGlnGlnAsnAlaAspThrValArgGluGluGlyArgValGlnLeuAspLysGlnLeuAla-523 |
| SEQ. ID. NO. 1621 | 525-LeuThrProLysProAsnLeuGlnGluLeuAlaGlu-536 |
| SEQ. ID. NO. 1622 | 538-LeuGlyTyrLysLysProGluLysGlyGlnIleSerAsnArgAlaIleGlnLysAlaCysGlyThrLeuAsnGluProProValPro-574 |
| SEQ. ID. NO. 1623 | 582-LysGlnSerLysIleLysLysGlyGlyLysAsnGlyVal-594 |
| SEQ. ID. NO. 1624 | 596-IleAspGlyGluAspGlyLeu-602 |
| SEQ. ID. NO. 1625 | 608-LysCysCysLysProAlaProProAspAspIleIleValThrArgGluGlyIleSerValHisArgLysThrCysProSerPhe-638 |
| SEQ. ID. NO. 1626 | 644-HisAlaProGluLysValLeuAspGlnIleGluIleArgAlaGlnAspArgSerGlyLeuLeuArgAspValSerAspAlaLeuAlaArgHisLysLeu-690 |
| SEQ. ID. NO. 1627 | 696-GlnThrGlnSerArgAspLeuGluAlaSerMet-706 |
| SEQ. ID. NO. 1628 | 710-LeuGluValLysGlnValAsnAspLeuProArg-720 |
| SEQ. ID. NO. 1629 | 726-GlyAspValLysGly-730 |
| Hydrophilic Regions - Hopp-Woods | |
| SEQ. ID. NO. 1630 | 8-GlnAspThrGlnSer-12 |
| SEQ. ID. NO. 1631 | 16-GlnGluLeuArgGluTrpPhe-22 |
| SEQ. ID. NO. 1632 | 30-ProAspAsnAspLysAsnLeu-36 |
| SEQ. ID. NO. 1633 | 48-TyrProAlaProLeuProHisAspLeuLeuPro-78 |
| SEQ. ID. NO. 1634 | 100-ValSerGluArgCysAsnSerThrGluLeuValLysGlyValAspGluValGlnLysHis-123 |
| SEQ. ID. NO. 1635 | 125-AlaArgValAspSer-129 |
| SEQ. ID. NO. 1636 | 131-AlaThrProGluGluArgAlaGlnGlnAlaGluThrMetArg-144 |
| SEQ. ID. NO. 1637 | 162-AlaMetArgThrArgThrAlaProAspSerProGluLysArgAlaValAlaLysGluThrLeu-188 |
| SEQ. ID. NO. 1638 | 209-AspLeuGlyPheArgHisGlnLysProGluLysTyrArgGluLeuAspGluLysArgThrGluArgLeuGluTyr-237 |
| SEQ. ID. NO. 1639 | 245-LeuArgGlyGluLeuLysLysTyr-252 |
| SEQ. ID. NO. 1640 | 258-ValAlaGlyArgLysHisLysMetValLysLysLysLeuSerPhe-279 |
| SEQ. ID. NO. 1641 | 283-PheArgAlaThrValPro-296 |
| SEQ. ID. NO. 1642 | 314-GlyGluPheAspAsp-318 |
| SEQ. ID. NO. 1643 | 323-ProLysGlyAsnGly-327 |
| SEQ. ID. NO. 1644 | 337-GlyProGluAspLysGlyValGluValGlnIleArgThr-349 |
| SEQ. ID. NO. 1645 | 351-AspGlnArgTyrLysGluGlyGlyLysGlyAspSerAlaTyrGluGlnLeuAspTrpArgGluAsnMetAlaGluSerGlyLysGluAspLeuAlaAla-403 |
| SEQ. ID. NO. 1646 | 405-PheLysLeuPheIleGlyAspArgCysArgGlyAlaLysValGluGlyLeuGluAsnGlyGlnArgValGluIleIleThrAlaLysGluGlyHisPro-479 |
| SEQ. ID. NO. 1647 | 489-ValLysSerAsnLysAlaIleGlyLysAla-500 |
| SEQ. ID. NO. 1648 | 502-IleGlnAsnAlaAspThrValArgGluGluGlyArgValGlnLeuAspLysGlnLeuAla-523 |
| SEQ. ID. NO. 1649 | 538-LeuGlyTyrLysLysProGluLysAspLeuGly-551 |
| SEQ. ID. NO. 1650 | 553-GlyGluIleSerAsn-557 |
| SEQ. ID. NO. 1651 | 582-LysGlnSerLysIleLysLysGlyGlyLysVal-594 |
| SEQ. ID. NO. 1652 | 596-IleAspGlyGluAspGlyLeu-602 |
| SEQ. ID. NO. 1653 | 608-LysCysCysLysProAlaProProAspAsp-617 |
| SEQ. ID. NO. 1654 | 623-ThrArgGluArgGlyIleSerValHisArgLysThrCysHisAlaProGluLysValLeu-650 |
| SEQ. ID. NO. 1655 | 658-GlnIleGluIleArgAlaGlnAspArgSerGlyLeuLeuArgAspValSerAspAlaLeuAlaArgHisLysLeuThrGlnSerArgAspLeuGluAlaSerMet-706 |
| SEQ. ID. NO. 1656 | 710-LeuGluValLysGlnValAsnAspLeuProArg-720 |

TABLE 1-continued

SEQ. ID. NO. 1657  726-GlyAspValLysGly-730
118-2
AMPHI Regions - AMPHI
SEQ. ID. NO. 1658  11-ArgArgAsnIleGlyLysTrpTyrAsp-31
SEQ. ID. NO. 1659  61-ProArgTyrIleGlyThrIleIleAspPheLeuMetValProAsn-79
SEQ. ID. NO. 1660  102-GluArgLeuLysThrMetLeuArg-109
Antigenic Index - Jameson-Wolf
SEQ. ID. NO. 1661  8-LysAsnPheArgArgAsnIleThrCysPheGluGlyTyrAspGluAsnSerPhe-25
SEQ. ID. NO. 1662  27-GlyLysTrpTyrAspAspGlyValTrpAspAspGluGluTyrTrpLysLeuGluAsnAspLeuIleGluValArgLysLysTyrProTyrPro
                   MetAspIle-60
SEQ. ID. NO. 1663  93-AspSerValGlyIleAsnGluArgTyrGluArgLeuLysThr-106
SEQ. ID. NO. 1664  112-PheThrGluLysAspIleValAspTyrTyrAsnLysLys-128
Hydrophilic Regions - Hopp-Woods
SEQ. ID. NO. 1665  8-LysAsnPheArgArgAsnIleThr-15
SEQ. ID. NO. 1666  33-GlyValTrpAspAspGluGluTyrTrpLysLeuGluAsnAspLeuIleGluValArgLysLysTyrProTyrAspIle-60
SEQ. ID. NO. 1667  95-ValGlyIleAsnGluArgTyrGluArgLeuLysThr-106
SEQ. ID. NO. 1668  112-PheThrGluLysAspIleVal-118
120-2
AMPHI Regions - AMPHI
SEQ. ID. NO. 1669  6-LysAsnIlePheSerAla-11
SEQ. ID. NO. 1670  49-SerGlyAsnAlaTyrLysIleValSerThrIleLys-60
SEQ. ID. NO. 1671  77-AsnThrLeuHisProThrTyrTyrArgAspIleArgArg-89
SEQ. ID. NO. 1672  142-IleThrAsnGlyLysLysLeuTyrSerValGlyGlyLeuAsnLysAlaGly-158
SEQ. ID. NO. 1673  189-ProSerLeuAsnAsnIleProAla-196
Antigenic Index - Jameson-Wolf
SEQ. ID. NO. 1674  3-LysThrPheLys-6
SEQ. ID. NO. 1675  35-SerGlySerTyrGly-39
SEQ. ID. NO. 1676  45-ThrPheGluArgSerGlyAsnAlaTyrLys-54
SEQ. ID. NO. 1677  68-PheGluSerGlyGlyThrValVal-75
SEQ. ID. NO. 1678  85-ArgAspIleArgArgGlyLysLeuTyrAlaGlu-95
SEQ. ID. NO. 1679  97-LysPheAlaAspGlySerValThrTyrGlyLysAlaGlyGluSerLysThrGluGlnSerProLysAla-119
SEQ. ID. NO. 1680  131-AlaAsnAspAlaLysLeuProProGlyLeuLysIleThrAsnGlyLysLysLeuTyrSer-150
SEQ. ID. NO. 1681  153-GlyLeuAsnLysAlaGlyThrGlyLysTyrSerIleGlyGlyValGluThrGluValValLysTyrArgValArgArgGlyAspAspAlaVal-183
SEQ. ID. NO. 1682  199-GlyTyrThrAspAspGlyLysThrTyr-207
SEQ. ID. NO. 1683  218-GlyGlnAlaAlaLysPro-223
Hydrophilic Regions - Hopp-Woods
SEQ. ID. NO. 1684  45-ThrPheGluArgSerGlyAsn-51
SEQ. ID. NO. 1685  85-ArgAspIleArgArgGlyLysLeuTyrAla-94
SEQ. ID. NO. 1686  107-LysAlaGlyGluSerLysThrGluGlnSerProLysAla-119
SEQ. ID. NO. 1687  131-AlaAsnAspAlaLysLeu-136
SEQ. ID. NO. 1688  143-ThrAsnGlyLysLysLeuTyr-149
SEQ. ID. NO. 1689  155-AsnLysAlaGlyThrGly-160
SEQ. ID. NO. 1690  167-ValGluThrGluValValLysTyrArgValArgArgGlyAspAspAla-182
SEQ. ID. NO. 1691  200-TyrThrAspAspGlyLysThrTyr-207
SEQ. ID. NO. 1692  219-GlnAlaAlaLysPro-223
121-1
AMPHI Regions - AMPHI
SEQ. ID. NO. 1693  42-ProGlyArgLeuArgArg-47
SEQ. ID. NO. 1694  68-GlnGluLeuSerArgLeuTyrAlaGlnThr-77
SEQ. ID. NO. 1695  101-ThrValArgHisAlaPro-106
SEQ. ID. NO. 1696  148-ProAlaPheHisGlu-152
SEQ. ID. NO. 1697  165-LeuAsnIleGlyGlyIleAlaAsnIle-173
SEQ. ID. NO. 1698  189-ProGlyAsnMetLeuMetAspAlaTrpThr-198
SEQ. ID. NO. 1699  216-GlyAsnIleLeuProGlnLeuLeuAspArgLeuLeu-227
SEQ. ID. NO. 1700  237-ProLysSerThrGly-241
SEQ. ID. NO. 1701  251-GluThrTyrLeuAsp-255
SEQ. ID. NO. 1702  262-AspValLeuArgThrLeuSerArgPheThrAlaGlnThrValCysAspAlaValSerHis-281
SEQ. ID. NO. 1703  303-AlaAspLeuAlaGluCysPhe-309
SEQ. ID. NO. 1704  341-IleAsnArgIleProGlySerPro-348
Antigenic Index - Jameson-Wolf
SEQ. ID. NO. 1705  13-ThrSerMetAspGlyAlaAsp-19
SEQ. ID. NO. 1706  23-IleArgMetAspGlyGlyLysTrpLeuGly-32
SEQ. ID. NO. 1707  40-ProTyrProGlyArgLeuArgArgGlnLeuLeuAspLeuGlnAspThrGlyAlaAspGluLeuHisArgSerArgIleLeuSer-67
SEQ. ID. NO. 1708  86-AsnLeuAlaProSerAspIleThrAla-94
SEQ. ID. NO. 1709  97-CysHisGlyGlnThrValArgHisAlaProGluHisGlyTyrSer-111
SEQ. ID. NO. 1710  119-LeuLeuAlaGluArgThrArg-125
SEQ. ID. NO. 1711  128-ThrValGlyAspPheArgSerArgAspLeuAlaAlaGlyGlyGlnGly-143
SEQ. ID. NO. 1712  154-LeuPheArgAspAsnArgGluThrArgAla-163
SEQ. ID. NO. 1713  177-ProProAspAlaPro-181
SEQ. ID. NO. 1714  184-GlyPheAspThrGlyProGlyAsn-191
SEQ. ID. NO. 1715  205-ProTyrAspLysAsnGlyAlaLysAlaAlaGlnGlyAsn-217
SEQ. ID. NO. 1716  235-ProHisProLysSerThrGlyArgGlu-243
SEQ. ID. NO. 1717  253-TyrLeuAspGlyGlyGluAsnArgTyrAspValLeuArgThrLeuSerArg-269
SEQ. ID. NO. 1718  283-AlaAlaAspAlaArgGln-288
SEQ. ID. NO. 1719  293-GlyGlyGlyIleArgAsnProValLeu-301
SEQ. ID. NO. 1720  321-LeuAsnLeuAspProGlnTrp-327
SEQ. ID. NO. 1721  344-IleProGlySerProHisLysAlaThrGlyAlaSerLysProCysIle-359
Hydrophilic Regions - Hopp-Woods
SEQ. ID. NO. 1722  13-ThrSerMetAspGlyAlaAsp-19
SEQ. ID. NO. 1723  43-GlyArgLeuArgArgGlnLeuLeuAspLeuGlnAspThrGlyAlaAspGluLeuHisArgSerArgIleLeuSer-67

TABLE 1-continued

| | |
|---|---|
| SEQ. ID. NO. 1724 | 101-ThrValArgHisAlaPro-106 |
| SEQ. ID. NO. 1725 | 119-LeuLeuAlaGluArgThrArg-125 |
| SEQ. ID. NO. 1726 | 131-AspPheArgSerArgAspLeuAlaAla-139 |
| SEQ. ID. NO. 1727 | 154-LeuPheArgAspAsnArgGluThrArgAla-163 |
| SEQ. ID. NO. 1728 | 206-TyrAspLysSerAsnGlyAlaLysAlaAlaGln-215 |
| SEQ. ID. NO. 1729 | 236-HisProLysSerThrGlyArgGlu-243 |
| SEQ. ID. NO. 1730 | 254-LeuAspGlyGlyGluAsnArgTyrAspVal-263 |
| SEQ. ID. NO. 1731 | 283-AlaAlaAspAlaArgGln-288 |
| SEQ. ID. NO. 1732 | 345-ProGlySerProHisLysAlaThrGlyAlaSer-355 |

122-1
AMPHI Regions - AMPHI

| | |
|---|---|
| SEQ. ID. NO. 1733 | 6-AsnIleHisLysThrPhe-11 |
| SEQ. ID. NO. 1734 | 42-ThrPheLeuArgCysLeuAsnAlaLeuGluMetProGlu-54 |
| SEQ. ID. NO. 1735 | 102-LeuGluAsnValMetGlu-107 |
| SEQ. ID. NO. 1736 | 126-LysLeuLeuGluLys-130 |
| SEQ. ID. NO. 1737 | 176-ProGluLeuValGlnAspValLeuAspThrMetLysGluLeuAla-190 |
| SEQ. ID. NO. 1738 | 227-ProGlnAspLeuPheAspHisPro-234 |

Antigenic Index - Jameson-Wolf

| | |
|---|---|
| SEQ. ID. NO. 1739 | 5-ArgAsnIleHisLysThrPheGlyGluAsnThrIle-16 |
| SEQ. ID. NO. 1740 | 23-AspValCysLysGlyGln-28 |
| SEQ. ID. NO. 1741 | 34-GlyProSerGlySerGlyLysThrThr-42 |
| SEQ. ID. NO. 1742 | 51-GluMetProGluAspGlyGlnIleGluPheAspAsnGluArgProLeuLysIleAspPheSerLysLysProSerLysHisAspIle-79 |
| SEQ. ID. NO. 1743 | 81-AlaLeuArgArgLysSerGlyMet-88 |
| SEQ. ID. NO. 1744 | 96-PheProHisLysThrAlaLeu-102 |
| SEQ. ID. NO. 1745 | 114-GlyLysProAlaAlaGlnAlaArgGluGluAlaLeuLysLeuLeuGlu-129 |
| SEQ. ID. NO. 1746 | 131-ValGlyLeuGlyAspLysValAspLeuTyr-140 |
| SEQ. ID. NO. 1747 | 142-TyrGlnLeuSerGlyGlyGlnGlnGlnArgValGlyIle-154 |
| SEQ. ID. NO. 1748 | 168-AspGluProThrSerAlaLeuAspProGluLeuVal-179 |
| SEQ. ID. NO. 1749 | 182-ValLeuAspThrMetLysGluLeuAlaGlnGluGly-193 |
| SEQ. ID. NO. 1750 | 216-MetAspGlyGlyVal-220 |
| SEQ. ID. NO. 1751 | 222-ValGluGlnGlySerProGlnAspLeuPheAspHisProLysHisGluArgThrArgArgPheLeuSer-244 |
| SEQ. ID. NO. 1752 | 246-IleGlnSerThrLysIle-251 |

Hydrophilic Regions - Hopp-Woods

| | |
|---|---|
| SEQ. ID. NO. 1753 | 51-GluMetProGluAspGlyGlnIleGluPheAspAsnGluArgProLeuLysIleAspPheSerLysLysProSerLysHisAsp-78 |
| SEQ. ID. NO. 1754 | 81-AlaLeuArgArgLysSerGly-87 |
| SEQ. ID. NO. 1755 | 114-GlyLysProAlaAlaGlnAlaArgGluGluAlaLeuLysLeuLeuGlu-129 |
| SEQ. ID. NO. 1756 | 131-ValGlyLeuGlyAspLysValAsp-138 |
| SEQ. ID. NO. 1757 | 168-AspGluProThrSerAlaLeuAspProGluLeuVal-179 |
| SEQ. ID. NO. 1758 | 182-ValLeuAspThrMetLysGluLeuAlaGln-191 |
| SEQ. ID. NO. 1759 | 229-AspLeuPheAspHisProLysHisGluArgThrArgArgPheLeu-243 |

126-1
AMPHI Regions - AMPHI

| | |
|---|---|
| SEQ. ID. NO. 1760 | 73-GlyCysGlnSerValGlnGluAla-80 |
| SEQ. ID. NO. 1761 | 112-PheGlnLeuValGluAla-117 |
| SEQ. ID. NO. 1762 | 143-LeuAspAlaGlyCysGln-148 |
| SEQ. ID. NO. 1763 | 150-LeuMetProTrpAlaAlaProIleGlyThrGlyLeuGlyAlaVal-164 |
| SEQ. ID. NO. 1764 | 213-SerGlyAspProValAsnMetAlaArgAlaPhe-223 |

Antigenic Index - Jameson-Wolf

| | |
|---|---|
| SEQ. ID. NO. 1765 | 7-GluThrPheProSerArgLeu-13 |
| SEQ. ID. NO. 1766 | 24-GluIleLeuLysGlnSerIle-30 |
| SEQ. ID. NO. 1767 | 41-SerLeuArgArgAlaGlySerGlyGlyGluAlaHisGlyGlnGlyPhe-56 |
| SEQ. ID. NO. 1768 | 85-GlnMetAlaArgGluValPheGlu-92 |
| SEQ. ID. NO. 1769 | 99-GluLeuIleGlyAspAspAspThrLeuGln-108 |
| SEQ. ID. NO. 1770 | 121-LeuIleLysAspGlyPheLysValLeu-129 |
| SEQ. ID. NO. 1771 | 141-ArgLeuLeuAspAlaGlyCys-147 |
| SEQ. ID. NO. 1772 | 171-ValLeuArgGluArgLeuProAspThrProLeu-181 |
| SEQ. ID. NO. 1773 | 209-AlaValSerArgSerGlyAspProValAsn-218 |
| SEQ. ID. NO. 1774 | 228-GluSerGlyArgLeuAlaPhe-234 |
| SEQ. ID. NO. 1775 | 237-GlyProValGluAlaArgAspLysAlaGlnAlaSerThrProThrVal-252 |

Hydrophilic Regions - Hopp-Woods

| | |
|---|---|
| SEQ. ID. NO. 1776 | 41-SerLeuArgArgAlaGlySerGlyGlyGluAlaHis-52 |
| SEQ. ID. NO. 1777 | 85-GlnMetAlaArgGluValPheGlu-92 |
| SEQ. ID. NO. 1778 | 100-LeuIleGlyAspAspAspThrLeuGln-108 |
| SEQ. ID. NO. 1779 | 171-ValLeuArgGluArgLeuProAsp-178 |
| SEQ. ID. NO. 1780 | 210-ValSerArgSerGlyAspPro-216 |
| SEQ. ID. NO. 1781 | 228-GluSerGlyArgLeuAlaPhe-234 |
| SEQ. ID. NO. 1782 | 237-GlyProValGluAlaArgAspLysAlaGlnAla-247 |

127
AMPHI Regions - AMPHI

| | |
|---|---|
| SEQ. ID. NO. 1783 | 6-MetLeuAspThrTrpLeuGlyAla-13 |
| SEQ. ID. NO. 1784 | 20-AlaValGluSerValAlaAla-26 |
| SEQ. ID. NO. 1785 | 119-ValGlyAspTyrIleGluIle-125 |
| SEQ. ID. NO. 1786 | 135-IleAsnLeuLeuAsnThrLeuMet-142 |
| SEQ. ID. NO. 1787 | 147-ProAsnProLeuValGlyGlnLeuAla-155 |
| SEQ. ID. NO. 1788 | 206-LeuGluProLeuCysAlaPro-212 |
| SEQ. ID. NO. 1789 | 214-IleProAlaIleGlnArgXxxLeuGluAsnValGln-225 |
| SEQ. ID. NO. 1790 | 250-ArgIleIleValArgPheAlaSerProVal-259 |
| SEQ. ID. NO. 1791 | 268-AlaValMetAspGluPheLeuArgVal-276 |

Antigenic Index - Jameson-Wolf

| | |
|---|---|
| SEQ. ID. NO. 1792 | 16-IleArgAlaGluAlaValGlu-22 |

TABLE 1-continued

| | |
|---|---|
| SEQ. ID. NO. 1793 | 41-HisPheLysArgHisProAspPheGlyIleGluSerLysArgArgPheLeuVal-58 |
| SEQ. ID. NO. 1794 | 112-SerAlaThrGlnGlnTyrSerVal-119 |
| SEQ. ID. NO. 1795 | 126-AsnGlyLeuArgGlyArgValValAsp-134 |
| SEQ. ID. NO. 1796 | 169-HisProValArgArgAspAsnIleLeu-177 |
| SEQ. ID. NO. 1797 | 193-LeuAspSerAspGluAlaValCysArg-201 |
| SEQ. ID. NO. 1798 | 234-AlaAlaArgProArgValThrArgValProTyrAspAspLysAlaTyr-249 |
| SEQ. ID. NO. 1799 | 257-SerProValSerLysArgLeuGluIle-265 |
| SEQ. ID. NO. 1800 | 282-AsnHisProAlaGlySerGluThrLeu-290 |
| Hydrophilic Regions - Hopp-Woods | |
| SEQ. ID. NO. 1801 | 16-IleArgAlaGluAlaValGlu-22 |
| SEQ. ID. NO. 1802 | 42-PheLysArgHisProAspPheGlyIleGluSerLysArgArgPheLeuVal-58 |
| SEQ. ID. NO. 1803 | 126-AsnGlyLeuArgGlyArgValVal-133 |
| SEQ. ID. NO. 1804 | 170-ProValArgArgAspAsnIleLeu-177 |
| SEQ. ID. NO. 1805 | 193-LeuAspSerAspGluAlaValCysArg-201 |
| SEQ. ID. NO. 1806 | 235-AlaArgProArgValThrArgValProTyrAspAspLysAlaTyr-249 |
| SEQ. ID. NO. 1807 | 259-ValSerLysArgLeuGluIle-265 |
| SEQ. ID. NO. 1808 | 285-AlaGlySerGluThrLeu-290 |
| 128-1 | |
| AMPHI Regions - AMPHI | |
| SEQ. ID. NO. 1809 | 43-AlaGlnThrHisThrGlyTrpAlaAsnThrValGluProLeuThrGlyIleThrGluArgValGlyArgIleTrpGlyValValSerHisLeuAsnSerValAlaAspThrProGluLeu-82 |
| SEQ. ID. NO. 1810 | 85-ValTyrAsnGluLeuMetProGluIle-93 |
| SEQ. ID. NO. 1811 | 102-GlnAspIleGluLeuTyrAsnArgPheLysThrIleLysAsnSerProGluPhe-119 |
| SEQ. ID. NO. 1812 | 166-PheSerGlnAsnValLeuAspAlaThrAsp-175 |
| SEQ. ID. NO. 1813 | 189-GlyIleProGluAspAla-194 |
| SEQ. ID. NO. 1814 | 218-HisTyrLeuAlaVal-222 |
| SEQ. ID. NO. 1815 | 245-GluLeuSerAspAspGlyLysPheAspAsnThrAlaAsnIleAspArgThrLeuAlaAsnAlaLeuGlnThrAlaLysLeuLeuGlyPheLysAsnTyrAlaGlu-279 |
| SEQ. ID. NO. 1816 | 286-MetAlaAspThrProGluGlnValLeuAsnPheLeuHisAspLeuAlaArgArgAla-304 |
| SEQ. ID. NO. 1817 | 313-AlaGluValLysAlaPheAlaArg-320 |
| SEQ. ID. NO. 1818 | 359-GlyLysValLeuAsnGlyLeuPheAlaGlnIleLysLysLeuTyrGly-374 |
| SEQ. ID. NO. 1819 | 472-LeuHisHisLeuLeuThrGlnValAspGluLeu-482 |
| SEQ. ID. NO. 1820 | 496-GluLeuProSerGlnPhe-501 |
| SEQ. ID. NO. 1821 | 565-GlyArgLeuLysAsnTrpGlnGlnValLeuAspSerVal-577 |
| SEQ. ID. NO. 1822 | 610-SerTyrAlaTrpAlaGlu-615 |
| SEQ. ID. NO. 1823 | 623-AlaAlaPheGluGluSerAspAsp-630 |
| SEQ. ID. NO. 1824 | 636-LysArgPheTrpGluIleLeuAla-644 |
| SEQ. ID. NO. 1825 | 651-AlaAlaGluSerPheLysAlaPheArg-659 |
| Antigenic Index - Jameson-Wolf | |
| SEQ. ID. NO. 1826 | 9-LeuGlyGluGluProArgPheAspGlnIleLysThrGluAspIleLysProAlaLeu-27 |
| SEQ. ID. NO. 1827 | 32-AlaGluAlaArgGluGlnIleAla-39 |
| SEQ. ID. NO. 1828 | 43-AlaGlnThrHisThrGlyTrp-49 |
| SEQ. ID. NO. 1829 | 51-AsnThrValGluProLeuThrGlyIleThrGluArgValGlyArgIleTrp-67 |
| SEQ. ID. NO. 1830 | 75-SerValAlaAspThrProGluLeu-82 |
| SEQ. ID. NO. 1831 | 100-IleGlyGlnAspIleGluLeuTyrAsnArgPheLysThrIleLysAsnSerProGluPheAspThrLeuSerProAlaGlnLysThrLysLeuAsnHisAspLeuArgAsp-136 |
| SEQ. ID. NO. 1832 | 138-ValLeuSerGlyAlaGluLeuProProGluGlnGlnAlaGluLeuAlaLysLeuGlnThrGluGlyAlaGlnLeu-162 |
| SEQ. ID. NO. 1833 | 165-LysPheSerGlnAsnVal-170 |
| SEQ. ID. NO. 1834 | 172-AspAlaThrAspAla-176 |
| SEQ. ID. NO. 1835 | 190-IleProGluAspAla-194 |
| SEQ. ID. NO. 1836 | 202-AlaGlnSerGluSerLysThrGlyTyrLysIle-212 |
| SEQ. ID. NO. 1837 | 226-AlaAspAsnArgGluLeuArgGluGlnIle-235 |
| SEQ. ID. NO. 1838 | 240-ValThrArgAlaSerGluLeuSerAspAspGlyLysPheAspAsnThrAlaAsnIleAspArgThrLeu-262 |
| SEQ. ID. NO. 1839 | 285-LysMetAlaAspThrProGluGln-292 |
| SEQ. ID. NO. 1840 | 300-LeuAlaArgArgAlaLysProTyrAlaGluLysAspLeuAlaGlu-314 |
| SEQ. ID. NO. 1841 | 316-LysAlaPheAlaArgGluSerLeuAsn-324 |
| SEQ. ID. NO. 1842 | 335-TyrAlaSerGluLysLeuLeuArgGluAlaLysTyrAlaPheSerGluThrGluValLysLys-354 |
| SEQ. ID. NO. 1843 | 376-GlyPheThrGluLysThrVal-382 |
| SEQ. ID. NO. 1844 | 387-LysAspValArgTyrPheGluLeuGlnGlnAsnGlyGluThrIle-401 |
| SEQ. ID. NO. 1845 | 409-TyrAlaArgGluGlyLysArgGlyGlyAla-418 |
| SEQ. ID. NO. 1846 | 420-MetAsnAspTyrLysGlyArgArgPheSerAspGlyThrLeu-434 |
| SEQ. ID. NO. 1847 | 447-ProProValGlyGlyArgGluAlaArgLeuSerHisAspGlu-460 |
| SEQ. ID. NO. 1848 | 478-GlnValAspGluLeuGlyVal-484 |
| SEQ. ID. NO. 1849 | 496-GluLeuProSerGln-500 |
| SEQ. ID. NO. 1850 | 516-SerAlaHisGluGluThrGlyVal-523 |
| SEQ. ID. NO. 1851 | 560-SerGluAspValAspGluGlyArgLeuLysAsn-569 |
| SEQ. ID. NO. 1852 | 575-AspSerValArgLysLysValAla-582 |
| SEQ. ID. NO. 1853 | 586-ProProGluTyrAsnArg-591 |
| SEQ. ID. NO. 1854 | 605-SerAlaGlyTyrTyrSerTyr-611 |
| SEQ. ID. NO. 1855 | 625-PheGluGluSerAspAspValAlaAlaThrGlyLysArgPheTrp-639 |
| SEQ. ID. NO. 1856 | 646-GlyGlySerArgSerAlaAlaGluSerPheLysAlaPheArgGlyArgGluProSerIle-665 |
| SEQ. ID. NO. 1857 | 669-LeuArgHisSerGlyPheAspAsnAlaVal-678 |
| Hydrophilic Regions - Hopp-Woods | |
| SEQ. ID. NO. 1858 | 9-LeuGlyGluGluProArgPheAspGlnIleLysThrGluAspIleLysPro-25 |
| SEQ. ID. NO. 1859 | 32-AlaGluAlaArgGluGlnIleAla-39 |
| SEQ. ID. NO. 1860 | 59-IleThrGluArgValGly-64 |
| SEQ. ID. NO. 1861 | 77-AlaAspThrProGluLeu-82 |
| SEQ. ID. NO. 1862 | 100-IleGlyGlnAspIleGluLeu-106 |
| SEQ. ID. NO. 1863 | 111-LysThrIleLysAsnSerProGluPheAspThr-121 |

TABLE 1-continued

| | |
|---|---|
| SEQ. ID. NO. 1864 | 123-SerProAlaGlnLysThrLysLeuAsnHisAspLeuArgAsp-136 |
| SEQ. ID. NO. 1865 | 143-GluLeuProProGluGlnGlnAlaGluLeuAlaLysLeuGlnThrGluGlyAlaGlnLeu-162 |
| SEQ. ID. NO. 1866 | 190-IleProGluAspAla-194 |
| SEQ. ID. NO. 1867 | 202-AlaGlnSerGluSerLysThrGlyTyr-210 |
| SEQ. ID. NO. 1868 | 226-AlaAspAsnArgGluLeuArgGluGlnIle-235 |
| SEQ. ID. NO. 1869 | 242-ArgAlaSerGluLeuSerAspAspGlyLysPheAspAsn-254 |
| SEQ. ID. NO. 1870 | 256-AlaAsnIleAspArgThrLeu-262 |
| SEQ. ID. NO. 1871 | 285-LysMetAlaAspThrProGlu-291 |
| SEQ. ID. NO. 1872 | 300-LeuAlaArgArgAlaLysProTyrAlaGluLysAspLeuAlaGlu-314 |
| SEQ. ID. NO. 1873 | 316-LysAlaPheAlaArgGluSerLeuAsn-324 |
| SEQ. ID. NO. 1874 | 335-TyrAlaSerGluLysLeuArgGluAlaLysTyrAlaPheSerGluThrGluValLysLys-354 |
| SEQ. ID. NO. 1875 | 377-PheThrGluLysThr-381 |
| SEQ. ID. NO. 1876 | 387-LysAspValArgTyr-391 |
| SEQ. ID. NO. 1877 | 396-GlnAsnGlyGluThr-400 |
| SEQ. ID. NO. 1878 | 409-TyrAlaArgGluGlyLysArgGlyGly-417 |
| SEQ. ID. NO. 1879 | 423-TyrLysGlyArgArgArgPheSerAsp-431 |
| SEQ. ID. NO. 1880 | 449-ValGlyGlyArgGluAlaArgLeuSerHisAspGlu-460 |
| SEQ. ID. NO. 1881 | 478-GlnValAspGluLeuGly-483 |
| SEQ. ID. NO. 1882 | 516-SerAlaHisGluGluThrGly-522 |
| SEQ. ID. NO. 1883 | 560-SerGluAspAspGluGlyArgLeuLysAsn-569 |
| SEQ. ID. NO. 1884 | 575-AspSerValArgLysLysValAla-582 |
| SEQ. ID. NO. 1885 | 625-PheGluGluSerAspAspValAlaAlaThrGly-635 |
| SEQ. ID. NO. 1886 | 647-GlySerArgSerAlaAlaGluSerPheLysAlaPheArgGlyArgGluProSerIle-665 |
| 130-2 | |
| AMPHI Regions - AMPHI | |
| SEQ. ID. NO. 1887 | 16-ThrLeuValSerGlyIle-21 |
| SEQ. ID. NO. 1888 | 36-GlySerGlySerPheGly-41 |
| SEQ. ID. NO. 1889 | 56-GlnProValGlyGlnLeu-61 |
| SEQ. ID. NO. 1890 | 91-AsnValProAsnAlaPro-96 |
| SEQ. ID. NO. 1891 | 110-GlnGlyPheAspThrLeuPheGlnHisAlaLeuAsnGlyPheAsnAlaMet-126 |
| SEQ. ID. NO. 1892 | 171-ThrAlaSerAlaPro-175 |
| SEQ. ID. NO. 1893 | 204-PheGluAlaThrCysGln-209 |
| SEQ. ID. NO. 1894 | 211-CysHisGlyGlySerIleProGlyIlePro-220 |
| SEQ. ID. NO. 1895 | 234-LysGlyLysGluThr-238 |
| SEQ. ID. NO. 1896 | 245-GluGlyPheAsnAlaMet-250 |
| Antigenic Index - Jameson-Wolf | |
| SEQ. ID. NO. 1897 | 1-MetLysGlnLeuArgAspAsnLysAlaGlnGlySer-12 |
| SEQ. ID. NO. 1898 | 35-AlaGlySerGlySerPheGlyAspValAspAlaThrThrGluAlaAlaThrGlnThrArgIleGlnProValGly-59 |
| SEQ. ID. NO. 1899 | 63-MetGlyAspGlyIleProValGlyGluArgGlnGlyGlu-75 |
| SEQ. ID. NO. 1900 | 87-AlaAlaAspSerAsnValProAsnAlaProLysLeuGluHisAsnGlyAspTrpAla-105 |
| SEQ. ID. NO. 1901 | 108-IleAlaGlnGlyPhe-112 |
| SEQ. ID. NO. 1902 | 126-MetProAlaLysGlyGlyAla-132 |
| SEQ. ID. NO. 1903 | 134-AspLeuThrAspGlnGluLeuLysArg-142 |
| SEQ. ID. NO. 1904 | 148-AlaAsnLysSerGlyGlySerPheProAsnProAspGluAlaAlaProAlaAspAsnAlaAlaSerGlyThrAlaSerAlaProAla AspSerAlaAlaProAlaGluAlaLysAlaGluAspLysGlyAlaAla-192 |
| SEQ. ID. NO. 1905 | 197-GlyValAspGlyLysLysValPheGlu-205 |
| SEQ. ID. NO. 1906 | 221-GlyIleGlyLysLysAspAspTrpAlaProArgIleLysLysGlyLysGluThrLeuHis-240 |
| SEQ. ID. NO. 1907 | 251-ProAlaLysGlyGlyAsnAlaGlyLeuSerAspAspGluValLysAla-266 |
| SEQ. ID. NO. 1908 | 274-GlnSerGlyAlaLys-278 |
| Hydrophilic Regions - Hopp-Woods | |
| SEQ. ID. NO. 1909 | 1-MetLysGlnLeuArgAspAsnLysAlaGlnGly-11 |
| SEQ. ID. NO. 1910 | 41-GlyAspValAspAlaThrThrGluAlaAlaThr-51 |
| SEQ. ID. NO. 1911 | 68-ProValGlyGluArgGlnGlyGlu-75 |
| SEQ. ID. NO. 1912 | 87-AlaAlaAspSerAsnVal-92 |
| SEQ. ID. NO. 1913 | 96-ProLysLeuGluHisAsnGly-102 |
| SEQ. ID. NO. 1914 | 127-ProAlaLysGlyGlyAla-132 |
| SEQ. ID. NO. 1915 | 134-AspLeuThrAspGlnGluLeuLysArg-142 |
| SEQ. ID. NO. 1916 | 156-ProAsnProAspGluAlaAlaProAlaAspAsnAlaAla-168 |
| SEQ. ID. NO. 1917 | 174-AlaProAlaAspSerAlaAlaProAlaGluAlaLysAlaGluAspLysGlyAlaAla-192 |
| SEQ. ID. NO. 1918 | 198-ValAspGlyLysLysValPheGlu-205 |
| SEQ. ID. NO. 1919 | 222-IleGlyLysLysAspAspTrpAlaProArgIleLysLysGlyLysGluThrLeuHis-240 |
| SEQ. ID. NO. 1920 | 251-ProAlaLysGlyGlyAsn-256 |
| SEQ. ID. NO. 1921 | 258-GlyLeuSerAspAspGluValLysAla-266 |
| 132-2 | |
| AMPHI Regions - AMPHI | |
| SEQ. ID. NO. 1922 | 13-IleIleSerAlaLeuAlaVal-19 |
| SEQ. ID. NO. 1923 | 70-AlaThrCysMetAlaMetVal-76 |
| SEQ. ID. NO. 1924 | 92-ValGlnGlnThrGlnGlnAlaProLysProValSerAsnThr-105 |
| Antigenic Index - Jameson-Wolf | |
| SEQ. ID. NO. 1925 | 26-GlnHisGlyLysGlyAlaAspAla-33 |
| SEQ. ID. NO. 1926 | 38-GlySerGlySerGlySerAla-44 |
| SEQ. ID. NO. 1927 | 81-HisThrThrLysHisGlyLeuAspPhe-89 |
| SEQ. ID. NO. 1928 | 91-AsnValGlnGlnThrGlnGlnAlaProLysProValSerAsnThrGluProSerAlaProValProGlnGlnGlnLys-116 |
| Hydrophilic Regions - Hopp-Woods | |
| SEQ. ID. NO. 1929 | 28-GlyLysGlyAlaAspAla-33 |
| SEQ. ID. NO. 1930 | 97-GlnAlaProLysProValSerAsnThrGluProSerAla-109 |
| 134 | |
| AMPHI Regions - AMPHI | |
| SEQ. ID. NO. 1931 | 39-IleGlnSerAlaGlyThrVal-45 |
| SEQ. ID. NO. 1932 | 47-GlyLysLysThrGly-51 |

TABLE 1-continued

| | |
|---|---|
| SEQ. ID. NO. 1933 | 58-TrpMetGluIleGluLysGlnArg-65 |
| SEQ. ID. NO. 1934 | 83-ValAsnLeuLeuAspThrProGlyHis-91 |
| SEQ. ID. NO. 1935 | 97-AspThrTyrArgValLeuThrAlaVal-105 |
| SEQ. ID. NO. 1936 | 114-AlaAlaGlyValGlu-119 |
| SEQ. ID. NO. 1937 | 123-IleLysLeuLeuAsnValCysArg-130 |
| SEQ. ID. NO. 1938 | 142-LysTyrAspArgGluVal-147 |
| SEQ. ID. NO. 1939 | 149-AspSerLeuGluLeuLeuAspGluValGluAsnIleLeuLys-162 |
| SEQ. ID. NO. 1940 | 176-LysAsnPheLysGlyValTyrHisIleLeu-185 |
| SEQ. ID. NO. 1941 | 201-HisGluPheAspIleIleLysGlyIleAspAsn-211 |
| SEQ. ID. NO. 1942 | 254-PheGlySerAlaIle-258 |
| SEQ. ID. NO. 1943 | 265-GluIleLeuAsnSerLeuIleAspTrpAlaPro-275 |
| SEQ. ID. NO. 1944 | 322-LysPheGluArgGlyMetLys-328 |
| SEQ. ID. NO. 1945 | 361-AspIleIleGlyIleProAsnHis-368 |
| SEQ. ID. NO. 1946 | 395-LeuPheArgSerValArgIleLys-402 |
| SEQ. ID. NO. 1947 | 404-ProLeuLysIleLysGln-409 |
| SEQ. ID. NO. 1948 | 411-GlnLysGlyLeuGlnGlnLeuGlyGlu-419 |
| SEQ. ID. NO. 1949 | 423-ValGlnValPheLysProMetSer-430 |
| SEQ. ID. NO. 1950 | 449-SerArgLeuAlaAsnGluTyr-455 |
| SEQ. ID. NO. 1951 | 481-AlaGluPheGluLysAlaAsn-487 |
| SEQ. ID. NO. 1952 | 515-ArgTrpProAspIle-519 |
| Antigenic Index - Jameson-Wolf | |
| SEQ. ID. NO. 1953 | 4-GluIleLeuAspGlnValArgArgArgArgThrPhe-15 |
| SEQ. ID. NO. 1954 | 19-SerHisProAspAlaGlyLysThrThrLeuThr-29 |
| SEQ. ID. NO. 1955 | 43-GlyThrValLysGlyLysLysThrGlyLysPheAlaThr-55 |
| SEQ. ID. NO. 1956 | 57-AspTrpMetGluIleGluLysGlnArgGly-66 |
| SEQ. ID. NO. 1957 | 76-PheAspTyrLysAspHisThrVal-83 |
| SEQ. ID. NO. 1958 | 85-LeuLeuAspThrProGlyHisGlnAspPheSerGluAspThrTyrArg-100 |
| SEQ. ID. NO. 1959 | 113-AspAlaAlaLysGlyValGlu-119 |
| SEQ. ID. NO. 1960 | 129-CysArgLeuArgAspThrPro-135 |
| SEQ. ID. NO. 1961 | 140-MetAsnLysTyrAspArgGluValArgAspSerLeuGluLeuLeuAspGluValGluAsn-159 |
| SEQ. ID. NO. 1962 | 173-GlyMetGlyLysAsnPheLys-179 |
| SEQ. ID. NO. 1963 | 194-AlaGlyGlyGluArgLeuProHis-201 |
| SEQ. ID. NO. 1964 | 207-LysGlyIleAspAsnProGluLeuGluGlnArgPheProLeu-220 |
| SEQ. ID. NO. 1965 | 223-GlnGlnLeuArgAspGluIleGluLeu-231 |
| SEQ. ID. NO. 1966 | 235-AlaSerAsnGluPheAsnLeu-241 |
| SEQ. ID. NO. 1967 | 275-ProAlaProLysProArgAspAlaThrValArgMetValGluProAspGluProLysPhe-294 |
| SEQ. ID. NO. 1968 | 302-GlnAlaAsnMetAspProLysHisArgAspArgIleAla-314 |
| SEQ. ID. NO. 1969 | 317-ArgValCysSerGlyLysPheGluArgGlyMetLysMetLysHisLeuArgIleAsnArgGluIleAla-339 |
| SEQ. ID. NO. 1970 | 348-SerHisAspArgGluLeuValGlu-355 |
| SEQ. ID. NO. 1971 | 365-IleProAsnHisGly-369 |
| SEQ. ID. NO. 1972 | 373-IleGlyAspSerPheSerGluGlyGluGln-382 |
| SEQ. ID. NO. 1973 | 399-ValArgIleLysAsnProLeuLysIleLysGlnLeuGlnLysGlyLeuGlnGlnLeuGlyGluGluGlyAla-422 |
| SEQ. ID. NO. 1974 | 450-ArgLeuAlaAsnGluTyrGlyVal-457 |
| SEQ. ID. NO. 1975 | 459-AlaValPheAspSer-463 |
| SEQ. ID. NO. 1976 | 473-SerCysAspAspLysLysLysLeuAlaGluPheGluLysAlaAsnAla-488 |
| SEQ. ID. NO. 1977 | 503-AlaProAsnArgValAsnLeu-509 |
| SEQ. ID. NO. 1978 | 511-LeuThrGlnGluArgTrpProAspIleVal-520 |
| SEQ. ID. NO. 1979 | 523-GluThrArgGluHisSerVal-529 |
| Hydrophilic Regions - Hopp-Woods | |
| SEQ. ID. NO. 1980 | 4-GluIleLeuAspGlnValArgArgArgArgThr-14 |
| SEQ. ID. NO. 1981 | 21-ProAspAlaGlyLys-25 |
| SEQ. ID. NO. 1982 | 43-GlyThrValLysGlyLysLysThrGlyLys-52 |
| SEQ. ID. NO. 1983 | 59-MetGluIleGluLysGlnArgGly-66 |
| SEQ. ID. NO. 1984 | 77-AspTyrLysAspHisThr-82 |
| SEQ. ID. NO. 1985 | 92-GlnAspPheSerGluAspThrTyr-99 |
| SEQ. ID. NO. 1986 | 113-AspAlaAlaLysGlyValGlu-119 |
| SEQ. ID. NO. 1987 | 129-CysArgLeuArgAspThrPro-135 |
| SEQ. ID. NO. 1988 | 142-LysTyrAspArgGluValArgAspSerLeuGluLeuLeuAspGluValGluAsn-159 |
| SEQ. ID. NO. 1989 | 194-AlaGlyGlyGluArgLeuProHis-201 |
| SEQ. ID. NO. 1990 | 207-LysGlyIleAspAsnProGluLeuGluGlnArgPheProLeu-220 |
| SEQ. ID. NO. 1991 | 223-GlnGlnLeuArgAspGluIleGluLeu-231 |
| SEQ. ID. NO. 1992 | 277-ProLysProArgAspAlaThrValArgMetValGluProAspGluProLysPhe-294 |
| SEQ. ID. NO. 1993 | 305-MetAspProLysHisArgAspArgIleAla-314 |
| SEQ. ID. NO. 1994 | 319-CysSerGlyLysPheGluArgGlyMetLysMetLysHisLeuArgIleAsnArgGluIleAla-339 |
| SEQ. ID. NO. 1995 | 348-SerHisAspArgGluLeuValGlu-355 |
| SEQ. ID. NO. 1996 | 376-SerPheSerGluGlyGluGln-382 |
| SEQ. ID. NO. 1997 | 399-ValArgIleLysAsnProLeuLysIleLysGlnLeuGlnLysGlyLeu-414 |
| SEQ. ID. NO. 1998 | 417-LeuGlyGluGluGlyAla-422 |
| SEQ. ID. NO. 1999 | 473-SerCysAspAspLysLysLysLeuAlaGluPheGluLysAlaAsnAla-488 |
| SEQ. ID. NO. 2000 | 512-ThrGlnGluArgTrpPro-517 |
| SEQ. ID. NO. 2001 135 | 523-GluThrArgGluHisSerVal-529 |
| AMPHI Regions - AMPHI | |
| SEQ. ID. NO. 2002 | 85-GluTyrThrAlaAsnLeu-90 |
| SEQ. ID. NO. 2003 | 169-AspIleAspGlyLeuTyrThr-175 |
| SEQ. ID. NO. 2004 | 185-ValArgLeuAspLysIleGluHis-192 |
| SEQ. ID. NO. 2005 | 212-GlyMetLeuThrLysIle-217 |
| SEQ. ID. NO. 2006 | 236-LeuLysProAspAla-240 |
| SEQ. ID. NO. 2007 | 242-AlaGluAlaAlaGlu-246 |
| SEQ. ID. NO. 2008 | 284-AlaGluHisAlaLeuSer-289 |

TABLE 1-continued

| | |
|---|---|
| SEQ. ID. NO. 2009 | 300-IleAlaGlyIleGluGly-305 |
| SEQ. ID. NO. 2010 | 308-SerArgMetAspThrValThrValTyr-316 |
| SEQ. ID. NO. 2011 | 318-LysAlaThrLysGlnPro-323 |
| Antigenic Index - Jameson-Wolf | |
| SEQ. ID. NO. 2012 | 1-MetLysTyrLysArgIleVal-7 |
| SEQ. ID. NO. 2013 | 11-GlyThrSerSerIleThrHisSerAspGlySerLeuSerArgGlyLysIleGlnThr-29 |
| SEQ. ID. NO. 2014 | 60-GlyPheLysLysArgProValLysIleAlaAspLysGlnAlaSer-74 |
| SEQ. ID. NO. 2015 | 90-LeuSerSerAspGlyIle-95 |
| SEQ. ID. NO. 2016 | 105-AlaAspPheAlaAspLysArgArgTyrGlnAsnAlaGlyGly-118 |
| SEQ. ID. NO. 2017 | 124-LeuGlnArgArgAlaVal-129 |
| SEQ. ID. NO. 2018 | 132-IleAsnGluAsnAspThrValSerValGluGluLeuLysIleGlyAspAsnAspThrLeu-151 |
| SEQ. ID. NO. 2019 | 176-GlyAsnProAsnSerAsnProAspAlaValArgLeuAspLysIleGluHisIleAsn-194 |
| SEQ. ID. NO. 2020 | 202-GlyGlySerGlySerAlaAsnGlyThrGly-211 |
| SEQ. ID. NO. 2021 | 215-ThrLysIleLysAla-219 |
| SEQ. ID. NO. 2022 | 224-AlaGluSerGlyVal-228 |
| SEQ. ID. NO. 2023 | 233-CysSerSerLeuLysProAspAlaLeuAlaGluAlaAlaGluHisGlnAlaAspGly-251 |
| SEQ. ID. NO. 2024 | 257-ArgAlaLysGlyLeuArgThrGlnLysGln-266 |
| SEQ. ID. NO. 2025 | 271-TyrSerGluSerArgGlySerValTyrValAspGluGlyAlaGluHisAlaLeuSerGluGlnGlyLysSerLeuLeu-296 |
| SEQ. ID. NO. 2026 | 305-GlyHisPheSerArgMetAspThr-312 |
| SEQ. ID. NO. 2027 | 317-SerLysAlaThrLysGlnProLeuGlyLysGlyArgVal-329 |
| SEQ. ID. NO. 2028 | 335-AlaAlaGluAspLeuLeuLysSerArgLysAlaLys-346 |
| SEQ. ID. NO. 2029 | 350-IleHisArgAspAspTrpIleSer-357 |
| Hydrophilic Regions - Hopp-Woods | |
| SEQ. ID. NO. 2030 | 1-MetLysTyrLysArgIleVal-7 |
| SEQ. ID. NO. 2031 | 16-ThrHisSerAspGlySerLeuSerArgGlyLysIle-27 |
| SEQ. ID. NO. 2032 | 60-GlyPheLysLysArgProValLysIleAlaAspLysGlnAlaSer-74 |
| SEQ. ID. NO. 2033 | 105-AlaAspPheAlaAspLysArgArgTyrGlnAsn-115 |
| SEQ. ID. NO. 2034 | 124-LeuGlnArgArgAlaVal-129 |
| SEQ. ID. NO. 2035 | 133-AsnGluAsnAspThrValSerValGluGluLeuLysIleGlyAspAsnAspThrLeu-151 |
| SEQ. ID. NO. 2036 | 178-ProAsnSerAsnProAspAlaValArgLeuAspLysIleGluHisIleAsn-194 |
| SEQ. ID. NO. 2037 | 215-ThrLysIleLysAla-219 |
| SEQ. ID. NO. 2038 | 236-LeuLysProAspAlaLeuAlaGluAlaAlaGluHisGlnAlaAsp-250 |
| SEQ. ID. NO. 2039 | 257-ArgAlaLysGlyLeuArgThrGlnLys-265 |
| SEQ. ID. NO. 2040 | 272-SerGluSerArgGly-276 |
| SEQ. ID. NO. 2041 | 278-ValTyrValAspGluGlyAlaGluHisAlaLeuSerGluGlnGlyLys-293 |
| SEQ. ID. NO. 2042 | 306-HisPheSerArgMetAspThr-312 |
| SEQ. ID. NO. 2043 | 318-LysAlaThrLysGlnProLeuGlyLysGlyArgVal-329 |
| SEQ. ID. NO. 2044 | 335-AlaAlaGluAspLeuLeuLysSerArgLysAlaLys-346 |
| SEQ. ID. NO. 2045 | 351-HisArgAspAspTrp-355 |
| 136 | |
| AMPHI Regions - AMPHI | |
| SEQ. ID. NO. 2046 | 37-LeuArgPheValAspAspCysLeuPro-45 |
| SEQ. ID. NO. 2047 | 50-IleArgGlnCysIleArgGln-56 |
| SEQ. ID. NO. 2048 | 84-GlnCysHisAspGlyIleLysGlnLeuPheLysArgPheIleIleAspGlyPheLysProIleGlyArgHis-107 |
| SEQ. ID. NO. 2049 | 119-CysValLysIleAla-123 |
| SEQ. ID. NO. 2050 | 148-ArgHisCysGlnAsn-152 |
| SEQ. ID. NO. 2051 | 170-GlnHisPheGlyGlnPro-175 |
| SEQ. ID. NO. 2052 | 177-GluArgCysGlnPheVal-182 |
| SEQ. ID. NO. 2053 | 194-AsnLeuValAlaThr-198 |
| SEQ. ID. NO. 2054 | 210-GlnPheAlaGlnPro-214 |
| SEQ. ID. NO. 2055 | 216-PheGlyCysPheGlyLysPheSerGlyIleHis-226 |
| Antigenic Index - Jameson-Wolf | |
| SEQ. ID. NO. 2056 | 1-MetGluThrAsnAla-5 |
| SEQ. ID. NO. 2057 | 38-ArgPheValAspAspCysLeu-44 |
| SEQ. ID. NO. 2058 | 48-ValAspIleArgGlnCysIle-54 |
| SEQ. ID. NO. 2059 | 69-LeuGlnThrAspSer-73 |
| SEQ. ID. NO. 2060 | 84-GlnCysHisAspGlyIleLysGlnLeuPhe-93 |
| SEQ. ID. NO. 2061 | 99-AspGlyPheLysProIleGlyArgHisAsnIle-109 |
| SEQ. ID. NO. 2062 | 139-IleArgHisArgGlyGlyCysPheHisArgHisCysGlnAsnGlnProPheAsp-156 |
| SEQ. ID. NO. 2063 | 159-ThrPheGlyGlyGlyLysLeuArg-166 |
| SEQ. ID. NO. 2064 | 171-HisPheGlyGlnProValGluArg-178 |
| SEQ. ID. NO. 2065 | 184-ProAlaGlnGlnArgArgHisLysThr-192 |
| SEQ. ID. NO. 2066 | 214-ProProPheGlyCysPheGlyLysPheSerGly-224 |
| SEQ. ID. NO. 2067 | 236-ProTyrTyrArgArgAsnAlaVal-243 |
| Hydrophilic Regions - Hopp-Woods | |
| SEQ. ID. NO. 2068 | 48-ValAspIleArgGlnCysIle-54 |
| SEQ. ID. NO. 2069 | 87-AspGlyIleLysGlnLeuPhe-93 |
| SEQ. ID. NO. 2070 | 185-AlaGlnGlnArgArgHisLysThr-192 |
| 137 | |
| AMPHI Regions - AMPHI | |
| SEQ. ID. NO. 2071 | 24-LeuSerTyrIleLeuGlyPhe-30 |
| SEQ. ID. NO. 2072 | 49-ThrLysGluSerLeu-53 |
| SEQ. ID. NO. 2073 | 55-AspPheLeuThrTrpGly-60 |
| SEQ. ID. NO. 2074 | 78-PheSerAspTyrLeuAlaHisProLeuAspIlePheLysValTrpGluGlyGly-95 |
| SEQ. ID. NO. 2075 | 120-PheLeuLysLeuMetAspThrValAlaProLeuValPro-132 |
| SEQ. ID. NO. 2076 | 139-ArgIleGlyAsnPheIle-144 |
| SEQ. ID. NO. 2077 | 149-TrpGlyArgValThrAspIleAsnAlaPhe-158 |
| SEQ. ID. NO. 2078 | 178-ProLeuTrpAlaGluTrpLeuGlnGlnTyr-187 |
| SEQ. ID. NO. 2079 | 190-LeuProArgHisProSerGlnLeu-197 |
| SEQ. ID. NO. 2080 | 232-TyrGlyIlePheArgPheIleAlaGluPheAlaArgGlnProAspAspTyrLeuGly-250 |

TABLE 1-continued

Antigenic Index - Jameson-Wolf
SEQ. ID. NO. 2081   36-LeuGlyArgArgArgIleAlaGln-43
SEQ. ID. NO. 2082   48-PheThrLysGluSerLeuAspAsp-55
SEQ. ID. NO. 2083   92-TrpGluGlyGlyMet-96
SEQ. ID. NO. 2084   111-LeuPheGlyArgLysHisGly-117
SEQ. ID. NO. 2085   136-AlaSerGlyArgIle-140
SEQ. ID. NO. 2086   164-ProGlnAlaArgTyrGluAspAlaGluAlaAlaAla-175
SEQ. ID. NO. 2087   191-ProArgHisProSerGlnLeu-197
SEQ. ID. NO. 2088   214-PheSerLysLysGlnArgSerThrGlyGln-223
SEQ. ID. NO. 2089   241-PheAlaArgGlnProAspAspTyrLeu-249
SEQ. ID. NO. 2090   277-PheGlyMetLysLysGlnHis-283
Hydrophilic Regions - Hopp-Woods
SEQ. ID. NO. 2091   37-GlyArgArgArgIleAla-42
SEQ. ID. NO. 2092   48-PheThrLysGluSerLeuAsp-54
SEQ. ID. NO. 2093   112-PheGlyArgLysHisGly-117
SEQ. ID. NO. 2094   166-AlaArgTyrGluAspAlaGluAlaAlaAla-175
SEQ. ID. NO. 2095   216-LysLysGlnArgSerThrGly-222
SEQ. ID. NO. 2096   241-PheAlaArgGlnProAspAspTyr-248
SEQ. ID. NO. 2097   278-GlyMetLysLysGlnHis-283
138
AMPHI Regions - AMPHI
SEQ. ID. NO. 2098   21-ProTyrIleArgArgPheSerGlySer-29
SEQ. ID. NO. 2099   74-AsnAlaMetLeuGluLysVal-80
SEQ. ID. NO. 2100   85-GluPheValGlnGlyMet-90
SEQ. ID. NO. 2101   109-ValAsnLysGluIleValSerMetIleAsnThrTyrGly-121
SEQ. ID. NO. 2102   152-IleGlyGlnValGlyThrValGluSerIle-161
SEQ. ID. NO. 2103   163-ThrGlyLeuValLysGlyLeu-169
SEQ. ID. NO. 2104   199-GlyLysLeuAlaGluGluLeu-205
SEQ. ID. NO. 2105   213-MetThrAsnIleAlaGlyValMetAspLysThrGlyAsnLeuLeuThrLysLeuThr-231
SEQ. ID. NO. 2106   234-ArgIleAspGluLeuIle-239
SEQ. ID. NO. 2107   247-GlyMetLeuProLysIleAlaSerAlaValGluAlaAlaValAsn-261
SEQ. ID. NO. 2108   276-AlaLeuLeuLeuGluIlePheThrAspAla-285
Antigenic Index - Jameson-Wolf
SEQ. ID. NO. 2109   1-MetGluSerGluAsnIle-6
SEQ. ID. NO. 2110   9-AlaAlaAspLysAlaArgIleLeu-16
SEQ. ID. NO. 2111   23-IleArgArgPheSerGlySer-29
SEQ. ID. NO. 2112   35-TyrGlyGlyAsnAlaMetThr-41
SEQ. ID. NO. 2113   43-ProAlaLeuLysGluGlyPheAla-50
SEQ. ID. NO. 2114   68-GlyGlyGlyProGln-72
SEQ. ID. NO. 2115   76-MetLeuGluLysValGlyLysLysGlyGluPhe-86
SEQ. ID. NO. 2116   91-ArgValThrAspLysGluAlaMetAsp-99
SEQ. ID. NO. 2117   109-ValAsnLysGluIle-113
SEQ. ID. NO. 2118   128-SerGlyArgAspAspHisPheIleLysAlaLysLysLeuLeuIleAspThrProGluGlnAsnGlyValAspIleGlyGln-154
SEQ. ID. NO. 2119   159-GluSerIleAspThrGlyLeu-165
SEQ. ID. NO. 2120   169-LeuIleGluArgGlyCysIle-175
SEQ. ID. NO. 2121   182-GlyValGlyGluLysGlyGluAla-189
SEQ. ID. NO. 2122   200-LysLeuAlaGluGluLeuAsnAlaGluLys-209
SEQ. ID. NO. 2123   219-ValMetAspLysThrGlyAsnLeuLeuThrLysLeuThrProLysArgIleAspGluLeuIleAla-240
SEQ. ID. NO. 2124   259-AlaValAsnGlyValLys-264
SEQ. ID. NO. 2125   269-IleAspGlyArgLeuProAsnAla-276
SEQ. ID. NO. 2126   292-LeuGlyGlyGlyGluAspAla-298
Hydrophilic Regions - Hopp-Woods
SEQ. ID. NO. 2127   1-MetGluSerGluAsn-5
SEQ. ID. NO. 2128   9-AlaAlaAspLysAlaArgIleLeu-16
SEQ. ID. NO. 2129   43-ProAlaLeuLysGluGlyPheAla-50
SEQ. ID. NO. 2130   76-MetLeuGluLysValGlyLysLysGlyGluPhe-86
SEQ. ID. NO. 2131   91-ArgValThrAspLysGluAlaMetAsp-99
SEQ. ID. NO. 2132   109-ValAsnLysGluIle-113
SEQ. ID. NO. 2133   128-SerGlyArgAspAspHisPheIleLysAlaLysLysLeuLeuIleAspThrProGluGlnAsnGlyValAsp-151
SEQ. ID. NO. 2134   183-ValGlyGluLysGlyGluAla-189
SEQ. ID. NO. 2135   200-LysLeuAlaGluGluLeuAsnAlaGluLys-209
SEQ. ID. NO. 2136   219-ValMetAspLysThrGly-224
SEQ. ID. NO. 2137   230-LeuThrProLysArgIleAspGluLeuIleAla-240
SEQ. ID. NO. 2138   269-IleAspGlyArgLeu-273
SEQ. ID. NO. 2139   294-GlyGlyGluAspAla-298
140-2
AMPHI Regions - AMPHI
SEQ. ID. NO. 2140   23-ThrThrLeuSerAlaCysLeuGly-30
SEQ. ID. NO. 2141   105-AspPheProAsnProAsnAspAlaTyrLysAsnLeuIle-117
SEQ. ID. NO. 2142   139-ThrGlyGluSerValGlySerIleSerPhePro-149
SEQ. ID. NO. 2143   201-AspIleArgHisValLysGluIleGlyHisIleAspLeuValSer-215
SEQ. ID. NO. 2144   253-AlaAlaIleArgAsnAlaTrpValLysLeuGly-263
SEQ. ID. NO. 2145   266-GlyValArgIleVal-270
SEQ. ID. NO. 2146   282-ThrAlaAspLeuPheGlnIle-288
SEQ. ID. NO. 2147   311-GlyIleArgLeuMetGlnGlnSerAsp-319
SEQ. ID. NO. 2148   370-AspArgSerGlyGluLysPheLysArgGluMetTyr-381
SEQ. ID. NO. 2149   415-ThrArgThrAsnPro-419
SEQ. ID. NO. 2150   458-ThrAlaGlnAspIle-462
SEQ. ID. NO. 2151   476-LeuAspAlaGlyLysAlaMetAsnGlyPro-485
SEQ. ID. NO. 2152   608-TyrThrArgLeuGlyLysLeuLeuLys-616

TABLE 1-continued

| | |
|---|---|
| SEQ. ID. NO. 2153 | 673-SerLeuAspSerValGluLysThrAlaGly-682 |
| SEQ. ID. NO. 2154 | 696-AsnAlaAlaArgThrAlaSer-702 |
| SEQ. ID. NO. 2155 | 736-SerAlaThrProGluThrValGluThrAlaAla-746 |
| SEQ. ID. NO. 2156 | 763-ArgAlaAlaAlaAlaValGlnHisAlaAsnAlaAlaAspGlyValArgIlePheAsnSerLeuAlaAlaThr-786 |
| SEQ. ID. NO. 2157 | 803-LeuLysAlaValSerAspGlyLeuAsp-811 |
| SEQ. ID. NO. 2158 | 817-LeuArgValIleAlaGln-822 |
| SEQ. ID. NO. 2159 | 882-SerLeuPheAlaGly-886 |
| SEQ. ID. NO. 2160 | 894-IleGlyTyrLeuLysGlyLeuPheSerTyr-903 |
| SEQ. ID. NO. 2161 | 918-GluHisAlaGluGlySer-923 |
| SEQ. ID. NO. 2162 | 931-LeuGlyAlaLeuGly-935 |
| SEQ. ID. NO. 2163 | 980-GlyThrLeuValGlyLeu-985 |
| SEQ. ID. NO. 2164 | 1019-GlyGlyPheThrGlyAlaThr-1025 |
| SEQ. ID. NO. 2165 | 1040-ArgLeuValAlaGlyLeu-1045 |
| SEQ. ID. NO. 2166 | 1053-AsnGlyTrpAsnGlyLeuAlaArg-1060 |
| Antigenic Index - Jameson-Wolf | |
| SEQ. ID. NO. 2167 | 1-MetArgThrThrPro-5 |
| SEQ. ID. NO. 2168 | 7-PheProThrLysThrPheLysProThr-15 |
| SEQ. ID. NO. 2169 | 30-GlyGlyGlyGlyGlyGlyThrSerAlaProAspPheAsnAlaGlyGlyThrGlyIleGlySerAsnSerArgAlaThrThrAlaLys-58 |
| SEQ. ID. NO. 2170 | 67-IleLysAsnGluMetCysLysAspArgSerMet-77 |
| SEQ. ID. NO. 2171 | 79-CysAlaGlyArgAspAspValAlaValThrAspArgAspAlaLysIleAsnAlaProProProAsnLeuHisThrGlyAspPheProAsnProAsnAspAlaTyrLysAsn-115 |
| SEQ. ID. NO. 2172 | 127-TyrThrGlyArgGlyValGlu-133 |
| SEQ. ID. NO. 2173 | 138-AspThrGlyGluSerValGlySerIleSerPhe-148 |
| SEQ. ID. NO. 2174 | 151-LeuTyrGlyArgLysGluHisGlyTyrAsnGluAsnTyrLysAsn-165 |
| SEQ. ID. NO. 2175 | 170-MetArgLysGluAlaProGluAspGlyGlyGlyLysAspIleGluAlaSerPheAspAspGluAlaValIleGluThrGluAlaLysProThrAspIleArgHisValLysGluIleGlyHis-210 |
| SEQ. ID. NO. 2176 | 220-GlyArgSerValAspGlyArgProAlaGlyGlyIleAlaProAspAla-235 |
| SEQ. ID. NO. 2177 | 241-AsnThrAsnAspGluThrLysAsnGluMet-250 |
| SEQ. ID. NO. 2178 | 262-LeuGlyGluArgGlyValArg-268 |
| SEQ. ID. NO. 2179 | 272-AsnSerPheGlyThrThrSerArgAlaGlyThrAlaAsp-284 |
| SEQ. ID. NO. 2180 | 288-IleAlaAsnSerGluGluGlnTyrArg-296 |
| SEQ. ID. NO. 2181 | 301-AspTyrSerGlyGlyAspLysThrAspGluGlyIleArg-313 |
| SEQ. ID. NO. 2182 | 315-MetGlnGlnSerAspTyrGlyAsn-322 |
| SEQ. ID. NO. 2183 | 327-IleArgAsnLysAsnMet-332 |
| SEQ. ID. NO. 2184 | 337-SerThrGlyAsnAspAlaGlnAlaGlnProAsnThr-348 |
| SEQ. ID. NO. 2185 | 355-TyrGluLysAspAlaGlnLys-361 |
| SEQ. ID. NO. 2186 | 368-GlyValAspArgSerGlyGluLysPheLysArgGluMetTyrGlyGluProGlyThrGluProLeuGluTyrGlySerAsnHis-395 |
| SEQ. ID. NO. 2187 | 412-ValArgPheThrArgThrAsnPro-419 |
| SEQ. ID. NO. 2188 | 446-MetSerAsnAspAsnLeuArgThr-453 |
| SEQ. ID. NO. 2189 | 467-ValAspSerLysPheGly-472 |
| SEQ. ID. NO. 2190 | 477-AspAlaGlyLysAlaMetAsnGlyProAla-486 |
| SEQ. ID. NO. 2191 | 492-AspPheThrAlaAspThrLysGlyThrSer-501 |
| SEQ. ID. NO. 2192 | 506-SerPheArgAsnAspIleSerGlyThr-514 |
| SEQ. ID. NO. 2193 | 516-GlyLeuIleLysLysGlyGlySerGln-524 |
| SEQ. ID. NO. 2194 | 529-GlyAsnAsnThrTyrThrGlyLysThrIleIleGluGlyGlySer-543 |
| SEQ. ID. NO. 2195 | 548-GlyAsnAsnLysSerAspMetArgValGluThrLysGly-560 |
| SEQ. ID. NO. 2196 | 568-AlaSerGlyGlySerLeuAsnSerAspGly-577 |
| SEQ. ID. NO. 2197 | 582-AlaAspThrAspGlnSerGlyAlaAsnGlu-591 |
| SEQ. ID. NO. 2198 | 593-ValHisIleLysGlySerLeuGlnLeuAspGlyLysGlyThrLeu-607 |
| SEQ. ID. NO. 2199 | 615-LeuLysValAspGly-619 |
| SEQ. ID. NO. 2200 | 629-MetSerAlaArgGlyLysGlyAlaGly-637 |
| SEQ. ID. NO. 2201 | 640-AsnSerThrGlyArgArgValPro-647 |
| SEQ. ID. NO. 2202 | 653-LysIleGlyGlnAspTyr-658 |
| SEQ. ID. NO. 2203 | 663-AsnIleGluThrAspGlyLeu-670 |
| SEQ. ID. NO. 2204 | 675-AspSerValGluLysThrAlaGlySerGluGlyAspThrLeu-688 |
| SEQ. ID. NO. 2205 | 691-TyrValArgArgGlyAsnAlaAlaArgThrAlaSer-702 |
| SEQ. ID. NO. 2206 | 714-HisAlaValGluGlnGlyGlySerAsnLeuGlu-724 |
| SEQ. ID. NO. 2207 | 730-LeuAspAlaSerGluSerSerAlaThrProGluThrValGlu-743 |
| SEQ. ID. NO. 2208 | 745-AlaAlaAlaAspArgThrAspMetProGlyIleArgProTyrGly-759 |
| SEQ. ID. NO. 2209 | 772-AsnAlaAlaAspGly-776 |
| SEQ. ID. NO. 2210 | 788-TyrAlaAspSerThrAlaAla-794 |
| SEQ. ID. NO. 2211 | 797-AspMetGlnGlyArgArgLeuLysAlaValSerAspGlyLeuAspHisAsnGlyThrGlyLeu-817 |
| SEQ. ID. NO. 2212 | 823-ThrGlnGlnAspGlyGlyThrTrpGluGlnGlyGlyValGluGlyLysMetArgGlySerThrGln-844 |
| SEQ. ID. NO. 2213 | 849-AlaAlaLysThrGlyGluAsnThrThr-857 |
| SEQ. ID. NO. 2214 | 863-GlyMetGlyArgSerThrTrpSerGluAsnSerAlaAsnAlaLysThrAspSerIle-881 |
| SEQ. ID. NO. 2215 | 887-IleArgHisAspAlaGlyAsp-893 |
| SEQ. ID. NO. 2216 | 902-SerTyrGlyArgTyrLysAsnSerIleSerArgSerThrGlyAlaAspGluHisAlaGluGlySerValAsn-925 |
| SEQ. ID. NO. 2217 | 943-AlaThrGlyAspLeuThrValGluGlyGlyLeuValArg-954 |
| SEQ. ID. NO. 2218 | 961-AspAlaPheAlaGluLysGlySerAlaLeuGlyTrpSerGlyAsnSerLeuThrGluGlyThr-981 |
| SEQ. ID. NO. 2219 | 990-LeuSerGlnProLeuSerAspLys-997 |
| SEQ. ID. NO. 2220 | 1005-GlyValGluArgAspLeuAsnGlyArgAspTyrThrVal-1017 |
| SEQ. ID. NO. 2221 | 1027-AlaThrGlyLysThrGlyAlaArgAsnMetProHisThr-1039 |
| SEQ. ID. NO. 2222 | 1049-ValGluPheGlyAsnGlyTrp-1055 |
| SEQ. ID. NO. 2223 | 1062-SerTyrAlaGlySerLysGlnTyrGlyAsnHisSerGlyArgValGlyVal-1078 |
| Hydrophilic Regions - Hopp-Woods | |
| SEQ. ID. NO. 2224 | 50-SerAsnSerArgAlaThrThrAlaLys-58 |
| SEQ. ID. NO. 2225 | 67-IleLysAsnGluMetCysLysAspArgSerMet-77 |
| SEQ. ID. NO. 2226 | 80-AlaGlyArgAspAspValAlaValThrAspArgAspAlaLysIleAsnAla-96 |
| SEQ. ID. NO. 2227 | 106-PheProAsnProAsnAspAlaTyr-113 |
| SEQ. ID. NO. 2228 | 138-AspThrGlyGluSerValGly-144 |

TABLE 1-continued

| SEQ. ID. NO. | Sequence |
|---|---|
| SEQ. ID. NO. 2229 | 152-TyrGlyArgLysGluHisGlyTyr-159 |
| SEQ. ID. NO. 2230 | 170-MetArgLysGluAlaProGluAspGlyGlyGlyLysAspIleGluAlaSerPheAspAspGluAlaValIleGluThrGluAlaLysProThrAspIle ArgHisValLysGluIleGlyHis-210 |
| SEQ. ID. NO. 2231 | 221-ArgSerValAspGlyArgProAlaGly-229 |
| SEQ. ID. NO. 2232 | 242-ThrAsnAspGluThrLysAsnGluMet-250 |
| SEQ. ID. NO. 2233 | 262-LeuGlyGluArgGlyValArg-268 |
| SEQ. ID. NO. 2234 | 278-SerArgAlaGlyThr-282 |
| SEQ. ID. NO. 2235 | 290-AsnSerGluGluGlnTyrArg-296 |
| SEQ. ID. NO. 2236 | 303-SerGlyGlyAspLysThrAspGluGlyIleArg-313 |
| SEQ. ID. NO. 2237 | 327-IleArgAsnLysAsn-331 |
| SEQ. ID. NO. 2238 | 339-GlyAsnAspAlaGlnAla-344 |
| SEQ. ID. NO. 2239 | 355-TyrGluLysAspAlaGlnLys-361 |
| SEQ. ID. NO. 2240 | 368-GlyValAspArgSerGlyGluLysPheLysArgGluMetTyrGly-382 |
| SEQ. ID. NO. 2241 | 384-ProGlyThrGluProLeuGlu-390 |
| SEQ. ID. NO. 2242 | 412-ValArgPheThrArg-416 |
| SEQ. ID. NO. 2243 | 477-AspAlaGlyLysAlaMetAsn-483 |
| SEQ. ID. NO. 2244 | 493-PheThrAlaAspThrLysGlyThrSer-501 |
| SEQ. ID. NO. 2245 | 509-AsnAspIleSerGly-513 |
| SEQ. ID. NO. 2246 | 517-LeuIleLysLysGlyGlySer-523 |
| SEQ. ID. NO. 2247 | 550-AsnLysSerAspMetArgValGluThrLysGly-560 |
| SEQ. ID. NO. 2248 | 583-AspThrAspGlnSerGlyAlaAsnGlu-591 |
| SEQ. ID. NO. 2249 | 601-LeuAspGlyLysGly-605 |
| SEQ. ID. NO. 2250 | 615-LeuLysValAspGly-619 |
| SEQ. ID. NO. 2251 | 631-AlaArgGlyLysGly-635 |
| SEQ. ID. NO. 2252 | 642-ThrGlyArgArgValPro-647 |
| SEQ. ID. NO. 2253 | 664-IleGluThrAspGly-668 |
| SEQ. ID. NO. 2254 | 675-AspSerValGluLysThrAlaGlySerGluGlyAspThr-687 |
| SEQ. ID. NO. 2255 | 692-ValArgArgGlyAsnAlaAlaArgThrAlaSer-702 |
| SEQ. ID. NO. 2256 | 714-HisAlaValGluGlnGlyGlySerAsnLeu-723 |
| SEQ. ID. NO. 2257 | 730-LeuAspAlaSerGluSerSerAlaThrProGluThrValGlu-743 |
| SEQ. ID. NO. 2258 | 745-AlaAlaAlaAspArgThrAspMetProGly-754 |
| SEQ. ID. NO. 2259 | 772-AsnAlaAlaAspGly-776 |
| SEQ. ID. NO. 2260 | 797-AspMetGlnGlyArgArgLeuLysAlaValSerAspGlyLeuAspHisAsnGlyThr-815 |
| SEQ. ID. NO. 2261 | 833-GlyGlyValGluGlyLysMetArgGlySerThr-843 |
| SEQ. ID. NO. 2262 | 851-LysThrGlyGluAsnThrThr-857 |
| SEQ. ID. NO. 2263 | 872-AsnSerAlaAsnAlaLysThrAspSer-880 |
| SEQ. ID. NO. 2264 | 887-IleArgHisAspAlaGlyAsp-893 |
| SEQ. ID. NO. 2265 | 905-ArgTyrLysAsnSerIleSerArgSerThrGlyAlaAspGluHisAlaGluGlySerVal-924 |
| SEQ. ID. NO. 2266 | 961-AspAlaPheAlaGluLysGlySer-968 |
| SEQ. ID. NO. 2267 | 992-GlnProLeuSerAspLys-997 |
| SEQ. ID. NO. 2268 | 1005-GlyValGluArgAspLeuAsnGlyArgAspTyrThr-1016 |
| SEQ. ID. NO. 2269 | 1027-AlaThrGlyLysThrGlyAlaArgAsnMetPro-1037 |
| 141 | |
| AMPHI Regions - AMPHI | |
| SEQ. ID. NO. 2270 | 11-GlnSerSerThrMetArgProIleGlyGluIle-21 |
| SEQ. ID. NO. 2271 | 44-ProAlaGluAlaPheLysLeuPro-51 |
| SEQ. ID. NO. 2272 | 80-AlaAspAlaLeuArgHisIle-86 |
| SEQ. ID. NO. 2273 | 131-PheHisAlaIleGlyAla-136 |
| SEQ. ID. NO. 2274 | 139-AsnLeuLeuAlaAlaMetLeuAspAsn-147 |
| SEQ. ID. NO. 2275 | 174-GlnLeuArgAsnIleIleAspGlyMetGlyLysProValAspGlyValMetArgPro-192 |
| SEQ. ID. NO. 2276 | 212-AspIleSerAspLeuLysGluArgLeuGlyIleLeuVal-225 |
| SEQ. ID. NO. 2277 | 245-MetAlaAlaLeuLeuLysAspAlaIleLysProAsnLeu-257 |
| SEQ. ID. NO. 2278 | 259-GlnThrIleGluGlyThrPro-265 |
| SEQ. ID. NO. 2279 | 272-ProPheAlaAsnIleAlaHisGlyCysAsnSerValThrAlaThrArgLeuAlaLysHisLeuAlaAspTyrAla-296 |
| SEQ. ID. NO. 2280 | 330-AlaThrValArgAla-334 |
| SEQ. ID. NO. 2281 | 351-LeuAspAlaLeuGluLysGlyLeuProAsnLeuLeuLysHisIleSersnLeuLysAsnValPheGly-373 |
| SEQ. ID. NO. 2282 | 406-SerLeuThrGluValTrpGlyLys-413 |
| SEQ. ID. NO. 2283 | 420-AspLeuAlaArgLysValValAsnAlaIleGluSerGln-432 |
| SEQ. ID. NO. 2284 | 473-IleAlaSerLeuGluLys-478 |
| SEQ. ID. NO. 2285 | 525-ValAlaLeuCysGlyAsnMetMetLysMetProGlyLeuProValProAlaAla-543 |
| Antigenic Index - Jameson-Wolf | |
| SEQ. ID. NO. 2286 | 3-PheLysThrAspAlaGluIleAlaGlnSerSerThrMetArgProIleGly-19 |
| SEQ. ID. NO. 2287 | 27-LeuAsnAlaAspAsnIleGluProTyrGly-36 |
| SEQ. ID. NO. 2288 | 38-TyrLysAlaLysIleAsnProAlaGluAlaPheLysLeuProGlnLysGlnGlyArg-56 |
| SEQ. ID. NO. 2289 | 64-AsnProThrProAlaGlyGluGlyLysThrThr-74 |
| SEQ. ID. NO. 2290 | 81-AspAlaLeuArgHisIleGlyLysAspAla-90 |
| SEQ. ID. NO. 2291 | 94-LeuArgGluProSerLeuGlyPro-101 |
| SEQ. ID. NO. 2292 | 105-ValLysGlyGlyAlaAlaGlyGlyGly-113 |
| SEQ. ID. NO. 2293 | 151-GlnGlyAsnGluLeuAsnIleAspProLysArgValLeuTrp-164 |
| SEQ. ID. NO. 2294 | 166-ArgValValAspMetAsnAspArgGlnLeuArgAsnIleIleAspGlyMetGlyLysProValAspGlyValMetArgProAspGlyPheAspIle-197 |
| SEQ. ID. NO. 2295 | 211-LysAspIleSerAspLeuLysGluArgLeuGly-221 |
| SEQ. ID. NO. 2296 | 227-TyrAlaLysAspGlySerProValTyr-235 |
| SEQ. ID. NO. 2297 | 237-LysAspLeuLysAlaAsnGly-243 |
| SEQ. ID. NO. 2298 | 251-AspAlaIleLysProAsnLeu-257 |
| SEQ. ID. NO. 2299 | 287-ArgLeuAlaLysHisLeuAla-293 |
| SEQ. ID. NO. 2300 | 306-LeuGlyAlaGluLysPheCysAspIleLysCysArgLeuAlaGlyLeuLysProAspAla-325 |
| SEQ. ID. NO. 2301 | 335-LeuLysTyrAsnGlyGlyValGluArgAlaAsnLeuGlyGluAsnLeuAspAlaLeuGluLysGlyLeuProAsnLeu-361 |
| SEQ. ID. NO. 2302 | 383-PheValSerAspAlaAspAlaGluLeuAlaMetIleGluLysAlaCysAla-399 |
| SEQ. ID. NO. 2303 | 411-TrpGlyLysGlyGlyAlaGlyGlyAlaAspLeuAlaArgLysValValAsn-427 |
| SEQ. ID. NO. 2304 | 429-IleGluSerGlnThrAsnAsnPheGly-437 |

TABLE 1-continued

| | |
|---|---|
| SEQ. ID. NO. 2305 | 444-LeuGlyIleLysAspLysIleArgAlaIleAla-454 |
| SEQ. ID. NO. 2306 | 458-TyrGlyAlaGluAspValAspPheSerAla-467 |
| SEQ. ID. NO. 2307 | 474-AlaSerLeuGluLysLeuGlyLeuAspLysMetPro-485 |
| SEQ. ID. NO. 2308 | 494-SerLeuSerAspAsnAlaLys-500 |
| SEQ. ID. NO. 2309 | 503-GlyCysProGluAspPheArgIle-510 |
| SEQ. ID. NO. 2310 | 534-MetProGlyLeuPro-538 |
| SEQ. ID. NO. 2311 | 541-ProAlaAlaGluLysIleAspValAspAlaGluGly-552 |
| Hydrophilic Regions - Hopp-Woods | |
| SEQ. ID. NO. 2312 | 3-PheLysThrAspAlaGluIleAlaGln-11 |
| SEQ. ID. NO. 2313 | 38-TyrLysAlaLysIleAsnPro-44 |
| SEQ. ID. NO. 2314 | 46-GluAlaPheLysLeuProGlnLysGlnGlyArg-56 |
| SEQ. ID. NO. 2315 | 67-ProAlaGlyGluGlyLysThr-73 |
| SEQ. ID. NO. 2316 | 81-AspAlaLeuArgHisIleGlyLysAspAla-90 |
| SEQ. ID. NO. 2317 | 94-LeuArgGluProSer-98 |
| SEQ. ID. NO. 2318 | 155-LeuAsnIleAspProLysArgValLeuTrp-164 |
| SEQ. ID. NO. 2319 | 166-ArgValValAspMetAsnAspArgGlnLeuArgAsnIleIle-179 |
| SEQ. ID. NO. 2320 | 181-GlyMetGlyLysProValAspGlyValMetArgProAspGlyPhe-195 |
| SEQ. ID. NO. 2321 | 211-LysAspIleSerAspLeuLysGluArgLeuGly-221 |
| SEQ. ID. NO. 2322 | 228-AlaLysAspGlySer-232 |
| SEQ. ID. NO. 2323 | 237-LysAspLeuLysAla-241 |
| SEQ. ID. NO. 2324 | 287-ArgLeuAlaLysHisLeuAla-293 |
| SEQ. ID. NO. 2325 | 306-LeuGlyAlaGluLysPheCysAspIleLysCysArgLeuAlaGlyLeuLysProAspAla-325 |
| SEQ. ID. NO. 2326 | 339-GlyGlyValGluArgAlaAsnLeuGlyGluGluAsnLeuAspAlaLeuGluLysGlyLeu-358 |
| SEQ. ID. NO. 2327 | 383-PheValSerAspAlaAspAlaGluLeuAlaMetIleGluLysAlaCysAla-399 |
| SEQ. ID. NO. 2328 | 420-AspLeuAlaArgLysValValAsn-427 |
| SEQ. ID. NO. 2329 | 444-LeuGlyIleLysAspLysIleArgAlaIleAla-454 |
| SEQ. ID. NO. 2330 | 458-TyrGlyAlaGluAspValAspPheSerAla-467 |
| SEQ. ID. NO. 2331 | 474-AlaSerLeuGluLysLeuGlyLeuAspLysMetPro-485 |
| SEQ. ID. NO. 2332 | 503-GlyCysProGluAspPheArgIle-510 |
| SEQ. ID. NO. 2333 | 541-ProAlaAlaGluLysIleAspValAspAlaGluGly-552 |
| 142-2 | |
| AMPHI Regions - AMPHI | |
| SEQ. ID. NO. 2334 | 26-ArgPheAlaAlaMetProAspValValGlyLys-36 |
| SEQ. ID. NO. 2335 | 44-GlyGlnProGlyLysMetPhe-50 |
| SEQ. ID. NO. 2336 | 100-AlaValThrProCysArg-105 |
| SEQ. ID. NO. 2337 | 107-ValCysArgAspAspMet-112 |
| SEQ. ID. NO. 2338 | 130-PheLeuGlnIleArgHisPheSerProLeu-139 |
| SEQ. ID. NO. 2339 | 174-LeuArgValGlnArgIleLeuAspPheGlyLysPheCysGlnGlnVal-189 |
| SEQ. ID. NO. 2340 | 202-LeuAspSerValValAlaPheValHisPhePheAlaAspPheLeuIle-217 |
| SEQ. ID. NO. 2341 | 239-AlaAspAsnGlnThrArgPhePheLysAlaGly-249 |
| SEQ. ID. NO. 2342 | 259-AsnAlaArgLeuIleArgGlnIleLeuLys-268 |
| Antigenic Index - Jameson-Wolf | |
| SEQ. ID. NO. 2343 | 31-ProAspValValGly-35 |
| SEQ. ID. NO. 2344 | 38-LeuPheGlyArgGlnAlaGlyGlnProGlyLysMet-49 |
| SEQ. ID. NO. 2345 | 59-GlnArgIleAspAlaGluAlaAlaValPheArgGlnAspArgAsnAspSerArgThrProValAspAlaGlnHisHisGlyArgArgLeuValGlyAsnArgArgAspArgArgHisCysAsnAla-100 |
| SEQ. ID. NO. 2346 | 102-ThrProCysArgThrValCysArgAspAspMetAsnAlaCysArgAlaArgCysHisArgIleThrGluArgSerLeu-127 |
| SEQ. ID. NO. 2347 | 147-AlaAlaHisLysAlaSerPro-153 |
| SEQ. ID. NO. 2348 | 155-CysSerSerPheAspSerLysSerArgArgSerAspValSerAlaArgTyr-171 |
| SEQ. ID. NO. 2349 | 180-LeuAspPheGlyLysPheCys-186 |
| SEQ. ID. NO. 2350 | 225-GlnLeuGlnLysAsnThrSer-231 |
| SEQ. ID. NO. 2351 | 237-PheGlnAlaAspAsnGlnThrArgPhePheLysAlaGlyGlnAspThrGlyGlnAlaGlyAlaGlnAsn-259 |
| SEQ. ID. NO. 2352 | 267-LeuLysValGlnArgAlaValPheArgGlnLysThrAspAsnProPro-282 |
| SEQ. ID. NO. 2353 | 291-IleGlnAsnArgProGluLeuGlyHisGlnGly-301 |
| SEQ. ID. NO. 2354 | 307-GlnThrAspIleAspArgArgMetPhe-315 |
| Hydrophilic Regions - Hopp-Woods | |
| SEQ. ID. NO. 2355 | 42-GlnAlaGlyGlnPro-46 |
| SEQ. ID. NO. 2356 | 59-GlnArgIleAspAlaGluAlaAlaValPheArgGlnAspArgAsnAspSerArgThrProValAspAlaGlnHisHisGlyArgArgLeuValGlyAsnArgArgAspArgArgHisCys-98 |
| SEQ. ID. NO. 2357 | 106-ThrValCysArgAspAspMetAsnAlaCysArgAlaArgCysHisArgIleThrGluArgSerLeu-127 |
| SEQ. ID. NO. 2358 | 147-AlaAlaHisLysAlaSerPro-153 |
| SEQ. ID. NO. 2359 | 158-PheAspSerLysSerArgArgSerAspValSerAla-169 |
| SEQ. ID. NO. 2360 | 237-PheGlnAlaAspAsnGlnThrArgPhePheLysAlaGlyGlnAspThrGlyGln-254 |
| SEQ. ID. NO. 2361 | 267-LeuLysValGlnArgAlaValPheArgGlnLysThrAspAsn-280 |
| SEQ. ID. NO. 2362 | 291-IleGlnAsnArgProGluLeuGly-298 |
| SEQ. ID. NO. 2363 | 309-AspIleAspArgArgMetPhe-315 |
| 144-2 | |
| AMPHI Regions - AMPHI | |
| SEQ. ID. NO. 2364 | 36-LeuGlyGlyIleValGlnGluPhe-43 |
| SEQ. ID. NO. 2365 | 45-ValLeuAlaAspGlyValArg-51 |
| SEQ. ID. NO. 2366 | 71-IleAsnLysGlnIleGlyArgValAlaGlyArg-81 |
| SEQ. ID. NO. 2367 | 136-SerAlaAspGlyTyr-140 |
| SEQ. ID. NO. 2368 | 212-SerAspAspLeuGluValPheAspPheSerArgProLys-224 |
| SEQ. ID. NO. 2369 | 234-ArgArgGluThrGlyArgAlaGlyPhe-242 |
| SEQ. ID. NO. 2370 | 244-AlaTyrArgValProSerAspIleGlyArgProAlaAla-257 |
| SEQ. ID. NO. 2371 | 283-ProGlnAspPheAlaArg-288 |
| SEQ. ID. NO. 2372 | 295-AspAlaLeuAlaThr-299 |
| SEQ. ID. NO. 2373 | 306-AspSerLeuAsnTrpProGluPheGlyAsn-315 |
| Antigenic Index - Jameson-Wolf | |
| SEQ. ID. NO. 2374 | 1-MetSerAspThrProAlaThrArgAspPheGlyLeuIleAspGlyArgAla-17 |

TABLE 1-continued

| | |
|---|---|
| SEQ. ID. NO. 2375 | 23-LeuSerAsnArgArgGlyThrArg-30 |
| SEQ. ID. NO. 2376 | 48-AspGlyValArgGlu-52 |
| SEQ. ID. NO. 2377 | 58-PheAspAspAlaAlaSerTyrAlaAspAsnProPheGlnIleAsn-72 |
| SEQ. ID. NO. 2378 | 78-ValAlaGlyArgIleArgGlyAlaAla-86 |
| SEQ. ID. NO. 2379 | 88-AspIleAsnGlyArgThrTyrArgValGluAlaAsnGluGlyArgAsnAlaLeuHisGlyGlySerHis-110 |
| SEQ. ID. NO. 2380 | 121-AlaAlaAspGlyArgSerValValLeu-129 |
| SEQ. ID. NO. 2381 | 131-SerArgLeuGlnGlnSerAlaAspGlyTyrProAsnAspLeuAspLeuAspIleSerTyrArgLeuAspGluAspAspArgLeuThrVal-160 |
| SEQ. ID. NO. 2382 | 199-MetProAlaAspAlaGluLysLeuPro-207 |
| SEQ. ID. NO. 2383 | 210-ThrValSerAspAspLeuGluValPheAspPheSerArgProLysProLeuAsp-227 |
| SEQ. ID. NO. 2384 | 232-AlaLeuArgArgGluThrGlyArgAlaGlyPheAspAspAlaTyrArgValProSerAspIleGlyArgPro-255 |
| SEQ. ID. NO. 2385 | 261-AlaGlyArgArgArgArgIleSerIleTyrSerAspArgAsnGly-275 |
| SEQ. ID. NO. 2386 | 282-AlaProGlnAspPheAlaArgHisAspAlaGlyVal-293 |
| SEQ. ID. NO. 2387 | 300-GluAlaGlnThrLeuProAspSerLeuAsnTrpProGlu-312 |
| SEQ. ID. NO. 2388 | 314-GlyAsnIleArgLeuAsnLysGlyAspThrArgGluAlaThr-327 |
| Hydrophilic Regions - Hopp-Woods | |
| SEQ. ID. NO. 2389 | 1-MetSerAspThrProAlaThrArgAsp-9 |
| SEQ. ID. NO. 2390 | 24-SerAsnArgArgGlyThrArg-30 |
| SEQ. ID. NO. 2391 | 48-AspGlyValArgGlu-52 |
| SEQ. ID. NO. 2392 | 58-PheAspAspAlaAlaSer-63 |
| SEQ. ID. NO. 2393 | 78-ValAlaGlyArgIleArgGlyAlaAla-86 |
| SEQ. ID. NO. 2394 | 89-IleAsnGlyArgThrTyrArgValGluAlaAsnGluGlyArgAsnAlaLeu-105 |
| SEQ. ID. NO. 2395 | 121-AlaAlaAspGlyArgSerValValLeu-129 |
| SEQ. ID. NO. 2396 | 131-SerArgLeuGlnGlnSerAlaAspGlyTyrProAsnAspLeuAspLeu-146 |
| SEQ. ID. NO. 2397 | 150-TyrArgLeuAspGluAspAspArgLeuThrVal-160 |
| SEQ. ID. NO. 2398 | 199-MetProAlaAspAlaGluLysLeuPro-207 |
| SEQ. ID. NO. 2399 | 210-ThrValSerAspAspLeuGluVal-217 |
| SEQ. ID. NO. 2400 | 221-SerArgProLysProLeuAsp-227 |
| SEQ. ID. NO. 2401 | 232-AlaLeuArgArgGluThrGlyArgAlaGlyPheAspAspAlaTyrArgValProSerAspIleGlyArg-254 |
| SEQ. ID. NO. 2402 | 261-AlaGlyArgArgArgArgIleSerIleTyrSerAspArgAsnGly-275 |
| SEQ. ID. NO. 2403 | 285-AspPheAlaArgHisAspAlaGlyVal-293 |
| SEQ. ID. NO. 2404 | 317-ArgLeuAsnLysGlyAspThrArgGluAlaThr-327 |
| 146 | |
| AMPHI Regions - AMPHI | |
| SEQ. ID. NO. 2405 | 19-LysGlnTyrGlyLeuLeuAspPheMetProCys-29 |
| SEQ. ID. NO. 2406 | 24-ProLeuAspAsnPheProThrVal-41 |
| SEQ. ID. NO. 2407 | 69-ValAlaAsnLeuArgArg-74 |
| SEQ. ID. NO. 2408 | 95-LeuArgAlaCysAlaValIleValAlaLysTyrValGlyValPheGlnLys-111 |
| SEQ. ID. NO. 2409 | 140-AlaArgArgValArg-144 |
| SEQ. ID. NO. 2410 | 158-ArgHisGlnArgGlyPheAlaArg-165 |
| SEQ. ID. NO. 2411 | 191-ProIleValSerGlnTrpThrPro-198 |
| Antigenic Index - Jameson-Wolf | |
| SEQ. ID. NO. 2412 | 6-LeuArgSerArgGlnValValIleAspHisAspLysValLysGln-20 |
| SEQ. ID. NO. 2413 | 30-LeuArgGlnProProLeuAspAsn-37 |
| SEQ. ID. NO. 2414 | 41-ValArgProAlaSerValGluAlaArgGlyLysTyrValGluArgArgArgGlnAspLysAspAlaAspGlyPheGlyGlnArg-68 |
| SEQ. ID. NO. 2415 | 70-AlaAsnLeuArgArgAlaLeu-76 |
| SEQ. ID. NO. 2416 | 86-AlaCysArgArgGlnArgIleHisThr-94 |
| SEQ. ID. NO. 2417 | 112-SerPheLeuArgAspLysArgLeuLys-120 |
| SEQ. ID. NO. 2418 | 138-ArgArgAlaArgArgValArgHisGlyAsnAlaGln-149 |
| SEQ. ID. NO. 2419 | 155-GlnGlnProArgHisGlnArgGlyPheAla-164 |
| SEQ. ID. NO. 2420 | 166-AlaGlySerGlyArgAsnAspLysAspValAlaPheSerIle-179 |
| Hydrophilic Regions - Hopp-Woods | |
| SEQ. ID. NO. 2421 | 6-LeuArgSerArgGlnValValIleAspHisAspLysValLysGln-20 |
| SEQ. ID. NO. 2422 | 44-AlaSerValGluAlaArgGlyLysTyrValGluArgArgArgGlnAspLysAspAlaAspGlyPheGly-66 |
| SEQ. ID. NO. 2423 | 70-AlaAsnLeuArgArgAlaLeu-76 |
| SEQ. ID. NO. 2424 | 86-AlaCysArgArgGlnArgIleHisThr-94 |
| SEQ. ID. NO. 2425 | 113-PheLeuArgAspLysArgLeuLys-120 |
| SEQ. ID. NO. 2426 | 138-ArgArgAlaArgArgValArgHisGlyAsn-147 |
| SEQ. ID. NO. 2427 | 156-GlnProArgHisGlnArgGlyPheAla-164 |
| SEQ. ID. NO. 2428 | 167-GlySerGlyArgAsnAspLysAspValAla-176 |
| 148 | |
| AMPHI Regions - AMPHI | |
| SEQ. ID. NO. 2429 | 25-AlaAspLysIleArgLysIleGluAsnTrpPro-35 |
| SEQ. ID. NO. 2430 | 49-GlnSerAlaGluTyrPheArgLeuLeuValAspLeu-60 |
| SEQ. ID. NO. 2431 | 150-AlaGlyLeuGluLeuIleArgLysLeuGlyGlyGluIle-162 |
| SEQ. ID. NO. 2432 | 165-AlaAlaAlaIleLeuGluPheThrAspLeuGlnGlyGlyLysAsnIleArg-181 |
| Antigenic Index - Jameson-Wolf | |
| SEQ. ID. NO. 2433 | 4-LysThrSerAsnLeu-8 |
| SEQ. ID. NO. 2434 | 24-LeuAlaAspLysIleArgLysIleGluAsnTrpProGlnLysGly-38 |
| SEQ. ID. NO. 2435 | 66-MetAspGlnLysIleAspIle-72 |
| SEQ. ID. NO. 2436 | 76-LeuAspAlaArgGly-80 |
| SEQ. ID. NO. 2437 | 97-ProIleArgLysLysGlyLysLeuPro-105 |
| SEQ. ID. NO. 2438 | 117-TyrGlyGluAlaAlaVal-122 |
| SEQ. ID. NO. 2439 | 124-IleHisThrAspAlaValLysLeuGlySer-133 |
| SEQ. ID. NO. 2440 | 153-GluLeuIleArgLysLeuGlyGlyGluIleValGlu-164 |
| SEQ. ID. NO. 2441 | 172-ThrAspLeuGlnGlyGlyLysAsnIleArgAlaSerGlyAlaPro-186 |
| SEQ. ID. NO. 2442 | 192-GlnAsnGluGlyCysMetLysGly-199 |
| Hydrophilic Regions - Hopp-Woods | |
| SEQ. ID. NO. 2443 | 24-LeuAlaAspLysIleArgLysIleGluAsnTrpPro-35 |
| SEQ. ID. NO. 2444 | 66-MetAspGlnLysIleAspIle-72 |
| SEQ. ID. NO. 2445 | 97-ProIleArgLysLysGlyLysLeuPro-105 |

TABLE 1-continued

| | |
|---|---|
| SEQ. ID. NO. 2446 | 117-TyrGlyGluAlaAlaVal-122 |
| SEQ. ID. NO. 2447 | 124-IleHisThrAspAlaValLysLeuGlySer-133 |
| SEQ. ID. NO. 2448 | 153-GluLeuIleArgLysLeuGlyGlyGluIleValGlu-164 |
| SEQ. ID. NO. 2449 | 178-LysAsnIleArgAlaSerGly-184 |
| SEQ. ID. NO. 2450 | 195-GlyCysMetLysGly-199 |
| 149-2 | |
| AMPHI Regions - AMPHI | |
| SEQ. ID. NO. 2451 | 78-AsnLeuGlyAspAlaLeuAspGlyValProGlyIle-89 |
| SEQ. ID. NO. 2452 | 107-ThrGlyArgArgIleLysValLeuAsnHisHisGlyGluThrGlyAspMet-123 |
| SEQ. ID. NO. 2453 | 141-GlnValGluIleLeuArgGlyProValThr-150 |
| SEQ. ID. NO. 2454 | 158-ValAlaGlyLeuValAsp-163 |
| SEQ. ID. NO. 2455 | 170-ProGluLysMetProGluAsnGlyVal-178 |
| SEQ. ID. NO. 2456 | 190-AsnLeuGluLysLeu-194 |
| SEQ. ID. NO. 2457 | 226-TyrArgAsnLeuLysArgLeuProAspSerHis-236 |
| SEQ. ID. NO. 2458 | 351-PheProGlyPheGlu-355 |
| SEQ. ID. NO. 2459 | 372-AlaGlyAspAlaValGluAsnPhePheAsnAsn-382 |
| SEQ. ID. NO. 2460 | 395-ProIleGlyArgLeuLys-400 |
| SEQ. ID. NO. 2461 | 415-LeuSerAlaIleSerGluAlaVal-422 |
| SEQ. ID. NO. 2462 | 571-ArgPheGlyAsnTyrIleTyrAlaGln-579 |
| SEQ. ID. NO. 2463 | 582-AsnAspGlyArgGlyProLysSerIleGluAsp-592 |
| SEQ. ID. NO. 2464 | 633-ArgGlyArgLeuLysAsnLeuProSer-641 |
| Antigenic Index - Jameson-Wolf | |
| SEQ. ID. NO. 2465 | 1-MetArgArgGluAlaLysMetAla-8 |
| SEQ. ID. NO. 2466 | 31-HisGluThrGluGlnSerValAspLeuGluThr-41 |
| SEQ. ID. NO. 2467 | 46-GlyLysSerArgProArgAlaThrSerGly-55 |
| SEQ. ID. NO. 2468 | 61-ThrAlaSerAspLysIleIleSerGlyAspThrLeuArgGlnLysAla-76 |
| SEQ. ID. NO. 2469 | 103-IleArgGlyGlnThrGlyArgArgIleLysVal-113 |
| SEQ. ID. NO. 2470 | 115-AsnHisHisGlyGluThrGlyAspMetAlaAspPheSerProAspHis-130 |
| SEQ. ID. NO. 2471 | 143-GluIleLeuArgGlyPro-148 |
| SEQ. ID. NO. 2472 | 163-AspValAlaAspGlyLysIleProGluLysMetProGluAsnGlyValSerGlyGluLeuGlyLeu-184 |
| SEQ. ID. NO. 2473 | 186-LeuSerSerGlyAsnLeuGluLysLeuThrSerGlyGly-198 |
| SEQ. ID. NO. 2474 | 213-GlyLeuTyrArgLysSerGlyAspTyrAlaValProArgTyrArgAsnLeuLysArgLeuProAspSerHisAlaAspSerGlnThrGly-242 |
| SEQ. ID. NO. 2475 | 250-GlyGluLysGlyPhe-254 |
| SEQ. ID. NO. 2476 | 258-AlaTyrSerAspArgArgAspGlnTyrGly-267 |
| SEQ. ID. NO. 2477 | 269-ProAlaHisSerHisGluTyrAspAspCysHisAla-280 |
| SEQ. ID. NO. 2478 | 287-SerLeuIleAsnLysArgTyrLeu-294 |
| SEQ. ID. NO. 2479 | 301-LeuThrGluGluAspIleAspTyrAspAsnProGlyLeu-313 |
| SEQ. ID. NO. 2480 | 316-GlyPheHisAspAspAspAsnAlaHis-324 |
| SEQ. ID. NO. 2481 | 326-HisThrHisSerGlyArgProTrpIleAspLeuArgAsnLysArgTyrGluLeuArgAlaGluTrpLysGlnProPheProGly-353 |
| SEQ. ID. NO. 2482 | 360-HisLeuAsnArgAsnAspTyrArgHisAspGluLysAlaGlyAspAlaVal-376 |
| SEQ. ID. NO. 2483 | 380-PheAsnAsnGlnThrGlnAsnAlaArgIleGluLeuArgHisGlnProIleGlyArgLeuLysGlySerTrp-403 |
| SEQ. ID. NO. 2484 | 408-LeuGlnGlnLysSerSerAla-414 |
| SEQ. ID. NO. 2485 | 428-LeuAspAsnLysVal-432 |
| SEQ. ID. NO. 2486 | 443-AlaAsnTrpAspAsnPheThrLeuGluGlyGlyValArgValGluLysGlnLysAlaSerIleGlnTyrAspLysAlaLeuIleAspArgGluAsnTyrTyrAsnHisProLeuProAsp-482 |
| SEQ. ID. NO. 2487 | 484-GlyAlaHisArgGlnThrAla-490 |
| SEQ. ID. NO. 2488 | 512-SerHisGlnGluArgLeuProSerThrGlnGluLeuTyrAlaHisGly-527 |
| SEQ. ID. NO. 2489 | 537-ValGlyAsnLysHisLeuAsnLysGluArgSerAsnAsnIle-550 |
| SEQ. ID. NO. 2490 | 556-TyrGluGlyAspArgTrpGln-562 |
| SEQ. ID. NO. 2491 | 568-TyrArgAsnArgPheGlyAsn-574 |
| SEQ. ID. NO. 2492 | 580-ThrLeuAsnAspGlyArgGlyProLysSerIleGluAspAspSerGluMetLysLeu-598 |
| SEQ. ID. NO. 2493 | 600-ArgTyrAsnGlnSerGlyAlaAspPheTyrGlyAlaGluGly-613 |
| SEQ. ID. NO. 2494 | 615-IleTyrPheLysProThrProArgTyrArgIle-625 |
| SEQ. ID. NO. 2495 | 627-ValSerGlyAspTyrValArgGlyArgLeuLysAsnLeuProSerLeuProGlyArgGluAspAlaTyrGlyAsnArgPro-653 |
| SEQ. ID. NO. 2496 | 655-IleAlaGlnAspAspGlnAsnAlaProArgValProAla-667 |
| SEQ. ID. NO. 2497 | 677-SerLeuThrAspArgIleAspAla-684 |
| SEQ. ID. NO. 2498 | 695-AsnLysLeuAlaArgTyrGluThrArgThrProGlyHis-707 |
| SEQ. ID. NO. 2499 | 713-GlyAlaAsnTyrArgArgAsnThrArgTyrGlyGluTrp-725 |
| SEQ. ID. NO. 2500 | 731-AlaAspAsnLeuLeu-735 |
| SEQ. ID. NO. 2501 | 745-PheLeuSerAspThrProGlnMetGlyArgSerPheThrGlyGlyVal-760 |
| Hydrophilic Regions - Hopp-Woods | |
| SEQ. ID. NO. 2502 | 1-MetArgArgGluAlaLysMetAla-8 |
| SEQ. ID. NO. 2503 | 31-HisGluThrGluGlnSerValAspLeuGluThr-41 |
| SEQ. ID. NO. 2504 | 46-GlyLysSerArgProArgAlaThr-53 |
| SEQ. ID. NO. 2505 | 61-ThrAlaSerAspLysIleIleSer-68 |
| SEQ. ID. NO. 2506 | 70-AspThrLeuArgGlnLysAla-76 |
| SEQ. ID. NO. 2507 | 106-GlnThrGlyArgArgIleLysVal-113 |
| SEQ. ID. NO. 2508 | 118-GlyGluThrGlyAspMetAlaAspPheSerPro-128 |
| SEQ. ID. NO. 2509 | 163-AspValAlaAspGlyLysIleProGluLysMetProGluAsnGlyValSer-179 |
| SEQ. ID. NO. 2510 | 187-SerSerGlyAsnLeuGluLysLeuThr-195 |
| SEQ. ID. NO. 2511 | 213-GlyLeuTyrArgLysSerGlyAsp-220 |
| SEQ. ID. NO. 2512 | 225-ArgTyrArgAsnLeuLysArgLeuProAspSerHisAlaAspSerGlnThr-241 |
| SEQ. ID. NO. 2513 | 259-TyrSerAspArgArgAspGlnTyr-266 |
| SEQ. ID. NO. 2514 | 273-HisGluTyrAspAspCysHisAla-280 |
| SEQ. ID. NO. 2515 | 301-LeuThrGluGluAspIleAspTyrAspAsn-310 |
| SEQ. ID. NO. 2516 | 317-PheHisAspAspAspAsnAlaHis-324 |
| SEQ. ID. NO. 2517 | 336-LeuArgAsnLysArgTyrGluLeuArgAlaGluTrp-347 |
| SEQ. ID. NO. 2518 | 360-HisLeuAsnArgAsnAspTyrArgHisAspGluLysAlaGlyAspAlaVal-376 |
| SEQ. ID. NO. 2519 | 384-ThrGlnAsnAlaArgIleGluLeuArgHis-393 |
| SEQ. ID. NO. 2520 | 397-GlyArgLeuLysGly-401 |

TABLE 1-continued

| | |
|---|---|
| SEQ. ID. NO. 2521 | 452-GlyGlyValArgValGluLysGlnLysAla-461 |
| SEQ. ID. NO. 2522 | 468-AlaLeuIleAspArgGluAsnTyr-475 |
| SEQ. ID. NO. 2523 | 484-GlyAlaHisArgGlnThrAla-490 |
| SEQ. ID. NO. 2524 | 512-SerHisGlnGluArgLeuProSer-519 |
| SEQ. ID. NO. 2525 | 541-HisLeuAsnLysGluArgSerAsnAsn-549 |
| SEQ. ID. NO. 2526 | 556-TyrGluGlyAspArgTrp-561 |
| SEQ. ID. NO. 2527 | 581-LeuAsnAspGlyArgGlyProLysSerIleGluAspAspSerGluMetLysLeu-598 |
| SEQ. ID. NO. 2528 | 609-TyrGlyAlaGluGly-613 |
| SEQ. ID. NO. 2529 | 619-ProThrProArgTyrArgIle-625 |
| SEQ. ID. NO. 2530 | 630-AspTyrValArgGlyArgLeuLysAsn-638 |
| SEQ. ID. NO. 2531 | 643-ProGlyArgGluAspAlaTyrGly-650 |
| SEQ. ID. NO. 2532 | 655-IleAlaGlnAspAspGlnAsnAlaProArgValProAla-667 |
| SEQ. ID. NO. 2533 | 677-SerLeuThrAspArgIleAspAla-684 |
| SEQ. ID. NO. 2534 | 696-LysLeuAlaArgTyrGluThrArgThrProGly-706 |
| SEQ. ID. NO. 2535 | 715-AsnTyrArgArgAsnThrArgTyrGly-723 |

150-2
AMPHI Regions - AMPHI

| | |
|---|---|
| SEQ. ID. NO. 2536 | 20-IleThrGlnLeuLeuSerGlyLeuAsp-28 |
| SEQ. ID. NO. 2537 | 80-ValAlaAspLysAlaAlaAspSerLeuGlu-89 |
| SEQ. ID. NO. 2538 | 138-AsnGlyLysLysAlaProLysLeu-145 |
| SEQ. ID. NO. 2539 | 159-SerTyrProAsnPheCysGlnAlaGlyLysAspPheAspArgArgPheGlu-175 |
| SEQ. ID. NO. 2540 | 198-AlaTrpThrAspAsnIleAla-204 |
| SEQ. ID. NO. 2541 | 223-ThrProProAlaGlyLeuGln-229 |
| SEQ. ID. NO. 2542 | 293-ArgGluIleLeuAspLeuLeu-299 |
| SEQ. ID. NO. 2543 | 316-ValAlaArgAlaLeuSer-321 |
| SEQ. ID. NO. 2544 | 333-PheValLysGlyTyrAlaAlaPheAlaHisTyrGluGluLeuAspLysIleIle-350 |
| SEQ. ID. NO. 2545 | 365-IleValAspValLeuHisArgPheProAlaSerLeu-376 |
| SEQ. ID. NO. 2546 | 379-GluGlnPheIleArgLeuLeuArgProLeuAla-389 |
| SEQ. ID. NO. 2547 | 468-GlyValAlaProPheArg-473 |
| SEQ. ID. NO. 2548 | 505-ThrGluTrpGlnGlnPheAlaLys-512 |
| SEQ. ID. NO. 2549 | 537-IleArgGluGlnAla-541 |
| SEQ. ID. NO. 2550 | 560-AlaAlaLysMetAlaLysAspValGluAlaAlaLeuLeuAspValIle-575 |
| SEQ. ID. NO. 2551 | 588-GluTyrLeuAspMetLeuArgGluGlu-596 |

Antigenic Index - Jameson-Wolf

| | |
|---|---|
| SEQ. ID. NO. 2552 | 1-MetSerGluHisAspMetGlnAsnThrAsnProPro-12 |
| SEQ. ID. NO. 2553 | 16-LeuProProGluIle-20 |
| SEQ. ID. NO. 2554 | 42-LysAlaGlyAsnGlyAlaSerAlaGlyLeu-51 |
| SEQ. ID. NO. 2555 | 72-SerGlnThrGlyAsnAlaLysSerValAlaAspLysAlaAlaAspSerLeuGlu-89 |
| SEQ. ID. NO. 2556 | 96-SerArgAlaGluLeuLysAspTyrLysAlaLysAsnIleAlaGlyGluArgArgLeu-114 |
| SEQ. ID. NO. 2557 | 118-ThrSerThrGlnGlyGluGlyGluProProLysGluAlaValVal-132 |
| SEQ. ID. NO. 2558 | 137-LeuAsnGlyLysLysAlaProLysLeuAspLys-147 |
| SEQ. ID. NO. 2559 | 154-GlyLeuGlyAspSerSerTyrProAsnPheCysGlnAlaGlyLysAspPheAspArgArgPheGluGluLeuGlyAlaLysArgLeuLeuGluArgVal AspAlaAspLeuAspPhe-192 |
| SEQ. ID. NO. 2560 | 207-LeuLysGluGluAlaAlaLysAsnArgAlaThrProAlaProGlnThrThrProProAlaGlyLeuGlnThrAlaProAspGlyArgTyrCysLys-238 |
| SEQ. ID. NO. 2561 | 250-GlnLysIleThrAlaArgGlnSerAspLysAspValArgHisIleGluIleAspLeuSerGlySerAspLeu-273 |
| SEQ. ID. NO. 2562 | 276-LeuProGlyAspAla-280 |
| SEQ. ID. NO. 2563 | 285-PheAspAsnAspProAlaLeuVal-292 |
| SEQ. ID. NO. 2564 | 302-AspProAlaThrGluIleGlnAlaGlyGlyLysMetMetPro-315 |
| SEQ. ID. NO. 2565 | 324-PheGluLeuThrGlnAsnThrProAlaPhe-333 |
| SEQ. ID. NO. 2566 | 344-GluGluLeuAspLysIleIleAla-351 |
| SEQ. ID. NO. 2567 | 397-SerAlaGlnAlaGluValGlyAspGluValHis-407 |
| SEQ. ID. NO. 2568 | 415-PheGluHisGluGlyArgAlaArgThrGlyGlyAlaSerGlyPheLeu-430 |
| SEQ. ID. NO. 2569 | 432-AspArgLeuGluGluAspGlyThrVal-440 |
| SEQ. ID. NO. 2570 | 443-PheValGluArgAsnAspGlyPheArgLeuProGluAspSerArgLysPro-459 |
| SEQ. ID. NO. 2571 | 464-GlySerGlyThrGly-468 |
| SEQ. ID. NO. 2572 | 478-GlnArgAlaAlaGluAsnAlaGluGlyLysAsn-488 |
| SEQ. ID. NO. 2573 | 509-GlnPheAlaLysAspGlyPheLeuHisArgTyrAspPheAlaTrpSerArgAspGlnGluGluLysIleTyrVal-533 |
| SEQ. ID. NO. 2574 | 535-AspLysIleArgGluGlnAlaGlu-542 |
| SEQ. ID. NO. 2575 | 559-AspAlaAlaLysMetAlaLysAspValGlu-568 |
| SEQ. ID. NO. 2576 | 579-GlyHisLeuAspGluGluGlyAlaGluGluTyrLeuAspMetLeuArgGluGluLysArgTyrGlnArgAspValTyr |

Hydrophilic Regions - Hopp-Woods

| | |
|---|---|
| SEQ. ID. NO. 2577 | 1-MetSerGluHisAspMetGlnAsn-8 |
| SEQ. ID. NO. 2578 | 75-GlyAsnAlaLysSerValAlaAspLysAlaAlaAspSerLeuGlu-89 |
| SEQ. ID. NO. 2579 | 96-SerArgAlaGluLeuLysAspTyrLysAlaLysAsnIleAlaGlyGluArgArgLeu-114 |
| SEQ. ID. NO. 2580 | 120-ThrGlnGlyGluGlyGluProProLysGluAlaValVal-132 |
| SEQ. ID. NO. 2581 | 137-LeuAsnGlyLysLysAlaProLysLeuAspLys-147 |
| SEQ. ID. NO. 2582 | 166-AlaGlyLysAspPheAspArgArgPheGluGluLeuGlyAlaLysArgLeuLeuGluArgValAspAlaAspLeuAspPhe-192 |
| SEQ. ID. NO. 2583 | 207-LeuLysGluGluAlaAlaLysAsnArgAlaThrPro-218 |
| SEQ. ID. NO. 2584 | 230-ThrAlaProAspGlyArgTyrCysLys-238 |
| SEQ. ID. NO. 2585 | 251-LysIleThrAlaArgGlnSerAspLysAspValArgHisIleGluIleAspLeuSerGly-270 |
| SEQ. ID. NO. 2586 | 288-AspProAlaLeuVal-292 |
| SEQ. ID. NO. 2587 | 344-GluGluLeuAspLysIleIleAla-351 |
| SEQ. ID. NO. 2588 | 398-AlaGlnAlaGluValGlyAspGluValHis-407 |
| SEQ. ID. NO. 2589 | 415-PheGluHisGluGlyArgAlaArgThrGlyGly-425 |
| SEQ. ID. NO. 2590 | 432-AspArgLeuGluGluAspGlyThrVal-440 |
| SEQ. ID. NO. 2591 | 443-PheValGluArgAsnAspGlyPheArgLeuProGluAspSerArgLysPro-459 |
| SEQ. ID. NO. 2592 | 479-ArgAlaAlaGluAsnAlaGluGlyLys-487 |
| SEQ. ID. NO. 2593 | 523-TrpSerArgAspGlnGluGluLysIleTyrVal-533 |
| SEQ. ID. NO. 2594 | 535-AspLysIleArgGluGlnAlaGlu-542 |
| SEQ. ID. NO. 2595 | 559-AspAlaAlaLysMetAlaLysAspValGlu-568 |

TABLE 1-continued

| SEQ. ID. NO. 2596 | 580-HisLeuAspGluGluGlyAlaGluGluTyrLeuAspMetLeuArgGluGluLysArgTyrGlnArgAspValTyr-604 |

151
AMPHI Regions - AMPHI
| SEQ. ID. NO. 2597 | 6-AsnIleAlaIleIleAla-11 |
| SEQ. ID. NO. 2598 | 22-AspGlnLeuLeuArg-26 |
| SEQ. ID. NO. 2599 | 72-ValAspThrProGlyHis-77 |
| SEQ. ID. NO. 2600 | 81-GlyGlyGluValGluArgValLeuGlyMetValAspCysVal-94 |
| SEQ. ID. NO. 2601 | 128-LysIleAspLysPro-132 |
| SEQ. ID. NO. 2602 | 144-PheGluLeuPheAspAsnLeuGlyAlaThr-153 |
| SEQ. ID. NO. 2603 | 165-SerGlyLeuSerGlyPheAlaLysLeuGluGluThrAspGluSerAsn-180 |
| SEQ. ID. NO. 2604 | 184-ProLeuPheAspThrIleLeuLysTyrThr-193 |
| SEQ. ID. NO. 2605 | 248-GlyArgIleAsnGlnLeuLeuGlyPheLysGlyLeuGluArgVal-262 |
| SEQ. ID. NO. 2606 | 273-ValIleIleSerGlyIleGlu-279 |
| SEQ. ID. NO. 2607 | 330-IleArgAspArgLeuGlnLysGluLeu-338 |
| SEQ. ID. NO. 2608 | 348-AspThrAlaAspAla-352 |
| SEQ. ID. NO. 2609 | 396-CysGluProTyrGluAsnLeuThrValAsp-405 |
| SEQ. ID. NO. 2610 | 457-LeuThrArgGlyValGly-462 |
| SEQ. ID. NO. 2611 | 464-MetSerHisValPheAsp-469 |
| SEQ. ID. NO. 2612 | 537-LysGlyLysLysLeuThrAsnIle-544 |
| SEQ. ID. NO. 2613 | 551-GluAlaValArgLeuThrThr-557 |

Antigenic Index - Jameson-Wolf
| SEQ. ID. NO. 2614 | 1-MetLysGlnIleArg-5 |
| SEQ. ID. NO. 2615 | 13-ValAspHisGlyLysThrThrLeu-20 |
| SEQ. ID. NO. 2616 | 24-LeuLeuArgGlnSerGlyThrPheArgAlaAsnGlnGlnValAspGluArgValMetAspSerAsnAspLeuGluLysGluArgGlyIle-53 |
| SEQ. ID. NO. 2617 | 59-AsnThrAlaIleAspTyrGluGlyTyr-67 |
| SEQ. ID. NO. 2618 | 72-ValAspThrProGlyHisAlaAspPheGlyGlyGluValGluArg-86 |
| SEQ. ID. NO. 2619 | 99-AspAlaGlnGluGlyProMetProGlnThrArgPheValThr-112 |
| SEQ. ID. NO. 2620 | 128-LysIleAspLysProSerAlaArgProSerTrp-138 |
| SEQ. ID. NO. 2621 | 151-GlyAlaThrAspGluGlnLeuAsp-158 |
| SEQ. ID. NO. 2622 | 171-AlaLysLeuGluGluThrAspGluSerAsnAspMetArgProLeu-185 |
| SEQ. ID. NO. 2623 | 193-ThrProAlaProSerGlySerAlaAspGluThrLeu-204 |
| SEQ. ID. NO. 2624 | 211-LeuAspTyrAspAsnTyrThrGly-218 |
| SEQ. ID. NO. 2625 | 226-LeuAsnGlyArgIleLysProGlyGln-234 |
| SEQ. ID. NO. 2626 | 240-AsnHisAspGlnGlnIleAla-246 |
| SEQ. ID. NO. 2627 | 257-LysGlyLeuGluArgValProLeuGluGluAlaGluAlaGlyAsp-271 |
| SEQ. ID. NO. 2628 | 277-GlyIleGluAspIleGly-282 |
| SEQ. ID. NO. 2629 | 287-IleThrAspLysAspAsnProLysGlyLeuPro-297 |
| SEQ. ID. NO. 2630 | 300-SerValAspGluProThrLeu-306 |
| SEQ. ID. NO. 2631 | 314-ThrSerProLeuAlaGlyThrGluGlyLysPheValThrSerArgGlnIleArgAspArgLeuGlnLysGluLeuLeu-339 |
| SEQ. ID. NO. 2632 | 344-LeuArgValGluAspThrAlaAspAlaAspValPheArgValSerGlyArgGlyGluLeu-363 |
| SEQ. ID. NO. 2633 | 371-AsnMetArgArgGluGlyTyr-377 |
| SEQ. ID. NO. 2634 | 381-ValGlyLysProArgValValTyrArgAspIleAspGlyGlnLysCysGluProTyrGluAsnLeuThrValAspValProAspAspAsnGlnGlyAla ValMetGluGluLeuGlyArgArgArgGlyGluLeuThrAsnMetGluSerAspGlyAsnGlyArgThrArgLeuGluTyr-440 |
| SEQ. ID. NO. 2635 | 467-ValPheAspAspTyrAlaProValLysProAspMetProGlyArgHisAsnGly-484 |
| SEQ. ID. NO. 2636 | 489-GlnGluGlnGlyGlu-493 |
| SEQ. ID. NO. 2637 | 501-AsnLeuGluAspArgGlyArgMetPheValSerProAsnAspLysIleTyr-517 |
| SEQ. ID. NO. 2638 | 524-IleHisSerArgAspAsnAspLeu-531 |
| SEQ. ID. NO. 2639 | 535-ProLeuLysGlyLysLysLeuThrAsnIleArgAlaSerGlyThrAspGluAlaValArg-554 |
| SEQ. ID. NO. 2640 | 569-PheIleAspAspAspGluLeuValGlu-577 |
| SEQ. ID. NO. 2641 | 579-ThrProGlnSerIleArgLeuArgLysArgTyrLeuSerGluLeuGluArgArgHisPheLysLysLeuAsp-603 |

Hydrophilic Regions - Hopp-Woods
| SEQ. ID. NO. 2642 | 1-MetLysGlnIleArg-5 |
| SEQ. ID. NO. 2643 | 29-GlyThrPheArgAla-33 |
| SEQ. ID. NO. 2644 | 35-GlnGlnValAspGluArgValMetAspSerAsnAspLeuGluLysGluArgGlyIle-53 |
| SEQ. ID. NO. 2645 | 80-PheGlyGlyGluValGluArg-86 |
| SEQ. ID. NO. 2646 | 99-AspAlaGlnGluGlyProMetPro-106 |
| SEQ. ID. NO. 2647 | 128-LysIleAspLysProSerAla-134 |
| SEQ. ID. NO. 2648 | 151-GlyAlaThrAspGluGlnLeuAsp-158 |
| SEQ. ID. NO. 2649 | 171-AlaLysLeuGluGluThrAspGluSerAsnAspMetArgProLeu-185 |
| SEQ. ID. NO. 2650 | 198-GlySerAlaAspGluThrLeu-204 |
| SEQ. ID. NO. 2651 | 226-LeuAsnGlyArgIleLysPro-232 |
| SEQ. ID. NO. 2652 | 241-HisAspGlnGlnIleAla-246 |
| SEQ. ID. NO. 2653 | 258-GlyLeuGluArgValProLeuGluGluAlaGluAlaGlyAsp-271 |
| SEQ. ID. NO. 2654 | 277-GlyIleGluAspIleGly-282 |
| SEQ. ID. NO. 2655 | 287-IleThrAspLysAspAsnProLysGly-295 |
| SEQ. ID. NO. 2656 | 300-SerValAspGluProThrLeu-306 |
| SEQ. ID. NO. 2657 | 318-AlaGlyThrGluGlyLysPheValThr-326 |
| SEQ. ID. NO. 2658 | 328-ArgGlnIleArgAspArgLeuGlnLysGluLeuLeu-339 |
| SEQ. ID. NO. 2659 | 344-LeuArgValGluAspThrAlaAspAlaAspValPheArgValSerGlyArgGlyGluLeu-363 |
| SEQ. ID. NO. 2660 | 371-AsnMetArgArgGluGlyTyr-377 |
| SEQ. ID. NO. 2661 | 381-ValGlyLysProArgValValTyrArgAspIleAspGlyGlnLysCysGluProTyrGlu-400 |
| SEQ. ID. NO. 2662 | 405-AspValProAspAspAsnGlnGlyAlaValMetGluGluLeuGlyArgArgArgGlyGluLeuThrAsnMetGluSerAspGlyAsnGlyArg ThrArgLeu-438 |
| SEQ. ID. NO. 2663 | 472-AlaProValLysProAspMetProGlyArgHis-482 |
| SEQ. ID. NO. 2664 | 489-GlnGluGlnGlyGlu-493 |
| SEQ. ID. NO. 2665 | 502-LeuGluAspArgGlyArgMet-508 |
| SEQ. ID. NO. 2666 | 512-ProAsnAspLysIleTyr-517 |
| SEQ. ID. NO. 2667 | 525-HisSerArgAspAsnAspLeu-531 |
| SEQ. ID. NO. 2668 | 536-LeuLysGlyLysLysLeuThrAsn-543 |
| SEQ. ID. NO. 2669 | 545-ArgAlaSerGlyThrAspGluAlaValArg-554 |

TABLE 1-continued

| | |
|---|---|
| SEQ. ID. NO. 2670 | 569-PheIleAspAspAspGluLeuValGlu-577 |
| SEQ. ID. NO. 2671 | 583-IleArgLeuArgLysArgTyrLeuSerGluLeuGluArgArgArgHisPheLysLysLeuAsp-603 |

152
AMPHI Regions - AMPHI
| | |
|---|---|
| SEQ. ID. NO. 2672 | 10-LeuProThrArgLeuPhe-15 |
| SEQ. ID. NO. 2673 | 66-ArgPheSerArgPheValGlnGlyTrpAlaGlyIleArgGlyTyrLeuLysAsnGlyIleProGluHisIleGlnProGlyHisAsnProLeu-96 |
| SEQ. ID. NO. 2674 | 103-AlaLeuLeuAlaAla-107 |
| SEQ. ID. NO. 2675 | 130-LeuAsnHisLeuValSerGluHisThrGlySerLeu-141 |
| SEQ. ID. NO. 2676 | 150-PheLysLeuLeuAlaValPheSerAlaIleHisIleAlaAlaValAlaAlaTyr-167 |

Antigenic Index - Jameson-Wolf
| | |
|---|---|
| SEQ. ID. NO. 2677 | 1-MetLysAsnLysThrLysVal-7 |
| SEQ. ID. NO. 2678 | 29-SerAlaLysAlaGlyGlyAsp-35 |
| SEQ. ID. NO. 2679 | 61-GlySerAspThrAlaArgPheSerArg-69 |
| SEQ. ID. NO. 2680 | 79-GlyTyrLeuLysAsnGlyIleProGluHisIleGlnProGlyHisAsnProLeu-96 |
| SEQ. ID. NO. 2681 | 118-AlaAlaAspGluAsnThrPheSerThrAsnGlyTyr-129 |
| SEQ. ID. NO. 2682 | 137-HisThrGlySerLeuMetArg-143 |
| SEQ. ID. NO. 2683 | 169-ValPheLysLysLysAsnLeu-175 |
| SEQ. ID. NO. 2684 | 186-IleGluGlyLysThrSerIle-192 |

Hydrophilic Regions - Hopp-Woods
| | |
|---|---|
| SEQ. ID. NO. 2685 | 1-MetLysAsnLysThrLysVal-7 |
| SEQ. ID. NO. 2686 | 63-AspThrAlaArgPhe-67 |
| SEQ. ID. NO. 2687 | 118-AlaAlaAspGluAsnThrPhe-124 |
| SEQ. ID. NO. 2688 | 169-ValPheLysLysLysAsnLeu-175 |
| SEQ. ID. NO. 2689 | 186-IleGluGlyLysThrSerIle-192 |

153
AMPHI Regions - AMPHI
| | |
|---|---|
| SEQ. ID. NO. 2690 | 17-AlaAlaSerValLeuSerLeuProGluMetMetArgLeuMetValPhe-32 |
| SEQ. ID. NO. 2691 | 96-ThrLeuValAlaTyrIleLysLeuSerSerValAlaGlu-108 |
| SEQ. ID. NO. 2692 | 130-ValSerValProGlnHisTrp-136 |
| SEQ. ID. NO. 2693 | 222-ValAsnThrIleLeuAsnGlyIleAlaTyr-231 |
| SEQ. ID. NO. 2694 | 274-AlaLysLeuSerHisLeuTyrArgIleThrGluAlaValGlyArgTrpSerMetIleAspIlePheValIle-298 |

Antigenic Index - Jameson-Wolf
| | |
|---|---|
| SEQ. ID. NO. 2695 | 65-IleArgLysGlnAla-69 |
| SEQ. ID. NO. 2696 | 81-ValArgLeuArgGln-85 |
| SEQ. ID. NO. 2697 | 107-AlaGluValArgPhe-111 |
| SEQ. ID. NO. 2698 | 143-ArgLeuThrGlyAspAsnAlaValGlnThrAlaSerGluGlyLysThrCysCysSer-161 |
| SEQ. ID. NO. 2699 | 165-TyrPheArgAspSerAlaGluSerProCysGly-175 |
| SEQ. ID. NO. 2700 | 180-GluLeuTyrArgArgArgProLysSerLeuSer-190 |
| SEQ. ID. NO. 2701 | 215-SerAsnProAlaAlaThr-220 |
| SEQ. ID. NO. 2702 | 234-AspGluGlyAspArgLeu-239 |
| SEQ. ID. NO. 2703 | 272-ThrGlyAlaLysLysLeu-277 |
| SEQ. ID. NO. 2704 | 339-LeuLeuTrpAspLysArgAlaSerAspGlyIleAla-350 |
| SEQ. ID. NO. 2705 | 352-AsnGluThrGluLysHisAsp-358 |

Hydrophilic Regions - Hopp-Woods
| | |
|---|---|
| SEQ. ID. NO. 2706 | 81-ValArgLeuArgGln-85 |
| SEQ. ID. NO. 2707 | 107-AlaGluValArgPhe-111 |
| SEQ. ID. NO. 2708 | 152-ThrAlaSerGluGlyLysThrCysCys-160 |
| SEQ. ID. NO. 2709 | 168-AspSerAlaGluSerPro-173 |
| SEQ. ID. NO. 2710 | 180-GluLeuTyrArgArgArgProLysSerLeuSer-190 |
| SEQ. ID. NO. 2711 | 234-AspGluGlyAspArgLeu-239 |
| SEQ. ID. NO. 2712 | 273-GlyAlaLysLysLeu-277 |
| SEQ. ID. NO. 2713 | 339-LeuLeuTrpAspLysArgAlaSerAsp-347 |
| SEQ. ID. NO. 2714 | 352-AsnGluThrGluLysHisAsp |

154
AMPHI Regions - AMPHI
| | |
|---|---|
| SEQ. ID. NO. 2715 | 122-GlyValThrGlyLeuGlyThrLeuLeu-130 |
| SEQ. ID. NO. 2716 | 152-GlnAspIleProProValThr-158 |
| SEQ. ID. NO. 2717 | 262-ThrLysAsnSerLysAsnValLysSer-270 |
| SEQ. ID. NO. 2718 | 298-PheLysGlnSerVal-302 |
| SEQ. ID. NO. 2719 | 360-SerLysGluHisTrpLysGlnGlnPheGlnThrAlaLeuAsnLysGlyLeuThrAla-378 |
| SEQ. ID. NO. 2720 | 389-SerLysMetIleGluLeuAsnAsp-396 |
| SEQ. ID. NO. 2721 | 429-LysLeuAlaAspLeuLeuAspLysPheAspLysLeuPro-441 |
| SEQ. ID. NO. 2722 | 446-ValAlaGluLeuAsnGly-451 |
| SEQ. ID. NO. 2723 | 467-LeuSerSerIleAspLysLeuValGlyLysProGlnThrGlnAsnIleProAsnGluLeuAsnGlnThrLeuLysGluLeuArgThrThr-496 |
| SEQ. ID. NO. 2724 | 506-IleTyrGlyAspValGlnAsnThrLeuGlnSerLeuAspLysThrLeuLysAspValGlnProValIleAsnThrLeuLysGluLys-534 |

Antigenic Index - Jameson-Wolf
| | |
|---|---|
| SEQ. ID. NO. 2725 | 1-MetThrAspAsnSerProProProAsnGlyHisAlaGlnAlaArgValArgLysAsnAsnThr-21 |
| SEQ. ID. NO. 2726 | 43-LysGluIleArgAsnArgGlyProVal-51 |
| SEQ. ID. NO. 2727 | 57-AspSerAlaGluGlyIleGluValAsnAsnThr-67 |
| SEQ. ID. NO. 2728 | 75-AspValGlyArgValThrArgIleLysLeuArgAspAspGlnLysGlyValGlu-92 |
| SEQ. ID. NO. 2729 | 100-AspValSerGlyLeuIleArgSerAspThrGln-110 |
| SEQ. ID. NO. 2730 | 114-ValLysProArgIleAspGlnSerGly-122 |
| SEQ. ID. NO. 2731 | 138-ThrProGlyLysSerAspGluAlaLysAspValPheGln-150 |
| SEQ. ID. NO. 2732 | 169-LeuIleGlyLysAsnAspArgIleLeuAsn-178 |
| SEQ. ID. NO. 2733 | 196-AlaHisPheAspProSerAspGlnSer-204 |
| SEQ. ID. NO. 2734 | 212-GlnSerProAsnAspLysLeuIle-219 |
| SEQ. ID. NO. 2735 | 228-GluSerGlyIleAsnIleGluThrThrGlySerGlyIleLeuAsnSer-244 |
| SEQ. ID. NO. 2736 | 256-SerPheAspSerProLysThrLysAsnSerLysAsnValLysSerGluAspSer-273 |
| SEQ. ID. NO. 2737 | 275-ThrLeuTyrAspSerArgSerGluValAlaAsnLeuProAspAspArgSerLeu-292 |
| SEQ. ID. NO. 2738 | 300-GlnSerValArgGlyLeu-305 |

TABLE 1-continued

| | |
|---|---|
| SEQ. ID. NO. 2739 | 311-ValGluTyrLysGlyLeuAsn-317 |
| SEQ. ID. NO. 2740 | 325-ProTyrPheAspArgAsnAspSer-332 |
| SEQ. ID. NO. 2741 | 345-IleArgIleGluProSerArgLeuGluIleAsnAlaAspGluGlnSerLysGluHisTrpLysGlnGlnPhe-368 |
| SEQ. ID. NO. 2742 | 371-AlaLeuAsnLysGlyLeu-376 |
| SEQ. ID. NO. 2743 | 386-LeuThrGlySerLysMetIleGluLeuAsnAspGlnProSerAlaSerProLysLeuArgPro-406 |
| SEQ. ID. NO. 2744 | 419-GlnGlyGlyGlyLeuAspAspLeuGlnValLysLeu-430 |
| SEQ. ID. NO. 2745 | 432-AspLeuLeuAspLysPheAspLysLeuProLeuAspLysThrValAla-447 |
| SEQ. ID. NO. 2746 | 450-AsnGlySerLeuAlaGluLeuLysSerThrLeuLysSerAlaAsn-464 |
| SEQ. ID. NO. 2747 | 469-SerIleAspLysLeuValGlyLysProGlnThrGlnAsnIleProAsnGluLeuAsnGlnThrLeuLysGluLeuArgThrThr-496 |
| SEQ. ID. NO. 2748 | 500-ValSerProGlnSer-504 |
| SEQ. ID. NO. 2749 | 516-SerLeuAspLysThrLeuLysAspValGln-525 |
| SEQ. ID. NO. 2750 | 530-ThrLeuLysGluLysProAsn-536 |
| SEQ. ID. NO. 2751 | 541-AsnSerSerSerLysAspProIleProLysGlySerArg-553 |
| Hydrophilic Regions - Hopp-Woods | |
| SEQ. ID. NO. 2752 | 1-MetThrAspAsnSerProProPro-8 |
| SEQ. ID. NO. 2753 | 12-AlaGlnAlaArgValArgLysAsnAsn-20 |
| SEQ. ID. NO. 2754 | 43-LysGluIleArgAsnArgGly-49 |
| SEQ. ID. NO. 2755 | 57-AspSerAlaGluGlyIleGlu-63 |
| SEQ. ID. NO. 2756 | 75-AspValGlyArgValThrArgIleLysLeuArgAspAspGlnLysGlyValGlu-92 |
| SEQ. ID. NO. 2757 | 105-IleArgSerAspThr-109 |
| SEQ. ID. NO. 2758 | 116-ProArgIleAspGln-120 |
| SEQ. ID. NO. 2759 | 140-GlyLysSerAspGluAlaLysAspValPheGln-150 |
| SEQ. ID. NO. 2760 | 171-GlyLysAsnAspArgIleLeu-177 |
| SEQ. ID. NO. 2761 | 196-AlaHisPheAspProSerAspGln-203 |
| SEQ. ID. NO. 2762 | 214-ProAsnAspLysLeuIle-219 |
| SEQ. ID. NO. 2763 | 258-AspSerProLysThrLysAsnSerLysAsnValLysSerGluAspSer-273 |
| SEQ. ID. NO. 2764 | 278-AspSerArgSerGluVal-283 |
| SEQ. ID. NO. 2765 | 285-AsnLeuProAspAspArgSer-291 |
| SEQ. ID. NO. 2766 | 311-ValGluTyrLysGly-315 |
| SEQ. ID. NO. 2767 | 328-AspArgAsnAspSer-332 |
| SEQ. ID. NO. 2768 | 345-IleArgIleGluProSerArgLeuGluIleAsnAlaAspGluGlnSerLysGluHisTrpLys-365 |
| SEQ. ID. NO. 2769 | 390-LysMetIleGluLeuAsnAspGlnProSerAlaSerProLysLeuArgPro-406 |
| SEQ. ID. NO. 2770 | 421-GlyGlyLeuAspAspLeuGlnValLysLeu-430 |
| SEQ. ID. NO. 2771 | 432-AspLeuLeuAspLysPheAspLysLeuProLeuAspLysThrValAla-447 |
| SEQ. ID. NO. 2772 | 454-AlaGluLeuLysSerThrLeuLysSerAlaAsn-464 |
| SEQ. ID. NO. 2773 | 469-SerIleAspLysLeuValGly-475 |
| SEQ. ID. NO. 2774 | 482-IleProAsnGluLeu-486 |
| SEQ. ID. NO. 2775 | 498-GlnThrLeuLysGluLeuArgThr-495 |
| SEQ. ID. NO. 2776 | 516-SerLeuAspLysThrLeuLysAspValGln-525 |
| SEQ. ID. NO. 2777 | 530-ThrLeuLysGluLysProAsn-536 |
| SEQ. ID. NO. 2778 | 543-SerSerLysAspProIleProLysGlySerArg-553 |
| 155 | |
| AMPHI Regions - AMPHI | |
| SEQ. ID. NO. 2779 | 28-LysLeuGlyPheGlu-32 |
| SEQ. ID. NO. 2780 | 42-AlaAlaSerLeuAsp-46 |
| SEQ. ID. NO. 2781 | 105-LeuArgAlaLysLysVal-110 |
| SEQ. ID. NO. 2782 | 118-ValProArgIleSerArgAlaGlnAlaLeuAspAlaLeuSerSerMetAlaAsnIleSerGlyTyrArgAlaValIleGluAlaAlaAsn AlaPheGlyArgPhePheThrGly-155 |
| SEQ. ID. NO. 2783 | 175-ValAlaGlyLeuAlaAlaIleGlyThrAlaAsnSerLeuGlyAlaValValArgAlaPhe-194 |
| SEQ. ID. NO. 2784 | 201-AlaGluGlnIleGluSerMetGlyGly-209 |
| SEQ. ID. NO. 2785 | 225-AspGlyTyrAlaLysValMet-231 |
| SEQ. ID. NO. 2786 | 262-LysProAlaProLysLeuIleThrLysGluMetValGluSerMetLys-277 |
| SEQ. ID. NO. 2787 | 295-LeuThrArgProGlyGlu-300 |
| SEQ. ID. NO. 2788 | 308-ValLysIleIleGlyTyrThrAspMetAlaAsnArgLeuAlaGlyGln-323 |
| SEQ. ID. NO. 2789 | 330-ThrAsnLeuValAsnLeuThrLysLeuLeuSer-340 |
| SEQ. ID. NO. 2790 | 404-LysLeuAlaProAlaVal-409 |
| SEQ. ID. NO. 2791 | 428-AsnHisPheIleVal-432 |
| SEQ. ID. NO. 2792 | 451-LeuHisThrProLeuMetSerValThrAsnAlaIleSerGlyIleIle-466 |
| SEQ. ID. NO. 2793 | 469-GlyAlaLeuLeuGln-473 |
| SEQ. ID. NO. 2794 | 478-AsnGlyPheValSerLeuLeuSerPheValAla-488 |
| SEQ. ID. NO. 2795 | 494-IleAsnIlePheGlyGly-499 |
| Antigenic Index - Jameson-Wolf | |
| SEQ. ID. NO. 2796 | 4-GlyIleProArgGluSerLeuSerGlyGluThrArgVal-16 |
| SEQ. ID. NO. 2797 | 44-SerLeuAspAspAlaAla-49 |
| SEQ. ID. NO. 2798 | 72-ValAsnAlaProSerGluGlnGluLeu-80 |
| SEQ. ID. NO. 2799 | 94-TrpProArgGlnAsnGluAlaLeu-101 |
| SEQ. ID. NO. 2800 | 105-LeuArgAlaLysLysValAsn-111 |
| SEQ. ID. NO. 2801 | 117-MetValProArgIleSerArg-123 |
| SEQ. ID. NO. 2802 | 159-AlaAlaGlyLysValProProAla-166 |
| SEQ. ID. NO. 2803 | 194-PheAspThrArgLeuGluValAlaGluGlnIleGluSerMetGlyGlyLys-210 |
| SEQ. ID. NO. 2804 | 215-AspPheProGlnGluSerGlyGlySerGlyAspGlyTyrAlaLysValMetSer-232 |
| SEQ. ID. NO. 2805 | 242-LeuPheAlaGluGlnAlaLysGluValAsp-251 |
| SEQ. ID. NO. 2806 | 259-IleProGlyLysProAlaProLysLeuIleThr-269 |
| SEQ. ID. NO. 2807 | 271-GluMetValGluSerMetLysSerGlySer-280 |
| SEQ. ID. NO. 2808 | 289-ThrGlyGlyAsnCysGluLeuThrArgProGlyGluLeuSerVal-303 |
| SEQ. ID. NO. 2809 | 320-LeuAlaGlyGlnSerSer-325 |
| SEQ. ID. NO. 2810 | 338-LeuLeuSerProAsnLysAspGlyGluIle-347 |
| SEQ. ID. NO. 2811 | 349-LeuAspPheGluAspValIle-355 |
| SEQ. ID. NO. 2812 | 361-ValThrHisAspGlyGluIleThrPhePro-370 |
| SEQ. ID. NO. 2813 | 378-AlaGlnProGlnGlnThrProSerGluLysAlaValProAlaAlaLysProGluProLysPro-398 |

TABLE 1-continued

Hydrophilic Regions - Hopp-Woods
SEQ. ID. NO. 2814   4-GlyIleProArgGluSerLeuSerGlyGluThrArgVal-16
SEQ. ID. NO. 2815   44-SerLeuAspAspAlaAla-49
SEQ. ID. NO. 2816   74-AlaProSerGluGlnGluLeu-80
SEQ. ID. NO. 2817   96-ArgGlnAsnGluAlaLeu-101
SEQ. ID. NO. 2818   105-LeuArgAlaLysLysValAsn-111
SEQ. ID. NO. 2819   117-MetValProArgIleSerArg-123
SEQ. ID. NO. 2820   194-PheAspThrArgLeuGluValAlaGluGlnIleGluSerMetGly-208
SEQ. ID. NO. 2821   215-AspPheProGlnGluSerGlyGlySerGlyAspGlyTyrAla-228
SEQ. ID. NO. 2822   242-LeuPheAlaGluGlnAlaLysGluValAsp-251
SEQ. ID. NO. 2823   260-ProGlyLysProAlaPro-265
SEQ. ID. NO. 2824   271-GluMetValGluSerMetLysSer-278
SEQ. ID. NO. 2825   291-GlyAsnCysGluLeuThrArgProGlyGlu-300
SEQ. ID. NO. 2826   340-SerProAsnLysAspGlyGluIle-347
SEQ. ID. NO. 2827   349-LeuAspPheGluAspValIle-355
SEQ. ID. NO. 2828   363-HisAspGlyGluIle-367
SEQ. ID. NO. 2829   382-GlnThrProSerGluLysAlaValProAlaAlaLysProGluProLysPro-398
156
AMPHI Regions - AMPHI
SEQ. ID. NO. 2830   56-AsnGlyPheGluAlaPheAlaProPhe-64
Antigenic Index - Jameson-Wolf
SEQ. ID. NO. 2831   21-TyrAlaLysLysAlaGlyGlyPheArgPheLysAspAsnHisAsnProArgGly-38
SEQ. ID. NO. 2832   44-GlnGlyAlaAlaAla-48
SEQ. ID. NO. 2833   51-HisAlaAlaGlnGlnAsnGlyPheGlu-59
SEQ. ID. NO. 2834   73-AlaThrGlyAsnAlaAla-78
SEQ. ID. NO. 2835   103-AspLysAlaAlaMet-107
Hydrophilic Regions - Hopp-Woods
SEQ. ID. NO. 2836   21-TyrAlaLysLysAlaGlyGlyPheArgPheLysAspAsnHisAsnPro-36
SEQ. ID. NO. 2837   103-AspLysAlaAlaMet-107
157
AMPHI Regions - AMPHI
SEQ. ID. NO. 2838   21-GlyArgAspValArgAlaAla-27
SEQ. ID. NO. 2839   32-IleAsnHisLeuLeuLysArg-38
SEQ. ID. NO. 2840   61-PheValArgAlaAlaGln-66
SEQ. ID. NO. 2841   167-GlnLeuValAspArg-171
SEQ. ID. NO. 2842   176-AlaHisAspArgSerLeuAspGlyPhe-184
Antigenic Index - Jameson-Wolf
SEQ. ID. NO. 2843   1-MetArgAsnGluGluLysArgAlaLeuArgArgGluLeuArgGlyArgArgSerGlnMetGlyArgAspValArgAla-26
SEQ. ID. NO. 2844   38-ArgTyrIleLysLysGlyArgLysIle-46
SEQ. ID. NO. 2845   51-ProMetGlyLysGluLeuArgLeuAspGlyPheVal-62
SEQ. ID. NO. 2846   64-AlaAlaGlnLysArgGlyAla-70
SEQ. ID. NO. 2847   77-IleGluProArgSerArgArgMetTrp-85
SEQ. ID. NO. 2848   89-TyrProAlaAspGlyValLysGlnGluArgLysArgGlyArgAlaLysLeuHis-106
SEQ. ID. NO. 2849   111-AlaGlyArgLysLysArgValHisAsp-119
SEQ. ID. NO. 2850   129-GlyMetAspArgLeuGlyTyr-135
SEQ. ID. NO. 2851   151-MetLysTyrArgLeuGlnAla-157
SEQ. ID. NO. 2852   172-LeuProValGluAlaHisAspArgSerLeuAspGlyPheVal-185
Hydrophilic Regions - Hopp-Woods
SEQ. ID. NO. 2853   1-MetArgAsnGluGluLysArgAlaLeuArgArgGluLeuArgGlyArgArgSerGlnMetGlyArgAspValArgAla-26
SEQ. ID. NO. 2854   38-ArgTyrIleLysLysGlyArgLysIle-46
SEQ. ID. NO. 2855   54-LysGluLeuArgLeu-58
SEQ. ID. NO. 2856   64-AlaAlaGlnLysArgGlyAla-70
SEQ. ID. NO. 2857   77-IleGluProArgSerArgArg-83
SEQ. ID. NO. 2858   92-AspGlyValLysGlnGluArgLysArgGlyArgAlaLysLeu-105
SEQ. ID. NO. 2859   111-AlaGlyArgLysLysArgValHisAsp-119
SEQ. ID. NO. 2860   131-AspArgLeuGlyTyr-135
SEQ. ID. NO. 2861   151-MetLysTyrArgLeuGlnAla-157
SEQ. ID. NO. 2862   172-LeuProValGluAlaHisAspArgSerLeuAsp-182
158
AMPHI Regions - AMPHI
SEQ. ID. NO. 2863   20-PheSerArgAlaAlaGluGlnLeu-27
SEQ. ID. NO. 2864   33-AlaValSerArgIleValLysArgLeuGlu-42
SEQ. ID. NO. 2865   46-GlyValAsnLeuLeuAsnArgThr-53
SEQ. ID. NO. 2866   63-GlyAlaGlnTyrPheArgArgAlaGlnArgIleLeuGlnGlu-76
SEQ. ID. NO. 2867   85-LeuAlaValHisGluIleProGln-92
SEQ. ID. NO. 2868   166-ValIleAlaSerPro-170
SEQ. ID. NO. 2869   178-ThrProGlnSerThrGluGluLeu-185
SEQ. ID. NO. 2870   188-HisGlnCysLeuGlyPheThrGluProGlySerLeuAsnThrTrpAlaVal-204
Antigenic Index - Jameson-Wolf
SEQ. ID. NO. 2871   1-MetLysThrAsnSerGluGluLeu-8
SEQ. ID. NO. 2872   16-GluSerGlySerPheSerArgAlaAlaGlu-25
SEQ. ID. NO. 2873   36-ArgIleValLysArgLeuGluGluLysLeuGly-46
SEQ. ID. NO. 2874   49-LeuLeuAsnArgThrThrArgGlnLeuSerLeuThrGluGluGlyAlaGlnTyrPheArgArgAlaGlnArgIleLeuGln-75
SEQ. ID. NO. 2875   78-AlaAlaAlaGluThrGluMet-84
SEQ. ID. NO. 2876   114-LysPheAsnGluArgTyrProHisIleArg-123
SEQ. ID. NO. 2877   136-IleGluArgLysValAspIle-142
SEQ. ID. NO. 2878   144-LeuArgAlaGlyGluLeuAspAspSerGlyLeuArgAla-156
SEQ. ID. NO. 2879   158-HisLeuPheAspSerArgPheArgVal-166
SEQ. ID. NO. 2880   168-AlaSerProGluTyrLeuAlaLysHisGlyThrProGlnSerThrGluGluLeuAla-186
SEQ. ID. NO. 2881   192-GlyPheThrGluProGlySerLeuAsn-200

TABLE 1-continued

| | |
|---|---|
| SEQ. ID. NO. 2882 | 207-AlaGlnGlyAsnProTyrLysIle-214 |
| SEQ. ID. NO. 2883 | 216-ProHisPheThrAlaSerSerGlyGluIleLeu-226 |
| SEQ. ID. NO. 2884 | 229-LeuCysLeuSerGlyCys-234 |
| SEQ. ID. NO. 2885 | 243-LeuValAspAsnAspIleAlaGluGlyLysPhe-253 |
| SEQ. ID. NO. 2886 | 259-GluGlnThrSerAspLysThrHisProPhe-268 |
| SEQ. ID. NO. 2887 | 273-TyrSerAspLysAlaValAsnLeu-280 |
| SEQ. ID. NO. 2888 | 292-GluLeuGlyAsnAsnLeuCysGly-299 |

Hydrophilic Regions - Hopp-Woods

| | |
|---|---|
| SEQ. ID. NO. 2889 | 1-MetLysThrAsnSerGluGluLeu-8 |
| SEQ. ID. NO. 2890 | 19-SerPheSerArgAlaAlaGlu-25 |
| SEQ. ID. NO. 2891 | 36-ArgIleValLysArgLeuGluGluLysLeuGly-46 |
| SEQ. ID. NO. 2892 | 58-SerLeuThrGluGluGlyAlaGlnTyrPheArgArgAlaGlnArgIleLeuGln-75 |
| SEQ. ID. NO. 2893 | 78-AlaAlaAlaGluThrGluMet-84 |
| SEQ. ID. NO. 2894 | 114-LysPheAsnGluArgTyrPro-120 |
| SEQ. ID. NO. 2895 | 136-IleGluArgLysValAspIle-142 |
| SEQ. ID. NO. 2896 | 144-LeuArgAlaGlyGluLeuAspAspSerGlyLeuArgAla-156 |
| SEQ. ID. NO. 2897 | 162-SerArgPheArgVal-166 |
| SEQ. ID. NO. 2898 | 180-GlnSerThrGluGluLeuAla-186 |
| SEQ. ID. NO. 2899 | 246-AsnAspIleAlaGluGlyLysLeu-253 |
| SEQ. ID. NO. 2900 | 260-GlnThrSerAspLysThrHis-266 |
| SEQ. ID. NO. 2901 | 276-LysAlaValAsnLeu-280 |

160
AMPHI Regions - AMPHI

| | |
|---|---|
| SEQ. ID. NO. 2902 | 6-LysLeuValAspPheAlaGlnLeuThrGly-15 |
| SEQ. ID. NO. 2903 | 72-GlyLeuGlyHisVal-76 |
| SEQ. ID. NO. 2904 | 121-AlaAspLeuMetAsnGlyLeuProGluThr-130 |
| SEQ. ID. NO. 2905 | 157-GlyThrValSerMetValAsnAlaLeuSerSer-167 |
| SEQ. ID. NO. 2906 | 186-LeuSerGlyValLeuLysGlyTrpGlnAspLysArg-197 |
| SEQ. ID. NO. 2907 | 200-HisLeuIleGlnLysValIleAspLysProGlu-210 |
| SEQ. ID. NO. 2908 | 218-MetValAlaAlaAlaAsn-223 |
| SEQ. ID. NO. 2909 | 229-LeuMetArgArgPhe-233 |
| SEQ. ID. NO. 2910 | 242-HisAlaPheValAsnHisIleArg-249 |
| SEQ. ID. NO. 2911 | 279-PheGlyLysAlaPheLys-284 |

Antigenic Index - Jameson-Wolf

| | |
|---|---|
| SEQ. ID. NO. 2912 | 2-AspIleLeuAspLysLeuVal-8 |
| SEQ. ID. NO. 2913 | 28-SerValArgHisGluThrLeuGlnArgGluGlyLeu-39 |
| SEQ. ID. NO. 2914 | 51-CysIleAspGlyGluThrSerProArgProValSerThrGlyAsp-65 |
| SEQ. ID. NO. 2915 | 77-LeuSerHisAspGlyLysCysGlyGluSerLeuGlnProAspMetArgGlnHisGly-95 |
| SEQ. ID. NO. 2916 | 101-GlnCysGlyAsnGlyGlnAspMet-108 |
| SEQ. ID. NO. 2917 | 115-PheArgTyrAspThrHisAla-121 |
| SEQ. ID. NO. 2918 | 123-LeuMetAsnGlyLeu-127 |
| SEQ. ID. NO. 2919 | 149-LeuGluSerLysLysProLeu-155 |
| SEQ. ID. NO. 2920 | 178-LeuGluGlnAspLysAspValGluLeu-186 |
| SEQ. ID. NO. 2921 | 192-GlyTrpGlnAspLysArgLeuGly-199 |
| SEQ. ID. NO. 2922 | 205-ValIleAspLysProGluAspGluTrpAsnValAspLysMetVal-219 |
| SEQ. ID. NO. 2923 | 228-GlnLeuMetArgArgPheLysSerArgValGlyLeuSerProHis-242 |
| SEQ. ID. NO. 2924 | 255-LeuLeuLeuLysLysAsnProAspSerVal-264 |
| SEQ. ID. NO. 2925 | 274-GlnSerGluThrHisPhe-279 |
| SEQ. ID. NO. 2926 | 281-LysAlaPheLysArg-285 |
| SEQ. ID. NO. 2927 | 290-SerProGlyGlnTyrArgLysGluGlyGlyGlnLys-301 |

Hydrophilic Regions - Hopp-Woods

| | |
|---|---|
| SEQ. ID. NO. 2928 | 2-AspIleLeuAspLysLeuVal-8 |
| SEQ. ID. NO. 2929 | 29-ValArgHisGluThrLeuGlnArgGluGlyLeu-39 |
| SEQ. ID. NO. 2930 | 53-AspGlyGluThrSerProArgProValSer-62 |
| SEQ. ID. NO. 2931 | 79-HisAspGlyLysCysGlyGluSerLeuGlnProAspMetArgGln-93 |
| SEQ. ID. NO. 2932 | 101-GlnCysGlyAsnGlyGlnAsp-107 |
| SEQ. ID. NO. 2933 | 149-LeuGluSerLysLysProLeu-155 |
| SEQ. ID. NO. 2934 | 178-LeuGluGlnAspLysAspValGluLeu-186 |
| SEQ. ID. NO. 2935 | 193-TrpGlnAspLysArgLeuGly-199 |
| SEQ. ID. NO. 2936 | 205-ValIleAspLysProGluAspGluTrpAsnVal-215 |
| SEQ. ID. NO. 2937 | 228-GlnLeuMetArgArgPheLysSerArgValGly-238 |
| SEQ. ID. NO. 2938 | 255-LeuLeuLeuLysLysAsnProAspSer-263 |
| SEQ. ID. NO. 2939 | 281-LysAlaPheLysArg-285 |
| SEQ. ID. NO. 2940 | 293-GlnTyrArgLysGluGlyGlyGlnLys-301 |

163
AMPHI Regions - AMPHI

| | |
|---|---|
| SEQ. ID. NO. 2941 | 60-SerSerLeuGlyAsnIle-65 |
| SEQ. ID. NO. 2942 | 67-LeuGlyArgAspGluAsp-72 |
| SEQ. ID. NO. 2943 | 76-PheGlyPheLeuSerTrpLeuAlaMetLeuPhe-86 |
| SEQ. ID. NO. 2944 | 100-AlaGluProLeuMetHisTyrPheSerAspIleThrAla-112 |
| SEQ. ID. NO. 2945 | 170-IleSerGlyArgPheGlyAspAlaIleAspIleMetAlaLeuLeuAlaThrPhePheGlyIleIleThrThr-193 |
| SEQ. ID. NO. 2946 | 227-MetSerLeuAlaValValSerAlaIleSerGlyValGlyLysGlyValLysValLeuSer-246 |
| SEQ. ID. NO. 2947 | 272-AlaPheGlyAspAsnIleGlyAsnTyrLeuGlyAsnLeuValArg-286 |
| SEQ. ID. NO. 2948 | 313-TrpCysSerTrpAlaProPheValGlyLeuPheIleAla-325 |
| SEQ. ID. NO. 2949 | 346-LeuPheGlyValLeuTrpPhe-352 |
| SEQ. ID. NO. 2950 | 367-AlaGlyGlyMetLeuGluLysMetThrSerSer-377 |
| SEQ. ID. NO. 2951 | 380-ThrLeuLeuPheLysPhePheAsnTyrLeuProLeuProGluLeuThrSerIleValSerLeuLeu-401 |
| SEQ. ID. NO. 2952 | 438-TrpGlyValLeuMetSerAla-444 |
| SEQ. ID. NO. 2953 | 454-GlyLeuGlyAsnLeuGlnSerMetThrLeu-463 |
| SEQ. ID. NO. 2954 | 520-GluGlnAspIleLeuLysPheLeuLysGlnThrAlaSerPro-533 |

TABLE 1-continued

| | |
|---|---|
| SEQ. ID. NO. 2955 | 535-MetHisGluLeuGlnArgGluLeu-542 |
| SEQ. ID. NO. 2956 | 574-AspPheMetTyrGlyIle-579 |
| SEQ. ID. NO. 2957 | 583-GlyGlnAspValSerAspGlnLeu-590 |
| SEQ. ID. NO. 2958 | 630-AlaAspIleLeuLysAsnTyr-636 |

Antigenic Index - Jameson-Wolf

| | |
|---|---|
| SEQ. ID. NO. 2959 | 29-AspArgAlaLysGlu-33 |
| SEQ. ID. NO. 2960 | 65-IleArgLeuGlyArgAspGluAspValPro-74 |
| SEQ. ID. NO. 2961 | 111-ThrAlaGlyThrProGluHisArgGlnGln-120 |
| SEQ. ID. NO. 2962 | 166-LeuLysGluLysIleSerGlyArgPheGlyAspAlaIleAsp-179 |
| SEQ. ID. NO. 2963 | 200-GlnLeuGlyAlaGlyLeu-205 |
| SEQ. ID. NO. 2964 | 237-GlyValGlyLysGlyValLysVal-244 |
| SEQ. ID. NO. 2965 | 293-AlaTyrGluArgGluHisLysProTrpPhe-302 |
| SEQ. ID. NO. 2966 | 326-ArgIleSerLysGlyArgThrIleArg-334 |
| SEQ. ID. NO. 2967 | 370-MetLeuGluLysMetThrSerSerProGlu-379 |
| SEQ. ID. NO. 2968 | 409-ThrSerAlaAspSerGlyIle-415 |
| SEQ. ID. NO. 2969 | 421-IleThrSerArgAspLysGlyLeuSerAlaProArgTrp-433 |
| SEQ. ID. NO. 2970 | 451-ArgSerGlyGlyLeuGlyAsn-457 |
| SEQ. ID. NO. 2971 | 484-LeuSerAlaAspLysLysTyrPheGluThrArgValAsnProThrSer-499 |
| SEQ. ID. NO. 2972 | 503-ThrGlyGlyLysTrpLysGluArgLeu-511 |
| SEQ. ID. NO. 2973 | 516-SerGlnThrGlnGluGlnAspIle-523 |
| SEQ. ID. NO. 2974 | 527-LeuLysGlnThrAlaSer-532 |
| SEQ. ID. NO. 2975 | 537-GluLeuGlnArgGluLeuSerGluGluTyrGlyLeu-548 |
| SEQ. ID. NO. 2976 | 550-ValArgValAspLysMetPheHisArgAspGluProAla-562 |
| SEQ. ID. NO. 2977 | 566-ValIleArgLysGluThrMetArg-573 |
| SEQ. ID. NO. 2978 | 581-SerValGlyGlnAspValSerAspGlnLeuIleAsnAspGlyLysLeuProHisIleArgHisGlnThrThrTyrLysProTyr-608 |
| SEQ. ID. NO. 2979 | 612-PheAspGlyArgValGlyTyr-618 |
| SEQ. ID. NO. 2980 | 622-TyrMetAsnLysAspGluLeuIle-629 |
| SEQ. ID. NO. 2981 | 632-IleLeuLysAsnTyrGlu-637 |
| SEQ. ID. NO. 2982 | 654-GluGlnValGluLeuAlaGlu-660 |

Hydrophilic Regions - Hopp-Woods

| | |
|---|---|
| SEQ. ID. NO. 2983 | 29-AspArgAlaLysGlu-33 |
| SEQ. ID. NO. 2984 | 66-ArgLeuGlyArgAspGluAspValPro-74 |
| SEQ. ID. NO. 2985 | 114-ThrProGluHisArgGlnGln-120 |
| SEQ. ID. NO. 2986 | 166-LeuLysGluLysIleSerGlyArgPheGlyAsp-176 |
| SEQ. ID. NO. 2987 | 238-ValGlyLysGlyValLysVal-244 |
| SEQ. ID. NO. 2988 | 293-AlaTyrGluArgGluHisLysPro-300 |
| SEQ. ID. NO. 2989 | 327-IleSerLysGlyArgThrIleArg-334 |
| SEQ. ID. NO. 2990 | 370-MetLeuGluLysMetThrSerPro-378 |
| SEQ. ID. NO. 2991 | 422-ThrSerArgAspLysGlyLeuSer-429 |
| SEQ. ID. NO. 2992 | 484-LeuSerAlaAspLysLysTyrPheGlu-492 |
| SEQ. ID. NO. 2993 | 506-LysTrpLysGluArgLeu-511 |
| SEQ. ID. NO. 2994 | 517-GlnThrGlnGluGlnAspIle-523 |
| SEQ. ID. NO. 2995 | 537-GluLeuGlnArgGluLeuSerGluGluTyrGlyLeu-548 |
| SEQ. ID. NO. 2996 | 550-ValArgValAspLysMetPheHisArgAspGluProAla-562 |
| SEQ. ID. NO. 2997 | 566-ValIleArgLysGluThrMetArg-573 |
| SEQ. ID. NO. 2998 | 581-SerValGlyGlnAspValSerAsp-588 |
| SEQ. ID. NO. 2999 | 590-LeuIleAsnAspGlyLysLeuProHis-598 |
| SEQ. ID. NO. 3000 | 622-TyrMetAsnLysAspGluLeuIle-629 |
| SEQ. ID. NO. 3001 | 654-GluGlnValGluLeuAlaGlu-660 |

164
AMPHI Regions - AMPHI

| | |
|---|---|
| SEQ. ID. NO. 3002 | 6-AlaAsnPheTyrGluMetLeuAlaAlaAla-15 |
| SEQ. ID. NO. 3003 | 33-AlaTyrArgAlaLeuLysGlnGlu-40 |
| SEQ. ID. NO. 3004 | 75-AlaIleSerAlaIleGlyAlaVal-82 |
| SEQ. ID. NO. 3005 | 97-TyrIleLeuAsnAspCys-102 |
| SEQ. ID. NO. 3006 | 113-LeuSerLysGluLeuAlaGlyLeuLysAla-122 |
| SEQ. ID. NO. 3007 | 148-PheGluAspValArgArgPheProGlu-156 |
| SEQ. ID. NO. 3008 | 160-LeuGlyArgGlnProArgIleAsnAspLeuAlaHis-171 |
| SEQ. ID. NO. 3009 | 189-TyrAlaAsnLeuPheAlaAsnLeuAsnGlyIleGluArgIlePheLys-204 |
| SEQ. ID. NO. 3010 | 264-ValProAlaIleTyrThr-269 |
| SEQ. ID. NO. 3011 | 282-TrpPheAsnArgIle-286 |
| SEQ. ID. NO. 3012 | 311-AlaLysLeuLeuGluGlyTyrGlyLeuSer-320 |
| SEQ. ID. NO. 3013 | 362-GluValGlyGluLeuIle-367 |
| SEQ. ID. NO. 3014 | 374-MetArgGlyTyrLeuAsn-379 |
| SEQ. ID. NO. 3015 | 387-ThrIleValAsnGlyTrpLeuLys-394 |
| SEQ. ID. NO. 3016 | 424-ValTyrProArgGluIleGluGluGlu-432 |
| SEQ. ID. NO. 3017 | 459-PheValGlnLeuLysGluGlyMet-466 |
| SEQ. ID. NO. 3018 | 472-GluIleArgArgHisLeuArgThrVal-480 |
| SEQ. ID. NO. 3019 | 484-PheLysIleProLysGln-489 |
| SEQ. ID. NO. 3020 | 499-AsnAlaThrGlyLysValLeuLysArgValLeuLysGluGlnPheAspGlyAsn-516 |

Antigenic Index - Jameson-Wolf

| | |
|---|---|
| SEQ. ID. NO. 3021 | 1-MetAsnArgThrTyr-5 |
| SEQ. ID. NO. 3022 | 15-AlaCysArgLysAsnGlyAsnGly-22 |
| SEQ. ID. NO. 3023 | 26-PheAspGlyLysGluLysThrAlaTyrArgAlaLeuLysGlnGluAlaGluAla-43 |
| SEQ. ID. NO. 3024 | 63-ValSerAsnSerThrGlu-68 |
| SEQ. ID. NO. 3025 | 88-ThrPheLeuLysAsnSerGlu-94 |
| SEQ. ID. NO. 3026 | 100-AsnAspCysLysAla-104 |
| SEQ. ID. NO. 3027 | 112-GlyLeuSerLysGluLeuAlaGly-119 |
| SEQ. ID. NO. 3028 | 121-LysAlaGlnThrProValGlu-127 |

TABLE 1-continued

| | |
|---|---|
| SEQ. ID. NO. 3029 | 130-IleTrpThrAspLysSerArgProThrGlyGluThrAlaGluGlyAsp AlaPhePheGluAspValArgArgPheProGluLysProAspLeuGlyArgGlnProArgIleAsnAsp-168 |
| SEQ. ID. NO. 3030 | 176-SerGlyThrThrGlyHisProLysGlyAla-185 |
| SEQ. ID. NO. 3031 | 196-LeuAsnGlyIleGluArgIlePheLysIleSerLysArgAspArgPhe-211 |
| SEQ. ID. NO. 3032 | 253-ThrLeuLeuLysArg-257 |
| SEQ. ID. NO. 3033 | 290-IleSerGlyGlyAlaProLeuAla-297 |
| SEQ. ID. NO. 3034 | 304-PheLysAlaLysPheProArg-310 |
| SEQ. ID. NO. 3035 | 317-TyrGlyLeuSerGluAlaSer-323 |
| SEQ. ID. NO. 3036 | 330-ThrProGluArgGlnLysAlaArgSer-338 |
| SEQ. ID. NO. 3037 | 343-LeuProGlyLeuGluAlaLysAlaValAspGluGluLeuValGluValProArgGlyGluValGly-364 |
| SEQ. ID. NO. 3038 | 367-IleValArgGlyGlySerValMet-374 |
| SEQ. ID. NO. 3039 | 382-AlaAlaThrAspGluThrIle-388 |
| SEQ. ID. NO. 3040 | 393-LeuLysThrGlyAsp-397 |
| SEQ. ID. NO. 3041 | 400-ThrIleAspGluAspGly-405 |
| SEQ. ID. NO. 3042 | 410-ValAspArgLysLysAspLeuIleIleSerLysGlyGlnAsnValTyrProArgGluIleGluGluGluIleTyrLys-435 |
| SEQ. ID. NO. 3043 | 446-GlyValLysAspArgTyrAlaAspGluGluIle-456 |
| SEQ. ID. NO. 3044 | 462-LeuLysGluGlyMetAspLeuGlyGluAsnGluIleArgArgHisLeuArg-478 |
| SEQ. ID. NO. 3045 | 490-IleHisPheLysAspGlyLeuProArgAsnAlaThrGlyLysValLeuLysArgValLeuLysGluGlnPheAspGlyAsnLys-517 |
| Hydrophilic Regions - Hopp-Woods | |
| SEQ. ID. NO. 3046 | 15-AlaCysArgLysAsnGlyAsn-21 |
| SEQ. ID. NO. 3047 | 26-PheAspGlyLysGluLysThrAlaTyrArgAlaLeuLysGlnGluAlaGluAla-43 |
| SEQ. ID. NO. 3048 | 112-GlyLeuSerLysGluLeuAlaGly-119 |
| SEQ. ID. NO. 3049 | 133-AspLysSerArgProThrGlyGluThrAlaGluGlyAspAlaPhePheGluAspValArgArgPheProGluLysProAspLeuGlyArgGlnProArg IleAsnAsp-168 |
| SEQ. ID. NO. 3050 | 198-GlyIleGluArgIlePheLysIleSerLysArgAspArgPhe-211 |
| SEQ. ID. NO. 3051 | 253-ThrLeuLeuLysArg-257 |
| SEQ. ID. NO. 3052 | 304-PheLysAlaLysPheProArg-310 |
| SEQ. ID. NO. 3053 | 330-ThrProGluArgGlnLysAlaArgSer-338 |
| SEQ. ID. NO. 3054 | 346-LeuGluAlaLysAlaValAspGluGluLeuValGluValProArgGlyGluValGly-364 |
| SEQ. ID. NO. 3055 | 382-AlaAlaThrAspGluThrIle-388 |
| SEQ. ID. NO. 3056 | 400-ThrIleAspGluAspGly-405 |
| SEQ. ID. NO. 3057 | 410-ValAspArgLysLysAspLeuIleIle-418 |
| SEQ. ID. NO. 3058 | 425-TyrProArgGluIleGluGluGluIleTyrLys-435 |
| SEQ. ID. NO. 3059 | 446-GlyValLysAspArgTyrAlaAspGluGluIle-456 |
| SEQ. ID. NO. 3060 | 462-LeuLysGluGlyMetAspLeuGlyGluAsnGluIleArgArgHisLeuArg-478 |
| SEQ. ID. NO. 3061 | 494-AspGlyLeuProArgAsnAlaThr-501 |
| SEQ. ID. NO. 3062 | 503-LysValLeuLysArgValLeuLysGluGlnPheAspGlyAsnLys-517 |
| 165-1 | |
| AMPHI Regions - AMPHI | |
| SEQ. ID. NO. 3063 | 17-AlaThrLeuGlyValLeuLeuLysGluLeu-26 |
| SEQ. ID. NO. 3064 | 33-ThrLeuIleGluArgLeuGluAsp-40 |
| SEQ. ID. NO. 3065 | 72-IleIleAspProAlaArgAlaLeuAsnIleAla-82 |
| SEQ. ID. NO. 3066 | 90-GlnPheTrpAlaThr-94 |
| SEQ. ID. NO. 3067 | 108-AsnAlaValProHis-112 |
| SEQ. ID. NO. 3068 | 125-LeuGlnLysArgTyrAspAlaPheLysThrGlnLysLeuPheGluAsnMet-141 |
| SEQ. ID. NO. 3069 | 182-ArgLeuThrArgGlnMetValLysTyrLeuGlnGly-193 |
| SEQ. ID. NO. 3070 | 198-ThrGluPheAsnArgHisValGluAspIleLysArgGlu-210 |
| SEQ. ID. NO. 3071 | 348-GlyTrpAlaAsnMetPro-353 |
| SEQ. ID. NO. 3072 | 364-LysThrLysGluGlu-368 |
| SEQ. ID. NO. 3073 | 371-AlaSerLeuLeuGluTyrTyr-377 |
| SEQ. ID. NO. 3074 | 453-TrpGluAspArgLeuLysGluLeu-460 |
| Antigenic Index - Jameson-Wolf | |
| SEQ. ID. NO. 3075 | 1-MetAlaGluAlaThrAsp-6 |
| SEQ. ID. NO. 3076 | 24-LysGluLeuGluProSerTrp-30 |
| SEQ. ID. NO. 3077 | 36-GluArgLeuGluAspValAlaLeuGluSerSerAsnAlaTrpAsnAsnAlaGlyThrGly-55 |
| SEQ. ID. NO. 3078 | 97-AlaGluGlyLysLeuGluAspAsnSer-105 |
| SEQ. ID. NO. 3079 | 117-MetAsnGluAspHisCysSerTyrLeuGlnLysArgTyrAspAlaPheLysThrGlnLysLeuPheGlu-139 |
| SEQ. ID. NO. 3080 | 141-MetGluPheSerThrAspArgAsnLysIleSerAsp-152 |
| SEQ. ID. NO. 3081 | 157-MetMetArgGlyArgAspGluAsnGlnPro-166 |
| SEQ. ID. NO. 3082 | 169-AlaAsnTyrSerAlaGluGlyThrAspValAspPheGlyArgLeuThrArgGlnMet-187 |
| SEQ. ID. NO. 3083 | 191-LeuGlnGlyLysGlyValLysThrGluPheAsnArgHisValGluAspIleLysArgGluSerAspGly-213 |
| SEQ. ID. NO. 3084 | 319-ThrAlaAspThrArgAsnProAspGlyGlnLeu-229 |
| SEQ. ID. NO. 3085 | 249-GlnLysSerGlyIleProGlyGlyLysGlyTyrGly-260 |
| SEQ. ID. NO. 3086 | 269-PheArgAsnSerAsnProGluThrAlaGluGlnHisAsn-281 |
| SEQ. ID. NO. 3087 | 300-LeuAspThrArgAsnValAspGlyLysArgHisLeu-311 |
| SEQ. ID. NO. 3088 | 322-AsnPheLeuLysGlnGlySerLeuMet-330 |
| SEQ. ID. NO. 3089 | 361-GluLeuArgLysThrLysGluGluArgPhe-370 |
| SEQ. ID. NO. 3090 | 377-TyrProGluAlaAsnProAspAspTrpGlu-386 |
| SEQ. ID. NO. 3091 | 395-GlnIleIleLysLysAspSerGluLysGlyGly-405 |
| SEQ. ID. NO. 3092 | 415-AlaHisAlaAspGlySer-420 |
| SEQ. ID. NO. 3093 | 428-SerProGlyAlaSerThr-433 |
| SEQ. ID. NO. 3094 | 446-PheProGluArgAlaProSerTrpGluAspArgLeuLysGluLeuValProGlyTyr-464 |
| SEQ. ID. NO. 3095 | 467-LysLeuAsnGluAsnProGluArgAlaAspGlu-477 |
| Hydrophilic Regions - Hopp-Woods | |
| SEQ. ID. NO. 3096 | 1-MetAlaGluAlaThrAsp-6 |
| SEQ. ID. NO. 3097 | 24-LysGluLeuGluPro-28 |
| SEQ. ID. NO. 3098 | 36-GluArgLeuGluAspValAlaLeuGluSer-45 |
| SEQ. ID. NO. 3099 | 97-AlaGluGlyLysLeuGluAspAsnSer-105 |
| SEQ. ID. NO. 3100 | 117-MetAsnGluAspHisCys-122 |
| SEQ. ID. NO. 3101 | 125-LeuGlnLysArgTyrAspAlaPheLysThr-134 |

TABLE 1-continued

| | |
|---|---|
| SEQ. ID. NO. 3102 | 141-MetGluPheSerThrAspArgAsnLysIleSerAsp-152 |
| SEQ. ID. NO. 3103 | 158-MetArgGlyArgAspGluAsnGlnPro-166 |
| SEQ. ID. NO. 3104 | 172-SerAlaGluGlyThrAspValAspPhe-180 |
| SEQ. ID. NO. 3105 | 182-ArgLeuThrArgGlnMet-187 |
| SEQ. ID. NO. 3106 | 194-LysGlyValLysThrGluPheAsnArgHisValGluAspIleLysArgGluSerAspGly-213 |
| SEQ. ID. NO. 3107 | 219-ThrAlaAspThrArgAsnProAspGly-227 |
| SEQ. ID. NO. 3108 | 252-GlyIleProGluGlyLysGly-258 |
| SEQ. ID. NO. 3109 | 272-SerAsnProGluThrAlaGluGlnHisAsn-281 |
| SEQ. ID. NO. 3110 | 300-LeuAspThrArgAsnValAspGlyLysArg-309 |
| SEQ. ID. NO. 3111 | 361-GluLeuArgLysThrLysGluGluArgPhe-370 |
| SEQ. ID. NO. 3112 | 380-AlaAsnProAspAspTrpGlu-386 |
| SEQ. ID. NO. 3113 | 395-GlnIleIleLysLysAspSerGluLysGlyGly-405 |
| SEQ. ID. NO. 3114 | 446-PheProGluArgAlaProSerTrpGluAspArgLeuLysGluLeuVal-461 |
| SEQ. ID. NO. 3115 | 467-LysLeuAsnGluAsnProGluArgAlaAspGlu-477 |
| Hydrophilic Regions - Hopp-Woods | |
| SEQ. ID. NO. 3116 | 1-MetAlaGluAlaThrAsp-6 |
| SEQ. ID. NO. 3117 | 24-LysGluLeuGluPro-28 |
| SEQ. ID. NO. 3118 | 36-GluArgLeuGluAspValAlaLeuGluSer-45 |
| SEQ. ID. NO. 3119 | 97-AlaGluGlyLysLeuGluAspAsnSer-105 |
| SEQ. ID. NO. 3120 | 117-MetAsnGluAspHisCys-122 |
| SEQ. ID. NO. 3121 | 125-LeuGlnLysArgTyrAspAlaPheLysThr-134 |
| SEQ. ID. NO. 3122 | 141-MetGluPheSerThrAspArgAsnLysIleSerAsp-152 |
| SEQ. ID. NO. 3123 | 158-MetArgGlyArgAspGluAsnGlnPro-166 |
| SEQ. ID. NO. 3124 | 172-SerAlaGluGlyThrAspValAspPhe-180 |
| SEQ. ID. NO. 3125 | 182-ArgLeuThrArgGlnMet-187 |
| SEQ. ID. NO. 3126 | 194-LysGlyValLysThrGluPheAsnArgHisValGluAspIleLysArgGluSerAspGly-213 |
| SEQ. ID. NO. 3127 | 219-ThrAlaAspThrArgAsnProAspGly-227 |
| SEQ. ID. NO. 3128 | 252-GlyIleProGluGlyLysGly-258 |
| SEQ. ID. NO. 3129 | 272-SerAsnProGluThrAlaGluGlnHisAsn-281 |
| SEQ. ID. NO. 3130 | 300-LeuAspThrArgAsnValAspGlyLysArg-309 |
| SEQ. ID. NO. 3131 | 361-GluLeuArgLysThrLysGluGluArgPhe-370 |
| SEQ. ID. NO. 3132 | 380-AlaAsnProAspAspTrpGlu-386 |
| SEQ. ID. NO. 3133 | 395-GlnIleIleLysLysAspSerGluLysGlyGly-405 |
| SEQ. ID. NO. 3134 | 446-PheProGluArgAlaProSerTrpGluAspArgLeuLysGluLeuVal-461 |
| SEQ. ID. NO. 3135 | 467-LysLeuAsnGluAsnProGluArgAlaAspGlu-477 |
| 204-2 | |
| AMPHI Regions - AMPHI | |
| SEQ. ID. NO. 3136 | 43-GlnAlaPheAsnArgIleThrAspLeuPhePhe-53 |
| SEQ. ID. NO. 3137 | 62-AlaLeuSerGlnIle-66 |
| SEQ. ID. NO. 3138 | 70-AsnArgArgIleValAspIlePheAspPheGluAsn-81 |
| SEQ. ID. NO. 3139 | 83-PheArgArgAlaLeuTyrArgValLeuArgLeuPheArgArgIlePheGly-99 |
| Antigenic Index - Jameson-Wolf | |
| SEQ. ID. NO. 3140 | 34-AspGlnSerAspAsnIleLeu-40 |
| SEQ. ID. NO. 3141 | 44-AlaPheAsnArgIle-48 |
| SEQ. ID. NO. 3142 | 66-IleGlnThrGlyAsnArgArgIleValAsp-75 |
| SEQ. ID. NO. 3143 | 77-PheAspPheGluAsnArgPheArgArgAlaLeu-87 |
| SEQ. ID. NO. 3144 | 101-AlaAlaGlyGlyLysGlnGlnAla-108 |
| SEQ. ID. NO. 3145 | 112-TyrGlyLysArgCysPhe-117 |
| SEQ. ID. NO. 3146 | 126-SerLysCysArgLeuLysArgGlyArgArgArgPheGlyArgHisArgValHisPheAsnGlyArgMetProThrAlaSerArgThrLeuSerAsn AsnSerArgAlaSerLeu-163 |
| SEQ. ID. NO. 3147 | 169-ProAlaCysLysIle-173 |
| SEQ. ID. NO. 3148 | 177-CysGluGlySerAla-181 |
| Hydrophilic Regions - Hopp-Woods | |
| SEQ. ID. NO. 3149 | 68-ThrGlyAsnArgArgIleValAsp-75 |
| SEQ. ID. NO. 3150 | 77-PheAspPheGluAsnArgPheArgArgAlaLeu-87 |
| SEQ. ID. NO. 3151 | 104-GlyLysGlnGlnAla-108 |
| SEQ. ID. NO. 3152 | 112-TyrGlyLysArgCysPhe-117 |
| SEQ. ID. NO. 3153 | 126-SerLysCysArgLeuLysArgGlyArgArgArgPheGlyArgHisArgVal-142 |
| SEQ. ID. NO. 3154 | 148-MetProThrAlaSerArgThrLeuSerAsnAsnSerArgAlaSerLeu-163 |
| 205-1 (same as orf108, so delete this one) | |
| AMPHI Regions - AMPHI | |
| SEQ. ID. NO. 3155 | 21-SerGluAsnThrAlaGluGlnProGlnAsnAlaValGlnSerAlaProLys-37 |
| SEQ. ID. NO. 3156 | 79-GluGlnAsnValIleArgLeuIleGlyLysHisProGlyAspLeu-93 |
| SEQ. ID. NO. 3157 | 119-HisThrLeuPheAlaLysLeuValGlyAsnIleAlaGluAspGlyGlyLys-135 |
| Antigenic Index - Jameson-Wolf | |
| SEQ. ID. NO. 3158 | 18-CysGlyLysSerGluAsnThrAlaGluGlnProGlnAsnAlaValGlnSerAlaProLysProValPhe-40 |
| SEQ. ID. NO. 3159 | 55-LeuGlyGlnSerSerGluGlyLysThrAsnAspGlyLysLysGlnIle-70 |
| SEQ. ID. NO. 3160 | 73-ProIleLysGlyLeuProGluGlnAsnVal-82 |
| SEQ. ID. NO. 3161 | 86-IleGlyLysHisProGlyAspLeuGluAlaValSerGlyLysCysMetGluThrAspAspLysAspSerProAlaGlyTrpAlaGlu-114 |
| SEQ. ID. NO. 3162 | 129-IleAlaGluAspGlyGlyLysLeuThr-137 |
| SEQ. ID. NO. 3163 | 149-TyrGlnAlaGlyLysSerGlyTyr-156 |
| SEQ. ID. NO. 3164 | 168-IleAspSerGluGly-172 |
| SEQ. ID. NO. 3165 | 175-TyrPheArgArgArgHisTyr-181 |
| Hydrophilic Regions - Hopp-Woods | |
| SEQ. ID. NO. 3166 | 19-GlyLysSerGluAsnThrAlaGluGlnProGln-29 |
| SEQ. ID. NO. 3167 | 56-GlyGlnSerSerGluGlyLysThrAsnAspGlyLysLysGlnIle-70 |
| SEQ. ID. NO. 3168 | 89-HisProGlyAspLeuGluAlaValSer-97 |
| SEQ. ID. NO. 3169 | 99-LysCysMetGluThrAspAspLysAspSerPro-109 |
| SEQ. ID. NO. 3170 | 129-IleAlaGluAspGlyGlyLysLeu-136 |
| SEQ. ID. NO. 3171 | 150-GlnAlaGlyLysSerGly-155 |

TABLE 1-continued

| | |
|---|---|
| SEQ. ID. NO. 3172 | 168-IleAspSerGluGly-172 |
| SEQ. ID. NO. 3173 | 176-PheArgArgArgHisTyr-181 |

206-2
AMPHI Regions - AMPHI
| | |
|---|---|
| SEQ. ID. NO. 3174 | 32-ProLysGlnThrValArgGlnIleGlnAlaVal-42 |
| SEQ. ID. NO. 3175 | 44-IleSerHisIleAspArgThrGlnGly-52 |
| SEQ. ID. NO. 3176 | 81-CysSerGlyMetIleGln-86 |
| SEQ. ID. NO. 3177 | 99-ArgThrAlaArgAspMet-104 |
| SEQ. ID. NO. 3178 | 150-SerGlyLysThrIleLysThrGlu-157 |

Antigenic Index - Jameson-Wolf
| | |
|---|---|
| SEQ. ID. NO. 3179 | 2-PheProProAspLysThrLeu-8 |
| SEQ. ID. NO. 3180 | 21-GlyThrThrSerGlyLysHisArgGlnProLysProLysGlnThrValArg-37 |
| SEQ. ID. NO. 3181 | 45-SerHisIleAspArgThrGlnGlySerGln-54 |
| SEQ. ID. NO. 3182 | 66-ThrProTyrLysTrpGlyGlySerSerThr-75 |
| SEQ. ID. NO. 3183 | 96-LysLeuProArgThrAlaArgAspMetAlaAlaAlaSerArgLysIleProAspSerArgLeuLysAlaGly-119 |
| SEQ. ID. NO. 3184 | 126-ThrGlyGlyAlaHisArgTyrSer-133 |
| SEQ. ID. NO. 3185 | 148-ProSerSerGlyLysThrIleLysThrGluLysLeuSer-160 |

Hydrophilic Regions - Hopp-Woods
| | |
|---|---|
| SEQ. ID. NO. 3186 | 23-ThrSerGlyLysHisArgGlnProLysProLysGlnThrVal-36 |
| SEQ. ID. NO. 3187 | 45-SerHisIleAspArgThrGlnGlySerGln-54 |
| SEQ. ID. NO. 3188 | 96-LysLeuProArgThrAlaArgAspMetAlaAlaAlaSerArgLysIleProAspSerArgLeuLysAlaGly-119 |
| SEQ. ID. NO. 3189 | 149-SerGlyLysThrIleLysThrGluLysLeuSer-160 |

211-2
AMPHI Regions - AMPHI
| | |
|---|---|
| SEQ. ID. NO. 3190 | 18-ValGlyAsnGlyValAspGluPheGlyArgGlyAla-29 |
| SEQ. ID. NO. 3191 | 57-GlnPheGluArgAla-61 |
| SEQ. ID. NO. 3192 | 98-IleGluGlyPheAspLysIleAsnProAla-107 |

Antigenic Index - Jameson-Wolf
| | |
|---|---|
| SEQ. ID. NO. 3193 | 8-AsnGlnLeuGlyGlyArgAsnGlyThrAlaValGlyAsnGlyValAspGluPheGlyArgGlyAlaAspAsnGlnValGluPheLeuGlu-37 |
| SEQ. ID. NO. 3194 | 44-GlyAlaSerGlyArgAlaAla-50 |
| SEQ. ID. NO. 3195 | 73-GlyGluAspAspValVal-78 |
| SEQ. ID. NO. 3196 | 100-GlyPheAspLysIleAsnProAlaVal-108 |

Hydrophilic Regions - Hopp-Woods
| | |
|---|---|
| SEQ. ID. NO. 3197 | 10-LeuGlyGlyArgAsnGlyThr-16 |
| SEQ. ID. NO. 3198 | 21-GlyValAspGluPheGlyArgGlyAlaAspAsnGlnValGluPheLeuGlu-37 |
| SEQ. ID. NO. 3199 | 73-GlyGluAspAspValVal-78 |
| SEQ. ID. NO. 3200 | 100-GlyPheAspLysIleAsn-105 |

212-2
AMPHI Regions - AMPHI
| | |
|---|---|
| SEQ. ID. NO. 3201 | 6-TrpAspGlyIleProAspIleArgThr-14 |
| SEQ. ID. NO. 3202 | 40-PheGlnThrAlaGlnAsp-45 |
| SEQ. ID. NO. 3203 | 64-LeuGlnPheAspSerIleAsnLeuIleGluHisIle-75 |
| SEQ. ID. NO. 3204 | 91-HisLeuHisGluHis-95 |
| SEQ. ID. NO. 3205 | 199-ArgLeuLeuGlyHis-203 |
| SEQ. ID. NO. 3206 | 238-HisAsnHisLeuTyrArgSerIleThrSerAlaGluAlaGluLysIle-253 |
| SEQ. ID. NO. 3207 | 397-TrpAsnGluAlaGluGluAla-403 |
| SEQ. ID. NO. 3208 | 439-AspSerProAspHis-443 |
| SEQ. ID. NO. 3209 | 445-ProLeuValGlyAlaLeuGlyAspIleAlaAlaMet-456 |
| SEQ. ID. NO. 3210 | 487-HisGlyThrArgGlyLeu-492 |
| SEQ. ID. NO. 3211 | 501-AlaIleAlaAlaAlaGlnIleLeuGlyLeuPro-510 |

Antigenic Index - Jameson-Wolf
| | |
|---|---|
| SEQ. ID. NO. 3212 | 8-GlyIleProAspIleArgThrLeuAspGlnAlaIleArgLysHisAlaProProLeuAsn-27 |
| SEQ. ID. NO. 3213 | 33-ProAspAsnGlnIleProAspPheGlnThrAlaGlnAspAlaSerAspAlaGluCysArgLeuLysHisArgLeuAspGln-59 |
| SEQ. ID. NO. 3214 | 85-ProProSerArgThr-89 |
| SEQ. ID. NO. 3215 | 105-AlaIleProGlnThrGluSerLysProAspLysProTrp-117 |
| SEQ. ID. NO. 3216 | 120-LeuProGlnThrSerGluArgGlnLysProGluHis-131 |
| SEQ. ID. NO. 3217 | 158-LeuGluAlaArgLysAlaAlaGln-165 |
| SEQ. ID. NO. 3218 | 168-SerGlyAsnArgGlnGly-173 |
| SEQ. ID. NO. 3219 | 178-LysIleSerProHisAspThrGluGlnThrGlu-188 |
| SEQ. ID. NO. 3220 | 193-GlyTyrGlyTyrThrLys-198 |
| SEQ. ID. NO. 3221 | 205-LeuProGluSerGluThrTrpGlyGlyAsnGly-215 |
| SEQ. ID. NO. 3222 | 220-AsnTyrSerArgThrGluGlnAsnArgAsnHisGluLeuGlyLeu-234 |
| SEQ. ID. NO. 3223 | 246-ThrSerAlaGluAlaGluLysIleAla-254 |
| SEQ. ID. NO. 3224 | 260-ValProTyrAspHisProSerCys-267 |
| SEQ. ID. NO. 3225 | 294-LeuHisGluAspThrProLeu-300 |
| SEQ. ID. NO. 3226 | 302-AspIleSerHisAspGlyGluLysTrpIle-311 |
| SEQ. ID. NO. 3227 | 328-ThrGlyAlaAsnSerProTyrLeuPro-336 |
| SEQ. ID. NO. 3228 | 346-ArgGlnIleArgGlyGlnThrGlyLeuThrProSerThrProPheSerGluGlnLeuArg-365 |
| SEQ. ID. NO. 3229 | 376-ProSerTrpHisGly-380 |
| SEQ. ID. NO. 3230 | 391-AsnSerSerHisThrGlyTrpAsnGluAlaGluGluAlaSerAsnArgGlnAla-408 |
| SEQ. ID. NO. 3231 | 424-AsnProAsnProGlnLysHisGlnGly-432 |
| SEQ. ID. NO. 3232 | 436-IleArgCysAspSerProAspHisLeuPro-445 |
| SEQ. ID. NO. 3233 | 464-AlaLeuAspLysAsnTyrArgIleAspThrProCys-475 |
| SEQ. ID. NO. 3234 | 487-HisGlyThrArgGlyLeuAla-493 |
| SEQ. ID. NO. 3235 | 511-HisProPheSerGlnArgLeuArgHisAlaLeuHisProAsnArgThrIle-527 |
| SEQ. ID. NO. 3236 | 531-IleValArgArgLysAspLeuThrPro-539 |

Hydrophilic Regions - Hopp-Woods
| | |
|---|---|
| SEQ. ID. NO. 3237 | 10-ProAspIleArgThrLeuAspGlnAlaIleArgLysHisAlaPro-24 |
| SEQ. ID. NO. 3238 | 44-GlnAspAlaSerAspAlaGluCysArgLeuLysHisArgLeuAspGln-59 |
| SEQ. ID. NO. 3239 | 105-AlaIleProGlnThrGluSerLysProAspLys-115 |

TABLE 1-continued

| | |
|---|---|
| SEQ. ID. NO. 3240 | 122-GlnThrSerGluArgGlnLysProGluHis-131 |
| SEQ. ID. NO. 3241 | 158-LeuGluAlaArgLysAlaAlaGln-165 |
| SEQ. ID. NO. 3242 | 180-SerProHisAspThrGluGlnThrGlu-188 |
| SEQ. ID. NO. 3243 | 206-ProGluSerGluThr-210 |
| SEQ. ID. NO. 3244 | 222-SerArgThrGluGlnArgAsnHisGlu-231 |
| SEQ. ID. NO. 3245 | 246-ThrSerAlaGluAlaGluLysIleAla-254 |
| SEQ. ID. NO. 3246 | 294-LeuHisGluAspThrProLeu-300 |
| SEQ. ID. NO. 3247 | 303-IleSerHisAspGlyGluLysTrpIle-311 |
| SEQ. ID. NO. 3248 | 346-ArgGlnIleArgGly-350 |
| SEQ. ID. NO. 3249 | 398-AsnGluAlaGluGluAlaSerAsnArgGlnAla-408 |
| SEQ. ID. NO. 3250 | 426-AsnProGlnLysHisGlnGly-432 |
| SEQ. ID. NO. 3251 | 436-IleArgCysAspSerProAsp-442 |
| SEQ. ID. NO. 3252 | 467-LysAsnTyrArgIleAspThr-473 |
| SEQ. ID. NO. 3253 | 515-GlnArgLeuArgHis-519 |
| SEQ. ID. NO. 3254 | 531-IleValArgArgLysAspLeuThrPro-539 |
| 214-1 | |
| AMPHI Regions - AMPHI | |
| SEQ. ID. NO. 3255 | 6-CysLysLeuPheValLeuIle-12 |
| SEQ. ID. NO. 3256 | 69-ValThrArgGlyGlyLysGlyGlyGluSerVal-79 |
| SEQ. ID. NO. 3257 | 88-PheSerGlnThrLeuAsp-93 |
| SEQ. ID. NO. 3258 | 122-LysValGlnArgGlyGlyAspVal-129 |
| SEQ. ID. NO. 3259 | 150-ThrLysSerGlyAlaLysSerAlaSerLys-159 |
| Antigenic Index - Jameson-Wolf | |
| SEQ. ID. NO. 3260 | 23-LeuGlnSerAspSerArgGlnProIle-31 |
| SEQ. ID. NO. 3261 | 33-IleGluAlaAspGlnGlySerLeuAspGlnAlaAsnGlnSerThrThrPheSerGlyAsn-52 |
| SEQ. ID. NO. 3262 | 71-ArgGlyGlyLysGlyGlyGluSerValArgAlaGluGlySerProValArgPheSerGlnThrLeuAspGlyGlyLysGlyThrValArgGlyGlnAlaAsnAsn-105 |
| SEQ. ID. NO. 3263 | 119-GlyAsnAlaLysValGlnArgGlyGlyAspValAlaGlu-131 |
| SEQ. ID. NO. 3264 | 137-TyrAsnThrLysThrGluVal-143 |
| SEQ. ID. NO. 3265 | 148-GlySerThrLysSerGlyAlaLysSerAlaSerLysSerGlyArgValSerVal-165 |
| SEQ. ID. NO. 3266 | 168-GlnProSerSerThrGlnLysSerGlu-176 |
| Hydrophilic Regions - Hopp-Woods | |
| SEQ. ID. NO. 3267 | 25-SerAspSerArgGlnProIle-31 |
| SEQ. ID. NO. 3268 | 33-IleGluAlaAspGlnGlySerLeuAspGlnAlaAsn-44 |
| SEQ. ID. NO. 3269 | 71-ArgGlyGlyLysGlyGlyGluSerValArgAlaGluGlySerPro-85 |
| SEQ. ID. NO. 3270 | 92-LeuAspGlyGlyLysGlyThrValArgGlyGlnAla-103 |
| SEQ. ID. NO. 3271 | 121-AlaLysValGlnArgGlyGlyAspValAlaGlu-131 |
| SEQ. ID. NO. 3272 | 148-GlySerThrLysSerGlyAlaLysSerAlaSerLysSerGlyArg-162 |
| SEQ. ID. NO. 3273 | 171-SerThrGlnLysSerGlu-176 |
| 215-2 | |
| AMPHI Regions - AMPHI | |
| SEQ. ID. NO. 3274 | 21-SerLeuSerAlaTrpLeuGlyArgIle-29 |
| SEQ. ID. NO. 3275 | 67-SerAlaLysGlyAlaLysGlnPheProGlu-76 |
| Antigenic Index - Jameson-Wolf | |
| SEQ. ID. NO. 3276 | 3-ValArgTrpArgTyrGly-8 |
| SEQ. ID. NO. 3277 | 28-ArgIleSerGluValGluIleGluGluValArgLeuAsnProAspGluProGlnTyrThrMetAspGlyLeuAspGlyArgArgPheAspGluGlnGlyTyrLeuLys-63 |
| SEQ. ID. NO. 3278 | 65-HisLeuSerAlaLysGlyAlaLysGlnPheProGluSerSerAspIleHisPheAspSerProHisLeu-87 |
| SEQ. ID. NO. 3279 | 99-ValGlySerAspGluAlaValTyrHisThrGluAsnLysGlnValLeuPhe-115 |
| SEQ. ID. NO. 3280 | 123-LysThrAlaAspGlyLysArgGlnAlaGlyLysValGluAlaGluLysLeuHisValAspThrGluSerGlnTyrAlaGlnThrAspThrProVal-154 |
| SEQ. ID. NO. 3281 | 160-AlaSerHisGlyGlnAlaGlyGlyMetThrTyrAspHisLysThrGly-175 |
| SEQ. ID. NO. 3282 | 179-PheSerSerLysValLys-184 |
| SEQ. ID. NO. 3283 | 187-IleTyrAspThrLysAspMet-193 |
| Hydrophilic Regions - Hopp-Woods | |
| SEQ. ID. NO. 3284 | 29-IleSerGluValGluIleGluGluValArgLeuAsnProAspGluProGlnTyr-46 |
| SEQ. ID. NO. 3285 | 49-AspGlyLeuAspGlyArgArgPheAspGlu-58 |
| SEQ. ID. NO. 3286 | 65-HisLeuSerAlaLysGlyAlaLysGlnPheProGluSerSerAspIleHisPhe-82 |
| SEQ. ID. NO. 3287 | 99-ValGlySerAspGluAlaValTyr-106 |
| SEQ. ID. NO. 3288 | 108-ThrGluAsnLysGlnValLeu-114 |
| SEQ. ID. NO. 3289 | 123-LysThrAlaAspGlyLysArgGlnAlaGlyLysValGluAlaGluLysLeuHisValAspThrGluSerGlnTyrAla-148 |
| SEQ. ID. NO. 3290 | 170-TyrAspHisLysThr-174 |
| SEQ. ID. NO. 3291 | 187-IleTyrAspThrLysAspMet-193 |
| 216-2 | |
| AMPHI Regions - AMPHI | |
| SEQ. ID. NO. 3292 | 6-LysTyrLeuAspTrpAlaArg-12 |
| SEQ. ID. NO. 3293 | 19-AlaGluGlyLeuArgGluIleAlaAlaGluLeu-29 |
| SEQ. ID. NO. 3294 | 60-ArgLysMetAlaAla-64 |
| SEQ. ID. NO. 3295 | 165-LeuGlyAspAlaLeuAlaVal-171 |
| SEQ. ID. NO. 3296 | 201-ValAlaAspIleMetHis-206 |
| SEQ. ID. NO. 3297 | 216-LeuGlyThrProLeuLysGlu-222 |
| SEQ. ID. NO. 3298 | 242-GlyArgLeuLysGlyVal-247 |
| SEQ. ID. NO. 3299 | 251-GlyAspLeuArgArgLeuPheGlnGluCysAspAsnPheThrGlyLeuSerIle-268 |
| SEQ. ID. NO. 3300 | 272-MetHisThrHisProLysThrIleSerAla-281 |
| SEQ. ID. NO. 3301 | 290-LysValMetGlnAlaAsn-295 |
| Antigenic Index - Jameson-Wolf | |
| SEQ. ID. NO. 3302 | 1-MetAlaGluAsnGlyLysTyr-7 |
| SEQ. ID. NO. 3303 | 14-ValLeuHisAlaGluAlaGluGlyLeuArgGluIleAlaAlaGluLeuAspLysAsnPhe-33 |
| SEQ. ID. NO. 3304 | 43-CysLysGlyArgVal-47 |
| SEQ. ID. NO. 3305 | 51-GlyMetGlyLysSerGlyHisIleGlyArgLysMetAla-63 |
| SEQ. ID. NO. 3306 | 80-GluAlaAlaHisGlyAspLeu-86 |

TABLE 1-continued

| | |
|---|---|
| SEQ. ID. NO. 3307 | 90-ValAspAsnAspVal-94 |
| SEQ. ID. NO. 3308 | 99-SerAsnSerGlyGluSerAspGluIle-107 |
| SEQ. ID. NO. 3309 | 113-AlaLeuLysArgLysAspIle-119 |
| SEQ. ID. NO. 3310 | 125-ThrAlaArgProAspSerThrMetAlaArgHisAlaAsp-137 |
| SEQ. ID. NO. 3311 | 144-ValSerLysGluAlaCysPro-150 |
| SEQ. ID. NO. 3312 | 177-ArgAlaPheThrProAspAspPheAla-185 |
| SEQ. ID. NO. 3313 | 188-HisProAlaGlySerLeuGlyLys-195 |
| SEQ. ID. NO. 3314 | 203-AspIleMetHisLysGlyGlyGlyLeuProAla-213 |
| SEQ. ID. NO. 3315 | 216-LeuGlyThrProLeuLysGluAlaIle-224 |
| SEQ. ID. NO. 3316 | 227-MetSerGluLysGlyLeu-232 |
| SEQ. ID. NO. 3317 | 237-ValThrAspGlyGlnGlyArgLeuLysGly-246 |
| SEQ. ID. NO. 3318 | 248-PheThrAspGlyAspLeuArgArgLeuPheGlnGluCysAspAsnPheThr-264 |
| SEQ. ID. NO. 3319 | 275-HisProLysThrIleSerAlaGluArgLeuAlaThrGluAlaLeuLys-290 |
| SEQ. ID. NO. 3320 | 303-ThrAspAlaAspGly-307 |
| Hydrophilic Regions - Hopp-Woods | |
| SEQ. ID. NO. 3321 | 1-MetAlaGluAsnGlyLys-6 |
| SEQ. ID. NO. 3322 | 14-ValLeuHisAlaGluAlaGluGlyLeuArgGluIleAlaAlaGluLeuAspLys-31 |
| SEQ. ID. NO. 3323 | 43-CysLysGlyArgVal-47 |
| SEQ. ID. NO. 3324 | 56-GlyHisIleGlyArgLysMetAla-63 |
| SEQ. ID. NO. 3325 | 100-AsnSerGlyGluSerAspGluIle-107 |
| SEQ. ID. NO. 3326 | 113-AlaLeuLysArgLysAspIle-119 |
| SEQ. ID. NO. 3327 | 126-AlaArgProAspSerThrMetAlaArgHisAlaAsp-137 |
| SEQ. ID. NO. 3328 | 144-ValSerLysGluAlaCys-149 |
| SEQ. ID. NO. 3329 | 177-ArgAlaPheThrProAspAspPheAla-185 |
| SEQ. ID. NO. 3330 | 218-ThrProLeuLysGluAlaIle-224 |
| SEQ. ID. NO. 3331 | 227-MetSerGluLysGlyLeu-232 |
| SEQ. ID. NO. 3332 | 239-AspGlyGlnGlyArgLeuLys-245 |
| SEQ. ID. NO. 3333 | 251-GlyAspLeuArgArgLeuPheGlnGluCysAspAsn-262 |
| SEQ. ID. NO. 3334 | 277-LysThrIleSerAlaGluArgLeuAlaThrGluAlaLeuLys-290 |
| SEQ. ID. NO. 3335 | 303-ThrAspAlaAspGly-307 |
| 218-2 | |
| AMPHI Regions - AMPHI | |
| SEQ. ID. NO. 3336 | 37-LeuLeuAlaValThr-41 |
| SEQ. ID. NO. 3337 | 121-AlaLysValValSerThrMet-127 |
| SEQ. ID. NO. 3338 | 136-ThrMetAspGluIleHisSer-142 |
| SEQ. ID. NO. 3339 | 190-AlaArgSerTrpTrpArgAsnLeuHisGlyThrPheGlyThrTrpValSerLeuIleLeu-209 |
| SEQ. ID. NO. 3340 | 223-TrpGlyGlyLysPheValGlnAlaTrpSerGlnPhePro-235 |
| SEQ. ID. NO. 3341 | 288-AspGluProMetThrLeuGluThrValAspArgPheAlaArgGlu-302 |
| SEQ. ID. NO. 3342 | 359-TyrAsnProPheGlyLysPheMet-366 |
| SEQ. ID. NO. 3343 | 377-LeuGlyTrpTrpSerValLeuAlaAsn-385 |
| Antigenic Index - Jameson-Wolf | |
| SEQ. ID. NO. 3344 | 3-ThrGlnIleLysThrGluAlaAspAsnGlnSerAsnArgArgTyrLeu-18 |
| SEQ. ID. NO. 3345 | 51-IleThrGlyLysGluGlyGluArgIleHis-60 |
| SEQ. ID. NO. 3346 | 74-AlaGluAlaAlaArgSerAlaValAsnProGluThrSerSer-87 |
| SEQ. ID. NO. 3347 | 94-ProArgAlaAspAspMet-99 |
| SEQ. ID. NO. 3348 | 105-ValAsnAsnGluGlyLysAla-111 |
| SEQ. ID. NO. 3349 | 125-SerThrMetProArgAsnGlnGlyTrp-133 |
| SEQ. ID. NO. 3350 | 174-ValLysArgArgGlyIleLysAla-181 |
| SEQ. ID. NO. 3351 | 183-LeuLeuProSerLysGlyArgAlaArgSerTrpTrp-194 |
| SEQ. ID. NO. 3352 | 196-AsnLeuHisGlyThrPheGly-202 |
| SEQ. ID. NO. 3353 | 235-ProAlaGlyLysTrpGlyValGluProAsnProVal-246 |
| SEQ. ID. NO. 3354 | 255-ValLeuAsnAspGlyLysValLysGlu-263 |
| SEQ. ID. NO. 3355 | 279-ThrValGlyLysAspGlyIleAsnProAspGluProMetThr-292 |
| SEQ. ID. NO. 3356 | 294-GluThrValAspArgPheAlaArg-301 |
| SEQ. ID. NO. 3357 | 303-IleGlyPheLysGlyArgTyrArgLeuAsnLeuProLysGlyGluAspGly-319 |
| SEQ. ID. NO. 3358 | 323-LeuSerGlnAspSerMetSerTyr-330 |
| SEQ. ID. NO. 3359 | 336-PheAlaAspArgThrValHis-342 |
| SEQ. ID. NO. 3360 | 344-AspGlnTyrSerGlyLysIleLeuAla-352 |
| SEQ. ID. NO. 3361 | 354-IleArgPheAspTyrAsnProPhe-362 |
| SEQ. ID. NO. 3362 | 404-TrpLysArgArgProThrGlyAla-411 |
| SEQ. ID. NO. 3363 | 417-ProAlaGlnLysValLysLeu-423 |
| Hydrophilic Regions - Hopp-Woods | |
| SEQ. ID. NO. 3364 | 3-ThrGlnIleLysThrGluAlaAspAsnGlnSerAsnArgArgTyr-17 |
| SEQ. ID. NO. 3365 | 52-ThrGlyLysGluGlyGluArgIleHis-60 |
| SEQ. ID. NO. 3366 | 74-AlaGluAlaAlaArgSerAlaValAsnProGluThrSerSer-87 |
| SEQ. ID. NO. 3367 | 94-ProArgAlaAspAspMet-99 |
| SEQ. ID. NO. 3368 | 105-ValAsnAsnGluGlyLysAla-111 |
| SEQ. ID. NO. 3369 | 175-LysArgArgGlyIleLys-180 |
| SEQ. ID. NO. 3370 | 186-SerLysGlyArgAla-190 |
| SEQ. ID. NO. 3371 | 255-ValLeuAsnAspGlyLysValLysGlu-263 |
| SEQ. ID. NO. 3372 | 279-ThrValGlyLysAspGlyIleAsnProAspGluProMetThr-292 |
| SEQ. ID. NO. 3373 | 294-GluThrValAspArgPheAlaArg-301 |
| SEQ. ID. NO. 3374 | 314-ProLysGlyGluAspGly-319 |
| SEQ. ID. NO. 3375 | 325-GlnAspSerMetSer-329 |
| SEQ. ID. NO. 3376 | 336-PheAlaAspArgThrValHis-342 |
| SEQ. ID. NO. 3377 | 354-IleArgPheAspAsp-358 |
| SEQ. ID. NO. 3378 | 405-LysArgArgProThrGly-410 |
| 219-2 (included in 218, so delete this one) | |
| AMPHI Regions - AMPHI | |
| SEQ. ID. NO. 3379 | 37-LeuLeuAlaValThr-41 |

TABLE 1-continued

| | |
|---|---|
| SEQ. ID. NO. 3380 | 121-AlaLysValValSerThrMet-127 |
| SEQ. ID. NO. 3381 | 136-ThrMetAspGluIleHisSer-142 |
| SEQ. ID. NO. 3382 | 190-AlaArgSerTrpTrpArgAsnLeuHisGlyThrPheGlyThrTrpValSerLeuIleLeu-209 |
| SEQ. ID. NO. 3383 | 223-TrpGlyGlyLysPheValGlnAlaTrpSerGlnPhePro-235 |
| SEQ. ID. NO. 3384 | 288-AspGluProMetThrLeuGluThrValAspArgPheAlaArgGlu-302 |
| SEQ. ID. NO. 3385 | 359-TyrAsnProPheGlyLysPheMet-366 |
| SEQ. ID. NO. 3386 | 377-LeuGlyTrpTrpSerValLeuAlaAsn-385 |

Antigenic Index - Jameson-Wolf

| | |
|---|---|
| SEQ. ID. NO. 3387 | 3-ThrGlnIleLysThrGluAlaAspAsnGlnSerAsnArgArgTyrLeu-18 |
| SEQ. ID. NO. 3388 | 51-IleThrGlyLysGluGlyGluArgIleHis-60 |
| SEQ. ID. NO. 3389 | 74-AlaGluAlaAlaArgSerAlaValAsnProGluThrSerSer-87 |
| SEQ. ID. NO. 3390 | 94-ProArgAlaAspAspMet-99 |
| SEQ. ID. NO. 3391 | 105-ValAsnAsnGluGlyLysAla-111 |
| SEQ. ID. NO. 3392 | 125-SerThrMetProArgAsnGlnGlyTrp-133 |
| SEQ. ID. NO. 3393 | 174-ValLysArgArgGlyIleLysAla-181 |
| SEQ. ID. NO. 3394 | 183-LeuLeuProSerLysGlyArgAlaArgSerTrpTrp-194 |
| SEQ. ID. NO. 3395 | 196-AsnLeuHisGlyThrPheGly-202 |
| SEQ. ID. NO. 3396 | 235-ProAlaGlyLysTrpGlyValGluProAsnProVal-246 |
| SEQ. ID. NO. 3397 | 255-ValLeuAsnAspGlyLysValLysGlu-263 |
| SEQ. ID. NO. 3398 | 279-ThrValGlyLysAspGlyIleAsnProAspGluProMetThr-292 |
| SEQ. ID. NO. 3399 | 294-GluThrValAspArgPheAlaArg-301 |
| SEQ. ID. NO. 3400 | 303-IleGlyPheLysGlyArgTyrGlnLeuAsnLeuProLysGlyGluAspGly-319 |
| SEQ. ID. NO. 3401 | 323-LeuSerGlnAspSerMetSerTyr-330 |
| SEQ. ID. NO. 3402 | 336-PheAlaAspArgThrValHis-342 |
| SEQ. ID. NO. 3403 | 344-AspGlnTyrSerGlyLysIleLeuAla-352 |
| SEQ. ID. NO. 3404 | 354-IleArgPheAspAspTyrAsnProPhe-362 |
| SEQ. ID. NO. 3405 | 404-TrpLysArgArgProThrGlyAla-411 |
| SEQ. ID. NO. 3406 | 417-ProAlaGlnLysValLysLeu-423 |

Hydrophilic Regions - Hopp-Woods

| | |
|---|---|
| SEQ. ID. NO. 3407 | 3-ThrGlnIleLysThrGluAlaAspAsnGlnSerAsnArgArgTyr-17 |
| SEQ. ID. NO. 3408 | 52-ThrGlyLysGluGlyGluArgIleHis-60 |
| SEQ. ID. NO. 3409 | 74-AlaGluAlaAlaArgSerAlaValAsnProGluThrSerSer-87 |
| SEQ. ID. NO. 3410 | 94-ProArgAlaAspAspMet-99 |
| SEQ. ID. NO. 3411 | 105-ValAsnAsnGluGlyLysAla-111 |
| SEQ. ID. NO. 3412 | 175-LysArgArgGlyIleLys-180 |
| SEQ. ID. NO. 3413 | 186-SerLysGlyArgAla-190 |
| SEQ. ID. NO. 3414 | 255-ValLeuAsnAspGlyLysValLysGlu-263 |
| SEQ. ID. NO. 3415 | 279-ThrValGlyLysAspGlyIleAsnProAspGluProMetThr-292 |
| SEQ. ID. NO. 3416 | 294-GluThrValAspArgPheAlaArg-301 |
| SEQ. ID. NO. 3417 | 314-ProLysGlyGluAspGly-319 |
| SEQ. ID. NO. 3418 | 325-GlnAspSerMetSer-329 |
| SEQ. ID. NO. 3419 | 336-PheAlaAspArgThrValHis-342 |
| SEQ. ID. NO. 3420 | 354-IleArgPheAspAsp-358 |
| SEQ. ID. NO. 3421 | 405-LysArgArgProThrGly-410 |

225-1
AMPHI Regions - AMPHI

| | |
|---|---|
| SEQ. ID. NO. 3422 | 23-LeuAlaAspGluLeuThrAsn-29 |
| SEQ. ID. NO. 3423 | 37-IleLeuArgGlnPhe-41 |
| SEQ. ID. NO. 3424 | 126-AsnAlaMetGlyLeu-130 |
| SEQ. ID. NO. 3425 | 151-PheMetGlnHisIlePheLys-157 |
| SEQ. ID. NO. 3426 | 217-ThrGlyLysAsnIle-221 |

Antigenic Index - Jameson-Wolf

| | |
|---|---|
| SEQ. ID. NO. 3427 | 22-AlaLeuAlaAspGluLeuThr-28 |
| SEQ. ID. NO. 3428 | 32-SerSerArgGluGlnIleLeu-38 |
| SEQ. ID. NO. 3429 | 41-PheAlaGluAspGluGlnProVal-48 |
| SEQ. ID. NO. 3430 | 52-AsnArgAlaProAlaArgArgAlaGlyAsnAlaAspGluLeuIle-66 |
| SEQ. ID. NO. 3431 | 71-GlyLeuAsnGluGlnProVal-77 |
| SEQ. ID. NO. 3432 | 81-AsnArgValProAlaArgArgAlaGlyAsnAlaAspGluLeuIle-95 |
| SEQ. ID. NO. 3433 | 100-GlyLeuAsnGluGlnProVal-106 |
| SEQ. ID. NO. 3434 | 108-ProValAsnArgAlaProAlaArgArgAlaGlyAsnAlaAspGluLeuIle-124 |
| SEQ. ID. NO. 3435 | 144-ThrGlyPheAspCysSerGly-150 |
| SEQ. ID. NO. 3436 | 164-LeuProArgThrSerAlaGluGlnAlaArgMet-174 |
| SEQ. ID. NO. 3437 | 176-ThrProValAlaArgSerGluLeuGlnProGlyAsp-187 |
| SEQ. ID. NO. 3438 | 194-LeuGlyGlySerArgIle-199 |
| SEQ. ID. NO. 3439 | 213-HisAlaProArgThrGlyLysAsnIleGlu-222 |
| SEQ. ID. NO. 3440 | 225-SerLeuSerHisLysTyrTrpSerGlyLys-234 |
| SEQ. ID. NO. 3441 | 239-ArgArgValLysLysAsnAspProSerArgPhe-249 |

Hydrophilic Regions - Hopp-Woods

| | |
|---|---|
| SEQ. ID. NO. 3442 | 22-AlaLeuAlaAspGluLeuThr-28 |
| SEQ. ID. NO. 3443 | 32-SerSerArgGluGlnIleLeu-38 |
| SEQ. ID. NO. 3444 | 41-PheAlaGluAspGluGlnPro-47 |
| SEQ. ID. NO. 3445 | 53-ArgAlaProAlaArgArgAlaGlyAsnAlaAspGluLeuIle-66 |
| SEQ. ID. NO. 3446 | 83-ValProAlaArgArgAlaGlyAsnAlaAspGluLeuIle-95 |
| SEQ. ID. NO. 3447 | 111-ArgAlaProAlaArgArgAlaGlyAsnAlaAspGluLeuIle-124 |
| SEQ. ID. NO. 3448 | 166-ArgThrSerAlaGluGlnAlaArgMet-174 |
| SEQ. ID. NO. 3449 | 178-ValAlaArgSerGluLeuGlnPro-185 |
| SEQ. ID. NO. 3450 | 216-ArgThrGlyLysAsnIleGlu-222 |
| SEQ. ID. NO. 3451 | 239-ArgArgValLysLysAsnAspProSerArg-248 |

TABLE 1-continued

226
AMPHI Regions - AMPHI
SEQ. ID. NO. 3452   44-LeuIleAlaTyrLeuLys-49
SEQ. ID. NO. 3453   61-AlaAlaGlnPheIleAspPheTrpLeu-69
SEQ. ID. NO. 3454   98-GlnLeuAlaGlySerValThrGlyIleValThr-108
SEQ. ID. NO. 3455   141-ArgSerIleGlyGlyIleProAlaIleThr-150
SEQ. ID. NO. 3456   157-AlaGlyLeuValGlyGlnIleAlaGlyTyrLys-167
SEQ. ID. NO. 3457   197-GluArgSerArgArg-201
Antigenic Index - Jameson-Wolf
SEQ. ID. NO. 3458   3-GluIleLeuArgGlnProSer-9
SEQ. ID. NO. 3459   25-ValArgThrArgThrGlyAsnIle-32
SEQ. ID. NO. 3460   81-TyrGlnAsnArgArgLysIle-87
SEQ. ID. NO. 3461   117-GlyAlaGluArgGluVal-122
SEQ. ID. NO. 3462   128-SerLysSerValThrAsn-133
SEQ. ID. NO. 3463   139-IleThrArgSerIleGlyGly-145
SEQ. ID. NO. 3464   167-LysMetLeuLysAsnThrVal-173
SEQ. ID. NO. 3465   195-SerLeuGluArgSerArgArgMetAla-203
Hydrophilic Regions - Hopp-Woods
SEQ. ID. NO. 3466   25-ValArgThrArgThr-29
SEQ. ID. NO. 3467   82-GlnAsnArgArgLysIle-87
SEQ. ID. NO. 3468   117-GlyAlaGluArgGluVal-122
SEQ. ID. NO. 3469   195-SerLeuGluArgSerArgArgMetAla-203
227-2
AMPHI Regions - AMPHI
SEQ. ID. NO. 3470   36-GlyValLeuPheAlaLeuLeuGlnAla-44
SEQ. ID. NO. 3471   52-LeuGlnGlnLeuThrAspAlaLeu-59
SEQ. ID. NO. 3472   74-ValIleSerTyrLeuAspLeuIleAlaAspAspTrpPheSer-87
228
AMPHI Regions - AMPHI
SEQ. ID. NO. 3473   24-GluValLysGluAlaValGlnAlaValGlu-33
SEQ. ID. NO. 3474   40-AlaAlaSerAlaAlaGluSerAlaAlaSerAlaValGluGluAlaLysAspGlnValLysAspAla-61
SEQ. ID. NO. 3475   78-GluAlaValThrGluAlaAlaLysAspThrLeuAsnLysAlaAlaAspAlaThrGlnGluAlaAlaAspLysMetLysAspAlaAla-106
Antigenic Index - Jameson-Wolf
SEQ. ID. NO. 3476   18-SerGlnGluAlaLysGlnGluValLysGluAlaValGln-30
SEQ. ID. NO. 3477   32-ValGluSerAspValLysAspThrAlaAlaSerAlaAlaGluSerAlaAlaSerAlaValGluGluAlaLysAspGlnValLysAspAlaAlaAlaAsp
                    AlaLysAlaSerAlaGluGluAlaValThrGluAlaLysGluAlaValThrGluAlaAlaLysAspThrLeuAsnLysAlaAlaAspAlaThrGlnGluAlaAla
                    AspLysMetLysAspAlaAlaLys-107
Hydrophilic Regions - Hopp-Woods
SEQ. ID. NO. 3478   18-SerGlnGluAlaLysGlnGluValLysGluAlaValGln-30
SEQ. ID. NO. 3479   32-ValGluSerAspValLysAspThrAlaAlaSerAlaAlaGluSerAlaAlaSerAlaValGluGluAlaLysAspGlnValLysAspAlaAlaAlaAsp
                    AlaLysAlaSerAlaGluGluAlaValThrGluAlaLysGluAlaValThrGluAlaAlaLysAspThrLeuAsnLysAlaAlaAspAlaThrGlnGluAla
                    AlaAspLysMetLysAspAlaAlaLys-107
230-1
AMPHI Regions - AMPHI
SEQ. ID. NO. 3480   6-GluLysTyrArgThr-10
SEQ. ID. NO. 3481   49-AspHisSerIleAsnAsn-54
SEQ. ID. NO. 3482   56-IleGlnAsnGluGln-60
SEQ. ID. NO. 3483   73-GlnSerLeuLeuGln-77
SEQ. ID. NO. 3484   81-LeuLysGlnGlyAlaLys-86
SEQ. ID. NO. 3485   96-GlnIleLysGlnIleIle-101
SEQ. ID. NO. 3486   133-PheValGluGluIleArgAspGlnPhe-141
SEQ. ID. NO. 3487   144-GlnAsnLeuValAsnLeuVal-150
SEQ. ID. NO. 3488   161-AlaGluGlnLeuIleArgLeuThrGlnValAsnArgThrIleArg-175
SEQ. ID. NO. 3489   184-PheIleAlaGlnVal-188
SEQ. ID. NO. 3490   194-AspLeuGlnLysPheTyrAsn-200
SEQ. ID. NO. 3491   234-GluValLysAsnAlaPheGluGluArgValAlaArgLeu-246
SEQ. ID. NO. 3492   272-ValAlaAspPheAsnLys-277
SEQ. ID. NO. 3493   284-AspAspAlaPheAsnHisProSerSerLeuAlaGluAla-296
SEQ. ID. NO. 3494   319-SerGlyMetProGluAsnLeuIleAsnAlaVal-329
SEQ. ID. NO. 3495   398-LeuAsnGlyGlyLys-402
SEQ. ID. NO. 3496   426-GluAlaTyrAlaGluLeu-431
SEQ. ID. NO. 3497   444-ValArgLeuIleGlyLeuProAlaPro-452
SEQ. ID. NO. 3498   456-GluValGlnAlaValThrProProAspAspIleAla-467
SEQ. ID. NO. 3499   488-LeuLeuIleArgTyrPheAsn-494
Antigenic Index - Jameson-Wolf
SEQ. ID. NO. 3500   4-SerIleGluLysTyrArgThrProAla-12
SEQ. ID. NO. 3501   32-SerHisProGlyAlaAsp-37
SEQ. ID. NO. 3502   42-ValGlyAspGluLysIleSerAspHisSerIle-52
SEQ. ID. NO. 3503   56-IleGlnAsnGluGlnAlaAspGlyGlyGlyProSerArgAspAlaVal-71
SEQ. ID. NO. 3504   80-TyrLeuLysGlnGlyAla-85
SEQ. ID. NO. 3505   92-ValSerSerGluGlnIleLys-98
SEQ. ID. NO. 3506   101-IleValAspAspProAsnPheHisAspAlaAsnGlyLysPheAsp-115
SEQ. ID. NO. 3507   122-TyrLeuSerGlnArgHisMetSerGluAspGlnPheValGluGluIleArgAsp-139
SEQ. ID. NO. 3508   169-GlnValAsnArgThrIleArgSerHisThrPheAsnProAspGluPhe-184
SEQ. ID. NO. 3509   189-LysValSerGluAlaAspLeu-195
SEQ. ID. NO. 3510   199-TyrAsnAlaAsnLysLysAspTyrLeu-207
SEQ. ID. NO. 3511   223-AspPheAlaAspLysGlnThrValSerGluThrGluValLysAsnAlaPheGluGluArgValAlaArg-245
SEQ. ID. NO. 3512   247-ProAlaAsnGluAlaLysProSerPheGluGlnGluLysAlaAlaValGluAsnGluLeuLysMetLysLysAlaValAlaAspPheAsnLysAlaLys
                    GluLysLeuGlyAspAspAlaPheAsnHisProSerSerLeuAlaGluAlaAlaLysAsnSerGlyLeuLysValGluThrGlnGluThrTrpLeuSerArgGln
                    AspAlaGlnMetSerGlyMetProGluAsn-324

TABLE 1-continued

| | |
|---|---|
| SEQ. ID. NO. 3513 | 330-PheSerAspAspValLeuLysLysLysHisAsnSerGlu-342 |
| SEQ. ID. NO. 3514 | 355-ArgAlaLysGluValArgGluGluLysThrLeuPro-366 |
| SEQ. ID. NO. 3515 | 368-AlaGluAlaLysAspAlaValArg-375 |
| SEQ. ID. NO. 3516 | 377-AlaTyrIleArgThrGluAlaAlaLysLeuAlaGluAsnLysAlaLysAspValLeu-395 |
| SEQ. ID. NO. 3517 | 399-AsnGlyGlyLysAlaValAsp-405 |
| SEQ. ID. NO. 3518 | 417-GlnGlnAlaArgGlnSerMetProProGluAlaTyr-428 |
| SEQ. ID. NO. 3519 | 432-LeuLysAlaLysProAlaAsnGlyLysProAla-442 |
| SEQ. ID. NO. 3520 | 459-AlaValThrProProAspAspIleAla-467 |
| SEQ. ID. NO. 3521 | 476-AlaLeuAlaGlnGlnGlnSerAlaAsnThrPhe-486 |
| SEQ. ID. NO. 3522 | 493-PheAsnGlyLysIleLysGlnThrLysGlyAlaGlnSerValAspAsnGlyAspGlyGln-512 |
| Hydrophilic Regions - Hopp-Woods | |
| SEQ. ID. NO. 3523 | 6-GluLysTyrArgThr-10 |
| SEQ. ID. NO. 3524 | 42-ValGlyAspGluLysIleSerAsp-49 |
| SEQ. ID. NO. 3525 | 56-IleGlnAsnGluGlnAlaAspGlyGlyGlyProSerArgAspAlaVal-71 |
| SEQ. ID. NO. 3526 | 92-ValSerSerGluGlnIleLys-98 |
| SEQ. ID. NO. 3527 | 101-IleValAspAspProAsnPhe-107 |
| SEQ. ID. NO. 3528 | 110-AlaAsnGlyLysPheAsp-115 |
| SEQ. ID. NO. 3529 | 126-ArgHisMetSerGluAspGlnPheValGluGluIleArgAsp-139 |
| SEQ. ID. NO. 3530 | 189-LysValSerGluAlaAspLeu-195 |
| SEQ. ID. NO. 3531 | 200-AsnAlaAsnLysLysAspTyrLeu-207 |
| SEQ. ID. NO. 3532 | 223-AspPheAlaAspLysGlnThrValSerGluThrGluValLysAsnAlaPheGluGluArgValAlaArg-245 |
| SEQ. ID. NO. 3533 | 247-ProAlaAsnGluAlaLysProSerPheGluGlnGluLysAlaAlaValGluAsnGluLeuLysMetLysLysAlaValAlaAspPheAsnLysAlaLys GluLysLeuGlyAspAspAlaPhe-287 |
| SEQ. ID. NO. 3534 | 292-SerLeuAlaGluAlaAlaLysAsnSerGlyLeuLysValGluThrGlnGlu-308 |
| SEQ. ID. NO. 3535 | 310-TrpLeuSerArgGlnAspAlaGlnMet-318 |
| SEQ. ID. NO. 3536 | 333-AspValLeuLysLysLysHisAsnSer-341 |
| SEQ. ID. NO. 3537 | 355-ArgAlaLysGluValArgGluGluLysThrLeuPro-366 |
| SEQ. ID. NO. 3538 | 368-AlaGluAlaLysAspAlaValArg-375 |
| SEQ. ID. NO. 3539 | 377-AlaTyrIleArgThrGluAlaAlaLysLeuAlaGluAsnLysAlaLysAspValLeu-395 |
| SEQ. ID. NO. 3540 | 417-GlnGlnAlaArgGlnSerMetPro-424 |
| SEQ. ID. NO. 3541 | 432-LeuLysAlaLysProAlaAsnGly-439 |
| SEQ. ID. NO. 3542 | 461-ThrProProAspAspIleAla-467 |
| SEQ. ID. NO. 3543 | 496-LysIleLysGlnThrLysGlyAlaGlnSerValAspAsnGlyAspGlyGln-512 |
| 231-1 | |
| AMPHI Regions - AMPHI | |
| SEQ. ID. NO. 3544 | 7-IleAsnArgProTyrGlnLysProAlaGluLeu-17 |
| SEQ. ID. NO. 3545 | 98-ArgIlePheSerPheProGln-104 |
| SEQ. ID. NO. 3546 | 209-AlaValAspAsnValLysGlyValAlaVal-218 |
| SEQ. ID. NO. 3547 | 228-AlaValAlaAlaGlyPheArgArgCysSerAlaAla-238 |
| SEQ. ID. NO. 3548 | 263-LeuAlaAlaValProArgIleThrGln-271 |
| SEQ. ID. NO. 3549 | 281-LysProPheHisAspPhePheAsnLeu-289 |
| Antigenic Index - Jameson-Wolf | |
| SEQ. ID. NO. 3550 | 1-MetSerLysArgLysSerIleAsnArgProTyrGlnLysProAlaGlu-16 |
| SEQ. ID. NO. 3551 | 18-ProProLeuGlnAsnAsnProProPheTyrArgLysAsnArgArgLeuAsn-34 |
| SEQ. ID. NO. 3552 | 39-AlaAspGlyGlyCysAlaSerProGlnLysCysArgAlaArgGlyPheGln-55 |
| SEQ. ID. NO. 3553 | 90-SerAlaValArgProArgArgLeuArg-98 |
| SEQ. ID. NO. 3554 | 135-MetProArgArgProVal-140 |
| SEQ. ID. NO. 3555 | 150-PheAlaAspArgAsnLeuArg-156 |
| SEQ. ID. NO. 3556 | 174-AlaPheArgArgArgAlaGlnVal-181 |
| SEQ. ID. NO. 3557 | 183-AlaArgThrArgAla-187 |
| SEQ. ID. NO. 3558 | 194-ArgArgValAspIleArgHisProAspPhe-203 |
| SEQ. ID. NO. 3559 | 211-AspAsnValLysGly-215 |
| SEQ. ID. NO. 3560 | 231-GlyPheArgArgCysSerAlaAlaGlyGlyArgValGlyThr-244 |
| SEQ. ID. NO. 3561 | 246-ValProCysArgAlaGluTyrValGluTyrGlyAsnArgArgProHisArgLeuAlaAla-265 |
| SEQ. ID. NO. 3562 | 269-IleThrGlnArgThrGlnLysArgGlnGlyAspGlyLysProPhe-283 |
| SEQ. ID. NO. 3563 | 294-MetProMetProSerGluHis |
| Hydrophilic Regions - Hopp-Woods | |
| SEQ. ID. NO. 3564 | 1-MetSerLysArgLysSerIleAsn-8 |
| SEQ. ID. NO. 3565 | 10-ProTyrGlnLysProAlaGlu-16 |
| SEQ. ID. NO. 3566 | 26-PheTyrArgLysAsnArgArg-32 |
| SEQ. ID. NO. 3567 | 45-SerProGlnLysCysArgAlaArgGly-53 |
| SEQ. ID. NO. 3568 | 92-ValArgProArgArgLeuArg-98 |
| SEQ. ID. NO. 3569 | 136-ProArgArgProVal-140 |
| SEQ. ID. NO. 3570 | 150-PheAlaAspArgAsnLeuArg-156 |
| SEQ. ID. NO. 3571 | 174-AlaPheArgArgArgAlaGlnVal-181 |
| SEQ. ID. NO. 3572 | 183-AlaArgThrArgAla-187 |
| SEQ. ID. NO. 3573 | 194-ArgArgValAspIleArgHis-200 |
| SEQ. ID. NO. 3574 | 231-GlyPheArgArgCysSerAlaAlaGlyGlyArgValGlyThr-244 |
| SEQ. ID. NO. 3575 | 246-ValProCysArgAlaGluTyr-252 |
| SEQ. ID. NO. 3576 | 254-GluTyrGlyAsnArgArgProHisArg-262 |
| SEQ. ID. NO. 3577 | 269-IleThrGlnArgThrGlnLysArgGlnGlyAspGlyLysProPhe-283 |
| 232-2 | |
| AMPHI Regions - AMPHI | |
| SEQ. ID. NO. 3578 | 23-GlnPheLeuGlyAlaPheAsnAspAsnVal-32 |
| SEQ. ID. NO. 3579 | 55-GlyGlnMetLeuAsn-59 |
| SEQ. ID. NO. 3580 | 74-SerLeuSerGlyGlnLeuGlyAsnLysPheAspLysAlaValLeuAlaArgTrpValLysValLeuGluMetIleIleMet-100 |
| SEQ. ID. NO. 3581 | 127-ThrLeuPheGlyProLeuLysTyr-134 |
| SEQ. ID. NO. 3582 | 160-AlaIleLeuPheGly-164 |
| SEQ. ID. NO. 3583 | 167-LeuGlyThrAlaValAlaGlyValProProTyrIleValGlyIleLeuVal-183 |
| SEQ. ID. NO. 3584 | 214-ValArgGlyThrLysSerLeuLeuArgGlu-223 |

TABLE 1-continued

| SEQ. ID. NO. 3585 | 251-LeuProThrPheThrGln-256 |
| SEQ. ID. NO. 3586 | 319-ArgPheGluGlyLeuAsn-324 |
| SEQ. ID. NO. 3587 | 340-AlaValMetThrLeuIleGlyPhePheGlyGlyPhePheSerValProLeuTyrThrTrpLeu-360 |

Antigenic Index - Jameson-Wolf

| SEQ. ID. NO. 3588 | 1-MetTyrAlaLysLysGlyGlyLeuGlyLeuValLysSerArgArgPhe-16 |
| SEQ. ID. NO. 3589 | 75-LeuSerGlyGlnLeuGlyAsnLysPheAspLys-85 |
| SEQ. ID. NO. 3590 | 139-AspTyrLeuAspAspLysGluLeuMetMet-148 |
| SEQ. ID. NO. 3591 | 200-ValProAlaLysAlaAlaAspThrGlnIle-209 |
| SEQ. ID. NO. 3592 | 215-ArgGlyThrLysSerLeuLeuArgGluThrValArgHisLysPro-229 |
| SEQ. ID. NO. 3593 | 258-HisLeuGlyGlyAsnAspAsnVal-265 |
| SEQ. ID. NO. 3594 | 286-LysPheSerArgGluArgLeu-292 |
| SEQ. ID. NO. 3595 | 316-HisGlyHisArgPheGluGly-322 |
| SEQ. ID. NO. 3596 | 363-AlaSerSerGluThrPheArgAlaArgAla-372 |
| SEQ. ID. NO. 3597 | 420-IleLysArgGluArgArgPheLeu-427 |
| SEQ. ID. NO. 3598 | 431-AlaIleArgLysLysPro-436 |

Hydrophilic Regions - Hopp-Woods

| SEQ. ID. NO. 3599 | 2-TyrAlaLysLysGlyGly-7 |
| SEQ. ID. NO. 3600 | 11-ValLysSerArgArgPhe-16 |
| SEQ. ID. NO. 3601 | 81-AsnLysPheAspLys-85 |
| SEQ. ID. NO. 3602 | 140-TyrLeuAspAspLysGluLeuMet-147 |
| SEQ. ID. NO. 3603 | 201-ProAlaLysAlaAlaAspThrGlnIle-209 |
| SEQ. ID. NO. 3604 | 215-ArgGlyThrLysSerLeuLeuArgGluThrValArgHis-227 |
| SEQ. ID. NO. 3605 | 286-LysPheSerArgGluArgLeu-292 |
| SEQ. ID. NO. 3606 | 318-HisArgPheGluGly-322 |
| SEQ. ID. NO. 3607 | 366-GluThrPheArgAlaArgAla-372 |
| SEQ. ID. NO. 3608 | 420-IleLysArgGluArgArgPheLeu-427 |
| SEQ. ID. NO. 3609 | 431-AlaIleArgLysLysPro-436 |

233-2
AMPHI Regions - AMPHI

| SEQ. ID. NO. 3610 | 61-PheAlaAspLysValGlnThr-67 |
| SEQ. ID. NO. 3611 | 71-GlnValArgValTrpLysAsn-77 |
| SEQ. ID. NO. 3612 | 88-AsnGlyValAlaLysLeuLeuGluThr-96 |
| SEQ. ID. NO. 3613 | 119-AlaLeuThrArgLeuIleGluGlnAlaGlyAsnAla-130 |
| SEQ. ID. NO. 3614 | 138-IleProIleAlaAspThrLeuLysCysAlaAspGlyGlyAsn-151 |
| SEQ. ID. NO. 3615 | 180-AlaAlaGluAsnLeuAspGlyIleThrAsp-189 |

Antigenic Index - Jameson-Wolf

| SEQ. ID. NO. 3616 | 1-MetLysArgLysAsnIle-6 |
| SEQ. ID. NO. 3617 | 16-AlaArgPheGlyAlaAspLysProLysGlnTyrValGluIleGlySerLysThrValLeu-35 |
| SEQ. ID. NO. 3618 | 43-GluArgHisGluAlaValAsp-49 |
| SEQ. ID. NO. 3619 | 56-SerProGluAspThrPheAlaAspLysValGln-66 |
| SEQ. ID. NO. 3620 | 75-TrpLysAsnGlyGlyGlnThrArgAlaGluThrValArgAsnGlyVal-90 |
| SEQ. ID. NO. 3621 | 100-AlaGluThrAspAsn-104 |
| SEQ. ID. NO. 3622 | 109-AspAlaAlaArgCys-113 |
| SEQ. ID. NO. 3623 | 115-LeuProSerGluAlaLeu-120 |
| SEQ. ID. NO. 3624 | 123-LeuIleGluGlnAlaGlyAsnAlaAlaGluGlyGly-134 |
| SEQ. ID. NO. 3625 | 142-AspThrLeuLysCysAlaAspGlyGlyAsnIle-152 |
| SEQ. ID. NO. 3626 | 155-ThrValGluArgThrSerLeu-161 |
| SEQ. ID. NO. 3627 | 182-GluAsnLeuAspGlyIleThrAspGluAlaSerAlaValGluLysLeuGlyVal-199 |
| SEQ. ID. NO. 3628 | 206-GlyAspValArgAsnLeuLysLeuThrGlnProGlnAspAlaTyr-220 |

Hydrophilic Regions - Hopp-Woods

| SEQ. ID. NO. 3629 | 1-MetLysArgLysAsnIle-6 |
| SEQ. ID. NO. 3630 | 18-PheGlyAlaAspLysProLysGlnTyrVal-27 |
| SEQ. ID. NO. 3631 | 43-GluArgHisGluAlaValAsp-49 |
| SEQ. ID. NO. 3632 | 56-SerProGluAspThrPheAlaAspLysValGln-66 |
| SEQ. ID. NO. 3633 | 79-GlyGlnThrArgAlaGluThrValArg-87 |
| SEQ. ID. NO. 3634 | 100-AlaGluThrAspAsn-104 |
| SEQ. ID. NO. 3635 | 127-AlaGlyAsnAlaAlaGlu-132 |
| SEQ. ID. NO. 3636 | 142-AspThrLeuLysCysAlaAsp-148 |
| SEQ. ID. NO. 3637 | 182-GluAsnLeuAspGlyIleThrAspGluAlaSerAlaValGluLysLeuGlyVal-199 |
| SEQ. ID. NO. 3638 | 206-GlyAspValArgAsnLeuLys-212 |

234-2
AMPHI Regions - AMPHI

| SEQ. ID. NO. 3639 | 26-ArgSerLeuGluValGluLysValAlaSer-35 |
| SEQ. ID. NO. 3640 | 68-AspArgLeuGlySerGln-73 |
| SEQ. ID. NO. 3641 | 83-GlnGlnThrAsnArgPheAsnValLeuAsnArgThrAsn-95 |
| SEQ. ID. NO. 3642 | 121-GlyAspValThrGluPhe-126 |
| SEQ. ID. NO. 3643 | 206-AlaValAsnSerLeuValGlnAlaValAsp-215 |

Antigenic Index - Jameson-Wolf

| SEQ. ID. NO. 3644 | 21-AlaThrGluSerSerArgSerLeuGluValGluLysValAlaSer-35 |
| SEQ. ID. NO. 3645 | 51-ThrPheAspAsnArgSerSerPhe-58 |
| SEQ. ID. NO. 3646 | 62-IlePheSerAspGlyGluAspArgLeuGlySerGlnAla-74 |
| SEQ. ID. NO. 3647 | 83-GlnGlnThrAsnArgPheAsnValLeuAsnArgThrAsn-95 |
| SEQ. ID. NO. 3648 | 99-LeuLysGlnGluSerGlyIleSerGlyLysAlaHisAsnLeuLysGlyAlaAspTyr-117 |
| SEQ. ID. NO. 3649 | 121-GlyAspValThrGluPheGlyArgArgAspValGlyAsp-133 |
| SEQ. ID. NO. 3650 | 140-LeuGlyArgGlyLysSerGlnIle-147 |
| SEQ. ID. NO. 3651 | 160-AsnThrSerGluIle-164 |
| SEQ. ID. NO. 3652 | 169-GlnGlyAlaGlyGlu-173 |
| SEQ. ID. NO. 3653 | 175-AlaLeuSerAsnArgGluIle-181 |
| SEQ. ID. NO. 3654 | 185-GlyGlyThrSerGlyTyrAspAlaThrLeuAsnGlyLysValLeu-199 |
| SEQ. ID. NO. 3655 | 214-ValAspAsnGlyAlaTrpGlnProAsnArg-223 |

TABLE 1-continued

Hydrophilic Regions - Hopp-Woods
SEQ. ID. NO. 3656    21-AlaThrGluSerSerArgSerLeuGluValGluLysValAla-34
SEQ. ID. NO. 3657    52-PheAspAsnArgSerSerPhe-58
SEQ. ID. NO. 3658    62-IlePheSerAspGlyGluAspArgLeuGlySerGlnAla-74
SEQ. ID. NO. 3659    99-LeuLysGlnGluSerGlyIleSerGlyLysAlaHisAsn-111
SEQ. ID. NO. 3660    122-AspValThrGluPheGlyArgArgAspValGlyAsp-133
SEQ. ID. NO. 3661    141-GlyArgGlyLysSer-145
SEQ. ID. NO. 3662    176-LeuSerAsnArgGluIle-181
235
AMPHI Regions - AMPHI
SEQ. ID. NO. 3663    8-LeuAlaAlaValLeuAlaLeu-14
SEQ. ID. NO. 3664    18-GlnValGlnLysAlaProAsp-24
SEQ. ID. NO. 3665    86-LeuThrAsnAlaAlaAspIle-92
SEQ. ID. NO. 3666    95-ValArgProGluLysLeuHisGlnIlePhe-104
SEQ. ID. NO. 3667    120-SerTyrGlnIleLeuAspSerValThrThr-129
SEQ. ID. NO. 3668    165-GlyAlaLeuValSerAlaValValAsnGlnIleAlaAsnSerLeuThr-180
SEQ. ID. NO. 3669    187-SerLysThrAlaAlaTyrAsnLeuLeuSerProTyr-198
Antigenic Index - Jameson-Wolf
SEQ. ID. NO. 3670    20-GlnLysAlaProAspPheAspTyrThrSerPheLysGluSerLysProAla-36
SEQ. ID. NO. 3671    43-ProLeuAsnGluSerProAspValAsnGlyThr-53
SEQ. ID. NO. 3672    62-AlaProLeuSerGlu-66
SEQ. ID. NO. 3673    79-GluThrPheLysGlnAsnGlyLeuThrAsn-88
SEQ. ID. NO. 3674    93-HisAlaValArgProGluLysLeu-100
SEQ. ID. NO. 3675    131-SerAlaLysAlaArgLeuValAspSerArgAsnGlyLysGluLeuTrpSerGlySerAlaSerIleArgGluGlySerAsnAsnSerAsnSer-161
SEQ. ID. NO. 3676    178-SerLeuThrAspArgGlyTyrGlnValSerLysThrAla-190
SEQ. ID. NO. 3677    202-GlyIleLeuLysGlyProArgPheValGluGluGlnProLys-215
Hydrophilic Regions - Hopp-Woods
SEQ. ID. NO. 3678    20-GlnLysAlaProAspPheAsp-26
SEQ. ID. NO. 3679    29-SerPheLysGluSerLysPro-35
SEQ. ID. NO. 3680    44-LeuAsnGluSerProAspVal-50
SEQ. ID. NO. 3681    93-HisAlaValArgProGluLysLeu-100
SEQ. ID. NO. 3682    131-SerAlaLysAlaArgLeuValAspSerArgAsnGlyLysGluLeuTrp-146
SEQ. ID. NO. 3683    150-AlaSerIleArgGluGlySerAsnAsnSer-159
SEQ. ID. NO. 3684    179-LeuThrAspArgGlyTyrGln-185
SEQ. ID. NO. 3685    207-ProArgPheValGluGluGlnProLys-215
236-2
AMPHI Regions - AMPHI
SEQ. ID. NO. 3686    11-LeuCysThrAlaPheAlaAsp-17
SEQ. ID. NO. 3687    107-PheAlaGlyPheAlaAspCysArgProPhe-116
SEQ. ID. NO. 3688    146-AspAspValProArgPhePheAlaGlyGlu-155
SEQ. ID. NO. 3689    178-AlaAlaCysMetAlaValCysPheGly-186
SEQ. ID. NO. 3690    214-LysValGluGlyIleThrArgIle-221
SEQ. ID. NO. 3691    245-IleArgLeuLeuHisGlyIlePheAsnArgIleLysValAla-258
SEQ. ID. NO. 3692    288-PheAlaAlaValIle-292
SEQ. ID. NO. 3693    311-LeuArgCysAsnAspValAlaAspGlyPheArgHisPhe-323
Antigenic Index - Jameson-Wolf
SEQ. ID. NO. 3694    42-GlyPheSerGlyAsnGlyLysPhe-49
SEQ. ID. NO. 3695    58-ArgHisGlnGlnSerLysAlaGln-65
SEQ. ID. NO. 3696    77-PhePheArgArgGlyAsnPheGlyPheGlyLeuGlnGlyArgThrAspGlyPhe-94
SEQ. ID. NO. 3697    98-GlnArgLeuAspGlyGlyGlyTyr-105
SEQ. ID. NO. 3698    109-GlyPheAlaAspCysArgProPhe-116
SEQ. ID. NO. 3699    126-ValAspGlyArgGluLeuValProSerMetGluGluAspAla-139
SEQ. ID. NO. 3700    145-AlaAspAspValPro-149
SEQ. ID. NO. 3701    155-GluAlaGlnAsnArgCysAsnGlnGluAsnGlnThrAla-167
SEQ. ID. NO. 3702    195-ValGluValGluArgThrGlnValPheArgAlaGluArgAsnAsnValPhe-211
SEQ. ID. NO. 3703    213-GlyLysValGluGlyIleThr-219
SEQ. ID. NO. 3704    261-GlyLysGlnLysAlaGlnGly-267
SEQ. ID. NO. 3705    292-IleGlyArgCysArgProGlnAlaGln-300
SEQ. ID. NO. 3706    312-ArgCysAsnAspValAlaAspGly-319
SEQ. ID. NO. 3707    328-ValAspAsnGluThrMet-333
Hydrophilic Regions - Hopp-Woods
SEQ. ID. NO. 3708    89-GlyArgThrAspGly-93
SEQ. ID. NO. 3709    98-GlnArgLeuAspGlyGlyGly-104
SEQ. ID. NO. 3710    127-AspGlyArgGluLeuValProSerMetGluGluAspAla-139
SEQ. ID. NO. 3711    145-AlaAspAspValPro-149
SEQ. ID. NO. 3712    156-AlaGlnAsnArgCysAsnGlnGluAsnGlnThr-166
SEQ. ID. NO. 3713    195-ValGluValGluArgThrGlnValPheArgAlaGluArgAsnAsn-209
SEQ. ID. NO. 3714    215-ValGluGlyIleThr-219
SEQ. ID. NO. 3715    261-GlyLysGlnLysAlaGlnGly-267
SEQ. ID. NO. 3716    293-GlyArgCysArgProGlnAlaGln-300
SEQ. ID. NO. 3717    312-ArgCysAsnAspValAlaAspGly-319
SEQ. ID. NO. 3718    328-ValAspAsnGluThrMet-333
238
AMPHI Regions - AMPHI
SEQ. ID. NO. 3719    103-ValHisSerProPhe-107
SEQ. ID. NO. 3720    112-SerLysSerThrSerAspPheSerGlyGlyVal-122
SEQ. ID. NO. 3721    129-TyrGlnLeuHisArgThrGlySer-136
SEQ. ID. NO. 3722    141-GluAspGlyTyrAspGlyProGlnGlySer-150
SEQ. ID. NO. 3723    158-AlaArgAspIleTyrSerTyrTyrVal-166
SEQ. ID. NO. 3724    224-AspAspValArgGlyIleValGlnGlyAlaValAsnPro-236

TABLE 1-continued

| | |
|---|---|
| SEQ. ID. NO. 3725 | 246-IleGlyAlaIleThrAspSerAlaValSerProValThrAspThrAlaAlaGlnGlnThrLeuGlnGlyIleAsnAspLeuGlyLysLeu-275 |
| SEQ. ID. NO. 3726 | 298-IleAsnSerAlaLysGlnTrpAlaAspAla-307 |
| SEQ. ID. NO. 3727 | 342-AspTrpValLysAsn-346 |
| SEQ. ID. NO. 3728 | 351-LysProAlaAlaArgHisMetGlnThrLeu-360 |
| SEQ. ID. NO. 3729 | 367-GlyAsnLysProIleLysSerLeuProAsn-376 |
| SEQ. ID. NO. 3730 | 398-PheAspSerValHisLysThrLeuThr-406 |
| SEQ. ID. NO. 3731 | 465-GlyLysGlnAlaLysAspTyrLeu-472 |
| Antigenic Index - Jameson-Wolf | |
| SEQ. ID. NO. 3732 | 25-HisAlaAsnGlyLeuAspAlaArgLeuArgAspAspMetGlnAlaLysHisTyrGluProGlyGlyLys-47 |
| SEQ. ID. NO. 3733 | 53-AsnAlaArgGlySerValLysLysArgValTyr-63 |
| SEQ. ID. NO. 3734 | 80-ThrHisGluArgThrGlyPheGluGly-88 |
| SEQ. ID. NO. 3735 | 96-PheSerGlyHisGlyHisGluValHisSerProPheAspHisHisAspSerLysSerThrSerAspPheSerGlyGlyValAspGlyGly-125 |
| SEQ. ID. NO. 3736 | 131-LeuHisArgThrGlySerGluIleHisProGluAspGlyTyrAspGlyProGlnGlySerAspTyrProProProGlyGlyAlaArgAsp-160 |
| SEQ. ID. NO. 3737 | 166-ValLysGlyThrSerThrLysThrLysThr-175 |
| SEQ. ID. NO. 3738 | 182-ProPheSerAspArgTrpLeuLysGluAsnAlaGlyAla-194 |
| SEQ. ID. NO. 3739 | 200-SerArgAlaAspGluAlaGly-206 |
| SEQ. ID. NO. 3740 | 210-TrpGluSerAspProAsnLysAsnTrp-218 |
| SEQ. ID. NO. 3741 | 221-AsnArgMetAspAspValArgGlyIle-229 |
| SEQ. ID. NO. 3742 | 268-GlyIleAsnAspLeuGlyLysLeuSerProGluAlaGln-280 |
| SEQ. ID. NO. 3743 | 292-PheAlaValLysAspGlyIleAsnSerAlaLysGlnTrpAla-305 |
| SEQ. ID. NO. 3744 | 307-AlaHisProAsnIle-311 |
| SEQ. ID. NO. 3745 | 329-TrpArgGlyLysLysValGluLeuAsnProThrLysTrpAspTrpValLysAsnThrGlyTyrLysLysProAlaAlaArg-355 |
| SEQ. ID. NO. 3746 | 360-LeuAspGlyGluMetAlaGlyGlyAsnLysProIleLysSerLeuProAsnSerAlaAlaGluLysArgLysGlnAsnPheGluLysPheAsnSerAsnTrpSer-394 |
| SEQ. ID. NO. 3747 | 396-AlaSerPheAspSerValHisLysThrLeuThrProAsnAla-409 |
| SEQ. ID. NO. 3748 | 413-LeuSerProAspLysValLysThrArgTyrThrSerLeuAspGlyLysIleThrIleIleLysAspAsnGluAsnAsnTyr-439 |
| SEQ. ID. NO. 3749 | 441-ArgIleHisAspAsnSerArgLysGlnTyrLeuAspSerAsnGlyAsnAlaValLysThrGlyAsnLeuGlnGlyLysGlnAlaLysAspTyrLeuGln-473 |
| SEQ. ID. NO. 3750 | 476-ThrHisIleArgAsnLeuAspLys-483 |
| Hydrophilic Regions - Hopp-Woods | |
| SEQ. ID. NO. 3751 | 29-LeuAspAlaArgLeuArgAspAspMetGlnAlaLysHisTyrGluProGlyGly-46 |
| SEQ. ID. NO. 3752 | 54-AlaArgGlySerValLysLysArgValTyr-63 |
| SEQ. ID. NO. 3753 | 80-ThrHisGluArgThrGlyPhe-86 |
| SEQ. ID. NO. 3754 | 108-AspHisHisAspSerLysSerThrSerAspPhe-118 |
| SEQ. ID. NO. 3755 | 133-ArgThrGlySerGluIleHisProGluAspGlyTyrAspGlyProGlnGlySerAspTyrProPro-154 |
| SEQ. ID. NO. 3756 | 156-GlyGlyAlaArgAsp-160 |
| SEQ. ID. NO. 3757 | 169-ThrSerThrLysThrLysThr-175 |
| SEQ. ID. NO. 3758 | 186-ArgTrpLeuLysGluAsnAlaGly-193 |
| SEQ. ID. NO. 3759 | 200-SerArgAlaAspGluAlaGly-206 |
| SEQ. ID. NO. 3760 | 222-ArgMetAspAspValArgGly-228 |
| SEQ. ID. NO. 3761 | 271-AspLeuGlyLysLeuSerPro-277 |
| SEQ. ID. NO. 3762 | 296-AspGlyIleAsnSer-300 |
| SEQ. ID. NO. 3763 | 329-TrpArgGlyLysLysValGluLeuAsnProThr-339 |
| SEQ. ID. NO. 3764 | 347-ThrGlyTyrLysLysProAlaAlaArg-355 |
| SEQ. ID. NO. 3765 | 360-LeuAspGlyGluMetAlaGlyGlyAsnLysProIleLys-372 |
| SEQ. ID. NO. 3766 | 377-SerAlaAlaGluLysArgLysGlnAsnPheGluLysPheAsn-390 |
| SEQ. ID. NO. 3767 | 414-SerProAspLysValLysThrArgTyrThrSerLeuAspGlyLysIleThrIleIleLysAspAsnGluAsnAsn-438 |
| SEQ. ID. NO. 3768 | 443-HisAspAsnSerArgLysGlnTyrLeu-451 |
| SEQ. ID. NO. 3769 | 454-AsnGlyAsnAlaValLys-459 |
| SEQ. ID. NO. 3770 | 462-AsnLeuGlnGlyLysGlnAlaLysAspTyrLeu-472 |
| SEQ. ID. NO. 3771 | 479-ArgAsnLeuAspLys-483 |
| 239-2 | |
| AMPHI Regions - AMPHI | |
| SEQ. ID. NO. 3772 | 49-PheArgLeuIleGlnSerCys-55 |
| SEQ. ID. NO. 3773 | 72-AsnAlaHisArgLysGln-77 |
| SEQ. ID. NO. 3774 | 123-ProGlyPheAsnAlaLeuProThrIlePhe-132 |
| SEQ. ID. NO. 3775 | 165-SerSerAsnGluTrp-169 |
| SEQ. ID. NO. 3776 | 221-PheCysAlaThrIleCysAlaSerLeuArg-230 |
| Antigenic Index - Jameson-Wolf | |
| SEQ. ID. NO. 3777 | 6-GlyIleAlaArgAsnArgArgMetGlu-14 |
| SEQ. ID. NO. 3778 | 19-CysArgArgProAspArgPheValValArgGlnThrArgLeuLeu-33 |
| SEQ. ID. NO. 3779 | 53-GlnSerCysGluIleGluPro-59 |
| SEQ. ID. NO. 3780 | 66-HisAsnGlyLysSerGlyAsnAlaHisArgLysGlnGlnLysGluIle-81 |
| SEQ. ID. NO. 3781 | 100-ProAlaValArgSerAlaThrArgLysThrAla-110 |
| SEQ. ID. NO. 3782 | 132-PheArgGlySerSerGlyLysSerAlaSer-141 |
| SEQ. ID. NO. 3783 | 144-AlaAlaGlnArgGlyArgGlyAlaCys-152 |
| SEQ. ID. NO. 3784 | 164-ArgSerSerAsnGluTrpLys-170 |
| SEQ. ID. NO. 3785 | 173-ThrAlaLysArgProProSerPheArgArgHisMetThrCysGlyAsnThrAlaProThrSerSerSerSerArgLeuIleLysMet-201 |
| SEQ. ID. NO. 3786 | 209-ValAlaGlySerCysProArgSerArgValArgThr-220 |
| SEQ. ID. NO. 3787 | 245-ArgAlaIleArgArgLeuAsnArgSerSerPro-255 |
| Hydrophilic Regions - Hopp-Woods | |
| SEQ. ID. NO. 3788 | 6-GlyIleAlaArgAsnArgArgMetGlu-14 |
| SEQ. ID. NO. 3789 | 20-ArgArgProAspArgPheValValArgGlnThrArg-31 |
| SEQ. ID. NO. 3790 | 67-AsnGlyLysSerGlyAsnAlaHisArgLysGlnGlnLysGluIle-81 |
| SEQ. ID. NO. 3791 | 102-ValArgSerAlaThrArgLysThrAla-110 |
| SEQ. ID. NO. 3792 | 135-SerSerGlyLysSerAlaSer-141 |
| SEQ. ID. NO. 3793 | 146-GlnArgGlyArgGlyAlaCys-152 |
| SEQ. ID. NO. 3794 | 165-SerSerAsnGluTrpLys-170 |
| SEQ. ID. NO. 3795 | 173-ThrAlaLysArgProProSerPheArgArgHisMet-184 |
| SEQ. ID. NO. 3796 | 193-SerSerSerSerArgLeuIleLysMet-201 |

TABLE 1-continued

| SEQ. ID. NO. 3797 | 211-GlySerCysProArgSerArgValArgThr-220 |
|---|---|
| SEQ. ID. NO. 3798 | 245-ArgAlaIleArgArgLeuAsnArgSerSerPro-255 |

240-2
AMPHI Regions - AMPHI

| SEQ. ID. NO. 3799 | 19-AlaAspValGlyArgPheLeuHis-26 |
|---|---|
| SEQ. ID. NO. 3800 | 63-IleGlnCysLeuArgAsnHis-69 |
| SEQ. ID. NO. 3801 | 87-AlaProLeuPheAlaValCysPro-94 |
| SEQ. ID. NO. 3802 | 107-GlnGlyGluAspPheProArgAlaGlyIleGlnAsnHis-119 |
| SEQ. ID. NO. 3803 | 154-ValPheArgGlyPheIleAlaArgGlyValGlnAlaValHisAsn-168 |
| SEQ. ID. NO. 3804 | 188-PheLysArgLysPheGln-193 |

Antigenic Index - Jameson-Wolf

| SEQ. ID. NO. 3805 | 9-GlyThrGluThrArgArgGlnPheAla-17 |
|---|---|
| SEQ. ID. NO. 3806 | 39-IleAlaHisGlyArgArgSerAspPheIleArg-49 |
| SEQ. ID. NO. 3807 | 67-ArgAsnHisLysArgPheAspCysArgThrGlyPheAsp-79 |
| SEQ. ID. NO. 3808 | 101-ValGlyGlyArgIleGlyGlnGlyGluAspPheProArgAlaGlyIleGlnAsnHisHisArgSerGly-123 |
| SEQ. ID. NO. 3809 | 139-GlnGlyLeuAsnProLeuIleGluGlyLysAspAspVal-151 |
| SEQ. ID. NO. 3810 | 173-ValProGlnAsnAspPheArg-179 |
| SEQ. ID. NO. 3811 | 187-ValPheLysArgLysPhe-192 |
| SEQ. ID. NO. 3812 | 201-AsnIleGlyLysSerAspAspValCysLys-210 |

Hydrophilic Regions - Hopp-Woods

| SEQ. ID. NO. 3813 | 10-ThrGluThrArgArgGlnPheAla-17 |
|---|---|
| SEQ. ID. NO. 3814 | 41-HisGlyArgArgSerAspPheIleArg-49 |
| SEQ. ID. NO. 3815 | 67-ArgAsnHisLysArgPheAspCys-74 |
| SEQ. ID. NO. 3816 | 105-IleGlyGlnGlyGluAspPheProArg-113 |
| SEQ. ID. NO. 3817 | 145-IleGluGlyLysAspAspVal-151 |
| SEQ. ID. NO. 3818 | 187-ValPheLysArgLysPhe-192 |
| SEQ. ID. NO. 3819 | 203-GlyLysSerAspAspValCysLys-210 |

241-1
AMPHI Regions - AMPHI

| SEQ. ID. NO. 3820 | 6-ThrArgAlaAlaAsnProPro-12 |
|---|---|
| SEQ. ID. NO. 3821 | 35-ThrArgThrProArgGluProAlaSer-43 |
| SEQ. ID. NO. 3822 | 109-PheLeuIleGlyCysIleAla-115 |
| SEQ. ID. NO. 3823 | 126-PheHisAlaCysGlnArgMetValAlaVal-135 |
| SEQ. ID. NO. 3824 | 194-ArgHisIleAspArgIleAlaGlyIleLeuThrValGln-206 |
| SEQ. ID. NO. 3825 | 229-PheValGlnLysLeuIleValGlyIleIleHis-239 |

Antigenic Index - Jameson-Wolf

| SEQ. ID. NO. 3826 | 1-MetProThrArgProThrArgAlaAlaAsnProProThrProProThr-16 |
|---|---|
| SEQ. ID. NO. 3827 | 23-CysProArgProProTyrArgProProSerValGlnThrArgThrProArgGluProAlaSerSerThrCysAlaAlaLysSerAlaAsnArgArgGlu<br>AsnSerHisAsnAlaGlnPro-62 |
| SEQ. ID. NO. 3828 | 68-ProSerAsnLysMetProSerGluThrGluGlnThrLeuPheArgArgHisGlnIleProProSerCysArgGlnSer-93 |
| SEQ. ID. NO. 3829 | 122-LeuLysAlaAspPhe-126 |
| SEQ. ID. NO. 3830 | 147-ThrIleAspAspAsnIleAla-153 |
| SEQ. ID. NO. 3831 | 166-PheAspPheAsnArgGluHisAlaArgIlePheAspThrAspGlnLeu-181 |
| SEQ. ID. NO. 3832 | 188-ArgIleValGlyArgGlnArgHisIleAspArgIleAla-200 |
| SEQ. ID. NO. 3833 | 209-PheHisGlnArgGluAsnAla-215 |
| SEQ. ID. NO. 3834 | 244-ArgAsnHisGlyIle-248 |
| SEQ. ID. NO. 3835 | 250-HisAspSerHisIleCysProPheArgAsnSerArgLeuIle-263 |

Hydrophilic Regions - Hopp-Woods

| SEQ. ID. NO. 3836 | 1-MetProThrArgProThrArgAlaAlaAsn-10 |
|---|---|
| SEQ. ID. NO. 3837 | 32-SerValGlnThrArgThrProArgGluProAlaSer-43 |
| SEQ. ID. NO. 3838 | 46-CysAlaAlaLysSerAlaAsnArgArgGluAsnSerHis-58 |
| SEQ. ID. NO. 3839 | 70-AsnLysMetProSerGluThrGluGlnThrLeuPheArg-82 |
| SEQ. ID. NO. 3840 | 122-LeuLysAlaAspPhe-126 |
| SEQ. ID. NO. 3841 | 166-PheAspPheAsnArgGluHisAlaArgIlePheAsp-177 |
| SEQ. ID. NO. 3842 | 188-ArgIleValGlyArgGlnArgHisIleAspArgIleAla-200 |
| SEQ. ID. NO. 3843 | 209-PheHisGlnArgGluAsnAla-215 |

242
AMPHI Regions - AMPHI

| SEQ. ID. NO. 3844 | 23-SerGluValValThrGlnPheValAspPheValGlu-34 |
|---|---|
| SEQ. ID. NO. 3845 | 42-AlaGlyPheCysHisIleLeuGlnAsn-50 |
| SEQ. ID. NO. 3846 | 100-AlaAspGlnAlaGln-104 |
| SEQ. ID. NO. 3847 | 122-AsnProPhePheAspPhePheGlnAlaValVal-132 |
| SEQ. ID. NO. 3848 | 137-HisGlnSerGlyPheGlyAspValPhe-145 |
| SEQ. ID. NO. 3849 | 156-LeuGluGlnSerVal-160 |
| SEQ. ID. NO. 3850 | 177-PheGluLeuPheGln-181 |
| SEQ. ID. NO. 3851 | 191-PheGlyHisThrArgLeuPheAspIleCys-200 |
| SEQ. ID. NO. 3852 | 262-HisProPheAlaAspPheGlyAsnPheGlnAsnLeuLeuAlaLeu-276 |

Antigenic Index - Jameson-Wolf

| SEQ. ID. NO. 3853 | 13-HisPheGluGlnArgAlaGlyGlyIleAla-22 |
|---|---|
| SEQ. ID. NO. 3854 | 33-ValGluGlnGluGln-37 |
| SEQ. ID. NO. 3855 | 52-ThrGlyHisArgAlaAspIle-58 |
| SEQ. ID. NO. 3856 | 75-SerHisAlaAspIlePheProProArgCysPheGlyAspGlyPheAlaGlnArgGlyPheAlaHisAlaArgArgAlaAspGlnAlaGlnAsnArgAla-107 |
| SEQ. ID. NO. 3857 | 137-HisGlnSerGlyPhe-141 |
| SEQ. ID. NO. 3858 | 154-ArgGlnLeuGluGlnSerVal-160 |
| SEQ. ID. NO. 3859 | 164-AlaTyrAspGlyGlyPheArgArgHisArgTrpHis-175 |
| SEQ. ID. NO. 3860 | 283-MetArgCysAspArgIleGly-289 |

Hydrophilic Regions - Hopp-Woods

| SEQ. ID. NO. 3861 | 13-HisPheGluGlnArgAlaGlyGlyIle-21 |
|---|---|
| SEQ. ID. NO. 3862 | 33-ValGluGlnGluGln-37 |
| SEQ. ID. NO. 3863 | 52-ThrGlyHisArgAlaAspIle-58 |

TABLE 1-continued

| | |
|---|---|
| SEQ. ID. NO. 3864 | 95-AlaHisAlaArgArgAlaAspGlnAlaGlnAsnArgAla-107 |
| SEQ. ID. NO. 3865 | 154-ArgGlnLeuGluGlnSerVal-160 |
| SEQ. ID. NO. 3866 | 167-GlyGlyPheArgArgHisArg-173 |
| SEQ. ID. NO. 3867 | 283-MetArgCysAspArgIleGly-289 |

243
AMPHI Regions - AMPHI

| | |
|---|---|
| SEQ. ID. NO. 3868 | 35-IleThrArgLeuAlaArgLysAlaValGlnArgLeuThr-47 |
| SEQ. ID. NO. 3869 | 50-HisIleGlnXxxPhePheThrGlu-57 |
| SEQ. ID. NO. 3870 | 80-AspSerSerArgIleThrSerThrIle-88 |

Antigenic Index - Jameson-Wolf

| | |
|---|---|
| SEQ. ID. NO. 3871 | 29-LeuProSerAsnAlaPro-34 |
| SEQ. ID. NO. 3872 | 37-ArgLeuAlaArgLysAlaValGln-44 |
| SEQ. ID. NO. 3873 | 58-SerHisThrGlyAlaAsnArgSerSerSerCysLysPro-71 |
| SEQ. ID. NO. 3874 | 77-SerAlaSerAspSerSerArgIle-84 |
| SEQ. ID. NO. 3875 | 102-SerThrThrGlyAlaValThrLysSer-110 |

Hydrophilic Regions - Hopp-Woods

| | |
|---|---|
| SEQ. ID. NO. 3876 | 37-ArgLeuAlaArgLysAlaValGln-44 |
| SEQ. ID. NO. 3877 | 59-HisThrGlyAlaAsnArgSerSerSerCysLys-70 |
| SEQ. ID. NO. 3878 | 78-AlaSerAspSerSerArgIle-84 |

244-2
AMPHI Regions - AMPHI

| | |
|---|---|
| SEQ. ID. NO. 3879 | 22-LysCysPheLeuGlnLeuValGln-29 |
| SEQ. ID. NO. 3880 | 31-HisLeuHisAlaHis-35 |
| SEQ. ID. NO. 3881 | 109-IleSerArgLeuCysGlySerLeuPhe-117 |
| SEQ. ID. NO. 3882 | 126-CysLeuAspGlyPheHisArgLeuHis-134 |
| SEQ. ID. NO. 3883 | 137-AsnArgPhePheThr-141 |
| SEQ. ID. NO. 3884 | 165-TyrProArgLysIleArgThrPheSerArgAsnPheLysGlnLys-179 |

Antigenic Index - Jameson-Wolf

| | |
|---|---|
| SEQ. ID. NO. 3885 | 1-MetAspIleArgIle-5 |
| SEQ. ID. NO. 3886 | 11-PheArgValAspPheLeuAsp-17 |
| SEQ. ID. NO. 3887 | 45-IleGlnLysArgHis-49 |
| SEQ. ID. NO. 3888 | 54-LeuAspArgGlnHisPheHisGlyLysLeuLeuSerGlyGluLeuValArg-70 |
| SEQ. ID. NO. 3889 | 99-GlnLeuGlyAsnProArgLeu-105 |
| SEQ. ID. NO. 3890 | 154-LeuLysThrAsnTrpLysSerLysSerSerTyrTyrProArgLysIleArgThrPheSerArgAsnPheLysGlnLysGlnArgIleSerAsnSerPheSerAsnProLeuProLysLys-193 |

Hydrophilic Regions - Hopp-Woods

| | |
|---|---|
| SEQ. ID. NO. 3891 | 1-MetAspIleArgIle-5 |
| SEQ. ID. NO. 3892 | 11-PheArgValAspPheLeuAsp-17 |
| SEQ. ID. NO. 3893 | 156-ThrAsnTrpLysSerLysSer-162 |
| SEQ. ID. NO. 3894 | 167-ArgLysIleArgThrPheSerArgAsnPheLysGlnLysGlnArgIle-182 |

246-2
AMPHI Regions - AMPHI

| | |
|---|---|
| SEQ. ID. NO. 3895 | 39-AlaValAsnIleAlaGlnCysPheThr-47 |
| SEQ. ID. NO. 3896 | 67-GluGlnPheAlaAsnLeuPhePhe-74 |
| SEQ. ID. NO. 3897 | 83-AspMetGlyArgPhe-87 |
| SEQ. ID. NO. 3898 | 132-PheGlyCysAspAspValValAspAsnLeuAlaGlyPheGlyArg-146 |
| SEQ. ID. NO. 3899 | 156-GlnLeuSerGlnValPhePheGlnLeuLeuGln-166 |

Antigenic Index - Jameson-Wolf

| | |
|---|---|
| SEQ. ID. NO. 3900 | 1-MetHisGlyArgTyrGlyGlyThrGln-9 |
| SEQ. ID. NO. 3901 | 18-GlnThrGlnArgThrCysPheSerAsnGlyLysValTyr-30 |
| SEQ. ID. NO. 3902 | 34-ThrAspIleGlySer-38 |
| SEQ. ID. NO. 3903 | 59-GlnArgArgThrGluValLeu-65 |
| SEQ. ID. NO. 3904 | 78-AspSerArgHisHisAspMetGlyArg-86 |
| SEQ. ID. NO. 3905 | 92-LeuAspAspGluLeuAla-97 |
| SEQ. ID. NO. 3906 | 133-GlyCysAspAspValValAspAsn-140 |
| SEQ. ID. NO. 3907 | 143-GlyPheGlyArgGlyPhe-148 |

Hydrophilic Regions - Hopp-Woods

| | |
|---|---|
| SEQ. ID. NO. 3908 | 59-GlnArgArgThrGluValLeu-65 |
| SEQ. ID. NO. 3909 | 78-AspSerArgHisHisAspMet-84 |
| SEQ. ID. NO. 3910 | 92-LeuAspAspGluLeuAla-97 |

247-1
AMPHI Regions - AMPHI

| | |
|---|---|
| SEQ. ID. NO. 3911 | 12-SerTyrAspGlyMetLysGlyPheThrIleIle-22 |
| SEQ. ID. NO. 3912 | 25-LeuValAlaGlyLeuLeuSerMetIleValLeu-35 |
| SEQ. ID. NO. 3913 | 48-LeuAsnAspAlaAlaAsn-53 |
| SEQ. ID. NO. 3914 | 81-CysPheAsnMetSerGlu-86 |
| SEQ. ID. NO. 3915 | 123-AsnTyrGlnAsnPhePheGln-129 |
| SEQ. ID. NO. 3916 | 150-ThrValValSerSerCysAlaAlaIleSerLysProGlyLysGlnIleProThrLeu-168 |
| SEQ. ID. NO. 3917 | 256-LysTyrThrAspLysPheAspSerAla-264 |

Antigenic Index - Jameson-Wolf

| | |
|---|---|
| SEQ. ID. NO. 3918 | 1-MetArgArgLysMetLeuAsnValProLysGlySerTyrAspGlyMetLys-17 |
| SEQ. ID. NO. 3919 | 42-TyrPheThrSerArgLysLeuAsnAspAlaAlaAsnGluArgLeuAlaAla-58 |
| SEQ. ID. NO. 3920 | 60-GlnAspLeuArgAsn-64 |
| SEQ. ID. NO. 3921 | 71-ArgAspAlaArgMetAlaGlyGlyPhe-79 |
| SEQ. ID. NO. 3922 | 83-AsnMetSerGluHisProAlaThrAspValIleProAspThrThrGlnGlnAsnSerProPheSerLeuLysArgAsnGlyIleAspLys-112 |
| SEQ. ID. NO. 3923 | 117-AlaGluSerSerAsnIleAsnTyrGln-125 |
| SEQ. ID. NO. 3924 | 140-IleAspAspValAsnAlaSerThr-147 |
| SEQ. ID. NO. 3925 | 157-AlaIleSerLysProGlyLysGlnIleProThrLeuGluAspAlaLysLysGluLeuLysIleProAspGlnAspLysGluGlnAsnGlyAsnIleAlaArgGlnArgHis-193 |
| SEQ. ID. NO. 3926 | 202-ArgIleAlaAspGluGluGlyLeu-209 |

TABLE 1-continued

| | |
|---|---|
| SEQ. ID. NO. 3927 | 212-PheGlnLeuAspAspLysGlyLysTrpGlyAsn-222 |
| SEQ. ID. NO. 3928 | 228-LysLysValArgHisMetLys-234 |
| SEQ. ID. NO. 3929 | 242-GlyCysProGluAspAspAspAlaGlyLysGluGluThrPheLysTyrThrAspLysPheAspSerAlaGln-265 |
| SEQ. ID. NO. 3930 | 279-SerGlyThrAspThrLysIleAlaAlaSerSerAspAsnHis-292 |
| SEQ. ID. NO. 3931 | 300-AlaThrIleArgGlyGlyAsnValCysAlaAsnArgThrLeu-313 |

Hydrophilic Regions - Hopp-Woods

| | |
|---|---|
| SEQ. ID. NO. 3932 | 1-MetArgArgLysMetLeuAsn-7 |
| SEQ. ID. NO. 3933 | 11-GlySerTyrAspGly-15 |
| SEQ. ID. NO. 3934 | 46-ArgLysLeuAsnAspAlaAlaAsnGluArgLeuAlaAla-58 |
| SEQ. ID. NO. 3935 | 60-GlnAspLeuArgAsn-64 |
| SEQ. ID. NO. 3936 | 71-ArgAspAlaArgMet-75 |
| SEQ. ID. NO. 3937 | 104-SerLeuLysArgAsnGlyIleAspLys-112 |
| SEQ. ID. NO. 3938 | 140-IleAspAspValAsnAla-145 |
| SEQ. ID. NO. 3939 | 159-SerLysProGlyLysGln-164 |
| SEQ. ID. NO. 3940 | 166-ProThrLeuGluAspAlaLysLysGluLeuLysIleProAspGlnAspLysGluGlnAsnGlyAsnIleAlaArgGlnArgHis-193 |
| SEQ. ID. NO. 3941 | 202-ArgIleAlaAspGluGluGlyLeu-209 |
| SEQ. ID. NO. 3942 | 213-GlnLeuAspAspLysGlyLysTrpGly-221 |
| SEQ. ID. NO. 3943 | 228-LysLysValArgHisMetLys-234 |
| SEQ. ID. NO. 3944 | 243-CysProGluAspAspAspAlaGlyLysGluGluThrPheLysTyrThrAspLysPheAspSerAlaGln-265 |
| SEQ. ID. NO. 3945 | 280-GlyThrAspThrLysIleAlaAlaSerSerAsp-290 |

248-2
Hydrophilic Regions - Hopp-Woods

| | |
|---|---|
| SEQ. ID. NO. 3946 | 1-MetArgArgLysMetLeuAsn-7 |
| SEQ. ID. NO. 3947 | 11-GlySerTyrAspGly-15 |
| SEQ. ID. NO. 3948 | 46-ArgLysLeuAsnAspAlaAlaAsnGluArgLeuAlaAla-58 |
| SEQ. ID. NO. 3949 | 60-GlnAspLeuArgAsn-64 |
| SEQ. ID. NO. 3950 | 71-ArgAspAlaArgMet-75 |
| SEQ. ID. NO. 3951 | 104-SerLeuLysArgAsnGlyIleAspLys-112 |
| SEQ. ID. NO. 3952 | 140-IleAspAspValAsnAla-145 |
| SEQ. ID. NO. 3953 | 159-SerLysProGlyLysGln-164 |
| SEQ. ID. NO. 3954 | 166-ProThrLeuGluAspAlaLysLysGluLeuLysIleProAspGlnAspLysGluGlnAsnGlyAsnIleAlaArgGlnArgHis-193 |
| SEQ. ID. NO. 3955 | 202-ArgIleAlaAspGluGluGlyLeu-209 |
| SEQ. ID. NO. 3956 | 213-GlnLeuAspAspLysGlyLysTrpGly-221 |
| SEQ. ID. NO. 3957 | 228-LysLysValArgHisMetLys-234 |
| SEQ. ID. NO. 3958 | 243-CysProGluAspAspAspAlaGlyLysGluGluThrPheLysTyrThrAspLysPheAspSerAlaGln-265 |
| SEQ. ID. NO. 3959 | 280-GlyThrAspThrLysIleAlaAlaSerSerAsp-290 |

Antigenic Index - Jameson-Wolf

| | |
|---|---|
| SEQ. ID. NO. 3960 | 1-MetArgLysGlnAsnThrLeuThr-8 |
| SEQ. ID. NO. 3961 | 11-ProThrSerAspGlyGlnArgGly-18 |
| SEQ. ID. NO. 3962 | 40-GlnSerTyrAsnThrGluGlnArgIleSerAlaAsnGluSerAspArgLysLeuAla-58 |
| SEQ. ID. NO. 3963 | 64-AlaAlaLeuArgGluGlyGluLeuGln-72 |
| SEQ. ID. NO. 3964 | 76-LeuGluTyrAspThrAspSerLysValThrPheSerGluAsnCysGlyLysGlyLeu-94 |
| SEQ. ID. NO. 3965 | 99-AsnValArgThrAsnAsnAspAsnGluGluAlaPhe-110 |
| SEQ. ID. NO. 3966 | 116-GlnGlyLysProThrValGluAlaValLysArgSerCysProAlaAsnSerThrAspLeuCysIleAspLysLysGlyMetGluTyrLysLysGlyThrArgSerValSerLysMetProArgTyr-157 |
| SEQ. ID. NO. 3967 | 162-LeuGlyValLysAsnGlyGluAsnValTyr-171 |
| SEQ. ID. NO. 3968 | 177-AlaTrpGlyLysAsnAlaAsnThr-184 |
| SEQ. ID. NO. 3969 | 192-ValSerAsnAsnAspGlu-197 |

Hydrophilic Regions - Hopp-Woods

| | |
|---|---|
| SEQ. ID. NO. 3970 | 1-MetArgLysGlnAsnThr-6 |
| SEQ. ID. NO. 3971 | 11-ProThrSerAspGlyGlnArg-17 |
| SEQ. ID. NO. 3972 | 42-TyrAsnThrGluGlnArgIleSerAlaAsnGluSerAspArgLysLeuAla-58 |
| SEQ. ID. NO. 3973 | 64-AlaAlaLeuArgGluGlyGluLeuGln-72 |
| SEQ. ID. NO. 3974 | 76-LeuGluTyrAspThrAspSerLysValThrPhe-86 |
| SEQ. ID. NO. 3975 | 101-ArgThrAsnAsnAspAsnGluGluAlaPhe-110 |
| SEQ. ID. NO. 3976 | 119-ProThrValGluAlaValLysArgSerCysPro-129 |
| SEQ. ID. NO. 3977 | 135-LeuCysIleAspLysLysGlyMetGluTyrLysLysGlyThrArgSerValSerLysMetPro-155 |
| SEQ. ID. NO. 3978 | 165-LysAsnGlyGluAsnValTyr-171 |
| SEQ. ID. NO. 3979 | 193-SerAsnAsnAspGlu-197 |

249-1
AMPHI Regions - AMPHI

| | |
|---|---|
| SEQ. ID. NO. 3980 | 6-CysPheArgLeuLys-10 |
| SEQ. ID. NO. 3981 | 17-AlaLeuIleGluValLeuVal-23 |
| SEQ. ID. NO. 3982 | 42-ThrValAlaSerValArgGluAla-49 |
| SEQ. ID. NO. 3983 | 53-ThrIleValSerGlnIleThrGlnAsnLeuMetGluGlyMet-66 |

Antigenic Index - Jameson-Wolf

| | |
|---|---|
| SEQ. ID. NO. 3984 | 1-MetLysAsnAsnAspCysPheArgLeuLysAspSerGlnSerGlyMetAla-17 |
| SEQ. ID. NO. 3985 | 44-AlaSerValArgGluAlaGluThr-51 |
| SEQ. ID. NO. 3986 | 70-ProThrIleAspSerAspSerAsnLysLysAsnTyr-81 |
| SEQ. ID. NO. 3987 | 93-ValAspGlyAspPheAla-98 |
| SEQ. ID. NO. 3988 | 101-AlaMetLysThrLysGlyGlnLeuAla-109 |
| SEQ. ID. NO. 3989 | 134-ValCysLysAspSerSerGlyAsnAlaProThrLeuSer-146 |
| SEQ. ID. NO. 3990 | 148-AsnAlaPheSerSerAsnCysAspAsnLysAlaAsnGlyAspThrLeu-163 |
| SEQ. ID. NO. 3991 | 171-AspSerAlaGlyAspSerAspIleSerArgThrAsnLeuGluValSerGlyAspAsn-189 |
| SEQ. ID. NO. 3992 | 196-AlaArgValGlyGlyArgGlu-202 |

Hydrophilic Regions - Hopp-Woods

| | |
|---|---|
| SEQ. ID. NO. 3993 | 1-MetLysAsnAsnAspCysPheArgLeuLysAspSerGlnSer-14 |
| SEQ. ID. NO. 3994 | 44-AlaSerValArgGluAlaGluThr-51 |
| SEQ. ID. NO. 3995 | 72-IleAspSerAspSerAsnLysLysAsn-80 |
| SEQ. ID. NO. 3996 | 101-AlaMetLysThrLysGlyGlnLeuAla-109 |

TABLE 1-continued

| | |
|---|---|
| SEQ. ID. NO. 3997 | 134-ValCysLysAspSerSerGly-140 |
| SEQ. ID. NO. 3998 | 153-AsnCysAspAsnLysAlaAsnGly-160 |
| SEQ. ID. NO. 3999 | 172-SerAlaGlyAspSerAspIleSerArgThrAsnLeu-183 |
| SEQ. ID. NO. 4000 | 198-ValGlyGlyArgGlu-202 |

250-2
AMPHI Regions - AMPHI
| | |
|---|---|
| SEQ. ID. NO. 4001 | 34-PheAlaGlyGlySerGlu-39 |
| SEQ. ID. NO. 4002 | 41-AlaThrValAsnLeuTrpAlaGluPro-49 |
| SEQ. ID. NO. 4003 | 123-LeuThrLysThrSerThrAlaLeuPro-131 |

Antigenic Index - Jameson-Wolf
| | |
|---|---|
| SEQ. ID. NO. 4004 | 14-MetGlnGlyGlyGlnLysGlyMetSer-22 |
| SEQ. ID. NO. 4005 | 35-AlaGlyGlySerGlu-39 |
| SEQ. ID. NO. 4006 | 80-IleProLeuLysLysAlaVal-86 |
| SEQ. ID. NO. 4007 | 103-GluIleGlnLysArgLysAlaAla-110 |
| SEQ. ID. NO. 4008 | 119-PheTyrSerGlyLeuThrLysThrSerThrAlaLeuProArgLeuSerSerLysLysThrIle-139 |

Hydrophilic Regions - Hopp-Woods
| | |
|---|---|
| SEQ. ID. NO. 4009 | 80-IleProLeuLysLysAlaVal-86 |
| SEQ. ID. NO. 4010 | 103-GluIleGlnLysArgLysAlaAla-110 |
| SEQ. ID. NO. 4011 | 133-LeuSerSerLysLysThrIle-139 |

251
AMPHI Regions - AMPHI
| | |
|---|---|
| SEQ. ID. NO. 4012 | 59-AlaTyrGlyAspProIleGlyAlaGlyPhe-68 |
| SEQ. ID. NO. 4013 | 114-GlnValValAlaAspPheGlyGlyIleGluGlyPhe-125 |
| SEQ. ID. NO. 4014 | 160-ArgThrValGlyArgThrValArgLeuLeuLysMetIle-172 |
| SEQ. ID. NO. 4015 | 215-AlaArgThrValPheArgAlaHis-222 |
| SEQ. ID. NO. 4016 | 260-LeuGlyGlnGluCysArg-265 |
| SEQ. ID. NO. 4017 | 267-ArgHisIleAlaArgValGluSerLeuLeuArgValPheGluTyrAlaAlaAsp-284 |

Antigenic Index - Jameson-Wolf
| | |
|---|---|
| SEQ. ID. NO. 4018 | 10-AlaArgAlaAspIleArgProProAlaGlnThrAspIleValProAsnCys-26 |
| SEQ. ID. NO. 4019 | 34-AspAlaAlaArgArgAlaValArg-41 |
| SEQ. ID. NO. 4020 | 49-AlaAspLeuProArgAsnAspIleSerProAlaTyrGlyAspProIleGlyAlaGly-67 |
| SEQ. ID. NO. 4021 | 80-LeuArgGlyArgValArgArgIleGly-88 |
| SEQ. ID. NO. 4022 | 101-GluIleArgAlaAlaLysAlaValLysProGluIle-111 |
| SEQ. ID. NO. 4023 | 149-ArgLeuValGlyThr-153 |
| SEQ. ID. NO. 4024 | 161-ThrValGlyArgThrValArg-167 |
| SEQ. ID. NO. 4025 | 179-ProValValArgGluAlaGlyIle-186 |
| SEQ. ID. NO. 4026 | 212-ValLysHisAlaArgThrValPhe-219 |
| SEQ. ID. NO. 4027 | 244-ValThrGlyGlnArgThrArg-250 |
| SEQ. ID. NO. 4028 | 256-IleLysAsnArgLeuGlyGlnGluCysArgAsnArgHisIleAlaArgValGluSer-274 |
| SEQ. ID. NO. 4029 | 290-LeuLysThrLysThrArgAlaGluGlnProArgProAlaPhe-303 |

Hydrophilic Regions - Hopp-Woods
| | |
|---|---|
| SEQ. ID. NO. 4030 | 10-AlaArgAlaAspIleArgProProAlaGln-19 |
| SEQ. ID. NO. 4031 | 34-AspAlaAlaArgArgAlaValArg-41 |
| SEQ. ID. NO. 4032 | 50-AspLeuProArgAsnAspIle-56 |
| SEQ. ID. NO. 4033 | 82-GlyArgValArgArgIleGly-88 |
| SEQ. ID. NO. 4034 | 101-GluIleArgAlaAlaLysAlaValLysProGluIle-111 |
| SEQ. ID. NO. 4035 | 161-ThrValGlyArgThrValArg-167 |
| SEQ. ID. NO. 4036 | 179-ProValValArgGluAlaGlyIle-186 |
| SEQ. ID. NO. 4037 | 212-ValLysHisAlaArgThrValPhe-219 |
| SEQ. ID. NO. 4038 | 258-AsnArgLeuGlyGlnGluCysArgAsnArgHisIleAlaArgValGluSer-274 |
| SEQ. ID. NO. 4039 | 292-ThrLysThrArgAlaGluGlnProArg-300 |

254-2
AMPHI Regions - AMPHI
| | |
|---|---|
| SEQ. ID. NO. 4040 | 6-ArgPheAsnThrTyrSerHis-12 |
| SEQ. ID. NO. 4041 | 32-GlyHisGlyAspGlyTyrArg-38 |
| SEQ. ID. NO. 4042 | 66-LysLeuLysSerIleLeuLys-72 |
| SEQ. ID. NO. 4043 | 142-ValLeuAlaValMetLysSerLeuThrAlaSerLeuPro-154 |

Antigenic Index - Jameson-Wolf
| | |
|---|---|
| SEQ. ID. NO. 4044 | 2-TyrThrGlyGluArgPheAsnThrTyrSer-11 |
| SEQ. ID. NO. 4045 | 32-GlyHisGlyAspGlyTyrArg-38 |
| SEQ. ID. NO. 4046 | 65-GlyLysLeuLysSerIleLeuLysLysThrAspHis-76 |
| SEQ. ID. NO. 4047 | 94-SerLeuArgAsnGlyProGly-100 |
| SEQ. ID. NO. 4048 | 120-ThrIleGlyArgLysSerGluLysArgLeu-129 |
| SEQ. ID. NO. 4049 | 177-AsnAspGluLysIleArgHisGlyHisGly-186 |

Hydrophilic Regions - Hopp-Woods
| | |
|---|---|
| SEQ. ID. NO. 4050 | 65-GlyLysLeuLysSerIleLeuLysLysThrAspHis-76 |
| SEQ. ID. NO. 4051 | 120-ThrIleGlyArgLysSerGluLysArgLeu-129 |
| SEQ. ID. NO. 4052 | 177-AsnAspGluLysIleArgHis-183 |

255
AMPHI Regions - AMPHI
| | |
|---|---|
| SEQ. ID. NO. 4053 | 23-ValLysThrCysAlaAspPheHisAlaPheAspGlyValAspAlaHisHisArg-40 |
| SEQ. ID. NO. 4054 | 71-GlyIleGlnGlyPheAlaHis-77 |
| SEQ. ID. NO. 4055 | 139-AlaGlyGlyGlyPhe-143 |

Antigenic Index - Jameson-Wolf
| | |
|---|---|
| SEQ. ID. NO. 4056 | 33-AspGlyValAspAlaHisHisArgValGlyAspPheGly-45 |
| SEQ. ID. NO. 4057 | 48-AlaValLysAsnArgPheAlaGlnAlaAspArgAspIleGlyCys-62 |
| SEQ. ID. NO. 4058 | 66-GlnLeuArgAlaAspGlyIleGln-73 |
| SEQ. ID. NO. 4059 | 91-ValGlyGlyLysLysArgIleLeu-98 |
| SEQ. ID. NO. 4060 | 115-GlyAsnValGlyGlyAspPheArgAla-123 |
| SEQ. ID. NO. 4061 | 130-PhePheGlyAsnGlySerGlySerAsnAlaGlyGly-141 |

TABLE 1-continued

| | |
|---|---|
| SEQ. ID. NO. 4062 | 143-PheThrGlyGlyAla-147 |
| SEQ. ID. NO. 4063 | 169-GlyAlaGluAlaGlyGly-174 |

Hydrophilic Regions - Hopp-Woods

| | |
|---|---|
| SEQ. ID. NO. 4064 | 33-AspGlyValAspAlaHisHisArgValGlyAspPheGly-45 |
| SEQ. ID. NO. 4065 | 48-AlaValLysAsnArgPheAlaGlnAlaAspArgAspIleGly-61 |
| SEQ. ID. NO. 4066 | 66-GlnLeuArgAlaAspGly-71 |
| SEQ. ID. NO. 4067 | 92-GlyGlyLysLysArgIleLeu-98 |
| SEQ. ID. NO. 4068 | 119-GlyAspPheArgAla-123 |
| SEQ. ID. NO. 4069 | 135-SerGlySerAsnAla-139 |
| SEQ. ID. NO. 4070 | 169-GlyAlaGluAlaGlyGly-174 |

256-1
AMPHI Regions - AMPHI

| | |
|---|---|
| SEQ. ID. NO. 4071 | 90-GlyValValValHisPheArgSerCysGlyGlyIleAlaAsn-103 |
| SEQ. ID. NO. 4072 | 127-ArgTyrArgGluIleTyrAlaVal-134 |
| SEQ. ID. NO. 4073 | 141-AsnAlaLeuAlaLysTyrLeuGlyGluGln-150 |
| SEQ. ID. NO. 4074 | 173-ArgArgPheAspSerGlyIleThrArgLeuLeu-183 |
| SEQ. ID. NO. 4075 | 197-LysSerLeuGlnGlyPheGlnThrAla-205 |
| SEQ. ID. NO. 4076 | 207-AlaAlaGlyCysLysThrLeuGlyGluPheAspAspArgPheThrAlaProLeuHisGly-226 |
| SEQ. ID. NO. 4077 | 233-TyrTyrArgGlnThrSerCysLysProLeuLeuLysHisValAla-247 |
| SEQ. ID. NO. 4078 | 267-ProArgAlaAspGluValSer-273 |

Antigenic Index - Jameson-Wolf

| | |
|---|---|
| SEQ. ID. NO. 4079 | 4-ThrProProAspThrProPhe-10 |
| SEQ. ID. NO. 4080 | 12-LeuArgAsnGlyAsnAlaAspThrIleAla-21 |
| SEQ. ID. NO. 4081 | 24-PheLeuGlnArgProAlaProAlaTyrArgArgGluLeuLeuProAspSerThrGlyLysThrLysVal-46 |
| SEQ. ID. NO. 4082 | 49-AspPheSerAspGlyIleSerProAspAla-58 |
| SEQ. ID. NO. 4083 | 67-LeuGluGlySerSerArgSerHisTyr-75 |
| SEQ. ID. NO. 4084 | 82-AlaValArgAspArgGlyTrpHis-89 |
| SEQ. ID. NO. 4085 | 112-GlyAspThrAlaGlu-116 |
| SEQ. ID. NO. 4086 | 147-LeuGlyGluGlnGlyLysLysAlaLeu-155 |
| SEQ. ID. NO. 4087 | 166-ValAspAlaGluAlaAlaGlyArgArgPheAspSerGlyIleThr-180 |
| SEQ. ID. NO. 4088 | 192-LeuIleProLysAlaLysSerLeuGln-200 |
| SEQ. ID. NO. 4089 | 212-ThrLeuGlyGluPheAspAspArgPheThr-221 |
| SEQ. ID. NO. 4090 | 227-PheAlaAspArgHisAspTyrTyrArgGlnThrSerCysLysProLeuLeu-243 |
| SEQ. ID. NO. 4091 | 259-ProPheLeuProProGluAlaLeuProArgAlaAspGluValSerGlu-274 |
| SEQ. ID. NO. 4092 | 291-SerSerThrGlyGlyArgLeu-297 |
| SEQ. ID. NO. 4093 | 311-AspSerPheArgThrAsnArgArg-318 |

Hydrophilic Regions - Hopp-Woods

| | |
|---|---|
| SEQ. ID. NO. 4094 | 30-ProAlaTyrArgArgGluLeuLeuPro-38 |
| SEQ. ID. NO. 4095 | 40-SerThrGlyLysThrLysVal-46 |
| SEQ. ID. NO. 4096 | 68-GluGlySerSerArgSer-73 |
| SEQ. ID. NO. 4097 | 83-ValArgAspArgGlyTrp-88 |
| SEQ. ID. NO. 4098 | 147-LeuGlyGluGlnGlyLysLysAlaLeu-155 |
| SEQ. ID. NO. 4099 | 166-ValAspAlaGluAlaAlaGlyArgArgPheAspSerGlyIle-179 |
| SEQ. ID. NO. 4100 | 192-LeuIleProLysAlaLysSer-198 |
| SEQ. ID. NO. 4101 | 212-ThrLeuGlyGluPheAspAspArgPheThr-221 |
| SEQ. ID. NO. 4102 | 227-PheAlaAspArgHisAspTyrTyrArg-235 |
| SEQ. ID. NO. 4103 | 265-AlaLeuProArgAlaAspGluValSerGlu-274 |
| SEQ. ID. NO. 4104 | 313-PheArgThrAsnArgArg-318 |

257-2
AMPHI Regions - AMPHI

| | |
|---|---|
| SEQ. ID. NO. 4105 | 24-SerPheLeuProAsn-28 |
| SEQ. ID. NO. 4106 | 73-AspLeuValAsnLysValLeuAlaGluValAlaArgLeuGluLysIleValGlnProLeu-92 |

Antigenic Index - Jameson-Wolf

| | |
|---|---|
| SEQ. ID. NO. 4107 | 1-MetGlyArgHisPheGlyArgArgArgPhe-10 |
| SEQ. ID. NO. 4108 | 31-AlaAlaAspAspGluLysArgAsnGlyAspGluLysArgAsnGluAsn-46 |
| SEQ. ID. NO. 4109 | 56-GlySerGlyAlaGlu-60 |
| SEQ. ID. NO. 4110 | 65-GlyValAspAspArgArgAlaAlaAspLeuVal-75 |
| SEQ. ID. NO. 4111 | 83-AlaArgLeuGluLysIleVal-89 |

Hydrophilic Regions - Hopp-Woods

| | |
|---|---|
| SEQ. ID. NO. 4112 | 4-HisPheGlyArgArgArgPhe-10 |
| SEQ. ID. NO. 4113 | 31-AlaAlaAspAspGluLysArgAsnGlyAspGluLysArgAsnGlu-45 |
| SEQ. ID. NO. 4114 | 65-GlyValAspAspArgArgAlaAlaAspLeuVal-75 |
| SEQ. ID. NO. 4115 | 83-AlaArgLeuGluLysIleVal-89 |

259-1
AMPHI Regions - AMPHI

| | |
|---|---|
| SEQ. ID. NO. 4116 | 154-TyrGlyArgValPheAlaAspIlePheGluLeuSer-165 |
| SEQ. ID. NO. 4117 | 172-AlaPheLysGlyMetLeuLysLeuThrAlaGluTyrLysAsnIlePheGlyAspAlaCysArg-192 |
| SEQ. ID. NO. 4118 | 203-AsnGlnAlaLeuGlnGluIleSerLysThrSerGlu-214 |

Antigenic Index - Jameson-Wolf

| | |
|---|---|
| SEQ. ID. NO. 4119 | 34-LysAlaTyrThrGluGluLeuProPro-42 |
| SEQ. ID. NO. 4120 | 61-SerAlaArgSerLysAlaLysAlaGluLysPheTyrArgGluLysMetIleGln-78 |
| SEQ. ID. NO. 4121 | 93-LeuGluHisLysPro-97 |
| SEQ. ID. NO. 4122 | 105-LysAsnHisGlyLysGlyMetAlaGluGlnValArgPheLysAla-119 |
| SEQ. ID. NO. 4123 | 121-ValLeuProAspAspGluAspAlaArgThrIleAla-132 |
| SEQ. ID. NO. 4124 | 144-GlyThrAspAlaValAlaSerGlyValThrTyrGlyArgVal-157 |
| SEQ. ID. NO. 4125 | 168-LeuGluGlyArgAlaPhe-173 |
| SEQ. ID. NO. 4126 | 189-AspAlaCysArgSerGluThrAlaLeu-197 |
| SEQ. ID. NO. 4127 | 208-GluIleSerLysThrSerGluLysSerLysArg-218 |

Hydrophilic Regions - Hopp-Woods

| | |
|---|---|
| SEQ. ID. NO. 4128 | 35-AlaTyrThrGluGluLeuPro-41 |

TABLE 1-continued

| | |
|---|---|
| SEQ. ID. NO. 4129 | 62-AlaArgSerLysAlaLysAlaGluLysPheTyrArgGluLysMetIleGln-78 |
| SEQ. ID. NO. 4130 | 93-LeuGluHisLysPro-97 |
| SEQ. ID. NO. 4131 | 106-AsnHisGlyLysGlyMetAlaGluGlnValArgPheLysAla-119 |
| SEQ. ID. NO. 4132 | 121-ValLeuProAspAspGluAspAlaArgThrIleAla-132 |
| SEQ. ID. NO. 4133 | 168-LeuGluGlyArgAlaPhe-173 |
| SEQ. ID. NO. 4134 | 189-AspAlaCysArgSerGluThrAlaLeu-197 |
| SEQ. ID. NO. 4135 | 208-GluIleSerLysThrSerGluLysSerLysArg-218 |

260-2
AMPHI Regions - AMPHI

| | |
|---|---|
| SEQ. ID. NO. 4136 | 12-ProPheSerSerLeuPheArgAlaLeuPhe-21 |
| SEQ. ID. NO. 4137 | 53-PheIleAspSerValGlyGlnValAlaAlaArgLeuPheGlnAlaPhe-68 |
| SEQ. ID. NO. 4138 | 158-GlnValGlyIleValAspLeuIlePro-166 |
| SEQ. ID. NO. 4139 | 175-LeuProArgAlaValGln-180 |

Antigenic Index - Jameson-Wolf

| | |
|---|---|
| SEQ. ID. NO. 4140 | 20-LeuPheGluAspArgValGlyIle-27 |
| SEQ. ID. NO. 4141 | 30-GlyAlaHisAspAlaAlaGlu-36 |
| SEQ. ID. NO. 4142 | 38-AspPheLeuProGluGluPheThrArg-46 |
| SEQ. ID. NO. 4143 | 80-ProAlaPheArgAlaArgGluGlnAlaArgArgGlySerGly-93 |
| SEQ. ID. NO. 4144 | 97-GlyAsnAspLeuArgMetProHisLysAspAlaValGluValAspIleAspGlyGlyAsnThrVal-118 |
| SEQ. ID. NO. 4145 | 126-ThrHisPheAspAspGlyAspAla-133 |
| SEQ. ID. NO. 4146 | 139-AlaGluAlaArgPhe-143 |
| SEQ. ID. NO. 4147 | 184-ArgAsnAlaProGlnGly-189 |
| SEQ. ID. NO. 4148 | 196-ValAlaPheArgArgValArgAla-203 |

Hydrophilic Regions - Hopp-Woods

| | |
|---|---|
| SEQ. ID. NO. 4149 | 20-LeuPheGluAspArgValGlyIle-27 |
| SEQ. ID. NO. 4150 | 30-GlyAlaHisAspAlaAlaGlu-36 |
| SEQ. ID. NO. 4151 | 82-PheArgAlaArgGluGlnAlaArgArgGlySer-92 |
| SEQ. ID. NO. 4152 | 98-AsnAspLeuArgMetProHisLysAspAlaValGluValAspIleAspGly-114 |
| SEQ. ID. NO. 4153 | 127-HisPheAspAspGlyAspAla-133 |
| SEQ. ID. NO. 4154 | 139-AlaGluAlaArgPhe-143 |
| SEQ. ID. NO. 4155 | 196-ValAlaPheArgArgValArgAla-203 |

261
AMPHI Regions - AMPHI

| | |
|---|---|
| SEQ. ID. NO. 4156 | 22-GlnIlePheArgGln-26 |
| SEQ. ID. NO. 4157 | 32-AspThrAlaArgAlaPheAlaAlaAla-40 |
| SEQ. ID. NO. 4158 | 50-GlyLeuLeuAlaAspIle-55 |
| SEQ. ID. NO. 4159 | 94-ArgPheAspLysHis-98 |
| SEQ. ID. NO. 4160 | 137-AlaValTyrLysGlyIleArgAsnAlaValPhe-147 |
| SEQ. ID. NO. 4161 | 158-GlnGlyIleValArgAsnLeu-164 |
| SEQ. ID. NO. 4162 | 203-AspValPheAlaProVal-208 |
| SEQ. ID. NO. 4163 | 212-CysLeuAsnGlnAlaGlyGly-218 |

Antigenic Index - Jameson-Wolf

| | |
|---|---|
| SEQ. ID. NO. 4164 | 40-AlaAlaAspAspAlaVal-45 |
| SEQ. ID. NO. 4165 | 62-ValArgGlnArgProArgLeuArgLeu-70 |
| SEQ. ID. NO. 4166 | 74-HisGlnArgArgValAspLeu-80 |
| SEQ. ID. NO. 4167 | 86-ArgGlnIleLysGlyAsnValHisArgPheAspLysHisVal-99 |
| SEQ. ID. NO. 4168 | 111-AlaHisAlaArgAspAspAspValProTyr-119 |
| SEQ. ID. NO. 4169 | 126-AsnArgGlyIleGluGlnGluLysArgVal-135 |
| SEQ. ID. NO. 4170 | 149-SerPheAspGlyGlyGly-154 |
| SEQ. ID. NO. 4171 | 181-ArgAsnProAlaGly-185 |
| SEQ. ID. NO. 4172 | 197-LeuGluSerAsnGlyLeuAsp-203 |
| SEQ. ID. NO. 4173 | 214-AsnGlnAlaGlyGlyArgIleLeuThrAlaArgLysAspAspGlnGlyLeu-230 |

Hydrophilic Regions - Hopp-Woods

| | |
|---|---|
| SEQ. ID. NO. 4174 | 40-AlaAlaAspAspAlaVal-45 |
| SEQ. ID. NO. 4175 | 62-ValArgGlnArgProArgLeuArgLeu-70 |
| SEQ. ID. NO. 4176 | 74-HisGlnArgArgValAspLeu-80 |
| SEQ. ID. NO. 4177 | 91-AsnValHisArgPheAspLysHisVal-99 |
| SEQ. ID. NO. 4178 | 112-HisAlaArgAspAspValPro-118 |
| SEQ. ID. NO. 4179 | 127-ArgGlyIleGluGlnGluLysArgVal-135 |
| SEQ. ID. NO. 4180 | 221-LeuThrAlaArgLysAspAspGlnGly-229 |

263-2
AMPHI Regions - AMPHI

| | |
|---|---|
| SEQ. ID. NO. 4181 | 32-AsnLeuIleGlyValLeuSerAsnAla-40 |
| SEQ. ID. NO. 4182 | 42-GluAlaLeuAlaPheTyrGlnGluValGlyLysLeuAsnAlaAlaAsnSerLeuThr-60 |
| SEQ. ID. NO. 4183 | 86-LysLeuAlaThrLeuLysLys-92 |
| SEQ. ID. NO. 4184 | 100-LysAlaAlaArgAlaLeuAlaAlaGlyGlu-109 |
| SEQ. ID. NO. 4185 | 115-LeuGlyAlaLeuAlaAlaPheThrGln-123 |
| SEQ. ID. NO. 4186 | 135-GluGluLeuLysAlaPhePheAspAla-143 |
| SEQ. ID. NO. 4187 | 157-ValAlaLeuAlaThrLeuCysAsnTyrValAsnAsnLeuGly-170 |

Antigenic Index - Jameson-Wolf

| | |
|---|---|
| SEQ. ID. NO. 4188 | 10-GluThrAlaProGluAlaAlaLysAlaArgValGluAla-22 |
| SEQ. ID. NO. 4189 | 37-LeuSerAsnAlaPro-41 |
| SEQ. ID. NO. 4190 | 72-AlaArgThrAsnGlnCysGly-78 |
| SEQ. ID. NO. 4191 | 97-GlnSerValLysAlaAlaArg-103 |
| SEQ. ID. NO. 4192 | 108-GlyGluPheAspAspAlaLysLeu-115 |
| SEQ. ID. NO. 4193 | 126-MetAlaLysLysGlyAlaValSerAspGluGluLeuLysAla-139 |
| SEQ. ID. NO. 4194 | 170-GlyGlnThrGluIleAsnProGluLeu-178 |

Hydrophilic Regions - Hopp-Woods

| | |
|---|---|
| SEQ. ID. NO. 4195 | 11-ThrAlaProGluAlaAlaLysAlaArgValGluAla-22 |
| SEQ. ID. NO. 4196 | 97-GlnSerValLysAlaAlaArg-103 |

TABLE 1-continued

SEQ. ID. NO. 4197 108-GlyGluPheAspAspAlaLysLeu-115
SEQ. ID. NO. 4198 126-MetAlaLysLysGlyAlaValSerAspGluGluLeuLysAla-139
264
AMPHI Regions - AMPHI
SEQ. ID. NO. 4199 55-ValAlaGluPheThrGlnThrGly-62
SEQ. ID. NO. 4200 96-IleProSerTyrValArgValThrAsnThrLys-106
SEQ. ID. NO. 4201 124-AsnArgIleIleAspValSer-130
SEQ. ID. NO. 4202 183-LeuAsnGlnAlaAla-187
Antigenic Index - Jameson-Wolf
SEQ. ID. NO. 4203 27-AlaValValLysAlaGluLysLeuHisAlaSerAlaAsnArgSerTyrLysValAlaGlyLysArgTyrThrProLysAsnGlnVal-55
SEQ. ID. NO. 4204 57-GluPheThrGlnThrGlyAsnAlaSerTrp-66
SEQ. ID. NO. 4205 68-GlyGlyArgPheHisGlyArgLysThrSerGlyGlyGluArgTyrAsp-83
SEQ. ID. NO. 4206 103-ThrAsnThrLysAsnGlyLysSerVal-111
SEQ. ID. NO. 4207 114-ArgValAsnAspArgGlyProPheHisGlyAsnArgIleIleAspValSerLysAlaAlaAla-134
SEQ. ID. NO. 4208 153-ValProGlyGlnSerAlaProValAlaGluAsnLysAspIlePheIle-168
SEQ. ID. NO. 4209 170-LeuLysSerPheGlyThrGluHisGluAla-179
SEQ. ID. NO. 4210 200-SerValGluLysArgArgTyrGluTyr-208
SEQ. ID. NO. 4211 213-GlyProPheThrSerGlnGluArgAlaAlaGluAlaGluAlaGlnAla-228
Hydrophilic Regions - Hopp-Woods
SEQ. ID. NO. 4212 27-AlaValValLysAlaGluLysLeuHisAlaSerAlaAsnArgSerTyrLysValAlaGlyLysArgTyrThrPro-51
SEQ. ID. NO. 4213 71-PheHisGlyArgLysThrSerGlyGlyGluArgTyrAsp-83
SEQ. ID. NO. 4214 103-ThrAsnThrLysAsnGlyLys-109
SEQ. ID. NO. 4215 115-ValAsnAspArgGlyProPheHis-122
SEQ. ID. NO. 4216 125-ArgIleIleAspValSerLysAlaAlaAla-134
SEQ. ID. NO. 4217 159-ProValAlaGluAsnLysAspIlePheIle-168
SEQ. ID. NO. 4218 171-LysSerPheGlyThrGluHisGluAla-179
SEQ. ID. NO. 4219 200-SerValGluLysArgArgTyrGluTyr-208
SEQ. ID. NO. 4220 216-ThrSerGlnGluArgAlaAlaGluAlaGluAlaGlnAla-228
266-2
Antigenic Index - Jameson-Wolf
SEQ. ID. NO. 4221 30-AlaLeuLysArgLysHisPhe-36
SEQ. ID. NO. 4222 57-LeuGluSerArgAlaGlySerValHisAspGlnGlyTrpGlu-70
SEQ. ID. NO. 4223 93-TrpHisThrArgAsnArgGlu-99
Hydrophilic Regions - Hopp-Woods
SEQ. ID. NO. 4224 30-AlaLeuLysArgLysHisPhe-36
SEQ. ID. NO. 4225 59-SerArgAlaGlySerValHis-65
268-1
AMPHI Regions - AMPHI
SEQ. ID. NO. 4226 6-AspGlyLeuHisLysPheLysHisIleCysSerAlaAla-18
SEQ. ID. NO. 4227 22-IleLysGluProLeuAspLysVal-29
SEQ. ID. NO. 4228 52-GlnGluAlaAlaArgValSerGluTrp-60
SEQ. ID. NO. 4229 70-GluPheGluGlnPheTrpLysGlyLeuProGlnThrValGlnAsn-84
SEQ. ID. NO. 4230 89-SerGlnLysThrTrpLysSerGlyMetAspLys-99
SEQ. ID. NO. 4231 110-LysThrProAsnGlyIleLys-116
Antigenic Index - Jameson-Wolf
SEQ. ID. NO. 4232 1-ValGlnSerArgTyrAspGly-7
SEQ. ID. NO. 4233 21-LeuIleLysGluProLeuAspLysValLysGlnArgAsnGluGluLeuGluAlaAlaGluGluAlaAlaAla-44
SEQ. ID. NO. 4234 47-AlaLeuGlyArgGluGlnGluAlaAlaArgValSerGluTrpGluGluArgTyrLysLeuSerArgSerGluPhe-71
SEQ. ID. NO. 4235 82-ValGlnAsnLysLeuGlnAlaSerGlnLysThrTrpLysSerGlyMetAspLysIleCysAlaAsnAsnAlaLysAlaGluGlyLysThrProAsnGly
 IleLysPhe-117
SEQ. ID. NO. 4236 119-GluLeuAlaCysLysThrAlaLysThrGluAlaArgLeuGluGluLeuHisAsnArgLysLysAlaLeuIleAspGluMetAlaArgGluAlaAspLys
 LysGluLeuSerLysArgLeu-158
Hydrophilic Regions - Hopp-Woods
SEQ. ID. NO. 4237 3-SerArgTyrAspGly-7
SEQ. ID. NO. 4238 21-LeuIleLysGluProLeuAspLysValLysGlnArgAsnGluGluLeuGluAlaAlaGluGluAlaAlaAla-44
SEQ. ID. NO. 4239 47-AlaLeuGlyArgGluGlnGluAlaAlaArgValSerGluTrpGluGluArgTyrLysLeuSerArgSerGluPhe-71
SEQ. ID. NO. 4240 91-LysThrTrpLysSerGlyMetAspLysIleCys-101
SEQ. ID. NO. 4241 104-AsnAlaLysAlaGluGlyLysThrProAsn-113
SEQ. ID. NO. 4242 119-GluLeuAlaCysLysThrAlaLysThrGluAlaArgLeuGluGluLeuHisAsnArgLysLysAlaLeuIleAspGluMetAlaArgGluAlaAspLys
 LysGluLeuSerLysArgLeu-158
269-2
AMPHI Regions - AMPHI
SEQ. ID. NO. 4243 39-AlaSerValProAla-43
SEQ. ID. NO. 4244 54-TrpAspPheIleGlnAsnThr-60
SEQ. ID. NO. 4245 73-PheLysThrArgAlaLeuGlyArgPheSerSerPro-84
Antigenic Index - Jameson-Wolf
SEQ. ID. NO. 4246 30-ArgSerAlaLeuSerCysLysProCysAlaSerValProAlaSerSer-45
SEQ. ID. NO. 4247 60-ThrAlaSerProLysValSer-66
SEQ. ID. NO. 4248 73-PheLysThrArgAlaLeuGlyArgPheSerSer-83
SEQ. ID. NO. 4249 90-LeuSerGluArgGlyValLysLysProLeu-99
SEQ. ID. NO. 4250 107-GlnValAspThrSerAla-112
SEQ. ID. NO. 4251 117-SerLeuArgSerSer-121
Hydrophilic Regions - Hopp-Woods
SEQ. ID. NO. 4252 61-AlaSerProLysVal-65
SEQ. ID. NO. 4253 73-PheLysThrArgAlaLeuGly-79
SEQ. ID. NO. 4254 90-LeuSerGluArgGlyValLysLysProLeu-99
270-2
AMPHI Regions - AMPHI
SEQ. ID. NO. 4255 41-AspLeuThrGluGlyCys-46
SEQ. ID. NO. 4256 49-ProAspGlySerArg-53

TABLE 1-continued

| | |
|---|---|
| SEQ. ID. NO. 4257 | 100-GlnProSerGlyThrTrp-105 |
| Antigenic Index - Jameson-Wolf | |
| SEQ. ID. NO. 4258 | 1-MetAsnLysAsnArgLysLeu-7 |
| SEQ. ID. NO. 4259 | 41-AspLeuThrGluGlyCysThrLeuProAspGlySerArgValArgAlaAlaAlaValSerThrLysLysProPhe-65 |
| SEQ. ID. NO. 4260 | 71-HisAlaProAlaGlyThrGlu-77 |
| SEQ. ID. NO. 4261 | 86-LysAsnMetAspMetGlyPhe-92 |
| SEQ. ID. NO. 4262 | 95-TyrMetPheGluArgGlnProSerGlyThr-104 |
| SEQ. ID. NO. 4263 | 116-ValGluGlyArgArgAspPheThrAla-124 |
| SEQ. ID. NO. 4264 | 128-IleGlySerArgThrPhe-133 |
| Hydrophilic Regions - Hopp-Woods | |
| SEQ. ID. NO. 4265 | 1-MetAsnLysAsnArgLysLeu-7 |
| SEQ. ID. NO. 4266 | 49-ProAspGlySerArgValArgAla-56 |
| SEQ. ID. NO. 4267 | 60-SerThrLysLysProPhe-65 |
| SEQ. ID. NO. 4268 | 73-ProAlaGlyThrGlu-77 |
| SEQ. ID. NO. 4269 | 96-MetPheGluArgGlnPro-101 |
| SEQ. ID. NO. 4270 | 116-ValGluGlyArgArgAspPheThrAla-124 |
| 271-2 | |
| AMPHI Regions - AMPHI | |
| SEQ. ID. NO. 4271 | 6-MetAlaArgIleTrp-10 |
| SEQ. ID. NO. 4272 | 20-SerProCysProAla-24 |
| SEQ. ID. NO. 4273 | 29-ProLysSerProAla-33 |
| Antigenic Index - Jameson-Wolf | |
| SEQ. ID. NO. 4274 | 2-PheSerSerArgMetAlaArg-8 |
| SEQ. ID. NO. 4275 | 25-LeuThrThrLysProLysSerProAlaLys-34 |
| SEQ. ID. NO. 4276 | 41-ArgSerAsnCysLeu-45 |
| SEQ. ID. NO. 4277 | 61-SerSerThrThrGlyAlaProThrSerArg-70 |
| SEQ. ID. NO. 4278 | 78-SerAlaSerIleAsnLysAspThrArgMetProAlaSerVal-91 |
| SEQ. ID. NO. 4279 | 102-CysCysAlaAsnThrSerLysProProSer-111 |
| Hydrophilic Regions - Hopp-Woods | |
| SEQ. ID. NO. 4280 | 27-ThrLysProLysSerProAlaLys-34 |
| SEQ. ID. NO. 4281 | 80-SerIleAsnLysAspThrArgMet-87 |
| SEQ. ID. NO. 4282 | 105-AsnThrSerLysProPro-110 |
| 272-2 | |
| AMPHI Regions - AMPHI | |
| SEQ. ID. NO. 4283 | 44-IleThrArgIleThrAspGlu-50 |
| SEQ. ID. NO. 4284 | 70-AlaGluGluPheSerSerThrAsn-77 |
| SEQ. ID. NO. 4285 | 106-PheArgThrIleThrSer-111 |
| SEQ. ID. NO. 4286 | 165-IleIleThrIleGluAspProIleGlu-173 |
| SEQ. ID. NO. 4287 | 194-AsnTrpMetAlaAlaLeuLysAsnThrLeuArgGlnAla-206 |
| SEQ. ID. NO. 4288 | 244-AsnGlnAlaLeuAspArgIleIleAsn-252 |
| SEQ. ID. NO. 4289 | 307-GlyAsnIleHisGluIleLysGluValMetLys-317 |
| SEQ. ID. NO. 4290 | 328-AspGlnHisLeuTyrGln-333 |
| SEQ. ID. NO. 4291 | 345-AlaLeuLysAsnAlaAspSer-351 |
| Antigenic Index - Jameson-Wolf | |
| SEQ. ID. NO. 4292 | 2-PheThrAspGluAsnMetThrAlaLysGluGluLeu-13 |
| SEQ. ID. NO. 4293 | 20-MetAsnGlnAsnLysGlySerAsp-27 |
| SEQ. ID. NO. 4294 | 38-MetLysLeuAspGlyLysIleThrArgIleThrAspGluProLeuThrAlaGluLysCysMet-58 |
| SEQ. ID. NO. 4295 | 68-LysGlnAlaGluGluPheSerSerThrAsnGlu-78 |
| SEQ. ID. NO. 4296 | 85-LeuProAspThrSerArgPheArgVal-93 |
| SEQ. ID. NO. 4297 | 109-IleThrSerLysIleProLysPheGluSerLeuAsn-120 |
| SEQ. ID. NO. 4298 | 128-ValAlaLeuLysLysArgGly-134 |
| SEQ. ID. NO. 4299 | 142-ThrGlySerGlyLysSerThrSerLeu-150 |
| SEQ. ID. NO. 4300 | 154-IleAspTyrArgAsnGluAsnSerPheGly-163 |
| SEQ. ID. NO. 4301 | 168-IleGluAspProIle-172 |
| SEQ. ID. NO. 4302 | 176-HisGluHisLysAsnCys-181 |
| SEQ. ID. NO. 4303 | 184-ThrGlnArgGluValGlyValAspThrGluAsn-194 |
| SEQ. ID. NO. 4304 | 199-LeuLysAsnThrLeuArgGlnAlaProAsp-208 |
| SEQ. ID. NO. 4305 | 214-GluIleArgAspArgGluThrMet-221 |
| SEQ. ID. NO. 4306 | 241-AsnSerThrAsnGlnAlaLeuAspArg-249 |
| SEQ. ID. NO. 4307 | 254-PheProGluGluArgArgGluGlnLeuLeu-263 |
| SEQ. ID. NO. 4308 | 278-LeuValProArgAspGlyGlyLysGlyArgValAlaAla-290 |
| SEQ. ID. NO. 4309 | 310-HisGluIleLysGluValMetLysLysSerThr-320 |
| SEQ. ID. NO. 4310 | 334-LeuTyrGluLysGlyAspIleSerLeu-342 |
| SEQ. ID. NO. 4311 | 344-GluAlaLeuLysAsnAlaAspSerAlaHisAspLeu-355 |
| SEQ. ID. NO. 4312 | 361-LeuArgSerArgArgAlaGlnSerSerSerProAspLeuGluLeu-375 |
| Hydrophilic Regions - Hopp-Woods | |
| SEQ. ID. NO. 4313 | 2-PheThrAspGluAsnMetThrAlaLysGluGluLeu-13 |
| SEQ. ID. NO. 4314 | 20-MetAsnGlnAsnLysGlySerAsp-27 |
| SEQ. ID. NO. 4315 | 38-MetLysLeuAspGlyLysIleThrArgIleThrAspGluProLeuThrAlaGluLysCysMet-58 |
| SEQ. ID. NO. 4316 | 68-LysGlnAlaGluGluPheSerSer-75 |
| SEQ. ID. NO. 4317 | 87-AspThrSerArgPheArgVal-93 |
| SEQ. ID. NO. 4318 | 112-LysIleProLysPheGluSer-118 |
| SEQ. ID. NO. 4319 | 128-ValAlaLeuLysLysArgGly-134 |
| SEQ. ID. NO. 4320 | 143-GlySerGlyLysSerThrSer-149 |
| SEQ. ID. NO. 4321 | 155-AspTyrArgAsnGluAsnSer-161 |
| SEQ. ID. NO. 4322 | 168-IleGluAspProIle-172 |
| SEQ. ID. NO. 4323 | 176-HisGluHisLysAsn-180 |
| SEQ. ID. NO. 4324 | 184-ThrGlnArgGluValGlyValAspThr-192 |
| SEQ. ID. NO. 4325 | 201-AsnThrLeuArgGlnAlaPro-207 |
| SEQ. ID. NO. 4326 | 214-GluIleArgAspArgGluThrMet-221 |

TABLE 1-continued

| | |
|---|---|
| SEQ. ID. NO. 4327 | 245-GlnAlaLeuAspArg-249 |
| SEQ. ID. NO. 4328 | 255-ProGluGluArgArgGluGlnLeuLeu-263 |
| SEQ. ID. NO. 4329 | 278-LeuValProArgAspGlyGlyLysGlyArgValAlaAla-290 |
| SEQ. ID. NO. 4330 | 310-HisGluIleLysGluValMetLysLysSerThr-320 |
| SEQ. ID. NO. 4331 | 336-GluLysGlyAspIleSerLeu-342 |
| SEQ. ID. NO. 4332 | 344-GluAlaLeuLysAsnAlaAspSerAlaHisAspLeu-355 |
| SEQ. ID. NO. 4333 | 361-LeuArgSerArgArgAlaGlnSerSerSerProAspLeuGluLeu |

274
AMPHI Regions - AMPHI

| | |
|---|---|
| SEQ. ID. NO. 4334 | 31-TyrLysAspGlyLys-35 |
| SEQ. ID. NO. 4335 | 111-GluAlaValPheLysThrLeuSerPro-119 |

Antigenic Index - Jameson-Wolf

| | |
|---|---|
| SEQ. ID. NO. 4336 | 25-LeuValThrAspAspTyrTyrLysAspGlyLysHisIleAsp-38 |
| SEQ. ID. NO. 4337 | 40-GlnLeuHisArgAspGluGluAlaValArgArgHisIle-52 |
| SEQ. ID. NO. 4338 | 60-ProAspMetAsnAla-64 |
| SEQ. ID. NO. 4339 | 71-GlyGluPheAspGlyLysGlnPro-78 |
| SEQ. ID. NO. 4340 | 85-HisProThrArgLysAlaAspAspGlnThrVal-95 |
| SEQ. ID. NO. 4341 | 99-ProValGlySerAlaGlnAsnGlyArgAlaGluTyr-110 |
| SEQ. ID. NO. 4342 | 117-LeuSerProThrAsnHis-122 |
| SEQ. ID. NO. 4343 | 126-ArgValGluAspAlaAlaGly-132 |
| SEQ. ID. NO. 4344 | 136-ValGluAsnLysTrpIleThrSerGlnGlyAsnAlaValAspLeuThrProMetAspLysLeuPheAsnAsnThrGluSerLys-163 |

Hydrophilic Regions - Hopp-Woods

| | |
|---|---|
| SEQ. ID. NO. 4345 | 29-AspTyrTyrLysAspGlyLysHisIleAsp-38 |
| SEQ. ID. NO. 4346 | 40-GlnLeuHisArgAspGluGluAlaValArgArgHisIle-52 |
| SEQ. ID. NO. 4347 | 72-GluPheAspGlyLysGln-77 |
| SEQ. ID. NO. 4348 | 86-ProThrArgLysAlaAspAspGlnThrVal-95 |
| SEQ. ID. NO. 4349 | 104-GlnAsnGlyArgAlaGluTyr-110 |
| SEQ. ID. NO. 4350 | 126-ArgValGluAspAlaAlaGly-132 |
| SEQ. ID. NO. 4351 | 151-ThrProMetAspLysLeuPheAsn-158 |

276
AMPHI Regions - AMPHI

| | |
|---|---|
| SEQ. ID. NO. 4352 | 9-MetMetArgSerAlaProSerMetValValArgArgTrpAlaThrMetMet-25 |
| SEQ. ID. NO. 4353 | 60-SerPheLysMetAlaArg-65 |
| SEQ. ID. NO. 4354 | 80-ProPheAspProMetGlyTrp-86 |
| SEQ. ID. NO. 4355 | 115-GlyArgLeuTyrArgThrPheSerAsn-123 |
| SEQ. ID. NO. 4356 | 164-ThrLysArgGlySerArgLeu-170 |
| SEQ. ID. NO. 4357 | 207-SerThrSerThrLeuArgLysLeuMetArgProSerThr-219 |

Antigenic Index - Jameson-Wolf

| | |
|---|---|
| SEQ. ID. NO. 4358 | 10-MetArgSerAlaProSerMetVal-17 |
| SEQ. ID. NO. 4359 | 29-PheSerIleArgArgSerSerAlaCysTrpThrArgArgSerAspSerLeuSer-46 |
| SEQ. ID. NO. 4360 | 52-SerSerAsnAsnAsnIle-57 |
| SEQ. ID. NO. 4361 | 67-MetAlaThrArgCysArgCysProProAspLysLeuLeuPro-80 |
| SEQ. ID. NO. 4362 | 82-AspProMetGlyTrpCysSerProSerGlyGluLeuSer-94 |
| SEQ. ID. NO. 4363 | 104-ArgAlaAsnArgThrSerAlaSerProAlaSerGlyArgLeuTyr-118 |
| SEQ. ID. NO. 4364 | 121-PheSerAsnArgValSerSerAsnArgAsnThrSerTrpGluThrArgAlaAsnTrpAlaArgArgGlnSerSerLeu-146 |
| SEQ. ID. NO. 4365 | 158-LeuProAlaAspGlySerThrLysArgGlySerArgLeuThrThr-172 |
| SEQ. ID. NO. 4366 | 176-ProLeuProGluArgProThrArgAlaThrArgSerProCysLeu-190 |
| SEQ. ID. NO. 4367 | 194-LeuLysLeuSerArg-198 |
| SEQ. ID. NO. 4368 | 200-LeuMetProSerGluArgTyrSerThrSerThrLeuArgLysLeuMetArgProSerThrArgCysGlyAla-223 |
| SEQ. ID. NO. 4369 | 229-CysSerGlyGlyValSerArgAsnAlaHisThrProSerAlaAlaArgAsn-245 |

Hydrophilic Regions - Hopp-Woods

| | |
|---|---|
| SEQ. ID. NO. 4370 | 29-PheSerIleArgArgSerSer-35 |
| SEQ. ID. NO. 4371 | 38-TrpThrArgArgSerAspSerLeu-45 |
| SEQ. ID. NO. 4372 | 67-MetAlaThrArgCysArgCysProProAspLys-77 |
| SEQ. ID. NO. 4373 | 90-SerGlyGluLeuSer-94 |
| SEQ. ID. NO. 4374 | 104-ArgAlaAsnArgThrSerAla-110 |
| SEQ. ID. NO. 4375 | 124-ArgValSerSerAsnArgAsnThrSerTrpGluThr-135 |
| SEQ. ID. NO. 4376 | 137-AlaAsnTrpAlaArgArgGlnSerSer-145 |
| SEQ. ID. NO. 4377 | 161-AspGlySerThrLysArgGlySerArg-169 |
| SEQ. ID. NO. 4378 | 176-ProLeuProGluArgProThrArgAlaThrArg-186 |
| SEQ. ID. NO. 4379 | 194-LeuLysLeuSerArg-198 |
| SEQ. ID. NO. 4380 | 200-LeuMetProSerGluArgTyrSer-207 |
| SEQ. ID. NO. 4381 | 210-ThrLeuArgLysLeuMetArgProSerThrArgCys-221 |
| SEQ. ID. NO. 4382 | 232-GlyValSerArgAsnAlaHis-238 |

277
AMPHI Regions - AMPHI

| | |
|---|---|
| SEQ. ID. NO. 4383 | 39-GlyIleAlaValPheGluValValGlyGlyLeuLeuAspPheValLeu-54 |
| SEQ. ID. NO. 4384 | 70-CysProAsnGluValValAspValPheTyrThr-80 |
| SEQ. ID. NO. 4385 | 87-AlaPheAspAlaValGlyAspPheAlaGluTyrGlyArgAlaValAspAlaAlaAspLeuLeuGluIleGlyLysLeuGlyTyrPheHis-116 |
| SEQ. ID. NO. 4386 | 180-AlaValGlyValValAlaValAla-187 |

Antigenic Index - Jameson-Wolf

| | |
|---|---|
| SEQ. ID. NO. 4387 | 2-ProArgPheGluAspLysLeuValGlyArgGlnGlyGluGlyGlyVal-17 |
| SEQ. ID. NO. 4388 | 60-ValGlyAspGlyValAlaVal-66 |
| SEQ. ID. NO. 4389 | 68-ArgPheCysProAsnGluVal-74 |
| SEQ. ID. NO. 4390 | 95-AlaGluTyrGlyArgAlaValAspAla-103 |
| SEQ. ID. NO. 4391 | 118-ValGluProAspPheProAlaGlnThrProArgAlaGluGlyGly-132 |
| SEQ. ID. NO. 4392 | 138-PheAspLysAlaAspValVal-144 |
| SEQ. ID. NO. 4393 | 156-ValGluIleGluVal-160 |
| SEQ. ID. NO. 4394 | 164-GlyGlySerGlyLeuGluGlyAspLeu-172 |
| SEQ. ID. NO. 4395 | 196-LeuAspValGlyGlyLysProArgLeuGlyAla-206 |

TABLE 1-continued

| | |
|---|---|
| SEQ. ID. NO. 4396 | 208-CysAlaGlnAlaGlyGlyGly-214 |
| SEQ. ID. NO. 4397 | 219-GlyThrAspPheHis-223 |
| SEQ. ID. NO. 4398 | 226-GlyLeuAspAspGlyAla-231 |
| SEQ. ID. NO. 4399 | 239-LeuGlnPheGluAspAspLeuLeuGluGlyLysHisGlyLeu-252 |
| Hydrophilic Regions - Hopp-Woods | |
| SEQ. ID. NO. 4400 | 2-ProArgPheGluAspLysLeuValGlyArgGlnGlyGlu-14 |
| SEQ. ID. NO. 4401 | 95-AlaGluTyrGlyArgAlaValAspAla-103 |
| SEQ. ID. NO. 4402 | 118-ValGluProAspPhe-122 |
| SEQ. ID. NO. 4403 | 126-ThrProArgAlaGluGly-131 |
| SEQ. ID. NO. 4404 | 138-PheAspLysAlaAspValVal-144 |
| SEQ. ID. NO. 4405 | 156-ValGluIleGluVal-160 |
| SEQ. ID. NO. 4406 | 167-GlyLeuGluGlyAspLeu-172 |
| SEQ. ID. NO. 4407 | 198-ValGlyGlyLysProArgLeuGlyAla-206 |
| SEQ. ID. NO. 4408 | 226-GlyLeuAspAspGlyAla-231 |
| SEQ. ID. NO. 4409 | 239-LeuGlnPheGluAspAspLeuLeuGluGlyLysHisGlyLeu-252 |
| 278 | |
| AMPHI Regions - AMPHI | |
| SEQ. ID. NO. 4410 | 7-GlyAlaIlePheSerIleGly-13 |
| SEQ. ID. NO. 4411 | 20-IleGlyProLeuProSerIleGlyArg-28 |
| SEQ. ID. NO. 4412 | 42-ThrGlyThrSerLys-46 |
| SEQ. ID. NO. 4413 | 101-ArgThrIleProSerValThrGluIle-109 |
| SEQ. ID. NO. 4414 | 123-PheSerIleLeuAlaLeuIleLysSerLeuIleSer-134 |
| SEQ. ID. NO. 4415 | 157-LeuTyrArgGlnIleGlnAsnLeuIleThrHisPheAsnPheTyrAlaAla-173 |
| SEQ. ID. NO. 4416 | 189-GluThrLeuIleGlnHisLeuHisGlnLeuAlaAsp-200 |
| Antigenic Index - Jameson-Wolf | |
| SEQ. ID. NO. 4417 | 25-SerIleGlyArgProAsnAlaSerThrThrArgProThrSerSerArgProThrGlyThrSerLysIleArgPro-49 |
| SEQ. ID. NO. 4418 | 63-SerProAsnThrThrAlaProThrGluSerArgSerArgPheIleAla-78 |
| SEQ. ID. NO. 4419 | 80-ProLysValLeuProGlyAsnSerSerIle-89 |
| SEQ. ID. NO. 4420 | 93-IleAlaSerAspLysProTrpMetArg-101 |
| SEQ. ID. NO. 4421 | 117-SerAlaPheThrAspArgPheSer-124 |
| SEQ. ID. NO. 4422 | 146-ArgHisSerArgValGlnGlyThr-153 |
| SEQ. ID. NO. 4423 | 178-PheAspPheAspArgAspPhe-184 |
| SEQ. ID. NO. 4424 | 209-ThrValAsnAspGlyArgPheAspMetValGlu-219 |
| Hydrophilic Regions - Hopp-Woods | |
| SEQ. ID. NO. 4425 | 27-GlyArgProAsnAlaSerThrThrArgProThrSerSerArgProThrGlyThrSerLysIleArgPro-49 |
| SEQ. ID. NO. 4426 | 68-AlaProThrGluSerArgSerArgPheIleAla-78 |
| SEQ. ID. NO. 4427 | 93-IleAlaSerAspLysProTrp-99 |
| SEQ. ID. NO. 4428 | 146-ArgHisSerArgValGln-151 |
| SEQ. ID. NO. 4429 | 178-PheAspPheAspArgAspPhe-184 |
| SEQ. ID. NO. 4430 | 211-AsnAspGlyArgPheAspMetValGlu-219 |
| 279 | |
| AMPHI Regions - AMPHI | |
| SEQ. ID. NO. 4431 | 6-GlyCysLeuIleSerThr-11 |
| SEQ. ID. NO. 4432 | 13-PheArgAlaSerAla-17 |
| SEQ. ID. NO. 4433 | 47-AlaAlaAlaMetAlaArgProThrAla-55 |
| Antigenic Index - Jameson-Wolf | |
| SEQ. ID. NO. 4434 | 28-GlnTrpGluGlyThrAspThrGlySerGlyArgAlaArgLeuAla-42 |
| SEQ. ID. NO. 4435 | 64-CysProGlyGluLeuLysLeuThr-71 |
| SEQ. ID. NO. 4436 | 88-CysSerSerSerLysProArgIle-95 |
| SEQ. ID. NO. 4437 | 101-ThrProCysGlyThrAlaAspCysIleSerSerAlaArgArgArgThrSerLeu-118 |
| Hydrophilic Regions - Hopp-Woods | |
| SEQ. ID. NO. 4438 | 29-TrpGluGlyThrAspThrGlySerGlyArgAlaArgLeuAla-42 |
| SEQ. ID. NO. 4439 | 66-GlyGluLeuLysLeu-70 |
| SEQ. ID. NO. 4440 | 89-SerSerSerLysProArgIle-95 |
| SEQ. ID. NO. 4441 | 110-SerSerAlaArgArgArgThrSerLeu-118 |
| 280 | |
| AMPHI Regions - AMPHI | |
| SEQ. ID. NO. 4442 | 27-SerPheSerIleLeuGlyAspValAlaLys-36 |
| SEQ. ID. NO. 4443 | 64-AspIleLysLysIleArgSerAla-71 |
| SEQ. ID. NO. 4444 | 85-AspValGlnArgAlaValLys-91 |
| SEQ. ID. NO. 4445 | 97-TyrThrGluAlaThrLysGlyIleGlnProLeuLys-108 |
| SEQ. ID. NO. 4446 | 146-AlaTyrAlaGlnAsnValAlaLysAlaLeuIleLys-157 |
| SEQ. ID. NO. 4447 | 233-ValAlaAlaIleIleArgGlnIleLys-241 |
| SEQ. ID. NO. 4448 | 243-GluGlyIleLysAlaValPheThrGlu-251 |
| SEQ. ID. NO. 4449 | 254-LysAspThrArgMetValAspArgIleAlaLysGluThr-266 |
| SEQ. ID. NO. 4450 | 274-LeuTyrSerAspAlaLeuGlyAsnAlaProAlaAspThrTyrIle-288 |
| Antigenic Index - Jameson-Wolf | |
| SEQ. ID. NO. 4451 | 38-IleGlyGlyGluArgValSer-44 |
| SEQ. ID. NO. 4452 | 51-AlaAsnGlnAspThrHis-56 |
| SEQ. ID. NO. 4453 | 61-ThrSerGlyAspIleLysLysIleArgSerAlaLys-72 |
| SEQ. ID. NO. 4454 | 82-GluAlaAlaAspValGlnArgAlaValLysGlnSerLysValSerTyrThrGluAlaThrLysGlyIleGln-105 |
| SEQ. ID. NO. 4455 | 107-LeuLysAlaGluGluGluGlyGlyHisHisHisAspHisAspHisAspGlyHisHisHisAspHisGlyGluTyrAspProHisValTrpAsnAspPro-141 |
| SEQ. ID. NO. 4456 | 155-LeuIleLysAlaAspProGluGlyLysValTyrTyr-166 |
| SEQ. ID. NO. 4457 | 176-GlnLeuLysLysLeuHisSerAspAla-184 |
| SEQ. ID. NO. 4458 | 192-ProAlaAlaLysArgLysValLeuThr-200 |
| SEQ. ID. NO. 4459 | 208-MetGlyLysArgTyrHis-213 |
| SEQ. ID. NO. 4460 | 218-AlaProGlnGlyValSerSerGluAlaGluProSerAlaLysGln-232 |
| SEQ. ID. NO. 4461 | 238-ArgGlnIleLysArgGluGlyIle-245 |
| SEQ. ID. NO. 4462 | 251-GluAsnIleLysAspThrArgMetValAspArgIleAlaLysGluThrGlyVal-268 |

TABLE 1-continued

| | |
|---|---|
| SEQ. ID. NO. 4463 | 270-ValSerGlyLysLeuTyrSer-276 |
| SEQ. ID. NO. 4464 | 282-AlaProAlaAspThr-286 |
| SEQ. ID. NO. 4465 | 291-TyrArgHisAsnIle-295 |
| Hydrophilic Regions - Hopp-Woods | |
| SEQ. ID. NO. 4466 | 38-IleGlyGlyGluArgValSer-44 |
| SEQ. ID. NO. 4467 | 63-GlyAspIleLysLysIleArgSerAlaLys-72 |
| SEQ. ID. NO. 4468 | 82-GluAlaAlaAspValGlnArgAlaValLysGlnSerLys-94 |
| SEQ. ID. NO. 4469 | 99-GluAlaThrLysGly-103 |
| SEQ. ID. NO. 4470 | 107-LeuLysAlaGluGluGluGlyGlyHisHisHisAspHisAspHisAspHisGluGlyHisHisHisAspHisGlyGluTyrAsp-134 |
| SEQ. ID. NO. 4471 | 155-LeuIleLysAlaAspProGluGly-162 |
| SEQ. ID. NO. 4472 | 176-GlnLeuLysLysLeuHisSerAspAla-184 |
| SEQ. ID. NO. 4473 | 192-ProAlaAlaLysArgLysValLeuThr-200 |
| SEQ. ID. NO. 4474 | 222-ValSerSerGluAlaGluProSerAlaLysGln-232 |
| SEQ. ID. NO. 4475 | 238-ArgGlnIleLysArgGluGlyIle-245 |
| SEQ. ID. NO. 4476 | 251-GluAsnIleLysAspThrArgMetValAspArgIleAlaLysGluThrGlyVal-268 |
| 281-2 | |
| AMPHI Regions - AMPHI | |
| SEQ. ID. NO. 4477 | 62-AlaAlaGlyMetLeuMetAlaLeuLeuAlaGlyLeuValSerArgPhe-77 |
| SEQ. ID. NO. 4478 | 126-LeuGlnLeuIleAlaAlaValSerSerLeuThr-136 |
| SEQ. ID. NO. 4479 | 179-LeuValSerGlyPheGlnAlaLeuGlyThrLeuMetSerVal-192 |
| SEQ. ID. NO. 4480 | 205-TrpAlaLysHisMet-209 |
| SEQ. ID. NO. 4481 | 216-SerValLeuThrAlaLeuLeuCysGly-224 |
| Antigenic Index - Jameson-Wolf | |
| SEQ. ID. NO. 4482 | 25-ArgArgMetSerLeu-29 |
| SEQ. ID. NO. 4483 | 78-ThrThrLeuLysGluAspAlaAsn-85 |
| SEQ. ID. NO. 4484 | 102-SerLysAsnGlySerSerVal-108 |
| SEQ. ID. NO. 4485 | 159-SerValGlyGlyLysGlyGly-165 |
| SEQ. ID. NO. 4486 | 236-IleProSerGlyPro-240 |
| SEQ. ID. NO. 4487 | 256-LeuGlyLysGluGlyGlyIle-262 |
| SEQ. ID. NO. 4488 | 270-HisArgHisHisThrThr-275 |
| Hydrophilic Regions - Hopp-Woods | |
| SEQ. ID. NO. 4489 | 25-ArgArgMetSerLeu-29 |
| SEQ. ID. NO. 4490 | 78-ThrThrLeuLysGluAspAlaAsn-85 |
| SEQ. ID. NO. 4491 | 103-LysAsnGlySerSer-107 |
| SEQ. ID. NO. 4492 | 256-LeuGlyLysGluGlyGlyIle-262 |
| SEQ. ID. NO. 4493 | 270-HisArgHisHisThr-274 |
| 282 | |
| AMPHI Regions - AMPHI | |
| SEQ. ID. NO. 4494 | 10-LeuIleValAlaPheLeuValLeuIleAsnProPheSerAlaLeu-24 |
| SEQ. ID. NO. 4495 | 50-ValPheAlaValIleAlaValPheAlaLeuIleGlyGlyThrLeu-64 |
| SEQ. ID. NO. 4496 | 112-ArgProAlaArgAsn-116 |
| SEQ. ID. NO. 4497 | 176-ValSerArgLeuLeu-180 |
| SEQ. ID. NO. 4498 | 186-ThrIleLeuAsnArgIleMetGlyMet-194 |
| Antigenic Index - Jameson-Wolf | |
| SEQ. ID. NO. 4499 | 31-ThrAsnGlyHisSerThrLysGluArgArgLysValAlaArg-44 |
| SEQ. ID. NO. 4500 | 92-AsnGlyAsnAspAsnProAlaLysGlnAsnLeuGlyAlaGlnProGluThrGlyGlnAlaArgProAlaArgAsnAlaGly-118 |
| Hydrophilic Regions - Hopp-Woods | |
| SEQ. ID. NO. 4501 | 34-HisSerThrLysGluArgArgLysValAlaArg-44 |
| SEQ. ID. NO. 4502 | 92-AsnGlyAsnAspAsnProAlaLysGlnAsnLeu-102 |
| SEQ. ID. NO. 4503 | 104-AlaGlnProGluThrGlyGlnAlaArgProAlaArgAsn-116 |
| 283 | |
| AMPHI Regions - AMPHI | |
| SEQ. ID. NO. 4504 | 11-ThrLeuAlaSerPheLeuPro-17 |
| SEQ. ID. NO. 4505 | 32-GlyGlyAsnSerTyrSerAspValProLysGlnLeuHis-44 |
| SEQ. ID. NO. 4506 | 67-AlaAspAlaGlyLysArgThr-73 |
| Antigenic Index - Jameson-Wolf | |
| SEQ. ID. NO. 4507 | 28-TrpLysAspGlyGlyGlyAsnSerTyrSerAspValProLysGlnLeuHisProAspGlnSerGln-49 |
| SEQ. ID. NO. 4508 | 53-LeuArgThrArgGlnThrLysProAlaValLysProAlaGlnAlaAspAlaGlyLysArgThrAspGlyAlaAlaGlnGluAsnAsnProAspThrAla GluLysAsnArgGlnLeuGluGluGluLysLysArgIleAlaGluThrGluArgGlnAsnLysGluGluAsnCysArgIleSerLysMetAsnLeu-117 |
| SEQ. ID. NO. 4509 | 121-GlyAsnSerAsnAlaLysAsnLysAspAspLeuIleArgLysTyrAsnAsnAlaValAsnLysTyrCysArg-144 |
| Hydrophilic Regions - Hopp-Woods | |
| SEQ. ID. NO. 4510 | 35-SerTyrSerAspValProLys-41 |
| SEQ. ID. NO. 4511 | 43-LeuHisProAspGlnSerGln-49 |
| SEQ. ID. NO. 4512 | 53-LeuArgThrArgGlnThrLysProAlaValLysProAlaGlnAlaAspAlaGlyLysArgThrAspGlyAlaAlaGlnGluAsnAsnProAspThrAla GluLysAsnArgGlnLeuGluGluGluLysLysArgIleAlaGluThrGluArgGlnAsnLysGluGluAsnCysArgIleSerLysMetAsnLeu-117 |
| SEQ. ID. NO. 4513 | 123-SerAsnAlaLysAsnLysAspAspLeuIleArgLysTyrAsn-136 |
| 284 | |
| AMPHI Regions - AMPHI | |
| SEQ. ID. NO. 4514 | 43-GluAlaPheAlaGlyPhePheGluThrVal-52 |
| SEQ. ID. NO. 4515 | 61-ThrPheAlaAlaArgPhe-66 |
| SEQ. ID. NO. 4516 | 125-ValAspPheAspValPhe-130 |
| SEQ. ID. NO. 4517 | 154-ValValPheArgLeuPheArgGlnValValValAsp-165 |
| SEQ. ID. NO. 4518 | 174-AspThrAlaCysGlyAsnIleGlyGly-182 |
| SEQ. ID. NO. 4519 | 186-PheAlaAlaAlaPheThrGlnIleHisGln-195 |
| SEQ. ID. NO. 4520 | 216-PheValGlnPheIleArgAsnAspPheGlyHisGly-227 |
| SEQ. ID. NO. 4521 | 277-PheArgValPheGlyGlnPheAlaArgGlnPheAla-288 |
| SEQ. ID. NO. 4522 | 307-CysPheHisAspGlyPheAspValValAspLys-317 |
| SEQ. ID. NO. 4523 | 342-LeuHisGlnValHisGlnThrAla-349 |
| SEQ. ID. NO. 4524 | 352-GlyAspAsnGlnIleAspArgPheAlaGln-361 |
| SEQ. ID. NO. 4525 | 372-AlaAspAspAlaAspGlyAla-378 |

TABLE 1-continued

| | |
|---|---|
| SEQ. ID. NO. 4526 | 405-GlnSerThrArgAlaPheAlaArgPhePheAlaAlaPheGlyGlnPheLeuGlnSer-423 |

Antigenic Index - Jameson-Wolf

| | |
|---|---|
| SEQ. ID. NO. 4527 | 1-MetProSerGluThrArgAsnArgPhe-9 |
| SEQ. ID. NO. 4528 | 109-PheAspGlyGlnPhe-113 |
| SEQ. ID. NO. 4529 | 132-HisPheGlyLysArgAsnArgAsnThrArgAla-142 |
| SEQ. ID. NO. 4530 | 147-GlyAlaProAspAlaVal-152 |
| SEQ. ID. NO. 4531 | 166-AsnValGlyAsnGlyArgTyrValAspThrAlaCysGlyAsnIleGlyGlyAsnGlnAsnPhe-186 |
| SEQ. ID. NO. 4532 | 220-IleArgAsnAspPheGlyHisGlyPheGlyGlyArgGluAsnHisAla-235 |
| SEQ. ID. NO. 4533 | 273-AspPheAspAspPheArg-278 |
| SEQ. ID. NO. 4534 | 286-GlnPheAlaAspArgAlaValProSerGlyGlyGluGlnGlnSer-300 |
| SEQ. ID. NO. 4535 | 303-ValAlaArgArgCysPheHisAspGlyPheAspValValAspLysAlaHis-319 |
| SEQ. ID. NO. 4536 | 347-GlnThrAlaArgArgGlyAspAsnGlnIleAspArgPheAlaGlnGlyThrGlyLeuValAlaGluArgArgAlaAlaAspAspAlaAspGlyAla Glu-379 |
| SEQ. ID. NO. 4537 | 398-PheAlaGlyArgGlyGlyGlnHisGlnSerThrArgAla-409 |

Hydrophilic Regions - Hopp-Woods

| | |
|---|---|
| SEQ. ID. NO. 4538 | 1-MetProSerGluThrArgAsnArgPhe-9 |
| SEQ. ID. NO. 4539 | 134-GlyLysArgAsnArgAsnThrArgAla-142 |
| SEQ. ID. NO. 4540 | 229-GlyGlyArgGluAsnHisAla-235 |
| SEQ. ID. NO. 4541 | 286-GlnPheAlaAspArgAlaValProSerGlyGlyGluGlnGln-299 |
| SEQ. ID. NO. 4542 | 313-AspValValAspLysAlaHis-319 |
| SEQ. ID. NO. 4543 | 347-GlnThrAlaArgArgGlyAspAsnGlnIleAspArgPheAla-360 |
| SEQ. ID. NO. 4544 | 366-ValAlaGluArgArgAlaAlaAspAspAlaAspGlyAlaGlu-379 |
| SEQ. ID. NO. 4545 | 402-GlyGlnHisGlnSer-406 |

285-1
AMPHI Regions - AMPHI

| | |
|---|---|
| SEQ. ID. NO. 4546 | 15-ValCysPheLeuGly-19 |
| SEQ. ID. NO. 4547 | 34-GlnIleProSerTrp-38 |
| SEQ. ID. NO. 4548 | 50-GlyThrLeuLeuAspGlyPheAsp-57 |
| SEQ. ID. NO. 4549 | 116-SerLeuProAspSerIleAspLeuPro-124 |
| SEQ. ID. NO. 4550 | 208-HisSerThrAlaArg-212 |
| SEQ. ID. NO. 4551 | 240-HisProPheAlaGluSerLeuAspLysThrLeuGluGluValLeu-254 |
| SEQ. ID. NO. 4552 | 266-ValProSerLeuPro-270 |
| SEQ. ID. NO. 4553 | 280-AlaIleProSerPheSerAsp-286 |
| SEQ. ID. NO. 4554 | 313-GlnValLeuGlyGly-317 |
| SEQ. ID. NO. 4555 | 592-IleGlyLysAlaAlaAspIle-598 |
| SEQ. ID. NO. 4556 | 609-ProAspThrSerArg-613 |
| SEQ. ID. NO. 4557 | 671-GlyIleAsnArgGluLeuThrArgTrp-679 |
| SEQ. ID. NO. 4558 | 747-IleAlaGluLeuHisAsnPhePheLysProProPhe-758 |
| SEQ. ID. NO. 4559 | 776-AlaArgGlyTyrLeu-780 |
| SEQ. ID. NO. 4560 | 836-PheGlyGlyAsnMetAlaAsn-842 |
| SEQ. ID. NO. 4561 | 848-ArgIleThrAlaSerLeu-853 |
| SEQ. ID. NO. 4562 | 855-AspLeuGlyAlaLeu-859 |
| SEQ. ID. NO. 4563 | 868-GlnAsnIleThrGlySerLeuAsnAlaAla-877 |
| SEQ. ID. NO. 4564 | 955-GlySerIleAlaAsp-959 |
| SEQ. ID. NO. 4565 | 1008-ThrAlaGluLeu-1012 |
| SEQ. ID. NO. 4566 | 1061-ValThrGlyMetIleLys-1066 |
| SEQ. ID. NO. 4567 | 1135-SerGlyGlySerValArgGlyValGlyThrValArg-1146 |
| SEQ. ID. NO. 4568 | 1165-ThrValSerPheValGlyProLeuAsn-1173 |
| SEQ. ID. NO. 4569 | 1190-AlaGlyValGluIleLeuGlySerLeuAsn-1199 |
| SEQ. ID. NO. 4570 | 1244-LeuAlaGlyGlnIle-1248 |
| SEQ. ID. NO. 4571 | 1305-ValLysLeuIleTyrArgLeuThrArgAlaIleGlnAlaValAlaArgIleGlySer-1323 |

Antigenic Index - Jameson-Wolf

| | |
|---|---|
| SEQ. ID. NO. 4572 | 43-IleSerSerGlnAsnLeuLysGlyThrLeuLeuAspGlyPheAspGlyAspAsnTrpSerIleGluThrGluGlyAlaAspLeuLysIleSerArg-74 |
| SEQ. ID. NO. 4573 | 80-LysProSerGluLeuMetArgArgSerLeuHis-90 |
| SEQ. ID. NO. 4574 | 104-LysProThrProProLysGluGluArgProProLeuSerLeuProAspSerIleAsp-122 |
| SEQ. ID. NO. 4575 | 130-AspArgPheGluThrGlyLysIleSerMetGlyLysAlaPheAspLysGlnThrValTyr-149 |
| SEQ. ID. NO. 4576 | 151-GluArgLeuAspAlaSerTyrArgTyrAspArgLysGlyHisArgLeuAspLeuAlaAlaAspThrProTrpSerSerSerGlyAlaAla-182 |
| SEQ. ID. NO. 4577 | 185-GlyLeuLysLysProPheAla-191 |
| SEQ. ID. NO. 4578 | 198-ThrLysGlyGlyLeuGluGlyLysThrIle-207 |
| SEQ. ID. NO. 4579 | 209-SerThrAlaArgLeuSerGlySerLeuLysAspValArgAla-222 |
| SEQ. ID. NO. 4580 | 224-LeuAlaIleAspGlyGlyAsnIleArgLeuSerGlyLysSer-237 |
| SEQ. ID. NO. 4581 | 244-GluSerLeuAspLysThrLeuGlu-251 |
| SEQ. ID. NO. 4582 | 268-SerLeuProAspAla-272 |
| SEQ. ID. NO. 4583 | 292-GlySerLeuAspLeuGluAsnThrLys-300 |
| SEQ. ID. NO. 4584 | 302-GlyPheAlaAspArgAsnGlyIleProVal-311 |
| SEQ. ID. NO. 4585 | 320-IleArgGlnAspGlyThrVal-326 |
| SEQ. ID. NO. 4586 | 337-GlyArgGlyIleArgLeuSerGlyLysIleAspThrGluLysAspIleLeu-354 |
| SEQ. ID. NO. 4587 | 362-SerValGlyAlaGluAspValLeu-369 |
| SEQ. ID. NO. 4588 | 372-AlaPheLysGlyArgLeuAspGlySerIle-381 |
| SEQ. ID. NO. 4589 | 387-ThrAlaSerProLysIle-392 |
| SEQ. ID. NO. 4590 | 400-ThrAlaArgThrAspGlySerLeu-407 |
| SEQ. ID. NO. 4591 | 411-SerAspProAlaAsnGlyGlnArgLysLeuVal-421 |
| SEQ. ID. NO. 4592 | 430-GlyGlnGlySerLeuThr-435 |
| SEQ. ID. NO. 4593 | 442-LeuPheLysAspArgLeuLeuLysLeuAspIleArgSerArgAlaPheAspProSerArgIleAspProGlnLeu-466 |
| SEQ. ID. NO. 4594 | 480-GluLeuAlaLysGluLysPheThrGlyLys-489 |
| SEQ. ID. NO. 4595 | 508-IleValTyrGluSerArgHisLeuProArgAlaAlaVal-520 |
| SEQ. ID. NO. 4596 | 522-LeuArgLeuGlyArgAsnIleIleLysThrAspGlyGlyPheGlyLysLysGlyAspArgLeuAsn-543 |
| SEQ. ID. NO. 4597 | 548-AlaProAspLeuSerArgPheGly-555 |
| SEQ. ID. NO. 4598 | 563-AsnValArgGlyHisLeuSerGlyAspLeuAspGlyGlyIleArgThrPheGluThrAspLeuSerGlyAlaAla-587 |
| SEQ. ID. NO. 4599 | 594-LysAlaAlaAspIleArgSer-600 |

TABLE 1-continued

| | |
|---|---|
| SEQ. ID. NO. 4600 | 605-LeuLysGlySerProAspThrSerArgProIleArgAlaAspIleLysGlySerArgLeuSerLeuSerGlyGly-629 |
| SEQ. ID. NO. 4601 | 634-AspThrAlaAspLeuMetLeuAspGlyThrGlyVal-645 |
| SEQ. ID. NO. 4602 | 647-HisArgIleArgThr-651 |
| SEQ. ID. NO. 4603 | 656-ThrLeuAspGlyLysProPheLysPheAspLeuAspAlaSerGlyGlyIleAsnArgGluLeuThrArgTrpLysGlySerIle-683 |
| SEQ. ID. NO. 4604 | 696-LeuGlnAsnArgMetThrLeu-702 |
| SEQ. ID. NO. 4605 | 704-AlaGlyAlaGluArgValAla-710 |
| SEQ. ID. NO. 4606 | 729-SerTrpAspLysLysThrGlyIleSerAlaLysGlyGlyAla-742 |
| SEQ. ID. NO. 4607 | 764-LeuAsnGlyAspTrp-768 |
| SEQ. ID. NO. 4608 | 772-TyrGlyArgAsnAlaArgGly-778 |
| SEQ. ID. NO. 4609 | 782-IleSerArgGlnSerGlyAspAlaValLeu-791 |
| SEQ. ID. NO. 4610 | 803-SerLeuLysThrArgPheGlnAsnAspArgIleGly-814 |
| SEQ. ID. NO. 4611 | 817-LeuAspGlyGlyAlaArgPheGlyArgIleAsnAla-828 |
| SEQ. ID. NO. 4612 | 844-ProLeuGlyGlyArgIleThr-850 |
| SEQ. ID. NO. 4613 | 882-GlyArgValGlySerProSerVal-889 |
| SEQ. ID. NO. 4614 | 893-ValAsnGlySerSerAsnTyrGlyLysIleAsnGly-904 |
| SEQ. ID. NO. 4615 | 908-ValGlyGlnSerArgSerPheAspThrAlaProLeuGlyGlyArgLeuAsn-924 |
| SEQ. ID. NO. 4616 | 941-GlnThrValLysGlySerLeu-947 |
| SEQ. ID. NO. 4617 | 956-SerIleAlaAspProHisLeuGlyGly-964 |
| SEQ. ID. NO. 4618 | 966-IleAsnGlyAspLysLeuTyrTyrArgAsnGlnThr-977 |
| SEQ. ID. NO. 4619 | 982-LeuAspAsnGlySerLeuArg-988 |
| SEQ. ID. NO. 4620 | 991-IleAlaGlyArgLysTrpVal-997 |
| SEQ. ID. NO. 4621 | 1001-LeuLysPheArgHisGluGlyThrAlaGluLeuSerGly-1013 |
| SEQ. ID. NO. 4622 | 1015-ValGlyMetGluAsnSerGlyProAspValAspIle-1026 |
| SEQ. ID. NO. 4623 | 1031-AspLysTyrArgIleLeuSerArgProAsnArgArgLeuThr-1044 |
| SEQ. ID. NO. 4624 | 1047-GlyAsnThrArgLeuArgTyrSerProGlnLysGlyIle-1059 |
| SEQ. ID. NO. 4625 | 1065-IleLysThrAspGlnGlyLeuPheGlySerGlnLysSerSerMetProSerValGlyAspAspVal-1086 |
| SEQ. ID. NO. 4626 | 1091-GluValLysLysGluAlaAla-1097 |
| SEQ. ID. NO. 4627 | 1109-AspLeuAsnAspGlyIleArg-1115 |
| SEQ. ID. NO. 4628 | 1134-GlnSerGlyGlySerValArgGlyValGly-1143 |
| SEQ. ID. NO. 4629 | 1146-ArgValIleLysGlyArgTyrLysAlaTyrGlyGlnAspLeuAspIle |
| SEQ. ID. NO. 4630 | ThrLysGlyThr-1165 |
| SEQ. ID. NO. 4631 | 1171-ProLeuAsnAspProAsnLeuAsnIleArgAlaGluArgArgLeuSerProValGly-1189 |
| SEQ. ID. NO. 4632 | 1197-SerLeuAsnSerProArgIle-1203 |
| SEQ. ID. NO. 4633 | 1207-AlaAsnGluProMetSerGluLysAspLysLeu-1217 |
| SEQ. ID. NO. 4634 | 1225-AlaGlySerGlySerSerGlyAspAsnAlaAla-1235 |
| SEQ. ID. NO. 4635 | 1246-GlyGlnIleAsnAspArgIleGlyLeu-1254 |
| SEQ. ID. NO. 4636 | 1256-AspAspLeuGlyPheThrSerLysArgSerArgAsnAlaGlnThrGlyGluLeuAsnProAlaGlu-1277 |
| SEQ. ID. NO. 4637 | 1283-GlyLysGlnLeuThrGlyLys-1289 |
| SEQ. ID. NO. 4638 | 1299-SerSerAlaGluGlnSerVal-1305 |
| SEQ. ID. NO. 4639 | 1321-IleGlySerArgSerSerGlyGlyGluLeu-1330 |
| SEQ. ID. NO. 4640 | 1335-ArgPheAspArgPheSerGlySerAspLysLysAspSerAlaGlyAsnGlyLysGlyLys-1354 |
| Hydrophilic Regions - Hopp-Woods | |
| SEQ. ID. NO. 4641 | 56-PheAspGlyAspAsnTrpSerIleGluThrGluGlyAlaAspLeuLysIleSerArg-74 |
| SEQ. ID. NO. 4642 | 83-GluLeuMetArgArgSerLeuHis-90 |
| SEQ. ID. NO. 4643 | 105-ProThrProProLysGluGluArgProPro-114 |
| SEQ. ID. NO. 4644 | 130-AspArgPheGluThrGlyLys-136 |
| SEQ. ID. NO. 4645 | 141-LysAlaPheAspLys-145 |
| SEQ. ID. NO. 4646 | 151-GluArgLeuAspAla-155 |
| SEQ. ID. NO. 4647 | 157-TyrArgTyrAspArgLysGlyHisArgLeuAspLeuLysAlaAlaAsp-172 |
| SEQ. ID. NO. 4648 | 200-GlyGlyLeuGluGlyLysThrIle-207 |
| SEQ. ID. NO. 4649 | 215-GlySerLeuLysAspValArgAla-222 |
| SEQ. ID. NO. 4650 | 244-GluSerLeuAspLysThrLeuGlu-251 |
| SEQ. ID. NO. 4651 | 292-GlySerLeuAspLeuGluAsnThrLys-300 |
| SEQ. ID. NO. 4652 | 302-GlyPheAlaAspArgAsnGlyIlePro-310 |
| SEQ. ID. NO. 4653 | 320-IleArgGlnAspGly-324 |
| SEQ. ID. NO. 4654 | 343-LeuSerGlyLysIleAspThrGluLysAspIleLeu-354 |
| SEQ. ID. NO. 4655 | 364-GlyAlaGluAspValLeu-369 |
| SEQ. ID. NO. 4656 | 373-PheLysGlyArgLeuAspGly-379 |
| SEQ. ID. NO. 4657 | 401-AlaArgThrAspGly-405 |
| SEQ. ID. NO. 4658 | 412-AspProAlaAsnGlyGlnArgLysLeuVal-421 |
| SEQ. ID. NO. 4659 | 442-LeuPheLysAspArgLeuLeuLysLeuAspIleArgSerArgAlaPheAspProSerArgIleAspPro-464 |
| SEQ. ID. NO. 4660 | 480-GluLeuAlaLysGluLysPheThrGly-488 |
| SEQ. ID. NO. 4661 | 508-IleValTyrGluSerArgHisLeuPro-516 |
| SEQ. ID. NO. 4662 | 522-LeuArgLeuGlyArgAsnIleIleLysThrAspGlyGlyPheGlyLysLysGlyAspArgLeuAsn-543 |
| SEQ. ID. NO. 4663 | 570-GlyAspLeuAspGlyGlyIleArgThrPheGluThrAspLeuSerGlyAlaAla-587 |
| SEQ. ID. NO. 4664 | 594-LysAlaAlaAspIleArgSer-600 |
| SEQ. ID. NO. 4665 | 607-GlySerProAspThrSerArgProIleArgAlaAspIleLysGlySerArgLeuSerLeu-626 |
| SEQ. ID. NO. 4666 | 634-AspThrAlaAspLeuMetLeu-640 |
| SEQ. ID. NO. 4667 | 647-HisArgIleArgThr-651 |
| SEQ. ID. NO. 4668 | 657-LeuAspGlyLysProPheLysPheAspLeuAspAla-668 |
| SEQ. ID. NO. 4669 | 670-GlyGlyIleAsnArgGluLeuThrArgTrpLysGly-681 |
| SEQ. ID. NO. 4670 | 704-AlaGlyAlaGluArgValAla-710 |
| SEQ. ID. NO. 4671 | 729-SerTrpAspLysLysThrGlyIleSerAlaLysGlyGlyAla-742 |
| SEQ. ID. NO. 4672 | 783-SerArgGlnSerGly-787 |
| SEQ. ID. NO. 4673 | 806-ThrArgPheGlnAsnAspArgIle-813 |
| SEQ. ID. NO. 4674 | 819-GlyGlyAlaArgPheGlyArgIleAsnAla-828 |
| SEQ. ID. NO. 4675 | 1001-LeuLysPheArgHisGluGlyThrAlaGluLeu-1011 |
| SEQ. ID. NO. 4676 | 1015-ValGlyMetGluAsnSerGlyProAspValAspIle-1026 |
| SEQ. ID. NO. 4677 | 1031-AspLysTyrArgIleLeuSerArgProAsnArgArgLeuThr-1044 |
| SEQ. ID. NO. 4678 | 1049-ThrArgLeuArgTyrSerPro-1055 |

TABLE 1-continued

| | |
|---|---|
| SEQ. ID. NO. 4679 | 1065-IleLysThrAspGln-1069 |
| SEQ. ID. NO. 4680 | 1075-GlnLysSerSerMet-1079 |
| SEQ. ID. NO. 4681 | 1081-SerValGlyAspAsp-1085 |
| SEQ. ID. NO. 4682 | 1091-GluValLysLysGluAlaAla-1097 |
| SEQ. ID. NO. 4683 | 1109-AspLeuAsnAspGlyIleArg-1115 |
| SEQ. ID. NO. 4684 | 1146-ArgValIleLysGlyArgTyrLysAlaTyrGlyGlnAspLeuAspIleThrLys-1163 |
| SEQ. ID. NO. 4685 | 1179-IleArgAlaGluArgArgLeuSer-1186 |
| SEQ. ID. NO. 4686 | 1209-GluProMetSerGluLysAspLysLeu-1217 |
| SEQ. ID. NO. 4687 | 1225-AlaGlySerGlySerSerGlyAspAsnAlaAla-1235 |
| SEQ. ID. NO. 4688 | 1248-IleAsnAspArgIleGlyLeu-1254 |
| SEQ. ID. NO. 4689 | 1259-GlyPheThrSerLysArgSerArgAsnAlaGlnThrGlyGluLeuAsnPro-1275 |
| SEQ. ID. NO. 4690 | 1300-SerAlaGluGlnSerVal-1305 |
| SEQ. ID. NO. 4691 | 1321-IleGlySerArgSerSerGlyGly-1328 |
| SEQ. ID. NO. 4692 | 1335-ArgPheAspArgPheSerGlySerAspLysLysAspSerAlaGlyAsnGlyLysGlyLys-1354 |
| 286 | |
| AMPHI Regions - AMPHI | |
| SEQ. ID. NO. 4693 | 69-GluIleLysAspMetVal-74 |
| SEQ. ID. NO. 4694 | 102-ProAspAsnValLysThr-107 |
| SEQ. ID. NO. 4695 | 145-ValAlaIleLeuGlyAsp-150 |
| SEQ. ID. NO. 4696 | 157-LeuAlaGluTyrTyrArgAsnAlaLeuGluAsnTrpGlnGlnProValGlySer-174 |
| SEQ. ID. NO. 4697 | 198-ProLeuAlaLysLeuGlyAsnThr-205 |
| SEQ. ID. NO. 4698 | 238-ThrGlnArgTyrProGluGlnIleValSerGlyLeuAlaArgPhe-252 |
| SEQ. ID. NO. 4699 | 326-AspTyrTyrAsnLeuPheAsnLys-333 |
| SEQ. ID. NO. 4700 | 354-IleSerGlnProArg-358 |
| SEQ. ID. NO. 4701 | 375-ThrThrGlnAsnLeu-379 |
| SEQ. ID. NO. 4702 | 428-ThrAlaSerTrpLysArgGlnLeuLeu-436 |
| SEQ. ID. NO. 4703 | 455-ThrLeuGlyThrPheLeu-460 |
| SEQ. ID. NO. 4704 | 513-GlyAlaSerSerVal-517 |
| SEQ. ID. NO. 4705 | 555-LeuSerGlyAlaValPheHisAspMetGlyAspAlaAlaAlaAsn-569 |
| SEQ. ID. NO. 4706 | 584-ArgTrpPheSerProLeu-589 |
| Antigenic Index - Jameson-Wolf | |
| SEQ. ID. NO. 4707 | 1-MetHisAspThrArgThrMetMet-8 |
| SEQ. ID. NO. 4708 | 30-AlaAspLeuSerGluAsnLysAla-37 |
| SEQ. ID. NO. 4709 | 43-PheLysAsnLysSerProAspThrGluSerValLysLeuLysProLysPheProVal-61 |
| SEQ. ID. NO. 4710 | 64-AspThrGlnAspSerGluIleLysAspMetValGluGluHisLeu-78 |
| SEQ. ID. NO. 4711 | 83-GlnGlnGlnGluGluValLeuAspLysGluGlnThr-94 |
| SEQ. ID. NO. 4712 | 97-LeuAlaGluGluAlaProAspAsnValLysThrMetLeuArgSerLysGlyTyrPheSerSerLysValSerLeuThrGluLysAspGlyAla-127 |
| SEQ. ID. NO. 4713 | 133-ThrProGlyProArgThrLysIle-140 |
| SEQ. ID. NO. 4714 | 151-IleLeuSerAspGlyAsnLeuAlaGluTyrTyrArgAsnAlaLeuGluAsnTrpGln-169 |
| SEQ. ID. NO. 4715 | 172-ValGlySerAspPheAspGlnAspSerTrpGluAsnSerLysThrSerVal-188 |
| SEQ. ID. NO. 4716 | 192-ValThrArgLysAlaTyrPro-198 |
| SEQ. ID. NO. 4717 | 208-AlaValAsnProAspThrAlaThr-215 |
| SEQ. ID. NO. 4718 | 223-AspSerGlyArgProIleAla-229 |
| SEQ. ID. NO. 4719 | 234-GluIleThrGlyThrGlnArgTyrProGluGlnIle-245 |
| SEQ. ID. NO. 4720 | 252-PheGlnProGlyMetProTyrAspLeu-260 |
| SEQ. ID. NO. 4721 | 270-LeuGluGlnAsnGlyHisTyrSerGly-278 |
| SEQ. ID. NO. 4722 | 283-AlaAspPheAspArgLeuGlnGlyAspArgValProVal-295 |
| SEQ. ID. NO. 4723 | 298-SerValThrGluValLysArgHisLysLeuGluThrGlyIleArgLeuAspSerGluTyrGlyLeuGlyGly-321 |
| SEQ. ID. NO. 4724 | 342-AspMetAspLysTyrGluThr-348 |
| SEQ. ID. NO. 4725 | 355-SerGlnProArgAsnTyrArgGlyAsnTyrTrp-365 |
| SEQ. ID. NO. 4726 | 368-AsnValSerTyrAsnArgSerThrThrGlnAsnLeuGluLysArgAlaPheSerGlyGly-387 |
| SEQ. ID. NO. 4727 | 390-TyrValArgAspArgAlaGlyIleAspAlaArgLeuGly-402 |
| SEQ. ID. NO. 4728 | 405-PheLeuAlaGlyGlyArgLysIleProGlySerAla-416 |
| SEQ. ID. NO. 4729 | 430-SerTrpLysArgGlnLeu-435 |
| SEQ. ID. NO. 4730 | 441-HisProGluAsnGlyHisTyrLeuAspGlyLysIle-452 |
| SEQ. ID. NO. 4731 | 468-ThrSerAlaArgAlaGly-473 |
| SEQ. ID. NO. 4732 | 476-PheThrProGluAsnLysLysLeu-483 |
| SEQ. ID. NO. 4733 | 496-ValAlaArgAspAsnAlaAspValProSer-505 |
| SEQ. ID. NO. 4734 | 509-PheArgSerGlyGlyAlaSerSerValArgGlyTyrGluLeuAspSer-524 |
| SEQ. ID. NO. 4735 | 534-ValLeuProGluArgAlaLeu-540 |
| SEQ. ID. NO. 4736 | 562-AspMetGlyAspAla-566 |
| SEQ. ID. NO. 4737 | 568-AlaAsnPheLysArgMetLysLeuLysHisGlySerGlyLeu-581 |
| SEQ. ID. NO. 4738 | 598-TyrGlyHisSerAspLysLysIleArg-606 |
| Hydrophilic Regions - Hopp-Woods | |
| SEQ. ID. NO. 4739 | 1-MetHisAspThrArgThrMetMet-8 |
| SEQ. ID. NO. 4740 | 30-AlaAspLeuSerGluAsnLysAla-37 |
| SEQ. ID. NO. 4741 | 44-LysAsnLysSerProAspThrGluSerValLysLeuLysProLysPhe-59 |
| SEQ. ID. NO. 4742 | 64-AspThrGlnAspSerGluIleLysAspMetValGluGluHisLeu-78 |
| SEQ. ID. NO. 4743 | 84-GlnGlnGluGluValLeuAspLysGluGlnThr-94 |
| SEQ. ID. NO. 4744 | 97-LeuAlaGluGluAlaProAspAsnValLysThrMetLeuArgSer-111 |
| SEQ. ID. NO. 4745 | 119-ValSerLeuThrGluLysAspGlyAla-127 |
| SEQ. ID. NO. 4746 | 134-ProGlyProArgThrLysIle-140 |
| SEQ. ID. NO. 4747 | 174-SerAspPheAspGlnAspSerTrpGluAsnSerLysThr-186 |
| SEQ. ID. NO. 4748 | 192-ValThrArgLysAlaTyrPro-198 |
| SEQ. ID. NO. 4749 | 209-ValAsnProAspThrAlaThr-215 |
| SEQ. ID. NO. 4750 | 239-GlnArgTyrProGlu-243 |
| SEQ. ID. NO. 4751 | 283-AlaAspPheAspArgLeuGlnGlyAspArgValProVal-295 |
| SEQ. ID. NO. 4752 | 298-SerValThrGluValLysArgHisLysLeuGluThrGlyIleArgLeuAspSerGluTyr-317 |
| SEQ. ID. NO. 4753 | 342-AspMetAspLysTyrGluThr-348 |
| SEQ. ID. NO. 4754 | 373-ArgSerThrThrGlnAsnLeuGluLysArgAlaPhe-384 |

TABLE 1-continued

| | |
|---|---|
| SEQ. ID. NO. 4755 | 391-ValArgAspArgAla395GlyIleAspAlaArgLeuGly-402 |
| SEQ. ID. NO. 4756 | 405-PheLeuAlaGluGlyArgLysIlePro-413 |
| SEQ. ID. NO. 4757 | 478-ProGluAsnLysLysLeu-483 |
| SEQ. ID. NO. 4758 | 496-ValAlaArgAspAsnAlaAspVal-503 |
| SEQ. ID. NO. 4759 | 518-ArgGlyTyrGluLeuAspSer-524 |
| SEQ. ID. NO. 4760 | 534-ValLeuProGluArgAlaLeu-540 |
| SEQ. ID. NO. 4761 | 562-AspMetGlyAspAla-566 |
| SEQ. ID. NO. 4762 | 568-AlaAsnPheLysArgMetLysLeuLysHis-577 |
| SEQ. ID. NO. 4763 | 600-HisSerAspLysLysIleArg-606 |
| 287 | |
| AMPHI Regions - AMPHI | |
| SEQ. ID. NO. 4764 | 29-LysSerAlaAspThrLeuSerLysProAlaAla-39 |
| SEQ. ID. NO. 4765 | 68-GlySerGlnAspMet-72 |
| SEQ. ID. NO. 4766 | 131-AlaThrAspAlaGlyGluSerSerGlnProAlaAsnGlnProAspMetAlaAsnAlaAlaAspGlyMet-153 |
| SEQ. ID. NO. 4767 | 164-AsnAlaGlyAsnThrAlaAlaGlnGlyAlaAsnGlnAlaGly-177 |
| SEQ. ID. NO. 4768 | 246-PheGluLysLeuSerAspAlaAspLysIleSerAsnTyrLys-259 |
| SEQ. ID. NO. 4769 | 291-ProThrSerPheAlaArgPheArgArgSerAlaArg-302 |
| SEQ. ID. NO. 4770 | 410-LysSerValAspGlyIleIleAspSer-418 |
| SEQ. ID. NO. 4771 | 437-GlyPheLysGlyThrTrpThr-443 |
| SEQ. ID. NO. 4772 | 450-ValSerGlyLysPheTyr-455 |
| Antigenic Index - Jameson-Wolf | |
| SEQ. ID. NO. 4773 | 18-CysGlyGlyGlyGlyGlyGlySerProAspValLysSerAlaAspThrLeuSerLysProAla-38 |
| SEQ. ID. NO. 4774 | 42-ValSerGluLysGluThrGluAlaLysGluAspAlaProGlnAlaGlySerGlnGlyGlnGlyAlaProSerAlaGlnGlySerGlnAspMet-72 |
| SEQ. ID. NO. 4775 | 74-AlaValSerGluGluAsnThrGlyAsnGlyGlyAlaValThrAlaAspAsnProLysAsnGluAspGluValAlaGlnAsnAspMetProGlnAsnAla
AlaGlyThrAspSerSerThrProAsnHisThrProAspProAsnMet-122 |
| SEQ. ID. NO. 4776 | 126-AsnMetGluAsnGlnAlaThrAspAlaGlyGluSerSerGlnProAlaAsnGlnProAspMetAlaAsnAlaAlaAspGlyMetGlnGlyAspAspPro
SerAlaGlyGlyGlnAsnAlaGlyAsnThrAlaAlaGlnGlyAlaAsnGlnAlaGlyAsnAsnGlnAlaAlaGlySerSerAspProIleProAlaSerAsnPro
AlaProAlaAsnGlyGlySerAsnPheGlyArgValAspLeuAlaAsn-209 |
| SEQ. ID. NO. 4777 | 214-AspGlyProSerGlnAsn-219 |
| SEQ. ID. NO. 4778 | 223-ThrHisCysLysGlyAspSerCysSerGlyAsnAsnPheLeuAspGluGluValGlnLeuLysSerGluPheGluLysLeuSerAspAlaAspLysIle
SerAsnTyrLysLysAspGlyLysAsnAspLysPhe-267 |
| SEQ. ID. NO. 4779 | 287-TyrLysProLysProThrSerPheAlaArgPheArgArgSerAlaArgSerArgArgSerLeuProAla-309 |
| SEQ. ID. NO. 4780 | 321-ThrLeuIleValAspGlyGluAla-328 |
| SEQ. ID. NO. 4781 | 340-AlaProGluGlyAsnTyrArgTyrLeu-348 |
| SEQ. ID. NO. 4782 | 351-GlyAlaGluLysLeuProGlyGlySerTyr-360 |
| SEQ. ID. NO. 4783 | 364-ValGlnGlyGluProAlaLysGlyGluMet-373 |
| SEQ. ID. NO. 4784 | 388-HisThrGluAsnGlyArgProTyrProThrArgGlyArgPheAlaAla-403 |
| SEQ. ID. NO. 4785 | 405-ValAspPheGlySerLysSerValAspGlyIleIleAspSerGlyAspAspLeuHisMetGlyThrGlnLysPheLysAlaAlaIleAspGlyAsnGly
PheLysGlyThrTrpThrGluAsnGlySerGlyAspValSerGly-452 |
| SEQ. ID. NO. 4786 | 454-PheTyrGlyProAlaGlyGluGluValAlaGlyLysTyrSerTyrArgProThrAspAlaGluLysGlyGlyPhe-478 |
| SEQ. ID. NO. 4787 | 482-AlaGlyLysLysGluGlnAsp-488 |
| Hydrophilic Regions - Hopp-Woods | |
| SEQ. ID. NO. 4788 | 22-GlyGlyGlySerProAspValLysSerAlaAspThrLeuSerLysProAla-38 |
| SEQ. ID. NO. 4789 | 42-ValSerGluLysGluThrGluAlaLysGluAspAlaProGln-55 |
| SEQ. ID. NO. 4790 | 57-GlySerGlnGlyGlnGly-62 |
| SEQ. ID. NO. 4791 | 67-GlnGlySerGlnAsp-71 |
| SEQ. ID. NO. 4792 | 74-AlaValSerGluGluAsnThrGly-81 |
| SEQ. ID. NO. 4793 | 86-ValThrAlaAspAsnProLysAsnGluAspGluValAlaGlnAsnAspMetProGln-104 |
| SEQ. ID. NO. 4794 | 107-AlaGlyThrAspSerSerThr-113 |
| SEQ. ID. NO. 4795 | 127-MetGluAsnGlnAlaThrAspAlaGlyGluSerSerGlnProAlaAsnGlnProAspMetAlaAsnAlaAlaAspGlyMetGlnGlyAspAspProSer
AlaGly-161 |
| SEQ. ID. NO. 4796 | 182-AlaGlySerSerAspProIlePro-189 |
| SEQ. ID. NO. 4797 | 225-CysLysGlyAspSerCysSer-231 |
| SEQ. ID. NO. 4798 | 235-PheLeuAspGluGluValGlnLeuLysSerGluPheGluLysLeuSerAspAlaAspLysIleSerAsnTyrLysLysAspGlyLysAsnAspLysPhe-
267 |
| SEQ. ID. NO. 4799 | 295-AlaArgPheArgArgSerAlaArgSerArgArgSerLeuPro-308 |
| SEQ. ID. NO. 4800 | 322-LeuIleValAspGlyGluAla-328 |
| SEQ. ID. NO. 4801 | 351-GlyAlaGluLysLeuPro-356 |
| SEQ. ID. NO. 4802 | 364-ValGlnGlyGluProAlaLysGlyGluMet-373 |
| SEQ. ID. NO. 4803 | 390-GluAsnGlyArgProTyrProThrArgGlyArgPheAlaAla-403 |
| SEQ. ID. NO. 4804 | 405-ValAspPheGlySerLysSerValAspGlyIleIleAspSerGlyAspAspLeuHis-423 |
| SEQ. ID. NO. 4805 | 427-GlnLysPheLysAlaAlaIleAsp-434 |
| SEQ. ID. NO. 4806 | 446-GlySerGlyAspValSerGly-452 |
| SEQ. ID. NO. 4807 | 458-AlaGlyGluGluValAlaGly-464 |
| SEQ. ID. NO. 4808 | 466-TyrSerTyrArgProThrAspAlaGluLysGlyGly-477 |
| SEQ. ID. NO. 4809 | 482-AlaGlyLysLysGluGlnAsp-488 |
| 288 | |
| AMPHI Regions - AMPHI | |
| SEQ. ID. NO. 4810 | 7-ValSerArgValLeu-11 |
| SEQ. ID. NO. 4811 | 54-IleValThrLysCysAla-59 |
| SEQ. ID. NO. 4812 | 61-ArgProTyrArgThrPheSerProLeuProVal-71 |
| SEQ. ID. NO. 4813 | 97-HisSerThrLeuArg-101 |
| SEQ. ID. NO. 4814 | 150-AlaLeuPheGlnAlaGlyPheAsp-157 |
| Antigenic Index - Jameson-Wolf | |
| SEQ. ID. NO. 4815 | 2-HisThrGlyGlnAla-6 |
| SEQ. ID. NO. 4816 | 28-AsnLeuProGluArgSerAlaGlySer-36 |
| SEQ. ID. NO. 4817 | 58-CysAlaValArgProTyrArgThrPheSerPro-68 |
| SEQ. ID. NO. 4818 | 72-LeuProLysGlnProSerAla-78 |
| SEQ. ID. NO. 4819 | 89-LeuProArgProAlaValAsnArgHisSerThrLeuArgSerProAspPheProProArgMet-109 |
| SEQ. ID. NO. 4820 | 113-IleArgGlyAspCysLeuPro-119 |

TABLE 1-continued

| | |
|---|---|
| SEQ. ID. NO. 4821 | 126-IleIleThrArgAsnThrLysMetProSerGluThrValGlnValSerAspGlyIleGlnProLys-147 |
| SEQ. ID. NO. 4822 | 155-GlyPheAspGluAlaVal-160 |

Hydrophilic Regions - Hopp-Woods

| | |
|---|---|
| SEQ. ID. NO. 4823 | 28-AsnLeuProGluArgSerAla-34 |
| SEQ. ID. NO. 4824 | 58-CysAlaValArgPro-62 |
| SEQ. ID. NO. 4825 | 98-SerThrLeuArgSerProAspPheProPro-107 |
| SEQ. ID. NO. 4826 | 113-IleArgGlyAspCys-117 |
| SEQ. ID. NO. 4827 | 126-IleIleThrArgAsnThrLysMetProSerGluThrValGlnVal-140 |
| SEQ. ID. NO. 4828 | 155-GlyPheAspGluAlaVal-160 |

292
AMPHI Regions - AMPHI

| | |
|---|---|
| SEQ. ID. NO. 4829 | 7-LysIleLeuThrProPheThrValLeuProLeu-17 |
| SEQ. ID. NO. 4830 | 40-GlyLysSerValAla-44 |
| SEQ. ID. NO. 4831 | 62-ValLeuSerValSerGlu-67 |
| SEQ. ID. NO. 4832 | 69-ProValLysGlyIleTyrGlu-75 |
| SEQ. ID. NO. 4833 | 110-GluArgAlaAlaAspLeu-115 |
| SEQ. ID. NO. 4834 | 124-ProLeuAspLysAlaIleLysGluValArgGly-134 |
| SEQ. ID. NO. 4835 | 150-PheCysLysArgLeuGluHisGluPheGluLysMetThrAspValThr-165 |
| SEQ. ID. NO. 4836 | 195-LysAlaTrpThrAspTrpMetArg-202 |
| SEQ. ID. NO. 4837 | 212-IleCysAspAsnProVal-217 |

Antigenic Index - Jameson-Wolf

| | |
|---|---|
| SEQ. ID. NO. 4838 | 1-MetLysThrLysLeu-5 |
| SEQ. ID. NO. 4839 | 23-ThrProValSerAsnAlaAsnAlaGluProAlaValLysAlaGluSerAlaGlyLysSerVal-43 |
| SEQ. ID. NO. 4840 | 47-LeuLysAlaArgLeuGluLysThrTyrSerAlaGlnAspLeuLys-61 |
| SEQ. ID. NO. 4841 | 66-SerGluThrProValLysGlyIle-73 |
| SEQ. ID. NO. 4842 | 85-TyrThrAspAlaGluGlyGlyTyr-92 |
| SEQ. ID. NO. 4843 | 99-IleAsnIleAspThrArgLysAsnLeuThrGluGluArgAlaAlaAspLeuAsnLys-117 |
| SEQ. ID. NO. 4844 | 124-ProLeuAspLysAlaIleLysGluValArgGlyAsnGlyLysLeuLysVal-140 |
| SEQ. ID. NO. 4845 | 142-ValPheSerAspProAspCysProPhe-150 |
| SEQ. ID. NO. 4846 | 152-LysArgLeuGluHisGluPheGluLysMetThrAsp-163 |
| SEQ. ID. NO. 4847 | 177-HisProAspAlaAlaArgLysAla-184 |
| SEQ. ID. NO. 4848 | 189-CysGlnProAspArgAlaLysAla-196 |
| SEQ. ID. NO. 4849 | 200-TrpMetArgLysGlyLysPheProVal-208 |
| SEQ. ID. NO. 4850 | 210-GlySerIleCysAspAsnProValAlaGluThrThrSerLeuGlyGlu-225 |
| SEQ. ID. NO. 4851 | 237-PheProAsnGlyArgSerGlnSerGlyTyrSerPro-248 |
| SEQ. ID. NO. 4852 | 250-ProGlnLeuGluGluIleIleArgLysAsnGln-260 |

Hydrophilic Regions - Hopp-Woods

| | |
|---|---|
| SEQ. ID. NO. 4853 | 1-MetLysThrLysLeu-5 |
| SEQ. ID. NO. 4854 | 28-AlaAsnAlaGluProAlaValLysAlaGluSerAlaGlyLysSerVal-43 |
| SEQ. ID. NO. 4855 | 47-LeuLysAlaArgLeuGluLysThrTyrSer-56 |
| SEQ. ID. NO. 4856 | 99-IleAsnIleAspThrArgLysAsnLeuThrGluGluArgAlaAlaAspLeuAsnLys-117 |
| SEQ. ID. NO. 4857 | 124-ProLeuAspLysAlaIleLysGluValArgGlyAsnGlyLysLeuLys-139 |
| SEQ. ID. NO. 4858 | 144-SerAspProAspCysProPhe-150 |
| SEQ. ID. NO. 4859 | 152-LysArgLeuGluHisGluPheGluLysMetThrAsp-163 |
| SEQ. ID. NO. 4860 | 179-AspAlaAlaArgLysAla-184 |
| SEQ. ID. NO. 4861 | 190-GlnProAspArgAlaLysAla-196 |
| SEQ. ID. NO. 4862 | 200-TrpMetArgLysGlyLysPhe-206 |
| SEQ. ID. NO. 4863 | 240-GlyArgSerGlnSer-244 |
| SEQ. ID. NO. 4864 | 250-ProGlnLeuGluGluIleIleArgLysAsnGln-260 |

294
AMPHI Regions - AMPHI

| | |
|---|---|
| SEQ. ID. NO. 4865 | 27-ArgPheProAlaAlaPheArgArgTyrSerAla-37 |
| SEQ. ID. NO. 4866 | 45-LysProAlaAspThr-49 |
| SEQ. ID. NO. 4867 | 51-TrpHisArgValArgArgPheLysSerAsnArgArgMetArgGlyGlyLysProLeuLysLysProTyrArg-74 |
| SEQ. ID. NO. 4868 | 84-ArgAlaTrpThrAlaLeuSerHisAsnIleAlaGluArgAlaArgGluSerProArgArgCysGlyLysArgTyrAlaAspIleGlyGly-113 |
| SEQ. ID. NO. 4869 | 132-TyrAlaValAlaHisIleValHisLeu-140 |
| SEQ. ID. NO. 4870 | 165-ValSerArgGluAlaArgArgGluVal-173 |
| SEQ. ID. NO. 4871 | 176-AlaMetSerTyrArg-180 |
| SEQ. ID. NO. 4872 | 206-SerIleLeuGlyGluProPheAlaThrSerPheGly-217 |
| SEQ. ID. NO. 4873 | 227-AlaPheSerValLeuAlaHisPhe-234 |
| SEQ. ID. NO. 4874 | 247-ThrValGlyTrpSerLysTyrIleHisAlaVal-257 |

Antigenic Index - Jameson-Wolf

| | |
|---|---|
| SEQ. ID. NO. 4875 | 20-ValValArgThrSerSerAsnArgPhe-28 |
| SEQ. ID. NO. 4876 | 32-PheArgArgTyrSerAlaPhe-38 |
| SEQ. ID. NO. 4877 | 43-PheProLysProAlaAspThrProTrpHisArgValArgArgPheLysSerAsnArgArgMetArgGlyGlyLysProLeuLysLysProTyrArgProArgGlyGlyGlyCysArgCysArgArgAla-85 |
| SEQ. ID. NO. 4878 | 93-IleAlaGluArgAlaArgGluSerProArgArgCysGlyLysArgTyrAlaAspIleGlyGlyAspSerAspThrIleArgIleArgValPheArgLeuGluHisArgMet-129 |
| SEQ. ID. NO. 4879 | 161-HisThrGlyArgValSerArgGluAlaArgArgGluValGluLysAlaMetSer-178 |
| SEQ. ID. NO. 4880 | 240-LysMetAlaArgSer-244 |

Hydrophilic Regions - Hopp-Woods

| | |
|---|---|
| SEQ. ID. NO. 4881 | 20-ValValArgThrSerSerAsnArg-27 |
| SEQ. ID. NO. 4882 | 50-ProTrpHisArgValArgArgPheLysSerAsnArgArgMetArgGlyGlyLysProLeuLysLysProTyrArgProArgGlyGlyGlyCysArgCysArgArgAla-85 |
| SEQ. ID. NO. 4883 | 93-IleAlaGluArgAlaArgGluSerProArgArgCysGlyLysArgTyrAlaAspIleGlyGlyAspSerAspThrIleArg-119 |
| SEQ. ID. NO. 4884 | 121-ArgValPheArgLeuGluHisArgMet-129 |
| SEQ. ID. NO. 4885 | 164-ArgValSerArgGluAlaArgArgGluValGluLysAlaMetSer-178 |

295
AMPHI Regions - AMPHI

| | |
|---|---|
| SEQ. ID. NO. 4886 | 79-PheArgGlnProArgArgIle-85 |

TABLE 1-continued

| | |
|---|---|
| SEQ. ID. NO. 4887 | 111-ValGlnArgPhePheArgGlnPro-118 |
| SEQ. ID. NO. 4888 | 163-ValIleArgLysIleAlaAlaLeu-170 |
| SEQ. ID. NO. 4889 | 189-HisGlnGlnArgArgIleGlyLysThr-197 |
| SEQ. ID. NO. 4890 | 240-IleCysArgGlyThrSerGly-246 |
| SEQ. ID. NO. 4891 | 263-TyrIleIleLysProLeuGluHis-270 |
| Antigenic Index - Jameson-Wolf | |
| SEQ. ID. NO. 4892 | 4-MetAlaArgHisAspAspGlnGlnArg-12 |
| SEQ. ID. NO. 4893 | 18-LeuProArgArgGlnGln-23 |
| SEQ. ID. NO. 4894 | 36-AlaAlaAlaHisGlyAsnArgProAlaSerAspAlaPhePheLysLeuProArgGlnArgPheHisLeu-58 |
| SEQ. ID. NO. 4895 | 73-HisGlyCysArgAlaGlnPheArgGlnProArgArgIleArgLeu-87 |
| SEQ. ID. NO. 4896 | 89-LeuArgGlnThrProArgGlnArgSerGlyGlyArgThrAspGlnAlaAla-105 |
| SEQ. ID. NO. 4897 | 115-PheArgGlnProArgIleArgGlnLysGlnArgHisThrArgAlaProAla-131 |
| SEQ. ID. NO. 4898 | 136-ValGlyProAspPheGly-141 |
| SEQ. ID. NO. 4899 | 144-GlnAsnAlaGluHisArgAla-150 |
| SEQ. ID. NO. 4900 | 171-ArgIleGlyLysGlnAsnLeuArgGlyPheProProArgArgGlyHisLeuArgHisGlnGlnArgArgIleGlyLysThrProProGlnLeuAla-202 |
| SEQ. ID. NO. 4901 | 207-GlyGlyThrArgPheSerAspArgAsnGlyValTyrProAsnArgAlaGlyAsnGlyIleArgIleArgLeu-230 |
| SEQ. ID. NO. 4902 | 239-ProIleCysArgGlyThrSerGly-246 |
| SEQ. ID. NO. 4903 | 253-ProTyrProTyrArgArgLysGlnProGlnTyr-263 |
| SEQ. ID. NO. 4904 | 273-IleSerCysLysThrAsnAla-279 |
| SEQ. ID. NO. 4905 | 287-PheArgGlnArgAsnGlnIleSer-294 |
| Hydrophilic Regions - Hopp-Woods | |
| SEQ. ID. NO. 4906 | 5-AlaArgHisAspAspGlnGlnArg-12 |
| SEQ. ID. NO. 4907 | 18-LeuProArgArgGlnGln-23 |
| SEQ. ID. NO. 4908 | 36-AlaAlaAlaHisGlyAsnArgProAlaSer-45 |
| SEQ. ID. NO. 4909 | 77-AlaGlnPheArgGlnProArgArgIleArgLeu-87 |
| SEQ. ID. NO. 4910 | 91-GlnThrProArgGlnArgSerGlyGlyArgThrAspGlnAlaAla-105 |
| SEQ. ID. NO. 4911 | 118-ProArgIleArgGlnLysGlnArgHisThrArg-128 |
| SEQ. ID. NO. 4912 | 146-AlaGluHisArgAla-150 |
| SEQ. ID. NO. 4913 | 171-ArgIleGlyLysGlnAsnLeu-177 |
| SEQ. ID. NO. 4914 | 180-PheProProArgArgGlyHisLeuArgHisGlnGlnArgArgIleGlyLysThrProPro-199 |
| SEQ. ID. NO. 4915 | 210-ArgPheSerAspArgAsnGly-216 |
| SEQ. ID. NO. 4916 | 226-IleArgIleArgLeu-230 |
| SEQ. ID. NO. 4917 | 239-ProIleCysArgGlyThr-244 |
| SEQ. ID. NO. 4918 | 255-ProTyrArgArgLysGlnPro-261 |
| SEQ. ID. NO. 4919 | 287-PheArgGlnArgAsnGlnIle-293 |
| 297 | |
| AMPHI Regions - AMPHI | |
| SEQ. ID. NO. 4920 | 35-ArgThrGluArgVal-39 |
| SEQ. ID. NO. 4921 | 69-GlnProGlyAspSerLeuAlaAspValLeuAla-79 |
| SEQ. ID. NO. 4922 | 86-AspGluIleAlaArgIleThrGluLysTyr-95 |
| SEQ. ID. NO. 4923 | 157-LeuProThrLeuArg-161 |
| SEQ. ID. NO. 4924 | 199-LeuLysGluGlyAspAla-204 |
| SEQ. ID. NO. 4925 | 272-LeuValTyrThrArgIleSerSer-279 |
| SEQ. ID. NO. 4926 | 333-HisAlaAsnGlyValGluThrLeuTyrAlaHisLeuSerAlaPheSer-348 |
| Antigenic Index - Jameson-Wolf | |
| SEQ. ID. NO. 4927 | 8-AlaLysHisArgLysTyrAla-14 |
| SEQ. ID. NO. 4928 | 32-SerThrGluArgThrGluArgValArgProGlnArgValGluGlnAsnLeuProProLeuSerTrpGlyGlySerGly-57 |
| SEQ. ID. NO. 4929 | 67-AlaValGlnProGlyAspSerLeuAla-75 |
| SEQ. ID. NO. 4930 | 78-LeuAlaArgSerGlyMetAlaArgAspGluIleAlaArgIleThrGluLysTyrGlyGlyGluAlaAspLeuArgHisLeuArgAlaAspGlnSerVal-110 |
| SEQ. ID. NO. 4931 | 115-GlyGlyAspGlyGlyAlaArgGluVal-123 |
| SEQ. ID. NO. 4932 | 127-ThrAspGluAspGlyGluArgAsnLeuValAlaLeuGluLysLysGlyGlyIleTrpArgArgSerAlaSerGluAlaAspMetLysVal-156 |
| SEQ. ID. NO. 4933 | 167-ThrSerAlaArgGlySerLeuAlaArgAlaGluValProValGluIleArgGluSerLeuSer-187 |
| SEQ. ID. NO. 4934 | 194-PheSerLeuAspGlyLeuLysGlyGlyAspAlaVal-205 |
| SEQ. ID. NO. 4935 | 228-GluValValLysGlyGlyThrArgHis-236 |
| SEQ. ID. NO. 4936 | 240-TyrTyrArgSerAspLysGluGlyGlyGlyGlyGlyAsnTyrTyrAspGluAspGlyLysValLeuGlnGluLysGlyGlyPheAsn-268 |
| SEQ. ID. NO. 4937 | 276-ArgIleSerSerProPheGlyTyr-283 |
| SEQ. ID. NO. 4938 | 295-HisThrGlyIleAspTyrAla-301 |
| SEQ. ID. NO. 4939 | 303-ProGlnGlyThrProValArgAlaSerAlaAspGly-314 |
| SEQ. ID. NO. 4940 | 318-PheLysGlyArgLysGlyGlyTyrGly-326 |
| SEQ. ID. NO. 4941 | 333-HisAlaAsnGlyValGlu-338 |
| SEQ. ID. NO. 4942 | 350-AlaGluGlyAsnValArgGlyGlyGlu-358 |
| SEQ. ID. NO. 4943 | 365-SerThrGlyArgSerThrGlyProHisLeu-374 |
| SEQ. ID. NO. 4944 | 376-TyrGluAlaArgIleAsnGlyGlnProValAsn-386 |
| SEQ. ID. NO. 4945 | 393-ProThrProGluLeuThrGlnAlaAspLysAlaAla-404 |
| SEQ. ID. NO. 4946 | 408-GlnLysGlnLysAlaAspAlaLeu-415 |
| SEQ. ID. NO. 4947 | 426-ValSerGlnSerAsp-430 |
| Hydrophilic Regions - Hopp-Woods | |
| SEQ. ID. NO. 4948 | 8-AlaLysHisArgLysTyrAla-14 |
| SEQ. ID. NO. 4949 | 32-SerThrGluArgThrGluArgValArgProGlnArgValGluGlnAsn-47 |
| SEQ. ID. NO. 4950 | 68-ValGlnProGlyAspSerLeuAla-75 |
| SEQ. ID. NO. 4951 | 82-GlyMetAlaArgAspGluIleAlaArgIleThrGluLysTyrGlyGlyGluAlaAspLeuArgHisLeuArgAlaAspGln-108 |
| SEQ. ID. NO. 4952 | 117-AspGlyGlyAlaArgGlu-122 |
| SEQ. ID. NO. 4953 | 127-ThrAspGluAspGlyGluArgAsnLeuValAlaLeuGluLysLysGlyGlyIleTrpArgArgSerAlaSerGluAlaAspMetLysVal-156 |
| SEQ. ID. NO. 4954 | 167-ThrSerAlaArgGlySerLeuAlaArgAlaGluValProValGluIleArgGluSerLeu-186 |
| SEQ. ID. NO. 4955 | 194-PheSerLeuAspGlyLeuLysGlyGlyAspAlaVal-205 |
| SEQ. ID. NO. 4956 | 228-GluValValLysGlyGlyThrArg-235 |
| SEQ. ID. NO. 4957 | 242-ArgSerAspLysGluGlyGlyGlyGly-249 |
| SEQ. ID. NO. 4958 | 253-TyrTyrAspGluAspGlyLysValLeuGlnGluLysGlyGlyPhe-267 |
| SEQ. ID. NO. 4959 | 306-ThrProValArgAlaSerAla-312 |
| SEQ. ID. NO. 4960 | 319-LysGlyArgLysGlyGlyTyr-325 |

TABLE 1-continued

| | |
|---|---|
| SEQ. ID. NO. 4961 | 350-AlaGluGlyAsnValArgGlyGlyGlu-358 |
| SEQ. ID. NO. 4962 | 366-ThrGlyArgSerThrGly-371 |
| SEQ. ID. NO. 4963 | 378-AlaArgIleAsnGly-382 |
| SEQ. ID. NO. 4964 | 396-GluLeuThrGlnAlaAspLysAlaAla-404 |
| SEQ. ID. NO. 4965 | 408-GlnLysGlnLysAlaAspAlaLeu-415 |

298
AMPHI Regions - AMPHI

| | |
|---|---|
| SEQ. ID. NO. 4966 | 6-SerLeuPheSerSerIle-11 |
| SEQ. ID. NO. 4967 | 13-MetSerAlaLeuIleAla-18 |
| SEQ. ID. NO. 4968 | 26-IleAsnAlaTyrTrpGlnGln-32 |
| SEQ. ID. NO. 4969 | 42-ProLeuAlaAlaTyr-46 |
| SEQ. ID. NO. 4970 | 62-LeuSerAspGlyIleLysAlaPhe-69 |
| SEQ. ID. NO. 4971 | 82-GlySerAlaAspMetProSerGlu-89 |
| SEQ. ID. NO. 4972 | 126-LeuMetGlnGlyValAla-131 |
| SEQ. ID. NO. 4973 | 134-ValGlnLysSerLeuLys-139 |
| SEQ. ID. NO. 4974 | 157-SerTyrProSerPhePheAspTrpProLysThrIleGluGluThrLeuGlnLysHisProGluIleSer-179 |
| SEQ. ID. NO. 4975 | 188-AsnAspProTrpAspPhe-193 |
| SEQ. ID. NO. 4976 | 208-AlaGlnGluTyrLeuLysArgValAspArgIleLeuGlu-220 |
| SEQ. ID. NO. 4977 | 245-GlnMetArgTyrLeuAspLysLeuLeuSerGluHisLeu-257 |
| SEQ. ID. NO. 4978 | 276-ArgTyrThrAspSer-280 |
| SEQ. ID. NO. 4979 | 308-AlaLysIleMetGluLys-313 |

Antigenic Index - Jameson-Wolf

| | |
|---|---|
| SEQ. ID. NO. 4980 | 22-SerGlnAsnProIleAsnAlaTyr-29 |
| SEQ. ID. NO. 4981 | 34-TyrHisArgAsnSerProLeuGluPro-42 |
| SEQ. ID. NO. 4982 | 47-GlyTrpTrpArgSerGlyAlaAlaLeuGlnGlu-57 |
| SEQ. ID. NO. 4983 | 70-LeuSerGlyGluThrProProThrAlaGlnAspGlyGlySerAlaAspMetProSerGluAlaAlaAla-92 |
| SEQ. ID. NO. 4984 | 94-GluAlaValProGlnThrGlyGluThrGluTrpLysGlnAspThrGluAlaAlaAlaValArgSerGlyAspLysValPhe-120 |
| SEQ. ID. NO. 4985 | 136-LysSerLeuLysGlnGlnTyrGlyIleGluSerValAsnLeuSerLysGlnSerThrGly-155 |
| SEQ. ID. NO. 4986 | 162-PheAspTrpProLysThrIleGluGluThrLeuGlnLysHisProGlu-177 |
| SEQ. ID. NO. 4987 | 186-GlyProAsnAspProTrpAspPheProVal-195 |
| SEQ. ID. NO. 4988 | 203-AlaSerAspGluTrpAla-208 |
| SEQ. ID. NO. 4989 | 211-TyrLeuLysArgValAspArgIleLeuGlu-220 |
| SEQ. ID. NO. 4990 | 236-TyrMetLysLysAlaLysLeuAspGlyGlnMetArgTyrLeuAsp-250 |
| SEQ. ID. NO. 4991 | 252-LeuLeuSerGluHisLeuLysGly-259 |
| SEQ. ID. NO. 4992 | 270-LeuSerGlyGlyLysAspArgTyrThrAspSerValAsnValAsnGlyLysProValArgTyrArgSerLysAspGlyIle-296 |
| SEQ. ID. NO. 4993 | 318-ProSerThrGlnProSerSerThrGlnPro-327 |

Hydrophilic Regions - Hopp-Woods

| | |
|---|---|
| SEQ. ID. NO. 4994 | 73-GluThrProProThrAlaGlnAspGlyGlySerAlaAspMetProSerGluAlaAlaAla-92 |
| SEQ. ID. NO. 4995 | 94-GluAlaValProGlnThrGlyGluThrGluTrpLysGlnAspThrGluAlaAlaAlaValArgSerGlyAsp-117 |
| SEQ. ID. NO. 4996 | 148-AsnLeuSerLysGlnSerThr-154 |
| SEQ. ID. NO. 4997 | 166-LysThrIleGluGluThrLeuGlnLysHisProGlu-177 |
| SEQ. ID. NO. 4998 | 211-TyrLeuLysArgValAspArgIleLeuGlu-220 |
| SEQ. ID. NO. 4999 | 236-TyrMetLysLysAlaLysLeuAspGlyGlnMetArgTyrLeuAsp-250 |
| SEQ. ID. NO. 5000 | 252-LeuLeuSerGluHisLeuLysGly-259 |
| SEQ. ID. NO. 5001 | 271-SerGlyGlyLysAspArgTyrThrAsp-279 |
| SEQ. ID. NO. 5002 | 281-ValAsnValAsnGlyLysProValArgTyrArgSerLysAspGlyIle-296 |
| SEQ. ID. NO. 5003 | 319-SerThrGlnProSerSerThrGlnPro-327 |

299
AMPHI Regions - AMPHI

| | |
|---|---|
| SEQ. ID. NO. 5004 | 54-AlaSerProTrpMetLysLysLeuGlnSerValAlaGlnGlySer-68 |
| SEQ. ID. NO. 5005 | 71-ThrPheArgIleLeuGlnIleGly-78 |
| SEQ. ID. NO. 5006 | 85-AspPhePheThrAspSerLeuArgLysArgLeuGlnLysThrTrpGly-100 |
| SEQ. ID. NO. 5007 | 238-GlnLeuThrGlnTrpSerLysTrp-245 |
| SEQ. ID. NO. 5008 | 247-AlaAspArgMetAsnAspLeuAlaGlnThr-256 |
| SEQ. ID. NO. 5009 | 281-GluGlnLysTrpLeuAspThrValArgGlnIleArgAspSerLeu-295 |
| SEQ. ID. NO. 5010 | 307-GluSerLeuLysAsnThrLeu-313 |
| SEQ. ID. NO. 5011 | 322-ArgLeuThrGluValGlnGlnMetGlnArgArgValAlaArgGln-336 |
| SEQ. ID. NO. 5012 | 344-TrpGlnAsnAlaMetGly-349 |
| SEQ. ID. NO. 5013 | 374-GlyTyrArgArgAlaAlaGluMetLeuAlaAspSerLeuGluGluLeuValArgSerAlaAlaIleArg-396 |

Antigenic Index - Jameson-Wolf

| | |
|---|---|
| SEQ. ID. NO. 5014 | 1-MetAsnProLysHis-5 |
| SEQ. ID. NO. 5015 | 35-ProSerAlaProTyrThrAspThrAsnGlyLeu-45 |
| SEQ. ID. NO. 5016 | 48-AspTyrGlyAsnAlaSerAlaSerProTrpMetLysLysLeuGln-62 |
| SEQ. ID. NO. 5017 | 65-AlaGlnGlySerGlyGluThr-71 |
| SEQ. ID. NO. 5018 | 78-GlyAspSerHisThrAlaGlyAspPhePheThrAspSerLeuArgLysArgLeuGlnLysThrTrpGlyAspGlyGly-103 |
| SEQ. ID. NO. 5019 | 110-AlaAsnValLysGlyGlnArg-116 |
| SEQ. ID. NO. 5020 | 121-ArgHisAsnGlyAsnTrpGlnSerLeuThrSerArgAsnAsnThrGlyAspPheProLeu-140 |
| SEQ. ID. NO. 5021 | 157-AlaSerAspGlyIleAlaSerLysGlnArgVal-167 |
| SEQ. ID. NO. 5022 | 184-GlyAsnThrValSerAlaAsnGlyGlyGly-193 |
| SEQ. ID. NO. 5023 | 221-GluAsnProAlaGlyGly-226 |
| SEQ. ID. NO. 5024 | 241-GlnTrpSerLysTrpArgAlaAspArgMetAsnAspLeuAlaGlnThrGlyAla-258 |
| SEQ. ID. NO. 5025 | 266-GlyThrAsnGluAlaPheAsnAsnAsnIleAspIleAlaAspThrGluGlnLysTrp-284 |
| SEQ. ID. NO. 5026 | 286-AspThrValArgGlnIleArgAspSerLeuPro-296 |
| SEQ. ID. NO. 5027 | 305-AlaProGluSerLeuLysAsnThr-312 |
| SEQ. ID. NO. 5028 | 319-ArgProValArgLeuThrGluValGlnGlnMetGlnArgArgValAlaArgGlnGlyGlnThr-339 |
| SEQ. ID. NO. 5029 | 361-GlyTrpAlaAlaLysAspGlyVal-368 |
| SEQ. ID. NO. 5030 | 370-PheSerAlaLysGlyTyrArgArgAlaAlaGluMetLeuAlaAspSerLeuGluGluLeuValArg-391 |
| SEQ. ID. NO. 5031 | 393-AlaAlaIleArgGln-397 |

Hydrophilic Regions - Hopp-Woods

| | |
|---|---|
| SEQ. ID. NO. 5032 | 67-GlySerGlyGluThr-71 |

TABLE 1-continued

| | |
|---|---|
| SEQ. ID. NO. 5033 | 90-SerLeuArgLysArgLeuGlnLysThrTrpGly-100 |
| SEQ. ID. NO. 5034 | 112-ValLysGlyGlnArg-116 |
| SEQ. ID. NO. 5035 | 130-ThrSerArgAsnAsnThrGly-136 |
| SEQ. ID. NO. 5036 | 159-AspGlyIleAlaSerLysGlnArgVal-167 |
| SEQ. ID. NO. 5037 | 245-TrpArgAlaAspArgMetAsnAsp-252 |
| SEQ. ID. NO. 5038 | 276-AspIleAlaAspThrGluGlnLysTrp-284 |
| SEQ. ID. NO. 5039 | 288-ValArgGlnIleArgAspSerLeuPro-296 |
| SEQ. ID. NO. 5040 | 319-ArgProValArgLeuThrGlu-325 |
| SEQ. ID. NO. 5041 | 327-GlnGlnMetGlnArgArgValAlaArgGlnGly-337 |
| SEQ. ID. NO. 5042 | 363-AlaAlaLysAspGlyVal-368 |
| SEQ. ID. NO. 5043 | 373-LysGlyTyrArgArgAlaAlaGluMetLeuAlaAspSerLeuGluGluLeuValArg-391 |
| SEQ. ID. NO. 5044 | 393-AlaAlaIleArgGln-397 |

302-2
AMPHI Regions - AMPHI

| | |
|---|---|
| SEQ. ID. NO. 5045 | 20-AspGlyArgPheLeuArgThrValGluTrpLeuGlyAsnMetLeuProHisPro-37 |
| SEQ. ID. NO. 5046 | 85-LeuAsnAlaAspGlyPheIleLysIleLeuThrHisThrValLysAsnPheThrGlyPheAlaProLeuGlyThrValLeuValSerLeu-114 |
| SEQ. ID. NO. 5047 | 127-SerAlaLeuMetArg-131 |
| SEQ. ID. NO. 5048 | 176-GlyArgHisProLeuAlaGlyLeuAlaAlaAlaPheAlaGlyValSerGly-192 |
| SEQ. ID. NO. 5049 | 201-GlyThrIleAspProLeuLeuAlaGlyIleThrGlnGlnAla-214 |
| SEQ. ID. NO. 5050 | 239-ValIleAlaLeuIleGly-244 |
| SEQ. ID. NO. 5051 | 271-ArgHisSerAsnGluIle-276 |
| SEQ. ID. NO. 5052 | 294-LeuSerAlaLeuLeuAlaTrp-300 |
| SEQ. ID. NO. 5053 | 308-IleLeuArgHisProGluThrGly-315 |
| SEQ. ID. NO. 5054 | 341-TyrGlyArgValThrArgSerLeuArgGlyGluGlnGluValValAsnAlaMetAlaGluSerMetSer-363 |
| SEQ. ID. NO. 5055 | 378-PheValAlaPhePheAsnTrpThrAsnIleGlyGlnTyrIle-391 |
| SEQ. ID. NO. 5056 | 448-AlaProGluValIleGlnAlaAlaTyrArgIleGlyAspSerValThrAsnIleIleThrProMetMetSerTyrPheGlyLeuIleMetAla-478 |
| SEQ. ID. NO. 5057 | 505-IleAlaTrpIleAlaLeuPheCysIle-513 |

Antigenic Index - Jameson-Wolf

| | |
|---|---|
| SEQ. ID. NO. 5058 | 8-LysGluLysGlnMetSerGlnThrAspThrGlnArgAspGlyArgPhe-23 |
| SEQ. ID. NO. 5059 | 61-SerValProAspProArgProValGlyAlaLysGlyArgAlaAspAspGlyLeu-78 |
| SEQ. ID. NO. 5060 | 119-IleAlaGluLysSerGly-124 |
| SEQ. ID. NO. 5061 | 134-LeuThrLysSerProArgLysLeuThr-142 |
| SEQ. ID. NO. 5062 | 152-LeuSerAsnThrAlaSerGlu-158 |
| SEQ. ID. NO. 5063 | 175-LeuGlyArgHisProLeu-180 |
| SEQ. ID. NO. 5064 | 250-LysIleValGluProGlnLeuGlyProTyrGlnSerAspLeuSerGlnGluGluLysAspIleArgHisSerAsnGluIleThrProLeuGluTyrLys-282 |
| SEQ. ID. NO. 5065 | 304-ProAlaAspGlyIleLeuArgHisProGluThrGlyLeuValSer-318 |
| SEQ. ID. NO. 5066 | 343-ArgValThrArgSerLeuArgGlyGluGlnGluVal-354 |
| SEQ. ID. NO. 5067 | 402-ValGlyLeuGlyGly-406 |
| SEQ. ID. NO. 5068 | 482-LysTyrLysLysAspAlaGlyVal-489 |

Hydrophilic Regions - Hopp-Woods

| | |
|---|---|
| SEQ. ID. NO. 5069 | 8-LysGluLysGlnMetSerGlnThrAspThrGlnArgAspGlyArgPhe-23 |
| SEQ. ID. NO. 5070 | 63-ProAspProArgProValGlyAlaLysGlyArgAlaAspAsp-76 |
| SEQ. ID. NO. 5071 | 119-IleAlaGluLysSerGly-124 |
| SEQ. ID. NO. 5072 | 136-LysSerProArgLysLeu-141 |
| SEQ. ID. NO. 5073 | 263-LeuSerGlnGluGluLysAspIleArgHisSerAsnGlu-275 |
| SEQ. ID. NO. 5074 | 307-GlyIleLeuArgHisProGlu-313 |
| SEQ. ID. NO. 5075 | 343-ArgValThrArgSerLeuArgGlyGluGlnGluVal-354 |
| SEQ. ID. NO. 5076 | 482-LysTyrLysLysAspAlaGly-488 |

305-2
AMPHI Regions - AMPHI

| | |
|---|---|
| SEQ. ID. NO. 5077 | 10-LeuMetMetGlyLeuValGluGlyPheThrGluPheLeuPro-23 |
| SEQ. ID. NO. 5078 | 33-PheGlyAsnLeuIleGly-38 |
| SEQ. ID. NO. 5079 | 66-PheSerAsnValLeuHis-71 |
| SEQ. ID. NO. 5080 | 93-AlaAlaValMetGly-97 |
| SEQ. ID. NO. 5081 | 99-LeuPheGlyLysGlnIleLysGluTyrLeuPhe-109 |
| SEQ. ID. NO. 5082 | 141-AspValAspAlaLeuArgProIleAspAla-150 |
| SEQ. ID. NO. 5083 | 155-ValAlaGlnValPheAla-160 |
| SEQ. ID. NO. 5084 | 202-AlaTyrAspValLeuLysHisTyrArgPhePheThrLeuHis-215 |
| SEQ. ID. NO. 5085 | 222-IleGlyPheIleAlaAlaPheValSer-230 |
| SEQ. ID. NO. 5086 | 235-ValLysAlaLeuLeuArg-240 |

Antigenic Index - Jameson-Wolf

| | |
|---|---|
| SEQ. ID. NO. 5087 | 41-SerAsnHisLysValPhe-469 |
| SEQ. ID. NO. 5088 | 61-GluTyrArgGlnArgPheSerAsn-68 |
| SEQ. ID. NO. 5089 | 72-GlyLeuGlyLysAspArgLysAlaAsn-80 |
| SEQ. ID. NO. 5090 | 128-ValGluLysArgGlnSerArgAlaGluProLysIleAlaAsp-141 |
| SEQ. ID. NO. 5091 | 143-AspAlaLeuArgProIleAsp-149 |
| SEQ. ID. NO. 5092 | 163-ProGlyThrSerArgSerGlySer-170 |
| SEQ. ID. NO. 5093 | 180-IleGluArgLysThrAlaThr-186 |
| SEQ. ID. NO. 5094 | 241-PheValSerLysLysAsnTyr-247 |

Hydrophilic Regions - Hopp-Woods

| | |
|---|---|
| SEQ. ID. NO. 5095 | 62-TyrArgGlnArgPhe-66 |
| SEQ. ID. NO. 5096 | 73-LeuGlyLysAspArgLysAlaAsn-80 |
| SEQ. ID. NO. 5097 | 128-ValGluLysArgGlnSerArgAlaGluProLysIleAlaAsp-141 |
| SEQ. ID. NO. 5098 | 143-AspAlaLeuArgProIleAsp-149 |
| SEQ. ID. NO. 5099 | 165-ThrSerArgSerGlySer-170 |
| SEQ. ID. NO. 5100 | 180-IleGluArgLysThrAlaThr-186 |
| SEQ. ID. NO. 5101 | 242-ValSerLysLysAsn-246 |

308-1
AMPHI Regions - AMPHI

| | |
|---|---|
| SEQ. ID. NO. 5102 | 6-PheTyrArgIleLeuGlyValAla-13 |

TABLE 1-continued

| | |
|---|---|
| SEQ. ID. NO. 5103 | 15-AsnLeuTyrProArgLeu-20 |
| SEQ. ID. NO. 5104 | 27-ThrIleIleAlaGlyLeu-32 |
| SEQ. ID. NO. 5105 | 64-AlaLeuGluLeuLeuArgAlaGln-71 |
| SEQ. ID. NO. 5106 | 83-AlaGluMetAlaArgAlaSerGlu-90 |
| SEQ. ID. NO. 5107 | 101-LeuAlaAspPheValHisProIleGlyAsnIleGlyAlaCys-114 |
| SEQ. ID. NO. 5108 | 131-SerMetArgThrLeuAlaSerValAlaHisGlyPheGlyAsp-144 |
| SEQ. ID. NO. 5109 | 172-LeuAlaHisLeuAspAsnMetLysArgValThrGlu-183 |
| Antigenic Index - Jameson-Wolf | |
| SEQ. ID. NO. 5110 | 16-LeuTyrProArgLeuSerAspPheCys-24 |
| SEQ. ID. NO. 5111 | 39-TrpGluArgArgMetMetVal-45 |
| SEQ. ID. NO. 5112 | 68-LeuArgAlaGlnAspValGluThr-75 |
| SEQ. ID. NO. 5113 | 80-SerLysGlyAlaGluMetAlaArgAlaSerGluThrAlaTyrAlaArgAspGluVal-98 |
| SEQ. ID. NO. 5114 | 118-GlyThrPheLysThrAspGlyMet-125 |
| SEQ. ID. NO. 5115 | 141-GlyPheGlyAspAsnLeuLeu-147 |
| SEQ. ID. NO. 5116 | 149-ArgAlaAlaAspValValLeuLysGluArgArgArgLeu-161 |
| SEQ. ID. NO. 5117 | 166-ArgGluThrProLeu-170 |
| SEQ. ID. NO. 5118 | 176-AspAsnMetLysArgValThrGluMetGly-185 |
| SEQ. ID. NO. 5119 | 195-MetTyrArgLysProGlnThrAlaAspAspIleVal-206 |
| SEQ. ID. NO. 5120 | 219-IleAspThrProAspSerAlaGlu-226 |
| Hydrophilic Regions - Hopp-Woods | |
| SEQ. ID. NO. 5121 | 39-TrpGluArgArgMetMetVal-45 |
| SEQ. ID. NO. 5122 | 68-LeuArgAlaGlnAspValGluThr-75 |
| SEQ. ID. NO. 5123 | 81-LysGlyAlaGluMetAlaArgAlaSerGlu-90 |
| SEQ. ID. NO. 5124 | 92-AlaTyrAlaArgAspGluVal-98 |
| SEQ. ID. NO. 5125 | 120-PheLysThrAspGly-124 |
| SEQ. ID. NO. 5126 | 149-ArgAlaAlaAspValValLeuLysGluArgArgArgLeu-161 |
| SEQ. ID. NO. 5127 | 176-AspAsnMetLysArgValThrGlu-183 |
| SEQ. ID. NO. 5128 | 195-MetTyrArgLysProGlnThrAlaAspAspIleVal-206 |
| SEQ. ID. NO. 5129 | 220-AspThrProAspSerAlaGlu-226 |
| 311-1 | |
| AMPHI Regions - AMPHI | |
| SEQ. ID. NO. 5130 | 7-SerHisTrpArgValLeuAlaGluLeuAlaAspGlyLeuProGlnHisValSerGlnLeuAlaArgMetAlaAsp-31 |
| SEQ. ID. NO. 5131 | 37-LeuAsnGlyPheTrpGlnGlnMetProAlaHisIleArgGlyLeuLeuArg-53 |
| SEQ. ID. NO. 5132 | 55-HisAspGlyTyrTrpArgLeuValArgProLeuAlaValPheAspAlaGluGlyLeuArgGluLeuGly-77 |
| SEQ. ID. NO. 5133 | 124-ArgGlnGlyArgLysTrpSerHisArgLeu-133 |
| SEQ. ID. NO. 5134 | 165-ArgAlaLeuSerArg-169 |
| SEQ. ID. NO. 5135 | 219-ValGluAsnAlaAlaSerValGlnSerLeuPheGln-230 |
| SEQ. ID. NO. 5136 | 291-PheGluGlyThrValLysGlyValAspGlyGlnGlyVal-303 |
| SEQ. ID. NO. 5137 | 362-ThrValGlySerAlaProTyrArgAspLeuSerProLeu-374 |
| SEQ. ID. NO. 5138 | 391-CysAlaValCysGlyGluPheLysLys-399 |
| SEQ. ID. NO. 5139 | 426-TyrArgHisProGluGluHisGlySerAspArgTrpPheAsnAlaLeuGlySer-443 |
| SEQ. ID. NO. 5140 | 493-AsnValAsnArgHisAla-498 |
| SEQ. ID. NO. 5141 | 511-AlaValAlaSerGlyMetMetAspAlaValCys-521 |
| SEQ. ID. NO. 5142 | 550-AlaAlaLysValAlaGluAlaLeuProPro-559 |
| SEQ. ID. NO. 5143 | 576-TyrGlyLeuLeuAsnMet-581 |
| Antigenic Index - Jameson-Wolf | |
| SEQ. ID. NO. 5144 | 28-ArgMetAlaAspMetLysProGlnGln-36 |
| SEQ. ID. NO. 5145 | 50-GlyLeuLeuArgGlnHisAspGlyTyr-58 |
| SEQ. ID. NO. 5146 | 71-GluGlyLeuArgGluLeuGlyGluArgSerGlyPhe-82 |
| SEQ. ID. NO. 5147 | 86-LeuLysHisGluCysAlaSerSerAsnAspGluIleLeuGlu-99 |
| SEQ. ID. NO. 5148 | 102-ArgIleAlaProAspLysAlaHisLys-110 |
| SEQ. ID. NO. 5149 | 116-HisLeuGlnSerLysGlyArgGlyArgGlnGlyArgLysTrpSerHisArgLeuGlyGlu-135 |
| SEQ. ID. NO. 5150 | 145-PheAspArgProGlnTyrGluLeuGlySer-154 |
| SEQ. ID. NO. 5151 | 162-AlaCysArgArgAlaLeuSer-168 |
| SEQ. ID. NO. 5152 | 182-LeuValValGlyArgAspLysLeuGly-190 |
| SEQ. ID. NO. 5153 | 196-ThrValArgThrGlyGlyLysThrVal-204 |
| SEQ. ID. NO. 5154 | 215-LeuProLysGluValGluAsn-221 |
| SEQ. ID. NO. 5155 | 231-ThrAlaSerArgArgGlyAsnAlaAsp-239 |
| SEQ. ID. NO. 5156 | 258-TyrAlaArgAspGlyPheAla-264 |
| SEQ. ID. NO. 5157 | 272-AlaAlaAsnArgAspHisGlyLys-279 |
| SEQ. ID. NO. 5158 | 284-LeuArgAspGlyGluThrValPhe-291 |
| SEQ. ID. NO. 5159 | 293-GlyThrValLysGlyValAspGlyGlnGly-302 |
| SEQ. ID. NO. 5160 | 307-GluThrAlaGluGlyLysGlnThrValValSerGlyGluIleSerLeuArgSerAspAspArgProValSerValProLysArgArgAspSerGluArg-339 |
| SEQ. ID. NO. 5161 | 344-AspGlyGlyAsnSerArgLeu-350 |
| SEQ. ID. NO. 5162 | 364-GlySerAlaProTyrArgAspLeuSerProLeuGly-375 |
| SEQ. ID. NO. 5163 | 378-TrpAlaGluLysAlaAspGlyAsnValArgIle-388 |
| SEQ. ID. NO. 5164 | 385-GlyGluPheLysLysAlaGlnValGln-403 |
| SEQ. ID. NO. 5165 | 405-GlnLeuAlaArgLysIleGlu-411 |
| SEQ. ID. NO. 5166 | 424-AsnHisTyrArgHisProGluGluHisGlySerAspArgTrp-437 |
| SEQ. ID. NO. 5167 | 440-AlaLeuGlySerArgArgPheSerArgAsnAla-450 |
| SEQ. ID. NO. 5168 | 464-AlaLeuThrAspAspGlyHisTyrLeuGly-473 |
| SEQ. ID. NO. 5169 | 483-MetLysGluSerLeuAla-488 |
| SEQ. ID. NO. 5170 | 492-AlaAsnLeuAsnArgHisAlaGlyLysArgTyrPro-503 |
| SEQ. ID. NO. 5171 | 529-GlyArgLeuLysGluLysThrGlyAlaGlyLysProVal-541 |
| SEQ. ID. NO. 5172 | 547-GlyGlyGlyAlaAlaLysValAlaGlu-555 |
| SEQ. ID. NO. 5173 | 565-AsnThrValArgValAlaAsp-571 |
| SEQ. ID. NO. 5174 | 584-AlaGluGlyArgGluTyrGluHis-591 |
| Hydrophilic Regions - Hopp-Woods | |
| SEQ. ID. NO. 5175 | 28-ArgMetAlaAspMetLysProGlnGln-36 |
| SEQ. ID. NO. 5176 | 50-GlyLeuLeuArgGlnHis-55 |

TABLE 1-continued

| | |
|---|---|
| SEQ. ID. NO. 5177 | 71-GluGlyLeuArgGluLeuGlyGluArgSerGlyPhe-82 |
| SEQ. ID. NO. 5178 | 86-LeuLysHisGluCysAlaSerSerAsnAspGluIleLeuGlu-99 |
| SEQ. ID. NO. 5179 | 102-ArgIleAlaProAspLysAlaHisLys-110 |
| SEQ. ID. NO. 5180 | 118-GlnSerLysGlyArgGlyArgGlnGlyArgLysTrpSerHisArgLeuGlyGlu-135 |
| SEQ. ID. NO. 5181 | 162-AlaCysArgArgAlaLeuSer-168 |
| SEQ. ID. NO. 5182 | 183-ValValGlyArgAspLysLeuGly-190 |
| SEQ. ID. NO. 5183 | 196-ThrValArgThrGlyGlyLys-202 |
| SEQ. ID. NO. 5184 | 217-LysGluValGluAsn-221 |
| SEQ. ID. NO. 5185 | 232-AlaSerArgArgGlyAsnAlaAsp-239 |
| SEQ. ID. NO. 5186 | 259-AlaArgAspGlyPhe-263 |
| SEQ. ID. NO. 5187 | 272-AlaAlaAsnArgAspHisGlyLys-279 |
| SEQ. ID. NO. 5188 | 285-ArgAspGlyGluThrValPhe-291 |
| SEQ. ID. NO. 5189 | 293-GlyThrValLysGlyValAspGly-300 |
| SEQ. ID. NO. 5190 | 307-GluThrAlaGluGlyLysGlnThrValVal-316 |
| SEQ. ID. NO. 5191 | 320-IleSerLeuArgSerAspAspArgProValSerValProLysArgArgAspSerGluArg-339 |
| SEQ. ID. NO. 5192 | 346-GlyAsnSerArgLeu-350 |
| SEQ. ID. NO. 5193 | 367-ProTyrArgAspLeuSer-372 |
| SEQ. ID. NO. 5194 | 378-TrpAlaGluLysAlaAspGlyAsnVal-386 |
| SEQ. ID. NO. 5195 | 395-GlyGluPheLysLysAlaGlnVal-402 |
| SEQ. ID. NO. 5196 | 405-GlnLeuAlaArgLysIleGlu-411 |
| SEQ. ID. NO. 5197 | 424-AsnHisTyrArgHisProGluHisGlySer-434 |
| SEQ. ID. NO. 5198 | 442-GlySerArgArgPheSerArg-448 |
| SEQ. ID. NO. 5199 | 464-AlaLeuThrAspAspGlyHis-470 |
| SEQ. ID. NO. 5200 | 483-MetLysGluSerLeuAla-488 |
| SEQ. ID. NO. 5201 | 493-AsnLeuAsnArgHisAlaGlyLysArgTyrPro-503 |
| SEQ. ID. NO. 5202 | 529-GlyArgLeuLysGluLysThrGlyAlaGlyLysProVal-541 |
| SEQ. ID. NO. 5203 | 549-GlyAlaAlaLysValAlaGlu-555 |
| SEQ. ID. NO. 5204 | 565-AsnThrValArgValAlaAsp-571 |
| SEQ. ID. NO. 5205 | 584-AlaGluGlyArgGluTyrGluHis-591 |
| 312-2 | |
| AMPHIRegions - AMPHI | |
| SEQ. ID. NO. 5206 | 6-GlyGluIleLeuGluThrValLysMetValAla-16 |
| SEQ. ID. NO. 5207 | 33-AspCysIleSerSer-37 |
| SEQ. ID. NO. 5208 | 44-GlnAsnIleTyrAsnLysIleThrThrValGlyLys-55 |
| SEQ. ID. NO. 5209 | 82-IleAlaGlnIleAlaAlaAlaThr-89 |
| SEQ. ID. NO. 5210 | 95-ValSerValAlaGlnThrLeuAspLysAlaAlaLys-106 |
| SEQ. ID. NO. 5211 | 109-GlyValSerPheIleGlyGlyPheSerAlaLeuValGln-121 |
| SEQ. ID. NO. 5212 | 133-ArgSerIleProGluAlaMetLysThr-141 |
| SEQ. ID. NO. 5213 | 167-GlyGluThrValLysArgThrAla-174 |
| SEQ. ID. NO. 5214 | 182-GlyCysAlaLysIleValValPheCys-190 |
| SEQ. ID. NO. 5215 | 230-SerAspAlaThrThrLeuThrGluValAlaGluValValLysLys-244 |
| SEQ. ID. NO. 5216 | 249-IleThrArgValGlyGluLeuIleGlyArgGluAlaSerLys-262 |
| SEQ. ID. NO. 5217 | 281-ValGlyAspSerValAlaArgIleLeuGluGluMetGly-293 |
| SEQ. ID. NO. 5218 | 309-LeuAsnAspAlaVal-313 |
| SEQ. ID. NO. 5219 | 322-SerAlaValGlyGlyLeuSerGly-329 |
| SEQ. ID. NO. 5220 | 349-LeuThrLeuAspLysLeuGluAlaMetThrAla-359 |
| SEQ. ID. NO. 5221 | 374-ThrProAlaHisThrIleSerGlyIleIle-383 |
| SEQ. ID. NO. 5222 | 409-ValGlyAspSerValGluPheGlyGlyLeuLeuGly-420 |
| Antigenic Index - Jameson-Wolf | |
| SEQ. ID. NO. 5223 | 4-GlnSerGlyGluIleLeuGlu-10 |
| SEQ. ID. NO. 5224 | 13-LysMetValAlaAspGlnAsnPheAspVal-22 |
| SEQ. ID. NO. 5225 | 35-IleSerSerAspIle-39 |
| SEQ. ID. NO. 5226 | 52-ThrValGlyLysAspLeuValThr-59 |
| SEQ. ID. NO. 5227 | 89-ThrHisAlaAspSer-93 |
| SEQ. ID. NO. 5228 | 100-ThrLeuAspLysAlaAlaLys-106 |
| SEQ. ID. NO. 5229 | 121-GlnLysGlyMetSerProSerAspGluValLeu-131 |
| SEQ. ID. NO. 5230 | 134-SerIleProGluAlaMetLysThrThrAsp-143 |
| SEQ. ID. NO. 5231 | 152-GlySerThrArgAla-156 |
| SEQ. ID. NO. 5232 | 161-AspAlaValLysLeuAlaGlyGluThrValLysArgThrAlaGluIleThrProGluGlyPheGly-182 |
| SEQ. ID. NO. 5233 | 192-AlaValGluAspAsnProPhe-198 |
| SEQ. ID. NO. 5234 | 204-HisGlySerGlyGluAlaAspAla-211 |
| SEQ. ID. NO. 5235 | 225-AlaAlaLeuGluAsnSerAspAla-232 |
| SEQ. ID. NO. 5236 | 237-GluValAlaGluValValLys-243 |
| SEQ. ID. NO. 5237 | 251-ArgValGlyGluLeuIleGlyArgGluAlaSerLys-262 |
| SEQ. ID. NO. 5238 | 280-AlaValGlyAspSerValAlaArgIleLeuGlu-290 |
| SEQ. ID. NO. 5239 | 311-AspAlaValLysLysGlyGlyMet-318 |
| SEQ. ID. NO. 5240 | 334-ValSerGluAspGluGlyMet-340 |
| SEQ. ID. NO. 5241 | 352-AspLysLeuGluAla-356 |
| SEQ. ID. NO. 5242 | 370-ValProGlyAspThrProAla-376 |
| SEQ. ID. NO. 5243 | 383-IleAlaAspGluAlaAla-388 |
| SEQ. ID. NO. 5244 | 392-IleAsnSerLysThrThrAla-398 |
| SEQ. ID. NO. 5245 | 405-ThrGlyLysThrValGlyAspSerValGlu-414 |
| SEQ. ID. NO. 5246 | 426-ProValLysGluGlySerCys-432 |
| SEQ. ID. NO. 5247 | 435-PheValAsnArgGlyGlyArgIle-442 |
| SEQ. ID. NO. 5248 | 447-GlnSerMetLysAsn-451 |
| Hydrophilic Regions - Hopp-Woods | |
| SEQ. ID. NO. 5249 | 18-GlnAsnPheAspVal-22 |
| SEQ. ID. NO. 5250 | 52-ThrValGlyLysAspLeuValThr-59 |
| SEQ. ID. NO. 5251 | 100-ThrLeuAspLysAlaAlaLys-106 |
| SEQ. ID. NO. 5252 | 123-GlyMetSerProSerAspGluValLeu-131 |

TABLE 1-continued

| | |
|---|---|
| SEQ. ID. NO. 5253 | 134-SerIleProGluAlaMetLysThrThrAsp-143 |
| SEQ. ID. NO. 5254 | 161-AspAlaValLysLeuAlaGlyGluThrValLysArgThrAlaGluIleThrPro-178 |
| SEQ. ID. NO. 5255 | 192-AlaValGluAspAsnPro-197 |
| SEQ. ID. NO. 5256 | 207-GlyGluAlaAspAla-211 |
| SEQ. ID. NO. 5257 | 225-AlaAlaLeuGluAsnSerAspAla-232 |
| SEQ. ID. NO. 5258 | 237-GluValAlaGluValValLys-243 |
| SEQ. ID. NO. 5259 | 251-ArgValGlyGluLeuIleGlyArgGluAlaSerLys-262 |
| SEQ. ID. NO. 5260 | 284-SerValAlaArgIleLeuGlu-290 |
| SEQ. ID. NO. 5261 | 311-AspAlaValLysLysGlyGlyMet-318 |
| SEQ. ID. NO. 5262 | 334-ValSerGluAspGluGlyMet-340 |
| SEQ. ID. NO. 5263 | 352-AspLysLeuGluAla-356 |
| SEQ. ID. NO. 5264 | 383-IleAlaAspGluAlaAla-388 |
| SEQ. ID. NO. 5265 | 408-ThrValGlyAspSerValGlu-414 |
| SEQ. ID. NO. 5266 | 426-ProValLysGluGlySerCys-432 |
| SEQ. ID. NO. 5267 | 438-ArgGlyGlyArgIle-442 |
| SEQ. ID. NO. 5268 | 447-GlnSerMetLysAsn-451 |

313-2
AMPHI Regions - AMPHI

| | |
|---|---|
| SEQ. ID. NO. 5269 | 27-GlyMetAspAspProArgThrTyrGlySerGly-37 |
| SEQ. ID. NO. 5270 | 41-AlaThrAsnValLeu-45 |
| SEQ. ID. NO. 5271 | 60-AspAlaAlaLysGly-64 |
| SEQ. ID. NO. 5272 | 66-ValAlaValLeuLeuAlaArgValLeuGlnGluPro-77 |
| SEQ. ID. NO. 5273 | 88-ValAlaLeuAlaAlaLeuValGlyHisMetTrpPro-99 |
| SEQ. ID. NO. 5274 | 143-SerLeuAlaAlaLeuThrAlaThrIleAlaAlaProVal-155 |

Antigenic Index - Jameson-Wolf

| | |
|---|---|
| SEQ. ID. NO. 5275 | 26-TyrGlyMetAspAspProArgThrTyrGlySerGlyAsnProGlyAla-41 |
| SEQ. ID. NO. 5276 | 46-ArgSerGlyLysLysLysAlaAla-53 |
| SEQ. ID. NO. 5277 | 73-ValLeuGlnGluProLeuGlyLeuSerAspSerAla-84 |
| SEQ. ID. NO. 5278 | 104-PheLysGlyGlyLysGlyVal-110 |
| SEQ. ID. NO. 5279 | 181-HisLysSerAsnIle-185 |
| SEQ. ID. NO. 5280 | 189-LeuGluGlyArgGluSerLysIleGlyGlySerArg-200 |

Hydrophilic Regions - Hopp-Woods

| | |
|---|---|
| SEQ. ID. NO. 5281 | 26-TyrGlyMetAspAspProArgThrTyrGly-35 |
| SEQ. ID. NO. 5282 | 46-ArgSerGlyLysLysLysAlaAla-53 |
| SEQ. ID. NO. 5283 | 105-LysGlyGlyLysGlyVal-110 |
| SEQ. ID. NO. 5284 | 181-HisLysSerAsnIle-185 |
| SEQ. ID. NO. 5285 | 189-LeuGluGlyArgGluSerLysIleGlyGlySerArg-200 |

401
AMPHI Regions - AMPHI

| | |
|---|---|
| SEQ. ID. NO. 5286 | 46-ValLysProTyrAsnAlaLeu-52 |
| SEQ. ID. NO. 5287 | 65-CysTyrAsnCysHisSerGlnMetIleArgProPheArg-77 |
| SEQ. ID. NO. 5288 | 112-ValGlyGlyArgTyrSerArgGluTrpHisArgIle-123 |
| SEQ. ID. NO. 5289 | 157-MetLysAlaLeuArgLysValGlyThr-165 |
| SEQ. ID. NO. 5290 | 172-IleAlaLysAlaProGluAlaLeu-179 |

Antigenic Index - Jameson-Wolf

| | |
|---|---|
| SEQ. ID. NO. 5291 | 5-GlnLeuAlaGluGluLysIle-11 |
| SEQ. ID. NO. 5292 | 38-AlaAlaThrGlnProAlaProGlyValLysProTyrAsn-50 |
| SEQ. ID. NO. 5293 | 55-AlaGlyArgAspIleTyrIleArgGluGlyCysTyrAsnCysHis-69 |
| SEQ. ID. NO. 5294 | 74-ArgProPheArgAlaGluThrGluArgTyrGlyHis-85 |
| SEQ. ID. NO. 5295 | 90-GlyGluSerValTyr-94 |
| SEQ. ID. NO. 5296 | 98-PheGlnTrpGlySerLysArgThrGlyProAspLeuAlaArgValGlyGlyArgTyrSerAspGluTrpHis-121 |
| SEQ. ID. NO. 5297 | 125-LeuLeuAsnProArgAspValValProGluSerAsnMetPro-138 |
| SEQ. ID. NO. 5298 | 146-AsnLysValAspValAspAla-152 |
| SEQ. ID. NO. 5299 | 158-LysAlaLeuArgLysValGlyThrProTyrSerAspGluGluIleAlaLysAlaProGlu-177 |
| SEQ. ID. NO. 5300 | 179-LeuAlaAsnLysSerGluLeuAspAla-187 |

Hydrophilic Regions - Hopp-Woods

| | |
|---|---|
| SEQ. ID. NO. 5301 | 5-GlnLeuAlaGluGluLysIle-11 |
| SEQ. ID. NO. 5302 | 76-PheArgAlaGluThrGluArgTyrGly-84 |
| SEQ. ID. NO. 5303 | 101-GlySerLysArgThrGlyProAspLeuAlaArgValGlyGlyArgTyrSerAspGluTrpHis-121 |
| SEQ. ID. NO. 5304 | 127-AsnProArgAspValValPro-133 |
| SEQ. ID. NO. 5305 | 146-AsnLysValAspValAspAla-152 |
| SEQ. ID. NO. 5306 | 158-LysAlaLeuArgLysValGly-164 |
| SEQ. ID. NO. 5307 | 167-TyrSerAspGluGluIleAlaLysAlaProGlu-177 |
| SEQ. ID. NO. 5308 | 179-LeuAlaAsnLysSerGluLeuAspAla-187 |

402-2
AMPHI Regions - AMPHI

| | |
|---|---|
| SEQ. ID. NO. 5309 | 18-PheLeuSerGlyLeu-22 |
| SEQ. ID. NO. 5310 | 85-AlaGlyIleAlaAspPhe-90 |
| SEQ. ID. NO. 5311 | 100-ThrGlyPheSerGlyPheValHis-107 |
| SEQ. ID. NO. 5312 | 117-AlaValValArgGlyLeu-122 |
| SEQ. ID. NO. 5313 | 136-LysSerGlyArgGln-140 |
| SEQ. ID. NO. 5314 | 146-PheAlaAsnValAlaGly-151 |
| SEQ. ID. NO. 5315 | 218-ValPheGlnAsnIleAlaAspArgProAspArgLeuIle-230 |
| SEQ. ID. NO. 5316 | 261-AspValPheAsnSerValAsnGlyIleGlu-270 |
| SEQ. ID. NO. 5317 | 279-LysSerGlyIleArg-283 |
| SEQ. ID. NO. 5318 | 294-SerTrpAlaArgValLeuSerAlaIleProGluMetGln-306 |
| SEQ. ID. NO. 5319 | 344-ArgLysTrpLeuArgArgHisPro-351 |
| SEQ. ID. NO. 5320 | 376-AlaGluPheLeuLysGlnValGlnSerHisLeu-386 |
| SEQ. ID. NO. 5321 | 398-HisSerProHisAlaPheAlaThrAlaValHisSerIlePro-411 |
| SEQ. ID. NO. 5322 | 437-GlnArgLeuSerArgLeu-442 |

TABLE 1-continued

SEQ. ID. NO. 5323 460-AlaAlaGlnLysVal-464
Antigenic Index - Jameson-Wolf
SEQ. ID. NO. 5324 4-ValAsnThrLysProAsnThrSer-11
SEQ. ID. NO. 5325 66-ArgIleCysArgSerArgPheValAsp-74
SEQ. ID. NO. 5326 130-ValGlyThrAspGlyAsnLysSerGlyArgGlnValSer-142
SEQ. ID. NO. 5327 222-IleAlaAspArgProAspArgLeuIleGluAsnLysHisGly-235
SEQ. ID. NO. 5328 240-TyrHisArgAspGlyAspLysValVal-248
SEQ. ID. NO. 5329 264-AsnSerValAsnGlyIleGluArg-271
SEQ. ID. NO. 5330 277-SerLeuLysSerGlyIleArgArg-284
SEQ. ID. NO. 5331 321-IleAlaAspGluProGln-326
SEQ. ID. NO. 5332 331-LeuGlnAspLysArgValGluIleValLeuAspAspGlyArgLysTrpLeuArgArgHisProAspGluLysPheAsp-356
SEQ. ID. NO. 5333 385-HisLeuThrProAspGly-390
SEQ. ID. NO. 5334 429-PheProAsnLysGluLeuLeuLysGlnArgLeuSer-440
SEQ. ID. NO. 5335 444-TrpProGluSerGlyArgHisValPheAspSerSerThrVal-457
SEQ. ID. NO. 5336 472-MetThrGluProSerAlaGly-478
SEQ. ID. NO. 5337 481-ValIleThrAspAspAsnMet-487
SEQ. ID. NO. 5338 489-ValGluTyrLysTyrGlyArgGlyIle-497
Hydrophilic Regions - Hopp-Woods
SEQ. ID. NO. 5339 131-GlyThrAspGlyAsnLysSerGlyArgGlnVal-141
SEQ. ID. NO. 5340 222-IleAlaAspArgProAspArgLeuIleGluAsnLysHis-234
SEQ. ID. NO. 5341 241-HisArgAspGlyAspLysValVal-248
SEQ. ID. NO. 5342 278-LeuLysSerGlyIleArg-283
SEQ. ID. NO. 5343 321-IleAlaAspGluProGln-326
SEQ. ID. NO. 5344 331-LeuGlnAspLysArgValGluIleValLeuAspAspGlyArgLysTrpLeuArgArgHisProAspGluLysPheAsp-356
SEQ. ID. NO. 5345 430-ProAsnLysGluLeuLeuLysGlnArgLeuSer-440
SEQ. ID. NO. 5346 446-GluSerGlyArgHisValPhe-452
SEQ. ID. NO. 5347 473-ThrGluProSerAlaGly-478
SEQ. ID. NO. 5348 481-ValIleThrAspAspAsnMet-487
501-2
AMPHI Regions - AMPHI
SEQ. ID. NO. 5349 63-ValGluValLeuGlnGluLeuPheArgGlnTyrArgValAlaArgGlnLeu-79
SEQ. ID. NO. 5350 88-ValPheAlaAlaPheGlnAlaVal-95
SEQ. ID. NO. 5351 97-PheGlnGlyPheAspAsnGlyPhe-104
SEQ. ID. NO. 5352 126-AlaAspAlaPheGlnGly-131
SEQ. ID. NO. 5353 139-ValPheGluValValGlyAspIleThrArgArgThrThrGluAla-153
SEQ. ID. NO. 5354 183-AspGlyPheThrArgIleAsnArgCysGlyGlnCys-194
SEQ. ID. NO. 5355 196-HisAlaPheGlyAspPheIleAsp-203
Antigenic Index - Jameson-Wolf
SEQ. ID. NO. 5356 6-LeuThrAlaAspAla-10
SEQ. ID. NO. 5357 17-AlaAlaGlyGlyAspGlyLysValGlnHisHisPheAspGlyArgValAlaPhe-34
SEQ. ID. NO. 5358 46-ValGluThrGluGlyGln-51
SEQ. ID. NO. 5359 56-ValArgAlaAspGlyGluAlaValGluVal-65
SEQ. ID. NO. 5360 100-PheAspAsnGlyPhe-104
SEQ. ID. NO. 5361 108-GlnSerAlaAspGluArgAsnHisAspPheAsnValGlyGln-121
SEQ. ID. NO. 5362 144-GlyAspIleThrArgArgThrThrGluAlaGlnHis-155
SEQ. ID. NO. 5363 179-GlyHisThrAspAspGlyPheThrArgIleAsnArgCysGlyGlnCysArgHisAlaPhe-198
SEQ. ID. NO. 5364 202-IleAspValGluValAspArgGlyArgValThrGlyAspThrAlaGlyAsnPhe-219
Hydrophilic Regions - Hopp-Woods
SEQ. ID. NO. 5365 6-LeuThrAlaAspAla-10
SEQ. ID. NO. 5366 19-GlyGlyAspGlyLysVal-24
SEQ. ID. NO. 5367 46-ValGluThrGluGlyGln-51
SEQ. ID. NO. 5368 56-ValArgAlaAspGlyGluAlaValGluVal-65
SEQ. ID. NO. 5369 108-GlnSerAlaAspGluArgAsnHisAsp-116
SEQ. ID. NO. 5370 144-GlyAspIleThrArgArgThrThrGluAlaGlnHis-155
SEQ. ID. NO. 5371 179-GlyHisThrAspAspGlyPheThrArgIleAsnArg-190
SEQ. ID. NO. 5372 202-IleAspValGluValAspArgGlyArgValThrGlyAspThr-215
502-1
AMPHI Regions - AMPHI
SEQ. ID. NO. 5373 6-AsnLeuPheGlnPheLeuAlaValCys-14
SEQ. ID. NO. 5374 26-GlyAlaValAspAlaLeuLysGlnPheAsnAsnAspAlaAspGlyIleSerGlySerPheThrGln-47
SEQ. ID. NO. 5375 98-GlnValThrLysSerSerGlnAsp-105
Antigenic Index - Jameson-Wolf
SEQ. ID. NO. 5376 32-LysGlnPheAsnAsnAspAlaAspGlyIleSerGlySer-44
SEQ. ID. NO. 5377 48-ThrValGlnSerLysLysLysThrGlnThrAlaHisGlyThr-61
SEQ. ID. NO. 5378 73-GluTyrThrLysProTyrArg-79
SEQ. ID. NO. 5379 98-GlnValThrLysSerSerGlnAspGlnAlaIleGlyGlySerPro-112
SEQ. ID. NO. 5380 116-LeuSerAsnLysThrAlaLeuGluSerSerTyrThrLeuLysGluAspGlySerSerAsnGly-136
SEQ. ID. NO. 5381 142-AlaThrProLysArgAsnAsnAlaGly-150
SEQ. ID. NO. 5382 158-PheLysGlyGlyAsn-162
SEQ. ID. NO. 5383 167-GlnLeuLysAspSerPheGlyAsnGlnThr-176
SEQ. ID. NO. 5384 184-AsnThrAsnProGlnLeuSerArgGlyAlaPhe-194
SEQ. ID. NO. 5385 196-PheThrProProLysGlyValAspVal-204
Hydrophilic Regions - Hopp-Woods
SEQ. ID. NO. 5386 34-PheAsnAsnAspAlaAspGlyIle-41
SEQ. ID. NO. 5387 49-ValGlnSerLysLysLysThrGlnThr-57
SEQ. ID. NO. 5388 ThrLysSerSerGlnAspGlnAlaIle-108
SEQ. ID. NO. 5389 126-TyrThrLeuLysGluAspGlySerSerAsn-135
SEQ. ID. NO. 5390 143-ThrProLysArgAsnAsnAla-149
SEQ. ID. NO. 5391 167-GlnLeuLysAspSerPheGly-173

TABLE 1-continued 503-1
AMPHI Regions - AMPHI
SEQ. ID. NO. 5392  96-SerSerThrSerAsnPheAlaSerAlaAlaGluMetArgSerLeu-110
Antigenic Index - Jameson-Wolf
SEQ. ID. NO. 5393  4-SerLeuTyrArgGluAlaAsnThrTrpCys-13
SEQ. ID. NO. 5394  32-ProAlaAsnAspAlaSerGlyArgSerSerAlaValAlaGluGluArgThrAlaThrGluMetSerAlaProProAla-57
SEQ. ID. NO. 5395  69-SerAlaSerSerCysSerGlyLysGlyValSer-79
SEQ. ID. NO. 5396  87-LeuProThrArgAlaSerSerAlaThrSerSerThrSerAsn-100
SEQ. ID. NO. 5397  105-AlaGluMetArgSerLeuArg-111
SEQ. ID. NO. 5398  113-LeuCysAlaArgAsnAlaArg-119
Hydrophilic Regions - Hopp-Woods
SEQ. ID. NO. 5399  4-SerLeuTyrArgGlu-8
SEQ. ID. NO. 5400  32-ProAlaAsnAspAlaSerGlyArgSerSerAlaValAlaGluGluArgThrAlaThrGluMetSerAla-54
SEQ. ID. NO. 5401  73-CysSerGlyLysGlyValSer-79
SEQ. ID. NO. 5402  89-ThrArgAlaSerSer-93
SEQ. ID. NO. 5403  105-AlaGluMetArgSerLeuArg-111
505-2
AMPHI Regions - AMPHI
SEQ. ID. NO. 5404  20-LeuThrAlaLeuLeuLysCysLeuSerLeuLeuProLeuSerCysLeu-35
SEQ. ID. NO. 5405  37-ThrLeuGlyAsnArg-41
SEQ. ID. NO. 5406  89-ProAlaPhePheArgLysProGluAspIleGluThrMetPheLysAlaValHisGlyTrpGluHisValGlnGlnAlaLeuAsp-116
SEQ. ID. NO. 5407  148-AlaMetTyrLysProProLysIleLysAlaIleAspLysIleMetGlnAlaGly-165
SEQ. ID. NO. 5408  178-IleGlnGlyValLysGlnIleIleLysAlaLeuArg-189
SEQ. ID. NO. 5409  210-GlyValTrpValAspPhePheGlyLysPro-219
Antigenic Index - Jameson-Wolf
SEQ. ID. NO. 5410  39-GlyAsnArgLeuGly-43
SEQ. ID. NO. 5411  50-LeuLysGluAspArgAlaArgIle-57
SEQ. ID. NO. 5412  64-AlaGlyLeuAsnProAspProLysThrValLys-74
SEQ. ID. NO. 5413  79-GluThrAlaLysGlyGlyLeu-85
SEQ. ID. NO. 5414  92-PheArgLysProGluAspIleGluThr-100
SEQ. ID. NO. 5415  114-AlaLeuAspLysHisGlu-119
SEQ. ID. NO. 5416  131-TyrAspLeuGlyGlyArgTyrIleSer-139
SEQ. ID. NO. 5417  150-TyrLysProProLysIleLysAlaIleAspLysIleMetGln-163
SEQ. ID. NO. 5418  165-GlyArgValArgGlyLysGlyLysThrAlaProThrSer-177
SEQ. ID. NO. 5419  183-GlnIleIleLysAlaLeuArgSerGlyGluAlaThr-194
SEQ. ID. NO. 5420  199-AspHisValProSerProGlnGluGlyGlyGluGlyVal-211
SEQ. ID. NO. 5421  243-GluArgLeuProGlyGlyGlnGly-250
SEQ. ID. NO. 5422  258-ValGlnGlyGluLeuAsnGlyAspLysAlaHisAsp-269
SEQ. ID. NO. 5423  293-AsnArgTyrLysMetPro-298
Hydrophilic Regions - Hopp-Woods
SEQ. ID. NO. 5424  50-LeuLysGluAspArgAlaArgIle-57
SEQ. ID. NO. 5425  65-GlyLeuAsnProAspProLysThrVal-73
SEQ. ID. NO. 5426  79-GluThrAlaLysGlyGlyLeu-85
SEQ. ID. NO. 5427  92-PheArgLysProGluAspIleGluThr-100
SEQ. ID. NO. 5428  114-AlaLeuAspLysHisGlu-119
SEQ. ID. NO. 5429  151-LysProProLysIleLysAlaIleAspLysIleMetGln-163
SEQ. ID. NO. 5430  165-GlyArgValArgGlyLysGlyLysThrAlaPro-175
SEQ. ID. NO. 5431  183-GlnIleIleLysAlaLeuArgSerGlyGlu-192
SEQ. ID. NO. 5432  201-ValProSerProGlnGluGlyGlyGlu-209
SEQ. ID. NO. 5433  258-ValGlnGlyGluLeuAsnGlyAspLysAlaHisAsp-269
506-2
AMPHI Regions - AMPHI
SEQ. ID. NO. 5434  6-GluValGlyArgValAlaHisCysGlyGlyGlyVal-17
SEQ. ID. NO. 5435  25-ArgValValHisGlnValGluGlnGlyAlaArg-35
SEQ. ID. NO. 5436  56-PheGlnArgArgPhe-60
SEQ. ID. NO. 5437  99-AlaThrArgThrIleAspGlyAsnLeuAlaGluValTyrAlaGlnThr-114
SEQ. ID. NO. 5438  138-GlyAsnGluValAlaArgCys-144
SEQ. ID. NO. 5439  180-GlnValLysArgMetIleArgTyrPhePheArgVal-191
Antigenic Index - Jameson-Wolf
SEQ. ID. NO. 5440  13-CysGlyGlyGlyValAla-18
SEQ. ID. NO. 5441  31-GluGlnGlyAlaArgLeu-36
SEQ. ID. NO. 5442  54-ValAspPheGlnArgArgPheGlyGluVal-63
SEQ. ID. NO. 5443  98-ArgAlaThrArgThrIleAspGlyAsnLeu-107
SEQ. ID. NO. 5444  134-GlyAlaAspThrGlyAsnGluValAlaArgCysGluGly-146
SEQ. ID. NO. 5445  176-ProAsnPheGlyGlnValLysArgMetIle-185
SEQ. ID. NO. 5446  195-HisAspLeuAspVal-199
SEQ. ID. NO. 5447  201-ArgProPheArgLys-205
Hydrophilic Regions - Hopp-Woods
SEQ. ID. NO. 5448  31-GluGlnGlyAlaArgLeu-36
SEQ. ID. NO. 5449  54-ValAspPheGlnArgArgPheGlyGlu-62
SEQ. ID. NO. 5450  98-ArgAlaThrArgThrIleAsp-104
SEQ. ID. NO. 5451  136-AspThrGlyAsnGluValAlaArgCysGluGly-146
SEQ. ID. NO. 5452  180-GlnValLysArgMetIle-185
SEQ. ID. NO. 5453  195-HisAspLeuAspVal-199
SEQ. ID. NO. 5454  201-ArgProPheArgLys-205
513
AMPHI Regions - AMPHI
SEQ. ID. NO. 5455  6-AsnAlaAlaAlaAlaAla-11
SEQ. ID. NO. 5456  19-GlnGlyMetIleGlnMetLeuGlyValPheValAsp-30
SEQ. ID. NO. 5457  48-ProTyrGlyAspLeu-52

TABLE 1-continued

| | |
|---|---|
| SEQ. ID. NO. 5458 | 63-ValSerGlnValGlyGlnTrp-69 |
| SEQ. ID. NO. 5459 | 107-ThrAlaValPheArgMet-112 |
| SEQ. ID. NO. 5460 | 119-TyrPheGlyAlaValAla-124 |
| SEQ. ID. NO. 5461 | 139-IleMetAlaTrpIleAsnLeuValAlaIleLeuLeuLeuSer-152 |

Antigenic Index - Jameson-Wolf

| | |
|---|---|
| SEQ. ID. NO. 5462 | 2-GlySerAlaProAsnAla-7 |
| SEQ. ID. NO. 5463 | 11-AlaGluValLysHisProVal-17 |
| SEQ. ID. NO. 5464 | 47-GlnProTyrGlyAspLeuSerGly-54 |
| SEQ. ID. NO. 5465 | 91-AlaTyrAlaGluSerAsnVal-97 |
| SEQ. ID. NO. 5466 | 160-ArgAspTyrThrAlaLysLeuLysMetGlyLysAspProGluPheLysLeuSerGluHisProGlyLeuLysArgArgIleLysSerAspValTrp-191 |

Hydrophilic Regions - Hopp-Woods

| | |
|---|---|
| SEQ. ID. NO. 5467 | 11-AlaGluValLysHis-15 |
| SEQ. ID. NO. 5468 | 166-LeuLysMetGlyLysAspProGluPheLysLeuSerGlu-178 |
| SEQ. ID. NO. 5469 | 180-ProGlyLeuLysArgArgIleLysSer-188 |

515-1
AMPHI Regions - AMPHI

| | |
|---|---|
| SEQ. ID. NO. 5470 | 8-ArgAlaAlaGlyValAlaArgGlyLeuHisThrGluPheAlaArgAlaVal-24 |
| SEQ. ID. NO. 5471 | 59-AspValArgPhePheAlaGlnValGluGluIleGlyGlnAspPhePheAlaAspAla-77 |
| SEQ. ID. NO. 5472 | 90-AlaGlyGluCysAlaAspGluValSerAspLysThr-101 |
| SEQ. ID. NO. 5473 | 122-GluSerAlaGlnSerAlaAlaGlyGlyGlyLeuThrAspGlyPheGly-137 |
| SEQ. ID. NO. 5474 | 176-CysGlyLysThrValGlyVal-182 |
| SEQ. ID. NO. 5475 | 198-GlyValPheAspAla-202 |
| SEQ. ID. NO. 5476 | 251-PheGlyGlyValAla-255 |
| SEQ. ID. NO. 5477 | 259-AspGlyGlyPheAspGlyValLeuGlnGlyPhePheGlyGluVal-273 |

Antigenic Index - Jameson-Wolf

| | |
|---|---|
| SEQ. ID. NO. 5478 | 24-ValThrAlaGluGluIleAlaPhe-31 |
| SEQ. ID. NO. 5479 | 38-HisGluAlaArgCysGlyGlyAsn-45 |
| SEQ. ID. NO. 5480 | 51-IleAlaAlaAlaGluArgAlaGlyAsp-59 |
| SEQ. ID. NO. 5481 | 67-GluGluIleGlyGln-71 |
| SEQ. ID. NO. 5482 | 77-AlaValAspGlnGluThr-82 |
| SEQ. ID. NO. 5483 | 84-LeuAlaValGluArgAlaAlaGlyGluCysAlaAspGluValSerAspLysThrAlaArgAsnGlyGlyIleGluGluAspGlyValAlaAlaCysArgAspAlaAlaAlaAlaGluSerAlaGln-125 |
| SEQ. ID. NO. 5484 | 128-AlaGlyGlyGlyLeuThrAspGly-135 |
| SEQ. ID. NO. 5485 | 160-GlyGlyAsnAspAlaAlaGlyAsn-167 |
| SEQ. ID. NO. 5486 | 192-LeuHisArgArgAla-196 |
| SEQ. ID. NO. 5487 | 217-AlaAspGlyGlyPheArg-222 |
| SEQ. ID. NO. 5488 | 239-HisGlnThrGlyIleGlyLysSerGly-247 |
| SEQ. ID. NO. 5489 | 256-GlyAspValAspGlyGlyPheAspGly-264 |
| SEQ. ID. NO. 5490 | 273-ValGlySerThrGlyAla-278 |
| SEQ. ID. NO. 5491 | 284-AspValAsnGlyAsnValGln-290 |

Hydrophilic Regions - Hopp-Woods

| | |
|---|---|
| SEQ. ID. NO. 5492 | 24-ValThrAlaGluGluIleAlaPhe-31 |
| SEQ. ID. NO. 5493 | 38-HisGluAlaArgCysGly-43 |
| SEQ. ID. NO. 5494 | 51-IleAlaAlaAlaGluArgAlaGlyAsp-59 |
| SEQ. ID. NO. 5495 | 77-AlaValAspGlnGluThr-82 |
| SEQ. ID. NO. 5496 | 84-LeuAlaValGluArgAlaAlaGlyGluCysAlaAspGluValSerAspLysThrAlaArgAsnGlyGlyIleGluGluAspGlyValAlaAlaCysArgAspAlaAlaAlaAlaGluSerAlaGln-125 |
| SEQ. ID. NO. 5497 | 162-AsnAspAlaAlaGly-166 |
| SEQ. ID. NO. 5498 | 192-LeuHisArgArgAla-196 |
| SEQ. ID. NO. 5499 | 242-GlyIleGlyLysSerGly-247 |
| SEQ. ID. NO. 5500 | 256-GlyAspValAspGlyGlyPhe-262 |

519-1
AMPHI Regions - AMPHI

| | |
|---|---|
| SEQ. ID. NO. 5501 | 15-GlyPheLysSerPhe-19 |
| SEQ. ID. NO. 5502 | 29-ValValGluArgLeuGlyArgPheHisArgAlaLeuThrAlaGly-43 |
| SEQ. ID. NO. 5503 | 105-MetAlaIleThrGlnLeuAlaGlnThrThrLeuArgSerVal-118 |
| SEQ. ID. NO. 5504 | 141-AlaLeuAspGluAlaAla-146 |
| SEQ. ID. NO. 5505 | 166-GluIleLeuArgSerMetGlnAla-173 |
| SEQ. ID. NO. 5506 | 192-LysIleGluGlnIle-196 |
| SEQ. ID. NO. 5507 | 221-SerAsnAlaGluLysIleAlaArgIleAsn-230 |
| SEQ. ID. NO. 5508 | 249-AlaIleArgGlnIleAlaAlaAla-256 |
| SEQ. ID. NO. 5509 | 273-GlnTyrValAlaAlaPheAsnAsnLeuAlaLys-283 |
| SEQ. ID. NO. 5510 | 292-AlaAsnValAlaAspIleGlySerLeuIleSerAlaGlyMetLysIleIleAspSerSerLysThrAla-314 |

Antigenic Index - Jameson-Wolf

| | |
|---|---|
| SEQ. ID. NO. 5511 | 31-GluArgLeuGlyArgPheHisArg-38 |
| SEQ. ID. NO. 5512 | 58-HisSerLeuLysGluIleProLeuAspValProSerGln-70 |
| SEQ. ID. NO. 5513 | 72-CysIleThrArgAspAsnThrGlnLeuThrVal-82 |
| SEQ. ID. NO. 5514 | 91-ThrAspProLysLeuAlaSer-97 |
| SEQ. ID. NO. 5515 | 122-MetGluLeuAspLysThrPheGluGluArgAspGluIleAsn-135 |
| SEQ. ID. NO. 5516 | 141-AlaLeuAspGluAlaAlaGly-147 |
| SEQ. ID. NO. 5517 | 154-LeuArgTyrGluIleLysAspLeuValPro-163 |
| SEQ. ID. NO. 5518 | 175-IleThrAlaGluArgGluLysArgAlaArgIleAlaGluSerGluGlyArgLysIleGluGln-195 |
| SEQ. ID. NO. 5519 | 197-AsnLeuAlaSerGlyGlnArgGluAlaGluIleGlnGlnSerGluGlyGluAlaGlnAla-216 |
| SEQ. ID. NO. 5520 | 219-AsnAlaSerAsnAlaGluLysIleAlaArgIleAsnArgAlaLysGlyGluAlaGluSerLeuArgLeu-241 |
| SEQ. ID. NO. 5521 | 245-AlaAsnAlaGluAlaIleArg-251 |
| SEQ. ID. NO. 5522 | 258-GlnThrGlnGlyGlyAlaAspAlaValAsn-267 |
| SEQ. ID. NO. 5523 | 281-LeuAlaLysGluSerAsnThr-287 |
| SEQ. ID. NO. 5524 | 303-AlaGlyMetLysIleIleAspSerSerLysThrAlaLys-315 |

Hydrophilic Regions - Hopp-Woods

| | |
|---|---|
| SEQ. ID. NO. 5525 | 31-GluArgLeuGlyArgPheHisArg-38 |

TABLE 1-continued

| | |
|---|---|
| SEQ. ID. NO. 5526 | 58-HisSerLeuLysGluIleProLeu-65 |
| SEQ. ID. NO. 5527 | 73-IleThrArgAspAsnThr-78 |
| SEQ. ID. NO. 5528 | 91-ThrAspProLysLeu-95 |
| SEQ. ID. NO. 5529 | 122-MetGluLeuAspLysThrPheGluGluArgAspGluIleAsn-135 |
| SEQ. ID. NO. 5530 | 141-AlaLeuAspGluAlaAla-146 |
| SEQ. ID. NO. 5531 | 154-LeuArgTyrGluIleLysAspLeuValPro-163 |
| SEQ. ID. NO. 5532 | 175-IleThrAlaGluArgGluLysArgAlaArgIleAlaGluSerGluGlyArgLysIleGluGln-195 |
| SEQ. ID. NO. 5533 | 200-SerGlyGlnArgGluAlaGluIleGlnGlnSerGluGlyGluAlaGlnAla-216 |
| SEQ. ID. NO. 5534 | 221-SerAsnAlaGluLysIleAlaArgIleAsnArgAlaLysGlyGluAlaGluSerLeuArgLeu-241 |
| SEQ. ID. NO. 5535 | 245-AlaAsnAlaGluAlaIleArg-251 |
| SEQ. ID. NO. 5536 | 281-LeuAlaLysGluSerAsn-286 |
| SEQ. ID. NO. 5537 | 306-LysIleIleAspSerSerLysThrAlaLys-315 |
| 520-1 | |
| AMPHI Regions - AMPHI | |
| SEQ. ID. NO. 5538 | 104-LeuThrLysAlaAlaAspGlyGlnValCysArgAlaPheSerSerLeu-119 |
| Antigenic Index - Jameson-Wolf | |
| SEQ. ID. NO. 5539 | 20-LysProSerArgArgAlaLeu-26 |
| SEQ. ID. NO. 5540 | 47-AlaSerGlyLysIleSerLeuPro-54 |
| SEQ. ID. NO. 5541 | 84-ProProAsnAsnSerThrThrThrSerThrSerSerArgAlaThrSerSerAsnGlySerLeuThrLysAlaAlaAspGlyGlnVal-112 |
| SEQ. ID. NO. 5542 | 117-SerSerLeuLysSerHisThrAlaGluIleArgIleSerArgProLysArgArgGluIleSerSerAlaLeuSerArgAsnThrAlaAla-146 |
| SEQ. ID. NO. 5543 | 150-ProThrValProLysProLysArgProMet-159 |
| SEQ. ID. NO. 5544 | 166-SerProCysLysProThrGluMet-173 |
| Hydrophilic Regions - Hopp-Woods | |
| SEQ. ID. NO. 5545 | 20-LysProSerArgArgAlaLeu-26 |
| SEQ. ID. NO. 5546 | 93-ThrSerSerArgAlaThrSerSer-100 |
| SEQ. ID. NO. 5547 | 103-SerLeuThrLysAlaAlaAsp-109 |
| SEQ. ID. NO. 5548 | 120-LysSerHisThrAlaGluIleArgIleSerArgProLysArgArgGluIleSer-137 |
| SEQ. ID. NO. 5549 | 140-LeuSerArgAsnThrAla-145 |
| SEQ. ID. NO. 5550 | 151-ThrValProLysProLysArgProMet-159 |
| SEQ. ID. NO. 5551 | 168-CysLysProThrGluMet-173 |
| 521-2 | |
| AMPHI Regions - AMPHI | |
| SEQ. ID. NO. 5552 | 39-ThrLysProSerLysSerCys-45 |
| SEQ. ID. NO. 5553 | 50-LeuProProIleGly-54 |
| SEQ. ID. NO. 5554 | 65-GlnThrProGluProValSerSerProSer-74 |
| SEQ. ID. NO. 5555 | 76-GlyGlyGlnValVal-80 |
| SEQ. ID. NO. 5556 | 86-ValLysThrValSerLysProAlaLys-94 |
| SEQ. ID. NO. 5557 | 133-GlnAlaArgLeuAlaLysGlyGlyAsn-141 |
| Antigenic Index - Jameson-Wolf | |
| SEQ. ID. NO. 5558 | 36-ValTyrThrThrLysProSerLysSerCysHisSerThrAspLeuProProIleGlyAsnTyrSerSerGluArgTyrIleProProGlnThrProGlu ProValSerSerProSerAsnGlyGlyGlnValValLysTyrLysAlaProValLysThrValSerLysProAlaLysSerAsnThrProProProGlnGlnAla ProSerAsnAsnSerArgArgSerIleLeuGluThrGluLeuSerAsnGluArgLysAlaLeuValGluAlaGlnLysMetLeuSer-132 |
| SEQ. ID. NO. 5559 | 135-ArgLeuAlaLysGlyGlyAsnIleAsn-143 |
| SEQ. ID. NO. 5560 | 152-SerAsnValLeuAspArgGlnGlnAsn-160 |
| SEQ. ID. NO. 5561 | 164-LeuGlnArgGluLeuGlyArg-170 |
| Hydrophilic Regions - Hopp-Woods | |
| SEQ. ID. NO. 5562 | 40-LysProSerLysSerCysHis-46 |
| SEQ. ID. NO. 5563 | 57-SerSerGluArgTyrIle-62 |
| SEQ. ID. NO. 5564 | 65-GlnThrProGluProValSer-71 |
| SEQ. ID. NO. 5565 | 80-ValLysTyrLysAlaProVal-86 |
| SEQ. ID. NO. 5566 | 88-ThrValSerLysProAlaLysSerAsnThrProPro-99 |
| SEQ. ID. NO. 5567 | 102-GlnAlaProSerAsnAsnSerArgArgSerIleLeuGluThrGluLeuSerAsnGluArgLysAlaLeuValGluAlaGlnLysMetLeuSer-132 |
| SEQ. ID. NO. 5568 | 154-ValLeuAspArgGlnGlnAsn-160 |
| SEQ. ID. NO. 5569 | 164-LeuGlnArgGluLeuGlyArg-170 |
| 522 | |
| AMPHI Regions - AMPHI | |
| SEQ. ID. NO. 5570 | 32-TrpValIleLeuAlaLeuLeuAlaLeuThrAlaLeuLeuSer-45 |
| SEQ. ID. NO. 5571 | 57-LysIleValGluSerCysValLys-64 |
| SEQ. ID. NO. 5572 | 96-MetTrpGluGlnProLeuAspArgLeuSerGluLysGlnIleArgSerPheGlyLysLeuGlyAlaGlnGluGlnLeuAspLeuLeuGlyGlyAla-127 |
| Antigenic Index - Jameson-Wolf | |
| SEQ. ID. NO. 5573 | 1-MetThrGluProLysHisGluMetLeuThrLysGluGlnValAlaAlaArgLysLysAlaLysAlaLysIleArgThr-26 |
| SEQ. ID. NO. 5574 | 48-AlaMetSerLysProGlnAlaLysGlnLysIleValGluSerCysValLys-64 |
| SEQ. ID. NO. 5575 | 71-LysTrpGlnAsnAspLeuArgAlaArgGlyLeuAspSerAsnAsnThrArgLeuAla-89 |
| SEQ. ID. NO. 5576 | 99-GlnProLeuAspArgLeuSerGluLysGlnIleArgSerPheGlyLysLeuGlyAla-117 |
| SEQ. ID. NO. 5577 | 128-AsnAlaPheGluAlaArgAspLysGlnCysValAlaAspLeuLysSerGlu-144 |
| Hydrophilic Regions - Hopp-Woods | |
| SEQ. ID. NO. 5578 | 1-MetThrGluProLysHisGluMetLeuThrLysGluGlnValAlaAlaArgLysLysAlaLysAlaLysIleArgThr-26 |
| SEQ. ID. NO. 5579 | 48-AlaMetSerLysProGlnAlaLysGlnLysIleValGluSerCysVal-63 |
| SEQ. ID. NO. 5580 | 71-LysTrpGlnAsnAspLeuArgAlaArgGlyLeuAspSerAsnAsnThr-86 |
| SEQ. ID. NO. 5581 | 100-ProLeuAspArgLeuSerGluLysGlnIleArgSerPheGly-113 |
| SEQ. ID. NO. 5582 | 130-PheGluAlaArgAspLysGlnCysValAlaAspLeuLysSerGlu-144 |
| 525-1 | |
| AMPHI Regions - AMPHI | |
| SEQ. ID. NO. 5583 | 59-GluPheAlaGluPheValAsnSerHisProGln-69 |
| SEQ. ID. NO. 5584 | 86-LysHisTrpMetLysAsnGly-92 |
| SEQ. ID. NO. 5585 | 125-ArgLeuProThrIleAspGluTrpGluPhe-134 |
| SEQ. ID. NO. 5586 | 154-ThrIleLeuAspTrpTyr-159 |
| SEQ. ID. NO. 5587 | 164-ArgLysGlyLeuHisAspValGly-171 |
| SEQ. ID. NO. 5588 | 178-TrpGlyValTyrAsp-182 |
| SEQ. ID. NO. 5589 | 188-TrpGluTrpThrGlu-192 |

TABLE 1-continued

Antigenic Index - Jameson-Wolf
SEQ. ID. NO. 5590    24-ValGlnIleGluGlyGlySerTyrArgProLeuTyrLeuLysLysAspThrGlyLeuIleLys-44
SEQ. ID. NO. 5591    46-LysProPheLysLeuAspLysTyrProValThr-56
SEQ. ID. NO. 5592    67-HisProGlnTrpGlnLysGlyArgIleGlySerLysGlnAlaGlu-81
SEQ. ID. NO. 5593    88-TrpMetLysAsnGlySerArgSerTyrAlaProLysAlaGlyGluLeuLysGlnPro-106
SEQ. ID. NO. 5594    122-GlnGlyLysArgLeuProThrIleAspGluTrpGlu-133
SEQ. ID. NO. 5595    140-AlaThrGlnLysAsnGlySerAsnGluProGlyTyrAsnArgThr-154
SEQ. ID. NO. 5596    159-TyrAlaAspGlyGlyArgLysGlyLeuHisAspValGlyLysGlyArgProAsnTyr-177
SEQ. ID. NO. 5597    190-TrpThrGluAspPheAsnSerSerLeuLeuSerSerGlyAsnAla-204
SEQ. ID. NO. 5598    213-AlaSerIleGlySerSerAspSerSerAsnTyr-223
SEQ. ID. NO. 5599    234-SerLeuGlnSerLysTyr-239
Hydrophilic Regions - Hopp-Woods
SEQ. ID. NO. 5600    35-TyrLeuLysLysAspThrGlyLeuIleLys-44
SEQ. ID. NO. 5601    46-LysProPheLysLeuAspLysTyrPro-54
SEQ. ID. NO. 5602    71-GlnLysGlyArgIleGlySerLysGlnAlaGlu-81
SEQ. ID. NO. 5603    91-AsnGlySerArgSerTyrAlaProLysAlaGlyGluLeuLysGln-105
SEQ. ID. NO. 5604    122-GlnGlyLysArgLeuProThr-128
SEQ. ID. NO. 5605    140-AlaThrGlnLysAsnGlySerAsnGluProGlyTyr-151
SEQ. ID. NO. 5606    162-GlyGlyArgLysGlyLeuHisAspValGlyLysGlyArgPro-175
SEQ. ID. NO. 5607    216-GlySerSerAspSerSerAsn-222
527-2
AMPHI Regions - AMPHI
SEQ. ID. NO. 5608    7-PhePheGlnProValGln-12
SEQ. ID. NO. 5609    28-SerAspAlaAlaGluLeuValGluLeuPheAlaLeuPhePro-41
SEQ. ID. NO. 5610    73-GlyLysGlyIleGluArgGlnValAspAsnIleAlaAspValTyrGlyPhe-89
Antigenic Index - Jameson-Wolf
SEQ. ID. NO. 5611    26-GlyGlySerAspAlaAlaGlu-32
SEQ. ID. NO. 5612    52-GlnLysProArgLeuGlyCys-58
SEQ. ID. NO. 5613    71-PheIleGlyLysGlyIleGluArgGlnValAspAsnIleAla-84
SEQ. ID. NO. 5614    107-LeuLeuArgLysGlyThrGlyLeuGluLysThrCysArgProLysProPheValGlnProHisGlyGlyArg-130
Hydrophilic Regions - Hopp-Woods
SEQ. ID. NO. 5615    27-GlySerAspAlaAlaGlu-32
SEQ. ID. NO. 5616    52-GlnLysProArgLeuGlyCys-58
SEQ. ID. NO. 5617    75-GlyIleGluArgGlnValAspAsnIleAla-84
SEQ. ID. NO. 5618    107-LeuLeuArgLysGlyThrGlyLeuGluLysThrCysArgProLysPro-122
528-1
AMPHI Regions - AMPHI
SEQ. ID. NO. 5619    7-LysTyrThrAlaMetAlaAlaLeuLeuAlaPhe-17
SEQ. ID. NO. 5620    23-ArgLeuAlaGlyTrpTyrGluCysSerSerLeuThrGlyTrpCysLysProArgLysProAlaAlaIle-45
SEQ. ID. NO. 5621    69-AsnArgSerValArg-73
SEQ. ID. NO. 5622    86-TyrArgLysIleGlyLysPhe-92
SEQ. ID. NO. 5623    106-ProLeuIleGluThrPheLys-112
Antigenic Index - Jameson-Wolf
SEQ. ID. NO. 5624    1-MetGluIleArgAla-5
SEQ. ID. NO. 5625    29-GluCysSerSerLeuThrGlyTrpCysLysProArgLysProAlaAla-44
SEQ. ID. NO. 5626    49-AspIleGlyGlyGluSerProProSerLeuGlyAspTyrGluIleProLeuSerAspGlyAsnArgSerValArgAlaAsnGluTyrGluSerAlaGln
                     GlnSer-83
SEQ. ID. NO. 5627    88-LysIleGlyLysPheGluAlaCysGlyLeuAspTrpArgThrArgAspGlyLysProLeu-107
SEQ. ID. NO. 5628    110-ThrPheLysGlnGlyGlyPheAspCysLeuGluLysGlnGlyLeuArgArgAsnGlyLeuSerGluArgValArgTrp-135
Hydrophilic Regions - Hopp-Woods
SEQ. ID. NO. 5629    1-MetGluIleArgAla-5
SEQ. ID. NO. 5630    37-CysLysProArgLysProAlaAla-44
SEQ. ID. NO. 5631    51-GlyGlyGluSerProProSer-57
SEQ. ID. NO. 5632    59-GlyAspTyrGluIleProLeu-65
SEQ. ID. NO. 5633    67-AspGlyAsnArgSerValArgAlaAsnGluTyrGluSerAlaGln-81
SEQ. ID. NO. 5634    88-LysIleGlyLysPheGluAlaCys-95
SEQ. ID. NO. 5635    99-TrpArgThrArgAspGlyLysProLeu-107
SEQ. ID. NO. 5636    117-AspCysLeuGluLysGlnGlyLeuArgArgAsnGlyLeuSerGluArgValArgTrp-135
529
AMPHI Regions - AMPHI
SEQ. ID. NO. 5637    11-LeuAlaLeuIleGlyLeuAlaAlaCysSer-20
SEQ. ID. NO. 5638    35-SerHisArgLeuIle-39
SEQ. ID. NO. 5639    49-AsnProAspGlnGlyAsnLeuTyrArgLeuProAla-60
SEQ. ID. NO. 5640    79-GlnGlnProAlaAspAlaGluValLeuLysSerValLysGlyValArg-94
SEQ. ID. NO. 5641    152-GlnAspSerLeuArgArgLeuPheAsp-160
SEQ. ID. NO. 5642    196-AlaMetLysGluVal-200
SEQ. ID. NO. 5643    223-AlaPheLeuThrArgPheMetGlnTyrLeu-232
SEQ. ID. NO. 5644    252-AlaAsnGluMetAla-256
SEQ. ID. NO. 5645    270-GlyArgAsnTrpArgArgThrVal-277
Antigenic Index - Jameson-Wolf
SEQ. ID. NO. 5646    19-CysSerGlySerLysThrGluGlnProLysLeuAspTyrGlnSerArgSerHisArgLeuIleLys-40
SEQ. ID. NO. 5647    42-GluValProProAspLeuAsnAsnProAspGlnGlyAsnLeuTyr-56
SEQ. ID. NO. 5648    60-AlaGlySerGlyAlaValArgAlaSerAspLeuGluLysArgArgThrProAlaVal-78
SEQ. ID. NO. 5649    80-GlnProAlaAspAlaGluValLeuLysSerValLysGlyValArgLeuGluArgAspGlySerGln-101
SEQ. ID. NO. 5650    105-ValValArgGlyLysSerProAlaGlu-113
SEQ. ID. NO. 5651    123-GlnGluAsnGlyPheAspIleLysSerGluGluProAla-135
SEQ. ID. NO. 5652    139-MetGluThrGluTrpAlaGluAsnArgAlaLysIleProGlnAspSerLeuArgArgLeuPheAsp-160
SEQ. ID. NO. 5653    169-SerThrGlyGluArgAspLysPheIleValArgIleGluGlnGlyLysAsnGlyValSer-188
SEQ. ID. NO. 5654    195-LysAlaMetLysGluValTyrGlyGlyLysAspLysAspThrThr-209
SEQ. ID. NO. 5655    212-GlnProSerProSerAspProAsnLeu-220

TABLE 1-continued

| | |
|---|---|
| SEQ. ID. NO. 5656 | 233-GlyValAspGlyGlnGlnAlaGluAsnAlaSerAlaLysLysProThrLeu-249 |
| SEQ. ID. NO. 5657 | 253-AsnGluMetAlaArgIleGluGlyLysSer-262 |
| SEQ. ID. NO. 5658 | 268-AspTyrGlyArgAsnTrpArgArgThrVal-277 |
| SEQ. ID. NO. 5659 | 289-GlyGlnAsnThrGluArgHisAla-296 |
| SEQ. ID. NO. 5660 | 300-GlnLysAlaProAsnGluSerAsnAlaValThrGluGlnLysProGlyLeu-316 |
| SEQ. ID. NO. 5661 | 320-LeuLeuGlyLysGlyLysAlaGluLysProAlaGluGlnProGlu-334 |
| SEQ. ID. NO. 5662 | 342-ValAlaAsnGlySerArg-347 |
| SEQ. ID. NO. 5663 | 350-LeuLeuAsnLysAspGlySerAlaTyrAlaGlyLysAspAlaSer-364 |
| SEQ. ID. NO. 5664 | 370-LeuHisSerGluLeuArg-375 |
| Hydrophilic Regions - Hopp-Woods | |
| SEQ. ID. NO. 5665 | 20-SerGlySerLysThrGluGlnProLysLeuAspTyrGlnSerArgSerHisArgLeuIleLys-40 |
| SEQ. ID. NO. 5666 | 42-GluValProProAspLeuAsnAsnProAspGln-52 |
| SEQ. ID. NO. 5667 | 63-GlyAlaValArgAlaSerAspLeuGluLysArgArgThrProAla-77 |
| SEQ. ID. NO. 5668 | 80-GlnProAlaAspAlaGluValLeuLysSerValLysGlyValArgLeuGluArgAspGlySerGln-101 |
| SEQ. ID. NO. 5669 | 107-AspGlyLysSerProAla-112 |
| SEQ. ID. NO. 5670 | 125-AsnGlyPheAspIleLysSerGluGluProAla-135 |
| SEQ. ID. NO. 5671 | 139-MetGluThrGluTrpAlaGluAsnArgAlaLysIleProGlnAspSerLeuArgArgLeuPheAsp-160 |
| SEQ. ID. NO. 5672 | 170-ThrGlyGluArgAspLysPheIleVal-178 |
| SEQ. ID. NO. 5673 | 180-IleGluGlnGlyLysAsnGlyVal-187 |
| SEQ. ID. NO. 5674 | 195-LysAlaMetLysGluValTyrGlyGlyLysAspLysAspThrThr-209 |
| SEQ. ID. NO. 5675 | 214-SerProSerAspProAsnLeu-220 |
| SEQ. ID. NO. 5676 | 235-AspGlyGlnGlnAlaGluAsnAlaSerAlaLysLysProThr-248 |
| SEQ. ID. NO. 5677 | 253-AsnGluMetAlaArgIleGluGlyLysSer-262 |
| SEQ. ID. NO. 5678 | 269-TyrGlyArgAsnTrpArg-274 |
| SEQ. ID. NO. 5679 | 291-AsnThrGluArgHis-295 |
| SEQ. ID. NO. 5680 | 302-AlaProAsnGluSerAsnAlaValThrGluGlnLysProGlyLeu-316 |
| SEQ. ID. NO. 5681 | 320-LeuLeuGlyLysGlyLysAlaGluLysProAlaGluGlnProGlu-334 |
| SEQ. ID. NO. 5682 | 352-AsnLysAspGlySer-356 |
| SEQ. ID. NO. 5683 | 359-AlaGlyLysAspAlaSer-364 |
| SEQ. ID. NO. 5684 | 370-LeuHisSerGluLeuArg-375 |
| 531 | |
| AMPHI Regions - AMPHI | |
| SEQ. ID. NO. 5685 | 59-SerLeuAlaGlyIleLeuAlaAspTyrValAlaGlyIleTrpGlyThr-74 |
| SEQ. ID. NO. 5686 | 90-GlySerIleIleGlyIlePhePheSerLeuProGlyLeuIleLeuGly-105 |
| SEQ. ID. NO. 5687 | 108-IleGlyAlaAlaAlaGly-113 |
| SEQ. ID. NO. 5688 | 132-LeuLeuGlyLeuValVal-137 |
| Antigenic Index - Jameson-Wolf | |
| SEQ. ID. NO. 5689 | 74-ThrLysTyrThrGlyAlaGlyLysLeuAlaVal-84 |
| SEQ. ID. NO. 5690 | 114-GluLeuIleGluArgArgAsnMet-121 |
| Hydrophilic Regions - Hopp-Woods | |
| SEQ. ID. NO. 5691 | 114-GluLeuIleGluArgArgAsnMet-121 |
| 532 | |
| AMPHI Regions - AMPHI | |
| SEQ. ID. NO. 5692 | 6-GlyLysGlyAlaAsp-10 |
| SEQ. ID. NO. 5693 | 27-AlaLeuLeuSerAlaValThrHisLeuLeuAlaIlePheValProMetIleThr-44 |
| SEQ. ID. NO. 5694 | 76-TyrLeuGlnValAsnArgPheGlyPro-84 |
| SEQ. ID. NO. 5695 | 122-SerThrLeuLeuGly-126 |
| SEQ. ID. NO. 5696 | 147-LysValIleThrProThrVal-153 |
| SEQ. ID. NO. 5697 | 184-ThrPheGlySerMetGluAsnLeuGly-192 |
| SEQ. ID. NO. 5698 | 206-CysMetLysAsnPro-210 |
| SEQ. ID. NO. 5699 | 224-GlyTyrIleValAlaLeu-229 |
| SEQ. ID. NO. 5700 | 236-PheSerAlaLeuGlnAsnLeuPro-243 |
| SEQ. ID. NO. 5701 | 271-LeuSerValPheGluAlaValGlyAspLeuThrAla-282 |
| SEQ. ID. NO. 5702 | 297-ThrLysArgLeuArgGlyGlyVal-304 |
| SEQ. ID. NO. 5703 | 307-AspGlyLeuValSerValIleAlaThrAlaLeuGly-318 |
| SEQ. ID. NO. 5704 | 338-AlaSerArgHisValGlyLysTyr-345 |
| SEQ. ID. NO. 5705 | 361-ArgAlaPheThrThrIleProSerProVal-370 |
| Antigenic Index - Jameson-Wolf | |
| SEQ. ID. NO. 5706 | 1-MetSerGlyGlnLeuGlyLysGlyAlaAspAlaPro-12 |
| SEQ. ID. NO. 5707 | 18-LeuGluAspArgProProPheGlyAsn-26 |
| SEQ. ID. NO. 5708 | 80-AsnArgPheGlyPro-84 |
| SEQ. ID. NO. 5709 | 108-AlaGlyMetLysGluGlyGlyLeuThrLysAspAlaMet-120 |
| SEQ. ID. NO. 5710 | 177-PheGlyAlaLysAlaAspGlyThrPheGlySer-187 |
| SEQ. ID. NO. 5711 | 207-MetLysAsnProLeuLeuArg-213 |
| SEQ. ID. NO. 5712 | 286-ValSerAspGlnProIleGluGlyGluGluTyrThrLysArgLeuArgGlyGlyValLeu-305 |
| SEQ. ID. NO. 5713 | 391-ValSerHisGlyIleArgArgArgGluAlaVal-401 |
| SEQ. ID. NO. 5714 | 445-LeuProGluAspLysThrGluAlaAlaValLysPheAspThrAspHisLeuGluHis-463 |
| Hydrophilic Regions - Hopp-Woods | |
| SEQ. ID. NO. 5715 | 4-GlnLeuGlyLysGlyAlaAspAlaPro-12 |
| SEQ. ID. NO. 5716 | 18-LeuGluAspArgProProPhe-24 |
| SEQ. ID. NO. 5717 | 109-GlyMetLysGluGlyGlyLeuThrLysAspAlaMet-120 |
| SEQ. ID. NO. 5718 | 179-AlaLysAlaAspGly-183 |
| SEQ. ID. NO. 5719 | 289-GlnProIleGluGlyGluGluTyrThrLysArgLeuArgGly-302 |
| SEQ. ID. NO. 5720 | 394-GlyIleArgArgArgGluAlaVal-401 |
| SEQ. ID. NO. 5721 | 445-LeuProGluAspLysThrGluAlaAlaValLysPheAspThrAspHisLeuGluHis-463 |
| 537-2 | |
| AMPHI Regions - AMPHI | |
| SEQ. ID. NO. 5722 | 38-GlnIleArgAspGlyGlyAspAlaLeuHisTyrLeuAsnArgIle-52 |
| SEQ. ID. NO. 5723 | 86-HisGlyGluHisHis-90 |
| SEQ. ID. NO. 5724 | 109-GlyTyrLeuTyrAsnGlyValHisGlu-117 |

TABLE 1-continued

| | |
|---|---|
| SEQ. ID. NO. 5725 | 138-ArgGlnValAspGlyLeuMetSerAlaIleTyr-148 |
| SEQ. ID. NO. 5726 | 182-ArgPheGluArgHisCys-187 |
| SEQ. ID. NO. 5727 | 194ProGluAlaGlyArgLysTyrTyrArgAsnAla-204 |
| SEQ. ID. NO. 5728 | 281-ArgProValArgValLeuThrAlaGly-289 |
| SEQ. ID. NO. 5729 | 315-TyrThrAlaValPheAspTyrValArgAsnGlyArgArgAla-328 |

Antigenic Index - Jameson-Wolf

| | |
|---|---|
| SEQ. ID. NO. 5730 | 21-ThrGlnAsnGlnSerLeuProAlaGly-29 |
| SEQ. ID. NO. 5731 | 32-ValTyrProSerAlaProGlnIleArgAspGlyGlyAspAla-45 |
| SEQ. ID. NO. 5732 | 69-AsnSerAlaArgArgHisAlaSer-76 |
| SEQ. ID. NO. 5733 | 80-LeuAsnProGluAspGlyHisGlyGluHisHisProAspAsnProHis-95 |
| SEQ. ID. NO. 5734 | 99-GlnLysLeuThrGluArgThrArgLeu-107 |
| SEQ. ID. NO. 5735 | 115-ValHisGluAsnIleSerThrGluGluGluAlaAlaGluSerSerAspSerAspIleArgThrGlnGlnArgGlnValAspGlyLeu-143 |
| SEQ. ID. NO. 5736 | 152-SerLeuLeuAspArgHisThrAspGluAlaGly-162 |
| SEQ. ID. NO. 5737 | 165-PheValArgGluAsnGlyLysThr-172 |
| SEQ. ID. NO. 5738 | 178-GlnGlyAsnGlyArgPheGluArgHisCysAlaGlnGlyArgAsnGlnProGluAlaGlyArgLysTyrTyrArgAsnAlaCysHisAsnGly-208 |
| SEQ. ID. NO. 5739 | 212-TyrThrAspGluAlaMetPro-218 |
| SEQ. ID. NO. 5740 | 237-PheHisGlyGluArgProAspProValProGluTyrGluIleThrGlyAsnProAlaSer-256 |
| SEQ. ID. NO. 5741 | 258-AspPheSerGluAlaAlaGly-264 |
| SEQ. ID. NO. 5742 | 266-IleThrMetLysSer-270 |
| SEQ. ID. NO. 5743 | 274-TyrGlnGlyLysAsnGluIleArgPro-282 |
| SEQ. ID. NO. 5744 | 287-ThrAlaGlyAsnAspProAsnGlyArgLeuThr-297 |
| SEQ. ID. NO. 5745 | 320-AspTyrValArgAsnGlyArgArgAlaGlnAla-330 |
| SEQ. ID. NO. 5746 | 334-PheArgThrArgLysProAspTyrProTyr-343 |
| SEQ. ID. NO. 5747 | 345-GluValAsnGlyGlyGluThrLeuAlaValArgLysGlyGluLys-359 |
| SEQ. ID. NO. 5748 | 364-TrpArgGlyArgTrpCysLeu-370 |
| SEQ. ID. NO. 5749 | 376-TyrThrTyrArgGlnArgProGlySerArgLeuSerIleGlyArgHisGluAlaGlyGly-395 |
| SEQ. ID. NO. 5750 | 401-AspGlyMetAlaGlySer-406 |
| SEQ. ID. NO. 5751 | 408-IleThrLeuAlaProGluGlyGluThrGluArgGly-419 |

Hydrophilic Regions - Hopp-Woods

| | |
|---|---|
| SEQ. ID. NO. 5752 | 37-ProGlnIleArgAspGlyGlyAsp-44 |
| SEQ. ID. NO. 5753 | 69-AsnSerAlaArgArgHisAla-75 |
| SEQ. ID. NO. 5754 | 81-AsnProGluAspGlyHisGlyGluHisHisProAsp-92 |
| SEQ. ID. NO. 5755 | 100-LysLeuThrGluArgThrArgLeu-107 |
| SEQ. ID. NO. 5756 | 119-IleSerThrGluGluGluAlaAlaGluSerSerAspSerAspIleArgThrGlnGlnArgGlnValAsp-141 |
| SEQ. ID. NO. 5757 | 152-SerLeuLeuAspArgHisThrAspGluAlaGly-162 |
| SEQ. ID. NO. 5758 | 165-PheValArgGluAsnGlyLys-171 |
| SEQ. ID. NO. 5759 | 179-GlyAsnGlyArgPheGluArgHisCysAlaGlnGlyArgAsnGlnProGluAlaGlyArgLysTyrTyrArg-202 |
| SEQ. ID. NO. 5760 | 238-HisGlyGluArgProAspProValProGlu-247 |
| SEQ. ID. NO. 5761 | 258-AspPheSerGluAlaAlaGly-264 |
| SEQ. ID. NO. 5762 | 266-IleThrMetLysSer-270 |
| SEQ. ID. NO. 5763 | 275-GlnGlyLysAsnGluIleArgPro-282 |
| SEQ. ID. NO. 5764 | 289-GlyAsnAspProAsnGlyArg-295 |
| SEQ. ID. NO. 5765 | 323-ArgAsnGlyArgArgAlaGlnAla-330 |
| SEQ. ID. NO. 5766 | 334-PheArgThrArgLysProAsp-340 |
| SEQ. ID. NO. 5767 | 352-LeuAlaValArgLysGlyGluLys-359 |
| SEQ. ID. NO. 5768 | 377-ThrTyrArgGlnArgProGlySer-384 |
| SEQ. ID. NO. 5769 | 387-SerIleGlyArgHisGluAla-393 |
| SEQ. ID. NO. 5770 | 412-ProGluGlyGluThrGluArgGly-419 |

538-2
AMPHI Regions - AMPHI

| | |
|---|---|
| SEQ. ID. NO. 5771 | 42-ThrAlaLeuAlaGluAlaValGluLeuValLysAlaAlaGly-55 |
| SEQ. ID. NO. 5772 | 79-LysAlaAlaGluLeuSerGluAlaValAla-88 |
| SEQ. ID. NO. 5773 | 145-GlnLeuSerHisLeuAlaGlyArgLeuIleArgGlyTyrGlyHisLeuGln-161 |
| SEQ. ID. NO. 5774 | 188-IleAsnAlaLeuLysLysGlnLeuAla-196 |
| SEQ. ID. NO. 5775 | 211-SerGlyThrIleLysThrPheAlaLeuValGlyTyrThrAsn-224 |
| SEQ. ID. NO. 5776 | 231-PheAsnArgLeuThrLys-236 |
| SEQ. ID. NO. 5777 | 271-GlyPheValSerAspLeuProHisLysLeuIleSerAlaPheSerAlaThrLeuGlu-289 |
| SEQ. ID. NO. 5778 | 307-AsnSerGlyGlnGlnIleGluAspValGluAsnValLeuGlnGluIleHis-323 |
| SEQ. ID. NO. 5779 | 365-GluAsnThrGlyIleAspAlaLeuArgGluAlaIleAlaGluSerCysAla-381 |

Antigenic Index - Jameson-Wolf

| | |
|---|---|
| SEQ. ID. NO. 5780 | 1-MetThrGlyArgThrGlyGlyAsnGlySerThrGlnAlaGlnProGluArg-17 |
| SEQ. ID. NO. 5781 | 24-MetLeuAspLysAspGlyThrGlySerSerAlaAlaArg-36 |
| SEQ. ID. NO. 5782 | 48-ValGluLeuValLys-52 |
| SEQ. ID. NO. 5783 | 54-AlaGlyGlyAspSerValArgValGluThrAlaLysArgAspArgProHisThr-71 |
| SEQ. ID. NO. 5784 | 77-ThrGlyLysAlaAlaGluLeuSerGlu-85 |
| SEQ. ID. NO. 5785 | 100-GluLeuThrProThrGlnGluArgAsnLeuGluLysGluLeuLysCysArgValLeuAsp-119 |
| SEQ. ID. NO. 5786 | 129-AlaArgArgAlaArgThrGlnGluGlyArgLeuGlnVal-141 |
| SEQ. ID. NO. 5787 | 161-GlnSerArgGlyGlyIleGlyMetLysGlyProGlyGluThrLysLeuGluThrAspArgArgLeuIle-184 |
| SEQ. ID. NO. 5788 | 189-AsnAlaLeuLysLysGlnLeuAlaAsnLeuLysLysGlnArgAlaLeuArgArgLysSerArgGluSerGlyThrIleLysThr-216 |
| SEQ. ID. NO. 5789 | 224-AsnValGlyLysSerSerLeu-230 |
| SEQ. ID. NO. 5790 | 233-ArgLeuThrLysSerArgGlyIleTyrAla-241 |
| SEQ. ID. NO. 5791 | 257-TyrIleSerProGluCys-262 |
| SEQ. ID. NO. 5792 | 287-ThrLeuGluGluThrAlaGln-293 |
| SEQ. ID. NO. 5793 | 304-AlaAlaProAsnSerGlyGlnGlnIleGluAspValGluAsnValLeu-319 |
| SEQ. ID. NO. 5794 | 323-HisAlaGlyAspIlePro-328 |
| SEQ. ID. NO. 5795 | 333-TyrAsnLysThrAspLeuLeuProSerGluGluGlnAsnThrGlyIle-348 |
| SEQ. ID. NO. 5796 | 365-GluAsnThrGlyIleAspAlaLeuArgGluAlaIleAla-377 |
| SEQ. ID. NO. 5797 | 380-CysAlaAlaAlaProAsnThrAspGluThrGluMetPro-392 |

Hydrophilic Regions - Hopp-Woods

| | |
|---|---|
| SEQ. ID. NO. 5798 | 1-MetThrGlyArgThrGlyGly-7 |

TABLE 1-continued

| | |
|---|---|
| SEQ. ID. NO. 5799 | 13-AlaGlnProGluArg-17 |
| SEQ. ID. NO. 5800 | 25-LeuAspLysAspGlyThrGly-31 |
| SEQ. ID. NO. 5801 | 48-ValGluLeuValLys-52 |
| SEQ. ID. NO. 5802 | 54-AlaGlyGlyAspSerValArgValGluThrAlaLysArgAspArgProHis-70 |
| SEQ. ID. NO. 5803 | 78-GlyLysAlaAlaGluLeuSerGlu-85 |
| SEQ. ID. NO. 5804 | 101-LeuThrProThrGlnGluArgAsnLeuGluLysGluLeuLysCysArgValLeuAsp-119 |
| SEQ. ID. NO. 5805 | 129-AlaArgArgAlaArgThrGlnGluGlyArgLeuGlnVal-141 |
| SEQ. ID. NO. 5806 | 161-GlnSerGlnArgGlyGlyIle-167 |
| SEQ. ID. NO. 5807 | 171-GlyProGlyGluThrLysLeuGluThrAspArgArgLeuIle-184 |
| SEQ. ID. NO. 5808 | 189-AsnAlaLeuLysLysGlnLeuAlaAsnLeuLysLysGlnArgAlaLeuArgArgLysSerArgGluSerGlyThr-213 |
| SEQ. ID. NO. 5809 | 287-ThrLeuGluGluThrAlaGln-293 |
| SEQ. ID. NO. 5810 | 310-GlnGlnIleGluAspValGluAsnValLeu-319 |
| SEQ. ID. NO. 5811 | 337-AspLeuLeuProSerGluGluGlnAsn-345 |
| SEQ. ID. NO. 5812 | 370-AspAlaLeuArgGluAlaIleAla-377 |
| SEQ. ID. NO. 5813 | 384-ProAsnThrAspGluThrGluMetPro-392 |

539-2
AMPHI Regions - AMPHI

| | |
|---|---|
| SEQ. ID. NO. 5814 | 18-ArgGlnArgGluHisHisArgLeu-25 |
| SEQ. ID. NO. 5815 | 44-LeuValGlyGlyPheAspPheLeuArgValIleGlyCysGlyGlyValAlaTyrLeuProAspPheGlnGln-67 |

Antigenic Index - Jameson-Wolf

| | |
|---|---|
| SEQ. ID. NO. 5816 | 1-MetGluAspLeuGlnGluIleGly-8 |
| SEQ. ID. NO. 5817 | 15-LysValGlyArgGlnArgGluHisHisArgLeuHisHisProGlnProGlyAsnGlyGluAlaAspAsp-37 |
| SEQ. ID. NO. 5818 | 63-ProAspPheGlnGlnAsnValGlyLysAlaAsp-73 |
| SEQ. ID. NO. 5819 | 77-ValProAspAspAlaAlaAla-83 |
| SEQ. ID. NO. 5820 | 88-IleGluValAspAlaAspAspAlaValCys-97 |
| SEQ. ID. NO. 5821 | 102-LeuPheAspGlnProAspAlaGlyGlyAlaGlyAspAlaAlaGluHis-117 |

Hydrophilic Regions - Hopp-Woods

| | |
|---|---|
| SEQ. ID. NO. 5822 | 1-MetGluAspLeuGlnGluIleGly-8 |
| SEQ. ID. NO. 5823 | 15-LysValGlyArgGlnArgGluHisHisArg-24 |
| SEQ. ID. NO. 5824 | 31-GlyAsnGlyGluAlaAspAsp-37 |
| SEQ. ID. NO. 5825 | 69-ValGlyLysAlaAsp-73 |
| SEQ. ID. NO. 5826 | 78-ProAspAspAlaAlaAla-83 |
| SEQ. ID. NO. 5827 | 88-IleGluValAspAlaAspAspAlaValCys-97 |
| SEQ. ID. NO. 5828 | 102-LeuPheAspGlnProAspAlaGlyGlyAlaGlyAspAlaAlaGluHis-117 |

542-2
AMPHI Regions - AMPHI

| | |
|---|---|
| SEQ. ID. NO. 5829 | 6-ArgIleArgArgCysSerVal-12 |

Antigenic Index - Jameson-Wolf

| | |
|---|---|
| SEQ. ID. NO. 5830 | 1-MetProLysTrpSerArgIleArgArgCysSerVal-12 |
| SEQ. ID. NO. 5831 | 37-ValArgLeuLysSerSerAspGlyIleAlaSer-47 |
| SEQ. ID. NO. 5832 | 56-GlyProMetProSerGluThrValSerHisLysSerAspSerSerArgAsnThrSerAlaSerArgArgAsnValSerProLysCysProPhe-86 |
| SEQ. ID. NO. 5833 | 90-PheArgGlnAspAlaAlaLysProArgArgPheGlyGlyLys-103 |
| SEQ. ID. NO. 5834 | 107-LeuThrGlySerArg-111 |

Hydrophilic Regions - Hopp-Woods

| | |
|---|---|
| SEQ. ID. NO. 5835 | 5-SerArgIleArgArgCysSer-11 |
| SEQ. ID. NO. 5836 | 37-ValArgLeuLysSerSerAspGlyIleAla-46 |
| SEQ. ID. NO. 5837 | 58-MetProSerGluThrValSerHisLysSerAspSerSerArgAsnThrSerAlaSerArgArgAsnValSerPro-82 |
| SEQ. ID. NO. 5838 | 90-PheGlnAspAlaAlaLysProArgArgPheGlyGly-102 |

544-2
AMPHI Regions - AMPHI

| | |
|---|---|
| SEQ. ID. NO. 5839 | 11-AlaLeuIleGlyIleLeu-16 |
| SEQ. ID. NO. 5840 | 55-PheTrpPheProSerCysProGlyCysValSerGluMetProLysIleIleLysThrAla-74 |
| SEQ. ID. NO. 5841 | 85-LeuAlaValAlaGlnProIleAspProIleGluSerValArgGlnTyrVal-101 |
| SEQ. ID. NO. 5842 | 116-LysAlaValGlyGlnAlaPhe-122 |

Antigenic Index - Jameson-Wolf

| | |
|---|---|
| SEQ. ID. NO. 5843 | 1-MetLysLysIleLeu-5 |
| SEQ. ID. NO. 5844 | 22-IleProAspSerLysThrAlaPro-29 |
| SEQ. ID. NO. 5845 | 35-AspLeuHisGlyLysThrValSerAsnAlaAspLeuGlnGly-48 |
| SEQ. ID. NO. 5846 | 59-SerCysProGlyCys-63 |
| SEQ. ID. NO. 5847 | 66-GluMetProLysIleIleLysThrAlaAsnAspTyrLysAsnLysAsnPhe-82 |
| SEQ. ID. NO. 5848 | 90-ProIleAspProIleGluSerValArgGlnTyrValLysAspTyrGly-105 |
| SEQ. ID. NO. 5849 | 113-AspAlaAspLysAlaVal-118 |
| SEQ. ID. NO. 5850 | 133-IleGlyLysLysGlyGluIleLeu-140 |
| SEQ. ID. NO. 5851 | 144-ValGlyGluProAspPheGlyLysLeuTyrGlnGluIleAspThrAlaTrpArgAsnSerAspAlaVal-166 |

Hydrophilic Regions - Hopp-Woods

| | |
|---|---|
| SEQ. ID. NO. 5852 | 1-MetLysLysIleLeu-5 |
| SEQ. ID. NO. 5853 | 23-ProAspSerLysThr-27 |
| SEQ. ID. NO. 5854 | 66-GluMetProLysIleIleLysThrAlaAsnAspTyrLysAsnLysAsn-81 |
| SEQ. ID. NO. 5855 | 92-AspProIleGluSerValArgGlnTyrValLys-102 |
| SEQ. ID. NO. 5856 | 113-AspAlaAspLysAlaVal-118 |
| SEQ. ID. NO. 5857 | 133-IleGlyLysLysGlyGluIle-139 |
| SEQ. ID. NO. 5858 | 156-IleAspThrAlaTrpArgAsnSerAspAlaVal-166 |

547-2
AMPHI Regions - AMPHI

| | |
|---|---|
| SEQ. ID. NO. 5859 | 7-PheAsnLysThrValAlaSerPheAlaGlnIleValGluThrPheAspVal-23 |
| SEQ. ID. NO. 5860 | 62-AsnArgSerPheLys-66 |
| SEQ. ID. NO. 5861 | 105-LeuHisIlePheThrAsnIle-111 |
| SEQ. ID. NO. 5862 | 121-GluLeuLeuThrIleLeuValLys-128 |

Antigenic Index - Jameson-Wolf

| | |
|---|---|
| SEQ. ID. NO. 5863 | 3-ValAspAsnGlyPheAsnLysThrVal-11 |

TABLE 1-continued

| | |
|---|---|
| SEQ. ID. NO. 5864 | 35-GlnMetLysGlnArgCysGly-41 |
| SEQ. ID. NO. 5865 | 53-PheProArgCysGlyPheGluIleProAsnArgSerPheLysGlu-67 |
| SEQ. ID. NO. 5866 | 76-LeuSerGluArgPheArgThrAsnAlaGluValGluMet-88 |
| SEQ. ID. NO. 5867 | 129-AsnLeuSerProAsnGlyLysLysArgPhe-138 |
| Hydrophilic Regions - Hopp-Woods | |
| SEQ. ID. NO. 5868 | 36-MetLysGlnArgCys-40 |
| SEQ. ID. NO. 5869 | 60-IleProAsnArgSerPheLysGlu-67 |
| SEQ. ID. NO. 5870 | 76-LeuSerGluArgPheArgThrAsnAlaGluValGluMet-88 |
| SEQ. ID. NO. 5871 | 130-LeuSerProAsnGlyLysLysArgPhe-138 |
| 548-2 (from 23) | |
| AMPHI Regions - AMPHI | |
| SEQ. ID. NO. 5872 | 14-ValLeuAlaAlaLeuAlaAlaCysLys-22 |
| SEQ. ID. NO. 5873 | 39-SerAlaAlaGluAsnAlaAlaLysPro-47 |
| SEQ. ID. NO. 5874 | 89-PheThrHisCysProAspValCysProThr-98 |
| SEQ. ID. NO. 5875 | 103-TyrSerAspThrLeuLysGlnLeuGlyGlyGln-113 |
| SEQ. ID. NO. 5876 | 132-GluIleIleGlyLysTyrAlaLys-139 |
| Antigenic Index - Jameson-Wolf | |
| SEQ. ID. NO. 5877 | 21-CysLysProGlnAspAsnSerAlaAla-29 |
| SEQ. ID. NO. 5878 | 39-SerAlaAlaGluAsnAlaAlaLysProGlnThrArgGlyThrAspMetArgLysGluAspIleGlyGlyAspPheThrLeuThrAspGlyGluGlyLysProPheAsn-74 |
| SEQ. ID. NO. 5879 | 76-SerAspLeuLysGly-80 |
| SEQ. ID. NO. 5880 | 91-HisCysProAspValCysPro-97 |
| SEQ. ID. NO. 5881 | 104-SerAspThrLeuLysGlnLeuGlyGlyGlnAlaLysAspValLys-118 |
| SEQ. ID. NO. 5882 | 124-IleAspProGluArgAspThrProGluIleIleGlyLysTyrAlaLysGlnPheAsnProAspPhe-145 |
| SEQ. ID. NO. 5883 | 150-AlaThrGlyGlyGln-154 |
| SEQ. ID. NO. 5884 | 169-LysValAsnGlnLysAspAspSerGluAsnTyrLeu-180 |
| SEQ. ID. NO. 5885 | 189-LeuIleAspLysAsnGlyGlu-195 |
| SEQ. ID. NO. 5886 | 200-SerProTyrGlySerGluProGluThrIleAlaAlaAspVal-213 |
| Hydrophilic Regions - Hopp-Woods | |
| SEQ. ID. NO. 5887 | 22-LysProGlnAspAsnSerAla-28 |
| SEQ. ID. NO. 5888 | 39-SerAlaAlaGluAsnAlaAlaLysProGlnThrArgGlyThrAspMetArgLysGluAspIleGlyGly-61 |
| SEQ. ID. NO. 5889 | 64-ThrLeuThrAspGlyGluGlyLysPro-72 |
| SEQ. ID. NO. 5890 | 76-SerAspLeuLysGly-80 |
| SEQ. ID. NO. 5891 | 111-GlyGlyGlnAlaLysAspValLys-118 |
| SEQ. ID. NO. 5892 | 124-IleAspProGluArgAspThrProGluIleIle-134 |
| SEQ. ID. NO. 5893 | 169-LysValAsnGlnLysAspAspSerGluAsnTyrLeu-180 |
| SEQ. ID. NO. 5894 | 191-AspLysAsnGlyGlu-195 |
| SEQ. ID. NO. 5895 | 203-GlySerGluProGluThrIleAlaAlaAspVal-213 |
| 548-2 (from earlier--to be deleted) | |
| AMPHI Regions - AMPHI | |
| SEQ. ID. NO. 5896 | 14-ValLeuAlaAlaLeuAlaAlaCysLys-22 |
| SEQ. ID. NO. 5897 | 39-SerAlaAlaGluAsnAlaAlaLysPro-47 |
| SEQ. ID. NO. 5898 | 89-PheThrHisCysProAspValCysProThr-98 |
| SEQ. ID. NO. 5899 | 103-TyrSerAspThrLeuLysGlnLeuGlyGlyGln-113 |
| SEQ. ID. NO. 5900 | 132-GluIleIleGlyLysTyrAlaLys-139 |
| Antigenic Index - Jameson-Wolf | |
| SEQ. ID. NO. 5901 | 21-CysLysProGlnAspAsnSerAlaAla-29 |
| SEQ. ID. NO. 5902 | 39-SerAlaAlaGluAsnAlaAlaLysProGlnThrArgGlyThrAspMetArgLysGluAspIleGlyGlyAspPheThrLeuThrAspGlyGluGlyLysProPheAsn-74 |
| SEQ. ID. NO. 5903 | 76-SerAspLeuLysGly-80 |
| SEQ. ID. NO. 5904 | 91-HisCysProAspValCysPro-97 |
| SEQ. ID. NO. 5905 | 104-SerAspThrLeuLysGlnLeuGlyGlyGlnAlaLysAspValLys-118 |
| SEQ. ID. NO. 5906 | 124-IleAspProGluArgAspThrProGluIleIleGlyLysTyrAlaLysGlnPheAsnProAspPhe-145 |
| SEQ. ID. NO. 5907 | 150-AlaThrGlyGlyGln-154 |
| SEQ. ID. NO. 5908 | 169-LysValAsnGlnLysAspAspSerGluAsnTyrLeu-180 |
| SEQ. ID. NO. 5909 | 189-LeuIleAspLysAsnGlyGlu-195 |
| SEQ. ID. NO. 5910 | 200-SerProTyrGlySerGluProGluThrIleAlaAlaAspVal-213 |
| Hydrophilic Regions - Hopp-Woods | |
| SEQ. ID. NO. 5911 | 22-LysProGlnAspAsnSerAla-28 |
| SEQ. ID. NO. 5912 | 39-SerAlaAlaGluAsnAlaAlaLysProGlnThrArgGlyThrAspMetArgLysGluAspIleGlyGly-61 |
| SEQ. ID. NO. 5913 | 64-ThrLeuThrAspGlyGluGlyLysPro-72 |
| SEQ. ID. NO. 5914 | 76-SerAspLeuLysGly-80 |
| SEQ. ID. NO. 5915 | 111-GlyGlyGlnAlaLysAspValLys-118 |
| SEQ. ID. NO. 5916 | 124-IleAspProGluArgAspThrProGluIleIle-134 |
| SEQ. ID. NO. 5917 | 169-LysValAsnGlnLysAspAspSerGluAsnTyrLeu-180 |
| SEQ. ID. NO. 5918 | 191-AspLysAsnGlyGlu-195 |
| SEQ. ID. NO. 5919 | 203-GlySerGluProGluThrIleAlaAlaAspVal-213 |
| 552-1 | |
| AMPHI Regions - AMPHI | |
| SEQ. ID. NO. 5920 | 18-CysThrAsnAlaPheAlaAlaPro-25 |
| SEQ. ID. NO. 5921 | 29-AlaSerLeuAlaArgTrpLeuAspThr-37 |
| SEQ. ID. NO. 5922 | 41-AspArgAspIleGluLysAsnMetIleGluGlyPheAsnAlaGlyPheLysProTyrAlaAspLysAlaLeuAlaGluMet-67 |
| SEQ. ID. NO. 5923 | 75-AlaAlaGluAlaPheAsnArgTyrArgGluAsnVal-86 |
| SEQ. ID. NO. 5924 | 89-AspLeuIleThrProGluValLys-96 |
| SEQ. ID. NO. 5925 | 116-IleAspGlyMetIleAla-121 |
| SEQ. ID. NO. 5926 | 139-IleLysLysSerMetSerGluIle-146 |
| SEQ. ID. NO. 5927 | 154-SerGlyLysIleAlaGlnHisHisLeuProGluPheThrGluGluLeuArgArg-171 |
| Antigenic Index - Jameson-Wolf | |
| SEQ. ID. NO. 5928 | 25-ProProSerAspAlaSerLeu-31 |
| SEQ. ID. NO. 5929 | 35-LeuAspThrGlnAsnPheAspArgAspIleGluLysAsnMetIle-49 |

TABLE 1-continued

| | |
|---|---|
| SEQ. ID. NO. 5930 | 58-ProTyrAlaAspLysAlaLeuAlaGluMetProGluAlaLysLysAspGlnAlaAla-76 |
| SEQ. ID. NO. 5931 | 78-AlaPheAsnArgTyrArgGluAsnValLeu-87 |
| SEQ. ID. NO. 5932 | 90-LeuIleThrProGluValLysGlnAlaVal-99 |
| SEQ. ID. NO. 5933 | 105-LysAsnAlaArgGluIleTyrThrGlnGluGluIleAspGly-118 |
| SEQ. ID. NO. 5934 | 131-ValValAlaLysAsnProArgLeuIleLysLysSerMetSer-144 |
| SEQ. ID. NO. 5935 | 153-LeuSerGlyLysIle-157 |
| SEQ. ID. NO. 5936 | 164-GluPheThrGluGluLeuArgArg-171 |
| SEQ. ID. NO. 5937 | 173-IleCysGlyGlyLysAsnProAspAlaGlyCysLysGlnAlaGlyGlnValGlyLysArgHisGlnLys-195 |
| Hydrophilic Regions - Hopp-Woods | |
| SEQ. ID. NO. 5938 | 26-ProSerAspAlaSerLeu-31 |
| SEQ. ID. NO. 5939 | 38-GlnAsnPheAspArgAspIleGluLysAsnMetIle-49 |
| SEQ. ID. NO. 5940 | 58-ProTyrAlaAspLysAlaLeuAlaGluMetProGluAlaLysLysAspGlnAlaAla-76 |
| SEQ. ID. NO. 5941 | 78-AlaPheAsnArgTyrArgGluAsnValLeu-87 |
| SEQ. ID. NO. 5942 | 90-LeuIleThrProGluValLysGlnAlaVal-99 |
| SEQ. ID. NO. 5943 | 105-LysAsnAlaArgGluIleTyrThr-112 |
| SEQ. ID. NO. 5944 | 114-GluGluIleAspGly-118 |
| SEQ. ID. NO. 5945 | 131-ValValAlaLysAsnProArgLeuIleLysLysSerMetSer-144 |
| SEQ. ID. NO. 5946 | 164-GluPheThrGluGluLeuArgArg-171 |
| SEQ. ID. NO. 5947 | 176-GlyLysAsnProAspAlaGlyCysLysGlnAlaGlyGlnValGlyLysArgHisGlnLys-195 |
| 553-2 | |
| AMPHI Regions - AMPHI | |
| SEQ. ID. NO. 5948 | 31-LeuThrSerIleLeuSerTyrTyrGly-39 |
| SEQ. ID. NO. 5949 | 59-AsnLeuAlaAspIleMetArgPheGlyAsn-68 |
| SEQ. ID. NO. 5950 | 83-GluLeuSerAsnLeu-87 |
| Antigenic Index - Jameson-Wolf | |
| SEQ. ID. NO. 5951 | 10-GlyPheAsnLysLysLeuPro-16 |
| SEQ. ID. NO. 5952 | 42-ThrAspLeuArgThrLeuArgGlnLysTyr-51 |
| SEQ. ID. NO. 5953 | 56-LysGlyAlaAsnLeu-60 |
| SEQ. ID. NO. 5954 | 65-ArgPheGlyAsnGluMetAsnLeuThrProArgAlaLeuArgLeuGluLeuAspGluLeuSerAsn-86 |
| SEQ. ID. NO. 5955 | 105-SerIleSerLysAspSerIle-111 |
| SEQ. ID. NO. 5956 | 116-ProAlaValGlyMetArgLysIleLysMetAspGluValSerGlnLys-131 |
| SEQ. ID. NO. 5957 | 143-ThrHisPheGluGluLysLysGluThrLysLysIleLys-155 |
| SEQ. ID. NO. 5958 | 160-LeuArgGlyGlyGlnAla-165 |
| Hydrophilic Regions - Hopp-Woods | |
| SEQ. ID. NO. 5959 | 42-ThrAspLeuArgThrLeuArgGln-49 |
| SEQ. ID. NO. 5960 | 75-ArgAlaLeuArgLeuGluLeuAspGluLeuSer-85 |
| SEQ. ID. NO. 5961 | 106-IleSerLysAspSer-110 |
| SEQ. ID. NO. 5962 | 118-ValGlyMetArgLysIleLysMetAspGluValSerGln-130 |
| SEQ. ID. NO. 5963 | 144-HisPheGluGluLysLysGluThrLysLysIleLys-155 |
| 554 | |
| AMPHI Regions - AMPHI | |
| SEQ. ID. NO. 5964 | 35-AlaProThrPheGlnThrProGluThrLeu-44 |
| SEQ. ID. NO. 5965 | 71-AlaAlaLeuThrGlnLeuMet-77 |
| SEQ. ID. NO. 5966 | 110-ArgMetPheValArgProGlyAspThrVal-119 |
| SEQ. ID. NO. 5967 | 124-LeuLeuLysGlyMet-128 |
| SEQ. ID. NO. 5968 | 148-SerIleGluAsnPheValGlnGlnMetAsnLysGlu-159 |
| SEQ. ID. NO. 5969 | 193-GluAlaLeuMetArgAspPheProGluTyrTyrProLeuPheSer-207 |
| SEQ. ID. NO. 5970 | 296-ThrValAlaGlnIle-300 |
| SEQ. ID. NO. 5971 | 331-GluGlnIleLeuGluThrIleGlnProIleProAla-342 |
| Antigenic Index - Jameson-Wolf | |
| SEQ. ID. NO. 5972 | 24-SerProAlaProAsnArgProThrVal-32 |
| SEQ. ID. NO. 5973 | 37-ThrPheGlnThrProGluThr-43 |
| SEQ. ID. NO. 5974 | 53-LeuGlnSerLysGln-57 |
| SEQ. ID. NO. 5975 | 61-AlaLysAsnIleAsnThrProValGlu-69 |
| SEQ. ID. NO. 5976 | 84-LysAsnMetLysSerGlyAsnIleGlnSerGluGluAsnLeuLysIleProGlu-101 |
| SEQ. ID. NO. 5977 | 104-TrpAlaSerGluGlyGlySerArgMetPheValArgProGlyAspThrValSerThrAspLysLeuLeu-125 |
| SEQ. ID. NO. 5978 | 143-ArgLeuGlyAsnGlySerIleGluAsnPhe-152 |
| SEQ. ID. NO. 5979 | 156-MetAsnLysGluAlaArgArgLeuGlyMetLysAsnThrValPheLysAsnProThrGlyLeuSerArgGluGlyGlnValSerThrAlaLysAsp-187 |
| SEQ. ID. NO. 5980 | 194-AlaLeuMetArgAspPheProGluTyrTyr-203 |
| SEQ. ID. NO. 5981 | 214-LysAsnIleGluGlnAsnAsnArgAsnIleLeu-224 |
| SEQ. ID. NO. 5982 | 226-TyrArgAspAsnAsnValAsnGlyLeuLysAlaGlyHisThrGluSerGlyGlyTyrAsn-245 |
| SEQ. ID. NO. 5983 | 250-TyrSerGlyAsnGlyArgHis-256 |
| SEQ. ID. NO. 5984 | 262-LeuGlySerGluSerAlaGluThrArgAlaSerAspAsnSerLys-276 |
| SEQ. ID. NO. 5985 | 285-PheAspThrProLysIleTyrProLysGlyLysThr-296 |
| SEQ. ID. NO. 5986 | 302-IleSerGlyGlySerLysLysThrValArg-311 |
| SEQ. ID. NO. 5987 | 323-ProHisLysGluAlaLysMetAlaGluGlnIleLeu-334 |
| SEQ. ID. NO. 5988 | 342-AlaProValLysLysGlyGlnIleLeuGlyLysIleLysIleArgGlnAsnGlyTyr-360 |
| SEQ. ID. NO. 5989 | 362-IleAlaGluLysGluIleValAla-369 |
| SEQ. ID. NO. 5990 | 371-GluAsnValLysLysArgSerArgTrpGlnArg-381 |
| Hydrophilic Regions - Hopp-Woods | |
| SEQ. ID. NO. 5991 | 26-AlaProAsnArgProThr-31 |
| SEQ. ID. NO. 5992 | 85-AsnMetLysSerGlyAsnIleGlnSerGluGluAsnLeuLysIleProGlu-101 |
| SEQ. ID. NO. 5993 | 107-GluGlySerArgMetPheValArgProGlyAspThrValSerThrAspLysLeuLeu-125 |
| SEQ. ID. NO. 5994 | 156-MetAsnLysGluAlaArgArgLeuGlyMet-165 |
| SEQ. ID. NO. 5995 | 174-ThrGlyLeuSerArgGluGlyGlnValSerThrAlaLysAsp-187 |
| SEQ. ID. NO. 5996 | 214-LysAsnIleGluGlnAsnAsnArg-221 |
| SEQ. ID. NO. 5997 | 227-ArgAspAsnAsnValAsn-232 |
| SEQ. ID. NO. 5998 | 237-GlyHisThrGluSerGly-242 |
| SEQ. ID. NO. 5999 | 264-SerGluSerAlaGluThrArgAlaSerAspAsnSerLys-276 |
| SEQ. ID. NO. 6000 | 289-LysIleTyrProLysGlyLysThr-296 |

TABLE 1-continued

| | |
|---|---|
| SEQ. ID. NO. 6001 | 304-GlyGlySerLysLysThrValArg-311 |
| SEQ. ID. NO. 6002 | 323-ProHisLysGluAlaLysMetAlaGluGlnIleLeu-334 |
| SEQ. ID. NO. 6003 | 343-ProValLysLysGlyGlnIle-349 |
| SEQ. ID. NO. 6004 | 353-IleLysIleArgGln-357 |
| SEQ. ID. NO. 6005 | 362-IleAlaGluLysGluIleValAla-369 |
| SEQ. ID. NO. 6006 | 371-GluAsnValLysLysArgSerArgTrp-379 |

556
AMPHI Regions - AMPHI
| | |
|---|---|
| SEQ. ID. NO. 6007 | 61-IleGluArgLeuLys-65 |

Antigenic Index - Jameson-Wolf
| | |
|---|---|
| SEQ. ID. NO. 6008 | 1-MetAspAsnLysThrLysLeuArgLeu-9 |
| SEQ. ID. NO. 6009 | 52-ThrSerArgArgGlnGlnArgGlnPheIleGluArgLeuLysLysPheAspIleAspProGluLysGlyArgIleAsnGluAlaAsnLeuArgArgMet TyrHisSerGlyGlyGlnHisGlnLysAspAla-95 |
| SEQ. ID. NO. 6010 | 102-SerGlnLysCysSerValAspGluAlaHisAlaMetPheLysLysArgProThrArgGlnGluIleAsn-124 |
| SEQ. ID. NO. 6011 | 127-AlaAlaLysGlnSerArgGlyGlnLysArgProHisArg-139 |

Hydrophilic Regions - Hopp-Woods
| | |
|---|---|
| SEQ. ID. NO. 6012 | 1-MetAspAsnLysThrLysLeuArgLeu-9 |
| SEQ. ID. NO. 6013 | 53-SerArgArgGlnGlnArgGlnPheIleGluArgLeuLysLysPheAspIleAspProGluLysGlyArgIleAsnGluAlaAsnLeuArgArgMet Tyr-85 |
| SEQ. ID. NO. 6014 | 90-GlnHisGlnLysAspAla-95 |
| SEQ. ID. NO. 6015 | 105-CysSerValAspGluAlaHisAlaMetPheLysLysArgProThrArgGlnGluIleAsn-124 |
| SEQ. ID. NO. 6016 | 127-AlaAlaLysGlnSerArgGlyGlnLysArgProHisArg-139 |

557
AMPHI Regions - AMPHI
| | |
|---|---|
| SEQ. ID. NO. 6017 | 22-GlyAlaAspGlyIle-26 |
| SEQ. ID. NO. 6018 | 55-SerGlyArgValAspAspAlaAla-62 |

Antigenic Index - Jameson-Wolf
| | |
|---|---|
| SEQ. ID. NO. 6019 | 20-LeuLysGlyAlaAspGlyIleSerProProLeuThrTyrArgSerTrpHisIleGluGlyGlyGlnAlaLeuArg-44 |
| SEQ. ID. NO. 6020 | 54-AlaSerGlyArgValAspAspAlaAlaGly-63 |
| SEQ. ID. NO. 6021 | 68-LeuArgIleAspSerValSerGlnAsnLysGluThrTyrThr-81 |
| SEQ. ID. NO. 6022 | 100-GlnValLeuLysArgGlyGluProValGlyLysProMet-112 |
| SEQ. ID. NO. 6023 | 123-AlaAspAsnGluIleLeuGlyLysGlnGluGluGluAla-135 |
| SEQ. ID. NO. 6024 | 141-MetArgGlnAspAlaAlaGluGlnIleValArg-151 |

Hydrophilic Regions - Hopp-Woods
| | |
|---|---|
| SEQ. ID. NO. 6025 | 21-LysGlyAlaAspGlyIle-26 |
| SEQ. ID. NO. 6026 | 56-GlyArgValAspAspAlaAlaGly-63 |
| SEQ. ID. NO. 6027 | 68-LeuArgIleAspSerValSerGlnAsnLysGluThrTyrThr-81 |
| SEQ. ID. NO. 6028 | 100-GlnValLeuLysArgGlyProValGly-109 |
| SEQ. ID. NO. 6029 | 126-GluIleLeuGlyLysGlnGluGluGluAla-135 |
| SEQ. ID. NO. 6030 | 141-MetArgGlnAspAlaAlaGluGlnIleValArg-151 |

560
AMPHI Regions - AMPHI
| | |
|---|---|
| SEQ. ID. NO. 6031 | 30-PheArgAspGlyAlaHisLysMetAlaArgValTrpValGly-43 |
| SEQ. ID. NO. 6032 | 167-ArgMetAlaLysMetPhe-172 |
| SEQ. ID. NO. 6033 | 192-PheLeuLysTyrProGlyGlu-198 |
| SEQ. ID. NO. 6034 | 216-GluLeuMetGluLysCysGluHisLeuIleGlu-226 |

Antigenic Index - Jameson-Wolf
| | |
|---|---|
| SEQ. ID. NO. 6035 | 29-ProPheArgAspGlyAlaHisLysMet-37 |
| SEQ. ID. NO. 6036 | 61-GlyAlaGluAsnIleProAspArgProAla-70 |
| SEQ. ID. NO. 6037 | 76-HisGlnSerGlyTrpGlu-81 |
| SEQ. ID. NO. 6038 | 95-ValAlaLysArgGluLeuPhe-101 |
| SEQ. ID. NO. 6039 | 116-IleGlyIleAspArgAsnAsnArgArgGluAlaAsnGluGlnLeuIle-131 |
| SEQ. ID. NO. 6040 | 134-GlyLeuValArgLysAsnGluGlyTyr-142 |
| SEQ. ID. NO. 6041 | 148-ProGluGlyThrArgLeuAlaProGlyLysArgGlyLysTyrLysLeuGlyGly-165 |
| SEQ. ID. NO. 6042 | 182-AsnSerGlyGluPheTrpProLysAsnSerPheLeuLysTyrProGlyGluIle-199 |
| SEQ. ID. NO. 6043 | 209-HisAlaSerGlySerGluAlaGluLeuMetGluLysCysGluHisLeuIle-225 |
| SEQ. ID. NO. 6044 | 242-MetProSerGluThrAla-247 |

Hydrophilic Regions - Hopp-Woods
| | |
|---|---|
| SEQ. ID. NO. 6045 | 29-ProPheArgAspGlyAlaHisLysMet-37 |
| SEQ. ID. NO. 6046 | 64-AsnIleProAspArgProAla-70 |
| SEQ. ID. NO. 6047 | 95-ValAlaLysArgGluLeuPhe-101 |
| SEQ. ID. NO. 6048 | 116-IleGlyIleAspArgAsnAsnArgArgGluAlaAsnGluGlnLeuIle-131 |
| SEQ. ID. NO. 6049 | 134-GlyLeuValArgLysAsnGlu-140 |
| SEQ. ID. NO. 6050 | 149-GluGlyThrArgLeuAlaProGlyLysArgGlyLysTyrLysLeuGlyGly-165 |
| SEQ. ID. NO. 6051 | 211-SerGlySerGluAlaGluLeuMetGluLysCysGluHisLeuIle-225 |
| SEQ. ID. NO. 6052 | 242-MetProSerGluThrAla-247 |

561
AMPHI Regions - AMPHI
| | |
|---|---|
| SEQ. ID. NO. 6053 | 22-GlyLeuTrpValGlyLeuAlaAla-29 |
| SEQ. ID. NO. 6054 | 46-AlaSerValIleGluGluAlaGlyAsn-54 |
| SEQ. ID. NO. 6055 | 79-ValAlaGluPheGluLysSerLeuLysArgIleAlaGln-91 |
| SEQ. ID. NO. 6056 | 128-SerTyrArgArgProThrGlnVal-135 |
| SEQ. ID. NO. 6057 | 172-MetThrLeuValSerSer-177 |
| SEQ. ID. NO. 6058 | 188-ValIleArgProLeuGlnAlaLeuArgGluGlyAlaGluArgIleGlyArgArgCysPheAspIle-209 |
| SEQ. ID. NO. 6059 | 219-PheLysGlnValGlyArgCysPheAsnGlnMet-229 |
| SEQ. ID. NO. 6060 | 238-AspAspLeuGluGlyGlnValAlaGluGlnThrArgSerLeuGluLysGln-254 |
| SEQ. ID. NO. 6061 | 265-ThrArgAspLeuHisGlnSer-271 |
| SEQ. ID. NO. 6062 | 275-GlnGlnAlaAlaGluHisPhe-281 |
| SEQ. ID. NO. 6063 | 283-AsnArgIleLeuPro-287 |
| SEQ. ID. NO. 6064 | 317-AlaSerAspLeuGlyLysTyrHisGlu-325 |

TABLE 1-continued

| | |
|---|---|
| SEQ. ID. NO. 6065 | 339-ArgLeuLeuLeuSerPheProAsnGly-347 |
| SEQ. ID. NO. 6066 | 358-LeuGlnThrLeuGlyArgGlnLeuGly-366 |
| SEQ. ID. NO. 6067 | 392-GlnGlyLeuHisAspSerIleAlaGlnAlaLeuThr-403 |
| SEQ. ID. NO. 6068 | 434-GlyValGlnGluCysTyrGluAspValArgGluLeu-445 |
| SEQ. ID. NO. 6069 | 456-LysGluPheProGluAlaValAlaAspLeuPheAlaArgPhe-469 |
| SEQ. ID. NO. 6070 | 504-LeuSerAsnIleArgLysHisAlaArg-512 |
| SEQ. ID. NO. 6071 | 540-ThrGluLysIleGlyGluProThr-547 |
| Antigenic Index - Jameson-Wolf | |
| SEQ. ID. NO. 6072 | 6-ArgPheSerAspGlyIleSer-12 |
| SEQ. ID. NO. 6073 | 48-ValIleGluGluAlaGlyAsn-54 |
| SEQ. ID. NO. 6074 | 66-AlaGlyGluGlySerProArgAlaGlnIleAspAsnGlnValAlaGluPheGluLysSerLeuLysArgIleAlaGlnSerAspAlaIleHisPro-97 |
| SEQ. ID. NO. 6075 | 99-IleProSerAspThrProLeu-105 |
| SEQ. ID. NO. 6076 | 124-ProProLeuGlnSerTyrArgArgProThrGlnValAspLeu-137 |
| SEQ. ID. NO. 6077 | 152-GluAsnAlaAsnGluLysAsnThr-159 |
| SEQ. ID. NO. 6078 | 193-GlnAlaLeuArgGluGlyAlaGluArgIleGlyArgArgCysPheAsp-208 |
| SEQ. ID. NO. 6079 | 210-ProValProGluGlyGlyThrProGluPheLysGlnValGlyArgCysPheAsnGlnMetGlyGlyArgLeuLysIleLeuTyrAspAspLeuGluGly GlnValAlaGluGlnThrArgSerLeuGluLysGlnAsnGlnAsnLeu-258 |
| SEQ. ID. NO. 6080 | 263-GlnThrThrArgAspLeuHisGlnSerTyrIle-273 |
| SEQ. ID. NO. 6081 | 289-ValGlyAlaAspSerGlyArgValCysLeuAspGlyGlySerAsp-303 |
| SEQ. ID. NO. 6082 | 310-HisAlaAspCysGlyThrAlaAlaSerAspLeuGlyLysTyrHisGlu-325 |
| SEQ. ID. NO. 6083 | 332-TyrGlnAsnGluThrLeuGly-338 |
| SEQ. ID. NO. 6084 | 344-PheProAsnGlyIleSerLeuAspGluAspArgIleLeu-357 |
| SEQ. ID. NO. 6085 | 360-ThrLeuArgGlnGlnLeu-365 |
| SEQ. ID. NO. 6086 | 371-GlyAlaLysGlnGluGluGluLysArgLeu-380 |
| SEQ. ID. NO. 6087 | 384-LeuGlnGluArgAsnLeu-389 |
| SEQ. ID. NO. 6088 | 394-LeuHisAspSerIle-398 |
| SEQ. ID. NO. 6089 | 415-AlaPheAlaGluAsnLysArgGluGluAlaAlaGlu-426 |
| SEQ. ID. NO. 6090 | 434-GlyValGlnGluCysTyrGluAspValArgGlu-444 |
| SEQ. ID. NO. 6091 | 450-ArgThrLysIleSerAsnLysGluPheProGluAlaVal-462 |
| SEQ. ID. NO. 6092 | 480-AlaTrpGluAsnGlySer-485 |
| SEQ. ID. NO. 6093 | 488-ProProGlnGluAla-492 |
| SEQ. ID. NO. 6094 | 503-SerLeuSerAsnIleArgLysHisAlaArg-512 |
| SEQ. ID. NO. 6095 | 519-ThrLeuSerGluHisGlyGlyArgPhe-527 |
| SEQ. ID. NO. 6096 | 531-IleGlnAspAsnGlyGlnGlyPheAspThrGluLysIleGlyGluProThrGlySerHis-550 |
| SEQ. ID. NO. 6097 | 556-MetGlnGluArgAlaLysArgIle-563 |
| SEQ. ID. NO. 6098 | 568-GluIleArgSerGlnAlaGlnGlnGlyThrThr-578 |
| SEQ. ID. NO. 6099 | 584-AlaSerGluGluSerLeuLys-590 |
| Hydrophilic Regions - Hopp-Woods | |
| SEQ. ID. NO. 6100 | 48-ValIleGluGluAlaGlyAsn-54 |
| SEQ. ID. NO. 6101 | 68-GluGlySerProArgAlaGlnIle-75 |
| SEQ. ID. NO. 6102 | 78-GlnValAlaGluPheGluLysSerLeuLysArgIleAlaGln-91 |
| SEQ. ID. NO. 6103 | 128-SerTyrArgArgProThrGln-134 |
| SEQ. ID. NO. 6104 | 152-GluAsnAlaAsnGluLys-157 |
| SEQ. ID. NO. 6105 | 193-GlnAlaLeuArgGluGlyAlaGluArgIleGlyArgArgCysPhe-207 |
| SEQ. ID. NO. 6106 | 213-GluGlyGlyThrProGluPheLysGlnValGly-223 |
| SEQ. ID. NO. 6107 | 235-IleLeuTyrAspAspLeuGluGlyGlnValAlaGluGlnThrArgSerLeuGluLysGlnAsnGln-256 |
| SEQ. ID. NO. 6108 | 264-ThrThrArgAspLeuHis-269 |
| SEQ. ID. NO. 6109 | 290-GlyAlaAspSerGlyArgValCysLeu-298 |
| SEQ. ID. NO. 6110 | 312-AspCysGlyThrAlaAlaSerAspLeuGlyLysTyrHisGlu-325 |
| SEQ. ID. NO. 6111 | 349-SerLeuAspGluAspAspArgIleLeu-357 |
| SEQ. ID. NO. 6112 | 371-GlyAlaLysGlnGluGluGluLysArgLeu-380 |
| SEQ. ID. NO. 6113 | 384-LeuGlnGluArgAsnLeu-389 |
| SEQ. ID. NO. 6114 | 415-AlaPheAlaGluAsnLysArgGluGluAlaAlaGlu-426 |
| SEQ. ID. NO. 6115 | 437-GluCysTyrGluAspValArgGlu-444 |
| SEQ. ID. NO. 6116 | 451-ThrLysIleSerAsnLysGluPheProGluAlaVal-462 |
| SEQ. ID. NO. 6117 | 503-SerLeuSerAsnIleArgLysHisAlaArg-512 |
| SEQ. ID. NO. 6118 | 533-AspAsnGlyGlnGlyPheAspThrGluLysIleGlyGluProThrGly-548 |
| SEQ. ID. NO. 6119 | 556-MetGlnGluArgAlaLysArgIle-563 |
| SEQ. ID. NO. 6120 | 568-GluIleArgSerGlnAlaGln-574 |
| SEQ. ID. NO. 6121 | 584-AlaSerGluGluSerLeuLys-590 |
| 562 | |
| AMPHI Regions - AMPHI | |
| SEQ. ID. NO. 6122 | 48-TrpSerLeuValSerAlaTrpMetValValIle-58 |
| SEQ. ID. NO. 6123 | 84-LeuGluThrThrValMetSerAlaValArgThrLeu-95 |
| SEQ. ID. NO. 6124 | 97-PheThrProTyrThrThrValAlaSerThrSer-107 |
| SEQ. ID. NO. 6125 | 116-ThrPhePheAlaProLeuSerArgTrp-124 |
| SEQ. ID. NO. 6126 | 133-AsnAlaProValHisSerMetThrLysSerThrProSerSerPheHis-148 |
| SEQ. ID. NO. 6127 | 184-ValSerAsnLeuValArgTrpAlaLeu-192 |
| Antigenic Index - Jameson-Wolf | |
| SEQ. ID. NO. 6128 | 9-PheAsnSerGlySerThrLysProThr-17 |
| SEQ. ID. NO. 6129 | 32-ProLeuArgAlaArgArgArgSerLeuTrpArg-42 |
| SEQ. ID. NO. 6130 | 72-AlaThrGlyGluArgGlnLeuVal-79 |
| SEQ. ID. NO. 6131 | 105-SerThrSerSerProProGlyAlaGluMet-114 |
| SEQ. ID. NO. 6132 | 139-MetThrLysSerThrProSerSerPheHisGlySerSerAla-152 |
| SEQ. ID. NO. 6133 | 154-LeuArgValGluLysLysGlyIleLeuSerProLeuThr-166 |
| SEQ. ID. NO. 6134 | 168-ArgLeuProProSerTrpAspThrSerAlaSerLysArgProCysThr-183 |
| Hydrophilic Regions - Hopp-Woods | |
| SEQ. ID. NO. 6135 | 33-LeuArgAlaArgArgArgSerLeuTrp-41 |
| SEQ. ID. NO. 6136 | 72-AlaThrGlyGluArgGlnLeuVal-79 |
| SEQ. ID. NO. 6137 | 110-ProGlyAlaGluMet-114 |

TABLE 1-continued

| | |
|---|---|
| SEQ. ID. NO. 6138 | 140-ThrLysSerThrPro-144 |
| SEQ. ID. NO. 6139 | 154-LeuArgValGluLysLysGlyIle-161 |
| SEQ. ID. NO. 6140 | 176-SerAlaSerLysArgProCysThr-183 |

563
AMPHI Regions - AMPHI

| | |
|---|---|
| SEQ. ID. NO. 6141 | 24-ThrLysArgGluGlyLys-29 |
| SEQ. ID. NO. 6142 | 120-AsnGlnTyrAlaGlnPhe-125 |
| SEQ. ID. NO. 6143 | 164-ValAsnGlnIleAsnSerSerHisSerSer-173 |
| SEQ. ID. NO. 6144 | 246-AspPheThrArgIleLeuSerTyrHisSer-255 |
| SEQ. ID. NO. 6145 | 290-AlaAlaAsnThrSerAsnAsnThrAla-298 |
| SEQ. ID. NO. 6146 | 313-LysLeuGlyGlyMetTyr-318 |
| SEQ. ID. NO. 6147 | 366-LysAspThrAspAsn-370 |
| SEQ. ID. NO. 6148 | 443-AsnAsnGlnGlyLysLeu-448 |
| SEQ. ID. NO. 6149 | 483-SerSerAsnGlnThrGlyAsn-489 |
| SEQ. ID. NO. 6150 | 516-SerAsnIleThrAlaProThr-522 |
| SEQ. ID. NO. 6151 | 529-ArgThrHisGlyAlaLeuAsp-535 |
| SEQ. ID. NO. 6152 | 551-GlnGlnGlyLeuAsnAsnAlaGlyGlnIle-560 |
| SEQ. ID. NO. 6153 | 611-LeuAspAsnAlaHisGlyLysLeuLeuSerAla-621 |
| SEQ. ID. NO. 6154 | 736-LeuAspAsnAlaAlaGlnGly-742 |
| SEQ. ID. NO. 6155 | 775-GlnMetAsnAsnIleGlyThr-781 |
| SEQ. ID. NO. 6156 | 848-ThrGlyLysAlaGlnArgIleHisAsnAlaGlyAlaThrIleGlu-862 |
| SEQ. ID. NO. 6157 | 874-LeuHisAsnThrAsnGlu-879 |
| SEQ. ID. NO. 6158 | 896-TyrGluAlaPheGlyArg-901 |
| SEQ. ID. NO. 6159 | 922-SerAspHisLeuArgThrProAspGlyAlaAlaHisGluAsnTrp-936 |
| SEQ. ID. NO. 6160 | 953-ThrAlaProAlaLys-957 |
| SEQ. ID. NO. 6161 | 1011-LeuHisSerTyrTrpArg-1016 |
| SEQ. ID. NO. 6162 | 1036-GluGluIleThrArg-1040 |
| SEQ. ID. NO. 6163 | 1131-LeuHisLysArgLeuGlyAspGlyTyr-1139 |
| SEQ. ID. NO. 6164 | 1147-GluGlnIleAlaGluLeuThrGlyHisArgArgLeuAspGlyTyrGlnAsn-1163 |
| SEQ. ID. NO. 6165 | 1169-LysAlaLeuMetAsp-1173 |
| SEQ. ID. NO. 6166 | 1194-GlnValAlaGlnLeu-1198 |
| SEQ. ID. NO. 6167 | 1272-ThrLeuAspAsnIleGlyGly-1278 |
| SEQ. ID. NO. 6168 | 1289-AlaThrGlnAspIleAsnAsnIleGlyGlyMetLeu-1300 |
| SEQ. ID. NO. 6169 | 1376-GlnAlaGlyArgAspIle-1381 |
| SEQ. ID. NO. 6170 | 1403-IleArgGlySerThrAsnGluValGlySerSer-1413 |
| SEQ. ID. NO. 6171 | 1461-ValAspAspAlaSerLysHisThrGlyArg-1470 |
| SEQ. ID. NO. 6172 | 1485-SerHisHisGluThr-1489 |
| SEQ. ID. NO. 6173 | 1524-GlnAlaGlyAsnHisVal-1529 |
| SEQ. ID. NO. 6174 | 1539-GlnSerGluThrTyrHisGln-1545 |
| SEQ. ID. NO. 6175 | 1594-LysHisTyrGluGlnIleGlySerThrVal-1603 |
| SEQ. ID. NO. 6176 | 1646-ProValThrAspLeuAla-1651 |
| SEQ. ID. NO. 6177 | 1685-TyrGlnThrGlyLysSerAlaGlnAsnLeuAlaAsnGlyThrThrAsn-1700 |
| SEQ. ID. NO. 6178 | 1777-GluGlnSerAsnThrGluArgGlyGln-1785 |
| SEQ. ID. NO. 6179 | 1811-GlyGlyAsnValGlyLysGlyTyrGly-1819 |
| SEQ. ID. NO. 6180 | 1964-LysAsnHisSerGlnTyr-1969 |
| SEQ. ID. NO. 6181 | 1987-LeuGlyGlnGlyAlaGlnAsnLysProGln-1996 |
| SEQ. ID. NO. 6182 | 2064-ThrAspThrAlaGluArgHisSerGlySerLeuLysAsnThrPheAsn-2079 |
| SEQ. ID. NO. 6183 | 2093-ValSerGlnAspPheSerLysAsnValGln-2102 |
| SEQ. ID. NO. 6184 | 2161-IleLeuAsnMetLeuAlaSerGlyLeuAla-2170 |
| SEQ. ID. NO. 6185 | 2193-GlyGlnHisPheLysAspLeuAlaGly-2201 |
| SEQ. ID. NO. 6186 | 2223-LeuGlyAlaAlaValAla-2228 |
| SEQ. ID. NO. 6187 | 2275-AlaIleThrAsnValLeuGlyThrAlaThrGly-2285 |
| SEQ. ID. NO. 6188 | 2289-GlyAsnSerAlaThrAspAlaAla-2296 |
| SEQ. ID. NO. 6189 | 2332-HisLysAspProGly-2336 |
| SEQ. ID. NO. 6190 | 2379-IleThrArgGluPheGlyLysAspIleAla-2388 |
| SEQ. ID. NO. 6191 | 2393-AsnSerHisGluSer-2397 |
| SEQ. ID. NO. 6192 | 2414-AlaAspGluMetIleAspGlnLeuAsnAsnGluIle-2425 |

Antigenic Index - Jameson-Wolf

| | |
|---|---|
| SEQ. ID. NO. 6193 | 1-MetAsnLysThrLeu-5 |
| SEQ. ID. NO. 6194 | 9-IlePheAsnArgLysArgGlyAlaVal-17 |
| SEQ. ID. NO. 6195 | 22-GluThrThrLysArgGluGlyLysSerCysAlaAspSerAspSerGlySerAlaHis-40 |
| SEQ. ID. NO. 6196 | 83-IleIleAlaAspLysAlaAlaProLysThrGlnGln-94 |
| SEQ. ID. NO. 6197 | 127-ValGlyAsnArgGlyAlaIleLeuAsnAsnSerArgSerAsnThrGlnThr-143 |
| SEQ. ID. NO. 6198 | 152-AsnProTrpLeuAla-156 |
| SEQ. ID. NO. 6199 | 158-GlyGluAlaArgVal-162 |
| SEQ. ID. NO. 6200 | 167-IleAsnSerSerHisSerSerGlnMetAsnGly-177 |
| SEQ. ID. NO. 6201 | 179-IleGluValGlyGlyArgArgAlaGluVal-188 |
| SEQ. ID. NO. 6202 | 205-AsnAlaSerArgAlaThrLeu-211 |
| SEQ. ID. NO. 6203 | 213-ThrGlyGlnProGlnTyrGlnAlaGlyAspLeuSerGlyPheLysIleArgGlnGlyAsn-232 |
| SEQ. ID. NO. 6204 | 239-GlyLeuAspAlaArgAspThrAspPhe-247 |
| SEQ. ID. NO. 6205 | 252-SerTyrHisSerLysIleAspAla-259 |
| SEQ. ID. NO. 6206 | 264-GlnAspValArgVal-268 |
| SEQ. ID. NO. 6207 | 292-AsnThrSerAsnAsnThrAlaAsnAsnGlyThr-302 |
| SEQ. ID. NO. 6208 | 310-AspThrGlyLysLeuGlyGly-316 |
| SEQ. ID. NO. 6209 | 331-AlaGlyIleArgAsnGlnGlyGlnLeu-339 |
| SEQ. ID. NO. 6210 | 349-AspAlaAsnGlyArgLeuValAsn-356 |
| SEQ. ID. NO. 6211 | 364-AsnAlaLysAspThrAspAsnThrAlaGluHisLysValAsnIleArgSerGlnGlyValGluAsnSerGlyThrAlaValSerGlnGlnGlyThrGlnIleHis-398 |
| SEQ. ID. NO. 6212 | 400-GlnSerIleGlnAsnThr-405 |

TABLE 1-continued

| | |
|---|---|
| SEQ. ID. NO. 6213 | 418-AsnSerGlySerLeuLysAsnGluThrSerGlyThrIleGluAlaAlaArgLeuAlaIleAspThrAspThrLeuAsnAsnGlnGlyLysLeuSerGln ThrGlySerGlnLysLeuHisIle-458 |
| SEQ. ID. NO. 6214 | 460-AlaGlnGlyLysMetAspAsnArgGlyArgMetGlyLeuGlnAspThrAlaProThrAlaSerAsnGlySerSerAsnGlnThrGlyAsnSerTyr-491 |
| SEQ. ID. NO. 6215 | 497-SerSerThrThrThrProThrThr-504 |
| SEQ. ID. NO. 6216 | 522-ThrPheAlaAspGlyThrIleArgThrHisGlyAlaLeuAspAsnSerGlySer-539 |
| SEQ. ID. NO. 6217 | 542-AlaAsnGlyGlnThrAspValSerAla-550 |
| SEQ. ID. NO. 6218 | 552-GlnGlyLeuAsnAsnAlaGlyGln-559 |
| SEQ. ID. NO. 6219 | 566-AsnAlaLysGlySerAla-571 |
| SEQ. ID. NO. 6220 | 573-AspAsnHisAsnGly-577 |
| SEQ. ID. NO. 6221 | 589-GlySerLeuAsnAsnGlnAsnGlyAsnIleThrThrArgGlnGlnLeuGluIleGluThrAspGlnLeuAspAsnAlaHisGly-616 |
| SEQ. ID. NO. 6222 | 631-SerLeuAsnAsnGlnAsnGlyGluIleAlaThrAsn-642 |
| SEQ. ID. NO. 6223 | 646-IleIleHisAspGlyGlnGlnSer-653 |
| SEQ. ID. NO. 6224 | 659-AsnThrAsnGlyThrIleGlnSerGlyArgAspValAlaIle-672 |
| SEQ. ID. NO. 6225 | 675-LysSerLeuSerAsnAsnGly-681 |
| SEQ. ID. NO. 6226 | 685-AlaAspAsnLysLeuAspIleAlaLeu-693 |
| SEQ. ID. NO. 6227 | 695-AspAspPheTyrValGlu-700 |
| SEQ. ID. NO. 6228 | 702-AsnIleValAlaGlyAsnGluLeu-709 |
| SEQ. ID. NO. 6229 | 711-LeuSerThrArgGlySerLeuLysAsnSerHisThr-722 |
| SEQ. ID. NO. 6230 | 725-AlaGlyLysArgIleArgIleLysAlaAsnAsnLeuAspAsnAlaAlaGlnGlyAsnIleGlnSerGlyGlyThrThrAspIleGlyThrGlnHisAsn LeuThrAsnArgGlyLeuIleAspGlyGlnGlnThrLysIleGln-772 |
| SEQ. ID. NO. 6231 | 793-AlaThrArgLeuAspAsnGlnAspGluAsnGlyThrGly-805 |
| SEQ. ID. NO. 6232 | 809-AlaAlaArgGluAsnLeuAsn-815 |
| SEQ. ID. NO. 6233 | 821-LeuAsnAsnArgGluAsnSerLeu-828 |
| SEQ. ID. NO. 6234 | 839-GlyAlaLeuAspThrAsnGlyGlnAlaThrGlyLysAlaGlnArgIleHisAsnAlaGlyAla-859 |
| SEQ. ID. NO. 6235 | 863-AlaAlaGlyLysMetArgLeuGlyValGluLysLeuHisAsnThrAsnGluHisLeuLys-882 |
| SEQ. ID. NO. 6236 | 887-GluThrGlyArgGluHisIleVal-894 |
| SEQ. ID. NO. 6237 | 903-GluLeuLeuArgGluGlyThrGlnHis-911 |
| SEQ. ID. NO. 6238 | 917-ValTyrAsnAspGluSerAspHisLeuArgThrProAspGlyAlaAlaHis-933 |
| SEQ. ID. NO. 6239 | 937-HisLysTyrAspTyrGluLysValThrGlnLysThrGlnVal-950 |
| SEQ. ID. NO. 6240 | 960-SerGlyAsnAspLeuThrIleAspGlyLysGluValPheAsnThrAspSer-976 |
| SEQ. ID. NO. 6241 | 987-GlnThrGluLysAspGlyLeuHisAsnGluGlnThrPheGlyGluLysLysValPheSerGluAsnGlyLysLeuHisSerTyrTrpArgGluLysHis LysGlyArgAspSerThrGlyHisSerGluGlnAsnTyrThrLeuProGluGluIleThrArgAsn-1041 |
| SEQ. ID. NO. 6242 | 1050-GluSerHisArgLysAlaLeu-1056 |
| SEQ. ID. NO. 6243 | 1059-HisAlaProSerGlnGlyThrGluLeuProGlnSerAsnGlyIle-1073 |
| SEQ. ID. NO. 6244 | 1100-TyrLeuValGluThrAspProArgPheAlaAsn-1110 |
| SEQ. ID. NO. 6245 | 1124-LeuLysLeuAspProAsnAsnLeuHisLysArgLeuGlyAspGlyTyrTyrGluGlnArgLeuIleAsn-1146 |
| SEQ. ID. NO. 6246 | 1153-ThrGlyHisArgArgLeuAspGlyTyrGlnAsnAspGluGluGlnPheLysAlaLeuMetAspAsnGlyAlaThrAlaAlaArgSerMetAsn-1183 |
| SEQ. ID. NO. 6247 | 1208-LysGluValLysLeuProAspGlyGlyThr-1217 |
| SEQ. ID. NO. 6248 | 1228-ArgValLysAsnGlyAspIleAspGlyLysGly-1238 |
| SEQ. ID. NO. 6249 | 1252-GlySerLeuLysAsSerGlyThrIleAlaGlyArgAsnAla-1265 |
| SEQ. ID. NO. 6250 | 1269-AsnThrAspThrLeuAspAsnIleGlyGly-1278 |
| SEQ. ID. NO. 6251 | 1280-IleHisAlaGlnLysSerAla-1286 |
| SEQ. ID. NO. 6252 | 1310-AlaGlyAsnAsnIleAsnSerGlnSerThrThrAlaSerSerGlnAsnThrGlnGlySerSerThrTyrLeu-1333 |
| SEQ. ID. NO. 6253 | 1342-ThrGlyLysGluLysGlyVal-1348 |
| SEQ. ID. NO. 6254 | 1353-AlaGlyLysAspIleAsnIle-1359 |
| SEQ. ID. NO. 6255 | 1364-IleSerAsnGlnSerGluGlnGlyGlnThrArgLeuGlnAlaGlyArgAspIleAsnLeuAspThrValGlnThrSerLysHisGln-1392 |
| SEQ. ID. NO. 6256 | 1396-PheAspAlaAspAsnHisValIleArgGlySerThrAsnGluValGlySerSerIleGlnThrLysGlyAspVal-1420 |
| SEQ. ID. NO. 6257 | 1425-GlyAsnAsnLeuAsnAlaLysAlaAlaGluValSerSerAlaAsnGly-1440 |
| SEQ. ID. NO. 6258 | 1446-AlaLysAsnAspIle-1450 |
| SEQ. ID. NO. 6259 | 1459-ThrHisValAspAspAlaSerLysHisThrGlyArgSerGlyGlyGlyAsnLysLeuValIle-1479 |
| SEQ. ID. NO. 6260 | 1481-AspLysAlaGlnSerHisHisGluThrAlaGlnSerSerThrPheGluGlyLysGln-1499 |
| SEQ. ID. NO. 6261 | 1503-GlnAlaGlyAsnAspAlaAsn-1509 |
| SEQ. ID. NO. 6262 | 1515-ValIleSerAspAsnGlyThrGlnIleGlnAla-1525 |
| SEQ. ID. NO. 6263 | 1532-GlyThrThrGlnThrGlnSerGlnSerGluThrTyrHisGlnThrGlnLysSerGlyLeu-1551 |
| SEQ. ID. NO. 6264 | 1561-GlySerLysThrAsnThrGlnGluAsnGlnSerGlnSerAsnGluHisThrGlySerThrValGlySerLeuLysGlyAspThrThrIle-1590 |
| SEQ. ID. NO. 6265 | 1592-AlaGlyLysHisTyrGluGlnIle-1599 |
| SEQ. ID. NO. 6266 | 1603-ValSerSerProGluGlyAsnAsn-1610 |
| SEQ. ID. NO. 6267 | 1621-AlaAlaHisAsnLysLeuAsnSerAsnThrThrGlnThrTyrGluGlnLysGlyLeu-1639 |
| SEQ. ID. NO. 6268 | 1659-GlnSerSerLysGlnValGlyGlnSerLysAsnAspArgValAsn-1673 |
| SEQ. ID. NO. 6269 | 1684-AlaTyrGlnThrGlyLysSerAlaGln-1692 |
| SEQ. ID. NO. 6270 | 1694-LeuAlaAsnGlyThrThrAsnAlaLys-1702 |
| SEQ. ID. NO. 6271 | 1710-TyrGlyGluGlnGlnAsnArgGlnThrThrGln-1720 |
| SEQ. ID. NO. 6272 | 1729-SerGlnIleGlnAlaGlyGlyLysThrThr-1738 |
| SEQ. ID. NO. 6273 | 1744-AlaAlaGluGlnSerAsn-1749 |
| SEQ. ID. NO. 6274 | 1754-GlySerAspValAlaGlyLys-1760 |
| SEQ. ID. NO. 6275 | 1767-AlaAspAsnAspIleThr-1772 |
| SEQ. ID. NO. 6276 | 1774-GlnSerAlaGluGlnSerAsnThrGluArgGlyGlnAsnLysSerAlaGlyTrpAsn-1792 |
| SEQ. ID. NO. 6277 | 1812-GlyAsnValGlyLysGlyTyrGlyAsnGlyAspSerIleThrHisArgHisSerHisIleGlyAspLysGlySer-1836 |
| SEQ. ID. NO. 6278 | 1841-GlnSerGlyGlyAspThrThrIleLys-1849 |
| SEQ. ID. NO. 6279 | 1851-AlaGlnValArgGlyLysGlyValGlnValAlaAsnAlaLysAsn-1864 |
| SEQ. ID. NO. 6280 | 1869-SerValGlnAspArgGlu1874ThrTyrGlnSerLysGlnAlaAsnAla-1883 |
| SEQ. ID. NO. 6281 | 1895-AlaGlyGlyAspTyrSerGlnSerLysIleArgAlaAspHis-1908 |
| SEQ. ID. NO. 6282 | 1912-ThrGluGlnSerGlyIleTyrAlaGlyGluAspGlyTyrGln-1925 |
| SEQ. ID. NO. 6283 | 1929-GlyAsnHisThrAspLeuLysGlyGlyIle-1938 |
| SEQ. ID. NO. 6284 | 1942-ThrGlnSerAlaGluAspLysGlyLysAsnArgPheGln-1954 |
| SEQ. ID. NO. 6285 | 1959-ThrHisSerAspIleLysAsnHisSerGlnTyrLysGlyGluSerPheGly-1975 |
| SEQ. ID. NO. 6286 | 1982-IleSerGlyLysThrLeuGlyGlnGlyAlaGlnAsnLysProGlnAsnLysHis-1999 |
| SEQ. ID. NO. 6287 | 2003-ValAlaAspLysAsnSerAlaSer Ser-2011 |
| SEQ. ID. NO. 6288 | 2014-GlyTyrGlySerAspSerAspSerGlnSerSerIleThrLysSerGlyIleAsnThrArgAsn-2034 |
| SEQ. ID. NO. 6289 | 2036-GlnIleThrAspGluAlaAlaGln-2043 |

TABLE 1-continued

| | |
|---|---|
| SEQ. ID. NO. 6290 | 2045-ArgLeuThrGlyLysThrAlaAlaGlnThrLyAlaAspIleAspThrAsnValThrThrAspThrAlaGluArgHisSerGlySerLeuLysAsnThr PheAsnLysGluAlaValGlnSerGluLeuAspLeuGlnArgThrValSerGlnAspPheSerLysAsnValGlnGlnAlaAsnThrGluIle-2108 |
| SEQ. ID. NO. 6291 | 2110-GlnHisLeuAspLysLeuLysAlaAspLysGluAlaAlaGluThrAlaAla-2126 |
| SEQ. ID. NO. 6292 | 2131-AlaAsnGlyAspMetGluThrAlaLysArgLysAlaHisGluAlaGlnAspAlaAlaLysAlaAspAsnTrpGlnGln-2157 |
| SEQ. ID. NO. 6293 | 2172-ProThrGlnSerGly-2176 |
| SEQ. ID. NO. 6294 | 2195-HisPheLysAspLeuAlaGlyGlnAsnAlaAsnGlyLysLeuThrAlaSerGlnGluThr-2214 |
| SEQ. ID. NO. 6295 | 2231-GlyAspAsnAsnAla-2235 |
| SEQ. ID. NO. 6296 | 2241-SerAlaGlyGlySerGluAla-2247 |
| SEQ. ID. NO. 6297 | 2256-LeuTyrGlyLysGluLysGlySerAspLeuThrAlaGluGluLysGluThrVal-2273 |
| SEQ. ID. NO. 6298 | 2288-ValGlyAsnSerAlaThrAspAlaAlaGlnGlySerLeuAsnAla-2302 |
| SEQ. ID. NO. 6299 | 2304-SerAlaValGluAsnAsnAspThrValGluGlnVal-2315 |
| SEQ. ID. NO. 6300 | 2319-LeuArgHisProArg-2323 |
| SEQ. ID. NO. 6301 | 2331-ValHisLysAspProGlySerThrLeuGluProAsnIle-2343 |
| SEQ. ID. NO. 6302 | 2355-PheProAsnSerGluPheGlyGlyGluGlyGlyVal-2366 |
| SEQ. ID. NO. 6303 | 2379-IleThrArgGluPheGlyLysAspIleAlaVal-2389 |
| SEQ. ID. NO. 6304 | 2391-ValGlyAsnSerHisGluSerGlyGluLysIleAsnTyrSerIleArgArgAsnLeuSerLeuAspLysAlaAspGluMetIleAsp-2419 |
| SEQ. ID. NO. 6305 | 2421-LeuAsnAsnGluIleGlyArgGluIleAla-2430 |
| SEQ. ID. NO. 6306 | 2432-AsnThrAsnArgLeuAsnThrLysGluLeu-2441 |
| SEQ. ID. NO. 6307 | 2447-GluThrTyrLysAsnAsnGlyPhe-2454 |
| SEQ. ID. NO. 6308 | 2456-GlnAlaGluArgAsnSerAsnGlyAsnTyrAspValValArgLysArgLeuSerGlyLysAspTyrGlnAsnThrSerAsn-2482 |
| SEQ. ID. NO. 6309 | 2496-IleGlnGlnArgArgLysGlnIleArg-2504 |
| SEQ. ID. NO. 6310 | 2510-ArgGlnTrpArgArg-2514 |
| Hydrophilic Regions - Hopp-Woods | |
| SEQ. ID. NO. 6311 | 10-PheAsnArgLysArgGlyAla-16 |
| SEQ. ID. NO. 6312 | 22-GluThrThrLysArgGluGlyLysSerCysAlaAspSerAspSerGlySerAlaHis-40 |
| SEQ. ID. NO. 6313 | 83-IleIleAlaAspLysAlaAlaProLysThrGlnGln-94 |
| SEQ. ID. NO. 6314 | 136-AsnSerArgSerAsnThr-141 |
| SEQ. ID. NO. 6315 | 158-GlyGluAlaArgVal-162 |
| SEQ. ID. NO. 6316 | 181-ValGlyGlyArgArgAlaGluVal-188 |
| SEQ. ID. NO. 6317 | 224-SerGlyPheLysIleArgGln-230 |
| SEQ. ID. NO. 6318 | 240-LeuAspAlaArgAspThrAspPhe-247 |
| SEQ. ID. NO. 6319 | 331-AlaGlyIleArgAsn-335 |
| SEQ. ID. NO. 6320 | 364-AsnAlaLysAspThrAspAsnThrAlaGluHisLysValAsnIleArgSerGlnGlyValGluAsnSerGly-387 |
| SEQ. ID. NO. 6321 | 420-GlySerLeuLysAsnGluThrSerGlyThrIleGluAlaAlaArgLeuAlaIleAspThrAspThrLeuAsnAsn-444 |
| SEQ. ID. NO. 6322 | 446-GlyLysLeuSerGln-450 |
| SEQ. ID. NO. 6323 | 460-AlaGlnGlyLysMetAspAsnArgGlyArgMetGlyLeu-472 |
| SEQ. ID. NO. 6324 | 481-AsnGlySerSerAsnGlnThr-487 |
| SEQ. ID. NO. 6325 | 534-LeuAspAsnSerGly-538 |
| SEQ. ID. NO. 6326 | 544-GlyGlnThrAspValSerAla-550 |
| SEQ. ID. NO. 6327 | 602-GlnGlnLeuGluIleGluThrAspGlnLeuAspAsnAlaHis-615 |
| SEQ. ID. NO. 6328 | 635-GlnAsnGlyGluIleAlaThr-641 |
| SEQ. ID. NO. 6329 | 665-GlnSerGlyArgAspValAlaIle-672 |
| SEQ. ID. NO. 6330 | 685-AlaAspAsnLysLeuAspIleAlaLeu-693 |
| SEQ. ID. NO. 6331 | 715-GlySerLeuLysAsn-719 |
| SEQ. ID. NO. 6332 | 725-AlaGlyLysArgIleArgIleLysAlaAsnAsnLeuAspAsnAlaAla-740 |
| SEQ. ID. NO. 6333 | 767-GlnGlnThrLysIleGln-772 |
| SEQ. ID. NO. 6334 | 794-ThrArgLeuAspAsnGlnAspGluAsnGlyThr-804 |
| SEQ. ID. NO. 6335 | 809-AlaAlaArgGluAsnLeu-814 |
| SEQ. ID. NO. 6336 | 822-AsnAsnArgGluAsnSer-827 |
| SEQ. ID. NO. 6337 | 841-LeuAspThrAsnGly-845 |
| SEQ. ID. NO. 6338 | 847-AlaThrGlyLysAlaGlnArgIleHis-855 |
| SEQ. ID. NO. 6339 | 863-AlaAlaGlyLysMetArgLeuGlyValGluLysLeuHisAsnThrAsnGluHisLeuLys-882 |
| SEQ. ID. NO. 6340 | 887-GluThrGlyArgGluHisIleVal-894 |
| SEQ. ID. NO. 6341 | 903-GluLeuLeuArgGluGlyThrGlnHis-911 |
| SEQ. ID. NO. 6342 | 919-AsnAspGluSerAspHisLeuArgThrProAspGlyAlaAla-932 |
| SEQ. ID. NO. 6343 | 939-TyrAspTyrGluLysValThrGln-946 |
| SEQ. ID. NO. 6344 | 964-LeuThrIleAspGlyLysGluValPheAsn-973 |
| SEQ. ID. NO. 6345 | 987-GlnThrGluLysAspGlyLeuHisAsn-995 |
| SEQ. ID. NO. 6346 | 998-ThrPheGlyGluLysLysValPheSerGluAsnGlyLys-1010 |
| SEQ. ID. NO. 6347 | 1015-TrpArgGluLysHisLysGlyArgAspSerThrGlyHisSerGluGln-1030 |
| SEQ. ID. NO. 6348 | 1036-GluGluIleThrArg-1040 |
| SEQ. ID. NO. 6349 | 1050-GluSerHisArgLysAlaLeu-1056 |
| SEQ. ID. NO. 6350 | 1063-GlnGlyThrGluLeuProGln-1069 |
| SEQ. ID. NO. 6351 | 1104-ThrAspProArgPheAlaAsn-1110 |
| SEQ. ID. NO. 6352 | 1124-LeuLysLeuAspPro-1128 |
| SEQ. ID. NO. 6353 | 1130-AsnLeuHisLysArgLeuGly-1136 |
| SEQ. ID. NO. 6354 | 1153-ThrGlyHisArgArgLeuAspGlyTyrGlnAsnAspGluGluGlnPheLysAlaLeuMet-1172 |
| SEQ. ID. NO. 6355 | 1175-GlyAlaThrAlaAlaArg-1180 |
| SEQ. ID. NO. 6356 | 1208-LysGluValLysLeuProAspGlyGlyThr-1217 |
| SEQ. ID. NO. 6357 | 1229-ValLysAsnGlyAspIleAspGlyLysGly-1238 |
| SEQ. ID. NO. 6358 | 1252-GlySerLeuLysAsn-1256 |
| SEQ. ID. NO. 6359 | 1280-IleHisAlaGlnLysSerAla-1286 |
| SEQ. ID. NO. 6360 | 1324-GlnAsnThrGlnGly-1328 |
| SEQ. ID. NO. 6361 | 1343-GlyLysGluLysGlyVal-1348 |
| SEQ. ID. NO. 6362 | 1353-AlaGlyLysAspIleAsn-1358 |
| SEQ. ID. NO. 6363 | 1366-AsnGlnSerGluGlnGlyGlnThrArgLeuGlnAlaGlyArgAspIleAsnLeu-1383 |
| SEQ. ID. NO. 6364 | 1387-GlnThrSerLysHisGln-1392 |
| SEQ. ID. NO. 6365 | 1396-PheAspAlaAspAsnHisVal-1402 |
| SEQ. ID. NO. 6366 | 1406-SerThrAsnGluValGlySer-1412 |
| SEQ. ID. NO. 6367 | 1414-IleGlnThrLysGlyAspVal-1420 |

TABLE 1-continued

| SEQ. ID. NO. | Sequence |
|---|---|
| SEQ. ID. NO. 6368 | 1428-LeuAsnAlaLysAlaAlaGluValSerSer-1437 |
| SEQ. ID. NO. 6369 | 1446-AlaLysAsnAspIle-1450 |
| SEQ. ID. NO. 6370 | 1460-HisValAspAspAlaSerLysHisThrGlyArgSerGlyGlyGly-1474 |
| SEQ. ID. NO. 6371 | 1481-AspLysAlaGlnSerHisHisGluThrAlaGln-1491 |
| SEQ. ID. NO. 6372 | 1493-SerThrPheGluGlyLysGln-1499 |
| SEQ. ID. NO. 6373 | 1537-GlnSerGlnSerGluThr-1542 |
| SEQ. ID. NO. 6374 | 1562-SerLysThrAsnThrGlnGluAsnGlnSerGlnSerAsnGluHisThrGly-1578 |
| SEQ. ID. NO. 6375 | 1584-LeuLysGlyAspThr-1588 |
| SEQ. ID. NO. 6376 | 1604-SerSerProGluGlyAsn-1609 |
| SEQ. ID. NO. 6377 | 1621-AlaAlaHisAsnLysLeuAsnSer-1628 |
| SEQ. ID. NO. 6378 | 1634-TyrGluGlnLysGly-1638 |
| SEQ. ID. NO. 6379 | 1659-GlnSerSerLysGlnValGlyGlnSerLysAsnAspArgValAsn-1673 |
| SEQ. ID. NO. 6380 | 1686-GlnThrGlyLysSerAlaGln-1692 |
| SEQ. ID. NO. 6381 | 1712-GluGlnGlnAsnArgGlnThrThr-1719 |
| SEQ. ID. NO. 6382 | 1744-AlaAlaGluGlnSerAsn-1749 |
| SEQ. ID. NO. 6383 | 1756-AspValAlaGlyLys-1760 |
| SEQ. ID. NO. 6384 | 1767-AlaAspAsnAspIle-1771 |
| SEQ. ID. NO. 6385 | 1775-SerAlaGluGlnSerAsnThrGluArgGlyGlnAsnLys-1787 |
| SEQ. ID. NO. 6386 | 1822-AspSerIleThrHis-1826 |
| SEQ. ID. NO. 6387 | 1830-HisIleGlyAspLysGlySer-1836 |
| SEQ. ID. NO. 6388 | 1843-GlyGlyAspThrThrIleLys-1849 |
| SEQ. ID. NO. 6389 | 1851-AlaGlnValArgGlyLysGlyVal-1858 |
| SEQ. ID. NO. 6390 | 1869-SerValGlnAspArgGluThrTyrGlnSerLysGlnGlnAsnAla-1883 |
| SEQ. ID. NO. 6391 | 1897-GlyAspTyrSerGlnSerLysIleArgAlaAspHis-1908 |
| SEQ. ID. NO. 6392 | 1919-AlaGlyGluAspGlyTyrGln-1925 |
| SEQ. ID. NO. 6393 | 1932-ThrAspLeuLysGly-1936 |
| SEQ. ID. NO. 6394 | 1943-GlnSerAlaGluAspLysGlyLysAsnArgPhe-1953 |
| SEQ. ID. NO. 6395 | 1961-SerAspIleLysAsn-1965 |
| SEQ. ID. NO. 6396 | 1967-SerGlnTyrLysGlyGluSer-1973 |
| SEQ. ID. NO. 6397 | 1991-AlaGlnAsnLysProGlnAsnLysHis-1999 |
| SEQ. ID. NO. 6398 | 2003-ValAlaAspLysAsnSerAla-2009 |
| SEQ. ID. NO. 6399 | 2017-SerAspSerAspSerGlnSerSerIleThr-2026 |
| SEQ. ID. NO. 6400 | 2036-GlnIleThrAspGluAlaAlaGln-2043 |
| SEQ. ID. NO. 6401 | 2050-ThrAlaAlaGlnThrLysAlaAspIleAspThr-2060 |
| SEQ. ID. NO. 6402 | 2065-AspThrAlaGluArgHisSerGlySerLeu-2074 |
| SEQ. ID. NO. 6403 | 2077-ThrPheAsnLysGluAlaValGlnSerGluLeuAspLeuGlnArg-2091 |
| SEQ. ID. NO. 6404 | 2104-AlaAsnThrGluIle-2108 |
| SEQ. ID. NO. 6405 | 2110-GlnHisLeuAspLysLeuLysAlaAspLysGluAlaAlaGluThrAlaAla-2126 |
| SEQ. ID. NO. 6406 | 2133-GlyAspMetGluThrAlaLysArgLysAlaHisGluAlaGlnAspAlaAlaAlaLysAlaAspAsn-2154 |
| SEQ. ID. NO. 6407 | 2195-HisPheLysAspLeuAlaGly-2201 |
| SEQ. ID. NO. 6408 | 2208-LeuThrAlaSerGlnGluThr-2214 |
| SEQ. ID. NO. 6409 | 2243-GlyGlySerGluAla-2247 |
| SEQ. ID. NO. 6410 | 2257-TyrGlyLysGluLysGlySerAspLeuThrAlaGluGluLysGluThrVal-2273 |
| SEQ. ID. NO. 6411 | 2291-SerAlaThrAspAlaAlaGln-2297 |
| SEQ. ID. NO. 6412 | 2304-SerAlaValGluAsnAsnAspThrValGluGlnVal-2315 |
| SEQ. ID. NO. 6413 | 2319-LeuArgHisProArg-2323 |
| SEQ. ID. NO. 6414 | 2331-ValHisLysAspProGlySerThrLeu-2339 |
| SEQ. ID. NO. 6415 | 2379-IleThrArgGluPheGlyLys-2385 |
| SEQ. ID. NO. 6416 | 2393-AsnSerHisGluSerGlyGluLysIleAsnTyrSerIleArgArgAsnLeuSerLeuAspLysAlaAspGluMetIleAsp-2419 |
| SEQ. ID. NO. 6417 | 2424-GluIleGlyArgGluIleAla-2430 |
| SEQ. ID. NO. 6418 | 2435-ArgLeuAsnThrLysGluLeu-2441 |
| SEQ. ID. NO. 6419 | 2456-GlnAlaGluArgAsnSerAsnGly-2463 |
| SEQ. ID. NO. 6420 | 2466-AspValValArgLysArgLeuSerGluLysAspTyrGlnAsn-2479 |
| SEQ. ID. NO. 6421 | 2496-IleGlnGlnArgArgLysGlnIleArg-2504 |
| SEQ. ID. NO. 6422 | 2510-ArgGlnTrpArgArg-2514 |

564-2
AMPHIRegions - AMPHI

| SEQ. ID. NO. | Sequence |
|---|---|
| SEQ. ID. NO. 6423 | 6-TyrLysValValPhe-10 |
| SEQ. ID. NO. 6424 | 25-LysArgGluGlyLysAsnThr-31 |
| SEQ. ID. NO. 6425 | 40-LeuProAsnAspIleAlaGlyPheAlaGlyPheIleHisSerIleSer-55 |
| SEQ. ID. NO. 6426 | 118-AsnGlnTyrAlaGlnPhe-123 |
| SEQ. ID. NO. 6427 | 162-ValAsnGlnIleAsnSerSerHisSerSerGlnLeuAsn-174 |
| SEQ. ID. NO. 6428 | 244-AspTyrThrArgIleLeuSerTyrHisSer-253 |
| SEQ. ID. NO. 6429 | 288-AlaAlaAsnThrSerAsnAsnThrAla-296 |
| SEQ. ID. NO. 6430 | 311-LysLeuGlyGlyMetTyr-316 |
| SEQ. ID. NO. 6431 | 322-LeuIleSerThrValGluGln-328 |
| SEQ. ID. NO. 6432 | 390-SerGlnThrLeuAsp-394 |
| SEQ. ID. NO. 6433 | 407-ValArgAsnLeuGlyArgLeuLysAsnGlnAsn-417 |
| SEQ. ID. NO. 6434 | 433-LeuAspAsnThrGlyAsnIleThrGlnThrGly-443 |
| SEQ. ID. NO. 6435 | 449-LeuValSerAlaGlyLysPheAspAsnSer-458 |
| SEQ. ID. NO. 6436 | 478-IleProGlnIleProSerThr-484 |
| SEQ. ID. NO. 6437 | 518-IleGlnThrThrGlyAlaPheAspAsnAlaGlySerIleAsnAla-532 |
| SEQ. ID. NO. 6438 | 561-SerPheAsnAsnThrValLys-567 |
| SEQ. ID. NO. 6439 | 600-LeuHisAsnAlaGly-604 |
| SEQ. ID. NO. 6440 | 638-GlyLeuHisAsnAlaGly-643 |
| SEQ. ID. NO. 6441 | 658-LeuArgAsnThrGlyLysVal-664 |
| SEQ. ID. NO. 6442 | 736-LeuTyrAsnGlnHisGly-741 |
| SEQ. ID. NO. 6443 | 765-AspGlyThrIleGlnSerAla-771 |
| SEQ. ID. NO. 6444 | 841-AspAsnGlnValThrGlyLys-847 |
| SEQ. ID. NO. 6445 | 871-AspGlyLeuThrHisIleGlyAlaGly-879 |

TABLE 1-continued

| SEQ. ID. NO. 6446 | 882-LeuThrAsnThrGlyThrGlyLysIleTyr-891 |
|---|---|
| SEQ. ID. NO. 6447 | 958-AlaGlyMetAlaAspThrPheVal-965 |
| SEQ. ID. NO. 6448 | 980-SerValArgAsnMetGlnAsnIleAsnAsnHis-990 |
| SEQ. ID. NO. 6449 | 1000-AlaGluLysGlnVal-1004 |
| SEQ. ID. NO. 6450 | 1125-ThrGlnTrpAspSerValThrLys-1132 |
| SEQ. ID. NO. 6451 | 1185-IleLysLeuIleAspGlyValSerThr-1193 |
| SEQ. ID. NO. 6452 | 1263-HisLysArgLeuGlyAspGlyTyr-1270 |
| SEQ. ID. NO. 6453 | 1278-GluGlnIleHisGlnLeuThrGlyTyrArgArgLeuAspGlyTyr-1292 |
| SEQ. ID. NO. 6454 | 1299-PheLysAlaLeuMetAspAsn-1305 |
| SEQ. ID. NO. 6455 | 1325-GlnValAlaArgLeu-1329 |
| SEQ. ID. NO. 6456 | 1461-ThrAlaIleAspArgMetAlaGlyIleAsnValValGlySerHisThrGluGlnValAspAsnArg-1482 |
| SEQ. ID. NO. 6457 | 1504-SerAsnGlnValLysAspGlyThrThr-1512 |
| SEQ. ID. NO. 6458 | 1515-ThrAlaGlyAsnAsn-1519 |
| SEQ. ID. NO. 6459 | 1542-ArgHisValArgGlnSerThrGluVal-1550 |
| SEQ. ID. NO. 6460 | 1596-ArgGlnIleThrGluLeu-1601 |
| SEQ. ID. NO. 6461 | 1720-IleIleGlySerLeuAsn-1725 |
| SEQ. ID. NO. 6462 | 1791-AlaGlnAsnPheIleGlnAlaAlaGlnAsnValGlyLysSer-1804 |
| SEQ. ID. NO. 6463 | 1822-TyrGlnAlaThrGlnGlnMet-1828 |
| SEQ. ID. NO. 6464 | 1870-GluAlaAlaAlaSerGln-1875 |
| SEQ. ID. NO. 6465 | 1925-GlySerGluGlnSer-1929 |
| SEQ. ID. NO. 6466 | 1955-GlyGlyAsnIleGlyLysGlyLys-1962 |
| SEQ. ID. NO. 6467 | 2106-AspIleGlnAsnHisSer-2111 |
| SEQ. ID. NO. 6468 | 2138-GlnGlyArgProThrAspArgIleSerProAla-2148 |
| SEQ. ID. NO. 6469 | 2177-AlaGlyGlnLeuAlaArgThrGlyArgThrAlaLys-2188 |
| SEQ. ID. NO. 6470 | 2204-AspGlnHisSerGlyHisLeuLysAsnSerPhe-2214 |
| SEQ. ID. NO. 6471 | 2228-GluValThrLysGluPheGlyArgAsnAlaAla-2238 |
| SEQ. ID. NO. 6472 | 2243-AlaValAlaAspLysLeuGlyAsnThrGlnSerTyrGluArgTyrGln-2258 |
| SEQ. ID. NO. 6473 | 2297-ArgTyrAspThrTrpLysGlu-2303 |
| SEQ. ID. NO. 6474 | 2308-ArgSerIleLeuHisGlyAlaAlaGly-2316 |
| SEQ. ID. NO. 6475 | 2320-ThrGlySerLeuGlyGlyIleLeuAla-2328 |
| SEQ. ID. NO. 6476 | 2336-AlaProTyrLeuAspLysAlaAlaGluAsnLeuGlyPro-2348 |
| SEQ. ID. NO. 6477 | 2352-AlaAlaValAsnAlaLeuGly-2358 |
| SEQ. ID. NO. 6478 | 2395-LysTyrAlaGluAlaLeuLysArg-2402 |
| SEQ. ID. NO. 6479 | 2404-ValGluLysArgGluGly-2409 |
| SEQ. ID. NO. 6480 | 2424-GlnIleLeuArgTrpValAspLysGlySerGlnAspGly-2436 |
| SEQ. ID. NO. 6481 | 2470-GlnThrTyrAsnAspProLysLeuPheGluGluTyr-2481 |
| SEQ. ID. NO. 6482 | 2520-GluGlyLeuThrSerLeuVal-2526 |
| SEQ. ID. NO. 6483 | 2537-LeuAlaGlyIleArgAsnLeuLysAsnIle-2546 |
| SEQ. ID. NO. 6484 | 2571-ValAlaLysGlyAspArg-2576 |
| SEQ. ID. NO. 6485 | 2620-LysProGlnArgGln-2624 |
| SEQ. ID. NO. 6486 | 2647-AspValCysThrGluCys-2652 |
| SEQ. ID. NO. 6487 | 2669-ProGluIleGluArg-2673 |
| Antigenic Index - Jameson-Wolf | |
| SEQ. ID. NO. 6488 | 10-PheAsnLysHisArgAsnCysMet-17 |
| SEQ. ID. NO. 6489 | 22-GluAsnAlaLysArgGluGlyLysAsnThrAlaAsp-33 |
| SEQ. ID. NO. 6490 | 82-ValAlaAspLysSerAlaProAlaGlnGlnGln-92 |
| SEQ. ID. NO. 6491 | 125-ValGlyAsnArgGlyAlaIleLeuAsnAsnSerArgSerAsnThrGlnThr-141 |
| SEQ. ID. NO. 6492 | 150-AsnProTrpLeuAla-154 |
| SEQ. ID. NO. 6493 | 156-GlyGluAlaArgVal-160 |
| SEQ. ID. NO. 6494 | 165-IleAsnSerSerHisSerSerGlnLeuAsnGly-175 |
| SEQ. ID. NO. 6495 | 177-IleGluValGlyGlyArgArgAlaGluVal-186 |
| SEQ. ID. NO. 6496 | 203-AsnAlaSerArgAlaThrLeu-209 |
| SEQ. ID. NO. 6497 | 214-ProGlnTyrGlnAlaGlyAspLeuSerGlyPheLysIleArgGlnGlyAsn-230 |
| SEQ. ID. NO. 6498 | 237-GlyLeuAspAlaArgAspThrAspTyrThrArg-247 |
| SEQ. ID. NO. 6499 | 250-SerTyrHisSerLysIleAspAla-257 |
| SEQ. ID. NO. 6500 | 262-GlnAspValArgVal-266 |
| SEQ. ID. NO. 6501 | 269-GlyGlnAsnAspValAlaAlaThrGlyAspAlaHisSerPro-282 |
| SEQ. ID. NO. 6502 | 290-AsnThrSerAsnAsnThrAlaAsnAsnGlyThr-300 |
| SEQ. ID. NO. 6503 | 308-AspThrGlyLysLeuGlyGly-314 |
| SEQ. ID. NO. 6504 | 327-GluGlnAlaGlyIleArgAsnGlnGlyGln-336 |
| SEQ. ID. NO. 6505 | 347-AsnAlaGluGlyLysLeuValAsn-354 |
| SEQ. ID. NO. 6506 | 361-ThrGlyGluAsnHis-365 |
| SEQ. ID. NO. 6507 | 373-AsnValHisAsnSerGlyThrValAlaSerGlnAspAspAlaAsnIleHis-389 |
| SEQ. ID. NO. 6508 | 391-GlnThrLeuAspAsnSerGlyThrVal-399 |
| SEQ. ID. NO. 6509 | 401-SerSerGlyArgLeuThrVal-407 |
| SEQ. ID. NO. 6510 | 409-AsnLeuGlyArgLeuLysAsnGlnAsnAsnGly-419 |
| SEQ. ID. NO. 6511 | 424-AlaArgLeuAspMetSerThrGlyGlyLeuAspAsnThrGlyAsnIleThrGlnThrGlySerGln-445 |
| SEQ. ID. NO. 6512 | 453-GlyLysPheAspAsnSerGlyLysIleGlyValSerAspValProGlnThrGlyLeuAsnProAsnProSerVal-477 |
| SEQ. ID. NO. 6513 | 486-ThrGlySerGlySer-490 |
| SEQ. ID. NO. 6514 | 493-ValSerValSerLysProGlySerAsnAsnProValSerProThrAlaProAlaLysAsnTyrAla-514 |
| SEQ. ID. NO. 6515 | 525-AspAsnAlaGlySerIleAsnAlaGlyGlyGlnIleAsp-537 |
| SEQ. ID. NO. 6516 | 542-AsnGlyLeuGlyAsnSerGlySer-549 |
| SEQ. ID. NO. 6517 | 553-AlaLysLeuArgValSerGlyAspSerPheAsnAsnThrValLysGlyLysLeuGlnAla-572 |
| SEQ. ID. NO. 6518 | 580-GlnThrAlaLysAsnSerGlyHis-587 |
| SEQ. ID. NO. 6519 | 591-GlnThrGlyLysIleAspAsnArgGluLeuHisAsnAlaGlyGlu-605 |
| SEQ. ID. NO. 6520 | 615-HisSerGlyArgLeuSerAsnAspLysLysGlyAsnIle-627 |
| SEQ. ID. NO. 6521 | 647-AlaAspSerGlyThrValThrThrLysAsnAsnLeuArgAsnThrGlyLysValSerValAlaArgLeuAsnThrGluGlyGlnThrLeuAspAsnThrArgGlyArgIleGluAlaGluThrValAsn-689 |
| SEQ. ID. NO. 6522 | 694-GlnLeuThrAsnGlnAsnGlyHis-701 |
| SEQ. ID. NO. 6523 | 710-IleAsnSerArgAsnValAspAsnGlnAsnGlyLysLeuLeuSer-724 |

TABLE 1-continued

| | |
|---|---|
| SEQ. ID. NO. 6524 | 732-ValSerAspGlyLeuTyrAsnGlnHisGly-741 |
| SEQ. ID. NO. 6525 | 750-SerIleHisAspLysAsnGlnAsnThr-758 |
| SEQ. ID. NO. 6526 | 761-LeuAsnAsnAlaAspGlyThrIle-768 |
| SEQ. ID. NO. 6527 | 780-SerLeuAlaAsnAsnGlyThr-786 |
| SEQ. ID. NO. 6528 | 789-AlaGlyAsnLysLeuAsp-794 |
| SEQ. ID. NO. 6529 | 797-LeuThrAspAspPheValValGluArgAspLeuThrAlaGlyLys-811 |
| SEQ. ID. NO. 6530 | 817-IleLysGlyArgLeuLysAsnThrHisThr-826 |
| SEQ. ID. NO. 6531 | 836-AsnAlaGlyAsnIleAspAsnGlnVal-844 |
| SEQ. ID. NO. 6532 | 849-IleGlyGlyGluGlnThrAspIleThrSerGluGlnHisValAspAsnArgGlyLeuIleAsnSerAspGly-872 |
| SEQ. ID. NO. 6533 | 881-ThrLeuThrAsnThrGlyThrGlyLysIleTyr-891 |
| SEQ. ID. NO. 6534 | 903-LeuAsnArgGluGluThrThrGluGlySerThrLysAla-915 |
| SEQ. ID. NO. 6535 | 919-AlaAlaArgLysArgLeuAspIleGlyAlaLysGluIleHisAsnGlnGluGly-936 |
| SEQ. ID. NO. 6536 | 939-LeuSerSerGluGly-943 |
| SEQ. ID. NO. 6537 | 948-GlyAsnArgLeuAspGluGlnHisHis-956 |
| SEQ. ID. NO. 6538 | 985-GlnAsnIleAsnAsnHisPheLysThrGluThrTyrLeuAlaLysAlaGluLysGlnValArgAsp-1006 |
| SEQ. ID. NO. 6539 | 1017-GlnAlaGlyLysAspGlyLeuPheAspAsnSerGlnGlyGlnLysAspGlnThrThr-1035 |
| SEQ. ID. NO. 6540 | 1039-HisLeuLysAsnGlySerArgIleGluAla-1048 |
| SEQ. ID. NO. 6541 | 1060-ThrTyrLysGluArgIleGluAsnArgProAlaHis-1072 |
| SEQ. ID. NO. 6542 | 1076-GlyGlyAspLeuThrAlaSerGlyGlnAsnTrpLeuAsnLysAspSerArgIle-1093 |
| SEQ. ID. NO. 6543 | 1098-ArgIleIleThrAspAspLeuAsnGlnLysGluIleThrAsnGlnSerThrThrGlyLysGlyArgThrAspAlaVal-1123 |
| SEQ. ID. NO. 6544 | 1126-GlnTrpAspSerValThrLysLysGlyTrpTyrSerGlyArgLysArgGlnArgArgThrGluArgAsnHisThrProTyrHisAsp-1154 |
| SEQ. ID. NO. 6545 | 1160-HisAspPheAspThrProVal-1166 |
| SEQ. ID. NO. 6546 | 1172-AsnAlaAlaSerProSerPhe-1178 |
| SEQ. ID. NO. 6547 | 1196-ValAsnGlyGlnArgIleHisThr-1203 |
| SEQ. ID. NO. 6548 | 1223-ThrThrHisProAspAsnLysGlyTrp-1231 |
| SEQ. ID. NO. 6549 | 1234-GluThrAspProGlnPheAlaAspTyrArgArgTrpLeuGlySerAspTyr-1250 |
| SEQ. ID. NO. 6550 | 1258-AspThrAsnHisLeuHisLysArgLeuGlyAspGlyTyrTyrGluGlnLysLeuValAsn-1277 |
| SEQ. ID. NO. 6551 | 1285-GlyTyrArgArgLeuAspGlyTyrArgSerAspGluGluGlnPheLysAlaLeuMetAspAsnGly-1306 |
| SEQ. ID. NO. 6552 | 1343-LeuSerAspGlySerThrGln-1349 |
| SEQ. ID. NO. 6553 | 1359-LeuAlaArgLysGlyAspLeuAsnThrSerGlyGly-1370 |
| SEQ. ID. NO. 6554 | 1382-GlnAsnGlyAsnLeuThrAsn-1388 |
| SEQ. ID. NO. 6555 | 1403-ArgAsnIleAsnSerAsnGlyAsnIleGln-1412 |
| SEQ. ID. NO. 6556 | 1416-IleGlyLeuLysAlaGluLysSerIleAsnIleAspGlyGlyGlnValGln-1432 |
| SEQ. ID. NO. 6557 | 1445-AsnLeuAsnGlyThrThrGlnThrSerGlyAsnGluArgAsnGlyAsnThrAlaIleAspArgMetAla-1467 |
| SEQ. ID. NO. 6558 | 1473-GlySerHisThrGluGlnValAspAsnArgThrSerAspGly-1486 |
| SEQ. ID. NO. 6559 | 1491-HisAlaSerAsnAspIle-1496 |
| SEQ. ID. NO. 6560 | 1503-ValSerAsnGlnValLysAspGlyThrThr-1512 |
| SEQ. ID. NO. 6561 | 1525-IleArgThrGluHisArgGluAlaTyrGlyThrLeuAspAspGluAsnHisArgHisValArgGlnSerThrGluValGlySerSerIleArgThrGln AsnGly-1559 |
| SEQ. ID. NO. 6562 | 1564-AlaGlyAsnAspLeuLysIleArgGlnGlyGluLeuGluAlaGluGluGlyLysThr-1582 |
| SEQ. ID. NO. 6563 | 1586-AlaGlyArgAspValThrIleSerGluGlyArgGlnIleThrGluLeuAspThrSerValSerGlyLysSerLysGlyIleLeuSerSerThrLysThr HisAspArgTyrArgPheSerHisAspGluAlaVal-1630 |
| SEQ. ID. NO. 6564 | 1633-AsnIleGlyGlyGlyLysMet-1639 |
| SEQ. ID. NO. 6565 | 1644-GlyGlnAspIleAsnValArgGlySerAsnLeuIleSerAspLysGlyIleVal-1661 |
| SEQ. ID. NO. 6566 | 1664-AlaGlyHisIleAspIleSerThrAlaHisAsnArgTyrThrGlyAsnGluTyrHisGluSerLysLysSerGlyVal-1690 |
| SEQ. ID. NO. 6567 | 1699-ThrIleGlyAsnArgLysThrThrArgAspThrAspArgThrAsnIle-1714 |
| SEQ. ID. NO. 6568 | 1723-SerLeuAsnGlyAspThr-1728 |
| SEQ. ID. NO. 6569 | 1732-AlaGlyAsnArgTyrArgGlnThrGlySerThrValSerSerProGluGlyArgAsnThrValThr-1753 |
| SEQ. ID. NO. 6570 | 1761-PheAlaAsnAsnArgTyrAlaThrAspTyrAlaHisThrGlnGluGlnLysGly-1778 |
| SEQ. ID. NO. 6571 | 1799-GlnAsnValGlyLysSerLysAsnLysArgValAsn-1810 |
| SEQ. ID. NO. 6572 | 1832-AlaProSerSerSerAlaGlyGlnGlyGlnAsnAsnAsnGlnSerProSerIle-1849 |
| SEQ. ID. NO. 6573 | 1854-ThrTyrGlyGluGlnLysSerArgAsnGluGlnLysArgHisTyrThr-1869 |
| SEQ. ID. NO. 6574 | 1878-GlyLysGlyGlnThr-1882 |
| SEQ. ID. NO. 6575 | 1886-AlaThrGlySerGlyGluGlnSerAsnIleAsn-1896 |
| SEQ. ID. NO. 6576 | 1898-ThrGlySerAspVal-1902 |
| SEQ. ID. NO. 6577 | 1919-GlnSerAlaLysGlnAspGlySerGluGlnSerLysAsnLysSerSerGlyTrpAsnAla-1938 |
| SEQ. ID. NO. 6578 | 1954-AlaGlyGlyAsnIleGlyLysGlyLysGlnGlyGlySerThrThrHisArgHisThrHisValGlySerThrThrGlyLysThrThrIleArgSer GlyGlyAspThrThrLeu-1992 |
| SEQ. ID. NO. 6579 | 1999-GlyLysGlyIleGlnAlaAspThrArgAsnLeuHis-2010 |
| SEQ. ID. NO. 6580 | 2013-SerValGlnAspThrGluThrTyrGlnSerLysGlnGlnAsnGlyAsn-2028 |
| SEQ. ID. NO. 6581 | 2038-SerAlaSerGlySerTyrArgGlnSerLysValLysAlaAspHis-2052 |
| SEQ. ID. NO. 6582 | 2062-TyrAlaGlyGluAspGlyTyrGlnIleLysValArgAspAsnThrAspLeuLysGly-2080 |
| SEQ. ID. NO. 6583 | 2086-SerGlnSerAlaGluAspLysGlyLysAsnLeuPhe-2097 |
| SEQ. ID. NO. 6584 | 2105-SerAspIleGlnAsnHisSerArgTyrGluGlyArgSerPheGly-2119 |
| SEQ. ID. NO. 6585 | 2126-LeuAsnGlyGlyTrpAspGlyThrValThrAspLysGlnGlyArgProThrAspArgIleSerPro-2147 |
| SEQ. ID. NO. 6586 | 2151-TyrGlySerAspGlyAspSerLysAsnSerThrThrArgSerGlyValAsnThrHis-2169 |
| SEQ. ID. NO. 6587 | 2173-IleThrAspGluAlaGlyGlnLeuAlaArgThrGlyArgThrAlaLysGluThrGluAlaArgIle-2194 |
| SEQ. ID. NO. 6588 | 2197-GlyIleAspThrGluThrAlaAspGlnHisSerGlyHisLeuLysAsnSerPheAspLysAspAlaValAlaLysGluIleAsnLeuGlnArgGluVal ThrLysGluPheGlyArgAsnAlaAla-2238 |
| SEQ. ID. NO. 6589 | 2244-ValAlaAspLysLeuGlyAsnThrGlnSerTyrGluArgTyrGlnGluAlaArgThrLeuLeu-2264 |
| SEQ. ID. NO. 6590 | 2266-AlaGluLeuGlnAsnThrAspSerGluAlaGluLysAlaAlaPhe-2280 |
| SEQ. ID. NO. 6591 | 2292-AlaGluAsnGlnSerArgTyrAspThrTrpLysGluGlyGlyIleGlyArgSerIle-2310 |
| SEQ. ID. NO. 6592 | 2338-TyrLeuAspLysAlaAlaGluAsnLeuGlyProAlaGly-2350 |
| SEQ. ID. NO. 6593 | 2378-ValAspTrpAsnAsnArgGlnLeuHisProLysGluMetAlaLeu-2392 |
| SEQ. ID. NO. 6594 | 2394-AspLysTyrAlaGluAlaLeuLysArgGluValGluLysArgGluGlyArgLysIleSerSerGlnGluAlaAlaMetArgIleArgArgGln Ile-2425 |
| SEQ. ID. NO. 6595 | 2428-TrpValAspLysGlySerGlnAspGlyTyrThrAspGlnSerVal-2442 |
| SEQ. ID. NO. 6596 | 2448-MetLysGlyGluAspLysAlaLeu-2455 |
| SEQ. ID. NO. 6597 | 2460-AspTyrArgAspTyrGlyAlaArgAsnProGlnThrTyrAsnAspProLysLeuPheGluGluTyrArgArgGlnAspLysProGluTyrArg Asn-2491 |

TABLE 1-continued

| | |
|---|---|
| SEQ. ID. NO. 6598 | 2496-HisSerGlyThrLysAspThrLysIleArgGlnGlyGluArgLysAsnGluGluPhe-2514 |
| SEQ. ID. NO. 6599 | 2527-AsnProAsnProArgIleLysVal-2534 |
| SEQ. ID. NO. 6600 | 2541-ArgAsnLeuLysAsnIleLysProThrValThrGlySerAspPro-2555 |
| SEQ. ID. NO. 6601 | 2569-GlyAsnValAlaLysGlyAspArgIleProAspThrAlaLeuAlaSerLysGlyIleLysHisLysAsnArgLysAspGlnLeuGluLysAsnLysLysSerGlyGluAspPheGluMet-2608 |
| SEQ. ID. NO. 6602 | 2610-IleTyrGlnLysLysValLysGlnGlyPheLysProGlnArgGlnIleThrValLysThrLysSerGlyValLysThrArgLeuAspIleIleSerLysGluGlyGlyLeuAspValCysThrGluCysLysAla-2654 |
| SEQ. ID. NO. 6603 | 2659-ProLeuThrLysAsnGlnLysLysAlaPheProGluIleGluArgThrGlyAla-2676 |
| SEQ. ID. NO. 6604 | 2680-GlyLysGlyLysProGlyTyrProLysGlyThrLysIleGluProThrLysValIleIleGluArgLysArg-2703 |
| Hydrophilic Regions - Hopp-Woods | |
| SEQ. ID. NO. 6605 | 10-PheAsnLysHisArgAsn-15 |
| SEQ. ID. NO. 6606 | 22-GluAsnAlaLysArgGluGlyLysAsnThrAlaAsp-33 |
| SEQ. ID. NO. 6607 | 82-ValAlaAspLysSerAlaPro-88 |
| SEQ. ID. NO. 6608 | 134-AsnSerArgSerAsnThr-139 |
| SEQ. ID. NO. 6609 | 156-GlyGluAlaArgVal-160 |
| SEQ. ID. NO. 6610 | 179-ValGlyGlyArgArgAlaGluVal-186 |
| SEQ. ID. NO. 6611 | 222-SerGlyPheLysIleArgGln-228 |
| SEQ. ID. NO. 6612 | 238-LeuAspAlaArgAspThrAspTyr-245 |
| SEQ. ID. NO. 6613 | 271-AsnAspValAlaAla-275 |
| SEQ. ID. NO. 6614 | 329-AlaGlyIleArgAsn-333 |
| SEQ. ID. NO. 6615 | 348-AlaGluGlyLysLeu-352 |
| SEQ. ID. NO. 6616 | 361-ThrGlyGluAsnHis-365 |
| SEQ. ID. NO. 6617 | 381-AlaSerGlnAspAspAlaAsnIle-388 |
| SEQ. ID. NO. 6618 | 409-AsnLeuGlyArgLeuLysAsnGlnAsn-417 |
| SEQ. ID. NO. 6619 | 424-AlaArgLeuAspMet-428 |
| SEQ. ID. NO. 6620 | 453-GlyLysPheAspAsnSerGlyLysIleGlyVal-463 |
| SEQ. ID. NO. 6621 | 494-SerValSerLysProGlySer-500 |
| SEQ. ID. NO. 6622 | 553-AlaLysLeuArgValSerGly-559 |
| SEQ. ID. NO. 6623 | 566-ValLysGlyLysLeuGlnAla-572 |
| SEQ. ID. NO. 6624 | 580-GlnThrAlaLysAsnSer-585 |
| SEQ. ID. NO. 6625 | 593-GlyLysIleAspAsnArgGluLeuHisAsn-602 |
| SEQ. ID. NO. 6626 | 618-ArgLeuSerAsnAspLysLysGlyAsnIle-627 |
| SEQ. ID. NO. 6627 | 650-GlyThrValThrThr-654 |
| SEQ. ID. NO. 6628 | 656-AsnAsnLeuArgAsnThrGlyLys-663 |
| SEQ. ID. NO. 6629 | 669-LeuAsnThrGluGlyGlnThrLeuAspAsnThrArgGlyArgIleGluAlaGluThr-687 |
| SEQ. ID. NO. 6630 | 713-ArgAsnValAspAsnGlnAsn-719 |
| SEQ. ID. NO. 6631 | 750-SerIleHisAspLysAsnGlnAsn-757 |
| SEQ. ID. NO. 6632 | 763-AsnAlaAspGlyThrIle-768 |
| SEQ. ID. NO. 6633 | 801-PheValValGluArgAspLeuThrAla-809 |
| SEQ. ID. NO. 6634 | 817-IleLysGlyArgLeuLysAsn-823 |
| SEQ. ID. NO. 6635 | 852-GluGlnThrAspIleThrSer-858 |
| SEQ. ID. NO. 6636 | 860-GlnHisValAspAsnArgGlyLeuIle-868 |
| SEQ. ID. NO. 6637 | 903-LeuAsnArgGluGluThrThrGluGlySerThrLysAla-915 |
| SEQ. ID. NO. 6638 | 919-AlaAlaArgLysArgLeuAspIleGlyAlaLysGluIleHisAsnGlnGlu-935 |
| SEQ. ID. NO. 6639 | 949-AsnArgLeuAspGluGlnHisHis-956 |
| SEQ. ID. NO. 6640 | 995-ThrTyrLeuAlaLysAlaAlaGluLysGlnValArgAsp-1006 |
| SEQ. ID. NO. 6641 | 1018-AlaGlyLysAspGlyLeuPhe-1024 |
| SEQ. ID. NO. 6642 | 1027-SerGlnGlyGlnLysAspGlnThr-1034 |
| SEQ. ID. NO. 6643 | 1042-AsnGlySerArgIleGluAla-1048 |
| SEQ. ID. NO. 6644 | 1060-ThrTyrLysGluArgIleIleGluAsnArgPro-1070 |
| SEQ. ID. NO. 6645 | 1087-LeuAsnLysAspSerArgIle-1093 |
| SEQ. ID. NO. 6646 | 1099-IleIleThrAspAspLeuAsnGlnLysGluIleThrAsn-1111 |
| SEQ. ID. NO. 6647 | 1114-ThrThrGlyLysGlyArgThrAspAlaVal-1123 |
| SEQ. ID. NO. 6648 | 1134-GlyTrpTyrSerGlyArgLysArgGlnArgArgThrGlyArgAsnHis-1149 |
| SEQ. ID. NO. 6649 | 1235-ThrAspProGlnPheAlaAspTyrArgArg-1244 |
| SEQ. ID. NO. 6650 | 1261-HisLeuHisLysArgLeuGly-1267 |
| SEQ. ID. NO. 6651 | 1287-ArgArgLeuAspGlyTyrArgSerAspGluGluGlnPheLysAlaLeuMet-1303 |
| SEQ. ID. NO. 6652 | 1360-AlaArgLysGlyAspLeuAsnThr-1367 |
| SEQ. ID. NO. 6653 | 1416-IleGlyLeuLysAlaGluLysSerIleAsn-1425 |
| SEQ. ID. NO. 6654 | 1453-SerGlyAsnGluArgAsnGlyAsnThrAlaIleAspArgMetAla-1467 |
| SEQ. ID. NO. 6655 | 1475-HisThrGluGlnValAspAsnArgThrSerAsp-1485 |
| SEQ. ID. NO. 6656 | 1505-AsnGlnAsnValLysAspGlyThrThr-1512 |
| SEQ. ID. NO. 6657 | 1525-IleArgThrGluHisArgGluAlaTyrGlyThrLeuAspAspGluAsnHisArgHisValArgGlnSerThrGluVal-1550 |
| SEQ. ID. NO. 6658 | 1554-IleArgThrGlnAsn-1558 |
| SEQ. ID. NO. 6659 | 1564-AlaGlyAsnAspLeuLysIleArgGlnGlyGluLeuGluAlaGluGluGlyLysThr-1582 |
| SEQ. ID. NO. 6660 | 1586-AlaGlyArgAspValThrIleSerGluGlyArgGlnIleThrGluLeuAspThr-1603 |
| SEQ. ID. NO. 6661 | 1605-ValSerGlyLysSerLysGlyIle-1612 |
| SEQ. ID. NO. 6662 | 1616-ThrLysThrHisAspArgTyrArgPheSerHisAspGluAlaVal-1630 |
| SEQ. ID. NO. 6663 | 1647-IleAsnValArgGly-1651 |
| SEQ. ID. NO. 6664 | 1653-AsnLeuIleSerAspLysGlyIleVal-1661 |
| SEQ. ID. NO. 6665 | 1664-AlaGlyHisAspIleAspIle-1670 |
| SEQ. ID. NO. 6666 | 1681-GluTyrHisGluSerLysLysSerGlyVal-1690 |
| SEQ. ID. NO. 6667 | 1701-GlyAsnArgLysThrThrAspAspThrAspArgThrAsn-1713 |
| SEQ. ID. NO. 6668 | 1734-AsnArgTyrArgGlnThrGly-1740 |
| SEQ. ID. NO. 6669 | 1744-SerSerProGluGlyArgAsnThrValThr-1753 |
| SEQ. ID. NO. 6670 | 1774-GlnGluGlnLysGly-1778 |
| SEQ. ID. NO. 6671 | 1800-AsnValGlyLysSerLysAsnLysArgValAsn-1810 |
| SEQ. ID. NO. 6672 | 1836-SerAlaGlyGlnGlyGlnAsnAsnAsnGln-1845 |
| SEQ. ID. NO. 6673 | 1856-GlyGluGlnLysSerArgAsnGluGlnLysArgHisTyrThr-1869 |
| SEQ. ID. NO. 6674 | 1888-GlySerGlyGluGlnSerAsn-1894 |

TABLE 1-continued

| | |
|---|---|
| SEQ. ID. NO. 6675 | 1919-GlnSerAlaLysGlnAspGlySerGluGlnSerLysAsnLysSerSer-1934 |
| SEQ. ID. NO. 6676 | 1957-AsnIleGlyLysGlyLysGluGlnGlyGly-1966 |
| SEQ. ID. NO. 6677 | 1982-ThrThrIleArgSerGlyGlyAspThrThrLeu-1992 |
| SEQ. ID. NO. 6678 | 2002-IleGlnAlaAspThrArgAsnLeuHis-2010 |
| SEQ. ID. NO. 6679 | 2013-SerValGlnAspThrGluThrTyrGlnSerLysGlnGlnAsn-2026 |
| SEQ. ID. NO. 6680 | 2041-GlySerTyrArgGlnSerLysValLysAlaAspHis-2052 |
| SEQ. ID. NO. 6681 | 2063-AlaGlyGluAspGlyTyrGlnIleLysValArgAspAsnThrAspLeuLysGly-2080 |
| SEQ. ID. NO. 6682 | 2087-GlnSerAlaGluAspLysGlyLysAsn-2095 |
| SEQ. ID. NO. 6683 | 2111-SerArgTyrGluGlyArgSer-2117 |
| SEQ. ID. NO. 6684 | 2133-ThrValThrAspLysGlnGlyArgProThrAspArgIleSerPro-2147 |
| SEQ. ID. NO. 6685 | 2152-GlySerAspGlyAspSerLysAsnSerThrThrArgSerGlyVal-2166 |
| SEQ. ID. NO. 6686 | 2173-IleThrAspGluAlaGlyGln-2179 |
| SEQ. ID. NO. 6687 | 2181-AlaArgThrGlyArgThrAlaLysGluThrGluAlaArgIle-2194 |
| SEQ. ID. NO. 6688 | 2198-IleAspThrGluThrAlaAspGlnHisSerGlyHisLeu-2210 |
| SEQ. ID. NO. 6689 | 2212-AsnSerPheAspLysAspAlaValAlaLysGluIleAsnLeuGlnArgGluValThrLysGluPheGlyArg-2235 |
| SEQ. ID. NO. 6690 | 2244-ValAlaAspLysLeuGlyAsn-2250 |
| SEQ. ID. NO. 6691 | 2252-GlnSerTyrGluArgTyrGlnGluAlaArgThrLeuLeu-2264 |
| SEQ. ID. NO. 6692 | 2266-AlaGluLeuGlnAsnThrAspSerGluAlaGluLysAlaAlaPhe-2280 |
| SEQ. ID. NO. 6693 | 2294-AsnGlnSerArgTyrAspThrTrpLysGluGlyGlyIle-2306 |
| SEQ. ID. NO. 6694 | 2338-TyrLeuAspLysAlaAlaGluAsnLeuGlyProAlaGly-2350 |
| SEQ. ID. NO. 6695 | 2384-GlnLeuHisProLysGluMetAlaLeu-2392 |
| SEQ. ID. NO. 6696 | 2394-AspLysTyrAlaGluAlaLeuLysArgGluValGluLysArgGluGlyArgLysIleSerSerGlnGluAlaAlaMetArgIleArgArgGlnIle-2425 |
| SEQ. ID. NO. 6697 | 2428-TrpValAspLysGlySerGlnAspGlyTyrThr-2438 |
| SEQ. ID. NO. 6698 | 2448-MetLysGlyGluAspLysAlaLeu-2455 |
| SEQ. ID. NO. 6699 | 2460-AspTyrArgAspTyrGlyAlaArgAsnProGlnThrTyrAsnAsp-2474 |
| SEQ. ID. NO. 6700 | 2476-LysLeuPheGluGluTyrArgArgGlnAspLysProGluTyrArg-2490 |
| SEQ. ID. NO. 6701 | 2498-GlyThrLysAspThrLysIleArgGlnGlyGluArgLysAsnGluGluPhe-2514 |
| SEQ. ID. NO. 6702 | 2528-ProAsnProArgIleLys-2533 |
| SEQ. ID. NO. 6703 | 2541-ArgAsnLeuLysAsnIleLys-2547 |
| SEQ. ID. NO. 6704 | 2570-AsnValAlaLysGlyAspArgIleProAsp-2579 |
| SEQ. ID. NO. 6705 | 2585-LysGlyIleLysHisLysAsnArgLysAspGlnLeuGluLysAsnLysLysSerGlyGluAspPheGluMet-2608 |
| SEQ. ID. NO. 6706 | 2610-IleTyrGlnLysLysValLysGlnGlyPheLysProGlnArg-2623 |
| SEQ. ID. NO. 6707 | 2625-IleThrValThrLysSerGlyValLysThrArgLeuAspIleIleSerLysGluGlyGlyLeu-2646 |
| SEQ. ID. NO. 6708 | 2648-ValCysThrGluCysLysAla-2654 |
| SEQ. ID. NO. 6709 | 2660-LeuThrLysAsnGlnLysLysAlaPheProGluIleGluArgThrGly-2675 |
| SEQ. ID. NO. 6710 | 2680-GlyLysGlyLysProGlyTyrProLysGlyThrLysIleGluProThrLysValIleIleGluArgLysArg-2703 |
| 565 | |
| AMPHI Regions - AMPHI | |
| SEQ. ID. NO. 6711 | 50-AlaThrCysThrArgAlaMetSerLysSer-59 |
| SEQ. ID. NO. 6712 | 66-SerSerTrpAlaArg-70 |
| SEQ. ID. NO. 6713 | 84-IleSerThrTrpSerAspLeu-90 |
| SEQ. ID. NO. 6714 | 103-AspPheMetSerGlnLeuAspLeuThr-111 |
| SEQ. ID. NO. 6715 | 140-SerHisSerGlyGluThrIleSerSerCysProAlaMetAlaSerIleThrLysProAsn-159 |
| SEQ. ID. NO. 6716 | 184-AlaAsnThrThrSerAlaPhe-190 |
| Antigenic Index - Jameson-Wolf | |
| SEQ. ID. NO. 6717 | 1-MetAspSerThrLeuSerLysThrCys-9 |
| SEQ. ID. NO. 6718 | 23-PheAlaArgProArgProAlaAlaSerAsnThrSerLeu-35 |
| SEQ. ID. NO. 6719 | 37-PheAlaSerProAsnAspThrGlySer-45 |
| SEQ. ID. NO. 6720 | 55-AlaMetSerLysSerSerAlaLysTyrGly-64 |
| SEQ. ID. NO. 6721 | 67-SerTrpAlaArgThrArgProThrValCysProProLeuProLysProThrIle-84 |
| SEQ. ID. NO. 6722 | 99-CysArgSerSerAspPheMetSer-106 |
| SEQ. ID. NO. 6723 | 109-AspLeuThrLysArgProThrSerAlaSerLeuProProLysArgLysGlyAlaIle-127 |
| SEQ. ID. NO. 6724 | 129-IleAspSerArgThrAlaAla-135 |
| SEQ. ID. NO. 6725 | 140-SerHisSerGlyGluThrIleSerSer-148 |
| SEQ. ID. NO. 6726 | 154-SerIleThrLysProAsnSerProProCysAlaArgTyr-166 |
| SEQ. ID. NO. 6727 | 170-LeuArgLeuSerProThrGlu-176 |
| SEQ. ID. NO. 6728 | 194-SerIleAlaAsnSerIleAsnThrCysArgGlnProPro-206 |
| Hydrophilic Regions - Hopp-Woods | |
| SEQ. ID. NO. 6729 | 24-AlaArgProArgProAlaAla-30 |
| SEQ. ID. NO. 6730 | 39-SerProAsnAspThrGlySer-45 |
| SEQ. ID. NO. 6731 | 55-AlaMetSerLysSerSerAla-61 |
| SEQ. ID. NO. 6732 | 69-AlaArgThrArgPro-73 |
| SEQ. ID. NO. 6733 | 100-ArgSerSerAspPhe-104 |
| SEQ. ID. NO. 6734 | 109-AspLeuThrLysArgProThrSer-116 |
| SEQ. ID. NO. 6735 | 119-LeuProProLysArgLysGlyAlaIle-127 |
| SEQ. ID. NO. 6736 | 129-IleAspSerArgThr-133 |
| SEQ. ID. NO. 6737 | 141-HisSerGlyGluThrIleSer-147 |
| SEQ. ID. NO. 6738 | 156-ThrLysProAsnSer-160 |
| 566 | |
| Hydrophilic Regions - Hopp-Woods | |
| SEQ. ID. NO. 6739 | 29-ProPheArgAspGlyAlaHisLysMet-37 |
| SEQ. ID. NO. 6740 | 64-AsnIleProAspArgProAla-70 |
| SEQ. ID. NO. 6741 | 95-ValAlaLysArgGluLeuPhe-101 |
| SEQ. ID. NO. 6742 | 116-IleGlyIleAspArgAsnAsnArgArgGluAlaAsnGluGlnLeuIle-131 |
| SEQ. ID. NO. 6743 | 134-GlyLeuValArgLysAsnGlu-140 |
| SEQ. ID. NO. 6744 | 149-GluGlyThrArgLeuAlaProGlyLysArgGlyLysTyrLysLeuGlyGly-165 |
| SEQ. ID. NO. 6745 | 211-SerGlySerGluAlaGluLeuMetGluLysCysGluHisLeuIle-225 |
| SEQ. ID. NO. 6746 | 242-MetProSerGluThrAla-247 |

TABLE 1-continued

Antigenic Index - Jameson-Wolf
SEQ. ID. NO. 6747   32-PheAlaValAspProAsnCysGlyAlaAspGlyThrGlyGlyLysGlyHisAla-49
SEQ. ID. NO. 6748   61-AlaValGlyGlyGluGluGlyGlyValValAlaAspAspValAlaCysAlaAspGlyGlyLysAlaAspGlyArgArgIleAlaArg-89
SEQ. ID. NO. 6749   105-SerAlaGluArgAlaGlyAspAspPheAla-114
Hydrophilic Regions - Hopp-Woods
SEQ. ID. NO. 6750   36-ProAsnCysGlyAlaAspGlyThrGlyGlyLysGlyHisAla-49
SEQ. ID. NO. 6751   63-GlyGlyGluGluGlyGlyValValAlaAspAspValAlaCys-76
SEQ. ID. NO. 6752   78-AspGlyGlyLysAlaAspGlyArgArgIleAlaArg-89
SEQ. ID. NO. 6753   105-SerAlaGluArgAlaGlyAspAspPheAla-114
567
AMPHI Regions - AMPHI
SEQ. ID. NO. 6754   60-GlyValTyrGlnVal-64
SEQ. ID. NO. 6755   98-GluLeuValGlnGluIleAlaArgGluVal-107
SEQ. ID. NO. 6756   112-AlaLeuLysAlaVal-116
SEQ. ID. NO. 6757   154-TyrAlaLeuGluGlyIleSerAspLeuIleAlaThrValArgLysIleArgGln-171
SEQ. ID. NO. 6758   180-ThrGlyIleValArg-184
SEQ. ID. NO. 6759   195-AlaGluValSerGluGlnLeuArgSerHisPheGlyAspLeuLeu-209
Antigenic Index - Jameson-Wolf
SEQ. ID. NO. 6760   10-AsnGlnLysGlyGlyValGlyLysThrThrThr-20
SEQ. ID. NO. 6761   28-LeuAlaSerArgGlyLysArg-34
SEQ. ID. NO. 6762   38-ValAspLeuAspProGlnGlyAsnAlaThrThrGlySerGlyIleAspLysAlaGlyLeuGlnSerGly-60
SEQ. ID. NO. 6763   67-GlyAspAlaAspValGln-72
SEQ. ID. NO. 6764   75-AlaValArgSerLysGluGlyGly-82
SEQ. ID. NO. 6765   95-AlaGluIleGluLeu-99
SEQ. ID. NO. 6766   101-GlnGluIleAlaArgGluValArgLeuLysAsnAlaLeuLysAlaValGluGluAspTyrAsp-121
SEQ. ID. NO. 6767   127-CysProProSerLeu-131
SEQ. ID. NO. 6768   164-AlaThrValArgLysIleArgGlnAlaValAsnProAspLeuAspIle-179
SEQ. ID. NO. 6769   185-ThrMetTyrAspSerArgSerArgLeuValAlaGluValSerGluGlnLeuArgSerHisPheGlyAspLeu-208
SEQ. ID. NO. 6770   214-IleProArgAsnIleArgLeuAlaGluAlaProSerHisGly-227
SEQ. ID. NO. 6771   235-AlaGlnAlaLysGlyThrLys-241
SEQ. ID. NO. 6772   248-AspGluLeuAlaAlaArgValSerGlyLys-257
Hydrophilic Regions - Hopp-Woods
SEQ. ID. NO. 6773   10-AsnGlnLysGlyGlyValGlyLys-17
SEQ. ID. NO. 6774   28-LeuAlaSerArgGlyLysArg-34
SEQ. ID. NO. 6775   40-LeuAspProGlnGly-44
SEQ. ID. NO. 6776   50-SerGlyIleAspLysAlaGlyLeu-57
SEQ. ID. NO. 6777   67-GlyAspAlaAspValGln-72
SEQ. ID. NO. 6778   75-AlaValArgSerLysGluGlyGly-82
SEQ. ID. NO. 6779   95-AlaGluIleGluLeu-99
SEQ. ID. NO. 6780   101-GlnGluIleAlaArgGluValArgLeuLysAsnAlaLeuLysAlaValGluGluAspTyrAsp-121
SEQ. ID. NO. 6781   164-AlaThrValArgLysIleArgGln-171
SEQ. ID. NO. 6782   175-ProAspLeuAspIle-179
SEQ. ID. NO. 6783   186-MetTyrAspSerArgSerArgLeuValAlaGluValSerGluGlnLeuArg-202
SEQ. ID. NO. 6784   216-ArgAsnIleArgLeuAlaGluAlaProSer-225
SEQ. ID. NO. 6785   235-AlaGlnAlaLysGlyThrLys-241
SEQ. ID. NO. 6786   248-AspGluLeuAlaAla-252
568
AMPHI Regions - AMPHI
SEQ. ID. NO. 6787   32-AsnIlePheArgArgIle-37
SEQ. ID. NO. 6788   49-LysAlaCysLysAsn-53
SEQ. ID. NO. 6789   71-GluLysAlaAsnThrValArgTyr-78
SEQ. ID. NO. 6790   82-SerLeuAlaGlnCysPheThr-88
SEQ. ID. NO. 6791   112-ArgProLeuProSerIleIleThrAla-120
SEQ. ID. NO. 6792   169-GluPheValGlyPheGlyAsnValPheValGlyGlnPheLeuAsnArgPhePhe-186
SEQ. ID. NO. 6793   200-GluGluPhePheAspValValVal-207
SEQ. ID. NO. 6794   228-PheAsnGlnValPheAlaAlaPheLeu-236
SEQ. ID. NO. 6795   241-HisArgHisAlaAspGlnValAlaAspSerCysArgValGlnSerGln-256
Antigenic Index - Jameson-Wolf
SEQ. ID. NO. 6796   14-SerAlaSerSerMetProCysArgIleCysArgLeuLysArgSerArgLeuProAsnIlePhe-34
SEQ. ID. NO. 6797   39-PheSerCysArgArgArgThrCysPheCysLysAlaCysLysAsnSerProIleArgAsnGluThrSerSerSerGlyArgArgGlnPheSerValGluLysAlaAsnThr-75
SEQ. ID. NO. 6798   91-SerAsnAlaSerLysProArgLeu-98
SEQ. ID. NO. 6799   100-ProIleMetArgGlyArgLysArgPhePheAla-110
SEQ. ID. NO. 6800   141-PheArgGlySerAlaPheLysCysArgLeuAsnAlaGluProCysArg-156
SEQ. ID. NO. 6801   213-ValAlaAspArgAspAlaAla-219
SEQ. ID. NO. 6802   237-GlyGlnHisGlyHisArgHisAlaAspGlnValAlaAspSerCysArgValGlnSerGln-256
Hydrophilic Regions - Hopp-Woods
SEQ. ID. NO. 6803   21-ArgIleCysArgLeuLysArgSerArgLeu-30
SEQ. ID. NO. 6804   41-CysArgArgArgThrCysPhe-47
SEQ. ID. NO. 6805   49-LysAlaCysLysAsnSerProIleArgAsnGluThrSerSerSerGlyArgArgGlnPheSerValGluLysAlaAsnThr-75
SEQ. ID. NO. 6806   93-AlaSerLysProArgLeu-98
SEQ. ID. NO. 6807   102-MetArgGlyArgLysArgPhePheAla-110
SEQ. ID. NO. 6808   144-SerAlaPheLysCysArgLeuAsnAlaGluProCysArg-156
SEQ. ID. NO. 6809   213-ValAlaAspArgAspAlaAla-219
SEQ. ID. NO. 6810   239HisGlyHisArgHisAlaAspGlnValAlaAspSerCysArgVal-253
569
AMPHI Regions - AMPHI
SEQ. ID. NO. 6811   29-AlaAlaPheCysGlyLeuIleAlaLeuIleAlaLeuTrpGluTyrAlaArgMetGlyGlyLeuCysLys-51
SEQ. ID. NO. 6812   86-PheTrpLeuAlaValMetPro-92
SEQ. ID. NO. 6813   166-SerProGlyLysSerTrpGluGlyAlaIle-175

TABLE 1-continued

| | |
|---|---|
| SEQ. ID. NO. 6814 | 203-ThrValLeuIleGlyLeu-208 |
| SEQ. ID. NO. 6815 | 210-LeuThrValValSerValCysGlyAspLeuLeuGluSerTrpLeuLys-225 |
| SEQ. ID. NO. 6816 | 229-GlyIleLysAspSerSer-234 |
| Antigenic Index - Jameson-Wolf | |
| SEQ. ID. NO. 6817 | 50-CysLysIleLysThrAsnHis-56 |
| SEQ. ID. NO. 6818 | 98-LysTrpArgLeuAsnGlyGlyTrp-105 |
| SEQ. ID. NO. 6819 | 124-SerLeuArgProHisProAspAspAlaLeu-133 |
| SEQ. ID. NO. 6820 | 154-LysAlaPheGlyLysHisLysIle-161 |
| SEQ. ID. NO. 6821 | 165-IleSerProGlyLysSerTrpGlu-172 |
| SEQ. ID. NO. 6822 | 227-AlaAlaGlyIleLysAspSerSerLysLeuLeuProGlyHis-240 |
| SEQ. ID. NO. 6823 | 242-GlyValPheAspArgThrAspSer-249 |
| Hydrophilic Regions - Hopp-Woods | |
| SEQ. ID. NO. 6824 | 50-CysLysIleLysThr-54 |
| SEQ. ID. NO. 6825 | 127-ProHisProAspAspAlaLeu-133 |
| SEQ. ID. NO. 6826 | 155-AlaPheGlyLysHisLysIle-161 |
| SEQ. ID. NO. 6827 | 227-AlaAlaGlyIleLysAspSerSerLys-235 |
| SEQ. ID. NO. 6828 | 243-ValPheAspArgThrAspSer-249 |
| 570 | |
| AMPHI Regions - AMPHI | |
| SEQ. ID. NO. 6829 | 6-ArgAlaPheAlaAlaAlaLeuIleGlyLeu-15 |
| SEQ. ID. NO. 6830 | 22-HisAlaAspThrPheGlnLysIleGlyPheIleAsn-33 |
| SEQ. ID. NO. 6831 | 43-GlnAlaArgLysIleGlnLysThrLeuAspSer-53 |
| SEQ. ID. NO. 6832 | 60-AspGluLeuGlnLysLeuGln-66 |
| SEQ. ID. NO. 6833 | 81-LeuArgAsnAlaLysLys-86 |
| SEQ. ID. NO. 6834 | 91-GluLysTrpArgGlyLeuValAla-98 |
| SEQ. ID. NO. 6835 | 122-LeuGlnGlnAsnAlaAsnArgValIleValLysIle-133 |
| Antigenic Index - Jameson-Wolf | |
| SEQ. ID. NO. 6836 | 33-AsnThrGluArgIleTyrLeuGluSerLysGlnAlaArgLysIleGlnLysThrLeuAspSerGluPheSerAlaArgGlnAspGluLeuGlnLysLeu GlnArgGluGlyLeuAspLeuGluArgGlnLeuAlaGluGlyLysLeuArgAsnAlaLysLysAlaGlnAlaGluGluLysTrpArg-94 |
| SEQ. ID. NO. 6837 | 100-PheArgLysLysGlnAlaGlnPheGluGluAspTyrAsnLeuArgArgAsnGluGluPheAla-120 |
| SEQ. ID. NO. 6838 | 123-GlnGlnAsnAlaAsnArgVal-129 |
| SEQ. ID. NO. 6839 | 133-IleAlaLysGlnGluGlyTyrAspVal-141 |
| SEQ. ID. NO. 6840 | 152-GlnTyrAspValThrAspSerValIleLysGluMetAsnAlaArg-166 |
| Hydrophilic Regions - Hopp-Woods | |
| SEQ. ID. NO. 6841 | 37-IleTyrLeuGluSerLysGlnAlaArgLysIleGlnLysThrLeuAspSerGluPheSerAlaArgGlnAspGluLeuGlnLysLeuGlnArgGluGly LeuAspLeuArgGlnLeuAlaGluGlyLysLeuArgAsnAlaLysLysAlaGlnAlaGluGluLysTrpArg-94 |
| SEQ. ID. NO. 6842 | 100-PheArgLysLysGlnAlaGlnPheGluGluAspTyrAsnLeuArgArgAsnGluGluPheAla-120 |
| SEQ. ID. NO. 6843 | 133-IleAlaLysGlnGluGlyTyr-139 |
| SEQ. ID. NO. 6844 | 154-AspValThrAspSerValIleLysGluMetAsnAlaArg-166 |
| 571 | |
| AMPHI Regions - AMPHI | |
| SEQ. ID. NO. 6845 | 6-AlaValAsnValLeu-10 |
| SEQ. ID. NO. 6846 | 40-AspGlyAlaArgValPheArgAlaGly-48 |
| SEQ. ID. NO. 6847 | 63-AlaAlaValAlaAspPhePheAlaVal-71 |
| SEQ. ID. NO. 6848 | 94-ValGluValPheLysGlu-99 |
| Antigenic Index - Jameson-Wolf | |
| SEQ. ID. NO. 6849 | 13-AlaAlaGlyArgGlyThr-18 |
| SEQ. ID. NO. 6850 | 35-LysGlnAlaGlnAlaAspGlyAlaArgValPheArgAlaGlyHisArgGluGluGlnLeuGlyGlyAspVal-58 |
| SEQ. ID. NO. 6851 | 76-PheArgThrGluArgAlaAla-82 |
| SEQ. ID. NO. 6852 | 96-ValPheLysGluGlyAspPhe-102 |
| SEQ. ID. NO. 6853 | 110-ArgAsnAlaAspPheAlaAlaGluHisGlnArGluGlyPheAlaGlnGlyGluGluProGlyLeu-131 |
| SEQ. ID. NO. 6854 | 142-AlaAlaArgGlnGlyAspPheGlyVal-150 |
| SEQ. ID. NO. 6855 | 155-ValAlaAlaArgArgPro-160 |
| Hydrophilic Regions - Hopp-Woods | |
| SEQ. ID. NO. 6856 | 13-AlaAlaGlyArgGly-17 |
| SEQ. ID. NO. 6857 | 35-LysGlnAlaGlnAlaAspGlyAlaArgValPheArgAlaGlyHisArgGluGluGlnLeuGly-55 |
| SEQ. ID. NO. 6858 | 76-PheArgThrGluArgAlaAla-82 |
| SEQ. ID. NO. 6859 | 96-ValPheLysGluGlyAspPhe-102 |
| SEQ. ID. NO. 6860 | 110-ArgAsnAlaAspPheAlaAlaGluHisGlnArgGluGlyPheAlaGlnGlyGluGluProGly-130 |
| SEQ. ID. NO. 6861 | 155-ValAlaAlaArgArgPro-160 |
| 572-2 | |
| AMPHI Regions - AMPHI | |
| SEQ. ID. NO. 6862 | 20-LeuAspValValSerArgHisProGluLysPheArgVal-32 |
| SEQ. ID. NO. 6863 | 39-LysGlnValGluLysLeuAlaAlaGlnCys-48 |
| SEQ. ID. NO. 6864 | 85-GlnAlaLeuValAspValAlaSerAlaAspGlu-95 |
| SEQ. ID. NO. 6865 | 101-CysAlaIleValGlyAlaValGlyLeuProSerAlaLeuAla-114 |
| SEQ. ID. NO. 6866 | 160-GlnValLeuProArgAspTyrAlaGlyArg-169 |
| SEQ. ID. NO. 6867 | 192-LeuAsnThrPheAspArgIleThrProAlaGlnAlaValLys-205 |
| SEQ. ID. NO. 6868 | 225-LysGlyLeuGluLeu-229 |
| SEQ. ID. NO. 6869 | 253-IleHisSerMetValArg-258 |
| SEQ. ID. NO. 6870 | 282-GlyLeuProGluArgIleAspSerGly-290 |
| SEQ. ID. NO. 6871 | 299-LeuSerAlaLeuThr-303 |
| SEQ. ID. NO. 6872 | 340-ValAlaAlaPheLeu-344 |
| SEQ. ID. NO. 6873 | 350-PheThrAspIleAlaLysThrValAlaHisCysLeuAlaGlnAspPheSerAspGlyIleGlyAspIleGlyGly-374 |
| Antigenic Index - Jameson-Wolf | |
| SEQ. ID. NO. 6874 | 11-SerThrGlySerIleGlyGluSerThrLeu-20 |
| SEQ. ID. NO. 6875 | 22-ValValSerArgHisProGluLysPheArg-31 |
| SEQ. ID. NO. 6876 | 39-LysGlnValGluLysLeuAla-45 |
| SEQ. ID. NO. 6877 | 59-AlaAspAlaGluHisAlaAlaArgLeu-67 |
| SEQ. ID. NO. 6878 | 69-AlaLeuLeuLysArgAspGlyThrAla-77 |

TABLE 1-continued

| | |
|---|---|
| SEQ. ID. NO. 6879 | 91-AlaSerAlaAspGluValSer-97 |
| SEQ. ID. NO. 6880 | 117-GlnLysGlyLysThr-121 |
| SEQ. ID. NO. 6881 | 125-AlaAsnLysGluThrLeu-130 |
| SEQ. ID. NO. 6882 | 140-ThrAlaArgAlaAsnGly-145 |
| SEQ. ID. NO. 6883 | 150-ProValAspSerGluHis-155 |
| SEQ. ID. NO. 6884 | 162-LeuProArgAspTyrAlaGlyArgLeuAsnGluHisGly-174 |
| SEQ. ID. NO. 6885 | 193-AsnThrPheAspArgIleThrProAlaGlnAlaValLysHisProAsnTrpArgMetGlyArgLysIleSerValAspSer-219 |
| SEQ. ID. NO. 6886 | 224-AsnLysGlyLeuGluLeu-229 |
| SEQ. ID. NO. 6887 | 237-AsnCysProProAspLysLeuGluVal-245 |
| SEQ. ID. NO. 6888 | 257-ValArgTyrArgAspGlySerVal-264 |
| SEQ. ID. NO. 6889 | 269-GlyAsnProAspMetArgThr-275 |
| SEQ. ID. NO. 6890 | 283-LeuProGluArgIleAspSerGlyValGlyAspLeuAspPhe-296 |
| SEQ. ID. NO. 6891 | 303-ThrPheGlnLysProAspPheAspArg-311 |
| SEQ. ID. NO. 6892 | 363-GlnAspPheSerAspGlyIleGlyAspIleGly-373 |
| SEQ. ID. NO. 6893 | 378-GlnAspAlaArgThrArgAlaGlnAla-386 |
| Hydrophilic Regions - Hopp-Woods | |
| SEQ. ID. NO. 6894 | 22-ValValSerArgHisProGluLysPheArg-31 |
| SEQ. ID. NO. 6895 | 39-LysGlnValGluLysLeuAla-45 |
| SEQ. ID. NO. 6896 | 59-AlaAspAlaGluHisAlaAlaArgLeu-67 |
| SEQ. ID. NO. 6897 | 69-AlaLeuLeuLysArgAspGlyThrAla-77 |
| SEQ. ID. NO. 6898 | 91-AlaSerAlaAspGluValSer-97 |
| SEQ. ID. NO. 6899 | 126-AsnLysGluThrLeu-130 |
| SEQ. ID. NO. 6900 | 140-ThrAlaArgAlaAsnGly-145 |
| SEQ. ID. NO. 6901 | 151-ValAspSerGluHis-155 |
| SEQ. ID. NO. 6902 | 165-AspTyrAlaGlyArgLeuAsnGlu-172 |
| SEQ. ID. NO. 6903 | 196-AspArgIleThrPro-200 |
| SEQ. ID. NO. 6904 | 210-ArgMetGlyArgLysIleSerVal-217 |
| SEQ. ID. NO. 6905 | 225-LysGlyLeuGluLeu-229 |
| SEQ. ID. NO. 6906 | 239-ProAspLysLeuGlu-244 |
| SEQ. ID. NO. 6907 | 257-ValArgTyrArgAspGlySer-263 |
| SEQ. ID. NO. 6908 | 269-GlyAsnProAspMetArgThr-275 |
| SEQ. ID. NO. 6909 | 283-LeuProGluArgIleAspSerGlyValGlyAspLeuAspPhe-296 |
| SEQ. ID. NO. 6910 | 305-GlnLysProAspPheAspArg-311 |
| SEQ. ID. NO. 6911 | 364-AspPheSerAspGlyIleGly-370 |
| SEQ. ID. NO. 6912 | 378-GlnAspAlaArgThrArgAlaGlnAla-386 |
| 574 | |
| AMPHI Regions - AMPHI | |
| SEQ. ID. NO. 6913 | 6-ProAsnSerLeuLysLys-11 |
| SEQ. ID. NO. 6914 | 47-LeuLysGlnAlaLysSerIleProSerGlyPheTyrLysSerLeuAspAlaLeuValAspArgAsnSerGlyArgAlaAlaArgGluLeuAlaGluVal ValAsp-81 |
| SEQ. ID. NO. 6915 | 94-GlyLysLeuTyrArgGln-99 |
| SEQ. ID. NO. 6916 | 113-MetLeuAspSerProAspThr-119 |
| SEQ. ID. NO. 6917 | 175-GluLysAlaValGluThrAlaArgLeu-183 |
| SEQ. ID. NO. 6918 | 218-AsnValGlyLysAlaLeuGluAlaAsnLysLysCys-229 |
| SEQ. ID. NO. 6919 | 246-PheProAlaAlaValGluAlaTyrAlaAlaIleGlu-257 |
| SEQ. ID. NO. 6920 | 266-MetValGlyLysLeuTyrGluAlaTyrAla-276 |
| SEQ. ID. NO. 6921 | 281-ProGluGluGlyLeuAsnArgLeuThrGlyTyrMetGlnThrPheProGluLeuAspLeu-300 |
| SEQ. ID. NO. 6922 | 332-AsnGlyValTyrArg-336 |
| SEQ. ID. NO. 6923 | 357-ArgSerValIleGlyArgGlnLeuGlnArgSer-367 |
| Antigenic Index - Jameson-Wolf | |
| SEQ. ID. NO. 6924 | 1-MetArgProAsnLeuProAsnSerLeuLysLysAlaAspMetAspAsn-16 |
| SEQ. ID. NO. 6925 | 45-ThrValLeuLysGlnAlaLysSerIleProSerGlyPheTyrLysSerLeuAspAlaLeuValAspArgAsnSerGlyArgAlaAlaArgGluLeuAla GluValValAspGlyArgProGlnSerTyrAsp-88 |
| SEQ. ID. NO. 6926 | 96-LeuTyrArgGlnArgGlyGluAsnAspLysAlaIleAsnIleHisArgThrMetLeuAspSerProAspThrValGlyGluLysArgAlaArgVal-127 |
| SEQ. ID. NO. 6927 | 135-TyrGlnSerAlaGlyLeuValAspArgAlaGlu-145 |
| SEQ. ID. NO. 6928 | 151-LeuGlnAspGlyLysMetAlaArgGluAlaArgGln-162 |
| SEQ. ID. NO. 6929 | 168-TyrGlnGlnAspArgAspTrpGluLysAlaValGluThr-180 |
| SEQ. ID. NO. 6930 | 182-ArgLeuLeuSerHisAspAspGlnThrTyr-191 |
| SEQ. ID. NO. 6931 | 221-LysAlaLeuGluAlaAsnLysLysCysThrArg-231 |
| SEQ. ID. NO. 6932 | 238-AspIleGluHisArgGlnGlyAsn-245 |
| SEQ. ID. NO. 6933 | 277-AlaGlnGlyLysProGluGluGlyLeuAsnArgLeuThrGlyTyr-291 |
| SEQ. ID. NO. 6934 | 312-LysCysGluLysGluAlaAla-318 |
| SEQ. ID. NO. 6935 | 323-GluLeuValArgArgLysProAspLeuAsnGly-333 |
| SEQ. ID. NO. 6936 | 341-LysSerAspMetAsnProAlaTrpLysAlaAspAlaAspMetMetArg-357 |
| SEQ. ID. NO. 6937 | 368-ValMetTyrArgCysArgAsnCysHisPheLys-378 |
| SEQ. ID. NO. 6938 | 386-CysProAlaCysAsnLysTrpGlnThrPheThrProAsnLysIleGluVal-402 |
| Hydrophilic Regions - Hopp-Woods | |
| SEQ. ID. NO. 6939 | 1-MetArgProAsnLeu-5 |
| SEQ. ID. NO. 6940 | 7-AsnSerLeuLysLysAlaAspMetAspAsn-16 |
| SEQ. ID. NO. 6941 | 45-ThrValLeuLysGlnAlaLysSerIle-53 |
| SEQ. ID. NO. 6942 | 62-AspAlaLeuValAspArgAsnSerGlyArgAlaAlaArgGluLeuAlaGluValValAspGlyArgProGlnSer-86 |
| SEQ. ID. NO. 6943 | 96-LeuTyrArgGlnArgGlyGluAsnAspLysAlaIleAsn-108 |
| SEQ. ID. NO. 6944 | 112-ThrMetLeuAspSerProAspThrValGlyGluLysArgAlaArgVal-127 |
| SEQ. ID. NO. 6945 | 140-LeuValAspArgAlaGlu-145 |
| SEQ. ID. NO. 6946 | 152-GlnAspGlyLysMetAlaArgGluAlaArgGln-162 |
| SEQ. ID. NO. 6947 | 169-GlnGlnAspArgAspTrpGluLysAlaValGluThr-180 |
| SEQ. ID. NO. 6948 | 184-LeuSerHisAspAspGlnThrTyr-191 |
| SEQ. ID. NO. 6949 | 221-LysAlaLeuGluAlaAsnLysLysCysThrArg-231 |
| SEQ. ID. NO. 6950 | 238-AspIleGluHisArgGlnGlyAsn-245 |
| SEQ. ID. NO. 6951 | 279-GlyLysProGluGluGlyLeuAsn-286 |

TABLE 1-continued

| | |
|---|---|
| SEQ. ID. NO. 6952 | 312-LysCysGluLysGluAlaAla-318 |
| SEQ. ID. NO. 6953 | 323-GluLeuValArgArgLysProAspLeu-331 |
| SEQ. ID. NO. 6954 | 349-TrpLysAlaAspAlaAspMetMetArg-357 |
| SEQ. ID. NO. 6955 | 368-ValMetTyrArgCysArgAsnCysHis-376 |
| SEQ. ID. NO. 6956 | 398-AsnLysIleGluVal-402 |

575
AMPHI Regions - AMPHI

| | |
|---|---|
| SEQ. ID. NO. 6957 | 8-PheArgLysProAlaSer-13 |
| SEQ. ID. NO. 6958 | 20-PheAlaGluAlaVal-24 |
| SEQ. ID. NO. 6959 | 42-SerThrValSerGlyLeuPheSerAla-50 |
| SEQ. ID. NO. 6960 | 114-LeuSerLysSerLysSer-119 |
| SEQ. ID. NO. 6961 | 139-SerSerAspSerPro-143 |
| SEQ. ID. NO. 6962 | 150-PheThrSerPhePheGly-155 |
| SEQ. ID. NO. 6963 | 163-ValSerThrSerAlaLysValIleSerMetPro-173 |
| SEQ. ID. NO. 6964 | 217-SerLysValTyrGluProProAsnArgProSerAsn-228 |
| SEQ. ID. NO. 6965 | 237-AlaGluThrCysSerThr-242 |
| SEQ. ID. NO. 6966 | 287-AlaGlyPheSerAlaPheAlaSerGlyAla-296 |
| SEQ. ID. NO. 6967 | 298-ThrPheAlaSerGlyPheSerThrGly-306 |
| SEQ. ID. NO. 6968 | 308-SerThrValAlaCys-312 |
| SEQ. ID. NO. 6969 | 315-GlySerAspGlyMetAspAlaValSerAlaLeu-325 |

Antigenic Index - Jameson-Wolf

| | |
|---|---|
| SEQ. ID. NO. 6970 | 2-ValSerGlyGluGluAlaPheArgLysProAlaSerProGluGlyGluAlaGlyPhe-20 |
| SEQ. ID. NO. 6971 | 34-GlyArgLeuSerGluLysSerValSer-42 |
| SEQ. ID. NO. 6972 | 54-ThrAspSerGlySerGlyVal-60 |
| SEQ. ID. NO. 6973 | 96-SerSerCysValSerAlaProAspLysMetProPhe-108 |
| SEQ. ID. NO. 6974 | 113-ArgLeuSerLysSerLysSerMetArgLeuGluGly-124 |
| SEQ. ID. NO. 6975 | 134-PheAlaAspAsnSerSerSerAspSerProSerLysAlaSerVal-148 |
| SEQ. ID. NO. 6976 | 155-GlyAlaGlySerGly-159 |
| SEQ. ID. NO. 6977 | 173-ProSerSerAlaAlaSerSerArgSerGlySerSerSerGlyThrAspSerSerValArgArgAlaArgLeuAspTrpAlaArgArgLysSerSerSerArgAlaIle-208 |
| SEQ. ID. NO. 6978 | 211-AlaProProProAlaSer-216 |
| SEQ. ID. NO. 6979 | 218-LysValTyrGluProProAsnArgProSerAsnSer-229 |
| SEQ. ID. NO. 6980 | 232-SerValSerSerSerAlaGluThrCysSerThrGlySerGluThr-246 |
| SEQ. ID. NO. 6981 | 265-GlyAlaAspSerAlaAlaVal-271 |
| SEQ. ID. NO. 6982 | 280-GlyThrGlySerGlyArgThrAla-287 |
| SEQ. ID. NO. 6983 | 303-PheSerThrGlyPhe-307 |
| SEQ. ID. NO. 6984 | 313-LeuAspGlySerAspGlyMetAsp-320 |

Hydrophilic Regions - Hopp-Woods

| | |
|---|---|
| SEQ. ID. NO. 6985 | 2-ValSerGlyGluGluAlaPheArgLysProAlaSerProGluGlyGluAlaGlyPhe-20 |
| SEQ. ID. NO. 6986 | 34-GlyArgLeuSerGluLysSerValSer-42 |
| SEQ. ID. NO. 6987 | 101-SerAlaProAspLysMetPro-107 |
| SEQ. ID. NO. 6988 | 113-ArgLeuSerLysSerLysSerMetArgLeuGluGly-124 |
| SEQ. ID. NO. 6989 | 137-AsnSerSerSerAspSerProSerLysAla-146 |
| SEQ. ID. NO. 6990 | 176-AlaAlaSerSerArgSerGlySerSerSerGlyThrAspSerSerValArgArgAlaArgLeuAspTrpAlaArgArgLysSerSerSerArgAlaIle-208 |
| SEQ. ID. NO. 6991 | 218-LysValTyrGluProProAsnArgProSerAsn-228 |
| SEQ. ID. NO. 6992 | 235-SerSerAlaGluThrCysSerThrGlySerGluThr-246 |
| SEQ. ID. NO. 6993 | 314-AspGlySerAspGlyMetAsp-320 |

576-1
AMPHI Regions - AMPHI

| | |
|---|---|
| SEQ. ID. NO. 6994 | 31-AlaSerGluProAlaAlaAla-37 |
| SEQ. ID. NO. 6995 | 46-SerIleGlySerThr-50 |
| SEQ. ID. NO. 6996 | 63-GlyArgSerLeuLysGlnMetLys-70 |
| SEQ. ID. NO. 6997 | 82-ThrGluAlaMetGln-86 |
| SEQ. ID. NO. 6998 | 102-GlnGluValMetMetLysPheLeuGlnGluGlnGlnAlaLysAlaValGluLysHis-120 |
| SEQ. ID. NO. 6999 | 140-AlaLysAspGlyValLysThrThr-147 |
| SEQ. ID. NO. 7000 | 199-SerGlnValIleProGlyTrpThrGluGlyVal-209 |

Antigenic Index - Jameson-Wolf

| | |
|---|---|
| SEQ. ID. NO. 7001 | 20-AlaCysGlyLysLysGluAlaAlaPro-28 |
| SEQ. ID. NO. 7002 | 30-SerAlaSerGluProAlaAla-36 |
| SEQ. ID. NO. 7003 | 38-SerSerAlaGlnGlyAspThrSerSerIleGly-48 |
| SEQ. ID. NO. 7004 | 61-AspIleGlyArgSerLeuLysGlnMetLysGluGlnGlyAlaGluIleAspLeu-78 |
| SEQ. ID. NO. 7005 | 89-TyrAspGlyLysGluIleLysMetThrGluGluGlnAlaGln-102 |
| SEQ. ID. NO. 7006 | 109-LeuGlnGluGlnGlnAlaLysAlaValGluLysHisLysAlaAspAlaLysAlaAsnLysGluLysGlyGluAlaPheLeuLysGluAsnAlaAlaLysAspGlyValLysThrThrAlaSerGlyLeu-151 |
| SEQ. ID. NO. 7007 | 154-LysIleThrLysGlnGlyGluGlyLysGlnProThrLysAspAspIleVal-170 |
| SEQ. ID. NO. 7008 | 173-GluTyrGluGlyArgLeuIleAsp-180 |
| SEQ. ID. NO. 7009 | 183-ValPheAspSerSerLysAlaAsnGlyGly-192 |
| SEQ. ID. NO. 7010 | 210-GlnLeuLeuLysGluGlyGlyGlu-217 |
| SEQ. ID. NO. 7011 | 224-SerAsnLeuAlaTyrArgGluGlnGlyAlaGlyAspLysIleGlyProAsnAla-241 |
| SEQ. ID. NO. 7012 | 253-GlyAlaProGluAsnAlaProAlaLysGlnProAla-264 |
| SEQ. ID. NO. 7013 | 266-ValAspIleLysLysValAsn-272 |

Hydrophilic Regions - Hopp-Woods

| | |
|---|---|
| SEQ. ID. NO. 7014 | 21-CysGlyLysLysGluAlaAlaPro-28 |
| SEQ. ID. NO. 7015 | 30-SerAlaSerGluProAlaAla-36 |
| SEQ. ID. NO. 7016 | 40-AlaGlnGlyAspThrSerSer-46 |
| SEQ. ID. NO. 7017 | 61-AspIleGlyArgSerLeuLysGlnMetLysGluGlnGlyAlaGluIleAspLeu-78 |
| SEQ. ID. NO. 7018 | 89-TyrAspGlyLysGluIleLysMetThrGluGluGlnAlaGln-102 |
| SEQ. ID. NO. 7019 | 112-GlnGlnAlaLysAlaValGluLysHisLysAlaAspAlaLysAlaAsnLysGluLysGlyGluAlaPheLeuLysGluAsnAlaAlaLysAspGlyValLysThrThrAla-148 |

TABLE 1-continued

| | |
|---|---|
| SEQ. ID. NO. 7020 | 155-IleThrLysGlnGlyGluGlyLysGlnProThrLysAspAspIleVal-170 |
| SEQ. ID. NO. 7021 | 173-GluTyrGluGlyArgLeuIleAsp-180 |
| SEQ. ID. NO. 7022 | 185-AspSerSerLysAlaAsnGly-191 |
| SEQ. ID. NO. 7023 | 210-GlnLeuLeuLysGluGlyGlyGlu-217 |
| SEQ. ID. NO. 7024 | 227-AlaTyrArgGluGlnGlyAlaGlyAspLysIleGlyPro-239 |
| SEQ. ID. NO. 7025 | 253-GlyAlaProGluAsnAlaProAlaLysGlnProAla-264 |
| SEQ. ID. NO. 7026 | 266-ValAspIleLysLysValAsn-272 |

577
AMPHI Regions - AMPHI

| | |
|---|---|
| SEQ. ID. NO. 7027 | 8-GlyLysIleValGlyAsn-13 |
| SEQ. ID. NO. 7028 | 24-AlaAlaSerTyrProLysProCysLysSerPheLysLeuAla-37 |
| SEQ. ID. NO. 7029 | 62-ThrValIleLysIleIle-67 |
| SEQ. ID. NO. 7030 | 104-AlaPheValValGlyIleIlePheGlyMetPheAlaLeuPheGlyArg-119 |
| SEQ. ID. NO. 7031 | 144-GluLeuThrAlaProProAlaGln-151 |

Antigenic Index - Jameson-Wolf

| | |
|---|---|
| SEQ. ID. NO. 7032 | 1-MetGluArgAsnGlyVal-6 |
| SEQ. ID. NO. 7033 | 14-ArgIleLeuArgMetSerSerGluHisAla-23 |
| SEQ. ID. NO. 7034 | 26-SerTyrProLysProCysLysSerPheLys-35 |
| SEQ. ID. NO. 7035 | 88-LeuProGlyGlnLysPheAspLeu-95 |
| SEQ. ID. NO. 7036 | 121-LeuSerLeuArgGlyGluAsnGlyArgLeuArgAlaGluValLysLysAsnAlaArgLeuThrGlyLysGluLeuThrAlaProProAlaGlnAsnAlaProGluSerThrLysGlnPro-160 |

Hydrophilic Regions - Hopp-Woods

| | |
|---|---|
| SEQ. ID. NO. 7037 | 1-MetGluArgAsnGlyVal-6 |
| SEQ. ID. NO. 7038 | 14-ArgIleLeuArgMetSerSerGluHisAla-23 |
| SEQ. ID. NO. 7039 | 29-LysProCysLysSerPheLys-35 |
| SEQ. ID. NO. 7040 | 121-LeuSerLeuArgGlyGluAsnGlyArgLeuArgAlaGluValLysLysAsnAlaArgLeuThrGlyLysGluLeuThr-146 |
| SEQ. ID. NO. 7041 | 152-AsnAlaProGluSerThrLysGlnPro-160 |

578
AMPHI Regions - AMPHI

| | |
|---|---|
| SEQ. ID. NO. 7042 | 10-PheAlaAspPhePheLysAspPheAlaProGlnPheGlyGlyPheGlnAsn-26 |
| SEQ. ID. NO. 7043 | 34-AspPhePheAlaAlaPheLeuGlyGlyLeuGluGlyAsnMetGlyAsnThrAla-51 |
| SEQ. ID. NO. 7044 | 71-AsnAlaAspAlaAlaArgPhe-77 |

Antigenic Index - Jameson-Wolf

| | |
|---|---|
| SEQ. ID. NO. 7045 | 2-GlyLysLeuAspIle-6 |
| SEQ. ID. NO. 7046 | 13-PhePheLysAspPheAlaProGlnPheGlyGly-23 |
| SEQ. ID. NO. 7047 | 43-LeuGluGlyAsnMetGlyAsnThrAla-51 |
| SEQ. ID. NO. 7048 | 73-AspAlaAlaArgPheAlaGlu-79 |
| SEQ. ID. NO. 7049 | 90-GlnAsnIleGlnThrGlyAsnAspPheArgLeuGlnArgGlyGlyValGly-106 |

Hydrophilic Regions - Hopp-Woods

| | |
|---|---|
| SEQ. ID. NO. 7050 | 2-GlyLysLeuAspIle-6 |
| SEQ. ID. NO. 7051 | 73-AspAlaAlaArgPheAlaGlu-79 |
| SEQ. ID. NO. 7052 | 96-AsnAspPheArgLeuGlnArg-102 |

579-1
AMPHI Regions - AMPHI

| | |
|---|---|
| SEQ. ID. NO. 7053 | 6-PheAspPheLeuHisLeuIleSerValSerGlyTrpGluHisLeuAlaGlu-22 |
| SEQ. ID. NO. 7054 | 49-ValAlaValMetArg-53 |
| SEQ. ID. NO. 7055 | 66-IleSerPheLeuCysAsn-71 |
| SEQ. ID. NO. 7056 | 115-LeuSerAsnPheAla-119 |
| SEQ. ID. NO. 7057 | 129-ProPheLysValGlyAspPheIleArgValGlyGlyPheGluGlyTyrValArgGluIleLys-149 |
| SEQ. ID. NO. 7058 | 258-GlnValValGluAsnLeuArg-264 |

Antigenic Index - Jameson-Wolf

| | |
|---|---|
| SEQ. ID. NO. 7059 | 110-SerLeuLysAspGlnLeuSer-116 |
| SEQ. ID. NO. 7060 | 128-ArgProPheLysVal-132 |
| SEQ. ID. NO. 7061 | 136-IleArgValGlyGlyPheGluGlyTyrValArgGluIleLysMet-150 |
| SEQ. ID. NO. 7062 | 154-SerLeuArgThrThrAspAsnGluGluValValLeu-165 |
| SEQ. ID. NO. 7063 | 175-IleValAsnArgSerThrLeu-181 |
| SEQ. ID. NO. 7064 | 198-LeuLysValAlaLysGluAlaValLeu-206 |
| SEQ. ID. NO. 7065 | 216-ValGlnAsnGluGluArgGlnAla-223 |
| SEQ. ID. NO. 7066 | 231-GlyAspAsnAlaIle-235 |
| SEQ. ID. NO. 7067 | 244-AsnGluAlaAspArgTrpThrLeu-251 |
| SEQ. ID. NO. 7068 | 253-CysAspLeuAsnGluGlnValValGluAsnLeuArgLysValAsn-267 |
| SEQ. ID. NO. 7069 | 271-ProPheProGlnArgAspIleHis-278 |

Hydrophilic Regions - Hopp-Woods

| | |
|---|---|
| SEQ. ID. NO. 7070 | 110-SerLeuLysAspGlnLeu-115 |
| SEQ. ID. NO. 7071 | 144-TyrValArgGluIleLysMet-150 |
| SEQ. ID. NO. 7072 | 155-LeuArgThrThrAspAsnGluGluVal-164 |
| SEQ. ID. NO. 7073 | 198-LeuLysValAlaLysGluAlaValLeu-206 |
| SEQ. ID. NO. 7074 | 216-ValGlnAsnGluGluArgGlnAla-223 |
| SEQ. ID. NO. 7075 | 244-AsnGluAlaAspArgTrp-249 |
| SEQ. ID. NO. 7076 | 254-AspLeuAsnGluGlnValValGluAsnLeuArgLysValAsn-267 |
| SEQ. ID. NO. 7077 | 273-ProGlnArgAspIleHis-278 |

580
AMPHI Regions - AMPHI

| | |
|---|---|
| SEQ. ID. NO. 7078 | 47-ProValSerAlaSerLys-52 |
| SEQ. ID. NO. 7079 | 54-SerLeuValLysProLeuSerGlnProLeuAla-64 |

Antigenic Index - Jameson-Wolf

| | |
|---|---|
| SEQ. ID. NO. 7080 | 1-MetAspSerProLysValGlyCysGly-9 |
| SEQ. ID. NO. 7081 | 35-ProPheGlyProThrMetPro-41 |
| SEQ. ID. NO. 7082 | 48-ValSerAlaSerLys-52 |
| SEQ. ID. NO. 7083 | 66-AlaArgProGluAlaAlaHis-72 |

TABLE 1-continued

| SEQ. ID. NO. 7084 | 81-ArgProGluAlaLeuAlaAspSerSerValSerProThrHisAlaThrSerGlyGluVal-100 |

Hydrophilic Regions - Hopp-Woods
| SEQ. ID. NO. 7085 | 1-MetAspSerProLysVal-6 |
| SEQ. ID. NO. 7086 | 66-AlaArgProGluAlaAlaHis-72 |
| SEQ. ID. NO. 7087 | 81-ArgProGluAlaLeuAla-86 |
| SEQ. ID. NO. 7088 | 96-ThrSerGlyGluVal-100 |

581
AMPHI Regions - AMPHI
| SEQ. ID. NO. 7089 | 43-SerHisPheIleSerLeu-48 |
| SEQ. ID. NO. 7090 | 56-ArgGluCysPheValGlyPhe-62 |
| SEQ. ID. NO. 7091 | 76-AlaThrAlaPheGlyArgIleAsnGln-84 |
| SEQ. ID. NO. 7092 | 91-ValHisGlyPheLeuThrThrPheAlaGlyArgIleAlaAsnProAlaHisCysGlnSerGlnThr-112 |

Antigenic Index - Jameson-Wolf
| SEQ. ID. NO. 7093 | 8-GlyGlnThrGlyIleGluGlnAsnThrPheCysArgArgGlyPheThrArgValAsnMetGlyGlyAsnThrAspVal-33 |
| SEQ. ID. NO. 7094 | 35-ValGlnAlaAspArgGlyLeuThrSer-43 |
| SEQ. ID. NO. 7095 | 49-SerLysLeuGluThrGluValArgGluCysPhe-59 |
| SEQ. ID. NO. 7096 | 100-GlyArgIleAlaAsnProAlaHisCysGlnSerGlnThrAla-113 |

Hydrophilic Regions - Hopp-Woods
| SEQ. ID. NO. 7097 | 35-ValGlnAlaAspArgGlyLeu-41 |
| SEQ. ID. NO. 7098 | 49-SerLysLeuGluThrGluValArgGlu-57 |

582
AMPHI Regions - AMPHI
| SEQ. ID. NO. 7099 | 27-ThrAspAsnValThrArgLeuAla-34 |
| SEQ. ID. NO. 7100 | 65-ValArgSerSerLeu-69 |
| SEQ. ID. NO. 7101 | 91-GlyGluThrAlaAspIleTyrThrProLeuSer-101 |
| SEQ. ID. NO. 7102 | 139-GlySerProThrArg-143 |
| SEQ. ID. NO. 7103 | 169-IleAlaGluAspLeuPhe-174 |
| SEQ. ID. NO. 7104 | 246-SerArgSerTrpAsnArgIleTyrAlaMet-255 |
| SEQ. ID. NO. 7105 | 263-LeuThrValIleProArgValTrpValArgAlaPheAspGlnSer-277 |
| SEQ. ID. NO. 7106 | 286-IleAlaAspTyrMetGlyTyr-292 |
| SEQ. ID. NO. 7107 | 334-LeuLysGlyValValArgGlyPheHisGlyTyrGlyGlu-346 |

Antigenic Index - Jameson-Wolf
| SEQ. ID. NO. 7108 | 26-LeuThrAspAsnValThr-31 |
| SEQ. ID. NO. 7109 | 34-AlaCysTyrAspArg-38 |
| SEQ. ID. NO. 7110 | 44-LeuProSerSerAlaGlyGlnGluGlyGlnGluSerLysAla-57 |
| SEQ. ID. NO. 7111 | 63-GluThrValArgSerSerLeuAspLysGlyGluAla-74 |
| SEQ. ID. NO. 7112 | 77-ValValGluLysGlyGlyAspAlaLeuProAlaAspSerAlaGlyGluThrAlaAsp-95 |
| SEQ. ID. NO. 7113 | 105-AspLeuAspLysAsnAspLeuArgGly-113 |
| SEQ. ID. NO. 7114 | 115-LeuGlyValArgGluHisAsnProMetTyr-124 |
| SEQ. ID. NO. 7115 | 131-AsnAsnSerProAsnTyrAlaProGlySerProThrArgGlyThrThrValGlnGluLysPheGlyGlnGlnLysArgAlaGluThrLysLeu-161 |
| SEQ. ID. NO. 7116 | 165-PheLysSerLysIleAlaGluAspLeuPheLysThrArgAla-178 |
| SEQ. ID. NO. 7117 | 183-GlyTyrThrGlnArgSerAspTrpGlnIleTyrAsnGlnGlyArgLysSerAlaProPheArgAsnThrAspTyrLysPro-209 |
| SEQ. ID. NO. 7118 | 216-ProValLysAlaAspLeuProPheGlyGlyArgLeuArgMet-229 |
| SEQ. ID. NO. 7119 | 237-GlnSerAsnGlyGlnSerArgProGluSerArgSerTrpAsn-250 |
| SEQ. ID. NO. 7120 | 273-AlaPheAspGlnSerGlyAspLysAsnAspAsnProAspIleAlaAsp-288 |
| SEQ. ID. NO. 7121 | 291-GlyTyrGlyAspValLysLeuGlnTyrArgLeuAsnAspArgGlnAsnVal-307 |
| SEQ. ID. NO. 7122 | 312-ArgTyrAsnProLysThrGlyTyr-319 |
| SEQ. ID. NO. 7123 | 330-IleLysGlyLysLeuLysGlyValVal-338 |
| SEQ. ID. NO. 7124 | 342-HisGlyTyrGlyGluSerLeuIleAspTyrAsnHisLysGlnAsnGly-357 |
| SEQ. ID. NO. 7125 | 365-AsnAspLeuAspGlyIle-370 |

Hydrophilic Regions - Hopp-Woods
| SEQ. ID. NO. 7126 | 48-AlaGlyGlnGluGlyGlnGluSerLysAla-57 |
| SEQ. ID. NO. 7127 | 63-GluThrValArgSerSerLeuAspLysGlyGluAla-74 |
| SEQ. ID. NO. 7128 | 79-GluLysGlyGlyAspAlaLeuProAlaAspSerAlaGlyGluThrAlaAsp-95 |
| SEQ. ID. NO. 7129 | 105-AspLeuAspLysAsnAspLeuArgGly-113 |
| SEQ. ID. NO. 7130 | 115-LeuGlyValArgGluHisAsn-121 |
| SEQ. ID. NO. 7131 | 140-SerProThrArgGlyThrThrValGlnGluLysPheGlyGlnGlnLysArgAlaGluThrLysLeu-161 |
| SEQ. ID. NO. 7132 | 165-PheLysSerLysIleAlaGluAspLeuPheLysThrArgAla-178 |
| SEQ. ID. NO. 7133 | 195-GlnGlyArgLysSerAlaProPheArgAsnThrAspTyrLysPro-209 |
| SEQ. ID. NO. 7134 | 225-GlyArgLeuArgMet-229 |
| SEQ. ID. NO. 7135 | 239-AsnGlyGlnSerArgProGluSerArgSerTrp-249 |
| SEQ. ID. NO. 7136 | 274-PheAspGlnSerGlyAspLysAsnAspAsnProAspIleAlaAsp-288 |
| SEQ. ID. NO. 7137 | 293-GlyAspValLysLeu-297 |
| SEQ. ID. NO. 7138 | 299-TyrArgLeuAsnAspArgGlnAsn-306 |
| SEQ. ID. NO. 7139 | 332-GlyLysLeuLysGlyValVal-338 |
| SEQ. ID. NO. 7140 | 352-AsnHisLysGlnAsn-356 |

583
AMPHI Regions - AMPHI
| SEQ. ID. NO. 7141 | 11-HisLeuAlaPheCysAlaPheCysGlyIle-20 |
| SEQ. ID. NO. 7142 | 28-ArgLeuHisAsnArgMetTyrAsnAlaAlaAlaAlaArg-40 |
| SEQ. ID. NO. 7143 | 58-ValThrAspAlaGln-62 |
| SEQ. ID. NO. 7144 | 66-SerLysAsnGlyAspLysGlnIle-73 |
| SEQ. ID. NO. 7145 | 75-AspThrHisProGlnPro-80 |
| SEQ. ID. NO. 7146 | 117-GlyTyrAlaGlyTyrCysAspGln-124 |
| SEQ. ID. NO. 7147 | 140-AspAsnGlyGlyAsnHisThrAsp-147 |
| SEQ. ID. NO. 7148 | 162-GlyTyrGlyGlnCysGlnAsnGlnGlyAla-171 |

Antigenic Index - Jameson-Wolf
| SEQ. ID. NO. 7149 | 24-ThrAlaGlyAsnArgLeuHisAsnArgMetTyr-34 |

TABLE 1-continued

| SEQ. ID. NO. 7150 | 41-GlyIleGlyArgGlyAsnGlySerGlnGlnGlnPheGlyLysSerGluThrValThrAspAlaGlnArgPheSerSerLysAsnGlyAspLysGlnIle SerAspThrHisProGlnProCysPheGluGlnThrAlaArgAsnHisAsnCysAspGlyAsnGlnProAsnGlnArgIleGlyGluArgThrGlnArgIleAla HisArgArgAlaArgPhe-114 |
|---|---|
| SEQ. ID. NO. 7151 | 117-GlyTyrAlaGlyTyCysAspGlnProAspGlyAsnAsnArgGlnArgAlaGlnArgHisGlyLeuAlaAspAsnGlyAspGlyAsnHisThrAspLysHis GlyGlnGlnArgProSerLeuArgLeuAspProValGlyTyrGlyGlnCysGlnAsnGlnGlyAlaGlnTyrCysGlyAsnGlyGluGlyTyrArgPhe-182 |
| SEQ. ID. NO. 7152 | 190-AspLeuArgLysLysAspArgProGluLysSerGluLys-202 |

Hydrophilic Regions - Hopp-Woods

| SEQ. ID. NO. 7153 | 27-AsnArgLeuHisAsn-31 |
|---|---|
| SEQ. ID. NO. 7154 | 41-GlyIleGlyArgGlyAsnGlySer-48 |
| SEQ. ID. NO. 7155 | 51-GlnPheGlyLysSerGluThrValThrAspAlaGlnArgPheSerSerLysAsnGlyAspLysGlnIleSerAspThrHisPro-78 |
| SEQ. ID. NO. 7156 | 84-GlnThrAlaArgAsnHisAsnCysAspGlyAsnGlnProAsnGlnArgIleGlyGluArgThrGlnArgIleAlaHisArgArgAlaArgPhe-114 |
| SEQ. ID. NO. 7157 | 123-AspGlnProAspGlyAsnAsnArgGlnArgAlaGlnArg-135 |
| SEQ. ID. NO. 7158 | 137-GlyLeuAlaAspAsnGlyGlyAsnHisThrAspLysHisGlyGlnGlnArgProSerLeuArgLeuAspPro-160 |
| SEQ. ID. NO. 7159 | 178-GluGlyTyrArgPhe-182 |
| SEQ. ID. NO. 7160 | 190-AspLeuArgLysLysAspArgProGluLysSerGluLys-202 |

584-2
AMPHI Regions - AMPHI

| SEQ. ID. NO. 7161 | 28-GluPheSerGluSerAlaGly-34 |
|---|---|
| SEQ. ID. NO. 7162 | 60-AlaGluPheValLysLysPheAsnLysPheIleArgLys-72 |
| SEQ. ID. NO. 7163 | 115-AspPheAspGluLeuAsnArgPheIleAlaAspIle-126 |
| SEQ. ID. NO. 7164 | 148-IleAspGlnValSerLysAsp-154 |
| SEQ. ID. NO. 7165 | 166-LeuAlaGlyValLeuGly-171 |
| SEQ. ID. NO. 7166 | 186-GlySerHisIleAla-190 |
| SEQ. ID. NO. 7167 | 196-GlnAlaLysMetLeuArgAlaMet-203 |

Antigenic Index - Jameson-Wolf

| SEQ. ID. NO. 7168 | 37-ValAlaGlnAspThrMetSer-43 |
|---|---|
| SEQ. ID. NO. 7169 | 50-AlaGluGlyArgAspLysAsnAlaVal-58 |
| SEQ. ID. NO. 7170 | 61-GluPheValLysLysPheAsnLysPheIleArgLysSerLysAsnGlySerPheLysThrGluLeuValSerArgSerAlaMetProArgTyrGlnTyr ThrAsnGlyArgArgIleGlnThrGlyTrpGluGluArgAlaGluPheLysValGluGlyArgAspPheAspGluLeuAsn-120 |
| SEQ. ID. NO. 7171 | 138-HisValSerArgGluArgArgAsnGluValIleAspGlnValSerLysAspAlaValLeu-157 |
| SEQ. ID. NO. 7172 | 159-PheLysAlaArgAlaGluLysLeuAla-167 |
| SEQ. ID. NO. 7173 | 189-IleAlaGlyGlyGly-193 |
| SEQ. ID. NO. 7174 | 210-AsnMetGluGlyAlaAspSerAlaAlaProGlyValGluGluIleSer-225 |

Hydrophilic Regions - Hopp-Woods

| SEQ. ID. NO. 7175 | 50-AlaGluGlyArgAspLysAsnAlaVal-58 |
|---|---|
| SEQ. ID. NO. 7176 | 61-GluPheValLysLysPheAsnLysPheIleArgLysSerLysAsnGlySerPheLysThrGluLeuValSer-84 |
| SEQ. ID. NO. 7177 | 95-AsnGlyArgArgIleGlnThrGlyTrpGluGluArgAlaGluPheLysValGluGlyArgAspPheAspGluLeuAsn-120 |
| SEQ. ID. NO. 7178 | 138-HisValSerArgGluArgArgAsnGluValIleAspGlnValSerLysAspAlaValLeu-157 |
| SEQ. ID. NO. 7179 | 159-PheLysAlaArgAlaGluLysLeuAla-167 |
| SEQ. ID. NO. 7180 | 210-AsnMetGluGlyAlaAspSerAlaAlaProGlyValGluGluIleSer-225 |

585
AMPHI Regions - AMPHI

| SEQ. ID. NO. 7181 | 6-ArgIlePheAlaThrPheCysAlaValIleValCys-17 |
|---|---|
| SEQ. ID. NO. 7182 | 46-ThrThrLeuMetGlySerIleIleSer-54 |
| SEQ. ID. NO. 7183 | 65-ArgGluIleLeuThrGluTrpLysAsp-73 |
| SEQ. ID. NO. 7184 | 93-AsnArgTyrIleAsp-97 |
| SEQ. ID. NO. 7185 | 133-LysAspTrpAspLysLeuGlnAlaArgArg-142 |
| SEQ. ID. NO. 7186 | 153-ProLeuAlaProIleTrp-158 |
| SEQ. ID. NO. 7187 | 178-LeuAlaGlyAsnIleAlaLysProIleArgIleLeuGlyAsnGlyMetAspArgValAla-197 |
| SEQ. ID. NO. 7188 | 223-PheAspLysMetValGluLysLeuGluLysLeuVal-234 |
| SEQ. ID. NO. 7189 | 247-GluMetArgSerPro-251 |
| SEQ. ID. NO. 7190 | 255-MetGlnAlaIleValGlyLeuIle-262 |
| SEQ. ID. NO. 7191 | 273-LeuLysArgLeuGluGly-278 |
| SEQ. ID. NO. 7192 | 353-LeuTyrArgAlaPheAspAsnValIleArgAsnAlaValAsn-366 |
| SEQ. ID. NO. 7193 | 430-IleIleGluGlnHisCysGlyLysIleIleAlaGlu-441 |

Antigenic Index - Jameson-Wolf

| SEQ. ID. NO. 7194 | 36-AsnGlnPheAsnGlnArgArgThrIleGlu-45 |
|---|---|
| SEQ. ID. NO. 7195 | 56-PheArgAlaArgGlyAspAlaGlyAlaArgGluIleLeuThrGluTrpLysAspSerProValSer-77 |
| SEQ. ID. NO. 7196 | 84-GlnGlyAspGluLysLysAspIleLeu-92 |
| SEQ. ID. NO. 7197 | 99-TyrThrIleGluArgAlaArgLeu-106 |
| SEQ. ID. NO. 7198 | 120-GluTyrAspArgPheGlyGlu-126 |
| SEQ. ID. NO. 7199 | 133-LysAspTrpAspLysLeuGlnAlaArgArgLeuProSerPro-146 |
| SEQ. ID. NO. 7200 | 189-LeuGlyAsnGlyMetAspArgValAlaAsnGlyGluLeuGluThrArgIle-205 |
| SEQ. ID. NO. 7201 | 207-GlnGlnValAspAspArgAspAspGluLeuSer-217 |
| SEQ. ID. NO. 7202 | 225-LysMetValGluLysLeuGluLysLeuValAlaLysGluArgHisLeu-240 |
| SEQ. ID. NO. 7203 | 246-HisGluMetArgSerProLeuAla-253 |
| SEQ. ID. NO. 7204 | 264-AlaGlnProGlnLysGlnGlnTyrLeuLysArgLeuGluGlyGluLeuThrArgMetAspThrLeuAla-287 |
| SEQ. ID. NO. 7205 | 294-SerArgLeuGluThrSerAsnMetAlaLeuGluLysGluSerLeuLys-309 |
| SEQ. ID. NO. 7206 | 317-LeuValGluAspAsnGlnSerIleAlaGlnLysAsnGlyGln-330 |
| SEQ. ID. NO. 7207 | 335-SerAlaAspGlyLysIleProGluAsnThr-344 |
| SEQ. ID. NO. 7208 | 367-TyrSerProGluGlySerThr-373 |
| SEQ. ID. NO. 7209 | 377-AsnIleGlyGlnAspHisLysHis-384 |
| SEQ. ID. NO. 7210 | 388-AspValThrAspAsnGlyProGlyValAspGluMetGln-400 |
| SEQ. ID. NO. 7211 | 409-TyrArgAlaAspSerSerAlaAsnLysProGlyThrGly-421 |
| SEQ. ID. NO. 7212 | 432-GluGlnHisCysGlyLysIleIleAlaGluAsnIleLysProAsnGlyLeuArg-449 |
| SEQ. ID. NO. 7213 | 453-IleLeuProLysLysLysThrGlySerLysThrGluLysSerAlaAsn-468 |

Hydrophilic Regions - Hopp-Woods

| SEQ. ID. NO. 7214 | 37-GlnPheAsnGlnArgArgThrIleGlu-45 |
|---|---|
| SEQ. ID. NO. 7215 | 56-PheArgAlaArgGlyAspAlaGlyAlaArgGluIleLeuThrGluTrpLysAspSerProVal-76 |
| SEQ. ID. NO. 7216 | 84-GlnGlyAspGluLysLysAspIleLeu-92 |

TABLE 1-continued

| SEQ. ID. NO. 7217 | 100-ThrIleGluArgAlaArgLeu-106 |
| SEQ. ID. NO. 7218 | 120-GluTyrAspArgPheGlyGlu-126 |
| SEQ. ID. NO. 7219 | 133-LysAspTrpAspLysLeuGlnAlaArgArgLeuPro-144 |
| SEQ. ID. NO. 7220 | 192-GlyMetAspArgValAlaAsnGlyGluLeuGluThrArgIle-205 |
| SEQ. ID. NO. 7221 | 207-GlnGlnValAspAspArgAspAspGluLeuSer-217 |
| SEQ. ID. NO. 7222 | 225-LysMetValGluLysLeuGluLysLeuValAlaLysGluArgHisLeu-240 |
| SEQ. ID. NO. 7223 | 246-HisGluMetArgSerProLeu-252 |
| SEQ. ID. NO. 7224 | 265-GlnProGlnLysGlnGluGlnTyrLeuLysArgLeuGluGlyGluLeuThrArgMetAspThrLeuAla-287 |
| SEQ. ID. NO. 7225 | 294-SerArgLeuGluThr-298 |
| SEQ. ID. NO. 7226 | 302-AlaLeuGluLysGluSerLeuLys-309 |
| SEQ. ID. NO. 7227 | 317-LeuValGluAspAsnGlnSerIleAlaGlnLysAsnGlyGln-330 |
| SEQ. ID. NO. 7228 | 336-AlaAspGlyLysIleProGlu-342 |
| SEQ. ID. NO. 7229 | 389-ValThrAspAsnGlyProGlyValAspGluMetGln-400 |
| SEQ. ID. NO. 7230 | 410-ArgAlaAspSerSerAlaAsnLysProGlyThr-420 |
| SEQ. ID. NO. 7231 | 438-IleIleAlaGluAsnIleLys-444 |
| SEQ. ID. NO. 7232 | 454-LeuProLysLysLysThrGlySerLysThrGluLysSerAlaAsn-468 |

586
AMPHI Regions - AMPHI
| SEQ. ID. NO. 7233 | 12-AspAsnPheLysTyrPheTrpLysThr-20 |
| SEQ. ID. NO. 7234 | 30-IleLeuAlaAlaLeuGly-35 |
| SEQ. ID. NO. 7235 | 56-ValLeuAlaAsnIleValGluLysAlaGlnSerLys-67 |
| SEQ. ID. NO. 7236 | 80-LeuGlnGlnSerTyrProHisSerIleSer-89 |
| SEQ. ID. NO. 7237 | 177-SerGlnGluAlaLeuLysAsnTyrGlyGlnAlaLeuGluLysMetProGlnAspSerValGlyArg-198 |

Antigenic Index - Jameson-Wolf
| SEQ. ID. NO. 7238 | 4-HisLeuGluGluGlnGlnGluLeuAspAsn-13 |
| SEQ. ID. NO. 7239 | 42-TyrGlnAsnArgLysValSerGlnAsnGlnGluAla-53 |
| SEQ. ID. NO. 7240 | 60-IleValGluLysAlaGlnSerLysAlaProGlnSerGluIleAsnAlaGluLeuThrLysLeuGlnGln-82 |
| SEQ. ID. NO. 7241 | 100-ThrGluPheAspAlaGlnArgTyrAspValAlaGluGly-112 |
| SEQ. ID. NO. 7242 | 118-LeuSerAsnGlnLysAspSerLeu-125 |
| SEQ. ID. NO. 7243 | 140-GlnGlnLysLysTyrAspAla-146 |
| SEQ. ID. NO. 7244 | 153-ThrProValGluAlaAspPhe-159 |
| SEQ. ID. NO. 7245 | 164-MetGluThrLysGlyAspVal-170 |
| SEQ. ID. NO. 7246 | 173-AlaGlnGlyLysSerGlnGluAlaLeuLysAsnTyrGlyGlnAlaLeuGluLysMetProGlnAspSerValGlyArgGluLeuVal-201 |
| SEQ. ID. NO. 7247 | 204-LysLeuAspSerLeuLys-209 |

Hydrophilic Regions - Hopp-Woods
| SEQ. ID. NO. 7248 | 4-HisLeuGluGluGlnGlnGluLeuAspAsn-13 |
| SEQ. ID. NO. 7249 | 43-GlnAsnArgLysValSerGlnAsnGlnGluAla-53 |
| SEQ. ID. NO. 7250 | 60-IleValGluLysAlaGlnSerLysAlaProGlnSerGluIleAsnAlaGluLeuThrLys-79 |
| SEQ. ID. NO. 7251 | 100-ThrGluPheAspAlaGlnArgTyrAspValAlaGluGly-112 |
| SEQ. ID. NO. 7252 | 120-AsnGlnLysAspSerLeu-125 |
| SEQ. ID. NO. 7253 | 140-GlnGlnLysLysTyrAspAla-146 |
| SEQ. ID. NO. 7254 | 153-ThrProValGluAlaAspPhe-159 |
| SEQ. ID. NO. 7255 | 164-MetGluThrLysGlyAspVal-170 |
| SEQ. ID. NO. 7256 | 174-GlnGlyLysSerGlnGluAlaLeuLys-182 |
| SEQ. ID. NO. 7257 | 187-AlaLeuGluLysMetProGlnAspSerValGlyArgGluLeuVal-201 |
| SEQ. ID. NO. 7258 | 204-LysLeuAspSerLeuLys-209 |

587
AMPHI Regions - AMPHI
| SEQ. ID. NO. 7259 | 6-LeuProAlaLeuProAlaIleLeuProLeuSerThr-17 |
| SEQ. ID. NO. 7260 | 190-AsnGlySerLysThrLeuSer-196 |

Antigenic Index - Jameson-Wolf
| SEQ. ID. NO. 7261 | 27-AspIleMetThrAspLysGlyLysTrpLysLeuGluThr-39 |
| SEQ. ID. NO. 7262 | 44-LeuAsnSerGluAsnAsnArgAlaGluLeu-53 |
| SEQ. ID. NO. 7263 | 72-GluIleGlnGluAsnGlySerAsnThrAsp-81 |
| SEQ. ID. NO. 7264 | 95-GlyAsnThrAspIleTyrGlySerGlySer-104 |
| SEQ. ID. NO. 7265 | 108-HisGluGluArgLysLeuAspGlyAsnSerLysThrArgAsnLysArgMetSerAsp-126 |
| SEQ. ID. NO. 7266 | 135-PheLeuLysAspAspLysAsnProAla-143 |
| SEQ. ID. NO. 7267 | 151-ThrValTyrGluLysSerArgAsnLysAlaSerSerGlyLysSer-165 |
| SEQ. ID. NO. 7268 | 187-TyrArgIleAsnGlySerLysThrLeuSerAspGlyIleArgTyrLysSerGlyAsnTyr-206 |
| SEQ. ID. NO. 7269 | 217-AlaAsnAspArgIleSerLeuThrGlyGly-226 |
| SEQ. ID. NO. 7270 | 231-GlyArgGlnProAspArgThrAspGlyLysArgGluSerSerArgAsnThrSerThr-249 |
| SEQ. ID. NO. 7271 | 273-ValSerGlyGlnSerSerSerGluLeuLysPhe-283 |

Hydrophilic Regions - Hopp-Woods
| SEQ. ID. NO. 7272 | 27-AspIleMetThrAspLysGlyLysTrpLysLeu-37 |
| SEQ. ID. NO. 7273 | 47-GluAsnAsnArgAlaGluLeu-53 |
| SEQ. ID. NO. 7274 | 72-GluIleGlnGluAsnGlySerAsnThr-80 |
| SEQ. ID. NO. 7275 | 108-HisGluGluArgLysLeuAspGlyAsnSerLysThrArgAsnLysArgMetSerAsp-126 |
| SEQ. ID. NO. 7276 | 135-PheLeuLysAspAspLysAsnPro-142 |
| SEQ. ID. NO. 7277 | 151-ThrValTyrGluLysSerArgAsnLysAlaSerSerGly-163 |
| SEQ. ID. NO. 7278 | 193-LysThrLeuSerAspGlyIleArgTyrLysSer-203 |
| SEQ. ID. NO. 7279 | 217-AlaAsnAspArgIleSer-222 |
| SEQ. ID. NO. 7280 | 232-ArgGlnProAspArgThrAspGlyLysArgGluSerSerArgAsnThr-247 |
| SEQ. ID. NO. 7281 | 277-SerSerSerGluLeuLysPhe-283 |

588
AMPHI Regions - AMPHI
| SEQ. ID. NO. 7282 | 52-GlnAspGlyArgAsnTyrThrGlySerPhe-61 |
| SEQ. ID. NO. 7283 | 99-GlyThrPheLysLys-103 |

Antigenic Index - Jameson-Wolf
| SEQ. ID. NO. 7284 | 25-SerTyrGlnGluProGlyCysThrTyrAspGlyAsnValGlyLysAspGlyLysProAlaGlyLysGlyThrTrpArgCysGlnAspGlyArgAsnTyrThrGlySerPheLysAsnGlyLysPheAspGlyGlnGly-70 |

TABLE 1-continued

| | |
|---|---|
| SEQ. ID. NO. 7285 | 80-IlePheIleGluProPheAsnSerAspSerThrLysPheArg-93 |
| SEQ. ID. NO. 7286 | 100-ThrPheLysLysGlyLeuAlaHisGlyArgPheThrValSerGlnAsnGlyGluThr-118 |
| SEQ. ID. NO. 7287 | 124-CysGluAsnGlyMetIleLysGluValLysLeuProLysAsnLys-138 |
| Hydrophilic Regions - Hopp-Woods | |
| SEQ. ID. NO. 7288 | 36-AsnValGlyLysAspGlyLysProAlaGly-45 |
| SEQ. ID. NO. 7289 | 47-GlyThrTrpArgCysGlnAspGlyArgAsnTyr-57 |
| SEQ. ID. NO. 7290 | 61-PheLysAsnGlyLysPheAspGly-68 |
| SEQ. ID. NO. 7291 | 85-PheAsnSerAspSerThrLysPheArg-93 |
| SEQ. ID. NO. 7292 | 100-ThrPheLysLysGlyLeuAla-106 |
| SEQ. ID. NO. 7293 | 124-CysGluAsnGlyMetIleLysGluValLysLeuProLysAsnLys-138 |
| 589 | |
| AMPHI Regions - AMPHI | |
| SEQ. ID. NO. 7294 | 18-AlaSerArgIleGluLysValLeu-25 |
| SEQ. ID. NO. 7295 | 54-ValAlaAspIleAlaLysIleIleGluLys-63 |
| SEQ. ID. NO. 7296 | 125-SerValValGlnLeuTrpLeuAla-132 |
| SEQ. ID. NO. 7297 | 150-MetAspValLeuValThrIle-156 |
| SEQ. ID. NO. 7298 | 193-PheValSerLeuGlyLysPheLeuGluHisArg-203 |
| SEQ. ID. NO. 7299 | 225-ValGlnArgAsnGlyGlu-230 |
| SEQ. ID. NO. 7300 | 240-GlnIleGlyAspLeuIleArg-246 |
| SEQ. ID. NO. 7301 | 307-GlnThrGlnLeuGlyAspMetMetAsnAlaLeuSerGluAlaGln-321 |
| SEQ. ID. NO. 7302 | 325-AlaProIleAlaArgValAlaAspLys-333 |
| SEQ. ID. NO. 7303 | 391-MetGlyLysAlaVal-395 |
| SEQ. ID. NO. 7304 | 466-IleValSerAlaAlaAlaGln-471 |
| SEQ. ID. NO. 7305 | 477-IleProAlaAlaGln-481 |
| SEQ. ID. NO. 7306 | 497-GlyValGlyLeuValLys-502 |
| SEQ. ID. NO. 7307 | 511-LeuAlaLeuProLysPheLeuAspGlyValTrpAspIleAlaSerIle-526 |
| SEQ. ID. NO. 7308 | 539-PheAlaLeuAlaAspAlaLeuLys-546 |
| SEQ. ID. NO. 7309 | 548-AspThrAlaGluAlaIleGlyArgLeu-556 |
| SEQ. ID. NO. 7310 | 598-GluValGlnLysLeuLysAlaAla-605 |
| SEQ. ID. NO. 7311 | 612-ValGlyAspGlyIleAsnAspAlaPro-620 |
| SEQ. ID. NO. 7312 | 635-AlaAspValAlaGluHisThr-641 |
| SEQ. ID. NO. 7313 | 648-GlnHisSerValAsnGlnLeuAlaAsp-656 |
| SEQ. ID. NO. 7314 | 675-AlaPhePheTyrAsnIleLeu-681 |
| Antigenic Index - Jameson-Wolf | |
| SEQ. ID. NO. 7315 | 1-MetGlnGlnLysIleArgPheGlnIle-9 |
| SEQ. ID. NO. 7316 | 17-CysAlaSerArgIleGluLysValLeuAsnLysLysAspPheValGluSer-33 |
| SEQ. ID. NO. 7317 | 39-AlaSerGluGluAlaGlnValValPheAspAspSerLysThrSerVal-54 |
| SEQ. ID. NO. 7318 | 59-LysIleIleGluLysThrGlyTyrGlyAlaLysGluLysThrGluAspThrLeuProGlnProGluAlaGluHis-83 |
| SEQ. ID. NO. 7319 | 109-GlyArgHisAspTrp-113 |
| SEQ. ID. NO. 7320 | 143-IleLysGlyGlyLeu-147 |
| SEQ. ID. NO. 7321 | 200-LeuGluHisArgThrLysLysSerSerLeuAsn-210 |
| SEQ. ID. NO. 7322 | 223-ValAsnValGlnArgAsnGlyGluTrpLysGlnLeuProIleAspGln-238 |
| SEQ. ID. NO. 7323 | 248-AsnHisGlyGluArgIleAlaAla-255 |
| SEQ. ID. NO. 7324 | 257-GlyIleIleGluSerGlySerGlyTrpAlaAspGluSerHisLeuThrGlyGluSerAsnProGluGluLysLysAlaGlyGly-284 |
| SEQ. ID. NO. 7325 | 293-ThrGluGlySerVal-297 |
| SEQ. ID. NO. 7326 | 318-SerGluAlaGlnGlySerLysAlaProIle-327 |
| SEQ. ID. NO. 7327 | 329-ArgValAlaAspLysAlaAla-335 |
| SEQ. ID. NO. 7328 | 356-IleLysGlyAspTrp-360 |
| SEQ. ID. NO. 7329 | 391-MetGlyLysAlaValLys-396 |
| SEQ. ID. NO. 7330 | 404-AlaAlaAlaMetGluGluAlaAlaHis-412 |
| SEQ. ID. NO. 7331 | 417-ValLeuAspLysThrGlyThrLeuThrGluGlySerProGln-430 |
| SEQ. ID. NO. 7332 | 438-ProAspSerGlyPheAspGluAspAlaLeu-447 |
| SEQ. ID. NO. 7333 | 454-ValGluGlnAsnAla-458 |
| SEQ. ID. NO. 7334 | 493-AlaGluValGluGly-497 |
| SEQ. ID. NO. 7335 | 502-LysAlaGlyLysAlaGluPheAla-509 |
| SEQ. ID. NO. 7336 | 530-SerValAspAsnLysProIleGly-537 |
| SEQ. ID. NO. 7337 | 543-AspAlaLeuLysAlaAspThrAlaGluAlaIleGlyArgLeuLysLysHisAsnIle-561 |
| SEQ. ID. NO. 7338 | 567-SerGlyAspAsnGlnGlyThrValGluTyrValAla-578 |
| SEQ. ID. NO. 7339 | 588-GlyAsnMetSerProArgAspLysAlaAlaGluValGlnLysLeuLysAlaAlaGly-606 |
| SEQ. ID. NO. 7340 | 612-ValGlyAspGlyIleAsnAspAla-619 |
| SEQ. ID. NO. 7341 | 631-MetLysGlyGlyAlaAspValAlaGlu-639 |
| SEQ. ID. NO. 7342 | 710-AsnAlaLeuArgLeuLysArgValLysIleAsp-720 |
| Hydrophilic Regions - Hopp-Woods | |
| SEQ. ID. NO. 7343 | 1-MetGlnGlnLysIleArgPheGlnIle-9 |
| SEQ. ID. NO. 7344 | 19-SerArgIleGluLysValLeuAsnLysLysAspPheValGlu-32 |
| SEQ. ID. NO. 7345 | 39-AlaSerGluGluAlaGlnValValPheAspAspSerLysThrSerVal-54 |
| SEQ. ID. NO. 7346 | 64-ThrGlyTyrGlyAlaLysGluLysThrGluAspThrLeuProGlnProGluAlaGluHis-83 |
| SEQ. ID. NO. 7347 | 200-LeuGluHisArgThrLysLysSerSerLeu-209 |
| SEQ. ID. NO. 7348 | 224-AsnValGlnArgAsnGlyGluTrpLys-232 |
| SEQ. ID. NO. 7349 | 248-AsnHisGlyGluArgIleAlaAla-255 |
| SEQ. ID. NO. 7350 | 257-GlyIleIleGluSer-261 |
| SEQ. ID. NO. 7351 | 265-TrpAlaAspGluSerHisLeuThrGlyGluSerAsnProGluGluLysLysAlaGlyGly-284 |
| SEQ. ID. NO. 7352 | 318-SerGluAlaGlnGlySerLysAlaProIle-327 |
| SEQ. ID. NO. 7353 | 329-ArgValAlaAspLysAlaAla-335 |
| SEQ. ID. NO. 7354 | 404-AlaAlaAlaMetGluGluAlaAlaHis-412 |
| SEQ. ID. NO. 7355 | 417-ValLeuAspLysThrGlyThrLeuThrGluGlySerPro-429 |
| SEQ. ID. NO. 7356 | 440-SerGlyPheAspGluAspAlaLeu-447 |
| SEQ. ID. NO. 7357 | 454-ValGluGlnAsnAla-458 |
| SEQ. ID. NO. 7358 | 493-AlaGluValGluGly-497 |
| SEQ. ID. NO. 7359 | 502-LysAlaGlyLysAlaGluPheAla-509 |

TABLE 1-continued

| | |
|---|---|
| SEQ. ID. NO. 7360 | 531-ValAspAsnLysPro-535 |
| SEQ. ID. NO. 7361 | 543-AspAlaLeuLysAlaAspThrAlaGluAlaIleGlyArgLeuLysLysHisAsnIle-561 |
| SEQ. ID. NO. 7362 | 568-GlyAspAsnGlnGly-572 |
| SEQ. ID. NO. 7363 | 591-SerProArgAspLysAlaAlaGluValGlnLysLeuLysAlaAlaGly-606 |
| SEQ. ID. NO. 7364 | 633-GlyGlyAlaAspValAlaGlu-639 |
| SEQ. ID. NO. 7365 | 712-LeuArgLeuLysArgValLysIleAsp-720 |

590-1
AMPHI Regions - AMPHI

| | |
|---|---|
| SEQ. ID. NO. 7366 | 77-TyrLeuProAspAsnLeuLysThrValLeuGluGlnProValThrLeuValAsnHisIleThrHis-98 |
| SEQ. ID. NO. 7367 | 100-ProPheAlaGlyGlyPhe-105 |
| SEQ. ID. NO. 7368 | 123-LysValLeuGluArgPhePheGly-130 |
| SEQ. ID. NO. 7369 | 132-GlnValProAlaSerLeu-137 |
| SEQ. ID. NO. 7370 | 177-TyrGlnLysGlyPheLysSerTyrArgAsnGly-187 |
| SEQ. ID. NO. 7371 | 214-ThrSerAspGlyIleAsnProLeu-221 |
| SEQ. ID. NO. 7372 | 248-AsnGluLeuValAsnLeuVal-254 |
| SEQ. ID. NO. 7373 | 331-LysArgLysPheAla-335 |
| SEQ. ID. NO. 7374 | 420-LysMetLeuGluAsp-424 |
| SEQ. ID. NO. 7375 | 450-AspIleAsnGluThrLeuArgLeuMet-458 |
| SEQ. ID. NO. 7376 | 460-AspSerThrValGln-464 |

Antigenic Index - Jameson-Wolf

| | |
|---|---|
| SEQ. ID. NO. 7377 | 1-MetLysLysProLeu-5 |
| SEQ. ID. NO. 7378 | 26-LysAlaGluGluSerLeuThrGlnGlnGlnLysIleLeuGln-39 |
| SEQ. ID. NO. 7379 | 47-GluSerHisGlnTyrGluArgGlyTrp-55 |
| SEQ. ID. NO. 7380 | 62-ThrValIleArgLeuLysProGluLeu-70 |
| SEQ. ID. NO. 7381 | 72-AsnAsnAlaArgLysTyrLeuProAspAsnLeuLysThrValLeu-86 |
| SEQ. ID. NO. 7382 | 113-ThrGluPheLysTyrAlaProGluThrGluLysValLeuGlu-126 |
| SEQ. ID. NO. 7383 | 128-PhePheGlyLysGlnValPro-134 |
| SEQ. ID. NO. 7384 | 144-AsnGlySerGlyLysMetGluVal-151 |
| SEQ. ID. NO. 7385 | 157-AspTyrGluGluLeuSerGly-163 |
| SEQ. ID. NO. 7386 | 175-ThrValTyrGlnLysGlyPheLysSerTyrArgAsnGlyTyrAspAlaPro-191 |
| SEQ. ID. NO. 7387 | 196-LysLeuAlaAspLysGlyAspAlaAlaPheGlu-206 |
| SEQ. ID. NO. 7388 | 208-ValHisPheAspSerGluThrSerAspGlyIleAsn-219 |
| SEQ. ID. NO. 7389 | 233-PheSerLeuGluTrpLysGluGlyValAspTyr-243 |
| SEQ. ID. NO. 7390 | 264-AsnProAsnGlySerIleAlaProSerLysIleGluValGly-277 |
| SEQ. ID. NO. 7391 | 281-PheSerThrLysThrGlyGluSerGlyAla-290 |
| SEQ. ID. NO. 7392 | 292-IleAsnSerGluGlyGlnPheArgPheAspThr-302 |
| SEQ. ID. NO. 7393 | 304-ValTyrGlyAspGluLysTyrGlyPro-312 |
| SEQ. ID. NO. 7394 | 330-LeuLysArgLysPheAla-335 |
| SEQ. ID. NO. 7395 | 338-SerAlaLysLysMetThrGluGluGlnIleArgAsnAspLeu-351 |
| SEQ. ID. NO. 7396 | 355-ValLysGlyGluAlaSerGlyLeuPheThrAsnAsnProValLeuAsp-370 |
| SEQ. ID. NO. 7397 | 378-LeuProSerGlyLysIleAspValGlyGly-387 |
| SEQ. ID. NO. 7398 | 389-IleMetPheLysAspMetLysLysGluAspLeuAsnGln-401 |
| SEQ. ID. NO. 7399 | 406-LeuLysLysThrGluAlaAspIleArgMet-415 |
| SEQ. ID. NO. 7400 | 437-AsnAlaGluAspGluAlaGluGlyArgAlaSerLeuAspAspIleAsnGluThrLeu-455 |
| SEQ. ID. NO. 7401 | 466-MetAlaArgGluLysTyr-471 |
| SEQ. ID. NO. 7402 | 475-AsnGlyAspGlnIleAsp-480 |
| SEQ. ID. NO. 7403 | 485-LeuLysAsnAsnGlnLeuLysLeuAsnGlyLysThrLeuGlnAsnGluProGluProAspPheAspGluGlyGlyMetValSerGluProGlnGln-516 |

Hydrophilic Regions - Hopp-Woods

| | |
|---|---|
| SEQ. ID. NO. 7404 | 1-MetLysLysProLeu-5 |
| SEQ. ID. NO. 7405 | 26-LysAlaGluGluSerLeuThrGln-33 |
| SEQ. ID. NO. 7406 | 62-ThrValIleArgLeuLysProGluLeu-70 |
| SEQ. ID. NO. 7407 | 72-AsnAsnAlaArgLysTyrLeuProAspAsnLeuLysThrValLeu-86 |
| SEQ. ID. NO. 7408 | 113-ThrGluPheLysTyrAlaProGluThrGluLysValLeuGlu-126 |
| SEQ. ID. NO. 7409 | 147-GlyLysMetGluVal-151 |
| SEQ. ID. NO. 7410 | 157-AspTyrGluGluLeuSerGly-163 |
| SEQ. ID. NO. 7411 | 180-GlyPheLysSerTyrArgAsnGlyTyr-188 |
| SEQ. ID. NO. 7412 | 196-LysLeuAlaAspLysGlyAspAlaAlaPheGlu-206 |
| SEQ. ID. NO. 7413 | 208-ValHisPheAspSerGluThrSerAspGly-217 |
| SEQ. ID. NO. 7414 | 233-PheSerLeuGluTrpLysGluGlyValAspTyr-243 |
| SEQ. ID. NO. 7415 | 272-SerLysIleGluValGly-277 |
| SEQ. ID. NO. 7416 | 306-GlyAspGluLysTyrGlyPro-312 |
| SEQ. ID. NO. 7417 | 330-LeuLysArgLysPheAla-335 |
| SEQ. ID. NO. 7418 | 338-SerAlaLysLysMetThrGluGluGlnIleArgAsnAspLeu-351 |
| SEQ. ID. NO. 7419 | 355-ValLysGlyGluAla-359 |
| SEQ. ID. NO. 7420 | 381-GlyLysIleAspValGlyGly-387 |
| SEQ. ID. NO. 7421 | 389-IleMetPheLysAspMetLysLysGluAspLeuAsn-400 |
| SEQ. ID. NO. 7422 | 406-LeuLysLysThrGluAlaAspIleArgMet-415 |
| SEQ. ID. NO. 7423 | 437-AsnAlaGluAspGluAlaGluGlyArgAlaSerLeuAspAspIleAsnGluThrLeu-455 |
| SEQ. ID. NO. 7424 | 466-MetAlaArgGluLysTyr-471 |
| SEQ. ID. NO. 7425 | 486-LysAsnAsnGlnLeuLysLeuAsnGly-494 |
| SEQ. ID. NO. 7426 | 496-ThrLeuGlnAsnGluProGluProAspPheAspGluGlyGlyMetValSerGluProGlnGln-516 |

591
AMPHI Regions - AMPHI

| | |
|---|---|
| SEQ. ID. NO. 7427 | 6-AlaPheIlePheAla-10 |
| SEQ. ID. NO. 7428 | 17-LeuHisGluPheGlyHisTyrIleValAla-26 |
| SEQ. ID. NO. 7429 | 61-LeuGlyGlyTyrValLysMetValAsp-69 |
| SEQ. ID. NO. 7430 | 143-GlyAspLysIleGlnSerValAsnGlyThrProValAlaAspTrp-157 |
| SEQ. ID. NO. 7431 | 181-SerGlyAlaGlnThrValArgThrIleAspAlaAlaGlyThrProGluAlaGlyIleAlaLys-202 |
| SEQ. ID. NO. 7432 | 218-AlaGlyGlyValGluLys-223 |
| SEQ. ID. NO. 7433 | 234-ProGlyAspArgLeu-238 |

TABLE 1-continued

| | |
|---|---|
| SEQ. ID. NO. 7434 | 245-ProIleAlaSerTrpGlnGluTrpAlaAsnLeuThrArg-257 |
| SEQ. ID. NO. 7435 | 270-ArgAlaGlyGlnThr-274 |
| SEQ. ID. NO. 7436 | 304-AlaTrpAspAlaGlnIleArg-310 |
| SEQ. ID. NO. 7437 | 313-TyrArgProSerValValArgAlaPheGly-322 |
| SEQ. ID. NO. 7438 | 324-GlyTrpGluLysThrValSerHis-331 |
| SEQ. ID. NO. 7439 | 335-ThrLeuLysPhePheGlyLysLeuIle-343 |
| SEQ. ID. NO. 7440 | 351-HisIleSerGlyProLeuThrIleAla-359 |
| SEQ. ID. NO. 7441 | 373-TyrLeuGluPheLeuAlaLeu-379 |

Antigenic Index - Jameson-Wolf

| | |
|---|---|
| SEQ. ID. NO. 7442 | 44-PhePheThrArgLysArgGlyAspThrGlu-53 |
| SEQ. ID. NO. 7443 | 68-ValAspThrArgGluGlyGluValSerGluAlaAspLeu-80 |
| SEQ. ID. NO. 7444 | 84-PheAspLysGlnHisProAlaLysArg-92 |
| SEQ. ID. NO. 7445 | 129-ValGluProAspThrIleAla-135 |
| SEQ. ID. NO. 7446 | 139-GlyPheGlnSerGlyAspLysIleGlnSer-148 |
| SEQ. ID. NO. 7447 | 157-TrpGlySerAlaGln-161 |
| SEQ. ID. NO. 7448 | 187-ArgThrIleAspAlaAlaGlyThrProGluAlaGlyLysIleLysAsnGlnGly-205 |
| SEQ. ID. NO. 7449 | 219-GlyGlyValGluLysGlySerProAlaGluLysAlaGlyLeuLysProGlyAspArgLeuThrAlaAlaAspGlyLysProIle-246 |
| SEQ. ID. NO. 7450 | 254-AsnLeuThrArgGlnSerProGlyLysLysIle-264 |
| SEQ. ID. NO. 7451 | 267-AsnTyrGluArgAlaGlyGlnThrHis-275 |
| SEQ. ID. NO. 7452 | 277-AlaAspIleArgProAspThrValGluGlnSerAspHis-289 |
| SEQ. ID. NO. 7453 | 295-ValGlyLeuArgProGlnProAspArgAlaTrp-305 |
| SEQ. ID. NO. 7454 | 307-AlaGlnIleArgArgSerTyrArgProSerVal-317 |
| SEQ. ID. NO. 7455 | 327-LysThrValSerHisSer-332 |
| SEQ. ID. NO. 7456 | 343-IleSerGlyAsnAla-347 |
| SEQ. ID. NO. 7457 | 362-AlaGlyGlnSerAla-366 |
| SEQ. ID. NO. 7458 | 408-IleArgGlyLysProLeuGlyGluArgValGln-418 |

Hydrophilic Regions - Hopp-Woods

| | |
|---|---|
| SEQ. ID. NO. 7459 | 44-PhePheThrArgLysArgGlyAspThr-52 |
| SEQ. ID. NO. 7460 | 68-ValAspThrArgGluGlyGluValSerGluAlaAspLeu-80 |
| SEQ. ID. NO. 7461 | 84-PheAspLysGlnHisProAlaLysArg-92 |
| SEQ. ID. NO. 7462 | 129-ValGluProAspThrIleAla-135 |
| SEQ. ID. NO. 7463 | 139-GlyPheGlnSerGlyAspLysIleGlnSer-148 |
| SEQ. ID. NO. 7464 | 193-GlyThrProGluAlaGlyLysIleAlaLys-202 |
| SEQ. ID. NO. 7465 | 220-GlyValGluLysGlySerProAlaGluLysAlaGlyLeuLysProGlyAspArgLeuThrAlaAlaAspGlyLysPro-245 |
| SEQ. ID. NO. 7466 | 256-ThrArgGlnSerProGlyLysLysIle-264 |
| SEQ. ID. NO. 7467 | 268-TyrGluArgAlaGlyGln-273 |
| SEQ. ID. NO. 7468 | 277-AlaAspIleArgProAspThrValGluGlnSerAsp-288 |
| SEQ. ID. NO. 7469 | 299-ProGlnProAspArgAlaTrp-305 |
| SEQ. ID. NO. 7470 | 308-GlnIleArgArgSerTyrArg-314 |
| SEQ. ID. NO. 7471 | 362-AlaGlyGlnSerAla-366 |
| SEQ. ID. NO. 7472 | 411-LysProLeuGlyGluArgValGln-418 |

592
AMPHI Regions - AMPHI

| | |
|---|---|
| SEQ. ID. NO. 7473 | 6-PheGlyGlnIlePheSer-11 |
| SEQ. ID. NO. 7474 | 21-GlyGlyLeuLeuGlyGlyLeuIle-28 |
| SEQ. ID. NO. 7475 | 50-AlaProAsnAlaAlaAlaAlaAla-57 |
| SEQ. ID. NO. 7476 | 65-GlnGlyMetIleGlnMetLeuGlyValPheValAsp-76 |
| SEQ. ID. NO. 7477 | 94-ProTyrGlyAspLeu-98 |
| SEQ. ID. NO. 7478 | 109-ValSerGlnValGlyGlnTrp-115 |
| SEQ. ID. NO. 7479 | 153-ThrAlaValPheArgMet-158 |
| SEQ. ID. NO. 7480 | 165-TyrPheGlyAlaValAla-170 |
| SEQ. ID. NO. 7481 | 185-IleMetAlaTrpIleAsnLeuValAlaIleLeuLeuLeuSer-198 |

Antigenic Index - Jameson-Wolf

| | |
|---|---|
| SEQ. ID. NO. 7482 | 35-GlyIleLysArgGlyLeuTyrSerAsnGluAlaGlyMetGlySerAlaProAsnAla-53 |
| SEQ. ID. NO. 7483 | 57-AlaGluValLysHisProVal-63 |
| SEQ. ID. NO. 7484 | 93-GlnProTyrGlyAspLeuSerGly-100 |
| SEQ. ID. NO. 7485 | 137-AlaTyrAlaGluSerAsnVal-143 |
| SEQ. ID. NO. 7486 | 206-ArgAspTyrThrAlaLysLeuLysMetGlyLysAspProGluPheLysLeuSerGluHisProGlyLeuLysArgArgIleLysSerAspValTrp-237 |

Hydrophilic Regions - Hopp-Woods

| | |
|---|---|
| SEQ. ID. NO. 7487 | 35-GlyIleLysArgGlyLeuTyr-41 |
| SEQ. ID. NO. 7488 | 57-AlaGluValLysHis-61 |
| SEQ. ID. NO. 7489 | 212-LeuLysMetGlyLysAspProGluPheLysLeuSerGlu-224 |
| SEQ. ID. NO. 7490 | 226-ProGlyLeuLysArgArgIleLysSer-234 |

593
AMPHI Regions - AMPHI

| | |
|---|---|
| SEQ. ID. NO. 7491 | 6-GlyLeuCysLysArgPheGlyAsnLysThr-15 |
| SEQ. ID. NO. 7492 | 41-SerThrLeuLeuAsnIleIleAlaGlyIle-50 |
| SEQ. ID. NO. 7493 | 87-HisMetSerAlaLeuGlu-92 |
| SEQ. ID. NO. 7494 | 125-AlaHisArgLysProGluLysLeuSerGlyGlyGlu-136 |
| SEQ. ID. NO. 7495 | 159-PheSerSerLeuAsp-163 |
| SEQ. ID. NO. 7496 | 165-HisLeuArgGlyThrLeuArg-171 |
| SEQ. ID. NO. 7497 | 216-ProGluThrLeuValLysThrProSerCysValGlnValAlaArgLeuMetGlyLeu-234 |

Antigenic Index - Jameson-Wolf

| | |
|---|---|
| SEQ. ID. NO. 7498 | 6-GlyLeuCysLysArgPheGlyAsnLysThrValAla-17 |
| SEQ. ID. NO. 7499 | 24-ValGlyArgGlyLysIle-29 |
| SEQ. ID. NO. 7500 | 33-LeuGlyArgSerGlyCysGlyLysSerThr-42 |
| SEQ. ID. NO. 7501 | 50-IleValArgProAspGlyGlyGlu-57 |
| SEQ. ID. NO. 7502 | 61-AsnGlyGluAsnIleThrArgMetProProGluLysArgArgIle-75 |
| SEQ. ID. NO. 7503 | 99-LysMetGlnLysMetProLysAlaGluAlaGluArgLeuAla-112 |
| SEQ. ID. NO. 7504 | 119-ValGlyLeuGluAsnGluAlaHisArgLysProGluLysLeuSerGlyGlyGluLysGlnArgLeuAlaLeu-142 |

TABLE 1-continued

| | |
|---|---|
| SEQ. ID. NO. 7505 | 157-GluSerPheSerSerLeu-162 |
| SEQ. ID. NO. 7506 | 168-GlyThrLeuArgArgMetThrAlaGluArgIleArgAsnGlyGlyIle-183 |
| SEQ. ID. NO. 7507 | 190-HisSerProGluGluAlaCysThrThrAlaAspGluIleAlaVal-204 |
| SEQ. ID. NO. 7508 | 206-HisLysGlyArgIle-210 |
| SEQ. ID. NO. 7509 | 214-GlyThrProGluThrLeuValLysThrProSer-224 |
| SEQ. ID. NO. 7510 | 233-GlyLeuProAsnThrAspAspAsnArgHisIle-243 |
| SEQ. ID. NO. 7511 | 248-ValArgPheAspGlnAspGlyMetGluCysArgValLeuSer-261 |
| SEQ. ID. NO. 7512 | 263-ThrCysLeuProGluSer-268 |
| SEQ. ID. NO. 7513 | 291-GlyAlaValSerGlyLysAspThrVal-299 |
| SEQ. ID. NO. 7514 | 302-HisIleGluGluArgGluIleValArgPheArg-312 |
| Hydrophilic Regions - Hopp-Woods | |
| SEQ. ID. NO. 7515 | 6-GlyLeuCysLysArgPheGlyAsn-13 |
| SEQ. ID. NO. 7516 | 25-GlyArgGlyLysIle-29 |
| SEQ. ID. NO. 7517 | 36-SerGlyCysGlyLys-40 |
| SEQ. ID. NO. 7518 | 51-ValArgProAspGlyGly-56 |
| SEQ. ID. NO. 7519 | 68-MetProProGluLysArgArgIle-75 |
| SEQ. ID. NO. 7520 | 99-LysMetGlnLysMetProLysAlaGluAlaGluArgLeuAla-112 |
| SEQ. ID. NO. 7521 | 119-ValGlyLeuGluAsnGluAlaHisArgLysProGluLysLeuSerGlyGlyGluLysGlnArgLeuAlaLeu-142 |
| SEQ. ID. NO. 7522 | 168-GlyThrLeuArgArgMetThrAlaGluArgIleArgAsn-180 |
| SEQ. ID. NO. 7523 | 191-SerProGluGluAlaCysThrThrAlaAspGluIleAlaVal-204 |
| SEQ. ID. NO. 7524 | 206-HisLysGlyArgIle-210 |
| SEQ. ID. NO. 7525 | 236-AsnThrAspAspAsnArgHisIle-243 |
| SEQ. ID. NO. 7526 | 248-ValArgPheAspGlnAspGlyMetGluCysArgValLeuSer-261 |
| SEQ. ID. NO. 7527 | 293-ValSerGlyLysAspThrVal-299 |
| SEQ. ID. NO. 7528 | 302-HisIleGluGluArgGluIleValArgPheArg-312 |
| 594 | |
| AMPHI Regions - AMPHI | |
| SEQ. ID. NO. 7529 | 21-SerIleLeuArgLeu-25 |
| SEQ. ID. NO. 7530 | 108-AlaGlyArgGluCysGlnGluThrAlaAlaAla-118 |
| SEQ. ID. NO. 7531 | 138-AlaIleLysArgCysAsn-143 |
| Antigenic Index - Jameson-Wolf | |
| SEQ. ID. NO. 7532 | 1-MetGlyAlaAspThrAspGlyAspLysAspValArgLeuAsnArgThr-16 |
| SEQ. ID. NO. 7533 | 51-ValGluHisProAsnArgPhe-57 |
| SEQ. ID. NO. 7534 | 75-HisLeuAspGlySerThrGlyGly-82 |
| SEQ. ID. NO. 7535 | 86-PheArgArgGluLysThrGlyHisLysArgArgCysHisThrGlnCys-101 |
| SEQ. ID. NO. 7536 | 103-HisSerAlaArgAlaAlaGlyArgGluCysGlnGluThr-115 |
| SEQ. ID. NO. 7537 | 137-ArgAlaIleLysArgCysAsn-143 |
| Hydrophilic Regions - Hopp-Woods | |
| SEQ. ID. NO. 7538 | 1-MetGlyAlaAspThrAspGlyAspLysAspValArgLeuAsnArg-15 |
| SEQ. ID. NO. 7539 | 86-PheArgArgGluLysThrGlyHisLysArgArgCysHis-98 |
| SEQ. ID. NO. 7540 | 105-AlaArgAlaAlaGlyArgGluCysGlnGluThr-115 |
| SEQ. ID. NO. 7541 | 137-ArgAlaIleLysArgCysAsn-143 |
| 595 | |
| AMPHI Regions - AMPHI | |
| SEQ. ID. NO. 7542 | 20-CysGlnProProGluAla-25 |
| SEQ. ID. NO. 7543 | 140-AlaAspLeuGluLysLeuSerGlnProLeuAla-150 |
| SEQ. ID. NO. 7544 | 157-GlnGlyGluValLysGluLeuVal-164 |
| SEQ. ID. NO. 7545 | 169-ThrPheThrGluAlaValLysAlaGlyAspIleGluLysAla-182 |
| SEQ. ID. NO. 7546 | 196-IleGluProIleAlaGluLeuPheSerGluLeuAspPro-208 |
| SEQ. ID. NO. 7547 | 224-AlaGlyPheThrGlyPheHisArg-231 |
| SEQ. ID. NO. 7548 | 243-SerGlyValLysGluIleAlaAlaLysLeuMetThrAspValGluAlaLeuGlnLysGluIleAsp-264 |
| SEQ. ID. NO. 7549 | 274-ValGlyGlyAlaSerGluLeuIleGluGluValAlaGly-286 |
| SEQ. ID. NO. 7550 | 309-AspGlySerLysLysIleValAspLeuPheArgProLeu-321 |
| SEQ. ID. NO. 7551 | 337-PheLysGlnValAsnGluIleLeuAlaLys-346 |
| SEQ. ID. NO. 7552 | 351-AspGlyPheGluThrTyrAspLysLeuGlyGlu-361 |
| SEQ. ID. NO. 7553 | 366-AlaLeuGlnAlaSerIleAsnAlaLeuAlaGluAspLeuAlaGlnLeuArgGlyIleLeuGlyLeu-387 |
| Antigenic Index - Jameson-Wolf | |
| SEQ. ID. NO. 7554 | 1-MetArgLysPheAsn-5 |
| SEQ. ID. NO. 7555 | 21-GlnProProGluAlaGluLysAlaAlaPro-30 |
| SEQ. ID. NO. 7556 | 32-AlaSerGlyGluAlaGlnThrAlaAsnGluGlyGlySer-44 |
| SEQ. ID. NO. 7557 | 50-AsnAspAsnAlaCysGluProMetGlu-58 |
| SEQ. ID. NO. 7558 | 70-IleLysAsnAsnSerGlyArgLysLeuGluTrpGluIle-82 |
| SEQ. ID. NO. 7559 | 87-MetValValAspGluArgGluAsnIleAla-96 |
| SEQ. ID. NO. 7560 | 98-GlyLeuSerAspLysMetThr-104 |
| SEQ. ID. NO. 7561 | 108-LeuProGlyGluTyrGluMet-114 |
| SEQ. ID. NO. 7562 | 120-ThrAsnProArgGlyLysLeuValValThrAspSerGlyPheLysAspThrAlaAsnGluAlaAspLeuGluLysLeuSer-146 |
| SEQ. ID. NO. 7563 | 158-GlyGluValLysGluLeuValAlaLysThrLysThrPheThrGluAlaValLysAlaGlyAspIleGluLysAlaLysSerLeuPheAla-187 |
| SEQ. ID. NO. 7564 | 189-ThrArgValHisTyrGluArgIleGluProIle-199 |
| SEQ. ID. NO. 7565 | 204-SerGluLeuAspProValIleAspAlaArgGluAspAspPheLysAspGlyAlaLysAspAlaGly-225 |
| SEQ. ID. NO. 7566 | 238-ValGluLysAspValSerGlyValLysGluIleAlaAla-250 |
| SEQ. ID. NO. 7567 | 252-LeuMetThrAspValGluAlaLeuGlnLysGluIleAsp-264 |
| SEQ. ID. NO. 7568 | 269-ProProGlyLysValValGlyGlyAla-277 |
| SEQ. ID. NO. 7569 | 279-GluLeuIleGluGluValAlaGlySerLysIleSerGlyGluGluAspArgTyrSerHisThrAspLeuSerAspPheGlnAlaAsnValAspGlySerLysLysIleValAsp-316 |
| SEQ. ID. NO. 7570 | 322-IleGluAlaLysAsnLysAlaLeuLeuGluLysThrAspThrAsnPheLysGlnValAsn-341 |
| SEQ. ID. NO. 7571 | 345-AlaLysTyrArgThrLysAspGlyPheGluThrTyrAspLysLeuGlyGluAlaAspArgLysAlaLeu-367 |
| SEQ. ID. NO. 7572 | 374-LeuAlaGluAspLeuAlaGln-380 |
| Hydrophilic Regions - Hopp-Woods | |
| SEQ. ID. NO. 7573 | 1-MetArgLysPheAsn-5 |
| SEQ. ID. NO. 7574 | 21-GlnProProGluAlaGluLysAlaAlaPro-30 |

TABLE 1-continued

| | |
|---|---|
| SEQ. ID. NO. 7575 | 32-AlaSerGlyGluAlaGlnThrAlaAsnGluGlyGlySer-44 |
| SEQ. ID. NO. 7576 | 52-AsnAlaCysGluProMetGlu-58 |
| SEQ. ID. NO. 7577 | 72-AsnAsnSerGlyArgLysLeuGluTrpGluIle-82 |
| SEQ. ID. NO. 7578 | 87-MetValValAspGluArgGluAsnIle-95 |
| SEQ. ID. NO. 7579 | 99-LeuSerAspLysMetThr-104 |
| SEQ. ID. NO. 7580 | 110-GlyGluTyrGluMet-114 |
| SEQ. ID. NO. 7581 | 122-ProArgGlyLysLeuValVal-128 |
| SEQ. ID. NO. 7582 | 131-SerGlyPheLysAspThrAlaAsnGluAlaAspLeuGluLysLeuSer-146 |
| SEQ. ID. NO. 7583 | 158-GlyGluValLysGluLeuValAlaAlaLysThrLysThrPheThrGluAlaValLysAlaGlyAspIleGluLysAlaLysSerLeuPheAla-187 |
| SEQ. ID. NO. 7584 | 189-ThrArgValHisTyrGluArgIleGluProIle-199 |
| SEQ. ID. NO. 7585 | 204-SerGluLeuAspProValIleAspAlaArgGluAspAspPheLysAspGlyAlaLysAspAlaGly-225 |
| SEQ. ID. NO. 7586 | 238-ValGluLysAspValSerGlyValLysGluIleAlaAla-250 |
| SEQ. ID. NO. 7587 | 252-LeuMetThrAspValGluAlaLeuGlnLysGluIleAsp-264 |
| SEQ. ID. NO. 7588 | 279-GluLeuIleGluGluValAlaGly-286 |
| SEQ. ID. NO. 7589 | 288-LysIleSerGlyGluGluAspArgTyrSerHis-298 |
| SEQ. ID. NO. 7590 | 308-ValAspGlySerLysLysIleValAsp-316 |
| SEQ. ID. NO. 7591 | 322-IleGluAlaLysAsnLysAlaLeuLeuGluLysThrAspThrAsnPhe-337 |
| SEQ. ID. NO. 7592 | 347-TyrArgThrLysAspGlyPheGluThrTyrAspLysLeuGlyGluAlaAspArgLysAlaLeu-367 |
| SEQ. ID. NO. 7593 | 374-LeuAlaGluAspLeuAlaGln-380 |
| 596 | |
| AMPHI Regions - AMPHI | |
| SEQ. ID. NO. 7594 | 9-MetLeuArgValSerLysValVal-16 |
| SEQ. ID. NO. 7595 | 50-LeuArgIleMetAlaGlyValAspLys-58 |
| SEQ. ID. NO. 7596 | 87-ValArgGluGluValGluSerGlyLeuGlyGluValAlaAlaAlaGlnLysArgLeuGluGluValTyrAlaGluTyr-112 |
| SEQ. ID. NO. 7597 | 192-ProThrAsnHisLeuAsp-197 |
| SEQ. ID. NO. 7598 | 202-GluTrpLeuGluGlnPheLeuValArgPheProGly-213 |
| SEQ. ID. NO. 7599 | 295-AlaArgPheGluGluMetSerAsnTyr-303 |
| SEQ. ID. NO. 7600 | 322-LeuGlyAsnGluValIleGluPheValAsnValSerLysSerPhe-336 |
| SEQ. ID. NO. 7601 | 366-SerThrLeuPheLysMet-371 |
| SEQ. ID. NO. 7602 | 409-AspAsnIleAlaGlu-413 |
| SEQ. ID. NO. 7603 | 440-AspGlnSerLysIleAlaGlyGlnLeuSerGlyGlyGlu-452 |
| SEQ. ID. NO. 7604 | 483-LeuArgAlaLeuGluAspAlaLeuLeuGluPheAla-494 |
| Antigenic Index - Jameson-Wolf | |
| SEQ. ID. NO. 7605 | 16-ValProProGlnLysThrIleIleLysAspIleSer-27 |
| SEQ. ID. NO. 7606 | 41-LeuAsnGlyAlaGlyLysSerThrVal-49 |
| SEQ. ID. NO. 7607 | 54-AlaGlyValAspLysGluPheGluGlyGluAla-64 |
| SEQ. ID. NO. 7608 | 75-LeuProGlnGluProGluLeuAspProGluLysThrValArgGluGluValGluSerGlyLeu-95 |
| SEQ. ID. NO. 7609 | 99-AlaAlaAlaGlnLysArgLeuGluGluValTyr-109 |
| SEQ. ID. NO. 7610 | 112-TyrAlaAsnProAspAlaAspPheAspAlaLeuAlaGluGluGlnGlyArgLeuGlu-130 |
| SEQ. ID. NO. 7611 | 136-GlySerSerThrGlyGlyGlyAlaGluHisGluLeuGluIleAlaAlaAspAlaLeuArg-155 |
| SEQ. ID. NO. 7612 | 157-ProGluTrpAspAlaLysIleAspAsnLeuSerGlyGlyGluLysArgArgValAla-175 |
| SEQ. ID. NO. 7613 | 181-LeuSerLysProAspMet-186 |
| SEQ. ID. NO. 7614 | 190-AspGluProThrAsnHisLeuAspAlaGluSer-200 |
| SEQ. ID. NO. 7615 | 219-ThrHisAspArgTyrPhe-224 |
| SEQ. ID. NO. 7616 | 233-LeuGluLeuAspArgGlyHisGlyIle-241 |
| SEQ. ID. NO. 7617 | 243-TrpLysGlyAsnTyrSerSer-249 |
| SEQ. ID. NO. 7618 | 251-LeuGluGlnLysGluLysArgLeuGluAsnGluAlaLysSerGluAlaAlaArgValLysAlaMetLysGlnGluLeuGluTrp-278 |
| SEQ. ID. NO. 7619 | 280-ArgGlnAsnAlaLysGlyArgGlnAlaLysSerLysAlaArgLeuAlaArgPheGluGluMetSerAsnTyrGluTyrGlnLysArgAsnGluThrGlnGlu-313 |
| SEQ. ID. NO. 7620 | 319-AlaGluArgLeuGlyAsnGluVal-326 |
| SEQ. ID. NO. 7621 | 333-SerLysSerPheGlyAsp-338 |
| SEQ. ID. NO. 7622 | 360-ProAsnGlyAlaGlyLysSerThrLeu-368 |
| SEQ. ID. NO. 7623 | 372-IleSerGlyLysGluGlnProAspSerGlyGluValLysIle-385 |
| SEQ. ID. NO. 7624 | 395-AspGlnSerArgGluGlyLeuGlnAsnAspLysThrVal-407 |
| SEQ. ID. NO. 7625 | 411-IleAlaGluGlyArgAspIleLeu-418 |
| SEQ. ID. NO. 7626 | 425-IleProAlaArgGlnTyrLeuGlyArgPheAsnPheLysGlySerAspGlnSerLysIleAla-445 |
| SEQ. ID. NO. 7627 | 447-GlnLeuSerGlyGlyGluArgGlyArgLeuHisLeu-458 |
| SEQ. ID. NO. 7628 | 471-LeuAspGluProSerAsnAspLeuAspValGluThr-482 |
| SEQ. ID. NO. 7629 | 501-SerHisAspArgTrpPhe-506 |
| SEQ. ID. NO. 7630 | 516-AlaCysGluGlyAspSerLysTrp-523 |
| SEQ. ID. NO. 7631 | 527-AspGlyAsnTyrGlnGluTyrGluAlaAspLysLysArgArgLeuGlyGluGluGlyAlaLysProLysArgIleLysTyrLysProValThrArg-558 |
| Hydrophilic Regions - Hopp-Woods | |
| SEQ. ID. NO. 7632 | 54-AlaGlyValAspLysGluPheGluGlyGluAla-64 |
| SEQ. ID. NO. 7633 | 77-GlnGluProGluLeuAspProGluLysThrValArgGluGluValGluSerGlyLeu-95 |
| SEQ. ID. NO. 7634 | 99-AlaAlaAlaGlnLysArgLeuGluGluValTyr-109 |
| SEQ. ID. NO. 7635 | 113-AlaAsnProAspAlaAspPheAspAlaLeuAlaGluGluGlnGlyArgLeuGlu-130 |
| SEQ. ID. NO. 7636 | 141-GlyGlyAlaGluHisGluLeuGluIleAlaAlaAspAlaLeuArg-155 |
| SEQ. ID. NO. 7637 | 157-ProGluTrpAspAlaLysIleAspAsn-165 |
| SEQ. ID. NO. 7638 | 167-SerGlyGlyGluLysArgArgValAla-175 |
| SEQ. ID. NO. 7639 | 181-LeuSerLysProAsp-185 |
| SEQ. ID. NO. 7640 | 190-AspGluProThrAsn-194 |
| SEQ. ID. NO. 7641 | 196-LeuAspAlaGluSer-200 |
| SEQ. ID. NO. 7642 | 233-LeuGluLeuAspArgGlyHis-239 |
| SEQ. ID. NO. 7643 | 251-LeuGluGlnLysGluLysArgLeuGluAsnGluAlaLysSerGluAlaAlaArgValLysAlaMetLysGlnGluLeuGluTrp-278 |
| SEQ. ID. NO. 7644 | 280-ArgGlnAsnAlaLysGlyArgGlnAlaLysSerLysAlaArgLeuAlaArgPheGluGluMetSerAsn-302 |
| SEQ. ID. NO. 7645 | 304-GluTyrGlnLysArgAsnGluThrGln-312 |
| SEQ. ID. NO. 7646 | 319-AlaGluArgLeuGlyAsnGluVal-326 |
| SEQ. ID. NO. 7647 | 372-IleSerGlyLysGluGlnProAspSerGlyGluValLysIle-385 |
| SEQ. ID. NO. 7648 | 395-AspGlnSerArgGluGlyLeuGlnAsnAspLysThrVal-407 |
| SEQ. ID. NO. 7649 | 411-IleAlaGluGlyArgAspIleLeu-418 |

TABLE 1-continued

| | |
|---|---|
| SEQ. ID. NO. 7650 | 435-AsnPheLysGlySerAspGlnSerLysIle-444 |
| SEQ. ID. NO. 7651 | 449-SerGlyGlyGluArgGlyArgLeuHisLeu-458 |
| SEQ. ID. NO. 7652 | 472-AspGluProSerAsnAspLeuAspValGluThr-482 |
| SEQ. ID. NO. 7653 | 517-CysGluGlyAspSer-521 |
| SEQ. ID. NO. 7654 | 529-AsnTyrGlnGluTyrGluAlaAspLysLysArgArgLeuGlyGluGluGlyAlaLysProLysArgIleLysTyr-553 |

597-2
AMPHI Regions - AMPHI

| | |
|---|---|
| SEQ. ID. NO. 7655 | 30-AlaGluValLysLys-34 |
| SEQ. ID. NO. 7656 | 66-LysGluAlaAlaLysGluGlyLysGluSerLysLysThrAlaLys-80 |
| SEQ. ID. NO. 7657 | 93-GlnSerAlaArgLysGlyArgGluGly-101 |
| SEQ. ID. NO. 7658 | 112-AlaHisGlyLysPro-116 |
| SEQ. ID. NO. 7659 | 141-GlnGlyAsnProArgLysGlyGlyLys-149 |
| SEQ. ID. NO. 7660 | 163-SerAspLysAsnGlyLysAlaValLysGlnAspLysLysTyrArgGluGluLysAsn-181 |
| SEQ. ID. NO. 7661 | 217-ValSerAsnSerLeuLysGlnLeuGlnGlu-226 |
| SEQ. ID. NO. 7662 | 252-TrpAspLysPheGlnLysLeu-258 |
| SEQ. ID. NO. 7663 | 275-GlnIleSerArgPheValSerGly-282 |
| SEQ. ID. NO. 7664 | 308-LeuArgTyrThrArgTyrValAsnAla-316 |
| SEQ. ID. NO. 7665 | 318-AsnArgGluValValLysAspLeuGluLysGlnGln-329 |
| SEQ. ID. NO. 7666 | 339-IleAsnAsnGluLeuAlaArgLeuLysLys-348 |
| SEQ. ID. NO. 7667 | 351-AlaAsnValGlnSerLeu-356 |
| SEQ. ID. NO. 7668 | 364-AspAlaAlaGluGlnThrGlu-370 |
| SEQ. ID. NO. 7669 | 376-AlaLysIleAlaLysAspAlaArg-383 |
| SEQ. ID. NO. 7670 | 396-AsnLysLeuLeuSer-400 |
| SEQ. ID. NO. 7671 | 460-ProSerValMetGlyIleGlySerAlaAspGlyPheSerArgMetGlnGlyArgLeuLysLysProValAspGlyValProThrGly-488 |
| SEQ. ID. NO. 7672 | 509-ProAlaThrValGluSerIleAla-516 |
| SEQ. ID. NO. 7673 | 521-SerTyrAlaAspGluLeuAspGlyTyrGlyLys-531 |
| SEQ. ID. NO. 7674 | 543-SerIleTyrAlaGlyLeu-548 |

Antigenic Index - Jameson-Wolf

| | |
|---|---|
| SEQ. ID. NO. 7675 | 23-AspAlaAlaHisAsnArgSerAlaGluValLysLysGlnThrLysAsnLysLysGluGlnProGluAlaAlaGluGlyLysLysGluLysGlyLysAsn GlyAlaValLysAspLysLysThrGlyGlyLysGluAlaAlaLysGluGlyLysGluSerLysLysThrAlaLysAsnArgLysGluAlaGluLysGluAlaThr SerArgGlnSerAlaArgLysGlyArgGluGlyAspLysLysSerLysAlaGluHisLysLysAlaHisGlyLysProValSerGlySerLysGluLysAsnAla LysThrGlnProGluAsnLysGlnGlyLysLysGluAlaLysGlyGlnGlyAsnProArgLysGlyGlyLysAlaGluLysAspThrValSerAlaAsnLysLys ValArgSerAspLysAsnGlyLysAlaValLysGlnAspLysLysTyrArgGluGluLysAsnAlaLysThrAspSerAspGluLeuLysAla-191 |
| SEQ. ID. NO. 7676 | 196-AlaThrAsnAspValGluAsnLysLysAlaLeuLeuLysGlnSerGluGly-212 |
| SEQ. ID. NO. 7677 | 219-AsnSerLeuLysGlnLeuGlnGluGluArgIleArgGlnGluArgIleArgGlnAlaArgGlyAsnLeu-241 |
| SEQ. ID. NO. 7678 | 243-SerValAsnArgLysGlnArgGluAlaTrpAspLysPheGlnLysLeuAsnThrGluLeuAsnArgLeuLysThrGluValAlaAla-271 |
| SEQ. ID. NO. 7679 | 281-SerGlyAsnTyrLysAsnSerGlnProAsn-290 |
| SEQ. ID. NO. 7680 | 298-AsnAlaGluProGlyGlnLysAsnArgPhe-307 |
| SEQ. ID. NO. 7681 | 314-ValAsnAlaSerAsnArgGluValValLysAspLeuGluLysGlnGlnLys-330 |
| SEQ. ID. NO. 7682 | 335-GlnGluGlnLysIleAsnAsnGluLeuAlaArgLeuLysLysIleGln-350 |
| SEQ. ID. NO. 7683 | 356-LeuLeuLysLysGlnGlyValThrAspAlaAlaGluGlnThrGluSerArgArgGlnAsnAlaLysIleAlaLysAspAlaArgLysLeuLeuGluGln LysGlyAsnGluGlnLeu-395 |
| SEQ. ID. NO. 7684 | 398-LeuLeuSerAsnLeuGluLysLysLysAlaGluHisArgIleGlnAspAlaGluAlaLysArgLysLeuAlaGluAlaArgLeuAlaAlaAlaGluLys AlaArgLysGluAlaAlaGlnGlnLysAlaGluAlaArgArgAlaGluMetSerAsnLeuThrAlaGluAspArgAsnIleGlnAlaProSer-461 |
| SEQ. ID. NO. 7685 | 466-GlySerAlaAspGlyPheSerArgMetGlnGlyArgLeuLysLysProValAspGlyValProThr-487 |
| SEQ. ID. NO. 7686 | 491-GlyGlnAsnArgSerGlyGlyAspIle-499 |
| SEQ. ID. NO. 7687 | 521-SerTyrAlaAspGluLeuAspGlyTyrGly-530 |
| SEQ. ID. NO. 7688 | 536-AspHisGlyGluAsnTyr-541 |
| SEQ. ID. NO. 7689 | 561-AlaGlySerLysIleGlySerSerGlySerLeuProAspGlyGluGluGlyLeu-578 |
| SEQ. ID. NO. 7690 | 588-ValLeuAsnProSerSerTrp-594 |

Hydrophilic Regions - Hopp-Woods

| | |
|---|---|
| SEQ. ID. NO. 7691 | 23-AspAlaAlaHisAsnArgSerAlaGluValLysLysGlnThrLysAsnLysLysGluGlnProGluAlaAlaGluGlyLysLysGluLysGlyLys AsnGlyAlaValLysAspLysLysThrGlyGlyLysGluAlaAlaLysGluGlyLysGluSerLysLysThrAlaLysAsnArgLysGluAlaGluLysGluAla ThrSerArgGlnSerAlaArgLysGlyArgGluGlyAspLysLysSerLysAlaGluHisLysLysAlaHisGlyLysProValSerGlySerLysGluLysAsn AlaLysThrGlnProGluAsnLysGlnGlyLysLysGluAlaLysGlyGlnGlyAsnProArgLysGlyGlyLysAlaGluLysAspThrValSerAlaAsnLys LysValArgSerAspLysAsnGlyLysAlaValLysGlnAspLysLysTyrArgGluGluLysAsnAlaLysThrAspSerAspGluLeuLysAla-191 |
| SEQ. ID. NO. 7692 | 198-AsnAspValGluAsnLysLysAlaLeuLeuLysGlnSerGlu-211 |
| SEQ. ID. NO. 7693 | 220-SerLeuLysGlnLeuGlnGluGluArgIleArgGlnGluArgIleArgGlnAlaArgGlyAsn-240 |
| SEQ. ID. NO. 7694 | 244-ValAsnArgLysGlnArgGluAlaTrpAspLysPheGlnLysLeuAsnThrGluLeuAsnArgLeuLysThrGluValAlaAla-271 |
| SEQ. ID. NO. 7695 | 284-TyrLysAsnSerGln-288 |
| SEQ. ID. NO. 7696 | 298-AsnAlaGluProGlyGlnLysAsnArgPhe-307 |
| SEQ. ID. NO. 7697 | 317-SerAsnArgGluValValLysAspLeuGluLysGlnGlnLys-330 |
| SEQ. ID. NO. 7698 | 335-GlnGluGlnLysIleAsnAsnGluLeuAlaArgLeuLysLysIleGln-350 |
| SEQ. ID. NO. 7699 | 356-LeuLeuLysLysGlnGlyValThrAspAlaAlaGluGlnThrGluSerArgArgGlnAsnAlaLysIleAlaLysAspAlaArgLysLeuLeuGluGln LysGlyAsnGluGlnGlnLeu-395 |
| SEQ. ID. NO. 7700 | 400-SerAsnLeuGluLysLysLysAlaGluHisArgIleGlnAspAlaGluAlaLysArgLysLeuAlaGluAlaArgLeuAlaAlaAlaGluLysAlaArg LysGluAlaAlaGlnGlnLysAlaGluAlaArgArgAlaGluMet-447 |
| SEQ. ID. NO. 7701 | 451-ThrAlaGluAspArgAsnIleGln-458 |
| SEQ. ID. NO. 7702 | 474-MetGlnGlyArgLeuLysLysProValAsp-483 |
| SEQ. ID. NO. 7703 | 493-AsnArgSerGlyGlyAspIle-499 |
| SEQ. ID. NO. 7704 | 522-TyrAlaAspGluLeuAspGlyTyrGly-530 |
| SEQ. ID. NO. 7705 | 563-SerLysIleGlySer-567 |
| SEQ. ID. NO. 7706 | 570-SerLeuProAspGlyGluGluGlyLeu-578 |

601-2
AMPHI Regions - AMPHI

| | |
|---|---|
| SEQ. ID. NO. 7707 | 29-AlaAlaArgGluAla-33 |
| SEQ. ID. NO. 7708 | 43-ArgValLeuGlySerPro-48 |
| SEQ. ID. NO. 7709 | 50-ProTyrGlyLysGlnIleAspGlyLeuGlyAsnAlaSerSerSer-64 |
| SEQ. ID. NO. 7710 | 94-PheValAspTrpSerGly-99 |
| SEQ. ID. NO. 7711 | 101-CysGlyAsnLeuThrAlaAla-107 |

TABLE 1-continued

| | |
|---|---|
| SEQ. ID. NO. 7712 | 134-TrpGlnLysAsnIleGlyLysThrIle-142 |
| SEQ. ID. NO. 7713 | 191-LeuValAspGluIleAspValProAsnIleGlyArg-202 |
| SEQ. ID. NO. 7714 | 210-AlaGlyIleProThrValPhe-216 |
| SEQ. ID. NO. 7715 | 226-GlyLysGluLeuGlnAspAspIleAsnAsnAspAlaAlaAlaLeuGluLysPheGluLysIleArgAlaTyrGlyAlaLeu-252 |
| SEQ. ID. NO. 7716 | 254-MetGlyLeuIleSerAspValSerGluAlaAla-264 |
| SEQ. ID. NO. 7717 | 284-SerSerGlyLysThrValAsn-290 |
| SEQ. ID. NO. 7718 | 321-AlaAlaAlaValProGlyThrLeuValAsnLeuAlaAla-333 |
| SEQ. ID. NO. 7719 | 353-GlyAlaAlaAlaGlu-357 |
| Antigenic Index - Jameson-Wolf | |
| SEQ. ID. NO. 7720 | 11-TyrArgGlyGlyThrSerLysGlyValPhePheLysArgSerAspLeuProGluAlaAlaArgGluAlaGlySerAlaArgAspLysIleLeu-41 |
| SEQ. ID. NO. 7721 | 46-GlySerProAspProTyrGlyLysGlnIleAspGlyLeuGlyAsnAlaSerSerThrSerLys-67 |
| SEQ. ID. NO. 7722 | 69-ValIleLeuAspLysSerGluArgAlaAspHisAspValAspTyr-83 |
| SEQ. ID. NO. 7723 | 89-SerIleAspLysProPhe-94 |
| SEQ. ID. NO. 7724 | 96-AspTrpSerGlyAsnCysGly-102 |
| SEQ. ID. NO. 7725 | 116-GlyLeuValAspLysGlyLysIleProSerAspGly-127 |
| SEQ. ID. NO. 7726 | 134-TrpGlnLysAsnIleGlyLysThrIle-142 |
| SEQ. ID. NO. 7727 | 155-GluThrGlyAspPheGluLeu-161 |
| SEQ. ID. NO. 7728 | 177-AspProAlaAspGlyGluGlySerMet-185 |
| SEQ. ID. NO. 7729 | 187-ProThrGlyAsnLeuValAspGluIleAspValProAsnIleGlyArgLeuLys-204 |
| SEQ. ID. NO. 7730 | 223-GlyTyrThrGlyLysGluLeuGlnAspAspIleAsnAsnAspAlaAlaAlaLeuGluLysPheGluLysIleArgAla-248 |
| SEQ. ID. NO. 7731 | 259-AspValSerGluAlaAlaAlaArgAlaHisThrPro-270 |
| SEQ. ID. NO. 7732 | 281-TyrThrAlaSerSerGlyLysThrValAsn-290 |
| SEQ. ID. NO. 7733 | 333-AlaGlyGlyGlyThrArgLysGluValArgPheGlyHisProSerGlyThrLeuArg-351 |
| SEQ. ID. NO. 7734 | 356-AlaGluCysGlnAspGlyGln-362 |
| SEQ. ID. NO. 7735 | 369-ValMetSerArgSerAlaArgValMet-377 |
| SEQ. ID. NO. 7736 | 382-ValArgValProGluAspCysPhe-389 |
| Hydrophilic Regions - Hopp-Woods | |
| SEQ. ID. NO. 7737 | 22-LysArgSerAspLeuProGluAlaAlaArgGluAlaGlySerAlaArgAspLysIleLeu-41 |
| SEQ. ID. NO. 7738 | 49-AspProTyrGlyLysGlnIleAsp-56 |
| SEQ. ID. NO. 7739 | 62-SerSerSerThrSer-66 |
| SEQ. ID. NO. 7740 | 69-ValIleLeuAspLysSerGluArgAlaAspHisAspVal-81 |
| SEQ. ID. NO. 7741 | 89-SerIleAspLysProPhe-94 |
| SEQ. ID. NO. 7742 | 116-GlyLeuValAspLysGlyLysIleProSer-125 |
| SEQ. ID. NO. 7743 | 157-GlyAspPheGluLeu-161 |
| SEQ. ID. NO. 7744 | 177-AspProAlaAspGlyGluGly-183 |
| SEQ. ID. NO. 7745 | 191-LeuValAspGluIleAspVal-197 |
| SEQ. ID. NO. 7746 | 224-TyrThrGlyLysGluLeuGlnAspAspIleAsnAsnAspAlaAlaAlaLeuGluLysPheGluLysIleArgAla-248 |
| SEQ. ID. NO. 7747 | 259-AspValSerGluAlaAlaAlaArgAlaHisThr-269 |
| SEQ. ID. NO. 7748 | 283-AlaSerSerGlyLysThrValAsn-290 |
| SEQ. ID. NO. 7749 | 335-GlyGlyThrArgLysGluValArgPhe-343 |
| SEQ. ID. NO. 7750 | 356-AlaGluCysGlnAsp-360 |
| SEQ. ID. NO. 7751 | 372-ArgSerAlaArgValMet-377 |
| SEQ. ID. NO. 7752 | 384-ValProGluAspCysPhe-389 |
| 602-2 | |
| AMPHI Regions - AMPHI | |
| SEQ. ID. NO. 7753 | 21-ValAsnArgHisGlyGln-26 |
| SEQ. ID. NO. 7754 | 30-GlyGlyLeuAspAlaPheCys-36 |
| SEQ. ID. NO. 7755 | 54-ArgGlnIleAlaGlnIle-59 |
| SEQ. ID. NO. 7756 | 61-AlaGlyLeuHisValCysAsnSerVal-69 |
| SEQ. ID. NO. 7757 | 78-HisValIleValGluMetCysAlaTrpTyrGly-88 |
| Antigenic Index - Jameson-Wolf | |
| SEQ. ID. NO. 7758 | 5-GlnCysAspLysThrArgHisMetArgPro-14 |
| SEQ. ID. NO. 7759 | 19-ArgGlnValAsnArgHisGlyGlnThrGlyAsnGlyGlyLeuAspAla-34 |
| SEQ. ID. NO. 7760 | 36-CysSerLeuGlnGlyAsnArgLysAlaGlnValPheAspThrAspLeuIleAspArgGlnIle-56 |
| SEQ. ID. NO. 7761 | 90-SerAlaGlyGluTyr-94 |
| SEQ. ID. NO. 7762 | 99-GlnMetArgAspTyrIle-104 |
| Hydrophilic Regions - Hopp-Woods | |
| SEQ. ID. NO. 7763 | 5-GlnCysAspLysThrArgHisMetArg-13 |
| SEQ. ID. NO. 7764 | 20-GlnValAsnArgHisGlyGln-26 |
| SEQ. ID. NO. 7765 | 39-GlnGlyAsnArgLysAlaGlnValPhe-47 |
| SEQ. ID. NO. 7766 | 50-AspLeuIleAspArgGlnIle-56 |
| 603-2 | |
| AMPHI Regions - AMPHI | |
| SEQ. ID. NO. 7767 | 69-MetLeuLeuAsnGluLeuGluLys-76 |
| SEQ. ID. NO. 7768 | 107-ValMetAspGluLeuAsnAlaCysIlePro-116 |
| SEQ. ID. NO. 7769 | 121-HisAsnProAlaAsnIleSerGlyIleLeuAla-131 |
| SEQ. ID. NO. 7770 | 135-HisPheProGlyLeuProAsnValGly-143 |
| SEQ. ID. NO. 7771 | 148-SerPheHisGlnThrMetPro-154 |
| SEQ. ID. NO. 7772 | 161-AlaValProArgGluLeu-166 |
| SEQ. ID. NO. 7773 | 188-GluAlaAlaArgIleLeuGlyLysProLeuGluAspIleArgMetIleIleAlaHis-206 |
| SEQ. ID. NO. 7774 | 209-AsnGlyAlaSerIleThrAlaIleLysAsnGlyLysSerVal-222 |
| SEQ. ID. NO. 7775 | 229-ThrProIleGluGly-233 |
| SEQ. ID. NO. 7776 | 248-TyrSerTyrLeuThrSer-253 |
| SEQ. ID. NO. 7777 | 273-LeuGlyIleSerGlu-277 |
| SEQ. ID. NO. 7778 | 279-SerAsnAspCysArg-283 |
| SEQ. ID. NO. 7779 | 306-ArgLeuAlaLysTyrIleAlaSerMet-314 |
| SEQ. ID. NO. 7780 | 342-ValSerTyrLeuAsp-346 |
| Antigenic Index - Jameson-Wolf | |
| SEQ. ID. NO. 7781 | 12-GlySerSerSerLeuLysGlyAlaValIleAspArgLysSerGlySer-27 |
| SEQ. ID. NO. 7782 | 33-LeuGlyGluArgLeuThrThrProGluAla-42 |

TABLE 1-continued

| | |
|---|---|
| SEQ. ID. NO. 7783 | 45-ThrPheAsnLysAspGlyAsnLysArgGlnValProLeuSerGlyArgAsnCysHis-63 |
| SEQ. ID. NO. 7784 | 73-GluLeuGluLysHisGlyLeuHisAspArgIleLysAlaIleGly-87 |
| SEQ. ID. NO. 7785 | 91-AlaHisGlyGlyGluLysTyrSerGlu-99 |
| SEQ. ID. NO. 7786 | 106-AlaValMetAspGluLeuAsn-112 |
| SEQ. ID. NO. 7787 | 152-ThrMetProGluArgAlaTyr-158 |
| SEQ. ID. NO. 7788 | 164-ArgGluLeuArgLysLysTyrAlaPheArgArgTyrGlyPheHisGlyThrSerMetArg-183 |
| SEQ. ID. NO. 7789 | 188-GluAlaAlaArgIleLeuGlyLysProLeuGluAspIleArg-201 |
| SEQ. ID. NO. 7790 | 207-LeuGlyAsnGlyAla-211 |
| SEQ. ID. NO. 7791 | 214-ThrAlaIleLysAsnGlyLysSerValAspThrSerMetGly-227 |
| SEQ. ID. NO. 7792 | 238-ThrArgCysGlyAspIleAspProGlyVal-247 |
| SEQ. ID. NO. 7793 | 260-AlaGlnValAspGluMetLeuAsnLysLysSerGly-271 |
| SEQ. ID. NO. 7794 | 276-SerGluLeuSerAsnAspCysArgThrLeuGluIleAlaAlaAspGluGlyHisGluGlyAlaArgLeu-298 |
| SEQ. ID. NO. 7795 | 329-GlyIleGlyGluAsnSerArgAsnIleArgAlaLysThr-341 |
| SEQ. ID. NO. 7796 | 352-IleAspThrLysAlaAsnMetGluLysArgTyrGlyAsnSerGlyIle-367 |
| SEQ. ID. NO. 7797 | 369-SerProThrAspSerSerPro-375 |
| SEQ. ID. NO. 7798 | 381-ProThrAsnGluGluLeu-386 |
| Hydrophilic Regions - Hopp-Woods | |
| SEQ. ID. NO. 7799 | 19-AlaValIleAspArgLysSerGly-26 |
| SEQ. ID. NO. 7800 | 33-LeuGlyGluArgLeuThrThr-39 |
| SEQ. ID. NO. 7801 | 46-PheAsnLysAspGlyAsnLysArgGlnValProLeuSerGlyArgAsnCysHis-63 |
| SEQ. ID. NO. 7802 | 73-GluLeuGluLysHisGlyLeuHisAspArgIleLysAlaIleGly-87 |
| SEQ. ID. NO. 7803 | 92-HisGlyGlyGluLysTyrSerGlu-99 |
| SEQ. ID. NO. 7804 | 106-AlaValMetAspGluLeuAsn-112 |
| SEQ. ID. NO. 7805 | 153-MetProGluArgAlaTyr-158 |
| SEQ. ID. NO. 7806 | 164-ArgGluLeuArgLysLysTyrAlaPhe-172 |
| SEQ. ID. NO. 7807 | 188-GluAlaAlaArgIleLeuGlyLysProLeuGluAspIleArg-201 |
| SEQ. ID. NO. 7808 | 217-LysAsnGlyLysSerValAspThr-224 |
| SEQ. ID. NO. 7809 | 239-ArgCysGlyAspIleAspPro-245 |
| SEQ. ID. NO. 7810 | 260-AlaGlnValAspGluMetLeuAsnLysLysSerGly-271 |
| SEQ. ID. NO. 7811 | 277-GluLeuSerAsnAspCysArgThrLeuGluIleAlaAlaAspGluGlyHisGluGlyAlaArgLeu-298 |
| SEQ. ID. NO. 7812 | 330-IleGlyGluAsnSerArgAsnIleArgAlaLysThr-341 |
| SEQ. ID. NO. 7813 | 352-IleAspThrLysAlaAsnMetGluLysArgTyrGly-363 |
| SEQ. ID. NO. 7814 | 382-ThrAsnGluGluLeu-386 |
| 604-2 | |
| AMPHI Regions - AMPHI | |
| SEQ. ID. NO. 7815 | 36-HisArgValValGlnPheAla-42 |
| SEQ. ID. NO. 7816 | 3-ValGlyGlyValHisGlyPheAlaThr-61 |
| SEQ. ID. NO. 7817 | 95-ArgThrValSerAlaAspPheLeuGluPhePhe-105 |
| SEQ. ID. NO. 7818 | 113-AspValLeuGlnLeuPheAlaCysValAlaGlnValGlyGlyIleGlnGluAsn-131 |
| SEQ. ID. NO. 7819 | 148-ArgHisIleAsnPheIleAspGlnIleAlaGlyTrpGlu-160 |
| SEQ. ID. NO. 7820 | 166-ValGlyTrpIleLysLysPheAsp-173 |
| SEQ. ID. NO. 7821 | 191-PheGlnAsnCysAlaValLeuHisArg-199 |
| Antigenic Index - Jameson-Wolf | |
| SEQ. ID. NO. 7822 | 11-AlaAlaCysGlyLysValAspGlnArgThrGlyTyrGlyGlyGlyGlyArgAsnGlyAsnArgGlyGlyThrHis-35 |
| SEQ. ID. NO. 7823 | 67-GlyGlyGlyArgAspGluGlyAspPheArgArgValArgAlaSerGlySerPhe-84 |
| SEQ. ID. NO. 7824 | 106-GlnSerArgGlyIle-110 |
| SEQ. ID. NO. 7825 | 127-GlyIleGlnGluGluAsnGlyArgAsnAlaArgValAspGluArgGlyPheGln-143 |
| SEQ. ID. NO. 7826 | 175-TyrPheGlyCysArgGluArgTyrAlaVal-184 |
| SEQ. ID. NO. 7827 | 201-MetGlyAsnAsnGly-205 |
| SEQ. ID. NO. 7828 | 211-LeuProAspPheAspArgAlaAspAlaVal-220 |
| Hydrophilic Regions - Hopp-Woods | |
| SEQ. ID. NO. 7829 | 14-GlyLysValAspGlnArgThrGlyTyr-22 |
| SEQ. ID. NO. 7830 | 24-GlyGlyGlyArgAsnGlyAsnArgGlyGlyThrHis-35 |
| SEQ. ID. NO. 7831 | 68-GlyGlyArgAspGluGlyAspPheArgArgValArgAla-80 |
| SEQ. ID. NO. 7832 | 127-GlyIleGlnGluGluAsnGlyArgAsnAlaArgValAspGluArgGlyPhe-142 |
| SEQ. ID. NO. 7833 | 178-CysArgGluArgTyrAlaVal-184 |
| SEQ. ID. NO. 7834 | 213-AspPheAspArgAlaAspAlaVal-220 |
| 605 | |
| AMPHI Regions - AMPHI | |
| SEQ. ID. NO. 7835 | 13-ArgGlnIleTrpLysIleAlaAsp-20 |
| SEQ. ID. NO. 7836 | 38-ThrLeuPheTyrArgPheIleSerGluAsnPheThrAspTyrMetGln-53 |
| SEQ. ID. NO. 7837 | 107-LysLeuLysGluIlePheThrAlaIle-115 |
| SEQ. ID. NO. 7838 | 128-IleLysGlyLeuPheAspAspPheAsp-136 |
| SEQ. ID. NO. 7839 | 141-ArgLeuGlySerThr-145 |
| SEQ. ID. NO. 7840 | 155-AlaValLeuLysGlyValAlaGluLeu-163 |
| SEQ. ID. NO. 7841 | 173-IleAspLeuPheGlyAspAlaTyrGluTyrLeuIleSerAsn-186 |
| SEQ. ID. NO. 7842 | 188-AlaAlaAsnAlaGlyLys-193 |
| SEQ. ID. NO. 7843 | 204-ValSerLysLeuIleAlaArg-210 |
| SEQ. ID. NO. 7844 | 217-GluLysValAsnLysIleTyrAspPro-225 |
| SEQ. ID. NO. 7845 | 240-PheAspGluHisIle-244 |
| SEQ. ID. NO. 7846 | 291-AspSerLysProPheAspAlaIleValSerAsn-301 |
| SEQ. ID. NO. 7847 | 341-HisAlaLeuAsnTyr-345 |
| SEQ. ID. NO. 7848 | 355-ValSerPheProGly-359 |
| SEQ. ID. NO. 7849 | 433-GluHisIleAlaGluIleValLysLeuPheAla-443 |
| SEQ. ID. NO. 7850 | 452-AlaGlnAsnAlaAlaAlaGlnGlnThr-459 |
| SEQ. ID. NO. 7851 | 478-ThrArgGluIleIleAspIle-484 |
| SEQ. ID. NO. 7852 | 489-AlaGluIleGlyGluThrValAlaLysIleGluArgLeuArgArgGluIleAspGluValIleAlaGluIleGlu-513 |
| Antigenic Index - Jameson-Wolf | |
| SEQ. ID. NO. 7853 | 5-MetGlnGlnArgAlaGlnLeu-11 |
| SEQ. ID. NO. 7854 | 18-IleAlaAspGluValArgGlyAlaValAspGlyTrpAsp-30 |

TABLE 1-continued

| | |
|---|---|
| SEQ. ID. NO. 7855 | 44-IleSerGluAsnPheThrAspTyrMetGlnAlaGlyAspSerSerIleAsp-60 |
| SEQ. ID. NO. 7856 | 63-AlaMetProAspSer-67 |
| SEQ. ID. NO. 7857 | 71-ProGluIleLysAspAspAlaValLysVal-80 |
| SEQ. ID. NO. 7858 | 98-AlaHisGlnAsnGluGluLeuAsnThrLysLeuLysGlu-110 |
| SEQ. ID. NO. 7859 | 116-GluSerSerAlaSerGlyTyrProSerGluGlnAspIleLysGlyLeuPheAspAspPheAspThrThrSerSerArgLeu-142 |
| SEQ. ID. NO. 7860 | 146-ValAlaAspLysAsnLysArgLeu-153 |
| SEQ. ID. NO. 7861 | 190-AsnAlaGlyLysSerGlyGlyGluPhePheThr-200 |
| SEQ. ID. NO. 7862 | 215-GlyGlnGluLysValAsnLysIleTyrAspProAlaCysGlySerGlySer-231 |
| SEQ. ID. NO. 7863 | 235-GlnAlaLysLysGlnPheAsp-241 |
| SEQ. ID. NO. 7864 | 253-GluIleAsnHisThrThrTyrAsn-260 |
| SEQ. ID. NO. 7865 | 280-LeuGlyAspThrLeuThrAsnProLysLeuLysAspSerLysProPheAsp-296 |
| SEQ. ID. NO. 7866 | 309-IleGlySerAspAspProThrLeuIleAsnAspAspArgPheAlaPro-324 |
| SEQ. ID. NO. 7867 | 330-ProLysSerLysAlaAsp-335 |
| SEQ. ID. NO. 7868 | 345-TyrLeuSerLysGlyArgGlyArgAlaAla-353 |
| SEQ. ID. NO. 7869 | 362-TyrArgGlyGlyAlaGluGlnLysIleArg-371 |
| SEQ. ID. NO. 7870 | 403-LeuSerLysHisLysAspAsnThrAsp-411 |
| SEQ. ID. NO. 7871 | 419-GlyPhePheLysLysGluThrAsnAsnAsnValLeuIle-431 |
| SEQ. ID. NO. 7872 | 442-PheAlaAspLysAlaAspVal-448 |
| SEQ. ID. NO. 7873 | 458-GlnThrValLysAspAsnGlyTyr-465 |
| SEQ. ID. NO. 7874 | 473-ValGluAlaGluAspThrArgGluIleIleAsp-483 |
| SEQ. ID. NO. 7875 | 490-GluIleGlyGluThrValAlaLysIleGluArgLeuArgArgGluIleAspGluValIleAla-510 |
| Hydrophilic Regions - Hopp-Woods | |
| SEQ. ID. NO. 7876 | 5-MetGlnGlnArgAlaGlnLeu-11 |
| SEQ. ID. NO. 7877 | 18-IleAlaAspGluValArgGlyAlaValAsp-27 |
| SEQ. ID. NO. 7878 | 55-GlyAspSerSerIle-59 |
| SEQ. ID. NO. 7879 | 71-ProGluIleLysAspAspAlaValLysVal-80 |
| SEQ. ID. NO. 7880 | 98-AlaHisGlnAsnGluGluLeuAsnThrLysLeuLysGlu-110 |
| SEQ. ID. NO. 7881 | 122-TyrProSerGluGlnAspIleLysGlyLeuPheAspAspPheAspThrThrSerSerArgLeu-142 |
| SEQ. ID. NO. 7882 | 146-ValAlaAspLysAsnLysArgLeu-153 |
| SEQ. ID. NO. 7883 | 191-AlaGlyLysSerGlyGly-196 |
| SEQ. ID. NO. 7884 | 215-GlyGlnGluLysValAsnLysIleTyrAsp-224 |
| SEQ. ID. NO. 7885 | 235-GlnAlaLysLysGlnPheAsp-241 |
| SEQ. ID. NO. 7886 | 287-ProLysLeuLysAspSerLysProPhe-295 |
| SEQ. ID. NO. 7887 | 310-GlySerAspAspProThrLeuIleAsnAspAspArgPheAla-323 |
| SEQ. ID. NO. 7888 | 330-ProLysSerLysAlaAsp-335 |
| SEQ. ID. NO. 7889 | 348-GlyArgGlyArgAla-352 |
| SEQ. ID. NO. 7890 | 364-GlyGlyAlaGluGlnLysIleArg-371 |
| SEQ. ID. NO. 7891 | 404-SerLysHisLysAspAsnThrAsp-411 |
| SEQ. ID. NO. 7892 | 419-GlyPhePheLysLysGluThrAsn-426 |
| SEQ. ID. NO. 7893 | 442-PheAlaAspLysAlaAspVal-448 |
| SEQ. ID. NO. 7894 | 458-GlnThrValLysAspAsnGly-464 |
| SEQ. ID. NO. 7895 | 473-ValGluAlaGluAspThrArgGluIleIleAsp-483 |
| SEQ. ID. NO. 7896 | 490-GluIleGlyGluThrValAlaLysIleGluArgLeuArgArgGluIleAspGluValIleAla-510 |
| 606 | |
| AMPHI Regions - AMPHI | |
| SEQ. ID. NO. 7897 | 72-LeuLeuAspHisMetThrArgAspGlu-80 |
| SEQ. ID. NO. 7898 | 90-AlaHisValGlyAsnGlyAsp-96 |
| SEQ. ID. NO. 7899 | 100-LeuThrLeuIleGlnGlyValValAsnThrPhe-110 |
| SEQ. ID. NO. 7900 | 116-ArgIleIleAlaAsn-120 |
| SEQ. ID. NO. 7901 | 139-SerMetValPheGlnIleLeuPheGlyPheLeuAlaSerLeuIleVal-154 |
| SEQ. ID. NO. 7902 | 171-LysLeuValGlyAlaProLysMetIleSerAlaLeuGlnArg-184 |
| SEQ. ID. NO. 7903 | 191-AspLeuProGluGluMetAsnAla-198 |
| Antigenic Index - Jameson-Wolf | |
| SEQ. ID. NO. 7904 | 13-GluValIleAspThrProArgThrGluGluGluAla-24 |
| SEQ. ID. NO. 7905 | 31-GluAlaGlnAlaArgGlnTrpAsnLeuLysThrProGlu-43 |
| SEQ. ID. NO. 7906 | 48-HisSerProGluProAsnAla-54 |
| SEQ. ID. NO. 7907 | 57-ThrGlyAlaSerArgAsnSerSer-64 |
| SEQ. ID. NO. 7908 | 75-HisMetThrArgAspGluValGluAla-83 |
| SEQ. ID. NO. 7909 | 92-ValGlyAsnGlyAsp-96 |
| SEQ. ID. NO. 7910 | 122-IleAlaArgAsnAsnAspGlySerGlnSerGlnGlyThr-134 |
| SEQ. ID. NO. 7911 | 159-ArgGlnArgGluTyrArgAlaAspAlaGlyAla-169 |
| SEQ. ID. NO. 7912 | 182-LeuGlnArgLeuLysGlyAsnProValAspLeuProGluGluMetAsn-197 |
| SEQ. ID. NO. 7913 | 203-GlyAspThrArgAspSerLeuLeuSerThrHisProSerLeuAspAsnArgIleAlaArgLeuLysSer-225 |
| Hydrophilic Regions - Hopp-Woods | |
| SEQ. ID. NO. 7914 | 13-GluValIleAspThrProArgThrGluGluGluAla-24 |
| SEQ. ID. NO. 7915 | 59-AlaSerArgAsnSer-63 |
| SEQ. ID. NO. 7916 | 75-HisMetThrArgAspGluValGluAla-83 |
| SEQ. ID. NO. 7917 | 124-ArgAsnAsnAspGlySerGlnSer-131 |
| SEQ. ID. NO. 7918 | 159-ArgGlnArgGluTyrArgAlaAspAlaGlyAla-169 |
| SEQ. ID. NO. 7919 | 183-GlnArgLeuLysGlyAsnPro-189 |
| SEQ. ID. NO. 7920 | 191-AspLeuProGluGluMetAsn-197 |
| SEQ. ID. NO. 7921 | 203-GlyAspThrArgAspSerLeu-209 |
| SEQ. ID. NO. 7922 | 214-ProSerLeuAspAsnArgIleAlaArgLeuLysSer-225 |
| 607 | |
| AMPHI Regions - AMPHI | |
| SEQ. ID. NO. 7923 | 18-ArgLeuLeuThrThrLeuAlaLeu-25 |
| SEQ. ID. NO. 7924 | 70-PheMetGlyIleMetAlaAlaLeuAsnProMetIleAlaGln-83 |
| SEQ. ID. NO. 7925 | 90-ThrAspGluValGlyGluThr-96 |
| SEQ. ID. NO. 7926 | 104-GlyLeuPheLeuGlyValPheGlyMetValLeuMetTrpAlaAlaIleThrProPheArgAsnTrpLeuThrLeuSerAspTyrValGluGlyThrMet-136 |

TABLE 1-continued

| | |
|---|---|
| SEQ. ID. NO. 7927 | 151-MetValHisArgAlaLeuHisAlaTyrThrSerSer-162 |
| SEQ. ID. NO. 7928 | 226-PhePheArgProPheGly-231 |
| SEQ. ID. NO. 7929 | 244-PheLysGlnIleTrpLysIleGlyAla-252 |
| SEQ. ID. NO. 7930 | 320-AlaArgTyrIleSerGlyVal-326 |
| SEQ. ID. NO. 7931 | 337-IleThrValLeuSerLeuVal-343 |
| SEQ. ID. NO. 7932 | 373-PheGlnProAlaAspPheThrGlnCysIleAlaSerTyrAla-386 |
| SEQ. ID. NO. 7933 | 424-TyrGlyPheTrpThrAlaLeuIleAla-432 |

Antigenic Index - Jameson-Wolf

| | |
|---|---|
| SEQ. ID. NO. 7934 | 15-LysGluValArgLeu-19 |
| SEQ. ID. NO. 7935 | 47-GlyAlaGlyLysGluAspLeuAla-54 |
| SEQ. ID. NO. 7936 | 86-GlyAlaGlyLysThrAspGluValGlyGluThrGlyArgGlnGlyIle-101 |
| SEQ. ID. NO. 7937 | 121-ProPheArgAsnTrp-125 |
| SEQ. ID. NO. 7938 | 128-LeuSerAspTyrValGluGlyThr-135 |
| SEQ. ID. NO. 7939 | 160-ThrSerSerLeuAsnArgProArgLeu-168 |
| SEQ. ID. NO. 7940 | 234-AlaLysPheGlyLysProAspTrp-241 |
| SEQ. ID. NO. 7941 | 311-SerLeuGlyArgArgGluPheSerArgAlaArgTyrIleSer-324 |
| SEQ. ID. NO. 7942 | 353-TyrAsnAsnAspPro-357 |
| SEQ. ID. NO. 7943 | 388-ArgGlyTyrLysValThrLys-394 |
| SEQ. ID. NO. 7944 | 447-LeuCysSerArgGluMetValArgSerHisLysAlaVal-459 |

Hydrophilic Regions - Hopp-Woods

| | |
|---|---|
| SEQ. ID. NO. 7945 | 15-LysGluValArgLeu-19 |
| SEQ. ID. NO. 7946 | 47-GlyAlaGlyLysGluAspLeuAla-54 |
| SEQ. ID. NO. 7947 | 88-GlyLysThrAspGluValGlyGluThrGlyArg-98 |
| SEQ. ID. NO. 7948 | 163-LeuAsnArgProArg-167 |
| SEQ. ID. NO. 7949 | 312-LeuGlyArgArgGluPheSerArg-319 |
| SEQ. ID. NO. 7950 | 390-TyrLysValThrLys-394 |
| SEQ. ID. NO. 7951 | 447-LeuCysSerArgGluMetValArgSerHisLysAlaVal-459 |

608
AMPHI Regions - AMPHI

| | |
|---|---|
| SEQ. ID. NO. 7952 | 66-AlaValGlnLysIleLeuGln-72 |
| SEQ. ID. NO. 7953 | 93-ValLeuSerLeuLeu-97 |
| SEQ. ID. NO. 7954 | 103-ArgAlaSerAspGluLeuAlaArgIlePheGlyThrGln-115 |
| SEQ. ID. NO. 7955 | 124-AspIleGlyHisGlyIleLysGlnIleGlyArgAsnIleAlaGluGlnIleGlyGlyPheSerArgGluSerGluSer-149 |
| SEQ. ID. NO. 7956 | 154-AsnGluAlaLeuAlaAspCysLeuAspGluIleSerArgLeuArgAspGlyValGluArgLeuAsnGluArgLeuAspArgLeu-181 |

Antigenic Index - Jameson-Wolf

| | |
|---|---|
| SEQ. ID. NO. 7957 | 13-LeuGlnSerProAspSerArgSerGluLeu-22 |
| SEQ. ID. NO. 7958 | 39-LeuAlaGlyArgIleThrGluAspGlyLeuLeuSerAlaGlyAsnGlyPheAlaAspThrGluIleThrPheArgAsnSerAla-66 |
| SEQ. ID. NO. 7959 | 71-LeuGlnGlyGlyGluProGlyAlaGlyAspIleGlyLeuGluGly-85 |
| SEQ. ID. NO. 7960 | 98-GlySerLeuArgSerArgAlaSerAspGluLeuAla-109 |
| SEQ. ID. NO. 7961 | 114-ThrGlnAlaAspIleGlySerArgAlaAlaAsp-124 |
| SEQ. ID. NO. 7962 | 131-GlnIleGlyArgAsnIleAla-137 |
| SEQ. ID. NO. 7963 | 140-IleGlyGlyPheSerArgGluSerGluSerAlaAsnIleGlyAsnGluAlaLeuAlaAspCysLeuAspGluIleSerArgLeuArg AspGlyValGluArgLeuAsnGluArgLeuAspArgLeuGluArgAspIleTrp-186 |

Hydrophilic Regions - Hopp-Woods

| | |
|---|---|
| SEQ. ID. NO. 7964 | 15-SerProAspSerArgSerGluLeu-22 |
| SEQ. ID. NO. 7965 | 39-LeuAlaGlyArgIleThrGluAspGlyLeu-48 |
| SEQ. ID. NO. 7966 | 56-AlaAspThrGluIleThrPhe-62 |
| SEQ. ID. NO. 7967 | 74-GlyGluProGlyAlaGly-79 |
| SEQ. ID. NO. 7968 | 81-IleGlyLeuGluGly-85 |
| SEQ. ID. NO. 7969 | 100-LeuArgSerArgAlaSerAspGluLeuAla-109 |
| SEQ. ID. NO. 7970 | 116-AlaAspIleGlySerArgAlaAlaAsp-124 |
| SEQ. ID. NO. 7971 | 143-PheSerArgGluSerGluSerAlaAsnIleGly-153 |
| SEQ. ID. NO. 7972 | 156-AlaLeuAlaAspCysLeuAspGluIleSerArgLeuArgAspGlyValGluArgLeuAsnGluArgLeuAspArgLeuGluArgAspIleTrp-186 |

609
AMPHI Regions - AMPHI

| | |
|---|---|
| SEQ. ID. NO. 7973 | 15-ThrLeuAspAlaPheVal-20 |
| SEQ. ID. NO. 7974 | 30-HisHisIlePheHisGluPheArgValPheValGlyPhePhe-43 |
| SEQ. ID. NO. 7975 | 52-PheGluGlnAlaValGlu-57 |
| SEQ. ID. NO. 7976 | 67-IleAspAspPheLeu-71 |
| SEQ. ID. NO. 7977 | 114-ValAlaValCysProVal-119 |

Antigenic Index - Jameson-Wolf

| | |
|---|---|
| SEQ. ID. NO. 7978 | 10-AlaLeuAspAspGluThrLeu-16 |
| SEQ. ID. NO. 7979 | 20-ValGlyAsnGlnArgSerSerAspIleAla-29 |
| SEQ. ID. NO. 7980 | 69-AspPheLeuAspThrAspPheGlyIle-77 |
| SEQ. ID. NO. 7981 | 79-SerGlnAlaAspGlyAsnValArg-86 |
| SEQ. ID. NO. 7982 | 99-GlyThrArgAlaLysArgGlyTyrGlyAsnHisAspLeu-111 |
| SEQ. ID. NO. 7983 | 122-PheAlaArgGluThrAspIle-128 |

Hydrophilic Regions - Hopp-Woods

| | |
|---|---|
| SEQ. ID. NO. 7984 | 10-AlaLeuAspAspGluThrLeu-16 |
| SEQ. ID. NO. 7985 | 23-GlnArgSerSerAspIle-28 |
| SEQ. ID. NO. 7986 | 79-SerGlnAlaAspGlyAsnVal-85 |
| SEQ. ID. NO. 7987 | 100-ThrArgAlaLysArgGlyTyrGly-107 |
| SEQ. ID. NO. 7988 | 122-PheAlaArgGluThrAspIle-128 |

610
AMPHI Regions - AMPHI

| | |
|---|---|
| SEQ. ID. NO. 7989 | 6-MetGlnPheProTyrArg-11 |
| SEQ. ID. NO. 7990 | 18-MetArgArgMetArgArg-23 |
| SEQ. ID. NO. 7991 | 98-GluArgAlaGlnGluAlaTyr-104 |
| SEQ. ID. NO. 7992 | 111-ProSerThrValArgAlaLeuArgGluArg-120 |
| SEQ. ID. NO. 7993 | 187-IleArgGluAlaLeuGlu-192 |

TABLE 1-continued

| | |
|---|---|
| SEQ. ID. NO. 7994 | 208-TyrAlaSerAlaPheTyrGlyProPheArgAsp-218 |
| SEQ. ID. NO. 7995 | 223-SerGlyAsnLeuGlyLysAlaAsp-230 |
| SEQ. ID. NO. 7996 | 268-LeuAspValValArgArgValLysAspGlu-277 |
| SEQ. ID. NO. 7997 | 296-AlaAlaIleAlaAsn-300 |

Antigenic Index - Jameson-Wolf

| | |
|---|---|
| SEQ. ID. NO. 7998 | 11-ArgAsnValProAlaSerArgMetArgArgMetArgArgAspAspPheSerArgArgLeuMetArgGluHisThrLeuThrAlaAspAsp-40 |
| SEQ. ID. NO. 7999 | 50-GlySerAlaArgGluGluAspValProSerMetProGlyValLysArgGlnSerLeuAsp-69 |
| SEQ. ID. NO. 8000 | 75-AlaGluGluAlaValLys-80 |
| SEQ. ID. NO. 8001 | 94-AlaAsnLysThrGluArgAlaGlnGluAlaTyrAsnProGluGlyLeuVal-110 |
| SEQ. ID. NO. 8002 | 115-ArgAlaLeuArgGluArgPhePro-122 |
| SEQ. ID. NO. 8003 | 139-GlyGlnAspGlyLeuThrAspGluAsnGlyTyrValMetAsnAspGluThrVal-156 |
| SEQ. ID. NO. 8004 | 175-AlaProSerAspMetMetAspGlyArgIleGlyAlaIleArgGluAlaLeuGluAspAlaGlyHis-196 |
| SEQ. ID. NO. 8005 | 215-ProPheArgAspAlaValGlySerSerGlyAsnLeuGlyLysAlaAspLysLysThrTyrGlnMetAspProAlaAsnThrAspGluAlaLeuHis-246 |
| SEQ. ID. NO. 8006 | 250-LeuAspIleGlnGluGlyAlaAsp-257 |
| SEQ. ID. NO. 8007 | 270-ValValArgArgValLysAspGluPheGlyVal-280 |
| SEQ. ID. NO. 8008 | 301-GlyTrpLeuAspGlyGlyLysValVal-309 |
| SEQ. ID. NO. 8009 | 317-LysArgAlaGlyAlaAspGly-323 |
| SEQ. ID. NO. 8010 | 331-GluAlaAlaLysMetLeuLysArg-338 |

Hydrophilic Regions - Hopp-Woods

| | |
|---|---|
| SEQ. ID. NO. 8011 | 14-ProAlaSerArgMetArgArgMetArgArgAspAspPheSerArgArgLeuMetArgGluHisThrLeuThrAla-38 |
| SEQ. ID. NO. 8012 | 50-GlySerAlaArgGluGluAspValProSer-59 |
| SEQ. ID. NO. 8013 | 61-ProGlyValLysArgGlnSerLeuAsp-69 |
| SEQ. ID. NO. 8014 | 75-AlaGluGluAlaValLys-80 |
| SEQ. ID. NO. 8015 | 95-AsnLysThrGluArgAlaGlnGluAlaTyrAsn-105 |
| SEQ. ID. NO. 8016 | 115-ArgAlaLeuArgGluArgPhePro-122 |
| SEQ. ID. NO. 8017 | 141-AspGlyLeuThrAspGluAsnGly-148 |
| SEQ. ID. NO. 8018 | 151-MetAsnAspGluThrVal-156 |
| SEQ. ID. NO. 8019 | 178-AspMetMetAspGlyArgIleGlyAlaIleArgGluAlaLeuGluAspAlaGly-195 |
| SEQ. ID. NO. 8020 | 216-PheArgAspAlaValGly-221 |
| SEQ. ID. NO. 8021 | 225-AsnLeuGlyLysAlaAspLysLysThrTyrGln-235 |
| SEQ. ID. NO. 8022 | 238-ProAlaAsnThrAspGluAlaLeuHis-246 |
| SEQ. ID. NO. 8023 | 250-LeuAspIleGlnGluGlyAlaAsp-257 |
| SEQ. ID. NO. 8024 | 270-ValValArgArgValLysAspGluPheGly-279 |
| SEQ. ID. NO. 8025 | 317-LysArgAlaGlyAla-321 |
| SEQ. ID. NO. 8026 | 331-GluAlaAlaLysMetLeuLysArg-338 |

611
AMPHI Regions - AMPHI

| | |
|---|---|
| SEQ. ID. NO. 8027 | 15-CysArgLeuPheGlyLysLeuSerLeu-23 |
| SEQ. ID. NO. 8028 | 26-ArgLeuLeuLeuGlyLeu-31 |
| SEQ. ID. NO. 8029 | 48-ArgSerValArgArgValIle-54 |
| SEQ. ID. NO. 8030 | 63-GlnValValAlaVal-67 |
| SEQ. ID. NO. 8031 | 104-ValPheIleGluAspPheVal-110 |
| SEQ. ID. NO. 8032 | 130-GlyPheLeuGlyAsnValLeuArgThr-138 |

Antigenic Index - Jameson-Wolf

| | |
|---|---|
| SEQ. ID. NO. 8033 | 1-MetProSerGluAsnGlyMetGlyLysArgGlnLeuAla-13 |
| SEQ. ID. NO. 8034 | 32-CysArgSerGlyValCysArgGlyArgCys-41 |
| SEQ. ID. NO. 8035 | 45-PheProSerArgSerValArgArgValIlePheArgArgValArgIle-60 |
| SEQ. ID. NO. 8036 | 119-AsnProAlaAspPheArgVal-125 |
| SEQ. ID. NO. 8037 | 142-AlaSerGlnGluAsp-146 |

Hydrophilic Regions - Hopp-Woods

| | |
|---|---|
| SEQ. ID. NO. 8038 | 1-MetProSerGluAsnGlyMetGlyLysArgGlnLeuAla-13 |
| SEQ. ID. NO. 8039 | 35-GlyValCysArgGlyArgCys-41 |
| SEQ. ID. NO. 8040 | 53-ValIlePheArgArgValArgIle-60 |
| SEQ. ID. NO. 8041 | 121-AlaAspPheArgVal-125 |
| SEQ. ID. NO. 8042 | 142-AlaSerGlnGluAsp-146 |

612-2
AMPHI Regions - AMPHI

| | |
|---|---|
| SEQ. ID. NO. 8043 | 6-AsnIleAlaLysLysLeuAlaGlyValAsp-15 |
| SEQ. ID. NO. 8044 | 57-LysAlaValGluLysCysAlaGluAsnValLeu-67 |
| SEQ. ID. NO. 8045 | 81-GlyAsnPheProAsn-85 |

Antigenic Index - Jameson-Wolf

| | |
|---|---|
| SEQ. ID. NO. 8046 | 7-IleAlaLysLysLeuAlaGlyValAsp-15 |
| SEQ. ID. NO. 8047 | 27-AspPheGlyArgAspAspAlaValArgHisSerGlyVal-39 |
| SEQ. ID. NO. 8048 | 57-LysAlaValGluLysCysAlaGlu-64 |
| SEQ. ID. NO. 8049 | 97-GlyHisHisArgAsnProTyrLysSer-105 |

Hydrophilic Regions - Hopp-Woods

| | |
|---|---|
| SEQ. ID. NO. 8050 | 7-IleAlaLysLysLeuAlaGlyValAsp-15 |
| SEQ. ID. NO. 8051 | 28-PheGlyArgAspAspAlaValArg-35 |
| SEQ. ID. NO. 8052 | 57-LysAlaValGluLysCysAlaGlu-64 |
| SEQ. ID. NO. 8053 | 101-AsnProTyrLysSer-105 |

613-2
AMPHI Regions - AMPHI

| | |
|---|---|
| SEQ. ID. NO. 8054 | 7-SerArgArgSerLeu-11 |
| SEQ. ID. NO. 8055 | 95-MetProArgMetArgSer-100 |
| SEQ. ID. NO. 8056 | 103-SerProMetSerProAla-108 |
| SEQ. ID. NO. 8057 | 115-ArgIlePheCysThrAlaLeuLeuArgLys-124 |
| SEQ. ID. NO. 8058 | 140-SerSerValMetArgProAla-146 |
| SEQ. ID. NO. 8059 | 168-LeuSerGlyLeuCysArgIle-174 |

Antigenic Index - Jameson-Wolf

| | |
|---|---|
| SEQ. ID. NO. 8060 | 1-MetSerArgSerSerArgSerArgArgSerLeuArgArgSerThrProSerArg-18 |

TABLE 1-continued

| | |
|---|---|
| SEQ. ID. NO. 8061 | 23-SerSerArgGlnSerAlaArgAla-30 |
| SEQ. ID. NO. 8062 | 35-PheAlaAspSerAspSerArgGluAsnProProIleCysSer-48 |
| SEQ. ID. NO. 8063 | 73-ProLysIleArgAlaAsnSerSerAspAlaArgGluArgArgLeuProSerArgAspSerThrAla-94 |
| SEQ. ID. NO. 8064 | 96-ProArgMetArgSerProSerSerProMetSerProAlaProGlySerProProTrp-114 |
| SEQ. ID. NO. 8065 | 130-AlaLysProPheProAlaGluSerLysProSerSerValMetArgProAlaSer-147 |
| SEQ. ID. NO. 8066 | 162-AlaAlaSerSerGluArgLeuSerGlyLeuCysArgIleArgArg-176 |
| SEQ. ID. NO. 8067 | 178-MetMetGlyArgArgAlaAspIlePheSerAspArgGlyGlyGlu-192 |
| SEQ. ID. NO. 8068 | 205-LeuSerArgTyrArgLysArgTyrGly-213 |
| Hydrophilic Regions - Hopp-Woods | |
| SEQ. ID. NO. 8069 | 1-MetSerSerSerArgSerArgArgSerLeuArgArgSerThrProSer-17 |
| SEQ. ID. NO. 8070 | 24-SerArgGlnSerAlaArgAla-30 |
| SEQ. ID. NO. 8071 | 36-AlaAspSerAspSerArgGluAsnProPro-45 |
| SEQ. ID. NO. 8072 | 73-ProLysIleArgAlaAsnSerSerAspAlaArgGluArgArgLeuProSerArgAspSerThrAla-94 |
| SEQ. ID. NO. 8073 | 96-ProArgMetArgSerProSer-102 |
| SEQ. ID. NO. 8074 | 133-PheProAlaGluSerLysProSerSerValMetArg-144 |
| SEQ. ID. NO. 8075 | 162-AlaAlaSerSerGluArgLeuSerGly-170 |
| SEQ. ID. NO. 8076 | 172-CysArgIleArgArg-176 |
| SEQ. ID. NO. 8077 | 178-MetMetGlyArgArgAlaAspIlePheSerAspArgGlyGlyGlu-192 |
| SEQ. ID. NO. 8078 | 206-SerArgTyrArgLysArgTyrGly-213 |
| 614-2 | |
| AMPHI Regions - AMPHI | |
| SEQ. ID. NO. 8079 | 20-SerGlnPheIleGlnGlnVal-26 |
| SEQ. ID. NO. 8080 | 65-AsnLeuIleLysThrLeuLeuAsp-72 |
| SEQ. ID. NO. 8081 | 90-AlaLeuPheTyrSerLeuLeuProValLeu-99 |
| SEQ. ID. NO. 8082 | 144-ValAlaGlyCysAspGluAlaLysGluGluValGlnGluIleValAspTyrLeuLysAlaProAsnArgTyrGlnSerLeu-170 |
| SEQ. ID. NO. 8083 | 210-AspPheValGluMetPheVal-216 |
| SEQ. ID. NO. 8084 | 222-ArgValArgAspMetPheGluGln-229 |
| SEQ. ID. NO. 8085 | 242-GluIleAspAlaValGlyArg-248 |
| SEQ. ID. NO. 8086 | 295-ProAlaLeuGlnArgProGlyArgPheAsp-304 |
| SEQ. ID. NO. 8087 | 333-SerValAspLeuLeuSerLeuAla-340 |
| SEQ. ID. NO. 8088 | 349-AlaAspLeuAlaAsnLeuValAsn-356 |
| SEQ. ID. NO. 8089 | 478-SerAsnAspPheGluArgAlaThrGlnMet-487 |
| SEQ. ID. NO. 8090 | 526-SerGluLysThrGln-530 |
| SEQ. ID. NO. 8091 | 536-GluIleArgArgIleLeuAsp-542 |
| SEQ. ID. NO. 8092 | 561-ThrMetCysLysAlaLeuMetGluTrpGluThr-571 |
| SEQ. ID. NO. 8093 | 591-AspTyrSerHisAsn-595 |
| SEQ. ID. NO. 8094 | 619-ProAlaProAlaAspThr-624 |
| Antigenic Index - Jameson-Wolf | |
| SEQ. ID. NO. 8095 | 7-LeuAspGlyLysLysGluAspAsnGlyGlnIleGlu-18 |
| SEQ. ID. NO. 8096 | 26-ValAsnAsnGlyGluValSerGly-33 |
| SEQ. ID. NO. 8097 | 45-LeuIleLysGlyGluArgThrAspLysSerThrPhe-56 |
| SEQ. ID. NO. 8098 | 60-AlaProLeuAspAspAsnLeuIle-67 |
| SEQ. ID. NO. 8099 | 70-LeuLeuAspLysAsnValArgValLysValThrProGluGluLysProSerAla-87 |
| SEQ. ID. NO. 8100 | 111-MetGlnThrGlyGlyGlyGlyLysGlyGly-120 |
| SEQ. ID. NO. 8101 | 123-SerPheGlyLysSerArgAlaArgLeuLeuAspLysAspAlaAsnLys-138 |
| SEQ. ID. NO. 8102 | 145-AlaGlyCysAspGluAlaLysGluGluValGlnGlu-156 |
| SEQ. ID. NO. 8103 | 161-LeuLysAlaProAsnArgTyrGlnSerLeuGlyGlyArgValProArgGly-177 |
| SEQ. ID. NO. 8104 | 182-GlySerProGlyThrGlyLysThrLeuLeu-191 |
| SEQ. ID. NO. 8105 | 207-SerGlySerAspPhe-211 |
| SEQ. ID. NO. 8106 | 219-GlyAlaSerArgValArgAspMetPheGluGlnAlaLysLysAsnAla-234 |
| SEQ. ID. NO. 8107 | 241-AspGluIleAspAlaValGlyArgGlnArgGlyAlaGlyLeuGlyGlyGlyAsnAspGluArgGluGlnThrLeu-265 |
| SEQ. ID. NO. 8108 | 272-MetAspGlyPheGluSerAsnGln-279 |
| SEQ. ID. NO. 8109 | 287-ThrAsnArgProAspValLeuAspProAlaLeuGlnArgProGlyArgPheAspArg-305 |
| SEQ. ID. NO. 8110 | 311-LeuProAspIleArgGlyArgGluGlnIle-320 |
| SEQ. ID. NO. 8111 | 323-ValHisSerLysLysValProLeuAspGluSerValAsp-335 |
| SEQ. ID. NO. 8112 | 341-ArgGlyThrProGlyPheSerGly-348 |
| SEQ. ID. NO. 8113 | 362-AlaGlyArgArgAsnLysValLysValAspGlnSerAspPheGluAspAlaLysAspLysIleTyrMetGlyProGluArgArgSerMetValMetHis GluAspGluLysArgAlaThrAla-402 |
| SEQ. ID. NO. 8114 | 425-ThrIleMetProArgGlyArgAla-432 |
| SEQ. ID. NO. 8115 | 438-GlnLeuProGluArgAspArgIleSerMetTyrLysAspGlnMet-452 |
| SEQ. ID. NO. 8116 | 460-PheGlyGlyArgIleAlaGlu-466 |
| SEQ. ID. NO. 8117 | 474-SerThrGlyAlaSerAsnAspPheGluArgAlaThrGlnMetAlaArgGluMetValThr-493 |
| SEQ. ID. NO. 8118 | 495-TyrGlyMetSerAspLysMetGly-502 |
| SEQ. ID. NO. 8119 | 507-AlaGluAsnGluGlyGluValPheLeu-515 |
| SEQ. ID. NO. 8120 | 518-SerValThrArgSerGlnAsnIleSerGluLysThrGlnGlnAspIleAspAlaGluIleArgArgIleLeuAspGluGlnTyr-545 |
| SEQ. ID. NO. 8121 | 551-IleLeuAspGluAsnArgAspLysMetGluThrMetCys-563 |
| SEQ. ID. NO. 8122 | 570-GluThrIleAspArgAspGlnVal-577 |
| SEQ. ID. NO. 8123 | 581-MetAlaGlyLysGlnProSerProProLysAspTyrSerHisAsnLeuArgGluAsnAlaAspAlaAlaGluAspAsnAlaProHisAlaProThrArg GluGluThrGluAlaProAlaProAlaAspThrAlaSerThrGluSerGluGlnGlnProGluAsnLysAla-637 |
| Hydrophilic Regions - Hopp-Woods | |
| SEQ. ID. NO. 8124 | 7-LeuAspGlyLysLysGluAspAsnGlyGln-16 |
| SEQ. ID. NO. 8125 | 27-AsnAsnGlyGluValSer-32 |
| SEQ. ID. NO. 8126 | 46-IleLysGlyGluArgThrAspLysSerThr-55 |
| SEQ. ID. NO. 8127 | 61-ProLeuAspAspAsnLeuIle-67 |
| SEQ. ID. NO. 8128 | 70-LeuLeuAspLysAsnValArgValLysValThrProGluGluLysProSerAla-87 |
| SEQ. ID. NO. 8129 | 115-GlyGlyGlyLysGlyGly-120 |
| SEQ. ID. NO. 8130 | 125-GlyLysSerArgAlaArgLeuLeuAspLysAspAlaAsnLys-138 |
| SEQ. ID. NO. 8131 | 145-AlaGlyCysAspGluAlaLysGluGluValGlnGlu-156 |
| SEQ. ID. NO. 8132 | 162-LysAlaProAsnArg-166 |
| SEQ. ID. NO. 8133 | 171-GlyGlyArgValProArg-176 |

TABLE 1-continued

| | |
|---|---|
| SEQ. ID. NO. 8134 | 221-SerArgValArgAspMetPheGluGlnAlaLysLysAsnAla-234 |
| SEQ. ID. NO. 8135 | 241-AspGluIleAspAlaValGlyArgGlnArgGlyAlaGly-253 |
| SEQ. ID. NO. 8136 | 256-GlyGlyAsnAspGluArgGluGlnThr-264 |
| SEQ. ID. NO. 8137 | 273-AspGlyPheGluSer-277 |
| SEQ. ID. NO. 8138 | 287-ThrAsnArgProAspValLeuAsp-294 |
| SEQ. ID. NO. 8139 | 296-AlaLeuGlnArgProGlyArgPheAspArg-305 |
| SEQ. ID. NO. 8140 | 312-ProAspIleArgGlyArgGluGlnIle-320 |
| SEQ. ID. NO. 8141 | 324-HisSerLysLysValProLeuAspGluSerValAsp-335 |
| SEQ. ID. NO. 8142 | 362-AlaGlyArgArgAsnLysValLysValAspGlnSerAspPheGluAspAlaLysAspLysIleTyrMetGlyProGluArgArgSerMetValMetHisGluAspGluLysArgAlaThrAla-402 |
| SEQ. ID. NO. 8143 | 428-ProArgGlyArgAla-432 |
| SEQ. ID. NO. 8144 | 439-LeuProGluArgAspArgIleSerMetTyrLys-449 |
| SEQ. ID. NO. 8145 | 477-AlaSerAsnAspPheGluArgAlaThrGlnMetAlaArgGluMetValThr-493 |
| SEQ. ID. NO. 8146 | 496-GlyMetSerAspLysMetGly-502 |
| SEQ. ID. NO. 8147 | 507-AlaGluAsnGluGlyGluValPheLeu-515 |
| SEQ. ID. NO. 8148 | 518-SerValThrArgSerGlnAsnIleSerGluLysThrGlnGlnAspIleAspAlaGluIleArgArgIleLeuAspGluGlnTyr-545 |
| SEQ. ID. NO. 8149 | 551-IleLeuAspGluAsnArgAspLysMetGluThrMetCys-563 |
| SEQ. ID. NO. 8150 | 570-GluThrIleAspArgAspGlnVal-577 |
| SEQ. ID. NO. 8151 | 584-LysGlnProSerProProLysAspTyrSerHisAsnLeuArgGluAsnAlaAspAlaAlaGluAspAsnAlaPro-608 |
| SEQ. ID. NO. 8152 | 610-AlaProThrArgGluGluThrGluAlaProAlaProAlaAspThrAlaSerThrGluSerGluGlnGlnProGluAsnLysAla-637 |

616-2
AMPHI Regions - AMPHI

| | |
|---|---|
| SEQ. ID. NO. 8153 | 6-LysMetValValGlyLeu-11 |
| SEQ. ID. NO. 8154 | 13-AsnProGlyLysGluTyrGlu-19 |
| SEQ. ID. NO. 8155 | 48-PheGlyGluValAlaArgAla-54 |
| SEQ. ID. NO. 8156 | 77-ValAlaAlaLeuAlaGlnPheTyrLys-85 |
| SEQ. ID. NO. 8157 | 115-GlyHisAsnGlyLeuLysAspIle-122 |
| SEQ. ID. NO. 8158 | 159-HisArgArgGlnIleAspAspAlaValAlaLysSerLeuGlnAlaIleProAspIleLeuAlaGlyLysTrpGluGluAlaThrArgPheLeuHisSer-191 |

Antigenic Index - Jameson-Wolf

| | |
|---|---|
| SEQ. ID. NO. 8159 | 11-LeuGlyAsnProGlyLysGluTyrGluGlnThrArgHisAsnAlaGlyPhe-27 |
| SEQ. ID. NO. 8160 | 39-AlaSerPheLysGluGluLysLysPhePhe-48 |
| SEQ. ID. NO. 8161 | 55-AlaLeuProAspGly-59 |
| SEQ. ID. NO. 8162 | 70-MetAsnArgSerGlyGlnAla-76 |
| SEQ. ID. NO. 8163 | 86-IleLysProGluGlu |
| SEQ. ID. NO. 8164 | 96-AspGluLeuAspIleProCysGlyArgIleLysPhe-107 |
| SEQ. ID. NO. 8165 | 109-LeuGlyGlyGlyAsnGlyGlyHisAsnGlyLeuLysAspIleGlnAla-124 |
| SEQ. ID. NO. 8166 | 127-GlyThrAlaAspTyrTyrArg-133 |
| SEQ. ID. NO. 8167 | 138-IleGlyHisProGlyAspArgAsnLeu-146 |
| SEQ. ID. NO. 8168 | 152-LeuAsnLysProSerThrGluHisArgArgGlnIleAspAspAlaValAla-168 |
| SEQ. ID. NO. 8169 | 181-LysTrpGluGluAlaThrArg-187 |

Hydrophilic Regions - Hopp-Woods

| | |
|---|---|
| SEQ. ID. NO. 8170 | 13-AsnProGlyLysGluTyrGluGlnThrArgHis-23 |
| SEQ. ID. NO. 8171 | 39-AlaSerPheLysGluGluLysLysPhePhe-48 |
| SEQ. ID. NO. 8172 | 86-IleLysProGluGlu-90 |
| SEQ. ID. NO. 8173 | 96-AspGluLeuAspIleProCysGlyArgIleLysPhe-107 |
| SEQ. ID. NO. 8174 | 117-AsnGlyLeuLysAspIleGlnAla-124 |
| SEQ. ID. NO. 8175 | 140-HisProGlyAspArgAsnLeu-146 |
| SEQ. ID. NO. 8176 | 155-ProSerThrGluHisArgArgGlnIleAspAspAlaValAla-168 |
| SEQ. ID. NO. 8177 | 181-LysTrpGluGluAlaThrArg-187 |

619
AMPHI Regions - AMPHI

| | |
|---|---|
| SEQ. ID. NO. 8178 | 50-LysLeuAlaAlaAlaLeuLeu-55 |
| SEQ. ID. NO. 8179 | 66-GlnLeuPheGlnThrLeuThrAsn-73 |
| SEQ. ID. NO. 8180 | 134-GlnGlyGlyArgAspLeu-139 |
| SEQ. ID. NO. 8181 | 146-GlyValIlePheGlyIleLeuPheArgSerLeuSerSerLeuLeuSerArg-162 |
| SEQ. ID. NO. 8182 | 165-AspProGluGluPhe-169 |
| SEQ. ID. NO. 8183 | 175-AsnMetPheAlaGlyPheAsnThrValHisSer-185 |
| SEQ. ID. NO. 8184 | 246-AlaValValGlyProValSerPhePheGlyLeuLeuAlaAlaSerLeuAlaAsnHisPheSer-266 |
| SEQ. ID. NO. 8185 | 294-GluHisLeuLeuGly-298 |
| SEQ. ID. NO. 8186 | 303-LeuSerValValValGluPhe-309 |

Antigenic Index - Jameson-Wolf

| | |
|---|---|
| SEQ. ID. NO. 8187 | 1-MetProSerGluLysAsnIle-7 |
| SEQ. ID. NO. 8188 | 11-AlaGlySerSerArgPro-16 |
| SEQ. ID. NO. 8189 | 35-AsnValLysGlyAspTrpAsp-41 |
| SEQ. ID. NO. 8190 | 132-IleLysGlnGlyGlyArgAspLeuSer-140 |
| SEQ. ID. NO. 8191 | 163-MetIleAspProGluGluPheThr-170 |
| SEQ. ID. NO. 8192 | 203-TrpArgGluArgTyrArgLeuAsp-210 |
| SEQ. ID. NO. 8193 | 215-GlyArgAspGlnAlaVal-220 |
| SEQ. ID. NO. 8194 | 265-PheSerProSerValLysHisSerVal-273 |

Hydrophilic Regions - Hopp-Woods

| | |
|---|---|
| SEQ. ID. NO. 8195 | 1-MetProSerGluLysAsnIle-7 |
| SEQ. ID. NO. 8196 | 134-GlnGlyGlyArgAspLeuSer-140 |
| SEQ. ID. NO. 8197 | 163-MetIleAspProGluGluPheThr-170 |
| SEQ. ID. NO. 8198 | 203-TrpArgGluArgTyrArgLeu-209 |
| SEQ. ID. NO. 8199 | 215-GlyArgAspGlnAla-219 |
| SEQ. ID. NO. 8200 | 269-ValLysHisSerVal-273 |

620
AMPHI Regions - AMPHI

| | |
|---|---|
| SEQ. ID. NO. 8201 | 9-ValAlaValSerAlaLeuSerAlaCysArgGlnAla-20 |
| SEQ. ID. NO. 8202 | 31-IleSerAspArgSerVal-36 |

TABLE 1-continued

| | |
|---|---|
| SEQ. ID. NO. 8203 | 67-SerThrIleLysGlnMetPheGlyTyrThrLysLeuProGluGluProLysGlyIleArgValIleTyrValThrAspMetGlyAsnValThrAspTrpThr-100 |
| SEQ. ID. NO. 8204 | 139-GlnAlaGluLysPhe-143 |
| Antigenic Index - Jameson-Wolf | |
| SEQ. ID. NO. 8205 | 15-SerAlaCysArgGlnAlaGluGluGlyProProProLeuProArgGlnIleSerAspArgSerValGlyHis-38 |
| SEQ. ID. NO. 8206 | 43-AsnLeuThrGluHisAsnGlyProLysAla-52 |
| SEQ. ID. NO. 8207 | 57-AsnGlyLysProAspGlnProVal-64 |
| SEQ. ID. NO. 8208 | 75-TyrThrLysLeuProGluGluProLysGlyIle-85 |
| SEQ. ID. NO. 8209 | 97-ThrAspTrpThrAsnProAsnAlaAspThrGluTrpMetAspAlaLysLys-113 |
| SEQ. ID. NO. 8210 | 125-GlyMetGlyAlaGluAspAlaLeuProPheGlyAsnLysGluGlnAlaGluLysPheAlaLysAspLysGlyGlyLysValValGlyPheAspAspMetProAspThrTyr-161 |
| Hydrophilic Regions - Hopp-Woods | |
| SEQ. ID. NO. 8211 | 18-ArgGlnAlaGluGluGlyProProProLeu-27 |
| SEQ. ID. NO. 8212 | 30-GlnIleSerAspArgSerVal-36 |
| SEQ. ID. NO. 8213 | 46-GluHisAsnGlyProLys-51 |
| SEQ. ID. NO. 8214 | 58-GlyLysProAspGln-62 |
| SEQ. ID. NO. 8215 | 77-LysLeuProGluGluProLysGlyIle-85 |
| SEQ. ID. NO. 8216 | 103-AsnAlaAspThrGluTrpMetAspAlaLysLys-113 |
| SEQ. ID. NO. 8217 | 127-GlyAlaGluAspAlaLeu-132 |
| SEQ. ID. NO. 8218 | 135-GlyAsnLysGluGlnAlaGluLysPheAlaLysAspLysGlyGlyLys-150 |
| SEQ. ID. NO. 8219 | 155-AspAspMetProAsp-159 |
| 622 | |
| AMPHI Regions - AMPHI | |
| SEQ. ID. NO. 8220 | 28-LeuProLysAlaValArgAsnLeuAlaArg-37 |
| SEQ. ID. NO. 8221 | 62-GluGluIleIleArgTrpLeuAlaAsp-70 |
| SEQ. ID. NO. 8222 | 112-IleLeuGlyGlnIleLysAspAlaValArgValAlaGln-124 |
| SEQ. ID. NO. 8223 | 131-LysLysLeuAsnAlaLeuPheGlnLys-139 |
| SEQ. ID. NO. 8224 | 142-SerValAlaLysGluVal-147 |
| SEQ. ID. NO. 8225 | 169-GluGlnIlePheProAspIleGlyAsp-177 |
| SEQ. ID. NO. 8226 | 187-GluMetIleGluLeuValAla-193 |
| SEQ. ID. NO. 8227 | 214-AlaGlnGluLeuCysAspLys-220 |
| SEQ. ID. NO. 8228 | 232-AspLeuProAlaIleLeuHis-238 |
| SEQ. ID. NO. 8229 | 288-AspLeuAsnAspAla-292 |
| SEQ. ID. NO. 8230 | 297-ValAspAspMetValAsnIleValGlnSerGly-307 |
| SEQ. ID. NO. 8231 | 324-GluLysValAlaGluPheValArgGlnGln-333 |
| SEQ. ID. NO. 8232 | 345-LeuArgAspGluGlyGluLys-351 |
| SEQ. ID. NO. 8233 | 354-LysGlnValLeuGluAsnAlaMetLysGlnLeuAlaLys-366 |
| SEQ. ID. NO. 8234 | 372-GluValLeuGluArgLeuSerValGlnLeuThr-382 |
| SEQ. ID. NO. 8235 | 384-LysLeuLeuHisSerProThrGlnThrLeuAsnLysAlaGlyGlu-398 |
| Antigenic Index - Jameson-Wolf | |
| SEQ. ID. NO. 8236 | 16-SerIleArgGluLysLeuAla-22 |
| SEQ. ID. NO. 8237 | 30-LysAlaValArgAsnLeuAlaArgSerAsnAlaAla-41 |
| SEQ. ID. NO. 8238 | 49-ThrCysAsnArgThrGlu-54 |
| SEQ. ID. NO. 8239 | 57-CysValGlyAspSerGluGluIleIle-65 |
| SEQ. ID. NO. 8240 | 75-ProIleGluGluIleArgPro-81 |
| SEQ. ID. NO. 8241 | 87-AspMetGlnGluThrValArgHis-94 |
| SEQ. ID. NO. 8242 | 115-GlnIleLysAspAlaValArgValAlaGlnGluGlnGluSerMetGlyLysLysLeu-133 |
| SEQ. ID. NO. 8243 | 142-SerValAlaLysGluValArgThrAspThrAlaValGlyGluAsnSerVal-158 |
| SEQ. ID. NO. 8244 | 174-AspIleGlyAspLeuAsn-179 |
| SEQ. ID. NO. 8245 | 199-LysSerProArgLeu-203 |
| SEQ. ID. NO. 8246 | 210-ThrLeuAlaArgAlaGlnGluLeuCysAspLysLeuGlyValAsnAlaGlu-226 |
| SEQ. ID. NO. 8247 | 257-GlyMetValGluArgAlaLeuLysGlnArgGlnSer-268 |
| SEQ. ID. NO. 8248 | 277-AlaValProArgAspIleGluAlaGluValGlyAspLeuAsnAsp-291 |
| SEQ. ID. NO. 8249 | 305-GlnSerGlyLysGluAlaArgGlnLysAlaAlaAlaAla-317 |
| SEQ. ID. NO. 8250 | 321-LeuValSerGluLysValAlaGluPheValArgGlnGlnGlnGlyArgGlnSerVal-339 |
| SEQ. ID. NO. 8251 | 343-LysAlaLeuArgAspGluGlyGluLysAlaArgLysGlnValLeu-357 |
| SEQ. ID. NO. 8252 | 368-AlaThrAlaGluGluValLeuGlu-375 |
| SEQ. ID. NO. 8253 | 381-LeuThrAsnLysLeuLeuHisSerProThrGlnThrLeuAsnLysAlaGlyGluGluAspLysAspLeuVal-404 |
| Hydrophilic Regions - Hopp-Woods | |
| SEQ. ID. NO. 8254 | 16-SerIleArgGluLysLeuAla-22 |
| SEQ. ID. NO. 8255 | 30-LysAlaValArgAsnLeuAlaArgSerAsnAlaAla-41 |
| SEQ. ID. NO. 8256 | 59-GlyAspSerGluGluIleIle-65 |
| SEQ. ID. NO. 8257 | 75-ProIleGluGluIleArg-80 |
| SEQ. ID. NO. 8258 | 87-AspMetGlnGluThrValArgHis-94 |
| SEQ. ID. NO. 8259 | 115-GlnIleLysAspAlaValArgValAlaGlnGluGlnGluSerMetGlyLysLysLeu-133 |
| SEQ. ID. NO. 8260 | 142-SerValAlaLysGluValArgThrAspThrAlaValGlyGluAsnSerVal-158 |
| SEQ. ID. NO. 8261 | 210-ThrLeuAlaArgAlaGlnGluLeuCysAsp-219 |
| SEQ. ID. NO. 8262 | 257-GlyMetValGluArgAlaLeuLysGlnArgGlnSer-268 |
| SEQ. ID. NO. 8263 | 277-AlaValProArgAspIleGluAlaGluValGlyAspLeuAsn-290 |
| SEQ. ID. NO. 8264 | 305-GlnSerGlyLysGluAlaArgGlnLysAlaAlaAlaAla-317 |
| SEQ. ID. NO. 8265 | 321-LeuValSerGluLysValAlaGluPheValArg-331 |
| SEQ. ID. NO. 8266 | 333-GlnGlnGlyArgGlnSer-338 |
| SEQ. ID. NO. 8267 | 343-LysAlaLeuArgAspGluGlyGluLysAlaArgLysGlnValLeu-357 |
| SEQ. ID. NO. 8268 | 368-AlaThrAlaGluGluValLeuGlu-375 |
| SEQ. ID. NO. 8269 | 392-ThrLeuAsnLysAlaGlyGluGluAspLysAspLeuVal-404 |
| 624 | |
| AMPHI Regions - AMPHI | |
| SEQ. ID. NO. 8270 | 14-LeuLeuLeuGlyIleIleGlyIlePheLeuPro-24 |
| SEQ. ID. NO. 8271 | 45-ArgPheTyrArgTrpLeuHisArg-52 |
| SEQ. ID. NO. 8272 | 58-ProMetValHisAsn-62 |

TABLE 1-continued

SEQ. ID. NO. 8273 92-PheProGlnArgTrpTrpValGlyAla-100
SEQ. ID. NO. 8274 102-SerSerValPheCysSerLeuValAlaIle-111
Antigenic Index - Jameson-Wolf
SEQ. ID. NO. 8275 41-LysAlaSerProArgPheTyr-47
SEQ. ID. NO. 8276 50-LeuHisArgHisArgTyrPheGlyPro-58
SEQ. ID. NO. 8277 63-TrpGluGlnAsnGlyAlaValProArgLysAlaLys-74
SEQ. ID. NO. 8278 115-ArgArgProGluSer-119
Hydrophilic Regions - Hopp-Woods
SEQ. ID. NO. 8279 67-GlyAlaValProArgLysAlaLys-74
SEQ. ID. NO. 8280 115-ArgArgProGluSer-119
625
AMPHI Regions - AMPHI
SEQ. ID. NO. 8281 25-SerGlyArgIleIleSerIleAlaAla-33
SEQ. ID. NO. 8282 64-LysMetProProGluMetValTyrArgAla-73
Antigenic Index - Jameson-Wolf
SEQ. ID. NO. 8283 5-ArgLysMetLysLysMetThrMetCysThrArgArgVal-17
SEQ. ID. NO. 8284 57-ProPheLysSerProGlnThrLysMetProPro-67
SEQ. ID. NO. 8285 73-AlaSerSerSerArgMetLysGly-80
SEQ. ID. NO. 8286 96-AspAlaProLysThrLysLeuAsnGlyMetArgLysSerAsnValGln-111
Hydrophilic Regions - Hopp-Woods
SEQ. ID. NO. 8287 5-ArgLysMetLysLysMetThrMetCysThrArgArgVal-17
SEQ. ID. NO. 8288 60-SerProGlnThrLysMetProPro-67
SEQ. ID. NO. 8289 74-SerSerSerArgMetLysGly-80
SEQ. ID. NO. 8290 96-AspAlaProLysThrLysLeuAsnGlyMetArgLysSerAsnValGln-111
627-2
AMPHI Regions - AMPHI
SEQ. ID. NO. 8291 52-TrpHisHisHisTyrGlyLysIleThrAlaPheTrpThrLeuLeuPheLeu-68
SEQ. ID. NO. 8292 83-ThrValAlaHisAlaLeu-88
SEQ. ID. NO. 8293 128-ValGlyThrAlaLeuAlaSerIleMetGly-137
SEQ. ID. NO. 8294 173-IleGlyGlyGlyLeuThrPro-179
SEQ. ID. NO. 8295 189-PheLeuLysGlyValAsp-194
SEQ. ID. NO. 8296 245-AlaIlePheGlyLysTrp-250
SEQ. ID. NO. 8297 258-ValValGlyAlaVal-262
SEQ. ID. NO. 8298 284-LeuGlnAsnLeuVal-288
SEQ. ID. NO. 8299 319-IleAlaGluValGlyLysLeuPheLeuGlyIlePheIleThrIlePheProValLeuSerIleLeuLysAlaGlyGluAlaGlyAlaLeuGlyGlyVal
ValSerLeuValHisAspThrAlaGlyHisProIle-363
SEQ. ID. NO. 8300 372-GlyIleLeuSerAlaPheLeuAspAsnAla-381
SEQ. ID. NO. 8301 404-PheHisSerLeuLeuAlaValSer-411
SEQ. ID. NO. 8302 416-PheMetGlyAlaLeuThrTyrIleGlyAsnAlaProAsnPheMetValLys-432
SEQ. ID. NO. 8303 444-ThrPhePheGlyTyr-448
Antigenic Index - Jameson-Wolf
SEQ. ID. NO. 8304 20-AspLeuAspGlyAlaAsn-25
SEQ. ID. NO. 8305 114-AspLeuAsnGlyThrProLysLeu-121
SEQ. ID. NO. 8306 149-LeuLeuLysAlaAsnGlnAsnArgThrArgArgVal-160
SEQ. ID. NO. 8307 172-AsnIleGlyGlyGly-176
SEQ. ID. NO. 8308 178-ThrProLeuGlyAspProPro-184
SEQ. ID. NO. 8309 223-ArgPhePheLysGlnGluSerIleAlaGlnAspThrProAlaGlnGlnGluLysProGluLys-243
SEQ. ID. NO. 8310 266-GlyLeuTrpLysProGluHisProGlyPhe-275
SEQ. ID. NO. 8311 304-ThrProLysGlnValArgAlaGlyAsnGluPheAsnPhe-316
SEQ. ID. NO. 8312 357-AspThrAlaGlyHis-361
SEQ. ID. NO. 8313 391-AlaGlyGlyAspAla-395
SEQ. ID. NO. 8314 433-AlaIleAlaGluGlnArgGlyValPro-441
Hydrophilic Regions - Hopp-Woods
SEQ. ID. NO. 8315 153-AsnGlnAsnArgThrArgArgVal-160
SEQ. ID. NO. 8316 228-GluSerIleAlaGln-232
SEQ. ID. NO. 8317 234-ThrProAlaGlnGlnGluLysProGluLys-243
SEQ. ID. NO. 8318 268-TrpLysProGluHisProGly-274
SEQ. ID. NO. 8319 306-LysGlnValArgAlaGlyAsn-312
SEQ. ID. NO. 8320 433-AlaIleAlaGluGlnArgGlyVal-440
628
AMPHI Regions - AMPHI
SEQ. ID. NO. 8321 10-CysGlyProProAsnSerCysValSerMetLeuAlaAlaPheSerAspGlyThrSerAlaProAlaAla-32
SEQ. ID. NO. 8322 34-GlnThrTrpIleLeuArgSer-40
Antigenic Index - Jameson-Wolf
SEQ. ID. NO. 8323 6-LysProAlaGlyCysGlyProProAsnSer-15
SEQ. ID. NO. 8324 23-PheSerAspGlyThrSerAla-29
SEQ. ID. NO. 8325 40-SerValLysArgLeuAsnThrAsnArgProArgLeuLysSerSerAla-55
SEQ. ID. NO. 8326 77-MetAlaAsnGlySerAlaSerThr-84
SEQ. ID. NO. 8327 91-GlyArgValArgSerAlaValHisLysProAspTrpIleArgLeuArgArgThrSerSerProLeuLys-113
Hydrophilic Regions - Hopp-Woods
SEQ. ID. NO. 8328 40-SerValLysArgLeuAsnThrAsnArgProArgLeuLysSerSerAla-55
SEQ. ID. NO. 8329 91-GlyArgValArgSerAlaValHisLys-99
SEQ. ID. NO. 8330 101-AspTrpIleArgLeuArgArgThrSerSer-110
629
AMPHI Regions - AMPHI
SEQ. ID. NO. 8331 32-ArgTrpSerAspValPheSer-38
SEQ. ID. NO. 8332 48-IleSerArgLeuProArgThrPhe-55
SEQ. ID. NO. 8333 116-ValAlaAlaLeuIleGlyMetLeu-123
SEQ. ID. NO. 8334 146-IlePheGlyGlyValIleGluAlaValAlaThr-156
SEQ. ID. NO. 8335 167-MetLeuGlyValTrpGlnGlnGlyAsp-175

TABLE 1-continued

| | |
|---|---|
| SEQ. ID. NO. 8336 | 206-IleLeuGlyLeuGlyGlu-211 |
| SEQ. ID. NO. 8337 | 252-ValValProAsnIleIleSerArgLeuMetGlyAspArgLeuArgGlnSer-268 |
| SEQ. ID. NO. 8338 | 285-IleIleGlyArgVal-289 |
| SEQ. ID. NO. 8339 | 300-ThrValPheGlyValLeu-305 |

Antigenic Index - Jameson-Wolf

| | |
|---|---|
| SEQ. ID. NO. 8340 | 38-SerLeuSerAspSerGln-43 |
| SEQ. ID. NO. 8341 | 50-ArgLeuProArgThr-54 |
| SEQ. ID. NO. 8342 | 77-AsnArgPheValGluProSerMetValGlyAlaSerGln-89 |
| SEQ. ID. NO. 8343 | 130-ArgArgLeuProProThrAla-136 |
| SEQ. ID. NO. 8344 | 260-LeuMetGlyAspArgLeuArgGlnSer-268 |

Hydrophilic Regions - Hopp-Woods

| | |
|---|---|
| SEQ. ID. NO. 8345 | 260-LeuMetGlyAspArgLeuArgGln-267 |

630-2
AMPHI Regions - AMPHI

| | |
|---|---|
| SEQ. ID. NO. 8346 | 6-PheLeuGluLysIleGluPro-12 |
| SEQ. ID. NO. 8347 | 23-TrpTyrAlaLeuTyrGlu-28 |
| SEQ. ID. NO. 8348 | 64-LeuPheProAlaMetPheTyrGlyMetTyrAsn-74 |
| SEQ. ID. NO. 8349 | 87-LeuLeuGlnGlnAsnIleAlaAsnAspTrpHisTyrAlaPhe-100 |
| SEQ. ID. NO. 8350 | 137-GlyPheTrpGluValLeuPheAla-144 |
| SEQ. ID. NO. 8351 | 190-PheGlyGlyThrGlyLysAsnPhe-197 |
| SEQ. ID. NO. 8352 | 224-AlaValAspGlyTyrSerGlyAlaThrAlaLeuAlaGlnTrp-237 |
| SEQ. ID. NO. 8353 | 242-AlaAspGlyLeuLysAsnAlaVal-249 |
| SEQ. ID. NO. 8354 | 258-AspAlaPheIleGlyLysLeuProGlySerIleGlyGluValSer-272 |
| SEQ. ID. NO. 8355 | 285-PheAlaArgIleAlaSerTrpArgIleIleAlaGlyValMet-298 |
| SEQ. ID. NO. 8356 | 302-IleAlaMetSerSerLeuPheAsnPhe-310 |
| SEQ. ID. NO. 8357 | 344-ValSerAlaSerPheThrAsnValGlyLysTrpTrpTyrGlyAlaLeuIleGlyValMetCysValLeuIleArgVal-369 |
| SEQ. ID. NO. 8358 | 382-IleLeuPheAlaAsnLeuPheAlaProIlePheAspTyrPhe-395 |

Antigenic Index - Jameson-Wolf

| | |
|---|---|
| SEQ. ID. NO. 8359 | 6-PheLeuGluLysIleGlu-11 |
| SEQ. ID. NO. 8360 | 16-ProGlyGlyLysHisGluLys-22 |
| SEQ. ID. NO. 8361 | 37-SerGlyAlaValThrArgLysAlaAlaHisValArgAspAlaLeuAspSerLysArgMet-56 |
| SEQ. ID. NO. 8362 | 107-AsnMetSerSerGluAlaGlyValSerAspLysMet-118 |
| SEQ. ID. NO. 8363 | 146-ValArgLysHisGluIleAsnGlu-153 |
| SEQ. ID. NO. 8364 | 189-ValPheGlyGlyThrGlyLysAsnPheMet-198 |
| SEQ. ID. NO. 8365 | 212-TyrProAlaAsnLeuSerGlyAspAla-220 |
| SEQ. ID. NO. 8366 | 241-GlyAlaAspGlyLeuLys-246 |
| SEQ. ID. NO. 8367 | 264-LeuProGlySerIleGly-269 |
| SEQ. ID. NO. 8368 | 312-GlySerAspThrAsnAla-317 |
| SEQ. ID. NO. 8369 | 400-AsnIleLysArgArgLysAlaArgSerAsnGly-410 |

Hydrophilic Regions - Hopp-Woods

| | |
|---|---|
| SEQ. ID. NO. 8370 | 6-PheLeuGluLysIleGlu-11 |
| SEQ. ID. NO. 8371 | 18-GlyLysHisGluLys-22 |
| SEQ. ID. NO. 8372 | 39-AlaValThrArgLysAlaAlaHisValArgAspAlaLeuAspSerLysArgMet-56 |
| SEQ. ID. NO. 8373 | 108-MetSerSerGluAlaGlyValSerAsp-116 |
| SEQ. ID. NO. 8374 | 146-ValArgLysHisGluIleAsn-152 |
| SEQ. ID. NO. 8375 | 400-AsnIleLysArgArgLysAlaArgSerAsnGly-410 |

638
AMPHI Regions - AMPHI

| | |
|---|---|
| SEQ. ID. NO. 8376 | 30-IleValAspIleValGluHis-36 |
| SEQ. ID. NO. 8377 | 46-AspIleValGluTyrPheGluProLeuGlyLys-56 |
| SEQ. ID. NO. 8378 | 108-ProPheGlyAsnValValAlaAspAspLeuArgThrGly-120 |
| SEQ. ID. NO. 8379 | 148-ArgIleGlyArgThrMet-153 |
| SEQ. ID. NO. 8380 | 198-GluArgTyrValArgArgValTyrGlyTyrGlyThrPro-210 |
| SEQ. ID. NO. 8381 | 212-ProValAlaPheAspGlyCysGlyThrValGlyArg-223 |
| SEQ. ID. NO. 8382 | 242-SerGlnPheGluArgIleAlaArgProGly-251 |

Antigenic Index - Jameson-Wolf

| | |
|---|---|
| SEQ. ID. NO. 8383 | 43-AlaAspGlyAspIle-47 |
| SEQ. ID. NO. 8384 | 53-ProLeuGlyLysHisGln-58 |
| SEQ. ID. NO. 8385 | 81-ValAspGlyGluThrGlnIle-87 |
| SEQ. ID. NO. 8386 | 99-AlaGlyIleGlyLysAsnAlaVal-106 |
| SEQ. ID. NO. 8387 | 113-ValAlaAspAspLeuArgThrGlyCysValProAsnGly-125 |
| SEQ. ID. NO. 8388 | 135-GlnSerArgValAlaAsp-140 |
| SEQ. ID. NO. 8389 | 156-TyrAlaAspArgIleIle-161 |
| SEQ. ID. NO. 8390 | 168-AsnGlnGlyAlaArgGlySerPhe-175 |
| SEQ. ID. NO. 8391 | 178-IleAsnThrGlyIleHis-183 |
| SEQ. ID. NO. 8392 | 188-HisThrGlyThrGlyAsnGlyGlnValAlaGluArgTyrValArg-202 |
| SEQ. ID. NO. 8393 | 205-TyrGlyTyrGlyThr-209 |
| SEQ. ID. NO. 8394 | 216-AspGlyCysGlyThrValGlyArgProPheAsnArgAsnArgPheVal-231 |
| SEQ. ID. NO. 8395 | 240-AlaGlySerGlnPheGluArgIleAlaArgProGlyAlaGlyLysCysGly-256 |

Hydrophilic Regions - Hopp-Woods

| | |
|---|---|
| SEQ. ID. NO. 8396 | 43-AlaAspGlyAspIle-47 |
| SEQ. ID. NO. 8397 | 81-ValAspGlyGluThrGlnIle-87 |
| SEQ. ID. NO. 8398 | 113-ValAlaAspAspLeuArgThr-119 |
| SEQ. ID. NO. 8399 | 136-SerArgValAlaAsp-140 |
| SEQ. ID. NO. 8400 | 195-GlnValAlaGluArgTyrValArg-202 |
| SEQ. ID. NO. 8401 | 243-GlnPheGluArgIleAlaArgProGlyAlaGly-253 |

639-1
AMPHI Regions - AMPHI

| | |
|---|---|
| SEQ. ID. NO. 8402 | 95-TyrLysAsnAsnArg-99 |
| SEQ. ID. NO. 8403 | 137-LeuLysValPheAspAsnIle-143 |

TABLE 1-continued

| | |
|---|---|
| SEQ. ID. NO. 8404 | 157-ValAsnTyrSerAspIleHisAspAsnIleIleAsnLysAla-170 |
| SEQ. ID. NO. 8405 | 181-TyrAspLysLeuPheAlaAsnHisPheGlu-190 |
| SEQ. ID. NO. 8406 | 269-AlaProValSerArg-273 |
| SEQ. ID. NO. 8407 | 290-GlnPheProAlaValLeuProGly-297 |
| SEQ. ID. NO. 8408 | 322-AspGluLeuLeuLysGluValGlu-329 |

Antigenic Index - Jameson-Wolf

| | |
|---|---|
| SEQ. ID. NO. 8409 | 13-GluGluThrAlaPro-17 |
| SEQ. ID. NO. 8410 | 23-HisAsnAsnIleLeuAspAsnSer30 |
| SEQ. ID. NO. 8411 | 41-AlaMetValArgGluAsnLysIleValGly-50 |
| SEQ. ID. NO. 8412 | 52-AlaThrLeuArgValAsnGluArgGlyAsnGly-62 |
| SEQ. ID. NO. 8413 | 75-GlyAsnAspIleSerLysGlyArgAspGlyIlePheSerAsnThrSerThrHisAsnThrTyrLysAsnAsnArgPheSerAsp-102 |
| SEQ. ID. NO. 8414 | 111-TyrThrAsnAspSerGluIleSerGly-119 |
| SEQ. ID. NO. 8415 | 121-IleSerValGlyAsnAsn-126 |
| SEQ. ID. NO. 8416 | 135-GluArgLeuLysVal-139 |
| SEQ. ID. NO. 8417 | 145-ValGlySerArgAspGlnGlyIle-152 |
| SEQ. ID. NO. 8418 | 160-SerAspIleHisAspAsnIleIleAsnLysAlaGlyLys-172 |
| SEQ. ID. NO. 8419 | 203-GluGlyThrSerLeuHisAspAsnSerPheIleAsnAsnGluSerGlnValLysTyrVal-222 |
| SEQ. ID. NO. 8420 | 228-AspTrpSerGluGlyGlyHisGlyAsnTyrTrpSerAspAsnSerAla-243 |
| SEQ. ID. NO. 8421 | 246-LeuAsnGlyAspGlyPheGlyAspSerAlaTyrArgProAsnGlyIleIle-262 |
| SEQ. ID. NO. 8422 | 297-GlyGlyValValAspSerLysProLeuMetLysProTyrAlaProLysIleGlnThr-315 |
| SEQ. ID. NO. 8423 | 318-GlnAlaMetLysAspGluLeuLeuLysGluValGluThrArgGlnSerGluTrpGlyArgAlaGluAsnGlySerLeuAsn-344 |

Hydrophilic Regions - Hopp-Woods

| | |
|---|---|
| SEQ. ID. NO. 8424 | 41-AlaMetValArgGluAsnLysIleValGly-50 |
| SEQ. ID. NO. 8425 | 52-AlaThrLeuArgValAsnGluArgGlyAsn-61 |
| SEQ. ID. NO. 8426 | 77-AspIleSerLysGlyArgAspGlyIle-85 |
| SEQ. ID. NO. 8427 | 95-TyrLysAsnAsnArgPheSerAsp-102 |
| SEQ. ID. NO. 8428 | 113-AsnAspSerGluIleSerGly-119 |
| SEQ. ID. NO. 8429 | 135-GluArgLeuLysVal-139 |
| SEQ. ID. NO. 8430 | 146-GlySerArgAspGlnGly-151 |
| SEQ. ID. NO. 8431 | 299-ValValAspSerLysProLeuMet-306 |
| SEQ. ID. NO. 8432 | 318-GlnAlaMetLysAspGluLeuLeuLysGluValGluThrArgGlnSerGluTrpGlyArgAlaGluAsnGlySer-342 |

640-2
AMPHI Regions - AMPHI

| | |
|---|---|
| SEQ. ID. NO. 8433 | 6-SerIleLeuLysSerIleGlyIle-13 |
| SEQ. ID. NO. 8434 | 22-SerIleLysArgMetSer-27 |
| SEQ. ID. NO. 8435 | 47-LeuProAlaTyrAlaGluArgLeuProAspPheLeuAlaLysIleGlnPro-63 |
| SEQ. ID. NO. 8436 | 72-ArgTyrGlyLysPro-76 |
| SEQ. ID. NO. 8437 | 127-AlaLysLeuValAspHisHis-133 |
| SEQ. ID. NO. 8438 | 141-IleProHisLeuProAlaProGlyArgAlaIle-151 |
| SEQ. ID. NO. 8439 | 153-SerAsnTrpLeuProAla-158 |

Antigenic Index - Jameson-Wolf

| | |
|---|---|
| SEQ. ID. NO. 8440 | 24-LysArgMetSerAlaPheArgAlaArgIle-33 |
| SEQ. ID. NO. 8441 | 50-TyrAlaGluArgLeuProAspPhe-57 |
| SEQ. ID. NO. 8442 | 59-AlaLysIleGlnProSerGluIlePheProGlyAlaAspArgTyrGlyLysProGluGlyLysProMetVal-82 |
| SEQ. ID. NO. 8443 | 84-ArgValTyrLysGlyAspGluGlnLeu-92 |
| SEQ. ID. NO. 8444 | 101-AlaValAsnThrArgGlyTyrSerSerLysProIleAsp-113 |
| SEQ. ID. NO. 8445 | 128-LysLeuValAspHisHisGlu-134 |
| SEQ. ID. NO. 8446 | 144-LeuProAlaProGlyArgAlaIleArg-152 |
| SEQ. ID. NO. 8447 | 168-AsnArgLeuArgLeuLysGlyLeuPro-176 |
| SEQ. ID. NO. 8448 | 178-ValProGlnProSerLysAlaThrGly-186 |

Hydrophilic Regions - Hopp-Woods

| | |
|---|---|
| SEQ. ID. NO. 8449 | 24-LysArgMetSerAlaPheArgAlaArgIle-33 |
| SEQ. ID. NO. 8450 | 50-TyrAlaGluArgLeuPro-55 |
| SEQ. ID. NO. 8451 | 68-ProGlyAlaAspArgTyrGlyLysProGluGlyLysProMetVal-82 |
| SEQ. ID. NO. 8452 | 85-ValTyrLysGlyAspGluGlnLeu-92 |
| SEQ. ID. NO. 8453 | 128-LysLeuValAspHisHisGlu-134 |
| SEQ. ID. NO. 8454 | 146-AlaProGlyArgAlaIleArg-152 |
| SEQ. ID. NO. 8455 | 168-AsnArgLeuArgLeuLysGly-174 |
| SEQ. ID. NO. 8456 | 180-GlnProSerLysAlaThrGly-186 |

642-2
AMPHI Regions - AMPHI

| | |
|---|---|
| SEQ. ID. NO. 8457 | 157-IleLysHisIleValArgAlaPhe-164 |
| SEQ. ID. NO. 8458 | 179-GlyValSerAlaPheLysThrLeuArgThrGlnGluPheLeuGlnHisLeuArgGlyGlyVal-199 |
| SEQ. ID. NO. 8459 | 202-PheArgGlyGluGly-206 |
| SEQ. ID. NO. 8460 | 208-AspAspValArgLeu-212 |
| SEQ. ID. NO. 8461 | 228-AspValAlaValLysAsnLeuGlyAsnLeuMetAlaAlaProAsp-242 |
| SEQ. ID. NO. 8462 | 259-PheGlnIlePheLysAspValPheHisAsnAlaValArgHisAlaAspGlnLeuGln-277 |
| SEQ. ID. NO. 8463 | 311-ValAspGlyValThrAspGlyAla-318 |
| SEQ. ID. NO. 8464 | 337-GlnValAspAspPheGlyGluPheAlaValPhe-347 |
| SEQ. ID. NO. 8465 | 366-PheArgGlyValAsp-370 |
| SEQ. ID. NO. 8466 | 409-HisLeuGlnThrLeuArgAspLeuArgPheIleAlaGluLeuLeuGlnTrpLeuGlnHisGlnArgAlaPheAspAlaGlyThr-436 |
| SEQ. ID. NO. 8467 | 445-ProArgAsnProGlnAsp-450 |

Antigenic Index - Jameson-Wolf

| | |
|---|---|
| SEQ. ID. NO. 8468 | 1-MetArgHisProProGlnSerAlaAlaLeu-10 |
| SEQ. ID. NO. 8469 | 17-LeuLeuHisArgProLysSerValCysArgArgArgLysCysArgLeuLysAla-34 |
| SEQ. ID. NO. 8470 | 36-ProLeuSerAspGlyIleAlaCys-43 |
| SEQ. ID. NO. 8471 | 63-ValGlnGlnGluGlyCysGly-69 |
| SEQ. ID. NO. 8472 | 75-LeuTyrGluAspLysGluSerGlyAspAspPheAlaAspLysAspPheLeuGln-92 |
| SEQ. ID. NO. 8473 | 104-GluAlaAlaAspValPheArg-110 |
| SEQ. ID. NO. 8474 | 115-AlaGlyAspGlyGlyLysAlaGly-122 |

TABLE 1-continued

| | |
|---|---|
| SEQ. ID. NO. 8475 | 144-PheGlyGlyGlyAlaAspLysLeu-151 |
| SEQ. ID. NO. 8476 | 164-PheLysAsnArgGluGlyAlaAspValAspSerAspIleAlaGly-178 |
| SEQ. ID. NO. 8477 | 184-LysThrLeuArgThrGlnGluI-190 |
| SEQ. ID. NO. 8478 | 202-PheArgGlyGluGlyPheAspAspValArgLeu-212 |
| SEQ. ID. NO. 8479 | 217-GlyAspGlyGlyAsnArgArgAsnGlyMetAla-227 |
| SEQ. ID. NO. 8480 | 249-AspGluPheAspVal-253 |
| SEQ. ID. NO. 8481 | 271-ArgHisAlaAspGlnLeuGlnAlaAlaAlaAspLysAspValLeuGluArgAlaGlnThrGly-291 |
| SEQ. ID. NO. 8482 | 300-HisGlyGlyCysArg-304 |
| SEQ. ID. NO. 8483 | 306-PheGlyIleAspAlaValAspGlyValThrAspGly-317 |
| SEQ. ID. NO. 8484 | 331-CysPheGlyAspGluGlnGlnValAspAspPheGly-342 |
| SEQ. ID. NO. 8485 | 350-PheGlyGlyAsnGluGluGluValAlaLeu-359 |
| SEQ. ID. NO. 8486 | 369-ValAspValAsnGly-373 |
| SEQ. ID. NO. 8487 | 387-CysAsnArgArgAlaGlyGlyPhe-394 |
| SEQ. ID. NO. 8488 | 396-PheGlyAsnThrGln-400 |
| SEQ. ID. NO. 8489 | 411-GlnThrLeuArgAspLeuArgPhe-418 |
| SEQ. ID. NO. 8490 | 430-ArgAlaPheAspAlaGlyThrGlnArgAsnGly-440 |
| SEQ. ID. NO. 8491 | 443-ValMetProArgAsnProGlnAspPheLeuAsp-453 |
| SEQ. ID. NO. 8492 | 468-GluGlyGlnGlnGlnThrArg-474 |
| Hydrophilic Regions - Hopp-Woods | |
| SEQ. ID. NO. 8493 | 1-MetArgHisProPro-5 |
| SEQ. ID. NO. 8494 | 17-LeuLeuHisArgProLysSerValCysArgArgArgLysCysArgLeuLysAla-34 |
| SEQ. ID. NO. 8495 | 75-LeuTyrGluAspLysGluSerGlyAspAspPheAlaAspLysAspPheLeu-91 |
| SEQ. ID. NO. 8496 | 104-GluAlaAlaAspValPheArg-110 |
| SEQ. ID. NO. 8497 | 117-AspGlyGlyLysAla-121 |
| SEQ. ID. NO. 8498 | 147-GlyAlaAspLysLeu-151 |
| SEQ. ID. NO. 8499 | 164-PheLysAsnArgGluGlyAlaAspValAspSerAspIle-176 |
| SEQ. ID. NO. 8500 | 184-LysThrLeuArgThr-188 |
| SEQ. ID. NO. 8501 | 205-GluGlyPheAspAspValArgLeu-212 |
| SEQ. ID. NO. 8502 | 217-GlyAspGlyGlyAsnArgArgAsnGlyMet-226 |
| SEQ. ID. NO. 8503 | 249-AspGluPheAspVal-253 |
| SEQ. ID. NO. 8504 | 271-ArgHisAlaAspGlnLeuGlnAlaAlaAlaAspLysAspValLeuGluArgAlaGlnThr-290 |
| SEQ. ID. NO. 8505 | 310-AlaValAspGlyValThrAspGly-317 |
| SEQ. ID. NO. 8506 | 331-CysPheGlyAspGluGlnGlnValAspAspPheGly-342 |
| SEQ. ID. NO. 8507 | 352-GlyAsnGluGluGluValAlaLeu-359 |
| SEQ. ID. NO. 8508 | 387-CysAsnArgArgAlaGly-392 |
| SEQ. ID. NO. 8509 | 412-ThrLeuArgAspLeuArgPhe-418 |
| SEQ. ID. NO. 8510 | 435-GlyThrGlnArgAsnGly-440 |
| SEQ. ID. NO. 8511 | 446-ArgAsnProGlnAsp-450 |
| SEQ. ID. NO. 8512 | 468-GluGlyGlnGlnGln-472 |
| 644-2 | |
| AMPHI Regions - AMPHI | |
| SEQ. ID. NO. 8513 | 13-MetAspThrAlaAlaPheLeuLysHisIleGluSerAlaPheArgArgIlePheSerAspGlyIleAspLeuMetArgTyrLeu-40 |
| SEQ. ID. NO. 8514 | 69-GlnPheGluIleGlnGluValLeuArgIleAlaGly-80 |
| SEQ. ID. NO. 8515 | 99-GlnProLeuGlnGluPheGlyAsp-106 |
| SEQ. ID. NO. 8516 | 139-ArgGluMetGlnSerTyrTyrGluTyrIleAspGly-150 |
| SEQ. ID. NO. 8517 | 160-TyrTrpGlnGlyAsn-164 |
| SEQ. ID. NO. 8518 | 182-LeuAlaLysValIleAspLeuLeu-189 |
| SEQ. ID. NO. 8519 | 234-AlaGlyLeuArgAlaPheGlnAsn-241 |
| SEQ. ID. NO. 8520 | 253-MetThrHisGlyIleMetGluTyrIleLeuGluAsnLeuGluArgTyrValArgAsn-271 |
| SEQ. ID. NO. 8521 | 291-GluIleLeuTyrArgTyrValCysHis-299 |
| SEQ. ID. NO. 8522 | 301-ValSerProValAlaProValAlaHis-309 |
| SEQ. ID. NO. 8523 | 314-AlaAsnIleValLysThrLeuAla-321 |
| SEQ. ID. NO. 8524 | 330-GlnMetLeuGlnLys-334 |
| SEQ. ID. NO. 8525 | 357-PheThrIlePheGluGlyProAsn-364 |
| SEQ. ID. NO. 8526 | 366-MetLeuTyrAlaGluIleTyrAspGlnPheValArgAla-378 |
| SEQ. ID. NO. 8527 | 397-AspArgLeuGlnThr-401 |
| SEQ. ID. NO. 8528 | 414-LeuProGluAspIleArgSerPhe-421 |
| SEQ. ID. NO. 8529 | 439-GlyLysIleIleAlaArgLeu-445 |
| Antigenic Index - Jameson-Wolf | |
| SEQ. ID. NO. 8530 | 3-HisThrGluProSerAlaGlnProSerThrMetAsp-14 |
| SEQ. ID. NO. 8531 | 22-IleGluSerAlaPhe-26 |
| SEQ. ID. NO. 8532 | 29-IlePheSerAspGlyIleAsp-35 |
| SEQ. ID. NO. 8533 | 40-LeuProGluAspLysTrpLeu-46 |
| SEQ. ID. NO. 8534 | 57-PheLeuAspLysLysTyrGlyGlyArgLysGlySerGlnPheGluIle-72 |
| SEQ. ID. NO. 8535 | 103-GluPheGlyAspGluAlaGlnVal-110 |
| SEQ. ID. NO. 8536 | 118-PheLysGlyGluGlyGlyGlyLeuGly-126 |
| SEQ. ID. NO. 8537 | 128-ThrGluProGluThrSerGly-134 |
| SEQ. ID. NO. 8538 | 136-AlaIleAlaArgGluMetGlnSer-143 |
| SEQ. ID. NO. 8539 | 145-TyrGluTyrIleAspGlyGlnThr-152 |
| SEQ. ID. NO. 8540 | 160-TyrTrpGlnGlyAsnSerGlnSerAspPhe-169 |
| SEQ. ID. NO. 8541 | 174-AlaLysGluArgLysAsnGlyLysLeuAlaLys-184 |
| SEQ. ID. NO. 8542 | 193-LysThrTyrIleArg-197 |
| SEQ. ID. NO. 8543 | 199-GluThrLeuAlaSerGluGlyLeuArg-207 |
| SEQ. ID. NO. 8544 | 212-AlaValAsnArgIleAspAlaGluMet-220 |
| SEQ. ID. NO. 8545 | 228-LeuSerGlnSerAspAlaAlaGly-235 |
| SEQ. ID. NO. 8546 | 264-AsnLeuGluArgTyrValArgAsnAspIleLysPheValAspTyrGluArgArgGluIleArgArgHisGlnVal-289 |
| SEQ. ID. NO. 8547 | 339-LysGlyPheGluArgGlyHisThrAlaGlyAsn-349 |
| SEQ. ID. NO. 8548 | 361-GluGlyProAsnAspMetLeu-367 |
| SEQ. ID. NO. 8549 | 378-AlaThrAlaGluGluLysGluAlaGlyMetLysLeuAspLysAsnGlnThrLeuLeuAspArgLeuGlnThrAspAlaArgPhe-405 |
| SEQ. ID. NO. 8550 | 407-AlaValAlaArgAspTyrThrLeuProGluAspIleArgSerPheLeu-422 |

TABLE 1-continued

| | |
|---|---|
| SEQ. ID. NO. 8551 | 451-AlaLysHisGluAspThrAla-457 |
| SEQ. ID. NO. 8552 | 463-AspIleArgLysAspIleLeuAspCysArgTyrCysGly-475 |

Hydrophilic Regions - Hopp-Woods

| | |
|---|---|
| SEQ. ID. NO. 8553 | 22-IleGluSerAlaPhe-26 |
| SEQ. ID. NO. 8554 | 29-IlePheSerAspGlyIleAsp-35 |
| SEQ. ID. NO. 8555 | 40-LeuProGluAspLysTrpLeu-46 |
| SEQ. ID. NO. 8556 | 58-LeuAspLysLysTyrGlyGlyArgLysGlySerGln-69 |
| SEQ. ID. NO. 8557 | 103-GluPheGlyAspGluAlaGlnVal-110 |
| SEQ. ID. NO. 8558 | 118-PheLysGlyGluGlyGly-123 |
| SEQ. ID. NO. 8559 | 128-ThrGluProGluThrSerGly-134 |
| SEQ. ID. NO. 8560 | 136-AlaIleAlaArgGluMetGlnSer-143 |
| SEQ. ID. NO. 8561 | 174-AlaLysGluArgLysAsnGlyLysLeuAlaLys-184 |
| SEQ. ID. NO. 8562 | 212-AlaValAsnArgIleAspAlaGluMet-220 |
| SEQ. ID. NO. 8563 | 229-SerGlnSerAspAlaAlaGly-235 |
| SEQ. ID. NO. 8564 | 264-AsnLeuGluArgTyrValArgAsnAspIleLysPheValAspTyrGluArgArgGluIleArgArgArgHisGlnVal-289 |
| SEQ. ID. NO. 8565 | 339-LysGlyPheGluArgGlyHisThr-346 |
| SEQ. ID. NO. 8566 | 378-AlaThrAlaGluGluLysGluAlaGlyMetLysLeuAspLysAsnGlnThrLeuLeuAspArgLeuGlnThrAspAlaArgPhe-405 |
| SEQ. ID. NO. 8567 | 416-GluAspIleArgSerPheLeu-422 |
| SEQ. ID. NO. 8568 | 451-AlaLysHisGluAspThrAla-457 |
| SEQ. ID. NO. 8569 | 463-AspIleArgLysAspIleLeuAsp-470 |

645-2
AMPHI Regions - AMPHI

| | |
|---|---|
| SEQ. ID. NO. 8570 | 21-AsnThrLeuAsnArgCysCysLys-28 |
| SEQ. ID. NO. 8571 | 87-ArgThrLeuProSerLeuLysGlyLeuThrLys-97 |

Antigenic Index - Jameson-Wolf

| | |
|---|---|
| SEQ. ID. NO. 8572 | 17-ValGluGlnSerAsnThrLeuAsnArgCysCysLysLysSerArgMetThrCysSerSerSerArgSerArgSerCysProCys-44 |
| SEQ. ID. NO. 8573 | 47-ProMetArgAlaSerGlySerArgValSerSerArgSerArgIle-61 |
| SEQ. ID. NO. 8574 | 68-SerLeuCysArgLysAsnThrCysProProArgLeuSerSerArgAsnThrAlaSerArgThrLeuProSerLeu-92 |
| SEQ. ID. NO. 8575 | 99-LeuThrAlaArgArgArgLeuGly-106 |
| SEQ. ID. NO. 8576 | 110-IleSerGluLysSerArgSerProSerAsn-119 |
| SEQ. ID. NO. 8577 | 137-ThrLeuAlaArgArgArgLeuSerCysSer-146 |

Hydrophilic Regions - Hopp-Woods

| | |
|---|---|
| SEQ. ID. NO. 8578 | 19-GlnSerAsnThrLeu-23 |
| SEQ. ID. NO. 8579 | 25-ArgCysCysLysLysSerArgMetThrCysSerSerSerArgSerArgSerCysPro-43 |
| SEQ. ID. NO. 8580 | 48-MetArgAlaSerGlySerArgValSerSerArgSerArgIle-61 |
| SEQ. ID. NO. 8581 | 69-LeuCysArgLysAsnThrCys-75 |
| SEQ. ID. NO. 8582 | 77-ProArgLeuSerSerArgAsnThrAlaSerArgThr-88 |
| SEQ. ID. NO. 8583 | 99-LeuThrAlaArgArgArgLeuGly-106 |
| SEQ. ID. NO. 8584 | 110-IleSerGluLysSerArgSerProSer-118 |
| SEQ. ID. NO. 8585 | 137-ThrLeuAlaArgArgArgLeuSer-144 |

647
AMPHI Regions - AMPHI

| | |
|---|---|
| SEQ. ID. NO. 8586 | 38-GlyLysValCysArgCysPheGluGlnVal-47 |
| SEQ. ID. NO. 8587 | 69-ThrValPheArgGlnIleIleSerIleVal-78 |

Antigenic Index - Jameson-Wolf

| | |
|---|---|
| SEQ. ID. NO. 8588 | 26-GlyLeuValLysGluArgAlaArg-33 |
| SEQ. ID. NO. 8589 | 39-LysValCysArgCysPhe-44 |
| SEQ. ID. NO. 8590 | 54-GlyThrValGlyGlnThrGluArgGlyThr-63 |
| SEQ. ID. NO. 8591 | 81-AlaAspAlaGluArgThrAlaAlaHisSerArgGlyThrArgGly-95 |

Hydrophilic Regions - Hopp-Woods

| | |
|---|---|
| SEQ. ID. NO. 8592 | 26-GlyLeuValLysGluArgAlaArg-33 |
| SEQ. ID. NO. 8593 | 56-ValGlyGlnThrGluArgGlyThr-63 |
| SEQ. ID. NO. 8594 | 81-AlaAspAlaGluArgThrAlaAlaHisSerArgGlyThrArgGly-95 |

648
AMPHI Regions - AMPHI

| | |
|---|---|
| SEQ. ID. NO. 8595 | 7-ArgIleGluArgAlaValArg-13 |
| SEQ. ID. NO. 8596 | 15-AlaValIleAspValLeuAsnValAsp-23 |
| SEQ. ID. NO. 8597 | 44-AlaLeuAlaAspIleArgValLeu-51 |
| SEQ. ID. NO. 8598 | 94-AlaValAspLeuHisAlaValIleLysLeuThrAspThr-106 |
| SEQ. ID. NO. 8599 | 127-GlnGlyValGluGlnGly-132 |
| SEQ. ID. NO. 8600 | 147-ArgArgLeuLysHisPheLysGluGlyAsnAlaAlaGlyMetProArgPhe-163 |
| SEQ. ID. NO. 8601 | 182-AlaArgThrLeuGlyAsnValPheHis-190 |
| SEQ. ID. NO. 8602 | 194-GlySerGlyIleAspGlyIleGlnThrIleValAlaPheAsnGlnHisThr-210 |

Antigenic Index - Jameson-Wolf

| | |
|---|---|
| SEQ. ID. NO. 8603 | 1-MetAsnArgArgAspAlaArgIleGluArgAlaValArg-13 |
| SEQ. ID. NO. 8604 | 23-AspAlaProGlySerGlyThrLeuLeuHisGlnArgGlyLysGlnValGlySerArgAsnAspAlaLeuAla-46 |
| SEQ. ID. NO. 8605 | 65-GlyLysLysArgPheValGlnSerArgAsnLeuValGlyArgLysGlnArgAsn-82 |
| SEQ. ID. NO. 8606 | 125-MetProGlnGlyValGluGlnGlyCysArgAla-135 |
| SEQ. ID. NO. 8607 | 143-ThrGlyPheAspArgArgLeuLysHisPheLysGluGlyAsnAla-157 |
| SEQ. ID. NO. 8608 | 172-ThrAlaAspThrSerGlyIleAspAlaAspAlaArgThr-184 |
| SEQ. ID. NO. 8609 | 191-AsnArgAlaGlySerGlyIleAspGly-199 |

Hydrophilic Regions - Hopp-Woods

| | |
|---|---|
| SEQ. ID. NO. 8610 | 1-MetAsnArgArgAspAlaArgIleGluArgAlaValArg-13 |
| SEQ. ID. NO. 8611 | 33-GlnArgGlyLysGlnValGlySerArgAsnAspAlaLeuAla-46 |
| SEQ. ID. NO. 8612 | 65-GlyLysLysArgPheValGln-71 |
| SEQ. ID. NO. 8613 | 74-AsnLeuValGlyArgLysGlnArgAsn-82 |
| SEQ. ID. NO. 8614 | 127-GlnGlyValGluGlnGlyCysArgAla-135 |
| SEQ. ID. NO. 8615 | 143-ThrGlyPheAspArgArgLeuLysHisPheLysGluGlyAsnAla-157 |
| SEQ. ID. NO. 8616 | 173-AlaAspThrSerGlyIleAspAlaAspAlaArgThr-184 |

TABLE 1-continued 649-2
AMPHI Regions - AMPHI
SEQ. ID. NO. 8617  8-AlaIleLeuLeuSerAlaIleLeuGlyLeuVal-18
SEQ. ID. NO. 8618  32-ArgAspThrLysHisIleArgLysAlaAsn-41
SEQ. ID. NO. 8619  62-SerGlnGlyAsnVal-66
SEQ. ID. NO. 8620  68-GluLeuArgGluAsnLys-73
SEQ. ID. NO. 8621  76-ArgLysAlaPheArgSerLeuPro-83
Antigenic Index - Jameson-Wolf
SEQ. ID. NO. 8622  1-MetSerValLysLys-5
SEQ. ID. NO. 8623  25-GlyThrSerGluProAlaHisArgAspThrLysHisIleArgLysAlaAsnLys-42
SEQ. ID. NO. 8624  45-LeuHisProGluCysArgLysTyrLeuGluArgArgAlaAla-58
SEQ. ID. NO. 8625  61-ArgSerGlnGlyAsnValGlnGluLeuArgGluAsnLysLysAlaArgLysAlaPheArg-80
SEQ. ID. NO. 8626  85-AlaGluGlnLysIleGlnCys-91
SEQ. ID. NO. 8627  97-AlaPheAspAspPheAspGlyGlySerPheArgArg-108
Hydrophilic Regions - Hopp-Woods
SEQ. ID. NO. 8628  1-MetSerValLysLys-5
SEQ. ID. NO. 8629  25-GlyThrSerGluProAlaHisArgAspThrLysHisIleArgLysAlaAsnLys-42
SEQ. ID. NO. 8630  47-ProGluCysArgLysTyrLeuGluArgArgAlaAla-58
SEQ. ID. NO. 8631  64-GlyAsnValGlnGluLeuArgGluAsnLysLysAlaArgLysAlaPheArg-80
SEQ. ID. NO. 8632  85-AlaGluGlnLysIleGlnCys-91
SEQ. ID. NO. 8633  97-AlaPheAspAspPheAspGlyGlySerPheArgArg-108
650-2
AMPHI Regions - AMPHI
SEQ. ID. NO. 8634  15-SerValCysProGly-19
SEQ. ID. NO. 8635  57-LeuTrpGlyGluLeuArgGln-63
SEQ. ID. NO. 8636  72-ProGluLeuValArgArgHisGlu-79
SEQ. ID. NO. 8637  89-PheAsnArgValIleAsn-94
SEQ. ID. NO. 8638  137-SerGlyLeuTrpGln-141
SEQ. ID. NO. 8639  173-AsnTyrLeuGlnTyrLeuTyrGlyLeuPheGlyAspTrpPro-186
SEQ. ID. NO. 8640  198-AsnValGlyArgAlaIleAsnArgAlaArg-207
SEQ. ID. NO. 8641  218-LeuArgMetProAsnGluThr-224
SEQ. ID. NO. 8642  269-GluAlaIleAlaArgLeuAlaGlyIleThrGlnSer-280
SEQ. ID. NO. 8643  314-SerAsnTyrLeuAsnAlaAlaProAsp-322
SEQ. ID. NO. 8644  341-IleSerThrAlaThrGlyMet-347
SEQ. ID. NO. 8645  349-IleAlaAspIleLysArgLeuAsnAsnLeu-358
SEQ. ID. NO. 8646  376-LysThrLeuGlnThrAlaSerGlu-383
SEQ. ID. NO. 8647  484-AlaAspGluLeuMetGln-489
SEQ. ID. NO. 8648  496-LeuArgArgGlnAlaGlu-501
SEQ. ID. NO. 8649  503-ThrIleSerAlaValIleGlyThrProAspThrValAlaGlu-516
SEQ. ID. NO. 8650  556-AlaSerIleHisArgValVal-562
SEQ. ID. NO. 8651  621-AspThrPheLysSerIle-626
SEQ. ID. NO. 8652  636-AspIleArgArgLeu-640
Antigenic Index - Jameson-Wolf
SEQ. ID. NO. 8653  1-MetSerLysLeuLys-5
SEQ. ID. NO. 8654  24-GlnAsnThrSerSerHis-29
SEQ. ID. NO. 8655  38-LeuAsnSerSerIleLeuAspLeuProProThrLysGlnTyrPhe-52
SEQ. ID. NO. 8656  59-GlyGluLeuArgGlnGlyPheArgMetGlyGluValAsnProGluLeuValArgArgHisGluSerLysPhe-82
SEQ. ID. NO. 8657  92-ValIleAsnArgSerArgProTyr-99
SEQ. ID. NO. 8658  105-AsnGluValLysLysArgAsnMetProAla-114
SEQ. ID. NO. 8659  128-ThrLysAlaLysSerHisValGlyAlaSerGly-138
SEQ. ID. NO. 8660  145-AlaThrGlyArgHisTyrGlyLeuGluLysThrProValTyrAspGlyArgHisAspVal-164
SEQ. ID. NO. 8661  192-TyrAsnTrpGlyGluGlyAsnValGlyArgAlaIleAsnArgAlaArgAlaGlnGlyLeuGluProThrTyrGluAsnLeuArgMetProAsnGluThr
ArgAsnTyrVal-228
SEQ. ID. NO. 8662  247-AsnIleSerAspIleAspAsnLysProTyr-256
SEQ. ID. NO. 8663  259-AlaValGluProAspArgProLeuAspAsnGluAlaIleAla-272
SEQ. ID. NO. 8664  296-ProLysSerLysArgLysLeu-302
SEQ. ID. NO. 8665  318-AsnAlaAlaProAspSer-323
SEQ. ID. NO. 8666  332-ProAlaAlaLysThrSerLeuSerAspIleSerThr-343
SEQ. ID. NO. 8667  350-AlaAspIleLysArgLeuAsnAsnLeuAsnGly-360
SEQ. ID. NO. 8668  370-LeuValAlaLysAsnGlyLysThrLeuGlnThrAlaSer-382
SEQ. ID. NO. 8669  388-IleAspIleAspAsnThrProAspThrTyrArgSerAsnMetProAla-403
SEQ. ID. NO. 8670  411-AlaArgIleArgPro-415
SEQ. ID. NO. 8671  428-LeuProGlnLysThrValArgThrGluProAspProLeuValArgIleAlaGlu-445
SEQ. ID. NO. 8672  454-GlnProGlnThrGluLysGlnThrAlaMetProSerGluThrGln-468
SEQ. ID. NO. 8673  477-ProGlnAsnAspMetGlnAlaAlaAspGluLeu-487
SEQ. ID. NO. 8674  491-ValAlaArgAsnAsnLeuArgArgGlnAlaGluGluThrIle-504
SEQ. ID. NO. 8675  509-GlyThrProAspThrValAlaGluHisLysIleSerAlaSerProGln-524
SEQ. ID. NO. 8676  527-AlaAlaAlaAspGlyLysArgArgValArgLeuGluThrArgValAlaLysAlaAlaAspGlyGluAlaGluIle-551
SEQ. ID. NO. 8677  560-ArgValValGluGlyAspThr-566
SEQ. ID. NO. 8678  583-ValAlaAsnAsnIleLysGlyAsnThrIleGlnLysGlyGlnValLeuArg-599
SEQ. ID. NO. 8679  606-AlaGlnThrArgIleGluLysValSerTyrThrAlaArgLysGlyAspThrPheLys-624
SEQ. ID. NO. 8680  634-IleAspAspIleArgArgLeuAsnProAsnLeu-644
SEQ. ID. NO. 8681  647-IleAsnProGlyGlnArgValLysLeu-655
Hydrophilic Regions - Hopp-Woods
SEQ. ID. NO. 8682  1-MetSerLysLeuLys-5
SEQ. ID. NO. 8683  61-LeuArgGlnGlyPheArgMetGlyGluValAsnProGluLeuValArgArgHisGluSerLysPhe-82
SEQ. ID. NO. 8684  92-ValIleAsnArgSerArgPro-98
SEQ. ID. NO. 8685  105-AsnGluValLysLysArgAsnMetProAla-114
SEQ. ID. NO. 8686  128-ThrLysAlaLysSerHisVal-134
SEQ. ID. NO. 8687  150-TyrGlyLeuGluLys-154

TABLE 1-continued

| | |
|---|---|
| SEQ. ID. NO. 8688 | 156-ProValTyrAspGlyArgHisAspVal-164 |
| SEQ. ID. NO. 8689 | 202-AlaIleAsnArgAlaArgAlaGlnGlyLeu-211 |
| SEQ. ID. NO. 8690 | 213-ProThrTyrGluAsnLeuArgMetProAsnGluThrArgAsnTyrVal-228 |
| SEQ. ID. NO. 8691 | 249-SerAspIleAspAsn-253 |
| SEQ. ID. NO. 8692 | 260-ValGluProAspArgProLeuAspAsnGluAlaIleAla-272 |
| SEQ. ID. NO. 8693 | 296-ProLysSerLysArgLysLeu-302 |
| SEQ. ID. NO. 8694 | 334-AlaLysThrSerLeu-338 |
| SEQ. ID. NO. 8695 | 350-AlaAspIleLysArgLeuAsn-356 |
| SEQ. ID. NO. 8696 | 373-LysAsnGlyLysThrLeuGlnThrAlaSer-382 |
| SEQ. ID. NO. 8697 | 389-AspIleAspAsnThrProAspThrTyrArg-398 |
| SEQ. ID. NO. 8698 | 411-AlaArgIleArgPro-415 |
| SEQ. ID. NO. 8699 | 431-LysThrValArgThrGluProAspProLeuValArgIleAlaGlu-445 |
| SEQ. ID. NO. 8700 | 455-ProGlnThrGluLysGlnThrAlaMetProSerGluThrGln-468 |
| SEQ. ID. NO. 8701 | 479-AsnAspMetGlnAlaAlaAspGluLeu-487 |
| SEQ. ID. NO. 8702 | 494-AsnAsnLeuArgArgGlnAlaGluGluThrIle-504 |
| SEQ. ID. NO. 8703 | 512-AspThrValAlaGluHisLysIleSerAla-521 |
| SEQ. ID. NO. 8704 | 527-AlaAlaAlaAspGlyLysArgArgValArgLeuGluThrArgValAlaLysAlaAlaAspGlyGluAlaGluIle-551 |
| SEQ. ID. NO. 8705 | 560-ArgValValGluGly-564 |
| SEQ. ID. NO. 8706 | 608-ThrArgIleGluLysValSerTyrThrAlaArgLysGlyAspThrPheLys-624 |
| SEQ. ID. NO. 8707 | 634-IleAspAspIleArgArgLeuAsn-641 |
| SEQ. ID. NO. 8708 | 649-ProGlyGlnArgValLysLeu-655 |

652-1
AMPHI Regions - AMPHI

| | |
|---|---|
| SEQ. ID. NO. 8709 | 6-AspIlePheAlaArg-10 |
| SEQ. ID. NO. 8710 | 52-ArgAspGlyAspLys-56 |
| SEQ. ID. NO. 8711 | 62-LysGlyValLeuLysAlaValGluHisValAsnAsnGlnIleAlaGlnAla-78 |
| SEQ. ID. NO. 8712 | 130-LeuTyrArgTyrLeuGlyGlyAlaGlyPro-139 |
| SEQ. ID. NO. 8713 | 149-ValIleAsnGlyGly-153 |
| SEQ. ID. NO. 8714 | 173-LysSerPheArgGluAlaLeuArgCys-181 |
| SEQ. ID. NO. 8715 | 184-GluIlePheHisAlaLeuLysLys-191 |
| SEQ. ID. NO. 8716 | 266-AlaGluPheAlaGluTyrLeuGluGlyLeuValAsn-277 |
| SEQ. ID. NO. 8717 | 323-AlaGluGlyIleGluLysGlyVal-330 |
| SEQ. ID. NO. 8718 | 338-ValAsnGlnIleGlyThrLeuSerGluThrLeuLysAlaValAspLeuAlaLys-355 |
| SEQ. ID. NO. 8719 | 377-AspLeuAlaValAla-381 |
| SEQ. ID. NO. 8720 | 391-SerLeuSerArgSerAspArgMetAlaLysTyrAsnGlnLeuLeuArgIleGluGlu-409 |
| SEQ. ID. NO. 8721 | 411-LeuAlaGluAlaAlaAspTyr-417 |

Antigenic Index - Jameson-Wolf

| | |
|---|---|
| SEQ. ID. NO. 8722 | 11-GluIleLeuAspSerArgGlyAsnProThrValGlu-22 |
| SEQ. ID. NO. 8723 | 36-AlaValProSerGlyAlaSerThrGlyGlnLysGluAlaLeuGluLeuArgAspGlyAspLysSerArgTyrSerGlyLysGlyValLeuLysAlaValGluHisValAsn-72 |
| SEQ. ID. NO. 8724 | 83-AspAlaAsnGluGlnSerTyr-89 |
| SEQ. ID. NO. 8725 | 97-LeuAspGlyThrGluAsnLysGlyAsnLeuGly-107 |
| SEQ. ID. NO. 8726 | 121-AlaAlaAlaGluAspSerGlyLeuPro-129 |
| SEQ. ID. NO. 8727 | 135-GlyGlyAlaGlyProMet-140 |
| SEQ. ID. NO. 8728 | 151-AsnGlyGlyGluHisAlaAsnAsnSer-159 |
| SEQ. ID. NO. 8729 | 173-LysSerPheArgGluAlaLeuArgCysGlyAla-183 |
| SEQ. ID. NO. 8730 | 190-LysLysLeuCysAspSerLysGlyPheProThrValGlyAspGluGlyGlyPhe-208 |
| SEQ. ID. NO. 8731 | 211-AsnLeuAsnSerHisLysGluAlaLeu-219 |
| SEQ. ID. NO. 8732 | 243-CysAlaSerSerGluPheTyrLysAspGlyLysTyrHisLeuGluAlaGluGlyArgSerTyrThrAsn-265 |
| SEQ. ID. NO. 8733 | 283-SerIleGluAspGlyMetAspGluAsnAspTrpGluGly-295 |
| SEQ. ID. NO. 8734 | 299-LeuThrGluLysLeuGlyGlyArgValGlnLeuValGlyAspAspLeu-314 |
| SEQ. ID. NO. 8735 | 318-AsnProLysIleLeuAlaGluGlyIleGluLysGlyVal-330 |
| SEQ. ID. NO. 8736 | 352-AspLeuAlaLysArgAsnArgTyrAla-360 |
| SEQ. ID. NO. 8737 | 363-MetSerHisArgSerGlyGluThrGluAspSerThrIle-375 |
| SEQ. ID. NO. 8738 | 388-LysThrGlySerLeuSerArgSerAspArgMetAlaLys-400 |
| SEQ. ID. NO. 8739 | 405-LeuArgIleGluGluGluLeuAlaGluAlaAlaAspTyrProSerLys-420 |

Hydrophilic Regions - Hopp-Woods

| | |
|---|---|
| SEQ. ID. NO. 8740 | 11-GluIleLeuAspSerArgGlyAsnProThrValGlu-22 |
| SEQ. ID. NO. 8741 | 43-ThrGlyGlnLysGluAlaLeuGluLeuArgAspGlyAspLysSerArgTyrSerGly-61 |
| SEQ. ID. NO. 8742 | 63-GlyValLeuLysAlaValGlu-69 |
| SEQ. ID. NO. 8743 | 97-LeuAspGlyThrGluAsnLysGlyAsnLeu-106 |
| SEQ. ID. NO. 8744 | 121-AlaAlaAlaGluAspSerGly-127 |
| SEQ. ID. NO. 8745 | 153-GlyGluHisAlaAsn-157 |
| SEQ. ID. NO. 8746 | 173-LysSerPheArgGluAlaLeuArgCysGlyAla-183 |
| SEQ. ID. NO. 8747 | 190-LysLysLeuCysAspSerLysGly-197 |
| SEQ. ID. NO. 8748 | 202-ValGlyAspGluGlyGlyPhe-208 |
| SEQ. ID. NO. 8749 | 213-AsnSerHisLysGluAlaLeu-219 |
| SEQ. ID. NO. 8750 | 247-GluPheTyrLysAspGlyLysTyrHisLeuGluAlaGluGlyArgSerTyrThr-264 |
| SEQ. ID. NO. 8751 | 283-SerIleGluAspGlyMetAspGluAsnAspTrpGluGly-295 |
| SEQ. ID. NO. 8752 | 299-LeuThrGluLysLeuGlyGly-305 |
| SEQ. ID. NO. 8753 | 321-IleLeuAlaGluGlyIleGluLysGlyVal-330 |
| SEQ. ID. NO. 8754 | 352-AspLeuAlaLysArgAsnArgTyr-359 |
| SEQ. ID. NO. 8755 | 364-SerHisArgSerGlyGluThrGluAspSerThrIle-375 |
| SEQ. ID. NO. 8756 | 391-SerLeuSerArgSerAspArgMetAlaLys-400 |
| SEQ. ID. NO. 8757 | 405-LeuArgIleGluGluGluLeuAlaGluAlaAlaAspTyrProSer-419 |

653
AMPHI Regions - AMPHI

| | |
|---|---|
| SEQ. ID. NO. 8758 | 6-MetArgMetProGluValThrLysGlyPheSerGlySer-18 |
| SEQ. ID. NO. 8759 | 60-ThrMetArgLysProArgLeuThr-67 |
| SEQ. ID. NO. 8760 | 75-AlaLeuIlePheThrCysPheAla-82 |

TABLE 1-continued

```
SEQ. ID. NO. 8761      96-ThrAlaLeuAlaAlaIleThrCysIle-104
SEQ. ID. NO. 8762      111-LeuGlyLysMetGluGluPheAsn-118
Antigenic Index - Jameson-Wolf
SEQ. ID. NO. 8763      4-GluProMetArgMetProGluValThrLysGlyPheSerGlySer-18
SEQ. ID. NO. 8764      45-GlyCysArgSerThrArgLysThr-52
SEQ. ID. NO. 8765      56-ValArgProGluThrMetArgLysProArgLeuThrAsnSerSerAla-71
SEQ. ID. NO. 8766      86-AsnSerGlyCysAsnAla-91
SEQ. ID. NO. 8767      103-CysIleSerGlyProProCysArgLeuGlyLysMetGluGlu-116
SEQ. ID. NO. 8768      125-SerArgHisLysIleThrProProArgGlyProArgArgVal-138
SEQ. ID. NO. 8769      145-ThrLysSerGlnAsnGlyThrGly-152
SEQ. ID. NO. 8770      154-GlyTyrSerProProAlaThrArgProAla-163
Hydrophilic Regions - Hopp-Woods
SEQ. ID. NO. 8771      4-GluProMetArgMetProGluValThrLys-13
SEQ. ID. NO. 8772      47-ArgSerThrArgLysThr-52
SEQ. ID. NO. 8773      57-ArgProGluThrMetArgLysProArgLeuThrAsn-68
SEQ. ID. NO. 8774      107-ProProCysArgLeuGlyLysMetGluGlu-116
SEQ. ID. NO. 8775      126-ArgHisLysIleThrProProArgGlyProArg-136
SEQ. ID. NO. 8776      158-ProAlaThrArgProAla-163
656
AMPHI Regions - AMPHI
SEQ. ID. NO. 8777      14-MetAlaArgThrLeuGlyAlaProGlu-22
SEQ. ID. NO. 8778      42-ArgArgProSerThr-46
SEQ. ID. NO. 8779      92-LeuAlaSerLeuAsnLysSerCys-99
SEQ. ID. NO. 8780      117-MetGlyArgThrIleThr-122
Antigenic Index - Jameson-Wolf
SEQ. ID. NO. 8781      6-GlySerThrSerSer-10
SEQ. ID. NO. 8782      19-GlyAlaProGluSerValProAlaGlyLysValAlaAla-31
SEQ. ID. NO. 8783      40-SerPheArgArgProSerThrLeuGlu-48
SEQ. ID. NO. 8784      74-ArgProThrSerLeuArgProLysSerIleAsn-84
SEQ. ID. NO. 8785      94-SerLeuAsnLysSerCysSerLeuAlaArgSerSerAlaGlyValLeuProArgArgArgValProAla-116
SEQ. ID. NO. 8786      122-ThrSerLeuArgSerArgArgThrArgIleSerGlyGluGluProThrMetTrpLysSerProLysSer-144
Hydrophilic Regions - Hopp-Woods
SEQ. ID. NO. 8787      40-SerPheArgArgProSerThr-46
SEQ. ID. NO. 8788      76-ThrSerLeuArgProLysSerIle-83
SEQ. ID. NO. 8789      99-CysSerLeuAlaArgSerSer-105
SEQ. ID. NO. 8790      109-LeuProArgArgArgValProAla-116
SEQ. ID. NO. 8791      124-LeuArgSerArgArgThrArgIleSerGlyGluGluProThrMet-138
SEQ. ID. NO. 8792      140-LysSerProLysSer-144
657
AMPHI Regions - AMPHI
SEQ. ID. NO. 8793      9-ProAlaMetLeuGly-13
SEQ. ID. NO. 8794      20-LeuGlyArgMetPheThr-25
SEQ. ID. NO. 8795      62-AlaAlaLeuAspGluLeuAlaLysCysAlaAla-72
SEQ. ID. NO. 8796      85-MetArgPheLeuAlaLys-90
SEQ. ID. NO. 8797      132-AspIleThrGluAlaSer-137
SEQ. ID. NO. 8798      139-GlnPheLeuProGlyIleLeuLysThr-147
SEQ. ID. NO. 8799      161-LysThrLeuAspGluLeuLysAlaAla-169
SEQ. ID. NO. 8800      178-CysValLeuGluLysMetValAspLeu-186
SEQ. ID. NO. 8801      203-GlnThrPheAspProAlaGluAsnIle-211
SEQ. ID. NO. 8802      232-GlnGlnAlaArgGlnMetAlaGlnArgLeuAlaAspGluLeuAspTyrValGlyValLeu-251
SEQ. ID. NO. 8803      314-AsnIleLeuGlyAsp-318
Antigenic Index - Jameson-Wolf
SEQ. ID. NO. 8804      16-GlyGlyGlyGlnLeuGly-21
SEQ. ID. NO. 8805      37-ValLeuAspProAspProAspAlaProAla-46
SEQ. ID. NO. 8806      62-AlaAlaLeuAspGluLeuAlaLys-69
SEQ. ID. NO. 8807      75-ThrGluPheGluAsnValAsnAlaAspAla-84
SEQ. ID. NO. 8808      91-HisThrAsnValSerProSerGlyAsp-99
SEQ. ID. NO. 8809      106-AsnArgIleGlnGluGlyLysAlaTrpIle-114
SEQ. ID. NO. 8810      128-CysLysAlaGluAspIleThrGluAla-136
SEQ. ID. NO. 8811      150-LeuGlyTyrAspGlyLysGlyGlnIleArgValLysThrLeuAspGluLeuLysAlaAlaPhe-170
SEQ. ID. NO. 8812      182-LysMetValAspLeuArgSerGluIle-190
SEQ. ID. NO. 8813      197-LeuAsnAsnAspAsnValGlnThrPheAspProAlaGluAsnIleHisGluAsnGly-215
SEQ. ID. NO. 8814      230-ValGlnGlnAlaArgGlnMetAla-238
SEQ. ID. NO. 8815      240-ArgLeuAlaAspGluLeuAsp-246
SEQ. ID. NO. 8816      269-IleAlaProArgProHisAsnSerGlyHisHis-279
SEQ. ID. NO. 8817      288-GlnPheGlnGlnGln-292
SEQ. ID. NO. 8818      300-ProProAlaAspThrLysLeuLeuSer-308
SEQ. ID. NO. 8819      319-ValTrpGlnGluAspGlyGlyGluProAspTrp-329
SEQ. ID. NO. 8820      333-GlnSerHisProAsnAla-338
SEQ. ID. NO. 8821      344-GlyLysLysThrAlaHisLysGlyArgLysMetGly-355
SEQ. ID. NO. 8822      361-ThrThrAspSerAspThrAlaPheGlnGluAlaLysLysLeuHis-375
Hydrophilic Regions - Hopp-Woods
SEQ. ID. NO. 8823      37-ValLeuAspProAspProAspAlaProAla-46
SEQ. ID. NO. 8824      62-AlaAlaLeuAspGluLeuAlaLys-69
SEQ. ID. NO. 8825      75-ThrGluPheGluAsnValAsn-81
SEQ. ID. NO. 8826      128-CysLysAlaGluAspIleThrGluAla-136
SEQ. ID. NO. 8827      152-TyrAspGlyLysGlyGlnIleArgValLysThrLeuAspGluLeuLysAlaAlaPhe-170
SEQ. ID. NO. 8828      182-LysMetValAspLeuArgSerGluIle-190
SEQ. ID. NO. 8829      197-LeuAsnAsnAspAsn-201
SEQ. ID. NO. 8830      206-AspProAlaGluAsnIleHis-212
```

TABLE 1-continued

| | |
|---|---|
| SEQ. ID. NO. 8831 | 230-ValGlnGlnGlnAlaArgGlnMetAla-238 |
| SEQ. ID. NO. 8832 | 240-ArgLeuAlaAspGluLeuAsp-246 |
| SEQ. ID. NO. 8833 | 269-IleAlaProArgProHisAsn-275 |
| SEQ. ID. NO. 8834 | 301-ProAlaAspThrLysLeu-306 |
| SEQ. ID. NO. 8835 | 320-TrpGlnGluAspGlyGlyGluProAsp-328 |
| SEQ. ID. NO. 8836 | 344-GlyLysLysThrAlaHisLysGlyArgLysMetGly-355 |
| SEQ. ID. NO. 8837 | 362-ThrAspSerAspThrAlaPheGlnGluAlaLysLysLeuHis-375 |

658
AMPHI Regions - AMPHI

| | |
|---|---|
| SEQ. ID. NO. 8838 | 28-ArgGlnTyrAlaAspIleIleGlnPheValArgGlnAlaLeuArgHisLeuProArgLeuLeuLeu-49 |
| SEQ. ID. NO. 8839 | 68-ValAspValPheGlyArgValGluSer-76 |
| SEQ. ID. NO. 8840 | 92-ThrAlaGlnIleHisHisPhePheGlnAsnAlaIleHisAla-105 |
| SEQ. ID. NO. 8841 | 139-GlnLysLeuArgAlaCysPheSerAspValPheSer-150 |

Antigenic Index - Jameson-Wolf

| | |
|---|---|
| SEQ. ID. NO. 8842 | 6-ValArgAlaArgGlyAspPheValAspAspGlnPheMetArgValThrAspAsnLysHisPhe-26 |
| SEQ. ID. NO. 8843 | 40-AlaLeuArgHisLeuPro-45 |
| SEQ. ID. NO. 8844 | 53-ThrGlnSerArgGlyAspAspGlyIleSerGlnAspAlaVal-66 |
| SEQ. ID. NO. 8845 | 72-GlyArgValGluSer-76 |
| SEQ. ID. NO. 8846 | 107-ValPheGlyLysArgGlyPheGlu-114 |
| SEQ. ID. NO. 8847 | 130-GlnArgSerArgPheGlnAspAlaGlyGlnLysLeuArgAlaCysPhe-145 |
| SEQ. ID. NO. 8848 | 155-LeuIleArgArgGlyLeuGlnSerArgPhe-164 |
| SEQ. ID. NO. 8849 | 177-AsnArgHisThrIleAlaAlaArgGlyAsnIle-187 |
| SEQ. ID. NO. 8850 | 193-LysAlaHisArgIleGly-198 |
| SEQ. ID. NO. 8851 | 202-PheLysPheSerGlyHisArgArgAla-210 |
| SEQ. ID. NO. 8852 | 219-LeuValValLysArgArgAlaGln-226 |
| SEQ. ID. NO. 8853 | 230-GlyLysPheCysCysArgArgValArgIleGlyValGluAsn-243 |
| SEQ. ID. NO. 8854 | 250-GlyPheGlyGlyAsnGlyLysHisSerAla-259 |

Hydrophilic Regions - Hopp-Woods

| | |
|---|---|
| SEQ. ID. NO. 8855 | 6-ValArgAlaArgGlyAspPheValAsp-14 |
| SEQ. ID. NO. 8856 | 16-GlnPheMetArgValThrAspAsnLysHisPhe-26 |
| SEQ. ID. NO. 8857 | 53-ThrGlnSerArgGlyAspAspGlyIleSer-62 |
| SEQ. ID. NO. 8858 | 72-GlyArgValGluSer-76 |
| SEQ. ID. NO. 8859 | 130-GlnArgSerArgPheGlnAspAlaGlyGlnLysLeuArgAlaCysPhe-145 |
| SEQ. ID. NO. 8860 | 155-LeuIleArgArgGlyLeuGln-161 |
| SEQ. ID. NO. 8861 | 193-LysAlaHisArgIleGly-198 |
| SEQ. ID. NO. 8862 | 205-SerGlyHisArgArgAla-210 |
| SEQ. ID. NO. 8863 | 220-ValValLysArgArgAlaGln-226 |
| SEQ. ID. NO. 8864 | 233-CysCysArgArgValArgIleGlyVal-241 |
| SEQ. ID. NO. 8865 | 253-GlyAsnGlyLysHisSerAla-259 |

661-2
AMPHI Regions - AMPHI

| | |
|---|---|
| SEQ. ID. NO. 8866 | 19-GlyIleThrAspLysProPheArgArgLeuCysArgAspPheGlyAlaGly-35 |
| SEQ. ID. NO. 8867 | 37-AlaValCysGluMetLeu-42 |
| SEQ. ID. NO. 8868 | 75-AspProGlnGlnMetAlaAspAlaAla-83 |
| SEQ. ID. NO. 8869 | 122-AlaAlaIleLeuGluAlaValValArg-130 |
| SEQ. ID. NO. 8870 | 152-ProValIleAlaLysIleAlaGlu-159 |
| SEQ. ID. NO. 8871 | 256-AlaAlaAlaIleLeuAsnHisIleArgAlaIleHisAlaPheTyrGly-271 |
| SEQ. ID. NO. 8872 | 297-ArgArgGluIleAsnArgLeuAspSer-305 |
| SEQ. ID. NO. 8873 | 310-TyrAspMetLeuAlaGlyTyrLeuGluArgLeuAlaGluLys-323 |

Antigenic Index - Jameson-Wolf

| | |
|---|---|
| SEQ. ID. NO. 8874 | 20-IleThrAspLysProPheArgArgLeuCysArgAspPheGlyAlaGly-35 |
| SEQ. ID. NO. 8875 | 42-LeuThrSerAspProThrLeuArgAsnThrArgLysThrLeuHisArgSerAspPheAlaAspGluGlyGly-65 |
| SEQ. ID. NO. 8876 | 72-AlaGlySerAspProGlnGlnMetAlaAspAlaAlaArg-84 |
| SEQ. ID. NO. 8877 | 97-AsnMetGlyCysProAlaLysLysValCys-106 |
| SEQ. ID. NO. 8878 | 143-GlyTrpHisAspAspHisGlnAsnLeu-151 |
| SEQ. ID. NO. 8879 | 157-IleAlaGluAspCysGly-162 |
| SEQ. ID. NO. 8880 | 169-HisGlyArgThrArgThrGlnMetTyrLysGlyGluAlaArgTyr-183 |
| SEQ. ID. NO. 8881 | 187-AlaGluThrLysCysArgLeu-193 |
| SEQ. ID. NO. 8882 | 200-AsnGlyAspIleThrSerProGlnLysAla-209 |
| SEQ. ID. NO. 8883 | 222-MetIleGlyArgGlyAlaGlnGlyArgProTrpPhe-233 |
| SEQ. ID. NO. 8884 | 236-AspLeuLysHisTyrAla-241 |
| SEQ. ID. NO. 8885 | 270-TyrGlyAspThrAlaGly-275 |
| SEQ. ID. NO. 8886 | 277-ArgIleAlaArgLysHis-282 |
| SEQ. ID. NO. 8887 | 288-AspGluMetProAspGlyGluGlnThrArgArgGluIleAsnArgLeuAspSerAla-306 |
| SEQ. ID. NO. 8888 | 319-ArgLeuAlaGluLysThrAspSerTrp-327 |
| SEQ. ID. NO. 8889 | 330-AlaTyrArgProAsnAla-335 |

Hydrophilic Regions - Hopp-Woods

| | |
|---|---|
| SEQ. ID. NO. 8890 | 20-IleThrAspLysProPheArgArgLeuCysArgAspPhe-32 |
| SEQ. ID. NO. 8891 | 46-ProThrLeuArgAsnThrArgLysThrLeuHisArgSerAspPheAlaAspGluGlyGly-65 |
| SEQ. ID. NO. 8892 | 73-GlySerAspProGlnGlnMetAlaAspAlaAlaArg-84 |
| SEQ. ID. NO. 8893 | 100-CysProAlaLysLysValCys-106 |
| SEQ. ID. NO. 8894 | 157-IleAlaGluAspCysGly-162 |
| SEQ. ID. NO. 8895 | 170-GlyArgThrArgThrGlnMetTyrLysGlyGluAlaArgTyr-183 |
| SEQ. ID. NO. 8896 | 187-AlaGluThrLysCysArgLeu-193 |
| SEQ. ID. NO. 8897 | 203-IleThrSerProGlnLysAla-209 |
| SEQ. ID. NO. 8898 | 236-AspLeuLysHisTyrAla-241 |
| SEQ. ID. NO. 8899 | 277-ArgIleAlaArgLys-281 |
| SEQ. ID. NO. 8900 | 289-GluMetProAspGlyGluGlnThrArgArgGluIleAsnArgLeuAspSerAla-306 |
| SEQ. ID. NO. 8901 | 319-ArgLeuAlaGluLysThrAspSer-326 |

TABLE 1-continued

```
663
AMPHI Regions - AMPHI
SEQ. ID. NO. 8902        19-ProPheAlaLeuLeuHisLysIleAlaAspLeuThrGlyLeuLeuAlaTyr-35
SEQ. ID. NO. 8903        47-IleAsnLeuAlaLysCysPheSerGluTrp-56
SEQ. ID. NO. 8904        66-LysGlnHisPheLysHisMetAlaLysLeu-75
SEQ. ID. NO. 8905        87-AlaGlyArgLeuLysSerLeuValArg-95
SEQ. ID. NO. 8906        168-GluGlyLeuArgAlaLeuValLysGlnPheArgLys-179
SEQ. ID. NO. 8907        209-ThrIleThrGlyLeuSerArgIleAlaAlaLeuAlaAsn-221
SEQ. ID. NO. 8908        243-ProAlaTrpLysSer-247
SEQ. ID. NO. 8909        258-GlnArgMetAsnArgPheIleGluAspArgValArgGluHis-271
Antigenic Index - Jameson-Wolf
SEQ. ID. NO. 8910        38-ValLysProArgArgArgIleGlyGlu-46
SEQ. ID. NO. 8911        56-TrpSerGluGluLysArgLysThrValLeu-65
SEQ. ID. NO. 8912        87-AlaGlyArgLeuLysSer-92
SEQ. ID. NO. 8913        94-ValArgTyrArgAsnLysHisTyrLeuAsp-103
SEQ. ID. NO. 8914        105-AlaLeuAlaAlaGlyGluLys-111
SEQ. ID. NO. 8915        139-TyrSerHisGlnLysAsnLysIleLeuAsp-148
SEQ. ID. NO. 8916        150-GlnIleLeuLysGlyArgAsnArgTyr-158
SEQ. ID. NO. 8917        166-ArgThrGluGlyLeuArgAlaLeu-173
SEQ. ID. NO. 8918        175-LysGlnPheArgLysSerSerAla-182
SEQ. ID. NO. 8919        188-ProAspGlnAspPheGlyArgAsnAspSerVal-198
SEQ. ID. NO. 8920        229-ProValArgGluAlaAspAsnThr-236
SEQ. ID. NO. 8921        243-ProAlaTrpLysSerPheProGlyGluAspAlaLysAlaAspAlaGlnArgMetAsnArgPheIleGluAspArgValArgGluHisProGlu-273
SEQ. ID. NO. 8922        280-LysArgPheLysThrArgProGluGlySerProAspPheTyr-293
Hydrophilic Regions - Hopp-Woods
SEQ. ID. NO. 8923        39-LysProArgArgArgIleGlyGlu-46
SEQ. ID. NO. 8924        56-TrpSerGluGluLysArgLysThrValLeu-65
SEQ. ID. NO. 8925        88-GlyArgLeuLysSer-92
SEQ. ID. NO. 8926        94-ValArgTyrArgAsn-98
SEQ. ID. NO. 8927        105-AlaLeuAlaAlaGlyGluLys-111
SEQ. ID. NO. 8928        142-GlnLysAsnLysIleLeuAsp-148
SEQ. ID. NO. 8929        150-GlnIleLeuLysGlyArgAsnArgTyr-158
SEQ. ID. NO. 8930        166-ArgThrGluGlyLeuArgAlaLeu-173
SEQ. ID. NO. 8931        176-GlnPheArgLysSerSer-181
SEQ. ID. NO. 8932        190-GlnAspPheGlyArgAsnAspSerVal-198
SEQ. ID. NO. 8933        229-ProValArgGluAlaAspAsn-235
SEQ. ID. NO. 8934        248-PheProGlyGluAspAlaLysAlaAspAlaGlnArgMetAsnArgPheIleGluAspArgValArgGluHisProGlu-273
SEQ. ID. NO. 8935        280-LysArgPheLysThrArgProGluGlySerPro-290
664-2
AMPHI Regions - AMPHI
SEQ. ID. NO. 8936        47-AlaAspValPheAspAlaAlaHisGlyAlaAlaGly-58
SEQ. ID. NO. 8937        90-ProValValGluIle-94
SEQ. ID. NO. 8938        158-PheHisArgValPheGlnArgPhe-165
SEQ. ID. NO. 8939        201-AlaArgAspGlnSerLysGlnIleAlaArgPheGlyLysArg-214
Antigenic Index - Jameson-Wolf
SEQ. ID. NO. 8940        27-GlyAlaHisArgMetGlyGlyArgAlaCysVal-37
SEQ. ID. NO. 8941        73-PheLeuGlnArgLysLeuGluPro-80
SEQ. ID. NO. 8942        108-IleGlyGlyGlyAlaAlaValGlyLysAspGluLeuGlyValLysAspValGln-125
SEQ. ID. NO. 8943        137-AlaHisGlyAspAspHisGluAsn-144
SEQ. ID. NO. 8944        165-PheHisGlyLysAlaAspLeuGly-172
SEQ. ID. NO. 8945        177-GlyGlyValLysLeuAspPhe-183
SEQ. ID. NO. 8946        199-GlnIleAlaArgAspGlnSerLysGlnIleAlaArgPheGlyLysArgValPhe-216
Hydrophilic Regions - Hopp-Woods
SEQ. ID. NO. 8947        28-AlaHisArgMetGlyGly-33
SEQ. ID. NO. 8948        74-LeuGlnArgLysLeuGluPro-80
SEQ. ID. NO. 8949        113-AlaValGlyLysAspGluLeuGlyValLysAspValGln-125
SEQ. ID. NO. 8950        137-AlaHisGlyAspAspHisGluAsn-144
SEQ. ID. NO. 8951        165-PheHisGlyLysAlaAspLeuGly-172
SEQ. ID. NO. 8952        177-GlyGlyValLysLeuAspPhe-183
SEQ. ID. NO. 8953        199-GlnIleAlaArgAspGlnSerLysGlnIleAlaArgPheGlyLys-213
665-1
Hydrophilic Regions - Hopp-Woods
SEQ. ID. NO. 8954        39-LysProArgArgArgIleGlyGlu-46
SEQ. ID. NO. 8955        56-TrpSerGluGluLysArgLysThrValLeu-65
SEQ. ID. NO. 8956        88-GlyArgLeuLysSer-92
SEQ. ID. NO. 8957        94-ValArgTyrArgAsn-98
SEQ. ID. NO. 8958        105-AlaLeuAlaAlaGlyGluLys-111
SEQ. ID. NO. 8959        142-GlnLysAsnLysIleLeuAsp-148
SEQ. ID. NO. 8960        150-GlnIleLeuLysGlyArgAsnArgTyr-158
SEQ. ID. NO. 8961        166-ArgThrGluGlyLeuArgAlaLeu-173
SEQ. ID. NO. 8962        176-GlnPheArgLysSerSer-181
SEQ. ID. NO. 8963        190-GlnAspPheGlyArgAsnAspSerVal-198
SEQ. ID. NO. 8964        229-ProValArgGluAlaAspAsn-235
SEQ. ID. NO. 8965        248-PheProGlyGluAspAlaLysAlaAspAlaGlnArgMetAsnArgPheIleGluAspArgValArgGluHisProGlu-273
SEQ. ID. NO. 8966        280-LysArgPheLysThrArgProGluGlySerPro-290
Antigenic Index - Jameson-Wolf
SEQ. ID. NO. 8967        8-LeuLysAspTyrGlnThrProAlaTyr-16
SEQ. ID. NO. 8968        26-AspIleAsnGluPro-30
SEQ. ID. NO. 8969        32-ThrValValLysSerArgLeuThrValGluProGlnArgValGlyGlu-47
SEQ. ID. NO. 8970        49-LeuValLeuAspGlySerAla-55
```

TABLE 1-continued

| SEQ. ID. NO. | Sequence |
|---|---|
| SEQ. ID. NO. 8971 | 80-GlyValProSerGluArgPheThrVal-88 |
| SEQ. ID. NO. 8972 | 90-ValGluThrGluIleLeuProAlaGluAsnLysSerLeu-102 |
| SEQ. ID. NO. 8973 | 115-GlnCysGluProGluGlyPheArgLys-123 |
| SEQ. ID. NO. 8974 | 128-IleAspArgProAspValMetSer-135 |
| SEQ. ID. NO. 8975 | 142-ValAlaAspLysLysArgTyrPro-149 |
| SEQ. ID. NO. 8976 | 153-SerAsnGlyAsnLysIleAspGlyGlyGluPheSerAspGlyArgHisTrpValLysTrpGluAspProPheSerLysProSer-180 |
| SEQ. ID. NO. 8977 | 191-AlaValThrGluAspTyr-196 |
| SEQ. ID. NO. 8978 | 200-MetSerGlyArgAsnValLysIle-207 |
| SEQ. ID. NO. 8979 | 211-ThrThrGluAlaAspLysProLysVal-219 |
| SEQ. ID. NO. 8980 | 230-MetLysTrpAspGluThrArgPhe-237 |
| SEQ. ID. NO. 8981 | 255-AsnMetGlyAlaMetGluAsnLysGlyLeu-264 |
| SEQ. ID. NO. 8982 | 275-AspSerArgThrAlaThrAspThrAspPheGluGlyIleGlu-288 |
| SEQ. ID. NO. 8983 | 295-TyrPheHisAsnTrpThrGlyAsnArgValThrCysArgAspTrp-309 |
| SEQ. ID. NO. 8984 | 313-SerLeuLysGluGly-317 |
| SEQ. ID. NO. 8985 | 322-ArgAspGlnGluPheSerGlyAspArgAlaSerArgAlaValArgArgIleGluAsn-340 |
| SEQ. ID. NO. 8986 | 347-HisGlnPheProGluAspAlaGlyProThrAlaHisProValArgProAlaSerTyrGluGluMetAsn-369 |
| SEQ. ID. NO. 8987 | 376-ValTyrGluLysGlyAlaGluVal-383 |
| SEQ. ID. NO. 8988 | 394-GluGlyPheGlnLysGlyMet-400 |
| SEQ. ID. NO. 8989 | 404-PheGlnArgHisAspGlyGlnAlaValThrCysAspAspPheArgAlaAlaMet-421 |
| SEQ. ID. NO. 8990 | 437-SerGlnAlaGlyThrPro-442 |
| SEQ. ID. NO. 8991 | 444-LeuGluAlaGluGlyArgLeuLysAsnAsnIle-454 |
| SEQ. ID. NO. 8992 | 459-ValLysGlnThrValProProThrProAspMetThrAspLysGlnPro-474 |
| SEQ. ID. NO. 8993 | 483-LeuLeuAsnArgAsnGlyGluAlaVal-491 |
| SEQ. ID. NO. 8994 | 494-AspTyrGlnGlyLysArgAlaThrGlu-502 |
| SEQ. ID. NO. 8995 | 537-LeuAsnTyrProTyrSerAspAspAspLeu-546 |
| SEQ. ID. NO. 8996 | 552-HisAspSerAspAla-556 |
| SEQ. ID. NO. 8997 | 578-LeuSerAspGlyValGluLeuProLysHisGluLysLeu-590 |
| SEQ. ID. NO. 8998 | 594-ValGluLysValIleSerAspAspLeuLeu-603 |
| SEQ. ID. NO. 8999 | 614-ValProSerGluAlaGluLeuTrpAspGlyAlaGluAsnIleAspProLeuArg-631 |
| SEQ. ID. NO. 9000 | 633-HisGlnAlaArgGluAlaLeu-639 |
| SEQ. ID. NO. 9001 | 652-HisGluLeuAsnArgGlnAlaAlaLysGlnGluAsnGlnSerTyrGluTyrSerProGluAlaAlaGly-674 |
| SEQ. ID. NO. 9002 | 677-ThrLeuArgAsnValCys-682 |
| SEQ. ID. NO. 9003 | 689-AlaAspProAlaHis-693 |
| SEQ. ID. NO. 9004 | 696-ThrValAlaGluLysTyrGlyGlu-703 |
| SEQ. ID. NO. 9005 | 719-AsnGlyAsnGluSerAspThrArgAsnArgLeu-729 |
| SEQ. ID. NO. 9006 | 733-PheAlaAspLysPheSerAspAspAlaLeuVal-743 |
| SEQ. ID. NO. 9007 | 752-GlySerSerArgArgSerAspThrLeuGlnGlnVal-763 |
| SEQ. ID. NO. 9008 | 768-GlnHisProLysPheSerLeuGluAsnProAsnLysAlaArgSer-782 |
| SEQ. ID. NO. 9009 | 785-GlySerPheSerArgAsnValPro-792 |
| SEQ. ID. NO. 9010 | 795-HisAlaGluAspGlySerGlyTyrArgPheIleAla-806 |
| SEQ. ID. NO. 9011 | 808-LysValIleGluIleAspArgPheAsnProGlnVal-819 |
| SEQ. ID. NO. 9012 | 831-AsnLysLeuGluProHisArgLysAsnLeuVal-841 |
| SEQ. ID. NO. 9013 | 844-AlaLeuGlnArgIleArgAlaGlnGluGlyLeuSerLysAspValGlyGluIleVal-862 |
| Hydrophilic Regions - Hopp-Woods | |
| SEQ. ID. NO. 9014 | 32-ThrValValLysSerArgLeuThrValGluProGlnArgValGlyGlu-47 |
| SEQ. ID. NO. 9015 | 82-ProSerGluArgPheThrVal-88 |
| SEQ. ID. NO. 9016 | 90-ValGluThrGluIleLeuProAlaGluAsnLysSer-101 |
| SEQ. ID. NO. 9017 | 116-CysGluProGluGlyPheArg-122 |
| SEQ. ID. NO. 9018 | 129-AspArgProAspValMetSer-135 |
| SEQ. ID. NO. 9019 | 142-ValAlaAspLysLysArgTyr-148 |
| SEQ. ID. NO. 9020 | 154-AsnGlyAsnLysIleAspGlyGlyGluPheSerAsp-165 |
| SEQ. ID. NO. 9021 | 170-ValLysTrpGluAspProPheSer-177 |
| SEQ. ID. NO. 9022 | 201-SerGlyArgAsnValLys-206 |
| SEQ. ID. NO. 9023 | 213-GluAlaAspLysProLysVal-219 |
| SEQ. ID. NO. 9024 | 230-MetLysTrpAspGluThrArgPhe-237 |
| SEQ. ID. NO. 9025 | 258-AlaMetGluAsnLysGly-263 |
| SEQ. ID. NO. 9026 | 275-AspSerArgThrAlaThrAspThrAspPheGluGlyIleGlu-288 |
| SEQ. ID. NO. 9027 | 313-SerLeuLysGluGly-317 |
| SEQ. ID. NO. 9028 | 322-ArgAspGlnGluPheSerGlyAspArgAlaSerArgAlaValArgArgIleGluAsn-340 |
| SEQ. ID. NO. 9029 | 348-GlnPheProGluAspAlaGlyPro-355 |
| SEQ. ID. NO. 9030 | 363-AlaSerTyrGluGluMetAsn-369 |
| SEQ. ID. NO. 9031 | 376-ValTyrGluLysGlyAlaGluVal-383 |
| SEQ. ID. NO. 9032 | 394-GluGlyPheGlnLysGlyMet-400 |
| SEQ. ID. NO. 9033 | 406-ArgHisAspGlyGln-410 |
| SEQ. ID. NO. 9034 | 413-ThrCysAspAspPheArgAlaAlaMet-421 |
| SEQ. ID. NO. 9035 | 444-LeuGluAlaGluGlyArgLeuLysAsnAsnIle-454 |
| SEQ. ID. NO. 9036 | 467-ProAspMetThrAspLysGlnPro-474 |
| SEQ. ID. NO. 9037 | 495-TyrGlnGlyLysArgAlaThrGlu-502 |
| SEQ. ID. NO. 9038 | 541-TyrSerAspAspAspLeu-546 |
| SEQ. ID. NO. 9039 | 552-HisAspSerAspAla-556 |
| SEQ. ID. NO. 9040 | 580-AspGlyValGluLeuProLysHisGluLysLeu-590 |
| SEQ. ID. NO. 9041 | 594-ValGluLysValIleSer-599 |
| SEQ. ID. NO. 9042 | 616-SerGluAlaGluLeu-620 |
| SEQ. ID. NO. 9043 | 622-AspGlyAlaGluAsnIleAspPro-629 |
| SEQ. ID. NO. 9044 | 633-HisGlnAlaArgGluAlaLeu-639 |
| SEQ. ID. NO. 9045 | 652-HisGluLeuAsnArgGlnAlaAlaLysGlnGluAsnGlnSer-665 |
| SEQ. ID. NO. 9046 | 689-AlaAspProAlaHis-693 |
| SEQ. ID. NO. 9047 | 696-ThrValAlaGluLysTyrGlyGlu-703 |
| SEQ. ID. NO. 9048 | 719-AsnGlyAsnGluSerAspThrArgAsnArgLeu-729 |
| SEQ. ID. NO. 9049 | 733-PheAlaAspLysPheSerAsp-739 |

TABLE 1-continued

| | |
|---|---|
| SEQ. ID. NO. 9050 | 753-SerSerArgArgSerAspThr-759 |
| SEQ. ID. NO. 9051 | 776-AsnProAsnLysAlaArgSer-782 |
| SEQ. ID. NO. 9052 | 795-HisAlaGluAspGlySerGly-801 |
| SEQ. ID. NO. 9053 | 808-LysValIleGluIleAspArgPheAsn-816 |
| SEQ. ID. NO. 9054 | 831-AsnLysLeuGluProHisArgLysAsnLeuVal-841 |
| SEQ. ID. NO. 9055 | 844-AlaLeuGlnArgIleArgAlaGlnGluGlyLeuSerLysAspValGlyGluIleVal-862 |
| 666-2 | |
| AMPHI Regions - AMPHI | |
| SEQ. ID. NO. 9056 | 89-GlyTyrAspIleLeuLysGlnGlyGlySer-98 |
| SEQ. ID. NO. 9057 | 162-LeuLysPheMetGluAla-167 |
| SEQ. ID. NO. 9058 | 177-ProAlaIleProLysLeuMetGluThrIleHisGln-188 |
| SEQ. ID. NO. 9059 | 193-LeuProTrpGlyLysLeuPheAspThrProIleArg-204 |
| SEQ. ID. NO. 9060 | 227-LeuAlaArgTyrProLys-232 |
| SEQ. ID. NO. 9061 | 249-LeuLeuLysAsnLeuGluPheAlaAspSerValGlnAlaLeu-262 |
| SEQ. ID. NO. 9062 | 265-GlnGlyAlaLysAlaLeuHisThr-272 |
| SEQ. ID. NO. 9063 | 274-LysTyrAlaGlnAsnIleValSerValVal-283 |
| SEQ. ID. NO. 9064 | 295-LeuGlnAspLeuSerAspTyrGln-302 |
| SEQ. ID. NO. 9065 | 313-TyrArgIleTyrGluValCysGlyMetGly-322 |
| SEQ. ID. NO. 9066 | 332-GlyGlnIleLeuGlyIleLeuAsnGluPheSer-342 |
| SEQ. ID. NO. 9067 | 353-LeuArgLeuLeuGlyAsp-358 |
| SEQ. ID. NO. 9068 | 411-AspPheIleHisGluTrp-416 |
| SEQ. ID. NO. 9069 | 424-LeuProSerThrSerHis-429 |
| SEQ. ID. NO. 9070 | 433-ValAspLysAlaGlyAsn-438 |
| SEQ. ID. NO. 9071 | 441-SerMetThrThrSerIleGluAsnAlaPheGlySer-452 |
| SEQ. ID. NO. 9072 | 511-ProGlyGlySerArgIleIleGlyTyrValAlaLys-522 |
| SEQ. ID. NO. 9073 | 537-AlaIleSerAlaProAsnLeuLeuAsnArgPheGly-548 |
| SEQ. ID. NO. 9074 | 562-GlnGlnAlaLeuAsnAsp-567 |
| SEQ. ID. NO. 9075 | 590-ArgLeuValGlyGly-594 |
| Antigenic Index - Jameson-Wolf | |
| SEQ. ID. NO. 9076 | 5-AsnHisGlnSerAsnSerGlyGluGlyValLeu-15 |
| SEQ. ID. NO. 9077 | 40-AsnGlnGlyLysValAsnThr-46 |
| SEQ. ID. NO. 9078 | 54-AlaAspAlaHisThrProGluHisAlaThr-63 |
| SEQ. ID. NO. 9079 | 65-LeuThrGluGlnLysGln-70 |
| SEQ. ID. NO. 9080 | 92-IleLeuLysGlnGlyGlySerAlaAla-100 |
| SEQ. ID. NO. 9081 | 114-GluProGlnSerSerGlyLeuGlyGly-122 |
| SEQ. ID. NO. 9082 | 130-AspAsnThrAlaLysThr-135 |
| SEQ. ID. NO. 9083 | 137-ThrThrPheAspGlyArgGluThrAlaPro-146 |
| SEQ. ID. NO. 9084 | 154-PheLeuAspLysAspGlyGlnPro-161 |
| SEQ. ID. NO. 9085 | 169-ValGlyGlyArgSerValGly-175 |
| SEQ. ID. NO. 9086 | 197-LysLeuPheAspThrProIleArgLeuAlaLysGlnGlyPhe-210 |
| SEQ. ID. NO. 9087 | 212-ValSerProArgLeu-216 |
| SEQ. ID. NO. 9088 | 221-GluGlnAsnGlnGlnHis-226 |
| SEQ. ID. NO. 9089 | 228-AlaArgTyrProLysThrAlaAla-235 |
| SEQ. ID. NO. 9090 | 271-HisThrGlyLysTyr-275 |
| SEQ. ID. NO. 9091 | 284-GlnAsnAlaLysAspAsnProGlyGln-292 |
| SEQ. ID. NO. 9092 | 296-GlnAspLeuSerAspTyrGlnValValGluArgProProValCys-310 |
| SEQ. ID. NO. 9093 | 320-GlyMetGlyAlaProSerSerGlyGly-328 |
| SEQ. ID. NO. 9094 | 340-GluPheSerProAsnGlnValGlyTyrAspAlaGluGlyLeuArgLeuLeuGlyAspAlaSerArg-361 |
| SEQ. ID. NO. 9095 | 363-AlaPheAlaAspArgAspValTyrLeuGlyAspProAspPheVal-377 |
| SEQ. ID. NO. 9096 | 384-LeuIleSerLysAspTyrLeuLysHisArgSerGlnLeuLeuGluGlnSerAspLysAlaLeu-404 |
| SEQ. ID. NO. 9097 | 431-SerIleValAspLysAlaGly-437 |
| SEQ. ID. NO. 9098 | 445-SerIleGluAsnAlaPhe-450 |
| SEQ. ID. NO. 9099 | 472-ProIleLysGlnGlyLysGlnValAlaAsnArgValGluProGlyLysArgProArgSerSerMet-493 |
| SEQ. ID. NO. 9100 | 500-LysAlaGlyLysProTyrMet-506 |
| SEQ. ID. NO. 9101 | 510-SerProGlyGlySerArgIle-516 |
| SEQ. ID. NO. 9102 | 548-GlySerTyrGluLeuGluThrGlyThr-556 |
| SEQ. ID. NO. 9103 | 566-AsnAspLeuGlyTyrLysThrAspValArgGluLeuAsnSerGlyVal-581 |
| SEQ. ID. NO. 9104 | 587-GluProSerArgLeuValGlyGlyAlaAspProArgArgGluGlyArgValMetGlyAsp-606 |
| Hydrophilic Regions - Hopp-Woods | |
| SEQ. ID. NO. 9105 | 8-SerAsnSerGlyGlu-12 |
| SEQ. ID. NO. 9106 | 40-AsnGlnGlyLysValAsnThr-46 |
| SEQ. ID. NO. 9107 | 55-AspAlaHisThrProGluHis-61 |
| SEQ. ID. NO. 9108 | 65-LeuThrGluGlnLysGln-70 |
| SEQ. ID. NO. 9109 | 96-GlyGlySerAlaAla-100 |
| SEQ. ID. NO. 9110 | 139-PheAspGlyArgGluThrAlaPro-146 |
| SEQ. ID. NO. 9111 | 154-PheLeuAspLysAspGlyGlnPro-161 |
| SEQ. ID. NO. 9112 | 203-IleArgLeuAlaLysGlnGlyPhe-210 |
| SEQ. ID. NO. 9113 | 284-GlnAsnAlaLysAspAsnProGly-291 |
| SEQ. ID. NO. 9114 | 302-GlnValValGluArgProPro-308 |
| SEQ. ID. NO. 9115 | 348-TyrAspAlaGluGlyLeuArgLeuLeuGlyAspAlaSerArg-361 |
| SEQ. ID. NO. 9116 | 363-AlaPheAlaAspArgAspValTyrLeuGly-372 |
| SEQ. ID. NO. 9117 | 388-AspTyrLeuLysHisArgSerGlnLeuLeuGluGlnSerAspLysAlaLeu-404 |
| SEQ. ID. NO. 9118 | 432-IleValAspLysAlaGly-437 |
| SEQ. ID. NO. 9119 | 472-ProIleLysGlnGlyLysGlnValAlaAsnArgValGluProGlyLysArgProArgSerSerMet-493 |
| SEQ. ID. NO. 9120 | 572-ThrAspValArgGluLeuAsnSer-579 |
| SEQ. ID. NO. 9121 | 595-AlaAspProArgArgGluGlyArgValMetGlyAsp-606 |
| 667-2 | |
| AMPHI Regions - AMPHI | |
| SEQ. ID. NO. 9122 | 6-GlyLeuCysGlyGlnValIlePro-13 |
| SEQ. ID. NO. 9123 | 48-IleIleAlaAspPheLeuGlnProAlaArg-57 |

TABLE 1-continued

| | |
|---|---|
| SEQ. ID. NO. 9124 | 59-GluCysLeuProAsnLeuAlaAla-66 |
| SEQ. ID. NO. 9125 | 74-LysThrAlaGlnPhe-78 |
| SEQ. ID. NO. 9126 | 115-IleAlaAlaValAlaGluIle-121 |
| SEQ. ID. NO. 9127 | 153-ThrAspGlnLeuArgArgMetPhePheAsnGlnPheGluLysPheSerAsnAspHis-171 |
| SEQ. ID. NO. 9128 | 202-LysMetMetLeuHisLys-207 |
| SEQ. ID. NO. 9129 | 234-ValGlnCysSerAspThr-239 |

Antigenic Index - Jameson-Wolf

| | |
|---|---|
| SEQ. ID. NO. 9130 | 27-ProAlaAlaAspGlnThrGluThrGln-35 |
| SEQ. ID. NO. 9131 | 56-AlaArgMetGluCysLeuPro-62 |
| SEQ. ID. NO. 9132 | 71-LeuAlaArgLysThrAlaGln-77 |
| SEQ. ID. NO. 9133 | 89-ArgLeuValLysArgGluGlnIle-96 |
| SEQ. ID. NO. 9134 | 152-ProThrAspGlnLeuArg-157 |
| SEQ. ID. NO. 9135 | 165-GluLysPheSerAsn-169 |
| SEQ. ID. NO. 9136 | 190-ProThrHisAlaAlaArgAsnArgHisAsnLeu-200 |
| SEQ. ID. NO. 9137 | 226-ValGlyGlnArgGlyArgGlnLeu-233 |
| SEQ. ID. NO. 9138 | 248-IleGluSerGlnAsnArgGlyHisAspSer-257 |

Hydrophilic Regions - Hopp-Woods

| | |
|---|---|
| SEQ. ID. NO. 9139 | 27-ProAlaAlaAspGlnThrGluThrGln-35 |
| SEQ. ID. NO. 9140 | 56-AlaArgMetGluCys-60 |
| SEQ. ID. NO. 9141 | 71-LeuAlaArgLysThrAlaGln-77 |
| SEQ. ID. NO. 9142 | 89-ArgLeuValLysArgGluGlnIle-96 |
| SEQ. ID. NO. 9143 | 165-GluLysPheSerAsn-169 |
| SEQ. ID. NO. 9144 | 192-HisAlaAlaArgOAsnArgHisAsnLeu-200 |
| SEQ. ID. NO. 9145 | 228-GlnArgGlyArgGln-232 |
| SEQ. ID. NO. 9146 | 250-SerGlnAsnArgGlyHisAsp-256 |

669-2
AMPHI Regions - AMPHI

| | |
|---|---|
| SEQ. ID. NO. 9147 | 24-PheLeuGlyIleLysArgPhePheArgGlnPro-34 |
| SEQ. ID. NO. 9148 | 60-LysLeuHisArgAlaPhe-65 |
| SEQ. ID. NO. 9149 | 95-GlnIlePheArgHisValGlnSer-102 |
| SEQ. ID. NO. 9150 | 119-ThrArgGlnAlaPhe-123 |

Antigenic Index - Jameson-Wolf

| | |
|---|---|
| SEQ. ID. NO. 9151 | 5-ArgLeuGlnAsnGlyArgThrGlyArgAsnProProPheValGlnLysArgLeuAsp-23 |
| SEQ. ID. NO. 9152 | 29-ArgPhePheArgGlnProLeuGluMetArgArgIleIleLysLysHisGlnProIleAsnAla-49 |
| SEQ. ID. NO. 9153 | 69-GlyArgLysArgProHisHisHisAspSerSerLeuArgArgGlnHisGlyIleGluGlyMetGlyPhe-91 |
| SEQ. ID. NO. 9154 | 99-HisValGlnSerSerAsnArgGlnAsnGlyArgGlnProVal-112 |
| SEQ. ID. NO. 9155 | 114-AlaProAsnArgGlnThrArgGlnAlaPhe-123 |
| SEQ. ID. NO. 9156 | 137-ProThrSerAsnGlyTyrCys-143 |
| SEQ. ID. NO. 9157 | 149-SerThrHisArgThrThrHisLysAlaProProTyr-160 |

Hydrophilic Regions - Hopp-Woods

| | |
|---|---|
| SEQ. ID. NO. 9158 | 7-GlnAsnGlyArgThrGlyArgAsn-14 |
| SEQ. ID. NO. 9159 | 18-ValGlnLysArgLeuAsp-23 |
| SEQ. ID. NO. 9160 | 34-ProLeuGluMetArgArgIleIleLysLysHisGlnPro-46 |
| SEQ. ID. NO. 9161 | 69-GlyArgLysArgProHisHisHisAspSerSerLeuArgArgGlnHisGly-85 |
| SEQ. ID. NO. 9162 | 101-GlnSerSerAsnArgGlnAsnGlyArg-109 |
| SEQ. ID. NO. 9163 | 116-AsnArgGlnThrArgGlnAlaPhe-123 |
| SEQ. ID. NO. 9164 | 151-HisArgThrThrHisLys-156 |

670-2
AMPHI Regions - AMPHI

| | |
|---|---|
| SEQ. ID. NO. 9165 | 10-ArgSerCysPheGly-14 |
| SEQ. ID. NO. 9166 | 16-ValLysAsnAlaSerGlyValSer-23 |
| SEQ. ID. NO. 9167 | 34-IleThrArgSerAla-38 |
| SEQ. ID. NO. 9168 | 77-ValGlySerSerAsnAsnIle-83 |

Antigenic Index - Jameson-Wolf

| | |
|---|---|
| SEQ. ID. NO. 9169 | 4-CysArgAsnCysLeuAlaArgSerCys-12 |
| SEQ. ID. NO. 9170 | 18-AsnAlaSerGlyValSerSerSerArgIleCysProLeuSer-31 |
| SEQ. ID. NO. 9171 | 33-LysIleThrArgSerAlaThrSerArgAlaAsnProIle-45 |
| SEQ. ID. NO. 9172 | 65-AsnThrSerProThrIleSerGlySerSerAlaGluValGlySerSerAsnAsnIleThrArgGlySerIleAlaLysProArgAlaIleAla-95 |
| SEQ. ID. NO. 9173 | 98-CysCysTrpProProGluSerTrpGluGlyLysAla-109 |
| SEQ. ID. NO. 9174 | 114-AlaSerProThrArgSerLysSerSer-122 |
| SEQ. ID. NO. 9175 | 128-AlaCysSerAlaPhe-132 |

Hydrophilic Regions - Hopp-Woods

| | |
|---|---|
| SEQ. ID. NO. 9176 | 33-LysIleThrArgSerAlaThrSerArgAlaAsn-43 |
| SEQ. ID. NO. 9177 | 73-SerSerAlaGluValGlySer-79 |
| SEQ. ID. NO. 9178 | 87-SerIleAlaLysProArgAlaIleAla-95 |
| SEQ. ID. NO. 9179 | 116-ProThrArgSerLysSer-121 |

671
AMPHI Regions - AMPHI

| | |
|---|---|
| SEQ. ID. NO. 9180 | 11-PheAsnAlaProAsn-15 |
| SEQ. ID. NO. 9181 | 72-LysGluAlaAlaLysSerLeu-78 |
| SEQ. ID. NO. 9182 | 96-ThrProArgIleAla-100 |
| SEQ. ID. NO. 9183 | 119-ArgLeuPheIleArgTyr-124 |

Antigenic Index - Jameson-Wolf

| | |
|---|---|
| SEQ. ID. NO. 9184 | 9-ThrProPheAsnAlaProAsnThrProProLysMetArgLeuAlaLysProLysProThrAlaGlu-30 |
| SEQ. ID. NO. 9185 | 45-GlnAlaMetThrAsnArgGluMetAsnAspArgAlaAsnAlaAsnArgArgGlyTrpAsnGluAlaLysAlaArgSerAlaLysGluAlaAlaLysSerLeuAlaLysLysLysGluThrThr-85 |
| SEQ. ID. NO. 9186 | 98-ArgIleAlaAspSerThrMet-104 |
| SEQ. ID. NO. 9187 | 110-AlaGluThrArgArgSerAlaMet-117 |
| SEQ. ID. NO. 9188 | 125-LeuThrGlyAspThr-129 |

TABLE 1-continued

Hydrophilic Regions - Hopp-Woods
SEQ. ID. NO. 9189  16-ThrProProLysMetArgLeuAlaLysProLysProThrAla-29
SEQ. ID. NO. 9190  47-MetThrAsnArgGluMetAsnAspArgAlaAsnAlaAsnArgArgGlyTrpAsnGluAlaLysAlaArgSerAlaLysGluAlaAlaLysSerLeuAlaLysLysLysGluThrThr-85
SEQ. ID. NO. 9191  110-AlaGluThrArgArgSerAlaMet-117
672
AMPHI Regions - AMPHI
SEQ. ID. NO. 9192  38-ArgAlaValAspIleAlaArgAlaLysLys-47
SEQ. ID. NO. 9193  50-AlaAlaLeuProProPheValSerValVal-59
SEQ. ID. NO. 9194  67-AlaGlnAsnIleArgArgIleLeuAlaGluValPro-78
SEQ. ID. NO. 9195  91-AlaPheCysArgGlnPheHisArgProTyr-100
SEQ. ID. NO. 9196  105-ArgValGlnThrAlaSerAspIle-112
SEQ. ID. NO. 9197  115-AlaAlaThrArgPheProAsp-121
SEQ. ID. NO. 9198  131-HisProSerGluTyrGlyGlyThr-138
SEQ. ID. NO. 9199  163-ProGluAsnValGlyGluAlaValArgIleThrGlyAlaGluSer-177
Antigenic Index - Jameson-Wolf
SEQ. ID. NO. 9200  1-MetArgLysIleArgThrLysIle-8
SEQ. ID. NO. 9201  13-ThrProGluAspAlaAlaAla-19
SEQ. ID. NO. 9202  35-GlySerSerArgAlaValAspIleAlaArgAlaLysLysIleThr-49
SEQ. ID. NO. 9203  65-GluSerAlaGlnAsnIleArgArgIleLeuAla-75
SEQ. ID. NO. 9204  84-PheHisGlyAspGluAspAspAlaPhe-92
SEQ. ID. NO. 9205  110-SerAspIleArgAsnAlaAlaThrArgPheProAspAla-122
SEQ. ID. NO. 9206  130-TyrHisProSerGluTyrGlyGlyThrGlyAsnArgPheAsp-143
SEQ. ID. NO. 9207  148-AlaGluTyrSerGlyLysPro-154
SEQ. ID. NO. 9208  160-GlyLeuThrProGluAsnValGlyGluAlaValArg-171
SEQ. ID. NO. 9209  176-GluSerValAspValSerGlyGlyValGluAlaSerLysGlyLysLysAspAlaAlaLys-195
SEQ. ID. NO. 9210  202-ThrAlaAsnArgLeuSerArg-208
Hydrophilic Regions - Hopp-Woods
SEQ. ID. NO. 9211  1-MetArgLysIleArgThrLysIle-8
SEQ. ID. NO. 9212  13-ThrProGluAspAlaAlaAla-19
SEQ. ID. NO. 9213  36-SerSerArgAlaValAspIleAlaArgAlaLysLysIleThr-49
SEQ. ID. NO. 9214  66-SerAlaGlnAsnIleArgArgIleLeuAla-75
SEQ. ID. NO. 9215  85-HisGlyAspGluAspAspAlaPhe-92
SEQ. ID. NO. 9216  110-SerAspIleArgAsnAlaAla-116
SEQ. ID. NO. 9217  134-GluTyrGlyGlyThrGlyAsn-140
SEQ. ID. NO. 9218  165-AsnValGlyGluAlaValArg-171
SEQ. ID. NO. 9219  176-GluSerValAspVal-180
SEQ. ID. NO. 9220  184-ValGluAlaSerLysGlyLysLysAspAlaAlaLys-195
SEQ. ID. NO. 9221  204-AsnArgLeuSerArg-208
673
AMPHI Regions - AMPHI
SEQ. ID. NO. 9222  84-LeuAsnAspArgLeuAsnGlnAsnValThrGluAlaLeuGlyGlyValAspVal-101
SEQ. ID. NO. 9223  110-ArgPheThrAspAla-114
SEQ. ID. NO. 9224  117-ValValLeuLysGlnLeuProLys-124
SEQ. ID. NO. 9225  172-ArgIleAlaAsnLeuLeuGluLeuIleLysProTyrLeu-184
SEQ. ID. NO. 9226  212-LysLeuPheArgTyrLeuGlyGluGlu-220
SEQ. ID. NO. 9227  261-GlyGluArgLeuLysLysIleSerThr-269
SEQ. ID. NO. 9228  275-MetGluLysLeuPhe-279
SEQ. ID. NO. 9229  285-LeuLysValTrpValLysValLys-292
Antigenic Index - Jameson-Wolf
SEQ. ID. NO. 9230  7-LeuAlaGlyGluArgAlaAlaGlyGlyTyrArg-17
SEQ. ID. NO. 9231  24-ValGlyArgProAsnValGlyLysSerThr-33
SEQ. ID. NO. 9232  44-SerIleThrSerLysLysAlaGlnThrThrArgAsnArgValThr-58
SEQ. ID. NO. 9233  61-TyrThrAspAspThrAla-66
SEQ. ID. NO. 9234  73-ThrProGlyPheGlnThrAspHisArgAsnAlaLeuAsnAspArgLeuAsnGlnAsnValThrGlu-94
SEQ. ID. NO. 9235  110-ArgPheThrAspAlaAspArgValVal-118
SEQ. ID. NO. 9236  121-GlnLeuProLysHisThr-126
SEQ. ID. NO. 9237  134-LysIleAspLysAspLysAlaLysAspArgTyrAla-145
SEQ. ID. NO. 9238  153-ValArgAlaGluPhe-157
SEQ. ID. NO. 9239  180-IleLysProTyrLeuProGluSerVal-188
SEQ. ID. NO. 9240  190-MetTyrProGluAspMetValThrAspLysSerAlaArg-202
SEQ. ID. NO. 9241  208-IleValArgGluLysLeuPhe-214
SEQ. ID. NO. 9242  217-LeuGlyGluGluLeuPro-222
SEQ. ID. NO. 9243  227-ValGluValGluGlnPheGluGluGluAspGlyLeuAsn-239
SEQ. ID. NO. 9244  247-ValAspLysGluSerGlnLys-253
SEQ. ID. NO. 9245  258-GlyLysGlyGlyGluArgLeuLysLysIleSerThrGluAlaArgLeuAspMetGluLysLeuPheAsp-280
SEQ. ID. NO. 9246  291-ValLysSerGlyTrpAlaAspAspIleArgPheLeuArg-303
Hydrophilic Regions - Hopp-Woods
SEQ. ID. NO. 9247  7-LeuAlaGlyGluArgAlaAlaGly-14
SEQ. ID. NO. 9248  45-IleThrSerLysLysAlaGlnThrThrArgAsnArgVal-57
SEQ. ID. NO. 9249  61-TyrThrAspAspThrAla-66
SEQ. ID. NO. 9250  78-ThrAspHisArgAsnAlaLeuAsnAspArgLeuAsn-89
SEQ. ID. NO. 9251  110-ArgPheThrAspAlaAspArgValVal-118
SEQ. ID. NO. 9252  134-LysIleAspLysAspLysAlaLysAspArgTyrAla-145
SEQ. ID. NO. 9253  153-ValArgAlaGluPhe-157
SEQ. ID. NO. 9254  194-AspMetValThrAspLysSerAlaArg-202
SEQ. ID. NO. 9255  208-IleValArgGluLysLeuPhe-214
SEQ. ID. NO. 9256  217-LeuGlyGluGluLeuPro-222
SEQ. ID. NO. 9257  227-ValGluValGluGlnPheGluGluGluAspGlyLeuAsn-239
SEQ. ID. NO. 9258  247-ValAspLysGluSerGlnLys-253

TABLE 1-continued

| | |
|---|---|
| SEQ. ID. NO. 9259 | 259-LysGlyGlyGluArgLeuLysLysIleSerThrGluAlaArgLeuAspMetGluLysLeuPheAsp-280 |
| SEQ. ID. NO. 9260 | 293-SerGlyTrpAlaAspAspIleArgPheLeuArg-303 |

674
AMPHI Regions - AMPHI

| | |
|---|---|
| SEQ. ID. NO. 9261 | 16-ValTyrGlnSerLeuIle-21 |
| SEQ. ID. NO. 9262 | 24-ThrAlaAlaProGluIleAlaLysAsnIleArgGluMetSerAspPheAlaLysAlaAspGluGluLeu-46 |
| SEQ. ID. NO. 9263 | 58-AlaAlaGluTyrIleArgGlnIleArgPro-67 |
| SEQ. ID. NO. 9264 | 86-ThrAlaCysHisGluLeuSerAlaMetProGluThr-97 |
| SEQ. ID. NO. 9265 | 107-IleGluValThrLysThrPheGlyGlyThrAspGlyHisLysPheValAsnGlyIleLeuAspLysLeuAla-130 |

Antigenic Index - Jameson-Wolf

| | |
|---|---|
| SEQ. ID. NO. 9266 | 1-MetLysThrAlaArgArgArgSerArgGluLeuAla-12 |
| SEQ. ID. NO. 9267 | 28-GluIleAlaLysAsnIleArgGluMetSerAspPheAlaLysAlaAspGluGluLeuPhe-47 |
| SEQ. ID. NO. 9268 | 54-ThrGlnThrAsnAla-58 |
| SEQ. ID. NO. 9269 | 63-ArgGlnIleArgProLeuLeuAspArgAspGluLysAspLeuAsnProIleGluArg-81 |
| SEQ. ID. NO. 9270 | 93-AlaMetProGluThrProTyr-99 |
| SEQ. ID. NO. 9271 | 105-GluAlaIleGluValThrLysThrPheGlyGlyThrAspGlyHisLysPhe-121 |
| SEQ. ID. NO. 9272 | 129-LeuAlaAlaGlnIleArgProAspGluProLysArgArg-141 |

Hydrophilic Regions - Hopp-Woods

| | |
|---|---|
| SEQ. ID. NO. 9273 | 1-MetLysThrAlaArgArgArgSerArgGluLeuAla-12 |
| SEQ. ID. NO. 9274 | 28-GluIleAlaLysAsnIleArgGluMetSerAspPheAlaLysAlaAspGluGluLeuPhe-47 |
| SEQ. ID. NO. 9275 | 63-ArgGlnIleArgProLeuLeuAspArgAspGluLysAspLeuAsnProIleGluArg-81 |
| SEQ. ID. NO. 9276 | 105-GluAlaIleGluVal-109 |
| SEQ. ID. NO. 9277 | 133-IleArgProAspGluProLysArgArg-141 |

675
AMPHI Regions - AMPHI

| | |
|---|---|
| SEQ. ID. NO. 9278 | 21-ArgPheThrAsnGluIleGlySerGluMetLeuLysValCysCysArgThrLeuGlnGluLeuGly-42 |
| SEQ. ID. NO. 9279 | 74-AlaLeuIleAlaIle-78 |
| SEQ. ID. NO. 9280 | 123-GlnAlaIleGluArgIleGluGluLysAlaSerAsp-134 |
| SEQ. ID. NO. 9281 | 141-GluCysAlaAsnLeuValAsnLeuLeuLeuGlu-151 |

Antigenic Index - Jameson-Wolf

| | |
|---|---|
| SEQ. ID. NO. 9282 | 6-ProAsnLeuAspGlyLysHisLeuArg-14 |
| SEQ. ID. NO. 9283 | 26-IleGlySerGluMetLeu-31 |
| SEQ. ID. NO. 9284 | 42-GlyValAlaAspGluAsnIle-48 |
| SEQ. ID. NO. 9285 | 68-SerSerGluLysPheAsp-73 |
| SEQ. ID. NO. 9286 | 82-IleArgGlyGluThrTyr-87 |
| SEQ. ID. NO. 9287 | 92-ValSerAsnGluSerGlyAlaGlyVal-100 |
| SEQ. ID. NO. 9288 | 118-ThrGluAsnAspAlaGlnAlaIleGluArgIleGluGluLysAlaSerAspAlaAlaLysValAlaVal-140 |
| SEQ. ID. NO. 9289 | 152-GluGlnPheGluAspGluGlu-158 |

Hydrophilic Regions - Hopp-Woods

| | |
|---|---|
| SEQ. ID. NO. 9290 | 8-LeuAspGlyLysHisLeuArg-14 |
| SEQ. ID. NO. 9291 | 26-IleGlySerGluMetLeu-31 |
| SEQ. ID. NO. 9292 | 42-GlyValAlaAspGluAsnIle-48 |
| SEQ. ID. NO. 9293 | 68-SerSerGluLysPheAsp-73 |
| SEQ. ID. NO. 9294 | 82-IleArgGlyGluThrTyr-87 |
| SEQ. ID. NO. 9295 | 92-ValSerAsnGluSerGlyAlaGly-99 |
| SEQ. ID. NO. 9296 | 118-ThrGluAsnAspAlaGlnAlaIleGluArgIleGluGluLysAlaSerAspAlaAlaLysValAlaVal-140 |
| SEQ. ID. NO. 9297 | 152-GluGlnPheGluAspGluGlu-158 |

677
AMPHI Regions - AMPHI

| | |
|---|---|
| SEQ. ID. NO. 9298 | 20-AlaArgPheCysArgPheArgArg-27 |
| SEQ. ID. NO. 9299 | 45-LeuThrProPheArgArgValGlnAsnHisPheValAlaPheAlaArgPheAsnGln-63 |
| SEQ. ID. NO. 9300 | 79-IleAspPheIleAspAlaAsp-85 |
| SEQ. ID. NO. 9301 | 87-PheAspGlyLeuLeuAlaPro-93 |
| SEQ. ID. NO. 9302 | 105-LysHisLeuValGlyArgPhe-111 |
| SEQ. ID. NO. 9303 | 155-CysArgProValAspAspLeuAspAspPheGlyAlaPhePheValAspGlnLeuIleLysLeuValPheGlnCys-179 |

Antigenic Index - Jameson-Wolf

| | |
|---|---|
| SEQ. ID. NO. 9304 | 23-CysArgPheArgArgHisSerArgSerValAsp-33 |
| SEQ. ID. NO. 9305 | 35-AspValPheAspArgLysAspPheAsn-43 |
| SEQ. ID. NO. 9306 | 47-ProPheArgArgValGln-52 |
| SEQ. ID. NO. 9307 | 61-PheAsnGlnThrThrSerGlnArgArgAsnProArgAsnPheVal-75 |
| SEQ. ID. NO. 9308 | 82-IleAspAlaAspAspPheAspGly-89 |
| SEQ. ID. NO. 9309 | 97-GlnGlnSerAspArgArgAlaGluLysHisLeu-107 |
| SEQ. ID. NO. 9310 | 115-GlyIleAspAspAspGlySerLeu-122 |
| SEQ. ID. NO. 9311 | 125-PheGlyGlnGluThrAspAlaAlaVal-133 |
| SEQ. ID. NO. 9312 | 156-ArgProValAspAspLeuAspAspPheGly-165 |
| SEQ. ID. NO. 9313 | 181-ProSerGlyGlyArgAsn-186 |

Hydrophilic Regions - Hopp-Woods

| | |
|---|---|
| SEQ. ID. NO. 9314 | 23-CysArgPheArgArgHisSerArgSerValAsp-33 |
| SEQ. ID. NO. 9315 | 35-AspValPheAspArgLysAspPhe-42 |
| SEQ. ID. NO. 9316 | 65-ThrSerGlnArgArgAsnProArg-72 |
| SEQ. ID. NO. 9317 | 82-IleAspAlaAspAspPheAsp-88 |
| SEQ. ID. NO. 9318 | 97-GlnGlnSerAspArgArgAlaGluLysHisLeu-107 |
| SEQ. ID. NO. 9319 | 115-GlyIleAspAspAspGlySer-121 |
| SEQ. ID. NO. 9320 | 126-GlyGlnGluThrAspAlaAlaVal-133 |
| SEQ. ID. NO. 9321 | 156-ArgProValAspAspLeuAspAsp-163 |

678
AMPHI Regions - AMPHI

| | |
|---|---|
| SEQ. ID. NO. 9322 | 10-LeuValSerAlaValIle-15 |
| SEQ. ID. NO. 9323 | 24-MetArgGlyValIle-28 |
| SEQ. ID. NO. 9324 | 80-IleGlnLysMetLeuArgSerLeuLeuThrSerAla-91 |

TABLE 1-continued

| | |
|---|---|
| SEQ. ID. NO. 9325 | 102-ArgIleLeuGlyGlyValPheGlyAlaLeu-111 |
| SEQ. ID. NO. 9326 | 130-ProAspThrGluGlu-134 |

Antigenic Index - Jameson-Wolf

| | |
|---|---|
| SEQ. ID. NO. 9327 | 125-SerLysThrAspLeuProAspThrGluGluTrpArgGlnSerTyrTh-140 |
| SEQ. ID. NO. 9328 | 154-HisSerGlyGlyThrAlaGluThrProGluAspAsp-165 |

Hydrophilic Regions - Hopp-Woods

| | |
|---|---|
| SEQ. ID. NO. 9329 | 125-SerLysThrAspLeuProAspThrGluGluTrpArgGln-137 |
| SEQ. ID. NO. 9330 | 157-GlyThrAlaGluThrProGluAspAsp-165 |

681-2
AMPHI Regions - AMPHI

| | |
|---|---|
| SEQ. ID. NO. 9331 | 12-PheSerGluGluAlaLysPheIleSerAlaMet-22 |
| SEQ. ID. NO. 9332 | 120-CysLeuArgValGlyArgAlaValArgArg-129 |

Antigenic Index - Jameson-Wolf

| | |
|---|---|
| SEQ. ID. NO. 9333 | 9-AlaSerAsnPheSerGluGluAlaLysPhe-18 |
| SEQ. ID. NO. 9334 | 39-AlaThrProAsnSerTrpArgValArgGlnGln-49 |
| SEQ. ID. NO. 9335 | 59-LeuValLysArgAlaCys-64 |
| SEQ. ID. NO. 9336 | 67-ProMetArgArgCysLeuProSerArgLeu-76 |
| SEQ. ID. NO. 9337 | 90-GlyPheGlyMetProSerGluGly-97 |
| SEQ. ID. NO. 9338 | 102-AlaAlaSerArgArgArgPheGlyMetCysArgLeuArgGlnAlaPrMetArgCysLeuArgValGlyArgAlaValArgArgPheGln-131 |
| SEQ. ID. NO. 9339 | 134-PheTrpArgCysArgArgGly-140 |

Hydrophilic Regions - Hopp-Woods

| | |
|---|---|
| SEQ. ID. NO. 9340 | 11-AsnPheSerGluGluAlaLysPhe-18 |
| SEQ. ID. NO. 9341 | 44-TrpArgValArgGln-48 |
| SEQ. ID. NO. 9342 | 59-LeuValLysArgAlaCys-64 |
| SEQ. ID. NO. 9343 | 67-ProMetArgArgCysLeuPro-73 |
| SEQ. ID. NO. 9344 | 102-AlaAlaSerArgArgArgPheGly-109 |
| SEQ. ID. NO. 9345 | 112-ArgLeuArgGlnAlaPro-117 |
| SEQ. ID. NO. 9346 | 119-ArgCysLeuArgValGlyArgAlaValArgArg-129 |

682-2
AMPHI Regions - AMPHI

| | |
|---|---|
| SEQ. ID. NO. 9347 | 33-ArgLeuArgLysCysGlyArgIleLeuSerGlyIleCysGluProPhe-48 |
| SEQ. ID. NO. 9348 | 99-CysArgLeuPheCysAspGly-105 |

Antigenic Index - Jameson-Wolf

| | |
|---|---|
| SEQ. ID. NO. 9349 | 9-SerTyrGlyLysTrpArgLysAsnTrpAspIle-19 |
| SEQ. ID. NO. 9350 | 30-SerSerThrArgLeuArgLysCysGlyArg-39 |
| SEQ. ID. NO. 9351 | 69-ArgThrLeuArgLeuArgGlySerArgThrArg-79 |
| SEQ. ID. NO. 9352 | 84-GlyProPheTrpPheCysHisArgProArgGlnSerHisGly-97 |
| SEQ. ID. NO. 9353 | 102-PheCysAspGlySerMetAspGlnThrArgAspArgArgCysArgSer-117 |
| SEQ. ID. NO. 9354 | 121-LeuHisSerAspArgTyrArgHisSerAsnLeuTrp-132 |

Hydrophilic Regions - Hopp-Woods

| | |
|---|---|
| SEQ. ID. NO. 9355 | 12-LysTrpArgLysAsnTrpAsp-18 |
| SEQ. ID. NO. 9356 | 32-ThrArgLeuArgLysCysGlyArg-39 |
| SEQ. ID. NO. 9357 | 69-ArgThrLeuArgLeuArgGlySerArgThr-78 |
| SEQ. ID. NO. 9358 | 91-ArgProArgGlnSerHisGly-97 |
| SEQ. ID. NO. 9359 | 105-GlySerMetAspGlnThrArgAspArgArgCysArgSer-117 |
| SEQ. ID. NO. 9360 | 122-HisSerAspArgTyrArgHis-128 |

683
AMPHI Regions - AMPHI

| | |
|---|---|
| SEQ. ID. NO. 9361 | 26-ThrProAspLysSerAlaArgTrpGluAsnIleGlyThrIleSerAsn-41 |
| SEQ. ID. NO. 9362 | 75-ArgPheAlaAsnThrPro-80 |
| SEQ. ID. NO. 9363 | 101-SerSerLeuGlnLeuPhe-106 |
| SEQ. ID. NO. 9364 | 124-ArgProMetSerIleLeuSerGly-131 |

Antigenic Index - Jameson-Wolf

| | |
|---|---|
| SEQ. ID. NO. 9365 | 24-CysSerThrProAspLysSerAlaArgTrpGluAsn-35 |
| SEQ. ID. NO. 9366 | 37-GlyThrIleSerAsnGly-42 |
| SEQ. ID. NO. 9367 | 48-IleAsnLysAspSerValArgLysAsnGlyAsn-58 |
| SEQ. ID. NO. 9368 | 63-GlnAspLysLysValValThrAsnLeuLysGlnGluArgPheAlaAsnThrProAlaTyr-82 |
| SEQ. ID. NO. 9369 | 93-CysAsnAsnLysThrTyrArgLeu-100 |
| SEQ. ID. NO. 9370 | 106-PheAspThrLysAsnThrGluIleSerThrGlnAsnTyrThrAlaSerSerLeuArgPro-125 |
| SEQ. ID. NO. 9371 | 131-GlyThrLeuThrGluLysGlnTyrGlu-139 |
| SEQ. ID. NO. 9372 | 141-ValCysGlyLysLysLeu-146 |

Hydrophilic Regions - Hopp-Woods

| | |
|---|---|
| SEQ. ID. NO. 9373 | 25-SerThrProAspLysSerAlaArgTrpGluAsn-35 |
| SEQ. ID. NO. 9374 | 48-IleAsnLysAspSerValArgLysAsnGly-57 |
| SEQ. ID. NO. 9375 | 63-GlnAspLysLysValValThr-69 |
| SEQ. ID. NO. 9376 | 71-LeuLysGlnGluArgPheAla-77 |
| SEQ. ID. NO. 9377 | 107-AspThrLysAsnThrGluIleSer-114 |
| SEQ. ID. NO. 9378 | 133-LeuThrGluLysGlnTyrGlu-139 |
| SEQ. ID. NO. 9379 | 141-ValCysGlyLysLysLeu-146 |

684
AMPHI Regions - AMPHI

| | |
|---|---|
| SEQ. ID. NO. 9380 | 13-AlaAlaCysGlyThrValGln-19 |
| SEQ. ID. NO. 9381 | 47-LeuAlaGluProLeu-51 |
| SEQ. ID. NO. 9382 | 73-TrpAlaAspThrLeuAspAspMetLeuGluAlaAlaLeuSerAsnAlaPheAsnArgLeuAspSerThr-95 |
| SEQ. ID. NO. 9383 | 110-TrpThrValTyrIleAspAlaPheGlnGlySerTyr-121 |
| SEQ. ID. NO. 9384 | 154-AlaMetThrAlaAlaLeuGluGlnGlyLeuLysGlnAlaAlaGlnGlnMetVal-171 |

Antigenic Index - Jameson-Wolf

| | |
|---|---|
| SEQ. ID. NO. 9385 | 26-LeuProAspSerArgTyrIleArgProAlaThrGlnGlyGlyGluThrAlaValGluValArgLeuAlaGluProLeuLysArgGlyGlyLeu-56 |
| SEQ. ID. NO. 9386 | 60-ThrAspProTyrArgLeuAsnThrAlaGln-69 |
| SEQ. ID. NO. 9387 | 76-ThrLeuAspAspMetLeuGlu-82 |

TABLE 1-continued

| | |
|---|---|
| SEQ. ID. NO. 9388 | 90-AsnArgLeuAspSerThrArg-96 |
| SEQ. ID. NO. 9389 | 101-AlaSerArgSerGlySerThrGluLys-109 |
| SEQ. ID. NO. 9390 | 117-PheGlnGlySerTyrThrGlyLysThrLeu-126 |
| SEQ. ID. NO. 9391 | 133-LeuProAspGlyThrAsnArgProPheHisIleGluThrGluGlnGlnGlyAspGlyTyrAla-153 |
| SEQ. ID. NO. 9392 | 161-GlnGlyLeuLysGlnAlaAla-167 |

Hydrophilic Regions - Hopp-Woods

| | |
|---|---|
| SEQ. ID. NO. 9393 | 27-ProAspSerArgTyrIleArg-33 |
| SEQ. ID. NO. 9394 | 35-AlaThrGlnGlyGlyGluThrAlaValGluValArgLeuAlaGluProLeuLysArgGlyGly-55 |
| SEQ. ID. NO. 9395 | 76-ThrLeuAspAspMetLeuGlu-82 |
| SEQ. ID. NO. 9396 | 90-AsnArgLeuAspSer-94 |
| SEQ. ID. NO. 9397 | 102-SerArgSerGlySerThrGluLys-109 |
| SEQ. ID. NO. 9398 | 141-PheHisIleGluThrGluGlnGlnGlyAsp-150 |
| SEQ. ID. NO. 9399 | 161-GlnGlyLeuLysGlnAlaAla-167 |

685
AMPHI Regions - AMPHI

| | |
|---|---|
| SEQ. ID. NO. 9400 | 7-AsnPheAlaPheCysGlyValVal-14 |
| SEQ. ID. NO. 9401 | 44-CysAlaValLeuLeu-48 |
| SEQ. ID. NO. 9402 | 94-TrpAlaAlaLeuAspThrLeuThrGluLeu-103 |
| SEQ. ID. NO. 9403 | 137-TyrGluAlaLeuHisArgTyr-143 |
| SEQ. ID. NO. 9404 | 154-GlyAlaGluAlaTyrGluGlnLeuAlaLysAsn-164 |
| SEQ. ID. NO. 9405 | 182-GluLysGlnMetGluThrLeuAlaArgIlePheGlyLysGlu-195 |
| SEQ. ID. NO. 9406 | 206-AspAlaLeuPheAla-210 |
| SEQ. ID. NO. 9407 | 296-AlaValGluValLeuAspAsnAlaLeuVal-305 |
| SEQ. ID. NO. 9408 | 336-AlaAlaGluGlnLeuLysAlaAla-343 |

Antigenic Index - Jameson-Wolf

| | |
|---|---|
| SEQ. ID. NO. 9409 | 20-LeuAsnAsnLysHisSerTyrSerTyrAlaLysGluProHisThrValLysProArgPhe-39 |
| SEQ. ID. NO. 9410 | 52-SerProGluProAlaAlaGluLysThrValSer-62 |
| SEQ. ID. NO. 9411 | 74-ProThrAlaArgGlyAspAlaValValProLysAsnProGluArgValAla-90 |
| SEQ. ID. NO. 9412 | 122-AlaPheAspLysAlaAla-127 |
| SEQ. ID. NO. 9413 | 133-PheGluProAspTyrGluAlaLeuHisArgTyrAsn-144 |
| SEQ. ID. NO. 9414 | 151-GlyGlyProGlyAlaGluAlaTyrGluGlnLeuAlaLysAsnAlaThr-166 |
| SEQ. ID. NO. 9415 | 170-LeuThrValAspAsnGlyAsnIleArgThrSerGlyGluLysGlnMetGluThrLeu-188 |
| SEQ. ID. NO. 9416 | 192-PheGlyLysGluAlaArgAlaAlaGluLeuLysAlaGlnIle-205 |
| SEQ. ID. NO. 9417 | 211-GlnThrArgGluAlaAlaLysGlyLysGlyArgGlyLeu-223 |
| SEQ. ID. NO. 9418 | 227-ValThrGlyAsnLysValSerAlaPheGlyThrGlnSerArgLeu-241 |
| SEQ. ID. NO. 9419 | 247-GlyAspIleGlyLeuProProValAspGluSerLeuArgAsnGluGlyHisGlyGln-265 |
| SEQ. ID. NO. 9420 | 271-TyrIleLysGluLysAsnProAspTrpIle-280 |
| SEQ. ID. NO. 9421 | 285-ArgThrAlaAlaIleGlyGlnGluGlyProAla-295 |
| SEQ. ID. NO. 9422 | 307-GlyThrAsnAlaTrpLysArgLysGln-315 |
| SEQ. ID. NO. 9423 | 338-GluGlnLeuLysAlaAlaPheLysLysAlaGluPro-349 |
| SEQ. ID. NO. 9424 | 351-AlaAlaGlyLysLys-355 |

Hydrophilic Regions - Hopp-Woods

| | |
|---|---|
| SEQ. ID. NO. 9425 | 28-TyrAlaLysGluProHisThrValLys-36 |
| SEQ. ID. NO. 9426 | 52-SerProGluProAlaAlaGluLysThrValSer-62 |
| SEQ. ID. NO. 9427 | 75-ThrAlaArgGlyAspAlaValVal-82 |
| SEQ. ID. NO. 9428 | 84-LysAsnProGluArgValAla-90 |
| SEQ. ID. NO. 9429 | 122-AlaPheAspLysAlaAla-127 |
| SEQ. ID. NO. 9430 | 135-ProAspTyrGluAla-139 |
| SEQ. ID. NO. 9431 | 156-GluAlaTyrGluGlnLeuAlaLys-163 |
| SEQ. ID. NO. 9432 | 175-GlyAsnIleArgThrSerGlyGluLysGlnMetGluThrLeu-188 |
| SEQ. ID. NO. 9433 | 192-PheGlyLysGluAlaArgAlaAlaGluLeuLysAlaGlnIle-205 |
| SEQ. ID. NO. 9434 | 211-GlnThrArgGluAlaAlaLysGlyLysGlyArgGly-222 |
| SEQ. ID. NO. 9435 | 253-ProValAspGluSerLeuArgAsnGluGlyHisGly-264 |
| SEQ. ID. NO. 9436 | 271-TyrIleLysGluLysAsnPro-277 |
| SEQ. ID. NO. 9437 | 290-GlyGlnGluGlyProAla-295 |
| SEQ. ID. NO. 9438 | 309-AsnAlaTrpLysArgLysGln-315 |
| SEQ. ID. NO. 9439 | 338-GluGlnLeuLysAlaAlaPheLysLysAlaGluPro-349 |
| SEQ. ID. NO. 9440 | 351-AlaAlaGlyLysLys-355 |

686-2
AMPHI Regions - AMPHI

| | |
|---|---|
| SEQ. ID. NO. 9441 | 7-ValLeuGlyGlyIleAlaAlaLeu-14 |
| SEQ. ID. NO. 9442 | 39-GlySerLeuIleGluArgIleAsnAsn-47 |
| SEQ. ID. NO. 9443 | 146-SerAsnIleLysSerIleAlaAspIleLysGlyValLysThrAlaGlnSerLeuThrSerAsnTyr-167 |
| SEQ. ID. NO. 9444 | 179-ValAlaValAspGlyLeuAlaGlnSerLeu-188 |
| SEQ. ID. NO. 9445 | 204-LeuAlaValLeuAspTyrLeuLysLysAsnPro-214 |
| SEQ. ID. NO. 9446 | 241-AspGluAlaValAlaLysPheSerThrAlaIle-251 |
| SEQ. ID. NO. 9447 | 255-LysAlaAspGlyThrLeuLysLysLeuGlyGluGlnPhe-267 |

Antigenic Index - Jameson-Wolf

| | |
|---|---|
| SEQ. ID. NO. 9448 | 20-GlyGlySerGluGlyGlySerGlyAlaSerSerAlaProAlaGlnSerAlaVal-37 |
| SEQ. ID. NO. 9449 | 40-SerLeuIleGluArgIleAsnAsnLysGlyThrVal-51 |
| SEQ. ID. NO. 9450 | 54-GlyThrGluGlyThr-58 |
| SEQ. ID. NO. 9451 | 64-TyrHisAspLysAspGlyLysLeuThrGlyTyrAspValGluValThrArgAlaValAlaGluLysLeuGlyVal-88 |
| SEQ. ID. NO. 9452 | 90-ValGluPheLysGluThrGlnTrp-97 |
| SEQ. ID. NO. 9453 | 118-LeuThrSerProGluArgGlnAlaThrPheAspLysSerAspProTyrSerTrp-135 |
| SEQ. ID. NO. 9454 | 143-ArgAsnAspSerAsnIleLysSerIleAlaAspIleLysGlyValLysThrAlaGln-161 |
| SEQ. ID. NO. 9455 | 163-LeuThrSerAsnTyrGlyGluLysAlaLysAlaAlaGly-175 |
| SEQ. ID. NO. 9456 | 191-IleGluGlnLysArgAlaAspAlaThrLeuAsnAspGluLeuAla-205 |
| SEQ. ID. NO. 9457 | 209-TyrLeuLysLysAsnProAsnAlaGly-217 |
| SEQ. ID. NO. 9458 | 225-ProAlaAspGluLysValGlySer-232 |
| SEQ. ID. NO. 9459 | 235-IleValAsnLysGlyAsnAspGluAlaValAla-245 |

TABLE 1-continued

| SEQ. ID. NO. 9460 | 252-AsnGluLeuLysAlaAspGlyThrLeuLysLysLeuGly-264 |
| --- | --- |
| SEQ. ID. NO. 9461 | 267-PhePheGlyLysAspIleSerValGln-275 |

Hydrophilic Regions - Hopp-Woods

| SEQ. ID. NO. 9462 | 20-GlyGlySerGluGlyGlyGlySerGly-27 |
| --- | --- |
| SEQ. ID. NO. 9463 | 41-LeuIleGluArgIleAsnAsn-47 |
| SEQ. ID. NO. 9464 | 64-TyrHisAspLysAspGlyLysLeuThrGlyTyrAspValGluValThrArgAlaValAlaGluLysLeuGlyVal-88 |
| SEQ. ID. NO. 9465 | 90-ValGluPheLysGluThrGlnTrp-97 |
| SEQ. ID. NO. 9466 | 120-SerProGluArgGlnAlaThrPheAspLysSerAspPro-132 |
| SEQ. ID. NO. 9467 | 143-ArgAsnAspSerAsnIle-148 |
| SEQ. ID. NO. 9468 | 150-SerIleAlaAspIleLysGlyValLysThr-159 |
| SEQ. ID. NO. 9469 | 167-TyrGlyGluLysAlaLysAlaAlaGly-175 |
| SEQ. ID. NO. 9470 | 191-IleGluGlnLysArgAlaAspAlaThrLeuAsnAspGluLeuAla-205 |
| SEQ. ID. NO. 9471 | 209-TyrLeuLysLysAsnProAsnAla-216 |
| SEQ. ID. NO. 9472 | 225-ProAlaAspGluLysValGly-231 |
| SEQ. ID. NO. 9473 | 238-LysGlyAsnAspGluAlaValAla-245 |
| SEQ. ID. NO. 9474 | 252-AsnGluLeuLysAlaAspGlyThrLeuLysLysLeuGly-264 |

687

AMPHI Regions - AMPHI

| SEQ. ID. NO. 9475 | 11-AlaAlaLeuPheAlaLeu-16 |
| --- | --- |
| SEQ. ID. NO. 9476 | 64-LysValGluValLeuGluPhePheGlyTyrPheCysPro-76 |
| SEQ. ID. NO. 9477 | 78-CysAlaHisLeuGluProValLeuSerLysHisAlaLysSerPhe-92 |
| SEQ. ID. NO. 9478 | 112-LeuAlaArgLeuAlaAlaAla-118 |
| SEQ. ID. NO. 9479 | 148-ProGluValLeuLysLysTrpLeu-155 |
| SEQ. ID. NO. 9480 | 176-GlnAlaArgAlaAspLysMetGlnGluLeuThrGluThrPhe-189 |

Antigenic Index - Jameson-Wolf

| SEQ. ID. NO. 9481 | 1-MetLysSerArgHis-5 |
| --- | --- |
| SEQ. ID. NO. 9482 | 19-CysAspSerLysValGlnThrSerValProAlaAspSerAlaPro-33 |
| SEQ. ID. NO. 9483 | 43-GlyLeuValGluGlyGlnAsnTyr-50 |
| SEQ. ID. NO. 9484 | 56-ProIleProGlnGlnAlaGlyLysValGluVal-67 |
| SEQ. ID. NO. 9485 | 87-LysHisAlaLysSerPheLysAspAspMetTyrLeu-98 |
| SEQ. ID. NO. 9486 | 122-AlaAlaAlaAspSerLysAspValAlaAsn-131 |
| SEQ. ID. NO. 9487 | 141-GlnLysIleLysLeuGlnAsnProGluValLeuLys-152 |
| SEQ. ID. NO. 9488 | 159-ThrAlaPheAspGlyLysLysVal-166 |
| SEQ. ID. NO. 9489 | 171-GluSerProGluSerGlnAlaArgAlaAspLysMetGlnGluLeuThrGlu-187 |
| SEQ. ID. NO. 9490 | 189-PheGlnIleAspGlyThrPro-195 |
| SEQ. ID. NO. 9491 | 199-ValGlyGlyLysTyrLysValGluPheAlaAsp-209 |
| SEQ. ID. NO. 9492 | 211-GluSerGlyMetAsnThr-216 |
| SEQ. ID. NO. 9493 | 220-LeuAlaAspLysValArgGluGluGlnLysAlaAlaGln-232 |

Hydrophilic Regions - Hopp-Woods

| SEQ. ID. NO. 9494 | 1-MetLysSerArgHis-5 |
| --- | --- |
| SEQ. ID. NO. 9495 | 19-CysAspSerLysValGlnThr-25 |
| SEQ. ID. NO. 9496 | 27-ValProAlaAspSerAlaPro-33 |
| SEQ. ID. NO. 9497 | 61-GlnAlaGlyLysValGluVal-67 |
| SEQ. ID. NO. 9498 | 87-LysHisAlaLysSerPheLysAspAspMetTyrLeu-98 |
| SEQ. ID. NO. 9499 | 122-AlaAlaAlaAspSerLysAspValAla-130 |
| SEQ. ID. NO. 9500 | 141-GlnLysIleLysLeuGlnAsn-147 |
| SEQ. ID. NO. 9501 | 159-ThrAlaPheAspGlyLysLysVal-166 |
| SEQ. ID. NO. 9502 | 171-GluSerProGluSerGlnAlaArgAlaAspLysMetGlnGluLeuThrGlu-187 |
| SEQ. ID. NO. 9503 | 201-GlyLysTyrLysValGluPheAlaAsp-209 |
| SEQ. ID. NO. 9504 | 220-LeuAlaAspLysValArgGluGluGlnLysAlaAlaGln-232 |

688

AMPHI Regions - AMPHI

| SEQ. ID. NO. 9505 | 23-LeuSerAlaLeuLeuGlyLeu-29 |
| --- | --- |
| SEQ. ID. NO. 9506 | 121-AspValLeuGlnAsnAlaAlaGluAlaLeuLysAsp-132 |

Antigenic Index - Jameson-Wolf

| SEQ. ID. NO. 9507 | 4-TyrProSerArgPheAlaGln-10 |
| --- | --- |
| SEQ. ID. NO. 9508 | 13-IleSerValAsnLys-17 |
| SEQ. ID. NO. 9509 | 33-SerAlaGluArgValSer-38 |
| SEQ. ID. NO. 9510 | 47-IleIleGlnGlyAsnGluLeuGluProArgAla-57 |
| SEQ. ID. NO. 9511 | 62-ArgProGlyMetThrLysAspGln-69 |
| SEQ. ID. NO. 9512 | 82-AlaPheHisThrAspArgTrpAspTyr-90 |
| SEQ. ID. NO. 9513 | 92-PheAsnThrSerArgAsnGlyIleIleLysGluArgSerAsnLeu-106 |
| SEQ. ID. NO. 9514 | 116-ValArgThrGluGlyAspVal-122 |
| SEQ. ID. NO. 9515 | 126-AlaAlaGluAlaLeuLysAspArgGlnAsnThrAspLysPro-139 |

Hydrophilic Regions - Hopp-Woods

| SEQ. ID. NO. 9516 | 33-SerAlaGluArgValSer-38 |
| --- | --- |
| SEQ. ID. NO. 9517 | 51-AsnGluLeuGluProArgAla-57 |
| SEQ. ID. NO. 9518 | 64-GlyMetThrLysAspGln-69 |
| SEQ. ID. NO. 9519 | 98-GlyIleIleLysGluArgSerAsn-105 |
| SEQ. ID. NO. 9520 | 116-ValArgThrGluGlyAspVal-122 |
| SEQ. ID. NO. 9521 | 126-AlaAlaGluAlaLeuLysAspArgGlnAsnThrAspLysPro-139 |

689

AMPHI Regions - AMPHI

| SEQ. ID. NO. 9522 | 55-TyrProGluMetSerGluLysLeuMet-63 |
| --- | --- |
| SEQ. ID. NO. 9523 | 65-ValLeuMetAlaMetLeuValThrLeu-73 |
| SEQ. ID. NO. 9524 | 82-LeuProAlaIleProGluMetAlaGln-90 |
| SEQ. ID. NO. 9525 | 111-AlaPheGlyGlnValValGlyGly-118 |
| SEQ. ID. NO. 9526 | 123-IleLysGlyArgLys-127 |
| SEQ. ID. NO. 9527 | 154-LeuAsnLeuArgValGlnAlaPheGlyAlaGly-165 |
| SEQ. ID. NO. 9528 | 188-PheAlaLeuIleGlyIleIleLeu-195 |

TABLE 1-continued

| | |
|---|---|
| SEQ. ID. NO. 9529 | 203-ProMetValGlyAlaLeuLeuGlnGlyLeuGlyGlyTrpGlnAlaIlePheVal-220 |
| SEQ. ID. NO. 9530 | 230-LeuGlyLeuValGlnTyrPhe-236 |
| SEQ. ID. NO. 9531 | 245-LysIleGlyArgAspVal-250 |
| SEQ. ID. NO. 9532 | 257-ArgPheLysArgValLeu-262 |
| SEQ. ID. NO. 9533 | 277-SerPheGlySerMetPheAla-283 |
| SEQ. ID. NO. 9534 | 293-GlnGlnLeuTyrArgVal-298 |
| SEQ. ID. NO. 9535 | 344-AlaAlaAsnLeuSerGlnLeuAlaAlaValLeuPhe-355 |
| SEQ. ID. NO. 9536 | 400-ValLeuGlyValPheGlnSerLeuIleGly-409 |
| Antigenic Index - Jameson-Wolf | |
| SEQ. ID. NO. 9537 | 36-PheArgArgArgAlaVal-41 |
| SEQ. ID. NO. 9538 | 45-IleGlyArgGluPheMetProSer-52 |
| SEQ. ID. NO. 9539 | 57-GluMetSerGluLysLeu-62 |
| SEQ. ID. NO. 9540 | 95-AspValHisArgIleGluGln-101 |
| SEQ. ID. NO. 9541 | 119-SerValSerAspIleLysGlyArgLysProVal-129 |
| SEQ. ID. NO. 9542 | 174-MetValArgAspTyrTyrSerGlyArgLysAlaAla-185 |
| SEQ. ID. NO. 9543 | 238-ProLysProAlaValGlyGlyLysIleGlyArgAspValPhe-251 |
| SEQ. ID. NO. 9544 | 257-ArgPheLysArgValLeuLysThrArgAla-266 |
| SEQ. ID. NO. 9545 | 325-LeuLysThrGlyValHis-330 |
| SEQ. ID. NO. 9546 | 390-PheLysGluGluGlyGlySer-396 |
| SEQ. ID. NO. 9547 | 448-ArgAlaTrpLysGluAsnGlyGlnSerGluTyrLeu-459 |
| Hydrophilic Regions - Hopp-Woods | |
| SEQ. ID. NO. 9548 | 36-PheArgArgArgAlaVal-41 |
| SEQ. ID. NO. 9549 | 45-IleGlyArgGluPheMet-50 |
| SEQ. ID. NO. 9550 | 57-GluMetSerGluLysLeu-62 |
| SEQ. ID. NO. 9551 | 95-AspValHisArgIleGluGln-101 |
| SEQ. ID. NO. 9552 | 119-SerValSerAspIleLysGlyArgLysProVal-129 |
| SEQ. ID. NO. 9553 | 178-TyrTyrSerGlyArgLysAlaAla-185 |
| SEQ. ID. NO. 9554 | 245-LysIleGlyArgAspVal-250 |
| SEQ. ID. NO. 9555 | 257-ArgPheLysArgValLeuLysThrArgAla-266 |
| SEQ. ID. NO. 9556 | 390-PheLysGluGluGlyGlySer-396 |
| SEQ. ID. NO. 9557 | 448-ArgAlaTrpLysGluAsnGlyGln-455 |
| 690 | |
| AMPHI Regions - AMPHI | |
| SEQ. ID. NO. 9558 | 38-SerSerAlaSerSerAla-43 |
| SEQ. ID. NO. 9559 | 54-SerAlaProAspAsnValLysGlnAla-62 |
| SEQ. ID. NO. 9560 | 68-SerAsnCysThrSerLeuHisProAlaThrGlyIleAspAspLeuMetGlnGlnIleAlaGluHisIle-90 |
| SEQ. ID. NO. 9561 | 113-GlyTyrAspAsnIleGlnArgLeu-120 |
| SEQ. ID. NO. 9562 | 148-ArgThrIleSerArgGlnAlaGlnAsnAla-157 |
| SEQ. ID. NO. 9563 | 186-ProLysArgThrArgTyrPhe-192 |
| SEQ. ID. NO. 9564 | 210-GlyAsnPheGlnTyrIleSerGlnLeuProGlyTyrLeuLys-223 |
| Antigenic Index - Jameson-Wolf | |
| SEQ. ID. NO. 9565 | 1-MetLysAsnLysThrSer-6 |
| SEQ. ID. NO. 9566 | 20-CysSerProSerLysAspAspLysThrLysGluValGlyAla-33 |
| SEQ. ID. NO. 9567 | 37-SerSerSerAlaSerSerAlaProSerGlnThrAspLeuGlnProThrAlaSerAlaProAspAsnValLysGlnAlaGluSerAlaProProSerAsnCys-70 |
| SEQ. ID. NO. 9568 | 76-AlaThrGlyIleAspAspLeuMet-83 |
| SEQ. ID. NO. 9569 | 88-GluHisIleAspSerAspCys-94 |
| SEQ. ID. NO. 9570 | 101-HisGluLeuGluThrArgPheGlyLeuProAspGlyGlyTyrAspAsnIleGln-118 |
| SEQ. ID. NO. 9571 | 123-ProAspIleArgProGluAspProAspTyrHisGln-134 |
| SEQ. ID. NO. 9572 | 141-GluAspLeuArgTyrGlyLysArgThrIleSerArgGlnAlaGln-155 |
| SEQ. ID. NO. 9573 | 159-MetGluGlnGluArgArgLeuArgGlu-167 |
| SEQ. ID. NO. 9574 | 175-GlySerGlnGluThrArgGlyGlnGlyGluGluProLysArgThrArgTyr-191 |
| SEQ. ID. NO. 9575 | 196-AlaThrProAlaTyrSerSerArgHisAsnAsnGlyLeuGlyGly-210 |
| SEQ. ID. NO. 9576 | 225-HisGlyGluMetLeuGluAsnGlnSerLeu-234 |
| SEQ. ID. NO. 9577 | 236-ArgLeuSerAsnArgGluArgAsnProAspLysProPheLeu-249 |
| SEQ. ID. NO. 9578 | 252-HisPheAspGluAsnGlyLysIleThr-260 |
| SEQ. ID. NO. 9579 | 264-ValTyrGluLysAsnIle-269 |
| SEQ. ID. NO. 9580 | 272-AsnProAsnThrGlyArgIle-278 |
| Hydrophilic Regions - Hopp-Woods | |
| SEQ. ID. NO. 9581 | 1-MetLysAsnLysThr-5 |
| SEQ. ID. NO. 9582 | 21-SerProSerLysAspAspLysThrLysGluValGlyAla-33 |
| SEQ. ID. NO. 9583 | 39-SerAlaSerSerAlaProSerGlnThrAspLeuGlnPro-51 |
| SEQ. ID. NO. 9584 | 54-SerAlaProAspAsnValLysGlnAlaGluSerAlaPro-66 |
| SEQ. ID. NO. 9585 | 78-GlyIleAspAspLeuMet-83 |
| SEQ. ID. NO. 9586 | 88-GluHisIleAspSer-92 |
| SEQ. ID. NO. 9587 | 101-HisGluLeuGluThr-105 |
| SEQ. ID. NO. 9588 | 125-IleArgProGluAspProAspTyrHis-133 |
| SEQ. ID. NO. 9589 | 141-GluAspLeuArgTyrGlyLysArgThrIleSerArgGlnAlaGln-155 |
| SEQ. ID. NO. 9590 | 159-MetGluGlnGluArgArgLeuArgGlu-167 |
| SEQ. ID. NO. 9591 | 175-GlySerGlnGluThrArgGlyGlnGlyGluGluProLysArgThrArgTyr-191 |
| SEQ. ID. NO. 9592 | 200-TyrSerSerArgHisAsnAsn-206 |
| SEQ. ID. NO. 9593 | 225-HisGlyGluMetLeuGlu-230 |
| SEQ. ID. NO. 9594 | 237-LeuSerAsnArgGluArgAsnProAspLysProPhe-248 |
| SEQ. ID. NO. 9595 | 252-HisPheAspGluAsnGlyLysIleThr-260 |
| SEQ. ID. NO. 9596 | 274-AsnThrGlyArgIle-278 |
| 691 | |
| AMPHI Regions - AMPHI | |
| SEQ. ID. NO. 9597 | 11-LysProAlaAlaSer-15 |
| SEQ. ID. NO. 9598 | 55-HisAsnGluLeuArgLysIleArgThrAla-64 |
| SEQ. ID. NO. 9599 | 108-ArgTyrLeuSerGly-112 |

TABLE 1-continued

Antigenic Index - Jameson-Wolf
SEQ. ID. NO. 9600    7-CysArgPheAlaLys-11
SEQ. ID. NO. 9601    35-ProProAsnAspPheGlnProAsnCysAspIleArgArgLeuGlyLeuThrGlnSerGlnHisAsnGluLeuArgLysIleArgThr-63
SEQ. ID. NO. 9602    67-MetAlaGlyAspArgAlaArgLeuLysValMetHis-78
SEQ. ID. NO. 9603    80-GluHisSerArgArgArgSerVal-87
SEQ. ID. NO. 9604    91-IleSerSerAspValPheAsnArgAsnGluAlaArgAspTyrValGluSerArgTyrLeuSerGlyMetAspPheAlaValAspGluLeuGluIle-122
SEQ. ID. NO. 9605    131-ThrProGlnGlnGlnGln-136
SEQ. ID. NO. 9606    140-SerSerCysLeuLys-144
Hydrophilic Regions - Hopp-Woods
SEQ. ID. NO. 9607    43-CysAspIleArgArgLeuGly-49
SEQ. ID. NO. 9608    54-GlnHisAsnGluLeuArgLysIleArgThr-63
SEQ. ID. NO. 9609    67-MetAlaGlyAspArgAlaArgLeuLysValMetHis-78
SEQ. ID. NO. 9610    80-GluHisSerArgArgArgSerVal-87
SEQ. ID. NO. 9611    95-ValPheAsnArgAsnGluAlaArgAspTyrValGlu-106
SEQ. ID. NO. 9612    115-PheAlaValAspGluLeuGluIle-122
692
AMPHI Regions - AMPHI
SEQ. ID. NO. 9613    6-CysArgCysSerGluSerIleArgArgIleArgArgAsn-18
SEQ. ID. NO. 9614    77-LeuGlyTyrValPheLysProLeuAlaValPheVal-88
SEQ. ID. NO. 9615    106-GlnGlyPheGlyGlnLeuHis-112
SEQ. ID. NO. 9616    132-ThrArgGlnLeuArgGlyPheLys-139
SEQ. ID. NO. 9617    143-PheAspValPheGlnValLeuGly-150
SEQ. ID. NO. 9618    170-GlnPheValGluHisHis-175
SEQ. ID. NO. 9619    177-AspAlaGlyGluValGlyArgValValGlyArgGlyTyrGlyAlaAlaValPheAspPhePheGlnArgPheGlnLeu-202
SEQ. ID. NO. 9620    205-ValGlnSerGlnArgArgGlyArgHisLeuGluAspPheGlyAsp-219
SEQ. ID. NO. 9621    253-IleValGlyLysLeuAspGlnPheAspGlyVal-263
SEQ. ID. NO. 9622    275-PheAspHisIleAlaGluValAlaAsp-283
Antigenic Index - Jameson-Wolf
SEQ. ID. NO. 9623    6-CysArgCysSerGluSerIleArgArgIleArgArgAsnGlyArgGluTrpArgIleLysGlyGlnLysCysArgLeuAsnThrAspThrValGln-37
SEQ. ID. NO. 9624    89-GlyGlyPheAspGlyArgProValAspIleGlyLysAlaArgPheLeu-104
SEQ. ID. NO. 9625    120-AlaValAspAspGlyLysIle-126
SEQ. ID. NO. 9626    131-AlaThrArgGlnLeuArgGlyPheLysLeuAspAspPheAsp-144
SEQ. ID. NO. 9627    150-GlyAspValArgPheGlyCysGlyGlnArgIleAspAla-162
SEQ. ID. NO. 9628    174-HisHisGlnAspAlaGlyGluValGlyArgValValGlyArgGlyTyr-189
SEQ. ID. NO. 9629    204-ArgValGlnSerGlnArgArgGlyArgHisLeuGluAspPheGlyAsp-219
SEQ. ID. NO. 9630    236-GluAspValAspVal-240
SEQ. ID. NO. 9631    255-GlyLysLeuAspGlnPheAspGly-262
SEQ. ID. NO. 9632    279-AlaGluValAlaAspGlyArgAlaGluAspAspPhePhePhe-292
SEQ. ID. NO. 9633    295-AlaValValGlyGlyGlyArgSerGlyCysGlyGlyArg-307
SEQ. ID. NO. 9634    313-AlaAlaGlyGlyGluAspGluArgGluCysGlyGlyGlyLysGlyPheGluGlu-330
Hydrophilic Regions - Hopp-Woods
SEQ. ID. NO. 9635    7-ArgCysSerGluSerIleArgArgIleArgArgAsnGlyArgGluTrpArgIleLysGlyGlnLysCysArgLeuAsnThr-33
SEQ. ID. NO. 9636    91-PheAspGlyArgProValAspIleGlyLys-100
SEQ. ID. NO. 9637    120-AlaValAspAspGlyLysIle-126
SEQ. ID. NO. 9638    131-AlaThrArgGlnLeuArgGlyPheLysLeuAspAspPheAsp-144
SEQ. ID. NO. 9639    174-HisHisGlnAspAlaGlyGluValGlyArgValValGly-186
SEQ. ID. NO. 9640    206-GlnSerGlnArgArgGlyArgHisLeuGluAspPheGlyAsp-219
SEQ. ID. NO. 9641    236-GluAspValAspVal-240
SEQ. ID. NO. 9642    256-LysLeuAspGlnPheAsp-261
SEQ. ID. NO. 9643    279-AlaGluValAlaAspGlyArgAlaGluAspAspPhePhePhe-292
SEQ. ID. NO. 9644    299-GlyGlyArgSerGlyCysGlyGly-306
SEQ. ID. NO. 9645    315-GlyGlyGluAspGluArgGluCysGlyGly-324
SEQ. ID. NO. 9646    326-LysGlyPheGluGlu-330
694
AMPHI Regions - AMPHI
SEQ. ID. NO. 9647    82-ArgGlyArgAlaCysArg-87
SEQ. ID. NO. 9648    116-CysArgHisPheAlaGln-121
SEQ. ID. NO. 9649    123-ValAlaValGlyArgIleGly-129
SEQ. ID. NO. 9650    140-PheCysGlnLeuPheAsp-145
SEQ. ID. NO. 9651    156-AspIlePheLeuVal-160
SEQ. ID. NO. 9652    162-IleAlaAspIleGlyGlu-167
SEQ. ID. NO. 9653    184-ArgGlyLeuAlaAspIleGlyGluPheValGlyValSerAsp-197
SEQ. ID. NO. 9654    251-HisGlnArgAlaSerArgIleLys-258
SEQ. ID. NO. 9655    283-ArgAlaArgArgHisPheArgGlnValPheAsn-293
SEQ. ID. NO. 9656    311-AspPheValAlaHisIle-316
SEQ. ID. NO. 9657    340-AlaAlaArgIleGly-344
Antigenic Index - Jameson-Wolf
SEQ. ID. NO. 9658    3-SerAlaSerGlyThrArgGlnLysCysArgLeuLysProVal-16
SEQ. ID. NO. 9659    23-ProLysHisSerThrProAlaSer-30
SEQ. ID. NO. 9660    47-GlyGlnAspGluHisAsnAla-53
SEQ. ID. NO. 9661    66-ProProSerAlaTyrGly-71
SEQ. ID. NO. 9662    79-HisPheGlyArgGlyArgAlaCysArgTyr-88
SEQ. ID. NO. 9663    110-ArgIleAspSerAlaArgCysArgHis-118
SEQ. ID. NO. 9664    127-ArgIleGlyArgThrAspHisAsnHisAsp-136
SEQ. ID. NO. 9665    144-PheAspGlyGlyLeuProValGlyArgArgIleAla-155
SEQ. ID. NO. 9666    163-AlaAspIleGlyGluThrArgValGlnArgGlyAspAspValPhe-177
SEQ. ID. NO. 9667    180-IleAspArgGluArgGlyLeuAlaAsp-188
SEQ. ID. NO. 9668    202-HisIleSerAspArgPheAspGlnLysHisPheAlaArgArgLysLeuProHisArgSerPheAspLeu-224
SEQ. ID. NO. 9669    228-LeuMetProAspHisAspAspPheThr-236
SEQ. ID. NO. 9670    250-ArgHisGlnArgAlaSerArgIleLysHisAlaGluThrAlaLeu-264

TABLE 1-continued

| SEQ. ID. NO. 9671 | 268-LeuProHisArgLeuArgTyrAla-275 |
| SEQ. ID. NO. 9672 | 280-AsnGlnCysArgAlaArgArgHisPhe-288 |
| SEQ. ID. NO. 9673 | 291-ValPheAsnLysHisArgThr-297 |
| SEQ. ID. NO. 9674 | 316-IleAsnArgArgAlaGluLeu-322 |
| SEQ. ID. NO. 9675 | 326-ThrPheAspAsnThrAspCysPro-333 |
| SEQ. ID. NO. 9676 | 336-ThrSerAlaGluAlaAlaArgIleGlyLysAspAspGlyPhe-349 |
| SEQ. ID. NO. 9677 | 370-TyrGlyGlyArgCysCysProThrProProThrProHisArgArgArg-385 |

Hydrophilic Regions - Hopp-Woods
| SEQ. ID. NO. 9678 | 5-SerGlyThrArgGlnLysCysArgLeuLysPro-15 |
| SEQ. ID. NO. 9679 | 47-GlyGlnAspGluHisAsnAla-53 |
| SEQ. ID. NO. 9680 | 81-GlyArgGlyArgAlaCysArg-87 |
| SEQ. ID. NO. 9681 | 110-ArgIleAspSerAlaArgCysArgHis-118 |
| SEQ. ID. NO. 9682 | 127-ArgIleGlyArgThrAspHisAsnHis-135 |
| SEQ. ID. NO. 9683 | 150-ValGlyArgArgIleAla-155 |
| SEQ. ID. NO. 9684 | 163-AlaAspIleGlyGluThrArgValGlnArgGlyAspAsp-175 |
| SEQ. ID. NO. 9685 | 180-IleAspArgGluArgGlyLeuAlaAsp-188 |
| SEQ. ID. NO. 9686 | 202-HisIleSerAspArgPheAspGlnLysHisPheAlaArgArgLysLeuProHisArgSerPheAspLeu-224 |
| SEQ. ID. NO. 9687 | 230-ProAspHisAspAsp-234 |
| SEQ. ID. NO. 9688 | 250-ArgHisGlnArgAlaSerArgIleLysHisAlaGluThrAlaLeu-264 |
| SEQ. ID. NO. 9689 | 280-AsnGlnCysArgAlaArgArgHisPhe-288 |
| SEQ. ID. NO. 9690 | 292-PheAsnLysHisArg-296 |
| SEQ. ID. NO. 9691 | 316-IleAsnArgArgAlaGluLeu-322 |
| SEQ. ID. NO. 9692 | 327-PheAspAsnThrAsp-331 |
| SEQ. ID. NO. 9693 | 338-AlaGluAlaAlaArgIleGlyLysAspAspGly-348 |
| SEQ. ID. NO. 9694 | 380-ThrProHisArgArgArg-385 |

695
AMPHI Regions - AMPHI
| SEQ. ID. NO. 9695 | 36-HisProGlnArgPheGlnSerLysProAlaGluArgProAlaHisArgPro-52 |
| SEQ. ID. NO. 9696 | 129-ValArgLeuSerAsnGluValGlu-136 |
| SEQ. ID. NO. 9697 | 144-AlaLeuGluHisAlaLysThrHisSer-152 |
| SEQ. ID. NO. 9698 | 156-AlaTyrValGlnLysLeuAsp-162 |
| SEQ. ID. NO. 9699 | 183-ValGluThrAlaGlnAsnLeuTyrAsnGlnAlaLeuLysHisTyrLysSerGly-200 |
| SEQ. ID. NO. 9700 | 205-AlaAlaSerLeuLeuLysGlyAla-212 |
| SEQ. ID. NO. 9701 | 238-CysGluSerValIleGluIle-244 |
| SEQ. ID. NO. 9702 | 248-TyrAlaAsnArgPheLysAspSer-255 |
| SEQ. ID. NO. 9703 | 278-AlaArgAlaThrTrpArgSerLeuIleGlnThrTyrProGly-291 |

Antigenic Index - Jameson-Wolf
| SEQ. ID. NO. 9704 | 1-LeuProGlnThrArgProSerArgArgHisHisArgHisArgGlnTyrPheAlaGluArgLysGlyAspAlaArgSerGlyPhe-28 |
| SEQ. ID. NO. 9705 | 31-AlaAlaGlnArgArgHisProGlnArgPheGlnSerLysProAlaGluArgProAlaHisArgProHisHisProAlaArgArgArgArgLeuAspPro AlaSerGluLysIleMetLys-70 |
| SEQ. ID. NO. 9706 | 83-SerAlaSerCysAlaSer-88 |
| SEQ. ID. NO. 9707 | 93-ProAlaGlySerGlnThrGluMetSerThrArgGluAsnAlaSerAspGlyIleProTyr-112 |
| SEQ. ID. NO. 9708 | 117-LeuGlnAspArgLeuAspTyrLeuGlu-125 |
| SEQ. ID. NO. 9709 | 127-LysIleValArgLeuSerAsnGluValGluThrLeuAsnGlyLysValLysAlaLeuGluHisAlaLysThrHisSerSerGlyArgAlaTyrValGln LysLeuAspAspArgLysLeuLysGlu-168 |
| SEQ. ID. NO. 9710 | 170-TyrLeuAsnThrGluGlyGlySerAla-178 |
| SEQ. ID. NO. 9711 | 193-AlaLeuLysHisTyrLysSerGlyLysPhe-202 |
| SEQ. ID. NO. 9712 | 209-LeuLysGlyAlaAspGlyGlyAspGlyGlySerIleAlaGln-222 |
| SEQ. ID. NO. 9713 | 230-GlnSerArgAlaArgMetGlyAsnCys-238 |
| SEQ. ID. NO. 9714 | 244-IleGlyGlyArgTyrAlaAsnArgPheLysAspSerProThrAlaPro-259 |
| SEQ. ID. NO. 9715 | 266-GlyGluCysGlnTyr-270 |
| SEQ. ID. NO. 9716 | 272-LeuGlnGlnLysAspIleAla-278 |
| SEQ. ID. NO. 9717 | 289-TyrProGlySerProAlaAlaLysArgAlaAlaAlaAlaValArgLysArg-305 |

Hydrophilic Regions - Hopp-Woods
| SEQ. ID. NO. 9718 | 2-ProGlnThrArgProSerArgArgHisHisArgHisArgGlnTyrPheAlaGluArgLysGlyAspAlaArgSerGlyPhe-28 |
| SEQ. ID. NO. 9719 | 31-AlaAlaGlnArgArgHisProGlnArgPheGlnSerLysProAlaGluArgProAlaHisArgProHisHisProAlaArgArgArgArgLeuAspPro AlaSerGluLysIleMetLys-70 |
| SEQ. ID. NO. 9720 | 96-SerGlnThrGluMetSerThrArgGluAsnAlaSerAsp-108 |
| SEQ. ID. NO. 9721 | 117-LeuGlnAspArgLeuAspTyrLeuGlu-125 |
| SEQ. ID. NO. 9722 | 127-LysIleValArgLeuSerAsnGluValGluThrLeuAsnGlyLysValLysAlaLeuGluHisAlaLysThrHisSerSerGly-154 |
| SEQ. ID. NO. 9723 | 157-TyrValGlnLysLeuAspAspArgLysLeuLysGlu-168 |
| SEQ. ID. NO. 9724 | 195-LysHisTyrLysSerGlyLysPhe-202 |
| SEQ. ID. NO. 9725 | 210-LysGlyAlaAspGlyGlyAspGlyGlySerIleAlaGln-222 |
| SEQ. ID. NO. 9726 | 231-SerArgAlaArgMetGlyAsn-237 |
| SEQ. ID. NO. 9727 | 248-TyrAlaAsnArgPheLysAspSerProThrAlaPro-259 |
| SEQ. ID. NO. 9728 | 266-GlyGluCysGlnTyr-270 |
| SEQ. ID. NO. 9729 | 272-LeuGlnGlnLysAspIleAla-278 |
| SEQ. ID. NO. 9730 | 293-ProAlaAlaLysArgAlaAlaAlaAlaValArgLysArg-305 |

696
AMPHI Regions - AMPHI
| SEQ. ID. NO. 9731 | 18-PheGlyGlyIlePheHisPheValCysArgPheLeuSerArgValGlySerPheValGlnSerIlePheSerCysPheSer-44 |
| SEQ. ID. NO. 9732 | 65-IlePheAspLeuValPhe-70 |
| SEQ. ID. NO. 9733 | 94-GlyLeuAsnArgPheLeuAsnLeuLeuPheGlyPheLeuArg-107 |

Antigenic Index - Jameson-Wolf
| SEQ. ID. NO. 9734 | 12-CysGlnGlyAsnLysLeu-17 |
| SEQ. ID. NO. 9735 | 73-PheAspGlyArgSerGlyArgLeuGlyGlyArgSerArgSer-86 |
| SEQ. ID. NO. 9736 | 108-ThrSerCysGlnGlyGlySerArgHisHisCysGlyAsnGln-120 |

Hydrophilic Regions - Hopp-Woods
| SEQ. ID. NO. 9737 | 73-PheAspGlyArgSerGlyArgLeuGlyGlyArgSerArgSer-86 |
| SEQ. ID. NO. 9738 | 109-SerCysGlnGlyGlySerArgHisHisCys-117 |

TABLE 1-continued

```
700
AMPHI Regions - AMPHI
SEQ. ID. NO. 9739    6-ThrLeuLeuSerValLeuIleProMetPheAlaGlyPhePheIleArgValProLys-24
SEQ. ID. NO. 9740    27-LeuProAlaLeuAspLysValLeuSerValLeu-37
SEQ. ID. NO. 9741    51-ArgValGluAspLeuGlySerArg-58
SEQ. ID. NO. 9742    80-AlaLeuAlaValLeuGlyLysLeu-87
SEQ. ID. NO. 9743    119-PheGlyLysLeuMetArgAsp-125
SEQ. ID. NO. 9744    191-SerTrpThrLysGlyLeu-196
SEQ. ID. NO. 9745    204-TrpTyrSerLeuSerGlyLeuVal-211
SEQ. ID. NO. 9746    216-TyrGlyAlaValTrp-220
SEQ. ID. NO. 9747    228-AspLeuAlaArgGluLeu-233
SEQ. ID. NO. 9748    268-GlyAlaGlyGlyLeu-272
Antigenic Index - Jameson-Wolf
SEQ. ID. NO. 9749    21-ArgValProLysProTyrLeu-27
SEQ. ID. NO. 9750    50-SerArgValGluAspLeuGlySerArgLeuAspAspMetAla-63
SEQ. ID. NO. 9751    90-TrpArgIleLysGlyLysGlyLysGlyVal-99
SEQ. ID. NO. 9752    128MetProSerGluSerAlaGlyMetTyr-136
SEQ. ID. NO. 9753    149-LeuLysSerSerGlyValSerLeu-156
SEQ. ID. NO. 9754    160-LeuValAsnArgArgGlyIleArgLeu-168
SEQ. ID. NO. 9755    185-AlaSerThrAspGlyValSer-191
SEQ. ID. NO. 9756    245-ArgPheProAspAla-249
SEQ. ID. NO. 9757    268-GlyAlaGlyGlyLeu-272
Hydrophilic Regions - Hopp-Woods
SEQ. ID. NO. 9758    50-SerArgValGluAspLeuGlySerArgLeuAspAspMetAla-63
SEQ. ID. NO. 9759    92-IleLysGlyLysGlyLysGlyVal-99
SEQ. ID. NO. 9760    149-LeuLysSerSerGlyValSer-155
SEQ. ID. NO. 9761    160-LeuValAsnArgArgGlyIleArg-167
701
AMPHI Regions - AMPHI
SEQ. ID. NO. 9762    6-PheHisValAlaGly-10
SEQ. ID. NO. 9763    30-CysLeuAspThrSer-34
SEQ. ID. NO. 9764    45-ProAsnSerPheAlaSerPheLysArgPheSerSerIle-57
SEQ. ID. NO. 9765    79-GlyProAlaProAlaMet-84
Antigenic Index - Jameson-Wolf
SEQ. ID. NO. 9766    17-AlaGlnSerThrProSerSerProThrMet-26
SEQ. ID. NO. 9767    29-ThrCysLeuAspThrSerProGluAlaGly-38
SEQ. ID. NO. 9768    52-LysArgPheSerSerIleSer-58
SEQ. ID. NO. 9769    72-AsnArgAlaAspIleProThrGlyProAla-81
SEQ. ID. NO. 9770    104-GlyLysAlaSerLeuAsnAsnArgAla-112
SEQ. ID. NO. 9771    119-SerGlySerGlyThrArgLeu-125
Hydrophilic Regions - Hopp-Woods
SEQ. ID. NO. 9772    72-AsnArgAlaAspIleProThr-78
702
AMPHI Regions - AMPHI
SEQ. ID. NO. 9773    51-CysSerGlyLeuValThrVal-57
SEQ. ID. NO. 9774    118-LysIleSerArgGly-122
Antigenic Index - Jameson-Wolf
SEQ. ID. NO. 9775    1-MetProCysSerLysAlaSer-7
SEQ. ID. NO. 9776    28-LeuAlaArgAspSerCysSerProGlyLeu-37
SEQ. ID. NO. 9777    41-ThrAlaProAlaSerSer-46
SEQ. ID. NO. 9778    68-LeuAlaIleArgArgMetAlaSerArgProThrGlyValArgArgValIleSer-85
SEQ. ID. NO. 9779    88-GlyMetProProSerThrArgAlaTrpAspLysSerMetAla-101
SEQ. ID. NO. 9780    118-LysIleSerArgGlyValSer-124
SEQ. ID. NO. 9781    139-ArgTrpAspArgLeu-143
Hydrophilic Regions - Hopp-Woods
SEQ. ID. NO. 9782    29-AlaArgAspSerCysSer-34
SEQ. ID. NO. 9783    69-AlaIleArgArgMetAlaSerArgProThrGlyValArgArgValIleSer-85
SEQ. ID. NO. 9784    94-ArgAlaTrpAspLys-98
SEQ. ID. NO. 9785    139-ArgTrpAspArgLeu-143
703
AMPHI Regions - AMPHI
SEQ. ID. NO. 9786    21-GlnThrLeuAlaThrValAsnGly-28
SEQ. ID. NO. 9787    64-GluValValAsnThrValValAlaGlnGlu-73
SEQ. ID. NO. 9788    79-LeuAspArgSerAlaGlu-84
SEQ. ID. NO. 9789    140-AlaAlaTyrAspAsnIleSerGlyPheTyrLysGly-151
SEQ. ID. NO. 9790    181-PheAspAlaValLeu-185
SEQ. ID. NO. 9791    204-ValProLeuLysAspLeuGluGlnGlyValProProLeuTyrGlnAlaIleLysAspLeuLysLys-225
SEQ. ID. NO. 9792    252-ValProSerPheAsp-256
SEQ. ID. NO. 9793    270-ArgIleAspArgAlaValGlyAlaLeu-278
Antigenic Index - Jameson-Wolf
SEQ. ID. NO. 9794    1-MetLysAlaLysIle-5
SEQ. ID. NO. 9795    26-ValAsnGlyGlnLysIleAspSerSerVal-35
SEQ. ID. NO. 9796    43-PheArgAlaGluAsnSerArgAlaGluAspThrProGlnLeuArg-57
SEQ. ID. NO. 9797    72-GlnGluValLysArgLeuLysLeuAspArgSerAlaGluPheLysAsnAlaLeuAlaLysLeuArgAlaGluAlaLysLysSerGlyAspAspLysLys
                     ProSerPheLysThr-109
SEQ. ID. NO. 9798    129-LysThrGlnProValSerGluGlnGluValLysAlaAlaTyr-142
SEQ. ID. NO. 9799    144-AsnIleSerGlyPheTyrLysGlyThrGlnGluValGlnLeu-157
SEQ. ID. NO. 9800    160-IleLeuThrAspLysGluGluAsnAlaLysLysAlaValAlaAspLeuLysAlaLysLysGlyPhe-181
SEQ. ID. NO. 9801    188-TyrSerLeuAsnAspArgThrLysGlnThrGlyAlaProValGly-202
SEQ. ID. NO. 9802    207-LysAspLeuGluGlnGlyValProPro-215
```

TABLE 1-continued

| | |
|---|---|
| SEQ. ID. NO. 9803 | 221-LysAspLeuLysLysGlyGluPheThrAlaThrProLeuLysAsnGlyAspPhe-238 |
| SEQ. ID. NO. 9804 | 243-TyrValAsnAspSerArgGluValLysValProSerPheAspGluMetLysGly-260 |
| SEQ. ID. NO. 9805 | 266-LeuGlnAlaGluArgIleAspArgAlaVal-275 |
| SEQ. ID. NO. 9806 | 282-AlaAsnIleLysProAlaLys-288 |
| Hydrophilic Regions - Hopp-Woods | |
| SEQ. ID. NO. 9807 | 1-MetLysAlaLysIle-5 |
| SEQ. ID. NO. 9808 | 29-GlnLysIleAspSerSerVal-35 |
| SEQ. ID. NO. 9809 | 43-PheArgAlaGluAsnSerArgAlaGluAspThrProGlnLeuArg-57 |
| SEQ. ID. NO. 9810 | 72-GlnGluValLysArgLeuLysLeuAspArgSerAlaGluPheLysAsnAlaLeuAlaLysLeuArgAlaGluAlaLysLysSerGlyAspAspLysLysProSerPhe-107 |
| SEQ. ID. NO. 9811 | 131-GlnProValSerGluGlnGluValLysAlaAlaTyr-142 |
| SEQ. ID. NO. 9812 | 160-IleLeuThrAspLysGluGluAsnAlaLysLysAlaValAlaAspLeuLysAlaLysLysGlyPhe-181 |
| SEQ. ID. NO. 9813 | 189-SerLeuAsnAspArgThrLysGlnThrGly-198 |
| SEQ. ID. NO. 9814 | 207-LysAspLeuGluGln-211 |
| SEQ. ID. NO. 9815 | 221-LysAspLeuLysLysGlyGluPhe-228 |
| SEQ. ID. NO. 9816 | 245-AsnAspSerArgGluValLysValProSerPheAspGluMetLysGly-260 |
| SEQ. ID. NO. 9817 | 266-LeuGlnAlaGluArgIleAspArgAlaVal-275 |
| SEQ. ID. NO. 9818 | 282-AlaAsnIleLysProAlaLys-288 |
| 704 | |
| AMPHI Regions - AMPHI | |
| SEQ. ID. NO. 9819 | 33-GlyCysGlnAlaValAlaGlnSerIleIleAspAlaGlyLeuGly-47 |
| SEQ. ID. NO. 9820 | 65-GlnGluIleLeuAspGlnIleArgLeuTyrAspLeuProGluValGlnSerAspPheValGluThrHis-87 |
| SEQ. ID. NO. 9821 | 184-LeuGlyMetMetGln-188 |
| SEQ. ID. NO. 9822 | 208-LeuGlnIleLeuHisTrpGlyGlyPheLeuMetValLeuPro-221 |
| SEQ. ID. NO. 9823 | 232-GlnGlyAlaLeuArgAspLeuLys-239 |
| SEQ. ID. NO. 9824 | 252-AlaIleIleMetThrPheIleAlaGlyValTyrSer-263 |
| SEQ. ID. NO. 9825 | 289-PheMetGluHisIleAlaArg-295 |
| SEQ. ID. NO. 9826 | 298-AlaGlyAspAlaAlaGluArgLeuValLysLeuIleProAlaPheCysHisHisMetProAspTyrProAspThrGlnGluThr-325 |
| SEQ. ID. NO. 9827 | 400-GlyGlyThrArgLeuSerHisIleValArgLeuLeuAspArgAlaLeuAla-416 |
| SEQ. ID. NO. 9828 | 423-GluLeuAlaGluGlnTyr-428 |
| SEQ. ID. NO. 9829 | 499-AlaIleGluThrLeuAlaGln-505 |
| SEQ. ID. NO. 9830 | 527-IleSerLeuLeuArg-531 |
| SEQ. ID. NO. 9831 | 576-LeuAsnArgIleGlyGluGlyValGly-584 |
| SEQ. ID. NO. 9832 | 639-LeuLysAspSerAlaAlaGluAlaValArgGlnLeuAla-651 |
| SEQ. ID. NO. 9833 | 670-GluThrAlaArgAlaLeuGlyVal-677 |
| SEQ. ID. NO. 9834 | 691-GluTyrValLysAlaLeuGlnLysGlu-699 |
| SEQ. ID. NO. 9835 | 744-AspLeuArgThrValAlaHisLeuLeuAsp-753 |
| SEQ. ID. NO. 9836 | 780-AlaValLeuGlyTyrValGlnProTrpIleAlaAla-791 |
| SEQ. ID. NO. 9837 | 799-LeuAlaValLeuGly-803 |
| SEQ. ID. NO. 9838 | 805-AlaLeuArgLeuHisLysArg-811 |
| Antigenic Index - Jameson-Wolf | |
| SEQ. ID. NO. 9839 | 1-MetLysLysThrCys-5 |
| SEQ. ID. NO. 9840 | 8-CysGlyLeuAspValProGlu-14 |
| SEQ. ID. NO. 9841 | 21-ArgTyrGluAsnGluAspArgGluThrCysCys-31 |
| SEQ. ID. NO. 9842 | 46-LeuGlySerTyrTyrLysGlnArgThrAlaAspAlaGlnLysThrGluLeuProProGlnGluIleLeuAsp-69 |
| SEQ. ID. NO. 9843 | 77-ProGluValGlnSerAspPheValGluThrHisGlyGlyThrArgGluAla-93 |
| SEQ. ID. NO. 9844 | 112-GlnLeuLeuArgThrAspGlyIleVal-120 |
| SEQ. ID. NO. 9845 | 124-LeuAsnTyrSerThrHisArgCys-131 |
| SEQ. ID. NO. 9846 | 133-ValValTrpAspAspGlyLysIleArgLeu-142 |
| SEQ. ID. NO. 9847 | 158-ProTyrAspAlaGlnLysIleGluAlaAlaAsnGlnLysGluArgLysGlnTyr-175 |
| SEQ. ID. NO. 9848 | 199-TyrGlyGlyAspIleGluProAspPhe-207 |
| SEQ. ID. NO. 9849 | 234-AlaLeuArgAspLeuLysAsnArgArgValGlyMetAspThrProIle-249 |
| SEQ. ID. NO. 9850 | 293-IleAlaArgArgLysAlaGlyAspAlaAlaGluArgLeuVal-306 |
| SEQ. ID. NO. 9851 | 316-MetProAspTyrProAspThrGlnGluThrCysGlu-327 |
| SEQ. ID. NO. 9852 | 329-AlaValValLysLeuLysAlaGlyAsp-337 |
| SEQ. ID. NO. 9853 | 342-LysProGlyGluThrIleProValAspGlyThrVal-353 |
| SEQ. ID. NO. 9854 | 356-GlySerSerAlaValAsnGluSerMetLeuThrGlyGluSer-369 |
| SEQ. ID. NO. 9855 | 374-LysMetProSerGluLysValThrAla-382 |
| SEQ. ID. NO. 9856 | 393-IleArgThrAspArgThrGlyGlyGlyThrArg-403 |
| SEQ. ID. NO. 9857 | 414-AlaLeuAlaGlnLysProArgThrAlaGluLeuAlaGlu-426 |
| SEQ. ID. NO. 9858 | 486-ThrLeuAlaArgGluGlyIle-492 |
| SEQ. ID. NO. 9859 | 495-GlyGlyLysGlnAlaIle-500 |
| SEQ. ID. NO. 9860 | 510-IlePheAspLysThrGlyThrLeuThrGlnGlyLysProAlaValArgArg-526 |
| SEQ. ID. NO. 9861 | 528-SerLeuLeuArgGlyThrAspGluAlaPhe-537 |
| SEQ. ID. NO. 9862 | 545-LeuGluGlnGlnSerGluHisProLeu-553 |
| SEQ. ID. NO. 9863 | 560-CysArgIleSerAspGlySerValPro-568 |
| SEQ. ID. NO. 9864 | 570-IleAlaIleLysGlnArgLeuAsnArgIleGlyGluGlyVal-583 |
| SEQ. ID. NO. 9865 | 589-ValAsnGlyGluThrGln-594 |
| SEQ. ID. NO. 9866 | 605-AlaGluIleSerGlyLysGluProGlnThrGluGlyGlyGlySer-619 |
| SEQ. ID. NO. 9867 | 637-AspProLeuLysAspSerAlaAlaGluAlaValArg-648 |
| SEQ. ID. NO. 9868 | 650-LeuAlaGlyLysAsnLeu-655 |
| SEQ. ID. NO. 9869 | 659-IleLeuSerGlyAspArgGluThrAlaVal-668 |
| SEQ. ID. NO. 9870 | 684-AlaMetProGluAspLysLeuGluTyr-692 |
| SEQ. ID. NO. 9871 | 694-LysAlaLeuGlnLysGluGlyLysLys-702 |
| SEQ. ID. NO. 9872 | 707-GlyAspGlyIleAsnAspAla-713 |
| SEQ. ID. NO. 9873 | 725-AlaAlaGlyGlyThrAspIleAlaArgAspGlyAlaAsp-737 |
| SEQ. ID. NO. 9874 | 743-GluAspLeuArgThr-747 |
| SEQ. ID. NO. 9875 | 753-AspGlnAlaArgThrArgHisIleIle-762 |
| SEQ. ID. NO. 9876 | 807-ArgLeuHisLysArgGlyLysMetGlnSerGluLysMetProSerGluGln-823 |

TABLE 1-continued

Hydrophilic Regions - Hopp-Woods
SEQ. ID. NO. 9877    1-MetLysLysThrCys-5
SEQ. ID. NO. 9878    21-ArgTyrGluAsnGluAspArgGluThrCys-30
SEQ. ID. NO. 9879    50-TyrLysGlnArgThrAlaAspAlaGlnLysThrGluLeuProPro-64
SEQ. ID. NO. 9880    77-ProGluValGlnSerAspPheValGlu-85
SEQ. ID. NO. 9881    87-HisGlyGlyThrArgGluAla-93
SEQ. ID. NO. 9882    112-GlnLeuLeuArgThrAspGlyIleVal-120
SEQ. ID. NO. 9883    133-ValValTrpAspAspGlyLysIleArgLeu-142
SEQ. ID. NO. 9884    160-AspAlaGlnLysIleGluAlaAlaAsnGlnLysGluArgLysGlnTyr-175
SEQ. ID. NO. 9885    201-GlyAspIleGluProAspPhe-207
SEQ. ID. NO. 9886    234-AlaLeuArgAspLeuLysAsnArgArgValGlyMet-245
SEQ. ID. NO. 9887    293-IleAlaArgArgLysAlaGlyAspAlaAlaGluArgLeuVal-306
SEQ. ID. NO. 9888    318-AspTyrProAspThrGlnGluThrCysGlu-327
SEQ. ID. NO. 9889    329-AlaValValLysLeuLysAlaGlyAsp-337
SEQ. ID. NO. 9890    374-LysMetProSerGluLysValThr-381
SEQ. ID. NO. 9891    393-IleArgThrAspArgThrGlyGlyGlyThrArg-403
SEQ. ID. NO. 9892    414-AlaLeuAlaGlnLysProArgThrAlaGluLeuAlaGlu-426
SEQ. ID. NO. 9893    486-ThrLeuAlaArgGluGlyIle-492
SEQ. ID. NO. 9894    518-ThrGlnGlyLysProAlaValArgArg-526
SEQ. ID. NO. 9895    531-ArgGlyThrAspGlu-535
SEQ. ID. NO. 9896    545-LeuGluGlnGlnSerGluHisProLeu-553
SEQ. ID. NO. 9897    561-ArgIleSerAspGlySerVal-567
SEQ. ID. NO. 9898    570-IleAlaIleLysGlnArgLeuAsnArgIleGlyGlu-581
SEQ. ID. NO. 9899    607-IleSerGlyLysGluProGlnThrGluGlyGlyGly-618
SEQ. ID. NO. 9900    638-ProLeuLysAspSerAlaAlaGluAlaValArg-648
SEQ. ID. NO. 9901    661-SerGlyAspArgGluThrAlaVal-668
SEQ. ID. NO. 9902    684-AlaMetProGluAspLysLeuGluTyr-692
SEQ. ID. NO. 9903    694-LysAlaLeuGlnLysGluGlyLysLys-702
SEQ. ID. NO. 9904    730-AspIleAlaArgAspGlyAlaAsp-737
SEQ. ID. NO. 9905    743-GluAspLeuArgThr-747
SEQ. ID. NO. 9906    753-AspGlnAlaArgArgThrArgHisIleIle-762
SEQ. ID. NO. 9907    807-ArgLeuHisLysArgGlyLysMetGlnSerGluLysMetProSerGluGln-823
705
AMPHI Regions - AMPHI
SEQ. ID. NO. 9908    67-LysIleLeuLeuLysLeu-72
SEQ. ID. NO. 9909    104-AspProIleProAla-108
SEQ. ID. NO. 9910    147-TyrMetGlnThrPheArgArgIleValAlaProGln-158
SEQ. ID. NO. 9911    169-AsnGluPheIleGlyLeuPheLysAsn-177
SEQ. ID. NO. 9912    183-ValValThrValThrGluLeuPheArgValAlaGln-194
SEQ. ID. NO. 9913    196-ThrAlaAsnArgThr-200
Antigenic Index - Jameson-Wolf
SEQ. ID. NO. 9914    13-ThrGluThrArgAlaAspMet-19
SEQ. ID. NO. 9915    132-ValProLysGlyGlnTrpGlu-138
SEQ. ID. NO. 9916    165-ProProLeuSerAsnGlu-170
SEQ. ID. NO. 9917    193-AlaGlnGluThrAlaAsnArgThrTyrAsp-202
SEQ. ID. NO. 9918    226-AlaArgLeuGluLysArgPheAspArgTyrValAla-237
Hydrophilic Regions - Hopp-Woods
SEQ. ID. NO. 9919    13-ThrGluThrArgAlaAspMet-19
SEQ. ID. NO. 9920    193-AlaGlnGluThrAlaAsnArgThr-200
SEQ. ID. NO. 9921    226-AlaArgLeuGluLysArgPheAspArgTyrValAla-237
706
AMPHI Regions - AMPHI
SEQ. ID. NO. 9922    9-LeuValSerArgTrpLeuAsnSerTyr-17
SEQ. ID. NO. 9923    24-ArgLeuIleHisAlaValArg-30
SEQ. ID. NO. 9924    70-IleTyrSerLysAlaValGluArgMetLeuGlyThrValIleGly-84
SEQ. ID. NO. 9925    111-ThrAlaSerAlaLeuAlaGlyTrpAlaAla-120
SEQ. ID. NO. 9926    153-ArgAlaMetAsnValLeu-158
SEQ. ID. NO. 9927    183-LeuAlaAspAsnLeuAlaAspCysSerLysMetIleAlaGluIleSerAsnGlyArg-201
SEQ. ID. NO. 9928    204-ThrArgGluArgLeuGluGluAsn-211
SEQ. ID. NO. 9929    243-MetGluAlaMetGlnHisAlaHisArgLysIleVal-254
SEQ. ID. NO. 9930    318-AlaLeuAlaGluHisLeuHis-324
Antigenic Index - Jameson-Wolf
SEQ. ID. NO. 9931    1-MetAsnThrSerGlnArgAsnArgLeu-9
SEQ. ID. NO. 9932    11-SerArgTrpLeuAsnSerTyrGluArgTyrArgTyrArgArg-24
SEQ. ID. NO. 9933    73-LysAlaValGluArgMetLeu-79
SEQ. ID. NO. 9934    97-HisTyrPheHisGlyAsnLeu-103
SEQ. ID. NO. 9935    122-GlyLysAsnGlyTyrVal-127
SEQ. ID. NO. 9936    140-GlyAspAsnGlySerGluTrpLeuAsp-148
SEQ. ID. NO. 9937    186-AsnLeuAlaAspCysSerLysMetIleAlaGluIleSerAsnGlyArgArgMetThrArgGluArgLeuGluGluAsnMetAlaLysMetArgGlnIleAsn-219
SEQ. ID. NO. 9938    221-ArgMetValLysSerArgSerHisLeuAlaAlaThrSerGlyGluSerArgIleSer-239
SEQ. ID. NO. 9939    249-AlaHisArgLysIleValAsn-255
SEQ. ID. NO. 9940    266-LysLeuGlnSerProLysLeuAsnGlySerGluIleArgLeuLeuAsp-281
SEQ. ID. NO. 9941    300-GlyArgHisAlaArgArgIleArgIleAspThrAlaIleAsnProGluLeuGluAlaLeuAla-320
SEQ. ID. NO. 9942    334-SerThrAsnMetArgGlnGluIle-341
SEQ. ID. NO. 9943    349-GlnArgThrArgArgLysTrpLeuAspAlaHisGluArgGlnHisLeu-364
SEQ. ID. NO. 9944    367-SerLeuLeuGluThrArgGluHisGly-375
Hydrophilic Regions - Hopp-Woods
SEQ. ID. NO. 9945    3-ThrSerGlnArgAsnArgLeu-9
SEQ. ID. NO. 9946    17-TyrGluArgTyrArgTyrArgArg-24

TABLE 1-continued

| | |
|---|---|
| SEQ. ID. NO. 9947 | 73-LysAlaValGluArgMetLeu-79 |
| SEQ. ID. NO. 9948 | 142-AsnGlySerGluTrpLeu-147 |
| SEQ. ID. NO. 9949 | 186-AsnLeuAlaAspCysSerLysMetIleAla-195 |
| SEQ. ID. NO. 9950 | 198-SerAsnGlyArgArgMetThrArgGluArgLeuGluGluAsnMetAlaLysMetArgGlnIleAsn-219 |
| SEQ. ID. NO. 9951 | 221-ArgMetValLysSerArgSerHis-228 |
| SEQ. ID. NO. 9952 | 232-ThrSerGlyGluSerArgIle-238 |
| SEQ. ID. NO. 9953 | 249-AlaHisArgLysIleValAsn-255 |
| SEQ. ID. NO. 9954 | 266-LysLeuGlnSerProLysLeuAsnGlySerGluIleArgLeuLeuAsp-281 |
| SEQ. ID. NO. 9955 | 301-ArgHisAlaArgArgIleArgIle-308 |
| SEQ. ID. NO. 9956 | 314-ProGluLeuGluAlaLeuAla-320 |
| SEQ. ID. NO. 9957 | 336-AsnMetArgGlnGluIle-341 |
| SEQ. ID. NO. 9958 | 349-GlnArgThrArgArgLysTrpLeuAspAlaHisGluArgGlnHisLeu-364 |
| SEQ. ID. NO. 9959 | 367-SerLeuLeuGluThrArgGluHisGly-375 |

707
AMPHI Regions - AMPHI

| | |
|---|---|
| SEQ. ID. NO. 9960 | 9-LeuIleArgSerMetGlnArgGln-16 |
| SEQ. ID. NO. 9961 | 88-AsnLeuSerArgLeuGlnLysAla-95 |
| SEQ. ID. NO. 9962 | 170-GluGlnGlyLeuGluAsnLeuArgArgLeuProSerVal-182 |
| SEQ. ID. NO. 9963 | 219-GlyGlyLysThrThrGlyLysTyr-226 |
| SEQ. ID. NO. 9964 | 241-SerAspLeuPheTyr-245 |
| SEQ. ID. NO. 9965 | 294-ArgTyrHisGluAlaThrGlu-300 |
| SEQ. ID. NO. 9966 | 339-ThrArgGlnThrTyrLysTyrIleAspAsp-348 |
| SEQ. ID. NO. 9967 | 539-HisLysProLysGlyPheGlnThrThrAsnThr-549 |

Antigenic Index - Jameson-Wolf

| | |
|---|---|
| SEQ. ID. NO. 9968 | 3-IleIleAsnAspAlaGluLeuIleArgSerMetGlnArgGlnGlnHisIleAsp-20 |
| SEQ. ID. NO. 9969 | 27-AlaAsnValArgPheGluGlnProLeuGluLysAsnAsnTyrValLeuSerGluAspGluThrProCysThrArg-51 |
| SEQ. ID. NO. 9970 | 56-SerLeuAspAspLysThrValArg-63 |
| SEQ. ID. NO. 9971 | 85-GlySerAsnAsnLeuSerArgLeuGlnLysAlaAla-96 |
| SEQ. ID. NO. 9972 | 114-ProGlnAsnMetAspSerGlyIleLeu-122 |
| SEQ. ID. NO. 9973 | 125-ArgValSerAlaGlyGluIleGlyAspIleArgTyrGluGluLysArgAspGlyLysSerAlaGluGlySerIle-149 |
| SEQ. ID. NO. 9974 | 157-ProLeuTyrArgAsnLysIleLeuAsn-165 |
| SEQ. ID. NO. 9975 | 167-ArgAspValGluGlnGlyLeuGluAsnLeuArgArgLeuProSerValLysThrAspIle-186 |
| SEQ. ID. NO. 9976 | 189-IleProSerGluGluGluGlyLysSerAspLeu-199 |
| SEQ. ID. NO. 9977 | 202-LysTrpGlnGlnAsnLysProIleArg-210 |
| SEQ. ID. NO. 9978 | 213-IleGlyIleAspAspAlaGlyGlyLysThrThrGlyLysTyrGlnGly-228 |
| SEQ. ID. NO. 9979 | 235-AspAsnProLeuGly-239 |
| SEQ. ID. NO. 9980 | 248-TyrGlyArgGlyLeuAlaHisLysThrAspLeuThrAspAlaThrGlyThrGluThrGluSerGlySerArgSerTyr-273 |
| SEQ. ID. NO. 9981 | 288-PheAsnHisAsnGlyHisArgTyrHisGluAlaThrGluGlyTyrSerValAsnTyrAspTyrAsnGlyLysGlnTyrGln-314 |
| SEQ. ID. NO. 9982 | 322-MetLeuTrpArgAsnArgLeuHisLysThrSerVal-333 |
| SEQ. ID. NO. 9983 | 341-GlnThrTyrLysTyrIleAspAspAlaGluIleGluValGlnArgArgArgSerAlaGlyTrpGluAlaGluLeuArgHis-367 |
| SEQ. ID. NO. 9984 | 374-TrpGlnLeuAspGlyLysLeuSerTyrLysArgGlyThrGlyMetArgGlnSerMetProAlaProGluGluAsnGlyGlyAspIleLeuProGlyThrSerArgMetLysIle-411 |
| SEQ. ID. NO. 9985 | 438-GlnTrpAsnLysThrPro-443 |
| SEQ. ID. NO. 9986 | 446-AlaGlnAspLysLeuSerIleGlySerArgTyrThrValArgGlyPheAspGlyGluGlnSerLeuPheGlyGluArgGlyPheTyrTrpGlnAsnThr-478 |
| SEQ. ID. NO. 9987 | 493-AlaAspTyrGlyArgValSerGlyGluSerAla-503 |
| SEQ. ID. NO. 9988 | 506-ValSerGlyLysGln-510 |
| SEQ. ID. NO. 9989 | 518-PheArgGlyGlyHisLysValGly-525 |
| SEQ. ID. NO. 9990 | 536-LysProLeuHisLysProLysGlyPheGln-545 |

Hydrophilic Regions - Hopp-Woods

| | |
|---|---|
| SEQ. ID. NO. 9991 | 3-IleIleAsnAspAlaGluLeuIleArgSerMetGlnArgGlnGlnHisIleAsp-20 |
| SEQ. ID. NO. 9992 | 27-AlaAsnValArgPheGluGlnProLeuGluLysAsnAsn-39 |
| SEQ. ID. NO. 9993 | 42-LeuSerGluAspGluThrProCys-49 |
| SEQ. ID. NO. 9994 | 56-SerLeuAspAspLysThrValArg-63 |
| SEQ. ID. NO. 9995 | 88-AsnLeuSerArgLeuGlnLysAlaAla-96 |
| SEQ. ID. NO. 9996 | 130-GluIleGlyAspIleArgTyrGluGluLysArgAspGlyLysSerAlaGluGlySer-148 |
| SEQ. ID. NO. 9997 | 167-ArgAspValGluGlnGlyLeuGluAsnLeuArgArgLeuProSerValLysThrAspIle-186 |
| SEQ. ID. NO. 9998 | 190-ProSerGluGluGluGlyLysSerAspLeu-199 |
| SEQ. ID. NO. 9999 | 213-IleGlyIleAspAspAlaGlyGlyLysThrThrGlyLysTyr-226 |
| SEQ. ID. NO. 10000 | 252-LeuAlaHisLysThrAspLeuThrAsp-260 |
| SEQ. ID. NO. 10001 | 262-ThrGlyThrGluThrGluSerGlySerArgSer-272 |
| SEQ. ID. NO. 10002 | 294-ArgTyrHisGluAlaThrGlu-300 |
| SEQ. ID. NO. 10003 | 345-TyrIleAspAspAlaGluIleGluValGlnArgArgArgSerAlaGlyTrp-361 |
| SEQ. ID. NO. 10004 | 363-AlaGluLeuArgHis-367 |
| SEQ. ID. NO. 10005 | 378-GlyLysLeuSerTyrLysArgGlyThrGlyMetArgGlnSerMetProAlaProGluGluAsnGlyGly-400 |
| SEQ. ID. NO. 10006 | 407-SerArgMetLysIle-411 |
| SEQ. ID. NO. 10007 | 446-AlaGlnAspLysLeuSerIle-452 |
| SEQ. ID. NO. 10008 | 460-GlyPheAspGlyGluGln-465 |
| SEQ. ID. NO. 10009 | 494-AspTyrGlyArgValSerGlyGluSer-502 |
| SEQ. ID. NO. 10010 | 537-ProLeuHisLysProLysGly-543 |

708
AMPHI Regions - AMPHI

| | |
|---|---|
| SEQ. ID. NO. 10011 | 26-ProSerArgAlaGluLysAlaAsnGlnValSerAsnIle-38 |
| SEQ. ID. NO. 10012 | 56-ThrAlaSerIleGluAspAlaLeuLysSerAspPro-67 |
| SEQ. ID. NO. 10013 | 79-IleTyrGlnTyrLeuLys-84 |
| SEQ. ID. NO. 10014 | 89-AlaGlnGluSerPhe-93 |
| SEQ. ID. NO. 10015 | 119-AsnArgProAlaGluSerMetAla-126 |
| SEQ. ID. NO. 10016 | 128-PheAspLysAlaLeu-132 |
| SEQ. ID. NO. 10017 | 142-IleAlaAsnLeuAsnLys-147 |
| SEQ. ID. NO. 10018 | 176-ProAlaPheLysGluLeuAlaArg-183 |

TABLE 1-continued

| SEQ. ID. NO. 10019 | 221-LysAlaLeuGlyAsnAlaGln-227 |

Antigenic Index - Jameson-Wolf

| SEQ. ID. NO. 10020 | 2-ProPheLysProSerLysArgIleSer-10 |
| SEQ. ID. NO. 10021 | 19-AlaCysSerThrSerTyrArgProSerArgAlaGluLysAlaAsnGln-34 |
| SEQ. ID. NO. 10022 | 46-TyrMetArgGlyGlnAspTyrArgGlnAlaThrAlaSerIleGluAspAlaLeuLysSerAspProLysAsnGlu-70 |
| SEQ. ID. NO. 10023 | 84-LysValAsnAspLysAlaGlnGluSerPheArg-94 |
| SEQ. ID. NO. 10024 | 97-LeuSerIleLysProAspSerAlaGluIleAsnAsnAsnTyrGlyTrp-112 |
| SEQ. ID. NO. 10025 | 115-CysGlyArgLeuAsnArgProAlaGlu-123 |
| SEQ. ID. NO. 10026 | 131-AlaLeuAlaAspProThrTyrProThr-139 |
| SEQ. ID. NO. 10027 | 145-LeuAsnLysGlyIleCysSerAlaLysGlnGlyGln-156 |
| SEQ. ID. NO. 10028 | 176-ProAlaPheLysGluLeuAlaArgThrLysMet-186 |
| SEQ. ID. NO. 10029 | 191-LeuGlyAspAlaAspTyrTyrPheLysLysTyrGlnSerArgValGluValLeuGlnAlaAspAspLeu-213 |
| SEQ. ID. NO. 10030 | 240-PheProTyrSerGluGluLeuGln-247 |

Hydrophilic Regions - Hopp-Woods

| SEQ. ID. NO. 10031 | 4-LysProSerLysArgIle-9 |
| SEQ. ID. NO. 10032 | 24-TyrArgProSerArgAlaGluLysAlaAsnGln-34 |
| SEQ. ID. NO. 10033 | 46-TyrMetArgGlyGlnAspTyrArgGln-54 |
| SEQ. ID. NO. 10034 | 56-ThrAlaSerIleGluAspAlaLeuLysSerAspProLysAsnGlu-70 |
| SEQ. ID. NO. 10035 | 84-LysValAsnAspLysAlaGlnGluSerPheArg-94 |
| SEQ. ID. NO. 10036 | 99-IleLysProAspSerAlaGluIle-106 |
| SEQ. ID. NO. 10037 | 117-ArgLeuAsnArgProAlaGlu-123 |
| SEQ. ID. NO. 10038 | 149-IleCysSerAlaLysGlnGly-155 |
| SEQ. ID. NO. 10039 | 177-AlaPheLysGluLeuAlaArgThrLysMet-186 |
| SEQ. ID. NO. 10040 | 201-TyrGlnSerArgValGluValLeuGlnAlaAspAspLeu-213 |

709
AMPHI Regions - AMPHI

| SEQ. ID. NO. 10041 | 6-SerLeuLeuAspMetProArgGlyGlu-14 |
| SEQ. ID. NO. 10042 | 18-ValValValAlaLeuIleAlaAlaMetGly-27 |
| SEQ. ID. NO. 10043 | 37-ProHisMetSerIleIleAlaAlaIleValValLeu-48 |
| SEQ. ID. NO. 10044 | 54-AlaArgGlyLeuLysTyrAsn-60 |
| SEQ. ID. NO. 10045 | 64-GlnGlyMetIleGlyAlaLeuAsnGlnGly-73 |
| SEQ. ID. NO. 10046 | 115-SerSerPheAlaLeuCysSerVal-122 |
| SEQ. ID. NO. 10047 | 130-SerLeuThrThrCysAla-135 |
| SEQ. ID. NO. 10048 | 171-ProLeuSerAspThr-175 |
| SEQ. ID. NO. 10049 | 185-IleAspLeuPheGluHisIleLysAsnMetMetTyrThrThr-198 |
| SEQ. ID. NO. 10050 | 221-LeuAsnSerValGluSerPheArg-228 |
| SEQ. ID. NO. 10051 | 253-LeuMetArgIleAsnAla-258 |
| SEQ. ID. NO. 10052 | 261-AlaMetLeuPheThr-265 |
| SEQ. ID. NO. 10053 | 278-ThrProAspLeuArgGlnLeuGlyAlaTrpPhe-288 |
| SEQ. ID. NO. 10054 | 298-AlaPheLysAspValValLysLeuIleSerArgGlyGly-310 |
| SEQ. ID. NO. 10055 | 334-LeuGlyValIleProSerLeuLeuGluAlaIleArgThrPheLeuThr-349 |
| SEQ. ID. NO. 10056 | 382-ThrPheLysProVal-386 |
| SEQ. ID. NO. 10057 | 395-ArgAsnLeuSerArgThrLeuGluAspAlaGlyThrValIleAsnProLeuValProTrpSerValCysGlyValPheIleSerHis-423 |

Antigenic Index - Jameson-Wolf

| SEQ. ID. NO. 10058 | 8-LeuAspMetProArgGlyGluAla-15 |
| SEQ. ID. NO. 10059 | 55-ArgGlyLeuLysTyrAsnAspMetGln-63 |
| SEQ. ID. NO. 10060 | 165-PheGlyAspLysMetSerProLeuSerAspThrThrGly-177 |
| SEQ. ID. NO. 10061 | 222-AsnSerValGluSerPheArgSerGlnLeuGlu-232 |
| SEQ. ID. NO. 10062 | 277-SerThrProAspLeuArgGln-283 |
| SEQ. ID. NO. 10063 | 290-GlyGlyTyrLysLeuGluGlyGluAlaPheLysAspValVal-303 |
| SEQ. ID. NO. 10064 | 306-IleSerArgGlyGlyLeuGlu-312 |
| SEQ. ID. NO. 10065 | 378-LeuSerGlyGlyThrPheLysProValTyrAspLysLeuGlyLeuHisSerArgAsnLeuSerArgThrLeuGluAspAlaGlyThr-406 |

Hydrophilic Regions - Hopp-Woods

| SEQ. ID. NO. 10066 | 8-LeuAspMetProArgGlyGluAla-15 |
| SEQ. ID. NO. 10067 | 57-LeuLysTyrAsnAspMetGln-63 |
| SEQ. ID. NO. 10068 | 168-LysMetSerProLeuSerAsp-174 |
| SEQ. ID. NO. 10069 | 225-GluSerPheArgSerGlnLeuGlu-232 |
| SEQ. ID. NO. 10070 | 279-ProAspLeuArgGln-283 |
| SEQ. ID. NO. 10071 | 293-LysLeuGluGlyGluAlaPheLysAspValVal-303 |
| SEQ. ID. NO. 10072 | 396-AsnLeuSerArgThrLeuGluAspAlaGly-405 |

710
AMPHI Regions - AMPHI

| SEQ. ID. NO. 10073 | 6-LysIleArgLeuMetArgGluLeuAsnLysTrpSerGln-18 |
| SEQ. ID. NO. 10074 | 31-GlyTyrAlaLysIleGlu-36 |
| SEQ. ID. NO. 10075 | 45-ProArgLeuGluGlnLeuAlaGlnIlePheLysIleAspMetTrpAspLeuLeuLys-63 |
| SEQ. ID. NO. 10076 | 104-CysLysGluMetLeuGlu-109 |

Antigenic Index - Jameson-Wolf

| SEQ. ID. NO. 10077 | 1-MetGluThrHisGluLysIleArgLeuMetArgGluLeuAsnLysTrpSerGlnGluAspMetAlaGluLysLeuAla-26 |
| SEQ. ID. NO. 10078 | 33-AlaLysIleGluArgGlyGluThrGlnLeuAsnIleProArgLeuGluGln-49 |
| SEQ. ID. NO. 10079 | 62-LeuLysSerGlyGlyGlyGly-68 |
| SEQ. ID. NO. 10080 | 73-IleAsnGluGlyAspSerGlyGlyAsp-81 |
| SEQ. ID. NO. 10081 | 86-AlaSerGlyAspValSerMet-92 |
| SEQ. ID. NO. 10082 | 95-GluPheLeuLysMetGluLeuLysHisCysLysGluMetLeuGluGlnLysAspLysGluIleGluLeuLeuArgLysLeuThrGlu-123 |

Hydrophilic Regions - Hopp-Woods

| SEQ. ID. NO. 10083 | 1-MetGluThrHisGluLysIleArgLeuMetArgGluLeuAsnLysTrpSerGlnGluAspMetAlaGluLysLeuAla-26 |
| SEQ. ID. NO. 10084 | 33-AlaLysIleGluArgGlyGluThr-40 |
| SEQ. ID. NO. 10085 | 45-ProArgLeuGluGln-49 |
| SEQ. ID. NO. 10086 | 74-AsnGluGlyAspSerGlyGly-80 |
| SEQ. ID. NO. 10087 | 95-GluPheLeuLysMetGluLeuLysHisCysLysGluMetLeuGluGlnLysAspLysGluIleGluLeuLeuArgLysLeuThrGlu-123 |

TABLE 1-continued

711
AMPHI Regions - AMPHI
SEQ. ID. NO. 10088    28-AlaGluSerTyrArgAsnLeuThrAlaSerGluIleAlaLysValTyrThrIleAlaArgMetThrAspLeuAspMetLeuAsnAspIleLys-58
SEQ. ID. NO. 10089    67-SerGlyGlnSerPheAspAspTrpArgLysGlyIleLeu-79
SEQ. ID. NO. 10090    95-GlyLysAspIleIleAspProAlaThrGlyGluValPheGlySerProArgArgLeuGluThrIleTyrArgThrAsnMet-121
SEQ. ID. NO. 10091    128-GlyGlnTyrGlnGlyTyrMet-134
SEQ. ID. NO. 10092    158-SerAlaIleAspGly-162
SEQ. ID. NO. 10093    195-ValGluArgGlnGly-199
SEQ. ID. NO. 10094    203-GlyGlnSerThrAlaAspAsnLeuValGluThrHis-214
SEQ. ID. NO. 10095    258-LysTyrAspArgAlaLeuAlaHisGlnPheAla-268
SEQ. ID. NO. 10096    281-PheLysGlnLeuGluLysGluPheTyr-289
SEQ. ID. NO. 10097    329-GlnGluLeuAlaGlyMetThr-335
SEQ. ID. NO. 10098    352-SerArgGluGlyGlnAsnPhe-358
SEQ. ID. NO. 10099    360-AspSerTyrTyrAlaPheLeuProAspMetLeuGlnAsnProGlu-374
SEQ. ID. NO. 10100    395-TrpAlaValLeuLysTyrIleLysGluValAspGluIle-407
SEQ. ID. NO. 10101    413-ArgIleSerAsnAspLysGluIleAlaLys-422
Antigenic Index - Jameson-Wolf
SEQ. ID. NO. 10102    11-SerLeuProProLysLysAlaIleGlu-19
SEQ. ID. NO. 10103    21-LeuGluSerLysLysValThrAlaGluSerTyrArgAsnLeuThr-35
SEQ. ID. NO. 10104    55-AsnAspIleLysThrSerMet-61
SEQ. ID. NO. 10105    63-GluSerAlaLysSerGlyGlnSerPheAspAspTrpArgLysGlyIle-78
SEQ. ID. NO. 10106    82-LeuSerAsnLysGlyTrpLeuHisProAsnGlyHisAsnGlyLysAspIleIleAspProAlaThrGlyGluValPheGlySerProArgArgLeuGlu
                      ThrIleTyrArgThrAsnMet-121
SEQ. ID. NO. 10107    126-AsnAlaGlyGlnTyrGlnGly-132
SEQ. ID. NO. 10108    135-AlaAsnIleAspAlaArgProTyrTrp-143
SEQ. ID. NO. 10109    147-AlaValGlyAspSerArgThrArgProAlaHisSerAla-159
SEQ. ID. NO. 10110    165-TyrArgTyrAspAspProPheTrp-172
SEQ. ID. NO. 10111    177-ProProAsnGlyTyrAsnCysArgCysSer-186
SEQ. ID. NO. 10112    190-LeuSerGluArgAspValGluArgGlnGlyArgIleValGlyGlnSerThrAlaAspAsnLeuValGlu-212
SEQ. ID. NO. 10113    215-LysIleTyrAsnLysLysGlyAspThr-223
SEQ. ID. NO. 10114    229-TyrLysAlaProAspGlySerLeuTyrThrThrAspArgGlyPheAspTyrAsnAlaGlyArgMetAsnTyrArgProAspLeuAspLysTyrAspArg
                      AlaLeu-263
SEQ. ID. NO. 10115    268-AlaLysAlaGluMetGlyGlyAlaAspPheLysThrSerPheLysGlnLeuGluLysGluPheTyrGluValLysGlnArgLeuAspIleAspGlyLys
                      ProAspLysGluGlnLysIleLysIleArgAsnAlaLeu-313
SEQ. ID. NO. 10116    324-LeuSerLysGluThrGlnGlu-330
SEQ. ID. NO. 10117    342-SerAspAspThrLeuValLysGlnValAspSerArgGluGlyGlnAsnPheAspAspSerTyrTyr-363
SEQ. ID. NO. 10118    370-LeuGlnAsnProGluHisValIleArgAspAsnArgGlu-382
SEQ. ID. NO. 10119    387-AlaArgTyrLysGlySer-392
SEQ. ID. NO. 10120    400-TyrIleLysGluValAspGlu-406
SEQ. ID. NO. 10121    411-SerTyrArgIleSerAsnAspLysGluIleAla-421
SEQ. ID. NO. 10122    424-MetAlaLysLysLysValLeuLys-431
Hydrophilic Regions - Hopp-Woods
SEQ. ID. NO. 10123    13-ProProLysLysAlaIleGlu-19
SEQ. ID. NO. 10124    21-LeuGluSerLysLysValThrAlaGluSerTyrArg-32
SEQ. ID. NO. 10125    55-AsnAspIleLysThrSerMet-61
SEQ. ID. NO. 10126    63-GluSerAlaLysSerGlyGlnSerPheAspAspTrpArgLys-76
SEQ. ID. NO. 10127    93-HisAsnGlyLysAspIleIleAsp-100
SEQ. ID. NO. 10128    108-GlySerProArgArgLeuGluThr-115
SEQ. ID. NO. 10129    147-AlaValGlyAspSerArgThrArgProAlaHisSerAla-159
SEQ. ID. NO. 10130    190-LeuSerGluArgAspValGluArgGlnGlyArgIleVal-202
SEQ. ID. NO. 10131    215-LysIleTyrAsnLysLysGlyAspThr-223
SEQ. ID. NO. 10132    238-ThrThrAspArgGlyPheAsp-244
SEQ. ID. NO. 10133    250-MetAsnTyrArgProAspLeuAspLysTyrAspArgAlaLeu-263
SEQ. ID. NO. 10134    268-AlaLysAlaGluMetGlyGlyAlaAspPheLysThrSerPheLysGlnLeuGluLysGluPheTyrGluValLysGlnArgLeuAspIleAspGlyLys
                      ProAspLysGluGlnLysIleLysIleArgAsnAlaLeu-313
SEQ. ID. NO. 10135    324-LeuSerLysGluThrGlnGlu-330
SEQ. ID. NO. 10136    344-AspThrLeuValLysGlnValAspSerArgGluGlyGlnAsnPheAsp-359
SEQ. ID. NO. 10137    375-HisValIleArgAspAsnArgGlu-382
SEQ. ID. NO. 10138    400-TyrIleLysGluValAspGlu-406
SEQ. ID. NO. 10139    414-IleSerAsnAspLysGluIleAla-421
SEQ. ID. NO. 10140    424-MetAlaLysLysLysValLeuLys-431
712
AMPHI Regions - AMPHI
SEQ. ID. NO. 10141    12-GlySerIleArgVal-16
SEQ. ID. NO. 10142    29-ValGlnGlyLeuProGlnAsnPro-36
SEQ. ID. NO. 10143    55-GluProValGlnLeuPhe-60
SEQ. ID. NO. 10144    72-GlySerLeuAlaHisLeuMet-78
SEQ. ID. NO. 10145    131-SerThrAlaValAsn-135
SEQ. ID. NO. 10146    142-ThrValAlaAspArgLeuLys-148
SEQ. ID. NO. 10147    210-ThrAlaLeuSerLysValAla-216
SEQ. ID. NO. 10148    231-AlaAsnAlaLysAlaLeuSerAsnHisIleThrAsnValSerAsnAlaIle-247
SEQ. ID. NO. 10149    306-ProAlaLysProLeuAsnThrLeuGlu-314
SEQ. ID. NO. 10150    329-PheAlaGluCysAsnAsnAlaLeuTyrAsnGlyLeuThrProLeu-343
SEQ. ID. NO. 10151    352-IleMetArgAlaValSerThrTyrThrLysSerAlaAsnAsn-365
SEQ. ID. NO. 10152    374-IleThrThrIleArgThrLeuAspTyrValArgArgSerVal-387
SEQ. ID. NO. 10153    411-GluIleLeuAspValLeuIle-417
SEQ. ID. NO. 10154    421-GlnAlaGluIleIleGluAsn-427
SEQ. ID. NO. 10155    441-GlnAsnAspProAsn-445
SEQ. ID. NO. 10156    454-AspValValAsnGlyLeu-459

TABLE 1-continued

Antigenic Index - Jameson-Wolf
SEQ. ID. NO. 10157  6-AspPheAspThrIleProGlySerIleArgValProGlyGln-19
SEQ. ID. NO. 10158  23-PheAsnThrArgAsnAlaVal-29
SEQ. ID. NO. 10159  32-LeuProGlnAsnProGlnLys-38
SEQ. ID. NO. 10160  61-SerAspAlaGluAlaAlaAsp-67
SEQ. ID. NO. 10161  125-IleGlyGlyLysGlnVal-130
SEQ. ID. NO. 10162  134-ValAsnThrGlyGluThrAla-140
SEQ. ID. NO. 10163  143-ValAlaAspArgLeuLysThr-149
SEQ. ID. NO. 10164  171-AlaLysHisLysGlyGluIleGlyAsnGluSerGlyLeu-183
SEQ. ID. NO. 10165  201-GlyGlyAlaLysAsnAlaAsp-207
SEQ. ID. NO. 10166  215-ValAlaGlyLysHis-219
SEQ. ID. NO. 10167  225-SerProPheSerAspAspAlaAsnAlaLysAlaLeuSer-237
SEQ. ID. NO. 10168  243-ValSerAsnAlaIleGluGlnArgGlyCys-252
SEQ. ID. NO. 10169  268-AlaThrGlyGluIleAsnAspGlyArgMet-277
SEQ. ID. NO. 10170  284-GlyAlaValGluProAsnGly-290
SEQ. ID. NO. 10171  302-PheGluGluAspProAlaLysProLeuAsn-311
SEQ. ID. NO. 10172  313-LeuGluIleLysGly-317
SEQ. ID. NO. 10173  320-ValThrProAspAlaGln-325
SEQ. ID. NO. 10174  332-CysAsnAsnAlaLeuTyrAsnGly-339
SEQ. ID. NO. 10175  358-ThrTyrThrLysSerAlaAsnAsnThrAspAspProAlaLeu-371
SEQ. ID. NO. 10176  381-AspTyrValArgArgSerValLysGluArgIleAlaLeuArgPheProArgAspLysLeuSerAspArgLeuLeuProLysValLysSerGluIle-412
SEQ. ID. NO. 10177  419-LeuAspGlnAlaGluIleIleGluAsnAlaGluAlaAsnLysGlyLysLeuValVal-437
SEQ. ID. NO. 10178  440-AlaGlnAsnAspProAsnArgValAsnAla-449
Hydrophilic Regions - Hopp-Woods
SEQ. ID. NO. 10179  61-SerAspAlaGluAlaAlaAsp-67
SEQ. ID. NO. 10180  135-AsnThrGlyGluThr-139
SEQ. ID. NO. 10181  143-ValAlaAspArgLeuLysThr-149
SEQ. ID. NO. 10182  171-AlaLysHisLysGlyGluIleGlyAsn-179
SEQ. ID. NO. 10183  203-AlaLysAsnAlaAsp-207
SEQ. ID. NO. 10184  227-PheSerAspAspAlaAsnAlaLysAlaLeu-236
SEQ. ID. NO. 10185  247-IleGluGlnArgGly-251
SEQ. ID. NO. 10186  270-GlyGluIleAsnAspGlyArgMet-277
SEQ. ID. NO. 10187  302-PheGluGluAspProAlaLysPro-309
SEQ. ID. NO. 10188  313-LeuGluIleLysGly-317
SEQ. ID. NO. 10189  362-SerAlaAsnAsnThrAspAspProAlaLeu-371
SEQ. ID. NO. 10190  381-AspTyrValArgArgSerValLysGluArgIleAla-392
SEQ. ID. NO. 10191  395-PheProArgAspLysLeuSerAspArgLeuLeuProLysValLysSerGluIle-412
SEQ. ID. NO. 10192  419-LeuAspGlnAlaGluIleIleGluAsnAlaGluAlaAsnLysGlyLysLeuValVal-437
SEQ. ID. NO. 10193  440-AlaGlnAsnAspProAsnArg-446
713
AMPHI Regions - AMPHI
SEQ. ID. NO. 10194  18-GluHisArgHisTrpGlu-23
SEQ. ID. NO. 10195  115-AspAlaAlaLysLysLeuAlaAlaProTrpProGlnIle-127
SEQ. ID. NO. 10196  150-ThrValTrpGlnAlaLeuThrHisIleAlaAsnSerVal-162
SEQ. ID. NO. 10197  257-AspAsnLeuAlaAlaLeuGln-263
SEQ. ID. NO. 10198  265-GlnAlaLysLysGln-269
Antigenic Index - Jameson-Wolf
SEQ. ID. NO. 10199  1-MetGlnAsnAsnSerTyrGly-7
SEQ. ID. NO. 10200  13-ArgValGlyGlyLysGluHisArgHisTrpGluArgTyrAspIleAspSerAspPhe-31
SEQ. ID. NO. 10201  44-ArgLeuGlyProGluAlaAlaIleProAspLeuSerGlySerCysGluValValIle-63
SEQ. ID. NO. 10202  74-GlySerGlnArgHisGlyLysSerLysGlySerArgGluLeuSerLeuSerGlyArgAspLeu-94
SEQ. ID. NO. 10203  106-LeuAsnValLysGly-110
SEQ. ID. NO. 10204  115-AspAlaAlaLysLysLeu-120
SEQ. ID. NO. 10205  131-ValLeuLysAlaGluAsnAsnProAlaLeuGlyLysIleAspIleGluProGlyGlu-149
SEQ. ID. NO. 10206  167-TrpLeuGluProAspGlyThrLeu-174
SEQ. ID. NO. 10207  177-GlyGlyAlaAspTyrSerSerProPro-185
SEQ. ID. NO. 10208  192-SerArgThrAspSerArgCysAsnIleGluArgMetAspIleGluTrpAspThrAspAsnArgPheSerGlu-215
SEQ. ID. NO. 10209  222-SerHisGlyArgSerGlyAspSerAlaLysHisAspLeu-234
SEQ. ID. NO. 10210  237-ValTyrLysAspProThrMetThrLeuHisArgProLysThrValVal-252
SEQ. ID. NO. 10211  254-SerAspAlaAspAsn-258
SEQ. ID. NO. 10212  263-GlnLysGlnAlaLysLysGlnLeuAla-271
SEQ. ID. NO. 10213  284-ValGlyGlyHisLysThrArgAspGly-292
SEQ. ID. NO. 10214  303-ValIleAspAspGluHisGlyIle-310
SEQ. ID. NO. 10215  321-PheMetLeuSerArgMetAspGlyThrGlnThrGluLeuArgLeuLysGluAspGlyIleTrpThrProAspAlaTyrProLysLysAlaGluAlaAla
                    ArgLysArgLysGlyLysArgLysGlyValSerHisLysGlyLysLysGlyGlyLysLysGlnAlaGlu-376
Hydrophilic Regions - Hopp-Woods
SEQ. ID. NO. 10216  14-ValGlyGlyLysGluHisArgHisTrpGluArgTyrAspIleAspSer-29
SEQ. ID. NO. 10217  54-LeuSerGlyGluSerCysGluValValIle-63
SEQ. ID. NO. 10218  76-GlnArgHisGlyLysSerLysGlySerArgGluLeuSerLeuSerGlyArgAspLeu-94
SEQ. ID. NO. 10219  115-AspAlaAlaLysLysLeu-120
SEQ. ID. NO. 10220  131-ValLeuLysAlaGluAsnAsnProAla-139
SEQ. ID. NO. 10221  141-GlyLysIleAspIleGluProGlyGlu-149
SEQ. ID. NO. 10222  168-LeuGluProAspGly-172
SEQ. ID. NO. 10223  193-ArgThrAspSerArgCysAsnIleGluArgMetAspIleGluTrpAspThrAspAsnArgPheSer-214
SEQ. ID. NO. 10224  222-SerHisGlyArgSerGlyAspSerAlaLysHisAspLeu-234
SEQ. ID. NO. 10225  246-HisArgProLysThr-250
SEQ. ID. NO. 10226  254-SerAspAlaAspAsn-258
SEQ. ID. NO. 10227  263-GlnLysGlnAlaLysLysGlnLeuAla-271
SEQ. ID. NO. 10228  286-GlyHisLysThrArgAsp-291
SEQ. ID. NO. 10229  303-ValIleAspAspGluHisGlyIle-310

TABLE 1-continued

| | |
|---|---|
| SEQ. ID. NO. 10230 | 325-ArgMetAspGlyThrGlnThrGluLeuArgLeuLysGluAspGlyIleTrp-341 |
| SEQ. ID. NO. 10231 | 345-AlaTyrProLysLysAlaGluAlaAlaArgLysArgLysGlyLysArgLysGlyValSerHisLysGlyLysLysGlyGlyLysLysGlnAlaGlu-376 |

714
AMPHI Regions - AMPHI

| | |
|---|---|
| SEQ. ID. NO. 10232 | 6-IleLeuArgGlyLeuLeuPro-12 |
| SEQ. ID. NO. 10233 | 34-LeuAspAlaValAlaGluSerAlaGlnSerValAla-45 |
| SEQ. ID. NO. 10234 | 54-GlyGlnMetLeuAlaAspTrpGluArgValLeuGlyLeu-66 |
| SEQ. ID. NO. 10235 | 79-AlaValMetAlaLysLeuAsnGluThrGly-88 |
| SEQ. ID. NO. 10236 | 98-LeuAlaGluAlaAla-102 |
| SEQ. ID. NO. 10237 | 110-GluProGlnProPhe-114 |
| SEQ. ID. NO. 10238 | 116-AlaGlyValAsnArgAlaGlyAspArgLeu-125 |
| SEQ. ID. NO. 10239 | 155-AlaGlyAspArgLeuThrAspTyrSerAspAlaValIleGluSerLeuPheAsnArgLeuLys-175 |

Antigenic Index - Jameson-Wolf

| | |
|---|---|
| SEQ. ID. NO. 10240 | 15-SerTyrAlaArgAsnAlaProArgValArgAlaGlnAlaGluIleAspGlyAlaAla-33 |
| SEQ. ID. NO. 10241 | 36-AlaValAlaGluSerAlaGlnSerVal-44 |
| SEQ. ID. NO. 10242 | 46-AspAlaValAspProArgSerAla-53 |
| SEQ. ID. NO. 10243 | 64-LeuGlyLeuAspGlyThrGlyLysAsnArgGlnHisArg-76 |
| SEQ. ID. NO. 10244 | 83-LysLeuAsnGluThrGlyGlyLeu-90 |
| SEQ. ID. NO. 10245 | 107-GlnIleAspGluProGlnProPheArgAlaGlyValAsnArgAlaGlyAspArgLeuAlaPro-127 |
| SEQ. ID. NO. 10246 | 138-ValArgGlyGlyAsnAsnArgIleThrArgPheArgAlaGlyIle-152 |
| SEQ. ID. NO. 10247 | 154-AlaAlaGlyAspArgLeuThrAspTyrSerAspAlaValIle-167 |
| SEQ. ID. NO. 10248 | 170-LeuPheAsnArgLeuLysPro-176 |

Hydrophilic Regions - Hopp-Woods

| | |
|---|---|
| SEQ. ID. NO. 10249 | 18-ArgAsnAlaProArgValArgAlaGlnAlaGluIleAspGlyAlaAla-33 |
| SEQ. ID. NO. 10250 | 36-AlaValAlaGluSerAlaGlnSerVal-44 |
| SEQ. ID. NO. 10251 | 46-AspAlaValAspProArgSerAla-53 |
| SEQ. ID. NO. 10252 | 68-GlyThrGlyLysAsnArgGlnHisArg-76 |
| SEQ. ID. NO. 10253 | 107-GlnIleAspGluProGlnProPhe-114 |
| SEQ. ID. NO. 10254 | 117-GlyValAsnArgAlaGlyAspArgLeuAlaPro-127 |
| SEQ. ID. NO. 10255 | 139-ArgGlyGlyAsnAsnArgIleThrArgPheArgAla-150 |
| SEQ. ID. NO. 10256 | 154-AlaAlaGlyAspArgLeuThrAspTyrSerAspAlaValIle-167 |
| SEQ. ID. NO. 10257 | 170-LeuPheAsnArgLeuLysPro-176 |

715
AMPHI Regions - AMPHI

| | |
|---|---|
| SEQ. ID. NO. 10258 | 15-GlnIleGluArgLeuGlyAsnGlyIle-23 |
| SEQ. ID. NO. 10259 | 31-ArgArgLeuSerGluThrMetHis-38 |
| SEQ. ID. NO. 10260 | 64-LeuSerAspSerGlyArgLeuLysAspSerPheSer-75 |
| SEQ. ID. NO. 10261 | 94-IleHisAsnPheGlyGly-99 |

Antigenic Index - Jameson-Wolf

| | |
|---|---|
| SEQ. ID. NO. 10262 | 15-GlnIleGluArgLeuGlyAsnGlyIleGluAsnArgTyrLeuLeu-29 |
| SEQ. ID. NO. 10263 | 47-TyrAlaGlyArgProLysTrpValGlyLeuLysTyrArgAspGlyLysProLeuSerAspSerGlyArgLeuLysAspSerPheSerThrLeuSerAspAsnAspThrAla-83 |
| SEQ. ID. NO. 10264 | 98-GlyGlyMetAlaGlyArgAsnArgLysValArgIleProGlnArgGluPhe-114 |
| SEQ. ID. NO. 10265 | 118-ThrAspAspAspLysGlnAlaLeuMetAspAspValGlnAsp-131 |

Hydrophilic Regions - Hopp-Woods

| | |
|---|---|
| SEQ. ID. NO. 10266 | 15-GlnIleGluArgLeuGlyAsn-21 |
| SEQ. ID. NO. 10267 | 57-LysTyrArgAspGlyLysProLeuSerAspSerGlyArgLeuLysAspSerPhe-74 |
| SEQ. ID. NO. 10268 | 78-SerAspAsnAspThr-82 |
| SEQ. ID. NO. 10269 | 101-AlaGlyArgAsnArgLysValArgIleProGlnArgGlu-113 |
| SEQ. ID. NO. 10270 | 118-ThrAspAspAspLysGlnAlaLeuMetAspAspValGlnAsp-131 |

716
AMPHI Regions - AMPHI

| | |
|---|---|
| SEQ. ID. NO. 10271 | 33-GlyValHisLysSerAlaHisGly-40 |
| SEQ. ID. NO. 10272 | 71-AlaThrValLysLysThrHisLysHisThrLysAla-82 |

Antigenic Index - Jameson-Wolf

| | |
|---|---|
| SEQ. ID. NO. 10273 | 1-MetAsnLysAsnIle-5 |
| SEQ. ID. NO. 10274 | 23-AlaAlaAsnLysProAlaSerAsnAlaThrGlyValHisLysSerAlaHisGlySerCysGlyAlaSerLysSerAlaGluGlySerCysGlyAlaAlaGlySerLysAlaGlyGluGlyLysCysGlyGluGlyLysCysGlyAlaThrValLysLysThrHisLysHisThrLysAlaSerLysAlaLysAlaLysSerAlaGluGlyLysCysGlyGluGlyLysCysGlySerLys-102 |

Hydrophilic Regions - Hopp-Woods

| | |
|---|---|
| SEQ. ID. NO. 10275 | 23-AlaAlaAsnLysProAlaSer-29 |
| SEQ. ID. NO. 10276 | 33-GlyValHisLysSerAlaHis-39 |
| SEQ. ID. NO. 10277 | 43-GlyAlaSerLysSerAlaGluGlySerCys-52 |
| SEQ. ID. NO. 10278 | 55-AlaGlySerLysAlaGlyGluGlyLysCysGlyGluGlyLysCys-69 |
| SEQ. ID. NO. 10279 | 71-AlaThrValLysLysThrHisLysHisThrLysAlaSerLysAlaLysAlaLysSerAlaGluGlyLysCysGlyGluGlyLysCysGlySerLys-102 |

717
AMPHI Regions - AMPHI

| | |
|---|---|
| SEQ. ID. NO. 10280 | 175-AlaValTyrAlaLeuAlaAsn-181 |
| SEQ. ID. NO. 10281 | 209-LeuHisArgGlyLeu-213 |
| SEQ. ID. NO. 10282 | 223-SerIleAlaTyrTrp-227 |
| SEQ. ID. NO. 10283 | 241-AlaGlyLeuGluGlnLeuGly-247 |
| SEQ. ID. NO. 10284 | 263-GlnSerIlePheSerThrValTrpThrProTyrIlePheArgAlaIleGluGlu-280 |
| SEQ. ID. NO. 10285 | 305-ThrGlyIlePheSerProLeuAlaSer-313 |
| SEQ. ID. NO. 10286 | 347-LeuAsnValValArgLysThr-353 |
| SEQ. ID. NO. 10287 | 358-LeuAlaThrLeuGlyAlaLeuAla-365 |
| SEQ. ID. NO. 10288 | 401-SerSerCysArgLeuTrpGlnProLeuLysArgLeu-412 |
| SEQ. ID. NO. 10289 | 430-CysPheGlyThrPro-434 |
| SEQ. ID. NO. 10290 | 442-GlyValTrpAlaAlaTyrLeuAlaGly-450 |
| SEQ. ID. NO. 10291 | 457-LysAspLeuHisLysLeuPheHisTyr-465 |

TABLE 1-continued

Antigenic Index - Jameson-Wolf
SEQ. ID. NO. 10292  1-MetAspThrLysGlu-5
SEQ. ID. NO. 10293  32-ProAlaAspAspIleGlyArg-38
SEQ. ID. NO. 10294  66-TyrAlaThrAlaAspLysAspThrLeu-74
SEQ. ID. NO. 10295  95-SerArgProSerLeuProSerGluIle-103
SEQ. ID. NO. 10296  135-MetGluGlyArgAla-139
SEQ. ID. NO. 10297  192-AsnArgCysArgLeuLysAlaValArg-200
SEQ. ID. NO. 10298  231-SerAlaAspArgLeuPheLeu-237
SEQ. ID. NO. 10299  277-AlaIleGluGluAsnAlaProProAlaArgLeu-287
SEQ. ID. NO. 10300  289-AlaThrAlaGluSer-293
SEQ. ID. NO. 10301  317-ProGluAsnTyrAla-321
SEQ. ID. NO. 10302  349-ValValArgLysThrArgProIleAla-357
SEQ. ID. NO. 10303  376-ProSerGlyGlyAlaArgGly-382
SEQ. ID. NO. 10304  397-PheLysThrGluSerSerCysArgLeu-405
SEQ. ID. NO. 10305  453-LeuArgHisArgLysAspLeuHis-460
Hydrophilic Regions - Hopp-Woods
SEQ. ID. NO. 10306  1-MetAspThrLysGlu-5
SEQ. ID. NO. 10307  66-TyrAlaThrAlaAspLysAspThrLeu-74
SEQ. ID. NO. 10308  135-MetGluGlyArgAla-139
SEQ. ID. NO. 10309  192-AsnArgCysArgLeuLysAlaValArg-200
SEQ. ID. NO. 10310  277-AlaIleGluGluAsnAlaProProAlaArgLeu-287
SEQ. ID. NO. 10311  289-AlaThrAlaGluSer-293
SEQ. ID. NO. 10312  349-ValValArgLysThrArgPro-355
SEQ. ID. NO. 10313  378-GlyGlyAlaArgGly-382
SEQ. ID. NO. 10314  398-LysThrGluSerSerCys-403
SEQ. ID. NO. 10315  453-LeuArgHisArgLysAspLeuHis-460
718-1
AMPHI Regions - AMPHI
SEQ. ID. NO. 10316  28-IleThrAlaThrGlyArgValIleAlaGluHisProSerAsnPheIleThrProGln-46
SEQ. ID. NO. 10317  49-ArgAlaLeuPheGlu-53
SEQ. ID. NO. 10318  110-AspGlnAlaTyrGluMetMetAspSerLeuProThr-121
SEQ. ID. NO. 10319  124-AspLeuIleMetAspLeuMetAspAlaValGlyHisGly-136
SEQ. ID. NO. 10320  160-ProGlnSerTrpPheLys-165
SEQ. ID. NO. 10321  198-ArgSerValGlnGln-202
SEQ. ID. NO. 10322  210-ThrLeuSerTrpLeuTyrMetPhe-217
SEQ. ID. NO. 10323  219-HisTyrAlaValHisAspPheAlaGluPheLeuGluLeu-231
SEQ. ID. NO. 10324  255-ArgAlaValAlaGluIle-260
SEQ. ID. NO. 10325  280-AlaAsnGlyThrThr-284
SEQ. ID. NO. 10326  320-ThrAsnAlaLeuGlyAsnIleHisAsnGluValArg-331
SEQ. ID. NO. 10327  341-GlnValAlaGlnThrIleThrSerGlnIleIleGlyProPhe-354
SEQ. ID. NO. 10328  363-AspProAsnArgVal-367
SEQ. ID. NO. 10329  376-GluProLysAspIleAlaValPheAlaAspAlaIleProLysLeuValAsp-392
SEQ. ID. NO. 10330  395-ValGlnIleProGlu-399
SEQ. ID. NO. 10331  420-ArgGlnValProAspAsnPro-426
SEQ. ID. NO. 10332  448-HisGlnGluIleLeuAspGlyAlaLeuAspAsp-458
SEQ. ID. NO. 10333  469-LeuAsnProMetValArgGlnAlaValAlaAlaLeuAsnAlaCysAsnSerTyrGlu-487
Antigenic Index - Jameson-Wolf
SEQ. ID. NO. 10334  4-IleMetAlaLysLysAsnAsnLysThrLysIleGlnLysProGluAlaAlaLeu-21
SEQ. ID. NO. 10335  30-AlaThrGlyArgValIleAla-36
SEQ. ID. NO. 10336  38-HisProSerAsnPhe-42
SEQ. ID. NO. 10337  44-ThrProGlnLysMetArgAlaLeuPheGluAspAlaGluSerGlyAspIleArgAlaGlnHis-64
SEQ. ID. NO. 10338  68-AlaAspIleGluGluArgAspSerAspIle-77
SEQ. ID. NO. 10339  81-MetGlyThrArgLysArgAla-87
SEQ. ID. NO. 10340  95-ValAlaProProArgAsnAlaThrProGluGluGluLysLeuSerAspGlnAlaTyrGluMet-115
SEQ. ID. NO. 10341  119-LeuProThrProLeuGlu-123
SEQ. ID. NO. 10342  148-AspGlyLeuTyrLeuProArgAsnPheIleHisArgProGlnSerTrpPheLysTrpAspLysAspAsnGlyLeu-172
SEQ. ID. NO. 10343  174-LeuArgThrArgGluAsnProGluGlyGluAla-184
SEQ. ID. NO. 10344  193-HisThrGlnLysSerArgSerValGlnGlnAlaArgAsnGlyLeuPhe-208
SEQ. ID. NO. 10345  237-ArgIleGlyLysTyrGlyAlaGlyAlaThrLysGluLysAsnThrLeu-253
SEQ. ID. NO. 10346  268-MetProGluGlyMetGluIleGluLeu-276
SEQ. ID. NO. 10347  280-AlaAsnGlyThrThrAlaThr-286
SEQ. ID. NO. 10348  295-AspTrpCysGluLysSerAlaAla-302
SEQ. ID. NO. 10349  310-LeuThrSerGlyAlaAspGlyLysSerSerThrAsnAlaLeuGly-324
SEQ. ID. NO. 10350  328-AsnGluValArgArgAspLeuLeuValSerAspAlaLysGlnVal-342
SEQ. ID. NO. 10351  359-TyrProHisAlaAspProAsnArgValProLysPheGluPheAspThrArgGluProLysAspIle-380
SEQ. ID. NO. 10352  397-IleProGluSerTrpValArgAspLysLeuVal-407
SEQ. ID. NO. 10353  410-AspValGlnGluGlyGlyAluAlaValLeu-418
SEQ. ID. NO. 10354  420-ArgGlnValProAspAsnProValAsnArg-429
SEQ. ID. NO. 10355  440-ValProSerLysAlaThrGlyArgHisGlnGluIleLeuAspGlyAlaLeuAsp-457
SEQ. ID. NO. 10356  459-AlaLeuValGluProAspPheAsnSerGlnLeu-469
SEQ. ID. NO. 10357  484-AsnSerTyrGluGluAlaAspAla-491
SEQ. ID. NO. 10358  499-AsnLeuAspAsnAlaLysLeuArgThr-507
SEQ. ID. NO. 10359  519-LeuGlyGlnAspHisAlaArgAla-526
Hydrophilic Regions - Hopp-Woods
SEQ. ID. NO. 10360  4-IleMetAlaLysLysAsnAsnLysThrLysIleGlnLysProGluAlaAlaLeu-21
SEQ. ID. NO. 10361  46-GlnLysMetArgAlaLeuPheGluAspAlaGluSerGlyAspIleArgAlaGlnHis-64
SEQ. ID. NO. 10362  68-AlaAspIleGluGluArgAspSerAspIle-77
SEQ. ID. NO. 10363  81-MetGlyThrArgLysArgAla-87
SEQ. ID. NO. 10364  96-AlaProProArgAsnAlaThrProGluGluGluLysLeuSerAspGlnAlaTyrGluMet-115
SEQ. ID. NO. 10365  165-LysTrpAspLysAspAsnGlyLeu-172

TABLE 1-continued

| | |
|---|---|
| SEQ. ID. NO. 10366 | 174-LeuArgThrArgGluAsnProGluGlyGluAla-184 |
| SEQ. ID. NO. 10367 | 195-GlnLysSerArgSerValGlnGlnAlaArg-204 |
| SEQ. ID. NO. 10368 | 245-AlaThrLysGluGluLysAsnThrLeu-253 |
| SEQ. ID. NO. 10369 | 270-GluGlyMetGluIleGluLeu-276 |
| SEQ. ID. NO. 10370 | 295-AspTrpCysGluLysSerAlaAla-302 |
| SEQ. ID. NO. 10371 | 312-SerGlyAlaAspGlyLysSerSerThr-320 |
| SEQ. ID. NO. 10372 | 328-AsnGluValArgArgAspLeuLeuValSerAspAlaLysGlnVal-342 |
| SEQ. ID. NO. 10373 | 363-AspProAsnArgValProLysPheGluPheAspThrArgGluProLysAsp-379 |
| SEQ. ID. NO. 10374 | 401-TrpValArgAspLysLeuVal-407 |
| SEQ. ID. NO. 10375 | 410-AspValGlnGluGlyGluAlaValLeu-418 |
| SEQ. ID. NO. 10376 | 421-GlnValProAspAsnProValAsn-428 |
| SEQ. ID. NO. 10377 | 440-ValProSerLysAlaThrGlyArgHisGlnGluIleLeuAspGlyAlaLeuAsp-457 |
| SEQ. ID. NO. 10378 | 485-SerTyrGluGluAlaAspAla-491 |
| SEQ. ID. NO. 10379 | 501-AspAsnAlaLysLeu-505 |
| SEQ. ID. NO. 10380 | 522-AspHisAlaArgAla-526 |
| 719 | |
| AMPHIRegions - AMPHI | |
| SEQ. ID. NO. 10381 | 21-ArgLeuLeuAlaAspThrGlnArgGlnLeuAspArgThrAla-34 |
| SEQ. ID. NO. 10382 | 68-AlaPheAsnArgLeuAlaArgSerGlyLys-77 |
| SEQ. ID. NO. 10383 | 79-SerGlnAsnAspLeu-83 |
| SEQ. ID. NO. 10384 | 104-GlyThrGlyPheAlaAspLysMetGlyLysIleGlyArgPheGlyAla-119 |
| SEQ. ID. NO. 10385 | 143-AspGluAsnIleAsnArgValSerArg-151 |
| SEQ. ID. NO. 10386 | 191-AlaLeuAspLeuIleSerGlyMetMet-199 |
| SEQ. ID. NO. 10387 | 229-ThrAlaLysLeuIleLysThrLeuLysAsp-238 |
| SEQ. ID. NO. 10388 | 254-LeuGlnSerGlyLeu-258 |
| SEQ. ID. NO. 10389 | 266-AspMetValArgGluLeuProSerLeuLeuSer-276 |
| SEQ. ID. NO. 10390 | 280-GlnAlaGlyMetAsnGlyValGlyGlyLeuAspTyrLeuLeuSerLeuLeu-296 |
| SEQ. ID. NO. 10391 | 308-GluAlaAlaThrAsnValGlnAsnLeuLeuSerLys-319 |
| SEQ. ID. NO. 10392 | 324-AspThrIleGlyArgLeuLysLysMetAlaAsnProAsnAspProLysLysGlyValAspTrpIleGlySer-347 |
| SEQ. ID. NO. 10393 | 360-GlnValLeuSerArgLeuAlaAsp-367 |
| SEQ. ID. NO. 10394 | 404-GlnLeuLeuProAspLeu-409 |
| SEQ. ID. NO. 10395 | 418-AlaThrAspMetThrGlnIleArgGluTyrMetAlaSerLeu-431 |
| SEQ. ID. NO. 10396 | 467-GluSerLeuThrGlyThr-472 |
| SEQ. ID. NO. 10397 | 477-GluThrSerPheLysLysLeuAlaAlaGlu-486 |
| SEQ. ID. NO. 10398 | 497-LeuThrThrAlaAla-501 |
| SEQ. ID. NO. 10399 | 519-GlyPheLeuLysAspValGly-525 |
| SEQ. ID. NO. 10400 | 557-AlaGlySerGlyLeu-561 |
| SEQ. ID. NO. 10401 | 588-LeuProLysGlyLeuArgGlyThr-595 |
| SEQ. ID. NO. 10402 | 597-ThrThrProGluMetIleAsnArgLeuLys-606 |
| SEQ. ID. NO. 10403 | 626-ProGlnTyrLeuAlaAlaPro-632 |
| SEQ. ID. NO. 10404 | 635-GlnProThrAspLysMetLeuSerProLeuPhe-645 |
| SEQ. ID. NO. 10405 | 676-ThrGlyLeuAlaGlnValGlnSerAlaMetAla-686 |
| SEQ. ID. NO. 10406 | 707-AsnGluValSerArg-711 |
| Antigenic Index - Jameson-Wolf | |
| SEQ. ID. NO. 10407 | 1-MetAlaAsnGlyAsnMet-6 |
| SEQ. ID. NO. 10408 | 14-AlaArgAspAspGlyAlaArgArgLeuLeuAlaAspThrGlnArgGlnLeuAspArgThrAlaLysSerArgAlaGlnLeuGluArgGlnSerHisThrTyr-47 |
| SEQ. ID. NO. 10409 | 51-GlyIleArgSerGluLysGlnIleGlnArg-60 |
| SEQ. ID. NO. 10410 | 71-ArgLeuAlaArgSerGlyLysAlaSerGlnAsnAspLeuAlaArg-85 |
| SEQ. ID. NO. 10411 | 90-ThrArgAsnArgIleArgGluLeuAsnAlaGluLeuLysGlnGlyThrGlyPheAlaAspLysMetGlyLysIleGlyArgPheGly-118 |
| SEQ. ID. NO. 10412 | 134-ProAlaMetAspAsnArgLysGlnLeuAspGluAsnIleAsnArgValSerArg-151 |
| SEQ. ID. NO. 10413 | 153-AlaPheIleGluAspAsnSerLysSerAla-162 |
| SEQ. ID. NO. 10414 | 168-GluGlyAlaGlnGlnIleLysAspLeuAla-177 |
| SEQ. ID. NO. 10415 | 180-LeuValGluLysAsnGlyGlyThrHisAspLysAlaLeuAsp-193 |
| SEQ. ID. NO. 10416 | 207-GlnThrLysAsnGluAla-212 |
| SEQ. ID. NO. 10417 | 222-SerGluGlySerGlyGluAspThrAlaLysLeu-232 |
| SEQ. ID. NO. 10418 | 234-LysThrLeuLysAspGlyGlyMetSerGlyLysAspLeuGlnLeu-248 |
| SEQ. ID. NO. 10419 | 256-SerGlyLeuAspGlyThrPheGluValArgAspMetValArgGluLeuProSer-273 |
| SEQ. ID. NO. 10420 | 299-AlaAlaAsnLysSerGlySerProAlaGluAla-309 |
| SEQ. ID. NO. 10421 | 318-SerLysThrLeuSerProAspThrIleGlyArgLeuLysLysMetAlaAsnProAsnAspProLysLysGlyValAspTrp-344 |
| SEQ. ID. NO. 10422 | 349-ValGlnGlyLysGlnAsnGlyGluAsn-357 |
| SEQ. ID. NO. 10423 | 369-MetLeuValLysAspLysGlnTyrGlnAspTyrLysLysArgAlaAlaAlaGlyAspLysThrAlaAlaGluGln-393 |
| SEQ. ID. NO. 10424 | 422-ThrGlnIleArgGluTyrMet-428 |
| SEQ. ID. NO. 10425 | 437-AspAsnGlyLysIleAlaLysAsnAsnGluAlaArgMet-449 |
| SEQ. ID. NO. 10426 | 454-AlaGlnGlnGluGlnGlnGluSer-461 |
| SEQ. ID. NO. 10427 | 463-AlaMetLeuArgGluSerLeu-469 |
| SEQ. ID. NO. 10428 | 474-ValAspMetGluThrSerPheLysLysLeuAlaAla-485 |
| SEQ. ID. NO. 10429 | 511-ThrAlaGlyGlyGlyLysGlyAlaGlyPhe-520 |
| SEQ. ID. NO. 10430 | 522-LysAspValGlySerLysAla-528 |
| SEQ. ID. NO. 10431 | 532-GlyLysAlaSerAlaGlyGly-538 |
| SEQ. ID. NO. 10432 | 545-AlaAlaGlyGlyLys-549 |
| SEQ. ID. NO. 10433 | 554-GlyLysSerAlaGlySerGlyLeuMetAsnAsnProAlaLeuValLysArgAlaGly-572 |
| SEQ. ID. NO. 10434 | 580-SerGluSerLeuGlyAspGlyThrLeuProLysGlyLeuArgGlyThrLysThrThrPro-599 |
| SEQ. ID. NO. 10435 | 601-MetIleAsnArgLeuLysAsnAsnGlyIleArgPheGluProAlaProLysArgGluGlnAlaArgGlyGlyValPro-626 |
| SEQ. ID. NO. 10436 | 631-AlaProSerProAlaGlnProThrAspLysMetLeuSerPro-643 |
| SEQ. ID. NO. 10437 | 687-SerAlaSerGlnThrIleAsnThrAsnValSerLeuAsnIleAspGlyArgValIleAla-706 |
| SEQ. ID. NO. 10438 | 708-GluValSerArgTyrGln-713 |
| SEQ. ID. NO. 10439 | 718-GlyArgGlyAlaGlyGln-723 |
| Hydrophilic Regions - Hopp-Woods | |
| SEQ. ID. NO. 10440 | 14-AlaArgAspAspGlyAlaArgArgLeuLeuAlaAspThrGlnArgGlnLeuAspArgThrAlaLysSerArgAlaGlnLeuGluArgGlnSer-44 |

TABLE 1-continued

| | |
|---|---|
| SEQ. ID. NO. 10441 | 52-IleArgSerGluLysGlnIleGlnArg-60 |
| SEQ. ID. NO. 10442 | 71-ArgLeuAlaArgSerGlyLysAlaSerGlnAsnAspLeuAlaArg-85 |
| SEQ. ID. NO. 10443 | 90-ThrArgAsnArgIleArgGluLeuAsnAlaGluLeuLysGln-103 |
| SEQ. ID. NO. 10444 | 107-PheAlaAspLysMetGlyLysIleGlyArg-116 |
| SEQ. ID. NO. 10445 | 134-ProAlaMetAspAsnArgLysGlnLeuAspGluAsnIleAsnArgValSerArg-151 |
| SEQ. ID. NO. 10446 | 153-AlaPheIleGluAspAsnSerLys-160 |
| SEQ. ID. NO. 10447 | 168-GluGlyAlaGlnGlnIleLysAspLeuAla-177 |
| SEQ. ID. NO. 10448 | 180-LeuValGluLysAsnGlyGlyThrHisAspLysAlaLeuAsp-193 |
| SEQ. ID. NO. 10449 | 207-GlnThrLysAsnGluAla-212 |
| SEQ. ID. NO. 10450 | 222-SerGluGlySerGlyGluAspThrAlaLysLeu-232 |
| SEQ. ID. NO. 10451 | 234-LysThrLeuLysAspGlyGlyMetSerGlyLysAspLeuGlnLeu-248 |
| SEQ. ID. NO. 10452 | 262-PheGluValArgAspMetValArgGluLeuPro-272 |
| SEQ. ID. NO. 10453 | 299-AlaAlaAsnLysSerGlySerProAlaGluAla-309 |
| SEQ. ID. NO. 10454 | 325-ThrIleGlyArgLeuLysLysMetAlaAsnProAsnAspProLysLysGlyVal-342 |
| SEQ. ID. NO. 10455 | 349-ValGlnGlyLysGlnAsnGlyGluAsn-357 |
| SEQ. ID. NO. 10456 | 369-MetLeuValLysAspLysGlnTyrGlnAspTyrLysLysArgAlaAlaAlaGlyAspLysThrAlaAlaGluGln-393 |
| SEQ. ID. NO. 10457 | 422-ThrGlnIleArgGluTyrMet-428 |
| SEQ. ID. NO. 10458 | 437-AspAsnGlyLysIleAlaLysAsnAsnGluAlaArgMet-449 |
| SEQ. ID. NO. 10459 | 454-AlaGlnGlnGluGlnGlnGluSer-461 |
| SEQ. ID. NO. 10460 | 463-AlaMetLeuArgGluSerLeu-469 |
| SEQ. ID. NO. 10461 | 474-ValAspMetGluThrSerPheLysLysLeuAlaAla-485 |
| SEQ. ID. NO. 10462 | 522-LysAspValGlySer-526 |
| SEQ. ID. NO. 10463 | 567-LeuValLysArgAlaGly-572 |
| SEQ. ID. NO. 10464 | 590-LysGlyLeuArgGlyThrLysThrThrPro-599 |
| SEQ. ID. NO. 10465 | 601-MetIleAsnArgLeuLysAsnAsnGlyIleArgPheGluProAlaProLysArgGluGlnAlaArgGlyGly-624 |
| SEQ. ID. NO. 10466 | 635-GlnProThrAspLysMetLeu-641 |
| SEQ. ID. NO. 10467 | 700-IleAspGlyArgValIleAla-706 |
| 720 | |
| AMPHI Regions - AMPHI | |
| SEQ. ID. NO. 10468 | 6-ThrLeuLeuGlnAspAlaSer-12 |
| SEQ. ID. NO. 10469 | 24-AspGluSerAsnGlyLysAlaLeuAlaGluHisAlaArgProPhe-38 |
| SEQ. ID. NO. 10470 | 65-TyrAlaGlyArgLeuLysLysLeuLeuAspAlaLeuGluGlnPro-79 |
| SEQ. ID. NO. 10471 | 87-ProValTrpGlyArgMetHisAsnMetIleAlaAla-98 |
| SEQ. ID. NO. 10472 | 142-IleAlaAsnIleAspThrTyrArg-149 |
| SEQ. ID. NO. 10473 | 166-ValSerAlaLeuTrpGlySerAlaLeuGly-175 |
| SEQ. ID. NO. 10474 | 184-PheGlyAlaValArgArgLeuPheAspLeuAspLysIleAla-197 |
| SEQ. ID. NO. 10475 | 212-GlySerAlaLysLeuPheAlaAspIleSerVal-222 |
| SEQ. ID. NO. 10476 | 268-LeuThrGlyArgPheSerAspGlyLeuGlnAsnArgLeuAsnArgLeu-283 |
| SEQ. ID. NO. 10477 | 293-GlnAlaValArgLeuLeuSerThrSer-301 |
| SEQ. ID. NO. 10478 | 320-AlaProAspLeuIleGluValAsn-327 |
| SEQ. ID. NO. 10479 | 340-AlaLeuArgAlaValGlnThrAla-347 |
| SEQ. ID. NO. 10480 | 365-GlnThrAlaGluSerLeu-370 |
| SEQ. ID. NO. 10481 | 376-ArgLeuAsnAlaLeuValAla-382 |
| SEQ. ID. NO. 10482 | 400-GlyThrIleHisGlnIleAlaHisGluPheTyrGlyAspIleAlaArgAlaAlaGluLeuVal-420 |
| Antigenic Index - Jameson-Wolf | |
| SEQ. ID. NO. 10483 | 8-LeuGlnAspAlaSerTyrLysGlyValGlyPhe-18 |
| SEQ. ID. NO. 10484 | 21-GluValValAspGluSerAsnGlyLysAlaLeuAlaGluHisAlaArg-36 |
| SEQ. ID. NO. 10485 | 42-IleAspLeuGluAspMetGlyMetThrGlyArg-52 |
| SEQ. ID. NO. 10486 | 62-GlyLysGlyTyrAlaGlyArgLeuLysLysLeuLeuAspAlaLeuGluGlnProGlyGlyGly-82 |
| SEQ. ID. NO. 10487 | 101-SerTyrArgHisGluAlaAspTyr-108 |
| SEQ. ID. NO. 10488 | 117-ThrPheArgGluAlaAlaGluAlaGln-125 |
| SEQ. ID. NO. 10489 | 146-AspThrTyrArgGluAlaAla-152 |
| SEQ. ID. NO. 10490 | 189-ArgLeuPheAspLeuAspLys-195 |
| SEQ. ID. NO. 10491 | 197-AlaPheProAspArgGlyGlyTyrSer-205 |
| SEQ. ID. NO. 10492 | 209-PheLysAsnGlySer-213 |
| SEQ. ID. NO. 10493 | 226-ThrGlyIleArgArgGluAlaGlyLeu-234 |
| SEQ. ID. NO. 10494 | 244-TrpSerProArgGlnArgPheAspGly-252 |
| SEQ. ID. NO. 10495 | 256-ValAlaAspArgAlaAlaAlaIleProAspAsn-266 |
| SEQ. ID. NO. 10496 | 270-GlyArgPheSerAspGlyLeuGlnAsnArgLeuAsnArgLeuThrAlaLysGlnVal-288 |
| SEQ. ID. NO. 10497 | 313-AlaHisGlyGluGluMetThrAla-320 |
| SEQ. ID. NO. 10498 | 322-AspLeuIleGluValAsnArgAlaMetArgArgArgMetGlnAla-336 |
| SEQ. ID. NO. 10499 | 348-AlaAlaGluSerGlyGlyLeuThrAla-356 |
| SEQ. ID. NO. 10500 | 365-GlnThrAlaGluSerLeuArgAlaAlaAla-374 |
| SEQ. ID. NO. 10501 | 386-AsnGlnLysProProLeu-391 |
| SEQ. ID. NO. 10502 | 395-GlnAlaProIleAspGlyThr-401 |
| SEQ. ID. NO. 10503 | 413-IleAlaArgAlaAlaGlu-418 |
| SEQ. ID. NO. 10504 | 431-PheIleLysArgGlyThrLeuValAsnSerTyrAlaLys-443 |
| Hydrophilic Regions - Hopp-Woods | |
| SEQ. ID. NO. 10505 | 21-GluValValAspGluSerAsnGlyLysAlaLeuAlaGluHisAlaArg-36 |
| SEQ. ID. NO. 10506 | 42-IleAspLeuGluAspMetGlyMetThr-50 |
| SEQ. ID. NO. 10507 | 65-TyrAlaGlyArgLeuLysLysLeuLeuAspAlaLeuGluGlnProGly-80 |
| SEQ. ID. NO. 10508 | 104-HisGluAlaAspTyr-108 |
| SEQ. ID. NO. 10509 | 117-ThrPheArgGluAlaAlaGluAlaGln-125 |
| SEQ. ID. NO. 10510 | 146-AspThrTyrArgGluAlaAla-152 |
| SEQ. ID. NO. 10511 | 189-ArgLeuPheAspLeuAspLys-195 |
| SEQ. ID. NO. 10512 | 197-AlaPheProAspArgGlyGly-203 |
| SEQ. ID. NO. 10513 | 226-ThrGlyIleArgArgGluAlaGlyLeu-234 |
| SEQ. ID. NO. 10514 | 246-ProArgGlnArgPheAspGly-252 |
| SEQ. ID. NO. 10515 | 256-ValAlaAspArgAlaAlaAla-262 |
| SEQ. ID. NO. 10516 | 276-LeuGlnAsnArgLeuAsnArgLeuThrAla-285 |

TABLE 1-continued

| | |
|---|---|
| SEQ. ID. NO. 10517 | 313-AlaHisGlyGluGluMetThrAla-320 |
| SEQ. ID. NO. 10518 | 322-AspLeuIleGluValAsnArgAlaMetArgArgMetGlnAla-336 |
| SEQ. ID. NO. 10519 | 348-AlaAlaGluSerGlyGly-353 |
| SEQ. ID. NO. 10520 | 368-GluSerLeuArgAlaAlaAla-374 |
| SEQ. ID. NO. 10521 | 413-IleAlaArgAlaAlaGlu-418 |

721
AMPHI Regions - AMPHI

| | |
|---|---|
| SEQ. ID. NO. 10522 | 87-AlaGlyTrpMetArgTrpLeuGlu-94 |
| SEQ. ID. NO. 10523 | 120-ArgTyrIleSerAlaVal-125 |
| SEQ. ID. NO. 10524 | 135-SerLysIlePheHisAlaAlaLeuThrAsnPheProAlaLeuAspGlyMetAspGluValLeuAla-156 |
| SEQ. ID. NO. 10525 | 170-AsnProMetLysGluLeuLeuGlnGlnLeuPheAspLeuPro-183 |
| SEQ. ID. NO. 10526 | 210-AspValPheAlaGln-214 |
| SEQ. ID. NO. 10527 | 236-LysTyrAlaProIleSerValValGlnGluLeuGln-247 |
| SEQ. ID. NO. 10528 | 282-TrpAlaLysGlyValLeuLysGlnProGlyGly-292 |
| SEQ. ID. NO. 10529 | 294-AlaPheLeuThrGlyPheIleGlu-301 |

Antigenic Index - Jameson-Wolf

| | |
|---|---|
| SEQ. ID. NO. 10530 | 1-MetSerLysAsnAlaGln-6 |
| SEQ. ID. NO. 10531 | 16-GluValGlnProLysAspGlyArgIle-24 |
| SEQ. ID. NO. 10532 | 27-LeuProTyrGlyGlu-31 |
| SEQ. ID. NO. 10533 | 33-ArgAlaValAspGlyArgProThrAspValProAla-44 |
| SEQ. ID. NO. 10534 | 48-ThrGluGluAsnGlyHisAsp-54 |
| SEQ. ID. NO. 10535 | 58-LeuAlaAsnSerSerArgAsnGlnLeu-66 |
| SEQ. ID. NO. 10536 | 74-ThrLeuTyrLysGluLysAsnGlyGlnProAlaPro-85 |
| SEQ. ID. NO. 10537 | 94-GluPheThrProLysGlyMetPheAla-102 |
| SEQ. ID. NO. 10538 | 105-GluTrpThrAspLysAlaAla-111 |
| SEQ. ID. NO. 10539 | 115-AlaAlaLysGluTyrArg-120 |
| SEQ. ID. NO. 10540 | 126-PheSerTyrAspThrLysGlyTyrVal-134 |
| SEQ. ID. NO. 10541 | 149-AspGlyMetAspGluValLeu-155 |
| SEQ. ID. NO. 10542 | 161-GlnIleLeuLysProGluThrGluGlnAsnProMetLysGluLeuLeu-176 |
| SEQ. ID. NO. 10543 | 183-ProAspAlaGlyGluGluGluLeuLysAla-192 |
| SEQ. ID. NO. 10544 | 198-ValGluAlaLysProLysAspValAlaLeu-207 |
| SEQ. ID. NO. 10545 | 215-LeuAlaGluLysAspSerArgIle-222 |
| SEQ. ID. NO. 10546 | 228-GlnThrAlaLysProAspLeuThrLysTyrAla-238 |
| SEQ. ID. NO. 10547 | 255-AlaLysGlnGluAlaAspLysGlyAsnGlu-264 |
| SEQ. ID. NO. 10548 | 277-ProAlaGlnLysGluTrpAla-283 |
| SEQ. ID. NO. 10549 | 286-ValLeuLysGlnProGlyGly-292 |
| SEQ. ID. NO. 10550 | 311-GlySerGlnThrGlyGlyLysAlaProAspGluArgValAla-324 |
| SEQ. ID. NO. 10551 | 327-ThrAlaGluGluAlaAlaAla-333 |
| SEQ. ID. NO. 10552 | 338-GlyMetSerGlyGluGluPheValLysIleLysGluSerGluGlyLys-353 |

Hydrophilic Regions - Hopp-Woods

| | |
|---|---|
| SEQ. ID. NO. 10553 | 1-MetSerLysAsnAlaGln-6 |
| SEQ. ID. NO. 10554 | 17-ValGlnProLysAspGlyArgIle-24 |
| SEQ. ID. NO. 10555 | 33-ArgAlaValAspGlyArgProThrAsp-41 |
| SEQ. ID. NO. 10556 | 49-GluGluAsnGlyHis-53 |
| SEQ. ID. NO. 10557 | 74-ThrLeuTyrLysGluLysAsnGlyGln-82 |
| SEQ. ID. NO. 10558 | 105-GluTrpThrAspLysAlaAla-111 |
| SEQ. ID. NO. 10559 | 115-AlaAlaLysGluTyrArg-120 |
| SEQ. ID. NO. 10560 | 149-AspGlyMetAspGluValLeu-155 |
| SEQ. ID. NO. 10561 | 163-LeuLysProGluThrGluGlnAsnProMetLysGluLeuLeu-176 |
| SEQ. ID. NO. 10562 | 183-ProAspAlaGlyGluGluGluLeuLysAla-192 |
| SEQ. ID. NO. 10563 | 198-ValGluAlaLysProLysAspValAlaLeu-207 |
| SEQ. ID. NO. 10564 | 215-LeuAlaGluLysAspSerArgIle-222 |
| SEQ. ID. NO. 10565 | 229-ThrAlaLysProAspLeuThrLys-236 |
| SEQ. ID. NO. 10566 | 255-AlaLysGlnGluAlaAspLysGlyAsnGlu-264 |
| SEQ. ID. NO. 10567 | 277-ProAlaGlnLysGluTrpAla-283 |
| SEQ. ID. NO. 10568 | 314-ThrGlyGlyLysAlaProAspGluArgValAla-324 |
| SEQ. ID. NO. 10569 | 327-ThrAlaGluGluAlaAlaAla-333 |
| SEQ. ID. NO. 10570 | 340-SerGlyGluGluPheValLysIleLysGluSerGluGlyLys-353 |

723
AMPHI Regions - AMPHI

| | |
|---|---|
| SEQ. ID. NO. 10571 | 57-ThrGlnGlnValGluHisValAspPheValAlaValAla-69 |
| SEQ. ID. NO. 10572 | 87-AsnValAlaAlaLys-91 |
| SEQ. ID. NO. 10573 | 123-CysAspLeuAlaVal-127 |
| SEQ. ID. NO. 10574 | 135-ValGlyGluLeuGlnAspPhe-141 |
| SEQ. ID. NO. 10575 | 208-SerIleThrSerArg-212 |
| SEQ. ID. NO. 10576 | 245-LysAlaValValSerIle-250 |

Antigenic Index - Jameson-Wolf

| | |
|---|---|
| SEQ. ID. NO. 10577 | 1-MetArgProLysProArgPheArgArgSerVal-11 |
| SEQ. ID. NO. 10578 | 55-HisSerThrGlnGln-59 |
| SEQ. ID. NO. 10579 | 76-HisAlaLeuSerArgArgGlnThrVal-84 |
| SEQ. ID. NO. 10580 | 92-AlaHisGlnAspGlyArgGlnIleLeuLysArgSerSerGluProProGlnIleArgValAspPheGlySerGlyValHisGlnArgGlyLeuCys-123 |
| SEQ. ID. NO. 10581 | 142-GlnLeuThrGluThrArgAsnHisIleLeuAsnArgArgValCysHis-157 |
| SEQ. ID. NO. 10582 | 164-CysSerIleGlySer-168 |
| SEQ. ID. NO. 10583 | 177-SerProThrSerAlaArgPheThrSerArgGlnProProSerAsnSerArgProProArgGlnAsnSerLeuPro-201 |
| SEQ. ID. NO. 10584 | 213-LeuSerAlaLysAlaSerAla-219 |
| SEQ. ID. NO. 10585 | 229-SerAlaSerSerAlaAspSer-235 |
| SEQ. ID. NO. 10586 | 260-SerAlaCysThrAlaSerAsn-266 |
| SEQ. ID. NO. 10587 | 269-LeuMetSerSerAsnAspGlyAlaAla-277 |
| SEQ. ID. NO. 10588 | 294-CysPheArgArgArgArgIleArgIle-302 |

TABLE 1-continued

Hydrophilic Regions - Hopp-Woods
SEQ. ID. NO. 10589  1-MetArgProLysProArgPheArgArgSerVal-11
SEQ. ID. NO. 10590  77-AlaLeuSerArgArgGlnThrVal-84
SEQ. ID. NO. 10591  92-AlaHisGlnAspGlyArgGlnIleLeuLysArgSerSerGluProProGlnIleArgValAspPhe-113
SEQ. ID. NO. 10592  142-GlnLeuThrGluThrArgAsn-148
SEQ. ID. NO. 10593  150-IleLeuAsnArgArgValCys-156
SEQ. ID. NO. 10594  183-PheThrSerArgGlnProProSerAsnSerArgProProArgGlnAsnSer-199
SEQ. ID. NO. 10595  213-LeuSerAlaLysAlaSerAla-219
SEQ. ID. NO. 10596  271-SerSerAsnAspGlyAlaAla-277
SEQ. ID. NO. 10597  294-CysPheArgArgArgArgIleArgIle-302
724
AMPHI Regions - AMPHI
SEQ. ID. NO. 10598  6-LeuAlaLysLysThr-10
SEQ. ID. NO. 10599  12-GlnThrAlaLysAsnIleGlyGluThrLeuArg-22
SEQ. ID. NO. 10600  40-ArgValGlnLeuSer-44
SEQ. ID. NO. 10601  47-AlaAspGluThrLeuGlnAspLeuGluHisLeuGlnGlu-59
Antigenic Index - Jameson-Wolf
SEQ. ID. NO. 10602  5-LysLeuAlaLysLysThrAlaGlnThrAlaLysAsnIleGlyGluThrLeuArgAlaAlaPheArgGlyLysIle-29
SEQ. ID. NO. 10603  34-SerSerGluProIleGlnArgValGlnLeuSerGlyLeuAlaAspGluThrLeuGlnAspLeuGluHis-56
SEQ. ID. NO. 10604  60-TyrGlyPheAlaSerHisProProAspGlySerGluAla-72
SEQ. ID. NO. 10605  77-LeuGlyGlyAsnThrSer-82
SEQ. ID. NO. 10606  90-GlnHisGlySerTyrArgIleLysAsnLeuLysProGlyGluThr-104
SEQ. ID. NO. 10607  108-AsnHisGluGlyAlaLysIleValIleLysGlnGlyLysIleIleGluAlaAspCysAspVal-128
SEQ. ID. NO. 10608  130-ArgValAsnCysLysGlnTyrGlu-137
SEQ. ID. NO. 10609  142-ThrAspAlaLysPhe-146
SEQ. ID. NO. 10610  162-GlnIleAsnGlyAsnGly-167
SEQ. ID. NO. 10611  170-AlaValGluGlyGlyAspGlyAlaThrPheSerGlyAspValAsnGlnThrGlyGlySerPheAsnThrAspGlyAspValValAla-198
SEQ. ID. NO. 10612  205-GlnHisProHisThrAspSerIleGlyGlyLysThrLeuProAlaGluProAla-222
Hydrophilic Regions - Hopp-Woods
SEQ. ID. NO. 10613  5-LysLeuAlaLysLysThrAlaGlnThrAlaLysAsnIleGlyGluThrLeuArgAlaAlaPheArgGly-27
SEQ. ID. NO. 10614  46-LeuAlaAspGluThrLeuGlnAspLeuGluHis-56
SEQ. ID. NO. 10615  66-ProProAspGlySerGlu-71
SEQ. ID. NO. 10616  94-TyrArgIleLysAsnLeuLysProGlyGlu-103
SEQ. ID. NO. 10617  110-GluGlyAlaLysIleValIleLysGlnGlyLysIleIleGluAlaAspCysAspVal-128
SEQ. ID. NO. 10618  132-AsnCysLysGlnTyrGlu-137
SEQ. ID. NO. 10619  142-ThrAspAlaLysPhe-146
SEQ. ID. NO. 10620  190-PheAsnThrAspGlyAspVal-196
SEQ. ID. NO. 10621  205-GlnHisProHisThrAspSerIleGly-213
725
AMPHI Regions - AMPHI
SEQ. ID. NO. 10622  11-GluAlaAspAspLeuAlaGlyGlnIleHisThrLeuProAlaValTrp-26
SEQ. ID. NO. 10623  41-GlyValCysGlyArgTyrGlnAsp-48
SEQ. ID. NO. 10624  81-AspLeuIleArgAlaValArgArgLeuLeuAsp-91
SEQ. ID. NO. 10625  104-ValProLysAlaValArgAlaIle-111
SEQ. ID. NO. 10626  144-ProGluArgThrAspAsnProAsp-151
SEQ. ID. NO. 10627  155-HisIlePheThrLysTyrGlnGlyThrLeuSerGluProTrpProAspPheGlu-172
SEQ. ID. NO. 10628  180-AspProGlnSerAla-184
Antigenic Index - Jameson-Wolf
SEQ. ID. NO. 10629  3-ArgThrValLysSerTyrAsnGlyGluAlaAspAspLeuAla-16
SEQ. ID. NO. 10630  29-TyrGlyGlySerLysValGluProAlaSerThrGlyGlyValCysGlyArgTyrGlnAspThrAla-50
SEQ. ID. NO. 10631  59-ArgAsnLeuArgAsnGluGlnAlaGlnArgGlnGlyGlyIleAspSerArgGluIleGlySerAsnAspLeuIleArgAlaValArgArgLeuLeuAsp
              GlyGlnArgLeuGlyPheAlaAspSerArgGlyLeuValProLysAlaValArg-109
SEQ. ID. NO. 10632  134-AsnThrCysGlyLeuGluAsnAspArgTyrProGluArgThrAspAsnProAspAspProAsn-154
SEQ. ID. NO. 10633  160-TyrGlnGlyThrLeuSerGluProTrpProAspPheGluGlyLeuAspGlyLysIleTyrAspProGlnSerAlaAspGluIlePro-188
SEQ. ID. NO. 10634  192-ThrLeuLysAspLysGln-197
Hydrophilic Regions - Hopp-Woods
SEQ. ID. NO. 10635  8-TyrAsnGlyGluAlaAspAspLeuAla-16
SEQ. ID. NO. 10636  32-SerLysValGluProAlaSer-38
SEQ. ID. NO. 10637  45-ArgTyrGlnAspThrAla-50
SEQ. ID. NO. 10638  59-ArgAsnLeuArgAsnGluGlnAlaGlnArgGlnGlyGlyIleAspSerArgGluIleGlySer-79
SEQ. ID. NO. 10639  81-AspLeuIleArgAlaValArgArgLeuLeuAspGlyGlnArg-94
SEQ. ID. NO. 10640  96-GlyPheAlaAspSerArgGlyLeuVal-104
SEQ. ID. NO. 10641  137-GlyLeuGluAsnAspArgTyrProGluArgThrAspAsnProAspAspProAsn-154
SEQ. ID. NO. 10642  172-GluGlyLeuAspGlyLysIleTyrAsp-180
SEQ. ID. NO. 10643  182-GlnSerAlaAspGluIlePro-188
SEQ. ID. NO. 10644  192-ThrLeuLysAspLysGln-197
726
AMPHI Regions - AMPHI
SEQ. ID. NO. 10645  12-AspThrLeuGlyGlyIleProGlu-19
SEQ. ID. NO. 10646  55-ProArgProSerAspTyrHisGlu-62
SEQ. ID. NO. 10647  74-AlaAlaAlaAlaArg-78
SEQ. ID. NO. 10648  110-IleAspSerPheTyrArg-115
SEQ. ID. NO. 10649  122-AlaArgGlnAlaAsp-126
SEQ. ID. NO. 10650  137-IleAlaAlaAlaArg-141
SEQ. ID. NO. 10651  180-IleGluThrAlaProGlyLeuAspAlaLeuGluLysGluIleGlu-194
Antigenic Index - Jameson-Wolf
SEQ. ID. NO. 10652  5-PheLysAsnGlyPheTyrAspAspThrLeuGlyGlyIleProGluGly-20
SEQ. ID. NO. 10653  24-ValArgAlaGluGluTyr-29
SEQ. ID. NO. 10654  37-AlaGlnGlyGlyGlnIleAlaAlaAspSerAspGlyArgProValLeuThrProProArgProSerAspTyrHisGluTrpAspGlyLysLysTrpLys
              IleSerLys-72

TABLE 1-continued

| | |
|---|---|
| SEQ. ID. NO. 10655 | 78-ArgPheAlaLysGlnLysThr-84 |
| SEQ. ID. NO. 10656 | 90-LeuAlaGluLysAlaAspGluLeuLysAsnSer-100 |
| SEQ. ID. NO. 10657 | 106-ProGlnValGluIleAspSerPheTyrArgGlnGluLysGluAlaLeuAlaArgGlnAlaAspAsnAsnAlaProThr-131 |
| SEQ. ID. NO. 10658 | 151-LysValIleGluLysSerAlaArg-158 |
| SEQ. ID. NO. 10659 | 167-IleGlyLysArgGlnGlnLeuGluAspLysLeuAsnThr-179 |
| SEQ. ID. NO. 10660 | 181-GluThrAlaProGlyLeuAspAlaLeuGluLysGluIleGluGlu-195 |

Hydrophilic Regions - Hopp-Woods

| | |
|---|---|
| SEQ. ID. NO. 10661 | 24-ValArgAlaGluGluTyr-29 |
| SEQ. ID. NO. 10662 | 42-IleAlaAlaAspSerAspGlyArgPro-50 |
| SEQ. ID. NO. 10663 | 55-ProArgProSerAspTyrHisGluTrpAspGlyLysLysTrpLysIleSerLys-72 |
| SEQ. ID. NO. 10664 | 78-ArgPheAlaLysGlnLysThr-84 |
| SEQ. ID. NO. 10665 | 90-LeuAlaGluLysAlaAspGluLeuLysAsn-99 |
| SEQ. ID. NO. 10666 | 114-TyrArgGlnGluLysGluAlaLeuAlaArgGlnAlaAspAsnAsnAla-129 |
| SEQ. ID. NO. 10667 | 151-LysValIleGluLysSerAlaArg-158 |
| SEQ. ID. NO. 10668 | 167-IleGlyLysArgGlnGlnLeuGluAspLysLeuAsnThr-179 |
| SEQ. ID. NO. 10669 | 187-AspAlaLeuGluLysGluIleGluGlu-195 |

727
AMPHI Regions - AMPHI

| | |
|---|---|
| SEQ. ID. NO. 10670 | 6-LeuLeuAlaAsnAsn-10 |
| SEQ. ID. NO. 10671 | 12-GlnProIleAlaIleIleAla-18 |

Antigenic Index - Jameson-Wolf

| | |
|---|---|
| SEQ. ID. NO. 10672 | 28-HisHisGlnGlyTyrLysSerAlaPheAlaLysGln-39 |
| SEQ. ID. NO. 10673 | 41-AlaValIleAspLysMetGluArgAspLysAlaGln-52 |
| SEQ. ID. NO. 10674 | 60-AsnTyrAlaArgGluLeuGluLeuAlaArgAlaGluAlaLysLysTyrGluValLysAla-79 |
| SEQ. ID. NO. 10675 | 86-LeuAlaLysLysGlnAlaGluValSerArgLeuLysThrGluArgAspLeuCysLys-104 |
| SEQ. ID. NO. 10676 | 106-ProPheProProAspSerArgAsnProAsnThrGlyPhe-118 |
| SEQ. ID. NO. 10677 | 122-SerProGlnIleProProAsnPhe-129 |

Hydrophilic Regions - Hopp-Woods

| | |
|---|---|
| SEQ. ID. NO. 10678 | 41-AlaValIleAspLysMetGluArgAspLysAlaGln-52 |
| SEQ. ID. NO. 10679 | 60-AsnTyrAlaArgGluLeuGluLeuAlaArgAlaGluAlaLysLysTyrGluValLysAla-79 |
| SEQ. ID. NO. 10680 | 86-LeuAlaLysLysGlnAlaGluValSerArgLeuLysThrGluArgAspLeuCys-103 |
| SEQ. ID. NO. 10681 | 109-ProAspSerArgAsnProAsnThr-116 |

728
AMPHI Regions - AMPHI

| | |
|---|---|
| SEQ. ID. NO. 10682 | 11-SerPhePheAlaLeuValPheAla-18 |
| SEQ. ID. NO. 10683 | 39-AlaThrGluValProLysAsnPro-46 |
| SEQ. ID. NO. 10684 | 48-AlaPheValAlaLysLeuAlaArgLeuPheArgAsnAla-60 |
| SEQ. ID. NO. 10685 | 76-AsnLeuAlaGlyThrValAspAsp-83 |
| SEQ. ID. NO. 10686 | 198-GluAspValTyrGluHisCysLeuGlyCysTyrGlnMet-210 |
| SEQ. ID. NO. 10687 | 218-TyrArgAspValAlaAsnAspGlu-225 |
| SEQ. ID. NO. 10688 | 235-SerAsnArgIleAlaSer-240 |
| SEQ. ID. NO. 10689 | 249-GlnAsnMetArgGluLeuMetProArg-257 |
| SEQ. ID. NO. 10690 | 355-GluLysGluValArgArgTyrAlaGluAlaAlaAlaArg-367 |

Antigenic Index - Jameson-Wolf

| | |
|---|---|
| SEQ. ID. NO. 10691 | 29-IleAsnProArgTrp-33 |
| SEQ. ID. NO. 10692 | 35-LeuSerAspThrAlaThrGluValProLysAsnProAsn-47 |
| SEQ. ID. NO. 10693 | 57-PheArgAsnAlaAspArgAla-63 |
| SEQ. ID. NO. 10694 | 69-GluSerIleArgThrGluGluAsnLeuAlaGlyThrValAspAspGlyProLeuGlnSerGluLysAspTyr-92 |
| SEQ. ID. NO. 10695 | 98-ArgLeuSerArgLeuLysGluLysAlaLys-107 |
| SEQ. ID. NO. 10696 | 112-ThrGluGlnGluHisGlyLys-118 |
| SEQ. ID. NO. 10697 | 125-HisIleGlyGluGlyGly-130 |
| SEQ. ID. NO. 10698 | 136-LeuSerGlnArgSerProGluAlaPheVal-145 |
| SEQ. ID. NO. 10699 | 149-TyrLeuTyrArgAsnAspArgProPheSer-158 |
| SEQ. ID. NO. 10700 | 166-ValHisGlyGluAsnTyrGluThrThrGlyGluTyrArgVal-179 |
| SEQ. ID. NO. 10701 | 182-GlnProAspGlySerVal-187 |
| SEQ. ID. NO. 10702 | 190-AlaAlaGlyArgGlyLysIleGlyGluAspValTyr-201 |
| SEQ. ID. NO. 10703 | 217-LysTyrArgAspValAlaAsnAspGluGlnLysValTrpAspPheArgLysGluSerAsnArgIleAlaSerAspSerArgAsnSerValPheTyrGln AsnMetArgGluLeuMetProArgGlyMetLysAlaAsnSer-263 |
| SEQ. ID. NO. 10704 | 267-GlyTyrAspAlaAspGlyLeuProGlnLys-276 |
| SEQ. ID. NO. 10705 | 280-SerPheAspAsnGlyLysLysArgGlnSerPheGluTyrTyrLeuLysAsnGlyAsn-298 |
| SEQ. ID. NO. 10706 | 309-LeuLysAlaAspGlyValThr-315 |
| SEQ. ID. NO. 10707 | 329-LeuAspGlyGlyArgIleValArgGluGluLysGlnGlyAspArgLeuProAspPhe-347 |
| SEQ. ID. NO. 10708 | 352-GluAsnLeuGluLysGluValArgArgTyrAlaGluAlaAlaAlaArgArgSerGlyGlyArgArgAspLeuSerHis-377 |

Hydrophilic Regions - Hopp-Woods

| | |
|---|---|
| SEQ. ID. NO. 10709 | 38-ThrAlaThrGluValProLysAsnPro-46 |
| SEQ. ID. NO. 10710 | 57-PheArgAsnAlaAspArgAla-63 |
| SEQ. ID. NO. 10711 | 69-GluSerIleArgThrGluGluAsnLeu-77 |
| SEQ. ID. NO. 10712 | 80-ThrValAspAspGlyProLeuGlnSerGluLysAspTyr-92 |
| SEQ. ID. NO. 10713 | 98-ArgLeuSerArgLeuLysGluLysAlaLys-107 |
| SEQ. ID. NO. 10714 | 112-ThrGluGlnGluHisGlyLys-118 |
| SEQ. ID. NO. 10715 | 136-LeuSerArgSerProGlu-142 |
| SEQ. ID. NO. 10716 | 151-TyrArgAsnAspArgProPhe-157 |
| SEQ. ID. NO. 10717 | 169-GluAsnTyrGluThrThrGlyGluTyr-177 |
| SEQ. ID. NO. 10718 | 190-AlaAlaGlyArgGlyLysIleGlyGluAspValTyr-201 |
| SEQ. ID. NO. 10719 | 217-LysTyrArgAspValAlaAsnAspGluGlnLysValTrpAspPheArgLysGluSerAsnArgIleAlaSerAspSerArgAsn-244 |
| SEQ. ID. NO. 10720 | 250-AsnMetArgGluLeuMetProArgGlyMetLys-260 |
| SEQ. ID. NO. 10721 | 268-TyrAspAlaAspGlyLeuPro-274 |
| SEQ. ID. NO. 10722 | 282-AspAsnGlyLysLysArgGlnSer-289 |
| SEQ. ID. NO. 10723 | 309-LeuLysAlaAspGlyValThr-315 |
| SEQ. ID. NO. 10724 | 331-GlyGlyArgIleValArgGluGluLysGlnGlyAspArgLeuPro-345 |

TABLE 1-continued

| SEQ. ID. NO. 10725 | 352-GluAsnLeuGluLysGluValArgArgTyrAlaGluAlaAlaAlaArgArgSerGlyGlyArgArgAspLeuSerHis-377 |

729
AMPHI Regions - AMPHI
| SEQ. ID. NO. 10726 | 21-CysThrMetIleProGlnTyr-27 |
| SEQ. ID. NO. 10727 | 33-GluValAlaGluThrPheLysAsnAspThr-42 |
| SEQ. ID. NO. 10728 | 55-HisAspTyrPheAla-59 |
| SEQ. ID. NO. 10729 | 61-ProArgLeuGlnLysLeuIleAspIle-69 |
| SEQ. ID. NO. 10730 | 149-GlnGlyTyrPheAla-153 |
| SEQ. ID. NO. 10731 | 164-SerLeuIleAlaThrValAlaLys-171 |
| SEQ. ID. NO. 10732 | 242-LeuAlaThrLeuIleAsn-247 |
| SEQ. ID. NO. 10733 | 268-LysLeuProAlaGlyLeu-273 |
| SEQ. ID. NO. 10734 | 322-LeuGlyGlyLeuPheLysSerGly-329 |
| SEQ. ID. NO. 10735 | 371-ValGlnSerAlaPheGlnAspValAlaAsnAla-381 |
| SEQ. ID. NO. 10736 | 388-LeuAspLysAlaTyrAspAlaLeuSerLysGlnSerArg-400 |
| SEQ. ID. NO. 10737 | 419-GlyAlaLeuAspLeuLeuAspAla-426 |
| SEQ. ID. NO. 10738 | 442-LeuThrArgAlaGluAsnLeuAlaAspLeuTyrLysAlaLeuGlyGlyGlyLeuLys-460 |

Antigenic Index - Jameson-Wolf
| SEQ. ID. NO. 10739 | 25-ProGlnTyrGluGlnProLysValGluVal-34 |
| SEQ. ID. NO. 10740 | 36-GluThrPheLysAsnAspThrAlaAspSerGlyIleArgAlaValAsp-51 |
| SEQ. ID. NO. 10741 | 53-GlyTrpHisAspTyrPheAlaAspProArgLeuGlnLys-65 |
| SEQ. ID. NO. 10742 | 70-AlaLeuGluArgAsnThrSerLeuArgThr-79 |
| SEQ. ID. NO. 10743 | 85-GluIleTyrArgLysGlnTyrMetIleGluArgAsnAsnLeuLeuPro-100 |
| SEQ. ID. NO. 10744 | 105-AsnAlaAsnAspSerArgGlnGlySerLeuSerGlyGlyAsnValSerSerSerTyrLysVal-125 |
| SEQ. ID. NO. 10745 | 138-GlyArgValArgSerSerSerGluAlaAla-147 |
| SEQ. ID. NO. 10746 | 155-ThrAlaAsnArgAspAlaAla-161 |
| SEQ. ID. NO. 10747 | 173-TyrPheAsnGluArgTyrAlaGluGluAlaMet-183 |
| SEQ. ID. NO. 10748 | 188-ArgValLeuLysThrArgGluGluThrTyrLysLeuSerGluLeuArgTyr-204 |
| SEQ. ID. NO. 10749 | 215-ArgGlnGlnGluAlaLeuIleGluSerAlaLysAlaAspTyr-228 |
| SEQ. ID. NO. 10750 | 232-AlaArgSerArgGluGlnAlaArgAsn-240 |
| SEQ. ID. NO. 10751 | 248-GlnProIleProGluAspLeuProAla-256 |
| SEQ. ID. NO. 10752 | 277-ValLeuLeuAspArgProAspIleArgAlaAlaGluHisAlaLeuLysGlnAlaAsnAla-296 |
| SEQ. ID. NO. 10753 | 315-ValGlyThrGlySerAlaGluLeu-322 |
| SEQ. ID. NO. 10754 | 325-LeuPheLysSerGlyThr-330 |
| SEQ. ID. NO. 10755 | 347-GlyThrAsnLysAlaAsnLeuAspValAlaLysLeuArgGlnGln-361 |
| SEQ. ID. NO. 10756 | 383-AlaAlaArgGluGlnLeuAspLysAlaTyrAspAlaLeuSerLysGlnSerArgAlaSerLysGluAlaLeuArg-407 |
| SEQ. ID. NO. 10757 | 411-LeuArgTyrLysHisGlyValSer-418 |
| SEQ. ID. NO. 10758 | 424-LeuAspAlaGluArgSerSerTyrAla-432 |
| SEQ. ID. NO. 10759 | 442-LeuThrArgAlaGluAsnLeu-448 |
| SEQ. ID. NO. 10760 | 455-LeuGlyGlyGlyLeuLysArgAspThrGlnThrAspLys-467 |

Hydrophilic Regions - Hopp-Woods
| SEQ. ID. NO. 10761 | 28-GluGlnProLysValGluVal-34 |
| SEQ. ID. NO. 10762 | 36-GluThrPheLysAsnAspThrAlaAspSerGlyIleArgAlaVal-50 |
| SEQ. ID. NO. 10763 | 61-ProArgLeuGlnLys-65 |
| SEQ. ID. NO. 10764 | 70-AlaLeuGluArgAsnThrSerLeu-77 |
| SEQ. ID. NO. 10765 | 91-TyrMetIleGluArgAsnAsn-97 |
| SEQ. ID. NO. 10766 | 105-AsnAlaAsnAspSerArgGlnGlySer-113 |
| SEQ. ID. NO. 10767 | 138-GlyArgValArgSerSerSerGluAlaAla-147 |
| SEQ. ID. NO. 10768 | 156-AlaAsnArgAspAlaAla-161 |
| SEQ. ID. NO. 10769 | 177-ArgTyrAlaGluGluAlaMet-183 |
| SEQ. ID. NO. 10770 | 188-ArgValLeuLysThrArgGluGluThrTyrLysLeuSerGluLeuArgTyr-204 |
| SEQ. ID. NO. 10771 | 215-ArgGlnGlnGluAlaLeuIleGluSerAlaLysAlaAspTyr-228 |
| SEQ. ID. NO. 10772 | 232-AlaArgSerArgGluGlnAlaArgAsn-240 |
| SEQ. ID. NO. 10773 | 250-IleProGluAspLeuPro-255 |
| SEQ. ID. NO. 10774 | 277-ValLeuLeuAspArgProAspIleArgAlaAlaGluHisAlaLeuLysGlnAlaAsn-295 |
| SEQ. ID. NO. 10775 | 350-LysAlaAsnLeuAspValAlaLysLeuArgGln-360 |
| SEQ. ID. NO. 10776 | 383-AlaAlaArgGluGlnLeuAspLysAlaTyrAspAlaLeuSerLysGlnSerArgAlaSerLysGluAlaLeuArg-407 |
| SEQ. ID. NO. 10777 | 424-LeuAspAlaGluArgSerSerTyrAla-432 |
| SEQ. ID. NO. 10778 | 442-LeuThrArgAlaGluAsnLeu-448 |
| SEQ. ID. NO. 10779 | 458-GlyLeuLysArgAspThrGlnThrAspLys-467 |

730
AMPHI Regions - AMPHI
| SEQ. ID. NO. 10780 | 6-ArgLeuThrAsnLeuLeuAlaAlaAlaCys-14 |
| SEQ. ID. NO. 10781 | 26-LeuAlaAlaAspLeu-30 |
| SEQ. ID. NO. 10782 | 67-LysIleAsnValIleGlnAspTyrThrHisGln-77 |
| SEQ. ID. NO. 10783 | 111-AsnHisAlaAlaAsp-115 |
| SEQ. ID. NO. 10784 | 141-HisProAlaAspAlaTyrAspGlyProLysGlyGlyAsnTyrProLysProThr-158 |
| SEQ. ID. NO. 10785 | 187-GlnArgIleSerAspAsnTyrSerAsnLeuGlySerAsnPheSerAspArgAlaAspGlu-206 |
| SEQ. ID. NO. 10786 | 214-HisAsnAlaLysLeu-218 |
| SEQ. ID. NO. 10787 | 220-ArgTrpGlyAsnSerMetGluPheIleAsnGlyValAla-232 |
| SEQ. ID. NO. 10788 | 234-GlyAlaLeuAsnProPheIleSer-241 |
| SEQ. ID. NO. 10789 | 262-AlaAlaMetArgAsnIleAla-268 |
| SEQ. ID. NO. 10790 | 277-AlaValIleGlyGlyLeuGlySerValAlaGlyPheGluLysAsnThrArgGluAlaValAspArgTrpIleGlnGlu-302 |
| SEQ. ID. NO. 10791 | 305-AsnAlaAlaGluThrValGluAlaValPheAsnValAlaAlaAlaAlaLysValAlaLysLeuAlaLysAlaAlaLysPro-331 |
| SEQ. ID. NO. 10792 | 338-GlyAspPheAlaAspSerTyr-344 |
| SEQ. ID. NO. 10793 | 387-AsnGlyArgGluIleAspAlaVal-394 |
| SEQ. ID. NO. 10794 | 405-ThrIleSerAlaIleAspLysProLys-413 |

Antigenic Index - Jameson-Wolf
| SEQ. ID. NO. 10795 | 2-LysProLeuArgArgLeuThr-8 |
| SEQ. ID. NO. 10796 | 35-PheIleThrAspAsnAlaGlnArgGlnHisTyrGluProGlyGlyLys-50 |
| SEQ. ID. NO. 10797 | 55-GlyAspProArgGlySerValSerAspArgThrGlyLysIleAsnVal-70 |

TABLE 1-continued

| SEQ. ID. NO. 10798 | 97-ArgPheSerGlyHisGlyHisGluGluHisAlaProPheAsp-110 |
| --- | --- |
| SEQ. ID. NO. 10799 | 112-HisAlaAlaAspSerAlaSerGluGluLysGlyAsnValAspGluGlyPhe-128 |
| SEQ. ID. NO. 10800 | 134-AsnTrpGluGlyHisGluHisHisProAlaAspAlaTyrAspGlyProLysGlyGlyAsnTyrProLysProThrGlyAlaArgAspGluTyrThr-165 |
| SEQ. ID. NO. 10801 | 167-HisValAsnGlyThrAlaArgSerIleLysLeuAsnProThrAspThrArgSerIleArgGlnArgIleSerAspAsnTyrSerAsn-195 |
| SEQ. ID. NO. 10802 | 197-GlySerAsnPheSerAspArgAlaAspGluAlaAsnArgLysMetPheGluHisAsnAlaLysLeuAspArgTrpGlyAsnSer-224 |
| SEQ. ID. NO. 10803 | 257-TyrAlaIleAspLysAlaAlaMet-264 |
| SEQ. ID. NO. 10804 | 271-ProAlaGluGlyLys-275 |
| SEQ. ID. NO. 10805 | 287-GlyPheGluLysAsnThrArgGluAlaValAsp-297 |
| SEQ. ID. NO. 10806 | 299-TrpIleGlnGluAsnProAsnAlaAlaGluThrVal-310 |
| SEQ. ID. NO. 10807 | 321-LysValAlaLysLeuAlaLysAlaAlaLysProGlyLysAlaAlaValSerGlyAspPheAlaAspSerTyrLysLysLysLeuAlaLeuSerAspSerAlaArgGln-356 |
| SEQ. ID. NO. 10808 | 359-GlnAsnAlaLysTyrArgGluAlaLeu-367 |
| SEQ. ID. NO. 10809 | 373-AspLeuIleArgArgLysThrAspGlySerSerLysPheIleAsnGlyArgGluIleAspAlaValThrAsnAsp-397 |
| SEQ. ID. NO. 10810 | 400-IleGlnAlaLysArgThrIleSerAlaIleAspLysProLysAsnPheLeuAsnGlnLysAsnArgLysGlnIleLysAlaThrIle-428 |
| SEQ. ID. NO. 10811 | 430-AlaAlaAsnGlnGlnGlyLysArgAlaGluPhe-440 |
| SEQ. ID. NO. 10812 | 452-SerTyrIleGluSerLysGlyGlyIleValLysThrGlyLeuGlyAsp-467 |

Hydrophilic Regions - Hopp-Woods

| SEQ. ID. NO. 10813 | 2-LysProLeuArgArgLeuThr-8 |
| --- | --- |
| SEQ. ID. NO. 10814 | 39-AsnAlaGlnArgGlnHisTyrGluProGlyGly-49 |
| SEQ. ID. NO. 10815 | 55-GlyAspProArgGlySerValSerAspArgThrGlyLys-67 |
| SEQ. ID. NO. 10816 | 102-GlyHisGluGluHisAlaPro-108 |
| SEQ. ID. NO. 10817 | 112-HisAlaAlaAspSerAlaSerGluGluLysGlyAsnValAspGluGly-127 |
| SEQ. ID. NO. 10818 | 135-TrpGluGlyHisGluHisHisPro-142 |
| SEQ. ID. NO. 10819 | 144-AspAlaTyrAspGlyProLysGlyGlyAsnTyrProLys-156 |
| SEQ. ID. NO. 10820 | 158-ThrGlyAlaArgAspGluTyr-164 |
| SEQ. ID. NO. 10821 | 170-GlyThrAlaArgSerIleLys-176 |
| SEQ. ID. NO. 10822 | 178-AsnProThrAspThrArgSerIleArgGlnArgIleSerAsp-191 |
| SEQ. ID. NO. 10823 | 200-PheSerAspArgAlaAspGluAlaAsnArgLysMetPheGluHisAsnAlaLysLeuAspArgTrpGlyAsn-223 |
| SEQ. ID. NO. 10824 | 257-TyrAlaIleAspLysAlaAlaMet-264 |
| SEQ. ID. NO. 10825 | 271-ProAlaGluGlyLys-275 |
| SEQ. ID. NO. 10826 | 287-GlyPheGluLysAsnThrArgGluAlaValAsp-297 |
| SEQ. ID. NO. 10827 | 303-AsnProAsnAlaAlaGluThrVal-310 |
| SEQ. ID. NO. 10828 | 321-LysValAlaLysLeuAlaLysAlaAlaLysProGlyLysAlaAlaVal-336 |
| SEQ. ID. NO. 10829 | 339-AspPheAlaAspSerTyrLysLysLysLeuAlaLeu-350 |
| SEQ. ID. NO. 10830 | 361-AlaLysTyrArgGluAlaLeu-367 |
| SEQ. ID. NO. 10831 | 373-AspLeuIleArgArgLysThrAspGlySerSer-383 |
| SEQ. ID. NO. 10832 | 386-IleAsnGlyArgGluIleAspAlaValThr-395 |
| SEQ. ID. NO. 10833 | 400-IleGlnAlaLysArgThrIleSerAlaIleAspLysProLysAsn-414 |
| SEQ. ID. NO. 10834 | 418-GlnLysAsnArgLysGlnIleLysAlaThrIle-428 |
| SEQ. ID. NO. 10835 | 430-AlaAlaAsnGlnGlnGlyLysArgAlaGluPhe-440 |
| SEQ. ID. NO. 10836 | 452-SerTyrIleGluSerLysGlyGlyIle-460 |

731
AMPHI Regions - AMPHI

| SEQ. ID. NO. 10837 | 17-AlaCysAlaValPro-21 |
| --- | --- |

Antigenic Index - Jameson-Wolf

| SEQ. ID. NO. 10838 | 22-GluAlaTyrAspAspGlyGlyArgGlyHis-31 |
| --- | --- |
| SEQ. ID. NO. 10839 | 34-ProValGlnAsnGlnAlaGlyThrAspAspPheArg-45 |
| SEQ. ID. NO. 10840 | 48-SerCysGluAsnGlyLeu-53 |
| SEQ. ID. NO. 10841 | 55-ValArgValArgHisLeuAspSerGlyLysValAlaLeuArgLeuAspGlyArgArgAlaValLeuSerSerAspValAlaAlaSerGlyGluArgTyrThrAla-89 |
| SEQ. ID. NO. 10842 | 98-ThrGluTrpHisGlnLysGlyGlyGluAla-107 |
| SEQ. ID. NO. 10843 | 113-AspAlaTyrGlyAsnSerValGluThrSerCysArgAlaArg-126 |

Hydrophilic Regions - Hopp-Woods

| SEQ. ID. NO. 10844 | 22-GluAlaTyrAspAspGlyGlyArgGlyHis-31 |
| --- | --- |
| SEQ. ID. NO. 10845 | 39-AlaGlyThrAspAspPheArg-45 |
| SEQ. ID. NO. 10846 | 55-ValArgValArgHisLeuAspSerGlyLysValAlaLeuArgLeuAspGlyArgArgAlaValLeu-76 |
| SEQ. ID. NO. 10847 | 80-ValAlaAlaSerGlyGluArgTyrThrAla-89 |
| SEQ. ID. NO. 10848 | 100-TrpHisGlnLysGlyGlyGlu-106 |
| SEQ. ID. NO. 10849 | 119-ValGluThrSerCysArgAlaArg-126 |

732
AMPHI Regions - AMPHI

| SEQ. ID. NO. 10850 | 14-LeuGlyAlaIleSer-18 |
| --- | --- |
| SEQ. ID. NO. 10851 | 43-ValGlnSerIleArgThrMetAlaGluValTyrGly-54 |
| SEQ. ID. NO. 10852 | 66-AspAlaAspLeuPheGluGlyAlaMetLysGlyMetVal-78 |
| SEQ. ID. NO. 10853 | 95-GluIleLysGluSerThrSerGly-102 |
| SEQ. ID. NO. 10854 | 115-AspGlyPheValLysValValSerProIleGluAsp-126 |
| SEQ. ID. NO. 10855 | 155-GluAlaValLysLysMet-160 |
| SEQ. ID. NO. 10856 | 183-ValAsnLeuThrArg-187 |
| SEQ. ID. NO. 10857 | 214-GluArgThrValGluSerValAsnThrAlaAlaLys-225 |
| SEQ. ID. NO. 10858 | 283-LysAlaIleProGluAsp-288 |
| SEQ. ID. NO. 10859 | 297-SerLeuAlaGlyIleProAlaGluLeu-305 |
| SEQ. ID. NO. 10860 | 322-SerGluIleValAlaGly-327 |
| SEQ. ID. NO. 10861 | 400-LeuValGlyHisIleGlyAsn-406 |
| SEQ. ID. NO. 10862 | 446-ArgArgIleProAsnProAlaLysAsp-454 |
| SEQ. ID. NO. 10863 | 459-LysAlaLeuAspLeuValLysSerProGluGlnTrpGlnLysSerLeu-474 |

Antigenic Index - Jameson-Wolf

| SEQ. ID. NO. 10864 | 30-AlaAlaGluLysAspArgArgAspAsnGluVal-40 |
| --- | --- |
| SEQ. ID. NO. 10865 | 59-AsnTyrTyrGlnAspLysProAspAlaAspLeuPhe-70 |
| SEQ. ID. NO. 10866 | 82-AspProHisSerGluTyrMetAspLysLysGlyTyrAlaGluIleLysGluSerThrSerGlyGluPheGlyGly-106 |
| SEQ. ID. NO. 10867 | 111-IleGlyGlnGluAspGlyPhe-117 |

TABLE 1-continued

| | |
|---|---|
| SEQ. ID. NO. 10868 | 122-SerProIleGluAspThrProAlaGluArgAlaGlyValLysSerGlyAspPhe-139 |
| SEQ. ID. NO. 10869 | 144-AspAsnValSerThrArgGlyMetThr-152 |
| SEQ. ID. NO. 10870 | 155-GluAlaValLysLysMetArgGlyLysProGlyThrLysIle-168 |
| SEQ. ID. NO. 10871 | 172-LeuSerArgLysAsnAlaAspLysProIle-181 |
| SEQ. ID. NO. 10872 | 199-LeuIleGluProAspTyrGlyTyr-206 |
| SEQ. ID. NO. 10873 | 211-GlnPheGlnGluArgThrValGlu-218 |
| SEQ. ID. NO. 10874 | 221-AsnThrAlaAlaLysGluLeuValLysGluAsnLysGlyLysProLeuLys-237 |
| SEQ. ID. NO. 10875 | 242-AspLeuArgAspAspProGlyGlyLeu-250 |
| SEQ. ID. NO. 10876 | 269-ValSerThrLysGlyArgAspGlyLysAspArgMetVal-281 |
| SEQ. ID. NO. 10877 | 284-AlaIleProGluAspTyr-289 |
| SEQ. ID. NO. 10878 | 292-GlyMetGlyGlyAspSer-297 |
| SEQ. ID. NO. 10879 | 303-AlaGluLeuLysThr-307 |
| SEQ. ID. NO. 10880 | 316-SerGlySerAlaSerAla-321 |
| SEQ. ID. NO. 10881 | 330-GlnAspHisLysArgAlaVal-336 |
| SEQ. ID. NO. 10882 | 340-ThrGlnSerPheGlyLysGlySerVal-348 |
| SEQ. ID. NO. 10883 | 354-LeuSerAsnGlySer-358 |
| SEQ. ID. NO. 10884 | 368-TyrThrProAsnAspArgSerIleGln-376 |
| SEQ. ID. NO. 10885 | 384-ValGluValLysAspLysGluArgIlePheGluSerArgGluAlaAspLeu-400 |
| SEQ. ID. NO. 10886 | 405-GlyAsnProLeuGlyGlyGluAspValAsnGly-415 |
| SEQ. ID. NO. 10887 | 421-ProLeuGluLysAspAlaAspLysProAlaValLysGluLysGlyLysLysLysLysAspGluAspLeuSerSerArgArgIleProAsnProAlaLysAspAspGlnLeuArgLysAlaLeuAspLeuValLysSerProGluGlnTrpGlnLys-472 |
| SEQ. ID. NO. 10888 | 477-AlaAlaLysLysProValSerAsnLysAspLysLysAspLysLysAspLysLys-494 |
| Hydrophilic Regions - Hopp-Woods | |
| SEQ. ID. NO. 10889 | 30-AlaAlaGluLysAspArgArgAspAsnGluVal-40 |
| SEQ. ID. NO. 10890 | 60-TyrTyrGlnAspLysProAspAlaAspLeuPhe-70 |
| SEQ. ID. NO. 10891 | 82-AspProHisSerGluTyrMetAspLysLysGlyTyrAlaGluIleLysGluSerThrSerGlyGlu-103 |
| SEQ. ID. NO. 10892 | 111-IleGlyGlnGluAspGlyPhe-117 |
| SEQ. ID. NO. 10893 | 122-SerProIleGluAspThrProAlaGluArgAlaGlyValLysSerGlyAspPhe-139 |
| SEQ. ID. NO. 10894 | 144-AspAsnValSerThr-148 |
| SEQ. ID. NO. 10895 | 155-GluAlaValLysLysMetArgGlyLysProGlyThr-166 |
| SEQ. ID. NO. 10896 | 172-LeuSerArgLysAsnAlaAspLysProIle-181 |
| SEQ. ID. NO. 10897 | 211-GlnPheGlnGluArgThrValGlu-218 |
| SEQ. ID. NO. 10898 | 221-AsnThrAlaAlaLysGluLeuValLysGluAsnLysGlyLysProLeuLys-237 |
| SEQ. ID. NO. 10899 | 242-AspLeuArgAspAspProGly-248 |
| SEQ. ID. NO. 10900 | 271-ThrLysGlyArgAspGlyLysAspArgMetVal-281 |
| SEQ. ID. NO. 10901 | 303-AlaGluLeuLysThr-307 |
| SEQ. ID. NO. 10902 | 330-GlnAspHisLysArgAlaVal-336 |
| SEQ. ID. NO. 10903 | 370-ProAsnAspArgSerIleGln-376 |
| SEQ. ID. NO. 10904 | 384-ValGluValLysAspLysGluArgIlePheGluSerArgGluAlaAspLeu-400 |
| SEQ. ID. NO. 10905 | 408-LeuGlyGlyGluAspValAsnGly-415 |
| SEQ. ID. NO. 10906 | 421-ProLeuGluLysAspAlaAspLysProAlaValLysGluLysGlyLysLysLysLysAspGluAspLeuSerSerArgArgIleProAsnProAlaLysAspAspGlnLeuArgLysAlaLeuAspLeuValLysSerProGluGlnTrpGln-471 |
| SEQ. ID. NO. 10907 | 477-AlaAlaLysLysProValSerAsnLysAspLysLysAspLysLysAspLysLys-494 |
| 733 | |
| AMPHI Regions - AMPHI | |
| SEQ. ID. NO. 10908 | 6-ThrLeuSerArgLeuSer-11 |
| SEQ. ID. NO. 10909 | 33-TyrGlyGlyTyrProAspThrValTyrGluGly-43 |
| SEQ. ID. NO. 10910 | 53-LysGlnThrGluLysMetGluLysTyrPheVal-63 |
| SEQ. ID. NO. 10911 | 92-GlyAlaPheArgGlnPheGluGlu-99 |
| Antigenic Index - Jameson-Wolf | |
| SEQ. ID. NO. 10912 | 2-MetAsnProLysThrLeuSer-8 |
| SEQ. ID. NO. 10913 | 22-CysGlyGlyAsnGlyGlnLysSer-29 |
| SEQ. ID. NO. 10914 | 33-TyrGlyGlyTyrProAspThrValTyrGluGlyLeuLysAsnAspAspThrSerLeuGlyLysGlnThrGluLysMetGluLysTyrPhe-62 |
| SEQ. ID. NO. 10915 | 65-AlaGlyAsnLysLysMetAsnAlaAlaProGlyAla-76 |
| SEQ. ID. NO. 10916 | 84-LeuSerArgSerGlyAspLysGluGlyAlaPheArgGlnPheGluGluGluLysArgLeuPheProGlu-106 |
| SEQ. ID. NO. 10917 | 115-MetLysThrGlyLysGlyGlyLysArg-123 |
| Hydrophilic Regions - Hopp-Woods | |
| SEQ. ID. NO. 10918 | 40-ValTyrGluGlyLeuLysAsnAspAspThrSerLeuGlyLysGlnThrGluLysMetGluLysTyrPhe-62 |
| SEQ. ID. NO. 10919 | 65-AlaGlyAsnLysLysMetAsnAla-72 |
| SEQ. ID. NO. 10920 | 86-ArgSerGlyAspLysGluGlyAlaPheArgGlnPheGluGluGluLysArgLeuPhePro-105 |
| SEQ. ID. NO. 10921 | 115-MetLysThrGlyLysGlyGlyLysArg-123 |
| 734-2 | |
| AMPHI Regions - AMPHI | |
| SEQ. ID. NO. 10922 | 19-ArgAlaAlaAspThrTyr-24 |
| SEQ. ID. NO. 10923 | 26-TyrLeuAlaValTrpGlnAsnProGlnAsnAlaAsp-37 |
| SEQ. ID. NO. 10924 | 53-GluAlaPheSerGluLeuGluAlaPheCysLys-63 |
| SEQ. ID. NO. 10925 | 77-ThrGlyCysArgSerValValSer-84 |
| SEQ. ID. NO. 10926 | 92-LeuAlaTyrProLysAlaLeuGlyAlaLeuArg-102 |
| SEQ. ID. NO. 10927 | 113-ArgPheThrSerVal-117 |
| SEQ. ID. NO. 10928 | 121-AlaLeuAsnGlnCysIleLys-127 |
| Antigenic Index - Jameson-Wolf | |
| SEQ. ID. NO. 10929 | 18-AlaArgAlaAlaAsp-22 |
| SEQ. ID. NO. 10930 | 31-GlnAsnProGlnAsnAlaAspAspValLeuGln-41 |
| SEQ. ID. NO. 10931 | 43-LysThrThrLysGluAspSerThrLysSerGluAlaPheSerGlu-57 |
| SEQ. ID. NO. 10932 | 59-GluAlaPheCysLysGlyGlnAspThr-67 |
| SEQ. ID. NO. 10933 | 71-IleAlaGluAspGluProThrGlyCysArgSer-81 |
| SEQ. ID. NO. 10934 | 101-LeuArgValAspAsn-105 |
| SEQ. ID. NO. 10935 | 111-SerProArgPheThrSer-116 |
| SEQ. ID. NO. 10936 | 125-CysIleLysLysTyrGlyVal-131 |
| SEQ. ID. NO. 10937 | 145-SerSerTyrTyrGly-149 |

TABLE 1-continued

Hydrophilic Regions - Hopp-Woods
SEQ. ID. NO. 10938  18-AlaArgAlaAlaAsp-22
SEQ. ID. NO. 10939  34-GlnAsnAlaAspAspValLeuGln-41
SEQ. ID. NO. 10940  43-LysThrThrLysGluAspSerThrLysSerGluAlaPheSerGlu-57
SEQ. ID. NO. 10941  59-GluAlaPheCysLysGlyGlnAspThr-67
SEQ. ID. NO. 10942  71-IleAlaGluAspGluProThrGlyCys-79
SEQ. ID. NO. 10943  101-LeuArgValAspAsn-105
735
AMPHI Regions - AMPHI
SEQ. ID. NO. 10944  6-LeuLeuAlaAsnAsn-10
SEQ. ID. NO. 10945  12-GlnProIleAlaIleIleAla-18
SEQ. ID. NO. 10946  118-GlyCysIleAspGlyPheGly-124
Antigenic Index - Jameson-Wolf
SEQ. ID. NO. 10947  28-HisHisGlnGlyTyrLysSerAlaPheAlaLysGln-39
SEQ. ID. NO. 10948  41-AlaValIleAspLysMetGluArgAspLysAlaGln-52
SEQ. ID. NO. 10949  60-AsnTyrAlaArgGluLeuGluLeuAlaArgAlaGluAlaLysLysTyrGluValLysAla-79
SEQ. ID. NO. 10950  86-LeuAlaLysLysGlnAlaGluValSerArgLeuLysThrGluAsnLysLysGluIleGluAsn-106
SEQ. ID. NO. 10951  108-LeuThrGlnAspArgLysAsnAlaSerGlyGlyCysIleAspGlyPheGlySerHisGly-127
SEQ. ID. NO. 10952  134-AlaLeuGlyTyrGlyAsn-139
Hydrophilic Regions - Hopp-Woods
SEQ. ID. NO. 10953  41-AlaValIleAspLysMetGluArgAspLysAlaGln-52
SEQ. ID. NO. 10954  60-AsnTyrAlaArgGluLeuGluLeuAlaArgAlaGluAlaLysLysTyrGluValLysAla-79
SEQ. ID. NO. 10955  86-LeuAlaLysLysGlnAlaGluValSerArgLeuLysThrGluAsnLysLysGluIleGluAsn-106
SEQ. ID. NO. 10956  108-LeuThrGlnAspArgLysAsnAlaSer-116
736
AMPHI Regions - AMPHI
SEQ. ID. NO. 10957  13-GlyLeuIleGlnSerLeuGlySer-20
SEQ. ID. NO. 10958  50-GlyValLeuSerVal-54
SEQ. ID. NO. 10959  61-GlyLeuPheValGly-65
SEQ. ID. NO. 10960  70-LeuGlnGlyTyrThrGlnLeuSerLysPheLysSerAlaAspIle-84
SEQ. ID. NO. 10961  93-LeuLeuArgGluLeuGlyProVal-100
SEQ. ID. NO. 10962  120-LeuMetLysThrThrGluGlnLeuGluAlaMetAsnValMet-133
SEQ. ID. NO. 10963  135-ValAsnProValAlaArgValVal-142
SEQ. ID. NO. 10964  144-ProArgPheTrpAlaGlyValPheSerMetPro-154
SEQ. ID. NO. 10965  156-LeuAlaSerIlePheAsnValAlaGlyIlePheGlyAla-168
SEQ. ID. NO. 10966  196-AspValIleAsnGlyLeu-201
SEQ. ID. NO. 10967  230-LeuArgAlaSerThrArgThr-236
Antigenic Index - Jameson-Wolf
SEQ. ID. NO. 10968  37-ValArgProArgLeuSerVal-43
SEQ. ID. NO. 10969  77-SerLysPheLysSer-81
SEQ. ID. NO. 10970  93-LeuLeuArgGluLeuGly-98
SEQ. ID. NO. 10971  109-SerAlaGlyGlyAlaMetThrSer-116
SEQ. ID. NO. 10972  122-LysThrThrGluGlnLeuGlu-128
SEQ. ID. NO. 10973  186-GlnMetGlnAsnAsn-190
SEQ. ID. NO. 10974  224-ProThrSerGluGlyIleLeuArgAlaSerThr-234
Hydrophilic Regions - Hopp-Woods
SEQ. ID. NO. 10975  39-ProArgLeuSerVal-43
SEQ. ID. NO. 10976  77-SerLysPheLysSer-81
SEQ. ID. NO. 10977  93-LeuLeuArgGluLeuGly-98
SEQ. ID. NO. 10978  122-LysThrThrGluGlnLeuGlu-128
737
AMPHI Regions - AMPHI
SEQ. ID. NO. 10979  56-AlaAlaLeuAlaArgValGlyGly-63
Antigenic Index - Jameson-Wolf
SEQ. ID. NO. 10980  24-AlaHisHisAspGlyHisGlyAspAspAspHisGlyHis-36
SEQ. ID. NO. 10981  38-AlaHisGlnHisAsnLysGlnAspLysIleIleSer-49
SEQ. ID. NO. 10982  51-AlaGlnAlaGluLysAlaAlaLeu-58
SEQ. ID. NO. 10983  60-ArgValGlyGlyLysIleThrAspIleAspLeuGluHisAspAsnGlyArgProHisTyrAspValGluIleValLysAsnGlyGlnGluTyr-90
SEQ. ID. NO. 10984  94-ValAspAlaArgThrGlyArgValIleSerSerArgArgAspAsp-108
Hydrophilic Regions - Hopp-Woods
SEQ. ID. NO. 10985  27-AspGlyHisGlyAspAspAspHisGlyHis-36
SEQ. ID. NO. 10986  40-GlnHisAsnLysGlnAspLysIleIleSer-49
SEQ. ID. NO. 10987  51-AlaGlnAlaGluLysAlaAlaLeu-58
SEQ. ID. NO. 10988  61-ValGlyGlyLysIleThrAspIleAspLeuGluHisAspAsnGlyArgProHisTyr-79
SEQ. ID. NO. 10989  82-GluIleValLysAsnGlyGlnGluTyr-90
SEQ. ID. NO. 10990  94-ValAspAlaArgThrGlyArg-100
SEQ. ID. NO. 10991  102-IleSerSerArgArgAspAsp-108
738
AMPHI Regions - AMPHI
SEQ. ID. NO. 10992  91-LeuMetAsnLeuIleTyrProGlyMetAsnAsp-101
SEQ. ID. NO. 10993  139-IleGlySerLeuLeuGlnSerCysIle-147
SEQ. ID. NO. 10994  228-ThrTyrIleAlaAlaIleAlaLeuIle-236
SEQ. ID. NO. 10995  271-ThrIleLeuGluThrPheThrGlyIle-279
SEQ. ID. NO. 10996  285-ValGluArgValAlaAsnGlyGlyPheThrAspLeuProArgGlnIleGluTrpAsn-303
SEQ. ID. NO. 10997  305-AlaLeuAlaAlaPheGlnSer-311
SEQ. ID. NO. 10998  316-GlyHisGlyTrpAsnSerPheAla-323
SEQ. ID. NO. 10999  338-AspAsnLeuLeuSerAsnLeuPheThr-346
SEQ. ID. NO. 11000  371-LeuLeuThrGlyIleAlaGlyLeuLeuLysArg-381
SEQ. ID. NO. 11001  398-MetCysHisSerMetLeu-403
SEQ. ID. NO. 11002  461-ArgLeuValAsnAlaPheSerPro-468

TABLE 1-continued

| | |
|---|---|
| SEQ. ID. NO. 11003 | 472-AspSerAlaLysThrLeuAsnArgLys-480 |
| SEQ. ID. NO. 11004 | 482-AsnGluLeuArgTyrIleSer-488 |
| SEQ. ID. NO. 11005 | 507-LeuProGluTyrProGluThr-513 |
| SEQ. ID. NO. 11006 | 549-AlaLysGlnTrpMetArgAlaThr-556 |
| SEQ. ID. NO. 11007 | 567-TyrAlaAspGluIleArgLysLeuProVal-576 |
| SEQ. ID. NO. 11008 | 579-ProLeuLeuProGluLeuLeuLysAspCysLysAlaPheAlaAlaAlaPro-595 |

Antigenic Index - Jameson-Wolf

| | |
|---|---|
| SEQ. ID. NO. 11009 | 37-LysLeuLysProSerProAspPheTyr-45 |
| SEQ. ID. NO. 11010 | 62-AlaGlyLysLysLeuPheAsp-68 |
| SEQ. ID. NO. 11011 | 124-PheGlyGlnGluArgIle-129 |
| SEQ. ID. NO. 11012 | 154-GlyTrpGluAspThrProLeu-160 |
| SEQ. ID. NO. 11013 | 177-GlyGlnArgAsnAsnLeuGly-183 |
| SEQ. ID. NO. 11014 | 196-LeuAsnGlyGlnArgLysIlePro-203 |
| SEQ. ID. NO. 11015 | 242-PheArgSerAspLysSerAsnArgArgThrMet-252 |
| SEQ. ID. NO. 11016 | 283-ThrAlaValGluArgValAlaAsnGlyGlyPheThrAspLeuProArgGlnIleGluTrp-302 |
| SEQ. ID. NO. 11017 | 316-GlyHisGlyTrpAsnSerPheAla-323 |
| SEQ. ID. NO. 11018 | 378-LeuLeuLysArgProLeuThr-384 |
| SEQ. ID. NO. 11019 | 424-ProAlaGluAlaSerAspGlyIleAlaPheLysLysAlaAla-437 |
| SEQ. ID. NO. 11020 | 468-ProAlaThrAspAspSerAlaLysThrLeuAsnArgLysIleAsnGlu-483 |
| SEQ. ID. NO. 11021 | 508-ProGluTyrProGluThrGlnThrTrpAlaGlu-518 |
| SEQ. ID. NO. 11022 | 520-AlaThrLeuLysSerLeuLysTyrArgProHisSerAla-532 |
| SEQ. ID. NO. 11023 | 542-ArgGlnGlyLysValAlaGluAlaLysGlnTrpMet-553 |
| SEQ. ID. NO. 11024 | 555-AlaThrGlnSerTyr-559 |
| SEQ. ID. NO. 11025 | 566-ArgTyrAlaAspGluIleArgLys-573 |
| SEQ. ID. NO. 11026 | 584-LeuLeuLysAspCysLysAla-590 |
| SEQ. ID. NO. 11027 | 595-ProGlyHisProGluAlaLysProCysLys-604 |

Hydrophilic Regions - Hopp-Woods

| | |
|---|---|
| SEQ. ID. NO. 11028 | 38-LeuLysProSerPro-42 |
| SEQ. ID. NO. 11029 | 62-AlaGlyLysLysLeuPheAsp-68 |
| SEQ. ID. NO. 11030 | 125-GlyGlnGluArgIle-129 |
| SEQ. ID. NO. 11031 | 198-GlyGlnArgLysIlePro-203 |
| SEQ. ID. NO. 11032 | 243-ArgSerAspLysSerAsnArgArgThrMet-252 |
| SEQ. ID. NO. 11033 | 283-ThrAlaValGluArgValAla-289 |
| SEQ. ID. NO. 11034 | 378-LeuLeuLysArgProLeuThr-384 |
| SEQ. ID. NO. 11035 | 425-AlaGluAlaSerAsp-429 |
| SEQ. ID. NO. 11036 | 431-IleAlaPheLysLysAlaAla-437 |
| SEQ. ID. NO. 11037 | 469-AlaThrAspAspSerAlaLysThrLeuAsnArgLysIleAsnGlu-483 |
| SEQ. ID. NO. 11038 | 525-LeuLysTyrArgPro-529 |
| SEQ. ID. NO. 11039 | 542-ArgGlnGlyLysValAlaGluAlaLysGlnTrpMet-553 |
| SEQ. ID. NO. 11040 | 566-ArgTyrAlaAspGluIleArgLys-573 |
| SEQ. ID. NO. 11041 | 584-LeuLeuLysAspCysLysAla-590 |
| SEQ. ID. NO. 11042 | 596-GlyHisProGluAlaLysProCysLys-604 |

739-2
AMPHI Regions - AMPHI

| | |
|---|---|
| SEQ. ID. NO. 11043 | 6-AsnLysProPheArgLeu-11 |
| SEQ. ID. NO. 11044 | 53-HisThrAspSerPro-57 |
| SEQ. ID. NO. 11045 | 88-GlnProAspGlyThrAsp-93 |
| SEQ. ID. NO. 11046 | 120-ThrAspArgGlnProAspAspAlaGlyThr-129 |
| SEQ. ID. NO. 11047 | 131-AlaGluAsnThrLeu-135 |

Antigenic Index - Jameson-Wolf

| | |
|---|---|
| SEQ. ID. NO. 11048 | 1-MetAlaLysLysProAsnLysProPheArgLeuThrPro-13 |
| SEQ. ID. NO. 11049 | 39-PheAsnProAsnGlyAspLysThrLeuGlnAlaGluProGlnHisThrAspSerProArgGluThrGluPhe-62 |
| SEQ. ID. NO. 11050 | 64-LeuProAsnGlyValValGlyGlnAspAlaAlaGlnProGluHisHisHis-80 |
| SEQ. ID. NO. 11051 | 82-AlaSerSerGluProAlaGlnProAspGlyThrAspGluSerGlySerGlyLeuProSerProAlaAlaProLysLysAsnArgValLysProGlnPro<br>AlaAspThrAlaGlnThrAspArgGlnProAspAspAlaGlyThrGlnAlaGluAsnThrLeuLysGluThrProValLeuProThrAsnValProArgPro<br>GluProArgLysGluThrProGluLysGlnAlaGlnProLysGluThrProLysGluAsnHisThrLysProAspThrProLysAsnThrProProLysPro<br>HisLysGluIleLeu-187 |

Hydrophilic Regions - Hopp-Woods

| | |
|---|---|
| SEQ. ID. NO. 11052 | 1-MetAlaLysLysProAsnLysProPheArgLeu-11 |
| SEQ. ID. NO. 11053 | 41-ProAsnGlyAspLysThrLeuGlnAlaGluProGlnHisThrAspSerProArgGluThrGlu-61 |
| SEQ. ID. NO. 11054 | 72-AspAlaAlaGlnProGluHisHisHis-80 |
| SEQ. ID. NO. 11055 | 82-AlaSerSerGluProAlaGlnProAspGlyThrAspGluSerGlySer-97 |
| SEQ. ID. NO. 11056 | 103-AlaAlaProLysLysAsnArgValLysProGlnProAlaAspThrAlaGlnThrAspArgGlnProAspAspAlaGlyThrGlnAlaGluAsnThrLeu<br>LysGluThrPro-139 |
| SEQ. ID. NO. 11057 | 145-ValProArgProGluProArgLysGluThrProGluLysGlnAlaGlnProLysGluThrProLysGluAsnHisThrLysProAspThrProLysAsn<br>ThrProProLysProHisLysGluIleLeu-187 |

740
AMPHI Regions - AMPHI

| | |
|---|---|
| SEQ. ID. NO. 11058 | 6-LeuValArgTrpLeuAlaVal-12 |
| SEQ. ID. NO. 11059 | 28-ProGluAspLysLeuGlnHisLeuIleAsnGlyIle-39 |

Antigenic Index - Jameson-Wolf

| | |
|---|---|
| SEQ. ID. NO. 11060 | 26-AsnProProGluAspLysLeuGln-33 |
| SEQ. ID. NO. 11061 | 57-IleLysHisHisLeuLysGlnGluPheAspLeuLysArgGlnThr-71 |

Hydrophilic Regions - Hopp-Woods

| | |
|---|---|
| SEQ. ID. NO. 11062 | 27-ProProGluAspLysLeuGln-33 |
| SEQ. ID. NO. 11063 | 57-IleLysHisHisLeuLysGlnGluPheAspLeuLysArgGlnThr-71 |

741
AMPHI Regions - AMPHI

| | |
|---|---|
| SEQ. ID. NO. 11064 | 32-GlyAlaGlyLeuAlaAspAlaLeuThrAla-41 |
| SEQ. ID. NO. 11065 | 93-SerArgPheAspPheIleArgGlnIleGlu-102 |

TABLE 1-continued

| | |
|---|---|
| SEQ. ID. NO. 11066 | 158-ThrSerPheAspLysLeuProGluGlyGlyArg-168 |
| SEQ. ID. NO. 11067 | 256-SerAlaGluValLysThrValAsnGlyIleArgHisIleGlyLeuAlaAlaLys-273 |
| Antigenic Index - Jameson-Wolf | |
| SEQ. ID. NO. 11068 | 21-SerSerGlyGlyGly-25 |
| SEQ. ID. NO. 11069 | 43-LeuAspHisLysAspLysGlyLeu-50 |
| SEQ. ID. NO. 11070 | 56-AspGlnSerValArgLysAsnGluLysLeuLysLeu-67 |
| SEQ. ID. NO. 11071 | 71-GlyAlaGluLysThrTyrGlyAsnGlyAspSerLeuAsnThrGlyLysLeuLysAsnAspLysValSerArgPheAspPhe-97 |
| SEQ. ID. NO. 11072 | 101-IleGluValAspGlyGlnLeu-107 |
| SEQ. ID. NO. 11073 | 117-ValTyrLysGlnSerHisSerAla-124 |
| SEQ. ID. NO. 11074 | 129-GlnThrGluGlnIleGlnAspSerGluHisSerGlyLysMetValAlaLysArgGlnPheArgIleGlyAspIleAlaGlyGluHisThrSerPheAsp LysLeuProGluGlyGlyArgAlaThrTyrArg-172 |
| SEQ. ID. NO. 11075 | 174-ThrAlaPheGlySerAspAspAlaGlyGly-183 |
| SEQ. ID. NO. 11076 | 191-PheAlaAlaLysGlnGlyAsnGlyLysIleGluHisLeuLysSerProGluLeuAsnVal-210 |
| SEQ. ID. NO. 11077 | 213-AlaAlaAlaAspIleLysProAspGlyLysArgHisAla-225 |
| SEQ. ID. NO. 11078 | 234-AsnGlnAlaGluLysGlySerTyrSer-242 |
| SEQ. ID. NO. 11079 | 247-GlyGlyLysAlaGlnGluValAlaGly-255 |
| SEQ. ID. NO. 11080 | 257-AlaGluValLysThrValAsnGly-264 |
| Hydrophilic Regions - Hopp-Woods | |
| SEQ. ID. NO. 11081 | 43-LeuAspHisLysAspLysGlyLeu-50 |
| SEQ. ID. NO. 11082 | 57-GlnSerValArgLysAsnGluLysLeuLysLeu-67 |
| SEQ. ID. NO. 11083 | 71-GlyAlaGluLysThrTyrGlyAsn-78 |
| SEQ. ID. NO. 11084 | 85-GlyLysLeuLysAsnAspLysValSerArg-94 |
| SEQ. ID. NO. 11085 | 101-IleGluValAspGly-105 |
| SEQ. ID. NO. 11086 | 132-GlnIleGlnAspSerGluHisSerGly-140 |
| SEQ. ID. NO. 11087 | 142-MetValAlaLysArgGlnPheArgIle-150 |
| SEQ. ID. NO. 11088 | 152-AspIleAlaGlyGlu-156 |
| SEQ. ID. NO. 11089 | 158-ThrSerPheAspLysLeuProGluGlyGlyArgAlaThrTyr-171 |
| SEQ. ID. NO. 11090 | 177-GlySerAspAspAlaGlyGly-183 |
| SEQ. ID. NO. 11091 | 195-GlnGlyAsnGlyLysIleGluHisLeuLysSerProGluLeuAsnVal-210 |
| SEQ. ID. NO. 11092 | 213-AlaAlaAlaAspIleLysProAspGlyLysArgHisAla-225 |
| SEQ. ID. NO. 11093 | 235-GlnAlaGluLysGlySer-240 |
| SEQ. ID. NO. 11094 | 249-LysAlaGlnGluValAlaGly-255 |
| SEQ. ID. NO. 11095 | 257-AlaGluValLysThr-261 |
| 742 | |
| AMPHI Regions - AMPHI | |
| SEQ. ID. NO. 11096 | 26-ArgGluValProAsp-30 |
| SEQ. ID. NO. 11097 | 53-AsnArgProLeuGln-57 |
| SEQ. ID. NO. 11098 | 66-GluAspTrpSerArgLeu-71 |
| SEQ. ID. NO. 11099 | 77-AsnLeuPheSerGlyPheLysHisValPheAsp-87 |
| SEQ. ID. NO. 11100 | 143-LysAlaLeuGluLysLeuLysAla-150 |
| SEQ. ID. NO. 11101 | 153-AspGluThrAlaLysGluTyrArg-160 |
| SEQ. ID. NO. 11102 | 234-AsnAlaAlaGlnArgPheProAsnSerLeuTyrAsp-245 |
| SEQ. ID. NO. 11103 | 326-ValTyrAlaGlySerCysGlnGlu-333 |
| SEQ. ID. NO. 11104 | 340-SerSerProLeuVal-344 |
| SEQ. ID. NO. 11105 | 369-ArgAsnAlaLysLysIle-374 |
| SEQ. ID. NO. 11106 | 422-ThrProAlaPheThrGlyPheSerGlyThrValProValTrpLysThrValLys-439 |
| SEQ. ID. NO. 11107 | 448-LeuTyrAsnTyrAlaLysTyrLeuAsnThrAsn-458 |
| SEQ. ID. NO. 11108 | 475-LeuHisLeuLeuGlyGlyLeuHisTyr-483 |
| SEQ. ID. NO. 11109 | 505-PheGlnThrAlaSerSer-510 |
| SEQ. ID. NO. 11110 | 543-IleTyrGlySerTyrThrLysIlePheLysGlnGlnAspAsn-556 |
| SEQ. ID. NO. 11111 | 616-GlySerPheGlnThrValAlaLysProIleGlyLysValValSerArg-631 |
| SEQ. ID. NO. 11112 | 643-GluAspTrpLysValPheAlaGly-650 |
| SEQ. ID. NO. 11113 | 657-ArgTyrLysAsnAla-661 |
| SEQ. ID. NO. 11114 | 670-AlaLysAsnSerSer-674 |
| SEQ. ID. NO. 11115 | 677-ProTyrAsnPheSerAsnPheThrProValHisIle-688 |
| SEQ. ID. NO. 11116 | 714-ThrSerSerLeuTyrAsnIle-720 |
| SEQ. ID. NO. 11117 | 725-TyrGlyLeuIleAspGlyPheValArgTyr-734 |
| SEQ. ID. NO. 11118 | 736-LeuGlyLysHisAlaLysLeu-742 |
| SEQ. ID. NO. 11119 | 759-TyrAsnArgThrArgGlyAlaAsnAsnPheTyrGlyGluPro-772 |
| Antigenic Index - Jameson-Wolf | |
| SEQ. ID. NO. 11120 | 6-AlaGluAlaAspAlaGlyAsp-12 |
| SEQ. ID. NO. 11121 | 21-MetTyrGlnLysSerArgGluValProAspPheSerGly-33 |
| SEQ. ID. NO. 11122 | 37-ProCysGluAsnGlnLysThrAlaProPheSerSerThrProAlaCysAsnArgProLeuGlnLeuProArgAsnThrTyrLeuGlyGluAspTrpSer ArgLeuSerAlaAspLysTyrAsn-77 |
| SEQ. ID. NO. 11123 | 86-PheAspAsnGlyTrp-90 |
| SEQ. ID. NO. 11124 | 97-SerTyrThrLysAsnGluSerAspAlaLysVal-107 |
| SEQ. ID. NO. 11125 | 120-LeuSerGlyGluAspAla-125 |
| SEQ. ID. NO. 11126 | 130-ThrGluLysAsnGluValIleProPheGluProLysAspLysAlaLeuGluLysLeuLysAlaTyrArgAspGluThrAlaLysGluTyrArgGluArg LysAspAspPheValLysAsnArgPheAspAsnThrAla-175 |
| SEQ. ID. NO. 11127 | 177-GluGlnTyrArgSerArgArgAlaAlaGluArgLysAlaGlyPheAspLysCysMetSerAspProPheAla-200 |
| SEQ. ID. NO. 11128 | 205-CysGlnGlySerTrpGlyArgProGlyValAspAlaAspLysAlaGluPheValAsp-223 |
| SEQ. ID. NO. 11129 | 235-AlaAlaGlnArgPheProAsnSerLeuTyrAspSerSerPheAsnArgLysAlaThrAlaAsnArgArgTyrSerTyrMetPro-262 |
| SEQ. ID. NO. 11130 | 264-ArgHisThrLysAspAspArgGlnTrp-272 |
| SEQ. ID. NO. 11131 | 286-GlyArgGluHisAsp-290 |
| SEQ. ID. NO. 11132 | 295-TyrAlaTyrGlyAspGluLysIleArgSerGluTyr-306 |
| SEQ. ID. NO. 11133 | 308-GluIleTyrGluArgArgTyrArgValArgProAsnThrGlyAla-322 |
| SEQ. ID. NO. 11134 | 328-AlaGlySerCysGlnGluGluProAspGlyAspLeuSer-340 |
| SEQ. ID. NO. 11135 | 345-ArgGlyHisLysGluProAspTrpGlnAlaTyrAspGluLysGlyAsnArgThrValTyrAlaGluGluCysArgAsnAlaLysLysIleLysThrGlu ProLysLeuAspAlaGluGlyLysGln-386 |
| SEQ. ID. NO. 11136 | 389-TyrTyrAspGluTyrSerGlySerArgThr-398 |

TABLE 1-continued

| | |
|---|---|
| SEQ. ID. NO. 11137 | 405-TyrGluLeuAspGluLysGlyAsnLysIleGlnGluThrAsnProAspGlyThrPro-423 |
| SEQ. ID. NO. 11138 | 439-LysValAlaAspAspHisVal-445 |
| SEQ. ID. NO. 11139 | 454-TyrLeuAsnThrAsnLysThrHis-461 |
| SEQ. ID. NO. 11140 | 485-ArgTyrGluThrSerGlnThrLysAspMetProValArgTyrGlyGlnProAlaSerAspPheGlnThr-507 |
| SEQ. ID. NO. 11141 | 509-SerSerIleArgAlaAspGlnAspHisTyrThr-519 |
| SEQ. ID. NO. 11142 | 521-LysMetGlnGlyHisLysLeuThrPro-529 |
| SEQ. ID. NO. 11143 | 545-GlySerTyrThrLys-549 |
| SEQ. ID. NO. 11144 | 551-PheLysGlnGlnAspAsnValAspValSerAla-561 |
| SEQ. ID. NO. 11145 | 584-GlyArgLeuAsnAla-588 |
| SEQ. ID. NO. 11146 | 595-LeuGluGlnLysAsnArgThrValVal-603 |
| SEQ. ID. NO. 11147 | 610-GlyAlaGlyGlyLysGlnGlySer-617 |
| SEQ. ID. NO. 11148 | 628-ValValSerArgGlyAlaGluPheGluLeuSerGlyGluLeuAsnGluAspTrpLys-646 |
| SEQ. ID. NO. 11149 | 652-ThrTyrAsnLysSerArgTyrLysAsnAlaAlaGluValAsnAlaGluArgLeuAlaLysAsnSerSerAlaAspProTyrAsnPheSerAsn-682 |
| SEQ. ID. NO. 11150 | 708-ValSerAlaGlnSerGlyThrSerSerLeuTyrAsnIleArgGlnGlyGly-724 |
| SEQ. ID. NO. 11151 | 735-GluLeuGlyLysHisAlaLys-741 |
| SEQ. ID. NO. 11152 | 746-GlyThrAsnLeuAsnGlyArgThrTyrPheGluAsnAsnTyrAsnArgThrArgGlyAlaAsnAsnPheTyrGlyGluProArgThrValSerMet-777 |
| Hydrophilic Regions - Hopp-Woods | |
| SEQ. ID. NO. 11153 | 6-AlaGluAlaAspAlaGlyAsp-12 |
| SEQ. ID. NO. 11154 | 23-GlnLysSerArgGluValProAsp-30 |
| SEQ. ID. NO. 11155 | 67-AspTrpSerArgLeuSerAlaAspLys-75 |
| SEQ. ID. NO. 11156 | 97-SerTyrThrLysAsnGluSerAspAlaLysVal-107 |
| SEQ. ID. NO. 11157 | 120-LeuSerGlyGluAspAla-125 |
| SEQ. ID. NO. 11158 | 130-ThrGluLysAsnGluValIleProPheGluProLysAspLysAlaLeuGluLysLeuLysAlaTyrArgAspGluThrAlaLysGluTyrArgGluArg LysAspAspPheValLysAsnArgPheAspAsnThrAla-175 |
| SEQ. ID. NO. 11159 | 177-GluGlnTyrArgSerArgArgAlaAlaGluArgLysAlaGlyPheAspLysCysMetSer-196 |
| SEQ. ID. NO. 11160 | 212-ProGlyValAspAlaAspLysAlaGluPheValAsp-223 |
| SEQ. ID. NO. 11161 | 247-SerPheAsnArgLysAlaThrAlaAsnArgArgTyrSer-259 |
| SEQ. ID. NO. 11162 | 264-ArgHisThrLysAspAspArgGlnTrp-272 |
| SEQ. ID. NO. 11163 | 286-GlyArgGluHisAsp-290 |
| SEQ. ID. NO. 11164 | 297-TyrGlyAspGluLysIleArgSerGluTyr-306 |
| SEQ. ID. NO. 11165 | 308-GluIleTyrGluArgArgTyrArgValArgProAsnThr-320 |
| SEQ. ID. NO. 11166 | 331-CysGlnGluProAspGlyAspLeu-339 |
| SEQ. ID. NO. 11167 | 345-ArgGlyHisLysGluProAsp-351 |
| SEQ. ID. NO. 11168 | 354-AlaTyrAspGluLysGlyAsnArg-361 |
| SEQ. ID. NO. 11169 | 363-ValTyrAlaGluGluCysArgAsnAlaLysLysIleLysThrGluProLysLeuAspAlaGluGlyLysGln-386 |
| SEQ. ID. NO. 11170 | 393-TyrSerGlySerArg-397 |
| SEQ. ID. NO. 11171 | 405-TyrGluLeuAspGluLysGlyAsnLysIleGlnGluThrAsnProAspGly-421 |
| SEQ. ID. NO. 11172 | 439-LysValAlaAspAspHisVal-445 |
| SEQ. ID. NO. 11173 | 485-ArgTyrGluThrSerGlnThrLysAspMetProVal-496 |
| SEQ. ID. NO. 11174 | 500-GlnProAlaSerAsp-504 |
| SEQ. ID. NO. 11175 | 509-SerSerIleArgAlaAspGlnAspHisTyrThr-519 |
| SEQ. ID. NO. 11176 | 551-PheLysGlnGlnAspAsnValAspValSerAla-561 |
| SEQ. ID. NO. 11177 | 597-GlnLysAsnArgThrValVal-603 |
| SEQ. ID. NO. 11178 | 611-AlaGlyGlyLysGlnGlySer-617 |
| SEQ. ID. NO. 11179 | 628-ValValSerArgGlyAlaGluPheGluLeuSerGlyGluLeuAsnGluAspTrpLys-646 |
| SEQ. ID. NO. 11180 | 654-AsnLysSerArgTyrLysAsnAlaAlaGluValAsnAlaGluArgLeuAlaLysAsnSerSerAlaAsp-676 |
| SEQ. ID. NO. 11181 | 735-GluLeuGlyLysHisAlaLys-741 |
| SEQ. ID. NO. 11182 | 758-AsnTyrAsnArgThrArgGly-764 |
| SEQ. ID. NO. 11183 | 770-GlyGluProArgThrValSerMet-777 |
| 743 | |
| AMPHI Regions - AMPHI | |
| SEQ. ID. NO. 11184 | 19-TyrGlyGlySerPhe-23 |
| SEQ. ID. NO. 11185 | 58-SerTyrThrIleAsp-62 |
| SEQ. ID. NO. 11186 | 64-MetSerThrAlaThrGly-69 |
| SEQ. ID. NO. 11187 | 96-ThrLeuGluGluAlaMetLysAsnThrThrGlyValAsnValValArgAsp-112 |
| SEQ. ID. NO. 11188 | 158-ValTyrAspHisIleGluValValArgGlyAlaThrGly-170 |
| Antigenic Index - Jameson-Wolf | |
| SEQ. ID. NO. 11189 | 1-MetAsnGlnAsnHis-5 |
| SEQ. ID. NO. 11190 | 30-ValSerAspGlyAsnThrVal-36 |
| SEQ. ID. NO. 11191 | 41-ValAsnValArgGlySer-46 |
| SEQ. ID. NO. 11192 | 51-GlyLysThrGluLysThrArgSerTyrThrIleAspArgMetSerThr-66 |
| SEQ. ID. NO. 11193 | 72-IleAlaGlyLysAspThrProGlnSer-80 |
| SEQ. ID. NO. 11194 | 85-ThrArgSerArgLeuAspAspLysAlaValHisThrLeuGluGluAlaMetLysAsnThrThrGly-106 |
| SEQ. ID. NO. 11195 | 109-ValValArgAspSerGlyLeuGlnThrArgPheLeuSerArgGlyPhe-124 |
| SEQ. ID. NO. 11196 | 128-GlnIleGlyGluAspGlyMet-134 |
| SEQ. ID. NO. 11197 | 140-GlyArgSerGlyTyrThrAlaLysIleAspValSerProSerThrAsp-155 |
| SEQ. ID. NO. 11198 | 163-GluValValArgGlyAlaThrGlyLeuThrGlnSerAsnSerGluProGlyGly-180 |
| Hydrophilic Regions - Hopp-Woods | |
| SEQ. ID. NO. 11199 | 51-GlyLysThrGluLysThrArgSerTyrThrIleAspArgMetSerThr-66 |
| SEQ. ID. NO. 11200 | 72-IleAlaGlyLysAspThrProGln-79 |
| SEQ. ID. NO. 11201 | 85-ThrArgSerArgLeuAspAspLysAlaValHisThrLeuGluGluAlaMetLysAsn-103 |
| SEQ. ID. NO. 11202 | 109-ValValArgAspSerGlyLeu-115 |
| SEQ. ID. NO. 11203 | 128-GlnIleGlyGluAspGlyMet-134 |
| SEQ. ID. NO. 11204 | 174-SerAsnSerGluProGlyGly-180 |
| 744 | |
| AMPHI Regions - AMPHI | |
| SEQ. ID. NO. 11205 | 36-LeuAspGluLeuCys-40 |
| SEQ. ID. NO. 11206 | 65-AsnPheTyrLysAsnIleHisAlaThrThrLysPheValArgGluThrAspTyrSerLysPheIleGlnLeuLysLysAlaArgHisLeuThrValSer AspPheThrSerIleTrpLysValIleLeuTyr-108 |
| SEQ. ID. NO. 11207 | 124-SerSerIlePheAsnLysPheLysAlaLeuAspGluAlaIleAsnGluTyrTyrTyr-142 |

TABLE 1-continued

| | |
|---|---|
| SEQ. ID. NO. 11208 | 165-MetIlePheGlyLysPheValLysLeuGly-174 |
| SEQ. ID. NO. 11209 | 197-ArgLysPheLysAspAla-202 |
| SEQ. ID. NO. 11210 | 228-PheAspGluTyrHisGluCysValLysGlyLeuAlaAsn-240 |
| SEQ. ID. NO. 11211 | 270-IlePheAspSerLeu-274 |
| SEQ. ID. NO. 11212 | 299-TyrArgSerSerLysIlePheGlyValPheAspHisLeuLeuArgThr-314 |
| SEQ. ID. NO. 11213 | 322-LeuGluLysGlyAsnSer-327 |
| SEQ. ID. NO. 11214 | 338-AsnLeuHisAspGluTyrLysAsnLeuThrSerPheIleSerPhe-352 |
| SEQ. ID. NO. 11215 | 361-ArgAspIleLeuGlnMetLeu-367 |
| SEQ. ID. NO. 11216 | 416-TyrGlnAsnPheLeuLysPhePheGluPhe-425 |
| SEQ. ID. NO. 11217 | 434-TyrSerAspPheLeuLysAlaPheGluArgLeuLysLysHis-447 |
| SEQ. ID. NO. 11218 | 454-GluIleProLysPheMetSerThrAlaAsnGlu-464 |
| SEQ. ID. NO. 11219 | 473-AsnValIleAlaTyrLeu-478 |
| SEQ. ID. NO. 11220 | 515-SerGlyLeuSerLysAlaLeuAspValGly-524 |
| Antigenic Index - Jameson-Wolf | |
| SEQ. ID. NO. 11221 | 15-AlaAsnTyrArgArgArgGluAsnLysAspLeuPhe-26 |
| SEQ. ID. NO. 11222 | 33-GlyGluTyrLeuAspGluLeuCysGluProAsnIle-44 |
| SEQ. ID. NO. 11223 | 48-IleGlyGluLysGlyThrGlyLysThr-56 |
| SEQ. ID. NO. 11224 | 64-AsnAsnPheTyrLys-68 |
| SEQ. ID. NO. 11225 | 75-LysPheValArgGluThrAspTyr-82 |
| SEQ. ID. NO. 11226 | 89-LysLysAlaArgHis-93 |
| SEQ. ID. NO. 11227 | 113-AsnGlnIleLysCysLysGluAsnGlyIle-122 |
| SEQ. ID. NO. 11228 | 131-LysAlaLeuAspGluAlaIleAsn-138 |
| SEQ. ID. NO. 11229 | 140-TyrTyrTyrGlyAlaPheAspProGluIle-149 |
| SEQ. ID. NO. 11230 | 157-GluAsnSerLysGluAlaAla-163 |
| SEQ. ID. NO. 11231 | 171-ValLysLeuGlyGluGluGluSerGln-179 |
| SEQ. ID. NO. 11232 | 184-ThrGluSerLysPhe-188 |
| SEQ. ID. NO. 11233 | 194-PheIleGluArgLysPheLysAspAlaLeuSer-204 |
| SEQ. ID. NO. 11234 | 206-LeuLysLeuLysAspAsn-211 |
| SEQ. ID. NO. 11235 | 217-AspGlyIleAspIleArgProSerGlnIleProPhe-228 |
| SEQ. ID. NO. 11236 | 230-GluTyrHisGluCysValLys-236 |
| SEQ. ID. NO. 11237 | 251-ProSerIleLysAspSerLysGlyArgMet-260 |
| SEQ. ID. NO. 11238 | 267-ArgProAspIlePheAspSerLeuGlyLeuGlnAsnGlnAsnThrLysLeuGlnAspAsnSerVal-288 |
| SEQ. ID. NO. 11239 | 291-AspTrpArgThrAspTyrLysSerTyrArgSerSerLysIle-304 |
| SEQ. ID. NO. 11240 | 312-LeuArgThrGlnGlnGluLysGlnAspSerLeuGluLysGlyAsnSerTrpAspTyrTyrPheProTrpAsnAlaProAsnLeuHisAspGluTyrLys AsnLeu-346 |
| SEQ. ID. NO. 11241 | 353-LeuArgLysSerTyrTyrArgProArgAspIle-363 |
| SEQ. ID. NO. 11242 | 371-GlnLysAsnLysLysSerLysGluAspTyrValVal-382 |
| SEQ. ID. NO. 11243 | 384-GluAspPheAspAsnThrSerPheGlnArgGluTyrSer-396 |
| SEQ. ID. NO. 11244 | 412-SerGlnSerAspTyrGlnAsn-418 |
| SEQ. ID. NO. 11245 | 427-AsnGlyLysAspArgPheLysTyrSerAspPhe-437 |
| SEQ. ID. NO. 11246 | 439-LysAlaPheGluArgLeuLysLysHisLeuGln-449 |
| SEQ. ID. NO. 11247 | 454-GluIleProLysPhe-458 |
| SEQ. ID. NO. 11248 | 478-LeuAspAsnProGluAspGluThrLysPro-487 |
| SEQ. ID. NO. 11249 | 493-PheLysAspArgAsnTyrAlaAsnIleSerProLysIleLysThrGluThr-509 |
| SEQ. ID. NO. 11250 | 518-SerLysAlaLeuAsp-522 |
| SEQ. ID. NO. 11251 | 524-GlyThrProPheLysAsnLysGln-531 |
| Hydrophilic Regions - Hopp-Woods | |
| SEQ. ID. NO. 11252 | 15-AlaAsnTyrArgArgArgGluAsnLysAspLeuPhe-26 |
| SEQ. ID. NO. 11253 | 34-GluTyrLeuAspGluLeuCysGlu-41 |
| SEQ. ID. NO. 11254 | 50-GluLysGlyThrGly-54 |
| SEQ. ID. NO. 11255 | 75-LysPheValArgGluThrAspTyr-82 |
| SEQ. ID. NO. 11256 | 89-LysLysAlaArgHis-93 |
| SEQ. ID. NO. 11257 | 115-IleLysCysLysGluAsnGlyIle-122 |
| SEQ. ID. NO. 11258 | 131-LysAlaLeuAspGluAlaIle-137 |
| SEQ. ID. NO. 11259 | 157-GluAsnSerLysGluAlaAla-163 |
| SEQ. ID. NO. 11260 | 171-ValLysLeuGlyGluGluGluSerGln-179 |
| SEQ. ID. NO. 11261 | 184-ThrGluSerLysPhe-188 |
| SEQ. ID. NO. 11262 | 194-PheIleGluArgLysPheLysAspAlaLeuSer-204 |
| SEQ. ID. NO. 11263 | 206-LeuLysLeuLysAspAsn-211 |
| SEQ. ID. NO. 11264 | 219-IleAspIleArgPro-223 |
| SEQ. ID. NO. 11265 | 230-GluTyrHisGluCysValLys-236 |
| SEQ. ID. NO. 11266 | 251-ProSerIleLysAspSerLysGlyArgMet-260 |
| SEQ. ID. NO. 11267 | 279-GlnAsnThrLysLeuGlnAsp-285 |
| SEQ. ID. NO. 11268 | 292-TrpArgThrAspTyrLysSerTyrArgSer-301 |
| SEQ. ID. NO. 11269 | 314-ThrGlnGlnGluLysGlnAspSerLeuGluLysGlyAsnSer-327 |
| SEQ. ID. NO. 11270 | 338-AsnLeuHisAspGluTyrLysAsn-345 |
| SEQ. ID. NO. 11271 | 356-SerTyrTyrArgProArgAspIle-363 |
| SEQ. ID. NO. 11272 | 371-GlnLysAsnLysLysSerLysGluAspTyrValVal-382 |
| SEQ. ID. NO. 11273 | 384-GluAspPheAspAsn-388 |
| SEQ. ID. NO. 11274 | 427-AsnGlyLysAspArgPheLysTyr-434 |
| SEQ. ID. NO. 11275 | 439-LysAlaPheGluArgLeuLysLysHisLeuGln-449 |
| SEQ. ID. NO. 11276 | 479-AspAsnProGluAspGluThrLysPro-487 |
| SEQ. ID. NO. 11277 | 493-PheLysAspArgAsnTyr-498 |
| SEQ. ID. NO. 11278 | 503-ProLysIleLysThrGluThr-509 |
| SEQ. ID. NO. 11279 | 527-PheLysAsnLysGln-531 |
| 745 | |
| AMPHI Regions - AMPHI | |
| SEQ. ID. NO. 11280 | 9-SerValThrAlaValIle-14 |
| SEQ. ID. NO. 11281 | 33-AspValIleLeuAsnAsp-38 |
| SEQ. ID. NO. 11282 | 116-CysThrAsnPheIleLysLeuTrpAsnAlaValSer-127 |

TABLE 1-continued

SEQ. ID. NO. 11283 145-GluLeuGluIleLeuVal-150
Antigenic Index - Jameson-Wolf
SEQ. ID. NO. 11284 21-IleAsnLysLysThrSerLysGlnLysAlaThr-31
SEQ. ID. NO. 11285 37-AsnAspTyrGlnAsp-41
SEQ. ID. NO. 11286 43-GlnPheValGluAlaAspAsnHisIleSerProTyrIle-55
SEQ. ID. NO. 11287 58-ThrAlaValAspAspAsnAsnAlaArg-66
SEQ. ID. NO. 11288 73-TyrGlnAsnLysGlyGlyGlnTrpGluLysGluArgGlyHis-86
SEQ. ID. NO. 11289 102-AsnSerGlyValLeuAspGluAspLeuPheLys-112
SEQ. ID. NO. 11290 132-LysIleArgGluGluGluArgLysAspThrIlePheArgGluLeuGlu-147
SEQ. ID. NO. 11291 156-AsnProLeuLysAlaSerAspLeu-163
Hydrophilic Regions - Hopp-Woods
SEQ. ID. NO. 11292 23-LysLysThrSerLysGlnLysAlaThr-31
SEQ. ID. NO. 11293 43-GlnPheValGluAlaAspAsnHis-50
SEQ. ID. NO. 11294 58-ThrAlaValAspAspAsnAsnAlaArg-66
SEQ. ID. NO. 11295 76-LysGlyGlyGlnTrpGluLysGluArgGlyHis-86
SEQ. ID. NO. 11296 105-ValLeuAspGluAspLeuPheLys-112
SEQ. ID. NO. 11297 132-LysIleArgGluGluGluArgLysAspThrIlePheArgGluLeuGlu-147
SEQ. ID. NO. 11298 156-AsnProLeuLysAlaSerAspLeu-163
746
AMPHI Regions - AMPHI
SEQ. ID. NO. 11299 10-LeuSerGlyTyrGluGlnLeuLys-17
SEQ. ID. NO. 11300 42-LeuSerSerGlyProAlaGluGlnThrAla-51
SEQ. ID. NO. 11301 72-SerAlaAlaAspLysProGlnAsp-79
SEQ. ID. NO. 11302 94-SerGluProGluAsn-98
SEQ. ID. NO. 11303 118-LeuGluAlaSerGluLysLeuGlnAlaGluThrAlaLysThrAlaPro-134
SEQ. ID. NO. 11304 153-AspThrValAlaValGlu-158
SEQ. ID. NO. 11305 160-ProLysArgThrAlaGluThr-166
SEQ. ID. NO. 11306 170-LysAlaGluArgThr-174
SEQ. ID. NO. 11307 184-ThrLysThrAlaGluLysValAlaAspLysProLys-195
SEQ. ID. NO. 11308 210-SerAlaValLysGluAlaLysLysAlaAspLysAlaGluSer-223
SEQ. ID. NO. 11309 238-GluThrAlaGlnLysThrAspLysAlaAspLysThrLysThrAlaGluLys-254
SEQ. ID. NO. 11310 287-SerThrIleThrGluIleMetThr-294
SEQ. ID. NO. 11311 307-TyrLysAsnAlaArgAspAlaGluArgAspLeu-317
Antigenic Index - Jameson-Wolf
SEQ. ID. NO. 11312 1-MetSerGluAsnLysGlnAsnGluValLeuSerGlyTyrGluGlnLeuLysArgArgAsnArgArgArgLeuValThr-26
SEQ. ID. NO. 11313 43-SerSerGlyProAlaGluGlnThrAlaGlyGluThrSerGlyValGluAsnLysAlaAlaGly-63
SEQ. ID. NO. 11314 68-ProAlaLeuLysSerAlaAlaAspLysProGlnAspLeuAlaGlyGluAspLysProSerAlaAlaAspSerGluIleSerGluProGluAsnVal-99
SEQ. ID. NO. 11315 108-GluArgLeuGluAspSerAsnIleLysGlyLeuGluAlaSerGluLysLeuGlnAlaGluThrAlaLysThrAlaProLysGlnAlaLysGlnArg
AlaAlaGluLysValProAlaThrAlaAspSerThrAspThrValAlaValGluLysProLysArgThrAlaGluThrLysProGlnLysAlaGluArgThrAla
LysAlaLysProLysAlaLysGluThrLysThrAlaGluLysValAlaAspLysProLysThrAlaAlaGluLysThrLysProAspThrAlaLysSerAspSer
AlaValLysGluAlaLysLysAlaAspLysAlaGluSerLysLysThrAlaGluLysAspArgSerAspGlyLysLysHisGluThrAlaGlnLysThrAspLys
AlaAspLysThrLysThrAlaGluLysGluLysSerGlyLysLysAlaAla-262
SEQ. ID. NO. 11316 266-GlyTyrAlaGluLysGluArgAlaLeuSerLeuGlnArgLysMetLysAlaAlaGlyIle-285
SEQ. ID. NO. 11317 292-IleMetThrAspAsnGlyLysValTyrArgValLysSerSerAsnTyrLysAsnAlaArgAspAlaGluArgAspLeuAsnLysLeuArgVal-322
Hydrophilic Regions - Hopp-Woods
SEQ. ID. NO. 11318 1-MetSerGluAsnLysGlnAsnGluVal-9
SEQ. ID. NO. 11319 14-GluGlnLeuLysArgArgAsnArgArgArgLeuVal-25
SEQ. ID. NO. 11320 45-GlyProAlaGluGlnThrAlaGlyGluThrSerGlyValGluAsnLysAlaAlaGly-63
SEQ. ID. NO. 11321 68-ProAlaLeuLysSerAlaAlaAspLysProGlnAspLeuAlaGlyGluAspLysProSerAlaAlaAspSerGluIleSerGluProGluAsnVal-99
SEQ. ID. NO. 11322 108-GluArgLeuGluAspSerAsnIleLysGlyLeuGluAlaSerGluLysLeuGlnAlaGluThrAlaLysThrAlaProLysGlnAlaLysGlnArg
AlaAlaGluLysValProAlaThrAlaAspSerThrAsp-153
SEQ. ID. NO. 11323 155-ValAlaValGluLysProLysArgThrAlaGluThrLysProGlnLysAlaGluArgThrAlaLysAlaLysProLysAlaLysGluThrLysThrAla
GluLysValAlaAspLysProLysThrAlaAlaGluLysThrLysProAspThrAlaLysSerAspSerAlaValLysGluAlaLysLysAlaAspLysAlaGlu
SerLysLysThrAlaGluLysAspArgSerAspGlyLysLysHisGluThrAlaGlnLysThrAspLysAlaAspLysThrLysThrAlaGluLysGluLysSer
rGlyLysLysAlaAla-262
SEQ. ID. NO. 11324 267-TyrAlaGluLysGluArgAlaLeuSerLeuGlnArgLysMetLysAlaAlaGlyIle-285
SEQ. ID. NO. 11325 292-IleMetThrAspAsnGlyLysValTyrArgValLysSerSerAsnTyrLysAsnAlaArgAspAlaGluArgAspLeuAsnLysLeuArgVal-322
747
AMPHI Regions - AMPHI
SEQ. ID. NO. 11326 24-AlaSerArgAspValSerLysSerAlaLysGlyTrp-35
Antigenic Index - Jameson-Wolf
SEQ. ID. NO. 11327 8-TyrAlaAspLeuArgGlyLysThrLysVal-17
SEQ. ID. NO. 11328 23-GlyAlaSerArgAspValSerLysSerAlaLysGlyTrp-35
SEQ. ID. NO. 11329 42-AsnValGlyLysGlnLeuThrAspSerValGlyLeuGluPheAspProTyrTyrArgHisLysThrIleTyrLysProArgGluIleValLeuAspGly
AspLysThrLysMetGlyArgSerLysSerAsnGluTyrGly-88
SEQ. ID. NO. 11330 97-SerGlnLeuLysSerLys-102
Hydrophilic Regions - Hopp-Woods
SEQ. ID. NO. 11331 8-TyrAlaAspLeuArgGlyLysThrLysVal-17
SEQ. ID. NO. 11332 23-GlyAlaSerArgAspValSerLysSerAlaLys-33
SEQ. ID. NO. 11333 63-ThrIleTyrLysProArgGluIleValLeuAspGlyAspLysThrLysMetGlyArgSerLysSerAsnGluTyr-87
748
AMPHI Regions - AMPHI
SEQ. ID. NO. 11334 22-GlyAlaValGlyAlaIleGlyGly-29
SEQ. ID. NO. 11335 37-GlyGluThrAlaGluArgThrAlaGluSerGlnHis-48
SEQ. ID. NO. 11336 82-SerAlaLysGlnLeuGluAsnLeuPheArgThrLeu-93
SEQ. ID. NO. 11337 155-LeuGlnGluMetArgAspPheSerAsnAspLysLeuGlnLysSerTrp-170
SEQ. ID. NO. 11338 188-GlnAlaAlaLeuArgAspIleIleLysHisThrValGln-200
SEQ. ID. NO. 11339 250-GlyValAlaAlaAsnSer-255
SEQ. ID. NO. 11340 257-AspGluProGluTrp-261
SEQ. ID. NO. 11341 268-GlnAlaValArgLeuIleArgHisPheValGluPheTrpAspArg-282

TABLE 1-continued

| | |
|---|---|
| SEQ. ID. NO. 11342 | 310-GlnProAspPheAlaLysAspProGlu-318 |
| SEQ. ID. NO. 11343 | 334-ArgAspProGluPheLeu-339 |
| SEQ. ID. NO. 11344 | 390-LeuGluGluTyrIleSerProPhe-397 |
| Antigenic Index - Jameson-Wolf | |
| SEQ. ID. NO. 11345 | 1-MetSerLysLysGlnProAlaGlnProThrArgArgThrLeuPhe-15 |
| SEQ. ID. NO. 11346 | 30-TyrLeuGlyGlyLysLysGlnGlyGluThrAlaGluArgThrAlaGluSerGlnHisSerProGlnAla-52 |
| SEQ. ID. NO. 11347 | 80-AlaGlnSerAlaLysGlnLeuGluAsn-88 |
| SEQ. ID. NO. 11348 | 101-ThrGlnGlyGlyGluTyrGlnAspGlyAspAspLysLeuProProAlaGlySerGly-119 |
| SEQ. ID. NO. 11349 | 125-PheAsnProAspGlyLeuThr-131 |
| SEQ. ID. NO. 11350 | 139-SerLeuPheAspGlyArgPheGlyLeuLysAspLysLysProIleHis-154 |
| SEQ. ID. NO. 11351 | 156-GlnGluMetArgAspPheSerAsnAspLysLeuGlnLysSerTrpCysAspGlyAspLeuSer-176 |
| SEQ. ID. NO. 11352 | 183-ThrProGluThrCys-187 |
| SEQ. ID. NO. 11353 | 208-IleAspGlyTrpGlnProLysSerGluProGlyAlaMetAla-221 |
| SEQ. ID. NO. 11354 | 226-LeuGlyPheArgAspGlyThrGlyAsnProLysValSerAspProLysThrAlaAspGlu-245 |
| SEQ. ID. NO. 11355 | 255-SerLeuAspGluProGluTrpAlaLysAsnGlySerTyrGlnAla-269 |
| SEQ. ID. NO. 11356 | 279-PheTrpAspArgThrProLeuGlnGluGlnThrAspIlePheGlyArgArgLysTyrSerGlyAlaProMetAspGlyLysLysGluAlaAspGlnProAspPheAlaLysAspProGluGlyAspIleThrProLysAspSerHisIleArgLeuAlaAsnProArgAspProGluPheLeuLysLysHisArgLeuPheArg-346 |
| SEQ. ID. NO. 11357 | 348-AlaTyrSerTyrSerArgGlyLeuAlaSerSerGlyGlnLeu-361 |
| SEQ. ID. NO. 11358 | 385-LeuAsnGlyGluProLeuGluGluTyr-393 |
| SEQ. ID. NO. 11359 | 406-ProGlyValGluLysGlyGlyPhe-413 |
| Hydrophilic Regions - Hopp-Woods | |
| SEQ. ID. NO. 11360 | 1-MetSerLysLysGlnProAlaGlnProThrArgArgThrLeuPhe-15 |
| SEQ. ID. NO. 11361 | 32-GlyGlyLysLysGlnGlyGluThrAlaGluArgThrAlaGluSerGlnHisSer-49 |
| SEQ. ID. NO. 11362 | 80-AlaGlnSerAlaLysGlnLeuGluAsn-88 |
| SEQ. ID. NO. 11363 | 104-GlyGluTyrGlnAspGlyAspAspLysLeuProPro-115 |
| SEQ. ID. NO. 11364 | 145-PheGlyLeuLysAspLysLysProIleHis-154 |
| SEQ. ID. NO. 11365 | 156-GlnGluMetArgAspPheSerAsnAspLysLeuGlnLysSerTrpCysAspGlyAspLeu-175 |
| SEQ. ID. NO. 11366 | 211-TrpGlnProLysSerGluProGlyAlaMetAla-221 |
| SEQ. ID. NO. 11367 | 229-ArgAspGlyThrGlyAsnProLysValSerAspProLysThrAlaAsp-244 |
| SEQ. ID. NO. 11368 | 255-SerLeuAspGluProGluTrpAlaLys-263 |
| SEQ. ID. NO. 11369 | 283-ThrProLeuGlnGluGlnThrAspIlePheGlyArgArgLysTyrSer-298 |
| SEQ. ID. NO. 11370 | 301-ProMetAspGlyLysLysGluAlaAspGlnProAspPheAlaLysAspProGluGlyAspIleThrProLysAspSerHisIle-328 |
| SEQ. ID. NO. 11371 | 331-AlaAsnProArgAspProGluPheLeuLysLysHisArgLeuPheArg-346 |
| SEQ. ID. NO. 11372 | 388-GluProLeuGluGluTyr-393 |
| SEQ. ID. NO. 11373 | 407-GlyValGluLysGlyGlyGly-412 |
| 749 | |
| AMPHI Regions - AMPHI | |
| SEQ. ID. NO. 11374 | 20-CysGlnProProGluAla-25 |
| SEQ. ID. NO. 11375 | 140-AlaAspLeuGluLysLeuSerGlnProLeuAla-150 |
| SEQ. ID. NO. 11376 | 157-GlnGlyGluValLysGluLeuVal-164 |
| SEQ. ID. NO. 11377 | 169-ThrPheThrGluAlaValLysAlaGlyAspIleGluLysAla-182 |
| SEQ. ID. NO. 11378 | 196-IleGluProIleAlaGluLeuPheSerGluLeuAspPro-208 |
| SEQ. ID. NO. 11379 | 224-AlaGlyPheThrGlyPheHisArg-231 |
| SEQ. ID. NO. 11380 | 243-SerGlyValLysGluIleAlaAlaLysLeuMetThrAspValGluAlaLeuGlnLysGluIleAsp-264 |
| SEQ. ID. NO. 11381 | 274-ValGlyGlyAlaSerGluLeuIleGluGluValAlaGly-286 |
| SEQ. ID. NO. 11382 | 309-AspGlySerLysLysIleValAspLeuPheArgProLeu-321 |
| SEQ. ID. NO. 11383 | 337-PheLysGlnValAsnGluIleLeuAlaLys-346 |
| SEQ. ID. NO. 11384 | 351-AspGlyPheGluThrTyrAspLysLeuGlyGlu-361 |
| SEQ. ID. NO. 11385 | 366-AlaLeuGlnAlaSerIleAsnAlaLeuAlaGluAspLeuAlaGlnLeuArgGlyIleLeuGlyLeu-387 |
| Antigenic Index - Jameson-Wolf | |
| SEQ. ID. NO. 11386 | 1-MetArgLysPheAsn-5 |
| SEQ. ID. NO. 11387 | 21-GlnProProGluAlaGluLysAlaAlaPro-30 |
| SEQ. ID. NO. 11388 | 32-AlaSerGlyGluAlaGlnThrAlaAsnGluGlyGlySer-44 |
| SEQ. ID. NO. 11389 | 50-AsnAspAsnAlaCysGluProMetGlu-58 |
| SEQ. ID. NO. 11390 | 70-IleLysAsnAsnSerGlyArgLysLeuGluTrpGluIle-82 |
| SEQ. ID. NO. 11391 | 87-MetValValAspGluArgGluAsnIleAla-96 |
| SEQ. ID. NO. 11392 | 98-GlyLeuSerAspLysMetThr-104 |
| SEQ. ID. NO. 11393 | 108-LeuProGlyTyrGluMet-114 |
| SEQ. ID. NO. 11394 | 120-ThrAsnProArgGlyLysLeuValValThrAspSerGlyPheLysAspThrAlaAsnGluAlaAspLeuGluLysLeuSer-146 |
| SEQ. ID. NO. 11395 | 158-GlyGluValLysGluLeuValAlaLysThrLysThrPheThrGluAlaValLysAlaGlyAspIleGluLysAlaLysSerLeuPheAla-187 |
| SEQ. ID. NO. 11396 | 189-ThrArgValHisTyrGluArgIleGluProIle-199 |
| SEQ. ID. NO. 11397 | 204-SerGlyLeuAspProValIleAspAlaArgGluAspAspPheLysAspGlyAlaLysAspAlaGly-225 |
| SEQ. ID. NO. 11398 | 238-ValGluLysAspValSerGlyValLysGluIleAlaAla-250 |
| SEQ. ID. NO. 11399 | 252-LeuMetThrAspValGluAlaLeuGlnLysGluIleAsp-264 |
| SEQ. ID. NO. 11400 | 269-ProProGlyLysValValGlyGlyAla-277 |
| SEQ. ID. NO. 11401 | 279-GluLeuIleGluGluValAlaAlaGlySerLysIleSerGlyGluGluAspArgTyrSerHisThrAspLeuSerAspPheGlnAlaAsnValAspGlySerLysLysIleValAsp-316 |
| SEQ. ID. NO. 11402 | 322-IleGluAlaLysAsnLysAlaLeuLeuGluLysThrAspThrAsnPheLysGlnValAsn-341 |
| SEQ. ID. NO. 11403 | 345-AlaLysTyrArgThrLysAspGlyPheGluThrTyrAspLysLeuGlyGluAlaAspArgLysAlaLeu-367 |
| SEQ. ID. NO. 11404 | 374-LeuAlaGluAspLeuAlaGln-380 |
| Hydrophilic Regions - Hopp-Woods | |
| SEQ. ID. NO. 11405 | 1-MetArgLysPheAsn-5 |
| SEQ. ID. NO. 11406 | 21-GlnProProGluAlaGluLysAlaAlaPro-30 |
| SEQ. ID. NO. 11407 | 32-AlaSerGlyGluAlaGlnThrAlaAsnGluGlyGlySer-44 |
| SEQ. ID. NO. 11408 | 52-AsnAlaCysGluProMetGlu-58 |
| SEQ. ID. NO. 11409 | 72-AsnAsnSerGlyArgLysLeuGluTrpGluIle-82 |
| SEQ. ID. NO. 11410 | 87-MetValValAspGluArgGluAsnIle-95 |
| SEQ. ID. NO. 11411 | 99-LeuSerAspLysMetThr-104 |
| SEQ. ID. NO. 11412 | 110-GlyGluTyrGluMet-114 |

TABLE 1-continued

| | |
|---|---|
| SEQ. ID. NO. 11413 | 122-ProArgGlyLysLeuValVal-128 |
| SEQ. ID. NO. 11414 | 131-SerGlyPheLysAspThrAlaAsnGluAlaAspLeuGluLysLeuSer-146 |
| SEQ. ID. NO. 11415 | 158-GlyGluValLysGluLeuValAlaLysThrLysThrPheThrGluAlaValLysAlaGlyAspIleGluLysAlaLysSerLeuPheAla-187 |
| SEQ. ID. NO. 11416 | 189-ThrArgValHisTyrGluArgIleGluProIle-199 |
| SEQ. ID. NO. 11417 | 204-SerGluLysAspProValIleAspAlaArgGluAspAspPheLysAspGlyAlaLysAspAlaGly-225 |
| SEQ. ID. NO. 11418 | 238-ValGluLysAspValSerGlyValLysGluIleAlaAla-250 |
| SEQ. ID. NO. 11419 | 252-LeuMetThrAspValGluAlaLeuGlnLysGluIleAsp-264 |
| SEQ. ID. NO. 11420 | 279-GluLeuIleGluGluValAlaGly-286 |
| SEQ. ID. NO. 11421 | 288-LysIleSerGlyGluGluAspArgTyrSerHis-298 |
| SEQ. ID. NO. 11422 | 308-ValAspGlySerLysLysIleValAsp-316 |
| SEQ. ID. NO. 11423 | 322-IleGluAlaLysAsnLysAlaLeuLeuGluLysThrAspThrAsnPhe-337 |
| SEQ. ID. NO. 11424 | 347-TyrArgThrLysAspGlyPheGluThrTyrAspLysLeuGlyGluAlaAspArgLysAlaLeu-367 |
| SEQ. ID. NO. 11425 | 374-LeuAlaGluAspLeuAlaGln-380 |

750
AMPHI Regions - AMPHI
SEQ. ID. NO. 11426  1-ValLysProArgPheTyrTrpAlaAlaCysAlaValLeuLeuThrAlaCysSerProGluProAlaAlaGluLysThrValSerAlaAlaSerAlaSerAla
AlaThrLeuThrValProThrAlaArgGlyAspAlaValValProLysAsnProGluArgValAlaValTyrAspTrpAlaAlaLeuAspThrLeuThrGlu
LeuGlyValAsnValGlyAlaThrThrAlaProValArgValAspTyrLeuGlnProAlaPheAspLysAlaAlaThrValGlyThrLeuPheGluProAspTyr
GluAlaLeuHisArgTyrAsnProGlnLeuValIleThrGlyGlyProGlyAlaGluAlaTyrGluGlnLeuAlaLysAsnAlaThrThrIleAspLeuThrVal
AspAsnGlyAsnIleArgThrSerGlyGluLysGlnMetGluThrLeuAlaArgIlePheGlyLysGluAlaArgAlaAlaGluLeuLysAlaGlnIleAspAla
LeuPheAlaGlnThrArgGluAlaAlaLysGlyLysGlyArgGlyLeuValLeuSerValThrGlyAsnLysValSerAlaPheGlyThrGlnSerArgLeuAla
SerTrpIleHisGlyAspIleGlyLeuProProValAspGluSerLeuArgAsnGluGlyHisGlyGlnProValSerPheGluTyrIleLysGluLysAsnPro
AspTrpIlePheIleIleAspArgThrAlaAlaIleGlyGlnGluGlyProAlaAlaValGluValLeuAspAsnAlaLeuValArgGlyThrAsnAlaTrpLys
ArgLysGlnIleIleValMetProAlaAlaAsnTyrIleValAlaGlyGlyAlaArgGlnLeuIleGlnAlaAlaGluGlnLeuLysAlaAlaPheLysLysAla
GluProValAlaAlaGlyLysLys-321
Antigenic Index - Jameson-Wolf (SEQ. ID. NO. 11426)
1-ValLysProArgPheTyrTrpAlaAlaCysAlaValLeuLeuThrAlaCysSerProGluProAlaAlaGluLys
ThrValSerAlaAlaSerAlaSerAlaAlaThrLeuThrValProThrAlaArgGlyAspAlaValValProLys
AsnProGluArgValAlaValTyrAspTrpAlaAlaLeuAspThrLeuThrGluLeuGlyValAsnValGlyAlaThr
ThrAlaProValArgValAspTyrLeuGlnProAlaPheAspLysAlaAlaThrValGlyThrLeuPheGluPro
AspTyrGluAlaLeuHisArgTyrAsnProGlnLeuValIleThrGlyGlyProGlyAlaGluAlaTyrGluGln
LeuAlaLysAsnAlaThrThrIleAspLeuThrValAspAsnGlyAsnIleArgThrSerGlyGluLysGlnMetGlu
ThrLeuAlaArgIlePheGlyLysGluAlaArgAlaAlaGluLeuLysAlaGlnIleAspAlaLeuPheAlaGln
ThrArgGluAlaAlaLysGlyLysGlyArgGlyLeuValLeuSerValThrGlyAsnLysValSerAlaPheGly
ThrGlnSerArgLeuAlaSerTrpIleHisGlyAspIleGlyLeuProProValAspGluSerLeuArgAsnGlu
glyHisGlyGlnProValSerPheGluTyrIleLysGluLysAsnProAspTrpIlePheIleIleAspArgThr
AlaAlaIleGlyGlnGluGlyProAlaAlaValGluValLeuAspAsnAlaLeuValArgGlyThrAsnAlaTrpLys
ArgLysGlnIleIleValMetProAlaAlaAsnTyrIleValAlaGlyGlyAlaArgGlnLeuIleGlnAlaAla
GluGlnLeuLysAlaAlaPheLysLysAlaGluProValAlaAlaGlyLysLys-321
Hydrophilic Regions - Hopp-Woods (SEQ. ID. NO. 11426)
1-ValLysProArgPheTyrTrpAlaAlaCysAlaValLeuLeuThrAlaCysSerProGluProAlaAlaGluLys
ThrValSerAlaAlaSerAlaSerAlaAlaThrLeuThrValProThrAlaArgGlyAspAlaValValProLys
AsnProGluArgValAlaValTyrAspTrpAlaAlaLeuAspThrLeuThrGluLeuGlyValAsnValGlyAla
ThrThrAlaProValArgValAspTyrLeuGlnProAlaPheAspLysAlaAlaThrValGlyThrLeuPheGluPro
AspTyrGluAlaLeuHisArgTyrAsnProGlnLeuValIleThrGlyGlyProGlyAlaGluAlaTyrGluGln
LeuAlaLysAsnAlaThrThrIleAspLeuThrValAspAsnGlyAsnIleArgThrSerGlyGluLysGlnMet
GluThrLeuAlaArgIlePheGlyLysGluAlaArgAlaAlaGluLeuLysAlaGlnIleAspAlaLeuPheAlaGln
ThrArgGluAlaAlaLysGlyLysGlyArgGlyLeuValLeuSerValThrGlyAsnLysValSerAlaPheGly
ThrGlnSerArgLeuAlaSerTrpIleHisGlyAspIleGlyLeuProProValAspGluSerLeuArgAsnGlu
GlyHisGlyGlnProValSerPheGluTyrIleLysGluLysAsnProAspTrpIlePheIleIleAspArgThrAla
AlaIleGlyGlnGluGlyProAlaAlaValGluValLeuAspAsnAlaLeuValArgGlyThrAsnAlaTrpLys
ArgLysGlnIleIleValMetProAlaAlaAsnTyrIleValAlaGlyGlyAlaArgGlnLeuIleGlnAlaAla
GluGlnLeuLysAlaAlaPheLysLysAlaGluProValAlaAlaGlyLysLys-321
751
AMPHI Regions - AMPHI

| | |
|---|---|
| SEQ. ID. NO. 11427 | 11-AlaAspArgAlaValArgSerAlaThr-19 |
| SEQ. ID. NO. 11428 | 59-IleGlnAspThrAsn-63 |
| SEQ. ID. NO. 11429 | 82-LeuSerAsnAlaAla-86 |
| SEQ. ID. NO. 11430 | 139-LeuAsnAsnLysValPheGlnGlyTyr-147 |
| SEQ. ID. NO. 11431 | 156-LeuAsnGlnAspIleTyrArgGluValGlnLysMetGly-168 |
| SEQ. ID. NO. 11432 | 215-AsnValGlnAsnAspTyrAlaAspValLeu-224 |
| SEQ. ID. NO. 11433 | 281-SerTyrPheAlaGluValProLysAlaGlyThrLysGluPheAspAsp TyrValLysIleTrpGlyGlu-303 |

Antigenic Index - Jameson-Wolf

| | |
|---|---|
| SEQ. ID. NO. 11434 | 9-ThrGlnAlaAspArgAlaValArg-16 |
| SEQ. ID. NO. 11435 | 18-AlaThrAlaProLys-22 |
| SEQ. ID. NO. 11436 | 29-LysIleIleAspGluLysThrGlyLysValSerPheAspThrArgGlnIle-45 |
| SEQ. ID. NO. 11437 | 50-AspLeuSerLysGluGluLeuAlaSerIleGlnAspThrAsnGlyLysVal-66 |
| SEQ. ID. NO. 11438 | 72-ProGlyIlePheAsnAsnArgGluAspSerLeuSerAsnAlaAlaLysGlnAsnArgAsnSerThrAsnGlySer-96 |
| SEQ. ID. NO. 11439 | 104-ProProThrGlyLysTyrLysSerAspSerAsnAsnLysIleLys-118 |
| SEQ. ID. NO. 11440 | 137-AspGlnLeuAsnAsnLys-142 |
| SEQ. ID. NO. 11441 | 147-TyrLeuProLysThrAsnSerGluLysGluLeuAsnGlnAspIleTyrArgGluValGlnLysMetGlyAsnGlyTrpSerValAspThrSerAsnHisSerArgGlyGlyIle-183 |
| SEQ. ID. NO. 11442 | 190-LysAspTrpValAsnAsnGlnLysGlnAsnGly-200 |
| SEQ. ID. NO. 11443 | 203-ProIleArgLysAlaArgPhe-209 |
| SEQ. ID. NO. 11444 | 214-ThrAsnValGlnAsnAspTyrAlaAspValLeuGlnLysAsnGlyTyr-229 |
| SEQ. ID. NO. 11445 | 233-GlyAlaAspGlyLysThrTyrAsnSerGlySer-243 |
| SEQ. ID. NO. 11446 | 247-ValHisAspLysAspPheValGlyAsnLys-256 |
| SEQ. ID. NO. 11447 | 263-GlyThrAsnAspThrThrGlnGlyThrCysLysGlyLeuCys-276 |
| SEQ. ID. NO. 11448 | 286-ValProLysAlaGlyThrLysGluPheAspAspTyrVal-298 |

TABLE 1-continued

| SEQ. ID. NO. 11449 | 304-ValGluTyrAspAlaGlnGlyLysProIleAsnLysSerLysProIleLeuValGluProAsnLysThrLysAspAsnGluLysTyrGluLysGluAlaPhe-337 |

Hydrophilic Regions - Hopp-Woods

| SEQ. ID. NO. 11450 | 10-GlnAlaAspArgAlaValArg-16 |
| SEQ. ID. NO. 11451 | 18-AlaThrAlaProLys-22 |
| SEQ. ID. NO. 11452 | 29-LysIleIleAspGluLysThrGlyLysValSerPheAspThr-42 |
| SEQ. ID. NO. 11453 | 50-AspLeuSerLysGluGluLeuAlaSer-58 |
| SEQ. ID. NO. 11454 | 60-GlnAspThrAsnGly-64 |
| SEQ. ID. NO. 11455 | 76-AsnAsnArgGluAspSerLeuSerAsnAlaAlaLysGlnAsnArgAsnSerThrAsn-94 |
| SEQ. ID. NO. 11456 | 105-ProThrGlyLysTyrLysSerAspSerAsnAsnLysIleLys-118 |
| SEQ. ID. NO. 11457 | 151-ThrAsnSerGluLysLeuAsnGlnAspIleTyrArgGluValGlnLysMet-167 |
| SEQ. ID. NO. 11458 | 175-ThrSerAsnHisSerArgGlyGlyIle-183 |
| SEQ. ID. NO. 11459 | 196-GlnLysGlnAsnGly-200 |
| SEQ. ID. NO. 11460 | 203-ProIleArgLysAlaArgPhe-209 |
| SEQ. ID. NO. 11461 | 219-AspTyrAlaAspValLeuGln-225 |
| SEQ. ID. NO. 11462 | 234-AlaAspGlyLysThrTyrAsn-240 |
| SEQ. ID. NO. 11463 | 247-ValHisAspLysAspPheVal-253 |
| SEQ. ID. NO. 11464 | 265-AsnAspThrThrGlnGlyThrCys-272 |
| SEQ. ID. NO. 11465 | 286-ValProLysAlaGlyThrLysGluPheAspAspTyrVal-298 |
| SEQ. ID. NO. 11466 | 304-ValGluTyrAspAlaGlnGlyLysProIleAsnLysSerLysProIleLeu-320 |
| SEQ. ID. NO. 11467 | 322-GluProAsnLysThrLysAspAsnGluLysTyrGluLysGluAlaPhe-337 |

752-2

AMPHI Regions - AMPHI

| SEQ. ID. NO. 11468 | 6-GluArgMetThrGlnIleAlaLysLeuLeuAsnSerSer-18 |
| SEQ. ID. NO. 11469 | 29-PheLeuThrGluIleLysAspTyrSerGluPhe-39 |
| SEQ. ID. NO. 11470 | 51-TrpAspLysPheArgArgIle-57 |
| SEQ. ID. NO. 11471 | 69-ValLysGluSerArgLysLysIleGlnLysProIleAsp-81 |
| SEQ. ID. NO. 11472 | 105-LysSerCysGlySerSerIleGly-112 |
| SEQ. ID. NO. 11473 | 114-SerSerLeuGlyGlyPheGly-120 |
| SEQ. ID. NO. 11474 | 145-GlyAlaAlaThrThrArgLysValAlaLysAspMetLeuLysSerGln-160 |
| SEQ. ID. NO. 11475 | 194-IleLeuAspLeuHisArgIleAlaThrSer-203 |
| SEQ. ID. NO. 11476 | 233-GlnProProHisGly-238 |
| SEQ. ID. NO. 11477 | 240-ValHisThrLeuMetGluGluVal-247 |
| SEQ. ID. NO. 11478 | 254-ThrTyrAspGlyValGluAsnProPheIleHisProValValGlnAlaIle-270 |
| SEQ. ID. NO. 11479 | 272-LeuHisPheLeuIleGlyTyrIleHisPro-281 |
| SEQ. ID. NO. 11480 | 309-IleSerIleSerArgLeuLeuLysAsnAlaProAlaGlnTyr-322 |
| SEQ. ID. NO. 11481 | 347-IleLysArgAlaValAlaAspLeuGluHis-356 |
| SEQ. ID. NO. 11482 | 371-AlaIleAlaGlnTyrThrGluLysIleGlyLysLeu-382 |
| SEQ. ID. NO. 11483 | 390-LeuGlnLysAlaValGluGluSerGly-398 |
| SEQ. ID. NO. 11484 | 422-SerLysLeuGlyGluTyrArgPhe-429 |
| SEQ. ID. NO. 11485 | 435-SerGlyAsnAlaLeuGluTyrValAlaPro-444 |

Antigenic Index - Jameson-Wolf

| SEQ. ID. NO. 11486 | 4-LeuThrGluArgMetThrGln-10 |
| SEQ. ID. NO. 11487 | 15-LeuAsnSerSerAlaAsnAsnProAspIleAspIleProAspPheLeuThrGluIleLysAspTyrSerGlu-38 |
| SEQ. ID. NO. 11488 | 40-SerValThrAspGluAsnGlyThr-47 |
| SEQ. ID. NO. 11489 | 52-AspLysPheArgArgIleHisThrGluAspThrArgMetLysTrpArgAlaValLysGluSerArgLysLysIleGlnLysProIleAsp-81 |
| SEQ. ID. NO. 11490 | 92-IleProAspSerLeuGln-97 |
| SEQ. ID. NO. 11491 | 102-LeuIleAspLysSerCysGlySerSerIleGly-112 |
| SEQ. ID. NO. 11492 | 117-GlyGlyPheGlyArgSerGluGlnAsnArgPheLeu-128 |
| SEQ. ID. NO. 11493 | 147-AlaThrThrArgLysValAlaLysAspMetLeuLysSerGlnArgLysProLysThrLysAspGluIle-169 |
| SEQ. ID. NO. 11494 | 179-LysLysAlaValGluLeuLysAsnThr-187 |
| SEQ. ID. NO. 11495 | 204-AsnAlaIleGluAsnLysAlaGluProGlyGlnPheArgGlnAspAspGluIlePhe-222 |
| SEQ. ID. NO. 11496 | 226-IleAsnGlyAsnSerLeuTyrGlnProProProHisGly-238 |
| SEQ. ID. NO. 11497 | 253-AsnThrTyrAspGlyValGluAsnProPhe-262 |
| SEQ. ID. NO. 11498 | 280-HisProPheGlyAspGlyAsnGlyArgThrAlaArg-291 |
| SEQ. ID. NO. 11499 | 313-ArgLeuLeuLysAsnAlaPro-319 |
| SEQ. ID. NO. 11500 | 330-GluThrAspAspLeuAsp-335 |
| SEQ. ID. NO. 11501 | 342-TyrGlnCysAspIleIleLys-348 |
| SEQ. ID. NO. 11502 | 358-IleSerAspLysGlnLysHisGlnGlnGluPheLysAla-370 |
| SEQ. ID. NO. 11503 | 375-TyrThrGluLysIleGlyLysLeuAsnGlnArgGln-386 |
| SEQ. ID. NO. 11504 | 392-LysAlaValGluGluSerGlyLys-399 |
| SEQ. ID. NO. 11505 | 415-AsnThrAlaArgSerAspLeuSerLysLeuGlyGluTyrArgPhe-429 |
| SEQ. ID. NO. 11506 | 433-PheLysSerGlyAsnAlaLeu-439 |
| SEQ. ID. NO. 11507 | 445-GlnAspLeuLeuGluArgLeuGluLysLys-454 |

Hydrophilic Regions - Hopp-Woods

| SEQ. ID. NO. 11508 | 4-LeuThrGluArgMetThrGln-10 |
| SEQ. ID. NO. 11509 | 19-AlaAsnAsnProAspIleAspIle-26 |
| SEQ. ID. NO. 11510 | 31-ThrGluIleLysAspTyrSerGlu-38 |
| SEQ. ID. NO. 11511 | 40-SerValThrAspGluAsnGly-46 |
| SEQ. ID. NO. 11512 | 52-AspLysPheArgArgIleHisThrGluAspThrArgMetLysTrpArgAlaValLysGluSerArgLysLysIleGlnLysProIle-80 |
| SEQ. ID. NO. 11513 | 102-LeuIleAspLysSerCysGly-108 |
| SEQ. ID. NO. 11514 | 120-GlyArgSerGluGlnAsnArgPheLeu-128 |
| SEQ. ID. NO. 11515 | 147-AlaThrThrArgLysValAlaLysAspMetLeuLysSerGlnArgLysProLysThrLysAspGluIle-169 |
| SEQ. ID. NO. 11516 | 179-LysLysAlaValGluLeuLysAsn-186 |
| SEQ. ID. NO. 11517 | 204-AsnAlaIleGluAsnLysAlaGluProGlyGlnPheArgGlnAspAspGluIlePhe-222 |
| SEQ. ID. NO. 11518 | 283-GlyAspGlyAsnGlyArgThrAlaArg-291 |
| SEQ. ID. NO. 11519 | 330-GluThrAspAspLeuAsp-335 |
| SEQ. ID. NO. 11520 | 358-IleSerAspLysGlnLysHisGlnGlnGluPheLysAla-370 |
| SEQ. ID. NO. 11521 | 375-TyrThrGluLysIleGlyLysLeuAsnGlnArgGln-386 |

TABLE 1-continued

| SEQ. ID. NO. 11522 | 392-LysAlaValGluGluSerGlyLys-399 |
| SEQ. ID. NO. 11523 | 416-ThrAlaArgSerAspLeuSerLysLeuGlyGlu-426 |
| SEQ. ID. NO. 11524 | 446-AspLeuLeuGluArgLeuGluLysLys-454 |

753
AMPHI Regions - AMPHI
SEQ. ID. NO. 11525    44-IleValGluMetMetThrTyrIleLeu-52
SEQ. ID. NO. 11526    75-TrpAlaTyrPheAspGluValAlaGln-83
SEQ. ID. NO. 11527    109-GlnTrpPheAlaProLeu-114
SEQ. ID. NO. 11528    121-ArgSerAlaValArgGlnLeu-127
SEQ. ID. NO. 11529    129-ProSerThrThrValArgAla-135
Antigenic Index - Jameson-Wolf
SEQ. ID. NO. 11530    13-LysLeuTyrProAsnGluGlnTrpAsnGluSerGluAla-25
SEQ. ID. NO. 11531    34-TyrGlnSerProThrHisArgGln-41
SEQ. ID. NO. 11532    55-LeuLysAsnGlyGln-59
SEQ. ID. NO. 11533    64-CysLysGlyThrGlnProIleGly-71
SEQ. ID. NO. 11534    85-HisTyrLeuGluSerAspArgHisLeuArgAspAsnSerAspTrpAsnCysGlyAspAsnIle-105
SEQ. ID. NO. 11535    112-AlaProLeuGlyHisSerHisGlnMetArgSerAlaVal-124
SEQ. ID. NO. 11536    136-LeuTyrHisLysGlySerAspLysGlyLeuArg-146
Hydrophilic Regions - Hopp-Woods
SEQ. ID. NO. 11537    19-GlnTrpAsnGluSerGluAla-25
SEQ. ID. NO. 11538    87-LeuGluSerAspArgHisLeuArgAspAsnSerAsp-98
SEQ. ID. NO. 11539    139-LysGlySerAspLysGlyLeuArg-146

754
AMPHI Regions - AMPHI
SEQ. ID. NO. 11540    29-ArgIleGlyThrLeuGluLysGlyAlaMet-38
SEQ. ID. NO. 11541    67-MetProHisIlePheAlaGlnTyrPheProGluGlyPheLeuAsp-81
SEQ. ID. NO. 11542    108-ArgGluThrLeuGlyArg-113
SEQ. ID. NO. 11543    121-ProLeuPheAsnGluTrpIleAspGlyLeuGlu-131
SEQ. ID. NO. 11544    152-PheGlnGlnTyrMetAlaGluIle-159
SEQ. ID. NO. 11545    161-HisHisGlyArgPheValSerValSer-169
SEQ. ID. NO. 11546    181-ArgArgAsnThrLys-185
SEQ. ID. NO. 11547    189-SerTyrIleAlaLysGly-194
SEQ. ID. NO. 11548    249-MetGluAspPheThrSerLeuArgGln-257
SEQ. ID. NO. 11549    269-AlaAlaIleAlaGlnIleIleArgGlnIleSerGlyArgProAsp-283
SEQ. ID. NO. 11550    288-HisPhePheAsnGlnLeuAlaAla-295
SEQ. ID. NO. 11551    324-ValTyrAspValLeuAspThr-330
SEQ. ID. NO. 11552    336-GlyThrGlnGlyIlePheAspAlaTyrAsp-345
SEQ. ID. NO. 11553    399-TyrSerAspValLeu-403
Antigenic Index - Jameson-Wolf
SEQ. ID. NO. 11554    8-ValSerGlyAsnArgMetArgLysProArg-17
SEQ. ID. NO. 11555    25-AlaAsnAspGluArgIleGlyThrLeuGluLysGlyAla-37
SEQ. ID. NO. 11556    43-TyrAspAsnProAsnSerSerLeu-50
SEQ. ID. NO. 11557    54-HisTyrGlnAspArgSerLysVal-61
SEQ. ID. NO. 11558    75-PheProGluGlyPheLeu-80
SEQ. ID. NO. 11559    93-AlaProPheGluAspAsnGluMetLeu-101
SEQ. ID. NO. 11560    114-IleHisValArgCysAsnAspProLeuPhe-123
SEQ. ID. NO. 11561    130-LeuGluMetLysAsnProArgIleLeuThrGluArgAspLeuLeu-144
SEQ. ID. NO. 11562    163-GlyArgPheValSer-167
SEQ. ID. NO. 11563    170-GlyIleGlnGlnLysMetSerLeuAspAlaIleArgArgAsnThrLysGlnThrAla-188
SEQ. ID. NO. 11564    194-GlyPheAspAlaSerGluTyrProCys-202
SEQ. ID. NO. 11565    224-ThrSerLeuSerGluAspSerSer-231
SEQ. ID. NO. 11566    236-ArgArgPheAspValSerGluGlnGlyTyr-245
SEQ. ID. NO. 11567    250-GluAspPheThrSer-254
SEQ. ID. NO. 11568    256-ArgGlnTyrSerValGluAspLysTyrLysGlySerTyr-268
SEQ. ID. NO. 11569    278-IleSerGlyArgProAspGluAspLeu-286
SEQ. ID. NO. 11570    299-LeuLysAsnGlyAspAlaHisLeu-306
SEQ. ID. NO. 11571    315-AspGluTyrAspVal-319
SEQ. ID. NO. 11572    343-AlaTyrAspAspThrLeu-348
SEQ. ID. NO. 11573    352-LeuThrAsnHisGlyLysLysThrTyrProSerLysAsnThr-365
SEQ. ID. NO. 11574    369-PheAlaGluLysTyrCysAspLeuGlyArgGluAspAlaSerPhe-383
SEQ. ID. NO. 11575    389-ValGlnAlaLysGluGlnVal-395
SEQ. ID. NO. 11576    399-TyrSerAspValLeuArgGluAsnGluTrpLeu-409
SEQ. ID. NO. 11577    415-PheIleProAspGluAsnGluGluGlyLeu-424
Hydrophilic Regions - Hopp-Woods
SEQ. ID. NO. 11578    10-GlyAsnArgMetArgLysProArg-17
SEQ. ID. NO. 11579    25-AlaAsnAspGluArgIleGlyThrLeuGluLysGlyAla-37
SEQ. ID. NO. 11580    55-TyrGlnAspArgSerLysVal-61
SEQ. ID. NO. 11581    93-AlaProPheGluAspAsnGluMetLeu-101
SEQ. ID. NO. 11582    114-IleHisValArgCysAsnAsp-120
SEQ. ID. NO. 11583    130-LeuGluMetLysAsnProArgIleLeuThrGluArgAspLeuLeu-144
SEQ. ID. NO. 11584    175-MetSerLeuAspAlaIleArgArgAsnThrLysGln-186
SEQ. ID. NO. 11585    194-GlyPheAspAlaSerGlu-199
SEQ. ID. NO. 11586    225-SerLeuSerGluAspSerSer-231
SEQ. ID. NO. 11587    236-ArgArgPheAspValSerGlu-242
SEQ. ID. NO. 11588    250-GluAspPheThrSer-254
SEQ. ID. NO. 11589    258-TyrSerValGluAspLysTyrLysGly-266
SEQ. ID. NO. 11590    278-IleSerGlyArgProAspGluAspLeu-286
SEQ. ID. NO. 11591    300-LysAsnGlyAspAlaHisLeu-306
SEQ. ID. NO. 11592    315-AspGluTyrAspVal-319
SEQ. ID. NO. 11593    354-AsnHisGlyLysLysThrTyrProSer-362

TABLE 1-continued

| | |
|---|---|
| SEQ. ID. NO. 11594 | 369-PheAlaGluLysTyrCysAspLeuGlyArgGluAspAlaSerPhe-383 |
| SEQ. ID. NO. 11595 | 389-ValGlnAlaLysGluGlnVal-395 |
| SEQ. ID. NO. 11596 | 401-AspValLeuArgGluAsnGluTrpLeu-409 |
| SEQ. ID. NO. 11597 | 417-ProAspGluAsnGluGluGlyLeu-424 |
| 755 | |
| AMPHI Regions - AMPHI | |
| SEQ. ID. NO. 11598 | 22-AsnAsnTyrThrAsnAlaTyrSerAspIleLysThrIle-34 |
| SEQ. ID. NO. 11599 | 38-HisGlyPheGluAsnIleGlnGly-45 |
| SEQ. ID. NO. 11600 | 75-SerCysIleSerAsnIleLysPhe-82 |
| SEQ. ID. NO. 11601 | 124-GluGlnIleAsnGlnValLeu-130 |
| Antigenic Index - Jameson-Wolf | |
| SEQ. ID. NO. 11602 | 10-MetAspThrAsnCysLeuLysAspAsnTyrHisGlyAsnAsnTyrThrAsnAlaTyrSerAsp-30 |
| SEQ. ID. NO. 11603 | 42-AsnIleGlnGlySer-46 |
| SEQ. ID. NO. 11604 | 48-TyrLeuGlyArgGluGlyIleSerGluAlaHis-58 |
| SEQ. ID. NO. 11605 | 83-TyrArgLeuGluSerAspLeu-89 |
| SEQ. ID. NO. 11606 | 108-ArgValGluGlnLeuArg-113 |
| SEQ. ID. NO. 11607 | 120-GlyLeuSerAspGluGlnIle-126 |
| SEQ. ID. NO. 11608 | 129-ValLeuGluLysGlnLysPheGluLeuGluSerProAsnLeuLys-143 |
| Hydrophilic Regions - Hopp-Woods | |
| SEQ. ID. NO. 11609 | 10-MetAspThrAsnCysLeuLysAspAsnTyrHis-20 |
| SEQ. ID. NO. 11610 | 49-LeuGlyArgGluGlyIleSerGluAlaHis-58 |
| SEQ. ID. NO. 11611 | 83-TyrArgLeuGluSerAspLeu-89 |
| SEQ. ID. NO. 11612 | 108-ArgValGluGlnLeuArg-113 |
| SEQ. ID. NO. 11613 | 120-GlyLeuSerAspGluGlnIle-126 |
| SEQ. ID. NO. 11614 | 129-ValLeuGluLysGlnLysPheGluLeuGluSerProAsnLeu-142 |
| 756 | |
| AMPHI Regions - AMPHI | |
| SEQ. ID. NO. 11615 | 6-AlaGlnThrLeuValGluIleGlnAspSerLeuTyrArgValValSerThrVal-23 |
| SEQ. ID. NO. 11616 | 29-AsnLeuLysArgLeuThr-34 |
| SEQ. ID. NO. 11617 | 57-AspPheLysGluThrLeuValArgPheGlyArgAspMetLeuGlnAspMetPro-74 |
| SEQ. ID. NO. 11618 | 98-TyrLeuGluTyrLeuLysGlnValAlaSer-107 |
| SEQ. ID. NO. 11619 | 113-GluArgLeuTyrAsnAlaValAspArgLeuAlaGluSerGlnGluArg-128 |
| SEQ. ID. NO. 11620 | 130-ThrSerAlaIleLeu-134 |
| SEQ. ID. NO. 11621 | 136-GlyAlaArgGlyAlaAspPhe-142 |
| Antigenic Index - Jameson-Wolf | |
| SEQ. ID. NO. 11622 | 11-GluIleGlnAspSerLeuTyr-17 |
| SEQ. ID. NO. 11623 | 24-GlnTyrGlyAspAspAsnLeuLysArgLeuThrAlaAspLysArgLysGlnTyr-41 |
| SEQ. ID. NO. 11624 | 45-PheLysIleSerGluGlySerThrArgValGluSerAspPheLysGluThrLeu-62 |
| SEQ. ID. NO. 11625 | 65-PheGlyArgAspMetLeuGlnAspMetProProLysIleArgSer-79 |
| SEQ. ID. NO. 11626 | 105-ValAlaSerGluGlyTyrGlnThrGluArgLeuTyrAsnAlaValAspArgLeuAlaGluSerGlnGluArgIleThr-130 |
| SEQ. ID. NO. 11627 | 135-LysGlyAlaArgGlyAlaAsp-141 |
| SEQ. ID. NO. 11628 | 44-GlnIleGlyArgArgSerTyrSerArgGluAspIleSerGluAlaAsnArgArgAlaGluArgValProTyr-167 |
| SEQ. ID. NO. 11629 | 171-LeuValSerArgGlyAsn-176 |
| SEQ. ID. NO. 11630 | 182-SerAspIleGlyAsp-186 |
| Hydrophilic Regions - Hopp-Woods | |
| SEQ. ID. NO. 11631 | 11-GluIleGlnAspSerLeu-16 |
| SEQ. ID. NO. 11632 | 25-TyrGlyAspAspAsnLeuLysArgLeuThrAlaAspLysArgLysGlnTyr-41 |
| SEQ. ID. NO. 11633 | 45-PheLysIleSerGluGlySerThrArgValGluSerAspPheLysGluThrLeu-62 |
| SEQ. ID. NO. 11634 | 65-PheGlyArgAspMetLeuGln-71 |
| SEQ. ID. NO. 11635 | 73-MetProProLysIleArgSer-79 |
| SEQ. ID. NO. 11636 | 114-ArgLeuTyrAsnAlaValAspArgLeuAlaGluSerGlnGluArgIleThr-130 |
| SEQ. ID. NO. 11637 | 135-LysGlyAlaArgGlyAlaAsp-141 |
| SEQ. ID. NO. 11638 | 144-GlnIleGlyArgArgSerTyrSerArgGluAspIleSerGluAlaAsnArgArgAlaGluArgValProTyr-167 |
| 757 | |
| AMPHI Regions - AMPHI | |
| SEQ. ID. NO. 11639 | 47-AspTyrGlnSerAlaAlaAsnLys-54 |
| SEQ. ID. NO. 11640 | 79-AsnLeuLeuHisAspPheSerAspGlyLeu-88 |
| SEQ. ID. NO. 11641 | 97-LysAlaAspLysIleThr-102 |
| SEQ. ID. NO. 11642 | 115-GlnLysAlaGluLysLeuSerLysAlaAla-124 |
| SEQ. ID. NO. 11643 | 140-ArgAspThrGlyAsp-144 |
| SEQ. ID. NO. 11644 | 154-AsnAlaGlnLysGluProThrArgGluTrpAla-164 |
| Antigenic Index - Jameson-Wolf | |
| SEQ. ID. NO. 11645 | 16-AlaCysGlySerGlnSerGluGluGlnProAlaSerAlaGlnProGlnGluGlnAlaGlnSerGluLeuLysThrMetPro-42 |
| SEQ. ID. NO. 11646 | 46-ThrAspTyrGlnSerAlaAlaAsnLysGlyLeuAsnAspGlnLysThrGlyLeuThrLeu-65 |
| SEQ. ID. NO. 11647 | 73-AspAsnAlaGluGlyLysAsnLeuLeuHisAspPheSerAspGlyLeu-88 |
| SEQ. ID. NO. 11648 | 93-ValAspThrAspLysAlaAspLysIleThrAla-103 |
| SEQ. ID. NO. 11649 | 108-TrpAsnThrAspAlaMetProGlnLysAlaGluLysLeuSerLys-122 |
| SEQ. ID. NO. 11650 | 132-AlaProGluAspArgThrMetLeuArgAspThrGlyAspGlnIleGluMetAlaIleAspSerHisAsnAlaGlnLysGluProThrArgGluTrpAlaArgGlyGlyIle-168 |
| Hydrophilic Regions - Hopp-Woods | |
| SEQ. ID. NO. 11651 | 19-SerGlnSerGluGluGlnProAla-26 |
| SEQ. ID. NO. 11652 | 29-GlnProGlnGluGlnAlaGlnSerGluLeuLysThr-40 |
| SEQ. ID. NO. 11653 | 50-SerAlaAlaAsnLysGlyLeuAsnAspGlnLysThr-61 |
| SEQ. ID. NO. 11654 | 73-AspAsnAlaGluGlyLysAsnLeu-80 |
| SEQ. ID. NO. 11655 | 93-ValAspThrAspLysAlaAspLysIleThrAla-103 |
| SEQ. ID. NO. 11656 | 112-AlaMetProGlnLysAlaGluLysLeuSerLys-122 |
| SEQ. ID. NO. 11657 | 132-AlaProGluAspArgThrMetLeuArgAspThrGlyAspGlnIleGluMetAlaIle-150 |
| SEQ. ID. NO. 11658 | 152-SerHisAsnAlaGlnLysGluProThrArgGluTrpAlaArg-165 |

TABLE 1-continued

758
AMPHI Regions - AMPHI
SEQ. ID. NO. 11659   15-AlaThrLeuAlaAspGluLeuGlnTyrVal-24
SEQ. ID. NO. 11660   53-AlaGluValAlaAla-57
SEQ. ID. NO. 11661   60-GlnThrValIleSerGluIleValArgArgHisThr-71
SEQ. ID. NO. 11662   87-ProTyrLeuGlyGlyLeuProGluAlaLeuHisThr-98
SEQ. ID. NO. 11663   125-PheAlaSerProGlyGlyTrpGlnIleIleGly-135
Antigenic Index - Jameson-Wolf
SEQ. ID. NO. 11664   9-ArgPheAspThrAspLeu-14
SEQ. ID. NO. 11665   32-AspHisGlnGlyLysLeuVal-38
SEQ. ID. NO. 11666   44-TyrGlyGlyGluTyrGlyProAspLeuAlaGlu-54
SEQ. ID. NO. 11667   66-IleValArgArgHisThrAla-72
SEQ. ID. NO. 11668   96-LeuHisThrProArgArgAlaValProArgThrSerValPro-109
SEQ. ID. NO. 11669   115-IleGlyGlySerGln-119
SEQ. ID. NO. 11670   145-AspLeuAsnProPro-149
SEQ. ID. NO. 11671   154-AlaGlyAspGlnValArgPheValAlaGluArgIleGluPro-167
Hydrophilic Regions - Hopp-Woods
SEQ. ID. NO. 11672   10-PheAspThrAspLeu-14
SEQ. ID. NO. 11673   32-AspHisGlnGlyLysLeuVal-38
SEQ. ID. NO. 11674   48-TyrGlyProAspLeuAlaGlu-54
SEQ. ID. NO. 11675   66-IleValArgArgHisThr-71
SEQ. ID. NO. 11676   97-HisThrProArgArgAlaValPro-104
SEQ. ID. NO. 11677   156-AspGlnValArgPheValAlaGluArgIleGluPro-167
759
AMPHI Regions - AMPHI
SEQ. ID. NO. 11678   8-ProPheCysSerValLeuSerThrLeuGlyLeu-18
SEQ. ID. NO. 11679   35-TyrGlnTyrPheArgAspPheAlaGlu-43
SEQ. ID. NO. 11680   63-LysIleLeuGlyArgValLeuAsnGlyIlePro-73
SEQ. ID. NO. 11681   94-TyrValAsnSerVal-98
SEQ. ID. NO. 11682   140-ArgLeuAsnLysLeuValThrGluIle-148
SEQ. ID. NO. 11683   185-ThrGlnGlnValArgLysAlaAsp-192
SEQ. ID. NO. 11684   207-GlyGlyThrProLeu-211
SEQ. ID. NO. 11685   261-LeuSerThrTyrAlaGlyPheAspAsnPhePheAsnLys-273
SEQ. ID. NO. 11686   282-IleArgSerThrIle-286
SEQ. ID. NO. 11687   313-ThrLeuGlnGlyLeu-317
SEQ. ID. NO. 11688   408-LysGlyAspArgLeuSerLysLeuGlyAla-417
SEQ. ID. NO. 11689   446-AlaSerAspGlySerLysGlnAla-453
SEQ. ID. NO. 11690   548-ValTyrGluTyrIle-552
SEQ. ID. NO. 11691   597-GluGlnValAlaGlnAlaGlu-603
SEQ. ID. NO. 11692   764-LysThrProGluCysTyrArgSerTyrHisSer-774
SEQ. ID. NO. 11693   788-GluAsnTyrArgAlaLeu-793
SEQ. ID. NO. 11694   820-SerIleArgAlaGlyLys-825
SEQ. ID. NO. 11695   878-ThrLeuAspGlyPheGlyThrPheArgPheLeuThrGlyIle-891
SEQ. ID. NO. 11696   921-ProGlnThrThrGlu-925
SEQ. ID. NO. 11697   948-TyrAlaAspLeuGlyAlaTyr-954
SEQ. ID. NO. 11698   967-LeuTyrAsnProLeuLys-972
SEQ. ID. NO. 11699   992-TyrAsnGlnLeuGlnAlaThrAspIleSerArgGlnValGln-1005
SEQ. ID. NO. 11700   1013-GlnAlaLeuGlnAlaTrpGlnAsnSerGln-1022
SEQ. ID. NO. 11701   1040-LysGlnThrAspProLeuThrGlyIleLeuThr-1050
SEQ. ID. NO. 11702   1062-SerAlaAspIleCysArgGlnValAlaLysAlaAlaAspThr-1075
SEQ. ID. NO. 11703   1084-GluLeuAspThrTyr-1088
SEQ. ID. NO. 11704   1102-AlaArgGlnGlyGlyAspAlaGlnAlaValGluThrAlaArgHisAlaTyrLeuAsnAlaLeuAsnArgLeuSerArgGlnIleHisSerLeu-1132
SEQ. ID. NO. 11705   1139-IleArgMetProAsnLeuAlaGluLeuIleSerArgSerAlaAsnThrAla-1155
SEQ. ID. NO. 11706   1168-GlnAlaGlyArgArgIleAspArgHisLeuThrAspPro-1180
SEQ. ID. NO. 11707   1199-GlyThrHisArgProTyrGlnGlnThrThrAsn-1209
SEQ. ID. NO. 11708   1234-ThrAsnAsnArgPheAspGlu-1240
SEQ. ID. NO. 11709   1328-GluIleAsnSerProAlaGlnIle-1335
SEQ. ID. NO. 11710   1346-AspLysThrValGlu-1350
SEQ. ID. NO. 11711   1385-GlnAlaAlaHisGlyThrLeu-1391
Antigenic Index - Jameson-Wolf
SEQ. ID. NO. 11712   29-ValArgAsnAspValAspTyrGlnTyr-37
SEQ. ID. NO. 11713   40-AspPheAlaGluAsnLysGlyAla-47
SEQ. ID. NO. 11714   56-SerIleGlnAspLysGlnGlyLysIleLeu-65
SEQ. ID. NO. 11715   73-ProMetProAspPheArgValSerAsnArgGlnThrAla-85
SEQ. ID. NO. 11716   110-GlyAsnAspThrGlnAsnProGluGluGlnAlaTyr-121
SEQ. ID. NO. 11717   125-LeuValSerArgAsnProHisProAspTyrAspTyrHisLeuProArgLeuAsnLysLeuValThr-146
SEQ. ID. NO. 11718   148-IleSerProThrAla-152
SEQ. ID. NO. 11719   160-GlyAsnGlyGlnProLysAla-166
SEQ. ID. NO. 11720   168-AlaTyrLeuAspThrAspArgPhePro-176
SEQ. ID. NO. 11721   181-LeuGlySerGlyThrGlnGlnValArgLysAlaAspGlyThrArgThrArgThrAlaPro-200
SEQ. ID. NO. 11722   206-ThrGlyGlyThrProLeuLys-212
SEQ. ID. NO. 11723   226-SerLeuThrAspGlnProLeuAsn-233
SEQ. ID. NO. 11724   238-AlaGlyAspSerGlySerPro-244
SEQ. ID. NO. 11725   249-AspLysHisGluAsnArg-254
SEQ. ID. NO. 11726   285-ThrIleArgGlnTyrGluThrArgLeuAspVal-295
SEQ. ID. NO. 11727   303-IleTrpArgAspAsnGlyAsnGlyAsnSerThr-313
SEQ. ID. NO. 11728   316-GlyLeuAsnGluArgIleThr-322
SEQ. ID. NO. 11729   327-AsnProSerLeuAlaProGlnAsnAspSerArgHisMetProSerGluAspAlaGlyLys-346
SEQ. ID. NO. 11730   350-LeuSerSerArgPheAspAsnLysThr-358
SEQ. ID. NO. 11731   364-AsnIleAsnGlnGlyAla-369

TABLE 1-continued

| SEQ. ID. NO. | Sequence |
|---|---|
| SEQ. ID. NO. 11732 | 382-GlyLysAsnHisThr-386 |
| SEQ. ID. NO. 11733 | 394-ValAlaAspGlyLysArgValPhe-401 |
| SEQ. ID. NO. 11734 | 404-ValSerAsnProLysGlyAspArgLeuSerLysLeuGlyAla-417 |
| SEQ. ID. NO. 11735 | 424-GlyGlnGlyIleAsnGlnGlyAspIleSerIleGlyGluGlyThr-438 |
| SEQ. ID. NO. 11736 | 444-LysAlaAlaSerAspGlySerLysGlnAla-453 |
| SEQ. ID. NO. 11737 | 459-IleThrSerGlyArgGlyThr-465 |
| SEQ. ID. NO. 11738 | 469-AlaAspSerGlnGlnIleLysProGluAsn-478 |
| SEQ. ID. NO. 11739 | 483-PheArgGlyGlyArgLeuAspLeuAsnGlyAsnAsnLeu-495 |
| SEQ. ID. NO. 11740 | 501-ArgHisAlaAspGlyGlyAla-507 |
| SEQ. ID. NO. 11741 | 512-HisAsnProAspGlnAlaAla-518 |
| SEQ. ID. NO. 11742 | 528-LeuSerProGluHisValGlu-534 |
| SEQ. ID. NO. 11743 | 538-TrpGlyAsnArgProGlnGlyAsn-545 |
| SEQ. ID. NO. 11744 | 553-AsnProHisArgAsnArgArgThrAsp-561 |
| SEQ. ID. NO. 11745 | 566-LysProGlyGlyAsnProArgGlu-573 |
| SEQ. ID. NO. 11746 | 577-LeuAsnMetLysAsnSerThrSer-584 |
| SEQ. ID. NO. 11747 | 589-GlyAsnAsnArgGlnAlaAlaGluGlnValAlaGlnAlaGluAsnAlaArgProAspLeu-609 |
| SEQ. ID. NO. 11748 | 614-GlyTyrLeuGlyGluAsnAlaGlnThrGlyLysAlaAlaProSerTyrSerLysThrAsnGluAlaAlaIleGluLysThrArgHis-642 |
| SEQ. ID. NO. 11749 | 650-GlyArgProGluTyrArgTyrAsnGly-658 |
| SEQ. ID. NO. 11750 | 664-TyrArgProLysArgThrAspSer-671 |
| SEQ. ID. NO. 11751 | 677-GlyGlyMetAsnLeuAsnGly-683 |
| SEQ. ID. NO. 11752 | 694-ValSerGlyArgProValProHisAlaTyrAspHisGlnAlaLysArgGluProValLeuGluAsnGluTrpThrAspGlySerPheLysAla-724 |
| SEQ. ID. NO. 11753 | 726-ArgPheThrLeuArgAsnHisAla-733 |
| SEQ. ID. NO. 11754 | 736-ThrAlaGlyArgAsnThrAlaHisLeuAspGlyAspIleThr-749 |
| SEQ. ID. NO. 11755 | 761-ThrGlnGlyLysThrProGluCysTyrArgSerTyrHisSerGlySerThrHis-778 |
| SEQ. ID. NO. 11756 | 785-LeuLysAlaGluAsnTyrArg-791 |
| SEQ. ID. NO. 11757 | 796-ThrGlnValArgGlyAspIleThrLeuAsnAspArgSerGluLeuArgLeuGlyLys-814 |
| SEQ. ID. NO. 11758 | 820-SerIleArgAlaGlyLysAspThrAlaValArgMetGluAlaAspSerAsnTrpThr-838 |
| SEQ. ID. NO. 11759 | 840-SerGlnSerSerHisThrGly-846 |
| SEQ. ID. NO. 11760 | 859-ProAspPheAlaAsnThrHisAsnAsnArgPheAsn-871 |
| SEQ. ID. NO. 11761 | 877-GlyThrLeuAspGly-881 |
| SEQ. ID. NO. 11762 | 891-IleValArgLysGlnAsnAlaProProLeuLysLeuGluGlyAspSerArgGlyAla-909 |
| SEQ. ID. NO. 11763 | 914-ValLysAsnThrGlyGlnGluProGlnThrThrGluSer-926 |
| SEQ. ID. NO. 11764 | 932-LeuAsnProLysHisSerHisGln-939 |
| SEQ. ID. NO. 11765 | 957-IleLeuArgLysAsnAsnAsnGlyTyr-965 |
| SEQ. ID. NO. 11766 | 969-AsnProLeuLysGluAlaGluLeuGlnIleGluAlaThrArgAlaGluHisGluArgAsnGlnGlnAla-991 |
| SEQ. ID. NO. 11767 | 999-AspIleSerArgGlnValGlnHisAspSerAspAlaThrArgGlnAla-1014 |
| SEQ. ID. NO. 11768 | 1018-TrpGlnAsnSerGlnThrGluLeuAlaArgIleAspSerGln-1031 |
| SEQ. ID. NO. 11769 | 1039-LeuLysGlnThrAspProLeuThr-1046 |
| SEQ. ID. NO. 11770 | 1064-AspIleCysArgGlnValAlaLysAlaAlaAspThrAsnAsp-1077 |
| SEQ. ID. NO. 11771 | 1083-ThrGluLeuAspThrTyrIleGluArgValGluMetAlaGluSerGluLeuAspLysAlaArgGlnGlyGlyAspAlaGlnAla-1110 |
| SEQ. ID. NO. 11772 | 1123-AsnArgLeuSerArg-1127 |
| SEQ. ID. NO. 11773 | 1147-LeuIleLeuSerArgSerAlaAsnThrAlaValSerGlu-1158 |
| SEQ. ID. NO. 11774 | 1160-AlaAlaTyrAsnThrGlyArgGlnGlnAlaGlyArgArgIleAspArgHisLeuThrAspProGlnGlnAsn-1184 |
| SEQ. ID. NO. 11775 | 1188-GluThrGlyThrGlnGlnThrAspTyrHisSerGlyThrHisArgProTyrGlnGlnThrThrAsn-1209 |
| SEQ. ID. NO. 11776 | 1219-IleThrAspArgLeuSer-1224 |
| SEQ. ID. NO. 11777 | 1229-LeuThrAspGluArgThrAsnAsnArgPheAspGluGlyValSerAlaArgAsnArgSerAsnGly-1250 |
| SEQ. ID. NO. 11778 | 1255-ValLysGlyGluAsnGlyAla-1261 |
| SEQ. ID. NO. 11779 | 1269-GlyTyrSerAsnSerArgThrArgPheThrAspTyrAspGlyAlaAlaValArg-1286 |
| SEQ. ID. NO. 11780 | 1288-HisAlaTrpAspAlaGlyIleAsnThrGlyIleLysIleAspThrGlyIle-1304 |
| SEQ. ID. NO. 11781 | 1313-ArgIleAsnArgSerAsnGlyAsnArgTyrVal-1323 |
| SEQ. ID. NO. 11782 | 1326-GlyAlaGluIleAsnSerProAlaGlnIleGln-1336 |
| SEQ. ID. NO. 11783 | 1343-IleArgLeuAspLysThrValGlu-1350 |
| SEQ. ID. NO. 11784 | 1360-PheSerSerAspTyrTyrHisThrArgGlnAsnSerGlySerAla-1374 |
| SEQ. ID. NO. 11785 | 1376-SerValAsnAspArgThrLeu-1382 |
| SEQ. ID. NO. 11786 | 1398-AlaGlyTyrLysGlyTrpAsn-1404 |
| SEQ. ID. NO. 11787 | 1411-TyrGlyLysAspSerAsnThrAlaArgHisLysGlnAlaGly-1424 |

Hydrophilic Regions - Hopp-Woods

| SEQ. ID. NO. | Sequence |
|---|---|
| SEQ. ID. NO. 11788 | 29-ValArgAsnAspValAsp-34 |
| SEQ. ID. NO. 11789 | 40-AspPheAlaGluAsnLysGly-46 |
| SEQ. ID. NO. 11790 | 56-SerIleGlnAspLysGlnGlyLysIleLeu-65 |
| SEQ. ID. NO. 11791 | 75-ProAspPheArgValSerAsnArgGlnThr-84 |
| SEQ. ID. NO. 11792 | 111-AsnAspThrGlnAsnProGluGluGlnAlaTyr-121 |
| SEQ. ID. NO. 11793 | 129-AsnProHisProAspTyr-134 |
| SEQ. ID. NO. 11794 | 140-ArgLeuAsnLysLeuValThr-146 |
| SEQ. ID. NO. 11795 | 162-GlyGlnProLysAla-166 |
| SEQ. ID. NO. 11796 | 170-LeuAspThrAspArg-174 |
| SEQ. ID. NO. 11797 | 186-GlnGlnValArgLysAlaAlaAspGlyThrArgThrArgThr-198 |
| SEQ. ID. NO. 11798 | 249-AspLysHisGluAsn-253 |
| SEQ. ID. NO. 11799 | 285-ThrIleArgGlnTyrGluThrArgLeuAspVal-295 |
| SEQ. ID. NO. 11800 | 306-AspAsnGlyAsnGly-310 |
| SEQ. ID. NO. 11801 | 317-LeuAsnGluArgIleThr-322 |
| SEQ. ID. NO. 11802 | 332-ProGlnAsnAspSerArgHisMetProSerGluAspAlaGlyLys-346 |
| SEQ. ID. NO. 11803 | 352-SerArgPheAspAsnLysThr-358 |
| SEQ. ID. NO. 11804 | 395-AlaAspGlyLysArg-399 |
| SEQ. ID. NO. 11805 | 406-AsnProLysGlyAspArgLeuSerLys-414 |
| SEQ. ID. NO. 11806 | 444-LysAlaAlaSerAspGlySerLysGlnAla-453 |
| SEQ. ID. NO. 11807 | 472-GlnGlnIleLysProGlu-477 |
| SEQ. ID. NO. 11808 | 484-ArgGlyGlyArgLeuAspLeuAsnGly-492 |
| SEQ. ID. NO. 11809 | 501-ArgHisAlaAspGlyGly-506 |
| SEQ. ID. NO. 11810 | 555-HisArgAsnArgArgThrAsp-561 |

TABLE 1-continued

| | |
|---|---|
| SEQ. ID. NO. 11811 | 568-GlyGlyAsnProArgGlu-573 |
| SEQ. ID. NO. 11812 | 591-AsnArgGlnGlnAlaAlaGluGlnValAlaGlnAlaGluAsnAlaArgProAsp-608 |
| SEQ. ID. NO. 11813 | 619-AsnAlaGlnThrGlyLysAlaAlaProSerTyrSerLysThrAsnGluAlaAlaIleGluLysThrArgHis-642 |
| SEQ. ID. NO. 11814 | 652-ProGluTyrArgTyr-656 |
| SEQ. ID. NO. 11815 | 664-TyrArgProLysArgThrAspSer-671 |
| SEQ. ID. NO. 11816 | 705-HisGlnAlaLysArgGluProValLeu-713 |
| SEQ. ID. NO. 11817 | 736-ThrAlaGlyArgAsn-740 |
| SEQ. ID. NO. 11818 | 744-LeuAspGlyAspIleThr-749 |
| SEQ. ID. NO. 11819 | 764-LysThrProGluCysTyrArg-770 |
| SEQ. ID. NO. 11820 | 785-LeuLysAlaGluAsnTyrArg-791 |
| SEQ. ID. NO. 11821 | 797-GlnValArgGlyAspIleThrLeuAsnAspArgSerGluLeuArgLeuGlyLys-814 |
| SEQ. ID. NO. 11822 | 822-ArgAlaGlyLysAspThrAlaValArgMetGluAlaAspSer-835 |
| SEQ. ID. NO. 11823 | 891-IleValArgLysGlnAsnAlaPro-898 |
| SEQ. ID. NO. 11824 | 900-LeuLysLeuGluGlyAspSerArgGly-908 |
| SEQ. ID. NO. 11825 | 916-AsnThrGlyGlnGluProGlnThrThrGlu-925 |
| SEQ. ID. NO. 11826 | 934-ProLysHisSerHis-938 |
| SEQ. ID. NO. 11827 | 957-IleLeuArgLysAsnAsnAsn-963 |
| SEQ. ID. NO. 11828 | 970-ProLeuLysGluAlaGluLeuGlnIleGluAlaThrArgAlaGluHisGluArgAsnGlnGln-990 |
| SEQ. ID. NO. 11829 | 1004-ValGlnHisAspSerAspAlaThrArgGlnAla-1014 |
| SEQ. ID. NO. 11830 | 1021-SerGlnThrGluLeuAlaArgIleAspSer-1030 |
| SEQ. ID. NO. 11831 | 1039-LeuLysGlnThrAspPro-1044 |
| SEQ. ID. NO. 11832 | 1064-AspIleCysArgGlnValAlaLysAlaAlaAspThrAsnAsp-1077 |
| SEQ. ID. NO. 11833 | 1087-ThrTyrIleGluArgValGluMetAlaGluSerGluLeuAspLysAlaArgGlnGlyGlyAspAlaGlnAla-1110 |
| SEQ. ID. NO. 11834 | 1164-ThrGlyArgGlnGlnAlaGlyArgArgIleAspArgHisLeuThrAspProGlnGln-1182 |
| SEQ. ID. NO. 11835 | 1200-ThrHisArgProTyrGln-1205 |
| SEQ. ID. NO. 11836 | 1219-IleThrAspArgLeuSer-1224 |
| SEQ. ID. NO. 11837 | 1229-LeuThrAspGluArgThrAsnAsnArgPheAspGluGlyValSerAlaArgAsnArgSerAsnGly-1250 |
| SEQ. ID. NO. 11838 | 1272-AsnSerArgThrArgPheThrAspTyrAspGlyAlaAlaValArg-1286 |
| SEQ. ID. NO. 11839 | 1298-IleLysIleAspThr-1302 |
| SEQ. ID. NO. 11840 | 1313-ArgIleAsnArgSerAsnGly-1319 |
| SEQ. ID. NO. 11841 | 1326-GlyAlaGluIleAsnSer-1331 |
| SEQ. ID. NO. 11842 | 1343-IleArgLeuAspLysThrValGlu-1350 |
| SEQ. ID. NO. 11843 | 1376-SerValAsnAspArgThrLeu-1382 |
| SEQ. ID. NO. 11844 | 1411-TyrGlyLysAspSerAsnThrAlaArgHisLysGlnAlaGly-1424 |
| 760 | |
| AMPHIRegions - AMPHI | |
| SEQ. ID. NO. 11845 | 16-ThrValLeuAlaAlaLeuSerSer-23 |
| SEQ. ID. NO. 11846 | 29-GlnThrGluGlyLeu-33 |
| SEQ. ID. NO. 11847 | 40-GlyGlnArgSerTyr-44 |
| SEQ. ID. NO. 11848 | 58-PheAlaAlaThrValGlyThrLys-65 |
| SEQ. ID. NO. 11849 | 67-ProAlaSerLeuArgGluIleProGlnSerVal-77 |
| SEQ. ID. NO. 11850 | 88-ArgAsnValAspThrPheAspGlnLeuAlaArg-98 |
| SEQ. ID. NO. 11851 | 131-ProAlaGlnMetGlnSerIleAsnGlyThrLeuProAsnLeuPheAlaPheAspArgValGluValMetArgGlyProSerGlyLeuPheAspSerSerGlyGluMetGlyGlyIleValAsnLeuValArgLysArgProThrLysAlaPheGlnGlyHisAlaAlaAla-187 |
| SEQ. ID. NO. 11852 | 190-GlyThrHisLysGln-194 |
| SEQ. ID. NO. 11853 | 277-SerLeuProGlnHis-281 |
| SEQ. ID. NO. 11854 | 296-HisAspValPheAlaAspLeuLysHis-304 |
| SEQ. ID. NO. 11855 | 334-LeuAsnAsnThrGlyGlnAla-340 |
| SEQ. ID. NO. 11856 | 381-ArgLeuArgSerThr |
| SEQ. ID. NO. 11857 | 385AsnGluGlnGlyArgSerThr-392 |
| SEQ. ID. NO. 11858 | 398-AlaLeuAspGlyPheArgAlaLeuPro-406 |
| SEQ. ID. NO. 11859 | 419-LysGlyPheAsnHisSer-424 |
| SEQ. ID. NO. 11860 | 438-LysThrValPheArgProLeuGluGlyLeuSerLeuIleAlaGly-452 |
| SEQ. ID. NO. 11861 | 465-GlyLysThrLeuHisLysAlaSerLys-473 |
| SEQ. ID. NO. 11862 | 515-ProArgGluGlyAsnGln-520 |
| SEQ. ID. NO. 11863 | 565-GlyLysArgValMetGluGlyValGlu-573 |
| SEQ. ID. NO. 11864 | 617-AlaAsnLeuTrpThrThrTyr-623 |
| SEQ. ID. NO. 11865 | 635-ValAsnAlaMetSerGlyIleThrSerSer-644 |
| SEQ. ID. NO. 11866 | 650-GlyGlyTyrAlaThrPheAspAlaMetAlaAla-660 |
| Antigenic Index - Jameson-Wolf | |
| SEQ. ID. NO. 11867 | 29-GlnThrGluGlyLeuGlu-34 |
| SEQ. ID. NO. 11868 | 37-HisIleLysGlyGlnArgSerTyrAsn-45 |
| SEQ. ID. NO. 11869 | 48-AlaThrGluLysAsnGlyAspTyrSerSer-57 |
| SEQ. ID. NO. 11870 | 68-AlaSerLeuArgGluIleProGln-75 |
| SEQ. ID. NO. 11871 | 83-GlnGlnValLysAspArgAsnValAspThrPheAspGlnLeuAlaArgLysThrProGlyLeuArgValLeuSerAsnAspAspGlyArgSer-113 |
| SEQ. ID. NO. 11872 | 118-ArgGlyTyrGluTyrSerGluTyrAsnIleAspGlyLeu-130 |
| SEQ. ID. NO. 11873 | 148-AspArgValGluValMetArgGlyProSerGlyLeuPheAspSerSerGlyGluMetGlyGly-168 |
| SEQ. ID. NO. 11874 | 173-ValArgLysArgProThrLysAlaPhe-181 |
| SEQ. ID. NO. 11875 | 190-GlyThrHisLysGlnTyrLysAlaGluAlaAspValSerGlySerLeuAsnSerAspGlySerValArgGlyArgVal-215 |
| SEQ. ID. NO. 11876 | 221-GlyAlaSerProArgProAlaGluLysAsnAsnArgArgGluThr-235 |
| SEQ. ID. NO. 11877 | 242-TrpAspIleAsnProAspThrValLeu-250 |
| SEQ. ID. NO. 11878 | 257-GlnGlnArgArgLeuAlaProTyrAsn-265 |
| SEQ. ID. NO. 11879 | 268-ProAlaAspAlaAsnAsnLysLeuProSerLeu-278 |
| SEQ. ID. NO. 11880 | 306-PheGlyAsnGlyGlyTyrGly-312 |
| SEQ. ID. NO. 11881 | 314-ValGlyMetArgTyrSerArgArgLysAlaAspSerAsnTyr-327 |
| SEQ. ID. NO. 11882 | 330-AlaGlySerLysLeuAsnAsnThrGlyGlnAlaAsp-341 |
| SEQ. ID. NO. 11883 | 346-GlyThrAspIleLysGlnLysAlaPheAlaValAspAlaSerTyrSerArgProPhe-364 |
| SEQ. ID. NO. 11884 | 378-AspTyrAsnArgLeuArgSerThrAsnGluGlnGlyArgSerThrLeuSerLysSerValAla-398 |
| SEQ. ID. NO. 11885 | 413-AsnAlaArgAlaGlyAsnLysGlyPheAsn-422 |
| SEQ. ID. NO. 11886 | 424-SerValThrGluGluAsnLeuAspGluThrGlyLeu-435 |

TABLE 1-continued

| SEQ. ID. NO. | Sequence |
|---|---|
| SEQ. ID. NO. 11887 | 451-AlaGlyGlyArgValGlyHisHisLysIleGluSerGlyAspGlyLysThrLeuHisLysAlaSerLysThrLysPhe-476 |
| SEQ. ID. NO. 11888 | 485-AspIleAspGlySerAsnSerLeu-492 |
| SEQ. ID. NO. 11889 | 501-ThrProGlnThrSerIleGlyThrAspGlyLysLeuLeuLysProArgGluGlyAsnGln-520 |
| SEQ. ID. NO. 11890 | 524-GlyTyrLysGlySerTyrMetAspAspArgLeuAsnThr-536 |
| SEQ. ID. NO. 11891 | 542-ArgMetLysAspLysAsnAla-548 |
| SEQ. ID. NO. 11892 | 551-ProLeuAspSerAsnAsnLysLysThrArgTyr-561 |
| SEQ. ID. NO. 11893 | 563-AlaLeuGlyLlGluThrGluIle-576 |
| SEQ. ID. NO. 11894 | 596-GlnIleLysThrAlaSerAsnSerArgAspGluGlyIle-608 |
| SEQ. ID. NO. 11895 | 614-LysHisSerAlaAsnLeu-619 |
| SEQ. ID. NO. 11896 | 663-PheThrProLysLeuLysLeu-669 |
| SEQ. ID. NO. 11897 | 671-IleAsnAlaAspAsnIlePhe-677 |
| SEQ. ID. NO. 11898 | 685-ValGlySerGluSerThrPheAsnIleProGlySerGluArgSerLeu-700 |

Hydrophilic Regions - Hopp-Woods

| SEQ. ID. NO. | Sequence |
|---|---|
| SEQ. ID. NO. 11899 | 39-LysGlyGlnArgSer-43 |
| SEQ. ID. NO. 11900 | 48-AlaThrGluLysAsnGlyAsp-54 |
| SEQ. ID. NO. 11901 | 68-AlaSerLeuArgGluIleProGln-75 |
| SEQ. ID. NO. 11902 | 84-GlnValLysAspArgAsnValAspThr-92 |
| SEQ. ID. NO. 11903 | 94-AspGlnLeuAlaArgLysThrProGly-102 |
| SEQ. ID. NO. 11904 | 106-LeuSerAsnAspAspGlyArgSer-113 |
| SEQ. ID. NO. 11905 | 148-AspArgValGluValMetArgGlyPro-156 |
| SEQ. ID. NO. 11906 | 162-SerSerGlyGluMet-166 |
| SEQ. ID. NO. 11907 | 173-ValArgLysArgProThrLys-179 |
| SEQ. ID. NO. 11908 | 193-LysGlnTyrLysAlaGluAlaAspVal-201 |
| SEQ. ID. NO. 11909 | 205-LeuAsnSerAspGlySerValArgGlyArgVal-215 |
| SEQ. ID. NO. 11910 | 222-AlaSerProArgProAlaGluLysAsnAsnArgArgGluThr-235 |
| SEQ. ID. NO. 11911 | 242-TrpAspIleAsnPro-246 |
| SEQ. ID. NO. 11912 | 257-GlnGlnArgArgLeuAla-262 |
| SEQ. ID. NO. 11913 | 268-ProAlaAspAlaAsnAsnLysLeu-275 |
| SEQ. ID. NO. 11914 | 314-ValGlyMetArgTyrSerArgArgLysAlaAspSer-325 |
| SEQ. ID. NO. 11915 | 247-ThrAspIleLysGlnLysAlaPheAla-355 |
| SEQ. ID. NO. 11916 | 378-AspTyrAsnArgLeuArgSerThrAsnGluGlnGlyArgSerThrLeuSer-394 |
| SEQ. ID. NO. 11917 | 414-AlaArgAlaGlyAsnLysGlyPhe-421 |
| SEQ. ID. NO. 11918 | 425-ValThrGluGluAsnLeuAspGlu-432 |
| SEQ. ID. NO. 11919 | 454-ArgValGlyHisHisLysIleGluSerGlyAspGlyLysThrLeuHisLysAlaSerLysThrLysPhe-476 |
| SEQ. ID. NO. 11920 | 506-IleGlyThrAspGlyLysLeuLeuLysProArgGluGlyAsnGln-520 |
| SEQ. ID. NO. 11921 | 528-SerTyrMetAspAspArgLeuAsnThr-536 |
| SEQ. ID. NO. 11922 | 542-ArgMetLysAspLysAsnAla-548 |
| SEQ. ID. NO. 11923 | 551-ProLeuAspSerAsnAsnLysLysThrArgTyr-561 |
| SEQ. ID. NO. 11924 | 563-AlaLeuGlyLysArgValMetGluGlyValGluThrGluIle-576 |
| SEQ. ID. NO. 11925 | 597-IleLysThrAlaSerAsnSerArgAspGluGly-607 |
| SEQ. ID. NO. 11926 | 695-GlySerGluArgSerLeu-700 |

761
AMPHI Regions - AMPHI

| SEQ. ID. NO. | Sequence |
|---|---|
| SEQ. ID. NO. 11927 | 51-LysGlyTyrIleAsn-55 |
| SEQ. ID. NO. 11928 | 70-GluThrProGlnThrIleAspThrLeuAsnIle-80 |
| SEQ. ID. NO. 11929 | 89-AsnAspLeuSerSerIleLeuGlu-96 |
| SEQ. ID. NO. 11930 | 125-TyrArgAspGlyValArg-130 |
| SEQ. ID. NO. 11931 | 137-ArgSerThrAlaAsn-141 |
| SEQ. ID. NO. 11932 | 143-GluArgValGluIleLeuLysGlyProSer-152 |
| SEQ. ID. NO. 11933 | 164-ValIleAsnMetValSerLysTyrAlaAsnPheLysGlnSerArgAsnIleGlyAlaValTyrGlySerTrpAla-188 |
| SEQ. ID. NO. 11934 | 249-TyrAspAsnValGluArgThrProAspArgSerProThrLysSerVal-264 |
| SEQ. ID. NO. 11935 | 316-AspPheAspHisPheTyrAla-322 |
| SEQ. ID. NO. 11936 | 388-IleAsnProTyrAspArg-393 |
| SEQ. ID. NO. 11937 | 452-SerSerArgGlnTyr-456 |
| SEQ. ID. NO. 11938 | 475-HisThrLeuTyrAlaSerTyrAsnLysGlyPhe-485 |
| SEQ. ID. NO. 11939 | 511-TyrThrArgGlnTyrGlu-516 |
| SEQ. ID. NO. 11940 | 526-AspArgLeuSerThrThr-531 |
| SEQ. ID. NO. 11941 | 568-LeuSerAlaIleGlyGlnIleIle-575 |
| SEQ. ID. NO. 11942 | 608-AsnThrSerAsnVal-612 |
| SEQ. ID. NO. 11943 | 651-LeuProGlyPheAlaArgValAspAlaMet-660 |

Antigenic Index - Jameson-Wolf

| SEQ. ID. NO. | Sequence |
|---|---|
| SEQ. ID. NO. 11944 | 23-AlaAspThrGlnAspAsnGlyGluHis-31 |
| SEQ. ID. NO. 11945 | 43-GlyGlnSerAspThrSerValLeu-50 |
| SEQ. ID. NO. 11946 | 54-IleAsnTyrAspGluAlaAlaValThrArgAsnGlyGlnLeuIleLysGluThrProGlnThrIle-75 |
| SEQ. ID. NO. 11947 | 79-AsnIleGlnLysAsnLysAsnTyrGlyThrAsnAsp-90 |
| SEQ. ID. NO. 11948 | 97-GlyAsnAlaGlyIle-101 |
| SEQ. ID. NO. 11949 | 103-AlaAlaTyrAspMetArgGlyGluSerIlePhe-113 |
| SEQ. ID. NO. 11950 | 117-PheGlnAlaAspAlaSerAspIleTyrArgAspGlyValArgGluSerGlyGlnValArgArgSerThrAlaAsnIleGluArgValGluIleLeuLysGlyProSerSer-153 |
| SEQ. ID. NO. 11951 | 157-GlyArgThrAsnGlyGlyGly-163 |
| SEQ. ID. NO. 11952 | 172-AlaAsnPheLysGlnSerArgAsnIleGly-181 |
| SEQ. ID. NO. 11953 | 187-TrpAlaAsnArgSerLeuAsnMetAspIle-196 |
| SEQ. ID. NO. 11954 | 198-GluValLeuAsnLysAsnValAlaIle-206 |
| SEQ. ID. NO. 11955 | 208-LeuThrGlyGluValGlyArgAlaAsnSerPheArgSerGlyIleAspSerLysAsnVal-227 |
| SEQ. ID. NO. 11956 | 235-ValLysLeuAspAsnGlyLeuLysTrpThrGlyGlnTyrThrTyrAspAsnValGluArgThrProAspArgSerProThrLysSerValTyrAspArgPheGlyLeuProTyr-272 |
| SEQ. ID. NO. 11957 | 276-PheAlaHisArgAsnAspPheValLysAspLysLeuGln-288 |
| SEQ. ID. NO. 11958 | 290-TrpArgSerAspLeuGluTyrAlaPheAsnAspLysTrpArgAlaGlnTrp-306 |
| SEQ. ID. NO. 11959 | 312-ThrAlaAlaGlnAspPhe-317 |
| SEQ. ID. NO. 11960 | 322-AlaGlySerGluAsnGlyAsnLeuIleLysArgAsnTyrAlaTrpGlnGlnThrAspAsnLysThrLeuSer-345 |

TABLE 1-continued

| | |
|---|---|
| SEQ. ID. NO. 11961 | 366-GlyMetAspTyrSerArgGluHisArgAsnProThrLeu-378 |
| SEQ. ID. NO. 11962 | 389-AsnProTyrAspArgAlaSerTrpProAlaSerGlyArgLeuGlnPro-404 |
| SEQ. ID. NO. 11963 | 407-ThrGlnAsnArgHisLysAlaAspSer-415 |
| SEQ. ID. NO. 11964 | 425-SerAlaThrProAspLeuLysPheValLeuGlyGlyArgTyrAspLysTyrThrPheAsnSerGluAsnLysLeuThrGlySerSerArgGlnTyrSerGlyHisSerPheSerProAsn-464 |
| SEQ. ID. NO. 11965 | 481-TyrAsnLysGlyPheAlaProTyrGlyGlyArgGlyGly-493 |
| SEQ. ID. NO. 11966 | 506-AsnAlaAspProGluTyrThrArgGlnTyrGluThrGlyValLysSerSerTrpLeuAspAspArgLeuSerThr-530 |
| SEQ. ID. NO. 11967 | 539-ArgPheAsnIleArgTyrArgProAspProLysAsnAsnPro-552 |
| SEQ. ID. NO. 11968 | 557-ValSerGlyLysHisArgSerArgGlyValGlu-567 |
| SEQ. ID. NO. 11969 | 575-IleProLysLysLeuTyrLeu-581 |
| SEQ. ID. NO. 11970 | 591-LysValValGluAspLysGluAsnProAspArgValGly-603 |
| SEQ. ID. NO. 11971 | 607-AsnAsnThrSerAsnVal-612 |
| SEQ. ID. NO. 11972 | 619-ArgTyrThrProThrGluAsnLeuTyr-627 |
| SEQ. ID. NO. 11973 | 634-GlyThrGlyLysArgTyrGlyTyrAsnSerArgAsnLysGluValThrThr-650 |
| SEQ. ID. NO. 11974 | 663-TrpAsnHisLysAsn-667 |
| SEQ. ID. NO. 11975 | 678-LeuAsnGlnLysTyrTrpArgSerAspSerMetProGlyAsnProArgGlyTyrThrAla-697 |
| Hydrophilic Regions - Hopp-Woods | |
| SEQ. ID. NO. 11976 | 24-AspThrGlnAspAsnGlyGlu-30 |
| SEQ. ID. NO. 11977 | 43-GlyGlnSerAspThrSerVal-49 |
| SEQ. ID. NO. 11978 | 57-AspGluAlaAlaValThrArg-63 |
| SEQ. ID. NO. 11979 | 66-GlnLeuIleLysGluThrProGlnThr-74 |
| SEQ. ID. NO. 11980 | 81-GlnLysAsnLysAsnTyrGly-87 |
| SEQ. ID. NO. 11981 | 105-TyrAspMetArgGlyGluSerIlePhe-113 |
| SEQ. ID. NO. 11982 | 117-PheGlnAlaAspAlaSerAspIleTyrArgAspGlyValArgGluSerGlyGlnValArgArgSerThrAlaAsnIleGluArgValGluIleLeuLysglyProSer-152 |
| SEQ. ID. NO. 11983 | 175-LysGlnSerArgAsn-179 |
| SEQ. ID. NO. 11984 | 208-LeuThrGlyGluValGlyArg-214 |
| SEQ. ID. NO. 11985 | 220-SerGlyIleAspSerLysAsn-226 |
| SEQ. ID. NO. 11986 | 235-ValLysLeuAspAsn-239 |
| SEQ. ID. NO. 11987 | 251-AsnValGluArgThrProAspArgSerProThr-261 |
| SEQ. ID. NO. 11988 | 278-HisArgAsnAspPheValLysAspLysLeuGln-288 |
| SEQ. ID. NO. 11989 | 312-ThrAlaAlaGlnAspPhe-317 |
| SEQ. ID. NO. 11990 | 324-SerGluAsnGlyAsnLeuIleLys-331 |
| SEQ. ID. NO. 11991 | 339-ThrAspAsnLysThrLeu-344 |
| SEQ. ID. NO. 11992 | 368-AspTyrSerArgGluHisArgAsnPro-376 |
| SEQ. ID. NO. 11993 | 390-ProTyrAspArgAlaSer-395 |
| SEQ. ID. NO. 11994 | 409-AsnArgHisLysAlaAspSer-415 |
| SEQ. ID. NO. 11995 | 436-GlyArgTyrAspLys-440 |
| SEQ. ID. NO. 11996 | 445-SerGluAsnLysLeuThrGlySerSerArgGlnTyrSer-457 |
| SEQ. ID. NO. 11997 | 507-AlaAspProGluTyrThrArgGlnTyrGluThrGlyVal-519 |
| SEQ. ID. NO. 11998 | 523-TrpLeuAspAspArgLeuSer-529 |
| SEQ. ID. NO. 11999 | 544-TyrArgProAspProLysAsn-550 |
| SEQ. ID. NO. 12000 | 559-GlyLysHisArgSerArgGlyValGlu-567 |
| SEQ. ID. NO. 12001 | 591-LysValValGluAspLysGluAsnProAspArgValGly-603 |
| SEQ. ID. NO. 12002 | 634-GlyThrGlyLysArgTyrGlyTyr-641 |
| SEQ. ID. NO. 12003 | 643-SerArgAsnLysGluValThr-649 |
| SEQ. ID. NO. 12004 | 686-AspSerMetProGlyAsnProArgGlyTyrThr-696 |

762
AMPHI Regions - AMPHI
SEQ. ID. NO. 12005    1-MetLysTrpLeuLeuAsnMetIleMetArgProIleLysPheSerMetValAsnThrLeuLeuPheIleValIleCysSerSerPhePheAspLeuLeuValGlnLeuCysThrIleLeuPheHisSerGlnLysIleTyrPheIleThrLeuPheLeuLeuPheIlePheAsnPheValThrLysSerIleTyrMetAlaIleIleTyrProIleLeuTyrPhePheThrIleLysLysTyrTyrProTyrSerArgLysValIleIleLeuLeuSerLeuAlaLeuSerIleTyrPheSerPheMetAspPheTyrPhePheSerIleTyrSerAspAsnLeuSerTyrGluThrGluProLeuHisLeuTyrIleProIleIleIleAsnPhePheSerLeuLeuValSerAsnPheIleLeuSerPheIleAsnLys-147

Antigenic Index - Jameson-Wolf (SEQ. ID. NO. 12005)
1-MetLysTrpLeuLeuAsnMetIleMetArgProIleLysPheSerMetValAsnThrLeuLeuPheIleVal
IleCysSerSerPhePheAspLeuLeuValGlnLeuCysThrIleLeuPheHisSerGlnLysIleTyrPheIleThr
LeuPheLeuLeuPheIlePheAsnPheValThrLysSerIleTyrMetAlaIleIleTyrProIleLeuTyrPhe
PheThrIleLysLysTyrTyrProTyrSerArgLysValIleIleLeuLeuSerLeuAlaLeuSerIleTyrPhe
SerPheMetAspPheTyrPhePheSerIleTyrSerAspAsnLeuSerTyrGluThrGluProLeuHisLeuTyrIle
ProIleIleIleAsnPhePheSerLeuLeuValSerAsnPheIleLeuSerPheIleAsnLys-147

Hydrophilic Regions - Hopp-Woods (SEQ. ID. NO. 12005)
1-MetLysTrpLeuLeuAsnMetIleMetArgProIleLysPheSerMetValAsnThrLeuLeuPheIleVal
IleCysSerSerPhePheAspLeuLeuValGlnLeuCysThrIleLeuPheHisSerGlnLysIleTyrPheIleThr
LeuPheLeuLeuPheIlePheAsnPheValThrLysSerIleTyrMetAlaIleIleTyrProIleLeuTyrPhe
PheThrIleLysLysTyrTyrProTyrSerArgLysValIleIleLeuLeuSerLeuAlaLeuSerIleTyrPhe
SerPheMetAspPheTyrPhePheSerIleTyrSerAspAsnLeuSerTyrGluThrGluProLeuHisLeuTyrIle
ProIleIleIleAsnPhePheSerLeuLeuValSerAsnPheIleLeuSerPheIleAsnLys-147

763
AMPHI Regions - AMPHI
SEQ. ID. NO. 12006    1-MetThrLeuLeuAsnLeuMetIleMetGlnAspTyrGlyIleSerValCysLeuThrLeuThrProTyrLeuGlnHisGluLeuPheSerAlaMetLysSerTyrPheSerLysTyrIleLeuProValSerLeuPheThrLeuProLeuSerLeuSerProSerValSerAlaPheThrLeuProGluAlaTrpArgAlaAlaGlnGlnHisSerAlaAspPheGlnAlaSerHisTyrGlnArgAspAlaValArgAlaArgGlnGlnGlnAlaLysAlaAlaPheLeuProHisValSerAlaAsnAlaSerTyrGlnArgGlnProProSerIleSerSerThrArgGluThrGlnGlyTrpSerValGlnValGlyGlnThrLeuPheAspAlaAlaLysPheAlaGlnTyrArgGlnSerArgPheAspThrGlnAlaAlaGluGlnAsnArgPheAspAlaAlaArgGlyGluLeuLeuLeuLysValAlaGlnSerTyrPheAsnValLeuLeuSerArgAspThrValAlaAlaHisAlaAlaGluLysGluAlaTyrAlaGlnGlnValArgGlnAlaGlnAlaLeuPheAsnLysGlyAlaAlaThrAlaLeuAspIleHisGluAlaLysAlaGlyTyrAspAsnAlaLeuAlaGlnGluIleAlaValLeuAlaGluLysGlnThrTyrGluAsnGlnLeuAsnAspTyrThrAspLeuAspSerLysGlnIleGluAlaIleAspThrAlaAsnLeuLeuAlaArgTyrLeuProLysLeuGluArgTyrSerLeuAspGluTrpGlnArgIleAlaLeuSerAsnAsnHisGluTyrArgMetGlnGlnLeuAlaLeuGlnSerSerGlyGlnAlaLeuArgAlaAlaGlnAsnSerArgTyrProThrValSerAlaHisValGlyTyrGlnAsnAsnLeuTyrThrSerSerAlaGlnAsnAsnAspTyrHisTyrArgGlyLysGlyMetSerValGlyValGlnLeuAsnLeuProLeuTyrThrGlyGly TABLE 1-continued GluLeuSerGlyLysIleHisGluAlaGluAlaGlnTyrGlyAlaAlaGluAlaGlnLeuThrAlaThrGluArgHisIleLysLeuAlaValArgGlnAlaTyr
ThrGluSerGlyAlaAlaArgTyrGlnIleMetAlaGlnGluArgValLeuGluSerSerArgLeuLysLeuLysSerThrGluThrGlyGlnGlnTyrGlyIle
ArgAsnArgLeuGluValIleArgAlaArgGlnGluValAlaGlnAlaGluGlnLysLeuAlaGlnAlaArgTyrLysPheMetLeuAlaTyrLeuArgLeuVal
LysGluSerGlyLeuGlyLeuGluThrValPheAlaGlu-467

Antigenic Index - Jameson-Wolf (SEQ. NO. ID. 12006)
1-MetThrLeuLeuAsnLeuMetIleMetGlnAspTyrGlyIleSerValCysLeuThrLeuThrProTyrLeuGln
nHisGluLeuPheSerAlaMetLysSerTyrPheSerLysTyrIleLeuProValSerLeuPheThrLeuProLeu
SerLeuSerProSerValSerAlaPheThrLeuProGluAlaTrpArgAlaAlaGlnGlnHisSerAlaAspPhe
GlnAlaSerHisTyrGlnArgAspAlaValArgAlaArgGlnGlnGlnAlaLysAlaAlaPheLeuProHisValSer
AlaAsnAlaSerTyrGlnArgGlnProProSerIleSerSerThrArgGluThrGlnGlyTrpSerValGlnVal
GlyGlnThrLeuPheAspAlaAlaLysPheAlaGlnTyrArgGlnSerArgPheAspThrGlnAlaAlaGluGln
ArgPheAspAlaAlaArgGluGluLeuLeuLeuLysValAlaGluSerTyrPheAsnValLeuLeuSerArgAspThr
ValAlaAlaHisAlaAlaGluLysGluAlaTyrAlaGlnGlnValArgGlnAlaGlnAlaLeuPheAsnLysGly
AlaAlaThrAlaLeuAspIleHisGluAlaLysAlaGlyTyrAspAsnAlaLeuAlaGlnGluIleAlaValLeu
AlaGluLysGlnThrTyrGluAsnGlnLeuAsnAspTyrThrAspLeuAspSerLysGlnIleGluAlaIleAspThr
AlaAsnLeuLeuAlaArgTyrLeuProLysLeuGluArgTyrSerLeuAspGluTrpGlnArgIleAlaLeuSer
AsnAsnHisGluTyrArgMetGlnGlnLeuAlaLeuGlnSerSerGlyGlnAlaLeuArgAlaAlaGlnAsnSer
ArgTyrProThrValSerAlaHisValGlyTyrGlnAsnAsnLeuTyrThrSerSerAlaGlnAsnAsnAspTyrHis
TyrArgGlyLysGlyMetSerValGlyValGlnLeuAsnLeuProLeuTyrThrGlyGlyGluLeuSerGlyLys
IleHisGluAlaGluAlaGlnTyrGlyAlaAlaGluAlaGlnLeuThrAlaThrGluArgHisIleLysLeuAla
ValArgGlnAlaTyrThrGluSerGlyAlaAlaArgTyrGlnIleMetAlaGlnGluArgValLeuGluSerSerArg
LeuLysLeuLysSerThrGluThrGlyGlnGlnTyrGlyIleArgAsnArgLeuGluValIleArgAlaArgGln
GluValAlaGlnAlaGluGlnLysLeuAlaGlnAlaArgTyrLysPheMetLeuAlaTyrLeuArgLeuValLys
GluSerGlyLeuGlyLeuGluThrValPheAlaGlu-467

Hydrophilic Regions - Hopp-Woods (SEQ. NO. ID. 12006)
1-MetThrLeuLeuAsnLeuMetIleMetGlnAspTyrGlyIleSerValCysLeuThrLeuThrProTyrLeuGlnHisGluLeuPheSerAlaMet
LysSerTyrPheSerLysTyrIleLeuProValSerLeuPheThrLeuProLeuSerLeuSerProSerValSerAlaPheThrLeuProGluAlaTrp
ArgAlaAlaGlnGlnHisSerAlaAspPheGlnAlaSerHisTyrGlnArgAspAlaValArgAlaArgGlnGlnGlnAlaLysAlaAlaPheLeuPro
HisValSerAlaAsnAlaSerTyrGlnArgGlnProProSerIleSerSerThrArgGluThrGlnGlyTrpSerValGlnValGlyGlnThrLeuPhe
AspAlaAlaLysPheAlaGlnTyrArgGlnSerArgPheAspThrGlnAlaAlaGluGlnArgPheAspAlaAlaArgGluGluLeuLeuLeuLysVal
AlaGluSerTyrPheAsnValLeuLeuSerArgAspThrValAlaAlaHisAlaAlaGluLysGluAlaTyrAlaGlnGlnValArgGlnAlaGlnAla
LeuPheAsnLysGlyAlaAlaThrAlaLeuAspIleHisGluAlaLysAlaGlyTyrAspAsnAlaLeuAlaGlnGluIleAlaValLeuAlaGluLys
GlnThrTyrGluAsnGlnLeuAsnAspTyrThrAspLeuAspSerLysGlnIleGluAlaIleAspThrAlaAsnLeuLeuAlaArgTyrLeuProLys
LeuGluArgTyrSerLeuAspGluTrpGlnArgIleAlaLeuSerAsnAsnHisGluTyrArgMetGlnGlnLeuAlaLeuGlnSerSerGlyGlnAla
LeuArgAlaAlaGlnAsnSerArgTyrProThrValSerAlaHisValGlyTyrGlnAsnAsnLeuTyrThrSerSerAlaGlnAsnAsnAspTyrHis
TyrArgGlyLysGlyMetSerValGlyValGlnLeuAsnLeuProLeuTyrThrGlyGlyGluLeuSerGlyLysIleHisGluAlaGluAlaGlnTyr
GlyAlaAlaGluAlaGlnLeuThrAlaThrGluArgHisIleLysLeuAlaValArgGlnAlaTyrThrGluSerGlyAlaAlaArgTyrGlnIleMet
AlaGlnGluArgValLeuGluSerSerArgLeuLysLeuLysSerThrGluThrGlyGlnGlnTyrGlyIleArgAsnArgLeuGluValIleArgAla
ArgGlnGluValAlaGlnAlaGluGlnLysLeuAlaGlnAlaArgTyrLysPheMetLeuAlaTyrLeuArgLeuValLysGluSerGlyLeuGlyLeu
GluThrValPheAlaGlu-467
764
AMPHI Regions - AMPHI
SEQ. ID. NO. 12007    1-MetPhePheSerAlaLeuLysSerPheLeuSerArgTyrIleThrValTrpArgAsnValTrpAlaValArgAspGlnLeuLysProProLysArgThrAla
GluGluGlnAlaPheLeuProAlaHisLeuGluLeuThrAspThrProValSerAlaAlaProLysTrpAlaAlaArgPheIleMetAlaPheAlaLeuLeu
AlaLeuLeuTrpSerTrpPheGlyLysIleAspIleValAlaAlaAlaSerGlyLysThrValSerGlyGlyArgSerLysThrIleGlnProLeuGluThr
AlaValValLysAlaValHisValArgAspGlyGlnHisValLysGlnGlyGluThrLeuAlaGluLeuGluAlaValGlyThrAspSerAspValValGln
SerGluGlnAlaLeuGlnAlaAlaGlnLeuSerLysLeuArgTyrGluAlaValLeuAlaAlaLeuGluSerArgThrValProHisIleAspMetAlaGln
AlaArgSerLeuGlyLeuSerAspAlaAspValGlnSerAlaGlnValLeuAlaGlnHisGlnTyrGlnAlaTrpAlaAlaGlnAspAlaGlnLeuGlnSer
AlaLeuArgGlyHisGlnAlaGluLeuGlnSerAlaLysAlaGlnGluGlnLysLeuValSerValGlyAlaIleGluGlnGlnLysThrAlaAspTyrArg
ArgLeuArgAlaAspAsnPheIleSerGluHisAlaPheLeuGluGlnSerLysSerValSerAsnTrpAsnAspLeuGluSerThrArgGlyGlnMet
ArgGlnIleGlnAlaAlaIleAlaGlnAlaGluGlnAsnArgValLeuAsnThrGlnAsnLeuLysArgAspThrLeuAspAlaLeuArgGlnAlaAsnGlu
GlnIleAspGlnTyrArgGlyGlnThrAspLysAlaLysGlnArgGlnGlnLeuMetThrIleGlnSerProAlaAspGlyThrValGlnGluLeuAlaThr
TyrThrValGlyGlyValValGlnAlaAlaGlnLysMetMetValIleAlaProAspAspAspLysMetAspValGluValLeuValLeuAsnLysAspIle
GlyPheValGluGlnGlyGlnAspAlaValValLysIleGluSerPheProTyrThrArgTyrGlyTyrLeuThrGlyLysValLysSerValSerHisAsp
AlaValSerHisGluGlnLeuGlyLeuValTyrThrAlaValValSerLeuAspLysHisThrLeuAsnIleAspGlyLysAlaValAsnLeuThrAlaGly
MetAsnValThrAlaGluIleLysThrGlyLysArgArgValLeuAspTyrLeuLeuSerProLeuGlnThrLysLeuAspGluSerPheArgGluArg-475

Antigenic Index - Jameson-Wolf (SEQ. ID. NO. 12007)
1-MetPhePheSerAlaLeuLysSerPheLeuSerArgTyrIleThrValTrpArgAsnValTrpAlaValArgAsp
GlnLeuLysProProLysArgThrAlaGluGluGlnAlaPheLeuProAlaHisLeuGluLeuThrAspThrPro
ValSerAlaAlaProLysTrpAlaAlaArgPheIleMetAlaPheAlaLeuLeuAlaLeuLeuTrpSerTrpPheGly
LysIleAspIleValAlaAlaAlaSerGlyLysThrValSerGlyGlyArgSerLysThrIleGlnProLeuGlu
ThrAlaValValLysAlaValHisValArgAspGlyGlnHisValLysGlnGlyGluThrLeuAlaGluLeuGlu
AlaValGlyThrAspSerAspValValGlnSerGluGlnAlaLeuGlnAlaAlaGlnLeuSerLysLeuArgTyrGlu
AlaValLeuAlaAlaLeuGluSerArgThrValProHisIleAspMetAlaGlnAlaArgSerLeuGlyLeuSer
AspAlaAspValGlnSerAlaGlnValLeuAlaGlnHisGlnTyrGlnAlaTrpAlaAlaGlnAspAlaGlnLeu
GlnSerAlaLeuArgGlyHisGlnAlaGluLeuGlnSerAlaLysAlaGlnGluGlnLysLeuValSerValGly
AlaIleGluGlnGlnLysThrAlaAspTyrArgArgLeuArgAlaAspAsnPheIleSerGluHisAlaPheLeuGlu
GlnSerLysSerValSerAsnTrpAsnAspLeuGluSerThrArgGlyGlnMetArgGlnIleGlnAlaAla
IleAlaGlnAlaGluGlnAsnArgValLeuAsnThrGlnAsnLeuLysArgAspThrLeuAspAlaLeuArgGln
AlaAsnGluGlnIleAspGlnTyrArgGlyGlnThrAspLysAlaLysGlnArgGlnGlnLeuMetThrIleGln
SerProAlaAspGlyThrValGlnGluLeuAlaThrTyrThrValGlyGlyValValGlnAlaAlaGlnLysMetMet
ValIleAlaProAspAspAspLysMetAspValGluValLeuValLeuAsnLysAspIleGlyPheValGluGln
GlyGlnAspAlaValValLysIleGluSerPheProTyrThrArgTyrGlyTyrLeuThrGlyLysValLysSer
ValSerHisAspAlaValSerHisGluGlnLeuGlyLeuValTyrThrAlaValValSerLeuAspLysHisThrLeu
AsnIleAspGlyLysAlaValAsnLeuThrAlaGlyMetAsnValThrAlaGluIleLysThrGlyLysArgArg
ValLeuAspTyrLeuLeuSerProLeuGlnThrLysLeuAspGluSerPheArgGluArg-475

Hydrophilic Regions - Hopp-Woods (SEQ. ID. NO. 12007)
1-MetPhePheSerAlaLeuLysSerPheLeuSerArgTyrIleThrValTrpArgAsnValTrpAlaValArgAsp
GlnLeuLysProProLysArgThrAlaGluGluGlnAlaPheLeuProAlaHisLeuGluLeuThrAspThrPro
ValSerAlaAlaProLysTrpAlaAlaArgPheIleMetAlaPheAlaLeuLeuAlaLeuLeuTrpSerTrpPhe TABLE 1-continued GlyLysIleAspIleValAlaAlaAlaSerGlyLysThrValSerGlyGlyArgSerLysThrIleGlnProLeuGlu
ThrAlaValValLysAlaValHisValArgAspGlyGlnHisValLysGlnGlyGluThrLeuAlaGluLeuGlu
AlaValGlyThrAspSerAspValValGlnSerGluGlnAlaLeuGlnAlaAlaGlnLeuSerLysLeuArgTyr
GluAlaValLeuAlaAlaLeuGluSerArgThrValProHisIleAspMetAlaGlnAlaArgSerLeuGlyLeuSer
AspAlaAspValGlnSerAlaGlnValLeuAlaGlnHisGlnTyrGlnAlaTrpAlaAlaGlnAspAlaGlnLeu
GlnSerAlaLeuArgGlyHisGlnAlaGluLeuGlnSerAlaLysAlaGlnGluGlnLysLeuValSerValGly
AlaIleGluGlnGlnLysThrAlaAspTyrArgArgLeuArgAlaAspAsnPheIleSerGluHisAlaPheLeuGlu
GlnGlnSerLysSerValSerAsnTrpAsnAspLeuGluSerThrArgGlyGlnMetArgGlnIleGlnAlaAla
IleAlaGlnAlaGluGlnAsnArgValLeuAsnThrGlnAsnLeuLysArgAspThrLeuAspAlaLeuArgGln
AlaAsnGluGlnIleAspGlnTyrArgGlyGlnThrAspLysAlaLysGlnArgGlnGlnLeuMetThrIleGlnSer
ProAlaAspGlyThrValGlnGluLeuAlaThrTyrThrValGlyGlyValValGlnAlaAlaGlnLysMetMet
ValIleAlaProAspAspAspLysMetAspValGluValLeuValLeuAsnLysAspIleGlyPheValGluGln
GlyGlnAspAlaValValLysIleGluSerPheProTyrThrArgTyrGlyTyrLeuThrGlyLysValLysSerVal
SerHisAspAlaValSerHisGluGlnLeuGlyLeuValTyrThrAlaValValSerLeuAspLysHisThrLeu
AsnIleAspGlyLysAlaValAsnLeuThrAlaGlyMetAsnValThrAlaGluIleLysThrGlyLysArgArg
ValLeuAspTyrLeuLeuSerProLeuGlnThrLysLeuAspGluSerPheArgGluArg-475
765
AMPHI Regions - AMPHI
SEQ. ID. NO. 12008   36-SerAlaIleSerSerPheCys-42
SEQ. ID. NO. 12009   45-LysIleIleHisThrTyr-50
SEQ. ID. NO. 12010   59-ValIleGlyIleIleAsnGly-65
SEQ. ID. NO. 12011   105-ArgPheLeuAsnArgGly-110
SEQ. ID. NO. 12012   147-PheGlyLeuCysTyrPro-152
Antigenic Index - Jameson-Wolf
SEQ. ID. NO. 12013   10-GlyAsnPheLysLysIleAlaThr-17
SEQ. ID. NO. 12014   19-GlnGlyLeuAspArgLysTyr-25
SEQ. ID. NO. 12015   76-ValLysAsnLysGlnLysPheLeu-83
SEQ. ID. NO. 12016   106-PheLeuAsnArgGlyMetLys-112
SEQ. ID. NO. 12017   132-LeuAsnGluGluGlyGlyTrpMet-139
SEQ. ID. NO. 12018   160-LeuSerArgAspTyrLysHisIle-167
Hydrophilic Regions - Hopp-Woods
SEQ. ID. NO. 12019   11-AsnPheLysLysIleAlaThr-17
SEQ. ID. NO. 12020   19-GlnGlyLeuAspArgLys-24
SEQ. ID. NO. 12021   76-ValLysAsnLysGlnLysPheLeu-83
SEQ. ID. NO. 12022   133-AsnGluGluGlyGly-137
SEQ. ID. NO. 12023   162-ArgAspTyrLysHis-166
767
AMPHI Regions - AMPHI
SEQ. ID. NO. 12024   1-MetLysLeuLysHisLeuLeuProLeuLeuLeuSerAlaValLeuSerAlaGlnAlaTyrAlaLeuThrGluGlyGluAspTyrLeuValLeuAspLysPro
IleProGlnGluGlnSerGlyLysIleGluValLeuGluPhePheGlyTyrPheCysValHisCysHisHisPheAspProLeuLeuLeuLysLeuGlyLysAla
LeuProSerAspAlaTyrLeuArgThrGluHisValValTrpGlnProGluMetLeuGlyLeuAlaArgMetAlaAlaAlaValAsnLeuSerGlyLeuLysTyr
GlnAlaAsnProAlaValPheLysAlaValTyrGluGlnLysIleArgLeuGluAsnArgSerValAlaGlyLysTrpAlaLeuSerGlnLysGlyPheAsp
GlyLysLysLeuMetArgAlaTyrAspSerProGluAlaAlaAlaAlaAlaLeuLysMetGlnLysLeuThrGluGlnTyrArgIleAspSerThrProThrVal
IleValGlyGlyLysTyrArgValIlePheAsnAsnGlyPheAspGlyGlyValHisThrIleLysGluLeuValAlaLysValArgGluGluArgLysArgGln
ThrProAlaValGlnLys-214)
Antigenic Index - Jameson-Wolf (SEQ. ID. NO. 12024)
1-MetLysLeuLysHisLeuLeuProLeuLeuLeuSerAlaValLeuSerAlaGlnAlaTyrAlaLeuThrGluGlyGluAspTyrLeuValLeuAspLysProIle
GlnGluGlnGlnGluGlnSerGlyLysIleGluValLeuGluPhePheGlyTyrPheCysValHisCysHisHisPheAspProLeuLeuLeuLysLeuGlyLys
AlaLeuProSerAspAlaTyrLeuArgThrGluHisValValTrpGlnProGluMetLeuGlyLeuAlaArgMetAlaAlaAlaValAsnLeuSerGlyLeuLys
TyrGlnAlaAsnProAlaValPheLysAlaValTyrGluGlnLysIleArgLeuGluAsnArgSerValAlaGlyLysTrpAlaLeuSerGlnLysGlyPheAsp
GlyLysLysLeuMetArgAlaTyrAspSerProGluAlaAlaAlaAlaAlaLeuLysMetGlnLysLeuThrGluGlnTyrArgIleAspSerThrProThrVal
IleValGlyGlyLysTyrArgValIlePheAsnAsnGlyPheAspGlyGlyValHisThrIleLysGluLeuValAlaLysValArgGluGluArgLysArgGln
ThrProAlaValGlnLys-214
Hydrophilic Regions - Hopp-Woods (SEQ. ID. NO. 12024)
1-MetLysLeuLysHisLeuLeuProLeuLeuLeuSerAlaValLeuSerAlaGlnAlaTyrAlaLeuThrGluGlyGluAspTyrLeuValLeuAspLysProIle
ProGlnGluGlnSerGlyLysIleGluValLeuGluPhePheGlyTyrPheCysValHisCysHisHisPheAspProLeuLeuLeuLysLeuGlyLysAlaLeu
ProSerAspAlaTyrLeuArgThrGluHisValValTrpGlnProGluMetLeuGlyLeuAlaArgMetAlaAlaAlaValAsnLeuSerGlyLeuLysTyrGln
AlaAsnProAlaValPheLysAlaValTyrGluGlnLysIleArgLeuGluAsnArgSerValAlaGlyLysTrpAlaLeuSerGlnLysGlyPheAspGlyLys
LysLeuMetArgAlaTyrAspSerProGluAlaAlaAlaAlaAlaLeuLysMetGlnLysLeuThrGluGlnTyrArgIleAspSerThrProThrValIleVal
GlyGlyLysTyrArgValIlePheAsnAsnGlyPheAspGlyGlyValHisThrIleLysGluLeuValAlaLysValArgGluGluArgLysArgGlnThrPro
AlaValGlnLys-214
768
AMPHI Regions - AMPHI
SEQ. ID. NO. 12025   23-ProGlnLysProValSerAlaAlaGlnThr-32
SEQ. ID. NO. 12026   60-ProValAspGlnIleValArgArgIleHisGluAlaAla-72
SEQ. ID. NO. 12027   93-LeuGlnGluLeuLysLysAlaGlyTyrThrAsnValAlaAsnHisGly-108
Antigenic Index - Jameson-Wolf
SEQ. ID. NO. 12028   21-AlaAlaProGlnLysProValSer-28
SEQ. ID. NO. 12029   42-ValArgSerGluGlnGluPheSerGluGlyHis-52
SEQ. ID. NO. 12030   63-GlnIleValArgArgIleHisGluAlaAlaProAspLysAspThrPro-78
SEQ. ID. NO. 12031   82-TyrCysArgSerGlyArgArgAlaGluAlaAlaLeuGlnGluLeuLysLysAlaGlyTyr-101
SEQ. ID. NO. 12032   106-AsnHisGlyGlyTyrGluAspLeuLeuLysLysGlyMetLys-119
Hydrophilic Regions - Hopp-Woods
SEQ. ID. NO. 12033   22-AlaProGlnLysProValSer-28
SEQ. ID. NO. 12034   42-ValArgSerGluGlnGluPheSerGlu-50
SEQ. ID. NO. 12035   63-GlnIleValArgArgIleHisGluAlaAlaProAspLysAspThrPro-78
SEQ. ID. NO. 12036   84-ArgSerGlyArgArgAlaGluAlaAlaLeuGlnGluLeuLysLysAlaGly-100
SEQ. ID. NO. 12037   109-GlyTyrGluAspLeuLeuLysLysGlyMetLys-119

TABLE 1-continued

769
AMPHI Regions - AMPHI
SEQ. ID. NO. 12038    1-LeuIleMetValIlePheTyrPheCysGlyLysThrPheMetProAlaArgAsnArgTrpMetLeuLeuLeuProLeuLeuAlaSerAlaAlaTyrAlaGlu
GluThrProArgGluProAspLeuArgSerArgProGluPheArgLeuHisGluAlaGluValLysProIleAspArgGluLysValProGlyGlnValArgGlu
LysGlyLysValLeuGlnIleAspGlyGluThrLeuLeuLysAsnProGluLeuLeuSerArgAlaMetTyrSerAlaValValSerAsnAsnIleAlaGlyIle
ArgValIleLeuProIleTyrLeuGlnGlnAlaGlnGlnAspLysMetLeuAlaLeuTyrAlaGlnGlyIleLeuAlaGlnAlaAspGlyArgValLysGlu
AlaIleSerHisTyrArgGluLeuIleAlaAlaGlnProAspAlaProAlaValArgMetArgLeuAlaAlaAlaLeuPheGluAsnArgGlnAsnGluAlaAla
AlaAspGlnPheAspArgLeuLysAlaGluAsnLeuProProGlnLeuMetGluGlnValGluLeuTyrArgLysAlaLeuArgGluArgAspAlaTrpLysVal
AsnGlyGlyPheSerValThrArgGluHisAsnIleAsnGlnAlaProLysArgGlnGlnTyrGlyLysTrpThrPheProLysGlnValAspGlyThrAla
ValAsnTyrArgLeuGlyAlaGluLysLysTrpSerLeuLysAsnGlyTrpTyrThrThrAlaGlyGlyAspValSerGlyArgValTyrProGlyAsnLysLys
PheAsnAspMetThrAlaGlyValSerGlyGlyIleGlyPheAlaAspArgArgLysAspAlaGlyLeuAlaValPheHisGluArgArgThrTyrGlyAsnAsp
AlaTyrSerTyrThrAsnGlyAlaArgLeuTyrPheAsnArgTrpGlnThrProLysTrpGlnThrLeuSerSerAlaGluTrpGlyArgLeuLysAsnThr
ArgArgAlaArgSerAspAsnThrHisLeuGlnIleSerAsnSerLeuValPheTyrArgAsnAlaArgGlnTyrTrpMetGlyGlyLeuAspPheTyrArgGlu
ArgAsnProAlaAspArgGlyAspAsnPheAsnArgTyrGlyLeuArgPheAlaTrpGlyGlnGluTrpGlyGlySerGlyLeuSerSerLeuLeuArgLeuGly
AlaAlaLysArgHisTyrGluLysProGlyPhePheSerGlyPheLysGlyGluArgArgArgAspLysGluLeuAsnThrSerLeuSerLeuTrpHisArg
AlaLeuHisPheLysGlyIleThrProArgLeuThrLeuSerHisArgGluThrArgSerAsnAspValPheAsnGluTyrGluLysAsnArgAlaPheValGlu
PheAsnLysThrPhe-490
Antigenic Index - Jameson-Wolf (SEQ. ID. NO. 12038)
1-LeuIleMetValIlePheTyrPheCysGlyLysThrPheMetProAlaArgAsnArgTrpMetLeuLeuLeuProLeuLeuAlaSerAlaAlaTyrAlaGluGlu
ThrProArgGluProAspLeuArgSerArgProGluPheArgLeuHisGluAlaGluValLysProIleAspArgGluLysValProGlyGlnValArgGluLys
GlyLysValLeuGlnIleAspGlyGluThrLeuLeuLysAsnProGluLeuLeuSerArgAlaMetTyrSerAlaValValSerAsnAsnIleAlaGlyIleArg
ValIleLeuProIleTyrLeuGlnGlnAlaGlnGlnAspLysMetLeuAlaLeuTyrAlaGlnGlyIleLeuAlaGlnAlaAspGlyArgValLysGluAlaIle
SerHisTyrArgGluLeuIleAlaAlaGlnProAspAlaProAlaValArgMetArgLeuAlaAlaAlaLeuPheGluAsnArgGlnAsnGluAlaAlaAlaAsp
GlnPheAspArgLeuLysAlaGluAsnLeuProProGlnLeuMetGluGlnValGluLeuTyrArgLysAlaLeuArgGluArgAspAlaTrpLysValAsnGly
GlyPheSerValThrArgGluHisAsnIleAsnGlnAlaProLysArgGlnGlnTyrGlyLysTrpThrPheProLysGlnValAspGlyThrAlaValAsnTyr
ArgLeuGlyAlaGluLysLysTrpSerLeuLysAsnGlyTrpTyrThrThrAlaGlyGlyAspValSerGlyArgValTyrProGlyAsnLysLysPheAsnAsp
MetThrAlaGlyValSerGlyGlyIleGlyPheAlaAspArgArgLysAspAlaGlyLeuAlaValPheHisGluArgArgThrTyrGlyAsnAspAlaTyrSer
TyrThrAsnGlyAlaArgLeuTyrPheAsnArgTrpGlnThrProLysTrpGlnThrLeuSerSerAlaGluTrpGlyArgLeuLysAsnThrArgArgAlaArg
SerAspAsnThrHisLeuGlnIleSerAsnSerLeuValPheTyrArgAsnAlaArgGlnTyrTrpMetGlyGlyLeuAspPheTyrArgGluArgAsnProAla
AspArgGlyAspAsnPheAsnArgTyrGlyLeuArgPheAlaTrpGlyGlnGluTrpGlyGlySerGlyLeuSerSerLeuLeuArgLeuGlyAlaAlaLysArg
HisTyrGluLysProGlyPhePheSerGlyPheLysGlyGluArgArgArgAspLysGluLeuAsnThrSerLeuSerLeuTrpHisArgAlaLeuHisPheLys
GlyIleThrProArgLeuThrLeuSerHisArgGluThrArgSerAsnAspValPheAsnGluTyrGluLysAsnArgAlaPheValGluPheAsnLysThr
Phe-490
Hydrophilic Regions - Hopp-Woods (SEQ. ID. NO. 12038)
1-LeuIleMetValIlePheTyrPheCysGlyLysThrPheMetProAlaArgAsnArgTrpMetLeuLeuLeuProLeuLeuAlaSerAlaAlaTyrAlaGluGlu
ThrProArgGluProAspLeuArgSerArgProGluPheArgLeuHisGluAlaGluValLysProIleAspArgGluLysValProGlyGlnValArgGluLys
GlyLysValLeuGlnIleAspGlyGluThrLeuLeuLysAsnProGluLeuLeuSerArgAlaMetTyrSerAlaValValSerAsnAsnIleAlaGlyIleArg
ValIleLeuProIleTyrLeuGlnGlnAlaGlnGlnAspLysMetLeuAlaLeuTyrAlaGlnGlyIleLeuAlaGlnAlaAspGlyArgValLysGluAlaIle
SerHisTyrArgGluLeuIleAlaAlaGlnProAspAlaProAlaValArgMetArgLeuAlaAlaAlaLeuPheGluAsnArgGlnAsnGluAlaAlaAlaAsp
GlnPheAspArgLeuLysAlaGluAsnLeuProProGlnLeuMetGluGlnValGluLeuTyrArgLysAlaLeuArgGluArgAspAlaTrpLysValAsnGly
GlyPheSerValThrArgGluHisAsnIleAsnGlnAlaProLysArgGlnGlnTyrGlyLysTrpThrPheProLysGlnValAspGlyThrAlaValAsnTyr
ArgLeuGlyAlaGluLysLysTrpSerLeuLysAsnGlyTrpTyrThrThrAlaGlyGlyAspValSerGlyArgValTyrProGlyAsnLysLysPheAsnAsp
MetThrAlaGlyValSerGlyGlyIleGlyPheAlaAspArgArgLysAspAlaGlyLeuAlaValPheHisGluArgArgThrTyrGlyAsnAspAlaTyrSer
TyrThrAsnGlyAlaArgLeuTyrPheAsnArgTrpGlnThrProLysTrpGlnThrLeuSerSerAlaGluTrpGlyArgLeuLysAsnThrArgArgAlaArg
SerAspAsnThrHisLeuGlnIleSerAsnSerLeuValPheTyrArgAsnAlaArgGlnTyrTrpMetGlyGlyLeuAspPheTyrArgGluArgAsnProAla
AspArgGlyAspAsnPheAsnArgTyrGlyLeuArgPheAlaTrpGlyGlnGluTrpGlyGlySerGlyLeuSerSerLeuLeuArgLeuGlyAlaAlaLysArg
HisTyrGluLysProGlyPhePheSerGlyPheLysGlyGluArgArgArgAspLysGluLeuAsnThrSerLeuSerLeuTrpHisArgAlaLeuHisPheLys
GlyIleThrProArgLeuThrLeuSerHisArgGluThrArgSerAsnAspValPheAsnGluTyrGluLysAsnArgAlaPheValGluPheAsnLysThr
Phe-490
770
AMPHI Regions - AMPHI
SEQ. ID. NO. 12039 1-MetAsnArgLeuLeuLeuLeuSerAlaAlaValLeuLeuThrAlaCysGlySerGlyGluThrAspLysIleGlyArgAlaSerThrValPheAsnIleLeu
GlyLysAsnAspArgIleGluValGluGlyPheAspAspProAspValGlnGlyValAlaCysTyrIleSerTyrAlaLysLysGlyGlyLeuLysGluMet
ValAsnLeuGluGluAspAlaSerAspAlaSerValSerCysValGlnThrAlaSerSerIleSerPheAspGluThrAlaValArgLysProLysGluVal
PheLysHisGlyAlaSerPheAlaPheLysSerArgGlnIleValArgTyrTyrAspProLysArgLysThrPheAlaTyrLeuValTyrSerAspLysIle
IleGlnGlySerProLysAsnSerLeuSerAlaValSerCysPheGlyGlyGlyIleProGlnThrAspGlyValGlnAlaAspThrSerGlyAsnLeuLeu
AlaGlyAlaCysMetIleSerAsnProIleGluAsnLeuAspLysArg-186
Antigenic Index - Jameson-Wolf (SEQ. ID. NO. 12039)
1-MetAsnArgLeuLeuLeuLeuSerAlaAlaValLeuLeuThrAlaCysGlySerGlyGluThrAspLysIleGlyArgAlaSerThrValPheAsnIleLeuGly
LysAsnAspArgIleGluValGluGlyPheAspAspProAspValGlnGlyValAlaCysTyrIleSerTyrAlaLysLysGlyGlyLeuLysGluMetValAsn
LeuGluGluAspAlaSerAspAlaSerValSerCysValGlnThrAlaSerSerIleSerPheAspGluThrAlaValArgLysProLysGluValPheLysHis
GlyAlaSerPheAlaPheLysSerArgGlnIleValArgTyrTyrAspProLysArgLysThrPheAlaTyrLeuValTyrSerAspLysIleIleGlnGlySer
ProLysAsnSerLeuSerAlaValSerCysPheGlyGlyGlyIleProGlnThrAspGlyValGlnAlaAspThrSerGlyAsnLeuLeuAlaGlyAlaCysMet
IleSerAsnProIleGluAsnLeuAspLysArg-186
Hydrophilic Regions - Hopp-Woods (SEQ. ID. NO. 12039)
1-MetAsnArgLeuLeuLeuLeuSerAlaAlaValLeuLeuThrAlaCysGlySerGlyGluThrAspLysIleGlyArgAlaSerThrValPheAsnIleLeuGly
LysAsnAspArgIleGluValGluGlyPheAspAspProAspValGlnGlyValAlaCysTyrIleSerTyrAlaLysLysGlyGlyLeuLysGluMetValAsn
LeuGluGluAspAlaSerAspAlaSerValSerCysValGlnThrAlaSerSerIleSerPheAspGluThrAlaValArgLysProLysGluValPheLysHis
GlyAlaSerPheAlaPheLysSerArgGlnIleValArgTyrTyrAspProLysArgLysThrPheAlaTyrLeuValTyrSerAspLysIleIleGlnGlySer
ProLysAsnSerLeuSerAlaValSerCysPheGlyGlyGlyIleProGlnThrAspGlyValGlnAlaAspThrSerGlyAsnLeuLeuAlaGlyAlaCysMet
IleSerAsnProIleGluAsnLeuAspLysArg-186
771
AMPHI Regions - AMPHI
SEQ. ID. NO. 12040 1-MetAspLeuLeuSerValPheHisLysTyrArgLeuLysTyrAlaValAlaValLeuThrIleLeuLeuLeuAlaAlaValGlyLeuHisAlaSerValTyr
ArgThrPheThrProGluAsnIleArgSerArgLeuGlnGlnSerIleAlaHisThrHisArgLysIleSerPheAspAlaAspIleGlnArgArgLeuLeuPro
ArgProThrValIleLeuLysAsnLeuThrIleThrGluProGlyGlyAspGlnThrAlaValSerValGlnGluThrLysIleGlyLeuSerTrpLysAsnLeu
TrpSerAspGlnIleGlnIleGluLysTrpValValSerSerAlaGluLeuAlaLeuThrArgAspGlyLysGlyValTrpAsnIleGlnAspLeuIleAsp
SerGlnLysArgGlnAlaSerValAsnArgIleIleValGluAsnSerThrValArgLeuAsnPheLeuGlnGluGlnLeuIleLeuLysGluIleAsnLeuAsn
LeuGlnSerProAspSerSerGlyGlnProPheGluSerSerGlyIleLeuValTrpGlyLysLeuSerValProTrpLysSerArgGlyLeuPheLeuSerAsn
GlyIleGlyProProGluIleSerProPheHisPheGluAlaSerThrSerLeuAspGlyHisGlyIleThrIleSerThrThrGlySerProSerValArg TABLE 1-continued PheAsnAlaGlyGlyAlaAspAlaAlaGlyLeuGlyLeuArgAlaAspThrSerPheArgAsnLeuHisLeuThrAlaGlnIleProAlaLeuAlaLeuArgAsn
AsnSerIleLysIleGluThrValAsnGlyAlaPheThrAlaGlyGlyGluTyrAlaArgTrpAspGlySerPheLysLeuAspLysAlaAsnLeuHisSer
GlyIleAlaAsnIleGlyAsnAlaGluIleSerGlySerPheLysThrProArgHisGlnThrAsnPheSerLeuAsnSerProLeuValTrpThrGluAsnLys
GlyLeuAspAlaProArgLeuTyrValSerThrLeuGlnAspThrValAsnArgLeuProGlnProArgPheIleSerArgLeuAspGlySerLeuSerValPro
AsnLeuGlnAsnTrpAsnAlaGluLeuAsnGlyThrPheAspArgGlnThrValAlaAlaLysPheArgTyrThrHisGluAspAlaProHisLeuGluAla
AlaValAlaLeuGlnLysLeuAsnLeuThrProTyrLeuAspAspValArgGlnGlnAsnGlyLysIlePheProAspThrLeuAlaLysLeuSerGlyAspIle
GluAlaHisLeuLysIleGlyLysValGlnLeuProGlyLeuGlnLeuAspAspMetGluThrTyrLeuHisAlaAspLysGlyHisIleAlaLeuSerArgPhe
LysSerGlyLeuTyrGlyGlyHisThrGluGlyGlyIleSerIleAlaAsnThrArgProAlaThrTyrArgLeuGlnGlnAsnAlaSerAsnIleGlnIle
GlnProLeuLeuGlnAspLeuPheGlyPheHisSerPheSerGlyAsnGlyAspAlaValIleAspLeuThrAlaGlyGlyGluThrArgLysGluLeuIleArg
SerLeuGlnGlySerLeuSerLeuAsnIleSerAsnGlyAlaTrpHisGlyIleAspMetAspAsnIleLeuLysAsnGlyIleSerGlyLysThrAlaAspAsn
AlaAlaProSerThrProPheHisArgPheThrLeuAsnSerGluIleSerAspGlyIleSerArgHisIleAspThrGluLeuPheSerAspSerLeuTyr
ValThrSerAsnGlyTyrThrAsnLeuAspThrGlnGluLeuSerGluAspValLeuIleArgAsnAlaValHisProLysAsnLysProIleProLeuLysIle
ThrGlyThrValAspLysProSerIleThrValAspTyrGlyArgLeuThrGlyGlyIleAsnSerArgLysGluLysGlnLysIleLeuGluAspThrLeuLeu
GluGlnTrpGlnTrpLeuLysProLysGluProAla-705

Antigenic Index - Jameson-Wolf (SEQ. ID. NO. 12040)
1-MetAspLeuLeuSerValPheHisLysTyrArgLeuLysTyrAlaValAlaValLeuThrIleLeuLeuLeuAla
AlaValGlyLeuHisAlaSerValTyrArgThrPheThrProGluAsnIleArgSerArgLeuGlnSerIle
AlaHisThrHisArgLysIleSerPheAspAlaAspIleGlnArgArgLeuLeuProArgProThrValIleLeuLys
AsnLeuThrIleThrGluProGlyGlyAspGlnThrAlaValSerValGlnGluThrLysIleGlyLeuSerTrp
LysAsnLeuTrpSerAspGlnIleGlnIleGluLysTrpValValSerSerAlaGluLeuAlaLeuThrArgAsp
GlyLysGlyValTrpAsnIleGlnAspLeuIleAspSerGlnLysArgGlnAlaSerValAsnArgIleIleVal
GluAsnSerThrValArgLeuAsnPheLeuGlnGluGlnLeuIleLeuLysGluIleAsnLeuAsnLeuGlnSer
ProAspSerSerGlyGlnProPheGluSerSerGlyIleLeuValTrpGlyLysLeuSerValProTrpLysSerArg
GlyLeuPheLeuSerAsnGlyIleGlyProProGluIleSerProPheHisPheGluAlaSerThrSerLeuAspGly
HisGlyIleThrIleSerThrThrGlySerProSerValArgPheAsnAlaGlyIleAlaAspAlaAlaGlyLeu
GlyLeuArgAlaAspThrSerPheArgAsnLeuHisLeuThrAlaGlnIleProAlaLeuAlaLeuArgAsnAsn
SerIleLysIleGluThrValAsnGlyAlaPheThrAlaGlyGlyGluTyrAlaArgTrpAspGlySerPheLys
LeuAspLysAlaAsnLeuHisSerGlyIleAlaAsnIleGlyAsnAlaGluIleSerGlySerPheLysThrProArg
HisGlnThrAsnPheSerLeuAsnSerProLeuValTrpThrGluAsnLysGlyLeuAspAlaProArgLeuTyr
ValSerThrLeuGlnAspThrValAsnArgLeuProGlnProArgPheIleSerArgLeuAspGlySerLeuSer
ValProAsnLeuGlnAsnTrpAsnAlaGluLeuAsnGlyThrPheAspArgGlnThrValAlaAlaLysPheArg
TyrThrHisGluAspAlaProHisLeuGluAlaAlaValAlaLeuGlnLysLeuAsnLeuThrProTyrLeuAspAsp
ValArgGlnGlnAsnGlyLysIlePheProAspThrLeuAlaLysLeuSerGlyAspIleGluAlaHisLeuLysIle
GlyLysValGlnLeuProGlyLeuGlnLeuAspAspMetGluThrTyrLeuHisAlaAspLysGlyHisIleAla
LeuSerArgPheLysSerGlyLeuTyrGlyGlyHisThrGluGlyGlyIleSerIleAlaAsnThrArgProAla
ThrTyrArgLeuGlnGlnAsnAlaSerAsnIleGlnIleGlnProLeuLeuGlnAspLeuPheGlyPheHisSer
PheSerGlyAsnGlyAspAlaValIleAspLeuThrAlaGlyGlyGluThrArgLysGluLeuIleArgSerLeuGln
GlySerLeuSerLeuAsnIleSerAsnGlyAlaTrpHisGlyIleAspMetAspAsnIleLeuLysAsnGlyIle
SerGlyLysThrAlaAspAsnAlaAlaProSerThrProPheHisArgPheThrLeuAsnSerGluIleSerAspGly
IleSerArgHisIleAspThrGluLeuPheSerAspSerLeuTyrValThrSerAsnGlyTyrThrAsnLeuAsp
ThrGlnGluLeuSerGluAspValLeuIleArgAsnAlaValHisProLysAsnLysProIleProLeuLysIle
ThrGlyThrValAspLysProSerIleThrValAspTyrGlyArgLeuThrGlyGlyIleAsnSerArgLysGlu
LysGlnLysIleLeuGluAspThrLeuLeuGluGlnTrpGlnTrpLeuLysProLysGluProAla-705

Hydrophilic Regions - Hopp-Woods (SEQ. ID. NO. 12040)
1-MetAspLeuLeuSerValPheHisLysTyrArgLeuLysTyrAlaValAlaValLeuThrIleLeuLeuLeuAla
AlaValGlyLeuHisAlaSerValTyrArgThrPheThrProGluAsnIleArgSerArgLeuGlnSerIle
AlaHisThrHisArgLysIleSerPheAspAlaAspIleGlnArgArgLeuLeuProArgProThrValIleLeu
LysAsnLeuThrIleThrGluProGlyGlyAspGlnThrAlaValSerValGlnGluThrLysIleGlyLeuSer
TrpLysAsnLeuTrpSerAspGlnIleGlnIleGluLysTrpValValSerSerAlaGluLeuAlaLeuThrArgAsp
GlyLysGlyValTrpAsnIleGlnAspLeuIleAspSerGlnLysArgGlnAlaSerValAsnArgIleIleVal
GluAsnSerThrValArgLeuAsnPheLeuGlnGluGlnLeuIleLeuLysGluIleAsnLeuAsnLeuGlnSerPro
AspSerSerGlyGlnProPheGluSerSerGlyIleLeuValTrpGlyLysLeuSerValProTrpLysSerArg
GlyLeuPheLeuSerAsnGlyIleGlyProProGluIleSerProPheHisPheGluAlaSerThrSerLeuAspGly
HisGlyIleThrIleSerThrThrGlySerProSerValArgPheAsnAlaGlyIleAlaAspAlaAlaGlyLeu
GlyLeuArgAlaAspThrSerPheArgAsnLeuHisLeuThrAlaGlnIleProAlaLeuAlaLeuArgAsnAsn
SerIleLysIleGluThrValAsnGlyAlaPheThrAlaGlyGlyGluTyrAlaArgTrpAspGlySerPheLysLeu
AspLysAlaAsnLeuHisSerGlyIleAlaAsnIleGlyAsnAlaGluIleSerGlySerPheLysThrProArg
HisGlnThrAsnPheSerLeuAsnSerProLeuValTrpThrGluAsnLysGlyLeuAspAlaProArgLeuTyr
ValSerThrLeuGlnAspThrValAsnArgLeuProGlnProArgPheIleSerArgLeuAspGlySerLeuSerVal
ProAsnLeuGlnAsnTrpAsnAlaGluLeuAsnGlyThrPheAspArgGlnThrValAlaAlaLysPheArgTyr
ThrHisGluAspAlaProHisLeuGluAlaAlaValAlaLeuGlnLysLeuAsnLeuThrProTyrLeuAspAsp
ValArgGlnGlnAsnGlyLysIlePheProAspThrLeuAlaLysLeuSerGlyAspIleGluAlaHisLeuLysIle
GlyLysValGlnLeuProGlyLeuGlnLeuAspAspMetGluThrTyrLeuHisAlaAspLysGlyHisIleAla
LeuSerArgPheLysSerGlyLeuTyrGlyGlyHisThrGluGlyGlyIleSerIleAlaAsnThrArgProAla
ThrTyrArgLeuGlnGlnAsnAlaSerAsnIleGlnIleGlnProLeuLeuGlnAspLeuPheGlyPheHisSer
PheSerGlyAsnGlyAspAlaValIleAspLeuThrAlaGlyGlyGluThrArgLysGluLeuIleArgSerLeuGln
GlySerLeuSerLeuAsnIleSerAsnGlyAlaTrpHisGlyIleAspMetAspAsnIleLeuLysAsnGlyIle
SerGlyLysThrAlaAspAsnAlaAlaProSerThrProPheHisArgPheThrLeuAsnSerGluIleSerAsp
GlyIleSerArgHisIleAspThrGluLeuPheSerAspSerLeuTyrValThrSerAsnGlyTyrThrAsnLeuAsp
ThrGlnGluLeuSerGluAspValLeuIleArgAsnAlaValHisProLysAsnLysProIleProLeuLysIle
ThrGlyThrValAspLysProSerIleThrValAspTyrGlyArgLeuThrGlyGlyIleAsnSerArgLysGlu
LysGlnLysIleLeuGluAspThrLeuLeuGluGlnTrpGlnTrpLeuLysProLysGluProAla-705
772

AMPHI Regions - AMPHI
SEQ. ID. NO. 12041    1-MetPheGlyAlaValLeuArgIleAspAlaAspCysLeuGlnIleIleValAlaCysLysLeuPheGlnIleValAlaTyrGlyPheAlaAlaLeuValGlu
GlyGluPheHisGluPheGlyLysMetLeuGluIleValArgLeuAlaAspAlaValPheHisArgAsnHisThrAspAspGlyGlyIleHisPheArgArg
ArgValGluArgPheGlyArgTyrValAsnGlnHisPheHisIleGluLysIleLeuGlnHisHisAlaGlnAlaAlaValValValAlaPheArgArgGly
AsnHisThrLeuAspHisPhePheLeuGlnHisLysValHisIleAspAspIleValArgHisLeuArgGlnLeuGluGlnLysArgCysGlyAsnValVal
ArgGluValAlaAspAspPheLeuPheAlaCysAspAlaValGluIleLysLeuGlnTyrIleAlaPheValAsnHisGlnPheIleArgLysArgGlnArg
PheGlnThrAlaTyrAspValAlaValAspPheAspAsnValGlnAlaValGlnLeuPheArgGlnArgPheGlyAsnArgArgGlnThrArgAlaAspPhe AsnHisAspIleIleArgLeuArgAlaHisGlyValAspAsnIleAlaAspAsnProArgValLeuGlnLysIleLeuProGluThrLeuAlaGlyPheVal
                    PhePheHisArgValSerPheSerValGluThrProProPheArgAlaValGluSerAspSerIleTrpGluGlyArgAsnSerPheGlnIleArgMetAla
                    HisArgAlaValLeuTyrValSerSerCysValLeuLysHisLysCysValTyrSerIleArgLeuMetSerAlaLeu-298

Antigenic Index - Jameson-Wolf (SEQ. ID. NO. 12041)
1-MetPheGlyAlaValLeuArgIleAspAlaAspCysLeuGlnIleIleValAlaCysLysLeuPheGlnIleVal
AlaTyrGlyPheAlaAlaLeuValGluGlyGluPheHisGluPheGlyLysMetLeuGluIleValArgLeuAla
AspAlaValPheHisArgAsnHisThrAspAspGlyGlyIleHisPheArgArgArgValGluArgPheGlyArg
TyrValAsnGlnHisPheHisIleGluLysIleLeuGlnHisHisAlaGlnAlaAlaValValValAlaPheArgArg
GlyAsnHisThrLeuAspHisPhePheLeuGlnHisLysValHisIleAspAspIleValArgHisLeuArgGln
LeuGluGlnLysArgCysGlyAsnValValArgGluValAlaAspAspPheLeuPheAlaCysAspAlaValGlu
IleLysLeuGlnTyrIleAlaPheValAsnHisGlnPheIleArgLysArgGlnArgPheGlnThrAlaTyrAspVal
AlaValAspPheAspAsnValGlnAlaValGlnLeuPheArgGlnArgPheGlyAsnArgArgGlnThrArgAla
AspPheAsnHisAspIleIleArgLeuArgAlaHisGlyValAspAsnIleAlaAspAsnProArgValLeuGln
LysIleLeuProGluThrLeuAlaGlyPheValPhePheHisArgValSerPheSerValGluThrProProPheArg
AlaValGluSerAspSerIleTrpGluGlyArgAsnSerPheGlnIleArgMetAlaHisArgAlaValLeuTyr
ValSerSerCysValLeuLysHisLysCysValTyrSerIleArgLeuMetSerAlaLeu-298

Hydrophilic Regions - Hopp-Woods (SEQ. ID. NO. 12041)
1-MetPheGlyAlaValLeuArgIleAspAlaAspCysLeuGlnIleIleValAlaCysLysLeuPheGlnIleVal
AlaTyrGlyPheAlaAlaLeuValGluGlyGluPheHisGluPheGlyLysMetLeuGluIleValArgLeuAla
AspAlaValPheHisArgAsnHisThrAspAspGlyGlyIleHisPheArgArgArgValGluArgPheGlyArgTyr
ValAsnGlnHisPheHisIleGluLysIleLeuGlnHisHisAlaGlnAlaAlaValValValAlaPheArgArg
GlyAsnHisThrLeuAspHisPhePheLeuGlnHisLysValHisIleAspAspIleValArgHisLeuArgGln
LeuGluGlnLysArgCysGlyAsnValValArgGluValAlaAspAspPheLeuPheAlaCysAspAlaValGluIle
LysLeuGlnTyrIleAlaPheValAsnHisGlnPheIleArgLysArgGlnArgPheGlnThrAlaTyrAspVal
AlaValAspPheAspAsnValGlnAlaValGlnLeuPheArgGlnArgPheGlyAsnArgArgGlnThrArgAla
AspPheAsnHisAspIleIleArgLeuArgAlaHisGlyValAspAsnIleAlaAspAsnProArgValLeuGln
LysIleLeuProGluThrLeuAlaGlyPheValPhePheHisArgValSerPheSerValGluThrProProPheArg
AlaValGluSerAspSerIleTrpGluGlyArgAsnSerPheGlnIleArgMetAlaHisArgAlaValLeuTyr
ValSerSerCysValLeuLysHisLysCysValTyrSerIleArgLeuMetSerAlaLeu-298

773
AMPHI Regions - AMPHI
SEQ. ID. NO. 12042    1-MetGlyLeuGlyAlaThrThrPheValGlySerGlyAlaIleGlyGlyGlyLeuCysSerThrGlyIleGlyCysAlaAlaGlyGlyLeuIleAlaThrAla
                     GlyMetThrGlyGlyTyrThrGlnAlaSerGluGlySerArgGlnLeuPheGlyThrTyrGlnSerAspPheGlyLysValValLeuSerLeuGlyThr
                     ProIleGluTyrGluSerProLeuValSerAspAlaLysAsnLeuAlaValTrpGlyLeuGluThrLeuIleThrArgLysLeuGlyAsnLeuAlaThrGly
                     ValLysThrSerLeuThrProLysThrAlaAspValGlnArgAsnIleLeuSerGlnSerGluValGlyIleLysTrpGlyLysGlyIleGluGlyGlnGly
                     MetProTrpGluAspTyrValGlyLysGlyLeuSerAlaAsnAlaArgLeuProLysAsnPheLysThrPheAspTyrPheAspArgGlyThrGlyThrAla
                     IleSerAlaLysThrLeuAspThrGlnThrThrAlaArgLeuSerLysProGluGlnLeuTyrSerThrMetLysGlyTyrIleAspLysThrAlaAsnPhe
                     LysSerTyrGluLeuSerGluValProLeuArgAlaAspMetIleLysGlnArgGluIleHisLeuAlaIleProAlaGlnThrAsnLysGluGlnArgLeu
                     GlnLeuGlnArgValValGluTyrGlyLysSerGlnAsnIleThrValLysIleThrGluIleGlu-260

Antigenic Index - Jameson-Wolf (SEQ. ID. NO. 12042)
1-MetGlyLeuGlyAlaThrThrPheValGlySerGlyAlaIleGlyGlyGlyLeuCysSerThrGlyIleGlyCys
AlaAlaGlyGlyLeuIleAlaThrAlaGlyMetThrGlyGlyTyrThrGlnAlaSerGluGlySerArgGlnLeu
PheGlyThrTyrGlnSerAspPheGlyLysLysValValLeuSerLeuGlyThrProIleGluTyrGluSerPro
LeuValSerAspAlaLysAsnLeuAlaValTrpGlyLeuGluThrLeuIleThrArgLysLeuGlyAsnLeuAlaThr
GlyValLysThrSerLeuThrProLysThrAlaAspValGlnArgAsnIleLeuSerGlnSerGluValGlyIle
LysTrpGlyLysGlyIleGluGlyGlnGlyMetProTrpGluAspTyrValGlyLysGlyLeuSerAlaAsnAlaA
ArgLeuProLysAsnPheLysThrPheAspTyrPheAspArgGlyThrGlyThrAlaIleSerAlaLysThrLeuAsp
ThrGlnThrThrAlaArgLeuSerLysProGluGlnLeuTyrSerThrMetLysGlyTyrIleAspLysThrAla
AsnPheLysSerTyrGluLeuSerGluValProLeuArgAlaAspMetIleLysGlnArgGluIleHisLeuAla
IleProAlaGlnThrAsnLysGluGlnArgLeuGlnLeuGlnArgValValGluTyrGlyLysSerGlnAsnIleThrValLysIleThrGluIleGlu-260

Hydrophilic Regions - Hopp-Woods (SEQ. ID. NO. 12042)
1-MetGlyLeuGlyAlaThrThrPheValGlySerGlyAlaIleGlyGlyGlyLeuCysSerThrGlyIleGlyCys
AlaAlaGlyGlyLeuIleAlaThrAlaGlyMetThrGlyGlyTyrThrGlnAlaSerGluGlySerArgGlnLeu
PheGlyThrTyrGlnSerAspPheGlyLysLysValValLeuSerLeuGlyThrProIleGluTyrGluSerPro
LeuValSerAspAlaLysAsnLeuAlaValTrpGlyLeuGluThrLeuIleThrArgLysLeuGlyAsnLeuAlaThr
GlyValLysThrSerLeuThrProLysThrAlaAspValGlnArgAsnIleLeuSerGlnSerGluValGlyIle
LysTrpGlyLysGlyIleGluGlyGlnGlyMetProTrpGluAspTyrValGlyLysGlyLeuSerAlaAsnAla
ArgLeuProLysAsnPheLysThrPheAspTyrPheAspArgGlyThrGlyThrAlaIleSerAlaLysThrLeuAsp
ThrGlnThrThrAlaArgLeuSerLysProGluGlnLeuTyrSerThrMetLysGlyTyrIleAspLysThrAla
AsnPheLysSerTyrGluLeuSerGluValProLeuArgAlaAspMetIleLysGlnArgGluIleHisLeuAla
IleProAlaGlnThrAsnLysGluGlnArgLeuGlnLeuGlnArgValValGluTyrGlyLysSerGlnAsnIleThrValLysIleThrGluIleGlu-260

774
AMPHI Regions - AMPHI
SEQ. ID. NO. 12043    1-MetLysIleLysLeuProLeuPheIleIleTrpLeuSerValSerAlaSerCysAlaSerValSerProValProAlaGlySerGlnThrGluMetSerThr
                     ArgGluAsnAlaSerAspGlyIleProTyrProValProThrLeuGlnAspArgLeuAspTyrLeuGluGlyLysIleValArgLeuSerAsnGluValGlu
                     ThrLeuAsnGlyLysValLysAlaLeuGluHisAlaLysThrHisSerSerGlyArgAlaTyrValGlnLysLeuAspAspArgLysLeuLysGluHisTyr
                     LeuAsnThrGluGlyGlySerAlaSerAlaHisThrValGluThrAlaGlnAsnLeuTyrAsnGlnAlaLeuLysHisTyrLysSerGlyLysPheSerAla
                     AlaAlaSerLeuLeuLysGlyAlaAspGlyGlyAspGlyGlySerIleAlaGlnArgSerMetTyrLeuLeuLeuGlnSerArgAlaArgMetGlyAsnCys
                     GluSerValIleGluIleGlyGlyArgTyrAlaAsnArgPheLysAspSerProThrAlaProGluAlaMetPheLysIleGlyGluCysGlnTyrArgLeu
                     GlnGlnLysAspIleAlaArgAlaThrTrpArgSerLeuIleGlnThrTyrProGlySerProAlaAlaLysArgAlaAlaAlaAlaValArgLysArg-237

Antigenic Index - Jameson-Wolf (SEQ. ID. NO. 12043)
1-MetLysIleLysLeuProLeuPheIleIleTrpLeuSerValSerAlaSerCysAlaSerValSerProValPro
AlaGlySerGlnThrGluMetSerThrArgGluAsnAlaSerAspGlyIleProTyrProValProThrLeuGln
AspArgLeuAspTyrLeuGluGlyLysIleValArgLeuSerAsnGluValGluThrLeuAsnGlyLysValLys
AlaLeuGluHisAlaLysThrHisSerSerGlyArgAlaTyrValGlnLysLeuAspAspArgLysLeuLysGluHis
TyrLeuAsnThrGluGlyGlySerAlaSerAlaHisThrValGluThrAlaGlnAsnLeuTyrAsnGlnAlaLeu
LysHisTyrLysSerGlyLysPheSerAlaAlaAlaSerLeuLeuLysGlyAlaAspGlyGlyAspGlyGlySer
IleAlaGlnArgSerMetTyrLeuLeuLeuGlnSerArgAlaArgMetGlyAsnCysGluSerValIleGluIleGly
GlyArgTyrAlaAsnArgPheLysAspSerProThrAlaProGluAlaMetPheLysIleGlyGluCysGlnTyr
ArgLeuGlnGlnLysAspIleAlaArgAlaThrTrpArgSerLeuIleGlnThrTyrProGlySerProAlaAlaLysArgAlaAlaAlaAlaValArgLysArg-237

TABLE 1-continued

Hydrophilic Regions - Hopp-Woods (SEQ. ID. NO. 12043)
1-MetLysIleLysLeuProLeuPheIleI-
leTrpLeuSerValSerAlaSerCysAlaSerValSerProValProAlaGlySerGlnThrGluMetSerThrArgGluAsnAlaSerAspGlyIleProTyrPro
ValProThrLeuGlnAspArgLeuAspTyrLeuGluGlyLysIleValArgLeuSerAsnGluValGluThrLeuAsnGly
LysValLysAlaLeuGluHisAlaLysThrHisSerSerGlyArgAlaTyrValGlnLysLeuAspAspArgLysLeuLys
GluHisTyrLeuAsnThrGluGlyGlySerAlaSerAlaHisThrValGluThrAlaGlnAsnLeuTyrAsnGlnAlaLeu
LysHisTyrLysSerGlyLysPheSerAlaAlaAlaSerLeuLeuLysGlyAlaAspGlyGlyAspGlyGlySerIleAla
GlnArgSerMetTyrLeuLeuLeuGlnSerArgAlaArgMetGlyAsnCysGluSerValIleGluIleGlyGlyArgTyr
AlaAsnArgPheLysAspSerProThrAlaProGluAlaMetPheLysIleGlyGluCysGlnTyrArgLeuGlnGlnLys
AspIleAlaArgAlaThrTrpArgSerLeuIleGlnThrTyrProGlySerProAlaAlaLysArgAlaAlaAlaAlaVal
ArgLysArg-237
790
AMPHI Regions - AMPHI
SEQ. ID. NO. 12044   10-GluAlaAlaAlaGluVal-15
SEQ. ID. NO. 12045   44-GlyAsnGlnThrCysSerArgTyrSerAsn-53
SEQ. ID. NO. 12046   89-LysGlnAlaValThr-93
SEQ. ID. NO. 12047   103-ThrGlnAlaTyrAsnGluMetThrLysSerVal-113
SEQ. ID. NO. 12048   166-PheAlaArgThrGlyLysLeu-172
SEQ. ID. NO. 12049   174-GlySerPheAspLeuPheAlaSerVal-182
SEQ. ID. NO. 12050   253-ProSerGluAlaPheAspLeuProGluGlySerThr-264
SEQ. ID. NO. 12051   320-PheLeuArgPheTrpGlnAlaThrArgGlyIle-330
Antigenic Index - Jameson-Wolf
SEQ. ID. NO. 12052   1-MetAlaArgArgSerLysThrPheGluGluAlaAlaAlaGluValGluGluArgPheGlyHisArgGlyIleLys-25
SEQ. ID. NO. 12053   30-GluGlyThrAlaLysProCysVal-37
SEQ. ID. NO. 12054   39-AsnCysProLysHisGlyAsnGlnThrCysSerArgTyrSer-52
SEQ. ID. NO. 12055   57-GlySerSerTrpGlyCysProSerCysGlyAsnGluGlnAlaAla-71
SEQ. ID. NO. 12056   77-ThrLeuArgLysAsnHisIle-83
SEQ. ID. NO. 12057   95-MetThrLysGlnGluArgIleThr-102
SEQ. ID. NO. 12058   123-AspValGlnGlyAspThrThrIle-130
SEQ. ID. NO. 12059   134-HisThrHisThrHisAsnHisSerAspAlaAspGlyLysAlaLeuSer-149
SEQ. ID. NO. 12060   152-LeuThrProArgProLeuLeuSerAspArgGlnAla-163
SEQ. ID. NO. 12061   167-AlaArgThrGlyLysLeuThrGly-174
SEQ. ID. NO. 12062   194-MetProAspThrSerMet-199
SEQ. ID. NO. 12063   201-ProValIleGluLysGlyAsp-207
SEQ. ID. NO. 12064   213-ProArgMetCysProAlaAspGluAspIleAla-223
SEQ. ID. NO. 12065   226-GluLeuSerAspLysArgLeuVal-233
SEQ. ID. NO. 12066   248-TyrGlnThrGlyArgProSerGluAlaPheAspLeuProGluGlySerThr-264
SEQ. ID. NO. 12067   270-LeuGluSerLysAsnGlyLeuCysProProHisArgGlnGluGlyVal-285
SEQ. ID. NO. 12068   301-SerAlaSerLysThrSerCysThrArgProThrAlaAlaArgLysSerAla-317
SEQ. ID. NO. 12069   326-AlaThrArgGlyIleProLysThrArgSerTrpArgAsnProAsnAsnAla-342
Hydrophilic Regions - Hopp-Woods
SEQ. ID. NO. 12070   1-MetAlaArgArgSerLysThrPheGluGluAlaAlaAlaGluValGluGluArgPheGlyHisArgGlyIleLys-25
SEQ. ID. NO. 12071   65-CysGlyAsnGluGlnAlaAla-71
SEQ. ID. NO. 12072   77-ThrLeuArgLysAsnHisIle-83
SEQ. ID. NO. 12073   96-ThrLysGlnGluArgIleThr-102
SEQ. ID. NO. 12074   139-AsnHisSerAspAlaAspGlyLysAlaLeuSer-149
SEQ. ID. NO. 12075   157-LeuLeuSerAspArgGlnAla-163
SEQ. ID. NO. 12076   168-ArgThrGlyLysLeu-172
SEQ. ID. NO. 12077   202-ValIleGluLysGlyAsp-207
SEQ. ID. NO. 12078   213-ProArgMetCysProAlaAspGluAspIleAla-223
SEQ. ID. NO. 12079   226-GluLeuSerAspLysArgLeuVal-233
SEQ. ID. NO. 12080   251-GlyArgProSerGluAlaPheAspLeuProGlu-261
SEQ. ID. NO. 12081   270-LeuGluSerLysAsnGlyLeu-276
SEQ. ID. NO. 12082   280-HisArgGlnGluGlyVal-285
SEQ. ID. NO. 12083   303-SerLysThrSerCysThrArgProThrAlaAlaArgLysSerAla-317
SEQ. ID. NO. 12084   328-ArgGlyIleProLysThrArgSerTrpArgAsn-338
900-2
AMPHI Regions - AMPHI
SEQ. ID. NO. 12085   9-ValValAlaPheAlaArgPhe-15
SEQ. ID. NO. 12086   36-ValGlyLysHisPheArgLysPheHisArgPheArgArgArgGlyGlu-51
SEQ. ID. NO. 12087   53-PheValAspPheLysGlnTrpAlaPheValGlyLeuPheArgLeuAlaArgLeuPheHisIleGlyAspAspPheValAspArgPheLeuGlyPhe
                     Phe-85
SEQ. ID. NO. 12088   121-GlyGluGluPheProGluAlaValValGluAlaAlaGlyAspValAlaArgHisPheAspValLeuAspLeuVal-145
SEQ. ID. NO. 12089   161-SerHisGlnAsnArgIle-166
SEQ. ID. NO. 12090   198-HisGlnThrLeuGlySerAspAlaGly-206
SEQ. ID. NO. 12091   210-ValGlnPheHisHisPheGly-216
SEQ. ID. NO. 12092   233-GlyLysProSerGlyGlyAsnGlyLeuGlyGlyLeuValAsnHisLeuArgLeuValAla-252
SEQ. ID. NO. 12093   268-IleGluValLeuArgArgAlaAspGlyGly-277
SEQ. ID. NO. 12094   279-AspGlyAlaAspValValAlaGlnMet-287
Antigenic Index - Jameson-Wolf
SEQ. ID. NO. 12095   1-LeuArgArgValGlyGlyGln-7
SEQ. ID. NO. 12096   19-GlyValAspPheArgArgGlnLysPhePheGlyPheThrProArgGlnAlaVal-36
SEQ. ID. NO. 12097   38-LysHisPheArgLysPheHisArgPheArgArgArgGlyGluGly-52
SEQ. ID. NO. 12098   74-GlyAspAspPheValAspArg-80
SEQ. ID. NO. 12099   88-PheProLysArgAsnGlyValAla-95
SEQ. ID. NO. 12100   103-SerValGlnThrAspGlnGluPhe-110
SEQ. ID. NO. 12101   118-PheGlyGlnGlyGluGluPheProGlu-126
SEQ. ID. NO. 12102   131-AlaAlaGlyAspValAlaArg-137
SEQ. ID. NO. 12103   145-ValAlaProAspGly-149
SEQ. ID. NO. 12104   157-GlnAsnIleGlySerHisGlnAsnArgIleThrGluGlnThrHisPhe-172

| | |
|---|---|
| SEQ. ID. NO. 12105 | 201-LeuGlySerAspAlaGlyGlnAsnProVal-210 |
| SEQ. ID. NO. 12106 | 230-GluSerAlaGlyLysProSerGlyGlyAsnGly-240 |
| SEQ. ID. NO. 12107 | 252-AlaPheAspAspThrValValIleGlyGluGluGluGluGlyPheGly-267 |
| SEQ. ID. NO. 12108 | 270-ValLeuArgArgAlaAspGlyGlyAlaAspGlyAlaAsp-282 |
| SEQ. ID. NO. 12109 | 285-AlaGlnMetArgAspAlaGlyGlyGlyTyrAlaGly-296 |
| SEQ. ID. NO. 12110 | 311-MetProSerGluArgGluLysAspValProIle-321 |
| SEQ. ID. NO. 12111 | 323-ProAspLeuProProThrSerSerArgGlnGlnThr-334 |

Hydrophilic Regions - Hopp-Woods

| | |
|---|---|
| SEQ. ID. NO. 12112 | 1-LeuArgArgValGly-5 |
| SEQ. ID. NO. 12113 | 20-ValAspPheArgArgGlnLys-26 |
| SEQ. ID. NO. 12114 | 38-LysHisPheArgLysPheHisArgPheArgArgArgGlyGluGly-52 |
| SEQ. ID. NO. 12115 | 89-ProLysArgAsnGly-93 |
| SEQ. ID. NO. 12116 | 105-GlnThrAspGlnGluPhe-110 |
| SEQ. ID. NO. 12117 | 120-GlnGlyGluGluPhePro-125 |
| SEQ. ID. NO. 12118 | 131-AlaAlaGlyAspValAlaArg-137 |
| SEQ. ID. NO. 12119 | 162-HisGlnAsnArgIleThrGlu-168 |
| SEQ. ID. NO. 12120 | 201-LeuGlySerAspAlaGlyGln-207 |
| SEQ. ID. NO. 12121 | 231-SerAlaGlyLysProSerGly-237 |
| SEQ. ID. NO. 12122 | 257-ValValIleGlyGluGluGluGluGlyPheGly-267 |
| SEQ. ID. NO. 12123 | 270-ValLeuArgArgAlaAspGlyGlyAlaAspGlyAlaAsp-282 |
| SEQ. ID. NO. 12124 | 285-AlaGlnMetArgAspAlaGly-291 |
| SEQ. ID. NO. 12125 | 311-MetProSerGluArgGluLysAspValProIle-321 |
| SEQ. ID. NO. 12126 | 326-ProProThrSerSerArgGlnGln-333 |

901-2
AMPHI Regions - AMPHI

| | |
|---|---|
| SEQ. ID. NO. 12127 | 20-GlyLeuPheThrValLeuGly-26 |
| SEQ. ID. NO. 12128 | 55-ValSerLeuThrGluIlePheSerLysSer-64 |
| SEQ. ID. NO. 12129 | 66-GluAlaPheAlaGluIleTyrAsp-73 |
| SEQ. ID. NO. 12130 | 84-AlaPheLeuAlaGlyMetGlyGlyIleAlaLeuIle-95 |
| SEQ. ID. NO. 12131 | 97-ArgLeuValProAsnProHisGluThrLeuAsp-107 |
| SEQ. ID. NO. 12132 | 124-ValGlyMetMetAlaAlaPhe-130 |
| SEQ. ID. NO. 12133 | 136-AsnPheProGluGlyLeuAlaThrPhePheAlaThrLeuGlu-149 |
| SEQ. ID. NO. 12134 | 164-HisAsnIleProGluGlyIleSer-171 |
| SEQ. ID. NO. 12135 | 190-CysLeuLeuSerGlyLeuAlaGluProLeuGlyAlaAla-202 |
| SEQ. ID. NO. 12136 | 217-PheGlySerValPheGlyValIleAlaGlyValMet-228 |
| SEQ. ID. NO. 12137 | 143-TyrSerAspGlyHisGlu-248 |

Antigenic Index - Jameson-Wolf

| | |
|---|---|
| SEQ. ID. NO. 12138 | 1-MetProAspPheSerMet-6 |
| SEQ. ID. NO. 12139 | 33-SerLysThrProAsnProArgVal-40 |
| SEQ. ID. NO. 12140 | 61-PheSerLysSerSerGluAlaPhe-68 |
| SEQ. ID. NO. 12141 | 71-IleTyrAspLysAspHisAla-77 |
| SEQ. ID. NO. 12142 | 98-LeuValProAsnProHisGluThrLeuAspAlaGlnAspProSerPheGlnGluSerLysArgArgHisIleAla-122 |
| SEQ. ID. NO. 12143 | 136-AsnPheProGluGly-140 |
| SEQ. ID. NO. 12144 | 179-AlaThrArgSerArgLysLysThr-186 |
| SEQ. ID. NO. 12145 | 193-SerGlyLeuAlaGluProLeuGly-200 |
| SEQ. ID. NO. 12146 | 235-GluLeuProAlaAlaLysArgTyrSerAspGlyHisGluThr-249 |

Hydrophilic Regions - Hopp-Woods

| | |
|---|---|
| SEQ. ID. NO. 12147 | 61-PheSerLysSerSerGluAlaPhe-68 |
| SEQ. ID. NO. 12148 | 71-IleTyrAspLysAspHisAla-77 |
| SEQ. ID. NO. 12149 | 102-ProHisGluThrLeuAspAlaGlnAspProSerPheGlnGluSerLysArgArgHisIleAla-122 |
| SEQ. ID. NO. 12150 | 180-ThrArgSerArgLysLysThr-186 |
| SEQ. ID. NO. 12151 | 235-GluLeuLeuProAlaAlaLysArgTyrSerAspGlyHisGlu-248 |

902
AMPHI Regions - AMPHI

| | |
|---|---|
| SEQ. ID. NO. 12152 | 1-LeuHisPheGlnArgIleIleLysCysSerGluGlyIleTrpAlaValGlyAlaArgProThrValGlyPhePheGlyLysSerPheLysIleThrCysLysHisValValLeuArgArgArgThrValGlnAlaValAspPheThrThrCysLeuPheAlaValGlyHisPheValAspValProAlaTyrValPheAlaCysAspAlaHisThrGlyGlyValAlaValLysArgValTyrGlyAlaAspValValGlnAsnSerGlyGlyAlaPheCysGlnThrGlnGlyArgArgGlnAsnThrValPheGlyIleMetPheGlnIleAlaGluGluProArgProAlaLeuArgAlaAlaProTyrHisAsnAlaValGlyGlyGlyLeuPheGluAspGlyLeuGlyPheLeuArgArgSerAsnValAlaValAspProAspArgAspValGlnThrAlaPheGlyPheGlyAspGluPheValThrArgPheAlaPheValHisLeuArgThrArgAlaSerValAspGlyLysGlyGlyAspAlaAlaIlePheGlyAspPheGlyAspAspGlyGlnValLeuMetValValValProThrGlnThrGlyPheGluGlyAsnGlyTyrAlaCysArgThrAspAspGlyPheGlnAsnGlyGlyAsnGlnArgLeuValLeuHisGlnArgAlaThrGlyLeuAspIleAlaAspPhePheSerGlyThrAlaHisValAspValAspLysLeuArgProLysAlaAspValValThrArgGlyIleArgHisLeuLeuArgIleAlaSerGlyAsnLeuHisGlyAsnAsnAlaAlaPheIleGlyLysIleAlaAlaValGlnGlyPheSerSerIleSerGluArgArgValAlaGlyGlnHisPheAlaHisArgProThrCysAlaLysIleSerAlaLysSerAlaGluArgPheValGlyAsnAlaArgHisArgArgLysCysAspGlyValValAspLysIleAlaAlaAspValHisAsnGlySerAlaPheGlnLysSerThrProLeuTyrIlePhe-360 |

Antigenic Index - Jameson-Wolf (SEQ. ID. NO. 12153)
1-LeuHisPheGlnArgIleIleLysCysSerGluGlyIleTrpAlaValGlyAlaArgProThrValGlyPhePhe
GlyLysSerPheLysIleThrCysLysHisValValLeuArgArgArgThrValGlnAlaValAspPheThrThr
CysLeuPheAlaValGlyHisPheValAspValProAlaTyrValPheAlaCysAspAlaHisThrGlyGlyVal
AlaValLysArgValTyrGlyAlaAspValValGlnAsnSerGlyGlyAlaPheCysGlnThrGlnGlyArgArgGln
AsnThrValPheGlyIleMetPheGlnIleAlaGluGluProArgProAlaLeuArgAlaAlaProTyrHisAsn
AlaValGlyGlyGlyLeuPheGluAspGlyLeuGlyPheLeuArgArgSerAsnValAlaValAspProAspArgAsp
ValGlnThrAlaPheGlyPheGlyAspGluPheValThrArgPheAlaPheValHisLeuArgThrArgAlaSer
ValAspGlyLysGlyGlyAspAlaAlaIlePheGlyAspPheGlyAspAspGlyGlnValLeuMetValValVal
ProThrGlnThrGlyPheGluGlyAsnGlyTyrAlaCysArgThrAspAspGlyPheGlnAsnGlyGlyAsnGlnArg
LeuValLeuHisGlnArgAlaThrGlyLeuAspIleAlaAspPhePheSerGlyThrAlaHisValAspValAsp
LysLeuArgProLysAlaAspValValThrArgGlyIleArgHisLeuLeuArgIleAlaSerGlyAsnLeuHis
GlyAsnAsnAlaAlaPheIleGlyLysIleAlaAlaValGlnGlyPheSerSerIleSerGluArgArgValAla
GlyGlnHisPheAlaHisArgProThrCysAlaLysIleSerAlaLysSerAlaGluArgPheValGlyAsnAlaArg TABLE 1-continued HisArgArgLysCysAspGlyValValAspLysIleAlaAlaAspValHisAsnGlySerAlaPheGlnLysSerThrProLeuTyrIlePhe-360
Hydrophilic Regions - Hopp-Woods (SEQ. ID. NO. 12153)
1-LeuHisPheGlnArgIleIleLysCysSerGluGlyIleTrpAlaValGlyAlaArgProThrValGlyPhePhe
GlyLysSerPheLysIleThrCysLysHisValValLeuArgArgArgThrValGlnAlaValAspPheThrThr
CysLeuPheAlaValGlyHisPheValAspValProAlaTyrValPheAlaCysAspAlaHisThrGlyGlyVal
AlaValLysArgValTyrGlyAlaAspValValGlnAsnSerGlyGlyAlaPheCysGlnThrGlnGlyArgArgGln
AsnThrValPheGlyIleMetPheGlnIleAlaGluGluProArgProAlaLeuArgAlaAlaProTyrHisAsn
AlaValGlyGlyGlyLeuPheGluAspGlyLeuGlyPheLeuArgArgSerAsnValAlaValAspProAspArg
AspValGlnThrAlaPheGlyPheGlyAspGluPheValThrArgPheAlaPheValHisLeuArgThrArgAlaSer
ValAspGlyLysGlyGlyAspAlaAlaIlePheGlyAspPheGlyAspAspGlyGlnValLeuMetValValVal
ProThrGlnThrGlyPheGluGlyAsnGlyTyrAlaCysArgThrAspAspGlyPheGlnAsnGlyGlyAsnGln
ArgLeuValLeuHisGlnArgAlaThrGlyLeuAspIleAlaAspPhePheSerGlyThrAlaHisValAspValAsp
LysLeuArgProLysAlaAspValValThrArgGlyIleArgHisLeuLeuArgIleAlaSerGlyAsnLeuHis
GlyAsnAsnAlaAlaPheIleGlyLysIleAlaAlaValGlnGlyPheSerSerIleSerGluArgArgValAla
GlyGlnHisPheAlaHisArgProThrCysAlaLysIleSerAlaLysSerAlaGluArgPheValGlyAsnAlaArg
HisArgArgLysCysAspGlyValValAspLysIleAlaAlaAspValHisAsnGlySerAlaPheGlnLysSerThrProLeuTyrIlePhe-360
903-2
AMPHI Regions - AMPHI
SEQ. ID. NO. 12153    29-GluLeuIleArgSerMetGlnArgGln-37
SEQ. ID. NO. 12154    109-AsnLeuSerArgLeuGlnLysAla-116
SEQ. ID. NO. 12155    191-GluGlnGlyLeuGluAsnLeuArgArgLeuProSerVal-203
SEQ. ID. NO. 12156    240-GlyGlyLysThrThrGlyLysTyr-247
SEQ. ID. NO. 12157    262-SerAspLeuPheTyr-266
SEQ. ID. NO. 12158    315-ArgTyrHisGluAlaThrGlu-321
SEQ. ID. NO. 12159    360-ThrArgGlnThrTyrLysTyrIleAspAsp-369
SEQ. ID. NO. 12160    560-HisLysProLysGlyPheGlnThrThrAsnThr-570
Antigenic Index - Jameson-Wolf
SEQ. ID. NO. 12161    21-LeuAlaAlaAspGluAsnAspAlaGluLeuIleArgSerMetGlnArgGlnGlnHisIleAsp-41
SEQ. ID. NO. 12162    48-AlaAsnValArgPheGluGlnProLeuGluLysAsnAsnTyrValLeuSerGluAspGluThrProCysThrArg-72
SEQ. ID. NO. 12163    77-SerLeuAspAspLysThrValArg-84
SEQ. ID. NO. 12164    106-GlySerAsnAsnLeuSerArgLeuGlnLysAlaAla-117
SEQ. ID. NO. 12165    135-ProGlnAsnMetAspSerGlyIleLeu-143
SEQ. ID. NO. 12166    146-ArgValSerAlaGlyGluIleGlyAspIleArgTyrGluGluLysArgAspGlyLysSerAlaGluGlySerIle-170
SEQ. ID. NO. 12167    178-ProLeuTyrArgAsnLysIleLeuAsn-186
SEQ. ID. NO. 12168    188-ArgAspValGluGlnGlyLeuGluAsnLeuArgArgLeuProSerValLysThrAspIle-207
SEQ. ID. NO. 12169    210-IleProSerGluGluGluGlyLysSerAspLeu-220
SEQ. ID. NO. 12170    223-LysTrpGlnGlnAsnLysProIleArg-231
SEQ. ID. NO. 12171    234-IleGlyIleAspAspAlaGlyGlyLysThrThrGlyLysTyrGlnGly-249
SEQ. ID. NO. 12172    256-AspAsnProLeuGly-260
SEQ. ID. NO. 12173    269-TyrGlyArgGlyLeuAlaHisLysThrAspLeuThrAspAlaThrGlyThrGluThrGluSerGlySerArgSerTyr-294
SEQ. ID. NO. 12174    309-PheAsnHisAsnGlyHisArgTyrHisGluAlaThrGluGlyTyrSerValAsnTyrAspTyrAsnGlyLysGlnTyrGln-335
SEQ. ID. NO. 12175    343-MetLeuTrpArgAsnArgLeuHisLysThrSerVal-354
SEQ. ID. NO. 12176    362-GlnThrTyrLysTyrIleAspAspAlaGluIleGluValGlnArgArgArgSerAlaGlyTrpGluAlaGluLeuArgHis-388
SEQ. ID. NO. 12177    395-TrpGlnLeuAspGlyLysLeuSerTyrLysArgGlyThrGlyMetArgGlnSerMetProAlaProGluGluAsnGlyGlyAspIleLeuProGlyThrSerArgMetLysIle-432
SEQ. ID. NO. 12178    459-GlnTrpAsnLysThrPro-464
SEQ. ID. NO. 12179    467-AlaGlnAspLysLeuSerIleGlySerArgTyrThrValArgGlyPheAspGlyGluGlnSerLeuPheGlyGluArgGlyPheTyrTrpGlnAsnThr-499
SEQ. ID. NO. 12180    514-AlaAspTyrGlyArgValSerGlyGluSerAla-524
SEQ. ID. NO. 12181    527-ValSerGlyLysGln-531
SEQ. ID. NO. 12182    539-PheArgGlyGlyHisLysValGly-546
SEQ. ID. NO. 12183    557-LysProLeuHisLysProLysGlyPheGln-566
Hydrophilic Regions - Hopp-Woods
SEQ. ID. NO. 12184    21-LeuAlaAlaAspGluAsnAspAlaGluLeuIleArgSerMetGlnArgGlnGlnHisIleAsp-41
SEQ. ID. NO. 12185    48-AlaAsnValArgPheGluGlnProLeuGluLysAsnAsn-60
SEQ. ID. NO. 12186    63-LeuSerGluAspGluThrProCys-70
SEQ. ID. NO. 12187    77-SerLeuAspAspLysThrValArg-84
SEQ. ID. NO. 12188    109-AsnLeuSerArgLeuGlnLysAlaAla-117
SEQ. ID. NO. 12189    151-GluIleGlyAspIleArgTyrGluGluLysArgAspGlyLysSerAlaGluGlySer-169
SEQ. ID. NO. 12190    188-ArgAspValGluGlnGlyLeuGluAsnLeuArgArgLeuProSerValLysThrAspIle-207
SEQ. ID. NO. 12191    211-ProSerGluGluGluGlyLysSerAspLeu-220
SEQ. ID. NO. 12192    234-IleGlyIleAspAspAlaGlyGlyLysThrThrGlyLysTyr-247
SEQ. ID. NO. 12193    273-LeuAlaHisLysThrAspLeuThrAsp-281
SEQ. ID. NO. 12194    283-ThrGlyThrGluThrGluSerGlySerArgSer-293
SEQ. ID. NO. 12195    315-ArgTyrHisGluAlaThrGlu-321
SEQ. ID. NO. 12196    366-TyrIleAspAspAlaGluIleGluValGlnArgArgArgSerAlaGlyTrp-382
SEQ. ID. NO. 12197    384-AlaGluLeuArgHis-388
SEQ. ID. NO. 12198    399-GlyLysLeuSerTyrLysArgGlyThrGlyMetArgGlnSerMetProAlaProGluGluAsnGlyGly-421
SEQ. ID. NO. 12199    428-SerArgMetLysIle-432
SEQ. ID. NO. 12200    467-AlaGlnAspLysLeuSerIle-473
SEQ. ID. NO. 12201    481-GlyPheAspGlyGluGln-486
SEQ. ID. NO. 12202    515-AspTyrGlyArgValSerGlyGluSer-523
SEQ. ID. NO. 12203    558-ProLeuHisLysProLysGly-564
904-2
AMPHI Regions - AMPHI
SEQ. ID. NO. 12204    23-AspPhePheAsnProPheGlnIleCysPheGlyValPheGlyGlnCysAla-39
SEQ. ID. NO. 12205    55-PheValAsnArgLeuAlaGlyPheHisArgIleGly-66
SEQ. ID. NO. 12206    89-PheAsnAlaValHisTyrIleGluPhe-97
SEQ. ID. NO. 12207    131-GluPheValSerAlaPheCysGlnThrTyr-140
SEQ. ID. NO. 12208    164-AlaGlnAsnIleIleGlnHisLeuArgThrTyrAlaArgAlaCysArgSerCysAlaArgGln-184

TABLE 1-continued

| | |
|---|---|
| SEQ. ID. NO. 12209 | 193-IleSerAlaValValAspVal-199 |
| SEQ. ID. NO. 12210 | 202-ArgThrLeuArgAlaPhe-207 |
| SEQ. ID. NO. 12211 | 250-GlyIleValGlnMetLeu-255 |
| SEQ. ID. NO. 12212 | 267-GlnPhePheThrGlnPhePheArgMetGlnGlnIleGlyGlyAlaAsn-282 |
| SEQ. ID. NO. 12213 | 308-ArgCysPheAlaGlyLeuValGlu-315 |
| SEQ. ID. NO. 12214 | 332-ThrAlaPheAspValPheHisAlaCys-340 |
| SEQ. ID. NO. 12215 | 364-ValGlnThrPheMetGlnAspAla-371 |
| SEQ. ID. NO. 12216 | 390-ArgIleValAlaAlaLeu-395 |
| SEQ. ID. NO. 12217 | 402-GlyPhePheArgGlnProValAsn-409 |
| SEQ. ID. NO. 12218 | 418-ProLeuCysAlaAspTyrTyrAsnIlePheSerHis-429 |
| Antigenic Index - Jameson-Wolf | |
| SEQ. ID. NO. 12219 | 11-GlyAlaGlyGlyAspAspGlyAspArgArgAlaAlaAsp-23 |
| SEQ. ID. NO. 12220 | 66-GlyThrAlaArgGlnAspVal-72 |
| SEQ. ID. NO. 12221 | 84-AlaAspIleAspGly-88 |
| SEQ. ID. NO. 12222 | 98-SerAsnThrHisThrGlyAsn-104 |
| SEQ. ID. NO. 12223 | 106-ValAspLeuAspGly-110 |
| SEQ. ID. NO. 12224 | 114-GlyGlyGlyIleLys-118 |
| SEQ. ID. NO. 12225 | 126-SerGlyTyrArgThrGluPhe-132 |
| SEQ. ID. NO. 12226 | 147-PheGlyArgGluArgAlaArgThrAspAlaArgGlyIleGlyPheAspAspAlaGln-165 |
| SEQ. ID. NO. 12227 | 173-ThrTyrAlaArgAlaCysArgSerCysAlaArgGlnThrValGlyArgGlyAsnGluGlyIle-193 |
| SEQ. ID. NO. 12228 | 199-ValGlnGlnArgThrLeuArgAlaPheLys-208 |
| SEQ. ID. NO. 12229 | 224-HisValGlyAsnHisArgArgAsnAlaArgArgAspPhePheAspAsnArgHisHis-242 |
| SEQ. ID. NO. 12230 | 261-IleGlyLysAspGlyIle-266 |
| SEQ. ID. NO. 12231 | 279-GlyGlyAlaAsnGly-283 |
| SEQ. ID. NO. 12232 | 293-ArgAlaAspAlaAlaAlaGlyArgAla-301 |
| SEQ. ID. NO. 12233 | 314-ValGluArgAspValValArgGlnAspGlnArgAlaGlyArgArgAspPheGlnThr-332 |
| SEQ. ID. NO. 12234 | 351-GlyPheGlyGlyAspAspAsnAlaArgThrAspGluAlaVal-364 |
| SEQ. ID. NO. 12235 | 370-AspAlaAlaArgAsnGlnAlaGlnAsnGly-379 |
| SEQ. ID. NO. 12236 | 384-AspAsnGlnGlyMet-388 |
| SEQ. ID. NO. 12237 | 407-ProValAsnAspPhe-411 |
| Hydrophilic Regions - Hopp-Woods | |
| SEQ. ID. NO. 12238 | 12-AlaGlyGlyAspAspGlyAspArgArgAlaAlaAsp-23 |
| SEQ. ID. NO. 12239 | 66-GlyThrAlaArgGlnAspVal-72 |
| SEQ. ID. NO. 12240 | 84-AlaAspIleAspGly-88 |
| SEQ. ID. NO. 12241 | 147-PheGlyArgGluArgAlaArgThrAspAlaArgGlyIleGlyPheAspAspAlaGln-165 |
| SEQ. ID. NO. 12242 | 173-ThrTyrAlaArgAlaCysArgSerCysAlaArg-183 |
| SEQ. ID. NO. 12243 | 185-ThrValGlyArgGlyAsnGluGly-192 |
| SEQ. ID. NO. 12244 | 199-ValGlnGlnArgThrLeuArgAlaPheLys-208 |
| SEQ. ID. NO. 12245 | 226-GlyAsnHisArgArgAsnAlaArgArgAspPhePheAspAsnArgHisHis-242 |
| SEQ. ID. NO. 12246 | 261-IleGlyLysAspGly-265 |
| SEQ. ID. NO. 12247 | 293-ArgAlaAspAlaAlaAlaGlyArgAla-301 |
| SEQ. ID. NO. 12248 | 314-ValGluArgAspValValArgGlnAspGlnArgAlaGlyArgArgAspPheGlnThr-332 |
| SEQ. ID. NO. 12249 | 352-PheGlyGlyAspAspAsnAlaArgThrAspGluAlaVal-364 |
| SEQ. ID. NO. 12250 | 370-AspAlaAlaArgAsnGlnAla-376 |
| 907-2 | |
| AMPHI Regions - AMPHI | |
| SEQ. ID. NO. 12251 | 42-AspAspValAlaSerValMetArgSer-50 |
| SEQ. ID. NO. 12252 | 66-LysGluGlyGluArgTrpLeuSerAlaMetSer-76 |
| SEQ. ID. NO. 12253 | 78-ArgLeuAlaArgPheVal-83 |
| SEQ. ID. NO. 12254 | 129-GlyAlaArgGlyLeu-133 |
| SEQ. ID. NO. 12255 | 142-AsnTyrIleGlyLysProAlaHis-149 |
| SEQ. ID. NO. 12256 | 165-LeuArgHisTyrArgAsnLeuGluLysGlyAsn-175 |
| SEQ. ID. NO. 12257 | 177-ValArgAlaLeuAlaArgPheAsnGly-185 |
| Antigenic Index - Jameson-Wolf | |
| SEQ. ID. NO. 12258 | 1-MetArgLysProThrAspThrLeuPro-9 |
| SEQ. ID. NO. 12259 | 12-LeuGlnArgArgArgLeuLeu-18 |
| SEQ. ID. NO. 12260 | 33-GlyAlaGlnArgGluGluThrLeuAlaAspAspValAlaSer-46 |
| SEQ. ID. NO. 12261 | 51-SerValGlySerValAsnProProArgLeuValPheAspAsnProLysGluGlyGluArgTrp-71 |
| SEQ. ID. NO. 12262 | 83-ValProGluGluGluGluArgArgArgLeu-92 |
| SEQ. ID. NO. 12263 | 97-GlnTyrGluSerSerArgAlaGlyLeu-105 |
| SEQ. ID. NO. 12264 | 115-GluValGluSerAlaPhe-120 |
| SEQ. ID. NO. 12265 | 142-AsnTyrIleGlyLysProAlaHisAsn-150 |
| SEQ. ID. NO. 12266 | 155-ArgThrAsnLeuArgTyrGly-161 |
| SEQ. ID. NO. 12267 | 168-TyrArgAsnLeuGluLysGlyAsnIle-176 |
| SEQ. ID. NO. 12268 | 184-AsnGlySerLeuGlySerAsnLysTyrProAsnAla-195 |
| SEQ. ID. NO. 12269 | 200-TrpArgAsnArgTrpGlnTrp-206 |
| Hydrophilic Regions - Hopp-Woods | |
| SEQ. ID. NO. 12270 | 1-MetArgLysProThrAsp-6 |
| SEQ. ID. NO. 12271 | 12-LeuGlnArgArgArgLeuLeu-18 |
| SEQ. ID. NO. 12272 | 33-GlyAlaGlnArgGluGluThrLeuAlaAspAspValAlaSer-46 |
| SEQ. ID. NO. 12273 | 60-LeuValPheAspAsnProLysGluGlyGluArgTrp-71 |
| SEQ. ID. NO. 12274 | 83-ValProGluGluGluGluArgArgArgLeu-92 |
| SEQ. ID. NO. 12275 | 99-GluSerSerArgAlaGlyLeu-105 |
| SEQ. ID. NO. 12276 | 115-GluValGluSerAlaPhe-120 |
| SEQ. ID. NO. 12277 | 169-ArgAsnLeuGluLysGlyAsnIle-176 |
| 908-2 | |
| AMPHI Regions - AMPHI | |
| SEQ. ID. NO. 12278 | 9-TyrLysGlnAsnLys-13 |
| SEQ. ID. NO. 12279 | 26-ThrAlaAlaGluLeu-30 |
| SEQ. ID. NO. 12280 | 127-ThrAspCysTyrArgSerTyrAspValLeuAspValArgGluPheSerHisPheSer-145 |

TABLE 1-continued

```
Antigenic Index - Jameson-Wolf
SEQ. ID. NO. 12281    1-MetArgLysSerArgLeuSerArgTyrLysGlnAsnLysLeu-14
SEQ. ID. NO. 12282    51-GlnAsnSerProHis-55
SEQ. ID. NO. 12283    59-PheAspGlyGluValGluAlaAspGluSerTyrPheGlyGlyGlnArgLysGlyLysArgGlyArgGlyAlaAlaGly-84
SEQ. ID. NO. 12284    91-LeuLeuLysArgAsnGlyLysVal-98
SEQ. ID. NO. 12285    115-IleArgGluGlnValLysProAspSerIleVal-125
SEQ. ID. NO. 12286    127-ThrAspCysTyrArgSerTyrAsp-134
SEQ. ID. NO. 12287    136-LeuAspValArgGlu-140
SEQ. ID. NO. 12288    161-ArgThrThrLysProTyr-166
Hydrophilic Regions - Hopp-Woods
SEQ. ID. NO. 12289    1-MetArgLysSerArgLeuSerArgTyrLysGlnAsnLysLeu-14
SEQ. ID. NO. 12290    59-PheAspGlyGluValGluAlaAspGluSerTyr-69
SEQ. ID. NO. 12291    72-GlyGlnArgLysGlyLysArgGlyArgGlyAlaAlaGly-84
SEQ. ID. NO. 12292    92-LeuLysArgAsnGlyLys-97
SEQ. ID. NO. 12293    115-IleArgGluGlnValLysProAspSer-123
SEQ. ID. NO. 12294    136-LeuAspValArgGlu-140
909
AMPHI Regions - AMPHI
SEQ. ID. NO. 12295    71-GlyAsnAsnAlaAspGlu-76
Antigenic Index - Jameson-Wolf
SEQ. ID. NO. 12296    22-ThrTyrGlnAspGlyAsnGlyLysThrAlaValArgGlnLysTyrProAlaGly-39
SEQ. ID. NO. 12297    45-GlnAspGlySerTyrSerLysAsnMetAsnTyrAsnGlnTyrArgProGluArgHisAla-64
SEQ. ID. NO. 12298    68-AsnGlnThrGlyAsnAsnAlaAspGluGluHisArgGlnHisTrpGlnLysProLysPheGlnAsnArg-90
Hydrophilic Regions - Hopp-Woods
SEQ. ID. NO. 12299    23-TyrGlnAspGlyAsnGlyLysThrAlaValArgGlnLysTyr-36
SEQ. ID. NO. 12300    58-TyrArgProGluArgHisAla-64
SEQ. ID. NO. 12301    72-AsnAsnAlaAspGluGluHisArgGlnHisTrpGln-83
SEQ. ID. NO. 12302    85-ProLysPheGlnAsnArg-90
910
AMPHI Regions - AMPHI
SEQ. ID. NO. 12303    10-ValSerLeuSerAlaAla-15
SEQ. ID. NO. 12304    22-SerAlaGluArgGlnIle-27
SEQ. ID. NO. 12305    39-LysAlaValLysMetLeuGlu-45
SEQ. ID. NO. 12306    58-AspHisTrpGlyLysPro-63
SEQ. ID. NO. 12307    69-AlaTyrLysAspGlyArg-74
Antigenic Index - Jameson-Wolf
SEQ. ID. NO. 12308    19-AlaGlyAspSerAlaGluArgGlnIleTyrGlyAspProHisPheGluGlnAsnArgThrLysAlaValLysMetLeuGluGlnArgGlyTyrGln-50
SEQ. ID. NO. 12309    53-AspValAspAlaAspAspHisTrpGlyLysProValLeuGlu-66
SEQ. ID. NO. 12310    68-GluAlaTyrLysAspGlyArgGluTyrAsp-77
SEQ. ID. NO. 12311    83-ProAspLeuLysIleIleLysGluGlnLeuAspArg-94
Hydrophilic Regions - Hopp-Woods
SEQ. ID. NO. 12312    21-AspSerAlaGluArgGlnIleTyr-28
SEQ. ID. NO. 12313    31-ProHisPheGluGlnAsnArgThrLysAlaValLysMetLeuGluGlnArgGly-48
SEQ. ID. NO. 12314    53-AspValAspAlaAspAspHisTrpGly-61
SEQ. ID. NO. 12315    68-GluAlaTyrLysAspGlyArgGluTyrAsp-77
SEQ. ID. NO. 12316    86-LysIleIleLysGluGlnLeuAspArg-94
911
AMPHI Regions - AMPHI
SEQ. ID. NO. 12317    6-LeuGluPheTrpValGlyLeuPhe-13
SEQ. ID. NO. 12318    43-ValTyrAlaAspPheGlyAspIleGly-51
SEQ. ID. NO. 12319    97-ValSerAlaGlnIle-101
SEQ. ID. NO. 12320    118-GlyAspThrGluAsnLeuAla-124
SEQ. ID. NO. 12321    140-AsnLeuIleGlyLysPheMetThrSerPhe-149
Antigenic Index - Jameson-Wolf
SEQ. ID. NO. 12322    1-MetLysLysAsnIle-5
SEQ. ID. NO. 12323    35-GlyGlySerAspLysThrTyr-41
SEQ. ID. NO. 12324    48-GlyAspIleGlyGlyLeuLysValAsnAlaProValLys-60
SEQ. ID. NO. 12325    74-LeuAspProLysSerTyrGlnAlaArgValArgLeuAspLeuAspGlyLysTyrGlnPheSerSerAspVal-97
SEQ. ID. NO. 12326    103-ThrSerGlyLeuLeuGly-108
SEQ. ID. NO. 12327    115-GlnGlnGlyGlyAspThrGluAsn-122
SEQ. ID. NO. 12328    149-PheAlaGluLysAsnAlaAspGlyGlyAsnAlaGluLysAlaAlaGlu-164
Hydrophilic Regions - Hopp-Woods
SEQ. ID. NO. 12329    1-MetLysLysAsnIle-5
SEQ. ID. NO. 12330    36-GlySerAspLysThr-40
SEQ. ID. NO. 12331    74-LeuAspProLysSerTyrGlnAlaArgValArgLeuAspLeuAspGly-89
SEQ. ID. NO. 12332    116-GlnGlyGlyAspThrGluAsn-122
SEQ. ID. NO. 12333    149-PheAlaGluLysAsnAlaAspGlyGlyAsnAlaGluLysAlaAlaGlu-164
912
AMPHI Regions - AMPHI
SEQ. ID. NO. 12334    24-ProAlaAspAlaValSerGlnIle-31
SEQ. ID. NO. 12335    62-PheAspPheGlnArgMetThrAlaLeuAlaValGlyAsnProTrpArgThrAlaSerAspAlaGlnLys-84
SEQ. ID. NO. 12336    89-LysGluPheGlnThrLeu-94
SEQ. ID. NO. 12337    169-TyrArgAsnGlnPheGlyGluIleIleLysAlaLys-180
Antigenic Index - Jameson-Wolf
SEQ. ID. NO. 12338    1-MetLysLysSerSer-5
SEQ. ID. NO. 12339    29-SerGlnIleArgGlnAsnAlaThrGln-37
SEQ. ID. NO. 12340    42-LeuLysAsnGlyAspAlaAsnThrAlaArgGlnLysAlaGluAla-56
SEQ. ID. NO. 12341    74-AsnProTrpArgThrAlaSerAspAlaGlnLysGlnAlaLeuAlaLysGluPhe-91
SEQ. ID. NO. 12342    104-LeuLysLeuLysAsnAlaAsnValAsnValLysAspAsnProIleValAsnLysGlyGlyLysGluIleIleVal-128
SEQ. ID. NO. 12343    130-AlaGluValGlyValProGlyGlnLysProValAsn-141
```

TABLE 1-continued

| | |
|---|---|
| SEQ. ID. NO. 12344 | 146-ThrTyrGlnSerGlyGlyLysTyrArgThr-155 |
| SEQ. ID. NO. 12345 | 169-TyrArgAsnGlnPhe-173 |
| SEQ. ID. NO. 12346 | 177-IleLysAlaLysGlyValAspGlyLeuIleAla-187 |
| SEQ. ID. NO. 12347 | 189-LeuLysAlaLysAsnGlyGlyLys-196 |

Hydrophilic Regions - Hopp-Woods

| | |
|---|---|
| SEQ. ID. NO. 12348 | 1-MetLysLysSerSer-5 |
| SEQ. ID. NO. 12349 | 31-IleArgGlnAsnAla-35 |
| SEQ. ID. NO. 12350 | 43-LysAsnGlyAspAlaAsnThrAlaArgGlnLysAlaGluAla-56 |
| SEQ. ID. NO. 12351 | 78-ThrAlaSerAspAlaGlnLysGlnAlaLeuAlaLysGluPhe-91 |
| SEQ. ID. NO. 12352 | 104-LeuLysLeuLysAsn-108 |
| SEQ. ID. NO. 12353 | 110-AsnValAsnValLysAspAsnProIleVal-119 |
| SEQ. ID. NO. 12354 | 121-LysGlyGlyLysGluIleIleVal-128 |
| SEQ. ID. NO. 12355 | 134-ValProGlyGlnLysProValAsn-141 |
| SEQ. ID. NO. 12356 | 177-IleLysAlaLysGlyValAsp-183 |
| SEQ. ID. NO. 12357 | 189-LeuLysAlaLysAsnGlyGlyLys-196 |

913
AMPHI Regions - AMPHI

| | |
|---|---|
| SEQ. ID. NO. 12358 | 22-GluThrArgProAlaAspProTyrGluGlyTyrAsnArg-34 |
| SEQ. ID. NO. 12359 | 53-ArgGlyTyrArgLysValAlaProLys-61 |
| SEQ. ID. NO. 12360 | 66-GlyValSerAsnPhePheAsnAsnLeuCysAspValValSer-79 |
| SEQ. ID. NO. 12361 | 107-LeuGlyGlyLeuIleAspIleAlaGlyAla-116 |
| SEQ. ID. NO. 12362 | 151-ValArgAspAlaLeuGlyThrGlyIleThrSerValTyrSer-164 |
| SEQ. ID. NO. 12363 | 193-AspLeuThrAspSerLeuAspGluAlaAla-202 |
| SEQ. ID. NO. 12364 | 238-LeuValGluSerAla-242 |
| SEQ. ID. NO. 12365 | 257-SerGluThrGlnAla-261 |

Antigenic Index - Jameson-Wolf

| | |
|---|---|
| SEQ. ID. NO. 12366 | 21-AlaGluThrArgProAlaAspProTyrGluGlyTyrAsn-33 |
| SEQ. ID. NO. 12367 | 39-PheAsnAspGlnAlaAspArgTyr-46 |
| SEQ. ID. NO. 12368 | 51-AlaAlaArgGlyTyrArgLysValAlaProLysProValArgAla-65 |
| SEQ. ID. NO. 12369 | 81-GlySerAsnIleLeu-85 |
| SEQ. ID. NO. 12370 | 87-LeuAspIleLysArgAlaSerGluAspLeuVal-97 |
| SEQ. ID. NO. 12371 | 117-GlyGlyIleProAspAsnLysAsnThrLeuGlyAsp-128 |
| SEQ. ID. NO. 12372 | 132-SerTrpGlyTrpLysAsnSerAsn-139 |
| SEQ. ID. NO. 12373 | 149-SerThrValArgAspAlaLeu-155 |
| SEQ. ID. NO. 12374 | 163-TyrSerProLysAsnIle-168 |
| SEQ. ID. NO. 12375 | 172-ThrProValGlyArgTrpGly-178 |
| SEQ. ID. NO. 12376 | 185-ValSerThrArgGluGlyLeuLeuAspLeuThrAspSerLeuAspGluAlaAlaIleAspLysTyrSerTyrThrArgAspLeuTyrMet-214 |
| SEQ. ID. NO. 12377 | 216-ValArgAlaArgGlnThrGlyAlaThrProAlaGluGlyThrGluAspAsnIleAspIleAspGluLeuValGluSerAlaGluThrGlyAlaAla-247 |
| SEQ. ID. NO. 12378 | 250-AlaValGlnGluAspSerValSerGluThrGlnAlaGluAlaAlaGlyGluAlaGluThrGlnProGlyThrGlnPro-275 |

Hydrophilic Regions - Hopp-Woods

| | |
|---|---|
| SEQ. ID. NO. 12379 | 21-AlaGluThrArgProAlaAspProTyrGluGlyTyrAsn-33 |
| SEQ. ID. NO. 12380 | 40-AsnAspGlnAlaAsp-44 |
| SEQ. ID. NO. 12381 | 53-ArgGlyTyrArgLysValAlaProLysProValArg-64 |
| SEQ. ID. NO. 12382 | 87-LeuAspIleLysArgAlaSerGluAspLeuVal-97 |
| SEQ. ID. NO. 12383 | 118-GlyIleProAspAsnLysAsnThrLeu-126 |
| SEQ. ID. NO. 12384 | 150-ThrValArgAspAlaLeu-155 |
| SEQ. ID. NO. 12385 | 186-SerThrArgGluGlyLeuLeuAspLeuThrAspSerLeuAspGluAlaAlaIleAsp-204 |
| SEQ. ID. NO. 12386 | 216-ValArgAlaArgGlnThrGly-222 |
| SEQ. ID. NO. 12387 | 224-ThrProAlaGluGlyThrGluAspAsnIleAspIleAspGluLeuValGluSerAlaGluThrGlyAlaAla-247 |
| SEQ. ID. NO. 12388 | 250-AlaValGlnGluAspSerValSerGluThrGlnAlaGluAlaAlaGlyGluAlaGluThrGlnPro-271 |

914-2
AMPHI Regions - AMPHI

| | |
|---|---|
| SEQ. ID. NO. 12389 | 6-LeuGlyIleLeuThrAlaCysAlaAlaMet-15 |
| SEQ. ID. NO. 12390 | 17-AlaPheAlaAspArgIleGlyAspLeu-25 |
| SEQ. ID. NO. 12391 | 65-PheGlnLysThrPheGlu-70 |
| SEQ. ID. NO. 12392 | 81-GlnLysValArgGlnAlaCys-87 |

Antigenic Index - Jameson-Wolf

| | |
|---|---|
| SEQ. ID. NO. 12393 | 18-PheAlaAspArgIleGlyAspLeuGluAlaArgLeuAlaGlnLeuGluHisArgValAlaValLeuGluSerGlyGlyAsnThrValLys-47 |
| SEQ. ID. NO. 12394 | 50-LeuPheGlySerAsnSer-55 |
| SEQ. ID. NO. 12395 | 64-ProPheGlnLysThrPheGluAlaSerAspArgAsnGluGlyValAlaArgGlnLysValArgGlnAlaCysAsnArgGluThrSerAla-93 |
| SEQ. ID. NO. 12396 | 95-PheCysGluAspGluAlaIleArgCysArgLysPheAsp-107 |

Hydrophilic Regions - Hopp-Woods

| | |
|---|---|
| SEQ. ID. NO. 12397 | 18-PheAlaAspArgIleGlyAspLeuGluAlaArgLeuAlaGlnLeuGluHisArgValAlaVal-38 |
| SEQ. ID. NO. 12398 | 67-LysThrPheGluAlaSerAspArgAsnGluGlyValAlaArgGlnLysValArgGlnAlaCysAsnArgGluThrSer-92 |
| SEQ. ID. NO. 12399 | 95-PheCysGluAspGluAlaIleArgCysArgLysPheAsp-107 |

915-2
AMPHI Regions - AMPHI

| | |
|---|---|
| SEQ. ID. NO. 12400 | 9-ValAlaValSerAlaLeuSerAlaCysArgGlnAla-20 |
| SEQ. ID. NO. 12401 | 31-IleSerAspArgSerVal-36 |
| SEQ. ID. NO. 12402 | 67-SerThrIleLysGlnMetPheGlyTyrThrLysLeuProGluGluProLysGlyIleArgValIleTyrValThrAspMetGlyAsnValThrAspTrpThr-100 |
| SEQ. ID. NO. 12403 | 139-GlnAlaGluLysPhe-143 |

Antigenic Index - Jameson-Wolf

| | |
|---|---|
| SEQ. ID. NO. 12404 | 15-SerAlaCysArgGlnAlaGluGluGlyProProProLeuProArgGlnIleSerAspArgSerValGlyHis-38 |
| SEQ. ID. NO. 12405 | 43-AsnLeuThrGluHisAsnGlyProLysAla-52 |
| SEQ. ID. NO. 12406 | 57-AsnGlyLysProAspGlnProVal-64 |
| SEQ. ID. NO. 12407 | 75-TyrThrLysLeuProGluGluProLysGlyIle-85 |
| SEQ. ID. NO. 12408 | 97-ThrAspTrpThrAsnProAsnAlaAspThrGluTrpMetAspAlaLysLys-113 |
| SEQ. ID. NO. 12409 | 125-GlyMetGlyAlaGluAlaAlaLeuProPheGlyAsnLysGluGlnAlaGluLysPheAlaLysAspLysGlyGlyLysValValGlyPheAspAspMetProAspThrTyr-161 |

TABLE 1-continued

Hydrophilic Regions - Hopp-Woods
SEQ. ID. NO. 12410   18-ArgGlnAlaGluGluGlyProProProLeu-27
SEQ. ID. NO. 12411   30-GlnIleSerAspArgSerVal-36
SEQ. ID. NO. 12412   46-GluHisAsnGlyProLys-51
SEQ. ID. NO. 12413   58-GlyLysProAspGln-62
SEQ. ID. NO. 12414   77-LysLeuProGluGluProLysGlyIle-85
SEQ. ID. NO. 12415   103-AsnAlaAspThrGluTrpMetAspAlaLysLys-113
SEQ. ID. NO. 12416   127-GlyAlaGluAspAlaLeu-132
SEQ. ID. NO. 12417   135-GlyAsnLysGluGlnAlaGluLysPheAlaLysAspLysGlyGlyLys-150
SEQ. ID. NO. 12418   155-AspAspMetProAsp-159
917
AMPHI Regions - AMPHI
SEQ. ID. NO. 12419   6-ProLeuAlaValLeuThrAlaLeuLeuLeu-15
SEQ. ID. NO. 12420   35-GlnAsnValLeuLysIleTyrAsnTrpSerGluTyrValAspProGluThrValAlaAsp-54
SEQ. ID. NO. 12421   99-IleLysAlaGlyAlaTyrGlnLysIleAspLysSerLeu-111
SEQ. ID. NO. 12422   124-ArgLeuMetAspGlyValAspPro-131
SEQ. ID. NO. 12423   152-ArgValLysLysAlaLeu-157
SEQ. ID. NO. 12424   188-AspSerAlaAlaGlu-192
SEQ. ID. NO. 12425   206-AsnSerSerAsnThrGluAspIleArgGluAlaThr-217
SEQ. ID. NO. 12426   292-AlaLysAsnValAlaAsnAlaHisLysTyrIleAsnAspPheLeuAsp-307
SEQ. ID. NO. 12427   325-LysProAlaArgGluLeuMetGluAsp-333
Antigenic Index - Jameson-Wolf
SEQ. ID. NO. 12428   18-CysGlyGlySerAspLysProProAlaGluLysProAlaProAlaGluAsnGlnAsnVal-37
SEQ. ID. NO. 12429   44-SerGluTyrValAspProGluThrValAlaAspPheGluLysLysAsnGlyIleLysValThr-64
SEQ. ID. NO. 12430   68-TyrAspSerAspGluThrLeuGluSerLysValLeuThrGlyLysSerGlyTyrAsp-86
SEQ. ID. NO. 12431   102-GlyAlaTyrGlnLysIleAspLysSerLeuIleProAsnTyrLysHisLeuAsnProGluMetMetArgLeuMetAspGlyValAspProGlyHisGluTyr-135
SEQ. ID. NO. 12432   149-AsnThrGluArgValLysLysAlaLeuGlyThrAspLysLeuProAspAsnGln-166
SEQ. ID. NO. 12433   171-PheAspProGluTyrThrSerLysLeuLysGlnCysGly-183
SEQ. ID. NO. 12434   201-LeuGlyLysAsnProAsnSerSerAsnThrGluAspIleArgGluAlaThrAlaLeuLeuLysLysAsnArgProAsnIleLysArgPheThrSerSerGlyPheIle-236
SEQ. ID. NO. 12435   238-AspLeuAlaArgGlyAspThr-244
SEQ. ID. NO. 12436   255-AsnIleAlaLysArgArgAlaGluGluAlaGlyGlyLysGluLysIleArgValMetMetProLysGluGlyValGly-280
SEQ. ID. NO. 12437   287-ValIleProLysAspAlaLysAsnValAlaAsn-297
SEQ. ID. NO. 12438   305-PheLeuAspProGluValSerAlaLysAsnGlyAsn-316
SEQ. ID. NO. 12439   320-TyrAlaProSerSerLysProAlaArgGluLeuMetGluAspGluPheLysAsnAspAsnThrIlePheProThrGluGluAspLeuLysAsn-350
SEQ. ID. NO. 12440   368-GlnTrpGlnAspValLysAlaGlyLys-376
Hydrophilic Regions - Hopp-Woods
SEQ. ID. NO. 12441   19-GlyGlySerAspLysProProAlaGluLysProAlaProAlaGluAsn-34
SEQ. ID. NO. 12442   47-ValAspProGluThrValAlaAspPheGluLysLysAsnGlyIle-61
SEQ. ID. NO. 12443   68-TyrAspSerAspGluThrLeuGluSerLysValLeuThr-80
SEQ. ID. NO. 12444   105-GlnLysIleAspLysSerLeu-111
SEQ. ID. NO. 12445   121-GluMetMetArgLeuMetAspGlyValAspProGlyHis-133
SEQ. ID. NO. 12446   149-AsnThrGluArgValLysLysAlaLeuGlyThrAspLysLeuProAspAsnGln-166
SEQ. ID. NO. 12447   174-GluTyrThrSerLysLeuLysGln-181
SEQ. ID. NO. 12448   204-AsnProAsnSerSerAsnThrGluAspIleArgGluAlaThrAlaLeuLeuLysLysAsnArgProAsnIleLysArgPheThr-231
SEQ. ID. NO. 12449   238-AspLeuAlaArgGlyAspThr-244
SEQ. ID. NO. 12450   255-AsnIleAlaLysArgArgAlaGluGluAlaGlyGlyLysGluLysIleArgValMetMetProLysGluGly-278
SEQ. ID. NO. 12451   290-LysAspAlaLysAsnValAlaAsn-297
SEQ. ID. NO. 12452   305-PheLeuAspProGluValSerAlaLysAsn-314
SEQ. ID. NO. 12453   322-ProSerSerLysProAlaArgGluLeuMetGluAspGluPheLysAsnAspAsn-339
SEQ. ID. NO. 12454   343-ProThrGluGluAspLeuLysAsn-350
SEQ. ID. NO. 12455   370-GlnAspValLysAlaGlyLys-376
919
AMPHI Regions - AMPHI
SEQ. ID. NO. 12456   12-GlyIleAlaAlaAlaIleLeu-18
SEQ. ID. NO. 12457   24-LysSerIleGlnThrPheProGln-31
SEQ. ID. NO. 12458   37-IleAsnGlyProAspArgProValGlyIleProAsp-48
SEQ. ID. NO. 12459   76-AspPheAlaLysSerLeuGln-82
SEQ. ID. NO. 12460   98-GlnAspValCysAlaGlnAlaPheGlnThrProVal-109
SEQ. ID. NO. 12461   119-GluArgTyrPheThr-123
SEQ. ID. NO. 12462   133-LeuAlaGlyThrValThrGlyTyrTyrGlu-142
SEQ. ID. NO. 12463   161-GlyIleProAspPheIleSerValPro-170
SEQ. ID. NO. 12464   176-ArgSerGlyLysAlaLeuValArgIleArgGln-186
SEQ. ID. NO. 12465   191-SerGlyThrIleAspAsnThrGlyGlyThr-200
SEQ. ID. NO. 12466   307-MetGlnGlyIleLysSerTyrMetArgGlnAsnProGlnArgLeuAlaGluValLeu-325
SEQ. ID. NO. 12467   348-AlaLeuGlyThrProLeuMetGlyGluTyrAlaGlyAlaVal-361
SEQ. ID. NO. 12468   382-ArgLysAlaLeuAsnArg-387
Antigenic Index - Jameson-Wolf
SEQ. ID. NO. 12469   21-CysGlnSerLysSerIleGlnThr-28
SEQ. ID. NO. 12470   30-ProGlnProAspThr-34
SEQ. ID. NO. 12471   36-ValIleAsnGlyProAspArgProValGlyIleProAspProAlaGlyThr-52
SEQ. ID. NO. 12472   54-ValGlyGlyGlyGly-58
SEQ. ID. NO. 12473   76-AspPheAlaLysSerLeuGln-82
SEQ. ID. NO. 12474   87-GlyCysAlaAsnLeuLysAsnArgGlnGlyTrpGln-98
SEQ. ID. NO. 12475   121-TyrPheThrProTrp-125
SEQ. ID. NO. 12476   143-ProValLeuLysGlyAspAspArgArgThrAlaGln-154
SEQ. ID. NO. 12477   162-IleProAspAspPheIle-167
SEQ. ID. NO. 12478   173-AlaGlyLeuArgSerGlyLysAlaLeuValArgIleArgGlnThrGlyLysAsnSerGlyThrIleAspAsnThrGlyGlyThrHis-201
SEQ. ID. NO. 12479   215-ThrAlaIleLysGlyArgPheGluGlySerArgPheLeuProTyrHisThrArgAsnGlnIleAsnGlyGlyAlaLeuAspGlyLysAlaPro-245

TABLE 1-continued

| | |
|---|---|
| SEQ. ID. NO. 12480 | 250-AlaGluAspProValGlu-255 |
| SEQ. ID. NO. 12481 | 262-GlnGlySerGlyArgLeuLysThrProSerGlyLysTyrIleArg-276 |
| SEQ. ID. NO. 12482 | 278-GlyTyrAlaAspLysAsnGluHisPro-286 |
| SEQ. ID. NO. 12483 | 293-TyrMetAlaAspLysGlyTyrLeuLysLeuGlyGln-304 |
| SEQ. ID. NO. 12484 | 308-GlnGlyIleLysSerTyrMetArgGlnAsnProGlnArgLeuAlaGlu-323 |
| SEQ. ID. NO. 12485 | 326-GlyGlnAsnProSer-330 |
| SEQ. ID. NO. 12486 | 337-LeuAlaGlySerSerAsnAspGlyProVal-346 |
| SEQ. ID. NO. 12487 | 359-GlyAlaValAspArgHisTyr-365 |
| SEQ. ID. NO. 12488 | 379-ProValThrArgLysAlaLeuAsn-386 |
| SEQ. ID. NO. 12489 | 393-AspThrGlySerAlaIleLysGlyAlaValArg-403 |
| SEQ. ID. NO. 12490 | 409-GlyTyrGlyAspGluAlaGlyGluLeuAlaGlyLysGlnLysThrThr-424 |
| SEQ. ID. NO. 12491 | 431-LeuProAsnGlyMetLysProGluTyrArgPro-441 |
| Hydrophilic Regions - Hopp-Woods | |
| SEQ. ID. NO. 12492 | 38-AsnGlyProAspArgProValGly-45 |
| SEQ. ID. NO. 12493 | 90-AsnLeuLysAsnArgGlnGlyTrp-97 |
| SEQ. ID. NO. 12494 | 144-ValLeuLysGlyAspAspArgArgThrAlaGln-154 |
| SEQ. ID. NO. 12495 | 175-LeuArgSerGlyLysAlaLeuValArgIleArgGlnThrGlyLysAsnSerGlyThrIleAspAsnThrGly-198 |
| SEQ. ID. NO. 12496 | 215-ThrAlaIleLysGlyArgPheGluGly-223 |
| SEQ. ID. NO. 12497 | 239-AlaLeuAspGlyLysAla-244 |
| SEQ. ID. NO. 12498 | 250-AlaGluAspProVal-254 |
| SEQ. ID. NO. 12499 | 265-GlyArgLeuLysThrProSer-271 |
| SEQ. ID. NO. 12500 | 279-TyrAlaAspLysAsnGluHis-285 |
| SEQ. ID. NO. 12501 | 317-AsnProGlnArgLeuAlaGlu-323 |
| SEQ. ID. NO. 12502 | 337-LeuAlaGlySerSerAsnAspGlyPro-345 |
| SEQ. ID. NO. 12503 | 380-ValThrArgLysAlaLeuAsn-386 |
| SEQ. ID. NO. 12504 | 393-AspThrGlySerAlaIle-398 |
| SEQ. ID. NO. 12505 | 412-AspGluAlaGlyGluLeuAlaGlyLysGlnLysThr-423 |
| SEQ. ID. NO. 12506 | 434-GlyMetLysProGluTyrArgPro-441 |
| 920-2 | |
| AMPHI Regions - AMPHI | |
| SEQ. ID. NO. 12507 | 43-GlyGluPheProGluLeuGluProIleAla-52 |
| SEQ. ID. NO. 12508 | 117-GlyIleLysGluMetProAsp-123 |
| SEQ. ID. NO. 12509 | 135-LysAsnIleValAsnVal-140 |
| SEQ. ID. NO. 12510 | 163-LeuAspAsnProAlaAsn-168 |
| SEQ. ID. NO. 12511 | 190-ThrValThrAlaThrPheAspGlyPheAspThrSerAspArgSerLys-205 |
| SEQ. ID. NO. 12512 | 212-GlnAlaPheSerAspSerThr-218 |
| Antigenic Index - Jameson-Wolf | |
| SEQ. ID. NO. 12513 | 40-LeuGlyTyrGlyGluPheProGlu-47 |
| SEQ. ID. NO. 12514 | 49-GluProIleAlaLysAspArgLeu-56 |
| SEQ. ID. NO. 12515 | 66-ValThrGluLysGlyLysGluAsnMetIle-75 |
| SEQ. ID. NO. 12516 | 77-ArgGlyThrTyrAsnTyrGlnTyrArgSerAsnArgProValLysAspGlySerTyr-95 |
| SEQ. ID. NO. 12517 | 104-ThrPheTrpSerLysAsnLysAlaGlyTrp-113 |
| SEQ. ID. NO. 12518 | 116-AlaGlyIleLysGluMetProAspAlaSerTyrCysGluGlnThrArgMetPheGlyLysAsnIleValAsnValGlyHisGluSerAlaAspThr-147 |
| SEQ. ID. NO. 12519 | 152-LysProValGlyGlnAsnLeuGlu-159 |
| SEQ. ID. NO. 12520 | 162-ProLeuAspAsnProAla-167 |
| SEQ. ID. NO. 12521 | 173-GluArgPheLysVal-177 |
| SEQ. ID. NO. 12522 | 181-PheArgGlyGluProLeuProAsnAla-189 |
| SEQ. ID. NO. 12523 | 194-ThrPheAspGlyPheAspThrSerAspArgSerLysThrHisLysThrGluAla-211 |
| SEQ. ID. NO. 12524 | 213-AlaPheSerAspSerThrAspAspLysGlyGluValAsp-225 |
| SEQ. ID. NO. 12525 | 237-AsnValGluHisLysThrAspPheProAspGlnSerValCysGlnLysGlnAlaAsnTyrSer-257 |
| Hydrophilic Regions - Hopp-Woods | |
| SEQ. ID. NO. 12526 | 49-GluProIleAlaLysAspArgLeu-56 |
| SEQ. ID. NO. 12527 | 66-ValThrGluLysGlyLysGluAsnMetIle-75 |
| SEQ. ID. NO. 12528 | 85-ArgSerAsnArgProValLysAspGlySer-94 |
| SEQ. ID. NO. 12529 | 107-SerLysAsnLysAlaGlyTrp-113 |
| SEQ. ID. NO. 12530 | 116-AlaGlyIleLysGluMetProAsp-123 |
| SEQ. ID. NO. 12531 | 128-GluGlnThrArgMetPheGly-134 |
| SEQ. ID. NO. 12532 | 142-HisGluSerAlaAsp-146 |
| SEQ. ID. NO. 12533 | 173-GluArgPheLysVal-177 |
| SEQ. ID. NO. 12534 | 196-AspGlyPheAspThrSerAspArgSerLysThrHisLysThrGluAla-211 |
| SEQ. ID. NO. 12535 | 213-AlaPheSerAspSerThrAspAspLysGlyGluValAsp-225 |
| SEQ. ID. NO. 12536 | 237-AsnValGluHisLysThrAspPheProAsp-246 |
| SEQ. ID. NO. 12537 | 248-SerValCysGlnLys-252 |
| 921 | |
| AMPHI Regions - AMPHI | |
| SEQ. ID. NO. 12538 | 12-AlaValLeuSerGlyCysGlnSerIleTyrValProThrLeuThrGluIleProValAsn-31 |
| SEQ. ID. NO. 12539 | 33-IleAsnThrValLysThr-38 |
| SEQ. ID. NO. 12540 | 51-HisTrpThrAspValAlaLysIleSerAspGlu-61 |
| SEQ. ID. NO. 12541 | 72-GlyLysMetThrLysValGlnAlaAlaGlnTyrLeuAsnAsnPheArgLys-88 |
| SEQ. ID. NO. 12542 | 98-AspSerMetTyrGluIleTyrLeuArg-106 |
| SEQ. ID. NO. 12543 | 126-GlnAsnAlaLeuArgGlyTrpGlnGlnArg-135 |
| Antigenic Index - Jameson-Wolf | |
| SEQ. ID. NO. 12544 | 36-ValLysThrGluAlaProAlaLysGlyPheArg-46 |
| SEQ. ID. NO. 12545 | 56-AlaLysIleSerAspGluAlaThrArg-64 |
| SEQ. ID. NO. 12546 | 72-GlyLysMetThrLys-76 |
| SEQ. ID. NO. 12547 | 84-AsnAsnPheArgLysArgLeuValGlyArgAsnAlaValAspAspSerMet-100 |
| SEQ. ID. NO. 12548 | 108-AlaIleAspSerGlnArgGlyAlaIleAsnThrGluGlnSerLys-122 |
| SEQ. ID. NO. 12549 | 128-AlaLeuArgGlyTrpGlnGlnArgTrpLysAsnMetAspValLysProAsnAsnProAla-147 |
| Hydrophilic Regions - Hopp-Woods | |
| SEQ. ID. NO. 12550 | 36-ValLysThrGluAlaProAlaLysGlyPheArg-46 |

TABLE 1-continued

| | |
|---|---|
| SEQ. ID. NO. 12551 | 56-AlaLysIleSerAspGluAlaThrArg-64 |
| SEQ. ID. NO. 12552 | 86-PheArgLysArgLeuValGly-92 |
| SEQ. ID. NO. 12553 | 94-AsnAlaValAspAspSerMet-100 |
| SEQ. ID. NO. 12554 | 108-AlaIleAspSerGlnArgGlyAlaIleAsnThrGluGlnSerLys-122 |
| SEQ. ID. NO. 12555 | 136-TrpLysAsnMetAspValLysProAsnAsn-145 |

922
AMPHI Regions - AMPHI

| | |
|---|---|
| SEQ. ID. NO. 12556 | 16-LeuSerAlaCysThr-20 |
| SEQ. ID. NO. 12557 | 28-ArgAlaAsnGluAlaGlnAlaPro-35 |
| SEQ. ID. NO. 12558 | 37-AlaValGluMetLysLys-42 |
| SEQ. ID. NO. 12559 | 72-ValArgArgPheValAspAsp-78 |
| SEQ. ID. NO. 12560 | 89-GluTrpGlnAspPhePheAspLys-96 |
| SEQ. ID. NO. 12561 | 104-ValLysIleMetHis-108 |
| SEQ. ID. NO. 12562 | 144-AspAspValAlaGln-148 |
| SEQ. ID. NO. 12563 | 172-GlySerPheArgValAlaAspAlaLeu-180 |
| SEQ. ID. NO. 12564 | 196-LysGluLeuValGluLeuLeuLysLeuAla-205 |
| SEQ. ID. NO. 12565 | 222-AlaMetGlyMetPro-226 |
| SEQ. ID. NO. 12566 | 245-HisArgAspIleTrpGlyAsnValGlyAspValAlaAlaSerValAlaAsnTyrMetLysGlnHis-266 |
| SEQ. ID. NO. 12567 | 298-ArgThrValAlaAspLeuLysAlaTyr-306 |
| SEQ. ID. NO. 12568 | 335-TyrLeuGlyLeuAsnAsnPheTyrThr-343 |

Antigenic Index - Jameson-Wolf

| | |
|---|---|
| SEQ. ID. NO. 12569 | 1-MetLysLysArgLysIleLeu-7 |
| SEQ. ID. NO. 12570 | 22-MetGluAlaArgProProArgAlaAsnGluAlaGlnAlaProArgAlaValGluMetLysLysGluSerArgProAlaPhe-48 |
| SEQ. ID. NO. 12571 | 61-ValSerAspSerGlyPhe-66 |
| SEQ. ID. NO. 12572 | 70-AlaAsnValArgArgPheValAspAspGluValGlyLysGlyAspPheSerArgAlaGluTrp-90 |
| SEQ. ID. NO. 12573 | 107-MetHisArgProSerThrSerArgPro-115 |
| SEQ. ID. NO. 12574 | 120-ArgThrGlyAsnSerGlyLysAlaLysPheArgGlyAlaArgArgPheTyrAlaGluAsnArgAlaLeuIle-143 |
| SEQ. ID. NO. 12575 | 145-AspValAlaGlnLysTyrGlyVal-152 |
| SEQ. ID. NO. 12576 | 163-IleGluThrAsnTyrGlyLysAsnThrGlySer-173 |
| SEQ. ID. NO. 12577 | 186-AspTyrProArgArgAlaGlyPhePhe-194 |
| SEQ. ID. NO. 12578 | 203-LysLeuAlaLysGluGluGlyGlyAsp-211 |
| SEQ. ID. NO. 12579 | 229-MetProSerSerTyrArgLysTrpAlaValAspTyrAspGlyAspGlyHisArgAspIle-248 |
| SEQ. ID. NO. 12580 | 266-HisGlyTrpArgThrGlyGlyLysMet-274 |
| SEQ. ID. NO. 12581 | 281-AlaProGlyAlaAsp-285 |
| SEQ. ID. NO. 12582 | 290-IleGlyGluLysThrAlaLeu-296 |
| SEQ. ID. NO. 12583 | 310-ProGlyGluGluLeuAlaAspAspGluLysAlaVal-321 |
| SEQ. ID. NO. 12584 | 326-GluThrAlaProGly-330 |
| SEQ. ID. NO. 12585 | 357-ValArgAspIleAlaAsnSerLeuGlyGlyProGlyLeu-369 |

Hydrophilic Regions - Hopp-Woods

| | |
|---|---|
| SEQ. ID. NO. 12586 | 1-MetLysLysArgLysIleLeu-7 |
| SEQ. ID. NO. 12587 | 22-MetGluAlaArgProProArgAlaAsnGluAlaGlnAlaProArgAlaValGluMetLysLysGluSerArgProAlaPhe-48 |
| SEQ. ID. NO. 12588 | 70-AlaAsnValArgArgPheValAspAspGluValGlyLysGlyAspPheSerArgAlaGluTrp-90 |
| SEQ. ID. NO. 12589 | 122-GlyAsnSerGlyLysAlaLysPheArgGlyAlaArgArgPheTyrAlaGluAsnArgAlaLeuIle-143 |
| SEQ. ID. NO. 12590 | 166-AsnTyrGlyLysAsnThrGly-172 |
| SEQ. ID. NO. 12591 | 187-TyrProArgArgAlaGlyPhePhe-194 |
| SEQ. ID. NO. 12592 | 203-LysLeuAlaLysGluGluGlyGlyAsp-211 |
| SEQ. ID. NO. 12593 | 240-TyrAspGlyAspGlyHisArgAspIle-248 |
| SEQ. ID. NO. 12594 | 290-IleGlyGluLysThrAlaLeu-296 |
| SEQ. ID. NO. 12595 | 310-ProGlyGluGluLeuAlaAspAspGluLysAlaVal-321 |
| SEQ. ID. NO. 12596 | 357-ValArgAspIleAla-361 |

923-2
AMPHI Regions - AMPHI

| | |
|---|---|
| SEQ. ID. NO. 12597 | 9-LeuMetAlaCysAlaAlaPheLeu-16 |
| SEQ. ID. NO. 12598 | 26-LeuGlyAlaCysTyrAlaIleLeuSerLeuTyrAla-37 |
| SEQ. ID. NO. 12599 | 63-ProAlaLeuLeuGlyGlyTrpValGlyAlaTyr-73 |
| SEQ. ID. NO. 12600 | 117-GlyValAlaSerProCysArgThrIleCysThrValCysGlyPheValAlaLeu-134 |

Antigenic Index - Jameson-Wolf

| | |
|---|---|
| SEQ. ID. NO. 12601 | 43-IleAspLysArgCysAlaIleArgGlyGlnArgArgIleProGluHisArgLeu-60 |
| SEQ. ID. NO. 12602 | 79-PheLysHisLysThrAlaLysLysArgPhe-88 |

Hydrophilic Regions - Hopp-Woods

| | |
|---|---|
| SEQ. ID. NO. 12603 | 43-IleAspLysArgCysAlaIleArgGlyGlnArgArgIleProGluHisArgLeu-60 |
| SEQ. ID. NO. 12604 | 79-PheLysHisLysThrAlaLysLysArgPhe-88 |

925-1
AMPHI Regions - AMPHI

| | |
|---|---|
| SEQ. ID. NO. 12605 | 8-ValGlyValValAlaValLeu-14 |
| SEQ. ID. NO. 12606 | 116-LysCysGlyGlnThrAlaGlnAlaTyrArgAspAla-127 |
| SEQ. ID. NO. 12607 | 139-GlnHisLeuAlaAlaIleGluGlnLeuLys-148 |
| SEQ. ID. NO. 12608 | 155-PheAspGluLeuGlu-159 |

Antigenic Index - Jameson-Wolf

| | |
|---|---|
| SEQ. ID. NO. 12609 | 15-AlaGlyCysGlyLysAspAlaGlyGlyTyrGluGlyTyrTrpArgGluLysSerAspLysLysGluGlyMetIleAlaValLysLysGluLysGlyAsn-47 |
| SEQ. ID. NO. 12610 | 57-ThrGlyLysGluGluSerLeuLeuLeuSerGluLysAspGlyAla-71 |
| SEQ. ID. NO. 12611 | 75-AsnThrGlyIleGly-79 |
| SEQ. ID. NO. 12612 | 81-IleProIleLysLeuSerAspAspGlyLysGluLeuTyrValGluArgArgGlnTyrValLysThrAspAlaAlaMetLysAspLysIleIleAlaHisGlnLysLysCysGlyGlnThr-120 |
| SEQ. ID. NO. 12613 | 123-AlaTyrArgAspAlaArgAsnAlaLeuProSerAsnGlnThrTyr-137 |
| SEQ. ID. NO. 12614 | 145-GluGlnLeuLysArgArgPheGluAlaGluPheAspGluLeuGluLysGluIleLysCysAsnGlyArgSerProAla-170 |

Hydrophilic Regions - Hopp-Woods

| | |
|---|---|
| SEQ. ID. NO. 12615 | 17-CysGlyLysAspAlaGlyGly-23 |
| SEQ. ID. NO. 12616 | 27-TyrTrpArgGluLysSerAspLysLysGluGlyMetIleAlaValLysLysGluLysGly-46 |

TABLE 1-continued

| | |
|---|---|
| SEQ. ID. NO. 12617 | 57-ThrGlyLysGluGluSerLeuLeuLeuSerGluLysAspGlyAla-71 |
| SEQ. ID. NO. 12618 | 81-IleProIleLysLeuSerAspAspGlyLysGluLeuTyrValGluArgArgGlnTyrValLysThrAspAlaAlaMetLysAspLysIleIleAla HisGlnLysLysCysGlyGln-119 |
| SEQ. ID. NO. 12619 | 123-AlaTyrArgAspAlaArgAsnAlaLeu-131 |
| SEQ. ID. NO. 12620 | 145-GluGlnLeuLysArgArgPheGluAlaGluPheAspGluLeuGluLysGluIleLysCysAsnGlyArgSer-168 |

926
AMPHI Regions - AMPHI

| | |
|---|---|
| SEQ. ID. NO. 12621 | 29-ProSerGluHisIleSerSerPhe-36 |
| SEQ. ID. NO. 12622 | 72-LeuGlySerThrLeuGlyGln-78 |
| SEQ. ID. NO. 12623 | 98-AlaGluSerAlaGluGluLeuSerArgGln-107 |
| SEQ. ID. NO. 12624 | 128-AlaGlyAlaProTyrArgIleLeuProAspGlyIle-139 |
| SEQ. ID. NO. 12625 | 151-AlaAspSerGlyGlyGlnVal-157 |

Antigenic Index - Jameson-Wolf

| | |
|---|---|
| SEQ. ID. NO. 12626 | 19-LeuProGlnAsnAsnGluAsnLeuTrpGlnProSerGluHisIleSer-34 |
| SEQ. ID. NO. 12627 | 37-AlaAlaGluGlyArgLeuAlaValLysAlaGluGlyLysGlySerTyrAla-53 |
| SEQ. ID. NO. 12628 | 70-ThrProLeuGlySer-74 |
| SEQ. ID. NO. 12629 | 79-LeuCysGlnAspArgAspGlyAlaLeu-87 |
| SEQ. ID. NO. 12630 | 89-ValAspGlyLysGlyAsnValTyr-96 |
| SEQ. ID. NO. 12631 | 99-GluSerAlaGluGluLeuSerArg-106 |
| SEQ. ID. NO. 12632 | 121-TrpAlaAspGlyArgArgValAla-128 |
| SEQ. ID. NO. 12633 | 134-IleLeuProAspGlyIleLeu-140 |
| SEQ. ID. NO. 12634 | 148-GlyArgThrAlaAspSerGlyGlyGln-156 |
| SEQ. ID. NO. 12635 | 177-GlyMetProSerGluThrGluThrProGluArgCysAlaAlaArgThrArg-193 |

Hydrophilic Regions - Hopp-Woods

| | |
|---|---|
| SEQ. ID. NO. 12636 | 37-AlaAlaGluGlyArgLeuAlaValLysAlaGluGlyLysGlySer-51 |
| SEQ. ID. NO. 12637 | 80-CysGlnAspArgAspGlyAlaLeu-87 |
| SEQ. ID. NO. 12638 | 89-ValAspGlyLysGly-93 |
| SEQ. ID. NO. 12639 | 99-GluSerAlaGluGluLeuSerArg-106 |
| SEQ. ID. NO. 12640 | 123-AspGlyArgArgValAla-128 |
| SEQ. ID. NO. 12641 | 149-ArgThrAlaAspSerGlyGlyGln-156 |
| SEQ. ID. NO. 12642 | 180-SerGluThrGluThrProGluArgCysAlaAlaArgThrArg-193 |

927-2
AMPHI Regions - AMPHI

| | |
|---|---|
| SEQ. ID. NO. 12643 | 13-LeuLeuThrAlaCys-17 |
| SEQ. ID. NO. 12644 | 48-SerTyrAspValAlaArgAspPheTyrLysGlu-58 |
| SEQ. ID. NO. 12645 | 120-LysGlyTrpGlnGlnAlaLeuPro-127 |
| SEQ. ID. NO. 12646 | 145-AsnProLysGlnIleArgAspTrpAsnAspLeuAlaLysAspGly-159 |
| SEQ. ID. NO. 12647 | 197-LysLeuValAlaSerIleLeu-203 |
| SEQ. ID. NO. 12648 | 223-ArgAsnIleGlyAspValLeu-229 |
| SEQ. ID. NO. 12649 | 275-ThrGlnLysThrAlaArgAla-281 |
| SEQ. ID. NO. 12650 | 283-LeuGluTyrLeuTrpSerGluProAlaGlnGluLeu-294 |
| SEQ. ID. NO. 12651 | 325-LysLysPheGlyGlyTrpAspAsnIleMetLysThr-336 |

Antigenic Index - Jameson-Wolf

| | |
|---|---|
| SEQ. ID. NO. 12652 | 18-SerProAlaAlaAspSerAsnHisProSerGlyGlnAsnAlaProAlaAsnThrGluSerAspGlyLysAsnIleThr-43 |
| SEQ. ID. NO. 12653 | 48-SerTyrAspValAlaArgAspPheTyrLysGluTyrAsnPro-61 |
| SEQ. ID. NO. 12654 | 67-TyrGlnSerGluHisProGlyThrSer-75 |
| SEQ. ID. NO. 12655 | 79-GlnGlnSerHisGlyGlySerSerLysGlnAla-89 |
| SEQ. ID. NO. 12656 | 104-AsnGlnSerSerAspIleAspLeuLeuGluLysLysGlyLeuVal-118 |
| SEQ. ID. NO. 12657 | 125-AlaLeuProAspHisAlaAlaProTyrThr-134 |
| SEQ. ID. NO. 12658 | 142-ArgLysAsnAsnProLysGlnIleArgAspTrpAsnAspLeuAlaLysAspGlyVal-160 |
| SEQ. ID. NO. 12659 | 166-AsnProLysThrSerGlyAsnGlyArg-174 |
| SEQ. ID. NO. 12660 | 185-LeuLysThrThrAsnGlyAsnGluGlnGluAlaGlnLys-197 |
| SEQ. ID. NO. 12661 | 203-LeuLysAsnThrProValPheGluAsnGlyGlyArgAlaAlaThr-217 |
| SEQ. ID. NO. 12662 | 220-PheThrGlnArgAsnIleGlyAsp-227 |
| SEQ. ID. NO. 12663 | 238-TyrValSerLysLysLeuThrGlnGlyGln-247 |
| SEQ. ID. NO. 12664 | 270-ValAlaLysLysGlyThrGlnLysThrAlaArgAla-281 |
| SEQ. ID. NO. 12665 | 300-LeuArgProArgAsnProGluValLeuAlaArgHisLysAlaAspPheProAspLeuAspThrPheSerProGluLysLysPheGlyGlyTrp-330 |
| SEQ. ID. NO. 12666 | 337-TyrPheAlaAspGlyGlyIle-343 |
| SEQ. ID. NO. 12667 | 347-LeuThrAlaGlnLys-351 |

Hydrophilic Regions - Hopp-Woods

| | |
|---|---|
| SEQ. ID. NO. 12668 | 19-ProAlaAlaAspSerAsnHisProSer-27 |
| SEQ. ID. NO. 12669 | 33-AlaAsnThrGluSerAspGlyLysAsn-41 |
| SEQ. ID. NO. 12670 | 50-AspValAlaArgAspPheTyrLys-57 |
| SEQ. ID. NO. 12671 | 67-TyrGlnSerGluHisProGly-73 |
| SEQ. ID. NO. 12672 | 82-HisGlyGlySerSerLysGlnAla-89 |
| SEQ. ID. NO. 12673 | 105-GlnSerSerAspIleAspLeuLeuGluLysLysGlyLeuVal-118 |
| SEQ. ID. NO. 12674 | 142-ArgLysAsnAsnProLysGlnIleArgAspTrpAsnAspLeuAlaLysAspGlyVal-160 |
| SEQ. ID. NO. 12675 | 167-ProLysThrSerGlyAsnGly-173 |
| SEQ. ID. NO. 12676 | 187-ThrThrAsnGlyAsnGluGlnGluAlaGlnLys-197 |
| SEQ. ID. NO. 12677 | 211-AsnGlyGlyArgAlaAla-216 |
| SEQ. ID. NO. 12678 | 238-TyrValSerLysLysLeuThr-244 |
| SEQ. ID. NO. 12679 | 270-ValAlaLysLysGlyThrGlnLysThrAlaArgAla-281 |
| SEQ. ID. NO. 12680 | 300-LeuArgProArgAsnProGluValLeuAlaArgHisLysAlaAspPheProAsp-317 |
| SEQ. ID. NO. 12681 | 319-AspThrPheSerProGluLysLysPheGlyGly-329 |
| SEQ. ID. NO. 12682 | 347-LeuThrAlaGlnLys-351 |

929-2
AMPHI Regions - AMPHI

| | |
|---|---|
| SEQ. ID. NO. 12683 | 25-ValProAspGlyValLys-30 |
| SEQ. ID. NO. 12684 | 34-TrpThrLeuLeuAlaMetPheValGlyValIleAlaAlaIleIle-48 |
| SEQ. ID. NO. 12685 | 76-GlyAlaAlaMetSerAspAlaLeuSerAlaPhe-86 |

TABLE 1-continued

| | |
|---|---|
| SEQ. ID. NO. 12686 | 155-HisProIleMetGlnSerIleAlaGlySerTyrGlySerAsnProAlaLys-171 |
| SEQ. ID. NO. 12687 | 180-TyrLeuAlaLeuVal-184 |
| SEQ. ID. NO. 12688 | 204-ProLeuIleValAsnLeuIleAlaGluAsnLeuGly-215 |
| SEQ. ID. NO. 12689 | 233-GlyValIleAlaPhePhe-238 |
| SEQ. ID. NO. 12690 | 265-ArgLeuArgGluMetGlyLysMetSer-273 |
| SEQ. ID. NO. 12691 | 280-AlaValIlePheGlyIle-285 |
| SEQ. ID. NO. 12692 | 355-LeuGlyLeuIleLysTrpPheSerGlyValLeuAlaGluSerValGlyGlyLeu-372 |
| SEQ. ID. NO. 12693 | 398-ThrAlaHisIleThrAlaMetPheGlyAlaPhePheAla-410 |
| SEQ. ID. NO. 12694 | 452-TyrThrThrMetGlyGluTrpTrp-459 |

Antigenic Index - Jameson-Wolf

| | |
|---|---|
| SEQ. ID. NO. 12695 | 25-ValProAspGlyValLysProGln-32 |
| SEQ. ID. NO. 12696 | 71-ThrAlaAspLysProGlyAlaAlaMet-79 |
| SEQ. ID. NO. 12697 | 122-GlyArgLysThrLeuGlyIle-128 |
| SEQ. ID. NO. 12698 | 143-ThrProSerAsnThrAlaArgGlyGlyGly-152 |
| SEQ. ID. NO. 12699 | 163-GlySerTyrGlySerAsnProAlaLysGlyThrGluGlyLysMetGlyLys-179 |
| SEQ. ID. NO. 12700 | 187-HisSerAsnProIleSer-192 |
| SEQ. ID. NO. 12701 | 213-AsnLeuGlySerSerPhe-218 |
| SEQ. ID. NO. 12702 | 248-TyrProProGluIleLysGluThrProAsn-257 |
| SEQ. ID. NO. 12703 | 261-PheAlaLysAspArgLeuArgGluMetGlyLysMetSerAlaAspGluIle-277 |
| SEQ. ID. NO. 12704 | 328-AspValLeuLysGluLysSerAlaTrp-336 |

Hydrophilic Regions - Hopp-Woods

| | |
|---|---|
| SEQ. ID. NO. 12705 | 71-ThrAlaAspLysProGlyAlaAlaMet-79 |
| SEQ. ID. NO. 12706 | 146-AsnThrAlaArgGly-150 |
| SEQ. ID. NO. 12707 | 168-AsnProAlaLysGlyThrGluGlyLysMetGlyLys-179 |
| SEQ. ID. NO. 12708 | 250-ProGluIleLysGluThrProAsn-257 |
| SEQ. ID. NO. 12709 | 261-PheAlaLysAspArgLeuArgGluMetGlyLysMetSerAlaAspGluIle-277 |
| SEQ. ID. NO. 12710 | 328-AspValLeuLysGluLysSerAlaTrp-336 |

930-1
AMPHI Regions - AMPHI

| | |
|---|---|
| SEQ. ID. NO. 12711 | 8-LeuProAsnIleArg-12 |
| SEQ. ID. NO. 12712 | 69-AsnThrGlyGluThrValAsnGlnLeuMetGly-79 |
| SEQ. ID. NO. 12713 | 121-LeuHisAlaGlyAsnIleAsnGlnIleMetSerLeu-132 |
| SEQ. ID. NO. 12714 | 147-IleLeuAlaAlaPro-151 |
| SEQ. ID. NO. 12715 | 165-ProSerTyrLeuArgSerIleArgIle-173 |
| SEQ. ID. NO. 12716 | 199-AspLeuLeuAsnLeuArgAsp-205 |
| SEQ. ID. NO. 12717 | 207-GluGlnGlyLeuGluAsnLeuLysArgLeuProThr-218 |
| SEQ. ID. NO. 12718 | 280-SerAspMetPheTyr-284 |
| SEQ. ID. NO. 12719 | 288-GlyArgSerIleGlyGlyThrProAsp-296 |
| SEQ. ID. NO. 12720 | 333-ArgTyrHisGlnAlaValSerGlyLeuSerGluValTyrAsp-346 |
| SEQ. ID. NO. 12721 | 400-TrpLeuAlaGluLeu-404 |
| SEQ. ID. NO. 12722 | 427-MetLysAspAlaLeuArgAlaProGluGluAlaPheGlyGluGly-441 |
| SEQ. ID. NO. 12723 | 472-HisAlaGlnTrpAsnLys-477 |

Antigenic Index - Jameson-Wolf

| | |
|---|---|
| SEQ. ID. NO. 12724 | 32-SerProAsnProAlaGluIleArgMetGlnGlnAspIleGlnGlnArgGlnArgGluGluGlnLeuArgGlnThrMetGlnProGluSerAsp<br>ValArgLeuHisGlnLysAsnThrGlyGluThr-73 |
| SEQ. ID. NO. 12725 | 77-LeuMetGlyAspAspSerSerGln-84 |
| SEQ. ID. NO. 12726 | 93-ValLeuGluGlyGluHisHisAla-100 |
| SEQ. ID. NO. 12727 | 108-ArgAlaLeuArgGluThrGly-114 |
| SEQ. ID. NO. 12728 | 118-GlyLysCysLeuHisAlaGlyAsn-125 |
| SEQ. ID. NO. 12729 | 151-ProGlnAspLeuAsnSerGlyLysLeu-159 |
| SEQ. ID. NO. 12730 | 171-IleArgIleAspArgSerAsnAspAspGlnThrHis-182 |
| SEQ. ID. NO. 12731 | 191-AsnLysPheProThrArgSerAsnAspLeuLeuAsn-202 |
| SEQ. ID. NO. 12732 | 204-ArgAspLeuGluGlnGlyLeuGluAsnLeuLysArgLeuProThrAlaGluAlaAspLeu-223 |
| SEQ. ID. NO. 12733 | 228-ValGluGlyGluProAsnGlnSerAspVal-237 |
| SEQ. ID. NO. 12734 | 242-ArgGlnArgLeuLeuPro-247 |
| SEQ. ID. NO. 12735 | 252-ValGlyMetAspAsnSerGlySerGluAlaThrGlyLysTyrGlnGly-267 |
| SEQ. ID. NO. 12736 | 273-AlaAspAsnProLeuGlyLeu-279 |
| SEQ. ID. NO. 12737 | 287-TyrGlyArgSerIleGlyGlyThrProAspGluGluSerPheAspGlyHisArgLysGluGlyGlySerAsn-310 |
| SEQ. ID. NO. 12738 | 329-HisAsnGlyTyrArg-333 |
| SEQ. ID. NO. 12739 | 343-GluValTyrAspTyrAsnGlyLysSerTyrAsnThrAspPheGlyPhe-358 |
| SEQ. ID. NO. 12740 | 362-LeuTyrArgAspAlaLysArgLysThr-370 |
| SEQ. ID. NO. 12741 | 377-TrpMetArgGluThrLysSerTyrIleAspAspAlaGluLeuThrValGlnArgArgLysThrAla-398 |
| SEQ. ID. NO. 12742 | 408-GluTyrIleGlyArgSerThrAlaAspPheLysLeuLysTyrLysArgGlyThrGlyMetLysAspAlaLeuArgAlaProGluGluAlaPhe<br>GlyGluGlyThrSerArg-444 |
| SEQ. ID. NO. 12743 | 451-SerAlaAspValAsnThrPro-457 |
| SEQ. ID. NO. 12744 | 474-GlnTrpAsnLysThrProLeuThrSerGlnAspLysLeuAla-487 |
| SEQ. ID. NO. 12745 | 492-HisThrValArgGlyPheAspGlyGluMet-501 |
| SEQ. ID. NO. 12746 | 503-LeuSerAlaGluArgGlyTrpTyrTrpArgAsnAspLeuSerTrpGlnPheLysProGlyHis-523 |
| SEQ. ID. NO. 12747 | 535-SerGlyGlnSerAlaLys-540 |
| SEQ. ID. NO. 12748 | 572-ArgAlaLeuLysLysProGluPhePheGlnSerArgLysTrpAlaSerGly-588 |

Hydrophilic Regions - Hopp-Woods

| | |
|---|---|
| SEQ. ID. NO. 12749 | 34-AsnProAlaGluIleArgMetGlnGlnAspIleGlnGlnArgGlnArgGluGluGlnLeuArgGln-55 |
| SEQ. ID. NO. 12750 | 57-MetGlnProGluSerAspValArgLeuHisGlnLysAsnThrGlyGluThr-73 |
| SEQ. ID. NO. 12751 | 78-MetGlyAspAspSerSerGln-84 |
| SEQ. ID. NO. 12752 | 93-ValLeuGluGlyGluHisHisAla-100 |
| SEQ. ID. NO. 12753 | 108-ArgAlaLeuArgGluThrGly-114 |
| SEQ. ID. NO. 12754 | 152-GlnAspLeuAsnSerGlyLys-158 |
| SEQ. ID. NO. 12755 | 171-IleArgIleAspArgSerAsnAspAspGlnThrHis-182 |
| SEQ. ID. NO. 12756 | 193-PheProThrArgSerAsnAsp-199 |
| SEQ. ID. NO. 12757 | 204-ArgAspLeuGluGlnGlyLeuGluAsnLeuLysArgLeuProThrAlaGluAlaAspLeu-223 |

TABLE 1-continued

| | |
|---|---|
| SEQ. ID. NO. 12758 | 228-ValGluGlyGluProAsnGlnSer-235 |
| SEQ. ID. NO. 12759 | 254-MetAspAsnSerGlySerGluAlaThrGly-263 |
| SEQ. ID. NO. 12760 | 291-IleGlyGlyThrProAspGluGluSerPheAspGlyHisArgLysGluGlyGlySer-309 |
| SEQ. ID. NO. 12761 | 345-TyrAspTyrAsnGly-349 |
| SEQ. ID. NO. 12762 | 362-LeuTyrArgAspAlaLysArgLysThr-370 |
| SEQ. ID. NO. 12763 | 377-TrpMetArgGluThrLysSerTyrIleAspAspAlaGluLeuThrValGlnArgArgLysThr-397 |
| SEQ. ID. NO. 12764 | 413-SerThrAlaAspPheLysLeuLysTyrLysArgGlyThrGlyMetLysAspAlaLeuArgAlaProGluGluAlaPheGly-439 |
| SEQ. ID. NO. 12765 | 479-ProLeuThrSerGlnAspLysLeuAla-487 |
| SEQ. ID. NO. 12766 | 495-ArgGlyPheAspGlyGluMet-501 |
| SEQ. ID. NO. 12767 | 503-LeuSerAlaGluArg-507 |
| SEQ. ID. NO. 12768 | 572-ArgAlaLeuLysLysProGluPhePheGln-581 |
| 931-2 | |
| AMPHI Regions - AMPHI | |
| SEQ. ID. NO. 12769 | 43-LysAlaProLysThrValAlaAsnPheValArgTyrAlaArgLys-57 |
| SEQ. ID. NO. 12770 | 65-PheHisArgValIleAspGly-71 |
| SEQ. ID. NO. 12771 | 81-GluAspLeuAlaGlnLysAlaSerAspLys-90 |
| SEQ. ID. NO. 12772 | 94-AsnGluSerGlyAsnGlyLeuLysAsnThr-103 |
| SEQ. ID. NO. 12773 | 142-ThrValPheGlyArgValGluSerGlyMetAsnThrValSerLysIleAlaArgValLysThrAlaThrArgGlyPhe-167 |
| Antigenic Index - Jameson-Wolf | |
| SEQ. ID. NO. 12774 | 1-MetLysProLysPhe-5 |
| SEQ. ID. NO. 12775 | 30-ThrAspMetGlyAsn-34 |
| SEQ. ID. NO. 12776 | 38-ValLeuAspGluSerLysAlaProLysThr-47 |
| SEQ. ID. NO. 12777 | 53-ArgTyrAlaArgLysGlyPheTyrAspAspThrValPhe-65 |
| SEQ. ID. NO. 12778 | 76-GlyGlyGlyLeuThrGluAspLeuAlaGlnLysAlaSerAspLysAlaValAlaAsnGluSerGlyAsnGlyLeuLysAsnThrAla-104 |
| SEQ. ID. NO. 12779 | 110-AlaArgThrThrAlaProAspSerAlaThr-119 |
| SEQ. ID. NO. 12780 | 128-AspAsnAlaSerLeuAspTyrLysAsnGlyGlnTyr-139 |
| SEQ. ID. NO. 12781 | 145-GlyArgValGluSerGlyMetAsnThrVal-154 |
| SEQ. ID. NO. 12782 | 156-LysIleAlaArgValLysThrAlaThrArgGlyPhe-167 |
| SEQ. ID. NO. 12783 | 176-ValLysIleArgArg-180 |
| Hydrophilic Regions - Hopp-Woods | |
| SEQ. ID. NO. 12784 | 1-MetLysProLysPhe-5 |
| SEQ. ID. NO. 12785 | 30-ThrAspMetGlyAsn-34 |
| SEQ. ID. NO. 12786 | 38-ValLeuAspGluSerLysAlaProLysThr-47 |
| SEQ. ID. NO. 12787 | 78-GlyLeuThrGluAspLeuAlaGlnLysAlaSerAspLysAlaValAlaAsnGluSerGlyAsnGlyLeuLysAsnThrAla-104 |
| SEQ. ID. NO. 12788 | 113-ThrAlaProAspSerAlaThr-119 |
| SEQ. ID. NO. 12789 | 130-AlaSerLeuAspTyrLysAsn-136 |
| SEQ. ID. NO. 12790 | 145-GlyArgValGluSerGlyMet-151 |
| SEQ. ID. NO. 12791 | 156-LysIleAlaArgValLysThrAlaThr-164 |
| SEQ. ID. NO. 12792 | 176-ValLysIleArgArg-180 |
| 932 | |
| AMPHI Regions - AMPHI | |
| SEQ. ID. NO. 12793 | 27-AspAlaAlaSerPheTrpGluLeuLysAsn-36 |
| SEQ. ID. NO. 12794 | 38-AlaAsnProTyrPro-42 |
| SEQ. ID. NO. 12795 | 46-SerAlaAlaLeuAspGlnTyrProSer-54 |
| SEQ. ID. NO. 12796 | 60-GlnLeuLysAspMetGlnGluCys-67 |
| Antigenic Index - Jameson-Wolf | |
| SEQ. ID. NO. 12797 | 18-PheGlyGlyPheLysProAsnProTrpAsp-27 |
| SEQ. ID. NO. 12798 | 34-LeuLysAsnTyrAlaAsnProTyrProGlySer-44 |
| SEQ. ID. NO. 12799 | 50-AspGlnTyrProSerLysAlaArgArgArgGlnLeuLysAspMetGlnGluCysGlyTyrAspProIleAspGlyGlyLysSerGluAlaAsp AlaCysLeuArgLysLysGlyTrpCysArgLysGlyPheAspProTyrProGluAsnLysLysTyrGluTrpPro ArgGluGluGlyLysThrLys-112 |
| Hydrophilic Regions - Hopp-Woods | |
| SEQ. ID. NO. 12800 | 52-TyrProSerLysAlaArgArgArgGlnLeuLysAspMetGlnGluCysGlyTyrAspProIleAspGlyGlyLysSerGluAlaAspAlaCysLeuArg LysLysGlyTrpCys-89 |
| SEQ. ID. NO. 12801 | 91-LysGlyPheAspProTyrProGluAsnLysLysTyrGluTrpProArgGluGluGlyLysThrLys-112 |
| 933 | |
| AMPHI Regions - AMPHI | |
| SEQ. ID. NO. 12802 | 6-LysThrSerGluTyr-10 |
| SEQ. ID. NO. 12803 | 37-GlnPheGluAsnIleAsnAsnSerLysLys-46 |
| SEQ. ID. NO. 12804 | 61-GlyPheAlaArgGlyLeu-66 |
| SEQ. ID. NO. 12805 | 75-ThrGluGluGlnIleArgLysTyrPheLysGluCysPheAsn-88 |
| SEQ. ID. NO. 12806 | 94-ArgAspTyrSerThrCysGlnAla-101 |
| SEQ. ID. NO. 12807 | 133-SerValGlyAsnTyrThrGluTrpAlaAsnGlnValIleHisHisIleGluAsnTyrValSerPheAlaAlaHisLeuTyrSerGlyLeuAspPro PheHisTyrIleGluVal-170 |
| SEQ. ID. NO. 12808 | 261-GluAsnProIleAspAspLeuLysSerLeuAspGlyHisGlnIleIleLysValAsn-279 |
| SEQ. ID. NO. 12809 | 308-GlyPhePheThrLys-312 |
| SEQ. ID. NO. 12810 | 355-TrpLeuArgValIleAspGlyHisSerAsn-364 |
| SEQ. ID. NO. 12811 | 373-ProValGluGlyTyrArgLysGly-380 |
| SEQ. ID. NO. 12812 | 430-AlaGlyValTyrAlaThrTrpHis-437 |
| SEQ. ID. NO. 12813 | 451-TrpMetGlnTyrGln-455 |
| SEQ. ID. NO. 12814 | 466-GlyThrGluArgPheThr-471 |
| SEQ. ID. NO. 12815 | 473-LysGlyIleThrAlaSer-478 |
| SEQ. ID. NO. 12816 | 482-GlyTyrAsnAlaLeuLeuAla-488 |
| SEQ. ID. NO. 12817 | 547-LeuTyrLysAsnIleAlaIleGlu-554 |
| SEQ. ID. NO. 12818 | 556-PheAlaAlaValAsn-560 |
| SEQ. ID. NO. 12819 | 605-PheAsnArgGlnThrGly-610 |
| Antigenic Index - Jameson-Wolf | |
| SEQ. ID. NO. 12820 | 1-LysLysLeuArgAspLysThrSerGluTyrTrpLysLysGluThr-15 |
| SEQ. ID. NO. 12821 | 19-ThrGluAspAsnProLysValProPro-27 |
| SEQ. ID. NO. 12822 | 32-TyrProArgThrTyrGln-37 |

TABLE 1-continued

| | |
|---|---|
| SEQ. ID. NO. 12823 | 39-GluAsnIleAsnAsnSerLysLysIleSer-48 |
| SEQ. ID. NO. 12824 | 50-TyrAspGlnGluTyrThrGluGlyTyr-58 |
| SEQ. ID. NO. 12825 | 67-GlyValAlaLysArgAsnGlyAspThrGluGluGlnIleArgLysTyrPheLys-84 |
| SEQ. ID. NO. 12826 | 86-CysPheAsnSerAsnThrLysIleArgAspTyrSerThrCysGlnAlaGluLysPheGlySerHisPro-108 |
| SEQ. ID. NO. 12827 | 118-LeuGlyProLysIleLysAsnSerHisIleAsnSerGluIle-131 |
| SEQ. ID. NO. 12828 | 159-TyrSerGlyLeuAspPro-164 |
| SEQ. ID. NO. 12829 | 169-GluValThrAspAsnSerHis-175 |
| SEQ. ID. NO. 12830 | 184-AspGluPheArgLeuGluAsnSerLeuTrpGluProArgTrpAspSerAsnValGlyLysLeuLysThrThrAsnAlaAspIleArg PheAsnThrLysSerGluSerLeuLeuValLysGluAspTyrAlaGlyGlyAlaArgPheArgPheAlaTyrAspProLysGluAlaLysAsn-243 |
| SEQ. ID. NO. 12831 | 249-GluLysAsnValThrGlyThrSer-256 |
| SEQ. ID. NO. 12832 | 259-IlePheGluAsnProIleAspAspLeuLysSerLeuAspGlyHisGlnIleIle-276 |
| SEQ. ID. NO. 12833 | 278-ValAsnGlyThrAlaAspLysHisAlaPheArgLeuSerGlyLysHisGlnLysGly-296 |
| SEQ. ID. NO. 12834 | 302-LeuGlnGlnArgProGluGlyPhe-309 |
| SEQ. ID. NO. 12835 | 312-LysValGlnGluArgAspAspMet-319 |
| SEQ. ID. NO. 12836 | 336-ArgLeuAsnAsnLysAsnSerAspIlePheAspArgThrLeuProArgLysGlyLeu-354 |
| SEQ. ID. NO. 12837 | 359-IleAspGlyHisSerAsnGlnTrpValGlnGlyLysThrAlaProValGluGlyTyrArgLysGlyVal-381 |
| SEQ. ID. NO. 12838 | 391-GlnAsnGluSerAsnGlnLeu-397 |
| SEQ. ID. NO. 12839 | 402-MetGlyGlyGlnAlaGluGlnArgSerThrPheHisAsnProAspThrAspAsnLeuThr-421 |
| SEQ. ID. NO. 12840 | 423-GlyAsnValLysGly-427 |
| SEQ. ID. NO. 12841 | 439-LeuGlnAspLysGlnThrGlyAlaTyrAlaAspSer-450 |
| SEQ. ID. NO. 12842 | 455-GlnArgPheArgHisArgIleAsnThrGluAspGlyThrGluArgPheThrSerLysGlyIleThrAla-477 |
| SEQ. ID. NO. 12843 | 490-HisPheThrLysLysGlyAsnSerLeu-498 |
| SEQ. ID. NO. 12844 | 513-ValAsnGlyLysPheSerAspSerGluAsnAla-523 |
| SEQ. ID. NO. 12845 | 528-LeuGlySerArgGlnLeuGlnThr-535 |
| SEQ. ID. NO. 12846 | 566-LysProPheGlyValGluMetAspGlyGluArgArgValIleAsnAsnLysThrAlaIleGluSer-587 |
| SEQ. ID. NO. 12847 | 593-ValLysIleLysSer-597 |
| SEQ. ID. NO. 12848 | 604-ThrPheAsnArgGlnThrGlyLysHisHisGlnAlaLysGlnGly-618 |
| Hydrophilic Regions - Hopp-Woods | |
| SEQ. ID. NO. 12849 | 1-LysLysLeuArgAspLysThrSerGluTyrTrpLysLysGluThr-15 |
| SEQ. ID. NO. 12850 | 20-GluAspAsnProLys-24 |
| SEQ. ID. NO. 12851 | 42-AsnAsnSerLysLysIleSer-48 |
| SEQ. ID. NO. 12852 | 67-GlyValAlaLysArgAsnGlyAspThrGluGluGlnIleArgLysTyrPheLys-84 |
| SEQ. ID. NO. 12853 | 91-ThrLysIleArgAspTyrSer-97 |
| SEQ. ID. NO. 12854 | 100-GlnAlaGluLysPheGly-105 |
| SEQ. ID. NO. 12855 | 120-ProLysIleLysAsn-124 |
| SEQ. ID. NO. 12856 | 184-AspGluPheArgLeuGlu-189 |
| SEQ. ID. NO. 12857 | 195-ProArgTrpAspSerAsnValGlyLysLeuLysThrThrAsnAlaAspIleArgPheAsnThrLysSerGluSerLeuLeuValLysGlu AspTyrAlaGly-228 |
| SEQ. ID. NO. 12858 | 236-TyrAspProLysGluAlaLysAsn-243 |
| SEQ. ID. NO. 12859 | 250-LysAsnValThrGly-254 |
| SEQ. ID. NO. 12860 | 262-AsnProIleAspAspLeuLysSerLeuAsp-271 |
| SEQ. ID. NO. 12861 | 280-GlyThrAlaAspLysHisAlaPhe-287 |
| SEQ. ID. NO. 12862 | 289-LeuSerGlyLysHisGlnLys-295 |
| SEQ. ID. NO. 12863 | 303-GlnGlnArgProGluGlyPhe-309 |
| SEQ. ID. NO. 12864 | 313-ValGlnGluArgAspAspMet-319 |
| SEQ. ID. NO. 12865 | 337-LeuAsnAsnLysAsnSerAspIlePheAsp-346 |
| SEQ. ID. NO. 12866 | 375-GluGlyTyrArgLysGlyVal-381 |
| SEQ. ID. NO. 12867 | 392-AsnGluSerAsnGln-396 |
| SEQ. ID. NO. 12868 | 405-GlnAlaGluGlnArgSerThrPheHis-413 |
| SEQ. ID. NO. 12869 | 415-ProAspThrAspAsnLeuThr-421 |
| SEQ. ID. NO. 12870 | 439-LeuGlnAspLysGlnThr-444 |
| SEQ. ID. NO. 12871 | 455-GlnArgPheArgHisArgIleAsnThrGluAspGlyThrGluArgPheThrSer-472 |
| SEQ. ID. NO. 12872 | 490-HisPheThrLysLysGlyAsnSer-497 |
| SEQ. ID. NO. 12873 | 516-LysPheSerAspSerGluAsnAla-523 |
| SEQ. ID. NO. 12874 | 568-PheGlyValGluMetAspGlyGluArgArgValIleAsn-580 |
| SEQ. ID. NO. 12875 | 593-ValLysIleLysSer-597 |
| SEQ. ID. NO. 12876 | 607-ArgGlnThrGlyLysHisHisGlnAlaLysGlnGly-618 |
| 935 | |
| AMPHI Regions - AMPHI | |
| SEQ. ID. NO. 12877 | 41-ValSerAspLysTrpAla-46 |
| SEQ. ID. NO. 12878 | 56-AlaProArgValVal-60 |
| SEQ. ID. NO. 12879 | 72-LeuGluHisSerLeuArgAsp-78 |
| SEQ. ID. NO. 12880 | 87-LeuIleAlaSerLeuAlaAspLeuTyrAlaLysLeu-98 |
| SEQ. ID. NO. 12881 | 111-AlaLeuLeuAlaLysLeuAlaGlyArgProAlaGluAlaValAlaArgTyrArgGlu-129 |
| SEQ. ID. NO. 12882 | 158-GluArgHisPheAlaGlu-163 |
| SEQ. ID. NO. 12883 | 172-ProValLeuGluAsnValGlyArgPheArgLysLysThrGlu-185 |
| SEQ. ID. NO. 12884 | 375-LysArgLeuGlyGluSerAlaThrValPheGlyGlyTrpGlnPheVal-390 |
| SEQ. ID. NO. 12885 | 415-AlaGlyTrpAlaGlnGluTrpArgGlnLeuGlyGlyLeu-427 |
| SEQ. ID. NO. 12886 | 435-TyrAlaArgArgAsnTyrLysGlyIleAlaAlaPhe-446 |
| Antigenic Index - Jameson-Wolf | |
| SEQ. ID. NO. 12887 | 27-AlaIleLeuAspAspLysAlaLeu-34 |
| SEQ. ID. NO. 12888 | 39-ArgSerValSerAspLysTrpAlaGluSerAspTrpLysValGluAsnAspAlaProArgValValAspGlyAspPhe-64 |
| SEQ. ID. NO. 12889 | 70-LysMetLeuGluHisSerLeuArgAspAlaLeuAsnGlyAsnGln-84 |
| SEQ. ID. NO. 12890 | 97-LysLeuProAspTyrAspAla-103 |
| SEQ. ID. NO. 12891 | 108-ArgAlaArgAlaLeu-112 |
| SEQ. ID. NO. 12892 | 116-LeuAlaGlyArgProAlaGluAlaValAlaArgTyrArgGluLeuHisGlyGluAsnAlaAlaAspGluArgIleLeu-141 |
| SEQ. ID. NO. 12893 | 145-AlaAlaAlaGluPheAspAspPheArgLeuLysSerAlaGluArgHisPheAlaGluAlaAlaLysLeuAspLeu-169 |
| SEQ. ID. NO. 12894 | 176-AsnValGlyArgPheArgLysLysThrGluGly-186 |
| SEQ. ID. NO. 12895 | 192-PheSerGlyGlyIle-196 |
| SEQ. ID. NO. 12896 | 199-AlaValAsnArgAsnAlaAsnAsnAlaAla-208 |

TABLE 1-continued

| SEQ. ID. NO. 12897 | 210-GlnTyrCysArgGlnAsnGlyGlyArgGln-219 |
| SEQ. ID. NO. 12898 | 224-SerArgAlaGluArgAlaAla-230 |
| SEQ. ID. NO. 12899 | 236-IleGluAlaGluLysLeuThrProLeuAlaAsp-246 |
| SEQ. ID. NO. 12900 | 253-ArgSerAsnIleGlyGlyThrSerTyr-261 |
| SEQ. ID. NO. 12901 | 263-PheSerLysLysSerAlaTyrAspAspGlyPheGlyArg-275 |
| SEQ. ID. NO. 12902 | 279-GlyTrpGlnTyrLysAsnAlaArgGlnThr-288 |
| SEQ. ID. NO. 12903 | 300-SerGlySerAspGlyPheAspAlaLysThrLysArgValAsnAsnArgArgLeuProProTyr-320 |
| SEQ. ID. NO. 12904 | 332-HisThrTyrArgProAsnProGlyTrp-340 |
| SEQ. ID. NO. 12905 | 347-GluHisTyrArgGlnArgTyrArgGluGlnAspArgAlaGluTyrAsnAsnGlyArgGlnAspGlyPheTyr-370 |
| SEQ. ID. NO. 12906 | 373-SerAlaLysArgLeuGlyGlu-379 |
| SEQ. ID. NO. 12907 | 392-PheValProLysArgGluThrVal-399 |
| SEQ. ID. NO. 12908 | 406-AlaAlaTyrArgArgAsnGlyValTyrAlaGly-416 |
| SEQ. ID. NO. 12909 | 425-GlyGlyLeuAsnSerArgValSerAlaSerTyrAlaArgArgAsnTyrLysGly-442 |
| SEQ. ID. NO. 12910 | 448-ThrGluAlaGlnArgAsnArgGluTrpAsn-457 |
| SEQ. ID. NO. 12911 | 463-SerHisAspLysLeuSerTyrLysGly-471 |
| SEQ. ID. NO. 12912 | 480-PheGlyArgThrGluSerAsnValProTyrAlaLysArgArgAsnSerGlu-496 |
| SEQ. ID. NO. 12913 | 501-AlaAspTrpArgPhe-505 |
| Hydrophilic Regions - Hopp-Woods | |
| SEQ. ID. NO. 12914 | 27-AlaIleLeuAspAspLysAlaLeu-34 |
| SEQ. ID. NO. 12915 | 39-ArgSerValSerAspLysTrpAlaGluSerAspTrpLysValGluAsnAspAlaProArgValValAsp-61 |
| SEQ. ID. NO. 12916 | 70-LysMetLeuGluHisSerLeuArgAspAlaLeuAsn-81 |
| SEQ. ID. NO. 12917 | 108-ArgAlaArgAlaLeu-112 |
| SEQ. ID. NO. 12918 | 116LeuAlaGlyArgProAlaGluAlaValAlaArgTyrArgGluLeuHisGly-132 |
| SEQ. ID. NO. 12919 | 134-AsnAlaAlaAspGluArgIleLeu-141 |
| SEQ. ID. NO. 12920 | 145-AlaAlaAlaGluPheAspAspPheArgLeuLysSerAlaGluArgHisPheAlaGluAlaAlaLysLeuAspLeu-169 |
| SEQ. ID. NO. 12921 | 176-AsnValGlyArgPheArgLysLysThrGluGly-186 |
| SEQ. ID. NO. 12922 | 200-ValAsnArgAsnAlaAsn-205 |
| SEQ. ID. NO. 12923 | 212-CysArgGlnAsnGlyGlyArgGln-219 |
| SEQ. ID. NO. 12924 | 224-SerArgAlaGluArgAlaAla-230 |
| SEQ. ID. NO. 12925 | 236-IleGluAlaGluLysLeuThrPro-243 |
| SEQ. ID. NO. 12926 | 265-LysLysSerAlaTyrAspAspGlyPheGly-274 |
| SEQ. ID. NO. 12927 | 283-LysAsnAlaArgGlnThr-288 |
| SEQ. ID. NO. 12928 | 303-AspGlyPheAspAlaLysThrLysArgValAsnAsnArgArgLeuPro-318 |
| SEQ. ID. NO. 12929 | 348-HisTyrArgGlnArgTyrArgGluGlnAspArgAlaGluTyrAsnAsnGlyArgGlnAsp-367 |
| SEQ. ID. NO. 12930 | 373-SerAlaLysArgLeuGlyGlu-379 |
| SEQ. ID. NO. 12931 | 393-ValProLysArgGluThrVal-399 |
| SEQ. ID. NO. 12932 | 407-AlaTyrArgArgAsnGly-412 |
| SEQ. ID. NO. 12933 | 435-TyrAlaArgArgAsnTyrLys-441 |
| SEQ. ID. NO. 12934 | 449-GluAlaGlnArgAsnArgGluTrp-456 |
| SEQ. ID. NO. 12935 | 463-SerHisAspLysLeuSerTyr-469 |
| SEQ. ID. NO. 12936 | 480-PheGlyArgThrGluSer-485 |
| SEQ. ID. NO. 12937 | 489-TyrAlaLysArgArgAsnSerGlu-496 |
| 936-1 | |
| AMPHI Regions - AMPHI | |
| SEQ. ID. NO. 12938 | 10-ThrLeuIleAlaAlaIle-15 |
| SEQ. ID. NO. 12939 | 22-GlyCysValSerAlaVal-27 |
| SEQ. ID. NO. 12940 | 100-GlnPheValGlyGlnIle-105 |
| SEQ. ID. NO. 12941 | 112-AlaGluGlyValTyrAsnTyrIleThrValAlaSerLeuProArgThrAlaGlyAspIleAlaGlyAsp-134 |
| Antigenic Index - Jameson-Wolf | |
| SEQ. ID. NO. 12942 | 1-MetLysProLysProHisThrVal-8 |
| SEQ. ID. NO. 12943 | 33-ValGlyAlaLysSerAlaValAspArgArgThrThrGlyAlaGlnThrAspAspAsnValMet-53 |
| SEQ. ID. NO. 12944 | 56-ArgIleGluThrThrAlaArgSerTyrLeuArgGlnAsnAsnGlnThrLysGlyTyr-74 |
| SEQ. ID. NO. 12945 | 94-AlaThrGluGlyGluLysGlnPhe-101 |
| SEQ. ID. NO. 12946 | 106-AlaArgSerGluGlnAlaAla-112 |
| SEQ. ID. NO. 12947 | 124-LeuProArgThrAlaGlyAspIleAlaGlyAspThrTrpAsnThrSerLysValArgAla-143 |
| SEQ. ID. NO. 12948 | 149-SerProAlaThrGlnAlaArgValLys-157 |
| SEQ. ID. NO. 12949 | 172-ThrProGluGluGlnAlaGlnIleThr-180 |
| Hydrophilic Regions - Hopp-Woods | |
| SEQ. ID. NO. 12950 | 1-MetLysProLysProHisThr-7 |
| SEQ. ID. NO. 12951 | 37-SerAlaValAspArgArgThrThrGlyAlaGlnThrAspAspAsnValMet-53 |
| SEQ. ID. NO. 12952 | 56-ArgIleGluThrThrAla-61 |
| SEQ. ID. NO. 12953 | 68-AsnAsnGlnThrLysGlyTyr-74 |
| SEQ. ID. NO. 12954 | 94-AlaThrGluGlyGluLysGlnPhe-101 |
| SEQ. ID. NO. 12955 | 106-AlaArgSerGluGlnAlaAla-112 |
| SEQ. ID. NO. 12956 | 125-ProArgThrAlaGly-129 |
| SEQ. ID. NO. 12957 | 152-ThrGlnAlaArgValLys-157 |
| SEQ. ID. NO. 12958 | 172-ThrProGluGluGlnAlaGlnIle-179 |
| 937 | |
| AMPHI Regions - AMPHI | |
| SEQ. ID. NO. 12959 | 6-LeuProAlaLeuProAlaIleLeuProLeuSerThr-17 |
| SEQ. ID. NO. 12960 | 190-AsnGlySerLysThrLeuSer-196 |
| Antigenic Index - Jameson-Wolf | |
| SEQ. ID. NO. 12961 | 27-AspIleMetThrAspLysGlyLysTrpLysLeuGluThr-39 |
| SEQ. ID. NO. 12962 | 44-LeuAsnSerGluAsnAsnArgAlaGluLeu-53 |
| SEQ. ID. NO. 12963 | 72-GluIleGlnGluAsnGlySerAsnThrAsp-81 |
| SEQ. ID. NO. 12964 | 95-GlyAsnThrAspIleTyrGlySerGlySer-104 |
| SEQ. ID. NO. 12965 | 108-HisGluGluArgLysLeuAspGlyAsnSerLysThrArgAsnLysArgMetSerAsp-126 |
| SEQ. ID. NO. 12966 | 135-PheLeuLysAspAspLysAsnProAla-143 |
| SEQ. ID. NO. 12967 | 151-ThrValTyrGluLysSerArgAsnLysAlaSerSerGlyLysSer-165 |
| SEQ. ID. NO. 12968 | 187-TyrArgIleAsnGlySerLysThrLeuSerAspGlyIleArgTyrLysSerGlyAsnTyr-206 |

TABLE 1-continued

| | |
|---|---|
| SEQ. ID. NO. 12969 | 217-AlaAsnAspArgIleSerLeuThrGlyGly-226 |
| SEQ. ID. NO. 12970 | 231-GlyArgGlnProAspArgThrAspGlyLysArgGluSerSerArgAsnThrSerThr-249 |
| SEQ. ID. NO. 12971 | 273-ValSerGlyGlnSerSerSerGluLeuLysPhe-283 |
| Hydrophilic Regions - Hopp-Woods | |
| SEQ. ID. NO. 12972 | 27-AspIleMetThrAspLysGlyLysTrpLysLeu-37 |
| SEQ. ID. NO. 12973 | 47-GluAsnAsnArgAlaGluLeu-53 |
| SEQ. ID. NO. 12974 | 72-GluIleGlnGluAsnGlySerAsnThr-80 |
| SEQ. ID. NO. 12975 | 108-HisGluGluArgLysLeuAspGlyAsnSerLysThrArgAsnLysArgMetSerAsp-126 |
| SEQ. ID. NO. 12976 | 135-PheLeuLysAspAspLysAsnPro-142 |
| SEQ. ID. NO. 12977 | 151-ThrValTyrGluLysSerArgAsnLysAlaSerSer-162 |
| SEQ. ID. NO. 12978 | 193-LysThrLeuSerAspGlyIleArgTyrLysSer-203 |
| SEQ. ID. NO. 12979 | 217-AlaAsnAspArgIleSer-222 |
| SEQ. ID. NO. 12980 | 232-ArgGlnProAspArgThrAspGlyLysArgGluSerSerArgAsnThr-247 |
| SEQ. ID. NO. 12981 | 277-SerSerSerGluLeuLysPhe-283 |
| 939-2 | |
| AMPHI Regions - AMPHI | |
| SEQ. ID. NO. 12982 | 32-AlaThrValCysAla-36 |
| SEQ. ID. NO. 12983 | 90-AspGlnAspIleLeu-94 |
| SEQ. ID. NO. 12984 | 121-LysIleTyrArgGly-125 |
| SEQ. ID. NO. 12985 | 135-CysMetSerCysHisGly-140 |
| SEQ. ID. NO. 12986 | 151-SerGluIleGlnAlaTyrProArgLeuGlyGly-161 |
| SEQ. ID. NO. 12987 | 169-GluGlnMetAsnAlaTyrLys-175 |
| SEQ. ID. NO. 12988 | 185-GluAspIleAlaAsnArgMetSer-192 |
| Antigenic Index - Jameson-Wolf | |
| SEQ. ID. NO. 12989 | 18-AlaSerProLysAlaAspValGluLysGlyLysGlnVal-30 |
| SEQ. ID. NO. 12990 | 40-AlaAlaAspGlyAsnSerGlyIle-47 |
| SEQ. ID. NO. 12991 | 66-IleGlyIleArgAspGlyLysArgThrHisGlySerAlaAlaVal-80 |
| SEQ. ID. NO. 12992 | 88-LeuSerAspGlnAspIle-93 |
| SEQ. ID. NO. 12993 | 102-LysGlnGlnProLysSerGlyGluAlaAsnProLysGluAsnProGluLeuGly-119 |
| SEQ. ID. NO. 12994 | 122-IleTyrArgGlyGlyLeuSerAspLysLysValPro-133 |
| SEQ. ID. NO. 12995 | 139-HisGlyProSerGlyAlaGlyMetProGlyGlyGlySerGluIleGlnAla-155 |
| SEQ. ID. NO. 12996 | 157-ProArgLeuGlyGlyGlnHisGln-164 |
| SEQ. ID. NO. 12997 | 172-AsnAlaTyrLysSerGlyGlnArgLysAsnThrIleMetGluAspIleAlaAsnArgMetSerGluGluAspLeuLysAla-198 |
| Hydrophilic Regions - Hopp-Woods | |
| SEQ. ID. NO. 12998 | 18-AlaSerProLysAlaAspValGluLysGlyLysGlnVal-30 |
| SEQ. ID. NO. 12999 | 40-AlaAlaAspGlyAsnSer-45 |
| SEQ. ID. NO. 13000 | 67-GlyIleArgAspGlyLysArgThrHisGly-76 |
| SEQ. ID. NO. 13001 | 89-SerAspGlnAspIle-93 |
| SEQ. ID. NO. 13002 | 103-GlnGlnProLysSerGlyGluAlaAsnProLysGluAsnProGluLeuGly-119 |
| SEQ. ID. NO. 13003 | 126-GlyLeuSerAspLysLysValPro-133 |
| SEQ. ID. NO. 13004 | 175-LysSerGlyGlnArgLysAsnThrIleMetGluAspIleAlaAsnArgMetSerGluGluAspLeuLysAla-198 |
| 950 | |
| AMPHI Regions - AMPHI | |
| SEQ. ID. NO. 13005 | 33-GlyValHisLysSerAlaHisGly-40 |
| SEQ. ID. NO. 13006 | 71-AlaThrValLysLysThrHisLysHisThrLysAla-82 |
| Antigenic Index - Jameson-Wolf | |
| SEQ. ID. NO. 13007 | 1-MetAsnLysAsnIle-5 |
| SEQ. ID. NO. 13008 | 23-AlaAlaAsnLysProAlaSerAsnAlaThrGlyValHisLysSerAlaHisGlySerCysGlyAlaSerLysSerAlaGluGlySerCysGlyAla AlaGlySerLysAlaGlyGluGlyLysCysGlyGluGlyLysCysGlyAlaThrValLysLysThrHisLysHisThrLysAlaSerLysAlaLysAlaLys SerAlaGluGlyLysCysGlyGluGlyLysCysGlySerLys-102 |
| Hydrophilic Regions - Hopp-Woods | |
| SEQ. ID. NO. 13009 | 23-AlaAlaAsnLysProAlaSer-29 |
| SEQ. ID. NO. 13010 | 33-GlyValHisLysSerAlaHis-39 |
| SEQ. ID. NO. 13011 | 43-GlyAlaSerLysSerAlaGluGlySerCys-52 |
| SEQ. ID. NO. 13012 | 55-AlaGlySerLysAlaGlyGluGlyLysCysGlyGluGlyLysCys-69 |
| SEQ. ID. NO. 13013 | 71-AlaThrValLysLysThrHisLysHisThrLysAlaSerLysAlaLysAlaLysSerAlaGluGlyLysCysGlyGluGlyLysCysGlySerLys-102 |
| 951 | |
| AMPHI Regions - AMPHI | |
| SEQ. ID. NO. 13014 | 9-LysMetLeuThrValLeuThrAla-16 |
| SEQ. ID. NO. 13015 | 32-AspMetLysGlnProLysGluValGlyLysValPheArgLysGlnGlnArgTyr-49 |
| SEQ. ID. NO. 13016 | 64-ValGlyGluArgValAsn-69 |
| SEQ. ID. NO. 13017 | 129-TrpArgGlnIleGluProIleProGlyLys-138 |
| SEQ. ID. NO. 13018 | 157-HisLeuAspGlyLeuGluGluValLeuAla-166 |
| SEQ. ID. NO. 13019 | 191-AlaGlnLysAlaSerLysAlaValArgArg-200 |
| SEQ. ID. NO. 13020 | 206-GluHisLeuProGluAlaAla-212 |
| SEQ. ID. NO. 13021 | 230-GlyAlaLeuGlnArgLeuAlaLysLeu-238 |
| SEQ. ID. NO. 13022 | 256-LysTyrProGluIleLeuAspGlyPhePheGlu-266 |
| SEQ. ID. NO. 13023 | 280-MetGluIleMetAsnLeuValSerLeuHisArgLeuAspAspAla-294 |
| SEQ. ID. NO. 13024 | 327-ValIleAspGlyTyrAlaGluLys-334 |
| SEQ. ID. NO. 13025 | 336-TyrGlyArgGlyThrGlu-341 |
| SEQ. ID. NO. 13026 | 364-ValArgGlnTrpLeuLys-369 |
| SEQ. ID. NO. 13027 | 397-AlaLeuArgGlnIleGlyArgValArgLysLeuProGluGlnGln-411 |
| SEQ. ID. NO. 13028 | 418-AspAsnLeuSerLysIle-423 |
| SEQ. ID. NO. 13029 | 425-MetLeuAlaLeuSer-429 |
| SEQ. ID. NO. 13030 | 436-GluAlaLeuArgGlyLeuAspLysIleIleGluLys-447 |
| SEQ. ID. NO. 13031 | 479-SerAspLeuGluArgAlaPheArg-486 |
| SEQ. ID. NO. 13032 | 497-AsnLeuGlyTyrSer-501 |
| SEQ. ID. NO. 13033 | 565-HisLeuGlyGluVal-569 |
| SEQ. ID. NO. 13034 | 581-AspValTrpThrGlnAla-586 |
| SEQ. ID. NO. 13035 | 596-TrpArgGluThrLeu-600 |

TABLE 1-continued

Antigenic Index - Jameson-Wolf
SEQ. ID. NO. 13036  25-AlaAlaGlyGlyGlyAlaGlyAspMetLysGlnProLysGluValGlyLysValPheArgLysGlnGlnArgTyrSerGluGluGluIleLys
AsnGluArgAlaArgLeu-61
SEQ. ID. NO. 13037  63-AlaValGlyGluArgValAsn-69
SEQ. ID. NO. 13038  79-ThrAlaLeuGlnLysGlyGlnAla-86
SEQ. ID. NO. 13039  98-GluArgThrLysSerProGluValAlaGluArgAlaLeuGlu-111
SEQ. ID. NO. 13040  128-LysTrpArgGlnIleGluProIleProGlyLysAlaGlnLysArgAlaGlyTrpLeuArgAsnValLeuArgGluArgGlyAsnGlnHisLeuAsp
GlyLeuGluGluValLeuAlaGlnAlaAspGluGlyGlnAsnArgArg-175
SEQ. ID. NO. 13041  185-ValGlnGlnAspGlyLeuAlaGlnLysAlaSerLysAlaValArgArgAlaAlaLeuLys-204
SEQ. ID. NO. 13042  221-GlnGlyArgGluLysGluLysAlaIle-229
SEQ. ID. NO. 13043  234-ArgLeuAlaLysLeuAspThrGluIleLeuPro-244
SEQ. ID. NO. 13044  252-LeuThrAlaArgLysTyrProGluIleLeuAspGlyPhePheGluGlnThrAspThrGlnAsn-272
SEQ. ID. NO. 13045  289-HisArgLeuAspAspAlaTyrAla-296
SEQ. ID. NO. 13046  302-LeuGluArgAsnProAsnAlaAsp-309
SEQ. ID. NO. 13047  319-AlaAsnArgLysGlyGlyAlaSer-326
SEQ. ID. NO. 13048  330-GlyTyrAlaGluLysAlaTyrGlyArgGlyThrGluGluGlnArgSerArgAla-347
SEQ. ID. NO. 13049  355-TyrAlaAspArgArgAspTyrAlaLys-363
SEQ. ID. NO. 13050  366-GlnTrpLeuLysLysValSerAla-373
SEQ. ID. NO. 13051  377-LeuPheAspLysGlyVal-382
SEQ. ID. NO. 13052  389-ValGluLeuAspGlyGlyArgAlaAlaLeu-398
SEQ. ID. NO. 13053  400-GlnIleGlyArgValArgLysLeuProGluGlnGlnGlyArgTyrPheThr-416
SEQ. ID. NO. 13054  430-LysLeuProAspLysArgGluAlaLeuArgGlyLeuAspLysIleIleGluLysProProAlaGlySerAsnThrGluLeuGlnAla-458
SEQ. ID. NO. 13055  470-ArgLeuGlyLysArgLysLysMetIleSerAspLeuGluArgAlaPheArgLeuAlaProAspAsn-491
SEQ. ID. NO. 13056  504-ThrAspSerLysArgLeuAspGluGlyPhe-513
SEQ. ID. NO. 13057  522-IleAsnProAspAspThrAlaValAsnAspSerIle-533
SEQ. ID. NO. 13058  539-LeuLysGlyAspAlaGluSerAla-546
SEQ. ID. NO. 13059  551-ArgTyrSerPheGluAsnAspProGluProGluVal-562
SEQ. ID. NO. 13060  574-GlyGluArgAspGlnAla-579
SEQ. ID. NO. 13061  588-HisLeuThrGlyAspLysLysIleTrpArgGluThrLeuLysArgHisGlyIleAlaLeuProGlnProSerArgLysProArgLys-616
Hydrophilic Regions - Hopp-Woods
SEQ. ID. NO. 13062  29-GlyAlaGlyAspMetLysGlnProLysGluValGlyLysValPheArgysGlnGlnArgTyrSerGluGluGluIleLysAsnGluArgAlaArgLeu-61
SEQ. ID. NO. 13063  63-AlaValGlyGluArgValAsn-69
SEQ. ID. NO. 13064  79-ThrAlaLeuGlnLysGlyGlnAla-86
SEQ. ID. NO. 13065  98-GluArgThrLysSerProGluValAlaGluArgAlaLeuGlu-111
SEQ. ID. NO. 13066  135-IleProGlyLysAlaGlnLysArgAlaGlyTrp-145
SEQ. ID. NO. 13067  149-ValLeuArgGluArgGlyAsnGlnHis-157
SEQ. ID. NO. 13068  159-AspGlyLeuGluGluValLeuAlaGlnAlaAspGluGlyGlnAsnArgArg-175
SEQ. ID. NO. 13069  189-GlyLeuAlaGlnLysAlaSerLysAlaValArgArgAlaAlaLeuLys-204
SEQ. ID. NO. 13070  221-GlnGlyArgGluLysGluLysAlaIle-229
SEQ. ID. NO. 13071  234-ArgLeuAlaLysLeuAspThrGluIle-242
SEQ. ID. NO. 13072  252-LeuThrAlaArgLysTyrProGluIle-260
SEQ. ID. NO. 13073  265-PheGluGlnThrAspThrGlnAsn-272
SEQ. ID. NO. 13074  289-HisArgLeuAspAspAlaTyrAla-296
SEQ. ID. NO. 13075  302-LeuGluArgAsnProAsn-307
SEQ. ID. NO. 13076  319-AlaAsnArgLysGlyGlyAlaSer-326
SEQ. ID. NO. 13077  331-TyrAlaGluLysAlaTyrGlyArgGlyThrGluGluGlnArgSerArgAla-347
SEQ. ID. NO. 13078  355-TyrAlaAspArgArgAspTyrAlaLys-363
SEQ. ID. NO. 13079  389-ValGluLeuAspGlyGlyArgAlaAlaLeu-398
SEQ. ID. NO. 13080  400-GlnIleGlyArgValArgLysLeuProGluGlnGlnGly-412
SEQ. ID. NO. 13081  430-LysLeuProAspLysArgGluAlaLeuArgGlyLeuAspLysIleIleGluLysProProAla-450
SEQ. ID. NO. 13082  452-SerAsnThrGluLeuGlnAla-458
SEQ. ID. NO. 13083  470-ArgLeuGlyLysArgLysLysMetIleSerAspLeuGluArgAlaPheArgLeuAlaProAspAsn-491
SEQ. ID. NO. 13084  504-ThrAspSerLysArgLeuAspGlu-511
SEQ. ID. NO. 13085  523-AsnProAspAspThrAlaVal-529
SEQ. ID. NO. 13086  541-GlyAspAlaGluSer-545
SEQ. ID. NO. 13087  554-PheGluAsnAspProGluProGluVal-562
SEQ. ID. NO. 13088  574-GlyGluArgAspGlnAla-579
SEQ. ID. NO. 13089  590-ThrGlyAspLysLysIleTrpArgGluThrLeuLysArgHisGly-604
SEQ. ID. NO. 13090  609-GlnProSerArgLysProArgLys-616
952
AMPHI Regions - AMPHI
SEQ. ID. NO. 13091  63-SerValAlaThrLeuLeuAsnAsnPheTyrGlyGln-74
SEQ. ID. NO. 13092  81-ValLeuLysLysLeuAsp-86
SEQ. ID. NO. 13093  94-PheGluAspMetArgArgIle-100
SEQ. ID. NO. 13094  116-GluGlnLeuAlaGlnLeu-121
SEQ. ID. NO. 13095  138-SerValLeuArgGlyIleAsp-144
SEQ. ID. NO. 13096  163-AlaGlnPheLeuAspAla-168
SEQ. ID. NO. 13097  179-LysIleLeuAlaVal-183
Antigenic Index - Jameson-Wolf
SEQ. ID. NO. 13098  40-GlnSerTrpLysAlaArgArgAspPheAsnIleValLysGlnAspLeuAspPheSerCys-59
SEQ. ID. NO. 13099  70-AsnPheTyrGlyGlnThrLeuThrGluGluGluValLeuLysLysLeuAspLysGluGlnMetArgAlaSerPheGluAspMetArgArgIle
MetPro-102
SEQ. ID. NO. 13100  104-LeuGlyPheGluAlaLysGlyTyr-111
SEQ. ID. NO. 13101  129-LeuLysTyrArgLysAspAspHisPheSer-138
SEQ. ID. NO. 13102  141-ArgGlyIleAspGlyAsnThr-147
SEQ. ID. NO. 13103  169-TrpGlnThrArgGluGlyAsnLeuAla-177
SEQ. ID. NO. 13104  184-IleProLysLysAlaGluThrIleSer-192
SEQ. ID. NO. 13105  199-GlnHisProLysArgGlnThrGlu-206
SEQ. ID. NO. 13106  213-ArgGlnAlaArgAlaGlu-218

TABLE 1-continued

Hydrophilic Regions - Hopp-Woods
SEQ. ID. NO. 13107    41-SerTrpLysAlaArgArgAspPheAsnIleValLysGlnAspLeuAspPhe-57
SEQ. ID. NO. 13108    76-LeuThrGluGluGluValLeuLysLysLeuAspLysGluGlnMetArgAlaSerPheGluAspMetArgArgIleMetPro-102
SEQ. ID. NO. 13109    104-LeuGlyPheGluAlaLysGly-110
SEQ. ID. NO. 13110    130-LysTyrArgLysAspAspHisPheSer-138
SEQ. ID. NO. 13111    169-TrpGlnThrArgGluGlyAsnLeu-176
SEQ. ID. NO. 13112    184-IleProLysLysAlaGluThrIleSer-192
SEQ. ID. NO. 13113    200-HisProLysArgGlnThrGlu-206
SEQ. ID. NO. 13114    213-ArgGlnAlaArgAlaGlu-218
953
AMPHI Regions - AMPHI
SEQ. ID. NO. 13115    39-AsnThrSerThrAsnValGlyGlyPheTyrGlyLeuThr-51
SEQ. ID. NO. 13116    75-GlnSerGlySerGlnHisPheThrAspHisLeuLysSerAlaAspIlePheAspAlaAlaGln-95
SEQ. ID. NO. 13117    151-GlyAspPheSerThrThr-156
Antigenic Index - Jameson-Wolf
SEQ. ID. NO. 13118    22-TyrLysValAspGluTyrHisAla-29
SEQ. ID. NO. 13119    38-PheAsnThrSerThrAsnVal-44
SEQ. ID. NO. 13120    54-ValGluPheAspGlnAlaLysArgAspGlyLysIleAspIle-67
SEQ. ID. NO. 13121    83-AspHisLeuLysSer-87
SEQ. ID. NO. 13122    95-GlnTyrProAspIleArgPheValSer-103
SEQ. ID. NO. 13123    105-LysPheAsnGlyLysLysLeuValSer-115
SEQ. ID. NO. 13124    122-MetHisGlyLysThrAlaProValLysLeuLysAlaGluLys-135
SEQ. ID. NO. 13125    137-AsnCysTyrGlnSerProMetGluLysThrGluValCysGlyGlyAsp-152
SEQ. ID. NO. 13126    154-SerThrThrIleAspArgThrLysTrpGly-163
SEQ. ID. NO. 13127    174-LysSerValArgIle-17
SEQ. ID. NO. 13128    180-IleGlnIleGluAlaAlaLysGln-187
Hydrophilic Regions - Hopp-Woods
SEQ. ID. NO. 13129    22-TyrLysValAspGluTyrHisAla-29
SEQ. ID. NO. 13130    54-ValGluPheAspGlnAlaLysArgAspGlyLysIleAspIle-67
SEQ. ID. NO. 13131    83-AspHisLeuLysSer-87
SEQ. ID. NO. 13132    108-PheAsnGlyLysLysLeuValSer-115
SEQ. ID. NO. 13133    125-LysThrAlaProValLysLeuLysAlaGluLys-135
SEQ. ID. NO. 13134    142-ProMetGluLysThrGluValCysGly-150
SEQ. ID. NO. 13135    155-ThrThrIleAspArgThrLysTrp-162
SEQ. ID. NO. 13136    174-LysSerValArgIle-178
SEQ. ID. NO. 13137    180-IleGlnIleGluAlaAlaLysGln-187
954
AMPHI Regions - AMPHI
SEQ. ID. NO. 13138    48-ArgAlaAlaArgPheArg-53
SEQ. ID. NO. 13139    57-GlnGlyLeuGlyGlyAspPheGluArgPheLeuLysGly-69
SEQ. ID. NO. 13140    74-GlnGluAsnLeuAlaLysTyrArgGluAsnIle-84
SEQ. ID. NO. 13141    100-ProTyrArgValCysLysGlnAla-107
SEQ. ID. NO. 13142    134-TyrGlnAsnTyrArgLysSerMetGlnGluCysArgLysThrIleThr-149
Antigenic Index - Jameson-Wolf
SEQ. ID. NO. 13143    17-GlyGlnGluGlnSerGlnLysAlaAspAlaGlu-27
SEQ. ID. NO. 13144    35-TyrGlnPheAlaAspGluLysGln-42
SEQ. ID. NO. 13145    58-GlyLeuGlyGlyAspPheGluArgPheLeuLysGlyGluIleProAsnGlnGluAsnLeuAlaLysTyrArgGluAsnIle-84
SEQ. ID. NO. 13146    92-AlaAspThrAsnGlyAspAspAspProTyrArgValCysLys-105
SEQ. ID. NO. 13147    107-AlaAlaGlnAspAlaGluIleLeuMet-115
SEQ. ID. NO. 13148    119-ValThrSerGlyGlyGlyGlyThrThrAspLeuAspLysGluSerTyrGlnAsnTyrArgLysSerMetGlnGluCysArgLysThrIleThrGlu
              AlaGluAlaAsnLeuProLysLys-158
Hydrophilic Regions - Hopp-Woods
SEQ. ID. NO. 13149    17-GlyGlnGluGlnSerGlnLysAlaAspAlaGlu-27
SEQ. ID. NO. 13150    36-GlnPheAlaAspGluLysGln-42
SEQ. ID. NO. 13151    61-GlyAspPheGluArgPheLeuLys-68
SEQ. ID. NO. 13152    70-GluIleProAsnGlnGluAsnLeuAlaLysTyrArgGluAsnIle-84
SEQ. ID. NO. 13153    94-ThrAsnGlyAspAspAspProTyrArgValCysLys-105
SEQ. ID. NO. 13154    107-AlaAlaGlnAspAlaGluIleLeuMet-115
SEQ. ID. NO. 13155    125-GlyThrThrAspLeuAspLysGluSerTyrGlnAsnTyrArgLysSerMetGlnGluCysArgLysThrIleThrGluAlaGluAlaAsnLeuProLys
              Lys-158
957
AMPHI Regions - AMPHI
SEQ. ID. NO. 13156    11-SerPhePheAlaLeuValPheAla-18
SEQ. ID. NO. 13157    39-AlaThrGluValProLysAsnPro-46
SEQ. ID. NO. 13158    48-AlaPheValAlaLysLeuAlaArgLeuPheArgAsnAla-60
SEQ. ID. NO. 13159    76-AsnLeuAlaGlyThrValAspAsp-83
SEQ. ID. NO. 13160    198-GluAspValTyrGluHisCysLeuGlyCysTyrGlnMet-210
SEQ. ID. NO. 13161    218-TyrArgAspValAlaAsnAspGlu-225
SEQ. ID. NO. 13162    235-SerAsnArgIleAlaSer-240
SEQ. ID. NO. 13163    249-GlnAsnMetArgGluLeuMetProArg-257
SEQ. ID. NO. 13164    335-GluLysGluValArgArgTyrAlaGluAlaAlaAlaArg-367
Antigenic Index - Jameson-Wolf
SEQ. ID. NO. 13165    29-IleAsnProArgTrp-33
SEQ. ID. NO. 13166    35-LeuSerAspThrAlaThrGluValProLysAsnProAsn-47
SEQ. ID. NO. 13167    57-PheArgAsnAlaAspArgAla-63
SEQ. ID. NO. 13168    69-GluSerIleArgThrGluGluAsnLeuAlaGlyThrValAspAspGlyProLeuGlnSerGluLysAspTyr-92
SEQ. ID. NO. 13169    98-ArgLeuSerArgLeuLysGluLysAlaLys-107
SEQ. ID. NO. 13170    112-ThrGluGlnGluHisGlyLys-118
SEQ. ID. NO. 13171    125-HisIleGlyGluGlyGly-130
SEQ. ID. NO. 13172    136-LeuSerGlnArgSerProGluAlaPheVal-145

TABLE 1-continued

| | |
|---|---|
| SEQ. ID. NO. 13173 | 149-TyrLeuTyrArgAsnAspArgProPheSer-158 |
| SEQ. ID. NO. 13174 | 166-ValHisGlyGluAsnTyrGluThrThrGlyGluTyrArgVal-179 |
| SEQ. ID. NO. 13175 | 182-GlnProAspGlySerVal-187 |
| SEQ. ID. NO. 13176 | 190-AlaAlaGlyArgGlyLysIleGlyGluAspValTyr-201 |
| SEQ. ID. NO. 13177 | 217-LysTyrArgAspValAlaAsnAspGluGlnLysValTrpAspPheArgLysGluSerAsnArgIleAlaSerAspSerArgAsnSerValPheTyrGlnAsnMetArgGluLeuMetProArgGlyMetLysAlaAsnSer-263 |
| SEQ. ID. NO. 13178 | 267-GlyTyrAspAlaAspGlyLeuProGlnLys-276 |
| SEQ. ID. NO. 13179 | 280-SerPheAspAsnGlyLysLysArgGlnSerPheGluTyrTyrLeuLysAsnGlyAsn-298 |
| SEQ. ID. NO. 13180 | 309-LeuLysAlaAspGlyValThr-315 |
| SEQ. ID. NO. 13181 | 329-LeuAspGlyGlyArgIleValArgGluGluLysGlnGlyAspArgLeuProAspPhe-347 |
| SEQ. ID. NO. 13182 | 352-GluAsnLeuGluLysGluValArgArgTyrAlaGluAlaAlaAlaArgArgSerGlyGlyArgArgAspLeuSerHis-377 Hydrophilic Regions - Hopp-Woods |
| SEQ. ID. NO. 13183 | 38-ThrAlaThrGluValProLysAsnPro-46 |
| SEQ. ID. NO. 13184 | 57-PheArgAsnAlaAspArgAla-63 |
| SEQ. ID. NO. 13185 | 69-GluSerIleArgThrGluGluAsnLeu-77 |
| SEQ. ID. NO. 13186 | 80-ThrValAspAspGlyProLeuGlnSerGluLysAspTyr-92 |
| SEQ. ID. NO. 13187 | 98-ArgLeuSerArgLeuLysGluLysAlaLys-107 |
| SEQ. ID. NO. 13188 | 112-ThrGluGlnGluHisGlyLys-118 |
| SEQ. ID. NO. 13189 | 136-LeuSerGlnArgSerProGlu-142 |
| SEQ. ID. NO. 13190 | 151-TyrArgAsnAspArgProPhe-157 |
| SEQ. ID. NO. 13191 | 169-GluAsnTyrGluThrThrGlyGluTyr-177 |
| SEQ. ID. NO. 13192 | 190-AlaAlaGlyArgGlyLysIleGlyGluAspValTyr-201 |
| SEQ. ID. NO. 13193 | 217-LysTyrArgAspValAlaAsnAspGluGlnLysValTrpAspPheArgLysGluSerAsnArgIleAlaSerAspSerArgAsn-244 |
| SEQ. ID. NO. 13194 | 250-AsnMetArgGluLeuMetProArgGlyMetLys-260 |
| SEQ. ID. NO. 13195 | 268-TyrAspAlaAspGlyLeuPro-274 |
| SEQ. ID. NO. 13196 | 282-AspAsnGlyLysLysArgGlnSer-289 |
| SEQ. ID. NO. 13197 | 309-LeuLysAlaAspGlyValThr-315 |
| SEQ. ID. NO. 13198 | 331-GlyGlyArgIleValArgGluGluLysGlnGlyAspArgLeuPro-345 |
| SEQ. ID. NO. 13199 | 352-GluAsnLeuGluLysGluValArgArgTyrAlaGluAlaAlaAlaArgArgSerGlyGlyArgArgAspLeuSerHis-377 |
| 958 | |
| AMPHI Regions - AMPHI | |
| SEQ. ID. NO. 13200 | 34-AspAsnProThrAlaGlyGluSerValArgSerValSerGluProIleGln-50 |
| SEQ. ID. NO. 13201 | 86-ProGluAspTyrThrArgIleValAlaAsp-95 |
| SEQ. ID. NO. 13202 | 127-TyrAspGlnSerGlyAsp-132 |
| SEQ. ID. NO. 13203 | 176-GlyArgArgLeuGlnSerValSerArgThrAlaGluMet-188 |
| SEQ. ID. NO. 13204 | 343-IleSerAspThrLeuGln-348 |
| SEQ. ID. NO. 13205 | 483-TyrTyrSerLeuAsnArgPhe-489 |
| SEQ. ID. NO. 13206 | 491-SerGlnGluAlaArgArgVal-497 |
| SEQ. ID. NO. 13207 | 500-ThrLeuProIleVal-504 |
| SEQ. ID. NO. 13208 | 521-GlyGluValLeuGlnThrLeuGluProArgLeu-531 |
| SEQ. ID. NO. 13209 | 541-GlnAsnAspLeuProAsnPheAsp-548 |
| SEQ. ID. NO. 13210 | 572-AsnThrAlaAsnSerLeuSerAlaAlaValGlnSer-583 |
| SEQ. ID. NO. 13211 | 616-ValGlyLysLysPro-620 |
| SEQ. ID. NO. 13212 | 693-AspLysLeuSerGln-697 |
| SEQ. ID. NO. 13213 | 723-LysLysProIleGlu-727 |
| SEQ. ID. NO. 13214 | 769-AspLeuSerValGlyArgAsnPro-777 |
| Antigenic Index - Jameson-Wolf | |
| SEQ. ID. NO. 13215 | 28-ValAlaAlaGluGluThrAspAsnProThrAlaGlyGluSerValArgSerValSerGluProIleGln-50 |
| SEQ. ID. NO. 13216 | 55-SerLeuGlySerThr-59 |
| SEQ. ID. NO. 13217 | 63-CysSerAsnGluSerGlySerProGluArgThrGluAlaAlaValGlnGlySerGlyGluAlaSerIleProGluAspTyrThrArgIleValAlaAspArgMetGluGlyGlnSerGlnValGlnValArgAlaGluGly-109 |
| SEQ. ID. NO. 13218 | 111-ValValValGluArgAsnArgThrThrLeuAsn-121 |
| SEQ. ID. NO. 13219 | 123-AspTrpAlaAspTyrAspGlnSerGlyAspThrValThrAlaGlyAspArgPheAlaLeuGlnGlnAspGlyThrLeuIleArgGlyGluThrLeu-154 |
| SEQ. ID. NO. 13220 | 158-LeuGluGlnGlnThrGlyGluAlaHisAsnValArgMetGluIleGluGlnGlyGlyArgArgLeuGlnSerValSerArgThrAlaGluMetLeuGlyGluGlyHisTyrLysLeuThrGluThrGlnPheAsnThrCysSerAlaGlyAspAlaGlyTrp-211 |
| SEQ. ID. NO. 13221 | 216-AlaSerValGluAlaAspArgGluLysGlyIleGly-227 |
| SEQ. ID. NO. 13222 | 249-PheProLeuAspGlyAsnArgLysSerGlyLeu-259 |
| SEQ. ID. NO. 13223 | 265-SerAlaGlySerAspGlyVal-271 |
| SEQ. ID. NO. 13224 | 293-ValIleGlyGluArgGlyAlaValPheAspGlyGlnValArgTyrLeuArgProAspTyrAlaGlyGlnSerAsp-317 |
| SEQ. ID. NO. 13225 | 321-LeuProHisAspLysLysSerGlyArgAsnAsnArgTyrGlnAla-335 |
| SEQ. ID. NO. 13226 | 337-TrpGlnHisArgHisAspIleSerAspThrLeu-347 |
| SEQ. ID. NO. 13227 | 352-AspPheAsnGlnValSerAspSerGlyTyrTyrArgAspPheTyrGlyAsnLysGluIleAlaGlyAsnValAsnLeuAsnArgArgValTrp-382 |
| SEQ. ID. NO. 13228 | 384-AspTyrGlyGlyArgAlaAlaGlyGlySerLeu-394 |
| SEQ. ID. NO. 13229 | 407-AlaAsnGlnSerGlyTyrLysAspLysProTyr-417 |
| SEQ. ID. NO. 13230 | 425-ValGluTrpArgLysAsnThrGlyArgAla-434 |
| SEQ. ID. NO. 13231 | 444-ArgPheSerHisAspSerArgGlnAspGlySerArg-455 |
| SEQ. ID. NO. 13232 | 460-ProAspIleLysTrpAspPheSerAsnSerTrpGly-471 |
| SEQ. ID. NO. 13233 | 487-AsnArgPheGlySerGlnAlaArgArgValSerArg-499 |
| SEQ. ID. NO. 13234 | 507-AspSerGlyAlaThrPheGluArgAsnThrArgMetPheGly-520 |
| SEQ. ID. NO. 13235 | 538-AlaLysSerGlnAsnAspLeuProAsnPheAspSerSerGluSerSerPheGly-555 |
| SEQ. ID. NO. 13236 | 560-PheArgGluAsnLeuTyrTyrGlyAsnAspArgIleAsnThrAlaAsnSer-576 |
| SEQ. ID. NO. 13237 | 581-ValGlnSerArgIleLeuAspGlyAlaThrGlyGluGluArgPheArgAlaGlyIleGlyGlnLysPheTyrPheLysAspAspAlaValMetLeuAspGlySerValGlyLysLysProArgAsnArgSerAspTrp-626 |
| SEQ. ID. NO. 13238 | 631-SerGlySerIleGlySer-636 |
| SEQ. ID. NO. 13239 | 642-SerSerIleHisTyrAsnGlnAsnAspLysArgAlaGluAsn-655 |
| SEQ. ID. NO. 13240 | 660-AlaSerTyrArgProAlaGlnGlyLysValLeuAsnAlaArgTyrLysTyrGlyArgAsnGluLysIleTyrLeuLysSerAspGlySerTyrPhe-691 |
| SEQ. ID. NO. 13241 | 693-AspLysLeuSerGln-697 |
| SEQ. ID. NO. 13242 | 718-TyrGlyPheGluAlaLysLysProIleGlu-727 |
| SEQ. ID. NO. 13243 | 732-AlaGluTyrLysSerSerCysGlyCysTrp-741 |
| SEQ. ID. NO. 13244 | 751-ValThrGlyGluAsnThrTyrLysAsn-759 |

TABLE 1-continued

| | |
|---|---|
| SEQ. ID. NO. 13245 | 766-GlnLeuLysAspLeuSerSerValGlyArgAsnProAlaAspArgMetAspVal-783 |
| SEQ. ID. NO. 13246 | 794-LeuSerAlaGlyArgAsnLysArgPro-802 |
| Hydrophilic Regions - Hopp-Woods | |
| SEQ. ID. NO. 13247 | 28-ValAlaAlaGluGluThrAspAsnProThrAlaGlyGluSerValArgSerValSerGluProIleGln-50 |
| SEQ. ID. NO. 13248 | 65-AsnGluSerGlySerProGluArgThrGluAlaAlaVal-77 |
| SEQ. ID. NO. 13249 | 79-GlySerGlyGluAlaSerIleProGluAspTyrThr-90 |
| SEQ. ID. NO. 13250 | 93-ValAlaAspArgMetGluGlyGlnSer-101 |
| SEQ. ID. NO. 13251 | 103-ValGlnValArgAlaGluGly-109 |
| SEQ. ID. NO. 13252 | 111-ValValValGlyArgAsnArgThrThrLeu-120 |
| SEQ. ID. NO. 13253 | 125-AlaAspTyrAspGlnSerGlyAspThrValThrAlaGlyAspArgPheAlaLeu-142 |
| SEQ. ID. NO. 13254 | 147-ThrLeuIleArgGlyGluThr-153 |
| SEQ. ID. NO. 13255 | 160-GlnGlnThrGlyGluAlaHisAsnValArgMetGluIleGluGlnGlyGlyArgArgLeuGlnSerValSerArgThrAlaGluMetLeuGly-190 |
| SEQ. ID. NO. 13256 | 192-GlyHisTyrLysLeuThrGlu-198 |
| SEQ. ID. NO. 13257 | 216-AlaSerValGluAlaAspArgGluLysGlyIleGly-227 |
| SEQ. ID. NO. 13258 | 250-ProLeuAspGlyAsnArgLysSerGly-258 |
| SEQ. ID. NO. 13259 | 266-AlaGlySerAspGlyVal-271 |
| SEQ. ID. NO. 13260 | 294-IleGlyGluArgGlyAlaVal-300 |
| SEQ. ID. NO. 13261 | 305-ValArgTyrLeuArg-309 |
| SEQ. ID. NO. 13262 | 323-HisAspLysLysSerGlyArgAsnAsnArgTyrGlnAla-335 |
| SEQ. ID. NO. 13263 | 337-TrpGlnHisArgHisAspIleSerAsp-345 |
| SEQ. ID. NO. 13264 | 410-SerGlyTyrLysAspLysProTyr-417 |
| SEQ. ID. NO. 13265 | 425-ValGluTrpLysAsnThrGlyArgAla-434 |
| SEQ. ID. NO. 13266 | 445-PheSerHisAspSerArgGlnAspGlySerArg-455 |
| SEQ. ID. NO. 13267 | 490-GlySerGlnGluAlaArgArgValSerArg-499 |
| SEQ. ID. NO. 13268 | 510-AlaThrPheGluArgAsnThrArg-517 |
| SEQ. ID. NO. 13269 | 539-LysSerGlnAsnAsp-543 |
| SEQ. ID. NO. 13270 | 548-AspSerSerGluSer-552 |
| SEQ. ID. NO. 13271 | 569-AspArgIleAsnThr-573 |
| SEQ. ID. NO. 13272 | 589-AlaThrGlyGluGluArgPheArgAla-597 |
| SEQ. ID. NO. 13273 | 604-TyrPheLysAspAspAlaValMet-611 |
| SEQ. ID. NO. 13274 | 615-SerValGlyLysLysProArgAsnArgSerAsp-625 |
| SEQ. ID. NO. 13275 | 648-GlnAsnAspLysArgAlaGluAsn-655 |
| SEQ. ID. NO. 13276 | 662-TyrArgProAlaGln-666 |
| SEQ. ID. NO. 13277 | 674-TyrLysTyrGlyArgAsnGluLysIleTyrLeuLysSerAspGly-688 |
| SEQ. ID. NO. 13278 | 720-PheGluAlaLysLysProIleGlu-727 |
| SEQ. ID. NO. 13279 | 732-AlaGluTyrLysSer-736 |
| SEQ. ID. NO. 13280 | 766-GlnLeuLysAspLeuSerSerValGlyArgAsnProAlaAspArgMetAspVal-783 |
| SEQ. ID. NO. 13281 | 795-SerAlaGlyArgAsnLysArgPro-802 |
| 959 | |
| AMPHI Regions - AMPHI | |
| SEQ. ID. NO. 13282 | 56-AlaAlaLeuAlaArgValGlyGly-63 |
| Antigenic Index - Jameson-Wolf | |
| SEQ. ID. NO. 13283 | 24-AlaHisHisAspGlyHisGlyAspAspAspHisGlyHis-36 |
| SEQ. ID. NO. 13284 | 38-AlaHisGlnHisAsnLysGlnAspLysIleIleSer-49 |
| SEQ. ID. NO. 13285 | 51-AlaGlnAlaGluLysAlaAlaLeu-58 |
| SEQ. ID. NO. 13286 | 60-ArgValGlyGlyLysIleThrAspIleAspLeuGluHisAspAsnGlyArgProHisTyrAspValGluIleValLysAsnGlyGlnGluTyr-90 |
| SEQ. ID. NO. 13287 | 94-ValAspAlaArgThrGlyArgValIleSerSerArgArgAspAsp-108 |
| Hydrophilic Regions - Hopp-Woods | |
| SEQ. ID. NO. 13288 | 27-AspGlyHisGlyAspAspAspHisGlyHis-36 |
| SEQ. ID. NO. 13289 | 40-GlnHisAsnLysGlnAspLysIleIleSer-49 |
| SEQ. ID. NO. 13290 | 51-AlaGlnAlaGluLysAlaAlaLeu-58 |
| SEQ. ID. NO. 13291 | 61-ValGlyGlyLysIleThrAspIleAspLeuGluHisAspAsnGlyArgProHisTyr-79 |
| SEQ. ID. NO. 13292 | 82-GluIleValLysAsnGlyGlnGluTyr-90 |
| SEQ. ID. NO. 13293 | 94-ValAspAlaArgThrGlyArg-100 |
| SEQ. ID. NO. 13294 | 102-IleSerSerArgArgAspAsp-108 |
| 960 | |
| AMPHI Regions - AMPHI | |
| SEQ. ID. NO. 13295 | 24-AlaProArgLeuLeuProSerPheThrAspPro-34 |
| SEQ. ID. NO. 13296 | 39-LeuSerAlaProGlyGlyTyrIleVal-47 |
| SEQ. ID. NO. 13297 | 58-IleGluLysLeuAlaLysGlnProGluTyrAlaTyrLeuLysGlnLeuGlnValAlaLysAsnValAsn-80 |
| SEQ. ID. NO. 13298 | 137-PheAlaSerLeuAlaSer-142 |
| SEQ. ID. NO. 13299 | 154-AspValGlyLysThrLeuLysGluLeuGlyArgSerArgThr-167 |
| SEQ. ID. NO. 13300 | 189-LeuAlaThrTrpSerGlu-194 |
| SEQ. ID. NO. 13301 | 230-AsnIleLeuAlaAlaLeuValAsnThrAla-239 |
| SEQ. ID. NO. 13302 | 245-SerLysIleLysGly-249 |
| SEQ. ID. NO. 13303 | 257-HisLysIleAlaHisAlaValAlaGlyCysAla-267 |
| SEQ. ID. NO. 13304 | 280-AlaIleGlyAlaAlaValGlyGluIleValGlyGlu-291 |
| SEQ. ID. NO. 13305 | 314-IleThrAlaTyrAlaLys-319 |
| SEQ. ID. NO. 13306 | 338-GlnThrAlaGlnAsnAla-343 |
| SEQ. ID. NO. 13307 | 345-GluAsnAsnAlaValLysAlaValValThr-354 |
| SEQ. ID. NO. 13308 | 359-ValTyrLysValAlaArgLysGly-366 |
| SEQ. ID. NO. 13309 | 387-AsnLeuAlaAspAsnLeuThrThrLeuPheAsp-397 |
| SEQ. ID. NO. 13310 | 418-AsnArgAlaAsnLysGlyGluAlaAlaGlnLysLysGluValLeu-433 |
| SEQ. ID. NO. 13311 | 460-LysGlnLeuAlaGlnIle-465 |
| Antigenic Index - Jameson-Wolf | |
| SEQ. ID. NO. 13312 | 11-LeuTyrArgArgGlySerValLysProProLeu-21 |
| SEQ. ID. NO. 13313 | 23-GluAlaProArgLeuLeuProSerPheThrAsp-33 |
| SEQ. ID. NO. 13314 | 35-ValValProLysLeuSerAlaProGly-43 |
| SEQ. ID. NO. 13315 | 48-AspIleProLysGlyAsnLeuLysThrGluIleGluLysLeuAlaLysGlnProGlu-66 |
| SEQ. ID. NO. 13316 | 77-LysAsnValAsnTrp-81 |

TABLE 1-continued

| | |
|---|---|
| SEQ. ID. NO. 13317 | 87-AlaTyrAspLysTrpAspTyrLysGlnGluGlyLeuThr-99 |
| SEQ. ID. NO. 13318 | 150-AsnAsnLysGlyAspValGlyLysThrLeuLysGluLeuGlyArgSerArgThrValLys-169 |
| SEQ. ID. NO. 13319 | 180-ValSerAsnLysLeuGlyAla-186 |
| SEQ. ID. NO. 13320 | 193-SerGluThrProTrp-197 |
| SEQ. ID. NO. 13321 | 218-ValAsnGlyGlySerLeuLysAspAsnLeuGlu-228 |
| SEQ. ID. NO. 13322 | 239-AlaHisGlyGluAlaAlaSerLysIleLysGlyLeuAsp-251 |
| SEQ. ID. NO. 13323 | 270-AlaAlaAsnLysGlyLysCysGlnAspGlyAla-280 |
| SEQ. ID. NO. 13324 | 292-AlaLeuValLysAsnThrAspPheSerAspMetThrProGluGlnLeuAspLeuGluValLysLys-313 |
| SEQ. ID. NO. 13325 | 329-ThrGlyGlyAspValAsnThr-335 |
| SEQ. ID. NO. 13326 | 362-ValAlaArgLysGlyLeuLysAsnGlyLysIleAsnValArgAspLeuLysGlnThrLeuLysAspGluGlyTyrAsnLeu-388 |
| SEQ. ID. NO. 13327 | 398-GluThrLeuAspTrpAsnAspAlaLysAla-407 |
| SEQ. ID. NO. 13328 | 415-ThrGluLeuAsnArgAlaAsnLysGlyGluAlaAlaGlnLysValLysGluValLeuGluLysAsnArgProTyrIleProAsnLysGlyAlaValPro-447 |
| SEQ. ID. NO. 13329 | 451-ThrTyrMetLysAsnAsnProPheGlyLysGln-461 |
| SEQ. ID. NO. 13330 | 465-IleSerGluLysThrThrLeuProThrGlnGlnGlyGlnSer-478 |
| SEQ. ID. NO. 13331 | 483-LysArgAsnGlnGlyLeuLeuLysThrGlyAspArgPheTyrLeuAspGlyGlnHisLysAsnHisLeu-505 |
| SEQ. ID. NO. 13332 | 507-ValPheAspLysAsnGlyAsnPheLys-515 |
| SEQ. ID. NO. 13333 | 520-MetAspGlySerLeuAsnGlnMetLysThrGlyAlaAlaLysGlyArgLysLeuAsnLeu-539 |
| Hydrophilic Regions - Hopp-Woods | |
| SEQ. ID. NO. 13334 | 13-ArgArgGlySerValLys-18 |
| SEQ. ID. NO. 13335 | 49-IleProLysGlyAsnLeuLysThrGluIleGluLysLeuAlaLysGlnProGlu-66 |
| SEQ. ID. NO. 13336 | 89-AspLysTrpAspTyrLysGlnGluGlyLeuThr-99 |
| SEQ. ID. NO. 13337 | 150-AsnAsnLysGlyAspValGlyLysThrLeuLysGluLeuGlyArgSerArgThrValLys-169 |
| SEQ. ID. NO. 13338 | 221-GlySerLeuLysAspAsnLeuGlu-228 |
| SEQ. ID. NO. 13339 | 239-AlaHisGlyGluAlaAlaSerLysIleLysGlyLeuAsp-251 |
| SEQ. ID. NO. 13340 | 270-AlaAlaAsnLysGlyLysCysGlnAsp-278 |
| SEQ. ID. NO. 13341 | 292-AlaLeuValLysAsnThrAspPheSerAspMetThrProGluGlnLeuAspLeuGluValLysLys-313 |
| SEQ. ID. NO. 13342 | 362-ValAlaArgLysGlyLeuLysAsnGlyLysIleAsnValArgAspLeuLysGlnThrLeuLysAspGluGlyTyrAsn-387 |
| SEQ. ID. NO. 13343 | 398-GluThrLeuAspTrpAsnAspAlaLysAla-407 |
| SEQ. ID. NO. 13344 | 416-GluLeuAsnArgAlaAsnLysGlyGluAlaAlaGlnLysValLysGluValLeuGluLysAsnArgPro-438 |
| SEQ. ID. NO. 13345 | 465-IleSerGluLysThrThrLeu-471 |
| SEQ. ID. NO. 13346 | 483-LysArgAsnGlnGly-487 |
| SEQ. ID. NO. 13347 | 499-GlyGlnHisLysAsnHis-504 |
| SEQ. ID. NO. 13348 | 507-ValPheAspLysAsnGlyAsn-513 |
| SEQ. ID. NO. 13349 | 522-GlySerLeuAsnGln-526 |
| SEQ. ID. NO. 13350 | 528-LysThrGlyAlaAlaLysGlyArgLysLeuAsnLeu-539 |
| 961-2 | |
| AMPHI Regions - AMPHI | |
| SEQ. ID. NO. 13351 | 6-PheProSerLysVal-10 |
| SEQ. ID. NO. 13352 | 13-ThrAlaIleLeuAlaThrPheCysSerGly-22 |
| SEQ. ID. NO. 13353 | 46-AsnGlyGlnGluIleAsnGlyPheLysAlaGlyGluThrIleTyrAspIle-62 |
| SEQ. ID. NO. 13354 | 90-LysValValThrAsnLeuThrLysThrVal-99 |
| SEQ. ID. NO. 13355 | 118-GluLysLeuThrThr-122 |
| SEQ. ID. NO. 13356 | 138-LeuAspGluThrThrAsnAlaLeuAsnLysLeuGlyGluAsnIleThrThrPheAla-156 |
| SEQ. ID. NO. 13357 | 170-LeuGluAlaValAlaAspThrValAspLysHisAlaGluAlaPheAsnAspIleAlaAspSerLeuAsp-192 |
| SEQ. ID. NO. 13358 | 200-GluAlaValLysThrAlaAsnGluAlaLysGlnThrAlaGlu-213 |
| SEQ. ID. NO. 13359 | 273-AlaArgIleAspSerLeuAspLysAsnValAlaAsnLeuArgLysGluThrArgGlnGlyLeu-293 |
| SEQ. ID. NO. 13360 | 300-SerGlyLeuPheGlnProTyrAsnVal-308 |
| Antigenic Index - Jameson-Wolf | |
| SEQ. ID. NO. 13361 | 27-ThrSerAspAspAspValLysLysAlaAla-36 |
| SEQ. ID. NO. 13362 | 45-AsnAsnGlyGlnGluIleAsnGlyPheLysAlaGlyGluThr-58 |
| SEQ. ID. NO. 13363 | 60-TyrAspIleGlyGluAspGlyThrIleThrGlnLysAspAlaThrAlaAlaAspValGluAlaAspAspPheLys-84 |
| SEQ. ID. NO. 13364 | 98-ThrValAsnGluAsnLysGlnAsnValAspAlaLysValLysAlaAlaGluSerGluIleGluLysLeuThrThrLysLeuAlaAspThrAspAlaAlaLeuAlaAspThrAspAlaAlaLeuAspGluThrThrAsnAlaLeuAsnLysLeuGlyGluAsnIleThr-153 |
| SEQ. ID. NO. 13365 | 155-PheAlaGluGluThrLysThrAsnIleValLysIleAspGluLysLeuGluAlaValAlaAspThrValAspLysHisAlaGluAlaPheAsnAspIleAlaAspSerLeuAspGluThrAsnThrLysAlaAspGluAlaValLysThrAlaAsnGluAlaLysGlnThrAlaGluGluThrLysGlnAsnValAspAlaLysValLysAlaAlaGluThrAlaAlaGlyLysAlaGluAlaAlaAla-237 |
| SEQ. ID. NO. 13366 | 239-ThrAlaAsnThrAlaAlaAspLysAlaGluAlaValAla-251 |
| SEQ. ID. NO. 13367 | 253-LysValThrAspIleLysAlaAspIleAlaThrAsnLysAlaAspIleAlaLysAsnSerAlaArgIleAspSerLeuAspLysAsnValAlaAsnLeuArgLysGluThrArgGlnGlyLeuAla-294 |
| SEQ. ID. NO. 13368 | 317-ValGlyGlyTyrLysSerGluSer-324 |
| SEQ. ID. NO. 13369 | 330-ThrGlyPheArgPhe-334 |
| SEQ. ID. NO. 13370 | 348-ThrSerSerGlySerSerAla-354 |
| Hydrophilic Regions - Hopp-Woods | |
| SEQ. ID. NO. 13371 | 27-ThrSerAspAspAspValLysLysAlaAla-36 |
| SEQ. ID. NO. 13372 | 54-LysAlaGlyGluThr-58 |
| SEQ. ID. NO. 13373 | 62-IleGlyGluAspGlyThrIleThrGlnLysAspAlaThrAlaAlaAspValGluAlaAspAspPheLys-84 |
| SEQ. ID. NO. 13374 | 98-ThrValAsnGluAsnLysGlnAsnValAspAlaLysValLysAlaAlaGluSerGluIleGluLysLeuThrThrLysLeuAlaAspThrAspAlaAlaLeuAlaAspThrAspAlaAlaLeuAspGluThrThrAsnAla-144 |
| SEQ. ID. NO. 37765 | 155-PheAlaGluGluThrLysThrAsnIleValLysIleAspGluLysLeuGluAlaValAlaAspThrValAspLysHisAlaGluAlaPheAsnAspIleAlaAspSerLeuAspGluThrAsnThrLysAlaAspGluAlaValLysThrAlaAsnGluAlaLysGlnThrAlaGluGluThrLysGlnAsnValAspAlaLysValLysAlaAlaGluThrAlaAlaGlyLysAlaGluAlaAlaAla-237 |
| SEQ. ID. NO. 13375 | 242-ThrAlaAlaAspLysAlaGluAlaValAla-251 |
| SEQ. ID. NO. 13376 | 253-LysValThrAspIleLysAlaAspIleAlaThrAsnLysAlaAspIleAlaLysAsnSerAlaArgIleAspSerLeuAspLysAsnValAlaAsnLeuArgLysGluThrArgGlnGlyLeuAla-294 |
| SEQ. ID. NO. 13377 | 320-TyrLysSerGluSer-324 |
| 972-2 | |
| AMPHI Regions - AMPHI | |
| SEQ. ID. NO. 13378 | 15-SerSerGluArgMetSerGluValGluTyrPheSerHis-27 |
| SEQ. ID. NO. 13379 | 83-ArgLysLeuGluGluIleLeuGly-90 |
| SEQ. ID. NO. 13380 | 100-ArgGlyAsnLysPheTyrGluSerMetTyrArgLeu-111 |

TABLE 1-continued

| SEQ. ID. NO. 13381 | 154-LeuAspAspSerIleArg-159 |
| SEQ. ID. NO. 13382 | 226-PheValArgValTyrGluLysGly-233 |
| SEQ. ID. NO. 13383 | 275-IleCysArgLysPheLysAsnMetProValPro-285 |
| SEQ. ID. NO. 13384 | 308-AsnAlaValGlyLysLeuValAsnPhe-316 |
| SEQ. ID. NO. 13385 | 326-GluIleValGluSerLeuLysAla-333 |
| SEQ. ID. NO. 13386 | 336-GlyPheProLysGlyLeuGlu-342 |
| SEQ. ID. NO. 13387 | 348-LeuGluMetLeuArgAspGlyLeuLys-356 |
| SEQ. ID. NO. 13388 | 382-AsnSerAspLysPheAspArg-388 |

Antigenic Index - Jameson-Wolf

| SEQ. ID. NO. 13389 | 1-LeuThrAsnArgGlyGlyAlaLysLeuLysThrAsnSerLysSerSerGluArgMetSerGlu-21 |
| SEQ. ID. NO. 13390 | 29-IleSerAspGlyLysGlyLysLeuLeuGluIleProGlnArgArgGlyLysGlnAspGlyVal-49 |
| SEQ. ID. NO. 13391 | 62-ThrLeuLeuLysValSerGly-68 |
| SEQ. ID. NO. 13392 | 83-ArgLysLeuGluGlu-87 |
| SEQ. ID. NO. 13393 | 93-IleThrArgLysCysLysSerArgGlyAsnLysPheTyrGlu-106 |
| SEQ. ID. NO. 13394 | 108-MetTyrArgLeuGlySerAspAspValAspTyrGly-119 |
| SEQ. ID. NO. 13395 | 122-HisPheGlyGlyGlnArgAsnThrVal-130 |
| SEQ. ID. NO. 13396 | 134-LeuLysGlyThrGlyCys-139 |
| SEQ. ID. NO. 13397 | 152-GlnPheLeuAspAspSerIleArgThrArgIleThrArg-164 |
| SEQ. ID. NO. 13398 | 172-PheAspGlyGluTyrThrProAspGlnAlaLeuLeuAspHisAspAsnGlyPhePheAspAsnSerAsnGlnArgProLysSerGluThrIleGly-203 |
| SEQ. ID. NO. 13399 | 205-AlaTrpArgAsnGluAspGlySerGlyLys-214 |
| SEQ. ID. NO. 13400 | 217-TyrValGlyArgLysLysAsnSerArgPhe-226 |
| SEQ. ID. NO. 13401 | 228-ArgValTyrGluLysGlyArgGlnLeuGlyAspLysGluSerLysTrpVal-244 |
| SEQ. ID. NO. 13402 | 251-AsnTyrGlyAspIleGluIle-257 |
| SEQ. ID. NO. 13403 | 263-IleAsnGlnGlySer-267 |
| SEQ. ID. NO. 13404 | 275-IleCysArgLysPheLysAsnMetProValProGluArgPheAspGlnArgLysLysLysLeu-295 |
| SEQ. ID. NO. 13405 | 321-GlyPheAspAsnSerGluIleValGluSerLeuLysAlaAspSerGlyPheProLysGlyLeuGluProGluLysTyrAla-347 |
| SEQ. ID. NO. 13406 | 350-MetLeuArgAspGlyLeuLys-356 |
| SEQ. ID. NO. 13407 | 361-HisGluGlnProAspIleAspLeuGluIleGluLeuAspGlu-374 |
| SEQ. ID. NO. 13408 | 380-PheLysAsnSerAspLysPheAspArgGluLysArgLeuPheSerProAspTyrAspValGluLysGluArgLysTyrGlnGluTyrLeu-409 |
| SEQ. ID. NO. 13409 | 417-ValAspTyrAspTyrPhe-422 |

Hydrophilic Regions - Hopp-Woods

| SEQ. ID. NO. 13410 | 1-LeuThrAsnArgGlyGlyAlaLysLeuLysThrAsnSerLysSerSerGluArgMetSerGlu-21 |
| SEQ. ID. NO. 13411 | 30-SerAspGlyLysGlyLysLeuLeuGluIleProGlnArgArgGlyLysGlnAspGlyVal-49 |
| SEQ. ID. NO. 13412 | 83-ArgLysLeuGluGlu-87 |
| SEQ. ID. NO. 13413 | 93-IleThrArgLysCysLysSerArgGlyAsnLysPheTyr-105 |
| SEQ. ID. NO. 13414 | 111-LeuGlySerAspAspValAspTyrGly-119 |
| SEQ. ID. NO. 13415 | 134-LeuLysGlyThrGly-138 |
| SEQ. ID. NO. 13416 | 152-GlnPheLeuAspAspSerIleArgThrArgIleThrArg-164 |
| SEQ. ID. NO. 13417 | 181-AlaLeuLeuAspHisAspAsnGlyPhe-189 |
| SEQ. ID. NO. 13418 | 193-SerAsnGlnArgProLysSerGluThrIle-202 |
| SEQ. ID. NO. 13419 | 206-TrpArgAsnGluAspGlySerGly-213 |
| SEQ. ID. NO. 13420 | 219-GlyArgLysLysAsnSerArgPhe-226 |
| SEQ. ID. NO. 13421 | 228-ArgValTyrGluLysGlyArgGlnLeuGlyAspLysGluSerLysTrpVal-244 |
| SEQ. ID. NO. 13422 | 277-ArgLysPheLysAsn-281 |
| SEQ. ID. NO. 13423 | 283-ProValProGluArgPheAspGlnArgLysLysLysLeu-295 |
| SEQ. ID. NO. 13424 | 321-GlyPheAspAsnSerGluIleValGluSerLeuLysAlaAspSerGlyPhe-337 |
| SEQ. ID. NO. 13425 | 339-LysGlyLeuGluProGluLysTyrAla-347 |
| SEQ. ID. NO. 13426 | 350-MetLeuArgAspGlyLeuLys-356 |
| SEQ. ID. NO. 13427 | 362-GluGlnProAspIleAspLeuGluIleGluLeuAspGlu-374 |
| SEQ. ID. NO. 13428 | 381-LysAsnSerAspLysPheAspArgGluLysArgLeuPhe-393 |
| SEQ. ID. NO. 13429 | 396-AspTyrAspValGluLysGluArgLysTyrGlnGluTyrLeu-409 |

973-2

AMPHI Regions - AMPHI

| SEQ. ID. NO. 13430 | 12-GluArgLeuIleAlaArgLeuAlaArgGluProAspSerAlaGluAspValLeuAsnLeuLeuArgGlnAla-35 |
| SEQ. ID. NO. 13431 | 44-AspThrLeuLeuArgLeuGluLysValLeuAspPhe-55 |
| SEQ. ID. NO. 13432 | 77-AspSerIleGluArgIleThrAlaTyr-85 |
| SEQ. ID. NO. 13433 | 112-AspLeuLeuLysTyrMet-117 |
| SEQ. ID. NO. 13434 | 143-AlaLeuLeuLysGluPheArgGluGln-151 |
| SEQ. ID. NO. 13435 | 171-PheGluAspIleIleGluGlnIleValGlyGluIleGluAsp-184 |
| SEQ. ID. NO. 13436 | 194-AsnIleHisAlaVal-198 |
| SEQ. ID. NO. 13437 | 208-AlaThrGluIleGluAspIleAsnThrPhe-217 |
| SEQ. ID. NO. 13438 | 235-IleGlnGluLeuGly-239 |

Antigenic Index - Jameson-Wolf

| SEQ. ID. NO. 13439 | 1-MetAspGlyAlaGlnProLysThrAsnPhe-10 |
| SEQ. ID. NO. 13440 | 18-LeuAlaArgGluProAspSerAlaGluAspVal-28 |
| SEQ. ID. NO. 13441 | 34-GlnAlaHisGluGlnGluValPheAspAlaAspThr-45 |
| SEQ. ID. NO. 13442 | 47-LeuArgLeuGluLysValLeuAsp-54 |
| SEQ. ID. NO. 13443 | 56-SerAspLeuGluValArgAspAlaMetIleThrArgSerArgMetAsnValLeuLysGluAsnAspSerIleGluArg-81 |
| SEQ. ID. NO. 13444 | 96-ValIleGlyGluAspLysAspGluVal-104 |
| SEQ. ID. NO. 13445 | 118-PheAsnProGluGlnPheHis-124 |
| SEQ. ID. NO. 13446 | 136-ProGluGlyLysSer-140 |
| SEQ. ID. NO. 13447 | 146-LysGluPheArgGluGlnArgAsnHis-154 |
| SEQ. ID. NO. 13448 | 159-IleAspGluTyrGlyGlyThrSerGly-167 |
| SEQ. ID. NO. 13449 | 178-IleValGlyGluIleGluAspGluPheAspGluAspSerAlaAspAsn-194 |
| SEQ. ID. NO. 13450 | 199-SerSerGluArgTrpArg-204 |
| SEQ. ID. NO. 13451 | 209-ThrGluIleGluAspIleAsn-215 |
| SEQ. ID. NO. 13452 | 218-PheGlyThrGluTyrSerSerGluGluAlaAspThr-229 |
| SEQ. ID. NO. 13453 | 239-GlyHisLeuProValArgGlyGluLysValLeu-249 |
| SEQ. ID. NO. 13454 | 258-AlaArgAlaAspAsnArgArgLeuHis-266 |

TABLE 1-continued

Hydrophilic Regions - Hopp-Woods
SEQ. ID. NO. 13455    1-MetAspGlyAlaGlnProLys-7
SEQ. ID. NO. 13456    18-LeuAlaArgGluProAspSerAlaGluAspVal-28
SEQ. ID. NO. 13457    34-GlnAlaHisGluGlnGluValPheAsp-42
SEQ. ID. NO. 13458    47-LeuArgLeuGluLysValLeuAsp-54
SEQ. ID. NO. 13459    56-SerAspLeuGluValArgAspAlaMetIleThrArgSerArgMetAsnValLeuLysGluAsnAspSerIleGluArg-81
SEQ. ID. NO. 13460    96-ValIleGlyGluAspLysAspGluVal-104
SEQ. ID. NO. 13461    136-ProGluGlyLysSer-140
SEQ. ID. NO. 13462    146-LysGluPheArgGluGlnArgAsn-153
SEQ. ID. NO. 13463    178-IleValGlyGluIleGluAspGluPheAspGluAspAspSerAlaAspAsn-194
SEQ. ID. NO. 13464    199-SerSerGluArgTrpArg-204
SEQ. ID. NO. 13465    209-ThrGluIleGluAsp-213
SEQ. ID. NO. 13466    222-TyrSerSerGluGluAlaAspThr-229
SEQ. ID. NO. 13467    243-ValArgGlyGluLysValLeu-249
SEQ. ID. NO. 13468    258-AlaArgAlaAspAsnArgArgLeuHis-266
981-2
AMPHI Regions - AMPHI
SEQ. ID. NO. 13469    33-AlaAsnProAspLysValTyrArgValAlaSer-43
SEQ. ID. NO. 13470    48-AlaProPheGluSerLeuAsp-54
SEQ. ID. NO. 13471    68-AsnAlaMetAlaLys-72
SEQ. ID. NO. 13472    134-LysValSerSerSerGluAspLeuLysAsnMetAsnLysValGlyValVal-150
SEQ. ID. NO. 13473    169-LysIleAlaArgPheGlu-174
SEQ. ID. NO. 13474    183-LeuGluAsnGlyGlyLeuAspSerValVal-192
SEQ. ID. NO. 13475    199-AlaAsnTyrValLysAsnAsnPro-206
SEQ. ID. NO. 13476    209-GlyMetAspPheValThrLeuPro-216
SEQ. ID. NO. 13477    235-ValLysMetLeuAsnAspAlaLeuGluLysValArgGluSerGlyGluTyr-251
Antigenic Index - Jameson-Wolf
SEQ. ID. NO. 13478    21-CysGlyGlyGlnGlyLysAspThrAlaAla-30
SEQ. ID. NO. 13479    33-AlaAsnProAspLysValTyrArg-40
SEQ. ID. NO. 13480    51-GluSerLeuAspSerLysGlyAsnValGluGlyPheAsp-63
SEQ. ID. NO. 13481    78-IleGluPheLysHisGlnProTrpAspSer-87
SEQ. ID. NO. 13482    92-LeuAsnAsnGlyAspAlaAspVal-99
SEQ. ID. NO. 13483    106-IleThrAspAspArgLysGlnSerMetAspPheSerAspProTyrPhe-121
SEQ. ID. NO. 13484    129-ValProLysGlyLysLysValSerSerSerGluAspLeuLysAsnMetAsnLys-146
SEQ. ID. NO. 13485    162-LeuLeuGlyAsnAspAsnProLysIleAlaArg-172
SEQ. ID. NO. 13486    181-LysGluLeuGluAsnGlyGlyLeuAspSerValValSerAspSerAla-196
SEQ. ID. NO. 13487    203-LysAsnAsnProAlaLysGlyMetAspPhe-212
SEQ. ID. NO. 13488    216-ProAspPheThrThr-220
SEQ. ID. NO. 13489    227-ValArgLysGlyAspGluAlaThrVal-235
SEQ. ID. NO. 13490    237-MetLeuAsnAspAlaLeuGluLysValArgGluSerGlyGluTyrAspLysIleTyr-255
SEQ. ID. NO. 13491    259-PheAlaLysGluAspGlyGlnAlaAlaLys-268
Hydrophilic Regions - Hopp-Woods
SEQ. ID. NO. 13492    23-GlyGlnGlyLysAspThrAlaAla-30
SEQ. ID. NO. 13493    33-AlaAsnProAspLysValTyrArg-40
SEQ. ID. NO. 13494    51-GluSerLeuAspSerLysGlyAsnValGluGlyPheAsp-63
SEQ. ID. NO. 13495    93-AsnAsnGlyAspAlaAspVal-99
SEQ. ID. NO. 13496    106-IleThrAspAspArgLysGlnSerMetAspPheSer-117
SEQ. ID. NO. 13497    130-ProLysGlyLysLysValSerSerSerGluAspLeuLysAsnMetAsn-145
SEQ. ID. NO. 13498    166-AspAsnProLysIleAlaArg-172
SEQ. ID. NO. 13499    181-LysGluLeuGluAsnGlyGlyLeu-188
SEQ. ID. NO. 13500    205-AsnProAlaLysGlyMetAsp-211
SEQ. ID. NO. 13501    227-ValArgLysGlyAspGluAlaThrVal-235
SEQ. ID. NO. 13502    237-MetLeuAsnAspAlaLeuGluLysValArgGluSerGlyGluTyrAspLysIleTyr-255
SEQ. ID. NO. 13503    259-PheAlaLysGluAspGlyGlnAlaAlaLys-268
982
AMPHI Regions - AMPHI
SEQ. ID. NO. 13504    12-ValArgGlnLysMetValAsnGlyValAsnIleLeuAlaAsnAlaVal-27
SEQ. ID. NO. 13505    71-AlaGlnMetValLysGluValAlaSerLysThr-81
SEQ. ID. NO. 13506    100-ValAlaGluGlyMetLysTyr-106
SEQ. ID. NO. 13507    115-AspLeuLysArgGlyIleAspLysAlaValAlaAlaLeuValAspGlu
                      LeuLysAsnIleAlaLysProCysAspThrSerLysGluIleAlaGlnValGlySer-149
SEQ. ID. NO. 13508    160-AlaIleIleAlaGluAlaMetGluLysValGly-170
SEQ. ID. NO. 13509    185-AsnGluLeuAspValValGluGlyMet-193
SEQ. ID. NO. 13510    209-GluLysGlnIleAlaAla-214
SEQ. ID. NO. 13511    227-IleSerAsnIleArgAspLeuLeuProValLeuGluGlnValAlaLysAla-243
SEQ. ID. NO. 13512    265-AsnAsnIleArgGlyIleLeuLysThrValAla-275
SEQ. ID. NO. 13513    313-ThrLeuAspAspLeuGlyGlnAlaLysArgIle-323
SEQ. ID. NO. 13514    331-ThrIleIleAspGlyPheGlyAspAlaAla-340
SEQ. ID. NO. 13515    367-GluArgValAlaLysLeuAlaGlyGlyVal-376
SEQ. ID. NO. 13516    426-LeuGluAsnLeuHisThr-431
SEQ. ID. NO. 13517    444-LeuArgAlaValGluSerProLeuArgGlnIleValAlaAsnAla-458
SEQ. ID. NO. 13518    484-GluTyrGlyAspMetIleGluMet-491
SEQ. ID. NO. 13519    500-ThrArgSerAlaLeu-504
Antigenic Index - Jameson-Wolf
SEQ. ID. NO. 13520    1-MetAlaAlaLysAspValGlnPhe-8
SEQ. ID. NO. 13521    10-AsnGluValArgGlnLysMetValAsn-18
SEQ. ID. NO. 13522    30-ThrLeuGlyProLysGlyArgAsnValValVal-40
SEQ. ID. NO. 13523    43-AlaPheGlyGlyProHisIleThrLysAspGlyValThrValAlaLysGluIleGluLeuLysAspLysPheGluAsnMetGly-70
SEQ. ID. NO. 13524    73-MetValLysGluValAlaSerLysThrAsnAspValAlaGlyAspGlyThrThr-90
SEQ. ID. NO. 13525    112-AsnProThrAspLeuLysArgGlyIleAspLysAlaVal-124

TABLE 1-continued

| | |
|---|---|
| SEQ. ID. NO. 13526 | 129-AspGluLeuLysAsnIleAlaLysProCysAspThrSerLysGluIleAla-145 |
| SEQ. ID. NO. 13527 | 150-IleSerAlaAsnSerAspGluGlnVal-158 |
| SEQ. ID. NO. 13528 | 164-GluAlaMetGluLysValGlyLysGluGlyValIleThrValGluAspGlyLysSerLeuGluAsnGluLeuAspVal-189 |
| SEQ. ID. NO. 13529 | 193-MetGlnPheAspArgGlyTyr-199 |
| SEQ. ID. NO. 13530 | 207-AspAlaGluLysGlnIleAla-213 |
| SEQ. ID. NO. 13531 | 223-PheAspLysLysIleSerAsnIleArgAsp-232 |
| SEQ. ID. NO. 13532 | 239-GlnValAlaLysAlaSerArg-245 |
| SEQ. ID. NO. 13533 | 252-GluAspValGluGlyGluAla-258 |
| SEQ. ID. NO. 13534 | 266-AsnIleArgGlyIleLeu-271 |
| SEQ. ID. NO. 13535 | 278-AlaProGlyPheGlyAspArgArgLysAlaMetLeu-289 |
| SEQ. ID. NO. 13536 | 303-GluGluValGlyLeuSerLeuGluLysAlaThrLeuAspAspLeuGlyGlnAlaLysArgIleGluIleGlyLysGluAsnThrThr-331 |
| SEQ. ID. NO. 13537 | 334-AspGlyPheGlyAspAlaAlaGlnIleGluAlaArgValAlaGluIleArgGlnGlnIleGluThrAlaThrSerAspTyrAspLysGluLysLeuGlnGluArgValAlaLysLeuAlaGly-374 |
| SEQ. ID. NO. 13538 | 385-ThrGluValGluMetLysGluLysLysAspArgValGluAspAlaLeuHis-401 |
| SEQ. ID. NO. 13539 | 405-AlaAlaValGluGluGlyVal-411 |
| SEQ. ID. NO. 13540 | 421-ArgAlaArgAlaAlaLeu-426 |
| SEQ. ID. NO. 13541 | 430-HisThrGlyAsnAlaAspGlnAspAlaGlyVal-440 |
| SEQ. ID. NO. 13542 | 446-AlaValGluSerProLeuArg-452 |
| SEQ. ID. NO. 13543 | 455-ValAlaAsnAlaGlyGlyGluProSerVal-464 |
| SEQ. ID. NO. 13544 | 469-ValLeuGluGlyLysGlyAsnTyrGlyTyr-478 |
| SEQ. ID. NO. 13545 | 480-AlaGlySerGlyGluTyrGlyAspMetIleGlu-490 |
| SEQ. ID. NO. 13546 | 495-AspProAlaLysValThrArgSerAlaLeu-504 |
| SEQ. ID. NO. 13547 | 523-GluIleProGluAspLysProAlaValProAspMetGlyGly-536 |
| Hydrophilic Regions - Hopp-Woods | |
| SEQ. ID. NO. 13548 | 1-MetAlaAlaLysAspValGlnPhe-8 |
| SEQ. ID. NO. 13549 | 10-AsnGluValArgGlnLysMet-16 |
| SEQ. ID. NO. 13550 | 33-ProLysGlyArgAsnValValVal-40 |
| SEQ. ID. NO. 13551 | 48-HisIleThrLysAspGlyValThrValAlaLysGluIleGluLeuLysAspLysPheGluAsn-68 |
| SEQ. ID. NO. 13552 | 73-MetValLysGluValAlaSerLysThrAsnAspValAlaGlyAspGlyThrThr-90 |
| SEQ. ID. NO. 13553 | 114-ThrAspLeuLysArgGlyIleAspLysAlaVal-124 |
| SEQ. ID. NO. 13554 | 129-AspGluLeuLysAsnIleAlaLysProCysAspThrSerLysGluIleAla-145 |
| SEQ. ID. NO. 13555 | 152-AlaAsnSerAspGluGlnVal-158 |
| SEQ. ID. NO. 13556 | 164-GluAlaMetGluLysValGlyLysGluGlyValIleThrValGluAspGlyLysSerLeuGluAsnGluLeuAspVal-189 |
| SEQ. ID. NO. 13557 | 207-AspAlaGluLysGlnIleAla-213 |
| SEQ. ID. NO. 13558 | 223-PheAspLysLysIleSerAsnIleArgAsp-232 |
| SEQ. ID. NO. 13559 | 239-GlnValAlaLysAlaSerArg-245 |
| SEQ. ID. NO. 13560 | 252-GluAspValGluGlyGluAla-258 |
| SEQ. ID. NO. 13561 | 280-GlyPheGlyAspArgArgLysAlaMetLeu-289 |
| SEQ. ID. NO. 13562 | 303-GluGluValGlyLeuSerLeuGluLysAlaThrLeuAspAspLeuGlyGlnAlaLysArgIleGluIleGlyLysGluAsnThrThr-331 |
| SEQ. ID. NO. 13563 | 340-AlaGlnIleGluAlaArgValAlaGluIleArgGlnGlnIleGluThrAlaThrSerAspTyrAspLysGluLysLeuGlnGluArgValAlaLys-371 |
| SEQ. ID. NO. 13564 | 385-ThrGluValGluMetLysGluLysLysAspArgValGluAspAlaLeuHis-401 |
| SEQ. ID. NO. 13565 | 405-AlaAlaValGluGluGlyVal-411 |
| SEQ. ID. NO. 13566 | 421-ArgAlaArgAlaAlaLeu-426 |
| SEQ. ID. NO. 13567 | 433-AsnAlaAspGlnAspAla-438 |
| SEQ. ID. NO. 13568 | 446-AlaValGluSerProLeu-451 |
| SEQ. ID. NO. 13569 | 458-AlaGlyGlyGluPro-462 |
| SEQ. ID. NO. 13570 | 469-ValLeuGluGlyLysGly-474 |
| SEQ. ID. NO. 13571 | 481-GlySerGlyGluTyrGlyAsp-487 |
| SEQ. ID. NO. 13572 | 495-AspProAlaLysValThrArg-501 |
| SEQ. ID. NO. 13573 | 523-GluIleProGluAspLysProAlaVal-531 |
| 986-2 | |
| AMPHI Regions - AMPHI | |
| SEQ. ID. NO. 13574 | 6-GlnTyrLeuAlaLeuAla-11 |
| SEQ. ID. NO. 13575 | 18-LeuAlaGlyCysAspLysAlaGly-25 |
| SEQ. ID. NO. 13576 | 36-SerPheValGluArgIleGluHis-43 |
| SEQ. ID. NO. 13577 | 55-ProAspPheAlaGlnLeuValGln-62 |
| SEQ. ID. NO. 13578 | 99-PheTyrGluPhePheLysArgLeuValProAsnMetProGluIleProGln-115 |
| SEQ. ID. NO. 13579 | 145-ThrGlyMetGlySerIle-150 |
| SEQ. ID. NO. 13580 | 162-AlaLysLeuIleGlySerAspVal-169 |
| SEQ. ID. NO. 13581 | 189-IleGlyAsnProLysAspLeuLysProGly-198 |
| SEQ. ID. NO. 13582 | 200-TrpValAlaAlaIleGly-205 |
| SEQ. ID. NO. 13583 | 287-AlaGluGlnLeuLysAsnThrGlyLysVal-296 |
| SEQ. ID. NO. 13584 | 393-AlaAlaGluHisIleGlyAlaSer-400 |
| SEQ. ID. NO. 13585 | 471-ArgLysAlaMetAspLysAla-477 |
| Antigenic Index - Jameson-Wolf | |
| SEQ. ID. NO. 13586 | 1-ValPheLysLysTyr-5 |
| SEQ. ID. NO. 13587 | 20-GlyCysAspLysAlaGly-25 |
| SEQ. ID. NO. 13588 | 29-GlyAlaAspLysLysGluAlaSerPheValGluArgIleGluHisThrLysAspAspGlySerVal-50 |
| SEQ. ID. NO. 13589 | 61-ValGlnSerGluGlyProAla-67 |
| SEQ. ID. NO. 13590 | 75-ProAlaProArgThrGlnAsnGlySerGlyAsnAlaGluAsnAspSerAspProIleAlaAspAsnAspProPhe-99 |
| SEQ. ID. NO. 13591 | 104-LysArgLeuValProAsnMetProGluIleProGlnGluGluAlaAspAspGlyGlyLeu-123 |
| SEQ. ID. NO. 13592 | 130-IleIleSerLysAspGlyTyr-136 |
| SEQ. ID. NO. 13593 | 154-LeuAsnAspLysArgGluTyrThr-161 |
| SEQ. ID. NO. 13594 | 165-IleGlySerAspValGlnSerAspValAla-174 |
| SEQ. ID. NO. 13595 | 179-AspAlaThrGluGluLeuPro-185 |
| SEQ. ID. NO. 13596 | 189-IleGlyAsnProLysAspLeuLysProGlyGlu-199 |

TABLE 1-continued

| | |
|---|---|
| SEQ. ID. NO. 13597 | 208-PheGlyPheAspAsnSerVal-214 |
| SEQ. ID. NO. 13598 | 219-ValSerAlaLysGlyArgSerLeuProAsnGluSerTyr-231 |
| SEQ. ID. NO. 13599 | 242-AsnProGlyAspAsnSerGlyGlyPro-249 |
| SEQ. ID. NO. 13600 | 265-TyrSerArgSerGlyGly-270 |
| SEQ. ID. NO. 13601 | 288-GluGlnLeuLysAsnThrGlyLysValGlnArgGlyGlnLeu-301 |
| SEQ. ID. NO. 13602 | 316-PheGlyLeuAspLysAlaGlyGly-323 |
| SEQ. ID. NO. 13603 | 330-LeuProGlySerProAlaGluArgAlaGlyLeuGlnAlaGlyAsp-344 |
| SEQ. ID. NO. 13604 | 349-LeuAspGlyGlyGluIleArgSerSerGlyAspLeu-360 |
| SEQ. ID. NO. 13605 | 368-ThrProGlyLysGluValSer-374 |
| SEQ. ID. NO. 13606 | 378-TrpArgLysGlyGluGluIleThrIle-386 |
| SEQ. ID. NO. 13607 | 397-IleGlyAlaSerSerLysThrAspGluAlaProTyrThrGluGlnGlnSerGlyThrPhe-416 |
| SEQ. ID. NO. 13608 | 427-ThrHisThrAspSerSerGlyGly-434 |
| SEQ. ID. NO. 13609 | 440-ArgValSerAspAlaAlaGluArgAlaGlyLeuArgArgGlyAspGluIleLeu-457 |
| SEQ. ID. NO. 13610 | 463-ProValAsnAspGluAlaGlyPheArgLysAlaMetAspLysAlaGlyLysAsnVal-481 |
| SEQ. ID. NO. 13611 | 486-MetArgArgGlyAsnThr-491 |
| Hydrophilic Regions - Hopp-Woods | |
| SEQ. ID. NO. 13612 | 20-GlyCysAspLysAlaGly-25 |
| SEQ. ID. NO. 13613 | 29-GlyAlaAspLysLysGluAlaSerPheValGluArgIleGluHisThrLysAspAspGlySer-49 |
| SEQ. ID. NO. 13614 | 75-ProAlaProArgThrGlnAsnGlySerGlyAsnAlaGluAsnAspSerAspProIleAlaAspAsnAspPro-98 |
| SEQ. ID. NO. 13615 | 111-ProGluIleProGlnGluGluAlaAspAspGlyGly-122 |
| SEQ. ID. NO. 13616 | 131-IleSerLysAspGly-135 |
| SEQ. ID. NO. 13617 | 154-LeuAsnAspLysArgGluTyrThr-161 |
| SEQ. ID. NO. 13618 | 179-AspAlaThrGluGluLeuPro-185 |
| SEQ. ID. NO. 13619 | 190-GlyAsnProLysAspLeuLysPro-197 |
| SEQ. ID. NO. 13620 | 221-AlaLysGlyArgSerLeuPro-227 |
| SEQ. ID. NO. 13621 | 288-GluGlnLeuLysAsnThrGlyLysValGlnArgGlyGln-300 |
| SEQ. ID. NO. 13622 | 317-GlyLeuAspLysAlaGly-322 |
| SEQ. ID. NO. 13623 | 333-SerProAlaGluArgAlaGlyLeuGln-341 |
| SEQ. ID. NO. 13624 | 350-AspGlyGlyGluIleArgSerSerGlyAsp-359 |
| SEQ. ID. NO. 13625 | 368-ThrProGlyLysGluValSer-374 |
| SEQ. ID. NO. 13626 | 379-ArgLysGlyGluGluIleThrIle-386 |
| SEQ. ID. NO. 13627 | 397-IleGlyAlaSerSerLysThrAspGluAlaProTyrThrGluGlnGlnSer-413 |
| SEQ. ID. NO. 13628 | 428-HisThrAspSerSerGly-433 |
| SEQ. ID. NO. 13629 | 440-ArgValSerAspAlaAlaGluArgAlaGlyLeuArgArgGlyAspGluIleLeu-457 |
| SEQ. ID. NO. 13630 | 463-ProValAsnAspGluAlaGlyPheArgLysAlaMetAspLysAlaGlyLys-479 |
| 987 | |
| AMPHI Regions - AMPHI | |
| SEQ. ID. NO. 13631 | 17-CysSerSerTrpLeu-21 |
| SEQ. ID. NO. 13632 | 33-PheAsnThrSerLysProValArgLeuAspAsnIleLeuGlnIle-47 |
| SEQ. ID. NO. 13633 | 65-ProHisGluAlaPhe-69 |
| SEQ. ID. NO. 13634 | 144-AsnProPheValLeuArgLysTrpArgAlaLeuGlyTyrLeuThrAspPheProArgLeuAsnArg-165 |
| SEQ. ID. NO. 13635 | 187-GlyAspIleLeuAlaThr-207 |
| SEQ. ID. NO. 13636 | 202-LeuAspIleLeuAlaThr-207 |
| SEQ. ID. NO. 13637 | 211-ValGlyGluValSerHisAspPheAspArgTyrTrpAla-223 |
| SEQ. ID. NO. 13638 | 230-AlaThrArgIleIleArgSerGlyAspIleGlyLysGlyLeuGlnAla-245 |
| SEQ. ID. NO. 13639 | 290-AspAspProAlaLysGlyLeuAspArg-298 |
| SEQ. ID. NO. 13640 | 307-GlyArgLeuGlnAspAlaLeuLysGlnPro-316 |
| SEQ. ID. NO. 13641 | 333-GlyThrAspAlaLeuAlaLysLeuValGlnAsp-343 |
| SEQ. ID. NO. 13642 | 355-GlnAlaThrAspValAlaAla-361 |
| SEQ. ID. NO. 13643 | 443-LysIleAlaGluGlnMetGluArgThrLeu-452 |
| SEQ. ID. NO. 13644 | 486-ProGluAlaLysLeuTrpLysArgIleAlaAlaLysIleLeuSerLeuLeuProIleGluGlyLeu-507 |
| Antigenic Index - Jameson-Wolf | |
| SEQ. ID. NO. 13645 | 1-MetLysThrArgSer-5 |
| SEQ. ID. NO. 13646 | 23-ProLeuGluGluArgThrGluSerArgHisPheAsnThrSerLysProValArgLeu-41 |
| SEQ. ID. NO. 13647 | 49-HisThrProHisThrAsnGlyLeuSer-57 |
| SEQ. ID. NO. 13648 | 77-GluSerAlaGluHisSerLeu-83 |
| SEQ. ID. NO. 13649 | 90-TrpArgAsnAspIleSerGlyArgLeu-98 |
| SEQ. ID. NO. 13650 | 107-AlaGluArgGlyValArg-112 |
| SEQ. ID. NO. 13651 | 115-LeuLeuLeuAspAspAsnAsnThrArgGlyLeuAsp-126 |
| SEQ. ID. NO. 13652 | 134-SerHisProAsnIleGluValArgLeu-142 |
| SEQ. ID. NO. 13653 | 159-AspPheProArgLeuAsnArgArgMetHisAsnLysSerPheThrAlaAspAsnArgAla-178 |
| SEQ. ID. NO. 13654 | 182-GlyGlyArgAsnIleGlyAspGluTyrPheLysValGlyGluAspThrVal-198 |
| SEQ. ID. NO. 13655 | 214-ValSerHisAspPheAspArgTyrTrp-222 |
| SEQ. ID. NO. 13656 | 225-HisSerAlaHisAsn-229 |
| SEQ. ID. NO. 13657 | 232-ArgIleIleArgSerGlyAspIleGlyLysGlyLeu-243 |
| SEQ. ID. NO. 13658 | 247-GlyTyrAsnAspGluThrSerArg-254 |
| SEQ. ID. NO. 13659 | 259-ArgTyrArgGluThrValGlu-265 |
| SEQ. ID. NO. 13660 | 267-SerProLeuTyrGln-271 |
| SEQ. ID. NO. 13661 | 282-SerValArgThrArgLeuIleSerAspAspProAlaLysGlyLeuAspArgAspArgArgLysProProIle-305 |
| SEQ. ID. NO. 13662 | 308-ArgLeuGlnAspAlaLeuLysGlnProGluLysSer-319 |
| SEQ. ID. NO. 13663 | 328-ValProThrLysSerGlyThrAspAlaLeu-337 |
| SEQ. ID. NO. 13664 | 340-LeuValGlnAspGlyIleAsp-346 |
| SEQ. ID. NO. 13665 | 367-ValLysTyrArgLysProLeuLeu-374 |
| SEQ. ID. NO. 13666 | 391-AlaThrLysAspLysGlyLeuThrGlySerSer-401 |
| SEQ. ID. NO. 13667 | 412-ValAspGlyLysArgIlePhe-418 |
| SEQ. ID. NO. 13668 | 422-PheAsnLeuAspProArgSerAlaArgLeuAsnThr-433 |
| SEQ. ID. NO. 13669 | 440-GluSerProLysIleAlaGluGlnMetGluArgThrLeuAlaAspThrThrPro-457 |
| SEQ. ID. NO. 13670 | 463-ValThrLeuAspArgHisAsnArgLeuGlnTrpHisAspProAlaThrArgLysThrTyrProAsnGluProGluAlaLysLeuTrpLys-492 |
| Hydrophilic Regions - Hopp-Woods | |
| SEQ. ID. NO. 13671 | 1-MetLysThrArgSer-5 |

TABLE 1-continued

| SEQ. ID. NO. | Sequence |
|---|---|
| SEQ. ID. NO. 13672 | 24-LeuGluGluArgThrGluSerArgHisPheAsnThr-35 |
| SEQ. ID. NO. 13673 | 37-LysProValArgLeu-41 |
| SEQ. ID. NO. 13674 | 77-GluSerAlaGluHisSerLeu-83 |
| SEQ. ID. NO. 13675 | 107-AlaGluArgGlyValArg-112 |
| SEQ. ID. NO. 13676 | 115-LeuLeuLeuAspAspAsnAsnThrArgGlyLeuAsp-126 |
| SEQ. ID. NO. 13677 | 161-ProArgLeuAsnArgArgMetHisAsn-169 |
| SEQ. ID. NO. 13678 | 172-PheThrAlaAspAsnArgAla-178 |
| SEQ. ID. NO. 13679 | 189-GluTyrPheLysValGlyGluAspThrVal-198 |
| SEQ. ID. NO. 13680 | 214-ValSerHisAspPheAspArg-220 |
| SEQ. ID. NO. 13681 | 232-ArgIleIleArgSerGlyAspIleGlyLys-241 |
| SEQ. ID. NO. 13682 | 248-TyrAsnAspGluThrSerArg-254 |
| SEQ. ID. NO. 13683 | 259-ArgTyrArgGluThrValGlu-265 |
| SEQ. ID. NO. 13684 | 282-SerValArgThrArgLeuIleSerAspAspProAlaLysGlyLeuAspArgAspArgArgLysProProIle-305 |
| SEQ. ID. NO. 13685 | 308-ArgLeuGlnAspAlaLeuLysGlnProGluLysSer-319 |
| SEQ. ID. NO. 13686 | 331-LysSerGlyThrAspAlaLeu-337 |
| SEQ. ID. NO. 13687 | 340-LeuValGlnAspGlyIleAsp-346 |
| SEQ. ID. NO. 13688 | 367-ValLysTyrArgLysProLeuLeu-374 |
| SEQ. ID. NO. 13689 | 391-AlaThrLysAspLysGlyLeuThr-398 |
| SEQ. ID. NO. 13690 | 424-LeuAspProArgSerAlaArgLeuAsnThr-433 |
| SEQ. ID. NO. 13691 | 440-GluSerProLysIleAlaGluGlnMetGluArgThrLeuAla-453 |
| SEQ. ID. NO. 13692 | 464-ThrLeuAspArgHisAsnArg-470 |
| SEQ. ID. NO. 13693 | 476-ProAlaThrArgLysThrTyrProAsnGluProGluAlaLysLeuTrpLys-492 |
| 988-2 | |
| AMPHI Regions - AMPHI | |
| SEQ. ID. NO. 13694 | 45-SerLysIleGluSerLeuAlaArg-52 |
| SEQ. ID. NO. 13695 | 125-GlnMetArgGlyIle-129 |
| SEQ. ID. NO. 13696 | 154-AspIleValGluArgAlaGlnSerLysVal-163 |
| SEQ. ID. NO. 13697 | 221-AlaLysIleIleGluValLeuGlyAspTyrAlaAsp-232 |
| SEQ. ID. NO. 13698 | 248-HisGlnPheSerGluAlaCysAlaLysAlaAlaLysLysIle-261 |
| SEQ. ID. NO. 13699 | 288-ThrAlaArgAspPheAspAsp-294 |
| SEQ. ID. NO. 13700 | 299-GluLysValGlyArgAsnTyr-305 |
| SEQ. ID. NO. 13701 | 310-AlaIleAlaAspValSerHisTyrValArgProAspAspValIleAsp-325 |
| SEQ. ID. NO. 13702 | 348-AsnLeuSerAsnGly-352 |
| SEQ. ID. NO. 13703 | 396-AsnGlnValTrpLysTrpIleSerAspGlyIleAspHisPro-409 |
| SEQ. ID. NO. 13704 | 411-LysAlaGlnIleAspThrLeuTyrLysLeuPheLysIleLeuGlnLys-426 |
| SEQ. ID. NO. 13705 | 494-LeuGlyProThrProGluLysLeuAlaThrLeu-504 |
| SEQ. ID. NO. 13706 | 526-TyrAlaAlaLeuValGlyGluGlnPheLys-534 |
| SEQ. ID. NO. 13707 | 544-ValMetMetLeuArgSerMetGlnGlnAla-553 |
| SEQ. ID. NO. 13708 | 569-AlaTyrAlaHisPheThrSerProIleArgArgTyrProAspLeuThrValHisArgAlaIleLysAlaValLeu-593 |
| SEQ. ID. NO. 13709 | 619-AspAspAlaSerArgAspValGluAsnTrpLeuLys-630 |
| SEQ. ID. NO. 13710 | 646-IleSerGlyMetThrSerPheGlyIlePheValThrLeu-658 |
| SEQ. ID. NO. 13711 | 662-HisIleAspGlyLeuValHisIleSerAspLeuGlyGlu-674 |
| Antigenic Index - Jameson-Wolf | |
| SEQ. ID. NO. 13712 | 1-MetAsnLysAsnIleLys-6 |
| SEQ. ID. NO. 13713 | 8-LeuAsnLeuArgGluLysAspProPheLeuSerArgGluLysGlnArgTyrGluHisProLeuProSerArgGluTrpIle-34 |
| SEQ. ID. NO. 13714 | 37-LeuLeuGluArgLysGlyValProSerLysIleGluSerLeuAlaArgGluLeuSerIleThrGluAspGluTyrValPhePheGluArgArgLeuLysAlaMetAlaArgAspGlyGln-76 |
| SEQ. ID. NO. 13715 | 79-IleAsnArgArgGlyAlaVal-85 |
| SEQ. ID. NO. 13716 | 87-AlaAlaAspLysLeuAspLeuValLysCysArgValGluAlaHisLysAspGlyPhe-105 |
| SEQ. ID. NO. 13717 | 111-LeuThrProAlaLysAspGlyAsp-118 |
| SEQ. ID. NO. 13718 | 124-ArgGlnMetArgGly-128 |
| SEQ. ID. NO. 13719 | 138-ArgProAlaGlyMetAspArgArgGlyArgArgGluGlyThrVal-152 |
| SEQ. ID. NO. 13720 | 155-IleValGluArgAlaGlnSerLysValVal-164 |
| SEQ. ID. NO. 13721 | 168-TyrMetAspArgGlyValAla-174 |
| SEQ. ID. NO. 13722 | 176-LeuGluProGluAspLysArgLeuAsnGln-185 |
| SEQ. ID. NO. 13723 | 189-LeuGluProAspGlyValAlaArgPheLysProGluSerGlyGln-203 |
| SEQ. ID. NO. 13724 | 210-GluValTyrProGluGlnAsnArgProAlaVal-220 |
| SEQ. ID. NO. 13725 | 227-LeuGlyAspTyrAlaAspSerGlyMetGluIle-237 |
| SEQ. ID. NO. 13726 | 239-IleAlaValArgLysHisHisLeu-246 |
| SEQ. ID. NO. 13727 | 253-AlaCysAlaLysAlaAlaAlaLysLysIleProValHisValArgLysSerAspLeuLysGlyArgValArgAspLeuArgAsp-278 |
| SEQ. ID. NO. 13728 | 283-ThrIleAspGlyGluThrAlaArgAspPheAspAsp-294 |
| SEQ. ID. NO. 13729 | 299-GluLysValGlyArgAsnTyrArg-306 |
| SEQ. ID. NO. 13730 | 316-HisTyrValArgProAspAspValIleAspAlaAspAlaGlnGluArgSerThrSer-334 |
| SEQ. ID. NO. 13731 | 337-PheProArgArgVal-341 |
| SEQ. ID. NO. 13732 | 345-LeuProGluAsnLeuSerAsnGly-352 |
| SEQ. ID. NO. 13733 | 356-LeuAsnProAspValGluArgLeu-363 |
| SEQ. ID. NO. 13734 | 374-AlaGlyAsnIleLysGluTyrArgPhe-382 |
| SEQ. ID. NO. 13735 | 402-IleSerAspGlyIleAspHisProTyrLysAlaGlnIle-414 |
| SEQ. ID. NO. 13736 | 424-LeuGlnLysLysArgPheGluArgGlyAlaValGluPheGluSerValGlu-440 |
| SEQ. ID. NO. 13737 | 443-MetIlePheAspAspAsnGlyLysIleGluLys-453 |
| SEQ. ID. NO. 13738 | 458-ValArgAsnAspAlaHisLysLeuIleGlu-467 |
| SEQ. ID. NO. 13739 | 482-LeuLysAsnLysHisThrAla-488 |
| SEQ. ID. NO. 13740 | 493-HisLeuGlyProThrProGluLysLeuAlaThrLeuArgGluGlnLeu-508 |
| SEQ. ID. NO. 13741 | 516-GlyGlyGlyAspAsnProSerProLysAspTyr-526 |
| SEQ. ID. NO. 13742 | 532-GlnPheLysGlyArgProAspAlaGluLeu-541 |
| SEQ. ID. NO. 13743 | 556-GluProHisCysAspGlyHis-562 |
| SEQ. ID. NO. 13744 | 575-SerProIleArgArgTyrProAspLeuThrVal-585 |
| SEQ. ID. NO. 13745 | 597-ThrTyrThrProLysLysSerTrp-604 |
| SEQ. ID. NO. 13746 | 613-PheCysGluArgAlaAspAspAlaSerArgAspValGluAsn-627 |
| SEQ. ID. NO. 13747 | 633-TyrMetArgAspLysValGlyGluValPheGluGlyLysIleSerGly-648 |

TABLE 1-continued

| | |
|---|---|
| SEQ. ID. NO. 13748 | 670-SerAspLeuGlyGluAspTyrPheAsnPheArgPro-681 |
| SEQ. ID. NO. 13749 | 683-IleMetAlaIleGluGlyGluArgSerGlyIleArgPheAsnMetGlyAspArgValAlaValArgValAlaArgAlaAspLeuAspAspGlyLys Ile-715 |
| SEQ. ID. NO. 13750 | 722-GlyGlySerGlyArgGlyArgLysValLysSerSerAlaSerAlaLysProAlaGlyThrAlaGlyLysGlyLysProLysThrAlaAlaGluLys LysThrAlaArgGlyGlyLysValArgGlyArgGlyAlaSerAlaAlaAlaGluSerArgLysLysAlaLysLysProValProIleLysValLysLysArg LysGlyLysSer-791 |

Hydrophilic Regions - Hopp-Woods

| | |
|---|---|
| SEQ. ID. NO. 13751 | 1-MetAsnLysAsnIleLys-6 |
| SEQ. ID. NO. 13752 | 8-LeuAsnLeuArgGluLysAspProPheLeuSerArgGluLysGlnArgTyrGluHis-26 |
| SEQ. ID. NO. 13753 | 37-LeuLeuGluArgLysGlyValProSerLysIleGluSerLeuAlaArgGluLeuSerIleThrGluAspGluTyrValPhePheGluArgArg LeuLysAlaMetAlaArgAspGlyGln-76 |
| SEQ. ID. NO. 13754 | 79-IleAsnArgArgGlyAla-84 |
| SEQ. ID. NO. 13755 | 87-AlaAlaAspLysLeuAspLeuValLysCysArgValGluAlaHisLysAspGlyPhe-105 |
| SEQ. ID. NO. 13756 | 113-ProAlaLysAspGlyAsp-118 |
| SEQ. ID. NO. 13757 | 140-AlaGlyMetAspArgArgGlyArgArgGluGlyThrVal-152 |
| SEQ. ID. NO. 13758 | 155-IleValGluArgAlaGlnSerLysValVal-164 |
| SEQ. ID. NO. 13759 | 176-LeuGluProGluAspLysArgLeuAsn-184 |
| SEQ. ID. NO. 13760 | 189-LeuGluProAspGlyValAlaArgPheLysProGluSerGly-202 |
| SEQ. ID. NO. 13761 | 210-GluValTyrProGluGlnAsnArgProAlaVal-220 |
| SEQ. ID. NO. 13762 | 230-TyrAlaAspSerGlyMetGluIle-237 |
| SEQ. ID. NO. 13763 | 239-IleAlaValArgLysHisHis-245 |
| SEQ. ID. NO. 13764 | 253-AlaCysAlaLysAlaAlaLysLysIleProValHisValArgLysSerAspLeuLysGlyArgValAspLeuArgAsp-278 |
| SEQ. ID. NO. 13765 | 284-IleAspGlyGluThrAlaArgAspPheAspAsp-294 |
| SEQ. ID. NO. 13766 | 299-GluLysValGlyArgAsnTyr-305 |
| SEQ. ID. NO. 13767 | 318-ValArgProAspAspValIleAspAlaAspAlaGlnGluArgSerThr-333 |
| SEQ. ID. NO. 13768 | 358-ProAspValGluArg-362 |
| SEQ. ID. NO. 13769 | 376-AsnIleLysGluTyrArg-381 |
| SEQ. ID. NO. 13770 | 405-GlyIleAspHisProTyr-410 |
| SEQ. ID. NO. 13771 | 424-LeuGlnLysLysArgPheGluArgGlyAlaValGluPheGluSerValGlu-440 |
| SEQ. ID. NO. 13772 | 443-MetIlePheAspAspAsnGlyLysIleGluLys-453 |
| SEQ. ID. NO. 13773 | 458-ValArgAsnAspAlaHisLysLeuIleGlu-467 |
| SEQ. ID. NO. 13774 | 496-ProThrProGluLysLeuAlaThrLeuArgGluGlnLeu-508 |
| SEQ. ID. NO. 13775 | 517-GlyGlyAspAsnProSerProLysAspTyr-526 |
| SEQ. ID. NO. 13776 | 532-GlnPheLysGlyArgProAlaGluLeu-541 |
| SEQ. ID. NO. 13777 | 576-ProIleArgArgTyrProAsp-582 |
| SEQ. ID. NO. 13778 | 598-TyrThrProLysLysSerTrp-604 |
| SEQ. ID. NO. 13779 | 613-PheCysGluArgArgAlaAspAspAlaSerArgAspValGluAsn-627 |
| SEQ. ID. NO. 13780 | 633-TyrMetArgArgAspLysValGlyGluValPheGluGlyLysIle-646 |
| SEQ. ID. NO. 13781 | 683-IleMetAlaIleGluGlyGluArgSerGlyIle-693 |
| SEQ. ID. NO. 13782 | 696-AsnMetGlyAspArgValAlaValArgValAlaArgAlaAspLeuAspAspGlyLysIle-715 |
| SEQ. ID. NO. 13783 | 723-GlySerGlyArgGlyArgLysValLysSerSerAlaSerAlaLysProAlaGlyThrAlaGlyLysGlyLysProLysThrAlaAlaGluLys LysThrAlaArgGlyGlyLysValArgGlyArgGlyAlaSerAlaAlaAlaGluSerArg gLysLysAlaLysLysProValProIleLysValLysLysArgLysGlyLys Ser-791 |

989
AMPHI Regions - AMPHI

| | |
|---|---|
| SEQ. ID. NO. 13784 | 58-AlaGlyLeuThrLysLeu-63 |
| SEQ. ID. NO. 13785 | 85-SerAlaThrAspPhe-89 |
| SEQ. ID. NO. 13786 | 98-LysSerGlyLysIleThr-103 |
| SEQ. ID. NO. 13787 | 109-ProHisIleTyrGlyAla-114 |
| SEQ. ID. NO. 13788 | 183-GluLeuArgLysTyrAlaAsp-189 |
| SEQ. ID. NO. 13789 | 205-LysProAsnGlyValAlaGluAla-212 |
| SEQ. ID. NO. 13790 | 273-AlaMetTrpSerThr-277 |
| SEQ. ID. NO. 13791 | 301-SerValHisGlyMetTyrLysValSer-309 |
| SEQ. ID. NO. 13792 | 320-TrpThrArgHisSerArg-325 |
| SEQ. ID. NO. 13793 | 364-SerTyrGlnIleSerGluProLeu-371 |
| SEQ. ID. NO. 13794 | 450-PheLysAsnHisAlaAsp-455 |

Antigenic Index - Jameson-Wolf

| | |
|---|---|
| SEQ. ID. NO. 13795 | 46-GluAlaAlaAspAlaSer-51 |
| SEQ. ID. NO. 13796 | 57-ProAlaGlyLeuThrLysLeuAspSerSerGlnIle-68 |
| SEQ. ID. NO. 13797 | 81-TyrGluAlaAspSerAlaThrAspPheThr-90 |
| SEQ. ID. NO. 13798 | 95-GlnGlySerLysSerGlyLysIleThrLysThrThr-106 |
| SEQ. ID. NO. 13799 | 116-LysValAsnAspAsnLeuThr-122 |
| SEQ. ID. NO. 13800 | 132-GlySerAlaThrGluTyrGluLysAspSerValLeu-143 |
| SEQ. ID. NO. 13801 | 146-AsnIleAsnLysLeuGly-151 |
| SEQ. ID. NO. 13802 | 164-LysLeuAsnAspArgHisSerPheGly-172 |
| SEQ. ID. NO. 13803 | 180-ThrSerAlaGluLeuArgLysTyrAla-188 |
| SEQ. ID. NO. 13804 | 191-GlyIleLysSerLysAlaGluIleLeuThrAlaLysProProLysProAsnGlyValAlaGluAlaAlaLysIleGlnAlaAspGlyHisAlaAsp ValLysGlySerAspTrpGly-229 |
| SEQ. ID. NO. 13805 | 239-AspIleAsnAspArgAlaArgValGlyValAsnTyrArgSerLysValSerHisThrLeuLysGlyAspAlaGluTrpAlaAla-266 |
| SEQ. ID. NO. 13806 | 285-ThrAlaAsnGluLysAlaArgValLysIleValThrProGluSer-299 |
| SEQ. ID. NO. 13807 | 306-TyrLysValSerArgSerLysAlaAspLeu-314 |
| SEQ. ID. NO. 13808 | 319-ThrTrpThrArgHisSerArgPheAspLysAlaGluLeuValPheGluLysGluLysThrValValLysGlyLysSerAspArgThrThrIle-349 |
| SEQ. ID. NO. 13809 | 351-ProAsnTrpArgAsnThrTyrLys-358 |
| SEQ. ID. NO. 13810 | 363-GlySerTyrGlnIleSerGlu-369 |
| SEQ. ID. NO. 13811 | 377-IleAlaPheAspLysSerProValArgAsnAlaAspTyrArgMetAsnSerLeuProAspGlyAsn-398 |
| SEQ. ID. NO. 13812 | 409-HisIleGlyLysAsnHisVal-415 |
| SEQ. ID. NO. 13813 | 426-AsnAspThrSerTyrArgThrAlaLysAlaSerGlyAsnAspValAspSerLysGlyAlaSerSerAlaArgPheLysAsnHisAla-454 |

Hydrophilic Regions - Hopp-Woods

| | |
|---|---|
| SEQ. ID. NO. 13814 | 61-ThrLysLeuAspSerSerGln-67 |
| SEQ. ID. NO. 13815 | 81-TyrGluAlaAspSerAlaThr-87 |

TABLE 1-continued

| | |
|---|---|
| SEQ. ID. NO. 13816 | 95-GlnGlySerLysSerGlyLysIleThrLys-104 |
| SEQ. ID. NO. 13817 | 135-ThrGluTyrGluLysAspSerValLeu-143 |
| SEQ. ID. NO. 13818 | 164-LysLeuAsnAspArgHisSer-170 |
| SEQ. ID. NO. 13819 | 180-ThrSerAlaGluLeuArgLysTyrAla-188 |
| SEQ. ID. NO. 13820 | 191-GlyIleLysSerLysAlaGluIleLeuThr-200 |
| SEQ. ID. NO. 13821 | 202-LysProProLysProAsnGlyValAlaGluAlaAlaLysIleGlnAla-217 |
| SEQ. ID. NO. 13822 | 219-GlyHisAlaAspValLysGlySerAsp-227 |
| SEQ. ID. NO. 13823 | 240-IleAsnAspArgAlaArgVal-246 |
| SEQ. ID. NO. 13824 | 250-TyrArgSerLysVal-254 |
| SEQ. ID. NO. 13825 | 258-LeuLysGlyAspAlaGluTrpAlaAla-266 |
| SEQ. ID. NO. 13826 | 285-ThrAlaAsnGluLysAlaArgValLysIleValThr-296 |
| SEQ. ID. NO. 13827 | 307-LysValSerAspLysAlaAspLeu-314 |
| SEQ. ID. NO. 13828 | 324-SerArgPheAspLysAlaGluLeuValPheGluLysGluLysThrValValLysGlyLysSerAspArgThrThrIle-349 |
| SEQ. ID. NO. 13829 | 377-IleAlaPheAspLysSerProValArgAsnAlaAspTyrArgMet-391 |
| SEQ. ID. NO. 13830 | 393-SerLeuProAspGlyAsn-398 |
| SEQ. ID. NO. 13831 | 428-ThrSerTyrArgThrAlaLysAlaSerGlyAsnAspValAspSerLysGlyAlaSerSerAlaArgPheLysAsnHisAla-454 |

990
AMPHI Regions - AMPHI

| | |
|---|---|
| SEQ. ID. NO. 13832 | 89-LysSerGlnLeuGlnAspLeuTyrLys-97 |
| SEQ. ID. NO. 13833 | 128-ThrMetProAspLeuIleAsnLysLeuVal-137 |
| SEQ. ID. NO. 13834 | 151-ThrSerLeuAsnAsnIlePhe-157 |
| SEQ. ID. NO. 13835 | 191-ArgArgHisSerAspIleHisThrLeuGluThrSerAsp-203 |
| SEQ. ID. NO. 13836 | 260-ProGluAsnLeuLysThrLeuAspGly-268 |
| SEQ. ID. NO. 13837 | 293-TyrGluLeuLeuLeuLysGlnCys-300 |
| SEQ. ID. NO. 13838 | 372-AlaAspGlyTrpArgLysGlyVal-379 |
| SEQ. ID. NO. 13839 | 423-GlyTyrGlyGlyGlyValTyrAlaAlaTrp-432 |
| SEQ. ID. NO. 13840 | 442-AlaTyrLeuAspGlyTrpLeuGlnTyr-450 |
| SEQ. ID. NO. 13841 | 472-ThrAlaSerValGluGlyGlyTyrAsnAlaLeu-482 |
| SEQ. ID. NO. 13842 | 550-GlnProPheAlaAlaPheAsnValLeuHisArg-560 |

Antigenic Index - Jameson-Wolf

| | |
|---|---|
| SEQ. ID. NO. 13843 | 6-LeuGlySerAsnThrArgSerThrLysIleGlyAspAspAlaAspPheSerPheSerAspLysProLysProGlyThr-31 |
| SEQ. ID. NO. 13844 | 35-PheSerSerGlyLysThrAspGlnAsnSerSerGluTyrGlyTyrAspGluIleGluAsnIleGlnGlyLysAsnTyrAsnSerGlyIle-63 |
| SEQ. ID. NO. 13845 | 75-TyrIleThrGluLysTyrGlyAlaAspLeuLysGlnAlaVal-88 |
| SEQ. ID. NO. 13846 | 90-SerGlnLeuGlnAspLeuTyrLysThrArgProGluAlaTrpAlaGluAsnLysLysArgThrGluGluAlaTyr-114 |
| SEQ. ID. NO. 13847 | 120-ThrLysPheSerThrLeuLysGlnThrMetPro-130 |
| SEQ. ID. NO. 13848 | 145-HisSerAsnThrSerGlnThrSer-152 |
| SEQ. ID. NO. 13849 | 157-PheAsnLysLysLeuHisValLysIleGluAsnLysSerHisVal-171 |
| SEQ. ID. NO. 13850 | 179-ThrLysMetThrLeuLysAspSerLeuTrpGluProArgArgHisSerAspIleHisThrLeuGluThrSerAspAsnAlaArgIleArgLeuAsnThrLysAspGluLysLeuThrValHisLysAspTyrAlaGlyGlyAlaAsp-227 |
| SEQ. ID. NO. 13851 | 232-TyrAspValArgGluSerAspGluProAlaLeuThrPheGluAspLysValSerGlyGlnSerGlyValValLeuGluArgArgProGluAsnLeuLysThrLeuAspGlyArgLysLeuIleAla-273 |
| SEQ. ID. NO. 13852 | 275-LysThrAlaAspSerGlySerPheAlaPheLysGlnAsnTyrArgGlnGlyLeu-292 |
| SEQ. ID. NO. 13853 | 298-LysGlnCysGluGlyGlyPhe-304 |
| SEQ. ID. NO. 13854 | 312-AlaIleProGluAlaGlu-317 |
| SEQ. ID. NO. 13855 | 335-ArgAlaAlaAspArgGlyAspAspValTyrAlaAlaAspProSerArgGlnLysLeu-353 |
| SEQ. ID. NO. 13856 | 358-IleGlyGlyArgSerHisGlnAsnIleArgGlyValAlaAlaAlaAspGlyTrpArgLysGlyVal-379 |
| SEQ. ID. NO. 13857 | 385-ValPheValArgGlnAsnGluGlySerArgLeuAla-396 |
| SEQ. ID. NO. 13858 | 400-MetGlyGlyArgAlaGlyGln-406 |
| SEQ. ID. NO. 13859 | 408-AlaSerValAsnGlyLysGlyGlyAlaAlaGlySerAspLeu-421 |
| SEQ. ID. NO. 13860 | 435-LeuArgAspLysGlnThrGlyAlaTyr-443 |
| SEQ. ID. NO. 13861 | 452-ArgPheLysHisArgIleAsnAspGluAsnArgAlaGluArgTyrLysThrLysGlyTrpThr-472 |
| SEQ. ID. NO. 13862 | 475-ValGluGlyGlyTyr-479 |
| SEQ. ID. NO. 13863 | 487-IleValGlyLysGlyAsnAsnValArg-495 |
| SEQ. ID. NO. 13864 | 510-AsnGlyGlyPheThrAspSerGluGlyThrAla-520 |
| SEQ. ID. NO. 13865 | 525-GlySerGlyGlnTrpGlnSerArgAlaGlyIleArgAlaLysThrArgPheAlaLeuArgAsnGlyValAsn-548 |
| SEQ. ID. NO. 13866 | 559-HisArgSerLysSerPheGlyValGluMetAspGlyGluLysGlnThrLeuAla-576 |
| SEQ. ID. NO. 13867 | 579-ThrAlaLeuGluLeuGlyArgPheGlyIle-587 |
| SEQ. ID. NO. 13868 | 589-AlaGlyTrpLysGlyHisMet-595 |
| SEQ. ID. NO. 13869 | 600-GlyTyrGlyLysArgThrAspGlyAspLysGluAlaAlaLeu-613 |

Hydrophilic Regions - Hopp-Woods

| | |
|---|---|
| SEQ. ID. NO. 13870 | 8-SerAsnThrArgSerThrLysIleGlyAspAspAlaAspPheSerPheSerAspLysProLysProGlyThr-31 |
| SEQ. ID. NO. 13871 | 38-GlyLysThrAspGlnAsnSerSer-45 |
| SEQ. ID. NO. 13872 | 79-LysTyrGlyAlaAspLeuLysGlnAlaVal-88 |
| SEQ. ID. NO. 13873 | 96-TyrLysThrArgProGluAlaTrpAlaGluAsnLysLysArgThrGluGluAlaTyr-114 |
| SEQ. ID. NO. 13874 | 161-LeuHisValLysIleGluAsnLysSerHisVal-171 |
| SEQ. ID. NO. 13875 | 179-ThrLysMetThrLeuLys-184 |
| SEQ. ID. NO. 13876 | 186-SerLeuTrpGluProArgArgHisSerAsp-195 |
| SEQ. ID. NO. 13877 | 200-GluThrSerAspAsnAlaArgIleArgLeuAsnThrLysAspGluLysLeuThrVal-218 |
| SEQ. ID. NO. 13878 | 220-LysAspTyrAlaGly-224 |
| SEQ. ID. NO. 13879 | 233-AspValArgGluSerAspGluProAlaLeuThrPheGluAspLysValSerGly-250 |
| SEQ. ID. NO. 13880 | 255-ValLeuGluArgArgProGluAsnLeuLysThrLeuAspGlyArgLysLeuIleAla-273 |
| SEQ. ID. NO. 13881 | 275-LysThrAlaAspSerGly-280 |
| SEQ. ID. NO. 13882 | 312-AlaIleProGluAlaGlu-317 |
| SEQ. ID. NO. 13883 | 335-ArgAlaAlaAspArgGlyAspAspValTyrAla-345 |
| SEQ. ID. NO. 13884 | 347-AspProSerArgGln-351 |
| SEQ. ID. NO. 13885 | 361-ArgSerHisGlnAsnIleArgGly-368 |
| SEQ. ID. NO. 13886 | 373-AspGlyTrpArgLys-377 |
| SEQ. ID. NO. 13887 | 385-ValPheValArgGlnAsnGluGlySerArg-394 |
| SEQ. ID. NO. 13888 | 410-ValAsnGlyLysGlyGlyAlaAlaGly-418 |
| SEQ. ID. NO. 13889 | 435-LeuArgAspLysGlnThr-440 |

TABLE 1-continued

| | |
|---|---|
| SEQ. ID. NO. 13890 | 452-ArgPheLysHisArgIleAsnAspGluAsnArgAlaGluArgTyrLysThr-468 |
| SEQ. ID. NO. 13891 | 513-PheThrAspSerGluGlyThr-519 |
| SEQ. ID. NO. 13892 | 533-AlaGlyIleArgAlaLysThrArgPheAlaLeu-543 |
| SEQ. ID. NO. 13893 | 559-HisArgSerLysSerPheGlyValGluMetAspGlyGluLysGlnThrLeuAla-576 |
| SEQ. ID. NO. 13894 | 579-ThrAlaLeuGluGly-583 |
| SEQ. ID. NO. 13895 | 600-GlyTyrGlyLysArgThrAspGlyAspLysGluAlaAlaLeu-613 |

992
AMPHI Regions - AMPHI

| | |
|---|---|
| SEQ. ID. NO. 13896 | 6-ArgHisLeuLysAsnMetGlnIleLysLysIleMetLysTrp-19 |
| SEQ. ID. NO. 13897 | 24-LeuSerLeuLeuGlyAlaLeuGlyTyr-32 |
| SEQ. ID. NO. 13898 | 45-AlaValLeuAspValLeuGlyAlaAla-53 |
| SEQ. ID. NO. 13899 | 72-HisArgTyrThrGlyThrValSerLysValTyr-82 |
| SEQ. ID. NO. 13900 | 158-GlnValGlnAspGly-162 |
| SEQ. ID. NO. 13901 | 179-AspPheAlaAspTyr-183 |

Antigenic Index - Jameson-Wolf

| | |
|---|---|
| SEQ. ID. NO. 13902 | 1-MetPheArgArgHisArgHisLeuLys-9 |
| SEQ. ID. NO. 13903 | 34-GlyTyrGlySerGluAlaValArg-41 |
| SEQ. ID. NO. 13904 | 52-AlaAlaGlyAspAlaGlySerAspAlaProAlaArgArgArgAlaSerAlaLysSerGlyHisArgTyrThr-75 |
| SEQ. ID. NO. 13905 | 79-SerLysValTyrAspGlyAspThr-86 |
| SEQ. ID. NO. 13906 | 90-IleAspGlyAspGlyAlaLysHisLysIle-99 |
| SEQ. ID. NO. 13907 | 105-AspAlaProGluMetLysGlnAlaTyrGlyThrArgSerArgAspAsnLeuArgAlaAlaAlaGluGlyArgLysValSer-131 |
| SEQ. ID. NO. 13908 | 134-ValPheAspThrAspArgTyrGlnArgGluValAla-145 |
| SEQ. ID. NO. 13909 | 148-SerValGlyLysThrAspLeuAsn-155 |
| SEQ. ID. NO. 13910 | 168-LysSerTyrAlaLysGluGlnGlnAspLysAlaAspPhe-180 |
| SEQ. ID. NO. 13911 | 187-GlnIleGlnAlaGluArgGluArgLysGlyLeuTrpLysAlaLysAsnProGlnAlaPro-206 |
| SEQ. ID. NO. 13912 | 208-AlaTyrArgArgAlaGlyArgSerGlyGlyGlyAsnLysAspTrpMetAsp-224 |

Hydrophilic Regions - Hopp-Woods

| | |
|---|---|
| SEQ. ID. NO. 13913 | 1-MetPheArgArgHisArgHisLeuLys-9 |
| SEQ. ID. NO. 13914 | 54-GlyAspAlaGlySerAspAlaProAlaArgArgArgAlaSerAlaLysSerGlyHisArg-73 |
| SEQ. ID. NO. 13915 | 90-IleAspGlyAspGlyAlaLysHisLysIle-99 |
| SEQ. ID. NO. 13916 | 105-AspAlaProGluMetLysGln-111 |
| SEQ. ID. NO. 13917 | 113-TyrGlyThrArgSerArgAspAsnLeuArgAlaAlaAlaGluGlyArgLysValSer-131 |
| SEQ. ID. NO. 13918 | 134-ValPheAspThrAspArgTyrGlnArgGluValAla-145 |
| SEQ. ID. NO. 13919 | 148-SerValGlyLysThrAspLeu-154 |
| SEQ. ID. NO. 13920 | 169-SerTyrAlaLysGluGlnGlnAspLysAlaAspPhe-180 |
| SEQ. ID. NO. 13921 | 187-GlnIleGlnAlaGluArgGluArgLysGlyLeuTrpLysAlaLysAsnPro-203 |
| SEQ. ID. NO. 13922 | 211-ArgAlaGlyArgSerGlyGlyGlyAsnLysAspTrpMet-223 |

993
AMPHI Regions - AMPHI

| | |
|---|---|
| SEQ. ID. NO. 13923 | 6-GlySerPheGlnGlyProLeuAspLeuLeuLeu-16 |
| SEQ. ID. NO. 13924 | 35-ThrGluGlnTyrLeuHisTyrIleAlaGlnIle-45 |
| SEQ. ID. NO. 13925 | 105-GlyLeuAspAlaLeuProArgAla-112 |
| SEQ. ID. NO. 13926 | 136-IleThrAspLeuThrGlnAlaTrpLeuGly-145 |
| SEQ. ID. NO. 13927 | 152-HisThrArgSerHisGluValIle-159 |
| SEQ. ID. NO. 13928 | 169-MetThrAlaIleLeuArgArgLeuAsnGlyHisGlyIleCysArgPheHisAspLeuPheAsn-189 |
| SEQ. ID. NO. 13929 | 199-ValAsnPheIleAlaLeuLeu-205 |
| SEQ. ID. NO. 13930 | 211-GlyLeuValArgIleValGln-217 |

Antigenic Index - Jameson-Wolf

| | |
|---|---|
| SEQ. ID. NO. 13931 | 20-ArgLysGlnAsnIleAsp-25 |
| SEQ. ID. NO. 13932 | 70-LeuLeuLeuProArgThrGluThrValGluAspGluGluAlaAspProArgAlaGluLeuValArg-91 |
| SEQ. ID. NO. 13933 | 108-AlaLeuProArgAlaGlyArgAspPhe-116 |
| SEQ. ID. NO. 13934 | 148-SerArgAlaLysHisThrArgSerHisGluValIleLysGluThrIleSer-164 |
| SEQ. ID. NO. 13935 | 172-IleLeuArgArgLeuAsnGlyHisGlyIle-181 |
| SEQ. ID. NO. 13936 | 186-AspLeuPheAsnProLysGlnGlyAla-194 |
| SEQ. ID. NO. 13937 | 207-LeuAlaLysGluGlyLeu-212 |
| SEQ. ID. NO. 13938 | 216-ValGlnGluAspGlyPheGlyGluIleArgIle-226 |
| SEQ. ID. NO. 13939 | 228-LeuAsnHisGluGlyAlaHisSerAspGlyIleSerGlyThrArgGlyGlyArgAspValPhe-248 |

Hydrophilic Regions - Hopp-Woods

| | |
|---|---|
| SEQ. ID. NO. 13940 | 20-ArgLysGlnAsnIleAsp-25 |
| SEQ. ID. NO. 13941 | 70-LeuLeuLeuProArgThrGluThrValGluAspGluGluAlaAspProArgAlaGluLeuValArg-91 |
| SEQ. ID. NO. 13942 | 108-AlaLeuProArgAlaGlyArg-114 |
| SEQ. ID. NO. 13943 | 148-SerArgAlaLysHisThrArgSerHisGluValIleLysGluThrIleSer-164 |
| SEQ. ID. NO. 13944 | 207-LeuAlaLysGluGlyLeu-212 |
| SEQ. ID. NO. 13945 | 216-ValGlnGluAspGlyPheGly-222 |
| SEQ. ID. NO. 13946 | 232-GlyAlaHisSerAspGlyIleSerGlyThrArgGlyGlyArgAspValPhe-248 |

996
AMPHI Regions - AMPHI

| | |
|---|---|
| SEQ. ID. NO. 13947 | 21-LysSerAlaArgThrHisAlaLysIlePro-30 |
| SEQ. ID. NO. 13948 | 50-ProGlyGluSerTyrProAlaGlnLeuGlnLysLeuThrGlyTrpAsn-65 |
| SEQ. ID. NO. 13949 | 75-ThrSerAlaGlnAlaLeuSerArgLeuProAla-85 |
| SEQ. ID. NO. 13950 | 104-LeuArgLysValProLysGlu-110 |
| SEQ. ID. NO. 13951 | 115-AsnIleAlaLysIleIleGluThrValGlnLys-125 |
| SEQ. ID. NO. 13952 | 140-LeuGlyAlaLeuPheGlyHisLeuSerAsp-149 |
| SEQ. ID. NO. 13953 | 167-GlyAlaTrpAlaGlu-171 |
| SEQ. ID. NO. 13954 | 186-AsnGlyLysGlyTyrArgLysPheAlaGluAspLeuAsnGlnPheLeuArgLysGlnGlyPhe-206 |

Antigenic Index - Jameson-Wolf

| | |
|---|---|
| SEQ. ID. NO. 13955 | 1-MetAsnArgArgThrPhe-6 |
| SEQ. ID. NO. 13956 | 18-CysGlyArgLysSerAlaArgThrHisAlaLysIleProGluGlySerThr-34 |
| SEQ. ID. NO. 13957 | 46-TyrGlyAlaAsnProGlyGluSerTyrPro-55 |
| SEQ. ID. NO. 13958 | 69-GlyGlyValSerGlyAspThrSerAla-77 |

TABLE 1-continued

| | |
|---|---|
| SEQ. ID. NO. 13959 | 87-LeuAlaArgLysProLys-92 |
| SEQ. ID. NO. 13960 | 99-GlyGlyAsnAspPheLeuArgLysValProLysGluGlnThrArgAlaAsnIle-116 |
| SEQ. ID. NO. 13961 | 121-GluThrValGlnLysGluAsnIlePro-129 |
| SEQ. ID. NO. 13962 | 148-SerAspHisProLeuTyrGluAspLeuSerGluGluTyrGly-161 |
| SEQ. ID. NO. 13963 | 173-LeuGlyAspAsnAsnLeuLysSerAspGlnIleHisAlaAsnGlyLysGlyTyrArgLysPheAlaGluAspLeuAsnGlnPheLeuArgLysGlnGlyPheArg-207 |

Hydrophilic Regions - Hopp-Woods

| | |
|---|---|
| SEQ. ID. NO. 13964 | 18-CysGlyArgLysSerAlaArgThrHisAlaLysIleProGlu-31 |
| SEQ. ID. NO. 13965 | 49-AsnProGlyGluSerTyr-54 |
| SEQ. ID. NO. 13966 | 71-ValSerGlyAspThrSerAla-77 |
| SEQ. ID. NO. 13967 | 87-LeuAlaArgLysProLys-92 |
| SEQ. ID. NO. 13968 | 102-AspPheLeuArgLysValProLysGluGlnThrArgAlaAsnIle-116 |
| SEQ. ID. NO. 13969 | 121-GluThrValGlnLysGluAsnIle-128 |
| SEQ. ID. NO. 13970 | 154-GluAspLeuSerGluGluTyrGly-161 |
| SEQ. ID. NO. 13971 | 176-AsnAsnLeuLysSerAspGlnIleHisAlaAsn-186 |
| SEQ. ID. NO. 13972 | 188-LysGlyTyrArgLysPheAlaGluAspLeuAsnGlnPheLeuArg-202 |

997
AMPHI Regions - AMPHI

| | |
|---|---|
| SEQ. ID. NO. 13973 | 18-TrpAlaGlyLeuSerAlaAlaVal-25 |
| SEQ. ID. NO. 13974 | 70-TyrArgGlyValLeuArgLeuMetLysThrIleGly-81 |
| SEQ. ID. NO. 13975 | 107-ProLeuProAlaProLeuHisIle-114 |
| SEQ. ID. NO. 13976 | 132-LeuLeuAlaAspMetSerAspLeuGlnLysSerAlaArgLeuGly-146 |
| SEQ. ID. NO. 13977 | 164-AlaAlaValMetGlnPheTrpGlnProLeuValTrpGly-176 |
| SEQ. ID. NO. 13978 | 189-ValLeuCysAsnValLeuSerAsp-196 |
| SEQ. ID. NO. 13979 | 222-AlaLeuAlaAspLeuGlnArg-228 |
| SEQ. ID. NO. 13980 | 241-ArgLeuAsnThrLeuPro-246 |
| SEQ. ID. NO. 13981 | 275-GluGlyThrProGluHisValGlnThrAla-284 |
| SEQ. ID. NO. 13982 | 300-TyrAlaGluProValArgLeuProAlaProLeuThrGlyLeuAlaAspGly-316 |
| SEQ. ID. NO. 13983 | 355-LysAlaHisAlaAspLeuLysArgIleLeuProHisLeu-367 |
| SEQ. ID. NO. 13984 | 369-GluProGluAlaVal-373 |

Antigenic Index - Jameson-Wolf

| | |
|---|---|
| SEQ. ID. NO. 13985 | 3-AsnThrProHisProArgProLysIle-11 |
| SEQ. ID. NO. 13986 | 37-GluAlaGlyArgGlnAlaGlyGlyArgAlaArgThrLeuAlaGlyAsnThrAspGlyPheGly-57 |
| SEQ. ID. NO. 13987 | 78-LysThrIleGlySerAspProArgAlaAla-87 |
| SEQ. ID. NO. 13988 | 122-ArgArgAlaProThr-126 |
| SEQ. ID. NO. 13989 | 132-LeuLeuAlaAspMetSerAspLeuGlnLysSerAlaArgLeuGlyGlnProAspThrThr-151 |
| SEQ. ID. NO. 13990 | 156-LeuLysGlnArgAsnValProArg-163 |
| SEQ. ID. NO. 13991 | 180-ThrProLeuGluThrAlaSer-186 |
| SEQ. ID. NO. 13992 | 197-GlyValLeuThrLysLysSerGlySerAspTyrLeuLeuProLysGlnAspLeu-214 |
| SEQ. ID. NO. 13993 | 225-AspLeuGlnArgLeuGlyAlaAspIleArgLeuGluThrArgValCysArg-241 |
| SEQ. ID. NO. 13994 | 243-AsnThrLeuProAspGlyLysVal-250 |
| SEQ. ID. NO. 13995 | 273-LeuProGlyThrProGluHisVal-281 |
| SEQ. ID. NO. 13996 | 312-GlyLeuAlaAspGlyThr-317 |
| SEQ. ID. NO. 13997 | 323-CysArgGlyArgLeuGlyLeuProGluAsnGluVal-334 |
| SEQ. ID. NO. 13998 | 340-ValSerAspArgValGlyAla-346 |
| SEQ. ID. NO. 13999 | 351-AlaTrpAlaAspLysAlaHisAlaAspLeuLysArgIleLeu-364 |
| SEQ. ID. NO. 14000 | 367-LeuGlyGluProGluAlaValArgValIleThrGluLysArgAlaThrThrAlaAlaAspAlaProProProAspLeu-392 |
| SEQ. ID. NO. 14001 | 402-ProAlaGlyAspTyrLeuHisProAspTyrProAla-413 |

Hydrophilic Regions - Hopp-Woods

| | |
|---|---|
| SEQ. ID. NO. 14002 | 5-ProHisProArgProLysIle-11 |
| SEQ. ID. NO. 14003 | 37-GluAlaGlyArgGlnAlaGlyGlyArgAlaArgThrLeuAlaGlyAsn-52 |
| SEQ. ID. NO. 14004 | 80-IleGlySerAspProArgAlaAla-87 |
| SEQ. ID. NO. 14005 | 122-ArgArgAlaProThr-126 |
| SEQ. ID. NO. 14006 | 132-LeuLeuAlaAspMetSerAspLeuGlnLysSerAlaArgLeuGlyGlnProAspThrThr-151 |
| SEQ. ID. NO. 14007 | 198-ValLeuThrLysLysSerGlySer-205 |
| SEQ. ID. NO. 14008 | 208-LeuLeuProLysGlnAspLeu-214 |
| SEQ. ID. NO. 14009 | 225-AspLeuGlnArgLeuGlyAlaAspIleArgLeuGluThrArgValCysArg-241 |
| SEQ. ID. NO. 14010 | 246-ProAspGlyLysVal-250 |
| SEQ. ID. NO. 14011 | 276-GlyThrProGluHisVal-281 |
| SEQ. ID. NO. 14012 | 325-GlyArgLeuGlyLeuProGluAsnGluVal-334 |
| SEQ. ID. NO. 14013 | 340-ValSerAspArgValGly-345 |
| SEQ. ID. NO. 14014 | 351-AlaTrpAlaAspLysAlaHisAlaAspLeuLysArgIleLeu-364 |
| SEQ. ID. NO. 14015 | 368-GlyGluProGluAlaValArgValIleThrGluLysArgAlaThrThrAlaAlaAspAlaProProPro-390 |

999
AMPHI Regions - AMPHI

| | |
|---|---|
| SEQ. ID. NO. 14016 | 6-LeuIleSerAlaIleCysValSerIle-14 |
| SEQ. ID. NO. 14017 | 30-GluProValGlnSerIleGlnAlaAla-38 |
| SEQ. ID. NO. 14018 | 117-GlyGlnAsnLeuValAsnAsnAlaIleAsnGlyLeuHisSerIleGlnAlaValLeuSer-136 |
| SEQ. ID. NO. 14019 | 138-ThrThrThrAspLys-142 |
| SEQ. ID. NO. 14020 | 151-GlnLeuPheThrAlaLeuThrGluValValLysGluSer-163 |

Antigenic Index - Jameson-Wolf

| | |
|---|---|
| SEQ. ID. NO. 14021 | 1-MetAsnMetLysLysLeuIle-7 |
| SEQ. ID. NO. 14022 | 18-AlaCysAsnGlnGlnSerLysThrAlaGlnAlaGluGluProValGln-33 |
| SEQ. ID. NO. 14023 | 42-AlaProMetAspIleThrVal-48 |
| SEQ. ID. NO. 14024 | 57-GlnAlaPheLysThrGlnAsnValSer-65 |
| SEQ. ID. NO. 14025 | 67-LysIleHisAsnLysAsnIleValLysThrAspCysGlyTyr-80 |
| SEQ. ID. NO. 14026 | 94-LysLeuAspGluGlnGlnLysIleArgAla-103 |
| SEQ. ID. NO. 14027 | 111-LysThrAspGlyGluLysGlyGlnAsnLeu-120 |
| SEQ. ID. NO. 14028 | 138-ThrThrThrAspLysLeuGlyGluSerGluAlaGlyLys-150 |
| SEQ. ID. NO. 14029 | 158-GluValValLysGluSerAsnGlnThrGly-167 |

TABLE 1-continued

| SEQ. ID. NO. 14030 | 169-ThrAlaGlnLysAspValProAlaAspGly-178 |

SEQ. ID. NO. 14031    185-PheGluLysGluThrAsnThr-191
SEQ. ID. NO. 14032    195-IleGlyArgLysGlnPro-200
Hydrophilic Regions - Hopp-Woods
SEQ. ID. NO. 14033    1-MetAsnMetLysLysLeuIle-7
SEQ. ID. NO. 14034    21-GlnGlnSerLysThrAlaGlnAlaGluGluProValGln-33
SEQ. ID. NO. 14035    72-AsnIleValLysThrAspCysGlyTyr-80
SEQ. ID. NO. 14036    94-LysLeuAspGluGlnGlnLysIleArgAla-103
SEQ. ID. NO. 14037    112-ThrAspGlyGluLysGlyGlnAsn-119
SEQ. ID. NO. 14038    139-ThrThrAspLysLeuGlyGluSerGluAlaGlyLys-150
SEQ. ID. NO. 14039    158-GluValValLysGluSerAsnGln-165
SEQ. ID. NO. 14040    169-ThrAlaGlnLysAspValProAla-176
SEQ. ID. NO. 14041    185-PheGluLysGluThrAsn-190
SEQ. ID. NO. 14042    195-IleGlyArgLysGlnPro-200
a001
AMPHI Regions - AMPHI
SEQ. ID. NO. 14043    7-AlaAlaArgArgMet-11
SEQ. ID. NO. 14044    69-PhePheGlySerAlaCysAsnSerAlaAla-78
Antigenic Index - Jameson-Wolf
SEQ. ID. NO. 14045    3-ProGlnGlyLysAlaAlaArgArgMetSerAlaAsnGluValCys-17
SEQ. ID. NO. 14046    31-ThrLeuProLysArgAspThrLeuAsnGlySerGlyThr-43
SEQ. ID. NO. 14047    53-ProArgSerLeuArgSerLysSerThr-61
SEQ. ID. NO. 14048    68-ArgPhePheGlySerAlaCysAsnSerAlaAlaArgArgSerSerCysProSerProLysIleGly-89
SEQ. ID. NO. 14049    100-ValProSerGluProIleLeuArgLysSerSerGlyGluLysHisSerVal-116
SEQ. ID. NO. 14050    118-AlaAspCysProCysAlaSerGlyArgTrpAspLysThrAla-131
Hydrophilic Regions - Hopp-Woods
SEQ. ID. NO. 14051    5-GlyLysAlaAlaArgArgMetSerAla-13
SEQ. ID. NO. 14052    32-LeuProLysArgAspThrLeuAsn-39
SEQ. ID. NO. 14053    54-ArgSerLeuArgSerLysSer-60
SEQ. ID. NO. 14054    76-SerAlaAlaArgArgSerSerCysProSerProLys-87
SEQ. ID. NO. 14055    104-ProIleLeuArgLysSerSerGlyGluLysHisSerVal-116
SEQ. ID. NO. 14056    125-GlyArgTrpAspLysThrAla-131
a003
AMPHI Regions - AMPHI
SEQ. ID. NO. 14057    72-AsnGlnValValLeu-76
SEQ. ID. NO. 14058    82-IleValGluValPheGlnArg-88
SEQ. ID. NO. 14059    138-ArgIleAsnAspAlaGluGluIleLeuGlnAspValValAlaGluPheValGlyIleValGlyHisPheAspGlyPheGlyVal-165
SEQ. ID. NO. 14060    174-PheIleAlaArgIlePheArgVal-181
Antigenic Index - Jameson-Wolf
SEQ. ID. NO. 14061    91-PheAsnAsnGluGlyGln-96
SEQ. ID. NO. 14062    104-PheGluGlyGlyGlyAspAspGlyPhe-112
SEQ. ID. NO. 14063    137-GlyArgIleAsnAspAlaGluGluIleLeu-146
SEQ. ID. NO. 14064    204-ProGluAlaAlaAlaGlyGluValAspGlyAlaArgValHisAsp-218
Hydrophilic Regions - Hopp-Woods
SEQ. ID. NO. 14065    106-GlyGlyGlyAspAspGlyPhe-112
SEQ. ID. NO. 14066    137-GlyArgIleAsnAspAlaGluGluIleLeu-146
SEQ. ID. NO. 14067    205-GluAlaAlaAlaGlyGluValAspGlyAlaArgValHisAsp-218
a005
AMPHI Regions - AMPHI
SEQ. ID. NO. 14068    14-IleGlnSerMetTrpLysGlu-20
SEQ. ID. NO. 14069    30-LeuGluLeuLeuThrValPheGlyAlaIleAla-40
SEQ. ID. NO. 14070    60-LeuThrAspPheSerGluAsnTyr-67
SEQ. ID. NO. 14071    105-ArgLeuLysGluGlyGlyGluLysSerSerGlu-115
SEQ. ID. NO. 14072    175-GlnLeuArgArgLeuArg-180
SEQ. ID. NO. 14073    214-AlaIleValGlySerValGlyValValAlaGluValProAsnIleHisArgLeuLeuLysLys-234
SEQ. ID. NO. 14074    247-PheLysArgThrVal-251
SEQ. ID. NO. 14075    272-ThrHisGlnLeuPheLysGln-278
SEQ. ID. NO. 14076    306-LeuAsnLeuIleAspGluIleSerThr-314
SEQ. ID. NO. 14077    318-LeuLeuLysLysAlaPhe-323
Antigenic Index - Jameson-Wolf
SEQ. ID. NO. 14078    8-MetProGluGlnGluGluIleGlnSerMetTrp-18
SEQ. ID. NO. 14079    48-GlnSerLysLysGlnSerGluSerGlySer-57
SEQ. ID. NO. 14080    62-AspPheSerGluAsnTyrLysLysGlnArgGlnSerPhe-74
SEQ. ID. NO. 14081    80-SerGlyGluGluAlaLysHisGlnGluLysGluGluLysLysLysGluLys
                      AlaGluAlaLysAlaGluLysLysArgLeuLysGluGlyGlyGluLysSerSerGluThrGlnLysSerArg-120
SEQ. ID. NO. 14082    136-GluSerLeuArgHisGluIle-142
SEQ. ID. NO. 14083    149-AlaLysProGluAspGluValLeuLeu-157
SEQ. ID. NO. 14084    159-LeuGluSerProGlyGlyVal-165
SEQ. ID. NO. 14085    175-GlnLeuArgArgLeuArgGluArgAsnIle-184
SEQ. ID. NO. 14086    189-AlaValAspLysValAlaAla-195
SEQ. ID. NO. 14087    230-ArgLeuLeuLysLysHisAspIleAspVal-239
SEQ. ID. NO. 14088    245-GlyGluPheLysArgThr-250
SEQ. ID. NO. 14089    256-GluAsnThrGluLysGlyLysGlnLysPheArgGlnGluLeuGluGluThrHisGln-274
SEQ. ID. NO. 14090    279-PheValSerGluAsnArgProGlnLeuAspIleGluGluValAlaThr-294
SEQ. ID. NO. 14091    310-AspGluIleSerThrSerAspAspLeuLeu-319
SEQ. ID. NO. 14092    323-PheGluAsnLysGlnValIle-329
SEQ. ID. NO. 14093    332-LysTyrGlnGluLysGlnSerLeu-339
SEQ. ID. NO. 14094    349-AlaSerValGluLysLeuPhe-355
SEQ. ID. NO. 14095    359-ValAsnArgArgAlaAspVal-365

TABLE 1-continued

Hydrophilic Regions - Hopp-Woods
SEQ. ID. NO. 14096  8-MetProGluGlnGluGluIleGlnSerMetTrp-18
SEQ. ID. NO. 14097  48-GlnSerLysLysGlnSerGluSerGly-56
SEQ. ID. NO. 14098  62-AspPheSerGluAsnTyrLysLysGlnArgGlnSerPhe-74
SEQ. ID. NO. 14099  81-GlyGluGluAlaLysHisGlnGluLysGluGluLysLysLysGluLysAlaGluAlaLysAlaGluLysLysArgLeuLysGluGlyGly
GluLysSerSerGluThrGlnLysSerArg-120
SEQ. ID. NO. 14100  136-GluSerLeuArgHisGluIle-142
SEQ. ID. NO. 14101  149-AlaLysProGluAspGluValLeuLeu-157
SEQ. ID. NO. 14102  159-LeuGluSerProGly-163
SEQ. ID. NO. 14103  175-GlnLeuArgArgLeuArgGluArgAsnIle-184
SEQ. ID. NO. 14104  189-AlaValAspLysValAlaAla-195
SEQ. ID. NO. 14105  230-ArgLeuLeuLysLysHisAspIleAspVal-239
SEQ. ID. NO. 14106  245-GlyGluPheLysArg-249
SEQ. ID. NO. 14107  256-GluAsnThrGluLysGlyLysGlnLysPheArgGlnGluLeuGluGluThrHisGln-274
SEQ. ID. NO. 14108  279-PheValSerGluAsnArgProGlnLeuAspIleGluGluValAlaThr-294
SEQ. ID. NO. 14109  310-AspGluIleSerThrSerAspAspLeuLeu-319
SEQ. ID. NO. 14110  323-PheGluAsnLysGlnValIle-329
SEQ. ID. NO. 14111  332-LysTyrGlnGluLysGlnSerLeu-339
SEQ. ID. NO. 14112  349-AlaSerValGluLysLeuPhe-355
SEQ. ID. NO. 14113  359-ValAsnArgArgAlaAspVal-365
a006-1
AMPHI Regions - AMPHI
SEQ. ID. NO. 14114  40-GlnAlaTrpGlnAlaLeuLeuTyrAlaLeuValValLeu-52
SEQ. ID. NO. 14115  61-ArgArgIleAlaAspThrArgThrPheThrArgIleTyrThrGlu-75
SEQ. ID. NO. 14116  103-GluPheValSerPhePheGlu-109
SEQ. ID. NO. 14117  117-ThrSerValValSerIlePheGlyAlaCysIleMetLeuLeu-130
SEQ. ID. NO. 14118  179-GlyAspGluArgGlnLeu-184
SEQ. ID. NO. 14119  186-ArgHisTyrGlyLeuLeuAlaArgLeu-194
SEQ. ID. NO. 14120  228-GlyTyrSerSerAlaGlyHisValTyrSer-237
SEQ. ID. NO. 14121  249-LeuAspAspValProArgLeuValGluGlnTyrSerAsnLeuLysAspIle-265
Antigenic Index - Jameson-Wolf
SEQ. ID. NO. 14122  1-SerGlnAsnHisArgLysArgLeu-8
SEQ. ID. NO. 14123  59-AlaAlaArgArgIleAlaAspThrArgThrPheThr-70
SEQ. ID. NO. 14124  82-LeuGluGlnArgGlnArgGlnValProHisSer-92
SEQ. ID. NO. 14125  163-PheArgLeuLysAsnSerLeuGluArgAspAsnHisPheIleArgLysGlyAspGluArgGlnLeuAspArgHisTyr-188
SEQ. ID. NO. 14126  198-IleSerAsnArgGluAlaPhe-204
SEQ. ID. NO. 14127  227-LysGlyTyrSerSer-231
SEQ. ID. NO. 14128  249-LeuAspAspValProArgLeuValGluGlnTyrSerAsnLeuLysAspIleGlyGln-267
SEQ. ID. NO. 14129  269-IleGluTrpSerLysArgAsnIleLysAlaGlyThr-280
Hydrophilic Regions - Hopp-Woods
SEQ. ID. NO. 14130  1-SerGlnAsnHisArgLysArgLeu-8
SEQ. ID. NO. 14131  59-AlaAlaArgArgIleAlaAspThrArgThrPhe-69
SEQ. ID. NO. 14132  82-LeuGluGlnArgGlnArgGlnValPro-90
SEQ. ID. NO. 14133  166-LysAsnSerLeuGluArgAspAsnHisPheIleArgLysGlyAspGluArgGlnLeuAspArg-186
SEQ. ID. NO. 14134  198-IleSerAsnArgGluAla-203
SEQ. ID. NO. 14135  249-LeuAspAspValProArgLeuValGlu-257
SEQ. ID. NO. 14136  260-SerAsnLeuLysAspIleGlyGln-267
SEQ. ID. NO. 14137  269-IleGluTrpSerLysArgAsnIleLysAlaGlyThr-280
a007-1
AMPHI Regions - AMPHI
SEQ. ID. NO. 14138  71-HisSerMetValLysGlyIleAsn-78
SEQ. ID. NO. 14139  105-ValAlaThrTyrIleMetAsnAlaPheAspAsnGlyGlyGly-118
Antigenic Index - Jameson-Wolf
SEQ. ID. NO. 14140  1-MetAsnThrThrArgLeu-6
SEQ. ID. NO. 14141  20-SerAlaAlaAspAsnSerIleMetThrLysGlyGlnLysValTyrGluSerAsnCys-38
SEQ. ID. NO. 14142  41-CysHisGlyLysLysGlyGluGlyArgGlyThr-51
SEQ. ID. NO. 14143  55-ProLeuTyrArgSerAspPheIleMetLysLysProGln-67
SEQ. ID. NO. 14144  83-ValAsnGlyLysThrTyrAsnGly-90
SEQ. ID. NO. 14145  98-SerAspAlaAspIle-102
SEQ. ID. NO. 14146  112-AlaPheAspAsnGlyGlyGlySerValThrGluLysAspValLysGlnAlaLysAsnLysLys-132
Hydrophilic Regions - Hopp-Woods
SEQ. ID. NO. 14147  26-IleMetThrLysGlyGlnLysValTyrGlu-35
SEQ. ID. NO. 14148  42-HisGlyLysLysGlyGluGlyArgGly-50
SEQ. ID. NO. 14149  61-PheIleMetLysLysProGln-67
SEQ. ID. NO. 14150  98-SerAspAlaAspIle-102
SEQ. ID. NO. 14151  119-SerValThrGluLysAspValLysGlnAlaLysAsnLysLys-132
a008
AMPHI Regions - AMPHI
SEQ. ID. NO. 14152  15-LeuGluAsnProAlaGlnGlnValArgAlaAlaLeuAspThrLeuSer-30
SEQ. ID. NO. 14153  54-GlnProAspPheValAsnAlaVal-61
SEQ. ID. NO. 14154  69-AspGlyIleAlaLeuLeuAlaGluLeuAsnArg-79
SEQ. ID. NO. 14155  90-PheArgAsnAlaPro-94
SEQ. ID. NO. 14156  129-ArgProLeuAlaGluIleLeuProAsp-137
SEQ. ID. NO. 14157  144-GlyLysValAlaGluLeuSerLysArgLeuGly-154
Antigenic Index - Jameson-Wolf
SEQ. ID. NO. 14158  1-MetAsnAsnArgHis-5
SEQ. ID. NO. 14159  12-GlySerAsnLeuGluAsnProAlaGlnGlnVal-22
SEQ. ID. NO. 14160  29-LeuSerSerHisProAspIleArgLeuLysGlnAlaSerSer-42
SEQ. ID. NO. 14161  49-ValGlyTyrAspAsnGlnProAspPhe-57

TABLE 1-continued

| | |
|---|---|
| SEQ. ID. NO. 14162 | 76-GluLeuAsnArgIleGluAlaAspPheGlyArgGluArgSerPheArgAsnAlaProArgThrLeuAspLeuAspIleIleAspPheAsp GlyIleSerSerAspAspProArgLeuThrLeuProHisProArgAlaHisGluArgSerPheVal-127 |
| SEQ. ID. NO. 14163 | 140-LeuGlyLysHisGlyLysValAlaGluLeuSerLysArgLeuGlyAsnGlnGlyIle-158 |
| SEQ. ID. NO. 14164 | 160-LeuLeuProAspLys-164 |
| Hydrophilic Regions - Hopp-Woods | |
| SEQ. ID. NO. 14165 | 14-AsnLeuGluAsnProAlaGlnGlnVal-22 |
| SEQ. ID. NO. 14166 | 33-ProAspIleArgLeuLysGln-39 |
| SEQ. ID. NO. 14167 | 76-GluLeuAsnArgIleGluAlaAspPheGlyArgGluArgSerPheArgAsnAlaProArgThrLeuAsp-98 |
| SEQ. ID. NO. 14168 | 105-AspGlyIleSerSerAspAspProArgLeu-114 |
| SEQ. ID. NO. 14169 | 120-ArgAlaHisGluArgSerPheVal-127 |
| SEQ. ID. NO. 14170 | 142-LysHisGlyLysValAlaGluLeuSerLysArgLeuGly-154 |
| SEQ. ID. NO. 14171 | 160-LeuLeuProAspLys-164 |
| a009 | |
| Antigenic Index - Jameson-Wolf | |
| SEQ. ID. NO. 14172 | 6-ValAlaPheGluArgHisHisHisLysSerLysAlaGluGlnAsnThrHisArgArgAlaAspAlaGluIleAlaGlu-31 |
| SEQ. ID. NO. 14173 | 37-AsnGlnHisThrGlnAlaArgLysGlnSer-46 |
| SEQ. ID. NO. 14174 | 57-PheSerAspLysVal-61 |
| SEQ. ID. NO. 14175 | 77-AlaAspGlyGlyLysThrTrpGlnLysPro-86 |
| Hydrophilic Regions - Hopp-Woods | |
| SEQ. ID. NO. 14176 | 6-ValAlaPheGluArgHisHisHisLysSerLysAlaGluGlnAsnThrHisArgArgAlaAspAlaGluIleAlaGlu-31 |
| SEQ. ID. NO. 14177 | 40-ThrGlnAlaArgLysGlnSer-46 |
| SEQ. ID. NO. 14178 | 78-AspGlyGlyLysThrTrpGln-84 |
| a010-1 | |
| AMPHI Regions - AMPHI | |
| SEQ. ID. NO. 14179 | 54-SerAlaSerLeuGly-58 |
| SEQ. ID. NO. 14180 | 70-TyrAspThrValLysGly-75 |
| SEQ. ID. NO. 14181 | 115-TyrGlnArgProPheGlyGlyHis-122 |
| SEQ. ID. NO. 14182 | 125-GluHisGlyLysArgAlaVal-131 |
| SEQ. ID. NO. 14183 | 146-LeuHisThrLeuTyrGln-151 |
| SEQ. ID. NO. 14184 | 210-AlaSerSerThrAsn-214 |
| SEQ. ID. NO. 14185 | 216-TyrMetAsnThrGlyAspGly-222 |
| SEQ. ID. NO. 14186 | 275-ArgTyrAlaProThrValLys-281 |
| SEQ. ID. NO. 14187 | 322-IleMetGluLysLeuProGlyIleArg-330 |
| SEQ. ID. NO. 14188 | 338-GlyIleAspProIleLysAspProIlePro-347 |
| SEQ. ID. NO. 14189 | 357-GlyGlyIleProThrAsnTyrHis-364 |
| SEQ. ID. NO. 14190 | 413-AlaAlaGlyAspSerMetIleLysPheIleLysGluGlnSerAspTrp-428 |
| SEQ. ID. NO. 14191 | 446-LeuAspAsnGlnThrAsp-451 |
| SEQ. ID. NO. 14192 | 453-GluAsnValAspAlaLeuArgArgGluLeu-462 |
| SEQ. ID. NO. 14193 | 479-LeuSerLysGlyValArgGluValMetAlaIleAlaGlu-491 |
| SEQ. ID. NO. 14194 | 505-TrpAsnThrAlaArg-509 |
| SEQ. ID. NO. 14195 | 514-GluLeuAspAsnLeuIleGluValAlaLys-523 |
| Antigenic Index - Jameson-Wolf | |
| SEQ. ID. NO. 14196 | 14-GlyGlyGlyGlyAlaGlyLeu-20 |
| SEQ. ID. NO. 14197 | 26-LeuSerLysSerGlyLeu-31 |
| SEQ. ID. NO. 14198 | 40-PheProThrArgSerHisThr-46 |
| SEQ. ID. NO. 14199 | 59-AsnValGlnGluAspArgTrpAsp-66 |
| SEQ. ID. NO. 14200 | 71-AspThrValLysGlySerAspTrpLeuGlyAspGlnAspAlaIle-85 |
| SEQ. ID. NO. 14201 | 104-MetProPheAspArgValGluSerGlyLysIleTyrGlnArgProPheGly-120 |
| SEQ. ID. NO. 14202 | 123-ThrAlaGluHisGlyLysArgAlaValGluArgAlaCysAlaValAlaAspArgThrGly-142 |
| SEQ. ID. NO. 14203 | 152-GlnAsnValArgAlaAsnThrGln-159 |
| SEQ. ID. NO. 14204 | 168-AspLeuIleArgAspGluAsnGlyAspVal-177 |
| SEQ. ID. NO. 14205 | 183-MetGluMetGluThrGlyGlu-189 |
| SEQ. ID. NO. 14206 | 202-ThrGlyGlyGlyGlyArgIle-208 |
| SEQ. ID. NO. 14207 | 211-SerSerThrAsnAla-215 |
| SEQ. ID. NO. 14208 | 218-AsnThrGlyAspGlyLeu-223 |
| SEQ. ID. NO. 14209 | 231-IleProLeuGluAspMetGlu-237 |
| SEQ. ID. NO. 14210 | 255-GluGlyValArgGlyGluGlyGlyIle-263 |
| SEQ. ID. NO. 14211 | 266-AsnAlaAspGlyGluArgPheMetGlu-274 |
| SEQ. ID. NO. 14212 | 276-TyrAlaProThrValLysAspLeuAlaSerArgAspValValSer-290 |
| SEQ. ID. NO. 14213 | 297-IleTyrGluGlyArgGlyCysGlyLysAsnLysAspHisVal-310 |
| SEQ. ID. NO. 14214 | 315-AspHisIleGlyAlaGluLysIleMetGluLysLeuProGlyIleArgGluIleSer-333 |
| SEQ. ID. NO. 14215 | 338-GlyIleAspProIleLysAspProIle-346 |
| SEQ. ID. NO. 14216 | 368-ValValProGlnGlyAspGlyTyrAsnValProVal-379 |
| SEQ. ID. NO. 14217 | 395-GlyAlaAsnArgLeuGlyThrAsnSerLeu-404 |
| SEQ. ID. NO. 14218 | 413-AlaAlaGlyAspSerMet-418 |
| SEQ. ID. NO. 14219 | 421-PheIleLysGluGlnSerAspTrpLysProLeuProAlaAsnAlaGlyGluLeuThrArgGlnArgIleGluArgLeuAspAsnGlnThr AspGlyGluAsnValAspAlaLeuArgArgGluLeuGlnArgSer-465 |
| SEQ. ID. NO. 14220 | 473-PheArgThrAspGluIleLeuSerLysGlyValArgGlu-485 |
| SEQ. ID. NO. 14221 | 487-MetAlaIleAlaGluArgValLysArgThrGluIleLysAspLysSerLysVal-504 |
| SEQ. ID. NO. 14222 | 508-AlaArgIleGluAlaLeuGluLeu-515 |
| SEQ. ID. NO. 14223 | 529-AlaGluAlaArgLysGluSerArgGlyAlaHisAlaSerAspAspHisProGluArgAspAspGluAsnTrpMet-553 |
| SEQ. ID. NO. 14224 | 558-TyrHisSerAspAlaAsnThrLeuSerTyrLysProValHisThrLysProLeuSer-576 |
| SEQ. ID. NO. 14225 | 581-LysProAlaLysArgValTyr-587 |
| Hydrophilic Regions - Hopp-Woods | |
| SEQ. ID. NO. 14226 | 26-LeuSerLysSerGlyLeu-31 |
| SEQ. ID. NO. 14227 | 59-AsnValGlnGluAspArgTrpAsp-66 |
| SEQ. ID. NO. 14228 | 71-AspThrValLysGly-75 |
| SEQ. ID. NO. 14229 | 77-AspTrpLeuGlyAspGlnAspAlaIle-85 |
| SEQ. ID. NO. 14230 | 105-ProPheAspArgValGluSerGlyLysIleTyr-115 |
| SEQ. ID. NO. 14231 | 123-ThrAlaGluHisGlyLysArgAlaValGluArgAlaCysAlaValAlaAspArgThrGly-142 |

TABLE 1-continued

| | |
|---|---|
| SEQ. ID. NO. 14232 | 168-AspLeuIleArgAspGluAsnGlyAsp-176 |
| SEQ. ID. NO. 14233 | 183-MetGluMetGluThrGlyGlu-189 |
| SEQ. ID. NO. 14234 | 231-IleProLeuGluAspMetGlu-237 |
| SEQ. ID. NO. 14235 | 255-GluGlyValArgGlyGluGly-261 |
| SEQ. ID. NO. 14236 | 267-AlaAspGlyGluArgPheMetGlu-274 |
| SEQ. ID. NO. 14237 | 276-TyrAlaProThrValLysAspLeuAlaSerArgAspValValSer-290 |
| SEQ. ID. NO. 14238 | 297-IleTyrGluGlyArgGlyCysGlyLysAsnLysAspHisVal-310 |
| SEQ. ID. NO. 14239 | 315-AspHisIleGlyAlaGluLysIleMetGluLysLeuProGlyIleArgGluIleSer-333 |
| SEQ. ID. NO. 14240 | 340-AspProIleLysAspProIle-346 |
| SEQ. ID. NO. 14241 | 371-GlnGlyAspGluTyrGluValProVal-379 |
| SEQ. ID. NO. 14242 | 421-PheIleLysGluGlnSerAspTrpLysPro-430 |
| SEQ. ID. NO. 14243 | 434-AsnAlaGlyGluLeuThrArgGlnArgIleGluArgLeuAspAsnGlnThrAspGlyGluAsnValAspAlaLeuArgArgGluLeuGlnArg-464 |
| SEQ. ID. NO. 14244 | 473-PheArgThrAspGluIleLeuSerLysGlyValArgGlu-485 |
| SEQ. ID. NO. 14245 | 487-MetAlaIleAlaGluArgValLysArgThrGluIleLysAspLysSerLysVal-504 |
| SEQ. ID. NO. 14246 | 508-AlaArgIleGluAlaLeuGluLeu-515 |
| SEQ. ID. NO. 14247 | 529-AlaGluAlaArgLysGluSerArgGlyAlaHisAlaSerAspAspHisProGluArgAspAspGluAsnTrpMet-553 |
| SEQ. ID. NO. 14248 | 581-LysProAlaLysArgValTyr-587 | a011
AMPHI Regions - AMPHI

| | |
|---|---|
| SEQ. ID. NO. 14249 | 58-IleArgLeuIleAsnAlaAla-64 |
| SEQ. ID. NO. 14250 | 83-AlaIleLeuThrLys-87 |
| SEQ. ID. NO. 14251 | 116-GluValLeuHisArgTyrLeuProGlnMetLeuSerAlaGly-129 |
| SEQ. ID. NO. 14252 | 147-MetAlaXxxMetGlyLysValMetGlyVal-156 |

Antigenic Index - Jameson-Wolf

| | |
|---|---|
| SEQ. ID. NO. 14253 | 1-MetArgThrHisArgLysThrCysSer-9 |
| SEQ. ID. NO. 14254 | 17-ThrAlaSerLysProAlaValSerIleArgHisProSerGluAsnIleMet-33 |
| SEQ. ID. NO. 14255 | 37-IleArgLeuThrGluAspMetLysThrAlaMetArgAlaLysAspGlnVal-53 |
| SEQ. ID. NO. 14256 | 66-LysGlnPheGluValAspGluArgThrGluAlaAspAspAlaLysIle-81 |
| SEQ. ID. NO. 14257 | 88-MetValLysGlnArgLysAspSerValLysIle-98 |
| SEQ. ID. NO. 14258 | 100-ThrGluAlaGlyArgGlnAspLeuAlaAspLysGluAsnAlaGluIle-115 |
| SEQ. ID. NO. 14259 | 127-SerAlaGlyGluIleArgThrAlaVal-135 |
| SEQ. ID. NO. 14260 | 157-XxxLysThrArgLeuAlaGlyLysAlaAspMetGlyGluValAsnLysIleLeu-174 |

Hydrophilic Regions - Hopp-Woods

| | |
|---|---|
| SEQ. ID. NO. 14261 | 1-MetArgThrHisArgLysThrCys-8 |
| SEQ. ID. NO. 14262 | 37-IleArgLeuThrGluAspMetLysThrAlaMetArgAlaLysAspGlnVal-53 |
| SEQ. ID. NO. 14263 | 66-LysGlnPheGluValAspGluArgThrGluAlaAspAspAlaLysIle-81 |
| SEQ. ID. NO. 14264 | 88-MetValLysGlnArgLysAspSerValLysIle-98 |
| SEQ. ID. NO. 14265 | 100-ThrGluAlaGlyArgGlnAspLeuAlaAspLysGluAsnAlaGluIle-115 |
| SEQ. ID. NO. 14266 | 129-GlyGluIleArgThrAlaVal-135 |
| SEQ. ID. NO. 14267 | 157-XxxLysThrArgLeuAlaGlyLysAlaAspMetGlyGluValAsnLysIleLeu-174 | a012-1
AMPHI Regions - AMPHI

| | |
|---|---|
| SEQ. ID. NO. 14268 | 19-LysLeuLeuGluGlnLeuMetArgPheLeuGlnPheLeuSerGluPheLeuPheAlaLeuPheArgIle-41 |
| SEQ. ID. NO. 14269 | 48-ArgAlaLeuLysPheAlaArgArg-55 |
| SEQ. ID. NO. 14270 | 89-AsnAsnPheIleArgHisThr-95 |
| SEQ. ID. NO. 14271 | 160-GlnGlyPheTyrGlyVal-165 |
| SEQ. ID. NO. 14272 | 179-GlyPheLeuArgPheGlyArgPheLeuProThrLeuLeuGlnThrLeu-194 |

Antigenic Index - Jameson-Wolf

| | |
|---|---|
| SEQ. ID. NO. 14273 | 42-PheThrHisLysSerAsnArgAlaLeuLysPheAlaArgArgHisHis-57 |
| SEQ. ID. NO. 14274 | 72-ArgTyrPheArgTyrAsnThrHisArgThrAspAsnArgLysArgSerGlyAsnAsnPhe-91 |
| SEQ. ID. NO. 14275 | 93-ArgHisThrArgHisHis-98 |
| SEQ. ID. NO. 14276 | 101-ThrAlaArgArgHisLeuIleAspGlyAspGlyGlnArgAsn-114 |
| SEQ. ID. NO. 14277 | 119-GlnThrProLysLeuArgSerArgGln-127 |
| SEQ. ID. NO. 14278 | 137-ThrPheGlnSerLysGlnAsnLeu-144 |
| SEQ. ID. NO. 14279 | 147-ArgLeuGlyAsnGlnLysHisArgArgAsnLeuMetThrGln-160 |
| SEQ. ID. NO. 14280 | 173-IleGlnHisLysLysAlaGly-179 |

Hydrophilic Regions - Hopp-Woods

| | |
|---|---|
| SEQ. ID. NO. 14281 | 45-LysSerAsnArgAlaLeuLysPheAlaArgArgHisHis-57 |
| SEQ. ID. NO. 14282 | 77-AsnThrHisArgThrAspAsnArgLysArgSerGly-88 |
| SEQ. ID. NO. 14283 | 101-ThrAlaArgArgHisLeuIleAspGlyAspGlyGlnArg-113 |
| SEQ. ID. NO. 14284 | 121-ProLysLeuArgSerArgGln-127 |
| SEQ. ID. NO. 14285 | 149-GlyAsnGlnLysHisArgArgAsnLeu-157 |
| SEQ. ID. NO. 14286 | 173-IleGlnHisLysLysAlaGly-179 | a015
AMPHI Regions - AMPHI

| | |
|---|---|
| SEQ. ID. NO. 14287 | 25-ValPheXxxLeuTrpLysAsnProGluLysProLeuAlaGlyPheTrpLysAlaLeuProHis-45 |
| SEQ. ID. NO. 14288 | 107-MetCysCysLeuThrCys-112 |

Antigenic Index - Jameson-Wolf

| | |
|---|---|
| SEQ. ID. NO. 14289 | 29-TrpLysAsnProGluLysProLeu-36 |
| SEQ. ID. NO. 14290 | 90-MetArgAlaArgProArgSerThrLys-98 |

Hydrophilic Regions - Hopp-Woods

| | |
|---|---|
| SEQ. ID. NO. 14291 | 30-LysAsnProGluLysProLeu-36 |
| SEQ. ID. NO. 14292 | 90-MetArgAlaArgProArgSerThrLys-98 | a018-2
AMPHI Regions - AMPHI

| | |
|---|---|
| SEQ. ID. NO. 14293 | 6-IleGlnHisLeuArg-10 |
| SEQ. ID. NO. 14294 | 100-AspGlyAlaAlaAla-104 |
| SEQ. ID. NO. 14295 | 152-ArgIleGlyAsnGlyTyr-157 |

Antigenic Index - Jameson-Wolf

| | |
|---|---|
| SEQ. ID. NO. 14296 | 1-MetValGluArgHisIleGln-7 |

TABLE 1-continued

| | |
|---|---|
| SEQ. ID. NO. 14297 | 9-LeuArgAsnGlyHis-13 |
| SEQ. ID. NO. 14298 | 19-ProSerGlnGlnValArg-24 |
| SEQ. ID. NO. 14299 | 27-PheGlyGlyArgThrTyrAspPheCysAlaAspGluAlaAla-40 |
| SEQ. ID. NO. 14300 | 67-TyrPheAlaAspAspLysPhe-73 |
| SEQ. ID. NO. 14301 | 78-LeuArgGlyAsnLeuArg-83 |
| SEQ. ID. NO. 14302 | 85-PheGlnThrAspLysAlaAspLeuArgThrGlyGluHisTyrAlaAspGlyAlaAla-103 |
| SEQ. ID. NO. 14303 | 108-AlaAspIleArgVal-112 |
| SEQ. ID. NO. 14304 | 136-ArgValAlaArgAsnLysAspMetArgAsnThrGlyLeuHisSerGlnArgIleGlyAsnGlyTyr-157 |
| Hydrophilic Regions - Hopp-Woods | |
| SEQ. ID. NO. 14305 | 1-MetValGluArgHisIleGln-7 |
| SEQ. ID. NO. 14306 | 35-CysAlaAspGluAlaAla-40 |
| SEQ. ID. NO. 14307 | 67-TyrPheAlaAspAspLysPhe-73 |
| SEQ. ID. NO. 14308 | 85-PheGlnThrAspLysAlaAspLeuArgThrGlyGluHisTyrAla-99 |
| SEQ. ID. NO. 14309 | 108-AlaAspIleArgVal-112 |
| SEQ. ID. NO. 14310 | 136-ArgValAlaArgAsnLysAspMetArgAsn-145 |
| a019-2 | |
| AMPHI Regions - AMPHI | |
| SEQ. ID. NO. 14311 | 33-ProAlaAspAsnIleGlu-38 |
| SEQ. ID. NO. 14312 | 55-GlyLysThrLeuAlaAspTyrGlyGlyTyrProSerAlaLeuAspAla-70 |
| SEQ. ID. NO. 14313 | 80-AlaAlaTyrLeuGluAsnAlaGlyAsp-88 |
| SEQ. ID. NO. 14314 | 90-AlaMetAlaGluAsnValArgAsnGluTrpLeuLysSer-102 |
| SEQ. ID. NO. 14315 | 142-AlaAlaGluLeuValLysAsnThrGlyLysLeuProSerGlyCysThrLysLeuLeuGluGlnAlaAlaAlaSer-166 |
| SEQ. ID. NO. 14316 | 173-AspAlaTrpArgArgValArg-179 |
| SEQ. ID. NO. 14317 | 193-LeuAlaAlaAlaLeuGlySerProPheAspGlyGlyThrGlnGly-207 |
| SEQ. ID. NO. 14318 | 215-AsnValIleGlyLysGluAlaArgLysSer-224 |
| SEQ. ID. NO. 14319 | 229-AlaLeuLeuSerGluMet-234 |
| SEQ. ID. NO. 14320 | 259-AsnValProAlaAlaLeuAspTyrTyrGly-268 |
| SEQ. ID. NO. 14321 | 292-ArgArgTrpAspGluLeuAlaSerValIleSerHisMetProGluLysLeuGlnLys-310 |
| SEQ. ID. NO. 14322 | 329-GlnGluAlaGluLysLeuTyrLysGlnAla-338 |
| SEQ. ID. NO. 14323 | 451-ArgTyrIleSerPro-455 |
| SEQ. ID. NO. 14324 | 495-GlnGlyLeuMetGlnValMet-501 |
| SEQ. ID. NO. 14325 | 582-ArgAspTyrValLysLysValMet-589 |
| Antigenic Index - Jameson-Wolf | |
| SEQ. ID. NO. 14326 | 3-ProProSerLeuLys-7 |
| SEQ. ID. NO. 14327 | 22-SerSerThrAsnThrLeuSerAlaAspLysThrProAlaAspAsnIleGluThrAlaAspLeuSerAlaSerValProThrArgProAlaGlu ProGluGlyLysThrLeuAlaAspTyrGlyGlyTyrProSerAla-67 |
| SEQ. ID. NO. 14328 | 69-AspAlaValLysGlnLysAsnAspAla-77 |
| SEQ. ID. NO. 14329 | 85-AsnAlaGlyAspSerAlaMet-91 |
| SEQ. ID. NO. 14330 | 103-LeuGlyAlaArgArgGln-108 |
| SEQ. ID. NO. 14331 | 115-GluTyrAlaLysLeuGluProAlaGlyArgAlaGlnGluValGluCysTyrAlaAspSerSerArgAsnAspTyrThrArgAlaAlaGluLeu ValLysAsnThrGlyLysLeuProSerGlyCys-156 |
| SEQ. ID. NO. 14332 | 167-GlyLeuLeuAspGlyAsnAspAlaTrpArgArgValArgGly-180 |
| SEQ. ID. NO. 14333 | 182-LeuAlaGlyArgGlnThrThrAspAlaArgAsn-192 |
| SEQ. ID. NO. 14334 | 199-SerProPheAspGlyGlyThrGlnGlySerArgGluTyr-211 |
| SEQ. ID. NO. 14335 | 217-IleGlyLysGluAlaArgLysSerProAsn-226 |
| SEQ. ID. NO. 14336 | 232-SerGluMetGluSerGlyLeuSerLeuGluGlnArgSer-244 |
| SEQ. ID. NO. 14337 | 254-GlnSerGlnAsnLeu-258 |
| SEQ. ID. NO. 14338 | 266-TyrTyrGlyLysValAlaAspArgArgGlnLeuThrAspAspGlnIle-281 |
| SEQ. ID. NO. 14339 | 287-AlaAlaLeuArgAlaArgArgTrpAspGlu-296 |
| SEQ. ID. NO. 14340 | 304-MetProGluLysLeuGlnLysSerProThr-313 |
| SEQ. ID. NO. 14341 | 320-ArgSerArgAlaAlaThrGlyAsnThrGlnGluAlaGluLysLeuTyrLys-336 |
| SEQ. ID. NO. 14342 | 339-AlaAlaThrGlyArgAsn-344 |
| SEQ. ID. NO. 14343 | 350-AlaGlyGluGluLeuGlyGlyArgLysIleAspThrArgAsnAsnValProAspAlaGlyLysAsnSerVal-372 |
| SEQ. ID. NO. 14344 | 374-ArgMetAlaGluAspGlyAlaIleLys-382 |
| SEQ. ID. NO. 14345 | 389-ArgAsnSerArgThrAlaGlyAspAlaLysMetArgArgGlnAlaGlnAla-405 |
| SEQ. ID. NO. 14346 | 409-PheAlaThrArgGlyPheAspGluAspLysLeuLeu-420 |
| SEQ. ID. NO. 14347 | 438-SerAlaGluArgThrAspArgLysLeuAsnTyr-448 |
| SEQ. ID. NO. 14348 | 454-SerProPheLysAspThrValIle-461 |
| SEQ. ID. NO. 14349 | 464-AlaGlnAsnValAsnValAspProAla-472 |
| SEQ. ID. NO. 14350 | 478-IleArgGlnGluSerArgPhe-484 |
| SEQ. ID. NO. 14351 | 488-AlaGlnSerArgValGlyAla-494 |
| SEQ. ID. NO. 14352 | 504-ThrAlaArgGluIleAlaGly-510 |
| SEQ. ID. NO. 14353 | 520-TyrThrArgGlyAsnIleArgMetGly-529 |
| SEQ. ID. NO. 14354 | 535-AspThrLysArgArgLeuGlnAsnAsnGluVal-545 |
| SEQ. ID. NO. 14355 | 550-GlyTyrAsnAlaGlyProGlyArgAlaArgArgTrpGlnAlaAspThrProLeuGlu-568 |
| SEQ. ID. NO. 14356 | 579-SerGluThrArgAspTyrValLys-586 |
| SEQ. ID. NO. 14357 | 606-LeuLysGlnArgMet-610 |
| Hydrophilic Regions - Hopp-Woods | |
| SEQ. ID. NO. 14358 | 27-LeuSerAlaAspLysThrProAlaAspAsnIleGluThrAlaAspLeu-42 |
| SEQ. ID. NO. 14359 | 46-ValProThrArgProAlaGluProGluGlyLysThrLeuAla-59 |
| SEQ. ID. NO. 14360 | 69-AspAlaValLysGlnLysAsnAspAla-77 |
| SEQ. ID. NO. 14361 | 85-AsnAlaGlyAspSerAlaMet-91 |
| SEQ. ID. NO. 14362 | 103-LeuGlyAlaArgArgGln-108 |
| SEQ. ID. NO. 14363 | 115-GluTyrAlaLysLeuGluProAlaGlyArgAlaGlnGluValGluCysTyrAlaAspSerSerArgAsnAspTyrThrArgAlaAlaGlu LeuValLysAsnThrGlyLysLeuProSerGlyCys-156 |
| SEQ. ID. NO. 14364 | 170-AspGlyAsnAspAlaTrpArgArgValArgGly-180 |
| SEQ. ID. NO. 14365 | 185-ArgGlnThrThrAspAlaArgAsn-192 |
| SEQ. ID. NO. 14366 | 201-PheAspGlyGlyThrGlnGlySerArgGlu-210 |
| SEQ. ID. NO. 14367 | 217-IleGlyLysGluAlaArgLysSerProAsn-226 |
| SEQ. ID. NO. 14368 | 232-SerGluMetGluSer-236 |

TABLE 1-continued

| | |
|---|---|
| SEQ. ID. NO. 14369 | 238-LeuSerLeuGluGlnArgSer-244 |
| SEQ. ID. NO. 14370 | 270-ValAlaAspArgArgGlnLeuThrAspAspGlnIle-281 |
| SEQ. ID. NO. 14371 | 287-AlaAlaLeuArgAlaArgArgTrpAspGlu-296 |
| SEQ. ID. NO. 14372 | 304-MetProGluLysLeuGlnLys-310 |
| SEQ. ID. NO. 14373 | 320-ArgSerArgAlaAlaThr-325 |
| SEQ. ID. NO. 14374 | 327-AsnThrGlnGluAlaGluLysLeuTyrLys-336 |
| SEQ. ID. NO. 14375 | 350-AlaGlyGluGluLeuGlyArgLysIleAspThrArgAsnAsnValProAspAlaGlyLys-369 |
| SEQ. ID. NO. 14376 | 374-ArgMetAlaGluAspGlyAlaIleLys-382 |
| SEQ. ID. NO. 14377 | 389-ArgAsnSerArgThrAlaGlyAspAlaLysMetArgArgGlnAlaGlnAla-405 |
| SEQ. ID. NO. 14378 | 411-ThrArgGlyPheAspGluAspLysLeuLeu-420 |
| SEQ. ID. NO. 14379 | 438-SerAlaGluArgThrAspArgLysLeu-446 |
| SEQ. ID. NO. 14380 | 478-IleArgGlnGluSerArgPhe-484 |
| SEQ. ID. NO. 14381 | 488-AlaGlnSerArgValGly-493 |
| SEQ. ID. NO. 14382 | 504-ThrAlaArgGluIleAlaGly-510 |
| SEQ. ID. NO. 14383 | 535-AspThrLysArgArgLeuGlnAsn-542 |
| SEQ. ID. NO. 14384 | 554-GlyProGlyArgAlaArgArgTrpGlnAla-563 |
| SEQ. ID. NO. 14385 | 579-SerGluThrArgAspTyrValLys-586 |
| SEQ. ID. NO. 14386 | 606-LeuLysGlnArgMet-610 |
| a023 | |
| AMPHI Regions - AMPHI | |
| SEQ. ID. NO. 14387 | 42-LysGluTyrSerAlaTrpGlnAlaPhePheSerGlnThrTrpValLys<br>ValPheThrGlnValSerPheIleAlaValPheLeuHisAlaTrpValGly-74 |
| SEQ. ID. NO. 14388 | 82-TyrXxxLysProPhe-86 |
| Antigenic Index - Jameson-Wolf | |
| SEQ. ID. NO. 14389 | 1-MetValGluArgLysLeuThr-7 |
| SEQ. ID. NO. 14390 | 41-ProLysGluTyrSer-45 |
| SEQ. ID. NO. 14391 | 81-AspTyrXxxLysProPheGlyVal-88 |
| Hydrophilic Regions - Hopp-Woods | |
| SEQ. ID. NO. 14392 | 1-MetValGluArgLysLeuThr-7 |
| a025 | |
| AMPHI Regions - AMPHI | |
| SEQ. ID. NO. 14393 | 15-AlaAlaGlnLeuGlyGlyCysProThrGlnHis-25 |
| SEQ. ID. NO. 14394 | 36-MetGlnThrValProSerAlaProValTyrAsnProTyrGlyAlaThrProTyr-53 |
| SEQ. ID. NO. 14395 | 111-AspThrValTyrLysIleSerLysCysTyrHisIle-122 |
| SEQ. ID. NO. 14396 | 126-AspPheArgAlaTrpAsnGlyMetThrAsp-135 |
| SEQ. ID. NO. 14397 | 140-IleGlyGlnIleValLysVal-146 |
| SEQ. ID. NO. 14398 | 206-AspPheArgAlaTrpAsnGlyMetThrAsp-215 |
| SEQ. ID. NO. 14399 | 220-IleGlyGlnIleValLysVal-226 |
| SEQ. ID. NO. 14400 | 248-AlaValGlnThrProValLysProAlaAla-257 |
| SEQ. ID. NO. 14401 | 261-ValGlnSerAlaProGlnPro-267 |
| SEQ. ID. NO. 14402 | 290-SerGlyThrArgSer-294 |
| SEQ. ID. NO. 14403 | 307-LysValValAlaAspPhe-312 |
| SEQ. ID. NO. 14404 | 343-GlyLeuArgGlyTyrGlyAsn-349 |
| Antigenic Index - Jameson-Wolf | |
| SEQ. ID. NO. 14405 | 22-ProThrGlnHisPro-26 |
| SEQ. ID. NO. 14406 | 33-AsnSerGlyMetGlnThr-38 |
| SEQ. ID. NO. 14407 | 58-AlaAlaAsnAspAlaPro-63 |
| SEQ. ID. NO. 14408 | 108-ValArgGlyAspThrValTyrLysIleSerLys-118 |
| SEQ. ID. NO. 14409 | 120-TyrHisIleSerGlnAspAspPheArgAla-129 |
| SEQ. ID. NO. 14410 | 131-AsnGlyMetThrAspAsnThrLeu-138 |
| SEQ. ID. NO. 14411 | 144-ValLysValLysProAlaGly-150 |
| SEQ. ID. NO. 14412 | 157-AlaAlaValLysSerArgProAla-164 |
| SEQ. ID. NO. 14413 | 188-ValArgGlyAspThr-192 |
| SEQ. ID. NO. 14414 | 195-AsnIleSerLysArgTyrHisIleSerGlnAspAspPheArgAla-209 |
| SEQ. ID. NO. 14415 | 211-AsnGlyMetThrAspAsnThrLeu-218 |
| SEQ. ID. NO. 14416 | 224-ValLysValLysProAlaGly-230 |
| SEQ. ID. NO. 14417 | 237-AlaAlaValLysSerArgProAla-244 |
| SEQ. ID. NO. 14418 | 252-ProValLysProAlaAlaGlnProProValGlnSerAlaProGlnPro-267 |
| SEQ. ID. NO. 14419 | 270-ProAlaAlaGluAsnLysAlaVal-277 |
| SEQ. ID. NO. 14420 | 280-ProAlaProGlnSerProAlaAlaSerProSerGlyThrArgSerValGly-296 |
| SEQ. ID. NO. 14421 | 302-ArgProThrGlnGlyLysValValAlaAspPheGlyGlyAsnAsnLysGlyValAsp-320 |
| SEQ. ID. NO. 14422 | 333-AlaAspGlyLysVal-337 |
| SEQ. ID. NO. 14423 | 342-SerGlyLeuArgGlyTyrGly-348 |
| SEQ. ID. NO. 14424 | 363-TyrGlyHisAsnGln-367 |
| SEQ. ID. NO. 14425 | 370-LeuValGlyGluGlyGlnGlnValLysArgGlyGlnGln-382 |
| SEQ. ID. NO. 14426 | 387-GlyAsnThrGluAlaSerArgThrGlnLeu-396 |
| SEQ. ID. NO. 14427 | 398-PheGluValArgGlnAsnGlyLysProValAsnProAsnSer-411 |
| Hydrophilic Regions - Hopp-Woods | |
| SEQ. ID. NO. 14428 | 108-ValArgGlyAspThr-112 |
| SEQ. ID. NO. 14429 | 123-SerGlnAspAspPheArg-128 |
| SEQ. ID. NO. 14430 | 144-ValLysValLysPro-148 |
| SEQ. ID. NO. 14431 | 157-AlaAlaValLysSerArgProAla-164 |
| SEQ. ID. NO. 14432 | 188-ValArgGlyAspThr-192 |
| SEQ. ID. NO. 14433 | 200-TyrHisIleSerGlnAspAspPheArg-208 |
| SEQ. ID. NO. 14434 | 224-ValLysValLysPro-228 |
| SEQ. ID. NO. 14435 | 237-AlaAlaValLysSerArgProAla-244 |
| SEQ. ID. NO. 14436 | 253-ValLysProAlaAla-257 |
| SEQ. ID. NO. 14437 | 270-ProAlaAlaGluAsnLysAlaVal-277 |
| SEQ. ID. NO. 14438 | 290-SerGlyThrArgSer-294 |
| SEQ. ID. NO. 14439 | 313-GlyGlyAsnAsnLysGlyValAsp-320 |

TABLE 1-continued

| | |
|---|---|
| SEQ. ID. NO. 14440 | 333-AlaAspGlyLysVal-337 |
| SEQ. ID. NO. 14441 | 373-GluGlyGlnGlnValLysArgGlyGln-381 |
| SEQ. ID. NO. 14442 | 389-ThrGluAlaSerArgThr-394 |
| SEQ. ID. NO. 14443 | 400-ValArgGlnAsnGlyLysProValAsn-408 | a032
AMPHI Regions - AMPHI

| | |
|---|---|
| SEQ. ID. NO. 14444 | 11-LeuArgArgProLeuArgGln-17 |
| SEQ. ID. NO. 14445 | 67-SerPheAlaGlyAsnValTyrProArgLeu-76 |
| SEQ. ID. NO. 14446 | 114-ValHisGlyGlnIleGlnHisProValGlnProPheLeuArg-127 |
| SEQ. ID. NO. 14447 | 134-LeuGlyLeuLeuArgArgPheAspVal-142 |

Antigenic Index - Jameson-Wolf

| | |
|---|---|
| SEQ. ID. NO. 14448 | 1-MetArgArgAsnVal-5 |
| SEQ. ID. NO. 14449 | 10-ValLeuArgArgProLeuArg-16 |
| SEQ. ID. NO. 14450 | 28-ArgAlaValProAlaGlyLysGlnGlyPhe-37 |
| SEQ. ID. NO. 14451 | 41-CysArgLeuThrGlnArgGln-47 |
| SEQ. ID. NO. 14452 | 57-AlaGlyGlnArgAsnLeuPro-63 |
| SEQ. ID. NO. 14453 | 104-ValIleAlaHisArgGlnArgVal-111 |
| SEQ. ID. NO. 14454 | 138-ArgArgPheAspValGlyGlyArgValGlyMet-148 |
| SEQ. ID. NO. 14455 | 151-ThrAlaPheAspGlnProGlyAla-158 |
| SEQ. ID. NO. 14456 | 160-LeuProProArgArgGlnLeuAlaArgGlnArgProArgIleGlnThrAlaLeuArgGlnProProGlnArgArgArgLysIleAlaLeu-189 |
| SEQ. ID. NO. 14457 | 203-HisLeuCysGlnGlnArgLysGln-210 |
| SEQ. ID. NO. 14458 | 236-ValLysMetArgArgLysProValGlnAsnHisAsnArgProThrGlnIleSerLysLysGln-256 |

Hydrophilic Regions - Hopp-Woods

| | |
|---|---|
| SEQ. ID. NO. 14459 | 1-MetArgArgAsnVal-5 |
| SEQ. ID. NO. 14460 | 10-ValLeuArgArgProLeuArg-16 |
| SEQ. ID. NO. 14461 | 28-ArgAlaValProAlaGlyLys-34 |
| SEQ. ID. NO. 14462 | 41-CysArgLeuThrGln-45 |
| SEQ. ID. NO. 14463 | 104-ValIleAlaHisArgGlnArgVal-111 |
| SEQ. ID. NO. 14464 | 138-ArgArgPheAspValGlyGly-144 |
| SEQ. ID. NO. 14465 | 161-ProProArgArgGlnLeuAlaArgGlnArgProArgIle-173 |
| SEQ. ID. NO. 14466 | 177-LeuArgGlnProProGlnArgArgArgLysIleAlaLeu-189 |
| SEQ. ID. NO. 14467 | 203-HisLeuCysGlnGlnArgLysGln-210 |
| SEQ. ID. NO. 14468 | 236-ValLysMetArgArgLysProValGlnAsnHisAsnArgProThrGlnIleSerLysLysGln-256 | a033-2
AMPHI Regions - AMPHI

| | |
|---|---|
| SEQ. ID. NO. 14469 | 6-GlnTyrGlyGlyLeuAlaGlyPheProLysArgCysGluSerGlu-20 |
| SEQ. ID. NO. 14470 | 64-GlyGlnAlaPheGluAlaLeuAsnCys-72 |
| SEQ. ID. NO. 14471 | 95-ValGlyAlaLeuProLysTyrLeuAlaSerAsnValValArgAspMetHisGlyLeuLeuSerThrVal-117 |
| SEQ. ID. NO. 14472 | 120-GlnThrGlyLysValLeuAspLysIleProGlyAlaMetGlu-133 |
| SEQ. ID. NO. 14473 | 142-IleLysThrLeuAlaGlu-147 |
| SEQ. ID. NO. 14474 | 157-SerLeuPheGluAsnPhe-162 |
| SEQ. ID. NO. 14475 | 168-GlyProValAspGlyHisAsnValGluAsnLeuValAspValLeuGluAspLeuArgGlyArg-188 |
| SEQ. ID. NO. 14476 | 207-AlaGluAsnAspPro-211 |
| SEQ. ID. NO. 14477 | 213-LysTyrHisAlaValAlaAsnLeuProLysGluSerAlaAla-226 |
| SEQ. ID. NO. 14478 | 242-TyrThrGlnValPheGlyLys-248 |
| SEQ. ID. NO. 14479 | 280-PheProAspArgTyrPheAspVal-287 |
| SEQ. ID. NO. 14480 | 307-LysProValValAlaIleTyrSer-314 |
| SEQ. ID. NO. 14481 | 316-PheLeuGlnArgAlaTyrAspGlnLeu-324 |
| SEQ. ID. NO. 14482 | 357-AspLeuSerPheLeuArgCysIleProAsnMetIleVal-369 |
| SEQ. ID. NO. 14483 | 390-AlaProAlaAlaValArgTyrProArg-398 |
| SEQ. ID. NO. 14484 | 407-SerAspGlyMetGluThrValGlu-414 |
| SEQ. ID. NO. 14485 | 419-IleIleArgArgGlu-423 |
| SEQ. ID. NO. 14486 | 432-PheGlySerMetValAla-437 |
| SEQ. ID. NO. 14487 | 453-MetArgPheValLysProIleAspGluGlu-462 |
| SEQ. ID. NO. 14488 | 469-ArgSerHisAspArgIle-474 |
| SEQ. ID. NO. 14489 | 489-AlaValLeuGluValLeu-494 |
| SEQ. ID. NO. 14490 | 510-AspThrValThrGlyHisGly-516 |
| SEQ. ID. NO. 14491 | 518-ProLysLysLeuLeu-522 |

Antigenic Index - Jameson-Wolf

| | |
|---|---|
| SEQ. ID. NO. 14492 | 11-AlaGlyPheProLysArgCysGluSerGluTyrAspAla-23 |
| SEQ. ID. NO. 14493 | 28-HisSerSerThrSerIle-33 |
| SEQ. ID. NO. 14494 | 41-AlaAlaAspLysGlnLeuGlySerAspArgArgSerVal-53 |
| SEQ. ID. NO. 14495 | 57-GlyAspGlyAlaMetThr-62 |
| SEQ. ID. NO. 14496 | 72-CysAlaGlyAspMetAspVal-78 |
| SEQ. ID. NO. 14497 | 85-AsnAspAsnGluMetSerIle-91 |
| SEQ. ID. NO. 14498 | 105-AsnValValArgAspMetHisGly-112 |
| SEQ. ID. NO. 14499 | 117-ValLysAlaGlnThrGlyLysValLeuAspLysIleProGly-130 |
| SEQ. ID. NO. 14500 | 134-PheAlaGlnLysValGluHisLysIleLysThrLeuAlaGluGluAlaGluHisAlaLysGln-154 |
| SEQ. ID. NO. 14501 | 166-TyrThrGlyProValAspGlyHisAsn-174 |
| SEQ. ID. NO. 14502 | 181-ValLeuGluAspLeuArgGlyArgLysGlyPro-191 |
| SEQ. ID. NO. 14503 | 197-IleThrLysLysGlyAsnGlyTyrLysLeuAlaGluAsnAspProValLys-213 |
| SEQ. ID. NO. 14504 | 220-LeuProLysGluSerAlaAla-226 |
| SEQ. ID. NO. 14505 | 228-MetProSerGluLysGluProLysProAlaAlaLysProThrTyr-242 |
| SEQ. ID. NO. 14506 | 253-ArgAlaAlaAlaAspSerArgLeu-260 |
| SEQ. ID. NO. 14507 | 266-AlaMetArgGluGlySerGlyLeuValGluPheGluGlnArgPheProAspArgTyrPhe-285 |
| SEQ. ID. NO. 14508 | 345-ValGlyAlaAspGlyProThrHis-352 |
| SEQ. ID. NO. 14509 | 370-AlaAlaProSerAspGluAsnGluCysArg-379 |
| SEQ. ID. NO. 14510 | 395-ArgTyrProArgGlyThrGlyThr-402 |
| SEQ. ID. NO. 14511 | 406-ValSerAspGlyMetGluThrValGluIleGlyLysGlyIleIleArgArgGluGlyGluLysThrAla-428 |
| SEQ. ID. NO. 14512 | 457-LysProIleAspGluGluLeuIle-464 |

TABLE 1-continued

| | |
|---|---|
| SEQ. ID. NO. 14513 | 467-LeuAlaArgSerHisAspArgIleValThrLeuGluGluAsnAlaGluGlnGlyGlyAlaGly-487 |
| SEQ. ID. NO. 14514 | 512-ValThrGlyHisGlyAspProLysLysLeuLeuAspAspLeuGlyLeu-527 |
| SEQ. ID. NO. 14515 | 530-GluAlaValGluArgArgValArg-537 |
| SEQ. ID. NO. 14516 | 540-LeuSerAspArgAspAlaAlaAsn-547 |

Hydrophilic Regions - Hopp-Woods

| | |
|---|---|
| SEQ. ID. NO. 14517 | 13-PheProLysArgCysGluSerGluTyrAsp-22 |
| SEQ. ID. NO. 14518 | 41-AlaAlaAspLysGlnLeuGlySerAspArgArgSerVal-53 |
| SEQ. ID. NO. 14519 | 74-GlyAspMetAspVal-78 |
| SEQ. ID. NO. 14520 | 85-AsnAspAsnGluMetSerIle-91 |
| SEQ. ID. NO. 14521 | 106-ValValArgAspMetHis-111 |
| SEQ. ID. NO. 14522 | 123-LysValLeuAspLysIleProGly-130 |
| SEQ. ID. NO. 14523 | 134-PheAlaGlnLysValGluHisLysIleLysThrLeuAlaGluGluAlaGluHisAlaLysGln-154 |
| SEQ. ID. NO. 14524 | 181-ValLeuGluAspLeuArgGlyArgLysGlyPro-191 |
| SEQ. ID. NO. 14525 | 197-IleThrLysLysGlyAsnGly-203 |
| SEQ. ID. NO. 14526 | 205-LysLeuAlaGluAsnAspProValLys-213 |
| SEQ. ID. NO. 14527 | 220-LeuProLysGluSerAlaAla-226 |
| SEQ. ID. NO. 14528 | 228-MetProSerGluLysGluProLysProAlaAla-238 |
| SEQ. ID. NO. 14529 | 253-ArgAlaAlaAlaAspSerArgLeu-260 |
| SEQ. ID. NO. 14530 | 266-AlaMetArgGluGlySerGly-272 |
| SEQ. ID. NO. 14531 | 274-ValGluPheGluGlnArgPheProAspArgTyrPhe-285 |
| SEQ. ID. NO. 14532 | 372-ProSerAspGluAsnGluCys-378 |
| SEQ. ID. NO. 14533 | 408-AspGlyMetGluThrValGluIleGlyLysGlyIleIleArgArgGluGlyGluLysThrAla-428 |
| SEQ. ID. NO. 14534 | 457-LysProIleAspGluGluLeuIle-464 |
| SEQ. ID. NO. 14535 | 467-LeuAlaArgSerHisAspArgIleValThrLeuGluGluAsnAlaGluGlnGlyGly-485 |
| SEQ. ID. NO. 14536 | 513-ThrGlyHisGlyAspProLysLysLeuLeuAsp-523 |
| SEQ. ID. NO. 14537 | 530-GluAlaValGluArgArgValArg-537 |
| SEQ. ID. NO. 14538 | 540-LeuSerAspArgAspAlaAlaAsn-547 | a034
AMPHI Regions - AMPHI

| | |
|---|---|
| SEQ. ID. NO. 14539 | 35-LeuAspHisAlaAla-39 |
| SEQ. ID. NO. 14540 | 52-AsnLeuGluGlnMetArgAlaIleMetGluAlaAlaAspGln-65 |
| SEQ. ID. NO. 14541 | 94-AlaValGluGluPheProHisIlePro-102 |
| SEQ. ID. NO. 14542 | 152-ThrValValAsnPheSer-157 |
| SEQ. ID. NO. 14543 | 168-IleGlyValLeuGlyAsnLeuGluThrGly-177 |
| SEQ. ID. NO. 14544 | 186-GlyAlaValGlyLysLeuSer-192 |
| SEQ. ID. NO. 14545 | 197-LeuThrSerValGluAspAlaValArgPheValLysAspThrGly-211 |
| SEQ. ID. NO. 14546 | 226-TyrLysPheThrArgProProThrGly-234 |
| SEQ. ID. NO. 14547 | 236-ValLeuArgIleAspArgIleLysGluIleHisGlnAlaLeu-249 |
| SEQ. ID. NO. 14548 | 261-SerValProGlnGluTrpLeuLysValIleAsnGluTyrGlyGlyAsn<br>IleGlyGluThrTyrGlyValProValGluGluIleValGluGlyIleLysHisGly-295 |
| SEQ. ID. NO. 14549 | 314-ArgArgTyrLeuAlaGluAsn-320 |
| SEQ. ID. NO. 14550 | 330-LeuSerLysThrIleGluAlaMetLys-338 |
| SEQ. ID. NO. 14551 | 360-ValSerLeuGluLysMetAlaAsnArgTyrAlaLysGlyGluLeuAsnGlnIleVal-378 |

Antigenic Index - Jameson-Wolf

| | |
|---|---|
| SEQ. ID. NO. 14552 | 20-LeuProLysGluThrGln-25 |
| SEQ. ID. NO. 14553 | 37-HisAlaAlaGluAsnSerTyrGly-44 |
| SEQ. ID. NO. 14554 | 54-GluGlnMetArgAlaIleMetGluAlaAlaAspGlnVal-66 |
| SEQ. ID. NO. 14555 | 75-SerAlaGlyAlaArgLysTyrAla-82 |
| SEQ. ID. NO. 14556 | 106-HisGlnAspHisGlyAlaSerProAspValCysGlnArgSerIle-120 |
| SEQ. ID. NO. 14557 | 129-MetAspGlySerLeuMetGluAspGlyLysThrProSerSerTyrGluTyr-145 |
| SEQ. ID. NO. 14558 | 164-ValGluGlyGluIle-168 |
| SEQ. ID. NO. 14559 | 173AsnLeuGluThrGlyGluAlaGlyGluGluAspGlyVal-185 |
| SEQ. ID. NO. 14560 | 191-LeuSerHisAspGln-195 |
| SEQ. ID. NO. 14561 | 199-SerValGluAspAlaValArgPheValLysAspThrGlyValAsp-213 |
| SEQ. ID. NO. 14562 | 221-ThrSerHisGlyAla-225 |
| SEQ. ID. NO. 14563 | 227-LysPheThrArgProProThrGlyAspValLeuArgIleAspArgIleLysGluIleHis-246 |
| SEQ. ID. NO. 14564 | 258-GlySerSerSerValPro-263 |
| SEQ. ID. NO. 14565 | 271-AsnGluTyrGlyGlyAsnIleGlyGlu-279 |
| SEQ. ID. NO. 14566 | 287-GluIleValGluGlyIleLysHisGlyValArgLysValAsnIleAspThrAspLeuArgLeuAlaSerThrGlyAlaVal-313 |
| SEQ. ID. NO. 14567 | 316-TyrLeuAlaGluAsnProSerAspPheAspProArgLysTyrLeuSerLysThrIleGluAlaMetLys-338 |
| SEQ. ID. NO. 14568 | 350-CysGluGlyGlnAlaGlyLysIleLysProValSerLeuGluLysMetAlaAsnArgTyrAlaLysGlyGluLeu-374 |

Hydrophilic Regions - Hopp-Woods

| | |
|---|---|
| SEQ. ID. NO. 14569 | 54-GluGlnMetArgAlaIleMetGluAlaAlaAspGlnVal-66 |
| SEQ. ID. NO. 14570 | 76-AlaGlyAlaArgLysTyrAla-82 |
| SEQ. ID. NO. 14571 | 108-AspHisGlyAlaSerProAspValCysGln-117 |
| SEQ. ID. NO. 14572 | 132-SerLeuMetGluAspGlyLysThrProSer-141 |
| SEQ. ID. NO. 14573 | 164-ValGluGlyGluIle-168 |
| SEQ. ID. NO. 14574 | 175-GluThrGlyGluAlaGlyGluGluAspGlyVal-185 |
| SEQ. ID. NO. 14575 | 199-SerValGluAspAlaValArgPheValLysAspThrGlyVal-212 |
| SEQ. ID. NO. 14576 | 235-AspValLeuArgIleAspArgIleLysGluIleHis-246 |
| SEQ. ID. NO. 14577 | 287-GluIleValGluGlyIleLysHisGlyValArgLysValAsnIleAspThrAspLeuArgLeu-307 |
| SEQ. ID. NO. 14578 | 320-AsnProSerAspPheAspProArgLysTyrLeuSerLysThrIleGluAlaMetLys-338 |
| SEQ. ID. NO. 14579 | 352-GlyGlnAlaGlyLysIleLysProValSerLeuGluLysMetAlaAsnArgTyrAlaLysGlyGluLeu-374 | a036
AMPHI Regions - AMPHI

| | |
|---|---|
| SEQ. ID. NO. 14580 | 6-AlaValTyrSerAlaCysAlaAla-13 |
| SEQ. ID. NO. 14581 | 29-GlyArgCysValAsnGlnTyr-35 |
| SEQ. ID. NO. 14582 | 59-SerSerGlyArgPheCysGlnThrIleLys-68 |
| SEQ. ID. NO. 14583 | 106-AlaAlaSerAlaAlaGlnSer-112 |
| SEQ. ID. NO. 14584 | 213-SerAlaCysArgThrMetHisLysThrLeuArgProTyrVal-226 |

TABLE 1-continued

| SEQ. ID. NO. 14585 | 250-ArgLeuLysGluTyr-254 |

Antigenic Index - Jameson-Wolf
SEQ. ID. NO. 14586    16-ProAlaArgThrSerSerSerArgArgCysValSerSerGlyArgCysValAsnGlnTyrSerSerArgAlaAspAla-41
SEQ. ID. NO. 14587    43-ProTrpArgArgHisSerGlyAla-50
SEQ. ID. NO. 14588    55-CysSerSerAspSerSerGlyArgPhe-63
SEQ. ID. NO. 14589    73-ProSerPheSerAlaArgLysThrCysSerAspGlyGluThrSerAlaAspSerAsnTrpArg-93
SEQ. ID. NO. 14590    96-HisAlaAspGlyLeuGlnThrAlaSerSer-105
SEQ. ID. NO. 14591    112-SerAlaXxxThrAlaArgArgMetPheThr-121
SEQ. ID. NO. 14592    132-GlnSerArgArgPheCysCysGlyArgArgAlaAlaArgArgValProGlnArgArgArgGluAsnArgLeuGlnProProAspXxxGly
                      SerArgArgArgSerAlaTyrArgValCysLeuArgArgAlaAspGlyPheProAlaArgThrHisCysArgCysArgLeuLysArgArgIleLeu-193
SEQ. ID. NO. 14593    199-LeuProProAspArgProAspAsnArgSerAsnGlyGlySerAlaCysArgThrMetHisLysThrLeuArgProTyrValArgProGlnArgGln
                      GlyCys-233
SEQ. ID. NO. 14594    239-AlaAlaArgArgArgHisArgAlaArgValArgArgLeuLysGluTyrGlnThr-256
SEQ. ID. NO. 14595    260-AsnLeuAlaProArgArgCysArgTyrAla-269
Hydrophilic Regions - Hopp-Woods
SEQ. ID. NO. 14596    18-ArgThrSerSerSerArgArgCysValSerSer-28
SEQ. ID. NO. 14597    35-TyrSerSerArgAlaAsp-40
SEQ. ID. NO. 14598    45-ArgArgHisSerGly-49
SEQ. ID. NO. 14599    55-CysSerSerAspSerSerGlyArg-62
SEQ. ID. NO. 14600    75-PheSerAlaArgLysThrCysSerAspGlyGluThrSerAla-88
SEQ. ID. NO. 14601    114-XxxThrAlaArgArgMetPhe-120
SEQ. ID. NO. 14602    135-ArgPheCysCysGlyArgArgAlaAlaArgArgValProGlnArgArg
                      ArgGluAsnArgLeuGlnProProAspXxxGlySerArgArgArgSerAlaTyr-168
SEQ. ID. NO. 14603    171-CysLeuArgArgAlaAspGlyPhePro-179
SEQ. ID. NO. 14604    182-ThrHisCysArgCysArgLeuLysArgArgIleLeu-193
SEQ. ID. NO. 14605    200-ProProAspArgProAspAsnArgSerAsnGlyGly-211
SEQ. ID. NO. 14606    217-ThrMetHisLysThrLeuArgProTyrValArgProGlnArgGlnGly-232
SEQ. ID. NO. 14607    239-AlaAlaArgArgArgHisArgAlaArgValArgArgLeuLysGluTyrGln-255
SEQ. ID. NO. 14608    262-AlaProArgArgCysArgTyr-268
a038
AMPHI Regions - AMPHI
SEQ. ID. NO. 14609    100-GluAlaLysAspHis-104
SEQ. ID. NO. 14610    157-GluLysGlyThrGlyGluLeuSerAlaValGlnGluValGluLys-171
SEQ. ID. NO. 14611    178-AlaProIleAlaSerLeuAsn-184
SEQ. ID. NO. 14612    195-GluPheGlyGlnPheLeuGluProValArgAlaTyrArgArgGlnTyrGlyVal-212
Antigenic Index - Jameson-Wolf
SEQ. ID. NO. 14613    2-ThrAspPheArgGlnAspPhe-8
SEQ. ID. NO. 14614    22-GluPheThrThrLysAlaGlyArgArgSerPro-32
SEQ. ID. NO. 14615    38-GlyLeuPheAsnAspGlyLeu-44
SEQ. ID. NO. 14616    58-IleGluSerGlyIleArg-63
SEQ. ID. NO. 14617    85-LeuAlaGluLysGlyVal-90
SEQ. ID. NO. 14618    96-TyrAsnArgLysGluAlaLysAspHisGlyGluGlyGly-108
SEQ. ID. NO. 14619    125-ValIleSerAlaGlyThrSerValArgGluSerIleLysLeuIleGluAlaGluGlyAlaThr-145
SEQ. ID. NO. 14620    153-LeuAspArgMetGluLysGlyThrGlyGlu-162
SEQ. ID. NO. 14621    167-GlnGluValGluLysGlnTyrGlyLeu-175
SEQ. ID. NO. 14622    191-GlnAsnAsnProGluPheGlyGln-198
SEQ. ID. NO. 14623    203-ValArgAlaTyrArgArgGlnTyrGlyValGlu-213
Hydrophilic Regions - Hopp-Woods
SEQ. ID. NO. 14624    2-ThrAspPheArgGlnAs/pPhe-8
SEQ. ID. NO. 14625    22-GluPheThrThrLysAlaGlyArgArgSer-31
SEQ. ID. NO. 14626    85-LeuAlaGluLysGlyVal-90
SEQ. ID. NO. 14627    96-TyrAsnArgLysGluAlaLysAspHisGlyGlu-106
SEQ. ID. NO. 14628    130-ThrSerValArgGluSerIleLysLeuIleGluAlaGluGlyAlaThr-145
SEQ. ID. NO. 14629    153-LeuAspArgMetGluLysGlyThrGlyGlu-162
SEQ. ID. NO. 14630    167-GlnGluValGluLysGlnTyr-173
SEQ. ID. NO. 14631    204-ArgAlaTyrArgArgGlnTyrGly-211
a040
AMPHI Regions - AMPHI
SEQ. ID. NO. 14632    14-AlaAlaProTyrIle-18
SEQ. ID. NO. 14633    28-AlaGlyIleAspAsp-32
SEQ. ID. NO. 14634    38-AspThrLeuAsnLysPhe-43
SEQ. ID. NO. 14635    78-ProHisTyrCysArgGlyLeuArgValThrAspGlu-89
SEQ. ID. NO. 14636    92-LeuGluGlnAlaGlnPheAlaGly-100
SEQ. ID. NO. 14637    113-SerValSerGlyPheAlaArgAlaPro-121
SEQ. ID. NO. 14638    134-ArgProIleGlyValIleAspGly-141
SEQ. ID. NO. 14639    146-TyrAlaGlyValIleArg-151
SEQ. ID. NO. 14640    207-LeuSerAspGlyIleSerArgProAsp-215
SEQ. ID. NO. 14641    226-GluAlaGlnSerLeuAlaGluHisAla-234
SEQ. ID. NO. 14642    244-SerAlaValAlaAlaLeuGluGly-251
SEQ. ID. NO. 14643    277-IleGlyThrSerIle-281
SEQ. ID. NO. 14644    289-IleArgGlnAlaHisSerGlyAspIleProHisIleAlaAlaLeuIleArgProLeuGlu-308
SEQ. ID. NO. 14645    320-TyrLeuGluAsnHisIleSerGluPheSerIle-330
SEQ. ID. NO. 14646    338-TyrGlyCysAlaAlaLeuLysThrPheAlaGluAlaAsp-350
SEQ. ID. NO. 14647    371-ArgLeuLeuAlaHisIle-376
SEQ. ID. NO. 14648    386-SerArgLeuPheAla-390
Antigenic Index - Jameson-Wolf
SEQ. ID. NO. 14649    11-PheArgGluAlaAlaProTyrIleArgGlnMetArgGlyLysThrLeu-26
SEQ. ID. NO. 14650    29-GlyIleAspAspArgLeuLeuGluGlyAspThrLeuAsn-41
SEQ. ID. NO. 14651    65-HisPheLeuAspArgHisAlaAlaAlaGlnGlyArgThrProHisTyrCysArgGlyLeuArgValThrAspGluThrSerLeuGluGlnAlaGln-96
SEQ. ID. NO. 14652    101-ThrValArgSerArgPheGlu-107

TABLE 1-continued

| | |
|---|---|
| SEQ. ID. NO. 14653 | 119-ArgAlaProSerVal-123 |
| SEQ. ID. NO. 14654 | 140-AspGlyThrAspMetGluTyr-146 |
| SEQ. ID. NO. 14655 | 150-IleArgLysThrAspThrAlaAla-157 |
| SEQ. ID. NO. 14656 | 173-LeuGlyHisSerTyrSerGlyLysThrPhe-182 |
| SEQ. ID. NO. 14657 | 208-SerAspGlyIleSerArgProAspGlyThrLeu-218 |
| SEQ. ID. NO. 14658 | 224-AlaGlnGluAlaGlnSerLeuAlaGluHisAlaGlyGlyGluThrArgArgLeuIle-242 |
| SEQ. ID. NO. 14659 | 249-LeuGluGlyGlyVal-253 |
| SEQ. ID. NO. 14660 | 261-GlyAlaAlaAspGlySerLeuLeu-268 |
| SEQ. ID. NO. 14661 | 272-PheThrArgAsnGlyIleGlyThrSerIleAlaLysGluAlaPheVal-287 |
| SEQ. ID. NO. 14662 | 289-IleArgGlnAlaHisSerGlyAspIle-297 |
| SEQ. ID. NO. 14663 | 305-ArgProLeuGluGluGlnGly-311 |
| SEQ. ID. NO. 14664 | 313-LeuLeuHisArgSerArgGluTyrLeu-321 |
| SEQ. ID. NO. 14665 | 331-LeuGluHisAspGlyAsnLeuTyr-338 |
| SEQ. ID. NO. 14666 | 345-ThrPheAlaGluAlaAspCysGlyGlu-353 |
| SEQ. ID. NO. 14667 | 361-ProGlnAlaGlnAspGlyGlyTyrGlyGluArgLeu-372 |
| SEQ. ID. NO. 14668 | 377-IleAspLysAlaArgGly-382 |
| SEQ. ID. NO. 14669 | 393-ThrAsnThrGlyGlu-397 |
| SEQ. ID. NO. 14670 | 402-ArgGlyPheGlnThrAlaSerGluAspGluLeuProGluThrArgArgLysAspTyrArgSerAsnGlyArgAsnSerHisIleLeu-430 |
| Hydrophilic Regions - Hopp-Woods | |
| SEQ. ID. NO. 14671 | 11-PheArgGluAlaAlaPro-16 |
| SEQ. ID. NO. 14672 | 19-ArgGlnMetArgGlyLysThr-25 |
| SEQ. ID. NO. 14673 | 29-GlyIleAspAspArgLeuLeuGluGlyAspThrLeuAsn-41 |
| SEQ. ID. NO. 14674 | 65-HisPheLeuAspArgHisAlaAlaAlaGlnGlyArgThr-77 |
| SEQ. ID. NO. 14675 | 84-LeuArgValThrAspGluThrSerLeuGluGln-94 |
| SEQ. ID. NO. 14676 | 102-ValArgSerArgPheGlu-107 |
| SEQ. ID. NO. 14677 | 140-AspGlyThrAspMetGluTyr-146 |
| SEQ. ID. NO. 14678 | 150-IleArgLysThrAspThrAlaAla-157 |
| SEQ. ID. NO. 14679 | 210-GlyIleSerArgProAspGly-216 |
| SEQ. ID. NO. 14680 | 224-AlaGlnGluAlaGlnSerLeuAlaGlu-232 |
| SEQ. ID. NO. 14681 | 234-AlaGlyGlyGluThrArgArgLeuIle-242 |
| SEQ. ID. NO. 14682 | 291-GlnAlaHisSerGlyAsp-296 |
| SEQ. ID. NO. 14683 | 305-ArgProLeuGluGluGlnGly-311 |
| SEQ. ID. NO. 14684 | 315-HisArgSerArgGluTyrLeu-321 |
| SEQ. ID. NO. 14685 | 345-ThrPheAlaGluAlaAspCysGlyGlu-353 |
| SEQ. ID. NO. 14686 | 362-GlnAlaGlnAspGlyGlyTyrGlyGlu-370 |
| SEQ. ID. NO. 14687 | 377-IleAspLysAlaArgGly-382 |
| SEQ. ID. NO. 14688 | 402-ArgGlyPheGlnThrAlaSerGluAspGluLeuProGluThrArgArg LysAspTyrArgSerAsnGlyArgAsn-426 |
| a041-1 | |
| AMPHI Regions - AMPHI | |
| SEQ. ID. NO. 14689 | 6-AspProTyrArgHisPheGluAsnLeuAspSerAlaGluThr-19 |
| SEQ. ID. NO. 14690 | 45-AspGlyIleLeuAla-49 |
| SEQ. ID. NO. 14691 | 78-LysGlyValTyrArgValCysThrAlaAla-87 |
| SEQ. ID. NO. 14692 | 102-ValAlaAspPheAspGluLeuLeu-109 |
| SEQ. ID. NO. 14693 | 117-GlyValSerHisLeuValGluGlnProAsn-126 |
| SEQ. ID. NO. 14694 | 218-MetValAsnAlaTrpArgTyrLeuAsp-226 |
| SEQ. ID. NO. 14695 | 232-IleAspLeuIleGluAlaSer-238 |
| SEQ. ID. NO. 14696 | 258-LeuAsnLeuProAsnAspCysAspValValGlyTyrLeu-270 |
| SEQ. ID. NO. 14697 | 317-GlnAlaLeuGluSerValGluThr-324 |
| SEQ. ID. NO. 14698 | 331-AlaSerLeuLeuGluAsnValGlnGlyArg-340 |
| SEQ. ID. NO. 14699 | 354-ThrGluLeuProArgLeuProSer-361 |
| SEQ. ID. NO. 14700 | 382-AspPheThrThrProLeu-387 |
| SEQ. ID. NO. 14701 | 405-GlnProGlnGlnPhe-409 |
| SEQ. ID. NO. 14702 | 451-GlyPheGlyIleProGluLeuProHisTyrLeuGlySerIleGlyLys-466 |
| SEQ. ID. NO. 14703 | 493-AlaAlaGlnGlyIleSerLysHisLysSerValAspAspLeuLeuAlaValValSer-511 |
| SEQ. ID. NO. 14704 | 519-SerSerProGluHis-523 |
| SEQ. ID. NO. 14705 | 541-ValArgGluProGlnSer-546 |
| SEQ. ID. NO. 14706 | 556-LeuThrAspMetIleArgTyr-562 |
| SEQ. ID. NO. 14707 | 571-TrpThrAspGluTyrGlyAsnProGlnLysTyrGlu-582 |
| SEQ. ID. NO. 14708 | 591-LeuSerProTyrHisAsnLeuSerAspGlyIleAspTyrProPro-605 |
| SEQ. ID. NO. 14709 | 620-AlaHisAlaLeuLys-624 |
| SEQ. ID. NO. 14710 | 645-GlyHisThrGlyAsnGlyThrGlnArgGluAla-655 |
| Antigenic Index - Jameson-Wolf | |
| SEQ. ID. NO. 14711 | 1-MetLysSerTyrProAspProTyrArgHisPheGluAsnLeuAspSerAlaGluThrGln-20 |
| SEQ. ID. NO. 14712 | 26-AlaAsnAlaGluThrArgAlaArgPheLeuAsnAsnAspLysAlaArgAlaLeuSerAspGly-46 |
| SEQ. ID. NO. 14713 | 51-LeuGlnAspThrArgGlnIleProPhe-59 |
| SEQ. ID. NO. 14714 | 61-GlnGluHisArgAlaArg-66 |
| SEQ. ID. NO. 14715 | 72-GlnAspAlaGluTyrProLysGlyVal-80 |
| SEQ. ID. NO. 14716 | 89-TyrArgSerGlyTyrProGluTrp-96 |
| SEQ. ID. NO. 14717 | 104-AspPheAspGluLeuLeuGlyAspAspValTyr-114 |
| SEQ. ID. NO. 14718 | 123-GluGlnProAsnArg-127 |
| SEQ. ID. NO. 14719 | 132-LeuSerLysSerGlyGlyAspThr-139 |
| SEQ. ID. NO. 14720 | 145-ValAspLeuGluAlaGlyGluLeuValGlu-154 |
| SEQ. ID. NO. 14721 | 161-AlaGlyLysAsnHisValSerTrpArgAspGluAsnSerVal-174 |
| SEQ. ID. NO. 14722 | 178-ProAlaTrpAspGluArgGlnLeuThrGluSerGlyTyrProArgGluValTrpLeuValGluArgGlyLysSerPheGluGluSerLeu-207 |
| SEQ. ID. NO. 14723 | 212-IleAlaGluAspGlyMet-217 |
| SEQ. ID. NO. 14724 | 223-ArgTyrLeuAspProGlnGlySerProIleAspLeuIleGluAlaSerAspGlyPheTyr-242 |
| SEQ. ID. NO. 14725 | 250-SerAlaGluGlyGluAlaLysProLeuAsnLeuProAsnAspCysAspVal-266 |
| SEQ. ID. NO. 14726 | 278-LeuArgLysAspTrpHisArgAlaAsnGlnSerTyrProSer-291 |
| SEQ. ID. NO. 14727 | 298-LysLeuAsnArgGlyGluLeuGly-305 |
| SEQ. ID. NO. 14728 | 312-AlaProAsnGluThrGlnAla-318 |

TABLE 1-continued

| SEQ. ID. NO. 14729 | 320-GluSerValGluThrThrLys-326 |
|---|---|
| SEQ. ID. NO. 14730 | 337-ValGlnGlyArgLeuLysAla-343 |
| SEQ. ID. NO. 14731 | 345-ArgPheThrAspGlyLysTrpGlnGluThrGluLeuProArgLeuProSerGly-362 |
| SEQ. ID. NO. 14732 | 365-GluMetThrAspGlnProTrpGlyGly-373 |
| SEQ. ID. NO. 14733 | 401-ValMetArgArgGlnProGlnGlnPheAspSerAspGlyIleAsn-415 |
| SEQ. ID. NO. 14734 | 422-ThrSerAlaAspGlyGluArgIle-429 |
| SEQ. ID. NO. 14735 | 435-GlyLysAsnAlaAlaProAspMet-442 |
| SEQ. ID. NO. 14736 | 479-AsnIleArgGlyGlyGlyGluPheGlyProArgTrpHis-491 |
| SEQ. ID. NO. 14737 | 496-GlyIleSerLysHisLysSerValAspAsp-505 |
| SEQ. ID. NO. 14738 | 512-AspLeuSerGluArgGlyIleSerSerProGluHis-523 |
| SEQ. ID. NO. 14739 | 528-GlyGlySerAsnGly-532 |
| SEQ. ID. NO. 14740 | 540-PheValArgGluProGlnSerIleGlyAla-549 |
| SEQ. ID. NO. 14741 | 568-GlySerSerTrpThrAspGluTyrGlyAsnProGlnLysTyrGluValCysLysArgArgLeuGlyGluLeuSerProTyr-594 |
| SEQ. ID. NO. 14742 | 596-AsnLeuSerAspGlyIleAspTyrPro-604 |
| SEQ. ID. NO. 14743 | 610-ThrSerLeuSerAspAspArgValHis-618 |
| SEQ. ID. NO. 14744 | 627-AlaLysLeuArgGluThrSerProGlnSer-636 |
| SEQ. ID. NO. 14745 | 639-TyrSerProAspGlyGlyGlyHisThrGlyAsnGlyThrGlnArgGluAlaAlaAspGluLeu-659 |
| Hydrophilic Regions - Hopp-Woods | |
| SEQ. ID. NO. 14746 | 3-SerTyrProAspProTyrArgHis-10 |
| SEQ. ID. NO. 14747 | 12-GluAsnLeuAspSerAlaGluThr-19 |
| SEQ. ID. NO. 14748 | 26-AlaAsnAlaGluThrArgAlaArgPheLeuAsnAsnAspLysAlaArgAlaLeuSer-44 |
| SEQ. ID. NO. 14749 | 52-GlnAspThrArgGln-56 |
| SEQ. ID. NO. 14750 | 61-GlnGluHisArgAlaArg-66 |
| SEQ. ID. NO. 14751 | 72-GlnAspAlaGluTyrPro-77 |
| SEQ. ID. NO. 14752 | 104-AspPheAspGluLeuLeuGly-110 |
| SEQ. ID. NO. 14753 | 134-LysSerGlyGlyAsp-138 |
| SEQ. ID. NO. 14754 | 145-ValAspLeuGluAlaGlyGluLeuValGlu-154 |
| SEQ. ID. NO. 14755 | 166-ValSerTrpArgAspGluAsnSer-173 |
| SEQ. ID. NO. 14756 | 180-TrpAspGluArgGlnLeuThr-186 |
| SEQ. ID. NO. 14757 | 198-GluArgGlyLysSerPheGluGluSerLeu-207 |
| SEQ. ID. NO. 14758 | 212-IleAlaGluAspGlyMet-217 |
| SEQ. ID. NO. 14759 | 233-AspLeuIleGluAlaSerAsp-239 |
| SEQ. ID. NO. 14760 | 251-AlaGluGlyGluAlaLysPro-257 |
| SEQ. ID. NO. 14761 | 278-LeuArgLysAspTrpHisArg-284 |
| SEQ. ID. NO. 14762 | 298-LysLeuAsnArgGlyGluLeuGly-305 |
| SEQ. ID. NO. 14763 | 320-GluSerValGluThrThrLys-326 |
| SEQ. ID. NO. 14764 | 337-ValGlnGlyArgLeuLysAla-343 |
| SEQ. ID. NO. 14765 | 350-LysTrpGlnGluThrGluLeuProArg-358 |
| SEQ. ID. NO. 14766 | 401-ValMetArgArgGlnProGlnGlnPheAspSerAspGlyIleAsn-415 |
| SEQ. ID. NO. 14767 | 424-AlaAspGlyGluArg-428 |
| SEQ. ID. NO. 14768 | 436-LysAsnAlaAlaProAsp-441 |
| SEQ. ID. NO. 14769 | 481-ArgGlyGlyGlyGluPheGly-487 |
| SEQ. ID. NO. 14770 | 496-GlyIleSerLysHisLysSerValAspAsp-505 |
| SEQ. ID. NO. 14771 | 512-AspLeuSerGluArgGlyIleSerSer-520 |
| SEQ. ID. NO. 14772 | 540-PheValArgGluProGlnSer-546 |
| SEQ. ID. NO. 14773 | 571-TrpThrAspGluTyrGlyAsn-577 |
| SEQ. ID. NO. 14774 | 579-GlnLysTyrGluValCysLysArgArgLeuGlyGlu-590 |
| SEQ. ID. NO. 14775 | 612-LeuSerAspAspArgValHis-618 |
| SEQ. ID. NO. 14776 | 627-AlaLysLeuArgGluThrSer-633 |
| SEQ. ID. NO. 14777 | 650-GlyThrGlnArgGluAlaAlaAspGluLeu-659 |
| a042-1 | |
| AMPHI Regions - AMPHI | |
| SEQ. ID. NO. 14778 | 17-AlaLeuSerAsnThrSerThr-23 |
| SEQ. ID. NO. 14779 | 33-AlaValArgSerMetMetLysIle-40 |
| SEQ. ID. NO. 14780 | 138-SerProLeuValArgIleLeuProLeuSer-147 |
| SEQ. ID. NO. 14781 | 151-SerMetValValAlaPhePheAlaAsn-159 |
| Antigenic Index - Jameson-Wolf | |
| SEQ. ID. NO. 14782 | 14-ArgThrSerAlaLeuSerAsnThrSerThrAlaAlaGlyProSerCys-29 |
| SEQ. ID. NO. 14783 | 49-TyrSerLysGluThrGlyCysProCysProSerLeuArgLysAspSerSerThrGlyGlyArgProMetSerProCys-74 |
| SEQ. ID. NO. 14784 | 77-LeuAlaAsnArgAspCysValProLysAlaAspThr-88 |
| SEQ. ID. NO. 14785 | 93-ThrAspSerThrSerProArgProLeu-101 |
| SEQ. ID. NO. 14786 | 122-AlaArgAlaSerLeuProLysIleArgAlaLysVal-133 |
| SEQ. ID. NO. 14787 | 160-CysSerTyrAlaSerAlaProGlyPro-168 |
| Hydrophilic Regions - Hopp-Woods | |
| SEQ. ID. NO. 14788 | 49-TyrSerLysGluThrGlyCys-55 |
| SEQ. ID. NO. 14789 | 59-SerLeuArgLysAspSerSerThrGlyGlyArgProMet-71 |
| SEQ. ID. NO. 14790 | 78-AlaAsnArgAspCysValProLysAlaAspThr-88 |
| SEQ. ID. NO. 14791 | 94-AspSerThrSerProArg-99 |
| SEQ. ID. NO. 14792 | 125-SerLeuProLysIleArgAlaLysVal-133 |
| a043-2 | |
| AMPHI Regions - AMPHI | |
| SEQ. ID. NO. 14793 | 24-ValGluProSerArg-28 |
| SEQ. ID. NO. 14794 | 36-HisGlyGlyLeuAspGlyAlaAlaGlyPheAspGluGlyGluArg-50 |
| SEQ. ID. NO. 14795 | 59-AlaSerGlyAspGlyPhe-64 |
| SEQ. ID. NO. 14796 | 83-AlaGlyAspPheGlyAspGlyGlnArg-91 |
| Antigenic Index - Jameson-Wolf | |
| SEQ. ID. NO. 14797 | 1-MetProProAlaPro-5 |
| SEQ. ID. NO. 14798 | 11-IleArgArgGlnLysSerValMetProSerGluArgPheValGluProSerArg-28 |
| SEQ. ID. NO. 14799 | 35-ValHisGlyGlyLeuAspGlyAlaAlaGlyPheAspGluGlyGluArgValPhe-52 |
| SEQ. ID. NO. 14800 | 56-AlaAlaGlnAlaSerGlyAspGlyPheAla-65 |

TABLE 1-continued

| | |
|---|---|
| SEQ. ID. NO. 14801 | 79-GlnSerAspAlaAlaGlyAspPheGlyAspGlyGlnArgThrGlyGlu-94 |
| SEQ. ID. NO. 14802 | 96-ValLeuGlnAspValGlyGly-102 |
| SEQ. ID. NO. 14803 | 116-AlaGluGlyGluAlaGln-121 |

Hydrophilic Regions - Hopp-Woods

| | |
|---|---|
| SEQ. ID. NO. 14804 | 11-IleArgArgGlnLysSerValMetProSerGluArgPheValGluProSerArg-28 |
| SEQ. ID. NO. 14805 | 43-AlaGlyPheAspGluGlyGluArgValPhe-52 |
| SEQ. ID. NO. 14806 | 81-AspAlaAlaGlyAspPheGlyAspGlyGlnArgThrGly-93 |
| SEQ. ID. NO. 14807 | 116-AlaGluGlyGluAlaGln-121 | a046
AMPHI Regions - AMPHI

| | |
|---|---|
| SEQ. ID. NO. 14808 | 6-ArgProThrSerSerPro-11 |
| SEQ. ID. NO. 14809 | 46-ThrSerCysSerGlyLeuMetValSer-54 |
| SEQ. ID. NO. 14810 | 64-PheSerLeuPheSerSer-69 |
| SEQ. ID. NO. 14811 | 113-LysSerAlaSerSer-117 |
| SEQ. ID. NO. 14812 | 143-SerCysAsnAlaPheSerSer-149 |
| SEQ. ID. NO. 14813 | 155-ThrSerLeuLeuGlyMetAlaAlaArgPheCysAlaThrVal-168 |

Antigenic Index - Jameson-Wolf

| | |
|---|---|
| SEQ. ID. NO. 14814 | 6-ArgProThrSerSerProProArgArgAlaCys-16 |
| SEQ. ID. NO. 14815 | 20-IleArgThrArgSerSerAlaLysArgLysThrCysAsnAlaProGlyGlnSerIleArgProAlaSerCysSer-44 |
| SEQ. ID. NO. 14816 | 57-ProAsnMetGluArgLeuPro-63 |
| SEQ. ID. NO. 14817 | 75-SerArgTyrSerLeuGluArgThrArgAlaMetArgProGlyMetLeuAsnArgSerAlaAla-95 |
| SEQ. ID. NO. 14818 | 105-SerLeuArgGluSerAlaSerSerLysSerAlaSerSerAlaProAlaArgSerAsnValLysGlyAspAlaProLeuProLysThrValTrpThrSerArgArgLeuProVal-142 |
| SEQ. ID. NO. 14819 | 169-GluProThrCysProLeuProLys-176 |

Hydrophilic Regions - Hopp-Woods

| | |
|---|---|
| SEQ. ID. NO. 14820 | 7-ProThrSerSerProProArgArgAlaCys-16 |
| SEQ. ID. NO. 14821 | 20-IleArgThrArgSerSerAlaLysArgLysThrCysAsn-32 |
| SEQ. ID. NO. 14822 | 36-GlnSerIleArgProAlaSer-42 |
| SEQ. ID. NO. 14823 | 58-AsnMetGluArgLeuPro-63 |
| SEQ. ID. NO. 14824 | 75-SerArgTyrSerLeuGluArgThrArgAlaMetArg-86 |
| SEQ. ID. NO. 14825 | 105-SerLeuArgGluSerAlaSerSerLysSerAlaSer-116 |
| SEQ. ID. NO. 14826 | 118-AlaProAlaArgSerAsnValLysGlyAspAlaProLeu-130 | a047
AMPHI Regions - AMPHI

| | |
|---|---|
| SEQ. ID. NO. 14827 | 17-IleAlaAspIleAlaGlnAspLeuProAspGlyAla-28 |
| SEQ. ID. NO. 14828 | 62-AlaGluAsnIleGlyAlaVal-68 |
| SEQ. ID. NO. 14829 | 93-ArgLeuAlaLysGlnLeuGlu-99 |
| SEQ. ID. NO. 14830 | 141-TyrIleAspGluIleAspValPhe-148 |
| SEQ. ID. NO. 14831 | 161-SerAlaLeuLeuAla-165 |
| SEQ. ID. NO. 14832 | 185-LeuLeuGluGlyAsn-189 |
| SEQ. ID. NO. 14833 | 202-IleGlySerIleLeuAla-207 |
| SEQ. ID. NO. 14834 | 247-SerGlyIleLysTrpProGluGlyCys-255 |
| SEQ. ID. NO. 14835 | 257-IleAlaAlaValValArgAlaGlyThrGly-266 |
| SEQ. ID. NO. 14836 | 293-IleLeuAsnGluLeuGluLysLeuIle-301 |

Antigenic Index - Jameson-Wolf

| | |
|---|---|
| SEQ. ID. NO. 14837 | 5-GlnAlaArgArgGlyGlyLeuLeu-12 |
| SEQ. ID. NO. 14838 | 20-IleAlaGlnAspLeuProAspGlyAlaAsp-29 |
| SEQ. ID. NO. 14839 | 36-TyrArgAsnAsnArgLeu-41 |
| SEQ. ID. NO. 14840 | 51-IleGluGlyAspGlu-55 |
| SEQ. ID. NO. 14841 | 70-ProGluLeuArgProLysGluThrSerThrArgArgIleMet-83 |
| SEQ. ID. NO. 14842 | 86-GlyGlyGlyAsnIle-90 |
| SEQ. ID. NO. 14843 | 96-LysGlnLeuGluHis-100 |
| SEQ. ID. NO. 14844 | 106-IleIleGluCysArgProArgArgAlaGluTrpIle-117 |
| SEQ. ID. NO. 14845 | 119-GluAsnLeuAspAsnThrLeu-125 |
| SEQ. ID. NO. 14846 | 130-SerAlaThrAspGluThrLeuLeuAspAsnGluTyrIleAspGluIleAsp-146 |
| SEQ. ID. NO. 14847 | 152-ThrAsnAspAspGluSerAsnIle-159 |
| SEQ. ID. NO. 14848 | 168-LeuGlyAlaLysArgVal-173 |
| SEQ. ID. NO. 14849 | 178-AsnArgSerSerTyr-182 |
| SEQ. ID. NO. 14850 | 186-LeuGluGlyAsnLysIle-191 |
| SEQ. ID. NO. 14851 | 208-HisIleArgArgGlyAspIleVal-215 |
| SEQ. ID. NO. 14852 | 219-ProIleArgArgGlyThrAlaGluAlaIleGlu-229 |
| SEQ. ID. NO. 14853 | 232-AlaHisGlyAspLysLysThrSer-239 |
| SEQ. ID. NO. 14854 | 242-IleGlyArgArgIleSerGlyIleLysTrpProGluGlyCysHis-256 |
| SEQ. ID. NO. 14855 | 262-ArgAlaGlyThrGlyGluThr-268 |
| SEQ. ID. NO. 14856 | 277-ValIleGlnAspGlyAspHis-283 |
| SEQ. ID. NO. 14857 | 288-ValSerArgArgArgIleLeuAsnGluLeuGluLys-299 |

Hydrophilic Regions - Hopp-Woods

| | |
|---|---|
| SEQ. ID. NO. 14858 | 5-GlnAlaArgArgGlyGly-10 |
| SEQ. ID. NO. 14859 | 20-IleAlaGlnAspLeuProAspGlyAlaAsp-29 |
| SEQ. ID. NO. 14860 | 51-IleGluGlyAspGlu-55 |
| SEQ. ID. NO. 14861 | 70-ProGluLeuArgProLysGluThrSerThrArgArgIleMet-83 |
| SEQ. ID. NO. 14862 | 106-IleIleGluCysArgProArgArgAlaGluTrpIle-117 |
| SEQ. ID. NO. 14863 | 130-SerAlaThrAspGluThrLeuLeu-137 |
| SEQ. ID. NO. 14864 | 140-GluTyrIleAspGluIleAsp-146 |
| SEQ. ID. NO. 14865 | 152-ThrAsnAspAspGluSerAsnIle-159 |
| SEQ. ID. NO. 14866 | 168-LeuGlyAlaLysArgVal-173 |
| SEQ. ID. NO. 14867 | 186-LeuGluGlyAsnLysIle-191 |
| SEQ. ID. NO. 14868 | 209-IleArgArgGlyAspIle-214 |
| SEQ. ID. NO. 14869 | 219-ProIleArgArgGlyThrAlaGluAlaIleGlu-229 |

TABLE 1-continued

| | |
|---|---|
| SEQ. ID. NO. 14870 | 232-AlaHisGlyAspLysLysThrSer-239 |
| SEQ. ID. NO. 14871 | 242-IleGlyArgArgIleSer-247 |
| SEQ. ID. NO. 14872 | 277-ValIleGlnAspGlyAsp-282 |
| SEQ. ID. NO. 14873 | 289-SerArgArgArgIleLeuAsnGluLeuGluLys-299 |
| a049-2 | |
| AMPHI Regions - AMPHI | |
| SEQ. ID. NO. 14874 | 15-GlnHisLeuLeuGlu-19 |
| SEQ. ID. NO. 14875 | 33-ThrAspAspThrValAspGlyIleGlyGlnMet-43 |
| SEQ. ID. NO. 14876 | 50-GlnProPheGlyGln-54 |
| SEQ. ID. NO. 14877 | 61-GluHisPheAlaProValAspGlyPheArg-70 |
| SEQ. ID. NO. 14878 | 79-HisGlnArgPhePhe-83 |
| SEQ. ID. NO. 14879 | 103-IleGlyValPheProAlaPhe-109 |
| SEQ. ID. NO. 14880 | 202-ArgGlyAlaGlyGlnArgArgValSerArgHisCys-213 |
| SEQ. ID. NO. 14881 | 217-AlaArgLeuThrGlnValPheGlnThrPhePhe-227 |
| Antigenic Index - Jameson-Wolf | |
| SEQ. ID. NO. 14882 | 6-PheAspTyrArgThrArgLeu-12 |
| SEQ. ID. NO. 14883 | 20-LeuIleGlyLysAsnArgHis-26 |
| SEQ. ID. NO. 14884 | 29-LeuHisArgArgThrAspAspThrValAspGly-39 |
| SEQ. ID. NO. 14885 | 49-AspGlnProPheGly-53 |
| SEQ. ID. NO. 14886 | 64-AlaProValAspGlyPheArgValGlnAsnIleAspLeuAspGlyHisGlnArgPhePhe-83 |
| SEQ. ID. NO. 14887 | 90-PheArgAsnProValCysArgArgThrArgPheCys-101 |
| SEQ. ID. NO. 14888 | 122-GlyIleLysProAspSerProProArgPhe-131 |
| SEQ. ID. NO. 14889 | 135-PheArgAsnArgHisLeuGlnGlySerLeuArgVal-146 |
| SEQ. ID. NO. 14890 | 150-PheLeuLysAspAspHisArgValGly-158 |
| SEQ. ID. NO. 14891 | 182-GlnHisThrGlySer-186 |
| SEQ. ID. NO. 14892 | 193-ArgHisArgArgValArgSerGlyPheArgGlyAlaGlyGlnArgArgValSerArgHisCys-213 |
| SEQ. ID. NO. 14893 | 246-ArgGlnThrAsnProArgProLysArgGlyLeu-256 |
| Hydrophilic Regions - Hopp-Woods | |
| SEQ. ID. NO. 14894 | 21-IleGlyLysAsnArgHis-26 |
| SEQ. ID. NO. 14895 | 31-ArgArgThrAspAspThrValAsp-38 |
| SEQ. ID. NO. 14896 | 72-GlnAsnIleAspLeuAspGlyHisGlnArgPhePhe-83 |
| SEQ. ID. NO. 14897 | 93-ProValCysArgArgThrArgPheCys-101 |
| SEQ. ID. NO. 14898 | 124-LysProAspSerProProArg-130 |
| SEQ. ID. NO. 14899 | 150-PheLeuLysAspAspHisArgVal-157 |
| SEQ. ID. NO. 14900 | 193-ArgHisArgArgValArgSerGlyPheArgGlyAlaGlyGlnArgArgValSerArg-211 |
| SEQ. ID. NO. 14901 | 246-ArgGlnThrAsnProArgProLysArgGlyLeu-256 |
| a050-1 | |
| AMPHI Regions - AMPHI | |
| SEQ. ID. NO. 14902 | 10-IleGlnSerIleCysAspAlaPheGlnPheIleSerTyrTyr-23 |
| SEQ. ID. NO. 14903 | 25-ProLysAspTyrIleAspAlaLeuTyrLysAlaTrpGlnLys-38 |
| SEQ. ID. NO. 14904 | 94-ValAsnGluGlyVal-98 |
| SEQ. ID. NO. 14905 | 163-AsnProSerAspAsnIleValAspTrpValLeuLys-174 |
| SEQ. ID. NO. 14906 | 177-ProThrMetGlyAla-181 |
| SEQ. ID. NO. 14907 | 235-LeuGluLeuPheGluLysValAsnAla-243 |
| SEQ. ID. NO. 14908 | 250-GlyLeuGlyGlyLeuThrThr-256 |
| SEQ. ID. NO. 14909 | 275-AlaMetIleProAsn-279 |
| SEQ. ID. NO. 14910 | 302-ArgValGluAspTrpProAspLeuThr-310 |
| SEQ. ID. NO. 14911 | 315-AsnGlyLysArgValAspValAsp-322 |
| SEQ. ID. NO. 14912 | 353-LysArgLeuValAspMetLeuAspLys-361 |
| SEQ. ID. NO. 14913 | 367-ValAspPheThrAsnArgLeu-373 |
| SEQ. ID. NO. 14914 | 379-ProValAspProValGlyAspGlu-386 |
| SEQ. ID. NO. 14915 | 396-AlaThrArgMetAspLysPheThrArgGlnMet-406 |
| SEQ. ID. NO. 14916 | 410-ThrAspLeuLeuGlyMet-415 |
| SEQ. ID. NO. 14917 | 452-LysSerSerLysValLeuAlaPhe-459 |
| Antigenic Index - Jameson-Wolf | |
| SEQ. ID. NO. 14918 | 4-IleLysGlnGluAspPheIle-10 |
| SEQ. ID. NO. 14919 | 23-TyrHisProLysAspTyrIleAspAlaLeu-32 |
| SEQ. ID. NO. 14920 | 36-TrpGlnLysGluGluAsnProAlaAlaLysAspAlaMet-48 |
| SEQ. ID. NO. 14921 | 55-SerArgMetCysAlaGluAsnAsnArgProIleCysGlnAspThrGly-70 |
| SEQ. ID. NO. 14922 | 88-MetSerValGluGluMetValAsnGluGlyValArgArgAlaTyrThrTrpGluGlyAsnThrLeuArgAlaSerVal-113 |
| SEQ. ID. NO. 14923 | 116-AspProAlaGlyLysArgGlnAsnThrLysAspAsnThr-128 |
| SEQ. ID. NO. 14924 | 137-ValProGlyAspLysValGluVal-144 |
| SEQ. ID. NO. 14925 | 146-CysAlaAlaLysGlyGlyGlySerGluAsnLysSerLysLeu-159 |
| SEQ. ID. NO. 14926 | 163-AsnProSerAspAsnIle-168 |
| SEQ. ID. NO. 14927 | 192-GlyIleGlyGlyThrProGluLysAlaValLeuMetAlaLysGluSerLeu-208 |
| SEQ. ID. NO. 14928 | 213-AspIleGlnGluLeuGlnGluLysAlaAlaSerGlyAlaGluLeuSerThr-229 |
| SEQ. ID. NO. 14929 | 284-ArgHisValGluPheGluLeuAspGlySerGlyProValGluLeuThrProProArgValGluAspTrpProAspLeuThrTyrSerProAsp AsnGlyLysArgValAspValAspLysLeuThrLysGluGluValAlaSer-331 |
| SEQ. ID. NO. 14930 | 345-LeuThrGlyArgAspAlaAlaHisLysArgLeuValAspMetLeuAspLysGlyGluGluLeuPro-366 |
| SEQ. ID. NO. 14931 | 379-ProValAspProValGlyAspGluIleValGlyProAlaGlyProThrThrAlaThrArgMetAspLysPheThrArgGlnMetLeuGluGln ThrAsp-411 |
| SEQ. ID. NO. 14932 | 417-GlyLysSerGluArgGlyAlaAlaThr-425 |
| SEQ. ID. NO. 14933 | 428-AlaIleAlaAspAsnLysAla-434 |
| SEQ. ID. NO. 14934 | 450-AlaIleLysSerSerLys-455 |
| SEQ. ID. NO. 14935 | 470-PheGluValLysAspMetPro-476 |
| SEQ. ID. NO. 14936 | 481-ValAspSerLysGlyGluSerIle-488 |
| SEQ. ID. NO. 14937 | 492-AlaProProGlnTrpGln-497 |
| Hydrophilic Regions - Hopp-Woods | |
| SEQ. ID. NO. 14938 | 4-IleLysGlnGluAspPheIle-10 |
| SEQ. ID. NO. 14939 | 36-TrpGlnLysGluGluAsnProAlaAlaLysAspAlaMet-48 |

TABLE 1-continued

| SEQ. ID. NO. | |
|---|---|
| SEQ. ID. NO. 14940 | 57-MetCysAlaGluAsnAsnArgProIleCys-66 |
| SEQ. ID. NO. 14941 | 88-MetSerValGluGluMetValAsnGluGlyValArgArg-100 |
| SEQ. ID. NO. 14942 | 117-ProAlaGlyLysArgGlnAsnThrLysAspAsnThr-128 |
| SEQ. ID. NO. 14943 | 138-ProGlyAspLysValGluVal-144 |
| SEQ. ID. NO. 14944 | 148-AlaLysGlyGlyGlySerGluAsnLysSerLysLeu-159 |
| SEQ. ID. NO. 14945 | 195-GlyThrProGluLysAlaValLeuMetAlaLysGluSerLeu-208 |
| SEQ. ID. NO. 14946 | 213-AspIleGlnGluLeuGlnGluLysAlaAlaSer-223 |
| SEQ. ID. NO. 14947 | 225-AlaGluLeuSerThr-229 |
| SEQ. ID. NO. 14948 | 284-ArgHisValGluPheGluLeuAspGly-292 |
| SEQ. ID. NO. 14949 | 299-ThrProProArgValGluAspTrpPro-307 |
| SEQ. ID. NO. 14950 | 313-ProAspAsnGlyLysArgValAspValAspLysLeuThrLysGluGluValAlaSer-331 |
| SEQ. ID. NO. 14951 | 345-LeuThrGlyArgAspAlaAlaHisLysArgLeuValAspMetLeuAspLysGlyGluGluLeuPro-366 |
| SEQ. ID. NO. 14952 | 382-ProValGlyAspGluIleVal-388 |
| SEQ. ID. NO. 14953 | 397-ThrArgMetAspLysPheThrArgGlnMetLeuGluGlnThrAsp-411 |
| SEQ. ID. NO. 14954 | 417-GlyLysSerGluArgGlyAlaAlaThr-425 |
| SEQ. ID. NO. 14955 | 428-AlaIleAlaAspAsnLysAla-434 |
| SEQ. ID. NO. 14956 | 450-AlaIleLysSerSerLys-455 |
| SEQ. ID. NO. 14957 | 470-PheGluValLysAspMetPro-476 |
| SEQ. ID. NO. 14958 | 481-ValAspSerLysGlyGluSerIle-488 | a052
AMPHI Regions - AMPHI

| SEQ. ID. NO. 14959 | 40-AlaLysAlaSerLysSerAlaThrSerProLysGlyLeuAspGlyValSerLys-57 |
|---|---|
| SEQ. ID. NO. 14960 | 66-ThrAlaAlaPheHisSerPheIleSerValGlyAspThrLeuThrSerMetProAsnLeuValThrMetLeu-89 |

Antigenic Index - Jameson-Wolf

| SEQ. ID. NO. 14961 | 4-ValAlaGluGluThrGluIle-10 |
|---|---|
| SEQ. ID. NO. 14962 | 14-CysPheLysGlyGluProThrGlyAspSerArgLeuLeuSerThrThrLysSerAlaPro-33 |
| SEQ. ID. NO. 14963 | 36-CysAlaAsnSerAlaLysAlaSerLysSerAlaThrSerProLysGlyLeuAspGlyValSerLysAsnSerSer-60 |
| SEQ. ID. NO. 14964 | 95-ValValProAsnArgLeuArgLeu-102 |
| SEQ. ID. NO. 14965 | 108-ProAlaCysLysLysValLysAsnAlaAla-117 |

Hydrophilic Regions - Hopp-Woods

| SEQ. ID. NO. 14966 | 4-ValAlaGluGluThrGluIle-10 |
|---|---|
| SEQ. ID. NO. 14967 | 15-PheLysGlyGluProThrGlyAspSerArgLeu-25 |
| SEQ. ID. NO. 14968 | 29-ThrLysSerAlaPro-33 |
| SEQ. ID. NO. 14969 | 38-AsnSerAlaLysAlaSerLysSerAlaThrSerProLysGlyLeuAspGlyValSerLysAsnSer-59 |
| SEQ. ID. NO. 14970 | 98-AsnArgLeuArgLeu-102 |
| SEQ. ID. NO. 14971 | 109-AlaCysLysLysValLysAsnAlaAla-117 | a075
AMPHI Regions - AMPHI

| SEQ. ID. NO. 14972 | 19-LysThrProThrThrIleGlnProAlaSerIleProSer-31 |
|---|---|
| SEQ. ID. NO. 14973 | 65-AlaProTyrLeuArgGlnValLeu-72 |
| SEQ. ID. NO. 14974 | 80-PheLysLysCysLeuAla-85 |
| SEQ. ID. NO. 14975 | 116-AspPhePheGlnThrCysValAsnArgPhePheGluValValGluIleIleGlyIleGly-135 |

Antigenic Index - Jameson-Wolf

| SEQ. ID. NO. 14976 | 10-ThrMetGluLysThrLysSerAlaAlaLysThrProThr-22 |
|---|---|
| SEQ. ID. NO. 14977 | 25-GlnProAlaSerIlePro-30 |
| SEQ. ID. NO. 14978 | 52-AlaLysAlaArgGly-56 |
| SEQ. ID. NO. 14979 | 91-PhePheArgArgProProAsnIleArgLysSerValPheGlnLysSerGluTyrAspLys-110 |

Hydrophilic Regions - Hopp-Woods

| SEQ. ID. NO. 14980 | 10-ThrMetGluLysThrLysSerAlaAlaLysThr-20 |
|---|---|
| SEQ. ID. NO. 14981 | 52-AlaLysAlaArgGly-56 |
| SEQ. ID. NO. 14982 | 91-PhePheArgArgProProAsnIleArgLysSerValPheGlnLysSerGuTyrAspLys-110 | a080
AMPHI Regions - AMPHI

| SEQ. ID. NO. 14983 | 6-GluAlaMetGluArgLeuThrArg-13 |
|---|---|
| SEQ. ID. NO. 14984 | 95-PheProAspThrValGlu-100 |
| SEQ. ID. NO. 14985 | 108-ProValAlaArgTrpGlyAspHis-115 |
| SEQ. ID. NO. 14986 | 144-SerAlaGluMetLeuArgArgTyrAspGluPheSerThrValLeu-158 |
| SEQ. ID. NO. 14987 | 195-LysArgLeuArgLeuPheThrGluAlaTrpGlnHis-206 |

Antigenic Index - Jameson-Wolf

| SEQ. ID. NO. 14988 | 1-MetTrpAspAsnAlaGluAlaMetGluArgLeuThr-12 |
|---|---|
| SEQ. ID. NO. 14989 | 33-AsnSerAsnHisLeuPro-38 |
| SEQ. ID. NO. 14990 | 42-ValSerLeuLysGly-46 |
| SEQ. ID. NO. 14991 | 50-TyrSerAspLysLysAlaLeu-56 |
| SEQ. ID. NO. 14992 | 67-AsnIleLeuArgThrAspIleAsnGlyAlaGlnGluAlaTyrArg-81 |
| SEQ. ID. NO. 14993 | 90-MetValArgArgArgPheProAspThrValGlu-100 |
| SEQ. ID. NO. 14994 | 103-LeuThrGluArgLysProValAlaArgTrpGly-113 |
| SEQ. ID. NO. 14995 | 116-AlaLeuValAspGlyGluGlyAsnValPhe-125 |
| SEQ. ID. NO. 14996 | 127-AlaArgLeuAspArgProGlyMetPro-135 |
| SEQ. ID. NO. 14997 | 138-ArgGlyAlaGluGlyThrSer-144 |
| SEQ. ID. NO. 14998 | 146-GluMetLeuArgArgTyrAspGlu-153 |
| SEQ. ID. NO. 14999 | 163-LeuGlyIleLysGlu-167 |
| SEQ. ID. NO. 15000 | 187-ArgLeuGlyArgGluAsnGluMetLysArgLeuArgLeu-199 |
| SEQ. ID. NO. 15001 | 207-LeuLeuArgLysAsnLysAsnArgLeuSer-216 |
| SEQ. ID. NO. 15002 | 220-MetArgTyrLysAspGlyPheSer-227 |
| SEQ. ID. NO. 15003 | 230-TyrAlaProAspGlyLeuProGluLysGluSerGluGlu-242 |

Hydrophilic Regions - Hopp-Woods

| SEQ. ID. NO. 15004 | 3-AspAsnAlaGluAlaMetGluArgLeuThr-12 |
|---|---|
| SEQ. ID. NO. 15005 | 50-TyrSerAspLysLysAlaLeu-56 |
| SEQ. ID. NO. 15006 | 69-LeuArgThrAspIleAsnGlyAlaGlnGluAlaTyrArg-81 |
| SEQ. ID. NO. 15007 | 90-MetValArgArgArgPheProAspThrVal-99 |

TABLE 1-continued

| | |
|---|---|
| SEQ. ID. NO. 15008 | 103-LeuThrGluArgLysProValAlaArgTrpGly-113 |
| SEQ. ID. NO. 15009 | 116-AlaLeuValAspGlyGluGlyAsnValPhe-125 |
| SEQ. ID. NO. 15010 | 127-AlaArgLeuAspArgProGly-133 |
| SEQ. ID. NO. 15011 | 138-ArgGlyAlaGluGlyThrSer-144 |
| SEQ. ID. NO. 15012 | 146-GluMetLeuArgArgTyrAspGlu-153 |
| SEQ. ID. NO. 15013 | 163-LeuGlyIleLysGlu-167 |
| SEQ. ID. NO. 15014 | 187-ArgLeuGlyArgGluAsnGluMetLysArgLeuArgLeu-199 |
| SEQ. ID. NO. 15015 | 208-LeuArgLysAsnLysAsnArgLeuSer-216 |
| SEQ. ID. NO. 15016 | 220-MetArgTyrLysAspGlyPheSer-227 |
| SEQ. ID. NO. 15017 | 234-GlyLeuProGluLysGluSerGluGlu-242 |
| a081 | |
| AMPHI Regions - AMPHI | |
| SEQ. ID. NO. 15018 | 22-LysProValSerArgIleValThrAspSer-31 |
| SEQ. ID. NO. 15019 | 86-ThrAlaLeuGlnMetLeuAlaLysAlaTrpArgGluAsn-98 |
| SEQ. ID. NO. 15020 | 116-LysGluMetLeuAlaAlaValLeuArgArg-125 |
| SEQ. ID. NO. 15021 | 135-ThrAlaGlyAsnPhe-139 |
| SEQ. ID. NO. 15022 | 165-MetAsnHisPheGlyGluLeuAlaValLeuThrGlnIleAlaLys-179 |
| SEQ. ID. NO. 15023 | 185-ValAsnAsnAlaMetArg-190 |
| SEQ. ID. NO. 15024 | 198-AspGlyValGlyAspIleAlaLysAla-206 |
| SEQ. ID. NO. 15025 | 303-LeuAsnAspValAlaGluGlyLeuLysGlyPheSerAsnIle-316 |
| SEQ. ID. NO. 15026 | 345-AlaAlaValAspValLeuAlaArgMetPro-354 |
| SEQ. ID. NO. 15027 | 360-ValMetGlyAspMetGlyGluLeuGlyGlu-369 |
| SEQ. ID. NO. 15028 | 399-ValGluAlaAlaGlu-403 |
| Antigenic Index - Jameson-Wolf | |
| SEQ. ID. NO. 15029 | 16-ProMetProSerGluSerLysProValSer-25 |
| SEQ. ID. NO. 15030 | 27-IleValThrAspSerArgAspIleArgAlaGlyAsp-38 |
| SEQ. ID. NO. 15031 | 44-AlaGlyGlyArgPheAspAla-50 |
| SEQ. ID. NO. 15032 | 67-ValSerArgGluAspCysValAla-74 |
| SEQ. ID. NO. 15033 | 77-GlyAlaLeuLysValAspAspThrLeu-85 |
| SEQ. ID. NO. 15034 | 94-AlaTrpArgGluAsnValAsnProPhe-102 |
| SEQ. ID. NO. 15035 | 108-GlySerGlyGlyGlyLysThrThrValLysGluMetLeu-119 |
| SEQ. ID. NO. 15036 | 123-LeuArgArgArgPheGlyAspAsnAlaVal-132 |
| SEQ. ID. NO. 15037 | 138-AsnPheAsnAsnHisIle-143 |
| SEQ. ID. NO. 15038 | 151-LysLeuAsnGluLysHisArg-157 |
| SEQ. ID. NO. 15039 | 178-AlaLysProAspAla-182 |
| SEQ. ID. NO. 15040 | 194-GlyCysGlyPheAspGlyValGlyAspIleAlaLysAlaLysSerGluIle-210 |
| SEQ. ID. NO. 15041 | 213-GlyLeuCysSerAspGly-218 |
| SEQ. ID. NO. 15042 | 223-ProGlnGluAspAlaAsn-228 |
| SEQ. ID. NO. 15043 | 239-LeuAsnThrArgThrPheGlyIleAspSerGlyAspValHisAla-253 |
| SEQ. ID. NO. 15044 | 280-ValProGlyArgHisAsnVal-286 |
| SEQ. ID. NO. 15045 | 305-AspValAlaGluGlyLeuLys-311 |
| SEQ. ID. NO. 15046 | 313-PheSerAsnIleLysGlyArgLeuAsnValLysSerGlyIleLysGly-328 |
| SEQ. ID. NO. 15047 | 330-ThrLeuIleAspAspThrTyrAsnAlaAsnProAspSerMetLysAlaAlaVal-347 |
| SEQ. ID. NO. 15048 | 363-AspMetGlyGluLeuGlyGluAspGluAlaAla-373 |
| SEQ. ID. NO. 15049 | 381-AlaTyrAlaArgAspGlnGlyIle-388 |
| SEQ. ID. NO. 15050 | 395-GlyAspAsnSerValGluAlaAlaGluLysPheGlyAla-407 |
| SEQ. ID. NO. 15051 | 422-LeuArgHisAspLeuProGluArgAlaThrVal-432 |
| SEQ. ID. NO. 15052 | 434-ValLysGlySerArg-438 |
| SEQ. ID. NO. 15053 | 443-GluGluValValGluAlaLeuGluAspLys-452 |
| Hydrophilic Regions - Hopp-Woods | |
| SEQ. ID. NO. 15054 | 17-MetProSerGluSerLysProValSer-25 |
| SEQ. ID. NO. 15055 | 27-IleValThrAspSerArgAspIleArgAla-36 |
| SEQ. ID. NO. 15056 | 46-GlyArgPheAspAla-50 |
| SEQ. ID. NO. 15057 | 67-ValSerArgGluAspCysValAla-74 |
| SEQ. ID. NO. 15058 | 77-GlyAlaLeuLysValAspAspThrLeu-85 |
| SEQ. ID. NO. 15059 | 94-AlaTrpArgGluAsnVal-99 |
| SEQ. ID. NO. 15060 | 109-SerGlyGlyLysThrThrValLysGluMetLeu-119 |
| SEQ. ID. NO. 15061 | 123-LeuArgArgArgPheGlyAsp-129 |
| SEQ. ID. NO. 15062 | 151-LysLeuAsnGluLysHisArg-157 |
| SEQ. ID. NO. 15063 | 178-AlaLysProAspAla-182 |
| SEQ. ID. NO. 15064 | 199-GlyValGlyAspIleAlaLysAlaLysSerGluIle-210 |
| SEQ. ID. NO. 15065 | 223-ProGlnGluAspAlaAsn-228 |
| SEQ. ID. NO. 15066 | 247-AspSerGlyAspValHisAla-253 |
| SEQ. ID. NO. 15067 | 305-AspValAlaGluGlyLeuLys-311 |
| SEQ. ID. NO. 15068 | 316-IleLysGlyArgLeuAsnVal-322 |
| SEQ. ID. NO. 15069 | 335-ThrTyrAsnAlaAsnProAspSerMetLysAlaAlaVal-347 |
| SEQ. ID. NO. 15070 | 363-AspMetGlyGluLeuGlyGluAspGluAlaAla-373 |
| SEQ. ID. NO. 15071 | 381-AlaTyrAlaArgAspGlnGlyIle-388 |
| SEQ. ID. NO. 15072 | 397-AsnSerValGluAlaAlaGluLysPheGlyAla-407 |
| SEQ. ID. NO. 15073 | 422-LeuArgHisAspLeuProGluArgAlaThrVal-432 |
| SEQ. ID. NO. 15074 | 443-GluGluValValGluAlaLeuGluAspLys-452 |
| a084-2 | |
| AMPHI Regions - AMPHI | |
| SEQ. ID. NO. 15075 | 6-ArgIleLysAsnMetAspGlnThrLeuLysAsnThrLeuGly-19 |
| SEQ. ID. NO. 15076 | 21-CysAlaLeuLeuAla-25 |
| SEQ. ID. NO. 15077 | 48-AlaValGlyAlaLeuAla-53 |
| SEQ. ID. NO. 15078 | 65-PheProArgValSer-69 |
| SEQ. ID. NO. 15079 | 96-GlnIleValGlySerIleLeuGluSer-104 |
| SEQ. ID. NO. 15080 | 111-GluPheValGlyAsnLeuProGly-118 |

TABLE 1-continued

Antigenic Index - Jameson-Wolf
SEQ. ID. NO. 15081    1-MetLysGlnSerAlaArgIleLysAsnMetAspGlnThrLeuLysAsnThr-17
SEQ. ID. NO. 15082    40-TyrGluTyrGlyTyrArgTyrSer-47
SEQ. ID. NO. 15083    102-LeuGluSerAsnProAlaGluAlaArgGluPheValGly-114
SEQ. ID. NO. 15084    139-ValSerGlyGlyGly-143
Hydrophilic Regions - Hopp-Woods
SEQ. ID. NO. 15085    1-MetLysGlnSerAlaArgIleLysAsnMetAspGlnThrLeu-14
SEQ. ID. NO. 15086    105-AsnProAlaGluAlaArgGluPheVal-113
a085-2
AMPHI Regions - AMPHI
SEQ. ID. NO. 15087    41-GluArgValSerGlnIleGlyLysMetPheAspGlyLeu-53
SEQ. ID. NO. 15088    60-LeuLysAspAlaLeuSerAsnGlyPheAsp-69
SEQ. ID. NO. 15089    89-ArgAsnGlyGlyArgValLeuGlyAspIleGluLeuLeuAlaAspIle-104
SEQ. ID. NO. 15090    125-ThrSerLeuValGlyTyr-130
SEQ. ID. NO. 15091    141-IleAlaGlyAsnIleGlyAla-147
SEQ. ID. NO. 15092    174-GluAsnThrGluSerLeu-179
SEQ. ID. NO. 15093    193-HisLeuAspArgTyrAspAspLeuLeuAspTyr-203
SEQ. ID. NO. 15094    212-ArgGlyAspGlyValGln-217
SEQ. ID. NO. 15095    225-PheCysArgAlaMetLysArgAla-232
SEQ. ID. NO. 15096    275-HisAsnAlaThrAsnValMetAlaAlaValAlaLeuCysGluAla-289
SEQ. ID. NO. 15097    300-HisValLysThrPheGlnGlyLeuProHisArgValGluLysIleGly-315
SEQ. ID. NO. 15098    336-AlaAlaIleAlaGlyLeu-341
SEQ. ID. NO. 15099    353-GlyLysGlyGlnAspPheThr-359
SEQ. ID. NO. 15100    395-AspCysAlaThrLeuGluGluAlaValGlnLysAla-406
SEQ. ID. NO. 15101    424-SerPheAspMetPheLysGlyTyr-431
Antigenic Index - Jameson-Wolf
SEQ. ID. NO. 15102    4-GlnAsnLysLysIleLeu-9
SEQ. ID. NO. 15103    23-TyrLeuArgLysAsnGlyAlaGluValAlaAlaTyrAspAlaGluLeuLysProGluArgValSerGlnIleGlyLysMetPheAsp-51
SEQ. ID. NO. 15104    58-GlyArgLeuLysAspAlaLeuSerAsnGly-67
SEQ. ID. NO. 15105    74-SerProGlyIleSerGluArgGlnProAspIleGluAlaPheLysArgAsnGlyGlyArgValLeuGly-96
SEQ. ID. NO. 15106    104-IleValAsnArgArgGlyAspLysValIle-113
SEQ. ID. NO. 15107    116-ThrGlySerAsnGlyLysThrThr-123
SEQ. ID. NO. 15108    150-LeuGluAlaGluLeuGlnArgGluGlyLysLysAlaAsp-162
SEQ. ID. NO. 15109    169-SerSerPheGlnLeuGluAsnThrGluSerLeuArgProThrAla-183
SEQ. ID. NO. 15110    189-IleSerGluAspHisLeuAspArgTyrAspAspLeuLeu-201
SEQ. ID. NO. 15111    204-AlaHisThrLysAlaLysIlePheArgGlyAspGlyVal-216
SEQ. ID. NO. 15112    220-AsnAlaAspAspAlaPheCysArgAlaMetLysArgAlaGlyArgGluValLys-237
SEQ. ID. NO. 15113    247-PheTrpLeuGluArgGluThrGlyArgLeuLysGlnGlyAsnGluAspLeuIleAla-265
SEQ. ID. NO. 15114    291-GlyLeuProArgGluAlaLeu-297
SEQ. ID. NO. 15115    307-LeuProHisArgValGluLysIleGlyGluLysAsnGly-319
SEQ. ID. NO. 15116    322-PheIleAspAspSerLysGlyThrAsnVal-331
SEQ. ID. NO. 15117    351-GlyMetGlyLysGlyGlnAspPheThrProLeuArgAspAlaLeuAlaGlyLysAlaLys-370
SEQ. ID. NO. 15118    378-AspAlaProGlnIleArgArgAspLeuAspGlyCysAspLeuAsnMetThrAspCysAlaThrLeuGluGluAlaValGln-404
SEQ. ID. NO. 15119    431-TyrAlaHisArgSer-435
Hydrophilic Regions - Hopp-Woods
SEQ. ID. NO. 15120    4-GlnAsnLysLysIleLeu-9
SEQ. ID. NO. 15121    25-ArgLysAsnGlyAlaGlu-30
SEQ. ID. NO. 15122    32-AlaAlaTyrAspAlaGluLeuLysProGluArgValSerGln-45
SEQ. ID. NO. 15123    59-ArgLeuLysAspAlaLeu-64
SEQ. ID. NO. 15124    76-GlyIleSerGluArgGlnProAspIleGluAlaPheLysArgAsnGlyGly-92
SEQ. ID. NO. 15125    104-IleValAsnArgArgGlyAspLysValIle-113
SEQ. ID. NO. 15126    118-SerAsnGlyLysThrThr-123
SEQ. ID. NO. 15127    150-LeuGluAlaGluLeuGlnArgGluGlyLysLysAlaAsp-162
SEQ. ID. NO. 15128    174-GluAsnThrGluSerLeuArgPro-181
SEQ. ID. NO. 15129    189-IleSerGluAspHisLeuArgArgTyrAspAspLeuLeu-201
SEQ. ID. NO. 15130    204-AlaHisThrLysAlaLysIlePheArgGlyAspGly-215
SEQ. ID. NO. 15131    220-AsnAlaAspAspAlaPheCysArgAlaMetLysArgAlaGlyArgGluValLys-237
SEQ. ID. NO. 15132    247-PheTrpLeuGluArgGluThrGlyArgLeuLysGlnGlyAsnGluAspLeuIleAla-265
SEQ. ID. NO. 15133    291-GlyLeuProArgGluAlaLeu-297
SEQ. ID. NO. 15134    309-HisArgValGluLysIleGlyGluLysAsnGly-319
SEQ. ID. NO. 15135    324-AspAspSerLysGlyThrAsn-330
SEQ. ID. NO. 15136    353-GlyLysGlyGlnAsp-357
SEQ. ID. NO. 15137    359-ThrProLeuArgAspAlaLeuAlaGlyLysAlaLys-370
SEQ. ID. NO. 15138    380-ProGlnIleArgArgAspLeuAspGlyCysAsp-390
SEQ. ID. NO. 15139    397-AlaThrLeuGluGluAlaValGln-404
SEQ. ID. NO. 15140    431-TyrAlaHisArgSer-435
a086
AMPHI Regions - AMPHI
SEQ. ID. NO. 15141    55-MetArgThrTrpArgArgLeuValPro-63
SEQ. ID. NO. 15142    83-IleAsnGlyAlaThrArg-88
SEQ. ID. NO. 15143    99-ProThrGluLeuPheLysLeuAlaVal-107
SEQ. ID. NO. 15144    120-GluValLeuArgSerMetGluSerLeuGlyTrpGlnSerIleTrpArgGlyThrAlaAsn-139
SEQ. ID. NO. 15145    155-GluMetTyrArgArgPhe-160
SEQ. ID. NO. 15146    185-SerPheValValIle-189
SEQ. ID. NO. 15147    228-ArgValGlnArgValValAlaPheLeuAspProTrpLysAspProGln-243
SEQ. ID. NO. 15148    293-GlyPhePheGlyMetCys-298
SEQ. ID. NO. 15149    336-TrpIleGlyIleGlnSerPhe-342
Antigenic Index - Jameson-Wolf
SEQ. ID. NO. 15150    20-LeuAlaSerLysGluGlyGlyAsp-27
SEQ. ID. NO. 15151    55-MetArgThrTrpArgArg-60

TABLE 1-continued

| | |
|---|---|
| SEQ. ID. NO. 15152 | 79-AlaGlyArgGluIleAsnGlyAlaThr-87 |
| SEQ. ID. NO. 15153 | 115-PheThrArgArgGluGluValLeuArgSerMetGlu-126 |
| SEQ. ID. NO. 15154 | 134-TrpArgGlyThrAla-138 |
| SEQ. ID. NO. 15155 | 144-AlaThrAsnProGlnAlaArgArgGluThrLeuGluMet-156 |
| SEQ. ID. NO. 15156 | 225-AlaProTyrArgVal-229 |
| SEQ. ID. NO. 15157 | 236-LeuAspProTrpLysAspProGlnGlyAla-245 |
| SEQ. ID. NO. 15158 | 265-GlyLeuGlyAlaSerLeuSerLysArgGlyPheLeu-276 |
| SEQ. ID. NO. 15159 | 313-SerIleGlyLysGlnSerArgAspLeuGly-322 |
| SEQ. ID. NO. 15160 | 352-LeuProThrLysGlyLeu-357 |
| SEQ. ID. NO. 15161 | 382-IleAspTyrGluAsnArgArgLysMetArgGlyTyrArgValGlu-396 |
| Hydrophilic Regions - Hopp-Woods | |
| SEQ. ID. NO. 15162 | 21-AlaSerLysGluGlyGlyAsp-27 |
| SEQ. ID. NO. 15163 | 79-AlaGlyArgGluIleAsnGly-85 |
| SEQ. ID. NO. 15164 | 115-PheThrArgArgGluGluValLeuArgSerMetGlu-126 |
| SEQ. ID. NO. 15165 | 147-ProGlnAlaArgArgGluThrLeuGluMet-156 |
| SEQ. ID. NO. 15166 | 238-ProTrpLysAspProGlnGly-244 |
| SEQ. ID. NO. 15167 | 270-LeuSerLysArgGlyPheLeu-276 |
| SEQ. ID. NO. 15168 | 316-LysGlnSerArgAspLeu-321 |
| SEQ. ID. NO. 15169 | 382-IleAspTyrGluAsnArgArgLysMetArgGlyTyrArgValGlu-396 |
| a087 | |
| AMPHI Regions - AMPHI | |
| SEQ. ID. NO. 15170 | 23-ValAlaAspSerLeuArg-28 |
| SEQ. ID. NO. 15171 | 80-GlnThrValArgGluAlaGlnGlnIle-88 |
| SEQ. ID. NO. 15172 | 99-GlyPheGlyGlyPheValThrPheProGlyGlyLeuAlaAlaLysLeuLeu-115 |
| SEQ. ID. NO. 15173 | 129-GlyLeuSerAsnArgHisLeuSerArgTrpAlaLysArgValLeuTyrAlaPheProLys-148 |
| SEQ. ID. NO. 15174 | 157-ValGlyAsnProValArg-162 |
| SEQ. ID. NO. 15175 | 192-GlyAlaAspValLeuAsnLysThrVal-200 |
| SEQ. ID. NO. 15176 | 239-GluCysValGluPheIleThrAspMetValSerAlaTyr-251 |
| SEQ. ID. NO. 15177 | 313-GluLysLeuAlaGluIleLeuGly-320 |
| SEQ. ID. NO. 15178 | 330-TrpAlaGluAsnAla-334 |
| Antigenic Index - Jameson-Wolf | |
| SEQ. ID. NO. 15179 | 25-AspSerLeuArgAlaArgGly-31 |
| SEQ. ID. NO. 15180 | 37-LeuGlySerLysAspSerMetGluGluArgIleValPro-49 |
| SEQ. ID. NO. 15181 | 61-LysGlyValArgGlyAsnGlyIleLysArgLysLeu-72 |
| SEQ. ID. NO. 15182 | 81-ThrValArgGluAlaGlnGlnIleIleArgLysHisArgVal-94 |
| SEQ. ID. NO. 15183 | 130-LeuSerAsnArgHisLeuSerArgTrpAlaLys-140 |
| SEQ. ID. NO. 15184 | 150-PheSerHisGluGlyGlyLeu-156 |
| SEQ. ID. NO. 15185 | 159-AsnProValArgAlaAspIleSer-166 |
| SEQ. ID. NO. 15186 | 171-ProAlaGluArgPheGlnGlyArgGluGlyArgLeu-182 |
| SEQ. ID. NO. 15187 | 195-ValLeuAsnLysThrVal-200 |
| SEQ. ID. NO. 15188 | 207-LeuProAspAsnAlaArgProGlnMetTyrHisGlnSerGlyArgGlyLysLeuGly-225 |
| SEQ. ID. NO. 15189 | 229-AlaAspTyrAspAla-233 |
| SEQ. ID. NO. 15190 | 249-SerAlaTyrArgAspAlaAsp-255 |
| SEQ. ID. NO. 15191 | 284-AlaValAspAspHisGlnThrAla-291 |
| SEQ. ID. NO. 15192 | 309-GlnLeuThrAlaGluLysLeuAlaGlu-317 |
| SEQ. ID. NO. 15193 | 321-GlyLeuAsnArgGluLysCysLeuLys-329 |
| SEQ. ID. NO. 15194 | 331-AlaGluAsnAlaArgThr-336 |
| SEQ. ID. NO. 15195 | 341-HisSerAlaAspAspValAlaGlu-348 |
| Hydrophilic Regions - Hopp-Woods | |
| SEQ. ID. NO. 15196 | 25-AspSerLeuArgAlaArgGly-31 |
| SEQ. ID. NO. 15197 | 39-SerLysAspSerMetGluGluArgIleValPro-49 |
| SEQ. ID. NO. 15198 | 66-AsnGlyIleLysArgLysLeu-72 |
| SEQ. ID. NO. 15199 | 81-ThrValArgGluAlaGlnGlnIleIleArgLysHisArgVal-94 |
| SEQ. ID. NO. 15200 | 134-HisLeuSerArgTrpAlaLys-140 |
| SEQ. ID. NO. 15201 | 161-ValArgAlaAspIle-165 |
| SEQ. ID. NO. 15202 | 171-ProAlaGluArgPheGlnGlyArgGluGlyArgLeu-182 |
| SEQ. ID. NO. 15203 | 219-SerGlyArgGlyLysLeu-224 |
| SEQ. ID. NO. 15204 | 249-SerAlaTyrArgAspAlaAsp-255 |
| SEQ. ID. NO. 15205 | 284-AlaValAspAspHisGlnThrAla-291 |
| SEQ. ID. NO. 15206 | 310-LeuThrAlaGluLysLeuAlaGlu-317 |
| SEQ. ID. NO. 15207 | 322-LeuAsnArgGluLysCysLeuLys-329 |
| SEQ. ID. NO. 15208 | 331-AlaGluAsnAlaArg-335 |
| SEQ. ID. NO. 15209 | 341-HisSerAlaAspAspValAlaGlu-348 |
| a088-2 | |
| AMPHI Regions - AMPHI | |
| SEQ. ID. NO. 15210 | 7-HisPheSerAsnTrpLeuThrGlyLeuAsnIlePheGlnTyrThrThr-22 |
| SEQ. ID. NO. 15211 | 24-ArgAlaValMetAlaAlaLeu-30 |
| SEQ. ID. NO. 15212 | 43-ThrIleArgArgLeuThrAlaLeuLysCysGlyGln-54 |
| SEQ. ID. NO. 15213 | 88-LeuTrpGlyAsnTrpAlaAsn-94 |
| SEQ. ID. NO. 15214 | 111-GlyPheTyrAspAspTrpArgLysValValTyr-121 |
| SEQ. ID. NO. 15215 | 140-AlaIleIleAlaGlyLeuAlaLeu-147 |
| SEQ. ID. NO. 15216 | 175-GlyPheLeuValLeuSerTyrLeuThrIle-184 |
| SEQ. ID. NO. 15217 | 187-ThrSerAsnAlaValAsnLeuThrAspGlyLeuAspGlyLeuAlaThr-202 |
| SEQ. ID. NO. 15218 | 221-HisSerGlnPheAlaGlnTyrLeuGlnLeuProTyr-232 |
| SEQ. ID. NO. 15219 | 245-AlaMetCysGlyAlaCysLeuGlyPhe-253 |
| Antigenic Index - Jameson-Wolf | |
| SEQ. ID. NO. 15220 | 48-ThrAlaLeuLysCysGlyGlnAlaValArgThrAspGlyProGln-62 |
| SEQ. ID. NO. 15221 | 66-ValLysAsnGlyThrProThrMet-73 |
| SEQ. ID. NO. 15222 | 114-AspAspTrpArgLysValValTyrLysAspProAsnGlyValSerAlaLysPhe-131 |
| SEQ. ID. NO. 15223 | 193-LeuThrAspGlyLeuAsp-198 |

TABLE 1-continued

| | |
|---|---|
| SEQ. ID. NO. 15224 | 312-LysLysThrLysLysArgIle-318 |
| SEQ. ID. NO. 15225 | 328-TyrGluGlnLysGlyTrpLysGluThrGlnVal-338 |

Hydrophilic Regions - Hopp-Woods

| | |
|---|---|
| SEQ. ID. NO. 15226 | 56-ValArgThrAspGlyProGln-62 |
| SEQ. ID. NO. 15227 | 114-AspAspTrpArgLysValValTyrLysAspProAsnGlyVal-127 |
| SEQ. ID. NO. 15228 | 312-LysLysThrLysLysArgIle-318 |
| SEQ. ID. NO. 15229 | 331-LysGlyTrpLysGlu-335 | a089
AMPHI Regions - AMPHI

| | |
|---|---|
| SEQ. ID. NO. 15230 | 44-CysGlyArgProXxxLysVal-50 |
| SEQ. ID. NO. 15231 | 73-ThrLeuValAlaLeuCysLysProCysSerGlyIle-84 |
| SEQ. ID. NO. 15232 | 118-SerArgProAlaArgPhe-123 |

Antigenic Index - Jameson-Wolf

| | |
|---|---|
| SEQ. ID. NO. 15233 | 1-MetProProLysIleThrLysSerGlyPhe-10 |
| SEQ. ID. NO. 15234 | 40-PheSerThrArgCysGlyArgProXxxLys-49 |
| SEQ. ID. NO. 15235 | 54-SerSerAsnAlaSerArgGlyLysProThrAlaSerHisLysAla-68 |
| SEQ. ID. NO. 15236 | 80-ProCysSerGlyIle-84 |
| SEQ. ID. NO. 15237 | 95-CysPheArgArgProValSerArgSerAsnGlnLysSerAlaSerTyrSerAsnGlu AsnHisPheThrSerArgProAlaArgPheIleAlaArgGlnAsnAlaSerSerAlaPheLysThrCysThrProSerProArgLysIleLeu-144 |

Hydrophilic Regions - Hopp-Woods

| | |
|---|---|
| SEQ. ID. NO. 15238 | 43-ArgCysGlyArgProXxxLys-49 |
| SEQ. ID. NO. 15239 | 56-AsnAlaSerArgGlyLysProThrAlaSerHisLysAla-68 |
| SEQ. ID. NO. 15240 | 95-CysPheArgArgProValSerArgSerAsnGlnLysSerAlaSerTyrSerAsn-112 |
| SEQ. ID. NO. 15241 | 119-ArgProAlaArgPheIleAla-125 |
| SEQ. ID. NO. 15242 | 137-ThrProSerProArgLysIle-143 | a090-1
AMPHI Regions - AMPHI

| | |
|---|---|
| SEQ. ID. NO. 15243 | 10-SerGlnSerLeuLysArgProAspLysHisPheArg-21 |
| SEQ. ID. NO. 15244 | 142-AspPhePheHisAlaValArgGlnAlaLeuLysGlyPheAspValPheGluGlnCysPheAla-162 |
| SEQ. ID. NO. 15245 | 164-GlnThrAspGlyPhe-168 |
| SEQ. ID. NO. 15246 | 177-ValSerGlyValValGlnAlaLeuGlnArg-186 |
| SEQ. ID. NO. 15247 | 226-LeuHisArgThrThrGluArgIleValArgIleGlnAsnLeuHisThrVal-242 |
| SEQ. ID. NO. 15248 | 253-ValValGluGlnVal-257 |
| SEQ. ID. NO. 15249 | 268-ValGlnHisCysArgArgSerArg-275 |
| SEQ. ID. NO. 15250 | 381-GlyAlaGluCysGlnAsnIleGluThrValGlyGluArg-393 |
| SEQ. ID. NO. 15251 | 404-ProValLysHisLeuThrAspLeuArg-412 |
| SEQ. ID. NO. 15252 | 425-AsnLeuArgAlaValPheAlaGlnValGlyAsnHisGlyAsnThrArgAlaAlaLysSer-444 |

Antigenic Index - Jameson-Wolf

| | |
|---|---|
| SEQ. ID. NO. 15253 | 9-ValSerGlnSerLeuLysArgProAspLysHisPheArg-21 |
| SEQ. ID. NO. 15254 | 29-HisIleGluThrArgAlaGlyGlyAlaGluGlnHisAspIleAla-43 |
| SEQ. ID. NO. 15255 | 56-PheGlnSerGlyAla-60 |
| SEQ. ID. NO. 15256 | 73-AlaAspLeuArgArgIleAspThrAspGlnGluHis-84 |
| SEQ. ID. NO. 15257 | 89-AlaGlyLysArgValAlaGlnGlyArgGluVal-99 |
| SEQ. ID. NO. 15258 | 107-XxxAsnHisGluGluArgIleLeuGlnThrGlyAsnArgGlyGlyGlyArgThrAspValArg-127 |
| SEQ. ID. NO. 15259 | 149-GlnAlaLeuLysGlyPheAsp-155 |
| SEQ. ID. NO. 15260 | 161-PheAlaArgGlnThrAspGlyPheAlaGlnGlyAsnGlySerHisHisValSer-178 |
| SEQ. ID. NO. 15261 | 187-AsnIleLeuArgGlyAsnGln-193 |
| SEQ. ID. NO. 15262 | 215-GlnArgLysProPheHisLeuAla-222 |
| SEQ. ID. NO. 15263 | 228-ArgThrThrGluArgIleValArg-235 |
| SEQ. ID. NO. 15264 | 269-GlnHisCysArgArgSerArgAlaGln-277 |
| SEQ. ID. NO. 15265 | 285-GluThrGlyLysLeuGlnHis-291 |
| SEQ. ID. NO. 15266 | 305-LeuGlnAsnArgArgAlaAspIleAlaArgAspAsnGlyIle-318 |
| SEQ. ID. NO. 15267 | 320-ProThrLeuAspAlaGluIleAlaAspGlnAlaArgTyrArgGly-334 |
| SEQ. ID. NO. 15268 | 339-AlaGlyAsnArgAsnHis-344 |
| SEQ. ID. NO. 15269 | 353-ValArgGlnGlnPhe-357 |
| SEQ. ID. NO. 15270 | 369-LysGlyLeuAspIle-373 |
| SEQ. ID. NO. 15271 | 380-AlaGlyAlaGluCysGlnAsn-386 |
| SEQ. ID. NO. 15272 | 398-AlaArgValLysHisGlnProVal-405 |
| SEQ. ID. NO. 15273 | 407-HisLeuThrAspLeuArgHis-413 |
| SEQ. ID. NO. 15274 | 421-IleIleArgSerAsnLeuArg-427 |
| SEQ. ID. NO. 15275 | 434-GlyAsnHisGlyAsnThrArgAlaAlaLysSerGlyAspGluAspPhePhe-450 |

Hydrophilic Regions - Hopp-Woods

| | |
|---|---|
| SEQ. ID. NO. 15276 | 11-GlnSerLeuLysArgProAspLysHisPheArg-21 |
| SEQ. ID. NO. 15277 | 29-HisIleGluThrArgAlaGlyGlyAlaGluGlnHisAspIleAla-43 |
| SEQ. ID. NO. 15278 | 73-AlaAspLeuArgArgIleAspThrAspGlnGluHis-84 |
| SEQ. ID. NO. 15279 | 89-AlaGlyLysArgValAlaGlnGlyArgGluVal-99 |
| SEQ. ID. NO. 15280 | 107-XxxAsnHisGluGluArgIleLeu-114 |
| SEQ. ID. NO. 15281 | 117-GlyAsnArgGlyGlyGlyArgThrAspValArg-127 |
| SEQ. ID. NO. 15282 | 228-ArgThrThrGluArgIleValArg-235 |
| SEQ. ID. NO. 15283 | 269-GlnHisCysArgArgSerArgAla-276 |
| SEQ. ID. NO. 15284 | 285-GluThrGlyLysLeuGln-290 |
| SEQ. ID. NO. 15285 | 305-LeuGlnAsnArgArgAlaAspIleAlaArgAspAsnGlyIle-318 |
| SEQ. ID. NO. 15286 | 322-LeuAspAlaGluIleAlaAspGlnAlaArgTyrArg-333 |
| SEQ. ID. NO. 15287 | 369-LysGlyLeuAspIle-373 |
| SEQ. ID. NO. 15288 | 380-AlaGlyAlaGluCysGlnAsn-386 |
| SEQ. ID. NO. 15289 | 398-AlaArgValLysHisGlnPro-404 |
| SEQ. ID. NO. 15290 | 409-ThrAspLeuArgHis-413 |
| SEQ. ID. NO. 15291 | 421-IleIleArgSerAsnLeu-426 |
| SEQ. ID. NO. 15292 | 437-GlyAsnThrArgAlaAlaLysSerGlyAspGluAspPhePhe-450 |

TABLE 1-continued a091
AMPHI Regions - AMPHI
SEQ. ID. NO. 15293    39-ProLeuSerAspGlyIleAlaSerCys-47
SEQ. ID. NO. 15294    49-IleThrArgPheGlnAlaLeuVal-56
SEQ. ID. NO. 15295    61-ValLeuValSerValLeuThrSerLeuAlaLys-71
Antigenic Index - Jameson-Wolf
SEQ. ID. NO. 15296    5-ValProProSerProAlaThr-11
SEQ. ID. NO. 15297    38-LysProLeuSerAspGlyIleAla-45
a092
AMPHI Regions - AMPHI
SEQ. ID. NO. 15298    55-GlyMetSerGlyIleAlaGluValLeuHis-64
SEQ. ID. NO. 15299    76-AlaArgAsnAlaAlaThrGluHisLeu-84
SEQ. ID. NO. 15300    95-HisThrAlaGluHisValAsnGly-102
SEQ. ID. NO. 15301    120-ValAlaAlaLeuGlu-124
SEQ. ID. NO. 15302    137-AlaGluLeuMetArgPheArgAsp-144
SEQ. ID. NO. 15303    209-LeuThrProIleMetSerValValThrAsnIleAsp-220
SEQ. ID. NO. 15304    226-ThrTyrGlyHisSerValGluLysLeuHisGlnAlaPheIleAspPheIleHisArg-244
SEQ. ID. NO. 15305    259-HisValArgAlaIleLeuProLysValSerLysProTyr-271
SEQ. ID. NO. 15306    273-ThrTyrGlyLeuAspAspThrAla-280
SEQ. ID. NO. 15307    321-AsnValLeuAsnAlaLeuAlaAlaIle-329
SEQ. ID. NO. 15308    339-ValGluAlaIleGlnLysGly-345
SEQ. ID. NO. 15309    353-GlyArgArgPheGlnLysTyrGlyAspIleLys-363
SEQ. ID. NO. 15310    407-ArgTyrThrArgThrArgAspLeuPheGluAspPheThrLysValLeuAsnThrValAspAlaLeu-428
SEQ. ID. NO. 15311    449-LeuAlaArgAlaIleArgValLeuGlyLysLeu-459
SEQ. ID. NO. 15312    464-CysGluAsnValAlaAspLeuProGluMetLeuLeuAsn-476
Antigenic Index - Jameson-Wolf
SEQ. ID. NO. 15313    14-LeuTrpArgAlaAsnGlyGlnProPheLys-23
SEQ. ID. NO. 15314    25-ThrProLeuArgIleGluAsnProProGluArgAsnIleMetMetLysAsnArgVal-43
SEQ. ID. NO. 15315    70-ValSerGlySerAspGlnAlaArgAsnAlaAla-80
SEQ. ID. NO. 15316    111-AlaValLysLysGluAsnProGluVal-119
SEQ. ID. NO. 15317    140-MetArgPheArgAspGlyIle-146
SEQ. ID. NO. 15318    150-GlyThrHisGlyLysThrThrThr-157
SEQ. ID. NO. 15319    184-GlyThrAsnAlaArgLeuGlyLysGlyGluTyr-194
SEQ. ID. NO. 15320    198-GluAlaAspGluSerAspAla-204
SEQ. ID. NO. 15321    218-AsnIleAspGluAspHisMetAspThrTyrGly-228
SEQ. ID. NO. 15322    230-SerValGluLysLeuHis-235
SEQ. ID. NO. 15323    255-IleAspSerGluHisVal-260
SEQ. ID. NO. 15324    263-IleLeuProLysValSerLysProTyrAla-272
SEQ. ID. NO. 15325    275-GlyLeuAspAspThrAlaAsp-281
SEQ. ID. NO. 15326    286-AspIleGluAsnValGlyAla-292
SEQ. ID. NO. 15327    302-MetLysGlyHisGluGlnGlySerPhe-310
SEQ. ID. NO. 15328    351-GlyValGlyArgArgPheGlnLysTyrGlyAspIleLysLeuProAsnGlyGly-368
SEQ. ID. NO. 15329    374-AspAspTyrGlyHisHisPro-380
SEQ. ID. NO. 15330    393-AlaTyrProGluLysArgLeu-399
SEQ. ID. NO. 15331    404-GlnProHisArgTyrThrArgThrArgAspLeuPheGluAspPheThrLys-420
SEQ. ID. NO. 15332    435-AlaAlaGlyGluGluProIleAlaAlaAlaAlaAspSerArgAlaLeuAlaArg-451
SEQ. ID. NO. 15333    466-AsnValAlaAspLeuPro-471
SEQ. ID. NO. 15334    478-LeuGlnAspGlyAspIle-483
SEQ. ID. NO. 15335    488-GlyAlaGlySerIleAsn-493
Hydrophilic Regions - Hopp-Woods
SEQ. ID. NO. 15336    26-ProLeuArgIleGluAsnProProGluArgAsnIleMetMetLysAsnArgVal-43
SEQ. ID. NO. 15337    71-SerGlySerAspGlnAlaArgAsnAlaAla-80
SEQ. ID. NO. 15338    111-AlaValLysLysGluAsnProGlu-118
SEQ. ID. NO. 15339    140-MetArgPheArgAsp-144
SEQ. ID. NO. 15340    152-HisGlyLysThrThr-156
SEQ. ID. NO. 15341    187-AlaArgLeuGlyLysGlyGlu-193
SEQ. ID. NO. 15342    198-GluAlaAspGluSerAspAla-204
SEQ. ID. NO. 15343    218-AsnIleAspGluAspHisMetAsp-225
SEQ. ID. NO. 15344    230-SerValGluLysLeuHis-235
SEQ. ID. NO. 15345    256-AspSerGluHisVal-260
SEQ. ID. NO. 15346    275-GlyLeuAspAspThrAlaAsp-281
SEQ. ID. NO. 15347    303-LysGlyHisGluGlnGlySer-309
SEQ. ID. NO. 15348    351-GlyValGlyArgArgPheGlnLys-358
SEQ. ID. NO. 15349    360-GlyAspIleLysLeu-364
SEQ. ID. NO. 15350    393-AlaTyrProGluLysArgLeu-399
SEQ. ID. NO. 15351    407-ArgTyrThrArgThrArgAspLeuPheGluAspPheThrLys-420
SEQ. ID. NO. 15352    435-AlaAlaGlyGluGluProIleAlaAlaAlaAlaAspSerArgAlaLeuAlaArg-451
SEQ. ID. NO. 15353    466-AsnValAlaAspLeuPro-471
SEQ. ID. NO. 15354    479-GlnAspGlyAspIle-483
a093-2
AMPHI Regions - AMPHI
SEQ. ID. NO. 15355    26-ThrAlaIleLeuAsn-30
SEQ. ID. NO. 15356    59-ThrAlaPheAsnIleLeuHisGly-66
SEQ. ID. NO. 15357    159-LysSerValTyrGluGluLeuLysHisPhe-168
SEQ. ID. NO. 15358    196-IleHisIleIleProAlaThrGluPhe-204
SEQ. ID. NO. 15359    254-PheLeuLysAspThr-258
SEQ. ID. NO. 15360    267-IleAsnThrLeuProGlyMetThrGly-275
Antigenic Index - Jameson-Wolf
SEQ. ID. NO. 15361    12-GlyGlyPheSerSerGluArgGluIleSerLeuAspSerGlyThr-26
SEQ. ID. NO. 15362    32-LeuLysSerLysGlyIleAsp-38

TABLE 1-continued

| | |
|---|---|
| SEQ. ID. NO. 15363 | 41-AlaPheAspProLysGluThrProLeuSerGluLeuLysAlaGlnGly-56 |
| SEQ. ID. NO. 15364 | 66-GlyThrTyrGlyGluAspGlyAlaVal-74 |
| SEQ. ID. NO. 15365 | 96-GlyMetAspLysTyrArgCys-102 |
| SEQ. ID. NO. 15366 | 120-HisAspAspThrAspPheAspAlaValGluGluLysLeuGly-133 |
| SEQ. ID. NO. 15367 | 140-ProAlaAlaGluGlySerSer-146 |
| SEQ. ID. NO. 15368 | 151-LysValLysGlyLysGlyArgLeuLysSerValTyrGluGluLeuLysHisPheGln-169 |
| SEQ. ID. NO. 15369 | 176-ArgPheIleGlyGlyGlyGluTyrSer-184 |
| SEQ. ID. NO. 15370 | 189-AsnGlyLysGlyLeuPro-194 |
| SEQ. ID. NO. 15371 | 203-GluPheTyrAspTyrGluAlaLysTyrAsnArgAsnAspThr-216 |
| SEQ. ID. NO. 15372 | 218-TyrGlnCysProSerGluAspLeuThrGluAlaGluGluSerLeuMetArg-234 |
| SEQ. ID. NO. 15373 | 245-GlyAlaGluGlyCysVal-250 |
| SEQ. ID. NO. 15374 | 253-AspPheLeuLysAspThrAspGly-260 |
| SEQ. ID. NO. 15375 | 269-ThrLeuProGlyMetThr-274 |
| Hydrophilic Regions - Hopp-Woods | |
| SEQ. ID. NO. 15376 | 15-SerSerGluArgGluIleSerLeu-22 |
| SEQ. ID. NO. 15377 | 32-LeuLysSerLysGlyIleAsp-38 |
| SEQ. ID. NO. 15378 | 41-AlaPheAspProLysGluThrProLeuSerGluLeuLysAla-54 |
| SEQ. ID. NO. 15379 | 68-TyrGlyGluAspGlyAlaVal-74 |
| SEQ. ID. NO. 15380 | 96-GlyMetAspLysTyrArgCys-102 |
| SEQ. ID. NO. 15381 | 120-HisAspAspThrAspPheAspAlaValGluGluLysLeuGly-133 |
| SEQ. ID. NO. 15382 | 140-ProAlaAlaGluGlySerSer-146 |
| SEQ. ID. NO. 15383 | 151-LysValLysGlyLysGlyArgLeuLysSerValTyrGluGluLeuLysHisPheGln-169 |
| SEQ. ID. NO. 15384 | 205-TyrAspTyrGluAlaLysTyrAsnArgAsnAspThr-216 |
| SEQ. ID. NO. 15385 | 221-ProSerGluAspLeuThrGluAlaGluGluSerLeuMetArg-234 |
| SEQ. ID. NO. 15386 | 253-AspPheLeuLysAspThrAspGly-260 |
| a094 | |
| AMPHI Regions - AMPHI | |
| SEQ. ID. NO. 15387 | 17-LeuProProIleThrLysValGlySer-25 |
| SEQ. ID. NO. 15388 | 80-PheSerPheLeuThrAlaVal-86 |
| Antigenic Index - Jameson-Wolf | |
| SEQ. ID. NO. 15389 | 3-SerProLeuProLysArgAlaLeu-10 |
| SEQ. ID. NO. 15390 | 24-GlySerSerProAlaAlaProArgMetGluAla-34 |
| SEQ. ID. NO. 15391 | 50-MetProSerArgLysArgIleAsnSerAlaAsnIleArgAlaArgGlyIleThr-67 |
| Hydrophilic Regions - Hopp-Woods | |
| SEQ. ID. NO. 15392 | 5-LeuProLysArgAlaLeu-10 |
| SEQ. ID. NO. 15393 | 28-AlaAlaProArgMetGluAla-34 |
| SEQ. ID. NO. 15394 | 51-ProSerArgLysArgIleAsn-57 |
| SEQ. ID. NO. 15395 | 60-AsnIleArgAlaArgGly-65 |
| a095-2 | |
| AMPHI Regions - AMPHI | |
| SEQ. ID. NO. 15396 | 9-CysAlaSerAsnLeuPheArgGlnPheGlnGlnArgGlyGlyAspAlaValAsp-26 |
| SEQ. ID. NO. 15397 | 38-ValLeuGlnAsnValGlnGlnHisPheGlyGlnIleGlyAsnValPheAlaVal-55 |
| SEQ. ID. NO. 15398 | 86-PheGlyGlnHisGlnArgValAsnGlyIleGluAspPheGlyLysValPheLysGlnIleAlaArg-107 |
| SEQ. ID. NO. 15399 | 132-GlyArgArgHisPheAspGlyValValSer-141 |
| SEQ. ID. NO. 15400 | 174-PheLeuAspArgPheAsnArgCysAlaAspPheGlnArgHisAlaAspGlyCysGlnCysValGlnHisVal-197 |
| SEQ. ID. NO. 15401 | 204-GlnHisAspPheLys-208 |
| SEQ. ID. NO. 15402 | 236-AspValGlyGlyIleValGlnThrValSerSerIle-247 |
| SEQ. ID. NO. 15403 | 274-ThrValAspGluIleAspLysArgLeuMetGlnLeuLeuAsnThrVal-289 |
| SEQ. ID. NO. 15404 | 313-GlyCysIleArgLeuValGly-319 |
| SEQ. ID. NO. 15405 | 370-AsnGlyAspAlaValThrGluAlaHisGlnLeuArgGlnHisGlnGlyAla-386 |
| SEQ. ID. NO. 15406 | 417-ValAsnValPheCysGly-422 |
| SEQ. ID. NO. 15407 | 435-MetLeuGlySerGlyIleSerArgLeuIleArgThrGly-447 |
| SEQ. ID. NO. 15408 | 451-ThrGlnIleValGlnAspPheGlyAspThrAlaHisAla-463 |
| Antigenic Index - Jameson-Wolf | |
| SEQ. ID. NO. 15409 | 6-SerGlyGlyCysAlaSerAsnLeu-13 |
| SEQ. ID. NO. 15410 | 17-PheGlnGlnArgGlyGlyAspAlaValAspAlaSerArgThrHisIle-32 |
| SEQ. ID. NO. 15411 | 62-GlnHisAlaAspGlyAlaGlyLysSerAlaGlyIleSerGlyGlyAsnArgLeuPhe-80 |
| SEQ. ID. NO. 15412 | 88-GlnHisGlnArgValAsnGlyIleGluAspPheGlyLys-100 |
| SEQ. ID. NO. 15413 | 112ValArgLeuGluGlyGluTyr-118 |
| SEQ. ID. NO. 15414 | 126-AlaAlaCysGlyGlyLysGlyArgArgHisPheAspGly-138 |
| SEQ. ID. NO. 15415 | 144-ValHisGlnGluArgGlySerThr-151 |
| SEQ. ID. NO. 15416 | 163-AlaAlaAlaAspThrPheLysAlaGluGlnAlaPhe-174 |
| SEQ. ID. NO. 15417 | 176-AspArgPheAsnArgCysAlaAspPheGlnArgHisAlaAspGlyCysGln-192 |
| SEQ. ID. NO. 15418 | 205-HisAspPheLysArg-209 |
| SEQ. ID. NO. 15419 | 253-GlyGlnAsnArgAlaAspVal-259 |
| SEQ. ID. NO. 15420 | 263-AsnThrGlnLysGlyPheAlaVal-270 |
| SEQ. ID. NO. 15421 | 273-HisThrValAspGluIleAspLysArgLeu-282 |
| SEQ. ID. NO. 15422 | 300-IleGlyAsnAspGlyHisAsnArgCysGlnValGlnLysGlyCys-314 |
| SEQ. ID. NO. 15423 | 339-PheAlaAlaAspAsnGluSerArgValLysSerCysArgAlaGluAsp GlyGlyGlyGlnAlaGlyGlyArgGlyPheAlaValArgAlaGlyAsnGlyAspAlaValThr-375 |
| SEQ. ID. NO. 15424 | 378-HisGlnLeuArgGlnHisGlnGlyAlaArgAsnAsnGlyAsn-391 |
| SEQ. ID. NO. 15425 | 394-LeuGlnArgSerAspAsnPheGly-401 |
| SEQ. ID. NO. 15426 | 405-PheAspGlyGlyArgGlyAsnAspIleArgThr-416 |
| SEQ. ID. NO. 15427 | 442-ArgLeuIleArgThrGlyAsnPheLysThr-451 |
| SEQ. ID. NO. 15428 | 455-GlnAspPheGlyAspThrAlaHisAlaAspAlaAlaAspThrAspLysMetAspVal-473 |
| Hydrophilic Regions - Hopp-Woods | |
| SEQ. ID. NO. 15429 | 17-PheGlnGlnArgGlyGlyAspAlaValAspAlaSerArgThrHisIle-32 |
| SEQ. ID. NO. 15430 | 64-AlaAspGlyAlaGlyLysSerAlaGly-72 |
| SEQ. ID. NO. 15431 | 93-AsnGlyIleGluAspPheGlyLys-100 |
| SEQ. ID. NO. 15432 | 112-ValArgLeuGluGlyGluTyr-118 |

TABLE 1-continued

| | |
|---|---|
| SEQ. ID. NO. 15433 | 128-CysGlyGlyLysGlyArgArgHisPhe-136 |
| SEQ. ID. NO. 15434 | 145-HisGlnGluArgGlySer-150 |
| SEQ. ID. NO. 15435 | 163-AlaAlaAlaAspThrPheLysAlaGluGlnAlaPhe-174 |
| SEQ. ID. NO. 15436 | 182-AlaAspPheGlnArgHisAlaAspGly-190 |
| SEQ. ID. NO. 15437 | 205-HisAspPheLysArg-209 |
| SEQ. ID. NO. 15438 | 273-HisThrValAspGluIleAspLysArgLeu-282 |
| SEQ. ID. NO. 15439 | 300-IleGlyAsnAspGlyHisAsnArgCysGlnVal-310 |
| SEQ. ID. NO. 15440 | 339-PheAlaAlaAspAsnGluSerArgValLysSerCysArgAlaGluAspGlyGlyGly-357 |
| SEQ. ID. NO. 15441 | 368-AlaGlyAsnGlyAspAlaValThr-375 |
| SEQ. ID. NO. 15442 | 378-HisGlnLeuArgGlnHisGlnGlyAlaArgAsnAsnGly-390 |
| SEQ. ID. NO. 15443 | 395-GlnArgSerAspAsn-399 |
| SEQ. ID. NO. 15444 | 407-GlyGlyArgGlyAsnAspAspIleArgThr-416 |
| SEQ. ID. NO. 15445 | 461-AlaHisAlaAspAlaAlaAspThrAspLysMetAspVal-473 | a096-2
AMPHI Regions - AMPHI
| | |
|---|---|
| SEQ. ID. NO. 15446 | 19-GlyIlePheGluGluIleAspAlaHis-27 |
| SEQ. ID. NO. 15447 | 37-AlaAlaAsnArgGln-41 |
| SEQ. ID. NO. 15448 | 61-GlyValValAlaVal-65 |
| SEQ. ID. NO. 15449 | 112-GlnPhePheValAsnAlaPheGln-119 |
| SEQ. ID. NO. 15450 | 129-AlaTyrAlaAlaAlaPheGlyArg-136 |
| SEQ. ID. NO. 15451 | 172-AsnGlnPheAlaAla-176 |
| SEQ. ID. NO. 15452 | 187-AspThrAlaAlaGlyIleGlyAsnAlaGln-196 |
| SEQ. ID. NO. 15453 | 228-GlnTrpGlyPheLeu-232 |

Antigenic Index - Jameson-Wolf
| | |
|---|---|
| SEQ. ID. NO. 15454 | 4-HisThrGlyGlnGly-8 |
| SEQ. ID. NO. 15455 | 22-GluGluIleAspAla-26 |
| SEQ. ID. NO. 15456 | 30-PheArgThrAspCysLeuArgAlaAlaAsn-39 |
| SEQ. ID. NO. 15457 | 73-LysLeuGlyArgGlyAspAspValTyrAla-82 |
| SEQ. ID. NO. 15458 | 97-AlaAlaAspLysProPheGlyAsnAspPhe-106 |
| SEQ. ID. NO. 15459 | 137-ArgPheHisLysHisArgGln-143 |
| SEQ. ID. NO. 15460 | 157-ValGlnAspGlyGluLeuGlyAsnGlyGlnSerGlnCysLeu-170 |
| SEQ. ID. NO. 15461 | 181-AlaAspGlyGlyCysGlyAspThr-188 |
| SEQ. ID. NO. 15462 | 211-ThrValLysAspValGluCysArgLeu-219 |

Hydrophilic Regions - Hopp-Woods
| | |
|---|---|
| SEQ. ID. NO. 15463 | 22-GluGluIleAspAla-26 |
| SEQ. ID. NO. 15464 | 33-AspCysLeuArgAlaAlaAsn-39 |
| SEQ. ID. NO. 15465 | 74-LeuGlyArgGlyAspAspValTyr-81 |
| SEQ. ID. NO. 15466 | 97-AlaAlaAspLysProPheGly-103 |
| SEQ. ID. NO. 15467 | 137-ArgPheHisLysHisArgGln-143 |
| SEQ. ID. NO. 15468 | 158-GlnAspGlyGluLeuGlyAsn-164 |
| SEQ. ID. NO. 15469 | 183-GlyGlyCysGlyAspThr-188 |
| SEQ. ID. NO. 15470 | 211-ThrValLysAspValGluCysArgLeu-219 | a097
AMPHI Regions - AMPHI
| | |
|---|---|
| SEQ. ID. NO. 15471 | 28-AlaGlyLeuThrThrPheLeuThrMetCysTyrIleVal-40 |
| SEQ. ID. NO. 15472 | 72-MetGlyPheValGly-76 |
| SEQ. ID. NO. 15473 | 166-AlaThrLeuValGlyLeuGlyValAspIleHisGlnProSerAlaLeuLeuAlaLeuPheGly-185 |
| SEQ. ID. NO. 15474 | 207-ThrIleThrValIleAlaSerLeuMetGlyLeuAsnGluPheHisGlyIleIleGlyGluValProSerIle-230 |
| SEQ. ID. NO. 15475 | 242-LeuPheThrValSer-246 |
| SEQ. ID. NO. 15476 | 260-PheAspSerThrGlyThr-265 |
| SEQ. ID. NO. 15477 | 342-LeuAlaLysSerValProAlaPheAlaThr-351 |
| SEQ. ID. NO. 15478 | 362-MetLeuArgSerAlaArgAspIle-369 |

Antigenic Index - Jameson-Wolf
| | |
|---|---|
| SEQ. ID. NO. 15479 | 1-MetAspThrSerLysGlnThrLeu-8 |
| SEQ. ID. NO. 15480 | 13-PheLysLeuLysAlaAsnGlyThrThrValArgThrGluLeu-26 |
| SEQ. ID. NO. 15481 | 125-LysValArgGluMetLeu-130 |
| SEQ. ID. NO. 15482 | 260-PheAspSerThrGly-264 |
| SEQ. ID. NO. 15483 | 277-ValAspGlyLysLeuProArgLeuLysArg-286 |
| SEQ. ID. NO. 15484 | 317-SerAlaGlyGlyArgThrGly-323 |
| SEQ. ID. NO. 15485 | 364-ArgSerAlaArgAspIleAspTrpAspAspMetThrGlu-376 |
| SEQ. ID. NO. 15486 | 410-LeuCysArgArgThrLysAspValProPro-419 |

Hydrophilic Regions - Hopp-Woods
| | |
|---|---|
| SEQ. ID. NO. 15487 | 1-MetAspThrSerLys-5 |
| SEQ. ID. NO. 15488 | 16-LysAlaAsnGlyThrThrValArgThrGluLeu-26 |
| SEQ. ID. NO. 15489 | 125-LysValArgGluMetLeu-130 |
| SEQ. ID. NO. 15490 | 279-GlyLysLeuProArgLeuLysArg-286 |
| SEQ. ID. NO. 15491 | 318-AlaGlyGlyArgThr-322 |
| SEQ. ID. NO. 15492 | 364-ArgSerAlaArgAspIleAspTrpAspAspMetThrGlu-376 |
| SEQ. ID. NO. 15493 | 410-LeuCysArgArgThrLysAspValPro-418 | a098-2
AMPHI Regions - AMPHI
| | |
|---|---|
| SEQ. ID. NO. 15494 | 28-AlaAlaGluAlaGlyGluGlnPheValGlyAsp-38 |
| SEQ. ID. NO. 15495 | 110-ValGlyAspPhePheLysLeuAlaPhe-118 |
| SEQ. ID. NO. 15496 | 120-CysGlnIleGlnAsnValValThrAlaIleAlaGlnIleValAla-134 |
| SEQ. ID. NO. 15497 | 163-LeuSerSerPheSerHisGly-169 |

Antigenic Index - Jameson-Wolf
| | |
|---|---|
| SEQ. ID. NO. 15498 | 24-ValGlnGluAspAlaAlaGluAlaGlyGlu-33 |
| SEQ. ID. NO. 15499 | 68-MetGlyMetCysArg-72 |
| SEQ. ID. NO. 15500 | 78-PheAsnHisThrAspArgGlnAlaAla-86 |
| SEQ. ID. NO. 15501 | 136-ThrAlaAsnGlyThrGlnSerGlyIleThrGlyArgAsnAlaArgLysArgAsnGlyPhe-155 |

TABLE 1-continued

| | |
|---|---|
| SEQ. ID. NO. 15502 | 158-PheGluGlyArgGlyLeuSerSerPheSerHisGlyIle-170 |
| SEQ. ID. NO. 15503 | 180-ValPheArgArgProMetArgIleCys-188 |

Hydrophilic Regions - Hopp-Woods

| | |
|---|---|
| SEQ. ID. NO. 15504 | 24-ValGlnGluAspAlaAlaGluAlaGlyGlu-33 |
| SEQ. ID. NO. 15505 | 79-AsnHisThrAspArgGlnAla-85 |
| SEQ. ID. NO. 15506 | 144-IleThrGlyArgAsnAlaArgLysArgAsnGly-154 |
| SEQ. ID. NO. 15507 | 158-PheGluGlyArgGly-162 |
| SEQ. ID. NO. 15508 | 180-ValPheArgArgProMetArg-186 | a099

AMPHI Regions - AMPHI

| | |
|---|---|
| SEQ. ID. NO. 15509 | 6-SerMetMetArgLeuProAspIle-13 |
| SEQ. ID. NO. 15510 | 47-AlaPheValGluPhePheGlyGluGly-55 |
| SEQ. ID. NO. 15511 | 102-LysLeuValGluThrTyrAlaLysThr-110 |
| SEQ. ID. NO. 15512 | 114-TrpAlaAspAlaLeuLysThrAla-121 |
| SEQ. ID. NO. 15513 | 135-ThrArgAsnMetAlaGlyProSerAsn-143 |
| SEQ. ID. NO. 15514 | 154-AlaGlyLysGlyLeuAlaLysProTyrGluGluProSerAspGlyGln-169 |
| SEQ. ID. NO. 15515 | 178-AlaAlaIleThrSerCysThrAsnThrSerAsnProArgAsnVal-192 |
| SEQ. ID. NO. 15516 | 251-ThrCysAsnGlyMetSer-256 |
| SEQ. ID. NO. 15517 | 341-IleAspAlaIleValAlaGluTyr-348 |
| SEQ. ID. NO. 15518 | 350-LysProGlnGlnPheArgAspVal-357 |
| SEQ. ID. NO. 15519 | 371-ProSerProLeuTyrAspTrpArg-378 |
| SEQ. ID. NO. 15520 | 381-SerThrTyrIleArg-385 |
| SEQ. ID. NO. 15521 | 400-LeuSerGlyMetArgProLeu-406 |
| SEQ. ID. NO. 15522 | 443-AspPheAsnSerTyrAlaThr-449 |
| SEQ. ID. NO. 15523 | 468-PheAsnGluMetValArg-473 |
| SEQ. ID. NO. 15524 | 494-MetArgMetTrpGluAlaIleGluThrTyrMet-504 |
| SEQ. ID. NO. 15525 | 532-ArgLeuAlaGlyVal-536 |
| SEQ. ID. NO. 15526 | 539-IleValAlaGluGlyPheGluArgIleHisArgThrAsn-551 |
| SEQ. ID. NO. 15527 | 575-GlyThrGluThrTyr-579 |

Antigenic Index - Jameson-Wolf

| | |
|---|---|
| SEQ. ID. NO. 15528 | 18-LeuAsnGlyLysArgLysAlaGly-25 |
| SEQ. ID. NO. 15529 | 38-PheLeuArgLysGluArgValVal-45 |
| SEQ. ID. NO. 15530 | 53-GlyGluGlyAlaArgSer-58 |
| SEQ. ID. NO. 15531 | 60-SerIleGlyAspArgAlaThr-66 |
| SEQ. ID. NO. 15532 | 70-MetThrProGluPhe-74 |
| SEQ. ID. NO. 15533 | 83-IleAspGluGlnThr-87 |
| SEQ. ID. NO. 15534 | 94-ThrGlyArgAspAspAlaGlnValLysLeu-103 |
| SEQ. ID. NO. 15535 | 133-SerValThrArgAsnMetAlaGlyProSerAsnProHis-145 |
| SEQ. ID. NO. 15536 | 153-LeuAlaGlyLysGlyLeuAlaLysProTyrGluGluProSerAspGlyGlnMetProAspGlyAla-174 |
| SEQ. ID. NO. 15537 | 183-CysThrAsnThrSerAsnProArgAsnVal-192 |
| SEQ. ID. NO. 15538 | 206-GlyLeuGlnArgLysProTrpValLysSerSerPheAlaProGlySerLysValAla-224 |
| SEQ. ID. NO. 15539 | 227-TyrLeuLysGluAlaAspLeuLeuProGluMetGluLysLeu-240 |
| SEQ. ID. NO. 15540 | 251-ThrCysAsnGlyMetSerGlyAlaLeuAspProLysIleGlnLysGluIleIleAspArgAspLeuTyr-273 |
| SEQ. ID. NO. 15541 | 279-SerGlyAsnArgAsnPheAspGlyArgIleHisProTyrAlaLys-293 |
| SEQ. ID. NO. 15542 | 312-IleArgPheAspIleGluAsnAspVal-320 |
| SEQ. ID. NO. 15543 | 322-GlyValAlaAspGlyLysGluIleArgLeuLysAspIleTrpProThrAspGluGluIleAsp-342 |
| SEQ. ID. NO. 15544 | 348-TyrValLysProGlnGlnPheArgAsp-356 |
| SEQ. ID. NO. 15545 | 363-AspThrGlyThrAlaGlnLysAlaProSerProLeuTyrAspTrpArgProMetSerThrTyrIleArgArgProProTyrTrp-390 |
| SEQ. ID. NO. 15546 | 394-LeuAlaGlyGluArgThrLeuSerGlyMetArg-404 |
| SEQ. ID. NO. 15547 | 409-LeuProAspAsnIleThrThrAspHisLeuSerProSerAsn-422 |
| SEQ. ID. NO. 15548 | 438-GlyLeuProGluGluAspPheAsnSerTyrAlaThrHisArgGlyAspHisLeuThr-456 |
| SEQ. ID. NO. 15549 | 463-AlaAsnProLysLeuPhe-468 |
| SEQ. ID. NO. 15550 | 471-MetValArgAsnGluAspGlySerValArgGlnGlySerLeuAlaArgValGluProGluGlyGlnThr-493 |
| SEQ. ID. NO. 15551 | 503-TyrMetAsnArgLysGlnPro-509 |
| SEQ. ID. NO. 15552 | 516-AlaAspTyrGlyGlnGlySerSerArgAspTrpAlaAlaLysGlyValArg-532 |
| SEQ. ID. NO. 15553 | 543-GlyPheGluArgIleHisArgThrAsnLeu-552 |
| SEQ. ID. NO. 15554 | 562-PheLysProGlyThrAsnArgHisThrLeuGlnLeuAspGlyThrGluThrTyrAspValValGlyGluArgThrProArgCysAspLeu-591 |
| SEQ. ID. NO. 15555 | 595-IleHisArgLysAsnGlyGluThrValGlu-604 |
| SEQ. ID. NO. 15556 | 609-CysArgLeuAspThrAlaGluGlu-616 |

Hydrophilic Regions - Hopp-Woods

| | |
|---|---|
| SEQ. ID. NO. 15557 | 18-LeuAsnGlyLysArgLysAlaGly-25 |
| SEQ. ID. NO. 15558 | 38-PheLeuArgLysGluArgValVal-45 |
| SEQ. ID. NO. 15559 | 53-GlyGluGlyAlaArg-57 |
| SEQ. ID. NO. 15560 | 60-SerIleGlyAspArgAlaThr-66 |
| SEQ. ID. NO. 15561 | 83-IleAspGluGlnThr-87 |
| SEQ. ID. NO. 15562 | 94-ThrGlyArgAspAspAlaGlnValLysLeu-103 |
| SEQ. ID. NO. 15563 | 157-GlyLeuAlaLysProTyrGluGluProSerAspGlyGlnMetPro-171 |
| SEQ. ID. NO. 15564 | 227-TyrLeuLysGluAlaAspLeuLeuProGluMetGluLysLeu-240 |
| SEQ. ID. NO. 15565 | 259-LeuAspProLysIleGlnLysGluIleIleAspArgAspLeuTyr-273 |
| SEQ. ID. NO. 15566 | 282-ArgAsnPheAspGlyArgIle-288 |
| SEQ. ID. NO. 15567 | 312-IleArgPheAspIleGluAsnAspVal-320 |
| SEQ. ID. NO. 15568 | 324-AlaAspGlyLysGluIleArgLeuLysAsp-333 |
| SEQ. ID. NO. 15569 | 335-TrpProThrAspGluGluIleAsp-342 |
| SEQ. ID. NO. 15570 | 366-ThrAlaGlnLysAlaPro-371 |
| SEQ. ID. NO. 15571 | 394-LeuAlaGlyGluArgThrLeuSer-401 |
| SEQ. ID. NO. 15572 | 438-GlyLeuProGluGluAspPheAsn-445 |
| SEQ. ID. NO. 15573 | 450-HisArgGlyAspHisLeuThr-456 |
| SEQ. ID. NO. 15574 | 471-MetValArgAsnGluAspGlySerValArgGln-481 |
| SEQ. ID. NO. 15575 | 485-AlaArgValGluProGluGlyGlnThr-493 |
| SEQ. ID. NO. 15576 | 503-TyrMetAsnArgLysGlnPro-509 |

TABLE 1-continued

| | |
|---|---|
| SEQ. ID. NO. 15577 | 518-TyrGlyGlnGlySerSerArgAspTrpAlaAlaLysGlyValArg-532 |
| SEQ. ID. NO. 15578 | 543-GlyPheGluArgIleHisArg-549 |
| SEQ. ID. NO. 15579 | 564-ProGlyThrAsnArgHis-569 |
| SEQ. ID. NO. 15580 | 574-AspGlyThrGluThr-578 |
| SEQ. ID. NO. 15581 | 580-AspValValGlyGluArgThrProArgCysAsp-590 |
| SEQ. ID. NO. 15582 | 595-IleHisArgLysAsnGlyGluThrValGlu-604 |
| SEQ. ID. NO. 15583 | 609-CysArgLeuAspThrAlaGluGlu-616 | a102
AMPHI Regions - AMPHI

| | |
|---|---|
| SEQ. ID. NO. 15584 | 42-ValLeuLeuTyrThrTrpPheSerMetLeu-51 |
| SEQ. ID. NO. 15585 | 67-GlyAlaXxxPheAspThrMetValLysAspLeuLeuGlyArgSerTrpAsnIleIleAsnGlyIleAla-89 |
| SEQ. ID. NO. 15586 | 109-ThrAlaLysGlyLeuGlySerAlaAla-117 |
| SEQ. ID. NO. 15587 | 128-LeuValPhePheGlyIleLeuAlaPheCys-137 |
| SEQ. ID. NO. 15588 | 144-LeuValAspArgPheThrSerValLeu-152 |
| SEQ. ID. NO. 15589 | 155-GlyMetValLeuThr-159 |
| SEQ. ID. NO. 15590 | 207-AsnValSerSerLeuLeuLysTyrPheLys-216 |
| SEQ. ID. NO. 15591 | 221-LysValAlaLysSerIle-226 |
| SEQ. ID. NO. 15592 | 267-IleGluThrLeuSerLysPheAlaGlnThrGlyAsnMetAspLysIleLeuSerLeuPheSerTyrMetAla-290 |
| SEQ. ID. NO. 15593 | 303-PheAspTyrIleAlaAspIlePheLysTrpAsnAsp-314 |
| SEQ. ID. NO. 15594 | 341-PheValThrAlaIleGlyTyr-347 |
| SEQ. ID. NO. 15595 | 352-AlaThrValTrpThrGlyIleIlePro-360 |
| SEQ. ID. NO. 15596 | 374-GlyLysThrTyrLysVal-379 |

Antigenic Index - Jameson-Wolf

| | |
|---|---|
| SEQ. ID. NO. 15597 | 1-MetProThrLysThrProSerLeu-8 |
| SEQ. ID. NO. 15598 | 77-LeuLeuGlyArgSer-81 |
| SEQ. ID. NO. 15599 | 107-AspLeuThrAlaLysGlyLeuGlySerAlaAlaGlyGly-119 |
| SEQ. ID. NO. 15600 | 143-ArgLeuValAspArgPheThr-149 |
| SEQ. ID. NO. 15601 | 179-ThrGlnAlaProThrGlyThrAsn-186 |
| SEQ. ID. NO. 15602 | 214-TyrPheLysGlyAspAlaProLysValAla-223 |
| SEQ. ID. NO. 15603 | 246-XxxAsnLeuProArgAsnGluPhe-253 |
| SEQ. ID. NO. 15604 | 274-AlaGlnThrGlyAsnMetAspLysIle-282 |
| SEQ. ID. NO. 15605 | 311-LysTrpAsnAspSerValSerGlyArgThrLysThr-322 |
| SEQ. ID. NO. 15606 | 364-LeuTyrArgSerArgLysLysPheGlyAlaGlyLysThrTyrLysVal-379 |

Hydrophilic Regions - Hopp-Woods

| | |
|---|---|
| SEQ. ID. NO. 15607 | 1-MetProThrLysThr-5 |
| SEQ. ID. NO. 15608 | 143-ArgLeuValAspArgPheThr-149 |
| SEQ. ID. NO. 15609 | 215-PheLysGlyAspAlaProLysValAla-223 |
| SEQ. ID. NO. 15610 | 248-LeuProArgAsnGluPhe-253 |
| SEQ. ID. NO. 15611 | 277-GlyAsnMetAspLys-281 |
| SEQ. ID. NO. 15612 | 316-ValSerGlyArgThrLysThr-322 |
| SEQ. ID. NO. 15613 | 366-ArgSerArgLysLysPheGlyAla-373 | a105
AMPHI Regions - AMPHI

| | |
|---|---|
| SEQ. ID. NO. 15614 | 11-TrpIleGlyLeuGly-15 |
| SEQ. ID. NO. 15615 | 22-ValThrArgLeuLeuAsp-27 |
| SEQ. ID. NO. 15616 | 51-LysValTyrGlyAsnThrAlaGluLeu-59 |
| SEQ. ID. NO. 15617 | 74-AlaAlaValCysAspIleLeuAsnGlyValArgAspGlyLeu-87 |
| SEQ. ID. NO. 15618 | 97-ThrIleSerProThr-101 |
| SEQ. ID. NO. 15619 | 110-ValGluAlaAlaGlyGlyGlnPheAlaGluAlaProVal-122 |
| SEQ. ID. NO. 15620 | 143-AlaValLeuAsnProLeuGlnLysIlePheSer-153 |
| SEQ. ID. NO. 15621 | 162-PheGlyAspValGlyLysGlySer-169 |
| SEQ. ID. NO. 15622 | 176-AsnSerLeuLeuGlyIlePheGlyGluAlaTyr-186 |
| SEQ. ID. NO. 15623 | 203-IleValGluAlaIleGlyGlySerAla-211 |
| SEQ. ID. NO. 15624 | 249-LeuGluGlnAlaGlyAsnThrLeuProAlaValGlu-260 |
| SEQ. ID. NO. 15625 | 263-AlaAlaSerTyrArgLysAlaValGluAla-272 |

Antigenic Index - Jameson-Wolf

| | |
|---|---|
| SEQ. ID. NO. 15626 | 2-SerAlaAsnGluTyrThr-7 |
| SEQ. ID. NO. 15627 | 25-LeuLeuAspGlyGlyIleGlu-31 |
| SEQ. ID. NO. 15628 | 34-ValTyrAsnArgSerProAspLysThrAlaProIleSerAlaLysGlyAlaLysValTyrGlyAsnThr-56 |
| SEQ. ID. NO. 15629 | 81-AsnGlyValArgAspGlyLeuAla-88 |
| SEQ. ID. NO. 15630 | 96-SerThrIleSerProThrGluAsnLeuAla-105 |
| SEQ. ID. NO. 15631 | 121-ProValSerGlySerValGlyProAlaThr-130 |
| SEQ. ID. NO. 15632 | 139-GlyGlySerGluAla-143 |
| SEQ. ID. NO. 15633 | 155-ValGlyLysLysThrPheHisPheGlyAspValGlyLysGlySerGly-170 |
| SEQ. ID. NO. 15634 | 196-PheGlyIleAspThrAspThrIleVal-204 |
| SEQ. ID. NO. 15635 | 210-SerAlaMetAspSerProMetPheGlnThrLysLysSerLeuTrpAlaAsnArgGluPheProPro-231 |
| SEQ. ID. NO. 15636 | 237-HisAlaSerLysAspLeuAsnLeuAlaValLysGluLeuGluGlnAlaGlyAsnThrLeuPro-257 |
| SEQ. ID. NO. 15637 | 264-AlaSerTyrArgLysAlaValGluAlaGlyTyrGlyGluGlnAspValSerGly-281 |

Hydrophilic Regions - Hopp-Woods

| | |
|---|---|
| SEQ. ID. NO. 15638 | 25-LeuLeuAspGlyGlyIle-30 |
| SEQ. ID. NO. 15639 | 37-ArgSerProAspLysThrAlaProIleSerAlaLysGlyAlaLys-51 |
| SEQ. ID. NO. 15640 | 81-AsnGlyValArgAspGlyLeuAla-88 |
| SEQ. ID. NO. 15641 | 164-AspValGlyLysGlySerGly-170 |
| SEQ. ID. NO. 15642 | 196-PheGlyIleAspThrAspThrIle-203 |
| SEQ. ID. NO. 15643 | 218-GlnThrLysLysSerLeuTrpAla-225 |
| SEQ. ID. NO. 15644 | 237-HisAlaSerLysAspLeuAsnLeuAlaValLysGluLeuGluGlnAlaGly-253 |
| SEQ. ID. NO. 15645 | 265-SerTyrArgLysAlaValGlu-271 |
| SEQ. ID. NO. 15646 | 273-GlyTyrGlyGluGlnAspVal-279 |

TABLE 1-continued a109-2
AMPHI Regions - AMPHI
SEQ. ID. NO. 15647  6-GlyThrTyrArgAspLeuHisArgProAlaSerGlu-17
SEQ. ID. NO. 15648  53-LeuIleProAlaMetAlaGlyThrIleGly-62
SEQ. ID. NO. 15649  69-AlaValAlaAlaAlaPhe-74
SEQ. ID. NO. 15650  145-GlyLeuLeuMetAla-149
SEQ. ID. NO. 15651  156-IleMetAlaLysLeuThrSer-162
SEQ. ID. NO. 15652  177-GlyThrThrGlyGlnValLysLysLeuPheSerTrpAlaGly-190
SEQ. ID. NO. 15653  207-ValMetTyrAlaLeuLeuGluHisTrpLysLysArgTrpLeu-220
SEQ. ID. NO. 15654  222-ValProLeuGlyCys-226
SEQ. ID. NO. 15655  294-HisGlnValPheGlnLysIle-300
SEQ. ID. NO. 15656  326-ValGlySerIleLeuGly-331
SEQ. ID. NO. 15657  336-ThrSerSerTrpGlyThr-341
SEQ. ID. NO. 15658  471-AlaValGlyMetLeuProGlyIleProProPheLeuGluHisPheLysSerLeu-488
Antigenic Index - Jameson-Wolf
SEQ. ID. NO. 15659  1-MetGluLysHisAsnGlyThrTyrArgAspLeuHisArgProAlaSer-16
SEQ. ID. NO. 15660  18-PheAlaThrArgAspGluTyrLeuGlu-26
SEQ. ID. NO. 15661  32-MetGlnProLysArgTrpArgProAsnLeuProPheArgAspTyrArgPheGluTrp-50
SEQ. ID. NO. 15662  78-LeuGlyLeuProAsp-82
SEQ. ID. NO. 15663  109-ProGlyAlaAsnLeuProGlyThrHis-117
SEQ. ID. NO. 15664  160-LeuThrSerAsnGlyVal-165
SEQ. ID. NO. 15665  179-ThrGlyGlnValLysLys-184
SEQ. ID. NO. 15666  245-AlaProGlyLeuProPro-250
SEQ. ID. NO. 15667  259-GluAsnSerGlyTrp-263
SEQ. ID. NO. 15668  301-SerTyrProGluLysThrAspLysVal-309
SEQ. ID. NO. 15669  312-AsnIleAspAspThrMetThr-318
SEQ. ID. NO. 15670  348-IleAlaLysArgProIleProGlyGly-356
SEQ. ID. NO. 15671  398-AlaGlyMetGluMetThrArgLysGlyLysThrThrGlnSer-411
SEQ. ID. NO. 15672  441-GlyCysLysGluArgSerAla-447
Hydrophilic Regions - Hopp-Woods
SEQ. ID. NO. 15673  1-MetGluLysHisAsnGlyThrTyrArgAspLeuHisArgProAlaSer-16
SEQ. ID. NO. 15674  18-PheAlaThrArgAspGluTyrLeuGlu-26
SEQ. ID. NO. 15675  35-LysArgTrpArgPro-39
SEQ. ID. NO. 15676  44-ArgAspTyrArgPheGluTrp-50
SEQ. ID. NO. 15677  180-GlyGlnValLysLys-184
SEQ. ID. NO. 15678  301-SerTyrProGluLysThrAspLysVal-309
SEQ. ID. NO. 15679  313-IleAspAspThrMetThr-318
SEQ. ID. NO. 15680  348-IleAlaLysArgProIlePro-354
SEQ. ID. NO. 15681  398-AlaGlyMetGluMetThrArgLysGlyLysThrThrGln-410
SEQ. ID. NO. 15682  441-GlyCysLysGluArgSerAla-447
a111
AMPHI Regions - AMPHI
SEQ. ID. NO. 15683  6-ArgLeuProAsnPheIleArgThrLeu-14
SEQ. ID. NO. 15684  58-ProSerProAlaGluIleGlnLysArgIleAspAspAlaLeuLysGluValAsnArgGlnMetSer-79
SEQ. ID. NO. 15685  90-PheAsnGlnHisThrAlaGly-96
SEQ. ID. NO. 15686  128-GlyProLeuValAsnLeuTrp-134
SEQ. ID. NO. 15687  151-IleLysGlnAlaAlaSerTyrThrGly-159
SEQ. ID. NO. 15688  170-AspTyrAlaSerLeu-174
SEQ. ID. NO. 15689  183-LeuAspLeuSerSerIleAlaLys-190
SEQ. ID. NO. 15690  209-TyrLeuValGluIleGlyGly-215
SEQ. ID. NO. 15691  314-GluThrGluAlaLeu-318
Antigenic Index - Jameson-Wolf
SEQ. ID. NO. 15692  1-MetProSerGluThrArgLeuProAsnPhe-10
SEQ. ID. NO. 15693  26-CysSerGluGlnThrAla-31
SEQ. ID. NO. 15694  37-GlnGlyGluThrMetGly-42
SEQ. ID. NO. 15695  49-TyrLeuSerAsnAsnArgAspLysLeuProSerProAlaGluIleGlnLysArgIleAspAspAlaLeuLysGluValAsnArgGlnMetSerThrTyr
                    GlnProAspSerGluIleSerArgPheAsnGlnHisThrAlaGlyLysProLeuArgIleSerSerAspPhe-105
SEQ. ID. NO. 15696  135-GlyPheGlyProAspLysSerValThrArgGluProSerProGluGlnIleLysGln-153
SEQ. ID. NO. 15697  163-IleIleLeuLysGlnGlyLysAspTyrAlaSerLeuSerLysThrHisProLysAla-181
SEQ. ID. NO. 15698  192-PheGlyValAspLysValAlaGlyGluLeuGluLysTyrGly-205
SEQ. ID. NO. 15699  213-IleGlyGlyGluLeuHisGlyLysGlyLysAsnAlaArgGlyGluProTrpArgIleGlyIleGluGlnProAsnIle-238
SEQ. ID. NO. 15700  250-LeuAsnAsnArgSerLeuAlaThrSerGlyAspTyrArg-262
SEQ. ID. NO. 15701  264-PheHisValAspLysSerGlyLysArgLeuSer-274
SEQ. ID. NO. 15702  277-IleAsnProAsnAsnLysArgProIleSer-286
SEQ. ID. NO. 15703  299-AlaMetThrAlaAspGlyLeuSer-306
SEQ. ID. NO. 15704  314-GluThrGluAlaLeuLysLeuAlaGluArgGluLysLeu-326
SEQ. ID. NO. 15705  332-ValArgAspLysGlyGlyTyrArg-339
SEQ. ID. NO. 15706  342-MetSerSerGluPheGluLysLeuLeuArg-351
Hydrophilic Regions - Hopp-Woods
SEQ. ID. NO. 15707  1-MetProSerGluThrArgLeu-7
SEQ. ID. NO. 15708  26-CysSerGluGlnThrAla-31
SEQ. ID. NO. 15709  51-SerAsnAsnArgAspLysLeuProSer-59
SEQ. ID. NO. 15710  61-AlaGluIleGlnLysArgIleAspAspAlaLeuLysGluValAsnArgGln-77
SEQ. ID. NO. 15711  82-GlnProAspSerGluIleSerArg-89
SEQ. ID. NO. 15712  97-LysProLeuArgIleSerSer-103
SEQ. ID. NO. 15713  137-GlyProAspLysSerValThrArgGluProSerProGluGlnIleLysGln-153
SEQ. ID. NO. 15714  163-IleIleLeuLysGlnGlyLysAspTyrAlaSer-173
SEQ. ID. NO. 15715  175-SerLysThrHisPro-179
SEQ. ID. NO. 15716  192-PheGlyValAspLysValAlaGlyGluLeuGluLysTyrGly-205
SEQ. ID. NO. 15717  217-LeuHisGlyLysGlyLysAsnAlaArgGlyGluProTrp-229

TABLE 1-continued

| | |
|---|---|
| SEQ. ID. NO. 15718 | 265-HisValAspLysSerGlyLysArgLeuSer-274 |
| SEQ. ID. NO. 15719 | 279-ProAsnAsnLysArgProIle-285 |
| SEQ. ID. NO. 15720 | 314-GluThrGluAlaLeuLysLeuAlaGluArgGluLysLeu-326 |
| SEQ. ID. NO. 15721 | 332-ValArgAspLysGlyGlyTyr-338 |
| SEQ. ID. NO. 15722 | 344-SerGluPheGluLysLeuLeuArg-351 | a117-1
AMPHI Regions - AMPHI

| | |
|---|---|
| SEQ. ID. NO. 15723 | 6-ProIleGlnAspThrGlnSerAla-13 |
| SEQ. ID. NO. 15724 | 15-LeuGlnGluLeuArgGluTrpPheAspSerTyrCysThr-27 |
| SEQ. ID. NO. 15725 | 57-GlyGluProLeuProAspHis-63 |
| SEQ. ID. NO. 15726 | 72-HisGluLeuAspLeuLeu-77 |
| SEQ. ID. NO. 15727 | 79-AspAlaValAlaAlaThrLeuLeuAlaAspIleGlyArgTyr-92 |
| SEQ. ID. NO. 15728 | 104-CysAsnSerThrValAlaGluLeuValLysGlyValAspGluValGlnLysLeuThrHisPheAlaArgValAspSerLeu-130 |
| SEQ. ID. NO. 15729 | 145-LysMetLeuLeuAlaMet-150 |
| SEQ. ID. NO. 15730 | 170-PheLeuSerAsnAlaProAspSerProGluLys-180 |
| SEQ. ID. NO. 15731 | 216-GluProGluLysTyrArg-221 |
| SEQ. ID. NO. 15732 | 234-ArgLeuGluTyrIleGluAsnPheLeuAsnIleLeuArg-246 |
| SEQ. ID. NO. 15733 | 260-GlyArgProLysHisIleTyrSerIleTyrLys-270 |
| SEQ. ID. NO. 15734 | 282-LeuPheAspIleArg-286 |
| SEQ. ID. NO. 15735 | 290-IleLeuValAspThrValProGluCysTyrThrThrLeuGlyIleVal HisSerLeuTrpGlnProIleProGlyGluPheAspAspTyrIleAla-321 |
| SEQ. ID. NO. 15736 | 327-GlyTyrLysSerLeuHisThr-333 |
| SEQ. ID. NO. 15737 | 351-AspMetHisGlnPheAsnGluPheGlyValAla-361 |
| SEQ. ID. NO. 15738 | 385-GlnLeuLeuAspTrp-389 |
| SEQ. ID. NO. 15739 | 440-HisSerSerIleGlyAspArg-446 |
| SEQ. ID. NO. 15740 | 493-LysAlaIleGlyLysIleArgAlaTyr-501 |
| SEQ. ID. NO. 15741 | 504-GlnGlnAsnAlaAsp-508 |
| SEQ. ID. NO. 15742 | 521-GlnLeuAlaLysLeu-525 |
| SEQ. ID. NO. 15743 | 532-GlnGluLeuAlaGlu-536 |
| SEQ. ID. NO. 15744 | 539-GlyTyrLysLysProGluAspLeuTyrThr-548 |
| SEQ. ID. NO. 15745 | 557-AsnArgAlaIleGlnLysAlaCysGlyThrLeuAsnGluProPro-571 |
| SEQ. ID. NO. 15746 | 585-LysIleLysLysGlyGly-590 |
| SEQ. ID. NO. 15747 | 603-MetThrThrLeuAlaLysCysCysLysProAla-613 |
| SEQ. ID. NO. 15748 | 616-AspAspIleValGly-620 |
| SEQ. ID. NO. 15749 | 637-SerPheArgHisLeuAlaGluHisAlaProGluLysValLeuAspAla-652 |
| SEQ. ID. NO. 15750 | 679-ArgAspValSerAspAla-684 |
| SEQ. ID. NO. 15751 | 714-GlnValThrAspLeuProArgValLeuAlaSerLeuGlyAspValLysGlyValLeuSerValThrArg-736 |

Antigenic Index - Jameson-Wolf

| | |
|---|---|
| SEQ. ID. NO. 15752 | 5-SerProIleGlnAspThrGlnSerAlaThr-14 |
| SEQ. ID. NO. 15753 | 16-GlnGluLeuArgGluTrpPheAspSerTyrCysThrAlaLeuProAsnAsnAspLysLysLeu-36 |
| SEQ. ID. NO. 15754 | 52-AlaAlaThrProTyrGlyGluProLeuProAspHisPhe-64 |
| SEQ. ID. NO. 15755 | 88-AspIleGlyArgTyrValProAspTrp-96 |
| SEQ. ID. NO. 15756 | 100-ValSerGluArgCysAsnSerThrVal-108 |
| SEQ. ID. NO. 15757 | 110-GluLeuValLysGlyValAspGluValGlnLys-120 |
| SEQ. ID. NO. 15758 | 125-AlaArgValAspSerLeuAlaThrProGluGluArgAlaGlnGlnAlaGluThrMetArg-144 |
| SEQ. ID. NO. 15759 | 162-AlaMetArgThrArgThr-167 |
| SEQ. ID. NO. 15760 | 173-AsnAlaProAspSerProGluLysArgAlaValAlaLysGluThrLeu-188 |
| SEQ. ID. NO. 15761 | 209-AspLeuGlyPheArgHisGlnGluProGluLysTyrArgGlu-222 |
| SEQ. ID. NO. 15762 | 227-LeuAspGluLysArgThrGluArgLeuGluTyr-237 |
| SEQ. ID. NO. 15763 | 245-LeuArgThrGluLeuLysLys-251 |
| SEQ. ID. NO. 15764 | 258-ValAlaGlyArgProLysHis-264 |
| SEQ. ID. NO. 15765 | 271-LysMetValLysLysLysLeuSerPhe-279 |
| SEQ. ID. NO. 15766 | 294-ThrValProGluCysTyr-299 |
| SEQ. ID. NO. 15767 | 311-ProIleProGlyGluPheAspAspTyrIleAlaAsnProLysGlyAsnGlyTyrLysSer-330 |
| SEQ. ID. NO. 15768 | 335-IleValGlyProGluAspLysGlyValGluValGlnIleArgThr-349 |
| SEQ. ID. NO. 15769 | 364-TrpArgTyrLysGluGlyGlyLysGlyAspSerAlaTyrGluGlnLys-379 |
| SEQ. ID. NO. 15770 | 387-LeuAspTrpArgGluAsnMetAlaGluSerGlyLysGluAspLeuAlaAla-403 |
| SEQ. ID. NO. 15771 | 418-ThrProHisGlyLys-422 |
| SEQ. ID. NO. 15772 | 440-HisSerSerIleGlyAspArgCysArgGlyAlaLysValGluGly-454 |
| SEQ. ID. NO. 15773 | 461-ThrProLeuGluAsnGlyGlnArgValGluIleIleThrAlaLysGluGlyHisProSerValAsn-482 |
| SEQ. ID. NO. 15774 | 487-GlyTrpValLysSerAsnLysAlaIleGlyLys-497 |
| SEQ. ID. NO. 15775 | 502-IleArgGlnGlnAsnAlaAspThrValArgGluGluGlyArgValGlnLeuAspLysGlnLeuAla-523 |
| SEQ. ID. NO. 15776 | 525-LeuThrProLysProAsnLeuGlnGluLeuAlaGlu-536 |
| SEQ. ID. NO. 15777 | 538-LeuGlyTyrLysLysProGluAspLeu-546 |
| SEQ. ID. NO. 15778 | 551-GlyGlnGlyGluIleSerAsnArgAlaIleGlnLysAlaCysGlyThrLeuAsnGluProProProValPro-574 |
| SEQ. ID. NO. 15779 | 582-LysGlnSerLysIleLysLysGlyGlyLysAsnGlyVal-594 |
| SEQ. ID. NO. 15780 | 596-IleAspGlyGluAspGlyLeu-602 |
| SEQ. ID. NO. 15781 | 608-LysCysCysLysProAlaProProAspAspIleVal-619 |
| SEQ. ID. NO. 15782 | 622-ValThrArgAspArgGlyIleSerValHisArgLysThrCysProSerPhe-638 |
| SEQ. ID. NO. 15783 | 644-HisAlaProGluLysValLeuAsp-651 |
| SEQ. ID. NO. 15784 | 667-IleGluIleArgAlaGlnAspArgSerGlyLeuLeuArgAspValSerAspAlaLeuAlaArgHisLysLeu-690 |
| SEQ. ID. NO. 15785 | 696-GlnThrGlnSerArgAspLeuGluAlaSerMet-706 |
| SEQ. ID. NO. 15786 | 710-LeuGluValLysGlnValThrAspLeuProArg-720 |
| SEQ. ID. NO. 15787 | 726-GlyAspValLysGly-730 |

Hydrophilic Regions - Hopp-Woods

| | |
|---|---|
| SEQ. ID. NO. 15788 | 8-GlnAspThrGlnSer-12 |
| SEQ. ID. NO. 15789 | 16-GlnGluLeuArgGluTrpPhe-22 |
| SEQ. ID. NO. 15790 | 30-ProAsnAsnAspLysLysLeu-36 |
| SEQ. ID. NO. 15791 | 100-ValSerGluArgCysAsnSerThr-107 |
| SEQ. ID. NO. 15792 | 110-GluLeuValLysGlyValAspGluValGlnLys-120 |

TABLE 1-continued

| SEQ. ID. NO. 15793 | 125-AlaArgValAspSer-129 |
| SEQ. ID. NO. 15794 | 131-AlaThrProGluGluArgAlaGlnGlnAlaGluThrMetArg-144 |
| SEQ. ID. NO. 15795 | 162-AlaMetArgThrArgThr-167 |
| SEQ. ID. NO. 15796 | 174-AlaProAspSerProGluLysArgAlaValAlaLysGluThrLeu-188 |
| SEQ. ID. NO. 15797 | 209-AspLeuGlyPheArgHisGlnGluProGluLysTyrArgGlu-222 |
| SEQ. ID. NO. 15798 | 227-LeuAspGluLysArgThrGluArgLeuGluTyr-237 |
| SEQ. ID. NO. 15799 | 245-LeuArgThrGluLeuLysLys-251 |
| SEQ. ID. NO. 15800 | 258-ValAlaGlyArgProLysHis-264 |
| SEQ. ID. NO. 15801 | 271-LysMetValLysLysLysLeuSerPhe-279 |
| SEQ. ID. NO. 15802 | 314-GlyGluPheAspAsp-318 |
| SEQ. ID. NO. 15803 | 323-ProLysGlyAsnGly-327 |
| SEQ. ID. NO. 15804 | 337-GlyProGluAspLysGlyValGluValGlnIleArgThr-349 |
| SEQ. ID. NO. 15805 | 365-ArgTyrLysGluGlyGlyLysGlyAspSerAlaTyrGluGln-378 |
| SEQ. ID. NO. 15806 | 387-LeuAspTrpArgGluAsnMetAlaGluSerGlyLysGluAspLeuAlaAla-403 |
| SEQ. ID. NO. 15807 | 443-IleGlyAspArgCysArgGlyAlaLysValGluGly-454 |
| SEQ. ID. NO. 15808 | 463-LeuGluAsnGlyGlnArgValGluIleIleThrAlaLysGluGlyHisPro-479 |
| SEQ. ID. NO. 15809 | 489-ValLysSerAsnLysAlaIleGlyLys-497 |
| SEQ. ID. NO. 15810 | 505-GlnAsnAlaAspThrValArgGluGluGlyArgValGlnLeuAspLysGlnLeuAla-523 |
| SEQ. ID. NO. 15811 | 538-LeuGlyTyrLysLysProGluAspLeu-546 |
| SEQ. ID. NO. 15812 | 553-GlyGluIleSerAsn-557 |
| SEQ. ID. NO. 15813 | 582-LysGlnSerLysIleLysLysGlyGlyLys-591 |
| SEQ. ID. NO. 15814 | 596-IleAspGlyGluAspGlyLeu-602 |
| SEQ. ID. NO. 15815 | 608-LysCysCysLysProAlaProProAspAspIle-618 |
| SEQ. ID. NO. 15816 | 622-ValThrArgAspArgGlyIleSerValHisArgLysThrCysPro-636 |
| SEQ. ID. NO. 15817 | 644-HisAlaProGluLysValLeu-650 |
| SEQ. ID. NO. 15818 | 667-IleGluIleArgAlaGlnAspArgSerGlyLeuLeuArgAspValSerAspAlaLeuAlaArgHisLysLeu-690 |
| SEQ. ID. NO. 15819 | 697-ThrGlnSerArgAspLeuGluAlaSerMet-706 |
| SEQ. ID. NO. 15820 | 710-LeuGluValLysGlnValThrAspLeuProArg-720 |
| SEQ. ID. NO. 15821 | 726-GlyAspValLysGly-730 | a118
AMPHI Regions - AMPHI
| SEQ. ID. NO. 15822 | 24-GlyLysTrpTyrAsp-28 |
| SEQ. ID. NO. 15823 | 57-IleProArgAspIle-61 |
| SEQ. ID. NO. 15824 | 65-IleGlyThrIleIleAspPheLeuMetValProAsn-76 |
| SEQ. ID. NO. 15825 | 94-IleHisGluArgTyrGluArgPheThrThrMetLeuArg-106 |

Antigenic Index - Jameson-Wolf
| SEQ. ID. NO. 15826 | 2-CysGluPheLysAspPheArgArgAsnIleProCys-13 |
| SEQ. ID. NO. 15827 | 15-GluGluTyrAspGluAsnSerPhe-22 |
| SEQ. ID. NO. 15828 | 24-GlyLysTrpTyrAspAspGlyValTrpAspAspGluGluTyrTrpLysLeuGluAsnAspLeuIleGluValArgLysLysTyrProTyrProMetAspIleProArgAspIle-61 |
| SEQ. ID. NO. 15829 | 86-ProTrpLeuProAspSer-91 |
| SEQ. ID. NO. 15830 | 93-GlyIleHisGluArgTyrGluArg-100 |
| SEQ. ID. NO. 15831 | 109-PheThrGluLysAspIleVal-115 |
| SEQ. ID. NO. 15832 | 119-PheAspTyrTyrAsnLysLys-125 |

Hydrophilic Regions - Hopp-Woods
| SEQ. ID. NO. 15833 | 2-CysGluPheLysAspPheArgArgAsnIleProCys-13 |
| SEQ. ID. NO. 15834 | 15-GluGluTyrAspGlu-19 |
| SEQ. ID. NO. 15835 | 30-GlyValTrpAspAspGluGluTyrTrpLysLeuGluAsnAspLeuIleGluValArgLysLysTyrProTyr-53 |
| SEQ. ID. NO. 15836 | 96-GluArgTyrGluArg-100 |
| SEQ. ID. NO. 15837 | 109-PheThrGluLysAspIleVal-115 |
| SEQ. ID. NO. 15838 | 121-TyrTyrAsnLysLys-125 | a120
AMPHI Regions - AMPHI
| SEQ. ID. NO. 15839 | 6-LysAsnIlePheSerAla-11 |
| SEQ. ID. NO. 15840 | 49-SerGlyAsnAlaTyrLysIleValSerThrIleLys-60 |
| SEQ. ID. NO. 15841 | 77-AsnThrLeuHisProThrTyrTyrArgAspIleArgArg-89 |
| SEQ. ID. NO. 15842 | 142-IleThrAsnGlyLysLysLeuTyrSerValGlyGlyLeuAsnLysAlaGly-158 |
| SEQ. ID. NO. 15843 | 189-ProSerLeuAsnAsnIleProAla-196 |

Antigenic Index - Jameson-Wolf
| SEQ. ID. NO. 15844 | 35-SerGlySerTyrGly-39 |
| SEQ. ID. NO. 15845 | 45-ThrPheGluArgSerGlyAsnAlaTyrLys-54 |
| SEQ. ID. NO. 15846 | 68-PheGluSerGlyGlyThrValVal-75 |
| SEQ. ID. NO. 15847 | 85-ArgAspIleArgArgGlyLysLeuTyrAlaGlu-95 |
| SEQ. ID. NO. 15848 | 97-LysPheAlaAspGlySerValThrTyrGlyLysAlaGlyGluSerLysThrGluGlnSerProLysAla-119 |
| SEQ. ID. NO. 15849 | 131-AlaAsnAspAlaLysLeuProProGlyLeuLysIleThrAsnGlyLysLysLeuTyrSer-150 |
| SEQ. ID. NO. 15850 | 153-GlyLeuAsnLysAlaGlyThrGlyLysTyrSerIleGlyGlyValGluThrGluValValLysTyrArgValArgArgGlyAspAspAlaVal-183 |
| SEQ. ID. NO. 15851 | 199-GlyTyrThrAspAspGlyLysThrTyr-207 |
| SEQ. ID. NO. 15852 | 218-GlyGlnAlaAlaLysPro-223 |

Hydrophilic Regions - Hopp-Woods
| SEQ. ID. NO. 15853 | 45-ThrPheGluArgSerGlyAsn-51 |
| SEQ. ID. NO. 15854 | 85-ArgAspIleArgArgGlyLysLeuTyrAla-94 |
| SEQ. ID. NO. 15855 | 107-LysAlaGlyGluSerLysThrGluGlnSerProLysAla-119 |
| SEQ. ID. NO. 15856 | 131-AlaAsnAspAlaLysLeu-136 |
| SEQ. ID. NO. 15857 | 143-ThrAsnGlyLysLysLeuTyr-149 |
| SEQ. ID. NO. 15858 | 155-AsnLysAlaGlyThrGly-160 |
| SEQ. ID. NO. 15859 | 167-ValGluThrGluValValLysTyrArgValArgArgGlyAspAspAla-182 |
| SEQ. ID. NO. 15860 | 200-TyrThrAspAspGlyLysThrTyr-207 |
| SEQ. ID. NO. 15861 | 219-GlnAlaAlaLysPro-223 |

TABLE 1-continued a121-1
AMPHI Regions - AMPHI
SEQ. ID. NO. 15862     68-GlnGluLeuSerArgLeuTyrAlaGlnThr-77
SEQ. ID. NO. 15863     101-ThrValArgHisAlaPro-106
SEQ. ID. NO. 15864     148-ProAlaPheHisGlu-152
SEQ. ID. NO. 15865     165-LeuAsnIleGlyGlyIleAlaAsnIle-173
SEQ. ID. NO. 15866     189-ProGlyAsnMetLeuMetAspAlaTrpMetGlnAla-200
SEQ. ID. NO. 15867     216-GlyAsnIleLeuProGlnLeuLeuAspArgLeuLeu-227
SEQ. ID. NO. 15868     237-ProLysSerThrGly-241
SEQ. ID. NO. 15869     251-GluThrTyrLeuAsp-255
SEQ. ID. NO. 15870     262-AspValLeuArgThrLeuSerArgPheThrAlaGlnThrValPheAspAlaValSerHis-281
SEQ. ID. NO. 15871     303-AlaAspLeuAlaGluCysPhe-309
SEQ. ID. NO. 15872     341-ValAsnArgIleProGlySerPro-348
Antigenic Index - Jameson-Wolf
SEQ. ID. NO. 15873     13-ThrSerMetAspGlyAlaAsp-19
SEQ. ID. NO. 15874     23-IleArgMetAspGlyGlyLysTrpLeuGly-32
SEQ. ID. NO. 15875     40-ProTyrProGlyArgLeuArgArgLysLeuLeuAspLeuGlnAspThrGlyAlaAspGluLeuHisArgSerArgMetLeuSer-67
SEQ. ID. NO. 15876     86-AsnLeuAlaProSerAspIleThrAla-94
SEQ. ID. NO. 15877     97-CysHisGlyGlnThrValArgHisAlaProGluHisSerTyrSer-111
SEQ. ID. NO. 15878     119-LeuLeuAlaGluArgThrGln-125
SEQ. ID. NO. 15879     129-ValGlyAspPheArgSerArgAspLeuAlaAlaGlyGlyGlnGly-143
SEQ. ID. NO. 15880     154-LeuPheArgAspAspArgGluThrArgAla-163
SEQ. ID. NO. 15881     177-ProProAspAlaPro-181
SEQ. ID. NO. 15882     184-GlyPheAspThrGlyProGlyAsn-191
SEQ. ID. NO. 15883     205-ProTyrAspLysAsnGlyAlaLysAlaAlaGlnGlyAsn-217
SEQ. ID. NO. 15884     235-ProHisProLysSerThrGlyArgGlu-243
SEQ. ID. NO. 15885     253-TyrLeuAspGlyGlyGluAsnArgTyrAspValLeuArgThrLeuSer-268
SEQ. ID. NO. 15886     283-AlaAlaAspAlaArgGln-288
SEQ. ID. NO. 15887     293-GlyGlyGlyIleArgAsnProValLeu-301
SEQ. ID. NO. 15888     344-IleProGlySerProHisLysAlaThrGlyAlaSerLysProCysIle-359
Hydrophilic Regions - Hopp-Woods
SEQ. ID. NO. 15889     13-ThrSerMetAspGlyAlaAsp-19
SEQ. ID. NO. 15890     43-GlyArgLeuArgArgLysLeuLeuAspLeuGlnAspThrGlyAlaAspGluLeuHisArgSerArgMetLeuSer-67
SEQ. ID. NO. 15891     101-ThrValArgHisAlaPro-106
SEQ. ID. NO. 15892     119-LeuLeuAlaGluArgThrGln-125
SEQ. ID. NO. 15893     131-AspPheArgSerArgAspLeuAlaAla-139
SEQ. ID. NO. 15894     154-LeuPheArgAspAspArgGluThrArgAla-163
SEQ. ID. NO. 15895     206-TyrAspLysAsnGlyAlaLysAlaAlaGln-215
SEQ. ID. NO. 15896     236-HisProLysSerThrGlyArgGlu-243
SEQ. ID. NO. 15897     254-LeuAspGlyGlyGluAsnArgTyrAspVal-263
SEQ. ID. NO. 15898     283-AlaAlaAspAlaArgGln-288
SEQ. ID. NO. 15899     344-IleProGlySerProHisLysAlaThrGlyAlaSer-355
a122-1
AMPHI Regions - AMPHI
SEQ. ID. NO. 15900     6-AsnIleHisLysThrPhe-11
SEQ. ID. NO. 15901     42-ThrPheLeuArgCysLeuAsnAlaLeuGluMetProGlu-54
SEQ. ID. NO. 15902     102-LeuGluAsnValMetGlu-107
SEQ. ID. NO. 15903     126-LysLeuLeuGluLys-130
SEQ. ID. NO. 15904     176-ProGluLeuValGlnAspValLeuAsnAlaMetLysGluLeuAlaArgGluGly-193
SEQ. ID. NO. 15905     227-ProLysGluLeuPheAspHisPro-234
Antigenic Index - Jameson-Wolf
SEQ. ID. NO. 15906     5-ArgAsnIleHisLysThrPheGlyLysAsnThrIle-16
SEQ. ID. NO. 15907     23-AspValCysLysGlyGln-28
SEQ. ID. NO. 15908     34-GlyProSerGlySerGlyLysThrThr-42
SEQ. ID. NO. 15909     51-GluMetProGluAspGlyGlnIleGluPheAspAsnGluArgProLeuLys
                       IleAspPheSerLysLysProSerLysHisAspIle-79
SEQ. ID. NO. 15910     81-AlaLeuArgArgLysSerGlyMet-88
SEQ. ID. NO. 15911     96-PheProHisLysThrAlaLeu-102
SEQ. ID. NO. 15912     114-GlyLysProAlaAlaGlnAlaArgGluGluAlaLeuLysLeuLeuGlu-129
SEQ. ID. NO. 15913     131-ValGlyLeuGlyAspLysValAspLeu-139
SEQ. ID. NO. 15914     145-SerGlyGlyGlnGlnGlnArgValGlyIle-154
SEQ. ID. NO. 15915     168-AspGluProThrSerAlaLeuAspProGluLeuVal-179
SEQ. ID. NO. 15916     184-AsnAlaMetLysGluLeuAlaArgGluGlyTrp-194
SEQ. ID. NO. 15917     222-ValGluGlnGlySerProLysGluLeuPheAspHisProLysHisGluArgThrArgArgPheLeuSer-244
Hydrophilic Regions - Hopp-Woods
SEQ. ID. NO. 15918     51-GluMetProGluAspGlyGlnIleGluPheAspAsnGluArgProLeuLysIleAspPheSerLysLysProSerLysHisAsp-78
SEQ. ID. NO. 15919     81-AlaLeuArgArgLysSerGly-87
SEQ. ID. NO. 15920     114-GlyLysProAlaAlaGlnAlaArgGluGluAlaLeuLysLeuLeuGlu-129
SEQ. ID. NO. 15921     131-ValGlyLeuGlyAspLysValAsp-138
SEQ. ID. NO. 15922     168-AspGluProThrSerAlaLeuAspProGluLeuVal-179
SEQ. ID. NO. 15923     184-AsnAlaMetLysGluLeuAlaArg-191
SEQ. ID. NO. 15924     224-GlnGlySerProLysGluLeuPheAspHisProLysHisGluArgThrArgArgPheLeu-243
a126-1
AMPHI Regions - AMPHI
SEQ. ID. NO. 15925     26-LeuLysGlnSerValArg-31
SEQ. ID. NO. 15926     73-GlyCysGlnSerValGlnGluAla-80
SEQ. ID. NO. 15927     112-PheGlnLeuValGluAla-117
SEQ. ID. NO. 15928     143-LeuAspAlaGlyCysGln-148
SEQ. ID. NO. 15929     150-LeuMetProTrpAlaAlaProIleGlyThrGlyLeuGlyAlaVal-164
SEQ. ID. NO. 15930     213-SerGlyAspProValAsnMetAlaArgAlaPhe-223

TABLE 1-continued

Antigenic Index - Jameson-Wolf
SEQ. ID. NO. 15931	7-GluThrPheProSerArgLeu-13
SEQ. ID. NO. 15932	24-GluIleLeuLysGlnSerValArgThrAlaArg-34
SEQ. ID. NO. 15933	41-SerLeuArgArgAlaGlyCysGlyGlyGluAlaHisGlyGlnGlyPhe-56
SEQ. ID. NO. 15934	85-GlnMetAlaArgGluValPheGlu-92
SEQ. ID. NO. 15935	99-GluLeuIleGlyAspAspAspThrLeuGln-108
SEQ. ID. NO. 15936	121-LeuIleLysAspGlyPheLysValLeu-129
SEQ. ID. NO. 15937	141-ArgLeuLeuAspAlaGlyCys-147
SEQ. ID. NO. 15938	171-ValLeuArgGluArgLeuProAspThrProLeu-181
SEQ. ID. NO. 15939	209-AlaValSerArgSerGlyAspProValAsn-218
SEQ. ID. NO. 15940	228-GluSerGlyArgLeuAlaPhe-234
SEQ. ID. NO. 15941	237-GlyProValGluAlaArgAspLysAlaGlnAlaSerThrProThrVal-252
Hydrophilic Regions - Hopp-Woods
SEQ. ID. NO. 15942	24-GluIleLeuLysGlnSerValArgThrAlaArg-34
SEQ. ID. NO. 15943	41-SerLeuArgArgAlaGlyCysGlyGlyGluAlaHis-52
SEQ. ID. NO. 15944	85-GlnMetAlaArgGluValPheGlu-92
SEQ. ID. NO. 15945	100-LeuIleGlyAspAspAspThrLeuGln-108
SEQ. ID. NO. 15946	171-ValLeuArgGluArgLeuProAsp-178
SEQ. ID. NO. 15947	210-ValSerArgSerGlyAspPro-216
SEQ. ID. NO. 15948	228-GluSerGlyArgLeuAlaPhe-234
SEQ. ID. NO. 15949	237-GlyProValGluAlaArgAspLysAlaGlnAla-247
a127
AMPHI Regions - AMPHI
SEQ. ID. NO. 15950	6-MetLeuAspThrTrpLeuGlyAla-13
SEQ. ID. NO. 15951	22-GluSerValAlaVal-26
SEQ. ID. NO. 15952	119-ValGlyAspTyrIleGluIle-125
SEQ. ID. NO. 15953	135-IleAsnLeuLeuAsnThrLeuMet-142
SEQ. ID. NO. 15954	147-ProAsnProLeuValGlyGlnLeuAla-155
SEQ. ID. NO. 15955	206-LeuGluProLeuCysAlaPro-212
SEQ. ID. NO. 15956	214-IleProAlaIleGlnArgHisLeuGluAsnValGln-225
SEQ. ID. NO. 15957	250-ArgIleIleValArgPheAlaSerProVal-259
SEQ. ID. NO. 15958	268-AlaValMetAspGluPheLeuArgVal-276
Antigenic Index - Jameson-Wolf
SEQ. ID. NO. 15959	16-IleArgAlaGluAlaValGlu-22
SEQ. ID. NO. 15960	41-HisPheLysArgHisProAspPheGlyIleGluSerLysArgArgPheLeuVal-58
SEQ. ID. NO. 15961	112-SerAlaThrGlnGlnTyrSerVal-119
SEQ. ID. NO. 15962	126-AsnGlyLeuArgGlyArgValValAsp-134
SEQ. ID. NO. 15963	169-HisProValArgArgAspAsnIleLeu-177
SEQ. ID. NO. 15964	193-LeuAspSerAspGluAlaValCysArg-201
SEQ. ID. NO. 15965	233-ProAlaAlaLysProArgValThrArgValProTyrAspAspLysAlaTyr-249
SEQ. ID. NO. 15966	257-SerProValSerLysArgLeuGluIle-265
SEQ. ID. NO. 15967	283-TyrProAlaGlySerGluThrLeu-290
Hydrophilic Regions - Hopp-Woods
SEQ. ID. NO. 15968	16-IleArgAlaGluAlaValGlu-22
SEQ. ID. NO. 15969	42-PheLysArgHisProAspPheGlyIleGluSerLysArgArgPheLeuVal-58
SEQ. ID. NO. 15970	126-AsnGlyLeuArgGlyArgValVal-133
SEQ. ID. NO. 15971	170-ProValArgArgAspAsnIleLeu-177
SEQ. ID. NO. 15972	193-LeuAspSerAspGluAlaValCysArg-201
SEQ. ID. NO. 15973	235-AlaLysProArgValThrArgValProTyrAspAspLysAlaTyr-249
SEQ. ID. NO. 15974	259-ValSerLysArgLeuGluIle-265
SEQ. ID. NO. 15975	285-AlaGlySerGluThrLeu-290
a128-1
AMPHI Regions - AMPHI
SEQ. ID. NO. 15976	43-AlaGlnThrHisThrGlyTrpAlaAsnThrValGluProLeuThrGlyIleThrGlu
	ArgValGlyArgIleTrpGlyValValSerHisLeuAsnSerValThrAspThrProGlu-81
SEQ. ID. NO. 15977	85-AlaTyrAsnGluLeuMetProGluIle-93
SEQ. ID. NO. 15978	102-GlnAspIleGluLeuTyrAsnArgPheLysThrIleLysAsnSerProGluPheAsp-120
SEQ. ID. NO. 15979	166-PheSerGlnAsnValLeuAspAlaThrAsp-175
SEQ. ID. NO. 15980	189-GlyIleProGluAspAla-194
SEQ. ID. NO. 15981	2118-HisTyrLeuAlaVal-222
SEQ. ID. NO. 15982	231-LeuArgGluGlnIleTyr-236
SEQ. ID. NO. 15983	245-GluLeuSerAspAspGlyLysPheAspAsnThrAlaAsnIleAspArgThrLeuGluAsnAlaLeu-266
SEQ. ID. NO. 15984	269-AlaLysLeuLeuGlyPheLysAsnTyrAlaGlu-279
SEQ. ID. NO. 15985	286-MetAlaAspThrProGluGlnValLeuAsnPheLeuHisAspLeuAlaArgArgAla-304
SEQ. ID. NO. 15986	313-AlaGluValLysAlaPhe-318
SEQ. ID. NO. 15987	359-GlyLysValLeuAsnGlyLeuPheAlaGlnIleLysLysLeuTyrGly-374
SEQ. ID. NO. 15988	425-GlyArgArgArgPhe-429
SEQ. ID. NO. 15989	472-LeuHisHisLeuLeuThrGlnValAspGluLeu-482
SEQ. ID. NO. 15990	496-GluLeuProSerGlnPhe-501
SEQ. ID. NO. 15991	565-GlyArgLeuLysAsnTrpGlnGlnValLeuAspSerVal-577
SEQ. ID. NO. 15992	584-ValArgProProGluTyrAsnArgPheAlaAsnSerPheGlyHisIlePheAlaGlyGly-603
SEQ. ID. NO. 15993	610-SerTyrAlaTrpAlaGlu-615
SEQ. ID. NO. 15994	623-AlaAlaPheGluGluSerAspAsp-630
SEQ. ID. NO. 15995	636-LysArgPheTrpGlnGluIleLeuAla-644
SEQ. ID. NO. 15996	651-AlaAlaGluSerPheLysAlaPheArg-659
Antigenic Index - Jameson-Wolf
SEQ. ID. NO. 15997	9-LeuGlyGluGluProArgPheAspGlnIleLysThrGluAspIleLysProAlaLeu-27
SEQ. ID. NO. 15998	32-AlaGluAlaArgGluGlnIleAla-39
SEQ. ID. NO. 15999	43-AlaGlnThrHisThrGlyTrp-49
SEQ. ID. NO. 16000	51-AsnThrValGluProLeuThr-57

TABLE 1-continued

| | |
|---|---|
| SEQ. ID. NO. 16001 | 59-IleThrGluArgValGlyArgIleTrp-67 |
| SEQ. ID. NO. 16002 | 75-SerValThrAspThrProGluLeuArgAlaAlaTyr-86 |
| SEQ. ID. NO. 16003 | 100-IleGlyGlnAspIleGluLeuTyrAsnArgPheLysThrIleLysAsnSerProGluPheAspThr-121 |
| SEQ. ID. NO. 16004 | 123-SerHisAlaGlnLysThrLysLeuAsnHisAspLeuArgAsp-136 |
| SEQ. ID. NO. 16005 | 140-SerGlyAlaGluLeuProProGluGlnGlnAlaGluLeuAlaLysLeuGlnThrGluGlyAlaGlnLeu-162 |
| SEQ. ID. NO. 16006 | 165-LysPheSerGlnAsnVal-170 |
| SEQ. ID. NO. 16007 | 172-AspAlaThrAspAla-176 |
| SEQ. ID. NO. 16008 | 190-IleProGluAspAla-194 |
| SEQ. ID. NO. 16009 | 202-AlaGlnSerGluGlyLysThrGlyTyrLys-211 |
| SEQ. ID. NO. 16010 | 226-AlaAspAsnArgLysLeuArgGluGlnIle-235 |
| SEQ. ID. NO. 16011 | 240-ValThrArgAlaSerGluLeuSerAspAspGlyLysPheAspAsnThrAlaAsnIleAspArgThrLeuGlu-263 |
| SEQ. ID. NO. 16012 | 285-LysMetAlaAspThrProGluGln-292 |
| SEQ. ID. NO. 16013 | 300-LeuAlaArgArgAlaLysProTyrAlaGluLysAspLeuAlaGlu-314 |
| SEQ. ID. NO. 16014 | 316-LysAlaPheAlaArgGluSerLeuGly-324 |
| SEQ. ID. NO. 16015 | 335-TyrAlaGlyGluLysLeuArgGluAlaLysTyrAlaPheSerGluThrGluValLysLys-354 |
| SEQ. ID. NO. 16016 | 376-GlyPheThrGluLysThrVal-382 |
| SEQ. ID. NO. 16017 | 387-LysAspValArgTyrPheGluLeuGlnGlnAsnGlyGluThrIle-401 |
| SEQ. ID. NO. 16018 | 409-TyrAlaArgGluGlyLysArgGlyGlyAla-418 |
| SEQ. ID. NO. 16019 | 420-MetAsnAspTyrLysGlyArgArgArgPheSerAspGlyThrLeu-434 |
| SEQ. ID. NO. 16020 | 446-ThrProProValGlyGlyLysGluAlaArgLeuSerHisAspGlu-460 |
| SEQ. ID. NO. 16021 | 478-GlnValAspGluLeuGlyVal-484 |
| SEQ. ID. NO. 16022 | 496-GluLeuProSerGln-500 |
| SEQ. ID. NO. 16023 | 516-SerAlaHisGluGluThrGlyVal-523 |
| SEQ. ID. NO. 16024 | 560-SerGluAspAspGluGlyArgLeuLysAsn-569 |
| SEQ. ID. NO. 16025 | 575-AspSerValArgLysGluValAlaValValArgProProGluTyrAsnArgPhe-592 |
| SEQ. ID. NO. 16026 | 605-SerAlaGlyTyrTyrSerTyr-611 |
| SEQ. ID. NO. 16027 | 625-PheGluGluSerAspAspValAlaAlaThrGlyLysArgPheTrp-639 |
| SEQ. ID. NO. 16028 | 646-GlyGlySerArgSerAlaAlaGluSerPheLysAlaPheArgGlyArgGluProSerIle-665 |
| SEQ. ID. NO. 16029 | 669-LeuArgHisSerGlyPheAspAsnAlaAla-678 |
| Hydrophilic Regions - Hopp-Woods | |
| SEQ. ID. NO. 16030 | 9-LeuGlyGluGluProArgPheAspGlnIleLysThrGluAspIleLysPro-25 |
| SEQ. ID. NO. 16031 | 32-AlaGluAlaArgGluGlnIleAla-39 |
| SEQ. ID. NO. 16032 | 59-IleThrGluArgValGly-64 |
| SEQ. ID. NO. 16033 | 77-ThrAspThrProGluLeuArgAlaAlaTyr-86 |
| SEQ. ID. NO. 16034 | 100-IleGlyGlnAspIleGluLeu-106 |
| SEQ. ID. NO. 16035 | 111-LysThrIleLysAsnSerProGluPheAspThr-121 |
| SEQ. ID. NO. 16036 | 123-SerHisAlaGlnLysThrLysLeuAsnHisAspLeuArgAsp-136 |
| SEQ. ID. NO. 16037 | 143-GluLeuProProGluGlnGlnAlaGluLeuAlaLysLeuGlnThrGluGlyAlaGlnLeu-162 |
| SEQ. ID. NO. 16038 | 190-IleProGluAspAla-194 |
| SEQ. ID. NO. 16039 | 202-AlaGlnSerGluGlyLysThrGlyTyr-210 |
| SEQ. ID. NO. 16040 | 226-AlaAspAsnArgLysLeuArgGluGlnIle-235 |
| SEQ. ID. NO. 16041 | 242-ArgAlaSerGluLeuSerAspAspGlyLysPheAspAsn-254 |
| SEQ. ID. NO. 16042 | 256-AlaAsnIleAspArgThrLeuGlu-263 |
| SEQ. ID. NO. 16043 | 285-LysMetAlaAspThrProGlu-291 |
| SEQ. ID. NO. 16044 | 300-LeuAlaArgArgAlaLysProTyrAlaGluLysAspLeuAlaGlu-314 |
| SEQ. ID. NO. 16045 | 316-LysAlaPheAlaArgGluSerLeuGly-324 |
| SEQ. ID. NO. 16046 | 335-TyrAlaGlyGluLysLeuArgGluAlaLysTyrAlaPheSerGluThrGluValLysLys-354 |
| SEQ. ID. NO. 16047 | 377-PheThrGluLysThr-381 |
| SEQ. ID. NO. 16048 | 387-LysAspValArgTyr-391 |
| SEQ. ID. NO. 16049 | 396-GlnAsnGlyGluThr-400 |
| SEQ. ID. NO. 16050 | 409-TyrAlaArgGluGlyLysArgGlyGly-417 |
| SEQ. ID. NO. 16051 | 423-TyrLysGlyArgArgArgPheSerAsp-431 |
| SEQ. ID. NO. 16052 | 449-ValGlyGlyLysGluAlaArgLeuSerHisAspGlu-460 |
| SEQ. ID. NO. 16053 | 478-GlnValAspGluLeuGly-483 |
| SEQ. ID. NO. 16054 | 516-SerAlaHisGluGluThrGly-522 |
| SEQ. ID. NO. 16055 | 560-SerGluAspAspGluGlyArgLeuLysAsn-569 |
| SEQ. ID. NO. 16056 | 575-AspSerValArgLysGluValAlaVal-583 |
| SEQ. ID. NO. 16057 | 585-ArgProProGluTyrAsnArg-591 |
| SEQ. ID. NO. 16058 | 625-PheGluGluSerAspAspValAlaAlaThrGly-635 |
| SEQ. ID. NO. 16059 | 647-GlySerArgSerAlaAlaGluSerPheLysAlaPheArgGlyArgGluProSerIle-665 |
| a130 | |
| AMPHI Regions - AMPHI | |
| SEQ. ID. NO. 16060 | 16-ThrLeuValSerGlyIle-21 |
| SEQ. ID. NO. 16061 | 36-GlySerGlySerPheGly-41 |
| SEQ. ID. NO. 16062 | 56-GlnProValGlyGlnLeu-61 |
| SEQ. ID. NO. 16063 | 91-AsnValProAsnAlaPro-96 |
| SEQ. ID. NO. 16064 | 110-GlnGlyPheAspThrLeuPheGlnHisAlaLeuAsnGlyPheAsnAlaMet-126 |
| SEQ. ID. NO. 16065 | 171-ThrAlaSerAlaPro-175 |
| SEQ. ID. NO. 16066 | 204-PheGluAlaThrCysGln-209 |
| SEQ. ID. NO. 16067 | 211-CysHisGlyGlySerIleProGlyIlePro-220 |
| SEQ. ID. NO. 16068 | 234-LysGlyLysGluThr-238 |
| SEQ. ID. NO. 16069 | 245-GluGlyPheAsnAlaMet-250 |
| Antigenic Index - Jameson-Wolf | |
| SEQ. ID. NO. 16070 | 1-MetLysGlnLeuArgAspAsnLysAlaGlnGlySer-12 |
| SEQ. ID. NO. 16071 | 35-AlaGlySerGlySerPheGlyAspValAspAlaThrThrGluAlaAlaThrGlnThrArgIleGlnProValGly-59 |
| SEQ. ID. NO. 16072 | 63-MetGlyAspGlyIleProValGlyGluArgGlnGlyGlu-75 |
| SEQ. ID. NO. 16073 | 87-AlaAlaAspSerAsnValProAsnAlaProLysLeuGluHisAsnGlyAspTrpAla-105 |
| SEQ. ID. NO. 16074 | 108-IleAlaGlnGlyPhe-112 |
| SEQ. ID. NO. 16075 | 126-MetProAlaLysGlyGlyAla-132 |
| SEQ. ID. NO. 16076 | 134-AspLeuThrAspGlnGluLeuLysArg-142 |

TABLE 1-continued

| | |
|---|---|
| SEQ. ID. NO. 16077 | 148-AlaAsnLysSerGlyGlySerPheProAsnProAspGluAlaAlaProAlaAspAsnAlaAla<br>SerGlyThrAlaSerAlaProAlaAspSerAlaAlaProAlaGluAlaLysAlaGluAspLysGlyAlaAla-192 |
| SEQ. ID. NO. 16078 | 197-GlyValAspGlyLysLysValPheGlu-205 |
| SEQ. ID. NO. 16079 | 221-GlyIleGlyLysLysAspAspTrpAlaProArgIleLysLysGlyLysGluThrLeuHis-240 |
| SEQ. ID. NO. 16080 | 251-ProAlaLysGlyGlyAsnAlaGlyLeuSerAspAspGluValLysAla-266 |
| SEQ. ID. NO. 16081 | 274-GlnSerGlyAlaLys-278 |
| Hydrophilic Regions - Hopp-Woods | |
| SEQ. ID. NO. 16082 | 1-MetLysGlnLeuArgAspAsnLysAlaGlnGly-11 |
| SEQ. ID. NO. 16083 | 41-GlyAspValAspAlaThrThrGluAlaAlaThr-51 |
| SEQ. ID. NO. 16084 | 68-ProValGlyGluArgGlnGlyGlu-75 |
| SEQ. ID. NO. 16085 | 87-AlaAlaAspSerAsnVal-92 |
| SEQ. ID. NO. 16086 | 96-ProLysLeuGluHisAsnGly-102 |
| SEQ. ID. NO. 16087 | 127-ProAlaLysGlyGlyAla-132 |
| SEQ. ID. NO. 16088 | 134-AspLeuThrAspGlnGluLeuLysArg-142 |
| SEQ. ID. NO. 16089 | 156-ProAsnProAspGluAlaAlaProAlaAspAsnAlaAla-168 |
| SEQ. ID. NO. 16090 | 174-AlaProAlaAspSerAlaAlaProAlaGluAlaLysAlaGluAspLysGlyAlaAla-192 |
| SEQ. ID. NO. 16091 | 198-ValAspGlyLysLysValPheGlu-205 |
| SEQ. ID. NO. 16092 | 222-IleGlyLysLysAspAspTrpAlaProArgIleLysLysGlyLysGluThrLeuHis-240 |
| SEQ. ID. NO. 16093 | 251-ProAlaLysGlyGlyAsn-256 |
| SEQ. ID. NO. 16094 | 258-GlyLeuSerAspAspGluValLysAla-266 |
| a132-2 | |
| AMPHI Regions - AMPHI | |
| SEQ. ID. NO. 16095 | 13-IleIleSerAlaLeuAlaVal-19 |
| SEQ. ID. NO. 16096 | 70-AlaThrCysMetAlaMetVal-76 |
| SEQ. ID. NO. 16097 | 92-ValGlnGlnThrGlnGlnAlaProLysProValSerAsnThr-105 |
| Antigenic Index - Jameson-Wolf | |
| SEQ. ID. NO. 16098 | 26-GlnHisGlyLysGlyAlaAspAla-33 |
| SEQ. ID. NO. 16099 | 38-GlySerGlySerGlySerAla-44 |
| SEQ. ID. NO. 16100 | 81-HisThrThrLysHisGlyLeuAspPhe-89 |
| SEQ. ID. NO. 16101 | 91-AsnValGlnGlnThrGlnGlnAlaProLysProValSerAsnThrGluProSerAlaProValProGlnGlnGlnLys-116 |
| Hydrophilic Regions - Hopp-Woods | |
| SEQ. ID. NO. 16102 | 28-GlyLysGlyAlaAspAla-33 |
| SEQ. ID. NO. 16103 | 97-GlnAlaProLysProValSerAsnThrGluProSerAla-109 |
| a134 | |
| AMPHI Regions - AMPHI | |
| SEQ. ID. NO. 16104 | 39-IleGlnSerAlaGlyThrVal-45 |
| SEQ. ID. NO. 16105 | 47-GlyLysLysThrGly-51 |
| SEQ. ID. NO. 16106 | 56-SerAspTrpMetAspIleGluLysGlnArg-65 |
| SEQ. ID. NO. 16107 | 83-ValAsnLeuLeuAspThrProGlyHis-91 |
| SEQ. ID. NO. 16108 | 97-AspThrTyrArgValLeuThrAlaVal-105 |
| SEQ. ID. NO. 16109 | 114-AlaAlaLysGlyValGlu-119 |
| SEQ. ID. NO. 16110 | 123-IleLysLeuLeuAsnValCysArg-130 |
| SEQ. ID. NO. 16111 | 142-LysTyrAspArgGluVal-147 |
| SEQ. ID. NO. 16112 | 149-AspSerLeuGluLeuLeuAspGluValGluAsnIleLeuGln-162 |
| SEQ. ID. NO. 16113 | 176-LysAsnPheLysGlyValTyrHisIleLeu-185 |
| SEQ. ID. NO. 16114 | 201-HisGluPheAspIleIleLysGlyIleAspAsn-211 |
| SEQ. ID. NO. 16115 | 254-PheGlySerAlaIle-258 |
| SEQ. ID. NO. 16116 | 265-GluIleLeuAsnSerLeuIleGluTrpAla-274 |
| SEQ. ID. NO. 16117 | 322-LysPheGluArgGlyMetLys-328 |
| SEQ. ID. NO. 16118 | 361-AspIleIleGlyIleProAsnHis-368 |
| SEQ. ID. NO. 16119 | 377-PheSerGluGlyGlu-381 |
| SEQ. ID. NO. 16120 | 395-LeuPheArgSerValArgIleLys-402 |
| SEQ. ID. NO. 16121 | 404-ProLeuLysIleLysGln-409 |
| SEQ. ID. NO. 16122 | 411-GlnLysGlyLeuGlnGlnLeuGlyGlu-419 |
| SEQ. ID. NO. 16123 | 423-ValGlnValPheLysProMetSer-430 |
| SEQ. ID. NO. 16124 | 449-SerArgLeuAlaAsnGluTyr-455 |
| SEQ. ID. NO. 16125 | 481-AlaGluPheGluLysAlaAsn-487 |
| SEQ. ID. NO. 16126 | 515-ArgTrpProAspIle-519 |
| Antigenic Index - Jameson-Wolf | |
| SEQ. ID. NO. 16127 | 4-GluIleLeuAspGlnValArgArgArgArgThrPhe-15 |
| SEQ. ID. NO. 16128 | 19-SerHisProAspAlaGlyLysThrThrLeuThr-29 |
| SEQ. ID. NO. 16129 | 43-GlyThrValLysGlyLysLysThrGlyLysPheAlaThr-55 |
| SEQ. ID. NO. 16130 | 57-AspTrpMetAspIleGluLysGlnArgGly-66 |
| SEQ. ID. NO. 16131 | 76-PheAspTyrLysAspHisThrVal-83 |
| SEQ. ID. NO. 16132 | 85-LeuLeuAspThrProGlyHisGlnAspPheSerGluAspThrTyrArg-100 |
| SEQ. ID. NO. 16133 | 113-AspAlaAlaLysGlyValGlu-119 |
| SEQ. ID. NO. 16134 | 129-CysArgLeuArgAsnThrPro-135 |
| SEQ. ID. NO. 16135 | 140-MetAsnLysTyrAspArgGluValArgAspSerLeuGluLeuLeuAspGluValGluAsn-159 |
| SEQ. ID. NO. 16136 | 173-GlyMetGlyLysAsnPheLys-179 |
| SEQ. ID. NO. 16137 | 194-AlaGlyGlyGluArgLeuProHis-201 |
| SEQ. ID. NO. 16138 | 207-LysGlyIleAspAsnProGluLeuGluGlnArgPheProLeu-220 |
| SEQ. ID. NO. 16139 | 223-GlnGlnLeuArgAspGluIleGluLeu-231 |
| SEQ. ID. NO. 16140 | 235-AlaSerAsnGluPheAsnLeu-241 |
| SEQ. ID. NO. 16141 | 275-ProAlaProLysProArgAspAlaThrValArgMetValGluProAspGluProLysPhe-294 |
| SEQ. ID. NO. 16142 | 302-GlnAlaAsnMetAspProLysHisArgAspArgIleAla-314 |
| SEQ. ID. NO. 16143 | 317-ArgValCysSerGlyLysPheGluArgGlyMetLysMetLysHisLeuArgIleAsnArgGluIleAla-339 |
| SEQ. ID. NO. 16144 | 348-SerHisAspArgGluLeuValGlu-355 |
| SEQ. ID. NO. 16145 | 365-IleProAsnHisGly-369 |
| SEQ. ID. NO. 16146 | 373-IleGlyAspSerPheSerGluGlyGluGln-382 |
| SEQ. ID. NO. 16147 | 399-ValArgIleLysAsnProLeuLysIleLysGlnLeuGlnLysGlyLeuGlnGlnLeuGlyGluGluGlyAla-422 |

| | |
|---|---|
| SEQ. ID. NO. 16148 | 450-ArgLeuAlaAsnGluTyrGlyVal-457 |
| SEQ. ID. NO. 16149 | 473-SerCysAspAspLysLysLysLeuAlaGluPheGluLysAlaAsnAla-488 |
| SEQ. ID. NO. 16150 | 503-AlaProAsnArgValAsnLeu-509 |
| SEQ. ID. NO. 16151 | 511-LeuThrGlnGluArgTrpProAspIleVal-520 |
| SEQ. ID. NO. 16152 | 523-GluThrArgGluHisSerVal-529 |
| Hydrophilic Regions - Hopp-Woods | |
| SEQ. ID. NO. 16153 | 4-GluIleLeuAspGlnValArgArgArgArgThr-14 |
| SEQ. ID. NO. 16154 | 21-ProAspAlaGlyLys-25 |
| SEQ. ID. NO. 16155 | 43-GlyThrValLysGlyLysLysThrGlyLys-52 |
| SEQ. ID. NO. 16156 | 59-MetAspIleGluLysGlnArgGly-66 |
| SEQ. ID. NO. 16157 | 77-AspTyrLysAspHisThr-82 |
| SEQ. ID. NO. 16158 | 92-GlnAspPheSerGluAspThrTyr-99 |
| SEQ. ID. NO. 16159 | 113-AspAlaAlaLysGlyValGlu-119 |
| SEQ. ID. NO. 16160 | 129-CysArgLeuArgAsn-133 |
| SEQ. ID. NO. 16161 | 142-LysTyrAspArgGluValArgAspSerLeuGluLeuLeuAspGluValGluAsn-159 |
| SEQ. ID. NO. 16162 | 194-AlaGlyGlyGluArgLeuProHis-201 |
| SEQ. ID. NO. 16163 | 207-LysGlyIleAspAsnProGluLeuGluGlnArgPheProLeu-220 |
| SEQ. ID. NO. 16164 | 223-GlnGlnLeuArgAspGluIleGluLeu-231 |
| SEQ. ID. NO. 16165 | 277-ProLysProArgAspAlaThrValArgMetValGluProAspGluProLysPhe-294 |
| SEQ. ID. NO. 16166 | 305-MetAspProLysHisArgAspArgIleAla-314 |
| SEQ. ID. NO. 16167 | 319-CysSerGlyLysPheGluArgGlyMetLysMetLysHisLeuArgIleAsnArgGluIleAla-339 |
| SEQ. ID. NO. 16168 | 348-SerHisAspArgGluLeuValGlu-355 |
| SEQ. ID. NO. 16169 | 376-SerPheSerGluGlyGluGln-382 |
| SEQ. ID. NO. 16170 | 399-ValArgIleLysAsnProLeuLysIleLysGlnLeuGlnLysGlyLeu-414 |
| SEQ. ID. NO. 16171 | 417-LeuGlyGluGluGlyAla-422 |
| SEQ. ID. NO. 16172 | 473-SerCysAspAspLysLysLysLeuAlaGluPheGluLysAlaAsnAla-488 |
| SEQ. ID. NO. 16173 | 512-ThrGlnGluArgTrpPro-517 |
| SEQ. ID. NO. 16174 | 523-GluThrArgGluHisSerVal-529 |
| a135 | |
| AMPHI Regions - AMPHI | |
| SEQ. ID. NO. 16175 | 29-ThrIleThrArgGlnLeuAlaAlaLeu-37 |
| SEQ. ID. NO. 16176 | 85-GluTyrThrAlaAsnLeu-90 |
| SEQ. ID. NO. 16177 | 169-AspIleAspGlyLeuTyrThr-175 |
| SEQ. ID. NO. 16178 | 185-ValArgLeuAspLysIleGluHis-192 |
| SEQ. ID. NO. 16179 | 212-GlyMetLeuThrLysIle-217 |
| SEQ. ID. NO. 16180 | 236-LeuLysProAspAla-240 |
| SEQ. ID. NO. 16181 | 242-AlaGluAlaAlaAspAsnGln-248 |
| SEQ. ID. NO. 16182 | 284-AlaGluHisAlaLeuSer-289 |
| SEQ. ID. NO. 16183 | 300-IleAlaGlyIleGluGly-305 |
| SEQ. ID. NO. 16184 | 308-SerArgMetAspThrValThrValTyr-316 |
| SEQ. ID. NO. 16185 | 318-LysAlaThrLysGlnPro-323 |
| SEQ. ID. NO. 16186 | 335-AlaAlaGluAspLeuLeuLysLeuArg-343 |
| Antigenic Index - Jameson-Wolf | |
| SEQ. ID. NO. 16187 | 1-MetLysTyrLysArgIleVal-7 |
| SEQ. ID. NO. 16188 | 11-GlyThrSerSerIleThrHisSerAspGlySerLeuSerArgGlyLysIle-27 |
| SEQ. ID. NO. 16189 | 60-GlyPheLysLysArgProValLysIleAlaAspLysGlnAlaSer-74 |
| SEQ. ID. NO. 16190 | 90-LeuSerSerAspGlyIle-95 |
| SEQ. ID. NO. 16191 | 105-AlaAspPheAlaAspLysArgArgTyrGlnAsnAlaGlyGly-118 |
| SEQ. ID. NO. 16192 | 124-LeuGlnArgArgAlaVal-129 |
| SEQ. ID. NO. 16193 | 132-IleAsnGluAsnAspThrValSerValGluGluLeuLysIleGlyAspAsnAspThrLeu-151 |
| SEQ. ID. NO. 16194 | 176-GlyAsnProAsnSerAsnProAspAlaValArgLeuAspLysIleGluHisIleAsn-194 |
| SEQ. ID. NO. 16195 | 202-GlyGlySerGlySerAlaAsnGlyThrGly-211 |
| SEQ. ID. NO. 16196 | 215-ThrLysIleLysAla-219 |
| SEQ. ID. NO. 16197 | 224-ThrGluSerGlyVal-228 |
| SEQ. ID. NO. 16198 | 233-CysSerSerLeuLysProAspAlaLeuAlaGluAlaAlaAspAsnGlnAlaAspGly-251 |
| SEQ. ID. NO. 16199 | 257-ArgAlaLysGlyLeuArgThrGlnLysGln-266 |
| SEQ. ID. NO. 16200 | 271-TyrSerGluSerArgGlyGlyValTyrValAspGluGlyAlaGluHisAlaLeuSerGluGlnGlyLysSerLeuLeu-296 |
| SEQ. ID. NO. 16201 | 305-GlyHisPheSerArgMetAspThr-312 |
| SEQ. ID. NO. 16202 | 317-SerLysAlaThrLysGlnProLeuGlyLysGlyArgVal-329 |
| SEQ. ID. NO. 16203 | 335-AlaAlaGluAspLeuLeuLysLeuArgLysAlaLys-346 |
| SEQ. ID. NO. 16204 | 350-IleHisArgAspAspTrpIleSer-357 |
| Hydrophilic Regions - Hopp-Woods | |
| SEQ. ID. NO. 16205 | 1-MetLysTyrLysArgIleVal-7 |
| SEQ. ID. NO. 16206 | 16-ThrHisSerAspGlySerLeuSerArgGlyLysIle-27 |
| SEQ. ID. NO. 16207 | 60-GlyPheLysLysArgProValLysIleAlaAspLysGlnAlaSer-74 |
| SEQ. ID. NO. 16208 | 105-AlaAspPheAlaAspLysArgArgTyrGlnAsn-115 |
| SEQ. ID. NO. 16209 | 124-LeuGlnArgArgAlaVal-129 |
| SEQ. ID. NO. 16210 | 133-AsnGluAsnAspThrValSerValGluGluLeuLysIleGlyAspAsnAspThrLeu-151 |
| SEQ. ID. NO. 16211 | 178-ProAsnSerAsnProAspAlaValArgLeuAspLysIleGluHisIleAsn-194 |
| SEQ. ID. NO. 16212 | 215-ThrLysIleLysAla-219 |
| SEQ. ID. NO. 16213 | 236-LeuLysProAspAlaLeuAlaGluAlaAlaAspAsnGlnAlaAsp-250 |
| SEQ. ID. NO. 16214 | 257-ArgAlaLysGlyLeuArgThrGlnLys-265 |
| SEQ. ID. NO. 16215 | 272-SerGluSerArgGly-276 |
| SEQ. ID. NO. 16216 | 278-ValTyrValAspGluGlyAlaGluHisAlaLeuSerGluGlnGlyLys-293 |
| SEQ. ID. NO. 16217 | 306-HisPheSerArgMetAspThr-312 |
| SEQ. ID. NO. 16218 | 318-LysAlaThrLysGlnProLeuGlyLysGlyArgVal-329 |
| SEQ. ID. NO. 16219 | 335-AlaAlaGluAspLeuLeuLysLeuArgLysAlaLys-346 |
| SEQ. ID. NO. 16220 | 351-HisArgAspAspTrp-355 |

TABLE 1-continued a136
AMPHI Regions - AMPHI
SEQ. ID. NO. 16221   50-IleArgGlnCysIleArgGln-56
SEQ. ID. NO. 16222   84-GlnCysHisAspGlyIleLysGlnLeuPheLysArgPheIleIleAspGlyPheLysProIleGlyArgHis-107
SEQ. ID. NO. 16223   119-CysValLysIleAla-123
SEQ. ID. NO. 16224   148-ArgHisCysGlnAsn-152
SEQ. ID. NO. 16225   170-GlnHisPheGlyGlnPro-175
SEQ. ID. NO. 16226   177-GluArgCysGlnPheVal-182
SEQ. ID. NO. 16227   194-AsnLeuValAlaThr-198
SEQ. ID. NO. 16228   210-GlnPheAlaGlnPro-214
SEQ. ID. NO. 16229   216-PheGlyCysPheGlyLysPheSerGlyIleHisHisPhe-228
SEQ. ID. NO. 16230   247-LysAlaThrLysProGlnThrValGlnIleValArg-258
Antigenic Index - Jameson-Wolf
SEQ. ID. NO. 16231   1-MetGluThrAsnAla-5
SEQ. ID. NO. 16232   34-AlaAspGlyLeuArgLeuValAspAspArgLeuProVal-46
SEQ. ID. NO. 16233   48-ValAspIleArgGlnCysIle-54
SEQ. ID. NO. 16234   69-LeuGlnThrAspSer-73
SEQ. ID. NO. 16235   84-GlnCysHisAspGlyIleLysGlnLeuPhe-93
SEQ. ID. NO. 16236   99-AspGlyPheLysProIleGlyArgHisAsnIle-109
SEQ. ID. NO. 16237   139-IleArgHisArgGlyGlyCysPheHisArgHisCysGlnAsnGlnProPheAsp-156
SEQ. ID. NO. 16238   159-ThrPheGlyGlyGlyLysLeuArg-166
SEQ. ID. NO. 16239   171-HisPheGlyGlnProValGluArg-178
SEQ. ID. NO. 16240   184-ProAlaGlnGlnArgArgHisLysThr-192
SEQ. ID. NO. 16241   214-ProProPheGlyCysPheGlyLysPheSerGly-224
SEQ. ID. NO. 16242   242-AsnLeuAsnGlnAspLysAlaThrLysProGln-252
SEQ. ID. NO. 16243   257-ValArgGlnGlyGluAlaThrProTyr-265
SEQ. ID. NO. 16244   270-AsnProLeuTyrArgArgAsnAlaVal-278
Hydrophilic Regions - Hopp-Woods
SEQ. ID. NO. 16245   35-AspGlyLeuArgLeuValAspAspArgLeuProVal-46
SEQ. ID. NO. 16246   48-ValAspIleArgGlnCysIle-54
SEQ. ID. NO. 16247   87-AspGlyIleLysGlnLeuPhe-93
SEQ. ID. NO. 16248   185-AlaGlnGlnArgArgHisLysThr-192
SEQ. ID. NO. 16249   244-AsnGlnAspLysAlaThrLysProGln-252
SEQ. ID. NO. 16250   273-TyrArgArgAsnAlaVal-278
a137
AMPHI Regions - AMPHI
SEQ. ID. NO. 16251   24-LeuSerTyrIleLeuGlyPhe-30
SEQ. ID. NO. 16252   49-ThrLysGluSerLeu-53
SEQ. ID. NO. 16253   55-AspPheLeuThrTrpGly-60
SEQ. ID. NO. 16254   78-PheSerAspTyrLeuAlaHisProLeuAspIlePheLysValTrpGluGlyGly-95
SEQ. ID. NO. 16255   101-GlyPheLeuGlyValValIle-107
SEQ. ID. NO. 16256   120-PheLeuLysLeuMetAspThrValAlaProLeuValPro-132
SEQ. ID. NO. 16257   139-ArgIleGlyAsnPheIle-144
SEQ. ID. NO. 16258   149-TrpGlyArgValThrAspIleAsnAlaPhe-158
SEQ. ID. NO. 16259   178-ProLeuTrpAlaGluTrpLeuGlnGlnTyr-187
SEQ. ID. NO. 16260   190-LeuProArgHisProSerGlnLeu-197
SEQ. ID. NO. 16261   232-TyrGlyIlePheArgPheIleAlaGluPheAlaArgGlnProAspAspTyrLeuGly-250
Antigenic Index - Jameson-Wolf
SEQ. ID. NO. 16262   36-LeuGlyArgArgArgIleAlaGln-43
SEQ. ID. NO. 16263   48-PheThrLysGluSerLeuAspAsp-55
SEQ. ID. NO. 16264   92-TrpGluGlyGlyMet-96
SEQ. ID. NO. 16265   113-GlyArgLysHisGlyIle-118
SEQ. ID. NO. 16266   136-AlaSerGlyArgIle-140
SEQ. ID. NO. 16267   164-ProGlnAlaArgTyrGluAspLeuGluAla-173
SEQ. ID. NO. 16268   191-ProArgHisProSerGlnLeu-197
SEQ. ID. NO. 16269   214-PheSerLysLysGlnArgProThrGly-222
SEQ. ID. NO. 16270   241-PheAlaArgGlnProAspAspTyrLeu-249
SEQ. ID. NO. 16271   277-PheGlyMetLysLysGlnHis-283
Hydrophilic Regions - Hopp-Woods
SEQ. ID. NO. 16272   37-GlyArgArgArgIleAla-42
SEQ. ID. NO. 16273   48-PheThrLysGluSerLeuAsp-54
SEQ. ID. NO. 16274   166-AlaArgTyrGluAspLeuGluAla-173
SEQ. ID. NO. 16275   216-LysLysGlnArgProThrGly-222
SEQ. ID. NO. 16276   241-PheAlaArgGlnProAspAspTyr-248
SEQ. ID. NO. 16277   278-GlyMetLysLysGlnHis-283
a138
AMPHI Regions - AMPHI
SEQ. ID. NO. 16278   21-ProTyrIleArgArgPheSerGlySer-29
SEQ. ID. NO. 16279   74-AsnAlaMetLeuGluLysVal-80
SEQ. ID. NO. 16280   85-GluPheValGlnGlyMet-90
SEQ. ID. NO. 16281   109-ValAsnLysGluIleValSerMetIleAsnThrTyrGly-121
SEQ. ID. NO. 16282   152-IleGlyGlnValGlyThrValGluSerIle-161
SEQ. ID. NO. 16283   163-ThrGlyLeuValLysGlyLeu-169
SEQ. ID. NO. 16284   199-GlyLysLeuAlaGluGluLeu-205
SEQ. ID. NO. 16285   213-MetThrAsnIleAlaGlyValMetAspLysThrGlyAsnLeuLeuThrLysLeuThr-231
SEQ. ID. NO. 16286   234-ArgIleAspGluLeuIle-239
SEQ. ID. NO. 16287   247-GlyMetLeuProLysIleAlaSerAlaValGluAlaAlaValAsn-261
SEQ. ID. NO. 16288   276-AlaLeuLeuLeuGluIlePheThrAspAla-285
Antigenic Index - Jameson-Wolf
SEQ. ID. NO. 16289   1-MetGluSerGluAsnIle-6

TABLE 1-continued

| | |
|---|---|
| SEQ. ID. NO. 16290 | 9-AlaAlaAspLysAlaArgIleLeu-16 |
| SEQ. ID. NO. 16291 | 23-IleArgArgPheSerGlySer-29 |
| SEQ. ID. NO. 16292 | 35-TyrGlyGlyAsnAlaMetThr-41 |
| SEQ. ID. NO. 16293 | 43-ProAlaLeuLysGluGlyPheAla-50 |
| SEQ. ID. NO. 16294 | 68-GlyGlyGlyProGln-72 |
| SEQ. ID. NO. 16295 | 76-MetLeuGluLysValGlyLysLysGlyGluPhe-86 |
| SEQ. ID. NO. 16296 | 91-ArgValThrAspLysGluAlaMetAsp-99 |
| SEQ. ID. NO. 16297 | 109-ValAsnLysGluIle-113 |
| SEQ. ID. NO. 16298 | 128-SerGlyArgAspAspHisPheIleLysAlaLysLysLeuLeuIleAspThrProGluGlnAsnGlyValAspIleGlyGln-154 |
| SEQ. ID. NO. 16299 | 159-GluSerIleAspThrGlyLeu-165 |
| SEQ. ID. NO. 16300 | 169-LeuIleGluArgGlyCysIle-175 |
| SEQ. ID. NO. 16301 | 182-GlyValGlyGluLysGlyGluAla-189 |
| SEQ. ID. NO. 16302 | 200-LysLeuAlaGluGluLeuAsnAlaGluLys-209 |
| SEQ. ID. NO. 16303 | 219-ValMetAspLysThrGlyAsnLeuLeuThrLysLeuThrProLysArgIleAspGluLeuIleAla-240 |
| SEQ. ID. NO. 16304 | 259-AlaValAsnGlyValLys-264 |
| SEQ. ID. NO. 16305 | 269-IleAspGlyArgValProAsnAla-276 |
| SEQ. ID. NO. 16306 | 292-LeuGlyGlyGlyGluAspAla-298 |
| Hydrophilic Regions - Hopp-Woods | |
| SEQ. ID. NO. 16307 | 1-MetGluSerGluAsn-5 |
| SEQ. ID. NO. 16308 | 9-AlaAlaAspLysAlaArgIleLeu-16 |
| SEQ. ID. NO. 16309 | 43-ProAlaLeuLysGluGlyPheAla-50 |
| SEQ. ID. NO. 16310 | 76-MetLeuGluLysValGlyLysLysGlyGluPhe-86 |
| SEQ. ID. NO. 16311 | 91-ArgValThrAspLysGluAlaMetAsp-99 |
| SEQ. ID. NO. 16312 | 109-ValAsnLysGluIle-113 |
| SEQ. ID. NO. 16313 | 128-SerGlyArgAspAspHisPheIleLysAlaLysLysLeuLeuIleAspThrProGluGlnAsnGlyValAsp-151 |
| SEQ. ID. NO. 16314 | 183-ValGlyGluLysGlyGluAla-189 |
| SEQ. ID. NO. 16315 | 200-LysLeuAlaGluGluLeuAsnAlaGluLys-209 |
| SEQ. ID. NO. 16316 | 219-ValMetAspLysThrGly-224 |
| SEQ. ID. NO. 16317 | 230-LeuThrProLysArgIleAspGluLeuIleAla-240 |
| SEQ. ID. NO. 16318 | 269-IleAspGlyArgVal-273 |
| SEQ. ID. NO. 16319 | 294-GlyGlyGluAspAla-298 |
| a140 | |
| AMPHI Regions - AMPHI | |
| SEQ. ID. NO. 16320 | 10-TyrLeuAsnArgThr-14 |
| SEQ. ID. NO. 16321 | 26-IleGlyArgAspTyrSerPhePhe-33 |
| SEQ. ID. NO. 16322 | 45-SerLeuAspSerValGluLysThrAlaGly-54 |
| SEQ. ID. NO. 16323 | 68-AsnAlaAlaArgThrAlaSer-74 |
| SEQ. ID. NO. 16324 | 108-SerAlaThrProGluThrValThrValGluThrAlaAla-118 |
| SEQ. ID. NO. 16325 | 135-ArgAlaAlaAlaAlaValGlnHisAlaAsnAlaAlaAspGlyValArgIlePheAsnAsnLeuAlaAlaThrVal-159 |
| SEQ. ID. NO. 16326 | 175-LeuLysAlaValSerAspGlyLeuAsp-183 |
| SEQ. ID. NO. 16327 | 189-LeuArgValIleAlaGln-194 |
| SEQ. ID. NO. 16328 | 254-SerLeuPheAlaGly-258 |
| SEQ. ID. NO. 16329 | 266-IleGlyTyrLeuLysGlyLeuPheSerTyr-275 |
| SEQ. ID. NO. 16330 | 290-GluHisAlaGluGlySer-295 |
| SEQ. ID. NO. 16331 | 303-LeuGlyAlaLeuGly-307 |
| SEQ. ID. NO. 16332 | 352-GlyThrLeuValGlyLeu-357 |
| SEQ. ID. NO. 16333 | 391-GlyGlyPheThrGlyAlaThr-397 |
| SEQ. ID. NO. 16334 | 412-ArgLeuValAlaGlyLeu-417 |
| SEQ. ID. NO. 16335 | 425-AsnGlyTrpAsnGlyLeuAlaArg-432 |
| Antigenic Index - Jameson-Wolf | |
| SEQ. ID. NO. 16336 | 2-SerAlaGlyGlyLysGlyAlaGlyTyrLeuAsnArgThrGlyGlnArgValPro-19 |
| SEQ. ID. NO. 16337 | 25-LysIleGlyArgAspTyrSer-31 |
| SEQ. ID. NO. 16338 | 35-AsnIleGluThrAspGlyGlyLeu-42 |
| SEQ. ID. NO. 16339 | 47-AspSerValGluLysThrAlaGlySerGluGlyAspThrLeu-60 |
| SEQ. ID. NO. 16340 | 63-TyrValArgArgGlyAsnAlaAlaArgThrAlaSer-74 |
| SEQ. ID. NO. 16341 | 86-HisAlaValGluGlnGlyGlySerAsnLeuGlu-96 |
| SEQ. ID. NO. 16342 | 102-LeuAspAlaSerGluSerSerAlaThrProGluThrValGlu-115 |
| SEQ. ID. NO. 16343 | 117-AlaAlaAlaAspArgThrAspMetProGlyIleArgProTyrGly-131 |
| SEQ. ID. NO. 16344 | 144-AsnAlaAlaAspGly-148 |
| SEQ. ID. NO. 16345 | 160-TyrAlaAspSerThrAlaAla-166 |
| SEQ. ID. NO. 16346 | 169-AspMetGlnGlyArgArgLeuLysAlaValSerAspGlyLeuAspHisAsnAlaThrGly-188 |
| SEQ. ID. NO. 16347 | 195-ThrGlnGlnAspGlyGlyThrTrpGluGlnGlyGlyValGluGlyLysMetArgGlySerThrGln-216 |
| SEQ. ID. NO. 16348 | 221-AlaAlaLysThrGlyGluAsnThrThr-229 |
| SEQ. ID. NO. 16349 | 240-ThrTrpSerGluAsnSerAlaAsnAlaLysThrAspSer-252 |
| SEQ. ID. NO. 16350 | 259-IleArgHisAspAlaGlyAsp-265 |
| SEQ. ID. NO. 16351 | 274-SerTyrGlyArgTyrLysAsnSerIleSerArgSerThrGlyAlaAspGluHisAlaGluGlySerValAsn-297 |
| SEQ. ID. NO. 16352 | 315-AlaThrGlyAspLeuThrValGluGlyGlyLeuArg-326 |
| SEQ. ID. NO. 16353 | 333-AspAlaPheAlaGluLysGlySerAlaLeuGlyTrpSerGlyAsnSerIleThrGluGlyThr-353 |
| SEQ. ID. NO. 16354 | 362-LeuSerGlnProLeuSerAspLysAla-370 |
| SEQ. ID. NO. 16355 | 377-GlyValGluArgAspLeuAsnGlyArgAspTyrThrVal-389 |
| SEQ. ID. NO. 16356 | 399-AlaThrGlyLysThrGlyAlaArgAsnMetProHisThr-411 |
| SEQ. ID. NO. 16357 | 421-ValGluPheGlyAsnGlyTrp-427 |
| SEQ. ID. NO. 16358 | 434-SerTyrAlaGlySerLysGlnTyrGlyAsnHisSerGlyArgValGlyVal-450 |
| Hydrophilic Regions - Hopp-Woods | |
| SEQ. ID. NO. 16359 | 3-AlaGlyGlyLysGly-7 |
| SEQ. ID. NO. 16360 | 36-IleGluThrAspGly-40 |
| SEQ. ID. NO. 16361 | 47-AspSerValGluLysThrAlaGlySerGluGlyAspThr-59 |
| SEQ. ID. NO. 16362 | 64-ValArgArgGlyAsnAlaAlaArgThrAlaSer-74 |
| SEQ. ID. NO. 16363 | 86-HisAlaValGluGlnGlyGlySerAsnLeu-95 |
| SEQ. ID. NO. 16364 | 102-LeuAspAlaSerGluSerSerAlaThrProGluThrValGlu-115 |

TABLE 1-continued

| | |
|---|---|
| SEQ. ID. NO. 16365 | 117-AlaAlaAlaAspArgThrAspMetProGly-126 |
| SEQ. ID. NO. 16366 | 144-AsnAlaAlaAspGly-148 |
| SEQ. ID. NO. 16367 | 169-AspMetGlnGlyArgArgLeuLysAlaValSerAspGlyLeuAspHisAsnAlaThr-187 |
| SEQ. ID. NO. 16368 | 205-GlyGlyValGluGlyLysMetArgGlySerThr-215 |
| SEQ. ID. NO. 16369 | 223-LysThrGlyGluAsnThrThr-229 |
| SEQ. ID. NO. 16370 | 244-AsnSerAlaAsnAlaLysThrAspSer-252 |
| SEQ. ID. NO. 16371 | 259-IleArgHisAspAlaGlyAsp-265 |
| SEQ. ID. NO. 16372 | 277-ArgTyrLysAsnSerIleSerArgSerThrGlyAlaAspGluHisAlaGluGlySerVal-296 |
| SEQ. ID. NO. 16373 | 333-AspAlaPheAlaGluLysGlySer-340 |
| SEQ. ID. NO. 16374 | 364-GlnProLeuSerAspLysAla-370 |
| SEQ. ID. NO. 16375 | 377-GlyValGluArgAspLeuAsnGlyArgAspTyrThr-388 |
| SEQ. ID. NO. 16376 | 399-AlaThrGlyLysThrGlyAlaArgAsnMetPro-409 |
| a141 | |
| AMPHI Regions - AMPHI | |
| SEQ. ID. NO. 16377 | 11-GlnSerSerThrMetArgProIleGlyGluIle-21 |
| SEQ. ID. NO. 16378 | 32-IleGluProTyrGly-36 |
| SEQ. ID. NO. 16379 | 44-ProAlaGluAlaPheLysLeuPro-51 |
| SEQ. ID. NO. 16380 | 80-AlaAspAlaLeuArgHisIle-86 |
| SEQ. ID. NO. 16381 | 131-PheHisAlaIleGlyAla-136 |
| SEQ. ID. NO. 16382 | 139-AsnLeuLeuAlaAlaMetLeuAspAsn-147 |
| SEQ. ID. NO. 16383 | 174-GlnLeuArgAsnIleIleAspGlyMetGlyLysProValAspGlyValMetArgPro-192 |
| SEQ. ID. NO. 16384 | 212-AspIleSerAspLeuLysGluArgLeuGly-221 |
| SEQ. ID. NO. 16385 | 245-MetAlaAlaLeuLeuLysAspAlaIleLysProAsnLeu-257 |
| SEQ. ID. NO. 16386 | 259-GlnThrIleGluGlyThrPro-265 |
| SEQ. ID. NO. 16387 | 272-ProPheAlaAsnIleAlaHisGlyCysAsnSerValThrAlaThrArgLeuAlaLysHisLeuAlaAspTyrAla-296 |
| SEQ. ID. NO. 16388 | 330-AlaThrValArgAla-334 |
| SEQ. ID. NO. 16389 | 351-LeuAspAlaLeuGluLysGlyLeuProAsnLeuLysHisIleSerAsnLeuLysAsnValPheGly-373 |
| SEQ. ID. NO. 16390 | 406-SerLeuThrGluValTrpGlyLys-413 |
| SEQ. ID. NO. 16391 | 420-AspLeuAlaArgLysValValAsnAlaIleGluSerGln-432 |
| SEQ. ID. NO. 16392 | 473-IleAlaSerLeuGluLys-478 |
| SEQ. ID. NO. 16393 | 525-ValAlaLeuCysGlyAsnMetMetLysMetProGlyLeuProLysValProAlaAla-543 |
| Antigenic Index - Jameson-Wolf | |
| SEQ. ID. NO. 16394 | 3-PheLysThrAspAlaGluIleAlaGlnSerSerThrMetArgProIleGly-19 |
| SEQ. ID. NO. 16395 | 27-LeuAsnValAspAsnIleGluProTyrGly-36 |
| SEQ. ID. NO. 16396 | 38-TyrLysAlaLysIleAsnProAlaGluAlaPheLysLeuProGlnLysGlnGlyArg-56 |
| SEQ. ID. NO. 16397 | 64-AsnProThrProAlaGlyGluGlyLysThrThr-74 |
| SEQ. ID. NO. 16398 | 81-AspAlaLeuArgHisIleGlyLysAspSerValIleAlaLeuArgGluProSerLeuGlyPro-101 |
| SEQ. ID. NO. 16399 | 105-ValLysGlyGlyAlaAlaGlyGlyGly-113 |
| SEQ. ID. NO. 16400 | 151-GlnGlyAsnGluLeuAsnIleAspProLysArgValLeuTrp-164 |
| SEQ. ID. NO. 16401 | 166-ArgValValAspMetAsnAspArgGlnLeuArgAsnIleIleAspGlyMetGlyLysProValAspGlyValMetArgProAspGlyPheAspIle-197 |
| SEQ. ID. NO. 16402 | 211-LysAspIleSerAspLeuLysGluArgLeuGly-221 |
| SEQ. ID. NO. 16403 | 227-TyrAlaLysAspGlySerProValTyr-235 |
| SEQ. ID. NO. 16404 | 237-LysAspLeuLysAlaAsnGly-243 |
| SEQ. ID. NO. 16405 | 251-AspAlaIleLysProAsnLeu-257 |
| SEQ. ID. NO. 16406 | 287-ArgLeuAlaLysHisLeuAla-293 |
| SEQ. ID. NO. 16407 | 306-LeuGlyAlaGluLysPheCysAspIleLysCysArgLeuAlaGlyLeuLysProAspAla-325 |
| SEQ. ID. NO. 16408 | 335-LeuLysTyrAsnGlyGlyValGluArgAlaAsnLeuGlyGluGluAsnLeuAspAlaLeuGluLysGlyLeuProAsnLeu-361 |
| SEQ. ID. NO. 16409 | 383-PheValSerAspSerAspAlaGluLeuAlaMetIleGluLysAlaCysAla-399 |
| SEQ. ID. NO. 16410 | 411-TrpGlyLysGlyGlyAlaGlyGlyAlaAspLeuAlaArgLysValValAsn-427 |
| SEQ. ID. NO. 16411 | 429-IleGluSerGlnThrAsnAsnPheGly-437 |
| SEQ. ID. NO. 16412 | 444-LeuGlyIleLysAspLysIleArgAlaIleAla-454 |
| SEQ. ID. NO. 16413 | 458-TyrGlyAlaGluAspValAspPheSerAla-467 |
| SEQ. ID. NO. 16414 | 474-AlaSerLeuGluLysLeuGlyLeuAspLysMetPro-485 |
| SEQ. ID. NO. 16415 | 494-SerLeuSerAspAsnAlaLysLeu-501 |
| SEQ. ID. NO. 16416 | 503-GlyCysProGluAspPheArgIle-510 |
| SEQ. ID. NO. 16417 | 534-MetProGlyLeuPro-538 |
| SEQ. ID. NO. 16418 | 541-ProAlaAlaGluLysIleAspValAspAlaGluGly-552 |
| Hydrophilic Regions - Hopp-Woods | |
| SEQ. ID. NO. 16419 | 3-PheLysThrAspAlaGluIleAlaGln-11 |
| SEQ. ID. NO. 16420 | 38-TyrLysAlaLysIleAsnPro-44 |
| SEQ. ID. NO. 16421 | 46-GluAlaPheLysLeuProGlnLysGlnGlyArg-56 |
| SEQ. ID. NO. 16422 | 67-ProAlaGlyGluGlyLysThr-73 |
| SEQ. ID. NO. 16423 | 81-AspAlaLeuArgHisIleGlyLysAspSerValIleAlaLeuArgGluProSer-98 |
| SEQ. ID. NO. 16424 | 155-LeuAsnIleAspProLysArgValLeuTrp-164 |
| SEQ. ID. NO. 16425 | 166-ArgValValAspMetAsnAspArgGlnLeuArgAsnIleIle-179 |
| SEQ. ID. NO. 16426 | 181-GlyMetGlyLysProValAspGlyValMetArgProAspGlyPhe-195 |
| SEQ. ID. NO. 16427 | 211-LysAspIleSerAspLeuLysGluArgLeuGly-221 |
| SEQ. ID. NO. 16428 | 228-AlaLysAspGlySer-232 |
| SEQ. ID. NO. 16429 | 237-LysAspLeuLysAla-241 |
| SEQ. ID. NO. 16430 | 287-ArgLeuAlaLysHisLeuAla-293 |
| SEQ. ID. NO. 16431 | 306-LeuGlyAlaGluLysPheCysAspIleLysCysArgLeuAlaGlyLeuLysProAspAla-325 |
| SEQ. ID. NO. 16432 | 339-GlyGlyValGluArgAlaAsnLeuGlyGluGluAsnLeuAspAlaLeuGluLysGlyLeu-358 |
| SEQ. ID. NO. 16433 | 383-PheValSerAspSerAspAlaGluLeuAlaMetIleGluLysAlaCysAla-399 |
| SEQ. ID. NO. 16434 | 420-AspLeuAlaArgLysValValAsn-427 |
| SEQ. ID. NO. 16435 | 444-LeuGlyIleLysAspLysIleArgAlaIleAla-454 |
| SEQ. ID. NO. 16436 | 458-TyrGlyAlaGluAspValAspPheSerAla-467 |
| SEQ. ID. NO. 16437 | 474-AlaSerLeuGluLysLeuGlyLeuAspLysMetPro-485 |
| SEQ. ID. NO. 16438 | 503-GlyCysProGluAspPheArgIle-510 |
| SEQ. ID. NO. 16439 | 541-ProAlaAlaGluLysIleAspValAspAlaGluGly-552 |

TABLE 1-continued a142
AMPHI Regions - AMPHI
SEQ. ID. NO. 16440    26-ArgPheAlaAlaMetProAspValValGlyLys-36
SEQ. ID. NO. 16441    44-GlyGlnProGlyLysMetPhe-50
SEQ. ID. NO. 16442    100-AlaValThrProCysArg-105
SEQ. ID. NO. 16443    107-ValCysArgAspAspMetAsn-113
SEQ. ID. NO. 16444    118-GlyCysHisArgIleThrGluArgSerLeuLysSerPheLeuGlnIleArgHisPheSerProLeu-139
SEQ. ID. NO. 16445    174-LeuArgValGlnArgIleLeuAspPheGlyLysPheCysGlnGlnVal-189
SEQ. ID. NO. 16446    202-LeuAspSerValValThrLeuValHisPhePheAlaAspPheLeuIle-217
SEQ. ID. NO. 16447    239-AlaAspAsnGlnThrArgPhePheLysAlaGly-249
SEQ. ID. NO. 16448    259-AsnAlaArgLeuIleArgGlnIleLeuLys-268
Antigenic Index - Jameson-Wolf
SEQ. ID. NO. 16449    31-ProAspValValGly-35
SEQ. ID. NO. 16450    38-LeuPheGlyArgGlnAlaGlyGlnProGlyLysMet-49
SEQ. ID. NO. 16451    59-GlnArgIleAspAlaGluAlaAlaValPheArgGlnAspArgAsnAspSerArgThrProValAspAlaGlnHisHisGlyArgArgLeuVal
                      ArgAsnArgArgAsnArgArgHisCysAsnAla-100
SEQ. ID. NO. 16452    102-ThrProCysArgThrValCysArgAspAspMetAsnAlaCysArgThrGlyCysHisArgIleThrGluArgSerLeuLys-128
SEQ. ID. NO. 16453    147-AlaAlaHisLysAla-151
SEQ. ID. NO. 16454    153-ProMetCysSerSerSerAspSerLysSerArgArgSerAspIleSerAlaArgTyr-171
SEQ. ID. NO. 16455    180-LeuAspPheGlyLysPheCys-186
SEQ. ID. NO. 16456    225-GlnLeuGlnLysAsnThrSer-231
SEQ. ID. NO. 16457    237-PheGlnAlaAspAsnGlnThrArgPhePheLysAlaGlyGlnAspThrGlyGlnAlaGlyAlaGlnAsn-259
SEQ. ID. NO. 16458    267-LeuLysValGlnArgAlaValPheArgGlnLysThrAspAsnProPro-282
SEQ. ID. NO. 16459    291-IleGlnAsnArgProGluLeuGlyHisGlnGly-301
SEQ. ID. NO. 16460    307-GlnThrAspIleAspArgArgMetPhe-315
Hydrophilic Regions - Hopp-Woods
SEQ. ID. NO. 16461    42-GlnAlaGlyGlnPro-46
SEQ. ID. NO. 16462    59-GlnArgIleAspAlaGluAlaAlaValPheArgGlnAspArgAsnAspSerArgThrProValAspAlaGlnHisHisGlyArgArgLeuVal
                      ArgAsnArgArgAsnArgArgHisCys-98
SEQ. ID. NO. 16463    106-ThrValCysArgAspAspMetAsnAlaCysArg-116
SEQ. ID. NO. 16464    121-ArgIleThrGluArgSerLeuLys-128
SEQ. ID. NO. 16465    147-AlaAlaHisLysAla-151
SEQ. ID. NO. 16466    156-SerSerSerAspSerLysSerArgArgSerAspIleSerAla-169
SEQ. ID. NO. 16467    237-PheGlnAlaAspAsnGlnThrArgPhePheLysAlaGlyGlnAspThrGlyGln-254
SEQ. ID. NO. 16468    267-LeuLysValGlnArgAlaValPheArgGlnLysThrAspAsn-280
SEQ. ID. NO. 16469    291-IleGlnAsnArgProGluLeuGly-298
SEQ. ID. NO. 16470    309-AspIleAspArgArgMetPhe-315
a144
AMPHI Regions - AMPHI
SEQ. ID. NO. 16471    36-LeuGlyGlyIleValGlnGluPhe-43
SEQ. ID. NO. 16472    45-ValLeuAlaAspGlyValArg-51
SEQ. ID. NO. 16473    71-IleAsnLysGlnIleGlyArgValAlaGlyArg-81
SEQ. ID. NO. 16474    136-ValGlyArgArgLeu-140
SEQ. ID. NO. 16475    159-TyrArgTyrLeuSerArgHis-165
SEQ. ID. NO. 16476    185-GlyProAlaArgCysGlySerAlaTyrSerAlaGly-196
SEQ. ID. NO. 16477    200-SerGlyArgCysArgLysThrAlaArgLeuAsnGlyPheArgArgProArgSer-217
Antigenic Index - Jameson-Wolf
SEQ. ID. NO. 16478    1-MetSerAspThrProAlaThrArgAspPheGlyLeuIleAspGlyArgAla-17
SEQ. ID. NO. 16479    23-LeuSerAsnArgArgGlyThrArg-30
SEQ. ID. NO. 16480    48-AspGlyValArgGlu-52
SEQ. ID. NO. 16481    58-PheAspAspAlaAlaSerTyrAlaAspAsnProPheGlnIleAsn-72
SEQ. ID. NO. 16482    78-ValAlaGlyArgIleArgGlyAlaAla-86
SEQ. ID. NO. 16483    88-AspIleAsnGlyArgThrTyrArgValGluAlaAsnGluGlyArgAsnAlaLeuHisGlyGlySerHis-110
SEQ. ID. NO. 16484    121-AlaAlaAspGlyArgSerValValLeu-129
SEQ. ID. NO. 16485    135-ThrValGlyArgArgLeuSerGlnArgPheGly-145
SEQ. ID. NO. 16486    151-ProLeuGlyArgGlyArgProAlaTyr-159
SEQ. ID. NO. 16487    161-TyrLeuSerArgHisArgAlaArgArgHisGlyValArgProAspAlaAlaHis-178
SEQ. ID. NO. 16488    182-AlaGlyArgGlyProAlaArgCysGlySer-191
SEQ. ID. NO. 16489    194-SerAlaGlyArgThrTyrSerGlyArgCysArgLysThrAlaArgLeuAsnGlyPheArgArgProArgSerIle-218
Hydrophilic Regions - Hopp-Woods
SEQ. ID. NO. 16490    1-MetSerAspThrProAlaThrArgAsp-9
SEQ. ID. NO. 16491    24-SerAsnArgArgGlyThrArg-30
SEQ. ID. NO. 16492    48-AspGlyValArgGlu-52
SEQ. ID. NO. 16493    58-PheAspAspAlaAlaSer-63
SEQ. ID. NO. 16494    78-ValAlaGlyArgIleArgGlyAlaAla-86
SEQ. ID. NO. 16495    89-IleAsnGlyArgThrTyrArgValGluAlaAsnGluGlyArgAsnAlaLeu-105
SEQ. ID. NO. 16496    121-AlaAlaAspGlyArgSerValValLeu-129
SEQ. ID. NO. 16497    135-ThrValGlyArgArgLeuSerGln-142
SEQ. ID. NO. 16498    153-GlyArgGlyArgProAla-158
SEQ. ID. NO. 16499    163-SerArgHisArgAlaArgArgHisGlyValArgProAspAla-176
SEQ. ID. NO. 16500    183-GlyArgGlyProAlaArgCys-189
SEQ. ID. NO. 16501    197-ArgThrTyrSerGlyArgCysArgLysThrAlaArg-208
SEQ. ID. NO. 16502    210-AsnGlyPheArgArgProArgSerIle-218
a146
AMPHI Regions - AMPHI
SEQ. ID. NO. 16503    19-GluGlnTyrGlyLeuPheAspPheMetProCys-29
SEQ. ID. NO. 16504    34-ProLeuAspAsnPheProThrVal-41
SEQ. ID. NO. 16505    64-GlyPheGlyGlnArgIleSerAsnLeuSerArg-74
SEQ. ID. NO. 16506    95-LeuArgAlaCysAla-99
SEQ. ID. NO. 16507    105-HisValArgValPheGlnLys-111

TABLE 1-continued

| | |
|---|---|
| SEQ. ID. NO. 16508 | 140-ThrArgArgValArg-144 |
| SEQ. ID. NO. 16509 | 158-ArgHisGlnArgGlyPheAlaArg-165 |

Antigenic Index - Jameson-Wolf

| | |
|---|---|
| SEQ. ID. NO. 16510 | 6-LeuArgProArgGlnValIleIleAspHisAspLysIleGluGln-20 |
| SEQ. ID. NO. 16511 | 29-CysLeuArgGlnProProLeuAspAsn-37 |
| SEQ. ID. NO. 16512 | 41-ValArgProAlaSerValGluThrArgSerLysHisIleGluArgArgArgGlnAspLysAspAlaAspGlyPheGlyGlnArgIleSerAsnLeuSer-73 |
| SEQ. ID. NO. 16513 | 86-ThrCysArgArgGlnArgIleHisThr-94 |
| SEQ. ID. NO. 16514 | 112-SerLeuLeuArgAspLysArgLeuLys-120 |
| SEQ. ID. NO. 16515 | 138-ArgArgThrArgArgValArgHisGlyAsnAlaGln-149 |
| SEQ. ID. NO. 16516 | 155-GlnGlnProArgHisGlnArgGlyPheAla-164 |
| SEQ. ID. NO. 16517 | 166-AlaGlySerGlyArgAsnAspLysAspValAlaPheSerIle-179 |
| SEQ. ID. NO. 16518 | 195-GlnArgThrProGlyPhe-200 |

Hydrophilic Regions - Hopp-Woods

| | |
|---|---|
| SEQ. ID. NO. 16519 | 6-LeuArgProArgGlnValIleIleAspHisAspLysIleGluGln-20 |
| SEQ. ID. NO. 16520 | 44-AlaSerValGluThrArgSerLysHisIleGluArgArgArgGlnAspLysAspAlaAspGlyPheGly-66 |
| SEQ. ID. NO. 16521 | 86-ThrCysArgArgGlnArgIleHisThr-94 |
| SEQ. ID. NO. 16522 | 112-SerLeuLeuArgAspLysArgLeuLys-120 |
| SEQ. ID. NO. 16523 | 138-ArgArgThrArgArgValArgHisGlyAsn-147 |
| SEQ. ID. NO. 16524 | 156-GlnProArgHisGlnArgGlyPheAla-164 |
| SEQ. ID. NO. 16525 | 167-GlySerGlyArgAsnAspLysAspValAla-176 | a148
AMPHI Regions - AMPHI

| | |
|---|---|
| SEQ. ID. NO. 16526 | 25-AlaAspLysIleArgLysIleGluAsnTrpPro-35 |
| SEQ. ID. NO. 16527 | 49-GlnSerAlaGluTyrPheArgLeuLeuValAspLeu-60 |
| SEQ. ID. NO. 16528 | 150-AlaGlyLeuGluLeuIleArgLysLeuGlyGlyGluIle-162 |
| SEQ. ID. NO. 16529 | 165-AlaAlaAlaIleLeuGluPheThrAspLeuGlnGlyGlyLysAsnIleArg-181 |

Antigenic Index - Jameson-Wolf

| | |
|---|---|
| SEQ. ID. NO. 16530 | 4-LysThrSerAsnLeu-8 |
| SEQ. ID. NO. 16531 | 24-LeuAlaAspLysIleArgLysIleGluAsnTrpProGlnLysGly-38 |
| SEQ. ID. NO. 16532 | 66-MetAspGlnLysIleAspIle-72 |
| SEQ. ID. NO. 16533 | 76-LeuAspAlaArgGly-80 |
| SEQ. ID. NO. 16534 | 97-ProIleArgLysLysGlyLysLeuPro-105 |
| SEQ. ID. NO. 16535 | 117-TyrGlyGluAlaAlaVal-122 |
| SEQ. ID. NO. 16536 | 124-IleHisThrAspAlaValLysLeuGlySer-133 |
| SEQ. ID. NO. 16537 | 153-GluLeuIleArgLysLeuGlyGlyGluIleValGlu-164 |
| SEQ. ID. NO. 16538 | 172-ThrAspLeuGlnGlyGlyLysAsnIleArgAlaSerGlyAlaPro-186 |
| SEQ. ID. NO. 16539 | 192-GlnAsnGluGlyCysMetLysGly-199 |

Hydrophilic Regions - Hopp-Woods

| | |
|---|---|
| SEQ. ID. NO. 16540 | 24-LeuAlaAspLysIleArgLysIleGluAsnTrpPro-35 |
| SEQ. ID. NO. 16541 | 66-MetAspGlnLysIleAspIle-72 |
| SEQ. ID. NO. 16542 | 97-ProIleArgLysLysGlyLysLeuPro-105 |
| SEQ. ID. NO. 16543 | 117-TyrGlyGluAlaAlaVal-122 |
| SEQ. ID. NO. 16544 | 124-IleHisThrAspAlaValLysLeuGlySer-133 |
| SEQ. ID. NO. 16545 | 153-GluLeuIleArgLysLeuGlyGlyGluIleValGlu-164 |
| SEQ. ID. NO. 16546 | 178-LysAsnIleArgAlaSerGly-184 |
| SEQ. ID. NO. 16547 | 195-GlyCysMetLysGly-199 | a149
AMPHI Regions - AMPHI

| | |
|---|---|
| SEQ. ID. NO. 16548 | 72-AsnLeuGlyAspAlaLeuAspGlyValProGlyIle-83 |
| SEQ. ID. NO. 16549 | 101-ThrGlyArgArgIleLysValLeuAsnHisHisGlyGluThrGlyAspMet-117 |
| SEQ. ID. NO. 16550 | 135-GlnValGluIleLeuArgGlyProValThr-144 |
| SEQ. ID. NO. 16551 | 152-ValAlaGlyLeuValAsp-157 |
| SEQ. ID. NO. 16552 | 164-ProGluLysMetProGluAsnGlyVal-172 |
| SEQ. ID. NO. 16553 | 184-AsnLeuGluLysLeu-188 |
| SEQ. ID. NO. 16554 | 220-TyrArgAsnLeuLysArgLeuProAspSerHis-230 |
| SEQ. ID. NO. 16555 | 345-PheProGlyPheGlu-349 |
| SEQ. ID. NO. 16556 | 366-AlaGlyAspAlaValGluAsnPhePheAsnAsn-376 |
| SEQ. ID. NO. 16557 | 389-ProIleGlyArgLeuLys-394 |
| SEQ. ID. NO. 16558 | 411-AlaThrSerGluAla-415 |
| SEQ. ID. NO. 16559 | 565-ArgPheGlyAsnTyrIleTyrAlaGln-573 |
| SEQ. ID. NO. 16560 | 576-AsnAspGlyArgGlyProLysSerIleGluAsp-586 |
| SEQ. ID. NO. 16561 | 627-ArgGlyArgLeuLysAsnLeuProSer-635 |

Antigenic Index - Jameson-Wolf

| | |
|---|---|
| SEQ. ID. NO. 16562 | 23-GlnAlaHisGlyThrGluGlnSerVal-31 |
| SEQ. ID. NO. 16563 | 40-GlyLysSerArgProArgAlaThrSerGly-49 |
| SEQ. ID. NO. 16564 | 55-ThrAlaSerAspLysIleIleSerGlyAspThrLeuArgGlnLysAla-70 |
| SEQ. ID. NO. 16565 | 97-IleArgGlyGlnThrGlyArgArgIleLysVal-107 |
| SEQ. ID. NO. 16566 | 109-AsnHisHisGlyGluThrGlyAspMetAlaAspPheSerProAspHis-124 |
| SEQ. ID. NO. 16567 | 137-GluIleLeuArgGlyPro-142 |
| SEQ. ID. NO. 16568 | 157-AspValAlaAspGlyLysIleProGluLysMetProGluAsnGlyValSerGlyGluLeuGlyLeu-178 |
| SEQ. ID. NO. 16569 | 180-LeuSerSerGlyAsnLeuGluLysLeuThrSerGlyGly-192 |
| SEQ. ID. NO. 16570 | 207-GlyLeuTyrArgLysSerGlyAspTyrAlaValProArgTyrArgAsnLeuLysArgLeuProAspSerHisAlaAspSerGlnThrGly-236 |
| SEQ. ID. NO. 16571 | 244-GlyGluLysGlyPhe-248 |
| SEQ. ID. NO. 16572 | 252-AlaTyrSerAspArgArgAspGlnTyrGly-261 |
| SEQ. ID. NO. 16573 | 263-ProAlaHisSerHisGluTyrAspAspCysHisAla-274 |
| SEQ. ID. NO. 16574 | 281-SerLeuIleAsnLysArgTyrLeu-288 |
| SEQ. ID. NO. 16575 | 295-LeuThrGluGluAspIleAspTyrAspAsnProGlyLeu-307 |
| SEQ. ID. NO. 16576 | 310-GlyPheHisAspAspAspAspAlaHis-318 |
| SEQ. ID. NO. 16577 | 321-AlaHisAsnGlyLysProTrpIleAspLeuArgAsnLysArgTyrGluLeuArgAlaGluTrpLysGlnProPheProGly-347 |

TABLE 1-continued

| | |
|---|---|
| SEQ. ID. NO. 16578 | 354-HisLeuAsnArgAsnAspTyrArgHisAspGluLysAlaGlyAspAlaVal-370 |
| SEQ. ID. NO. 16579 | 374-PheAsnAsnGlnThrGlnAsnAlaArgIleGluLeuArgHisGlnProIleGlyArgLeuLysGlySerTrp-397 |
| SEQ. ID. NO. 16580 | 402-LeuGlyGlnLysSerSerAlaLeu-409 |
| SEQ. ID. NO. 16581 | 411-AlaThrSerGluAlaValLys-417 |
| SEQ. ID. NO. 16582 | 422-LeuAspAsnLysVal-426 |
| SEQ. ID. NO. 16583 | 437-AlaAsnTrpAspAsnPheThrLeuGluGlyGlyValArgValGluLys GlnLysAlaSerIleArgTyrAspLysAlaLeuIleAspArgGluAsnTyrTyrAsnHisProLeuProAsp-476 |
| SEQ. ID. NO. 16584 | 478-GlyAlaHisArgGlnThrAla-484 |
| SEQ. ID. NO. 16585 | 506-SerHisGlnGluArgLeuProSerThrGlnGluLeuTyrAlaHisGly-521 |
| SEQ. ID. NO. 16586 | 531-ValGlyAsnLysHisLeuAsnLysGluArgSerAsnAsnIle-544 |
| SEQ. ID. NO. 16587 | 550-TyrGluGlyAspArgTrpGln-556 |
| SEQ. ID. NO. 16588 | 562-TyrArgAsnArgPheGlyAsn-568 |
| SEQ. ID. NO. 16589 | 574-ThrLeuAsnAspGlyArgGlyProLysSerIleGluAspAspSerGluMetLysLeu-592 |
| SEQ. ID. NO. 16590 | 594-ArgTyrAsnGlnSerGlyAlaAspPheTyrGlyAlaGluGly-607 |
| SEQ. ID. NO. 16591 | 609-IleTyrPheLysProThrProArgTyrArgIle-619 |
| SEQ. ID. NO. 16592 | 621-ValSerGlyAspTyrValArgGlyArgLeuLysAsnLeuProSerLeuProGlyArgGluAspAlaTyrGlyAsnArg-646 |
| SEQ. ID. NO. 16593 | 651-GlnAlaAspGlnAsnAlaProArgValProAla-661 |
| SEQ. ID. NO. 16594 | 671-SerLeuThrAspArgIleAspAla-678 |
| SEQ. ID. NO. 16595 | 689-AsnLysLeuAlaArgTyrGluThrArgThrProGlyHis-701 |
| SEQ. ID. NO. 16596 | 707-GlyAlaAsnTyrArgArgAsnThrArgTyrGlyGluTrp-719 |
| SEQ. ID. NO. 16597 | 725-AlaAspAsnLeuLeu-729 |
| SEQ. ID. NO. 16598 | 739-PheLeuSerAspThrProGlnMetGlyArgSerPheThrGlyGlyVal-754 |
| Hydrophilic Regions - Hopp-Woods | |
| SEQ. ID. NO. 16599 | 25-HisGlyThrGluGln-29 |
| SEQ. ID. NO. 16600 | 40-GlyLysSerArgProArgAlaThr-47 |
| SEQ. ID. NO. 16601 | 55-ThrAlaSerAspLysIleIleSer-62 |
| SEQ. ID. NO. 16602 | 64-AspThrLeuArgGlnLysAla-70 |
| SEQ. ID. NO. 16603 | 100-GlnThrGlyArgArgIleLysVal-107 |
| SEQ. ID. NO. 16604 | 112-GlyGluThrGlyAspMetAlaAspPheSerPro-122 |
| SEQ. ID. NO. 16605 | 157-AspValAlaAspGlyLysIleProGluLysMetProGluAsnGlyValSer-173 |
| SEQ. ID. NO. 16606 | 181-SerSerGlyAsnLeuGluLysLeuThr-189 |
| SEQ. ID. NO. 16607 | 207-GlyLeuTyrArgLysSerGlyAsp-214 |
| SEQ. ID. NO. 16608 | 219-ArgTyrArgAsnLeuLysArgLeuProAspSerHisAlaAspSerGlnThr-235 |
| SEQ. ID. NO. 16609 | 253-TyrSerAspArgArgAspGlnTyr-260 |
| SEQ. ID. NO. 16610 | 267-HisGluTyrAspAspCysHisAla-274 |
| SEQ. ID. NO. 16611 | 295-LeuThrGluGluAspIleAspTyrAspAsn-304 |
| SEQ. ID. NO. 16612 | 311-PheHisAspAspAspAspAlaHis-318 |
| SEQ. ID. NO. 16613 | 330-LeuArgAsnLysArgTyrGluLeuArgAlaGluTrp-341 |
| SEQ. ID. NO. 16614 | 354-HisLeuAsnArgAsnAspTyrArgHisAspGluLysAlaGlyAspAlaVal-370 |
| SEQ. ID. NO. 16615 | 378-ThrGlnAsnAlaArgIleGluLeuArgHis-387 |
| SEQ. ID. NO. 16616 | 391-GlyArgLeuLysGly-395 |
| SEQ. ID. NO. 16617 | 411-AlaThrSerGluAlaValLys-417 |
| SEQ. ID. NO. 16618 | 446-GlyGlyValArgValGluLysGlnLysAlaSerIleArgTyrAspLysAlaLeuIleAspArgGluAsnTyr-469 |
| SEQ. ID. NO. 16619 | 478-GlyAlaHisArgGlnThrAla-484 |
| SEQ. ID. NO. 16620 | 506-SerHisGlnGluArgLeuProSer-513 |
| SEQ. ID. NO. 16621 | 535-HisLeuAsnLysGluArgSerAsnAsn-543 |
| SEQ. ID. NO. 16622 | 550-TyrGluGlyAspArgTrp-555 |
| SEQ. ID. NO. 16623 | 575-LeuAsnAspGlyArgGlyProLysSerIleGluAspAspSerGluMetLysLeu-592 |
| SEQ. ID. NO. 16624 | 603-TyrGlyAlaGluGly-607 |
| SEQ. ID. NO. 16625 | 613-ProThrProArgTyrArgIle-619 |
| SEQ. ID. NO. 16626 | 624-AspTyrValArgGlyArgLeuLysAsn-632 |
| SEQ. ID. NO. 16627 | 637-ProGlyArgGluAspAlaTyrGly-644 |
| SEQ. ID. NO. 16628 | 652-AlaAspGlnAsnAlaProArgValProAla-661 |
| SEQ. ID. NO. 16629 | 671-SerLeuThrAspArgIleAspAla-678 |
| SEQ. ID. NO. 16630 | 690-LysLeuAlaArgTyrGluThrArgThrProGly-700 |
| SEQ. ID. NO. 16631 | 709-AsnTyrArgArgAsnThrArgTyrGly-717 |
| a150 | |
| AMPHI Regions - AMPHI | |
| SEQ. ID. NO. 16632 | 1-MetGlnAsnThrAsnProProLeuProProMetProProGluIleThrGlnLeuLeuSerGlyLeuAspAlaAlaGlnTrpAlaTrpLeuSerGlyTyrAlaTrpAlaLysAlaGlyAsnGlyAlaSerAlaGlyLeuProAlaLeuGlnThrAlaLeuProThrAlaGluProPheSerValThrValLeuSerAlaSerGlnThrGlyAsnAlaLysSerValAlaAspLysAlaAlaAspSerLeuGluAlaAlaGlyIleGlnValSerArgAlaGluLeuLysAspTyrLysAlaLysAsnIleAlaGlyGluArgArgLeuLeuGluValThrSerThrGlnGlyGluGlyProGluGluAlaValValLeuHisLysLeuLeuAsnGlyLysLysLeuAspLysLeuGlnPheAlaValLeuGlyLeuGlyAspSerSerTyrProAsnPheCysArgAlaGlyLysAspPheAspLysArgPheGluGluLeuGlyAlaLysArgLeuLeuGluArgValAspAlaAspLeuAspPheAlaAlaAlaAlaAspGlyTrpThrAspAsnIleAlaAlaLeuLeuLysGluGluAlaAlaLysAsnArgAlaThrProAlaProGlnThrThrProProAlaGlyLeuGlnThrAlaProAspGlyArgTyrCysLysAlaAspProPheProAlaAlaLeuLeuAlaAsnGlnLysIleThrAlaArgGlnSerAspLysAspValArgHisIleGlyIleIleAspLeuSerGlySerAspLeuHisTyrLeuProGlyAspLysAlaLeuValValTrpPheAspAsnAspProAlaLeuValArgGluIleLeuAspLeuLeuGlyIleAspGlnAlaThrGluIleGlnAlaGlyGlyLysThrLeuProValAlaSerAlaLeuLeuSerHisPheGluLeuThrGlnAsnThrProAlaPheValLysGlyTyrAlaProPheAlaAspAspAspGluLeuAspArgIleAlaAlaAspAsnAlaValLeuGlnGlyPheValGlnSerThrProIleAlaAspValLeuHisArgPheProAlaLysLeuThrAlaGluGlnPheAlaGlyLeuLeuArgProLeuAlaProArgLeuTyrSerIleSerSerSerGlnAlaGluValGlyAspGluValHisLeuThrValGlyAlaValArgPheGluHisGlyGlyAlaArgAlaAlaGlyGlyAlaSerGlyPheLeuAlaAsnArgLeuGluGluAspGlyAspGluValHisLeuThrValGlyAlaValArgPheGluHisGlyGlyAlaArgAlaAlaGlyGlyAlaSerGlyPheLeuAlaAsnArgLeuGluGluAspGlyAspGlyAspGlyAspGlyAspGlyTyrThrValArgValPheValGluGlyAsnAspGlyPheArgLeuProGluAspSerArgLysProIleValMetIleGlySerGlyThrGlyValAlaProPheAlaArgAlaPheValGlnGlnArgAlaAlaGluAsnAlaGluGlyLysAsnTrpLeuPhePheGlyAsnProHisPheAlaArgAspPheLeuTyrGlnThrGluTrpGlnGlnPheAlaLysAspGlyPheLeuHisArgTyrAspPheAlaTrpSerArgAspGlnGluGluLysIleTyrValGlnAspLysIleArgGluGlnAlaGlyLeuTrpGlnTrpLeuGluGlnGlyAlaAlaHisIleTyrValCysGlyAspAlaAlaLysMetAlaLysAspValGluAlaAlaLeuLeuAspValIleIleGlyAlaGlyHisLeuAspGluGluGlyAlaGluGluTyrLeuAspMetLeuArgGluGluLysGlyTyrGlnArgAspValTyr-599 |
| Antigenic Index - Jameson-Wolf (SEQ. ID. NO. 16633) | |

1-MetGlnAsnThrAsnProProLeuProProMetProProGluIleThrGlnLeuLeuSerGlyLeuAspAlaAlaGlnTrpAlaTrpLeuSerGlyTyrAlaTrpAlaLysAlaGlyAsnGlyAlaSerAlaGlyLeuProAlaLeuGlnThrAlaLeuProThrAlaGluProPheSerValThrValLeuSerAlaSerGlnThrGlyAsnAlaLysSerValA

TABLE 1-continued laAspLysAlaAlaAspSerLeuGluAlaAlaGlyIleGlnValSerArgAlaGluLeuLysAspTyrLysAlaLy
sAsnIleAlaGlyGluArgArgLeuLeuLeuValThrSerThrGlnGlyGluGlyGluProProGluGluAlaVal
ValLeuHisLysLeuLeuAsnGlyLysLysAlaProLysLeuAspLysLeuGlnPheAlaValLeuGlyLeuGlyA
spSerSerTyrProAsnPheCysArgAlaGlyLysAspPheAspLysArgPheGluGluLeuGlyAlaLysArgLe
uLeuGluArgValAspAlaAspLeuAspPheAlaAlaAlaAlaAspGlyTrpThrAspAsnIleAlaAlaLeuLeu
LysGluGluAlaAlaLysAsnArgAlaThrProAlaProGlnThrThrProProAlaGlyLeuGlnThrAlaProA
spGlyArgTyrCysLysAlaAspProPheProAlaAlaLeuLeuAlaAsnGlnLysIleThrAlaArgGlnSerAs
pLysAspValArgHisIleGluIleAspLeuSerGlySerAspLeuHisTyrLeuProGlyAspAlaLeuGlyVal
TrpPheAspAsnAspProAlaLeuValArgGluIleLeuAspLeuLeuGlyIleAspGlnAlaThrGluIleGlnA
laGlyGlyLysThrLeuProValAlaSerAlaLeuLeuSerHisPheGluLeuThrGlnAsnThrProAlaPheVa
lLysGlyTyrAlaProPheAlaAspAspAspGluLeuAspArgIleAlaAlaAspAsnAlaValLeuGlnGlyPhe
ValGlnSerThrProIleAlaAspValLeuHisArgPheProAlaLysLeuThrAlaGluGlnPheAlaGlyLeuL
euArgProLeuAlaProArgLeuTyrSerIleSerSerSerGlnAlaGluValGlyAspGluValHisLeuThrVa
lGlyAlaValArgPheGluHisGluGlyArgAlaArgAlaGlyGlyAlaSerGlyPheLeuAlaAspArgLeuGlu
GluAspGlyThrValArgValPheValGluArgAsnAspGlyPheArgLeuProGluAspSerArgLysProIleV
alMetIleGlySerGlyThrGlyValAlaProPheArgAlaPheValGlnGlnArgAlaAlaGluAsnAlaGluGl
yLysAsnTrpLeuPhePheGlyAsnProHisPheAlaArgAspPheLeuTyrGlnThrGluTrpGlnGlnPheAla
LysAspGlyPheLeuHisArgTyrAspPheAlaTrpSerArgAspGlnGluGluLysIleTyrValGlnAspLysI
leArgGluGlnAlaGluGlyLeuTrpGlnTrpLeuGlnGluGlyAlaHisIleTyrValCysGlyAspAlaAlaLy
sMetAlaLysAspValGluAlaAlaLeuLeuAspValIleIleGlyAlaGlyHisLeuAspGluGluGlyAlaGlu
GluTyrLeuAspMetLeuArgGluGluLysArgTyrGlnArgAspValTyr-599

Hydrophilic Regions - Hopp-Woods (SEQ. ID. NO. 16633)
1-MetGlnAsnThrAsnProProLeuProProMetProProGluIleThrGlnLeuLeuSerGlyLeuAspAlaAl
aGlnTrpAlaTrpLeuSerGlyTyrAlaTrpAlaLysAlaGlyAsnGlyAlaSerAlaGlyLeuProAlaLeuGln
ThrAlaLeuProThrAlaGluProPheSerValThrValLeuSerAlaSerGlnThrGlyAsnAlaLysSerValA
laAspLysAlaAlaAspSerLeuGluAlaAlaGlyIleGlnValSerArgAlaGluLeuLysAspTyrLysAlaLy
sAsnIleAlaGlyGluArgArgLeuLeuLeuValThrSerThrGlnGlyGluGlyGluProProGluGluAlaVal
ValLeuHisLysLeuLeuAsnGlyLysLysAlaProLysLeuAspLysLeuGlnPheAlaValLeuGlyLeuGlyA
spSerSerTyrProAsnPheCysArgAlaGlyLysAspPheAspLysArgPheGluGluLeuGlyAlaLysArgLe
uLeuGluArgValAspAlaAspLeuAspPheAlaAlaAlaAlaAspGlyTrpThrAspAsnIleAlaAlaLeuLeu
LysGluGluAlaAlaLysAsnArgAlaThrProAlaProGlnThrThrProProAlaGlyLeuGlnThrAlaProA
spGlyArgTyrCysLysAlaAspProPheProAlaAlaLeuLeuAlaAsnGlnLysIleThrAlaArgGlnSerAs
pLysAspValArgHisIleGluIleAspLeuSerGlySerAspLeuHisTyrLeuProGlyAspAlaLeuGlyVal
TrpPheAspAsnAspProAlaLeuValArgGluIleLeuAspLeuLeuGlyIleAspGlnAlaThrGluIleGlnA
laGlyGlyLysThrLeuProValAlaSerAlaLeuLeuSerHisPheGluLeuThrGlnAsnThrProAlaPheVa
lLysGlyTyrAlaProPheAlaAspAspAspGluLeuAspArgIleAlaAlaAspAsnAlaValLeuGlnGlyPhe
ValGlnSerThrProIleAlaAspValLeuHisArgPheProAlaLysLeuThrAlaGluGlnPheAlaGlyLeuL
euArgProLeuAlaProArgLeuTyrSerIleSerSerSerGlnAlaGluValGlyAspGluValHisLeuThrVa
lGlyAlaValArgPheGluHisGluGlyArgAlaArgAlaGlyGlyAlaSerGlyPheLeuAlaAspArgLeuGlu
GluAspGlyThrValArgValPheValGluArgAsnAspGlyPheArgLeuProGluAspSerArgLysProIleV
alMetIleGlySerGlyThrGlyValAlaProPheArgAlaPheValGlnGlnArgAlaAlaGluAsnAlaGluGl
yLysAsnTrpLeuPhePheGlyAsnProHisPheAlaArgAspPheLeuTyrGlnThrGluTrpGlnGlnPheAla
LysAspGlyPheLeuHisArgTyrAspPheAlaTrpSerArgAspGlnGluGluLysIleTyrValGlnAspLysI
leArgGluGlnAlaGluGlyLeuTrpGlnTrpLeuGlnGluGlyAlaHisIleTyrValCysGlyAspAlaAlaLy
sMetAlaLysAspValGluAlaAlaLeuLeuAspValIleIleGlyAlaGlyHisLeuAspGluGluGlyAlaGlu
GluTyrLeuAspMetLeuArgGluGluLysArgTyrGlnArgAspValTyr-599
a151
AMPHI Regions - AMPHI

| | |
|---|---|
| SEQ. ID. NO. 16633 | 6-AsnIleAlaIleIleAla-11 |
| SEQ. ID. NO. 16634 | 22-AspGlnLeuLeuArg-26 |
| SEQ. ID. NO. 16635 | 72-ValAspThrProGlyHis-77 |
| SEQ. ID. NO. 16636 | 81-GlyGlyGluValGluArgValLeuGlyMetValAspCysVal-94 |
| SEQ. ID. NO. 16637 | 128-LysIleAspLysPro-132 |
| SEQ. ID. NO. 16638 | 144-PheGluLeuPheAspAsnLeuGlyAlaThr-153 |
| SEQ. ID. NO. 16639 | 165-SerGlyLeuSerGlyPheAlaLysLeuGluGluThrAspGluSerAsn-180 |
| SEQ. ID. NO. 16640 | 184-ProLeuPheAspThrIleLeuLysTyrThr-193 |
| SEQ. ID. NO. 16641 | 248-GlyArgIleAsnGlnLeuLeuGlyPheLysGlyLeuGluArgVal-262 |
| SEQ. ID. NO. 16642 | 273-ValIleIleSerGlyIleGlu-279 |
| SEQ. ID. NO. 16643 | 330-IleArgAspArgLeuGlnLysGluLeu-338 |
| SEQ. ID. NO. 16644 | 348-AspThrAlaAspAla-352 |
| SEQ. ID. NO. 16645 | 396-CysGluProTyrGluAsnLeuThrValAsp-405 |
| SEQ. ID. NO. 16646 | 457-LeuThrArgGlyValGly-462 |
| SEQ. ID. NO. 16647 | 464-MetSerHisValPheAsp-469 |
| SEQ. ID. NO. 16648 | 537-LysGlyLysLysLeuThrAsnIle-544 |
| SEQ. ID. NO. 16649 | 551-GluAlaValArgLeuThrThr-557 |

Antigenic Index - Jameson-Wolf

| | |
|---|---|
| SEQ. ID. NO. 16650 | 1-MetLysGlnIleArg-5 |
| SEQ. ID. NO. 16651 | 13-ValAspHisGlyLysThrThrLeu-20 |
| SEQ. ID. NO. 16652 | 24-LeuLeuArgGlnSerGlyThrPheArgAlaAsnGlnGlnValAspGluArgValMetAspSerAsnAspLeuGluLysGluArgGlyIle-53 |
| SEQ. ID. NO. 16653 | 59-AsnThrAlaIleAspTyrGluGlyTyr-67 |
| SEQ. ID. NO. 16654 | 72-ValAspThrProGlyHisAlaAspPheGlyGlyValGluArg-86 |
| SEQ. ID. NO. 16655 | 99-AspAlaGlnGluGlyProMetProGlnThrArgPheValThr-112 |
| SEQ. ID. NO. 16656 | 128-LysIleAspLysProSerAlaArgProSerTrp-138 |
| SEQ. ID. NO. 16657 | 151-GlyAlaThrAspGluGlnLeuAsp-158 |
| SEQ. ID. NO. 16658 | 171-AlaLysLeuGluGluThrAspGluSerAsnAspMetArgProLeu-185 |
| SEQ. ID. NO. 16659 | 193-ThrProAlaProSerProGlySerAlaAspGluThrLeu-204 |
| SEQ. ID. NO. 16660 | 211-LeuAspTyrAspAsnTyrThrGly-218 |
| SEQ. ID. NO. 16661 | 226-LeuAsnGlyArgIleLysProGlyGln-234 |
| SEQ. ID. NO. 16662 | 240-AsnHisAspGlnGlnIleAla-246 |
| SEQ. ID. NO. 16663 | 257-LysGlyLeuGluArgValProLeuGluGluAlaGluAlaGlyAsp-271 |

TABLE 1-continued

| | |
|---|---|
| SEQ. ID. NO. 16664 | 277-GlyIleGluAspIleGly-282 |
| SEQ. ID. NO. 16665 | 287-IleThrAspLysAspAsnProLysGlyLeuPro-297 |
| SEQ. ID. NO. 16666 | 300-SerValAspGluProThrLeu-306 |
| SEQ. ID. NO. 16667 | 314-ThrSerProLeuAlaGlyThrGluGlyLysPheValThrSerArgGlnIleArgAspArgLeuGlnLysGluLeuLeu-339 |
| SEQ. ID. NO. 16668 | 344-LeuArgValGluAspThrAlaAspAlaAspValPheArgValSerGlyArgGlyGluLeu-363 |
| SEQ. ID. NO. 16669 | 371-AsnMetArgArgGluGlyTyr-377 |
| SEQ. ID. NO. 16670 | 381-ValGlyLysProArgValValTyrArgAspIleAspGlyGlnLysCysGluProTyrGluAsnLeuThrValAspValProAspAspAsnGln GlyAlaValMetGluGluLeuGlyArgArgArgGlyGluLeuThrAsnMetGluSerAspGlyAsnGlyArgThrArgLeuGluTyr-440 |
| SEQ. ID. NO. 16671 | 467-ValPheAspAspTyrAlaProValLysProAspMetProGlyArgHisAsnGly-484 |
| SEQ. ID. NO. 16672 | 489-GlnGluGlnGlyGlu-493 |
| SEQ. ID. NO. 16673 | 501-AsnLeuGluAspArgGlyArgMetPheValSerProAsnAspLysIleTyr-517 |
| SEQ. ID. NO. 16674 | 524-IleHisSerArgAspAsnAspLeu-531 |
| SEQ. ID. NO. 16675 | 535-ProLeuLysGlyLysLysLeuThrAsnIleArgAlaSerGlyThrAspGluAlaValArg-554 |
| SEQ. ID. NO. 16676 | 569-PheIleAspAspAspGluLeuValGlu-577 |
| SEQ. ID. NO. 16677 | 579-ThrProGlnSerIleArgLeuArgLysArgTyrLeuSerGluLeuGluArgArgHisPheLysLysLeuAsp-603 |

Hydrophilic Regions - Hopp-Woods

| | |
|---|---|
| SEQ. ID. NO. 16678 | 1-MetLysGlnIleArg-5 |
| SEQ. ID. NO. 16679 | 29-GlyThrPheArgAla-33 |
| SEQ. ID. NO. 16680 | 35-GlnGlnValAspGluArgValMetAspSerAsnAspLeuGluLysGluArgGlyIle-53 |
| SEQ. ID. NO. 16681 | 80-PheGlyGlyGluValGluArg-86 |
| SEQ. ID. NO. 16682 | 99-AspAlaGlnGluGlyProMetPro-106 |
| SEQ. ID. NO. 16683 | 128-LysIleAspLysProSerAla-134 |
| SEQ. ID. NO. 16684 | 151-GlyAlaThrAspGluGlnLeuAsp-158 |
| SEQ. ID. NO. 16685 | 171-AlaLysLeuGluGluThrAspGluSerAsnAspMetArgProLeu-185 |
| SEQ. ID. NO. 16686 | 198-GlySerAlaAspGluThrLeu-204 |
| SEQ. ID. NO. 16687 | 226-LeuAsnGlyArgIleLysPro-232 |
| SEQ. ID. NO. 16688 | 241-HisAspGlnGlnIleAla-246 |
| SEQ. ID. NO. 16689 | 258-GlyLeuGluArgValProLeuGluGluAlaGluAlaGlyAsp-271 |
| SEQ. ID. NO. 16690 | 277-GlyIleGluAspIleGly-282 |
| SEQ. ID. NO. 16691 | 287-IleThrAspLysAspAsnProLysGly-295 |
| SEQ. ID. NO. 16692 | 300-SerValAspGluProThrLeu-306 |
| SEQ. ID. NO. 16693 | 318-AlaGlyThrGluGlyLysPheValThr-326 |
| SEQ. ID. NO. 16694 | 328-ArgGlnIleArgAspArgLeuGlnLysGluLeuLeu-339 |
| SEQ. ID. NO. 16695 | 344-LeuArgValGluAspThrAlaAspAlaAspValPheArgValSerGlyArgGlyGluLeu-363 |
| SEQ. ID. NO. 16696 | 371-AsnMetArgArgGluGlyTyr-377 |
| SEQ. ID. NO. 16697 | 381-ValGlyLysProArgValValTyrArgAspIleAspGlyGlnLysCysGluProTyrGlu-400 |
| SEQ. ID. NO. 16698 | 405-AspValProAspAspAsnGlnGlyAlaValMetGluGluLeuGlyArgArgArgGlyGluLeuThrAsnMetGluSerAspGlyAsnGlyArg ThrArgLeu-438 |
| SEQ. ID. NO. 16699 | 472-AlaProValLysProAspMetProGlyArgHis-482 |
| SEQ. ID. NO. 16700 | 489-GlnGluGlnGlyGlu-493 |
| SEQ. ID. NO. 16701 | 502-LeuGluAspArgGlyArgMet-508 |
| SEQ. ID. NO. 16702 | 512-ProAsnAspLysIleTyr-517 |
| SEQ. ID. NO. 16703 | 525-HisSerArgAspAsnAspLeu-531 |
| SEQ. ID. NO. 16704 | 536-LeuLysGlyLysLysLeuThrAsn-543 |
| SEQ. ID. NO. 16705 | 545-ArgAlaSerGlyThrAspGluAlaValArg-554 |
| SEQ. ID. NO. 16706 | 569-PheIleAspAspAspGluLeuValGlu-577 |
| SEQ. ID. NO. 16707 | 583-IleArgLeuArgLysArgTyrLeuSerGluLeuGluArgArgArgHisPheLysLysLeuAsp-603 | a152
AMPHI Regions - AMPHI

| | |
|---|---|
| SEQ. ID. NO. 16708 | 10-PheProThrArgLeuPhe-15 |
| SEQ. ID. NO. 16709 | 66-ArgPheSerArgPheValArgGlyTrpSerGlyIleArgGluTyrMetLysAsnGlyIleProGluHisValGlnProGlyHisAsnProLeu-96 |
| SEQ. ID. NO. 16710 | 103-AlaLeuLeuAlaAla-107 |
| SEQ. ID. NO. 16711 | 130-LeuAsnHisLeuValSerGluHisThrGlySerLeu-141 |
| SEQ. ID. NO. 16712 | 150-PheLysLeuLeuAlaValPheSerAlaValHisIleAlaXxxValAlaAlaTyr-167 |

Antigenic Index - Jameson-Wolf

| | |
|---|---|
| SEQ. ID. NO. 16713 | 1-MetLysAsnLysThrLysValTrp-8 |
| SEQ. ID. NO. 16714 | 28-TyrSerAlaLysThrGlyGlyAsp-35 |
| SEQ. ID. NO. 16715 | 61-GlySerAspThrAlaArgPhe-67 |
| SEQ. ID. NO. 16716 | 74-TrpSerGlyIleArgGluTyrMetLysAsnGlyIleProGluHisValGlnProGlyHisAsnProLeu-96 |
| SEQ. ID. NO. 16717 | 125-SerThrAsnGlyTyr-129 |
| SEQ. ID. NO. 16718 | 137-HisThrGlySerLeuMetArg-143 |
| SEQ. ID. NO. 16719 | 169-ValPheLysLysLysAsnLeu-175 |
| SEQ. ID. NO. 16720 | 186-IleGluGlyLysThrSerIle-192 |

Hydrophilic Regions - Hopp-Woods

| | |
|---|---|
| SEQ. ID. NO. 16721 | 1-MetLysAsnLysThrLysVal-7 |
| SEQ. ID. NO. 16722 | 63-AspThrAlaArgPhe-67 |
| SEQ. ID. NO. 16723 | 78-ArgGluTyrMetLys-82 |
| SEQ. ID. NO. 16724 | 169-ValPheLysLysLysAsnLeu-175 |
| SEQ. ID. NO. 16725 | 186-IleGluGlyLysThrSerIle-192 | a153
AMPHI Regions - AMPHI

| | |
|---|---|
| SEQ. ID. NO. 16726 | 17-AlaAlaSerValLeuSerLeuProGluMetMetArgLeuMetValPhe-32 |
| SEQ. ID. NO. 16727 | 96-ThrLeuValAlaTyrIleLysLeuSerSerValAlaGlu-108 |
| SEQ. ID. NO. 16728 | 130-ValSerValProGlnHisTrp-136 |
| SEQ. ID. NO. 16729 | 222-ValAsnThrIleLeuAsnGlyIleAlaTyr-231 |
| SEQ. ID. NO. 16730 | 274-AlaLysLysLeuSerHisLeuTyrArgIleThrGluAlaValGlyArgTrpSerMetIleAspIlePheValIle-298 |

Antigenic Index - Jameson-Wolf

| | |
|---|---|
| SEQ. ID. NO. 16731 | 65-IleArgLysGlnAla-69 |
| SEQ. ID. NO. 16732 | 81-ValArgLeuArgGln-85 |
| SEQ. ID. NO. 16733 | 107-AlaGluValArgPhe-111 |

TABLE 1-continued

| | |
|---|---|
| SEQ. ID. NO. 16734 | 143-ArgLeuThrGlyAspAsnAlaValGlnThrAlaSerGluGlyLysThrCysCysSer-161 |
| SEQ. ID. NO. 16735 | 165-TyrPheArgAspSerAlaGluSerProCysGly-175 |
| SEQ. ID. NO. 16736 | 180-GluLeuTyrArgArgArgProLysSerLeuSer-190 |
| SEQ. ID. NO. 16737 | 215-SerAsnProAlaAlaThr-220 |
| SEQ. ID. NO. 16738 | 234-AspGluGlyAspArgLeu-239 |
| SEQ. ID. NO. 16739 | 272-ThrGlyAlaLysLysLeu-277 |
| SEQ. ID. NO. 16740 | 339-LeuLeuTrpAspLysArgAlaSerAspGlyIleAla-350 |
| SEQ. ID. NO. 16741 | 352-AsnGluThrGluLysHisAsp-358 |
| Hydrophilic Regions - Hopp-Woods | |
| SEQ. ID. NO. 16742 | 81-ValArgLeuArgGln-85 |
| SEQ. ID. NO. 16743 | 107-AlaGluValArgPhe-111 |
| SEQ. ID. NO. 16744 | 152-ThrAlaSerGluGlyLysThrCysCys-160 |
| SEQ. ID. NO. 16745 | 168-AspSerAlaGluSerPro-173 |
| SEQ. ID. NO. 16746 | 180-GluLeuTyrArgArgArgProLysSerLeuSer-190 |
| SEQ. ID. NO. 16747 | 234-AspGluGlyAspArgLeu-239 |
| SEQ. ID. NO. 16748 | 273-GlyAlaLysLysLeu-277 |
| SEQ. ID. NO. 16749 | 339-LeuLeuTrpAspLysArgAlaSerAsp-347 |
| SEQ. ID. NO. 16750 | 352-AsnGluThrGluLysHisAsp-358 |
| a154 | |
| AMPHI Regions - AMPHI | |
| SEQ. ID. NO. 16751 | 122-GlyValThrGlyLeuGlyThrLeuLeu-130 |
| SEQ. ID. NO. 16752 | 152-GlnAspIleProProValThr-158 |
| SEQ. ID. NO. 16753 | 262-ThrLysAsnSerLysAsnValLysSer-270 |
| SEQ. ID. NO. 16754 | 298-PheLysGlnSerVal-302 |
| SEQ. ID. NO. 16755 | 360-SerLysGluHisTrpLysGlnGlnPheGlnThrAlaLeuAsnLysGlyLeuThrAla-378 |
| SEQ. ID. NO. 16756 | 389-SerLysMetIleGluLeuAsnAsp-396 |
| SEQ. ID. NO. 16757 | 429-LysLeuAlaAspLeuLeuAspLysPheAspLysLeuPro-441 |
| SEQ. ID. NO. 16758 | 446-ValAlaGluLeuAsnGly-451 |
| SEQ. ID. NO. 16759 | 467-LeuSerSerIleAspLysLeuValGlyLysProGlnThrGlnAsnIleProAsnGluLeuAsnGlnThrLeuLysGluLeuArgThrThr-496 |
| SEQ. ID. NO. 16760 | 506-IleTyrGlyAspValGlnAsnThrLeuGlnSerLeuAspLysThrLeuLysAspValGlnProValIleAsnThrLeuLysGluLys-534 |
| Antigenic Index - Jameson-Wolf | |
| SEQ. ID. NO. 16761 | 1-MetThrAspAsnSerProProProAsnGlyHisAlaGlnAlaArgValArgLysAsnAsnThr-21 |
| SEQ. ID. NO. 16762 | 43-LysGluIleArgAsnArgGlyProVal-51 |
| SEQ. ID. NO. 16763 | 57-AspSerAlaGluGlyIleGluValAsnAsnThr-67 |
| SEQ. ID. NO. 16764 | 75-AspValGlyArgValThrArgIleLysLeuArgAspAspGlnLysGlyValGlu-92 |
| SEQ. ID. NO. 16765 | 100-AspValSerGlyLeuIleArgSerAspThrGln-110 |
| SEQ. ID. NO. 16766 | 114-ValLysProArgIleAspGlnSerGly-122 |
| SEQ. ID. NO. 16767 | 138-ThrProGlyLysSerAspGluAlaLysAspValPheGln-150 |
| SEQ. ID. NO. 16768 | 169-LeuIleGlyLysAsnAspArgIleLeuAsn-178 |
| SEQ. ID. NO. 16769 | 196-AlaHisPheAspProSerAspGlnSer-204 |
| SEQ. ID. NO. 16770 | 212-GlnSerProAsnAspLysLeuIle-219 |
| SEQ. ID. NO. 16771 | 228-GluSerGlyIleAsnIleGluThrThrGlySerGlyIleLysLeuAsnSer-244 |
| SEQ. ID. NO. 16772 | 256-SerPheAspSerProLysThrLysAsnSerLysAsnValLysSerGluAspSer-273 |
| SEQ. ID. NO. 16773 | 275-ThrLeuTyrAspSerArgSerGluValAlaAsnLeuProAspAspArgSerLeu-292 |
| SEQ. ID. NO. 16774 | 300-GlnSerValArgGlyLeu-305 |
| SEQ. ID. NO. 16775 | 311-ValGluTyrLysGlyLeuAsn-317 |
| SEQ. ID. NO. 16776 | 325-ProTyrPheArgAsnAspSer-332 |
| SEQ. ID. NO. 16777 | 345-IleArgIleGluProSerArgLeuGluIleAsnAlaAspGluGlnSerLysGluHisTrpLysGlnGlnPhe-368 |
| SEQ. ID. NO. 16778 | 371-AlaLeuAsnLysGlyLeu-376 |
| SEQ. ID. NO. 16779 | 386-LeuThrGlySerLysMetIleGluLeuAsnAspGlnProSerAlaSerProLysLeuArgPro-406 |
| SEQ. ID. NO. 16780 | 419-GlnGlyGlyGlyLeuAspAspLeuGlnValLysLeu-430 |
| SEQ. ID. NO. 16781 | 432-AspLeuLeuAspLysPheAspLysLeuProLeuAspLysThrValAla-447 |
| SEQ. ID. NO. 16782 | 450-AsnGlySerLeuAlaGluLeuLysSerThrLeuLysSerAlaAsn-464 |
| SEQ. ID. NO. 16783 | 469-SerIleAspLysLeuValGlyLysProGlnThrGlnAsnIleProAsnGluLeuAsnGlnThrLeuLysGluLeuArgThrThr-496 |
| SEQ. ID. NO. 16784 | 500-ValSerProGlnSer-504 |
| SEQ. ID. NO. 16785 | 516-SerLeuAspLysThrLeuLysAspValGln-525 |
| SEQ. ID. NO. 16786 | 530-ThrLeuLysGluLysProAsn-536 |
| SEQ. ID. NO. 16787 | 541-AsnSerSerLysAspProIleProLysGlySerArg-553 |
| Hydrophilic Regions - Hopp-Woods | |
| SEQ. ID. NO. 16788 | 1-MetThrAspAsnSerProProPro-8 |
| SEQ. ID. NO. 16789 | 12-AlaGlnAlaArgValArgLysAsnAsn-20 |
| SEQ. ID. NO. 16790 | 43-LysGluIleArgAsnArgGly-49 |
| SEQ. ID. NO. 16791 | 57-AspSerAlaGluGlyIleGlu-63 |
| SEQ. ID. NO. 16792 | 75-AspValGlyArgValThrArgIleLysLeuArgAspAspGlnLysGlyValGlu-92 |
| SEQ. ID. NO. 16793 | 105-IleArgSerAspThr-109 |
| SEQ. ID. NO. 16794 | 116-ProArgIleAspGln-120 |
| SEQ. ID. NO. 16795 | 140-GlyLysSerAspGluAlaLysAspValPheGln-150 |
| SEQ. ID. NO. 16796 | 171-GlyLysAsnAspArgIleLeu-177 |
| SEQ. ID. NO. 16797 | 196-AlaHisPheAspProSerAspGln-203 |
| SEQ. ID. NO. 16798 | 214-ProAsnAspLysLeuIle-219 |
| SEQ. ID. NO. 16799 | 258-AspSerProLysThrLysAsnSerLysAsnValLysSerGluAspSer-273 |
| SEQ. ID. NO. 16800 | 278-AspSerArgSerGluVal-283 |
| SEQ. ID. NO. 16801 | 285-AsnLeuProAspAspArgSer-291 |
| SEQ. ID. NO. 16802 | 311-ValGluTyrLysGly-315 |
| SEQ. ID. NO. 16803 | 328-AspArgAsnAspSer-332 |
| SEQ. ID. NO. 16804 | 345-IleArgIleGluProSerArgLeuGluIleAsnAlaAspGluGlnSerLysGluHisTrpLys-365 |
| SEQ. ID. NO. 16805 | 390-LysMetIleGluLeuAsnAspGlnProSerAlaSerProLysLeuArgPro-406 |
| SEQ. ID. NO. 16806 | 421-GlyGlyLeuAspAspLeuGlnValLysLeu-430 |
| SEQ. ID. NO. 16807 | 432-AspLeuLeuAspLysPheAspLysLeuProLeuAspLysThrValAla-447 |
| SEQ. ID. NO. 16808 | 454-AlaGluLeuLysSerThrLeuLysSerAlaAsn-464 |

TABLE 1-continued

| | |
|---|---|
| SEQ. ID. NO. 16809 | 469-SerIleAspLysLeuValGly-475 |
| SEQ. ID. NO. 16810 | 482-11eProAsnGluLeu-486 |
| SEQ. ID. NO. 16811 | 488-GlnThrLeuLysGluLeuArgThr-495 |
| SEQ. ID. NO. 16812 | 516-SerLeuAspLysThrLeuLysAspValGln-525 |
| SEQ. ID. NO. 16813 | 530-ThrLeuLysGluLysProAsn-536 |
| SEQ. ID. NO. 16814 | 543-SerSerLysAspProIleProLysGlySerArg-553 | a155
AMPHI Regions - AMPHI

| | |
|---|---|
| SEQ. ID. NO. 16815 | 28-LysLeuGlyPheGlu-32 |
| SEQ. ID. NO. 16816 | 42-AlaAlaSerLeuAsp-46 |
| SEQ. ID. NO. 16817 | 105-LeuArgAlaLysLysVal-110 |
| SEQ. ID. NO. 16818 | 118-ValProArgIleSerArgAlaGlnAlaLeuAspXxxLeuSerXxxMetAlaAsnIleSerGlyTyrArgAlaValIleGluAlaAlaAsnAlaPheGlyArgXxxPheThrGlyGlnIleThrAlaAlaGly-161 |
| SEQ. ID. NO. 16819 | 175-ValAlaGlyLeuAlaAlaIleGlyThrAlaAsnSerLeuGlyAlaValValArgValPhe-194 |
| SEQ. ID. NO. 16820 | 201-AlaGluGlnLeuGluSerMetGlyGly-209 |
| SEQ. ID. NO. 16821 | 225-AspGlyTyrAlaLysValMet-231 |
| SEQ. ID. NO. 16822 | 264-AlaProLysXxxXxxXxxLysGluMetValGluSerMetLys-277 |
| SEQ. ID. NO. 16823 | 281-ValIleValAspLeu-285 |
| SEQ. ID. NO. 16824 | 307-GlyValLysIleIleGlyTyrThrAspMetAlaAsnArgLeuAlaGlyGln-323 |
| SEQ. ID. NO. 16825 | 330-ThrAsnLeuValAsnLeuThrLysLeuLeuSer-340 |
| SEQ. ID. NO. 16826 | 404-LysLeuAlaProAlaXxxIle-410 |
| SEQ. ID. NO. 16827 | 428-AsnHisPheIleVal-432 |
| SEQ. ID. NO. 16828 | 451-LeuHisThrProLeuMetSerValThrAsnAlaIleSerGlyIleIle-466 |
| SEQ. ID. NO. 16829 | 469-GlyAlaLeuLeuGln-473 |
| SEQ. ID. NO. 16830 | 478-AsnGlyPheValSerLeuLeuSerPheValAla-488 |
| SEQ. ID. NO. 16831 | 494-IleAsnIlePheGlyGly-499 |

Antigenic Index - Jameson-Wolf

| | |
|---|---|
| SEQ. ID. NO. 16832 | 4-GlyIleProArgGluSerLeuSerGlyGluThrArgVal-16 |
| SEQ. ID. NO. 16833 | 44-SerLeuAspAspAlaAla-49 |
| SEQ. ID. NO. 16834 | 72-ValAsnAlaProSerGluAspGluLeuProLeuLeuLysGluGlyGln-87 |
| SEQ. ID. NO. 16835 | 94-TrpProArgGlnAsnGluAlaLeu-101 |
| SEQ. ID. NO. 16836 | 105-LeuArgAlaLysLysValAsn-111 |
| SEQ. ID. NO. 16837 | 117-MetValProArgIleSerArg-123 |
| SEQ. ID. NO. 16838 | 159-AlaAlaGlyLysValProProAla-166 |
| SEQ. ID. NO. 16839 | 202-GluGlnLeuGluSerMetGlyGlyLys-210 |
| SEQ. ID. NO. 16840 | 215-AspPheProGlnSerGlyGlySerGlyAspGlyTyrAlaLysValMetSer-232 |
| SEQ. ID. NO. 16841 | 242-LeuPheAlaGluGlnAlaLysGluValAsp-251 |
| SEQ. ID. NO. 16842 | 259-IleProGlyLysProAlaProLysXxxXxxXxxLysGluMetValGluSerMetLysProGlySer-280 |
| SEQ. ID. NO. 16843 | 290-GlyGlyAsnCysGluLeuThrLysGlnGlyGlu-300 |
| SEQ. ID. NO. 16844 | 320-LeuAlaGlyGlnSerSer-325 |
| SEQ. ID. NO. 16845 | 338-LeuLeuSerProAsnLysAspGlyGluIle-347 |
| SEQ. ID. NO. 16846 | 349-LeuAspPheGluAspValIle-355 |
| SEQ. ID. NO. 16847 | 360-ThrValThrArgAspGlyGluIleThrPhePro-370 |
| SEQ. ID. NO. 16848 | 378-AlaGlnProGlnGlnThrProSerGluLysAlaAlaProAlaAlaLysProGluProLysPro-398 |
| SEQ. ID. NO. 16849 | 509-MetPheArgLysGly-513 |

Hydrophilic Regions - Hopp-Woods

| | |
|---|---|
| SEQ. ID. NO. 16850 | 4-GlyIleProArgGluSerLeuSerGlyGluThrArgVal-16 |
| SEQ. ID. NO. 16851 | 44-SerLeuAspAspAlaAla-49 |
| SEQ. ID. NO. 16852 | 74-AlaProSerGluAspGluLeuProLeuLeuLysGluGlyGln-87 |
| SEQ. ID. NO. 16853 | 96-ArgGlnAsnGluAlaLeu-101 |
| SEQ. ID. NO. 16854 | 105-LeuArgAlaLysLysValAsn-111 |
| SEQ. ID. NO. 16855 | 117-MetValProArgIleSerArg-123 |
| SEQ. ID. NO. 16856 | 202-GluGlnLeuGluSerMetGly-208 |
| SEQ. ID. NO. 16857 | 215-AspPheProGlnSerGlyGlySerGlyAspGlyTyrAla-228 |
| SEQ. ID. NO. 16858 | 242-LeuPheAlaGluGlnAlaLysGluValAsp-251 |
| SEQ. ID. NO. 16859 | 260-ProGlyLysProAlaProLysXxxXxxXxxLysGluMetValGluSerMetLysPro-278 |
| SEQ. ID. NO. 16860 | 291-GlyAsnCysGluLeuThrLysGlnGlyGlu-300 |
| SEQ. ID. NO. 16861 | 340-SerProAsnLysAspGlyGluIle-347 |
| SEQ. ID. NO. 16862 | 349-LeuAspPheGluAspValIle-355 |
| SEQ. ID. NO. 16863 | 360-ThrValThrArgAspGlyGluIle-367 |
| SEQ. ID. NO. 16864 | 382-GlnThrProSerGluLysAlaAlaProAlaAlaLysProGluProLysPro-398 | a156
AMPHI Regions - AMPHI

| | |
|---|---|
| SEQ. ID. NO. 16865 | 56-AsnGlyPheGluAlaPheAlaProPhe-64 |
| SEQ. ID. NO. 16866 | 80-AlaThrValAsnThr-84 |

Antigenic Index - Jameson-Wolf

| | |
|---|---|
| SEQ. ID. NO. 16867 | 21-TyrAlaLysLysAlaGlyGlyPheArgPheLysAspAsnHisAsnProArgAspPheLeuAlaArgThrGlnGlyThrAlaAlaArgAlaHisAlaAlaGlnGlnAsnGlyPheGlu-59 |
| SEQ. ID. NO. 16868 | 73-AlaThrGlyAsnAlaGlyGln-79 |
| SEQ. ID. NO. 16869 | 103-AspLysAlaAlaLeu-107 |

Hydrophilic Regions - Hopp-Woods

| | |
|---|---|
| SEQ. ID. NO. 16870 | 21-TyrAlaLysLysAlaGlyGlyPheArgPheLysAspAsnHisAsnProArgAspPheLeuAla-41 |
| SEQ. ID. NO. 16871 | 43-ThrGlnGlyThrAlaAlaArgAlaHisAla-52 |
| SEQ. ID. NO. 16872 | 103-AspLysAlaAlaLeu-107 | a157
AMPHI Regions - AMPHI

| | |
|---|---|
| SEQ. ID. NO. 16873 | 10-ArgArgGluLeuArgArgAla-16 |
| SEQ. ID. NO. 16874 | 32-IleAsnArgLeuLeuLysArgTyrIleLysArgGly-43 |
| SEQ. ID. NO. 16875 | 61-PheValArgAlaAlaGln-66 |
| SEQ. ID. NO. 16876 | 137-LeuGlyGlnAlaGlyGly-142 |

TABLE 1-continued

| SEQ. ID. NO. 16877 | 167-GlnPheValAspArgLeuProArgGluProHisAspLeuLeuLeuAspGly-183 |

Antigenic Index - Jameson-Wolf

| SEQ. ID. NO. 16878 | 1-MetArgAsnGluGluLysHisAlaLeuArgArgGluLeuArgArgAlaArgAlaGlnMetGlyHisGlnGlyArgLeuAlaAla-28 |
| SEQ. ID. NO. 16879 | 34-ArgLeuLeuLysArgTyrIleLysArgGlyArgLysIle-46 |
| SEQ. ID. NO. 16880 | 51-ProMetGlyLysGluLeuArgLeuAspGlyPheVal-62 |
| SEQ. ID. NO. 16881 | 64-AlaAlaGlnLysArgGlyAlaLysLeu-72 |
| SEQ. ID. NO. 16882 | 77-IleGluProArgSerArgArgMetTrp-85 |
| SEQ. ID. NO. 16883 | 88-ProTyrProGluSerGlyMetGluArgGluArgIleArgGlyArgAlaLysLeuAsnVal-107 |
| SEQ. ID. NO. 16884 | 110-PheAlaGlyArgLysIleArgVal-117 |
| SEQ. ID. NO. 16885 | 129-GlyIleAspArgGluGlyTyrArgLeuGlyGln-139 |
| SEQ. ID. NO. 16886 | 153-TyrArgLeuGlnAla-157 |
| SEQ. ID. NO. 16887 | 168-PheValAspArgLeuProArgGluProHisAspLeuLeuLeu-181 |

Hydrophilic Regions - Hopp-Woods

| SEQ. ID. NO. 16888 | 1-MetArgAsnGluGluLysHisAlaLeuArgArgGluLeuArgArgAlaArgAlaGlnMet-20 |
| SEQ. ID. NO. 16889 | 34-ArgLeuLeuLysArgTyrIleLysArgGlyArgLysIle-46 |
| SEQ. ID. NO. 16890 | 54-LysGluLeuArgLeu-58 |
| SEQ. ID. NO. 16891 | 64-AlaAlaGlnLysArgGlyAla-70 |
| SEQ. ID. NO. 16892 | 77-IleGluProArgSerArgArg-83 |
| SEQ. ID. NO. 16893 | 92-SerGlyMetGluArgGluArgIleArgGlyArgAlaLysLeu-105 |
| SEQ. ID. NO. 16894 | 111-AlaGlyArgLysIleArgVal-117 |
| SEQ. ID. NO. 16895 | 129-GlyIleAspArgGluGlyTyrArg-136 |
| SEQ. ID. NO. 16896 | 153-TyrArgLeuGlnAla-157 |
| SEQ. ID. NO. 16897 | 170-AspArgLeuProArgGluProHisAspLeuLeu-180 | a158
AMPHI Regions - AMPHI

| SEQ. ID. NO. 16898 | 20-PheSerArgAlaAlaGluGlnLeu-27 |
| SEQ. ID. NO. 16899 | 33-AlaValSerArgIleValLysArgLeuGlu-42 |
| SEQ. ID. NO. 16900 | 46-GlyValAsnLeuLeuAsnArgThr-53 |
| SEQ. ID. NO. 16901 | 63-GlyAlaGlnTyrPheArgArgAlaGlnArgIleLeuGlnGlu-76 |
| SEQ. ID. NO. 16902 | 85-LeuAlaValHisGluIleProGln-92 |
| SEQ. ID. NO. 16903 | 166-ValIleAlaSerPro-170 |
| SEQ. ID. NO. 16904 | 178-ThrProGlnSerThrGluGluLeu-185 |
| SEQ. ID. NO. 16905 | 188-HisGlnCysLeuGlyPheThrGluProGlySerLeuAsnThrTrpAlaVal-204 |

Antigenic Index - Jameson-Wolf

| SEQ. ID. NO. 16906 | 1-MetLysThrAsnSerGluGluLeu-8 |
| SEQ. ID. NO. 16907 | 16-GluSerGlySerPheSerArgAlaAlaGlu-25 |
| SEQ. ID. NO. 16908 | 36-ArgIleValLysArgLeuGluGluLysLeuGly-46 |
| SEQ. ID. NO. 16909 | 49-LeuLeuAsnArgThrThrArgGlnLeuSerLeuThrGluGluGlyAlaGlnTyrPheArgArgAlaGlnArgIleLeuGln-75 |
| SEQ. ID. NO. 16910 | 78-AlaAlaAlaGluThrGluMet-84 |
| SEQ. ID. NO. 16911 | 90-IleProGlnGlyValLeuArgValAspSer-99 |
| SEQ. ID. NO. 16912 | 114-LysPheAsnGluArgTyrProHisIleArg-123 |
| SEQ. ID. NO. 16913 | 136-IleGluArgLysValAspIle-142 |
| SEQ. ID. NO. 16914 | 144-LeuArgAlaGlyGluLeuAspAspSerGlyLeuArgAla-156 |
| SEQ. ID. NO. 16915 | 158-HisLeuPheAspSerArgPheArgVal-166 |
| SEQ. ID. NO. 16916 | 168-AlaSerProGluTyrLeuAlaLysHisGlyThrProGlnSerThrGluGluLeuAla-186 |
| SEQ. ID. NO. 16917 | 192-GlyPheThrGluProGlySerLeuAsn-200 |
| SEQ. ID. NO. 16918 | 207-AlaGlnGlyAsnProTyrLysIle-214 |
| SEQ. ID. NO. 16919 | 216-ProHisPheThrAlaSerSerGlyGluIleLeu-226 |
| SEQ. ID. NO. 16920 | 229-LeuCysLeuSerGlyCysGly-235 |
| SEQ. ID. NO. 16921 | 243-LeuValAspAsnAspIleAlaGluGlyLysLeu-253 |
| SEQ. ID. NO. 16922 | 258-AlaGluGlnThrSerAsnLysThrHisProPhe-268 |
| SEQ. ID. NO. 16923 | 273-TyrSerAspLysAlaValAsnLeu-280 |
| SEQ. ID. NO. 16924 | 292-GluLeuGlyAsnAsnLeuCysGly-299 |

Hydrophilic Regions - Hopp-Woods

| SEQ. ID. NO. 16925 | 1-MetLysThrAsnSerGluGluLeu-8 |
| SEQ. ID. NO. 16926 | 19-SerPheSerArgAlaAlaGlu-25 |
| SEQ. ID. NO. 16927 | 36-ArgIleValLysArgLeuGluGluLysLeuGly-46 |
| SEQ. ID. NO. 16928 | 58-SerLeuThrGluGluGlyAlaGlnTyrPheArgArgAlaGlnArgIleLeuGln-75 |
| SEQ. ID. NO. 16929 | 78-AlaAlaAlaGluThrGluMet-84 |
| SEQ. ID. NO. 16930 | 95-LeuArgValAspSer-99 |
| SEQ. ID. NO. 16931 | 114-LysPheAsnGluArgTyrPro-120 |
| SEQ. ID. NO. 16932 | 136-IleGluArgLysValAspIle-142 |
| SEQ. ID. NO. 16933 | 144-LeuArgAlaGlyGluLeuAspAspSerGlyLeuArgAla-156 |
| SEQ. ID. NO. 16934 | 162-SerArgPheArgVal-166 |
| SEQ. ID. NO. 16935 | 180-GlnSerThrGluGluLeuAla-186 |
| SEQ. ID. NO. 16936 | 246-AsnAspIleAlaGluGlyLysLeu-253 |
| SEQ. ID. NO. 16937 | 260-GlnThrSerAsnLysThrHis-266 |
| SEQ. ID. NO. 16938 | 276-LysAlaValAsnLeu-280 | a160
AMPHI Regions - AMPHI

| SEQ. ID. NO. 16939 | 6-LysLeuValAspPheAlaGlnLeuThrGly-15 |
| SEQ. ID. NO. 16940 | 72-GlyLeuGlyHisVal-76 |
| SEQ. ID. NO. 16941 | 121-AlaAspLeuMetAsnGlyLeuProGluThr-130 |
| SEQ. ID. NO. 16942 | 157-GlyThrValSerMetValAsnAlaLeuSerSer-167 |
| SEQ. ID. NO. 16943 | 186-LeuSerGlyValLeuLysGlyTrpGlnAspLysArg-197 |
| SEQ. ID. NO. 16944 | 200-HisLeuIleGlnLysValIleAspLysProGlu-210 |
| SEQ. ID. NO. 16945 | 218-MetValAlaAlaAlaAsn-223 |
| SEQ. ID. NO. 16946 | 229-LeuMetArgArgPhe-233 |
| SEQ. ID. NO. 16947 | 242-HisAlaPheValAsnHisIleArg-249 |
| SEQ. ID. NO. 16948 | 279-PheGlyLysAlaPheLys-284 |

TABLE 1-continued

Antigenic Index - Jameson-Wolf
SEQ. ID. NO. 16949  2-AspIleLeuAspLysLeuVal-8
SEQ. ID. NO. 16950  28-SerValArgHisGluThrLeuGlnArgGluGlyLeu-39
SEQ. ID. NO. 16951  51-CysIleAspGlyGluThrSerProArgProValSerThrGlyAsp-65
SEQ. ID. NO. 16952  77-LeuSerHisAspGlyLysCysGlyGluSerLeuGlnProAspMetArgGlnHisGly-95
SEQ. ID. NO. 16953  101-GlnCysGlyAsnGlyGlnAspMet-108
SEQ. ID. NO. 16954  115-PheArgTyrAspThrHisAla-121
SEQ. ID. NO. 16955  123-LeuMetAsnGlyLeu-127
SEQ. ID. NO. 16956  149-LeuGluSerLysLysProLeu-155
SEQ. ID. NO. 16957  178-LeuGluGlnAspLysAspValGluLeu-186
SEQ. ID. NO. 16958  192-GlyTrpGlnAspLysArgLeuGly-199
SEQ. ID. NO. 16959  205-ValIleAspLysProGluAspGluTrpAsnValAspLysMetVal-219
SEQ. ID. NO. 16960  228-GlnLeuMetArgArgPheLysSerArgValGlyLeuSerProHis-242
SEQ. ID. NO. 16961  255-LeuLeuLeuLysLysAsnProAspSerVal-264
SEQ. ID. NO. 16962  274-GlnSerGluThrHisPhe-279
SEQ. ID. NO. 16963  281-LysAlaPheLysArg-285
SEQ. ID. NO. 16964  290-SerProGlyGlnTyrArgLysGluGlyGlyGlnLys-301
Hydrophilic Regions - Hopp-Woods
SEQ. ID. NO. 16965  2-AspIleLeuAspLysLeuVal-8
SEQ. ID. NO. 16966  29-ValArgHisGluThrLeuGlnArgGluGlyLeu-39
SEQ. ID. NO. 16967  53-AspGlyGluThrSerProArgProValSer-62
SEQ. ID. NO. 16968  79-HisAspGlyLysCysGlyGluSerLeuGlnProAspMetArgGln-93
SEQ. ID. NO. 16969  101-GlnCysGlyAsnGlyGlnAsp-107
SEQ. ID. NO. 16970  149-LeuGluSerLysLysProLeu-155
SEQ. ID. NO. 16971  178-LeuGluGlnAspLysAspValGluLeu-186
SEQ. ID. NO. 16972  193-TrpGlnAspLysArgLeuGly-199
SEQ. ID. NO. 16973  205-ValIleAspLysProGluAspGluTrpAsnVal-215
SEQ. ID. NO. 16974  228-GlnLeuMetArgArgPheLysSerArgValGly-238
SEQ. ID. NO. 16975  255-LeuLeuLeuLysLysAsnProAspSer-263
SEQ. ID. NO. 16976  281-LysAlaPheLysArg-285
SEQ. ID. NO. 16977  293-GlnTyrArgLysGluGlyGlyGlnLys-301
a163
AMPHI Regions - AMPHI
SEQ. ID. NO. 16978  60-SerSerLeuGlyAsnIle-65
SEQ. ID. NO. 16979  67-LeuGlyArgAspGluAsp-72
SEQ. ID. NO. 16980  76-PheGlyPheLeuSerTrpLeuAlaMetLeuPhe-86
SEQ. ID. NO. 16981  100-AlaGluProLeuMetHisTyrPheSerAspIleThrAla-112
SEQ. ID. NO. 16982  170-IleSerGlyArgPheGlyAspAlaIleAspIleMetAlaLeuLeuAlaThrPhePheGlyIleIleThrThr-193
SEQ. ID. NO. 16983  227-MetSerLeuAlaValValSerAlaIleSerGlyValGlyLysGlyValLysValLeuSer-246
SEQ. ID. NO. 16984  272-AlaPheGlyAspAsnIleGlyAsnTyrLeuGlyAsnLeuValArg-286
SEQ. ID. NO. 16985  313-TrpCysSerTrpAlaProPheValGlyLeuPheIleAla-325
SEQ. ID. NO. 16986  346-LeuPheGlyValLeuTrpPhe-352
SEQ. ID. NO. 16987  367-AlaGlyGlyValLeuGluLysMetThrSerSer-377
SEQ. ID. NO. 16988  380-ThrLeuLeuPheLysPhePheAsnTyrLeuProLeuProGluLeuThrSerIleValSerLeuLeu-401
SEQ. ID. NO. 16989  438-TrpGlyValLeuMetSerAla-444
SEQ. ID. NO. 16990  454-GlyLeuGlyAsnLeuGlnSerMetThrLeu-463
SEQ. ID. NO. 16991  520-GluGlnAspIleLeuLysPheLeuLysHisThrAla-531
SEQ. ID. NO. 16992  535-MetHisGluLeuGlnArgGluLeu-542
SEQ. ID. NO. 16993  574-AspPheMetTyrGlyIle-579
SEQ. ID. NO. 16994  583-GlyGlnAspValSerAspGlnLeu-590
SEQ. ID. NO. 16995  630-AlaAspIleLeuLysAsnTyr-636
Antigenic Index - Jameson-Wolf
SEQ. ID. NO. 16996  29-AspArgAlaLysGlu-33
SEQ. ID. NO. 16997  65-IleArgLeuGlyArgAspGluAspValPro-74
SEQ. ID. NO. 16998  111-ThrAlaGlyThrProGluHisArgGlnGln-120
SEQ. ID. NO. 16999  166-LeuLysGluLysIleSerGlyArgPheGlyAspAlaIleAsp-179
SEQ. ID. NO. 17000  200-GlnLeuGlyAlaGlyLeu-205
SEQ. ID. NO. 17001  237-GlyValGlyLysGlyValLysVal-244
SEQ. ID. NO. 17002  293-AlaTyrGluArgGluHisLysProTrpPhe-302
SEQ. ID. NO. 17003  326-ArgIleSerLysGlyArgThrIleArg-334
SEQ. ID. NO. 17004  370-ValLeuGluLysMetThrSerSerProGluThr-380
SEQ. ID. NO. 17005  409-ThrSerAlaAspSerGlyIle-415
SEQ. ID. NO. 17006  421-IleThrSerArgAspLysGlyLeuSerAlaProArgTrp-433
SEQ. ID. NO. 17007  451-ArgSerGlyGlyLeuGlyAsn-457
SEQ. ID. NO. 17008  484-LeuSerAlaAspLysLysTyrPheGluThrArgValAsnProThrSer-499
SEQ. ID. NO. 17009  503-ThrGlyGlyLysTrpLysGluArgLeu-511
SEQ. ID. NO. 17010  516-SerGlnThrGlnGluGlnAspIle-523
SEQ. ID. NO. 17011  537-GluLeuGlnArgGluLeuSerGluThrTyrGlyLeu-548
SEQ. ID. NO. 17012  550-ValArgValAspLysMetPheHisGlnAspGluProAla-562
SEQ. ID. NO. 17013  566-ValIleArgLysGluThrMetArg-573
SEQ. ID. NO. 17014  581-SerValGlyGlnAspValSerAspGlnLeuIleAsnAspGlyLysLeuProHisIleArgHisGlnThrThrTyrLysProTyr-608
SEQ. ID. NO. 17015  612-PheAspGlyArgValGlyTyr-618
SEQ. ID. NO. 17016  622-TyrMetAsnLysAspGluLeuIle-629
SEQ. ID. NO. 17017  632-IleLeuLysAsnTyrGlu-637
SEQ. ID. NO. 17018  654-GluGlnValGluLeuAlaGlu-660
Hydrophilic Regions - Hopp-Woods
SEQ. ID. NO. 17019  29-AspArgAlaLysGlu-33
SEQ. ID. NO. 17020  66-ArgLeuGlyArgAspGluAspValPro-74
SEQ. ID. NO. 17021  114-ThrProGluHisArgGlnGln-120
SEQ. ID. NO. 17022  166-LeuLysGluLysIleSerGlyArgPheGlyAsp-176

TABLE 1-continued

| | |
|---|---|
| SEQ. ID. NO. 17023 | 238-ValGlyLysGlyValLysVal-244 |
| SEQ. ID. NO. 17024 | 293-AlaTyrGluArgGluHisLysPro-300 |
| SEQ. ID. NO. 17025 | 327-IleSerLysGlyArgThrIleArg-334 |
| SEQ. ID. NO. 17026 | 370-ValLeuGluLysMetThrSerSerPro-378 |
| SEQ. ID. NO. 17027 | 422-ThrSerArgAspLysGlyLeuSer-429 |
| SEQ. ID. NO. 17028 | 484-LeuSerAlaAspLysLysTyrPheGlu-492 |
| SEQ. ID. NO. 17029 | 506-LysTrpLysGluArgLeu-511 |
| SEQ. ID. NO. 17030 | 517-GlnThrGlnGluGlnAspIle-523 |
| SEQ. ID. NO. 17031 | 537-GluLeuGlnArgGluLeuSerGluGluTyrGlyLeu-548 |
| SEQ. ID. NO. 17032 | 550-ValArgValAspLysMetPheHisGlnAspGluProAla-562 |
| SEQ. ID. NO. 17033 | 566-ValIleArgLysGluThrMetArg-573 |
| SEQ. ID. NO. 17034 | 581-SerValGlyGlnAspValSerAsp-588 |
| SEQ. ID. NO. 17035 | 590-LeuIleAsnAspGlyLysLeuProHis-598 |
| SEQ. ID. NO. 17036 | 622-TyrMetAsnLysAspGluLeuIle-629 |
| SEQ. ID. NO. 17037 | 654-GluGlnValGluLeuAlaGlu-660 |
| a164 | |
| AMPHI Regions - AMPHI | |
| SEQ. ID. NO. 17038 | 6-AlaAsnPheTyrGluMetLeuThrAlaAla-15 |
| SEQ. ID. NO. 17039 | 33-AlaTyrArgAlaLeuLysGlnGlu-40 |
| SEQ. ID. NO. 17040 | 75-AlaValSerAlaIleGlyAlaVal-82 |
| SEQ. ID. NO. 17041 | 97-TyrIleLeuAsnAspCys-102 |
| SEQ. ID. NO. 17042 | 113-LeuSerLysGluLeuAlaGlyLeuLysAla-122 |
| SEQ. ID. NO. 17043 | 148-PheGluAspValArgArgPheProGlu-156 |
| SEQ. ID. NO. 17044 | 160-LeuGlyArgGlnProArgIleAsnAspLeuAlaHis-171 |
| SEQ. ID. NO. 17045 | 189-TyrAlaAsnLeuPheAlaAsnLeuAsnGlyIleGluArgIlePheLys-204 |
| SEQ. ID. NO. 17046 | 264-ValProAlaIleTyrThr-269 |
| SEQ. ID. NO. 17047 | 282-TrpPheAsnArgIle-286 |
| SEQ. ID. NO. 17048 | 311-AlaLysLeuLeuGluGlyTyrGlyLeuSer-320 |
| SEQ. ID. NO. 17049 | 362-GluValGlyGluLeuIle-367 |
| SEQ. ID. NO. 17050 | 374-MetArgGlyTyrLeuAsn-379 |
| SEQ. ID. NO. 17051 | 387-ThrIleValAsnGlyTrpLeuLys-394 |
| SEQ. ID. NO. 17052 | 424-ValTyrProArgGluIleGluGluGlu-432 |
| SEQ. ID. NO. 17053 | 459-PheValGlnLeuLysGluGlyMet-466 |
| SEQ. ID. NO. 17054 | 472-GluIleArgArgHisLeuArgThrVal-480 |
| SEQ. ID. NO. 17055 | 484-PheLysIleProLysGln-489 |
| SEQ. ID. NO. 17056 | 499-AsnAlaThrGlyLysValLeuLysArgValLeuLysGluGlnPheAspGlyAsn-516 |
| Antigenic Index - Jameson-Wolf | |
| SEQ. ID. NO. 17057 | 1-MetAsnArgThrTyr-5 |
| SEQ. ID. NO. 17058 | 15-AlaCysArgLysAsnGlyAsnGly-22 |
| SEQ. ID. NO. 17059 | 26-PheAspGlyLysGluLysThrAlaTyrArgAlaLeuLysGlnGluAlaGluAla-43 |
| SEQ. ID. NO. 17060 | 63-ValSerAsnSerThrGlu-68 |
| SEQ. ID. NO. 17061 | 88-ThrPheLeuLysAsnSerGlu-94 |
| SEQ. ID. NO. 17062 | 100-AsnAspCysLysAla-104 |
| SEQ. ID. NO. 17063 | 112-GlyLeuSerLysGluLeuAlaGly-119 |
| SEQ. ID. NO. 17064 | 121-LysAlaGlnThrProValGlu-127 |
| SEQ. ID. NO. 17065 | 133-GlyGlnSerArgProAspGlyGluMetAlaGluGlyAspAlaPhePheGluAspValArgArgPheProGluLysProAspLeuGlyArgGlnProArgIleAsnAsp-168 |
| SEQ. ID. NO. 17066 | 176-SerGlyThrThrGlyHisProLysGlyAla-185 |
| SEQ. ID. NO. 17067 | 196-LeuAsnGlyIleGluArgIlePheLysIleSerLysArgAspArgPhe-211 |
| SEQ. ID. NO. 17068 | 270-AlaMetSerLysThrLysIle-276 |
| SEQ. ID. NO. 17069 | 291-SerGlyGlyAlaProLeuAla-297 |
| SEQ. ID. NO. 17070 | 304-PheLysAlaLysPheProArg-310 |
| SEQ. ID. NO. 17071 | 317-TyrGlyLeuSerGluAlaSer-323 |
| SEQ. ID. NO. 17072 | 330-ThrProGluArgGlnLysAlaArgSer-338 |
| SEQ. ID. NO. 17073 | 343-LeuProGlyLeuGluValLysAlaValAspGluGluLeuValGluValProArgGlyGluValGly-364 |
| SEQ. ID. NO. 17074 | 367-IleValArgGlyGlySerValMet-374 |
| SEQ. ID. NO. 17075 | 382-AlaAlaThrAspGluThrIle-388 |
| SEQ. ID. NO. 17076 | 393-LeuLysThrGlyAsp-397 |
| SEQ. ID. NO. 17077 | 400-ThrIleAspGluAspGly-405 |
| SEQ. ID. NO. 17078 | 410-ValAspArgLysLysAspLeuIleIleSerLysGlyGlnAsnValTyrProArgGluIleGluGluGluIleTyrLys-435 |
| SEQ. ID. NO. 17079 | 446-GlyValLysAspArgTyrAlaAspGluGluIle-456 |
| SEQ. ID. NO. 17080 | 462-LeuLysGluGlyMetAspLeuGlyGluAsnGluIleArgArgHisLeuArg-478 |
| SEQ. ID. NO. 17081 | 490-IleHisPheLysAspGlyLeuProArgAsnAlaThrGlyLysValLeuLysArgValLeuLysGluGlnPheAspGlyAsnLys-517 |
| Hydrophilic Regions - Hopp-Woods | |
| SEQ. ID. NO. 17082 | 15-AlaCysArgLysAsnGlyAsn-21 |
| SEQ. ID. NO. 17083 | 26-PheAspGlyLysGluLysThrAlaTyrArgAlaLeuLysGlnGluAlaGluAla-43 |
| SEQ. ID. NO. 17084 | 112-GlyLeuSerLysGluLeuAlaGly-119 |
| SEQ. ID. NO. 17085 | 135-SerArgProAspGlyGluMetAlaGluGlyAspAlaPhePheGluAspValArgArgPheProGluLysProAspLeuGlyArgGlnProArgIleAsnAsp-168 |
| SEQ. ID. NO. 17086 | 198-GlyIleGluArgIlePheLysIleSerLysArgAspArgPhe-211 |
| SEQ. ID. NO. 17087 | 304-PheLysAlaLysPheProArg-310 |
| SEQ. ID. NO. 17088 | 330-ThrProGluArgGlnLysAlaArgSer-338 |
| SEQ. ID. NO. 17089 | 346-LeuGluValLysAlaValAspGluGluLeuValGluValProArgGlyGluValGly-364 |
| SEQ. ID. NO. 17090 | 382-AlaAlaThrAspGluThrIle-388 |
| SEQ. ID. NO. 17091 | 400-ThrIleAspGluAspGly-405 |
| SEQ. ID. NO. 17092 | 410-ValAspArgLysLysAspLeuIleIle-418 |
| SEQ. ID. NO. 17093 | 425-TyrProArgGluIleGluGluGluIleTyrLys-435 |
| SEQ. ID. NO. 17094 | 446-GlyValLysAspArgTyrAlaAspGluGluIle-456 |
| SEQ. ID. NO. 17095 | 462-LeuLysGluGlyMetAspLeuGlyGluAsnGluIleArgArgHisLeuArg-478 |
| SEQ. ID. NO. 17096 | 494-AspGlyLeuProArgAsnAlaThr-501 |

TABLE 1-continued

SEQ. ID. NO. 17097 503-LysValLeuLysArgValLeuLysGluGlnPheAspGlyAsnLys-517
a165-1
AMPHI Regions - AMPHI
SEQ. ID. NO. 17098 17-AlaThrLeuGlyValLeuLeuLysGluLeu-26
SEQ. ID. NO. 17099 33-ThrLeuIleGluArgLeuGluAsp-40
SEQ. ID. NO. 17100 72-IleIleAspProAlaArgAlaLeuAsnIleAla-82
SEQ. ID. NO. 17101 90-GlnPheTrpAlaThr-94
SEQ. ID. NO. 17102 108-AsnAlaValProHis-112
SEQ. ID. NO. 17103 125-LeuGlnLysArgTyrAspAlaPheLysThrGlnLysLeuPheGluAsnMet-141
SEQ. ID. NO. 17104 182-ArgLeuThrArgGlnMetValLysTyrLeuGlnGly-193
SEQ. ID. NO. 17105 198-ThrGluPheAsnArgHisValGluAspIleLysArgGlu-210
SEQ. ID. NO. 17106 364-LysThrLysGluGlu-368
SEQ. ID. NO. 17107 371-AlaSerLeuLeuGluTyrTyr-377
SEQ. ID. NO. 17108 456-ArgLeuLysGluLeu-460
Antigenic Index - Jameson-Wolf
SEQ. ID. NO. 17109 1-MetAlaGluAlaThrAsp-6
SEQ. ID. NO. 17110 24-LysGluLeuGluProSerTrp-30
SEQ. ID. NO. 17111 36-GluArgLeuGluAspValAlaLeuGluSerSerAsnAlaTrpAsnAsnAlaGlyThrGly-55
SEQ. ID. NO. 17112 97-AlaGluGlyLysLeuGluAspAsnSer-105
SEQ. ID. NO. 17113 117-MetAsnGluAspHisCysSerTyrLeuGlnLysArgTyrAspAlaPheLysThrGlnLysLeuPheGlu-139
SEQ. ID. NO. 17114 141-MetGluPheSerThrAspArgAsnLysIleSerAsp-152
SEQ. ID. NO. 17115 157-MetMetArgGlyArgAspGluAsnGlnPro-166
SEQ. ID. NO. 17116 169-AlaAsnTyrSerAlaGluGlyThrAspValAspPheGlyArgLeuThrArgGlnMet-187
SEQ. ID. NO. 17117 191-LeuGlnGlyLysGlyValLysThrGluPheAsnArgHisValGluAspIleLysArgGluSerAspGly-213
SEQ. ID. NO. 17118 219-ThrAlaAspThrArgAsnProAspGlyGlnLeu-229
SEQ. ID. NO. 17119 249-GlnLysSerGlyIleProGluGlyLysGlyTyrGly-260
SEQ. ID. NO. 17120 269-PheArgAsnSerAsnProGluThrAlaGluGlnHisAsn-281
SEQ. ID. NO. 17121 300-LeuAspThrArgAsnValAspGlyLysArgHisLeu-311
SEQ. ID. NO. 17122 322-AsnPheLeuLysGlnAsnGlySerLeuMet-330
SEQ. ID. NO. 17123 361-GluLeuArgLysThrLysGluGluArgPhe-370
SEQ. ID. NO. 17124 377-TyrProGluAlaAsnProAspAspTrpGlu-386
SEQ. ID. NO. 17125 395-GlnIleIleLysLysAspSerGluLysGlyGly-405
SEQ. ID. NO. 17126 415-AlaHisAlaAspGlySer-420
SEQ. ID. NO. 17127 428-SerProGlyAlaSerThr-433
SEQ. ID. NO. 17128 446-PheProGluArgThrProSerTrpGluGlyArgLeuLysGluLeuValProGlyTyr-464
SEQ. ID. NO. 17129 467-LysLeuAsnGluAsnProGluArgAlaAspGlu-477
Hydrophilic Regions - Hopp-Woods
SEQ. ID. NO. 17130 1-MetAlaGluAlaThrAsp-6
SEQ. ID. NO. 17131 24-LysGluLeuGluPro-28
SEQ. ID. NO. 17132 36-GluArgLeuGluAspValAlaLeuGluSer-45
SEQ. ID. NO. 17133 97-AlaGluGlyLysLeuGluAspAsnSer-105
SEQ. ID. NO. 17134 117-MetAsnGluAspHisCys-122
SEQ. ID. NO. 17135 125-LeuGlnLysArgTyrAspAlaPheLysThr-134
SEQ. ID. NO. 17136 141-MetGluPheSerThrAspArgAsnLysIleSerAsp-152
SEQ. ID. NO. 17137 158-MetArgGlyArgAspGluAsnGlnPro-166
SEQ. ID. NO. 17138 172-SerAlaGluGlyThrAspValAspPhe-180
SEQ. ID. NO. 17139 182-ArgLeuThrArgGlnMet-187
SEQ. ID. NO. 17140 194-LysGlyValLysThrGluPheAsnArgHisValGluAspIleLysArgGluSerAspGly-213
SEQ. ID. NO. 17141 219-ThrAlaAspThrArgAsnProAspGly-227
SEQ. ID. NO. 17142 252-GlyIleProGluGlyLysGly-258
SEQ. ID. NO. 17143 272-SerAsnProGluThrAlaGluGlnHisAsn-281
SEQ. ID. NO. 17144 300-LeuAspThrArgAsnValAspGlyLysArg-309
SEQ. ID. NO. 17145 361-GluLeuArgLysThrLysGluGluArgPhe-370
SEQ. ID. NO. 17146 380-AlaAsnProAspAspTrpGlu-386
SEQ. ID. NO. 17147 395-GlnIleIleLysLysAspSerGluLysGlyGly-405
SEQ. ID. NO. 17148 446-PheProGluArgThrProSerTrpGluGlyArgLeuLysGluLeuVal-461
SEQ. ID. NO. 17149 467-LysLeuAsnGluAsnProGluArgAlaAspGlu-477
a205-1
AMPHI Regions - AMPHI
SEQ. ID. NO. 17150 6-ProGluGlnAsnValValArgLeuThrGlyLysHisProAsnAspLeuGluAlaValValGlyLys-27
SEQ. ID. NO. 17151 46-CysHisThrLeuPheAlaLysLeuValGlyAsnIleAlaGluAspGlyGlyLys-63
SEQ. ID. NO. 17152 75-GlnProTyrGlnAla-79
Antigenic Index - Jameson-Wolf
SEQ. ID. NO. 17153 1-ProLeuLysGlyLeuProGluGlnAsnVal-10
SEQ. ID. NO. 17154 13-LeuThrGlyLysHisProAsnAspLeuGluAlaValVal-25
SEQ. ID. NO. 17155 27-LysCysMetGluThrAspGlyLysGlyAlaProSerGly-39
SEQ. ID. NO. 17156 57-IleAlaGluAspGlyGlyLysLeuThr-65
SEQ. ID. NO. 17157 77-TyrGlnAlaGlyLysSerGlyTyr-84
SEQ. ID. NO. 17158 96-IleAspSerGluGly-100
SEQ. ID. NO. 17159 103-TyrPheArgArgArgHisTyr-109
Hydrophilic Regions - Hopp-Woods
SEQ. ID. NO. 17160 13-LeuThrGlyLysHisProAsnAspLeuGluAlaValVal-25
SEQ. ID. NO. 17161 27-LysCysMetGluThrAspGlyLysGlyAla-36
SEQ. ID. NO. 17162 57-IleAlaGluAspGlyGlyLysLeu-64
SEQ. ID. NO. 17163 78-GlnAlaGlyLysSerGly-83
SEQ. ID. NO. 17164 96-IleAspSerGluGly-100
SEQ. ID. NO. 17165 104-PheArgArgArgHisTyr-109
a206
AMPHI Regions - AMPHI
SEQ. ID. NO. 17166 32-ProLysGlnThrValArgGlnIleGlnAlaVal-42

TABLE 1-continued

| | |
|---|---|
| SEQ. ID. NO. 17167 | 44-IleSerHisIleAspArgThrGlnGly-52 |
| SEQ. ID. NO. 17168 | 81-CysSerGlyMetIleGln-86 |
| SEQ. ID. NO. 17169 | 99-ArgThrAlaArgAspMet-104 |
| SEQ. ID. NO. 17170 | 150-SerGlyLysThrIleLysThrGlu-157 |

Antigenic Index - Jameson-Wolf

| | |
|---|---|
| SEQ. ID. NO. 17171 | 2-PheProProAspLysThrLeu-8 |
| SEQ. ID. NO. 17172 | 21-GlyThrThrSerGlyLysHisArgGlnProLysProLysGlnThrValArg-37 |
| SEQ. ID. NO. 17173 | 45-SerHisIleAspArgThrGlnGlySerGln-54 |
| SEQ. ID. NO. 17174 | 66-ThrProTyrLysTrpGlyGlySerSerThr-75 |
| SEQ. ID. NO. 17175 | 96-LysLeuProArgThrAlaArgAspMetAlaAlaAlaSerArgLysIleProAspSerArgLeuLysAlaGly-119 |
| SEQ. ID. NO. 17176 | 126-ThrGlyGlyAlaHisArgTyrSer-133 |
| SEQ. ID. NO. 17177 | 148-ProSerSerGlyLysThrIleLysThrGluLysLeuSer-160 |

Hydrophilic Regions - Hopp-Woods

| | |
|---|---|
| SEQ. ID. NO. 17178 | 23-ThrSerGlyLysHisArgGlnProLysProLysGlnThrVal-36 |
| SEQ. ID. NO. 17179 | 45-SerHisIleAspArgThrGlnGlySerGln-54 |
| SEQ. ID. NO. 17180 | 96-LysLeuProArgThrAlaArgAspMetAlaAlaAlaSerArgLysIleProAspSerArgLeuLysAlaGly-119 |
| SEQ. ID. NO. 17181 | 149-SerSerGlyLysThrIleLysThrGluLysLeuSer-160 | a211
AMPHI Regions - AMPHI

| | |
|---|---|
| SEQ. ID. NO. 17182 | 18-ValGlyAsnGlyValAspGluPheGlyArgGlyAla-29 |
| SEQ. ID. NO. 17183 | 57-GlnPheGluArgAla-61 |
| SEQ. ID. NO. 17184 | 98-IleGluGlyPheAspLysIleAsnProAla-107 |

Antigenic Index - Jameson-Wolf

| | |
|---|---|
| SEQ. ID. NO. 17185 | 8-AsnGlnLeuGlyGlyArgAsnGlyThrAlaValGlyAsnGlyValAspGluPheGlyArgGlyAlaAspAsnGlnValGluPheLeuGlu-37 |
| SEQ. ID. NO. 17186 | 44-GlyAlaSerGlyArgAlaAla-50 |
| SEQ. ID. NO. 17187 | 73-GlyGluAspAspValVal-78 |
| SEQ. ID. NO. 17188 | 100-GlyPheAspLysIleAsnProAlaVal-108 |
| SEQ. ID. NO. 17189 | 141-ArgTyrHisProLysLeuHisAspGlyAsnGlnAsnGlyLysArgHisGlyLysLeuHisHisArgAla-163 |
| SEQ. ID. NO. 17190 | 169-CysGlnSerAlaGly-173 |

Hydrophilic Regions - Hopp-Woods

| | |
|---|---|
| SEQ. ID. NO. 17191 | 10-LeuGlyGlyArgAsnGlyThr-16 |
| SEQ. ID. NO. 17192 | 21-GlyValAspGluPheGlyArgGlyAlaAspAsnGlnValGluPheLeuGlu-37 |
| SEQ. ID. NO. 17193 | 73-GlyGluAspAspValVal-78 |
| SEQ. ID. NO. 17194 | 100-GlyPheAspLysIleAsn-105 |
| SEQ. ID. NO. 17195 | 142-TyrHisProLysLeuHisAspGlyAsnGlnAsnGlyLysArgHisGlyLysLeuHisHis-161 | a212
AMPHI Regions - AMPHI

| | |
|---|---|
| SEQ. ID. NO. 17196 | 6-TrpAsnGlyIleProAspIleArgThr-14 |
| SEQ. ID. NO. 17197 | 16-AspGlnThrIleArgLysHisAlaHis-24 |
| SEQ. ID. NO. 17198 | 40-PheGlnThrAlaGlnAsp-45 |
| SEQ. ID. NO. 17199 | 63-CysLeuGlnPheAspSerIleAsnLeuIleGluHisIle-75 |
| SEQ. ID. NO. 17200 | 89-ThrArgLeuHisGluHis-95 |
| SEQ. ID. NO. 17201 | 199-ArgLeuLeuGlyHis-203 |
| SEQ. ID. NO. 17202 | 238-HisAsnHisLeuTyrArgSerIleThrGlnAlaGluAlaGluLysIle-253 |
| SEQ. ID. NO. 17203 | 262-TyrAlaGluProLeuCysGlyLeu-269 |
| SEQ. ID. NO. 17204 | 397-TrpAsnGluAlaGluGluAla-403 |
| SEQ. ID. NO. 17205 | 439-AspSerProAspHis-443 |
| SEQ. ID. NO. 17206 | 445-ProLeuValGlyAlaLeuGlyAspIleAlaAlaMetGlnGlnThr-459 |
| SEQ. ID. NO. 17207 | 481-AlaTyrAlaAsnThrAlaHisGlyThrArgGlyLeu-492 |
| SEQ. ID. NO. 17208 | 506-IleLeuGlyLeuPro-510 |
| SEQ. ID. NO. 17209 | 512-ProLeuSerLysArgLeuArg-518 |

Antigenic Index - Jameson-Wolf

| | |
|---|---|
| SEQ. ID. NO. 17210 | 10-ProAspIleArgThrLeuAspGlnThrIleArgLysHisAlaHisProLeu-26 |
| SEQ. ID. NO. 17211 | 33-ProAspAsnGlnIleProAsnPhe-40 |
| SEQ. ID. NO. 17212 | 42-ThrAlaGlnAspAlaSerAspAlaGluCysArgLeuLysHisArgLeuAspGln-59 |
| SEQ. ID. NO. 17213 | 85-ProProSerArgThrArgArgLeuHisGlu-94 |
| SEQ. ID. NO. 17214 | 105-AlaIleProGlnThrGluSerLysProAspLysProTrp-117 |
| SEQ. ID. NO. 17215 | 120-LeuProGlnThrSerGluArgGlnLysProGluHis-131 |
| SEQ. ID. NO. 17216 | 158-LeuGluAlaArgLysAlaAlaGln-165 |
| SEQ. ID. NO. 17217 | 168-SerGlyAsnArgGlnGly-173 |
| SEQ. ID. NO. 17218 | 178-LysIleSerProHisAspThrGluGlnThrGlu-188 |
| SEQ. ID. NO. 17219 | 193-GlyTyrGlyTyrThrLys-198 |
| SEQ. ID. NO. 17220 | 205-LeuProGluSerGluThrTrpGlyGlyAsnGly-215 |
| SEQ. ID. NO. 17221 | 220-AsnTyrSerArgThrGluGlnGlnArgAsnHisGluLeuGlyLeu-234 |
| SEQ. ID. NO. 17222 | 236-LysHisHisAsnHisLeu-241 |
| SEQ. ID. NO. 17223 | 245-IleThrGlnAlaGluAlaGluLysIleAla-254 |
| SEQ. ID. NO. 17224 | 258-LeuAsnThrProTyrAla-263 |
| SEQ. ID. NO. 17225 | 294-LeuHisGluAspThrProLeu-300 |
| SEQ. ID. NO. 17226 | 302-AspIleSerHisAspGlyGluLysTrpIle-311 |
| SEQ. ID. NO. 17227 | 328-ThrGlyAlaAsnSerProTyrLeuPro-336 |
| SEQ. ID. NO. 17228 | 346-ArgGlnIleArgGlyGlnThrGlyLeuThrProSerThrProPheSerGluGlnLeuArg-365 |
| SEQ. ID. NO. 17229 | 376-ProSerTrpHisGly-380 |
| SEQ. ID. NO. 17230 | 391-AsnSerSerHisThrGlyTrpAsnGluAlaGluGluAlaSerAsnArgGlnAla-408 |
| SEQ. ID. NO. 17231 | 424-AsnProAsnProGlnLysHisGlnGly-432 |
| SEQ. ID. NO. 17232 | 436-IleArgCysAspSerProHisLeuPro-445 |
| SEQ. ID. NO. 17233 | 464-AlaLeuAspLysAsnTyrArgIleAspAla-473 |
| SEQ. ID. NO. 17234 | 486-AlaHisGlyThrArgGlyLeuAla-493 |
| SEQ. ID. NO. 17235 | 511-HisProLeuSerLysArgLeuArgHis-519 |
| SEQ. ID. NO. 17236 | 522-HisProAsnArgAlaIle-527 |
| SEQ. ID. NO. 17237 | 531-IleValArgArgLysAspLeuThrPro-539 |

TABLE 1-continued

Hydrophilic Regions - Hopp-Woods
SEQ. ID. NO. 17238    10-ProAspIleArgThrLeuAspGlnThrIleArgLysHisAla-23
SEQ. ID. NO. 17239    44-GlnAspAlaSerAspAlaGluCysArgLeuLysHisArgLeuAspGln-59
SEQ. ID. NO. 17240    87-SerArgThrArgArgLeuHisGlu-94
SEQ. ID. NO. 17241    105-AlaIleProGlnThrGluSerLysProAspLys-115
SEQ. ID. NO. 17242    122-GlnThrSerGluArgGlnLysProGluHis-131
SEQ. ID. NO. 17243    158-LeuGluAlaArgLysAlaAlaGln-165
SEQ. ID. NO. 17244    180-SerProHisAspThrGluGlnThrGlu-188
SEQ. ID. NO. 17245    206-ProGluSerGluThr-210
SEQ. ID. NO. 17246    222-SerArgThrGluGlnGlnArgAsnHisGlu-231
SEQ. ID. NO. 17247    246-ThrGlnAlaGluAlaGluLysIleAla-254
SEQ. ID. NO. 17248    294-LeuHisGluAspThrProLeu-300
SEQ. ID. NO. 17249    303-IleSerHisAspGlyGluLysTrpIle-311
SEQ. ID. NO. 17250    346-ArgGlnIleArgGly-350
SEQ. ID. NO. 17251    398-AsnGluAlaGluGluAlaSerAsnArgGlnAla-408
SEQ. ID. NO. 17252    426-AsnProGlnLysHisGlnGly-432
SEQ. ID. NO. 17253    436-IleArgCysAspSerProAsp-442
SEQ. ID. NO. 17254    467-LysAsnTyrArgIleAspAla-473
SEQ. ID. NO. 17255    513-LeuSerLysArgLeuArgHis-519
SEQ. ID. NO. 17256    531-IleValArgArgLysAspLeuThrPro-539
a214-1
AMPHI Regions - AMPHI
SEQ. ID. NO. 17257    6-CysLysLeuPheValLeuIle-12
SEQ. ID. NO. 17258    69-ValThrArgGlyGlyLysGlyGlyGluSerVal-79
SEQ. ID. NO. 17259    88-PheSerGlnThrLeuAsp-93
SEQ. ID. NO. 17260    122-LysValGlnArgGlyGlyAspVal-129
SEQ. ID. NO. 17261    150-ThrLysSerGlyAlaLysSerAlaSerLys-159
Antigenic Index - Jameson-Wolf
SEQ. ID. NO. 17262    23-LeuGlnSerAspSerArgGlnProIle-31
SEQ. ID. NO. 17263    33-IleGluAlaAspGlnGlySerLeuAspGlnAlaAsnGlnSerThrThrPheSerGlyAsn-52
SEQ. ID. NO. 17264    71-ArgGlyGlyLysGlyGlyGluSerValArgAlaGluGlySerProValArgPheSerGlnThrLeuAspGlyGlyLysGlyThrValArg
                      GlyGlnAlaAsnAsn-105
SEQ. ID. NO. 17265    119-GlyAsnAlaLysValGlnArgGlyGlyAspValAlaGlu-131
SEQ. ID. NO. 17266    137-TyrAsnThrLysThrGluVal-143
SEQ. ID. NO. 17267    148-GlySerThrLysSerGlyAlaLysSerAlaSerLysSerGlyArgValSerVal-165
SEQ. ID. NO. 17268    168-GlnProSerSerThrGlnLysSerGlu-176
Hydrophilic Regions - Hopp-Woods
SEQ. ID. NO. 17269    25-SerAspSerArgGlnProIle-31
SEQ. ID. NO. 17270    33-IleGluAlaAspGlnGlySerLeuAspGlnAlaAsn-44
SEQ. ID. NO. 17271    71-ArgGlyGlyLysGlyGlyGluSerValArgAlaGluGlySerPro-85
SEQ. ID. NO. 17272    92-LeuAspGlyGlyLysGlyThrValArgGlyGlnAla-103
SEQ. ID. NO. 17273    121-AlaLysValGlnArgGlyGlyAspValAlaGlu-131
SEQ. ID. NO. 17274    148-GlySerThrLysSerGlyAlaLysSerAlaSerLysSerGlyArg-162
SEQ. ID. NO. 17275    171-SerThrGlnLysSerGlu-176
a215
AMPHI Regions - AMPHI
SEQ. ID. NO. 17276    21-SerLeuSerAlaTrpLeuGlyArgIle-29
SEQ. ID. NO. 17277    67-SerSerLysGlyAlaLysGlnPheProGlu-76
Antigenic Index - Jameson-Wolf
SEQ. ID. NO. 17278    3-ValArgTrpArgTyrGly-8
SEQ. ID. NO. 17279    28-ArgIleSerGluValGluIleGluGluValArgLeuAsnProAspGluProGlnTyrThrMetAspGlyLeuAspGlyArgArgPhe
                      AspGluGlnGlyTyrLeuLys-63
SEQ. ID. NO. 17280    65-HisLeuSerSerLysGlyAlaLysGlnPheProGluSerSerAspIleHisPheAspSerProHisLeu-87
SEQ. ID. NO. 17281    99-ValGlySerAspGluAlaValTyrHisThrGluAsnLysGlnValLeuPhe-115
SEQ. ID. NO. 17282    123-LysThrAlaAspGlyLysArgGlnAlaGlyLysValGluAlaGluLysLeuHisValAspThrGluSerGlnTyrAlaGlnThrAspThrProVal-154
SEQ. ID. NO. 17283    160-AlaSerHisGlyGlnAlaGlyGlyMetThrTyrAspHisLysThrGly-175
SEQ. ID. NO. 17284    179-PheSerSerLysValLys-184
SEQ. ID. NO. 17285    187-IleTyrAspThrLysAspMet-193
Hydrophilic Regions - Hopp-Woods
SEQ. ID. NO. 17286    29-IleSerGluValGluIleGluGluValArgLeuAsnProAspGluProGlnTyr-46
SEQ. ID. NO. 17287    49-AspGlyLeuAspGlyArgArgPheAspGlu-58
SEQ. ID. NO. 17288    65-HisLeuSerSerLysGlyAlaLysGlnPheProGluSerSerAspIleHisPhe-82
SEQ. ID. NO. 17289    99-ValGlySerAspGluAlaValTyr-106
SEQ. ID. NO. 17290    108-ThrGluAsnLysGlnValLeu-114
SEQ. ID. NO. 17291    123-LysThrAlaAspGlyLysArgGlnAlaGlyLysValGluAlaGluLysLeuHisValAspThrGluSerGlnTyrAla-148
SEQ. ID. NO. 17292    170-TyrAspHisLysThr-174
SEQ. ID. NO. 17293    187-IleTyrAspThrLysAspMet-193
a216
AMPHI Regions - AMPHI
SEQ. ID. NO. 17294    21-AlaGluGlyLeuArgGluIleAlaAlaAspLeu-31
SEQ. ID. NO. 17295    62-ArgLysMetAlaAla-66
SEQ. ID. NO. 17296    167-LeuGlyAspAlaLeuAlaVal-173
SEQ. ID. NO. 17297    203-ValAlaAspIleMetHis-208
SEQ. ID. NO. 17298    218-LeuGlyThrProLeuLysGlu-224
SEQ. ID. NO. 17299    244-GlyArgLeuLysGlyVal-249
SEQ. ID. NO. 17300    253-GlyAspLeuArgArgLeuPheGlnGluCysAspAsnPheThrGlyLeuSerIle-270
SEQ. ID. NO. 17301    274-MetHisThrHisProLysThrIleSerAla-283
SEQ. ID. NO. 17302    292-LysValMetGlnAlaAsn-297
Antigenic Index - Jameson-Wolf
SEQ. ID. NO. 17303    4-AlaGlyAsnGluLysTyrLeuAspTrpAlaArg-14

TABLE 1-continued

| SEQ. ID. NO. 17304 | 16-ValLeuHisThrGluAlaGluGlyLeuArgGluIleAlaAlaAspLeuAspGlu-33 |
| --- | --- |
| SEQ. ID. NO. 17305 | 45-CysLysGlyArgVal-49 |
| SEQ. ID. NO. 17306 | 53-GlyMetGlyLysSerGlyHisIleGlyArgLysMetAla-65 |
| SEQ. ID. NO. 17307 | 82-GluAlaAlaHisGlyAspLeu-88 |
| SEQ. ID. NO. 17308 | 92-ValAspAsnAspVal-96 |
| SEQ. ID. NO. 17309 | 101-SerAsnSerGlyGluSerAspGluIle-109 |
| SEQ. ID. NO. 17310 | 115-AlaLeuLysArgLysAspIle-121 |
| SEQ. ID. NO. 17311 | 127-ThrAlaArgProAspSerThrMetAlaArgHisAlaAsp-139 |
| SEQ. ID. NO. 17312 | 146-ValSerLysGluAlaCysPro-152 |
| SEQ. ID. NO. 17313 | 179-ArgAlaPheThrProAspAspPheAla-187 |
| SEQ. ID. NO. 17314 | 190-HisProAlaGlySerLeuGlyLys-197 |
| SEQ. ID. NO. 17315 | 205-AspIleMetHisLysGlyGlyGlyLeuProAla-215 |
| SEQ. ID. NO. 17316 | 218-LeuGlyThrProLeuLysGluAlaIle-226 |
| SEQ. ID. NO. 17317 | 229-MetSerGluLysGlyLeu-234 |
| SEQ. ID. NO. 17318 | 239-ValThrAspGlyGlnGlyArgLeuLysGly-248 |
| SEQ. ID. NO. 17319 | 250-PheThrAspGlyAspLeuArgArgLeuPheGlnGluCysAspAsnPheThr-266 |
| SEQ. ID. NO. 17320 | 277-HisProLysThrIleSerAlaGluArgLeuAlaThrGluAlaLeuLys-292 |
| SEQ. ID. NO. 17321 | 305-ThrAspAlaAspGly-309 |
| Hydrophilic Regions - Hopp-Woods | |
| SEQ. ID. NO. 17322 | 5-GlyAsnGluLysTyrLeuAspTrpAlaArg-14 |
| SEQ. ID. NO. 17323 | 16-ValLeuHisThrGluAlaGluGlyLeuArgGluIleAlaAlaAspLeuAspGlu-33 |
| SEQ. ID. NO. 17324 | 45-CysLysGlyArgVal-49 |
| SEQ. ID. NO. 17325 | 58-GlyHisIleGlyArgLysMetAla-65 |
| SEQ. ID. NO. 17326 | 102-AsnSerGlyGluSerAspGluIle-109 |
| SEQ. ID. NO. 17327 | 115-AlaLeuLysArgLysAspIle-121 |
| SEQ. ID. NO. 17328 | 128-AlaArgProAspSerThrMetAlaArgHisAlaAsp-139 |
| SEQ. ID. NO. 17329 | 146-ValSerLysGluAlaCys-151 |
| SEQ. ID. NO. 17330 | 179-ArgAlaPheThrProAspAspPheAla-187 |
| SEQ. ID. NO. 17331 | 220-ThrProLeuLysGluAlaIle-226 |
| SEQ. ID. NO. 17332 | 229-MetSerGluLysGlyLeu-234 |
| SEQ. ID. NO. 17333 | 241-AspGlyGlnGlyArgLeuLys-247 |
| SEQ. ID. NO. 17334 | 253-GlyAspLeuArgArgLeuPheGlnGluCysAspAsn-264 |
| SEQ. ID. NO. 17335 | 279-LysThrIleSerAlaGluArgLeuAlaThrGluAlaLeuLys-292 |
| SEQ. ID. NO. 17336 | 305-ThrAspAlaAspGly-309 |
| a218 | |
| AMPHI Regions - AMPHI | |
| SEQ. ID. NO. 17337 | 9-AlaLysValValSerThrMet-15 |
| SEQ. ID. NO. 17338 | 24-AlaMetAspGluIleHisSer-30 |
| SEQ. ID. NO. 17339 | 78-AlaArgSerTrpTrpArgAsnLeuHisGlyAlaPheGlyThrTrpValSerLeuIleLeu-97 |
| SEQ. ID. NO. 17340 | 111-TrpGlyGlyLysPheValGlnAlaTrpSerGlnPhePro-123 |
| SEQ. ID. NO. 17341 | 176-AspGluProMetThrLeuGluThrValAspArgPheAlaArgXxxAsnArgPheGlnArgAlaLeuSerAla-199 |
| Antigenic Index - Jameson-Wolf | |
| SEQ. ID. NO. 17342 | 13-SerThrMetProArgAsnGlnGlyTrp-21 |
| SEQ. ID. NO. 17343 | 35-GlySerThrGlyAsp-39 |
| SEQ. ID. NO. 17344 | 62-ValLysArgArgGlyIleLysAla-69 |
| SEQ. ID. NO. 17345 | 71-LeuLeuProProLysGlyArgAlaArgSerTrpTrp-82 |
| SEQ. ID. NO. 17346 | 86-HisGlyAlaPheGly-90 |
| SEQ. ID. NO. 17347 | 123-ProAlaGlyLysTrpGlyValGluProAsnProVal-134 |
| SEQ. ID. NO. 17348 | 143-ValLeuAsnAspGlyLysValLysGlu-151 |
| SEQ. ID. NO. 17349 | 167-ThrValGlyLysAspGlyIleAsnProAspGluProMetThr-180 |
| SEQ. ID. NO. 17350 | 182-GluThrValAspArgPheAlaArgXxxAsnArgPheGlnArg-195 |
| SEQ. ID. NO. 17351 | 201-PheAlaGlnArgArgGlyArgArgMetAspPhe-211 |
| Hydrophilic Regions - Hopp-Woods | |
| SEQ. ID. NO. 17352 | 63-LysArgArgGlyIleLys-68 |
| SEQ. ID. NO. 17353 | 74-ProLysGlyArgAla-78 |
| SEQ. ID. NO. 17354 | 143-ValLeuAsnAspGlyLysValLysGlu-151 |
| SEQ. ID. NO. 17355 | 167-ThrValGlyLysAspGlyIleAsnProAspGluProMetThr-180 |
| SEQ. ID. NO. 17356 | 182-GluThrValAspArgPheAlaArgXxxAsnArgPheGlnArg-195 |
| SEQ. ID. NO. 17357 | 201-PheAlaGlnArgArgGlyArgArgMetAspPhe-211 |
| a225-1 | |
| AMPHI Regions - AMPHI | |
| SEQ. ID. NO. 17358 | 23-LeuAlaAspGluLeuThrAsn-29 |
| SEQ. ID. NO. 17359 | 37-IleLeuArgGlnPhe-41 |
| SEQ. ID. NO. 17360 | 155-AsnAlaMetGlyLeu-159 |
| SEQ. ID. NO. 17361 | 180-PheMetGlnHisIlePheLys-186 |
| SEQ. ID. NO. 17362 | 215-GlyAspMetValXxxPheArgThrLeuGlyGlySerArg-227 |
| SEQ. ID. NO. 17363 | 246-ThrGlyLysAsnIle-250 |
| Antigenic Index - Jameson-Wolf | |
| SEQ. ID. NO. 17364 | 22-AlaLeuAlaAspGluLeuThr-28 |
| SEQ. ID. NO. 17365 | 32-SerSerArgGluGlnIleLeu-38 |
| SEQ. ID. NO. 17366 | 41-PheAlaGluAspGluGlnProVal-48 |
| SEQ. ID. NO. 17367 | 52-AsnArgXxxProAlaArgArgAlaGlyAsnAlaAspGluLeuIle-66 |
| SEQ. ID. NO. 17368 | 71-GlyLeuAsnGluGlnProVal-77 |
| SEQ. ID. NO. 17369 | 81-AsnArgXxxProAlaArgArgAlaGlyAsnAlaAspXxx-93 |
| SEQ. ID. NO. 17370 | 100-GlyLeuAsnGluGlnProVal-106 |
| SEQ. ID. NO. 17371 | 110-AsnArgValProAlaArgArgAlaGlyAsnAlaAspGluLeuIle-124 |
| SEQ. ID. NO. 17372 | 129-GlyLeuAsnGluGlnProVal-135 |
| SEQ. ID. NO. 17373 | 137-ProValAsnArgAlaProAlaArgArgAlaGlyAsnAlaAspGluLeuIle-153 |
| SEQ. ID. NO. 17374 | 173-ThrGlyPheAspCysSerGly-179 |
| SEQ. ID. NO. 17375 | 193-LeuProArgThrSerAlaGluGlnAlaArgMet-203 |

TABLE 1-continued

| | |
|---|---|
| SEQ. ID. NO. 17376 | 205-ThrProValAlaArgSerGluLeuGlnProGlyAspMetValXxx-219 |
| SEQ. ID. NO. 17377 | 222-ThrLeuGlyGlySerArgIle-228 |
| SEQ. ID. NO. 17378 | 242-HisAlaProArgThrGlyLysAsnIleGlu-251 |
| SEQ. ID. NO. 17379 | 254-SerLeuSerHisLysTyrTrpSerGlyLys-263 |
| SEQ. ID. NO. 17380 | 268-ArgArgValLysLysAsnAspProSerArgPhe-278 |

Hydrophilic Regions - Hopp-Woods

| | |
|---|---|
| SEQ. ID. NO. 17381 | 22-AlaLeuAlaAspGluLeuThr-28 |
| SEQ. ID. NO. 17382 | 32-SerSerArgGluGlnIleLeu-38 |
| SEQ. ID. NO. 17383 | 41-PheAlaGluAspGluGlnPro-47 |
| SEQ. ID. NO. 17384 | 53-ArgXxxProAlaArgArgAlaGlyAsnAlaAspGluLeuIle-66 |
| SEQ. ID. NO. 17385 | 82-ArgXxxProAlaArgArgAlaGlyAsnAla-91 |
| SEQ. ID. NO. 17386 | 112-ValProAlaArgArgAlaGlyAsnAlaAspGluLeuIle-124 |
| SEQ. ID. NO. 17387 | 140-ArgAlaProAlaArgArgAlaGlyAsnAlaAspGluLeuIle-153 |
| SEQ. ID. NO. 17388 | 195-ArgThrSerAlaGluGlnAlaArgMet-203 |
| SEQ. ID. NO. 17389 | 207-ValAlaArgSerGluLeuGlnPro-214 |
| SEQ. ID. NO. 17390 | 245-ArgThrGlyLysAsnIleGlu-251 |
| SEQ. ID. NO. 17391 | 268-ArgArgValLysLysAsnAspProSerArg-277 | a226
AMPHI Regions - AMPHI

| | |
|---|---|
| SEQ. ID. NO. 17392 | 44-LeuIleAlaTyrLeuLys-49 |
| SEQ. ID. NO. 17393 | 61-AlaAlaGlnPheIleAspPheTrpLeu-69 |
| SEQ. ID. NO. 17394 | 98-GlnLeuAlaGlySerValThrGlyIleValThr-108 |
| SEQ. ID. NO. 17395 | 141-ArgSerIleGlyGlyIleProAlaIleThr-150 |
| SEQ. ID. NO. 17396 | 157-AlaGlyLeuValGlyGlnIleAlaGlyTyrLys-167 |
| SEQ. ID. NO. 17397 | 197-GluArgSerArgArg-201 |

Antigenic Index - Jameson-Wolf

| | |
|---|---|
| SEQ. ID. NO. 17398 | 3-GluIleLeuArgGlnProSer-9 |
| SEQ. ID. NO. 17399 | 25-ValArgThrArgThrGlyAsnIle-32 |
| SEQ. ID. NO. 17400 | 81-TyrGlnAsnArgArgLysIle-87 |
| SEQ. ID. NO. 17401 | 117-GlyAlaGluArgGluVal-122 |
| SEQ. ID. NO. 17402 | 128-SerLysSerValThrAsn-133 |
| SEQ. ID. NO. 17403 | 139-IleThrArgSerIleGlyGly-145 |
| SEQ. ID. NO. 17404 | 167-LysMetLeuLysAsnThrVal-173 |
| SEQ. ID. NO. 17405 | 195-SerLeuGluArgSerArgArgMetAla-203 |

Hydrophilic Regions - Hopp-Woods

| | |
|---|---|
| SEQ. ID. NO. 17406 | 25-ValArgThrArgThr-29 |
| SEQ. ID. NO. 17407 | 82-GlnAsnArgArgLysIle-87 |
| SEQ. ID. NO. 17408 | 117-GlyAlaGluArgGluVal-122 |
| SEQ. ID. NO. 17409 | 195-SerLeuGluArgSerArgArgMetAla-203 | a227
AMPHI Regions - AMPHI

| | |
|---|---|
| SEQ. ID. NO. 17410 | 36-GlyValLeuPheAlaLeuLeuGlnAla-44 |
| SEQ. ID. NO. 17411 | 52-LeuGlnGlnLeuThrAspAlaLeu-59 |
| SEQ. ID. NO. 17412 | 74-ValIleSerTyrLeuAspLeuIleAlaAspAspTrpPheSer-87 | a228
AMPHI Regions - AMPHI

| | |
|---|---|
| SEQ. ID. NO. 17413 | 24-GluValLysGluAlaValGlnAlaValGlu-33 |
| SEQ. ID. NO. 17414 | 40-AlaAlaSerAlaAlaGluSerAlaAlaSerAlaValGluGluAlaLysAspGlnValLysAspAla-61 |
| SEQ. ID. NO. 17415 | 78-GluAlaValThrGluAlaAlaLysAspThrLeuAsnLysAlaAlaAspAlaThrGlnGluAlaAlaAspLysMetLysAspAlaAla-106 |

Antigenic Index - Jameson-Wolf

| | |
|---|---|
| SEQ. ID. NO. 17416 | 18-SerGlnGluAlaLysGlnGluValLysGluAlaValGln-30 |
| SEQ. ID. NO. 17417 | 32-ValGluSerAspValLysAspThrAlaAlaSerAlaAlaGluSerAlaAlaSerAlaValGluGluAlaLysAspGlnValLysAspAla AlaAlaAspAlaLysAlaSerAlaGluGluAlaValThrGluAlaLysGluAlaValThrGlu AlaAlaLysAspThrLeuAsnLysAlaAlaAspAlaThrGlnGluAlaAlaAspLysMetLysAspAlaAlaLys-107 |

Hydrophilic Regions - Hopp-Woods

| | |
|---|---|
| (SEQ. ID. NO. 17416) | 18-SerGlnGluAlaLysGlnGluValLysGluAlaValGln-30 |
| (SEQ. ID. NO. 17417) | 32-ValGluSerAspValLysAspThrAlaAlaSerAlaAlaGluSerAlaAlaSerAlaValGluGluAlaLysAspGlnVal LysAspAlaAlaAlaAspAlaLysAlaSerAlaGluGluAlaValThrGluAlaLysGluAlaValThrGluAlaAlaLysAspThrLeuAsnLysAlaAla AspAlaThrGlnGluAlaAlaAspLysMetLysAspAlaAlaLys-107 | a230-1
AMPHI Regions - AMPHI

| | |
|---|---|
| SEQ. ID. NO. 17418 | 6-GluLysTyrArgThr-10 |
| SEQ. ID. NO. 17419 | 49-AspHisSerIleAsnAsn-54 |
| SEQ. ID. NO. 17420 | 56-IleGlnAsnGluGln-60 |
| SEQ. ID. NO. 17421 | 73-GlnSerLeuLeuGln-77 |
| SEQ. ID. NO. 17422 | 81-LeuLysGlnGlyAlaLys-86 |
| SEQ. ID. NO. 17423 | 96-GlnIleLysGlnIleIle-101 |
| SEQ. ID. NO. 17424 | 133-PheValGluGluIleArgAspGlnPhe-141 |
| SEQ. ID. NO. 17425 | 144-GlnAsnLeuValAsnLeuVal-150 |
| SEQ. ID. NO. 17426 | 161-AlaGluGlnLeuIleArgLeuThrGlnValAsnArgThrIleArg-175 |
| SEQ. ID. NO. 17427 | 184-PheIleAlaGlnVal-188 |
| SEQ. ID. NO. 17428 | 194-AspLeuGlnLysPheTyrAsn-200 |
| SEQ. ID. NO. 17429 | 234-GluValLysAsnAlaPheGluGluArgValAlaArgLeu-246 |
| SEQ. ID. NO. 17430 | 272-ValAlaAspPheAsnLys-277 |
| SEQ. ID. NO. 17431 | 284-AspAspAlaPheAsnHisProSerSerLeuAlaGluAla-296 |
| SEQ. ID. NO. 17432 | 319-SerGlyMetProGluAsnLeuIleAsnAlaVal-329 |
| SEQ. ID. NO. 17433 | 398-LeuAsnGlyGlyLys-402 |
| SEQ. ID. NO. 17434 | 426-GluAlaTyrAlaGluLeu-431 |
| SEQ. ID. NO. 17435 | 444-ValArgLeuIleGlyLeuProAlaPro-452 |
| SEQ. ID. NO. 17436 | 456-GluValGlnAlaValThrProProAspAspIleAla-467 |

TABLE 1-continued

| | |
|---|---|
| SEQ. ID. NO. 17437 | 488-LeuLeuIleArgTyrPheAsn-494 |
| Antigenic Index - Jameson-Wolf | |
| SEQ. ID. NO. 17438 | 4-SerIleGluLysTyrArgThrProAla-12 |
| SEQ. ID. NO. 17439 | 32-SerHisProGlyAlaAsp-37 |
| SEQ. ID. NO. 17440 | 42-ValGlyAspGluLysIleSerAspHisSerIle-52 |
| SEQ. ID. NO. 17441 | 56-IleGlnAsnGluGlnAlaAspGlyGlyGlyProSerArgAspAlaVal-71 |
| SEQ. ID. NO. 17442 | 80-TyrLeuLysGlnGlyAla-85 |
| SEQ. ID. NO. 17443 | 92-ValSerSerGluGlnIleLys-98 |
| SEQ. ID. NO. 17444 | 101-IleValAspAspProAsnPheHisAspAlaAsnGlyLysPheAsp-115 |
| SEQ. ID. NO. 17445 | 122-TyrLeuSerGlnArgHisMetSerGluAspGlnPheValGluGluIleArgAsp-139 |
| SEQ. ID. NO. 17446 | 169-GlnValAsnArgThrIleArgSerHisThrPheAsnProAspGluPhe-184 |
| SEQ. ID. NO. 17447 | 189-LysValSerGluAlaAspLeu-195 |
| SEQ. ID. NO. 17448 | 199-TyrAsnAlaAsnLysLysAspTyrLeu-207 |
| SEQ. ID. NO. 17449 | 223-AspPheAlaAspLysGlnThrValSerGluThrGluValLysAsnAlaPheGluGluArgValAlaArg-245 |
| SEQ. ID. NO. 17450 | 247-ProAlaAsnGluAlaLysProSerPheGluGlnGluLysAlaAlaValGluAsnGluLeuLysMetLysLysAlaValAlaAspPheAsn LysAlaLysGluLysLeuGlyAspAspAlaPheAsnHisProSerSerLeuAlaGluAlaAl aLysAsnSerGlyLeuLysValGluThrGlnGluThrTrpLeuSerArgGlnAspAlaGlnMetSerGlyMetProGluAsn-324 |
| SEQ. ID. NO. 17451 | 330-PheSerAspAspValLeuLysLysLysHisAsnSerGlu-342 |
| SEQ. ID. NO. 17452 | 355-ArgAlaLysGluValArgGluGluLysThrLeuPro-366 |
| SEQ. ID. NO. 17453 | 368-AlaGluAlaLysAspAlaValArg-375 |
| SEQ. ID. NO. 17454 | 377-AlaTyrIleArgThrGluAlaAlaLysLeuAlaGluAsnLysAlaLysAspValLeu-395 |
| SEQ. ID. NO. 17455 | 399-AsnGlyGlyLysAlaValAsp-405 |
| SEQ. ID. NO. 17456 | 417-GlnGlnAlaArgGlnSerMetProProGluAlaTyr-428 |
| SEQ. ID. NO. 17457 | 432-LeuLysAlaLysProAlaAsnGlyLysProAla-442 |
| SEQ. ID. NO. 17458 | 459-AlaValThrProProAspAspIleAla-467 |
| SEQ. ID. NO. 17459 | 476-AlaLeuAlaGlnGlnGlnSerAlaAsnThrPhe-486 |
| SEQ. ID. NO. 17460 | 493-PheAsnGlyLysIleLysGlnThrLysGlyAlaGlnSerValAspAsnGlyAspGlyGln-512 |
| Hydrophilic Regions - Hopp-Woods | |
| SEQ. ID. NO. 17461 | 6-GluLysTyrArgThr-10 |
| SEQ. ID. NO. 17462 | 42-ValGlyAspGluLysIleSerAsp-49 |
| SEQ. ID. NO. 17463 | 56-IleGlnAsnGluGlnAlaAspGlyGlyGlyProSerArgAspAlaVal-71 |
| SEQ. ID. NO. 17464 | 92-ValSerSerGluGlnIleLys-98 |
| SEQ. ID. NO. 17465 | 101-IleValAspAspProAsnPhe-107 |
| SEQ. ID. NO. 17466 | 110-AlaAsnGlyLysPheAsp-115 |
| SEQ. ID. NO. 17467 | 126-ArgHisMetSerGluAspGlnPheValGluGluIleArgAsp-139 |
| SEQ. ID. NO. 17468 | 189-LysValSerGluAlaAspLeu-195 |
| SEQ. ID. NO. 17469 | 200-AsnAlaAsnLysLysAspTyrLeu-207 |
| SEQ. ID. NO. 17470 | 223-AspPheAlaAspLysGlnThrValSerGluThrGluValLysAsnAlaPheGluGluArgValAlaArg-245 |
| SEQ. ID. NO. 17471 | 247-ProAlaAsnGluAlaLysProSerPheGluGlnGluLysAlaAlaValGluAsnGluLeuLysMetLysLysAlaValAlaAspPheAsn LysAlaLysGluLysLeuGlyAspAspAlaPheAsn-288 |
| SEQ. ID. NO. 17472 | 292-SerLeuAlaGluAlaAlaLysAsnSerGlyLeuLysValGluThrGlnGlu-308 |
| SEQ. ID. NO. 17473 | 310-TrpLeuSerArgGlnAspAlaGlnMet-318 |
| SEQ. ID. NO. 17474 | 333-AspValLeuLysLysLysHisAsnSer-341 |
| SEQ. ID. NO. 17475 | 355-ArgAlaLysGluValArgGluGluLysThrLeuPro-366 |
| SEQ. ID. NO. 17476 | 368-AlaGluAlaLysAspAlaValArg-375 |
| SEQ. ID. NO. 17477 | 377-AlaTyrIleArgThrGluAlaAlaLysLeuAlaGluAsnLysAlaLysAspValLeu-395 |
| SEQ. ID. NO. 17478 | 417-GlnGlnAlaArgGlnSerMetPro-424 |
| SEQ. ID. NO. 17479 | 432-LeuLysAlaLysProAlaAsnGly-439 |
| SEQ. ID. NO. 17480 | 461-ThrProProAspAspIleAla-467 |
| SEQ. ID. NO. 17481 | 496-LysIleLysGlnThrLysGlyAlaGlnSerValAspAsnGlyAspGlyGln-512 |
| a231-1 | |
| AMPHI Regions - AMPHI | |
| SEQ. ID. NO. 17482 | 7-IleAsnArgProTyrGlnLysProAlaGluLeu-17 |
| SEQ. ID. NO. 17483 | 98-ArgIlePheSerPheProGln-104 |
| SEQ. ID. NO. 17484 | 209-AlaValAspAsnValLysGlyValAlaVal-218 |
| SEQ. ID. NO. 17485 | 228-AlaValAlaGlyPheArgArgCysSerAlaAla-238 |
| SEQ. ID. NO. 17486 | 263-LeuAlaAlaValProArgIleThrGln-271 |
| SEQ. ID. NO. 17487 | 281-LysProPheHisAspPhePheAsnLeu-289 |
| Antigenic Index - Jameson-Wolf | |
| SEQ. ID. NO. 17488 | 1-MetSerLysArgLysSerIleAsnArgProTyrGlnLysProAlaGlu-16 |
| SEQ. ID. NO. 17489 | 18-ProProLeuGlnAsnAsnProProPheTyrArgLysAsnArgArgLeuAsn-34 |
| SEQ. ID. NO. 17490 | 39-AlaAspGlyGlyCysAlaSerProGlnLysCysArgAlaArgGlyPheGln-55 |
| SEQ. ID. NO. 17491 | 90-ProAlaValArgProArgArgLeuArg-98 |
| SEQ. ID. NO. 17492 | 135-MetProArgArgProVal-140 |
| SEQ. ID. NO. 17493 | 150-PheAlaAspArgAsnLeuArg-156 |
| SEQ. ID. NO. 17494 | 166-GluHisAlaAspAlaAsp-171 |
| SEQ. ID. NO. 17495 | 174-AlaPheArgArgAlaGlnVal-181 |
| SEQ. ID. NO. 17496 | 183-AlaArgThrArgAla-187 |
| SEQ. ID. NO. 17497 | 194-ArgArgValAspIleArgHisProAspPhe-203 |
| SEQ. ID. NO. 17498 | 211-AspAsnValLysGly-215 |
| SEQ. ID. NO. 17499 | 231-GlyPheArgArgCysSerAlaAlaGlyGlyArgValGlyThr-244 |
| SEQ. ID. NO. 17500 | 246-ValProCysAlaGluTyrValGluTyrGlyAsnArgArgProHisArgLeuAlaAla-265 |
| SEQ. ID. NO. 17501 | 269-IleThrGlnArgThrGlnLysArgGlnGlyAspGlyLysProPhe-283 |
| SEQ. ID. NO. 17502 | 294-MetProMetProSerGluHis-300 |
| Hydrophilic Regions - Hopp-Woods | |
| SEQ. ID. NO. 17503 | 1-MetSerLysArgLysSerIleAsn-8 |
| SEQ. ID. NO. 17504 | 10-ProTyrGlnLysProAlaGlu-16 |
| SEQ. ID. NO. 17505 | 26-PheTyrArgLysAsnArgArg-32 |
| SEQ. ID. NO. 17506 | 45-SerProGlnLysCysArgAlaArgGly-53 |
| SEQ. ID. NO. 17507 | 92-ValArgProArgArgLeuArg-98 |

TABLE 1-continued

| | |
|---|---|
| SEQ. ID. NO. 17508 | 136-ProArgArgProVal-140 |
| SEQ. ID. NO. 17509 | 150-PheAlaAspArgAsnLeuArg-156 |
| SEQ. ID. NO. 17510 | 166-GluHisAlaAspAlaAsp-171 |
| SEQ. ID. NO. 17511 | 174-AlaPheArgArgArgAlaGlnVal-181 |
| SEQ. ID. NO. 17512 | 183-AlaArgThrArgAla-187 |
| SEQ. ID. NO. 17513 | 194-ArgArgValAspIleArgHis-200 |
| SEQ. ID. NO. 17514 | 231-GlyPheArgArgCysSerAlaAlaGlyGlyArgValGlyThr-244 |
| SEQ. ID. NO. 17515 | 246-ValProCysArgAlaGluTyr-252 |
| SEQ. ID. NO. 17516 | 254-GluTyrGlyAsnArgArgProHisArg-262 |
| SEQ. ID. NO. 17517 | 269-IleThrGlnArgThrGlnLysArgGlnGlyAspGlyLysProPhe-283 | a232
AMPHI Regions - AMPHI

| | |
|---|---|
| SEQ. ID. NO. 17518 | 23-GlnPheLeuGlyAlaPheAsnAspAsnVal-32 |
| SEQ. ID. NO. 17519 | 55-GlyGlnMetLeuAsn-59 |
| SEQ. ID. NO. 17520 | 74-SerLeuSerGlyGlnLeuGlyAsnLysPheAspLysAlaValLeuAlaArgTrpAlaLysValLeuGluMetIleIleMet-100 |
| SEQ. ID. NO. 17521 | 127-ThrLeuPheGlyProLeuLysTyr-134 |
| SEQ. ID. NO. 17522 | 160-AlaIleLeuPheGly-164 |
| SEQ. ID. NO. 17523 | 167-LeuGlyThrAlaValAlaGlyValProProTyrIleValGlyIleLeuVal-183 |
| SEQ. ID. NO. 17524 | 214-ValArgGlyThrLysSerLeuLeuArgGlu-223 |
| SEQ. ID. NO. 17525 | 251-LeuProThrPheThrGln-256 |
| SEQ. ID. NO. 17526 | 319-ArgPheGluGlyLeuAsn-324 |
| SEQ. ID. NO. 17527 | 340-AlaValMetThrLeuIleGlyPhePheGlyGlyPhePheSerValProLeuTyrThrTrpLeu-360 |

Antigenic Index - Jameson-Wolf

| | |
|---|---|
| SEQ. ID. NO. 17528 | 1-MetTyrAlaLysLysGlyGlyLeuGlyLeuValLysSerArgArgPhe-16 |
| SEQ. ID. NO. 17529 | 75-LeuSerGlyGlnLeuGlyAsnLysPheAspLys-85 |
| SEQ. ID. NO. 17530 | 139-AspTyrLeuAspAspLysGluLeuMetMet-148 |
| SEQ. ID. NO. 17531 | 200-ValProAlaLysAlaAlaAspThrGlnIle-209 |
| SEQ. ID. NO. 17532 | 215-ArgGlyThrLysSerLeuLeuArgGluThrValArgHisLysPro-229 |
| SEQ. ID. NO. 17533 | 258-HisLeuGlyGlyAsnAspAsnVal-265 |
| SEQ. ID. NO. 17534 | 286-LysPheSerArgGluArgLeuArg-293 |
| SEQ. ID. NO. 17535 | 316-HisGlyHisArgPheGluGly-322 |
| SEQ. ID. NO. 17536 | 363-AlaSerSerGluThrPheArgAlaArgAla-372 |
| SEQ. ID. NO. 17537 | 420-IleLysArgGluArgArgPheLeu-427 |
| SEQ. ID. NO. 17538 | 431-AlaIleArgLysLysPro-436 |

Hydrophilic Regions - Hopp-Woods

| | |
|---|---|
| SEQ. ID. NO. 17539 | 2-TyrAlaLysLysGlyGly-7 |
| SEQ. ID. NO. 17540 | 11-ValLysSerArgArgPhe-16 |
| SEQ. ID. NO. 17541 | 81-AsnLysPheAspLys-85 |
| SEQ. ID. NO. 17542 | 140-TyrLeuAspAspLysGluLeuMet-147 |
| SEQ. ID. NO. 17543 | 201-ProAlaLysAlaAlaAspThrGlnIle-209 |
| SEQ. ID. NO. 17544 | 215-ArgGlyThrLysSerLeuLeuArgGluThrValArgHis-227 |
| SEQ. ID. NO. 17545 | 286-LysPheSerArgGluArgLeuArg-293 |
| SEQ. ID. NO. 17546 | 318-HisArgPheGluGly-322 |
| SEQ. ID. NO. 17547 | 366-GluThrPheArgAlaArgAla-372 |
| SEQ. ID. NO. 17548 | 420-IleLysArgGluArgArgPheLeu-427 |
| SEQ. ID. NO. 17549 | 431-AlaIleArgLysLysPro-436 | a233
AMPHI Regions - AMPHI

| | |
|---|---|
| SEQ. ID. NO. 17550 | 61-PheAlaAspLysValGlnThr-67 |
| SEQ. ID. NO. 17551 | 71-GlnValArgValTrpLysAsn-77 |
| SEQ. ID. NO. 17552 | 88-AsnGlyValAlaLysLeuLeuGluThr-96 |
| SEQ. ID. NO. 17553 | 119-AlaLeuThrArgLeuIleGluGlnAlaGlyAsnAla-130 |
| SEQ. ID. NO. 17554 | 139-ProValAlaAspThrLeuLysCysAlaAspGlyGlyAsn-151 |
| SEQ. ID. NO. 17555 | 180-AlaAlaGluAsnLeuAspGlyIleThrAsp-189 |

Antigenic Index - Jameson-Wolf

| | |
|---|---|
| SEQ. ID. NO. 17556 | 1-MetLysArgLysAsnIle-6 |
| SEQ. ID. NO. 17557 | 16-AlaArgPheGlyAlaAspLysProLysGlnTyrValGluIleGlySerLysThrValLeu-35 |
| SEQ. ID. NO. 17558 | 43-GluArgHisGluAlaValAsp-49 |
| SEQ. ID. NO. 17559 | 56-SerProGluAspThrPheAlaAspLysValGln-66 |
| SEQ. ID. NO. 17560 | 75-TrpLysAsnGlyGlyGlnThrArgAlaGluThrValArgAsnGlyVal-90 |
| SEQ. ID. NO. 17561 | 100-AlaGluThrAspAsn-104 |
| SEQ. ID. NO. 17562 | 109-AspAlaAlaArgCys-113 |
| SEQ. ID. NO. 17563 | 115-LeuProSerGluAlaLeu-120 |
| SEQ. ID. NO. 17564 | 123-LeuIleGluGlnAlaGlyAsnAlaAlaGluGlyGly-134 |
| SEQ. ID. NO. 17565 | 142-AspThrLeuLysCysAlaAspGlyGlyAsnIle-152 |
| SEQ. ID. NO. 17566 | 155-ThrValGluArgThrSerLeu-161 |
| SEQ. ID. NO. 17567 | 182-GluAsnLeuAspGlyIleThrAspGluAlaSerAlaValGluLysLeuGlyIle-199 |
| SEQ. ID. NO. 17568 | 206-GlyAspAlaArgAsnLeuLysLeuThrGlnProGlnAspAlaTyr-220 |

Hydrophilic Regions - Hopp-Woods

| | |
|---|---|
| SEQ. ID. NO. 17569 | 1-MetLysArgLysAsnIle-6 |
| SEQ. ID. NO. 17570 | 18-PheGlyAlaAspLysProLysGlnTyrVal-27 |
| SEQ. ID. NO. 17571 | 43-GluArgHisGluAlaValAsp-49 |
| SEQ. ID. NO. 17572 | 56-SerProGluAspThrPheAlaAspLysValGln-66 |
| SEQ. ID. NO. 17573 | 79-GlyGlnThrArgAlaGluThrValArg-87 |
| SEQ. ID. NO. 17574 | 100-AlaGluThrAspAsn-104 |
| SEQ. ID. NO. 17575 | 127-AlaGlyAsnAlaAlaGlu-132 |
| SEQ. ID. NO. 17576 | 142-AspThrLeuLysCysAlaAsp-148 |
| SEQ. ID. NO. 17577 | 182-GluAsnLeuAspGlyIleThrAspGluAlaSerAlaValGluLysLeuGlyIle-199 |
| SEQ. ID. NO. 17578 | 206-GlyAspAlaArgAsnLeuLys-212 |

TABLE 1-continued a234-2
AMPHI Regions - AMPHI
SEQ. ID. NO. 17579 26-ArgSerLeuGluValGluLysValAlaSer-35
SEQ. ID. NO. 17580 68-AspArgLeuGlySerGln-73
SEQ. ID. NO. 17581 83-GlnGlnThrAsnArgPheAsnValLeuAsnArgThrAsn-95
SEQ. ID. NO. 17582 121-GlyAspValThrGluPhe-126
SEQ. ID. NO. 17583 206-AlaValAsnSerLeuValGlnAlaValAsp-215
Antigenic Index - Jameson-Wolf
SEQ. ID. NO. 17584 21-AlaThrGluSerSerArgSerLeuGluValGluLysValAlaSer-35
SEQ. ID. NO. 17585 51-ThrPheAspAsnArgSerSerPhe-58
SEQ. ID. NO. 17586 62-IlePheSerAspGlyGluAspArgLeuGlySerGlnAla-74
SEQ. ID. NO. 17587 83-GlnGlnThrAsnArgPheAsnValLeuAsnArgThrAsn-95
SEQ. ID. NO. 17588 99-LeuLysGlnGluSerGlyIleSerGlyLysAlaHisAsnLeuLysGlyAlaAspTyr-117
SEQ. ID. NO. 17589 121-GlyAspValThrGluPheGlyArgArgAspValGlyAsp-133
SEQ. ID. NO. 17590 140-LeuGlyArgGlyLysSerGlnIle-147
SEQ. ID. NO. 17591 160-AsnThrSerGluIle-164
SEQ. ID. NO. 17592 169-GlnGlyAlaGlyGlu-173
SEQ. ID. NO. 17593 175-AlaLeuSerAsnArgGluIle-181
SEQ. ID. NO. 17594 185-GlyGlyThrSerGlyTyrAspAlaThrLeuAsnGlyLysValLeu-199
SEQ. ID. NO. 17595 214-ValAspAsnGlyAlaTrpGlnProAsnArg-223
Hydrophilic Regions - Hopp-Woods
SEQ. ID. NO. 17596 21-AlaThrGluSerSerArgSerLeuGluValGluLysValAla-34
SEQ. ID. NO. 17597 52-PheAspAsnArgSerSerPhe-58
SEQ. ID. NO. 17598 62-IlePheSerAspGlyGluAspArgLeuGlySerGlnAla-74
SEQ. ID. NO. 17599 99-LeuLysGlnGluSerGlyIleSerGlyLysAlaHisAsn-111
SEQ. ID. NO. 17600 122-AspValThrGluPheGlyArgArgAspValGlyAsp-133
SEQ. ID. NO. 17601 141-GlyArgGlyLysSer-145
SEQ. ID. NO. 17602 176-LeuSerAsnArgGluIle-181
a235
AMPHI Regions - AMPHI
SEQ. ID. NO. 17603 8-LeuAlaAlaValLeuAlaLeu-14
SEQ. ID. NO. 17604 18-GlnValGlnLysAlaProAsp-24
SEQ. ID. NO. 17605 86-LeuThrAsnAlaAlaAspIle-92
SEQ. ID. NO. 17606 95-ValArgProGluLysHisGlnIlePhe-104
SEQ. ID. NO. 17607 120-SerTyrGlnIleLeuAspSerValThrThr-129
SEQ. ID. NO. 17608 165-GlyAlaLeuValSerAlaValValAsnGlnIleAlaAsnSerLeuThr-180
SEQ. ID. NO. 17609 187-SerLysThrAlaAlaTyrAsnLeuLeuSerProTyr-198
Antigenic Index - Jameson-Wolf
SEQ. ID. NO. 17610 20-GlnLysAlaProAspPheAspTyrThrSerPheLysGluSerLysProAla-36
SEQ. ID. NO. 17611 43-ProLeuAsnGluSerProAspValAsnGlyThr-53
SEQ. ID. NO. 17612 62-AlaProLeuSerGlu-66
SEQ. ID. NO. 17613 79-GluThrPheLysGlnAsnGlyLeuThrAsn-88
SEQ. ID. NO. 17614 93-HisAlaValArgProGluLysLeu-100
SEQ. ID. NO. 17615 131-SerAlaLysAlaArgLeuValAspSerArgAsnGlyLysGluLeuTrpSerGlySerAlaSerIleArgGluGlySerAsnAsnSerAsnSer-161
SEQ. ID. NO. 17616 178-SerLeuThrAspArgGlyTyrGlnValSerLysThrAla-190
SEQ. ID. NO. 17617 202-GlyIleLeuLysGlyProArgPheValGluGluGlnProLys-215
Hydrophilic Regions - Hopp-Woods
SEQ. ID. NO. 17618 20-GlnLysAlaProAspPheAsp-26
SEQ. ID. NO. 17619 29-SerPheLysGluSerLysPro-35
SEQ. ID. NO. 17620 44-LeuAsnGluSerProAspVal-50
SEQ. ID. NO. 17621 93-HisAlaValArgProGluLysLeu-100
SEQ. ID. NO. 17622 131-SerAlaLysAlaArgLeuValAspSerArgAsnGlyLysGluLeuTrp-146
SEQ. ID. NO. 17623 150-AlaSerIleArgGluGlySerAsnAsnSer-159
SEQ. ID. NO. 17624 179-LeuThrAspArgGlyTyrGln-185
SEQ. ID. NO. 17625 207-ProArgPheValGluGluGlnProLys-215
a236
AMPHI Regions - AMPHI
SEQ. ID. NO. 17626 11-LeuCysThrAlaPheAlaAspGlyPhe-19
SEQ. ID. NO. 17627 107-PheAlaGlyPheAlaAspCysArgProPhe-116
SEQ. ID. NO. 17628 145-AlaAspAspValProArgPhePheAlaGlyGlu-155
SEQ. ID. NO. 17629 168-ArgAspValValGlnGlyGlyLeu-175
SEQ. ID. NO. 17630 215-ValGluGlyIleThrArgIle-221
SEQ. ID. NO. 17631 245-IleArgLeuLeuHisGlyIlePheAsnArgIleGluValAla-258
SEQ. ID. NO. 17632 316-ValAlaAspGlyPheArgHisPhe-323
Antigenic Index - Jameson-Wolf
SEQ. ID. NO. 17633 42-GlyPheSerGlyAsnGlyLysPhe-49
SEQ. ID. NO. 17634 58-ArgHisGlnGlnSerLysAlaGln-65
SEQ. ID. NO. 17635 77-PhePheArgArgGlyAsnPheGlyPheGlyLeuGlnGlyArgThrAspGlyPhe-94
SEQ. ID. NO. 17636 98-GlnArgLeuAspGlyGlyGlyTyr-105
SEQ. ID. NO. 17637 109-GlyPheAlaAspCysArgProPhe-116
SEQ. ID. NO. 17638 126-ValAspGlyArgGluLeuValProSerMetGluLys-137
SEQ. ID. NO. 17639 144-AlaAlaAspAspValPro-149
SEQ. ID. NO. 17640 155-GluAlaGlnAsnArgCysAsnGlnGluAsnGlnAlaAlaArgAspValValGlnGlyGlyLeu-175
SEQ. ID. NO. 17641 195-IleGluValGluArgAlaGlnValPheArgAlaGluArgAsnHis-209
SEQ. ID. NO. 17642 213-GlyLysValGluGlyIleThrArg-220
SEQ. ID. NO. 17643 222-LysIleThrGlyAsnAlaPheLeu-229
SEQ. ID. NO. 17644 261-GlyLysGlnLysAlaGlnGly-267
SEQ. ID. NO. 17645 292-IleGlyGlyCysArgProGlnAlaGlnAspValArgAla-304
SEQ. ID. NO. 17646 310-PheLeuArgArgAspAspValAlaAspGly-319

TABLE 1-continued

Hydrophilic Regions - Hopp-Woods
SEQ. ID. NO. 17647    89-GlyArgThrAspGly-93
SEQ. ID. NO. 17648    98-GlnArgLeuAspGlyGlyGly-104
SEQ. ID. NO. 17649    127-AspGlyArgGluLeuValProSerMetGluLys-137
SEQ. ID. NO. 17650    144-AlaAlaAspAspValPro-149
SEQ. ID. NO. 17651    156-AlaGlnAsnArgCysAsnGlnGluAsnGlnAlaAlaArgAspValVal-171
SEQ. ID. NO. 17652    195-IleGluValGluArgAlaGlnValPheArgAlaGluArgAsnHis-209
SEQ. ID. NO. 17653    214-LysValGluGlyIleThrArg-220
SEQ. ID. NO. 17654    261-GlyLysGlnLysAlaGlnGly-267
SEQ. ID. NO. 17655    295-CysArgProGlnAlaGlnAspValArgAla-304
SEQ. ID. NO. 17656    311-LeuArgArgAspAspValAlaAspGly-319
a239
AMPHI Regions - AMPHI
SEQ. ID. NO. 17657    49-PheArgLeuIleGlnSerCys-55
SEQ. ID. NO. 17658    72-AsnAlaHisArgLysGln-77
SEQ. ID. NO. 17659    123-ProGlyPheAsnAlaLeuProAlaIlePhe-132
SEQ. ID. NO. 17660    165-SerSerAsnGluTrp-169
SEQ. ID. NO. 17661    221-PheCysAlaThrIleCysAlaSerLeuArg-230
Antigenic Index - Jameson-Wolf
SEQ. ID. NO. 17662    6-GlyIleAlaArgAsnArgArgMetGlu-14
SEQ. ID. NO. 17663    19-CysArgArgProAspArgPheValValArgGlnThrArgLeuLeu-33
SEQ. ID. NO. 17664    52-IleGlnSerCysGluValGluPro-59
SEQ. ID. NO. 17665    66-HisAsnGlyLysSerGlyAsnAlaHisArgLysGlnGlnLysGluIle-81
SEQ. ID. NO. 17666    100-ProAlaValArgSerAlaThrArgLysThrAla-110
SEQ. ID. NO. 17667    132-PheArgGlyGlySerGlyLysSerAlaSer-141
SEQ. ID. NO. 17668    144-AlaAlaGlnArgGlyArgGlyAlaCys-152
SEQ. ID. NO. 17669    164-ArgSerSerAsnGluTrpLys-170
SEQ. ID. NO. 17670    173-ThrAlaLysArgProProSerPheArgArgHisMetThrCysGlyAsnThrAlaProThrSerSerSerSerArgLeuIleLys-200
SEQ. ID. NO. 17671    209-ValAlaGlySerCysProArgSerArgValArgThr-220
SEQ. ID. NO. 17672    248-TrpArgLeuAsnArgSerSerPro-255
Hydrophilic Regions - Hopp-Woods
SEQ. ID. NO. 17673    6-GlyIleAlaArgAsnArgArgMetGlu14
SEQ. ID. NO. 17674    20-ArgArgProAspArgPheValValArgGlnThrArg-31
SEQ. ID. NO. 17675    67-AsnGlyLysSerGlyAsnAlaHisArgLysGlnGlnLysGluIle-81
SEQ. ID. NO. 17676    102-ValArgSerAlaThrArgLysThrAla-110
SEQ. ID. NO. 17677    135-GlySerGlyLysSerAlaSer-141
SEQ. ID. NO. 17678    146-GlnArgGlyArgGlyAlaCys-152
SEQ. ID. NO. 17679    165-SerSerAsnGluTrpLys-170
SEQ. ID. NO. 17680    173-ThrAlaLysArgProProSerPheArgArgHisMet-184
SEQ. ID. NO. 17681    193-SerSerSerArgLeuIleLys-200
SEQ. ID. NO. 17682    211-GlySerCysProArgSerArgValArgThr-220
SEQ. ID. NO. 17683    251-AsnArgSerSerPro-255
a240
AMPHI Regions - AMPHI
SEQ. ID. NO. 17684    19-AlaAspValGlyArgPheLeuHis-26
SEQ. ID. NO. 17685    63-IleGlnCysLeuArgAsnHis-69
SEQ. ID. NO. 17686    87-AlaProLeuPheAlaValCysPro-94
SEQ. ID. NO. 17687    107-GlnGlyGluAspPheProArgAlaGlyIleGlnAsnHis-119
SEQ. ID. NO. 17688    154-ValPheArgGlyPheIleAlaArgGlyValGlnAlaValHisAsn-168
SEQ. ID. NO. 17689    188-PheLysArgLysPheGln-193
Antigenic Index - Jameson-Wolf
SEQ. ID. NO. 17690    9-GlyThrGluThrArgArgGlnPheAla-17
SEQ. ID. NO. 17691    39-IleAlaHisGlyArgArgSerAspPheIleArg-49
SEQ. ID. NO. 17692    67-ArgAsnHisLysArgPheAspCysArgThrGlyPheAsp-79
SEQ. ID. NO. 17693    101-ValGlyGlyArgIleGlyGlnGlyGlyArgAspPheProArgAlaGlyIleGlnAsnHisHisArgSerGly-123
SEQ. ID. NO. 17694    139-GlnGlyLeuAsnProLeuIleGluGlyLysAspAspVal-151
SEQ. ID. NO. 17695    173-ValProGlnAsnAspPheArg-179
SEQ. ID. NO. 17696    187-ValPheLysArgLysPhe-192
SEQ. ID. NO. 17697    201-AsnIleGlyLysSerAspAspValCysLys-210
Hydrophilic Regions - Hopp-Woods
SEQ. ID. NO. 17698    10-ThrGluThrArgArgGlnPheAla-17
SEQ. ID. NO. 17699    41-HisGlyArgArgSerAspPheIleArg-49
SEQ. ID. NO. 17700    67-ArgAsnHisLysArgPheAspCys-74
SEQ. ID. NO. 17701    105-IleGlyGlnGlyGluAspPheProArg-113
SEQ. ID. NO. 17702    145-IleGluGlyLysAspAspVal-151
SEQ. ID. NO. 17703    187-ValPheLysArgLysPhe-192
SEQ. ID. NO. 17704    203-GlyLysSerAspAspValCysLys-210
a241-1
AMPHI Regions - AMPHI
SEQ. ID. NO. 17705    6-ThrArgAlaAlaLysHis-11
SEQ. ID. NO. 17706    35-ThrHisThrProHisGluProAlaSerSer-44
SEQ. ID. NO. 17707    71-LysMetProSerGluMetGluGlnThrLeu-80
SEQ. ID. NO. 17708    109-PheLeuIleGlyCysIleAlaHisThrPheAsnArgSerLeuLys-123
SEQ. ID. NO. 17709    126-PheHisAlaCysGlnArgMetValAlaVal-135
SEQ. ID. NO. 17710    195-HisIleAspArgIleAlaGlyIleLeuThrValGln-206
SEQ. ID. NO. 17711    229-PheValGlnLysLeuIleValGlyIleIleHis-239
Antigenic Index - Jameson-Wolf
SEQ. ID. NO. 17712    1-MetProThrArgProThrArgAlaAlaLysHisProThrProProThrTrp-17
SEQ. ID. NO. 17713    23-CysProArgProProTyrArgProProSerValGlnThrHisThrProHisGluProAlaSerSerThrCysAlaAlaLysSer
                       AlaAsnArgArgGluAsnPheHis-58

TABLE 1-continued

| | |
|---|---|
| SEQ. ID. NO. 17714 | 68-ProSerAsnLysMetProSerGluMetGluGlnThrLeuPheArgArgHisGlnIleProProSerCysArgGlnSer-93 |
| SEQ. ID. NO. 17715 | 119-AsnArgSerLeuLysAlaAspPhe-126 |
| SEQ. ID. NO. 17716 | 147-ThrIleAspAspAsnIleAla-153 |
| SEQ. ID. NO. 17717 | 166-PheAspPheAsnArgGluHisAlaArg-174 |
| SEQ. ID. NO. 17718 | 176-PheAsnThrAspGlnLeu181 |
| SEQ. ID. NO. 17719 | 188-ArgIleValGlyArgLysArgHisIleAspArgIleAla-200 |
| SEQ. ID. NO. 17720 | 209-PheHisGlnArgGluAsnAla-215 |
| SEQ. ID. NO. 17721 | 244-ArgAsnHisGlyIle-248 |
| SEQ. ID. NO. 17722 | 251-AspSerHisIleCysProPheArgAsnSerArgLeuIle-263 |
| Hydrophilic Regions - Hopp-Woods | |
| SEQ. ID. NO. 17723 | 1-MetProThrArgProThrArgAlaAlaLysHisProThr-13 |
| SEQ. ID. NO. 17724 | 37-ThrProHisGluProAlaSer-43 |
| SEQ. ID. NO. 17725 | 46-CysAlaAlaLysSerAlaAsnArgArgGluAsnPheHis-58 |
| SEQ. ID. NO. 17726 | 70-AsnLysMetProSerGluMetGluGlnThrLeuPheArg-82 |
| SEQ. ID. NO. 17727 | 120-ArgSerLeuLysAlaAspPhe-126 |
| SEQ. ID. NO. 17728 | 166-PheAspPheAsnArgGluHisAlaArg-174 |
| SEQ. ID. NO. 17729 | 188-ArgIleValGlyArgLysArgHisIleAspArgIleAla-200 |
| SEQ. ID. NO. 17730 | 209-PheHisGlnArgGluAsnAla-215 |
| a242 | |
| AMPHI Regions - AMPHI | |
| SEQ. ID. NO. 17731 | 23-ProGluValAlaXxxGlnPheValAspPheValGlu-34 |
| SEQ. ID. NO. 17732 | 43-GlyPheCysHisIleLeuGlnAsnLeuThrGly-53 |
| SEQ. ID. NO. 17733 | 122-AsnProPhePheAspPhePheGlnAlaValVal-132 |
| SEQ. ID. NO. 17734 | 137-HisGlnSerGlyPheGlyAspValPhe-145 |
| SEQ. ID. NO. 17735 | 156-PheGluGlnGlyVal-160 |
| SEQ. ID. NO. 17736 | 191-PheGlyHisThrArgLeuPheAspIleCys-200 |
| SEQ. ID. NO. 17737 | 262-HisProPheAlaAspPheGlyAsnPheGlnAsnLeuLeuAlaLeu-276 |
| Antigenic Index - Jameson-Wolf | |
| SEQ. ID. NO. 17738 | 13-HisPheGluGlnArgAlaGlyGlyIleAla-22 |
| SEQ. ID. NO. 17739 | 52-ThrGlyHisGlyAla-56 |
| SEQ. ID. NO. 17740 | 75-SerHisAlaAspIlePheProProArgCysPheGlyAspGlyPheAlaGlnArgGlyPhe-94 |
| SEQ. ID. NO. 17741 | 98-TrpArgAlaAspGlnAlaGlnAsnArgAla-107 |
| SEQ. ID. NO. 17742 | 137-HisGlnSerGlyPhe-141 |
| SEQ. ID. NO. 17743 | 152-LeuProArgGlnPheGluGlnGlyVal-160 |
| SEQ. ID. NO. 17744 | 164-AlaTyrAspGlyGlyPheGlyArgHisArgHisHis-176 |
| SEQ. ID. NO. 17745 | 283-MetArgCysAspArgIleGly-289 |
| Hydrophilic Regions - Hopp-Woods | |
| SEQ. ID. NO. 17746 | 13-HisPheGluGlnArgAlaGlyGlyIle-21 |
| SEQ. ID. NO. 17747 | 98-TrpArgAlaAspGlnAlaGlnAsnArgAla-107 |
| SEQ. ID. NO. 17748 | 155-GlnPheGluGlnGlyVal-160 |
| SEQ. ID. NO. 17749 | 168-GlyPheGlyArgHisArgArgHisHis-176 |
| SEQ. ID. NO. 17750 | 283-MetArgCysAspArgIleGly-289 |
| a243 | |
| AMPHI Regions - AMPHI | |
| SEQ. ID. NO. 17751 | 25-IlePheSerMetLeu-29 |
| SEQ. ID. NO. 17752 | 35-IleThrArgLeuAlaArgLysAlaValGlnArgLeuThrAlaSerHisIleGlnArgPheLeu-55 |
| SEQ. ID. NO. 17753 | 80-AspSerSerArgIleThrSerThrIleSerSer-90 |
| Antigenic Index - Jameson-Wolf | |
| SEQ. ID. NO. 17754 | 29-LeuProSerAsnAlaPro-34 |
| SEQ. ID. NO. 17755 | 37-ArgLeuAlaArgLysAlaValGln-44 |
| SEQ. ID. NO. 17756 | 55-LeuThrGluSerLysThrGlyAlaAsnLysSerSerSerSerCysLysPro-71 |
| SEQ. ID. NO. 17757 | 77-SerAlaSerAspSerSerArgIle-84 |
| SEQ. ID. NO. 17758 | 102-SerThrThrGlyAlaValThrLysSer-110 |
| Hydrophilic Regions - Hopp-Woods | |
| SEQ. ID. NO. 17759 | 37-ArgLeuAlaArgLysAlaValGln-44 |
| SEQ. ID. NO. 17760 | 55-LeuThrGluSerLysThrGlyAlaAsnLysSerSerSerSerCysLys-70 |
| SEQ. ID. NO. 17761 | 78-AlaSerAspSerSerArgIle-84 |
| a244-1 | |
| AMPHI Regions - AMPHI | |
| SEQ. ID. NO. 17762 | 13-IleAlaAlaLeuLeuArg-18 |
| SEQ. ID. NO. 17763 | 24-AsnAlaLeuGlnGluIleAsnGlnIleIleProGlnThr-36 |
| SEQ. ID. NO. 17764 | 72-PheAlaCysHisArgLeuHisArgLeu-80 |
| SEQ. ID. NO. 17765 | 102-LysCysPheLeuGlnLeuValGln-109 |
| SEQ. ID. NO. 17766 | 111-HisLeuHisAlaHis-115 |
| SEQ. ID. NO. 17767 | 189-IleSerArgLeuCysGlySerLeuPhe-197 |
| SEQ. ID. NO. 17768 | 206-CysLeuAspGlyPheHisArgLeuHis-214 |
| SEQ. ID. NO. 17769 | 217-AsnArgPhePheThr-221 |
| SEQ. ID. NO. 17770 | 245-TyrProArgLysIleArgThrPheSerArgAsnPheLysGlnArg-259 |
| Antigenic Index - Jameson-Wolf | |
| SEQ. ID. NO. 17771 | 1-MetProSerGluAlaArgGlnAlaGlySerAspGly-12 |
| SEQ. ID. NO. 17772 | 20-ValTyrThrGlnAsnAla-25 |
| SEQ. ID. NO. 17773 | 35-GlnThrProSerGly-39 |
| SEQ. ID. NO. 17774 | 44-HisArgAsnHisSerArgAlaGlnHis-52 |
| SEQ. ID. NO. 17775 | 81-MetAspIleArgIle-85 |
| SEQ. ID. NO. 17776 | 91-PheArgIleAspPheLeuAsp-97 |
| SEQ. ID. NO. 17777 | 125-IleGlnLysArgHis-129 |
| SEQ. ID. NO. 17778 | 134-LeuAspArgGlnHisPheHisGlyLysLeuLeuSerGlyGluLeuValArg-150 |
| SEQ. ID. NO. 17779 | 179-GlnLeuGlyAsnProArgLeu-185 |
| SEQ. ID. NO. 17780 | 234-LeuLysThrAsnTrpLysSerLysSerSerTyrTyrProArgLysIleArgThrPheSerArgAsnPheLysGlnArgGlnArgIleSerAsnSerPheSerAsnProLeuProLysLys-273 |

TABLE 1-continued

Hydrophilic Regions - Hopp-Woods
SEQ. ID. NO. 17781  1-MetProSerGluAlaArgGlnAlaGlySerAspGly-12
SEQ. ID. NO. 17782  46-AsnHisSerArgAlaGlnHis-52
SEQ. ID. NO. 17783  81-MetAspIleArgIle-85
SEQ. ID. NO. 17784  91-PheArgIleAspPheLeuAsp-97
SEQ. ID. NO. 17785  236-ThrAsnTrpLysSerLysSer-242
SEQ. ID. NO. 17786  247-ArgLysIleArgThrPheSerArgAsnPheLysGlnArgGlnArgIle-262
a246-2
AMPHI Regions - AMPHI
SEQ. ID. NO. 17787  39-AlaValAsnIleAlaGlnCysPheThr-47
SEQ. ID. NO. 17788  60-ArgCysAlaGluValLeuValGluGlnPheAlaAsnLeuPhePhe-74
SEQ. ID. NO. 17789  83-AspMetGlyArgPhe-87
SEQ. ID. NO. 17790  132-PheGlyCysAspAspValValAspAspPheAlaGlyPheGlyArgCysPheArgProVal-151
SEQ. ID. NO. 17791  156-GlnLeuGlyGlnValPhePheGln-163
Antigenic Index - Jameson-Wolf
SEQ. ID. NO. 17792  1-MetHisGlyArgAsnGlyGlyThrGln-9
SEQ. ID. NO. 17793  18-GlnThrGlnArgThrCysPheSerAsnGlyGluValHisAlaThrGlnThrAspIleGlySer-38
SEQ. ID. NO. 17794  78-AspCysGlyHisHisAspMetGlyArg-86
SEQ. ID. NO. 17795  92-LeuAspAspGluLeuAla-97
SEQ. ID. NO. 17796  133-GlyCysAspAspValValAspAspPheAlaGlyPheGlyArgCysPheArg-149
SEQ. ID. NO. 17797  166-GlnGlnGlyArgGlnPheArgGln-173
Hydrophilic Regions - Hopp-Woods
SEQ. ID. NO. 17798  1-MetHisGlyArgAsnGlyGly-7
SEQ. ID. NO. 17799  92-LeuAspAspGluLeuAla-97
SEQ. ID. NO. 17800  136-AspValValAspAsp-140
SEQ. ID. NO. 17801  169-ArgGlnPheArgGln-173
a247-1
AMPHI Regions - AMPHI
SEQ. ID. NO. 17802  44-ValValSerSerCysSerLysIleAlaLysProGlyLysLysIleSerThrLeuGlnGlu-63
SEQ. ID. NO. 17803  153-PheAspSerSerThr-157
Antigenic Index - Jameson-Wolf
SEQ. ID. NO. 17804  11-GluSerThrAspIleLysTyrProGly-19
SEQ. ID. NO. 17805  33-IleAspAspLeuAspAlaSerAla-40
SEQ. ID. NO. 17806  47-SerCysSerLysIleAlaLysProGlyLysLysIleSerThrLeuGlnGluAlaLysSer-66
SEQ. ID. NO. 17807  70-IleThrAsnAspAspLysGlnAsnGlyAsnIleThrArgGlnArgHis-85
SEQ. ID. NO. 17808  95-IleAlaGlyGluGluGlyLeu-101
SEQ. ID. NO. 17809  104-PheGlnLeuAspAspLysGlyLysTrpGlyAsn-114
SEQ. ID. NO. 17810  120-LysLysIleArgHisMetLys-126
SEQ. ID. NO. 17811  133-SerAspCysProGluAspAspAspAlaGlyLysGluGluLysPheLysTyrThrGlyThrPheAspSerSerThrAsnAla-159
SEQ. ID. NO. 17812  171-SerGlyThrAspThrLysIleAlaAlaSerSerAspAsnHis-184
SEQ. ID. NO. 17813  192-AlaThrIleArgGlyGlyAsnValCysAlaAsnArgThrLeu-205
Hydrophilic Regions - Hopp-Woods
SEQ. ID. NO. 17814  11-GluSerThrAspIleLys-16
SEQ. ID. NO. 17815  33-IleAspAspLeuAspAlaSerAla-40
SEQ. ID. NO. 17816  49-SerLysIleAlaLysProGlyLysLysIleSerThr-60
SEQ. ID. NO. 17817  62-GlnGluAlaLysSer-66
SEQ. ID. NO. 17818  71-ThrAsnAspAspLysGlnAsnGlyAsnIleThrArgGlnArgHis-85
SEQ. ID. NO. 17819  95-IleAlaGlyGluGluGlyLeu-101
SEQ. ID. NO. 17820  105-GlnLeuAspAspLysGlyLysTrpGly-113
SEQ. ID. NO. 17821  120-LysLysIleArgHisMetLys-126
SEQ. ID. NO. 17822  134-AspCysProGluAspAspAspAlaGlyLysGluGluLysPheLysTyr-149
SEQ. ID. NO. 17823  153-PheAspSerSerThr-157
SEQ. ID. NO. 17824  172-GlyThrAspThrLysIleAlaAlaSerSerAsp-182
a248-1
AMPHI Regions - AMPHI
SEQ. ID. NO. 17825  88-GluAsnCysGlyLysGlyLeu-94
SEQ. ID. NO. 17826  121-ValGluAlaValLysArg-126
SEQ. ID. NO. 17827  148-ThrGlnSerValSerLysMetProArgTyrIleIleGlu-160
SEQ. ID. NO. 17828  168-GluAsnValTyrArgValThrAlaLysAlaTrpGlyLysAsn-181
Antigenic Index - Jameson-Wolf
SEQ. ID. NO. 17829  1-MetArgLysGlnAsnThrLeuThr-8
SEQ. ID. NO. 17830  11-ProThrSerAspGlyGlnArgGly-18
SEQ. ID. NO. 17831  40-GlnSerTyrAsnThrGluGlnArgIleSerAlaAsnGluSerAspArgLysLeuAla-58
SEQ. ID. NO. 17832  64-AlaAlaLeuArgGluGlyGluLeuGln-72
SEQ. ID. NO. 17833  76-LeuGluTyrAspThrAspSerLysValThrPheSerGluAsnCysGlyLysGlyLeu-94
SEQ. ID. NO. 17834  99-AsnValArgThrAsnAsnAspAsnGluGluAlaPhe-110
SEQ. ID. NO. 17835  116-GlnGlyLysProThrValGluValAlaValLysArgSerCysThrAlaLysSerThrGlyLeu-135
SEQ. ID. NO. 17836  137-IleAspAsnLysGlyMetGluTyrLysLysGlyThrGlnSerValSerLysMetProArgTyr-157
SEQ. ID. NO. 17837  162-LeuGlyValLysAsnGlyGluAsnValTyr-171
SEQ. ID. NO. 17838  177-AlaTrpGlyLysAsnAlaAsnThr-184
SEQ. ID. NO. 17839  192-ValSerAsnAsnAspGlu-197
Hydrophilic Regions - Hopp-Woods
SEQ. ID. NO. 17840  1-MetArgLysGlnAsnThr-6
SEQ. ID. NO. 17841  11-ProThrSerAspGlyGlnArg-17
SEQ. ID. NO. 17842  42-TyrAsnThrGluGlnArgIleSerAlaAsnGluSerAspArgLysLeuAla-58
SEQ. ID. NO. 17843  64-AlaAlaLeuArgGluGlyGluLeuGln-72
SEQ. ID. NO. 17844  76-LeuGluTyrAspThrAspSerLysValThrPhe-86
SEQ. ID. NO. 17845  101-ArgThrAsnAsnAspAsnGluGluAlaPhe-110
SEQ. ID. NO. 17846  119-ProThrValGluAlaValLysArgSerCysThrAlaLysSer-132
SEQ. ID. NO. 17847  137-IleAspAsnLysGlyMetGluTyrLysLysGlyThrGlnSerValSerLysMetPro-155

TABLE 1-continued

| SEQ. ID. NO. 17848 | 165-LysAsnGlyGluAsnValTyr-171 |
| SEQ. ID. NO. 17849 | 193-SerAsnAsnAspGlu-197 | a249-1
AMPHI Regions - AMPHI
SEQ. ID. NO. 17850   6-CysPheArgLeuLys-10
SEQ. ID. NO. 17851   15-GlyMetAlaLeuIleGluValLeuVal-23
SEQ. ID. NO. 17852   42-ThrValAlaSerValArgGluAla-49
SEQ. ID. NO. 17853   53-ThrIleValSerGlnIleThrGlnAsnLeuMetGluGlyMet-66
Antigenic Index - Jameson-Wolf
SEQ. ID. NO. 17854   1-MetLysAsnAsnAspCysPheArgLeuLysAsnProGlnSerGly-15
SEQ. ID. NO. 17855   44-AlaSerValArgGluAlaGluThr-51
SEQ. ID. NO. 17856   70-ProThrIleAspSerAspSerAsnLysLysAsnTyr-81
SEQ. ID. NO. 17857   94-ValAspGlyAspPheGln-99
SEQ. ID. NO. 17858   102-AlaIleLysThrLysThrGlnLeuAla-110
SEQ. ID. NO. 17859   135-ValCysLysAspSerSerGlyValAla-143
SEQ. ID. NO. 17860   154-SerAsnCysAspGlySerAlaAsnGlyAspThrLeu-165
SEQ. ID. NO. 17861   173-AspSerAlaGlyAspSerAspIleAlaArgThrAsnLeuGluThrAsnGlyAsnAsn-191
SEQ. ID. NO. 17862   198-AlaArgValGlyGlyArgGlu-204
Hydrophilic Regions - Hopp-Woods
SEQ. ID. NO. 17863   1-MetLysAsnAsnAspCysPheArgLeuLysAsnProGln-13
SEQ. ID. NO. 17864   44-AlaSerValArgGluAlaGluThr-51
SEQ. ID. NO. 17865   72-IleAspSerAspSerAsnLysLysAsn-80
SEQ. ID. NO. 17866   94-ValAspGlyAspPheGln-99
SEQ. ID. NO. 17867   102-AlaIleLysThrLysThrGlnLeuAla-110
SEQ. ID. NO. 17868   135-ValCysLysAspSerSerGly-141
SEQ. ID. NO. 17869   155-AsnCysAspGlySerAlaAsnGly-162
SEQ. ID. NO. 17870   174-SerAlaGlyAspSerAspIleAlaArgThrAsnLeuGluThrAsnGly-189
SEQ. ID. NO. 17871   200-ValGlyGlyArgGlu-204
a250
AMPHI Regions - AMPHI
SEQ. ID. NO. 17872   8-ArgAsnGluPheIleArgGlyIleLysGlu-17
SEQ. ID. NO. 17873   54-PheAlaGlyGlySerGlu-59
SEQ. ID. NO. 17874   61-AlaThrValAsnLeuTrpAlaGluPro-69
Antigenic Index - Jameson-Wolf
SEQ. ID. NO. 17875   5-SerSerProArgAsnGluPheIleArgGlyIleLysGluSerSer-19
SEQ. ID. NO. 17876   34-MetGlnGlyGlyGlnLysGlyMetSer-42
SEQ. ID. NO. 17877   54-PheAlaGlyGlySerGlu-59
SEQ. ID. NO. 17878   90-GlyXxxGlyThrCysProAlaProGluArgAsnThrAlaGluLysSerArgAlaArg-108
Hydrophilic Regions - Hopp-Woods
SEQ. ID. NO. 17879   5-SerSerProArgAsnGluPheIleArgGlyIleLysGluSerSer-19
SEQ. ID. NO. 17880   95-ProAlaProGluArgAsnThrAlaGluLysSerArgAlaArg-108
a251
AMPHI Regions - AMPHI
SEQ. ID. NO. 17881   47-GlnAlaAlaAspLeuProArgAsnHisIleSerProAlaTyr-60
SEQ. ID. NO. 17882   81-ArgArgIleGlyAla-85
SEQ. ID. NO. 17883   110-GlnValValAlaAspPheGlyGlyIleGluGlyPhe-121
SEQ. ID. NO. 17884   156-ArgThrValGlyArgThrValArgLeuLeuLysMetIle-168
SEQ. ID. NO. 17885   211-AlaArgThrValPheArgAlaHis-218
SEQ. ID. NO. 17886   255-LeuGlyGlnGluCysArg-260
SEQ. ID. NO. 17887   262-ArgHisIleAlaArgValGluSerLeuLeuArgValPheGluTyrAlaAlaAsp-279
Antigenic Index - Jameson-Wolf
SEQ. ID. NO. 17888   9-GlnProArgAlaAspIleArgProProAlaGlnThrAspIleValProAsnCys-26
SEQ. ID. NO. 17889   34-AspAlaAlaArgArgAlaValArg-41
SEQ. ID. NO. 17890   50-AspLeuProArgAsnHisIleSer-57
SEQ. ID. NO. 17891   74-GlyGlyPheArgGlyArgPheArgArg-82
SEQ. ID. NO. 17892   98-IleArgValLysAlaValLysThrGluIle-107
SEQ. ID. NO. 17893   145-ArgLeuValGlyThr-149
SEQ. ID. NO. 17894   157-ThrValGlyArgThrValArg-163
SEQ. ID. NO. 17895   175-ProValValArgGluAlaGly-181
SEQ. ID. NO. 17896   208-ValLysHisAlaArgThrValPhe-215
SEQ. ID. NO. 17897   251-IleLysAsnArgLeuGlyGlnGluCysArgAsnArgHisIleAlaArgValGluSer-269
SEQ. ID. NO. 17898   286-LysThrLysThrArgAlaGluGlnProArgSerAla-297
Hydrophilic Regions - Hopp-Woods
SEQ. ID. NO. 17899   10-ProArgAlaAspIleArgProProAlaGln-19
SEQ. ID. NO. 17900   34-AspAlaAlaArgArgAlaValArg-41
SEQ. ID. NO. 17901   76-PheArgGlyArgPheArgArg-82
SEQ. ID. NO. 17902   98-IleArgValLysAlaValLysThrGluIle-107
SEQ. ID. NO. 17903   157-ThrValGlyArgThrValArg-163
SEQ. ID. NO. 17904   175-ProValValArgGluAlaGly-181
SEQ. ID. NO. 17905   208-ValLysHisAlaArgThrValPhe-215
SEQ. ID. NO. 17906   253-AsnArgLeuGlyGlnGluCysArgAsnArgHisIleAlaArgValGluSer-269
SEQ. ID. NO. 17907   287-ThrLysThrArgAlaGluGlnProArg-295
a254
AMPHI Regions - AMPHI
SEQ. ID. NO. 17908   6-ArgPheAsnThrTyrSerHis-12
SEQ. ID. NO. 17909   32-GlyHisGlyAspGlyTyrArg-38
SEQ. ID. NO. 17910   66-LysLeuLysSerIleLeuLys-72
SEQ. ID. NO. 17911   142-ValLeuAlaValMetLysSerLeuThrAlaSer-152
Antigenic Index - Jameson-Wolf
SEQ. ID. NO. 17912   2-TyrThrGlyGluArgPheAsnThrTyrSer-11

TABLE 1-continued

| | |
|---|---|
| SEQ. ID. NO. 17913 | 32-GlyHisGlyAspGlyTyrArg-38 |
| SEQ. ID. NO. 17914 | 65-GlyLysLeuLysSerIleLeuLysLysThrAspHis-76 |
| SEQ. ID. NO. 17915 | 94-SerLeuArgAsnGlyProGly-100 |
| SEQ. ID. NO. 17916 | 120-ThrIleGlyArgLysSerGluLysArgLeuLeu-130 |
| SEQ. ID. NO. 17917 | 177-AsnAspGluLysIleArgHisGlyHisGly-186 |

Hydrophilic Regions - Hopp-Woods

| | |
|---|---|
| SEQ. ID. NO. 17918 | 65-GlyLysLeuLysSerIleLeuLysLysThrAspHis-76 |
| SEQ. ID. NO. 17919 | 120-ThrIleGlyArgLysSerGluLysArgLeuLeu-130 |
| SEQ. ID. NO. 17920 | 177-AsnAspGluLysIleArgHis-183 | a255
AMPHI Regions - AMPHI

| | |
|---|---|
| SEQ. ID. NO. 17921 | 23-ValLysThrCysAlaAspPheHisAlaPheAspGlyValAspAlaHisHisGly-40 |
| SEQ. ID. NO. 17922 | 71-GlyIleGlnGlyPheAlaHis-77 |
| SEQ. ID. NO. 17923 | 139-AlaGlyGlyGlyPhe-143 |

Antigenic Index - Jameson-Wolf

| | |
|---|---|
| SEQ. ID. NO. 17924 | 40-GlyValGlyAspPheGly-45 |
| SEQ. ID. NO. 17925 | 54-AlaGlnAlaAspGlyAspValGlyGly-62 |
| SEQ. ID. NO. 17926 | 67-LeuArgAlaAspGlyIleGln-73 |
| SEQ. ID. NO. 17927 | 91-ValGlyGlyLysLysArgIleLeu-98 |
| SEQ. ID. NO. 17928 | 115-GlyAsnValGlyGlyAspPheArgAla-123 |
| SEQ. ID. NO. 17929 | 130-PhePheGlyAsnGlySerGlyGlyAsnAlaGly-140 |
| SEQ. ID. NO. 17930 | 145-GlyGlyThrProAla-149 |

Hydrophilic Regions - Hopp-Woods

| | |
|---|---|
| SEQ. ID. NO. 17931 | 56-AlaAspGlyAspVal-60 |
| SEQ. ID. NO. 17932 | 67-LeuArgAlaAspGly-71 |
| SEQ. ID. NO. 17933 | 92-GlyGlyLysLysArgIleLeu-98 |
| SEQ. ID. NO. 17934 | 119-GlyAspPheArgAla-123 | a256-1
AMPHI Regions - AMPHI

| | |
|---|---|
| SEQ. ID. NO. 17935 | 90-GlyValValValHisPheArgSerCysGlyGlyValAla-102 |
| SEQ. ID. NO. 17936 | 127-ArgTyrArgGluIleTyrAlaVal-134 |
| SEQ. ID. NO. 17937 | 141-AsnAlaLeuAlaLysTyrLeuGlyGluGln-150 |
| SEQ. ID. NO. 17938 | 174-ArgPheAspSerGlyIleThrArgLeuLeu-183 |
| SEQ. ID. NO. 17939 | 197-ArgSerLeuGlnGlyPheGlnThrAla-205 |
| SEQ. ID. NO. 17940 | 207-AlaAlaGlyCysLysThrLeuGlyGluPheAspAspArgPheThrAlaProLeuHisGly-226 |
| SEQ. ID. NO. 17941 | 233-TyrTyrArgGlnThrSerCysLysProLeuLeuLysHisValAla-247 |
| SEQ. ID. NO. 17942 | 267-ProArgAlaAspGluValSer-273 |

Antigenic Index - Jameson-Wolf

| | |
|---|---|
| SEQ. ID. NO. 17943 | 4-ThrProProAspThrProPhe-10 |
| SEQ. ID. NO. 17944 | 12-LeuArgAsnGlyAsnAlaAspThrIleAla-21 |
| SEQ. ID. NO. 17945 | 24-PheLeuGlnArgSerAlaProAlaTyrArgArgGluLeuLeuProAspSerThrGlyLysThrLysThrAlaTyrAspPheSerAspGlyIleSerProAspAla-58 |
| SEQ. ID. NO. 17946 | 67-LeuGluGlyGlySerGlySer-73 |
| SEQ. ID. NO. 17947 | 82-AlaValArgAspArgGlyTrpAsn-89 |
| SEQ. ID. NO. 17948 | 97-SerCysGlyGlyValAlaAsn-103 |
| SEQ. ID. NO. 17949 | 112-GlyAspThrAlaGlu-116 |
| SEQ. ID. NO. 17950 | 124-LeuAlaAlaArgTyrArgGlu-130 |
| SEQ. ID. NO. 17951 | 147-LeuGlyGluGlnGlyGluAsnAlaLeu-155 |
| SEQ. ID. NO. 17952 | 166-ValAspAlaGluAlaAlaGlyAsnArgPheAspSerGlyIle-179 |
| SEQ. ID. NO. 17953 | 192-LeuIleProLysAlaArgSerLeuGln-200 |
| SEQ. ID. NO. 17954 | 212-ThrLeuGlyGluPheAspAspArgPheThr-221 |
| SEQ. ID. NO. 17955 | 227-PheAlaAspArgHisAspTyrTyrArgGlnThrSerCysLysProLeuLeu-243 |
| SEQ. ID. NO. 17956 | 259-ProPheLeuProProGluAlaLeuProArgAlaAspGluValSerGlu-274 |
| SEQ. ID. NO. 17957 | 292-SerThrGlyGlyArgLeu-297 |
| SEQ. ID. NO. 17958 | 311-AspSerPheArgThrAsnArgArg-318 |

Hydrophilic Regions - Hopp-Woods

| | |
|---|---|
| SEQ. ID. NO. 17959 | 28-SerAlaProAlaTyrArgArgGluLeuLeuPro-38 |
| SEQ. ID. NO. 17960 | 40-SerThrGlyLysThrLysThr-46 |
| SEQ. ID. NO. 17961 | 83-ValArgAspArgGlyTrp-88 |
| SEQ. ID. NO. 17962 | 124-LeuAlaAlaArgTyrArgGlu-130 |
| SEQ. ID. NO. 17963 | 147-LeuGlyGluGlnGlyGluAsnAlaLeu-155 |
| SEQ. ID. NO. 17964 | 166-ValAspAlaGluAlaAlaGlyAsnArgPheAspSerGlyIle-179 |
| SEQ. ID. NO. 17965 | 192-LeuIleProLysAlaArgSer-198 |
| SEQ. ID. NO. 17966 | 212-ThrLeuGlyGluPheAspAspArgPheThr-221 |
| SEQ. ID. NO. 17967 | 227-PheAlaAspArgHisAspTyrTyrArg-235 |
| SEQ. ID. NO. 17968 | 265-AlaLeuProArgAlaAspGluValSerGlu-274 |
| SEQ. ID. NO. 17969 | 313-PheArgThrAsnArgArg-318 | a257
AMPHI Regions - AMPHI

| | |
|---|---|
| SEQ. ID. NO. 17970 | 24-SerPheLeuProAsn-28 |
| SEQ. ID. NO. 17971 | 73-AspLeuValAsnLysValLeuAlaGluValAlaArgLeuGluLysMetPhe-89 |
| SEQ. ID. NO. 17972 | 109-SerProProAlaAspPheLeuGluLeuLeuSerLeuAlaValIlePheThr-125 |

Antigenic Index - Jameson-Wolf

| | |
|---|---|
| SEQ. ID. NO. 17973 | 1-MetGlyArgHisPheGlyArgArgArgPhe-10 |
| SEQ. ID. NO. 17974 | 31-AlaAlaAspAspGluLysArgAsnLysAspGluLysArgAsnGluAsn-46 |
| SEQ. ID. NO. 17975 | 56-GlySerGlyAlaGlu-60 |
| SEQ. ID. NO. 17976 | 65-GlyValAspAspArgArgAlaAlaAspLeuVal-75 |
| SEQ. ID. NO. 17977 | 83-AlaArgLeuGluLys-87 |
| SEQ. ID. NO. 17978 | 92-TyrArgGluAspSerLeuIleSerArgLeuAsnArgAspGlyTyrLeuThrSerProProAlaAspPhe-114 |

TABLE 1-continued

Hydrophilic Regions - Hopp-Woods
SEQ. ID. NO. 17979  4-HisPheGlyArgArgArgPhe-10
SEQ. ID. NO. 17980  31-AlaAlaAspAspGluLysArgAsnLysAspGluLysArgAsnGlu-45
SEQ. ID. NO. 17981  65-GlyValAspAspArgArgAlaAlaAspLeuVal-75
SEQ. ID. NO. 17982  83-AlaArgLeuGluLys-87
SEQ. ID. NO. 17983  92-TyrArgGluAspSerLeuIle-98
SEQ. ID. NO. 17984  100-ArgLeuAsnArgAspGlyTyr-106
a259-1
AMPHI Regions - AMPHI
SEQ. ID. NO. 17985  154-TyrGlyArgValPheAlaAspIlePheGluLeuSer-165
SEQ. ID. NO. 17986  172-AlaPheLysGlyMetLeuLysLeuThrAlaGluTyrLysAsnIlePheGlyAspAlaCysArg-192
SEQ. ID. NO. 17987  203-AsnGlnAlaLeuGlnGluIleSerLysThrSerGlu-214
Antigenic Index - Jameson-Wolf
SEQ. ID. NO. 17988  34-LysAlaTyrThrGluGluLeuProPro-42
SEQ. ID. NO. 17989  61-SerAlaArgSerLysAlaLysAlaGluLysPheTyrArgGluLysMetIleGln-78
SEQ. ID. NO. 17990  93-LeuGluHisLysPro-97
SEQ. ID. NO. 17991  105-LysAsnHisGlyLysGlyMetAlaGluGlnValArgPheLysAla-119
SEQ. ID. NO. 17992  121-ValLeuProAspAspGluAspAlaArgThrIleAla-132
SEQ. ID. NO. 17993  144-GlyThrAspAlaValAlaSerGlyGluThrTyrGlyArgVal-157
SEQ. ID. NO. 17994  168-LeuGluGlyArgAlaPhe-173
SEQ. ID. NO. 17995  189-AspAlaCysArgSerGluThrAlaLeu-197
SEQ. ID. NO. 17996  208-GluIleSerLysThrSerGluLysSerLysArg-218
Hydrophilic Regions - Hopp-Woods
SEQ. ID. NO. 17997  35-AlaTyrThrGluGluLeuPro-41
SEQ. ID. NO. 17998  62-AlaArgSerLysAlaLysAlaGluLysPheTyrArgGluLysMetIleGln-78
SEQ. ID. NO. 17999  93-LeuGluHisLysPro-97
SEQ. ID. NO. 18000  106-AsnHisGlyLysGlyMetAlaGluGlnValArgPheLysAla-119
SEQ. ID. NO. 18001  121-ValLeuProAspAspGluAspAlaArgThrIleAla-132
SEQ. ID. NO. 18002  168-LeuGluGlyArgAlaPhe-173
SEQ. ID. NO. 18003  189-AspAlaCysArgSerGluThrAlaLeu-197
SEQ. ID. NO. 18004  208-GluIleSerLysThrSerGluLysSerLysArg-218
a260
AMPHI Regions - AMPHI
SEQ. ID. NO. 18005  12-ProPheSerSerLeuPheArgAlaLeuPhe-21
SEQ. ID. NO. 18006  53-PheIleAspSerValGlyGlnValAlaAlaArgLeuPheGlnAlaPhe-68
SEQ. ID. NO. 18007  154-ValGlnIleAsnGlnValGlyIleValAspLeuIlePro-166
SEQ. ID. NO. 18008  176-AlaThrGlyCysThrGlyIleCysProLysCysProThrGlyCysArgPro-192
Antigenic Index - Jameson-Wolf
SEQ. ID. NO. 18009  20-LeuPheGluAspArgValGlyIle-27
SEQ. ID. NO. 18010  30-GlyAlaHisAspAlaAlaGlu-36
SEQ. ID. NO. 18011  38-AspPheLeuProGluGluPheThrArg-46
SEQ. ID. NO. 18012  80-ProAlaPheArgAlaArgGluGlnAlaArgArgGlySerGly-93
SEQ. ID. NO. 18013  96-AlaGlyAsnAspLeuArgValProHisLysAspAlaValGluValAspIleAspGlyGlyAsnThrVal-118
SEQ. ID. NO. 18014  126-ThrHisPheAspAspGlyAspAla-133
SEQ. ID. NO. 18015  139-AlaGluAlaArgPhe-143
SEQ. ID. NO. 18016  184-ProLysCysProThrGlyCysArgProVal-193
Hydrophilic Regions - Hopp-Woods
SEQ. ID. NO. 18017  20-LeuPheGluAspArgValGlyIle-27
SEQ. ID. NO. 18018  30-GlyAlaHisAspAlaAlaGlu-36
SEQ. ID. NO. 18019  82-PheArgAlaArgGluGlnAlaArgArgGlySer-92
SEQ. ID. NO. 18020  98-AsnAspLeuArgValProHisLysAspAlaValGluValAspIleAspGly-114
SEQ. ID. NO. 18021  127-HisPheAspAspGlyAspAla-133
SEQ. ID. NO. 18022  139-AlaGluAlaArgPhe-143
SEQ. ID. NO. 18023  186-CysProThrGlyCysArgProVal-193
a261
AMPHI Regions - AMPHI
SEQ. ID. NO. 18024  22-GlnIlePheArgGln-26
SEQ. ID. NO. 18025  32-AspThrAlaArgAlaPheAlaAlaAla-40
SEQ. ID. NO. 18026  50-GlyLeuLeuAlaAspIleVal-56
SEQ. ID. NO. 18027  92-ValHisGlyPheAspLysHis-98
SEQ. ID. NO. 18028  137-AlaValTyrLysGlyIleArgAsnAlaValPhe-147
SEQ. ID. NO. 18029  158-GlnGlyIleValArgAsnLeu-164
SEQ. ID. NO. 18030  203-AspValPheAlaProVal-208
SEQ. ID. NO. 18031  212-CysLeuAsnGlnAlaGlyGly-218
Antigenic Index - Jameson-Wolf
SEQ. ID. NO. 18032  40-AlaAlaAspAspAlaVal-45
SEQ. ID. NO. 18033  60-HisPheValArgGlnArgProSerLeuArgLeu-70
SEQ. ID. NO. 18034  74-HisGlnArgArgValAspLeu-80
SEQ. ID. NO. 18035  86-ArgGlnIleLysGlyAsnValHisGlyPheAspLysHisVal-99
SEQ. ID. NO. 18036  111-AlaHisAlaArgAspAspValProTyr-119
SEQ. ID. NO. 18037  126-AsnArgGlyIleGluGlnGluLysArgVal-135
SEQ. ID. NO. 18038  149-SerPheAspGlyGlyGly-154
SEQ. ID. NO. 18039  181-ArgAsnProAlaGly-185
SEQ. ID. NO. 18040  197-LeuGluSerAsnGlyLeuAsp-203
SEQ. ID. NO. 18041  214-AsnGlnAlaGlyGlyArgIleLeuThrAlaArgLysAspAspGlnGlyPhe-230
Hydrophilic Regions - Hopp-Woods
SEQ. ID. NO. 18042  40-AlaAlaAspAspAlaVal-45
SEQ. ID. NO. 18043  60-HisPheValArgGlnArgProSerLeu-68
SEQ. ID. NO. 18044  74-HisGlnArgArgValAspLeu-80
SEQ. ID. NO. 18045  94-GlyPheAspLysHisVal-99

TABLE 1-continued

| | |
|---|---|
| SEQ. ID. NO. 18046 | 112-HisAlaArgAspAspValPro-118 |
| SEQ. ID. NO. 18047 | 127-ArgGlyIleGluGlnGluLysArgVal-135 |
| SEQ. ID. NO. 18048 | 221-LeuThrAlaArgLysAspAspGlnGly-229 | a263
AMPHI Regions - AMPHI

| | |
|---|---|
| SEQ. ID. NO. 18049 | 32-AsnLeuIleGlyValLeuSerAsnAla-40 |
| SEQ. ID. NO. 18050 | 42-GluAlaLeuAlaPheTyrGlnGluValGlyLysLeuAsnAlaAlaAsnSerLeuThr-60 |
| SEQ. ID. NO. 18051 | 86-LysLeuAlaThrLeuLysLys-92 |
| SEQ. ID. NO. 18052 | 100-LysAlaAlaArgAlaLeuAlaAlaAlaGlyGlu-109 |
| SEQ. ID. NO. 18053 | 115-LeuGlyAlaLeuAlaAlaPheThrGln-123 |
| SEQ. ID. NO. 18054 | 135-GluGluLeuLysAlaPhePheAspAla-143 |
| SEQ. ID. NO. 18055 | 157-ValAlaLeuAlaThrLeuCysAsnTyrValAsnAsnLeuGly-170 |

Antigenic Index - Jameson-Wolf

| | |
|---|---|
| SEQ. ID. NO. 18056 | 10-GluThrAlaProGluAlaAlaLysAlaArgValGluAla-22 |
| SEQ. ID. NO. 18057 | 37-LeuSerAsnAlaPro-41 |
| SEQ. ID. NO. 18058 | 72-AlaArgThrAsnGlnCysGly-78 |
| SEQ. ID. NO. 18059 | 97-GlnSerValLysAlaAlaArg-103 |
| SEQ. ID. NO. 18060 | 108-GlyGluPheAspAspAlaLysLeu-115 |
| SEQ. ID. NO. 18061 | 126-MetAlaLysLysGlyAlaValSerAspGluGluLeuLysAla-139 |
| SEQ. ID. NO. 18062 | 170-GlyGlnThrGluIleAsnProGluLeu-178 |

Hydrophilic Regions - Hopp-Woods

| | |
|---|---|
| SEQ. ID. NO. 18063 | 11-ThrAlaProGluAlaAlaLysAlaArgValGluAla-22 |
| SEQ. ID. NO. 18064 | 97-GlnSerValLysAlaAlaArg-103 |
| SEQ. ID. NO. 18065 | 108-GlyGluPheAspAspAlaLysLeu-115 |
| SEQ. ID. NO. 18066 | 126-MetAlaLysLysGlyAlaValSerAspGluGluLeuLysAla-139 | a264
AMPHI Regions - AMPHI

| | |
|---|---|
| SEQ. ID. NO. 18067 | 55-ValAlaGluPheThrGlnThrGly-62 |
| SEQ. ID. NO. 18068 | 96-IleProSerTyrValArgValThrAsnThrLys-106 |
| SEQ. ID. NO. 18069 | 124-AsnArgIleIleAspValSer-130 |
| SEQ. ID. NO. 18070 | 183-LeuAsnGlnAlaAlaGlnAsnLeuAlaSerSer-193 |

Antigenic Index - Jameson-Wolf

| | |
|---|---|
| SEQ. ID. NO. 18071 | 27-AlaValValArgAlaGluLysLeuHisAlaSerAlaAsnArgSerTyrLysValAlaGlyLysArgTyrThrProLysAsnGlnVal-55 |
| SEQ. ID. NO. 18072 | 57-GluPheThrGlnThrGlyAsnAlaSerTrp-66 |
| SEQ. ID. NO. 18073 | 68-GlyGlyArgPheHisGlyArgLysThrSerGlyGlyGluArgTyrAsp-83 |
| SEQ. ID. NO. 18074 | 103-ThrAsnThrLysAsnGlyLysSerVal-111 |
| SEQ. ID. NO. 18075 | 114-ArgValAsnAspArgGlyProPheHisGlyAsnArgIleIleAspValSerLysAlaAlaAla-134 |
| SEQ. ID. NO. 18076 | 153-ValProGlyGlnSerAlaProValAlaGluAsnLysAspIlePheIle-168 |
| SEQ. ID. NO. 18077 | 170-LeuLysSerPheGlyThrGluHisGluAla-179 |
| SEQ. ID. NO. 18078 | 192-SerSerAlaSerAsnProAsnLeuSerValGluLysArgArgTyrGluTyr-208 |
| SEQ. ID. NO. 18079 | 216-AlaSerGlnGluArgAlaAlaGluAlaGluAlaGlnAla-228 |

Hydrophilic Regions - Hopp-Woods

| | |
|---|---|
| SEQ. ID. NO. 18080 | 27-AlaValValArgAlaGluLysLeuHisAlaSerAlaAsnArgSerTyrLysValAlaGlyLysArgTyrThrPro-51 |
| SEQ. ID. NO. 18081 | 71-PheHisGlyArgLysThrSerGlyGlyGluArgTyrAsp-83 |
| SEQ. ID. NO. 18082 | 103-ThrAsnThrLysAsnGlyLys-109 |
| SEQ. ID. NO. 18083 | 115-ValAsnAspArgGlyProPheHis-122 |
| SEQ. ID. NO. 18084 | 125-ArgIleIleAspValSerLysAlaAlaAla-134 |
| SEQ. ID. NO. 18085 | 159-ProValAlaGluAsnLysAspIlePheIle-168 |
| SEQ. ID. NO. 18086 | 171-LysSerPheGlyThrGluHisGluAla-179 |
| SEQ. ID. NO. 18087 | 199-LeuSerValGluLysArgArgTyrGluTyr-208 |
| SEQ. ID. NO. 18088 | 216-AlaSerGlnGluArgAlaAlaGluAlaGluAlaGlnAla-228 | a266
Antigenic Index - Jameson-Wolf

| | |
|---|---|
| SEQ. ID. NO. 18089 | 5-AsnAlaPheArgArgHisArgArgArgGlnCysProAsnArgLysProAlaMet-22 |
| SEQ. ID. NO. 18090 | 51-ProLeuLysArgLysHisPhe-57 |
| SEQ. ID. NO. 18091 | 80-SerArgAlaGlyAlaValHisAspGlnGlyTrpGlu-91 |
| SEQ. ID. NO. 18092 | 114-TrpHisThrArgAsnArgGlu-120 |

Hydrophilic Regions - Hopp-Woods

| | |
|---|---|
| SEQ. ID. NO. 18093 | 5-AsnAlaPheArgArgHisArgArgArgGlnCysProAsnArgLysProAlaMet-22 |
| SEQ. ID. NO. 18094 | 51-ProLeuLysArgLysHisPhe-57 |
| SEQ. ID. NO. 18095 | 80-SerArgAlaGlyAlaValHis-86 | a268-1
AMPHI Regions - AMPHI

| | |
|---|---|
| SEQ. ID. NO. 18096 | 6-AspGlyLeuHisLysPheLysHisIleCysSerAlaAla-18 |
| SEQ. ID. NO. 18097 | 22-IleLysGluProLeuAspLys-28 |
| SEQ. ID. NO. 18098 | 52-GlnGluValAspArgValSerGluTrp-60 |
| SEQ. ID. NO. 18099 | 70-GluPheGluGlnPheTrpLysGlyLeuProGlnThrValGlnAsn-84 |
| SEQ. ID. NO. 18100 | 89-SerGlnLysThrTrpLysSerGlyMetAspLys-99 |
| SEQ. ID. NO. 18101 | 110-GluThrProAsnGlyIleLys-116 |

Antigenic Index - Jameson-Wolf

| | |
|---|---|
| SEQ. ID. NO. 18102 | 1-ValGlnSerArgTyrAspGly-7 |
| SEQ. ID. NO. 18103 | 21-LeuIleLysGluProLeuAspLysAlaLysGlnArgAsnGluGluLeuGluAlaAlaGluGluAlaAlaAla-44 |
| SEQ. ID. NO. 18104 | 47-AlaLeuGlyArgGluGlnGluValAspArgValSerGluTrpGluGluArgTyrLysLeuSerArgSerGluPhe-71 |
| SEQ. ID. NO. 18105 | 82-ValGlnAsnLysLeuGlnAlaSerGlnLysThrTrpLysSerGlyMetAspLysIleCysAlaAsnAsnAlaLysAlaGluGlyGluThrProAsnGly-114 |
| SEQ. ID. NO. 18106 | 119-GluLeuAlaCysLysThrAlaGluThrGluAlaArgLeuGluGluLeuHisAsnArgLysLysAlaLeuLeuAspGluMetAlaArgGluAlaAspLysLysGluLeuProLysArgLeu-158 |

Hydrophilic Regions - Hopp-Woods

| | |
|---|---|
| SEQ. ID. NO. 18107 | 3-SerArgTyrAspGly-7 |

TABLE 1-continued

| | |
|---|---|
| SEQ. ID. NO. 18108 | 21-LeuIleLysGluProLeuAspLysAlaLysGlnArgAsnGluGluLeuGluAlaAlaGluGluAlaAlaAla-44 |
| SEQ. ID. NO. 18109 | 47-AlaLeuGlyArgGluGlnGluValAspArgValSerGluTrpGluGluArgTyrLysLeuSerArgSerGluPhe-71 |
| SEQ. ID. NO. 18110 | 91-LysThrTrpLysSerGlyMetAspLysIleCys-101 |
| SEQ. ID. NO. 18111 | 104-AsnAlaLysAlaGluGlyGluThrProAsn-113 |
| SEQ. ID. NO. 18112 | 119-GluLeuAlaCysLysThrAlaGluThrGluAlaArgLeuGluGluLeuHisAsnArgLysLysAlaLeuLeuAspGluMetAlaArgGluAla AspLysLysGluLeuProLysArgLeu-158 | a269
AMPHI Regions - AMPHI
SEQ. ID. NO. 18113    54-TrpAspPheIleGlnAsnThr-60
SEQ. ID. NO. 18114    73-PheLysThrArgAlaLeuGlyArgPheSerSerPro-84
Antigenic Index - Jameson-Wolf
SEQ. ID. NO. 18115    42-ProAlaSerSerAla-46
SEQ. ID. NO. 18116    60-ThrAlaSerProLysValSer-66
SEQ. ID. NO. 18117    73-PheLysThrArgAlaLeuGlyArgPheSerSerPro-84
SEQ. ID. NO. 18118    90-LeuSerGlyArgGlyValLysLysProLeu-99
SEQ. ID. NO. 18119    107-GlnValAspThrSerAla-112
Hydrophilic Regions - Hopp-Woods
SEQ. ID. NO. 18120    61-AlaSerProLysVal-65
SEQ. ID. NO. 18121    73-PheLysThrArgAlaLeuGly-79
SEQ. ID. NO. 18122    93-ArgGlyValLysLysProLeu-99
a270
AMPHI Regions - AMPHI
SEQ. ID. NO. 18123    41-AspLeuThrGluGlyCys-46
SEQ. ID. NO. 18124    49-ProAspGlySerArg-53
SEQ. ID. NO. 18125    100-GlnProSerGlyThrTrp-105
Antigenic Index - Jameson-Wolf
SEQ. ID. NO. 18126    1-MetAsnLysAsnArgLysLeu-7
SEQ. ID. NO. 18127    41-AspLeuThrGluGlyCysThrLeuProAspGlySerArgValArgAlaAlaAlaValSerThrLysLysProPhe-65
SEQ. ID. NO. 18128    71-HisAlaProAlaGlyThrGlu-77
SEQ. ID. NO. 18129    86-LysAsnMetAspMetGlyPhe-92
SEQ. ID. NO. 18130    95-TyrMetPheArgGlnProSerGlyThr-104
SEQ. ID. NO. 18131    116-ValGluGlyArgArgAspPheThrAla-124
SEQ. ID. NO. 18132    128-IleGlySerArgThrPhe-133
Hydrophilic Regions - Hopp-Woods
SEQ. ID. NO. 18133    1-MetAsnLysAsnArgLysLeu-7
SEQ. ID. NO. 18134    49-ProAspGlySerArgValArgAla-56
SEQ. ID. NO. 18135    60-SerThrLysLysProPhe-65
SEQ. ID. NO. 18136    73-ProAlaGlyThrGlu-77
SEQ. ID. NO. 18137    96-MetPheGluArgGlnPro-101
SEQ. ID. NO. 18138    116-ValGluGlyArgArgAspPheThrAla-124
a271-2
AMPHI Regions - AMPHI
SEQ. ID. NO. 18139    6-MetAlaArgIleTrp-10
SEQ. ID. NO. 18140    20-SerProCysProAla-24
SEQ. ID. NO. 18141    29-ProLysSerLeuAlaLysCysAla-36
Antigenic Index - Jameson-Wolf
SEQ. ID. NO. 18142    26-ThrThrLysProLysSerLeuAlaLys-34
SEQ. ID. NO. 18143    41-ArgSerAsnCysLeu-45
SEQ. ID. NO. 18144    60-CysSerSerThrThrGlyAlaProThrSerArg-70
SEQ. ID. NO. 18145    78-SerAlaSerIleAsnLysAspThrArgMetProAlaSerVal-91
SEQ. ID. NO. 18146    102-CysCysAlaAsnThrSerLysProProSer-111
Hydrophilic Regions - Hopp-Woods
SEQ. ID. NO. 18147    27-ThrLysProLysSerLeuAla-33
SEQ. ID. NO. 18148    80-SerIleAsnLysAspThrArgMet-87
SEQ. ID. NO. 18149    105-AsnThrSerLysProPro-110
a272-2
AMPHI Regions - AMPHI
SEQ. ID. NO. 18150    44-IleThrArgIleThrAspGlu-50
SEQ. ID. NO. 18151    70-AlaGluGluPheSerSerThrAsn-77
SEQ. ID. NO. 18152    106-PheArgAlaIleThrSer-111
SEQ. ID. NO. 18153    165-IleIleThrIleGluAspProIleGlu-173
SEQ. ID. NO. 18154    194-AsnTrpMetAlaAlaLeuLysAsnThrLeuArgGlnAla-206
SEQ. ID. NO. 18155    244-AsnGlnAlaLeuAspArgIleIleAsn-252
SEQ. ID. NO. 18156    307-GlyAsnIleHisGluIleLysGluValMetLys-317
SEQ. ID. NO. 18157    328-AspGlnHisLeuTyrGln-333
SEQ. ID. NO. 18158    343-GlnAspAlaLeuLysAsnAlaAspSer-351
Antigenic Index - Jameson-Wolf
SEQ. ID. NO. 18159    2-PheThrAspGluAsnMetThrAlaLysGluGluLeu-13
SEQ. ID. NO. 18160    19-HisMetAsnLysAsnLysGlySerAsp-27
SEQ. ID. NO. 18161    38-MetLysLeuAspGlyLysIleThrArgIleThrAspGluProLeuThrAlaGluLysCysMet-58
SEQ. ID. NO. 18162    68-LysGlnAlaGluGluPheSerSerThrAsnGlu-78
SEQ. ID. NO. 18163    85-LeuProAspThrSerArgPheArgVal-93
SEQ. ID. NO. 18164    109-IleThrSerLysIleProLysPheGluSerLeuAsn-120
SEQ. ID. NO. 18165    128-ValAlaLeuLysLysArgGly-134
SEQ. ID. NO. 18166    142-ThrGlySerGlyLysSerThrSerLeu-150
SEQ. ID. NO. 18167    154-IleAspTyrArgAsnGluAsnSerPheGly-163
SEQ. ID. NO. 18168    168-IleGluAspProIle-172
SEQ. ID. NO. 18169    176-HisGluHisLysAsnCys-181
SEQ. ID. NO. 18170    184-ThrGlnArgGluValGlyValAspThrGluAsn-194
SEQ. ID. NO. 18171    199-LeuLysAsnThrLeuArgGlnAlaProAsp-208

TABLE 1-continued

| | |
|---|---|
| SEQ. ID. NO. 18172 | 214-GluIleArgAspArgGluThrMet-221 |
| SEQ. ID. NO. 18173 | 241-AsnSerThrAsnGlnAlaLeuAspArg-249 |
| SEQ. ID. NO. 18174 | 254-PheProGluGluArgArgGluGlnLeuLeu-263 |
| SEQ. ID. NO. 18175 | 278-LeuValProArgAspGlyGlyLysGlyArgValAlaAla-290 |
| SEQ. ID. NO. 18176 | 310-HisGluIleLysGluValMetLysLysSerThr-320 |
| SEQ. ID. NO. 18177 | 336-GluLysGlyGluIleSerLeu-342 |
| SEQ. ID. NO. 18178 | 344-AspAlaLeuLysAsnAlaAspSerAlaHisAspLeu-355 |
| SEQ. ID. NO. 18179 | 361-LeuArgSerArgGlnAlaGlnSerSerGlyProAspLeuGluLeuLeu-376 |

Hydrophilic Regions - Hopp-Woods

| | |
|---|---|
| SEQ. ID. NO. 18180 | 2-PheThrAspGluAsnMetThrAlaLysGluGluLeu-13 |
| SEQ. ID. NO. 18181 | 20-MetAsnLysAsnLysGlySerAsp-27 |
| SEQ. ID. NO. 18182 | 38-MetLysLeuAspGlyLysIleThrArgIleThrAspGluProLeuThrAlaGluLysCysMet-58 |
| SEQ. ID. NO. 18183 | 68-LysGlnAlaGluGluPheSerSer-75 |
| SEQ. ID. NO. 18184 | 87-AspThrSerArgPheArgVal-93 |
| SEQ. ID. NO. 18185 | 112-LysIleProLysPheGluSer-118 |
| SEQ. ID. NO. 18186 | 128-ValAlaLeuLysLysArgGly-134 |
| SEQ. ID. NO. 18187 | 143-GlySerGlyLysSerThrSer-149 |
| SEQ. ID. NO. 18188 | 155-AspTyrArgAsnGluAsnSer-161 |
| SEQ. ID. NO. 18189 | 168-IleGluAspProIle-172 |
| SEQ. ID. NO. 18190 | 176-HisGluHisLysAsn-180 |
| SEQ. ID. NO. 18191 | 184-ThrGlnArgGluValGlyValAspThr-192 |
| SEQ. ID. NO. 18192 | 201-AsnThrLeuArgGlnAlaPro-207 |
| SEQ. ID. NO. 18193 | 214-GluIleArgAspArgGluThrMet-221 |
| SEQ. ID. NO. 18194 | 245-GlnAlaLeuAspArg-249 |
| SEQ. ID. NO. 18195 | 255-ProGluGluArgArgGluGlnLeuLeu-263 |
| SEQ. ID. NO. 18196 | 278-LeuValProArgAspGlyGlyLysGlyArgValAlaAla-290 |
| SEQ. ID. NO. 18197 | 310-HisGluIleLysGluValMetLysLysSerThr-320 |
| SEQ. ID. NO. 18198 | 336-GluLysGlyGluIleSerLeu-342 |
| SEQ. ID. NO. 18199 | 344-AspAlaLeuLysAsnAlaAspSerAlaHisAspLeu-355 |
| SEQ. ID. NO. 18200 | 361-LeuArgSerArgGlnAlaGlnSerSerGlyProAspLeuGluLeu-375 | a274
AMPHI Regions - AMPHI

| | |
|---|---|
| SEQ. ID. NO. 18201 | 31-TyrLysAspGlyLys-35 |
| SEQ. ID. NO. 18202 | 111-GluAlaValPheLysThrLeuSerPro-119 |

Antigenic Index - Jameson-Wolf

| | |
|---|---|
| SEQ. ID. NO. 18203 | 25-LeuValThrAspAspTyrTyrLysAspGlyLysHisIleAsp-38 |
| SEQ. ID. NO. 18204 | 40-GlnLeuHisArgAspGluGluAlaValArgArgHisIle-52 |
| SEQ. ID. NO. 18205 | 60-ProAspMetAsnAla-64 |
| SEQ. ID. NO. 18206 | 71-GlyGluPheAspGlyLysGlnPro-78 |
| SEQ. ID. NO. 18207 | 85-HisProThrArgLysAlaAspAspGlnThrVal-95 |
| SEQ. ID. NO. 18208 | 99-ProValGlySerAlaGlnAsnGlyArgAlaGluTyr-110 |
| SEQ. ID. NO. 18209 | 117-LeuSerProThrAsnHis-122 |
| SEQ. ID. NO. 18210 | 126-ArgValGluAspAlaAlaGly-132 |
| SEQ. ID. NO. 18211 | 136-ValGluAsnLysTrpIleThrSerGlnGlyAsnAlaValAspLeuThrProMetAspLysLeuPheAsnAsnThrGluSerLys-163 |

Hydrophilic Regions - Hopp-Woods

| | |
|---|---|
| SEQ. ID. NO. 18212 | 29-AspTyrTyrLysAspGlyLysHisIleAsp-38 |
| SEQ. ID. NO. 18213 | 40-GlnLeuHisArgAspGluGluAlaValArgArgHisIle-52 |
| SEQ. ID. NO. 18214 | 72-GluPheAspGlyLysGln-77 |
| SEQ. ID. NO. 18215 | 86-ProThrArgLysAlaAspAspGlnThrVal-95 |
| SEQ. ID. NO. 18216 | 104-GlnAsnGlyArgAlaGluTyr-110 |
| SEQ. ID. NO. 18217 | 126-ArgValGluAspAlaAlaGly-132 |
| SEQ. ID. NO. 18218 | 151-ThrProMetAspLysLeuPheAsn-158 | a276
AMPHI Regions - AMPHI

| | |
|---|---|
| SEQ. ID. NO. 18219 | 9-MetMetArgSerAlaProSerMetValValArgArgTrpAlaThrMetMet-25 |
| SEQ. ID. NO. 18220 | 60-SerPheLysMetAlaArg-65 |
| SEQ. ID. NO. 18221 | 80-ProPheAspProMetGlyTrp-86 |
| SEQ. ID. NO. 18222 | 115-GlyArgLeuTyrArgThrPheSerAsn-123 |
| SEQ. ID. NO. 18223 | 164-ThrLysArgGlySerArgLeu-170 |
| SEQ. ID. NO. 18224 | 207-SerThrSerThrLeuArgLysLeuMetArgProSerThr-219 |

Antigenic Index - Jameson-Wolf

| | |
|---|---|
| SEQ. ID. NO. 18225 | 10-MetArgSerAlaProSerMetVal-17 |
| SEQ. ID. NO. 18226 | 29-PheSerIleArgArgSerSerAlaCysTrpThrArgArgSerAspSerLeuSer-46 |
| SEQ. ID. NO. 18227 | 52-SerSerAsnAsnAsnIle-57 |
| SEQ. ID. NO. 18228 | 67-MetAlaThrArgCysArgCysProProAspLysLeuLeuPro-80 |
| SEQ. ID. NO. 18229 | 82-AspProMetGlyTrp-86 |
| SEQ. ID. NO. 18230 | 88-SerProSerGlyAspAlaSerIleArg-96 |
| SEQ. ID. NO. 18231 | 103-TrpArgAlaAspArgThrSerAlaSerProAlaSerGlyArgLeuTyr-118 |
| SEQ. ID. NO. 18232 | 121-PheSerAsnArgValSerSerAsnArgAsnThrSerTrpGluThrArgAlaAsnTrpAlaArgArgGlnSerSerLeu-146 |
| SEQ. ID. NO. 18233 | 158-LeuProAlaAspGlySerThrLysArgGlySerArgLeuThrThr-172 |
| SEQ. ID. NO. 18234 | 176-ProLeuProGluArgProThrArgAlaThrArgSerProCysLeuMetSerArgLeuLysProSerArgAlaLeuMetProSerGluArgTyrSerThrSerThrLeuArgLysLeuMetArgProSerThrArgCysGlyAla-223 |
| SEQ. ID. NO. 18235 | 229-CysSerGlyGlyValSerArgAsnAlaHisThrProSerAlaAlaArgAsn-245 |

Hydrophilic Regions - Hopp-Woods

| | |
|---|---|
| SEQ. ID. NO. 18236 | 29-PheSerIleArgArgSerSer-35 |
| SEQ. ID. NO. 18237 | 38-TrpThrArgArgSerAspSerLeu-45 |
| SEQ. ID. NO. 18238 | 67-MetAlaThrArgCysArgCysProProAspLys-77 |
| SEQ. ID. NO. 18239 | 90-SerGlyAspAlaSerIleArg-96 |
| SEQ. ID. NO. 18240 | 104-ArgAlaAspArgThrSerAla-110 |

TABLE 1-continued

| | |
|---|---|
| SEQ. ID. NO. 18241 | 124-ArgValSerSerAsnArgAsnThrSerTrpGluThr-135 |
| SEQ. ID. NO. 18242 | 137-AlaAsnTrpAlaArgArgGlnSerSer-145 |
| SEQ. ID. NO. 18243 | 161-AspGlySerThrLysArgGlySerArg-169 |
| SEQ. ID. NO. 18244 | 176-ProLeuProGluArgProThrArgAlaThrArg-186 |
| SEQ. ID. NO. 18245 | 192-SerArgLeuLysProSerArg-198 |
| SEQ. ID. NO. 18246 | 200-LeuMetProSerGluArgTyrSer-207 |
| SEQ. ID. NO. 18247 | 210-ThrLeuArgLysLeuMetArgProSerThrArgCys-221 |
| SEQ. ID. NO. 18248 | 232-GlyValSerArgAsnAlaHis-238 | a277
AMPHI Regions - AMPHI

| | |
|---|---|
| SEQ. ID. NO. 18249 | 43-PheGluValValGlyGlyLeuPheAspPheValLeu-54 |
| SEQ. ID. NO. 18250 | 70-CysProAsnGluValIleAspValPheHisAlaLeuGln-82 |
| SEQ. ID. NO. 18251 | 87-AlaPheAspAlaValGlyAspPheAlaGluTyrGlyGlyAlaValAspAlaAlaAspLeuLeuGluIleGlyGluLeuGlyTyrPheHis-116 |
| SEQ. ID. NO. 18252 | 180-AlaValGlyValValAlaValAla-187 |

Antigenic Index - Jameson-Wolf

| | |
|---|---|
| SEQ. ID. NO. 18253 | 2-ProArgPheGluAspLysLeuValGlyArgGlnGlyGluGlyGlyVal-17 |
| SEQ. ID. NO. 18254 | 69-PheCysProAsnGluVal-74 |
| SEQ. ID. NO. 18255 | 95-AlaGluTyrGlyGly-99 |
| SEQ. ID. NO. 18256 | 118-ValGluProAspPheProAlaGlnThrProArgAlaGluGlyGly-132 |
| SEQ. ID. NO. 18257 | 138-PheAspLysAlaAsp-142 |
| SEQ. ID. NO. 18258 | 162-AspIleGlyGlySerGlyLeuGluGlyAspLeu-172 |
| SEQ. ID. NO. 18259 | 196-LeuAspValGlyGlyLysProArgLeuGlyAla-206 |
| SEQ. ID. NO. 18260 | 208-CysAlaGlnThrGlyGlyGlyMetGly-216 |
| SEQ. ID. NO. 18261 | 219-GlyThrAspPheHis-223 |
| SEQ. ID. NO. 18262 | 226-GlyLeuAspAspGlyAla-231 |
| SEQ. ID. NO. 18263 | 239-LeuGlnPheGluAspAspLeuLeuGluGlyLysHisGlyLeu-252 |

Hydrophilic Regions - Hopp-Woods

| | |
|---|---|
| SEQ. ID. NO. 18264 | 2-ProArgPheGluAspLysLeuValGlyArgGlnGlyGlu-14 |
| SEQ. ID. NO. 18265 | 118-ValGluProAspPhe-122 |
| SEQ. ID. NO. 18266 | 126-ThrProArgAlaGluGly-131 |
| SEQ. ID. NO. 18267 | 138-PheAspLysAlaAsp-142 |
| SEQ. ID. NO. 18268 | 167-GlyLeuGluGlyAspLeu-172 |
| SEQ. ID. NO. 18269 | 198-ValGlyGlyLysProArgLeuGlyAla-206 |
| SEQ. ID. NO. 18270 | 226-GlyLeuAspAspGlyAla-231 |
| SEQ. ID. NO. 18271 | 239-LeuGlnPheGluAspAspLeuLeuGluGlyLysHisGlyLeu-252 | a278
AMPHI Regions - AMPHI

| | |
|---|---|
| SEQ. ID. NO. 18272 | 7-GlyAlaIlePheSerIleGly-13 |
| SEQ. ID. NO. 18273 | 20-IleGlyProLeuProSerIleGlyArg-28 |
| SEQ. ID. NO. 18274 | 42-ThrGlyThrSerLys-46 |
| SEQ. ID. NO. 18275 | 101-ArgThrIleProSerValThrGluIle-109 |
| SEQ. ID. NO. 18276 | 123-PheSerIleLeuAlaLeuIleLysSerLeuIleSer-134 |
| SEQ. ID. NO. 18277 | 157-LeuTyrArgGlnIleGlnAsnLeuIleThrHisPheAsnPheTyrAlaAla-173 |
| SEQ. ID. NO. 18278 | 189-GluThrLeuIleGlnHisLeuArgGlnLeuAlaAsp-200 |

Antigenic Index - Jameson-Wolf

| | |
|---|---|
| SEQ. ID. NO. 18279 | 25-SerIleGlyArgProAsnAlaSerThrThrArgProThrSerSerArgProThrGlyThrSerLysIleArgPro-49 |
| SEQ. ID. NO. 18280 | 63-SerProAsnThrThrAlaProThrGluSerArgSerArgPheIleAla-78 |
| SEQ. ID. NO. 18281 | 80-ProLysValLeuProGlyAsnSerSerIle-89 |
| SEQ. ID. NO. 18282 | 93-IleAlaSerAspLysProTrpMetArg-101 |
| SEQ. ID. NO. 18283 | 110-ThrValProArgValArgThrSerAlaPheThrAspArgPheSer-124 |
| SEQ. ID. NO. 18284 | 146-ArgHisSerArgValGlnGlyThr-153 |
| SEQ. ID. NO. 18285 | 178-PheAspPheAspArgAspPhe-184 |
| SEQ. ID. NO. 18286 | 209-ThrValAsnAspGlyArgPheAspMetValGlu-219 |

Hydrophilic Regions - Hopp-Woods

| | |
|---|---|
| SEQ. ID. NO. 18287 | 27-GlyArgProAsnAlaSerThrThrArgProThrSerSerArgProThrGlyThrSerLysIleArgPro-49 |
| SEQ. ID. NO. 18288 | 68-AlaProThrGluSerArgSerArgPheIleAla-78 |
| SEQ. ID. NO. 18289 | 93-IleAlaSerAspLysProTrp-99 |
| SEQ. ID. NO. 18290 | 110-ThrValProArgValArgThr-116 |
| SEQ. ID. NO. 18291 | 146-ArgHisSerArgValGln-151 |
| SEQ. ID. NO. 18292 | 178-PheAspPheAspArgAspPhe-184 |
| SEQ. ID. NO. 18293 | 211-AsnAspGlyArgPheAspMetValGlu-219 | a279
AMPHI Regions - AMPHI

| | |
|---|---|
| SEQ. ID. NO. 18294 | 6-GlyCysLeuIleSer-10 |
| SEQ. ID. NO. 18295 | 47-AlaAlaSerIleAlaArgSerThrAla-55 |
| SEQ. ID. NO. 18296 | 58-LeuProAlaIleThrThr-63 |
| SEQ. ID. NO. 18297 | 74-ThrThrSerSerCysAlaAsp-80 |

Antigenic Index - Jameson-Wolf

| | |
|---|---|
| SEQ. ID. NO. 18298 | 13-XxxArgAlaSerAla-17 |
| SEQ. ID. NO. 18299 | 29-TrpGluGlyThrAspThrGlySerGlyArgAlaArgLeuAla-42 |
| SEQ. ID. NO. 18300 | 64-CysProGlyGluLeuLysLeuThr-71 |
| SEQ. ID. NO. 18301 | 74-ThrThrSerSerCysAlaAspSer-81 |
| SEQ. ID. NO. 18302 | 88-CysSerSerSerLysProArgIle-95 |
| SEQ. ID. NO. 18303 | 101-ThrProCysGlyThrAlaAspCysIleSerSerAlaArgXxxArgThrSerLeu-118 |
| SEQ. ID. NO. 18304 | 120-AlaSerAlaLysSerAsnAlaProAla-128 |
| SEQ. ID. NO. 18305 | 148-ProProAlaSerGlu-152 |

Hydrophilic Regions - Hopp-Woods

| | |
|---|---|
| SEQ. ID. NO. 18306 | 13-XxxArgAlaSerAla-17 |
| SEQ. ID. NO. 18307 | 29-TrpGluGlyThrAspThrGlySerGlyArgAlaArgLeuAla-42 |
| SEQ. ID. NO. 18308 | 66-GlyGluLeuLysLeu-70 |

TABLE 1-continued

| | |
|---|---|
| SEQ. ID. NO. 18309 | 89-SerSerSerLysProArgIle-95 |
| SEQ. ID. NO. 18310 | 110-SerSerAlaArgXxxArgThrSerLeu-118 |
| SEQ. ID. NO. 18311 | 120-AlaSerAlaLysSerAsnAla-126 | a280
AMPHI Regions - AMPHI

| | |
|---|---|
| SEQ. ID. NO. 18312 | 27-SerPheSerIleLeuGlyAspValAlaLys-36 |
| SEQ. ID. NO. 18313 | 64-AspIleLysLysIleArgSerAla-71 |
| SEQ. ID. NO. 18314 | 85-AspIleGlnArgAlaValLys-91 |
| SEQ. ID. NO. 18315 | 97-TyrAlaGluAlaThrLysGlyIleGlnProLeuLys-108 |
| SEQ. ID. NO. 18316 | 150-AlaTyrAlaGlnAsnValAlaGluAlaLeuIleLys-161 |
| SEQ. ID. NO. 18317 | 237-ValAlaAlaIleIleArgGlnIleLys-245 |
| SEQ. ID. NO. 18318 | 247-GluGlyIleLysAlaValPheThrGlu-255 |
| SEQ. ID. NO. 18319 | 258-LysAspThrArgMetValAspArgIleAlaLysGluThr-270 |
| SEQ. ID. NO. 18320 | 278-LeuTyrSerAspAlaLeuGlyAsnAlaProAlaAspThrTyrIle-292 |

Antigenic Index - Jameson-Wolf

| | |
|---|---|
| SEQ. ID. NO. 18321 | 1-MetLysHisProLys-5 |
| SEQ. ID. NO. 18322 | 38-IleGlyGlyGluArgValSer-44 |
| SEQ. ID. NO. 18323 | 51-AlaAsnGlnAspThrHis-56 |
| SEQ. ID. NO. 18324 | 61-ThrSerGlyAspIleLysLysIleArgSerAlaLys-72 |
| SEQ. ID. NO. 18325 | 82-GluAlaAlaAspIleGlnArgAlaValLysGlnSerLysValSerTyrAlaGluAlaThrLysGlyIleGln-105 |
| SEQ. ID. NO. 18326 | 107-LeuLysAlaGluGluGluGlyGlyHisHisHisAspHisAspHisAspHisAspHisAspHisGluGlyHisHisHisAspHisGlyGluTyrAsp ProHisValTrpAsnAspPro-145 |
| SEQ. ID. NO. 18327 | 159-LeuIleLysAlaAspProGluGlyLysValTyrTyr-170 |
| SEQ. ID. NO. 18328 | 180-GlnLeuLysLysLeuHisSerAspAla-188 |
| SEQ. ID. NO. 18329 | 196-ProAlaAlaLysArgLysValLeuThr-204 |
| SEQ. ID. NO. 18330 | 212-MetGlyLysArgTyrHis-217 |
| SEQ. ID. NO. 18331 | 222-AlaProGlnGlyValSerSerGluAlaGluProSerAlaLysGln-236 |
| SEQ. ID. NO. 18332 | 242-ArgGlnIleLysArgGluGlyIle-249 |
| SEQ. ID. NO. 18333 | 255-GluAsnIleLysAspThrArgMetValAspArgIleAlaLysGluThrGlyVal-272 |
| SEQ. ID. NO. 18334 | 274-ValSerGlyLysLeuTyrSer-280 |
| SEQ. ID. NO. 18335 | 286-AlaProAlaAspThr-290 |
| SEQ. ID. NO. 18336 | 295-TyrArgHisAsnIle-299 |

Hydrophilic Regions - Hopp-Woods

| | |
|---|---|
| SEQ. ID. NO. 18337 | 1-MetLysHisProLys-5 |
| SEQ. ID. NO. 18338 | 38-IleGlyGlyGluArgValSer-44 |
| SEQ. ID. NO. 18339 | 63-GlyAspIleLysLysIleArgSerAlaLys-72 |
| SEQ. ID. NO. 18340 | 82-GluAlaAlaAspIleGlnArgAlaValLysGlnSerLys-94 |
| SEQ. ID. NO. 18341 | 99-GluAlaThrLysGly-103 |
| SEQ. ID. NO. 18342 | 107-LeuLysAlaGluGluGluGlyGlyHisHisHisAspHisAspHisAspHisAspHisAspHisGluGlyHisHisHisAspHisGlyGluTyrAsp-138 |
| SEQ. ID. NO. 18343 | 159-LeuIleLysAlaAspProGluGly-166 |
| SEQ. ID. NO. 18344 | 180-GlnLeuLysLysLeuHisSerAspAla-188 |
| SEQ. ID. NO. 18345 | 196-ProAlaAlaLysArgLysValLeuThr-204 |
| SEQ. ID. NO. 18346 | 226-ValSerSerGluAlaGluProSerAlaLysGln-236 |
| SEQ. ID. NO. 18347 | 242-ArgGlnIleLysArgGluGlyIle-249 |
| SEQ. ID. NO. 18348 | 255-GluAsnIleLysAspThrArgMetValAspArgIleAlaLysGluThrGlyVal-272 | a281
AMPHI Regions - AMPHI

| | |
|---|---|
| SEQ. ID. NO. 18349 | 62-AlaAlaGlyMetLeuMetAlaLeuLeuAlaGlyLeuValSerArgPhe-77 |
| SEQ. ID. NO. 18350 | 126-LeuGlnLeuIleAlaAlaValSerThrLeuThr-136 |
| SEQ. ID. NO. 18351 | 140-LeuAlaValIleTyrArg-145 |
| SEQ. ID. NO. 18352 | 179-LeuValSerGlyPheGlnAlaLeuGlyThrLeuMetSerVal-192 |
| SEQ. ID. NO. 18353 | 205-TrpAlaLysHisMet-209 |
| SEQ. ID. NO. 18354 | 216-SerValLeuThrAlaLeuLeuCysGly-224 |

Antigenic Index - Jameson-Wolf

| | |
|---|---|
| SEQ. ID. NO. 18355 | 25-ArgArgMetSerLeu-29 |
| SEQ. ID. NO. 18356 | 78-ThrThrLeuLysGluAspAlaAsn-85 |
| SEQ. ID. NO. 18357 | 102-SerLysAsnGlySerSerVal-108 |
| SEQ. ID. NO. 18358 | 159-SerValGlyGlyLysGlyGly-165 |
| SEQ. ID. NO. 18359 | 236-IleProSerGlyPro-240 |
| SEQ. ID. NO. 18360 | 256-LeuGlyLysGluGlyGlyIle-262 |
| SEQ. ID. NO. 18361 | 266-TrpLeuLysAsnHisArgHisHisThrThr-275 |

Hydrophilic Regions - Hopp-Woods

| | |
|---|---|
| SEQ. ID. NO. 18362 | 25-ArgArgMetSerLeu-29 |
| SEQ. ID. NO. 18363 | 78-ThrThrLeuLysGluAspAlaAsn-85 |
| SEQ. ID. NO. 18364 | 103-LysAsnGlySerSer-107 |
| SEQ. ID. NO. 18365 | 256-LeuGlyLysGluGlyGlyIle-262 |
| SEQ. ID. NO. 18366 | 267-LeuLysAsnHisArgHisHisThr-274 | a282
AMPHI Regions - AMPHI

| | |
|---|---|
| SEQ. ID. NO. 18367 | 10-LeuIleValAlaPheLeuValLeuIleAsnProPheSerAlaLeu-24 |
| SEQ. ID. NO. 18368 | 50-ValPheAlaValIleAlaValPheAlaLeuIleGlyGlyThrLeu-64 |
| SEQ. ID. NO. 18369 | 111-ValArgProAlaArgAsn-116 |
| SEQ. ID. NO. 18370 | 176-ValSerArgLeuLeu-180 |
| SEQ. ID. NO. 18371 | 186-ThrIleLeuAsnArgIleMetGlyMet-194 |

Antigenic Index - Jameson-Wolf

| | |
|---|---|
| SEQ. ID. NO. 18372 | 31-ThrAsnGlyHisSerThrLysGluArgArgLysValAlaArg-44 |
| SEQ. ID. NO. 18373 | 92-AsnGlyAsnAspAsnProAlaLysGlnAsnLeuGlyAlaGlnProGluThrGlyGlnValArgProAlaArgAsnAlaGlyAla-119 |

Hydrophilic Regions - Hopp-Woods

| | |
|---|---|
| SEQ. ID. NO. 18374 | 34-HisSerThrLysGluArgArgLysValAlaArg-44 |
| SEQ. ID. NO. 18375 | 92-AsnGlyAsnAspAsnProAlaLysGlnAsnLeu-102 |

TABLE 1-continued

SEQ. ID. NO. 18376   104-AlaGlnProGluThrGlyGlnValArgProAlaArgAsn-116
a283
AMPHI Regions - AMPHI
SEQ. ID. NO. 18377   11-ThrLeuAlaSerPheLeuPro-17
SEQ. ID. NO. 18378   32-GlyGlyAsnSerTyrSerAspValProLysGlnLeuHis-44
SEQ. ID. NO. 18379   67-AlaAspAlaGlyLysArgThr-73
Antigenic Index - Jameson-Wolf
SEQ. ID. NO. 18380   28-TrpLysAspGlyGlyGlyAsnSerTyrSerAspValProLysGlnLeuHisProAspGlnSerGln-49
SEQ. ID. NO. 18381   53-LeuArgThrArgGlnThrLysProAlaValLysProAlaGlnAlaAspAlaGlyLysArgThrAspGlyAlaAlaGlnGluAsnAsnProAspThrAlaGlu
LysAsnArgGlnLeuGluGluGluLysLysArgIleAlaGluThrGluArgGlnAsnLysGluGluAsnCysArgIleSerLysMetAsnLeu-117
SEQ. ID. NO. 18382   121-GlyAsnSerAsnAlaLysAsnLysAspAspLeuIleArgLysTyrAsnAsnAlaValAsnLysTyrCysArg-144
Hydrophilic Regions - Hopp-Woods
SEQ. ID. NO. 18383   35-SerTyrSerAspValProLys-41
SEQ. ID. NO. 18384   43-LeuHisProAspGlnSerGln-49
(SEQ. ID. NO. 18381)
53-LeuArgThrArgGlnThrLysProAlaValLysProAlaGlnAlaAspAlaGlyLysArgThrAspGlyAlaAlaGlnGluAsnAsnProAspThrAlaGl
uLysAsnArgGlnLeuGluGluGluLysLysArgIleAlaGluThrGluArgGlnAsnLysGluGluAsnCysArgIleSerLysMetAsnLeu-117
SEQ. ID. NO. 18385   123-SerAsnAlaLysAsnLysAspAspLeuIleArgLysTyrAsn-136
a284
AMPHI Regions - AMPHI
SEQ. ID. NO. 18386   43-GluAlaPheAlaGlyPhePheGluThrVal-52
SEQ. ID. NO. 18387   61-ThrPheAlaAlaArgPhe-66
SEQ. ID. NO. 18388   125-ValAspPheAspValPhe-130
SEQ. ID. NO. 18389   154-ValValPheArgLeuPheArgGlnValValValAsp-165
SEQ. ID. NO. 18390   174-AspThrAlaCysGlyAsnValGlyGly-182
SEQ. ID. NO. 18391   187-AlaAlaAlaPheAlaGlnIleHisGln-195
SEQ. ID. NO. 18392   216-PheValGlnPheIleArgAspAspPheGlyHisGly-227
SEQ. ID. NO. 18393   277-PheArgValPheGlyGlnPheAlaArgGlnPheAla-288
SEQ. ID. NO. 18394   304-PheArgArgGlyPheAspAspGlyPheAspValValAspLys-317
SEQ. ID. NO. 18395   340-AlaAlaLeuHisGlnValHisGlnThrAla-349
SEQ. ID. NO. 18396   352-GlyAspAsnGlnIleAspArgPheAlaGln-361
SEQ. ID. NO. 18397   407-AlaArgAlaPheAlaArgPhePheAlaAlaPheGlyGlnSerLeuGlnSer-423
Antigenic Index - Jameson-Wolf
SEQ. ID. NO. 18398   1-MetProSerGluThrArgAsnArgPhe-9
SEQ. ID. NO. 18399   109-PheAspGlyGlnPhe-113
SEQ. ID. NO. 18400   132-HisPheGlyLysArgAsnArgAsnThrArgAla-142
SEQ. ID. NO. 18401   147-GlyAlaProAspAlaVal-152
SEQ. ID. NO. 18402   166-AsnValGlyAsnGlyArgTyrValAspThrAlaCysGlyAsnValGlyGlyAsnGlnAsn-185
SEQ. ID. NO. 18403   209-AlaValGlyGlyGlu-213
SEQ. ID. NO. 18404   219-PheIleArgAspAspPheGlyHisGlyPheGlyGlyArgGluAsnHisAla-235
SEQ. ID. NO. 18405   273-AspPheAspAspPheArg-278
SEQ. ID. NO. 18406   286-GlnPheAlaAspArgAlaValProSerGlyGlyGluGlnGlnSer-300
SEQ. ID. NO. 18407   303-ValPheArgArgGlyPheAspAspGlyPheAspValValAspLysAlaHis-319
SEQ. ID. NO. 18408   347-GlnThrAlaArgArgGlyAspAsnGlnIleAspArgPheAla-360
SEQ. ID. NO. 18409   362-GlyAlaGlyLeuValAlaGluArgCysThrThrAspAspAlaAspGlyThrGluProThr-381
SEQ. ID. NO. 18410   398-PheAlaGlyArgArgGlnHisGlnArgAlaArgAla-409
SEQ. ID. NO. 18411   419-GlnSerLeuGlnSerArg-424
Hydrophilic Regions - Hopp-Woods
SEQ. ID. NO. 18412   1-MetProSerGluThrArgAsnArgPhe-9
SEQ. ID. NO. 18413   134-GlyLysArgAsnArgAsnThrArgAla-142
SEQ. ID. NO. 18414   220-IleArgAspAspPheGly-225
SEQ. ID. NO. 18415   229-GlyGlyArgGluAsnHisAla-235
SEQ. ID. NO. 18416   286-GlnPheAlaAspArgAlaValProSerGlyGlyGluGlnGln-299
SEQ. ID. NO. 18417   306-ArgGlyPheAspAspGlyPheAspValValAspLysAlaHis-319
SEQ. ID. NO. 18418   347-GlnThrAlaArgArgGlyAspAsnGlnIleAspArgPheAla-360
SEQ. ID. NO. 18419   366-ValAlaGluArgCysThrThrAspAspAlaAspGlyThrGlu-379
SEQ. ID. NO. 18420   398-PheAlaGlyArgArgGlnHisGlnArgAlaArgAla-409
a285-1
AMPHI Regions - AMPHI
SEQ. ID. NO. 18421   15-ValCysPheLeuGly-19
SEQ. ID. NO. 18422   34-GlnIleProSerTrp-38
SEQ. ID. NO. 18423   50-GlyThrLeuLeuAspGlyPheAsp-57
SEQ. ID. NO. 18424   116-SerLeuProAspSerIleAspLeuPro-124
SEQ. ID. NO. 18425   208-HisSerThrAlaArg-212
SEQ. ID. NO. 18426   240-HisProPheAlaGluSerLeuAspLysThrLeuGluGluValLeu-254
SEQ. ID. NO. 18427   266-ValProSerLeuPro-270
SEQ. ID. NO. 18428   280-AlaIleProSerPheSerAsp-286
SEQ. ID. NO. 18429   313-GlnValLeuGlySer-317
SEQ. ID. NO. 18430   592-IleGlyLysAlaAlaAspIle-598
SEQ. ID. NO. 18431   609-ProAspThrSerArg-613
SEQ. ID. NO. 18432   629-GlyAlaGluValValAsp-634
SEQ. ID. NO. 18433   671-GlyIleAsnArgGluLeuThrArgTrp-679
SEQ. ID. NO. 18434   747-IleAlaGluLeuHisAsnPhePheLysProProPhe-758
SEQ. ID. NO. 18435   776-AlaArgGlyTyrLeu-780
SEQ. ID. NO. 18436   836-PheGlyGlyAsnMetAlaAsn-842
SEQ. ID. NO. 18437   848-ArgIleThrAlaSerLeuProAspLeuGlyThrLeu-859
SEQ. ID. NO. 18438   868-GlnAsnIleThrGlySerLeuAsnAlaAla-877
SEQ. ID. NO. 18439   955-GlySerIleAlaAsp-959
SEQ. ID. NO. 18440   1008-ThrAlaGluLeuSer-1012
SEQ. ID. NO. 18441   1061-ValThrGlyMetIleLys-1066

TABLE 1-continued

| SEQ. ID. NO. 18442 | 1135-SerGlyGlySerValArgGlyValGlyThrValArg-1146 |
|---|---|
| SEQ. ID. NO. 18443 | 1165-ThrValSerPheValGlyProLeuAsn-1173 |
| SEQ. ID. NO. 18444 | 1190-AlaGlyValGluIleLeuGlySerLeuAsn-1199 |
| SEQ. ID. NO. 18445 | 1244-LeuAlaGlyGlnIle-1248 |
| SEQ. ID. NO. 18446 | 1305-ValLysLeuIleTyrArgLeuThrArgAlaIleGlnAlaValAlaArgIleGlySer-1323 |

Antigenic Index - Jameson-Wolf

| SEQ. ID. NO. 18447 | 43-IleSerSerGlnAsnLeuLysGlyThrLeuLeuAspGlyPheAspGlyAspAsnTrpSerIleGluThrGluGlyAlaAspLeuLysIleSerArg-74 |
|---|---|
| SEQ. ID. NO. 18448 | 80-LysProSerGluLeuMetArgArgSerLeuHis-90 |
| SEQ. ID. NO. 18449 | 104-LysProThrProProLysGluGluArgProProLeuSerLeuProAspSerIleAsp-122 |
| SEQ. ID. NO. 18450 | 130-AspArgPheGluThrGlyLysIleSerMetGlyLysAlaPheAspLysGlnThrValTyr-149 |
| SEQ. ID. NO. 18451 | 151-GluArgLeuAspAlaSerTyrArgTyrAspArgLysGlyHisArgLeuAspLeuLysAlaAlaAspThrProTrpSerSerSerSerGlySerAla-182 |
| SEQ. ID. NO. 18452 | 185-GlyLeuLysLysProPheAla-191 |
| SEQ. ID. NO. 18453 | 198-ThrLysGlyGlyLeuGluGlyLysThrIle-207 |
| SEQ. ID. NO. 18454 | 209-SerThrAlaArgLeuSerGlySerLeuLysAspValArgAla-222 |
| SEQ. ID. NO. 18455 | 224-LeuAlaIleAspGlyGlyAsnIleArgLeuSerGlyLysSer-237 |
| SEQ. ID. NO. 18456 | 244-GluSerLeuAspLysThrLeuGlu-251 |
| SEQ. ID. NO. 18457 | 268-SerLeuProAspAla-272 |
| SEQ. ID. NO. 18458 | 292-GlySerLeuAspLeuGluAsnThrLys-300 |
| SEQ. ID. NO. 18459 | 302-GlyPheAlaAspArgAsnGlyIleProVal-311 |
| SEQ. ID. NO. 18460 | 320-IleArgGlnAspGlyThrValHis-327 |
| SEQ. ID. NO. 18461 | 337-GlyArgGlyGlyIleArgLeuSerGlyLysIleAspThrGluLysAspIleLeu-354 |
| SEQ. ID. NO. 18462 | 362-SerValGlyAlaGluAspValLeu-369 |
| SEQ. ID. NO. 18463 | 372-AlaPheLysGlyArgLeuAspGlySerIle-381 |
| SEQ. ID. NO. 18464 | 387-ThrAlaSerProLysIle-392 |
| SEQ. ID. NO. 18465 | 400-ThrAlaArgThrAspGlySerLeu-407 |
| SEQ. ID. NO. 18466 | 411-SerAspProAlaAsnGlyGlnArgLysLeuVal-421 |
| SEQ. ID. NO. 18467 | 430-GlyGlnGlySerLeuThr-435 |
| SEQ. ID. NO. 18468 | 442-LeuPheLysAspArgLeuLeuLysLeuAspIleArgSerArgAlaPheAspProSerArgIleAspProGlnLeu-466 |
| SEQ. ID. NO. 18469 | 480-GluLeuAlaLysGluLysPheThrGlyLys-489 |
| SEQ. ID. NO. 18470 | 508-IleValTyrGluSerArgHisLeuProArgAlaAlaVal-520 |
| SEQ. ID. NO. 18471 | 522-LeuArgLeuGlyArgAsnIleIleLysThrAspGlyGlyPheGlyLysLysGlyAspArgLeuAsn-543 |
| SEQ. ID. NO. 18472 | 548-AlaProAspLeuSerArgPheGly-555 |
| SEQ. ID. NO. 18473 | 563-AsnValArgGlyHisLeuSerGlyAspLeuAspGlyGlyIleArgThrPheGluThrAspLeuSerGlyAlaAla-587 |
| SEQ. ID. NO. 18474 | 594-LysAlaAlaAspIleArgSer-600 |
| SEQ. ID. NO. 18475 | 605-LeuLysGlySerProAspThrSerArgProIleArgAlaAspIleLysGlySerArgLeuSerLeuSerGlyGlyAlaGluValValAspThrAlaAspLeuMetLeuAspGlyThrGlyVal-645 |
| SEQ. ID. NO. 18476 | 647-HisArgIleArgThr-651 |
| SEQ. ID. NO. 18477 | 656-ThrLeuAspGlyLysProPheLysPheAspLeuAspAlaSerGlyGlyIleAsnArgGluLeuThrArgTrpLysGlySerIle-683 |
| SEQ. ID. NO. 18478 | 696-LeuGlnAsnArgMetThrLeu-702 |
| SEQ. ID. NO. 18479 | 704-AlaGlyAlaGluArgValAla-710 |
| SEQ. ID. NO. 18480 | 729-SerTrpAspLysLysThrGlyIleSerAlaLysGlyGlyAla-742 |
| SEQ. ID. NO. 18481 | 764-LeuAsnGlyAspTrp-768 |
| SEQ. ID. NO. 18482 | 772-TyrGlyArgAsnAlaArgGly-778 |
| SEQ. ID. NO. 18483 | 782-IleSerArgGlnSerGlyAspAlaValLeu-791 |
| SEQ. ID. NO. 18484 | 803-SerLeuLysThrArgPheGlnAsnAspArgIleGly-814 |
| SEQ. ID. NO. 18485 | 817-LeuAspGlyGlyAlaArgPheGlyArgIleAsnAlaAspLeuAspIle-832 |
| SEQ. ID. NO. 18486 | 844-ProLeuGlyGlyArgIleThr-850 |
| SEQ. ID. NO. 18487 | 882-GlyArgValGlySerProSerVal-889 |
| SEQ. ID. NO. 18488 | 893-ValAsnGlySerSerAsnTyrGlyLysIleAsnGly-904 |
| SEQ. ID. NO. 18489 | 908-ValGlyGlnSerArgSerPheAspThrAlaProLeuGlyGlyArgLeuAsn-924 |
| SEQ. ID. NO. 18490 | 941-GlnThrValLysGlySerLeu-947 |
| SEQ. ID. NO. 18491 | 956-SerIleAlaAspProHisLeuGlyGly-964 |
| SEQ. ID. NO. 18492 | 966-IleAsnGlyAspLysLeuTyrTyrArgAsnGlnThr-977 |
| SEQ. ID. NO. 18493 | 982-LeuAspAsnGlySerLeuArg-988 |
| SEQ. ID. NO. 18494 | 991-IleAlaGlyArgLysTrpVal-997 |
| SEQ. ID. NO. 18495 | 1001-LeuLysPheArgHisGluGlyThrAlaGluLeuSerGly-1013 |
| SEQ. ID. NO. 18496 | 1015-ValGlyMetGluAsnSerGlyProAspValAspIle-1026 |
| SEQ. ID. NO. 18497 | 1031-AspLysTyrArgIleLeuSerArgProAsnArgArgLeuThr-1044 |
| SEQ. ID. NO. 18498 | 1047-GlyAsnThrArgLeuArgTyrSerProGlnLysGlyIle-1059 |
| SEQ. ID. NO. 18499 | 1065-IleLysThrAspGlnGlyLeuPheGlySerGlnLysSerSerMetProSerValGlyAspAspVal-1086 |
| SEQ. ID. NO. 18500 | 1091-GluValLysLysGluAlaAla-1097 |
| SEQ. ID. NO. 18501 | 1109-AspLeuAsnAspGlyIleArg-1115 |
| SEQ. ID. NO. 18502 | 1134-GlnSerGlyGlySerValArgGlyValGly-1143 |
| SEQ. ID. NO. 18503 | 1146-ArgValIleLysGlyArgTyrLysAlaTyrGlyGlnAspLeuAspIleThrLysGlyThr-1165 |
| SEQ. ID. NO. 18504 | 1171-ProLeuAsnAspProAsnLeuAsnIleArgAlaGluArgArgLeuSerProValGly-1189 |
| SEQ. ID. NO. 18505 | 1197-SerLeuAsnSerProArgIle-1203 |
| SEQ. ID. NO. 18506 | 1207-AlaAsnGluProMetSerGluLysAspLysLeu-1217 |
| SEQ. ID. NO. 18507 | 1225-AlaGlySerGlySerSerGlyAspAsnAlaAla-1235 |
| SEQ. ID. NO. 18508 | 1246-GlyGlnIleAsnAspArgIleGlyLeu-1254 |
| SEQ. ID. NO. 18509 | 1256-AspAspLeuGlyPheThrSerLysArgSerArgAsnAlaGlnThrGlyGluLeuAsnProAlaGlu-1277 |
| SEQ. ID. NO. 18510 | 1283-GlyLysGlnLeuThrGlyLys-1289 |
| SEQ. ID. NO. 18511 | 1299-SerSerAlaGluGlnSerVal-1305 |
| SEQ. ID. NO. 18512 | 1321-IleGlySerArgSerSerGlyGlyGluLeu-1330 |
| SEQ. ID. NO. 18513 | 1335-ArgPheAspArgPheSerGlySerAspLysLysAspSerAlaGlyAsnSerLysGlyLys-1354 |

Hydrophilic Regions - Hopp-Woods

| SEQ. ID. NO. 18514 | 56-PheAspGlyAspAsnTrpSerIleGluThrGluGlyAlaAspLeuLysIleSerArg-74 |
|---|---|
| SEQ. ID. NO. 18515 | 83-GluLeuMetArgArgSerLeuHis-90 |
| SEQ. ID. NO. 18516 | 105-ProThrProProLysGluGluArgProPro-114 |
| SEQ. ID. NO. 18517 | 130-AspArgPheGluThrGlyLys-136 |
| SEQ. ID. NO. 18518 | 141-LysAlaPheAspLys-145 |

TABLE 1-continued

| | |
|---|---|
| SEQ. ID. NO. 18519 | 151-GluArgLeuAspAla-155 |
| SEQ. ID. NO. 18520 | 157-TyrArgTyrAspArgLysGlyHisArgLeuAspLeuLysAlaAlaAsp-172 |
| SEQ. ID. NO. 18521 | 200-GlyGlyLeuGluGlyLysThrIle-207 |
| SEQ. ID. NO. 18522 | 215-GlySerLeuLysAspValArgAla-222 |
| SEQ. ID. NO. 18523 | 244-GluSerLeuAspLysThrLeuGlu-251 |
| SEQ. ID. NO. 18524 | 292-GlySerLeuAspLeuGluAsnThrLys-300 |
| SEQ. ID. NO. 18525 | 302-GlyPheAlaAspArgAsnGlyIlePro-310 |
| SEQ. ID. NO. 18526 | 320-IleArgGlnAspGly-324 |
| SEQ. ID. NO. 18527 | 343-LeuSerGlyLysIleAspThrGluLysAspIleLeu-354 |
| SEQ. ID. NO. 18528 | 364-GlyAlaGluAspValLeu-369 |
| SEQ. ID. NO. 18529 | 373-PheLysGlyArgLeuAspGly-379 |
| SEQ. ID. NO. 18530 | 401-AlaArgThrAspGly-405 |
| SEQ. ID. NO. 18531 | 412-AspProAlaAsnGlyGlnArgLysLeuVal-421 |
| SEQ. ID. NO. 18532 | 442-LeuPheLysAspArgLeuLeuLysLeuAspIleArgSerArgAlaPheAspProSerArgIleAspPro-464 |
| SEQ. ID. NO. 18533 | 480-GluLeuAlaLysGluLysPheThrGly-488 |
| SEQ. ID. NO. 18534 | 508-IleValTyrGluSerArgHisLeuPro-516 |
| SEQ. ID. NO. 18535 | 522-LeuArgLeuGlyArgAsnIleIleLysThrArgSerGlyGlyPheGlyLysLysGlyAspArgLeuAsn-543 |
| SEQ. ID. NO. 18536 | 570-GlyAspLeuAspGlyGlyIleArgThrPheGluThrAspLeuSerGlyAlaAla-587 |
| SEQ. ID. NO. 18537 | 594-LysAlaAlaAspIleArgSer-600 |
| SEQ. ID. NO. 18538 | 607-GlySerProAspThrSerArgProIleArgAlaAspIleLysGlySerArgLeuSerLeu-626 |
| SEQ. ID. NO. 18539 | 631-GluValValAspThrAlaAspLeuMetLeu-640 |
| SEQ. ID. NO. 18540 | 647-HisArgIleArgThr-651 |
| SEQ. ID. NO. 18541 | 657-LeuAspGlyLysProPheLysPheAspLeuAspAla-668 |
| SEQ. ID. NO. 18542 | 670-GlyGlyIleAsnArgGluLeuThrArgTrpLysGly-681 |
| SEQ. ID. NO. 18543 | 704-AlaGlyAlaGluArgValAla-710 |
| SEQ. ID. NO. 18544 | 729-SerTrpAspLysLysThrGlyIleSerAlaLysGlyGlyAla-742 |
| SEQ. ID. NO. 18545 | 783-SerArgGlnSerGly-787 |
| SEQ. ID. NO. 18546 | 806-ThrArgPheGlnAsnAspArgIle-813 |
| SEQ. ID. NO. 18547 | 819-GlyGlyAlaArgPheGlyArgIleAsnAlaAspLeuAspIle-832 |
| SEQ. ID. NO. 18548 | 1001-LeuLysPheArgHisGluGlyThrAlaGluLeu-1011 |
| SEQ. ID. NO. 18549 | 1017-MetGluAsnSerGlyProAspValAspIle-1026 |
| SEQ. ID. NO. 18550 | 1031-AspLysTyrArgIleLeuSerArgProAsnArgArgLeuThr-1044 |
| SEQ. ID. NO. 18551 | 1049-ThrArgLeuArgTyrSerPro-1055 |
| SEQ. ID. NO. 18552 | 1065-IleLysThrAspGln-1069 |
| SEQ. ID. NO. 18553 | 1075-GlnLysSerSerMet-1079 |
| SEQ. ID. NO. 18554 | 1091-GluValLysLysGluAlaAla-1097 |
| SEQ. ID. NO. 18555 | 1109-AspLeuAsnAspGlyIleArg-1115 |
| SEQ. ID. NO. 18556 | 1146-ArgValIleLysGlyArgTyrLysAlaTyrGlyLysGlnAspLeuAspIleThrLys-1163 |
| SEQ. ID. NO. 18557 | 1179-IleArgAlaGluArgArgLeuSer-1186 |
| SEQ. ID. NO. 18558 | 1209-GluProMetSerGluLysAspLysLeu-1217 |
| SEQ. ID. NO. 18559 | 1225-AlaGlySerGlySerSerGlyAspAsnAlaAla-1235 |
| SEQ. ID. NO. 18560 | 1248-IleAsnAspArgIleGlyLeu-1254 |
| SEQ. ID. NO. 18561 | 1259-GlyPheThrSerLysArgSerArgAsnAlaGlnThrGlyGluLeuAsnPro-1275 |
| SEQ. ID. NO. 18562 | 1300-SerAlaGluGlnSerVal-1305 |
| SEQ. ID. NO. 18563 | 1321-IleGlySerArgSerSerGlyGly-1328 |
| SEQ. ID. NO. 18564 a286 | 1335-ArgPheAspArgPheSerGlySerAspLysLysAspSerAlaGlyAsnSerLysGlyLys-1354 |
| AMPHI Regions - AMPHI | |
| SEQ. ID. NO. 18565 | 69-GluIleLysAspMetVal-74 |
| SEQ. ID. NO. 18566 | 102-ProAspAsnValLysThr-107 |
| SEQ. ID. NO. 18567 | 145-ValAlaAlaIleLeuGlyAsp-150 |
| SEQ. ID. NO. 18568 | 157-LeuAlaGluTyrTyrArgAsnAlaLeuGluAsnTrpGlnGlnProValGlySer-174 |
| SEQ. ID. NO. 18569 | 198-ProLeuAlaLysLeuGlyAsn-204 |
| SEQ. ID. NO. 18570 | 238-ThrGlnArgTyrProGluGlnIleValSerGlyLeuAlaArgPheGlnProGlyThr-256 |
| SEQ. ID. NO. 18571 | 326-AspTyrTyrAsnLeuPheAsnLys-333 |
| SEQ. ID. NO. 18572 | 354-11eSerGlnProArg-358 |
| SEQ. ID. NO. 18573 | 375-ThrThrGlnAsnLeu-379 |
| SEQ. ID. NO. 18574 | 428-ThrAlaSerTrpLysArgGlnLeuLeu-436 |
| SEQ. ID. NO. 18575 | 455-ThrLeuGlyAlaPhe-459 |
| SEQ. ID. NO. 18576 | 513-GlyAlaSerSerVal-517 |
| SEQ. ID. NO. 18577 | 555-LeuSerGlyAlaValPheHisAspMetGlyAspAlaAlaAlaAsn-569 |
| SEQ. ID. NO. 18578 | 584-ArgTrpPheSerProLeu-589 |
| Antigenic Index - Jameson-Wolf | |
| SEQ. ID. NO. 18579 | 1-MetHisAspThrArgThrMetMet-8 |
| SEQ. ID. NO. 18580 | 30-AlaAspLeuSerGluAsnLysAla-37 |
| SEQ. ID. NO. 18581 | 43-PheLysAsnLysSerProAspThrGluSerValLysLeuLysProLysPheProVal-61 |
| SEQ. ID. NO. 18582 | 63-IleAspThrGlnAspSerGluIleLysAspMetValGluGluHisLeu-78 |
| SEQ. ID. NO. 18583 | 83-GlnGlnGlnGluGluValLeuAspLysGluGlnThr-94 |
| SEQ. ID. NO. 18584 | 97-LeuAlaGluGluAlaProAspAsnValLysThrMetLeuArgSerLysGlyTyrPheSerSerLysValSerLeuThrGluLysAspGlyAla-127 |
| SEQ. ID. NO. 18585 | 133-ThrProGlyProArgThrLysIle-140 |
| SEQ. ID. NO. 18586 | 151-IleLeuSerAspGlyAsnLeuAlaGluTyrTyrArgAsnAlaLeuGluAsnTrpGln-169 |
| SEQ. ID. NO. 18587 | 172-ValGlySerAspPheAspGlnAspSerTrpGluAsnSerLysThrSerVal-188 |
| SEQ. ID. NO. 18588 | 192-ValThrArgLysAlaTyrPro-198 |
| SEQ. ID. NO. 18589 | 201-LysLeuGlyAsnThrArgAlaAlaValAsnProAspThrAlaThrAla-216 |
| SEQ. ID. NO. 18590 | 223-AspSerGlyArgProIleAla-229 |
| SEQ. ID. NO. 18591 | 234-GluIleThrGlyThrGlnArgTyrProGluGlnIle-245 |
| SEQ. ID. NO. 18592 | 252-PheGlnProGlyThrProTyrAspLeu-260 |
| SEQ. ID. NO. 18593 | 270-LeuGluGlnAsnGlyHisTyrSerGly-278 |
| SEQ. ID. NO. 18594 | 283-AlaAspPheAspArgLeuGlnGlyAspArgValProVal-295 |
| SEQ. ID. NO. 18595 | 298-SerValThrGluValLysArgHisLysLeuGluThrGlyIleArgLeuAspSerGluTyrGlyLeuGlyGly-321 |

TABLE 1-continued

| | |
|---|---|
| SEQ. ID. NO. 18596 | 342-AspMetAspLysTyrGluThr-348 |
| SEQ. ID. NO. 18597 | 355-SerGlnProArgAsnTyrArgGlyAsnTyrTrp-365 |
| SEQ. ID. NO. 18598 | 368-AsnValSerTyrAsnArgSerThrThrGlnAsnLeuGluLysArgAlaPheSerGlyGly-387 |
| SEQ. ID. NO. 18599 | 391-ValArgAspArgAlaGlyIleAspAlaArgLeuGly-402 |
| SEQ. ID. NO. 18600 | 405-PheLeuAlaGluGlyArgLysIleProGlySerAspIleAspLeuGlyAsnSerHisAla-424 |
| SEQ. ID. NO. 18601 | 430-SerTrpLysArgGlnLeu-435 |
| SEQ. ID. NO. 18602 | 441-HisProGluAsnGlyHisTyrLeuAspGlyLysIle-452 |
| SEQ. ID. NO. 18603 | 468-ThrSerAlaArgAlaGly-473 |
| SEQ. ID. NO. 18604 | 476-PheThrProGluAsnLysLysLeu-483 |
| SEQ. ID. NO. 18605 | 496-ValAlaArgAspAsnAlaAsnValPro-504 |
| SEQ. ID. NO. 18606 | 509-PheArgSerGlyGlyAlaSerSerValArgGlyTyrGluLeuAspSer-524 |
| SEQ. ID. NO. 18607 | 534-ValLeuProGluArgAlaLeu-540 |
| SEQ. ID. NO. 18608 | 562-AspMetGlyAspAla-566 |
| SEQ. ID. NO. 18609 | 568-AlaAsnPheLysArgMetLysLeuLysHisGlySerGlyLeu-581 |
| SEQ. ID. NO. 18610 | 598-TyrGlyHisSerAspLysLysIleArg-606 |
| Hydrophilic Regions - Hopp-Woods | |
| SEQ. ID. NO. 18611 | 1-MetHisAspThrArgThrMetMet-8 |
| SEQ. ID. NO. 18612 | 30-AlaAspLeuSerGluAsnLysAla-37 |
| SEQ. ID. NO. 18613 | 44-LysAsnLysSerProAspThrGluSerValLysLeuLysProLysPheProVal-61 |
| SEQ. ID. NO. 18614 | 63-IleAspThrGlnAspSerGluIleLysAspMetValGluGluHisLeu-78 |
| SEQ. ID. NO. 18615 | 84-GlnGlnGluGluValLeuAspLysGluGlnThr-94 |
| SEQ. ID. NO. 18616 | 97-LeuAlaGluGluAlaProAspAsnValLysThrMetLeuArgSer-111 |
| SEQ. ID. NO. 18617 | 119-ValSerLeuThrGluLysAspGlyAla-127 |
| SEQ. ID. NO. 18618 | 134-ProGlyProArgThrLysIle-140 |
| SEQ. ID. NO. 18619 | 174-SerAspPheAspGlnAspSerTrpGluAsnSerLysThr-186 |
| SEQ. ID. NO. 18620 | 192-ValThrArgLysAlaTyrPro-198 |
| SEQ. ID. NO. 18621 | 206-ArgAlaAlaValAsnProAspThrAlaThr-215 |
| SEQ. ID. NO. 18622 | 239-GlnArgTyrProGlu-243 |
| SEQ. ID. NO. 18623 | 283-AlaAspPheAspArgLeuGlnGlyAspArgValProVal-295 |
| SEQ. ID. NO. 18624 | 298-SerValThrGluValLysArgHisLysLeuGluThrGlyIleArgLeuAspSerGluTyr-317 |
| SEQ. ID. NO. 18625 | 342-AspMetAspLysTyrGluThr-348 |
| SEQ. ID. NO. 18626 | 373-ArgSerThrThrGlnAsnLeuGluLysArgAlaPhe-384 |
| SEQ. ID. NO. 18627 | 392-ArgAspArgAlaGlyIleAspAlaArgLeuGly-402 |
| SEQ. ID. NO. 18628 | 405-PheLeuAlaGluGlyArgLysIleProGlySerAspIleAspLeu-419 |
| SEQ. ID. NO. 18629 | 478-ProGluAsnLysLysLeu-483 |
| SEQ. ID. NO. 18630 | 496-ValAlaArgAspAsnAlaAsn-502 |
| SEQ. ID. NO. 18631 | 518-ArgGlyTyrGluLeuAspSer-524 |
| SEQ. ID. NO. 18632 | 534-ValLeuProGluArgAlaLeu-540 |
| SEQ. ID. NO. 18633 | 562-AspMetGlyAspAla-566 |
| SEQ. ID. NO. 18634 | 568-AlaAsnPheLysArgMetLysLeuLysHis-577 |
| SEQ. ID. NO. 18635 | 600-HisSerAspLysLysIleArg-606 |
| a287 | |
| AMPHI Regions - AMPHI | |
| SEQ. ID. NO. 18636 | 29-LysSerAlaAspThrLeuSerLysProAlaAla-39 |
| SEQ. ID. NO. 18637 | 77-GlyGlyGlnAspMet-81 |
| SEQ. ID. NO. 18638 | 109-AsnAspMetProGlnAsn-114 |
| SEQ. ID. NO. 18639 | 131-MetProThrArgAspMetGlyAsnGlnAlaProAspAlaGlyGluSerAlaGlnProAlaAsnGlnProAspMetAlaAsnAlaAlaAspGlyMet-162 |
| SEQ. ID. NO. 18640 | 171-GluAsnAlaGlyAsnThrAlaAspGlnAlaAlaAsnGlnAlaGluAsn-186 |
| SEQ. ID. NO. 18641 | 192-SerGlnAsnProAla-196 |
| SEQ. ID. NO. 18642 | 206-GlyGlySerAspPhe-210 |
| SEQ. ID. NO. 18643 | 213-IleAsnValAlaAsnGly-218 |
| SEQ. ID. NO. 18644 | 256-LeuSerAspGluGluLysIleAsnLysTyrLysLys-267 |
| SEQ. ID. NO. 18645 | 306-PheArgArgSerAlaArg-311 |
| SEQ. ID. NO. 18646 | 419-LysSerValAspGlyIleIleAspSer-427 |
| SEQ. ID. NO. 18647 | 447-PheLysGlyThrTrpThr-452 |
| SEQ. ID. NO. 18648 | 459-ValSerGlyArgPheTyr-464 |
| Antigenic Index - Jameson-Wolf | |
| SEQ. ID. NO. 18649 | 17-AlaCysGlyGlyGlyGlyGlyGlySerProAspValLysSerAlaAspThrLeuSerLysProAla-38 |
| SEQ. ID. NO. 18650 | 42-ValThrGluAspValGlyGluGluValLeuProLysGluLysLysAspGluGluAlaValSerGlyAlaProGlnAlaAspThrGlnAspAlaThrAlaGlyLysGlyGlyGlnAspMet-81 |
| SEQ. ID. NO. 18651 | 85-SerAlaGluAsnThrGlyAsnGlyGlyAlaAlaThrThrAspAsnProGluAsnLysAspGluGlyProGlnAsnAspMetProGlnAsnAlaAlaAspThrAspSerSerThrProAsnHisThrProAlaProAsnMetProThrArgAspMetGlyAsnGlnAlaProAspAlaGlyGluSerAlaGlnProAlaAsnGlnProAspMetAlaAsnAlaAlaAspGlyMetGlnGlyAspAsnProSerAlaGlyGluAsnAlaGlyAsnThrAlaAspGlnAlaAlaAsnGlnAlaGluAsnGlnValGlyGlySerGlnAsnProAlaSerSerThrAsnProAsnAlaThrAsnGlyGlySerAspPheGlyArg-212 |
| SEQ. ID. NO. 18652 | 214-AsnValAlaAsnGlyIleLysLeuAspSerGlySerGluAsnVal-228 |
| SEQ. ID. NO. 18653 | 232-HisCysLysAspLysValCysAspArgAspPheLeuAspGluGluAlaProProLysSerGluPheGluLysLeuSerAspGluGluLysIleAsnLysTyrLysLysAspGluGlnArgGluAsnPhe-274 |
| SEQ. ID. NO. 18654 | 278-ValAlaAsnArgValGluLysAsnGlyThrAsnLys-289 |
| SEQ. ID. NO. 18655 | 293-IleTyrLysAspLysSerAlaSerSerSerAlaArgPheArgArgSerAlaArgSerArgArgSerLeuProAla-318 |
| SEQ. ID. NO. 18656 | 332-IleValAspGlyGluAla-337 |
| SEQ. ID. NO. 18657 | 342-GlyHisSerGlyAsn-346 |
| SEQ. ID. NO. 18658 | 349-AlaProGluGlyAsnTyrArgTyrLeu-357 |
| SEQ. ID. NO. 18659 | 360-GlyAlaGluLysLeuSerGlyGlySer-368 |
| SEQ. ID. NO. 18660 | 374-GlnGlyGluProAlaLysGlyGluMet-382 |
| SEQ. ID. NO. 18661 | 397-HisMetGluAsnGlyArgProSerProGlyGlyArgPheAlaAla-412 |
| SEQ. ID. NO. 18662 | 414-ValAspPheGlySerLysSerValAspGlyIleIleAspSerGlyAspAspLeuHisMetGlyThrGlnLysPhe-438 |
| SEQ. ID. NO. 18663 | 442-IleAspGlyAsnGlyPheLysGlyThrTrpThrGluAsnGlyGlyGlyAspValSerGly-461 |
| SEQ. ID. NO. 18664 | 463-PheTyrGlyProAlaGlyGluGluValAlaGlyLysTyrSerTyrArgProThrAspAlaGluLysGlyGlyPhe-487 |
| SEQ. ID. NO. 18665 | 491-AlaGlyLysLysGluGlnAsp-497 |

TABLE 1-continued

Hydrophilic Regions - Hopp-Woods
SEQ. ID. NO. 18666   22-GlyGlyGlySerProAspValLysSerAlaAspThrLeuSerLysProAla-38
SEQ. ID. NO. 18667   42-ValThrGluAspValGlyGluGluValLeuProLysGluLysLysAspGluGluAlaValSer-62
SEQ. ID. NO. 18668   65-ProGlnAlaAspThrGlnAspAlaThrAlaGlyLysGlyGlyGlnAsp-80
SEQ. ID. NO. 18669   85-SerAlaGluAsnThrGly-90
SEQ. ID. NO. 18670   95-AlaThrThrAspAsnProGluAsnLysAspGluGlyProGlnAsnAspMetProGlnAsnAlaAlaAspThrAspSerSerThr-122
SEQ. ID. NO. 18671   131-MetProThrArgAspMetGlyAsnGlnAlaProAspAlaGlyGluSerAlaGln-148
SEQ. ID. NO. 18672   151-AsnGlnProAspMetAlaAsnAlaAlaAspGlyMetGlnGlyAspAspProSerAlaGlyGluAsnAlaGlyAsnThrAlaAspGlnAlaAlaAsnGln
                     AlaGluAsnAsnGln-188
SEQ. ID. NO. 18673   193-GlnAsnProAlaSer-197
SEQ. ID. NO. 18674   206-GlyGlySerAspPheGlyArg-212
SEQ. ID. NO. 18675   219-IleLysLeuAspSerGlySerGlu-226
SEQ. ID. NO. 18676   232-HisCysLysAspLysValCysAspArgAspPheLeuAspGluGluAlaProProLysSerGluPheGluLysLeuSerAspGluGluLysIleAsnLys
                     TyrLysLysAspGluGlnArgGluAsnPhe-274
SEQ. ID. NO. 18677   278-ValAlaAspArgValGluLysAsnGlyThr-287
SEQ. ID. NO. 18678   294-TyrLysAspLysSerAlaSerSerSerSerAlaArgPheArgArgSerAlaArgSerArgArgSerLeuPro-317
SEQ. ID. NO. 18679   332-IleValAspGlyGluAla-337
SEQ. ID. NO. 18680   360-GlyAlaGluLysLeuSer-365
SEQ. ID. NO. 18681   374-GlnGlyGluProAlaLysGlyGluMet-382
SEQ. ID. NO. 18682   399-GluAsnGlyArgProSerProSerGlyGly-408
SEQ. ID. NO. 18683   414-ValAspPheGlySerLysSerValAspGlyIleIleAspSerGlyAspAspLeuHis-432
SEQ. ID. NO. 18684   455-GlyGlyGlyAspValSer-460
SEQ. ID. NO. 18685   467-AlaGlyGluGluValAlaGly-473
SEQ. ID. NO. 18686   475-TyrSerTyrArgProThrAspAlaGluLysGlyGly-486
SEQ. ID. NO. 18687   491-AlaGlyLysLysGluGlnAsp-497
a288
AMPHI Regions - AMPHI
SEQ. ID. NO. 18688   7-ValSerArgValLeu-11
SEQ. ID. NO. 18689   54-IleValThrLysCysAla-59
SEQ. ID. NO. 18690   61-ArgProTyrArgThrPheSerProLeuProVal-71
SEQ. ID. NO. 18691   97-HisSerThrLeuArg-101
SEQ. ID. NO. 18692   150-AlaLeuPheGlnAlaGlyPheAspLysAlaValGln-161
Antigenic Index - Jameson-Wolf
SEQ. ID. NO. 18693   2-HisThrGlyGlnAla-6
SEQ. ID. NO. 18694   28-AsnLeuProGluArgSerAlaGlySer-36
SEQ. ID. NO. 18695   58-CysAlaValArgProTyrArgThrPheSerPro-68
SEQ. ID. NO. 18696   72-LeuProLysGlnProSerAla-78
SEQ. ID. NO. 18697   89-LeuProArgProAlaValAsnArgHisSerThrLeuArgSerProAspPheProProArgMet-109
SEQ. ID. NO. 18698   113-IleArgGlyAspCysLeuPro-119
SEQ. ID. NO. 18699   126-IleIleThrArgAsnAlaLysMetProSerGluThrValGlnValSerAspGlyIleGlnProLys-147
SEQ. ID. NO. 18700   155-GlyPheAspLysAlaVal-160
Hydrophilic Regions - Hopp-Woods
SEQ. ID. NO. 18701   28-AsnLeuProGluArgSerAla-34
SEQ. ID. NO. 18702   58-CysAlaValArgPro-62
SEQ. ID. NO. 18703   98-SerThrLeuArgSerProAspPheProPro-107
SEQ. ID. NO. 18704   113-IleArgGlyAspCys-117
SEQ. ID. NO. 18705   126-IleIleThrArgAsnAlaLysMetProSerGluThrValGlnVal-140
SEQ. ID. NO. 18706   155-GlyPheAspLysAlaVal-160
a292
AMPHI Regions - AMPHI
SEQ. ID. NO. 18707   7-LysIleLeuThrProPheThrValLeuProLeu-17
SEQ. ID. NO. 18708   40-GlyLysSerValAla-44
SEQ. ID. NO. 18709   62-ValLeuSerValSerGlu-67
SEQ. ID. NO. 18710   69-ProValLysGlyIleTyrGlu-75
SEQ. ID. NO. 18711   110-GluArgAlaAlaAspLeu-115
SEQ. ID. NO. 18712   124-ProLeuAspLysAlaIleLysGluValArgGly-134
SEQ. ID. NO. 18713   150-PheCysLysArgLeuGluHisGluPheGluLysMetThrAspValThr-165
SEQ. ID. NO. 18714   195-LysAlaTrpThrAspTrpMetArg-202
SEQ. ID. NO. 18715   212-IleCysAspAsnProVal-217
Antigenic Index - Jameson-Wolf
SEQ. ID. NO. 18716   1-MetLysThrLysLeu-5
SEQ. ID. NO. 18717   23-ThrProValSerAsnAlaAsnAlaGluProAlaValLysAlaGluSerAlaGlyLysSerVal-43
SEQ. ID. NO. 18718   47-LeuLysAlaArgLeuGluLysThrTyrSerAlaGlnAspLeuLys-61
SEQ. ID. NO. 18719   66-SerGluThrProValLysGlyIle-73
SEQ. ID. NO. 18720   85-TyrThrAspAlaGluGlyGlyTyr-92
SEQ. ID. NO. 18721   99-IleAsnIleAspThrArgLysAsnLeuThrGluGluArgAlaAlaAspLeuAsnLys-117
SEQ. ID. NO. 18722   124-ProLeuAspLysAlaIleLysGluValArgGlyAsnGlyLysLeuLysVal-140
SEQ. ID. NO. 18723   142-ValPheSerAspProAspCysProPhe-150
SEQ. ID. NO. 18724   152-LysArgLeuGluHisGluPheGluLysMetThrAsp-163
SEQ. ID. NO. 18725   177-HisProAspAlaAlaArgLysAla-184
SEQ. ID. NO. 18726   189-CysGlnProAspArgAlaLysAla-196
SEQ. ID. NO. 18727   200-TrpMetArgLysGlyLysPheProVal-208
SEQ. ID. NO. 18728   210-GlySerIleCysAspAsnProValAlaGluThrThrSerLeuGlyGlu-225
SEQ. ID. NO. 18729   237-PheProAsnGlyArgSerGlnSerGlyTyrSerPro-248
SEQ. ID. NO. 18730   250-ProGlnLeuGluGluIleIleArgLysAsnGln-260
Hydrophilic Regions - Hopp-Woods
SEQ. ID. NO. 18731   1-MetLysThrLysLeu-5
SEQ. ID. NO. 18732   28-AlaAsnAlaGluProAlaValLysAlaGluSerAlaGlyLysSerVal-43
SEQ. ID. NO. 18733   47-LeuLysAlaArgLeuGluLysThrTyrSer-56
SEQ. ID. NO. 18734   99-IleAsnIleAspThrArgLysAsnLeuThrGluGluArgAlaAlaAspLeuAsnLys-117

TABLE 1-continued

| | |
|---|---|
| SEQ. ID. NO. 18735 | 124-ProLeuAspLysAlaIleLysGluValArgGlyAsnGlyLysLeuLys-139 |
| SEQ. ID. NO. 18736 | 144-SerAspProAspCysProPhe-150 |
| SEQ. ID. NO. 18737 | 152-LysArgLeuGluHisGluPheGluLysMetThrAsp-163 |
| SEQ. ID. NO. 18738 | 179-AspAlaAlaArgLysAla-184 |
| SEQ. ID. NO. 18739 | 190-GlnProAspAlaLysAla-196 |
| SEQ. ID. NO. 18740 | 200-TrpMetArgLysGlyLysPhe-206 |
| SEQ. ID. NO. 18741 | 240-GlyArgSerGlnSer-244 |
| SEQ. ID. NO. 18742 | 250-ProGlnLeuGluGluIleIleArgLysAsnGln-260 | a294
AMPHI Regions - AMPHI

| | |
|---|---|
| SEQ. ID. NO. 18743 | 27-ArgPheProAlaAlaPheArgArgTyrSer-36 |
| SEQ. ID. NO. 18744 | 45-LysProAlaGlyThr-49 |
| SEQ. ID. NO. 18745 | 51-TrpHisArgValArgArgPheLysSerAsnArgArgThr-63 |
| SEQ. ID. NO. 18746 | 65-GlyGlyLysProLeuLysLysThrTyrArg-74 |
| SEQ. ID. NO. 18747 | 92-AsnIleAlaGluArgAlaArgGluSerProArgArgTyrGlyLysArgTyrAlaAspIleGlyAspAsp-114 |
| SEQ. ID. NO. 18748 | 133-AlaValAlaHisIleValHisLeu-140 |
| SEQ. ID. NO. 18749 | 176-AlaMetSerTyrArg-180 |
| SEQ. ID. NO. 18750 | 206-SerIleLeuGlyGluProPheAlaThrSerPheGly-217 |
| SEQ. ID. NO. 18751 | 227-AlaPheSerValLeuAlaHisPhe-234 |
| SEQ. ID. NO. 18752 | 247-ThrValGlyTrpSerLysTyrIleHisThrVal-257 |

Antigenic Index - Jameson-Wolf

| | |
|---|---|
| SEQ. ID. NO. 18753 | 20-AlaValArgThrSerSerAsnArgPhe-28 |
| SEQ. ID. NO. 18754 | 32-PheArgArgTyrSerAlaPheArg-39 |
| SEQ. ID. NO. 18755 | 44-ProLysProAlaGlyThrProTrpHisArgValArgArgPheLysSerAsnArgArgThrArgGlyGlyLysProLeuLysLysThrTyrArgPro ArgArgAlaGluCysArgCysArgArgAlaArgThr-87 |
| SEQ. ID. NO. 18756 | 93-IleAlaGluArgAlaArgGluSerProArgArgTyrGlyLysArgTyrAlaAspIleGlyAspAspSerAspThrIleArg-119 |
| SEQ. ID. NO. 18757 | 121-ArgValPheArgLeuGluTyr-127 |
| SEQ. ID. NO. 18758 | 161-HisThrGlyArgValSerCysGluAlaArgArgGluValGluLysAlaMetSer-178 |
| SEQ. ID. NO. 18759 | 240-LysMetAlaArgSer-244 |

Hydrophilic Regions - Hopp-Woods

| | |
|---|---|
| SEQ. ID. NO. 18760 | 20-AlaValArgThrSerSerAsnArg-27 |
| SEQ. ID. NO. 18761 | 52-HisArgValArgArgPheLysSerAsnArgArgThrArgGlyGlyLysProLeuLysLysThrTyrArgProArgArgAlaGluCysArgCysArgArg AlaArgThr-87 |
| SEQ. ID. NO. 18762 | 93-IleAlaGluArgAlaArgGluSerProArgArgTyrGlyLysArgTyrAlaAspIleGlyAspAspSerAspThrIleArg-119 |
| SEQ. ID. NO. 18763 | 121-ArgValPheArgLeuGluTyr-127 |
| SEQ. ID. NO. 18764 | 165-ValSerCysGluAlaArgArgGluValGluLysAlaMetSer-178 | a295
AMPHI Regions - AMPHI

| | |
|---|---|
| SEQ. ID. NO. 18765 | 79-PheArgGlnProArg-83 |
| SEQ. ID. NO. 18766 | 112-ArgPhePheArgGlnPro-117 |
| SEQ. ID. NO. 18767 | 130-AlaPheLeuHisGlnIle-135 |
| SEQ. ID. NO. 18768 | 175-AsnLeuArgGlyPhePro-180 |
| SEQ. ID. NO. 18769 | 188-HisGlnGlnArgArgIleGlyLysThrLeuProGlnLeu-200 |
| SEQ. ID. NO. 18770 | 232-ThrLeuAlaProMetArgProIleCysArgGlyThrSerGly-245 |
| SEQ. ID. NO. 18771 | 262-TyrIleIleLysProLeuGluHis-269 |

Antigenic Index - Jameson-Wolf

| | |
|---|---|
| SEQ. ID. NO. 18772 | 4-MetAlaArgHisAspAspGlnGlnGly-12 |
| SEQ. ID. NO. 18773 | 18-LeuProArgArgGlnGln-23 |
| SEQ. ID. NO. 18774 | 49-PheLysLeuProArgGlnArgPheHisLeu-58 |
| SEQ. ID. NO. 18775 | 73-HisGlyCysArgAlaGlnPheArgGlnProArgArgIleArgLeu-87 |
| SEQ. ID. NO. 18776 | 91-GlnThrAlaArgGlnArgSerGlyGlyArgThrAspGlnAlaAla-105 |
| SEQ. ID. NO. 18777 | 114-PheArgGlnProArgIleArgGlnLysGlnArgHisThrArg-127 |
| SEQ. ID. NO. 18778 | 136-GlyProAspPheGly-140 |
| SEQ. ID. NO. 18779 | 143-GlnAsnAlaGluHisArgAla-149 |
| SEQ. ID. NO. 18780 | 170-CysIleArgLysGlnAsnLeuArgGlyPheProSerArgArgGlyHisLeuArgHisGlnGlnArgArgIleGlyLysThrLeu-197 |
| SEQ. ID. NO. 18781 | 205-LeuGlyGlyThrArgPheProAspArgAsnGlyValTyrProAsnArgAlaGlyAsnGlyIleArgIleArgLeu-229 |
| SEQ. ID. NO. 18782 | 238-ProIleCysArgGlyThrSerGly-245 |
| SEQ. ID. NO. 18783 | 252-ProTyrProTyrArgArgLysGlnProGlnTyr-262 |
| SEQ. ID. NO. 18784 | 273-SerCysLysThrAsnAlaValArgThrValArgThrAlaPheArgGlnArgAsnGlnIleSer-293 |

Hydrophilic Regions - Hopp-Woods

| | |
|---|---|
| SEQ. ID. NO. 18785 | 5-AlaArgHisAspAspGlnGlnGly-12 |
| SEQ. ID. NO. 18786 | 18-LeuProArgArgGlnGln-23 |
| SEQ. ID. NO. 18787 | 77-AlaGlnPheArgGlnProArgArgIleArgLeu-87 |
| SEQ. ID. NO. 18788 | 93-AlaArgGlnArgSerGlyGlyArgThrAspGlnAlaAla-105 |
| SEQ. ID. NO. 18789 | 117-ProArgIleArgGlnLysGlnArgHisThrArg-127 |
| SEQ. ID. NO. 18790 | 145-AlaGluHisArgAla-149 |
| SEQ. ID. NO. 18791 | 170-CysIleArgLysGlnAsnLeu-176 |
| SEQ. ID. NO. 18792 | 179-PheProSerArgArgGlyHisLeuArgHisGlnGlnArgArgIleGlyLys-195 |
| SEQ. ID. NO. 18793 | 209-ArgPheProAspArgAsnGly-215 |
| SEQ. ID. NO. 18794 | 225-IleArgIleArgLeu-229 |
| SEQ. ID. NO. 18795 | 238-ProIleCysArgGlyThr-243 |
| SEQ. ID. NO. 18796 | 254-ProTyrArgArgLysGlnPro-260 |
| SEQ. ID. NO. 18797 | 280-ArgThrValArgThrAlaPheArgGlnArgAsnGlnIle-292 | a297
AMPHI Regions - AMPHI

| | |
|---|---|
| SEQ. ID. NO. 18798 | 35-ArgThrGluArgVal-39 |
| SEQ. ID. NO. 18799 | 69-GlnProGlyAspSerLeuAlaAspValLeuAla-79 |
| SEQ. ID. NO. 18800 | 86-AspGluIleAlaArgIleThrGluLysTyr-95 |
| SEQ. ID. NO. 18801 | 157-LeuProThrLeuArg-161 |
| SEQ. ID. NO. 18802 | 199-LeuLysGluGlyAspAla-204 |

TABLE 1-continued

| | |
|---|---|
| SEQ. ID. NO. 18803 | 272-LeuValTyrThrArgIleSerSer-279 |
| SEQ. ID. NO. 18804 | 333-HisAlaAsnGlyValGluThrLeuTyrAlaHisLeuSerAlaPheSer-348 |
| Antigenic Index - Jameson-Wolf | |
| SEQ. ID. NO. 18805 | 8-AlaLysHisArgLysTyrAla-14 |
| SEQ. ID. NO. 18806 | 32-SerThrGluArgThrGluArgValArgProGlnArgValGluGlnLysLeuPro-49 |
| SEQ. ID. NO. 18807 | 52-SerTrpGlyGlySerGly-57 |
| SEQ. ID. NO. 18808 | 67-AlaValGlnProGlyAspSerLeuAla-75 |
| SEQ. ID. NO. 18809 | 78-LeuAlaArgSerGlyMetAlaArgAspGluIleAlaArgIleThrGluLysTyrGlyGlyGluAlaAspLeuArgHisLeuArgAlaAspGln SerVal-110 |
| SEQ. ID. NO. 18810 | 115-GlyGlyAspGlyGlyAlaArgGluVal-123 |
| SEQ. ID. NO. 18811 | 127-ThrAspGluAspGlyGluArgAsnLeuValAlaLeuGluLysLysGlyGlyIleTrpArgArgSerAlaSerGluAlaAspMetLysVal-156 |
| SEQ. ID. NO. 18812 | 167-ThrSerAlaArgGlySerLeuAlaArgAlaGluValProValGluIleArgGluSerLeuSer-187 |
| SEQ. ID. NO. 18813 | 194-PheSerLeuAspGlyLeuLysGluGlyAspAlaVal-205 |
| SEQ. ID. NO. 18814 | 228-GluValValLysGlyGlyThrArgHis-236 |
| SEQ. ID. NO. 18815 | 240-TyrTyrArgSerAspLysGluGlyGlyGlyGlyGlyAsnTyrTyrAspGluAspGlyArgValLeuGlnGluLysGlyGlyPheAsn-268 |
| SEQ. ID. NO. 18816 | 276-ArgIleSerSerProPheGlyTyr-283 |
| SEQ. ID. NO. 18817 | 295-HisThrGlyIleAspTyrAla-301 |
| SEQ. ID. NO. 18818 | 303-ProGlnGlyThrProValArgAlaSerAlaAspGly-314 |
| SEQ. ID. NO. 18819 | 318-PheLysGlyArgLysGlyGlyTyrGly-326 |
| SEQ. ID. NO. 18820 | 333-HisAlaAsnGlyValGlu-338 |
| SEQ. ID. NO. 18821 | 350-AlaGluGlyAsnValArgGlyGlyGlu-358 |
| SEQ. ID. NO. 18822 | 365-SerThrGlyArgSerThrGlyProHisLeu-374 |
| SEQ. ID. NO. 18823 | 376-TyrGluAlaArgIleAsnGlyGlnProValAsn-386 |
| SEQ. ID. NO. 18824 | 393-ProThrProGluLeuThrGlnAlaAspLysAlaAla-404 |
| SEQ. ID. NO. 18825 | 408-GlnLysGlnLysAlaAspAlaLeu-415 |
| SEQ. ID. NO. 18826 | 426-ValSerGlnSerAsp-430 |
| Hydrophilic Regions - Hopp-Woods | |
| SEQ. ID. NO. 18827 | 8-AlaLysHisArgLysTyrAla-14 |
| SEQ. ID. NO. 18828 | 32-SerThrGluArgThrGluArgValArgProGlnArgValGluGlnLysLeu-48 |
| SEQ. ID. NO. 18829 | 68-ValGlnProGlyAspSerLeuAla-75 |
| SEQ. ID. NO. 18830 | 82-GlyMetAlaArgAspGluIleAlaArgIleThrGluLysTyrGlyGlyGluAlaAspLeuArgHisLeuArgAlaAspGln-108 |
| SEQ. ID. NO. 18831 | 117-AspGlyGlyAlaArgGlu-122 |
| SEQ. ID. NO. 18832 | 127-ThrAspGluAspGlyGluArgAsnLeuValAlaLeuGluLysLysGlyGlyIleTrpArgArgSerAlaSerGluAlaAspMetLysVal-156 |
| SEQ. ID. NO. 18833 | 167-ThrSerAlaArgGlySerLeuAlaArgAlaGluValProValGluIleArgGluSerLeu-186 |
| SEQ. ID. NO. 18834 | 194-PheSerLeuAspGlyLeuLysGluGlyAspAlaVal-205 |
| SEQ. ID. NO. 18835 | 228-GluValValLysGlyGlyThrArg-235 |
| SEQ. ID. NO. 18836 | 242-ArgSerAspLysGluGlyGlyGly-249 |
| SEQ. ID. NO. 18837 | 253-TyrTyrAspGluAspGlyArgValLeuGlnGluLysGlyGlyPhe-267 |
| SEQ. ID. NO. 18838 | 306-ThrProValArgAlaSerAla-312 |
| SEQ. ID. NO. 18839 | 319-LysGlyArgLysGlyGlyTyr-325 |
| SEQ. ID. NO. 18840 | 350-AlaGluGlyAsnValArgGlyGlyGlu-358 |
| SEQ. ID. NO. 18841 | 366-ThrGlyArgSerThrGly-371 |
| SEQ. ID. NO. 18842 | 378-AlaArgIleAsnGly-382 |
| SEQ. ID. NO. 18843 | 396-GluLeuThrGlnAlaAspLysAlaAla-404 |
| SEQ. ID. NO. 18844 | 408-GlnLysGlnLysAlaAspAlaLeu-415 |
| a298 | |
| AMPHI Regions - AMPHI | |
| SEQ. ID. NO. 18845 | 6-SerLeuPheAlaSerIleLeuMetSerAlaLeuIleAla-18 |
| SEQ. ID. NO. 18846 | 26-IleAsnAlaTyrTrpGlnGln-32 |
| SEQ. ID. NO. 18847 | 42-ProLeuAlaAlaTyr-46 |
| SEQ. ID. NO. 18848 | 62-LeuSerAspGlyIleLysAlaPhe-69 |
| SEQ. ID. NO. 18849 | 82-GlySerAlaAspMetPro-87 |
| SEQ. ID. NO. 18850 | 134-ValGlnLysSerLeuLys-139 |
| SEQ. ID. NO. 18851 | 157-SerTyrProSerPhePheAspTrpProLysThrIleGluGluThrLeuLysLysHisProGlu-177 |
| SEQ. ID. NO. 18852 | 188-AsnAspProTrpAsp-192 |
| SEQ. ID. NO. 18853 | 208-AlaGlnGluTyrLeuLysArgValAspArgIleLeuGluAlaAlaHis-223 |
| SEQ. ID. NO. 18854 | 245-GlnMetArgTyrLeuAspLysLeuLeuSerGluTyrLeu-257 |
| SEQ. ID. NO. 18855 | 276-ArgTyrThrAspSer-280 |
| SEQ. ID. NO. 18856 | 308-AlaLysIleMetGluLys-313 |
| Antigenic Index - Jameson-Wolf | |
| SEQ. ID. NO. 18857 | 22-SerGlnAsnProIleAsnAlaTyr-29 |
| SEQ. ID. NO. 18858 | 34-TyrHisArgAsnSerProLeuGluPro-42 |
| SEQ. ID. NO. 18859 | 47-GlyTrpTrpArgSerGlyAlaAlaLeuGlnGlu-57 |
| SEQ. ID. NO. 18860 | 70-LeuSerGlyGluThrProProThrAlaGlnAspGlyGlySerAlaAspMetProSerGluAlaAlaAlaProGluThrAlaProGlnThrGlyGluThr GluTrpLysGlnAsnThrGlu-109 |
| SEQ. ID. NO. 18861 | 114-ArgThrGlyAspLys-118 |
| SEQ. ID. NO. 18862 | 136-LysSerLeuLysGlnGlnTyrGlyIleGluSerValAsnLeuSerLysGlnSerThrGly-155 |
| SEQ. ID. NO. 18863 | 162-PheAspTrpProLysThrIleGluGluThrLeuLysLysHisProGlu-177 |
| SEQ. ID. NO. 18864 | 186-GlyProAsnAspProTrp-191 |
| SEQ. ID. NO. 18865 | 194-ProValGlyLysArgTyrLeu-200 |
| SEQ. ID. NO. 18866 | 203-AlaSerAspGluTrpAla-208 |
| SEQ. ID. NO. 18867 | 211-TyrLeuLysArgValAspArgIleLeuGlu-220 |
| SEQ. ID. NO. 18868 | 236-TyrMetLysLysAlaLysLeuAspGlyGlnMetArgTyrLeuAsp-250 |
| SEQ. ID. NO. 18869 | 270-LeuSerGlyGlyLysAspArgTyrThrAspSerValAsnValAsnGlyLysProValArgTyrArgSerLysAspGlyIle-296 |
| SEQ. ID. NO. 18870 | 318-ProSerThrGlnProSerSerThrGlnPro-327 |
| Hydrophilic Regions - Hopp-Woods | |
| SEQ. ID. NO. 18871 | 73-GluThrProProThrAlaGlnAspGlyGlySerAlaAspMetProSerGluAlaAlaAlaProGluThrAlaProGlnThrGlyGluThrGluTrpLys GlnAsnThrGlu-109 |
| SEQ. ID. NO. 18872 | 148-AsnLeuSerLysGlnSerThr-154 |
| SEQ. ID. NO. 18873 | 166-LysThrIleGluGluThrLeuLysLysHisProGlu-177 |

TABLE 1-continued

| | |
|---|---|
| SEQ. ID. NO. 18874 | 211-TyrLeuLysArgValAspArgIleLeuGlu-220 |
| SEQ. ID. NO. 18875 | 236-TyrMetLysLysAlaLysLeuAspGlyGlnMetArgTyrLeuAsp-250 |
| SEQ. ID. NO. 18876 | 271-SerGlyGlyLysAspArgTyrThrAsp-279 |
| SEQ. ID. NO. 18877 | 281-ValAsnValAsnGlyLysProValArgTyrArgSerLysAspGlyIle-296 |
| SEQ. ID. NO. 18878 | 319-SerThrGlnProSerSerThrGlnPro-327 | a299
AMPHI Regions - AMPHI

| | |
|---|---|
| SEQ. ID. NO. 18879 | 54-AlaSerProTrpMetLysLysLeuGlnSerValAlaGlnGlySer-68 |
| SEQ. ID. NO. 18880 | 71-ThrPheArgIleLeuGlnIleGly-78 |
| SEQ. ID. NO. 18881 | 85-AspPhePheThrAspSerLeuArgLysArgLeuGlnLysThrTrpGly-100 |
| SEQ. ID. NO. 18882 | 238-GlnLeuThrGlnTrpSerLysTrp-245 |
| SEQ. ID. NO. 18883 | 247-AlaAspArgMetAsnAspLeuAlaGlnThr-256 |
| SEQ. ID. NO. 18884 | 281-GluGlnLysTrpLeuAspThrValArgGlnIleArgAspSerLeu-295 |
| SEQ. ID. NO. 18885 | 307-GluSerLeuLysAsnThrLeu-313 |
| SEQ. ID. NO. 18886 | 322-ArgLeuThrGluValGlnGlnMetGlnArgArgIleAlaArgGln-336 |
| SEQ. ID. NO. 18887 | 375-TyrGlnArgSerAlaGluMetLeuAlaAspSerLeuGluGluLeuValArgSerAlaAlaIleArg-396 |

Antigenic Index - Jameson-Wolf

| | |
|---|---|
| SEQ. ID. NO. 18888 | 1-MetAsnProLysHis-5 |
| SEQ. ID. NO. 18889 | 35-ProSerAlaProTyrThrAspThrAsnGlyLeu-45 |
| SEQ. ID. NO. 18890 | 48-AspTyrGlyAsnAlaSerAlaSerProTrpMetLysLysLeuGln-62 |
| SEQ. ID. NO. 18891 | 65-AlaGlnGlySerGlyGluThr-71 |
| SEQ. ID. NO. 18892 | 78-GlyAspSerHisThrAlaGlyAspPhePheThrAspSerLeuArgLysArgLeuGlnLysThrTrpGlyAspGlyGly-103 |
| SEQ. ID. NO. 18893 | 110-AlaAsnValLysGlyGlnArg-116 |
| SEQ. ID. NO. 18894 | 121-ArgHisAsnGlyAsnTrpGlnSerLeuThrSerArgAsnAsnThrGlyAspPheProLeu-140 |
| SEQ. ID. NO. 18895 | 157-AlaSerAspGlyIleAlaSerLysGlnArgVal-167 |
| SEQ. ID. NO. 18896 | 184-GlyAsnThrValSerAlaAsnGlyGlyGly-193 |
| SEQ. ID. NO. 18897 | 221-GluAsnProAlaGlyGly-226 |
| SEQ. ID. NO. 18898 | 241-GlnTrpSerLysTrpArgAlaAspArgMetAsnAspLeuAlaGlnThrGlyAla-258 |
| SEQ. ID. NO. 18899 | 266-GlyThrAsnGluAlaPheGlyAspAsnIleAspIleAlaAspThrGluGlnLysTrp-284 |
| SEQ. ID. NO. 18900 | 286-AspThrValArgGlnIleArgAspSerLeuPro-296 |
| SEQ. ID. NO. 18901 | 305-AlaProGluSerLeuLysAsnThr-312 |
| SEQ. ID. NO. 18902 | 319-ArgProValArgLeuThrGluValGlnGlnMetGlnArgArgIleAlaArgGlnGlyGlnThr-339 |
| SEQ. ID. NO. 18903 | 361-GlyTrpAlaAlaLysAspGlyVal-368 |
| SEQ. ID. NO. 18904 | 371-SerAlaLysGlyTyrGlnArgSerAlaGluMetLeuAlaAspSerLeuGluGluLeuValArg-391 |
| SEQ. ID. NO. 18905 | 393-AlaAlaIleArgGln-397 |

Hydrophilic Regions - Hopp-Woods

| | |
|---|---|
| SEQ. ID. NO. 18906 | 67-GlySerGlyGluThr-71 |
| SEQ. ID. NO. 18907 | 90-SerLeuArgLysArgLeuGlnLysThrTrpGly-100 |
| SEQ. ID. NO. 18908 | 112-ValLysGlyGlnArg-116 |
| SEQ. ID. NO. 18909 | 130-ThrSerArgAsnAsnThrGly-136 |
| SEQ. ID. NO. 18910 | 159-AspGlyIleAlaSerLysGlnArgVal-167 |
| SEQ. ID. NO. 18911 | 245-TrpArgAlaAspArgMetAsnAsp-252 |
| SEQ. ID. NO. 18912 | 270-AlaPheGlyAspAsnIleAspIleAlaAspThrGluGlnLysTrp-284 |
| SEQ. ID. NO. 18913 | 288-ValArgGlnIleArgAspSerLeuPro-296 |
| SEQ. ID. NO. 18914 | 319-ArgProValArgLeuThrGlu-325 |
| SEQ. ID. NO. 18915 | 327-GlnGlnMetGlnArgArgIleAlaArgGlnGly-337 |
| SEQ. ID. NO. 18916 | 363-AlaAlaLysAspGlyVal-368 |
| SEQ. ID. NO. 18917 | 374-GlyTyrGlnArgSerAlaGluMetLeuAlaAspSerLeuGluGluLeuValArg-391 |
| SEQ. ID. NO. 18918 | 393-AlaAlaIleArgGln-397 | a302
AMPHI Regions - AMPHI

| | |
|---|---|
| SEQ. ID. NO. 18919 | 20-AspGlyArgPheLeuArgThrValGluTrpLeuGlyAsnMetLeuProHisPro-37 |
| SEQ. ID. NO. 18920 | 81-ValValSerLeuLeuAspAlaAspGlyLeuIleLysIleLeuThrHisThrValLysAsnPheThrGlyPheAlaProLeuGlyThrValLeuValSerLeu-114 |
| SEQ. ID. NO. 18921 | 127-SerAlaLeuMetArg-131 |
| SEQ. ID. NO. 18922 | 176-GlyArgHisProLeuAlaGlyLeuAlaAlaAlaPheAlaGlyValSerGly-192 |
| SEQ. ID. NO. 18923 | 201-GlyThrIleAspProLeuLeuAlaGlyIleThrGlnGlnAla-214 |
| SEQ. ID. NO. 18924 | 239-ValIleAlaLeuIleGly-244 |
| SEQ. ID. NO. 18925 | 271-ArgHisSerAsnGluIle-276 |
| SEQ. ID. NO. 18926 | 294-LeuSerAlaLeuLeuAlaTrp-300 |
| SEQ. ID. NO. 18927 | 308-IleLeuArgHisProGluThrGly-315 |
| SEQ. ID. NO. 18928 | 341-TyrGlyArgValThrArgSerLeuArgGlyGluGlnGluValValAsnAlaMetAlaGluSerMetSer-363 |
| SEQ. ID. NO. 18929 | 378-PheValAlaPhePheAsnTrpThrAsnIleGlyGlnTyrIle-391 |
| SEQ. ID. NO. 18930 | 448-AlaProGluValIleGlnAlaAlaTyrArgIleGlyAspSerValThrAsnIleIleThrProMetMetSerTyrPheGlyLeuIleMetAla-478 |
| SEQ. ID. NO. 18931 | 505-IleAlaTrpIleAlaLeuPheCysIle-513 |

Antigenic Index - Jameson-Wolf

| | |
|---|---|
| SEQ. ID. NO. 18932 | 8-LysGluLysGlnMetSerGlnThrAspThrGlnArgAspGlyArgPhe-23 |
| SEQ. ID. NO. 18933 | 61-SerValProAspProArgProValGlyAlaLysGlyArgAlaAspAspGlyLeu-78 |
| SEQ. ID. NO. 18934 | 85-LeuAspAlaAspGlyLeu-90 |
| SEQ. ID. NO. 18935 | 119-IleAlaGluLysSerGly-124 |
| SEQ. ID. NO. 18936 | 134-LeuThrLysSerProArgLysLeuThr-142 |
| SEQ. ID. NO. 18937 | 152-LeuSerAsnThrAlaSerGlu-158 |
| SEQ. ID. NO. 18938 | 175-LeuGlyArgHisProLeu-180 |
| SEQ. ID. NO. 18939 | 250-LysIleValGluProGlnLeuGlyProTyrGlnSerAspLeuSerGlnGluGluLysAspIleArgHisSerAsnGluIleThrProLeuGluTyrLys-282 |
| SEQ. ID. NO. 18940 | 304-ProAlaAspGlyIleLeuArgHisProGluThrGlyLeuValSer-318 |
| SEQ. ID. NO. 18941 | 343-ArgValThrArgSerLeuArgGlyGluGlnGluVal-354 |
| SEQ. ID. NO. 18942 | 402-ValGlyLeuGlyGly-406 |
| SEQ. ID. NO. 18943 | 482-LysTyrLysLysAspAlaGlyVal-489 |

TABLE 1-continued

Hydrophilic Regions - Hopp-Woods
SEQ. ID. NO. 18944  8-LysGluLysGlnMetSerGlnThrAspThrGlnArgAspGlyArgPhe-23
SEQ. ID. NO. 18945  63-ProAspProArgProValGlyAlaLysGlyArgAlaAspAspGlyLeu-78
SEQ. ID. NO. 18946  85-LeuAspAlaAspGlyLeu-90
SEQ. ID. NO. 18947  119-IleAlaGluLysSerGly-124
SEQ. ID. NO. 18948  136-LysSerProArgLysLeu-141
SEQ. ID. NO. 18949  263-LeuSerGlnGluGluLysAspIleArgHisSerAsnGlu-275
SEQ. ID. NO. 18950  307-GlyIleLeuArgHisProGlu-313
SEQ. ID. NO. 18951  343-ArgValThrArgSerLeuArgGlyGluGlnGluVal-354
SEQ. ID. NO. 18952  482-LysTyrLysLysAspAlaGly-488
a305
AMPHI Regions - AMPHI
SEQ. ID. NO. 18953  10-LeuMetMetGlyLeuValGluGlyPheThrGluPheLeuPro-23
SEQ. ID. NO. 18954  33-PheGlyAsnLeuIleAspPheHisSer-41
SEQ. ID. NO. 18955  66-PheSerAsnValLeuHis-71
SEQ. ID. NO. 18956  93-AlaAlaValMetGly-97
SEQ. ID. NO. 18957  99-LeuPheGlyLysGlnIleLysGluTyrLeuPhe-109
SEQ. ID. NO. 18958  141-AspValAspAlaLeuArgProIleAspAla-150
SEQ. ID. NO. 18959  155-ValAlaGlnValPheAla-160
SEQ. ID. NO. 18960  202-AlaTyrAspValLeuLysHisTyrArgPhePheThrLeuHis-215
SEQ. ID. NO. 18961  222-IleGlyPheValAlaAlaPheValSer-230
SEQ. ID. NO. 18962  235-ValLysAlaLeuLeuArg-240
Antigenic Index - Jameson-Wolf
SEQ. ID. NO. 18963  40-HisSerAsnHisLys-44
SEQ. ID. NO. 18964  61-GluTyrArgGlnArgPheSerAsn-68
SEQ. ID. NO. 18965  72-GlyValGlyLysAspArgLysAlaAsn-80
SEQ. ID. NO. 18966  128-ValGluLysArgGlnSerArgAlaGluProLysIleValAsp-141
SEQ. ID. NO. 18967  143-AspAlaLeuArgProIleAsp-149
SEQ. ID. NO. 18968  163-ProGlyThrSerArgSerGlySer-170
SEQ. ID. NO. 18969  180-IleGluArgLysThrAlaThr-186
SEQ. ID. NO. 18970  241-PheValSerLysLysAsnTyr-247
Hydrophilic Regions - Hopp-Woods
SEQ. ID. NO. 18971  62-TyrArgGlnArgPhe-66
SEQ. ID. NO. 18972  73-ValGlyLysAspArgLysAlaAsn-80
SEQ. ID. NO. 18973  128-ValGluLysArgGlnSerArgAlaGluProLysIleValAsp-141
SEQ. ID. NO. 18974  143-AspAlaLeuArgProIleAsp-149
SEQ. ID. NO. 18975  165-ThrSerArgSerGlySer-170
SEQ. ID. NO. 18976  180-IleGluArgLysThrAlaThr-186
SEQ. ID. NO. 18977  242-ValSerLysLysAsn-246
a308-2
AMPHI Regions - AMPHI
SEQ. ID. NO. 18978  6-PheTyrArgIleLeuGlyValAlaAspAsnLeuTyrProTyrLeu-20
SEQ. ID. NO. 18979  27-ThrIleIleAlaGlyLeu-32
SEQ. ID. NO. 18980  64-AlaLeuGluLeuLeuArgAlaGlnAsp-72
SEQ. ID. NO. 18981  83-AlaGluMetAlaArgAlaSerGlu-90
SEQ. ID. NO. 18982  101-LeuAlaAspPheValHisProIleGlyAsnIleGlyAlaCys-114
SEQ. ID. NO. 18983  131-SerMetArgThrLeuAlaSerValValHisGlyPheGlyAsp-144
SEQ. ID. NO. 18984  172-LeuAlaHisLeuAspAsnMetLysArgValThrGlu-183
Antigenic Index - Jameson-Wolf
SEQ. ID. NO. 18985  39-TrpGluArgArgMetMetVal-45
SEQ. ID. NO. 18986  68-LeuArgAlaGlnAspIleGluThr-75
SEQ. ID. NO. 18987  80-SerLysGlyAlaGluMetAlaArgAlaSerGluThrAlaTyrAlaArgAspGluVal-98
SEQ. ID. NO. 18988  118-GlyThrPheLysThrAspGlyMet-125
SEQ. ID. NO. 18989  142-PheGlyAspAsnLeuLeu-147
SEQ. ID. NO. 18990  149-ArgAlaAlaAspValValLeuLysGluArgArgArgLeu-161
SEQ. ID. NO. 18991  166-ArgGluThrProLeu-170
SEQ. ID. NO. 18992  176-AspAsnMetLysArgValThrGluMetGly-185
SEQ. ID. NO. 18993  195-MetTyrArgLysProGlnThrAlaAspAspIleVal-206
SEQ. ID. NO. 18994  219-IleAspThrProAspSerAlaGlu-226
Hydrophilic Regions - Hopp-Woods
SEQ. ID. NO. 18995  39-TrpGluArgArgMetMetVal-45
SEQ. ID. NO. 18996  68-LeuArgAlaGlnAspIleGluThr-75
SEQ. ID. NO. 18997  81-LysGlyAlaGluMetAlaArgAlaSerGlu-90
SEQ. ID. NO. 18998  92-AlaTyrAlaArgAspGluVal-98
SEQ. ID. NO. 18999  120-PheLysThrAspGly-124
SEQ. ID. NO. 19000  149-ArgAlaAlaAspValValLeuLysGluArgArgArgLeu-161
SEQ. ID. NO. 19001  176-AspAsnMetLysArgValThrGlu-183
SEQ. ID. NO. 19002  195-MetTyrArgLysProGlnThrAlaAspAspIleVal-206
SEQ. ID. NO. 19003  220-AspThrProAspSerAlaGlu-226
a311-1
AMPHI Regions - AMPHI
SEQ. ID. NO. 19004  7-SerHisTrpArgValLeuAlaGluLeuAlaAspGlyLeuProGlnHisValSerGlnLeuAlaArgMetAlaAsp-31
SEQ. ID. NO. 19005  37-LeuAsnGlyPheTrpGlnGlnMetProAlaHisIleArgGlyLeuLeuArg-53
SEQ. ID. NO. 19006  55-HisAspGlyTyrTrpArgLeuValArgProLeuAlaValPheAspAlaGluGlyLeuArgGluLeuGly-77
SEQ. ID. NO. 19007  124-ArgGlnGlyArgLysTrpSerHisArgLeu-133
SEQ. ID. NO. 19008  165-ArgAlaLeuSerArgLeu-170
SEQ. ID. NO. 19009  219-ValGluAsnAlaAlaSerValGlnSerLeuPheGln-230
SEQ. ID. NO. 19010  245-GluThrLeuLeuAlaGlu-250
SEQ. ID. NO. 19011  291-PheGluGlyThrValLysGlyValAspGlyGlnGlyVal-303
SEQ. ID. NO. 19012  362-ThrValGlySerAlaProTyrArgAspLeuSerProLeu-374

TABLE 1-continued

| SEQ. ID. NO. 19013 | 376-AlaGluTrpAlaGluLysVal-382 |
| SEQ. ID. NO. 19014 | 391-CysAlaValCysGlyGluPheLysLys-399 |
| SEQ. ID. NO. 19015 | 426-TyrArgHisProGluGluHisGlySerAspArgTrpPheAsnAlaLeuGlySer-443 |
| SEQ. ID. NO. 19016 | 493-AsnLeuAsnArgHisAla-498 |
| SEQ. ID. NO. 19017 | 511-AlaValAlaSerGlyMetMetAspAlaValCys-521 |
| SEQ. ID. NO. 19018 | 550-AlaAlaLysValAlaGluAlaLeuProPro-559 |
| SEQ. ID. NO. 19019 | 576-HisGlyLeuLeuAsnLeu-581 |

Antigenic Index - Jameson-Wolf

| SEQ. ID. NO. 19020 | 28-ArgMetAlaAspMetLysProGlnGln-36 |
| SEQ. ID. NO. 19021 | 50-GlyLeuLeuArgGlnHisAspGlyTyr-58 |
| SEQ. ID. NO. 19022 | 71-GluGlyLeuArgGluLeuGlyGluArgSerGlyPhe-82 |
| SEQ. ID. NO. 19023 | 86-LeuLysHisGluCysAlaSerSerAsnAspGluIleLeuGlu-99 |
| SEQ. ID. NO. 19024 | 102-ArgIleAlaProAspLysAlaHisLys-110 |
| SEQ. ID. NO. 19025 | 116-HisLeuGlnSerLysGlyArgGlyArgGlnGlyArgLysTrpSerHisArgLeuGlyGlu-135 |
| SEQ. ID. NO. 19026 | 145-PheAspArgProGlnTyrGluLeuGlySer-154 |
| SEQ. ID. NO. 19027 | 162-AlaCysArgArgAlaLeuSer-168 |
| SEQ. ID. NO. 19028 | 174-ThrGlnIleLysTrpProAsn-180 |
| SEQ. ID. NO. 19029 | 182-LeuValValGlyArgAspLysLeuGly-190 |
| SEQ. ID. NO. 19030 | 196-ThrValArgThrGlyGlyLysThrVal-204 |
| SEQ. ID. NO. 19031 | 215-LeuProLysGluValGluAsn-221 |
| SEQ. ID. NO. 19032 | 231-ThrAlaSerArgArgGlyAsnAlaAsp-239 |
| SEQ. ID. NO. 19033 | 258-TyrAlaArgAspGlyPheAla-264 |
| SEQ. ID. NO. 19034 | 272-AlaAlaAsnArgAspHisGlyLys-279 |
| SEQ. ID. NO. 19035 | 284-LeuArgAspGlyGluThrValPhe-291 |
| SEQ. ID. NO. 19036 | 293-GlyThrValLysGlyValAspGlyGlnGly-302 |
| SEQ. ID. NO. 19037 | 307-GluThrAlaGluGlyLysGlnThrValValSerGlyGluIleSerLeuArgSerAspAspArgProValSerValProLysArgArgAspSerGluArg-339 |
| SEQ. ID. NO. 19038 | 344-AspGlyGlyAsnSerArgLeu-350 |
| SEQ. ID. NO. 19039 | 364-GlySerAlaProTyrArgAspLeuSerProLeuGly-375 |
| SEQ. ID. NO. 19040 | 378-TrpAlaGluLysValAspGlyAsnValArgIle-388 |
| SEQ. ID. NO. 19041 | 395-GlyGluPheLysLysAlaGlnValGln-403 |
| SEQ. ID. NO. 19042 | 405-GlnLeuAlaArgLysIleGlu-411 |
| SEQ. ID. NO. 19043 | 424-AsnHisTyrArgHisProGluGluHisGlySerAspArgTrp-437 |
| SEQ. ID. NO. 19044 | 440-AlaLeuGlySerArgArgPheSerArgAsnAla-450 |
| SEQ. ID. NO. 19045 | 464-AlaLeuThrAspAspGlyHisTyrLeuGly-473 |
| SEQ. ID. NO. 19046 | 483-MetLysGluSerLeuAla-488 |
| SEQ. ID. NO. 19047 | 492-AlaAsnLeuAsnArgHisAlaGlyLysArgTyrPro-503 |
| SEQ. ID. NO. 19048 | 529-GlyArgLeuLysGluLysThrGlyAlaGlyLysProVal-541 |
| SEQ. ID. NO. 19049 | 547-GlyGlyGlyAlaAlaLysValAlaGlu-555 |
| SEQ. ID. NO. 19050 | 565-AsnThrValArgValAlaAsp-571 |
| SEQ. ID. NO. 19051 | 584-AlaGluGlyGlyGluSerGluHisThr-592 |

Hydrophilic Regions - Hopp-Woods

| SEQ. ID. NO. 19052 | 28-ArgMetAlaAspMetLysProGlnGln-36 |
| SEQ. ID. NO. 19053 | 50-GlyLeuLeuArgGlnHis-55 |
| SEQ. ID. NO. 19054 | 71-GluGlyLeuArgGluLeuGlyGluArgSerGlyPhe-82 |
| SEQ. ID. NO. 19055 | 86-LeuLysHisGluCysAlaSerSerAsnAspGluIleLeuGlu-99 |
| SEQ. ID. NO. 19056 | 102-ArgIleAlaProAspLysAlaHisLys-110 |
| SEQ. ID. NO. 19057 | 118-GlnSerLysGlyArgGlyArgGlnGlyArgLysTrpSerHisArgLeuGlyGlu-135 |
| SEQ. ID. NO. 19058 | 162-AlaCysArgArgAlaLeuSer-168 |
| SEQ. ID. NO. 19059 | 183-ValValGlyArgAspLysLeuGly-190 |
| SEQ. ID. NO. 19060 | 196-ThrValArgThrGlyGlyLys-202 |
| SEQ. ID. NO. 19061 | 217-LysGluValGluAsn-221 |
| SEQ. ID. NO. 19062 | 232-AlaSerArgArgGlyAsnAlaAsp-239 |
| SEQ. ID. NO. 19063 | 259-AlaArgAspGlyPhe-263 |
| SEQ. ID. NO. 19064 | 272-AlaAlaAsnArgAspHisGlyLys-279 |
| SEQ. ID. NO. 19065 | 285-ArgAspGlyGluThrValPhe-291 |
| SEQ. ID. NO. 19066 | 293-GlyThrValLysGlyValAspGly-300 |
| SEQ. ID. NO. 19067 | 307-GluThrAlaGluGlyLysGlnThrValVal-316 |
| SEQ. ID. NO. 19068 | 320-IleSerLeuArgSerAspAspArgProValSerValProLysArgArgAspSerGluArg-339 |
| SEQ. ID. NO. 19069 | 346-GlyAsnSerArgLeu-350 |
| SEQ. ID. NO. 19070 | 367-ProTyrArgAspLeuSer-372 |
| SEQ. ID. NO. 19071 | 378-TrpAlaGluLysValAspGlyAsnVal-386 |
| SEQ. ID. NO. 19072 | 395-GlyGluPheLysLysAlaGlnVal-402 |
| SEQ. ID. NO. 19073 | 405-GlnLeuAlaArgLysIleGlu-411 |
| SEQ. ID. NO. 19074 | 424-AsnHisTyrArgHisProGluGluHisGlySer-434 |
| SEQ. ID. NO. 19075 | 442-GlySerArgArgPheSerArg-448 |
| SEQ. ID. NO. 19076 | 464-AlaLeuThrAspAspGlyHis-470 |
| SEQ. ID. NO. 19077 | 483-MetLysGluSerLeuAla-488 |
| SEQ. ID. NO. 19078 | 493-AsnLeuAsnArgHisAlaGlyLysArgTyrPro-503 |
| SEQ. ID. NO. 19079 | 529-GlyArgLeuLysGluLysThrGlyAlaGlyLysProVal-541 |
| SEQ. ID. NO. 19080 | 549-GlyAlaAlaLysValAlaGlu-555 |
| SEQ. ID. NO. 19081 | 565-AsnThrValArgValAlaAsp-571 |
| SEQ. ID. NO. 19082 | 585-GluGlyGlyGluSerGluHisThr-592 | a312
AMPHI Regions - AMPHI

| SEQ. ID. NO. 19083 | 6-GlyGluIleLeuGluThrValLysMetValAla-16 |
| SEQ. ID. NO. 19084 | 44-GlnAsnIleTyrAsnLysIleThrThrValGlyLys-55 |
| SEQ. ID. NO. 19085 | 82-IleAlaGlnIleAlaAlaAlaThr-89 |
| SEQ. ID. NO. 19086 | 95-ValSerValAlaGlnThrLeuAspLysAlaAlaLys-106 |
| SEQ. ID. NO. 19087 | 109-GlyValSerPheIleGlyGlyPheSerAlaLeuValGln-121 |

TABLE 1-continued

| | |
|---|---|
| SEQ. ID. NO. 19088 | 133-ArgSerIleProGluAlaMetLysThr-141 |
| SEQ. ID. NO. 19089 | 167-GlyGluThrIleLysArgThr-173 |
| SEQ. ID. NO. 19090 | 182-GlyCysAlaLysIleValValPheCys-190 |
| SEQ. ID. NO. 19091 | 230-SerAspAlaThrThrLeuThrGluValAlaGluValValLysLys-244 |
| SEQ. ID. NO. 19092 | 249-IleThrArgValGlyGluLeuIleGlyArgGluAlaSerLys-262 |
| SEQ. ID. NO. 19093 | 281-ValGlyAspSerValAlaArgIleLeuGluGluMetGly-293 |
| SEQ. ID. NO. 19094 | 309-LeuAsnAspAlaVal-313 |
| SEQ. ID. NO. 19095 | 322-SerAlaValGlyGlyLeuSerGly-329 |
| SEQ. ID. NO. 19096 | 349-LeuThrLeuAspLysLeuGluAlaMetThrAla-359 |
| SEQ. ID. NO. 19097 | 374-ThrProAlaHisThrIleSerGlyIleIle-383 |
| SEQ. ID. NO. 19098 | 409-ValGlyAspSerValGluPheGlyGlyLeuLeuGly-420 |
| Antigenic Index - Jameson-Wolf | |
| SEQ. ID. NO. 19099 | 4-GlnSerGlyGluIleLeuGlu-10 |
| SEQ. ID. NO. 19100 | 13-LysMetValAlaAspGlnAsnPheAspVal-22 |
| SEQ. ID. NO. 19101 | 35-IleSerThrAspIleAspVal-41 |
| SEQ. ID. NO. 19102 | 52-ThrValGlyLysAspLeuValAla-59 |
| SEQ. ID. NO. 19103 | 89-ThrHisAlaAspSer-93 |
| SEQ. ID. NO. 19104 | 100-ThrLeuAspLysAlaAlaLys-106 |
| SEQ. ID. NO. 19105 | 121-GlnLysGlyMetSerProSerAspGluValLeu-131 |
| SEQ. ID. NO. 19106 | 134-SerIleProGluAlaMetLysThrThrAsp-143 |
| SEQ. ID. NO. 19107 | 152-GlySerThrArgAla-156 |
| SEQ. ID. NO. 19108 | 161-AspAlaValArgLeuAlaGlyGluThrIleLysArgThrAlaGluIleThr-177 |
| SEQ. ID. NO. 19109 | 192-AlaValGluAspAsnProPhe-198 |
| SEQ. ID. NO. 19110 | 204-HisGlySerGlyGluAlaAspAla-211 |
| SEQ. ID. NO. 19111 | 225-AlaAlaLeuGluAsnSerAspAla-232 |
| SEQ. ID. NO. 19112 | 237-GluValAlaGluValValLys-243 |
| SEQ. ID. NO. 19113 | 251-ArgValGlyGluLeuIleGlyArgGluAlaSerLys-262 |
| SEQ. ID. NO. 19114 | 280-AlaValGlyAspSerValAlaArgIleLeuGlu-290 |
| SEQ. ID. NO. 19115 | 311-AspAlaValLysLysGlyGlyMet-318 |
| SEQ. ID. NO. 19116 | 334-ValSerGluAspGluGlyMet-340 |
| SEQ. ID. NO. 19117 | 352-AspLysLeuGluAla-356 |
| SEQ. ID. NO. 19118 | 370-ValProGlyAspThrProAla-376 |
| SEQ. ID. NO. 19119 | 383-IleAlaAspGluAlaAla-388 |
| SEQ. ID. NO. 19120 | 392-IleAsnSerLysThrThrAla-398 |
| SEQ. ID. NO. 19121 | 405-ThrGlyLysThrValGlyAspSerValGlu-414 |
| SEQ. ID. NO. 19122 | 426-ProValLysGluGlySerCys-432 |
| SEQ. ID. NO. 19123 | 435-PheValAsnArgGlyGlyArgIle-442 |
| SEQ. ID. NO. 19124 | 447-GlnSerMetLysAsn-451 |
| Hydrophilic Regions - Hopp-Woods | |
| SEQ. ID. NO. 19125 | 18-GlnAsnPheAspVal-22 |
| SEQ. ID. NO. 19126 | 35-IleSerThrAspIleAspVal-41 |
| SEQ. ID. NO. 19127 | 52-ThrValGlyLysAspLeuValAla-59 |
| SEQ. ID. NO. 19128 | 100-ThrLeuAspLysAlaAlaLys-106 |
| SEQ. ID. NO. 19129 | 123-GlyMetSerProSerAspGluValLeu-131 |
| SEQ. ID. NO. 19130 | 134-SerIleProGluAlaMetLysThrThrAsp-143 |
| SEQ. ID. NO. 19131 | 161-AspAlaValArgLeuAlaGlyGluThrIleLysArgThrAlaGluIleThr-177 |
| SEQ. ID. NO. 19132 | 192-AlaValGluAspAsnPro-197 |
| SEQ. ID. NO. 19133 | 207-GlyGluAlaAspAla-211 |
| SEQ. ID. NO. 19134 | 225-AlaAlaLeuGluAsnSerAspAla-232 |
| SEQ. ID. NO. 19135 | 237-GluValAlaGluValValLys-243 |
| SEQ. ID. NO. 19136 | 251-ArgValGlyGluLeuIleGlyArgGluAlaSerLys-262 |
| SEQ. ID. NO. 19137 | 284-SerValAlaArgIleLeuGlu-290 |
| SEQ. ID. NO. 19138 | 311-AspAlaValLysLysGlyGlyMet-318 |
| SEQ. ID. NO. 19139 | 334-ValSerGluAspGluGlyMet-340 |
| SEQ. ID. NO. 19140 | 352-AspLysLeuGluAla-356 |
| SEQ. ID. NO. 19141 | 383-IleAlaAspGluAlaAla-388 |
| SEQ. ID. NO. 19142 | 408-ThrValGlyAspSerValGlu-414 |
| SEQ. ID. NO. 19143 | 426-ProValLysGluGlySerCys-432 |
| SEQ. ID. NO. 19144 | 438-ArgGlyGlyArgIle-442 |
| SEQ. ID. NO. 19145 | 447-GlnSerMetLysAsn-451 |
| a313-2 | |
| AMPHI Regions - AMPHI | |
| SEQ. ID. NO. 19146 | 27-GlyMetAspAspProArgThrTyrGlySerGly-37 |
| SEQ. ID. NO. 19147 | 41-AlaThrAsnValLeu-45 |
| SEQ. ID. NO. 19148 | 60-AspAlaAlaLysGly-64 |
| SEQ. ID. NO. 19149 | 66-ValAlaValLeuLeuAlaArgValLeuGlnGluPro-77 |
| SEQ. ID. NO. 19150 | 88-ValAlaLeuAlaAlaLeuValGlyHisMetTrpPro-99 |
| SEQ. ID. NO. 19151 | 143-SerLeuAlaAlaLeuThrAlaThrIleAlaAlaProLeuAlaAla-157 |
| Antigenic Index - Jameson-Wolf | |
| SEQ. ID. NO. 19152 | 26-TyrGlyMetAspAspProArgThrTyrGlySerGlyAsnProGlyAla-41 |
| SEQ. ID. NO. 19153 | 46-ArgSerGlyLysLysLysAlaAla-53 |
| SEQ. ID. NO. 19154 | 73-ValLeuGlnGluProLeuGlyLeuSerAspSerAla-84 |
| SEQ. ID. NO. 19155 | 104-PheLysGlyGlyLysGlyVal-110 |
| SEQ. ID. NO. 19156 | 180-ArgHisLysSerAsn-184 |
| SEQ. ID. NO. 19157 | 189-IleLysGlyLysGluSerLysIleGlyGluLysArg-200 |
| Hydrophilic Regions - Hopp-Woods | |
| SEQ. ID. NO. 19158 | 26-TyrGlyMetAspAspProArgThrTyrGly-35 |
| SEQ. ID. NO. 19159 | 46-ArgSerGlyLysLysLysAlaAla-53 |
| SEQ. ID. NO. 19160 | 105-LysGlyGlyLysGlyVal-110 |
| SEQ. ID. NO. 19161 | 189-IleLysGlyLysGluSerLysIleGlyGluLysArg-200 |

TABLE 1-continued a401
AMPHI Regions - AMPHI
SEQ. ID. NO. 19162    44-SerGlyValLysProTyrAsnAlaLeu-52
SEQ. ID. NO. 19163    65-CysTyrAsnCysHisSerGlnMetIleArgProPheArg-77
SEQ. ID. NO. 19164    112-ValGlyGlyArgTyrSerAspGluTrpHisArgIle-123
SEQ. ID. NO. 19165    157-MetLysAlaLeuArgLysValGlyThr-165
SEQ. ID. NO. 19166    172-IleAlaLysAlaProGluAlaLeu-179
Antigenic Index - Jameson-Wolf
SEQ. ID. NO. 19167    5-GlnLeuAlaGluGluLysIle-11
SEQ. ID. NO. 19168    38-AlaAlaThrGlnProAlaSerGlyValLysProTyrAsn-50
SEQ. ID. NO. 19169    55-AlaGlyArgAspIleTyrIleArgGluGlyCysTyrAsnCysHis-69
SEQ. ID. NO. 19170    74-ArgProPheArgAlaGluThrGluArgTyrGlyHis-85
SEQ. ID. NO. 19171    90-GlyGluSerValTyr-94
SEQ. ID. NO. 19172    98-PheGlnTrpGlySerLysArgThrGlyProAspLeuAlaArgValGlyGlyArgTyrSerAspGluTrpHis-121
SEQ. ID. NO. 19173    125-LeuLeuAsnProArgAspValValProGluSerAsnMetPro-138
SEQ. ID. NO. 19174    146-AsnLysValAspValAspAla-152
SEQ. ID. NO. 19175    158-LysAlaLeuArgLysValGlyThrProTyrSerAspGluGluIleAlaLysAlaProGlu-177
SEQ. ID. NO. 19176    179-LeuAlaAsnLysSerGluLeuAspAla-187
Hydrophilic Regions - Hopp-Woods
SEQ. ID. NO. 19177    5-GlnLeuAlaGluGluLysIle-11
SEQ. ID. NO. 19178    76-PheArgAlaGluThrGluArgTyrGly-84
SEQ. ID. NO. 19179    101-GlySerLysArgThrGlyProAspLeuAlaArgValGlyGlyArgTyrSerAspGluTrpHis-121
SEQ. ID. NO. 19180    127-AsnProArgAspValValPro-133
SEQ. ID. NO. 19181    146-AsnLysValAspValAspAla-152
SEQ. ID. NO. 19182    158-LysAlaLeuArgLysValGly-164
SEQ. ID. NO. 19183    167-TyrSerAspGluGluIleAlaLysAlaProGlu-177
SEQ. ID. NO. 19184    179-LeuAlaAsnLysSerGluLeuAspAla-187
a402
AMPHI Regions - AMPHI
SEQ. ID. NO. 19185    18-PheLeuSerGlyLeu-22
SEQ. ID. NO. 19186    85-AlaGlyIleAlaAspPhe-90
SEQ. ID. NO. 19187    100-ThrGlyPheSerGlyPheValHis-107
SEQ. ID. NO. 19188    117-AlaValValArgGlyLeu-122
SEQ. ID. NO. 19189    136-LysSerGlyArgGln-140
SEQ. ID. NO. 19190    146-PheAlaAsnValAlaGly-151
SEQ. ID. NO. 19191    218-ValPheGlnAsnIleAlaAspArgProAspArgLeuIle-230
SEQ. ID. NO. 19192    261-AspValPheAsnSerValAsnGlyIleGlu-270
SEQ. ID. NO. 19193    279-LysSerGlyIleArg-283
SEQ. ID. NO. 19194    294-SerTrpAlaArgValLeuSerAlaIleProGluMetGln-306
SEQ. ID. NO. 19195    344-ArgLysTrpLeuArgArgHisPro-351
SEQ. ID. NO. 19196    376-AlaGluPheLeuLysGlnValGlnSerHisLeu-386
SEQ. ID. NO. 19197    398-HisSerProHisAlaPheAlaThrAlaValHisSerIlePro-411
SEQ. ID. NO. 19198    437-GlnArgLeuSerArgLeu-442
SEQ. ID. NO. 19199    460-AlaAlaGlnLysVal-464
Antigenic Index - Jameson-Wolf
SEQ. ID. NO. 19200    4-ValAsnThrLysProAsnThrSer-11
SEQ. ID. NO. 19201    66-ArgIleCysArgSerArgPheValAsp-74
SEQ. ID. NO. 19202    130-ValGlyThrAspGlyAsnLysSerGlyArgGlnValSer-142
SEQ. ID. NO. 19203    222-IleAlaAspArgProAspArgLeuIleGluAsnLysHisGly-235
SEQ. ID. NO. 19204    240-TyrHisArgAspGlyAspLysValVal-248
SEQ. ID. NO. 19205    264-AsnSerValAsnGlyIleGluArg-271
SEQ. ID. NO. 19206    277-SerLeuLysSerGlyIleArgArg-284
SEQ. ID. NO. 19207    321-IleAlaAspGluProGln-326
SEQ. ID. NO. 19208    331-LeuGlnAspLysArgValGluIleValLeuAspAspGlyArgLysTrpLeuArgArgHisProAspGluLysPheAsp-356
SEQ. ID. NO. 19209    385-HisLeuThrProAspGly-390
SEQ. ID. NO. 19210    429-PheProAsnLysGluLeuLeuLysGlnArgLeuSer-440
SEQ. ID. NO. 19211    444-TrpProGluSerGlyArgHisValPheAspSerSerThrVal-457
SEQ. ID. NO. 19212    472-MetThrGluProSerAlaGly-478
SEQ. ID. NO. 19213    481-ValIleThrAspAspAsnMet-487
SEQ. ID. NO. 19214    489-ValGluTyrLysTyrGlyArgGlyIle-497
Hydrophilic Regions - Hopp-Woods
SEQ. ID. NO. 19215    131-GlyThrAspGlyAsnLysSerGlyArgGlnVal-141
SEQ. ID. NO. 19216    222-IleAlaAspArgProAspArgLeuIleGluAsnLysHis-234
SEQ. ID. NO. 19217    241-HisArgAspGlyAspLysValVal-248
SEQ. ID. NO. 19218    278-LeuLysSerGlyIleArg-283
SEQ. ID. NO. 19219    321-IleAlaAspGluProGln-326
SEQ. ID. NO. 19220    331-LeuGlnAspLysArgValGluIleValLeuAspAspGlyArgLysTrpLeuArgArgHisProAspGluLysPheAsp-356
SEQ. ID. NO. 19221    430-ProAsnLysGluLeuLeuLysGlnArgLeuSer-440
SEQ. ID. NO. 19222    446-GluSerGlyArgHisValPhe-452
SEQ. ID. NO. 19223    473-ThrGluProSerAlaGly-478
SEQ. ID. NO. 19224    481-ValIleThrAspAspAsnMet-487
a501
AMPHI Regions - AMPHI
SEQ. ID. NO. 19225    63-ValGluValLeuGlnGluLeuPheArgGlnTyrArgValAlaArgGlnLeu-79
SEQ. ID. NO. 19226    88-ValPheAlaAlaPheGlnAlaVal-95
SEQ. ID. NO. 19227    97-PheGlnGlyPheAspAsnGlyPhe-104
SEQ. ID. NO. 19228    126-AlaAspAlaPheGlnGly-131
SEQ. ID. NO. 19229    139-ValPheGluValValGlyAspIleThrArgArgThrThrGluAla-153
SEQ. ID. NO. 19230    183-AspGlyPheThrArgIleAsnArgCysGlyGlnCys-194
SEQ. ID. NO. 19231    196-HisAlaPheGlyAspPheIleAsp-203

TABLE 1-continued

| | |
|---|---|
| SEQ. ID. NO. 19232 | 252-AlaPheAlaGlyGlnVal-257 |
| SEQ. ID. NO. 19233 | 270-HisHisAspPheTyrArgCysPheArgHisValValGlnSerAsnIleGlyAsnLeu-288 |
| SEQ. ID. NO. 19234 | 306-TyrGlyAsnPheLeuThrValPheGlnGlnPheGlyCys-318 |
| SEQ. ID. NO. 19235 | 364-GlyAsnGlnTyrValAlaGlyPhe-371 |
| SEQ. ID. NO. 19236 | 438-AlaSerProPheAsp-442 |
| SEQ. ID. NO. 19237 | 458-ArgGlnLeuGlyAspPhe-463 |
| SEQ. ID. NO. 19238 | 511-PheGlnArgGlyPheGluHisIleGlu-519 |
| SEQ. ID. NO. 19239 | 528-TyrAspValPheAlaGln-533 |
| Antigenic Index - Jameson-Wolf | |
| SEQ. ID. NO. 19240 | 6-LeuThrAlaAspAla-10 |
| SEQ. ID. NO. 19241 | 17-AlaAlaGlyGlyAspGlyLysVal-24 |
| SEQ. ID. NO. 19242 | 26-HisHisPheAspGly-30 |
| SEQ. ID. NO. 19243 | 46-ValGluThrGluGlyGln-51 |
| SEQ. ID. NO. 19244 | 56-ValArgAlaAspGlyGluAlaValGluVal-65 |
| SEQ. ID. NO. 19245 | 100-PheAspAsnGlyPhe-104 |
| SEQ. ID. NO. 19246 | 108-GlnSerAlaAspGluArgAsnHisAspPheAsnValGlyGln-121 |
| SEQ. ID. NO. 19247 | 144-GlyAspIleThrArgArgThrThrGluAlaGlnHis-155 |
| SEQ. ID. NO. 19248 | 179-GlyHisThrAspAspGlyPheThrArgIleAsnArgCysGlyGlnCys-194 |
| SEQ. ID. NO. 19249 | 202-IleAspValGluValAspArgGlyArgValThrGlyAspThrAlaGlyAsnPhe-219 |
| SEQ. ID. NO. 19250 | 230-GlnGlnGlyPheGlyValAspThrAspLeuAlaValAspAspLysPheHisThrArgGlnAlaAsp-251 |
| SEQ. ID. NO. 19251 | 257-ValGlyGluAlaGluCysGluPheGly-265 |
| SEQ. ID. NO. 19252 | 269-ValHisHisAspPheTyrArgCys-276 |
| SEQ. ID. NO. 19253 | 294-GlyValAspGluAlaGly-299 |
| SEQ. ID. NO. 19254 | 320-AlaAlaAlaAspAsnGlyArgAsnThrGlnPheAlaArgAspAspGlyGlyValAlaGlyThrSerAlaProValGlyHisAspGlyGlySer-350 |
| SEQ. ID. NO. 19255 | 405-ValAspArgLysAlaAla-410 |
| SEQ. ID. NO. 19256 | 420-PheAspGlyPheGlyThrGlyLeuGlnAsp-429 |
| SEQ. ID. NO. 19257 | 439-SerProPheAspValHisArg-445 |
| SEQ. ID. NO. 19258 | 477-AspIleAspValGlyTyr-482 |
| SEQ. ID. NO. 19259 | 490-ValGlyLysAsnHisPheAsp-496 |
| SEQ. ID. NO. 19260 | 502-PheAlaGlnAspGlyArgPhe-508 |
| SEQ. ID. NO. 19261 | 512-GlnArgGlyPheGluHis-517 |
| SEQ. ID. NO. 19262 | 535-ValGlySerAspLysAspAspLeuVal-543 |
| SEQ. ID. NO. 19263 | 548-GlyIleGluGlyGluHisHisThr-555 |
| Hydrophilic Regions - Hopp-Woods | |
| SEQ. ID. NO. 19264 | 6-LeuThrAlaAspAla-10 |
| SEQ. ID. NO. 19265 | 19-GlyGlyAspGlyLysVal-24 |
| SEQ. ID. NO. 19266 | 46-ValGluThrGluGlyGln-51 |
| SEQ. ID. NO. 19267 | 56-ValArgAlaAspGlyGluAlaValGluVal-65 |
| SEQ. ID. NO. 19268 | 108-GlnSerAlaAspGluArgAsnHisAsp-116 |
| SEQ. ID. NO. 19269 | 144-GlyAspIleThrArgArgThrThrGluAlaGlnHis-155 |
| SEQ. ID. NO. 19270 | 179-GlyHisThrAspAspGlyPheThrArgIleAsnArg-190 |
| SEQ. ID. NO. 19271 | 202-IleAspValGluValAspArgGlyArgValThrGlyAspThr-215 |
| SEQ. ID. NO. 19272 | 237-ThrAspLeuAlaValAspAspLysPheHisThrArgGlnAlaAsp-251 |
| SEQ. ID. NO. 19273 | 257-ValGlyGluAlaGluCysGluPheGly-265 |
| SEQ. ID. NO. 19274 | 294-GlyValAspGluAlaGly-299 |
| SEQ. ID. NO. 19275 | 323-AspAsnGlyArgAsnThrGlnPheAlaArgAspAspGlyGlyVal-337 |
| SEQ. ID. NO. 19276 | 344-ValGlyHisAspGly-348 |
| SEQ. ID. NO. 19277 | 405-ValAspArgLysAlaAla-410 |
| SEQ. ID. NO. 19278 | 535-ValGlySerAspLysAspAspLeuVal-543 |
| SEQ. ID. NO. 19279 | 549-IleGluGlyGluHisHisThr-555 |
| a502-1 | |
| AMPHI Regions - AMPHI | |
| SEQ. ID. NO. 19280 | 6-AsnLeuPheGlnPheLeuAlaVal-13 |
| SEQ. ID. NO. 19281 | 26-GlyAlaValAspAlaLeuLysGlnPheAsnAsnAspAlaAspGlyIleSerGlySerPheThrGln-47 |
| SEQ. ID. NO. 19282 | 98-GlnValThrLysSerSerGlnAsp-105 |
| Antigenic Index - Jameson-Wolf | |
| SEQ. ID. NO. 19283 | 32-LysGlnPheAsnAsnAspAlaAspGlyIleSerGlySer-44 |
| SEQ. ID. NO. 19284 | 48-ThrValGlnSerLysLysLysThrGlnThrAlaHisGlyThr-61 |
| SEQ. ID. NO. 19285 | 74-TyrThrSerProTyrLysGlnThrIle-82 |
| SEQ. ID. NO. 19286 | 98-GlnValThrLysSerSerGlnAspGlnAlaIleGlyGlySerPro-112 |
| SEQ. ID. NO. 19287 | 116-LeuSerAsnLysThrAlaLeuGluSerSerTyrThrLeuLysGluAspGlySerSerAsnGly-136 |
| SEQ. ID. NO. 19288 | 142-AlaThrProLysArgAsnAsnAlaGly-150 |
| SEQ. ID. NO. 19289 | 158-PheLysGlyGlyAsn-162 |
| SEQ. ID. NO. 19290 | 167-GlnLeuLysAspSerPheGlyAsnGlnThr-176 |
| SEQ. ID. NO. 19291 | 184-AsnThrAsnProGlnLeuSerArgGlyAlaPhe-194 |
| SEQ. ID. NO. 19292 | 196-PheThrProProLysGlyValAspVal-204 |
| Hydrophilic Regions - Hopp-Woods | |
| SEQ. ID. NO. 19293 | 34-PheAsnAsnAspAlaAspGlyIle-41 |
| SEQ. ID. NO. 19294 | 49-ValGlnSerLysLysLysThrGlnThr-57 |
| SEQ. ID. NO. 19295 | 100-ThrLysSerSerGlnAspGlnAlaIle-108 |
| SEQ. ID. NO. 19296 | 126-TyrThrLeuLysGluAspGlySerSerAsn-135 |
| SEQ. ID. NO. 19297 | 143-ThrProLysArgAsnAsnAla-149 |
| SEQ. ID. NO. 19298 | 167-GlnLeuLysAspSerPheGly-173 |
| a503-1 | |
| AMPHI Regions - AMPHI | |
| SEQ. ID. NO. 19299 | 6-TyrArgGluAlaAsnThrTrp-12 |
| SEQ. ID. NO. 19300 | 96-SerSerThrSerAsnPheAlaSerAlaAlaGluMetArgSerLeu-110 |
| Antigenic Index - Jameson-Wolf | |
| SEQ. ID. NO. 19301 | 4-SerLeuTyrArgGluAlaAsnThr-11 |
| SEQ. ID. NO. 19302 | 26-ArgLysValSerCys-30 |

TABLE 1-continued

| | |
|---|---|
| SEQ. ID. NO. 19303 | 32-ProAlaAsnAspAlaSerGlyArgSerSerAlaValAlaGluGluArgThrAlaThrGluMetSerAlaProProAla-57 |
| SEQ. ID. NO. 19304 | 69-SerAlaSerSerCysSerGlyLysGlyValSer-79 |
| SEQ. ID. NO. 19305 | 87-LeuProThrArgAlaSerSerAlaThrSerSerThrSerAsn-100 |
| SEQ. ID. NO. 19306 | 105-AlaGluMetArgSerLeuArg-111 |
| SEQ. ID. NO. 19307 | 113-LeuCysAlaArgAsnAlaArg-119 |
| Hydrophilic Regions - Hopp-Woods | |
| SEQ. ID. NO. 19308 | 4-SerLeuTyrArgGlu-8 |
| SEQ. ID. NO. 19309 | 35-AspAlaSerGlyArgSerSerAlaValAlaGluGluArgThrAlaThrGluMetSerAla-54 |
| SEQ. ID. NO. 19310 | 73-CysSerGlyLysGlyValSer-79 |
| SEQ. ID. NO. 19311 | 89-ThrArgAlaSerSer-93 |
| SEQ. ID. NO. 19312 | 105-AlaGluMetArgSerLeuArg-111 |
| a505 | |
| AMPHI Regions - AMPHI | |
| SEQ. ID. NO. 19313 | 20-LeuThrAlaLeuLeuLysCysLeuSerLeuLeuProLeuSerCysLeu-35 |
| SEQ. ID. NO. 19314 | 37-ThrLeuGlyAsnArg-41 |
| SEQ. ID. NO. 19315 | 89-ProAlaPhePheArgLysProGluAspIleGluThrMetPheLysAlaValHisGlyTrpGluHisValGlnGlnAlaLeuAsp-116 |
| SEQ. ID. NO. 19316 | 148-AlaMetTyrLysProProLysIleLysAlaIleAspLysIleMetGlnAlaGly-165 |
| SEQ. ID. NO. 19317 | 178-IleGlnGlyValLysGlnIleIleLysAlaLeuArg-189 |
| SEQ. ID. NO. 19318 | 210-GlyValTrpValAspPhePheGlyLysPro-219 |
| Antigenic Index - Jameson-Wolf | |
| SEQ. ID. NO. 19319 | 38-LeuGlyAsnArgLeuGly-43 |
| SEQ. ID. NO. 19320 | 50-LeuLysGluAspArgAlaArgIle-57 |
| SEQ. ID. NO. 19321 | 62-ArgGlnAlaGlyMetAsnProAspProLysThrVal-73 |
| SEQ. ID. NO. 19322 | 79-GluThrAlaLysGlyGlyLeu-85 |
| SEQ. ID. NO. 19323 | 92-PheArgLysProGluAspIleGluThr-100 |
| SEQ. ID. NO. 19324 | 114-AlaLeuAspLysHisGlu-119 |
| SEQ. ID. NO. 19325 | 129-GlySerTyrAspLeuGlyGlyArgTyrIleSer-139 |
| SEQ. ID. NO. 19326 | 142-LeuProPheProLeu-146 |
| SEQ. ID. NO. 19327 | 150-TyrLysProProLysIleLysAlaIleAspLysIleMetGln-163 |
| SEQ. ID. NO. 19328 | 165-GlyArgValArgGlyLysGlyLysThrAlaProThrSer-177 |
| SEQ. ID. NO. 19329 | 183-GlnIleIleLysAlaLeuArgSerGlyGluAlaThr-194 |
| SEQ. ID. NO. 19330 | 198-ProAspHisValProSerProGlnGluGlyGlyGluGlyVal-211 |
| SEQ. ID. NO. 19331 | 242-CysGluArgLeuProGlyGlyGlnGly-250 |
| SEQ. ID. NO. 19332 | 257-ProValGlnGlyGluLeuAsnGlyAspLysAlaHisAsp-269 |
| SEQ. ID. NO. 19333 | 292-TyrAsnArgTyrLysMetPro-298 |
| Hydrophilic Regions - Hopp-Woods | |
| SEQ. ID. NO. 19334 | 50-LeuLysGluAspArgAlaArgIle-57 |
| SEQ. ID. NO. 19335 | 62-ArgGlnAlaGlyMetAsnProAspProLysThrVal-73 |
| SEQ. ID. NO. 19336 | 79-GluThrAlaLysGlyGlyLeu-85 |
| SEQ. ID. NO. 19337 | 92-PheArgLysProGluAspIleGluThr-100 |
| SEQ. ID. NO. 19338 | 114-AlaLeuAspLysHisGlu-119 |
| SEQ. ID. NO. 19339 | 151-LysProProLysIleLysAlaIleAspLysIleMetGln-163 |
| SEQ. ID. NO. 19340 | 165-GlyArgValArgGlyLysGlyLysThrAlaPro-175 |
| SEQ. ID. NO. 19341 | 183-GlnIleIleLysAlaLeuArgSerGlyGlu-192 |
| SEQ. ID. NO. 19342 | 201-ValProSerProGlnGluGlyGlyGlu-209 |
| SEQ. ID. NO. 19343 | 258-ValGlnGlyGluLeuAsnGlyAspLysAlaHisAsp-269 |
| a506 | |
| AMPHI Regions - AMPHI | |
| SEQ. ID. NO. 19344 | 6-GluValGlyArgValAlaHisCysGlyGlyGlyVal-17 |
| SEQ. ID. NO. 19345 | 25-ArgValValHisGlnValGluGlnGlyAlaArg-35 |
| SEQ. ID. NO. 19346 | 53-AlaValAspPheGlnArgArgPhe-60 |
| SEQ. ID. NO. 19347 | 99-AlaThrArgThrValAspArgAspLeuAlaGluVal-110 |
| SEQ. ID. NO. 19348 | 138-GlyAsnGluValAlaArgCys-144 |
| SEQ. ID. NO. 19349 | 180-GlnValLysArgMetIleArgHisPhePheArg-190 |
| SEQ. ID. NO. 19350 | 199-ValHisArgProPheArgLysLeuAlaAlaLeuAspGlyPheValGlnVal-215 |
| SEQ. ID. NO. 19351 | 224-GlyAspAspPheGlyGlyPhePheValGlyGlnValPheAsnAlaLeuLeu-240 |
| SEQ. ID. NO. 19352 | 313-PheValGlnValGlyGluLeuThrArgValAlaGlnGluGlu-326 |
| SEQ. ID. NO. 19353 | 372-GlyPhePheAlaAspPheAlaGluAspPheGlyAlaGlyValPheGlyAspValValArgTyrGlyLysArgThr-396 |
| SEQ. ID. NO. 19354 | 408-PheGlyAspAspPheAlaHisGluValGlyGlu-418 |
| SEQ. ID. NO. 19355 | 427-ArgGlnGlnArgAlaAlaArgThr-434 |
| Antigenic Index - Jameson-Wolf | |
| SEQ. ID. NO. 19356 | 13-CysGlyGlyGlyValAla-18 |
| SEQ. ID. NO. 19357 | 31-GluGlnGlyAlaArgLeu-36 |
| SEQ. ID. NO. 19358 | 48-ProValArgArgValAlaValAspPheGlnArgArgPheGlyGluVal-63 |
| SEQ. ID. NO. 19359 | 98-ArgAlaThrArgThrValAspArgAspLeuAlaGlu-109 |
| SEQ. ID. NO. 19360 | 134-GlyAlaAspThrGlyAsnGluValAlaArgCysGluGly-146 |
| SEQ. ID. NO. 19361 | 176-ProAsnPheGlyGlnValLysArgMetIle-185 |
| SEQ. ID. NO. 19362 | 192-GlyPheArgHisAspLeuAspValHisArgProPheArgLys-205 |
| SEQ. ID. NO. 19363 | 223-ValGlyAspAspPheGlyGly-229 |
| SEQ. ID. NO. 19364 | 244-MetGluPheHisProLysThr-250 |
| SEQ. ID. NO. 19365 | 259-ValGlyMetArgThrGluAla-265 |
| SEQ. ID. NO. 19366 | 289-GlyGlnGlnArgProGluValProVal-297 |
| SEQ. ID. NO. 19367 | 318-GluLeuThrArgValAlaGlnGluGluHisGlyArgValValAla-332 |
| SEQ. ID. NO. 19368 | 343-GluLeuGlnArgLysThrAlaAsp-350 |
| SEQ. ID. NO. 19369 | 362-CysHisGlyGlyGluThrGlyGlu-369 |
| SEQ. ID. NO. 19370 | 377-PheAlaGluAspPheGly-382 |
| SEQ. ID. NO. 19371 | 389-ValValArgTyrGlyLysArgThrGluArgAlaArgThr-401 |
| SEQ. ID. NO. 19372 | 408-PheGlyAspAspPheAlaHisGluVal-416 |
| SEQ. ID. NO. 19373 | 424-GlnIleLeuArgGlnGlnArgAlaAlaArgThrGlyGlyGln-437 |
| SEQ. ID. NO. 19374 | 442-ValGlyAsnArgArgAlaVal-448 |

TABLE 1-continued

| | |
|---|---|
| SEQ. ID. NO. 19375 | 458-PheGlyGlyXxxHisArgSerCysSer-466 |
| SEQ. ID. NO. 19376 | 471-GlyGlnXxxGlyGlyLysArgLeuThrValArgPheGlyGlyLysArgIleArgAsnArgPheLeuAspCysAsnLysPheLeuGlu-499 |
| SEQ. ID. NO. 19377 | 510-MetAspAlaThrIleArgGlnAspPheArgTyr-520 |

Hydrophilic Regions - Hopp-Woods

| | |
|---|---|
| SEQ. ID. NO. 19378 | 31-GluGlnGlyAlaArgLeu-36 |
| SEQ. ID. NO. 19379 | 48-ProValArgArgValAlaValAspPheGlnArgArgPheGlyGlu-62 |
| SEQ. ID. NO. 19380 | 98-ArgAlaThrArgThrValAspArgAspLeuAlaGlu-109 |
| SEQ. ID. NO. 19381 | 136-AspThrGlyAsnGluValAlaArgCysGluGly-146 |
| SEQ. ID. NO. 19382 | 180-GlnValLysArgMetIle-185 |
| SEQ. ID. NO. 19383 | 195-HisAspLeuAspVal-199 |
| SEQ. ID. NO. 19384 | 201-ArgProPheArgLys-205 |
| SEQ. ID. NO. 19385 | 223-ValGlyAspAspPhe-227 |
| SEQ. ID. NO. 19386 | 244-MetGluPheHisPro-248 |
| SEQ. ID. NO. 19387 | 259-ValGlyMetArgThrGluAla-265 |
| SEQ. ID. NO. 19388 | 291-GlnArgProGluVal-295 |
| SEQ. ID. NO. 19389 | 318-GluLeuThrArgValAlaGlnGluGluHisGlyArgValValAla-332 |
| SEQ. ID. NO. 19390 | 343-GluLeuGlnArgLysThrAlaAsp-350 |
| SEQ. ID. NO. 19391 | 364-GlyGlyGluThrGlyGlu-369 |
| SEQ. ID. NO. 19392 | 377-PheAlaGluAspPheGly-382 |
| SEQ. ID. NO. 19393 | 390-ValArgTyrGlyLysArgThrGluArgAlaArgThr-401 |
| SEQ. ID. NO. 19394 | 408-PheGlyAspAspPheAlaHisGluVal-416 |
| SEQ. ID. NO. 19395 | 425-IleLeuArgGlnGlnArgAlaAlaArgThrGlyGly-436 |
| SEQ. ID. NO. 19396 | 443-GlyAsnArgArgAlaVal-448 |
| SEQ. ID. NO. 19397 | 473-XxxGlyGlyLysArgLeuThr-479 |
| SEQ. ID. NO. 19398 | 482-PheGlyGlyLysArgIleArgAsnArgPheLeuAsp-493 |
| SEQ. ID. NO. 19399 | 510-MetAspAlaThrIleArgGlnAspPheArgTyr-520 | a513
AMPHI Regions - AMPHI

| | |
|---|---|
| SEQ. ID. NO. 19400 | 6-ThrGluTrpLeuHisGlyTrpValGlyAlaIleAsnAspProMetTrp-21 |
| SEQ. ID. NO. 19401 | 23-TyrLeuValTyrXxxLeu-28 |
| SEQ. ID. NO. 19402 | 48-GlyArgSerIleLysGlu-53 |
| SEQ. ID. NO. 19403 | 66-GlyIleThrProPheGlnAlaPheValThrGlyLeuAla-78 |
| SEQ. ID. NO. 19404 | 119-SerSerLeuAlaGlnLeuPheLysValArgAsp-129 |
| SEQ. ID. NO. 19405 | 146-GlyLeuGlyGlnLysTrpLeuGlyVal-154 |
| SEQ. ID. NO. 19406 | 176-IleAlaAspThrVal-180 |
| SEQ. ID. NO. 19407 | 205-GlyGlyIleArgArgIleSerLysAlaAla-214 |
| SEQ. ID. NO. 19408 | 243-ValPheGlyGlnIlePheSer-249 |
| SEQ. ID. NO. 19409 | 259-GlyGlyLeuLeuGlyGlyLeuIle-266 |
| SEQ. ID. NO. 19410 | 288-AlaProAsnAlaAlaAlaAlaAla-295 |
| SEQ. ID. NO. 19411 | 303-GlnGlyMetIleGlnMetLeuGlyValPheValAsp-314 |
| SEQ. ID. NO. 19412 | 332-ProTyrGlyAspLeu-336 |
| SEQ. ID. NO. 19413 | 347-ValSerGlnValGlyGlnTrp-353 |
| SEQ. ID. NO. 19414 | 391-ThrAlaValPheArgMet-396 |
| SEQ. ID. NO. 19415 | 403-TyrPheGlyAlaValAla-408 |
| SEQ. ID. NO. 19416 | 423-IleMetAlaTrpIleAsnLeuValAlaIleLeuLeuLeuSer-436 |

Antigenic Index - Jameson-Wolf

| | |
|---|---|
| SEQ. ID. NO. 19417 | 1-MetAsnGluAsnPhe-5 |
| SEQ. ID. NO. 19418 | 48-GlyArgSerIleLysGluMetLeuGlyGlyArgLysGlnGlyAspAspProHisGly-66 |
| SEQ. ID. NO. 19419 | 126-LysValArgAspTyrAspAsnHisHisPheArgGlyGlyProAla-140 |
| SEQ. ID. NO. 19420 | 208-ArgArgIleSerLysAlaAlaGlu-215 |
| SEQ. ID. NO. 19421 | 273-GlyIleLysArgGlyLeuTyrSerAsnGluAlaGlyMetGlySerAlaProAsnAla-291 |
| SEQ. ID. NO. 19422 | 295-AlaGluValLysHisProVal-301 |
| SEQ. ID. NO. 19423 | 331-GlnProTyrGlyAspLeuSerGly |
| SEQ. ID. NO. 19424 | 375-AlaTyrAlaGluSerAsnVal-381 |
| SEQ. ID. NO. 19425 | 444-ArgAspTyrThrAlaLysLeuLysMetGlyLysAspProGluPheLysLeuSerGluHisProGlyLeuLysArgArgIleLysSerAspValTrp-475 |

Hydrophilic Regions - Hopp-Woods

| | |
|---|---|
| SEQ. ID. NO. 19426 | 48-GlyArgSerIleLysGluMetLeuGlyGlyArgLysGlnGlyAspAspProHisGly-66 |
| SEQ. ID. NO. 19427 | 126-LysValArgAspTyrAspAsnHisHis-134 |
| SEQ. ID. NO. 19428 | 208-ArgArgIleSerLysAlaAlaGlu-215 |
| SEQ. ID. NO. 19429 | 273-GlyIleLysArgGlyLeuTyr-279 |
| SEQ. ID. NO. 19430 | 295-AlaGluValLysHis-299 |
| SEQ. ID. NO. 19431 | 450-LeuLysMetGlyLysAspProGluPheLysLeuSerGlu-462 |
| SEQ. ID. NO. 19432 | 464-ProGlyLeuLysArgArgIleLysSer-472 | a515-1
AMPHI Regions - AMPHI

| | |
|---|---|
| SEQ. ID. NO. 19433 | 8-ArgAlaAlaGlyValAlaArgGlyLeuHisSerGluPheAlaArg-22 |
| SEQ. ID. NO. 19434 | 59-AspValArgPhePheAlaGlnValGluGluIleGlyGlnAspPhePheAlaAspAla-77 |
| SEQ. ID. NO. 19435 | 90-AlaGlyGluCysAlaAspGluValSerAspLysThr-101 |
| SEQ. ID. NO. 19436 | 122-GluSerAlaGlnSerAlaAlaGlyGlyGlyLeuThrAspGlyPheGly-137 |
| SEQ. ID. NO. 19437 | 176-CysGlyLysThrValGlyVal-182 |
| SEQ. ID. NO. 19438 | 198-GlyValPheAspAla-202 |
| SEQ. ID. NO. 19439 | 233-ValAlaAspValLeuArg-238 |
| SEQ. ID. NO. 19440 | 251-PheGlyGlyValAlaGlyAspValGlyGlyGlyAlaAspGlyValAlaGlnGlyLeuPheGlyGluIleGlyGlyAla-276 |

Antigenic Index - Jameson-Wolf

| | |
|---|---|
| SEQ. ID. NO. 19441 | 24-ValThrAlaGluGluIleAlaPhe-31 |
| SEQ. ID. NO. 19442 | 38-HisGluAlaArgCysGlyGlyAsn-45 |
| SEQ. ID. NO. 19443 | 51-IleAlaAlaAlaGluArgAlaGlyAsp-59 |
| SEQ. ID. NO. 19444 | 67-GluGluIleGlyGln-71 |
| SEQ. ID. NO. 19445 | 77-AlaValAspGlnGluThr-82 |

TABLE 1-continued

| | |
|---|---|
| SEQ. ID. NO. 19446 | 84-LeuAlaValGluArgSerAlaGlyGluCysAlaAspGluValSerAspLysThrAlaArgAsnGlyGlyIleGluGluAspGlyValValAlaCysArgAspAlaAlaAlaAlaGluSerAlaGln-125 |
| SEQ. ID. NO. 19447 | 128-AlaGlyGlyGlyLeuThrAspGly-135 |
| SEQ. ID. NO. 19448 | 160-GlyGlyAsnAspAlaAlaGlyAsn-167 |
| SEQ. ID. NO. 19449 | 192-LeuHisArgArgAla-196 |
| SEQ. ID. NO. 19450 | 217-AlaAspGlyGlyPheArg-222 |
| SEQ. ID. NO. 19451 | 242-GlyValGlyLysSerGlyAla-248 |
| SEQ. ID. NO. 19452 | 257-AspValGlyGlyGlyAlaAspGlyVal-265 |
| SEQ. ID. NO. 19453 | 284-AspValAsnGlyAsnValGln-290 |
| Hydrophilic Regions - Hopp-Woods | |
| SEQ. ID. NO. 19454 | 24-ValThrAlaGluGluIleAlaPhe-31 |
| SEQ. ID. NO. 19455 | 38-HisGluAlaArgCysGly-43 |
| SEQ. ID. NO. 19456 | 51-IleAlaAlaAlaGluArgAlaGlyAsp-59 |
| SEQ. ID. NO. 19457 | 77-AlaValAspGlnGluThr-82 |
| SEQ. ID. NO. 19458 | 84-LeuAlaValGluArgSerAlaGlyGluCysAlaAspGluValSerAspLysThrAlaArgAsnGlyGlyIleGluGluAspGlyValValAlaCysArgAspAlaAlaAlaAlaGluSerAlaGln-125 |
| SEQ. ID. NO. 19459 | 162-AsnAspAlaAlaGly-166 |
| SEQ. ID. NO. 19460 | 192-LeuHisArgArgAla-196 |
| SEQ. ID. NO. 19461 | 258-ValGlyGlyGlyAlaAspGlyVal-265 |
| a519-1 | |
| AMPHI Regions - AMPHI | |
| SEQ. ID. NO. 19462 | 29-ValValGluArgLeuGlyArgPheHisArgAlaLeuThrAlaGly-43 |
| SEQ. ID. NO. 19463 | 105-MetAlaIleThrGlnLeuAlaGlnThrThrLeuArgSerVal-118 |
| SEQ. ID. NO. 19464 | 139-ValSerAlaLeuAspGluAlaAla-146 |
| SEQ. ID. NO. 19465 | 166-GluIleLeuArgSerMetGlnAla-173 |
| SEQ. ID. NO. 19466 | 192-LysIleGluGlnIle-196 |
| SEQ. ID. NO. 19467 | 221-SerAsnAlaGluLysIleAlaArgIleAsn-230 |
| SEQ. ID. NO. 19468 | 249-AlaIleArgGlnIleAlaAlaAla-256 |
| SEQ. ID. NO. 19469 | 273-GlnTyrValAlaAlaPheAsnAsnLeuAlaLys-283 |
| SEQ. ID. NO. 19470 | 292-AlaAsnValAlaAspIleGlySerLeuIleSerAlaGlyMetLysIleIleAspSerSerLysThrAla-314 |
| Antigenic Index - Jameson-Wolf | |
| SEQ. ID. NO. 19471 | 31-GluArgLeuGlyArgPheHisArg-38 |
| SEQ. ID. NO. 19472 | 58-HisSerLeuLysGluIleProLeuAspValProSerGln-70 |
| SEQ. ID. NO. 19473 | 72-CysIleThrArgAspAsnThrGlnLeuThrVal-82 |
| SEQ. ID. NO. 19474 | 91-ThrAspProLysLeuAlaSer-97 |
| SEQ. ID. NO. 19475 | 122-MetGluLeuAspLysThrPheGluGluArgAspGluIleAsn-135 |
| SEQ. ID. NO. 19476 | 141-AlaLeuAspGluAlaAlaGly-147 |
| SEQ. ID. NO. 19477 | 154-LeuArgTyrGluIleLysAspLeuValPro-163 |
| SEQ. ID. NO. 19478 | 175-IleThrAlaGluArgGluLysArgAlaArgIleAlaGluSerGluGlyArgLysIleGluGln-195 |
| SEQ. ID. NO. 19479 | 197-AsnLeuAlaSerGlyGlnArgGluAlaGluIleGlnGlnSerGluGlyGluAlaGlnAla-216 |
| SEQ. ID. NO. 19480 | 219-AsnAlaSerAsnAlaGluLysIleAlaArgIleAsnArgAlaLysGlyGluAlaGluSerLeuArgLeu-241 |
| SEQ. ID. NO. 19481 | 245-AlaAsnAlaGluAlaIleArg-251 |
| SEQ. ID. NO. 19482 | 258-GlnThrGlnGlyGlyAlaAspAlaValAsn-267 |
| SEQ. ID. NO. 19483 | 281-LeuAlaLysGluSerAsnThr-287 |
| SEQ. ID. NO. 19484 | 303-AlaGlyMetLysIleIleAspSerSerLysThrAlaLys-315 |
| Hydrophilic Regions - Hopp-Woods | |
| SEQ. ID. NO. 19485 | 31-GluArgLeuGlyArgPheHisArg-38 |
| SEQ. ID. NO. 19486 | 58-HisSerLeuLysGluIleProLeu-65 |
| SEQ. ID. NO. 19487 | 73-IleThrArgAspAsnThr-78 |
| SEQ. ID. NO. 19488 | 91-ThrAspProLysLeu-95 |
| SEQ. ID. NO. 19489 | 122-MetGluLeuAspLysThrPheGluGluArgAspGluIleAsn-135 |
| SEQ. ID. NO. 19490 | 141-AlaLeuAspGluAlaAla-146 |
| SEQ. ID. NO. 19491 | 154-LeuArgTyrGluIleLysAspLeuValPro-163 |
| SEQ. ID. NO. 19492 | 175-IleThrAlaGluArgGluLysArgAlaArgIleAlaGluSerGluGlyArgLysIleGluGln-195 |
| SEQ. ID. NO. 19493 | 200-SerGlyGlnArgGluAlaGluIleGlnGlnSerGluGlyGluAlaGlnAla-216 |
| SEQ. ID. NO. 19494 | 221-SerAsnAlaGluLysIleAlaArgIleAsnArgAlaLysGlyGluAlaGluSerLeuArgLeu-241 |
| SEQ. ID. NO. 19495 | 245-AlaAsnAlaGluAlaIleArg-251 |
| SEQ. ID. NO. 19496 | 281-LeuAlaLysGluSerAsn-286 |
| SEQ. ID. NO. 19497 | 306-LysIleIleAspSerSerLysThrAlaLys-315 |
| a520-1 | |
| AMPHI Regions - AMPHI | |
| SEQ. ID. NO. 19498 | 104-LeuThrLysAlaAlaAspGlyGlnValCysArgAlaPheSerSerLeu-119 |
| Antigenic Index - Jameson-Wolf | |
| SEQ. ID. NO. 19499 | 20-LysProSerArgArgAlaLeu-26 |
| SEQ. ID. NO. 19500 | 47-AlaSerGlyLysIleSerLeuPro-54 |
| SEQ. ID. NO. 19501 | 84-ProProAsnAsnSerThrThrThrSerThrSerSerArgAlaThrSerSerAsnGlySerLeuThrLysAlaAlaAspGlyGlnVal-112 |
| SEQ. ID. NO. 19502 | 117-SerSerLeuLysSerHisThrAlaGluIleArgIleSerArgProLysArgArgGluIleSerSerAlaLeuSerArgAsnThrAlaAla-146 |
| SEQ. ID. NO. 19503 | 150-ProThrValProLysProLysArgProMet-159 |
| SEQ. ID. NO. 19504 | 166-SerProCysLysProThrGluMet-173 |
| Hydrophilic Regions - Hopp-Woods | |
| SEQ. ID. NO. 19505 | 20-LysProSerArgArgAlaLeu-26 |
| SEQ. ID. NO. 19506 | 93-ThrSerSerArgAlaThrSerSer-100 |
| SEQ. ID. NO. 19507 | 103-SerLeuThrLysAlaAlaAsp-109 |
| SEQ. ID. NO. 19508 | 120-LysSerHisThrAlaGluIleArgIleSerArgProLysArgArgGluIleSer-137 |
| SEQ. ID. NO. 19509 | 140-LeuSerArgAsnThrAla-145 |
| SEQ. ID. NO. 19510 | 151-ThrValProLysProLysArgProMet-159 |
| SEQ. ID. NO. 19511 | 168-CysLysProThrGluMet-173 |
| a521 | |
| AMPHI Regions - AMPHI | |
| SEQ. ID. NO. 19512 | 86-ValLysThrValSerLysProAlaLys-94 |

TABLE 1-continued

| | |
|---|---|
| SEQ. ID. NO. 19513 | 133-GlnAlaArgLeuAlaLysGlyGlyAsn-141 |
| SEQ. ID. NO. 19514 | 147-IleAsnAlaLeuGlnSerValLeuAsp-155 |
| Antigenic Index - Jameson-Wolf | |
| SEQ. ID. NO. 19515 | 1-MetLysSerLysLeu-5 |
| SEQ. ID. NO. 19516 | 36-ValTyrThrThrLysProSerLysSerCysLeuSerThrAspLeuProProIle-53 |
| SEQ. ID. NO. 19517 | 55-AsnTyrSerSerGluArgTyrIleProProGlnThrSerGluProThrProSerProSerAsnGlyGlyGln-78 |
| SEQ. ID. NO. 19518 | 80-ValLysTyrLysAlaProVal-86 |
| SEQ. ID. NO. 19519 | 88-ThrValSerLysProAlaLysSerAsnThrProProProGlnGlnAlaProSerAsnAsnSerArgArgSerIleLeuGluThrGluLeuSerAsnGlu ArgLysAlaLeuValGluAlaGlnLysMetLeuSer-132 |
| SEQ. ID. NO. 19520 | 135-ArgLeuAlaLysGlyGlyAsnIleAsn-143 |
| SEQ. ID. NO. 19521 | 153-ValLeuAspArgGlnGlnAsn-159 |
| SEQ. ID. NO. 19522 | 163-LeuGlnArgGluLeuGlyArg-169 |
| Hydrophilic Regions - Hopp-Woods | |
| SEQ. ID. NO. 19523 | 1-MetLysSerLysLeu-5 |
| SEQ. ID. NO. 19524 | 40-LysProSerLysSerCysLeu-46 |
| SEQ. ID. NO. 19525 | 57-SerSerGluArgTyrIle-62 |
| SEQ. ID. NO. 19526 | 65-GlnThrSerGluProThrProSerProSerAsnGly-76 |
| SEQ. ID. NO. 19527 | 80-ValLysTyrLysAlaProVal-86 |
| SEQ. ID. NO. 19528 | 88-ThrValSerLysProAlaLysSerAsnThrProPro-99 |
| SEQ. ID. NO. 19529 | 102-GlnAlaProSerAsnAsnSerArgArgSerIleLeuGluThrGluLeuSerAsnGluArgLysAlaLeuValGluAlaGlnLysMetLeuSer-132 |
| SEQ. ID. NO. 19530 | 153-ValLeuAspArgGlnGlnAsn-159 |
| SEQ. ID. NO. 19531 | 163-LeuGlnArgGluLeuGlyArg-169 |
| a522 | |
| AMPHI Regions - AMPHI | |
| SEQ. ID. NO. 19532 | 57-LysIleValGluSerCysValLys-64 |
| SEQ. ID. NO. 19533 | 96-MetTrpGluGlnProLeuAspArgLeuSerGluLysGlnIleSerSerPheGlyLysLeuGlyAlaGlnGluGlnLeuAspLeuLeuGlyGlyAla-127 |
| Antigenic Index - Jameson-Wolf | |
| SEQ. ID. NO. 19534 | 1-MetThrGluProLysHisGluMetProThrGluGluGlnValAlaAlaArgLysLysAlaLysAlaLysIleArgThr-26 |
| SEQ. ID. NO. 19535 | 48-AlaMetSerLysProGlnAlaLysGlnLysIleValGluSerCysValLys-64 |
| SEQ. ID. NO. 19536 | 71-LysTrpGlnAsnAspLeuArgAlaArgGlyLeuAspSerAsnAsnThrArgLeuThr-89 |
| SEQ. ID. NO. 19537 | 99-GlnProLeuAspArgLeuSerGluLysGlnIleSerSerPheGlyLysLeuGlyAla-117 |
| SEQ. ID. NO. 19538 | 128-AsnAlaPheGluThrArgAspLysGlnCysValAlaAspLeuLysSerGlu-144 |
| Hydrophilic Regions - Hopp-Woods | |
| SEQ. ID. NO. 19539 | 1-MetThrGluProLysHisGluMetProThrGluGluGlnValAlaAlaArgLysLysAlaLysAlaLysIleArgThr-26 |
| SEQ. ID. NO. 19540 | 48-AlaMetSerLysProGlnAlaLysGlnLysIleValGluSerCysVal-63 |
| SEQ. ID. NO. 19541 | 72-TrpGlnAsnAspLeuArgAlaArgGlyLeuAspSerAsnAsnThr-86 |
| SEQ. ID. NO. 19542 | 100-ProLeuAspArgLeuSerGluLysGlnIle-109 |
| SEQ. ID. NO. 19543 | 130-PheGluThrArgAspLysGlnCysValAlaAspLeuLysSerGlu-144 |
| a525-1 | |
| AMPHI Regions - AMPHI | |
| SEQ. ID. NO. 19544 | 59-GluPheAlaGluPheValAsnSerHisProGln-69 |
| SEQ. ID. NO. 19545 | 86-LysHisTrpMetLysAsnGly-92 |
| SEQ. ID. NO. 19546 | 125-ArgLeuProThrIleAspGluTrpGluPhe-134 |
| SEQ. ID. NO. 19547 | 166-AspLeuHisAspValGly-171 |
| SEQ. ID. NO. 19548 | 178-TrpGlyValTyrAsp-182 |
| SEQ. ID. NO. 19549 | 188-TrpGluTrpThrGlu-192 |
| Antigenic Index - Jameson-Wolf | |
| SEQ. ID. NO. 19550 | 24-ValGlnIleGluGlyGlySerTyrArgProLeuTyrLeuLysLysAspThrGlyLeuIleLys-44 |
| SEQ. ID. NO. 19551 | 46-LysProPheLysLeuAspLysTyrProValThr-56 |
| SEQ. ID. NO. 19552 | 67-HisProGlnTrpGlnLysGlyArgIleGlySerLysGlnAlaGlu-81 |
| SEQ. ID. NO. 19553 | 88-TrpMetLysAsnGlySerArgSerTyrAlaProLysAlaGlyAspLeuLysGlnPro-106 |
| SEQ. ID. NO. 19554 | 122-GlnGlyLysArgLeuProThrIleAspGluTrpGlu-133 |
| SEQ. ID. NO. 19555 | 140-AlaThrGlnLysAsnGlySerAsnGluProGlyTyrAsnArgThr-154 |
| SEQ. ID. NO. 19556 | 159-TyrAlaAspGlyAspArgLysAspLeuHisAspValGlyLysGlyArgProAsnTyr-177 |
| SEQ. ID. NO. 19557 | 190-TrpThrGluAspPheAsnSerSerLeuLeuSerSerGlyAsnAla-204 |
| SEQ. ID. NO. 19558 | 213-AlaSerIleGlySerSerAspSerSerAsnTyr-223 |
| SEQ. ID. NO. 19559 | 234-SerLeuGlnSerLysTyr-239 |
| Hydrophilic Regions - Hopp-Woods | |
| SEQ. ID. NO. 19560 | 35-TyrLeuLysLysAspThrGlyLeuIleLys-44 |
| SEQ. ID. NO. 19561 | 46-LysProPheLysLeuAspLysTyrPro-54 |
| SEQ. ID. NO. 19562 | 71-GlnLysGlyArgIleGlySerLysGlnAlaGlu-81 |
| SEQ. ID. NO. 19563 | 91-AsnGlySerArgSerTyrAla-97 |
| SEQ. ID. NO. 19564 | 99-LysAlaGlyAspLeuLysGln-105 |
| SEQ. ID. NO. 19565 | 122-GlnGlyLysArgLeuProThr-128 |
| SEQ. ID. NO. 19566 | 140-AlaThrGlnLysAsnGlySerAsnGluProGlyTyr-151 |
| SEQ. ID. NO. 19567 | 160-AlaAspGlyAspArgLysAspLeuHisAspValGlyLysGlyArgPro-175 |
| SEQ. ID. NO. 19568 | 216-GlySerSerAspSerSerAsn-222 |
| a527 | |
| AMPHI Regions - AMPHI | |
| SEQ. ID. NO. 19569 | 7-PhePheGlnProValGln-12 |
| SEQ. ID. NO. 19570 | 28-SerAspAlaAlaGluLeuValGluLeuPheAlaLeuPhePro-41 |
| SEQ. ID. NO. 19571 | 73-GlyLysGlyIleGluArgGlnValAspAsnIleAlaAspValTyrGlyPhe-89 |
| Antigenic Index - Jameson-Wolf | |
| SEQ. ID. NO. 19572 | 26-GlyGlySerAspAlaAlaGlu-32 |
| SEQ. ID. NO. 19573 | 52-GlnLysProArgLeuGlyCys-58 |
| SEQ. ID. NO. 19574 | 71-PheIleGlyLysGlyIleGluArgGlnValAspAsnIleAla-84 |
| SEQ. ID. NO. 19575 | 107-LeuLeuArgLysGlyThrGlyLeuGluLysThrCysArgProLysProPheValGlnProHisGlyGlyArg-130 |
| Hydrophilic Regions - Hopp-Woods | |
| SEQ. ID. NO. 19576 | 27-GlySerAspAlaAlaGlu-32 |
| SEQ. ID. NO. 19577 | 52-GlnLysProArgLeuGlyCys-58 |

TABLE 1-continued

| | |
|---|---|
| SEQ. ID. NO. 19578 | 75-GlyIleGluArgGlnValAspAsnIleAla-84 |
| SEQ. ID. NO. 19579 | 107-LeuLeuArgLysGlyThrGlyLeuGluLysThrCysArgProLysPro-122 | a528
AMPHI Regions - AMPHI

| | |
|---|---|
| SEQ. ID. NO. 19580 | 7-LysTyrThrAlaMetAlaAlaLeuLeuAlaPhe-17 |
| SEQ. ID. NO. 19581 | 23-ArgLeuAlaGlyTrpTyrGluCysSerSerLeuSerGlyTrpCysLysProArgLysProAlaAlaIle-45 |
| SEQ. ID. NO. 19582 | 69-AsnArgSerValArg-73 |
| SEQ. ID. NO. 19583 | 86-TyrArgLysIleGlyLysPhe-92 |
| SEQ. ID. NO. 19584 | 106-ProLeuIleGluThrPheLys-112 |

Antigenic Index - Jameson-Wolf

| | |
|---|---|
| SEQ. ID. NO. 19585 | 1-MetGluIleArgAla-5 |
| SEQ. ID. NO. 19586 | 29-GluCysSerSerLeuSerGlyTrpCysLysProArgLysProAlaAla-44 |
| SEQ. ID. NO. 19587 | 49-AspIleGlyGlyGluSerProProSerLeuGluAspTyrGluIleProLeuSerAspGlyAsnArgSerValArgAlaAsnGluTyrGluSerAlaGln GlnSer-83 |
| SEQ. ID. NO. 19588 | 88-LysIleGlyLysPheGluAlaCysGlyLeuAspTrpArgThrArgAspGlyLysProLeu-107 |
| SEQ. ID. NO. 19589 | 110-ThrPheLysGlnGluGlyPheAspCysLeuLysLysGlnGlyLeuArgArgAsnGlyLeuSerGluArgValArgTrp-135 |

Hydrophilic Regions - Hopp-Woods

| | |
|---|---|
| SEQ. ID. NO. 19590 | 1-MetGluIleArgAla-5 |
| SEQ. ID. NO. 19591 | 37-CysLysProArgLysProAlaAla-44 |
| SEQ. ID. NO. 19592 | 51-GlyGlyGluSerProProSerLeuGluAspTyrGluIleProLeu-65 |
| SEQ. ID. NO. 19593 | 67-AspGlyAsnArgSerValArgAlaAsnGluTyrGluSerAlaGln-81 |
| SEQ. ID. NO. 19594 | 88-LysIleGlyLysPheGluAlaCys-95 |
| SEQ. ID. NO. 19595 | 99-TrpArgThrArgAspGlyLysProLeu-107 |
| SEQ. ID. NO. 19596 | 111-PheLysGlnGluGlyPheAspCysLeuLysLysGlnGlyLeuArgArgAsnGlyLeuSerGluArgValArgTrp-135 | a529
AMPHI Regions - AMPHI

| | |
|---|---|
| SEQ. ID. NO. 19597 | 11-LeuAlaLeuIleGlyLeuAlaAlaCysSer-20 |
| SEQ. ID. NO. 19598 | 35-SerHisArgLeuIle-39 |
| SEQ. ID. NO. 19599 | 49-AsnProAspGlnGlyAsnLeuTyrArgLeuProAla-60 |
| SEQ. ID. NO. 19600 | 79-GlnGlnProAlaAspAlaGluValLeuLysSerValLysGlyValArg-94 |
| SEQ. ID. NO. 19601 | 152-GlnAspSerLeuArgArgLeuPheAsp-160 |
| SEQ. ID. NO. 19602 | 162-ValGlyLeuGlyGlyIleTyr-168 |
| SEQ. ID. NO. 19603 | 196-AlaMetLysGluVal-200 |
| SEQ. ID. NO. 19604 | 223-AlaPheLeuThrArgPheMetGlnTyrLeu-232 |
| SEQ. ID. NO. 19605 | 252-AlaAsnGluMetAla-256 |
| SEQ. ID. NO. 19606 | 270-GlyArgAsnTrpArg-274 |

Antigenic Index - Jameson-Wolf

| | |
|---|---|
| SEQ. ID. NO. 19607 | 19-CysSerGlySerLysThrGluGlnProLysLeuAspTyrGlnSerArgSerHisArgLeuIleLys-40 |
| SEQ. ID. NO. 19608 | 42-GluValProProAspLeuAsnAsnProAspGlnGlyAsnLeuTyr-56 |
| SEQ. ID. NO. 19609 | 60-AlaGlySerGlyAlaValArgAlaSerAspLeuGluLysArgArgThrProAlaVal-78 |
| SEQ. ID. NO. 19610 | 80-GlnProAlaAspAlaGluValLeuLysSerValLysGlyValArgLeuGluArgAspGlySerGln-101 |
| SEQ. ID. NO. 19611 | 105-ValValAlaGlyLysSerHisAla-112 |
| SEQ. ID. NO. 19612 | 123-GlnGluAsnGlyPheAspIleLysSerGluGluProAla-135 |
| SEQ. ID. NO. 19613 | 139-MetGluThrGluTrpAlaGluAsnArgAlaLysIleProGlnAspSerLeuArgArgLeuPhe-159 |
| SEQ. ID. NO. 19614 | 169-SerThrGlyGluArgAspLysPheIleValArgIleGluGlnGlyLysAsnGlyValSer-188 |
| SEQ. ID. NO. 19615 | 195-LysAlaMetLysGluValTyrGlyGlyLysAspLysAspThrThr-209 |
| SEQ. ID. NO. 19616 | 212-GlnProSerProSerAspProAsnLeu-220 |
| SEQ. ID. NO. 19617 | 233-GlyValAspGlyGlnGlnAlaGluAsnAlaSerAlaLysLysProThrLeu-249 |
| SEQ. ID. NO. 19618 | 253-AsnGluMetAlaArgIleGluGlyLysSer-262 |
| SEQ. ID. NO. 19619 | 268-AspTyrGlyArgAsnTrpArgArgThrAlaLeuAla-279 |
| SEQ. ID. NO. 19620 | 289-GlyGlnAsnThrGluArgHisAla-296 |
| SEQ. ID. NO. 19621 | 300-GlnLysAlaProAsnGluSerAsnAlaValThrGluGlnLysProGlyLeu-316 |
| SEQ. ID. NO. 19622 | 320-LeuLeuGlyLysGlyLysAlaGluLysProAlaGluGlnProGlu-334 |
| SEQ. ID. NO. 19623 | 342-ValAlaAsnGlySerArg-347 |
| SEQ. ID. NO. 19624 | 350-LeuLeuAsnLysAspGlySerAlaTyrAlaGlyLysAspAlaSer-364 |
| SEQ. ID. NO. 19625 | 370-LeuHisSerGluLeuArg-375 |

Hydrophilic Regions - Hopp-Woods

| | |
|---|---|
| SEQ. ID. NO. 19626 | 20-SerGlySerLysThrGluGlnProLysLeuAspTyrGlnSerArgSerHisArgLeuIleLys-40 |
| SEQ. ID. NO. 19627 | 42-GluValProProAspLeuAsnAsnProAspGln-52 |
| SEQ. ID. NO. 19628 | 63-GlyAlaValArgAlaSerAspLeuGluLysArgArgThrProAla-77 |
| SEQ. ID. NO. 19629 | 80-GlnProAlaAspAlaGluValLeuLysSerValLysGlyValArgLeuGluArgAspGlySerGln-101 |
| SEQ. ID. NO. 19630 | 107-AspGlyLysSerHisAla-112 |
| SEQ. ID. NO. 19631 | 125-AsnGlyPheAspIleLysSerGluGluProAla-135 |
| SEQ. ID. NO. 19632 | 139-MetGluThrGluTrpAlaGluAsnArgAlaLysIleProGlnAspSerLeuArgArgLeuPhe-159 |
| SEQ. ID. NO. 19633 | 170-ThrGlyGluArgAspLysPheIleVal-178 |
| SEQ. ID. NO. 19634 | 180-IleGluGlnGlyLysAsnGlyVal-187 |
| SEQ. ID. NO. 19635 | 195-LysAlaMetLysGluValTyrGlyGlyLysAspLysAspThrThr-209 |
| SEQ. ID. NO. 19636 | 214-SerProSerAspProAsnLeu-220 |
| SEQ. ID. NO. 19637 | 235-AspGlyGlnGlnAlaGluAsnAlaSerAlaLysLysProThr-248 |
| SEQ. ID. NO. 19638 | 253-AsnGluMetAlaArgIleGluGlyLysSer-262 |
| SEQ. ID. NO. 19639 | 269-TyrGlyArgAsnTrpArgArg-275 |
| SEQ. ID. NO. 19640 | 291-AsnThrGluArgHis-295 |
| SEQ. ID. NO. 19641 | 302-AlaProAsnGluSerAsnAlaValThrGluGlnLysProGlyLeu-316 |
| SEQ. ID. NO. 19642 | 320-LeuLeuGlyLysGlyLysAlaGluLysProAlaGluGlnProGlu-334 |
| SEQ. ID. NO. 19643 | 352-AsnLysAspGlySer-356 |
| SEQ. ID. NO. 19644 | 359-AlaGlyLysAspAlaSer-364 |
| SEQ. ID. NO. 19645 | 370-LeuHisSerGluLeuArg-375 | a531
AMPHI Regions - AMPHI

| | |
|---|---|
| SEQ. ID. NO. 19646 | 59-SerLeuAlaGlyIleLeuAlaAspTyrValAlaGlyIleTrpGlyThr-74 |

TABLE 1-continued

| | |
|---|---|
| SEQ. ID. NO. 19647 | 90-GlySerIleIleGlyIlePhePheSerLeuProGlyLeuIleLeuGly-105 |
| SEQ. ID. NO. 19648 | 108-IleGlyAlaAlaAlaGly-113 |
| SEQ. ID. NO. 19649 | 131-ThrLeuLeuGlyLeuIleVal-137 |

Antigenic Index - Jameson-Wolf

| | |
|---|---|
| SEQ. ID. NO. 19650 | 74-ThrLysTyrThrGlyAlaGlyLysLeuAlaVal-84 |
| SEQ. ID. NO. 19651 | 114-GluLeuIleGluArgArgAsnMet-121 |

Hydrophilic Regions - Hopp-Woods

| | |
|---|---|
| SEQ. ID. NO. 19652 | 114-GluLeuIleGluArgArgAsnMet-121 | a532
AMPHI Regions - AMPHI

| | |
|---|---|
| SEQ. ID. NO. 19653 | 6-GlyLysGlyAlaAsp-10 |
| SEQ. ID. NO. 19654 | 27-AlaLeuLeuSerAlaValThrHisLeuLeuAlaIlePheValProMetIleThr-44 |
| SEQ. ID. NO. 19655 | 76-TyrLeuGlnValAsnArgPheGlyPro-84 |
| SEQ. ID. NO. 19656 | 122-SerThrLeuLeuGly-126 |
| SEQ. ID. NO. 19657 | 147-LysValIleThrProThrVal-153 |
| SEQ. ID. NO. 19658 | 184-ThrPheGlySerMetGluAsnLeuGly-192 |
| SEQ. ID. NO. 19659 | 206-CysMetLysAsnPro-210 |
| SEQ. ID. NO. 19660 | 224-GlyTyrIleValAlaLeu-229 |
| SEQ. ID. NO. 19661 | 236-PheSerAlaLeuGlnAsnLeuPro-243 |
| SEQ. ID. NO. 19662 | 271-LeuSerValPheGluAlaValGlyAspLeuThrAla-282 |
| SEQ. ID. NO. 19663 | 297-ThrLysArgLeuArgGlyGlyVal-304 |
| SEQ. ID. NO. 19664 | 307-AspGlyLeuValSerValIleAlaThrAlaLeuGly-318 |
| SEQ. ID. NO. 19665 | 338-AlaSerArgHisValGlyLysTyr-345 |
| SEQ. ID. NO. 19666 | 361-ArgAlaPheThrThrIleProSerProVal-370 |

Antigenic Index - Jameson-Wolf

| | |
|---|---|
| SEQ. ID. NO. 19667 | 1-MetSerGlyGlnLeuGlyLysGlyAlaAspAlaPro-12 |
| SEQ. ID. NO. 19668 | 18-LeuGluAspArgProProPheGlyAsn-26 |
| SEQ. ID. NO. 19669 | 80-AsnArgPheGlyPro-84 |
| SEQ. ID. NO. 19670 | 108-AlaGlyMetLysGluGlyGlyLeuThrLysAspAlaMet-120 |
| SEQ. ID. NO. 19671 | 177-PheGlyAlaLysAlaAspGlyThrPheGlySer-187 |
| SEQ. ID. NO. 19672 | 207-MetLysAsnProLeuLeuArg-213 |
| SEQ. ID. NO. 19673 | 286-ValSerAspGlnProIleGluGlyGluGluTyrThrLysArgLeuArgGlyGlyValLeu-305 |
| SEQ. ID. NO. 19674 | 391-ValSerHisGlyIleArgArgArgGluAlaVal-401 |
| SEQ. ID. NO. 19675 | 445-LeuProGluAspLysThrGluAlaAlaValLysPheAspThrAspHisLeuGluHis-463 |

Hydrophilic Regions - Hopp-Woods

| | |
|---|---|
| SEQ. ID. NO. 19676 | 4-GlnLeuGlyLysGlyAlaAspAlaPro-12 |
| SEQ. ID. NO. 19677 | 18-LeuGluAspArgProProPhe-24 |
| SEQ. ID. NO. 19678 | 109-GlyMetLysGluGlyGlyLeuThrLysAspAlaMet-120 |
| SEQ. ID. NO. 19679 | 179-AlaLysAlaAspGly-183 |
| SEQ. ID. NO. 19680 | 289-GlnProIleGluGlyGluGluTyrThrLysArgLeuArgGly-302 |
| SEQ. ID. NO. 19681 | 394-GlyIleArgArgArgGluAlaVal-401 |
| SEQ. ID. NO. 19682 | 445-LeuProGluAspLysThrGluAlaAlaValLysPheAspThrAspHisLeuGluHis-463 | a537
AMPHI Regions - AMPHI

| | |
|---|---|
| SEQ. ID. NO. 19683 | 38-GlnIleArgAspGlyGlyAspAlaLeuHisTyrLeuAsnArgIle-52 |
| SEQ. ID. NO. 19684 | 86-HisGlyGluHisHis-90 |
| SEQ. ID. NO. 19685 | 109-GlyTyrLeuTyrAsnGlyValHisGlu-117 |
| SEQ. ID. NO. 19686 | 138-ArgGlnValAspGlyLeuMetSerAlaIleTyr-148 |
| SEQ. ID. NO. 19687 | 182-ArgPheGluArgHisCys-187 |
| SEQ. ID. NO. 19688 | 194-ProGluAlaGlyArgLysTyrTyrArgAsnAla-204 |
| SEQ. ID. NO. 19689 | 281-ArgProValArgValLeuThrAlaGly-289 |
| SEQ. ID. NO. 19690 | 315-TyrThrAlaValPheAspTyrValArgAsnGlyArgArgAla-328 |

Antigenic Index - Jameson-Wolf

| | |
|---|---|
| SEQ. ID. NO. 19691 | 21-ThrGlnAsnGlnSerLeuProAlaGly-29 |
| SEQ. ID. NO. 19692 | 32-ValTyrProSerAlaProGlnIleArgAspGlyGlyAspAla-45 |
| SEQ. ID. NO. 19693 | 69-AsnSerAlaArgArgHisAlaArg-76 |
| SEQ. ID. NO. 19694 | 80-LeuAsnProGluAspGlyHisGlyGluHisHisProAspAsnProHis-95 |
| SEQ. ID. NO. 19695 | 99-GlnLysLeuThrGluArgThrArgLeu-107 |
| SEQ. ID. NO. 19696 | 115-ValHisGluAsnIleSerThrGluGluGluAlaAlaGluSerSerAspSerAspIleArgThrGlnGlnArgGlnValAspGlyLeu-143 |
| SEQ. ID. NO. 19697 | 152-SerLeuLeuAspArgHisThrAspGluAlaGly-162 |
| SEQ. ID. NO. 19698 | 165-PheValArgGluAsnGlyLysThr-172 |
| SEQ. ID. NO. 19699 | 178-GlnGlyAsnGlyArgPheGluArgHisCysAlaGlnGlyArgAsnGlnProGluAlaGlyArgLysTyrTyrArgAsnAlaCysHisAsnGly-208 |
| SEQ. ID. NO. 19700 | 212-TyrThrAspGluAlaMetPro-218 |
| SEQ. ID. NO. 19701 | 237-PheHisGlyGluArgProAspProValProGluTyrGluIleThrGlyAsnProAlaSer-256 |
| SEQ. ID. NO. 19702 | 258-AspPheSerGluAlaAlaGly-264 |
| SEQ. ID. NO. 19703 | 266-IleThrMetLysSer-270 |
| SEQ. ID. NO. 19704 | 274-TyrGlnGlyLysAsnGluIleArgPro-282 |
| SEQ. ID. NO. 19705 | 287-ThrAlaGlyAsnAspProAsnGlyArgLeuThr-297 |
| SEQ. ID. NO. 19706 | 320-AspTyrValArgAsnGlyArgArgAlaGlnAla-330 |
| SEQ. ID. NO. 19707 | 334-PheArgThrArgLysProAspTyrProTyr-343 |
| SEQ. ID. NO. 19708 | 345-GluValAsnGlyGlyGluThrLeuAlaValArgLysGlyGluLys-359 |
| SEQ. ID. NO. 19709 | 364-TrpArgGlyArgTrpCysLeu-370 |
| SEQ. ID. NO. 19710 | 376-TyrThrTyrArgGlnArgProGlySerArgLeuSerIleGlyArgHisLysAlaGlyGly-395 |
| SEQ. ID. NO. 19711 | 401-AspGlyMetAlaGlySer-406 |
| SEQ. ID. NO. 19712 | 408-IleThrLeuAlaProGluGlyGluThrGluArgGly-419 |

Hydrophilic Regions - Hopp-Woods

| | |
|---|---|
| SEQ. ID. NO. 19713 | 37-ProGlnIleArgAspGlyGlyAsp-44 |
| SEQ. ID. NO. 19714 | 69-AsnSerAlaArgArgHisAlaArg-76 |
| SEQ. ID. NO. 19715 | 81-AsnProGluAspGlyHisGlyGluHisHisProAsp-92 |
| SEQ. ID. NO. 19716 | 100-LysLeuThrGluArgThrArgLeu-107 |

TABLE 1-continued

| | |
|---|---|
| SEQ. ID. NO. 19717 | 119-IleSerThrGluGluGluAlaAlaGluSerSerAspSerAspIleArgThrGlnGlnArgGlnValAsp-141 |
| SEQ. ID. NO. 19718 | 152-SerLeuLeuAspArgHisThrAspGluAlaGly-162 |
| SEQ. ID. NO. 19719 | 165-PheValArgGluAsnGlyLys-171 |
| SEQ. ID. NO. 19720 | 179-GlyAsnGlyArgPheGluArgHisCysAlaGlnGlyArgAsnGlnProGluAlaGlyArgLysTyrTyrArg-202 |
| SEQ. ID. NO. 19721 | 238-HisGlyGluArgProAspProValProGlu-247 |
| SEQ. ID. NO. 19722 | 258-AspPheSerGluAlaAlaGly-264 |
| SEQ. ID. NO. 19723 | 266-IleThrMetLysSer-270 |
| SEQ. ID. NO. 19724 | 275-GlnGlyLysAsnGluIleArgPro-282 |
| SEQ. ID. NO. 19725 | 289-GlyAsnAspProAsnGlyArg-295 |
| SEQ. ID. NO. 19726 | 323-ArgAsnGlyArgArgAlaGlnAla-330 |
| SEQ. ID. NO. 19727 | 334-PheArgThrArgLysProAsp-340 |
| SEQ. ID. NO. 19728 | 352-LeuAlaValArgLysGlyGluLys-359 |
| SEQ. ID. NO. 19729 | 377-ThrTyrArgGlnArgProGlySer-384 |
| SEQ. ID. NO. 19730 | 387-SerIleGlyArgHisLysAla-393 |
| SEQ. ID. NO. 19731 | 412-ProGluGlyGluThrGluArgGly-419 | a538
AMPHI Regions - AMPHI

| | |
|---|---|
| SEQ. ID. NO. 19732 | 42-ThrAlaLeuAlaGluAlaValGluLeuValLysAlaAlaGly-55 |
| SEQ. ID. NO. 19733 | 79-LysAlaAlaGluLeuSerGluAlaValAla-88 |
| SEQ. ID. NO. 19734 | 105-GlnGluArgAsnLeuGluLysIleLeuGlnCysArgValLeuAspArgVal-121 |
| SEQ. ID. NO. 19735 | 145-GlnLeuSerHisLeuAlaGlyArgLeuIleArgGlyTyrGlyHisLeuGln-161 |
| SEQ. ID. NO. 19736 | 188-IleAsnAlaLeuLysLysGlnLeuAla-196 |
| SEQ. ID. NO. 19737 | 211-SerGlyThrIleLysThrPheAlaLeuValGlyTyrThrAsn-224 |
| SEQ. ID. NO. 19738 | 231-PheAsnArgLeuThrLys-236 |
| SEQ. ID. NO. 19739 | 271-GlyPheValSerAspLeuProHisLysLeuIleSerAlaPheSerAlaThrLeuGlu-289 |
| SEQ. ID. NO. 19740 | 307-AsnSerGlyGlnGlnIleGluAspValGluAsnValLeuGlnGluIleHis-323 |
| SEQ. ID. NO. 19741 | 365-GluAsnThrGlyIleAspAlaLeuArgGluAlaIleAlaGluTyrCysAla-381 |

Antigenic Index - Jameson-Wolf

| | |
|---|---|
| SEQ. ID. NO. 19742 | 1-MetThrGlyArgThrGlyArgAsnGlySerThrGlnAlaGlnProGluArgVal-18 |
| SEQ. ID. NO. 19743 | 24-MetLeuAspLysAspGlyThrGlySerSerAlaThrArgLeuAsnGly-39 |
| SEQ. ID. NO. 19744 | 48-ValGluLeuValLys-52 |
| SEQ. ID. NO. 19745 | 54-AlaGlyGlyAspSerValArgValGluThrAlaLysArgAspArgProHisThr-71 |
| SEQ. ID. NO. 19746 | 77-ThrGlyLysAlaAlaGluLeuSerGlu-85 |
| SEQ. ID. NO. 19747 | 100-GluLeuThrProThrGlnGluArgAsnLeuGluLys-111 |
| SEQ. ID. NO. 19748 | 129-AlaArgArgAlaArgThrGlnGluGlyArgLeuGlnVal-141 |
| SEQ. ID. NO. 19749 | 161-GlnSerGlnArgGlyGlyIleGlyMetLysGlyProGlyGluThrLysLeuGluThrAspArgArgLeuIle-184 |
| SEQ. ID. NO. 19750 | 189-AsnAlaLeuLysLysGlnLeuAlaAsnLeuLysLysGlnArgAlaLeuArgArgLysSerArgGluSerGlyThrIleLysThr-216 |
| SEQ. ID. NO. 19751 | 224-AsnValGlyLysSerSerLeu-230 |
| SEQ. ID. NO. 19752 | 233-ArgLeuThrLysSerGlyIleTyrAla-241 |
| SEQ. ID. NO. 19753 | 257-TyrIleSerProGluCys-262 |
| SEQ. ID. NO. 19754 | 287-ThrLeuGluGluThrAlaGln-293 |
| SEQ. ID. NO. 19755 | 304-AlaAlaProAsnSerGlyGlnGlnIleGluAspValGluAsnValLeu-319 |
| SEQ. ID. NO. 19756 | 323-HisAlaGlyAspIlePro-328 |
| SEQ. ID. NO. 19757 | 333-TyrAsnLysThrAspLeuLeuProSerGluGluGlnAsnThrGlyIle-348 |
| SEQ. ID. NO. 19758 | 365-GluAsnThrGlyIleAspAlaLeuArgGluAlaIle-376 |
| SEQ. ID. NO. 19759 | 381-AlaAlaAlaProAsnThrAspGluThrGluMetPro-392 |

Hydrophilic Regions - Hopp-Woods

| | |
|---|---|
| SEQ. ID. NO. 19760 | 1-MetThrGlyArgThrGlyArgAsnGlySerThr-11 |
| SEQ. ID. NO. 19761 | 13-AlaGlnProGluArg-17 |
| SEQ. ID. NO. 19762 | 25-LeuAspLysAspGlyThrGly-31 |
| SEQ. ID. NO. 19763 | 48-ValGluLeuValLys-52 |
| SEQ. ID. NO. 19764 | 54-AlaGlyGlyAspSerValArgValGluThrAlaLysArgAspArgProHis-70 |
| SEQ. ID. NO. 19765 | 78-GlyLysAlaAlaGluLeuSerGlu-85 |
| SEQ. ID. NO. 19766 | 101-LeuThrProThrGlnGluArgAsnLeuGluLys-111 |
| SEQ. ID. NO. 19767 | 129-AlaArgArgAlaArgThrGlnGluGlyArgLeuGlnVal-141 |
| SEQ. ID. NO. 19768 | 161-GlnSerGlnArgGlyGlyIle-167 |
| SEQ. ID. NO. 19769 | 171-GlyProGlyGluThrLysLeuGluThrAspArgArgLeuIle-184 |
| SEQ. ID. NO. 19770 | 189-AsnAlaLeuLysLysGlnLeuAlaAsnLeuLysLysGlnArgAlaLeuArgArgLysSerArgGluSerGlyThr-213 |
| SEQ. ID. NO. 19771 | 287-ThrLeuGluGluThrAlaGln-293 |
| SEQ. ID. NO. 19772 | 310-GlnGlnIleGluAspValGluAsnValLeu-319 |
| SEQ. ID. NO. 19773 | 337-AspLeuLeuProSerGluGluGlnAsn-345 |
| SEQ. ID. NO. 19774 | 370-AspAlaLeuArgGluAlaIle-376 |
| SEQ. ID. NO. 19775 | 384-ProAsnThrAspGluThrGluMetPro-392 | a539-2
AMPHI Regions - AMPHI

| | |
|---|---|
| SEQ. ID. NO. 19776 | 18-ArgGlnArgGluHisHisArgLeu-25 |
| SEQ. ID. NO. 19777 | 44-LeuValGlyGlyPheAspPheLeuArgValIleGlyCysGlyGlyValAlaTyrLeuProAspPheGlnGln-67 |

Antigenic Index - Jameson-Wolf

| | |
|---|---|
| SEQ. ID. NO. 19778 | 1-MetGluAspLeuGlnGluIleGly-8 |
| SEQ. ID. NO. 19779 | 15-LysValGlyArgGlnArgGluHisHisArgLeuHisHisProGlnProGlyAsnGlyGluAlaAspAsp-37 |
| SEQ. ID. NO. 19780 | 63-ProAspPheGlnGlnAsnValGlyLysAlaAsp-73 |
| SEQ. ID. NO. 19781 | 77-ValProAspAspAlaAlaAla-83 |
| SEQ. ID. NO. 19782 | 88-IleGluValAspAlaAspAspAlaValCys-97 |
| SEQ. ID. NO. 19783 | 102-LeuPheAspGlnProAspAlaGlyGlyAlaGlyAspAlaAlaGluHis-117 |

Hydrophilic Regions - Hopp-Woods

| | |
|---|---|
| SEQ. ID. NO. 19784 | 1-MetGluAspLeuGlnGluIleGly-8 |
| SEQ. ID. NO. 19785 | 15-LysValGlyArgGlnArgGluHisHisArg-24 |
| SEQ. ID. NO. 19786 | 31-GlyAsnGlyGluAlaAspAsp-37 |
| SEQ. ID. NO. 19787 | 69-ValGlyLysAlaAsp-73 |
| SEQ. ID. NO. 19788 | 78-ProAspAspAlaAlaAla-83 |

TABLE 1-continued

```
SEQ. ID. NO. 19789    88-IleGluValAspAlaAspAspAlaValCys-97
SEQ. ID. NO. 19790    102-LeuPheAspGlnProAspAlaGlyGlyAlaGlyAspAlaAlaGluHis-117
a542
AMPHI Regions - AMPHI
SEQ. ID. NO. 19791    6-ArgIleArgArgCysSerVal-12
Antigenic Index - Jameson-Wolf
SEQ. ID. NO. 19792    1-MetProLysTrpSerArgIleArgArgCysSerVal-12
SEQ. ID. NO. 19793    20-SerAlaSerArgLeuThrCys-26
SEQ. ID. NO. 19794    36-MetArgLeuLysSerSerAspGlyIleAlaSer-46
SEQ. ID. NO. 19795    55-GlyProMetProSerGluThrValSerHisLysSerAspSerSerArgAsnThrSerAlaSerArgArgAsnValSerProLysCysProPhe-85
SEQ. ID. NO. 19796    89-PheArgGlnAspAlaAlaLysProArgArgPheGlyGlyLys-102
SEQ. ID. NO. 19797    106-LeuThrGlySerArg-110
Hydrophilic Regions - Hopp-Woods
SEQ. ID. NO. 19798    5-SerArgIleArgArgCysSer-11
SEQ. ID. NO. 19799    36-MetArgLeuLysSerSerAspGlyIleAla-45
SEQ. ID. NO. 19800    57-MetProSerGluThrValSerHisLysSerAspSerSerArgAsnThrSerAlaSerArgArgAsnValSerPro-81
SEQ. ID. NO. 19801    89-PheArgGlnAspAlaAlaLysProArgArgPheGlyGly-101
a544-2
AMPHI Regions - AMPHI
SEQ. ID. NO. 19802    11-AlaLeuIleGlyIleLeu-16
SEQ. ID. NO. 19803    55-PheTrpPheProSerCysProGlyCysValSerGluMetProLysIleIleLysThrAla-74
SEQ. ID. NO. 19804    85-LeuAlaValAlaGlnProIleAspProIleGluSerValArgGlnTyrVal-101
SEQ. ID. NO. 19805    116-LysAlaValGlyGlnAlaPhe-122
Antigenic Index - Jameson-Wolf
SEQ. ID. NO. 19806    1-MetLysLysIleLeu-5
SEQ. ID. NO. 19807    22-IleProAspSerLysThrAlaPro-29
SEQ. ID. NO. 19808    35-AspLeuHisGlyLysThrValSerAsnAlaAspLeuGlnGly-48
SEQ. ID. NO. 19809    59-SerCysProGlyCys-63
SEQ. ID. NO. 19810    66-GluMetProLysIleIleLysThrAlaAsnAspTyrLysAsnLysAsnPhe-82
SEQ. ID. NO. 19811    90-ProIleAspProIleGluSerValArgGlnTyrValLysAspTyrGly-105
SEQ. ID. NO. 19812    113-AspAlaAspLysAlaVal-118
SEQ. ID. NO. 19813    133-IleGlyLysLysGlyGluIleLeu-140
SEQ. ID. NO. 19814    144-ValGlyGluProAspPheGlyLysLeuTyrGlnGluIleAspThr-158
Hydrophilic Regions - Hopp-Woods
SEQ. ID. NO. 19815    1-MetLysLysIleLeu-5
SEQ. ID. NO. 19816    23-ProAspSerLysThr-27
SEQ. ID. NO. 19817    66-GluMetProLysIleIleLysThrAlaAsnAspTyrLysAsnLysAsn-81
SEQ. ID. NO. 19818    92-AspProIleGluSerValArgGlnTyrValLys-102
SEQ. ID. NO. 19819    113-AspAlaAspLysAlaVal-118
SEQ. ID. NO. 19820    133-IleGlyLysLysGlyGluIle-139
a547
AMPHI Regions - AMPHI
SEQ. ID. NO. 19821    7-PheAsnLysThrValAlaSerPheAlaGlnIleValGluThrPheAspVal-23
SEQ. ID. NO. 19822    62-AsnArgSerPheLys-66
SEQ. ID. NO. 19823    105-LeuHisIlePheThrAsnIleLys-112
Antigenic Index - Jameson-Wolf
SEQ. ID. NO. 19824    3-ValAspAsnGlyPheAsnLysThrVal-11
SEQ. ID. NO. 19825    35-GlnMetLysGlnArgCysGlyTrp-42
SEQ. ID. NO. 19826    53-PheProArgCysGlyPheGluIleProAsnArgSerPheLysGlu-67
SEQ. ID. NO. 19827    76-LeuSerGluArgPheArgThrAsnAlaGluValGluIle-88
Hydrophilic Regions - Hopp-Woods
SEQ. ID. NO. 19828    36-MetLysGlnArgCys-40
SEQ. ID. NO. 19829    60-IleProAsnArgSerPheLysGlu-67
SEQ. ID. NO. 19830    76-LeuSerGluArgPheArgThrAsnAlaGluValGluIle-88
a548
AMPHI Regions - AMPHI
SEQ. ID. NO. 19831    14-ValLeuAlaAlaLeuAlaAlaCysLys-22
SEQ. ID. NO. 19832    39-SerAlaAlaGluAsnAlaAlaLysPro-47
SEQ. ID. NO. 19833    89-PheThrHisCysProAspValCysProThr-98
SEQ. ID. NO. 19834    103-TyrSerAspThrLeuLysGlnLeuGlyGlyGln-113
SEQ. ID. NO. 19835    132-GluIleIleGlyLysTyrAlaLys-139
Antigenic Index - Jameson-Wolf
SEQ. ID. NO. 19836    21-CysLysProGlnAspAsnSerAlaAla-29
SEQ. ID. NO. 19837    39-SerAlaAlaGluAsnAlaAlaLysProGlnThrArgGlyThrAspMetArgLysGluAspIleGlyGlyAspPheThrLeuThrAspGlyGluGlyLys
                      ProPheAsn-74
SEQ. ID. NO. 19838    76-SerAspLeuLysGly-80
SEQ. ID. NO. 19839    91-HisCysProAspValCysPro-97
SEQ. ID. NO. 19840    104-SerAspThrLeuLysGlnLeuGlyGlyGlnAlaLysAspValLys-118
SEQ. ID. NO. 19841    124-IleAspProGluArgAspThrProGluIleIleGlyLysTyrAlaLysGlnPheAsnProAspPhe-145
SEQ. ID. NO. 19842    150-AlaThrGlyAspGlnAsnLeu-156
SEQ. ID. NO. 19843    169-LysValAsnGlnLysAspAspSerGluAsnTyrLeu-180
SEQ. ID. NO. 19844    189-LeuIleAspLysAsnGlyGlu-195
SEQ. ID. NO. 19845    200-SerProTyrGlySerGluProGluThrIleAlaAlaAspVal-213
Hydrophilic Regions - Hopp-Woods
SEQ. ID. NO. 19846    22-LysProGlnAspAsnSerAla-28
SEQ. ID. NO. 19847    39-SerAlaAlaGluAsnAlaAlaLysProGlnThrArgGlyThrAspMetArgLysGluAspIleGlyGly-61
SEQ. ID. NO. 19848    64-ThrLeuThrAspGlyGluGlyLysPro-72
SEQ. ID. NO. 19849    76-SerAspLeuLysGly-80
SEQ. ID. NO. 19850    111-GlyGlyGlnAlaLysAspValLys-118
SEQ. ID. NO. 19851    124-IleAspProGluArgAspThrProGluIleIle-134
```

TABLE 1-continued

| | |
|---|---|
| SEQ. ID. NO. 19852 | 151-ThrGlyAspGlnAsn-155 |
| SEQ. ID. NO. 19853 | 169-LysValAsnGlnLysAspAspSerGluAsnTyrLeu-180 |
| SEQ. ID. NO. 19854 | 191-AspLysAsnGlyGlu-195 |
| SEQ. ID. NO. 19855 | 203-GlySerGluProGluThrIleAlaAlaAspVal-213 |
| a552-1 | |
| AMPHI Regions - AMPHI | |
| SEQ. ID. NO. 19856 | 18-CysThrAsnAlaPheAlaAlaPro-25 |
| SEQ. ID. NO. 19857 | 29-AlaSerLeuAlaArgTrpLeuAspThr-37 |
| SEQ. ID. NO. 19858 | 41-AspArgAspIleGluLysAsnMetIleGluGlyPheAsnAlaGlyPheLysProTyrAlaAspLysAlaLeuAlaGluMet-67 |
| SEQ. ID. NO. 19859 | 75-AlaAlaGluAlaPheAsnArgTyrArgGluAsnVal-86 |
| SEQ. ID. NO. 19860 | 89-AspLeuIleThrProGluValLys-96 |
| SEQ. ID. NO. 19861 | 116-IleAspGlyMetIleAla-121 |
| SEQ. ID. NO. 19862 | 139-IleLysLysSerMetSerGluIle-146 |
| SEQ. ID. NO. 19863 | 154-SerGlyLysIleAlaGlnHisHisLeuProGluPheThrGluGluLeuArgArg-171 |
| Antigenic Index - Jameson-Wolf | |
| SEQ. ID. NO. 19864 | 25-ProProSerAspAlaSerLeu-31 |
| SEQ. ID. NO. 19865 | 35-LeuAspThrGlnAsnPheAspArgAspIleGluLysAsnMetIle-49 |
| SEQ. ID. NO. 19866 | 53-AsnAlaGlyPheLysProTyrAlaAspLysAlaLeuAlaGluMetProGluAlaLysLysAspGlnAlaAla-76 |
| SEQ. ID. NO. 19867 | 78-AlaPheAsnArgTyrArgGluAsnValLeu-87 |
| SEQ. ID. NO. 19868 | 90-LeuIleThrProGluValLysGlnAlaVal-99 |
| SEQ. ID. NO. 19869 | 105-LysAsnAlaArgGluIleTyrThrGlnGluGluIleAspGly-118 |
| SEQ. ID. NO. 19870 | 131-ValValAlaLysAsnProArgLeuIleLysLysSerMetSer-144 |
| SEQ. ID. NO. 19871 | 153-LeuSerGlyLysIle-157 |
| SEQ. ID. NO. 19872 | 164-GluPheThrGluGluLeuArgArg-171 |
| SEQ. ID. NO. 19873 | 173-IleCysGlyGlyLysAsnProAspAlaGlyCysLysGlnAlaGlyGlnValGlyLysArgHisGlnLys-195 |
| Hydrophilic Regions - Hopp-Woods | |
| SEQ. ID. NO. 19874 | 26-ProSerAspAlaSerLeu-31 |
| SEQ. ID. NO. 19875 | 38-GlnAsnPheAspArgAspIleGluLysAsnMetIle-49 |
| SEQ. ID. NO. 19876 | 58-ProTyrAlaAspLysAlaLeuAlaGluMetProGluAlaLysLysAspGlnAlaAla-76 |
| SEQ. ID. NO. 19877 | 78-AlaPheAsnArgTyrArgGluAsnValLeu-87 |
| SEQ. ID. NO. 19878 | 90-LeuIleThrProGluValLysGlnAlaVal-99 |
| SEQ. ID. NO. 19879 | 105-LysAsnAlaArgGluIleTyrThr-112 |
| SEQ. ID. NO. 19880 | 114-GluGluIleAspGly-118 |
| SEQ. ID. NO. 19881 | 131-ValValAlaLysAsnProArgLeuIleLysLysSerMetSer-144 |
| SEQ. ID. NO. 19882 | 164-GluPheThrGluGluLeuArgArg-171 |
| SEQ. ID. NO. 19883 | 176-GlyLysAsnProAspAlaGlyCysLysGlnAlaGlyGlnValGlyLysArgHisGlnLys-195 |
| a554 | |
| AMPHI Regions - AMPHI | |
| SEQ. ID. NO. 19884 | 38-PheGlnThrProGluThrLeu-44 |
| SEQ. ID. NO. 19885 | 71-AlaAlaLeuThrGlnLeuMet-77 |
| SEQ. ID. NO. 19886 | 110-ArgMetPheValArgProGlyAspThrVal-119 |
| SEQ. ID. NO. 19887 | 124-LeuLeuLysGlyMet-128 |
| SEQ. ID. NO. 19888 | 148-SerIleGluAsnPheValGlnGlnMetAsnLysGlu-159 |
| SEQ. ID. NO. 19889 | 185-AlaLysAspLeuAlaGlnLeuSerGluAlaLeuMetArgAspPheProGluTyrTyrProLeuPheSer-207 |
| SEQ. ID. NO. 19890 | 296-ThrValAlaGlnIle-300 |
| SEQ. ID. NO. 19891 | 331-GluGlnIleLeuGluThrIleGlnProIleProAla-342 |
| Antigenic Index - Jameson-Wolf | |
| SEQ. ID. NO. 19892 | 23-AlaSerProAlaProAsnArgProThrAla-32 |
| SEQ. ID. NO. 19893 | 37-ThrPheGlnThrProGluThr-43 |
| SEQ. ID. NO. 19894 | 53-LeuGlnSerLysGln-57 |
| SEQ. ID. NO. 19895 | 61-AlaLysAsnIleAsnThrProValGlu-69 |
| SEQ. ID. NO. 19896 | 84-LysAsnMetLysSerGlyAsnIleArgSerGluGluAsnLeuLysIleProGlu-101 |
| SEQ. ID. NO. 19897 | 104-TrpAlaSerGluGlySerArgMetPheValArgProGlyAspThrValSerThrAspLysLeuLeu-125 |
| SEQ. ID. NO. 19898 | 143-ArgLeuGlyAsnGlySerIleGluAsnPhe-152 |
| SEQ. ID. NO. 19899 | 156-MetAsnLysGluAlaArgArgLeuGlyMetLysAsnThrValPheLysAsnProThrGlyLeuSerArgGluGlyGlnValSerThrAlaLysAspLeu AlaGln-190 |
| SEQ. ID. NO. 19900 | 194-AlaLeuMetArgAspPheProGluTyrTyr-203 |
| SEQ. ID. NO. 19901 | 214-LysAsnIleGluGlnAsnAsnArgAsnIleLeu-224 |
| SEQ. ID. NO. 19902 | 226-TyrArgAspAsnAsnValAsnGlyLeuLysAlaGlyHisThrGluSerGlyGlyTyrAsn-245 |
| SEQ. ID. NO. 19903 | 250-TyrSerGlyAsnGlyArgHis-256 |
| SEQ. ID. NO. 19904 | 262-LeuGlySerGluSerAlaGluThrArgAlaSerAspAsnSerLys-276 |
| SEQ. ID. NO. 19905 | 285-PheAspThrProLysIleTyrProLysGlyLysThr-296 |
| SEQ. ID. NO. 19906 | 302-IleSerGlyGlySerLysLysThrValArg-311 |
| SEQ. ID. NO. 19907 | 323-ProHisLysGluAlaLysMetAlaGluGlnIleLeu-334 |
| SEQ. ID. NO. 19908 | 342-AlaProValLysLysGlyGlnIleLeuGlyLysIleLysIleArgGlnAsnGlyTyr-360 |
| SEQ. ID. NO. 19909 | 362-IleAlaGluLysGluIleValAla-369 |
| SEQ. ID. NO. 19910 | 371-GluAsnValLysLysArgSerArgTrpGlnArg-381 |
| Hydrophilic Regions - Hopp-Woods | |
| SEQ. ID. NO. 19911 | 26-AlaProAsnArgProThrAla-32 |
| SEQ. ID. NO. 19912 | 85-AsnMetLysSerGlyAsnIleArgSerGluGluAsnLeuLysIleProGlu-101 |
| SEQ. ID. NO. 19913 | 107-GluGlySerArgMetPheValArgProGlyAspThrValSerThrAspLysLeuLeu-125 |
| SEQ. ID. NO. 19914 | 156-MetAsnLysGluAlaArgArgLeuGlyMet-165 |
| SEQ. ID. NO. 19915 | 174-ThrGlyLeuSerArgGluGlyGlnValSerThrAlaLysAspLeuAlaGln-190 |
| SEQ. ID. NO. 19916 | 214-LysAsnIleGluGlnAsnAsnArg-221 |
| SEQ. ID. NO. 19917 | 227-ArgAspAsnAsnValAsn-232 |
| SEQ. ID. NO. 19918 | 237-GlyHisThrGluSerGly-242 |
| SEQ. ID. NO. 19919 | 264-SerGluSerAlaGluThrArgAlaSerAspAsnSerLys-276 |
| SEQ. ID. NO. 19920 | 289-LysIleTyrProLysGlyLysThr-296 |
| SEQ. ID. NO. 19921 | 304-GlyGlySerLysLysThrValArg-311 |
| SEQ. ID. NO. 19922 | 323-ProHisLysGluAlaLysMetAlaGluGlnIleLeu-334 |

TABLE 1-continued

| | |
|---|---|
| SEQ. ID. NO. 19923 | 343-ProValLysLysGlyGlnIle-349 |
| SEQ. ID. NO. 19924 | 353-IleLysIleArgGln-357 |
| SEQ. ID. NO. 19925 | 362-IleAlaGluLysGluIleValAla-369 |
| SEQ. ID. NO. 19926 | 371-GluAsnValLysLysArgSerArgTrp-379 | a556
AMPHI Regions - AMPHI
SEQ. ID. NO. 19927    61-IleGluArgLeuLys-65
Antigenic Index - Jameson-Wolf
SEQ. ID. NO. 19928    1-MetAspAsnLysThrLysLeuArgLeu-9
SEQ. ID. NO. 19929    52-ThrSerArgArgGlnGlnArgGlnPheIleGluArgLeuLysLysPheAspIleAspProGluLysGlyArgIleAsnGluAlaAsnLeuArgArgMet
                     TyrHisSerGlyGlyGlnHisGlnLysAspAla-95
SEQ. ID. NO. 19930    102-SerGlnLysCysSerValAspGluAlaHisAlaMetPheLysLysArgProThrArgGlnGluIleAsn-124
SEQ. ID. NO. 19931    127-AlaAlaLysGlnSerArgGlyGlnLysArgProHisArg-139
Hydrophilic Regions - Hopp-Woods
SEQ. ID. NO. 19932    1-MetAspAsnLysThrLysLeuArgLeu-9
SEQ. ID. NO. 19933    53-SerArgArgGlnGlnArgGlnPheIleGluArgLeuLysLysPheAspIleAspProGluLysGlyArgIleAsnGluAlaAsnLeuArgArgMetTyr-85
SEQ. ID. NO. 19934    90-GlnHisGlnLysAspAla-95
SEQ. ID. NO. 19935    105-CysSerValAspGluAlaHisAlaMetPheLysLysArgProThrArgGlnGluIleAsn-124
SEQ. ID. NO. 19936    127-AlaAlaLysGlnSerArgGlyGlnLysArgProHisArg-139
a557
AMPHI Regions - AMPHI
SEQ. ID. NO. 19937    22-GlyAlaAspGlyIle-26
SEQ. ID. NO. 19938    55-SerGlyArgValAspAspAlaAla-62
Antigenic Index - Jameson-Wolf
SEQ. ID. NO. 19939    20-LeuLysGlyAlaAspGlyIleSerProProLeuThrTyrArgSerTrpHisIleGluGlyGlyGlnAlaLeu-43
SEQ. ID. NO. 19940    54-AlaSerGlyArgValAspAspAlaAlaGly-63
SEQ. ID. NO. 19941    68-LeuArgIleAspSerValSerGlnAsnLysGluThrTyrThr-81
SEQ. ID. NO. 19942    100-GlnValLeuLysArgGlyGluProValGlyLysProMet-112
SEQ. ID. NO. 19943    123-AlaAspAsnGluIleLeuGlyLysGlnGluGluGluAla-135
SEQ. ID. NO. 19944    141-MetArgGlnAspAlaAlaGluGlnIleValArg-151
Hydrophilic Regions - Hopp-Woods
SEQ. ID. NO. 19945    21-LysGlyAlaAspGlyIle-26
SEQ. ID. NO. 19946    56-GlyArgValAspAspAlaAlaGly-63
SEQ. ID. NO. 19947    68-LeuArgIleAspSerValSerGlnAsnLysGluThrTyrThr-81
SEQ. ID. NO. 19948    100-GlnValLeuLysArgGlyGluProValGly-109
SEQ. ID. NO. 19949    126-GluIleLeuGlyLysGlnGluGluGluAla-135
SEQ. ID. NO. 19950    141-MetArgGlnAspAlaAlaGluGlnIleValArg-151
a560
AMPHI Regions - AMPHI
SEQ. ID. NO. 19951    30-PheArgAspGlyAlaHisLysMetAlaArgValTrpValLysIleLeu-45
SEQ. ID. NO. 19952    167-ArgMetAlaLysMetPhe-172
SEQ. ID. NO. 19953    192-PheLeuLysTyrProGlyGlu-198
SEQ. ID. NO. 19954    218-MetGlyLysCysGluHisLeuIleGlu-226
Antigenic Index - Jameson-Wolf
SEQ. ID. NO. 19955    29-ProPheArgAspGlyAlaHisLysMet-37
SEQ. ID. NO. 19956    61-GlyAlaGluAsnIleProAspArgProAla-70
SEQ. ID. NO. 19957    76-HisGlnSerGlyTrpGlu-81
SEQ. ID. NO. 19958    95-ValAlaLysArgGluLeuPhe-101
SEQ. ID. NO. 19959    116-IleGlyIleAspArgAsnAsnArgArgGluAlaAsnGluGlnLeuIle-131
SEQ. ID. NO. 19960    134-GlyLeuAlaArgLysAsnGluGlyTyr-142
SEQ. ID. NO. 19961    148-ProGluGlyThrArgLeuAlaProGlyLysArgGlyLysTyrLysLeuGlyGly-165
SEQ. ID. NO. 19962    182-AsnSerGlyGluPheTrpProLysAsnSerPheLeuLysTyrProGlyGluIle-199
SEQ. ID. NO. 19963    209-HisAlaSerGlySerGluAlaGluLeuMetGlyLysCysGluHisLeuIle-225
SEQ. ID. NO. 19964    242-MetProSerGluThrAla-247
Hydrophilic Regions - Hopp-Woods
SEQ. ID. NO. 19965    29-ProPheArgAspGlyAlaHisLysMet-37
SEQ. ID. NO. 19966    64-AsnIleProAspArgProAla-70
SEQ. ID. NO. 19967    95-ValAlaLysArgGluLeuPhe-101
SEQ. ID. NO. 19968    116-IleGlyIleAspArgAsnAsnArgArgGluAlaAsnGluGlnLeuIle-131
SEQ. ID. NO. 19969    134-GlyLeuAlaArgLysAsnGlu-140
SEQ. ID. NO. 19970    149-GluGlyThrArgLeuAlaProGlyLysArgGlyLysTyrLysLeuGlyGly-165
SEQ. ID. NO. 19971    211-SerGlySerGluAlaGluLeuMetGlyLysCysGluHisLeuIle-225
SEQ. ID. NO. 19972    242-MetProSerGluThrAla-247
a561
AMPHI Regions - AMPHI
SEQ. ID. NO. 19973    22-GlyLeuTrpValGlyLeuAlaAla-29
SEQ. ID. NO. 19974    46-AlaSerValIleGluGluAlaGlyAsn-54
SEQ. ID. NO. 19975    79-ValAlaGluPheGluLysSerLeuLysArgIleAlaGln-91
SEQ. ID. NO. 19976    128-SerTyrArgArgProThrGlnVal-135
SEQ. ID. NO. 19977    172-MetThrLeuValSerSer-177
SEQ. ID. NO. 19978    188-ValIleArgProLeuGlnAlaLeuArgGluGlyAlaGluArgIleGlyArgArgCysPheAspIle-209
SEQ. ID. NO. 19979    219-PheLysGlnValGlyArgCysPheAsnGlnMet-229
SEQ. ID. NO. 19980    238-AspAspLeuGluGlyGlnValAlaGluGlnThrArgSerLeuGluLysGln-254
SEQ. ID. NO. 19981    265-ThrArgAspLeuHisGlnSer-271
SEQ. ID. NO. 19982    275-GlnGlnAlaAlaGluHisPhe-281
SEQ. ID. NO. 19983    283-AsnArgIleLeuPro-287
SEQ. ID. NO. 19984    317-AlaSerAspLeuGlyLysTyrHisGlu-325
SEQ. ID. NO. 19985    339-ArgLeuLeuLeuSerPheProAsnGly-347
SEQ. ID. NO. 19986    358-LeuGlnThrLeuGlyArgGlnLeuGly-366
SEQ. ID. NO. 19987    392-GlnGlyLeuHisAspSerIleAlaGlnAlaLeuThr-403

TABLE 1-continued

| SEQ. ID. NO. 19988 | 434-GlyValGlnGluCysTyrGluAspValArgGluLeu-445 |
|---|---|
| SEQ. ID. NO. 19989 | 456-LysGluPheProGluAlaValAlaAspLeuPheSerArgPheThrGlnGlnThrGly-474 |
| SEQ. ID. NO. 19990 | 504-LeuSerAsnIleArgLysHisAla-511 |
| SEQ. ID. NO. 19991 | 540-ThrGluAsnIleGlyGluProSer-547 |

Antigenic Index - Jameson-Wolf

| SEQ. ID. NO. 19992 | 6-ArgPheSerAspGlyIleSer-12 |
|---|---|
| SEQ. ID. NO. 19993 | 48-ValIleGluGluAlaGlyAsn-54 |
| SEQ. ID. NO. 19994 | 66-AlaGlyGluGlySerProArgAlaGlnIleAspAsnGlnValAlaGluPheGluLysSerLeuLysArgIleAlaGlnSerAspAlaIleHisPro-97 |
| SEQ. ID. NO. 19995 | 99-IleProSerAspThrProLeu-105 |
| SEQ. ID. NO. 19996 | 124-ProProLeuGlnSerTyrArgArgProThrGlnValAspLeu-137 |
| SEQ. ID. NO. 19997 | 152-GluAsnAlaAsnGluLysAsnThr-159 |
| SEQ. ID. NO. 19998 | 193-GlnAlaLeuArgGluGlyAlaGluArgIleGlyArgArgCysPheAsp-208 |
| SEQ. ID. NO. 19999 | 210-ProValProGluGlyGlyThrProGluPheLysGlnValGlyArgCysPheAsnGlnMetGlyGlyArgLeuLysIleLeuTyrAspAspLeuGluGly GlnValAlaGluGlnThrArgSerLeuGluLysGlnAsnGlnAsnLeu-258 |
| SEQ. ID. NO. 20000 | 263-GlnThrThrArgAspLeuHisGlnSerTyrIle-273 |
| SEQ. ID. NO. 20001 | 289-ValGlyAlaAspSerGlyArgValCysLeuAspGlyGlySerAsp-303 |
| SEQ. ID. NO. 20002 | 310-HisAlaAspCysGlyThrAlaAlaSerAspLeuGlyLysTyrHisGlu-325 |
| SEQ. ID. NO. 20003 | 332-TyrGlnAsnGluThrLeuGly-338 |
| SEQ. ID. NO. 20004 | 344-PheProAsnGlyIleSerLeuAspGluAspAspArgIleLeu-357 |
| SEQ. ID. NO. 20005 | 360-ThrLeuGlyArgGlnLeu-365 |
| SEQ. ID. NO. 20006 | 371-GlyAlaLysGlnGluGluGluLysArgLeu-380 |
| SEQ. ID. NO. 20007 | 384-LeuGlnGluArgAsnLeu-389 |
| SEQ. ID. NO. 20008 | 394-LeuHisAspSerIle-398 |
| SEQ. ID. NO. 20009 | 415-AlaPheAlaGluAsnLysArgGluGluAlaAlaGlu-426 |
| SEQ. ID. NO. 20010 | 434-GlyValGlnGluCysTyrGluAspValArgGlu-444 |
| SEQ. ID. NO. 20011 | 450-ArgThrLysIleSerAsnLysGluPheProGluAlaVal-462 |
| SEQ. ID. NO. 20012 | 468-ArgPheThrGlnGlnThrGlyThrThrVal-477 |
| SEQ. ID. NO. 20013 | 480-AlaTrpGluAsnGlyThrHisLeuProThrGlnAspGluGlnLeu-494 |
| SEQ. ID. NO. 20014 | 503-SerLeuSerAsnIleArgLysHisAlaHis-512 |
| SEQ. ID. NO. 20015 | 519-ArgLeuLeuLysGlnAspGlySerPheThr-528 |
| SEQ. ID. NO. 20016 | 531-IleGlnAspAsnGlyGlnGlyPheAspThrGluAsnIleGlyGluProSerGlySerHis-550 |
| SEQ. ID. NO. 20017 | 556-MetGlnGluArgAlaLysArgIle-563 |
| SEQ. ID. NO. 20018 | 568-GluIleArgSerGlnAlaGlnGlnGlyThrThr-578 |
| SEQ. ID. NO. 20019 | 584-AlaSerGluGluSerLeuLys-590 |

Hydrophilic Regions - Hopp-Woods

| SEQ. ID. NO. 20020 | 48-ValIleGluGluAlaGlyAsn-54 |
|---|---|
| SEQ. ID. NO. 20021 | 68-GluGlySerProArgAlaGlnIle-75 |
| SEQ. ID. NO. 20022 | 78-GlnValAlaGluPheGluLysSerLeuLysArgIleAlaGln-91 |
| SEQ. ID. NO. 20023 | 128-SerTyrArgArgProThrGln-134 |
| SEQ. ID. NO. 20024 | 152-GluAsnAlaAsnGluLys-157 |
| SEQ. ID. NO. 20025 | 193-GlnAlaLeuArgGluGlyAlaGluArgIleGlyArgArgCysPhe-207 |
| SEQ. ID. NO. 20026 | 213-GluGlyGlyThrProGluPheLysGlnValGly-223 |
| SEQ. ID. NO. 20027 | 235-IleLeuTyrAspAspLeuGluGlyGlnValAlaGluGlnThrArgSerLeuGluLysGlnAsnGln-256 |
| SEQ. ID. NO. 20028 | 264-ThrThrArgAspLeuHis-269 |
| SEQ. ID. NO. 20029 | 290-GlyAlaAspSerGlyArgValCysLeu-298 |
| SEQ. ID. NO. 20030 | 312-AspCysGlyThrAlaAlaSerAspLeuGlyLysTyrHisGlu-325 |
| SEQ. ID. NO. 20031 | 349-SerLeuAspGluAspAspArgIleLeu-357 |
| SEQ. ID. NO. 20032 | 371-GlyAlaLysGlnGluGluGluLysArgLeu-380 |
| SEQ. ID. NO. 20033 | 384-LeuGlnGluArgAsnLeu-389 |
| SEQ. ID. NO. 20034 | 415-AlaPheAlaGluAsnLysArgGluGluAlaAlaGlu-426 |
| SEQ. ID. NO. 20035 | 437-GluCysTyrGluAspValArgGlu-444 |
| SEQ. ID. NO. 20036 | 451-ThrLysIleSerAsnLysGluPheProGluAlaVal-462 |
| SEQ. ID. NO. 20037 | 488-ProThrGlnAspGluGlnLeu-494 |
| SEQ. ID. NO. 20038 | 503-SerLeuSerAsnIleArgLysHisAlaHis-512 |
| SEQ. ID. NO. 20039 | 519-ArgLeuLeuLysGlnAspGly-525 |
| SEQ. ID. NO. 20040 | 533-AspAsnGlyGlnGlyPheAspThrGluAsnIleGlyGluProSerGly-548 |
| SEQ. ID. NO. 20041 | 556-MetGlnGluArgAlaLysArgIle-563 |
| SEQ. ID. NO. 20042 | 568-GluIleArgSerGlnAlaGln-574 |
| SEQ. ID. NO. 20043 | 584-AlaSerGluGluSerLeuLys-590 | a562

AMPHI Regions - AMPHI

| SEQ. ID. NO. 20044 | 48-TrpSerLeuValSerAlaTrpMetValValIle-58 |
|---|---|
| SEQ. ID. NO. 20045 | 84-LeuGluThrThrVal-88 |
| SEQ. ID. NO. 20046 | 90-SerAlaValArgMetLeu-95 |
| SEQ. ID. NO. 20047 | 97-PheThrProTyrThrThrValAlaSerThrSer-107 |
| SEQ. ID. NO. 20048 | 116-ThrPhePheAlaProLeuSerArgThrLeu-125 |
| SEQ. ID. NO. 20049 | 132-AsnAlaProValHisSerMetThrLysSerThrProSerSerPheHis-147 |
| SEQ. ID. NO. 20050 | 183-ValSerAsnLeuValArgTrpAlaLeu-191 |

Antigenic Index - Jameson-Wolf

| SEQ. ID. NO. 20051 | 10-AsnSerGlySerThrLysProThr-17 |
|---|---|
| SEQ. ID. NO. 20052 | 32-ProLeuArgAlaArgArgArgSerLeuTrpArg-42 |
| SEQ. ID. NO. 20053 | 72-AlaThrGlyGluArgGlnLeuVal-79 |
| SEQ. ID. NO. 20054 | 105-SerThrSerSerProProGlyAlaGluMet-114 |
| SEQ. ID. NO. 20055 | 138-MetThrLysSerThrProSerSerPheHisGlySerSerAla-151 |
| SEQ. ID. NO. 20056 | 154-ArgValXxxLysXxxGlyIle-160 |
| SEQ. ID. NO. 20057 | 167-ArgLeuProProSerTrpAspThrSerAlaSerLysArgProCysThr-182 |

Hydrophilic Regions - Hopp-Woods

| SEQ. ID. NO. 20058 | 33-LeuArgAlaArgArgArgSerLeuTrp-41 |
|---|---|
| SEQ. ID. NO. 20059 | 72-AlaThrGlyGluArgGlnLeuVal-79 |
| SEQ. ID. NO. 20060 | 110-ProGlyAlaGluMet-114 |

TABLE 1-continued

| | |
|---|---|
| SEQ. ID. NO. 20061 | 139-ThrLysSerThrPro-143 |
| SEQ. ID. NO. 20062 | 175-SerAlaSerLysArgProCysThr-182 | a565
AMPHI Regions - AMPHI

| | |
|---|---|
| SEQ. ID. NO. 20063 | 50-AlaThrCysThrArgAlaMetSerLysSer-59 |
| SEQ. ID. NO. 20064 | 66-SerSerTrpAlaArg-70 |
| SEQ. ID. NO. 20065 | 84-IleSerThrTrpSerAspLeu-90 |
| SEQ. ID. NO. 20066 | 103-AspPheMetSerGlnLeuAspLeuThr-111 |
| SEQ. ID. NO. 20067 | 140-SerHisSerSerGluThrIleSerSerCysProAlaMetAlaSerIleThrLysProAsn-159 |
| SEQ. ID. NO. 20068 | 184-AlaAsnThrThrSerAlaPhe-190 |

Antigenic Index - Jameson-Wolf

| | |
|---|---|
| SEQ. ID. NO. 20069 | 1-MetAspSerThrLeuSerLysThrCys-9 |
| SEQ. ID. NO. 20070 | 23-AlaArgProArgProAlaAlaSerAsnThrSerLeu-35 |
| SEQ. ID. NO. 20071 | 37-PheAlaSerProAsnAspThrGlySer-45 |
| SEQ. ID. NO. 20072 | 55-AlaMetSerLysSerSerAlaLysTyrGly-64 |
| SEQ. ID. NO. 20073 | 67-SerTrpAlaArgThrArgProThrValCysProProLeuProLysProThrIle-84 |
| SEQ. ID. NO. 20074 | 99-CysArgSerSerAspPheMetSer-106 |
| SEQ. ID. NO. 20075 | 109-AspLeuThrLysArgProThrSerAlaSerLeuProProLysArgLysGlyAlaIle-127 |
| SEQ. ID. NO. 20076 | 129-IleAspSerArgThrAlaAla-135 |
| SEQ. ID. NO. 20077 | 140-SerHisSerSerGluThrIleSerSerCysProAla-151 |
| SEQ. ID. NO. 20078 | 155-IleThrLysProAsnSerProProCysAlaArgTyr-166 |
| SEQ. ID. NO. 20079 | 170-LeuArgLeuSerProThrGlu-176 |
| SEQ. ID. NO. 20080 | 194-SerIleAlaAsnSerIleAsnThrCysArgGlnProPro-206 |

Hydrophilic Regions - Hopp-Woods

| | |
|---|---|
| SEQ. ID. NO. 20081 | 24-AlaArgProArgProAlaAla-30 |
| SEQ. ID. NO. 20082 | 39-SerProAsnAspThrGlySer-45 |
| SEQ. ID. NO. 20083 | 55-AlaMetSerLysSerSerAla-61 |
| SEQ. ID. NO. 20084 | 69-AlaArgThrArgPro-73 |
| SEQ. ID. NO. 20085 | 100-ArgSerSerAspPhe-104 |
| SEQ. ID. NO. 20086 | 109-AspLeuThrLysArgProThrSer-116 |
| SEQ. ID. NO. 20087 | 119-LeuProProLysArgLysGlyAlaIle-127 |
| SEQ. ID. NO. 20088 | 129-IleAspSerArgThr-133 |
| SEQ. ID. NO. 20089 | 141-HisSerSerGluThrIleSer-147 |
| SEQ. ID. NO. 20090 | 156-ThrLysProAsnSer-160 | a566
Antigenic Index - Jameson-Wolf

| | |
|---|---|
| SEQ. ID. NO. 20091 | 35-TyrProAsnCysGlyAlaAspGlyAlaGlyGlyLysGlyHis-48 |
| SEQ. ID. NO. 20092 | 61-AlaValGlyGlyGluGluGlyGlyValValAlaAspAspValAlaArgAlaAspGlyGlyLysAlaAspGlyGlyArgIleAlaArg-89 |
| SEQ. ID. NO. 20093 | 105-SerAlaGluArgAlaGlyAspAspPheAla-114 |

Hydrophilic Regions - Hopp-Woods

| | |
|---|---|
| SEQ. ID. NO. 20094 | 39-GlyAlaAspGlyAlaGlyGlyLysGlyHis-48 |
| SEQ. ID. NO. 20095 | 63-GlyGlyGluGluGlyGlyValValAlaAspAspValAlaArgAlaAspGlyGlyLysAlaAspGlyGlyArgIleAlaArg-89 |
| SEQ. ID. NO. 20096 | 105-SerAlaGluArgAlaGlyAspAspPheAla-114 | a567
AMPHI Regions - AMPHI

| | |
|---|---|
| SEQ. ID. NO. 20097 | 60-GlyValTyrGlnVal-64 |
| SEQ. ID. NO. 20098 | 98-GluLeuValGlnGluIleAlaArgGluVal-107 |
| SEQ. ID. NO. 20099 | 112-AlaLeuLysAlaVal-116 |
| SEQ. ID. NO. 20100 | 154-TyrAlaLeuGluGlyIleSerAspLeuIleAlaThrValArgLysIleArgGln-171 |
| SEQ. ID. NO. 20101 | 180-ThrGlyIleValArg-184 |
| SEQ. ID. NO. 20102 | 195-AlaGluValSerGluGlnLeuArgSerHisPheGlyAspLeuLeu-209 |

Antigenic Index - Jameson-Wolf

| | |
|---|---|
| SEQ. ID. NO. 20103 | 10-AsnGlnLysGlyGlyValGlyLysThrThrThr-20 |
| SEQ. ID. NO. 20104 | 28-LeuAlaSerArgGlyLysArg-34 |
| SEQ. ID. NO. 20105 | 38-ValAspLeuAspProGlnGlyAsnAlaThrThrGlySerGlyIleAspLysAlaSerLeuGlnSerGly-60 |
| SEQ. ID. NO. 20106 | 67-GlyAspAlaAspValLysSerAlaAlaValArgSerLysGluGlyGlyTyr-83 |
| SEQ. ID. NO. 20107 | 95-AlaGluIleGluLeu-99 |
| SEQ. ID. NO. 20108 | 101-GlnGluIleAlaArgGluValArgLeuLysAsnAlaLeu-113 |
| SEQ. ID. NO. 20109 | 115-AlaValAlaGluAspTyrAsp-121 |
| SEQ. ID. NO. 20110 | 127-CysProProSerLeu-131 |
| SEQ. ID. NO. 20111 | 164-AlaThrValArgLysIleArgGlnAlaValAsnProAspLeuAspIle-179 |
| SEQ. ID. NO. 20112 | 185-ThrMetTyrAspSerArgSerArgLeuValAlaGluValSerGluGlnLeuArgSerHisPheGlyAspLeu-208 |
| SEQ. ID. NO. 20113 | 214-IleProArgAsnIleArgLeuAlaGluAlaProSerHisGly-227 |
| SEQ. ID. NO. 20114 | 235-AlaGlnAlaLysGlyAlaLys-241 |
| SEQ. ID. NO. 20115 | 248-AspGluLeuMetAla-252 |

Hydrophilic Regions - Hopp-Woods

| | |
|---|---|
| SEQ. ID. NO. 20116 | 10-AsnGlnLysGlyGlyValGlyLys-17 |
| SEQ. ID. NO. 20117 | 28-LeuAlaSerArgGlyLysArg-34 |
| SEQ. ID. NO. 20118 | 40-LeuAspProGlnGly-44 |
| SEQ. ID. NO. 20119 | 50-SerGlyIleAspLysAlaSerLeu-57 |
| SEQ. ID. NO. 20120 | 67-GlyAspAlaAspValLysSerAlaAlaValArgSerLysGluGlyGly-82 |
| SEQ. ID. NO. 20121 | 95-AlaGluIleGluLeu-99 |
| SEQ. ID. NO. 20122 | 101-GlnGluIleAlaArgGluValArgLeuLysAsnAlaLeu-113 |
| SEQ. ID. NO. 20123 | 115-AlaValAlaGluAspTyrAsp-121 |
| SEQ. ID. NO. 20124 | 164-AlaThrValArgLysIleArgGln-171 |
| SEQ. ID. NO. 20125 | 175-ProAspLeuAspIle-179 |
| SEQ. ID. NO. 20126 | 186-MetTyrAspSerArgSerArgLeuValAlaGluValSerGluGlnLeuArg-202 |
| SEQ. ID. NO. 20127 | 216-ArgAsnIleArgLeuAlaGluAlaProSer-225 |
| SEQ. ID. NO. 20128 | 235-AlaGlnAlaLysGlyAlaLys-241 |
| SEQ. ID. NO. 20129 | 248-AspGluLeuMetAla-252 |

TABLE 1-continued a568
AMPHI Regions - AMPHI
SEQ. ID. NO. 20130    31-SerIlePheArgArg-35
SEQ. ID. NO. 20131    48-LysAlaCysLysAsn-52
SEQ. ID. NO. 20132    70-GluLysAlaAsnThrValArgTyr-77
SEQ. ID. NO. 20133    81-SerLeuAlaGlnCysPheThr-87
SEQ. ID. NO. 20134    111-ArgProLeuProSerIleIleThrAla-119
SEQ. ID. NO. 20135    168-GluPheValGlyPheGlyAsnValPheValGlyGlnPheLeuAsnArgPhePhe-185
SEQ. ID. NO. 20136    199-GluGluPhePheAspValValVal-206
SEQ. ID. NO. 20137    227-PheAsnGlnValPheAlaAlaPheLeu-235
SEQ. ID. NO. 20138    240-HisArgHisAlaAspGlnValAlaAspSerCysArgValGlnSerGln-255
Antigenic Index - Jameson-Wolf
SEQ. ID. NO. 20139    22-IleArgLeuLysArgSerArgLeuProSerIlePhe-33
SEQ. ID. NO. 20140    38-PheSerCysArgArgArgThrCysPheCysLysAlaCysLysAsnSerProIleArgAsnGluThrSerSerSerGlyArgArgGlnPheSerValGlu
                      LysAlaAsnThr-74
SEQ. ID. NO. 20141    90-SerAsnAlaSerLysProArgLeu-97
SEQ. ID. NO. 20142    99-ProIleMetArgGlyArgLysArgPhePheAla-109
SEQ. ID. NO. 20143    140-PheArgGlySerAlaPheLysCysArgLeuAsnAlaGluProCysArg-155
SEQ. ID. NO. 20144    213-AlaAspGlyAspAla-217
SEQ. ID. NO. 20145    236-GlyGlnHisGlyHisArgHisAlaAspGlnValAlaAspSerCysArgValGlnSerGln-255
Hydrophilic Regions - Hopp-Woods
SEQ. ID. NO. 20146    22-IleArgLeuLysArgSerArgLeu-29
SEQ. ID. NO. 20147    40-CysArgArgArgThrCysPhe-46
SEQ. ID. NO. 20148    48-LysAlaCysLysAsnSerProIleArgAsnGluThrSerSerSerGlyArgArgGlnPheSerValGluLysAlaAsnThr-74
SEQ. ID. NO. 20149    92-AlaSerLysProArgLeu-97
SEQ. ID. NO. 20150    101-MetArgGlyArgLysArgPhePheAla-109
SEQ. ID. NO. 20151    143-SerAlaPheLysCysArgLeuAsnAlaGluProCysArg-155
SEQ. ID. NO. 20152    238-HisGlyHisArgHisAlaAspGlnValAlaAspSerCysArgVal-252
a569-2
AMPHI Regions - AMPHI
SEQ. ID. NO. 20153    29-AlaAlaPheCysGlyLeuIleAlaLeuThrAlaLeuTrpGluTyrAlaArgMetAlaGlyLeuCysLys-51
SEQ. ID. NO. 20154    86-PheTrpLeuAlaValMetPro-92
SEQ. ID. NO. 20155    161-IleAlaArgAlaIleSerProGlyLysSerTrpGluGlyAlaIle-175
SEQ. ID. NO. 20156    203-ThrValLeuIleGlyLeu-208
SEQ. ID. NO. 20157    210-LeuThrValValSerValCysGlyAspLeuLeuGluSerTrpLeuLys-225
Antigenic Index - Jameson-Wolf
SEQ. ID. NO. 20158    50-CysLysThrGluThrAsnHis-56
SEQ. ID. NO. 20159    98-LysTrpArgLeuAsnGlyGlyTrp-105
SEQ. ID. NO. 20160    124-SerLeuArgProHisProAspAspAlaLeu-133
SEQ. ID. NO. 20161    154-LysAlaLeuGlyLysHisLysIleAlaArg-163
SEQ. ID. NO. 20162    165-IleSerProGlyLysSerTrpGlu-172
SEQ. ID. NO. 20163    227-AlaAlaGlyIleLysAspSerSerAsnLeuLeuProGlyHis-240
SEQ. ID. NO. 20164    242-GlyValPheAspArgThrAspSer-249
Hydrophilic Regions - Hopp-Woods
SEQ. ID. NO. 20165    50-CysLysThrGluThr-54
SEQ. ID. NO. 20166    127-ProHisProAspAspAlaLeu-133
SEQ. ID. NO. 20167    155-AlaLeuGlyLysHisLysIleAlaArg-163
SEQ. ID. NO. 20168    227-AlaAlaGlyIleLysAspSerSerAsn-235
SEQ. ID. NO. 20169    243-ValPheAspArgThrAspSer-249
a570
AMPHI Regions - AMPHI
SEQ. ID. NO. 20170    6-ArgAlaPheAlaAlaAlaLeuIleGlyLeu-15
SEQ. ID. NO. 20171    22-HisAlaAspThrPheGlnLysIleGlyPheIleAsn-33
SEQ. ID. NO. 20172    43-GlnAlaArgLysIleGlnLysThrLeuAspSer-53
SEQ. ID. NO. 20173    60-AspGluGlnLysLeuGln-66
SEQ. ID. NO. 20174    81-LeuLysAspAlaLysLys-86
SEQ. ID. NO. 20175    122-LeuGlnGlnAsnAlaAsnArgValIleValLysIle-133
Antigenic Index - Jameson-Wolf
SEQ. ID. NO. 20176    33-AsnThrGluArgIleTyrLeuGluSerLysGlnAlaArgLysIleGlnLysThrLeuAspSerGluPheSerAlaArgGlnAspGluLeuGlnLysLeu
                      GlnArgGluGlyLeuAspLeuGluArgGlnLeuAlaGluGlyLysLeuLysAspAlaLysLysAlaGlnAlaGluGluLysTrp-93
SEQ. ID. NO. 20177    100-PheArgLysLysGlnAlaGlnPheGluGluAspTyrAsnLeuArgArgAsnGluGluPheAla-120
SEQ. ID. NO. 20178    123-GlnGlnAsnAlaAsnArgVal-129
SEQ. ID. NO. 20179    133-IleAlaLysGlnGluGlyTyrAspValIle-142
SEQ. ID. NO. 20180    150-AsnThrGlnTyrAspValThrAspSerValIleLysGluMetAsnAlaArg-166
Hydrophilic Regions - Hopp-Woods
SEQ. ID. NO. 20181    37-IleTyrLeuGluSerLysGlnAlaArgLysIleGlnLysThrLeuAspSerGluPheSerAlaArgGlnAspGluLeuGlnLysLeuGlnArgGluGly
                      LeuAspLeuGluArgGlnLeuAlaGluGlyLysLeuLysAspAlaLysLysAlaGlnAlaGluGluLysTrp-93
SEQ. ID. NO. 20182    100-PheArgLysLysGlnAlaGlnPheGluGluAspTyrAsnLeuArgArgAsnGluGluPheAla-120
SEQ. ID. NO. 20183    133-IleAlaLysGlnGluGlyTyr-139
SEQ. ID. NO. 20184    154-AspValThrAspSerValIleLysGluMetAsnAlaArg-166
a571
AMPHI Regions - AMPHI
SEQ. ID. NO. 20185    6-AlaValAsnValLeu-10
SEQ. ID. NO. 20186    40-AspGlyAlaArgValPheArgAlaGly-48
SEQ. ID. NO. 20187    63-AlaAlaValAlaAspPhePheAlaVal-71
SEQ. ID. NO. 20188    94-ValGluValPheLysGlu-99
Antigenic Index - Jameson-Wolf
SEQ. ID. NO. 20189    13-AlaAlaGlyArgGlyThr-18
SEQ. ID. NO. 20190    35-LysGlnAlaGlnAlaAspGlyAlaArgValPheArgAlaGlyHisArgGluGluGlnLeuGlyGlyAspVal-58
SEQ. ID. NO. 20191    77-ArgThrGluArgAlaAla-82

TABLE 1-continued

| | |
|---|---|
| SEQ. ID. NO. 20192 | 96-ValPheLysGluGlyAspPhe-102 |
| SEQ. ID. NO. 20193 | 110-ArgAsnAlaAspPheAlaAlaGluHisGlnArgGluGlyPheAlaGlyGluGluProGlyLeuValValGly-133 |
| SEQ. ID. NO. 20194 | 143-GlyGlnGlyAspPheGlyVal-149 |
| SEQ. ID. NO. 20195 | 154-ValAlaAlaArgArgPro-159 |

Hydrophilic Regions - Hopp-Woods

| | |
|---|---|
| SEQ. ID. NO. 20196 | 13-AlaAlaGlyArgGly-17 |
| SEQ. ID. NO. 20197 | 35-LysGlnAlaGlnAlaAspGlyAlaArgValPheArgAlaGlyHisArgGluGluGlnLeuGly-55 |
| SEQ. ID. NO. 20198 | 77-ArgThrGluArgAlaAla-82 |
| SEQ. ID. NO. 20199 | 96-ValPheLysGluGlyAspPhe-102 |
| SEQ. ID. NO. 20200 | 110-ArgAsnAlaAspPheAlaAlaGluHisGlnArgGluGlyPheAlaGlyGluGluProGly-129 |
| SEQ. ID. NO. 20201 | 154-ValAlaAlaArgArgPro-159 | a572
AMPHI Regions - AMPHI

| | |
|---|---|
| SEQ. ID. NO. 20202 | 6-GlyAlaValGlyLeuProSerAlaLeuAla-15 |
| SEQ. ID. NO. 20203 | 61-GlnValLeuProArgAspTyrThrGlyArg-70 |
| SEQ. ID. NO. 20204 | 94-AsnThrPheAspSerIle-99 |
| SEQ. ID. NO. 20205 | 126-LysGlyLeuGluLeu-130 |
| SEQ. ID. NO. 20206 | 154-IleHisSerMetValArg-159 |
| SEQ. ID. NO. 20207 | 183-GlyLeuProGluArgIleAspSerGly-191 |
| SEQ. ID. NO. 20208 | 200-LeuSerAlaLeuThr-204 |
| SEQ. ID. NO. 20209 | 241-ValAlaAlaPheLeu-245 |
| SEQ. ID. NO. 20210 | 251-PheThrAspIleAlaLysThrValAlaHisCysLeuSerGlnAspPheSerAspGlyIleGlyAspIleGlyGly-275 |

Antigenic Index - Jameson-Wolf

| | |
|---|---|
| SEQ. ID. NO. 20211 | 18-GlnLysGlyLysThr-22 |
| SEQ. ID. NO. 20212 | 26-AlaAsnLysGluThrLeu-31 |
| SEQ. ID. NO. 20213 | 41-ThrAlaArgAlaAsnGly-46 |
| SEQ. ID. NO. 20214 | 51-ProValAspSerGluHis-56 |
| SEQ. ID. NO. 20215 | 63-LeuProArgAspTyrThrGlyArgLeuAsnGluHisGly-75 |
| SEQ. ID. NO. 20216 | 94-AsnThrPheAspSerIleThrProAspGlnAlaValLysHisProAsnTrpArgMetGlyArgLysIleSerValAspSer-120 |
| SEQ. ID. NO. 20217 | 125-AsnLysGlyLeuGluLeu-130 |
| SEQ. ID. NO. 20218 | 138-AsnCysProProAspLysLeuGluVal-146 |
| SEQ. ID. NO. 20219 | 158-ValArgTyrArgAspGlySerVal-165 |
| SEQ. ID. NO. 20220 | 170-GlyAsnProAspMetArgThr-176 |
| SEQ. ID. NO. 20221 | 184-LeuProGluArgIleAspSerGlyValGlyAspLeuAspPhe-197 |
| SEQ. ID. NO. 20222 | 204-ThrPheGlnLysProAspPheAspArg-212 |
| SEQ. ID. NO. 20223 | 263-SerGlnAspPheSerAspGlyIleGlyAspIleGly-274 |
| SEQ. ID. NO. 20224 | 279-GlnAspAlaArgThrArgAlaGlnAla-287 |

Hydrophilic Regions - Hopp-Woods

| | |
|---|---|
| SEQ. ID. NO. 20225 | 27-AsnLysGluThrLeu-31 |
| SEQ. ID. NO. 20226 | 41-ThrAlaArgAlaAsnGly-46 |
| SEQ. ID. NO. 20227 | 52-ValAspSerGluHis-56 |
| SEQ. ID. NO. 20228 | 66-AspTyrThrGlyArgLeuAsnGlu-73 |
| SEQ. ID. NO. 20229 | 111-ArgMetGlyArgLysIleSerVal-118 |
| SEQ. ID. NO. 20230 | 126-LysGlyLeuGluLeu-130 |
| SEQ. ID. NO. 20231 | 140-ProProAspLysLeuGlu-145 |
| SEQ. ID. NO. 20232 | 158-ValArgTyrArgAspGlySer-164 |
| SEQ. ID. NO. 20233 | 170-GlyAsnProAspMetArgThr-176 |
| SEQ. ID. NO. 20234 | 184-LeuProGluArgIleAspSerGlyValGlyAspLeuAspPhe-197 |
| SEQ. ID. NO. 20235 | 206-GlnLysProAspPheAspArg-212 |
| SEQ. ID. NO. 20236 | 265-AspPheSerAspGlyIleGly-271 |
| SEQ. ID. NO. 20237 | 279-GlnAspAlaArgThrArgAlaGlnAla-287 | a574
AMPHI Regions - AMPHI

| | |
|---|---|
| SEQ. ID. NO. 20238 | 6-ProAsnSerLeuGluLys-11 |
| SEQ. ID. NO. 20239 | 47-LeuValGlnAlaLysSerIleProSerGlyPheTyrLysSerLeuAspAlaLeuValAspArgAsnSerGlyArgAlaAlaArgGluLeuAlaGluVal ValAsp-81 |
| SEQ. ID. NO. 20240 | 94-GlyLysLeuTyrArgGln-99 |
| SEQ. ID. NO. 20241 | 110-HisGlnThrLeuLeuAspSerProAspThrThrGly-121 |
| SEQ. ID. NO. 20242 | 175-GluLysAlaValGluThrAlaArgLeu-183 |
| SEQ. ID. NO. 20243 | 218-AsnValGlyLysAlaLeuGluAlaAsnLysLysCys-229 |
| SEQ. ID. NO. 20244 | 246-PheProAlaAlaValGluAlaTyrAlaAlaIleGlu-257 |
| SEQ. ID. NO. 20245 | 266-MetValGlyGluLysLeuTyrGluAlaTyrAla-276 |
| SEQ. ID. NO. 20246 | 281-ProGluGluGlyLeuAsnArgLeuThrGlyTyrMetGlnThrPheProGluLeuAspLeu-300 |
| SEQ. ID. NO. 20247 | 332-AsnGlyValTyrArg-336 |
| SEQ. ID. NO. 20248 | 357-ArgSerValIleGlyArgGlnLeuGlnArgSer-367 |

Antigenic Index - Jameson-Wolf

| | |
|---|---|
| SEQ. ID. NO. 20249 | 1-MetArgProAsnLeuProAsnSerLeuGluLysAlaAspMetAspAsn-16 |
| SEQ. ID. NO. 20250 | 45-ThrValLeuLysGlnAlaLysSerIleProSerGlyPheTyrLysSerLeuAspAlaLeuValAspArgAsnSerGlyArgAlaAlaArgGluLeuAla GluValValAspGlyArgProGlnSerTyrAsp-88 |
| SEQ. ID. NO. 20251 | 96-LeuTyrArgGlnArgGlyGluAsnAspLysAlaIle-107 |
| SEQ. ID. NO. 20252 | 113-LeuLeuAspSerProAspThrThrGlyAlaLysArgAlaArgVal-127 |
| SEQ. ID. NO. 20253 | 135-TyrGlnSerAlaGlyLeuValAspArgAlaGlu-145 |
| SEQ. ID. NO. 20254 | 151-LeuGlnAspGlyGluMetAlaArgGluAlaArgGln-162 |
| SEQ. ID. NO. 20255 | 168-TyrGlnGlnAspArgAspTrpGluLysAlaValGluThr-180 |
| SEQ. ID. NO. 20256 | 182-ArgLeuLeuSerHisAspAspGlnThrTyr-191 |
| SEQ. ID. NO. 20257 | 210-SerAsnPheAspAlaAlaArg-216 |
| SEQ. ID. NO. 20258 | 221-LysAlaLeuGluAlaAsnLysLysCysThrArg-231 |
| SEQ. ID. NO. 20259 | 238-AspIleGluHisArgGlnGlyAsn-245 |
| SEQ. ID. NO. 20260 | 277-AlaGlnGlyLysProGluGluGlyLeuAsnArgLeuThrGlyTyr-291 |
| SEQ. ID. NO. 20261 | 312-LysCysGluLysGluAlaAla-318 |

TABLE 1-continued

| | |
|---|---|
| SEQ. ID. NO. 20262 | 323-GluLeuValArgArgLysProAspLeuAsnGly-333 |
| SEQ. ID. NO. 20263 | 341-LysLeuSerAspLeuAspProAlaTrpLysAlaAspAlaAspMetMetArg-357 |
| SEQ. ID. NO. 20264 | 368-ValMetTyrArgCysArgAsnCysHisPheLys-378 |
| SEQ. ID. NO. 20265 | 386-CysProAlaCysAsnLysTrpGlnThrPheThrProAsnLysIleGluVal-402 |
| Hydrophilic Regions - Hopp-Woods | |
| SEQ. ID. NO. 20266 | 1-MetArgProAsnLeu-5 |
| SEQ. ID. NO. 20267 | 7-AsnSerLeuGluLysAlaAspMetAspAsn-16 |
| SEQ. ID. NO. 20268 | 45-ThrValLeuLysGlnAlaLysSerIle-53 |
| SEQ. ID. NO. 20269 | 62-AspAlaLeuValAspArgAsnSerGlyArgAlaAlaArgGluLeuAlaGluValValAspGlyArgProGlnSer-86 |
| SEQ. ID. NO. 20270 | 96-LeuTyrArgGlnArgGlyGluAsnAspLysAlaIle-107 |
| SEQ. ID. NO. 20271 | 115-AspSerProAspThrThrGlyAlaLysArgAlaArgVal-127 |
| SEQ. ID. NO. 20272 | 140-LeuValAspArgAlaGlu-145 |
| SEQ. ID. NO. 20273 | 152-GlnAspGlyGluMetAlaArgGluAlaArgGln-162 |
| SEQ. ID. NO. 20274 | 169-GlnGlnAspArgAspTrpGluLysAlaValGluThr-180 |
| SEQ. ID. NO. 20275 | 184-LeuSerHisAspAspGlnThrTyr-191 |
| SEQ. ID. NO. 20276 | 211-AsnPheAspAlaAlaArg-216 |
| SEQ. ID. NO. 20277 | 221-LysAlaLeuGluAlaAsnLysLysCysThrArg-231 |
| SEQ. ID. NO. 20278 | 238-AspIleGluHisArgGlnGlyAsn-245 |
| SEQ. ID. NO. 20279 | 279-GlyLysProGluGluGlyLeuAsn-286 |
| SEQ. ID. NO. 20280 | 312-LysCysGluLysGluAlaAla-318 |
| SEQ. ID. NO. 20281 | 323-GluLeuValArgArgLysProAspLeu-331 |
| SEQ. ID. NO. 20282 | 341-LysLeuSerAspLeuAspPro-347 |
| SEQ. ID. NO. 20283 | 349-TrpLysAlaAspAlaAspMetMetArg-357 |
| SEQ. ID. NO. 20284 | 368-ValMetTyrArgCysArgAsnCysHis-376 |
| SEQ. ID. NO. 20285 | 398-AsnLysIleGluVal-402 |
| a575 | |
| AMPHI Regions - AMPHI | |
| SEQ. ID. NO. 20286 | 8-PheArgLysProAlaSer-13 |
| SEQ. ID. NO. 20287 | 20-PheAlaGluAlaVal-24 |
| SEQ. ID. NO. 20288 | 42-SerThrValSerGlyLeuPheSerAla-50 |
| SEQ. ID. NO. 20289 | 114-LeuSerLysSerLysSer-119 |
| SEQ. ID. NO. 20290 | 139-SerSerAspSerPro-143 |
| SEQ. ID. NO. 20291 | 150-PheThrSerPhePheGly-155 |
| SEQ. ID. NO. 20292 | 163-ValSerThrSerAlaLysValIleSerMetPro-173 |
| SEQ. ID. NO. 20293 | 217-SerLysValTyrGluProProAsn-224 |
| SEQ. ID. NO. 20294 | 233-AlaGluThrCysSerThr-238 |
| SEQ. ID. NO. 20295 | 283-AlaGlyPheSerAlaPheAlaSerGlyAla-292 |
| SEQ. ID. NO. 20296 | 294-ThrPheAlaSerGlyPheSerThrGly-302 |
| SEQ. ID. NO. 20297 | 304-SerThrValAlaCys-308 |
| SEQ. ID. NO. 20298 | 311-GlySerAspGlyMetAspAlaValSerAlaLeu-321 |
| Antigenic Index - Jameson-Wolf | |
| SEQ. ID. NO. 20299 | 2-ValSerGlyGluGluAlaPheArgLysProAlaSerProGluGlyGluAlaGlyPhe-20 |
| SEQ. ID. NO. 20300 | 34-GlyArgLeuSerGluLysSerValSer-42 |
| SEQ. ID. NO. 20301 | 54-ThrAspSerGlySerGlyVal-60 |
| SEQ. ID. NO. 20302 | 96-SerSerSerCysValSerAlaProAspLysMetProPhe-108 |
| SEQ. ID. NO. 20303 | 113-ArgLeuSerLysSerLysSerMetArgLeuGluGly-124 |
| SEQ. ID. NO. 20304 | 134-PheAlaAspAsnSerSerSerAspSerProSerLysAlaSerVal-148 |
| SEQ. ID. NO. 20305 | 155-GlyAlaGlySerGly-159 |
| SEQ. ID. NO. 20306 | 173-ProSerSerAlaAlaSerSerArgSerGlySerSerSerGlyThrAspSerSerValArgArgAlaArgLeuAspTrpAlaArgArgLysSerSerSerArgAlaIle-208 |
| SEQ. ID. NO. 20307 | 211-AlaProProProAlaSer-216 |
| SEQ. ID. NO. 20308 | 218-LysValTyrGluProProAsnSerProLeu-227 |
| SEQ. ID. NO. 20309 | 230-SerSerSerAlaGluThrCysSerThrGlySerGluThr-242 |
| SEQ. ID. NO. 20310 | 261-GlyAlaAspSerAlaAlaVal-267 |
| SEQ. ID. NO. 20311 | 276-GlyThrGlySerGlyArgThrAla-283 |
| SEQ. ID. NO. 20312 | 299-PheSerThrGlyPhe-303 |
| SEQ. ID. NO. 20313 | 309-LeuAspGlySerAspGlyMetAsp-316 |
| Hydrophilic Regions - Hopp-Woods | |
| SEQ. ID. NO. 20314 | 2-ValSerGlyGluGluAlaPheArgLysProAlaSerProGluGlyGluAlaGlyPhe-20 |
| SEQ. ID. NO. 20315 | 34-GlyArgLeuSerGluLysSerValSer-42 |
| SEQ. ID. NO. 20316 | 101-SerAlaProAspLysMetPro-107 |
| SEQ. ID. NO. 20317 | 113-ArgLeuSerLysSerLysSerMetArgLeuGluGly-124 |
| SEQ. ID. NO. 20318 | 137-AsnSerSerSerAspSerProSerLysAla-146 |
| SEQ. ID. NO. 20319 | 176-AlaAlaSerSerArgSerGlySerSerSerGlyThrAspSerSerValArgArgAlaArgLeuAspTrpAlaArgArgLysSerSerSerArgAlaIle-208 |
| SEQ. ID. NO. 20320 | 231-SerSerAlaGluThrCysSerThrGlySerGluThr-242 |
| SEQ. ID. NO. 20321 | 310-AspGlySerAspGlyMetAsp-316 |
| a576-1 | |
| AMPHI Regions - AMPHI | |
| SEQ. ID. NO. 20322 | 31-AlaSerGluProAlaAlaAla-37 |
| SEQ. ID. NO. 20323 | 46-SerIleGlySerThr-50 |
| SEQ. ID. NO. 20324 | 63-GlyArgSerLeuLysGlnMetLys-70 |
| SEQ. ID. NO. 20325 | 82-ThrGluAlaMetGln-86 |
| SEQ. ID. NO. 20326 | 102-GlnGluValMetMetLysPheLeuGlnGluGlnAlaLysAlaValGluLysHis-120 |
| SEQ. ID. NO. 20327 | 140-AlaLysAspGlyValLysThrThr-147 |
| SEQ. ID. NO. 20328 | 202-IleLeuGlyTrpThrGluGlyVal-209 |
| Antigenic Index - Jameson-Wolf | |
| SEQ. ID. NO. 20329 | 20-AlaCysGlyLysLysGluAlaAlaPro-28 |
| SEQ. ID. NO. 20330 | 30-SerAlaSerGluProAlaAla-36 |
| SEQ. ID. NO. 20331 | 38-SerSerAlaGlnGlyAspThrSerSerIleGly-48 |
| SEQ. ID. NO. 20332 | 61-AspIleGlyArgSerLeuLysGlnMetLysGluGlnGlyAlaGluIleAspLeu-78 |

TABLE 1-continued

| | |
|---|---|
| SEQ. ID. NO. 20333 | 89-TyrAspGlyLysGluIleLysMetThrGluGluGlnAlaGln-102 |
| SEQ. ID. NO. 20334 | 109-LeuGlnGluGlnGlnAlaLysAlaValGluLysHisLysAlaAspAlaLysAlaAsnLysGluLysGlyGluAlaPheLeuLysGluAsnAlaAlaLys AspGlyValLysThrThrAlaSerGlyLeu-151 |
| SEQ. ID. NO. 20335 | 154-LysIleThrLysGlnGlyGluGlyLysGlnProThrLysAspAspIleVal-170 |
| SEQ. ID. NO. 20336 | 173-GluTyrGluGlyArgLeuIleAsp-180 |
| SEQ. ID. NO. 20337 | 183-ValPheAspSerSerLysAlaAsnGlyGly-192 |
| SEQ. ID. NO. 20338 | 210-GlnLeuLeuLysGluGlyGlyGlu-217 |
| SEQ. ID. NO. 20339 | 224-SerAsnLeuAlaTyrArgGluGlnGlyAlaGlyAspLysIleGlyProAsnAla-241 |
| SEQ. ID. NO. 20340 | 253-GlyAlaProGluAsnAlaProAlaLysGlnProAla-264 |
| SEQ. ID. NO. 20341 | 266-ValAspIleLysLysValAsn-272 |
| Hydrophilic Regions - Hopp-Woods | |
| SEQ. ID. NO. 20342 | 21-CysGlyLysLysGluAlaAlaPro-28 |
| SEQ. ID. NO. 20343 | 30-SerAlaSerGluProAlaAla-36 |
| SEQ. ID. NO. 20344 | 40-AlaGlnGlyAspThrSerSer-46 |
| SEQ. ID. NO. 20345 | 61-AspIleGlyArgSerLeuLysGlnMetLysGluGlnGlyAlaGluIleAspLeu-78 |
| SEQ. ID. NO. 20346 | 89-TyrAspGlyLysGluIleLysMetThrGluGluGlnAlaGln-102 |
| SEQ. ID. NO. 20347 | 112-GlnGlnAlaLysAlaValGluLysHisLysAlaAspAlaLysAlaAsnLysGluLysGlyGluAlaPheLeuLysGluAsnAlaAlaLysAspGlyVal LysThrThrAla-148 |
| SEQ. ID. NO. 20348 | 155-IleThrLysGlnGlyGluGlyLysGlnProThrLysAspAspIleVal-170 |
| SEQ. ID. NO. 20349 | 173-GluTyrGluGlyArgLeuIleAsp-180 |
| SEQ. ID. NO. 20350 | 185-AspSerSerLysAlaAsnGly-191 |
| SEQ. ID. NO. 20351 | 210-GlnLeuLeuLysGluGlyGlyGlu-217 |
| SEQ. ID. NO. 20352 | 227-AlaTyrArgGluGlnGlyAlaGlyAspLysIleGlyPro-239 |
| SEQ. ID. NO. 20353 | 253-GlyAlaProGluAsnAlaProAlaLysGlnProAla-264 |
| SEQ. ID. NO. 20354 | 266-ValAspIleLysLysValAsn-272 |
| a577 | |
| AMPHI Regions - AMPHI | |
| SEQ. ID. NO. 20355 | 8-GlyLysIleValGlyAsn-13 |
| SEQ. ID. NO. 20356 | 24-AlaAlaSerTyrProLysProCysLysSerPheLysLeuAla-37 |
| SEQ. ID. NO. 20357 | 62-ThrValIleLysIleIle-67 |
| SEQ. ID. NO. 20358 | 104-AlaPheValValGlyIle-109 |
| SEQ. ID. NO. 20359 | 112-GlyMetPheAlaLeuPheGlyArg-119 |
| SEQ. ID. NO. 20360 | 144-GluLeuThrAlaProProAlaGln-151 |
| Antigenic Index - Jameson-Wolf | |
| SEQ. ID. NO. 20361 | 1-MetGluArgAsnGlyVal-6 |
| SEQ. ID. NO. 20362 | 14-ArgIleLeuArgMetSerSerGluHisAla-23 |
| SEQ. ID. NO. 20363 | 26-SerTyrProLysProCysLysSerPheLys-35 |
| SEQ. ID. NO. 20364 | 44-ArgSerCysProGlyGly-49 |
| SEQ. ID. NO. 20365 | 88-LeuProGlyGlnLysPheAspLeu-95 |
| SEQ. ID. NO. 20366 | 121-LeuSerLeuArgGlyGluAsnGlyArgLeuArgAlaGluValLysLysAsnAlaArgLeuThrGlyLysGluLeuThrAlaProProAlaGlnAsnAla ProGluSerAlaLysGlnPro-160 |
| Hydrophilic Regions - Hopp-Woods | |
| SEQ. ID. NO. 20367 | 1-MetGluArgAsnGlyVal-6 |
| SEQ. ID. NO. 20368 | 14-ArgIleLeuArgMetSerSerGluHisAla-23 |
| SEQ. ID. NO. 20369 | 29-LysProCysLysSerPheLys-35 |
| SEQ. ID. NO. 20370 | 121-LeuSerLeuArgGlyGluAsnGlyArgLeuArgAlaGluValLysLysAsnAlaArgLeuThrGlyLysGluLeuThr-146 |
| SEQ. ID. NO. 20371 | 152-AsnAlaProGluSerAlaLysGlnPro-160 |
| a578 | |
| AMPHI Regions - AMPHI | |
| SEQ. ID. NO. 20372 | 10-PheAlaAspPhePheLysAspPheAlaProGlnPheGlyGlyPheGlnAsn-26 |
| SEQ. ID. NO. 20373 | 34-AspPhePheAlaAlaPheLeuGlyGlyLeuGlu-44 |
| SEQ. ID. NO. 20374 | 71-AsnThrAspAlaAlaArgPhe-77 |
| Antigenic Index - Jameson-Wolf | |
| SEQ. ID. NO. 20375 | 2-GlyLysLeuAspIle-6 |
| SEQ. ID. NO. 20376 | 13-PhePheLysAspPheAlaProGlnPheGlyGly-23 |
| SEQ. ID. NO. 20377 | 43-LeuGluGlyAspValGlyAsnThrAla-51 |
| SEQ. ID. NO. 20378 | 71-AsnThrAspAlaAlaArgPheAla-78 |
| SEQ. ID. NO. 20379 | 88-HisAsnGlnAsnIleGlnThrArgAsnAspPheArgLeuGluArgGlyGlyValGly-106 |
| Hydrophilic Regions - Hopp-Woods | |
| SEQ. ID. NO. 20380 | 2-GlyLysLeuAspIle-6 |
| SEQ. ID. NO. 20381 | 43-LeuGluGlyAspValGlyAsn-49 |
| SEQ. ID. NO. 20382 | 73-AspAlaAlaArgPheAla-78 |
| SEQ. ID. NO. 20383 | 92-IleGlnThrArgAsnAspPheArgLeuGluArgGlyGlyVal-105 |
| a579 | |
| AMPHI Regions - AMPHI | |
| SEQ. ID. NO. 20384 | 6-PheAspPheLeuHisLeuIleSerAlaSerGlyTrpGluHisLeuAlaGlu-22 |
| SEQ. ID. NO. 20385 | 49-ValAlaValMetArg-53 |
| SEQ. ID. NO. 20386 | 66-IleSerPheLeuCysAsn-71 |
| SEQ. ID. NO. 20387 | 115-LeuSerAsnPheAla-119 |
| SEQ. ID. NO. 20388 | 129-ProPheLysValGlyAspPheIleArgValGlyGlyPheGluGlyTyrValArgGluIleLys-149 |
| SEQ. ID. NO. 20389 | 258-GlnValValGluAsnLeuArg-264 |
| Antigenic Index - Jameson-Wolf | |
| SEQ. ID. NO. 20390 | 110-SerLeuLysAspGlnLeuSer-116 |
| SEQ. ID. NO. 20391 | 128-ArgProPheLysVal-132 |
| SEQ. ID. NO. 20392 | 136-IleArgValGlyGlyPheGluGlyTyrValArgGluIleLysMet-150 |
| SEQ. ID. NO. 20393 | 154-SerLeuArgThrThrAspAsnGluGluValValLeu-165 |
| SEQ. ID. NO. 20394 | 175-IleValAsnArgSerThrLeu-181 |
| SEQ. ID. NO. 20395 | 198-LeuLysValAlaLysGluAlaValLeu-206 |
| SEQ. ID. NO. 20396 | 216-ValGlnAsnGluGluArgGlnAla-223 |
| SEQ. ID. NO. 20397 | 231-GlyAspAsnAlaIle-235 |

TABLE 1-continued

| | |
|---|---|
| SEQ. ID. NO. 20398 | 244-AsnGluAlaAspArgTrpThrLeu-251 |
| SEQ. ID. NO. 20399 | 253-CysAspLeuAsnGluGlnValValGluAsnLeuArgLysValAsn-267 |
| SEQ. ID. NO. 20400 | 271-ProPheProGlnArgAspIleHis-278 |

Hydrophilic Regions - Hopp-Woods

| | |
|---|---|
| SEQ. ID. NO. 20401 | 110-SerLeuLysAspGlnLeu-115 |
| SEQ. ID. NO. 20402 | 144-TyrValArgGluIleLysMet-150 |
| SEQ. ID. NO. 20403 | 155-LeuArgThrThrAspAsnGluGluValVal-164 |
| SEQ. ID. NO. 20404 | 198-LeuLysValAlaLysGluAlaValLeu-206 |
| SEQ. ID. NO. 20405 | 216-ValGlnAsnGluGluArgGlnAla-223 |
| SEQ. ID. NO. 20406 | 244-AsnGluAlaAspArgTrp-249 |
| SEQ. ID. NO. 20407 | 254-AspLeuAsnGluGlnValValGluAsnLeuArgLysValAsn-267 |
| SEQ. ID. NO. 20408 | 273-ProGlnArgAspIleHis-278 | a580
AMPHI Regions - AMPHI

| | |
|---|---|
| SEQ. ID. NO. 20409 | 47-ProValSerAlaSerLys-52 |
| SEQ. ID. NO. 20410 | 54-SerLeuValLysProLeuSerGlnProLeuAla-64 |

Antigenic Index - Jameson-Wolf

| | |
|---|---|
| SEQ. ID. NO. 20411 | 1-MetAspSerProLysValGlyCysGly-9 |
| SEQ. ID. NO. 20412 | 48-ValSerAlaSerLys-52 |
| SEQ. ID. NO. 20413 | 66-AlaArgProGluAlaAlaHis-72 |
| SEQ. ID. NO. 20414 | 81-ArgProGluAlaLeuAlaAspAsnSerValSerProThrHisAlaThrSerGlyGluVal-100 |

Hydrophilic Regions - Hopp-Woods

| | |
|---|---|
| SEQ. ID. NO. 20415 | 1-MetAspSerProLysVal-6 |
| SEQ. ID. NO. 20416 | 66-AlaArgProGluAlaAlaHis-72 |
| SEQ. ID. NO. 20417 | 81-ArgProGluAlaLeuAla-86 |
| SEQ. ID. NO. 20418 | 96-ThrSerGlyGluVal-100 | a581
AMPHI Regions - AMPHI

| | |
|---|---|
| SEQ. ID. NO. 20419 | 43-SerHisPheIleSerLeu-48 |
| SEQ. ID. NO. 20420 | 56-ArgGluCysPheValGlyPhe-62 |
| SEQ. ID. NO. 20421 | 76-AlaThrAlaPheGlyArgIleAsnGln-84 |
| SEQ. ID. NO. 20422 | 91-ValHisGlyPheLeuThrThrPheAla-99 |

Antigenic Index - Jameson-Wolf

| | |
|---|---|
| SEQ. ID. NO. 20423 | 8-GlyGlnThrGlyIleGluGlnAsnThrPheCysArgArgGlyPheThrArgIleAspMetGlyGlyAsnThrAspVal-33 |
| SEQ. ID. NO. 20424 | 35-ValGlnAlaAspArgGlyLeuThrSer-43 |
| SEQ. ID. NO. 20425 | 49-SerLysLeuGluThrGluValArgGluCysPhe-59 |
| SEQ. ID. NO. 20426 | 98-PheAlaGlyArgIleAsnProAlaHisCysGlnSerGlnThrAla-112 |

Hydrophilic Regions - Hopp-Woods

| | |
|---|---|
| SEQ. ID. NO. 20427 | 35-ValGlnAlaAspArgGlyLeu-41 |
| SEQ. ID. NO. 20428 | 49-SerLysLeuGluThrGluValArgGlu-57 | a582
AMPHI Regions - AMPHI

| | |
|---|---|
| SEQ. ID. NO. 20429 | 27-ThrAspAsnValThrArgLeuAla-34 |
| SEQ. ID. NO. 20430 | 65-ValArgSerSerLeu-69 |
| SEQ. ID. NO. 20431 | 91-GlyGluThrAlaAspIleTyrThrProLeuSer-101 |
| SEQ. ID. NO. 20432 | 139-GlySerProThrArg-143 |
| SEQ. ID. NO. 20433 | 169-IleAlaGluAspLeuPhe-174 |
| SEQ. ID. NO. 20434 | 246-SerArgSerTrpAsnArgIleTyrAlaMet-255 |
| SEQ. ID. NO. 20435 | 263-LeuThrValIleProArgValTrpValArgAlaPheAspGlnSer-277 |
| SEQ. ID. NO. 20436 | 286-IleAlaAspTyrMetGlyTyr-292 |
| SEQ. ID. NO. 20437 | 334-LeuLysGlyValValArgGlyPheHisGlyTyrGlyGlu-346 |

Antigenic Index - Jameson-Wolf

| | |
|---|---|
| SEQ. ID. NO. 20438 | 26-LeuThrAspAsnValThr-31 |
| SEQ. ID. NO. 20439 | 34-AlaCysTyrAspArg-38 |
| SEQ. ID. NO. 20440 | 44-LeuProSerSerAlaGlyGlnGluGlyGlnGluSerLysAla-57 |
| SEQ. ID. NO. 20441 | 63-GluThrValArgSerSerLeuAspLysGlyGluAla-74 |
| SEQ. ID. NO. 20442 | 77-ValValGluLysGlyGlyAspAlaLeuProAlaAspSerAlaGlyGluThrAlaAsp-95 |
| SEQ. ID. NO. 20443 | 105-AspLeuAspLysAsnAspLeuArgGly-113 |
| SEQ. ID. NO. 20444 | 115-LeuGlyValArgGluHisAsnProMetTyr-124 |
| SEQ. ID. NO. 20445 | 131-AsnAsnSerProAsnTyrAlaProGlySerProThrArgGlyThrThrValGlnGluLysPheGlyGlnGlnLysArgAlaGluThrLysLeu-161 |
| SEQ. ID. NO. 20446 | 165-PheLysSerLysIleAlaGluAspLeuPheLysThrArgAla-178 |
| SEQ. ID. NO. 20447 | 183-GlyTyrThrGlnArgSerAspTrpGlnIleTyrAsnGlnGlyArgLysSerAlaProPheArgAsnThrAspTyrLysPro-209 |
| SEQ. ID. NO. 20448 | 216-ProValLysAlaAspLeuProPheGlyGlyArgLeuArgMet-229 |
| SEQ. ID. NO. 20449 | 237-GlnSerAsnGlyGlnSerArgProGluSerArgSerTrpAsn-250 |
| SEQ. ID. NO. 20450 | 273-AlaPheAspGlnSerGlyAspLysAsnAspAsnProAspIleAlaAsp-288 |
| SEQ. ID. NO. 20451 | 291-GlyTyrGlyAspValLysLeuGlnTyrArgLeuAsnAspArgGlnAsnVal-307 |
| SEQ. ID. NO. 20452 | 312-ArgTyrAsnProLysThrGlyTyr-319 |
| SEQ. ID. NO. 20453 | 330-IleLysGlyLysLeuLysGlyValVal-338 |
| SEQ. ID. NO. 20454 | 342-HisGlyTyrGlyGluSerLeuIleAspTyrAsnHisLysGlnAsnGly-357 |
| SEQ. ID. NO. 20455 | 365-AsnAspLeuAspGlyIle-370 |

Hydrophilic Regions - Hopp-Woods

| | |
|---|---|
| SEQ. ID. NO. 20456 | 48-AlaGlyGlnGluGlyGlnGluSerLysAla-57 |
| SEQ. ID. NO. 20457 | 63-GluThrValArgSerSerLeuAspLysGlyGluAla-74 |
| SEQ. ID. NO. 20458 | 79-GluLysGlyGlyAspAlaLeuPro-86 |
| SEQ. ID. NO. 20459 | 88-AspSerAlaGlyGluThrAlaAsp-95 |
| SEQ. ID. NO. 20460 | 105-AspLeuAspLysAsnAspLeuArgGly-113 |
| SEQ. ID. NO. 20461 | 115-LeuGlyValArgGluHisAsn-121 |
| SEQ. ID. NO. 20462 | 140-SerProThrArgGlyThrThrValGlnGluLysPheGlyGlnGlnLysArgAlaGluThrLysLeu-161 |
| SEQ. ID. NO. 20463 | 165-PheLysSerLysIleAlaGluAspLeuPheLysThrArgAla-178 |
| SEQ. ID. NO. 20464 | 195-GlnGlyArgLysSerAlaProPheArgAsnThrAspTyrLysPro-209 |

TABLE 1-continued

| | |
|---|---|
| SEQ. ID. NO. 20465 | 225-GlyArgLeuArgMet-229 |
| SEQ. ID. NO. 20466 | 239-AsnGlyGlnSerArgProGluSerArgSerTrp-249 |
| SEQ. ID. NO. 20467 | 274-PheAspGlnSerGlyAspLysAsnAspAsnProAspIleAlaAsp-288 |
| SEQ. ID. NO. 20468 | 293-GlyAspValLysLeu-297 |
| SEQ. ID. NO. 20469 | 299-TyrArgLeuAsnAspArgGlnAsn-306 |
| SEQ. ID. NO. 20470 | 332-GlyLysLeuLysGlyValVal-338 |
| SEQ. ID. NO. 20471 | 352-AsnHisLysGlnAsn-356 |
| a583 | |
| AMPHI Regions - AMPHI | |
| SEQ. ID. NO. 20472 | 11-HisLeuAlaPheCysAlaPheCysGlyIle-20 |
| SEQ. ID. NO. 20473 | 28-ArgLeuHisAsnArgMetTyrAsnAlaAlaAlaAlaArg-40 |
| SEQ. ID. NO. 20474 | 58-ValThrAspAlaGln-62 |
| SEQ. ID. NO. 20475 | 66-SerLysAsnGlyAspLysGlnIle-73 |
| SEQ. ID. NO. 20476 | 75-AspThrHisProGlnPro-80 |
| SEQ. ID. NO. 20477 | 117-GlyTyrAlaGlyTyrCysAspGln-124 |
| SEQ. ID. NO. 20478 | 140-AspAsnGlyGlyAsnHisThrAsp-147 |
| SEQ. ID. NO. 20479 | 162-GlyTyrGlyGlnCysGlnAsnGlnGlyAla-171 |
| Antigenic Index - Jameson-Wolf | |
| SEQ. ID. NO. 20480 | 24-ThrAlaGlyAsnArgLeuHisAsnArgMetTyr-34 |
| SEQ. ID. NO. 20481 | 41-GlyIleGlyArgGlyAsnGlySerGlnGlnGlnPheGlyLysSerGluThrValThrAspAlaGlnArgPheSerSerLysAsnGlyAspLysGlnIle<br>SerAspThrHisProGlnProCysPheGluGlnThrAlaArgAsnHisAsnCysAspGlyAsnGlnProAsnGlnArgIleGly<br>GluArgThrGlnArgIleAlaHisArgArgThrArgPheValGlyGlyTyrAlaGlyTyrCysAspGlnProAspGlyAsnAsn<br>ArgGlnArgThrGlnArgHisGlyLeuAlaAspAsnGlyGlyAsnHisThrAspLysHisGlyGlnGlnArgProSerLeuArg<br>LeuAspProValGlyTyrGlyGlnCysGlnAsnGlnGlyAlaGlnTyrCysGlyAsnGlyGluGlyTyrArgPhe-182 |
| SEQ. ID. NO. 20482 | 190-AspLeuArgLysLysAspArgProGluLysSerGluLys-202 |
| Hydrophilic Regions - Hopp-Woods | |
| SEQ. ID. NO. 20483 | 27-AsnArgLeuHisAsn-31 |
| SEQ. ID. NO. 20484 | 41-GlyIleGlyArgGlyAsnGlySer-48 |
| SEQ. ID. NO. 20485 | 51-GlnPheGlyLysSerGluThrValThrAspAlaGlnArgPheSerSerLysAsnGlyAspLysGlnIleSerAspThrHisPro-78 |
| SEQ. ID. NO. 20486 | 84-GlnThrAlaArgAsnHisAsnCysAspGlyAsnGlnProAsnGlnArgIleGlyGluArgThrGlnArgIleAlaHisArgArgThrArgPhe-114 |
| SEQ. ID. NO. 20487 | 123-AspGlnProAspGlyAsnAsnArgGlnArgThrGlnArg-135 |
| SEQ. ID. NO. 20488 | 137-GlyLeuAlaAspAsnGlyGlyAsnHisThrAspLysHisGlyGlnGlnArgProSerLeuArgLeuAspPro-160 |
| SEQ. ID. NO. 20489 | 178-GluGlyTyrArgPhe-182 |
| SEQ. ID. NO. 20490 | 190-AspLeuArgLysLysAspArgProGluLysSerGluLys-202 |
| a584-2 | |
| AMPHI Regions - AMPHI | |
| SEQ. ID. NO. 20491 | 28-GluPheSerGluSerAlaGlyValGluAlaValGlnAspThrMet-42 |
| SEQ. ID. NO. 20492 | 60-AlaGluPheValLysLysPheAsnAsnPheThrArgLys-72 |
| SEQ. ID. NO. 20493 | 116-PheAspAlaLeuAsnArgPheIleAlaAspVal-126 |
| SEQ. ID. NO. 20494 | 148-IleAspGlnValSerLysAsp-154 |
| SEQ. ID. NO. 20495 | 166-LeuAlaGlyValLeuGly-171 |
| SEQ. ID. NO. 20496 | 186-GlySerHisIleAla-190 |
| SEQ. ID. NO. 20497 | 196-GlnAlaLysMetLeuArgAlaMet-203 |
| Antigenic Index - Jameson-Wolf | |
| SEQ. ID. NO. 20498 | 50-AlaGluGlyArgAspLysAsnAlaVal-58 |
| SEQ. ID. NO. 20499 | 61-GluPheValLysLysPheAsnAsnPheThrArgLysSerLysAsnGlySerPheLysThrGluLeuValSerArgSerAlaMetProArgTyrGlnTyr<br>ThrAsnGlyArgArgIleGlnThrGlyTrpGluGluArgAlaGluPheLysValGluGlyArgAsnPheAspAla-118 |
| SEQ. ID. NO. 20500 | 138-HisValSerArgGluArgArgAsnGluValIleAspGlnValSerLysAspAlaValLeu-157 |
| SEQ. ID. NO. 20501 | 159-PheLysAlaArgAlaGluLysLeuAla-167 |
| SEQ. ID. NO. 20502 | 189-IleAlaGlyGlyGly-193 |
| SEQ. ID. NO. 20503 | 210-AsnMetGluGlyAlaAspSerAlaAlaProGlyValGluGluIleSer-225 |
| Hydrophilic Regions - Hopp-Woods | |
| SEQ. ID. NO. 20504 | 50-AlaGluGlyArgAspLysAsnAlaVal-58 |
| SEQ. ID. NO. 20505 | 67-AsnAsnPheThrArgLysSerLysAsnGlySerPheLysThrGluLeuValSer-84 |
| SEQ. ID. NO. 20506 | 95-AsnGlyArgArgIleGlnThrGlyTrpGluGluArgAlaGluPheLysValGluGlyArgAsnPheAspAla-118 |
| SEQ. ID. NO. 20507 | 138-HisValSerArgGluArgArgAsnGluValIleAspGlnValSerLysAspAlaValLeu-157 |
| SEQ. ID. NO. 20508 | 159-PheLysAlaArgAlaGluLysLeuAla-167 |
| SEQ. ID. NO. 20509 | 210-AsnMetGluGlyAlaAspSerAlaAlaProGlyValGluGluIleSer-225 |
| a585 | |
| AMPHI Regions - AMPHI | |
| SEQ. ID. NO. 20510 | 6-ArgIlePheAlaThrPheCysAlaValIleValCys-17 |
| SEQ. ID. NO. 20511 | 46-ThrThrLeuMetGlySerIleIleSer-54 |
| SEQ. ID. NO. 20512 | 65-ArgGluIleLeuThrGluTrpLysAsp-73 |
| SEQ. ID. NO. 20513 | 93-HisArgTyrIleAspSer-98 |
| SEQ. ID. NO. 20514 | 133-LysAspTrpAspLysLeuGlnAlaArgArg-142 |
| SEQ. ID. NO. 20515 | 153-ProLeuAlaProIleTrp-158 |
| SEQ. ID. NO. 20516 | 178-LeuAlaGlyAsnIleAlaLysProIleArgIleLeuGlyAsnGlyMetAspArgValAla-197 |
| SEQ. ID. NO. 20517 | 223-PheAspLysMetValGluLysLeuGluLysLeuVal-234 |
| SEQ. ID. NO. 20518 | 247-GluMetArgSerPro-251 |
| SEQ. ID. NO. 20519 | 255-MetGlnAlaIleValGlyLeuIle-262 |
| SEQ. ID. NO. 20520 | 273-LeuLysArgLeuGluGly-278 |
| SEQ. ID. NO. 20521 | 353-LeuTyrArgAlaPheAspAsnValIleArgAsnAlaValAsn-366 |
| SEQ. ID. NO. 20522 | 430-IleIleGluGlnHisCysGlyLysIleIleAlaGlu-441 |
| Antigenic Index - Jameson-Wolf | |
| SEQ. ID. NO. 20523 | 36-AsnGlnPheAsnGlnArgArgThrIleGlu-45 |
| SEQ. ID. NO. 20524 | 56-PheArgAlaArgGlyAspAlaGlyAlaArgGluIleLeuThrGluTrpLysAspSerProValSer-77 |
| SEQ. ID. NO. 20525 | 84-GlnGlyAspGluLysLysAspIleLeu-92 |
| SEQ. ID. NO. 20526 | 97-AspSerTyrThrIleGluArgAlaArgLeu-106 |
| SEQ. ID. NO. 20527 | 120-GluTyrAspArgPheGlyGlu-126 |
| SEQ. ID. NO. 20528 | 133-LysAspTrpAspLysLeuGlnAlaArgArgLeuProSerPro-146 |

TABLE 1-continued

| | |
|---|---|
| SEQ. ID. NO. 20529 | 189-LeuGlyAsnGlyMetAspArgValAlaAsnGlyGluLeuGluThrArgIle-205 |
| SEQ. ID. NO. 20530 | 207-GlnGlnValAspAspArgAspAspGluLeuSer-217 |
| SEQ. ID. NO. 20531 | 225-LysMetValGluLysLeuGluLysLeuValAlaLysGluArgHisLeu-240 |
| SEQ. ID. NO. 20532 | 246-HisGluMetArgSerProLeuAla-253 |
| SEQ. ID. NO. 20533 | 264-AlaGlnProGlnLysGlnGluGlnTyrLeuLysArgLeuGluGlyGluLeuThrArgMetAspThrLeuAla-287 |
| SEQ. ID. NO. 20534 | 294-SerArgLeuGluThrSerAsnMetAlaLeuGluLysGluSerLeuLys-309 |
| SEQ. ID. NO. 20535 | 317-LeuValGluAspAsnGlnSerIleAlaGlnLysAsnGlyGln-330 |
| SEQ. ID. NO. 20536 | 335-SerAlaAspGlyLysIleProGluAsnThr-344 |
| SEQ. ID. NO. 20537 | 367-TyrSerProGluGlySerThr-373 |
| SEQ. ID. NO. 20538 | 377-AsnIleGlyGlnAspHisLysHis-384 |
| SEQ. ID. NO. 20539 | 388-AspValThrAspAsnGlyProGlyValAspGluMetGln-400 |
| SEQ. ID. NO. 20540 | 409-TyrArgAlaAspSerSerAlaAsnLysProGlyThrGly-421 |
| SEQ. ID. NO. 20541 | 432-GluGlnHisCysGlyLysIleIleAlaGluAsnIleLysProAsnGlyLeuArg-449 |
| SEQ. ID. NO. 20542 | 453-IleLeuProLysLysLysThrGlySerLysThrGluLysSerAlaAsn-468 |
| Hydrophilic Regions - Hopp-Woods | |
| SEQ. ID. NO. 20543 | 37-GlnPheAsnGlnArgArgThrIleGlu-45 |
| SEQ. ID. NO. 20544 | 56-PheArgAlaArgGlyAspAlaGlyAlaArgGluIleLeuThrGluTrpLysAspSerProVal-76 |
| SEQ. ID. NO. 20545 | 84-GlnGlyAspGluLysLysAspIleLeu-92 |
| SEQ. ID. NO. 20546 | 100-ThrIleGluArgAlaArgLeu-106 |
| SEQ. ID. NO. 20547 | 120-GluTyrAspArgPheGlyGlu-126 |
| SEQ. ID. NO. 20548 | 133-LysAspTrpAspLysLeuGlnAlaArgArgLeuPro-144 |
| SEQ. ID. NO. 20549 | 192-GlyMetAspArgValAlaAsnGlyGluLeuGluThrArgIle-205 |
| SEQ. ID. NO. 20550 | 207-GlnGlnValAspAspArgAspAspGluLeuSer-217 |
| SEQ. ID. NO. 20551 | 225-LysMetValGluLysLeuGluLysLeuValAlaLysGluArgHisLeu-240 |
| SEQ. ID. NO. 20552 | 246-HisGluMetArgSerProLeu-252 |
| SEQ. ID. NO. 20553 | 265-GlnProGlnLysGlnGluGlnTyrLeuLysArgLeuGluGlyGluLeuThrArgMetAspThrLeuAla-287 |
| SEQ. ID. NO. 20554 | 294-SerArgLeuGluThr-298 |
| SEQ. ID. NO. 20555 | 302-AlaLeuGluLysGluSerLeuLys-309 |
| SEQ. ID. NO. 20556 | 317-LeuValGluAspAsnGlnSerIleAlaGlnLysAsnGlyGln-330 |
| SEQ. ID. NO. 20557 | 336-AlaAspGlyLysIleProGlu-342 |
| SEQ. ID. NO. 20558 | 389-ValThrAspAsnGlyProGlyValAspGluMetGln-400 |
| SEQ. ID. NO. 20559 | 410-ArgAlaAspSerSerAlaAsnLysProGlyThr-420 |
| SEQ. ID. NO. 20560 | 438-IleIleAlaGluAsnIleLys-444 |
| SEQ. ID. NO. 20561 | 454-LeuProLysLysLysThrGlySerLysThrGluLysSerAlaAsn-468 |
| a586 | |
| AMPHI Regions - AMPHI | |
| SEQ. ID. NO. 20562 | 12-AspAsnPheLysTyrPheTrpLysThr-20 |
| SEQ. ID. NO. 20563 | 30-IleLeuAlaAlaLeuGly-35 |
| SEQ. ID. NO. 20564 | 56-ValLeuAlaAsnIleValGluLysAlaGlnAsnLysAlaPro-69 |
| SEQ. ID. NO. 20565 | 80-LeuGlnGlnSerTyrProHisSerIleSer-89 |
| SEQ. ID. NO. 20566 | 177-SerGlnGluAlaLeuLysAsnTyrGlyGlnAlaLeuGluLysMetProGlnAspSerValGlyArg-198 |
| Antigenic Index - Jameson-Wolf | |
| SEQ. ID. NO. 20567 | 4-HisLeuGluGluGlnGlnGluLeuAspAsn-13 |
| SEQ. ID. NO. 20568 | 43-GlnAsnArgAlaAlaSerGlnAsnGlnGluAla-53 |
| SEQ. ID. NO. 20569 | 60-IleValGluLysAlaGlnAsnLysAlaProGlnSerGluIleAsnAlaGluLeuAlaLysLeuGlnGln-82 |
| SEQ. ID. NO. 20570 | 100-ThrGluPheAspAlaGlnArgTyrAspValAlaGluGly-112 |
| SEQ. ID. NO. 20571 | 118-LeuSerAsnGlnLysAspSerLeu-125 |
| SEQ. ID. NO. 20572 | 140-GlnGlnLysLysTyrAspAla-146 |
| SEQ. ID. NO. 20573 | 153-ThrProValGluAlaAspPhe-159 |
| SEQ. ID. NO. 20574 | 164-MetGluThrLysGlyAspVal-170 |
| SEQ. ID. NO. 20575 | 173-AlaGlnGlyLysSerGlnGluAlaLeuLysAsnTyrGlyGlnAlaLeuGluLysMetProGlnAspSerValGlyArgGluLeuVal-201 |
| SEQ. ID. NO. 20576 | 204-LysLeuAspSerLeuLys-209 |
| Hydrophilic Regions - Hopp-Woods | |
| SEQ. ID. NO. 20577 | 4-HisLeuGluGluGlnGlnGluLeuAspAsn-13 |
| SEQ. ID. NO. 20578 | 45-ArgAlaAlaSerGlnAsnGlnGluAla-53 |
| SEQ. ID. NO. 20579 | 60-IleValGluLysAlaGlnAsnLysAlaProGlnSerGluIleAsnAlaGluLeuAlaLys-79 |
| SEQ. ID. NO. 20580 | 100-ThrGluPheAspAlaGlnArgTyrAspValAlaGluGly-112 |
| SEQ. ID. NO. 20581 | 120-AsnGlnLysAspSerLeu-125 |
| SEQ. ID. NO. 20582 | 140-GlnGlnLysLysTyrAspAla-146 |
| SEQ. ID. NO. 20583 | 153-ThrProValGluAlaAspPhe-159 |
| SEQ. ID. NO. 20584 | 164-MetGluThrLysGlyAspVal-170 |
| SEQ. ID. NO. 20585 | 174-GlnGlyLysSerGlnGluAlaLeuLys-182 |
| SEQ. ID. NO. 20586 | 187-AlaLeuGluLysMetProGlnAspSerValGlyArgGluLeuVal-201 |
| SEQ. ID. NO. 20587 | 204-LysLeuAspSerLeuLys-209 |
| a587 | |
| AMPHI Regions - AMPHI | |
| SEQ. ID. NO. 20588 | 6-LeuProAlaLeuProAlaIleLeuProLeuSerAla-17 |
| SEQ. ID. NO. 20589 | 232-LysGlnProAspArgLeuAsp-238 |
| Antigenic Index - Jameson-Wolf | |
| SEQ. ID. NO. 20590 | 27-AspIleMetThrAspLysGlyLysTrpLysLeuGluThr-39 |
| SEQ. ID. NO. 20591 | 44-LeuAsnSerGluAsnAsnArgAlaGluLeu-53 |
| SEQ. ID. NO. 20592 | 71-ThrGluIleGlnGluAsnGlySerAsnThr-80 |
| SEQ. ID. NO. 20593 | 95-GlyAsnThrAspIleTyrGlySerGlySer-104 |
| SEQ. ID. NO. 20594 | 108-HisGluGluArgLysLeuAspGlyAsnGlyLysThrArgAsnLysArgMetSerAsp-126 |
| SEQ. ID. NO. 20595 | 135-PheLeuLysAspAspLysAsnProAla-143 |
| SEQ. ID. NO. 20596 | 151-ThrValTyrGluLysSerArgAsnLysAlaSerSerGlyLysSer-165 |
| SEQ. ID. NO. 20597 | 187-TyrArgIleAsnGlySerLysThrLeuSerSerAsnThrLysTyrLysAlaGly-204 |
| SEQ. ID. NO. 20598 | 217-AlaAsnAspArgIleSerLeuThrGlyGly-226 |
| SEQ. ID. NO. 20599 | 231-GlyLysGlnProAspArgLeuAspGlyLysLysGluSerAlaArgAsnThrSerThr-249 |
| SEQ. ID. NO. 20600 | 273-ValSerGlyGlnSerSerSerGluLeuLysPhe-283 |

TABLE 1-continued

Hydrophilic Regions - Hopp-Woods
SEQ. ID. NO. 20601   27-AspIleMetThrAspLysGlyLysTrpLysLeu-37
SEQ. ID. NO. 20602   47-GluAsnAsnArgAlaGluLeu-53
SEQ. ID. NO. 20603   72-GluIleGlnGluAsnGlySerAsn-79
SEQ. ID. NO. 20604   108-HisGluGluArgLysLeuAspGlyAsnGlyLysThrArgAsnLysArgMetSerAsp-126
SEQ. ID. NO. 20605   135-PheLeuLysAspAspLysAsnPro-142
SEQ. ID. NO. 20606   151-ThrValTyrGluLysSerArgAsnLysAlaSerSerGly-163
SEQ. ID. NO. 20607   193-LysThrLeuSerSer-197
SEQ. ID. NO. 20608   199-ThrLysTyrLysAla-203
SEQ. ID. NO. 20609   217-AlaAsnAspArgIleSer-222
SEQ. ID. NO. 20610   232-LysGlnProAspArgLeuAspGlyLysLysGluSerAlaArgAsn-246
SEQ. ID. NO. 20611   277-SerSerSerGluLeuLysPhe-283
a588
AMPHI Regions - AMPHI
SEQ. ID. NO. 20612   52-GlnAspGlyArgAsnTyrThrGlySerPhe-61
SEQ. ID. NO. 20613   99-GlyThrPheLysLys-103
Antigenic Index - Jameson-Wolf
SEQ. ID. NO. 20614   25-SerTyrGlnGluProGlyCysThrTyrGluGlyAspValGlyLysAspGlyLysProAlaGlyLysGlyThrTrpArgCysGlnAspGlyArgAsn
                     TyrThrGlySerPheLysAsnGlyLysPheAspGlyGlnGly-70
SEQ. ID. NO. 20615   80-IlePheIleGluProPheAsnSerAspSerThrLysPheArg-93
SEQ. ID. NO. 20616   100-ThrPheLysLysGlyLeuAlaHisGlyArgPheThrValSerGlnAsnGlyGluThr-118
SEQ. ID. NO. 20617   124-CysGluAsnGlyMetIleLysGluValLysLeuProLysAsnLys-138
Hydrophilic Regions - Hopp-Woods
SEQ. ID. NO. 20618   33-TyrGluGlyAspValGlyLysAspGlyLysProAlaGly-45
SEQ. ID. NO. 20619   47-GlyThrTrpArgCysGlnAspGlyArgAsnTyr-57
SEQ. ID. NO. 20620   61-PheLysAsnGlyLysPheAspGly-68
SEQ. ID. NO. 20621   85-PheAsnSerAspSerThrLysPheArg-93
SEQ. ID. NO. 20622   100-ThrPheLysLysGlyLeuAla-106
SEQ. ID. NO. 20623   124-CysGluAsnGlyMetIleLysGluValLysLeuProLysAsnLys-138
a589
AMPHI Regions - AMPHI
SEQ. ID. NO. 20624   18-AlaSerArgIleGluLysValLeu-25
SEQ. ID. NO. 20625   54-ValAlaAspIleAlaLysIleIleGluLys-63
SEQ. ID. NO. 20626   103-MetValGlyMetMet-107
SEQ. ID. NO. 20627   128-LeuAlaSerValValGlnLeuTrp-135
SEQ. ID. NO. 20628   155-MetAspValLeuValThrIle-161
SEQ. ID. NO. 20629   198-PheValSerLeuGlyLysPheLeuGluHisArg-208
SEQ. ID. NO. 20630   230-ValGlnArgAspGlyGlu-235
SEQ. ID. NO. 20631   245-GlnIleGlyAspLeuIleArg-251
SEQ. ID. NO. 20632   315-LeuGlyAspMetMetAsnAlaLeuSerGluAlaGln-326
SEQ. ID. NO. 20633   330-AlaProIleAlaArgValAlaAspLys-338
SEQ. ID. NO. 20634   349-GlyIleAlaLeuLeuThrPheIleAlaThr-358
SEQ. ID. NO. 20635   396-MetGlyLysAlaVal-400
SEQ. ID. NO. 20636   471-IleValSerAlaAlaGln-476
SEQ. ID. NO. 20637   482-IleProThrAlaGln-486
SEQ. ID. NO. 20638   502-GlyAlaGlyLeuValLys-507
SEQ. ID. NO. 20639   539-LysProIleGlyAlaPheAlaLeuAlaAspAlaLeuLys-551
SEQ. ID. NO. 20640   553-AspThrAlaGluAlaIleGlyArgLeu-561
SEQ. ID. NO. 20641   603-GluValGlnLysLeuLysAlaAla-610
SEQ. ID. NO. 20642   617-ValGlyAspGlyIleAsnAspAlaPro-625
SEQ. ID. NO. 20643   640-AlaAspValAlaGluHisThr-646
SEQ. ID. NO. 20644   653-GlnHisSerValAsnGlnLeuAlaAspAlaLeuSer-664
SEQ. ID. NO. 20645   680-AlaPhePheTyrAsnIleLeu-686
Antigenic Index - Jameson-Wolf
SEQ. ID. NO. 20646   1-MetGlnGlnLysValArgPheGlnIleGluGlyMetThr-13
SEQ. ID. NO. 20647   17-CysAlaSerArgIleGluLysValLeuAsnLysLysAspPheValGluSer-33
SEQ. ID. NO. 20648   39-AlaSerGluGluAlaGlnValValPheAspAspSerLysThrSerVal-54
SEQ. ID. NO. 20649   59-LysIleIleGluLysThrGlyTyrGlyAlaLysGluLysThrGluAspThrLeuProGlnProGluAlaGluHis-83
SEQ. ID. NO. 20650   114-ThrArgHisAspTrp-118
SEQ. ID. NO. 20651   148-IleLysGlyGlyLeu-152
SEQ. ID. NO. 20652   205-LeuGluHisArgThrLysLysSerSerLeuAsn-215
SEQ. ID. NO. 20653   228-ValAsnValGlnArgAspGlyGluTrpArg-237
SEQ. ID. NO. 20654   253-AsnHisGlyGluArgIleAlaAla-260
SEQ. ID. NO. 20655   262-GlyIleIleGluSerGlySerGlyTrpAlaAspGluSerHisLeuThrGlyGluSerAsnProGluGluLysLysAlaGlyGly-289
SEQ. ID. NO. 20656   298-ThrGluGlySerVal-302
SEQ. ID. NO. 20657   323-SerGluAlaGlnGlySerLysAlaProIle-332
SEQ. ID. NO. 20658   334-ArgValAlaAspLysAlaAla-340
SEQ. ID. NO. 20659   361-IleLysGlyAspTrp-365
SEQ. ID. NO. 20660   396-MetGlyLysAlaValLys-401
SEQ. ID. NO. 20661   409-AlaAlaAlaMetGluGluAlaAlaHis-417
SEQ. ID. NO. 20662   422-ValLeuAspLysThrGlyThrLeuThrGlyGlyLysProGlnVal-436
SEQ. ID. NO. 20663   443-ProAspSerGlyPheAspGluAspAlaLeu-452
SEQ. ID. NO. 20664   459-ValGluGlnAsnAla-463
SEQ. ID. NO. 20665   498-AlaGluValLysGlyAlaGlyLeu-505
SEQ. ID. NO. 20666   507-LysAlaGlyLysAlaGluPheAla-514
SEQ. ID. NO. 20667   520-LysPheSerArgGlyVal-525
SEQ. ID. NO. 20668   535-SerValAsnGlyLysProIle-541
SEQ. ID. NO. 20669   548-AspAlaLeuLysAlaAspThrAlaGluAlaIleGlyArgLeuLysLysHisAsnIle-566
SEQ. ID. NO. 20670   572-SerGlyAspAsnGlnAsnGlyThrValGluTyrValAla-583
SEQ. ID. NO. 20671   593-GlyAsnMetSerProArgAspLysAlaAlaGluValGlnLysLeuLysAlaAlaGly-611

TABLE 1-continued

| | |
|---|---|
| SEQ. ID. NO. 20672 | 617-ValGlyAspGlyIleAsnAspAla-624 |
| SEQ. ID. NO. 20673 | 636-MetLysGlyGlyAlaAspValAlaGlu-644 |
| SEQ. ID. NO. 20674 | 668-AlaThrLeuLysAsnIleLys-674 |
| SEQ. ID. NO. 20675 | 715-AsnAlaLeuArgLeuLysArgValLysIleAsp-725 |
| Hydrophilic Regions - Hopp-Woods | |
| SEQ. ID. NO. 20676 | 1-MetGlnGlnLysValArgPheGlnIle-9 |
| SEQ. ID. NO. 20677 | 19-SerArgIleGluLysValLeuAsnLysLysAspPheValGlu-32 |
| SEQ. ID. NO. 20678 | 39-AlaSerGluGluAlaGlnValValPheAspAspSerLysThrSerVal-54 |
| SEQ. ID. NO. 20679 | 64-ThrGlyTyrGlyAlaLysGluLysThrGluAspThrLeuProGlnProGluAlaGluHis-83 |
| SEQ. ID. NO. 20680 | 205-LeuGluHisArgThrLysLysSerSerLeu-214 |
| SEQ. ID. NO. 20681 | 229-AsnValGlnArgAspGlyGluTrpArg-237 |
| SEQ. ID. NO. 20682 | 253-AsnHisGlyGluArgIleAlaAla-260 |
| SEQ. ID. NO. 20683 | 262-GlyIleIleGluSer-266 |
| SEQ. ID. NO. 20684 | 270-TrpAlaAspGluSerHisLeuThrGlyGluSerAsnProGluGluLysLysAlaGlyGly-289 |
| SEQ. ID. NO. 20685 | 323-SerGluAlaGlnGlySerLysAlaProIle-332 |
| SEQ. ID. NO. 20686 | 334-ArgValAlaAspLysAlaAla-340 |
| SEQ. ID. NO. 20687 | 409-AlaAlaAlaMetGluAlaAlaHis-417 |
| SEQ. ID. NO. 20688 | 422-ValLeuAspLysThrGlyThr-428 |
| SEQ. ID. NO. 20689 | 430-ThrGluGlyLysProGln-435 |
| SEQ. ID. NO. 20690 | 445-SerGlyPheAspGluAspAlaLeu-452 |
| SEQ. ID. NO. 20691 | 459-ValGluGlnAsnAla-463 |
| SEQ. ID. NO. 20692 | 498-AlaGluValLysGly-502 |
| SEQ. ID. NO. 20693 | 507-LysAlaGlyLysAlaGluPheAla-514 |
| SEQ. ID. NO. 20694 | 548-AspAlaLeuLysAlaAspThrAlaGluAlaIleGlyArgLeuLysLysHisAsnIle-566 |
| SEQ. ID. NO. 20695 | 573-GlyAspAsnGlnGly-577 |
| SEQ. ID. NO. 20696 | 596-SerProArgAspLysAlaAlaGluValGlnLysLeuLysAlaAlaGly-611 |
| SEQ. ID. NO. 20697 | 638-GlyGlyAlaAspValAlaGlu-644 |
| SEQ. ID. NO. 20698 | 668-AlaThrLeuLysAsnIleLys-674 |
| SEQ. ID. NO. 20699 | 717-LeuArgLeuLysArgValLysIleAsp-725 |
| a590 | |
| AMPHI Regions - AMPHI | |
| SEQ. ID. NO. 20700 | 77-TyrLeuProAspAsnLeuLysThrValLeuGluGlnProValThrLeuValAsnHisIleThrHis-98 |
| SEQ. ID. NO. 20701 | 100-ProPheAlaGlyGlyPhe-105 |
| SEQ. ID. NO. 20702 | 123-LysValLeuGluArgPhePhe-129 |
| SEQ. ID. NO. 20703 | 132-GlnValProValSerLeu-137 |
| SEQ. ID. NO. 20704 | 177-TyrGlnLysGlyPheLysSerTyrArgAsnGly-187 |
| SEQ. ID. NO. 20705 | 214-ThrSerAspGlyIleAsnProLeu-221 |
| SEQ. ID. NO. 20706 | 248-AsnGluLeuValAsnLeuVal-254 |
| SEQ. ID. NO. 20707 | 331-LysArgLysPheAlaArgIle-337 |
| SEQ. ID. NO. 20708 | 420-LysMetLeuGluAsp-424 |
| SEQ. ID. NO. 20709 | 450-AspIleAsnGluThrLeuArgLeuMet-458 |
| SEQ. ID. NO. 20710 | 460-AspSerThrValGln-464 |
| Antigenic Index - Jameson-Wolf | |
| SEQ. ID. NO. 20711 | 1-MetLysLysProLeu-5 |
| SEQ. ID. NO. 20712 | 26-LysAlaGluGluSerLeuThrGlnGlnGlnLysIleLeuGln-39 |
| SEQ. ID. NO. 20713 | 48-SerHisGlnTyrGluArgGlyTrpPheThrSerThrGluThrThrValIleArgLeuLysProGluLeu-70 |
| SEQ. ID. NO. 20714 | 75-GlnLysTyrLeuProAspAsnLeuLysThrValLeu-86 |
| SEQ. ID. NO. 20715 | 113-ThrGluPheLysTyrAlaProGluThrGluLysValLeuGlu-126 |
| SEQ. ID. NO. 20716 | 128-PhePheGlyLysGlnVal-133 |
| SEQ. ID. NO. 20717 | 144-AsnGlySerGlyLysMetGluVal-151 |
| SEQ. ID. NO. 20718 | 157-AspTyrGluGluLeuSerGly-163 |
| SEQ. ID. NO. 20719 | 175-ThrValTyrGlnLysGlyPheLysSerTyrArgAsnGlyTyrAspAlaPro-191 |
| SEQ. ID. NO. 20720 | 196-LysLeuAlaAspLysGlyAspAlaAlaPheGlu-206 |
| SEQ. ID. NO. 20721 | 208-ValHisPheAspSerGluThrSerAspGlyIleAsn-219 |
| SEQ. ID. NO. 20722 | 233-PheSerLeuGluTrpLysGluGlyValAspTyr-243 |
| SEQ. ID. NO. 20723 | 264-AsnProAsnGlySerIleAlaProSerLysIleGluValGly-277 |
| SEQ. ID. NO. 20724 | 281-PheSerThrLysThrGlyGluSerGlyAla-290 |
| SEQ. ID. NO. 20725 | 292-IleAspSerGluGlyGlnPheArgPhe-300 |
| SEQ. ID. NO. 20726 | 305-TyrGlyAspGluLysTyrGlyPro-312 |
| SEQ. ID. NO. 20727 | 330-LeuLysArgLysPheAlaArgIleSerAlaLysLysMetThrGluGluGlnIleArgAsnAspLeu-351 |
| SEQ. ID. NO. 20728 | 355-ValLysGlyGluAlaSerGly-361 |
| SEQ. ID. NO. 20729 | 366-AsnProValLeuAsp-370 |
| SEQ. ID. NO. 20730 | 378-LeuProSerGlyLysIleAspValGlyGly-387 |
| SEQ. ID. NO. 20731 | 389-IleMetPheLysAspMetLysLysGluAspLeuAsnGln-401 |
| SEQ. ID. NO. 20732 | 406-LeuLysLysThrGluAlaAspIleArgMet-415 |
| SEQ. ID. NO. 20733 | 437-AsnAlaGluAspGluAlaGluGlyArgAlaSerLeuAspAspIleAsnGluThrLeu-455 |
| SEQ. ID. NO. 20734 | 466-MetAlaArgGluLysTyr-471 |
| SEQ. ID. NO. 20735 | 475-AsnGlyAspGlnIleAsp-480 |
| SEQ. ID. NO. 20736 | 485-LeuLysAsnAsnGlnLeuLysLeuAsnGlyLysThrLeuGlnAsnGluProGluProAspPheAspGluGlyGlyMetValSerGluProGlnGln-516 |
| Hydrophilic Regions - Hopp-Woods | |
| SEQ. ID. NO. 20737 | 1-MetLysLysProLeu-5 |
| SEQ. ID. NO. 20738 | 26-LysAlaGluGluSerLeuThrGln-33 |
| SEQ. ID. NO. 20739 | 62-ThrValIleArgLeuLysProGluLeu-70 |
| SEQ. ID. NO. 20740 | 77-TyrLeuProAspAsnLeuLysThrValLeu-86 |
| SEQ. ID. NO. 20741 | 113-ThrGluPheLysTyrAlaProGluThrGluLysValLeuGlu-126 |
| SEQ. ID. NO. 20742 | 147-GlyLysMetGluVal-151 |
| SEQ. ID. NO. 20743 | 157-AspTyrGluGluLeuSerGly-163 |
| SEQ. ID. NO. 20744 | 180-GlyPheLysSerTyrArgAsnGlyTyr-188 |
| SEQ. ID. NO. 20745 | 196-LysLeuAlaAspLysGlyAspAlaAlaPheGlu-206 |
| SEQ. ID. NO. 20746 | 208-ValHisPheAspSerGluThrSerAspGly-217 |

TABLE 1-continued

| | |
|---|---|
| SEQ. ID. NO. 20747 | 233-PheSerLeuGluTrpLysGluGlyValAspTyr-243 |
| SEQ. ID. NO. 20748 | 272-SerLysIleGluValGly-277 |
| SEQ. ID. NO. 20749 | 292-IleAspSerGluGlyGlnPhe-298 |
| SEQ. ID. NO. 20750 | 306-GlyAspGluLysTyrGlyPro-312 |
| SEQ. ID. NO. 20751 | 330-LeuLysArgLysPheAlaArgIleSerAlaLysLysMetThrGluGluGlnIleArgAsnAspLeu-351 |
| SEQ. ID. NO. 20752 | 355-ValLysGlyGluAla-359 |
| SEQ. ID. NO. 20753 | 381-GlyLysIleAspValGlyGly-387 |
| SEQ. ID. NO. 20754 | 389-IleMetPheLysAspMetLysLysGluAspLeuAsn-400 |
| SEQ. ID. NO. 20755 | 406-LeuLysLysThrGluAlaAspIleArgMet-415 |
| SEQ. ID. NO. 20756 | 437-AsnAlaGluAspGluAlaGluGlyArgAlaSerLeuAspAspIleAsnGluThrLeu-455 |
| SEQ. ID. NO. 20757 | 466-MetAlaArgGluLysTyr-471 |
| SEQ. ID. NO. 20758 | 486-LysAsnAsnGlnLeuLysLeuAsnGly-494 |
| SEQ. ID. NO. 20759 | 496-ThrLeuGlnAsnGluProGluProGlnAspPheAspGluGlyGlyMetValSerGluProGlnGln-516 | a591
AMPHI Regions - AMPHI

| | |
|---|---|
| SEQ. ID. NO. 20760 | 6-AlaPheIlePheAla-10 |
| SEQ. ID. NO. 20761 | 17-LeuHisGluPheGlyHisTyrIleValAla-26 |
| SEQ. ID. NO. 20762 | 61-LeuGlyGlyTyrValLysMetValAsp-69 |
| SEQ. ID. NO. 20763 | 143-GlyAspLysIleGlnSerValAsnGlyThrProValAlaAspTrp-157 |
| SEQ. ID. NO. 20764 | 181-SerGlyAlaGlnThrValArgThrIleAspAlaAlaGlyThrProGluAlaGlyLysIleAlaLys-202 |
| SEQ. ID. NO. 20765 | 218-AlaGlyGlyValGluLys-223 |
| SEQ. ID. NO. 20766 | 234-ProGlyAspArgLeu-238 |
| SEQ. ID. NO. 20767 | 245-ProIleAlaSerTrpGlnGluTrpAlaAsnLeuThrArg-257 |
| SEQ. ID. NO. 20768 | 304-AlaTrpAspAlaGlnIleArg-310 |
| SEQ. ID. NO. 20769 | 313-TyrArgProSerValValArgAlaPheGly-322 |
| SEQ. ID. NO. 20770 | 324-GlyTrpGluLysThrValSerHis-331 |
| SEQ. ID. NO. 20771 | 335-ThrLeuLysPhePheGlyLysLeuIle-343 |
| SEQ. ID. NO. 20772 | 351-HisIleSerGlyProLeuThrIleAla-359 |
| SEQ. ID. NO. 20773 | 373-TyrLeuGluPheLeuAlaLeu-379 |

Antigenic Index - Jameson-Wolf

| | |
|---|---|
| SEQ. ID. NO. 20774 | 44-PhePheThrArgLysArgGlyAspThrGlu-53 |
| SEQ. ID. NO. 20775 | 68-ValAspThrArgGluGlyGluValSerGluAlaAspLeu-80 |
| SEQ. ID. NO. 20776 | 84-PheAspLysGlnHisProAlaLysArg-92 |
| SEQ. ID. NO. 20777 | 129-ValGluProAspThrIleAla-135 |
| SEQ. ID. NO. 20778 | 139-GlyPheGlnSerGlyAspLysIleGlnSer-148 |
| SEQ. ID. NO. 20779 | 157-TrpGlySerAlaGln-161 |
| SEQ. ID. NO. 20780 | 187-ArgThrIleAspAlaAlaGlyThrProGluAlaGlyLysIleAlaLysAsnGlnGly-205 |
| SEQ. ID. NO. 20781 | 219-GlyGlyValGluLysGlySerProAlaGluLysAlaGlyLeuLysProGlyAspArgLeuThrAlaAlaAspGlyLysProIle-246 |
| SEQ. ID. NO. 20782 | 254-AsnLeuThrArgGlnSerProGlyLysLysIle-264 |
| SEQ. ID. NO. 20783 | 268-TyrGluArgAlaGlyGlnThrHisThrAlaAspIleArgProAspThrValGluGlnProAspHisThrLeu-291 |
| SEQ. ID. NO. 20784 | 295-ValGlyLeuArgProGlnProAspArgAlaTrp-305 |
| SEQ. ID. NO. 20785 | 307-AlaGlnIleArgArgSerTyrArgProSerVal-317 |
| SEQ. ID. NO. 20786 | 327-LysThrValSerHisSer-332 |
| SEQ. ID. NO. 20787 | 343-IleSerGlyAsnAla-347 |
| SEQ. ID. NO. 20788 | 362-AlaGlyGlnSerAla-366 |
| SEQ. ID. NO. 20789 | 408-IleArgGlyLysProLeuGlyGluArgValGln-418 |

Hydrophilic Regions - Hopp-Woods

| | |
|---|---|
| SEQ. ID. NO. 20790 | 44-PhePheThrArgLysArgGlyAspThr-52 |
| SEQ. ID. NO. 20791 | 68-ValAspThrArgGluGlyGluValSerGluAlaAspLeu-80 |
| SEQ. ID. NO. 20792 | 84-PheAspLysGlnHisProAlaLysArg-92 |
| SEQ. ID. NO. 20793 | 129-ValGluProAspThrIleAla-135 |
| SEQ. ID. NO. 20794 | 139-GlyPheGlnSerGlyAspLysIleGlnSer-148 |
| SEQ. ID. NO. 20795 | 193-GlyThrProGluAlaGlyLysIleAlaLys-202 |
| SEQ. ID. NO. 20796 | 220-GlyValGluLysGlyGlySerProAlaGluLysAlaGlyLeuLysProGlyAspArgLeuThrAlaAlaAspGlyLysPro-245 |
| SEQ. ID. NO. 20797 | 256-ThrArgGlnSerProGlyLysLysIle-264 |
| SEQ. ID. NO. 20798 | 268-TyrGluArgAlaGlyGln-273 |
| SEQ. ID. NO. 20799 | 277-AlaAspIleArgProAspThrValGluGlnProAsp-288 |
| SEQ. ID. NO. 20800 | 299-ProGlnProAspArgAlaTrp-305 |
| SEQ. ID. NO. 20801 | 308-GlnIleArgArgSerTyrArg-314 |
| SEQ. ID. NO. 20802 | 362-AlaGlyGlnSerAla-366 |
| SEQ. ID. NO. 20803 | 411-LysProLeuGlyGluArgValGln-418 | a592
AMPHI Regions - AMPHI

| | |
|---|---|
| SEQ. ID. NO. 20804 | 6-PheGlyGlnIlePheSer-11 |
| SEQ. ID. NO. 20805 | 21-GlyGlyLeuLeuGlyGlyLeuIle-28 |
| SEQ. ID. NO. 20806 | 50-AlaProAsnAlaAlaAlaAlaAla-57 |
| SEQ. ID. NO. 20807 | 65-GlnGlyMetIleGlnMetLeuGlyValPheValAsp-76 |
| SEQ. ID. NO. 20808 | 94-ProTyrGlyAspLeu-98 |
| SEQ. ID. NO. 20809 | 109-ValSerGlnValGlyGlnTrp-115 |
| SEQ. ID. NO. 20810 | 153-ThrAlaValPheArgMet-158 |
| SEQ. ID. NO. 20811 | 165-TyrPheGlyAlaValAla-170 |
| SEQ. ID. NO. 20812 | 185-IleMetAlaTrpIleAsnLeuValAlaIleLeuLeuLeuSer-198 |

Antigenic Index - Jameson-Wolf

| | |
|---|---|
| SEQ. ID. NO. 20813 | 35-GlyIleLysArgGlyLeuTyrSerAsnGluAlaGlyMetGlySerAlaProAsnAla-53 |
| SEQ. ID. NO. 20814 | 57-AlaGluValLysHisProValSer-64 |
| SEQ. ID. NO. 20815 | 93-GlnProTyrGlyAspLeuSerGly-100 |
| SEQ. ID. NO. 20816 | 137-AlaTyrAlaGluSerAsnVal-143 |
| SEQ. ID. NO. 20817 | 206-ArgAspTyrThrAlaLysLeuLysMetGlyLysAspProGluPheLysLeuSerGluHisProGlyLeuLysArgArgIleLysSerAspValTrp-237 |

Hydrophilic Regions - Hopp-Woods

| | |
|---|---|
| SEQ. ID. NO. 20818 | 35-GlyIleLysArgGlyLeuTyr-41 |

TABLE 1-continued

| | |
|---|---|
| SEQ. ID. NO. 20819 | 57-AlaGluValLysHisProVal-63 |
| SEQ. ID. NO. 20820 | 212-LeuLysMetGlyLysAspProGluPheLysLeuSerGlu-224 |
| SEQ. ID. NO. 20821 | 226-ProGlyLeuLysArgArgIleLysSer-234 | a593
AMPHI Regions - AMPHI

| | |
|---|---|
| SEQ. ID. NO. 20822 | 6-GlyLeuCysLysArgPheGlyGlyLysThr-15 |
| SEQ. ID. NO. 20823 | 41-SerThrLeuLeuAsnMetIleAlaGlyIleValArg-52 |
| SEQ. ID. NO. 20824 | 87-HisMetSerAlaLeuGlu-92 |
| SEQ. ID. NO. 20825 | 102-LysMetProLysAla-106 |
| SEQ. ID. NO. 20826 | 125-AlaHisArgLysProXxxLysLeuSerGlyGlyGlu-136 |
| SEQ. ID. NO. 20827 | 159-PheSerSerLeuAsp-163 |
| SEQ. ID. NO. 20828 | 165-HisLeuArgAspArgLeuArgArgMet-173 |
| SEQ. ID. NO. 20829 | 213-CysGlyThrProGluThrLeuValGlnThrProAlaGlyValGlnValAlaHisLeuMetGly-233 |

Antigenic Index - Jameson-Wolf

| | |
|---|---|
| SEQ. ID. NO. 20830 | 6-GlyLeuCysLysArgPheGlyGlyLysThrValAlaAsp-18 |
| SEQ. ID. NO. 20831 | 24-ValGlyArgGlyLysIle-29 |
| SEQ. ID. NO. 20832 | 33-LeuGlyArgSerGlyCysGlyLysSerThr-42 |
| SEQ. ID. NO. 20833 | 50-IleValArgProAspGlyGlyGlu-57 |
| SEQ. ID. NO. 20834 | 61-AsnGlyGluAsnIleThrArgMetProProGluLysArgArgIle-75 |
| SEQ. ID. NO. 20835 | 99-LysMetGlnLysMetProLysAlaGluAlaGluSer-110 |
| SEQ. ID. NO. 20836 | 119-ValGlyLeuGluAsnGluAlaHisArgLysProXxxLysLeuSerGlyGlyGluLysGlnArgLeuAlaLeu-142 |
| SEQ. ID. NO. 20837 | 157-GluSerPheSerSerLeu-162 |
| SEQ. ID. NO. 20838 | 164-ThrHisLeuArgAspArgLeuArgArgMetThrAlaGluArgIleArgLysGlyGlyIle-183 |
| SEQ. ID. NO. 20839 | 190-HisSerProGluGluAlaCysThrAlaAlaAspGluIleAlaVal-204 |
| SEQ. ID. NO. 20840 | 206-HisGluGlyLysIleLeuGlnCysGlyThrProGluThrLeu-219 |
| SEQ. ID. NO. 20841 | 233-GlyLeuProAsnThrAspAspAspArgHisIle-243 |
| SEQ. ID. NO. 20842 | 248-ValArgPheAspGlnAspGlyMetGluCysArgValLeuSer-261 |
| SEQ. ID. NO. 20843 | 263-ThrCysLeuProGluSer-268 |
| SEQ. ID. NO. 20844 | 291-GlyGluIleSerGlyAsnAspThrValArgIleHisIleGluAspArgGluIleValArgPheArg-312 |

Hydrophilic Regions - Hopp-Woods

| | |
|---|---|
| SEQ. ID. NO. 20845 | 6-GlyLeuCysLysArgPheGlyGly-13 |
| SEQ. ID. NO. 20846 | 25-GlyArgGlyLysIle-29 |
| SEQ. ID. NO. 20847 | 36-SerGlyCysGlyLys-40 |
| SEQ. ID. NO. 20848 | 51-ValArgProAspGlyGly-56 |
| SEQ. ID. NO. 20849 | 68-MetProProGluLysArgArgIle-75 |
| SEQ. ID. NO. 20850 | 99-LysMetGlnLysMetProLysAlaGluAlaGluSer-110 |
| SEQ. ID. NO. 20851 | 119-ValGlyLeuGluAsnGluAlaHisArgLysProXxxLysLeuSerGlyGlyGluLysGlnArgLeuAlaLeu-142 |
| SEQ. ID. NO. 20852 | 164-ThrHisLeuArgAspArgLeuArgArgMetThrAlaGluArgIleArgLysGlyGly-182 |
| SEQ. ID. NO. 20853 | 191-SerProGluGluAlaCysThrAlaAlaAspGluIleAlaVal-204 |
| SEQ. ID. NO. 20854 | 206-HisGluGlyLysIle-210 |
| SEQ. ID. NO. 20855 | 236-AsnThrAspAspAspArgHisIle-243 |
| SEQ. ID. NO. 20856 | 248-ValArgPheAspGlnAspGlyMetGluCysArgValLeuSer-261 |
| SEQ. ID. NO. 20857 | 291-GlyGluIleSerGly-295 |
| SEQ. ID. NO. 20858 | 297-AspThrValArgIleHisIleGluAspArgGluIleValArgPheArga594-312 |

AMPHI Regions - AMPHI

| | |
|---|---|
| SEQ. ID. NO. 20859 | 21-SerIleLeuArgLeu-25 |
| SEQ. ID. NO. 20860 | 108-AlaGlyArgGluCysGlnGluThrAlaAlaAla-118 |
| SEQ. ID. NO. 20861 | 138-AlaIleLysArgCysAsn-143 |

Antigenic Index - Jameson-Wolf

| | |
|---|---|
| SEQ. ID. NO. 20862 | 1-MetGlyAlaAspThrAspGlyAspLysAspValArgLeuAsnArgThr-16 |
| SEQ. ID. NO. 20863 | 51-ValGluHisProAsnArgPhe-57 |
| SEQ. ID. NO. 20864 | 75-HisLeuAspGlySerThrGlyGly-82 |
| SEQ. ID. NO. 20865 | 86-PheArgArgGluLysThrGlyHisLysArgArgCysHisThrGlnCys-101 |
| SEQ. ID. NO. 20866 | 103-HisSerAlaArgAlaAlaAlaGlyArgGluCysGlnGluThr-115 |
| SEQ. ID. NO. 20867 | 137-ArgAlaIleLysArgCysAsn-143 |

Hydrophilic Regions - Hopp-Woods

| | |
|---|---|
| SEQ. ID. NO. 20868 | 1-MetGlyAlaAspThrAspGlyAspLysAspValArgLeuAsnArg-15 |
| SEQ. ID. NO. 20869 | 86-PheArgArgGluLysThrGlyHisLysArgArgCysHis-98 |
| SEQ. ID. NO. 20870 | 105-AlaArgAlaAlaAlaGlyArgGluCysGlnGluThr-115 |
| SEQ. ID. NO. 20871 | 137-ArgAlaIleLysArgCysAsn-143 | a595
AMPHI Regions - AMPHI

| | |
|---|---|
| SEQ. ID. NO. 20872 | 20-CysGlnProProGluAla-25 |
| SEQ. ID. NO. 20873 | 140-AlaAspLeuGluLysLeuSerGlnProLeuAla-150 |
| SEQ. ID. NO. 20874 | 157-GlnGlyGluValLysGluLeuVal-164 |
| SEQ. ID. NO. 20875 | 169-ThrPheThrGluAlaValLysAlaGlyAspIleGluLysAla-182 |
| SEQ. ID. NO. 20876 | 196-IleGluProIleAlaGluLeuPheSerGluLeuAspPro-208 |
| SEQ. ID. NO. 20877 | 224-AlaGlyPheThrGlyPheHisArg-231 |
| SEQ. ID. NO. 20878 | 243-SerGlyValLysGluIleAlaAlaLysLeuMetThrAspValGluAlaLeuGlnLysGluIleAsp-264 |
| SEQ. ID. NO. 20879 | 274-ValGlyGlyAlaSerGluLeuIleGluGluValAlaGly-286 |
| SEQ. ID. NO. 20880 | 309-AspGlySerLysLysIleValAspLeuPheArgProLeu-321 |
| SEQ. ID. NO. 20881 | 337-PheLysGlnValAsnGluIleLeuAlaLys-346 |
| SEQ. ID. NO. 20882 | 351-AspGlyPheGluThrTyrAspLysLeuGlyGlu-361 |
| SEQ. ID. NO. 20883 | 366-AlaLeuGlnAlaSerIleAsnAlaLeuAlaGluAspLeuAlaGlnLeuArgGlyIleLeuGlyLeu-387 |

Antigenic Index - Jameson-Wolf

| | |
|---|---|
| SEQ. ID. NO. 20884 | 1-MetArgLysPheAsn-5 |
| SEQ. ID. NO. 20885 | 21-GlnProProGluAlaGluLysAlaAlaPro-30 |
| SEQ. ID. NO. 20886 | 32-AlaSerGlyGluAlaGlnThrAlaAsnGluGlyGlySer-44 |
| SEQ. ID. NO. 20887 | 50-AsnAspAsnAlaCysGluProMetGlu-58 |
| SEQ. ID. NO. 20888 | 70-IleLysAsnAsnSerGlyArgLysLeuGluTrpGluIle-82 |

TABLE 1-continued

| | |
|---|---|
| SEQ. ID. NO. 20889 | 87-MetValValAspGluArgGluAsnIleAla-96 |
| SEQ. ID. NO. 20890 | 98-GlyLeuSerAspLysMetThr-104 |
| SEQ. ID. NO. 20891 | 108-LeuProGlyGluTyrGluMet-114 |
| SEQ. ID. NO. 20892 | 120-ThrAsnProArgGlyLysLeuValValThrAspSerGlyPheLysAspThrAlaAsnGluAlaAspLeuGluLysLeuSer-146 |
| SEQ. ID. NO. 20893 | 158-GlyGluValLysGluLeuValAlaLysThrLysThrPheThrGluAlaValLysAlaGlyAspIleGluLysAlaLysSerLeuPheAla-187 |
| SEQ. ID. NO. 20894 | 189-ThrArgValHisTyrGluArgIleGluProIle-199 |
| SEQ. ID. NO. 20895 | 204-SerGluLeuAspProValIleAspAlaArgGluAspAspPheLysAspGlyAlaLysAspAlaGly-225 |
| SEQ. ID. NO. 20896 | 238-ValGluLysAspValSerGlyValLysGluIleAlaAla-250 |
| SEQ. ID. NO. 20897 | 252-LeuMetThrAspValGluAlaLeuGlnLysGluIleAsp-264 |
| SEQ. ID. NO. 20898 | 269-ProProGlyLysValValGlyGlyAla-277 |
| SEQ. ID. NO. 20899 | 279-GluLeuIleGluGluValAlaGlySerLysIleSerGlyGluGluAspArgTyrSerHisThrAspLeuSerAspPheGlnAlaAsnValAspGlySerLysLysIleValAsp-316 |
| SEQ. ID. NO. 20900 | 322-IleGluThrLysAsnLysAlaLeuLeuGluLysThrAspThrAsnPheLysGlnValAsn-341 |
| SEQ. ID. NO. 20901 | 345-AlaLysTyrArgThrLysAspGlyPheGluThrTyrAspLysLeuGlyGluAlaAspArgLysAlaLeu-367 |
| SEQ. ID. NO. 20902 | 374-LeuAlaGluAspLeuAlaGln-380 |
| Hydrophilic Regions - Hopp-Woods | |
| SEQ. ID. NO. 20903 | 1-MetArgLysPheAsn-5 |
| SEQ. ID. NO. 20904 | 21-GlnProProGluAlaGluLysAlaAlaPro-30 |
| SEQ. ID. NO. 20905 | 32-AlaSerGlyGluAlaGlnThrAlaAsnGluGlyGlySer-44 |
| SEQ. ID. NO. 20906 | 52-AsnAlaCysGluProMetGlu-58 |
| SEQ. ID. NO. 20907 | 72-AsnAsnSerGlyArgLysLeuGluTrpGluIle-82 |
| SEQ. ID. NO. 20908 | 87-MetValValAspGluArgGluAsnIle-95 |
| SEQ. ID. NO. 20909 | 99-LeuSerAspLysMetThr-104 |
| SEQ. ID. NO. 20910 | 110-GlyGluTyrGluMet-114 |
| SEQ. ID. NO. 20911 | 122-ProArgGlyLysLeuValVal-128 |
| SEQ. ID. NO. 20912 | 131-SerGlyPheLysAspThrAlaAsnGluAlaAspLeuGluLysLeuSer-146 |
| SEQ. ID. NO. 20913 | 158-GlyGluValLysGluLeuValAlaLysThrLysThrPheThrGluAlaValLysAlaGlyAspIleGluLysAlaLysSerLeuPheAla-187 |
| SEQ. ID. NO. 20914 | 189-ThrArgValHisTyrGluArgIleGluProIle-199 |
| SEQ. ID. NO. 20915 | 204-SerGluLeuAspProValIleAspAlaArgGluAspAspPheLysAspGlyAlaLysAspAlaGly-225 |
| SEQ. ID. NO. 20916 | 238-ValGluLysAspValSerGlyValLysGluIleAlaAla-250 |
| SEQ. ID. NO. 20917 | 252-LeuMetThrAspValGluAlaLeuGlnLysGluIleAsp-264 |
| SEQ. ID. NO. 20918 | 279-GluLeuIleGluGluValAlaGly-286 |
| SEQ. ID. NO. 20919 | 288-LysIleSerGlyGluGluAspArgTyrSerHis-298 |
| SEQ. ID. NO. 20920 | 308-ValAspGlySerLysLysIleValAsp-316 |
| SEQ. ID. NO. 20921 | 322-IleGluThrLysAsnLysAlaLeuLeuGluLysThrAspThrAsnPhe-337 |
| SEQ. ID. NO. 20922 | 347-TyrArgThrLysAspGlyPheGluThrTyrAspLysLeuGlyGluAlaAspArgLysAlaLeu-367 |
| SEQ. ID. NO. 20923 | 374-LeuAlaGluAspLeuAlaGln-380 |
| a596 | |
| AMPHI Regions - AMPHI | |
| SEQ. ID. NO. 20924 | 9-MetLeuArgValSerLysValVal-16 |
| SEQ. ID. NO. 20925 | 50-LeuArgIleMetAlaGlyValAspLys-58 |
| SEQ. ID. NO. 20926 | 87-ValArgGluGluValGluSerGlyLeuGlyGluValAlaAlaAlaGlnLysArgLeuGluGluValTyrAlaGluTyr-112 |
| SEQ. ID. NO. 20927 | 192-ProThrAsnHisLeuAsp-197 |
| SEQ. ID. NO. 20928 | 202-GluTrpLeuGluGlnPheLeuValArgPheProGly-213 |
| SEQ. ID. NO. 20929 | 295-AlaArgPheGluGluMetSerAsnTyr-303 |
| SEQ. ID. NO. 20930 | 322-LeuGlyAsnGluValIleGluPheValAsnValSerLysSerPhe-336 |
| SEQ. ID. NO. 20931 | 366-SerThrLeuPheLysMet-371 |
| SEQ. ID. NO. 20932 | 409-AspAsnIleAlaGlu-413 |
| SEQ. ID. NO. 20933 | 444-IleThrGlyGlnLeuSer-449 |
| SEQ. ID. NO. 20934 | 483-LeuArgAlaLeuGluAspAlaLeuLeuGluPheAla-494 |
| Antigenic Index - Jameson-Wolf | |
| SEQ. ID. NO. 20935 | 16-ValProProGlnLysThrIleIleLysAspIleSer-27 |
| SEQ. ID. NO. 20936 | 41-LeuAsnGlyAlaGlyLysSerThrVal-49 |
| SEQ. ID. NO. 20937 | 54-AlaGlyValAspLysGluPheGluGlyGluAla-64 |
| SEQ. ID. NO. 20938 | 75-LeuProGlnGluProGluLeuAspProGluLysThrValArgGluGluValGluSerGlyLeu-95 |
| SEQ. ID. NO. 20939 | 99-AlaAlaAlaGlnLysArgLeuGluGluValTyr-109 |
| SEQ. ID. NO. 20940 | 112-TyrAlaAsnProAspAlaAspPheAspAlaLeuAlaGluGluGlnGlyArgLeuGlu-130 |
| SEQ. ID. NO. 20941 | 136-GlySerSerThrGlyGlyGlyAlaGluHisGluLeuGluIleAlaAlaAspAlaLeuArg-155 |
| SEQ. ID. NO. 20942 | 157-ProGluTrpAspAlaLysIleAspAsnLeuSerGlyGlyGluLysArgArgValAla-175 |
| SEQ. ID. NO. 20943 | 181-LeuSerLysProAspMet-186 |
| SEQ. ID. NO. 20944 | 190-AspGluProThrAsnHisLeuAspAlaGluSer-200 |
| SEQ. ID. NO. 20945 | 219-ThrHisAspArgTyrPhe-224 |
| SEQ. ID. NO. 20946 | 233-LeuGluLeuAspArgGlyHisGlyIleProTrpLysGlyAsnTyrSerSer-249 |
| SEQ. ID. NO. 20947 | 251-LeuGluGlnLysGluLysArgLeuGluAsnGluAlaLysSerGluAlaAlaArgValLysAlaMetLysGlnGluLeuGluTrp-278 |
| SEQ. ID. NO. 20948 | 280-ArgGlnAsnAlaLysGlyArgGlnAlaLysSerLysAlaArgLeuAlaArgPheGluGluMetSerAsnTyrGluTyrGlnLysArgAsnGluThrGlnGlu-313 |
| SEQ. ID. NO. 20949 | 319-AlaGluArgLeuGlyAsnGluVal-326 |
| SEQ. ID. NO. 20950 | 333-SerLysSerPheGlyAsp-338 |
| SEQ. ID. NO. 20951 | 359-GlyProAsnGlyAlaGlyLysSerThrLeu-368 |
| SEQ. ID. NO. 20952 | 373-AlaGlyLysGluGlnProAspSerGlyGluValLysIle-385 |
| SEQ. ID. NO. 20953 | 395-AspGlnSerArgGluGlyLeuGlnAsnAspLysThrValPhe-408 |
| SEQ. ID. NO. 20954 | 411-IleAlaGluGlyArgAspIleLeu-418 |
| SEQ. ID. NO. 20955 | 421-GlyGlnPheGluIleProAlaArgGlnTyrLeuGlyArgPheAsnPheLysGlySerAspGlnSerLysIle-444 |
| SEQ. ID. NO. 20956 | 446-GlyGlnLeuSerGlyGlyGluArgGlyArgLeuHisLeu-458 |
| SEQ. ID. NO. 20957 | 462-LeuLeuGlyGlyGlyAsn-467 |
| SEQ. ID. NO. 20958 | 471-LeuAspGluProSerAsnAspLeuAspValGluThr-482 |
| SEQ. ID. NO. 20959 | 501-SerHisAspArgTrpPhe-506 |
| SEQ. ID. NO. 20960 | 516-AlaCysGluGlyAspSerLysTrp-523 |
| SEQ. ID. NO. 20961 | 526-PheAspGlyAsnTyrGlnGluGlyTyrGluAlaAspLysLysArgArgLeuGlyGluGluGlyThrLysProLysArgIleLysTyrLysProValThrArg-558 |

TABLE 1-continued

Hydrophilic Regions - Hopp-Woods
SEQ. ID. NO. 20962   54-AlaGlyValAspLysGluPheGluGlyGluAla-64
SEQ. ID. NO. 20963   77-GlnGluProGluLeuAspProGluLysThrValArgGluGluValGluSerGlyLeu-95
SEQ. ID. NO. 20964   99-AlaAlaAlaGlnLysArgLeuGluGluValTyr-109
SEQ. ID. NO. 20965   113-AlaAsnProAspAlaAspPheAspAlaLeuAlaGluGluGlnGlyArgLeuGlu-130
SEQ. ID. NO. 20966   141-GlyGlyAlaGluHisGluLeuGluIleAlaAlaAspAlaLeuArg-155
SEQ. ID. NO. 20967   157-ProGluTrpAspAlaLysIleAspAsn-165
SEQ. ID. NO. 20968   167-SerGlyGlyLysArgArgValAla-175
SEQ. ID. NO. 20969   181-LeuSerLysProAsp-185
SEQ. ID. NO. 20970   190-AspGluProThrAsnHisLeuAspAlaGluSer-200
SEQ. ID. NO. 20971   233-LeuGluLeuAspArgGlyHis-239
SEQ. ID. NO. 20972   251-LeuGluGlnLysGluLysArgLeuGluAsnGluAlaLysSerGluAlaAlaArgValLysAlaMetLysGlnGluLeuGluTrp-278
SEQ. ID. NO. 20973   280-ArgGlnAsnAlaLysGlyArgGlnAlaLysSerLysAlaArgLeuAlaArgPheGluGluMetSerAsn-302
SEQ. ID. NO. 20974   304-GluTyrGlnLysArgAsnGluThrGln-312
SEQ. ID. NO. 20975   319-AlaGluArgLeuGlyAsnGluVal-326
SEQ. ID. NO. 20976   373-AlaGlyLysGluGlnProAspSerGlyGluValLysIle-385
SEQ. ID. NO. 20977   395-AspGlnSerArgGluGlyLeuGlnAsnAspLysThrValPhe-408
SEQ. ID. NO. 20978   411-IleAlaGluGlyArgAspIleLeu-418
SEQ. ID. NO. 20979   435-AsnPheLysGlySerAspGlnSerLysIle-444
SEQ. ID. NO. 20980   449-SerGlyGlyGluArgGlyArgLeuHisLeu-458
SEQ. ID. NO. 20981   472-AspGluProSerAsnAspLeuAspValGluThr-482
SEQ. ID. NO. 20982   517-CysGluGlyAspSer-521
SEQ. ID. NO. 20983   529-AsnTyrGlnGluTyrGluAlaAspLysLysArgArgLeuGlyGluGluGlyThrLysProLysArgIleLysTyr-553
a597
AMPHI Regions - AMPHI
SEQ. ID. NO. 20984   6-SerAsnSerLeuLysGlnLeuGlnGlu-14
SEQ. ID. NO. 20985   45-TrpAspLysPheGlnLysLeu-51
SEQ. ID. NO. 20986   68-GlnIleSerArgPheValSerGly-75
SEQ. ID. NO. 20987   101-LeuArgTyrThrArgTyrValAsnAla-109
SEQ. ID. NO. 20988   111-AsnArgGluValValLysAspLeuGluLysGlnGln-122
SEQ. ID. NO. 20989   132-IleAsnAsnGluLeuAlaArgLeuLysLys-141
SEQ. ID. NO. 20990   144-AlaAsnValGlnSerLeu-149
SEQ. ID. NO. 20991   157-AspAlaAlaGluGlnThrGlu-163
SEQ. ID. NO. 20992   169-AlaLysIleAlaLysAspAlaArg-176
SEQ. ID. NO. 20993   189-AsnLysLeuLeuSer-193
SEQ. ID. NO. 20994   253-ProSerValMetGlyIleGlySerAlaAspGlyPheSerArgMetGlnGlyArgLeuLysLysProValAspGlyValProThrGly-281
SEQ. ID. NO. 20995   302-ProAlThrValGluSerIleAla-309
SEQ. ID. NO. 20996   314-SerTyrAlaAspGluLeuAspGlyTyrGlyLys-324
SEQ. ID. NO. 20997   336-SerIleTyrAlaGlyLeu-341
Antigenic Index - Jameson-Wolf
SEQ. ID. NO. 20998   7-AsnSerLeuLysGlnLeuGlnGluGluArgIleArgGlnGluArgIleArgGlnGluArgIleArgGlnAlaArgGlyAsnLeu-34
SEQ. ID. NO. 20999   36-SerValAsnArgLysGlnArgGluAlaTrpAspLysPheGlnLysLeuAsnThrGluLeuAsnArgLeuLysThrGluValAlaAla-64
SEQ. ID. NO. 21000   74-SerGlyAsnTyrLysAsnSerGlnProAsn-83
SEQ. ID. NO. 21001   91-AsnAlaGluProGlyGlnLysAsnArgPhe-100
SEQ. ID. NO. 21002   107-ValAsnAlaSerAsnArgGluValValLysAspLeuGluLysGlnGlnLys-123
SEQ. ID. NO. 21003   128-GlnGluGlnLysIleAsnAsnGluLeuAlaArgLeuLysLysIleGln-143
SEQ. ID. NO. 21004   149-LeuLeuLysLysGlnGlyValThrAspAlaAlaGluGlnThrGluSerArgArgGlnAsnAlaLysIleAlaLysAspAlaArgLysLeuLeuGluGln
                     LysGlyAsnGluGlnGlnLeu-188
SEQ. ID. NO. 21005   191-LeuLeuSerAsnLeuGluLysLysLysAlaGluHisArgIleGlnAspAlaGluAlaLysArgLysLeuAlaGluAlaArgLeuAlaAlaAlaGluLys
                     AlaArgLysGluAlaAlaGlnGlnLysAlaGluAlaAlaArgArgAlaGluMetSerAsnLeuThrAlaGluAspArgAsnIleGlnAlaProSer-254
SEQ. ID. NO. 21006   259-GlySerAlaAspGlyPheSerArgMetGlnGlyArgLeuLysLysProValAspGlyValProThr-280
SEQ. ID. NO. 21007   284-GlyGlnAsnArgSerGlyGlyAspVal-292
SEQ. ID. NO. 21008   314-SerTyrAlaAspGluLeuAspGlyTyrGly-323
SEQ. ID. NO. 21009   329-AspHisGlyGluAsnTyr-334
SEQ. ID. NO. 21010   345-SerValGlyLysGlyTyr-350
SEQ. ID. NO. 21011   354-AlaGlySerLysIleGlySerSerGlySerLeuProAspGlyGluGluGlyLeu-371
SEQ. ID. NO. 21012   381-ValLeuAsnProSerSerTrp-387
Hydrophilic Regions - Hopp-Woods
SEQ. ID. NO. 21013   7-AsnSerLeuLysGlnLeuGlnGluGluArgIleArgGlnGluArgIleArgGlnGluArgIleArgGlnAlaArgGlyAsn-33
SEQ. ID. NO. 21014   37-ValAsnArgLysGlnArgGluAlaTrpAspLysPheGlnLysLeuAsnThrGluLeuAsnArgLeuLysThrGluValAlaAla-64
SEQ. ID. NO. 21015   77-TyrLysAsnSerGln-81
SEQ. ID. NO. 21016   91-AsnAlaGluProGlyGlnLysAsnArgPhe-100
SEQ. ID. NO. 21017   110-SerAsnArgGluValValLysAspLeuGluLysGlnGlnLys-123
SEQ. ID. NO. 21018   128-GlnGluGlnLysIleAsnAsnGluLeuAlaArgLeuLysLysIleGln-143
SEQ. ID. NO. 21019   149-LeuLeuLysLysGlnGlyValThrAspAlaAlaGluGlnThrGluSerArgArgGlnAsnAlaLysIleAlaLysAspAlaArgLysLeuLeuGluGln
                     LysGlyAsnGluGlnGlnLeu-188
SEQ. ID. NO. 21020   193-SerAsnLeuGluLysLysLysAlaGluHisArgIleGlnAspAlaGluAlaLysArgLysLeuAlaGluAlaArgLeuAlaAlaAlaGluLysAlaArg
                     LysGluAlaAlaGlnGlnLysAlaGluAlaArgArgAlaGluMet-240
SEQ. ID. NO. 21021   244-ThrAlaGluAspArgAsnIleGln-251
SEQ. ID. NO. 21022   267-MetGlnGlyArgLeuLysLysProValAsp-276
SEQ. ID. NO. 21023   286-AsnArgSerGlyGlyAspVal-292
SEQ. ID. NO. 21024   315-TyrAlaAspGluLeuAspGlyTyrGly-323
SEQ. ID. NO. 21025   356-SerLysIleGlySer-360
SEQ. ID. NO. 21026   363-SerLeuProAspGlyGluGluGlyLeu-371
a601
AMPHI Regions - AMPHI
SEQ. ID. NO. 21027   7-LeuValAspGluIleAspValProAsnIleGlyArg-18
SEQ. ID. NO. 21028   26-AlaGlyIleProThrValPhe-32
SEQ. ID. NO. 21029   42-GlyLysGluLeuGlnAspAspIleAsnAsnAspAlaAlaAlaLeuGluLysPheGluLysIleArgAlaTyrGlyAlaLeu-68
SEQ. ID. NO. 21030   70-MetGlyLeuIleSerAspValSerGluAlaAla-80

TABLE 1-continued

| | |
|---|---|
| SEQ. ID. NO. 21031 | 100-SerSerGlyLysThrValAsn-106 |
| SEQ. ID. NO. 21032 | 137-AlaAlaAlaValProGlyThrLeuValAsnLeuAlaAla-149 |
| SEQ. ID. NO. 21033 | 169-GlyAlaAlaAlaGlu-173 |

Antigenic Index - Jameson-Wolf

| | |
|---|---|
| SEQ. ID. NO. 21034 | 3-ProThrGlyAsnLeuValAspGluIleAspValProAsnIleGlyArgLeuLys-20 |
| SEQ. ID. NO. 21035 | 39-GlyTyrThrGlyLysGluLeuGlnAspAspIleAsnAsnAspAlaAlaAlaLeuGluLysPheGluLysIleArgAla-64 |
| SEQ. ID. NO. 21036 | 75-AspValSerGluAlaAlaAlaArgAlaHisThrPro-86 |
| SEQ. ID. NO. 21037 | 97-TyrThrAlaSerSerGlyLysThrValAsn-106 |
| SEQ. ID. NO. 21038 | 149-AlaGlyGlyGlyThrArgLysGluValArgPheGlyHisProSerGlyThrLeuArg-167 |
| SEQ. ID. NO. 21039 | 172-AlaGluCysGlnAspGlyGln-178 |
| SEQ. ID. NO. 21040 | 185-ValMetSerArgSerAlaArgValMet-193 |
| SEQ. ID. NO. 21041 | 198-ValArgValProGluAspCysPhe-205 |

Hydrophilic Regions - Hopp-Woods

| | |
|---|---|
| SEQ. ID. NO. 21042 | 7-LeuValAspGluIleAspVal-13 |
| SEQ. ID. NO. 21043 | 40-TyrThrGlyLysGluLeuGlnAspAspIleAsnAsnAspAlaAlaAlaLeuGluLysPheGluLysIleArgAla-64 |
| SEQ. ID. NO. 21044 | 75-AspValSerGluAlaAlaAlaArgAlaHisThr-85 |
| SEQ. ID. NO. 21045 | 99-AlaSerGlyLysThrValAsn-106 |
| SEQ. ID. NO. 21046 | 151-GlyGlyThrArgLysGluValArgPhe-159 |
| SEQ. ID. NO. 21047 | 172-AlaGluCysGlnAsp-176 |
| SEQ. ID. NO. 21048 | 188-ArgSerAlaArgValMet-193 |
| SEQ. ID. NO. 21049 | 200-ValProGluAspCysPhe-205 | a602
AMPHI Regions - AMPHI

| | |
|---|---|
| SEQ. ID. NO. 21050 | 7-AspLysAlaArgHis-11 |
| SEQ. ID. NO. 21051 | 21-ValAsnArgHisGlyGln-26 |
| SEQ. ID. NO. 21052 | 54-ArgGlnIleAlaGlnIle-59 |
| SEQ. ID. NO. 21053 | 61-AlaGlyLeuHisValCysAsnSerVal-69 |
| SEQ. ID. NO. 21054 | 78-HisValIleValGluMetCysAlaTrpTyr-87 |

Antigenic Index - Jameson-Wolf

| | |
|---|---|
| SEQ. ID. NO. 21055 | 5-GlnCysAspLysAlaArgHisMetArg-13 |
| SEQ. ID. NO. 21056 | 20-GlnValAsnArgHisGlyGlnThrGlyAsnCysGly-31 |
| SEQ. ID. NO. 21057 | 36-CysSerLeuGlnGlyAsnArgLysAlaGlnValPheAspThrAspLeuIleAspArgGlnIle-56 |
| SEQ. ID. NO. 21058 | 90-SerThrGlyGluTyr-94 |
| SEQ. ID. NO. 21059 | 99-GlnMetArgAspTyrIle-104 |

Hydrophilic Regions - Hopp-Woods

| | |
|---|---|
| SEQ. ID. NO. 21060 | 5-GlnCysAspLysAlaArgHisMetArg-13 |
| SEQ. ID. NO. 21061 | 20-GlnValAsnArgHisGlyGln-26 |
| SEQ. ID. NO. 21062 | 39-GlnGlyAsnArgLysAlaGlnValPheAsp-48 |
| SEQ. ID. NO. 21063 | 50-AspLeuIleAspArgGlnIle-56 | a603
AMPHI Regions - AMPHI

| | |
|---|---|
| SEQ. ID. NO. 21064 | 158-ValMetAspGluLeuAsnAlaCysIlePro-167 |
| SEQ. ID. NO. 21065 | 172-HisAsnProAlaAsnIleSerGlyIleLeuAla-182 |
| SEQ. ID. NO. 21066 | 186-HisPheProGlyLeuProAsnValGly-194 |
| SEQ. ID. NO. 21067 | 199-SerPheHisGlnThrMetPro-205 |
| SEQ. ID. NO. 21068 | 212-AlaValProArgGluLeu-217 |
| SEQ. ID. NO. 21069 | 245-GlyLysProLeuGluAspIleArgMetIleIleAlaHis-257 |
| SEQ. ID. NO. 21070 | 260-AsnGlyAlaSerIleThrAlaIleLysAsnGlyLysSerVal-273 |
| SEQ. ID. NO. 21071 | 280-ThrProIleGluGly-284 |
| SEQ. ID. NO. 21072 | 299-TyrSerTyrLeuThrSer-304 |
| SEQ. ID. NO. 21073 | 324-LeuGlyIleSerGlu-328 |
| SEQ. ID. NO. 21074 | 330-SerAsnAspCysArg-334 |
| SEQ. ID. NO. 21075 | 357-ArgLeuAlaLysTyrIleAlaSerMet-365 |
| SEQ. ID. NO. 21076 | 393-ValSerTyrLeuAsp-397 |

Antigenic Index - Jameson-Wolf

| | |
|---|---|
| SEQ. ID. NO. 21077 | 1-LeuSerSerArgArgArgGlyArgAsnAsnAspArgLysCysGlyIle-16 |
| SEQ. ID. NO. 21078 | 18-PheAlaGlnArgGlyArgLeuLysHisThrProProAsnAlaHisProPheSerAspAspProThrXxxLysLysGlnProGlnThrThrArgArgAsnIleMetSer-53 |
| SEQ. ID. NO. 21079 | 63-GlySerSerSerLeuLysGlyAlaValIleAspArgLysSerGlySer-78 |
| SEQ. ID. NO. 21080 | 84-LeuGlyGluArgLeuThrThrProGluAla-93 |
| SEQ. ID. NO. 21081 | 96-ThrPheSerLysAspGlyAsnLysArgGlnValProLeuSerGlyArgAsnCysHis-114 |
| SEQ. ID. NO. 21082 | 124-GluLeuGluLysHisGluLeuHisAspArgIleGln-135 |
| SEQ. ID. NO. 21083 | 142-AlaHisGlyGlyGluLysTyrSerGlu-150 |
| SEQ. ID. NO. 21084 | 157-AlaValMetAspGluLeuAsn-163 |
| SEQ. ID. NO. 21085 | 203-ThrMetProGluArgAlaTyr-209 |
| SEQ. ID. NO. 21086 | 215-ArgGluLeuArgLysLysTyrAlaPheArgArgTyrGlyPheHisGlyThrSerMetArg-234 |
| SEQ. ID. NO. 21087 | 246-LysProLeuGluAspIleArg-252 |
| SEQ. ID. NO. 21088 | 258-LeuGlyAsnGlyAla-262 |
| SEQ. ID. NO. 21089 | 265-ThrAlaIleLysAsnGlyLysSerValAspThrSerMetGly-278 |
| SEQ. ID. NO. 21090 | 289-ThrArgCysGlyAspIleAspProGlyVal-298 |
| SEQ. ID. NO. 21091 | 311-AlaGlnValAspGluMetLeuAsnLysLysSerGly-322 |
| SEQ. ID. NO. 21092 | 327-SerGluLeuSerAsnAspCysArgThrLeuGluIleAlaAlaAspGluGlyHisGluGlyAlaArgLeu-349 |
| SEQ. ID. NO. 21093 | 380-GlyIleGlyGluAsnSerArgAsnIleArgAlaLysThr-392 |
| SEQ. ID. NO. 21094 | 403-IleAspThrLysAlaAsnMetGluLysArgTyrGlyAsnSerGlyIle-418 |
| SEQ. ID. NO. 21095 | 420-SerProThrAspSerSerPro-426 |
| SEQ. ID. NO. 21096 | 432-ProThrAsnGluGluLeu-437 |

Hydrophilic Regions - Hopp-Woods

| | |
|---|---|
| SEQ. ID. NO. 21097 | 1-LeuSerSerArgArgArgGlyArgAsnAsnAspArgLysCysGlyIle-16 |
| SEQ. ID. NO. 21098 | 18-PheAlaGlnArgGlyArgLeuLysHisThrPro-28 |
| SEQ. ID. NO. 21099 | 34-PheSerAspAspProThrXxxLysLysGlnProGlnThrThrArgArgAsnIleMet-52 |

TABLE 1-continued

| | |
|---|---|
| SEQ. ID. NO. 21100 | 70-AlaValIleAspArgLysSerGly-77 |
| SEQ. ID. NO. 21101 | 84-LeuGlyGluArgLeuThrThr-90 |
| SEQ. ID. NO. 21102 | 97-PheSerLysAspGlyAsnLysArgGlnValProLeuSerGlyArgAsnCysHis-114 |
| SEQ. ID. NO. 21103 | 124-GluLeuGluLysHisGluLeuHisAspArgIleGln-135 |
| SEQ. ID. NO. 21104 | 143-HisGlyGlyGluLysTyrSerGlu-150 |
| SEQ. ID. NO. 21105 | 157-AlaValMetAspGluLeuAsn-163 |
| SEQ. ID. NO. 21106 | 204-MetProGluArgAlaTyr-209 |
| SEQ. ID. NO. 21107 | 215-ArgGluLeuArgLysLysTyrAlaPhe-223 |
| SEQ. ID. NO. 21108 | 246-LysProLeuGluAspIleArg-252 |
| SEQ. ID. NO. 21109 | 268-LysAsnGlyLysSerValAspThr-275 |
| SEQ. ID. NO. 21110 | 290-ArgCysGlyAspIleAspPro-296 |
| SEQ. ID. NO. 21111 | 311-AlaGlnValAspGluMetLeuAsnLysLysSerGly-322 |
| SEQ. ID. NO. 21112 | 328-GluLeuSerAsnAspCysArgThrLeuGluIleAlaAlaAspGluGlyHisGluGlyAlaArgLeu-349 |
| SEQ. ID. NO. 21113 | 381-IleGlyGluAsnSerArgAsnIleArgAlaLysThr-392 |
| SEQ. ID. NO. 21114 | 403-IleAspThrLysAlaAsnMetGluLysArgTyrGly-414 |
| SEQ. ID. NO. 21115 | 433-ThrAsnGluGluLeu-437 | a604
AMPHI Regions - AMPHI

| | |
|---|---|
| SEQ. ID. NO. 21116 | 36-HisArgValValGlnPheAla-42 |
| SEQ. ID. NO. 21117 | 53-ValGlyGlyIleHisGlyPheAlaThr-61 |
| SEQ. ID. NO. 21118 | 78-ValArgAlaGlyGlySerPhe-84 |
| SEQ. ID. NO. 21119 | 95-ArgThrValSerAlaAspPheLeuGluPhePheGlnSerCysGlyIle-110 |
| SEQ. ID. NO. 21120 | 114-ValValLeuGlnLeuPheAlaArgValAlaGlnValGlyGlyIleGlnGluAsn-131 |
| SEQ. ID. NO. 21121 | 148-ArgHisIleAsnPheIleAspGlnIleAlaGlyTrpGlu-160 |
| SEQ. ID. NO. 21122 | 166-ValGlyTrpIleLysLysPheAsp-173 |
| SEQ. ID. NO. 21123 | 191-PheGlnAsnCysAlaValLeuHisArg-199 |

Antigenic Index - Jameson-Wolf

| | |
|---|---|
| SEQ. ID. NO. 21124 | 11-AlaAlaCysGlyLysValAspGlnArgThrGlyHisGlyGlyGlyGlyArgAsnGlyAsnArgGlyGlyThrHis-35 |
| SEQ. ID. NO. 21125 | 67-GlyGlyGlyArgAspGluGlyAspPheArgArgValArgAlaGlyGlySerPhe-84 |
| SEQ. ID. NO. 21126 | 127-GlyIleGlnGluAsnGlyArgAsnAlaArgValAspGluArgGlyPheGln-143 |
| SEQ. ID. NO. 21127 | 175-TyrPheGlyCysArgGluArgTyrAlaVal-184 |
| SEQ. ID. NO. 21128 | 201-MetGlyAsnAsnGly-205 |
| SEQ. ID. NO. 21129 | 211-LeuProAspPheAspCysAlaAsp-218 |

Hydrophilic Regions - Hopp-Woods

| | |
|---|---|
| SEQ. ID. NO. 21130 | 14-GlyLysValAspGlnArgThrGlyHis-22 |
| SEQ. ID. NO. 21131 | 24-GlyGlyGlyArgAsnGlyAsnArgGlyGlyThrHis-35 |
| SEQ. ID. NO. 21132 | 68-GlyGlyArgAspGluGlyAspPheArgArgValArgAla-80 |
| SEQ. ID. NO. 21133 | 127-GlyIleGlnGluAsnGlyArgAsnAlaArgValAspGluArgGlyPhe-142 |
| SEQ. ID. NO. 21134 | 178-CysArgGluArgTyrAlaVal-184 |
| SEQ. ID. NO. 21135 | 214-PheAspCysAlaAsp-218 | a605
AMPHI Regions - AMPHI

| | |
|---|---|
| SEQ. ID. NO. 21136 | 13-ArgGlnIleTrpLysIleAlaAsp-20 |
| SEQ. ID. NO. 21137 | 38-ThrLeuPheTyrArgPheIleSerGluAsnPheThrAspTyrMetGln-53 |
| SEQ. ID. NO. 21138 | 107-LysLeuLysGluIlePheThrAlaIle-115 |
| SEQ. ID. NO. 21139 | 128-IleLysGlyLeuPheAspAspPheAsp-136 |
| SEQ. ID. NO. 21140 | 141-ArgLeuGlySerThr-145 |
| SEQ. ID. NO. 21141 | 155-AlaValLeuLysGlyValAlaGluLeu-163 |
| SEQ. ID. NO. 21142 | 173-IleAspLeuPheGlyAspAlaTyrGluTyrLeuIleSerAsn-186 |
| SEQ. ID. NO. 21143 | 188-AlaAlaAsnAlaGlyLys-193 |
| SEQ. ID. NO. 21144 | 204-ValSerLysLeuIleAlaArg-210 |
| SEQ. ID. NO. 21145 | 217-GluLysValAsnLysIleTyrAspPro-225 |
| SEQ. ID. NO. 21146 | 240-PheAspGluHisIle-244 |
| SEQ. ID. NO. 21147 | 291-AspSerLysProPheAspAlaValValSerAsn-301 |
| SEQ. ID. NO. 21148 | 341-HisAlaLeuAsnTyr-345 |
| SEQ. ID. NO. 21149 | 355-ValSerPheProGly-359 |
| SEQ. ID. NO. 21150 | 433-GluHisIleAlaGluIleValLysLeuPheAla-443 |
| SEQ. ID. NO. 21151 | 452-AlaGlnAsnAlaAlaGlnGlnThr-459 |
| SEQ. ID. NO. 21152 | 471-SerTyrValGluProGlu-476 |
| SEQ. ID. NO. 21153 | 478-ThrArgGlnIleIleAspIle-484 |
| SEQ. ID. NO. 21154 | 489-AlaGluIleSerGluThrValAlaLysIleGluArgLeuArgArgGluIleAspGluValIleAlaGluIleGlu-513 |

Antigenic Index - Jameson-Wolf

| | |
|---|---|
| SEQ. ID. NO. 21155 | 5-IleGlnGlnArgAlaGlnLeu-11 |
| SEQ. ID. NO. 21156 | 18-IleAlaAspGluValArgGlyAlaValAspGlyTrpAsp-30 |
| SEQ. ID. NO. 21157 | 44-IleSerGluAsnPheThrAspTyrMetGlnAlaGlyAspSerSerIleAsp-60 |
| SEQ. ID. NO. 21158 | 63-AlaMetProAspSer-67 |
| SEQ. ID. NO. 21159 | 71-ProGluIleLysAspAspAlaValLysVal-80 |
| SEQ. ID. NO. 21160 | 98-AlaHisGlnAsnGluGluLeuAsnThrLysLeuLysGlu-110 |
| SEQ. ID. NO. 21161 | 116-GluSerSerAlaSerGlyTyrProSerGluGlnAspIleLysGlyLeuPheAspAspPheAspThrThrSerSerArgLeu-142 |
| SEQ. ID. NO. 21162 | 146-ValAlaAspLysAsnLysArgLeu-153 |
| SEQ. ID. NO. 21163 | 164-AspPheGlySerPheGluAspHisHis-172 |
| SEQ. ID. NO. 21164 | 190-AsnAlaGlyLysSerGlyGlyGluPhePheThr-200 |
| SEQ. ID. NO. 21165 | 215-GlyGlnGluLysValAsnLysIleTyrAspProAlaCysGlySerGlySer-231 |
| SEQ. ID. NO. 21166 | 235-GlnAlaLysLysGlnPheAsp-241 |
| SEQ. ID. NO. 21167 | 253-GluIleAsnHisThrThrTyrAsn-260 |
| SEQ. ID. NO. 21168 | 280-LeuGlyAspThrLeuThrAsnProLysLeuLysAspSerLysProPheAspAla-297 |
| SEQ. ID. NO. 21169 | 310-GlySerGlyAspProThrLeuIleAsnAspAspArgPheAlaPro-324 |
| SEQ. ID. NO. 21170 | 330-ProLysSerLysAlaAsp-335 |
| SEQ. ID. NO. 21171 | 345-TyrLeuSerGlyArgGlyArgAlaAla-353 |
| SEQ. ID. NO. 21172 | 362-TyrArgGlyGlyAlaGluGlnLysIleArg-371 |

TABLE 1-continued

| SEQ. ID. NO. 21173 | 403-LeuSerLysHisLysAspAsnThrAsp-411 |
| SEQ. ID. NO. 21174 | 418-GlyGlyPhePheLysLysGluThrAsnAsnAsnValLeuThrGluGluHisIle-435 |
| SEQ. ID. NO. 21175 | 442-PheAlaAspLysAlaAspVal-448 |
| SEQ. ID. NO. 21176 | 458-GlnThrValLysAspAsnGlyTyr-465 |
| SEQ. ID. NO. 21177 | 473-ValGluProGluAspThrArgGluIleIleAsp-483 |
| SEQ. ID. NO. 21178 | 490-GluIleSerGluThrValAlaLysIleGluArgLeuArgArgGluIleAspGluValIleAla-510 |

Hydrophilic Regions - Hopp-Woods

| SEQ. ID. NO. 21179 | 18-IleAlaAspGluValArgGlyAlaValAsp-27 |
| SEQ. ID. NO. 21180 | 55-GlyAspSerSerIle-59 |
| SEQ. ID. NO. 21181 | 71-ProGluIleLysAspAspAlaValLysVal-80 |
| SEQ. ID. NO. 21182 | 98-AlaHisGlnAsnGluGluLeuAsnThrLysLeuLysGlu-110 |
| SEQ. ID. NO. 21183 | 122-TyrProSerGluGlnAspIleLysGlyLeuPheAspAspPheAspThrThrSerSerArgLeu-142 |
| SEQ. ID. NO. 21184 | 146-ValAlaAspLysAsnLysArgLeu-153 |
| SEQ. ID. NO. 21185 | 167-SerPheGluAspHisHis-172 |
| SEQ. ID. NO. 21186 | 191-AlaGlyLysSerGlyGly-196 |
| SEQ. ID. NO. 21187 | 215-GlyGlnGluLysValAsnLysIleTyrAsp-224 |
| SEQ. ID. NO. 21188 | 235-GlnAlaLysLysGlnPheAsp-241 |
| SEQ. ID. NO. 21189 | 287-ProLysLeuLysAspSerLysProPhe-295 |
| SEQ. ID. NO. 21190 | 316-LeuIleAsnAspAspArgPheAla-323 |
| SEQ. ID. NO. 21191 | 330-ProLysSerLysAlaAsp-335 |
| SEQ. ID. NO. 21192 | 348-GlyArgGlyArgAla-352 |
| SEQ. ID. NO. 21193 | 364-GlyGlyAlaGluGlnLysIleArg-371 |
| SEQ. ID. NO. 21194 | 404-SerLysHisLysAspAsnThrAsp-411 |
| SEQ. ID. NO. 21195 | 419-GlyPhePheLysLysGluThrAsn-426 |
| SEQ. ID. NO. 21196 | 430-LeuThrGluGluHisIle-435 |
| SEQ. ID. NO. 21197 | 442-PheAlaAspLysAlaAspVal-448 |
| SEQ. ID. NO. 21198 | 458-GlnThrValLysAspAsnGly-464 |
| SEQ. ID. NO. 21199 | 473-ValGluProGluAspThrArgGluIleIleAsp-483 |
| SEQ. ID. NO. 21200 | 490-GluIleSerGluThrValAlaLysIleGluArgLeuArgArgGluIleAspGluValIleAla-510 | a606
AMPHI Regions - AMPHI

| SEQ. ID. NO. 21201 | 72-LeuLeuAspHisMetThrArgAspGlu-80 |
| SEQ. ID. NO. 21202 | 90-AlaHisValGlyAsnGlyAsp-96 |
| SEQ. ID. NO. 21203 | 100-LeuThrLeuIleGlnGlyValValAsnThrPhe-110 |
| SEQ. ID. NO. 21204 | 116-ArgIleIleAlaAsn-120 |
| SEQ. ID. NO. 21205 | 139-SerMetValPheGlnIleLeuPheGlyPheLeuAlaSerLeuIleVal-154 |
| SEQ. ID. NO. 21206 | 171-LysLeuValGlyAlaProLysMetIleSerAlaLeuGlnArg-184 |
| SEQ. ID. NO. 21207 | 191-AspLeuProGluGluMetAsnAla-198 |

Antigenic Index - Jameson-Wolf

| SEQ. ID. NO. 21208 | 13-GluValIleAspThrProArgThrGluGluGluAla-24 |
| SEQ. ID. NO. 21209 | 31-GluAlaGlnAlaArgGlnTrpAsnLeuLysThrProGlu-43 |
| SEQ. ID. NO. 21210 | 48-HisSerProGluProAsnAla-54 |
| SEQ. ID. NO. 21211 | 57-ThrGlyAlaSerArgAsnSerSer-64 |
| SEQ. ID. NO. 21212 | 75-HisMetThrArgAspGluValGluAla-83 |
| SEQ. ID. NO. 21213 | 92-ValGlyAsnGlyAsp-96 |
| SEQ. ID. NO. 21214 | 122-IleAlaArgAsnAsnAspGlySerGlnSerGlnGlyThr-134 |
| SEQ. ID. NO. 21215 | 159-ArgGlnArgGluTyrArgAlaAspAlaGlyAla-169 |
| SEQ. ID. NO. 21216 | 182-LeuGlnArgLeuLysGlyAsnProValAspLeuProGluGluMetAsn-197 |
| SEQ. ID. NO. 21217 | 203-GlyAspThrArgAspSerLeuLeuSerThrHisProSerLeuAspAsnArgIleAlaArgLeuLysSer-225 |

Hydrophilic Regions - Hopp-Woods

| SEQ. ID. NO. 21218 | 13-GluValIleAspThrProArgThrGluGluGluAla-24 |
| SEQ. ID. NO. 21219 | 59-AlaSerArgAsnSer-63 |
| SEQ. ID. NO. 21220 | 75-HisMetThrArgAspGluValGluAla-83 |
| SEQ. ID. NO. 21221 | 124-ArgAsnAsnAspGlySerGlnSer-131 |
| SEQ. ID. NO. 21222 | 159-ArgGlnArgGluTyrArgAlaAspAlaGlyAla-169 |
| SEQ. ID. NO. 21223 | 183-GlnArgLeuLysGlyAsnPro-189 |
| SEQ. ID. NO. 21224 | 191-AspLeuProGluGluMetAsn-197 |
| SEQ. ID. NO. 21225 | 203-GlyAspThrArgAspSerLeu-209 |
| SEQ. ID. NO. 21226 | 214-ProSerLeuAspAsnArgIleAlaArgLeuLysSer-225 | a607
AMPHI Regions - AMPHI

| SEQ. ID. NO. 21227 | 18-ArgLeuLeuThrAlaLeuAlaLeu-25 |
| SEQ. ID. NO. 21228 | 70-PheMetGlyIleMetAlaAlaLeuAsnProMetIleAlaGln-83 |
| SEQ. ID. NO. 21229 | 90-ThrAspGluValGlyGluThr-96 |
| SEQ. ID. NO. 21230 | 104-GlyLeuPheLeuGlyValPheGlyMetValLeuMetTrpAlaAlaIleThrProPheArgAsnTrpLeuThrLeuSerAspTyrValGluGlyThrMet-136 |
| SEQ. ID. NO. 21231 | 151-MetValHisArgAlaLeuHisAlaTyrAlaSerSer-162 |
| SEQ. ID. NO. 21232 | 226-PhePheArgProPheGly-231 |
| SEQ. ID. NO. 21233 | 244-PheLysGlnIleTrpLysIleGlyAla-252 |
| SEQ. ID. NO. 21234 | 320-AlaArgTyrIleSerGlyValSerLeu-328 |
| SEQ. ID. NO. 21235 | 337-IleThrValLeuSerLeuVal-343 |
| SEQ. ID. NO. 21236 | 373-PheGlnProAlaAspPheThrGlnCysIleAlaSerTyrAla-386 |
| SEQ. ID. NO. 21237 | 424-TyrGlyPheTrpThrAlaLeuIleAla-432 |

Antigenic Index - Jameson-Wolf

| SEQ. ID. NO. 21238 | 15-LysGluValArgLeu-19 |
| SEQ. ID. NO. 21239 | 47-GlyAlaGlyLysGluAspLeuAla-54 |
| SEQ. ID. NO. 21240 | 86-GlyAlaGlyLysThrAspGluValGlyGluThrGlyArgGlnGlyIle-101 |
| SEQ. ID. NO. 21241 | 121-ProPheArgAsnTrp-125 |
| SEQ. ID. NO. 21242 | 128-LeuSerAspTyrValGluGlyThr-135 |
| SEQ. ID. NO. 21243 | 160-AlaSerSerLeuAsnArgProArgLeu-168 |

TABLE 1-continued

| | |
|---|---|
| SEQ. ID. NO. 21244 | 234-AlaLysPheGlyLysProAspTrp-241 |
| SEQ. ID. NO. 21245 | 311-SerLeuGlyArgArgGluPheSerArgAlaArgTyrIleSer-324 |
| SEQ. ID. NO. 21246 | 353-TyrAsnAsnAspPro-357 |
| SEQ. ID. NO. 21247 | 388-ArgGlyTyrLysValThrLys-394 |
| SEQ. ID. NO. 21248 | 447-LeuCysSerArgGluMetValArgSerHisLysAlaVal-459 |

Hydrophilic Regions - Hopp-Woods

| | |
|---|---|
| SEQ. ID. NO. 21249 | 15-LysGluValArgLeu-19 |
| SEQ. ID. NO. 21250 | 47-GlyAlaGlyLysGluAspLeuAla-54 |
| SEQ. ID. NO. 21251 | 88-GlyLysThrArgAspGluValGlyGluThrGlyArg-98 |
| SEQ. ID. NO. 21252 | 163-LeuAsnArgProArg-167 |
| SEQ. ID. NO. 21253 | 312-LeuGlyArgArgGluPheSerArg-319 |
| SEQ. ID. NO. 21254 | 390-TyrLysValThrLys-394 |
| SEQ. ID. NO. 21255 | 447-LeuCysSerArgGluMetValArgSerHisLysAlaVal-459 | a608
AMPHI Regions - AMPHI

| | |
|---|---|
| SEQ. ID. NO. 21256 | 66-AlaValGlnLysIleLeuGln-72 |
| SEQ. ID. NO. 21257 | 93-ValLeuSerLeuLeu-97 |
| SEQ. ID. NO. 21258 | 103-ArgAlaSerAspGluLeuAlaArgIlePheGlyThrGln-115 |
| SEQ. ID. NO. 21259 | 124-AspIleGlyHisGlyIleLysGlnIleGlyArgAsnIleAlaGluGlnIleGlyArgPheSerArgGluProGluSerAla-150 |
| SEQ. ID. NO. 21260 | 154-AsnGluAlaLeuAlaAspCysLeuAspGluIleSerArgLeuArgAspGlyValGluArgLeuAsnGluArgLeuAspArgLeu-181 |

Antigenic Index - Jameson-Wolf

| | |
|---|---|
| SEQ. ID. NO. 21261 | 13-LeuGlnSerProAspSerArgSerGluLeu-22 |
| SEQ. ID. NO. 21262 | 39-LeuAlaGlyArgIleThrGluAspGlyLeuLeuSerAlaGlyAsnGlyPheAlaAspThrGluIleThrPheArgAsnSerAla-66 |
| SEQ. ID. NO. 21263 | 71-LeuGlnGlyGlyGluProGlyAlaGlyAspIleGlyLeuGluGly-85 |
| SEQ. ID. NO. 21264 | 98-GlySerLeuArgSerArgAlaSerAspGluLeuAla-109 |
| SEQ. ID. NO. 21265 | 114-ThrGlnAlaAspIleGlySerArgAlaAlaAsp-124 |
| SEQ. ID. NO. 21266 | 131-GlnIleGlyArgAsnIleAla-137 |
| SEQ. ID. NO. 21267 | 139-GlnIleGlyArgPheSerArgGluProGluSerAlaAsnIleGlyAsn-154 |
| SEQ. ID. NO. 21268 | 156-AlaLeuAlaAspCysLeuAspGluIleSerArgLeuArgAspGlyValGluArgLeuAsnGluArgLeuAspArgLeuGluArgAspIleTrp-186 |

Hydrophilic Regions - Hopp-Woods

| | |
|---|---|
| SEQ. ID. NO. 21269 | 15-SerProAspSerArgSerGluLeu-22 |
| SEQ. ID. NO. 21270 | 39-LeuAlaGlyArgIleThrGluAspGlyLeu-48 |
| SEQ. ID. NO. 21271 | 56-AlaAspThrGluIleThrPhe-62 |
| SEQ. ID. NO. 21272 | 74-GlyGluProGlyAlaGly-79 |
| SEQ. ID. NO. 21273 | 81-IleGlyLeuGluGly-85 |
| SEQ. ID. NO. 21274 | 100-LeuArgSerArgAlaSerAspGluLeuAla-109 |
| SEQ. ID. NO. 21275 | 116-AlaAspIleGlySerArgAlaAlaAsp-124 |
| SEQ. ID. NO. 21276 | 139-GlnIleGlyArgPheSerArgGluProGluSerAlaAsnIleGly-153 |
| SEQ. ID. NO. 21277 | 156-AlaLeuAlaAspCysLeuAspGluIleSerArgLeuArgAspGlyValGluArgLeuAsnGluArgLeuAspArgLeuGluArgAspIleTrp-186 | a609
AMPHI Regions - AMPHI

| | |
|---|---|
| SEQ. ID. NO. 21278 | 15-ThrLeuAspAlaPheVal-20 |
| SEQ. ID. NO. 21279 | 30-HisHisIlePheHisGluPheArgValPheValGlyPhePhe-43 |
| SEQ. ID. NO. 21280 | 52-PheGluGlnAlaValGlu-57 |
| SEQ. ID. NO. 21281 | 67-IleAspAspPheLeu-71 |
| SEQ. ID. NO. 21282 | 114-ValAlaValCysThrVal-119 |

Antigenic Index - Jameson-Wolf

| | |
|---|---|
| SEQ. ID. NO. 21283 | 10-AlaLeuAspAspGluThrLeu-16 |
| SEQ. ID. NO. 21284 | 20-ValGlyAsnGlnArgSerSerAspIleAla-29 |
| SEQ. ID. NO. 21285 | 69-AspPheLeuAspThrAspPheGlyIle-77 |
| SEQ. ID. NO. 21286 | 79-SerGlnAlaAspGlyAsnValArg-86 |
| SEQ. ID. NO. 21287 | 99-GlyThrArgAlaLysArgGlyTyrGlyAsnHisAspLeu-111 |
| SEQ. ID. NO. 21288 | 124-ArgGluAlaAspIle-128 |

Hydrophilic Regions - Hopp-Woods

| | |
|---|---|
| SEQ. ID. NO. 21289 | 10-AlaLeuAspAspGluThrLeu-16 |
| SEQ. ID. NO. 21290 | 23-GlnArgSerSerAspIle-28 |
| SEQ. ID. NO. 21291 | 79-SerGlnAlaAspGlyAsnVal-85 |
| SEQ. ID. NO. 21292 | 100-ThrArgAlaLysArgGlyTyrGly-107 |
| SEQ. ID. NO. 21293 | 124-ArgGluAlaAspIle-128 | a610
AMPHI Regions - AMPHI

| | |
|---|---|
| SEQ. ID. NO. 21294 | 6-MetGlnPheProTyr-10 |
| SEQ. ID. NO. 21295 | 14-SerAlaSerArgMetArgArgMetArgArg-23 |
| SEQ. ID. NO. 21296 | 98-GluArgAlaGlnGluAlaTyr-104 |
| SEQ. ID. NO. 21297 | 111-ProSerThrValArgAlaLeuArgGluArg-120 |
| SEQ. ID. NO. 21298 | 187-IleArgGluAlaLeuGlu-192 |
| SEQ. ID. NO. 21299 | 208-TyrAlaSerAlaPheTyrGlyProPheArgAsp-218 |
| SEQ. ID. NO. 21300 | 223-SerGlyAsnLeuGlyLysAlaAsp-230 |
| SEQ. ID. NO. 21301 | 268-LeuAspValValArgArgValLysAspGlu-277 |
| SEQ. ID. NO. 21302 | 296-AlaAlaValAlaAsn-300 |

Antigenic Index - Jameson-Wolf

| | |
|---|---|
| SEQ. ID. NO. 21303 | 11-ArgAsnValSerAlaSerArgMetArgArgMetArgArgAspAspPheSerArgArgLeuMetArgGluHisThrLeuThrAlaAspAsp-40 |
| SEQ. ID. NO. 21304 | 50-GlySerAlaArgGluGluAspValProSerMetProGlyValLysArgGlnSerLeuAsp-69 |
| SEQ. ID. NO. 21305 | 75-AlaGluGluAlaValLys-80 |
| SEQ. ID. NO. 21306 | 94-AlaAsnLysThrGluArgAlaGlnGluAlaTyrAsnProGluGlyLeuVal-110 |
| SEQ. ID. NO. 21307 | 115-ArgAlaLeuArgGluArgPhePro-122 |
| SEQ. ID. NO. 21308 | 139-GlyGlnAspGlyLeuThrAspGluAsnGlyTyrValMetAsnAspGluThrVal-156 |
| SEQ. ID. NO. 21309 | 175-AlaProSerAspMetMetAspGlyArgIleGlyAlaIleArgGluAlaLeuGluAspAlaGlyHis-196 |
| SEQ. ID. NO. 21310 | 215-ProPheArgAspAlaValGlySerSerGlyAsnLeuGlyLysAlaAspLysLysThrTyrGlnMetAspProAlaAsnThrAspGluAlaLeuHis-246 |
| SEQ. ID. NO. 21311 | 250-LeuAspIleGlnGluGlyAlaAsp-257 |

TABLE 1-continued

| SEQ. ID. NO. 21312 | 270-ValValArgArgValLysAspGluPheGlyVal-280 |

SEQ. ID. NO. 21312    270-ValValArgArgValLysAspGluPheGlyVal-280
SEQ. ID. NO. 21313    302-TrpLeuAspGlyGlyLysValVal-309
SEQ. ID. NO. 21314    317-LysArgAlaGlyAlaAspGly-323
SEQ. ID. NO. 21315    331-GluAlaAlaLysMetLeuLysArg-338
Hydrophilic Regions - Hopp-Woods
SEQ. ID. NO. 21316    14-SerAlaSerArgMetArgArgMetArgArgAspAspPheSerArgArgLeuMetArgGluHisThrLeuThrAla-38
SEQ. ID. NO. 21317    50-GlySerAlaArgGluGluAspValProSer-59
SEQ. ID. NO. 21318    61-ProGlyValLysArgGlnSerLeuAsp-69
SEQ. ID. NO. 21319    75-AlaGluGluAlaValLys-80
SEQ. ID. NO. 21320    95-AsnLysThrGluArgAlaGlnGluAlaTyrAsn-105
SEQ. ID. NO. 21321    115-ArgAlaLeuArgGluArgPhePro-122
SEQ. ID. NO. 21322    141-AspGlyLeuThrAspGluAsnGly-148
SEQ. ID. NO. 21323    151-MetAsnAspGluThrVal-156
SEQ. ID. NO. 21324    178-AspMetMetAspGlyArgIleGlyAlaIleArgGluAlaLeuGluAspAlaGly-195
SEQ. ID. NO. 21325    216-PheArgAspAlaValGly-221
SEQ. ID. NO. 21326    225-AsnLeuGlyLysAlaAspLysLysThrTyrGln-235
SEQ. ID. NO. 21327    238-ProAlaAsnThrAspGluAlaLeuHis-246
SEQ. ID. NO. 21328    250-LeuAspIleGlnGluGlyAlaAsp-257
SEQ. ID. NO. 21329    270-ValValArgArgValLysAspGluPheGly-279
SEQ. ID. NO. 21330    317-LysArgAlaGlyAla-321
SEQ. ID. NO. 21331    331-GluAlaAlaLysMetLeuLysArg-338
a611
AMPHI Regions - AMPHI
SEQ. ID. NO. 21332    15-CysArgLeuPheGlyLysLeuSerLeu-23
SEQ. ID. NO. 21333    26-ArgLeuLeuLeuGlyLeu-31
SEQ. ID. NO. 21334    48-ArgSerValArgArgValIle-54
SEQ. ID. NO. 21335    63-GlnValValAlaVal-67
SEQ. ID. NO. 21336    104-ValPheIleGluAspPheVal-110
SEQ. ID. NO. 21337    129-LeuGlyPheLeuGlyAsnValLeuArgThr-138
Antigenic Index - Jameson-Wolf
SEQ. ID. NO. 21338    1-MetProSerGluAsnArgMetGlyLysArgGlnLeuAla-13
SEQ. ID. NO. 21339    32-CysArgSerGlyValCysArgGlyArgCys-41
SEQ. ID. NO. 21340    45-PheProSerArgSerValArgArgValIlePheArgArgValArgIle-60
SEQ. ID. NO. 21341    119-AsnProAlaAspPheArgIle-125
SEQ. ID. NO. 21342    142-AlaSerGlnGluAsp-146
Hydrophilic Regions - Hopp-Woods
SEQ. ID. NO. 21343    1-MetProSerGluAsnArgMetGlyLysArgGlnLeuAla-13
SEQ. ID. NO. 21344    35-GlyValCysArgGlyArgCys-41
SEQ. ID. NO. 21345    53-ValIlePheArgArgValArgIle-60
SEQ. ID. NO. 21346    121-AlaAspPheArgIle-125
SEQ. ID. NO. 21347    142-AlaSerGlnGluAsp-146
a612
AMPHI Regions - AMPHI
SEQ. ID. NO. 21348    6-AsnIleAlaLysLysLeuAlaGlyVal-14
SEQ. ID. NO. 21349    55-AlaAspLysAlaValGluLysCysAlaGluAsnValLeu-67
SEQ. ID. NO. 21350    81-GlyAsnPheProAsn-85
SEQ. ID. NO. 21351    101-AsnProTyrXxxLysLeuAsnLysSerLysSerProAspIlePheArgArgPhePheXxxGlyHisSer-123
Antigenic Index - Jameson-Wolf
SEQ. ID. NO. 21352    7-IleAlaLysLysLeuAlaGlyValAsp-15
SEQ. ID. NO. 21353    17-IleAlaPheAspPheAspGly-23
SEQ. ID. NO. 21354    27-AspPheGlyArgAspAspAlaValArgHisSerGlyVal-39
SEQ. ID. NO. 21355    57-LysAlaValGluLysCysAlaGlu-64
SEQ. ID. NO. 21356    97-GlyHisHisArgAsnProTyrXxxLysLeuAsnLysSerLysSerProAspIlePheArg-116
Hydrophilic Regions - Hopp-Woods
SEQ. ID. NO. 21357    7-IleAlaLysLysLeuAlaGlyValAsp-15
SEQ. ID. NO. 21358    28-PheGlyArgAspAspAlaValArg-35
SEQ. ID. NO. 21359    57-LysAlaValGluLysCysAlaGlu-64
SEQ. ID. NO. 21360    105-LysLeuAsnLysSerLysSerProAspIlePhe-115
a613
AMPHI Regions - AMPHI
SEQ. ID. NO. 21361    7-SerArgArgSerLeu-11
SEQ. ID. NO. 21362    95-MetProArgMetArgSer-100
SEQ. ID. NO. 21363    103-SerProMetSerProAla-108
SEQ. ID. NO. 21364    115-ArgIlePheCysThrAlaLeuLeuArgLys-124
SEQ. ID. NO. 21365    140-SerSerValMetArgPro-145
SEQ. ID. NO. 21366    168-LeuSerGlyLeuCysArgIle-174
Antigenic Index - Jameson-Wolf
SEQ. ID. NO. 21367    1-MetSerArgSerSerArgSerArgArgSerLeuArgArgSerThrProSerArg-18
SEQ. ID. NO. 21368    23-SerSerArgGlnSerAlaArgAla-30
SEQ. ID. NO. 21369    35-PheAlaAspSerGlySerArgGluAsnLeu-44
SEQ. ID. NO. 21370    73-ProLysIleArgAlaAsnSerSerAspAlaArgGluArgArgLeuProSerArgAspSerThrAla-94
SEQ. ID. NO. 21371    96-ProArgMetArgSerProSerSerProMetSerProAlaProGlySerProProTrp-114
SEQ. ID. NO. 21372    130-AlaLysProPheProAlaGluSerLysProSerSerValMetArgProAlaSer-147
SEQ. ID. NO. 21373    161-LysAlaAlaSerSerGluArgLeuSerGlyLeuCysArgIleArgArg-176
SEQ. ID. NO. 21374    178-MetMetGlyArgArgAlaAspIlePheSerAspArgGlyGlyGlu-192
Hydrophilic Regions - Hopp-Woods
SEQ. ID. NO. 21375    1-MetSerArgSerSerArgSerArgArgSerLeuArgArgSerThrProSer-17
SEQ. ID. NO. 21376    24-SerArgGlnSerAlaArgAla-30
SEQ. ID. NO. 21377    38-SerGlySerArgGluAsnLeu-44
SEQ. ID. NO. 21378    73-ProLysIleArgAlaAsnSerSerAspAlaArgGluArgArgLeuProSerArgAspSerThrAla-94

TABLE 1-continued

| | |
|---|---|
| SEQ. ID. NO. 21379 | 96-ProArgMetArgSerProSer-102 |
| SEQ. ID. NO. 21380 | 133-PheProAlaGluSerLysProSerSerValMetArg-144 |
| SEQ. ID. NO. 21381 | 161-LysAlaAlaSerSerGluArgLeuSerGly-170 |
| SEQ. ID. NO. 21382 | 172-CysArgIleArgArg-176 |
| SEQ. ID. NO. 21383 | 178-MetMetGlyArgArgAlaAspIlePheSerAspArgGlyGlyGlu-192 | a614
AMPHI Regions - AMPHI

| | |
|---|---|
| SEQ. ID. NO. 21384 | 20-SerGlnPheIleGlnGlnVal-26 |
| SEQ. ID. NO. 21385 | 65-AsnLeuIleLysThrLeuLeuAsp-72 |
| SEQ. ID. NO. 21386 | 90-AlaLeuPheTyrSerLeuLeuProValLeu-99 |
| SEQ. ID. NO. 21387 | 144-ValAlaGlyCysAspGluAlaLysGluGluValGlnGluIleValAspTyrLeuLysAlaProAsnArgTyrGlnSerLeu-170 |
| SEQ. ID. NO. 21388 | 210-AspPheValGluMetPheVal-216 |
| SEQ. ID. NO. 21389 | 222-ArgValArgAspMetPheGluGln-229 |
| SEQ. ID. NO. 21390 | 242-GluIleAspAlaValGlyArg-248 |
| SEQ. ID. NO. 21391 | 295-ProAlaLeuGlnArgProGlyArgPheAsp-304 |
| SEQ. ID. NO. 21392 | 333-SerValAspLeuLeuSerLeuAla-340 |
| SEQ. ID. NO. 21393 | 349-AlaLeuAlaAsnLeuValAsn-356 |

Antigenic Index - Jameson-Wolf

| | |
|---|---|
| SEQ. ID. NO. 21394 | 7-LeuAspGlyLysLysGluAspAsnGlyGlnIleGlu-18 |
| SEQ. ID. NO. 21395 | 26-ValAsnAsnGlyGluValSerGly-33 |
| SEQ. ID. NO. 21396 | 45-LeuIleLysGlyGluArgThrAspLysSerThrPhe-56 |
| SEQ. ID. NO. 21397 | 60-AlaProLeuAspAspAsnLeuIle-67 |
| SEQ. ID. NO. 21398 | 70-LeuLeuAspLysAsnValArgValLysValThrProGluGluLysProSerAla-87 |
| SEQ. ID. NO. 21399 | 111-MetGlnThrGlyGlyGlyGlyLysGlyGly-120 |
| SEQ. ID. NO. 21400 | 123-SerPheGlyLysSerArgAlaArgLeuLeuAspLysAspAlaAsnLys-138 |
| SEQ. ID. NO. 21401 | 145-AlaGlyCysAspGluAlaLysGluGluValGlnGlu-156 |
| SEQ. ID. NO. 21402 | 161-LeuLysAlaProAsnArgTyrGlnSerLeuGlyGlyArgValProArgGly-177 |
| SEQ. ID. NO. 21403 | 182-GlySerProGlyThrGlyLysThrLeuLeu-191 |
| SEQ. ID. NO. 21404 | 207-SerGlySerAspPhe-211 |
| SEQ. ID. NO. 21405 | 219-GlyAlaSerArgValArgAspMetPheGluGlnAlaLysLysAsnAla-234 |
| SEQ. ID. NO. 21406 | 241-AspGluIleAspAlaValGlyArgGlnArgGlyAlaGlyLeuGlyGlyGlyAsnAspGluArgGluGlnThrLeu-265 |
| SEQ. ID. NO. 21407 | 272-MetAspGlyPheGluSerAsnGln-279 |
| SEQ. ID. NO. 21408 | 287-ThrAsnArgProAspValLeuAspProAlaLeuGlnArgProGlyArgPheAspArg-305 |
| SEQ. ID. NO. 21409 | 311-LeuProAspIleArgGlyArgGluGlnIle-320 |
| SEQ. ID. NO. 21410 | 323-ValHisSerLysLysValProLeuAspLysSerValAsp-335 |
| SEQ. ID. NO. 21411 | 341-ArgGlyThrProGlyPheSerGly-348 |
| SEQ. ID. NO. 21412 | 362-AlaGlyArgArgAsnLysValLysValAspGlnSerAspLeuLysThrProLysThrLysSer-382 |

Hydrophilic Regions - Hopp-Woods

| | |
|---|---|
| SEQ. ID. NO. 21413 | 7-LeuAspGlyLysLysGluAspAsnGlyGln-16 |
| SEQ. ID. NO. 21414 | 27-AsnAsnGlyGluValSer-32 |
| SEQ. ID. NO. 21415 | 46-IleLysGlyGluArgThrAspLysSerThr-55 |
| SEQ. ID. NO. 21416 | 61-ProLeuAspAspAsnLeuIle-67 |
| SEQ. ID. NO. 21417 | 70-LeuLeuAspLysAsnValArgValLysValThrProGluGluLysProSer-86 |
| SEQ. ID. NO. 21418 | 125-GlyLysSerArgAlaArgLeuLeuAspLysAspAlaAsnLys-138 |
| SEQ. ID. NO. 21419 | 145-AlaGlyCysAspGluAlaLysGluGluValGlnGlu-156 |
| SEQ. ID. NO. 21420 | 162-LysAlaProAsnArg-166 |
| SEQ. ID. NO. 21421 | 171-GlyGlyArgValProArg-176 |
| SEQ. ID. NO. 21422 | 221-SerArgValArgAspMetPheGluGlnAlaLysLysAsnAla-234 |
| SEQ. ID. NO. 21423 | 241-AspGluIleAspAlaValGlyArgGlnArgGlyAlaGly-253 |
| SEQ. ID. NO. 21424 | 256-GlyGlyAsnAspGluArgGluGlnThr-264 |
| SEQ. ID. NO. 21425 | 273-AspGlyPheGluSer-277 |
| SEQ. ID. NO. 21426 | 287-ThrAsnArgProAspValLeuAsp-294 |
| SEQ. ID. NO. 21427 | 296-AlaLeuGlnArgProGlyArgPheAspArg-305 |
| SEQ. ID. NO. 21428 | 312-ProAspIleArgGlyArgGluGlnIle-320 |
| SEQ. ID. NO. 21429 | 324-HisSerLysLysValProLeuAspLysSerValAsp-335 |
| SEQ. ID. NO. 21430 | 362-AlaGlyArgArgAsnLysValLysValAspGlnSerAspLeuLysThrProLysThrLys-381 | a616
AMPHI Regions - AMPHI

| | |
|---|---|
| SEQ. ID. NO. 21431 | 6-LysMetValValGlyLeu-11 |
| SEQ. ID. NO. 21432 | 13-AsnProGlyLysGluTyrGlu-19 |
| SEQ. ID. NO. 21433 | 48-PheGlyGluValAlaArgAla-54 |
| SEQ. ID. NO. 21434 | 77-ValAlaAlaLeuAlaGlnPheTyrLys-85 |
| SEQ. ID. NO. 21435 | 115-GlyHisAsnGlyLeuLysAspIle-122 |
| SEQ. ID. NO. 21436 | 161-ProThrAspArgCysArgArgGlnIlePro-170 |
| SEQ. ID. NO. 21437 | 174-ThrArgHisProCysArgGlnMetArgGly-183 |
| SEQ. ID. NO. 21438 | 201-ThrAlaCysSerArgPheProTyr-208 |
| SEQ. ID. NO. 21439 | 265-AlaProValGlnAsnLeuProAsnValAla-274 |
| SEQ. ID. NO. 21440 | 297-GlyGlyIleTyrSerLeuLeuPhe-304 |
| SEQ. ID. NO. 21441 | 317-PheAspLysAlaAla-321 |
| SEQ. ID. NO. 21442 | 355-CysPheAlaLeuPheSerGluCysAlaGlnAlaPhe-366 |
| SEQ. ID. NO. 21443 | 368-AlaThrArgThrGlySerLeuGlyAspValLeuAlaAspMetAlaGlyThrValLeu-386 |

Antigenic Index - Jameson-Wolf

| | |
|---|---|
| SEQ. ID. NO. 21444 | 11-LeuGlyAsnProGlyLysGluTyrGluGlnThrArgHisAsnAlaGlyPhe-27 |
| SEQ. ID. NO. 21445 | 39-AlaSerPheLysGluGluLysLysPhePhe-48 |
| SEQ. ID. NO. 21446 | 51-ValAlaArgAlaThrLeuProAspGlyAsp-60 |
| SEQ. ID. NO. 21447 | 65-LysProThrThrPheMetAsnArgSerGlyGlnAla-76 |
| SEQ. ID. NO. 21448 | 86-IleLysProGluGlu-90 |
| SEQ. ID. NO. 21449 | 96-AspGluLeuAspIleProCysGlyArgIleLysPhe-107 |
| SEQ. ID. NO. 21450 | 109-LeuGlyGlyGlyAsnGlyGlyHisAsnGlyLeuLysAspIleGlnAla-124 |
| SEQ. ID. NO. 21451 | 127-GlyThrAlaAspTyrTyrArg-133 |

TABLE 1-continued

| | |
|---|---|
| SEQ. ID. NO. 21452 | 138-IleGlyHisProGlyAspArgAsnLeu-146 |
| SEQ. ID. NO. 21453 | 152-LeuAsnLysProSerThrGluXxxProProThrAspArgCysArgArgGlnIleProAlaSerHisThrArgHisProCysArgGlnMetArgGlyAsnProLeuPro-187 |
| SEQ. ID. NO. 21454 | 190-GlnMetThrArgCysArgLeuLysProPheGlnThrAlaCysSerArgPheProTyrProAsnSerHisAspArgThrGlnAla-217 |
| SEQ. ID. NO. 21455 | 219-TyrProAsnArgIleHisProArgHisArgArgAsnProArgPheProAla-235 |
| SEQ. ID. NO. 21456 | 238-MetGlnHisArgArgArgThrIleArgArgArgSerGlyThrMetAlaArgHisThrCysArgThrArgArgGlnIlePro-264 |
| SEQ. ID. NO. 21457 | 266-ProValGlnAsnLeuProAsnValAlaGlyArgGlyGlyGlyMetLysLeuProArgAsnArgPheSer-288 |
| SEQ. ID. NO. 21458 | 306-AlaAlaAspThrAlaProProProPheProHisPheAspLysAlaAla-321 |
| SEQ. ID. NO. 21459 | 336-AlaPheLysThrGlyLysLeuProIle-344 |
| SEQ. ID. NO. 21460 | 368-AlaThrArgThrGlySerLeuGly-375 |
| SEQ. ID. NO. 21461 | 392-ArgAlaAlaAspArgProAsp-398 |
| Hydrophilic Regions - Hopp-Woods | |
| SEQ. ID. NO. 21462 | 13-AsnProGlyLysGluTyrGluGlnThrArgHis-23 |
| SEQ. ID. NO. 21463 | 39-AlaSerPheLysGluGluLysLysPhePhe-48 |
| SEQ. ID. NO. 21464 | 86-IleLysProGluGlu-90 |
| SEQ. ID. NO. 21465 | 96-AspGluLeuAspIleProCysGlyArgIleLysPhe-107 |
| SEQ. ID. NO. 21466 | 117-AsnGlyLeuLysAspIleGlnAla-124 |
| SEQ. ID. NO. 21467 | 140-HisProGlyAspArgAsnLeu-146 |
| SEQ. ID. NO. 21468 | 155-ProSerThrGluXxxProProThrAspArgCysArgArgGlnIlePro-170 |
| SEQ. ID. NO. 21469 | 172-SerHisThrArgHisProCysArgGlnMetArgGlyAsnPro-185 |
| SEQ. ID. NO. 21470 | 190-GlnMetThrArgCysArgLeuLysPro-198 |
| SEQ. ID. NO. 21471 | 210-AsnSerHisAspArgThrGln-216 |
| SEQ. ID. NO. 21472 | 223-IleHisProArgHisArgArgAsnProArg-232 |
| SEQ. ID. NO. 21473 | 238-MetGlnHisArgArgArgThrIleArgArgArgSerGlyThrMet-252 |
| SEQ. ID. NO. 21474 | 255-HisThrCysArgThrArgArgGlnIle-263 |
| SEQ. ID. NO. 21475 | 274-AlaGlyArgGlyGlyGly-279 |
| SEQ. ID. NO. 21476 | 281-LysLeuProArgAsnArgPhe-287 |
| SEQ. ID. NO. 21477 | 306-AlaAlaAspThrAla-310 |
| SEQ. ID. NO. 21478 | 316-HisPheAspLysAlaAla-321 |
| SEQ. ID. NO. 21479 | 336-AlaPheLysThrGlyLys-341 |
| SEQ. ID. NO. 21480 | 392-ArgAlaAlaAspArgProAsp-398 |
| a619 | |
| AMPHI Regions - AMPHI | |
| SEQ. ID. NO. 21481 | 50-LysLeuAlaAlaLeuLeu-55 |
| SEQ. ID. NO. 21482 | 66-GlnLeuPheGlnThrLeuThrAsn-73 |
| SEQ. ID. NO. 21483 | 134-GlnGlyGlyArgAspLeu-139 |
| SEQ. ID. NO. 21484 | 146-GlyValIlePheGlyIleLeuPheArgSerLeuSerSerLeuLeuSerArg-162 |
| SEQ. ID. NO. 21485 | 165-AspProGluGluPhe-169 |
| SEQ. ID. NO. 21486 | 175-AsnMetPheAlaGlyPheAsnThrValHisSer-185 |
| SEQ. ID. NO. 21487 | 246-AlaValValGlyProValSerPhePheGlyLeuLeuAlaAlaSerLeuAlaAsnHisPheSer-266 |
| SEQ. ID. NO. 21488 | 303-LeuSerValValValGluPhe-309 |
| Antigenic Index - Jameson-Wolf | |
| SEQ. ID. NO. 21489 | 1-MetProSerGluLysAsnIle-7 |
| SEQ. ID. NO. 21490 | 11-AlaGlySerSerArgPro-16 |
| SEQ. ID. NO. 21491 | 35-AsnValLysGlyAspTrpAsp-41 |
| SEQ. ID. NO. 21492 | 132-IleLysGlnGlyGlyArgAspLeuPro-140 |
| SEQ. ID. NO. 21493 | 163-MetIleAspProGluGluPheThr-170 |
| SEQ. ID. NO. 21494 | 203-TrpArgGluArgTyrArgLeu-209 |
| SEQ. ID. NO. 21495 | 213-LeuLeuGlyArgAspGlnAla-219 |
| SEQ. ID. NO. 21496 | 265-PheSerProSerValLysHisSerVal-273 |
| Hydrophilic Regions - Hopp-Woods | |
| SEQ. ID. NO. 21497 | 1-MetProSerGluLysAsnIle-7 |
| SEQ. ID. NO. 21498 | 134-GlnGlyGlyArgAspLeuPro-140 |
| SEQ. ID. NO. 21499 | 163-MetIleAspProGluGluPheThr-170 |
| SEQ. ID. NO. 21500 | 203-TrpArgGluArgTyrArgLeu-209 |
| SEQ. ID. NO. 21501 | 213-LeuLeuGlyArgAspGlnAla-219 |
| SEQ. ID. NO. 21502 | 269-ValLysHisSerVal-273 |
| a620 | |
| AMPHI Regions - AMPHI | |
| SEQ. ID. NO. 21503 | 9-ValAlaValSerAlaLeuSerAlaCysArgGlnAla-20 |
| SEQ. ID. NO. 21504 | 31-IleSerAspArgSerVal-36 |
| SEQ. ID. NO. 21505 | 67-SerThrIleLysGlnMetPheGlyTyrThrLysLeuProGluGluProLysGlyIleArgValIleTyrValThrAspMetGlyAsnValThrAspTrpThr-100 |
| SEQ. ID. NO. 21506 | 139-GlnAlaGluLysPhe-143 |
| Antigenic Index - Jameson-Wolf | |
| SEQ. ID. NO. 21507 | 15-SerAlaCysArgGlnAlaGluGluGlyProProProLeuProArgGlnIleSerAspArgSerValGlyHis-38 |
| SEQ. ID. NO. 21508 | 43-AsnLeuThrGluHisAsnGlyProLysAla-52 |
| SEQ. ID. NO. 21509 | 57-AsnGlyLysProAspGlnProVal-64 |
| SEQ. ID. NO. 21510 | 75-TyrThrLysLeuProGluGluProLysGlyIle-85 |
| SEQ. ID. NO. 21511 | 97-ThrAspTrpThrAsnProAsnAlaAspThrGluTrpMetAspAlaLysLys-113 |
| SEQ. ID. NO. 21512 | 125-GlyMetGlyAlaGluAspAlaLeuProPheGlyAsnLysGluGlnAlaGluLysPheAlaLysAspLysGlyGlyLysValValGlyPheAspAspMetProAspThrTyr-161 |
| Hydrophilic Regions - Hopp-Woods | |
| SEQ. ID. NO. 21513 | 18-ArgGlnAlaGluGluGlyProProProLeu-27 |
| SEQ. ID. NO. 21514 | 30-GlnIleSerAspArgSerVal-36 |
| SEQ. ID. NO. 21515 | 46-GluHisAsnGlyProLys-51 |
| SEQ. ID. NO. 21516 | 58-GlyLysProAspGln-62 |
| SEQ. ID. NO. 21517 | 77-LysLeuProGluGluProLysGlyIle-85 |
| SEQ. ID. NO. 21518 | 103-AsnAlaAspThrGluTrpMetAspAlaLysLys-113 |
| SEQ. ID. NO. 21519 | 127-GlyAlaGluAspAlaLeu-132 |

TABLE 1-continued

| | |
|---|---|
| SEQ. ID. NO. 21520 | 135-GlyAsnLysGluGlnAlaGluLysPheAlaLysAspLysGlyGlyLys-150 |
| SEQ. ID. NO. 21521 | 155-AspAspMetProAsp-159 | a622
AMPHI Regions - AMPHI

| | |
|---|---|
| SEQ. ID. NO. 21522 | 28-LeuProGluAlaValArgAsnLeuAlaArg-37 |
| SEQ. ID. NO. 21523 | 62-GluGluIleIleArgTrpLeuAlaAsp-70 |
| SEQ. ID. NO. 21524 | 112-IleLeuGlyGlnIleLysAspAlaValArgValAlaGln-124 |
| SEQ. ID. NO. 21525 | 131-LysLysLeuAsnAlaLeuPheGlnLys-139 |
| SEQ. ID. NO. 21526 | 142-SerValAlaLysGluVal-147 |
| SEQ. ID. NO. 21527 | 169-GluGlnIlePheProAspIleGlyAsp-177 |
| SEQ. ID. NO. 21528 | 187-GluMetIleGluLeuValAla-193 |
| SEQ. ID. NO. 21529 | 214-AlaGlnGluLeuCysAspLys-220 |
| SEQ. ID. NO. 21530 | 232-AspLeuProAlaIleLeuHis-238 |
| SEQ. ID. NO. 21531 | 288-AspLeuAsnAspAla-292 |
| SEQ. ID. NO. 21532 | 297-ValAspAspMetValAsnIleValGlnSerGly-307 |
| SEQ. ID. NO. 21533 | 324-GluLysValAlaGluPheValArgGlnGln-333 |
| SEQ. ID. NO. 21534 | 345-LeuArgAspGluGlyGluLys-351 |
| SEQ. ID. NO. 21535 | 354-LysGlnValLeuGluAsnAlaMetLysGlnLeuAlaLys-366 |
| SEQ. ID. NO. 21536 | 384-LysLeuLeuHisSerProThrGlnThrLeuAsnLysAlaGlyGlu-398 |

Antigenic Index - Jameson-Wolf

| | |
|---|---|
| SEQ. ID. NO. 21537 | 16-SerIleArgGluLysLeuAla-22 |
| SEQ. ID. NO. 21538 | 30-GluAlaValArgAsnLeuAlaArgSerAsnAlaAla-41 |
| SEQ. ID. NO. 21539 | 49-ThrCysAsnArgThrGlu-54 |
| SEQ. ID. NO. 21540 | 57-CysValGlyAspSerGluGluIleIle-65 |
| SEQ. ID. NO. 21541 | 75-ProIleGluGluIleSerProTyrLeu-83 |
| SEQ. ID. NO. 21542 | 90-GluThrValArgHis-94 |
| SEQ. ID. NO. 21543 | 115-GlnIleLysAspAlaValArgValAlaGlnGluGlnGluSerMetGlyLysLysLeu-133 |
| SEQ. ID. NO. 21544 | 142-SerValAlaLysGluValArgThrAspThrAlaValGlyGluAsnSerVal-158 |
| SEQ. ID. NO. 21545 | 174-AspIleGlyAspLeuAsn-179 |
| SEQ. ID. NO. 21546 | 199-LysSerProArgLeu-203 |
| SEQ. ID. NO. 21547 | 210-ThrLeuAlaArgAlaGlnGluLeuCysAspLysLeuGlyValAsnAlaGlu-226 |
| SEQ. ID. NO. 21548 | 257-GlyMetValGluArgAlaLeuLysGlnArgGlnSer-268 |
| SEQ. ID. NO. 21549 | 277-AlaValProArgAspIleGluAlaGluValGlyAspLeuAsnAsp-291 |
| SEQ. ID. NO. 21550 | 305-GlnSerGlyLysGluAlaArgGlnLysAlaAlaAlaAla-317 |
| SEQ. ID. NO. 21551 | 321-LeuValSerGluLysValAlaGluPheValArgGlnGlnGlnGlyArgGlnSerVal-339 |
| SEQ. ID. NO. 21552 | 343-ArgAlaLeuArgAspGluGlyGluLysAlaArgLysGlnValLeu-357 |
| SEQ. ID. NO. 21553 | 368-AlaThrAlaGluGluValLeuGlu-375 |
| SEQ. ID. NO. 21554 | 381-LeuThrAsnLysLeuLeuHisSerProThrGlnThrLeuAsnLysAlaGlyGluGluAspLysAspLeuVal-404 |

Hydrophilic Regions - Hopp-Woods

| | |
|---|---|
| SEQ. ID. NO. 21555 | 16-SerIleArgGluLysLeuAla-22 |
| SEQ. ID. NO. 21556 | 30-GluAlaValArgAsnLeuAlaArgSerAsnAlaAla-41 |
| SEQ. ID. NO. 21557 | 59-GlyAspSerGluGluIleIle-65 |
| SEQ. ID. NO. 21558 | 75-ProIleGluGluIleSer-80 |
| SEQ. ID. NO. 21559 | 90-GluThrValArgHis-94 |
| SEQ. ID. NO. 21560 | 115-GlnIleLysAspAlaValArgValAlaGlnGluGlnGluSerMetGlyLysLysLeu-133 |
| SEQ. ID. NO. 21561 | 142-SerValAlaLysGluValArgThrAspThrAlaValGlyGluAsnSerVal-158 |
| SEQ. ID. NO. 21562 | 210-ThrLeuAlaArgAlaGlnGluLeuCysAsp-219 |
| SEQ. ID. NO. 21563 | 257-GlyMetValGluArgAlaLeuLysGlnArgGlnSer-268 |
| SEQ. ID. NO. 21564 | 277-AlaValProArgAspIleGluAlaGluValGlyAspLeuAsn-290 |
| SEQ. ID. NO. 21565 | 305-GlnSerGlyLysGluAlaArgGlnLysAlaAlaAlaAla-317 |
| SEQ. ID. NO. 21566 | 321-LeuValSerGluLysValAlaGluPheValArg-331 |
| SEQ. ID. NO. 21567 | 333-GlnGlnGlyArgGlnSer-338 |
| SEQ. ID. NO. 21568 | 343-ArgAlaLeuArgAspGluGlyGluLysAlaArgLysGlnValLeu-357 |
| SEQ. ID. NO. 21569 | 368-AlaThrAlaGluGluValLeuGlu-375 |
| SEQ. ID. NO. 21570 | 392-ThrLeuAsnLysAlaGlyGluGluAspLysAspLeuVal-404 | a624
AMPHI Regions - AMPHI

| | |
|---|---|
| SEQ. ID. NO. 21571 | 14-LeuLeuLeuGlyIleIleGlyIlePheLeuPro-24 |
| SEQ. ID. NO. 21572 | 45-ArgPheHisArgTrpLeuHis-51 |
| SEQ. ID. NO. 21573 | 58-ProMetValHisAsn-62 |
| SEQ. ID. NO. 21574 | 92-PheProGlnArgTrpTrpValGlyAla-100 |
| SEQ. ID. NO. 21575 | 102-SerSerValPheCysSerLeuValAlaIle-111 |

Antigenic Index - Jameson-Wolf

| | |
|---|---|
| SEQ. ID. NO. 21576 | 41-LysAlaSerProArgPheHisArgTrp-49 |
| SEQ. ID. NO. 21577 | 51-HisArgHisArgTyrPheGlyProMet-59 |
| SEQ. ID. NO. 21578 | 63-TrpGluGlnAsnGlyAlaValProArgLysAlaLys-74 |
| SEQ. ID. NO. 21579 | 115-ArgArgProGluSer-119 |

Hydrophilic Regions - Hopp-Woods

| | |
|---|---|
| SEQ. ID. NO. 21580 | 67-GlyAlaValProArgLysAlaLys-74 |
| SEQ. ID. NO. 21581 | 115-ArgArgProGluSer-119 | a625
AMPHI Regions - AMPHI

| | |
|---|---|
| SEQ. ID. NO. 21582 | 25-SerGlyArgIleIleSerIleAlaAla-33 |
| SEQ. ID. NO. 21583 | 64-LysMetProProGluMetValTyrArgAla-73 |

Antigenic Index - Jameson-Wolf

| | |
|---|---|
| SEQ. ID. NO. 21584 | 5-ArgLysMetLysLysMetThrMetCysThrArgArgVal-17 |
| SEQ. ID. NO. 21585 | 57-ProPheLysSerProGlnThrLysMetProPro-67 |
| SEQ. ID. NO. 21586 | 73-AlaSerSerSerArgMetLysGly-80 |
| SEQ. ID. NO. 21587 | 96-AspAlaProLysThrLysLeuAsnGlyMetArgLysSerAsnValGln-111 |

TABLE 1-continued

Hydrophilic Regions - Hopp-Woods
SEQ. ID. NO. 21588  5-ArgLysMetLysLysMetThrMetCysThrArgArgVal-17
SEQ. ID. NO. 21589  60-SerProGlnThrLysMetProPro-67
SEQ. ID. NO. 21590  74-SerSerSerArgMetLysGly-80
SEQ. ID. NO. 21591  96-AspAlaProLysThrLysLeuAsnGlyMetArgLysSerAsnValGln-111
a627
AMPHI Regions - AMPHI
SEQ. ID. NO. 21592  21-LeuGlnAsnLeuVal-25
SEQ. ID. NO. 21593  56-IleAlaGluValGlyLysLeuPheLeuGlyIlePheIleThrIlePheProValLeuSerIleLeuLysAlaGlyGluAlaGlyAlaLeuGlyGlyVal
ValSerLeuValHisAspThrAlaGlyHisProIle-100
SEQ. ID. NO. 21594  109-GlyIleLeuSerAlaPheLeuAspAsnAla-118
SEQ. ID. NO. 21595  141-PheHisSerLeuLeuAlaValSer-148
SEQ. ID. NO. 21596  153-PheMetGlyAlaLeuThrTyrIleGlyAsnAlaProAsnPheMetValLys-169
SEQ. ID. NO. 21597  181-ThrPhePheGlyTyr-185
Antigenic Index - Jameson-Wolf
SEQ. ID. NO. 21598  3-GlyLeuTrpLysProGluHisProGlyPhe-12
SEQ. ID. NO. 21599  41-ThrProLysGlnValArgAlaGlyAsnGluPheAsnPhe-53
SEQ. ID. NO. 21600  94-AspThrAlaGlyHis-98
SEQ. ID. NO. 21601  128-AlaGlyGlyAspAla-132
SEQ. ID. NO. 21602  170-AlaIleAlaGluGlnArgGlyValPro-178
Hydrophilic Regions - Hopp-Woods
SEQ. ID. NO. 21603  5-TrpLysProGluHisProGly-11
SEQ. ID. NO. 21604  43-LysGlnValArgAlaGlyAsn-49
SEQ. ID. NO. 21605  170-AlaIleAlaGluGlnArgGlyVal-177
a628
AMPHI Regions - AMPHI
SEQ. ID. NO. 21606  10-CysGlyProProAsnSerCysValSerMetLeuAlaAlaPheSerAspGlyThrSerAlaProAlaAla-32
SEQ. ID. NO. 21607  34-HisThrTrpIleLeuArgSer-40
Antigenic Index - Jameson-Wolf
SEQ. ID. NO. 21608  6-LysProAlaGlyCysGlyProProAsnSer-15
SEQ. ID. NO. 21609  23-PheSerAspGlyThrSerAla-29
SEQ. ID. NO. 21610  40-SerValLysArgLeuAsnThrSerLysProArgLeuLysSerSerAla-55
SEQ. ID. NO. 21611  77-MetAlaAsnGlySerAlaSerThr-84
SEQ. ID. NO. 21612  91-GlyArgValArgSerAlaValHisLysProAspTrpIleArgLeuArgArgThrSerSerProLeuLys-113
SEQ. ID. NO. 21613  116-AsnAlaSerGlyAla-120
Hydrophilic Regions - Hopp-Woods
SEQ. ID. NO. 21614  40-SerValLysArgLeuAsnThrSerLysProArgLeuLysSerSerAla-55
SEQ. ID. NO. 21615  91-GlyArgValArgSerAlaValHisLys-99
SEQ. ID. NO. 21616  101-AspTrpIleArgLeuArgArgThrSerSer-110
a629
AMPHI Regions - AMPHI
SEQ. ID. NO. 21617  32-ArgTrpSerAspValPheSer-38
SEQ. ID. NO. 21618  48-IleSerArgLeuProArgThrPhe-55
SEQ. ID. NO. 21619  116-ValAlaAlaLeuIleGlyMetLeuValPhe-125
SEQ. ID. NO. 21620  146-IlePheGlyGlyValValGluAlaValAlaThr-156
SEQ. ID. NO. 21621  167-MetLeuGlyValTrpGlnGlnGlyAsp-175
SEQ. ID. NO. 21622  191-GlyIleLeuAlaLeuPheAla-197
SEQ. ID. NO. 21623  205-ThrIleLeuGlyLeuGlyGlu-211
SEQ. ID. NO. 21624  252-ValValProAsnIleIleSerArgLeuIleGlyAspArgLeuArgGlnSer-268
SEQ. ID. NO. 21625  285-IleIleGlyArgVal-289
SEQ. ID. NO. 21626  300-ThrValPheGlyValLeu-305
Antigenic Index - Jameson-Wolf
SEQ. ID. NO. 21627  38-SerLeuSerAspSerGln-43
SEQ. ID. NO. 21628  50-ArgLeuProArgThr-54
SEQ. ID. NO. 21629  77-AsnArgPheValGluProSerMetAlaGlyAlaGlyGln-89
SEQ. ID. NO. 21630  131-ArgLeuProProThrAla-136
SEQ. ID. NO. 21631  174-GlyAspPheSerGly-178
SEQ. ID. NO. 21632  260-LeuIleGlyAspArgLeuArgGlnSer-268
SEQ. ID. NO. 21633  316-ArgLysProAlaHis-320
Hydrophilic Regions - Hopp-Woods
SEQ. ID. NO. 21634  260-LeuIleGlyAspArgLeuArgGln-267
SEQ. ID. NO. 21635  316-ArgLysProAlaHis-320
a630
AMPHI Regions - AMPHI
SEQ. ID. NO. 21636  9-LeuPheProAlaMetPheTyrGlyMetTyrAsn-19
SEQ. ID. NO. 21637  30-ProAspLeuLeuGlnGlnSerIleAlaAsnAspTrpHisTyrAlaLeu-45
SEQ. ID. NO. 21638  81-GlyGlyPheTrpGluValLeuPheAla-89
SEQ. ID. NO. 21639  135-PheGlyGlyThrGlyLysAsnPhe-142
SEQ. ID. NO. 21640  169-AlaValAspGlyTyrSerGlyAlaThrAlaLeuAlaGlnTrp-182
SEQ. ID. NO. 21641  187-AlaAspGlyLeuLysAsnAlaIle-194
SEQ. ID. NO. 21642  203-AspAlaPheIleGlyLysLeuProGlySerIleGlyGluValSer-217
SEQ. ID. NO. 21643  230-PheAlaArgIleAlaSerTrpArgIleIleAlaGlyValMet-243
SEQ. ID. NO. 21644  247-IleAlaMetSerSerLeuPheAsnPhe-255
SEQ. ID. NO. 21645  289-ValSerAlaSerPheThrAsnValGlyLysTrpTrpTyrGlyAlaLeuIleGlyValMetCysValLeuIleArgVal-314
SEQ. ID. NO. 21646  327-IleLeuPheAlaAsnLeuPheAlaProIlePheAspTyrPhe-340
Antigenic Index - Jameson-Wolf
SEQ. ID. NO. 21647  91-ValArgLysHisGluIleAsnGlu-98
SEQ. ID. NO. 21648  133-GluValPheGlyGlyThrGlyLysAsnPheMet-143
SEQ. ID. NO. 21649  157-TyrProAlaAsnLeuSerGlyAspAla-165
SEQ. ID. NO. 21650  186-GlyAlaAspGlyLeuLys-191

TABLE 1-continued

SEQ. ID. NO. 21651    209-LeuProGlySerIleGly-214
SEQ. ID. NO. 21652    257-GlySerAspThrAsnAla-262
SEQ. ID. NO. 21653    345-AsnIleLysArgArgLysAlaArgSerAsnGly-355
Hydrophilic Regions - Hopp-Woods
SEQ. ID. NO. 21654    91-ValArgLysHisGluIleAsn-97
SEQ. ID. NO. 21655    345-AsnIleLysArgArgLysAlaArgSerAsnGly-355
a638
AMPHI Regions - AMPHI
SEQ. ID. NO. 21656    17-LeuAlaArgPheValAspAsnVal-24
SEQ. ID. NO. 21657    30-IleValAspIleValGluHis-36
SEQ. ID. NO. 21658    46-AspIleValLysHisPheGluProLeuGlyLys-56
SEQ. ID. NO. 21659    118-ArgAlaGlyArgValPro-123
SEQ. ID. NO. 21660    149-IleGlyArgThrMetGln-154
SEQ. ID. NO. 21661    198-GluArgTyrValArgValTyrGlyTyrGlyThrPro-210
SEQ. ID. NO. 21662    212-ProValSerPheAspGlyCysArgThrValGlyArgPro-224
SEQ. ID. NO. 21663    242-SerGlnPheGluArgIleAlaArgProGly-251
Antigenic Index - Jameson-Wolf
SEQ. ID. NO. 21664    13-GlyLysAsnAlaLeu-17
SEQ. ID. NO. 21665    43-AlaAspGlyAspIle-47
SEQ. ID. NO. 21666    52-GluProLeuGlyLysHisGln-58
SEQ. ID. NO. 21667    81-ValAspGlyGluThrGlnIle-87
SEQ. ID. NO. 21668    99-AlaGlyIleGlyLysAsnAlaVal-106
SEQ. ID. NO. 21669    113-ValAlaAspAspLeuArgAlaGlyArgValProAsnGlyAsn-126
SEQ. ID. NO. 21670    135-GlnSerArgValAlaAsp-140
SEQ. ID. NO. 21671    153-MetGlnIleAspAlaAspArgIleIle-161
SEQ. ID. NO. 21672    168-AsnGlnGlyAlaArgGlySerPhe-175
SEQ. ID. NO. 21673    178-IleAsnThrGlyIleHis-183
SEQ. ID. NO. 21674    188-HisThrGlyThrGlyAsnGlyGlnValAlaGluArgTyrValArg-202
SEQ. ID. NO. 21675    213-ValSerPheAspGlyCysArgThrValGlyArgProPheAsnArgAsnArgPheValAsp-232
SEQ. ID. NO. 21676    240-AlaGlySerGlnPheGluArgIleAlaArgProGlyAlaGlyLysCysGly-256
Hydrophilic Regions - Hopp-Woods
SEQ. ID. NO. 21677    43-AlaAspGlyAspIle-47
SEQ. ID. NO. 21678    52-GluProLeuGlyLys-56
SEQ. ID. NO. 21679    81-ValAspGlyGluThrGlnIle-87
SEQ. ID. NO. 21680    113-ValAlaAspAspLeuArgAlaGlyArgValProAsn-124
SEQ. ID. NO. 21681    136-SerArgValAlaAsp-140
SEQ. ID. NO. 21682    153-MetGlnIleAspAlaAspArgIleIle-161
SEQ. ID. NO. 21683    195-GlnValAlaGluArgTyrValArg-202
SEQ. ID. NO. 21684    216-AspGlyCysArgThrValGly-222
SEQ. ID. NO. 21685    243-GlnPheGluArgIleAlaArgProGlyAlaGly-253
a639-1
AMPHI Regions - AMPHI
SEQ. ID. NO. 21686    95-TyrLysAsnAsnArg-99
SEQ. ID. NO. 21687    137-LeuLysValPheAspAsnIle-143
SEQ. ID. NO. 21688    157-ValAsnTyrSerAspIleHisAspAsnIleIleAsnLysAla-170
SEQ. ID. NO. 21689    269-AlaProValSerArg-273
SEQ. ID. NO. 21690    290-GlnPheProAlaValLeuProGly-297
SEQ. ID. NO. 21691    322-AspGlyLeuLeuLysLysValGlu-329
Antigenic Index - Jameson-Wolf
SEQ. ID. NO. 21692    13-GluGluThrAlaPro-17
SEQ. ID. NO. 21693    23-HisAsnAsnIleLeuAspAsnSer-30
SEQ. ID. NO. 21694    41-AlaMetValArgGluAsnLysIleValGly-50
SEQ. ID. NO. 21695    52-AlaThrLeuArgValAsnGluArgGlyAsnGly-62
SEQ. ID. NO. 21696    75-GlyAsnAspIleSerLysGlyArgAspGlyIlePheSerAsnThrSerThrHisAsnThrTyrLysAsnAsnArgPheSerAsp-102
SEQ. ID. NO. 21697    111-TyrThrAsnAspSerGluIleSerGly-119
SEQ. ID. NO. 21698    121-IleSerValGlyAsnAsn-126
SEQ. ID. NO. 21699    135-GluArgLeuLysVal-139
SEQ. ID. NO. 21700    145-ValGlySerArgAspGlnGlyIle-152
SEQ. ID. NO. 21701    160-SerAspIleHisAspAsnIleIleAsnLysAlaGlyLys-172
SEQ. ID. NO. 21702    179-AlaAsnTyrAspLysLeuSerAlaAsnHis-188
SEQ. ID. NO. 21703    203-GluGlyThrSerLeuHisAspAsnSerPheIleAsnAsnGluSerGlnValLysTyrVal-222
SEQ. ID. NO. 21704    228-AspTrpSerGluGlyGlyHisGlyAsnTyrTrpSerAspAsnSerAla-243
SEQ. ID. NO. 21705    246-LeuAsnGlyAspGlyPheGlyAspSerAlaTyrArgProAsnGlyIleIle-262
SEQ. ID. NO. 21706    297-GlyGlyValValAspSerLysProLeuMetLysProTyrAlaProLysIleGlnThr-315
SEQ. ID. NO. 21707    318-GlnAlaMetLysAspGlyLeuLeuLysLysValGluThrArgGlnLeuGluTrpGlyArgAlaGluAsnGlySerLeuAsn-344
Hydrophilic Regions - Hopp-Woods
SEQ. ID. NO. 21708    41-AlaMetValArgGluAsnLysIleValGly-50
SEQ. ID. NO. 21709    52-AlaThrLeuArgValAsnGluArgGlyAsn-61
SEQ. ID. NO. 21710    77-AspIleSerLysGlyArgAspGlyIle-85
SEQ. ID. NO. 21711    95-TyrLysAsnAsnArgPheSerAsp-102
SEQ. ID. NO. 21712    113-AsnAspSerGluIleSerGly-119
SEQ. ID. NO. 21713    135-GluArgLeuLysVal-139
SEQ. ID. NO. 21714    146-GlySerArgAspGlnGly-151
SEQ. ID. NO. 21715    180-AsnTyrAspLysLeuSer-185
SEQ. ID. NO. 21716    299-ValValAspSerLysProLeuMet-306
SEQ. ID. NO. 21717    318-GlnAlaMetLysAspGlyLeuLeuLysLysValGluThrArgGlnLeuGluTrpGlyArgAlaGluAsnGlySer-342
a640
AMPHI Regions - AMPHI
SEQ. ID. NO. 21718    6-SerIleLeuLysSerIleGlyIle-13
SEQ. ID. NO. 21719    22-SerIleLysArgMetSer-27

TABLE 1-continued

| | |
|---|---|
| SEQ. ID. NO. 21720 | 47-LeuProAlaTyrAlaGluArgLeuProAspPheLeuAlaLysIleGlnPro-63 |
| SEQ. ID. NO. 21721 | 72-ArgTyrSerLysPro-76 |
| SEQ. ID. NO. 21722 | 109-SerLysProIleAspThrLeuMetAla-117 |
| SEQ. ID. NO. 21723 | 127-AlaLysLeuValAspHis-132 |
| Antigenic Index - Jameson-Wolf | |
| SEQ. ID. NO. 21724 | 24-LysArgMetSerAlaPheArgAlaArgIle-33 |
| SEQ. ID. NO. 21725 | 50-TyrAlaGluArgLeuProAspPheLeuAlaLysIleGlnProSerGluIleValProGlyAlaAspArgTyrSerLysProGluGlyLysProMetVal-82 |
| SEQ. ID. NO. 21726 | 85-ValTyrLysGlyAspGluGlnLeu-92 |
| SEQ. ID. NO. 21727 | 101-AlaValAsnThrArgGlyTyrSerSerLysProIleAsp-113 |
| SEQ. ID. NO. 21728 | 118-LeuAlaLysAspGlyThr-123 |
| SEQ. ID. NO. 21729 | 128-LysLeuValAspHisHisGlu-134 |
| Hydrophilic Regions - Hopp-Woods | |
| SEQ. ID. NO. 21730 | 24-LysArgMetSerAlaPheArgAlaArgIle-33 |
| SEQ. ID. NO. 21731 | 50-TyrAlaGluArgLeuPro-55 |
| SEQ. ID. NO. 21732 | 68-ProGlyAlaAspArgTyrSerLysProGluGlyLysProMetVal-82 |
| SEQ. ID. NO. 21733 | 85-ValTyrLysGlyAspGluGlnLeu-92 |
| SEQ. ID. NO. 21734 | 118-LeuAlaLysAspGlyThr-123 |
| SEQ. ID. NO. 21735 | 128-LysLeuValAspHisHisGlu-134 |
| a642 | |
| AMPHI Regions - AMPHI | |
| SEQ. ID. NO. 21736 | 6-CysProLeuSerAlaIleSerAlaVal-14 |
| SEQ. ID. NO. 21737 | 116-IleLysHisIleValArgAlaPhe-123 |
| SEQ. ID. NO. 21738 | 138-GlyValSerAlaPheLysThrLeuArgAlaGlnGluPheLeuGlnHisLeuArgGlyGlyVal-158 |
| SEQ. ID. NO. 21739 | 161-PheArgGlyGluGly-165 |
| SEQ. ID. NO. 21740 | 167-AspAspValArgLeu-171 |
| SEQ. ID. NO. 21741 | 186-AlaAspValAlaValLysAsnLeuGlyAsnLeuMetAlaAlaProAsp-201 |
| SEQ. ID. NO. 21742 | 220-ValPheLysGlyValPheHisAsnAlaValArgHisAlaAspGlnLeuGln-236 |
| SEQ. ID. NO. 21743 | 270-ValAspGlyValThrAspGlyAla-277 |
| SEQ. ID. NO. 21744 | 296-GlnValAspAspPheGlyGluPheAlaValPhe-306 |
| SEQ. ID. NO. 21745 | 325-PheArgGlyValAsp-329 |
| SEQ. ID. NO. 21746 | 378-AlaGluLeuLeuGlnTrpLeuGlnHisGlnArgAlaPheAspAlaGlyThr-394 |
| Antigenic Index - Jameson-Wolf | |
| SEQ. ID. NO. 21747 | 1-AlaCysArgArgIleCysPro-7 |
| SEQ. ID. NO. 21748 | 22-ValGlnGlnGluGlyCysGly-28 |
| SEQ. ID. NO. 21749 | 34-LeuTyrGluAspLysGluSerGlyAspAspPheAlaAspLysAspPheLeuGln-51 |
| SEQ. ID. NO. 21750 | 73-ValAlaGlyAspGlyGlyLysAlaGly-81 |
| SEQ. ID. NO. 21751 | 103-PheGlyGlyGlyAlaAspLysLeu-110 |
| SEQ. ID. NO. 21752 | 123-PheLysAsnArgGluGlyAlaAspValAspSerAspIleAla-136 |
| SEQ. ID. NO. 21753 | 143-LysThrLeuArgAla-147 |
| SEQ. ID. NO. 21754 | 161-PheArgGlyGluGlyPheAspAspValArgLeu-171 |
| SEQ. ID. NO. 21755 | 175-MetGlyAspGlyCysAsnGlyArgAsnGlyMet-185 |
| SEQ. ID. NO. 21756 | 208-AspGluSerAspValValAla-214 |
| SEQ. ID. NO. 21757 | 230-ArgHisAlaAspGlnLeuGlnAlaAlaAlaAspLysAspValLeuGluArgAlaGlnThrGly-250 |
| SEQ. ID. NO. 21758 | 259-HisGlyGlyCysArg-263 |
| SEQ. ID. NO. 21759 | 265-PheGlyIleAspAlaValAspGlyValThrAspGly-276 |
| SEQ. ID. NO. 21760 | 290-CysPheGlyAspGluGlnGlnValAspAspPheGly-301 |
| SEQ. ID. NO. 21761 | 309-PheGlyGlyAsnGluGluGluValAlaLeu-318 |
| SEQ. ID. NO. 21762 | 328-ValAspValAsnGly-332 |
| SEQ. ID. NO. 21763 | 344-PheSerGlyAsnArgArgAlaGlyGly-352 |
| SEQ. ID. NO. 21764 | 388-ArgAlaPheAspAlaGlyThrGlnArgAsnGly-398 |
| SEQ. ID. NO. 21765 | 401-ValMetProArgAsnPro-406 |
| Hydrophilic Regions - Hopp-Woods | |
| SEQ. ID. NO. 21766 | 1-AlaCysArgArgIleCys-6 |
| SEQ. ID. NO. 21767 | 34-LeuTyrGluAspLysGluSerGlyAspAspPheAlaAspLysAspPheLeu-50 |
| SEQ. ID. NO. 21768 | 76-AspGlyGlyLysAla-80 |
| SEQ. ID. NO. 21769 | 106-GlyAlaAspLysLeu-110 |
| SEQ. ID. NO. 21770 | 123-PheLysAsnArgGluGlyAlaAspValAspSerAspIle-135 |
| SEQ. ID. NO. 21771 | 143-LysThrLeuArgAla-147 |
| SEQ. ID. NO. 21772 | 164-GluGlyPheAspAspValArgLeu-171 |
| SEQ. ID. NO. 21773 | 178-GlyCysAsnGlyArgAsnGlyMet-185 |
| SEQ. ID. NO. 21774 | 208-AspGluSerAspValValAla-214 |
| SEQ. ID. NO. 21775 | 230-ArgHisAlaAspGlnLeuGlnAlaAlaAlaAspLysAspValLeuGluArgAlaGlnThr-249 |
| SEQ. ID. NO. 21776 | 269-AlaValAspGlyValThrAspGly-276 |
| SEQ. ID. NO. 21777 | 290-CysPheGlyAspGluGlnGlnValAspAspPheGly-301 |
| SEQ. ID. NO. 21778 | 311-GlyAsnGluGluGluValAlaLeu-318 |
| SEQ. ID. NO. 21779 | 346-GlyAsnArgArgAlaGly-351 |
| SEQ. ID. NO. 21780 | 393-GlyThrGlnArgAsnGly-398 |
| a644 | |
| AMPHI Regions - AMPHI | |
| SEQ. ID. NO. 21781 | 25-CysGlyArgArgPheAspArgPro-32 |
| SEQ. ID. NO. 21782 | 55-MetAspThrAlaAlaPheLeuLysHisIleGluSerAlaPheArgArgIlePheAlaAspGlyIleAspLeuMetArgTyrLeu-82 |
| SEQ. ID. NO. 21783 | 111-GlnPheGluIleGlnGluValLeuArgIleAlaGly-122 |
| SEQ. ID. NO. 21784 | 141-GlnProLeuGlnGluPheGlyAsp-148 |
| SEQ. ID. NO. 21785 | 181-ArgGluMetGlnSerTyrTyrGluTyrThrAsp-191 |
| SEQ. ID. NO. 21786 | 202-TyrTrpGlnGlyAsn-206 |
| SEQ. ID. NO. 21787 | 224-LeuAlaLysValIleAspLeuLeu-231 |
| SEQ. ID. NO. 21788 | 276-AlaGlyLeuArgAlaPheGlnAsn-283 |
| SEQ. ID. NO. 21789 | 304-LeuGluAsnLeuGluArgTyrValArgAsn-313 |
| SEQ. ID. NO. 21790 | 333-GluIleLeuTyrArgTyrValCysHis-341 |
| SEQ. ID. NO. 21791 | 343-ValSerProValAlaProValAlaHis-351 |

TABLE 1-continued

| | |
|---|---|
| SEQ. ID. NO. 21792 | 356-AlaAsnIleValLysThrLeuAla-363 |
| SEQ. ID. NO. 21793 | 372-GlnMetLeuGlnLys-376 |
| SEQ. ID. NO. 21794 | 399-PheThrIlePheGluGlyProAsn-406 |
| SEQ. ID. NO. 21795 | 408-MetLeuTyrAlaGluIleTyrAspGlnPheValArgAla-420 |
| SEQ. ID. NO. 21796 | 439-AspArgLeuGlnThr-443 |
| SEQ. ID. NO. 21797 | 456-LeuProGluAspIleArgSerPhe-463 |
| SEQ. ID. NO. 21798 | 481-GlyLysIleIleAlaArgLeu-487 |

Antigenic Index - Jameson-Wolf

| | |
|---|---|
| SEQ. ID. NO. 21799 | 1-MetProSerGluArgSerAlaAspCysCysPro-11 |
| SEQ. ID. NO. 21800 | 16-ValLysPheArgLysSerThrLeuAsnCysGlyArgArgPheAspArgProProIleAsnGlyAsnArgGlnArgLysProMetIleHisThrGluProSerAlaGlnProSerThrMetAsp-56 |
| SEQ. ID. NO. 21801 | 64-IleGluSerAlaPhe-68 |
| SEQ. ID. NO. 21802 | 71-IlePheAlaAspGlyIleAsp-77 |
| SEQ. ID. NO. 21803 | 82-LeuProGluAspLysTrpLeu-88 |
| SEQ. ID. NO. 21804 | 99-PheLeuAspLysLysTyrGlyGlyArgLysGlySerGlnPheGluIle-114 |
| SEQ. ID. NO. 21805 | 132-XxxXxxXxxGluGly-136 |
| SEQ. ID. NO. 21806 | 145-GluPheGlyAspGluAlaGlnIle-152 |
| SEQ. ID. NO. 21807 | 159-ValPheLysGlyGluGlyGlyGlyLeu-167 |
| SEQ. ID. NO. 21808 | 170-ThrGluProGluThrSerGly-176 |
| SEQ. ID. NO. 21809 | 178-AlaIleAlaArgGluMetGlnSerTyrTyrGluTyrThrAspGlyGlnThr-194 |
| SEQ. ID. NO. 21810 | 202-TyrTrpGlnGlyAsnSerGlnSerAspPhe-211 |
| SEQ. ID. NO. 21811 | 216-AlaLysGluArgLysAsnGlyLysLeuAlaLys-226 |
| SEQ. ID. NO. 21812 | 235-LysThrTyrIleArg-239 |
| SEQ. ID. NO. 21813 | 241-GluThrLeuAlaSerGluGlyLeuArg-249 |
| SEQ. ID. NO. 21814 | 254-AlaValAsnArgIleAspAlaGluMet-262 |
| SEQ. ID. NO. 21815 | 270-LeuSerGlnSerAspAlaAlaGly-277 |
| SEQ. ID. NO. 21816 | 306-AsnLeuGluArgTyrValArgAsnAspIleArgPheValAspTyrGluArgArgGluIleArgArgArgHisGlnVal-331 |
| SEQ. ID. NO. 21817 | 381-LysGlyPheGluArgGlyHisThrAlaGlyAsn-391 |
| SEQ. ID. NO. 21818 | 403-GluGlyProAsnAspMetLeu-409 |
| SEQ. ID. NO. 21819 | 420-AlaThrAlaGluGluLysGluAlaGlyMetLysLeuAspLysAsnGlnThrLeuLeuAspArgLeuGlnThrAspAlaArgPhe-447 |
| SEQ. ID. NO. 21820 | 449-AlaValAlaArgAspTyrThrLeuProGluAspIleArgSerPheLeu-464 |
| SEQ. ID. NO. 21821 | 493-AlaGluHisGluAspThrAla-499 |
| SEQ. ID. NO. 21822 | 505-AspIleArgLysAspIleLeuAspCysArgTyrCysGly-517 |

Hydrophilic Regions - Hopp-Woods

| | |
|---|---|
| SEQ. ID. NO. 21823 | 1-MetProSerGluArgSerAlaAspCys-9 |
| SEQ. ID. NO. 21824 | 17-LysPheArgLysSerThrLeuAsnCysGlyArgArgPheAspArgProProIleAsnGlyAsnArgGlnArgLysProMetIle-44 |
| SEQ. ID. NO. 21825 | 64-IleGluSerAlaPhe-68 |
| SEQ. ID. NO. 21826 | 82-LeuProGluAspLysTrpLeu-88 |
| SEQ. ID. NO. 21827 | 100-LeuAspLysLysTyrGlyGlyArgLysGlySerGln-111 |
| SEQ. ID. NO. 21828 | 145-GluPheGlyAspGluAlaGlnIle-152 |
| SEQ. ID. NO. 21829 | 160-PheLysGlyGluGlyGlyGly-165 |
| SEQ. ID. NO. 21830 | 170-ThrGluProGluThrSerGly-176 |
| SEQ. ID. NO. 21831 | 178-AlaIleAlaArgGluMetGlnSer-185 |
| SEQ. ID. NO. 21832 | 216-AlaLysGluArgLysAsnGlyLysLeuAlaLys-226 |
| SEQ. ID. NO. 21833 | 254-AlaValAsnArgIleAspAlaGluMet-262 |
| SEQ. ID. NO. 21834 | 271-SerGlnSerAspAlaAlaGly-277 |
| SEQ. ID. NO. 21835 | 306-AsnLeuGluArgTyrValArgAsnAspIleArgPheValAspTyrGluArgArgGluIleArgArgArgHisGlnVal-331 |
| SEQ. ID. NO. 21836 | 381-LysGlyPheGluArgGlyHisThr-388 |
| SEQ. ID. NO. 21837 | 420-AlaThrAlaGluGluLysGluAlaGlyMetLysLeuAspLysAsnGlnThrLeuLeuAspArgLeuGlnThrAspAlaArgPhe-447 |
| SEQ. ID. NO. 21838 | 458-GluAspIleArgSerPheLeu-464 |
| SEQ. ID. NO. 21839 | 493-AlaGluHisGluAspThrAla-499 |
| SEQ. ID. NO. 21840 | 505-AspIleArgLysAspIleLeuAsp-512 | a645

AMPHI Regions - AMPHI

| | |
|---|---|
| SEQ. ID. NO. 21841 | 21-AsnThrLeuAsnArgCysCysLys-28 |
| SEQ. ID. NO. 21842 | 87-ArgThrLeuProSerLeuAsnGlyLeuThrLys-97 |
| SEQ. ID. NO. 21843 | 149-ThrProLysArgCysSerSerSerIle-157 |
| SEQ. ID. NO. 21844 | 163-PheLeuAsnPheMetSerSerCysThrSerLeu-173 |
| SEQ. ID. NO. 21845 | 210-SerAlaLysArgSer-214 |
| SEQ. ID. NO. 21846 | 249-SerValLeuProLysPro-254 |

Antigenic Index - Jameson-Wolf

| | |
|---|---|
| SEQ. ID. NO. 21847 | 18-GluGlnSerAsnThrLeuAsnArgCysCysLysLysSerArgMetThrCysSerSerSerArgSerArgSerCysProCys-44 |
| SEQ. ID. NO. 21848 | 47-ProMetArgAlaSerGlySerArgValSerSerArgSerArgMet-61 |
| SEQ. ID. NO. 21849 | 68-SerLeuCysArgLysAsnThrCysProProArgLeuSerSerArgAsnThrAlaSerArgThrLeuProSer-91 |
| SEQ. ID. NO. 21850 | 99-LeuThrAlaArgArgArgLeuGly-106 |
| SEQ. ID. NO. 21851 | 110-IleSerGluLysSerArgSerProSerSer-119 |
| SEQ. ID. NO. 21852 | 137-ThrLeuAlaArgArgArgLeuSerCysSerPheArgThrProLysArgCysSerSer-155 |
| SEQ. ID. NO. 21853 | 184-SerAlaMetProSer-188 |
| SEQ. ID. NO. 21854 | 198-LeuLysArgGluArgLeuAla-204 |
| SEQ. ID. NO. 21855 | 207-ThrGlyLysSerAlaLysArgSerAlaLys-216 |
| SEQ. ID. NO. 21856 | 221-CysSerThrArgSerValValGlyAla-229 |
| SEQ. ID. NO. 21857 | 242-AsnAlaAlaArgArgAlaThr-248 |
| SEQ. ID. NO. 21858 | 250-ValLeuProLysProThrSerProHisThrArgArgSerIle-263 |

Hydrophilic Regions - Hopp-Woods

| | |
|---|---|
| SEQ. ID. NO. 21859 | 19-GlnSerAsnThrLeu-23 |
| SEQ. ID. NO. 21860 | 25-ArgCysCysLysLysSerArgMetThrCysSerSerSerArgSerArgSerCysPro-43 |
| SEQ. ID. NO. 21861 | 48-MetArgAlaSerGlySerArgValSerSerArgSerArgMet-61 |
| SEQ. ID. NO. 21862 | 69-LeuCysArgLysAsnThrCysProProArgLeuSerSerArgAsnThrAlaSerArgThr-88 |
| SEQ. ID. NO. 21863 | 99-LeuThrAlaArgArgArgLeuGly-106 |
| SEQ. ID. NO. 21864 | 110-IleSerGluLysSerArgSerProSer-118 |

TABLE 1-continued

| SEQ. ID. NO. | Sequence |
|---|---|
| SEQ. ID. NO. 21865 | 137-ThrLeuAlaArgArgArgLeuSerCys-145 |
| SEQ. ID. NO. 21866 | 148-ArgThrProLysArgCysSer-154 |
| SEQ. ID. NO. 21867 | 198-LeuLysArgGluArgLeuAla-204 |
| SEQ. ID. NO. 21868 | 209-LysSerAlaLysArgSerAlaLys-216 |
| SEQ. ID. NO. 21869 | 242-AsnAlaAlaArgArgAlaThr-248 |
| SEQ. ID. NO. 21870 | 254-ProThrSerProHisThrArgArgSerIle-263 | a647
AMPHI Regions - AMPHI
SEQ. ID. NO. 21871    38-GlyLysValCysArgCysPheGluGlnVal-47
SEQ. ID. NO. 21872    69-ThrValPheArgGlnIleIleArgIleValAspHisAla-81
Antigenic Index - Jameson-Wolf
SEQ. ID. NO. 21873    26-GlyLeuValLysGluArgAlaArg-33
SEQ. ID. NO. 21874    39-LysValCysArgCysPhe-44
SEQ. ID. NO. 21875    54-GlyThrValGlyGlnThrGluArgGlyAla-63
SEQ. ID. NO. 21876    79-AspHisAlaAspThrGluArgThrAlaAlaHisSerGlyGlyThrArgGly-95
Hydrophilic Regions - Hopp-Woods
SEQ. ID. NO. 21877    26-GlyLeuValLysGluArgAlaArg-33
SEQ. ID. NO. 21878    40-ValCysArgCysPhe-44
SEQ. ID. NO. 21879    56-ValGlyGlnThrGluArgGlyAla-63
SEQ. ID. NO. 21880    79-AspHisAlaAspThrGluArgThrAlaAla-88
a648
AMPHI Regions - AMPHI
SEQ. ID. NO. 21881    7-ArgIleGluArgAlaValArg-13
SEQ. ID. NO. 21882    15-AlaValIleAspValLeuAsnValAsp-23
SEQ. ID. NO. 21883    44-AlaLeuAlaAspIleArgValLeu-51
SEQ. ID. NO. 21884    94-AlaValAspLeuHisAlaValIleLysLeuThrAspThrVal-107
SEQ. ID. NO. 21885    127-GlnGlyValGluGlnGly-132
SEQ. ID. NO. 21886    152-PheLysGluGlyAsn-156
SEQ. ID. NO. 21887    182-AlaArgThrLeuGlyAsnValPheHis-190
SEQ. ID. NO. 21888    194-GlySerGlyValAspGlyIleGlnAlaValValAlaPheAspGlnTyrAla-210
Antigenic Index - Jameson-Wolf
SEQ. ID. NO. 21889    1-MetAsnArgArgAsnAlaArgIleGluArgAlaValArg-13
SEQ. ID. NO. 21890    23-AspAlaProGlySerGlyThrLeuLeuHisGlnArgGlyLysGlnValGlySerArgAsnAspAlaLeuAla-46
SEQ. ID. NO. 21891    65-GlyLysLysArgPheValGlnSerArgAsnLeuValGlyArgLysGlnArgAsn-82
SEQ. ID. NO. 21892    125-MetProGlnGlyValGluGlnGlyCysArg-134
SEQ. ID. NO. 21893    142-ArgThrGlyPheAspCysArgLeuLysHisPheLysGluGlyAsnAla-157
SEQ. ID. NO. 21894    172-SerAlaAspThrSerGlyIleAspAlaAspAlaArgThr-184
SEQ. ID. NO. 21895    191-AsnArgAlaGlySerGlyValAspGly-199
Hydrophilic Regions - Hopp-Woods
SEQ. ID. NO. 21896    1-MetAsnArgArgAsnAlaArgIleGluArgAlaValArg-13
SEQ. ID. NO. 21897    33-GlnArgGlyLysGlnValGlySerArgAsnAspAlaLeuAla-46
SEQ. ID. NO. 21898    65-GlyLysLysArgPheValGln-71
SEQ. ID. NO. 21899    74-AsnLeuValGlyArgLysGlnArgAsn-82
SEQ. ID. NO. 21900    127-GlnGlyValGluGlnGlyCysArg-134
SEQ. ID. NO. 21901    143-ThrGlyPheAspCysArgLeuLysHisPheLysGluGlyAsnAla-157
SEQ. ID. NO. 21902    172-SerAlaAspThrSerGlyIleAspAlaAspAlaArgThr-184
a649
AMPHI Regions - AMPHI
SEQ. ID. NO. 21903    6-LeuSerAlaIleLeuGlyLeuVal-13
SEQ. ID. NO. 21904    27-ArgAspThrLysHisIleArgLysAlaAsn-36
SEQ. ID. NO. 21905    57-SerGlnGlyAsnVal-61
SEQ. ID. NO. 21906    63-GluLeuArgGluAsnLys-68
SEQ. ID. NO. 21907    71-ArgLysAlaPheArgSerLeu-77
Antigenic Index - Jameson-Wolf
SEQ. ID. NO. 21908    20-GlyThrSerGluProAlaHisArgAspThrLysHisIleArgLysAlaAsnLys-37
SEQ. ID. NO. 21909    40-LeuHisProGluCysArgLysTyrLeuGluArgArgAlaAla-53
SEQ. ID. NO. 21910    56-ArgSerGlnGlyAsnValGlnGluLeuArgGluAsnLysLysAlaArgLysAlaPheArgSerLeuProTyrLysGluGlnLysThrGlnCys-86
SEQ. ID. NO. 21911    92-AlaPheAspAspPheAspGlySerArgPheArgArg-103
Hydrophilic Regions - Hopp-Woods
SEQ. ID. NO. 21912    20-GlyThrSerGluProAlaHisArgAspThrLysHisIleArgLysAlaAsnLys-37
SEQ. ID. NO. 21913    42-ProGluCysArgLysTyrLeuGluArgArgAlaAla-53
SEQ. ID. NO. 21914    59-GlyAsnValGlnGluLeuArgGluAsnLysLysAlaArgLysAlaPheArg-75
SEQ. ID. NO. 21915    78-ProTyrLysGluGlnLysThrGlnCys-86
SEQ. ID. NO. 21916    92-AlaPheAspAspPheAspGlySerArgPheArgArg-103
a650
AMPHI Regions - AMPHI
SEQ. ID. NO. 21917    15-SerValCysProGly-19
SEQ. ID. NO. 21918    57-LeuTrpSerGluLeuArgGln-63
SEQ. ID. NO. 21919    72-ProGluLeuValArgArgHisGlu-79
SEQ. ID. NO. 21920    89-PheAsnArgValIleAsn-94
SEQ. ID. NO. 21921    137-SerGlyLeuTrpGln-141
SEQ. ID. NO. 21922    173-AsnTyrLeuGlnTyrLeuTyrGlyLeuPheGlyAspTrpPro-186
SEQ. ID. NO. 21923    198-AsnValGlyArgAlaIleAsnArgAlaArg-207
SEQ. ID. NO. 21924    218-LeuArgMetProAsnGluThr-224
SEQ. ID. NO. 21925    269-GluAlaIleAlaArgLeuAlaGlyIleThrGlnSer-280
SEQ. ID. NO. 21926    314-SerAsnTyrLeuAsnAlaAlaProAsp-322
SEQ. ID. NO. 21927    341-IleSerThrAlaThrGlyMet-347
SEQ. ID. NO. 21928    349-IleAlaAspIleLysArgLeuAsnAsnLeu-358
SEQ. ID. NO. 21929    376-LysThrLeuGlnThrAlaSerGlu-383
SEQ. ID. NO. 21930    433-ValArgThrXxxThr-437

TABLE 1-continued

Antigenic Index - Jameson-Wolf
SEQ. ID. NO. 21931    1-MetSerLysLeuLys-5
SEQ. ID. NO. 21932    24-GlnAsnThrSerSerHis-29
SEQ. ID. NO. 21933    38-LeuAsnSerSerIleLeuAspLeuProProThrLysGlnTyrPhe-52
SEQ. ID. NO. 21934    59-SerGluLeuArgGlnGlyPheArgMetGlyGluValAsnProGluLeuValArgArgHisGluSerLysPheIle-83
SEQ. ID. NO. 21935    92-ValIleAsnArgSerArgProTyr-99
SEQ. ID. NO. 21936    105-AsnGluValLysLysArgAsnMetProAla-114
SEQ. ID. NO. 21937    128-ThrLysAlaLysSerHisValGlyAlaSerGly-138
SEQ. ID. NO. 21938    145-AlaThrGlyArgHisTyrGlyLeuGluLysThrProValTyrAspGlyArgHisAspIle-164
SEQ. ID. NO. 21939    192-TyrAsnTrpGlyGluGlyAsnValGlyArgAlaIleAsnArgAlaArgAlaGlnGlyLeuGluProThrTyrGluAsnLeuArgMetProAsnGluThr
                      ArgAsnTyrVal-228
SEQ. ID. NO. 21940    247-AsnIleSerAspIleAspAsnLysProTyr-256
SEQ. ID. NO. 21941    259-AlaValGluProAspArgProLeuAspAsnGluAlaIleAla-272
SEQ. ID. NO. 21942    294-PheIleProLysSerLysArgLysLeu-302
SEQ. ID. NO. 21943    318-AsnAlaAlaProAspSer-323
SEQ. ID. NO. 21944    332-ProAlaAlaLysThrSerLeuSerAspIleSerThr-343
SEQ. ID. NO. 21945    350-AlaAspIleLysArgLeuAsnAsnLeuAsnGly-360
SEQ. ID. NO. 21946    370-LeuValAlaLysAsnGlyLysThrLeuGlnThrAlaSer-382
SEQ. ID. NO. 21947    388-IleAspIleAspAsnThrProAsnThrTyrArgSerAsnMetProAlaGlyThr-405
SEQ. ID. NO. 21948    411-AlaArgIleArgProAlaAla-417
SEQ. ID. NO. 21949    428-LeuProGlnLysThrValArgThrXxxThrArgSerProCysProTyrCys-444
SEQ. ID. NO. 21950    446-ThrCysProCysAspSerArgSerAlaThrSerAsnArgLysThrAspArgHisAlaVal-465
Hydrophilic Regions - Hopp-Woods
SEQ. ID. NO. 21951    1-MetSerLysLeuLys-5
SEQ. ID. NO. 21952    61-LeuArgGlnGlyPheArgMetGlyGluValAsnProGluLeuValArgArgHisGluSerLysPhe-82
SEQ. ID. NO. 21953    92-ValIleAsnArgSerArgPro-98
SEQ. ID. NO. 21954    105-AsnGluValLysLysArgAsnMetProAla-114
SEQ. ID. NO. 21955    128-ThrLysAlaLysSerHisVal-134
SEQ. ID. NO. 21956    150-TyrGlyLeuGluLysThrProValTyrAspGlyArgHisAspIle-164
SEQ. ID. NO. 21957    202-AlaIleAsnArgAlaArgAlaGlnGlyLeu-211
SEQ. ID. NO. 21958    213-ProThrTyrGluAsnLeuArgMetProAsnGluThrArgAsnTyrVal-228
SEQ. ID. NO. 21959    249-SerAspIleAspAsn-253
SEQ. ID. NO. 21960    260-ValGluProAspArgProLeuAspAsnGluAlaIleAla-272
SEQ. ID. NO. 21961    296-ProLysSerLysArgLysLeu-302
SEQ. ID. NO. 21962    334-AlaLysThrSerLeu-338
SEQ. ID. NO. 21963    350-AlaAspIleLysArgLeuAsn-356
SEQ. ID. NO. 21964    373-LysAsnGlyLysThrLeuGlnThrAlaSer-382
SEQ. ID. NO. 21965    389-AspIleAspAsnThrProAsnThrTyr-397
SEQ. ID. NO. 21966    411-AlaArgIleArgPro-415
SEQ. ID. NO. 21967    431-LysThrValArgThrXxxThrArgSer-439
SEQ. ID. NO. 21968    447-CysProCysAspSerArgSerAlaThrSerAsnArgLysThrAspArgHisAlaVal-465
a652-1
AMPHI Regions - AMPHI
SEQ. ID. NO. 21969    6-AspIlePheAlaArg-10
SEQ. ID. NO. 21970    52-ArgAspGlyAspLys-56
SEQ. ID. NO. 21971    62-LysGlyValLeuLysAlaValGluHisValAsnAsnGlnIleAlaGlnAla-78
SEQ. ID. NO. 21972    130-LeuTyrArgTyrLeuGlyGlyAlaGlyPro-39
SEQ. ID. NO. 21973    149-ValIleAsnGlyGly-153
SEQ. ID. NO. 21974    173-LysSerPheArgGluAlaLeuArgCys-181
SEQ. ID. NO. 21975    184-GluIlePheHisAlaLeuLysLys-191
SEQ. ID. NO. 21976    266-AlaGluPheAlaGluTyrLeuGluGlyLeuValAsn-277
SEQ. ID. NO. 21977    323-AlaGluGlyIleGluLysGlyVal-330
SEQ. ID. NO. 21978    338-ValAsnGlnIleGlyThrLeuSerGluThrLeuLysAlaValAspLeuAlaLys-355
SEQ. ID. NO. 21979    377-AspLeuAlaValAla-381
SEQ. ID. NO. 21980    391-SerLeuSerArgSerAspArgMetAlaLysTyrAsnGlnLeuLeuArgIleGluGluLeuAlaGluAlaAlaAspTyr-417
Antigenic Index - Jameson-Wolf
SEQ. ID. NO. 21981    11-GluIleLeuAspSerArgGlyAsnProThrValGlu-22
SEQ. ID. NO. 21982    36-AlaValProSerGlyAlaSerThrGlyGlnLysGluAlaLeuGluLeuArgAspGlyAspLysSerArgTyrSerGlyLysGlyValLeuLysAlaVal
                      GluHisValAsn-72
SEQ. ID. NO. 21983    83-AspAlaAsnGluGlnSerTyr-89
SEQ. ID. NO. 21984    97-LeuAspGlyThrGluAsnLysGlyAsnLeuGly-107
SEQ. ID. NO. 21985    121-AlaAlaAlaGluAspSerGlyLeuPro-129
SEQ. ID. NO. 21986    135-GlyGlyAlaGlyProMet-140
SEQ. ID. NO. 21987    151-AsnGlyGlyGluHisAlaAsnAsnSerAsn-161
SEQ. ID. NO. 21988    173-LysSerPheArgGluAlaLeuArgCysGlyAla-183
SEQ. ID. NO. 21989    190-LysLysLeuCysAspSerLysGlyPheProThrThrValGlyAspGluGlyGlyPhe-208
SEQ. ID. NO. 21990    211-AsnLeuAsnSerHisLysGluAlaLeu-219
SEQ. ID. NO. 21991    243-CysAlaSerSerGluPheTyrLysAspGlyLysTyrHisLeuGluAlaGluGlyArgSerTyrThrAsn-265
SEQ. ID. NO. 21992    283-SerIleGluAspGlyMetAspGluAsnAspTrpGluGly-295
SEQ. ID. NO. 21993    299-LeuThrGluLysLeuGlyGlyLys-306
SEQ. ID. NO. 21994    309-LeuValGlyAspAspLeu-314
SEQ. ID. NO. 21995    318-AsnProLysIleLeuAlaGluGlyIleGluLysGlyVal-330
SEQ. ID. NO. 21996    352-AspLeuAlaLysArgAsnArgTyrAla-360
SEQ. ID. NO. 21997    363-MetSerHisArgSerGlyGluThrGluAspSerThrIle-375
SEQ. ID. NO. 21998    388-LysThrGlySerLeuSerArgSerAspArgMetAlaLys-400
SEQ. ID. NO. 21999    405-LeuArgIleGluGluGluLeuAlaGluAlaAlaAspTyrProSerLys-420
Hydrophilic Regions - Hopp-Woods
SEQ. ID. NO. 22000    11-GluIleLeuAspSerArgGlyAsnProThrValGlu-22
SEQ. ID. NO. 22001    43-ThrGlyGlnLysGluAlaLeuGluLeuArgAspGlyAspLysSerArgTyrSerGly-61
SEQ. ID. NO. 22002    63-GlyValLeuLysAlaValGlu-69

TABLE 1-continued

| | |
|---|---|
| SEQ. ID. NO. 22003 | 97-LeuAspGlyThrGluAsnLysGlyAsnLeu-106 |
| SEQ. ID. NO. 22004 | 121-AlaAlaAlaGluAspSerGly-127 |
| SEQ. ID. NO. 22005 | 153-GlyGluHisAlaAsn-157 |
| SEQ. ID. NO. 22006 | 173-LysSerPheArgGluAlaLeuArgCysGlyAla-183 |
| SEQ. ID. NO. 22007 | 190-LysLysLeuCysAspSerLysGly-197 |
| SEQ. ID. NO. 22008 | 202-ValGlyAspGluGlyGlyPhe-208 |
| SEQ. ID. NO. 22009 | 213-AsnSerHisLysGluAlaLeu-219 |
| SEQ. ID. NO. 22010 | 247-GluPheTyrLysAspGlyLysTyrHisLeuGluAlaGluGlyArgSerTyrThr-264 |
| SEQ. ID. NO. 22011 | 283-SerIleGluAspGlyMetAspGluAsnAspTrpGluGly-295 |
| SEQ. ID. NO. 22012 | 299-LeuThrGluLysLeuGlyGly-305 |
| SEQ. ID. NO. 22013 | 321-IleLeuAlaGluGlyIleGluLysGlyVal-330 |
| SEQ. ID. NO. 22014 | 352-AspLeuAlaLysArgAsnArgTyr-359 |
| SEQ. ID. NO. 22015 | 364-SerHisArgSerGlyGluThrGluAspSerThrIle-375 |
| SEQ. ID. NO. 22016 | 391-SerLeuSerArgSerAspArgMetAlaLys-400 |
| SEQ. ID. NO. 22017 | 405-LeuArgIleGluGluGluLeuAlaGluAlaAlaAspTyrProSer-419 | a653
AMPHI Regions - AMPHI

| | |
|---|---|
| SEQ. ID. NO. 22018 | 6-MetArgMetProGluValThrLysGlyPheSerGlySer-18 |
| SEQ. ID. NO. 22019 | 60-ThrMetArgLysProArgLeuThr-67 |
| SEQ. ID. NO. 22020 | 75-AlaLeuIlePheThrCysPheAla-82 |
| SEQ. ID. NO. 22021 | 96-ThrAlaLeuAlaAlaIleThrCysIle-104 |
| SEQ. ID. NO. 22022 | 111-LeuGlyLysMetGluGluPheAsn-118 |

Antigenic Index - Jameson-Wolf

| | |
|---|---|
| SEQ. ID. NO. 22023 | 4-GluProMetArgMetProGluValThrLysGlyPheSerGlySer-18 |
| SEQ. ID. NO. 22024 | 45-GlyCysArgSerThrArgLysThr-52 |
| SEQ. ID. NO. 22025 | 56-ValArgProGluThrMetArgLysProArgLeuThrAsnSerSerAla-71 |
| SEQ. ID. NO. 22026 | 86-AsnSerGlyCysAsnAla-91 |
| SEQ. ID. NO. 22027 | 103-CysIleSerGlyProProCysArgLeuGlyLysMetGluGlu-116 |
| SEQ. ID. NO. 22028 | 125-SerArgHisLysIleThrProProArgGlyProArgArgVal-138 |
| SEQ. ID. NO. 22029 | 145-ThrLysSerGlnAsnGlyThrGly-152 |
| SEQ. ID. NO. 22030 | 154-GlyTyrSerProProAlaThrArgProAla-163 |

Hydrophilic Regions - Hopp-Woods

| | |
|---|---|
| SEQ. ID. NO. 22031 | 4-GluProMetArgMetProGluValThrLys-13 |
| SEQ. ID. NO. 22032 | 47-ArgSerThrArgLysThr-52 |
| SEQ. ID. NO. 22033 | 57-ArgProGluThrMetArgLysProArgLeuThrAsn-68 |
| SEQ. ID. NO. 22034 | 107-ProProCysArgLeuGlyLysMetGluGlu-116 |
| SEQ. ID. NO. 22035 | 126-ArgHisLysIleThrProProArgGlyProArg-136 |
| SEQ. ID. NO. 22036 | 158-ProAlaThrArgProAla-163 | a656
AMPHI Regions - AMPHI

| | |
|---|---|
| SEQ. ID. NO. 22037 | 14-MetAlaArgThrLeuGlyAlaProGlu-22 |
| SEQ. ID. NO. 22038 | 42-ArgArgProSerThr-46 |
| SEQ. ID. NO. 22039 | 92-LeuAlaSerLeuAsnLysSerCys-99 |

Antigenic Index - Jameson-Wolf

| | |
|---|---|
| SEQ. ID. NO. 22040 | 6-GlySerThrSerSer-10 |
| SEQ. ID. NO. 22041 | 19-GlyAlaProGluSerValProAlaGlyLysValAlaAla-31 |
| SEQ. ID. NO. 22042 | 40-SerPheArgArgProSerThrLeuGlu-48 |
| SEQ. ID. NO. 22043 | 74-ArgProThrSerLeuArgProLysSerIleAsn-84 |
| SEQ. ID. NO. 22044 | 94-SerLeuAsnLysSerCysSerLeuAlaArgSerSerAlaGlyValLeuProArgArgArgValProAla-116 |
| SEQ. ID. NO. 22045 | 120-ThrMetThrSerSerArgSerArgArgThrArgIleSerGlyGluGluProThrMetTrpLysSerProLysSer-144 |

Hydrophilic Regions - Hopp-Woods

| | |
|---|---|
| SEQ. ID. NO. 22046 | 40-SerPheArgArgProSerThr-46 |
| SEQ. ID. NO. 22047 | 76-ThrSerLeuArgProLysSer-82 |
| SEQ. ID. NO. 22048 | 99-CysSerLeuAlaArgSerSer-105 |
| SEQ. ID. NO. 22049 | 109-LeuProArgArgArgValProAla-116 |
| SEQ. ID. NO. 22050 | 121-MetThrSerSerArgSerArgArgThrArgIleSerGlyGluGluProThrMet-138 |
| SEQ. ID. NO. 22051 | 140-LysSerProLysSer-144 | a657
AMPHI Regions - AMPHI

| | |
|---|---|
| SEQ. ID. NO. 22052 | 9-ProAlaMetLeuGly-13 |
| SEQ. ID. NO. 22053 | 20-LeuGlyArgMetPheThr-25 |
| SEQ. ID. NO. 22054 | 62-ThrAlaLeuGluGluLeuAlaLysCysAlaAla-72 |
| SEQ. ID. NO. 22055 | 85-MetArgPheLeuAlaLys-90 |
| SEQ. ID. NO. 22056 | 140-PheLeuProGlyIleLeuLysThr-147 |
| SEQ. ID. NO. 22057 | 161-LysThrValAspGluLeuLysAla-168 |
| SEQ. ID. NO. 22058 | 178-CysValLeuGluLysMetValAsp-185 |
| SEQ. ID. NO. 22059 | 203-GlnThrPheAspProAlaGluAsnIle-211 |
| SEQ. ID. NO. 22060 | 232-GlnGlnAlaArgGlnMetAlaGlnArgLeuAlaAspGluLeuAsnTyrValGlyValLeu-251 |
| SEQ. ID. NO. 22061 | 279-HisThrValAspAlaCysAlaAla-286 |
| SEQ. ID. NO. 22062 | 314-AsnIleLeuGlyAsp-318 |

Antigenic Index - Jameson-Wolf

| | |
|---|---|
| SEQ. ID. NO. 22063 | 1-MetLysAsnIleSerLeu-6 |
| SEQ. ID. NO. 22064 | 16-GlyGlyGlyGlnLeuGlyArg-22 |
| SEQ. ID. NO. 22065 | 37-ValLeuAspProAsnProAsnAlaPro-45 |
| SEQ. ID. NO. 22066 | 57-ProPheAspAsnGlnThrAlaLeuGluGluLeuAlaLys-69 |
| SEQ. ID. NO. 22067 | 75-ThrGluPheGluAsnValAsnAlaAspAla-84 |
| SEQ. ID. NO. 22068 | 91-HisThrAsnValSerProSerGlyAsp-99 |
| SEQ. ID. NO. 22069 | 106-AsnArgIleGlnGluLysAlaTrpIle-114 |
| SEQ. ID. NO. 22070 | 128-CysLysAlaGluAspIleThrGluGluSerIle-138 |
| SEQ. ID. NO. 22071 | 150-LeuGlyTyrAspGlyLysGlyGlnIleArgValLysThrValAspGluLeuLysAlaAlaPheAlaGluHisArgGlyValAspCysValLeu-180 |

TABLE 1-continued

| | |
|---|---|
| SEQ. ID. NO. 22072 | 182-LysMetValAspLeuArgGlyGluIle-190 |
| SEQ. ID. NO. 22073 | 196-ArgLeuAsnAsnAspAsnValGlnThrPheAspProAlaGluAsnIleHisGluAsnGly-215 |
| SEQ. ID. NO. 22074 | 230-IleGlnGlnGlnAlaArgGlnMetAla-238 |
| SEQ. ID. NO. 22075 | 269-IleAlaProArgProHisAsnSerGlyHisHis-279 |
| SEQ. ID. NO. 22076 | 288-GlnPheGlnGlnGlnVal-293 |
| SEQ. ID. NO. 22077 | 300-ProProAlaAspThrLysLeuLeuSer-308 |
| SEQ. ID. NO. 22078 | 319-ValTrpGlnGluAspGlyGlyGluProAspTrp-329 |
| SEQ. ID. NO. 22079 | 331-ProLeuGlnSerArgProAspAlaHis-339 |
| SEQ. ID. NO. 22080 | 344-GlyLysLysThrAlaHisLysGlyArgLysMetGly-355 |
| SEQ. ID. NO. 22081 | 360-LeuSerThrAspSerAspThrAlaPheGlnGluAlaLysLysLeuHis-375 |
| Hydrophilic Regions - Hopp-Woods | |
| SEQ. ID. NO. 22082 | 62-ThrAlaLeuGluGluLeuAlaLys-69 |
| SEQ. ID. NO. 22083 | 75-ThrGluPheGluAsnValAsn-81 |
| SEQ. ID. NO. 22084 | 128-CysLysAlaGluAspIleThrGluGluSerIle-138 |
| SEQ. ID. NO. 22085 | 152-TyrAspGlyLysGlyGlnIleArgValLysThrValAspGluLeuLysAlaAlaPheAlaGluHisArgGlyValAspCysValLeu-180 |
| SEQ. ID. NO. 22086 | 182-LysMetValAspLeuArgGlyGluIle-190 |
| SEQ. ID. NO. 22087 | 197-LeuAsnAsnAspAsn-201 |
| SEQ. ID. NO. 22088 | 206-AspProAlaGluAsnIleHis-212 |
| SEQ. ID. NO. 22089 | 230-IleGlnGlnGlnAlaArgGlnMetAla-238 |
| SEQ. ID. NO. 22090 | 269-IleAlaProArgProHisAsn-275 |
| SEQ. ID. NO. 22091 | 301-ProAlaAspThrLysLeu-306 |
| SEQ. ID. NO. 22092 | 320-TrpGlnGluAspGlyGlyGluProAsp-328 |
| SEQ. ID. NO. 22093 | 334-SerArgProAspAla-338 |
| SEQ. ID. NO. 22094 | 344-GlyLysLysThrAlaHisLysGlyArgLysMetGly-355 |
| SEQ. ID. NO. 22095 | 362-ThrAspSerAspThrAlaPheGlnGluAlaLysLysLeuHis-375 |
| a658 | |
| AMPHI Regions - AMPHI | |
| SEQ. ID. NO. 22096 | 28-ArgGlnTyrAlaAspValValGlnPheIleGlyGlnThrLeuArgHisLeuSerArgLeuLeuLeuAsn-50 |
| SEQ. ID. NO. 22097 | 57-TrpAspAspGlyVal-61 |
| SEQ. ID. NO. 22098 | 68-ValAsnValPheGlyArgIleGluSer-76 |
| SEQ. ID. NO. 22099 | 94-GlnValHisHisPhePheGlnAsnAlaIleHisAla-105 |
| SEQ. ID. NO. 22100 | 128-IleAlaGlnCysSerGlyPheGlnAspAlaGlyGln-139 |
| SEQ. ID. NO. 22101 | 143-AlaPhePheSerAspValPheGly-150 |
| Antigenic Index - Jameson-Wolf | |
| SEQ. ID. NO. 22102 | 6-ValArgThrArgArgAspPheValAspAspGlnPheMetArgValAlaAspAsnLysHisPhe-26 |
| SEQ. ID. NO. 22103 | 55-SerGlyTrpAspAspGlyValGlyGluAspThrVal-66 |
| SEQ. ID. NO. 22104 | 72-GlyArgIleGluSer-76 |
| SEQ. ID. NO. 22105 | 84-ThrAlaTyrAspAsnGlyAsn-90 |
| SEQ. ID. NO. 22106 | 108-PheGlyLysArgGlyPhe-113 |
| SEQ. ID. NO. 22107 | 131-CysSerGlyPheGlnAspAlaGlyGlnLys-140 |
| SEQ. ID. NO. 22108 | 155-LeuIleArgArgGlyLeuGln-161 |
| SEQ. ID. NO. 22109 | 174-ValLeuArgAspGlyAsnAla-180 |
| SEQ. ID. NO. 22110 | 189-MetPheGlyGluLysThrHisArgIleGly-198 |
| SEQ. ID. NO. 22111 | 202-PheGluLeuGlyArgAsnSerArgThr-210 |
| SEQ. ID. NO. 22112 | 216-GlnSerGlyLeuValValLysArgArgThrGln-226 |
| SEQ. ID. NO. 22113 | 230-GlyLysPheArgCysArgArgIleArgVal-239 |
| SEQ. ID. NO. 22114 | 251-PheGlySerAsnSerLysHisSerAla-259 |
| Hydrophilic Regions - Hopp-Woods | |
| SEQ. ID. NO. 22115 | 6-ValArgThrArgArgAspPheValAsp-14 |
| SEQ. ID. NO. 22116 | 16-GlnPheMetArgValAlaAspAsnLysHisPhe-26 |
| SEQ. ID. NO. 22117 | 56-GlyTrpAspAspGlyValGlyGluAspThrVal-66 |
| SEQ. ID. NO. 22118 | 72-GlyArgIleGluSer-76 |
| SEQ. ID. NO. 22119 | 135-GlnAspAlaGlyGln-139 |
| SEQ. ID. NO. 22120 | 174-ValLeuArgAspGlyAsnAla-180 |
| SEQ. ID. NO. 22121 | 190-PheGlyGluLysThrHisArgIleGly-198 |
| SEQ. ID. NO. 22122 | 203-GluLeuGlyArgAsnSerArg-209 |
| SEQ. ID. NO. 22123 | 220-ValValLysArgArgThrGln-226 |
| SEQ. ID. NO. 22124 | 230-GlyLysPheArgCysArgArgIleArgVal-239 |
| SEQ. ID. NO. 22125 | 253-SerAsnSerLysHisSerAla-259 |
| a661 | |
| AMPHI Regions - AMPHI | |
| SEQ. ID. NO. 22126 | 19-GlyIleThrAspLysProPheArgArgLeuCysArgAspPheGlyAlaGly-35 |
| SEQ. ID. NO. 22127 | 37-AlaValCysGluMetLeu-42 |
| SEQ. ID. NO. 22128 | 75-AspProGlnGlnMetAlaAspAlaAla-83 |
| SEQ. ID. NO. 22129 | 122-AlaAlaIleLeuGluAlaValValLys-130 |
| SEQ. ID. NO. 22130 | 152-ProValIleAlaLysIleAlaGlu-159 |
| SEQ. ID. NO. 22131 | 222-TyrAspArgAlaArgArg-227 |
| SEQ. ID. NO. 22132 | 235-ProArgPheGluThrLeuArgArgThrArgCys-245 |
| SEQ. ID. NO. 22133 | 248-AlaCysLeuGluPheGlyArgMetTyrArgHisTyrPheGluPro-262 |
| SEQ. ID. NO. 22134 | 267-AlaArgValLeuArgArgHis-273 |
| Antigenic Index - Jameson-Wolf | |
| SEQ. ID. NO. 22135 | 20-IleThrAspLysProPheArgArgLeuCysArgAspPheGlyAlaGly-35 |
| SEQ. ID. NO. 22136 | 42-LeuThrSerAspProThrLeuArgAsnThrArgLysThrLeuHisArgSerAspPheAlaAspGluGlyGly-65 |
| SEQ. ID. NO. 22137 | 72-AlaGlySerAspProGlnGlnMetAlaAspAlaAlaArg-84 |
| SEQ. ID. NO. 22138 | 97-AsnMetGlyCysProAlaLysLysValCys-106 |
| SEQ. ID. NO. 22139 | 143-GlyTrpHisAspAspHisGlnAsnLeu-151 |
| SEQ. ID. NO. 22140 | 157-IleAlaGluAspCysGly-162 |
| SEQ. ID. NO. 22141 | 168-XxxProArgThrHisAla-173 |
| SEQ. ID. NO. 22142 | 176-AsnValGlnArgArgSerGlyLeuArgProAspCysArgAsnGlnMetProSerGluHisProGlyLeuGlyGlnArgArgHisTyrLeuAlaAlaLys SerProSerArgProGlnThrAsnArgArgArgArgHisTyrAspArgAlaArgArgAlaArgGln-230 |

TABLE 1-continued

| | |
|---|---|
| SEQ. ID. NO. 22143 | 235-ProArgPheGluThrLeuArgArgThrArgCysPhe-246 |
| SEQ. ID. NO. 22144 | 256-TyrArgHisTyrPheGluProHisProSerHisAlaArgValLeuArgArgHisArgArgCysAlaHisArgThrGlnThrHisArgLeuValHisArgArgAsnAlaArgArgArgThrAspThrSer-298 |

Hydrophilic Regions - Hopp-Woods

| | |
|---|---|
| SEQ. ID. NO. 22145 | 20-IleThrAspLysProPheArgArgLeuCysArgAspPhe-32 |
| SEQ. ID. NO. 22146 | 46-ProThrLeuArgAsnThrArgLysThrLeuHisArgSerAspPheAlaAspGluGlyGly-65 |
| SEQ. ID. NO. 22147 | 73-GlySerAspProGlnGlnMetAlaAspAlaAlaArg-84 |
| SEQ. ID. NO. 22148 | 100-CysProAlaLysLysValCys-106 |
| SEQ. ID. NO. 22149 | 157-IleAlaGluAspCysGly-162 |
| SEQ. ID. NO. 22150 | 176-AsnValGlnArgArgSerGlyLeuArgProAspCysArgAsnGlnMetProSerGluHisProGlyLeuGlyGlnArgArgHisTyrLeu-205 |
| SEQ. ID. NO. 22151 | 208-LysSerProSerArgProGlnThrAsnArgArgArgArgHisTyrAspArgAlaArgArgAlaArgGln-230 |
| SEQ. ID. NO. 22152 | 238-GluThrLeuArgArgThrArgCys-245 |
| SEQ. ID. NO. 22153 | 268-ArgValLeuArgArgHisArgArgCysAlaHisArgThrGlnThr-282 |
| SEQ. ID. NO. 22154 | 285-LeuValHisArgArgAsnAlaArgArgArgThrAspThrSer-298 | a663
AMPHI Regions - AMPHI

| | |
|---|---|
| SEQ. ID. NO. 22155 | 19-ProPheAlaLeuLeuHisLysLeuAlaAspLeuThrGlyLeuLeuAlaTyr-35 |
| SEQ. ID. NO. 22156 | 66-LysGlnHisPheLysHisMetAlaLysLeu-75 |
| SEQ. ID. NO. 22157 | 87-AlaGlyArgLeuLysSerLeuValArg-95 |
| SEQ. ID. NO. 22158 | 168-GluGlyLeuArgAlaLeuValLysGlnPheArgLys-179 |
| SEQ. ID. NO. 22159 | 209-ThrIleThrGlyLeuSerArgIleAlaAlaLeuAlaAsn-221 |
| SEQ. ID. NO. 22160 | 243-ProAlaTrpGluSer-247 |
| SEQ. ID. NO. 22161 | 258-GlnArgMetAsnArgPheIleGluGluArgValArgGluHis-271 |

Antigenic Index - Jameson-Wolf

| | |
|---|---|
| SEQ. ID. NO. 22162 | 38-ValLysProArgArgArgIleGlyGlu-46 |
| SEQ. ID. NO. 22163 | 56-TrpAspGlyLysLysArgLysThrValLeu-65 |
| SEQ. ID. NO. 22164 | 87-AlaGlyArgLeuLysSer-92 |
| SEQ. ID. NO. 22165 | 94-ValArgTyrArgAsnLysHisTyrLeuAsp-103 |
| SEQ. ID. NO. 22166 | 105-AlaLeuAlaAlaGlyGluLys-111 |
| SEQ. ID. NO. 22167 | 139-TyrSerHisGlnLysAsnLysIleLeuAsp-148 |
| SEQ. ID. NO. 22168 | 150-GlnIleLeuLysGlyArgAsnArgTyr-158 |
| SEQ. ID. NO. 22169 | 166-ArgThrGluGlyLeuArgAlaLeu-173 |
| SEQ. ID. NO. 22170 | 175-LysGlnPheArgLysSerSerAla-182 |
| SEQ. ID. NO. 22171 | 188-ProAspGlnAspPheGlyArgAsnAspSerVal-198 |
| SEQ. ID. NO. 22172 | 229-ProValArgGluAlaAspAsnThr-236 |
| SEQ. ID. NO. 22173 | 243-ProAlaTrpGluSerPheProSerGluAspAlaGlnAlaAspAlaGlnArgMetAsnArgPheIleGluGluArgValArgGluHisProGlu-273 |
| SEQ. ID. NO. 22174 | 280-LysArgPheLysThrArgProGluGlySerProAspPheTyr-293 |

Hydrophilic Regions - Hopp-Woods

| | |
|---|---|
| SEQ. ID. NO. 22175 | 39-LysProArgArgArgIleGlyGlu-46 |
| SEQ. ID. NO. 22176 | 56-TrpAspGlyLysLysArgLysThrValLeu-65 |
| SEQ. ID. NO. 22177 | 88-GlyArgLeuLysSer-92 |
| SEQ. ID. NO. 22178 | 94-ValArgTyrArgAsn-98 |
| SEQ. ID. NO. 22179 | 105-AlaLeuAlaAlaGlyGluLys-111 |
| SEQ. ID. NO. 22180 | 142-GlnLysAsnLysIleLeuAsp-148 |
| SEQ. ID. NO. 22181 | 150-GlnIleLeuLysGlyArgAsnArgTyr-158 |
| SEQ. ID. NO. 22182 | 166-ArgThrGluGlyLeuArgAlaLeu-173 |
| SEQ. ID. NO. 22183 | 176-GlnPheArgLysSerSer-181 |
| SEQ. ID. NO. 22184 | 190-GlnAspPheGlyArgAsnAspSerVal-198 |
| SEQ. ID. NO. 22185 | 229-ProValArgGluAlaAspAsn-235 |
| SEQ. ID. NO. 22186 | 248-PheProSerGluAspAlaGlnAlaAspAlaGlnArgMetAsnArgPheIleGluGluArgValArgGluHisProGlu-273 |
| SEQ. ID. NO. 22187 | 280-LysArgPheLysThrArgProGluGlySerPro-290 | a664
AMPHI Regions - AMPHI

| | |
|---|---|
| SEQ. ID. NO. 22188 | 28-AlaHisArgMetCys-32 |
| SEQ. ID. NO. 22189 | 47-AlaAspValPheAspThrAlaHisGlyAlaAlaGly-58 |
| SEQ. ID. NO. 22190 | 88-AlaArgProValValGluIle-94 |

Antigenic Index - Jameson-Wolf

| | |
|---|---|
| SEQ. ID. NO. 22191 | 25-SerGlyGlyAlaHisArgMetCysGlyArg-34 |
| SEQ. ID. NO. 22192 | 48-AspValPheAspThrAlaHisGly-55 |
| SEQ. ID. NO. 22193 | 73-PheLeuGlnArgLysLeuGluPro-80 |
| SEQ. ID. NO. 22194 | 108-IleGlyGlyGlyThrAlaValGlyLysAspGluLeuGlyValLysAspValGln-125 |
| SEQ. ID. NO. 22195 | 137-AlaHisGlyAspAspHisGluAsn-144 |
| SEQ. ID. NO. 22196 | 164-AlaIleProArgGlnSerArgProTrp-172 |
| SEQ. ID. NO. 22197 | 175-ProLeuArgTrpCysLysThrArgPhe-183 |

Hydrophilic Regions - Hopp-Woods

| | |
|---|---|
| SEQ. ID. NO. 22198 | 74-LeuGlnArgLysLeuGluPro-80 |
| SEQ. ID. NO. 22199 | 113-AlaValGlyLysAspGluLeuGlyValLysAspValGln-125 |
| SEQ. ID. NO. 22200 | 137-AlaHisGlyAspAspHisGluAsn-144 |
| SEQ. ID. NO. 22201 | 166-ProArgGlnSerArg-170 | a665-1
AMPHI Regions - AMPHI

| | |
|---|---|
| SEQ. ID. NO. 22202 | 6-HisTyrLeuLysAspTyrGln-12 |
| SEQ. ID. NO. 22203 | 105-LeuTyrAlaSerAla-109 |
| SEQ. ID. NO. 22204 | 111-AsnLeuPheThrGlnCysGluProGlyPheArgLysIleThr-125 |
| SEQ. ID. NO. 22205 | 132-AspValMetSerLysPheThrThrThr-140 |
| SEQ. ID. NO. 22206 | 167-ArgHisTrpValLysTrpGluAspProPhe-176 |
| SEQ. ID. NO. 22207 | 225-SerLeuLysAsnAlaMetLys-231 |
| SEQ. ID. NO. 22208 | 286-GlyIleGluSerValVal-291 |
| SEQ. ID. NO. 22209 | 294-GluTyrPheHisAsnTrpThr-300 |
| SEQ. ID. NO. 22210 | 307-ArgAspTrpPheGlnLeuSerLeu-314 |

TABLE 1-continued

| | |
|---|---|
| SEQ. ID. NO. 22211 | 329-AspArgAlaSerArgAlaValArgArgIleGluAsnIleArgLeuLeuArgGln-346 |
| SEQ. ID. NO. 22212 | 360-ValArgProAlaArgTyrGluGluMetAsnAsnPheTyrThr-373 |
| SEQ. ID. NO. 22213 | 380-GlyAlaGluValValArgMetTyrHisThrLeu-390 |
| SEQ. ID. NO. 22214 | 396-PheGlnLysGlyMetLys-401 |
| SEQ. ID. NO. 22215 | 520-ThrGluAlaValValProSerLeuLeuArgGlyPheSerAlaPro-534 |
| SEQ. ID. NO. 22216 | 555-AspAlaPheThrArgTrpGluAlaAlaGln-564 |
| SEQ. ID. NO. 22217 | 575-LeuAlaAlaLeuSerAspGlyValGluLeuProLysHisGluLysLeuLeuAlaAlaValGlu-595 |
| SEQ. ID. NO. 22218 | 603-LeuAspAsnAlaPheLysAlaLeu-610 |
| SEQ. ID. NO. 22219 | 622-AspGlyAlaGluAsnIleAspProLeu-630 |
| SEQ. ID. NO. 22220 | 648-LeuProLysTrpHisGluLeuAsnArg-656 |
| SEQ. ID. NO. 22221 | G674-lyTrpArgThrLeuArgAsnValCysArgAla-684 |
| SEQ. ID. NO. 22222 | 696-ThrValAlaGluLysTyrAlaGluMetAlaGlnAsnMet-708 |
| SEQ. ID. NO. 22223 | 712-TrpGlyIleLeuSer-716 |
| SEQ. ID. NO. 22224 | 728-ArgLeuLeuAlaGlnPheAlaAspLysPheSer-738 |
| SEQ. ID. NO. 22225 | 758-AspThrLeuGlnGlnValGlnThrAla-766 |
| SEQ. ID. NO. 22226 | 782-SerLeuIleGlySerPheSerArgAsnVal-791 |
| SEQ. ID. NO. 22227 | 822-ArgLeuValGlnAlaPheAsnLeuCysAsnLysLeu-833 |
| Antigenic Index - Jameson-Wolf | |
| SEQ. ID. NO. 22228 | 8-LeuLysAspTyrGlnThrProAlaTyr-16 |
| SEQ. ID. NO. 22229 | 26-AspIleAsnGluPro-30 |
| SEQ. ID. NO. 22230 | 34-ValLysSerArgLeuThrValGluProLysArgValGlyGlu-47 |
| SEQ. ID. NO. 22231 | 49-LeuValLeuAspGlySerAla-55 |
| SEQ. ID. NO. 22232 | 79-AlaAspValProSerGluArgPheThrVal-88 |
| SEQ. ID. NO. 22233 | 90-ValGluThrGluIleLeuProAlaGluAsnLysSerLeu-102 |
| SEQ. ID. NO. 22234 | 114-ThrGlnCysGluProGluGlyPheArgLys-123 |
| SEQ. ID. NO. 22235 | 128-IleAspArgProAspValMetSer-135 |
| SEQ. ID. NO. 22236 | 142-ValAlaAspLysLysArgTyrPro-149 |
| SEQ. ID. NO. 22237 | 154-AsnGlyAsnLysIleAspGlyGlyGluTyrSerAspGlyArgHisTrpValLysTrpGluAspProPheAlaLysProSer-180 |
| SEQ. ID. NO. 22238 | 191-AlaValThrGluAspTyr-196 |
| SEQ. ID. NO. 22239 | 200-MetSerGlyArgAsnValLysIle-207 |
| SEQ. ID. NO. 22240 | 211-ThrThrGluAlaAspLysProLysVal-219 |
| SEQ. ID. NO. 22241 | 230-MetLysTrpAspGluThrArgPhe-237 |
| SEQ. ID. NO. 22242 | 255-AsnMetGlyAlaMetGluAsnLysGlyLeu-264 |
| SEQ. ID. NO. 22243 | 275-AspSerArgThrAlaThrAspThrAspPheGluGlyIleGlu-288 |
| SEQ. ID. NO. 22244 | 295-TyrPheHisAsnTrpThrGlyAsnArgValThrCysArgAspTrp-309 |
| SEQ. ID. NO. 22245 | 313-SerLeuLysGluGly-317 |
| SEQ. ID. NO. 22246 | 322-ArgAspGlnGluPheSerGlyAspArgAlaSerArgAlaValArgArgIleGluAsn-340 |
| SEQ. ID. NO. 22247 | 347-HisGlnPheProGluAspAlaGlyProThrAlaHisProValArgProAlaArgTyrGluGluMetAsn-369 |
| SEQ. ID. NO. 22248 | 376-ValTyrGluLysGlyAlaGluVal-383 |
| SEQ. ID. NO. 22249 | 394-GluGlyPheGlnLysGlyMet-400 |
| SEQ. ID. NO. 22250 | 404-PheGlnArgHisAspGlyGlnAlaValThrCysAspAspPheArg-418 |
| SEQ. ID. NO. 22251 | 437-SerGlnAlaGlyThrPro-442 |
| SEQ. ID. NO. 22252 | 446-AlaGlnGlyArgLeuLysAsnAsnVal-454 |
| SEQ. ID. NO. 22253 | 459-IleLysGlnThrValProProThrProAspMetAlaAspLysGlnPro-474 |
| SEQ. ID. NO. 22254 | 485-AsnCysAsnGlyGluAlaVal-491 |
| SEQ. ID. NO. 22255 | 494-AspTyrGlnGlyLysArgAlaThrGlu-502 |
| SEQ. ID. NO. 22256 | 509-GluAlaGluGlnThrPhe-514 |
| SEQ. ID. NO. 22257 | 537-LeuAsnTyrProTyrSerAspAspAspLeu-546 |
| SEQ. ID. NO. 22258 | 552-HisAspSerAspAla-556 |
| SEQ. ID. NO. 22259 | 578-LeuSerAspGlyValGluLeuProLysHisGluLysLeu-590 |
| SEQ. ID. NO. 22260 | 594-ValGluLysValIleSerAspAspLeuLeu-603 |
| SEQ. ID. NO. 22261 | 614-ValProSerGluAlaGluLeuTrpAspGlyAlaGluAsnIleAspProLeuArg-631 |
| SEQ. ID. NO. 22262 | 633-HisGlnAlaArgGluAlaLeu-639 |
| SEQ. ID. NO. 22263 | 652-HisGluLeuAsnArgGlnAlaAlaLysGlnGluAsnGlnSerTyrGluTyrSerProGluAlaAlaGly-674 |
| SEQ. ID. NO. 22264 | 677-ThrLeuArgAsnValCys-682 |
| SEQ. ID. NO. 22265 | 689-AlaAspProAlaHis-693 |
| SEQ. ID. NO. 22266 | 696-ThrValAlaGluLysTyrAlaGlu-703 |
| SEQ. ID. NO. 22267 | 719-AsnGlyAsnGluSerAspThrArgAsnArgLeu-729 |
| SEQ. ID. NO. 22268 | 733-PheAlaAspLysPheSerAspAspAlaLeuVal-743 |
| SEQ. ID. NO. 22269 | 752-GlySerSerArgArgSerAspThrLeuGln-761 |
| SEQ. ID. NO. 22270 | 768-GlnHisProLysPheSerLeuGluAsnProAsnLysAlaArgSer-782 |
| SEQ. ID. NO. 22271 | 785-GlySerPheSerArgAsnValPro-792 |
| SEQ. ID. NO. 22272 | 795-HisAlaGluAspGlySerGlyTyrArgPheIleAla-806 |
| SEQ. ID. NO. 22273 | 808-LysValIleGluIleAspArgPheAsnProGlnVal-819 |
| SEQ. ID. NO. 22274 | 831-AsnLysLeuGluProHisArgLysAsnLeuVal-841 |
| SEQ. ID. NO. 22275 | 844-AlaLeuGlnArgIleArgAlaGlnGluGlyLeuSerLysAspValGlyGluIleVal-862 |
| Hydrophilic Regions - Hopp-Woods | |
| SEQ. ID. NO. 22276 | 34-ValLysSerArgLeuThrValGluProLysArgValGlyGlu-47 |
| SEQ. ID. NO. 22277 | 81-ValProSerGluArgPheThrVal-88 |
| SEQ. ID. NO. 22278 | 90-ValGluThrGluIleLeuProAlaGluAsnLysSer-101 |
| SEQ. ID. NO. 22279 | 116-CysGluProGluGlyPheArg-122 |
| SEQ. ID. NO. 22280 | 129-AspArgProAspValMetSer-135 |
| SEQ. ID. NO. 22281 | 142-ValAlaAspLysLysArgTyr-148 |
| SEQ. ID. NO. 22282 | 154-AsnGlyAsnLysIleAspGlyGlyGluTyrSerAspGlyArgHis-168 |
| SEQ. ID. NO. 22283 | 170-ValLysTrpGluAspProPheAla-177 |
| SEQ. ID. NO. 22284 | 201-SerGlyArgAsnValLys-206 |
| SEQ. ID. NO. 22285 | 213-GluAlaAspLysProLysVal-219 |
| SEQ. ID. NO. 22286 | 230-MetLysTrpAspGluThrArgPhe-237 |
| SEQ. ID. NO. 22287 | 258-AlaMetGluAsnLysGly-263 |
| SEQ. ID. NO. 22288 | 275-AspSerArgThrAlaThrAspThrAspPheGluGlyIleGlu-288 |

TABLE 1-continued

| | |
|---|---|
| SEQ. ID. NO. 22289 | 313-SerLeuLysGluGly-317 |
| SEQ. ID. NO. 22290 | 322-ArgAspGlnGluPheSerGlyAspArgAlaSerArgAlaValArgArgIleGluAsn-340 |
| SEQ. ID. NO. 22291 | 348-GlnPheProGluAspAlaGlyPro-355 |
| SEQ. ID. NO. 22292 | 361-ArgProAlaArgTyrGluGluMetAsn-369 |
| SEQ. ID. NO. 22293 | 376-ValTyrGluLysGlyAlaGluVal-383 |
| SEQ. ID. NO. 22294 | 394-GluGlyPheGlnLysGlyMet-400 |
| SEQ. ID. NO. 22295 | 406-ArgHisAspGlyGln-410 |
| SEQ. ID. NO. 22296 | 413-ThrCysAspAspPheArg-418 |
| SEQ. ID. NO. 22297 | 446-AlaGlnGlyArgLeuLysAsnAsnVal-454 |
| SEQ. ID. NO. 22298 | 467-ProAspMetAlaAspLysGlnPro-474 |
| SEQ. ID. NO. 22299 | 495-TyrGlnGlyLysArgAlaThrGlu-502 |
| SEQ. ID. NO. 22300 | 541-TyrSerAspAspAspLeu-546 |
| SEQ. ID. NO. 22301 | 552-HisAspSerAspAla-556 |
| SEQ. ID. NO. 22302 | 580-AspGlyValGluLeuProLysHisGluLysLeu-590 |
| SEQ. ID. NO. 22303 | 594-ValGluLysValIleSer-599 |
| SEQ. ID. NO. 22304 | 616-SerGluAlaGluLeu-620 |
| SEQ. ID. NO. 22305 | 622-AspGlyAlaGluAsnIleAspPro-629 |
| SEQ. ID. NO. 22306 | 633-HisGlnAlaArgGluAlaLeu-639 |
| SEQ. ID. NO. 22307 | 652-HisGluLeuAsnArgGlnAlaAlaLysGlnGluAsnGlnSer-665 |
| SEQ. ID. NO. 22308 | 689-AlaAspProAlaHis-693 |
| SEQ. ID. NO. 22309 | 696-ThrValAlaGluLysTyrAlaGlu-703 |
| SEQ. ID. NO. 22310 | 719-AsnGlyAsnGluSerAspThrArgAsnArgLeu-729 |
| SEQ. ID. NO. 22311 | 733-PheAlaAspLysPheSerAsp-739 |
| SEQ. ID. NO. 22312 | 753-SerSerArgArgSerAspThr-759 |
| SEQ. ID. NO. 22313 | 776-AsnProAsnLysAlaArgSer-782 |
| SEQ. ID. NO. 22314 | 795-HisAlaGluAspGlySerGly-801 |
| SEQ. ID. NO. 22315 | 808-LysValIleGluIleAspArgPheAsn-816 |
| SEQ. ID. NO. 22316 | 831-AsnLysLeuGluProHisArgLysAsnLeuVal-841 |
| SEQ. ID. NO. 22317 | 844-AlaLeuGlnArgIleArgAlaGlnGluGlyLeuSerLysAspValGlyGluIleVal-862 | a666
AMPHI Regions - AMPHI

| | |
|---|---|
| SEQ. ID. NO. 22318 | 89-GlyTyrAspIleLeuLysGlnGlyGlySer-98 |
| SEQ. ID. NO. 22319 | 162-LeuLysPheMetGluAlaVal-168 |

Antigenic Index - Jameson-Wolf

| | |
|---|---|
| SEQ. ID. NO. 22320 | 5-AsnHisGlnSerAsnSerGlyGluGlyValLeu-15 |
| SEQ. ID. NO. 22321 | 40-AsnGlnGlyLysValAsnThr-46 |
| SEQ. ID. NO. 22322 | 54-AlaAspAlaHisThrProGluHisAlaThr-63 |
| SEQ. ID. NO. 22323 | 65-LeuThrGluGlnLysGln-70 |
| SEQ. ID. NO. 22324 | 92-IleLeuLysGlnGlyGlySerAlaAla-100 |
| SEQ. ID. NO. 22325 | 114-GluProGlnSerSerGlyLeuGlyGly-122 |
| SEQ. ID. NO. 22326 | 130-AspAsnThrAlaLysThr-135 |
| SEQ. ID. NO. 22327 | 137-ThrThrPheAspGlyArgGluThrAlaPro-146 |
| SEQ. ID. NO. 22328 | 154-PheLeuAspLysAspGlyGlnPro-161 |

Hydrophilic Regions - Hopp-Woods

| | |
|---|---|
| SEQ. ID. NO. 22329 | 8-SerAsnSerGlyGlu-12 |
| SEQ. ID. NO. 22330 | 40-AsnGlnGlyLysValAsnThr-46 |
| SEQ. ID. NO. 22331 | 55-AspAlaHisThrProGluHis-61 |
| SEQ. ID. NO. 22332 | 65-LeuThrGluGlnLysGln-70 |
| SEQ. ID. NO. 22333 | 96-GlyGlySerAlaAla-100 |
| SEQ. ID. NO. 22334 | 139-PheAspGlyArgGluThrAlaPro-146 |
| SEQ. ID. NO. 22335 | 154-PheLeuAspLysAspGlyGlnPro-161 | a667
AMPHI Regions - AMPHI

| | |
|---|---|
| SEQ. ID. NO. 22336 | 49-IleAlaAspPheLeuGlnProAlaArgValGluArgLeuProHisLeuAlaAla-66 |
| SEQ. ID. NO. 22337 | 74-LysThrAlaGlnPhe-78 |
| SEQ. ID. NO. 22338 | 115-IleAlaAlaValAlaGluIle-121 |
| SEQ. ID. NO. 22339 | 128-IleAlaArgGlyValAspAlaValGlnArg-137 |
| SEQ. ID. NO. 22340 | 152-ThrAspGlnLeuArgArgMetPhePheAsnGlnLeuGluLysPheGlyAspAsnHis-170 |
| SEQ. ID. NO. 22341 | 174-ValIleHisLeuAlaAspCysThrAsp-182 |
| SEQ. ID. NO. 22342 | 201-LysMetMetLeuHisLysIleProThrArgLeu-211 |

Antigenic Index - Jameson-Wolf

| | |
|---|---|
| SEQ. ID. NO. 22343 | 11-IleValSerAspProLeuAsp-17 |
| SEQ. ID. NO. 22344 | 27-SerAlaAlaAspGlnThrGluThrGln-35 |
| SEQ. ID. NO. 22345 | 56-AlaArgValGluArgLeuPro-62 |
| SEQ. ID. NO. 22346 | 71-LeuAlaArgLysThrAlaGln-77 |
| SEQ. ID. NO. 22347 | 84-ArgHisIleArgProArgLeuValLysArgGluGlnIle-96 |
| SEQ. ID. NO. 22348 | 130-ArgGlyValAspAlaValGln-136 |
| SEQ. ID. NO. 22349 | 139-ValMetGlnAsnArgGlnValGlu-146 |
| SEQ. ID. NO. 22350 | 151-ProThrAspGlnLeuArg-156 |
| SEQ. ID. NO. 22351 | 163-LeuGluLysPheGlyAsp-168 |
| SEQ. ID. NO. 22352 | 179-AspCysThrAspMet-183 |
| SEQ. ID. NO. 22353 | 188-ProProThrHisAlaAlaArgAsnArgHisAsnLeu-199 |
| SEQ. ID. NO. 22354 | 207-IleProThrArgLeu-211 |
| SEQ. ID. NO. 22355 | 226-GlyGlnArgGlyArgGlnValIleGlnArgThrAspThrLeu-239 |
| SEQ. ID. NO. 22356 | 247-IleGluSerGlnAsnArgGlyHisAspSer-256 |

Hydrophilic Regions - Hopp-Woods

| | |
|---|---|
| SEQ. ID. NO. 22357 | 11-IleValSerAspProLeu-16 |
| SEQ. ID. NO. 22358 | 27-SerAlaAlaAspGlnThrGluThrGln-35 |
| SEQ. ID. NO. 22359 | 56-AlaArgValGluArgLeuPro-62 |
| SEQ. ID. NO. 22360 | 71-LeuAlaArgLysThrAlaGln-77 |

TABLE 1-continued

| | |
|---|---|
| SEQ. ID. NO. 22361 | 84-ArgHisIleArgProArgLeuValLysArgGluGlnIle-96 |
| SEQ. ID. NO. 22362 | 130-ArgGlyValAspAlaValGln-136 |
| SEQ. ID. NO. 22363 | 164-GluLysPheGlyAsp-168 |
| SEQ. ID. NO. 22364 | 191-HisAlaAlaArgAsnArgHisAsnLeu-199 |
| SEQ. ID. NO. 22365 | 227-GlnArgGlyArgGlnValIleGlnArgThrAspThr-238 |
| SEQ. ID. NO. 22366 | 249-SerGlnAsnArgGlyHisAsp-255 | a669
AMPHI Regions - AMPHI

| | |
|---|---|
| SEQ. ID. NO. 22367 | 24-LysLeuHisArgAlaPhe-29 |
| SEQ. ID. NO. 22368 | 59-GlnIlePheArgHisValGlnSer-66 |
| SEQ. ID. NO. 22369 | 79-LysProProAsnThrAla-84 |

Antigenic Index - Jameson-Wolf

| | |
|---|---|
| SEQ. ID. NO. 22370 | 1-MetArgArgIleIleLysLysHisGlnProValAsn-12 |
| SEQ. ID. NO. 22371 | 33-GlyArgLysArgProHisHisHisAspArgSerLeuArgArgGlnHisGlyIle-50 |
| SEQ. ID. NO. 22372 | 64-ValGlnSerSerAsnArgGlnAsnGlyArgGlnProValCysThrLysProProAsnThrAlaSer-85 |
| SEQ. ID. NO. 22373 | 100-AlaAspIleLysArgIleLeu-106 |

Hydrophilic Regions - Hopp-Woods

| | |
|---|---|
| SEQ. ID. NO. 22374 | 1-MetArgArgIleIleLysLysHisGlnPro-10 |
| SEQ. ID. NO. 22375 | 33-GlyArgLysArgProHisHisHisAspArgSerLeuArgArgGlnHisGly-49 |
| SEQ. ID. NO. 22376 | 65-GlnSerSerAsnArgGlnAsnGlyArgGlnProValCysThrLysProProAsn-82 |
| SEQ. ID. NO. 22377 | 100-AlaAspIleLysArgIleLeu-106 | a670
AMPHI Regions - AMPHI

| | |
|---|---|
| SEQ. ID. NO. 22378 | 10-ArgSerCysPheGly-14 |
| SEQ. ID. NO. 22379 | 16-ValLysAsnAlaSerGlyValSer-23 |
| SEQ. ID. NO. 22380 | 34-IleThrArgSerAla-38 |
| SEQ. ID. NO. 22381 | 77-ValGlySerSerAsnAsnIle-83 |
| SEQ. ID. NO. 22382 | 126-PheSerAlaCysSer-130 |

Antigenic Index - Jameson-Wolf

| | |
|---|---|
| SEQ. ID. NO. 22383 | 4-CysArgAsnCysLeuAlaArgSerCys-12 |
| SEQ. ID. NO. 22384 | 18-AsnAlaSerGlyValSerSerSerArgIleCysProLeuSer-31 |
| SEQ. ID. NO. 22385 | 33-LysIleThrArgSerAlaThrSerArgAlaAsnProIle-45 |
| SEQ. ID. NO. 22386 | 65-AsnThrSerProThrIleSerGlySerSerAlaGluValGlySerSerAsnAsnIleThrArgGlySerIleAlaLysProArgAlaIleAla-95 |
| SEQ. ID. NO. 22387 | 98-CysCysTrpProProGluSerTrpGluGlyLysAla-109 |
| SEQ. ID. NO. 22388 | 114-AlaSerProThrArgSerLysSerSer-122 |
| SEQ. ID. NO. 22389 | 145-AsnThrValArgCysGly-150 |

Hydrophilic Regions - Hopp-Woods

| | |
|---|---|
| SEQ. ID. NO. 22390 | 33-LysIleThrArgSerAlaThrSerArgAlaAsn-43 |
| SEQ. ID. NO. 22391 | 73-SerSerAlaGluValGlySer-79 |
| SEQ. ID. NO. 22392 | 87-SerIleAlaLysProArgAlaIleAla-95 |
| SEQ. ID. NO. 22393 | 116-ProThrArgSerLysSer-121 | a671
AMPHI Regions - AMPHI

| | |
|---|---|
| SEQ. ID. NO. 22394 | 96-ThrProArgIleAla-100 |
| SEQ. ID. NO. 22395 | 119-ArgLeuPheIleArgTyr-124 |

Antigenic Index - Jameson-Wolf

| | |
|---|---|
| SEQ. ID. NO. 22396 | 11-PheAsnAlaProAsnThrProProLysMetArgLeuAlaLysProLysProThrAlaGluThrAlaProValSerSerGluArg-38 |
| SEQ. ID. NO. 22397 | 45-GlnAlaMetThrAsnArgGluMetAsnAspArgAlaAsnAlaAsnArgArgGlyTrpAsnAspAlaLysAlaMetSerAlaLysGlyAlaAlaLysSerLeuAlaLysLysLysAlaThrThr-85 |
| SEQ. ID. NO. 22398 | 98-ArgIleAlaAspSerThrMet-104 |
| SEQ. ID. NO. 22399 | 110-AlaGluThrArgArgSerAlaThrGlyArgLeu-120 |
| SEQ. ID. NO. 22400 | 125-LeuThrGlyAspThr-129 |

Hydrophilic Regions - Hopp-Woods

| | |
|---|---|
| SEQ. ID. NO. 22401 | 16-ThrProProLysMetArgLeuAlaLysProLysProThrAlaGlu-30 |
| SEQ. ID. NO. 22402 | 32-AlaProValSerSerGluArg-38 |
| SEQ. ID. NO. 22403 | 47-MetThrAsnArgGluMetAsnAspArgAlaAsnAlaAsnArgArgGlyTrpAsnAspAlaLysAlaMetSerAlaLysGlyAlaAlaLysSerLeuAlaLysLysLysAlaThrThr-85 |
| SEQ. ID. NO. 22404 | 110-AlaGluThrArgArgSerAlaThr-117 | a672
AMPHI Regions - AMPHI

| | |
|---|---|
| SEQ. ID. NO. 22405 | 38-ArgAlaValAspIleIleLysAlaGlnLys-47 |
| SEQ. ID. NO. 22406 | 50-AlaAlaLeuProProPheValSerValVal-59 |
| SEQ. ID. NO. 22407 | 67-AlaGlnAsnIleArgArgIleLeuAlaGluValPro-78 |
| SEQ. ID. NO. 22408 | 91-AlaPheCysArgGlnPheHisArgProTyr-100 |
| SEQ. ID. NO. 22409 | 105-ArgValGlnThrAlaSerAspIleArgAsnAlaAlaAspArgPhe-119 |
| SEQ. ID. NO. 22410 | 131-HisProSerGluTyrGly-136 |
| SEQ. ID. NO. 22411 | 165-AsnValAspGluAlaIle-170 |
| SEQ. ID. NO. 22412 | 173-ThrGlyAlaGluAla-177 |

Antigenic Index - Jameson-Wolf

| | |
|---|---|
| SEQ. ID. NO. 22413 | 1-MetArgLysIleArgThrLysIleCysGlyIleThrThrProGluAspAlaLeu-18 |
| SEQ. ID. NO. 22414 | 34-ProGlnSerProArgAlaValAspIleIleLysAlaGlnLys-47 |
| SEQ. ID. NO. 22415 | 65-GluSerAlaGlnAsnIleArgArgIleLeuAla-75 |
| SEQ. ID. NO. 22416 | 84-PheHisGlyAspGluAspAspAlaPhe-92 |
| SEQ. ID. NO. 22417 | 107-GlnThrAlaSerAspIleArgAsnAlaAlaAspArgPheProAspAla-122 |
| SEQ. ID. NO. 22418 | 130-TyrHisProSerGluTyrGlyGlyThrGlyHisArgPheAsp-143 |
| SEQ. ID. NO. 22419 | 149-GluTyrSerGlyLysPro-154 |
| SEQ. ID. NO. 22420 | 159-GlyGlyLeuThrProGluAsnValAspGluAlaIleArg-171 |
| SEQ. ID. NO. 22421 | 176-GluAlaValAspValSerGlyGlyValGluAlaSerLysGlyLysLysAspProAlaLys-195 |
| SEQ. ID. NO. 22422 | 202-ThrAlaAsnArgLeuSerArg-208 |

TABLE 1-continued

Hydrophilic Regions - Hopp-Woods
SEQ. ID. NO. 22423    1-MetArgLysIleArgThrLysIle-8
SEQ. ID. NO. 22424    13-ThrProGluAspAlaLeu-18
SEQ. ID. NO. 22425    36-SerProArgAlaValAsp-41
SEQ. ID. NO. 22426    43-IleLysAlaGlnLys-47
SEQ. ID. NO. 22427    66-SerAlaGlnAsnIleArgArgIleLeuAla-75
SEQ. ID. NO. 22428    85-HisGlyAspGluAspAspAlaPhe-92
SEQ. ID. NO. 22429    110-SerAspIleArgAsnAlaAlaAspArgPheProAsp-121
SEQ. ID. NO. 22430    164-GluAsnValAspGluAlaIleArg-171
SEQ. ID. NO. 22431    184-ValGluAlaSerLysGlyLysLysAspProAlaLys-195
SEQ. ID. NO. 22432    204-AsnArgLeuSerArg-208
a673
AMPHI Regions - AMPHI
SEQ. ID. NO. 22433    84-LeuAsnAspArgLeuAsnGlnAsnValThrGluAlaLeuGlyGlyValAspVal-101
SEQ. ID. NO. 22434    110-ArgPheThrAspAla-114
SEQ. ID. NO. 22435    117-ValValLeuLysGlnLeuProLys-124
SEQ. ID. NO. 22436    172-ArgIleAlaAsnLeuLeuGluLeuIleLysProTyrLeu-184
SEQ. ID. NO. 22437    212-LysLeuPheArgTyrLeuGlyGluGlu-220
SEQ. ID. NO. 22438    261-GlyGluArgLeuLysLysIleSerThr-269
SEQ. ID. NO. 22439    275-MetGluLysLeuPhe-279
SEQ. ID. NO. 22440    285-LeuLysValTrpValLysValLys-292
Antigenic Index - Jameson-Wolf
SEQ. ID. NO. 22441    7-LeuAlaGlyGluArgAlaAlaAspGlyTyrArg-17
SEQ. ID. NO. 22442    24-ValGlyArgProAsnValGlyLysSerThr-33
SEQ. ID. NO. 22443    44-SerIleThrSerLysLysAlaGlnThrThrArgAsnArgValThr-58
SEQ. ID. NO. 22444    61-TyrThrAspAspThrAla-66
SEQ. ID. NO. 22445    73-ThrProGlyPheGlnThrAspHisArgAsnAlaLeuAsnAspArgLeuAsnGlnAsnValThrGlu-94
SEQ. ID. NO. 22446    110-ArgPheThrAspAlaAspArgValVal-118
SEQ. ID. NO. 22447    121-GlnLeuProLysHisThr-126
SEQ. ID. NO. 22448    134-LysIleAspLysAspLysAlaLysAspArgTyrAla-145
SEQ. ID. NO. 22449    153-ValArgAlaGluPhe-157
SEQ. ID. NO. 22450    180-IleLysProTyrLeuProGluSerVal-188
SEQ. ID. NO. 22451    190-MetTyrProGluAspMetValThrAspLysSerAlaArg-202
SEQ. ID. NO. 22452    208-IleValArgGluLysLeuPhe-214
SEQ. ID. NO. 22453    217-LeuGlyGluGluLeuPro-222
SEQ. ID. NO. 22454    227-ValGluValGluGlnPheGluGluGluAspGlyLeuAsn-239
SEQ. ID. NO. 22455    247-ValAspLysGluSerGlnLys-253
SEQ. ID. NO. 22456    258-GlyLysGlyGlyGluArgLeuLysLysIleSerThrGluAlaArgLeuAspMetGluLysLeuPheAsp-280
SEQ. ID. NO. 22457    291-ValLysSerGlyTrpAlaAspAspIleArgPheLeuArg-303
Hydrophilic Regions - Hopp-Woods
SEQ. ID. NO. 22458    7-LeuAlaGlyGluArgAlaAlaAspGlyTyrArg-17
SEQ. ID. NO. 22459    45-IleThrSerLysLysAlaGlnThrThrArgAsnArgVal-57
SEQ. ID. NO. 22460    61-TyrThrAspAspThrAla-66
SEQ. ID. NO. 22461    78-ThrAspHisArgAsnAlaLeuAsnAspArgLeuAsn-89
SEQ. ID. NO. 22462    110-ArgPheThrAspAlaAspArgValVal-118
SEQ. ID. NO. 22463    134-LysIleAspLysAspLysAlaLysAspArgTyrAla-145
SEQ. ID. NO. 22464    153-ValArgAlaGluPhe-157
SEQ. ID. NO. 22465    194-AspMetValThrAspLysSerAlaArg-202
SEQ. ID. NO. 22466    208-IleValArgGluLysLeuPhe-214
SEQ. ID. NO. 22467    217-LeuGlyGluGluLeuPro-222
SEQ. ID. NO. 22468    227-ValGluValGluGlnPheGluGluGluAspGlyLeuAsn-239
SEQ. ID. NO. 22469    247-ValAspLysGluSerGlnLys-253
SEQ. ID. NO. 22470    259-LysGlyGlyGluArgLeuLysLysIleSerThrGluAlaArgLeuAspMetGluLysLeuPheAsp-280
SEQ. ID. NO. 22471    293-SerGlyTrpAlaAspAspIleArgPheLeuArg-303
a674
AMPHI Regions - AMPHI
SEQ. ID. NO. 22472    16-ValTyrGlnSerLeuIle-21
SEQ. ID. NO. 22473    24-ThrAlaAlaProGluIleAlaLysAsnIleArgGluMetProAspPheAlaLys-41
SEQ. ID. NO. 22474    58-AlaAlaGluTyrIleArgGlnIleArgPro-67
SEQ. ID. NO. 22475    86-ThrAlaCysHisGluLeuSerAlaMetProGluThr-97
SEQ. ID. NO. 22476    107-IleGluValThrLysThrPheGlyGlyThrAspGlyHisLysPheValAsnGlyIleLeuAspLysLeuAla-130
Antigenic Index - Jameson-Wolf
SEQ. ID. NO. 22477    1-MetLysThrAlaArgArgArgSerArgGluLeuAla-12
SEQ. ID. NO. 22478    28-GluIleAlaLysAsnIleArgGluMetProAspPheAlaLysAlaAspGluGluLeuPhe-47
SEQ. ID. NO. 22479    54-ThrGlnThrAsnAla-58
SEQ. ID. NO. 22480    63-ArgGlnIleArgProLeuLeuAspArgAspGluLysAspLeuAsnProIleGluArg-81
SEQ. ID. NO. 22481    93-AlaMetProGluThrProTyr-99
SEQ. ID. NO. 22482    105-GluAlaIleGluValThrLysThrPheGlyGlyThrAspGlyHisLysPhe-121
SEQ. ID. NO. 22483    129-LeuAlaAlaGlnIleArgProAspGluProLysArgArg-141
Hydrophilic Regions - Hopp-Woods
SEQ. ID. NO. 22484    1-MetLysThrAlaArgArgArgSerArgGluLeuAla-12
SEQ. ID. NO. 22485    28-GluIleAlaLysAsnIleArgGluMetProAspPheAlaLysAlaAspGluGluLeuPhe-47
SEQ. ID. NO. 22486    63-ArgGlnIleArgProLeuLeuAspArgAspGluLysAspLeuAsnProIleGluArg-81
SEQ. ID. NO. 22487    105-GluAlaIleGluVal-109
SEQ. ID. NO. 22488    133-IleArgProAspGluProLysArgArg-141
a675
AMPHI Regions - AMPHI
SEQ. ID. NO. 22489    21-ArgPheThrAsnGluIleGlySerGluMetLeuLysValCysCysArgThrLeuGlnGluLeuGly-42
SEQ. ID. NO. 22490    74-AlaLeuIleAlaIle-78
SEQ. ID. NO. 22491    123-GlnAlaIleGluArgIleGluGluLysAlaSerAsp-134

TABLE 1-continued

SEQ. ID. NO. 22492  141-GluCysAlaAsnLeuValAsnLeuLeuLeuGlu-151
Antigenic Index - Jameson-Wolf
SEQ. ID. NO. 22493  6-ProAsnLeuAspGlyLysHisLeuArg-14
SEQ. ID. NO. 22494  26-IleGlySerGluMetLeu-31
SEQ. ID. NO. 22495  42-GlyValAlaAspGluAsnIle-48
SEQ. ID. NO. 22496  68-SerSerGluLysPheAsp-73
SEQ. ID. NO. 22497  82IleArgGlyGluThrTyr-87
SEQ. ID. NO. 22498  92-ValSerAsnGluSerGlyAlaGlyVal-100
SEQ. ID. NO. 22499  118-ThrGluAsnAspAlaGlnAlaIleGluArgIleGluGluLysAlaSerAspAlaAlaLysValAlaVal-140
SEQ. ID. NO. 22500  152-GluGlnPheGluAspGluGlu-158
Hydrophilic Regions - Hopp-Woods
SEQ. ID. NO. 22501  8-LeuAspGlyLysHisLeuArg-14
SEQ. ID. NO. 22502  26-IleGlySerGluMetLeu-31
SEQ. ID. NO. 22503  42-GlyValAlaAspGluAsnIle-48
SEQ. ID. NO. 22504  68-SerSerGluLysPheAsp-73
SEQ. ID. NO. 22505  82-IleArgGlyGluThrTyr-87
SEQ. ID. NO. 22506  92-ValSerAsnGluSerGlyAlaGly-99
SEQ. ID. NO. 22507  118-ThrGluAsnAspAlaGlnAlaIleGluArgIleGluGluLysAlaSerAspAlaAlaLysValAlaVal-140
SEQ. ID. NO. 22508  152-GluGlnPheGluAspGluGlu-158
a677
AMPHI Regions - AMPHI
SEQ. ID. NO. 22509  20-AlaArgLeuCysArgPheArgArg-27
SEQ. ID. NO. 22510  45-LeuThrProPheArgArgValAsnHisPheValAlaPheThrArgPheAsnGln-62
SEQ. ID. NO. 22511  78-IleAspPheIleAspAlaAsp-84
SEQ. ID. NO. 22512  86-PheAspGlyLeuLeuAla-91
SEQ. ID. NO. 22513  105-HisLeuValGlyArgPhe-110
SEQ. ID. NO. 22514  154-CysArgProValAspAspLeuAspAsp-162
SEQ. ID. NO. 22515  165-AlaPhePheIleAsnGlnLeuIleLysLeuValPheGlnCys-178
Antigenic Index - Jameson-Wolf
SEQ. ID. NO. 22516  23-CysArgPheArgArgHisSerArgSerValAsp-33
SEQ. ID. NO. 22517  35-AspValPheAspArgLysAspPheAsn-43
SEQ. ID. NO. 22518  59-ArgPheAsnGlnThrThrSerGlnArgArgAsnProArgAsnPheVal-74
SEQ. ID. NO. 22519  81-IleAspAlaAspAspPheAspGly-88
SEQ. ID. NO. 22520  96-GlnGlnThrAspGlyArgAlaGluLysHisLeu-106
SEQ. ID. NO. 22521  114-GlyIleAsnAspAspGlyGlyPhe-121
SEQ. ID. NO. 22522  124-LeuGlyGlnGluThrAspAlaAlaVal-132
SEQ. ID. NO. 22523  155-ArgProValAspAspLeuAspAspPheGly-164
SEQ. ID. NO. 22524  180-ProSerGlyGlyArgAsn-185
Hydrophilic Regions - Hopp-Woods
SEQ. ID. NO. 22525  23-CysArgPheArgArgHisSerArgSerValAsp-33
SEQ. ID. NO. 22526  35-AspValPheAspArgLysAspPhe-42
SEQ. ID. NO. 22527  64-ThrSerGlnArgArgAsnProArg-71
SEQ. ID. NO. 22528  81-IleAspAlaAspAspPheAsp-87
SEQ. ID. NO. 22529  96-GlnGlnThrAspGlyArgAlaGluLysHisLeu-106
SEQ. ID. NO. 22530  115-IleAsnAspAspGlyGly-120
SEQ. ID. NO. 22531  125-GlyGlnGluThrAspAlaAlaVal-132
SEQ. ID. NO. 22532  155-ArgProValAspAspLeuAspAsp-162
a678
AMPHI Regions - AMPHI
SEQ. ID. NO. 22533  10-LeuValSerAlaIleIle-15
SEQ. ID. NO. 22534  24-MetArgGlyValIle-28
SEQ. ID. NO. 22535  47-PheAlaAlaProPhe-51
SEQ. ID. NO. 22536  79-LeuIleGlnLysIleLeuArgSerLeuLeuThrGlyAla-91
SEQ. ID. NO. 22537  102-ArgIleLeuGlyGlyValPheGlyAlaLeuLysGlyIleLeu-115
SEQ. ID. NO. 22538  130-ProAspThrGluGlu-134
Antigenic Index - Jameson-Wolf
SEQ. ID. NO. 22539  125-SerLysThrAspLeuProAspThrGluGluTrpArgGlnSerTyrThr-140
SEQ. ID. NO. 22540  154-HisSerGlyGlyThrAlaGluThrProGluAspAsp-165
Hydrophilic Regions - Hopp-Woods
SEQ. ID. NO. 22541  125-SerLysThrAspLeuProAspThrGluGluTrpArgGln-137
SEQ. ID. NO. 22542  157-GlyThrAlaGluThrProGluAspAsp-165
a681
AMPHI Regions - AMPHI
SEQ. ID. NO. 22543  12-PheSerGluGluAlaLysPheIleSerAlaMet-22
SEQ. ID. NO. 22544  102-LeuProValGlyAsp-106
SEQ. ID. NO. 22545  122-ArgLeuGlyGluGlnCys-127
SEQ. ID. NO. 22546  137-IleGlyGluAlaAspAspAlaGluValValArgValValGlyValPheValGly-154
SEQ. ID. NO. 22547  202-LysCysValHisCysGly-207
SEQ. ID. NO. 22548  210-XxxGlyGlyLysLeuAlaAspPheThrThrIle-220
SEQ. ID. NO. 22549  234-CysAlaProPheAlaAlaLeuArgCysPheCysIlePheGlyValTrpLysArgIleArgAlaValPheCysGlyArg-259
Antigenic Index - Jameson-Wolf
SEQ. ID. NO. 22550  11-AsnPheSerGluGluAlaLysPhe-18
SEQ. ID. NO. 22551  39-AlaThrProAsnSerTrpArgValArgGlnGln-49
SEQ. ID. NO. 22552  59-LeuValLysArgAlaCys-64
SEQ. ID. NO. 22553  67-ProMetArgArgCysLeuProSerArgLeu-76
SEQ. ID. NO. 22554  89-GlyGlyPheGlyMetProSerGluGlySerVal-99
SEQ. ID. NO. 22555  103-ProValGlyAspGlyLeuGlu-109
SEQ. ID. NO. 22556  120-AlaPheArgLeuGlyGluGlnCysGlyGlyPhe-130
SEQ. ID. NO. 22557  136-AspIleGlyGluAlaAspAspAlaGluVal-145
SEQ. ID. NO. 22558  157-AlaAlaGluGluThrPro-162

TABLE 1-continued

| | |
|---|---|
| SEQ. ID. NO. 22559 | 167-PheLysAsnGlyGly-171 |
| SEQ. ID. NO. 22560 | 173-AlaValGluGluAlaAspGly-179 |
| SEQ. ID. NO. 22561 | 185-AspGlyValGlyGlyAspAlaAlaValGluCysArgGlyLysCysLeuCys-201 |
| SEQ. ID. NO. 22562 | 207-GlyAsnThrXxxGlyGlyLysLeuAlaAsp-216 |
| SEQ. ID. NO. 22563 | 224-SerAlaAspGlyGlyGly-229 |
| SEQ. ID. NO. 22564 | 256-PheCysGlyArgArg-260 |
| Hydrophilic Regions - Hopp-Woods | |
| SEQ. ID. NO. 22565 | 11-AsnPheSerGluGluAlaLysPhe-18 |
| SEQ. ID. NO. 22566 | 44-TrpArgValArgGln-48 |
| SEQ. ID. NO. 22567 | 59-LeuValLysArgAlaCys-64 |
| SEQ. ID. NO. 22568 | 67-ProMetArgArgCysLeuPro-73 |
| SEQ. ID. NO. 22569 | 95-SerGluGlySerVal-99 |
| SEQ. ID. NO. 22570 | 120-AlaPheArgLeuGlyGluGln-126 |
| SEQ. ID. NO. 22571 | 136-AspIleGlyGluAlaAspAspAlaGluVal-145 |
| SEQ. ID. NO. 22572 | 157-AlaAlaGluGluThrPro-162 |
| SEQ. ID. NO. 22573 | 173-AlaValGluGluAlaAspGly-179 |
| SEQ. ID. NO. 22574 | 191-AlaAlaValGluCysArgGlyLysCysLeu-200 |
| SEQ. ID. NO. 22575 | 210-XxxGlyGlyLysLeuAlaAsp-216 |
| SEQ. ID. NO. 22576 | 256-PheCysGlyArgArg-260 |
| a682 | |
| AMPHI Regions - AMPHI | |
| SEQ. ID. NO. 22577 | 33-ArgLeuArgLysCysGlyArgIleLeuSerGlyIleCysGluProPhe-48 |
| Antigenic Index - Jameson-Wolf | |
| SEQ. ID. NO. 22578 | 9-SerTyrGlyLysTrpArgLysAsnTrpAspIle-19 |
| SEQ. ID. NO. 22579 | 30-SerSerThrArgLeuArgLysCysGlyArg-39 |
| SEQ. ID. NO. 22580 | 95-ArgPheProThrAspArgProIleLeu-103 |
| SEQ. ID. NO. 22581 | 112-IleSerProArgThrGlyPheArgTyrProThrArgSerLeuProLysSerLysLysAlaTyrGly-133 |
| Hydrophilic Regions - Hopp-Woods | |
| SEQ. ID. NO. 22582 | 12-LysTrpArgLysAsnTrpAsp-18 |
| SEQ. ID. NO. 22583 | 32-ThrArgLeuArgLysCysGlyArg-39 |
| SEQ. ID. NO. 22584 | 97-ProThrAspArgProIleLeu-103 |
| SEQ. ID. NO. 22585 | 124-SerLeuProLysSerLysLysAlaTyrGly-133 |
| a683 | |
| AMPHI Regions - AMPHI | |
| SEQ. ID. NO. 22586 | 26-ThrProAspLysSerAlaArgTrpGluAsnIleGlyThrIleSerAsn-41 |
| SEQ. ID. NO. 22587 | 101-SerSerLeuGlnLeuPhe-106 |
| SEQ. ID. NO. 22588 | 124-ArgProMetSerIleLeuSerGly-131 |
| Antigenic Index - Jameson-Wolf | |
| SEQ. ID. NO. 22589 | 24-CysSerThrProAspLysSerAlaArgTrpGluAsn-35 |
| SEQ. ID. NO. 22590 | 37-GlyThrIleSerAsnGly-42 |
| SEQ. ID. NO. 22591 | 48-IleAsnLysAspSerValArgLysAsnGlyAsn-58 |
| SEQ. ID. NO. 22592 | 63-XxxAspLysLysValValThrAsnLeuLysGlnGluArgPheAla-77 |
| SEQ. ID. NO. 22593 | 93-CysAsnAsnLysThrTyrArgLeu-100 |
| SEQ. ID. NO. 22594 | 106-PheAspThrLysAsnThrGluIleSerThr-115 |
| SEQ. ID. NO. 22595 | 119-ThrAlaSerSerLeuArgPro-125 |
| SEQ. ID. NO. 22596 | 131-GlyThrLeuThrGluLysGlnTyrGlu-139 |
| SEQ. ID. NO. 22597 | 141-ValCysGlyLysLysLeu-146 |
| Hydrophilic Regions - Hopp-Woods | |
| SEQ. ID. NO. 22598 | 25-SerThrProAspLysSerAlaArgTrpGluAsn-35 |
| SEQ. ID. NO. 22599 | 48-IleAsnLysAspSerValArgLysAsnGly-57 |
| SEQ. ID. NO. 22600 | 63-XxxAspLysLysValValThr-69 |
| SEQ. ID. NO. 22601 | 71-LeuLysGlnGluArgPheAla-77 |
| SEQ. ID. NO. 22602 | 107-AspThrLysAsnThrGluIleSer-114 |
| SEQ. ID. NO. 22603 | 133-LeuThrGluLysGlnTyrGlu-139 |
| SEQ. ID. NO. 22604 | 141-ValCysGlyLysLysLeu-146 |
| a684 | |
| AMPHI Regions - AMPHI | |
| SEQ. ID. NO. 22605 | 13-AlaAlaCysGlyThrValGln-19 |
| SEQ. ID. NO. 22606 | 47-LeuAlaGluProLeu-51 |
| SEQ. ID. NO. 22607 | 73-TrpAlaAspThrLeuAspAspMetLeuGluAlaAlaLeuSerAsnAlaPheAsnArgLeuAspSerThr-95 |
| SEQ. ID. NO. 22608 | 110-TrpThrValTyrIleAspAlaPheGlnGlySerTyr-121 |
| SEQ. ID. NO. 22609 | 154-AlaMetThrAlaAlaLeuGluGlnGlyLeuLysGlnAlaAlaGlnGlnMetVal-171 |
| Antigenic Index - Jameson-Wolf | |
| SEQ. ID. NO. 22610 | 26-LeuProAspSerArgTyrIleArgProAlaThrGlnGlyGlyGluThrAlaValGluValArgLeuAlaGluProLeuLysArgGlyGlyLeu-56 |
| SEQ. ID. NO. 22611 | 60-ThrAspProTyrArgLeuAsnThrAlaGln-69 |
| SEQ. ID. NO. 22612 | 76-ThrLeuAspAspMetLeuGlu-82 |
| SEQ. ID. NO. 22613 | 90-AsnArgLeuAspSerThrArg-96 |
| SEQ. ID. NO. 22614 | 101-AlaSerArgSerGlySerThrGluLys-109 |
| SEQ. ID. NO. 22615 | 117-PheGlnGlySerTyrThrGlyLysThrLeu-126 |
| SEQ. ID. NO. 22616 | 133-LeuProAspGlyThrAsnArgProPheHisIleGluThrGluGlnGlnGlyAspGlyTyrAla-153 |
| SEQ. ID. NO. 22617 | 161-GlnGlyLeuLysGlnAlaAla-167 |
| Hydrophilic Regions - Hopp-Woods | |
| SEQ. ID. NO. 22618 | 27-ProAspSerArgTyrIleArg-33 |
| SEQ. ID. NO. 22619 | 35-AlaThrGlnGlyGlyGluThrAlaValGluValArgLeuAlaGluProLeuLysArgGlyGly-55 |
| SEQ. ID. NO. 22620 | 76-ThrLeuAspAspMetLeuGlu-82 |
| SEQ. ID. NO. 22621 | 90-AsnArgLeuAspSer-94 |
| SEQ. ID. NO. 22622 | 102-SerArgSerGlySerThrGluLys-109 |
| SEQ. ID. NO. 22623 | 141-PheHisIleGluThrGluGlnGlnGlyAsp-150 |
| SEQ. ID. NO. 22624 | 161-GlnGlyLeuLysGlnAlaAla-167 |

TABLE 1-continued a685
AMPHI Regions - AMPHI
SEQ. ID. NO. 22625   7-AsnPheAlaPheCysGlyValVal-14
SEQ. ID. NO. 22626   44-CysAlaValLeuLeu-48
SEQ. ID. NO. 22627   94-TrpAlaAlaLeuAspThrLeuThrGluLeu-103
SEQ. ID. NO. 22628   137-TyrGluAlaLeuHisArgTyr-143
SEQ. ID. NO. 22629   154-GlyAlaGluAlaTyrGluGlnLeuAlaLysAsn-164
SEQ. ID. NO. 22630   182-GluLysGlnMetGluThrLeuAlaArgIlePheGlyLysGlu-195
SEQ. ID. NO. 22631   206-AspAlaLeuPheAla-210
SEQ. ID. NO. 22632   296-AlaValGluValLeuAspAsnAlaLeuVal-305
SEQ. ID. NO. 22633   336-AlaAlaGluGlnLeuLysGluAlaPhe-344
Antigenic Index - Jameson-Wolf
SEQ. ID. NO. 22634   20-LeuAsnAsnLysHisSerTyrSerTyrAlaLysGluProHisThrValLysProArgPhe-39
SEQ. ID. NO. 22635   52-SerProGluProAlaAlaGluLysThrValSer-62
SEQ. ID. NO. 22636   74-ProThrAlaArgGlyAspAlaValValProLysAsnProGluArgValAla-90
SEQ. ID. NO. 22637   122-AlaPheAspLysAlaAla-127
SEQ. ID. NO. 22638   133-PheGluProAspTyrGluAlaLeuHisArgTyrAsn-144
SEQ. ID. NO. 22639   151-GlyGlyProGlyAlaGluAlaTyrGluGlnLeuAlaLysAsnAlaThr-166
SEQ. ID. NO. 22640   170-LeuThrValAspAsnGlyAsnIleArgThrSerGlyGluLysGlnMetGluThrLeu-188
SEQ. ID. NO. 22641   192-PheGlyLysGluAlaArgAlaAlaGluLeuLysAlaGlnIle-205
SEQ. ID. NO. 22642   211-GlnThrArgGluAlaAlaLysGlyLysGlyArgGlyLeu-223
SEQ. ID. NO. 22643   227-ValThrGlyAsnLysValSerAlaPheGlyThrGlnSerArgLeu-241
SEQ. ID. NO. 22644   247-GlyAspIleGlyLeuProProValAspGluSerLeuArgAsnGluGlyHisGlyGln-265
SEQ. ID. NO. 22645   271-TyrIleLysGluLysAsnProAspTrpIle-280
SEQ. ID. NO. 22646   285-ArgThrAlaAlaIleGlyGlnGluGlyProAla-295
SEQ. ID. NO. 22647   307-GlyThrAsnAlaTrpLysArgLysGln-315
SEQ. ID. NO. 22648   328-GlyGlySerArgGlnLeu-333
SEQ. ID. NO. 22649   338-GluGlnLeuLysGluAlaPheGluLysAlaGluPro-349
SEQ. ID. NO. 22650   351-AlaAlaGlyLysGlu-355
Hydrophilic Regions - Hopp-Woods
SEQ. ID. NO. 22651   28-TyrAlaLysGluProHisThrValLys-36
SEQ. ID. NO. 22652   52-SerProGluProAlaAlaGluLysThrValSer-62
SEQ. ID. NO. 22653   75-ThrAlaArgGlyAspAlaValVal-82
SEQ. ID. NO. 22654   84-LysAsnProGluArgValAla-90
SEQ. ID. NO. 22655   122-AlaPheAspLysAlaAla-127
SEQ. ID. NO. 22656   135-ProAspTyrGluAla-139
SEQ. ID. NO. 22657   156-GluAlaTyrGluGlnLeuAlaLys-163
SEQ. ID. NO. 22658   175-GlyAsnIleArgThrSerGlyGluLysGlnMetGluThrLeu-188
SEQ. ID. NO. 22659   192-PheGlyLysGluAlaArgAlaAlaGluLeuLysAlaGlnIle-205
SEQ. ID. NO. 22660   211-GlnThrArgGluAlaAlaLysGlyLysGlyArgGly-222
SEQ. ID. NO. 22661   253-ProValAspGluSerLeuArgAsnGluGlyHisGly-264
SEQ. ID. NO. 22662   271-TyrIleLysGluLysAsnPro-277
SEQ. ID. NO. 22663   290-GlyGlnGluGlyProAla-295
SEQ. ID. NO. 22664   309-AsnAlaTrpLysArgLysGln-315
SEQ. ID. NO. 22665   338-GluGlnLeuLysGluAlaPheGluLysAlaGluPro-349
SEQ. ID. NO. 22666   351-AlaAlaGlyLysGlu-355
a686
AMPHI Regions - AMPHI
SEQ. ID. NO. 22667   10-AspValPheAspAspIleCysSerAlaValGluSerPheGlyGlyIleAlaArgSerValGlnLeu-31
SEQ. ID. NO. 22668   50-ThrThrGlyIleValGluThrValAspLysProLeu-61
SEQ. ID. NO. 22669   70-ValGluAlaAspIle-74
SEQ. ID. NO. 22670   86-IleProArgAlaPheGlySerGlyIleAlaAlaAlaLeu-98
Antigenic Index - Jameson-Wolf
SEQ. ID. NO. 22671   1-TerTerAsnPheSerCysArgAlaAspAspValPheAsp-13
SEQ. ID. NO. 22672   46-LeuArgGlnHisThrThrGlyIle-53
SEQ. ID. NO. 22673   55-GluThrValAspLysProLeuSerGlyAla-64
SEQ. ID. NO. 22674   70-ValGluAlaAspIle-74
SEQ. ID. NO. 22675   115-AspAlaValLysAlaGluSerValAsnGlyThrThrGly-127
Hydrophilic Regions - Hopp-Woods
SEQ. ID. NO. 22676   6-CysArgAlaAspAspValPheAsp-13
SEQ. ID. NO. 22677   55-GluThrValAspLysProLeuSer-62
SEQ. ID. NO. 22678   70-ValGluAlaAspIle-74
SEQ. ID. NO. 22679   115-AspAlaValLysAlaGluSerValAsn-123
a687
AMPHI Regions - AMPHI
SEQ. ID. NO. 22680   11-AlaAlaLeuPheAlaLeu-16
SEQ. ID. NO. 22681   64-LysValGluValLeuGluPhePheGlyTyrPheCysPro-76
SEQ. ID. NO. 22682   78-CysAlaHisLeuGluProValLeuSerLysHisAlaLysSerPhe-92
SEQ. ID. NO. 22683   112-LeuAlaArgLeuAlaAlaAla-118
SEQ. ID. NO. 22684   135-PheAspAlaMetVal-139
SEQ. ID. NO. 22685   148-ProValLeuLysLysTrpLeu-155
SEQ. ID. NO. 22686   176-GlnAlaArgAlaAspLysMetGlnGluLeuThrGluThrPhe-189
Antigenic Index - Jameson-Wolf
SEQ. ID. NO. 22687   1-MetLysSerLysHis-5
SEQ. ID. NO. 22688   19-CysAspSerLysValGlnThrSerValProAlaAspSerAlaPro-33
SEQ. ID. NO. 22689   43-GlyLeuValGluGlyGlnAsnTyr-50
SEQ. ID. NO. 22690   56-ProIleProGlnGlnGlnAlaGlyLysValGluVal-67
SEQ. ID. NO. 22691   87-LysHisAlaLysSerPheLysAspAspMetTyrLeu-98
SEQ. ID. NO. 22692   122-AlaAlaAlaAspSerLysAspValAlaAsn-131
SEQ. ID. NO. 22693   141-GlnLysIleLysLeuGlnGluProGluValLeuLys-152

TABLE 1-continued

| | |
|---|---|
| SEQ. ID. NO. 22694 | 159-ThrAlaPheAspGlyLysLysVal-166 |
| SEQ. ID. NO. 22695 | 171-GluSerProGluSerGlnAlaArgAlaAspLysMetGlnGluLeuThrGlu-187 |
| SEQ. ID. NO. 22696 | 189-PheGlnIleAspGlyThrPro-195 |
| SEQ. ID. NO. 22697 | 199-ValGlyGlyLysTyrLysValGluPheAlaAsp-209 |
| SEQ. ID. NO. 22698 | 211-GluSerGlyMetAsnThr-216 |
| SEQ. ID. NO. 22699 | 220-LeuAlaAspLysValArgGluGluGlnLysAlaAlaHis-232 |

Hydrophilic Regions - Hopp-Woods

| | |
|---|---|
| SEQ. ID. NO. 22700 | 1-MetLysSerLysHis-5 |
| SEQ. ID. NO. 22701 | 19-CysAspSerLysValGlnThr-25 |
| SEQ. ID. NO. 22702 | 27-ValProAlaAspSerAlaPro-33 |
| SEQ. ID. NO. 22703 | 61-GlnAlaGlyLysValGluVal-67 |
| SEQ. ID. NO. 22704 | 87-LysHisAlaLysSerPheLysAspAspMetTyrLeu-98 |
| SEQ. ID. NO. 22705 | 122-AlaAlaAlaAspSerLysAspValAla-130 |
| SEQ. ID. NO. 22706 | 141-GlnLysIleLysLeuGlnGluProGluValLeuLys-152 |
| SEQ. ID. NO. 22707 | 159-ThrAlaPheAspGlyLysLysVal-166 |
| SEQ. ID. NO. 22708 | 171-GluSerProGluSerGlnAlaArgAlaAspLysMetGlnGluLeuThrGlu-187 |
| SEQ. ID. NO. 22709 | 201-GlyLysTyrLysValGluPheAlaAsp-209 |
| SEQ. ID. NO. 22710 | 220-LeuAlaAspLysValArgGluGluGlnLysAlaAlaHis-232 | a688
AMPHI Regions - AMPHI

| | |
|---|---|
| SEQ. ID. NO. 22711 | 23-LeuSerAlaLeuLeuGlyLeu-29 |
| SEQ. ID. NO. 22712 | 120-GlyAsnAlaLeuGlnAsnAlaAla-127 |

Antigenic Index - Jameson-Wolf

| | |
|---|---|
| SEQ. ID. NO. 22713 | 4-TyrProSerArgPheAlaGln-10 |
| SEQ. ID. NO. 22714 | 13-IleSerValAsnLys-17 |
| SEQ. ID. NO. 22715 | 47-IleIleGlnGlyAsnGluLeuGluProArgAla-57 |
| SEQ. ID. NO. 22716 | 61-LeuArgProGlyMetThrLysAspGln-69 |
| SEQ. ID. NO. 22717 | 82-AlaPheHisThrAspArgTrpAspTyr-90 |
| SEQ. ID. NO. 22718 | 93-AsnThrSerArgAsnGlyIleIleLysAspArgSerAsn-105 |
| SEQ. ID. NO. 22719 | 116-ValArgThrGluGlyAsnAla-122 |
| SEQ. ID. NO. 22720 | 125-AsnAlaAlaGluAlaLeuArgValLysGlnAsnAlaAspLysGln-139 |

Hydrophilic Regions - Hopp-Woods

| | |
|---|---|
| SEQ. ID. NO. 22721 | 51-AsnGluLeuGluProArgAla-57 |
| SEQ. ID. NO. 22722 | 64-GlyMetThrLysAspGln-69 |
| SEQ. ID. NO. 22723 | 98-GlyIleIleLysAspArgSerAsn-105 |
| SEQ. ID. NO. 22724 | 116-ValArgThrGluGlyAsnAla-122 |
| SEQ. ID. NO. 22725 | 125-AsnAlaAlaGluAlaLeuArgValLysGlnAsnAlaAspLysGln-139 | a689
AMPHI Regions - AMPHI

| | |
|---|---|
| SEQ. ID. NO. 22726 | 55-TyrProGluMetSerGluLysLeuMet-63 |
| SEQ. ID. NO. 22727 | 65-ValLeuMetAlaMetLeuValThrLeu-73 |
| SEQ. ID. NO. 22728 | 82-LeuProAlaIleProGluMetAlaGln-90 |
| SEQ. ID. NO. 22729 | 111-AlaPheGlyGlnValValGlyGly-118 |
| SEQ. ID. NO. 22730 | 123-IleLysGlyArgLys-127 |
| SEQ. ID. NO. 22731 | 154-LeuAsnLeuArgValValGlnAlaPheGlyAlaGly-165 |
| SEQ. ID. NO. 22732 | 188-PheAlaLeuIleGlyIleIleLeu-195 |
| SEQ. ID. NO. 22733 | 203-ProMetValGlyAlaLeuLeuGlnGlyLeuGlyGlyTrpGlnAlaIlePheVal-220 |
| SEQ. ID. NO. 22734 | 230-LeuGlyLeuValGlnTyrPhe-236 |
| SEQ. ID. NO. 22735 | 245-LysIleGlyArgAspVal-250 |
| SEQ. ID. NO. 22736 | 257-ArgPheLysArgValLeu-262 |
| SEQ. ID. NO. 22737 | 277-SerPheGlySerMetPheAla-283 |
| SEQ. ID. NO. 22738 | 314-MetMetPhePheAsnArgIleThr-321 |
| SEQ. ID. NO. 22739 | 344-AlaAlaAsnLeuSerGlnLeuAlaAlaValLeuPhe-355 |
| SEQ. ID. NO. 22740 | 400-ValLeuGlyValPheGlnSerLeuIleGly-409 |

Antigenic Index - Jameson-Wolf

| | |
|---|---|
| SEQ. ID. NO. 22741 | 36-PheArgArgArgAlaVal-41 |
| SEQ. ID. NO. 22742 | 45-IleGlyArgGluPheMetProSer-52 |
| SEQ. ID. NO. 22743 | 57-GluMetSerGluLysLeu-62 |
| SEQ. ID. NO. 22744 | 95-AspValHisArgIleGluGln-101 |
| SEQ. ID. NO. 22745 | 119-SerValSerAspIleLysGlyArgLysProVal-129 |
| SEQ. ID. NO. 22746 | 174-MetValArgAspTyrTyrSerGlyArgLysAlaAla-185 |
| SEQ. ID. NO. 22747 | 238-ProLysProAlaValGlyGlyLysIleGlyArgAspValPhe-251 |
| SEQ. ID. NO. 22748 | 257-ArgPheLysArgValLeuLysThrArgAla-266 |
| SEQ. ID. NO. 22749 | 325-LeuLysThrGlyValHis-330 |
| SEQ. ID. NO. 22750 | 390-PheLysGluGluGlyGlySer-396 |
| SEQ. ID. NO. 22751 | 448-ArgAlaTrpLysGluAsnGlyGlnSerGluTyrLeu-459 |

Hydrophilic Regions - Hopp-Woods

| | |
|---|---|
| SEQ. ID. NO. 22752 | 36-PheArgArgArgAlaVal-41 |
| SEQ. ID. NO. 22753 | 45-IleGlyArgGluPheMet-50 |
| SEQ. ID. NO. 22754 | 57-GluMetSerGluLysLeu-62 |
| SEQ. ID. NO. 22755 | 95-AspValHisArgIleGluGln-101 |
| SEQ. ID. NO. 22756 | 119-SerValSerAspIleLysGlyArgLysProVal-129 |
| SEQ. ID. NO. 22757 | 178-TyrTyrSerGlyArgLysAlaAla-185 |
| SEQ. ID. NO. 22758 | 245-LysIleGlyArgAspVal-250 |
| SEQ. ID. NO. 22759 | 257-ArgPheLysArgValLeuLysThrArgAla-266 |
| SEQ. ID. NO. 22760 | 390-PheLysGluGluGlyGlySer-396 |
| SEQ. ID. NO. 22761 | 448-ArgAlaTrpLysGluAsnGlyGln-455 | a690
AMPHI Regions - AMPHI

| | |
|---|---|
| SEQ. ID. NO. 22762 | 36-AlaSerSerThrAlaSerAla-42 |

TABLE 1-continued

| | |
|---|---|
| SEQ. ID. NO. 22763 | 57-SerAlaProAspAsnValLysGlnAlaGlu-66 |
| SEQ. ID. NO. 22764 | 68-ValProProSerAsnCysThrAspLeuHisProAlaThrGlyIleAspAspLeuMetGlnGlnIleAlaGluHisIle-93 |
| SEQ. ID. NO. 22765 | 116-GlyTyrAspAsnIleGlnArgLeu-123 |
| SEQ. ID. NO. 22766 | 151-ArgThrIleSerArgGlnAlaGlnAspAla-160 |
| SEQ. ID. NO. 22767 | 189-ProLysArgThrArgTyrPhe-195 |
| SEQ. ID. NO. 22768 | 213-GlyAsnPheGlnTyrIleGlyGlnLeuProGlyTyrLeuLys-226 |

Antigenic Index - Jameson-Wolf

| | |
|---|---|
| SEQ. ID. NO. 22769 | 1-MetLysAsnLysThrSer-6 |
| SEQ. ID. NO. 22770 | 21-SerProSerLysGluAspLysThrLysGluAsnGlyAla-33 |
| SEQ. ID. NO. 22771 | 43-AlaSerSerSerAlaProGlnThrAspLeu-52 |
| SEQ. ID. NO. 22772 | 57-SerAlaProAspAsnValLysGlnAlaGluSerValProProSerAsnCysThrAspLeuHisProAlaThrGlyIleAspAspLeuMet-86 |
| SEQ. ID. NO. 22773 | 91-GluHisIleAspSerAspCys-97 |
| SEQ. ID. NO. 22774 | 104-HisGluLeuGluThrArgPhe-110 |
| SEQ. ID. NO. 22775 | 112-LeuProGlyGlyGlyTyrAspAsnIleGln-121 |
| SEQ. ID. NO. 22776 | 126-ProAspIleArgProGluAspProAspTyrHisGln-137 |
| SEQ. ID. NO. 22777 | 144-GluAspLeuArgTyrGlyLysArgThrIleSerArgGlnAlaGln-158 |
| SEQ. ID. NO. 22778 | 160-AlaLeuMetGluGlnGluArgArgLeuArgGlu-170 |
| SEQ. ID. NO. 22779 | 177-GlnGlySerGlnGluThrArgGlyGlnGlyGluGluProLysArgThrArgTyr-194 |
| SEQ. ID. NO. 22780 | 198-SerAlaThrProAlaTyrSerSerArgHisAsnAsnGlyLeuGlyGlyAsn-214 |
| SEQ. ID. NO. 22781 | 228-HisGlyGluMetLeuGluAsnGlnSerLeu-237 |
| SEQ. ID. NO. 22782 | 239-ArgLeuSerAsnArgGluArgAsnProAspLysProPheLeu-252 |
| SEQ. ID. NO. 22783 | 255-HisPheAspGluAsnGlyLysIleThr-263 |
| SEQ. ID. NO. 22784 | 267-ValTyrGluLysAsnIleTyrPheAsnProAsnLeuGlyArgArg-281 |

Hydrophilic Regions - Hopp-Woods

| | |
|---|---|
| SEQ. ID. NO. 22785 | 1-MetLysAsnLysThr-5 |
| SEQ. ID. NO. 22786 | 21-SerProSerLysGluAspLysThrLysGluAsnGlyAla-33 |
| SEQ. ID. NO. 22787 | 46-SerAlaProGlnThrAspLeu-52 |
| SEQ. ID. NO. 22788 | 57-SerAlaProAspAsnValLysGlnAlaGluSerValPro-69 |
| SEQ. ID. NO. 22789 | 81-GlyIleAspAspLeuMet-86 |
| SEQ. ID. NO. 22790 | 91-GluHisIleAspSer-95 |
| SEQ. ID. NO. 22791 | 104-HisGluLeuGluThr-108 |
| SEQ. ID. NO. 22792 | 128-IleArgProGluAspProAspTyrHis-136 |
| SEQ. ID. NO. 22793 | 144-GluAspLeuArgTyrGlyLysArgThrIleSerArgGlnAlaGln-158 |
| SEQ. ID. NO. 22794 | 160-AlaLeuMetGluGlnGluArgArgLeuArgGlu-170 |
| SEQ. ID. NO. 22795 | 178-GlySerGlnGluThrArgGlyGlnGlyGluGluProLysArgThrArgTyr-194 |
| SEQ. ID. NO. 22796 | 203-TyrSerSerArgHisAsnAsn-209 |
| SEQ. ID. NO. 22797 | 228-HisGlyGluMetLeuGlu-233 |
| SEQ. ID. NO. 22798 | 240-LeuSerAsnArgGluArgAsnProAspLysProPhe-251 |
| SEQ. ID. NO. 22799 | 255-HisPheAspGluAsnGlyLysIleThr-263 | a691
AMPHI Regions - AMPHI

| | |
|---|---|
| SEQ. ID. NO. 22800 | 11-LysProAlaAlaSer-15 |
| SEQ. ID. NO. 22801 | 55-HisAsnGluLeuArgLysIleArgAla-63 |
| SEQ. ID. NO. 22802 | 108-ArgTyrLeuSerGly-112 |

Antigenic Index - Jameson-Wolf

| | |
|---|---|
| SEQ. ID. NO. 22803 | 7-CysArgPheAlaLys-11 |
| SEQ. ID. NO. 22804 | 36-LeuAsnAspPheGlnProAsnCysAspIleArgArgLeuGlyLeuThrGlnGlyGlnHisAsnGluLeuArgLysIleArgAla-63 |
| SEQ. ID. NO. 22805 | 67-MetAlaGlyAspArgAlaArgLeuLysValMetHis-78 |
| SEQ. ID. NO. 22806 | 80-GluHisSerArgArgArgSerVal-87 |
| SEQ. ID. NO. 22807 | 91-IleSerSerAspValPheAsnArgAsnGluAlaArgAspTyrValGluSerArgTyrLeuSerGlyMetAspPheAlaValAspGluLeuGluIle-122 |
| SEQ. ID. NO. 22808 | 131-ThrProGlnGlnGlnGln-136 |
| SEQ. ID. NO. 22809 | 140-SerSerCysLeuLys-144 |

Hydrophilic Regions - Hopp-Woods

| | |
|---|---|
| SEQ. ID. NO. 22810 | 43-CysAspIleArgArgLeuGly-49 |
| SEQ. ID. NO. 22811 | 54-GlnHisAsnGluLeuArgLysIleArgAla-63 |
| SEQ. ID. NO. 22812 | 67-MetAlaGlyAspArgAlaArgLeuLysValMetHis-78 |
| SEQ. ID. NO. 22813 | 80-GluHisSerArgArgArgSerVal-87 |
| SEQ. ID. NO. 22814 | 95-ValPheAsnArgAsnGluAlaArgAspTyrValGlu-106 |
| SEQ. ID. NO. 22815 | 115-PheAlaValAspGluLeuGluIle-122 | a692
AMPHI Regions - AMPHI

| | |
|---|---|
| SEQ. ID. NO. 22816 | 6-CysArgCysSerGluSerIleArgArgIleArgArgAsn-18 |
| SEQ. ID. NO. 22817 | 77-LeuGlyTyrPheLysProLeuAlaValPheVal-88 |
| SEQ. ID. NO. 22818 | 106-GlnGlyPheGlyGlnLeuHis-112 |
| SEQ. ID. NO. 22819 | 132-ThrArgGlnLeuArgGlyPheLys-139 |
| SEQ. ID. NO. 22820 | 143-PheAspValPheGlnValPheGlyAsn-151 |
| SEQ. ID. NO. 22821 | 170-GlnPheValGluHisHis-175 |
| SEQ. ID. NO. 22822 | 177-AspAlaGlyGluValGlyArgValValGlyArgGlyTyrGlyAlaAlaValPheAspPhePheGlnArgPheGlnLeu-202 |
| SEQ. ID. NO. 22823 | 205-ValGlnSerGlnArgArgGlyArgHisLeuGluAspPheGlyAsp-219 |
| SEQ. ID. NO. 22824 | 254-ValGlyLysLeuAspGlnPheAspGlyVal-263 |
| SEQ. ID. NO. 22825 | 275-PheAspHisIleAlaGluValAlaAsp-283 |

Antigenic Index - Jameson-Wolf

| | |
|---|---|
| SEQ. ID. NO. 22826 | 6-CysArgCysSerGluSerIleArgArgIleArgArgAsnGlyArgGluTrpArgIleLysGlyGlnLysCysArgLeuAsnThrAspThrValGln-37 |
| SEQ. ID. NO. 22827 | 89-GlyGlyPheAspGlyArgProValAspIleGlyLysAlaArgPheLeu-104 |
| SEQ. ID. NO. 22828 | 120-AlaValAspAspGlyLysIle-126 |
| SEQ. ID. NO. 22829 | 131-AlaThrArgGlnLeuArgGlyPheLysLeuAspAspPheAspVal-145 |
| SEQ. ID. NO. 22830 | 153-ArgPheGlyCysGlyGlnIleAspAla-162 |
| SEQ. ID. NO. 22831 | 174-HisHisGlnAspAlaGlyGluValGlyArgValValGlyArgGlyTyr-189 |
| SEQ. ID. NO. 22832 | 204-ArgValGlnSerGlnArgArgGlyArgHisLeuGluAspPheGlyAsp-219 |
| SEQ. ID. NO. 22833 | 236-GluAspValAspVal-240 |

| | |
|---|---|
| SEQ. ID. NO. 22834 | 255-GlyLysLeuAspGlnPheAspGly-262 |
| SEQ. ID. NO. 22835 | 279-AlaGluValAlaAspGlyArgAlaGluAspAspPhePhePhe-292 |
| SEQ. ID. NO. 22836 | 295-AlaValValGlyGlyGlyArgSerGlyCysGlyGlyArg-307 |
| SEQ. ID. NO. 22837 | 313-AlaAlaGlyGlyGluAspGluArgGluCysGlyGlyGlyLysGlyPheGluGlu-330 |

Hydrophilic Regions - Hopp-Woods

| | |
|---|---|
| SEQ. ID. NO. 22838 | 7-ArgCysSerGluSerIleArgArgIleArgArgAsnGlyArgGluTrpArgIleLysGlyGlnLysCysArgLeuAsnThr-33 |
| SEQ. ID. NO. 22839 | 91-PheAspGlyArgProValAspIleGlyLys-100 |
| SEQ. ID. NO. 22840 | 120-AlaValAspAspGlyLysIle-126 |
| SEQ. ID. NO. 22841 | 131-AlaThrArgGlnLeuArgGlyPheLysLeuAspAspPheAsp-144 |
| SEQ. ID. NO. 22842 | 174-HisHisGlnAspAlaGlyGluValGlyArgValValGly-186 |
| SEQ. ID. NO. 22843 | 206-GlnSerGlnArgArgGlyArgHisLeuGluAspPheGlyAsp-219 |
| SEQ. ID. NO. 22844 | 236-GluAspValAspVal-240 |
| SEQ. ID. NO. 22845 | 255-GlyLysLeuAspGlnPheAsp-261 |
| SEQ. ID. NO. 22846 | 279-AlaGluValAlaAspGlyArgAlaGluAspAspPhePhePhe-292 |
| SEQ. ID. NO. 22847 | 299-GlyGlyArgSerGlyCysGly-305 |
| SEQ. ID. NO. 22848 | 315-GlyGlyGluAspGluArgGluCysGlyGly-324 |
| SEQ. ID. NO. 22849 | 326-LysGlyPheGluGlu-330 | a694

AMPHI Regions - AMPHI

| | |
|---|---|
| SEQ. ID. NO. 22850 | 82-ArgGlyArgAlaCysArg-87 |
| SEQ. ID. NO. 22851 | 116-CysArgHisPheAlaGln-121 |
| SEQ. ID. NO. 22852 | 123-ValAlaValGlyArgIleGly-129 |
| SEQ. ID. NO. 22853 | 140-PheCysGlnLeuPheAsp-145 |
| SEQ. ID. NO. 22854 | 156-AspIlePheLeuVal-160 |
| SEQ. ID. NO. 22855 | 162-IleAlaAspIleGlyGlu-167 |
| SEQ. ID. NO. 22856 | 184-ArgGlyLeuAlaAspIleGlyGluPheValGlyValSerAsp-197 |
| SEQ. ID. NO. 22857 | 251-HisGlnArgAlaSerArgIleLys-258 |
| SEQ. ID. NO. 22858 | 283-ArgAlaArgArgHisPheArgGlnValPheAsn-293 |
| SEQ. ID. NO. 22859 | 311-AspPheValAlaHisIle-316 |
| SEQ. ID. NO. 22860 | 340-AlaAlaArgIleGly-344 |

Antigenic Index - Jameson-Wolf

| | |
|---|---|
| SEQ. ID. NO. 22861 | 3-SerAlaSerGlyThrArgGlnLysCysArgLeuLysProVal-16 |
| SEQ. ID. NO. 22862 | 23-ProLysHisSerThrProAlaSer-30 |
| SEQ. ID. NO. 22863 | 47-GlyGlnAspGluHisAsnAla-53 |
| SEQ. ID. NO. 22864 | 66-ProProSerAlaTyrGly-71 |
| SEQ. ID. NO. 22865 | 79-HisPheGlyArgGlyArgAlaCysArgTyr-88 |
| SEQ. ID. NO. 22866 | 110-ArgIleAspSerAlaArgCysArgHis-118 |
| SEQ. ID. NO. 22867 | 127-ArgIleGlyArgThrAspHisAsnHisAsp-136 |
| SEQ. ID. NO. 22868 | 144-PheAspGlyGlyLeuProValGlyArgArgIleAla-155 |
| SEQ. ID. NO. 22869 | 163-AlaAspIleGlyGluThrArgValGlnArgGlyAspAspValPhe-177 |
| SEQ. ID. NO. 22870 | 180-IleAspArgGluArgGlyLeuAlaAsp-188 |
| SEQ. ID. NO. 22871 | 202-HisIleSerAspArgPheAspGlnLysHisPheAlaArgArgLysLeuProHisArgSerPheAspLeu-224 |
| SEQ. ID. NO. 22872 | 228-LeuMetProAspHisAspAspPheThr-236 |
| SEQ. ID. NO. 22873 | 250-ArgHisGlnArgAlaSerArgIleLysHisAlaGluThrAlaLeu-264 |
| SEQ. ID. NO. 22874 | 268-LeuProHisArgLeuArgTyrAla-275 |
| SEQ. ID. NO. 22875 | 280-AsnGlnCysArgAlaArgArgHisPhe-288 |
| SEQ. ID. NO. 22876 | 291-ValPheAsnLysHisArgThr-297 |
| SEQ. ID. NO. 22877 | 316-IleAsnArgArgAlaGluLeu-322 |
| SEQ. ID. NO. 22878 | 326-ThrPheAspAsnThrAspCysPro-333 |
| SEQ. ID. NO. 22879 | 336-ThrSerAlaGluAlaAlaAlaArgIleGlyLysAspAspGlyPhe-349 |
| SEQ. ID. NO. 22880 | 370-TyrGlyGlyArgCysCysProThrProProThrProHisArgArgArg-385 |

Hydrophilic Regions - Hopp-Woods

| | |
|---|---|
| SEQ. ID. NO. 22881 | 5-SerGlyThrArgGlnLysCysArgLeuLysPro-15 |
| SEQ. ID. NO. 22882 | 47-GlyGlnAspGluHisAsnAla-53 |
| SEQ. ID. NO. 22883 | 81-GlyArgGlyArgAlaCysArg-87 |
| SEQ. ID. NO. 22884 | 110-ArgIleAspSerAlaArgCysArgHis-118 |
| SEQ. ID. NO. 22885 | 127-ArgIleGlyArgThrAspHisAsnHis-135 |
| SEQ. ID. NO. 22886 | 150-ValGlyArgArgIleAla-155 |
| SEQ. ID. NO. 22887 | 163-AlaAspIleGlyGluThrArgValGlnArgGlyAspAsp-175 |
| SEQ. ID. NO. 22888 | 180-IleAspArgGluArgGlyLeuAlaAsp-188 |
| SEQ. ID. NO. 22889 | 202-HisIleSerAspArgPheAspGlnLysHisPheAlaArgArgLysLeuProHisArgSerPheAspLeu-224 |
| SEQ. ID. NO. 22890 | 230-ProAspHisAspAsp-234 |
| SEQ. ID. NO. 22891 | 250-ArgHisGlnArgAlaSerArgIleLysHisAlaGluThrAlaLeu-264 |
| SEQ. ID. NO. 22892 | 280-AsnGlnCysArgAlaArgArgHisPhe-288 |
| SEQ. ID. NO. 22893 | 292-PheAsnLysHisArg-296 |
| SEQ. ID. NO. 22894 | 316-IleAsnArgArgAlaGluLeu-322 |
| SEQ. ID. NO. 22895 | 327-PheAspAsnThrAsp-331 |
| SEQ. ID. NO. 22896 | 338-AlaGluAlaAlaAlaArgIleGlyLysAspAspGly-348 |
| SEQ. ID. NO. 22897 | 380-ThrProHisArgArgArg-385 | a695

AMPHI Regions - AMPHI

| | |
|---|---|
| SEQ. ID. NO. 22898 | 36-HisProGlnArgPheSerLysProAlaGluArgTyrAlaAspCysProHis-52 |
| SEQ. ID. NO. 22899 | 85-CysSerSerProValSerArgAsn-92 |
| SEQ. ID. NO. 22900 | 119-AspArgLeuAspTyr-123 |
| SEQ. ID. NO. 22901 | 129-ValArgLeuSerAsnGluValGlu-136 |
| SEQ. ID. NO. 22902 | 144-AlaLeuGluHisAla-148 |
| SEQ. ID. NO. 22903 | 158-ValGlnLysLeuAsp-162 |
| SEQ. ID. NO. 22904 | 183-ValGluThrAlaGlnAsnLeuTyrAsnGlnAlaLeuLysHisTyrLysSerGly-200 |
| SEQ. ID. NO. 22905 | 205-AlaAlaSerLeuLeuLysGlyAla-212 |
| SEQ. ID. NO. 22906 | 238-CysGluSerValIleGluIle-244 |

TABLE 1-continued

| | |
|---|---|
| SEQ. ID. NO. 22907 | 248-TyrAlaAsnArgPheLysAspSer-255 |
| SEQ. ID. NO. 22908 | 278-AlaArgAlaThrTrpArgSerLeuIleGlnThrTyrProGly-291 |

Antigenic Index - Jameson-Wolf

| | |
|---|---|
| SEQ. ID. NO. 22909 | 5-CysProAlaArgArgHisHisCysHis-13 |
| SEQ. ID. NO. 22910 | 17-PheValGluArgLysGlyAspAlaArgSerGlyPhe-28 |
| SEQ. ID. NO. 22911 | 31-AlaAlaGlnArgArgHisProGlnArgPheSerLysProAlaGluArgTyrAlaAspCysProHisHisProAlaArgArgArgPheAspProAlaSerGluLysIleMetLysThrLys-71 |
| SEQ. ID. NO. 22912 | 87-SerProValSerArgAsnIleGlnAspMetArgLeuGluProGlnAlaGluAlaGlySerSerAspAlaIleProTyr-112 |
| SEQ. ID. NO. 22913 | 117-LeuGlnAspArgLeuAspTyr-123 |
| SEQ. ID. NO. 22914 | 131-LeuSerAsnGluValGluThrLeuAsnGlyLysValLysAlaLeuGluHisAlaLysThrHisProSerSerArgAlaTyrValGlnLysLeuAspAspArgLysLeuLysGlu-168 |
| SEQ. ID. NO. 22915 | 170-TyrLeuAsnThrGluGlyGlySerAla-178 |
| SEQ. ID. NO. 22916 | 193-AlaLeuLysHisTyrLysSerGlyArgPhe-202 |
| SEQ. ID. NO. 22917 | 210-LysGlyAlaAspGlyGlyAspGlyGlySerIleAlaGln-222 |
| SEQ. ID. NO. 22918 | 230-GlnSerArgAlaArgMetGlyAsnCys-238 |
| SEQ. ID. NO. 22919 | 244-IleGlyGlyArgTyrAlaAsnArgPheLysAspSerProThrAlaPro-259 |
| SEQ. ID. NO. 22920 | 266-GlyGluCysGlnTyr-270 |
| SEQ. ID. NO. 22921 | 272-LeuGlnGlnLysAspIleAla-278 |
| SEQ. ID. NO. 22922 | 289-TyrProGlySerProAlaAlaLysArgAlaAlaAlaAlaValArgLysArg-305 |

Hydrophilic Regions - Hopp-Woods

| | |
|---|---|
| SEQ. ID. NO. 22923 | 5-CysProAlaArgArgHisHisCys-12 |
| SEQ. ID. NO. 22924 | 17-PheValGluArgLysGlyAspAlaArgSerGlyPhe-28 |
| SEQ. ID. NO. 22925 | 31-AlaAlaGlnArgArgHisProGlnArgPheSerLysProAlaGluArgTyrAlaAsp-49 |
| SEQ. ID. NO. 22926 | 51-ProHisHisProAlaArgArgArgArgPheAspProAlaSerGluLysIleMetLysThrLys71 |
| SEQ. ID. NO. 22927 | 88-ProValSerArgAsnIleGlnAspMetArgLeuGluProGlnAlaGluAlaGlySerSerAsp-108 |
| SEQ. ID. NO. 22928 | 117-LeuGlnAspArgLeuAspTyr-123 |
| SEQ. ID. NO. 22929 | 131-LeuSerAsnGluValGluThrLeuAsnGlyLysValLysAlaLeuGluHisAlaLysThrHisProSerSer-154 |
| SEQ. ID. NO. 22930 | 157-TyrValGlnLysLeuAspAspArgLysLeuLysGlu-168 |
| SEQ. ID. NO. 22931 | 195-LysHisTyrLysSerGlyArgPhe-202 |
| SEQ. ID. NO. 22932 | 210-LysGlyAlaAspGlyGlyAspGlyGlySerIleAlaGln-222 |
| SEQ. ID. NO. 22933 | 231-SerArgAlaArgMetGlyAsn-237 |
| SEQ. ID. NO. 22934 | 248-TyrAlaAsnArgPheLysAspSerProThrAlaPro-259 |
| SEQ. ID. NO. 22935 | 266-GlyGluCysGlnTyr-270 |
| SEQ. ID. NO. 22936 | 272-LeuGlnGlnLysAspIleAla-278 |
| SEQ. ID. NO. 22937 | 293-ProAlaAlaLysArgAlaAlaAlaAlaValArgLysArg-305 | a696
AMPHI Regions - AMPHI

| | |
|---|---|
| SEQ. ID. NO. 22938 | 18-PheGlyGlyIlePheHisPheValCysArgPheLeuSerArgValGlySerPheValGlnSerIlePheSerCysPheSer-44 |
| SEQ. ID. NO. 22939 | 65-IlePheAspLeuValPhe-70 |
| SEQ. ID. NO. 22940 | 94-GlyLeuAsnArgPheLeuAsnLeuLeuPheGlyPheLeuArg-107 |

Antigenic Index - Jameson-Wolf

| | |
|---|---|
| SEQ. ID. NO. 22941 | 12-CysGlnGlyAsnLysLeu-17 |
| SEQ. ID. NO. 22942 | 73-PheAspGlyArgSerGlyArgLeuGlyGlyArgSerArgSer-86 |
| SEQ. ID. NO. 22943 | 108-ThrSerCysGlnGlySerArgHisHisCysGlyAsnGln-120 |

Hydrophilic Regions - Hopp-Woods

| | |
|---|---|
| SEQ. ID. NO. 22944 | 73-PheAspGlyArgSerGlyArgLeuGlyGlyArgSerArgSer-86 |
| SEQ. ID. NO. 22945 | 109-SerCysGlnGlySerArgHisHisCys-117 | a700
AMPHI Regions - AMPHI

| | |
|---|---|
| SEQ. ID. NO. 22946 | 6-ThrLeuLeuSerValLeuIleProMetPheAlaGlyPhePheIleArgValProLys-24 |
| SEQ. ID. NO. 22947 | 27-LeuProAlaLeuAspLysValLeuSerValLeu-37 |
| SEQ. ID. NO. 22948 | 51-ArgValGluAspLeuGlySerArg-58 |
| SEQ. ID. NO. 22949 | 80-AlaLeuAlaValLeuGlyLysLeu-87 |
| SEQ. ID. NO. 22950 | 191-SerTrpValLysGlyLeu-196 |
| SEQ. ID. NO. 22951 | 204-TrpTyrSerLeuSerGlyLeuVal-211 |
| SEQ. ID. NO. 22952 | 216-TyrGlyAlaValTrpGlySerIleAlaLeuLeuAsnAspLeuAlaArgGluLeu-233 |
| SEQ. ID. NO. 22953 | 267-ArgGlyAlaGlyGlyLeu-272 |

Antigenic Index - Jameson-Wolf

| | |
|---|---|
| SEQ. ID. NO. 22954 | 21-ArgValProLysProTyrLeu-27 |
| SEQ. ID. NO. 22955 | 50-SerArgValGluAspLeuGlySerArgLeuAspAspMetAla-63 |
| SEQ. ID. NO. 22956 | 90-TrpArgIleLysGlyLysGlyLysGlyVal-99 |
| SEQ. ID. NO. 22957 | 118-AlaSerGlyLysLeuMetArg-124 |
| SEQ. ID. NO. 22958 | 128-MetProSerGluAsnAlaGlyMet-135 |
| SEQ. ID. NO. 22959 | 149-LeuLysSerSerGlyValSerLeu-156 |
| SEQ. ID. NO. 22960 | 160-LeuValAsnArgArgGlyIleArgLeu-168 |
| SEQ. ID. NO. 22961 | 245-ArgPheProAspAla-249 |
| SEQ. ID. NO. 22962 | 268-GlyAlaGlyGlyLeuGluAla-274 |

Hydrophilic Regions - Hopp-Woods

| | |
|---|---|
| SEQ. ID. NO. 22963 | 50-SerArgValGluAspLeuGlySerArgLeuAspAspMetAla-63 |
| SEQ. ID. NO. 22964 | 92-IleLysGlyLysGlyLysGlyVal-99 |
| SEQ. ID. NO. 22965 | 149-LeuLysSerSerGlyValSer-155 |
| SEQ. ID. NO. 22966 | 160-LeuValAsnArgArgGlyIleArg-167 | a701
AMPHI Regions - AMPHI

| | |
|---|---|
| SEQ. ID. NO. 22967 | 6-PheGlnValAlaGly-10 |
| SEQ. ID. NO. 22968 | 45-ProAsnSerPheAlaSerPheLysArgPheSerSerIle-57 |

Antigenic Index - Jameson-Wolf

| | |
|---|---|
| SEQ. ID. NO. 22969 | 18-GlnSerThrProSerSerProThr-25 |
| SEQ. ID. NO. 22970 | 33-ThrSerProGluAlaGly-38 |
| SEQ. ID. NO. 22971 | 52LysArgPheSerSerIleSer-58 |

TABLE 1-continued

| | |
|---|---|
| SEQ. ID. NO. 22972 | 72-GlyLysAlaAspIleProThr-78 |
| SEQ. ID. NO. 22973 | 105-LysAlaSerLeuAsnAsnArgAlaThrSerSer-115 |
| SEQ. ID. NO. 22974 | 119-SerGlySerGlyThrArgLeu-125 |
| Hydrophilic Regions - Hopp-Woods | |
| SEQ. ID. NO. 22975 | 72-GlyLysAlaAspIle-76 |
| SEQ. ID. NO. 22976 | 107-SerLeuAsnAsnArgAlaThrSer-114 |
| a702 | |
| AMPHI Regions - AMPHI | |
| SEQ. ID. NO. 22977 | 51-CysSerGlyLeuValThrVal-57 |
| SEQ. ID. NO. 22978 | 118-LysIleSerArgGly-122 |
| Antigenic Index - Jameson-Wolf | |
| SEQ. ID. NO. 22979 | 1-MetProCysSerLysAlaSer-7 |
| SEQ. ID. NO. 22980 | 28-LeuAlaArgAspSerCysSerProGlyLeu-37 |
| SEQ. ID. NO. 22981 | 41-ThrAlaProAlaSerSer-46 |
| SEQ. ID. NO. 22982 | 68-LeuAlaIleArgArgMetAlaSerArgProThrGlyValArgArgValIleSer-85 |
| SEQ. ID. NO. 22983 | 88-GlyMetProProSerThrArgAlaTrpAspLysSerMetAla-101 |
| SEQ. ID. NO. 22984 | 118-LysIleSerArgGlyValSer-124 |
| SEQ. ID. NO. 22985 | 139-ArgTrpAspArgLeu-143 |
| Hydrophilic Regions - Hopp-Woods | |
| SEQ. ID. NO. 22986 | 29-AlaArgAspSerCysSer-34 |
| SEQ. ID. NO. 22987 | 69-AlaIleArgArgMetAlaSerArgProThrGlyValArgArgValIleSer-85 |
| SEQ. ID. NO. 22988 | 94-ArgAlaTrpAspLys-98 |
| SEQ. ID. NO. 22989 | 139-ArgTrpAspArgLeu-143 |
| a703 | |
| AMPHI Regions - AMPHI | |
| SEQ. ID. NO. 22990 | 21-GlnThrLeuAlaThrValAsnGly-28 |
| SEQ. ID. NO. 22991 | 64-GluValValAsnThrValValAlaGlnGlu-73 |
| SEQ. ID. NO. 22992 | 79-LeuAspArgSerAlaGlu-84 |
| SEQ. ID. NO. 22993 | 140-AlaAlaTyrAspAsnIleSerGlyPheTyrLysGly-151 |
| SEQ. ID. NO. 22994 | 181-PheAspAlaValLeu-185 |
| SEQ. ID. NO. 22995 | 204-ValProLeuLysAspLeuGluGlnGlyValProProLeuTyrGlnAlaIleLysAspLeuLysLys-225 |
| SEQ. ID. NO. 22996 | 252-ValProSerPheAsp-256 |
| SEQ. ID. NO. 22997 | 270-ArgIleAspArgAlaValGlyAlaLeu-278 |
| Antigenic Index - Jameson-Wolf | |
| SEQ. ID. NO. 22998 | 1-MetLysAlaLysIle-5 |
| SEQ. ID. NO. 22999 | 26-ValAsnGlyGlnLysIleAspSerSerVal-35 |
| SEQ. ID. NO. 23000 | 43-PheArgAlaGluAsnSerArgAlaGluAspThrProGlnLeuArg-57 |
| SEQ. ID. NO. 23001 | 72-GlnGluValLysArgLeuLysLeuAspArgSerAlaGluPheLysAsnAlaLeuAlaLysLeuArgAlaGluAlaLysLysSerGlyAspAspLysLys ProSerPheLysThr-109 |
| SEQ. ID. NO. 23002 | 129-LysThrGlnProValSerGluGlnGluValLysAlaAlaTyr-142 |
| SEQ. ID. NO. 23003 | 144-AsnIleSerGlyPheTyrLysGlyThrGlnGluValGlnLeu-157 |
| SEQ. ID. NO. 23004 | 160-IleLeuThrAspLysGluGluAsnAlaLysLysAlaValAlaAspLeuLysAlaLysLysGlyPhe-181 |
| SEQ. ID. NO. 23005 | 188-TyrSerLeuAsnAspArgThrLysGlnThrGlyAlaProValGly-202 |
| SEQ. ID. NO. 23006 | 207-LysAspLeuGluGlnGlyValProPro-215 |
| SEQ. ID. NO. 23007 | 221-LysAspLeuLysLysGlyGluPheThrAlaThrProLeuLysAsnGlyAspPhe-238 |
| SEQ. ID. NO. 23008 | 243-TyrValAsnAspSerArgGluValLysValProSerPheAspGluMetLysGly-260 |
| SEQ. ID. NO. 23009 | 266-LeuGlnAlaGluArgIleAspArgAlaVal-275 |
| SEQ. ID. NO. 23010 | 282-AlaAsnIleLysProAlaLys-288 |
| Hydrophilic Regions - Hopp-Woods | |
| SEQ. ID. NO. 23011 | 1-MetLysAlaLysIle-5 |
| SEQ. ID. NO. 23012 | 29-GlnLysIleAspSerSerVal-35 |
| SEQ. ID. NO. 23013 | 43-PheArgAlaGluAsnSerArgAlaGluAspThrProGlnLeuArg-57 |
| SEQ. ID. NO. 23014 | 72-GlnGluValLysArgLeuLysLeuAspArgSerAlaGluPheLysAsnAlaLeuAlaLysLeuArgAlaGluAlaLysLysSerGlyAspAspLysLys ProSerPhe-107 |
| SEQ. ID. NO. 23015 | 131-GlnProValSerGluGlnGluValLysAlaAlaTyr-142 |
| SEQ. ID. NO. 23016 | 160-IleLeuThrAspLysGluGluAsnAlaLysLysAlaValAlaAspLeuLysAlaLysLysGlyPhe-181 |
| SEQ. ID. NO. 23017 | 189-SerLeuAsnAspArgThrLysGlnThrGly-198 |
| SEQ. ID. NO. 23018 | 207-LysAspLeuGluGln-211 |
| SEQ. ID. NO. 23019 | 221-LysAspLeuLysLysGlyGluPhe-228 |
| SEQ. ID. NO. 23020 | 245-AsnAspSerArgGluValLysValProSerPheAspGluMetLysGly-260 |
| SEQ. ID. NO. 23021 | 266-LeuGlnAlaGluArgIleAspArgAlaVal-275 |
| SEQ. ID. NO. 23022 | 282-AlaAsnIleLysProAlaLys-288 |
| a704 | |
| AMPHI Regions - AMPHI | |
| SEQ. ID. NO. 23023 | 33-GlyCysGlnAlaValAlaGlnSerIleIleAspAlaGlyLeuGly-47 |
| SEQ. ID. NO. 23024 | 65-GlnGluIleLeuAspGlnIleArgLeuTyrAspLeuProGluValGlnSerAspPheValGluThrHis-87 |
| SEQ. ID. NO. 23025 | 184-LeuGlyMetMetGln-188 |
| SEQ. ID. NO. 23026 | 208-LeuGlnIleLeuHisTrpGlyGlyPheLeuMetValLeuPro-221 |
| SEQ. ID. NO. 23027 | 232-GlnGlyAlaLeuArgAspLeuLys-239 |
| SEQ. ID. NO. 23028 | 252-AlaIleIleMetThrPheIleAlaGlyValTyrSer-263 |
| SEQ. ID. NO. 23029 | 289-PheMetGluHisIleAlaArg-295 |
| SEQ. ID. NO. 23030 | 298-AlaGlyAspAlaAlaGluArgLeuValLysLeuIleProAlaPheCysHisHisMetProAspTyrProAspThrGlnGluThr-325 |
| SEQ. ID. NO. 23031 | 400-GlyGlyThrArgLeuSerHisIleValArgLeuLeuAspArgAlaLeuAla-416 |
| SEQ. ID. NO. 23032 | 423-GluLeuAlaGluGlnTyr-428 |
| SEQ. ID. NO. 23033 | 499-AlaIleGluThrLeuAlaGln-505 |
| SEQ. ID. NO. 23034 | 527-IleSerLeuLeuArg-531 |
| SEQ. ID. NO. 23035 | 576-LeuAsnArgIleGlyGluGlyValGly-584 |
| SEQ. ID. NO. 23036 | 639-LeuLysAspSerAlaAlaGluAlaValArgGlnLeuAla-651 |
| SEQ. ID. NO. 23037 | 670-GluThrAlaArgAlaLeuGlyVal-677 |
| SEQ. ID. NO. 23038 | 691-GluTyrValLysAlaLeuGlnLysGlu-699 |

TABLE 1-continued

| | |
|---|---|
| SEQ. ID. NO. 23039 | 744-AspLeuArgThrValAlaHisLeuLeuAsp-753 |
| SEQ. ID. NO. 23040 | 780-AlaValLeuGlyTyrValGlnProTrpIleAlaAla-791 |
| SEQ. ID. NO. 23041 | 799-LeuAlaValLeuGly-803 |
| SEQ. ID. NO. 23042 | 805-AlaLeuArgLeuHisLysArg-811 |

Antigenic Index - Jameson-Wolf

| | |
|---|---|
| SEQ. ID. NO. 23043 | 1-MetLysLysThrCys-5 |
| SEQ. ID. NO. 23044 | 9-GlyLeuAspValProGluAsn-15 |
| SEQ. ID. NO. 23045 | 21-ArgTyrGluAsnGluAspArgGluThrCysCys-31 |
| SEQ. ID. NO. 23046 | 46-LeuGlySerTyrTyrLysGlnArgThrAlaAspAlaGlnLysThrGluLeuProProGlnGluIleLeuAsp-69 |
| SEQ. ID. NO. 23047 | 77-ProGluValGlnSerAspPheValGluThrHisGlyGlyThrArgGluAla-93 |
| SEQ. ID. NO. 23048 | 112-GlnLeuLeuArgThrAspGlyIleVal-120 |
| SEQ. ID. NO. 23049 | 124-LeuAsnTyrSerThrHisArgCys-131 |
| SEQ. ID. NO. 23050 | 133-ValValTrpAspAspGlyLysIleArgLeu-142 |
| SEQ. ID. NO. 23051 | 158-ProTyrAspAlaGlnLysIleGluAlaAlaAsnGlnLysGluArgLysGlnTyr-175 |
| SEQ. ID. NO. 23052 | 199-TyrGlyGlyAspIleGluProAspPhe-207 |
| SEQ. ID. NO. 23053 | 234-AlaLeuArgAspLeuLysAsnArgArgValGlyMetAspThrProIle-249 |
| SEQ. ID. NO. 23054 | 293-IleAlaArgArgLysAlaGlyAspAlaAlaGluArgLeuVal-306 |
| SEQ. ID. NO. 23055 | 316-MetProAspTyrProAspThrGlnGluThrCysGlu-327 |
| SEQ. ID. NO. 23056 | 329-AlaValValLysLeuLysAlaGlyAsp-337 |
| SEQ. ID. NO. 23057 | 342-LysProGlyGluThrIleProValAspGlyThrVal-353 |
| SEQ. ID. NO. 23058 | 356-GlySerSerAlaValAsnGluSer-363 |
| SEQ. ID. NO. 23059 | 365-LeuThrGlyGluSer-369 |
| SEQ. ID. NO. 23060 | 374-LysMetProSerGluLysValThrAla-382 |
| SEQ. ID. NO. 23061 | 393-IleArgThrAspArgThrGlyGlyGlyThrArg-403 |
| SEQ. ID. NO. 23062 | 414-AlaLeuAlaGlnLysProArgThrAlaGluLeuAlaGlu-426 |
| SEQ. ID. NO. 23063 | 486-ThrLeuAlaArgGluGlyIle-492 |
| SEQ. ID. NO. 23064 | 495-GlyGlyLysGlnAlaIle-500 |
| SEQ. ID. NO. 23065 | 510-IlePheAspLysThrGlyThrLeuThrGlnGlyLysProAlaValArgArg-526 |
| SEQ. ID. NO. 23066 | 528-SerLeuLeuArgGlyThrAspGluAlaPhe-537 |
| SEQ. ID. NO. 23067 | 545-LeuGluGlnGlnSerGluHisProLeu-553 |
| SEQ. ID. NO. 23068 | 560-CysArgIleSerAspGlySerValPro-568 |
| SEQ. ID. NO. 23069 | 570-IleAlaIleLysGlnArgLeuAsnArgIleGlyGluGlyVal-583 |
| SEQ. ID. NO. 23070 | 589-ValAsnGlyGluThrGln-594 |
| SEQ. ID. NO. 23071 | 605-AlaGluIleSerGlyLysGluProGlnThrGluGlyGlyGlySer-619 |
| SEQ. ID. NO. 23072 | 635-LeuGlnAspProLeuLysAspSerAlaAlaGluAlaValArg-648 |
| SEQ. ID. NO. 23073 | 650-LeuAlaGlyLysAsnLeu-655 |
| SEQ. ID. NO. 23074 | 659-IleLeuSerGlyAspArgGluThrAlaVal-668 |
| SEQ. ID. NO. 23075 | 684-AlaMetProGluAspLysLeuGluTyr-692 |
| SEQ. ID. NO. 23076 | 694-LysAlaLeuGlnLysGluGlyLysLys-702 |
| SEQ. ID. NO. 23077 | 707-GlyAspGlyIleAsnAspAla-713 |
| SEQ. ID. NO. 23078 | 725-AlaAlaGlyGlyThrAspIleAlaArgAspGlyAlaAsp-737 |
| SEQ. ID. NO. 23079 | 743-GluAspLeuArgThr-747 |
| SEQ. ID. NO. 23080 | 753-AspGlnAlaArgArgThrArgHisIleIle-762 |
| SEQ. ID. NO. 23081 | 807-ArgLeuHisLysArgGlyLysMetGlnSerGluLysMetProSerGluGln-823 |

Hydrophilic Regions - Hopp-Woods

| | |
|---|---|
| SEQ. ID. NO. 23082 | 1-MetLysLysThrCys-5 |
| SEQ. ID. NO. 23083 | 21-ArgTyrGluAsnGluAspArgGluThrCys-30 |
| SEQ. ID. NO. 23084 | 50-TyrLysGlnArgThrAlaAspAlaGlnLysThrGluLeuProPro-64 |
| SEQ. ID. NO. 23085 | 77-ProGluValGlnSerAspPheValGlu-85 |
| SEQ. ID. NO. 23086 | 87-HisGlyGlyThrArgGluAla-93 |
| SEQ. ID. NO. 23087 | 112-GlnLeuLeuArgThrAspGlyIleVal-120 |
| SEQ. ID. NO. 23088 | 133-ValValTrpAspAspGlyLysIleArgLeu-142 |
| SEQ. ID. NO. 23089 | 160-AspAlaGlnLysIleGluAlaAlaAsnGlnLysGluArgLysGlnTyr-175 |
| SEQ. ID. NO. 23090 | 201-GlyAspIleGluProAspPhe-207 |
| SEQ. ID. NO. 23091 | 234-AlaLeuArgAspLeuLysAsnArgArgValGlyMet-245 |
| SEQ. ID. NO. 23092 | 293-IleAlaArgArgLysAlaGlyAspAlaAlaGluArgLeuVal-306 |
| SEQ. ID. NO. 23093 | 318-AspTyrProAspThrGlnGluThrCysGlu-327 |
| SEQ. ID. NO. 23094 | 329-AlaValValLysLeuLysAlaGlyAsp-337 |
| SEQ. ID. NO. 23095 | 375-MetProSerGluLysValThr-381 |
| SEQ. ID. NO. 23096 | 393-IleArgThrAspArgThrGlyGlyGlyThrArg-403 |
| SEQ. ID. NO. 23097 | 414-AlaLeuAlaGlnLysProArgThrAlaGluLeuAlaGlu-426 |
| SEQ. ID. NO. 23098 | 486-ThrLeuAlaArgGluGlyIle-492 |
| SEQ. ID. NO. 23099 | 518-ThrGlnGlyLysProAlaValArgArg-526 |
| SEQ. ID. NO. 23100 | 531-ArgGlyThrAspGlu-535 |
| SEQ. ID. NO. 23101 | 545-LeuGluGlnGlnSerGluHisProLeu-553 |
| SEQ. ID. NO. 23102 | 561-ArgIleSerAspGlySerVal-567 |
| SEQ. ID. NO. 23103 | 570-IleAlaIleLysGlnArgLeuAsnArgIleGlyGlu-581 |
| SEQ. ID. NO. 23104 | 607-IleSerGlyLysGluProGlnThrGluGlyGlyGly-618 |
| SEQ. ID. NO. 23105 | 637-AspProLeuLysAspSerAlaAlaGluAlaValArg-648 |
| SEQ. ID. NO. 23106 | 661-SerGlyAspArgGluThrAlaVal-668 |
| SEQ. ID. NO. 23107 | 684-AlaMetProGluAspLysLeuGluTyr-692 |
| SEQ. ID. NO. 23108 | 694-LysAlaLeuGlnLysGluGlyLysLys-702 |
| SEQ. ID. NO. 23109 | 730-AspIleAlaArgAspGlyAlaAsp-737 |
| SEQ. ID. NO. 23110 | 743-GluAspLeuArgThr-747 |
| SEQ. ID. NO. 23111 | 753-AspGlnAlaArgArgThrArgHisIleIle-762 |
| SEQ. ID. NO. 23112 | 807-ArgLeuHisLysArgGlyLysMetGlnSerGluLysMetProSerGluGln-823 | a705
AMPHI Regions - AMPHI

| | |
|---|---|
| SEQ. ID. NO. 23113 | 67-LysIleLeuLeuLysLeu-72 |
| SEQ. ID. NO. 23114 | 104-AspProIleProAla-108 |

TABLE 1-continued

| | |
|---|---|
| SEQ. ID. NO. 23115 | 147-TyrMetGlnThrPheArgArgIleValAlaProGln-158 |
| SEQ. ID. NO. 23116 | 169-AsnGluPheIleGlyLeuPheLysAsn-177 |
| SEQ. ID. NO. 23117 | 183-ValValThrValThrGluLeuPheArgValAlaGln-194 |
| SEQ. ID. NO. 23118 | 196-ThrAlaAsnArgThr-200 |

Antigenic Index - Jameson-Wolf

| | |
|---|---|
| SEQ. ID. NO. 23119 | 13-ThrGluThrArgAlaAspMet-19 |
| SEQ. ID. NO. 23120 | 132-ValProLysGlyGlnTrpGlu-138 |
| SEQ. ID. NO. 23121 | 165-ProProLeuSerAsnGlu-170 |
| SEQ. ID. NO. 23122 | 193-AlaGlnGluThrAlaAsnArgThrTyrAsp-202 |
| SEQ. ID. NO. 23123 | 226-AlaArgLeuGluLysArgPheAspArgTyrValAla-237 |

Hydrophilic Regions - Hopp-Woods

| | |
|---|---|
| SEQ. ID. NO. 23124 | 13-ThrGluThrArgAlaAspMet-19 |
| SEQ. ID. NO. 23125 | 193-AlaGlnGluThrAlaAsnArgThr-200 |
| SEQ. ID. NO. 23126 | 226-AlaArgLeuGluLysArgPheAspArgTyrValAla-237 | a706
AMPHI Regions - AMPHI

| | |
|---|---|
| SEQ. ID. NO. 23127 | 9-LeuValSerArgTrpLeuAsnSerTyr-17 |
| SEQ. ID. NO. 23128 | 24-ArgLeuIleHisAlaValArg-30 |
| SEQ. ID. NO. 23129 | 70-IleTyrSerLysAlaValGluArgMetLeuGlyThrValIleGly-84 |
| SEQ. ID. NO. 23130 | 111-ThrAlaSerAlaLeuAlaGlyTrpAlaAla-120 |
| SEQ. ID. NO. 23131 | 153-ArgAlaMetAsnValLeu-158 |
| SEQ. ID. NO. 23132 | 183-LeuAlaAspAsnLeuThrAspCysSerLysMetIleAlaGluIleSerAsnGlyArg-201 |
| SEQ. ID. NO. 23133 | 204-ThrArgGluArgLeuGluGluAsn-211 |
| SEQ. ID. NO. 23134 | 243-MetGluAlaMetGlnHisAlaHisArgLysIleVal-254 |
| SEQ. ID. NO. 23135 | 318-AlaLeuAlaGluHisLeuHis-324 |

Antigenic Index - Jameson-Wolf

| | |
|---|---|
| SEQ. ID. NO. 23136 | 1-MetAsnThrSerGlnArgAsnArgLeu-9 |
| SEQ. ID. NO. 23137 | 11-SerArgTrpLeuAsnSerTyrGluArgTyrArgTyrArgArg-24 |
| SEQ. ID. NO. 23138 | 73-LysAlaValGluArgMetLeu-79 |
| SEQ. ID. NO. 23139 | 97-HisTyrPheHisGlyAsnLeu-103 |
| SEQ. ID. NO. 23140 | 122-GlyLysAsnGlyTyrVal-127 |
| SEQ. ID. NO. 23141 | 140-GlyAspAsnGlySerGluTrpPheAsp-148 |
| SEQ. ID. NO. 23142 | 186-AsnLeuThrAspCysSerLysMetIleAlaGluIleSerAsnGlyArgArgMetThrArgGluArgLeuGluGluAsnMetAlaLysMetArgGlnIleAsn-219 |
| SEQ. ID. NO. 23143 | 221-ArgMetValLysSerArgSerHisLeuAlaAlaThrSerGlyGluSerArgIleSer-239 |
| SEQ. ID. NO. 23144 | 249-AlaHisArgLysIleValAsn-255 |
| SEQ. ID. NO. 23145 | 266-LysLeuGlnSerProLysLeuAsnGlySerGluIleArgLeuLeuAsp-281 |
| SEQ. ID. NO. 23146 | 300-GlyArgHisAlaArgArgIleArgIleAspThrAlaIleAsnProGluLeuGluAlaLeuAla-320 |
| SEQ. ID. NO. 23147 | 334-SerThrAsnMetArgGlnGluIle-341 |
| SEQ. ID. NO. 23148 | 349-GlnArgThrArgArgLysTrpLeuAspAlaHisGluArgGlnHisLeu-364 |
| SEQ. ID. NO. 23149 | 367-SerLeuLeuGluThrArgGluHisSer-375 |

Hydrophilic Regions - Hopp-Woods

| | |
|---|---|
| SEQ. ID. NO. 23150 | 3-ThrSerGlnArgAsnArgLeu-9 |
| SEQ. ID. NO. 23151 | 17-TyrGluArgTyrArgTyrArgArg-24 |
| SEQ. ID. NO. 23152 | 73-LysAlaValGluArgMetLeu-79 |
| SEQ. ID. NO. 23153 | 142-AsnGlySerGluTrpPhe-147 |
| SEQ. ID. NO. 23154 | 186-AsnLeuThrAspCysSerLysMetIleAla-195 |
| SEQ. ID. NO. 23155 | 198-SerAsnGlyArgArgMetThrArgGluArgLeuGluGluAsnMetAlaLysMetArgGlnIleAsn-219 |
| SEQ. ID. NO. 23156 | 221-ArgMetValLysSerArgSerHis-228 |
| SEQ. ID. NO. 23157 | 232-ThrSerGlyGluSerArgIle-238 |
| SEQ. ID. NO. 23158 | 249-AlaHisArgLysIleValAsn-255 |
| SEQ. ID. NO. 23159 | 266-LysLeuGlnSerProLysLeuAsnGlySerGluIleArgLeuLeuAsp-281 |
| SEQ. ID. NO. 23160 | 301-ArgHisAlaArgArgIleArgIle-308 |
| SEQ. ID. NO. 23161 | 314-ProGluLeuGluAlaLeuAla-320 |
| SEQ. ID. NO. 23162 | 336-AsnMetArgGlnGluIle-341 |
| SEQ. ID. NO. 23163 | 349-GlnArgThrArgArgLysTrpLeuAspAlaHisGluArgGlnHisLeu-364 |
| SEQ. ID. NO. 23164 | 367-SerLeuLeuGluThrArgGluHisSer-375 | a707
AMPHI Regions - AMPHI

| | |
|---|---|
| SEQ. ID. NO. 23165 | 16-AsnLeuSerArgLeuGlnLysAla-23 |
| SEQ. ID. NO. 23166 | 98-GluGlnGlyLeuGluAsnLeuArgArgLeuProSerVal-110 |
| SEQ. ID. NO. 23167 | 147-GlyGlyLysThrThrGlyLysTyr-154 |
| SEQ. ID. NO. 23168 | 222-ArgTyrHisGluAlaThrGlu-228 |
| SEQ. ID. NO. 23169 | 267-ThrArgGlnThrTyrLysTyrIleAspAsp-276 |
| SEQ. ID. NO. 23170 | 467-HisLysProGlyPheGlnThrThrAsnThr-477 |

Antigenic Index - Jameson-Wolf

| | |
|---|---|
| SEQ. ID. NO. 23171 | 1-XxxLysGluThrAlaPhe-6 |
| SEQ. ID. NO. 23172 | 13-GlySerAsnAsnLeuSerArgLeuGlnLysAlaAla-24 |
| SEQ. ID. NO. 23173 | 42-ProGlnAsnMetAspSerGlyIleLeu-50 |
| SEQ. ID. NO. 23174 | 53-ArgValSerAlaGlyGluIleGlyAspIleArgTyrGluGluLysArgAspXxxLysSerAlaGluGlySerIle-77 |
| SEQ. ID. NO. 23175 | 79-AlaPheAsnAsnLysXxxProLeuTyrArgAsnLysIleLeuAsn-93 |
| SEQ. ID. NO. 23176 | 95-ArgAspValGluGlnGlyLeuGluAsnLeuArgArgLeuProSerValLysThrAspIle-114 |
| SEQ. ID. NO. 23177 | 117-IleProSerGluGluGluGlyLysSerAspLeu-127 |
| SEQ. ID. NO. 23178 | 130-LysTrpGlnGlnAsnLysProIleArg-138 |
| SEQ. ID. NO. 23179 | 141-IleGlyIleAspAspAlaGlyGlyLysThrThrGlyLysTyrGlnGly-156 |
| SEQ. ID. NO. 23180 | 162-XxxAspAsnProLeuGlyLeuSer-169 |
| SEQ. ID. NO. 23181 | 180-LeuValHisLysThrAspLeuThrXxxAlaThrGlyThrGluThrGluSerGlySerArgSerTyr-201 |
| SEQ. ID. NO. 23182 | 216-PheAsnHisAsnGlyHisArgTyrHisGluAlaThrGluGlyTyrSerValAsnTyrAspTyrAsnGlyLysGlnTyrGln-242 |
| SEQ. ID. NO. 23183 | 269-GlnThrTyrLysTyrIleAspAspAlaGluIleGluValGlnArgArgSerAlaGlyTrpGluAlaGluLeuArgHis-295 |

TABLE 1-continued

| | |
|---|---|
| SEQ. ID. NO. 23184 | 303-GlnLeuAspGlyLysLeuSerTyrLysArgGlyThrGlyMetArgGlnSerMetProAlaProGluGluAsnGlyGlyGlyThrIleProXxxXxxSerArgMetLysIle-339 |
| SEQ. ID. NO. 23185 | 366-GlnTrpAsnLysThrPro-371 |
| SEQ. ID. NO. 23186 | 374-AlaGlnAspLysLeuSerIleGlySerArgTyrThrValArgGlyPheAspGlyGluGlnSerLeuPheGlyGluArgGlyPheTyrTrpGlnAsnThr-406 |
| SEQ. ID. NO. 23187 | 421-AlaAspTyrGlyArgValSerGlyGluSerAla-431 |
| SEQ. ID. NO. 23188 | 434-ValSerGlyLysGln-438 |
| SEQ. ID. NO. 23189 | 446-PheArgGlyGlyHisLysValGlyGly-454 |
| SEQ. ID. NO. 23190 | 464-LysProLeuHisLysProLysGlyPheGln-473 |
| Hydrophilic Regions - Hopp-Woods | |
| SEQ. ID. NO. 23191 | 1-XxxLysGluThrAlaPhe-6 |
| SEQ. ID. NO. 23192 | 16-AsnLeuSerArgLeuGlnLysAlaAla-24 |
| SEQ. ID. NO. 23193 | 58-GluIleGlyAspIleArgTyrGluGluLysArgAspXxxLysSerAlaGluGlySer-76 |
| SEQ. ID. NO. 23194 | 95-ArgAspValGluGlnGlyLeuGluAsnLeuArgArgLeuProSerValLysThrAspIle-114 |
| SEQ. ID. NO. 23195 | 118-ProSerGluGluGluGlyLysSerAspLeu-127 |
| SEQ. ID. NO. 23196 | 141-IleGlyIleAspAspAlaGlyGlyLysThrThrGlyLysTyr-154 |
| SEQ. ID. NO. 23197 | 180-LeuValHisLysThrAspLeu-186 |
| SEQ. ID. NO. 23198 | 190-ThrGlyThrGluThrGluSerGlySerArgSer-200 |
| SEQ. ID. NO. 23199 | 222-ArgTyrHisGluAlaThrGlu-228 |
| SEQ. ID. NO. 23200 | 273-TyrIleAspAspAlaGluIleGluValGlnArgArgArgSerAlaGlyTrp-289 |
| SEQ. ID. NO. 23201 | 291-AlaGluLeuArgHis-295 |
| SEQ. ID. NO. 23202 | 306-GlyLysLeuSerTyrLysArgGlyThrGlyMetArgGlnSerMetProAlaProGluGluAsnGlyGly-328 |
| SEQ. ID. NO. 23203 | 333-XxxXxxSerArgMetLysIle-339 |
| SEQ. ID. NO. 23204 | 374-AlaGlnAspLysLeuSerIle-380 |
| SEQ. ID. NO. 23205 | 388-GlyPheAspGlyGluGln-393 |
| SEQ. ID. NO. 23206 | 422-AspTyrGlyArgValSerGlyGluSer-430 |
| SEQ. ID. NO. 23207 | 465-ProLeuHisLysProLysGly-471 |
| a708 | |
| AMPHI Regions - AMPHI | |
| SEQ. ID. NO. 23208 | 26-ProSerArgAlaGluLysAlaAsnGlnValSerAsnIle-38 |
| SEQ. ID. NO. 23209 | 57-AlaSerIleGluAspAlaLeuLysSerAspPro-67 |
| SEQ. ID. NO. 23210 | 79-IleTyrGlnTyrLeuLys-84 |
| SEQ. ID. NO. 23211 | 89-AlaGlnGluSerPhe-93 |
| SEQ. ID. NO. 23212 | 119-AsnArgProAlaGluSerMetAla-126 |
| SEQ. ID. NO. 23213 | 128-PheAspLysAlaLeu-132 |
| SEQ. ID. NO. 23214 | 142-IleAlaAsnLeuAsnLys-147 |
| SEQ. ID. NO. 23215 | 176-ProAlaPheLysGluLeuAlaArg-183 |
| SEQ. ID. NO. 23216 | 221-LysAlaLeuGlyAsnAlaGln-227 |
| Antigenic Index - Jameson-Wolf | |
| SEQ. ID. NO. 23217 | 2-ProPheLysProSerLysArgIleSer-10 |
| SEQ. ID. NO. 23218 | 19-AlaCysSerThrSerTyrArgProSerArgAlaGluLysAlaAsnGln-34 |
| SEQ. ID. NO. 23219 | 46-TyrMetArgGlyGlnAspTyrArgGlnXxxThrAlaSerIleGluAspAlaLeuLysSerAspProLysAsnGlu-70 |
| SEQ. ID. NO. 23220 | 84-LysValAsnAspLysAlaGlnGluSerPheArg-94 |
| SEQ. ID. NO. 23221 | 97-LeuSerIleLysProAspSerAlaGluIleAsnAsnAsnTyr-110 |
| SEQ. ID. NO. 23222 | 115-CysGlyArgLeuAsnArgProAlaGlu-123 |
| SEQ. ID. NO. 23223 | 131-AlaLeuAlaAspProThrTyrProXxx-139 |
| SEQ. ID. NO. 23224 | 146-AsnLysGlyIleCysSerAlaLysGlnGlyGln-156 |
| SEQ. ID. NO. 23225 | 176-ProAlaPheLysGluLeuAlaArgThrLysMet-186 |
| SEQ. ID. NO. 23226 | 191-LeuGlyAspAlaAspTyrTyrPheLysLysTyrGlnSerArgValGluValLeuGlnAlaAspAspLeu-213 |
| SEQ. ID. NO. 23227 | 240-PheProTyrSerGluGluLeuGln-247 |
| Hydrophilic Regions - Hopp-Woods | |
| SEQ. ID. NO. 23228 | 4-LysProSerLysArgIle-9 |
| SEQ. ID. NO. 23229 | 24-TyrArgProSerArgAlaGluLysAlaAsnGln-34 |
| SEQ. ID. NO. 23230 | 46-TyrMetArgGlyGlnAspTyrArgGlnXxxThrAlaSerIleGluAspAlaLeuLysSerAspProLysAsnGlu-70 |
| SEQ. ID. NO. 23231 | 84-LysValAsnAspLysAlaGlnGluSerPheArg-94 |
| SEQ. ID. NO. 23232 | 99-IleLysProAspSerAlaGluIle-106 |
| SEQ. ID. NO. 23233 | 117-ArgLeuAsnArgProAlaGlu-123 |
| SEQ. ID. NO. 23234 | 149-IleCysSerAlaLysGlnGly-155 |
| SEQ. ID. NO. 23235 | 177-AlaPheLysGluLeuAlaArgThrLysMet-186 |
| SEQ. ID. NO. 23236 | 201-TyrGlnSerArgValGluValLeuGlnAlaAspAspLeu-213 |
| a709 | |
| AMPHI Regions - AMPHI | |
| SEQ. ID. NO. 23237 | 6-SerLeuLeuAspMetProArgGlyGlu-14 |
| SEQ. ID. NO. 23238 | 18-ValValValAlaLeuIleAlaAlaMetGly-27 |
| SEQ. ID. NO. 23239 | 37-ProHisMetSerIleIleAlaAlaIleValValLeu-48 |
| SEQ. ID. NO. 23240 | 54-AlaArgGlyLeuLysTyrAsn-60 |
| SEQ. ID. NO. 23241 | 64-GlnGlyMetIleGlyAlaLeuAsnGlnGly-73 |
| SEQ. ID. NO. 23242 | 115-SerAlaPheAlaLeuCysSerVal-122 |
| SEQ. ID. NO. 23243 | 130-SerLeuThrThrCysAlaThrVal-137 |
| SEQ. ID. NO. 23244 | 168-LysMetSerProLeuSerAspThrXxx-176 |
| SEQ. ID. NO. 23245 | 185-IleAspLeuPheGluHisIleLysAsnMetMetTyrThrThr-198 |
| SEQ. ID. NO. 23246 | 209-MetLeuXxxLeuLeuPro-214 |
| SEQ. ID. NO. 23247 | 221-LeuAsnSerValGluSerPheArg-228 |
| SEQ. ID. NO. 23248 | 234-ThrGlyLeuValHisCysTyrSerLeuIleProPheAlaLeuLeuValValLeu-251 |
| SEQ. ID. NO. 23249 | 261-AlaMetLeuPheThrValIleAlaAlaValAlaValThrTyr-274 |
| SEQ. ID. NO. 23250 | 278-ThrProAspLeuArgGlnLeuGlyAlaTrpPhe-288 |
| SEQ. ID. NO. 23251 | 299-XxxXxxAspIleAlaLysLeuIleSerArgGlyGly-310 |
| SEQ. ID. NO. 23252 | 334-LeuGlyAlaIleProSerLeuLeuAspAlaValArgSerPheLeuThr-349 |
| SEQ. ID. NO. 23253 | 382-ThrPheLysProVal-386 |
| SEQ. ID. NO. 23254 | 395-ArgAsnLeuSerArgThrLeuGluAspAlaGlyThrValIleAsnProLeuValProTrpSerValCysGlyValPheIleXxxHis-423 |

TABLE 1-continued

Antigenic Index - Jameson-Wolf
SEQ. ID. NO. 23255   9-AspMetProArgGlyGluAla-15
SEQ. ID. NO. 23256   55-ArgGlyLeuLysTyrAsnAspMetGln-63
SEQ. ID. NO. 23257   164-XxxXxxGlyXxxLysMetSerProLeuSerAspThrXxxGlyXxxSer-179
SEQ. ID. NO. 23258   222-AsnSerValGluSerPheArgSerGlnLeuGlu-232
SEQ. ID. NO. 23259   277-SerThrProAspLeuArgGln-283
SEQ. ID. NO. 23260   290-GlyGlyTyrLysLeuGluGlyGluAlaXxxXxxAspIleAlaLysLeuIleSerArgGlyGlyLeuGlu-312
SEQ. ID. NO. 23261   349-ThrAsnAlaGlyArgXxxThr-355
SEQ. ID. NO. 23262   378-LeuSerGlyGluThrPheLysProValTyrAspLysLeuGlyLeuHisSerArgAsnLeuSerArgThrLeuGluAspAlaGlyThr-406
Hydrophilic Regions - Hopp-Woods
SEQ. ID. NO. 23263   9-AspMetProArgGlyGluAla-15
SEQ. ID. NO. 23264   57-LeuLysTyrAsnAspMetGln-63
SEQ. ID. NO. 23265   165-XxxGlyXxxLysMetSerProLeuSerAspThrXxxGly-177
SEQ. ID. NO. 23266   225-GluSerPheArgSerGlnLeuGlu-232
SEQ. ID. NO. 23267   279-ProAspLeuArgGln-283
SEQ. ID. NO. 23268   293-LysLeuGluGlyGluAlaXxxXxxAspIleAlaLysLeuIleSer-307
SEQ. ID. NO. 23269   396-AsnLeuSerArgThrLeuGluAspAlaGly-405
a710
AMPHI Regions - AMPHI
SEQ. ID. NO. 23270   6-LysIleArgLeuMetArgGluLeuAsnLysTrpSerGln-18
SEQ. ID. NO. 23271   31-GlyTyrAlaLysIleGlu-36
SEQ. ID. NO. 23272   45-ProArgLeuGluGlnLeuAlaGlnIlePheLysIleAspMetTrpAspLeuLeuLys-63
SEQ. ID. NO. 23273   105-CysLysGluMetLeuGlu-110
Antigenic Index - Jameson-Wolf
SEQ. ID. NO. 23274   1-MetGluThrHisGluLysIleArgLeuMetArgGluLeuAsnLysTrpSerGlnGluAspMetAlaGluLysLeuAla-26
SEQ. ID. NO. 23275   33-AlaLysIleGluArgGlyGluThrGlnLeuAsnIleProArgLeuGluGln-49
SEQ. ID. NO. 23276   62-LeuLysSerGlyGlyGlyGly-68
SEQ. ID. NO. 23277   74-AsnAspValAspThrAsnSerGlyGlu-82
SEQ. ID. NO. 23278   88-AlaGlnAspAlaSerGlyLys-94
SEQ. ID. NO. 23279   100-MetGluLeuLysHisCysLysGluMetLeuGluHisLysAspLysGluIleGluLeuLeuArgLysLeuThrGlu-124
Hydrophilic Regions - Hopp-Woods
SEQ. ID. NO. 23280   1-MetGluThrHisGluLysIleArgLeuMetArgGluLeuAsnLysTrpSerGlnGluAspMetAlaGluLysLeuAla-26
SEQ. ID. NO. 23281   33-AlaLysIleGluArgGlyGluThr-40
SEQ. ID. NO. 23282   45-ProArgLeuGluGln-49
SEQ. ID. NO. 23283   74-AsnAspValAspThrAsnSerGly-81
SEQ. ID. NO. 23284   100-MetGluLeuLysHisCysLysGluMetLeuGluHisLysAspLysGluIleGluLeuLeuArgLysLeuThrGlu-124
a711
AMPHI Regions - AMPHI
SEQ. ID. NO. 23285   28-AlaGluSerTyrArgAsnLeuThrAlaSerGluIleAlaLysValTyrThrIleAlaArgMetThr-49
SEQ. ID. NO. 23286   AspLeuAspMetLeuAsnAspIleLys-58
SEQ. ID. NO. 23287   67-SerGlyGlnSerPheAspAspTrpArgLysGlyIleLeu-79
SEQ. ID. NO. 23288   95-GlyLysAspIleIleAspProAlaThrGlyGluValPheGlySerProArgArgLeuGluThrIleTyrArgThrAsnMet-121
SEQ. ID. NO. 23289   128-GlyGlnTyrGlnGlyTyrMet-134
SEQ. ID. NO. 23290   158-SerAlaIleAspGly-162
SEQ. ID. NO. 23291   195-ValGluArgGlnGly-199
SEQ. ID. NO. 23292   207-SerAspAsnLeuValGluThrHis-214
SEQ. ID. NO. 23293   258-LysTyrAspArgAlaLeuAlaHisGlnPheAla-268
SEQ. ID. NO. 23294   281-PheLysGlnLeuGluLysGluPheTyr-289
SEQ. ID. NO. 23295   329-GlnGluLeuAlaGlyMetThr-335
SEQ. ID. NO. 23296   352-SerArgGluGlyGlnAsnPhe-358
SEQ. ID. NO. 23297   360-AspSerTyrTyrAlaPheLeuProAspMetLeuGlnAsnProGlu-374
SEQ. ID. NO. 23298   395-TrpAlaValLeuLysTyrIleLysGluValAspGluIle-407
SEQ. ID. NO. 23299   413-ArgIleSerAsnAspLysGluIleAlaLys-422
Antigenic Index - Jameson-Wolf
SEQ. ID. NO. 23300   11-SerLeuProProLysLysAlaIleGlu-19
SEQ. ID. NO. 23301   21-LeuGluSerLysLysValThrAlaGluSerTyrArgAsnLeuThr-35
SEQ. ID. NO. 23302   55-AsnAspIleLysThrSerMet-61
SEQ. ID. NO. 23303   63-GluSerAlaLysSerGlyGlnSerPheAspAspTrpArgLysGlyIle-78
SEQ. ID. NO. 23304   82-LeuSerAsnLysGlyTrpLeuHisProAsnGlyHisAsnGlyLysAspIleIleAspProAlaThrGlyGluValPheGlySerProArgArgLeu
                    GluThrIleTyrArgThrAsnMet-121
SEQ. ID. NO. 23305   126-AsnAlaGlyGlnTyrGlnGly-132
SEQ. ID. NO. 23306   135-AlaAsnIleAspAlaArgProTyrTrp-143
SEQ. ID. NO. 23307   147-AlaValGlyAspSerArgThrArgProAlaHisSerAla-159
SEQ. ID. NO. 23308   165-TyrArgTyrAspAspProPheTrp-172
SEQ. ID. NO. 23309   177-ProProAsnGlyTyrAsnCysArgCysSer-186
SEQ. ID. NO. 23310   190-LeuSerGluArgAspValGluArgGlnGlyArgIleValGlyGlnSerThrSerAspAsnLeuValGlu-212
SEQ. ID. NO. 23311   215-LysIleTyrAsnLysLysGlyAspThr-223
SEQ. ID. NO. 23312   229-TyrLysAlaProAspGlySerLeuTyrThrThrAspArgGlyPheAspTyrAsnAlaGlyArgMetAsnTyrArgProAspLeuAspLysTyrAsp
                    ArgAlaLeu-263
SEQ. ID. NO. 23313   268-AlaLysAlaGluMetGlyGlyAlaAspPheLysThrSerPheLysGlnLeuGluLysGluPheTyrGluValLysGlnArgLeuAspIleAspGly
                    LysProAspLysGluGlnLysIleLysIleArgAsnAlaLeu-313
SEQ. ID. NO. 23314   324-LeuSerLysGluThrGlnGlu-330
SEQ. ID. NO. 23315   342-SerAspAspThrLeuValLysGlnValAspSerArgGluGlyGlnAsnPheAspAspSerTyrTyr-363
SEQ. ID. NO. 23316   370-LeuGlnAsnProGluHisValIleArgAspAsnArgGlu-382
SEQ. ID. NO. 23317   387-AlaArgTyrLysGlySer-392
SEQ. ID. NO. 23318   400-TyrIleLysGluValAspGlu-406
SEQ. ID. NO. 23319   411-SerTyrArgIleSerAsnAspLysGluIleAla-421
SEQ. ID. NO. 23320   424-MetAlaLysLysLysValLeuLys-431
Hydrophilic Regions - Hopp-Woods
SEQ. ID. NO. 23321   13-ProProLysLysAlaIleGlu-19

TABLE 1-continued

| SEQ. ID. NO. | Sequence |
|---|---|
| SEQ. ID. NO. 23322 | 21-LeuGluSerLysLysValThrAlaGluSerTyrArg-32 |
| SEQ. ID. NO. 23323 | 55-AsnAspIleLysThrSerMet-61 |
| SEQ. ID. NO. 23324 | 63-GluSerAlaLysSerGlyGlnSerPheAspAspTrpArgLys-76 |
| SEQ. ID. NO. 23325 | 93-HisAsnGlyLysAspIleIleAsp-100 |
| SEQ. ID. NO. 23326 | 108-GlySerProArgArgLeuGluThr-115 |
| SEQ. ID. NO. 23327 | 147-AlaValGlyAspSerArgThrArgProAla-156 |
| SEQ. ID. NO. 23328 | 190-LeuSerGluArgAspValGluArgGlnGlyArgIleVal-202 |
| SEQ. ID. NO. 23329 | 205-SerThrSerAspAsnLeuValGlu-212 |
| SEQ. ID. NO. 23330 | 215-LysIleTyrAsnLysLysGlyAspThr-223 |
| SEQ. ID. NO. 23331 | 238-ThrThrAspArgGlyPheAsp-244 |
| SEQ. ID. NO. 23332 | 250-MetAsnTyrArgProAspLeuAspLysTyrAspArgAlaLeu-263 |
| SEQ. ID. NO. 23333 | 268-AlaLysAlaGluMetGlyGlyAlaAspPheLysThrSerPheLysGlnLeuGluLysGluPheTyrGluValLysGlnArgLeuAspIleAspGlyLysProAspLysGluGlnLysIleLysIleArgAsnAlaLeu-313 |
| SEQ. ID. NO. 23334 | 324-LeuSerLysGluThrGlnGlu-330 |
| SEQ. ID. NO. 23335 | 344-AspThrLeuValLysGlnValAspSerArgGluGlyGlnAsnPheAsp-359 |
| SEQ. ID. NO. 23336 | 375-HisValIleArgAspAsnArgGlu-382 |
| SEQ. ID. NO. 23337 | 400-TyrIleLysGluValAspGlu-406 |
| SEQ. ID. NO. 23338 | 414-IleSerAsnAspLysGluIleAla-421 |
| SEQ. ID. NO. 23339 | 424-MetAlaLysLysLysValLeuLys-431 | a713
AMPHI Regions - AMPHI

| SEQ. ID. NO. | Sequence |
|---|---|
| SEQ. ID. NO. 23340 | 18-GluHisArgHisTrpGlu-23 |
| SEQ. ID. NO. 23341 | 115-AspAlaAlaLysLysLeuAlaAlaProTrpProGlnIle-127 |
| SEQ. ID. NO. 23342 | 150-ThrValTrpGlnAlaLeuThrHisIleAlaAsnSerVal-162 |
| SEQ. ID. NO. 23343 | 257-AspAsnLeuAlaAlaLeuGln-263 |
| SEQ. ID. NO. 23344 | 265-GlnAlaLysLysGln-269 |

Antigenic Index - Jameson-Wolf

| SEQ. ID. NO. | Sequence |
|---|---|
| SEQ. ID. NO. 23345 | 1-MetGlnAsnAsnSerTyrGly-7 |
| SEQ. ID. NO. 23346 | 13-ArgValGlyGlyLysGluHisArgHisTrpGluArgTyrAspIleAspSerAspPhe-31 |
| SEQ. ID. NO. 23347 | 44-ArgLeuGlyProGluAlaAlaIleProAspLeuSerGlyGluSerCysGluValValIle-63 |
| SEQ. ID. NO. 23348 | 74-GlySerGlnArgHisGlyLysSerLysGlyGlyArgGluLeuSerLeuSerGlyArgAspLeu-94 |
| SEQ. ID. NO. 23349 | 106-LeuAsnValLysGly-110 |
| SEQ. ID. NO. 23350 | 115-AspAlaAlaLysLysLeu-120 |
| SEQ. ID. NO. 23351 | 134-ValGluAsnAsnProAlaLeuAspLysIleAspIleGluProGlyGluThrVal-151 |
| SEQ. ID. NO. 23352 | 167-TrpLeuGluProAspGlyThrLeu-174 |
| SEQ. ID. NO. 23353 | 192-SerArgThrAspSerArgArgAsnIleGluArgMetAspIleGluTrpAspThrAspAsnArgPheSerGlu-215 |
| SEQ. ID. NO. 23354 | 222-SerHisGlyArgSerGlyAspSerAlaLysHisAspLeu-234 |
| SEQ. ID. NO. 23355 | 236-TrpValTyrLysAspProThrMetThrLeuHisArgProLysThrValVal-252 |
| SEQ. ID. NO. 23356 | 254-SerAspAlaAspAsn-258 |
| SEQ. ID. NO. 23357 | 263-GlnLysGlnAlaLysLysGlnLeuAla-271 |
| SEQ. ID. NO. 23358 | 284-ValGlyGlyHisLysThrArgAspGly-292 |
| SEQ. ID. NO. 23359 | 302-HisValIleAspAspGluHisGlyIle-310 |
| SEQ. ID. NO. 23360 | 321-PheMetLeuSerArgMetAspGlyThrGlnThrGluLeuArgLeuLysGluAspGlyIleTrpThrProAspAlaTyrProLysLysAlaGluAlaAlaArgLysArgLysGlyLysArgLysGlyValSerHisLysGlyLysLysGlyGlyLysLysGlnAlaGlu-376 |

Hydrophilic Regions - Hopp-Woods

| SEQ. ID. NO. | Sequence |
|---|---|
| SEQ. ID. NO. 23361 | 14-ValGlyGlyLysGluHisArgHisTrpGluArgTyrAspIleAspSer-29 |
| SEQ. ID. NO. 23362 | 54-LeuSerGlyGluSerCysGluValValIle-63 |
| SEQ. ID. NO. 23363 | 76-GlnArgHisGlyLysSerLysGlyGlyArgGluLeuSerLeuSerGlyArgAspLeu-94 |
| SEQ. ID. NO. 23364 | 115-AspAlaAlaLysLysLeu-120 |
| SEQ. ID. NO. 23365 | 138-ProAlaLeuAspLysIleAspIleGluProGlyGlu-149 |
| SEQ. ID. NO. 23366 | 168-LeuGluProAspGly-172 |
| SEQ. ID. NO. 23367 | 193-ArgThrAspSerArgArgAsnIleGluArgMetAspIleGluTrpAspThrAspAsnArgPheSer-214 |
| SEQ. ID. NO. 23368 | 222-SerHisGlyArgSerGlyAspSerAlaLysHisAspLeu-234 |
| SEQ. ID. NO. 23369 | 246-HisArgProLysThr-250 |
| SEQ. ID. NO. 23370 | 254-SerAspAlaAspAsn-258 |
| SEQ. ID. NO. 23371 | 263-GlnLysGlnAlaLysLysGlnLeuAla-271 |
| SEQ. ID. NO. 23372 | 286-GlyHisLysThrArgAsp-291 |
| SEQ. ID. NO. 23373 | 302-HisValIleAspAspGluHisGlyIle-310 |
| SEQ. ID. NO. 23374 | 325-ArgMetAspGlyThrGlnThrGluLeuArgLeuLysGluAspGlyIleTrp-341 |
| SEQ. ID. NO. 23375 | 345-AlaTyrProLysLysAlaGluAlaAlaArgLysArgLysGlyLysArgLysGlyValSerHisLysGlyLysLysGlyGlyLysLysGlnAlaGlu-376 | a714
AMPHI Regions - AMPHI

| SEQ. ID. NO. | Sequence |
|---|---|
| SEQ. ID. NO. 23376 | 6-IleLeuArgGlyLeuLeuPro-12 |
| SEQ. ID. NO. 23377 | 34-LeuAspAlaValAlaGluSerAlaGlnSerValAlaAspAlaValAspProSer-51 |
| SEQ. ID. NO. 23378 | 55-GlnMetLeuAlaAspTrpGluArgValLeuGlyLeu-66 |
| SEQ. ID. NO. 23379 | 79-AlaValMetAlaLysLeuAsnGluThrGly-88 |
| SEQ. ID. NO. 23380 | 98-LeuAlaGluAlaAla-102 |
| SEQ. ID. NO. 23381 | 110-GluProGlnProPhe-114 |
| SEQ. ID. NO. 23382 | 116-AlaGlyValAsnArgAlaGlyAspArgLeu-125 |
| SEQ. ID. NO. 23383 | 155-AlaGlyAspArgLeuThrAspTyrSerAspAlaValIleGluSerLeuPheAsnArgLeuLys-175 |

Antigenic Index - Jameson-Wolf

| SEQ. ID. NO. | Sequence |
|---|---|
| SEQ. ID. NO. 23384 | 15-SerTyrAlaArgAsnAlaProArgValArgAlaGlnAlaGluIleAspGlyAlaAla-33 |
| SEQ. ID. NO. 23385 | 36-AlaValAlaGluSerAlaGlnSerVal-44 |
| SEQ. ID. NO. 23386 | 46-AspAlaValAspProSerSerAlaGly-54 |
| SEQ. ID. NO. 23387 | 64-LeuGlyLeuAspGlyThrGlyLysAsnArgGlnArgArgVal-77 |
| SEQ. ID. NO. 23388 | 83-LysLeuAsnGluThrGlyGlyLeu-90 |
| SEQ. ID. NO. 23389 | 107-GlnIleAspGluProGlnProPheArgAlaGlyValAsnArgAlaGlyAspArgLeuAlaPro-127 |
| SEQ. ID. NO. 23390 | 138-ValArgGlyGlyAsnAsnArgIleThrArgPheArgAlaGlyIle-152 |
| SEQ. ID. NO. 23391 | 154-AlaAlaGlyAspArgLeuThrAspTyrSerAspAlaValIle-167 |
| SEQ. ID. NO. 23392 | 170-LeuPheAsnArgLeuLysPro-176 |

TABLE 1-continued

Hydrophilic Regions - Hopp-Woods
SEQ. ID. NO. 23393    18-ArgAsnAlaProArgValArgAlaGlnAlaGluIleAspGlyAlaAla-33
SEQ. ID. NO. 23394    36-AlaValAlaGluSerAlaGlnSerVal-44
SEQ. ID. NO. 23395    46-AspAlaValAspProSerSer-52
SEQ. ID. NO. 23396    68-GlyThrGlyLysAsnArgGlnArgArgVal-77
SEQ. ID. NO. 23397    107-GlnIleAspGluProGlnProPhe-114
SEQ. ID. NO. 23398    117-GlyValAsnArgAlaGlyAspArgLeuAlaPro-127
SEQ. ID. NO. 23399    139-ArgGlyGlyAsnAsnArgIleThrArgPheArgAla-150
SEQ. ID. NO. 23400    154-AlaAlaGlyAspArgLeuThrAspTyrSerAspAlaValIle-167
SEQ. ID. NO. 23401    170-LeuPheAsnArgLeuLysPro-176
a715
AMPHI Regions - AMPHI
SEQ. ID. NO. 23402    15-GlnIleGluArgLeuGlyAsnGlyIle-23
SEQ. ID. NO. 23403    31-ArgArgLeuSerGluThrMetHis-38
SEQ. ID. NO. 23404    64-LeuSerAspSerGlyArgLeuLysAspSerPheSer-75
SEQ. ID. NO. 23405    94-IleHisAsnPheGlyGly-99
Antigenic Index - Jameson-Wolf
SEQ. ID. NO. 23406    15-GlnIleGluArgLeuGlyAsnGlyIleGluAsnArgTyrLeuLeu-29
SEQ. ID. NO. 23407    47-TyrAlaGlyArgProLysTrpLeuGlyLeuLysTyrArgAspGlyLysProLeuSerAspSerGlyArgLeuLysAspSerPheSerThrLeuSerAsp
                     AsnAspThrAla-83
SEQ. ID. NO. 23408    98-GlyGlyMetAlaGlyArgAsnArgLysValArgIleProGlnArgGluPhe-114
SEQ. ID. NO. 23409    118-ThrAspAspAspLysGlnAlaLeuMetAspAspValGlnAsp-131
Hydrophilic Regions - Hopp-Woods
SEQ. ID. NO. 23410    15-GlnIleGluArgLeuGlyAsn-21
SEQ. ID. NO. 23411    57-LysTyrArgAspGlyLysProLeuSerAspSerGlyArgLeuLysAspSerPhe-74
SEQ. ID. NO. 23412    78-SerAspAsnAspThr-82
SEQ. ID. NO. 23413    101-AlaGlyArgAsnArgLysValArgIleProGlnArgGlu-113
SEQ. ID. NO. 23414    118-ThrAspAspAspLysGlnAlaLeuMetAspAspValGlnAsp-131
a716
AMPHI Regions - AMPHI
SEQ. ID. NO. 23415    33-GlyValHisLysSerAlaHisGly-40
SEQ. ID. NO. 23416    71-AlaThrValLysLysThrHisLysHisThrLysAla-82
Antigenic Index - Jameson-Wolf
SEQ. ID. NO. 23417    1-MetAsnLysAsnIle-5
SEQ. ID. NO. 23418    23-AlaAlaAsnLysProAlaSerAsnAlaThrGlyValHisLysSerAlaHisGlySerCysGlyAlaSerLysSerAlaGluGlySerCysGlyAlaAla
                     GlySerLysAlaGlyGluGlyLysCysGlyGluGlyLysCysGlyAlaThrValLysLysThrHisLysHisThrLysAlaSerLysAlaLysAlaLysSerAla
                     GluGlyLysCysGlyGluGlyLysCysGlySerLys-102
Hydrophilic Regions - Hopp-Woods
SEQ. ID. NO. 23419    23-AlaAlaAsnLysProAlaSer-29
SEQ. ID. NO. 23420    33-GlyValHisLysSerAlaHis-39
SEQ. ID. NO. 23421    43-GlyAlaSerLysSerAlaGluGlySerCys-52
SEQ. ID. NO. 23422    55-AlaGlySerLysAlaGlyGluGlyLysCysGlyGluGlyLysCys-69
SEQ. ID. NO. 23423    71-AlaThrValLysLysThrHisLysHisThrLysAlaSerLysAlaLysAlaLysSerAlaGluGlyLysCysGlyGluGlyLysCysGlySerLys-102
a717
AMPHI Regions - AMPHI
SEQ. ID. NO. 23424    175-AlaValTyrAlaLeuAlaAsn-181
SEQ. ID. NO. 23425    209-LeuHisArgGlyLeu-213
SEQ. ID. NO. 23426    223-SerIleAlaTyrTrp-227
SEQ. ID. NO. 23427    241-AlaGlyLeuGluGlnLeuGly-247
SEQ. ID. NO. 23428    263-GlnSerIlePheSerThrValTrpThrProTyrIlePheArgAlaIleGluAla-280
SEQ. ID. NO. 23429    305-ThrGlyIlePheSerProLeuAlaSer-313
SEQ. ID. NO. 23430    347-LeuAsnValValArgLysThr-353
SEQ. ID. NO. 23431    358-LeuAlaThrLeuGlyAlaLeuAla-365
SEQ. ID. NO. 23432    401-SerSerCysArgLeuTrpGlnProLeuLysArgLeu-412
SEQ. ID. NO. 23433    430-CysPheGlyThrPro-434
SEQ. ID. NO. 23434    442-GlyValTrpAlaValTyrLeuAla-449
SEQ. ID. NO. 23435    457-LysAspLeuHisLysLeuPheHisTyr-465
Antigenic Index - Jameson-Wolf
SEQ. ID. NO. 23436    1-MetAspThrLysGlu-5
SEQ. ID. NO. 23437    32-ProAlaAspAspIleGlyArg-38
SEQ. ID. NO. 23438    69-AlaAspLysAspThrLeu-74
SEQ. ID. NO. 23439    95-SerArgProSerLeuProSerGluIle-103
SEQ. ID. NO. 23440    135-MetGluGlyArgAla-139
SEQ. ID. NO. 23441    192-AsnArgCysArgLeuLysAlaValArgArgAlaProPheSerSer-206
SEQ. ID. NO. 23442    231-SerAlaAspArgLeuPheLeu-237
SEQ. ID. NO. 23443    278-IleGluAlaAsnAlaProProAlaArgLeu-287
SEQ. ID. NO. 23444    289-AlaThrAlaGluSer-293
SEQ. ID. NO. 23445    317-ProGluAsnTyrAla-321
SEQ. ID. NO. 23446    349-ValValArgLysThrArgProIleAla-357
SEQ. ID. NO. 23447    376-ProSerGlyGlyAlaArgGly-382
SEQ. ID. NO. 23448    398-LysThrGluSerSerCysArgLeu-405
SEQ. ID. NO. 23449    453-LeuArgHisArgLysAspLeuHis-460
Hydrophilic Regions - Hopp-Woods
SEQ. ID. NO. 23450    1-MetAspThrLysGlu-5
SEQ. ID. NO. 23451    69-AlaAspLysAspThrLeu-74
SEQ. ID. NO. 23452    135-MetGluGlyArgAla-139
SEQ. ID. NO. 23453    192-AsnArgCysArgLeuLysAlaValArgArgAlaProPhe-204
SEQ. ID. NO. 23454    281-AsnAlaProProAlaArgLeu-287
SEQ. ID. NO. 23455    289-AlaThrAlaGluSer-293
SEQ. ID. NO. 23456    349-ValValArgLysThrArgPro-355

TABLE 1-continued

| | |
|---|---|
| SEQ. ID. NO. 23457 | 378-GlyGlyAlaArgGly-382 |
| SEQ. ID. NO. 23458 | 399-ThrGluSerSerCys-403 |
| SEQ. ID. NO. 23459 | 453-LeuArgHisArgLysAspLeuHis-460 |
| a718-1 | |
| AMPHI Regions - AMPHI | |
| SEQ. ID. NO. 23460 | 28-IleThrAlaThrGlyArgValIleAlaGluHisProSerAsnPheIleThrProGln-46 |
| SEQ. ID. NO. 23461 | 49-ArgAlaLeuPheGlu-53 |
| SEQ. ID. NO. 23462 | 110-AspGlnAlaTyrGluMetMetAspSerLeuProThr-121 |
| SEQ. ID. NO. 23463 | 124-AspLeuIleMetAspLeuMetAspAlaValGlyHisGly-136 |
| SEQ. ID. NO. 23464 | 160-ProGlnSerTrpPheLys-165 |
| SEQ. ID. NO. 23465 | 198-ArgSerValGlnGln-202 |
| SEQ. ID. NO. 23466 | 210-ThrLeuSerTrpLeuTyrMetPhe-217 |
| SEQ. ID. NO. 23467 | 219-HisTyrAlaValHisAspPheAlaGluPheLeuGluLeu-231 |
| SEQ. ID. NO. 23468 | 255-ArgAlaValAlaGluIle-260 |
| SEQ. ID. NO. 23469 | 279-AlaAlaAsnGlyMetThrSer-285 |
| SEQ. ID. NO. 23470 | 320-ThrAsnAlaLeuGlyAsnIleHisAsnGluIleArg-331 |
| SEQ. ID. NO. 23471 | 341-GlnValAlaGlnThrIleThrSerGlnIleIleGlyProPhe-354 |
| SEQ. ID. NO. 23472 | 363-AspProAsnArgVal-367 |
| SEQ. ID. NO. 23473 | 376-GluProLysAspIleAlaValPheAlaAspAlaIleProLysLeuValAsp-392 |
| SEQ. ID. NO. 23474 | 395-ValGlnIleProGlu-399 |
| SEQ. ID. NO. 23475 | 420-ArgGlnValProAspAsnPro-426 |
| SEQ. ID. NO. 23476 | 448-HisGlnGluIleLeuAspGlyAlaLeuAspAsp-458 |
| SEQ. ID. NO. 23477 | 469-LeuAsnProMetValArgGlnAlaValAlaAlaLeuAsnAlaCysAsnSerTyrGlu-487 |
| Antigenic Index - Jameson-Wolf | |
| SEQ. ID. NO. 23478 | 4-IleMetAlaLysLysAsnAsnLysThrLysIleGlnLysProGluAlaAlaLeu-21 |
| SEQ. ID. NO. 23479 | 30-AlaThrGlyArgValIleAla-36 |
| SEQ. ID. NO. 23480 | 38-HisProSerAsnPhe-42 |
| SEQ. ID. NO. 23481 | 44-ThrProGlnLysMetArgAlaLeuPheGluAspAlaGluSerGlyAspIleArgAlaGlnHis-64 |
| SEQ. ID. NO. 23482 | 68-AlaAspIleGluGluArgAspSerAspIle-77 |
| SEQ. ID. NO. 23483 | 81-MetGlyThrArgLysArgAla-87 |
| SEQ. ID. NO. 23484 | 95-ValAlaProProArgAsnAlaThrProGluGluGluLysLeuSerAspGlnAlaTyrGluMet-115 |
| SEQ. ID. NO. 23485 | 119-LeuProThrLeuGlu-123 |
| SEQ. ID. NO. 23486 | 148-AspGlyLeuTyrLeuProArgAsnPheIleHisArgProGlnSerTrpPheLysTrpAspLysAspAsnGlyLeu-172 |
| SEQ. ID. NO. 23487 | 174-LeuArgThrArgGluAsnProGluGlyGluAla-184 |
| SEQ. ID. NO. 23488 | 193-HisThrGlnLysSerArgSerValGlnGlnAlaArgAsnGlyLeuPhe-208 |
| SEQ. ID. NO. 23489 | 237-ArgIleGlyLysTyrGlyAlaGlyAlaThrLysGluGluLysAsnThrLeu-253 |
| SEQ. ID. NO. 23490 | 268-MetProGluGlyMetGluIleGluLeu-276 |
| SEQ. ID. NO. 23491 | 280-AlaAlaAsnGlyMetThrSerAla-286 |
| SEQ. ID. NO. 23492 | 295-AspTrpCysGluLysSerAlaAla-302 |
| SEQ. ID. NO. 23493 | 310-LeuThrSerGlyAlaAspGlyLysSerSerThrAsnAlaLeuGly-324 |
| SEQ. ID. NO. 23494 | 328-AsnGluIleArgArgAspLeuLeuValSerAspAlaLysGlnVal-342 |
| SEQ. ID. NO. 23495 | 359-TyrProHisAlaAspProAsnArgValProLysPheGluPheAspThrArgGluProLysAspIle-380 |
| SEQ. ID. NO. 23496 | 397-IleProGluSerTrpValArgAspLysLeuVal-407 |
| SEQ. ID. NO. 23497 | 410-AspValGlnGluGlyGlyGluAlaValLeu-418 |
| SEQ. ID. NO. 23498 | 420-ArgGlnValProAspAsnProValAsnArg-429 |
| SEQ. ID. NO. 23499 | 440-ValProSerLysAlaThrGlyArgHisGlnGluIleLeuAspGlyAlaLeuAsp-457 |
| SEQ. ID. NO. 23500 | 459-AlaLeuValGluProAspPheAsnSerGlnLeu-469 |
| SEQ. ID. NO. 23501 | 484-AsnSerTyrGluGluAlaAspAla-491 |
| SEQ. ID. NO. 23502 | 499-AsnLeuAspAsnAlaLysLeuArgThr-507 |
| SEQ. ID. NO. 23503 | 519-LeuGlyGlnAspHisAlaArgAla-526 |
| Hydrophilic Regions - Hopp-Woods | |
| SEQ. ID. NO. 23504 | 4-IleMetAlaLysLysAsnAsnLysThrLysIleGlnLysProGluAlaAlaLeu-21 |
| SEQ. ID. NO. 23505 | 46-GlnLysMetArgAlaLeuPheGluAspAlaGluSerGlyAspIleArgAlaGlnHis-64 |
| SEQ. ID. NO. 23506 | 68-AlaAspIleGluGluArgAspSerAspIle-77 |
| SEQ. ID. NO. 23507 | 81-MetGlyThrArgLysArgAla-87 |
| SEQ. ID. NO. 23508 | 96-AlaProProArgAsnAlaThrProGluGluGluLysLeuSerAspGlnAlaTyrGluMet-115 |
| SEQ. ID. NO. 23509 | 165-LysTrpAspLysAspAsnGlyLeu-172 |
| SEQ. ID. NO. 23510 | 174-LeuArgThrArgGluAsnProGluGlyGluAla-184 |
| SEQ. ID. NO. 23511 | 195-GlnLysSerArgSerValGlnGlnAlaArg-204 |
| SEQ. ID. NO. 23512 | 245-AlaThrLysGluGluLysAsnThrLeu-253 |
| SEQ. ID. NO. 23513 | 270-GluGlyMetGluIleGluLeu-276 |
| SEQ. ID. NO. 23514 | 295-AspTrpCysGluLysSerAlaAla-302 |
| SEQ. ID. NO. 23515 | 312-SerGlyAlaAspGlyLysSerSerThr-320 |
| SEQ. ID. NO. 23516 | 328-AsnGluIleArgArgAspLeuLeuValSerAspAlaLysGlnVal-342 |
| SEQ. ID. NO. 23517 | 363-AspProAsnArgValProLysPheGluPheAspThrArgGluProLysAsp-379 |
| SEQ. ID. NO. 23518 | 401-TrpValArgAspLysLeuVal-407 |
| SEQ. ID. NO. 23519 | 410-AspValGlnGluGlyGlyGluAlaValLeu-418 |
| SEQ. ID. NO. 23520 | 421-GlnValProAspAsnProValAsn-428 |
| SEQ. ID. NO. 23521 | 440-ValProSerLysAlaThrGlyArgHisGlnGluIleLeuAspGlyAlaLeuAsp-457 |
| SEQ. ID. NO. 23522 | 485-SerTyrGluGluAlaAspAla-491 |
| SEQ. ID. NO. 23523 | 501-AspAsnAlaLysLeu-505 |
| SEQ. ID. NO. 23524 | 522-AspHisAlaArgAla-526 |
| a720 | |
| AMPHI Regions - AMPHI | |
| SEQ. ID. NO. 23525 | 19-GlnAlaValArgLeuLeuSerThrSer-27 |
| SEQ. ID. NO. 23526 | 46-AlaProAspLeuIleGluValAsn-53 |
| SEQ. ID. NO. 23527 | 66-AlaLeuArgAlaValGlnThrAla-73 |
| SEQ. ID. NO. 23528 | 91-GlnThrAlaGluSerLeu-96 |
| SEQ. ID. NO. 23529 | 102-ArgLeuAsnAlaLeuValAla-108 |
| SEQ. ID. NO. 23530 | 126-GlyThrIleHisGlnIleAlaHisGluPheTyrGlyAspIleAlaArgAlaAlaGluLeuVal-146 |

TABLE 1-continued

Antigenic Index - Jameson-Wolf
SEQ. ID. NO. 23531　1-GlyLeuGlnAsnArgLeuAsnArgLeuThrAlaLysGlnVal-14
SEQ. ID. NO. 23532　39-AlaHisGlyGluGluMetThrAla-46
SEQ. ID. NO. 23533　48-AspLeuIleGluValAsnArgAlaMetArgArgArgMetGlnAla-62
SEQ. ID. NO. 23534　74-AlaAlaGluSerGlyGlyLeuThrAla-82
SEQ. ID. NO. 23535　91-GlnThrAlaGluSerLeuArgAlaAlaAla-100
SEQ. ID. NO. 23536　112-AsnGlnLysProProLeu-117
SEQ. ID. NO. 23537　121-GlnAlaProIleAspGlyThr-127
SEQ. ID. NO. 23538　139-IleAlaArgAlaAlaGlu-144
SEQ. ID. NO. 23539　157-PheIleLysArgGlyThrLeuValAsnSerTyrAlaLys-169
Hydrophilic Regions - Hopp-Woods
SEQ. ID. NO. 23540　4-AsnArgLeuAsnArgLeuThrAla-11
SEQ. ID. NO. 23541　39-AlaHisGlyGluGluMetThrAla-46
SEQ. ID. NO. 23542　48-AspLeuIleGluValAsnArgAlaMetArgArgArgMetGlnAla-62
SEQ. ID. NO. 23543　74-AlaAlaGluSerGlyGly-79
SEQ. ID. NO. 23544　94-GluSerLeuArgAlaAlaAla-100
SEQ. ID. NO. 23545　139-IleAlaArgAlaAlaGlu-144
a721
AMPHI Regions - AMPHI
SEQ. ID. NO. 23546　86-AlaGlyTrpMetArgTrpLeuGlu-93
SEQ. ID. NO. 23547　119-ArgTyrIleSerAlaVal-124
SEQ. ID. NO. 23548　134-SerLysIlePheHisAlaAlaLeuThrAsnPheProAlaLeuAspGlyMetAspGluValLeuAla-155
SEQ. ID. NO. 23549　169-AsnProMetLysGluLeuLeuGlnGlnLeuPheGlyLeu-181
SEQ. ID. NO. 23550　209-AspValPheAlaGln-213
SEQ. ID. NO. 23551　235-LysTyrAlaProIleSerValValGlnGluLeuGln-246
SEQ. ID. NO. 23552　281-TrpAlaGluGlyValLeuLysGlnProGlyGly-291
SEQ. ID. NO. 23553　293-AlaPheLeuThrGlyPheIleGlu-300
Antigenic Index - Jameson-Wolf
SEQ. ID. NO. 23554　1-MetSerLysAsnAlaGln-6
SEQ. ID. NO. 23555　16-GluValGlnProLysAspGlyArgIle-24
SEQ. ID. NO. 23556　27-LeuProTyrGlyGlu-31
SEQ. ID. NO. 23557　33-ArgAlaValAspGlyArgProThrAspValProAla-44
SEQ. ID. NO. 23558　48-ThrGluGluAsnGlyHisAsp-54
SEQ. ID. NO. 23559　58-LeuAlaAsnSerSerArgAsnGlnLeu-66
SEQ. ID. NO. 23560　74-LeuTyrLysGluLysAsnGlyGlnProAlaPro-84
SEQ. ID. NO. 23561　93-GluPheThrProLysGlyMetPheAla-101
SEQ. ID. NO. 23562　104-GluTrpThrAspLysAlaAla-110
SEQ. ID. NO. 23563　114-AlaAlaLysGluTyrArg-119
SEQ. ID. NO. 23564　125-PheSerTyrAspThrLysGlyTyrVal-133
SEQ. ID. NO. 23565　148-AspGlyMetAspGluValLeu-154
SEQ. ID. NO. 23566　160-GlnIleLeuLysProGluThrGluGlnAsnProMetLysGluLeuLeu-175
SEQ. ID. NO. 23567　182-ProAspAlaGlyGluGluGluLeuLysAla-191
SEQ. ID. NO. 23568　197-ValGluAlaLysProLysAspValAlaLeu-206
SEQ. ID. NO. 23569　214-LeuAlaGluLysAspSerArgIle-221
SEQ. ID. NO. 23570　227-GlnThrAlaLysProAspLeuThrLysTyrAla-237
SEQ. ID. NO. 23571　254-AlaLysGlnGluAlaAspLysGlyAsnGlu-263
SEQ. ID. NO. 23572　276-ProAlaGlnLysGluTrpAla-282
SEQ. ID. NO. 23573　285-ValLeuLysGlnProGlyGly-291
SEQ. ID. NO. 23574　310-GlySerGlnThrGlyGlyLysAlaProAspGluArgValAla-323
SEQ. ID. NO. 23575　326-ThrAlaGluGluAlaAlaAla-332
SEQ. ID. NO. 23576　337-GlyMetSerGlyGluGluPheValLysIleLysGluSerGluGlyLys-352
Hydrophilic Regions - Hopp-Woods
SEQ. ID. NO. 23577　1-MetSerLysAsnAlaGln-6
SEQ. ID. NO. 23578　17-ValGlnProLysAspGlyArgIle-24
SEQ. ID. NO. 23579　33-ArgAlaValAspGlyArgProThrAsp-41
SEQ. ID. NO. 23580　49-GluGluAsnGlyHis-53
SEQ. ID. NO. 23581　74-LeuTyrLysGluLysAsnGlyGln-81
SEQ. ID. NO. 23582　104-GluTrpThrAspLysAlaAla-110
SEQ. ID. NO. 23583　114-AlaAlaLysGluTyrArg-119
SEQ. ID. NO. 23584　148-AspGlyMetAspGluValLeu-154
SEQ. ID. NO. 23585　162-LeuLysProGluThrGluGlnAsnProMetLysGluLeuLeu-175
SEQ. ID. NO. 23586　183-AspAlaGlyGluGluGluLeuLysAla-191
SEQ. ID. NO. 23587　197-ValGluAlaLysProLysAspValAlaLeu-206
SEQ. ID. NO. 23588　214-LeuAlaGluLysAspSerArgIle-221
SEQ. ID. NO. 23589　228-ThrAlaLysProAspLeuThrLys-235
SEQ. ID. NO. 23590　254-AlaLysGlnGluAlaAspLysGlyAsnGlu-263
SEQ. ID. NO. 23591　276-ProAlaGlnLysGluTrpAla-282
SEQ. ID. NO. 23592　313-ThrGlyGlyLysAlaProAspGluArgValAla-323
SEQ. ID. NO. 23593　326-ThrAlaGluGluAlaAlaAla-332
SEQ. ID. NO. 23594　339-SerGlyGluGluPheValLysIleLysGluSerGluGlyLys-352
a724
AMPHI Regions - AMPHI
SEQ. ID. NO. 23595　6-LeuAlaLysLysThr-10
SEQ. ID. NO. 23596　12-GlnThrAlaLysAsnIleGlyGluThrLeuArg-22
SEQ. ID. NO. 23597　40-ArgValGlnLeuSer-44
SEQ. ID. NO. 23598　47-AlaAspGluThrLeuGlnAspLeuGluHisLeuGlnGlu-59
Antigenic Index - Jameson-Wolf
SEQ. ID. NO. 23599　5-LysLeuAlaLysLysThrAlaGlnThrAlaLysAsnIleGlyGluThrLeuArgAlaAlaPheArgGlyLysIle-29
SEQ. ID. NO. 23600　34-SerSerGluProIleGlnArgValGlnLeuSerGlyLeuAlaAspGluThrLeuGlnAspLeuGluHis-56
SEQ. ID. NO. 23601　60-TyrGlyPheAlaSerHisProProAspGlySerGluAla-72

TABLE 1-continued

| | |
|---|---|
| SEQ. ID. NO. 23602 | 77-LeuGlyGlyAsnThrSer-82 |
| SEQ. ID. NO. 23603 | 90-GlnHisGlySerTyrArgIleLysAsnLeuLysProGlyGluThr-104 |
| SEQ. ID. NO. 23604 | 108-AsnHisGluGlyAlaLysIleValIleLysGlnGlyLysIleIleGluAlaAspCysAspVal-128 |
| SEQ. ID. NO. 23605 | 130-ArgValAsnCysLysGlnTyrGlu-137 |
| SEQ. ID. NO. 23606 | 142-ThrAspAlaLysPhe-146 |
| SEQ. ID. NO. 23607 | 162-GlnIleAsnGlyAsnGly-167 |
| SEQ. ID. NO. 23608 | 170-AlaValGluGlyGlyAspGlyAlaThrPheSerGlyAspValAsnGlnThrGlyGlySerPheAsnThrAspGlyAspValValAla-198 |
| SEQ. ID. NO. 23609 | 205-GlnHisProHisThrAspSerIleGlyGlyLysThrLeuProAlaGluProAla-222 |
| Hydrophilic Regions - Hopp-Woods | |
| SEQ. ID. NO. 23610 | 5-LysLeuAlaLysLysThrAlaGlnThrAlaLysAsnIleGlyGluThrLeuArgAlaAlaPheArgGly-27 |
| SEQ. ID. NO. 23611 | 46-LeuAlaAspGluThrLeuGlnAspLeuGluHis-56 |
| SEQ. ID. NO. 23612 | 66-ProProAspGlySerGlu-71 |
| SEQ. ID. NO. 23613 | 94-TyrArgIleLysAsnLeuLysProGlyGlu-103 |
| SEQ. ID. NO. 23614 | 110-GluGlyAlaLysIleValIleLysGlnGlyLysIleIleGluAlaAspCysAspVal-128 |
| SEQ. ID. NO. 23615 | 132-AsnCysLysGlnTyrGlu-137 |
| SEQ. ID. NO. 23616 | 142-ThrAspAlaLysPhe-146 |
| SEQ. ID. NO. 23617 | 190-PheAsnThrAspGlyAspVal-196 |
| SEQ. ID. NO. 23618 | 207-ProHisThrAspSerIleGly-213 |
| a726 | |
| AMPHI Regions - AMPHI | |
| SEQ. ID. NO. 23619 | 12-AspThrLeuGlySerIleProGlu-19 |
| SEQ. ID. NO. 23620 | 55-ProArgProSerGluTyrHisGlu-62 |
| SEQ. ID. NO. 23621 | 74-AlaAlaAlaAlaArg-78 |
| SEQ. ID. NO. 23622 | 110-IleAspSerPheTyrArg-115 |
| SEQ. ID. NO. 23623 | 122-AlaArgGlnAlaAsp-126 |
| SEQ. ID. NO. 23624 | 137-IleAlaAlaAlaArg-141 |
| SEQ. ID. NO. 23625 | 180-IleGluThrAlaProGlyLeuAspAlaLeuGluLysGluIleGlu-194 |
| Antigenic Index - Jameson-Wolf | |
| SEQ. ID. NO. 23626 | 5-PheLysAsnGlyPheTyrAspAspThrLeuGlySerIleProGluGly-20 |
| SEQ. ID. NO. 23627 | 24-ValArgAlaGluGluTyr-29 |
| SEQ. ID. NO. 23628 | 37-AlaGlnGlyGlyGlnIleAlaAlaAspSerAspGlyArgProValLeuThrProProArgProSerGluTyrHisGluTrpAspGlyLysLysTrpGluIle-70 |
| SEQ. ID. NO. 23629 | 78-ArgPheAlaGluGlnLysThr-84 |
| SEQ. ID. NO. 23630 | 90-LeuAlaAlaLysAlaAspGluLeuLysAsnSer-100 |
| SEQ. ID. NO. 23631 | 106-ProGlnValGluIleAspSerPheTyrArgGlnGluLysGluAlaLeuAlaArgGlnAlaAspAsnAsnAlaProThr-131 |
| SEQ. ID. NO. 23632 | 151-LysValValGluLysSerAlaArg-158 |
| SEQ. ID. NO. 23633 | 167-IleGlyLysArgGlnGlnLeuGluAspLysLeuAsnThr-179 |
| SEQ. ID. NO. 23634 | 181-GluThrAlaProGlyLeuAspAlaLeuGluLysGluIleGluGlu-195 |
| Hydrophilic Regions - Hopp-Woods | |
| SEQ. ID. NO. 23635 | 24-ValArgAlaGluGluTyr-29 |
| SEQ. ID. NO. 23636 | 42-IleAlaAlaAspSerAspGlyArgPro-50 |
| SEQ. ID. NO. 23637 | 55-ProArgProSerGluTyrHisGluTrpAspGlyLysLysTrpGluIle-70 |
| SEQ. ID. NO. 23638 | 78-ArgPheAlaGluGlnLysThr-84 |
| SEQ. ID. NO. 23639 | 90-LeuAlaAlaLysAlaAspGluLeuLysAsn-99 |
| SEQ. ID. NO. 23640 | 114-TyrArgGlnGluLysGluAlaLeuAlaArgGlnAlaAspAsnAsnAla-129 |
| SEQ. ID. NO. 23641 | 151-LysValValGluLysSerAlaArg-158 |
| SEQ. ID. NO. 23642 | 167-IleGlyLysArgGlnGlnLeuGluAspLysLeuAsnThr-179 |
| SEQ. ID. NO. 23643 | 187-AspAlaLeuGluLysGluIleGluGlu-195 |
| a727 | |
| AMPHI Regions - AMPHI | |
| SEQ. ID. NO. 23644 | 6-LeuLeuAlaAsnAsn-10 |
| SEQ. ID. NO. 23645 | 12-GlnProIleAlaIleIleAla-18 |
| SEQ. ID. NO. 23646 | 61-TyrAlaArgGluLeuGlu-66 |
| SEQ. ID. NO. 23647 | 118-GlyCysIleAspGlyPheGly-124 |
| Antigenic Index - Jameson-Wolf | |
| SEQ. ID. NO. 23648 | 28-HisHisGlnGlyTyrLysSerAlaPheAlaLysGln-39 |
| SEQ. ID. NO. 23649 | 41-AlaValIleGluLysMetLysArgAspLysAlaGln-52 |
| SEQ. ID. NO. 23650 | 60-AsnTyrAlaArgGluLeuGluGlnAlaArgAlaGluAlaLysLysTyrGluValLysAla-79 |
| SEQ. ID. NO. 23651 | 86-LeuAlaLysLysGlnAlaGluValSerArgLeuLysThrGluAsnLysLysGluIleGluAsn-106 |
| SEQ. ID. NO. 23652 | 108-LeuThrGlnAspArgLysAsnAlaGlyGlyGlyCysIleAspGlyPheGly-124 |
| SEQ. ID. NO. 23653 | 135-LeuGlyTyrGlyAsn-139 |
| Hydrophilic Regions - Hopp-Woods | |
| SEQ. ID. NO. 23654 | 41-AlaValIleGluLysMetLysArgAspLysAlaGln-52 |
| SEQ. ID. NO. 23655 | 60-AsnTyrAlaArgGluLeuGluGlnAlaArgAlaGluAlaLysLysTyrGluValLysAla-79 |
| SEQ. ID. NO. 23656 | 86-LeuAlaLysLysGlnAlaGluValSerArgLeuLysThrGluAsnLysLysGluIleGluAsn-106 |
| SEQ. ID. NO. 23657 | 108-LeuThrGlnAspArgLysAsnAlaGly-116 |
| a728 | |
| AMPHI Regions - AMPHI | |
| SEQ. ID. NO. 23658 | 11-SerPhePheAlaLeuValPheAla-18 |
| SEQ. ID. NO. 23659 | 39-AlaThrGluValProLysAsnPro-46 |
| SEQ. ID. NO. 23660 | 48-AlaPheValAlaAlaLysLeuAlaArgLeuPheArgAsnAla-60 |
| SEQ. ID. NO. 23661 | 76-AsnLeuAlaGlyThrValAspAsp-83 |
| SEQ. ID. NO. 23662 | 198-GluAspValTyrGluHisCysLeuGlyCysTyrGlnMet-210 |
| SEQ. ID. NO. 23663 | 218-TyrArgAspValAlaAsnAspGlu-225 |
| SEQ. ID. NO. 23664 | 235-SerAsnArgIleAlaSer-240 |
| SEQ. ID. NO. 23665 | 249-GlnAsnMetArgGluLeuMetProArg-257 |
| SEQ. ID. NO. 23666 | 355-GluLysGluValArgArgTyrAlaGluAlaAlaAlaArg-367 |
| Antigenic Index - Jameson-Wolf | |
| SEQ. ID. NO. 23667 | 29-IleAsnProArgTrp-33 |
| SEQ. ID. NO. 23668 | 35-LeuSerAspThrAlaThrGluValProLysAsnProAsn-47 |
| SEQ. ID. NO. 23669 | 57-PheArgAsnAlaAspArgAla-63 |

TABLE 1-continued

| | |
|---|---|
| SEQ. ID. NO. 23670 | 69-GluSerIleArgThrGluGluAsnLeuAlaGlyThrValAspAspGlyProLeuGlnSerGluLysAspTyr-92 |
| SEQ. ID. NO. 23671 | 98-ArgLeuSerArgLeuLysGluLysAlaLys-107 |
| SEQ. ID. NO. 23672 | 112-ThrGluGlnGluHisGlyLys-118 |
| SEQ. ID. NO. 23673 | 125-HisIleGlyGluGlyGly-130 |
| SEQ. ID. NO. 23674 | 136-LeuSerGlnArgSerProGluAlaPheVal-145 |
| SEQ. ID. NO. 23675 | 149-TyrLeuTyrArgAsnAspArgProPheSer-158 |
| SEQ. ID. NO. 23676 | 166-ValHisGlyGluAsnTyrGluThrThrGlyGluTyrArgVal-179 |
| SEQ. ID. NO. 23677 | 182-GlnProAspGlySerVal-187 |
| SEQ. ID. NO. 23678 | 190-AlaAlaGlyArgGlyLysIleGlyGluAspValTyr-201 |
| SEQ. ID. NO. 23679 | 217-LysTyrArgAspValAlaAsnAspGluGlnLysValTrpAspPheArgLysGluSerAsnArgIleAlaSerAspSerArgAsnSerValPheTyrGln AsnMetArgGluLeuMetProArgGlyMetLysAlaAsnSer-263 |
| SEQ. ID. NO. 23680 | 267-GlyTyrAspAlaAspGlyLeuProGlnLys-276 |
| SEQ. ID. NO. 23681 | 280-SerPheAspAsnGlyLysLysArgGlnSerPheGluTyrTyrLeuLysAsnGlyAsn-298 |
| SEQ. ID. NO. 23682 | 309-LeuLysAlaAspGlyValThr-315 |
| SEQ. ID. NO. 23683 | 329-LeuAspGlyGlyArgIleValArgGluGluLysGlnGlyAspArgLeuProAspPhe-347 |
| SEQ. ID. NO. 23684 | 352-GluAsnLeuGluLysGluValArgArgTyrAlaGluAlaAlaAlaArgArgSerGlyGlyArgArgAspLeuSerHis-377 |
| Hydrophilic Regions - Hopp-Woods | |
| SEQ. ID. NO. 23685 | 38-ThrAlaThrGluValProLysAsnPro-46 |
| SEQ. ID. NO. 23686 | 57-PheArgAsnAlaAspArgAla-63 |
| SEQ. ID. NO. 23687 | 69-GluSerIleArgThrGluGluAsnLeu-77 |
| SEQ. ID. NO. 23688 | 80-ThrValAspAspGlyProLeuGlnSerGluLysAspTyr-92 |
| SEQ. ID. NO. 23689 | 98-ArgLeuSerArgLeuLysGluLysAlaLys-107 |
| SEQ. ID. NO. 23690 | 112-ThrGluGlnGluHisGlyLys-118 |
| SEQ. ID. NO. 23691 | 136-LeuSerGlnArgSerProGlu-142 |
| SEQ. ID. NO. 23692 | 151-TyrArgAsnAspArgProPhe-157 |
| SEQ. ID. NO. 23693 | 169-GluAsnTyrGluThrThrGlyGluTyr-177 |
| SEQ. ID. NO. 23694 | 190-AlaAlaGlyArgGlyLysIleGlyGluAspValTyr-201 |
| SEQ. ID. NO. 23695 | 217-LysTyrArgAspValAlaAsnAspGluGlnLysValTrpAspPheArgLysGluSerAsnArgIleAlaSerAspSerArgAsn-244 |
| SEQ. ID. NO. 23696 | 250-AsnMetArgGluLeuMetProArgGlyMetLys-260 |
| SEQ. ID. NO. 23697 | 268-TyrAspAlaAspGlyLeuPro-274 |
| SEQ. ID. NO. 23698 | 282-AspAsnGlyLysLysArgGlnSer-289 |
| SEQ. ID. NO. 23699 | 309-LeuLysAlaAspGlyValThr-315 |
| SEQ. ID. NO. 23700 | 331-GlyGlyArgIleValArgGluGluLysGlnGlyAspArgLeuPro-345 |
| SEQ. ID. NO. 23701 | 352-GluAsnLeuGluLysGluValArgArgTyrAlaGluAlaAlaAlaArgArgSerGlyGlyArgArgAspLeuSerHis-377 |
| a729 | |
| AMPHI Regions - AMPHI | |
| SEQ. ID. NO. 23702 | 21-CysThrMetIleProGlnTyr-27 |
| SEQ. ID. NO. 23703 | 33-GluValAlaGluThrPheLysAsnAspThr-42 |
| SEQ. ID. NO. 23704 | 55-HisAspTyrPheAla-59 |
| SEQ. ID. NO. 23705 | 61-ProArgLeuGlnLysLeuIleAspIle-69 |
| SEQ. ID. NO. 23706 | 149-GlnGlyTyrPheAla-153 |
| SEQ. ID. NO. 23707 | 164-SerLeuIleAlaThrValAlaLys-171 |
| SEQ. ID. NO. 23708 | 242-LeuAlaThrLeuIleAsn-247 |
| SEQ. ID. NO. 23709 | 268-LysLeuProAlaGlyLeu-273 |
| SEQ. ID. NO. 23710 | 322-LeuGlyGlyLeuPheLysSer-328 |
| SEQ. ID. NO. 23711 | 371-ValGlnSerAlaPheGlnAspValAlaAsnAla-381 |
| SEQ. ID. NO. 23712 | 388-LeuAspLysAlaTyrAspAlaLeuSerLysGlnSerArg-400 |
| SEQ. ID. NO. 23713 | 419-GlyAlaLeuAspLeuLeuAspAla-426 |
| SEQ. ID. NO. 23714 | 442-LeuThrArgAlaGluAsnLeuAlaAspLeuTyrLysAlaLeuGlyGlyGlyLeuLys-460 |
| Antigenic Index - Jameson-Wolf | |
| SEQ. ID. NO. 23715 | 25-ProGlnTyrGluGlnProLysValGluVal-34 |
| SEQ. ID. NO. 23716 | 36-GluThrPheLysAsnAspThrAlaAspSerGlyIleArgAlaValAsp-51 |
| SEQ. ID. NO. 23717 | 53-GlyTrpHisAspTyrPheAlaAspProArgLeuGlnLys-65 |
| SEQ. ID. NO. 23718 | 70-AlaLeuGluArgAsnThrSerLeuArgThr-79 |
| SEQ. ID. NO. 23719 | 85-GluIleTyrArgLysGlnTyrMetIleGluArgAsnAsnLeuLeuPro-100 |
| SEQ. ID. NO. 23720 | 105-AsnAlaAsnAspSerArgGlnGlySerLeuSerGlyGlyAsnValSerSerSerTyrLysVal-125 |
| SEQ. ID. NO. 23721 | 138-GlyArgValArgSerSerSerGluAlaAla-147 |
| SEQ. ID. NO. 23722 | 155-ThrAlaAsnArgAspAlaAla-161 |
| SEQ. ID. NO. 23723 | 173-TyrPheAsnGlnArgTyrAlaGluGluAlaMet-183 |
| SEQ. ID. NO. 23724 | 188-ArgValLeuLysThrArgGluGluThrTyrLysLeuSerGluLeuArgTyr-204 |
| SEQ. ID. NO. 23725 | 215-ArgGlnGlnGluAlaLeuIleGluSerAlaLysAlaAspTyr-228 |
| SEQ. ID. NO. 23726 | 232-AlaArgSerArgGluGlnAlaArgAsn-240 |
| SEQ. ID. NO. 23727 | 248-GlnProIleProAspAspProLeuProAla-256 |
| SEQ. ID. NO. 23728 | 277-ValLeuLeuAspArgProAspIleArgAlaAlaGluHisAlaLeuLysGlnAlaAsnAla-296 |
| SEQ. ID. NO. 23729 | 310-ArgLeuThrGlySerValAspThrHisSerAlaGlu-321 |
| SEQ. ID. NO. 23730 | 325-LeuPheLysSerGlyThr-330 |
| SEQ. ID. NO. 23731 | 347-GlyThrAsnLysAlaAsnLeuAsnAspValAlaLysLeuArgGlnGln-361 |
| SEQ. ID. NO. 23732 | 383-ThrAlaArgGluGlnLeuAspLysAlaTyrAspAlaLeuSerLysGlnSerArgAlaSerLysGluAlaLeuArg-407 |
| SEQ. ID. NO. 23733 | 411-LeuArgTyrLysHisGlyValSer-418 |
| SEQ. ID. NO. 23734 | 424-LeuAspAlaGluArgSerSerTyrSerAla-433 |
| SEQ. ID. NO. 23735 | 442-LeuThrArgAlaGluAsnLeu-448 |
| SEQ. ID. NO. 23736 | 455-LeuGlyGlyGlyLeuLysArgAspThrGlnThrAspLys-467 |
| Hydrophilic Regions - Hopp-Woods | |
| SEQ. ID. NO. 23737 | 28-GluGlnProLysValGluVal-34 |
| SEQ. ID. NO. 23738 | 36-GluThrPheLysAsnAspThrAlaAspSerGlyIleArgAlaVal-50 |
| SEQ. ID. NO. 23739 | 61-ProArgLeuGlnLys-65 |
| SEQ. ID. NO. 23740 | 70-AlaLeuGluArgAsnThrSerLeu-77 |
| SEQ. ID. NO. 23741 | 91-TyrMetIleGluArgAsnAsn-97 |
| SEQ. ID. NO. 23742 | 105-AsnAlaAsnAspSerArgGlnGlySer-113 |
| SEQ. ID. NO. 23743 | 138-GlyArgValArgSerSerSerGluAlaAla-147 |

TABLE 1-continued

| | |
|---|---|
| SEQ. ID. NO. 23744 | 156-AlaAsnArgAspAlaAla-161 |
| SEQ. ID. NO. 23745 | 177-ArgTyrAlaGluGluAlaMet-183 |
| SEQ. ID. NO. 23746 | 188-ArgValLeuLysThrArgGluGluThrTyrLysLeuSerGluLeuArgTyr-204 |
| SEQ. ID. NO. 23747 | 215-ArgGlnGlnGluAlaLeuIleGluSerAlaLysAlaAspTyr-228 |
| SEQ. ID. NO. 23748 | 232-AlaArgSerArgGluGlnAlaArgAsn-240 |
| SEQ. ID. NO. 23749 | 250-IleProAspAspLeuPro-255 |
| SEQ. ID. NO. 23750 | 277-ValLeuLeuAspArgProAspIleArgAlaAlaGluHisAlaLeuLysGlnAlaAsn-295 |
| SEQ. ID. NO. 23751 | 315-ValAspThrHisSerAlaGlu-321 |
| SEQ. ID. NO. 23752 | 350-LysAlaAsnLeuAspValAlaLysLeuArgGln-360 |
| SEQ. ID. NO. 23753 | 383-ThrAlaArgGluGlnLeuAspLysAlaTyrAspAlaLeuSerLysGlnSerArgAlaSerLysGluAlaLeuArg-407 |
| SEQ. ID. NO. 23754 | 424-LeuAspAlaGluArgSerSerTyrSerAla-433 |
| SEQ. ID. NO. 23755 | 442-LeuThrArgAlaGluAsnLeu-448 |
| SEQ. ID. NO. 23756 | 458-GlyLeuLysArgAspThrGlnThrAspLys-467 |
| a730 | |
| AMPHIRegions - AMPHI | |
| SEQ. ID. NO. 23757 | 6-ArgLeuIleLysLeuLeuAlaAlaCys-14 |
| SEQ. ID. NO. 23758 | 26-LeuAlaAlaAspLeu-30 |
| SEQ. ID. NO. 23759 | 67-GlnIleAsnValIleGlnAspTyrThrHisArg-77 |
| SEQ. ID. NO. 23760 | 111-AsnHisAlaAlaAsp-115 |
| SEQ. ID. NO. 23761 | 141-HisProAlaAspAlaTyrAspGlyProLysGlyGlyAsnTyrProLysProThr-158 |
| SEQ. ID. NO. 23762 | 187-GlnArgIleSerAspAsnTyrSerAsnLeuGlySerAsnPheSerAspArgAlaAspGlu-206 |
| SEQ. ID. NO. 23763 | 214-HisAsnAlaLysLeu-218 |
| SEQ. ID. NO. 23764 | 220-ArgTrpGlyAsnSerMetGluPheIleAsnGlyValAla-232 |
| SEQ. ID. NO. 23765 | 234-GlyAlaLeuAsnProPheIleSer-241 |
| SEQ. ID. NO. 23766 | 262-AlaAlaMetArgAsnIleAla-268 |
| SEQ. ID. NO. 23767 | 277-AlaValIleGlyGlyLeuGlySerValAlaGlyPheGluLysAsnThrArgGluAlaValAspArgTrpIleGlnGlu-302 |
| SEQ. ID. NO. 23768 | 305-AsnAlaAlaGluThrValGluAlaLeuValAsnValLeuProPheAlaLysValLysAsnLeuThrLysAlaAlaLysPro-331 |
| SEQ. ID. NO. 23769 | 347-ArgThrThrArgLysValThr-353 |
| SEQ. ID. NO. 23770 | 355-GluThrGluGlyLeuAsnArgIleArgGln-364 |
| SEQ. ID. NO. 23771 | 384-IleAsnValLeuSerGlyAsnSerIleGlnHis-394 |
| SEQ. ID. NO. 23772 | 426-ThrHisGluIleSerAspIleValThr-434 |
| SEQ. ID. NO. 23773 | 475-GluProAlaThrGlyLysValValThrAlaPheProAsp-487 |
| Antigenic Index - Jameson-Wolf | |
| SEQ. ID. NO. 23774 | 2-LysProLeuArgArgLeuIle-8 |
| SEQ. ID. NO. 23775 | 35-PheIleThrAspAsnAlaGlnArgGlnHisTyrGluProGlyGlyLys-50 |
| SEQ. ID. NO. 23776 | 55-GlyAspProArgGlySerValSerAspArgThrGlyGlnIle-68 |
| SEQ. ID. NO. 23777 | 74-TyrThrHisArgMetGly-79 |
| SEQ. ID. NO. 23778 | 97-ArgPheSerGlyHisGlyTyrGluGluHisAlaProPheAsp-110 |
| SEQ. ID. NO. 23779 | 112-HisAlaAlaAspSerAlaSerGluGluLysGlyAsnValAspGluGlyPhe-128 |
| SEQ. ID. NO. 23780 | 133-LeuAsnTrpGluGlyHisGluHisHisProAlaAspAlaTyrAspGlyProLysGlyGlyAsnTyrProLysProThrGlyAlaArgAspGluTyrThrTyrHisVal-168 |
| SEQ. ID. NO. 23781 | 170-GlyThrAlaArgSerIleLysLeuAsnProThrAspThrArgSerIleArgGlnArgIleSerAspAsnTyrSerAsn-195 |
| SEQ. ID. NO. 23782 | 197-GlySerAsnPheSerAspArgAlaAspGluAlaAsnArgLysMetPheGluHisAsnAlaLysLeuAspArgTrpGlyAsnSer-224 |
| SEQ. ID. NO. 23783 | 257-TyrAlaIleAspLysAlaAlaMet-264 |
| SEQ. ID. NO. 23784 | 271-ProAlaGluGlyLys-275 |
| SEQ. ID. NO. 23785 | 287-GlyPheGluLysAsnThrArgGluAlaValAsp-297 |
| SEQ. ID. NO. 23786 | 299-TrpIleGlnGluAsnProAsnAlaAlaGluThrValGlu-311 |
| SEQ. ID. NO. 23787 | 323-LysAsnLeuThrLysAlaAlaLysProGlyLysAlaAlaValSerGlyAspPhe-340 |
| SEQ. ID. NO. 23788 | 344-TyrAsnThrArgThrThrArgLysValThrThrGluThrGluGlyLeuAsnArgIleArgGlnAsnGlnLysAsnSerAsnIleHisGluLysAsnTyrGlyArgAspAsnProAsnHisIle-384 |
| SEQ. ID. NO. 23789 | 397-TyrGlyAspGluAlaGlyGlyGly-404 |
| SEQ. ID. NO. 23790 | 407-PheProGlyLysProGlyLysThrThrPhePro-417 |
| SEQ. ID. NO. 23791 | 419-HisTrpSerAlaSerLysIleThrHisGluIleSerAsp-431 |
| SEQ. ID. NO. 23792 | 433-ValThrSerProLysThrGln-439 |
| SEQ. ID. NO. 23793 | 450-TyrIleAlaLysGlyArgProAlaArg-458 |
| SEQ. ID. NO. 23794 | 461-SerTyrGluThrArgAspGlyIleArgIle-470 |
| SEQ. ID. NO. 23795 | 472-ThrValTyrGluProAlaThrGlyLys-480 |
| SEQ. ID. NO. 23796 | 485-PheProAspArgThrSerAsnProLysTyrAsnProValLys-498 |
| Hydrophilic Regions - Hopp-Woods | |
| SEQ. ID. NO. 23797 | 2-LysProLeuArgArgLeuIle-8 |
| SEQ. ID. NO. 23798 | 39-AsnAlaGlnArgGlnHisTyrGluProGlyGly-49 |
| SEQ. ID. NO. 23799 | 55-GlyAspProArgGlySerValSerAspArgThrGly-66 |
| SEQ. ID. NO. 23800 | 102-GlyTyrGluGluHisAlaPro-108 |
| SEQ. ID. NO. 23801 | 112-HisAlaAlaAspSerAlaSerGluGluLysGlyAsnValAspGluGly-127 |
| SEQ. ID. NO. 23802 | 135-TrpGluGlyHisGluHisHisPro-142 |
| SEQ. ID. NO. 23803 | 144-AspAlaTyrAspGlyProLysGlyGlyAsnTyrProLys-156 |
| SEQ. ID. NO. 23804 | 158-ThrGlyAlaArgAspGluTyr-164 |
| SEQ. ID. NO. 23805 | 170-GlyThrAlaArgSerIleLys-176 |
| SEQ. ID. NO. 23806 | 178-AsnProThrAspThrArgSerIleArgGlnArgIleSerAsp-191 |
| SEQ. ID. NO. 23807 | 200-PheSerAspArgAlaAspGluAlaAsnArgLysMetPheGluHisAsnAlaLysLeuAspArgTrpGlyAsn-223 |
| SEQ. ID. NO. 23808 | 257-TyrAlaIleAspLysAlaAlaMet-264 |
| SEQ. ID. NO. 23809 | 271-ProAlaGluGlyLys-275 |
| SEQ. ID. NO. 23810 | 287-GlyPheGluLysAsnThrArgGluAlaValAsp-297 |
| SEQ. ID. NO. 23811 | 303-AsnProAsnAlaAlaGluThrValGlu-311 |
| SEQ. ID. NO. 23812 | 323-LysAsnLeuThrLysAlaAlaLysProGlyLysAlaAlaVal-336 |
| SEQ. ID. NO. 23813 | 347-ArgThrThrArgLysValThrThrGluThrGluGlyLeuAsnArgIleArgGlnAsnGlnLysAsnSerAsnIleHisGluLysAsnTyrGlyArgAspAsnProAsn-382 |
| SEQ. ID. NO. 23814 | 399-AspGluAlaGlyGlyGly-403 |
| SEQ. ID. NO. 23815 | 424-LysIleThrHisGluIleSerAsp-431 |
| SEQ. ID. NO. 23816 | 450-TyrIleAlaLysGlyArgProAlaArg-458 |

TABLE 1-continued

| | |
|---|---|
| SEQ. ID. NO. 23817 | 463-GluThrArgAspGlyIleArgIle-470 |
| SEQ. ID. NO. 23818 | 485-PheProAspArgThrSerAsnProLys-493 | a731
AMPHI Regions - AMPHI

| | |
|---|---|
| SEQ. ID. NO. 23819 | 17-AlaCysAlaValPro-21 |

Antigenic Index - Jameson-Wolf

| | |
|---|---|
| SEQ. ID. NO. 23820 | 22-GluAlaTyrAspAspGlyGlyArgGlyHis-31 |
| SEQ. ID. NO. 23821 | 34-ProValGlnAsnGlnAlaGlyThrAlaAsp-43 |
| SEQ. ID. NO. 23822 | 45-ArgAlaPheSerCysGluAsnGly-52 |
| SEQ. ID. NO. 23823 | 56-HisValArgArgLeuAspGlyGlyArgIleAlaLeuArgLeuAspGlyArgArgAlaValLeuSerSerAspValAlaAlaSerGlyGluArgTyrThrAla-89 |
| SEQ. ID. NO. 23824 | 92-GlyLeuPheGlyAsnGlyThrGluTrpHisGlnLysGlyGlyGluAla-107 |
| SEQ. ID. NO. 23825 | 113-AspAlaTyrGlyAsnSerValGluThrSerCysArgAlaArg-126 |

Hydrophilic Regions - Hopp-Woods

| | |
|---|---|
| SEQ. ID. NO. 23826 | 22-GluAlaTyrAspAspGlyGlyArgGlyHis-31 |
| SEQ. ID. NO. 23827 | 56-HisValArgArgLeuAspGlyGlyArgIleAlaLeuArgLeuAspGlyArgArgAlaValLeu-76 |
| SEQ. ID. NO. 23828 | 80-ValAlaAlaSerGlyGluArgTyrThrAla-89 |
| SEQ. ID. NO. 23829 | 100-TrpHisGlnLysGlyGlyGlu-106 |
| SEQ. ID. NO. 23830 | 119-ValGluThrSerCysArgAlaArg-126 | a732
AMPHI Regions - AMPHI

| | |
|---|---|
| SEQ. ID. NO. 23831 | 14-LeuGlyAlaIleSer-18 |
| SEQ. ID. NO. 23832 | 43-ValGlnSerIleArgThrMetAlaGluValTyrGly-54 |
| SEQ. ID. NO. 23833 | 66-AspAlaAspLeuPheGluGlyAlaMetLysGlyMetVal-78 |
| SEQ. ID. NO. 23834 | 95-GluIleLysGluSerThrSerGly-102 |
| SEQ. ID. NO. 23835 | 115-AspGlyPheValLysValValSerProIleGluAsp-126 |
| SEQ. ID. NO. 23836 | 155-GluAlaValLysLysMet-160 |
| SEQ. ID. NO. 23837 | 183-ValAsnLeuThrArg-187 |
| SEQ. ID. NO. 23838 | 214-GluArgThrValGluSerValAsnThrAlaAlaLys-225 |
| SEQ. ID. NO. 23839 | 283-LysAlaValProGluAspTyrValTyr-291 |
| SEQ. ID. NO. 23840 | 297-SerLeuAlaGlyIleProAlaGluLeu-305 |
| SEQ. ID. NO. 23841 | 322-SerGluIleValAlaGly-327 |
| SEQ. ID. NO. 23842 | 400-LeuValGlyHisIleGlyAsn-406 |
| SEQ. ID. NO. 23843 | 446-ArgArgIleProAsnProAlaLysAsp-454 |
| SEQ. ID. NO. 23844 | 459-LysAlaLeuAspLeuValLysSerProGluGlnTrpGlnLysSerLeu-474 |

Antigenic Index - Jameson-Wolf

| | |
|---|---|
| SEQ. ID. NO. 23845 | 30-AlaAlaGluLysAspArgArgAspAsnGluVal-40 |
| SEQ. ID. NO. 23846 | 59-AsnTyrTyrGlnAspLysProAspAlaAspLeuPhe-70 |
| SEQ. ID. NO. 23847 | 82-AspProHisSerGluTyrMetAspLysLysGlyTyrAlaGluIleLysGluSerThrSerGlyGluPheGlyGly-106 |
| SEQ. ID. NO. 23848 | 111-IleGlyGlnGluAspGlyPhe-117 |
| SEQ. ID. NO. 23849 | 122-SerProIleGluAspThrProAlaGluArgAlaGlyValLysSerGlyAspPhe-139 |
| SEQ. ID. NO. 23850 | 144-AspAsnValSerThrArgGlyMetThr-152 |
| SEQ. ID. NO. 23851 | 155-GluAlaValLysLysMetArgGlyLysProGlyThrLysIle-168 |
| SEQ. ID. NO. 23852 | 172-LeuSerArgLysAsnAlaAspLysProIle-181 |
| SEQ. ID. NO. 23853 | 199-LeuIleGluProAspTyrGlyTyr-206 |
| SEQ. ID. NO. 23854 | 211-GlnPheGlnGluArgThrValGlu-218 |
| SEQ. ID. NO. 23855 | 221-AsnThrAlaAlaLysGluLeuValLysGluAsnLysGlyLysProLeuLys-237 |
| SEQ. ID. NO. 23856 | 242-AspLeuArgAspAspProGlyGlyLeu-250 |
| SEQ. ID. NO. 23857 | 269-ValSerThrLysGlyArgAspGlyLysAspArgMetVal-281 |
| SEQ. ID. NO. 23858 | 284-AlaValProGluAspTyrVal-290 |
| SEQ. ID. NO. 23859 | 293-MetGlyGlyAspSerLeuAla-299 |
| SEQ. ID. NO. 23860 | 303-AlaGluLeuLysThr-307 |
| SEQ. ID. NO. 23861 | 316-SerGlySerAlaSerAla-321 |
| SEQ. ID. NO. 23862 | 330-GlnAspHisLysArgAlaVal-336 |
| SEQ. ID. NO. 23863 | 340-ThrGlnSerPheGlyLysGlySerVal-348 |
| SEQ. ID. NO. 23864 | 354-LeuSerAsnGlySer-358 |
| SEQ. ID. NO. 23865 | 368-TyrThrProAsnAspArgSerIleGln-376 |
| SEQ. ID. NO. 23866 | 384-ValGluValLysAspLysGluArgIlePheGluSerArgGluAlaAspLeu-400 |
| SEQ. ID. NO. 23867 | 405-GlyAsnProLeuGlyGlyGluAspValAsnSerGlu-416 |
| SEQ. ID. NO. 23868 | 421-ProLeuGluLysAspAlaAspLysProAlaValLysGluLysGlyLysLysLysLysAspGluAspLeuSerSerArgArgIleProAsnProAlaLysAspAspGlnLeuArgLysAlaLeuAspLeuValLysSerProGluGlnTrpGlnLys-472 |
| SEQ. ID. NO. 23869 | 477-AlaAlaLysLysProValSerAsnLysAspLysLysAspLysLysAspLysLys-494 |

Hydrophilic Regions - Hopp-Woods

| | |
|---|---|
| SEQ. ID. NO. 23870 | 30-AlaAlaGluLysAspArgArgAspAsnGluVal-40 |
| SEQ. ID. NO. 23871 | 60-TyrTyrGlnAspLysProAspAlaAspLeuPhe-70 |
| SEQ. ID. NO. 23872 | 82-AspProHisSerGluTyrMetAspLysLysGlyTyrAlaGluIleLysGluSerThrSerGlyGlu-103 |
| SEQ. ID. NO. 23873 | 111-IleGlyGlnGluAspGlyPhe-117 |
| SEQ. ID. NO. 23874 | 122-SerProIleGluAspThrProAlaGluArgAlaGlyValLysSerGlyAspPhe-139 |
| SEQ. ID. NO. 23875 | 144-AspAsnValSerThr-148 |
| SEQ. ID. NO. 23876 | 155-GluAlaValLysLysMetArgGlyLysProGlyThr-166 |
| SEQ. ID. NO. 23877 | 172-LeuSerArgLysAsnAlaAspLysProIle-181 |
| SEQ. ID. NO. 23878 | 211-GlnPheGlnGluArgThrValGlu-218 |
| SEQ. ID. NO. 23879 | 221-AsnThrAlaAlaLysGluLeuValLysGluAsnLysGlyLysProLeuLys-237 |
| SEQ. ID. NO. 23880 | 242-AspLeuArgAspAspProGly-248 |
| SEQ. ID. NO. 23881 | 271-ThrLysGlyArgAspGlyLysAspArgMetVal-281 |
| SEQ. ID. NO. 23882 | 303-AlaGluLeuLysThr-307 |
| SEQ. ID. NO. 23883 | 330-GlnAspHisLysArgAlaVal-336 |
| SEQ. ID. NO. 23884 | 370-ProAsnAspArgSerIleGln-376 |
| SEQ. ID. NO. 23885 | 384-ValGluValLysAspLysGluArgIlePheGluSerArgGluAlaAspLeu-400 |
| SEQ. ID. NO. 23886 | 408-LeuGlyGlyGluAspValAsnSer-415 |

TABLE 1-continued

| SEQ. ID. NO. 23887 | 421-ProLeuGluLysAspAlaAspLysProAlaValLysGluLysGlyLysLysLysLysAspGluAspLeuSerSerArgArgIleProAsnProAla LysAspAspGlnLeuArgLysAlaLeuAspLeuValLysSerProGluGlnTrpGln-471 |
|---|---|
| SEQ. ID. NO. 23888 | 477-AlaAlaLysLysProValSerAsnLysAspLysLysAspLysLysAspLysLys-494 | a733
AMPHI Regions - AMPHI
SEQ. ID. NO. 23889    6-ThrLeuSerArgLeuSer-11
SEQ. ID. NO. 23890    33-TyrGlyGlyTyrProAspThrValTyrGluGly-43
SEQ. ID. NO. 23891    53-LysGlnThrGluLysMetGluLysTyrPheVal-63
SEQ. ID. NO. 23892    92-GlyAlaPheArgGlnPheGluGlu-99
Antigenic Index - Jameson-Wolf
SEQ. ID. NO. 23893    2-MetAsnProLysThrLeuSer-8
SEQ. ID. NO. 23894    22-CysGlyGlyAsnGlyGlnLysSer-29
SEQ. ID. NO. 23895    33-TyrGlyGlyTyrProAspThrValTyrGluGlyLeuLysAsnAspAspThrSerLeuGlyLysGlnThrGluLysMetGluLysTyrPhe-62
SEQ. ID. NO. 23896    65-AlaGlyAsnLysLysMetAsnAlaAlaProGlyAla-76
SEQ. ID. NO. 23897    84-LeuSerArgSerGlyAspLysGluGlyAlaPheArgGlnPheGluGluGluLysArgLeuPheProGlu-106
SEQ. ID. NO. 23898    115-MetLysThrGlyLysGlyGlyLysArg-123
Hydrophilic Regions - Hopp-Woods
SEQ. ID. NO. 23899    40-ValTyrGluGlyLeuLysAsnAspAspThrSerLeuGlyLysGlnThrGluLysMetGluLysTyrPhe-62
SEQ. ID. NO. 23900    65-AlaGlyAsnLysLysMetAsnAla-72
SEQ. ID. NO. 23901    86-ArgSerGlyAspLysGluGlyAlaPheArgGlnPheGluGluGluLysArgLeuPhePro-105
SEQ. ID. NO. 23902    115-MetLysThrGlyLysGlyGlyLysArg-123
a734
AMPHI Regions - AMPHI
SEQ. ID. NO. 23903    19-ArgAlaAlaAspThrTyr-24
SEQ. ID. NO. 23904    26-TyrLeuAlaValTrpGlnAsnProGlnAsnAlaAsnAspValLeuGlnVal-42
SEQ. ID. NO. 23905    53-GluAlaPheAlaGluLeuGluAlaPheCysLys-63
SEQ. ID. NO. 23906    77-ThrGlyCysArgSerValValSer-84
SEQ. ID. NO. 23907    92-LeuAlaTyrProLysAlaLeuGlyAlaMetArg-102
SEQ. ID. NO. 23908    113-ArgPheThrSerVal-117
SEQ. ID. NO. 23909    119-GlnValAlaLeuAsnGlnCysIleLysLys-128
Antigenic Index - Jameson-Wolf
SEQ. ID. NO. 23910    18-AlaArgAlaAlaAsp-22
SEQ. ID. NO. 23911    31-GlnAsnProGlnAsnAlaAsnAsp-38
SEQ. ID. NO. 23912    43-LysThrThrLysGluAspSerThrLysSerGluAlaPheAlaGlu-57
SEQ. ID. NO. 23913    60-AlaPheCysLysGlyGlnAspThr-67
SEQ. ID. NO. 23914    71-IleAlaGluAspGluProThrGlyCysArgSer-81
SEQ. ID. NO. 23915    101-MetArgValGluAsn-105
SEQ. ID. NO. 23916    125-CysIleLysLysTyrGlyAlaGlnGly-133
SEQ. ID. NO. 23917    145-SerSerTyrTyrGly-149
Hydrophilic Regions - Hopp-Woods
SEQ. ID. NO. 23918    18-AlaArgAlaAlaAsp-22
SEQ. ID. NO. 23919    43-LysThrThrLysGluAspSerThrLysSerGluAlaPheAlaGlu-57
SEQ. ID. NO. 23920    60-AlaPheCysLysGlyGlnAspThr-67
SEQ. ID. NO. 23921    71-IleAlaGluAspGluProThrGlyCys-79
SEQ. ID. NO. 23922    101-MetArgValGluAsn-105
SEQ. ID. NO. 23923    125-CysIleLysLysTyrGlyAla-131
a735
AMPHI Regions - AMPHI
SEQ. ID. NO. 23924    6-LeuLeuAlaAsnAsn-10
SEQ. ID. NO. 23925    12-GlnProIleAlaIleIleAla-18
SEQ. ID. NO. 23926    61-TyrAlaArgGluLeuGlu-66
SEQ. ID. NO. 23927    118-GlyCysIleAspGlyPheGly-124
Antigenic Index - Jameson-Wolf
SEQ. ID. NO. 23928    28-HisHisGlnGlyTyrLysSerAlaPheAlaLysGln-39
SEQ. ID. NO. 23929    41-AlaValIleGluLysMetLysArgAspLysAlaGln-52
SEQ. ID. NO. 23930    60-AsnTyrAlaArgGluLeuGluGlnAlaArgAlaGluAlaLysLysTyrGluValLysAla-79
SEQ. ID. NO. 23931    86-LeuAlaLysLysGlnAlaGluValSerArgLeuLysThrGluAsnLysLysGluIleGluAsn-106
SEQ. ID. NO. 23932    108-LeuThrGlnAspArgLysAsnAlaGlyGlyGlyCysIleAspGlyPheGly-124
SEQ. ID. NO. 23933    135-LeuGlyTyrGlyAsn-139
Hydrophilic Regions - Hopp-Woods
SEQ. ID. NO. 23934    41-AlaValIleGluLysMetLysArgAspLysAlaGln-52
SEQ. ID. NO. 23935    60-AsnTyrAlaArgGluLeuGluGlnAlaArgAlaGluAlaLysLysTyrGluValLysAla-79
SEQ. ID. NO. 23936    86-LeuAlaLysLysGlnAlaGluValSerArgLeuLysThrGluAsnLysLysGluIleGluAsn-106
SEQ. ID. NO. 23937    108-LeuThrGlnAspArgLysAsnAlaGly-116
a736
AMPHI Regions - AMPHI
SEQ. ID. NO. 23938    13-GlyLeuIleGlnSerLeuGlySer-20
SEQ. ID. NO. 23939    50-GlyValLeuSerVal-54
SEQ. ID. NO. 23940    61-GlyLeuPheValGly-65
SEQ. ID. NO. 23941    70-LeuGlnGlyTyrThrGlnLeuSerLysPheLysSerAlaAspIle-84
SEQ. ID. NO. 23942    93-LeuLeuArgGluLeuGlyProVal-100
SEQ. ID. NO. 23943    120-LeuMetLysThrThrGluGlnLeuGluAlaMetAsnValMet-133
SEQ. ID. NO. 23944    135-ValAsnProValAlaArgValVal-142
SEQ. ID. NO. 23945    144-ProArgPheTrpAlaGlyValPheSerMetPro-154
SEQ. ID. NO. 23946    156-LeuAlaSerIlePheAsnValAlaGlyIlePheGlyAla-168
SEQ. ID. NO. 23947    196-AspValIleAsnGlyLeu-201
SEQ. ID. NO. 23948    230-LeuArgAlaSerThrArgThr-236
Antigenic Index - Jameson-Wolf
SEQ. ID. NO. 23949    37-ValArgProArgLeuSerVal-43
SEQ. ID. NO. 23950    77-SerLysPheLysSer-81

TABLE 1-continued

SEQ. ID. NO. 23951  93-LeuLeuArgGluLeuGly-98
SEQ. ID. NO. 23952  109-SerAlaGlyGlyAlaMetThrSer-116
SEQ. ID. NO. 23953  122-LysThrThrGluGlnLeuGlu-128
SEQ. ID. NO. 23954  186-GlnMetGlnAsnAsn-190
SEQ. ID. NO. 23955  224-ProThrSerGluGlyIleLeuArgAlaSerThr-234
Hydrophilic Regions - Hopp-Woods
SEQ. ID. NO. 23956  39-ProArgLeuSerVal-43
SEQ. ID. NO. 23957  77-SerLysPheLysSer-81
SEQ. ID. NO. 23958  93-LeuLeuArgGluLeuGly-98
SEQ. ID. NO. 23959  122-LysThrThrGluGlnLeuGlu-128
a737
AMPHI Regions - AMPHI
SEQ. ID. NO. 23960  56-AlaAlaLeuAlaArgValGlyGly-63
Antigenic Index - Jameson-Wolf
SEQ. ID. NO. 23961  24-AlaHisHisAspGlyHisGlyAspAspAspHisGlyHis-36
SEQ. ID. NO. 23962  40-GlnHisSerLysGlnAspLysIleIleSer-49
SEQ. ID. NO. 23963  51-AlaGlnAlaGluLysAlaAlaLeu-58
SEQ. ID. NO. 23964  60-ArgValGlyGlyLysIleThrAspIleAspLeuGluHisAspAsnGlyArgProHisTyrAspValGluIleValLysAsnGlyGlnGluTyr-90
SEQ. ID. NO. 23965  94-ValAspAlaArgThrGlyArgValIleSerSerArgArgAspAsp-108
Hydrophilic Regions - Hopp-Woods
SEQ. ID. NO. 23966  27-AspGlyHisGlyAspAspAspHisGlyHis-36
SEQ. ID. NO. 23967  40-GlnHisSerLysGlnAspLysIleIleSer-49
SEQ. ID. NO. 23968  51-AlaGlnAlaGluLysAlaAlaLeu-58
SEQ. ID. NO. 23969  61-ValGlyGlyLysIleThrAspIleAspLeuGluHisAspAsnGlyArgProHisTyr-79
SEQ. ID. NO. 23970  82-GluIleValLysAsnGlyGlnGluTyr-90
SEQ. ID. NO. 23971  94-ValAspAlaArgThrGlyArg-100
SEQ. ID. NO. 23972  102-IleSerSerArgArgAspAsp-108
a738
AMPHI Regions - AMPHI
SEQ. ID. NO. 23973  91-LeuMetAsnLeuIleTyrProGlyMetAsnAsp-101
SEQ. ID. NO. 23974  139-IleGlySerLeuLeuGlnSerCysIle-147
SEQ. ID. NO. 23975  228-ThrTyrIleAlaAlaIleAlaLeuIle-236
SEQ. ID. NO. 23976  271-ThrIleLeuGluThrPheThrGlyIle-279
SEQ. ID. NO. 23977  285-ValGluArgValAlaAsnGlyGlyPheThrAspLeuProArgGlnIle-300
SEQ. ID. NO. 23978  306-LeuAlaAlaPheGlnSer-311
SEQ. ID. NO. 23979  316-GlyHisGlyTrpAsnSerPheAla-323
SEQ. ID. NO. 23980  338-AspAsnLeuLeuSerAsnLeuPheThr-346
SEQ. ID. NO. 23981  371-LeuLeuThrGlyIleAlaGlyLeuLeuLysArg-381
SEQ. ID. NO. 23982  398-MetCysHisSerMetLeu-403
SEQ. ID. NO. 23983  461-ArgMetValAsnAlaPheSerPro-468
SEQ. ID. NO. 23984  472-AspSerAlaLysThrLeuAsnArgLys-480
SEQ. ID. NO. 23985  482-AsnGluLeuArgTyrIleSer-488
SEQ. ID. NO. 23986  507-LeuProGluTyrProGluThr-513
SEQ. ID. NO. 23987  549-AlaLysGlnTrpMetArgAlaThr-556
SEQ. ID. NO. 23988  567-TyrAlaAspGluIleArgLysLeuProVal-576
SEQ. ID. NO. 23989  579-ProLeuProGluLeuLeuLysAspCysLysAlaPheAlaAlaAlaPro-595
Antigenic Index - Jameson-Wolf
SEQ. ID. NO. 23990  38-LeuGlnProSerProAspPheTyrHis-46
SEQ. ID. NO. 23991  62-AlaGlyLysLysLeuPheAsp-68
SEQ. ID. NO. 23992  123-HisTyrGlyGlnGluArgIle-129
SEQ. ID. NO. 23993  154-GlyTrpGluAspThrProLeu-160
SEQ. ID. NO. 23994  177-GlyGlnArgAsnAsnLeuGly-183
SEQ. ID. NO. 23995  196-LeuAsnGlyGlnArgLysIleProPro-204
SEQ. ID. NO. 23996  242-PheArgSerAspLysSerAsnArgArgThrIle-252
SEQ. ID. NO. 23997  283-ThrAlaValGluArgValAlaAsnGlyGlyPheThrAspLeuProArgGlnIleGluTrpArgLys-304
SEQ. ID. NO. 23998  316-GlyHisGlyTrpAsnSerPheAla-323
SEQ. ID. NO. 23999  332-GluGlnHisAsnIleHisAspAsnLeuLeu-341
SEQ. ID. NO. 24000  378-LeuLeuLysArgProLeuThr-384
SEQ. ID. NO. 24001  424-ProAlaGluAlaSerAspGlyIleAlaPheLysLysAlaAla-437
SEQ. ID. NO. 24002  468-ProAlaThrAspAspSerAlaLysThrLeuAsnArgLysIleAsnGlu-483
SEQ. ID. NO. 24003  508-ProGluTyrProGluThrGlnThrTrpAlaGlu-518
SEQ. ID. NO. 24004  520-AlaThrLeuLysSerLeuLysTyrArgProHisSerAla-532
SEQ. ID. NO. 24005  542-ArgGlnGlyLysValAlaGluAlaLysGlnTrpMet-553
SEQ. ID. NO. 24006  555-AlaThrGlnSerTyr-559
SEQ. ID. NO. 24007  566-ArgTyrAlaAspGluIleArgLys-573
SEQ. ID. NO. 24008  584-LeuLeuLysAspCysLysAla-590
SEQ. ID. NO. 24009  595-ProGlyHisProGluAlaLysProCysLys-604
Hydrophilic Regions - Hopp-Woods
SEQ. ID. NO. 24010  62-AlaGlyLysLysLeuPheAsp-68
SEQ. ID. NO. 24011  125-GlyGlnGluArgIle-129
SEQ. ID. NO. 24012  198-GlyGlnArgLysIlePro-203
SEQ. ID. NO. 24013  243-ArgSerAspLysSerAsnArgArgThrIle-252
SEQ. ID. NO. 24014  283-ThrAlaValGluArgValAla-289
SEQ. ID. NO. 24015  300-IleGluTrpArgLys-304
SEQ. ID. NO. 24016  332-GluGlnHisAsnIle-336
SEQ. ID. NO. 24017  378-LeuLeuLysArgProLeuThr-384
SEQ. ID. NO. 24018  425-AlaGluAlaSerAsp-429
SEQ. ID. NO. 24019  431-IleAlaPheLysLysAlaAla-437
SEQ. ID. NO. 24020  469-AlaThrAspAspSerAlaLysThrLeuAsnArgLysIleAsnGlu-483
SEQ. ID. NO. 24021  525-LeuLysTyrArgPro-529

TABLE 1-continued

| | |
|---|---|
| SEQ. ID. NO. 24022 | 542-ArgGlnGlyLysValAlaGluAlaLysGlnTrpMet-553 |
| SEQ. ID. NO. 24023 | 566-ArgTyrAlaAspGluIleArgLys-573 |
| SEQ. ID. NO. 24024 | 584-LeuLeuLysAspCysLysAla-590 |
| SEQ. ID. NO. 24025 | 596-GlyHisProGluAlaLysProCysLys-604 | a739
AMPHI Regions - AMPHI
| | |
|---|---|
| SEQ. ID. NO. 24026 | 6-AsnLysProPheArgLeu-11 |
| SEQ. ID. NO. 24027 | 53-HisThrAspSerPro-57 |
| SEQ. ID. NO. 24028 | 86-ProAlaGlnProAspGlyThrAsp-93 |
| SEQ. ID. NO. 24029 | 120-ThrAspArgGlnProAspAspAlaGlyAla-129 |
| SEQ. ID. NO. 24030 | 131-AlaGluAsnThrLeu-135 |

Antigenic Index - Jameson-Wolf
| | |
|---|---|
| SEQ. ID. NO. 24031 | 1-MetAlaLysLysProAsnLysProPheArgLeuThrPro-13 |
| SEQ. ID. NO. 24032 | 39-PheAsnProAsnGlyAspLysThrLeuGlnThrGluProGlnHisThrAspSerProArgGluThrGluPhe-62 |
| SEQ. ID. NO. 24033 | 64-LeuProAsnGlyValValGlyGlnAspAlaAlaGlnProGluHisHisHisAlaSerSerSerAlaProAlaGlnProAspGlyThrAspGluSer GlySerGlyLeuProSerProAlaAlaProLysLysAsnArgValLysProGlnProAlaAspThrAlaGlnThrAspArgGlnProAspAspAlaGlyAla GlnAlaGluAsnThrLeuLysGluThrProValLeuProThrAsnValProArgProGluProArgLysGluThrProGluLysGlnAlaGlnProLysGlu ThrProLysGluThrProLysGluAsnHisThrLysProAspThrProLysAsnThrProProLysProHisLysGluIleLeu-193 |

Hydrophilic Regions - Hopp-Woods
| | |
|---|---|
| SEQ. ID. NO. 24034 | 1-MetAlaLysLysProAsnLysProPheArgLeu-11 |
| SEQ. ID. NO. 24035 | 41-ProAsnGlyAspLysThrLeuGlnThrGluProGlnHisThrAspSerProArgGluThrGlu-61 |
| SEQ. ID. NO. 24036 | 72-AspAlaAlaGlnProGluHisHisHis-80 |
| SEQ. ID. NO. 24037 | 87-AlaGlnProAspGlyThrAspGluSerGlySer-97 |
| SEQ. ID. NO. 24038 | 103-AlaAlaProLysLysAsnArgValLysProGlnProAlaAspThrAlaGlnThrAspArgGlnProAspAspAlaGlyAlaGlnAlaGluAsnThrLeu LysGluThrPro-139 |
| SEQ. ID. NO. 24039 | 145-ValProArgProGluProArgLysGluThrProGluLysGlnAlaGlnProLysGluThrProLysGluLysGluThrProLysGluAsnHisThrLys ProAspThrProLysAsnThrProProLysProHisLysGluIleLeu-193 | a740
Antigenic Index - Jameson-Wolf
| | |
|---|---|
| SEQ. ID. NO. 24040 | 25-AlaAsnProProGluAspLysProGln-33 |
| SEQ. ID. NO. 24041 | 57-IleLysHisHisLeuLysGlnGluPheAspLeuLysArgGlnThr-71 |

Hydrophilic Regions - Hopp-Woods
| | |
|---|---|
| SEQ. ID. NO. 24042 | 27-ProProGluAspLysProGln-33 |
| SEQ. ID. NO. 24043 | 57-IleLysHisHisLeuLysGlnGluPheAspLeuLysArgGlnThr-71 | a741
AMPHI Regions - AMPHI
| | |
|---|---|
| SEQ. ID. NO. 24044 | 30-AspIleGlyAlaValLeuAlaAspAlaLeuThrAla-41 |
| SEQ. ID. NO. 24045 | 93-SerArgPheAspPheIleArgGlnIleGlu-102 |
| SEQ. ID. NO. 24046 | 158-ThrSerPheAspLysLeuProGluGlyGlyArg-168 |
| SEQ. ID. NO. 24047 | 200-IleGluHisLeuLys-204 |
| SEQ. ID. NO. 24048 | 251-GlnGluValAlaGlySerAlaGlu-258 |

Antigenic Index - Jameson-Wolf
| | |
|---|---|
| SEQ. ID. NO. 24049 | 21-SerSerGlyGlyGly-25 |
| SEQ. ID. NO. 24050 | 43-LeuAspHisLysAspLysSerLeu-50 |
| SEQ. ID. NO. 24051 | 56-AspGlnSerValArgLysAsnGluLysLeuLysLeu-67 |
| SEQ. ID. NO. 24052 | 71-GlyAlaGluLysThrTyrGlyAsnGlyAspSerLeuAsnThrGlyLysLeuLysAsnAspLysValSerArgPheAspPhe-97 |
| SEQ. ID. NO. 24053 | 101-IleGluValAspGlyGlnLeu-107 |
| SEQ. ID. NO. 24054 | 117-ValTyrLysGlnSerHisSerAla-124 |
| SEQ. ID. NO. 24055 | 129-GlnThrGluGlnValGlnAspSerGlu- HisSerGlyLysMetValAlaLysArgGlnPheArgIleGlyAspIleAlaGlyGluHisThrSerPheAspLysLeuProGluGlyGlyArgAlaThrTyrArg-172 |
| SEQ. ID. NO. 24056 | 174-ThrAlaPheGlySerAspAspAlaSerGlyLysLeu-185 |
| SEQ. ID. NO. 24057 | 191-PheAlaAlaLysGlnGlyHisGlyLysIleGluHisLeuLysSerProGluLeuAsnVal-210 |
| SEQ. ID. NO. 24058 | 213-AlaAlaSerAspIleLysProAspLysLysArgHisAla-225 |
| SEQ. ID. NO. 24059 | 234-AsnGlnAlaGluLysGlySerTyrSer-242 |
| SEQ. ID. NO. 24060 | 247-GlyGlyGlnAlaGlnGluValAlaGly-255 |
| SEQ. ID. NO. 24061 | 257-AlaGluValGluThrAlaAsnGly-264 |

Hydrophilic Regions - Hopp-Woods
| | |
|---|---|
| SEQ. ID. NO. 24062 | 43-LeuAspHisLysAspLysSerLeu-50 |
| SEQ. ID. NO. 24063 | 57-GlnSerValArgLysAsnGluLysLeuLysLeu-67 |
| SEQ. ID. NO. 24064 | 71-GlyAlaGluLysThrTyrGlyAsn-78 |
| SEQ. ID. NO. 24065 | 85-GlyLysLeuLysAsnAspLysValSerArg-94 |
| SEQ. ID. NO. 24066 | 101-IleGluValAspGly-105 |
| SEQ. ID. NO. 24067 | 132-GlnValGlnAspSerGluHisSerGly-140 |
| SEQ. ID. NO. 24068 | 142-MetValAlaLysArgGlnPheArgIle-150 |
| SEQ. ID. NO. 24069 | 152-AspIleAlaGlyGlu-156 |
| SEQ. ID. NO. 24070 | 158-ThrSerPheAspLysLeuProGluGlyGlyArgAlaThrTyr-171 |
| SEQ. ID. NO. 24071 | 177-GlySerAspAspAlaSerGly-183 |
| SEQ. ID. NO. 24072 | 195-GlnGlyHisGlyLysIleGluHisLeuLysSerProGluLeuAsnVal-210 |
| SEQ. ID. NO. 24073 | 213-AlaAlaSerAspIleLysProAspLysLysArgHisAla-225 |
| SEQ. ID. NO. 24074 | 235-GlnAlaGluLysGlySer-240 |
| SEQ. ID. NO. 24075 | 249-GlnAlaGlnGluValAlaGly-255 |
| SEQ. ID. NO. 24076 | 257-AlaGluValGluThr-261 | a742
AMPHI Regions - AMPHI
| | |
|---|---|
| SEQ. ID. NO. 24077 | 26-ArgGluValProAsp-30 |
| SEQ. ID. NO. 24078 | 53-AsnArgProLeuGln-57 |
| SEQ. ID. NO. 24079 | 66-GluAspTrpSerArgLeu-71 |
| SEQ. ID. NO. 24080 | 77-AsnLeuPheSerGlyPheLysHisValPheAsp-87 |
| SEQ. ID. NO. 24081 | 143-LysAlaLeuGluLysLeuLysAla-150 |
| SEQ. ID. NO. 24082 | 153-AspGluThrAlaLysGluTyrArg-160 |

TABLE 1-continued

| | |
|---|---|
| SEQ. ID. NO. 24083 | 234-AsnAlaAlaGlnArgPheProAsnSerLeuTyrAsp-245 |
| SEQ. ID. NO. 24084 | 326-ValTyrAlaGlySer-330 |
| SEQ. ID. NO. 24085 | 340-SerSerProLeuVal-344 |
| SEQ. ID. NO. 24086 | 369-ArgAsnAlaLysLysIle-374 |
| SEQ. ID. NO. 24087 | 422-ThrProAlaPheThrGlyPheSerGlyThrValProValTrpLysThrValLys-439 |
| SEQ. ID. NO. 24088 | 448-LeuTyrAsnTyrAlaLysTyrLeuAsnThrAsn-458 |
| SEQ. ID. NO. 24089 | 475-LeuHisLeuLeuGlyGlyLeuHisTyr-483 |
| SEQ. ID. NO. 24090 | 505-PheGlnThrAlaSerSer-510 |
| SEQ. ID. NO. 24091 | 543-IleTyrGlySerTyrThrLysIlePheLysGlnGlnAspAsn-556 |
| SEQ. ID. NO. 24092 | 616-GlySerPheGlnThrValAlaLysProIleGlyLysValValSerArg-631 |
| SEQ. ID. NO. 24093 | 643-GluAspTrpLysValPheAlaGly-650 |
| SEQ. ID. NO. 24094 | 657-ArgTyrLysAsnAla-661 |
| SEQ. ID. NO. 24095 | 670-AlaLysAsnThrGly-674 |
| SEQ. ID. NO. 24096 | 677-ProTyrAsnPheSerAsnPheThrProValHisIle-688 |
| SEQ. ID. NO. 24097 | 714-ThrSerSerLeuTyrAsnIle-720 |
| SEQ. ID. NO. 24098 | 725-TyrGlyLeuIleAspGlyPheValArgTyr-734 |
| SEQ. ID. NO. 24099 | 736-LeuGlyLysHisAlaLysLeu-742 |
| SEQ. ID. NO. 24100 | 759-TyrAsnArgThrArgGlyAlaAsnAsnPheTyrGlyGluPro-772 |
| Antigenic Index - Jameson-Wolf | |
| SEQ. ID. NO. 24101 | 6-AlaGluAlaAspAlaGlyAsp-12 |
| SEQ. ID. NO. 24102 | 21-MetTyrGlnLysSerArgGluValProAspPheSerGly-33 |
| SEQ. ID. NO. 24103 | 37-SerCysGluAsnGlnLysThrAlaProPheSerSerThrProAlaCysAsnArgProLeuGlnLeuProArgAsnThrTyrLeuGlyGluAspTrpSer ArgLeuSerAlaAspLysTyrAsn-77 |
| SEQ. ID. NO. 24104 | 86-PheAspAsnGlyTrp-90 |
| SEQ. ID. NO. 24105 | 97-SerTyrThrLysAsnGluSerAspAlaLysVal-107 |
| SEQ. ID. NO. 24106 | 120-LeuSerAspGluAspAla-125 |
| SEQ. ID. NO. 24107 | 130-ThrGluLysAsnGluValIleProPheGluProLysAspLysAlaLeuGluLysLeuLysAlaTyrArgAspGluThrAlaLysGluTyrArgGlu ArgLysAspAspPheValLysAsnArgPheAspAsnThrAla-175 |
| SEQ. ID. NO. 24108 | 177-GluGlnTyrArgSerArgArgAlaAlaGluArgLysAlaGlyPheAspGluCysMet-195 |
| SEQ. ID. NO. 24109 | 205-CysGlnGlySerTrpGlyAspProGlyValAspAlaAspLysSerGluPheValAsp-223 |
| SEQ. ID. NO. 24110 | 235-AlaAlaGlnArgPheProAsnSerLeuTyrAspSerSerPheAsnArgLysAlaThrAlaAsnArgArgTyrSerTyrMetPro-262 |
| SEQ. ID. NO. 24111 | 264-ArgHisThrLysAspAspArgGlnTrp-272 |
| SEQ. ID. NO. 24112 | 286-GlyArgGluHisAsp-290 |
| SEQ. ID. NO. 24113 | 295-TyrAlaTyrGlyAspGluLysIleArgSerGluTyr-306 |
| SEQ. ID. NO. 24114 | 308-GluIleTyrGluArgArgHisArgValArgProAsnThrGlyAla-322 |
| SEQ. ID. NO. 24115 | 331-CysGlnGlyGluProAspGlyAspLeuSer-340 |
| SEQ. ID. NO. 24116 | 345-ArgGlyHisLysGluProAspTrpGlnAlaTyrAspGluLysGlyAsnArgThrValTyrAlaGluGluCysArgAsnAlaLysLysIleLysThrGlu ProLysLeuAspAlaGluGlyLysGln-386 |
| SEQ. ID. NO. 24117 | 389-TyrTyrAspGluTyrSerGlySerArgThr-398 |
| SEQ. ID. NO. 24118 | 405-TyrGluLeuAspGluLysGlyAsnLysIleGlnGluThrAsnProAspGlyThrPro-423 |
| SEQ. ID. NO. 24119 | 439-LysValAlaAspAspHisVal-445 |
| SEQ. ID. NO. 24120 | 454-TyrLeuAsnThrAsnLysThrHis-461 |
| SEQ. ID. NO. 24121 | 485-ArgTyrGluThrSerGlnThrLysAspMetProValArgTyrGlyGlnProAlaSerAspPheGlnThr-507 |
| SEQ. ID. NO. 24122 | 509-SerSerIleLysAlaAspGlnAspHisTyrThr-519 |
| SEQ. ID. NO. 24123 | 521-LysMetGlnGlyHisLysLeuThrPro-529 |
| SEQ. ID. NO. 24124 | 545-GlySerTyrThrLys-549 |
| SEQ. ID. NO. 24125 | 551-PheLysGlnGlnAspAsnValAspValSerAla-561 |
| SEQ. ID. NO. 24126 | 584-GlyArgLeuAsnAla-588 |
| SEQ. ID. NO. 24127 | 595-LeuGluGlnLysAsnArgThrValVal-603 |
| SEQ. ID. NO. 24128 | 610-GlyAlaGlyGlyLysGlnGlySer-617 |
| SEQ. ID. NO. 24129 | 628-ValValSerArgGlyAlaGluPheGluLeuSerGlyGluLeuAsnGluAspTrpLys-646 |
| SEQ. ID. NO. 24130 | 652-ThrTyrAsnLysSerArgTyrLysAsnAlaAlaGluValAsnAlaGluArgLeuAlaLysAsnThrGlyAlaAspProTyrAsnPheSerAsn-682 |
| SEQ. ID. NO. 24131 | 708-ValSerAlaGlnSerGlyThrSerSerLeuTyrAsnIleArgGlnGlyGly-724 |
| SEQ. ID. NO. 24132 | 735-GluLeuGlyLysHisAlaLys-741 |
| SEQ. ID. NO. 24133 | 746-GlyThrAsnLeuAsnGlyArgThrTyrPheGluAsnAsnTyrAsnArgThrArgGlyAlaAsnAsnPheTyrGlyGluProArgThrValSerMet-777 |
| Hydrophilic Regions - Hopp-Woods | |
| SEQ. ID. NO. 24134 | 6-AlaGluAlaAspAlaGlyAsp-12 |
| SEQ. ID. NO. 24135 | 23-GlnLysSerArgGluValProAsp-30 |
| SEQ. ID. NO. 24136 | 67-AspTrpSerArgLeuSerAlaAspLys-75 |
| SEQ. ID. NO. 24137 | 97-SerTyrThrLysAsnGluSerAspAlaLysVal-107 |
| SEQ. ID. NO. 24138 | 120-LeuSerAspGluAspAla-125 |
| SEQ. ID. NO. 24139 | 130-ThrGluLysAsnGluValIleProPheGluProLysAspLysAlaLeuGluLysLeuLysAlaTyrArgAspGluThrAlaLysGluTyrArgGlu ArgLysAspAspPheValLysAsnArgPheAspAsnThrAla-175 |
| SEQ. ID. NO. 24140 | 177-GluGlnTyrArgSerArgArgAlaAlaGluArgLysAlaGlyPheAspGluCysMet-195 |
| SEQ. ID. NO. 24141 | 212-ProGlyValAspAlaAspLysSerGluPheValAsp-223 |
| SEQ. ID. NO. 24142 | 247-SerPheAsnArgLysAlaThrAlaAsnArgArgTyrSer-259 |
| SEQ. ID. NO. 24143 | 264-ArgHisThrLysAspAspArgGlnTrp-272 |
| SEQ. ID. NO. 24144 | 286-GlyArgGluHisAsp-290 |
| SEQ. ID. NO. 24145 | 297-TyrGlyAspGluLysIleArgSerGluTyr-306 |
| SEQ. ID. NO. 24146 | 308-GluIleTyrGluArgArgHisArgValArgProAsnThr-320 |
| SEQ. ID. NO. 24147 | 331-CysGlnGlyGluProAspGlyAspLeu-339 |
| SEQ. ID. NO. 24148 | 345-ArgGlyHisLysGluProAsp-351 |
| SEQ. ID. NO. 24149 | 354-AlaTyrAspGluLysGlyAsnArg-361 |
| SEQ. ID. NO. 24150 | 363-ValTyrAlaGluGluCysArgAsnAlaLysLysIleLysThrGluProLysLeuAspAlaGluGlyLysGln-386 |
| SEQ. ID. NO. 24151 | 393-TyrSerGlySerArg-397 |
| SEQ. ID. NO. 24152 | 405-TyrGluLeuAspGluLysGlyAsnLysIleGlnGluThrAsnProAspGly-421 |
| SEQ. ID. NO. 24153 | 439-LysValAlaAspAspHisVal-445 |
| SEQ. ID. NO. 24154 | 485-ArgTyrGluThrSerGlnThrLysAspMetProVal-496 |
| SEQ. ID. NO. 24155 | 500-GlnProAlaSerAsp-504 |
| SEQ. ID. NO. 24156 | 509-SerSerIleLysAlaAspGlnAspHisTyrThr-519 |

TABLE 1-continued

| | |
|---|---|
| SEQ. ID. NO. 24157 | 551-PheLysGlnGlnAspAsnValAspValSerAla-561 |
| SEQ. ID. NO. 24158 | 597-GlnLysAsnArgThrValVal-603 |
| SEQ. ID. NO. 24159 | 611-AlaGlyGlyLysGlnGlySer-617 |
| SEQ. ID. NO. 24160 | 628-ValValSerArgGlyAlaGluPheGluLeuSerGlyGluLeuAsnGluAspTrpLys-646 |
| SEQ. ID. NO. 24161 | 654-AsnLysSerArgTyrLysAsnAlaAlaGluValAsnAlaGluArgLeuAlaLys-671 |
| SEQ. ID. NO. 24162 | 735-GluLeuGlyLysHisAlaLys-741 |
| SEQ. ID. NO. 24163 | 758-AsnTyrAsnArgThrArgGly-764 |
| SEQ. ID. NO. 24164 | 770-GlyGluProArgThrValSerMet-777 | a743
AMPHI Regions - AMPHI

| | |
|---|---|
| SEQ. ID. NO. 24165 | 19-TyrGlyGlySerPhe-23 |
| SEQ. ID. NO. 24166 | 58-SerTyrThrIleAsp-62 |
| SEQ. ID. NO. 24167 | 64-MetSerThrAlaThrGly-69 |
| SEQ. ID. NO. 24168 | 96-ThrLeuGluGluAlaMetLysAsnThrThrGlyValAsnValValArgAsp-112 |
| SEQ. ID. NO. 24169 | 158-ValTyrAspHisIleGluValValArgGlyAlaThrGly-170 |

Antigenic Index - Jameson-Wolf

| | |
|---|---|
| SEQ. ID. NO. 24170 | 1-MetAsnGlnAsnHis-5 |
| SEQ. ID. NO. 24171 | 30-ValSerAspGlyAsnThrVal-36 |
| SEQ. ID. NO. 24172 | 41-ValAsnValArgGlySerHisAlaLeuSerGlyLysThrGluLysThrArgSerTyrThrIleAspArgMetSerThr-66 |
| SEQ. ID. NO. 24173 | 72-IleAlaGlyLysAspThrProGlnSer-80 |
| SEQ. ID. NO. 24174 | 85-ThrArgSerArgLeuAspAspLysAlaValHisThrLeuGluGluAlaMetLysAsnThrThrGly-106 |
| SEQ. ID. NO. 24175 | 109-ValValArgAspSerGlyLeuGlnThrArgPheLeuSerArgGlyPhe-124 |
| SEQ. ID. NO. 24176 | 128-GlnIleGlyGluAspGlyIle-134 |
| SEQ. ID. NO. 24177 | 140-GlyArgSerGlyTyrThrAlaLysIleAspValSerProSerThrAsp-155 |
| SEQ. ID. NO. 24178 | 163-GluValValArgGlyAlaThrGlyLeuThrGlnSerAsnSerGluProGlyGly-180 |
| SEQ. ID. NO. 24179 | 184-LeuIleArgLysArg-188 |

Hydrophilic Regions - Hopp-Woods

| | |
|---|---|
| SEQ. ID. NO. 24180 | 49-LeuSerGlyLysThrGluLysThrArgSerTyrThrIleAspArgMetSerThr-66 |
| SEQ. ID. NO. 24181 | 72-IleAlaGlyLysAspThrProGln-79 |
| SEQ. ID. NO. 24182 | 85-ThrArgSerArgLeuAspAspLysAlaValHisThrLeuGluGluAlaMetLysAsn-103 |
| SEQ. ID. NO. 24183 | 109-ValValArgAspSerGlyLeu-115 |
| SEQ. ID. NO. 24184 | 128-GlnIleGlyGluAspGlyIle-134 |
| SEQ. ID. NO. 24185 | 174-SerAsnSerGluProGlyGly-180 |
| SEQ. ID. NO. 24186 | 184-LeuIleArgLysArg-188 | a746
AMPHI Regions - AMPHI

| | |
|---|---|
| SEQ. ID. NO. 24187 | 10-LeuSerGlyTyrGluGlnLeuLys-17 |
| SEQ. ID. NO. 24188 | 42-LeuSerSerGlyProAlaGluGlnThrAla-51 |
| SEQ. ID. NO. 24189 | 72-SerAlaAlaAspLysProGlnAsp-79 |
| SEQ. ID. NO. 24190 | 94-SerGluProGluAsn-98 |
| SEQ. ID. NO. 24191 | 118-LeuGluAlaSerGluLysLeuGlnGlnAlaGluThrAlaLysThrAlaPro-134 |
| SEQ. ID. NO. 24192 | 153-AspThrValAlaValGlu-158 |
| SEQ. ID. NO. 24193 | 160-ProLysArgThrAlaGluThr-166 |
| SEQ. ID. NO. 24194 | 170-LysAlaGluArgThr-174 |
| SEQ. ID. NO. 24195 | 184-ThrLysThrAlaGluLysValAlaAspLysProLys-195 |
| SEQ. ID. NO. 24196 | 210-SerAlaValLysGluAlaLysLysAlaAspLysAlaGluSer-223 |
| SEQ. ID. NO. 24197 | 238-GluThrAlaGlnLysThrAspLysAlaAspLysThrLysThrAlaGluLys-254 |
| SEQ. ID. NO. 24198 | 287-SerThrIleThrGluIleMetThr-294 |
| SEQ. ID. NO. 24199 | 307-TyrLysAsnAlaArgAspAlaGluArgAspLeu-317 |

Antigenic Index - Jameson-Wolf

| | |
|---|---|
| SEQ. ID. NO. 24200 | 1-MetSerGluAsnLysGlnAsnGluValLeuSerGlyTyrGluGlnLeuLysArgArgAsnArgArgLeuValThr-26 |
| SEQ. ID. NO. 24201 | 43-SerSerGlyProAlaGluGlnThrAlaGlyGluThrSerGlyValGluAsnLysAlaAlaGly-63 |
| SEQ. ID. NO. 24202 | 72-SerAlaAlaAspLysProGlnAspLeuAlaGlyGluAspLysProSerAlaAlaAspSerGluIleSerGluProGluAsnVal-99 |
| SEQ. ID. NO. 24203 | 107-AsnAspArgLeuGluAspSerAsnIleLysGlyLeuGluAlaSerGluLysLeuGlnGlnAlaGluThrAlaLysThrAlaProLysGlnAlaLys
GlnArgAlaAlaGluLysValProAlaThrAlaAspSerThrAspThrValAlaValGluLysProLysArgThrAlaGluThrLysProGlnLysAla
GluArgThrAlaLysAlaLysProLysAlaLysGluThrLysThrAlaGluLysValAlaAspLysProLysThrAlaAlaGluLysThrLysProAsp
ThrAlaLysSerAspSerAlaValLysGluAlaLysLysAlaAspLysAlaGluSerLysLysThrAlaGluLysAspArgSerAspGlyLysLysHis
GluThrAlaGlnLysThrAspLysAlaAspLysThrLysThrAlaGluLysGluLysSerGlyLysLysAlaAla-262 |
| SEQ. ID. NO. 24204 | 266-GlyTyrAlaGluLysGluArgAlaLeuSerLeuGlnArgLysMetLysAlaAlaGlyIle-285 |
| SEQ. ID. NO. 24205 | 292-IleMetThrAspAsnGlyLysValTyrArgValLysSerSerAsnTyrLysAsnAlaArgAspAlaGluArgAspLeuAsnLysLeuArgVal-322 |

Hydrophilic Regions - Hopp-Woods

| | |
|---|---|
| SEQ. ID. NO. 24206 | 1-MetSerGluAsnLysGlnAsnGluVal-9 |
| SEQ. ID. NO. 24207 | 14-GluGlnLeuLysArgArgAsnArgArgLeuVal-25 |
| SEQ. ID. NO. 24208 | 45-GlyProAlaGluGlnThrAlaGlyGluThrSerGlyValGluAsnLysAlaAlaGly-63 |
| SEQ. ID. NO. 24209 | 72-SerAlaAlaAspLysProGlnAspLeuAlaGlyGluAspLysProSerAlaAlaAspSerGluIleSerGluProGluAsnVal-99 |
| SEQ. ID. NO. 24210 | 108-AspArgLeuGluAspSerAsnIleLysGlyLeuGluAlaSerGluLysLeuGlnGlnAlaGluThrAlaLysThrAlaProLysGlnAlaLysGln
ArgAlaAlaGluLysValProAlaThrAlaAspSerThrAsp-153 |
| SEQ. ID. NO. 24211 | 155-ValAlaValGluLysProLysArgThrAlaGluThrLysProGlnLysAlaGluArgThrAlaLysAlaLysProLysAlaLysGluThrLysThr
AlaGluLysValAlaAspLysProLysThrAlaAlaGluLysThrLysProAspThrAlaLysSerAspSerAlaValLysGluAlaLysLysAlaAspLys
AlaGluSerLysLysThrAlaGluLysAspArgSerAspGlyLysLysHisGluThrAlaGlnLysThrAspLysAlaAspLysThrLysThrAlaGluLys
GluLysSerGlyLysLysAlaAla-262 |
| SEQ. ID. NO. 24212 | 267-TyrAlaGluLysGluArgAlaLeuSerLeuGlnArgLysMetLysAlaAlaGlyIle-285 |
| SEQ. ID. NO. 24213 | 292-IleMetThrAspAsnGlyLysValTyrArgValLysSerSerAsnTyrLysAsnAlaArgAspAlaGluArgAspLeuAsnLysLeuArgVal-322 | a747
AMPHI Regions - AMPHI

| | |
|---|---|
| SEQ. ID. NO. 24214 | 28-ValSerLysSerAlaLysGlyTrp-35 |

Antigenic Index - Jameson-Wolf

| | |
|---|---|
| SEQ. ID. NO. 24215 | 8-TyrAlaAspLeuArgGlyLysThrLysVal-17 |
| SEQ. ID. NO. 24216 | 23-CysAlaSerArgAspValSerLysSerAlaLysGlyTrp-35 |

TABLE 1-continued

| | |
|---|---|
| SEQ. ID. NO. 24217 | 42-AsnValGlyLysGlnLeuThrAspSerValGlyLeuGluPheAspProTyrTyrArgHisLysThrIleCysLysProArgGluIleValLeuAsp GlyAspLysThrLysMetGlyArgSerLysSerAsnGluTyrGly-88 |
| SEQ. ID. NO. 24218 | 97-SerGlnLeuLysSerLys-102 |

Hydrophilic Regions - Hopp-Woods

| | |
|---|---|
| SEQ. ID. NO. 24219 | 8-TyrAlaAspLeuArgGlyLysThrLysVal-17 |
| SEQ. ID. NO. 24220 | 23-CysAlaSerArgAspValSerLysSerAlaLys-33 |
| SEQ. ID. NO. 24221 | 63-ThrIleCysLysProArgGluIleValLeuAspGlyAspLysThrLysMetGlyArgSerLysSerAsnGluTyr-87 | a748
AMPHI Regions - AMPHI

| | |
|---|---|
| SEQ. ID. NO. 24222 | 22-GlyAlaValGlyAlaIleGlyGly-29 |
| SEQ. ID. NO. 24223 | 40-AlaGluArgThrAlaGluSerGlnHis-48 |
| SEQ. ID. NO. 24224 | 82-SerAlaLysGlnLeuGluAsnLeuPheArgThrLeu-93 |
| SEQ. ID. NO. 24225 | 155-LeuGlnGluMetArgAspPheSerAsnAspLysLeuGlnLysSerTrp-170 |
| SEQ. ID. NO. 24226 | 188-GlnAlaAlaLeuArgAspIleIleLysHisThrValGln-200 |
| SEQ. ID. NO. 24227 | 250-GlyValAlaAlaAsnSer-255 |
| SEQ. ID. NO. 24228 | 257-AspGluProGluTrp-261 |
| SEQ. ID. NO. 24229 | 268-GlnAlaValArgLeuIleArgHisPheValGluPheTrpAspArg-282 |
| SEQ. ID. NO. 24230 | 310-GlnProAspPheAlaLys-315 |
| SEQ. ID. NO. 24231 | 334-ArgAspProGluPheLeu-339 |
| SEQ. ID. NO. 24232 | 390-LeuGluGluTyrIleSerProPhe-397 |

Antigenic Index - Jameson-Wolf

| | |
|---|---|
| SEQ. ID. NO. 24233 | 1-MetSerLysAsnGlnProAlaGlnProThrArgArgThrLeuPhe-15 |
| SEQ. ID. NO. 24234 | 29-GlyTyrLeuGlyGlyLysLysArgGlyGluThrAlaGluArgThrAlaGluSerGlnHisSerProGlnAla-52 |
| SEQ. ID. NO. 24235 | 80-AlaGlnSerAlaLysGlnLeuGluAsn-88 |
| SEQ. ID. NO. 24236 | 101-ThrGlnGlyGlyGluTyrGlnAspGlyAspAspLysLeuProProAlaGlySerGly-119 |
| SEQ. ID. NO. 24237 | 125-PheAsnProAspGlyLeuThr-131 |
| SEQ. ID. NO. 24238 | 139-SerLeuPheAspGlyArgPheGlyLeuLysAspLysLysProIleHis-154 |
| SEQ. ID. NO. 24239 | 156-GlnGluMetArgAspPheSerAsnAspLysLeuGlnLysSerTrpCysAspGlyAspLeuSer-176 |
| SEQ. ID. NO. 24240 | 183-ThrProGluThrCys-187 |
| SEQ. ID. NO. 24241 | 208-IleAspGlyTrpGlnProLysSerGluProGlyAlaMetAla-221 |
| SEQ. ID. NO. 24242 | 226-LeuGlyPheArgAspGlyThrGlyAsnProLysValSerAspProLysThrAlaAspGlu-245 |
| SEQ. ID. NO. 24243 | 255-SerLeuAspGluProGluTrpAlaLysAsnGlySerTyrGlnAla-269 |
| SEQ. ID. NO. 24244 | 279-PheTrpAspArgThrProLeuGlnGluGlnThrAspIlePheGlyArgArgLysTyrSerGlyAlaProMetAspGlyLysLysGluAlaAspGln ProAspPheAlaLysAspProGluGlyAsnThrThrProLysAspSerHisIleArgLeuAlaAsnProArgAspProGluPheLeuLysLysHis ArgLeuPheArg-346 |
| SEQ. ID. NO. 24245 | 348-AlaTyrSerTyrSerArgGlyLeuAlaSerSerGlyGlnLeu-361 |
| SEQ. ID. NO. 24246 | 385-LeuAsnGlyGluProLeuGluGluTyr-393 |
| SEQ. ID. NO. 24247 | 406-ProGlyValGluLysGlyGlyPhe-413 |

Hydrophilic Regions - Hopp-Woods

| | |
|---|---|
| SEQ. ID. NO. 24248 | 1-MetSerLysAsnGlnPro-6 |
| SEQ. ID. NO. 24249 | 8-GlnProThrArgArgThrLeuPhe-15 |
| SEQ. ID. NO. 24250 | 32-GlyGlyLysLysArgGlyGluThrAlaGluArgThrAlaGluSerGlnHis-48 |
| SEQ. ID. NO. 24251 | 80-AlaGlnSerAlaLysGlnLeuGluAsn-88 |
| SEQ. ID. NO. 24252 | 104-GlyGluTyrGlnAspGlyAspAspLysLeuProPro-115 |
| SEQ. ID. NO. 24253 | 145-PheGlyLeuLysAspLysLysProIleHis-154 |
| SEQ. ID. NO. 24254 | 156-GlnGluMetArgAspPheSerAsnAspLysLeuGlnLysSerTrpCysAspGlyAspLeu-175 |
| SEQ. ID. NO. 24255 | 211-TrpGlnProLysSerGluProGlyAlaMetAla-221 |
| SEQ. ID. NO. 24256 | 229-ArgAspGlyThrGlyAsnProLysValSerAspProLysThrAlaAsp-244 |
| SEQ. ID. NO. 24257 | 255-SerLeuAspGluProGluTrpAlaLys-263 |
| SEQ. ID. NO. 24258 | 283-ThrProLeuGlnGluGlnThrAspIlePheGlyArgArgLysTyrSer-298 |
| SEQ. ID. NO. 24259 | 301-ProMetAspGlyLysLysGluAlaAspGlnProAspPheAlaLysAspProGluGlyAsnThrThrProLysAspSerHisIle-328 |
| SEQ. ID. NO. 24260 | 331-AlaAsnProArgAspProGluPheLeuLysLysHisArgLeuPheArg-346 |
| SEQ. ID. NO. 24261 | 388-GluProLeuGluGluTyr-393 |
| SEQ. ID. NO. 24262 | 407-GlyValGluLysGlyGly-412 | a749
AMPHI Regions - AMPHI

| | |
|---|---|
| SEQ. ID. NO. 24263 | 1-MetArgLysPheAsnLeuThrAlaLeuSerValMetLeuAlaLeuGlyLeuThrAlaCysGlnProProGluAlaGluLysAlaAlaProAlaAla SerGlyGluAlaGlnThrAlaAsnGluGlyGlySerValSerIleAlaValAsnAspAsnAlaCysGluProMetGluLeuThrValProSerGlyGlnVal ValPheAsnIleLysAsnAsnSerGlyArgLysLeuGluTrpGluIleLeuLysGlyValMetValValAspGluArgGluAsnIleAlaProGlyLeuSer AspLysMetThrValThrLeuLeuProGlyGluTyrGluMetThrCysGlyLeuLeuThrAsnProArgGlyLysLeuValValThrAspSerGlyPheLys AspThrAlaAsnGluAlaAspLeuGluLysLeuSerGlnProLeuAlaAspTyrLysAlaTyrValGlnGlyGluValLysGluLeuValAlaLysThrLys ThrPheThrGluAlaValLysAlaGlyAspIleGluLysAlaLysSerLeuPheAlaAspThrArgValHisTyrGluArgIleGluProIleAlaGluLeu PheSerGluLeuAspProValIleAspAlaArgGluAspAspPheLysAspGlyAlaLysAspAlaGlyPheThrGlyPheHisArgIleGluTyrAlaLeu TrpValGluLysAspValSerGlyValLysGluIleAlaAlaLysLeuMetThrAspValGluAlaLeuGlnLysGluIleAspAlaLeuAlaPheProPro GlyLysValValGlyGlyAlaSerGluLeuIleGluGluValAlaGlySerLysIleSerGlyGluGluAspArgTyrSerHisThrAspLeuSerAspPhe GlnAlaAsnValAspGlySerLysLysIleValAspLeuPheArgProLeuIleGluThrLysAsnLysAlaLeuLeuGluLysThrAspThrAsnPheLys GlnValAsnGluIleLeuAlaLysTyrArgThrLysAspGlyPheGluThrTyrAspLysLeuGlyGluAlaAspArgLysAlaLeuGlnAlaSerIleAsn AlaLeuAlaGluAspLeuAlaGlnLeuArgGlyIleLeuGlyLeuLys-388 |

Antigenic Index - Jameson-Wolf (SEQ. ID. NO. 24263)
1-MetArgLysPheAsnLeuThrAlaLeuSerValMetLeuAlaLeuGlyLeuThrAlaCysGlnProProGluAlaGluLysAlaAlaProAlaAlaSerGlyGluAlaGlnThrAlaAsnGlu
GlyGlySerValSerIleAlaValAsnAspAsnAlaCysGluProMetGluLeuThrValProSerGlyGlnValValPheAsnIleLysAsnAsnSerGlyArgLysLeuGluTrpGluIle
LeuLysGlyValMetValValAspGluArgGluAsnIleAlaProGlyLeuSerAspLysMetThrValThrLeuLeuProGlyGluTyrGluMetThrCysGlyLeuLeuThrAsnProArg
GlyLysLeuValValThrAspSerGlyPheLysAspThrAlaAsnGluAlaAspLeuGluLysLeuSerGlnProLeuAlaAspTyrLysAlaTyrValGlnGlyGluValLysGluLeuVal
AlaLysThrLysThrPheThrGluAlaValLysAlaGlyAspIleGluLysAlaLysSerLeuPheAlaAspThrArgValHisTyrGluArgIleGluProIleAlaGluLeuPheSerGlu
LeuAspProValIleAspAlaArgGluAspAspPheLysAspGlyAlaLysAspAlaGlyPheThrGlyPheHisArgIleGluTyrAlaLeuTrpValGluLysAspValSerGlyValLys
GluIleAlaAlaLysLeuMetThrAspValGluAlaLeuGlnLysGluIleAspAlaLeuAlaPheProProGlyLysValValGlyGlyAlaSerGluLeuIleGluGluValAlaGlySer
LysIleSerGlyGluGluAspArgTyrSerHisThrAspLeuSerAspPheGlnAlaAsnValAspGlySerLysLysIleValAspLeuPheArgProLeuIleGluThrLysAsnLysAla
LeuLeuGluLysThrAspThrAsnPheLysGlnValAsnGluIleLeuAlaLysTyrArgThrLysAspGlyPheGluThrTyrAspLysLeuGlyGluAlaAspArgLysAlaLeuGlnAla
SerIleAsnAlaLeuAlaGluAspLeuAlaGlnLeuArgGlyIleLeuGlyLeuLys-388

TABLE 1-continued

Hydrophilic Regions - Hopp-Woods (SEQ. ID. NO. 24263)
1-MetArgLysPheAsnLeuThrAlaLeuSerValMetLeuAlaLeuGlyLeuThrAlaCysGlnProProGluAlaGluLysAlaAlaProAlaAlaSerGlyGluAlaGlnThrAlaAsnGlu
GlyGlySerValSerIleAlaValAsnAspAsnAlaCysGluProMetGluLeuThrValProSerGlyGlnValValPheAsnIleLysAsnAsnSerGlyArgLysLeuGluTrpGluIle
LeuLysGlyValMetValValAspGluArgGluAsnIleAlaProGlyLeuSerAspLysMetThrValThrLeuLeuProGlyGluTyrGluMetThrCysGlyLeuLeuThrAsnProArg
GlyLysLeuValValThrAspSerGlyPheLysAspThrAlaAsnGluAlaAspLeuGluLysLeuSerGlnProLeuAlaAspTyrLysAlaTyrValGlnGlyGluValLysGluLeuVal
AlaLysThrLysThrProTheThrGluAlaValLysAlaGlyAspIleGluLysAlaLysSerLeuPheAlaAspThrArgValHisTyrGluArgIleGluProIleAlaGluLeuPheSerGlu
LeuAspProValIleAspAlaArgGluAspAspPheLysAspGlyAlaLysAspAlaGlyPheThrGlyPheHisArgIleGluTyrAlaLeuTrpValGluLysAspValSerGlyValLys
GluIleAlaAlaLysLeuMetThrAspValGluAlaLeuGlnLysGluIleAspAlaLeuAlaPheProProGlyLysValValGlyGlyAlaSerGluLeuIleGluGluValAlaGlySer
LysIleSerGlyGluGluAspArgTyrSerHisThrAspLeuSerAspPheGlnAlaAsnValAspGlySerLysIleValAspLeuPheArgProLeuIleGluThrLysAsnLysAla
LeuLeuGluLysThrAspThrAsnPheLysGlnValAsnGluIleLeuAlaLysTyrArgThrLysAspGlyPheGluThrTyrAspLysLeuGlyGluAlaAspArgLysAlaLeuGlnAla
SerIleAsnAlaLeuAlaGluAspLeuAlaGlnLeuArgGlyIleLeuGlyLeuLys-388
a750
AMPHI Regions - AMPHI
SEQ. ID. NO. 24264 1-ValLysProArgPheTyrTrpAlaAlaCysAlaValLeuLeuThrAlaCysSerProGluProAlaAlaGluLysThrValSerAlaAlaSerAla
SerAlaAlaThrLeuThrValProThrAlaArgGlyAspAlaValValProLysAsnProGluArgValAlaValTyrAspTrpAla
AlaLeuAspThrLeuThrGluLeuGlyValAsnValGlyAlaThrThrAlaProValArgValAspTyrLeuGln
ProAlaPheAspLysAlaAlaThrValGlyThrLeuPheGluProAspTyrGlu
AlaLeuHisArgTyrAsnProGlnLeuValIleThrGlyGlyProGlyAlaGlu
AlaTyrGluGlnLeuAlaLysAsnAlaThrThrIleAspLeuThrValAspAsn
GlyAsnIleArgThrSerGlyGluLysGlnMetGluThrLeuAlaArgIlePhe
GlyLysGluAlaArgAlaAlaGluLeuLysAlaGlnIleAspAlaLeuPheAla
GlnThrArgGluAlaAlaLysGlyLysGlyArgGlyLeuValLeuSerValThr
GlyAsnLysValSerAlaPheGlyThrGlnSerArgLeuAlaSerTrpIleHis
GlyAspIleGlyLeuProProValAspGluSerLeuArgAsnGluGlyHisGly
GlnProValSerPheGluTyrIleLysGluLysAsnProAspTrpIlePhePheIle
IleAspArgThrAlaAlaIleGlyGlnGluGlyProAlaAlaValGluValLeu
AspAsnAlaLeuValArgGlyThrAsnAlaTrpLysArgLysGlnIleIleVal
MetProAlaAlaAsnTyrIleValAlaGlyGlySerArgGlnLeuIleGlnAla
AlaGluGlnLeuLysGluAlaPheGluLysAlaGluProValAlaAlaGlyLysGlu-321
Antigenic Index - Jameson-Wolf (SEQ. ID. NO. 24264)
1-ValLysProArgPheTyrTrpAlaAlaCysAlaValLeuLeuThrAlaCysSerProGluProAlaAlaGluLys
ThrValSerAlaAlaSerAlaSerAlaAlaThrLeuThrValProThrAlaArgGlyAspAlaValValProLys
AsnProGluArgValAlaValTyrAspTrpAlaAlaLeuAspThrLeuThrGluLeuGlyValAsnValGlyAlaThr
ThrAlaProValArgValAspTyrLeuGlnProAlaPheAspLysAlaAlaThrValGlyThrLeuPheGluPro
AspTyrGluAlaLeuHisArgTyrAsnProGlnLeuValIleThrGlyGlyProGlyAlaGluAlaTyrGluGln
LeuAlaLysAsnAlaThrThrIleAspLeuThrValAspAsnGlyAsnIleArgThrSerGlyGluLysGlnMetGlu
ThrLeuAlaArgIlePheGlyLysGluAlaArgAlaAlaGluLeuLysAlaGlnIleAspAlaLeuPheAlaGln
ThrArgGluAlaAlaLysGlyLysGlyArgGlyLeuValLeuSerValThrGlyAsnLysValSerAlaPheGly
ThrGlnSerArgLeuAlaSerTrpIleHisGlyAspIleGlyLeuProProValAspGluSerLeuArgAsnGluGly
HisGlyGlnProValSerPheGluTyrIleLysGluLysAsnProAspTrpIlePhePheIleIleAspArgThrAla
AlaIleGlyGlnGluGlyProAlaAlaValGluValLeuAspAsnAlaLeuValArgGlyThrAsnAlaTrpLys
ArgLysGlnIleIleValMetProAlaA-
laAsnTyrIleValAlaGlyGlySerArgGlnLeuIleGlnAlaAlaGluGlnLeuLysGluAlaPheGluLysAlaGluProValAlaAlaGlyLysGlu-321
Hydrophilic Regions - Hopp-Woods (SEQ. ID. NO. 24264)
1-ValLysProArgPheTyrTrpAlaAlaCysAlaValLeuLeuThrAlaCysSerProGluProAlaAlaGluLys
ThrValSerAlaAlaSerAlaSerAlaAlaThrLeuThrValProThrAlaArgGlyAspAlaValValProLys
AsnProGluArgValAlaValTyrAspTrpAlaAlaLeuAspThrLeuThrGluLeuGlyValAsnValGlyAlaThr
ThrAlaProValArgValAspTyrLeuGlnProAlaPheAspLysAlaAlaThrValGlyThrLeuPheGluPro
AspTyrGluAlaLeuHisArgTyrAsnProGlnLeuValIleThrGlyGlyProGlyAlaGluAlaTyrGluGln
LeuAlaLysAsnAlaThrThrIleAspLeuThrValAspAsnGlyAsnIleArgThrSerGlyGluLysGlnMetGlu
ThrLeuAlaArgIlePheGlyLysGluAlaArgAlaAlaGluLeuLysAlaGlnIleAspAlaLeuPheAlaGln
ThrArgGluAlaAlaLysGlyLysGlyArgGlyLeuValLeuSerValThrGlyAsnLysValSerAlaPheGly
ThrGlnSerArgLeuAlaSerTrpIleHisGlyAspIleGlyLeuProProValAspGluSerLeuArgAsnGluGly
HisGlyGlnProValSerPheGluTyrIleLysGluLysAsnProAspTrpIlePhePheIleIleAspArgThrAla
AlaIleGlyGlnGluGlyProAlaAlaValGluValLeuAspAsnAlaLeuValArgGlyThrAsnAlaTrpLys
ArgLysGlnIleIleValMetProAlaA-
laAsnTyrIleValAlaGlyGlySerArgGlnLeuIleGlnAlaAlaGluluGlnLeuLysGluAlaPheGluLysAlaGluProValAlaAlaGlyLysGlu-321
a756
AMPHI Regions - AMPHI
SEQ. ID. NO. 24265 1-MetThrAlaAsnPheAlaGlnThrLeuValGluIleGlnAspSerLeuXxxArgValValSerThrValGlnTyrGlyAspAspAsnLeuLysArg
LeuThrAlaAspLysArgLysGlnTyrGluLeuAsnPheLysIleSerGluGlySerThrArgValGluSerAspPheLysGluThrLeuValArgPheGly
ArgAspMetLeuGlnAspMetProProLysIleArgSerAlaThrLeuValAlaLeuThrThrLeuLeuValGlyGlyAlaLeuGlyTyrGlyTyrLeuGlu
TyrLeuLysGlnValAlaSerGluGlyTyrGlnThrGluArgLeuTyrAsnAlaValAspArgLeuAlaGluSerGlnGluArgIleThrSerAlaIleLeu
LysGlyAlaArgGlyAlaAspPheValGlnIleGlyArgArgSerTyrSerArgGluAspIleSerGluAlaAsnArgArgAlaGluArgValProTyrGly
AlaGluLeuValSerAspGlyAsnPheThrAlaValLeuSerAspIleGlyAsp-186
Antigenic Index - Jameson-Wolf (SEQ. ID. NO. 24265)
1-MetThrAlaAsnPheAlaGlnThrLeuValGluIleGlnAspSerLeuXxxArgValValSerThrValGlnTy
rGlyAspAspAsnLeuLysArgLeuThrAlaAspLysArgLysGlnTyrGluLeuAsnPheLysIleSerGluGly
SerThrArgValGluSerAspPheLysGluThrLeuValArgPheGlyArgAspMetLeuGlnAspMetProProL
ysIleArgSerAlaThrLeuValAlaLeuThrThrLeuLeuValGlyGlyAlaLeuGlyTyrGlyTyrLeuGluTy
rLeuLysGlnValAlaSerGluGlyTyrGlnThrGluArgLeuTyrAsnAlaValAspArgLeuAlaGluSerGln
GluArgIleThrSerAlaIleLeuLysGlyAlaArgGlyAlaAspPheValGlnIleGlyArgArgSerTyrSerA
rgGluAspIleSerGluAlaAsnArgArgAlaGluArgValProTyrGlyAlaGluLeuValSerAspGlyAsnPh
eThrAlaValLeuSerAspIleGlyAsp-186
Hydrophilic Regions - Hopp-Woods (SEQ. ID. NO. 24265)
1-MetThrAlaAsnPheAlaGlnThrLeuValGluIleGlnAspSerLeuXxxArgValValSerThrValGlnTy
rGlyAspAspAsnLeuLysArgLeuThrAlaAspLysArgLysGlnTyrGluLeuAsnPheLysIleSerGluGly
SerThrArgValGluSerAspPheLysGluThrLeuValArgPheGlyArgAspMetLeuGlnAspMetProProL
ysIleArgSerAlaThrLeuValAlaLeuThrThrLeuLeuValGlyGlyAlaLeuGlyTyrGlyTyrLeuGluTy
rLeuLysGlnValAlaSerGluGlyTyrGlnThrGluArgLeuTyrAsnAlaValAspArgLeuAlaGluSerGln TABLE 1-continued GluArgIleThrSerAlaIleLeuLysGlyAlaArgGlyAlaAspPheValGlnIleGlyArgArgSerTyrSerA
rgGluAspIleSerGluAlaAsnArgArgAlaGluArgValProTyrGlyAlaGluLeuValSerAspGlyAsnPh
eThrAlaValLeuSerAspIleGlyAsp-186 a758

AMPHI Regions - AMPHI

SEQ. ID. NO. 24266  1-MetAsnAsnLeuThrValPheThrArgPheAspThrAspLeuAlaThrLeuAlaAspGluLeuGlnTyrValTrpGluHisThrAlaValThr
AspHisGlnGlyLysLeuValGluIleProValCysTyrGlyGlyGluTyrGlyProAspLeuAlaGluValAlaAlaPheHisGlnThrValIleSerGlu
IleValArgArgHisThrAlaGlnThrTyrThrValPheMetMetGlyPheGlnProGlyPheProTyrLeuGlyGlyLeuProGluAlaLeuHisThrPro
ArgArgAlaValProArgThrSerValProAlaGlySerValGlyIleGlyGlySerGlnThrGlyValTyrProPheAlaSerProGlyGlyTrpGlnIle
IleGlyArgThrGluLeuProLeuPheArgAlaAspLeuAsnProProThrLeuLeuAlaAlaGlyAspGlnValArgPheValAlaGluArgIleGlu
Pro-167

Antigenic Index - Jameson-Wolf (SEQ. ID. NO. 24266)
1-MetAsnAsnLeuThrValPheThrArgPheAspThrAspLeuAlaThrLeuAlaAspGluLeuGlnTyrValTr
pGluHisThrAlaValThrAspHisGlnGlyLysLeuValGluIleProValCysTyrGlyGlyGluTyrGlyPro
AspLeuAlaGluValAlaAlaPheHisGlnThrValIleSerGluIleValArgArgHisThrAlaGlnThrTyrT
hrValPheMetMetGlyPheGlnProGlyPheProTyrLeuGlyGlyLeuProGluAlaLeuHisThrProArgAr
gAlaValProArgThrSerValProAlaGlySerValGlyIleGlyGlySerGlnThrGlyValTyrProPheAla
SerProGlyGlyTrpGlnIleIleGlyArgThrGluLeuProLeuPheArgAlaAspLeuAsnProProThrLeuL
euAlaAlaGlyAspGlnValArgPheValAlaGluArgIleGluPro-167

Hydrophilic Regions - Hopp-Woods (SEQ. ID. NO. 24266)
1-MetAsnAsnLeuThrValPheThrArgPheAspThrAspLeuAlaThrLeuAlaAspGluLeuGlnTyrValTr
pGluHisThrAlaValThrAspHisGlnGlyLysLeuValGluIleProValCysTyrGlyGlyGluTyrGlyPro
AspLeuAlaGluValAlaAlaPheHisGlnThrValIleSerGluIleValArgArgHisThrAlaGlnThrTyrT
hrValPheMetMetGlyPheGlnProGlyPheProTyrLeuGlyGlyLeuProGluAlaLeuHisThrProArgAr
gAlaValProArgThrSerValProAlaGlySerValGlyIleGlyGlySerGlnThrGlyValTyrProPheAla
SerProGlyGlyTrpGlnIleIleGlyArgThrGluLeuProLeuPheArgAlaAspLeuAsnProProThrLeuL
euAlaAlaGlyAspGlnValArgPheValAlaGluArgIleGluPro-167 a761

AMPHI Regions - AMPHI

SEQ. ID. NO. 24267  1-MetLysIleSerPheHisLeuAlaLeuLeuProThrLeuIleIleAlaSe
rPheProValAlaAlaAlaAspThrGlnAspAsnGlyGluHisTyrThrAlaThrLeuProThrValSerValValGlyGlnSerAspThrSerValLeuLysG
lyTyrIleAsnTyrAspGluAlaAlaValThrArgAsnGlyGlnLeuIleLysGluThrProGlnThrIleAspThrLeuAsnIleGlnLysAsnLysAsnTyr
GlyThrAsnAspLeuSerSerIleLeuGluGlyAsnAlaGlyIleAspAlaAlaTyrAspMetArgGlyGluSerIlePheLeuArgGlyPheGlnAlaAspAl
aSerAspIleTyrArgAspGlyValArgGluSerGlyGlnValArgArgSerThrAlaAsnIleGluArgValGluIleLeuLysGlyProSerSerValLeuT
yrGlyArgThrAsnGlyGlyGlyValIleAsnMetValSerLysTyrAlaAsnPheLysGlnSerArgAsnIleGlyThrValTyrGlySerTrpAlaAsnArg
SerLeuAsnMetAspIleAsnGluValLeuAsnLysAsnValAlaIleArgLeuThrGlyGluValGlyArgAlaAsnSerPheArgSerGlyIleAspSerLy
sAsnValMetValSerProSerIleThrValLysLeuAspAsnGlyLeuLysTrpThrGlyGlnTyrThrTyrAspAsnValGluArgThrProAspArgSerP
roThrLysSerValTyrAspArgPheGlyLeuProTyrArgMetGlyPheAlaHisArgAsnAspPheValLysAspLysLeuGlnValTrpArgSerAspLeu
GluTyrAlaPheAsnAspLysTrpArgAlaGlnTrpGlnLeuAlaHisArgThrAlaAlaGlnAspPheAspHisPheTyrAlaGlySerGluAsnGlyAsnLe
uIleLysArgAsnTyrAlaTrpGlnGlnThrAspAsnLysThrLeuSerSerAsnLeuThrLeuAsnGlyAspTyrThrIleGlyArgPheGluAsnHisLeuT
hrValGlyMetAspTyrSerArgGluHisArgAsnProThrLeuGlyPheSerSerAlaPheSerAlaSerIleAsnProTyrAspArgAlaSerTrpProAla
SerGlyArgLeuGlnProIleLeuThrGlnAsnArgHisLysAlaAspSerTyrGlyIlePheValGlnAsnIlePheSerAlaThrProAspLeuLysPheVa
lLeuGlyGlyArgTyrAspLysTyrThrPheAsnSerGluAsnLysLeuThrGlySerSerArgGlnTyrSerGlyHisSerPheSerProAsnIleGlyAlaV
alTrpAsnIleAsnProValHisThrLeuTyrAlaSerTyrAsnLysGlyPheAlaProTyrGlyGlyArgGlyGlyTyrLeuSerIleAspThrLeuSerSer
AlaValPheAsnAlaAspProGluTyrThrArgGlnTyrGluThrGlyValLysSerSerTrpLeuAspAspArgLeuSerThrThrLeuSerAlaTyrGlnI1
eGluArgPheAsnIleArgTyrArgProAspProLysAsnAsnProTyrIleTyrAlaValSerGlyLysHisArgSerArgGlyValGluLeuSerAlaIleG
lyGlnIleIleProLysLysLeuTyrLeuArgGlySerLeuGlyValMetGlnAlaLysValValGluAspLysGluAsnProAspArgValGlyIleHisLeu
AsnAsnThrSerAsnValThrGlyAsnLeuPhePheArgTyrThrProThrGluAsnLeuTyrGlyGluIleGlyValThrGlyThrGlyLysArgTyrGlyTy
rAspSerArgAsnLysGluValThrThrLeuProGlyPheAlaArgValAspAlaMetLeuGlyTrpAsnHisLysAsnValAsnValThrPheAlaAlaAlaA
snLeuPheAsnGlnLysTyrTrpArgSerAspSerMetProGlyAsnProArgGlyTyrThrAlaArgValAsnTyrArgPhe-703

Antigenic Index - Jameson-Wolf (SEQ. ID. NO. 24267)
1-MetLysIleSerPheHisLeuAlaLeuLeuProThrLeuIleIleAlaSerPheProValAlaAlaAlaAspTh
rGlnAspAsnGlyGluHisTyrThrAlaThrLeuProThrValSerValValGlyGlnSerAspThrSerValLeu
LysGlyTyrIleAsnTyrAspGluAlaAlaValThrArgAsnGlyGlnLeuIleLysGluThrProGlnThrIleA
spThrLeuAsnIleGlnLysAsnLysAsnTyrGlyThrAsnAspLeuSerSerIleLeuGluGlyAsnAlaGlyIl
eAspAlaAlaTyrAspMetArgGlyGluSerIlePheLeuArgGlyPheGlnAlaAspAlaSerAspIleTyrArg
AspGlyValArgGluSerGlyGlnValArgArgSerThrAlaAsnIleGluArgValGluIleLeuLysGlyProS
erSerValLeuTyrGlyArgThrAsnGlyGlyGlyValIleAsnMetValSerLysTyrAlaAsnPheLysGlnSe
rArgAsnIleGlyThrValTyrGlySerTrpAlaAsnArgSerLeuAsnMetAspIleAsnGluValLeuAsnLys
AsnValAlaIleArgLeuThrGlyGluValGlyArgAlaAsnSerPheArgSerGlyIleAspSerLysAsnValM
etValSerProSerIleThrValLysLeuAspAsnGlyLeuLysTrpThrGlyGlnTyrThrTyrAspAsnValGl
uArgThrProAspArgSerProThrLysSerValTyrAspArgPheGlyLeuProTyrArgMetGlyPheAlaHis
ArgAsnAspPheValLysAspLysLeuGlnValTrpArgSerAspLeuGluTyrAlaPheAsnAspLysTrpArgA
laGlnTrpGlnLeuAlaHisArgThrAlaAlaGlnAspPheAspHisPheTyrAlaGlySerGluAsnGlyAsnLe
uIleLysArgAsnTyrAlaTrpGlnGlnThrAspAsnLysThrLeuSerSerAsnLeuThrLeuAsnGlyAspTyr
ThrIleGlyArgPheGluAsnHisLeuThrValGlyMetAspTyrSerArgGluHisArgAsnProThrLeuGlyP
heSerSerAlaPheSerAlaSerIleAsnProTyrAspArgAlaSerTrpProAlaSerGlyArgLeuGlnProIl
eLeuThrGlnAsnArgHisLysAlaAspSerTyrGlyIlePheValGlnAsnIlePheSerAlaThrProAspLeu
LysPheValLeuGlyGlyArgTyrAspLysTyrThrPheAsnSerGluAsnLysLeuThrGlySerSerArgGlnT
yrSerGlyHisSerPheSerProAsnIleGlyAlaValTrpAsnIleAsnProValHisThrLeuTyrAlaSerTy
rAsnLysGlyPheAlaProTyrGlyGlyArgGlyGlyTyrLeuSerIleAspThrLeuSerSerAlaValPheAsn
AlaAspProGluTyrThrArgGlnTyrGluThrGlyValLysSerSerTrpLeuAspAspArgLeuSerThrThrL
euSerAlaTyrGlnIleGluArgPheAsnIleArgTyrArgProAspProLysAsnAsnProTyrIleTyrAlaVa
1SerGlyLysHisArgSerArgGlyValGluLeuSerAlaIleGlyGlnIleIleProLysLysLeuTyrLeuArg
GlySerLeuGlyValMetGlnAlaLysValValGluAspLysGluAsnProAspArgValGlyIleHisLeuAsnA
snThrSerAsnValThrGlyAsnLeuPhePheArgTyrThrProThrGluAsnLeuTyrGlyGluIleGlyValTh
rGlyThrGlyLysArgTyrGlyTyrAspSerArgAsnLysGluValThrThrLeuProGlyPheAlaArgValAsp
AlaMetLeuGlyTrpAsnHisLysAsnValAsnValThrPheAlaAlaAlaAsnLeuPheAsnGlnLysTyrTrpA
rgSerAspSerMetProGlyAsnProArgGlyTyrThrAlaArgValAsnTyrArgPhe-703

TABLE 1-continued

Hydrophilic Regions - Hopp-Woods (SEQ. ID. NO. 24267)
1-MetLysIleSerPheHisLeuAlaLeuLeuProThrLeuIleIleAlaSerPheProValAlaAlaAlaAspTh
rGlnAspAsnGlyGluHisTyrThrAlaThrLeuProThrValSerValValGlyGlnSerAspThrSerValLeu
LysGlyTyrIleAsnTyrAspGluAlaAlaValThrArgAsnGlyGlnLeuIleLysGluThrProGlnThrIleA
spThrLeuAsnIleGlnLysAsnLysAsnTyrGlyThrAsnAspLeuSerSerIleLeuGluGlyAsnAlaGlyIl
eAspAlaAlaTyrAspMetArgGlyGluSerIlePheLeuArgGlyPheGlnAlaAspAlaSerAspIleTyrArg
AspGlyValArgGluSerGlyGlnValArgArgSerThrAlaAsnIleGluArgValGluIleLeuLysGlyProS
erSerValLeuTyrGlyArgThrAsnGlyGlyGlyValIleAsnMetValSerLysTyrAlaAsnPheLysGlnSe
rArgAsnIleGlyThrValTyrGlySerTrpAlaAsnArgSerLeuAsnMetAspIleAsnGluValLeuAsnLys
AsnValAlaIleArgLeuThrGlyGluValGlyArgAlaAsnSerPheArgSerGlyIleAspSerLysAsnValM
etValSerProSerIleThrValLysLeuAspAsnGlyLeuLysTrpThrGlyGlnTyrThrTyrAspAsnValGl
uArgThrProAspArgSerProThrLysSerValTyrAspArgPheGlyLeuProTyrArgMetGlyPheAlaHis
ArgAsnAspPheValLysAspLysLeuGlnValTrpArgSerAspLeuGluTyrAlaPheAsnAspLysTrpArgA
laGlnTrpGlnLeuAlaHisArgThrAlaAlaGlnAspPheAspHisPheTyrAlaGlySerGluAsnGlyAsnLe
uIleLysArgAsnTyrAlaTrpGlnGlnThrAspAsnLysThrLeuSerSerAsnLeuThrLeuAsnGlyAspTyr
ThrIleGlyArgPheGluAsnHisLeuThrValGlyMetAspTyrSerArgGluHisArgAsnProThrLeuGlyP
heSerSerAlaPheSerAlaSerIleAsnProTyrAspArgAlaSerTrpProAlaSerGlyArgLeuGlnProIl
eLeuThrGlnAsnArgHisLysAlaAspSerTyrGlyIlePheValGlnAsnIlePheSerAlaThrProAspLeu
LysPheValLeuGlyGlyArgTyrAspLysTyrThrPheAsnSerGluAsnLysLeuThrGlySerSerArgGlnT
yrSerGlyHisSerPheSerProAsnIleGlyAlaValTrpAsnIleAsnProValHisThrLeuTyrAlaSerTy
rAsnLysGlyPheAlaProTyrGlyGlyArgGlyGlyTyrLeuSerIleAspThrLeuSerSerAlaValPheAsn
AlaAspProGluTyrThrArgGlnTyrGluThrGlyValLysSerSerTrpLeuAspAspArgLeuSerThrThrL
euSerAlaTyrGlnIleGluArgPheAsnIleArgTyrArgProAspProLysAsnAsnProTyrIleTyrAlaVa
lSerGlyLysHisArgSerArgGlyValGluLeuSerAlaIleGlyGlnIleIleProLysLysLeuTyrLeuArg
GlySerLeuGlyValMetGlnAlaLysValValGluAspLysGluAsnProAspArgValGlyIleHisLeuAsnA
snThrSerAsnValThrGlyAsnLeuPhePheArgTyrThrProThrGluAsnLeuTyrGlyGluIleGlyValTh
rGlyThrGlyLysArgTyrGlyTyrAspSerArgAsnLysGluValThrThrLeuProGlyPheAlaArgValAsp
AlaMetLeuGlyTrpAsnHisLysAsnValAsnValThrPheAlaAlaAlaAsnLeuPheAsnGlnLysTyrTrpA
rgSerAspSerMetProGlyAsnProArgGlyTyrThrAlaArgValAsnTyrArgPhe-703
a762
AMPHI Regions - AMPHI
SEQ. ID. NO. 24268 1-MetLysTrpLeuLeuAsnMetIleMetArgProIleLysPheSerMetVa
lAsnThrLeuLeuPheIleValIleCysSerSerPhePheAspLeuLeuValGlnLeuCysThrIleLeuPheHisSerGlnLysIleTyrPheIleThrLeuP
heLeuLeuPheIlePheAsnPheValThrLysSerIleTyrMetAlaIleIleTyrProIleLeuTyrPhePheThrIleLysLysTyrTyrProTyrSerArg
LysValIleIleLeuLeuSerLeuAlaLeuSerIleTyrPheSerPheMetAspPheTyrPhePheSerIleTyrSerAspAsnLeuSerTyrGluThrGluPr
oLeuHisLeuTyrIleProIleIleIleAsnPhePheSerLeuLeuValSerAsnPheIleLeuSerPheIleAsnLys-147
Antigenic Index - Jameson-Wolf (SEQ. ID. NO. 24268)
1-MetLysTrpLeuLeuAsnMetIleMetArgProIleLysPheSerMetValAsnThrLeuLeuPheIleValIl
eCysSerSerPhePheAspLeuLeuValGlnLeuCysThrIleLeuPheHisSerGlnLysIleTyrPheIleThr
LeuPheLeuLeuPheIlePheAsnPheValThrLysSerIleTyrMetAlaIleIleTyrProIleLeuTyrPheP
heThrIleLysLysTyrTyrProTyrSerArgLysValIleIleLeuLeuSerLeuAlaLeuSerIleTyrPheSe
rPheMetAspPheTyrPhePheSerIleTyrSerAspAsnLeuSerTyrGluThrGluProLeuHisLeuTyrIle
ProIleIleIleAsnPhePheSerLeuLeuValSerAsnPheIleLeuSerPheIleAsnLys-147
Hydrophilic Regions - Hopp-Woods (SEQ. ID. NO. 24268)
1-MetLysTrpLeuLeuAsnMetIleMetArgProIleLysPheSerMetValAsnThrLeuLeuPheIleValIl
eCysSerSerPhePheAspLeuLeuValGlnLeuCysThrIleLeuPheHisSerGlnLysIleTyrPheIleThr
LeuPheLeuLeuPheIlePheAsnPheValThrLysSerIleTyrMetAlaIleIleTyrProIleLeuTyrPheP
heThrIleLysLysTyrTyrProTyrSerArgLysValIleIleLeuLeuSerLeuAlaLeuSerIleTyrPheSe
rPheMetAspPheTyrPhePheSerIleTyrSerAspAsnLeuSerTyrGluThrGluProLeuHisLeuTyrIle
ProIleIleIleAsnPhePheSerLeuLeuValSerAsnPheIleLeuSerPheIleAsnLys-147
a763
AMPHI Regions - AMPHI
SEQ. ID. NO. 24269 1-MetThrLeuLeuAsnLeuMetIleMetGlnAspTyrGlyIleSerValCy
sLeuThrLeuThrProTyrLeuGlnHisGluLeuPheSerAlaMetLysSerTyrPheSerLysTyrIleLeuProValSerLeuPheThrLeuProLeuSerL
euSerProSerValSerAlaPheThrLeuProGluAlaTrpArgAlaAlaGlnGlnHisSerAlaAspPheGlnAlaSerHisTyrGlnArgAspAlaValArg
AlaArgGlnGlnGlnAlaLysAlaAlaPheLeuProHisValSerAlaAsnAlaSerTyrGlnArgGlnProProSerIleSerSerThrArgGluThrGlnGl
yTrpSerValGlnValGlyGlnThrLeuPheAspAlaAlaLysPheAlaGlnTyrArgGlnSerArgPheAspThrGlnAlaAlaGluGlnArgPheAspAlaA
laArgGluGluLeuLeuLeuLysValAlaGluSerTyrPheAsnValLeuLeuSerArgAspThrValAlaAlaHisAlaAlaGluLysGluAlaTyrAlaGln
GlnValArgGlnAlaGlnAlaLeuPheAsnLysGlyAlaAlaThrAlaLeuAspIleHisGluAlaLysAlaGlyTyrAspAsnAlaLeuAlaGlnGluIleAl
aValLeuAlaGluLysGlnThrTyrGluAsnGlnLeuAsnAspTyrThrGlyLeuAspSerLysGlnIleGluAlaIleAspThrAlaAsnLeuLeuAlaArgT
yrLeuProLysLeuGluArgTyrSerLeuAspGluTrpGlnArgIleAlaLeuSerAsnAsnHisGluTyrArgMetGlnGlnLeuAlaLeuGlnSerSerGly
GlnAlaLeuArgAlaAlaGlnAsnSerArgTyrProThrValSerAlaHisValGlyTyrGlnAsnAsnLeuTyrThrSerSerAlaGlnAsnAsnAspTyrHi
sTyrArgGlyLysGlyMetSerValGlyValGlnLeuAsnLeuProLeuTyrThrGlyGlyGluLeuSerGlyLysIleHisGluAlaGluAlaGlnTyrGlyA
laAlaGluAlaGlnLeuThrAlaThrGluArgHisIleLysLeuAlaValArgGlnAlaTyrThrGluSerGlyAlaAlaArgTyrGlnIleMetAlaGlnGlu
ArgValLeuGluSerSerArgLeuLysLeuLysSerThrGluThrGlyGlnGlnTyrGlyIleArgAsnArgLeuGluValIleArgAlaArgGlnGluValAl
aGlnAlaGluGlnLysLeuAlaGlnAlaArgTyrLysPheMetLeuAlaTyrLeuArgLeuValLysGluSerGlyLeuGlyLeuGluThrValPheAlaGlu-
467
Antigenic Index - Jameson-Wolf (SEQ. ID. NO. 24269)
1-MetThrLeuLeuAsnLeuMetIleMetGlnAspTyrGlyIleSerValCysLeuThrLeuThrProTyrLeuGl
nHisGluLeuPheSerAlaMetLysSerTyrPheSerLysTyrIleLeuProValSerLeuPheThrLeuProLeu
SerLeuSerProSerValSerAlaPheThrLeuProGluAlaTrpArgAlaAlaGlnGlnHisSerAlaAspPheG
lnAlaSerHisTyrGlnArgAspAlaValArgAlaArgGlnGlnGlnAlaLysAlaAlaPheLeuProHisValSe
rAlaAsnAlaSerTyrGlnArgGlnProProSerIleSerSerThrArgGluThrGlnGlyTrpSerValGlnVal
GlyGlnThrLeuPheAspAlaAlaLysPheAlaGlnTyrArgGlnSerArgPheAspThrGlnAlaAlaGluGlnA
rgPheAspAlaAlaArgGluGluLeuLeuLeuLysValAlaGluSerTyrPheAsnValLeuLeuSerArgAspTh
rValAlaAlaHisAlaAlaGluLysGluAlaTyrAlaGlnGlnValArgGlnAlaGlnAlaLeuPheAsnLysGly
AlaAlaThrAlaLeuAspIleHisGluAlaLysAlaGlyTyrAspAsnAlaLeuAlaGlnGluIleAlaValLeuA
laGluLysGlnThrTyrGluAsnGlnLeuAsnAspTyrThrGlyLeuAspSerLysGlnIleGluAlaIleAspTh
rAlaAsnLeuLeuAlaArgTyrLeuProLysLeuGluArgTyrSerLeuAspGluTrpGlnArgIleAlaLeuSer
AsnAsnHisGluTyrArgMetGlnGlnLeuAlaLeuGlnSerSerGlyGlnAlaLeuArgAlaAlaGlnAsnSerA TABLE 1-continued rgTyrProThrValSerAlaHisValGlyTyrGlnAsnAsnLeuTyrThrSerSerAlaGlnAsnAsnAspTyrHisTyrArgGlyLysGlyMetSerValGlyValGlnLeuAsnLeuProLeuTyrThrGlyGlyGluLeuSerGlyLysIleHisGluAlaGluAlaGlnTyrGlyAlaAlaGluAlaGlnLeuThrAlaThrGluArgHisIleLysLeuAlaValArgGlnAlaTyrThrGluSerGlyAlaAlaArgTyrGlnIleMetAlaGlnGluArgValLeuGluSerSerArgLeuLysLeuLysSerThrGluThrGlyGlnGlnTyrGlyIleArgAsnArgLeuGluValIleArgAlaArgGlnGluValAlaGlnAlaGluGlnLysLeuAlaGlnAlaArgTyrLysPheMetLeuAlaTyrLeuArgLeuValLysGluSerGlyLeuGlyLeuGluThrValPheAlaGlu-467

Hydrophilic Regions - Hopp-Woods (SEQ. ID. NO. 24269)

1-MetThrLeuLeuAsnLeuMetIleMetGlnAspTyrGlyIleSerValCysLeuThrLeuThrProTyrLeuGlnHisGluLeuPheSerAlaMetLysSerTyrPheSerLysTyrIleLeuProValSerLeuPheThrLeuProLeuSerLeuSerProSerValSerAlaPheThrLeuProGluAlaTrpArgAlaAlaGlnGlnHisSerAlaAspPheGlnAlaSerHisTyrGlnArgAspAlaValArgAlaArgGlnGlnGlnAlaLysAlaAlaPheLeuProHisValSerAlaAsnAlaSerTyrGlnArgGlnProProSerIleSerSerThrArgGluThrGlnGlyTrpSerValGlnValGlyGlnThrLeuPheAspAlaAlaLysPheAlaGlnTyrArgGlnSerArgPheAspThrGlnAlaAlaGluGlnArgPheAspAlaAlaArgGluGluLeuLeuLeuLysValAlaGluSerTyrPheAsnValLeuLeuSerArgAspThrValAlaAlaHisAlaAlaGluLysGluAlaTyrAlaGlnGlnValArgGlnAlaGlnAlaLeuPheAsnLysGlyAlaAlaThrAlaLeuAspIleHisGluAlaLysAlaGlyTyrAspAsnAlaLeuAlaGlnGluIleAlaValLeuAlaGluLysGlnThrTyrGluAsnGlnLeuAsnAspTyrThrGlyLeuAspSerLysGlnIleGluAlaIleAspThrAlaAsnLeuLeuAlaArgTyrLeuProLysLeuGluArgTyrSerLeuAspGluTrpGlnArgIleAlaLeuSerAsnAsnHisGluTyrArgMetGlnGlnLeuAlaLeuGlnSerSerGlyGlnAlaLeuArgAlaAlaGlnAsnSerArgTyrProThrValSerAlaHisValGlyTyrGlnAsnAsnLeuTyrThrSerSerAlaGlnAsnAsnAspTyrHisTyrArgGlyLysGlyMetSerValGlyValGlnLeuAsnLeuProLeuTyrThrGlyGlyGluLeuSerGlyLysIleHisGluAlaGluAlaGlnTyrGlyAlaAlaGluAlaGlnLeuThrAlaThrGluArgHisIleLysLeuAlaValArgGlnAlaTyrThrGluSerGlyAlaAlaArgTyrGlnIleMetAlaGlnGluArgValLeuGluSerSerArgLeuLysLeuLysSerThrGluThrGlyGlnGlnTyrGlyIleArgAsnArgLeuGluValIleArgAlaArgGlnGluValAlaGlnAlaGluGlnLysLeuAlaGlnAlaArgTyrLysPheMetLeuAlaTyrLeuArgLeuValLysGluSerGlyLeuGlyLeuGluThrValPheAlaGlu-467 a764

AMPHI Regions - AMPHI

SEQ. ID. NO. 24270  1-MetPhePheSerAlaLeuLysSerPheLeuSerArgTyrIleThrValTrpArgAsnValTrpAlaValArgAspGlnLeuGluProProLysArgThrAlaGluGluGlnAlaPheLeuProAlaHisLeuGluLeuThrAspThrProValSerAlaAlaProLysTrpAlaAlaArgPheIleMetAlaPheAlaLeuLeuAlaLeuLeuTrpSerTrpPheGlyLysIleAspIleValAlaAlaAlaSerGlyLysThrValSerGlyGlyArgSerLysThrIleGlnProLeuGlyThrValValValLysAlaValHisValArgAspGlyGlnHisValLysGlnGlyGluThrLeuAlaGluLeuGluAlaValGlyThrAspSerAspValValGlnSerGluGlnAlaLeuGlnAlaAlaGlnLeuSerLysLeuArgTyrArgLeuAlaValLeuAlaAlaLeuGluSerArgThrValProHisIleAspMetAlaGlnAlaArgSerLeuGlyLeuSerAspAlaAspValGlnSerAlaGlnValLeuAlaGlnHisGlnTyrGlnAlaTrpAlaAlaGlnAspAlaGlnLeuGlnSerAlaLeuArgGlyHisGlnAlaGluLeuGlnSerAlaLysAlaGlnGluGlnLysLeuValSerValGlyAlaIleGluGlnGlnLysThrAlaAspTyrArgArgLeuArgAlaAspAsnPheIleSerGluHisAlaPheLeuGlnGlnSerLysSerValSerAsnTrpAsnAspLeuGluSerThrArgGlyGlnMetArgGlnIleGlnAlaAlaIleAlaGlnAlaGluGlnAsnArgValLeuAsnThrGlnAsnLeuLysArgAspThrLeuAspAlaLeuArgGlnAlaAsnGluGlnIleAspGlnTyrArgGlyGlnThrAspLysAlaLysGlnArgGlnGlnLeuMetThrIleGlnSerProAlaAspGlyThrValGlnGluLeuAlaThrTyrThrValGlyGlyValValGlnAlaAlaGlnLysMetMetValValAlaProAspAspAspLysMetAspValGluValLeuValLeuAsnLysAspIleGlyPheValGluGlnGlyGlnAspAlaValValLysIleGluSerPheProTyrThrArgTyrGlyTyrLeuThrGlyLysValLysSerValSerHisAspAlaValSerHisGluGlnLeuGlyLeuValTyrThrAlaValValSerLeuAspLysHisThrLeuAsnIleAspGlyLys-435

Antigenic Index - Jameson-Wolf (SEQ. ID. NO. 24270)

1-MetPhePheSerAlaLeuLysSerPheLeuSerArgTyrIleThrValTrpArgAsnValTrpAlaValArgAspGlnLeuGluProProLysArgThrAlaGluGluGlnAlaPheLeuProAlaHisLeuGluLeuThrAspThrProValSerAlaAlaProLysTrpAlaAlaArgPheIleMetAlaPheAlaLeuLeuAlaLeuLeuTrpSerTrpPheGlyLysIleAspIleValAlaAlaAlaSerGlyLysThrValSerGlyGlyArgSerLysThrIleGlnProLeuGluThrValValValLysAlaValHisValArgAspGlyGlnHisValLysGlnGlyGluThrLeuAlaGluLeuGluAlaValGlyThrAspSerAspValValGlnSerGluGlnAlaLeuGlnAlaAlaGlnLeuSerLysLeuArgTyrArgLeuAlaValLeuAlaAlaLeuGluSerArgThrValProHisIleAspMetAlaGlnAlaArgSerLeuGlyLeuSerAspAlaAspValGlnSerAlaGlnValLeuAlaGlnHisGlnTyrGlnAlaTrpAlaAlaGlnAspAlaGlnLeuGlnSerAlaLeuArgGlyHisGlnAlaGluLeuGlnSerAlaLysAlaGlnGluGlnLysLeuValSerValGlyAlaIleGluGlnGlnLysThrAlaAspTyrArgArgLeuArgAlaAlaAspAsnPheIleSerGluHisAlaPheLeuGlnGlnSerLysSerValSerAsnTrpAsnAspLeuGluSerThrArgGlyGlnMetArgGlnIleGlnAlaAlaIleAlaGlnAlaGluGlnAsnArgValLeuAsnThrGlnAsnLeuLysArgAspThrLeuAspAlaLeuArgGlnAlaAsnGluGlnIleAspGlnTyrArgGlyGlnThrAspLysAlaLysGlnArgGlnGlnLeuMetThrIleGlnSerProAlaAspGlyThrValGlnGluLeuAlaThrTyrThrValGlyGlyValValGlnAlaAlaGlnLysMetMetValValAlaProAspAspAspLysMetAspValGluValLeuValLeuAsnLysAspIleGlyPheValGluGlnGlyGlnAspAlaValValLysIleGluSerPheProTyrThrArgTyrGlyTyrLeuThrGlyLysValLysSerValSerHisAspAlaValSerHisGluGlnLeuGlyLeuValTyrThrAlaValValSerLeuAspLysHisThrLeuAsnIleAspGlyLys-435

Hydrophilic Regions - Hopp-Woods (SEQ. ID. NO. 24270)

1-MetPhePheSerAlaLeuLysSerPheLeuSerArgTyrIleThrValTrpArgAsnValTrpAlaValArgAspGlnLeuGluProProLysArgThrAlaGluGluGlnAlaPheLeuProAlaHisLeuGluLeuThrAspThrProValSerAlaAlaProLysTrpAlaAlaArgPheIleMetAlaPheAlaLeuLeuAlaLeuLeuTrpSerTrpPheGlyLysIleAspIleValAlaAlaAlaSerGlyLysThrValSerGlyGlyArgSerLysThrIleGlnProLeuGluThrValValValLysAlaValHisValArgAspGlyGlnHisValLysGlnGlyGluThrLeuAlaGluLeuGluAlaValGlyThrAspSerAspValValGlnSerGluGlnAlaLeuGlnAlaAlaGlnLeuSerLysLeuArgTyrArgLeuAlaValLeuAlaAlaLeuGluSerArgThrValProHisIleAspMetAlaGlnAlaArgSerLeuGlyLeuSerAspAlaAspValGlnSerAlaGlnValLeuAlaGlnHisGlnTyrGlnAlaTrpAlaAlaGlnAspAlaGlnLeuGlnSerAlaLeuArgGlyHisGlnAlaGluLeuGlnSerAlaLysAlaGlnGluGlnLysLeuValSerValGlyAlaIleGluGlnGlnLysThrAlaAspTyrArgArgLeuArgAlaAlaAspAsnPheIleSerGluHisAlaPheLeuGlnGlnSerLysSerValSerAsnTrpAsnAspLeuGluSerThrArgGlyGlnMetArgGlnIleGlnAlaAlaIleAlaGlnAlaGluGlnAsnArgValLeuAsnThrGlnAsnLeuLysArgAspThrLeuAspAlaLeuArgGlnAlaAsnGluGlnIleAspGlnTyrArgGlyGlnThrAspLysAlaLysGlnArgGlnGlnLeuMetThrIleGlnSerProAlaAspGlyThrValGlnGluLeuAlaThrTyrThrValGlyGlyValValGlnAlaAlaGlnLysMetMetValValAlaProAspAspAspLysMetAspValGluValLeuValLeuAsnLysAspIleGlyPheValGluGlnGlyGlnAspAlaValValLysIleGluSerPheProTyrThrArgTyrGlyTyrLeuThrGlyLysValLysSerVa

TABLE 1-continued

1SerHisAspAlaValSerHisGluGlnLeuGlyLeuValTyrThrAlaValValSerLeuAspLysHisThrLeu
AsnIleAspGlyLys-435
a765
AMPHI Regions - AMPHI
SEQ. ID. NO. 24271    36-SerAlaIleSerSerPheCys-42
SEQ. ID. NO. 24272    45-LysIleIleHisThrTyr-50
SEQ. ID. NO. 24273    59-ValIleGlyIleIleAsnGly-65
SEQ. ID. NO. 24274    105-ArgPheLeuAsnArgGly-110
SEQ. ID. NO. 24275    147-PheGlyLeuCysTyrPro-152
Antigenic Index - Jameson-Wolf
SEQ. ID. NO. 24276    10-GlyAsnPheLysLysIleAlaThr-17
SEQ. ID. NO. 24277    19-GlnGlyLeuAspArgLysTyr-25
SEQ. ID. NO. 24278    76-ValLysAsnLysGlnLysPheLeu-83
SEQ. ID. NO. 24279    106-PheLeuAsnArgGlyMetLys-112
SEQ. ID. NO. 24280    132-LeuAsnGluGluGlyGlyTrpMet-139
SEQ. ID. NO. 24281    160-LeuSerArgAspTyrLysHisIle-167
Hydrophilic Regions - Hopp-Woods
SEQ. ID. NO. 24282    11-AsnPheLysLysIleAlaThr-17
SEQ. ID. NO. 24283    19-GlnGlyLeuAspArgLys-24
SEQ. ID. NO. 24284    76-ValLysAsnLysGlnLysPheLeu-83
SEQ. ID. NO. 24285    133-AsnGluGluGlyGly-137
SEQ. ID. NO. 24286    162-ArgAspTyrLysHis-166
a767
AMPHI Regions - AMPHI
SEQ. ID. NO. 24287    42-LysIleGluValLeuGluPhePheGlyTyrPheCysVal-54
SEQ. ID. NO. 24288    89-GlyLeuAlaArgMetAlaAlaAlaValLys-98
SEQ. ID. NO. 24289    140-LysLysLeuMetArgAlaTyrAspSerProAlaAla-151
SEQ. ID. NO. 24290    156-SerLysMetGlnGlnLeuThrGluGlnTyrArg-166
SEQ. ID. NO. 24291    187-PheAspGlyGlyValHisThrIleLysGluLeuValAla-199
Antigenic Index - Jameson-Wolf
SEQ. ID. NO. 24292    23-ThrGluGlyGluAspTyrLeuVal-30
SEQ. ID. NO. 24293    33-LysProIleProGlnLysGlnSerGlyLysIleGluVal-45
SEQ. ID. NO. 24294    70-LeuProSerAspAlaTyrLeuArg-77
SEQ. ID. NO. 24295    99-LeuSerGlyLeuLysTyrGlnAla-106
SEQ. ID. NO. 24296    115-TyrGluGlnLysIleArgLeuGluAsnArgSerValAlaGlu-128
SEQ. ID. NO. 24297    130-TrpAlaLeuSerGlnLysGlyPheAspGlyLysLysLeuMetArgAlaTyrAspSerProAla-150
SEQ. ID. NO. 24298    156-SerLysMetGlnGlnLeuThrGluGlnTyrArgIleAspSerThrProThr-172
SEQ. ID. NO. 24299    175-ValGlyGlyLysTyrArgVal-181
SEQ. ID. NO. 24300    183-PheAsnAsnGlyPheAspGlyGly-190
SEQ. ID. NO. 24301    197-LeuValAlaLysValArgGluGluArgLysArgGlnThrProAlaValGlnLys-214
Hydrophilic Regions - Hopp-Woods
SEQ. ID. NO. 24302    23-ThrGluGlyGluAsp-27
SEQ. ID. NO. 24303    33-LysProIleProGlnLysGlnSerGlyLysIleGluVal-45
SEQ. ID. NO. 24304    115-TyrGluGlnLysIleArgLeuGluAsnArgSerValAlaGlu-128
SEQ. ID. NO. 24305    135-LysGlyPheAspGlyLysLysLeuMetArgAlaTyrAsp-147
SEQ. ID. NO. 24306    156-SerLysMetGlnGlnLeu-161
SEQ. ID. NO. 24307    165-TyrArgIleAspSer-169
SEQ. ID. NO. 24308    197-LeuValAlaLysValArgGluGluArgLysArgGlnThrProAlaValGlnLys-214
a768
AMPHI Regions - AMPHI
SEQ. ID. NO. 24309    1-MetAsnIleLysHisLeuIleThrAlaAlaLeuIleAlaSerAlaAlaPheAlaAlaGlnAlaAlaProGlnLysProValSerAlaAlaGln
                        ThrAlaGlnHisSerAlaValTrpIleAspValArgSerGluGlnGluPheSerGluGlyHisLeuHisAsnAlaValAsnIleProValAspGlnIleValArgArg
                        IleHisGluAlaAlaProAspLysAspThrProValAsnLeuTyrCysArgSerGlyArgArgAlaGluAlaAlaLeuGlnGluLeuLysLysAlaGlyTyrThrAsn
                        ValAlaAsnHisGlyGlyTyrGluAspLeuLeuLysLysGlyMetLys
Antigenic Index - Jameson-Wolf (SEQ. ID. NO. 24309)
1-MetAsnIleLysHisLeuIleThrAlaAlaLeuIleAlaSerAlaAlaPheAlaAlaGlnAlaAlaProGlnLy
sProValSerAlaAlaGlnThrAlaGlnHisSerAlaValTrpIleAspValArgSerGluGlnGluPheSerGlu
GlyHisLeuHisAsnAlaValAsnIleProValAspGlnIleValArgArgIleHisGluAlaAlaProAspLysA
spThrProValAsnLeuTyrCysArgSerGlyArgArgAlaGluAlaAlaLeuGlnGluLeuLysLysAlaGlyTy
rThrAsnValAlaAsnHisGlyGlyTyrGluAspLeuLeuLysLysGlyMetLys
Hydrophilic Regions - Hopp-Woods (SEQ. ID. NO. 24309)
1-MetAsnIleLysHisLeuIleThrAlaAlaLeuIleAlaSerAlaAlaPheAlaAlaGlnAlaAlaProGlnLy
sProValSerAlaAlaGlnThrAlaGlnHisSerAlaValTrpIleAspValArgSerGluGlnGluPheSerGlu
GlyHisLeuHisAsnAlaValAsnIleProValAspGlnIleValArgArgIleHisGluAlaAlaProAspLysA
spThrProValAsnLeuTyrCysArgSerGlyArgArgAlaGluAlaAlaLeuGlnGluLeuLysLysAlaGlyTy
rThrAsnValAlaAsnHisGlyGlyTyrGluAspLeuLeuLysLysGlyMetLys-119
a769
AMPHI Regions - AMPHI
SEQ. ID. NO. 24310    1-LeuIleMetValIlePheTyrPheCysGlyLysThrPheMetProAlaAr
                        gAsnArgTrpMetLeuLeuLeuProLeuLeuAlaSerAlaAlaTyrAlaGluGluThrProArgGluProAspLeuArgSerArgProGluPheArgLeuHisG
                        luAlaGluValLysProIleAspArgGluLysValProGlyGlnValArgGluLysGlyLysValLeuGlnIleAspGlyGluThrLeuLeuLysAsnProGlu
                        LeuLeuSerArgAlaMetTyrSerAlaValValSerAsnAsnIleAlaGlyIleArgValIleLeuProIleTyrLeuGlnGlnAlaGlnGlnAspLysMetLe
                        uAlaLeuTyrAlaGlnGlyIleLeuAlaGlnAlaAspGlyArgValLysGluAlaIleSerHisTyrArgGluLeuIleValAlaGlnProAspAlaProAlaV
                        alArgMetArgLeuAlaAlaAlaLeuPheGluAsnArgGlnAsnGluAlaAlaAlaAspGlnPheAspArgLeuLysAlaGluAsnLeuProProGlnLeuMet
                        GluGlnValGluLeuTyrArgLysAlaLeuArgGluArgAspAlaTrpLysValAsnGlyGlyPheSerValThrArgGluHisAsnIleAsnGlnAlaProLy
                        sArgGlnGlnTyrGlyLysTrpThrPheProLysGlnValAspGlyThrAlaValAsnTyrArgLeuGlyAlaGluLysLysTrpSerLeuLysAsnGlyTrpT
                        yrThrThrAlaGlyGlyAspValSerGlyArgValTyrProGlyAsnLysLysPheAsnAspMetThrAlaGlyValSerGlyGlyIleGlyPheAlaAspArg
                        ArgLysAspAlaGlyLeuAlaValPheHisGluArgArgThrTyrGlyAsnAspAlaTyrSerTyrThrAsnGlyAlaArgLeuTyrPheAsnArgTrpGlnTh
                        rProLysTrpGlnThrLeuSerSerAlaGluTrpGlyArgLeuLysAsnThrArgArgAlaArgSerAspAsnThrHisLeuGlnIleSerAsnSerLeuValPh
                        eTyrArgAsnAlaArgGlnTyrTrpMetGlyGlyLeuAspPheTyrArgGluArgAsnProAlaAspArgGlyAspAsnPheAsnArgTyrGlyLeuArgPhe TABLE 1-continued AlaTrpGlyGlnGluTrpGlyGlySerGlyLeuSerSerLeuLeuArgLeuGlyAlaAlaLysArgHisTyrGluLysProGlyPhePheSerGlyPheLysGl
yGluArgArgArgAspLysGluLeuAsnThrSerLeuSerLeuTrpHisArgAlaLeuHisPheLysGlyIleThrProArgLeuThrLeuSerHisArgGluT
hrArgSerAsnAspValPheAsnGluTyrGluLysAsnArgAlaPheValGluPheAsnLysThrPhe-490

Antigenic Index - Jameson-Wolf (SEQ. ID. NO. 24310)
1-LeuIleMetValIlePheTyrPheCysGlyLysThrPheMetProAlaArgAsnArgTrpMetLeuLeuLeuPr
oLeuLeuAlaSerAlaAlaTyrAlaGluGluThrProArgGluProAspLeuArgSerArgProGluPheArgLeu
HisGluAlaGluValLysProIleAspArgGluLysValProGlyGlnValArgGluLysGlyLysValLeuGlnI
leAspGlyGluThrLeuLeuLysAsnProGluLeuLeuSerArgAlaMetTyrSerAlaValValSerAsnAsnI1
eAlaGlyIleArgValIleLeuProIleTyrLeuGlnGlnAlaGlnGlnAspLysMetLeuAlaLeuTyrAlaGln
GlyIleLeuAlaGlnAlaAspGlyArgValLysGluAlaIleSerHisTyrArgGluLeuIleValAlaGlnProA
spAlaProAlaValArgMetArgLeuAlaAlaAlaLeuPheGluAsnArgGlnAsnGluAlaAlaAlaAspGlnPh
eAspArgLeuLysAlaGluAsnLeuProProGlnLeuMetGluGlnValGluLeuTyrArgLysAlaLeuArgGlu
ArgAspAlaTrpLysValAsnGlyGlyPheSerValThrArgGluHisAsnIleAsnGlnAlaProLysArgGlnG
lnTyrGlyLysTrpThrPheProLysGlnValAspGlyThrAlaValAsnTyrArgLeuGlyAlaGluLysLysTr
pSerLeuLysAsnGlyTrpTyrThrThrAlaGlyGlyAspValSerGlyArgValTyrProGlyAsnLysLysPhe
AsnAspMetThrAlaGlyValSerGlyGlyIleGlyPheAlaAspArgArgLysAspAlaGlyLeuAlaValPheH
isGluArgArgThrTyrGlyAsnAspAlaTyrSerTyrThrAsnGlyAlaArgLeuTyrPheAsnArgTrpGlnTh
rProLysTrpGlnThrLeuSerSerAlaGluTrpGlyArgLeuLysAsnThrArgArgAlaArgSerAspAsnThr
HisLeuGlnIleSerAsnSerLeuValPheTyrArgAsnAlaArgGlnTyrTrpMetGlyGlyLeuAspPheTyrA
rgGluArgAsnProAlaAspArgGlyAspAsnPheAsnArgTyrGlyLeuArgPheAlaTrpGlyGlnGluTrpGl
yGlySerGlyLeuSerSerLeuLeuArgLeuGlyAlaAlaLysArgHisTyrGluLysProGlyPhePheSerGly
PheLysGlyGluArgArgArgAspLysGluLeuAsnThrSerLeuSerLeuTrpHisArgAlaLeuHisPheLysG
lyIleThrProArgLeuThrLeuSerHisArgGluThrArgSerAsnAspValPheAsnGluTyrGluLysAsnAr
gAlaPheValGluPheAsnLysThrPhe-490

Hydrophilic Regions - Hopp-Woods (SEQ. ID. NO. 24310)
1-LeuIleMetValIlePheTyrPheCysGlyLysThrPheMetProAlaArgAsnArgTrpMetLeuLeuLeuPr
oLeuLeuAlaSerAlaAlaTyrAlaGluGluThrProArgGluProAspLeuArgSerArgProGluPheArgLeu
HisGluAlaGluValLysProIleAspArgGluLysValProGlyGlnValArgGluLysGlyLysValLeuGlnI
leAspGlyGluThrLeuLeuLysAsnProGluLeuLeuSerArgAlaMetTyrSerAlaValValSerAsnAsnI1
eAlaGlyIleArgValIleLeuProIleTyrLeuGlnGlnAlaGlnGlnAspLysMetLeuAlaLeuTyrAlaGln
GlyIleLeuAlaGlnAlaAspGlyArgValLysGluAlaIleSerHisTyrArgGluLeuIleValAlaGlnProA
spAlaProAlaValArgMetArgLeuAlaAlaAlaLeuPheGluAsnArgGlnAsnGluAlaAlaAlaAspGlnPh
eAspArgLeuLysAlaGluAsnLeuProProGlnLeuMetGluGlnValGluLeuTyrArgLysAlaLeuArgGlu
ArgAspAlaTrpLysValAsnGlyGlyPheSerValThrArgGluHisAsnIleAsnGlnAlaProLysArgGlnG
lnTyrGlyLysTrpThrPheProLysGlnValAspGlyThrAlaValAsnTyrArgLeuGlyAlaGluLysLysTr
pSerLeuLysAsnGlyTrpTyrThrThrAlaGlyGlyAspValSerGlyArgValTyrProGlyAsnLysLysPhe
AsnAspMetThrAlaGlyValSerGlyGlyIleGlyPheAlaAspArgArgLysAspAlaGlyLeuAlaValPheH
isGluArgArgThrTyrGlyAsnAspAlaTyrSerTyrThrAsnGlyAlaArgLeuTyrPheAsnArgTrpGlnTh
rProLysTrpGlnThrLeuSerSerAlaGluTrpGlyArgLeuLysAsnThrArgArgAlaArgSerAspAsnThr
HisLeuGlnIleSerAsnSerLeuValPheTyrArgAsnAlaArgGlnTyrTrpMetGlyGlyLeuAspPheTyrA
rgGluArgAsnProAlaAspArgGlyAspAsnPheAsnArgTyrGlyLeuArgPheAlaTrpGlyGlnGluTrpGl
yGlySerGlyLeuSerSerLeuLeuArgLeuGlyAlaAlaLysArgHisTyrGluLysProGlyPhePheSerGly
PheLysGlyGluArgArgArgAspLysGluLeuAsnThrSerLeuSerLeuTrpHisArgAlaLeuHisPheLysG
lyIleThrProArgLeuThrLeuSerHisArgGluThrArgSerAsnAspValPheAsnGluTyrGluLysAsnAr
gAlaPheValGluPheAsnLysThrPhe-490
a770

AMPHI Regions - AMPHI
SEQ. ID. NO. 24311    1-MetAsnArgLeuLeuLeuLeuSerAlaAlaValLeuLeuThrAlaCysGl
ySerGlyGluThrAspLysIleGlyArgAlaSerThrValPheAsnIleLeuGlyLysAsnAspArgIleGluValGluGlyPheAspAspProAspValGlnG
lyValAlaCysTyrIleSerTyrAlaLysLysGlyGlyLeuLysGluMetValAsnLeuGluGluAspAlaSerArgAlaSerValSerCysValGlnThrAla
SerSerIleSerPheAspGluThrAlaValArgLysProLysGluValPheLysHisGlyAlaSerPheAlaPheLysSerArgGlnIleValArgTyrTyrAs
pProLysArgLysThrPheAlaTyrLeuValTyrSerAspLysIleIleGlnGlySerProLysAsnSerLeuSerAlaValSerCysPheGlyGlyGlyIleP
roGlnThrAspGlyValGlnAlaAspThrSerGlyAsnLeuLeuAlaGlyAlaCysMetIleSerAsnProIleGluAsnProAspLysArg-186

Antigenic Index - Jameson-Wolf (SEQ. ID. NO. 24311)
1-MetAsnArgLeuLeuLeuLeuSerAlaAlaValLeuLeuThrAlaCysGlySerGlyGluThrAspLysIleGl
yArgAlaSerThrValPheAsnIleLeuGlyLysAsnAspArgIleGluValGluGlyPheAspAspProAspVal
GlnGlyValAlaCysTyrIleSerTyrAlaLysLysGlyGlyLeuLysGluMetValAsnLeuGluGluAspAlaS
erAspAlaSerValSerCysValGlnThrAlaSerSerIleSerPheAspGluThrAlaValArgLysProLysGl
uValPheLysHisGlyAlaSerPheAlaPheLysSerArgGlnIleValArgTyrTyrAspProLysArgLysThr
PheAlaTyrLeuValTyrSerAspLysIleIleGlnGlySerProLysAsnSerLeuSerAlaValSerCysPheG
lyGlyGlyIleProGlnThrAspGlyValGlnAlaAspThrSerGlyAsnLeuLeuAlaGlyAlaCysMetIleSe
rAsnProIleGluAsnProAspLysArg-186

Hydrophilic Regions - Hopp-Woods (SEQ. ID. NO. 24311)
1-MetAsnArgLeuLeuLeuLeuSerAlaAlaValLeuLeuThrAlaCysGlySerGlyGluThrAspLysIleGl
yArgAlaSerThrValPheAsnIleLeuGlyLysAsnAspArgIleGluValGluGlyPheAspAspProAspVal
GlnGlyValAlaCysTyrIleSerTyrAlaLysLysGlyGlyLeuLysGluMetValAsnLeuGluGluAspAlaS
erAspAlaSerValSerCysValGlnThrAlaSerSerIleSerPheAspGluThrAlaValArgLysProLysGl
uValPheLysHisGlyAlaSerPheAlaPheLysSerArgGlnIleValArgTyrTyrAspProLysArgLysThr
PheAlaTyrLeuValTyrSerAspLysIleIleGlnGlySerProLysAsnSerLeuSerAlaValSerCysPheG
lyGlyGlyIleProGlnThrAspGlyValGlnAlaAspThrSerGlyAsnLeuLeuAlaGlyAlaCysMetIleSe
rAsnProIleGluAsnProAspLysArg-186
a771

AMPHI Regions - AMPHI
SEQ. ID. NO. 24312    1-MetAspLeuLeuSerValPheHisLysTyrArgLeuLysTyrAlaValAl
aValLeuThrIleLeuLeuLeuAlaAlaIleGlyLeuHisAlaSerValTyrArgIlePheThrProGluAsnIleArgSerArgLeuGlnGlnSerIleAlaH
isThrHisArgArgIleSerPheAspAlaAspIleGlnArgArgLeuLeuProArgProThrValIleLeuLysAsnLeuThrIleThrGluProGlyGlyAsp
ArgThrAlaValSerValGlnGluThrLysIleGlyLeuSerTrpLysAsnLeuTrpSerAspGlnIleGlnIleGluLysTrpValValSerSerAlaGluLe
uAlaLeuThrArgAspGlyLysGlyValTrpAsnIleGlnAspLeuIleAspSerGlnLysArgGlnAlaSerValAsnArgIleIleValGluAsnSerThrV
alArgLeuAsnPheLeuGlnGluGlnLeuIleLeuLysGluIleAsnLeuAsnLeuGlnSerProAspSerSerGlyGlnProPheGluSerSerGlyIleLeu
ValTrpGlyLysLeuSerValProTrpLysSerArgGlyLeuPheLeuSerArgAspGlyIleGlyThrProLysIleSerProPheHisPheGluAlaSerThrSe TABLE 1-continued rLeuAspGlyHisGlyIleThrIleSerThrThrGlySerProSerValArgPheAsnAlaGlyGlyAlaAspAlaAlaGlyLeuGlyLeuArgAlaAspThrS
erPheArgAsnLeuHisLeuThrAlaGlnIleProThrLeuAlaLeuArgAsnAsnSerIleLysIleGluThrValAsnGlyAlaPheThrAlaGlyGlyGlu
TyrAlaGlnTrpAspGlySerPheLysLeuAspLysAlaAsnLeuHisSerGlyIleAlaAsnIleGlyAsnAlaGluIleSerGlySerPheLysThrProAr
gHisGlnThrAsnPheSerLeuAsnSerProLeuValTrpThrGluAsnLysGlyLeuAspAlaProArgLeuTyrValSerThrLeuGlnAspThrValAsnA
rgLeuProGlnProArgPheIleSerArgLeuAspGlySerLeuSerValProAsnLeuGlnAsnTrpAsnAlaGluLeuAsnGlyThrPheAspArgGlnThr
ValAlaAlaLysPheArgTyrThrHisGluAspAlaProHisLeuGluAlaAlaValAlaLeuGlnLysLeuAsnLeuThrProTyrLeuAspAspValArgGl
nGlnAsnGlyLysIlePheProAspThrLeuAlaLysLeuSerGlyAspIleGluAlaHisLeuLysIleGlyLysValGlnLeuProGlyLeuGlnLeuAspA
spMetGluThrTyrLeuHisAlaAspLysGlyHisIleAlaLeuSerArgPheLysSerGlyLeuTyrGlyGlyHisThrGluGlyGlyIleSerIleAlaAsn
ThrArgProAlaThrTyrArgLeuGlnGlnAsnAlaSerAsnIleGlnIleGlnProLeuLeuGlnAspLeuPheGlyPheHisSerPheSerGlyAsnGlyAs
pAlaValIleAspLeuThrAlaGlyGlyGluThrArgLysGluLeuIleArgSerLeuGlnGlySerLeuSerLeuAsnIleSerAsnGlyAlaTrpHisGlyI
leAspMetAspAsnIleLeuLysAsnGlyIleSerGlyLysThrAlaAspAsnAlaAlaProSerThrProPheHisArgPheThrLeuAsnSerGluIleSer
AspGlyIleSerArgHisIleAspThrGluLeuPheSerAspSerLeuTyrValThrSerAsnGlyTyrThrAsnLeuAspThrGlnGluLeuSerGluAspVa
lLeuIleArgAsnAlaValHisProLysAsnLysProIleProLeuLysIleThrGlyThrValAspLysProSerIleThrValAspTyrGlyArgLeuThrG
lyGlyIleAsnSerArgLysGluLysGlnLysIleLeuGluAspThrLeuLeuGluGlnTrpGlnTrpLeuLysProLysGluPro-704

Antigenic Index - Jameson-Wolf (SEQ. ID. NO. 24312)
1-MetAspLeuLeuSerValPheHisLysTyrArgLeuLysTyrAlaValAlaValLeuThrIleLeuLeuLeuAl
aAlaIleGlyLeuHisAlaSerValTyrArgIlePheThrProGluAsnIleArgSerArgLeuGlnGlnSerIle
AlaHisThrHisArgLysIleSerPheAspAlaAspIleGlnArgArgLeuLeuProArgProThrValIleLeuL
ysAsnLeuThrIleThrGluProGlyGlyAspArgThrAlaValSerValGlnGluThrLysIleGlyLeuSerTr
pLysAsnLeuTrpSerAspGlnIleGlnIleGluLysTrpValValSerSerAlaGluLeuAlaLeuThrArgAsp
GlyLysGlyValTrpAsnIleGlnAspLeuIleAspSerGlnLysArgGlnAlaSerValAsnArgIleIleValG
luAsnSerThrValArgLeuAsnPheLeuGlnGluGlnLeuIleLeuLysGluIleAsnLeuAsnLeuGlnSerPr
oAspSerSerGlyGlnProPheGluSerSerGlyIleLeuValTrpGlyLysLeuSerValProTrpLysSerArg
GlyLeuPheLeuSerAspGlyIleGlyThrProLysIleSerProPheHisPheGluAlaSerThrSerLeuAspG
lyHisGlyIleThrIleSerThrThrThrGlySerProSerValArgPheAsnAlaGlyGlyAlaAspAlaAlaGlyLe
uGlyLeuArgAlaAspThrSerPheArgAsnLeuHisLeuThrAlaGlnIleProThrLeuAlaLeuArgAsnAsn
SerIleLysIleGluThrValAsnGlyAlaPheThrAlaGlyGlyGluTyrAlaGlnTrpAspGlySerPheLysL
euAspLysAlaAsnLeuHisSerGlyIleAlaAsnIleGlyAsnAlaGluIleSerGlySerPheLysThrProAr
gHisGlnThrAsnPheSerLeuAsnSerProLeuValTrpThrGluAsnLysGlyLeuAspAlaProArgLeuTyr
ValSerThrLeuGlnAspThrValAsnArgLeuProGlnProArgPheIleSerArgLeuAspGlySerLeuSerV
alProAsnLeuGlnAsnTrpAsnAlaGluLeuAsnGlyThrPheAspArgGlnThrValAlaAlaLysPheArgTy
rThrHisGluAspAlaProHisLeuGluAlaAlaValAlaLeuGlnLysLeuAsnLeuThrProTyrLeuAspAsp
ValArgGlnGlnAsnGlyLysIlePheProAspThrLeuAlaLysLeuSerGlyAspIleGluAlaHisLeuLysI
leGlyLysValGlnLeuProGlyLeuGlnLeuAspAspMetGluThrTyrLeuHisAlaAspLysGlyHisIleAl
aLeuSerArgPheLysSerGlyLeuTyrGlyGlyHisThrGluGlyGlyIleSerIleAlaAsnThrArgProAla
ThrTyrArgLeuGlnGlnAsnAlaSerAsnIleGlnIleGlnProLeuLeuGlnAspLeuPheGlyPheHisSerP
heSerGlyAsnGlyAspAlaValIleAspLeuThrAlaGlyGlyGluThrArgLysGluLeuIleArgSerLeuGl
nGlySerLeuSerLeuAsnIleSerAsnGlyAlaTrpHisGlyIleAspMetAspAsnIleLeuLysAsnGlyIle
SerGlyLysThrAlaAspAsnAlaAlaProSerThrProPheHisArgPheThrLeuAsnSerGluIleSerAspG
lyIleSerArgHisIleAspThrGluLeuPheSerAspSerLeuTyrValThrSerAsnGlyTyrThrAsnLeuAs
pThrGlnGluLeuSerGluAspValLeuIleArgAsnAlaValHisProLysAsnLysProIleProLeuLysIle
ThrGlyThrValAspLysProSerIleThrValAspTyrGlyArgLeuThrGlyGlyIleAsnSerArgLysGluL
ysGlnLysIleLeuGluAspThrLeuLeuGluGlnTrpGlnTrpLeuLysProLysGluPro-704

Hydrophilic Regions - Hopp-Woods (SEQ. ID. NO. 24312)
1-MetAspLeuLeuSerValPheHisLysTyrArgLeuLysTyrAlaValAlaValLeuThrIleLeuLeuLeuAl
aAlaIleGlyLeuHisAlaSerValTyrArgIlePheThrProGluAsnIleArgSerArgLeuGlnGlnSerIle
AlaHisThrHisArgLysIleSerPheAspAlaAspIleGlnArgArgLeuLeuProArgProThrValIleLeuL
ysAsnLeuThrIleThrGluProGlyGlyAspArgThrAlaValSerValGlnGluThrLysIleGlyLeuSerTr
pLysAsnLeuTrpSerAspGlnIleGlnIleGluLysTrpValValSerSerAlaGluLeuAlaLeuThrArgAsp
GlyLysGlyValTrpAsnIleGlnAspLeuIleAspSerGlnLysArgGlnAlaSerValAsnArgIleIleValG
luAsnSerThrValArgLeuAsnPheLeuGlnGluGlnLeuIleLeuLysGluIleAsnLeuAsnLeuGlnSerPr
oAspSerSerGlyGlnProPheGluSerSerGlyIleLeuValTrpGlyLysLeuSerValProTrpLysSerArg
GlyLeuPheLeuSerAspGlyIleGlyThrProLysIleSerProPheHisPheGluAlaSerThrSerLeuAspG
lyHisGlyIleThrIleSerThrThrThrGlySerProSerValArgPheAsnAlaGlyGlyAlaAspAlaAlaGlyLe
uGlyLeuArgAlaAspThrSerPheArgAsnLeuHisLeuThrAlaGlnIleProThrLeuAlaLeuArgAsnAsn
SerIleLysIleGluThrValAsnGlyAlaPheThrAlaGlyGlyGluTyrAlaGlnTrpAspGlySerPheLysL
euAspLysAlaAsnLeuHisSerGlyIleAlaAsnIleGlyAsnAlaGluIleSerGlySerPheLysThrProAr
gHisGlnThrAsnPheSerLeuAsnSerProLeuValTrpThrGluAsnLysGlyLeuAspAlaProArgLeuTyr
ValSerThrLeuGlnAspThrValAsnArgLeuProGlnProArgPheIleSerArgLeuAspGlySerLeuSerV
alProAsnLeuGlnAsnTrpAsnAlaGluLeuAsnGlyThrPheAspArgGlnThrValAlaAlaLysPheArgTy
rThrHisGluAspAlaProHisLeuGluAlaAlaValAlaLeuGlnLysLeuAsnLeuThrProTyrLeuAspAsp
ValArgGlnGlnAsnGlyLysIlePheProAspThrLeuAlaLysLeuSerGlyAspIleGluAlaHisLeuLysI
leGlyLysValGlnLeuProGlyLeuGlnLeuAspAspMetGluThrTyrLeuHisAlaAspLysGlyHisIleAl
aLeuSerArgPheLysSerGlyLeuTyrGlyGlyHisThrGluGlyGlyIleSerIleAlaAsnThrArgProAla
ThrTyrArgLeuGlnGlnAsnAlaSerAsnIleGlnIleGlnProLeuLeuGlnAspLeuPheGlyPheHisSerP
heSerGlyAsnGlyAspAlaValIleAspLeuThrAlaGlyGlyGluThrArgLysGluLeuIleArgSerLeuGl
nGlySerLeuSerLeuAsnIleSerAsnGlyAlaTrpHisGlyIleAspMetAspAsnIleLeuLysAsnGlyIle
SerGlyLysThrAlaAspAsnAlaAlaProSerThrProPheHisArgPheThrLeuAsnSerGluIleSerAspG
lyIleSerArgHisIleAspThrGluLeuPheSerAspSerLeuTyrValThrSerAsnGlyTyrThrAsnLeuAs
pThrGlnGluLeuSerGluAspValLeuIleArgAsnAlaValHisProLysAsnLysProIleProLeuLysIle
ThrGlyThrValAspLysProSerIleThrValAspTyrGlyArgLeuThrGlyGlyIleAsnSerArgLysGluL
ysGlnLysIleLeuGluAspThrLeuLeuGluGlnTrpGlnTrpLeuLysProLysGluPro-704
a772

AMPHI Regions - AMPHI
SEQ. ID. NO. 24313    1-MetPheGlyAlaValLeuArgIleAspAlaAspCysLeuGlnIleIleVa
lAlaCysLysLeuPheGlnIleValAlaTyrGlyPheAlaAlaLeuValGluGlyGluPheHisGluPheGlyGluMetLeuGluIleValArgLeuAlaAspT
hrValPheHisArgAsnHisAlaAspAspGlyArgIleHisPheArgArgGlyValGluArgPheGlyArgHisValAsnGlnHisPheHisIleGluGluIle
LeuGlnHisHisAlaGlnAlaAlaValValValAlaPheArgArgGlyAsnHisThrIleAspHisPhePheLeuGlnHisLysValHisIleAspAspIleVa
lArgHisLeuArgGlnLeuGluGlnLysArgArgGlyAsnValValGlyGlnValAlaAspAspPheLeuPheAlaCysAspAlaValGluIleLysLeuGlnT
yrIleAlaPheValAsnHisGlnPheIleArgLysArgGlnArgPheGlnThrAlaTyrAspValAlaValAspPheAspAsnValGlnAlaValGlnLeuPhe TABLE 1-continued ArgGlnArgPheGlyAsnArgArgGlnThrArgThrAspPheAsnHisAspIleIleArgLeuArgAlaHisGlyValAspAsnIleAlaAspAsnProArgVa
lLeuGlnLysIleLeuProGluThrLeuAlaGlyPheValPhePheHisArgValSerPheSerValGluThrProProPheArgAlaValGluSerAspSerI
leTrpGluGlyArgAsnSerPheGlnIleArgThrAlaHisArgAlaValLeuTyrValSerSerCysValLeuLysHisLysCysValTyrSerIleArgLeu
MetSerAlaLeu-298
Antigenic Index - Jameson-Wolf (SEQ. ID. NO. 24313)
1-MetPheGlyAlaValLeuArgIleAspAlaAspCysLeuGlnIleIleValAlaCysLysLeuPheGlnIleVa
lAlaTyrGlyPheAlaAlaLeuValGluGlyGluPheHisGluPheGlyGluMetLeuGluIleValArgLeuAla
AspThrValPheHisArgAsnHisAlaAspAspGlyArgIleHisPheArgArgGlyValGluArgPheGlyArgH
isValAsnGlnHisPheHisIleGluGluIleLeuGlnHisHisAlaGlnAlaAlaValValValAlaPheArgAr
gGlyAsnHisThrIleAspHisPhePheLeuGlnHisLysValHisIleAspAspIleValArgHisLeuArgGln
LeuGluGlnLysArgArgGlyAsnValValGlyGlnValAlaAspAspPheLeuPheAlaCysAspAlaValGluI
leLysLeuGlnTyrIleAlaPheValAsnHisGlnPheIleArgLysArgGlnArgPheGlnThrAlaTyrAspVa
lAlaValAspPheAspAsnValGlnAlaValGlnLeuPheArgGlnArgPheGlyAsnArgArgGlnThrArgThr
AspPheAsnHisAspIleIleArgLeuArgAlaHisGlyValAspAsnIleAlaAspAsnProArgValLeuGlnL
ysIleLeuProGluThrLeuAlaGlyPheValPhePheHisArgValSerPheSerValGluThrProProPheAr
gAlaValGluSerAspSerIleTrpGluGlyArgAsnSerPheGlnIleArgThrAlaHisArgAlaValLeuTyr
ValSerSerCysValLeuLysHisLysCysValTyrSerIleArgLeuMetSerAlaLeu-298
Hydrophilic Regions - Hopp-Woods (SEQ. ID. NO. 24313)
1-MetPheGlyAlaValLeuArgIleAspAlaAspCysLeuGlnIleIleValAlaCysLysLeuPheGlnIleVa
lAlaTyrGlyPheAlaAlaLeuValGluGlyGluPheHisGluPheGlyGluMetLeuGluIleValArgLeuAla
AspThrValPheHisArgAsnHisAlaAspAspGlyArgIleHisPheArgArgGlyValGluArgPheGlyArgH
isValAsnGlnHisPheHisIleGluGluIleLeuGlnHisHisAlaGlnAlaAlaValValValAlaPheArgAr
gGlyAsnHisThrIleAspHisPhePheLeuGlnHisLysValHisIleAspAspIleValArgHisLeuArgGln
LeuGluGlnLysArgArgGlyAsnValValGlyGlnValAlaAspAspPheLeuPheAlaCysAspAlaValGluI
leLysLeuGlnTyrIleAlaPheValAsnHisGlnPheIleArgLysArgGlnArgPheGlnThrAlaTyrAspVa
lAlaValAspPheAspAsnValGlnAlaValGlnLeuPheArgGlnArgPheGlyAsnArgArgGlnThrArgThr
AspPheAsnHisAspIleIleArgLeuArgAlaHisGlyValAspAsnIleAlaAspAsnProArgValLeuGlnL
ysIleLeuProGluThrLeuAlaGlyPheValPhePheHisArgValSerPheSerValGluThrProProPheAr
gAlaValGluSerAspSerIleTrpGluGlyArgAsnSerPheGlnIleArgThrAlaHisArgAlaValLeuTyr
ValSerSerCysValLeuLysHisLysCysValTyrSerIleArgLeuMetSerAlaLeu-298
a774
AMPHI Regions - AMPHI
SEQ. ID. NO. 24314    1-MetLysThrLysLeuProLeuPheIleIleTrpLeuSerValSerAlaAl
aCysSerSerProValSerArgAsnIleGlnAspMetArgLeuGluProGlnAlaGluAlaGlySerSerAspAlaIleProTyrProValProThrLeuGlnA
spArgLeuAspTyrLeuGluGlyThrLeuValArgLeuSerAsnGluValGluThrLeuAsnGlyLysValLysAlaLeuGluHisAlaLysThrHisProSer
SerArgAlaTyrValGlnLysLeuAspAspArgLysLeuLysGluHisTyrLeuAsnThrGluGlyGlySerAlaSerAlaHisThrValGluThrAlaGlnAs
nLeuTyrAsnGlnAlaLeuLysHisTyrLysSerGlyArgPheSerAlaAlaAlaSerLeuLeuLysGlyAlaAspGlyGlyAspGlyGlySerIleAlaGlnA
rgSerMetTyrLeuLeuLeuGlnSerArgAlaArgMetGlyAsnCysGluSerValIleGluIleGlyGlyArgTyrAlaAsnArgPheLysAspSerProThr
AlaProGluAlaMetPheLysIleGlyGluCysGlnTyrArgLeuGlnLysAspIleAlaArgAlaThrTrpArgSerLeuIleGlnThrTyrProGlySe
rProAlaAlaLysArgAlaAlaAlaAlaValArgLysArg-238
Antigenic Index - Jameson-Wolf (SEQ. ID. NO. 24314)
1-MetLysThrLysLeuProLeuPheIleIleTrpLeuSerValSerAlaAlaCysSerSerProValSerArgAs
nIleGlnAspMetArgLeuGluProGlnAlaGluAlaGlySerSerAspAlaIleProTyrProValProThrLeu
GlnAspArgLeuAspTyrLeuGluGlyThrLeuValArgLeuSerAsnGluValGluThrLeuAsnGlyLysValL
ysAlaLeuGluHisAlaLysThrHisProSerSerArgAlaTyrValGlnLysLeuAspAspArgLysLeuLysGl
uHisTyrLeuAsnThrGluGlyGlySerAlaSerAlaHisThrValGluThrAlaGlnAsnLeuTyrAsnGlnAla
LeuLysHisTyrLysSerGlyArgPheSerAlaAlaAlaSerLeuLeuLysGlyAlaAspGlyGlyAspGlyGlyS
erIleAlaGlnArgSerMetTyrLeuLeuLeuGlnSerArgAlaArgMetGlyAsnCysGluSerValIleGluIl
eGlyGlyArgTyrAlaAsnArgPheLysAspSerProThrAlaProGluAlaMetPheLysIleGlyGluCysGln
TyrArgLeuGlnLysAspIleAlaArgAlaThrTrpArgSerLeuIleGlnThrTyrProGlySerProAlaA
laLysArgAlaAlaAlaAlaValArgLysArg-238
Hydrophilic Regions - Hopp-Woods (SEQ. ID. NO. 24314)
1-MetLysThrLysLeuProLeuPheIleIleTrpLeuSerValSerAlaAlaCysSerSerProValSerArgAs
nIleGlnAspMetArgLeuGluProGlnAlaGluAlaGlySerSerAspAlaIleProTyrProValProThrLeu
GlnAspArgLeuAspTyrLeuGluGlyThrLeuValArgLeuSerAsnGluValGluThrLeuAsnGlyLysValL
ysAlaLeuGluHisAlaLysThrHisProSerSerArgAlaTyrValGlnLysLeuAspAspArgLysLeuLysGl
uHisTyrLeuAsnThrGluGlyGlySerAlaSerAlaHisThrValGluThrAlaGlnAsnLeuTyrAsnGlnAla
LeuLysHisTyrLysSerGlyArgPheSerAlaAlaAlaSerLeuLeuLysGlyAlaAspGlyGlyAspGlyGlyS
erIleAlaGlnArgSerMetTyrLeuLeuLeuGlnSerArgAlaArgMetGlyAsnCysGluSerValIleGluIl
eGlyGlyArgTyrAlaAsnArgPheLysAspSerProThrAlaProGluAlaMetPheLysIleGlyGluCysGln
TyrArgLeuGlnLysAspIleAlaArgAlaThrTrpArgSerLeuIleGlnThrTyrProGlySerProAlaA
laLysArgAlaAlaAlaAlaValArgLysArg-238
a790
AMPHI Regions - AMPHI
SEQ. ID. NO. 24315    10-GluAlaAlaAlaGluVal-15
SEQ. ID. NO. 24316    44-GlyAsnGlnThrCysSerArgTyrSerAsn-53
SEQ. ID. NO. 24317    89-LysGlnAlaValThr-93
SEQ. ID. NO. 24318    103-ThrGlnAlaTyrAsnGluMetThrLysSerVal-113
SEQ. ID. NO. 24319    166-PheAlaArgThrGlyLysLeu-172
SEQ. ID. NO. 24320    174-GlySerPheAspLeuPheAlaSerVal-182
SEQ. ID. NO. 24321    253-ProSerGluAlaLeuAsp-258
SEQ. ID. NO. 24322    290-ThrAlaProAspValTrpThrVal-297
SEQ. ID. NO. 24323    320-PheLeuArgPheTrpGlnAlaThrArgGlyIle-330
Antigenic Index - Jameson-Wolf
SEQ. ID. NO. 24324    1-MetAlaArgArgSerLysThrPheGluGluAlaAlaAlaGluValGluGluArgPheGlyHisArgGlyIleLys-25
SEQ. ID. NO. 24325    30-GluGlyThrAlaLysProCysVal-37
SEQ. ID. NO. 24326    39-AsnCysProLysHisGlyAsnGlnThrCysSerArgTyrSer-52
SEQ. ID. NO. 24327    57-GlySerSerTrpGlyCysProSerCysGlyAsnGluGlnAlaAla-71
SEQ. ID. NO. 24328    77-ThrLeuArgLysAsnHisIle-83
SEQ. ID. NO. 24329    95-MetThrLysGlnGluArgIleThr-102

TABLE 1-continued

| | |
|---|---|
| SEQ. ID. NO. 24330 | 123-AspValGlnGlyAspThrThrIle-130 |
| SEQ. ID. NO. 24331 | 134-HisThrHisThrHisAsnHisSerAspAlaAspGlyLysAlaLeuSer-149 |
| SEQ. ID. NO. 24332 | 152-LeuThrProArgProLeuLeuSerAspArgGlnAla-163 |
| SEQ. ID. NO. 24333 | 167-AlaArgThrGlyLysLeuThrGly-174 |
| SEQ. ID. NO. 24334 | 194-MetProAspThrSerMet-199 |
| SEQ. ID. NO. 24335 | 201-ProValIleGluLysGlyAsp-207 |
| SEQ. ID. NO. 24336 | 213-ProArgMetArgProAlaAspGluAspIleVal-223 |
| SEQ. ID. NO. 24337 | 227-LeuSerAspLysArgLeuVal-233 |
| SEQ. ID. NO. 24338 | 248-TyrGlnThrGlyArgProSerGluAlaLeuAspLeuProGluGly-262 |
| SEQ. ID. NO. 24339 | 270-LeuGluSerLysAsnGlyLeuCysProProHisArgGlnGluGlyVal-285 |
| SEQ. ID. NO. 24340 | 301-SerAlaSerLysThrSerCysThrArgProThrAlaAlaArgLysSerAla-317 |
| SEQ. ID. NO. 24341 | 326-AlaThrArgGlyIleProLysThrArgSerTrpArgAsnProAsnAsnAlaCys-343 |
| Hydrophilic Regions - Hopp-Woods | |
| SEQ. ID. NO. 24342 | 1-MetAlaArgSerLysThrPheGluGluAlaAlaAlaGluValGluGluArgPheGlyHisArgGlyIleLys-25 |
| SEQ. ID. NO. 24343 | 65-CysGlyAsnGluGlnAlaAla-71 |
| SEQ. ID. NO. 24344 | 77-ThrLeuArgLysAsnHisIle-83 |
| SEQ. ID. NO. 24345 | 96-ThrLysGlnGluArgIleThr-102 |
| SEQ. ID. NO. 24346 | 139-AsnHisSerAspAlaAspGlyLysAlaLeuSer-149 |
| SEQ. ID. NO. 24347 | 157-LeuLeuSerAspArgGlnAla-163 |
| SEQ. ID. NO. 24348 | 168-ArgThrGlyLysLeu-172 |
| SEQ. ID. NO. 24349 | 202-ValIleGluLysGlyAsp-207 |
| SEQ. ID. NO. 24350 | 213-ProArgMetArgProAlaAspGluAspIleVal-223 |
| SEQ. ID. NO. 24351 | 227-LeuSerAspLysArgLeuVal-233 |
| SEQ. ID. NO. 24352 | 251-GlyArgProSerGluAlaLeuAspLeuProGlu-261 |
| SEQ. ID. NO. 24353 | 270-LeuGluSerLysAsnGlyLeu-276 |
| SEQ. ID. NO. 24354 | 280-HisArgGlnGluGlyVal-285 |
| SEQ. ID. NO. 24355 | 301-SerAlaSerLysThrSerCysThrArgProThrAlaAlaArgLysSerAla-317 |
| SEQ. ID. NO. 24356 | 328-ArgGlyIleProLysThrArgSerTrpArgAsn-338 |
| a900-2 | |
| AMPHI Regions - AMPHI | |
| SEQ. ID. NO. 24357 | 9-ValValAlaPheAlaArgPhe-15 |
| SEQ. ID. NO. 24358 | 36-ValGlyLysHisPheArgLysPheCysArgPheArg-47 |
| SEQ. ID. NO. 24359 | 62-ValGlyLeuLeuArgLeuAlaArgLeuPheHisIleGlyAspAspPheValAspArgPheLeuGlyPhePhe-85 |
| SEQ. ID. NO. 24360 | 120-GlnCysGluGluPheProGluAlaValValGluAla-131 |
| SEQ. ID. NO. 24361 | 198-HisGlnThrLeuGlyGlyAspAlaGly-206 |
| SEQ. ID. NO. 24362 | 210-ValGlnPheHisHisPheGly-216 |
| SEQ. ID. NO. 24363 | 233-GlyLysProSerGlyGlyAsnGlyLeuGlyGlyLeuValAsnHisLeuArgLeuValAla-252 |
| SEQ. ID. NO. 24364 | 268-IleArgValLeuArgAlaAspGlyGly-277 |
| SEQ. ID. NO. 24365 | 279-AspSerThrAspValValAlaGlnMet-287 |
| Antigenic Index - Jameson-Wolf | |
| SEQ. ID. NO. 24366 | 1-LeuArgArgValGlyGlyGln-7 |
| SEQ. ID. NO. 24367 | 20-ValAspPheArgArgGlnLys-26 |
| SEQ. ID. NO. 24368 | 38-LysHisPheArgLysPheCysArgPheArgArgArgGlyGluSer-52 |
| SEQ. ID. NO. 24369 | 56-PheLysGlnArgAla-60 |
| SEQ. ID. NO. 24370 | 74-GlyAspAspPheValAspArg-80 |
| SEQ. ID. NO. 24371 | 88-PheProLysArgAsnGlyValAla-95 |
| SEQ. ID. NO. 24372 | 105-GlnThrAsnGlnGlu-109 |
| SEQ. ID. NO. 24373 | 118-PheGlyGlnCysGluGluPhePro-125 |
| SEQ. ID. NO. 24374 | 155-GluHisGluAsnValGlySerHisGluAspArgValAla-167 |
| SEQ. ID. NO. 24375 | 201-LeuGlyGlyAspAlaGlyGlnAsnPro-209 |
| SEQ. ID. NO. 24376 | 229-ValGluSerAlaGlyLysProSerGlyGlyAsnGly-240 |
| SEQ. ID. NO. 24377 | 252-AlaPheAspAspThrValValIleGlyGluGluGluGluGlyPheGly-267 |
| SEQ. ID. NO. 24378 | 270-ValLeuArgArgAlaAspGlyGlyAlaAspSerThrAsp-282 |
| SEQ. ID. NO. 24379 | 285-AlaGlnMetArgAspAlaGlyGly-292 |
| SEQ. ID. NO. 24380 | 311-MetProSerGluArgGluLysAspAlaProIle-321 |
| SEQ. ID. NO. 24381 | 323-ProAspLeuProProThrSerSerArgGlnGlnThr-334 |
| Hydrophilic Regions - Hopp-Woods | |
| SEQ. ID. NO. 24382 | 1-LeuArgArgValGly-5 |
| SEQ. ID. NO. 24383 | 20-ValAspPheArgArgGlnLys-26 |
| SEQ. ID. NO. 24384 | 38-LysHisPheArgLysPheCysArgPheArgArgArgGlyGluSer-52 |
| SEQ. ID. NO. 24385 | 89-ProLysArgAsnGly-93 |
| SEQ. ID. NO. 24386 | 120-GlnCysGluGluPhePro-125 |
| SEQ. ID. NO. 24387 | 155-GluHisGluAsnValGlySerHisGluAspArgValAla-167 |
| SEQ. ID. NO. 24388 | 201-LeuGlyGlyAspAlaGlyGln-207 |
| SEQ. ID. NO. 24389 | 231-SerAlaGlyLysProSerGly-237 |
| SEQ. ID. NO. 24390 | 257-ValValIleGlyGluGluGluGluGlyPheGly-267 |
| SEQ. ID. NO. 24391 | 270-ValLeuArgArgAlaAspGlyGlyAlaAspSerThrAsp-282 |
| SEQ. ID. NO. 24392 | 285-AlaGlnMetArgAspAlaGly-291 |
| SEQ. ID. NO. 24393 | 311-MetProSerGluArgGluLysAspAlaProIle-321 |
| SEQ. ID. NO. 24394 | 326-ProProThrSerSerArgGlnGln-333 |
| a901 | |
| AMPHI Regions - AMPHI | |
| SEQ. ID. NO. 24395 | 20-GlyLeuPheThrValLeuGly-26 |
| SEQ. ID. NO. 24396 | 55-ValSerLeuThrGluIlePheSerLysSer-64 |
| SEQ. ID. NO. 24397 | 66-GluAlaPheAlaGluIleTyrAsp-73 |
| SEQ. ID. NO. 24398 | 84-AlaPheLeuAlaGlyMetGlyGlyIleAlaLeuIle-95 |
| SEQ. ID. NO. 24399 | 97-ArgLeuValProAsnProHisGluThrLeuAsp-107 |
| SEQ. ID. NO. 24400 | 124-ValGlyMetMetAlaAlaPhe-130 |
| SEQ. ID. NO. 24401 | 136-AsnPheProGluGlyLeuAlaThrPhePheAlaThrLeuGlu-149 |
| SEQ. ID. NO. 24402 | 164-HisAsnIleProGluGlyIleSer-171 |

TABLE 1-continued

SEQ. ID. NO. 24403  190-CysLeuLeuSerGlyLeuAlaGluProLeuGlyAlaAla-202
SEQ. ID. NO. 24404  217-PheGlySerValPheGlyValIleAlaGlyValMet-228
SEQ. ID. NO. 24405  243-TyrSerAspGlyHisGlu-248
Antigenic Index - Jameson-Wolf
SEQ. ID. NO. 24406  1-MetProAspPheSerMet-6
SEQ. ID. NO. 24407  33-SerLysThrProAsnProArgVal-40
SEQ. ID. NO. 24408  61-PheSerLysSerSerGluAlaPhe-68
SEQ. ID. NO. 24409  71-IleTyrAspLysAspHisAla-77
SEQ. ID. NO. 24410  98-LeuValProAsnProHisGluThrLeuAspAlaGlnAspProSerPheGlnGluSerLysArgArgHisIleAla-122
SEQ. ID. NO. 24411  136-AsnPheProGluGly-140
SEQ. ID. NO. 24412  179-AlaThrArgSerArgLysLysThr-186
SEQ. ID. NO. 24413  193-SerGlyLeuAlaGluProLeuGly-200
SEQ. ID. NO. 24414  235-GluLeuLeuProAlaAlaLysArgTyrSerAspGlyHisGluThr-249
Hydrophilic Regions - Hopp-Woods
SEQ. ID. NO. 24415  61-PheSerLysSerSerGluAlaPhe-68
SEQ. ID. NO. 24416  71-IleTyrAspLysAspHisAla-77
SEQ. ID. NO. 24417  102-ProHisGluThrLeuAspAlaGlnAspProSerPheGlnGluSerLys
ArgArgHisIleAla-122
SEQ. ID. NO. 24418  180-ThrArgSerArgLysLysThr-186
SEQ. ID. NO. 24419  235-GluLeuLeuProAlaAlaLysArgTyrSerAspGlyHisGlu-248
a902
AMPHI Regions - AMPHI
SEQ. ID. NO. 24420  1-LeuHisPheGlnArgIleIleLysCysSerGluGlyIleTrpAlaValGlyAlaArgProThrValGlyPhePheGlyLysSerPheLysIleThrCysLys
HisValValLeuArgArgArgThrValGlnAlaValAspPheThrThrCysLeuPheAlaValGlyHisPheValAspValProAlaTyrValPheAlaCysAs
pAlaHisThrGlyGlyValAlaValLysArgValHisGlySerAspValValGlnAsnSerGlyGlyThrPheCysGlnThrGlnGlyArgArgAsnThrValP
heGlyValMetPheGlnIleAlaGluGluProArgSerAlaLeuArgAlaAlaProTyrHisAsnAlaValCysGlyGlyLeuPheGluAspGlyLeuGlyPhe
LeuArgArgGlyAsnValAlaValAspProAspArgAspValGlnThrAlaPheGlyPheGlyAsnGlnValValSerArgPheAlaPheValHisLeuArgAl
aArgAlaSerValAspGlyLysGlyGlyAsnAlaAlaIlePheGlyAspPheGlyAspAspGlyGlnValLeuMetValValValProThrGlnThrGlyPheG
luGlyAsnGlyTyrAlaArgArgPheAspHisArgLeuGlnAsnGlyGlyAsnGlnArgLeuValLeuHisGlnArgAlaThrGlyLeuAspIleAlaAspPhe
PheSerGlyThrAlaHisValAspValAspLysLeuArgProLysAlaAspValValThrArgGlyIleArgHisLeuLeuArgIleAlaSerGlyAsnLeuHi
sGlyAsnAsnAlaAlaPheIleGlyLysIleAlaAlaValGlnGlyPheSerSerIleSerGluArgArgValAlaGlyGlnHisPheAlaHisArgProThrC
ysAlaLysIleSerAlaLysSerAlaGluArgPheValGlyAsnAlaArgHisArgArgLysCysAspGlyValValAspLysIleAlaAlaAspValHisAsn
GlySerAlaPheGlnLysSerThrProLeuTyrIlePhe-359
Antigenic Index - Jameson-Wolf (SEQ. ID. NO. 24420)
1-LeuHisPheGlnArgIleIleLysCysSerGluGlyIleTrpAlaValGlyAlaArgProThrValGlyPhePh
eGlyLysSerPheLysIleThrCysLysHisValValLeuArgArgArgThrValGlnAlaValAspPheThrThr
CysLeuPheAlaValGlyHisPheValAspValProAlaTyrValPheAlaCysAspAlaHisThrGlyGlyValA
laValLysArgValHisGlySerAspValValGlnAsnSerGlyGlyThrPheCysGlnThrGlnGlyArgArgAs
nThrValPheGlyValMetPheGlnIleAlaGluGluProArgSerAlaLeuArgAlaAlaProTyrHisAsnAla
ValCysGlyGlyLeuPheGluAspGlyLeuGlyPheLeuArgArgGlyAsnValAlaValAspProAspArgAspV
alGlnThrAlaPheGlyPheGlyAsnGlnValValSerArgPheAlaPheValHisLeuArgAlaArgAlaSerVa
lAspGlyLysGlyGlyAsnAlaAlaIlePheGlyAspPheGlyAspAspGlyGlnValLeuMetValValValPro
ThrGlnThrGlyPheGluGlyAsnGlyTyrAlaArgArgPheAspHisArgLeuGlnAsnGlyGlyAsnGlnArgL
euValLeuHisGlnArgAlaThrGlyLeuAspIleAlaAspPhePheSerGlyThrAlaHisValAspValAspLy
sLeuArgProLysAlaAspValValThrArgGlyIleArgHisLeuLeuArgIleAlaSerGlyAsnLeuHisGly
AsnAsnAlaAlaPheIleGlyLysIleAlaAlaValGlnGlyPheSerSerIleSerGluArgArgValAlaGlyG
lnHisPheAlaHisArgProThrCysAlaLysIleSerAlaLysSerAlaGluArgPheValGlyAsnAlaArgHi
sArgArgLysCysAspGlyValValAspLysIleAlaAlaAspValHisAsnGlySerAlaPheGlnLysSerThr
ProLeuTyrIlePhe-359
Hydrophilic Regions - Hopp-Woods (SEQ. ID. NO. 24420)
1-LeuHisPheGlnArgIleIleLysCysSerGluGlyIleTrpAlaValGlyAlaArgProThrValGlyPhePh
eGlyLysSerPheLysIleThrCysLysHisValValLeuArgArgArgThrValGlnAlaValAspPheThrThr
CysLeuPheAlaValGlyHisPheValAspValProAlaTyrValPheAlaCysAspAlaHisThrGlyGlyValA
laValLysArgValHisGlySerAspValValGlnAsnSerGlyGlyThrPheCysGlnThrGlnGlyArgArgAs
nThrValPheGlyValMetPheGlnIleAlaGluGluProArgSerAlaLeuArgAlaAlaProTyrHisAsnAla
ValCysGlyGlyLeuPheGluAspGlyLeuGlyPheLeuArgArgGlyAsnValAlaValAspProAspArgAspV
alGlnThrAlaPheGlyPheGlyAsnGlnValValSerArgPheAlaPheValHisLeuArgAlaArgAlaSerVa
lAspGlyLysGlyGlyAsnAlaAlaIlePheGlyAspPheGlyAspAspGlyGlnValLeuMetValValValPro
ThrGlnThrGlyPheGluGlyAsnGlyTyrAlaArgArgPheAspHisArgLeuGlnAsnGlyGlyAsnGlnArgL
euValLeuHisGlnArgAlaThrGlyLeuAspIleAlaAspPhePheSerGlyThrAlaHisValAspValAspLy
sLeuArgProLysAlaAspValValThrArgGlyIleArgHisLeuLeuArgIleAlaSerGlyAsnLeuHisGly
AsnAsnAlaAlaPheIleGlyLysIleAlaAlaValGlnGlyPheSerSerIleSerGluArgArgValAlaGlyG
lnHisPheAlaHisArgProThrCysAlaLysIleSerAlaLysSerAlaGluArgPheValGlyAsnAlaArgHi
sArgArgLysCysAspGlyValValAspLysIleAlaAlaAspValHisAsnGlySerAlaPheGlnLysSerThr
ProLeuTyrIlePhe-359
a903-1
AMPHI Regions - AMPHI
SEQ. ID. NO. 24421  1-MetLysPhePheProAlaProCysLeuLeuValIleLeuAlaValIlePr
oLeuLysThrLeuAlaAlaAspGluAsnAspAlaGluLeuIleArgSerMetGlnArgGlnGlnHisIleAspAlaGluLeuLeuThrAspAlaAsnValArgP
heGluGlnProLeuGluLysAsnAsnTyrValLeuSerGluAspGluThrProCysThrArgValAsnTyrIleSerLeuAspAspLysThrAlaArgLysPhe
SerPheLeuProSerValLeuMetLysGluThrAlaPheLysThrGlyMetCysLeuGlySerAsnAsnLeuSerArgLeuGlnLysAlaAlaGlnGlnIleLe
uIleValArgGlyTyrLeuThrSerGlnAlaIleIleGlnProGlnAsnMetAspSerGlyIleLeuLysLeuArgValSerAlaGlyGluIleGlyAspIleA
rgTyrGluGluLysArgAspGlyLysSerAlaGluGlySerIleSerAlaPheAsnAsnLysPheProLeuTyrArgAsnLysIleLeuAsnLeuArgAspVal
GluGlnGlyLeuGluAsnLeuArgArgLeuProSerValLysThrAspIleGlnIleIleProSerGluGluGluGlyLysSerAspLeuGlnIleLysTrpGl
nGlnAsnLysProIleArgPheSerIleGlyIleAspAspAlaGlyGlyLysThrThrGlyLysTyrGlnGlyAsnValAlaLeuSerPheAspAsnProLeuG
lyLeuSerAspLeuPheTyrValSerTyrGlyArgGlyLeuValHisLysThrAspLeuThrAspAlaThrGlyThrGluThrGluSerGlySerArgSerTyr
SerValHisTyrSerValProValLysLysTrpLeuPheSerPheAsnHisAsnGlyHisArgTyrHisGluAlaThrGluGlyTyrSerValAsnTyrAspTy
rAsnGlyLysGlnTyrGlnSerSerLeuAlaAlaGluArgMetLeuTrpArgAsnArgPheHisLysThrSerValGlyMetLysLeuTrpThrArgGlnThrT
yrLeuTyrIleAspAspAlaGluIleGluValGlnArgArgArgSerAlaGlyTrpGluAlaGluLeuArgHisArgAlaTyrLeuAsnArgTrpGlnLeuAsp
GlyLysLeuSerTyrLysArgGlyThrGlyMetArgGlnSerMetProAlaProGluGluAsnGlyGlyGlyThrIleProGlyThrSerArgMetLysIleIl TABLE 1-continued eThrAlaGlyLeuAspAlaAlaAlaProPheMetLeuGlyLysGlnGlnPhePheTyrAlaThrAlaIleGlnAlaGlnTrpAsnLysThrProLeuValAlaG
lnAspLysLeuSerIleGlySerArgTyrThrValArgGlyPheAspGlyGluGlnSerLeuPheGlyGluArgGlyPheTyrTrpGlnAsnThrLeuThrTrp
TyrPheHisProAsnHisGlnPheTyrLeuGlyAlaAspTyrGlyArgValSerGlyGluSerAlaGlnTyrValSerGlyLysGlnLeuMetGlyAlaValVa
lGlyPheArgGlyGlyHisLysValGlyGlyMetPheAlaTyrAspLeuPheAlaGlyLysProLeuHisLysProLysGlyPheGlnThrThrAsnThrVal
TyrGlyPheAsnLeuAsnTyrSerPhe-580

Antigenic Index - Jameson-Wolf (SEQ. ID. NO. 24421)
1-MetLysPhePheProAlaProCysLeuLeuValIleLeuAlaValIleProLeuLysThrLeuAlaAlaAspGl
uAsnAspAlaGluLeuIleArgSerMetGlnArgGlnGlnHisIleAspAlaGluLeuLeuThrAspAlaAsnVal
ArgPheGluGlnProLeuGluLysAsnAsnTyrValLeuSerGluAspGluThrProCysThrArgValAsnTyrI
leSerLeuAspAspLysThrAlaArgLysPheSerPheLeuProSerValLeuMetLysGluThrAlaPheLysTh
rGlyMetCysLeuGlySerAsnAsnLeuSerArgLeuGlnLysAlaAlaGlnGlnIleLeuIleValArgGlyTyr
LeuThrSerGlnAlaIleIleGlnProGlnAsnMetAspSerGlyIleLeuLysLeuArgValSerAlaGlyGluI
leGlyAspIleArgTyrGluGluLysArgAspGlyLysSerAlaGluGlySerIleSerAlaPheAsnAsnLysPh
eProLeuTyrArgAsnLysIleLeuAsnLeuArgAspValGluGlnGlyLeuGluAsnLeuArgArgLeuProSer
ValLysThrAspIleGlnIleIleProSerGluGluGluGlyLysSerAspLeuGlnIleLysTrpGlnGlnAsnL
ysProIleArgPheSerIleGlyIleAspAspAlaGlyGlyLysThrThrGlyLysTyrGlnGlyAsnValAlaLe
uSerPheAspAsnProLeuGlyLeuSerAspLeuPheTyrValSerTyrGlyArgGlyLeuValHisLysThrAsp
LeuThrAspAlaThrGlyThrGluThrGluSerGlySerArgSerTyrSerValHisTyrSerValProValLysL
ysTrpLeuPheSerPheAsnHisAsnGlyHisArgTyrHisGluAlaThrGluGlyTyrSerValAsnTyrAspTy
rAsnGlyLysGlnTyrGlnSerSerLeuAlaAlaGluArgMetLeuTrpArgAsnArgPheHisLysThrSerVal
GlyMetLysLeuTrpThrArgGlnThrTyrLysTyrIleAspAspAlaGluIleGluValGlnArgArgArgSerA
laGlyTrpGluAlaGluLeuArgHisArgAlaTyrLeuAsnArgTrpGlnLeuAspGlyLysLeuSerTyrLysAr
gGlyThrGlyMetArgGlnSerMetProAlaProGluGluAsnGlyGlyGlyThrIleProGlyThrSerArgMet
LysIleIleThrAlaGlyLeuAspAlaAlaAlaProPheMetLeuGlyLysGlnGlnPhePheTyrAlaThrAlaI
leGlnAlaGlnTrpAsnLysThrProLeuValAlaGlnAspLysLeuSerIleGlySerArgTyrThrValArgGl
yPheAspGlyGluGlnSerLeuPheGlyGluArgGlyPheTyrTrpGlnAsnThrLeuThrTrpTyrPheHisPro
AsnHisGlnPheTyrLeuGlyAlaAspTyrGlyArgValSerGlyGluSerAlaGlnTyrValSerGlyLysGlnL
euMetGlyAlaValValGlyPheArgGlyGlyHisLysValGlyGlyMetPheAlaTyrAspLeuPheAlaGlyLy
sProLeuHisLysProLysGlyPheGlnThrThrAsnThrValTyrGlyPheAsnLeuAsnTyrSerPhe-580

Hydrophilic Regions - Hopp-Woods (SEQ. ID. NO. 24421)
1-MetLysPhePheProAlaProCysLeuLeuValIleLeuAlaValIleProLeuLysThrLeuAlaAlaAspGl
uAsnAspAlaGluLeuIleArgSerMetGlnArgGlnGlnHisIleAspAlaGluLeuLeuThrAspAlaAsnVal
ArgPheGluGlnProLeuGluLysAsnAsnTyrValLeuSerGluAspGluThrProCysThrArgValAsnTyrI
leSerLeuAspAspLysThrAlaArgLysPheSerPheLeuProSerValLeuMetLysGluThrAlaPheLysTh
rGlyMetCysLeuGlySerAsnAsnLeuSerArgLeuGlnLysAlaAlaGlnGlnIleLeuIleValArgGlyTyr
LeuThrSerGlnAlaIleIleGlnProGlnAsnMetAspSerGlyIleLeuLysLeuArgValSerAlaGlyGluI
leGlyAspIleArgTyrGluGluLysArgAspGlyLysSerAlaGluGlySerIleSerAlaPheAsnAsnLysPh
eProLeuTyrArgAsnLysIleLeuAsnLeuArgAspValGluGlnGlyLeuGluAsnLeuArgArgLeuProSer
ValLysThrAspIleGlnIleIleProSerGluGluGluGlyLysSerAspLeuGlnIleLysTrpGlnGlnAsnL
ysProIleArgPheSerIleGlyIleAspAspAlaGlyGlyLysThrThrGlyLysTyrGlnGlyAsnValAlaLe
uSerPheAspAsnProLeuGlyLeuSerAspLeuPheTyrValSerTyrGlyArgGlyLeuValHisLysThrAsp
LeuThrAspAlaThrGlyThrGluThrGluSerGlySerArgSerTyrSerValHisTyrSerValProValLysL
ysTrpLeuPheSerPheAsnHisAsnGlyHisArgTyrHisGluAlaThrGluGlyTyrSerValAsnTyrAspTy
rAsnGlyLysGlnTyrGlnSerSerLeuAlaAlaGluArgMetLeuTrpArgAsnArgPheHisLysThrSerVal
GlyMetLysLeuTrpThrArgGlnThrTyrLysTyrIleAspAspAlaGluIleGluValGlnArgArgArgSerA
laGlyTrpGluAlaGluLeuArgHisArgAlaTyrLeuAsnArgTrpGlnLeuAspGlyLysLeuSerTyrLysAr
gGlyThrGlyMetArgGlnSerMetProAlaProGluGluAsnGlyGlyGlyThrIleProGlyThrSerArgMet
LysIleIleThrAlaGlyLeuAspAlaAlaAlaProPheMetLeuGlyLysGlnGlnPhePheTyrAlaThrAlaI
leGlnAlaGlnTrpAsnLysThrProLeuValAlaGlnAspLysLeuSerIleGlySerArgTyrThrValArgGl
yPheAspGlyGluGlnSerLeuPheGlyGluArgGlyPheTyrTrpGlnAsnThrLeuThrTrpTyrPheHisPro
AsnHisGlnPheTyrLeuGlyAlaAspTyrGlyArgValSerGlyGluSerAlaGlnTyrValSerGlyLysGlnL
euMetGlyAlaValValGlyPheArgGlyGlyHisLysValGlyGlyMetPheAlaTyrAspLeuPheAlaGlyLy
sProLeuHisLysProLysGlyPheGlnThrThrAsnThrValTyrGlyPheAsnLeuAsnTyrSerPhe-580
a904

AMPHI Regions - AMPHI
SEQ. ID. NO. 24422    1-MetMetGlnHisAsnArgPhePheAlaValGlyAlaGlyGlyAspAspGlyAspArgArgThrAlaAspPhePh
eAsnProPheGlnIleCysPheGlyIleGlyArgCysValValAlaPheHisAlaGluSerGlyPheAlaProThrGlyH
isGlyPheValAsnArgLeuAlaGlyPheTyrArgIleArgAlaAlaArgGlnAspValGlyPheAlaAlaValGlyPheValAlaAspAlaAspIleAsp
GlyPheAsnAlaValHisTyrIleGluPheGlyAsnThrHisThrGlyAsnAlaValAspLeuAspGlyAlaPheGlnGlyGlyGlyIleLysProAlaAlaAlaAl
aAlaCysAlaSerGlyTyrArgThrGluPheValSerAlaPheCysGlnThrCysSerAspPheValGluGlnPheGlyArgGluArgAlaArgThrAspAlaA
rgGlyIleGlyPheAspAspAlaGlnAsnIleIleGlnHisLeuArgAlaTyrAlaArgAlaCysArgSerArgAlaGlyGluAlaValGlyArgSerAsnGlu
GlyValSerAlaValValAspValGlnGlnArgThrLeuArgAlaPheLysGlnGlnPhePheAlaValPheValPheValGlnHisAlaGlyHisValGl
yAsnHisArgArgAsnAlaArgArgAspPhePheAspAsnArgHisHisValPheArgPheHisArgLeuGlyIleValGlnMetLeuGlnLeuAspValValI
leSerLysAspGlyIleGlnPhePheThrGlnPhePheArgMetGlnGlnIleGlyGlyAlaAsnGlyAlaAlaCysHisPheValPheValGlyArgAlaAsp
AlaAlaAlaGlyArgAlaAspPheAlaPheAlaAlaArgCysPheSerGlyLeuValGluArgAspValIleArgGlnAspGlnArgAlaGlyArgArgAspPh
eGlnThrAlaPheAspValPheHisAlaCysArgValGlnLeuValAspPheAlaGlnGlnGlyPheGlyGlyAspAspAsnAlaArgThrAspGluAlaValG
lnThrPheMetGlnAspAlaAlaArgAsnGlnAlaGlnAsnGlyPhePheAlaAlaAspAsnGlnGlyMetThrArgIleValAlaAlaLeuGluAlaHisHis
AlaSerGlyPhePheArgPheGlnProValAsnAspPheThrPheThrLeuValAlaProLeuCysAlaAspTyrTyrAsnIlePheSerHisSerHisIleThr
XxxArgTyr-435

Antigenic Index - Jameson-Wolf (SEQ. ID. NO. 24422)
1-MetMetGlnHisAsnArgPhePheAlaValGlyAlaGlyGlyAspAspGlyAspArgArgThrAlaAspPhePh
eAsnProPheGlnIleCysPheGlyIleGlyArgCysValValAlaPheHisAlaGluSerGlyPheAlaProThr
GlyHisGlyPheValAsnArgLeuAlaGlyPheTyrArgIleArgAlaAlaArgGlnAspValGlyPheAlaAlaV
alGlyGlnPheValAlaAspAlaAspIleAspGlyPheAsnAlaValHisTyrIleGluPheGlyAsnThrHisTh
rGlyAsnAlaValAspLeuAspGlyAlaPheGlnGlyGlyGlyIleLysProAlaAlaAlaAlaAlaCysAlaSerGly
TyrArgThrGluPheValSerAlaPheCysGlnThrCysSerAspPheValGluGlnPheGlyArgGluArgAlaA
rgThrAspAlaArgGlyIleGlyPheAspAspAlaGlnAsnIleIleGlnHisLeuArgAlaTyrAlaArgAlaCy
sArgSerArgAlaGlyGluAlaValGlyArgSerAsnGluGlyValSerAlaValValAspValGlnGlnArgThr
LeuArgAlaPheLysGlnGlnPhePheAlaValPheValPhePheValGlnHisAlaGlyHisValGlyAsnHisA
rgArgAsnAlaArgArgAspPhePheAspAsnArgHisHisValPheArgPheHisArgLeuGlyIleValGlnMe TABLE 1-continued tLeuGlnLeuAspValValIleSerLysAspGlyIleGlnPhePheThrGlnPhePheArgMetGlnGlnIleGly
GlyAlaAsnGlyAlaAlaCysHisPheValPheValGlyArgAlaAspAlaAlaAlaGlyArgAlaAspPheAlaP
heAlaAlaArgCysPheSerGlyLeuValGluArgAspValIleArgGlnAspGlnArgAlaGlyArgArgAspPh
eGlnThrAlaPheAspValPheHisAlaCysArgValGlnLeuValAspPheAlaGlnGlnGlyPheGlyGlyAsp
AspAsnAlaArgThrAspGluAlaValGlnThrPheMetGlnAspAlaAlaArgAsnGlnAlaGlnAsnGlyPheP
heAlaAlaAspAsnGlnGlyMetThrArgIleValAlaAlaLeuGluAlaHisHisAlaSerGlyPhePheArgGl
nProValAsnAspPheThrPheThrLeuValAlaProLeuCysAlaAspTyrTyrAsnIlePheSerHisSerHis
IleThrXxxArgTyr-435

Hydrophilic Regions - Hopp-Woods (SEQ. ID. NO. 24422)
1-MetMetGlnHisAsnArgPhePheAlaValGlyAlaGlyGlyAspAspGlyAspArgArgThrAlaAspPhePh
eAsnProPheGlnIleCysPheGlyIleGlyArgCysValValAlaPheHisAlaGluSerGlyPheAlaProThr
GlyHisGlyPheValAlaAsnArgLeuAlaGlyPheTyrArgIleArgAlaAlaArgGlnAspValGlyPheAlaV
alGlyGlnPheValAlaAspAlaAspIleAspGlyPheAsnAlaValHisTyrIleGluPheGlyAsnThrHisTh
rGlyAsnAlaValAspLeuAspGlyAlaPheGlnGlyGlyGlyIleLysProAlaAlaAlaAlaCysAlaSerGly
TyrArgThrGluPheValSerAlaPheCysGlnThrCysSerAspPheValGluGlnPheGlyArgGluArgAlaA
rgThrAspAlaArgGlyIleGlyPheAspAspAlaGlnAsnIleIleGlnHisLeuArgAlaTyrAlaArgAlaCy
sArgSerArgAlaGlyGluAlaValGlyArgSerAsnGluGlyValSerAlaValValAspValGlnGlnArgThr
LeuArgAlaPheLysGlnGlnPhePheAlaValPheValPhePheValGlnHisAlaGlyHisValGlyAsnHisA
rgArgAsnAlaArgArgAspPhePheAspAsnArgHisHisValPheArgPheHisArgLeuGlyIleValGlnMe
tLeuGlnLeuAspValValIleSerLysAspGlyIleGlnPhePheThrGlnPhePheArgMetGlnGlnIleGly
GlyAlaAsnGlyAlaAlaCysHisPheValPheValGlyArgAlaAspAlaAlaAlaGlyArgAlaAspPheAlaP
heAlaAlaArgCysPheSerGlyLeuValGluArgAspValIleArgGlnAspGlnArgAlaGlyArgArgAspPh
eGlnThrAlaPheAspValPheHisAlaCysArgValGlnLeuValAspPheAlaGlnGlnGlyPheGlyGlyAsp
AspAsnAlaArgThrAspGluAlaValGlnThrPheMetGlnAspAlaAlaArgAsnGlnAlaGlnAsnGlyPheP
heAlaAlaAspAsnGlnGlyMetThrArgIleValAlaAlaLeuGluAlaHisHisAlaSerGlyPhePheArgGl
nProValAsnAspPheThrPheThrLeuValAlaProLeuCysAlaAspTyrTyrAsnIlePheSerHisSerHis
IleThrXxxArgTyr-435 a907
AMPHI Regions - AMPHI
SEQ. ID. NO. 24423    1-MetLysLysProThrAspThrLeuProValAsnLeuGlnArgArgArgLe
uLeuCysAlaAlaGlyAlaLeuLeuLeuSerProLeuAlaGlnAlaGlyAlaGlnArgGluGluThrLeuAlaAspAspValAlaSerValMetArgSerSerV
alGlySerIleAsnProProArgLeuValPheAspAsnProLysGluGlyGluArgTrpLeuSerAlaMetSerAlaArgLeuAlaArgPheValProAspGlu
GluGluArgArgArgLeuLeuValAsnIleGlnTyrGluSerSerArgAlaGlyLeuAspThrGlnIleValLeuGlyLeuIleGluValGluSerAlaPheAr
gGlnTyrAlaIleSerGlyValGlyAlaArgGlyLeuMetGlnValMetProPheTrpLysAsnTyrIleGlyLysProAlaHisAsnLeuPheAspIleArgT
hrAsnLeuArgTyrGlyCysThrIleLeuArgHisTyrArgAsnLeuGluLysGlyAsnIleValArgAlaLeuAlaArgPheAsnGlySerLeuGlySerAsn
LysTyrProAsnAlaValLeuGlyAlaTrpArgAsnArgTrpGlnTrpArg-207

Antigenic Index - Jameson-Wolf (SEQ. ID. NO. 24423)
1-MetLysLysProThrAspThrLeuProValAsnLeuGlnArgArgArgLeuLeuCysAlaAlaGlyAlaLeuLe
uLeuSerProLeuAlaGlnAlaGlyAlaGlnArgGluGluThrLeuAlaAspAspValAlaSerValMetArgSer
SerValGlySerIleAsnProProArgLeuValPheAspAsnProLysGluGlyGluArgTrpLeuSerAlaMetS
erAlaArgLeuAlaArgPheValProAspGluGluGluArgArgArgLeuLeuValAsnIleGlnTyrGluSerSe
rArgAlaGlyLeuAspThrGlnIleValLeuGlyLeuIleGluValGluSerAlaPheArgGlnTyrAlaIleSer
GlyValGlyAlaArgGlyLeuMetGlnValMetProPheTrpLysAsnTyrIleGlyLysProAlaHisAsnLeuP
heAspIleArgThrAsnLeuArgTyrGlyCysThrIleLeuArgHisTyrArgAsnLeuGluLysGlyAsnIleVa
lArgAlaLeuAlaArgPheAsnGlySerLeuGlySerAsnLysTyrProAsnAlaValLeuGlyAlaTrpArgAsn
ArgTrpGlnTrpArg-207

Hydrophilic Regions - Hopp-Woods (SEQ. ID. NO. 24423)
1-MetLysLysProThrAspThrLeuProValAsnLeuGlnArgArgArgLeuLeuCysAlaAlaGlyAlaLeuLe
uLeuSerProLeuAlaGlnAlaGlyAlaGlnArgGluGluThrLeuAlaAspAspValAlaSerValMetArgSer
SerValGlySerIleAsnProProArgLeuValPheAspAsnProLysGluGlyGluArgTrpLeuSerAlaMetS
erAlaArgLeuAlaArgPheValProAspGluGluGluArgArgArgLeuLeuValAsnIleGlnTyrGluSerSe
rArgAlaGlyLeuAspThrGlnIleValLeuGlyLeuIleGluValGluSerAlaPheArgGlnTyrAlaIleSer
GlyValGlyAlaArgGlyLeuMetGlnValMetProPheTrpLysAsnTyrIleGlyLysProAlaHisAsnLeuP
heAspIleArgThrAsnLeuArgTyrGlyCysThrIleLeuArgHisTyrArgAsnLeuGluLysGlyAsnIleVa
lArgAlaLeuAlaArgPheAsnGlySerLeuGlySerAsnLysTyrProAsnAlaValLeuGlyAlaTrpArgAsn
ArgTrpGlnTrpArg-207 a908
AMPHI Regions - AMPHI
SEQ. ID. NO. 24424    1-MetArgLysSerArgLeuSerGlnTyrLysGlnAsnLysLeuIleGluLe
uPheValAlaGlyValThrAlaArgThrAlaAlaGluLeuValGlyValAsnLysAsnThrAlaAlaTyrTyrPheHisArgLeuArgLeuLeuIleTyrGlnA
snSerProHisLeuGluMetPheAspGlyGluValGluAlaAspGluSerTyrPheGlyGlyGlnArgLysGlyLysArgGlyArgGlyAlaAlaGlyLysVal
AlaValPheGlyLeuLeuLysArgAsnGlyLysValTyrThrValThrValProAsnThrGlnThrAlaThrLeuPheProIleIleArgGluGlnValLysPr
oAspSerIleValTyrThrAspCysTyrArgSerTyrAspValLeuAspValArgGluPheSerHisPheSerPheAlaGluThrSerPheSerTyrGlnSer
GlnHisThrPheCysArgThrThrLysProTyr-166

Antigenic Index - Jameson-Wolf (SEQ. ID. NO. 24424)
1-MetArgLysSerArgLeuSerGlnTyrLysGlnAsnLysLeuIleGluLeuPheValAlaGlyValThrAlaAr
gThrAlaAlaGluLeuValGlyValAsnLysAsnThrAlaAlaTyrTyrPheHisArgLeuArgLeuLeuIleTyr
GlnAsnSerProHisLeuGluMetPheAspGlyGluValGluAlaAspGluSerTyrPheGlyGlyGlnArgLysG
lyLysArgGlyArgGlyAlaAlaGlyLysValAlaValPheGlyLeuLeuLysArgAsnGlyLysValTyrThrVa
lThrValProAsnThrGlnThrAlaThrLeuPheProIleIleArgGluGlnValLysProAspSerIleValTyr
ThrAspCysTyrArgSerTyrAspValLeuAspValArgGluPheSerHisPheSerPheAlaGluThrSerPheS
erTyrGlnSerGlnHisThrPheCysArgThrThrLysProTyr-166

Hydrophilic Regions - Hopp-Woods (SEQ. ID. NO. 24424)
1-MetArgLysSerArgLeuSerGlnTyrLysGlnAsnLysLeuIleGluLeuPheValAlaGlyValThrAlaAr
gThrAlaAlaGluLeuValGlyValAsnLysAsnThrAlaAlaTyrTyrPheHisArgLeuArgLeuLeuIleTyr
GlnAsnSerProHisLeuGluMetPheAspGlyGluValGluAlaAspGluSerTyrPheGlyGlyGlnArgLysG
lyLysArgGlyArgGlyAlaAlaGlyLysValAlaValPheGlyLeuLeuLysArgAsnGlyLysValTyrThrVa
lThrValProAsnThrGlnThrAlaThrLeuPheProIleIleArgGluGlnValLysProAspSerIleValTyr
ThrAspCysTyrArgSerTyrAspValLeuAspValArgGluPheSerHisPheSerPheAlaGluThrSerPheS
erTyrGlnSerGlnHisThrPheCysArgThrThrLysProTyr-166

TABLE 1-continued a909
AMPHI Regions - AMPHI
SEQ. ID. NO. 24425   71-GlyAsnAsnAlaAspGlu-76
Antigenic Index - Jameson-Wolf
SEQ. ID. NO. 24426   22-ThrTyrGlnAspGlyAsnGlyLysThrAlaValArgGlnLysTyrProAlaGly-39
SEQ. ID. NO. 24427   45-GlnAspGlySerTyrSerLysAsnMetAsnTyrAsnGlnTyrArgProGluArgHisAla-64
SEQ. ID. NO. 24428   68-AsnGlnThrGlyAsnAsnAlaAspGluGluHisArgGlnHisTrpGlnLysProLysPheGlnAsnArg-90
Hydrophilic Regions - Hopp-Woods
SEQ. ID. NO. 24429   23-TyrGlnAspGlyAsnGlyLysThrAlaValArgGlnLysTyr-36
SEQ. ID. NO. 24430   58-TyrArgProGluArgHisAla-64
SEQ. ID. NO. 24431   72-AsnAsnAlaAspGluGluHisArgGlnHisTrpGln-83
SEQ. ID. NO. 24432   85-ProLysPheGlnAsnArg-90
a910
AMPHI Regions - AMPHI
SEQ. ID. NO. 24433   22-SerAlaGluArgGlnIle-27
SEQ. ID. NO. 24434   39-LysAlaValLysMetLeuGlu-45
SEQ. ID. NO. 24435   58-AspHisTrpGlyLysPro-63
SEQ. ID. NO. 24436   69-AlaTyrLysAspGlyArg-74
Antigenic Index - Jameson-Wolf
SEQ. ID. NO. 24437   19-AlaGlyAspSerAlaGluArgGlnIleTyr-28
SEQ. ID. NO. 24438   30-AspProTyrPheGluGlnAsnArgThrLysAlaValLysMetLeuGluGlnArgGlyTyrGln-50
SEQ. ID. NO. 24439   52-HisAspValAspAlaAspAspHisTrpGly-61
SEQ. ID. NO. 24440   68-GluAlaTyrLysAspGlyArgGluTyrAsp-77
SEQ. ID. NO. 24441   83-ProAspLeuLysIleIleLysGluGlnLeuAspArg-94
Hydrophilic Regions - Hopp-Woods
SEQ. ID. NO. 24442   21-AspSerAlaGluArgGlnIleTyr-28
SEQ. ID. NO. 24443   32-TyrPheGluGlnAsnArgThrLysAlaValLysMetLeuGluGlnArgGly-48
SEQ. ID. NO. 24444   52-HisAspValAspAlaAspAspHisTrpGly-61
SEQ. ID. NO. 24445   68-GluAlaTyrLysAspGlyArgGluTyrAsp-77
SEQ. ID. NO. 24446   86-LysIleIleLysGluGlnLeuAspArg-94
a911
AMPHI Regions - AMPHI
SEQ. ID. NO. 24447   6-LeuGluPheTrpValGlyLeuPhe-13
SEQ. ID. NO. 24448   43-ValTyrAlaAspPheGlyAspIleGly-51
SEQ. ID. NO. 24449   97-ValSerAlaGlnIle-101
SEQ. ID. NO. 24450   118-GlyAspThrGluAsnLeuAla-124
SEQ. ID. NO. 24451   140-AsnLeuIleGlyLysPheMetThrSerPhe-149
Antigenic Index - Jameson-Wolf
SEQ. ID. NO. 24452   1-MetLysLysAsnIle-5
SEQ. ID. NO. 24453   35-GlyGlySerAspLysThrTyr-41
SEQ. ID. NO. 24454   48-GlyAspIleGlyGlyLeuLysValAsnAlaProValLys-60
SEQ. ID. NO. 24455   74-LeuAspProLysSerTyrGlnAlaArgValArgLeuAspLeuAspGlyLysTyrGlnPheSerSerAspVal-97
SEQ. ID. NO. 24456   103-ThrSerGlyLeuLeuGly-108
SEQ. ID. NO. 24457   115-GlnGlnGlyGlyAspThrGluAsn-122
SEQ. ID. NO. 24458   149-PheAlaGluLysAsnAlaAspGlyGlyAsnAlaGluLysAlaAlaGlu-164
Hydrophilic Regions - Hopp-Woods
SEQ. ID. NO. 24459   1-MetLysLysAsnIle-5
SEQ. ID. NO. 24460   36-GlySerAspLysThr-40
SEQ. ID. NO. 24461   74-LeuAspProLysSerTyrGlnAlaArgValArgLeuAspLeuAspGly-89
SEQ. ID. NO. 24462   116-GlnGlyGlyAspThrGluAsn-122
SEQ. ID. NO. 24463   149-PheAlaGluLysAsnAlaAspGlyGlyAsnAlaGluLysAlaAlaGlu-164
a912
AMPHI Regions - AMPHI
SEQ. ID. NO. 24464   24-ProAlaAspAlaValAsnGlnIle-31
SEQ. ID. NO. 24465   38-ValLeuSerIleLeu-42
SEQ. ID. NO. 24466   62-PheAspPheGlnArgMetThrAlaLeuAlaValGlyAsnProTrpArgThrAlaSerAspAlaGlnLys-84
SEQ. ID. NO. 24467   89-LysGluPheGlnThrLeu-94
SEQ. ID. NO. 24468   169-TyrArgAsnGlnPheGlyGluIleIleLysAlaLys-180
Antigenic Index - Jameson-Wolf
SEQ. ID. NO. 24469   1-MetLysLysSerSer-5
SEQ. ID. NO. 24470   29-AsnGlnIleArgGlnAsnAlaThrGln-37
SEQ. ID. NO. 24471   42-LeuLysSerGlyAspAlaAsnThrAlaArgGlnLysAlaGluAla-56
SEQ. ID. NO. 24472   74-AsnProTrpArgThrAlaSerAspAlaGlnLysGlnAlaLeuAlaLysGluPhe-91
SEQ. ID. NO. 24473   104-LeuLysLeuLysAsnAlaAsnValAsnValLysAspAsnProIleValAsnLysGlyGlyLysGluIleIleVal-128
SEQ. ID. NO. 24474   130-AlaGluValGlyValProGlyGlnLysProValAsn-141
SEQ. ID. NO. 24475   146-ThrTyrGlnSerGlyGlyLysTyrArgThr-155
SEQ. ID. NO. 24476   169-TyrArgAsnGlnPhe-173
SEQ. ID. NO. 24477   177-IleLysAlaLysGlyValAspGlyLeuIleAla-187
SEQ. ID. NO. 24478   189-LeuLysAlaLysAsnGlySerLys-196
Hydrophilic Regions - Hopp-Woods
SEQ. ID. NO. 24479   1-MetLysLysSerSer-5
SEQ. ID. NO. 24480   31-IleArgGlnAsnAla-35
SEQ. ID. NO. 24481   43-LysSerGlyAspAlaAsnThrAlaArgGlnLysAlaGluAla-56
SEQ. ID. NO. 24482   78-ThrAlaSerAspAlaGlnLysGlnAlaLeuAlaLysGluPhe-91
SEQ. ID. NO. 24483   104-LeuLysLeuLysAsn-108
SEQ. ID. NO. 24484   110-AsnValAsnValLysAspAsnProIleVal-119
SEQ. ID. NO. 24485   121-LysGlyGlyLysGluIleIleVal-128
SEQ. ID. NO. 24486   134-ValProGlyGlnLysProValAsn-141
SEQ. ID. NO. 24487   177-IleLysAlaLysGlyValAsp-183
SEQ. ID. NO. 24488   189-LeuLysAlaLysAsnGlySerLys-196

TABLE 1-continued a913
AMPHI Regions - AMPHI
SEQ. ID. NO. 24489     22-GluThrArgProAlaAspProTyrGluGlyTyrAsnArg-34
SEQ. ID. NO. 24490     53-ArgGlyTyrArgLysValAlaProLys-61
SEQ. ID. NO. 24491     66-GlyValSerAsnPhePheAsnAsnLeuCysAspValValSer-79
SEQ. ID. NO. 24492     107-LeuGlyGlyLeuIleAspIleAlaGlyAla-116
SEQ. ID. NO. 24493     151-ValArgAspAlaLeuGlyThrGlyIleThrSerValTyrSer-164
SEQ. ID. NO. 24494     193-AspLeuThrAspSerLeuAspGluAlaAla-202
SEQ. ID. NO. 24495     238-LeuValGluSerAla-242
SEQ. ID. NO. 24496     257-SerGluThrGlnAla-261
Antigenic Index - Jameson-Wolf
SEQ. ID. NO. 24497     21-AlaGluThrArgProAlaAspProTyrGluGlyTyrAsn-33
SEQ. ID. NO. 24498     39-PheAsnAspGlnAlaAspArgTyr-46
SEQ. ID. NO. 24499     51-AlaAlaArgGlyTyrArgLysValAlaProLysProValArgAla-65
SEQ. ID. NO. 24500     81-GlySerAsnIleLeu-85
SEQ. ID. NO. 24501     87-LeuAspIleLysArgAlaSerGluAspLeuVal-97
SEQ. ID. NO. 24502     117-GlyGlyIleProAspAsnLysAsnThrLeuGlyAsp-128
SEQ. ID. NO. 24503     132-SerTrpGlyTrpLysAsnSerAsn-139
SEQ. ID. NO. 24504     149-SerThrValArgAspAlaLeu-155
SEQ. ID. NO. 24505     163-TyrSerProLysAsnIle-168
SEQ. ID. NO. 24506     172-ThrProValGlyArgTrpGly-178
SEQ. ID. NO. 24507     185-ValSerThrArgGluGlyLeuLeuAspLeuThrAspSerLeuAspGluAlaAlaIleAspLysTyrSerTyrThrArgAspLeuTyrMet-214
SEQ. ID. NO. 24508     216-ValArgAlaArgGlnThrGlyAlaThrProAlaGluGlyThrGluAspAsnIleAspIleAspGluLeuValGluSerAlaGluThrGlyAlaAla-247
SEQ. ID. NO. 24509     250-AlaValGlnGluAspSerValSerGluThrGlnAlaGluAlaAlaGlyGluAlaGluThrGlnProGlyThrGlnProGlyThrGlnPro-279
Hydrophilic Regions - Hopp-Woods
SEQ. ID. NO. 24510     21-AlaGluThrArgProAlaAspProTyrGluGlyTyrAsn-33
SEQ. ID. NO. 24511     40-AsnAspGlnAlaAsp-44
SEQ. ID. NO. 24512     53-ArgGlyTyrArgLysValAlaProLysProValArg-64
SEQ. ID. NO. 24513     87-LeuAspIleLysArgAlaSerGluAspLeuVal-97
SEQ. ID. NO. 24514     118-GlyIleProAspAsnLysAsnThrLeu-126
SEQ. ID. NO. 24515     150-ThrValArgAspAlaLeu-155
SEQ. ID. NO. 24516     186-SerThrArgGluGlyLeuLeuAspLeuThrAspSerLeuAspGluAlaAlaIleAsp-204
SEQ. ID. NO. 24517     216-ValArgAlaArgGlnThrGly-222
SEQ. ID. NO. 24518     224-ThrProAlaGluGlyThrGluAspAsnIleAspIleAspGluLeuValGluSerAlaGluThrGlyAlaAla-247
SEQ. ID. NO. 24519     250-AlaValGlnGluAspSerValSerGluThrGlnAlaGluAlaAlaGlyGluAlaGluThrGlnPro-271
a914-2
AMPHI Regions - AMPHI
SEQ. ID. NO. 24520     6-LeuGlyIleLeuThrAlaCysAlaAlaMet-15
SEQ. ID. NO. 24521     17-AlaPheAlaAspArgIleGlyAspLeu-25
SEQ. ID. NO. 24522     65-PheGlnLysThrPheGlu-70
SEQ. ID. NO. 24523     81-GlnLysValArgGlnAlaCys-87
Antigenic Index - Jameson-Wolf
SEQ. ID. NO. 24524     18-PheAlaAspArgIleGlyAspLeuGluAlaArgLeuAlaGlnLeuGluHisArgValAlaVal-38
SEQ. ID. NO. 24525     40-GluSerGlySerAsnThrValLys-47
SEQ. ID. NO. 24526     50-LeuPheGlySerAsnSer-55
SEQ. ID. NO. 24527     64-ProPheGlnLysThrPheGluAlaSerAspArgAsnGluGlyValAlaArgGlnLysValArgGlnAlaCysAsnArgGluThrSerAla-93
SEQ. ID. NO. 24528     95-PheCysGluAspGluAlaIleArgCysArgLysPheAsp-107
Hydrophilic Regions - Hopp-Woods
SEQ. ID. NO. 24529     18-PheAlaAspArgIleGlyAspLeuGluAlaArgLeuAlaGlnLeuGluHisArgValAlaVal-38
SEQ. ID. NO. 24530     67-LysThrPheGluAlaSerAspArgAsnGluGlyValAlaArgGlnLysValArgGlnAlaCysAsnArgGluThrSer-92
SEQ. ID. NO. 24531     95-PheCysGluAspGluAlaIleArgCysArgLysPheAsp-107
a915
AMPHI Regions - AMPHI
SEQ. ID. NO. 24532     9-ValAlaValSerAlaLeuSerAlaCysArgGlnAla-20
SEQ. ID. NO. 24533     31-IleSerAspArgSerVal-36
SEQ. ID. NO. 24534     67-SerThrIleLysGlnMetPheGlyTyrThrLysLeuProGluGluProLysGlyIleArgValIleTyrValThrAspMetGlyAsnValThrAspTrpThr-100
SEQ. ID. NO. 24535     139-GlnAlaGluLysPhe-143
Antigenic Index - Jameson-Wolf
SEQ. ID. NO. 24536     15-SerAlaCysArgGlnAlaGluGluGlyProProProLeuProArgGlnIleSerAspArgSerValGlyHis-38
SEQ. ID. NO. 24537     43-AsnLeuThrGluHisAsnGlyProLysAla-52
SEQ. ID. NO. 24538     57-AsnGlyLysProAspGlnProVal-64
SEQ. ID. NO. 24539     75-TyrThrLysLeuProGluGluProLysGlyIle-85
SEQ. ID. NO. 24540     97-ThrAspTrpThrAsnProAsnAlaAspThrGluTrpMetAspAlaLysLys-113
SEQ. ID. NO. 24541     125-GlyMetGlyAlaGluAspAlaLeuProPheGlyAsnLysGluGlnAlaGluLysPheAlaLysAspLysGlyGlyLysValValGlyPheAspAspMetProAspThrTyr-161
Hydrophilic Regions - Hopp-Woods
SEQ. ID. NO. 24542     18-ArgGlnAlaGluGluGlyProProProLeu-27
SEQ. ID. NO. 24543     30-GlnIleSerAspArgSerVal-36
SEQ. ID. NO. 24544     46-GluHisAsnGlyProLys-51
SEQ. ID. NO. 24545     58-GlyLysProAspGln-62
SEQ. ID. NO. 24546     77-LysLeuProGluGluProLysGlyIle-85
SEQ. ID. NO. 24547     103-AsnAlaAspThrGluTrpMetAspAlaLysLys-113
SEQ. ID. NO. 24548     127-GlyAlaGluAspAlaLeu-132
SEQ. ID. NO. 24549     135-GlyAsnLysGluGlnAlaGluLysPheAlaLysAspLysGlyGlyLys-150
SEQ. ID. NO. 24550     155-AspAspMetProAsp-159
a917
AMPHI Regions - AMPHI
SEQ. ID. NO. 24551     6-ProLeuAlaValLeuThrAlaLeuLeuLeu-15
SEQ. ID. NO. 24552     37-ValLeuLysIleTyrAsnTrpSerGluTyrValAspProGluThrValAlaAsp-54

TABLE 1-continued

| | |
|---|---|
| SEQ. ID. NO. 24553 | 99-IleLysAlaGlyAlaTyrGlnLysIleAspLysSerLeu-111 |
| SEQ. ID. NO. 24554 | 124-ArgLeuMetAspGlyValAspPro-131 |
| SEQ. ID. NO. 24555 | 152-ArgValLysLysAlaLeu-157 |
| SEQ. ID. NO. 24556 | 188-AspSerAlaAlaGlu-192 |
| SEQ. ID. NO. 24557 | 206-AsnSerSerAsnThrGluAspIleArgGluAlaThr-217 |
| SEQ. ID. NO. 24558 | 292-AlaLysAsnValAlaAsnAlaHisLysTyrIleAsnAspPheLeuAsp-307 |
| SEQ. ID. NO. 24559 | 325-LysProAlaArgGluLeuMetGluAsp-333 |
| Antigenic Index - Jameson-Wolf | |
| SEQ. ID. NO. 24560 | 18-CysGlyGlySerAspLysProProAlaGluLysProAlaProAlaGluAsnArgAsnVal-37 |
| SEQ. ID. NO. 24561 | 44-SerGluTyrValAspProGluThrValAlaAspPheGluLysLysAsnGlyIleLysValThr-64 |
| SEQ. ID. NO. 24562 | 68-TyrAspSerAspGluThrLeuGluSerLysValLeuThrGlyLysSerGlyTyrAsp-86 |
| SEQ. ID. NO. 24563 | 102-GlyAlaTyrGlnLysIleAspLysSerLeuIleProAsnTyrLysHisLeuAsnProGluMetMetArgLeuMetAspGlyValAspProGlyHisGluTyr-135 |
| SEQ. ID. NO. 24564 | 149-AsnThrGluArgValLysLysAlaLeuGlyThrAspLysLeuProAspAsnGln-166 |
| SEQ. ID. NO. 24565 | 171-PheAspProGluTyrThrSerLysLeuLysGlnCysGly-183 |
| SEQ. ID. NO. 24566 | 201-LeuGlyLysAsnProAsnSerSerAsnThrGluAspIleArgGluAlaThrAlaLeuLeuLysLysAsnArgProAsnIleLysArgPheThrSerSerGlyPheIle-236 |
| SEQ. ID. NO. 24567 | 238-AspLeuAlaArgGlyAspThr-244 |
| SEQ. ID. NO. 24568 | 255-AsnIleAlaLysArgArgAlaGluGluAlaGlyGlyLysGluLysIleArgValMetMetProLysGluGlyValGly-280 |
| SEQ. ID. NO. 24569 | 287-ValIleProLysAspAlaLysAsnValAlaAsn-297 |
| SEQ. ID. NO. 24570 | 305-PheLeuAspProGluValSerAlaLysAsnGlyAsn-316 |
| SEQ. ID. NO. 24571 | 320-TyrAlaProSerSerLysProAlaArgGluLeuMetGluAspGluPheLysAsnAspAsnThrIlePheProThrGluGluAspLeuLysAsn-350 |
| SEQ. ID. NO. 24572 | 368-GlnTrpGlnAspValLysAlaGlyLys-376 |
| Hydrophilic Regions - Hopp-Woods | |
| SEQ. ID. NO. 24573 | 19-GlyGlySerAspLysProProAlaGluLysProAlaProAlaGluAsnArgAsnVal-37 |
| SEQ. ID. NO. 24574 | 47-ValAspProGluThrValAlaAspPheGluLysLysAsnGlyIle-61 |
| SEQ. ID. NO. 24575 | 68-TyrAspSerAspGluThrLeuGluSerLysValLeuThr-80 |
| SEQ. ID. NO. 24576 | 105-GlnLysIleAspLysSerLeu-111 |
| SEQ. ID. NO. 24577 | 121-GluMetMetArgLeuMetAspGlyValAspProGlyHis-133 |
| SEQ. ID. NO. 24578 | 149-AsnThrGluArgValLysLysAlaLeuGlyThrAspLysLeuProAspAsnGln-166 |
| SEQ. ID. NO. 24579 | 174-GluTyrThrSerLysLeuLysGln-181 |
| SEQ. ID. NO. 24580 | 204-AsnProAsnSerSerAsnThrGluAspIleArgGluAlaThrAlaLeuLeuLysLysAsnArgProAsnIleLysArgPheThr-231 |
| SEQ. ID. NO. 24581 | 238-AspLeuAlaArgGlyAspThr-244 |
| SEQ. ID. NO. 24582 | 255-AsnIleAlaLysArgArgAlaGluGluAlaGlyGlyLysGluLysIleArgValMetMetProLysGluGly-278 |
| SEQ. ID. NO. 24583 | 290-LysAspAlaLysAsnValAlaAsn-297 |
| SEQ. ID. NO. 24584 | 305-PheLeuAspProGluValSerAlaLysAsn-314 |
| SEQ. ID. NO. 24585 | 322-ProSerSerLysProAlaArgGluLeuMetGluAspGluPheLysAsnAspAsn-339 |
| SEQ. ID. NO. 24586 | 343-ProThrGluGluAspLeuLysAsn-350 |
| SEQ. ID. NO. 24587 | 370-GlnAspValLysAlaGlyLys-376 |
| a919 | |
| AMPHI Regions - AMPHI | |
| SEQ. ID. NO. 24588 | 13-IleAlaAlaAlaIleLeu-18 |
| SEQ. ID. NO. 24589 | 24-LysSerIleGlnThrPheProGln-31 |
| SEQ. ID. NO. 24590 | 37-IleAsnGlyProAspArgProValGlyIleProAsp-48 |
| SEQ. ID. NO. 24591 | 76-AspPheAlaLysSerLeuGln-82 |
| SEQ. ID. NO. 24592 | 98-GlnAspValCysAlaGlnAlaPheGlnThrProVal-109 |
| SEQ. ID. NO. 24593 | 119-GluArgTyrPheThr-123 |
| SEQ. ID. NO. 24594 | 133-LeuAlaGlyThrValThrGlyTyrTyrGlu-142 |
| SEQ. ID. NO. 24595 | 161-GlyIleProAspAspPheIleSerValPro-170 |
| SEQ. ID. NO. 24596 | 176-ArgSerGlyLysAlaLeuValArgIleArgGln-186 |
| SEQ. ID. NO. 24597 | 191-SerGlyThrIleAspAsnThrGlyGlyThr-200 |
| SEQ. ID. NO. 24598 | 308-GlnGlyIleLysAlaTyrMetGlnGlnAsnProGlnArgLeuAlaGluValLeu-325 |
| SEQ. ID. NO. 24599 | 348-AlaLeuGlyThrProLeuMetGlyGluTyrAlaGlyAlaVal-361 |
| SEQ. ID. NO. 24600 | 382-ArgLysAlaLeuAsnArg-387 |
| Antigenic Index - Jameson-Wolf | |
| SEQ. ID. NO. 24601 | 21-CysGlnSerLysSerIleGlnThr-28 |
| SEQ. ID. NO. 24602 | 30-ProGlnProAspThr-34 |
| SEQ. ID. NO. 24603 | 36-ValIleAsnGlyProAspArgProValGlyIleProAspProAlaGlyThr-52 |
| SEQ. ID. NO. 24604 | 54-ValGlyGlyGlyGly-58 |
| SEQ. ID. NO. 24605 | 76-AspPheAlaLysSerLeuGln-82 |
| SEQ. ID. NO. 24606 | 87-GlyCysAlaAsnLeuLysAsnArgGlnGlyTrpGln-98 |
| SEQ. ID. NO. 24607 | 121-TyrPheThrProTrp-125 |
| SEQ. ID. NO. 24608 | 143-ProValLeuLysGlyAspAspArgArgThrAlaGln-154 |
| SEQ. ID. NO. 24609 | 162-IleProAspAspPheIle-167 |
| SEQ. ID. NO. 24610 | 173-AlaGlyLeuArgSerGlyLysAlaLeuValArgIleArgGlnThrGlyLysAsnSerGlyThrIleAspAsnThrGlyGlyThrHis-201 |
| SEQ. ID. NO. 24611 | 215-ThrAlaIleLysGlyArgPheGluGlySerArgPheLeuProTyrHisThrArgAsnGlnIleAsnGlyGlyAlaLeuAspGlyLysAlaPro-245 |
| SEQ. ID. NO. 24612 | 250-AlaGluAspProValGlu-255 |
| SEQ. ID. NO. 24613 | 262-GlnGlySerGlyArgLeuLysThrProSerGlyLysTyrIleArg-276 |
| SEQ. ID. NO. 24614 | 278-GlyTyrAlaAspLysAsnGluHisPro-286 |
| SEQ. ID. NO. 24615 | 293-TyrMetAlaAspLysGlyTyrLeuLysLeuGlyGln-304 |
| SEQ. ID. NO. 24616 | 316-GlnAsnProGlnArgLeuAlaGlu-323 |
| SEQ. ID. NO. 24617 | 326-GlyGlnAsnProSer-330 |
| SEQ. ID. NO. 24618 | 337-LeuThrGlySerSerAsnAspGlyProVal-346 |
| SEQ. ID. NO. 24619 | 359-GlyAlaValAspArgHisTyr-365 |
| SEQ. ID. NO. 24620 | 379-ProValThrArgLysAlaLeuAsn-386 |
| SEQ. ID. NO. 24621 | 393-AspThrGlySerAlaIleLysGlyAlaValArg-403 |
| SEQ. ID. NO. 24622 | 409-GlyTyrGlyAspGluAlaGlyGluLeuAlaGlyLysGlnLysThrThr-424 |
| SEQ. ID. NO. 24623 | 431-LeuProAsnGlyMetLysProGluTyrArgPro-441 |
| Hydrophilic Regions - Hopp-Woods | |
| SEQ. ID. NO. 24624 | 38-AsnGlyProAspArgProValGly-45 |

TABLE 1-continued

| SEQ. ID. NO. 24625 | 90-AsnLeuLysAsnArgGlnGlyTrp-97 |
| SEQ. ID. NO. 24626 | 144-ValLeuLysGlyAspAspArgArgThrAlaGln-154 |
| SEQ. ID. NO. 24627 | 175-LeuArgSerGlyLysAlaLeuValArgIleArgGlnThrGlyLysAsnSerGlyThrIleAspAsnThrGly-198 |
| SEQ. ID. NO. 24628 | 215-ThrAlaIleLysGlyArgPheGluGly-223 |
| SEQ. ID. NO. 24629 | 239-AlaLeuAspGlyLysAla-244 |
| SEQ. ID. NO. 24630 | 250-AlaGluAspProVal-254 |
| SEQ. ID. NO. 24631 | 265-GlyArgLeuLysThrProSer-271 |
| SEQ. ID. NO. 24632 | 279-TyrAlaAspLysAsnGluHis-285 |
| SEQ. ID. NO. 24633 | 317-AsnProGlnArgLeuAlaGlu-323 |
| SEQ. ID. NO. 24634 | 337-LeuThrGlySerSerAsnAspGlyPro-345 |
| SEQ. ID. NO. 24635 | 380-ValThrArgLysAlaLeuAsn-386 |
| SEQ. ID. NO. 24636 | 393-AspThrGlySerAlaIle-398 |
| SEQ. ID. NO. 24637 | 412-AspGluAlaGlyGluLeuAlaGlyLysGlnLysThr-423 |
| SEQ. ID. NO. 24638 | 434-GlyMetLysProGluTyrArgPro-441 | a919
AMPHI Regions - AMPHI

| SEQ. ID. NO. 24639 | 13-IleAlaAlaAlaIleLeu-18 |
| SEQ. ID. NO. 24640 | 24-LysSerIleGlnThrPheProGln-31 |
| SEQ. ID. NO. 24641 | 37-IleAsnGlyProAspArgProValGlyIleProAsp-48 |
| SEQ. ID. NO. 24642 | 76-AspPheAlaLysSerLeuGln-82 |
| SEQ. ID. NO. 24643 | 98-GlnAspValCysAlaGlnAlaPheGlnThrProVal-109 |
| SEQ. ID. NO. 24644 | 119-GluArgTyrPheThr-123 |
| SEQ. ID. NO. 24645 | 133-LeuAlaGlyThrValThrGlyTyrTyrGlu-142 |
| SEQ. ID. NO. 24646 | 161-GlyIleProAspAspPheIleSerValPro-170 |
| SEQ. ID. NO. 24647 | 176-ArgSerGlyLysAlaLeuValArgIleArgGln-186 |
| SEQ. ID. NO. 24648 | 191-SerGlyThrIleAspAsnThrGlyGlyThr-200 |
| SEQ. ID. NO. 24649 | 308-GlnGlyIleLysAlaTyrMetGlnGlnAsnProGlnArgLeuAlaGluValLeu-325 |
| SEQ. ID. NO. 24650 | 348-AlaLeuGlyThrProLeuMetGlyGluTyrAlaGlyAlaVal-361 |
| SEQ. ID. NO. 24651 | 382-ArgLysAlaLeuAsnArg-387 |

Antigenic Index - Jameson-Wolf

| SEQ. ID. NO. 24652 | 21-CysGlnSerLysSerIleGlnThr-28 |
| SEQ. ID. NO. 24653 | 30-ProGlnProAspThr-34 |
| SEQ. ID. NO. 24654 | 36-ValIleAsnGlyProAspArgProValGlyIleProAspProAlaGlyThr-52 |
| SEQ. ID. NO. 24655 | 54-ValGlyGlyGlyGly-58 |
| SEQ. ID. NO. 24656 | 76-AspPheAlaLysSerLeuGln-82 |
| SEQ. ID. NO. 24657 | 87-GlyCysAlaAsnLeuLysAsnArgGlnGlyTrpGln-98 |
| SEQ. ID. NO. 24658 | 121-TyrPheThrProTrp-125 |
| SEQ. ID. NO. 24659 | 143-ProValLeuLysGlyAspAspArgArgThrAlaGln-154 |
| SEQ. ID. NO. 24660 | 162-IleProAspAspPheIle-167 |
| SEQ. ID. NO. 24661 | 173-AlaGlyLeuArgSerGlyLysAlaLeuValArgIleArgGlnThrGlyLysAsnSerGlyThrIleAspAsnThrGlyGlyThrHis-201 |
| SEQ. ID. NO. 24662 | 215-ThrAlaIleLysGlyArgPheGluGlySerArgPheLeuProTyrHisThrArgAsnGlnIleAsnGlyGlyAlaLeuAspGlyLysAlaPro-245 |
| SEQ. ID. NO. 24663 | 250-AlaGluAspProValGlu-255 |
| SEQ. ID. NO. 24664 | 262-GlnGlySerGlyArgLeuLysThrProSerGlyLysTyrIleArg-276 |
| SEQ. ID. NO. 24665 | 278-GlyTyrAlaAspLysAsnGluHisPro-286 |
| SEQ. ID. NO. 24666 | 293-TyrMetAlaAspLysGlyTyrLeuLysLeuGlyGln-304 |
| SEQ. ID. NO. 24667 | 316-GlnAsnProGlnArgLeuAlaGlu-323 |
| SEQ. ID. NO. 24668 | 326-GlyGlnAsnProSer-330 |
| SEQ. ID. NO. 24669 | 337-LeuThrGlySerSerAsnAspGlyProVal-346 |
| SEQ. ID. NO. 24670 | 359-GlyAlaValAspArgHisTyr-365 |
| SEQ. ID. NO. 24671 | 379-ProValThrArgLysAlaLeuAsn-386 |
| SEQ. ID. NO. 24672 | 393-AspThrGlySerAlaIleLysGlyAlaValArg-403 |
| SEQ. ID. NO. 24673 | 409-GlyTyrGlyAspGluAlaGlyGluLeuAlaGlyLysGlnLysThrThr-424 |
| SEQ. ID. NO. 24674 | 431-LeuProAsnGlyMetLysProGluTyrArgPro-441 |

Hydrophilic Regions - Hopp-Woods

| SEQ. ID. NO. 24675 | 38-AsnGlyProAspArgProValGly-45 |
| SEQ. ID. NO. 24676 | 90-AsnLeuLysAsnArgGlnGlyTrp-97 |
| SEQ. ID. NO. 24677 | 144-ValLeuLysGlyAspAspArgArgThrAlaGln-154 |
| SEQ. ID. NO. 24678 | 175-LeuArgSerGlyLysAlaLeuValArgIleArgGlnThrGlyLysAsnSerGlyThrIleAspAsnThrGly-198 |
| SEQ. ID. NO. 24679 | 215-ThrAlaIleLysGlyArgPheGluGly-223 |
| SEQ. ID. NO. 24680 | 239-AlaLeuAspGlyLysAla-244 |
| SEQ. ID. NO. 24681 | 250-AlaGluAspProVal-254 |
| SEQ. ID. NO. 24682 | 265-GlyArgLeuLysThrProSer-271 |
| SEQ. ID. NO. 24683 | 279-TyrAlaAspLysAsnGluHis-285 |
| SEQ. ID. NO. 24684 | 317-AsnProGlnArgLeuAlaGlu-323 |
| SEQ. ID. NO. 24685 | 337-LeuThrGlySerSerAsnAspGlyPro-345 |
| SEQ. ID. NO. 24686 | 380-ValThrArgLysAlaLeuAsn-386 |
| SEQ. ID. NO. 24687 | 393-AspThrGlySerAlaIle-398 |
| SEQ. ID. NO. 24688 | 412-AspGluAlaGlyGluLeuAlaGlyLysGlnLysThr-423 |
| SEQ. ID. NO. 24689 | 434-GlyMetLysProGluTyrArgPro-441 | a920-2
AMPHI Regions - AMPHI

| SEQ. ID. NO. 24690 | 43-GlyGluPheProGluLeuGluProIleAla-52 |
| SEQ. ID. NO. 24691 | 118-IleLysGlnMetProAsp-123 |
| SEQ. ID. NO. 24692 | 135-LysAsnIleValAsnVal-140 |
| SEQ. ID. NO. 24693 | 163-LeuAspAsnProAlaAsn-168 |
| SEQ. ID. NO. 24694 | 190-ThrValThrAlaThrPheAspGlyPheAspThrSerAspArgSerLys-205 |
| SEQ. ID. NO. 24695 | 212-GlnAlaPheSerAspSerThr-218 |

Antigenic Index - Jameson-Wolf

| SEQ. ID. NO. 24696 | 40-LeuGlyTyrGlyGlu-44 |
| SEQ. ID. NO. 24697 | 49-GluProIleAlaLysAspArgLeu-56 |

TABLE 1-continued

SEQ. ID. NO. 24698    66-ValThrGluLysGlyLysGluAsnMetIle-75
SEQ. ID. NO. 24699    82-TyrGlnTyrArgSerAsnArgProValLysAspGlySerTyr-95
SEQ. ID. NO. 24700    104-ThrPheTrpSerLysAsnLysAlaGlyTrp-113
SEQ. ID. NO. 24701    120-GlnMetProAspAlaSerTyrCysGluGlnThrArgMetPheGlyLysAsnIleValAsnValGlyHisGluSerAlaAspThr-147
SEQ. ID. NO. 24702    152-LysProValGlyGlnAsnLeuGlu-159
SEQ. ID. NO. 24703    162-ProLeuAspAsnProAla-167
SEQ. ID. NO. 24704    173-GluArgPheLysVal-177
SEQ. ID. NO. 24705    181-PheArgGlyGluProLeuProAsnAla-189
SEQ. ID. NO. 24706    194-ThrPheAspGlyPheAspThrSerAspArgSerLysThrHisLysThrGluAla-211
SEQ. ID. NO. 24707    213-AlaPheSerAspSerThrAspAspLysGlyGluValAsp-225
SEQ. ID. NO. 24708    237-AsnValGluHisLysAlaAspPheProAspGlnSerValCysGlnLysGlnAlaAsnTyrSer-257
Hydrophilic Regions - Hopp-Woods
SEQ. ID. NO. 24709    49-GluProIleAlaLysAspArgLeu-56
SEQ. ID. NO. 24710    66-ValThrGluLysGlyLysGluAsnMetIle-75
SEQ. ID. NO. 24711    85-ArgSerAsnArgProValLysAspGlySer-94
SEQ. ID. NO. 24712    107-SerLysAsnLysAlaGlyTrp-113
SEQ. ID. NO. 24713    128-GluGlnThrArgMetPheGly-134
SEQ. ID. NO. 24714    142-HisGluSerAlaAsp-146
SEQ. ID. NO. 24715    173-GluArgPheLysVal-177
SEQ. ID. NO. 24716    196-AspGlyPheAspThrSerAspArgSerLysThrHisLysThrGluAla-211
SEQ. ID. NO. 24717    213-AlaPheSerAspSerThrAspAspLysGlyGluValAsp-225
SEQ. ID. NO. 24718    237-AsnValGluHisLysAlaAspPheProAsp-246
SEQ. ID. NO. 24719    248-SerValCysGlnLys-252
a921
AMPHI Regions - AMPHI
SEQ. ID. NO. 24720    10-IleValAlaValLeuSerGlyCysGlnSerIleTyrValProThrLeuThrGluIleProValAsn-31
SEQ. ID. NO. 24721    33-IleAsnThrValLysThr-38
SEQ. ID. NO. 24722    51-HisTrpThrAspValAlaLysIleSerAspGlu-61
SEQ. ID. NO. 24723    72-GlyLysMetThrLysValGlnAlaAlaGlnTyrLeuAsnAsnPheArgLys-88
SEQ. ID. NO. 24724    98-AspSerMetTyrGluIleTyrLeuArg-106
SEQ. ID. NO. 24725    126-GlnAsnAlaLeuArgGlyTrpGlnGlnArg-135
Antigenic Index - Jameson-Wolf
SEQ. ID. NO. 24726    36-ValLysThrGluAlaProAlaLysGlyPheArg-46
SEQ. ID. NO. 24727    56-AlaLysIleSerAspGluAlaThrArg-64
SEQ. ID. NO. 24728    72-GlyLysMetThrLys-76
SEQ. ID. NO. 24729    84-AsnAsnPheArgLysArgLeuValGlyArgAsnAlaValAspAspSerMet-100
SEQ. ID. NO. 24730    108-AlaIleAspSerGlnArgGlyAlaIleAsnThrGluGlnSerLys-122
SEQ. ID. NO. 24731    128-AlaLeuArgGlyTrpGlnGlnArgTrpLysAsnMetAspValLysProAsnAsnProAla-147
Hydrophilic Regions - Hopp-Woods
SEQ. ID. NO. 24732    36-ValLysThrGluAlaProAlaLysGlyPheArg-46
SEQ. ID. NO. 24733    56-AlaLysIleSerAspGluAlaThrArg-64
SEQ. ID. NO. 24734    86-PheArgLysArgLeuValGly-92
SEQ. ID. NO. 24735    94-AsnAlaValAspAspSerMet-100
SEQ. ID. NO. 24736    108-AlaIleAspSerGlnArgGlyAlaIleAsnThrGluGlnSerLys-122
SEQ. ID. NO. 24737    136-TrpLysAsnMetAspValLysProAsnAsn-145
a922
AMPHI Regions - AMPHI
SEQ. ID. NO. 24738    16-LeuSerAlaCysThr-20
SEQ. ID. NO. 24739    28-ArgAlaAsnGluAlaGlnAlaPro-35
SEQ. ID. NO. 24740    72-ValArgArgPheValAspAsp-78
SEQ. ID. NO. 24741    89-GluTrpGlnAspPhePheAspLys-96
SEQ. ID. NO. 24742    104-ValLysIleMetHis-108
SEQ. ID. NO. 24743    144-AspAspValAlaGln-148
SEQ. ID. NO. 24744    172-GlySerPheArgValAlaAspAlaLeu-180
SEQ. ID. NO. 24745    196-LysGluLeuValGluLeuLeuLysLeuAla-205
SEQ. ID. NO. 24746    222-AlaMetGlyMetPro-226
SEQ. ID. NO. 24747    245-HisArgAspIleTrpGlyAsnValGlyAspValAlaAlaSerIleAlaAsnTyrMetLysGlnHis-266
SEQ. ID. NO. 24748    298-ArgThrValAlaAspLeuLysAlaTyr-306
SEQ. ID. NO. 24749    335-TyrLeuGlyLeuAsnAsnPheTyrThr-343
Antigenic Index - Jameson-Wolf
SEQ. ID. NO. 24750    1-MetLysAsnArgLysIleLeu-7
SEQ. ID. NO. 24751    22-MetGluAlaArgProProArgAlaAsnGluAlaGlnAlaProArgAlaAspGluMetLysLysGluSerArgProAlaPhe-48
SEQ. ID. NO. 24752    61-ValSerAspSerGlyPhe-66
SEQ. ID. NO. 24753    70-AlaAsnValArgArgPheValAspAspGluValGlyLysGlyAspPheSerArgAlaGluTrp-90
SEQ. ID. NO. 24754    107-MetHisArgProSerThrSerArgPro-115
SEQ. ID. NO. 24755    120-ArgThrGlyAsnSerGlyLysAlaLysPheArgGlyAlaArgArgPheTyrAlaGluAsnArgAlaLeuIle-143
SEQ. ID. NO. 24756    145-AspValAlaGlnLysTyrGlyVal-152
SEQ. ID. NO. 24757    163-IleGluThrAsnTyrGlyLysAsnThrGlySer-173
SEQ. ID. NO. 24758    186-AspTyrProArgArgAlaGlyPhePhe-194
SEQ. ID. NO. 24759    203-LysLeuAlaLysGluGluGlyGlyAsp-211
SEQ. ID. NO. 24760    229-MetProSerSerTyrArgLysTrpAlaValAspTyrAspGlyAspGlyHisArgAspIle-248
SEQ. ID. NO. 24761    266-HisGlyTrpArgThrGlyGlyLys-273
SEQ. ID. NO. 24762    281-AlaProGlyAlaAsp-285
SEQ. ID. NO. 24763    290-IleGlyGluLysThrAlaLeu-296
SEQ. ID. NO. 24764    310-ProGlyGluLeuAlaAspAspGluLysAlaVal-321
SEQ. ID. NO. 24765    326-GluThrAlaProGly-330
SEQ. ID. NO. 24766    357-ValArgAspIleAlaAsnSerLeuGlyGlyProGlyLeu-369
Hydrophilic Regions - Hopp-Woods
SEQ. ID. NO. 24767    1-MetLysAsnArgLysIleLeu-7
SEQ. ID. NO. 24768    22-MetGluAlaArgProProArgAlaAsnGluAlaGlnAlaProArgAlaAspGluMetLysLysGluSerArgProAlaPhe-48

TABLE 1-continued

| | |
|---|---|
| SEQ. ID. NO. 24769 | 70-AlaAsnValArgArgPheValAspAspGluValGlyLysGlyAspPheSerArgAlaGluTrp-90 |
| SEQ. ID. NO. 24770 | 122-GlyAsnSerGlyLysAlaLysPheArgGlyAlaArgArgPheTyrAlaGluAsnArgAlaLeuIle-143 |
| SEQ. ID. NO. 24771 | 166-AsnTyrGlyLysAsnThrGly-172 |
| SEQ. ID. NO. 24772 | 187-TyrProArgArgAlaGlyPhePhe-194 |
| SEQ. ID. NO. 24773 | 203-LysLeuAlaLysGluGluGlyGlyAsp-211 |
| SEQ. ID. NO. 24774 | 240-TyrAspGlyAspGlyHisArgAspIle-248 |
| SEQ. ID. NO. 24775 | 290-IleGlyGluLysThrAlaLeu-296 |
| SEQ. ID. NO. 24776 | 310-ProGlyGluGluLeuAlaAspAspGluLysAlaVal-321 |
| SEQ. ID. NO. 24777 | 357-ValArgAspIleAla-361 | a923-2
AMPHI Regions - AMPHI

| | |
|---|---|
| SEQ. ID. NO. 24778 | 9-LeuMetAlaCysAlaAlaPheLeu-16 |
| SEQ. ID. NO. 24779 | 26-LeuGlyAlaCysTyrAlaIleLeuSerLeuTyrAla-37 |
| SEQ. ID. NO. 24780 | 63-ProAlaLeuPheGlyGlyTrpAlaGly-71 |

Antigenic Index - Jameson-Wolf

| | |
|---|---|
| SEQ. ID. NO. 24781 | 43-IleAspLysArgArgAlaValArgGlyLysArgArgIleProGluHisArgLeu-60 |
| SEQ. ID. NO. 24782 | 77-ArgIlePheArgHisLysThrAlaLysLysArgPhe-88 |

Hydrophilic Regions - Hopp-Woods

| | |
|---|---|
| SEQ. ID. NO. 24783 | 43-IleAspLysArgArgAlaValArgGlyLysArgArgIleProGluHisArgLeu-60 |
| SEQ. ID. NO. 24784 | 77-ArgIlePheArgHisLysThrAlaLysLysArgPhe-88 | a925-1
AMPHI Regions - AMPHI

| | |
|---|---|
| SEQ. ID. NO. 24785 | 66-LysCysGlyGlnThrAlaGln-72 |
| SEQ. ID. NO. 24786 | 90-HisGlnAlaAlaIleGluGlnLeuLys-98 |
| SEQ. ID. NO. 24787 | 105-PheAspGluLeuGlu-109 |

Antigenic Index - Jameson-Wolf

| | |
|---|---|
| SEQ. ID. NO. 24788 | 6-PheThrGlyLysGluGluSerMetLeuLeuSerGluLysAspGlyAla-21 |
| SEQ. ID. NO. 24789 | 25-AsnThrGlyIleGly-29 |
| SEQ. ID. NO. 24790 | 31-IleProIleLysLeuSerAspAspGlyLysGluLeuTyrValGluArgArgGlnTyrValLysThrAspAlaAlaMetLysAspLysIleIleAlaHisGlnLysLysCysGlyGlnThr-70 |
| SEQ. ID. NO. 24791 | 75-LeuAspAlaArgAsnAlaLeuProSerAsnGlnThrTyrGln-88 |
| SEQ. ID. NO. 24792 | 95-GluGlnLeuLysArgArgPheGluAlaGluPheAspGluLeuGluLysGluIleLysCysAsnGlyLysProThr-119 |

Hydrophilic Regions - Hopp-Woods

| | |
|---|---|
| SEQ. ID. NO. 24793 | 7-ThrGlyLysGluGluSerMetLeuLeuSerGluLysAspGlyAla-21 |
| SEQ. ID. NO. 24794 | 31-IleProIleLysLeuSerAspAspGlyLysGluLeuTyrValGluArgArgGlnTyrValLysThrAspAlaAlaMetLysAspLysIleIleAlaHisGlnLysLysCysGlyGln-69 |
| SEQ. ID. NO. 24795 | 75-LeuAspAlaArgAsnAlaLeu-81 |
| SEQ. ID. NO. 24796 | 95-GluGlnLeuLysArgArgPheGluAlaGluPheAspGluLeuGluLysGluIleLysCysAsnGlyLys-117 | a926
AMPHI Regions - AMPHI

| | |
|---|---|
| SEQ. ID. NO. 24797 | 32-HisThrArgSerPhe-36 |
| SEQ. ID. NO. 24798 | 72-LeuGlySerThrLeuGlyGln-78 |
| SEQ. ID. NO. 24799 | 98-AlaGluSerAlaGluGluLeuSerArgGln-107 |
| SEQ. ID. NO. 24800 | 129-GlyAlaProTyrArgIleLeuProAspGlyIle-139 |
| SEQ. ID. NO. 24801 | 151-AlaAspSerGlyGlyGlnVal-157 |

Antigenic Index - Jameson-Wolf

| | |
|---|---|
| SEQ. ID. NO. 24802 | 19-LeuProGlnAsnAsnGluAsnLeuTrpGlnProSerGluHisThrArgSerPheThrAlaGluGlyArgLeuAlaValLysAlaGluGlyLysGlySerTyrAla-53 |
| SEQ. ID. NO. 24803 | 70-ThrProLeuGlySer-74 |
| SEQ. ID. NO. 24804 | 79-LeuCysGlnAspArgAspGlyAlaLeu-87 |
| SEQ. ID. NO. 24805 | 89-ValAspGlyLysGlyAsnValTyr-96 |
| SEQ. ID. NO. 24806 | 99-GluSerAlaGluGluLeuSerArg-106 |
| SEQ. ID. NO. 24807 | 122-AlaAspGlyArgProValAlaGlyAlaPro-131 |
| SEQ. ID. NO. 24808 | 134-IleLeuProAspGlyIleLeu-140 |
| SEQ. ID. NO. 24809 | 148-GlyArgThrAlaAspSerGlyGlyGln-156 |
| SEQ. ID. NO. 24810 | 177-GlyMetProSerGluThrGluThrGlnGluGlnCysAla-189 |

Hydrophilic Regions - Hopp-Woods

| | |
|---|---|
| SEQ. ID. NO. 24811 | 36-PheThrAlaGluGlyArgLeuAlaValLysAlaGluGlyLysGlySer-51 |
| SEQ. ID. NO. 24812 | 80-CysGlnAspArgAspGlyAlaLeu-87 |
| SEQ. ID. NO. 24813 | 89-ValAspGlyLysGly-93 |
| SEQ. ID. NO. 24814 | 99-GluSerAlaGluGluLeuSerArg-106 |
| SEQ. ID. NO. 24815 | 123-AspGlyArgProValAla-128 |
| SEQ. ID. NO. 24816 | 149-ArgThrAlaAspSerGlyGlyGln-156 |
| SEQ. ID. NO. 24817 | 180-SerGluThrGluThrGlnGluGlnCysAla-189 | a927
AMPHI Regions - AMPHI

| | |
|---|---|
| SEQ. ID. NO. 24818 | 13-LeuLeuSerAlaCysSer-18 |
| SEQ. ID. NO. 24819 | 48-SerTyrAspValAlaArgAspPheTyrLysGlu-58 |
| SEQ. ID. NO. 24820 | 120-LysGlyTrpGlnGlnAlaLeuPro-127 |
| SEQ. ID. NO. 24821 | 145-AsnProLysGlnIleArgAspTrpAsnAspLeuAlaLysAspGly-159 |
| SEQ. ID. NO. 24822 | 197-LysLeuValAlaSerIleLeu-203 |

Antigenic Index - Jameson-Wolf

| | |
|---|---|
| SEQ. ID. NO. 24823 | 18-SerProAlaAlaAspSerAsnHisProSerGlyGlnAsnAlaProAlaAsnThrGluSerAspGlyLysAsnIleThr-43 |
| SEQ. ID. NO. 24824 | 48-SerTyrAspValAlaArgAspPheTyrLysGluTyrAsnPro-61 |
| SEQ. ID. NO. 24825 | 67-TyrGlnSerGluHisProGlyThrSer-75 |
| SEQ. ID. NO. 24826 | 80-GlnSerHisGlyGlySerSerLysGln-88 |
| SEQ. ID. NO. 24827 | 104-AsnGlnSerSerAspIleAspLeuLeuGluLysLysGlyLeuVal-118 |
| SEQ. ID. NO. 24828 | 126-LeuProAspHisAlaAlaProTyrThr-134 |
| SEQ. ID. NO. 24829 | 142-ArgLysAsnAsnProLysGlnIleArgAspTrpAsnAspLeuAlaLysAspGlyVal-160 |
| SEQ. ID. NO. 24830 | 166-AsnProLysThrSerGlyAsnGlyArg-174 |

TABLE 1-continued

| | |
|---|---|
| SEQ. ID. NO. 24831 | 185-LeuLysThrThrAsnGlyAsnGluGlnGluAlaGlnLys-197 |
| SEQ. ID. NO. 24832 | 203-LeuLysAsnThrProValPheGluAsnGlyGlyArgAlaProPrProProSerHisAsnAlaThrSer-225 |
| SEQ. ID. NO. 24833 | 230-SerLeuLeuLysThrLysProThrThrSerAlaLysAsn-242 |

Hydrophilic Regions - Hopp-Woods

| | |
|---|---|
| SEQ. ID. NO. 24834 | 19-ProAlaAlaAspSerAsnHisProSer-27 |
| SEQ. ID. NO. 24835 | 33-AlaAsnThrGluSerAspGlyLysAsn-41 |
| SEQ. ID. NO. 24836 | 50-AspValAlaArgAspPheTyrLys-57 |
| SEQ. ID. NO. 24837 | 67-TyrGlnSerGluHisProGly-73 |
| SEQ. ID. NO. 24838 | 82-HisGlyGlySerSerLysGln-88 |
| SEQ. ID. NO. 24839 | 105-GlnSerSerAspIleAspLeuLeuGluLysLysGlyLeuVal-118 |
| SEQ. ID. NO. 24840 | 142-ArgLysAsnAsnProLysGlnIleArgAspTrpAsnAspLeuAlaLysAspGlyVal-160 |
| SEQ. ID. NO. 24841 | 167-ProLysThrSerGlyAsnGly-173 |
| SEQ. ID. NO. 24842 | 187-ThrThrAsnGlyAsnGluGlnGluAlaGlnLys-197 |
| SEQ. ID. NO. 24843 | 211-AsnGlyGlyArgAlaProPro-217 |
| SEQ. ID. NO. 24844 | 232-LeuLysThrLysProThrThrSerAlaLysAsn-242 | a929
AMPHI Regions - AMPHI

| | |
|---|---|
| SEQ. ID. NO. 24845 | 25-ValProAspGlyValLys-30 |
| SEQ. ID. NO. 24846 | 34-TrpThrLeuLeuAlaMetPheIleGlyValIleAlaAlaIleIle-48 |
| SEQ. ID. NO. 24847 | 76-GlyAlaAlaMetSerAspAlaLeuSerAlaPhe-86 |
| SEQ. ID. NO. 24848 | 155-HisProIleMetGlnSerIleAlaGlySerTyrGlySerAsnProAlaLys-171 |
| SEQ. ID. NO. 24849 | 180-TyrLeuAlaLeuVal-184 |
| SEQ. ID. NO. 24850 | 204-ProLeuIleValAsnLeuIleAlaGluAsnLeuGly-215 |
| SEQ. ID. NO. 24851 | 233-GlyValIleAlaPhePhe-238 |
| SEQ. ID. NO. 24852 | 265-ArgLeuArgGluMetGlyLysMetSer-273 |
| SEQ. ID. NO. 24853 | 280-AlaAlaIlePheGlyIle-285 |
| SEQ. ID. NO. 24854 | 355-LeuGlyLeuIleLysTrpPheSerGlyValLeuAlaGluSerValGlyGlyLeu-372 |
| SEQ. ID. NO. 24855 | 398-ThrAlaHisIleThrAlaMetPheGlyAlaPhePheAla-410 |
| SEQ. ID. NO. 24856 | 452-TyrThrThrMetGlyGluTrpTrp-459 |

Antigenic Index - Jameson-Wolf

| | |
|---|---|
| SEQ. ID. NO. 24857 | 25-ValProAspGlyValLysProGln-32 |
| SEQ. ID. NO. 24858 | 71-ThrAlaAspLysProGlyAlaAlaMet-79 |
| SEQ. ID. NO. 24859 | 122-GlyArgLysThrLeuGlyIle-128 |
| SEQ. ID. NO. 24860 | 143-ThrProSerAsnThrAlaArgGlyGlyGly-152 |
| SEQ. ID. NO. 24861 | 163-GlySerTyrGlySerAsnProAlaLysGlyThrGluGlyLysMetGlyLys-179 |
| SEQ. ID. NO. 24862 | 187-HisSerAsnProIleSer-192 |
| SEQ. ID. NO. 24863 | 213-AsnLeuGlySerSerPhe-218 |
| SEQ. ID. NO. 24864 | 248-TyrProProGluIleLysGluThrProAsn-257 |
| SEQ. ID. NO. 24865 | 261-PheAlaLysAspArgLeuArgGluMetGlyLysMetSerAlaAspGluIle-277 |
| SEQ. ID. NO. 24866 | 328-AspValLeuLysGluLysSerAlaTrp-336 |

Hydrophilic Regions - Hopp-Woods

| | |
|---|---|
| SEQ. ID. NO. 24867 | 71-ThrAlaAspLysProGlyAlaAlaMet-79 |
| SEQ. ID. NO. 24868 | 146-AsnThrAlaArgGly-150 |
| SEQ. ID. NO. 24869 | 168-AsnProAlaLysGlyThrGluGlyLysMetGlyLys-179 |
| SEQ. ID. NO. 24870 | 250-ProGluIleLysGluThrProAsn-257 |
| SEQ. ID. NO. 24871 | 261-PheAlaLysAspArgLeuArgGluMetGlyLysMetSerAlaAspGluIle-277 |
| SEQ. ID. NO. 24872 | 328-AspValLeuLysGluLysSerAlaTrp-336 | a931
AMPHI Regions - AMPHI

| | |
|---|---|
| SEQ. ID. NO. 24873 | 43-LysAlaProLysThrValAlaAsnPheValArgTyrAlaArgLys-57 |
| SEQ. ID. NO. 24874 | 67-ArgValIleGlyGly-71 |
| SEQ. ID. NO. 24875 | 81-GluAspLeuAlaGlnLysAlaSerAspLys-90 |
| SEQ. ID. NO. 24876 | 94-AsnGluSerGlyAsnGlyLeuLysAsnThrValGly-105 |
| SEQ. ID. NO. 24877 | 107-IleAlaMetAlaArgThrAlaAspProAsp-116 |
| SEQ. ID. NO. 24878 | 120-SerGlnPhePheIle-124 |
| SEQ. ID. NO. 24879 | 142-ThrValPheGlyArgValGluSerGlyMetAsnThrValSerLysIleAlaArgValLysThrAlaThrArgGlyPhe-167 |

Antigenic Index - Jameson-Wolf

| | |
|---|---|
| SEQ. ID. NO. 24880 | 1-MetLysProLysPhe-5 |
| SEQ. ID. NO. 24881 | 30-ThrAspMetGlyAsn-34 |
| SEQ. ID. NO. 24882 | 38-ValLeuAspGluSerLysAlaProLysThr-47 |
| SEQ. ID. NO. 24883 | 53-ArgTyrAlaArgLysGlyPheTyrAspAsnThrIle-64 |
| SEQ. ID. NO. 24884 | 76-GlyGlyGlyLeuThrGluAspLeuAlaGlnLysAlaSerAspLysAlaValAlaAsnGluSerGlyAsnGlyLeuLysAsnThrVal-104 |
| SEQ. ID. NO. 24885 | 111-ArgThrAlaAspProAspSerAlaThr-119 |
| SEQ. ID. NO. 24886 | 127-ValAspAsnAspSerLeuAsnTyrLysAsnGlyGln-138 |
| SEQ. ID. NO. 24887 | 145-GlyArgValGluSerGlyMetAsnThrVal-154 |
| SEQ. ID. NO. 24888 | 156-LysIleAlaArgValLysThrAlaThrArgGlyPhe-167 |
| SEQ. ID. NO. 24889 | 176-ValLysIleArgArg-180 |

Hydrophilic Regions - Hopp-Woods

| | |
|---|---|
| SEQ. ID. NO. 24890 | 1-MetLysProLysPhe-5 |
| SEQ. ID. NO. 24891 | 30-ThrAspMetGlyAsn-34 |
| SEQ. ID. NO. 24892 | 38-ValLeuAspGluSerLysAlaProLysThr-47 |
| SEQ. ID. NO. 24893 | 78-GlyLeuThrGluAspLeuAlaGlnLysAlaSerAspLysAlaValAlaAsnGluSerGlyAsnGlyLeu-100 |
| SEQ. ID. NO. 24894 | 111-ArgThrAlaAspProAspSerAlaThr-119 |
| SEQ. ID. NO. 24895 | 127-ValAspAsnAspSerLeuAsn-133 |
| SEQ. ID. NO. 24896 | 145-GlyArgValGluSerGlyMet-151 |
| SEQ. ID. NO. 24897 | 156-LysIleAlaArgValLysThrAlaThr-164 |
| SEQ. ID. NO. 24898 | 176-ValLysIleArgArg-180 | a933
AMPHI Regions - AMPHI

| | |
|---|---|
| SEQ. ID. NO. 24899 | 27-AsnIleProAlaLeuPheProLysHisProPheAspProPheGluAsnIleAsnAsnSerLysArg-48 |

TABLE 1-continued

| | |
|---|---|
| SEQ. ID. NO. 24900 | 63-GlyPheAlaGlnGlyLeu-68 |
| SEQ. ID. NO. 24901 | 78-GluLysProIleArgGlnTyrPheLysGluCysLeuAsnThrGly-92 |
| SEQ. ID. NO. 24902 | 95-SerAspAspThrCys-99 |
| SEQ. ID. NO. 24903 | 131-ValGlyAsnTyrIleGluTrpLeu-138 |
| SEQ. ID. NO. 24904 | 155-AspValAspProPheHisTyrIleGluVal-164 |
| SEQ. ID. NO. 24905 | 257-GluAsnProIleAspAspLeuLysSerLeuAspGlyHisGlnIleIleLysValAsn-275 |
| SEQ. ID. NO. 24906 | 304-GlyPhePheThrLys-308 |
| SEQ. ID. NO. 24907 | 351-TrpLeuArgValIleAspGlyHisSerAsn-360 |
| SEQ. ID. NO. 24908 | 426-AlaGlyIleTyrAlaThrTrpHis-433 |
| SEQ. ID. NO. 24909 | 447-TrpValGlnTyrGln-451 |
| SEQ. ID. NO. 24910 | 462-AlaThrGluArgPheThr-467 |
| SEQ. ID. NO. 24911 | 469-LysGlyIleThrAlaSer-474 |
| SEQ. ID. NO. 24912 | 478-GlyTyrAsnAlaLeuLeuAla-484 |
| SEQ. ID. NO. 24913 | 543-LeuTyrLysAsnIleAlaIleGlu-550 |
| SEQ. ID. NO. 24914 | 552-PheAlaAlaValAsn-556 |
| SEQ. ID. NO. 24915 | 601-PheAsnArgGlnThrGly-606 |
| Antigenic Index - Jameson-Wolf | |
| SEQ. ID. NO. 24916 | 1-LysLysLeuArgAspArgAsnSerGluTyrTrpLysGluGluThrTyrHisIleLysSerAsnAsnArgValTyrPro-26 |
| SEQ. ID. NO. 24917 | 33-ProLysHisProPheAspProPheGluAsnIleAsnAsnSerLysArgIleSerPheTyrAspLysGluTyrThrGluAspTyr-60 |
| SEQ. ID. NO. 24918 | 69-GlyValAlaLysArgAsnGlyGluThrGluLysProIleArg-82 |
| SEQ. ID. NO. 24919 | 88-CysLeuAsnThrGlyLysTyrSerAspAspThrCysLysSerGlnGlnSer-104 |
| SEQ. ID. NO. 24920 | 108-ValArgSerAspIle-112 |
| SEQ. ID. NO. 24921 | 117-ThrLysIleLysAsnSerHisIleAsnSerGluIle-128 |
| SEQ. ID. NO. 24922 | 145-LeuSerSerSerGlnGluHisLeuTyrSerAspValAspProPheHis-160 |
| SEQ. ID. NO. 24923 | 163-GluValThrAspAsnSerHis-169 |
| SEQ. ID. NO. 24924 | 178-AspGluPheArgLeuGluAsnSerLeuTrpGluProArgTrpAspSerAspValGlyGluLeuLysThrThrAsnAlaAspIleArgPheAsnThr LysSerGluSerLeuLeuValLysGluAspTyrAlaGlyGlyAlaArgPhe-226 |
| SEQ. ID. NO. 24925 | 231-GlyLeuLysAspLysValProGluThrPro-240 |
| SEQ. ID. NO. 24926 | 244-PheGluLysAsnIleThrGlyThrSer-252 |
| SEQ. ID. NO. 24927 | 255-IlePheGluAsnProIleAspAspLeuLysSerLeuAspGlyHisGlnIleIle-272 |
| SEQ. ID. NO. 24928 | 274-ValAsnGlyThrAlaAspLysHisAlaPheArgLeuSerGlyLysHisGlnLysGly-292 |
| SEQ. ID. NO. 24929 | 298-LeuGlnGlnArgProGluGlyPhe-305 |
| SEQ. ID. NO. 24930 | 308-LysValGlnGluArgAspAspIleSer-316 |
| SEQ. ID. NO. 24931 | 332-ArgLeuAsnAspLysAsnSerAspIlePheAspArgThrLeuProArgLysGlyLeu-350 |
| SEQ. ID. NO. 24932 | 355-IleAspGlyHisSerAsnGlnTrpValGlnGlyLysThrAlaProValGluSerAsnArgLysGlyVal-377 |
| SEQ. ID. NO. 24933 | 387-GlnAsnGluSerAsnGlnLeu-393 |
| SEQ. ID. NO. 24934 | 399-SerGlyGlnAlaGluGlnArgSerThrPheArgAsnProAspThrAspAsnLeuThrThrGlyAsnValLysGlyPheGly-425 |
| SEQ. ID. NO. 24935 | 435-LeuGlnAspLysGlnThrGlyAlaTyrAlaAspSer-446 |
| SEQ. ID. NO. 24936 | 451-GlnArgPheArgHisArgIleAsnThrGluAspAlaThrGluArgPheThrSerLysGlyIle-471 |
| SEQ. ID. NO. 24937 | 486-HisPheThrLysLysGlyAsnArgVal-494 |
| SEQ. ID. NO. 24938 | 509-ValAsnGlyLysPheSerAspSerGluAsnAla-519 |
| SEQ. ID. NO. 24939 | 524-LeuGlySerArgGlnLeuGlnSer-531 |
| SEQ. ID. NO. 24940 | 562-LysProPheGlyValGluMetAspGlyGluArgArgMetIleAsnAsnLysThrAlaIleGluSer-583 |
| SEQ. ID. NO. 24941 | 589-ValLysIleLysSer-593 |
| SEQ. ID. NO. 24942 | 600-ThrPheAsnArgGlnThrGlyLysHisHisGlnAlaLysGlnGly-614 |
| Hydrophilic Regions - Hopp-Woods | |
| SEQ. ID. NO. 24943 | 1-LysLysLeuArgAspArgAsnSerGluTyrTrpLysGluGluThrTyrHis-17 |
| SEQ. ID. NO. 24944 | 35-HisProPheAspPro-39 |
| SEQ. ID. NO. 24945 | 44-AsnAsnSerLysArgIleSerPheTyrAspLysGluTyrThrGlu-58 |
| SEQ. ID. NO. 24946 | 70-ValAlaLysArgAsnGlyGluThrGluLysProIle-81 |
| SEQ. ID. NO. 24947 | 93-LysTyrSerAspAspThrCysLysSerGlnGln-103 |
| SEQ. ID. NO. 24948 | 117-ThrLysIleLysAsn-121 |
| SEQ. ID. NO. 24949 | 152-LeuTyrSerAspValAsp-157 |
| SEQ. ID. NO. 24950 | 178-AspGluPheArgLeuGlu-183 |
| SEQ. ID. NO. 24951 | 189-ProArgTrpAspSerAspValGlyGluLeuLysThrThrAsnAlaAspIleArgPheAsnThrLysSerGluSerLeuLeuValLysGluAsp TyrAlaGly-222 |
| SEQ. ID. NO. 24952 | 232-LeuLysAspLysValProGlu-238 |
| SEQ. ID. NO. 24953 | 246-LysAsnIleThrGly-250 |
| SEQ. ID. NO. 24954 | 258-AsnProIleAspAspLeuLysSerLeuAsp-267 |
| SEQ. ID. NO. 24955 | 276-GlyThrAlaAspLysHisAlaPhe-283 |
| SEQ. ID. NO. 24956 | 285-LeuSerGlyLysHisGlnLys-291 |
| SEQ. ID. NO. 24957 | 299-GlnGlnArgProGluGlyPhe-305 |
| SEQ. ID. NO. 24958 | 309-ValGlnGluArgAspAspIle-315 |
| SEQ. ID. NO. 24959 | 333-LeuAsnAspLysAsnSerAspIlePheAsp-342 |
| SEQ. ID. NO. 24960 | 366-LysThrAlaProValGluSerAsnArgLysGlyVal-377 |
| SEQ. ID. NO. 24961 | 388-AsnGluSerAsnGln-392 |
| SEQ. ID. NO. 24962 | 401-GlnAlaGluGlnArgSerThrPheArgAsnProAspThrAspAsnLeuThr-417 |
| SEQ. ID. NO. 24963 | 435-LeuGlnAspLysGlnThr-440 |
| SEQ. ID. NO. 24964 | 451-GlnArgPheArgHisArgIleAsnThrGluAspAlaThrGluArgPheThrSer-468 |
| SEQ. ID. NO. 24965 | 486-HisPheThrLysLysGlyAsnArg-493 |
| SEQ. ID. NO. 24966 | 512-LysPheSerAspSerGluAsnAla-519 |
| SEQ. ID. NO. 24967 | 527-ArgGlnLeuGlnSer-531 |
| SEQ. ID. NO. 24968 | 564-PheGlyValGluMetAspGlyGluArgArgMetIleAsn-576 |
| SEQ. ID. NO. 24969 | 589-ValLysIleLysSer-593 |
| SEQ. ID. NO. 24970 | 603-ArgGlnThrGlyLysHisHisGlnAlaLysGlnGly-614 |
| a935 | |
| AMPHI Regions - AMPHI | |
| SEQ. ID. NO. 24971 | 41-ValSerAspLysTrpAla-46 |
| SEQ. ID. NO. 24972 | 56-AlaProArgValVal-60 |
| SEQ. ID. NO. 24973 | 72-LeuGluHisSerLeuArgAsp-78 |

TABLE 1-continued

| | |
|---|---|
| SEQ. ID. NO. 24974 | 87-LeuIleAlaSerLeuAlaAspLeuTyrAlaLysLeu-98 |
| SEQ. ID. NO. 24975 | 111-AlaLeuLeuAlaLysLeuAlaGlyArgProAlaGluAlaValAlaArgTyrArgGlu-129 |
| SEQ. ID. NO. 24976 | 172-ProValLeuGluAsnValGlyArgPheArgLysLysAlaGlu-185 |
| SEQ. ID. NO. 24977 | 375-LysArgLeuGlyGluSerAlaThrValPheGlyGlyTrpGlnPheVal-390 |
| SEQ. ID. NO. 24978 | 415-AlaGlyTrpAlaGlnGluTrpArgGlnLeuGlyGlyLeu-427 |
| SEQ. ID. NO. 24979 | 435-TyrAlaArgArgAsnTyr-440 |
| Antigenic Index - Jameson-Wolf | |
| SEQ. ID. NO. 24980 | 27-AlaIleLeuAspAspLysAlaLeu-34 |
| SEQ. ID. NO. 24981 | 39-ArgSerValSerAspLysTrpAlaGluSerAspTrpLysValAspAsnAspAlaProArgValValAspGlyAspPhe-64 |
| SEQ. ID. NO. 24982 | 70-LysMetLeuGluHisSerLeuArgAspValLeuAsnGlyAsnGlnAlaAsp-86 |
| SEQ. ID. NO. 24983 | 97-LysLeuProAspTyrAspAla-103 |
| SEQ. ID. NO. 24984 | 108-ArgAlaArgAlaLeu-112 |
| SEQ. ID. NO. 24985 | 116-LeuAlaGlyArgProAlaGluAlaValAlaArgTyrArgGluLeuHisGlyGluAsnAlaAlaAspGluArgIleLeu-141 |
| SEQ. ID. NO. 24986 | 145-AlaAlaAlaGluPheAspAspPheArgLeuLysSerAlaGluArgHisPheAlaGluAlaGluLysLeuAspLeu-169 |
| SEQ. ID. NO. 24987 | 176-AsnValGlyArgPheArgLysLysAlaGluGlyLeuThrGly-189 |
| SEQ. ID. NO. 24988 | 192-PheSerGlyGlyIle-196 |
| SEQ. ID. NO. 24989 | 199-AlaValAsnArgAsnAlaAsnAsnAlaAla-208 |
| SEQ. ID. NO. 24990 | 210-GlnTyrCysArgGlnAsnGlyGlyArgGln-219 |
| SEQ. ID. NO. 24991 | 224-SerArgAlaGluArgAlaAla-230 |
| SEQ. ID. NO. 24992 | 236-IleGluAlaGluLysLeuThrAla-243 |
| SEQ. ID. NO. 24993 | 253-ArgSerAsnIleGlyGlyThrSerTyr-261 |
| SEQ. ID. NO. 24994 | 263-PheSerLysLysSerAlaTyrAspAspGlyPheGlyArg-275 |
| SEQ. ID. NO. 24995 | 279-GlyTrpGlnTyrLysAsnAlaArgGlnThr-288 |
| SEQ. ID. NO. 24996 | 300-SerGlySerAspGlyPheAspAlaLysThrLysArgValAsnAsnArgArgLeuProProTyr-320 |
| SEQ. ID. NO. 24997 | 332-HisThrTyrArgProAsnProGlyTrp-340 |
| SEQ. ID. NO. 24998 | 347-GluHisTyrArgGlnArgTyrArgGluGlnAspArgAlaGluTyrAsnAsnGlyArgGlnAspGlyPheTyr-370 |
| SEQ. ID. NO. 24999 | 373-SerAlaLysArgLeuGlyGlu-379 |
| SEQ. ID. NO. 25000 | 392-PheValProLysArgGluThrVal-399 |
| SEQ. ID. NO. 25001 | 406-AlaAlaTyrArgArgAsnGlyValTyrAlaGly-416 |
| SEQ. ID. NO. 25002 | 425-GlyGlyLeuAsnSerArgValSerAlaSerTyrAlaArgArgAsnTyrLysGly-442 |
| SEQ. ID. NO. 25003 | 448-ThrGluAlaGlnArgAsnArgGluTrpAsn-457 |
| SEQ. ID. NO. 25004 | 463-SerHisAspLysLeuSerTyrLysGly-471 |
| SEQ. ID. NO. 25005 | 480-PheGlyArgThrGluSerAsnValProTyrAlaLysArgArgAsnSerGlu-496 |
| SEQ. ID. NO. 25006 | 501-AlaAspTrpArgPhe-505 |
| Hydrophilic Regions - Hopp-Woods | |
| SEQ. ID. NO. 25007 | 27-AlaIleLeuAspAspLysAlaLeu-34 |
| SEQ. ID. NO. 25008 | 39-ArgSerValSerAspLysTrpAlaGluSerAspTrpLysValAspAsnAspAlaProArgValValAsp-61 |
| SEQ. ID. NO. 25009 | 70-LysMetLeuGluHisSerLeuArgAspValLeuAsn-81 |
| SEQ. ID. NO. 25010 | 108-ArgAlaArgAlaLeu-112 |
| SEQ. ID. NO. 25011 | 116-LeuAlaGlyArgProAlaGluAlaValAlaArgTyrArgGluLeuHisGly-132 |
| SEQ. ID. NO. 25012 | 134-AsnAlaAlaAspGluArgIleLeu-141 |
| SEQ. ID. NO. 25013 | 145-AlaAlaAlaGluPheAspAspPheArgLeuLysSerAlaGluArgHisPheAlaGluAlaGluLysLeuAspLeu-169 |
| SEQ. ID. NO. 25014 | 176-AsnValGlyArgPheArgLysLysAlaGluGly-186 |
| SEQ. ID. NO. 25015 | 200-ValAsnArgAsnAlaAsn-205 |
| SEQ. ID. NO. 25016 | 212-CysArgGlnAsnGlyGlyArgGln-219 |
| SEQ. ID. NO. 25017 | 224-SerArgAlaGluArgAlaAla-230 |
| SEQ. ID. NO. 25018 | 236-IleGluAlaGluLysLeuThrAla-243 |
| SEQ. ID. NO. 25019 | 265-LysLysSerAlaTyrAspAspGlyPheGly-274 |
| SEQ. ID. NO. 25020 | 283-LysAsnAlaArgGlnThr-288 |
| SEQ. ID. NO. 25021 | 303-AspGlyPheAspAlaLysThrLysArgValAsnAsnArgArgLeuPro-318 |
| SEQ. ID. NO. 25022 | 348-HisTyrArgGlnArgTyrArgGluGlnAspArgAlaGluTyrAsnAsnGlyArgGlnAsp-367 |
| SEQ. ID. NO. 25023 | 373-SerAlaLysArgLeuGlyGlu-379 |
| SEQ. ID. NO. 25024 | 393-ValProLysArgGluThrVal-399 |
| SEQ. ID. NO. 25025 | 407-AlaTyrArgArgAsnGly-412 |
| SEQ. ID. NO. 25026 | 435-TyrAlaArgArgAsnTyrLys-441 |
| SEQ. ID. NO. 25027 | 449-GluAlaGlnArgAsnArgGluTrp-456 |
| SEQ. ID. NO. 25028 | 463-SerHisAspLysLeuSerTyr-469 |
| SEQ. ID. NO. 25029 | 480-PheGlyArgThrGluSer-485 |
| SEQ. ID. NO. 25030 | 489-TyrAlaLysArgArgAsnSerGlu-496 |
| a936-1 | |
| AMPHI Regions - AMPHI | |
| SEQ. ID. NO. 25031 | 8-ValArgThrLeuThrAla-13 |
| SEQ. ID. NO. 25032 | 22-GlyCysValSerAlaVal-27 |
| SEQ. ID. NO. 25033 | 100-GlnPheValGlyGlnIle-105 |
| SEQ. ID. NO. 25034 | 112-AlaGluGlyValTyrAsnTyrIleThrValAlaSerLeuProArgThrAlaGlyAspIleAlaGlyAsp-134 |
| Antigenic Index - Jameson-Wolf | |
| SEQ. ID. NO. 25035 | 1-MetLysProLysProHisThrValArg-9 |
| SEQ. ID. NO. 25036 | 33-ValGlyAlaLysSerAlaValAspArgArgThrThrGlyAlaGlnThrAspAspAsnValMet-53 |
| SEQ. ID. NO. 25037 | 56-ArgIleGluThrThrAlaArgSerTyrLeuArgGlnAsnAsnGlnThrLysGlyTyr-74 |
| SEQ. ID. NO. 25038 | 94-AlaThrGluGlyGluLysGlnPhe-101 |
| SEQ. ID. NO. 25039 | 106-AlaArgSerGluGlnAlaAla-112 |
| SEQ. ID. NO. 25040 | 124-LeuProArgThrAlaGlyAspIleAlaGlyAspThrTrpAsnThrSerLysValArgAla-143 |
| SEQ. ID. NO. 25041 | 149-SerProAlaThrGlnAlaArgValLys-157 |
| SEQ. ID. NO. 25042 | 172-ThrProGluGluGlnAlaGlnIleThr-180 |
| Hydrophilic Regions - Hopp-Woods | |
| SEQ. ID. NO. 25043 | 1-MetLysProLysProHisThr-7 |
| SEQ. ID. NO. 25044 | 37-SerAlaValAspArgArgThrThrGlyAlaGlnThrAspAspAsnValMet-53 |
| SEQ. ID. NO. 25045 | 56-ArgIleGluThrThrAla-61 |
| SEQ. ID. NO. 25046 | 68-AsnAsnGlnThrLysGlyTyr-74 |
| SEQ. ID. NO. 25047 | 94-AlaThrGluGlyGluLysGlnPhe-101 |

TABLE 1-continued

SEQ. ID. NO. 25048    106-AlaArgSerGluGlnAlaAla-112
SEQ. ID. NO. 25049    125-ProArgThrAlaGly-129
SEQ. ID. NO. 25050    152-ThrGlnAlaArgValLys-157
SEQ. ID. NO. 25051    172-ThrProGluGluGlnAlaGlnIle-179
a937
AMPHI Regions - AMPHI
SEQ. ID. NO. 25052    6-LeuProAlaLeuProAlaIleLeuProLeuSerAla-17
SEQ. ID. NO. 25053    232-LysGlnProAspArgLeuAsp-238
Antigenic Index - Jameson-Wolf
SEQ. ID. NO. 25054    27-AspIleMetThrAspLysGlyLysTrpLysLeuGluThr-39
SEQ. ID. NO. 25055    44-LeuAsnSerGluAsnAsnArgAlaGluLeu-53
SEQ. ID. NO. 25056    71-ThrGluIleGlnGluAsnGlySerAsnThr-80
SEQ. ID. NO. 25057    95-GlyAsnThrAspIleTyrGlySerGlySer-104
SEQ. ID. NO. 25058    108-HisGluGluArgLysLeuAspGlyAsnGlyLysThrArgAsnLysArgMetSerAsp-126
SEQ. ID. NO. 25059    135-PheLeuLysAspAspLysAsnProAla-143
SEQ. ID. NO. 25060    151-ThrValTyrGluLysSerArgAsnLysAlaSerSerGlyLysSer-165
SEQ. ID. NO. 25061    187-TyrArgIleAsnGlySerLysThrLeuSerSerAsnThrLysTyrLysAlaGly-204
SEQ. ID. NO. 25062    217-AlaAsnAspArgIleSerLeuThrGlyGly-226
SEQ. ID. NO. 25063    231-GlyLysGlnProAspArgLeuAspGlyLysLysGluSerAlaArgAsnThrSerThr-249
SEQ. ID. NO. 25064    273-ValSerGlyGlnSerSerSerGluLeuLysPhe-283
Hydrophilic Regions - Hopp-Woods
SEQ. ID. NO. 25065    27-AspIleMetThrAspLysGlyLysTrpLysLeu-37
SEQ. ID. NO. 25066    47-GluAsnAsnArgAlaGluLeu-53
SEQ. ID. NO. 25067    72-GluIleGlnGluAsnGlySerAsn-79
SEQ. ID. NO. 25068    108-HisGluGluArgLysLeuAspGlyAsnGlyLysThrArgAsnLysArgMetSerAsp-126
SEQ. ID. NO. 25069    135-PheLeuLysAspAspLysAsnPro-142
SEQ. ID. NO. 25070    151-ThrValTyrGluLysSerArgAsnLysAlaSerSer-162
SEQ. ID. NO. 25071    193-LysThrLeuSerSer-197
SEQ. ID. NO. 25072    199-ThrLysTyrLysAla-203
SEQ. ID. NO. 25073    217-AlaAsnAspArgIleSer-222
SEQ. ID. NO. 25074    232-LysGlnProAspArgLeuAspGlyLysLysGluSerAlaArgAsn-246
SEQ. ID. NO. 25075    277-SerSerSerGluLeuLysPhe-283
a939
AMPHI Regions - AMPHI
SEQ. ID. NO. 25076    32-AlaThrValCysAla-36
SEQ. ID. NO. 25077    90-AspGlnAspIleLeu-94
SEQ. ID. NO. 25078    121-LysIleTyrArgGly-125
SEQ. ID. NO. 25079    135-CysMetSerCysHisGly-140
SEQ. ID. NO. 25080    151-SerGluIleGlnAlaTyrProArgLeuGlyGly-161
SEQ. ID. NO. 25081    169-GluGlnMetAsnAlaTyrLys-175
SEQ. ID. NO. 25082    185-GluAspIleAlaAsnArgMetSer-192
Antigenic Index - Jameson-Wolf
SEQ. ID. NO. 25083    18-AlaSerProLysAlaAspValGluLysGlyLysGlnVal-30
SEQ. ID. NO. 25084    40-AlaAlaAspGlyAsnSerGlyIle-47
SEQ. ID. NO. 25085    66-IleGlyIleArgAspGlyLysArgThrHisGlySerAlaAlaVal-80
SEQ. ID. NO. 25086    88-LeuSerAspGlnAspIle-93
SEQ. ID. NO. 25087    102-LysGlnGlnProLysSerGlyGluAlaAsnProLysGluAsnProGluLeuGly-119
SEQ. ID. NO. 25088    122-IleTyrArgGlyGlyLeuSerAspLysLysValPro-133
SEQ. ID. NO. 25089    139-HisGlyProSerGlyAlaGlyMetProGlyGlyGlySerGluIleGlnAla-155
SEQ. ID. NO. 25090    157-ProArgLeuGlyGlyGlnHisGln-164
SEQ. ID. NO. 25091    172-AsnAlaTyrLysSerGlyGlnArgLysAsnThrIleMetGluAspIleAlaAsnArgMetSerGluGluAspLeuLysAla-198
Hydrophilic Regions - Hopp-Woods
SEQ. ID. NO. 25092    18-AlaSerProLysAlaAspValGluLysGlyLysGlnVal-30
SEQ. ID. NO. 25093    40-AlaAlaAspGlyAsnSer-45
SEQ. ID. NO. 25094    67-GlyIleArgAspGlyLysArgThrHisGly-76
SEQ. ID. NO. 25095    89-SerAspGlnAspIle-93
SEQ. ID. NO. 25096    103-GlnGlnProLysSerGlyGluAlaAsnProLysGluAsnProGluLeuGly-119
SEQ. ID. NO. 25097    126-GlyLeuSerAspLysLysValPro-133
SEQ. ID. NO. 25098    175-LysSerGlyGlnArgLysAsnThrIleMetGluAspIleAlaAsnArgMetSerGluGluAspLeuLysAla-198
a950
AMPHI Regions - AMPHI
SEQ. ID. NO. 25099    33-GlyValHisLysSerAlaHisGly-40
SEQ. ID. NO. 25100    71-AlaThrValLysLysThrHisLysHisThrLysAla-82
Antigenic Index - Jameson-Wolf
SEQ. ID. NO. 25101    1-MetAsnLysAsnIle-5
SEQ. ID. NO. 25102    23-AlaAlaAsnLysProAlaSerAsnAlaThrGlyValHisLysSerAlaHisGlySerCysGlyAlaSerLysSerAlaGluGlySerCysGlyAla
                      AlaGlySerLysAlaGlyGluGlyLysCysGlyGluGlyLysCysGlyAlaThrValLysLysThrHisLysHisThrLysAlaSerLysAlaLysAlaLysSer
                      AlaGluGlyLysCysGlyGluGlyLysCysGlySerLys-102
Hydrophilic Regions - Hopp-Woods
SEQ. ID. NO. 25103    23-AlaAlaAsnLysProAlaSer-29
SEQ. ID. NO. 25104    33-GlyValHisLysSerAlaHis-39
SEQ. ID. NO. 25105    43-GlyAlaSerLysSerAlaGluGlySerCys-52
SEQ. ID. NO. 25106    55-AlaGlySerLysAlaGlyGluGlyLysCysGlyGluGlyLysCys-69
SEQ. ID. NO. 25107    71-AlaThrValLysLysThrHisLysHisThrLysAlaSerLysAlaLysAlaLysSerAlaGluGlyLysCysGlyGluGlyLysCysGlySerLys-102
a951
AMPHI Regions - AMPHI
SEQ. ID. NO. 25108    7-ThrIleLeuSerValLeuAlaAla-14
SEQ. ID. NO. 25109    28-AspAlaLysProProLysGluValGlyLysValPheArgLysGlnGlnArgTyr-45
SEQ. ID. NO. 25110    60-ValGlyGluArgValAsn-65
SEQ. ID. NO. 25111    125-TrpArgGlnIleGluProIleProGlyLys-134

TABLE 1-continued

| SEQ. ID. NO. | Sequence |
|---|---|
| SEQ. ID. NO. 25112 | 153-HisLeuAspGlyLeuGluGluValLeuAla-162 |
| SEQ. ID. NO. 25113 | 187-AlaGlnLysAlaSerLysAlaValArgArg-196 |
| SEQ. ID. NO. 25114 | 202-GluHisLeuProGluAlaAla-208 |
| SEQ. ID. NO. 25115 | 226-GlyAlaLeuGlnArgLeuAlaLysLeu-234 |
| SEQ. ID. NO. 25116 | 252-LysTyrProGluIleLeuAspGlyPhePheGlu-262 |
| SEQ. ID. NO. 25117 | 276-MetGluIleMetAsnLeuValSerLeuHisArgLeuAspAspAla-290 |
| SEQ. ID. NO. 25118 | 323-ValIleAspGlyTyrAlaGluLys-330 |
| SEQ. ID. NO. 25119 | 360-ValArgGlnTrpLeuLys-365 |
| SEQ. ID. NO. 25120 | 393-AlaLeuArgGlnIleGlyArgValArgLysLeuProGluGlnGln-407 |
| SEQ. ID. NO. 25121 | 414-AspAsnLeuSerLysIle-419 |
| SEQ. ID. NO. 25122 | 421-MetPheAlaLeuSer-425 |
| SEQ. ID. NO. 25123 | 432-GluAlaLeuArgGlyLeuAspLysIleIleGluLys-443 |
| SEQ. ID. NO. 25124 | 475-SerAspLeuGluArgAlaPheArg-482 |
| SEQ. ID. NO. 25125 | 493-AsnLeuGlyTyrSer-497 |
| SEQ. ID. NO. 25126 | 501-AspSerLysArgLeu-505 |
| SEQ. ID. NO. 25127 | 561-HisLeuGlyGluVal-565 |
| SEQ. ID. NO. 25128 | 577-AspValTrpThrGlnAla-582 |
| SEQ. ID. NO. 25129 | 592-TrpArgGluThrLeu-596 |

Antigenic Index - Jameson-Wolf

| SEQ. ID. NO. | Sequence |
|---|---|
| SEQ. ID. NO. 25130 | 26-AlaAlaAspAlaLysProProLysGluValGlyLysValPheArgLysGlnGlnArgTyrSerGluGluGluIleLysAsnGluArgAlaArgLeu-57 |
| SEQ. ID. NO. 25131 | 59-AlaValGlyGluArgValAsn-65 |
| SEQ. ID. NO. 25132 | 75-ThrAlaLeuGlnLysGlyGlnAla-82 |
| SEQ. ID. NO. 25133 | 94-GluArgThrLysSerProGluValAlaGluArgAlaLeuGlu-107 |
| SEQ. ID. NO. 25134 | 124-LysTrpArgGlnIleGluProIleProGlyLysAlaGlnLysArgAlaGlyTrpLeuArgAsnValLeuArgGluArgGlyAsnGlnHisLeuAspGlyLeuGluGluValLeuAlaGlnAlaAspGluGlyGlnAsnArgArg-171 |
| SEQ. ID. NO. 25135 | 181-ValGlnGlnAspGlyLeuAlaGlnLysAlaSerLysAlaValArgArgAlaAlaLeuArg-200 |
| SEQ. ID. NO. 25136 | 217-GlnGlyArgGluLysGluLysAlaIle-225 |
| SEQ. ID. NO. 25137 | 230-ArgLeuAlaLysLeuAspThrGluIleLeuPro-240 |
| SEQ. ID. NO. 25138 | 248-LeuThrAlaArgLysTyrProGluIleLeuAspGlyPhePheGluGlnThrAspThrGlnAsn-268 |
| SEQ. ID. NO. 25139 | 285-HisArgLeuAspAspAlaTyrAla-292 |
| SEQ. ID. NO. 25140 | 298-LeuGluArgAsnProAsnAlaAsp-305 |
| SEQ. ID. NO. 25141 | 315-AlaAsnArgLysGluGlyAlaSer-322 |
| SEQ. ID. NO. 25142 | 326-GlyTyrAlaGluLysAlaTyrGlyArgGlyThrGlyGluGlnArgGlyArgAla-343 |
| SEQ. ID. NO. 25143 | 352-AlaAspArgArgAspTyrThrLysValArgGlnTrpLeuLysLysValSerAlaPro-370 |
| SEQ. ID. NO. 25144 | 373-LeuPheAspLysGlyVal-378 |
| SEQ. ID. NO. 25145 | 385-ValGluLeuAspGlyGlyArgAlaAlaLeu-394 |
| SEQ. ID. NO. 25146 | 396-GlnIleGlyArgValArgLysLeuProGluGlnGlnGlyArgTyrPheThr-412 |
| SEQ. ID. NO. 25147 | 426-LysLeuProAspLysArgGluAlaLeuArgGlyLeuAspLysIleIleGluLysProProAlaGlySerAsnThrGluLeuGlnAla-454 |
| SEQ. ID. NO. 25148 | 466-ArgLeuGlyLysArgLysLysMetIleSerAspLeuGluArgAlaPheArgLeuAlaProAspAsn-487 |
| SEQ. ID. NO. 25149 | 499-LeuSerAspSerLysArgLeuAspGluGlyPhe-509 |
| SEQ. ID. NO. 25150 | 518-IleAsnProAspAspThrAlaValAsnAspSerIle-529 |
| SEQ. ID. NO. 25151 | 535-LeuLysGlyAspAlaGluSerAla-542 |
| SEQ. ID. NO. 25152 | 547-ArgTyrSerPheGluAsnAspProGluProVal-558 |
| SEQ. ID. NO. 25153 | 570-GlyGluArgAspGlnAla-575 |
| SEQ. ID. NO. 25154 | 584-HisLeuThrGlyAspLysLysIleTrpArgGluThrLeuLysArgHisGlyIleAlaLeuProGlnProSerArgLysProArgLys-612 |

Hydrophilic Regions - Hopp-Woods

| SEQ. ID. NO. | Sequence |
|---|---|
| SEQ. ID. NO. 25155 | 26-AlaAlaAspAlaLysProProLysGluValGlyLysValPheArgLysGlnGlnArgTyrSerGluGluGluIleLysAsnGluArgAlaArgLeu-57 |
| SEQ. ID. NO. 25156 | 59-AlaValGlyGluArgValAsn-65 |
| SEQ. ID. NO. 25157 | 75-ThrAlaLeuGlnLysGlyGlnAla-82 |
| SEQ. ID. NO. 25158 | 94-GluArgThrLysSerProGluValAlaGluArgAlaLeuGlu-107 |
| SEQ. ID. NO. 25159 | 131-IleProGlyLysAlaGlnLysArgAlaGlyTrp-141 |
| SEQ. ID. NO. 25160 | 145-ValLeuArgGluArgGlyAsnGlnHis-153 |
| SEQ. ID. NO. 25161 | 155-AspGlyLeuGluGluValLeuAlaGlnAlaAspGluGlyGlnAsnArgArg-171 |
| SEQ. ID. NO. 25162 | 185-GlyLeuAlaGlnLysAlaSerLysAlaValArgArgAlaAlaLeuArg-200 |
| SEQ. ID. NO. 25163 | 217-GlnGlyArgGluLysGluLysAlaIle-225 |
| SEQ. ID. NO. 25164 | 230-ArgLeuAlaLysLeuAspThrGluIle-238 |
| SEQ. ID. NO. 25165 | 248-LeuThrAlaArgLysTyrProGluIle-256 |
| SEQ. ID. NO. 25166 | 261-PheGluGlnThrAspThrGlnAsn-268 |
| SEQ. ID. NO. 25167 | 285-HisArgLeuAspAspAlaTyrAla-292 |
| SEQ. ID. NO. 25168 | 298-LeuGluArgAsnProAsn-303 |
| SEQ. ID. NO. 25169 | 315-AlaAsnArgLysGluGlyAlaSer-322 |
| SEQ. ID. NO. 25170 | 327-TyrAlaGluLysAlaTyrGly-333 |
| SEQ. ID. NO. 25171 | 335-GlyThrGlyGluGlnArgGlyArgAla-343 |
| SEQ. ID. NO. 25172 | 352-AlaAspArgArgAspTyrThrLys-359 |
| SEQ. ID. NO. 25173 | 385-ValGluLeuAspGlyGlyArgAlaAlaLeu-394 |
| SEQ. ID. NO. 25174 | 396-GlnIleGlyArgValArgLysLeuProGluGlnGlnGly-408 |
| SEQ. ID. NO. 25175 | 426-LysLeuProAspLysArgGluAlaLeuArgGlyLeuAspLysIleIleGluLysProProAla-446 |
| SEQ. ID. NO. 25176 | 448-SerAsnThrGluLeuGlnAla-454 |
| SEQ. ID. NO. 25177 | 466-ArgLeuGlyLysArgLysLysMetIleSerAspLeuGluArgAlaPheArgLeuAlaProAspAsn-487 |
| SEQ. ID. NO. 25178 | 500-SerAspSerLysArgLeuAspGlu-507 |
| SEQ. ID. NO. 25179 | 519-AsnProAspAspThrAlaVal-525 |
| SEQ. ID. NO. 25180 | 537-GlyAspAlaGluSer-541 |
| SEQ. ID. NO. 25181 | 550-PheGluAsnAspProGluProVal-558 |
| SEQ. ID. NO. 25182 | 570-GlyGluArgAspGlnAla-575 |
| SEQ. ID. NO. 25183 | 586-ThrGlyAspLysLysIleTrpArgGluThrLeuLysArgHisGly-600 |
| SEQ. ID. NO. 25184 | 605-GlnProSerArgLysProArgLys-612 | a952
AMPHI Regions - AMPHI

| SEQ. ID. NO. | Sequence |
|---|---|
| SEQ. ID. NO. 25185 | 63-SerValAlaThrLeuLeuAsnAsnPheTyrGlyGln-74 |
| SEQ. ID. NO. 25186 | 81-ValLeuLysLysLeuAsp-86 |

TABLE 1-continued

| | |
|---|---|
| SEQ. ID. NO. 25187 | 94-PheGluAspMetArgArgIle-100 |
| SEQ. ID. NO. 25188 | 116-GluGlnLeuAlaGlnLeu-121 |
| SEQ. ID. NO. 25189 | 138-SerValLeuArgGlyIleAsp-144 |

Antigenic Index - Jameson-Wolf

| | |
|---|---|
| SEQ. ID. NO. 25190 | 40-GlnSerTrpLysGluArgArgAspPheAsnIleValLysGlnAspLeuAspPheSerCys-59 |
| SEQ. ID. NO. 25191 | 70-AsnPheTyrGlyGlnThrLeuThrGluGluGluValLeuLysLysLeuAspLysGluGlnMetArgAlaSerPheGluAspMetArgArgIleMetPro-102 |
| SEQ. ID. NO. 25192 | 104-LeuGlyPheGluAlaLysGlyTyr-111 |
| SEQ. ID. NO. 25193 | 129-LeuLysTyrArgLysAspAspHisPheSer-138 |
| SEQ. ID. NO. 25194 | 141-ArgGlyIleAspGlyAsnThr-147 |
| SEQ. ID. NO. 25195 | 169-TrpGlnThrArgGluGlyAsnLeuAla-177 |
| SEQ. ID. NO. 25196 | 184-ValProLysLysAlaGluThrIleSer-192 |
| SEQ. ID. NO. 25197 | 199-HisHisProLysArgGlnThrGlu-206 |
| SEQ. ID. NO. 25198 | 213-ArgGlnAlaArgAlaGlu-218 |

Hydrophilic Regions - Hopp-Woods

| | |
|---|---|
| SEQ. ID. NO. 25199 | 41-SerTrpLysGluArgArgAspPheAsnIleValLysGlnAspLeuAspPhe-57 |
| SEQ. ID. NO. 25200 | 76-LeuThrGluGluGluValLeuLysLysLeuAspLysGluGlnMetArgAlaSerPheGluAspMetArgArgIleMetPro-102 |
| SEQ. ID. NO. 25201 | 104-LeuGlyPheGluAlaLysGly-110 |
| SEQ. ID. NO. 25202 | 130-LysTyrArgLysAspAspHisPheSer-138 |
| SEQ. ID. NO. 25203 | 169-TrpGlnThrArgGluGlyAsnLeu-176 |
| SEQ. ID. NO. 25204 | 184-ValProLysLysAlaGluThrIleSer-192 |
| SEQ. ID. NO. 25205 | 200-HisProLysArgGlnThrGlu-206 |
| SEQ. ID. NO. 25206 | 213-ArgGlnAlaArgAlaGlu-218 | a953
AMPHI Regions - AMPHI

| | |
|---|---|
| SEQ. ID. NO. 25207 | 39-AsnThrSerThrAsnValGlyGlyPheTyrGlyLeuThr-51 |
| SEQ. ID. NO. 25208 | 75-GlnSerGlySerGlnHisPheThrAspHisLeuLysSerAlaAspIlePheAspAlaAlaGln-95 |
| SEQ. ID. NO. 25209 | 151-GlyAspPheSerThrThr-156 |

Antigenic Index - Jameson-Wolf

| | |
|---|---|
| SEQ. ID. NO. 25210 | 22-TyrLysValAspGluTyrHisAla-29 |
| SEQ. ID. NO. 25211 | 38-PheAsnThrSerThrAsnVal-44 |
| SEQ. ID. NO. 25212 | 54-ValGluPheAspGlnAlaLysArgAspGlyLysIleAspIle-67 |
| SEQ. ID. NO. 25213 | 83-AspHisLeuLysSer-87 |
| SEQ. ID. NO. 25214 | 95-GlnTyrProAspIleArgPheValSer-103 |
| SEQ. ID. NO. 25215 | 105-LysPheAsnPheAsnGlyLysLysLeuValSer-115 |
| SEQ. ID. NO. 25216 | 122-MetHisGlyLysThrAlaProValLysLeuLysAlaGluLys-135 |
| SEQ. ID. NO. 25217 | 137-AsnCysTyrGlnSerProMetLeuLys-145 |
| SEQ. ID. NO. 25218 | 147-GluValCysGlyGlyAsp-152 |
| SEQ. ID. NO. 25219 | 154-SerThrThrIleAspArgThrLysTrpGly-163 |
| SEQ. ID. NO. 25220 | 174-LysSerValArgIle-178 |
| SEQ. ID. NO. 25221 | 180-IleGlnIleGluAlaAlaLysGln-187 |

Hydrophilic Regions - Hopp-Woods

| | |
|---|---|
| SEQ. ID. NO. 25222 | 22-TyrLysValAspGluTyrHisAla-29 |
| SEQ. ID. NO. 25223 | 54-ValGluPheAspGlnAlaLysArgAspGlyLysIleAspIle-67 |
| SEQ. ID. NO. 25224 | 83-AspHisLeuLysSer-87 |
| SEQ. ID. NO. 25225 | 108-PheAsnGlyLysLysLeuValSer-115 |
| SEQ. ID. NO. 25226 | 125-LysThrAlaProValLysLeuLysAlaGluLys-135 |
| SEQ. ID. NO. 25227 | 155-ThrThrIleAspArgThrLysTrp-162 |
| SEQ. ID. NO. 25228 | 174-LysSerValArgIle-178 |
| SEQ. ID. NO. 25229 | 180-IleGlnIleGluAlaAlaLysGln-187 | a957
AMPHI Regions - AMPHI

| | |
|---|---|
| SEQ. ID. NO. 25230 | 11-SerPhePheAlaLeuValPheAla-18 |
| SEQ. ID. NO. 25231 | 45-AlaPheValAlaLysLeuAlaArgLeuPheArgAsnAla-57 |
| SEQ. ID. NO. 25232 | 71-GluGluSerLeuAlaGlyAlaValAspAsp-80 |
| SEQ. ID. NO. 25233 | 195-GluAspValTyrGluHisCysLeuGlyCysTyrGlnMet-207 |
| SEQ. ID. NO. 25234 | 215-TyrArgAspValAlaAsnAspGlu-222 |
| SEQ. ID. NO. 25235 | 232-SerAsnArgIleAlaSer-237 |
| SEQ. ID. NO. 25236 | 246-GlnAsnMetArgGluLeuMetProArg-254 |
| SEQ. ID. NO. 25237 | 352-GluLysGluValSerArgTyrAlaGluAlaAlaAlaArg-364 |

Antigenic Index - Jameson-Wolf

| | |
|---|---|
| SEQ. ID. NO. 25238 | 29-IleAsnProArgTrp-33 |
| SEQ. ID. NO. 25239 | 35-LeuSerAspThrAlaThrGluAsnProAsn-44 |
| SEQ. ID. NO. 25240 | 54-PheArgAsnAlaAspArgAla-60 |
| SEQ. ID. NO. 25241 | 64-ValLysGluSerMetArgThrGluGluSerLeu-74 |
| SEQ. ID. NO. 25242 | 77-AlaValAspAspGlyProLeuGlnSerGluLysAspTyr-89 |
| SEQ. ID. NO. 25243 | 95-ArgLeuSerArgLeuLysGluLysAlaLys-104 |
| SEQ. ID. NO. 25244 | 109-ThrGluGlnGluHisGlyGlu-115 |
| SEQ. ID. NO. 25245 | 122-TyrIleGlyGluGlyGly-127 |
| SEQ. ID. NO. 25246 | 133-LeuSerGlnArgSerProGluAlaPheVal-142 |
| SEQ. ID. NO. 25247 | 146-TyrLeuTyrArgAsnAspArgProPheSer-155 |
| SEQ. ID. NO. 25248 | 163-ValHisGlyGluAsnTyrGluThrThrGlyGluTyrArgVal-176 |
| SEQ. ID. NO. 25249 | 179-GlnProAspGlySerValPheAspAlaSerGlyArgGlyLysIleGlyGluAspValTyr-198 |
| SEQ. ID. NO. 25250 | 214-LysTyrArgAspValAlaAsnAspGluGlnLysValTrpAspPheArgGluGluSerAsnArgIleAlaSerAspSerArgAspSerValPhe-244 |
| SEQ. ID. NO. 25251 | 247-AsnMetArgGluLeuMetProArgGlyMetLysAlaAsnSer-260 |
| SEQ. ID. NO. 25252 | 265-TyrAspAlaAspGlyLeuProGln-272 |
| SEQ. ID. NO. 25253 | 277-SerPheAspAsnGlyLysLysArgGlnSerPheGluTyrTyrLeuLysAsnGlyAsn-295 |
| SEQ. ID. NO. 25254 | 306-LeuLysAlaAspGlyValThr-312 |
| SEQ. ID. NO. 25255 | 326-LeuAspGlyGlyArgIleValArgGluGluLysGlnGlyAspArgLeuProAspPhe-344 |
| SEQ. ID. NO. 25256 | 346-LeuAsnLeuGluAspLeuGluLysGluValSerArgTyrAlaGluAlaAlaAlaArgArgSerGlyGlyArgArgAspLeuSerHis-374 |

TABLE 1-continued

Hydrophilic Regions - Hopp-Woods
| | |
|---|---|
| SEQ. ID. NO. 25257 | 38-ThrAlaThrGluAsnPro-43 |
| SEQ. ID. NO. 25258 | 54-PheArgAsnAlaAspArgAla-60 |
| SEQ. ID. NO. 25259 | 64-ValLysGluSerMetArgThrGluGluSerLeu-74 |
| SEQ. ID. NO. 25260 | 77-AlaValAspAspGlyProLeuGlnSerGluLysAspTyr-89 |
| SEQ. ID. NO. 25261 | 95-ArgLeuSerArgLeuLysGluLysAlaLys-104 |
| SEQ. ID. NO. 25262 | 109-ThrGluGlnGluHisGlyGlu-115 |
| SEQ. ID. NO. 25263 | 133-LeuSerGlnArgSerProGlu-139 |
| SEQ. ID. NO. 25264 | 148-TyrArgAsnAspArgProPhe-154 |
| SEQ. ID. NO. 25265 | 166-GluAsnTyrGluThrThrGlyGluTyr-174 |
| SEQ. ID. NO. 25266 | 187-AlaSerGlyArgGlyLysIleGlyGluAspValTyr-198 |
| SEQ. ID. NO. 25267 | 214-LysTyrArgAspValAlaAsnAspGluGlnLysValTrpAspPheArgGluGluSerAsnArgIleAlaSerAspSerArgAspSerVal-243 |
| SEQ. ID. NO. 25268 | 247-AsnMetArgGluLeuMetProArgGlyMetLys-257 |
| SEQ. ID. NO. 25269 | 265-TyrAspAlaAspGlyLeuPro-271 |
| SEQ. ID. NO. 25270 | 279-AspAsnGlyLysLysArgGlnSer-286 |
| SEQ. ID. NO. 25271 | 306-LeuLysAlaAspGlyValThr-312 |
| SEQ. ID. NO. 25272 | 328-GlyGlyArgIleValArgGluGluLysGlnGlyAspArgLeuPro-342 |
| SEQ. ID. NO. 25273 | 346-LeuAsnLeuGluAspLeuGluLysGluValSerArgTyrAlaGluAlaAlaAlaArgArgSerGlyGlyArgArgAspLeuSerHis-374 | a958

AMPHI Regions - AMPHI
| | |
|---|---|
| SEQ. ID. NO. 25274 | 39-GlyGlySerValArgSerValSerGluProIleGln-50 |
| SEQ. ID. NO. 25275 | 86-ProGluAspTyrThrArgIleValAlaAsp-95 |
| SEQ. ID. NO. 25276 | 127-TyrAspGlnSerGlyAsp-132 |
| SEQ. ID. NO. 25277 | 177-ArgArgLeuGlnSerValSerArgThrAlaGluMet-188 |
| SEQ. ID. NO. 25278 | 343-IleSerAspThrLeuGln-348 |
| SEQ. ID. NO. 25279 | 483-TyrTyrSerLeuAsnArgPhe-489 |
| SEQ. ID. NO. 25280 | 491-SerGlnGluAlaArgArgVal-497 |
| SEQ. ID. NO. 25281 | 500-ThrLeuProIleVal-504 |
| SEQ. ID. NO. 25282 | 541-GlnAsnAspLeuProAsnPheAsp-548 |
| SEQ. ID. NO. 25283 | 572-AsnThrAlaAsnSerLeuSerAlaAlaValGlnSer-583 |
| SEQ. ID. NO. 25284 | 693-AspLysLeuSerGln-697 |
| SEQ. ID. NO. 25285 | 723-LysLysProIleGlu-727 |
| SEQ. ID. NO. 25286 | 769-AspLeuSerSerValGlyArgAsnPro-777 |

Antigenic Index - Jameson-Wolf
| | |
|---|---|
| SEQ. ID. NO. 25287 | 18-PheGlyThrHisCys-22 |
| SEQ. ID. NO. 25288 | 28-ValAlaAlaGluGluThrAspAsnProThrAlaGlyGlySerValArgSerValSerGluProIleGln-50 |
| SEQ. ID. NO. 25289 | 55-SerLeuGlySerThr-59 |
| SEQ. ID. NO. 25290 | 63-CysSerAsnGluSerGlySerProGluArgThrGluAlaAlaValGlnGlySerGlyGluAlaSerIleProGluAspTyrThrArgIleValAla AspArgMetGluGlyGlnSerGlnValGlnValArgAlaGluGly-109 |
| SEQ. ID. NO. 25291 | 111-ValValValGluArgAsnArgThrThrLeuAsn-121 |
| SEQ. ID. NO. 25292 | 123-AspTrpAlaAspTyrAspGlnSerGlyAspThrValThrAlaGlyAspArgPheAlaLeuGlnGlnAspGlyThrLeuIleArgGlyGluThrLeu-154 |
| SEQ. ID. NO. 25293 | 158-LeuGluGlnGlnThrGlyGluAlaHisAsnValArgMetGluThrGluHisGlyGlyArgArgLeuGlnSerValSerArgThrAlaGluMet LeuGlyGluGlyHisTyrLysLeuThrGluThrGlnPheAsnThrCysSerAlaGlyAspAlaGlyTrp-211 |
| SEQ. ID. NO. 25294 | 216-AlaSerValGluAlaAspArgGluLysGlyIleGly-227 |
| SEQ. ID. NO. 25295 | 249-PheProLeuAspGlyAsnArgLysSerGlyLeu-259 |
| SEQ. ID. NO. 25296 | 265-SerAlaGlySerAspGlyVal-271 |
| SEQ. ID. NO. 25297 | 292-GlyValIleGlyGluArgGlyAlaValPheAspGlyGlnValArgTyrLeuArgProAspTyrAlaGlyGlnSerAsp-317 |
| SEQ. ID. NO. 25298 | 321-LeuProHisAspLysLysSerGlyArgAsnAsnArgTyrGlnAla-335 |
| SEQ. ID. NO. 25299 | 337-TrpGlnHisArgHisAspIleSerAspThrLeu-347 |
| SEQ. ID. NO. 25300 | 352-AspPheAsnGlnValSerAspSerGlyTyrTyrArgAspPheTyrGlyAsnLysGluIleAlaGlyAsnValAsnLeuAsnArgArgValTrp-382 |
| SEQ. ID. NO. 25301 | 384-AspTyrGlyGlyArgAlaAlaGlyGlySerLeu-394 |
| SEQ. ID. NO. 25302 | 407-AlaAsnGlnSerGlyTyrLysAspLysProTyr-417 |
| SEQ. ID. NO. 25303 | 422-ArgLeuSerAlaAspTrpArgLysAsnThrGlyArgAla-434 |
| SEQ. ID. NO. 25304 | 444-ArgPheSerHisAspSerArgGlnAspGlySerArg-455 |
| SEQ. ID. NO. 25305 | 460-ProAspIleLysTrpAspPheSerAsnSerTrpGly-471 |
| SEQ. ID. NO. 25306 | 487-AsnArgPheGlySerGlnGluAlaArgArgValSerArg-499 |
| SEQ. ID. NO. 25307 | 507-AspSerGlyMetThrPheGluArgAsnThrArgMetPheGlyGlyGly-522 |
| SEQ. ID. NO. 25308 | 525-GlnThrLeuGluProArg-530 |
| SEQ. ID. NO. 25309 | 538-AlaLysSerGlnAsnAspLeuProAsnPheAspSerSerGluSerSerPheGly-555 |
| SEQ. ID. NO. 25310 | 560-PheArgGluAsnLeuTyrTyrGlyAsnAspArgIleAsnThrAlaAsnSer-576 |
| SEQ. ID. NO. 25311 | 581-ValGlnSerArgIleLeuAspGlyAlaThrGlyGluGluArgPheArgAlaGlyIleGlyGlnLysPheTyrPheLysAsnAspAlaValMetLeu AspGlySerValGlyLysLysProArgSerArgSerAspTrp-626 |
| SEQ. ID. NO. 25312 | 631-SerSerGlyIleGlySerArgPheIleLeuAspSerSerIleHisTyrAsnGlnAsnAspLysArgAlaGluAsn-655 |
| SEQ. ID. NO. 25313 | 660-AlaSerTyrArgProAlaGlnGlyLysValLeuAsnAlaArgTyrLysTyrGlyArgAsnGluLysIleTyrLeuLysSerAspGlySerTyrPhe-691 |
| SEQ. ID. NO. 25314 | 693-AspLysLeuSerGln-697 |
| SEQ. ID. NO. 25315 | 718-TyrGlyPheGluAlaLysLysProIleGlu-727 |
| SEQ. ID. NO. 25316 | 732-AlaGluTyrLysSerSerCysSerGlyCysTrp-741 |
| SEQ. ID. NO. 25317 | 751-ValThrGlyGluAsnThrTyrLysAsn-759 |
| SEQ. ID. NO. 25318 | 766-GlnLeuLysAspLeuSerSerValGlyArgAsnProAlaAspArgMetAspVal-783 |

Hydrophilic Regions - Hopp-Woods
| | |
|---|---|
| SEQ. ID. NO. 25319 | 28-ValAlaAlaGluGluThrAspAsnProThr-37 |
| SEQ. ID. NO. 25320 | 40-GlySerValArgSerValSerGluProIleGln-50 |
| SEQ. ID. NO. 25321 | 65-AsnGluSerGlySerProGluArgThrGluAlaAlaVal-77 |
| SEQ. ID. NO. 25322 | 79-GlySerGlyGluAlaSerIleProGluAspTyrThr-90 |
| SEQ. ID. NO. 25323 | 93-ValAlaAspArgMetGluGlyGlnSer-101 |
| SEQ. ID. NO. 25324 | 103-ValGlnValArgAlaGluGly-109 |
| SEQ. ID. NO. 25325 | 111-ValValValGluArgAsnArgThrThrLeu-120 |
| SEQ. ID. NO. 25326 | 125-AlaAspTyrAspGlnSerGlyAspThrValThrAlaGlyAspArgPheAlaLeu-142 |
| SEQ. ID. NO. 25327 | 147-ThrLeuIleArgGlyGluThr-153 |
| SEQ. ID. NO. 25328 | 160-GlnGlnThrGlyGluAlaHisAsnValArgMetGluThrGluHisGlyGlyArgArgLeuGlnSerValSerArgThrAlaGluMetLeuGly-190 |

TABLE 1-continued

| | |
|---|---|
| SEQ. ID. NO. 25329 | 192-GlyHisTyrLysLeuThrGlu-198 |
| SEQ. ID. NO. 25330 | 216-AlaSerValGluAlaAspArgGluLysGlyIleGly-227 |
| SEQ. ID. NO. 25331 | 250-ProLeuAspGlyAsnArgLysSerGly-258 |
| SEQ. ID. NO. 25332 | 266-AlaGlySerAspGlyVal-271 |
| SEQ. ID. NO. 25333 | 294-IleGlyGluArgGlyAlaVal-300 |
| SEQ. ID. NO. 25334 | 305-ValArgTyrLeuArg-309 |
| SEQ. ID. NO. 25335 | 323-HisAspLysLysSerGlyArgAsnAsnArgTyrGlnAla-335 |
| SEQ. ID. NO. 25336 | 337-TrpGlnHisArgHisAspIleSerAsp-345 |
| SEQ. ID. NO. 25337 | 410-SerGlyTyrLysAspLysProTyr-417 |
| SEQ. ID. NO. 25338 | 423-LeuSerAlaAspTrpArgLysAsnThrGlyArgAla-434 |
| SEQ. ID. NO. 25339 | 445-PheSerHisAspSerArgGlnAspGlySerArg-455 |
| SEQ. ID. NO. 25340 | 490-GlySerGlnGluAlaArgArgValSerArg-499 |
| SEQ. ID. NO. 25341 | 510-MetThrPheGluArgAsnThrArg-517 |
| SEQ. ID. NO. 25342 | 539-LysSerGlnAsnAsp-543 |
| SEQ. ID. NO. 25343 | 548-AspSerSerGluSer-552 |
| SEQ. ID. NO. 25344 | 569-AspArgIleAsnThr-573 |
| SEQ. ID. NO. 25345 | 589-AlaThrGlyGluGluArgPheArgAla-597 |
| SEQ. ID. NO. 25346 | 615-SerValGlyLysLysProArgSerArgSerAsp-625 |
| SEQ. ID. NO. 25347 | 648-GlnAsnAspLysArgAlaGluAsn-655 |
| SEQ. ID. NO. 25348 | 662-TyrArgProAlaGln-666 |
| SEQ. ID. NO. 25349 | 674-TyrLysTyrGlyArgAsnGluLysIleTyrLeuLysSerAspGly-688 |
| SEQ. ID. NO. 25350 | 720-PheGluAlaLysLysProIleGlu-727 |
| SEQ. ID. NO. 25351 | 732-AlaGluTyrLysSer-736 |
| SEQ. ID. NO. 25352 | 766-GlnLeuLysAspLeuSerSerValGlyArgAsnProAlaAspArgMetAspVal-783 |
| a959 | |
| AMPHI Regions - AMPHI | |
| SEQ. ID. NO. 25353 | 56-AlaAlaLeuAlaArgValGlyGly-63 |
| Antigenic Index - Jameson-Wolf | |
| SEQ. ID. NO. 25354 | 24-AlaHisHisAspGlyHisGlyAspAspAspHisGlyHis-36 |
| SEQ. ID. NO. 25355 | 40-GlnHisSerLysGlnAspLysIleIleSer-49 |
| SEQ. ID. NO. 25356 | 51-AlaGlnAlaGluLysAlaAlaLeu-58 |
| SEQ. ID. NO. 25357 | 60-ArgValGlyGlyLysIleThrAspIleAspLeuGluHisAspAsnGlyArgProHisTyrAspValGluIleValLysAsnGlyGlnGluTyr-90 |
| SEQ. ID. NO. 25358 | 94-ValAspAlaArgThrGlyArgValIleSerSerArgArgAspAsp-108 |
| Hydrophilic Regions - Hopp-Woods | |
| SEQ. ID. NO. 25359 | 27-AspGlyHisGlyAspAspAspHisGlyHis-36 |
| SEQ. ID. NO. 25360 | 40-GlnHisSerLysGlnAspLysIleIleSer-49 |
| SEQ. ID. NO. 25361 | 51-AlaGlnAlaGluLysAlaAlaLeu-58 |
| SEQ. ID. NO. 25362 | 61-ValGlyGlyLysIleThrAspIleAspLeuGluHisAspAsnGlyArgProHisTyr-79 |
| SEQ. ID. NO. 25363 | 82-GluIleValLysAsnGlyGlnGluTyr-90 |
| SEQ. ID. NO. 25364 | 94-ValAspAlaArgThrGlyArg-100 |
| SEQ. ID. NO. 25365 | 102-IleSerSerArgArgAspAsp-108 |
| a972 | |
| AMPHI Regions - AMPHI | |
| SEQ. ID. NO. 25366 | 15-SerSerGluArgMetSerGluValGluTyrPheSerHis-27 |
| SEQ. ID. NO. 25367 | 83-ArgLysLeuGluGluIleLeuGly-90 |
| SEQ. ID. NO. 25368 | 100-ArgGlyAsnLysPheTyrGluSerMetTyrArgLeu-111 |
| SEQ. ID. NO. 25369 | 154-LeuAspAspSerIleArg-159 |
| SEQ. ID. NO. 25370 | 226-PheValArgValTyrGluLysGly-233 |
| SEQ. ID. NO. 25371 | 275-IleCysArgLysPheLysAsnMetProValPro-285 |
| SEQ. ID. NO. 25372 | 308-AsnAlaValGlyLysLeuValAsnPhe-316 |
| SEQ. ID. NO. 25373 | 326-GluIleValGluSerLeuLysAla-333 |
| SEQ. ID. NO. 25374 | 336-GlyPheProLysGlyLeuGlu-342 |
| SEQ. ID. NO. 25375 | 348-LeuGluMetLeuArgAspGlyLeuLys-356 |
| SEQ. ID. NO. 25376 | 382-AsnSerAspLysPheAspArg-388 |
| Antigenic Index - Jameson-Wolf | |
| SEQ. ID. NO. 25377 | 1-LeuThrAsnArgGlyGlyAlaLysLeuLysThrAsnSerLysSerSerGluArgMetSerGlu-21 |
| SEQ. ID. NO. 25378 | 29-IleSerAspGlyLysGlyLysLeuLeuGluIleProGlnArgArgGlyLysGlnAspGlyVal-49 |
| SEQ. ID. NO. 25379 | 62-ThrLeuLeuLysValSerGly-68 |
| SEQ. ID. NO. 25380 | 83-ArgLysLeuGluGlu-87 |
| SEQ. ID. NO. 25381 | 93-IleThrArgLysCysLysSerArgGlyAsnLysPheTyrGlu-106 |
| SEQ. ID. NO. 25382 | 108-MetTyrArgLeuGlySerAspAspValAspTyrGly-119 |
| SEQ. ID. NO. 25383 | 122-HisPheGlyGlyGlnArgAsnThrVal-130 |
| SEQ. ID. NO. 25384 | 134-LeuLysGlyThrGlyCys-139 |
| SEQ. ID. NO. 25385 | 152-GlnPheLeuAspAspSerIleArgThrArgIleThrArg-164 |
| SEQ. ID. NO. 25386 | 172-PheAspGlyGluTyrThrProAspGlnAlaLeuLeuAspHisAspAsnGlyPhePheAspAsnSerAsnGlnArgProLysSerGluThrIleGly-203 |
| SEQ. ID. NO. 25387 | 205-AlaTrpArgAsnGluAspGlySerGlyLys-214 |
| SEQ. ID. NO. 25388 | 217-TyrValGlyArgLysLysAsnSerArgPhe-226 |
| SEQ. ID. NO. 25389 | 228-ArgValTyrGluLysGlyArgGlnLeuGlyAspLysGluSerLysTrpVal-244 |
| SEQ. ID. NO. 25390 | 251-AsnTyrGlyAspIleGluIle-257 |
| SEQ. ID. NO. 25391 | 263-IleAsnGlnGlySer-267 |
| SEQ. ID. NO. 25392 | 275-IleCysArgLysPheLysAsnMetProValProGluArgPheAspGlnArgLysLysThrLeu-295 |
| SEQ. ID. NO. 25393 | 321-GlyPheAspAsnSerGluIleValGluSerLeuLysAlaAspSerGlyPheProLysGlyLeuGluProGluLysTyrAla-347 |
| SEQ. ID. NO. 25394 | 350-MetLeuArgAspGlyLeuLys-356 |
| SEQ. ID. NO. 25395 | 361-HisGluGlnProAspIleAspLeuGluIleGluLeuAspGlu-374 |
| SEQ. ID. NO. 25396 | 380-PheLysAsnSerAspLysPheAspArgGluLysArgLeuPheSerProAspTyrAspValGluLysGluArgLysTyrGlnGluTyrLeu-409 |
| SEQ. ID. NO. 25397 | 417-ValAspTyrAspTyrPhe-422 |
| Hydrophilic Regions - Hopp-Woods | |
| SEQ. ID. NO. 25398 | 1-LeuThrAsnArgGlyGlyAlaLysLeuLysThrAsnSerLysSerSerGluArgMetSerGlu-21 |
| SEQ. ID. NO. 25399 | 30-SerAspGlyLysGlyLysLeuLeuGluIleProGlnArgArgGlyLysGlnAspGlyVal-49 |
| SEQ. ID. NO. 25400 | 83-ArgLysLeuGluGlu-87 |

TABLE 1-continued

| | |
|---|---|
| SEQ. ID. NO. 25401 | 93-IleThrArgLysCysLysSerArgGlyAsnLysPheTyr-105 |
| SEQ. ID. NO. 25402 | 111-LeuGlySerAspAspValAspTyrGly-119 |
| SEQ. ID. NO. 25403 | 134-LeuLysGlyThrGly-138 |
| SEQ. ID. NO. 25404 | 152-GlnPheLeuAspAspSerIleArgThrArgIleThrArg-164 |
| SEQ. ID. NO. 25405 | 181-AlaLeuLeuAspHisAspAsnGlyPhe-189 |
| SEQ. ID. NO. 25406 | 193-SerAsnGlnArgProLysSerGluThrIle-202 |
| SEQ. ID. NO. 25407 | 206-TrpArgAsnGluAspGlySerGly-213 |
| SEQ. ID. NO. 25408 | 219-GlyArgLysLysAsnSerArgPhe-226 |
| SEQ. ID. NO. 25409 | 228-ArgValTyrGluLysGlyArgGlnLeuGlyAspLysGluSerLysTrpVal-244 |
| SEQ. ID. NO. 25410 | 277-ArgLysPheLysAsn-281 |
| SEQ. ID. NO. 25411 | 283-ProValProGluArgPheAspGlnArgLysLysThrLeu-295 |
| SEQ. ID. NO. 25412 | 321-GlyPheAspAsnSerGluIleValGluSerLeuLysAlaAspSerGlyPhe-337 |
| SEQ. ID. NO. 25413 | 339-LysGlyLeuGluProGluLysTyrAla-347 |
| SEQ. ID. NO. 25414 | 350-MetLeuArgAspGlyLeuLys-356 |
| SEQ. ID. NO. 25415 | 362-GluGlnProAspIleAspLeuGluIleGluLeuAspGlu-374 |
| SEQ. ID. NO. 25416 | 381-LysAsnSerAspLysPheAspArgGluLysArgLeuPhe-393 |
| SEQ. ID. NO. 25417 | 396-AspTyrAspValGluLysGluArgLysTyrGlnGluTyrLeu-409 | a973
AMPHI Regions - AMPHI

| | |
|---|---|
| SEQ. ID. NO. 25418 | 12-GluArgLeuIleAlaArgLeuAlaArgGluProAspSerAla-25 |
| SEQ. ID. NO. 25419 | 44-AspThrLeuLeuArgLeuGluLysValLeuAspPhe-55 |
| SEQ. ID. NO. 25420 | 77-AspSerIleGluArgIleThrAlaTyr-85 |
| SEQ. ID. NO. 25421 | 112-AspLeuLeuLysTyrMet-117 |
| SEQ. ID. NO. 25422 | 143-AlaLeuLeuLysGluPheArgGluGln-151 |
| SEQ. ID. NO. 25423 | 171-PheGluAspIleIleGluGlnIleValGlyAspIleGluAsp-184 |
| SEQ. ID. NO. 25424 | 208-AlaThrGluIleGluAspIleAsnAlaPhe-217 |
| SEQ. ID. NO. 25425 | 235-IleGlnGluLeuGly-239 |

Antigenic Index - Jameson-Wolf

| | |
|---|---|
| SEQ. ID. NO. 25426 | 1-MetAspGlyAlaGlnProLysThrAsnPhe-10 |
| SEQ. ID. NO. 25427 | 18-LeuAlaArgGluProAspSerAlaGluAsp-27 |
| SEQ. ID. NO. 25428 | 34-GlnAlaHisGluGlnGluValPheAspAlaAspThr-45 |
| SEQ. ID. NO. 25429 | 47-LeuArgLeuGluLysValLeuAsp-54 |
| SEQ. ID. NO. 25430 | 56-SerAspLeuGluValArgAspAlaMetIleThrArgSerArgMetAsnValLeuLysGluAsnAspSerIleGluArg-81 |
| SEQ. ID. NO. 25431 | 96-ValIleGlyGluAspLysAspGluVal-104 |
| SEQ. ID. NO. 25432 | 118-PheAsnProGluGlnPheHis-124 |
| SEQ. ID. NO. 25433 | 136-ProGluGlyLysSer-140 |
| SEQ. ID. NO. 25434 | 146-LysGluPheArgGluGlnArgAsnHis-154 |
| SEQ. ID. NO. 25435 | 159-IleAspGluTyrGlyGlyThrSerGly-167 |
| SEQ. ID. NO. 25436 | 178-IleValGlyAspIleGluAspGluPheAspGluAspGluSerAlaAspAsn-194 |
| SEQ. ID. NO. 25437 | 199-SerAlaGluArgTrpArg-204 |
| SEQ. ID. NO. 25438 | 209-ThrGluIleGluAsp-213 |
| SEQ. ID. NO. 25439 | 219-GlyThrGluTyrSerSerGluGluAlaAspThr-229 |
| SEQ. ID. NO. 25440 | 239-GlyHisLeuProValArgGlyGluLysValLeu-249 |
| SEQ. ID. NO. 25441 | 258-AlaArgAlaAspAsnArgArgLeuHis-266 |

Hydrophilic Regions - Hopp-Woods

| | |
|---|---|
| SEQ. ID. NO. 25442 | 1-MetAspGlyAlaGlnProLys-7 |
| SEQ. ID. NO. 25443 | 18-LeuAlaArgGluProAspSerAlaGluAsp-27 |
| SEQ. ID. NO. 25444 | 34-GlnAlaHisGluGlnGluValPheAsp-42 |
| SEQ. ID. NO. 25445 | 47-LeuArgLeuGluLysValLeuAsp-54 |
| SEQ. ID. NO. 25446 | 56-SerAspLeuGluValArgAspAlaMetIleThrArgSerArgMetAsnValLeuLysGluAsnAspSerIleGluArg-81 |
| SEQ. ID. NO. 25447 | 96-ValIleGlyGluAspLysAspGluVal-104 |
| SEQ. ID. NO. 25448 | 136-ProGluGlyLysSer-140 |
| SEQ. ID. NO. 25449 | 146-LysGluPheArgGluGlnArgAsn-153 |
| SEQ. ID. NO. 25450 | 178-IleValGlyAspIleGluAspGluPheAspGluAspGluSerAlaAspAsn-194 |
| SEQ. ID. NO. 25451 | 199-SerAlaGluArgTrpArg-204 |
| SEQ. ID. NO. 25452 | 209-ThrGluIleGluAsp-213 |
| SEQ. ID. NO. 25453 | 222-TyrSerSerGluGluAlaAspThr-229 |
| SEQ. ID. NO. 25454 | 243-ValArgGlyGluLysValLeu-249 |
| SEQ. ID. NO. 25455 | 258-AlaArgAlaAspAsnArgArgLeuHis-266 | a981
AMPHI Regions - AMPHI

| | |
|---|---|
| SEQ. ID. NO. 25456 | 31-AlaAsnProAspLysValTyrArgValAlaSer-41 |
| SEQ. ID. NO. 25457 | 46-AlaProPheGluSerLeuAsp-52 |
| SEQ. ID. NO. 25458 | 66-AsnAlaMetAlaLys-70 |
| SEQ. ID. NO. 25459 | 132-LysIleSerSerSerGluAspLeuLysAsnMetAsnLysValGlyValVal-148 |
| SEQ. ID. NO. 25460 | 167-LysIleAlaArgPheGlu-172 |
| SEQ. ID. NO. 25461 | 181-LeuGluAsnGlyGlyLeuAspSerValVal-190 |
| SEQ. ID. NO. 25462 | 197-AlaAsnTyrValLysAsnAsnPro-204 |
| SEQ. ID. NO. 25463 | 207-GlyMetAspPheValThrLeuPro-214 |
| SEQ. ID. NO. 25464 | 233-ValLysMetLeuAsnAspAlaLeuLysLysValArgGluSerGlyGluTyr-249 |

Antigenic Index - Jameson-Wolf

| | |
|---|---|
| SEQ. ID. NO. 25465 | 19-CysGlyGlyGlnGlyLysAspAlaAlaAla-28 |
| SEQ. ID. NO. 25466 | 31-AlaAsnProAspLysValTyrArg-38 |
| SEQ. ID. NO. 25467 | 49-GluSerLeuAspSerLysGlyAsnValGluGlyPheAsp-61 |
| SEQ. ID. NO. 25468 | 76-IleGluPheLysHisGlnProTrpAspSer-85 |
| SEQ. ID. NO. 25469 | 90-LeuAsnAsnGlyAspAlaAspVal-97 |
| SEQ. ID. NO. 25470 | 104-IleThrAspAspArgLysGlnSerMetAspPheSerAspProTyrPhe-119 |
| SEQ. ID. NO. 25471 | 127-ValProLysGlyLysLysIleSerSerSerGluAspLeuLysAsnMetAsnLys-144 |
| SEQ. ID. NO. 25472 | 160-LeuLeuGlyAsnAspAsnProLysIleAlaArg-170 |
| SEQ. ID. NO. 25473 | 179-LysGluLeuGluAsnGlyGlyLeuAspSerValValSerAspSerAla-194 |

TABLE 1-continued

| SEQ. ID. NO. 25474 | 201-LysAsnAsnProThrLysGlyMetAspPhe-210 |
|---|---|
| SEQ. ID. NO. 25475 | 214-ProAspPheThrThr-218 |
| SEQ. ID. NO. 25476 | 225-ValArgLysGlyAspGluAlaThrVal-233 |
| SEQ. ID. NO. 25477 | 235-MetLeuAsnAspAlaLeuLysLysValArgGluSerGlyGluTyrAspLysIleTyr-253 |
| SEQ. ID. NO. 25478 | 257-PheAlaLysGluAspGlyGlnAlaAlaLys-266 |

Hydrophilic Regions - Hopp-Woods

| SEQ. ID. NO. 25479 | 21-GlyGlnGlyLysAspAlaAlaAla-28 |
|---|---|
| SEQ. ID. NO. 25480 | 31-AlaAsnProAspLysValTyrArg-38 |
| SEQ. ID. NO. 25481 | 49-GluSerLeuAspSerLysGlyAsnValGluGlyPheAsp-61 |
| SEQ. ID. NO. 25482 | 91-AsnAsnGlyAspAlaAspVal-97 |
| SEQ. ID. NO. 25483 | 104-IleThrAspAspArgLysGlnSerMetAspPheSer-115 |
| SEQ. ID. NO. 25484 | 128-ProLysGlyLysLysIleSerSerSerGluAspLeuLysAsnMetAsn-143 |
| SEQ. ID. NO. 25485 | 164-AspAsnProLysIleAlaArg-170 |
| SEQ. ID. NO. 25486 | 179-LysGluLeuGluAsnGlyGlyLeu-186 |
| SEQ. ID. NO. 25487 | 203-AsnProThrLysGlyMetAsp-209 |
| SEQ. ID. NO. 25488 | 225-ValArgLysGlyAspGluAlaThrVal-233 |
| SEQ. ID. NO. 25489 | 235-MetLeuAsnAspAlaLeuLysLysValArgGluSerGlyGluTyrAspLysIleTyr-253 |
| SEQ. ID. NO. 25490 | 257-PheAlaLysGluAspGlyGlnAlaAlaLys-266 | a982
AMPHI Regions - AMPHI

| SEQ. ID. NO. 25491 | 12-ValArgGlnLysMetValAsnGlyValAsnIleLeuAlaAsnAlaVal-27 |
|---|---|
| SEQ. ID. NO. 25492 | 71-AlaGlnMetValLysGluValAlaSerLysThr-81 |
| SEQ. ID. NO. 25493 | 100-ValAlaGluGlyMetLysTyr-106 |
| SEQ. ID. NO. 25494 | 115-AspLeuLysArgGlyIleAspLysAlaValAlaAlaLeuValGluGluLeuLysAsnIleAlaLysProCysAspThrSerLysGluIleAlaGln ValGlySer-149 |
| SEQ. ID. NO. 25495 | 160-AlaIleIleAlaGluAlaMetGluLysValGly-170 |
| SEQ. ID. NO. 25496 | 185-AsnGluLeuAspValValGluGlyMet-193 |
| SEQ. ID. NO. 25497 | 209-GluLysGlnIleAlaGlyLeuAsp-216 |
| SEQ. ID. NO. 25498 | 227-IleSerAsnIleArgAspLeuLeuProValLeuGluGlnValAlaLysAla-243 |
| SEQ. ID. NO. 25499 | 265-AsnAsnIleArgGlyIleLeuLysThrValAla-275 |
| SEQ. ID. NO. 25500 | 313-ThrLeuAspAspLeuGlyGlnAlaLysArgIle-323 |
| SEQ. ID. NO. 25501 | 331-ThrIleIleAspGlyPheGlyAspAlaAla-340 |
| SEQ. ID. NO. 25502 | 367-GluArgValAlaLysLeuAlaGlyGlyVal-376 |
| SEQ. ID. NO. 25503 | 426-LeuGluAsnLeuHisThr-431 |
| SEQ. ID. NO. 25504 | 444-LeuArgAlaValGluSerProLeuArgGlnIleValAlaAsnAla-458 |
| SEQ. ID. NO. 25505 | 484-GluTyrGlyAspMetIleGluMet-491 |
| SEQ. ID. NO. 25506 | 500-ThrArgSerAlaLeu-504 |

Antigenic Index - Jameson-Wolf

| SEQ. ID. NO. 25507 | 1-MetAlaAlaLysAspValGlnPhe-8 |
|---|---|
| SEQ. ID. NO. 25508 | 10-AsnGluValArgGlnLysMetValAsn-18 |
| SEQ. ID. NO. 25509 | 30-ThrLeuGlyProLysGlyArgAsnValValVal-40 |
| SEQ. ID. NO. 25510 | 43-AlaPheGlyGlyProHisIleThrLysAspGlyValThrValAlaLysGluIleGluLeuLysAspLysPheGluAsnMetGly-70 |
| SEQ. ID. NO. 25511 | 73-MetValLysGluValAlaSerLysThrAsnAspValAlaGlyAspGlyThrThr-90 |
| SEQ. ID. NO. 25512 | 112-AsnProThrAspLeuLysArgGlyIleAspLysAlaVal-124 |
| SEQ. ID. NO. 25513 | 129-GluGluLeuLysAsnIleAlaLysProCysAspThrSerLysGluIleAla-145 |
| SEQ. ID. NO. 25514 | 150-IleSerAlaAsnSerAspGluGlnVal-158 |
| SEQ. ID. NO. 25515 | 164-GluAlaMetGluLysValGlyLysGluGlyValIleThrValGluAspGlyLysSerLeuGluAsnGluLeuAspVal-189 |
| SEQ. ID. NO. 25516 | 193-MetGlnPheAspArgGlyTyr-199 |
| SEQ. ID. NO. 25517 | 207-AspAlaGluLysGlnIleAla-213 |
| SEQ. ID. NO. 25518 | 223-PheAspLysLysIleSerAsnIleArgAsp-232 |
| SEQ. ID. NO. 25519 | 239-GlnValAlaLysAlaSerArg-245 |
| SEQ. ID. NO. 25520 | 252-GluAspValGluGlyGluAla-258 |
| SEQ. ID. NO. 25521 | 266-AsnIleArgGlyIleLeu-271 |
| SEQ. ID. NO. 25522 | 278-AlaProGlyPheGlyAspArgArgLysAlaMetLeu-289 |
| SEQ. ID. NO. 25523 | 301-IleSerGluGluValGlyLeuSerLeuGluLysAlaThrLeuAspAspLeuGlyGlnAlaLysArgIleGluIleGlyLysGluAsnThrThr-331 |
| SEQ. ID. NO. 25524 | 334-AspGlyPheGlyAspAlaAlaGlnIleGluAlaArgValAlaGluIleArgGlnGlnIleGluThrAlaThrSerAspTyrAspLysGluLysLeu GlnGluArgValAlaLysLeuAlaGly-374 |
| SEQ. ID. NO. 25525 | 385-ThrGluValGluMetLysGluLysLysAspArgValGluAspAlaLeuHis-401 |
| SEQ. ID. NO. 25526 | 405-AlaAlaValGluGluGlyVal-411 |
| SEQ. ID. NO. 25527 | 421-ArgAlaArgAlaAlaLeu-426 |
| SEQ. ID. NO. 25528 | 429-LeuHisThrGlyAsnAlaAspGlnAspAlaGlyVal-440 |
| SEQ. ID. NO. 25529 | 446-AlaValGluSerProLeuArg-452 |
| SEQ. ID. NO. 25530 | 457-AsnAlaGlyGlyGluProSerVal-464 |
| SEQ. ID. NO. 25531 | 469-ValLeuGlyGlyLysGlyAsnTyrGlyTyr-478 |
| SEQ. ID. NO. 25532 | 480-AlaGlySerGlyGluTyrGlyAspMetIleGlu-490 |
| SEQ. ID. NO. 25533 | 495-AspProAlaLysValThrArgSerAlaLeu-504 |
| SEQ. ID. NO. 25534 | 523-GluIleProGluAspLysProAlaMetProAspMetGlyGly-536 |

Hydrophilic Regions - Hopp-Woods

| SEQ. ID. NO. 25535 | 1-MetAlaAlaLysAspValGlnPhe-8 |
|---|---|
| SEQ. ID. NO. 25536 | 10-AsnGluValArgGlnLysMet-16 |
| SEQ. ID. NO. 25537 | 33-ProLysGlyArgAsnValValVal-40 |
| SEQ. ID. NO. 25538 | 48-HisIleThrLysAspGlyValThrValAlaLysGluIleGluLeuLysAspLysPheGluAsn-68 |
| SEQ. ID. NO. 25539 | 73-MetValLysGluValAlaSerLysThrAsnAspValAlaGlyAspGlyThrThr-90 |
| SEQ. ID. NO. 25540 | 114-ThrAspLeuLysArgGlyIleAspLysAlaVal-124 |
| SEQ. ID. NO. 25541 | 129-GluGluLeuLysAsnIleAlaLysProCysAspThrSerLysGluIleAla-145 |
| SEQ. ID. NO. 25542 | 152-AlaAsnSerAspGluGlnVal-158 |
| SEQ. ID. NO. 25543 | 164-GluAlaMetGluLysValGlyLysGluGlyValIleThrValGluAspGlyLysSerLeuGluAsnGluLeuAspVal-189 |
| SEQ. ID. NO. 25544 | 207-AspAlaGluLysGlnIleAla-213 |
| SEQ. ID. NO. 25545 | 223-PheAspLysLysIleSerAsnIleArgAsp-232 |
| SEQ. ID. NO. 25546 | 239-GlnValAlaLysAlaSerArg-245 |

TABLE 1-continued

| | |
|---|---|
| SEQ. ID. NO. 25547 | 252-GluAspValGluGlyGluAla-258 |
| SEQ. ID. NO. 25548 | 280-GlyPheGlyAspArgArgLysAlaMetLeu-289 |
| SEQ. ID. NO. 25549 | 301-IleSerGluGluValGlyLeuSerLeuGluLysAlaThrLeuAspAspLeuGlyGlnAlaLysArgIleGluIleGlyLysGluAsnThrThr-331 |
| SEQ. ID. NO. 25550 | 340-AlaGlnIleGluAlaArgValAlaGluIleArgGlnGlnIleGluThrAlaThrSerAspTyrAspLysGluLysLeuGlnGluArgValAlaLys-371 |
| SEQ. ID. NO. 25551 | 385-ThrGluValGluMetLysGluLysLysAspArgValGluAspAlaLeuHis-401 |
| SEQ. ID. NO. 25552 | 405-AlaAlaValGluGluGlyVal-411 |
| SEQ. ID. NO. 25553 | 421-ArgAlaArgAlaAlaLeu-426 |
| SEQ. ID. NO. 25554 | 432-GlyAsnAlaAspGlnAspAla-438 |
| SEQ. ID. NO. 25555 | 446-AlaValGluSerProLeu-451 |
| SEQ. ID. NO. 25556 | 458-AlaGlyGlyGluPro-462 |
| SEQ. ID. NO. 25557 | 469-ValLeuGluGlyLysGly-474 |
| SEQ. ID. NO. 25558 | 481-GlySerGlyGluTyrGlyAsp-487 |
| SEQ. ID. NO. 25559 | 495-AspProAlaLysValThrArg-501 |
| SEQ. ID. NO. 25560 | 523-GluIleProGluAspLysProAlaMet-531 | a986
AMPHI Regions - AMPHI

| | |
|---|---|
| SEQ. ID. NO. 25561 | 6-GlnTyrLeuAlaLeuAla-11 |
| SEQ. ID. NO. 25562 | 18-LeuAlaGlyCysAspLysAlaGly-25 |
| SEQ. ID. NO. 25563 | 36-SerPheValGluArgIleLysHis-43 |
| SEQ. ID. NO. 25564 | 52-MetLeuLeuProAspPheValGlnLeuVal-61 |
| SEQ. ID. NO. 25565 | 97-AspProPheTyrGluPhePheLysArgLeuValProAsnMetProGluIleProGln-115 |
| SEQ. ID. NO. 25566 | 145-ThrGlyMetGlySerIle-150 |
| SEQ. ID. NO. 25567 | 162-AlaLysLeuIleGlySerAspVal-169 |
| SEQ. ID. NO. 25568 | 189-IleGlyAsnProLysAspLeuLysProGly-198 |
| SEQ. ID. NO. 25569 | 200-TrpValAlaAlaIleGly-205 |
| SEQ. ID. NO. 25570 | 287-AlaGluGlnLeuLysAsnThrGlyLysVal-296 |
| SEQ. ID. NO. 25571 | 393-AlaAlaGluHisIleGlyAlaSer-400 |
| SEQ. ID. NO. 25572 | 471-ArgLysAlaMetAspLysAla-477 |

Antigenic Index - Jameson-Wolf

| | |
|---|---|
| SEQ. ID. NO. 25573 | 1-ValPheLysLysTyr-5 |
| SEQ. ID. NO. 25574 | 20-GlyCysAspLysAlaGly-25 |
| SEQ. ID. NO. 25575 | 29-GlyAlaAspLysLysGluAlaSerPheValGluArgIleLysHisThrLysAspAspGlySerVal-50 |
| SEQ. ID. NO. 25576 | 61-ValGlnSerGluGlyProAla-67 |
| SEQ. ID. NO. 25577 | 75-ProAlaProArgThrGlnAsnGlySerSerAsnAlaGluThrAspSerAspProLeuAlaAspSerAspProPhe-99 |
| SEQ. ID. NO. 25578 | 104-LysArgLeuValProAsnMetProGluIleProGlnGluGluAlaAspAspGlyGlyLeu-123 |
| SEQ. ID. NO. 25579 | 130-IleIleSerLysAspGlyTyr-136 |
| SEQ. ID. NO. 25580 | 154-LeuAsnAspLysArgGluTyrThr-161 |
| SEQ. ID. NO. 25581 | 165-IleGlySerAspValGlnSerAspValAla-174 |
| SEQ. ID. NO. 25582 | 179-AspAlaThrGluGluLeuPro-185 |
| SEQ. ID. NO. 25583 | 189-IleGlyAsnProLysAspLeuLysProGlyGlu-199 |
| SEQ. ID. NO. 25584 | 208-PheGlyPheAspAsnSerValThr-215 |
| SEQ. ID. NO. 25585 | 218-XxxValSerAlaLysGlyArgSerLeuProAsnGluSerTyr-231 |
| SEQ. ID. NO. 25586 | 242-AsnProGlyAsnSerGlyGlyPro-249 |
| SEQ. ID. NO. 25587 | 265-TyrSerArgSerGlyGly-270 |
| SEQ. ID. NO. 25588 | 288-GluGlnLeuLysAsnThrGlyLysValGlnArgGlyGlnLeu-301 |
| SEQ. ID. NO. 25589 | 316-PheGlyLeuAspLysAlaGlyGly-323 |
| SEQ. ID. NO. 25590 | 330-LeuProGlySerProAlaGluArgAlaGlyLeuArgAlaGlyAsp-344 |
| SEQ. ID. NO. 25591 | 349-LeuAspGlyGlyGluIleArgSerSerGlyAspLeu-360 |
| SEQ. ID. NO. 25592 | 368-ThrProGlyLysGluValSer-374 |
| SEQ. ID. NO. 25593 | 378-TrpArgLysGlyGluGluIleThrIle-386 |
| SEQ. ID. NO. 25594 | 397-IleGlyAlaSerSerLysThrAspGluAlaProTyrThrGluGlnGlnSerGlyThrPhe-416 |
| SEQ. ID. NO. 25595 | 427-ThrHisThrAspSerSerGlyGly-434 |
| SEQ. ID. NO. 25596 | 440-ArgValSerAspAlaAlaGluArgAlaGlyLeuArgArgGlyAspGluIleLeu-457 |
| SEQ. ID. NO. 25597 | 463-ProValAsnAspGluAlaGlyPheArgLysAlaMetAspLysAlaGlyLysAsnVal-481 |
| SEQ. ID. NO. 25598 | 486-MetArgArgGlyAsnThr-491 |

Hydrophilic Regions - Hopp-Woods

| | |
|---|---|
| SEQ. ID. NO. 25599 | 20-GlyCysAspLysAlaGly-25 |
| SEQ. ID. NO. 25600 | 29-GlyAlaAspLysLysGluAlaSerPheValGluArgIleLysHisThrLysAspAspGlySer-49 |
| SEQ. ID. NO. 25601 | 75-ProAlaProArgThrGlnAsnGlySerSerAsnAlaGluThrAspSerAspProLeuAlaAspSerAspPro-98 |
| SEQ. ID. NO. 25602 | 111-ProGluIleProGlnGluGluAlaAspAspGlyGly-122 |
| SEQ. ID. NO. 25603 | 131-IleSerLysAspGly-135 |
| SEQ. ID. NO. 25604 | 154-LeuAsnAspLysArgGluTyrThr-161 |
| SEQ. ID. NO. 25605 | 179-AspAlaThrGluGluLeuPro-185 |
| SEQ. ID. NO. 25606 | 190-GlyAsnProLysAspLeuLysPro-197 |
| SEQ. ID. NO. 25607 | 219-ValSerAlaLysGlyArgSerLeuPro-227 |
| SEQ. ID. NO. 25608 | 288-GluGlnLeuLysAsnThrGlyLysValGlnArgGlyGln-300 |
| SEQ. ID. NO. 25609 | 317-GlyLeuAspLysAlaGly-322 |
| SEQ. ID. NO. 25610 | 333-SerProAlaGluArgAlaGlyLeuArgAlaGlyAsp-344 |
| SEQ. ID. NO. 25611 | 350-AspGlyGlyGluIleArgSerSerGlyAsp-359 |
| SEQ. ID. NO. 25612 | 368-ThrProGlyLysGluValSer-374 |
| SEQ. ID. NO. 25613 | 379-ArgLysGlyGluGluIleThrIle-386 |
| SEQ. ID. NO. 25614 | 397-IleGlyAlaSerSerLysThrAspGluAlaProTyrThrGluGlnGlnSer-413 |
| SEQ. ID. NO. 25615 | 428-HisThrAspSerSerGly-433 |
| SEQ. ID. NO. 25616 | 440-ArgValSerAspAlaAlaGluArgAlaGlyLeuArgArgGlyAspGluIleLeu-457 |
| SEQ. ID. NO. 25617 | 463-ProValAsnAspGluAlaGlyPheArgLysAlaMetAspLysAlaGlyLys-479 | a987
AMPHI Regions - AMPHI

| | |
|---|---|
| SEQ. ID. NO. 25618 | 17-CysSerSerTrpLeu-21 |
| SEQ. ID. NO. 25619 | 33-PheAsnThrSerLysProValArgLeuAspAsnIleLeuGlnIle-47 |
| SEQ. ID. NO. 25620 | 65-ProHisGluAlaPhe-69 |

TABLE 1-continued

| | |
|---|---|
| SEQ. ID. NO. 25621 | 144-AsnProPheValLeuArgLysTrpArgAlaLeuGlyTyrLeuThrAspPheProArgLeuAsnArg-165 |
| SEQ. ID. NO. 25622 | 187-GlyAspGluTyrPheLysVal-193 |
| SEQ. ID. NO. 25623 | 202-LeuAspIleLeuAlaThr-207 |
| SEQ. ID. NO. 25624 | 211-ValGlyGluValSerHisAspPheAspArgTyrTrpAla-223 |
| SEQ. ID. NO. 25625 | 230-AlaThrArgIleIleArgSerGly-237 |
| SEQ. ID. NO. 25626 | 239-IleGlyLysGlyLeuGlnAla-245 |
| SEQ. ID. NO. 25627 | 289-SerAspAspProAlaLysGlyLeuAspArg-298 |
| SEQ. ID. NO. 25628 | 307-GlyArgLeuGlnAspAlaLeuLysGlnPro-316 |
| SEQ. ID. NO. 25629 | 333-GlyThrAspAlaLeuAlaLysLeuValGlnAsp-343 |
| SEQ. ID. NO. 25630 | 355-GlnAlaThrAspValAlaAla-361 |
| SEQ. ID. NO. 25631 | 443-LysIleAlaGluGlnMetGluArgThrLeuAlaAspThr-455 |
| SEQ. ID. NO. 25632 | 486-ProGluAlaLysLeuTrpLysArgIleAlaAlaLysIleLeuSerLeuLeuProIleGluSerLeu-507 |
| Antigenic Index - Jameson-Wolf | |
| SEQ. ID. NO. 25633 | 1-MetLysThrArgSer-5 |
| SEQ. ID. NO. 25634 | 23-ProLeuGluGluArgThrGluSerArgHisPheAsnThrSerLysProValArgLeu-41 |
| SEQ. ID. NO. 25635 | 49-HisThrProHisThrAsnGlyLeuSer-57 |
| SEQ. ID. NO. 25636 | 77-GluSerAlaGluHisSerLeu-83 |
| SEQ. ID. NO. 25637 | 90-TrpArgAsnAspIleSerGlyArgLeu-98 |
| SEQ. ID. NO. 25638 | 107-AlaGluArgGlyValArg-112 |
| SEQ. ID. NO. 25639 | 115-LeuLeuLeuAspAspAsnAsnThrArgGlyLeuAsp-126 |
| SEQ. ID. NO. 25640 | 134-SerHisProAsnIleGluValArgLeu-142 |
| SEQ. ID. NO. 25641 | 159-AspPheProArgLeuAsnArgArgMetHisAsnLysSerPheThrAlaAspAsnArgAla-178 |
| SEQ. ID. NO. 25642 | 182-GlyGlyArgAsnIleGlyAspGluTyrPheLysValGlyGluAspThrVal-198 |
| SEQ. ID. NO. 25643 | 214-ValSerHisAspPheAspArgTyrTrp-222 |
| SEQ. ID. NO. 25644 | 225-HisSerAlaHisAsn-229 |
| SEQ. ID. NO. 25645 | 232-ArgIleIleArgSerGlyAsnIleGlyLysGlyLeu-243 |
| SEQ. ID. NO. 25646 | 247-GlyTyrAsnAspGluThrSerArg-254 |
| SEQ. ID. NO. 25647 | 259-ArgTyrArgGluThrValGlu-265 |
| SEQ. ID. NO. 25648 | 267-SerProLeuTyrGln-271 |
| SEQ. ID. NO. 25649 | 273-IleGlnThrGlyArgIleAsp-279 |
| SEQ. ID. NO. 25650 | 287-LeuIleSerAspAspProAlaLysGlyLeuAspArgAspArgArgLysProProIle-305 |
| SEQ. ID. NO. 25651 | 308-ArgLeuGlnAspAlaLeuLysGlnProGluLysSer-319 |
| SEQ. ID. NO. 25652 | 328-ValProThrLysSerGlyThrAspAlaLeu-337 |
| SEQ. ID. NO. 25653 | 340-LeuValGlnAspGlyIleAsp-346 |
| SEQ. ID. NO. 25654 | 367-ValLysTyrArgLysProLeuLeu-374 |
| SEQ. ID. NO. 25655 | 391-AlaThrLysAspLysGlyLeuThrGlySerSer-401 |
| SEQ. ID. NO. 25656 | 412-ValAspGlyLysArgIlePhe-418 |
| SEQ. ID. NO. 25657 | 422-PheAsnLeuAspProArgSerAlaArgLeuAsnThr-433 |
| SEQ. ID. NO. 25658 | 440-GluSerProLysIleAlaGluGlnMetGluArgThrLeuAlaAspThrSerProGluTyrAla-460 |
| SEQ. ID. NO. 25659 | 463-ValThrLeuAspArgHisAsnArgLeuGlnTrpAspProAlaThrArgLysThrTyrProAsnGluProGluAlaLysLeuTrpLys-492 |
| Hydrophilic Regions - Hopp-Woods | |
| SEQ. ID. NO. 25660 | 1-MetLysThrArgSer-5 |
| SEQ. ID. NO. 25661 | 24-LeuGluGluArgThrGluSerArgHisPheAsnThr-35 |
| SEQ. ID. NO. 25662 | 37-LysProValArgLeu-41 |
| SEQ. ID. NO. 25663 | 77-GluSerAlaGluHisSerLeu-83 |
| SEQ. ID. NO. 25664 | 107-AlaGluArgGlyValArg-112 |
| SEQ. ID. NO. 25665 | 115-LeuLeuLeuAspAspAsnAsnThrArgGlyLeuAsp-126 |
| SEQ. ID. NO. 25666 | 161-ProArgLeuAsnArgArgMetHisAsn-169 |
| SEQ. ID. NO. 25667 | 172-PheThrAlaAspAsnArgAla-178 |
| SEQ. ID. NO. 25668 | 189-GluTyrPheLysValGlyGluAspThrVal-198 |
| SEQ. ID. NO. 25669 | 214-ValSerHisAspPheAspArg-220 |
| SEQ. ID. NO. 25670 | 248-TyrAsnAspGluThrSerArg-254 |
| SEQ. ID. NO. 25671 | 259-ArgTyrArgGluThrValGlu-265 |
| SEQ. ID. NO. 25672 | 274-GlnThrGlyArgIleAsp-279 |
| SEQ. ID. NO. 25673 | 287-LeuIleSerAspAspProAlaLysGlyLeuAspArgAspArgArgLysProProIle-305 |
| SEQ. ID. NO. 25674 | 308-ArgLeuGlnAspAlaLeuLysGlnProGluLysSer-319 |
| SEQ. ID. NO. 25675 | 331-LysSerGlyThrAspAlaLeu-337 |
| SEQ. ID. NO. 25676 | 340-LeuValGlnAspGlyIleAsp-346 |
| SEQ. ID. NO. 25677 | 367-ValLysTyrArgLysProLeuLeu-374 |
| SEQ. ID. NO. 25678 | 391-AlaThrLysAspLysGlyLeuThr-398 |
| SEQ. ID. NO. 25679 | 424-LeuAspProArgSerAlaArgLeuAsnThr-433 |
| SEQ. ID. NO. 25680 | 440-GluSerProLysIleAlaGluGlnMetGluArgThrLeuAlaAspThrSerPro-457 |
| SEQ. ID. NO. 25681 | 464-ThrLeuAspArgHisAsnArg-470 |
| SEQ. ID. NO. 25682 | 476-ProAlaThrArgLysThrTyrProAsnGluProGluAlaLysLeuTrpLys-492 |
| a988 | |
| AMPHI Regions - AMPHI | |
| SEQ. ID. NO. 25683 | 45-SerLysIleGluAlaLeu-50 |
| SEQ. ID. NO. 25684 | 66-ArgArgLeuLysAlaMet-71 |
| SEQ. ID. NO. 25685 | 125-GlnMetArgGlyIle-129 |
| SEQ. ID. NO. 25686 | 154-AspIleValGluArgAlaGlnSerLysVal-163 |
| SEQ. ID. NO. 25687 | 221-AlaLysIleIleGluValLeuGlyAspTyrAlaAsp-232 |
| SEQ. ID. NO. 25688 | 248-HisGlnPheSerGluAlaCysAlaLysAlaAlaLysLysIleProAspHisValArgLys-267 |
| SEQ. ID. NO. 25689 | 288-ThrAlaArgAspPheAspAsp-294 |
| SEQ. ID. NO. 25690 | 299-GluLysIleGlyArgAsnTyrArg-306 |
| SEQ. ID. NO. 25691 | 310-AlaIleAlaAspValSerHisTyrValArgProAspAsp-322 |
| SEQ. ID. NO. 25692 | 348-AsnLeuSerAsnGly-352 |
| SEQ. ID. NO. 25693 | 396-AsnGlnValTrpLysTrpLeuSer-403 |
| SEQ. ID. NO. 25694 | 405-GlyIleGluHisPro-409 |
| SEQ. ID. NO. 25695 | 411-LysThrGlnIleAspThrLeuTyrLysLeuPheLysIleLeuGlnLys-426 |
| SEQ. ID. NO. 25696 | 494-LeuGlyProThrProGluLysLeuAlaAlaLeu-504 |

TABLE 1-continued

| | |
|---|---|
| SEQ. ID. NO. 25697 | 524-LysAspTyrAlaAlaLeuAla-530 |
| SEQ. ID. NO. 25698 | 544-ValMetMetLeuArgSerMetGlnGlnAla-553 |
| SEQ. ID. NO. 25699 | 569-AlaTyrAlaHisPheThrSerProIleArgArgTyrProAspLeuThrValHisArgAlaIleLysAlaValLeu-593 |
| SEQ. ID. NO. 25700 | 619-AspAspAlaSerArgAspValGluAsnTrpLeuLys-630 |
| SEQ. ID. NO. 25701 | 646-IleSerGlyMetThrSerPheGlyIlePheValThrLeu-658 |
| SEQ. ID. NO. 25702 | 662-HisIleAspGlyLeuValHisIleSerAspLeuGlyGlu-674 |
| Antigenic Index - Jameson-Wolf | |
| SEQ. ID. NO. 25703 | 1-MetAsnLysAsnIleLys-6 |
| SEQ. ID. NO. 25704 | 8-LeuAsnLeuArgGluLysAspProPheLeuSerArgGluLysGlnArgTyrGluHisProLeuProSerArgGluTrpIle-34 |
| SEQ. ID. NO. 25705 | 37-LeuLeuGluArgLysGlyValProSerLysIleGluAlaLeuValArg-52 |
| SEQ. ID. NO. 25706 | 54-LeuSerIleLysGluGluGluTyrGluPhePheGluArgArgLeuLysAlaMetAlaArgAspGlyGln-76 |
| SEQ. ID. NO. 25707 | 79-IleAsnArgArgGlyAlaVal-85 |
| SEQ. ID. NO. 25708 | 87-AlaAlaAspLysLeuAspLeuValLysCysArgValLysAlaHisLysAspArgPheGlyPhe-107 |
| SEQ. ID. NO. 25709 | 111-LeuThrProAlaLysAspGlyAsp-118 |
| SEQ. ID. NO. 25710 | 124-ArgGlnMetArgGly-128 |
| SEQ. ID. NO. 25711 | 140-AlaGlyMetAspGlyArgGlyArgArgGluGlyThrVal-152 |
| SEQ. ID. NO. 25712 | 155-IleValGluArgAlaGlnSerLysValValGly-165 |
| SEQ. ID. NO. 25713 | 167-PheXxxMetAspArgGlyValAla-174 |
| SEQ. ID. NO. 25714 | 176-LeuGluProGluAspLysArgLeuAsnGln-185 |
| SEQ. ID. NO. 25715 | 189-LeuGluProAspGlyValAlaArgPheLysProGluSerGlyGln-203 |
| SEQ. ID. NO. 25716 | 210-GluValTyrProGluGlnAsnArgProAlaVal-220 |
| SEQ. ID. NO. 25717 | 227-LeuGlyAspTyrAlaAspSerGlyMetGluIle-237 |
| SEQ. ID. NO. 25718 | 239-IleAlaValArgLysHisHisLeu-246 |
| SEQ. ID. NO. 25719 | 253-AlaCysAlaLysAlaAlaLysLysIleProAspHisValArgLysSerAspLeuLysGlyArgValAspLeuArgAsp-278 |
| SEQ. ID. NO. 25720 | 283-ThrIleAspGlyGluThrAlaArgAspPheAspAsp-294 |
| SEQ. ID. NO. 25721 | 299-GluLysIleGlyArgAsnTyrArg-306 |
| SEQ. ID. NO. 25722 | 316-HisTyrValArgProAspAspAlaIleAspThrAspAlaGlnGluArgSerThrSerVal-335 |
| SEQ. ID. NO. 25723 | 337-PheProArgArgVal-341 |
| SEQ. ID. NO. 25724 | 345-LeuProGluAsnLeuSerAsnGly-352 |
| SEQ. ID. NO. 25725 | 374-AlaGlyAsnIleLysGluTyrArgPhe-382 |
| SEQ. ID. NO. 25726 | 402-LeuSerGlyGlyIleGluHisProPheLysThrGlnIle-414 |
| SEQ. ID. NO. 25727 | 424-LeuGlnLysLysArgPheGluArgGlyAlaValGluPheAspSerIleGlu-440 |
| SEQ. ID. NO. 25728 | 443-MetLeuPheAspAspAsnGlyLysIleGluLys-453 |
| SEQ. ID. NO. 25729 | 458-ValArgAsnAspAlaHisLysLeuIleGlu-467 |
| SEQ. ID. NO. 25730 | 482-LeuLysAsnLysHisThrAla-488 |
| SEQ. ID. NO. 25731 | 493-HisLeuGlyProThrProGluLysLeuAlaAlaLeuArgGluGlnLeu-508 |
| SEQ. ID. NO. 25732 | 516-GlyGlyGlyAspAsnProSerProLysAspTyrAla-527 |
| SEQ. ID. NO. 25733 | 532-GlnPheLysGlyArgProAspAlaGluLeu-541 |
| SEQ. ID. NO. 25734 | 556-GluProHisCysAspGlyHis-562 |
| SEQ. ID. NO. 25735 | 575-SerProIleArgArgTyrProAspLeuThrVal-585 |
| SEQ. ID. NO. 25736 | 597-ThrTyrThrProLysLysSerTrp-604 |
| SEQ. ID. NO. 25737 | 613-PheCysGluArgArgAlaAspAspAlaSerArgAspValGluAsn-627 |
| SEQ. ID. NO. 25738 | 633-TyrMetArgAspLysValGlyGluValPheGluGlyLysIleSerGly-648 |
| SEQ. ID. NO. 25739 | 670-SerAspLeuGlyGluAspTyrPheAsnPheArgPro-681 |
| SEQ. ID. NO. 25740 | 683-IleMetAlaIleGluGlyGluArgSerGlyIleArgPheAsnMetGlyAspArgValAlaValArgValAlaArgAlaAspLeuAspAspGlyLysIle-715 |
| SEQ. ID. NO. 25741 | 722-GlyGlySerGlyArgGlyArgLysValLysSerSerAlaSerAlaLysProAlaGlyThrAlaGlyLysGlyLysProLysThrAlaAlaGluLysLysThrAlaArgGlyGlyLysValArgGlyArgGlyAlaSerAlaAlaAlaGluSerArgLysLysAlaLysLysProValProIleLysValLysLysArgLysGlyLysSer-791 |
| Hydrophilic Regions - Hopp-Woods | |
| SEQ. ID. NO. 25742 | 1-MetAsnLysAsnIleLys-6 |
| SEQ. ID. NO. 25743 | 8-LeuAsnLeuArgGluLysAspProPheLeuSerArgGluLysGlnArgTyrGluHis-26 |
| SEQ. ID. NO. 25744 | 37-LeuLeuGluArgLysGlyValProSerLysIleGluAlaLeuValArg-52 |
| SEQ. ID. NO. 25745 | 54-LeuSerIleLysGluGluGluTyrGluPhePheGluArgArgLeuLysAlaMetAlaArgAspGlyGln-76 |
| SEQ. ID. NO. 25746 | 79-IleAsnArgArgGlyAla-84 |
| SEQ. ID. NO. 25747 | 87-AlaAlaAspLysLeuAspLeuValLysCysArgValLysAlaHisLysAspArgPhe-105 |
| SEQ. ID. NO. 25748 | 113-ProAlaLysAspGlyAsp-118 |
| SEQ. ID. NO. 25749 | 140-AlaGlyMetAspGlyArgGlyArgArgGluGlyThrVal-152 |
| SEQ. ID. NO. 25750 | 155-IleValGluArgAlaGlnSerLysValValGly-165 |
| SEQ. ID. NO. 25751 | 167-PheXxxMetAspArgGlyValAla-174 |
| SEQ. ID. NO. 25752 | 176-LeuGluProGluAspLysArgLeuAsn-184 |
| SEQ. ID. NO. 25753 | 189-LeuGluProAspGlyValAlaArgPheLysProGluSerGly-202 |
| SEQ. ID. NO. 25754 | 210-GluValTyrProGluGlnAsnArgProAlaVal-220 |
| SEQ. ID. NO. 25755 | 230-TyrAlaAspSerGlyMetGluIle-237 |
| SEQ. ID. NO. 25756 | 239-IleAlaValArgLysHisHis-245 |
| SEQ. ID. NO. 25757 | 253-AlaCysAlaLysAlaAlaLysLysIleProAspHisValArgLysSerAspLeuLysGlyArgValAspLeuArgAsp-278 |
| SEQ. ID. NO. 25758 | 284-IleAspGlyGluThrAlaArgAspPheAspAsp-294 |
| SEQ. ID. NO. 25759 | 300-LysIleGlyArgAsnTyr-305 |
| SEQ. ID. NO. 25760 | 318-ValArgProAspAspAlaIleAspThrAspAlaGlnGluArgSerThr-333 |
| SEQ. ID. NO. 25761 | 376-AsnIleLysGluTyrArg-381 |
| SEQ. ID. NO. 25762 | 424-LeuGlnLysLysArgPheGluArgGlyAlaValGluPheAspSerIleGlu-440 |
| SEQ. ID. NO. 25763 | 443-MetLeuPheAspAspAsnGlyLysIleGluLys-453 |
| SEQ. ID. NO. 25764 | 458-ValArgAsnAspAlaHisLysLeuIleGlu-467 |
| SEQ. ID. NO. 25765 | 496-ProThrProGluLysLeuAlaAlaLeuArgGluGlnLeu-508 |
| SEQ. ID. NO. 25766 | 517-GlyGlyAspAsnProSerProLysAspTyrAla-527 |
| SEQ. ID. NO. 25767 | 533-PheLysGlyArgProAspAlaGluLeu-541 |
| SEQ. ID. NO. 25768 | 576-ProIleArgArgTyrProAsp-582 |
| SEQ. ID. NO. 25769 | 598-TyrThrProLysLysSerTrp-604 |
| SEQ. ID. NO. 25770 | 613-PheCysGluArgArgAlaAspAspAlaSerArgAspValGluAsn-627 |
| SEQ. ID. NO. 25771 | 633-TyrMetArgAspLysValGlyGluValPheGluGlyLysIle-646 |

TABLE 1-continued

| | |
|---|---|
| SEQ. ID. NO. 25772 | 683-IleMetAlaIleGluGlyGluArgSerGlyIle-693 |
| SEQ. ID. NO. 25773 | 696-AsnMetGlyAspArgValAlaValArgValAlaArgAlaAspLeuAspAspGlyLysIle-715 |
| SEQ. ID. NO. 25774 | 723-GlySerGlyArgGlyArgLysValLysSerSerAlaSerAlaLysProAlaGlyThrAlaGlyLysGlyLysProLysThrAlaAlaGluLys LysThrAlaArgGlyGlyLysValArgGlyArgGlyAlaSerAlaAlaAlaGluSerArgLysLysAlaLysLysProValProIleLysValLysLysArgLys GlyLysSer-791 | a989
AMPHIRegions - AMPHI

| | |
|---|---|
| SEQ. ID. NO. 25775 | 58-AlaGlyLeuThrLysLeu-63 |
| SEQ. ID. NO. 25776 | 85-SerAlaThrAspPhe-89 |
| SEQ. ID. NO. 25777 | 98-LysSerGlyLysIleThr-103 |
| SEQ. ID. NO. 25778 | 109-ProHisIleTyrGlyAla-114 |
| SEQ. ID. NO. 25779 | 183-GluLeuArgLysTyrAlaAspTrpGlyIleMetGluLysAlaLysAlaLeu-199 |
| SEQ. ID. NO. 25780 | 201-GluThrProProAsnProThrLysAla-209 |
| SEQ. ID. NO. 25781 | 299-SerValHisGlyMetTyrLysValSer-307 |
| SEQ. ID. NO. 25782 | 318-TrpThrArgHisSerArg-323 |
| SEQ. ID. NO. 25783 | 362-SerTyrGlnIleSerGluProLeu-369 |
| SEQ. ID. NO. 25784 | 448-PheLysAsnHisAlaAsp-453 |

Antigenic Index - Jameson-Wolf

| | |
|---|---|
| SEQ. ID. NO. 25785 | 43-AlaAlaAlaGluAlaAlaAspAlaSer-51 |
| SEQ. ID. NO. 25786 | 57-ProAlaGlyLeuThrLysLeuAspSerSerGlnIleSer-69 |
| SEQ. ID. NO. 25787 | 81-TyrGluAlaAspSerAlaThrAspPheThr-90 |
| SEQ. ID. NO. 25788 | 94-ValGlnGlySerLysSerGlyLysIleThrLysThrThr-106 |
| SEQ. ID. NO. 25789 | 116-LysValAsnAspAsnLeuThr-122 |
| SEQ. ID. NO. 25790 | 132-GlySerAlaThrGluTyrGluLysAspSerValLeu-143 |
| SEQ. ID. NO. 25791 | 146-AsnIleAsnLysLeuGly-151 |
| SEQ. ID. NO. 25792 | 164-LysLeuAsnGluArgHisSerPheGly-172 |
| SEQ. ID. NO. 25793 | 180-ThrSerAlaGluLeuArgLysTyrAla-188 |
| SEQ. ID. NO. 25794 | 194-GluLysAlaLysAlaLeuLysGluThrProProAsnProThrLysAlaAlaGlnIleLysAlaAspGlyHisAlaAspValLysGlySerAspTrpGly-226 |
| SEQ. ID. NO. 25795 | 236-AspIleAsnAspArgAlaArgValGlyValAsnTyrArgSerLysValSerHisThrLeuLysGlyAspAlaGluTrpAlaAla-263 |
| SEQ. ID. NO. 25796 | 272-TrpAspAlaAsnLys-276 |
| SEQ. ID. NO. 25797 | 283-ThrProSerGluLysAlaArgValLysIleValThrProGluSer-297 |
| SEQ. ID. NO. 25798 | 304-TyrLysValSerAspLysAlaAspLeu-312 |
| SEQ. ID. NO. 25799 | 317-ThrTrpThrArgHisSerArgPheAspLysAlaGluLeuValPheGluLysGluLysThrIleValAsnGlyLysSerAspArgThrThrIle-347 |
| SEQ. ID. NO. 25800 | 349-ProAsnTrpArgAsnThrTyrLysValGlyPhe-359 |
| SEQ. ID. NO. 25801 | 361-GlySerTyrGlnIleSerGluLeuGln-370 |
| SEQ. ID. NO. 25802 | 375-IleAlaPheAspLysSerProValArgAsnAlaAspTyrArgMetAsnSerLeuProAspGlyAsn-396 |
| SEQ. ID. NO. 25803 | 407-HisIleGlyLysAsnHisVal-413 |
| SEQ. ID. NO. 25804 | 424-AsnAspThrSerTyrArgThrAlaLysAlaSerGlyAsnAspValAspSerLysGlyAlaSerSerAlaArgPheLysAsnHisAla-452 |

Hydrophilic Regions - Hopp-Woods

| | |
|---|---|
| SEQ. ID. NO. 25805 | 43-AlaAlaAlaGluAlaAlaAsp-49 |
| SEQ. ID. NO. 25806 | 61-ThrLysLeuAspSerSerGln-67 |
| SEQ. ID. NO. 25807 | 81-TyrGluAlaAspSerAlaThr-87 |
| SEQ. ID. NO. 25808 | 95-GlnGlySerLysSerGlyLysIleThrLys-104 |
| SEQ. ID. NO. 25809 | 135-ThrGluTyrGluLysAspSerValLeu-143 |
| SEQ. ID. NO. 25810 | 164-LysLeuAsnGluArgHisSer-170 |
| SEQ. ID. NO. 25811 | 180-ThrSerAlaGluLeuArgLysTyrAla-188 |
| SEQ. ID. NO. 25812 | 194-GluLysAlaLysAlaLeuLysGluThrProProAsnProThrLysAlaAlaGlnIleLysAlaAspGlyHisAlaAspValLysGlySerAsp-224 |
| SEQ. ID. NO. 25813 | 237-IleAsnAspArgAlaArgVal-243 |
| SEQ. ID. NO. 25814 | 247-TyrArgSerLysVal-251 |
| SEQ. ID. NO. 25815 | 255-LeuLysGlyAspAlaGluTrpAlaAla-263 |
| SEQ. ID. NO. 25816 | 284-ProSerGluLysAlaArgValLysIleValThr-294 |
| SEQ. ID. NO. 25817 | 305-LysValSerAspLysAlaAspLeu-312 |
| SEQ. ID. NO. 25818 | 322-SerArgPheAspLysAlaGluLeuValPheGluLysGluLysThrIleVal-338 |
| SEQ. ID. NO. 25819 | 340-GlyLysSerAspArgThrThrIle-347 |
| SEQ. ID. NO. 25820 | 375-IleAlaPheAspLysSerProValArgAsnAlaAspTyrArgMet-389 |
| SEQ. ID. NO. 25821 | 391-SerLeuProAspGlyAsn-396 |
| SEQ. ID. NO. 25822 | 426-ThrSerTyrArgThrAlaLysAlaSerGlyAsnAspValAspSerLysGlyAlaSerSerAlaArgPheLysAsnHisAla-452 | a990
AMPHI Regions - AMPHI

| | |
|---|---|
| SEQ. ID. NO. 25823 | 76-IleThrAspThrTyrGlyAspAsnLeuLysAspAlaValLysLysGlnLeuGlnAspLeuTyrLys-97 |
| SEQ. ID. NO. 25824 | 131-AspLeuIleAsnLysLeuVal-137 |
| SEQ. ID. NO. 25825 | 151-ThrSerLeuAsnAsnIlePhe-157 |
| SEQ. ID. NO. 25826 | 195-AspIleHisMetLeu-199 |
| SEQ. ID. NO. 25827 | 260-ProGluAsnLeuLysThrLeuAspGly-268 |
| SEQ. ID. NO. 25828 | 293-TyrGluLeuLeuLeuLysGlnCys-300 |
| SEQ. ID. NO. 25829 | 419-SerTyrLeuHisGlyTyrGlyGlyGlyValTyrAlaAlaTrp-432 |
| SEQ. ID. NO. 25830 | 442-AlaTyrLeuAspGlyTrpLeuGlnTyr-450 |
| SEQ. ID. NO. 25831 | 472-ThrAlaSerValGluGlyGlyTyrAsnAlaLeu-482 |
| SEQ. ID. NO. 25832 | 550-GlnProPheAlaAlaPheAsnValLeuHisArg-560 |

Antigenic Index - Jameson-Wolf

| | |
|---|---|
| SEQ. ID. NO. 25833 | 6-LeuGlySerAsnThrArgSerThrLysIleGlyAspAspAlaAspPheSerPheSerAspLysProLysProGlyThr-31 |
| SEQ. ID. NO. 25834 | 35-PheSerSerGlyLysThrAspGlnAsnSerSerGluTyrGlyTyrAspGluIleAsnIleGlnGlyLysAsnTyrAsnSerGlyIle-63 |
| SEQ. ID. NO. 25835 | 75-TyrIleThrAspThrTyrGlyAspAsnLeuLysAspAlaValLysLysGlnLeuGlnAspLeuTyrLysThrArgProGluAlaTrpGluGluAsn LysLysArgThrGluGluAlaTyr-114 |
| SEQ. ID. NO. 25836 | 123-SerIleLeuLysGlnLysAsnProAspLeuIle-133 |
| SEQ. ID. NO. 25837 | 145-HisSerAsnThrSerGlnThrSer-152 |
| SEQ. ID. NO. 25838 | 157-PheAsnLysLysLeuHisValLysLysIleGluAsnLysSerHisVal-171 |
| SEQ. ID. NO. 25839 | 179-ThrLysMetThrLeuLysAspSerLeuTrpGluProArgArgHisSerAspIleHisMet-198 |
| SEQ. ID. NO. 25840 | 200-GluThrSerAspAsnAlaArgIleArgLeuAsnThrLysAspGluLysLeuThrVal-218 |
| SEQ. ID. NO. 25841 | 222-TyrGlnGlyGlyAla-226 |

TABLE 1-continued

| | |
|---|---|
| SEQ. ID. NO. 25842 | 233-AspValArgGluSerAspLysProAlaLeuThrPheGluGluLysValSerGlyGlnSerGlyValValLeuGluArgArgProGluAsnLeuLys ThrLeuAspGlyArgLysLeuIleAlaAlaGluLysAlaAspSerAsnSerPheAlaPheLysGlnAsnTyrArgGlnGlyLeu-292 |
| SEQ. ID. NO. 25843 | 298-LysGlnCysGluGlyGlyPhe-304 |
| SEQ. ID. NO. 25844 | 312-AlaIleProGluAlaGlu-317 |
| SEQ. ID. NO. 25845 | 335-ArgAlaAlaAspArgGlyAspAspValTyrAlaAlaAspProSerArgGlnLysLeu-353 |
| SEQ. ID. NO. 25846 | 358-IleGlyGlyArgSerHisGlnAsnIleArgGlyGlyAlaAlaAlaAspGlyArgArgLysGlyVal-379 |
| SEQ. ID. NO. 25847 | 385-ValPheValArgGlnAsnGluGlySerArgLeuAla-396 |
| SEQ. ID. NO. 25848 | 400-MetGlyGlyArgAlaGlyGln-406 |
| SEQ. ID. NO. 25849 | 408-AlaSerValAsnGlyLysGlyGlyAla-416 |
| SEQ. ID. NO. 25850 | 435-LeuArgAspLysGlnThrGlyAlaTyr-443 |
| SEQ. ID. NO. 25851 | 452-ArgPheLysHisArgIleAsnAspGluAsnArgAlaGluArgTyrLysThrLysGlyTrpThr-472 |
| SEQ. ID. NO. 25852 | 475-ValGluGlyGlyTyr-479 |
| SEQ. ID. NO. 25853 | 487-ValValGlyLysGlyAsnAsnValArg-495 |
| SEQ. ID. NO. 25854 | 510-AsnGlyGlyPheThrAspSerGluGlyThrAla-520 |
| SEQ. ID. NO. 25855 | 525-GlySerGlyGlnTrpGlnSerArgAlaGlyIleArgAlaLysThrArgPheAlaLeuArgAsnGlyValAsn-548 |
| SEQ. ID. NO. 25856 | 559-HisArgSerLysSerPheGlyValGluMetAspGlyGluLysGlnThrLeuAla-576 |
| SEQ. ID. NO. 25857 | 579-ThrAlaLeuGluGlyArgPheGlyIle-587 |
| SEQ. ID. NO. 25858 | 589-AlaGlyTrpLysGlyHisMet-595 |
| SEQ. ID. NO. 25859 | 600-GlyTyrGlyLysArgThrAspGlyAspLysGluAlaAlaLeu-613 |
| Hydrophilic Regions - Hopp-Woods | |
| SEQ. ID. NO. 25860 | 8-SerAsnThrArgSerThrLysIleGlyAspAspAlaAspPheSerPheSerAspLysProLysProGlyThr-31 |
| SEQ. ID. NO. 25861 | 38-GlyLysThrAspGlnAsnSerSer-45 |
| SEQ. ID. NO. 25862 | 79-ThrTyrGlyAspAsnLeuLysAspAlaValLysLysGlnLeuGlnAsp-94 |
| SEQ. ID. NO. 25863 | 96-TyrLysThrArgProGluAlaTrpGluGluAsnLysLysArgThrGluGluAlaTyr-114 |
| SEQ. ID. NO. 25864 | 123-SerIleLeuLysGlnLysAsnProAspLeuIle-133 |
| SEQ. ID. NO. 25865 | 161-LeuHisValLysIleGluAsnLysSerHisVal-171 |
| SEQ. ID. NO. 25866 | 179-ThrLysMetThrLeuLys-184 |
| SEQ. ID. NO. 25867 | 186-SerLeuTrpGluProArgArgHisSerAsp-195 |
| SEQ. ID. NO. 25868 | 200-GluThrSerAspAsnAlaArgIleArgLeuAsnThrLysAspGluLysLeuThrVal-218 |
| SEQ. ID. NO. 25869 | 233-AspValArgGluSerAspLysProAlaLeuThrPheGluGluLysValSerGly-250 |
| SEQ. ID. NO. 25870 | 255-ValLeuGluArgArgProGluAsnLeuLysThrLeuAspGlyArgLysLeuIleAlaAlaGluLysAlaAspSerAsn-280 |
| SEQ. ID. NO. 25871 | 312-AlaIleProGluAlaGlu-317 |
| SEQ. ID. NO. 25872 | 335-ArgAlaAlaAspArgGlyAspAspValTyrAla-345 |
| SEQ. ID. NO. 25873 | 347-AspProSerArgGln-351 |
| SEQ. ID. NO. 25874 | 361-ArgSerHisGlnAsnIleArgGly-368 |
| SEQ. ID. NO. 25875 | 370-AlaAlaAlaAspGlyArgArgLysGlyVal-379 |
| SEQ. ID. NO. 25876 | 385-ValPheValArgGlnAsnGluGlySerArg-394 |
| SEQ. ID. NO. 25877 | 410-ValAsnGlyLysGlyGlyAla-416 |
| SEQ. ID. NO. 25878 | 435-LeuArgAspLysGlnThr-440 |
| SEQ. ID. NO. 25879 | 452-ArgPheLysHisArgIleAsnAspGluAsnArgAlaGluArgTyrLysThr-468 |
| SEQ. ID. NO. 25880 | 487-ValValGlyLysGlyAsnAsn-493 |
| SEQ. ID. NO. 25881 | 513-PheThrAspSerGluGlyThr-519 |
| SEQ. ID. NO. 25882 | 533-AlaGlyIleArgAlaLysThrArgPheAlaLeu-543 |
| SEQ. ID. NO. 25883 | 559-HisArgSerLysSerPheGlyValGluMetAspGlyGluLysGlnThrLeuAla-576 |
| SEQ. ID. NO. 25884 | 579-ThrAlaLeuGluGly-583 |
| SEQ. ID. NO. 25885 | 600-GlyTyrGlyLysArgThrAspGlyAspLysGluAlaAlaLeu-613 |
| a990 | |
| AMPHI Regions - AMPHI | |
| SEQ. ID. NO. 25886 | 76-IleThrAspThrTyrGlyAspAsnLeuLysAspAlaValLysLysGlnLeuGlnAspLeuTyrLys-97 |
| SEQ. ID. NO. 25887 | 131-AspLeuIleAsnLysLeuVal-137 |
| SEQ. ID. NO. 25888 | 151-ThrSerLeuAsnAsnIlePhe-157 |
| SEQ. ID. NO. 25889 | 195-AspIleHisMetLeu-199 |
| SEQ. ID. NO. 25890 | 260-ProGluAsnLeuLysThrLeuAspGly-268 |
| SEQ. ID. NO. 25891 | 293-TyrGluLeuLeuLeuLysGlnCys-300 |
| SEQ. ID. NO. 25892 | 419-SerTyrLeuHisGlyTyrGlyGlyGlyValTyrAlaAlaTrp-432 |
| SEQ. ID. NO. 25893 | 442-AlaTyrLeuAspGlyTrpLeuGlnTyr-450 |
| SEQ. ID. NO. 25894 | 472-ThrAlaSerValGluGlyGlyTyrAsnAlaLeu-482 |
| SEQ. ID. NO. 25895 | 550-GlnProPheAlaAlaPheAsnValLeuHisArg-560 |
| Antigenic Index - Jameson-Wolf | |
| SEQ. ID. NO. 25896 | 6-LeuGlySerAsnThrArgSerThrLysIleGlyAspAspAlaAspPheSerPheSerAspLysProLysProGlyThr-31 |
| SEQ. ID. NO. 25897 | 35-PheSerSerGlyLysThrAspGlnAsnSerSerGluTyrGlyTyrAspGluIleGluAsnIleGlnGlyLysAsnTyrAsnSerGlyIle-63 |
| SEQ. ID. NO. 25898 | 75-TyrIleThrAspThrTyrGlyAspAsnLeuLysAspAlaValLysLysGlnLeuGlnAspLeuTyrLysThrArgProGluAlaTrpGluGluAsn LysLysArgThrGluGluAlaTyr-114 |
| SEQ. ID. NO. 25899 | 123-SerIleLeuLysGlnLysAsnProAspLeuIle-133 |
| SEQ. ID. NO. 25900 | 145-HisSerAsnThrSerGlnThrSer-152 |
| SEQ. ID. NO. 25901 | 157-PheAsnLysLysLeuHisValLysIleGluAsnLysSerHisVal-171 |
| SEQ. ID. NO. 25902 | 179-ThrLysMetThrLeuLysAspSerLeuTrpGluProArgArgHisSerAspIleHisMet-198 |
| SEQ. ID. NO. 25903 | 200-GluThrSerAspAsnAlaArgIleArgLeuAsnThrLysAspGluLysLeuThrVal-218 |
| SEQ. ID. NO. 25904 | 222-TyrGlnGlyGlyAla-226 |
| SEQ. ID. NO. 25905 | 233-AspValArgGluSerAspLysProAlaLeuThrPheGluGluLysValSerGlyGlnSerGlyValValLeuGluArgArgProGluAsnLeuLys ThrLeuAspGlyArgLysLeuIleAlaAlaGluLysAlaAspSerAsnSerPheAlaPheLysGlnAsnTyrArgGlnGlyLeu-292 |
| SEQ. ID. NO. 25906 | 298-LysGlnCysGluGlyGlyPhe-304 |
| SEQ. ID. NO. 25907 | 312-AlaIleProGluAlaGlu-317 |
| SEQ. ID. NO. 25908 | 335-ArgAlaAlaAspArgGlyAspAspValTyrAlaAlaAspProSerArgGlnLysLeu-353 |
| SEQ. ID. NO. 25909 | 358-IleGlyGlyArgSerHisGlnAsnIleArgGlyGlyAlaAlaAlaAspGlyArgArgLysGlyVal-379 |
| SEQ. ID. NO. 25910 | 385-ValPheValArgGlnAsnGluGlySerArgLeuAla-396 |
| SEQ. ID. NO. 25911 | 400-MetGlyGlyArgAlaGlyGln-406 |
| SEQ. ID. NO. 25912 | 408-AlaSerValAsnGlyLysGlyGlyAla-416 |
| SEQ. ID. NO. 25913 | 435-LeuArgAspLysGlnThrGlyAlaTyr-443 |
| SEQ. ID. NO. 25914 | 452-ArgPheLysHisArgIleAsnAspGluAsnArgAlaGluArgTyrLysThrLysGlyTrpThr-472 |

TABLE 1-continued

| | |
|---|---|
| SEQ. ID. NO. 25915 | 475-ValGluGlyGlyTyr-479 |
| SEQ. ID. NO. 25916 | 487-ValValGlyLysGlyAsnAsnValArg-495 |
| SEQ. ID. NO. 25917 | 510-AsnGlyGlyPheThrAspSerGluGlyThrAla-520 |
| SEQ. ID. NO. 25918 | 525-GlySerGlyGlnTrpGlnSerArgAlaGlyIleArgAlaLysThrArgPheAlaLeuArgAsnGlyValAsn-548 |
| SEQ. ID. NO. 25919 | 559-HisArgSerLysSerPheGlyValGluMetAspGlyGluLysGlnThrLeuAla-576 |
| SEQ. ID. NO. 25920 | 579-ThrAlaLeuGluGlyArgPheGlyIle-587 |
| SEQ. ID. NO. 25921 | 589-AlaGlyTrpLysGlyHisMet-595 |
| SEQ. ID. NO. 25922 | 600-GlyTyrGlyLysArgThrAspGlyAspLysGluAlaAlaLeu-613 |

Hydrophilic Regions - Hopp-Woods

| | |
|---|---|
| SEQ. ID. NO. 25923 | 8-SerAsnThrArgSerThrLysIleGlyAspAspAlaAspPheSerPheSerAspLysProLysProGlyThr-31 |
| SEQ. ID. NO. 25924 | 38-GlyLysThrAspGlnAsnSerSer-45 |
| SEQ. ID. NO. 25925 | 79-ThrTyrGlyAspAsnLeuLysAspAlaValLysLysGlnLeuGlnAsp-94 |
| SEQ. ID. NO. 25926 | 96-TyrLysThrArgProGluAlaTrpGluGluAsnLysLysArgThrGluGluAlaTyr-114 |
| SEQ. ID. NO. 25927 | 123-SerIleLeuLysGlnLysAsnProAspLeuIle-133 |
| SEQ. ID. NO. 25928 | 161-LeuHisValLysIleGluAsnLysSerHisVal-171 |
| SEQ. ID. NO. 25929 | 179-ThrLysMetThrLeuLys-184 |
| SEQ. ID. NO. 25930 | 186-SerLeuTrpGluProArgArgHisSerAsp-195 |
| SEQ. ID. NO. 25931 | 200-GluThrSerAspAsnAlaArgIleArgLeuAsnThrLysAspGluLysLeuThrVal-218 |
| SEQ. ID. NO. 25932 | 233-AspValArgGluSerAspLysProAlaLeuThrPheGluGluLysValSerGly-250 |
| SEQ. ID. NO. 25933 | 255-ValLeuGluArgArgProGluAsnLeuLysThrLeuAspGlyArgLysLeuIleAlaAlaGluLysAlaAspSerAsn-280 |
| SEQ. ID. NO. 25934 | 312-AlaIleProGluAlaGlu-317 |
| SEQ. ID. NO. 25935 | 335-ArgAlaAlaAspArgGlyAspAspValTyrAla-345 |
| SEQ. ID. NO. 25936 | 347-AspProSerArgGln-351 |
| SEQ. ID. NO. 25937 | 361-ArgSerHisGlnAsnIleArgGly-368 |
| SEQ. ID. NO. 25938 | 370-AlaAlaAlaAspGlyArgArgLysGlyVal-379 |
| SEQ. ID. NO. 25939 | 385-ValPheValArgGlnAsnGluGlySerArg-394 |
| SEQ. ID. NO. 25940 | 410-ValAsnGlyLysGlyGlyAla-416 |
| SEQ. ID. NO. 25941 | 435-LeuArgAspLysGlnThr-440 |
| SEQ. ID. NO. 25942 | 452-ArgPheLysHisArgIleAsnAspGluAsnArgAlaGluArgTyrLysThr-468 |
| SEQ. ID. NO. 25943 | 487-ValValGlyLysGlyAsnAsn-493 |
| SEQ. ID. NO. 25944 | 513-PheThrAspSerGluGlyThr-519 |
| SEQ. ID. NO. 25945 | 533-AlaGlyIleArgAlaLysThrArgPheAlaLeu-543 |
| SEQ. ID. NO. 25946 | 559-HisArgSerLysSerPheGlyValGluMetAspGlyGluLysGlnThrLeuAla-576 |
| SEQ. ID. NO. 25947 | 579-ThrAlaLeuGluGly-583 |
| SEQ. ID. NO. 25948 | 600-GlyTyrGlyLysArgThrAspGlyAspLysGluAlaAlaLeu-613 | a992
AMPHI Regions - AMPHI

| | |
|---|---|
| SEQ. ID. NO. 25949 | 6-ArgHisLeuLysAsnMetGlnIleLysLysIleMetLysTrp-19 |
| SEQ. ID. NO. 25950 | 24-LeuSerLeuLeuGlyAlaLeuGlyTyr-32 |
| SEQ. ID. NO. 25951 | 45-AlaValLeuAspValLeuGlyAlaAla-53 |
| SEQ. ID. NO. 25952 | 72-HisArgTyrThrGlyThrValSerLysValTyr-82 |
| SEQ. ID. NO. 25953 | 158-GlnValGlnAspGly-162 |
| SEQ. ID. NO. 25954 | 179-AspPheAlaAspTyr-183 |

Antigenic Index - Jameson-Wolf

| | |
|---|---|
| SEQ. ID. NO. 25955 | 1-MetPheArgArgHisArgHisLeuLys-9 |
| SEQ. ID. NO. 25956 | 34-GlyTyrGlySerGluAlaValArg-41 |
| SEQ. ID. NO. 25957 | 52-AlaAlaGlyAspAlaGlySerAspAlaProAlaArgArgArgAlaSerAlaLysSerGlyHisArgTyrThr-75 |
| SEQ. ID. NO. 25958 | 79-SerLysValTyrAspGlyAspThr-86 |
| SEQ. ID. NO. 25959 | 90-IleAspGlyAspGlyAlaLysHisLysIle-99 |
| SEQ. ID. NO. 25960 | 105-AspAlaProGluMetLysGlnAlaTyrGlyThrArgSerArgAspAsnLeuArgAlaAlaAlaGluGlyArgLysValSer-131 |
| SEQ. ID. NO. 25961 | 134-ValPheAspThrAspArgTyrGlnArgGluValAla-145 |
| SEQ. ID. NO. 25962 | 148-SerValGlyLysThrAspLeuAsn-155 |
| SEQ. ID. NO. 25963 | 168-LysSerTyrAlaLysGluGlnGlnAspLysAlaAspPhe-180 |
| SEQ. ID. NO. 25964 | 187-GlnIleGlnAlaGluArgGluArgLysGlyLeuTrpLysAlaLysAsnProGlnAlaPro-206 |
| SEQ. ID. NO. 25965 | 208-AlaTyrArgArgAlaGlyArgSerGlyGlyGlyAsnLysAspTrpMetAsp-224 |

Hydrophilic Regions - Hopp-Woods

| | |
|---|---|
| SEQ. ID. NO. 25966 | 1-MetPheArgArgHisArgHisLeuLys-9 |
| SEQ. ID. NO. 25967 | 54-GlyAspAlaGlySerAspAlaProAlaArgArgArgAlaSerAlaLysSerGlyHisArg-73 |
| SEQ. ID. NO. 25968 | 90-IleAspGlyAspGlyAlaLysHisLysIle-99 |
| SEQ. ID. NO. 25969 | 105-AspAlaProGluMetLysGln-111 |
| SEQ. ID. NO. 25970 | 113-TyrGlyThrArgSerArgAspAsnLeuArgAlaAlaAlaAlaGluGlyArgLysValSer-131 |
| SEQ. ID. NO. 25971 | 134-ValPheAspThrAspArgTyrGlnArgGluValAla-145 |
| SEQ. ID. NO. 25972 | 148-SerValGlyLysThrAspLeu-154 |
| SEQ. ID. NO. 25973 | 169-SerTyrAlaLysGluGlnGlnAspLysAlaAspPhe-180 |
| SEQ. ID. NO. 25974 | 187-GlnIleGlnAlaGluArgGluArgLysGlyLeuTrpLysAlaLysAsnPro-203 |
| SEQ. ID. NO. 25975 | 211-ArgAlaGlyArgSerGlyGlyGlyAsnLysAspTrpMet-223 | a993
AMPHI Regions - AMPHI

| | |
|---|---|
| SEQ. ID. NO. 25976 | 6-SerSerPheGlnGlyProLeuAspLeuLeuLeu-16 |
| SEQ. ID. NO. 25977 | 35-ThrGluGlnTyrLeuHisTyrIleAlaGlnIle-45 |
| SEQ. ID. NO. 25978 | 105-GlyLeuAspAlaLeuProArgAla-112 |
| SEQ. ID. NO. 25979 | 136-IleThrAspLeuThrGlnAlaTrpLeuSer-145 |
| SEQ. ID. NO. 25980 | 152-HisThrArgSerHisGluValIle-159 |
| SEQ. ID. NO. 25981 | 169-MetThrAlaIleLeuArgArgLeuAsnLysHisGlyIleCysArgPheHisAspLeuPheAsnProGlu-191 |
| SEQ. ID. NO. 25982 | 199-ValAsnPheIleAlaAlaLeuLeu-205 |

Antigenic Index - Jameson-Wolf

| | |
|---|---|
| SEQ. ID. NO. 25983 | 7-SerPheGlnGlyProLeu-12 |
| SEQ. ID. NO. 25984 | 20-ArgLysGlnAsnIleAsp-25 |
| SEQ. ID. NO. 25985 | 70-LeuLeuLeuProArgThrGluThrValGluAspGluGluAlaAspProArgAlaGluLeuValArg-91 |
| SEQ. ID. NO. 25986 | 108-AlaLeuProArgAlaGlyArgAspPhe-116 |

TABLE 1-continued

| SEQ. ID. NO. 25987 | 148-SerArgAlaLysHisThrArgSerHisGluValIleLysGluThrIleSer-164 |
| SEQ. ID. NO. 25988 | 174-ArgArgLeuAsnLysHisGlyIle-181 |
| SEQ. ID. NO. 25989 | 188-PheAsnProGluGlnGly-193 |
| SEQ. ID. NO. 25990 | 207-LeuAlaLysGluGlyLeu-212 |
| SEQ. ID. NO. 25991 | 228-LeuAsnHisGluGlyAlaHisSerAspGlyIleSerGlyThrArgGlyGlyArgAspValPhe-248 |

Hydrophilic Regions - Hopp-Woods

| SEQ. ID. NO. 25992 | 20-ArgLysGlnAsnIleAsp-25 |
| SEQ. ID. NO. 25993 | 70-LeuLeuLeuProArgThrGluThrValGluAspGluGluAlaAspProArgAlaGluLeuValArg-91 |
| SEQ. ID. NO. 25994 | 108-AlaLeuProArgAlaGlyArg-114 |
| SEQ. ID. NO. 25995 | 148-SerArgAlaLysHisThrArgSerHisGluValIleLysGluThrIleSer-164 |
| SEQ. ID. NO. 25996 | 174-ArgArgLeuAsnLys-178 |
| SEQ. ID. NO. 25997 | 207-LeuAlaLysGluGlyLeu-212 |
| SEQ. ID. NO. 25998 | 232-GlyAlaHisSerAspGlyIleSerGlyThrArgGlyGlyArgAspValPhe-248 | a996
AMPHI Regions - AMPHI

| SEQ. ID. NO. 25999 | 21-LysSerAlaArgThrHisAlaLysIlePro-30 |
| SEQ. ID. NO. 26000 | 50-ProGlyGluSerTyrProAlaGlnLeuGlnLysLeuThrGlyTrpAsn-65 |
| SEQ. ID. NO. 26001 | 75-ThrSerAlaGlnAlaLeuSerArgLeuProAla-85 |
| SEQ. ID. NO. 26002 | 104-LeuArgLysValProLysGlu-110 |
| SEQ. ID. NO. 26003 | 115-AsnIleAlaLysIleIleGluThrValGlnLys-125 |
| SEQ. ID. NO. 26004 | 140-LeuGlyAlaLeuPheGlyHisLeuSerAsp-149 |
| SEQ. ID. NO. 26005 | 167-GlyAlaTrpAlaGlu-171 |
| SEQ. ID. NO. 26006 | 186-AsnGlyLysGlyTyrArgLysPheAlaGluAspLeuAsnGlnPheLeuArgLysGlnGlyPhe-206 |

Antigenic Index - Jameson-Wolf

| SEQ. ID. NO. 26007 | 1-MetAsnArgArgThrPhe-6 |
| SEQ. ID. NO. 26008 | 18-CysGlyArgLysSerAlaArgThrHisAlaLysIleProGluGlySerThr-34 |
| SEQ. ID. NO. 26009 | 46-TyrGlyAlaAsnProGlyGluSerTyrPro-55 |
| SEQ. ID. NO. 26010 | 69-GlyGlyValSerGlyAspThrSerAla-77 |
| SEQ. ID. NO. 26011 | 87-LeuAlaArgLysProLys-92 |
| SEQ. ID. NO. 26012 | 99-GlyGlyAsnAspPheLeuArgLysValProLysGluGlnThrArgAlaAsnIle-116 |
| SEQ. ID. NO. 26013 | 121-GluThrValGlnLysGluAsnIlePro-129 |
| SEQ. ID. NO. 26014 | 148-SerAspHisProLeuTyrGluAspLeuSerGluGluTyrGly-161 |
| SEQ. ID. NO. 26015 | 173-LeuGlyAspAsnAsnLeuLysSerAspGlnIleHisAlaAsnGlyLysGlyTyrArgLysPheAlaGluAspLeuAsnGlnPheLeuArgLysGlnGlyPheArg-207 |

Hydrophilic Regions - Hopp-Woods

| SEQ. ID. NO. 26016 | 18-CysGlyArgLysSerAlaArgThrHisAlaLysIleProGlu-31 |
| SEQ. ID. NO. 26017 | 49-AsnProGlyGluSerTyr-54 |
| SEQ. ID. NO. 26018 | 71-ValSerGlyAspThrSerAla-77 |
| SEQ. ID. NO. 26019 | 87-LeuAlaArgLysProLys-92 |
| SEQ. ID. NO. 26020 | 102-AspPheLeuArgLysValProLysGluGlnThrArgAlaAsnIle-116 |
| SEQ. ID. NO. 26021 | 121-GluThrValGlnLysGluAsnIle-128 |
| SEQ. ID. NO. 26022 | 154-GluAspLeuSerGluGluTyrGly-161 |
| SEQ. ID. NO. 26023 | 176-AsnAsnLeuLysSerAspGlnIleHisAlaAsn-186 |
| SEQ. ID. NO. 26024 | 188-LysGlyTyrArgLysPheAlaGluAspLeuAsnGlnPheLeuArg-202 | a997
AMPHI Regions - AMPHI

| SEQ. ID. NO. 26025 | 18-TrpAlaGlyLeuSerAlaAlaVal-25 |
| SEQ. ID. NO. 26026 | 70-TyrArgGlyValLeuArgLeuMetLysThrIleGlySerAsp-83 |
| SEQ. ID. NO. 26027 | 107-ProLeuProAlaProLeuHisIle-114 |
| SEQ. ID. NO. 26028 | 123-ArgValProSerAlaPheLysAlaLysLeuLeuAlaAspMetSerAspLeuGlnLysSerAlaArgLeuGly-146 |
| SEQ. ID. NO. 26029 | 164-AlaAlaValMetGlnPheTrpGlnProLeuValTrpGly-176 |
| SEQ. ID. NO. 26030 | 189-ValLeuCysAsnValLeuSerAsp-196 |
| SEQ. ID. NO. 26031 | 222-AlaLeuAlaGluLeuGlnArg-228 |
| SEQ. ID. NO. 26032 | 241-ArgLeuAsnThrLeuPro-246 |
| SEQ. ID. NO. 26033 | 275-GluGlyThrProGluHisValGlnThrAla-284 |
| SEQ. ID. NO. 26034 | 300-TyrAlaGluProValArgLeuProAlaProLeuThrGlyLeuAlaAspGly-316 |
| SEQ. ID. NO. 26035 | 354-AspLysValHisAlaAspLeuLysArgIleLeuProHisLeu-367 |
| SEQ. ID. NO. 26036 | 369-GluProGluAlaVal-373 |

Antigenic Index - Jameson-Wolf

| SEQ. ID. NO. 26037 | 3-AsnThrProHisProArgProLysIle-11 |
| SEQ. ID. NO. 26038 | 37-GluAlaGlyArgGlnAlaGlyGlyArgAlaArgAla-48 |
| SEQ. ID. NO. 26039 | 50-AlaGlyAsnThrAspGlyPheGly-57 |
| SEQ. ID. NO. 26040 | 78-LysThrIleGlySerAspProHisAla-86 |
| SEQ. ID. NO. 26041 | 122-ArgArgValProSerAlaPheLys-129 |
| SEQ. ID. NO. 26042 | 132-LeuLeuAlaAspMetSerAspLeuGlnLysSerAlaArgLeuGlyGlnProAspThrThr-151 |
| SEQ. ID. NO. 26043 | 156-LeuLysGlnArgAsnValProArg-163 |
| SEQ. ID. NO. 26044 | 180-ThrProLeuGluThrAlaSer-186 |
| SEQ. ID. NO. 26045 | 197-GlyValLeuThrLysLysSerGlySerAspTyrLeuLeuProLysGlnAspLeu-214 |
| SEQ. ID. NO. 26046 | 225-GluLeuGlnArgLeuGlyAlaAspIleArgLeuGluThrArgIleCysArg-241 |
| SEQ. ID. NO. 26047 | 243-AsnThrLeuProAspGlyLysVal-250 |
| SEQ. ID. NO. 26048 | 273-LeuProGluGlyThrProGluHisVal-281 |
| SEQ. ID. NO. 26049 | 312-GlyLeuAlaAspGlyThr-317 |
| SEQ. ID. NO. 26050 | 323-CysArgGlyArgLeuGlyLeuProGluAsnGluVal-334 |
| SEQ. ID. NO. 26051 | 340-ValSerAspArgValGlyAla-346 |
| SEQ. ID. NO. 26052 | 356-ValHisAlaAspLeuLysArgIleLeu-364 |
| SEQ. ID. NO. 26053 | 367-LeuGlyGluProGluAlaValArgValIleThrGluLysArgAlaThrThrAlaAlaAspAlaProProProAspLeu-392 |
| SEQ. ID. NO. 26054 | 402-ProAlaGlyAspTyrLeuHisProAspTyrProAla-413 |

Hydrophilic Regions - Hopp-Woods

| SEQ. ID. NO. 26055 | 5-ProHisProArgProLysIle-11 |
| SEQ. ID. NO. 26056 | 37-GluAlaGlyArgGlnAlaGlyGlyArgAlaArgAla-48 |

TABLE 1-continued

| | |
|---|---|
| SEQ. ID. NO. 26057 | 80-IleGlySerAspPro-84 |
| SEQ. ID. NO. 26058 | 122-ArgArgValProSer-126 |
| SEQ. ID. NO. 26059 | 132-LeuLeuAlaAspMetSerAspLeuGlnLysSerAlaArgLeuGlyGlnProAspThrThr-151 |
| SEQ. ID. NO. 26060 | 198-ValLeuThrLysLysSerGlySer-205 |
| SEQ. ID. NO. 26061 | 208-LeuLeuProLysGlnAspLeu-214 |
| SEQ. ID. NO. 26062 | 225-GluLeuGlnArgLeuGlyAlaAspIleArgLeuGluThrArgIleCysArg-241 |
| SEQ. ID. NO. 26063 | 246-ProAspGlyLysVal-250 |
| SEQ. ID. NO. 26064 | 276-GlyThrProGluHisVal-281 |
| SEQ. ID. NO. 26065 | 325-GlyArgLeuGlyLeuProGluAsnGluVal-334 |
| SEQ. ID. NO. 26066 | 340-ValSerAspArgValGly-345 |
| SEQ. ID. NO. 26067 | 356-ValHisAlaAspLeuLysArgIleLeu-364 |
| SEQ. ID. NO. 26068 | 368-GlyGluProGluAlaValArgValIleThrGluLysArgAlaThrThrAlaAlaAspAlaProProPro-390 |
| g001 | |
| AMPHI Regions - AMPHI | |
| SEQ. ID. NO. 26069 | 7-AlaAlaArgArgValSer-12 |
| SEQ. ID. NO. 26070 | 17-SerGlyArgAlaCys-21 |
| SEQ. ID. NO. 26071 | 67-AlaArgPhePheGlySerValCysAsnSerAla-77 |
| Antigenic Index - Jameson-Wolf | |
| SEQ. ID. NO. 26072 | 3-ProGlnGlyLysAlaAlaArgArgValSerAlaAsnGluValSerGlyArAlaCysAla-22 |
| SEQ. ID. NO. 26073 | 31-ThrLeuProLysArgAspThrLeuAsnGlySerGlyThr-43 |
| SEQ. ID. NO. 26074 | 53-ProArgSerLeuArgSerLysSerThr-61 |
| SEQ. ID. NO. 26075 | 68-ArgPhePheGlySer-72 |
| SEQ. ID. NO. 26076 | 74-CysAsnSerAlaAlaArgArgSerSerCysProSerProLysIleGly-89 |
| SEQ. ID. NO. 26077 | 100-ValProSerGluAlaMetLeuArgLysSerSerGlyGluLysHisSerVal-116 |
| SEQ. ID. NO. 26078 | 119-AspCysProAlaSerSerGlyArgTrpAspAsnThrAla-131 |
| Hydrophilic Regions - Hopp-Woods | |
| SEQ. ID. NO. 26079 | 5-GlyLysAlaAlaArgArgValSerAlaAsnGluValSerGly-18 |
| SEQ. ID. NO. 26080 | 32-LeuProLysArgAspThrLeuAsn-39 |
| SEQ. ID. NO. 26081 | 54-ArgSerLeuArgSerLysSer-60 |
| SEQ. ID. NO. 26082 | 77-AlaAlaArgArgSerSerCysProSerProLys-87 |
| SEQ. ID. NO. 26083 | 104-AlaMetLeuArgLysSerSerGlyGluLysHisSerVal-116 |
| SEQ. ID. NO. 26084 | 125-GlyArgTrpAspAsn-129 |
| g003 | |
| AMPHI Regions - AMPHI | |
| SEQ. ID. NO. 26085 | 72-AsnGlnValValLeu-76 |
| SEQ. ID. NO. 26086 | 82-ValValGluValPheGlnArg-88 |
| SEQ. ID. NO. 26087 | 150-ValGlnAlaGluPheValGlyIleValGlyHisPheAspGlyLeuGlyMet-166 |
| SEQ. ID. NO. 26088 | 173-HisPhePheValArgValPheArg-180 |
| Antigenic Index - Jameson-Wolf | |
| SEQ. ID. NO. 26089 | 104-PheGluGlyGlyGlyAspAspGlyPhe-112 |
| SEQ. ID. NO. 26090 | 137-GlyArgIleAsnAspAlaGluIleIle-145 |
| SEQ. ID. NO. 26091 | 204-ProLysAlaAlaAlaGlyGluValAsnGly-213 |
| SEQ. ID. NO. 26092 | 215-ArgValHisAspCys-219 |
| Hydrophilic Regions - Hopp-Woods | |
| SEQ. ID. NO. 26093 | 106-GlyGlyGlyAspAspGlyPhe-112 |
| SEQ. ID. NO. 26094 | 137-GlyArgIleAsnAspAlaGluIleIle-145 |
| SEQ. ID. NO. 26095 | 205-LysAlaAlaAlaGlyGluValAsnGly-213 |
| SEQ. ID. NO. 26096 | 215-ArgValHisAspCys-219 |
| g005 | |
| AMPHI Regions - AMPHI | |
| SEQ. ID. NO. 26097 | 16-IleGlnSerMetTrpLysGlu-22 |
| SEQ. ID. NO. 26098 | 32-LeuGluLeuLeuThrValPheGlyAlaIleAla-42 |
| SEQ. ID. NO. 26099 | 62-LeuThrAspPheSerGluAsnTyr-69 |
| SEQ. ID. NO. 26100 | 107-ArgLeuLysGlyGlyGlyGluLysSerAlaGlu-117 |
| SEQ. ID. NO. 26101 | 177-GlnLeuArgArgLeuArg-182 |
| SEQ. ID. NO. 26102 | 213-AlaProPheAlaValIleGlySerValGlyValValAlaGluValProAsnIleHisArgLeuLeuLysLys-236 |
| SEQ. ID. NO. 26103 | 249-PheLysArgThrVal-253 |
| SEQ. ID. NO. 26104 | 274-ThrHisGlnLeuPheLysGln-280 |
| SEQ. ID. NO. 26105 | 308-LeuAsnLeuIleAspGluIleSerThr-316 |
| SEQ. ID. NO. 26106 | 320-LeuLeuLeuLysAlaPhe-325 |
| Antigenic Index - Jameson-Wolf | |
| SEQ. ID. NO. 26107 | 1-MetGlyMetAspAsn-5 |
| SEQ. ID. NO. 26108 | 10-MetProGluGlnGluGluIleGlnSerMetTrp-20 |
| SEQ. ID. NO. 26109 | 50-GlnSerLysLysGlnSerGluSerGlySer-59 |
| SEQ. ID. NO. 26110 | 64-AspPheSerGluAsnTyrLysLysGlnArgGlnSerPhe-76 |
| SEQ. ID. NO. 26111 | 82-SerGluGluGluThrLysHisGlnGluLysLysGluLysLysLysGluLysAlaGluAlaLysAlaGluLysLysArgLeuLysGluGly GlyGluLysSerAlaGluThrGlnLysSerArg-122 |
| SEQ. ID. NO. 26112 | 138-GluSerLeuArgHisGluIle-144 |
| SEQ. ID. NO. 26113 | 151-AlaLysProGluAspGluValLeuLeu-159 |
| SEQ. ID. NO. 26114 | 161-LeuGluSerProGlyGlyVal-167 |
| SEQ. ID. NO. 26115 | 177-GlnLeuArgArgLeuArgGluArgAsnIle-186 |
| SEQ. ID. NO. 26116 | 191-AlaValAspLysValAlaAla-197 |
| SEQ. ID. NO. 26117 | 232-ArgLeuLeuLysLysHisAspIleAspVal-241 |
| SEQ. ID. NO. 26118 | 247-GlyGluPheLysArgThr-252 |
| SEQ. ID. NO. 26119 | 258-GluAsnThrGluLysGlyLysGlnLysPheArgGlnGluLeuGluGluThrHisGln-276 |
| SEQ. ID. NO. 26120 | 281-PheValSerGluAsnArgProGlyLeuAspIleGluLysIleAlaThr-296 |
| SEQ. ID. NO. 26121 | 312-AspGluIleSerThrSerAspAspLeuLeu-321 |
| SEQ. ID. NO. 26122 | 325-PheGluAsnLysGlnValIle-331 |
| SEQ. ID. NO. 26123 | 334-LysTyrGlnGluLysArgSerLeuIle-342 |
| SEQ. ID. NO. 26124 | 351-AlaSerValGluLysLeuPhe-357 |

TABLE 1-continued

| | |
|---|---|
| SEQ. ID. NO. 26125 | 361-ValAsnArgArgAlaAspVal-367 |

Hydrophilic Regions - Hopp-Woods

| | |
|---|---|
| SEQ. ID. NO. 26126 | 10-MetProGluGlnGluGluIleGlnSerMetTrp-20 |
| SEQ. ID. NO. 26127 | 50-GlnSerLysLysGlnSerGluSerGly-58 |
| SEQ. ID. NO. 26128 | 64-AspPheSerGluAsnTyrLysLysGlnArgGlnSerPhe-76 |
| SEQ. ID. NO. 26129 | 82-SerGluGluGluThrLysHisGlnGluLysLysGluLysLysLysGluLysAlaGluAlaLysAlaGluLysLysArgLeuLysGluGlyGlyGluLysSerAlaGluThrGlnLysSerArg-122 |
| SEQ. ID. NO. 26130 | 138-GluSerLeuArgHisGluIle-144 |
| SEQ. ID. NO. 26131 | 151-AlaLysProGluAspGluValLeuLeu-159 |
| SEQ. ID. NO. 26132 | 161-LeuGluSerProGly-165 |
| SEQ. ID. NO. 26133 | 177-GlnLeuArgArgLeuArgGluArgAsnIle-186 |
| SEQ. ID. NO. 26134 | 191-AlaValAspLysValAlaAla-197 |
| SEQ. ID. NO. 26135 | 232-ArgLeuLeuLysLysHisAspIleAspVal-241 |
| SEQ. ID. NO. 26136 | 247-GlyGluPheLysArg-251 |
| SEQ. ID. NO. 26137 | 258-GluAsnThrGluLysGlyLysGlnLysPheArgGlnGluLeuGluGluThrHisGln-276 |
| SEQ. ID. NO. 26138 | 281-PheValSerGluAsnArgProGlyLeuAspIleGluLysIleAlaThr-296 |
| SEQ. ID. NO. 26139 | 312-AspGluIleSerThrSerAspAspLeuLeu-321 |
| SEQ. ID. NO. 26140 | 325-PheGluAsnLysGlnValIle-331 |
| SEQ. ID. NO. 26141 | 334-LysTyrGlnGluLysArgSerLeuIle-342 |
| SEQ. ID. NO. 26142 | 351-AlaSerValGluLysLeuPhe-357 |
| SEQ. ID. NO. 26143 | 361-ValAsnArgArgAlaAspVal-367 | g006-1
AMPHI Regions - AMPHI

| | |
|---|---|
| SEQ. ID. NO. 26144 | 6-LysHisIleAlaLysThrHisArgLysArg-15 |
| SEQ. ID. NO. 26145 | 19-ThrPheSerProValGlyLeuGluAsnLeuLeu-29 |
| SEQ. ID. NO. 26146 | 48-ArgValTrpGlnAlaLeuLeuTyrAlaLeuValValPhe-60 |
| SEQ. ID. NO. 26147 | 69-ArgArgIleAlaAspThrArgThrPheThrArgIleTyrThrGlu-83 |
| SEQ. ID. NO. 26148 | 111-GluPheValSerPhePheGlu-117 |
| SEQ. ID. NO. 26149 | 125-ThrSerValValSerIlePheGlyAlaCysIleMetLeuLeu-138 |
| SEQ. ID. NO. 26150 | 195-HisTyrGlyLeuValSerArgLeu-202 |
| SEQ. ID. NO. 26151 | 236-GlyTyrGlySerAlaGlyHisIleTyrSer-245 |
| SEQ. ID. NO. 26152 | 257-LeuAspAspValProArgLeuValGluGlnTyrSerAsnLeuLysAspIle-273 |

Antigenic Index - Jameson-Wolf

| | |
|---|---|
| SEQ. ID. NO. 26153 | 6-LysHisIleAlaLysThrHisArgLysArgLeu-16 |
| SEQ. ID. NO. 26154 | 67-AlaAlaArgArgIleAlaAspThrArgThrPheThr-78 |
| SEQ. ID. NO. 26155 | 90-LeuGluGlnArgGlnArgGlnValProHisSer-100 |
| SEQ. ID. NO. 26156 | 173-LeuAsnAsnSerLeuGluArgAspAsnHisPheIleArgLysGlyAspGluArgGlnLeuTyr-193 |
| SEQ. ID. NO. 26157 | 206-IleSerAsnArgGluAlaPhe-212 |
| SEQ. ID. NO. 26158 | 256-SerLeuAspAspValProArgLeuValGluGlnTyrSerAsnLeuLysAspIleGlyGlnArgIleGluTrpSerGluArgAsnIleLysAlaGlyThr-288 |

Hydrophilic Regions - Hopp-Woods

| | |
|---|---|
| SEQ. ID. NO. 26159 | 6-LysHisIleAlaLysThrHisArgLysArgLeu-16 |
| SEQ. ID. NO. 26160 | 67-AlaAlaArgArgIleAlaAspThrArgThrPhe-77 |
| SEQ. ID. NO. 26161 | 90-LeuGluGlnArgGlnArgGlnValPro-98 |
| SEQ. ID. NO. 26162 | 175-AsnSerLeuGluArgAspAsnHisPheIleArgLysGlyAspGluArgGlnLeu-192 |
| SEQ. ID. NO. 26163 | 206-IleSerAsnArgGluAla-211 |
| SEQ. ID. NO. 26164 | 256-SerLeuAspAspValProArgLeuValGlu-265 |
| SEQ. ID. NO. 26165 | 268-SerAsnLeuLysAspIleGlyGln-275 |
| SEQ. ID. NO. 26166 | 277-IleGluTrpSerGluArgAsnIleLysAlaGlyThr-288 | g007-1
AMPHI Regions - AMPHI

| | |
|---|---|
| SEQ. ID. NO. 26167 | 71-HisSerMetValLysGlyIleAsn-78 |
| SEQ. ID. NO. 26168 | 105-ValAlaThrTyrIleMetAsnAlaPheAspAsnGlyGlyGly-118 |

Antigenic Index - Jameson-Wolf

| | |
|---|---|
| SEQ. ID. NO. 26169 | 1-MetAsnThrThrArgLeuProThr-8 |
| SEQ. ID. NO. 26170 | 20-SerAlaAlaAspAsnSerIleMetThrLysGlyGlnLysValTyrGluSerAsnCys-38 |
| SEQ. ID. NO. 26171 | 41-CysHisGlyLysLysGlyGluGlyArgGlyThrAlaPhePro-54 |
| SEQ. ID. NO. 26172 | 56-LeuPheArgSerAspTyrIleMetAsnLysPro-66 |
| SEQ. ID. NO. 26173 | 81-IleLysValAsnGlyLysThrTyrAsnGly-90 |
| SEQ. ID. NO. 26174 | 98-SerAspAlaAspIle-102 |
| SEQ. ID. NO. 26175 | 112-AlaPheAspAsnGlyGlyGlySerValThrGluLysAspValLysGlnAlaLysGlyLysLysAsn-133 |

Hydrophilic Regions - Hopp-Woods

| | |
|---|---|
| SEQ. ID. NO. 26176 | 26-IleMetThrLysGlyGlnLysValTyrGlu-35 |
| SEQ. ID. NO. 26177 | 42-HisGlyLysLysGlyGluGlyArgGly-50 |
| SEQ. ID. NO. 26178 | 98-SerAspAlaAspIle-102 |
| SEQ. ID. NO. 26179 | 119-SerValThrGluLysAspValLysGlnAlaLysGlyLysLyAsn-133 | g008
AMPHI Regions - AMPHI

| | |
|---|---|
| SEQ. ID. NO. 26180 | 15-LeuAspAsnProAlaGlnGlnIleArgGlyAlaLeuAspAlaLeuSer-30 |
| SEQ. ID. NO. 26181 | 54-GlnProAspPheIleAsnAlaVal-61 |
| SEQ. ID. NO. 26182 | 63-ThrValSerThrThr-67 |
| SEQ. ID. NO. 26183 | 69-AspGlyIleAlaLeuLeuAlaGluLeuAsnArg-79 |
| SEQ. ID. NO. 26184 | 90-PheArgAsnAlaPro-94 |
| SEQ. ID. NO. 26185 | 129-ArgProLeuAlaGluIleLeuProAsp-137 |
| SEQ. ID. NO. 26186 | 140-LeuGlyLysTyrGlyLysValValGluLeuSerLysArgLeuGly-154 |

Antigenic Index - Jameson-Wolf

| | |
|---|---|
| SEQ. ID. NO. 26187 | 1-MetAsnAsnArgHis-5 |
| SEQ. ID. NO. 26188 | 12-GlySerAsnLeuAspAsnProAlaGlnGlnIleArgGlyAlaLeu-26 |
| SEQ. ID. NO. 26189 | 29-LeuSerSerHisProAspIleArgLeuGluGln-39 |
| SEQ. ID. NO. 26190 | 49-ValGlyTyrAspAsnGlnPrAspPhe-57 |

TABLE 1-continued

| | |
|---|---|
| SEQ. ID. NO. 26191 | 76-GluLeuAsnArgIleGluAlaAspPheGlyArgGluArgSerPheArgAsnAlaProArgThrLeuAspLeuAspIleIleAspPheAspGly IleSerSerAspAspProArgLeuThrLeuProHisProArgAlaHisGluArgSerPheVal-127 |
| SEQ. ID. NO. 26192 | 139-IleLeuGlyLysTyrGlyLysValValGluLeuSerLysArgLeuGlyAsnGlnGlyIle-158 |
| SEQ. ID. NO. 26193 | 160-LeuLeuProAspArg-164 |

Hydrophilic Regions - Hopp-Woods

| | |
|---|---|
| SEQ. ID. NO. 26194 | 14-AsnLeuAspAsnProAlaGlnGlnIle-22 |
| SEQ. ID. NO. 26195 | 33-ProAspIleArgLeuGluGln-39 |
| SEQ. ID. NO. 26196 | 76-GluLeuAsnArgIleGluAlaAspPheGlyArgGluArgSerPheArgAsnAlaProArgThrLeuAsp-98 |
| SEQ. ID. NO. 26197 | 105-AspGlyIleSerSerAspAspProArgLeu-114 |
| SEQ. ID. NO. 26198 | 120-ArgAlaHisGluArgSerPheVal-127 |
| SEQ. ID. NO. 26199 | 147-ValGluLeuSerLysArgLeuGly-154 |
| SEQ. ID. NO. 26200 | 160-LeuLeuProAspArg-164 | g009
Antigenic Index - Jameson-Wolf

| | |
|---|---|
| SEQ. ID. NO. 26201 | 6-ValAlaPheGluArgHisHisHisLysSerLysAlaGluGlnAsnThrHisArgArgAlaAspAlaGluIleAlaGlu-31 |
| SEQ. ID. NO. 26202 | 37-AsnGlnHisThrGlnAlaArgAsnGlnSerVal-47 |
| SEQ. ID. NO. 26203 | 57-PheSerAspLysVal-61 |
| SEQ. ID. NO. 26204 | 77-AlaAspGlyGlyLysThrTrpGlnLysPro-86 |

Hydrophilic Regions - Hopp-Woods

| | |
|---|---|
| SEQ. ID. NO. 26205 | 6-ValAlaPheGluArgHisHisHisLysSerLysAlaGluGlnAsnThrHisArgArgAlaAspAlaGluIleAlaGlu-31 |
| SEQ. ID. NO. 26206 | 40-ThrGlnAlaArgAsnGlnSer-46 |
| SEQ. ID. NO. 26207 | 78-AspGlyGlyLysThrTrpGln-84 | g010-1
AMPHI Regions - AMPHI

| | |
|---|---|
| SEQ. ID. NO. 26208 | 54-SerAlaSerLeuGly-58 |
| SEQ. ID. NO. 26209 | 70-TyrAspThrValLysGly-75 |
| SEQ. ID. NO. 26210 | 115-TyrGlnArgProPheGlyGlyHis-122 |
| SEQ. ID. NO. 26211 | 125-GluHisGlyLysArgAlaVal-131 |
| SEQ. ID. NO. 26212 | 146-LeuHisThrLeuTyrGln-151 |
| SEQ. ID. NO. 26213 | 210-AlaSerSerThrAsn-214 |
| SEQ. ID. NO. 26214 | 216-TyrMetAsnThrGlyAspGly-222 |
| SEQ. ID. NO. 26215 | 275-ArgTyrAlaProThrValLys-281 |
| SEQ. ID. NO. 26216 | 322-IleMetGluLysLeuProGlyIleArg-330 |
| SEQ. ID. NO. 26217 | 338-GlyIleAspProIleLysAspProPro-347 |
| SEQ. ID. NO. 26218 | 357-GlyGlyIleProThrAsnTyrHis-364 |

Antigenic Index - Jameson-Wolf

| | |
|---|---|
| SEQ. ID. NO. 26219 | 15-GlyGlyGlyAlaGly-19 |
| SEQ. ID. NO. 26220 | 26-LeuSerLysSerGlyLeu-31 |
| SEQ. ID. NO. 26221 | 40-PheProThrArgSerHis-45 |
| SEQ. ID. NO. 26222 | 59-AsnValGlnGluAspArgTrpAsp-66 |
| SEQ. ID. NO. 26223 | 71-AspThrValLysGlySerAspTrpLeuGlyAspGlnAspAlaIle-85 |
| SEQ. ID. NO. 26224 | 104-MetProPheAspArgValGluSerGlyLysIleTyrGlnArgProPheGly-120 |
| SEQ. ID. NO. 26225 | 123-ThrAlaGluHisGlyLysArgAlaValGluArgAlaCysAlaValAlaAspArgThrGly-142 |
| SEQ. ID. NO. 26226 | 152-GlnAsnValArgAlaAsnThr-158 |
| SEQ. ID. NO. 26227 | 168-AspLeuIleArgAspGluAsnGlyAspVal-177 |
| SEQ. ID. NO. 26228 | 183-MetGluMetGluThrGlyGlu-189 |
| SEQ. ID. NO. 26229 | 202-ThrGlyGlyGlyGlyArgIle-208 |
| SEQ. ID. NO. 26230 | 218-AsnThrGlyAspGly-222 |
| SEQ. ID. NO. 26231 | 231-IleProLeuGluAspMetGlu-237 |
| SEQ. ID. NO. 26232 | 255-GluGlyValArgGlyGluGlyGlyIle-263 |
| SEQ. ID. NO. 26233 | 266-AsnAlaAspGlyGluArgPheMetGlu-274 |
| SEQ. ID. NO. 26234 | 276-TyrAlaProThrValLysAspLeuAlaSerArgAspValValSer-290 |
| SEQ. ID. NO. 26235 | 297-IleTyrGluGlyArgGlyCysGlyLysAsnLysAspHisVal-310 |
| SEQ. ID. NO. 26236 | 315-AspHisIleGlyAlaGluLysIleMetGluLysLeuProGlyIleArgGluIleSer-333 |
| SEQ. ID. NO. 26237 | 338-GlyIleAspProIleLysAspProIle-346 |
| SEQ. ID. NO. 26238 | 368-ValValProGlnGlyAspGluTyrGluValProVal-379 |
| SEQ. ID. NO. 26239 | 395-GlyAlaAsnArgLeuGlyThrAsnSerLeu-404 |
| SEQ. ID. NO. 26240 | 411-ArgProThrProArg-415 |

Hydrophilic Regions - Hopp-Woods

| | |
|---|---|
| SEQ. ID. NO. 26241 | 27-SerLysSerGlyLeu-31 |
| SEQ. ID. NO. 26242 | 59-AsnValGlnGluAspArgTrpAsp-66 |
| SEQ. ID. NO. 26243 | 71-AspThrValLysGly-75 |
| SEQ. ID. NO. 26244 | 77-AspTrpLeuGlyAspGlnAspAlaIle-85 |
| SEQ. ID. NO. 26245 | 105-ProPheAspArgValGluSerGlyLysIleTyr-115 |
| SEQ. ID. NO. 26246 | 123-ThrAlaGluHisGlyLysArgAlaValGluArgAlaCysAlaValAlaAspArgThrGly-142 |
| SEQ. ID. NO. 26247 | 168-AspLeuIleArgAspGluAsnGlyAsp-176 |
| SEQ. ID. NO. 26248 | 183-MetGluMetGluThrGlyGlu-189 |
| SEQ. ID. NO. 26249 | 231-IleProLeuGluAspMetGlu-237 |
| SEQ. ID. NO. 26250 | 255-GluGlyValArgGlyGluGly-261 |
| SEQ. ID. NO. 26251 | 267-AlaAspGlyGluArgPheMetGlu-274 |
| SEQ. ID. NO. 26252 | 276-TyrAlaProThrValLysAspLeuAlaSerArgAspValValSer-290 |
| SEQ. ID. NO. 26253 | 297-IleTyrGluGlyArgGlyCysGlyLysAsnLysAspHisVal-310 |
| SEQ. ID. NO. 26254 | 315-AspHisIleGlyAlaGluLysIleMetGluLysLeuProGlyIleArgGluIleSer-333 |
| SEQ. ID. NO. 26255 | 340-AspProIleLysAspProIle-346 |
| SEQ. ID. NO. 26256 | 371-GlnGlyAspGluTyrGluValProVal-379 | g011
AMPHI Regions - AMPHI

| | |
|---|---|
| SEQ. ID. NO. 26257 | 58-IleArgLeuIleAsnAlaAla-64 |
| SEQ. ID. NO. 26258 | 83-AlaIleLeuThrLys-87 |
| SEQ. ID. NO. 26259 | 116-AspValLeuHisArgTyrLeuProGlnMetLeuSerAlaGly-129 |

TABLE 1-continued

| SEQ. ID. NO. 26260 | 142-ThrGlyAlaAlaGlyMetAlaAspMetGlyLysValMet-154 |

Antigenic Index - Jameson-Wolf
| SEQ. ID. NO. 26261 | 1-MetLysThrHisArgLysThrCysSer-9 |
| SEQ. ID. NO. 26262 | 17-ThrAlaSerLysProAlaValSerIleArgHisProSerGluAspIleMetSerLeuLysThrArgLeuThrGluAspMetLysThrAlaMetArgAlaLysAspGlnVal-53 |
| SEQ. ID. NO. 26263 | 66-LysGlnPheGluValAspGluArgThrGluAlaAspAspAlaLysIle-81 |
| SEQ. ID. NO. 26264 | 88-MetValLysGlnArgLysAspGlyAlaLysIleTyrThrGluAlaGlyArgGlnAspLeuAlaAspLysGluAsnAlaGluIle-115 |
| SEQ. ID. NO. 26265 | 127-SerAlaGlyGluIleArgThrAlaVal-135 |
| SEQ. ID. NO. 26266 | 159-ThrArgLeuAlaGlyLysAlaAspMetGlyGluValAsnLysIleLeu-174 |

Hydrophilic Regions - Hopp-Woods
| SEQ. ID. NO. 26267 | 1-MetLysThrHisArgLysThrCys-8 |
| SEQ. ID. NO. 26268 | 27-HisProSerGluAspIleMetSerLeuLysThrArgLeuThrGluAspMetLysThrAlaMetArgAlaLysAspGlnVal-53 |
| SEQ. ID. NO. 26269 | 66-LysGlnPheGluValAspGluArgThrGluAlaAspAspAlaLysIle-81 |
| SEQ. ID. NO. 26270 | 88-MetValLysGlnArgLysAspGlyAlaLysIleTyrThrGluAlaGlyArgGlnAspLeuAlaAspLysGluAsnAlaGluIle-115 |
| SEQ. ID. NO. 26271 | 129-GlyGluIleArgThrAlaVal-135 |
| SEQ. ID. NO. 26272 | 159-ThrArgLeuAlaGlyLysAlaAspMetGlyGluValAsnLysIleLeu-174 | g012-1
AMPHI Regions - AMPHI
| SEQ. ID. NO. 26273 | 18-AspLysLeuLeuGluGlnLeuMetArgPheLeuGlnPheLeuProGluPheLeuPheAlaLeuPheArgIle-41 |
| SEQ. ID. NO. 26274 | 48-ArgAlaLeuLysPheAlaArgArg-55 |
| SEQ. ID. NO. 26275 | 89-AsnAsnPheIleArgHisThr-95 |
| SEQ. ID. NO. 26276 | 100-AlaAlaAlaCysArgAsp-105 |
| SEQ. ID. NO. 26277 | 133-HisAlaAlaArgThrPhe-138 |
| SEQ. ID. NO. 26278 | 160-GlnGlyPheTyrGlyVal-165 |
| SEQ. ID. NO. 26279 | 179-GlyPheLeuArgPheGlyArgPheLeuProAlaLeuLeuGlnThrLeu-194 |

Antigenic Index - Jameson-Wolf
| SEQ. ID. NO. 26280 | 42-PheThrHisLysSerAsnArgAlaLeuLysPheAlaArgArgHisHis-57 |
| SEQ. ID. NO. 26281 | 72-ArgHisPheArgHisHisThrHisArgThrAspAspArgLysArgSerGlyAsnAsnPheIleArgHisThrArg-96 |
| SEQ. ID. NO. 26282 | 102-AlaCysArgAspLeuIleAspGlyAspGlyGlnArgAsn-114 |
| SEQ. ID. NO. 26283 | 119-GlnThrProLysLeuArgSerArgGln-127 |
| SEQ. ID. NO. 26284 | 137-ThrPheGlnSerGluGlnAsnLeu-144 |
| SEQ. ID. NO. 26285 | 147-ArgLeuGlyAsnGlnLysHisArgArgAsnLeuMetThrGln-160 |
| SEQ. ID. NO. 26286 | 173-IleGlnHisLysLysAlaGly-179 |

Hydrophilic Regions - Hopp-Woods
| SEQ. ID. NO. 26287 | 45-LysSerAsnArgAlaLeuLysPheAlaArgArgHisHis-57 |
| SEQ. ID. NO. 26288 | 77-HisThrHisArgThrAspAspArgLysArgSerGly-88 |
| SEQ. ID. NO. 26289 | 102-AlaCysArgAspLeuIleAspGlyAspGlyGlnArg-113 |
| SEQ. ID. NO. 26290 | 121-ProLysLeuArgSerArgGln-127 |
| SEQ. ID. NO. 26291 | 149-GlyAsnGlnLysHisArgArgAsnLeu-157 |
| SEQ. ID. NO. 26292 | 173-IleGlnHisLysLysAlaGly-179 | g015
AMPHI Regions - AMPHI
| SEQ. ID. NO. 26293 | 36-LeuValGlyPheTrpLysAlaLeuProHis-45 |
| SEQ. ID. NO. 26294 | 107-MetCysCysIleAlaCys-112 |

Antigenic Index - Jameson-Wolf
| SEQ. ID. NO. 26295 | 29-TrpLysAsnProGluLysProLeu-36 |
| SEQ. ID. NO. 26296 | 90-MetArgAlaArgProArgSerThrLys-98 |

Hydrophilic Regions - Hopp-Woods
| SEQ. ID. NO. 26297 | 31-AsnProGluLysProLeu-36 |
| SEQ. ID. NO. 26298 | 90-MetArgAlaArgProArgSerThrLys-98 | g018-2
AMPHI Regions - AMPHI
| SEQ. ID. NO. 26299 | 6-IleGlnHisLeuArg-10 |
| SEQ. ID. NO. 26300 | 15-HisLeuMetArgProCysGlnGlnValSerGlnMetPheGly-28 |
| SEQ. ID. NO. 26301 | 152-ArgIleGlyAsnGlyTyr-157 |

Antigenic Index - Jameson-Wolf
| SEQ. ID. NO. 26302 | 1-MetValGluArgHisIleGln-7 |
| SEQ. ID. NO. 26303 | 9-LeuArgAsnGlyHisLeu-14 |
| SEQ. ID. NO. 26304 | 27-PheGlyGlyArgAlaTyrAspPheArgAlaAspLysAlaAlaGly-41 |
| SEQ. ID. NO. 26305 | 67-TyrPheAlaAspAspLysPhe-73 |
| SEQ. ID. NO. 26306 | 78-LeuArgGlyAsnLeuArg-83 |
| SEQ. ID. NO. 26307 | 85-PheGlnThrAspLysAlaAspLeuArgThrGlyLysHisHisAlaAsnGly-101 |
| SEQ. ID. NO. 26308 | 108-AlaAspIleArgValAlaAla-114 |
| SEQ. ID. NO. 26309 | 136-ArgValAlaArgAsnLysAspMetArgAsnAlaGlyLeuHis-149 |
| SEQ. ID. NO. 26310 | 152-ArgIleGlyAsnGlyTyr-157 |
| SEQ. ID. NO. 26311 | 176-ArgThrAlaThrTyr-180 |
| SEQ. ID. NO. 26312 | 223-SerGluHisGlyPheArg-228 |

Hydrophilic Regions - Hopp-Woods
| SEQ. ID. NO. 26313 | 1-MetValGluArgHisIleGln-7 |
| SEQ. ID. NO. 26314 | 30-ArgAlaTyrAspPheArgAlaAspLysAlaAla-40 |
| SEQ. ID. NO. 26315 | 67-TyrPheAlaAspAspLysPhe-73 |
| SEQ. ID. NO. 26316 | 85-PheGlnThrAspLysAlaAspLeuArgThrGlyLysHisHisAla-99 |
| SEQ. ID. NO. 26317 | 108-AlaAspIleArgValAlaAla-114 |
| SEQ. ID. NO. 26318 | 136-ArgValAlaArgAsnLysAspMetArgAsn-145 | g019-2
AMPHI Regions - AMPHI
| SEQ. ID. NO. 26319 | 33-ProAlaAspAsnIleGlu-38 |
| SEQ. ID. NO. 26320 | 55-GlyLysThrLeuAlaAspTyrGlyGlyTyrProSerAlaLeuAspAlaValLysGln-73 |
| SEQ. ID. NO. 26321 | 83-LeuGluAsnThrGlyAsp-88 |
| SEQ. ID. NO. 26322 | 90-AlaMetAlaGluAsnValArgLysGluTrpLeuLysSer-102 |

TABLE 1-continued

| | |
|---|---|
| SEQ. ID. NO. 26323 | 142-AlaAlaGluLeuValXxxAsnThrGlyLysLeuProSerGlyCysThrLysLeuLeuGluGlnAla-163 |
| SEQ. ID. NO. 26324 | 173-AspAlaTrpArgGlyValArgGlyLeu-181 |
| SEQ. ID. NO. 26325 | 195-AlaAlaLeuGlySerProPheAspGlyGlyThrGlnGly-207 |
| SEQ. ID. NO. 26326 | 215-AsnValIleGlyLysGluAlaArgLysSer-224 |
| SEQ. ID. NO. 26327 | 229-AlaLeuLeuSerGluMetGlu-235 |
| SEQ. ID. NO. 26328 | 259-AsnValProAlaAlaLeuAspTyrTyrGly-268 |
| SEQ. ID. NO. 26329 | 292-ArgArgTrpAspGluLeuAlaSerValIleSerHisMetProGluLysLeuGlnLys-310 |
| SEQ. ID. NO. 26330 | 329-GlnGluAlaGluLysLeuTyrLysGlnAla-338 |
| SEQ. ID. NO. 26331 | 451-ArgTyrIleSerPro-455 |
| SEQ. ID. NO. 26332 | 495-GlnGlyLeuMetGlnValMet-501 |
| SEQ. ID. NO. 26333 | 582-ArgAspTyrValLysLysValMet-589 |
| Antigenic Index - Jameson-Wolf | |
| SEQ. ID. NO. 26334 | 22-SerSerThrAsnThr-26 |
| SEQ. ID. NO. 26335 | 28-ProAlaGlyLysThrProAlaAspAsnIleGluThrAlaAspLeuSerAlaSerValProThrArgProAlaGluProGluGlyLysThrLeuAlaAspTyrGlyGlyTyrProSerAla-67 |
| SEQ. ID. NO. 26336 | 69-AspAlaValLysGlnAsnAsnAspAlaAla-78 |
| SEQ. ID. NO. 26337 | 84-GluAsnThrGlyAspSerAlaMet-91 |
| SEQ. ID. NO. 26338 | 93-GluAsnValArgLysGluTrpLeu-100 |
| SEQ. ID. NO. 26339 | 103-LeuGlyAlaArgArgGln-108 |
| SEQ. ID. NO. 26340 | 115-GluTyrAlaLysLeuLysProGluGlyGlyAlaGlnGluValGluCysTyrAlaAspSerSerArgAsnAspTyrThrArgAlaAlaGlu-144 |
| SEQ. ID. NO. 26341 | 147-XxxAsnThrGlyLysLeuProSerGlyCys-156 |
| SEQ. ID. NO. 26342 | 170-GlyGlyAsnAspAlaTrpArgGlyValArg-179 |
| SEQ. ID. NO. 26343 | 182-LeuAlaGlyArgProThrThrAspGlyArgAsn-192 |
| SEQ. ID. NO. 26344 | 199-SerProPheAspGlyGlyThrGlnGlySerArgGluTyr-211 |
| SEQ. ID. NO. 26345 | 217-IleGlyLysGluAlaArgLysSerProAsnAla-227 |
| SEQ. ID. NO. 26346 | 232-SerGluMetGluSerGlyLeuSerProGlnArgSer-244 |
| SEQ. ID. NO. 26347 | 254-GlnSerGlnSerLeu-258 |
| SEQ. ID. NO. 26348 | 266-TyrTyrGlyLysValAlaAspArgArgGlnLeuThrAspAspGlnIle-281 |
| SEQ. ID. NO. 26349 | 287-AlaAlaLeuArgAlaArgArgTrpAspGlu-296 |
| SEQ. ID. NO. 26350 | 304-MetProGluLysLeuGlnLysSerProThr-313 |
| SEQ. ID. NO. 26351 | 320-ArgSerArgAlaAlaThrGlyAsnThrGlnGluAlaGluLysLeuTyrLys-336 |
| SEQ. ID. NO. 26352 | 339-AlaAlaThrGlyArgAsn-344 |
| SEQ. ID. NO. 26353 | 350-AlaGlyGluGluLeuGlyArgLysIleAspThrArgAsnAsnValProAspAlaGlyLysAsnSerVal-372 |
| SEQ. ID. NO. 26354 | 374-ArgMetAlaGluAspGlyAlaIleLys-382 |
| SEQ. ID. NO. 26355 | 389-ArgAsnSerArgThrAlaGlyAspAlaLysMetArgArgGlnAlaGlnAla-405 |
| SEQ. ID. NO. 26356 | 409-PheAlaThrArgGlyPheAspGluAspLysLeuLeu-420 |
| SEQ. ID. NO. 26357 | 438-SerAlaGluArgThrAspArgLysLeuAsnTyr-448 |
| SEQ. ID. NO. 26358 | 454-SerProPheLysAspThrValIle-461 |
| SEQ. ID. NO. 26359 | 464-AlaGlnAsnValAsnValAspProAla-472 |
| SEQ. ID. NO. 26360 | 478-IleArgGlnGluSerArgPhe-484 |
| SEQ. ID. NO. 26361 | 488-AlaGlnSerArgValGlyAla-494 |
| SEQ. ID. NO. 26362 | 504-ThrAlaArgGluIleAlaGly-510 |
| SEQ. ID. NO. 26363 | 520-TyrThrAlaAspGlyAsnIleArgMetGly-529 |
| SEQ. ID. NO. 26364 | 535-AspThrLysArgArgLeuGlnAsnAsnGluIle-545 |
| SEQ. ID. NO. 26365 | 550-GlyTyrAsnAlaGlyProGlyArgAlaArgArgTrpGlnAlaAspThrProLeuGlu-568 |
| SEQ. ID. NO. 26366 | 579-SerGluThrArgAspTyrValLys-586 |
| SEQ. ID. NO. 26367 | 605-ProLeuLysGlnArgMetGlyThrValProAlaArg-616 |
| Hydrophilic Regions - Hopp-Woods | |
| SEQ. ID. NO. 26368 | 30-GlyLysThrProAlaAspAsnIleGluThrAlaAspLeu-42 |
| SEQ. ID. NO. 26369 | 46-ValProThrArgProAlaGluProGluGlyLysThrLeuAla-59 |
| SEQ. ID. NO. 26370 | 69-AspAlaValLysGlnAsnAsnAspAlaAla-78 |
| SEQ. ID. NO. 26371 | 85-AsnThrGlyAspSerAlaMet-91 |
| SEQ. ID. NO. 26372 | 93-GluAsnValArgLysGluTrpLeu-100 |
| SEQ. ID. NO. 26373 | 103-LeuGlyAlaArgArgGln-108 |
| SEQ. ID. NO. 26374 | 115-GluTyrAlaLysLeuLysProGluGlyGlyAlaGlnGluValGluCysTyrAlaAspSerSerArgAsnAspTyrThrArgAlaAlaGlu-144 |
| SEQ. ID. NO. 26375 | 150-GlyLysLeuProSerGlyCys-156 |
| SEQ. ID. NO. 26376 | 173-AspAlaTrpArgGly-177 |
| SEQ. ID. NO. 26377 | 186-ProThrThrAspGlyArgAsn-192 |
| SEQ. ID. NO. 26378 | 201-PheAspGlyGlyThrGlnGlySerArgGlu-210 |
| SEQ. ID. NO. 26379 | 217-IleGlyLysGluAlaArgLysSerProAsn-226 |
| SEQ. ID. NO. 26380 | 232-SerGluMetGluSerGlyLeuSerProGlnArgSer-244 |
| SEQ. ID. NO. 26381 | 270-ValAlaAspArgArgGlnLeuThrAspAspGlnIle-281 |
| SEQ. ID. NO. 26382 | 287-AlaAlaLeuArgAlaArgArgTrpAspGlu-296 |
| SEQ. ID. NO. 26383 | 304-MetProGluLysLeuGlnLys-310 |
| SEQ. ID. NO. 26384 | 320-ArgSerArgAlaAlaThr-325 |
| SEQ. ID. NO. 26385 | 327-AsnThrGlnGluAlaGluLysLeuTyrLys-336 |
| SEQ. ID. NO. 26386 | 350-AlaGlyGluGluLeuGlyArgLysIleAspThrArgAsnAsnValProAspAlaGlyLys-369 |
| SEQ. ID. NO. 26387 | 374-ArgMetAlaGluAspGlyAlaIleLys-382 |
| SEQ. ID. NO. 26388 | 389-ArgAsnSerArgThrAlaGlyAspAlaLysMetArgArgGlnAlaGlnAla-405 |
| SEQ. ID. NO. 26389 | 411-ThrArgGlyPheAspGluAspLysLeuLeu-420 |
| SEQ. ID. NO. 26390 | 438-SerAlaGluArgThrAspArgLysLeu-446 |
| SEQ. ID. NO. 26391 | 478-IleArgGlnGluSerArgPhe-484 |
| SEQ. ID. NO. 26392 | 504-ThrAlaArgGluIleAlaGly-510 |
| SEQ. ID. NO. 26393 | 535-AspThrLysArgArgLeuGlnAsn-542 |
| SEQ. ID. NO. 26394 | 554-GlyProGlyArgAlaArgArgTrpGlnAla-563 |
| SEQ. ID. NO. 26395 | 579-SerGluThrArgAspTyrValLys-586 |
| SEQ. ID. NO. 26396 | 606-LeuLysGlnArgMetGly-611 |

TABLE 1-continued g023
AMPHI Regions - AMPHI
SEQ. ID. NO. 26397 43-GluTyrProAlaTrpGlnAlaPhePheSerGlnAlaTrpValLysValPheThrGlnValSerPheIleAlaValPheLeuHis
AlaTrpValGly-74
SEQ. ID. NO. 26398 77-AspLeuTrpMetAspTyrIleLys-84
Antigenic Index - Jameson-Wolf
SEQ. ID. NO. 26399 1-MetValGluArgLysLeuThr-7
SEQ. ID. NO. 26400 40-LeuProLysGluTyrProAlaTrp-47
Hydrophilic Regions - Hopp-Woods
SEQ. ID. NO. 26401 1-MetValGluArgLysLeuThr-7
g025
AMPHI Regions - AMPHI
SEQ. ID. NO. 26402 9-AlaAlaCysThrAlaValAlaAlaLeuLeuGlyGlyCysAla-22
SEQ. ID. NO. 26403 35-GlyMetGlnThrValSerSer-41
SEQ. ID. NO. 26404 46-AsnProTyrGlyAlaThrProTyr-53
SEQ. ID. NO. 26405 126-AspPheArgAlaTrpAsnGlyMetThrAsp-135
SEQ. ID. NO. 26406 140-IleGlyGlnIleValLysVal-146
SEQ. ID. NO. 26407 173-ValLysProAlaAla-177
SEQ. ID. NO. 26408 181-ValGlnSerAlaProGlnPro-187
SEQ. ID. NO. 26409 212-SerGlyThrArgSer-216
SEQ. ID. NO. 26410 229-LysValValAlaAspPhe-234
SEQ. ID. NO. 26411 265-GlyLeuArgGlyTyrGlyAsn-271
Antigenic Index - Jameson-Wolf
SEQ. ID. NO. 26412 22-AlaThrGlnGlnPro-26
SEQ. ID. NO. 26413 108-ValArgGlyAspThr-112
SEQ. ID. NO. 26414 115-AsnIleSerLysArgTyrHisIleSerGlnAspAspPheArgAla-129
SEQ. ID. NO. 26415 131-AsnGlyMetThrAspAsnThrLeu-138
SEQ. ID. NO. 26416 144-ValLysValLysProAlaGly-150
SEQ. ID. NO. 26417 152-AlaAlaProLysThrAlaAlaValGluSerArgProAlaValPro-166
SEQ. ID. NO. 26418 171-ThrProValLysProAlaAlaGlnProProValGlnSerAlaProGlnPro-187
SEQ. ID. NO. 26419 190-ProAlaAlaGluAsnLysAlaValPro-198
SEQ. ID. NO. 26420 202-ProAlaProGlnSerProAlaAlaSerProSerGlyThrArgSerValGly-218
SEQ. ID. NO. 26421 224-ArgProThrGlnGlyLysValValAlaAspPheGlyGlyGlyAsnLysGlyValAsp-242
SEQ. ID. NO. 26422 255-AlaAspGlyLysVal-259
SEQ. ID. NO. 26423 264-SerGlyLeuArgGlyTyrGly-270
SEQ. ID. NO. 26424 285-TyrGlyHisAsnGln-289
SEQ. ID. NO. 26425 292-LeuValGlyGluGlyGlnGlnValLysArgGlyGlnGln-304
SEQ. ID. NO. 26426 309-GlyAsnThrAspAlaSerArgThrGlnLeu-318
SEQ. ID. NO. 26427 320-PheGluValArgGlnAsnGlyLysProValAsnProAsnSer-333
Hydrophilic Regions - Hopp-Woods
SEQ. ID. NO. 26428 108-ValArgGlyAspThr-112
SEQ. ID. NO. 26429 120-TyrHisIleSerGlnAspAspPheArg-128
SEQ. ID. NO. 26430 144-ValLysValLysPro-148
SEQ. ID. NO. 26431 157-AlaAlaValGluSerArgProAla-164
SEQ. ID. NO. 26432 171-ThrProValLysProAlaAla-177
SEQ. ID. NO. 26433 190-ProAlaAlaGluAsnLysAlaValPro-198
SEQ. ID. NO. 26434 212-SerGlyThrArgSer
SEQ. ID. NO. 26435 235-GlyGlyGlyAsnLysGlyValAsp-242
SEQ. ID. NO. 26436 255-AlaAspGlyLysVal-259
SEQ. ID. NO. 26437 295-GluGlyGlnGlnValLysArgGlyGln-303
SEQ. ID. NO. 26438 311-ThrAspAlaSerArgThr-316
SEQ. ID. NO. 26439 322-ValArgGlnAsnGlyLysProValAsn-330
g032
AMPHI Regions - AMPHI
SEQ. ID. NO. 26440 9-AlaValLeuArgArgProArgPheGlu-17
SEQ. ID. NO. 26441 67-ProPheAlaGlyAsnValTyrProArgPheValGlnIle-79
SEQ. ID. NO. 26442 114-ValHisGlyGlnIleGlnHisProValGlnProPheLeuArg-127
SEQ. ID. NO. 26443 134-LeuGlyLeuLeuArgArgPheAspVal-142
SEQ. ID. NO. 26444 174-GlnThrAlaLeuArg-178
SEQ. ID. NO. 26445 204-LeuCysGlnGlnCysLysGlnPhePheGlnIleAla-215
Antigenic Index - Jameson-Wolf
SEQ. ID. NO. 26446 1-MetArgArgAsnVal-5
SEQ. ID. NO. 26447 10-ValLeuArgArgProArgPhe-16
SEQ. ID. NO. 26448 28-ArgAlaValProAlaGlyLysGlnGlyPhe-37
SEQ. ID. NO. 26449 41-CysArgLeuThrGlnArg-46
SEQ. ID. NO. 26450 58-GlyGlnArgAsnLeu-62
SEQ. ID. NO. 26451 100-LeuGluGlnArgValValAlaHisArgGlnArgVal-111
SEQ. ID. NO. 26452 138-ArgArgPheAspValGlyGlyArgValGlyAla-148
SEQ. ID. NO. 26453 151-ProAlaPheAspGlnProGlyAla-158
SEQ. ID. NO. 26454 160-LeuProProArgArgGlnLeuAlaArgGlnArgProThrVal-173
SEQ. ID. NO. 26455 176-AlaLeuArgGlnProProGlnArgArgArgLysIleAlaProArgGlnValLeu-193
SEQ. ID. NO. 26456 202-ArgHisLeuCysGlnGlnCysLys-209
SEQ. ID. NO. 26457 216-ProValCysArgAsnArgValLeuArg-224
SEQ. ID. NO. 26458 236-ValLysIleArgArgLysProValGlnAsnHisAsnArgProThrGlnIleSerLysAsnGln-256
Hydrophilic Regions - Hopp-Woods
SEQ. ID. NO. 26459 1-MetArgArgAsnVal-5
SEQ. ID. NO. 26460 10-ValLeuArgArgProArgPhe-16
SEQ. ID. NO. 26461 41-CysArgLeuThrGln-45
SEQ. ID. NO. 26462 100-LeuGluGlnArgValValAlaHisArgGlnArgVal-111
SEQ. ID. NO. 26463 138-ArgArgPheAspValGlyGly-144

TABLE 1-continued

| | |
|---|---|
| SEQ. ID. NO. 26464 | 161-ProProArgArgGlnLeuAlaArgGlnArgProThrVal-173 |
| SEQ. ID. NO. 26465 | 177-LeuArgGlnProProGlnArgArgArgLysIleAlaPro-189 |
| SEQ. ID. NO. 26466 | 218-CysArgAsnArgValLeu-223 |
| SEQ. ID. NO. 26467 | 236-ValLysIleArgArgLysProValGlnAsnHisAsnArgProThrGlnIleSerLysAsnGln-256 |
| g033-2 | |
| AMPHI Regions - AMPHI | |
| SEQ. ID. NO. 26468 | 6-GlnTyrGlyGlyLeuAlaGlyPheProLysArgCysGluSerGlu-20 |
| SEQ. ID. NO. 26469 | 64-GlyGlnAlaPheGluAlaLeuAsnCys-72 |
| SEQ. ID. NO. 26470 | 95-ValGlyAlaLeuProLysTyrLeuAlaSerAsnValValArgAspMetHisGlyLeuLeuSerThrVal-117 |
| SEQ. ID. NO. 26471 | 120-GlnThrGlyLysValLeuAspLysIleProGlyAlaMetGlu-133 |
| SEQ. ID. NO. 26472 | 142-IleLysThrLeuAlaGlu-147 |
| SEQ. ID. NO. 26473 | 157-SerLeu |
| SEQ. ID. NO. 26474 | PheGluAsnPhe-162 |
| SEQ. ID. NO. 26475 | 168-GlyProValAspGlyHisAsnValGluAsnLeuValAspValLeuLysAspLeuArgSerArg-188 |
| SEQ. ID. NO. 26476 | 207-AlaGluAsnAspPro-211 |
| SEQ. ID. NO. 26477 | 213-LysTyrHisAlaValAlaAsnLeuProLysGluGlyGlyAla-226 |
| SEQ. ID. NO. 26478 | 242-TyrThrGlnValPheGlyLys-248 |
| SEQ. ID. NO. 26479 | 280-PheProAspArgTyrPheAspVal-287 |
| SEQ. ID. NO. 26480 | 307-LysProValValAlaIleTyrSer-314 |
| SEQ. ID. NO. 26481 | 316-PheLeuGlnArgAlaTyrAspGlnLeu-324 |
| SEQ. ID. NO. 26482 | 363-CysValProAsnMet-367 |
| SEQ. ID. NO. 26483 | 390-AlaProAlaAlaValArgTyrProArgGlyThr-400 |
| SEQ. ID. NO. 26484 | 406-ValSerAspGlyMetGluThrValGlu-414 |
| SEQ. ID. NO. 26485 | 419-IleIleArgArgGlu-423 |
| SEQ. ID. NO. 26486 | 453-MetArgPheValLysProIleAspGluGlu-462 |
| SEQ. ID. NO. 26487 | 469-ArgSerHisAspArgIle-474 |
| SEQ. ID. NO. 26488 | 489-AlaValLeuGluValLeu-494 |
| SEQ. ID. NO. 26489 | 510-AspThrValThrGluHisGlyAspProLysLysLeuLeu-522 |
| Antigenic Index - Jameson-Wolf | |
| SEQ. ID. NO. 26490 | 11-AlaGlyPheProLysArgCysGluSerGluTyrAspAla-23 |
| SEQ. ID. NO. 26491 | 28-HisSerSerThrSerIle-33 |
| SEQ. ID. NO. 26492 | 41-AlaAlaAspLysLeuLeuGlyGlyAspArgArgSerVal-53 |
| SEQ. ID. NO. 26493 | 57-GlyAspGlyAlaMetThr-62 |
| SEQ. ID. NO. 26494 | 72-CysAlaGlyAspMetAspVal-78 |
| SEQ. ID. NO. 26495 | 85-AsnAspAsnGluMetSerIle-91 |
| SEQ. ID. NO. 26496 | 105-AsnValValArgAspMetHisGly-112 |
| SEQ. ID. NO. 26497 | 117-ValLysAlaGlnThrGlyLysValLeuAspLysIleProGly-130 |
| SEQ. ID. NO. 26498 | 134-PheAlaGlnLysValGluHisLysIleLysThrLeuAlaGluGluAlaGluHisAlaLysGln-154 |
| SEQ. ID. NO. 26499 | 166-TyrThrGlyProValAspGlyHisAsn-174 |
| SEQ. ID. NO. 26500 | 181-ValLeuLysAspLeuArgSerArgLysGlyProGln-192 |
| SEQ. ID. NO. 26501 | 197-IleThrLysLysGlyAsnGlyTyrLysLeuAlaGluAsnAspProValLys-213 |
| SEQ. ID. NO. 26502 | 219-AsnLeuProLysGluGlyGlyAlaGlnMetProSerGluLysGluProLysProAlaAlaLysProThrTyr-242 |
| SEQ. ID. NO. 26503 | 253-ArgAlaAlaAlaAspSerArgLeu-260 |
| SEQ. ID. NO. 26504 | 266-AlaMetArgGluGlySerGlyLeuValGluPheGluGlnArgPheProAspArgTyrPhe-285 |
| SEQ. ID. NO. 26505 | 345-ValGlyAlaAspGlyProThrHis-352 |
| SEQ. ID. NO. 26506 | 370-AlaAlaProSerAspGluAsnGluCysArg-379 |
| SEQ. ID. NO. 26507 | 395-ArgTyrProArgGlyThrGlyThrGlyAlaProValSerAspGlyMetGluThrValGluIleGlyLysGlyIleIleArgArgGluGlyGluLysThrAla-428 |
| SEQ. ID. NO. 26508 | 457-LysProIleAspGluGluLeuIle-464 |
| SEQ. ID. NO. 26509 | 467-LeuAlaArgSerHisAspArgIleValThrLeuGluGluAsnAlaGluGlnGlyGlyAlaGlyGly-488 |
| SEQ. ID. NO. 26510 | 511-ThrValThrGluHisGlyAspProLysLysLeuLeuAspAspLeuGlyLeu-527 |
| SEQ. ID. NO. 26511 | 530-GluAlaValGluArgArgValArgGluTrpLeuProAspArgAspAlaAlaAsn-547 |
| Hydrophilic Regions - Hopp-Woods | |
| SEQ. ID. NO. 26512 | 13-PheProLysArgCysGluSerGluTyrAsp-22 |
| SEQ. ID. NO. 26513 | 41-AlaAlaAspLysLeuLeuGlyGlyAspArgArgSerVal-53 |
| SEQ. ID. NO. 26514 | 74-GlyAspMetAspVal-78 |
| SEQ. ID. NO. 26515 | 85-AsnAspAsnGluMetSerIle-91 |
| SEQ. ID. NO. 26516 | 106-ValValArgAspMetHis-111 |
| SEQ. ID. NO. 26517 | 123-LysValLeuAspLysIleProGly-130 |
| SEQ. ID. NO. 26518 | 134-PheAlaGlnLysValGluHisLysIleLysThrLeuAlaGluGluAlaGluHisAlaLysGln-154 |
| SEQ. ID. NO. 26519 | 181-ValLeuLysAspLeuArgSerArgLysGlyPro-191 |
| SEQ. ID. NO. 26520 | 197-IleThrLysLysGlyAsnGly-203 |
| | 205-LysLeuAlaGluAsnAspProValLys-213 |
| SEQ. ID. NO. 26521 | 220-LeuProLysGluGlyGlyAla-226 |
| SEQ. ID. NO. 26522 | 228-MetProSerGluLysGluProLysProAlaAla-238 |
| SEQ. ID. NO. 26523 | 253-ArgAlaAlaAlaAspSerArgLeu-260 |
| SEQ. ID. NO. 26524 | 266-AlaMetArgGluGlySerGly-272 |
| SEQ. ID. NO. 26525 | 274-ValGluPheGluGlnArgPheProAspArgTyrPhe-285 |
| SEQ. ID. NO. 26526 | 372-ProSerAspGluAsnGluCys-378 |
| SEQ. ID. NO. 26527 | 405-ProValSerAspGlyMetGluThrValGluIleGlyLysGlyIleIleArgArgGluGlyGluLysThrAla-428 |
| SEQ. ID. NO. 26528 | 457-LysProIleAspGluGluLeuIle-464 |
| SEQ. ID. NO. 26529 | 467-LeuAlaArgSerHisAspArgIleValThrLeuGluGluAsnAlaGluGlnGlyGly-485 |
| SEQ. ID. NO. 26530 | 511-ThrValThrGluHisGlyAspProLysLysLeuLeuAsp-523 |
| SEQ. ID. NO. 26531 | 530-GluAlaValGluArgArgValArgGluTrpLeuProAspArgAspAlaAlaAsn-547 |
| g034 | |
| AMPHI Regions - AMPHI | |
| SEQ. ID. NO. 26532 | 35-LeuAspHisAlaAla-39 |
| SEQ. ID. NO. 26533 | 52-AsnLeuGluGlnMetArgAlaIleMetGluAlaAlaAspGln-65 |
| SEQ. ID. NO. 26534 | 94-AlaValGluGluPheProHisIlePro-102 |
| SEQ. ID. NO. 26535 | 152-ThrValValAsnPheSer-157 |

TABLE 1-continued

| | |
|---|---|
| SEQ. ID. NO. 26536 | 168-IleGlyValLeuGlyAsnLeuGluThrGly-177 |
| SEQ. ID. NO. 26537 | 197-LeuThrSerValGluAspAlaValArgPheValLysAspThrGly-211 |
| SEQ. ID. NO. 26538 | 226-TyrLysPheThrArgProProThrGly-234 |
| SEQ. ID. NO. 26539 | 236-ValLeuArgIleAspArgIleLysGluIleHisGlnAlaLeu-249 |
| SEQ. ID. NO. 26540 | 261-SerValProGlnGluTrpLeuLysValIleAsnGluTyrGlyGlyAsnIleGlyGluThrTyrGlyValProValGluGluIleValGluGly IleLysHisGly-295 |
| SEQ. ID. NO. 26541 | 314-ArgArgTyrLeuAlaGluAsn-320 |
| SEQ. ID. NO. 26542 | 330-LeuGlyLysThrIleGluAlaMetLys-338 |

Antigenic Index - Jameson-Wolf

| | |
|---|---|
| SEQ. ID. NO. 26543 | 20-LeuProLysGluThrGln-25 |
| SEQ. ID. NO. 26544 | 37-HisAlaAlaGluAsnSerTyrGly-44 |
| SEQ. ID. NO. 26545 | 54-GluGlnMetArgAlaIleMetGluAlaAlaAspGlnVal-66 |
| SEQ. ID. NO. 26546 | 75-SerAlaGlyAlaArgLysTyrAla-82 |
| SEQ. ID. NO. 26547 | 106-HisGlnAspHisGlyAlaSerProAspValCysGlnArgSerIle-120 |
| SEQ. ID. NO. 26548 | 132-SerLeuLeuGluAspGlyLysThrProSerSerTyrGluTyr-145 |
| SEQ. ID. NO. 26549 | 164-ValGluGlyGluIle-168 |
| SEQ. ID. NO. 26550 | 173-AsnLeuGluThrGlyGluAlaGlyGluGluAspGlyValGlyAla-187 |
| SEQ. ID. NO. 26551 | 191-LeuSerHisAspGln-195 |
| SEQ. ID. NO. 26552 | 199-SerValGluAspAlaValArgPheValLysAspThrGlyValAsp-213 |
| SEQ. ID. NO. 26553 | 221-ThrSerHisGlyAla-225 |
| SEQ. ID. NO. 26554 | 227-LysPheThrArgProProThrGlyAspValLeuArgIleAspArgIleLysGluIleHis-246 |
| SEQ. ID. NO. 26555 | 258-GlySerSerSerValPro-263 |
| SEQ. ID. NO. 26556 | 271-AsnGluTyrGlyGlyAsnIleGlyGlu-279 |
| SEQ. ID. NO. 26557 | 287-GluIleValGluGlyIleLysHisGlyValArgLysValAsnIleAspThrAspLeuArgLeuAlaSerThrGlyAlaVal-313 |
| SEQ. ID. NO. 26558 | 316-TyrLeuAlaGluAsnProSerAspPheAspProArgLysTyrLeuGlyLysThrIleGluAlaMetLys-338 |
| SEQ. ID. NO. 26559 | 350-CysGluGlyGlnAlaGlyLysIleLysProValSerLeuGluLysMetAlaSerArgTyrAlaLysGlyGluLeu-374 |

Hydrophilic Regions - Hopp-Woods

| | |
|---|---|
| SEQ. ID. NO. 26560 | 54-GluGlnMetArgAlaIleMetGluAlaAlaAspGlnVal-66 |
| SEQ. ID. NO. 26561 | 76-AlaGlyAlaArgLysTyrAla-82 |
| SEQ. ID. NO. 26562 | 108-AspHisGlyAlaSerProAspValCysGln-117 |
| SEQ. ID. NO. 26563 | 132-SerLeuLeuGluAspGlyLysThrProSer-141 |
| SEQ. ID. NO. 26564 | 164-ValGluGlyGluIle-168 |
| SEQ. ID. NO. 26565 | 175-GluThrGlyGluAlaGlyGluGluAspGlyValGlyAla-187 |
| SEQ. ID. NO. 26566 | 199-SerValGluAspAlaValArgPheValLysAspThrGlyVal-212 |
| SEQ. ID. NO. 26567 | 235-AspValLeuArgIleAspArgIleLysGluIleHis-246 |
| SEQ. ID. NO. 26568 | 287-GluIleValGluGlyIleLysHisGlyValArgLysValAsnIleAspThrAspLeuArgLeu-307 |
| SEQ. ID. NO. 26569 | 320-AsnProSerAspPheAspProArgLysTyrLeu-330 |
| SEQ. ID. NO. 26570 | 333-ThrIleGluAlaMetLys-338 |
| SEQ. ID. NO. 26571 | 352-GlyGlnAlaGlyLysIleLysProValSerLeuGluLysMetAlaSerArgTyrAlaLysGlyGluLeu-374 | g036
AMPHI Regions - AMPHI

| | |
|---|---|
| SEQ. ID. NO. 26572 | 59-SerSerGlyArgPheCysGlnThrIleLysAlaAla-70 |
| SEQ. ID. NO. 26573 | 97-AlaAspGlyLeuGlnThrValSerSerAlaAla-107 |
| SEQ. ID. NO. 26574 | 142-AlaValArgArgValProArgGlnLeuArgAspSerArg-154 |
| SEQ. ID. NO. 26575 | 215-CysArgThrThrHisLysThrLeuArgProTyrAlaArgProGlnArgArg-231 |

Antigenic Index - Jameson-Wolf

| | |
|---|---|
| SEQ. ID. NO. 26576 | 16-ProAlaArgThrSerSerSerArgArgCysValProSerGlyArgCys-31 |
| SEQ. ID. NO. 26577 | 35-TyrSerSerArgAlaAspAlaThrProArgArgArgHisSerGlyAlaVal-51 |
| SEQ. ID. NO. 26578 | 55-CysSerSerAspSerSerGlyArgPhe-63 |
| SEQ. ID. NO. 26579 | 74-SerPheSerAlaArgLysThrCysSerAspGlyGluThrSerAlaAspSerAsnTrpArg-93 |
| SEQ. ID. NO. 26580 | 109-AlaAlaGlnSerAspGlyGluAlaGlyArg-118 |
| SEQ. ID. NO. 26581 | 133-SerGlyArgPheCysCysGlyArgArgAlaValArgArgValProArgGlnLeuArgAspSerArgArgArgGlyArgAlaArgGluAsnArg ArgArgSerAlaTyr-168 |
| SEQ. ID. NO. 26582 | 171-CysLeuArgArgAlaAspGlyPheProVal-180 |
| SEQ. ID. NO. 26583 | 182-ThrHisCysArgCysArgLeuLysArgArgThrProArgGlyGlyGlnCys-198 |
| SEQ. ID. NO. 26584 | 200-ProProTyrArgLeuAspAsnArgSerAsnGlyGlyGlySerAlaCysArgThrThrHisLysThrLeuArgProTyrAlaArgProGlnArg ArgValCysSer-234 |
| SEQ. ID. NO. 26585 | 239-AlaAlaArgArgArgHisArgAlaTrpGlyCysArgLeuLysAlaCysArg-255 |
| SEQ. ID. NO. 26586 | 258-LeuProAsnLeuAlaProArgArgCysArgTyrAlaVal-270 |

Hydrophilic Regions - Hopp-Woods

| | |
|---|---|
| SEQ. ID. NO. 26587 | 17-AlaArgThrSerSerSerArgArgCysValPro-27 |
| SEQ. ID. NO. 26588 | 37-SerArgAlaAspAlaThrProArgArgArgHisSerGly-49 |
| SEQ. ID. NO. 26589 | 55-CysSerSerAspSerSerGlyArg-62 |
| SEQ. ID. NO. 26590 | 76-SerAlaArgLysThrCysSerAspGlyGluThrSerAla-88 |
| SEQ. ID. NO. 26591 | 110-AlaGlnSerAspGlyGluAlaGlyArg-118 |
| SEQ. ID. NO. 26592 | 137-CysCysGlyArgArgAlaValArgArgValProArgGlnLeuArgAspSerArgArgArgGlyArgAlaArgGluAsnArgArgArgSerAlaTyr-168 |
| SEQ. ID. NO. 26593 | 171-CysLeuArgArgAlaAspGlyPhePro-179 |
| SEQ. ID. NO. 26594 | 182-ThrHisCysArgCysArgLeuLysArgArgThrProArgGlyGlyGln-197 |
| SEQ. ID. NO. 26595 | 202-TyrArgLeuAspAsnArgSerAsnGlyGly-211 |
| SEQ. ID. NO. 26596 | 213-SerAlaCysArgThrThrHisLysThrLeuArgProTyrAlaArgProGlnArgArgValCys-233 |
| SEQ. ID. NO. 26597 | 239-AlaAlaArgArgArgHisArgAlaTrp-247 |
| SEQ. ID. NO. 26598 | 251-LeuLysAlaCysArg-255 |
| SEQ. ID. NO. 26599 | 262-AlaProArgArgCysArgTyrAlaVal-270 | g038
AMPHI Regions - AMPHI

| | |
|---|---|
| SEQ. ID. NO. 26600 | 161-GlyLysLeuSerAlaValGlnGluValGluLys-171 |
| SEQ. ID. NO. 26601 | 178-AlaProIleAlaSerLeuAsn-184 |
| SEQ. ID. NO. 26602 | 195-GluPheGlyGlnPheLeuGluProValArgThrTyrArgArgGlnTyrGlyVal-212 |

Antigenic Index - Jameson-Wolf

| | |
|---|---|
| SEQ. ID. NO. 26603 | 2-ThrAspPheArgGlnAspPhe-8 |

TABLE 1-continued

| | |
|---|---|
| SEQ. ID. NO. 26604 | 22-GluPheThrThrLysAlaGlyArgArgSerPro-32 |
| SEQ. ID. NO. 26605 | 38-GlyLeuPheAsnAspGlyAlaSer-45 |
| SEQ. ID. NO. 26606 | 58-IleGluSerGlyIleArg-63 |
| SEQ. ID. NO. 26607 | 85-LeuAlaGluLysGlyVal-90 |
| SEQ. ID. NO. 26608 | 96-TyrAsnArgLysGluAlaLysAspArgGlyGluGlyGlyVal-109 |
| SEQ. ID. NO. 26609 | 125-ValIleSerAlaGlyThrSerValArgGluSerIleLysLeuIleGluAlaGluGlyAlaThr-145 |
| SEQ. ID. NO. 26610 | 153-LeuAspArgMetGluLysGlyThrGlyLysLeuSerAla-165 |
| SEQ. ID. NO. 26611 | 167-GlnGluValGluLysGlnTyrGlyLeu-175 |
| SEQ. ID. NO. 26612 | 191-GlnAsnAsnProGluPheGlyGln-198 |
| SEQ. ID. NO. 26613 | 201-GluProValArgThrTyrArgArgGlnTyrGlyValGlu-213 |

Hydrophilic Regions - Hopp-Woods

| | |
|---|---|
| SEQ. ID. NO. 26614 | 2-ThrAspPheArgGlnAspPhe-8 |
| SEQ. ID. NO. 26615 | 22-GluPheThrThrLysAlaGlyArgArgSer-31 |
| SEQ. ID. NO. 26616 | 85-LeuAlaGluLysGlyVal-90 |
| SEQ. ID. NO. 26617 | 96-TyrAsnArgLysGluAlaLysAspArgGlyGluGly-107 |
| SEQ. ID. NO. 26618 | 130-ThrSerValArgGluSerIleLysLeuIleGluAlaGluGlyAlaThr-145 |
| SEQ. ID. NO. 26619 | 153-LeuAspArgMetGluLysGlyThrGlyLys-162 |
| SEQ. ID. NO. 26620 | 167-GlnGluValGluLysGlnTyr-173 |
| SEQ. ID. NO. 26621 | 204-ArgThrTyrArgArgGlnTyrGly-211 | g040
AMPHI Regions - AMPHI

| | |
|---|---|
| SEQ. ID. NO. 26622 | 6-SerPheValAlaHisPhe-11 |
| SEQ. ID. NO. 26623 | 14-AlaAlaProTyrIleArgGlnMetArgGlyThr-24 |
| SEQ. ID. NO. 26624 | 38-GlyThrLeuAsnLysLeu-43 |
| SEQ. ID. NO. 26625 | 65-HisPheLeuAspArg-69 |
| SEQ. ID. NO. 26626 | 78-ProHisTyrCysArgGlyLeuArgValThrAspGluThr-90 |
| SEQ. ID. NO. 26627 | 95-AlaGlnGlnPheAlaGly-100 |
| SEQ. ID. NO. 26628 | 113-SerValSerGlyPheAlaArgAlaPro-121 |
| SEQ. ID. NO. 26629 | 136-MetGlyValIleAsp-140 |
| SEQ. ID. NO. 26630 | 146-TyrAlaGlyValIleArg-151 |
| SEQ. ID. NO. 26631 | 207-LeuSerAspGlyIleSerArgProAspGlyThrLeuAlaGlu-220 |
| SEQ. ID. NO. 26632 | 223-SerAlaGlnGluAlaGlnSerLeuAlaGluHisAla-234 |
| SEQ. ID. NO. 26633 | 244-SerAlaValAlaAlaLeuGluGly-251 |
| SEQ. ID. NO. 26634 | 277-IleGlyThrSerIle-281 |
| SEQ. ID. NO. 26635 | 289-IleArgGlnAlaHisSerGlyAspIleProHisIleAlaAlaLeuIleArgProLeuGlu-308 |
| SEQ. ID. NO. 26636 | 320-TyrLeuGluAsnHisIleSerGluPheSerIle-330 |
| SEQ. ID. NO. 26637 | 338-TyrGlyCysAlaAlaLeuLysThrPheAlaGluAlaAsp-350 |
| SEQ. ID. NO. 26638 | 371-ArgLeuLeuAlaHisIle-376 |
| SEQ. ID. NO. 26639 | 386-SerArgLeuPheAla-390 |

Antigenic Index - Jameson-Wolf

| | |
|---|---|
| SEQ. ID. NO. 26640 | 2-AsnAlaProAspSer-6 |
| SEQ. ID. NO. 26641 | 11-PheArgGluAlaAlaProTyrIleArgGlnMetArgGlyThrThr-25 |
| SEQ. ID. NO. 26642 | 29-GlyIleAspGlyArgLeuLeuGluGlyGlyThr-39 |
| SEQ. ID. NO. 26643 | 74-GlnGlyArgThrProHisTyrCysArgGlyLeuArgValThrAspGluThrSerLeuGlyGln-94 |
| SEQ. ID. NO. 26644 | 101-ThrValArgSerArgPheGlu-107 |
| SEQ. ID. NO. 26645 | 119-ArgAlaProSerVal-123 |
| SEQ. ID. NO. 26646 | 134-ArgProMetGlyVal-138 |
| SEQ. ID. NO. 26647 | 140-AspGlyThrAspMetGluTyr-146 |
| SEQ. ID. NO. 26648 | 150-IleArgLysThrAspThrAlaAla-157 |
| SEQ. ID. NO. 26649 | 162-LeuAspAlaGlyAsn-166 |
| SEQ. ID. NO. 26650 | 173-LeuGlyHisSerTyrGlyGlyLysThrPheAsn-183 |
| SEQ. ID. NO. 26651 | 208-SerAspGlyIleSerArgProAspGlyThrLeuAla-219 |
| SEQ. ID. NO. 26652 | 222-LeuSerAlaGlnGluAlaGlnSerLeuAla-231 |
| SEQ. ID. NO. 26653 | 234-AlaAlaSerGluThrArgArgLeuIle-242 |
| SEQ. ID. NO. 26654 | 249-LeuGluGlyGlyVal-253 |
| SEQ. ID. NO. 26655 | 261-GlyAlaAlaAspGlySerLeuLeu-268 |
| SEQ. ID. NO. 26656 | 272-PheThrArgAsnGlyIleGlyThrSerIleAlaLysGluAla-285 |
| SEQ. ID. NO. 26657 | 290-ArgGlnAlaHisSerGlyAspIle-297 |
| SEQ. ID. NO. 26658 | 305-ArgProLeuGluGluGlnGly-311 |
| SEQ. ID. NO. 26659 | 315-HisArgSerArgGluTyrLeu-321 |
| SEQ. ID. NO. 26660 | 329-SerIleLeuGluHisAspGlyAspLeuTyr-338 |
| SEQ. ID. NO. 26661 | 345-ThrPheAlaGluAlaAspCysGlyGlu-353 |
| SEQ. ID. NO. 26662 | 361-ProGlnAlaGlnAspGlyGlyTyrGlyGluArgLeu-372 |
| SEQ. ID. NO. 26663 | 377-IleAspLysAlaArgGly-382 |
| SEQ. ID. NO. 26664 | 393-ThrAsnThrGlyGlu-397 |
| SEQ. ID. NO. 26665 | 402-ArgGlyPheGlnThrAlaSerGluAspGluLeuProGluThrArgArgLysAspTyrArgSerAsnGlyArgAsnProHisIleLeu-430 |

Hydrophilic Regions - Hopp-Woods

| | |
|---|---|
| SEQ. ID. NO. 26666 | 11-PheArgGluAlaAlaPro-16 |
| SEQ. ID. NO. 26667 | 30-IleAspGlyArgLeuLeuGlu-36 |
| SEQ. ID. NO. 26668 | 84-LeuArgValThrAspGluThrSerLeu-92 |
| SEQ. ID. NO. 26669 | 102-ValArgSerArgPheGlu-107 |
| SEQ. ID. NO. 26670 | 140-AspGlyThrAspMetGluTyr-146 |
| SEQ. ID. NO. 26671 | 150-IleArgLysThrAspThrAlaAla-157 |
| SEQ. ID. NO. 26672 | 210-GlyIleSerArgProAspGlyThrLeu-218 |
| SEQ. ID. NO. 26673 | 222-LeuSerAlaGlnGluAlaGlnSerLeuAla-231 |
| SEQ. ID. NO. 26674 | 234-AlaAlaSerGluThrArgArgLeuIle-242 |
| SEQ. ID. NO. 26675 | 291-GlnAlaHisSerGlyAsp-296 |
| SEQ. ID. NO. 26676 | 305-ArgProLeuGluGluGlnGly-311 |
| SEQ. ID. NO. 26677 | 315-HisArgSerArgGluTyrLeu-321 |
| SEQ. ID. NO. 26678 | 332-GluHisAspGlyAspLeu-337 |

TABLE 1-continued

| | |
|---|---|
| SEQ. ID. NO. 26679 | 345-ThrPheAlaGluAlaAspCysGlyGlu-353 |
| SEQ. ID. NO. 26680 | 362-GlnAlaGlnAspGlyGlyTyrGlyGlu-370 |
| SEQ. ID. NO. 26681 | 377-IleAspLysAlaArgGly-382 |
| SEQ. ID. NO. 26682 | 402-ArgGlyPheGlnThrAlaSerGluAspGluLeuProGluThrArgArgLysAspTyrArgSerAsnGlyArgAsn-426 | g041-1
AMPHI Regions - AMPHI

| | |
|---|---|
| SEQ. ID. NO. 26683 | 6-AspProTyrArgHisPheGluAsnLeuAspSerAlaGluThr-19 |
| SEQ. ID. NO. 26684 | 45-AspGlyIleLeuAsnGlnMetGlnAsp-53 |
| SEQ. ID. NO. 26685 | 77-ProLysGlyValTyrArgMetCysThrAlaAla-87 |
| SEQ. ID. NO. 26686 | 102-ValAlaAspPheAspGluLeuLeu-109 |
| SEQ. ID. NO. 26687 | 117-GlyValSerHisLeuValGluGlnProAsn-126 |
| SEQ. ID. NO. 26688 | 218-MetValAsnAlaTrpArgTyrLeuAsp-226 |
| SEQ. ID. NO. 26689 | 232-IleAspLeuIleGluAlaSer-238 |
| SEQ. ID. NO. 26690 | 257-ProLeuAsnLeuProAsnAspCysAspValValGlyTyrLeu-270 |
| SEQ. ID. NO. 26691 | 317-GlnAlaLeuGluSerValGluThr-324 |
| SEQ. ID. NO. 26692 | 331-AlaSerLeuLeuGluAsnValGlnGlyArg-340 |
| SEQ. ID. NO. 26693 | 382-AspPheThrThrProLeu-387 |
| SEQ. ID. NO. 26694 | 451-GlyPheGlyIleProGluLeuProHisTyrLeuGlySerValGlyLys-466 |
| SEQ. ID. NO. 26695 | 493-AlaAlaGlnGlyIleSerLysHisLysSerValAspAspLeuLeuAlaValValArgAspLeuSerGluArg-516 |
| SEQ. ID. NO. 26696 | 519-SerSerProLysHis-523 |
| SEQ. ID. NO. 26697 | 541-ValArgGluProGlnSer-546 |
| SEQ. ID. NO. 26698 | 556-LeuThrAspMetIleArgTyr-562 |
| SEQ. ID. NO. 26699 | 571-TrpThrAspGluTyrGlyAsnProGlnLysTyrGluAlaCysLysArgArgLeuGly-589 |
| SEQ. ID. NO. 26700 | 591-LeuSerProTyrHisAsnLeuSerAspGlyIleAspTyrProPro-605 |
| SEQ. ID. NO. 26701 | 620-AlaHisAlaLeuLys-624 |
| SEQ. ID. NO. 26702 | 645-GlyHisThrGlyAsn-649 |
| SEQ. ID. NO. 26703 | 651-ThrGlnArgGluSer-655 |

Antigenic Index - Jameson-Wolf

| | |
|---|---|
| SEQ. ID. NO. 26704 | 1-MetLysSerTyrProAspProTyrArgHisPheGluAsnLeuAspSerAlaGluThrGln-20 |
| SEQ. ID. NO. 26705 | 26-AlaAsnAlaGluThrArgAlaArgPheLeuAsnAsnAspLysAlaArgAlaLeuSerAspGlyIle-47 |
| SEQ. ID. NO. 26706 | 51-MetGlnAspThrArgGlnIleProPhe-59 |
| SEQ. ID. NO. 26707 | 61-GlnGluHisArgAlaArg-66 |
| SEQ. ID. NO. 26708 | 72-GlnAsnAlaGluTyrProLysGlyVal-80 |
| SEQ. ID. NO. 26709 | 89-TyrArgSerGlyTyrProGluTrp-96 |
| SEQ. ID. NO. 26710 | 104-AspPheAspGluLeuLeuGlyAspAspValTyr-114 |
| SEQ. ID. NO. 26711 | 123-GluGlnProAsnArg-127 |
| SEQ. ID. NO. 26712 | 132-LeuAsnLysSerGlyGlyAspThr-139 |
| SEQ. ID. NO. 26713 | 145-ValAspLeuAlaGlyGluLeuValGlu-154 |
| SEQ. ID. NO. 26714 | 161-AlaGlyLysAsnHisValSerTrpArgAspGluAsnSerVal-174 |
| SEQ. ID. NO. 26715 | 178-ProAlaTrpAspGluArgGlnLeuThrGluSerGlyTyrProArgGluValTrpLeuValGluArgGlyLysSerPheGluGluSerLeuPro-208 |
| SEQ. ID. NO. 26716 | 211-GlnIleAspLysGlyAla-216 |
| SEQ. ID. NO. 26717 | 223-ArgTyrLeuAspProGlnGlySerProIleAspLeuIleGluAlaSerAspGlyPheTyr-242 |
| SEQ. ID. NO. 26718 | 249-ValSerSerGluGlyGlyAlaLysProLeuAsnLeuProAsnAspCysAspVal-266 |
| SEQ. ID. NO. 26719 | 278-LeuArgLysAspTrpHisArgAlaAsnGlnSerTyrProSer-291 |
| SEQ. ID. NO. 26720 | 298-LysLeuAsnArgGlyGluLeuGly-305 |
| SEQ. ID. NO. 26721 | 313-ProAspGluThrGlnAla-318 |
| SEQ. ID. NO. 26722 | 320-GluSerValGluThrThrLys-326 |
| SEQ. ID. NO. 26723 | 337-ValGlnGlyArgLeuLysAla-343 |
| SEQ. ID. NO. 26724 | 345-ArgPheAlaAspSerLysTrpGlnGluAlaGluLeuProHisLeuProSerGly-362 |
| SEQ. ID. NO. 26725 | 365-GluMetThrAspGlnProTrpGlyGly-373 |
| SEQ. ID. NO. 26726 | 405-GlnProGlnGlnPheValSerAspGlyIleGluVal-416 |
| SEQ. ID. NO. 26727 | 422-ValSerSerAspGlyGluArgIle-429 |
| SEQ. ID. NO. 26728 | 435-GlyLysAsnAlaAlaProAspThr-442 |
| SEQ. ID. NO. 26729 | 479-AsnIleArgGlyGlyGlyGluPheGlyProArgTrpHis-491 |
| SEQ. ID. NO. 26730 | 496-GlyIleSerLysHisLysSerValAspAsp-505 |
| SEQ. ID. NO. 26731 | 511-ArgAspLeuSerGluArgGlyMetSerSerProLysHis-523 |
| SEQ. ID. NO. 26732 | 528-GlyGlySerAsnGly-532 |
| SEQ. ID. NO. 26733 | 540-PheValArgGluProGlnSerIleGlyAla-549 |
| SEQ. ID. NO. 26734 | 568-GlySerSerTrpThrAspGluTyrGlyAsnProGlnLysTyrGluAlaCysLysArgArgLeuGlyGluLeuSerProTyr-594 |
| SEQ. ID. NO. 26735 | 596-AsnLeuSerAspGlyIleAspTyrPro-604 |
| SEQ. ID. NO. 26736 | 610-ThrSerLeuSerAspAspArgValHis-618 |
| SEQ. ID. NO. 26737 | 627-AlaLysLeuArgGluThrSerProGlnSer-636 |
| SEQ. ID. NO. 26738 | 639-TyrSerProAspGlyGlyGlyHisThrGlyAsnGlyThrGlnArgGluSerAlaAspLysLeu-659 |

Hydrophilic Regions - Hopp-Woods

| | |
|---|---|
| SEQ. ID. NO. 26739 | 3-SerTyrProAspProTyrArgHis-10 |
| SEQ. ID. NO. 26740 | 12-GluAsnLeuAspSerAlaGluThr-19 |
| SEQ. ID. NO. 26741 | 26-AlaAsnAlaGluThrArgAlaArgPheLeuAsnAsnAspLysAlaArgAlaLeuSer-44 |
| SEQ. ID. NO. 26742 | 51-MetGlnAspThrArgGln-56 |
| SEQ. ID. NO. 26743 | 61-GlnGluHisArgAlaArg-66 |
| SEQ. ID. NO. 26744 | 104-AspPheAspGluLeuLeuGly-110 |
| SEQ. ID. NO. 26745 | 134-LysSerGlyGlyAsp-138 |
| SEQ. ID. NO. 26746 | 145-ValAspLeuGluAlaGlyGluLeuValGlu-154 |
| SEQ. ID. NO. 26747 | 166-ValSerTrpArgAspGluAsnSer-173 |
| SEQ. ID. NO. 26748 | 180-TrpAspGluArgGlnLeuThr-186 |
| SEQ. ID. NO. 26749 | 198-GluArgGlyLysSerPheGluGluSerLeu-207 |
| SEQ. ID. NO. 26750 | 211-GlnIleAspLysGlyAla-216 |
| SEQ. ID. NO. 26751 | 233-AspLeuIleGluAlaSerAsp-239 |
| SEQ. ID. NO. 26752 | 250-SerSerGluGlyGlyAlaLys-256 |
| SEQ. ID. NO. 26753 | 278-LeuArgLysAspTrpHisArg-284 |
| SEQ. ID. NO. 26754 | 298-LysLeuAsnArgGlyGluLeuGly-305 |

TABLE 1-continued

| SEQ. ID. NO. 26755 | 313-ProAspGluThrGlnAla-318 |
| SEQ. ID. NO. 26756 | 320-GluSerValGluThrThrLys-326 |
| SEQ. ID. NO. 26757 | 337-ValGlnGlyArgLeuLysAla-343 |
| SEQ. ID. NO. 26758 | 347-AlaAspSerLysTrpGlnGluAlaGluLeu-356 |
| SEQ. ID. NO. 26759 | 412-AspGlyIleGluVal-416 |
| SEQ. ID. NO. 26760 | 424-SerAspGlyGluArg-428 |
| SEQ. ID. NO. 26761 | 436-LysAsnAlaAlaProAsp-441 |
| SEQ. ID. NO. 26762 | 481-ArgGlyGlyGlyGluPheGly-487 |
| SEQ. ID. NO. 26763 | 496-GlyIleSerLysHisLysSerValAspAsp-505 |
| SEQ. ID. NO. 26764 | 511-ArgAspLeuSerGluArgGlyMetSerSer-520 |
| SEQ. ID. NO. 26765 | 540-PheValArgGluProGlnSer-546 |
| SEQ. ID. NO. 26766 | 571-TrpThrAspGluTyrGlyAsn-577 |
| SEQ. ID. NO. 26767 | 579-GlnLysTyrGluAlaCysLysArgArgLeuGlyGlu-590 |
| SEQ. ID. NO. 26768 | 612-LeuSerAspAspArgValHis-618 |
| SEQ. ID. NO. 26769 | 627-AlaLysLeuArgGluThrSer-633 |
| SEQ. ID. NO. 26770 | 650-GlyThrGlnArgGluSerAlaAspLysLeu-659 | g042
AMPHI Regions - AMPHI

| SEQ. ID. NO. 26771 | 18-LeuSerAsnThrSerThr-23 |
| SEQ. ID. NO. 26772 | 33-AlaValArgSerMet-37 |
| SEQ. ID. NO. 26773 | 138-SerProLeuValArgIleLeuProLeuSer-147 |
| SEQ. ID. NO. 26774 | 151-SerMetValValAlaPhePheAlaAsn-159 |

Antigenic Index - Jameson-Wolf

| SEQ. ID. NO. 26775 | 16-SerAlaLeuSerAsnThrSerThrAlaAlaGlyProSerCys-29 |
| SEQ. ID. NO. 26776 | 49-TyrSerLysGluThrGlyCysProCysProSerLeuArgLysAspSerSerThrGlyGlyArgProMetSerProCys-74 |
| SEQ. ID. NO. 26777 | 77-LeuAlaAsnArgAspCysValProLysAlaAspThr-88 |
| SEQ. ID. NO. 26778 | 93-ThrAspSerThrSerProArgProLeu-101 |
| SEQ. ID. NO. 26779 | 109-TrpAlaAsnSerAlaSer-114 |
| SEQ. ID. NO. 26780 | 120-SerAlaThrArgAlaSerLeuProLysIleArgAspArgVal-133 |
| SEQ. ID. NO. 26781 | 160-CysSerTyrAlaSerAlaProGlyPro-168 |
| SEQ. ID. NO. 26782 | 175-GlyLeuTrpArgCysArgAspSerGlnSerGlySerAsnSer-188 |
| SEQ. ID. NO. 26783 | 197-AsnAlaGlyCysLys-201 |

Hydrophilic Regions - Hopp-Woods

| SEQ. ID. NO. 26784 | 49-TyrSerLysGluThrGlyCys-55 |
| SEQ. ID. NO. 26785 | 59-SerLeuArgLysAspSerSerThrGlyGlyArgProMet-71 |
| SEQ. ID. NO. 26786 | 78-AlaAsnArgAspCysValProLysAlaAspThr-88 |
| SEQ. ID. NO. 26787 | 94-AspSerThrSerProArg-99 |
| SEQ. ID. NO. 26788 | 122-ThrArgAlaSerLeuProLysIleArgAspArgVal-133 |
| SEQ. ID. NO. 26789 | 178-ArgCysArgAspSerGlnSerGly-185 | g043-2
AMPHI Regions - AMPHI

| SEQ. ID. NO. 26790 | 21-GluArgPheValGluProSerArg-28 |
| SEQ. ID. NO. 26791 | 34-LysValHisArgGlyLeuAspGlyAlaAlaArgPheAspGluGlyGluArg-50 |
| SEQ. ID. NO. 26792 | 59-AlaSerGlyAspGlyPhe-64 |
| SEQ. ID. NO. 26793 | 81-AspAlaAlaGlyAspPheGlyAspGlyGlnArg-91 |
| SEQ. ID. NO. 26794 | 98-GlnAsnIleGlyGlyPheValTyr-105 |

Antigenic Index - Jameson-Wolf

| SEQ. ID. NO. 26795 | 1-MetProSerAlaPro-5 |
| SEQ. ID. NO. 26796 | 12-ArgArgGlnLysSerValMetProProGluArgPheValGluProSerArg-28 |
| SEQ. ID. NO. 26797 | 34-LysValHisArgGlyLeuAspGlyAlaAlaArgPheAspGluGlyGluArgValPhe-52 |
| SEQ. ID. NO. 26798 | 56-AlaAlaGlnAlaSerGlyAspGlyPheAla-65 |
| SEQ. ID. NO. 26799 | 79-GlnProAspAlaAlaGlyAspPheGlyAspGlyGlnArgAlaGlyGlu-94 |
| SEQ. ID. NO. 26800 | 116-AlaGluGlyGluAla-120 |

Hydrophilic Regions - Hopp-Woods

| SEQ. ID. NO. 26801 | 12-ArgArgGlnLysSerValMetProProGluArgPheValGluProSerArg-28 |
| SEQ. ID. NO. 26802 | 34-LysValHisArgGlyLeuAspGlyAlaAlaArgPheAspGluGlyGluArgValPhe-52 |
| SEQ. ID. NO. 26803 | 81-AspAlaAlaGlyAspPheGlyAspGlyGlnArgAlaGlyGlu-94 |
| SEQ. ID. NO. 26804 | 116-AlaGluGlyGluAla-120 | g046
AMPHI Regions - AMPHI

| SEQ. ID. NO. 26805 | 6-ArgProThrSerSerPro-11 |
| SEQ. ID. NO. 26806 | 46-ThrSerCysSerGlyLeuMetValSer-54 |
| SEQ. ID. NO. 26807 | 64-PheSerLeuPheSerSer-69 |
| SEQ. ID. NO. 26808 | 113-LysSerAlaSerSer-117 |
| SEQ. ID. NO. 26809 | 143-SerCysAsnAlaPheSerSer-149 |

Antigenic Index - Jameson-Wolf

| SEQ. ID. NO. 26810 | 6-ArgProThrSerSerProProArgArgAlaCys-16 |
| SEQ. ID. NO. 26811 | 20-IleArgThrArgSerSerAlaLysArgLysThrCysAsnAlaProGlyGlnSerIleArgProAlaSerCysSer-44 |
| SEQ. ID. NO. 26812 | 57-ProAsnMetGluArgLeuPro-63 |
| SEQ. ID. NO. 26813 | 75-SerArgTyrSerLeuGluArgThrArgAlaMetArgProGlyMetLeuAsnArgSerAlaAla-95 |
| SEQ. ID. NO. 26814 | 105-SerLeuArgGluSerAlaSerSerLysSerAlaSerSerAlaProAlaArgTyrAsnValLysGlyAspAlaProLeuPro-131 |
| SEQ. ID. NO. 26815 | 133-ThrValTrpThrSerArgArgLeuProVal-142 |
| SEQ. ID. NO. 26816 | 169-GluProThrCysProLeuProLys-176 |

Hydrophilic Regions - Hopp-Woods

| SEQ. ID. NO. 26817 | 7-ProThrSerSerProProArgArgAlaCys-16 |
| SEQ. ID. NO. 26818 | 20-IleArgThrArgSerSerAlaLysArgLysThrCysAsn-32 |
| SEQ. ID. NO. 26819 | 36-GlnSerIleArgProAlaSer-42 |
| SEQ. ID. NO. 26820 | 58-AsnMetGluArgLeuPro-63 |
| SEQ. ID. NO. 26821 | 75-SerArgTyrSerLeuGluArgThrArgAlaMetArg-86 |
| SEQ. ID. NO. 26822 | 105-SerLeuArgGluSerAlaSerSerLysSerAlaSer-116 |

TABLE 1-continued

| | |
|---|---|
| SEQ. ID. NO. 26823 | 122-TyrAsnValLysGlyAspAlaProLeu-130 | g047
AMPHI Regions - AMPHI

| | |
|---|---|
| SEQ. ID. NO. 26824 | 17-IleAlaAspIleAlaGlnAspLeuProAspGlyAla-28 |
| SEQ. ID. NO. 26825 | 62-AlaGluAsnIleGlyAlaVal-68 |
| SEQ. ID. NO. 26826 | 89-AsnIleCysTyrArgLeuAlaLysGlnLeuGlu-99 |
| SEQ. ID. NO. 26827 | 141-TyrIleAspGluIleAspValPhe-148 |
| SEQ. ID. NO. 26828 | 161-SerAlaLeuLeuAla-165 |
| SEQ. ID. NO. 26829 | 185-LeuLeuGluGlyAsn-189 |
| SEQ. ID. NO. 26830 | 202-IleGlySerIleLeuAla-207 |
| SEQ. ID. NO. 26831 | 247-SerGlyIleLysTrpProGluGlyCys-255 |
| SEQ. ID. NO. 26832 | 257-IleAlaAlaValValArgAlaGlyThrGly-266 |
| SEQ. ID. NO. 26833 | 293-IleLeuAsnGluLeuGluLysLeuIle-301 |

Antigenic Index - Jameson-Wolf

| | |
|---|---|
| SEQ. ID. NO. 26834 | 5-GlnAlaArgArgGlyGlyLeuLeu-12 |
| SEQ. ID. NO. 26835 | 20-IleAlaGlnAspLeuProAspGlyAlaAsp-29 |
| SEQ. ID. NO. 26836 | 36-TyrArgAsnAsnArgLeu-41 |
| SEQ. ID. NO. 26837 | 51-IleGluGlyAspGlu-55 |
| SEQ. ID. NO. 26838 | 70-ProGluLeuArgProLysGluThrSerThrArgArgIleMet-83 |
| SEQ. ID. NO. 26839 | 96-LysGlnLeuGluHis-100 |
| SEQ. ID. NO. 26840 | 106-IleIleGluCysArgProArgArgAlaGluTrpIle-117 |
| SEQ. ID. NO. 26841 | 119-GluAsnLeuAspAsnThrLeu-125 |
| SEQ. ID. NO. 26842 | 130-SerAlaThrAspGluThrLeuLeuAspAsnGluTyrIleAspGluIleAsp-146 |
| SEQ. ID. NO. 26843 | 152-ThrAsnAspAspGluSerAsnIle-159 |
| SEQ. ID. NO. 26844 | 168-LeuGlyAlaLysArgVal-173 |
| SEQ. ID. NO. 26845 | 178-AsnArgSerSerTyr-182 |
| SEQ. ID. NO. 26846 | 186-LeuGluGlyAsnLysIle-191 |
| SEQ. ID. NO. 26847 | 208-HisIleArgArgGlyAspIleVal-215 |
| SEQ. ID. NO. 26848 | 219-ProIleArgArgGlyThrAlaGluAlaIleGlu-229 |
| SEQ. ID. NO. 26849 | 232-AlaHisGlyAspLysLysThrSer-239 |
| SEQ. ID. NO. 26850 | 242-IleGlyArgArgIleSerGlyIleLysTrpProGlyGlyCysHis-256 |
| SEQ. ID. NO. 26851 | 262-ArgAlaGlyThrGlyGluThr-268 |
| SEQ. ID. NO. 26852 | 277-ValIleGlnAspGlyAspHis-283 |
| SEQ. ID. NO. 26853 | 288-ValSerArgArgArgIleLeuAsnGluLeuGluLys-299 |

Hydrophilic Regions - Hopp-Woods

| | |
|---|---|
| SEQ. ID. NO. 26854 | 5-GlnAlaArgArgGlyGly-10 |
| SEQ. ID. NO. 26855 | 20-IleAlaGlnAspLeuProAspGlyAlaAsp-29 |
| SEQ. ID. NO. 26856 | 51-IleGluGlyAspGlu-55 |
| SEQ. ID. NO. 26857 | 70-ProGluLeuArgProLysGluThrSerThrArgArgIleMet-83 |
| SEQ. ID. NO. 26858 | 106-IleIleGluCysArgProArgArgAlaGluTrpIle-117 |
| SEQ. ID. NO. 26859 | 130-SerAlaThrAspGluThrLeuLeu-137 |
| SEQ. ID. NO. 26860 | 140-GluTyrIleAspGluIleAsp-146 |
| SEQ. ID. NO. 26861 | 152-ThrAsnAspAspGluSerAsnIle-159 |
| SEQ. ID. NO. 26862 | 168-LeuGlyAlaLysArgVal-173 |
| SEQ. ID. NO. 26863 | 186-LeuGluGlyAsnLysIle-191 |
| SEQ. ID. NO. 26864 | 209-IleArgArgGlyAspIle-214 |
| SEQ. ID. NO. 26865 | 219-ProIleArgArgGlyThrAlaGluAlaIleGlu-229 |
| SEQ. ID. NO. 26866 | 232-AlaHisGlyAspLysLysThrSer-239 |
| SEQ. ID. NO. 26867 | 242-IleGlyArgArgIleSer-247 |
| SEQ. ID. NO. 26868 | 277-ValIleGlnAspGlyAsp-282 |
| SEQ. ID. NO. 26869 | 289-SerArgArgArgIleLeuAsnGluLeuGluLys-299 | g049-2
AMPHI Regions - AMPHI

| | |
|---|---|
| SEQ. ID. NO. 26870 | 15-GlnHisLeuLeuGlu-19 |
| SEQ. ID. NO. 26871 | 34-AspHisAlaValAspGlyIleGlyGlnMet-43 |
| SEQ. ID. NO. 26872 | 50-GlnProPheGlyGln-54 |
| SEQ. ID. NO. 26873 | 61-GluHisPheAlaProValAspGlyPheArg-70 |
| SEQ. ID. NO. 26874 | 103-IleGlyValPheProAlaLeu-109 |
| SEQ. ID. NO. 26875 | 199-SerAspPheArgArg-203 |
| SEQ. ID. NO. 26876 | 217-AlaArgLeuThrGlnValPheGlnAlaPhePhe-227 |
| SEQ. ID. NO. 26877 | 241-ValLeuAsnLeuCysArgArgAla-248 |

Antigenic Index - Jameson-Wolf

| | |
|---|---|
| SEQ. ID. NO. 26878 | 6-PheAspTyrArgThrArgLeu-12 |
| SEQ. ID. NO. 26879 | 21-IleSerLysGluArgHis-26 |
| SEQ. ID. NO. 26880 | 31-ArgArgThrAspHisAlaValAspGly-39 |
| SEQ. ID. NO. 26881 | 49-AspGlnProPheGly-53 |
| SEQ. ID. NO. 26882 | 64-AlaProValAspGlyPheArgValGlnAspIleAspLeuAspGlyHisGlnArgLeuPhe-83 |
| SEQ. ID. NO. 26883 | 90-PheArgAsnProValCysArgArgThrGlyPhe-100 |
| SEQ. ID. NO. 26884 | 122-GlyIleGluProAspSerProProArgPhe-131 |
| SEQ. ID. NO. 26885 | 135-PheArgAsnArgHisLeuGlnGlySerLeuArgVal-146 |
| SEQ. ID. NO. 26886 | 150-PheLeuLysAspAspHisArgValGly-158 |
| SEQ. ID. NO. 26887 | 199-SerAspPheArgArgPheGlyGlnArgHisIleGlyArgArgGlyIleHis-215 |
| SEQ. ID. NO. 26888 | 244-LeuCysArgArgAlaAsnProArgProLysArgSerLeu-256 |

Hydrophilic Regions - Hopp-Woods

| | |
|---|---|
| SEQ. ID. NO. 26889 | 21-IleSerLysGluArgHis-26 |
| SEQ. ID. NO. 26890 | 31-ArgArgThrAspHisAlaVal-37 |
| SEQ. ID. NO. 26891 | 67-AspGlyPheArgValGlnAspIleAspLeuAspGlyHisGlnArgLeuPhe-83 |
| SEQ. ID. NO. 26892 | 93-ProValCysArgArgThrGlyPhe-100 |
| SEQ. ID. NO. 26893 | 124-GluProAspSerProProArg-130 |
| SEQ. ID. NO. 26894 | 150-PheLeuLysAspAspHisArgVal-157 |

TABLE 1-continued

| | |
|---|---|
| SEQ. ID. NO. 26895 | 200-AspPheArgArgPheGlyGln-206 |
| SEQ. ID. NO. 26896 | 208-HisIleGlyArgArgGlyIleHis-215 |
| SEQ. ID. NO. 26897 | 244-LeuCysArgArgAlaAsnProArgProLysArgSerLeu-256 | g050-1
AMPHI Regions - AMPHI

| | |
|---|---|
| SEQ. ID. NO. 26898 | 10-IleGlnSerIleCysAspAlaPheGlnPheIleSerTyrTyr-23 |
| SEQ. ID. NO. 26899 | 25-ProLysAspTyrIleAspAlaLeuTyrLysAlaTrpGlnLys-38 |
| SEQ. ID. NO. 26900 | 94-ValAsnGluGlyVal-98 |
| SEQ. ID. NO. 26901 | 163-AsnProSerAspAsnIleValAspTrpValLeuLys-174 |
| SEQ. ID. NO. 26902 | 177-ProThrMetGlyAla-181 |
| SEQ. ID. NO. 26903 | 235-LeuGluLeuPheGluLysValAsnAla-243 |
| SEQ. ID. NO. 26904 | 250-GlyLeuGlyGlyLeuThrThr-256 |
| SEQ. ID. NO. 26905 | 275-AlaMetIleProAsn-279 |
| SEQ. ID. NO. 26906 | 315-AsnGlyLysArgValAspValAsp-322 |
| SEQ. ID. NO. 26907 | 353-LysArgLeuValAsMetLeuAspLys-361 |
| SEQ. ID. NO. 26908 | 367-ValAspPheThrAsnArgLeu-373 |
| SEQ. ID. NO. 26909 | 379-ProValAspProValGlyAspGlu-386 |
| SEQ. ID. NO. 26910 | 396-AlaThrArgMetAspLysPheThrArgGlnMet-406 |
| SEQ. ID. NO. 26911 | 452-LysSerSerLysValLeuAlaPhe-459 |
| SEQ. ID. NO. 26912 | 490-AlaThrAlaProArgLysTrp-496 |

Antigenic Index - Jameson-Wolf

| | |
|---|---|
| SEQ. ID. NO. 26913 | 4-IleLysGlnGluAspPheIle-10 |
| SEQ. ID. NO. 26914 | 23-TyrHisProLysAspTyrIleAspAlaLeu-32 |
| SEQ. ID. NO. 26915 | 36-TrpGlnLysGluGluAsnProAlaAlaLysAspAlaMet-48 |
| SEQ. ID. NO. 26916 | 55-SerArgMetCysAlaGluAsnAsnArgProIleCysGlnAspThrGly-70 |
| SEQ. ID. NO. 26917 | 88-MetSerValGluLysMetValAsnGluGlyValArgArgAlaTyrThrTrpGluGlyAsnThrLeuArgAlaSerVal-113 |
| SEQ. ID. NO. 26918 | 116-AspProAlaGlyLysArgGlnAsnThrLysAspAsnThr-128 |
| SEQ. ID. NO. 26919 | 138-ProGlyGlyLysValGluVal-144 |
| SEQ. ID. NO. 26920 | 148-AlaLysGlyGlyGlySerGluAsnLysSerLysLeu-159 |
| SEQ. ID. NO. 26921 | 163-AsnProSerAspAsnIle-168 |
| SEQ. ID. NO. 26922 | 192-GlyIleGlyGlyThrProGluLysAlaValLeuMetAlaLysGluSerLeu-208 |
| SEQ. ID. NO. 26923 | 213-AspIleGlnGluLeuGlnGluLysAlaAlaSerGlyAlaGluLeuSerThr-229 |
| SEQ. ID. NO. 26924 | 284-ArgHisValGluPheGluLeuAspGlySerGlyProValGluLeuThrProProArgValGluAspXxxProAspLeuThrTyrSerProAsp AsnGlyLysArgValAspValAspLysLeuThrLysGluGluValAlaSer |
| SEQ. ID. NO. 26925 | LysThrGlyAsp-336 |
| SEQ. ID. NO. 26926 | 345-LeuThrGlyArgAspAlaAlaHisLysArgLeu-355 |
| SEQ. ID. NO. 26927 | 359-LeuAspLysGlyGluGluLeuPro-366 |
| SEQ. ID. NO. 26928 | 379-ProValAspProValGlyAspGluValValGlyProAlaGlyProThrThrAlaThrArgMetAspLysPheThrArgGlnMetLeu-407 |
| SEQ. ID. NO. 26929 | 416-IleGlyLysSerGluArgGlyAlaAlaThr-425 |
| SEQ. ID. NO. 26930 | 428-AlaIleAlaAspAsnLysAla-434 |
| SEQ. ID. NO. 26931 | 450-AlaIleLysSerSerLys-455 |
| SEQ. ID. NO. 26932 | 470-PheGluValLysAspMetPro-476 |
| SEQ. ID. NO. 26933 | 481-ValAspSerLysGlyGluSerIle-488 |
| SEQ. ID. NO. 26934 | 492-AlaProArgLysTrpGlnAla-498 |

Hydrophilic Regions - Hopp-Woods

| | |
|---|---|
| SEQ. ID. NO. 26935 | 4-IleLysGlnGluAspPheIle-10 |
| SEQ. ID. NO. 26936 | 36-TrpGlnLysGluGluAsnProAlaAlaLysAspAlaMet-48 |
| SEQ. ID. NO. 26937 | 57-MetCysAlaGluAsnAsnArgProIleCys-66 |
| SEQ. ID. NO. 26938 | 88-MetSerValGluLysMetValAsnGluGlyValArgArg-100 |
| SEQ. ID. NO. 26939 | 117-ProAlaGlyLysArgGlnAsnThrLysAspAsnThr-128 |
| SEQ. ID. NO. 26940 | 140-GlyLysValGluVal-144 |
| SEQ. ID. NO. 26941 | 148-AlaLysGlyGlyGlySerGluAsnLysSerLysLeu-159 |
| SEQ. ID. NO. 26942 | 195-GlyThrProGluLysAlaValLeuMetAlaLysGluSerLeu-208 |
| SEQ. ID. NO. 26943 | 213-AspIleGlnGluLeuGlnGluLysAlaAlaSer-223 |
| SEQ. ID. NO. 26944 | 225-AlaGluLeuSerThr-229 |
| SEQ. ID. NO. 26945 | 284-ArgHisValGluPheGluLeuAspGly-292 |
| SEQ. ID. NO. 26946 | 299-ThrProProArgValGluAspXxxProAsp-308 |
| SEQ. ID. NO. 26947 | 313-ProAspAsnGlyLysArgValAspValAspLysLeuThrLysGluGluValAlaSer-331 |
| SEQ. ID. NO. 26948 | 345-LeuThrGlyArgAspAlaAlaHisLysArgLeu-355 |
| SEQ. ID. NO. 26949 | 359-LeuAspLysGlyGluGluLeuPro-366 |
| SEQ. ID. NO. 26950 | 382-ProValGlyAspGluValVal-388 |
| SEQ. ID. NO. 26951 | 397-ThrArgMetAspLysPheThrArgGlnMetLeu-407 |
| SEQ. ID. NO. 26952 | 417-GlyLysSerGluArgGlyAlaAlaThr-425 |
| SEQ. ID. NO. 26953 | 428-AlaIleAlaAspAsnLysAla-434 |
| SEQ. ID. NO. 26954 | 450-AlaIleLysSerSerLys-455 |
| SEQ. ID. NO. 26955 | 470-PheGluValLysAspMetPro-476 |
| SEQ. ID. NO. 26956 | 481-ValAspSerLysGlyGluSerIle-488 |
| SEQ. ID. NO. 26957 | 492-AlaProArgLysTrpGlnAla-498 | g052
AMPHI Regions - AMPHI

| | |
|---|---|
| SEQ. ID. NO. 26958 | 12-AlaProCysPheLysGlyCysGluProThrGlyAsp-23 |
| SEQ. ID. NO. 26959 | 41-AlaLysAlaSerLysSerAlaThrSerProLysGlyLeuAspGlyValSerLys-58 |
| SEQ. ID. NO. 26960 | 67-ThrAlaAlaPheHisSerPheIleSer-75 |
| SEQ. ID. NO. 26961 | 84-MetProAsnLeuValThrMetLeu-91 |

Antigenic Index - Jameson-Wolf

| | |
|---|---|
| SEQ. ID. NO. 26962 | 4-ValAlaGluGluThrGluIle-10 |
| SEQ. ID. NO. 26963 | 14-CysPheLysGlyCysGluProThrGlyAspSerArgLeuLeuSerThrThrLysSerAlaPro-34 |
| SEQ. ID. NO. 26964 | 37-CysAlaAsnSerAlaLysAlaSerLysSerAlaThrSerProLysGlyLeuAspGlyValSerLysAsnSerSer-61 |
| SEQ. ID. NO. 26965 | 75-SerValGlyAspThrArgLeuThrProMet-84 |
| SEQ. ID. NO. 26966 | 97-ValValProAsnArgLeuArgLeuGluThrThrTrpSerProAlaCysArgLysValLysAsnAlaAla-119 |

TABLE 1-continued

```
Hydrophilic Regions - Hopp-Woods
SEQ. ID. NO. 26967    4-ValAlaGluGluThrGluIle-10
SEQ. ID. NO. 26968    16-LysGlyCysGluProThrGlyAspSerArgLeu-26
SEQ. ID. NO. 26969    30-ThrLysSerAlaPro-34
SEQ. ID. NO. 26970    39-AsnSerAlaLysAlaSerLysSerAlaThrSerProLysGlyLeuAspGlyValSerLysAsnSer-60
SEQ. ID. NO. 26971    77-GlyAspThrArgLeu-81
SEQ. ID. NO. 26972    100-AsnArgLeuArgLeu-104
SEQ. ID. NO. 26973    111-AlaCysArgLysValLysAsnAlaAla-119
g075-2
AMPHI Regions - AMPHI
SEQ. ID. NO. 26974    15-LysSerAlaAlaLysThrProThrThrIleGlnProAlaSerIleProSer-31
SEQ. ID. NO. 26975    65-AlaProTyrLeuArgGlnValLeu-72
SEQ. ID. NO. 26976    80-PheLysLysCysLeuAla-85
SEQ. ID. NO. 26977    92-PheArgArgProProAsn-97
SEQ. ID. NO. 26978    114-ValAlaAspPhePheGlnThrCysValAsnArgPhePheGluValValGluIleIleGlyIleGly-135
Antigenic Index - Jameson-Wolf
SEQ. ID. NO. 26979    12-GluAsnThrLysSerAlaAlaLysThrProThr-22
SEQ. ID. NO. 26980    25-GlnProAlaSerIlePro-30
SEQ. ID. NO. 26981    52-AlaLysAlaSerGly-56
SEQ. ID. NO. 26982    90-GluPhePheArgArgProProAsnIleArgLysSerValPheGlnLysSerGluTyrAspLys-110
Hydrophilic Regions - Hopp-Woods
SEQ. ID. NO. 26983    12-GluAsnThrLysSerAlaAlaLysThr-20
SEQ. ID. NO. 26984    52-AlaLysAlaSerGly-56
SEQ. ID. NO. 26985    90-GluPhePheArgArgProProAsnIleArgLysSerValPheGlnLysSerGluTyrAspLys-110
g080-2
AMPHI Regions - AMPHI
SEQ. ID. NO. 26986    6-GluAlaMetGluArgLeuThrArg-13
SEQ. ID. NO. 26987    95-PheProAspThrValGlu-100
SEQ. ID. NO. 26988    108-ProValAlaArgTrpGlyAspHis-115
SEQ. ID. NO. 26989    144-SerAlaGluMetLeuArgArgTyrAspGluPheSerThrValLeu-158
SEQ. ID. NO. 26990    195-LysArgLeuArgLeuPheThrGluAlaTrpGlnHis-206
Antigenic Index - Jameson-Wolf
SEQ. ID. NO. 26991    1-MetTrpAspAsnAlaGluAlaMetGluArgLeuThr-12
SEQ. ID. NO. 26992    33-AsnSerAsnHisLeuPro-38
SEQ. ID. NO. 26993    42-ValSerLeuLysGly-46
SEQ. ID. NO. 26994    50-TyrSerAspLysLysAlaLeu-56
SEQ. ID. NO. 26995    67-AsnIleLeuArgThrAspIleAsnGlyAlaGlnGluAlaTyrArg-81
SEQ. ID. NO. 26996    90-MetValArgArgArgPheProAspThrValGlu-100
SEQ. ID. NO. 26997    103-LeuThrGluArgLysProValAlaArgTrpGly-113
SEQ. ID. NO. 26998    116-AlaLeuValAspGlyGluGlyAsnValPhe-125
SEQ. ID. NO. 26999    127-AlaArgLeuAspArgProGlyMetPro-135
SEQ. ID. NO. 27000    138-ArgGlyAlaGluGlyThrSer-144
SEQ. ID. NO. 27001    146-GluMetLeuArgArgTyrAspGlu-153
SEQ. ID. NO. 27002    163-LeuGlyIleLysGlu-167
SEQ. ID. NO. 27003    180-LeuAspAsnGlyIle-184
SEQ. ID. NO. 27004    187-ArgLeuGlyArgGluAsnGluMetLysArgLeuArgLeu-199
SEQ. ID. NO. 27005    207-LeuLeuArgLysAsnLysAsnArgLeuSer-216
SEQ. ID. NO. 27006    220-MetArgTyrLysAspGlyPheSerVal-228
SEQ. ID. NO. 27007    230-HisAlaProAspGlyLeuProGluLysGluSerGluGlu-242
Hydrophilic Regions - Hopp-Woods
SEQ. ID. NO. 27008    3-AspAsnAlaGluAlaMetGluArgLeuThr-12
SEQ. ID. NO. 27009    50-TyrSerAspLysLysAlaLeu-56
SEQ. ID. NO. 27010    69-LeuArgThrAspIleAsnGlyAlaGlnGluAlaTyrArg-81
SEQ. ID. NO. 27011    90-MetValArgArgArgPheProAspThrVal-99
SEQ. ID. NO. 27012    103-LeuThrGluArgLysProValAlaArgTrpGly-113
SEQ. ID. NO. 27013    116-AlaLeuValAspGlyGluGlyAsnValPhe-125
SEQ. ID. NO. 27014    127-AlaArgLeuAspArgProGly-133
SEQ. ID. NO. 27015    138-ArgGlyAlaGluGlyThrSer-144
SEQ. ID. NO. 27016    146-GluMetLeuArgArgTyrAspGlu-153
SEQ. ID. NO. 27017    163-LeuGlyIleLysGlu-167
SEQ. ID. NO. 27018    187-ArgLeuGlyArgGluAsnGluMetLysArgLeuArgLeu-199
SEQ. ID. NO. 27019    208-LeuArgLysAsnLysAsnArgLeuSer-216
SEQ. ID. NO. 27020    220-MetArgTyrLysAspGlyPheSer-227
SEQ. ID. NO. 27021    230-HisAlaProAspGlyLeuProGluLysGluSerGluGlu-242
g081
AMPHI Regions - AMPHI
SEQ. ID. NO. 27022    22-LysProValSerArgIleValThrAspSerArgAspIleArg-35
SEQ. ID. NO. 27023    54-ValGlyGlyValLeuSer-59
SEQ. ID. NO. 27024    78-AlaLeuLysValAspAsp-83
SEQ. ID. NO. 27025    85-LeuAlaAlaLeuGlnThrLeuAlaLysAlaTrpArgAspAsn-98
SEQ. ID. NO. 27026    116-LysGluMetLeuAlaAlaValLeuArg-124
SEQ. ID. NO. 27027    130-AspAlaValSerAla-134
SEQ. ID. NO. 27028    165-MetAsnHisPheGlyGluLeuAlaValLeuThrGlnIleAlaLys-179
SEQ. ID. NO. 27029    186-AsnAsnAlaLeuArg-190
SEQ. ID. NO. 27030    198-AspGlyValGlyAspIleAlaLysAla-206
SEQ. ID. NO. 27031    303-LeuAsnAspValAlaGluGlyLeuGlnGlyPheSerAsn-315
SEQ. ID. NO. 27032    345-AlaAlaValAspValLeuAlaArgMetPro-354
SEQ. ID. NO. 27033    360-ValMetGlyAspMetGlyGluLeuGlyGlu-369
SEQ. ID. NO. 27034    399-ValGluAlaAlaGlu-403
```

TABLE 1-continued

Antigenic Index - Jameson-Wolf
SEQ. ID. NO. 27035    15-LeuProMetProSerGluAsnLysProValSer-25
SEQ. ID. NO. 27036    27-IleValThrAspSerArgAspIleArgGluGlyAsp-38
SEQ. ID. NO. 27037    44-AlaGlyGlyArgPheAspAla-50
SEQ. ID. NO. 27038    67-ValSerArgGluAspCysAla-73
SEQ. ID. NO. 27039    79-LeuLysValAspAspThrLeu-85
SEQ. ID. NO. 27040    94-AlaTrpArgAspAsnValAsnProPhe-102
SEQ. ID. NO. 27041    102-GlySerGlyGlyLysThrThrValLysGluMetLeu-119
SEQ. ID. NO. 27042    123-LeuArgArgArgPheGlyAspAspAlaVal-132
SEQ. ID. NO. 27043    138-AsnPheAsnAsnHisIle-143
SEQ. ID. NO. 27044    151-LysLeuAsnGluLysHisArg-157
SEQ. ID. NO. 27045    178-AlaLysProAspAla-182
SEQ. ID. NO. 27046    194-GlyCysGlyPheAspGlyValGlyAspIleAlaLysAlaLysSerGluIle-210
SEQ. ID. NO. 27047    223-ProGlnGluAspAlaAsn-228
SEQ. ID. NO. 27048    245-GlyValAspSerGlyAspValArgAlaGluAsnIleVal-257
SEQ. ID. NO. 27049    269-CysGlyAspGluArgThrAla-275
SEQ. ID. NO. 27050    280-ValProGlyArgHisAsnVal-286
SEQ. ID. NO. 27051    314-SerAsnIleLysGlyArgLeuAsnVal-322
SEQ. ID. NO. 27052    330-ThrLeuIleAspAspThrTyrAsnAlaAsnProAspSerMetLysAlaAlaVal-347
SEQ. ID. NO. 27053    363-AspMetGlyGluLeuGlyGluAspGluAlaAla-373
SEQ. ID. NO. 27054    381-AlaTyrAlaArgAspGlnGlyIle-388
SEQ. ID. NO. 27055    395-GlyAspAsnSerValGluAlaAlaGluLysPheGlyAla-407
SEQ. ID. NO. 27056    425-AspLeuProGluArgAlaThrVal-432
SEQ. ID. NO. 27057    434-ValLysGlySerArg-438
SEQ. ID. NO. 27058    443-GluGluValValGluAlaLeuGluAspLys-452
Hydrophilic Regions - Hopp-Woods
SEQ. ID. NO. 27059    17-MetProSerGluAsnLysProValSer-25
SEQ. ID. NO. 27060    27-IleValThrAspSerArgAspIleArgGluGlyAsp-38
SEQ. ID. NO. 27061    46-GlyArgPheAspAla-50
SEQ. ID. NO. 27062    67-ValSerArgGluAspCysAla-73
SEQ. ID. NO. 27063    79-LeuLysValAspAspThrLeu-85
SEQ. ID. NO. 27064    94-AlaTrpArgAspAsnVal-99
SEQ. ID. NO. 27065    109-SerGlyLysThrThrValLysGluMetLeu-119
SEQ. ID. NO. 27066    123-LeuArgArgArgPheGlyAspAspAlaVal-132
SEQ. ID. NO. 27067    151-LysLeuAsnGluLysHisArg-157
SEQ. ID. NO. 27068    178-AlaLysProAspAla-182
SEQ. ID. NO. 27069    199-GlyValGlyAspIleAlaLysAlaLysSerGluIle-210
SEQ. ID. NO. 27070    223-ProGlnGluAspAlaAsn-228
SEQ. ID. NO. 27071    247-AspSerGlyAspValArgAlaGluAsnIleVal-257
SEQ. ID. NO. 27072    269-CysGlyAspGluArgThrAla-275
SEQ. ID. NO. 27073    316-IleLysGlyArgLeuAsnVal-322
SEQ. ID. NO. 27074    335-ThrTyrAsnAlaAsnProAspSerMetLysAlaAlaVal-347
SEQ. ID. NO. 27075    363-AspMetGlyGluLeuGlyGluAspGluAlaAla-373
SEQ. ID. NO. 27076    381-AlaTyrAlaArgAspGlnGlyIle-388
SEQ. ID. NO. 27077    397-AsnSerValGluAlaAlaGluLysPheGlyAla-407
SEQ. ID. NO. 27078    425-AspLeuProGluArgAlaThrVal-432
SEQ. ID. NO. 27079    443-GluGluValValGluAlaLeuGluAspLys-452
g084-2
AMPHI Regions - AMPHI
SEQ. ID. NO. 27080    6-ArgIleLysAsnMetAspGlnThrLeuLysAsnThrLeuGly-19
SEQ. ID. NO. 27081    21-CysAlaLeuLeuAla-25
SEQ. ID. NO. 27082    48-AlaValGlyAlaLeuAla-53
SEQ. ID. NO. 27083    65-PheProArgValSer-69
SEQ. ID. NO. 27084    96-GlnIleValGlySerIleLeuGluSer-104
SEQ. ID. NO. 27085    111-GluPheValGlyAsnLeuProGly-118
Antigenic Index - Jameson-Wolf
SEQ. ID. NO. 27086    1-MetLysGlnSerAlaArgIleLysAsnMetAspGlnThrLeuLysAsnThr-17
SEQ. ID. NO. 27087    40-TyrGluTyrGlyTyrArgTyrSer-47
SEQ. ID. NO. 27088    102-LeuGluSerAsnProAlaGluAlaArgGluPheValGly-114
Hydrophilic Regions - Hopp-Woods
SEQ. ID. NO. 27089    1-MetLysGlnSerAlaArgIleLysAsnMetAspGlnThrLeu-14
SEQ. ID. NO. 27090    105-AsnProAlaGluAlaArgGluPheVal-113
g085-2
AMPHI Regions - AMPHI
SEQ. ID. NO. 27091    41-GluArgValAlaGlnIleGlyLysMetPheAspGlyLeu-53
SEQ. ID. NO. 27092    60-LeuLysAspAlaLeuAspAsnGlyPheAsp-69
SEQ. ID. NO. 27093    90-AsnGlyGlyArgValLeuGlyAspIleGluLeuLeuAlaAspIle-104
SEQ. ID. NO. 27094    125-ThrSerLeuValGlyTyr-130
SEQ. ID. NO. 27095    141-IleAlaGlyAsnIleGlyThr-147
SEQ. ID. NO. 27096    174-GluAsnThrGluSerLeu-179
SEQ. ID. NO. 27097    191-GluAspHisLeuAspArgTyrAspAspLeuLeuAspTyr-203
SEQ. ID. NO. 27098    213-GlyAspGlyValGln-217
SEQ. ID. NO. 27099    225-PheCysArgAlaMetLysArgAlaGlyArgGluVal-236
SEQ. ID. NO. 27100    275-HisAsnAlaAlaAsnValMetAlaAlaValAlaLeuCysGluAla-289
SEQ. ID. NO. 27101    300-HisValLysThrPheGlnGlyLeuProHisArgValGluLysIleGly-315
SEQ. ID. NO. 27102    336-AlaAlaIleAlaGlyLeu-341
SEQ. ID. NO. 27103    353-GlyLysGlyGlnAspPheThr-359
SEQ. ID. NO. 27104    394-ThrAspCysValThrLeuGluGluAlaValGlnThr-405
SEQ. ID. NO. 27105    424-SerPheAspMetPheLysGlyTyr-431

TABLE 1-continued

| | |
|---|---|
| Antigenic Index - Jameson-Wolf | |
| SEQ. ID. NO. 27106 | 4-GlnAsnLysLysIleLeu-9 |
| SEQ. ID. NO. 27107 | 23-TyrLeuArgLysAsnGlyAlaGluValAlaAlaTyrAspAlaGluLeuLysAlaGluArgValAlaGln-45 |
| SEQ. ID. NO. 27108 | 58-GlyArgLeuLysAspAlaLeuAspAsnGlyPhe-68 |
| SEQ. ID. NO. 27109 | 74-SerProGlyIleSerGluArgGlnProAspIleGluAlaPheLysGlnAsnGlyGlyArgValLeuGly-96 |
| SEQ. ID. NO. 27110 | 104-IleValAsnArgArgGlyAspLysVal-112 |
| SEQ. ID. NO. 27111 | 116-ThrGlySerAsnGlyLysThrThr-123 |
| SEQ. ID. NO. 27112 | 150-LeuGluAlaGluLeuGlnArgGluGlyLysLysAlaAsp-162 |
| SEQ. ID. NO. 27113 | 169-SerSerPheGlnLeuGluAsnThrGluSerLeuArgProThrAla-183 |
| SEQ. ID. NO. 27114 | 189-IleSerGluAspHisLeuAspArgTyrAspAspLeuLeu-201 |
| SEQ. ID. NO. 27115 | 204-AlaHisThrLysAlaGluIlePheArgGlyAspGlyVal-216 |
| SEQ. ID. NO. 27116 | 220-AsnAlaAspAspValPhe-225 |
| SEQ. ID. NO. 27117 | 228-AlaMetLysArgAlaGlyArgGluValLysArgPheSerLeuGluHisGluAla-245 |
| SEQ. ID. NO. 27118 | 251-ArgGlyThrGlyCysLeuLysGlnGlyAsnGluAspLeuIleSerThrGlnAspIlePro-270 |
| SEQ. ID. NO. 27119 | 291-GlyLeuProArgGluAlaLeu-297 |
| SEQ. ID. NO. 27120 | 307-LeuProHisArgValGluLysIleGlyGluLysAsnGly-319 |
| SEQ. ID. NO. 27121 | 322-PheIleAspAspSerLysGlyThrAsnVal-331 |
| SEQ. ID. NO. 27122 | 351-GlyMetGlyLysGlyGlnAspPheThrProLeuArgAspAlaLeuLysAspLysAlaLys-370 |
| SEQ. ID. NO. 27123 | 378-AspAlaProGlnIleArgArgAspLeuAspGlyCysGly-390 |
| SEQ. ID. NO. 27124 | 397-ValThrLeuGluGluAlaVal-403 |
| SEQ. ID. NO. 27125 | 431-TyrAlaHisArgSer-435 |
| Hydrophilic Regions - Hopp-Woods | |
| SEQ. ID. NO. 27126 | 4-GlnAsnLysLysIleLeu-9 |
| SEQ. ID. NO. 27127 | 25-ArgLysAsnGlyAlaGlu-30 |
| SEQ. ID. NO. 27128 | 32-AlaAlaTyrAspAlaGluLeuLysAlaGluArgValAlaGln-45 |
| SEQ. ID. NO. 27129 | 59-ArgLeuLysAspAlaLeuAspAsnGlyPhe-68 |
| SEQ. ID. NO. 27130 | 77-IleSerGluArgGlnProAspIleGluAlaPheLysGlnAsnGlyGly-92 |
| SEQ. ID. NO. 27131 | 104-IleValAsnArgArgGlyAspLysVal-112 |
| SEQ. ID. NO. 27132 | 118-SerAsnGlyLysThrThr-123 |
| SEQ. ID. NO. 27133 | 150-LeuGluAlaGluLeuGlnArgGluGlyLysLysAlaAsp-162 |
| SEQ. ID. NO. 27134 | 174-GluAsnThrGluSerLeuArgPro-181 |
| SEQ. ID. NO. 27135 | 189-IleSerGluAspHisLeuAspArgTyrAspAspLeuLeu-201 |
| SEQ. ID. NO. 27136 | 204-AlaHisThrLysAlaGluIlePheArgGlyAspGly-215 |
| SEQ. ID. NO. 27137 | 228-AlaMetLysArgAlaGlyArgGluValLysArgPheSerLeuGluHisGluAla-245 |
| SEQ. ID. NO. 27138 | 251-ArgGlyThrGlyCysLeuLysGlnGlyAsnGluAspLeuIleSer-265 |
| SEQ. ID. NO. 27139 | 291-GlyLeuProArgGluAlaLeu-297 |
| SEQ. ID. NO. 27140 | 309-HisArgValGluLysIleGlyGluLysAsnGly-319 |
| SEQ. ID. NO. 27141 | 324-AspAspSerLysGlyThrAsn-330 |
| SEQ. ID. NO. 27142 | 353-GlyLysGlyGlnAsp-357 |
| SEQ. ID. NO. 27143 | 359-ThrProLeuArgAspAlaLeuLysAspLysAlaLys-370 |
| SEQ. ID. NO. 27144 | 380-ProGlnIleArgArgAspLeuAspGly-388 |
| SEQ. ID. NO. 27145 | 397-ValThrLeuGluGluAlaVal-403 |
| SEQ. ID. NO. 27146 | 431-TyrAlaHisArgSer-435 |
| g086 | |
| AMPHI Regions - AMPHI | |
| SEQ. ID. NO. 27147 | 55-MetArgThrTrpArgArgLeuValPro-63 |
| SEQ. ID. NO. 27148 | 83-IleAsnGlyAlaThrArg-88 |
| SEQ. ID. NO. 27149 | 99-ProThrGluLeuPheLysLeuAlaVal-107 |
| SEQ. ID. NO. 27150 | 120-GluValLeuArgSerMetGluSerLeuGlyTrpGlnSerIleTrpArgGlyThrAlaAsn-139 |
| SEQ. ID. NO. 27151 | 155-GluMetTyrGlyArgPhe-160 |
| SEQ. ID. NO. 27152 | 185-SerPheValValIle-189 |
| SEQ. ID. NO. 27153 | 228-ArgValGlnArgValValAlaPheLeuAspProTrpLysAspProGln-243 |
| SEQ. ID. NO. 27154 | 293-GlyPhePheGlyMetCys-298 |
| SEQ. ID. NO. 27155 | 336-TrpIleGlyIleGlnSerPhe-342 |
| Antigenic Index - Jameson-Wolf | |
| SEQ. ID. NO. 27156 | 20-LeuAlaSerLysGluGlyGlyAsp-27 |
| SEQ. ID. NO. 27157 | 54-ArgMetArgThrTrpArgArg-60 |
| SEQ. ID. NO. 27158 | 79-AlaGlyArgGluIleAsnGlyAla-86 |
| SEQ. ID. NO. 27159 | 115-PheThrArgArgGluGluValLeuArgSerMetGlu-126 |
| SEQ. ID. NO. 27160 | 134-TrpArgGlyThrAla-138 |
| SEQ. ID. NO. 27161 | 144-AlaThrAsnProGlnAlaArgArgGluThrLeuGluMet-156 |
| SEQ. ID. NO. 27162 | 225-AlaProTyrArgVal-229 |
| SEQ. ID. NO. 27163 | 236-LeuAspProTrpLysAspProGlnGlyAla-245 |
| SEQ. ID. NO. 27164 | 265-GlyLeuGlyAlaSerLeuSerLysArgGlyPheLeu-276 |
| SEQ. ID. NO. 27165 | 313-SerIleGlyLysGlnSerArgAspLeuGly-322 |
| SEQ. ID. NO. 27166 | 352-LeuProThrLysGlyLeu-357 |
| SEQ. ID. NO. 27167 | 382-IleAspTyrGluAsnArgGlnLysMetArgGlyTyrArgValGlu-396 |
| Hydrophilic Regions - Hopp-Woods | |
| SEQ. ID. NO. 27168 | 21-AlaSerLysGluGlyGlyAsp-27 |
| SEQ. ID. NO. 27169 | 79-AlaGlyArgGluIleAsnGly-85 |
| SEQ. ID. NO. 27170 | 115-PheThrArgArgGluGluValLeuArgSerMetGlu-126 |
| SEQ. ID. NO. 27171 | 147-ProGlnAlaArgArgGluThrLeuGluMet-156 |
| SEQ. ID. NO. 27172 | 238-ProTrpLysAspProGlnGly-244 |
| SEQ. ID. NO. 27173 | 270-LeuSerLysArgGlyPheLeu-276 |
| SEQ. ID. NO. 27174 | 316-LysGlnSerArgAspLeu-321 |
| SEQ. ID. NO. 27175 | 382-IleAspTyrGluAsnArgGlnLysMetArgGlyTyrArgValGlu-396 |
| g087 | |
| AMPHI Regions - AMPHI | |
| SEQ. ID. NO. 27176 | 80-LysThrValArgGluAlaGlnArgIleIle-89 |
| SEQ. ID. NO. 27177 | 99-GlyPheGlyGlyPheValThrPheProGlyGlyLeuAlaAlaLysLeuLeu-115 |

TABLE 1-continued

| | |
|---|---|
| SEQ. ID. NO. 27178 | 129-GlyLeuSerAsnArgHisLeuSerArgTrpAlaLysArgValLeuTyrAlaPheProLys-148 |
| SEQ. ID. NO. 27179 | 157-ValGlyAsnProValArg-162 |
| SEQ. ID. NO. 27180 | 192-GlyAlaAspValLeuAsnLysThrVal-200 |
| SEQ. ID. NO. 27181 | 241-ValGluPheIleThrAspMetValSerAlaTyr-251 |
| SEQ. ID. NO. 27182 | 313-GluLysLeuAlaGluIleLeuGly-320 |
| SEQ. ID. NO. 27183 | 330-TrpAlaGluAsnAla-334 |
| Antigenic Index - Jameson-Wolf | |
| SEQ. ID. NO. 27184 | 25-AspSerLeuArgValArgGly-31 |
| SEQ. ID. NO. 27185 | 37-LeuGlySerLysAspSerMetGluGluArgIleValProGlnTyrGlyIle-53 |
| SEQ. ID. NO. 27186 | 61-LysGlyIleArgGlyAsnGlyIleLysArgLysLeu-72 |
| SEQ. ID. NO. 27187 | 80-LysThrValArgGluAlaGlnArgIleIleArgLysHisArgVal-94 |
| SEQ. ID. NO. 27188 | 130-LeuSerAsnArgHisLeuSerArgTrpAlaLys-140 |
| SEQ. ID. NO. 27189 | 150-PheSerHisGluGlyGlyLeu-156 |
| SEQ. ID. NO. 27190 | 159-AsnProValArgAlaAspIleSer-166 |
| SEQ. ID. NO. 27191 | 171-ProAlaGluArgPheGlnGlyArgGluGlyArgLeu-182 |
| SEQ. ID. NO. 27192 | 195-ValLeuAsnLysThrVal-200 |
| SEQ. ID. NO. 27193 | 207-LeuProGluGluValArgProGlnMetTyrHisGlnSerGlyArgAsnLysLeuGly-225 |
| SEQ. ID. NO. 27194 | 229-AlaAspTyrAspAla-233 |
| SEQ. ID. NO. 27195 | 235-GlyValLysAlaGluCys-240 |
| SEQ. ID. NO. 27196 | 249-SerAlaTyrArgAspAlaAsp-255 |
| SEQ. ID. NO. 27197 | 284-AlaValAspAspHisGlnThrAla-291 |
| SEQ. ID. NO. 27198 | 309-GlnLeuThrAlaGluLysLeuAlaGlu-317 |
| SEQ. ID. NO. 27199 | 321-SerLeuAsnArgGluLysCysLeuLys-329 |
| SEQ. ID. NO. 27200 | 332-GluAsnAlaArgThr-336 |
| SEQ. ID. NO. 27201 | 341-HisSerAlaAspAspValAlaGlu-348 |
| Hydrophilic Regions - Hopp-Woods | |
| SEQ. ID. NO. 27202 | 25-AspSerLeuArgValArgGly-31 |
| SEQ. ID. NO. 27203 | 39-SerLysAspSerMetGluGluArgIleVal-48 |
| SEQ. ID. NO. 27204 | 66-AsnGlyIleLysArgLysLeu-72 |
| SEQ. ID. NO. 27205 | 81-ThrValArgGluAlaGlnArgIleIleArgLysHisArgVal-94 |
| SEQ. ID. NO. 27206 | 134-HisLeuSerArgTrpAlaLys-140 |
| SEQ. ID. NO. 27207 | 161-ValArgAlaAspIle-165 |
| SEQ. ID. NO. 27208 | 171-ProAlaGluArgPheGlnGlyArgGluGlyArgLeu-182 |
| SEQ. ID. NO. 27209 | 207-LeuProGluValArgPro-213 |
| SEQ. ID. NO. 27210 | 219-SerGlyArgAsnLysLeu-224 |
| SEQ. ID. NO. 27211 | 235-GlyValLysAlaGluCys-240 |
| SEQ. ID. NO. 27212 | 249-SerAlaTyrArgAspAlaAsp-255 |
| SEQ. ID. NO. 27213 | 284-AlaValAspAspHisGlnThrAla-291 |
| SEQ. ID. NO. 27214 | 310-LeuThrAlaGluLysLeuAlaGlu-317 |
| SEQ. ID. NO. 27215 | 322-LeuAsnArgGluLysCysLeuLys-329 |
| SEQ. ID. NO. 27216 | 341-HisSerAlaAspAspValAlaGlu-348 |
| g088-2 | |
| AMPHI Regions - AMPHI | |
| SEQ. ID. NO. 27217 | 7-HisPheSerAsnTrpLeuThrGlyLeuAsnIlePheGlnTyrThrThr-22 |
| SEQ. ID. NO. 27218 | 24-ArgAlaValMetAlaAlaLeu-30 |
| SEQ. ID. NO. 27219 | 43-ThrIleArgArgLeuThrAlaLeuLysCysGlyGln-54 |
| SEQ. ID. NO. 27220 | 88-LeuTrpGlyAsnTrpAlaAsn-94 |
| SEQ. ID. NO. 27221 | 111-GlyPheTyrAspAspTrpArgLysValValTyr-121 |
| SEQ. ID. NO. 27222 | 140-AlaValIleAlaGlyLeuAlaLeu-147 |
| SEQ. ID. NO. 27223 | 175-GlyPheLeuValLeuSerTyrLeuThrIle-184 |
| SEQ. ID. NO. 27224 | 187-ThrSerAsnAlaValAsnLeuThrAspGlyLeuAspGlyLeuAlaAla-202 |
| SEQ. ID. NO. 27225 | 221-HisTyrGlnPheSerGlnTyrLeuGlnLeuProTyr-232 |
| SEQ. ID. NO. 27226 | 244-ThrAlaMetCysGlyAlaCysLeuGlyPhe-253 |
| Antigenic Index - Jameson-Wolf | |
| SEQ. ID. NO. 27227 | 48-ThrAlaLeuLysCysGlyGlnAlaValArgThrAspGlyProGln-62 |
| SEQ. ID. NO. 27228 | 66-ValLysAsnGlyThrProThrMet-73 |
| SEQ. ID. NO. 27229 | 114-AspAspTrpArgLysValValTyrLysAspProAsnGlyValSerAlaLysPhe-131 |
| SEQ. ID. NO. 27230 | 193-LeuThrAspGlyLeuAsp-198 |
| SEQ. ID. NO. 27231 | 312-LysLysThrLysLysArgIle-318 |
| SEQ. ID. NO. 27232 | 328-TyrGluGlnLysGlyTrpLysGluThrGlnVal-338 |
| Hydrophilic Regions - Hopp-Woods | |
| SEQ. ID. NO. 27233 | 56-ValArgThrAspGlyProGln-62 |
| SEQ. ID. NO. 27234 | 114-AspAspTrpArgLysValValTyrLysAspProAsnGlyVal-127 |
| SEQ. ID. NO. 27235 | 312-LysLysThrLysLysArgIle-318 |
| SEQ. ID. NO. 27236 | 331-LysGlyTrpLysGlu-335 |
| g089 | |
| AMPHI Regions - AMPHI | |
| SEQ. ID. NO. 27237 | 40-PheSerThrArgCysGlyLysProTrpLysValLeu-51 |
| SEQ. ID. NO. 27238 | 74-LeuAlaAlaLeuCysLysProCysSerGlyMetSerCys-86 |
| SEQ. ID. NO. 27239 | 119-ArgProAlaArgPhe-123 |
| Antigenic Index - Jameson-Wolf | |
| SEQ. ID. NO. 27240 | 1-MetProProLysIleThrLysSerGlyPhe-10 |
| SEQ. ID. NO. 27241 | 40-PheSerThrArgCysGlyLysProTrpLys-49 |
| SEQ. ID. NO. 27242 | 53-CysSerSerAsnAlaSerArgGlyLysProThrAlaSerHisLysAla-68 |
| SEQ. ID. NO. 27243 | 77-LeuCysLysProCysSerGlyMetSer-85 |
| SEQ. ID. NO. 27244 | 87-ValGluIleLysSerSerLeuProCysPheLysGlnProValProArgSerAsnGlnLysSerAlaSerCysSerLysGluAsnArgPheThrSer<br>ArgProAlaArgPheMetAlaArgGlnAsnThrSerSerAlaPheLysThrCysThrProSerProArgLysIleSer-144 |
| Hydrophilic Regions - Hopp-Woods | |
| SEQ. ID. NO. 27245 | 43-ArgCysGlyLysPro-47 |
| SEQ. ID. NO. 27246 | 56-AsnAlaSerArgGlyLysProThrAlaSerHisLysAla-68 |

TABLE 1-continued

| | |
|---|---|
| SEQ. ID. NO. 27247 | 87-ValGluIleLysSer-91 |
| SEQ. ID. NO. 27248 | 99-ProValProArgSerAsnGlnLysSerAlaSerCysSerLysGluAsnArgPheThrSerArgProAlaArgPheMetAla-125 |
| SEQ. ID. NO. 27249 | 137-ThrProSerProArgLysIleSer-144 | g090-1
AMPHI Regions - AMPHI

| | |
|---|---|
| SEQ. ID. NO. 27250 | 10-SerGlnSerLeuLysArgPheAspLysHisPheArg-21 |
| SEQ. ID. NO. 27251 | 51-ArgLeuAsnArgLeuPhe-56 |
| SEQ. ID. NO. 27252 | 59-AspAlaValGlyGlnVal-64 |
| SEQ. ID. NO. 27253 | 129-PheAlaValValAspGlu-134 |
| SEQ. ID. NO. 27254 | 141-AlaAspPhePheHisThrValArgGlnAla-150 |
| SEQ. ID. NO. 27255 | 152-GluGlyPheAspValPheGlnGlnCysPheAla-162 |
| SEQ. ID. NO. 27256 | 164-GlnThrAspGlyLeuAlaGln-170 |
| SEQ. ID. NO. 27257 | 177-ValGlyGlyValValGlnThrLeuGlnArg-186 |
| SEQ. ID. NO. 27258 | 233-ValValArgIleGlnAsnLeuHisSerIle-242 |
| SEQ. ID. NO. 27259 | 253-ValValGluGlnIle-257 |
| SEQ. ID. NO. 27260 | 388-GluThrValValGlnArgIlePheGlnThrThr-398 |
| SEQ. ID. NO. 27261 | 404-ProValLysHisLeuThrAspLeuArg-412 |
| SEQ. ID. NO. 27262 | 425-AsnLeuArgAlaValPheAlaGlnIleGlyAsnHisGlyAsnThrArgAlaAlaLysSer-444 |

Antigenic Index - Jameson-Wolf

| | |
|---|---|
| SEQ. ID. NO. 27263 | 8-ThrAlaSerGlnSerLeuLysArgPheAspLysHisPheArg-21 |
| SEQ. ID. NO. 27264 | 29-HisIleGluThrArgAlaGlyGlyAlaGluGlnAspAsnIleAla-43 |
| SEQ. ID. NO. 27265 | 51-ArgLeuAsnArgLeuPheGlnSerAspAlaVal-61 |
| SEQ. ID. NO. 27266 | 73-AlaAspLeuArgArgIleAspAlaAspGlnGluHis-84 |
| SEQ. ID. NO. 27267 | 94-AlaGlnGlyArgGluVal-99 |
| SEQ. ID. NO. 27268 | 107-GlnAsnHisGluGluArgValLeuGlnThrGlyAsnArgGlyGlyGlyArgAlaAspIleArg-127 |
| SEQ. ID. NO. 27269 | 149-GlnAlaLeuGluGlyPhe-154 |
| SEQ. ID. NO. 27270 | 161-PheAlaArgGlnThrAspGlyLeuAlaGlnSerHisGlySerHisAsnValGlyGly-179 |
| SEQ. ID. NO. 27271 | 183-ThrLeuGlnArgAspValLeuArgArgAsnGln-193 |
| SEQ. ID. NO. 27272 | 201-ThrAlaArgProAlaPheGlnPro-208 |
| SEQ. ID. NO. 27273 | 214-PheGlnGlyLysProPheHisPheThrProCysPro-225 |
| SEQ. ID. NO. 27274 | 268-ValHisHisArgArgArgSerArgAlaGln-277 |
| SEQ. ID. NO. 27275 | 285-GluAlaGlyLysLeuGln-290 |
| SEQ. ID. NO. 27276 | 305-LeuGlnAsnArgArgThrAspIleAlaArgAsnAspGlyIleGlnPro-320 |
| SEQ. ID. NO. 27277 | 322-LeuAspAlaGluIleAlaAspGlnAlaArgTyrArgGly-334 |
| SEQ. ID. NO. 27278 | 339-AlaGlyAsnArgAsnHis-344 |
| SEQ. ID. NO. 27279 | 353-ValArgGlnGlnPhe-357 |
| SEQ. ID. NO. 27280 | 369-GluArgLeuAspIle-373 |
| SEQ. ID. NO. 27281 | 379-AspAlaGlyThrGluArgGlnAsnIle-387 |
| SEQ. ID. NO. 27282 | 396-GlnThrThrArgValLysHisGlnProVal-405 |
| SEQ. ID. NO. 27283 | 407-HisLeuThrAspLeuArgHis-413 |
| SEQ. ID. NO. 27284 | 422-IleSerGlyAsnLeu-426 |
| SEQ. ID. NO. 27285 | 435-AsnHisGlyAsnThrArgAlaAlaLysSerGlyAspGluAspPhePhe-450 |

Hydrophilic Regions - Hopp-Woods

| | |
|---|---|
| SEQ. ID. NO. 27286 | 9-AlaSerGlnSerLeuLysArgPheAspLysHisPheArg-21 |
| SEQ. ID. NO. 27287 | 29-HisIleGluThrArgAlaGlyGlyAlaGluGlnAspAsnIleAla-43 |
| SEQ. ID. NO. 27288 | 73-AlaAspLeuArgArgIleAspAlaAspGlnGluHis-84 |
| SEQ. ID. NO. 27289 | 94-AlaGlnGlyArgGluVal-99 |
| SEQ. ID. NO. 27290 | 107-GlnAsnHisGluGluArgValLeu-114 |
| SEQ. ID. NO. 27291 | 117-GlyAsnArgGlyGlyGlyArgAlaAspIleArg-127 |
| SEQ. ID. NO. 27292 | 163-ArgGlnThrAspGlyLeuAla-169 |
| SEQ. ID. NO. 27293 | 184-LeuGlnArgAspValLeuArgArgAsnGln-193 |
| SEQ. ID. NO. 27294 | 269-HisHisArgArgArgSerArgAla-276 |
| SEQ. ID. NO. 27295 | 285-GluAlaGlyLysLeuGln-290 |
| SEQ. ID. NO. 27296 | 306-GlnAsnArgArgThrAspIleAlaArgAsnAspGlyIle-318 |
| SEQ. ID. NO. 27297 | 322-LeuAspAlaGluIleAlaAspGlnAlaArgTyrArg-333 |
| SEQ. ID. NO. 27298 | 369-GluArgLeuAspIle-373 |
| SEQ. ID. NO. 27299 | 380-AlaGlyThrGluArgGlnAsnIle-387 |
| SEQ. ID. NO. 27300 | 398-ThrArgValLysHisGlnPro-404 |
| SEQ. ID. NO. 27301 | 409-ThrAspLeuArgHis-413 |
| SEQ. ID. NO. 27302 | 437-GlyAsnThrArgAlaAlaLysSerGlyAspGluAspPhePhe-450 | g091
AMPHI Regions - AMPHI

| | |
|---|---|
| SEQ. ID. NO. 27303 | 38-LysProLeuSerAspGlyIleAlaSerArgLeuIleThrArgLeu-52 |
| SEQ. ID. NO. 27304 | 61-ValLeuValSerValLeuThrSerLeuAlaLys-71 |

Antigenic Index - Jameson-Wolf

| | |
|---|---|
| SEQ. ID. NO. 27305 | 5-ValProProSerProAlaThr-11 |
| SEQ. ID. NO. 27306 | 28-IleLeuGlyArgArgArgProProLeuProLysProLeuSerAspGlyIleAla-45 |
| SEQ. ID. NO. 27307 | 73-LeuLeuSerGluArgLysValLeu-80 |

Hydrophilic Regions - Hopp-Woods

| | |
|---|---|
| SEQ. ID. NO. 27308 | 28-IleLeuGlyArgArgArgProProLeu-36 |
| SEQ. ID. NO. 27309 | 73-LeuLeuSerGluArgLysValLeu-80 | g092
AMPHI Regions - AMPHI

| | |
|---|---|
| SEQ. ID. NO. 27310 | 55-GlyMetSerGlyIleAlaGluValLeuHis-64 |
| SEQ. ID. NO. 27311 | 76-AlaArgAsnAlaAlaThrGluHisLeu-84 |
| SEQ. ID. NO. 27312 | 95-HisThrAlaGluHisValAsnGly-102 |
| SEQ. ID. NO. 27313 | 122-AlaLeuGluArgGln-126 |
| SEQ. ID. NO. 27314 | 137-AlaGluLeuMetArgPheArgAsp-144 |
| SEQ. ID. NO. 27315 | 209-LeuThrProIleMetSerValValThrAsnIleAsp-220 |
| SEQ. ID. NO. 27316 | 226-ThrTyrGlyHisSerValGluLysLeuHisGlnAlaPheIleAspPheIleHisArg-244 |

TABLE 1-continued

| | |
|---|---|
| SEQ. ID. NO. 27317 | 260-ValArgAlaIleLeuProLysValSerLysProTyr-271 |
| SEQ. ID. NO. 27318 | 273-ThrTyrGlyLeuAspAspThrAla-280 |
| SEQ. ID. NO. 27319 | 321-AsnValLeuAsnAlaLeuAlaAlaIle-329 |
| SEQ. ID. NO. 27320 | 339-ValGluAlaIleGlnLysGly-345 |
| SEQ. ID. NO. 27321 | 353-GlyArgArgPheGlnLysTyrGlyAspIleLys-363 |
| SEQ. ID. NO. 27322 | 407-ArgTyrThrArgThrArgAspLeuPheGluAspPheThrLysValLeuAsnThrValAspAlaLeu-428 |
| SEQ. ID. NO. 27323 | 449-LeuAlaArgAlaIleArgValLeuGlyLysLeu-459 |
| SEQ. ID. NO. 27324 | 464-CysGluAsnValAlaAspLeuProGlnMetLeuMetAsn-476 |

Antigenic Index - Jameson-Wolf

| | |
|---|---|
| SEQ. ID. NO. 27325 | 17-AlaAsnGlyGlnThrPhe-22 |
| SEQ. ID. NO. 27326 | 25-ThrProLeuArgThrLysAsnGlnProGluArgAsnIleMetMetLysAsnArgVal-43 |
| SEQ. ID. NO. 27327 | 70-ValSerGlySerAspGlnAlaArgAsnAlaAla-80 |
| SEQ. ID. NO. 27328 | 111-AlaValLysLysGluAsnProGluVal-119 |
| SEQ. ID. NO. 27329 | 121-AlaAlaLeuGluArgGlnIle-127 |
| SEQ. ID. NO. 27330 | 140-MetArgPheArgAspGlyIle-146 |
| SEQ. ID. NO. 27331 | 150-GlyThrHisGlyLysThrThrThr-157 |
| SEQ. ID. NO. 27332 | 184-GlyThrAsnAlaArgLeuGlyLysGlyGluTyr-194 |
| SEQ. ID. NO. 27333 | 198-GluAlaAspGluSerAspAla-204 |
| SEQ. ID. NO. 27334 | 218-AsnIleAspGluAspHisMetAspThrTyrGly-228 |
| SEQ. ID. NO. 27335 | 230-SerValGluLysLeuHis-235 |
| SEQ. ID. NO. 27336 | 255-ValAspSerGluHisVal-260 |
| SEQ. ID. NO. 27337 | 263-IleLeuProLysValSerLysProTyrAla-272 |
| SEQ. ID. NO. 27338 | 275-GlyLeuAspAspThrAlaAsp-281 |
| SEQ. ID. NO. 27339 | 286-AspIleGluAsnValGlyAla-292 |
| SEQ. ID. NO. 27340 | 302-MetLysGlyHisGluGlnGlySerPhe-310 |
| SEQ. ID. NO. 27341 | 351-GlyValGlyArgArgPheGlnLysTyrGlyAspIleLysLeuProAsnGlyGly-368 |
| SEQ. ID. NO. 27342 | 374-AspAspTyrGlyHisHisPro-380 |
| SEQ. ID. NO. 27343 | 393-AlaTyrProGluLysArgLeu-399 |
| SEQ. ID. NO. 27344 | 404-GlnProHisArgTyrThrArgThrArgAspLeuPheGluAspPheThrLys-420 |
| SEQ. ID. NO. 27345 | 435-AlaAlaGlyGluGluProValAlaAlaAlaAspSerArgAlaLeuAlaArg-451 |
| SEQ. ID. NO. 27346 | 478-LeuGlnAspGlyAspVal-483 |
| SEQ. ID. NO. 27347 | 488-GlyAlaGlySerIleAsnArgValProSerAla-498 |

Hydrophilic Regions - Hopp-Woods

| | |
|---|---|
| SEQ. ID. NO. 27348 | 26-ProLeuArgThrLysAsnGlnProGluArgAsnIleMetMetLysAsnArgVal-43 |
| SEQ. ID. NO. 27349 | 71-SerGlySerAspGlnAlaArgAsnAlaAla-80 |
| SEQ. ID. NO. 27350 | 111-AlaValLysLysGluAsnProGlu-118 |
| SEQ. ID. NO. 27351 | 121-AlaAlaLeuGluArgGlnIle-127 |
| SEQ. ID. NO. 27352 | 140-MetArgPheArgAsp-144 |
| SEQ. ID. NO. 27353 | 152-HisGlyLysThrThr-156 |
| SEQ. ID. NO. 27354 | 187-AlaArgLeuGlyLysGlyGlu-193 |
| SEQ. ID. NO. 27355 | 198-GluAlaAspGluSerAspAla-204 |
| SEQ. ID. NO. 27356 | 218-AsnIleAspGluAspHisMetAsp-225 |
| SEQ. ID. NO. 27357 | 230-SerValGluLysLeuHis-235 |
| SEQ. ID. NO. 27358 | 256-AspSerGluHisVal-260 |
| SEQ. ID. NO. 27359 | 275-GlyLeuAspAspThrAlaAsp-281 |
| SEQ. ID. NO. 27360 | 303-LysGlyHisGluGlnGlySer-309 |
| SEQ. ID. NO. 27361 | 351-GlyValGlyArgArgPheGlnLys-358 |
| SEQ. ID. NO. 27362 | 360-GlyAspIleLysLeu-364 |
| SEQ. ID. NO. 27363 | 393-AlaTyrProGluLysArgLeu-399 |
| SEQ. ID. NO. 27364 | 407-ArgTyrThrArgThrArgAspLeuPheGluAspPheThrLys-420 |
| SEQ. ID. NO. 27365 | 435-AlaAlaGlyGluGluProValAlaAlaAlaAspSerArgAlaLeuAlaArg-451 |
| SEQ. ID. NO. 27366 | 479-GlnAspGlyAspVal-483 | g093-2
AMPHI Regions - AMPHI

| | |
|---|---|
| SEQ. ID. NO. 27367 | 26-ThrAlaIleLeuAsn-30 |
| SEQ. ID. NO. 27368 | 59-ThrAlaPheAsnIleLeuHisGly-66 |
| SEQ. ID. NO. 27369 | 156-GlyArgLeuLysSerValTyrGluGluLeuLysHisLeu-168 |
| SEQ. ID. NO. 27370 | 196-IleHisIleIleProAlaThrGluPhe-204 |
| SEQ. ID. NO. 27371 | 254-PheLeuLysAspThr-258 |
| SEQ. ID. NO. 27372 | 267-IleAsnThrLeuProGlyMetThrGly-275 |

Antigenic Index - Jameson-Wolf

| | |
|---|---|
| SEQ. ID. NO. 27373 | 12-GlyGlyPheSerSerGluArgGluIleSerLeuAspSerGlyThr-26 |
| SEQ. ID. NO. 27374 | 32-LeuLysSerLysGlyIleAsp-38 |
| SEQ. ID. NO. 27375 | 41-AlaPheAspProLysGluThrProLeuSerGluLeuLysGluArgGlyPhe-57 |
| SEQ. ID. NO. 27376 | 66-GlyThrTyrGlyGluAspGlyAlaVal-74 |
| SEQ. ID. NO. 27377 | 96-GlyMetAspLysTyrArgCys-102 |
| SEQ. ID. NO. 27378 | 121-AspAspThrAspPheAspAlaValGluGluLysLeuGly-133 |
| SEQ. ID. NO. 27379 | 140-ProAlaAlaGluGlySerSer-146 |
| SEQ. ID. NO. 27380 | 151-LysValLysGluLysGlyArgLeuLysSerValTyrGluGluLeuLysHisLeuGln-169 |
| SEQ. ID. NO. 27381 | 176-ArgPheIleGlyGlyGlyGluTyrSer-184 |
| SEQ. ID. NO. 27382 | 189-AsnGlyLysGlyLeuPro-194 |
| SEQ. ID. NO. 27383 | 203-GluPheTyrAspTyrGluAlaLysTyrAsnArgAspAspThrIleTyrGlnCysProSerGluAspLeuThrGluAlaGluGluSerLeuMetArg-234 |
| SEQ. ID. NO. 27384 | 245-GlyAlaGluGlyCysVal-250 |
| SEQ. ID. NO. 27385 | 253-AspPheLeuLysAspThrAspGly-260 |
| SEQ. ID. NO. 27386 | 269-ThrLeuProGlyMetThr-274 |
| SEQ. ID. NO. 27387 | 279-ValProLysSerAlaAla-284 |

Hydrophilic Regions - Hopp-Woods

| | |
|---|---|
| SEQ. ID. NO. 27388 | 15-SerSerGluArgGluIleSerLeu-22 |
| SEQ. ID. NO. 27389 | 32-LeuLysSerLysGlyIleAsp-38 |
| SEQ. ID. NO. 27390 | 41-AlaPheAspProLysGluThrProLeuSerGluLeuLysGluArgGlyPhe-57 |

TABLE 1-continued

| | |
|---|---|
| SEQ. ID. NO. 27391 | 68-TyrGlyGluAspGlyAlaVal-74 |
| SEQ. ID. NO. 27392 | 96-GlyMetAspLysTyrArgCys-102 |
| SEQ. ID. NO. 27393 | 121-AspAspThrAspPheAspAlaValGluGluLysLeuGly-133 |
| SEQ. ID. NO. 27394 | 140-ProAlaAlaGluGlySerSer-146 |
| SEQ. ID. NO. 27395 | 151-LysValLysGluLysGlyArgLeuLysSerValTyrGluGluLeuLysHisLeuGln-169 |
| SEQ. ID. NO. 27396 | 205-TyrAspTyrGluAlaLysTyrAsnArgAspAspThrIle-217 |
| SEQ. ID. NO. 27397 | 221-ProSerGluAspLeuThrGluAlaGluGluSerLeuMetArg-234 |
| SEQ. ID. NO. 27398 | 253-AspPheLeuLysAspThrAspGly-260 | g094
AMPHI Regions - AMPHI

| | |
|---|---|
| SEQ. ID. NO. 27399 | 17-LeuProProIleThrLysValGlySer-25 |
| SEQ. ID. NO. 27400 | 64-ArgGlyIleThrGlyIleCysArg-71 |
| SEQ. ID. NO. 27401 | 80-PheSerPheLeuThrAlaVal-86 |

Antigenic Index - Jameson-Wolf

| | |
|---|---|
| SEQ. ID. NO. 27402 | 4-ProLeuProLysArgAlaLeu-10 |
| SEQ. ID. NO. 27403 | 24-GlySerSerProAlaAlaProArgMetGluAla-34 |
| SEQ. ID. NO. 27404 | 50-MetProSerArgLysArgIleSer-57 |
| SEQ. ID. NO. 27405 | 60-SerIleLysAlaArgGly-65 |
| SEQ. ID. NO. 27406 | 70-CysArgSerAsnAlaAlaThrThrSer-78 |

Hydrophilic Regions - Hopp-Woods

| | |
|---|---|
| SEQ. ID. NO. 27407 | 5-LeuProLysArgAlaLeu-10 |
| SEQ. ID. NO. 27408 | 28-AlaAlaProArgMetGluAla-34 |
| SEQ. ID. NO. 27409 | 51-ProSerArgLysArgIleSer-57 |
| SEQ. ID. NO. 27410 | 60-SerIleLysAlaArgGly-65 | g095-2
AMPHI Regions - AMPHI

| | |
|---|---|
| SEQ. ID. NO. 27411 | 7-GlyGlyCysIleSerAsnLeuPheArgGlnPheGlnGlnArgGlyGlyAsnAlaValAsp-26 |
| SEQ. ID. NO. 27412 | 38-IleLeuXxxAsnIleHisGlnHisLeuArgGlnValGlyAspValPheAlaVal-55 |
| SEQ. ID. NO. 27413 | 63-TyrAlaAspSerThr-67 |
| SEQ. ID. NO. 27414 | 86-PheGlyGlnTyrGlnArgIleAsnGlyIleGluTyrPheGlyLysValPheLysGlnIleAlaArg-107 |
| SEQ. ID. NO. 27415 | 131-LysGlyCysArgHisPheAspGlyValValSer-141 |
| SEQ. ID. NO. 27416 | 174-PheLeuAspArgPheAsnArgCysAlaAspPheGlnArgHisAlaAspGlyCysGlnCysValGlnHisVal-197 |
| SEQ. ID. NO. 27417 | 204-GlnHisAspPheLys-208 |
| SEQ. ID. NO. 27418 | 236-AspValGlyGlyIleValGlnThrValSerSerIle-247 |
| SEQ. ID. NO. 27419 | 274-ThrValAspGluIleAspLysArgLeuMetGlnPhePheAspAlaVal-289 |
| SEQ. ID. NO. 27420 | 370-AsnGlyAspAlaValThrGluAlaHis-378 |
| SEQ. ID. NO. 27421 | 417-ValAsnValPheCysGly-422 |
| SEQ. ID. NO. 27422 | 435-MetLeuGlySerGlyIleSerArgLeuIleArgThrGly-447 |
| SEQ. ID. NO. 27423 | 451-AlaGlnIleValGlnAspPheGlyAspThrAlaHisAla-463 |

Antigenic Index - Jameson-Wolf

| | |
|---|---|
| SEQ. ID. NO. 27424 | 17-PheGlnGlnArgGlyGlyAsnAlaValAspAlaSerArgThrHisIle-32 |
| SEQ. ID. NO. 27425 | 62-GlnTyrAlaAspSerThrArgGlnGlyAlaGlyValGlyGlyGlyAsnArg-78 |
| SEQ. ID. NO. 27426 | 112-ValArgLeuGluGlyGluHisGlnThr-120 |
| SEQ. ID. NO. 27427 | 126-AlaAlaCysSerGlyLysGlyCysArgHisPheAspGly-138 |
| SEQ. ID. NO. 27428 | 163-AlaAlaAlaAspAlaPheLysAlaGluGlnAlaPhe-174 |
| SEQ. ID. NO. 27429 | 176-AspArgPheAsnArgCysAlaAspPheGlnArgHisAlaAspGlyCysGln-192 |
| SEQ. ID. NO. 27430 | 205-HisAspPheLysArg-209 |
| SEQ. ID. NO. 27431 | 253-GlyGlnAsnArgAlaAspVal-259 |
| SEQ. ID. NO. 27432 | 263-AsnThrGlnLysGlyPheAlaVal-270 |
| SEQ. ID. NO. 27433 | 273-HisThrValAspGluIleAspLysArgLeu-282 |
| SEQ. ID. NO. 27434 | 299-AspIleGlyAsnAspGlyHisAsnArgGlyGlnMetXxxGluArgGlyIle-315 |
| SEQ. ID. NO. 27435 | 339-PheAlaAlaAspAsnGluSerGlyValGluSerCysArgAlaGluAspGlyGlyGlyGlnAlaGlyGlyArg-362 |
| SEQ. ID. NO. 27436 | 364-PheAlaValArgThrGlyAsnGlyAspAlaValThr-375 |
| SEQ. ID. NO. 27437 | 384-GlnGlyAlaArgAsnAsnGlyAsnLeuProLeuGlnArgSerAspAsnPheGly-401 |
| SEQ. ID. NO. 27438 | 405-LeuAspGlyGlyArgGlyAsnAspAspIleArgThr-416 |
| SEQ. ID. NO. 27439 | 442-ArgLeuIleArgThrGlyAsnPheLys-450 |
| SEQ. ID. NO. 27440 | 455-GlnAspPheGlyAspThrAlaHisAlaAspAlaAlaAspThrAspLysMetAspVal-473 |

Hydrophilic Regions - Hopp-Woods

| | |
|---|---|
| SEQ. ID. NO. 27441 | 17-PheGlnGlnArgGlyGlyAsnAlaValAspAlaSerArgThrHisIle-32 |
| SEQ. ID. NO. 27442 | 65-AspSerThrArgGlnGlyAla-71 |
| SEQ. ID. NO. 27443 | 112-ValArgLeuGluGlyGluHis-118 |
| SEQ. ID. NO. 27444 | 128-CysSerGlyLysGlyCysArgHisPheAsp-137 |
| SEQ. ID. NO. 27445 | 163-AlaAlaAlaAspAlaPheLysAlaGluGlnAlaPhe-174 |
| SEQ. ID. NO. 27446 | 182-AlaAspPheGlnArgHisAlaAspGly-190 |
| SEQ. ID. NO. 27447 | 205-HisAspPheLysArg-209 |
| SEQ. ID. NO. 27448 | 273-HisThrValAspGluIleAspLysArgLeu-282 |
| SEQ. ID. NO. 27449 | 300-IleGlyAsnAspGlyHisAsnArgGlyGlnMetXxxGluArgGlyIle-315 |
| SEQ. ID. NO. 27450 | 339-PheAlaAlaAspAsnGluSerGlyValGluSerCysArgAlaGluAspGlyGlyGlyGly-357 |
| SEQ. ID. NO. 27451 | 368-ThrGlyAsnGlyAspAlaValThr-375 |
| SEQ. ID. NO. 27452 | 384-GlnGlyAlaArgAsnAsnGly-390 |
| SEQ. ID. NO. 27453 | 394-LeuGlnArgSerAspAsn-399 |
| SEQ. ID. NO. 27454 | 407-GlyGlyArgGlyAsnAspAspIleArgThr-416 |
| SEQ. ID. NO. 27455 | 461-AlaHisAlaAspAlaAlaAspThrAspLysMetAspVal-473 | g096-2
AMPHI Regions - AMPHI

| | |
|---|---|
| SEQ. ID. NO. 27456 | 19-GlyIlePheGluGluIleAspAlaHis-27 |
| SEQ. ID. NO. 27457 | 59-IleAsnGlyValValSerVal-65 |
| SEQ. ID. NO. 27458 | 112-GlnPhePheValAsnAlaPheGlnThrAlaPhePhePheAsp-125 |
| SEQ. ID. NO. 27459 | 161-GluLeuGlyAsnGlyXxx-166 |
| SEQ. ID. NO. 27460 | 172-AsnGlnPheAlaAla-176 |

TABLE 1-continued

| | |
|---|---|
| SEQ. ID. NO. 27461 | 188-ThrAlaAlaGlyIleGlyAsnAlaGln-196 |
| SEQ. ID. NO. 27462 | 228-XxxArgArgPheLeu-232 |

Antigenic Index - Jameson-Wolf

| | |
|---|---|
| SEQ. ID. NO. 27463 | 4-HisThrGlyGlnGly-8 |
| SEQ. ID. NO. 27464 | 22-GluGluIleAspAla-26 |
| SEQ. ID. NO. 27465 | 30-PheArgThrAspCys-34 |
| SEQ. ID. NO. 27466 | 74-LeuGlyCysGlyAspAspValTyrAla-82 |
| SEQ. ID. NO. 27467 | 88-ValGlnAspGlyAla-92 |
| SEQ. ID. NO. 27468 | 97-AlaAlaAspLysThrPheGlyAsn-104 |
| SEQ. ID. NO. 27469 | 133-AlaPheGlyArgArgLeuHisLysHisArgGlnThr-144 |
| SEQ. ID. NO. 27470 | 161-GluLeuGlyAsnGlyXxxSerGlnCysLeu-170 |
| SEQ. ID. NO. 27471 | 181-AlaAspGlyGlyGlyGlyAspThr-188 |
| SEQ. ID. NO. 27472 | 211-ThrValLysAspValGluCysArgLeuLysAla-221 |

Hydrophilic Regions - Hopp-Woods

| | |
|---|---|
| SEQ. ID. NO. 27473 | 22-GluGluIleAspAla-26 |
| SEQ. ID. NO. 27474 | 75-GlyCysGlyAspAspValTyr-81 |
| SEQ. ID. NO. 27475 | 97-AlaAlaAspLysThrPheGly-103 |
| SEQ. ID. NO. 27476 | 133-AlaPheGlyArgArgLeuHisLysHisArgGln-143 |
| SEQ. ID. NO. 27477 | 182-AspGlyGlyGlyGlyAspThr-188 |
| SEQ. ID. NO. 27478 | 211-ThrValLysAspValGluCysArgLeuLysAla-221 | g097
AMPHI Regions - AMPHI

| | |
|---|---|
| SEQ. ID. NO. 27479 | 28-AlaGlyLeuThrThrPheLeuThrMetCysTyrIleVal-40 |
| SEQ. ID. NO. 27480 | 166-AlaThrLeuValGlyLeuGlyAspIleHisGlnProSerAlaLeuLeuAlaLeuPheGlyPheValMetValValValLeu-192 |
| SEQ. ID. NO. 27481 | 207-ThrIleThrValIleAlaSerLeuMetGlyLeuAsnGluPheHisGlyValValGlyGluValProGlyIle-230 |
| SEQ. ID. NO. 27482 | 242-LeuPheThrValSer-246 |
| SEQ. ID. NO. 27483 | 260-PheAspSerThrGlyThr-265 |
| SEQ. ID. NO. 27484 | 362-MetLeuArgSerAlaArgAspIle-369 |

Antigenic Index - Jameson-Wolf

| | |
|---|---|
| SEQ. ID. NO. 27485 | 1-MetAspIleSerLysGlThrLeuLeu-9 |
| SEQ. ID. NO. 27486 | 16-LysAlaAsnGlyThrThrValArgThrGluLeu-26 |
| SEQ. ID. NO. 27487 | 125-LysValArgGluMetLeu-130 |
| SEQ. ID. NO. 27488 | 260-PheAspSerThrGly-264 |
| SEQ. ID. NO. 27489 | 277-ValAspGlyLysLeuProArgLeuLysArg-286 |
| SEQ. ID. NO. 27490 | 317-SerAlaGlyGlyArgThrGly-323 |
| SEQ. ID. NO. 27491 | 364-ArgSerAlaArgAspIleAspTrpAspAspMetThrGlu-376 |
| SEQ. ID. NO. 27492 | 410-LeuCysArgArgThrGlyAspValPro-418 |

Hydrophilic Regions - Hopp-Woods

| | |
|---|---|
| SEQ. ID. NO. 27493 | 1-MetAspIleSerLys-5 |
| SEQ. ID. NO. 27494 | 17-AlaAsnGlyThrThrValArgThrGluLeu-26 |
| SEQ. ID. NO. 27495 | 125-LysValArgGluMetLeu-130 |
| SEQ. ID. NO. 27496 | 279-GlyLysLeuProArgLeuLysArg-286 |
| SEQ. ID. NO. 27497 | 318-AlaGlyGlyArgThr-322 |
| SEQ. ID. NO. 27498 | 364-ArgSerAlaArgAspIleAspTrpAspAspMetThrGlu-376 |
| SEQ. ID. NO. 27499 | 410-LeuCysArgArgThrGlyAsp-416 | g098
AMPHI Regions - AMPHI

| | |
|---|---|
| SEQ. ID. NO. 27500 | 33-AspGlnPheValGlyAspValAlaArg-41 |
| SEQ. ID. NO. 27501 | 62-ThrHisHisValHisArgMetGly-69 |

Antigenic Index - Jameson-Wolf

| | |
|---|---|
| SEQ. ID. NO. 27502 | 25-GlnGlnAspAlaAlaGlnAlaGlyAspGlnPheVal-36 |
| SEQ. ID. NO. 27503 | 53-AsnAlaAlaGluHisGlyHisAlaGly-61 |
| SEQ. ID. NO. 27504 | 67-ArgMetGlyMetCysArg-72 |
| SEQ. ID. NO. 27505 | 79-AsnHisThrAspArgGlnAla-85 |

Hydrophilic Regions - Hopp-Woods

| | |
|---|---|
| SEQ. ID. NO. 27506 | 26-GlnAspAlaAlaGlnAla-31 |
| SEQ. ID. NO. 27507 | 54-AlaAlaGluHisGlyHis-59 |
| SEQ. ID. NO. 27508 | 79-AsnHisThrAspArgGlnAla-85 | g099
AMPHI Regions - AMPHI

| | |
|---|---|
| SEQ. ID. NO. 27509 | 6-SerMetMetArgLeuProAspIleVal-14 |
| SEQ. ID. NO. 27510 | 47-AlaPheValGluPhePheGlyGluGly-55 |
| SEQ. ID. NO. 27511 | 102-LysLeuValGluThrTyrAlaLysThr-110 |
| SEQ. ID. NO. 27512 | 114-TrpAlaGlyGlyLeuLys-119 |
| SEQ. ID. NO. 27513 | 135-ThrArgAsnMetAlaGlyProSerAsn-143 |
| SEQ. ID. NO. 27514 | 154-AlaAlaLysGlyLeuAlaLysProTyrGluGluProSerAspGlyGln-169 |
| SEQ. ID. NO. 27515 | 178-AlaAlaIleThrSerCysThrAsnThrSerAsnProArgAsnVal-192 |
| SEQ. ID. NO. 27516 | 251-ThrCysAsnGlyMetSer-256 |
| SEQ. ID. NO. 27517 | 341-IleAspAlaIleValAlaGluTyr-348 |
| SEQ. ID. NO. 27518 | 350-LysProGlnGlnPheArgAspIle-357 |
| SEQ. ID. NO. 27519 | 371-ProSerProLeuTyrAspTrpArg-378 |
| SEQ. ID. NO. 27520 | 381-SerThrTyrIleArg-385 |
| SEQ. ID. NO. 27521 | 398-ArgThrLeuArgGlyMetArgProPro-406 |
| SEQ. ID. NO. 27522 | 443-AspPheAsnSerTyrAlaThr-449 |
| SEQ. ID. NO. 27523 | 468-PheAsnGluMetValArg-473 |
| SEQ. ID. NO. 27524 | 494-MetArgMetTrpGluAlaIleGluThrTyrMet-504 |
| SEQ. ID. NO. 27525 | 532-ArgLeuAlaGlyValGluAlaIle-539 |
| SEQ. ID. NO. 27526 | 541-AlaGluGlyPheGluArgIleHisArgThrAsn-551 |
| SEQ. ID. NO. 27527 | 575-GlyThrGluThrTyr-579 |

TABLE 1-continued

Antigenic Index - Jameson-Wolf
SEQ. ID. NO. 27528  18-LeuThrGlyLysArgGlnAla-24
SEQ. ID. NO. 27529  38-PheLeuArgLysGluArgValVal-45
SEQ. ID. NO. 27530  53-GlyGluGlyAlaArgSer-58
SEQ. ID. NO. 27531  60-SerIleGlyAspArgAlaThr-66
SEQ. ID. NO. 27532  70-MetThrProGluPhe-74
SEQ. ID. NO. 27533  94-ThrGlyArgAspAspAlaGlnValLysLeu-103
SEQ. ID. NO. 27534  133-SerValThrArgAsnMetAlaGlyProSerAsnProHis-145
SEQ. ID. NO. 27535  157-GlyLeuAlaLysProTyrGluGluProSerAspGlyGlnMetProAspGly-173
SEQ. ID. NO. 27536  183-CysThrAsnThrSerAsnProArgAsnVal-192
SEQ. ID. NO. 27537  201-AsnAlaAsnArgLeuGlyLeuLysArgLysProTrpVal-213
SEQ. ID. NO. 27538  216-SerPheAlaProGlySerLysValAla-224
SEQ. ID. NO. 27539  235-ProGluMetGluLysLeu-240
SEQ. ID. NO. 27540  251-ThrCysAsnGlyMetSerGlyAlaLeuAspProLysIleGlnGlnGluIleIleAspArgAspLeuTyr-273
SEQ. ID. NO. 27541  279-SerGlyAsnArgAsnPheAspGlyArgIleHisProTyrAlaLys-293
SEQ. ID. NO. 27542  312-IleArgPheAspIleGluAsnAspVal-320
SEQ. ID. NO. 27543  322-GlyValAlaAspGlyArgGluIleArgLeuLysAspIleTrpProThrAspGluGluIleAsp-342
SEQ. ID. NO. 27544  348-TyrValLysProGlnGlnPheArgAsp-356
SEQ. ID. NO. 27545  361-MetSerAspThrGlyThrAlaGlnLysAlaProSerProLeuTyrAspTrpArgProMetSerThrTyrIleArgArgProProTyrTrp-390
SEQ. ID. NO. 27546  394-LeuAlaGlyGluArgThrLeuArgGlyMetArgProProAlaIleLeuProAspAsnIleThrThrAspHisIleSerProSerAsn-422
SEQ. ID. NO. 27547  438-GlyLeuProGluGluAspPheAsnSerTyrAlaThrHisArgGlyAspHisLeuThr-456
SEQ. ID. NO. 27548  463-AlaAsnProLysLeuPhe-468
SEQ. ID. NO. 27549  471-MetValArgAsnGluAspGlySerValArgGlnGlySerLeuAlaArgValGluProGluGlyGlnThr-493
SEQ. ID. NO. 27550  503-TyrMetAsnArgLysGlnPro-509
SEQ. ID. NO. 27551  516-AlaAspTyrGlyGlnGlySerSerArgAspTrpAlaAlaLysGlyValArg-532
SEQ. ID. NO. 27552  542-GluGlyPheGluArgIleHisArgThrAsnLeu-552
SEQ. ID. NO. 27553  562-PheLysProGlyThrAsnArgHisThrLeuGlnLeuAspGlyThrGluThrTyrAspValValGlyGluArgThrProArgCysGly-590
SEQ. ID. NO. 27554  595-IleHisArgLysAsnGlyGluThrValGlu-604
SEQ. ID. NO. 27555  607-ValThrCysArgProAspThrAlaGluGlu-616
Hydrophilic Regions - Hopp-Woods
SEQ. ID. NO. 27556  18-LeuThrGlyLysArgGlnAla-24
SEQ. ID. NO. 27557  38-PheLeuArgLysGluArgValVal-45
SEQ. ID. NO. 27558  53-GlyGluGlyAlaArg-57
SEQ. ID. NO. 27559  60-SerIleGlyAspArgAlaThr-66
SEQ. ID. NO. 27560  94-ThrGlyArgAspAspAlaGlnValLysLeu-103
SEQ. ID. NO. 27561  157-GlyLeuAlaLysProTyrGluGluProSerAspGlyGlnMetPro-171
SEQ. ID. NO. 27562  205-LeuGlyLeuLysArgLysProTrpVal-213
SEQ. ID. NO. 27563  235-ProGluMetGluLysLeu-240
SEQ. ID. NO. 27564  259-LeuAspProLysIleGlnGlnGluIleIleAspArgAspLeuTyr-273
SEQ. ID. NO. 27565  282-ArgAsnPheAspGlyArgIle-288
SEQ. ID. NO. 27566  312-IleArgPheAspIleGluAsnAspVal-320
SEQ. ID. NO. 27567  324-AlaAspGlyArgGluIleArgLeuLysAsp-333
SEQ. ID. NO. 27568  335-TrpProThrAspGluGluIleAsp-342
SEQ. ID. NO. 27569  363-AspThrGlyThrAlaGlnLysAlaPro-371
SEQ. ID. NO. 27570  394-LeuAlaGlyGluArgThrLeuArgGlyMetArg-404
SEQ. ID. NO. 27571  438-GlyLeuProGluGluAspPheAsn-445
SEQ. ID. NO. 27572  450-HisArgGlyAspHis-454
SEQ. ID. NO. 27573  471-MetValArgAsnGluAspGlySerValArgGln-481
SEQ. ID. NO. 27574  485-AlaArgValGluProGluGlyGlnThr-493
SEQ. ID. NO. 27575  503-TyrMetAsnArgLysGlnPro-509
SEQ. ID. NO. 27576  518-TyrGlyGlnGlySerSerArgAspTrpAlaAlaLysGlyValArg-532
SEQ. ID. NO. 27577  542-GluGlyPheGluArgIleHisArg-549
SEQ. ID. NO. 27578  564-ProGlyThrAsnArgHis-569
SEQ. ID. NO. 27579  574-AspGlyThrGluThr-578
SEQ. ID. NO. 27580  580-AspValValGlyGluArgThrProArg-588
SEQ. ID. NO. 27581  596-HisArgLysAsnGlyGluThrValGlu-604
SEQ. ID. NO. 27582  609-CysArgProAspThrAlaGluGlu-616
g102
AMPHI Regions - AMPHI
SEQ. ID. NO. 27583  26-ProAsnProThrAlaAsnLeuGlyAspGlyLeu-36
SEQ. ID. NO. 27584  70-PheAspThrMetValLysAspLeuLeuGlyArgGlyTrpAsnIleIleAsnGlyIleAla-89
SEQ. ID. NO. 27585  109-ThrAlaLysGlyIleGlySerAlaVal-117
SEQ. ID. NO. 27586  128-LeuValPhePheGlyIleLeuAlaPheCys-137
SEQ. ID. NO. 27587  144-LeuValAlaAspArgPheThrGlyValLeu-152
SEQ. ID. NO. 27588  155-GlyMetValLeuThr-159
SEQ. ID. NO. 27589  207-AsnValSerSerLeuLeuLysTyrPheLys-216
SEQ. ID. NO. 27590  221-LysValAlaLysSerIle-226
SEQ. ID. NO. 27591  266-LeuAsnGluThrLeuSerLysPheAlaGlnThrGlyAspMetAspLysIleLeuSerLeuPheProTyr-288
SEQ. ID. NO. 27592  300-LeuGlyLeuPheAspAsnIleAlaAspIlePheLysTrpAsnAsp-314
SEQ. ID. NO. 27593  316-MetSerGlyArgGly-320
SEQ. ID. NO. 27594  342-PhePheThrAlaIleGlyAla-348
SEQ. ID. NO. 27595  374-GlyAlaGlyLysThrTyrLysVal-381
Antigenic Index - Jameson-Wolf
SEQ. ID. NO. 27596  1-MetSerAlaLysThrProSerLeu-8
SEQ. ID. NO. 27597  26-ProAsnProThrAlaAsnLeuGlyAspGlyLeu-36
SEQ. ID. NO. 27598  62-ThrHisAsnProArgGlyAlaSer-69
SEQ. ID. NO. 27599  77-LeuLeuGlyArgGly-81
SEQ. ID. NO. 27600  106-GlyAspLeuThrAla-110
SEQ. ID. NO. 27601  169-AlaAspAlaLysPro-173
SEQ. ID. NO. 27602  179-ThrGlnAlaProValGlyThr-185

TABLE 1-continued

| | |
|---|---|
| SEQ. ID. NO. 27603 | 214-TyrPheLysGlyAspAlaProLysValAla-223 |
| SEQ. ID. NO. 27604 | 246-SerAsnLeuProArgAsnGluPhe-253 |
| SEQ. ID. NO. 27605 | 258-AlaAlaGluArgGlnLeu-263 |
| SEQ. ID. NO. 27606 | 274-AlaGlnThrGlyAspMetAspLys-281 |
| SEQ. ID. NO. 27607 | 311-LysTrpAsnAspSerMetSerGlyArgGlyThrLys-322 |
| SEQ. ID. NO. 27608 | 369-SerProGlnLysIleGlyAlaGlyLysThrTyr-379 |

Hydrophilic Regions - Hopp-Woods

| | |
|---|---|
| SEQ. ID. NO. 27609 | 1-MetSerAlaLysThr-5 |
| SEQ. ID. NO. 27610 | 62-ThrHisAsnProArgGlyAlaSer-69 |
| SEQ. ID. NO. 27611 | 169-AlaAspAlaLysPro-173 |
| SEQ. ID. NO. 27612 | 215-PheLysGlyAspAlaProLysValAla-223 |
| SEQ. ID. NO. 27613 | 247-AsnLeuProArgAsnGluPhe-253 |
| SEQ. ID. NO. 27614 | 258-AlaAlaGluArgGlnLeu-263 |
| SEQ. ID. NO. 27615 | 277-GlyAspMetAspLys-281 |
| SEQ. ID. NO. 27616 | 316-MetSerGlyArgGlyThrLys-322 |
| SEQ. ID. NO. 27617 | 371-GlnLysIleGlyAla-375 | g105
AMPHI Regions - AMPHI

| | |
|---|---|
| SEQ. ID. NO. 27618 | 11-TrpValGlyLeuGly-15 |
| SEQ. ID. NO. 27619 | 22-ValThrArgLeuLeuAsp-27 |
| SEQ. ID. NO. 27620 | 51-LysValTyrGlySerThrAlaGluLeuValArgAlaCys-63 |
| SEQ. ID. NO. 27621 | 74-AlaAlaValCysAspIleLeuAsnGlyValArgAspGlyLeu-87 |
| SEQ. ID. NO. 27622 | 97-ThrIleSerProThr-101 |
| SEQ. ID. NO. 27623 | 110-ValGluAlaAlaGlyGlyGlnPheAlaGluAlaProVal-122 |
| SEQ. ID. NO. 27624 | 143-AlaValLeuAsnProLeuGlnLysIlePheSer-153 |
| SEQ. ID. NO. 27625 | 162-PheGlyAspValGlyLysGlySer-169 |
| SEQ. ID. NO. 27626 | 176-AsnSerLeuLeuGlyIlePheGlyGluAlaTyr-186 |
| SEQ. ID. NO. 27627 | 203-IleValGluAlaIleGlyGlySerAla-211 |
| SEQ. ID. NO. 27628 | 249-LeuGluGlnAlaGlyAsnThrLeuProAlaValGlu-260 |
| SEQ. ID. NO. 27629 | 263-AlaAlaSerTyrArgLysAlaValGluAla-272 |

Antigenic Index - Jameson-Wolf

| | |
|---|---|
| SEQ. ID. NO. 27630 | 25-LeuLeuAspGlyGlyIleGlu-31 |
| SEQ. ID. NO. 27631 | 34-ValTyrAsnArgSerProAspLysThrAlaProIleSerAlaLysGlyAlaLysValTyrGlySer-55 |
| SEQ. ID. NO. 27632 | 81-AsnGlyValArgAspGlyLeuAla-88 |
| SEQ. ID. NO. 27633 | 96-SerThrIleSerProThrGluAsnLeuAla-105 |
| SEQ. ID. NO. 27634 | 121-ProValSerGlySerValGlyProAlaThr-130 |
| SEQ. ID. NO. 27635 | 139-GlyGlySerGluAla-143 |
| SEQ. ID. NO. 27636 | 155-ValGlyLysLysThrPheHisPheGlyAspValGlyLysGlySerGly-170 |
| SEQ. ID. NO. 27637 | 196-PheGlyIleAspThrAspThrIleVal-204 |
| SEQ. ID. NO. 27638 | 210-SerAlaMetAspSerProMetPheGlnThrLysLysSerLeuTrpAlaAsnArgGluPheProPro-231 |
| SEQ. ID. NO. 27639 | 237-HisAlaSerLysAspLeuAsnLeuAlaValLysGluLeuGluGlnAlaGlyAsnThrLeuPro-257 |
| SEQ. ID. NO. 27640 | 264-AlaSerTyrArgLysAlaValGluAlaGlyTyrGlyGluGlnAspValSerGly-281 |

Hydrophilic Regions - Hopp-Woods

| | |
|---|---|
| SEQ. ID. NO. 27641 | 25-LeuLeuAspGlyGlyIle-30 |
| SEQ. ID. NO. 27642 | 37-ArgSerProAspLysThrAlaProIleSerAlaLysGlyAlaLys-51 |
| SEQ. ID. NO. 27643 | 81-AsnGlyValArgAspGlyLeuAla-88 |
| SEQ. ID. NO. 27644 | 164-AspValGlyLysGlySerGly-170 |
| SEQ. ID. NO. 27645 | 196-PheGlyIleAspThrAspThrIle-203 |
| SEQ. ID. NO. 27646 | 218-GlnThrLysLysSerLeuTrpAla-225 |
| SEQ. ID. NO. 27647 | 237-HisAlaSerLysAspLeuAsnLeuAlaValLysGluLeuGluGlnAlaGly-253 |
| SEQ. ID. NO. 27648 | 265-SerTyrArgLysAlaValGlu-271 |
| SEQ. ID. NO. 27649 | 273-GlyTyrGlyGluGlnAspVal-279 | g109-2
AMPHI Regions - AMPHI

| | |
|---|---|
| SEQ. ID. NO. 27650 | 6-GlyThrTyrArgAspLeuHisArgProAlaSerGlu-17 |
| SEQ. ID. NO. 27651 | 53-LeuIleProAlaMetAlaGlyThrIleGly-62 |
| SEQ. ID. NO. 27652 | 143-GlyLeuLeuMetAla-147 |
| SEQ. ID. NO. 27653 | 154-IleMetAlaLysLeuThrSer-160 |
| SEQ. ID. NO. 27654 | 175-GlyThrThrGlyGlnValLysLysLeuPheSerTrpAlaGly-188 |
| SEQ. ID. NO. 27655 | 205-ValMetTyrAlaLeuLeuGluHisTrpLysLysArgTrpLeu-218 |
| SEQ. ID. NO. 27656 | 220-ValProLeuGlyCys-224 |
| SEQ. ID. NO. 27657 | 292-HisGlnValPheGlnLysIle-298 |
| SEQ. ID. NO. 27658 | 324-ValGlySerIleLeuGly-329 |
| SEQ. ID. NO. 27659 | 334-ThrSerSerTrpGlyThr-339 |
| SEQ. ID. NO. 27660 | 465-AlaValGlyMetLeuProGlyIleProProPheLeuGluGlnPheLysSerLeu-482 |

Antigenic Index - Jameson-Wolf

| | |
|---|---|
| SEQ. ID. NO. 27661 | 1-MetGluLysHisAsnGlyThrTyrArgAspLeuHisArgProAlaSer-16 |
| SEQ. ID. NO. 27662 | 18-PheAlaThrArgAspGluTyrLeuGlu-26 |
| SEQ. ID. NO. 27663 | 32-MetGlnProLysArgTrpArgProAsnLeuProPheArgAspTyrArgPheGluTrp-50 |
| SEQ. ID. NO. 27664 | 76-LeuGlyLeuProAsp-80 |
| SEQ. ID. NO. 27665 | 107-ProGlyAlaAsnLeuProGlyThrHis-115 |
| SEQ. ID. NO. 27666 | 158-LeuThrSerAsnGlyVal-163 |
| SEQ. ID. NO. 27667 | 177-ThrGlyGlnValLysLys-182 |
| SEQ. ID. NO. 27668 | 243-AlaProGlyLeuProPro-248 |
| SEQ. ID. NO. 27669 | 254-TrpXxxGlyGluAsnSerGlyTrpHis-262 |
| SEQ. ID. NO. 27670 | 299-SerTyrProGluLysThrAspLysVal-307 |
| SEQ. ID. NO. 27671 | 310-AsnIleAspAspThrMetThr-316 |
| SEQ. ID. NO. 27672 | 350-ProIleProGlyGly-354 |
| SEQ. ID. NO. 27673 | 392-AlaGlyMetGluMetThrArgLysGlyLysThrThrGln-404 |
| SEQ. ID. NO. 27674 | 435-GlyCysLysGluArgSerAla-441 |

TABLE 1-continued

Hydrophilic Regions - Hopp-Woods
SEQ. ID. NO. 27675   1-MetGluLysHisAsnGlyThrTyrArgAspLeuHisArgProAlaSer-16
SEQ. ID. NO. 27676   18-PheAlaThrArgAspGluTyrLeuGlu-26
SEQ. ID. NO. 27677   35-LysArgTrpArgPro-39
SEQ. ID. NO. 27678   44-ArgAspTyrArgPheGluTrp-50
SEQ. ID. NO. 27679   178-GlyGlnValLysLys-182
SEQ. ID. NO. 27680   299-SerTyrProGluLysThrAspLysVal-307
SEQ. ID. NO. 27681   311-IleAspAspThrMetThr-316
SEQ. ID. NO. 27682   392-AlaGlyMetGluMetThrArgLysGlyLysThrThrGln-404
SEQ. ID. NO. 27683   435-GlyCysLysGluArgSerAla-441
g111-2
AMPHI Regions - AMPHI
SEQ. ID. NO. 27684   6-ArgLeuProAsnLeuIleArgAlaLeu-14
SEQ. ID. NO. 27685   58-ProSerProAlaLysIleGlnLysArgIleAspAspAlaLeuLysGluValAsnArgGlnMetSer-79
SEQ. ID. NO. 27686   90-PheAsnGlnHisThrAlaGly-96
SEQ. ID. NO. 27687   128-GlyProLeuValAsnLeuTrp-134
SEQ. ID. NO. 27688   151-IleLysGlnAlaAlaSerTyrThrGly-159
SEQ. ID. NO. 27689   170-AspTyrAlaSerLeu-174
SEQ. ID. NO. 27690   183-LeuAspLeuSerSerIleAlaLys-190
SEQ. ID. NO. 27691   209-TyrLeuValGluIleGlyGly-215
SEQ. ID. NO. 27692   314-GluThrGluAlaLeu-318
SEQ. ID. NO. 27693   320-LeuAlaGluGlnGlu-324
Antigenic Index - Jameson-Wolf
SEQ. ID. NO. 27694   1-MetProSerGluThrArgLeuProAsnLeu-10
SEQ. ID. NO. 27695   26-CysSerGluGlnThrAla-31
SEQ. ID. NO. 27696   37-GlnGlyGluThrMetGly-42
SEQ. ID. NO. 27697   49-TyrLeuSerAsnAsnArgAspLysLeuProSerProAlaLysIleGlnLysArgIleAspAspAlaLeuLysGluValAsnArgGlnMetSer-79
SEQ. ID. NO. 27698   81-TyrGlnThrAspSerGluIleSerArgPheAsnGlnHisThrAlaGlyLysProLeuArgIleSerSerAspPhe-105
SEQ. ID. NO. 27699   111-GluAlaValArgLeuAsnArg-117
SEQ. ID. NO. 27700   135-GlyPheGlyProAspLysSerValThrArgGluProSerProGluGlnIleLysGln-153
SEQ. ID. NO. 27701   164-IleLeuGlnGlnGlyLysAspTyrAlaSerLeuSerLysThrHisProLysAla-181
SEQ. ID. NO. 27702   192-PheGlyValAspLysValAlaGlyGluLeuGluLysTyrGly-205
SEQ. ID. NO. 27703   213-IleGlyGlyGluLeuHisGlyLysGlyLysAsnAlaHisGlyLysGluProTrpArgIleGlyIleGluGlnProAsn-237
SEQ. ID. NO. 27704   250-LeuAsnAsnArgSerLeuAlaThrSerGlyAspTyrArg-262
SEQ. ID. NO. 27705   264-PheHisValAspLysAsnGlyLysArgLeuSer-274
SEQ. ID. NO. 27706   277-IleAsnProAsnAsnLysArgProIleSer-286
SEQ. ID. NO. 27707   295-ValSerAspSerAlaMetThrAlaAspGlyLeuSer-306
SEQ. ID. NO. 27708   314-GluThrGluAlaLeuArgLeuAlaGluGlnGluLys-325
SEQ. ID. NO. 27709   332-ValArgAspLysAspGlyTyrArg-339
SEQ. ID. NO. 27710   342-MetSerSerGluPhe-346
Hydrophilic Regions - Hopp-Woods
SEQ. ID. NO. 27711   1-MetProSerGluThrArgLeu-7
SEQ. ID. NO. 27712   26-CysSerGluGlnThrAla-31
SEQ. ID. NO. 27713   51-SerAsnAsnArgAspLysLeuProSer-59
SEQ. ID. NO. 27714   61-AlaLysIleGlnLysArgIleAspAspAlaLeuLysGluValAsnArgGln-77
SEQ. ID. NO. 27715   82-GlnThrAspSerGluIleSerArg-89
SEQ. ID. NO. 27716   97-LysProLeuArgIleSerSer-103
SEQ. ID. NO. 27717   111-GluAlaValArgLeuAsnArg-117
SEQ. ID. NO. 27718   137-GlyProAspLysSerValThrArgGluProSerProGluGlnIleLysGln-153
SEQ. ID. NO. 27719   167-GlnGlyLysAspTyrAlaSer-173
SEQ. ID. NO. 27720   175-SerLysThrHisPro-179
SEQ. ID. NO. 27721   192-PheGlyValAspLysValAlaGlyGluLeuGluLysTyrGly-205
SEQ. ID. NO. 27722   217-LeuHisGlyLysGlyLysAsnAlaHis-225
SEQ. ID. NO. 27723   267-AspLysAsnGlyLysArgLeuSer-274
SEQ. ID. NO. 27724   279-ProAsnAsnLysArgProIle-285
SEQ. ID. NO. 27725   314-GluThrGluAlaLeuArgLeuAlaGluGlnGluLys-325
SEQ. ID. NO. 27726   332-ValArgAspLysAspGlyTyrArg-339
g117-1
AMPHI Regions - AMPHI
SEQ. ID. NO. 27727   6-ProIleGlnAspThrGlnSerAla-13
SEQ. ID. NO. 27728   15-LeuGlnGluLeuArgGluTrpPheAspSerTyrCysAla-27
SEQ. ID. NO. 27729   57-GlyGluProLeuProAspHis-63
SEQ. ID. NO. 27730   69-GlnMetValAspGluLeuAspLeuLeu-77
SEQ. ID. NO. 27731   79-AspAlaValAlaAlaThrLeuLeuAlaAspIleGlyArgTyr-92
SEQ. ID. NO. 27732   104-CysAsnSerThrValAlaGluLeuValLysGlyValAspGluValGlnLysLeuThrHisPheAlaArgValAspSerLeu-130
SEQ. ID. NO. 27733   145-LysMetLeuLeuAlaMet-150
SEQ. ID. NO. 27734   170-PheLeuSerAsnAlaProAspSerProGluLys-180
SEQ. ID. NO. 27735   216-GluProGluLysTyrArg-221
SEQ. ID. NO. 27736   234-ArgLeuGluTyrIleGluAsnPheLeuAspIleLeuArg-246
SEQ. ID. NO. 27737   260-GlyArgProLysHisIleTyrSerIleTyrLys-270
SEQ. ID. NO. 27738   282-LeuPheAspIleArg-286
SEQ. ID. NO. 27739   290-IleLeuValAspThrValProGluCysTyrThrThrLeuGlyIleValHisSerLeuTrpGlnProIleProGlyGluPheAspAspTyrIleAla-321
SEQ. ID. NO. 27740   327-GlyTyrLysSerLeuHisThr-333
SEQ. ID. NO. 27741   351-AspMetHisGlnPheAsnGluPheGlyValAla-361
SEQ. ID. NO. 27742   385-GlnLeuLeuAspTrp-389
SEQ. ID. NO. 27743   440-HisSerSerIleGlyAspArg-446
SEQ. ID. NO. 27744   489-ValLysSerGlyLysAlaIleGlyLysIleArgAlaTyr-501
SEQ. ID. NO. 27745   504-GlnGlnAsnAlaAsp-508
SEQ. ID. NO. 27746   521-GlnLeuAlaLysLeu-525
SEQ. ID. NO. 27747   532-GlnGluLeuAlaGlu-536

TABLE 1-continued

| | |
|---|---|
| SEQ. ID. NO. 27748 | 539-GlyTyrLysLysProGluAspLeuTyrThr-548 |
| SEQ. ID. NO. 27749 | 557-AsnArgAlaIleGlnLysAlaCysGlyThrLeuAsnGluProPro-571 |
| SEQ. ID. NO. 27750 | 585-LysIleLysLysGlyGly-590 |
| SEQ. ID. NO. 27751 | 603-MetThrThrLeuAlaLysCysCysLysProAlaProProAspAspIleAlaGly-620 |
| SEQ. ID. NO. 27752 | 637-SerPheArgHisLeuAlaGluHisAlaProGluLysValLeuAspAla-652 |
| SEQ. ID. NO. 27753 | 679-ArgAspValSerAspAla-684 |
| SEQ. ID. NO. 27754 | 714-GlnValAsnAspLeuProArgValLeuAlaGlyLeuGlyAspValLysGlyValLeuSerValThrArg-736 |
| Antigenic I Index - Jameson-Wolf | |
| SEQ. ID. NO. 27755 | 5-SerProIleGlnAspThrGlnSerAlaThr-14 |
| SEQ. ID. NO. 27756 | 16-GlnGluLeuArgGluTrpPheAspSerTyrCysAlaAlaLeuProAspAsnAspLysAsnLeu-36 |
| SEQ. ID. NO. 27757 | 46-GluHisTyrProAla-50 |
| SEQ. ID. NO. 27758 | 52-AlaAlaThrProTyrGlyGluProLeuProAspHisPhe-64 |
| SEQ. ID. NO. 27759 | 70-MetValAspGluLeuAspLeuLeuPro-78 |
| SEQ. ID. NO. 27760 | 88-AspIleGlyArgTyrValProAspTrp-96 |
| SEQ. ID. NO. 27761 | 100-ValSerGluArgCysAsnSerThrVal-108 |
| SEQ. ID. NO. 27762 | 110-GluLeuValLysGlyValAspGluValGlnLys-120 |
| SEQ. ID. NO. 27763 | 125-AlaArgValAspSerLeuAlaThrProGluGluArgAlaGlnGlnAlaGluThrMetArg-144 |
| SEQ. ID. NO. 27764 | 162-AlaMetArgThrArgThr-167 |
| SEQ. ID. NO. 27765 | 173-AsnAlaProAspSerProGluLysArgAlaValAlaLysGluThrLeu-188 |
| SEQ. ID. NO. 27766 | 209-AspLeuGlyPheArgHisGlnGluProGluLysTyrArgGlu-222 |
| SEQ. ID. NO. 27767 | 227-LeuArgGluLysArgThrGluArgLeuGluTyr-237 |
| SEQ. ID. NO. 27768 | 245-LeuArgThrGluLeuLysLys-251 |
| SEQ. ID. NO. 27769 | 258-ValAlaGlyArgProLysHis-264 |
| SEQ. ID. NO. 27770 | 271-LysMetValLysLysLysLeuSerPhe-279 |
| SEQ. ID. NO. 27771 | 294-ThrValProGluCysTyr-299 |
| SEQ. ID. NO. 27772 | 311-ProIleProGlyGluPheAspAspTyrIleAlaAsnProLysGlyAsnGlyTyrLysSer-330 |
| SEQ. ID. NO. 27773 | 335-IleValGlyProGluGluLysGlyValGluValGlnIleArgThr-349 |
| SEQ. ID. NO. 27774 | 364-TrpArgTyrLysGluGlyGlyLysGlyAspSerAlaTyrGluGlnLys-379 |
| SEQ. ID. NO. 27775 | 387-LeuAspTrpArgGluAsnMetAlaGluSerGlyLysGluAspLeuAlaAla-403 |
| SEQ. ID. NO. 27776 | 418-ThrProHisGlyLys-422 |
| SEQ. ID. NO. 27777 | 440-HisSerSerIleGlyAspArgCysArgGlyAlaLysValGluGly-454 |
| SEQ. ID. NO. 27778 | 461-ThrProLeuGluAsnGlyGlnArgValGluIleIleThrAlaLysGluGlyHisProSerValAsn-482 |
| SEQ. ID. NO. 27779 | 487-GlyTrpValLysSerGlyLysAlaIleGlyLys-497 |
| SEQ. ID. NO. 27780 | 502-IleArgGlnGlnAsnAlaAspThrValArgGluGluGlyArgValGlnLeuAspLysGlnLeuAla-523 |
| SEQ. ID. NO. 27781 | 525-LeuThrProLysProAsnLeuGlnGluLeuAlaGlu-536 |
| SEQ. ID. NO. 27782 | 538-LeuGlyTyrLysLysProGluAspLeu-546 |
| SEQ. ID. NO. 27783 | 551-GlyGlnGlyGluIleSerAsnArgAlaIleGlnLysAlaCysGlyThrLeuAsnGluProProVal-573 |
| SEQ. ID. NO. 27784 | 582-LysGlnSerLysIleLysLysGlyGlyLysThr-592 |
| SEQ. ID. NO. 27785 | 596-IleAspGlyGluAspGlyLeu-602 |
| SEQ. ID. NO. 27786 | 608-LysCysCysLysProAlaProProAspAspIleAla-619 |
| SEQ. ID. NO. 27787 | 622-ValThrArgGluArgGlyIleSerValHisArgLysThrCysProSerPhe-638 |
| SEQ. ID. NO. 27788 | 644-HisAlaProGluLysValLeuAsp-651 |
| SEQ. ID. NO. 27789 | 667-IleGluIleArgAlaGlnAspArgSerGlyLeuLeuArgAspValSerAspAlaLeuAlaArgHisLysLeu-690 |
| SEQ. ID. NO. 27790 | 696-GlnThrGlnSerArgAspLeuGluAlaSerMet-706 |
| SEQ. ID. NO. 27791 | 710-LeuGluValLysGlnValAsnAspLeuProArg-720 |
| SEQ. ID. NO. 27792 | 726-GlyAspValLysGly-730 |
| Hydrophilic Regions - Hopp-Woods | |
| SEQ. ID. NO. 27793 | 8-GlnAspThrGlnSer-12 |
| SEQ. ID. NO. 27794 | 16-GlnGluLeuArgGluTrpPhe-22 |
| SEQ. ID. NO. 27795 | 30-ProAspAsnAspLysAsnLeu-36 |
| SEQ. ID. NO. 27796 | 70-MetValAspGluLeuAspLeuLeuPro-78 |
| SEQ. ID. NO. 27797 | 100-ValSerGluArgCysAsnSerThr-107 |
| SEQ. ID. NO. 27798 | 110-GluLeuValLysGlyValAspGluValGlnLys-120 |
| SEQ. ID. NO. 27799 | 125-AlaArgValAspSer-129 |
| SEQ. ID. NO. 27800 | 131-AlaThrProGluGluArgAlaGlnGlnAlaGluThrMetArg-144 |
| SEQ. ID. NO. 27801 | 162-AlaMetArgThrArgThr-167 |
| SEQ. ID. NO. 27802 | 174-AlaProAspSerProGluLysArgAlaValAlaLysGluThrLeu-188 |
| SEQ. ID. NO. 27803 | 209-AspLeuGlyPheArgHisGlnGluProGluLysTyrArgGlu-222 |
| SEQ. ID. NO. 27804 | 227-LeuAspGluLysArgThrGluArgLeuGluTyr-237 |
| SEQ. ID. NO. 27805 | 245-LeuArgThrGluLeuLysLys-251 |
| SEQ. ID. NO. 27806 | 258-ValAlaGlyArgProLysHis-264 |
| SEQ. ID. NO. 27807 | 271-LysMetValLysLysLysLeuSerPhe-279 |
| SEQ. ID. NO. 27808 | 314-GlyGluPheAspAsp-318 |
| SEQ. ID. NO. 27809 | 323-ProLysGlyAsnGly-327 |
| SEQ. ID. NO. 27810 | 337-GlyProGluGluLysGlyValGluValGlnIleArgThr-349 |
| SEQ. ID. NO. 27811 | 365-ArgTyrLysGluGlyGlyLysGlyAspSerAlaTyrGluGln-378 |
| SEQ. ID. NO. 27812 | 387-LeuAspTrpArgGluAsnMetAlaGluSerGlyLysGluAspLeuAlaAla-403 |
| SEQ. ID. NO. 27813 | 443-IleGlyAspArgCysArgGlyAlaLysValGluGly-454 |
| SEQ. ID. NO. 27814 | 463-LeuGluAsnGlyGlnArgValGluIleIleThrAlaLysGluGlyHisPro-479 |
| SEQ. ID. NO. 27815 | 489-ValLysSerGlyLysAlaIleGlyLys-497 |
| SEQ. ID. NO. 27816 | 505-GlnAsnAlaAspThrValArgGluGluGlyArgValGlnLeuAspLysGlnLeuAla-523 |
| SEQ. ID. NO. 27817 | 538-LeuGlyTyrLysLysProGluAspLeu-546 |
| SEQ. ID. NO. 27818 | 553-GlyGluIleSerAsn-557 |
| SEQ. ID. NO. 27819 | 582-LysGlnSerLysIleLysLysGlyGlyLys-591 |
| SEQ. ID. NO. 27820 | 596-IleAspGlyGluAspGlyLeu-602 |
| SEQ. ID. NO. 27821 | 608-LysCysCysLysProAlaProProAspAspIle-618 |
| SEQ. ID. NO. 27822 | 622-ValThrArgGluArgGlyIleSerValHisArgLysThrCysPro-636 |
| SEQ. ID. NO. 27823 | 644-HisAlaProGluLysValLeu-650 |
| SEQ. ID. NO. 27824 | 667-IleGluIleArgAlaGlnAspArgSerGlyLeuLeuArgAspValSerAspAlaLeuAlaArgHisLysLeu-690 |
| SEQ. ID. NO. 27825 | 697-ThrGlnSerArgAspLeuGluAlaSerMet-706 |

TABLE 1-continued

| SEQ. ID. NO. 27826 | 710-LeuGluValLysGlnValAsnAspLeuProArg-720 |
| SEQ. ID. NO. 27827 | 726-GlyAspValLysGly-730 | g118
AMPHI Regions - AMPHI
| SEQ. ID. NO. 27828 | 24-GlyLysTrpTyrAsp-28 |
| SEQ. ID. NO. 27829 | 57-IleProArgAspIle-61 |
| SEQ. ID. NO. 27830 | 65-IleGlyThrIleIleAspPheLeuMetValProAsn-76 |
| SEQ. ID. NO. 27831 | 94-IleHisGluArgTyrGluArgPheThrThrMetLeuArg-106 |

Antigenic Index - Jameson-Wolf
| SEQ. ID. NO. 27832 | 2-CysGluPheLysAspPheArgArgAsnIleProCys-13 |
| SEQ. ID. NO. 27833 | 15-GluGluTyrAspGluAsnSerPhe-22 |
| SEQ. ID. NO. 27834 | 24-GlyLysTrpTyrAspAspGlyValTrpAspAspGluGluTyrTrpLysLeuGluAsnAspLeuIleGluValArgArgLysTyrProTyrPro MetAspIleProArgAspIle-61 |
| SEQ. ID. NO. 27835 | 86-ProTrpLeuProAspSerValGlyIleHisGluArgTyrGluArg-100 |
| SEQ. ID. NO. 27836 | 109-PheThrGluLysAspIleVal-115 |
| SEQ. ID. NO. 27837 | 119-PheAspTyrTyrAsnLysLys-125 |

Hydrophilic Regions - Hopp-Woods
| SEQ. ID. NO. 27838 | 2-CysGluPheLysAspPheArgArgAsnIleProCys-13 |
| SEQ. ID. NO. 27839 | 15-GluGluTyrAspGlu-19 |
| SEQ. ID. NO. 27840 | 30-GlyValTrpAspAspGluGluTyrTrpLysLeuGluAsnAspLeuIleGluValArgArgLysTyrProTyr-53 |
| SEQ. ID. NO. 27841 | 96-GluArgTyrGluArg-100 |
| SEQ. ID. NO. 27842 | 109-PheThrGluLysAspIleVal-115 |
| SEQ. ID. NO. 27843 | 121-TyrTyrAsnLysLys-125 | g120
AMPHI Regions - AMPHI
| SEQ. ID. NO. 27844 | 6-LysAsnIlePheSerAla-11 |
| SEQ. ID. NO. 27845 | 49-SerGlyAsnAlaTyrLysIleValSerThrIleLys-60 |
| SEQ. ID. NO. 27846 | 77-AsnThrLeuHisProAlaTyrTyrLysAspIleArgArg-89 |
| SEQ. ID. NO. 27847 | 142-IleThrAsnGlyLysLysLeuTyrSerValGlyGlyLeuAsnLysAlaGly-158 |
| SEQ. ID. NO. 27848 | 188-AlaProSerLeuAsnAsnIleProAla-196 |

Antigenic Index - Jameson-Wolf
| SEQ. ID. NO. 27849 | 35-SerGlySerTyrGly-39 |
| SEQ. ID. NO. 27850 | 45-ThrPheGluArgSerGlyAsnAlaTyrLys-54 |
| SEQ. ID. NO. 27851 | 68-PheGluSerGlyGlyThrValVal-75 |
| SEQ. ID. NO. 27852 | 83-TyrTyrLysAspIleArgArgGlyLysLeuTyrAla-94 |
| SEQ. ID. NO. 27853 | 97-LysPheAlaAspGlySerValThrTyrGlyLysAlaGlyGluSerLysThrGluGlnSerProLysAla-119 |
| SEQ. ID. NO. 27854 | 131-AlaAsnAspAlaLysLeuProProGlyLeuLysIleThrAsnGlyLysLysLeuTyrSer-150 |
| SEQ. ID. NO. 27855 | 153-GlyLeuAsnLysAlaGlyThrGlyLysTyrSerIleGlyGlyValGluThrGluValValLysTyrArgValArgArgGlyAspAspThrVal-183 |
| SEQ. ID. NO. 27856 | 199-GlyTyrThrAspAspGlyLysThrTyr-207 |
| SEQ. ID. NO. 27857 | 218-GlyGlnAlaAlaLysPro-223 |

Hydrophilic Regions - Hopp-Woods
| SEQ. ID. NO. 27858 | 45-ThrPheGluArgSerGlyAsn-51 |
| SEQ. ID. NO. 27859 | 85-LysAspIleArgArgGlyLysLeuTyrAla-94 |
| SEQ. ID. NO. 27860 | 107-LysAlaGlyGluSerLysThrGluGlnSerProLysAla-119 |
| SEQ. ID. NO. 27861 | 131-AlaAsnAspAlaLysLeu-136 |
| SEQ. ID. NO. 27862 | 143-ThrAsnGlyLysLysLeuTyr-149 |
| SEQ. ID. NO. 27863 | 155-AsnLysAlaGlyThrGly-160 |
| SEQ. ID. NO. 27864 | 167-ValGluThrGluValValLysTyrArgValArgArgGlyAspAspThr-182 |
| SEQ. ID. NO. 27865 | 200-TyrThrAspAspGlyLysThrTyr-207 |
| SEQ. ID. NO. 27866 | 219-GlnAlaAlaLysPro-223 | g121-1
AMPHI Regions - AMPHI
| SEQ. ID. NO. 27867 | 40-ProTyrProAspArgLeuArgArgLysLeu-49 |
| SEQ. ID. NO. 27868 | 68-GlnGluLeuSerArgLeuTyrAlaGlnThr-77 |
| SEQ. ID. NO. 27869 | 101-ThrValArgHisAlaPro-106 |
| SEQ. ID. NO. 27870 | 117-LeuProLeuLeuAlaGluLeuThrArgIlePheThrValGly-130 |
| SEQ. ID. NO. 27871 | 148-ProAlaPheHisGlu-152 |
| SEQ. ID. NO. 27872 | 167-IleGlyGlyIleAlaAsnIleSerVal-175 |
| SEQ. ID. NO. 27873 | 189-ProGlyAsnMetLeuMetAspAlaTrpThr-198 |
| SEQ. ID. NO. 27874 | 216-GlyAsnIleLeuProGlnLeuLeuGlyArgLeuLeuAlaHisPro-230 |
| SEQ. ID. NO. 27875 | 236-HisProLysSerThrGly-241 |
| SEQ. ID. NO. 27876 | 251-GluThrTyrLeuAsp-255 |
| SEQ. ID. NO. 27877 | 262-AspValLeuArgThrLeuSerArgPheThrAlaGlnThrValTrpAspAlaValSerHis-281 |
| SEQ. ID. NO. 27878 | 303-AlaAspLeuAlaGluCysPhe-309 |
| SEQ. ID. NO. 27879 | 341-IleAsnArgIleProGlySerPro-348 |

Antigenic Index - Jameson-Wolf
| SEQ. ID. NO. 27880 | 13-ThrSerMetAspGlyAlaAsp-19 |
| SEQ. ID. NO. 27881 | 23-ValArgMetAspGlyGlyLysTrpLeuGly-32 |
| SEQ. ID. NO. 27882 | 40-ProTyrProAspArgLeuArgArgLysLeuLeuAspLeuGlnAspThrGlyThrAspGluLeuHisArgSerArgMetLeuSer-67 |
| SEQ. ID. NO. 27883 | 85-GlnAsnLeuAlaProCysAsp-91 |
| SEQ. ID. NO. 27884 | 97-CysHisGlyGlnThrValArgHisAlaProGluHisGlyTyrSer-111 |
| SEQ. ID. NO. 27885 | 128-ThrValGlyAspPheArgSerArgAspLeuAlaAlaGlyGlyGlnGly-143 |
| SEQ. ID. NO. 27886 | 154-LeuPheArgAspAspArgGluThrArgVal-163 |
| SEQ. ID. NO. 27887 | 186-AspThrGlyProGlyAsnMet-192 |
| SEQ. ID. NO. 27888 | 205-ProTyrAspLysAsnGlyAlaLysAlaAlaGlnGlyAsn-217 |
| SEQ. ID. NO. 27889 | 235-ProHisProLysSerThrGlyArgGlu-243 |
| SEQ. ID. NO. 27890 | 253-TyrLeuAspGlyGlyGluAsnArgTyrAspValLeuArgThrLeuSer-268 |
| SEQ. ID. NO. 27891 | 283-AlaAlaAspAlaArgGln-288 |
| SEQ. ID. NO. 27892 | 293-GlyGlyGlyIleArgAsnProValLeu-301 |
| SEQ. ID. NO. 27893 | 344-IleProGlySerProHisLysAlaThrGlyAlaSerLysProCysIle-359 |

TABLE 1-continued

Hydrophilic Regions - Hopp-Woods
SEQ. ID. NO. 27894   13-ThrSerMetAspGlyAlaAsp-19
SEQ. ID. NO. 27895   41-TyrProAspArgLeuArgArgLysLeuLeuAspLeuGlnAspThrGlyThrAspGluLeuHisArgSerArgMetLeuSer-67
SEQ. ID. NO. 27896   101-ThrValArgHisAlaPro-106
SEQ. ID. NO. 27897   131-AspPheArgSerArgAspLeuAlaAla-139
SEQ. ID. NO. 27898   154-LeuPheArgAspAspArgGluThrArgVal-163
SEQ. ID. NO. 27899   206-TyrAspLysAsnGlyAlaLysAlaAlaGln-215
SEQ. ID. NO. 27900   235-ProHisProLysSerThrGlyArgGlu-243
SEQ. ID. NO. 27901   254-LeuAspGlyGlyGluAsnArgTyrAspVal-263
SEQ. ID. NO. 27902   283-AlaAlaAspAlaArgGln-288
SEQ. ID. NO. 27903   345-ProGlySerProHisLysAlaThrGlyAlaSerLys-356
g122-1
AMPHI Regions - AMPHI
SEQ. ID. NO. 27904   6-AsnIleHisLysThrPhe-11
SEQ. ID. NO. 27905   42-ThrPheLeuArgCysLeuAsnAlaLeuGluMetProGlu-54
SEQ. ID. NO. 27906   102-LeuGluAsnValMetGlu-107
SEQ. ID. NO. 27907   126-LysLeuLeuGluLys-130
SEQ. ID. NO. 27908   176-ProGluLeuValGlnAspValLeuAspAlaMetLysGluLeuAlaArgGluGly-193
SEQ. ID. NO. 27909   227-ProLysGluLeuPheAspHisLeuLysHisGlu-237
Antigenic Index - Jameson-Wolf
SEQ. ID. NO. 27910   5-ArgAsnIleHisLysThrPheGlyGluAsnThrIle-16
SEQ. ID. NO. 27911   20-IleAspLeuAspValGlyLysGlyGln-28
SEQ. ID. NO. 27912   34-GlyProSerGlySerGlyLysThrThr-42
SEQ. ID. NO. 27913   51-GluMetProGluAspGlyGlnIleGluPheAspAsnAlaArgProLeuArgIleAspPheSerLysLysThrSerLysHisAsp-78
SEQ. ID. NO. 27914   81-AlaLeuArgArgLysSerGlyMet-88
SEQ. ID. NO. 27915   96-PheProHisLysThrValLeu-102
SEQ. ID. NO. 27916   114-GlyLysProAlaAlaGlnAlaArgGluGluAlaLeuLysLeuLeuGlu-129
SEQ. ID. NO. 27917   131-ValGlyLeuGlyAspLysValAspLeuTyr-140
SEQ. ID. NO. 27918   142-TyrGlnLeuSerGlyGlyGlnGlnGlnArgValGlyIle-154
SEQ. ID. NO. 27919   168-AspGluProThrSerAlaLeuAspProGluLeuVal-179
SEQ. ID. NO. 27920   182-ValLeuAspAlaMetLysGluLeuAlaArgGluGlyTrp-194
SEQ. ID. NO. 27921   216-MetAspGlyGlyVal-220
SEQ. ID. NO. 27922   222-ValGluGlnGlSerProLysGluLeuPheAsp-232
SEQ. ID. NO. 27923   234-LeuLysHisGluArgThrArgArgPheLeu-243
Hydrophilic Regions - Hopp-Woods
SEQ. ID. NO. 27924   20-IleAspLeuAspValGlyLys-26
SEQ. ID. NO. 27925   51-GluMetProGluAspGlyGlnIleGluPheAspAsnAlaArgProLeuArgIleAspPheSerLysLysThrSerLysHisAsp-78
SEQ. ID. NO. 27926   81-AlaLeuArgArgLysSerGly-87
SEQ. ID. NO. 27927   114-GlyLysProAlaAlaGlnAlaArgGluGluAlaLeuLysLeuLeuGlu-129
SEQ. ID. NO. 27928   131-ValGlyLeuGlyAspLysValAsp-138
SEQ. ID. NO. 27929   168-AspGluProThrSerAlaLeuAspProGluLeuVal-179
SEQ. ID. NO. 27930   182-ValLeuAspAlaMetLysGluLeuAlaArg-191
SEQ. ID. NO. 27931   224-GlnGlySerProLysGluLeuPheAsp-232
SEQ. ID. NO. 27932   234-LeuLysHisGluArgThrArgArgPheLeu-243
g126-1
AMPHI Regions - AMPHI
SEQ. ID. NO. 27933   26-LeuLysGlnSerValArg-31
SEQ. ID. NO. 27934   73-GlyCysGlnSerValGlnGluAla-80
SEQ. ID. NO. 27935   112-PheGlnLeuValGluAla-117
SEQ. ID. NO. 27936   143-LeuAspAlaGlyCysGln-148
SEQ. ID. NO. 27937   150-LeuMetProTrpAlaAlaProIleGlyThrGlyLeuGlyAlaVal-164
SEQ. ID. NO. 27938   213-SerGlyAspProValAsnMetAlaArgAlaPhe-223
Antigenic Index - Jameson-Wolf
SEQ. ID. NO. 27939   7-GluThrPheProSerArgLeu-13
SEQ. ID. NO. 27940   24-GluIleLeuLysGlnSerValArgThrAlaArg-34
SEQ. ID. NO. 27941   41-SerLeuArgArgThrGlyCysGlyGlyGluAlaHisGlyGlnGlyPhe-56
SEQ. ID. NO. 27942   85-GlnMetAlaArgGluValPheGlu-92
SEQ. ID. NO. 27943   99-GluLeuIleGlyAspAspAspThrLeuGln-108
SEQ. ID. NO. 27944   121-LeuIleLysAspGlyPheLysValLeu-129
SEQ. ID. NO. 27945   141-ArgLeuLeuAspAlaGlyCys-147
SEQ. ID. NO. 27946   171-IleLeuArgGluArgLeuProAspThrProLeu-181
SEQ. ID. NO. 27947   209-AlaValSerArgSerGlyAspProValAsn-218
SEQ. ID. NO. 27948   228-GluSerGlyArgLeuAlaPhe-234
SEQ. ID. NO. 27949   237-GlyProValGluAlaArghrLysAlaGlnAlaSerThrProThrVal-252
Hydrophilic Regions - Hopp-Woods
SEQ. ID. NO. 27950   24-GluIleLeuLysGlnSerValArgThrAlaArg-34
SEQ. ID. NO. 27951   41-SerLeuArgArgThrGlyCysGlyGlyGluAlaHis-52
SEQ. ID. NO. 27952   85-GlnMetAlaArgGluValPheGlu-92
SEQ. ID. NO. 27953   100-LeuIleGlyAspAspAspThrLeuGln-108
SEQ. ID. NO. 27954   171-IleLeuArgGluArgLeuProAsp-178
SEQ. ID. NO. 27955   210-ValSerArgSerGlyAspPro-216
SEQ. ID. NO. 27956   228-GluSerGlyArgLeuAlaPhe-234
SEQ. ID. NO. 27957   237-GlyProValGluAlaArgThrLysAlaGlnAla-247
g127
AMPHI Regions - AMPHI
SEQ. ID. NO. 27958   6-MetLeuAsnThrTrpProAsp-12
SEQ. ID. NO. 27959   22-GluSerValAlaAla-26
SEQ. ID. NO. 27960   119-ValGlyAspTyrIleGluIle-125
SEQ. ID. NO. 27961   135-IleAsnLeuLeuAsnThrLeuMet-142
SEQ. ID. NO. 27962   147-ProAsnProLeuValGlyGlnLeuAla-155

TABLE 1-continued

| | |
|---|---|
| SEQ. ID. NO. 27963 | 206-LeuGluProLeuCysAlaPro-212 |
| SEQ. ID. NO. 27964 | 214-IleProAlaIleGlnArgTyrLeuGluAsnValGln-225 |
| SEQ. ID. NO. 27965 | 250-ArgIleIleValArgPheAlaSerProVal-259 |
| SEQ. ID. NO. 27966 | 268-AlaValMetAspGluPheLeuArgVal-276 |
| Antigenic Index - Jameson-Wolf | |
| SEQ. ID. NO. 27967 | 14-ValProIleArgAlaGluAlaAlaGlu-22 |
| SEQ. ID. NO. 27968 | 41-HisPheArgArgHisProAspPheGlyIleGluSerLysArgArgPheLeuVal-58 |
| SEQ. ID. NO. 27969 | 112-SerAlaThrGlnGlnTyrSerVal-119 |
| SEQ. ID. NO. 27970 | 126-AsnGlyLeuArgGlyArgValValAsp-134 |
| SEQ. ID. NO. 27971 | 169-HisProValArgArgAspAsnIleLeu-177 |
| SEQ. ID. NO. 27972 | 193-LeuAspSerAspGluAlaValCysArg-201 |
| SEQ. ID. NO. 27973 | 234-AlaAlaArgProArgValThrArgValProTyrAspAspLysAlaTyr-249 |
| SEQ. ID. NO. 27974 | 257-SerProValSerLysArgLeuGluIle-265 |
| SEQ. ID. NO. 27975 | 282-AsnHisProAlaGlySerGluThrLeu-290 |
| Hydrophilic Regions - Hopp-Woods | |
| SEQ. ID. NO. 27976 | 14-ValProIleArgAlaGluAlaAlaGlu-22 |
| SEQ. ID. NO. 27977 | 42-PheArgArgHisProAspPheGlyIleGluSerLysArgArgPheLeuVal-58 |
| SEQ. ID. NO. 27978 | 126-AsnGlyLeuArgGlyArgValVal-133 |
| SEQ. ID. NO. 27979 | 170-ProValArgArgAspAsnIleLeu-177 |
| SEQ. ID. NO. 27980 | 193-LeuAspSerAspGluAlaValCysArg-201 |
| SEQ. ID. NO. 27981 | 235-AlaArgProArgValThrArgValProTyrAspAspLysAlaTyr-249 |
| SEQ. ID. NO. 27982 | 259-ValSerLysArgLeuGluIle-265 |
| SEQ. ID. NO. 27983 | 285-AlaGlySerGluThrLeu-290 |
| g128-2 | |
| AMPHI Regions - AMPHI | |
| SEQ. ID. NO. 27984 | 43-AlaGlnThrHisThrGlyTrpAlaAsnThrValGluArgLeuThrGlyIleThrGluArgValGlyArgIleTrpGlyValValSerHisLeuAsnSerValVal-77 |
| SEQ. ID. NO. 27985 | 85-ValTyrAsnGluLeuMetProGluIle-93 |
| SEQ. ID. NO. 27986 | 102-GlnAspIleGluLeuTyrAsnArgPheLysThrIleLysAsnSerProGlu-118 |
| SEQ. ID. NO. 27987 | 166-PheSerGlnAsnValLeuAspAlaThrAsp-175 |
| SEQ. ID. NO. 27988 | 189-GlyIleProGluAspAla-194 |
| SEQ. ID. NO. 27989 | 218-HisTyrLeuAlaVal-222 |
| SEQ. ID. NO. 27990 | 231-LeuArgGluGlnIleTyr-236 |
| SEQ. ID. NO. 27991 | 245-GluLeuSerAsnAspGlyLysPheAspAsnThrAlaAsnIleAspArgThrLeuGluAsnAlaLeuLysThrAlaLysLeuLeuGlyPheLysAsnTyrAlaGlu-279 |
| SEQ. ID. NO. 27992 | 286-MetAlaAspThrProGluGlnValLeuAsnPheLeuHisAspLeuAlaArgArgAla-304 |
| SEQ. ID. NO. 27993 | 313-AlaGluValLysAlaPhe-318 |
| SEQ. ID. NO. 27994 | 360-LysValLeuAlaGlyLeuPheAlaGlnIleLysLysLeuTyrGly-374 |
| SEQ. ID. NO. 27995 | 472-LeuHisHisLeuLeuThrGlnValAspGluLeu-482 |
| SEQ. ID. NO. 27996 | 496-GluLeuProSerGlnPhe-501 |
| SEQ. ID. NO. 27997 | 522-GlyGluProLeuProLysGluLeuPheAspLys-532 |
| SEQ. ID. NO. 27998 | 570-TrpGlnGlnValLeuAspSerVal-577 |
| SEQ. ID. NO. 27999 | 584-IleGlnProProGluTyrAsnArgPheAlaAsnSerPheGlyHisIlePheAlaGlyGly-603 |
| SEQ. ID. NO. 28000 | 610-SerTyrAlaTrpAlaGlu-615 |
| SEQ. ID. NO. 28001 | 623-AlaAlaPheGluGluSerAspAsp-630 |
| SEQ. ID. NO. 28002 | 636-LysArgPheTrpGlnGluIleLeuAla-644 |
| SEQ. ID. NO. 28003 | 651-AlaAlaGluSerPheLysAlaPheArg-659 |
| Antigenic Index - Jameson-Wolf | |
| SEQ. ID. NO. 28004 | 9-LeuGlyGluGluProArgPheAsnGlnIleLysThrGluAspIleLysProAlaVal-27 |
| SEQ. ID. NO. 28005 | 32-AlaGluAlaArgGly-36 |
| SEQ. ID. NO. 28006 | 43-AlaGlnThrHisThrGlyTrp-49 |
| SEQ. ID. NO. 28007 | 52-ThrValGluArgLeuThrGlyIleThrGluArgValGlyArgIleTrp-67 |
| SEQ. ID. NO. 28008 | 77-ValAspThrProGluLeu-82 |
| SEQ. ID. NO. 28009 | 100-IleGlyGlnAspIleGluLeuTyrAsnArgPheLysThrIleLysAsnSerProGluPhe-119 |
| SEQ. ID. NO. 28010 | 123-SerProAlaGlnLysThrLysLeuAspHisAspLeuArgAsp-136 |
| SEQ. ID. NO. 28011 | 140-SerGlyAlaGluLeuProProGluArgGlnAlaGluLeuAlaLysLeuGlnThrGluGlyAlaGlnLeu-162 |
| SEQ. ID. NO. 28012 | 165-LysPheSerGlnAsnVal-170 |
| SEQ. ID. NO. 28013 | 172-AspAlaThrAspAla-176 |
| SEQ. ID. NO. 28014 | 190-IleProGluAspAla-194 |
| SEQ. ID. NO. 28015 | 202-AlaGlnSerGluGlyLysThrGlyTyrLys-211 |
| SEQ. ID. NO. 28016 | 225-TyrAlaGlyAsnArgGluLeuArgGluGlnIle-235 |
| SEQ. ID. NO. 28017 | 242-ArgAlaSerGluLeuSerAsnAspGlyLysPheAspAsnThrAlaAsnIleAspArgThrLeuGluAsnAlaLeuLysThr-268 |
| SEQ. ID. NO. 28018 | 285-LysMetAlaAspThrProGluGln-292 |
| SEQ. ID. NO. 28019 | 300-LeuAlaArgArgAlaLysProTyrAlaGluLysAspLeuAlaGlu-314 |
| SEQ. ID. NO. 28020 | 316-LysAlaPheAlaArgGluHisLeuGlyLeuAlaAspProGlnProTrpAspLeu-333 |
| SEQ. ID. NO. 28021 | 335-TyrAlaGlyGluLysLeuArgGluAlaLysTyrAlaPheSerGluThrGluValLysLys-354 |
| SEQ. ID. NO. 28022 | 377-PheAlaGluLysThr-381 |
| SEQ. ID. NO. 28023 | 387-LysAspValArgTyrPheGluLeuGlnGlnAsnGlyLysThrIle-401 |
| SEQ. ID. NO. 28024 | 409-TyrAlaArgGluGlyLysArgGlyGlyAla-418 |
| SEQ. ID. NO. 28025 | 420-MetAsnAspTyrLysGlyArgArgArgPheAlaAspGlyThrLeu-434 |
| SEQ. ID. NO. 28026 | 447-ProProValGlyGlyLysGluAlaArgLeuSerHisAspGlu-460 |
| SEQ. ID. NO. 28027 | 478-GlnValAspGluLeuGlyVal-484 |
| SEQ. ID. NO. 28028 | 496-GluLeuProSerGln-500 |
| SEQ. ID. NO. 28029 | 516-SerAlaHisGluGluThrGlyGluProLeuPro-526 |
| SEQ. ID. NO. 28030 | 560-SerGluSerAspGluCysArgLeuLysAsn-569 |
| SEQ. ID. NO. 28031 | 575-AspSerValArgLysGluValAla-582 |
| SEQ. ID. NO. 28032 | 585-GlnProProGluTyrAsnArgPheAlaAsnSerPheGly-597 |
| SEQ. ID. NO. 28033 | 605-SerAlaGlyTyrTyrSerTyr-611 |
| SEQ. ID. NO. 28034 | 625-PheGluGluSerAspAspValAlaAlaThrGlyLysArgPheTrp-639 |
| SEQ. ID. NO. 28035 | 646-GlyGlySerArgSerAlaAlaGluSerPheLysAlaPheArgGlyArgGluProSerIle-665 |

TABLE 1-continued

| | |
|---|---|
| SEQ. ID. NO. 28036 | 669-LeuArgHisSerGlyPheAspAsnAlaAla-678 |

Hydrophilic Regions - Hopp-Woods

| | |
|---|---|
| SEQ. ID. NO. 28037 | 9-LeuGlyGluGluProArgPheAsnGlnIleLysThrGluAspIleLysPro-25 |
| SEQ. ID. NO. 28038 | 32-AlaGluAlaArgGly-36 |
| SEQ. ID. NO. 28039 | 52-ThrValGluArgLeuThrGlyIleThrGluArgValGly-64 |
| SEQ. ID. NO. 28040 | 77-ValAspThrProGluLeu-82 |
| SEQ. ID. NO. 28041 | 100-IleGlyGlnAspIleGluLeu-106 |
| SEQ. ID. NO. 28042 | 111-LysThrIleLysAsnSerProGlu-118 |
| SEQ. ID. NO. 28043 | 124-ProAlaGlnLysThrLysLeuAspHisAspLeuArgAsp-136 |
| SEQ. ID. NO. 28044 | 143-GluLeuProProGluArgGlnAlaGluLeuAlaLysLeuGlnThrGluGlyAlaGlnLeu-162 |
| SEQ. ID. NO. 28045 | 190-IleProGluAspAla-194 |
| SEQ. ID. NO. 28046 | 202-AlaGlnSerGluGlyLysThrGlyTyr-210 |
| SEQ. ID. NO. 28047 | 227-GlyAsnArgGluLeuArgGluGlnIle-235 |
| SEQ. ID. NO. 28048 | 242-ArgAlaSerGluLeuSerAsnAspGlyLysPheAspAsn-254 |
| SEQ. ID. NO. 28049 | 256-AlaAsnIleAspArgThrLeuGluAsnAlaLeuLysThr-268 |
| SEQ. ID. NO. 28050 | 285-LysMetAlaAspThrProGlu-291 |
| SEQ. ID. NO. 28051 | 300-LeuAlaArgArgAlaLysProTyrAlaGluLysAspLeuAlaGlu-314 |
| SEQ. ID. NO. 28052 | 316-LysAlaPheAlaArgGluHisLeuGly-324 |
| SEQ. ID. NO. 28053 | 335-TyrAlaGlyGluLysLeuArgGluAlaLysTyrAlaPheSerGluThrGluValLysLys-354 |
| SEQ. ID. NO. 28054 | 377-PheAlaGluLysThr-381 |
| SEQ. ID. NO. 28055 | 387-LysAspValArgTyr-391 |
| SEQ. ID. NO. 28056 | 396-GlnAsnGlyLysThr-400 |
| SEQ. ID. NO. 28057 | 409-TyrAlaArgGluGlyLysArgGlyGly-417 |
| SEQ. ID. NO. 28058 | 423-TyrLysGlyArgArgArgPheAlaAsp-431 |
| SEQ. ID. NO. 28059 | 449-ValGlyGlyLysGluAlaArgLeuSerHisAspGlu-460 |
| SEQ. ID. NO. 28060 | 478-GlnValAspGluLeuGly-483 |
| SEQ. ID. NO. 28061 | 516-SerAlaHisGluGluThrGlyGluProLeuPro-526 |
| SEQ. ID. NO. 28062 | 560-SerGluSerAspGluCysArgLeuLysAsn-569 |
| SEQ. ID. NO. 28063 | 575-AspSerValArgLysGluValAla-582 |
| SEQ. ID. NO. 28064 | 625-PheGluGluSerAspAspValAlaAlaThrGly-635 |
| SEQ. ID. NO. 28065 | 647-GlySerArgSerAlaAlaGluSerPheLysAlaPheArgGlyArgGluProSerIle-665 | g130
AMPHI Regions - AMPHI

| | |
|---|---|
| SEQ. ID. NO. 28066 | 16-ThrLeuValSerGlyIle-21 |
| SEQ. ID. NO. 28067 | 36-GlySerGlySerPheGly-41 |
| SEQ. ID. NO. 28068 | 56-GlnProValGlyGlnLeu-61 |
| SEQ. ID. NO. 28069 | 91-AsnValProAsnAlaPro-96 |
| SEQ. ID. NO. 28070 | 110-GlnGlyPheAspThrLeuPheGlnHisAlaLeuAsnGlyPheAsnAlaMet-126 |
| SEQ. ID. NO. 28071 | 171-ThrAlaSerAlaPro-175 |
| SEQ. ID. NO. 28072 | 204-PheGluAlaThrCysGln-209 |
| SEQ. ID. NO. 28073 | 211-CysHisGlyGlySerIleProGlyIlePro-220 |
| SEQ. ID. NO. 28074 | 234-LysGlyLysGluThr-238 |
| SEQ. ID. NO. 28075 | 245-GluGlyPheAsnAlaMet-250 |

Antigenic Index - Jameson-Wolf

| | |
|---|---|
| SEQ. ID. NO. 28076 | 1-MetLysGlnLeuArgAspAsnLysAlaGlnGlySer-12 |
| SEQ. ID. NO. 28077 | 35-AlaGlySerGlySerPheGlyAspValAspAlaThrThrGluAlaAlaThrGlnThrArgIleGlnProValGly-59 |
| SEQ. ID. NO. 28078 | 63-MetGlyAspGlyIleProValGlyGluArgGlnGlyGlu-75 |
| SEQ. ID. NO. 28079 | 87-AlaAlaAspSerAsnValProAsnAlaProLysLeuGluHisAsnGlyAspTrpAla-105 |
| SEQ. ID. NO. 28080 | 108-IleAlaGlnGlyPhe-112 |
| SEQ. ID. NO. 28081 | 126-MetProAlaLysGlyGlyAla-132 |
| SEQ. ID. NO. 28082 | 134-AspLeuThrAspGlnGluLeuLysArg-142 |
| SEQ. ID. NO. 28083 | 148-AlaAsnLysSerGlyGlySerPheProAsnProAspGluAlaAlaProAlaAspAsnAlaAlaSerGlyThrAlaSerAlaProAlaAspSerAlaAla ProAlaGluAlaLysAlaGluAspLysGlyAlaAla-192 |
| SEQ. ID. NO. 28084 | 197-GlyValAspGlyLysLysValPheGlu-205 |
| SEQ. ID. NO. 28085 | 221-GlyIleGlyLysLysAspAspTrpAlaProArgIleLysLysGlyLysGluThrLeuHis-240 |
| SEQ. ID. NO. 28086 | 251-ProAlaLysGlyGlyAsnAlaGlyLeuSerAspAspGluValLysAla-266 |
| SEQ. ID. NO. 28087 | 274-GlnSerGlyAlaLys-278 |

Hydrophilic Regions - Hopp-Woods

| | |
|---|---|
| SEQ. ID. NO. 28088 | 1-MetLysGlnLeuArgAspAsnLysAlaGlnGly-11 |
| SEQ. ID. NO. 28089 | 41-GlyAspValAspAlaThrThrGluAlaAlaThr-51 |
| SEQ. ID. NO. 28090 | 68-ProValGlyGluArgGlnGlyGlu-75 |
| SEQ. ID. NO. 28091 | 87-AlaAlaAspSerAsnVal-92 |
| SEQ. ID. NO. 28092 | 96-ProLysLeuGluHisAsnGly-102 |
| SEQ. ID. NO. 28093 | 127-ProAlaLysGlyGlyAla-132 |
| SEQ. ID. NO. 28094 | 134-AspLeuThrAspGlnGluLeuLysArg-142 |
| SEQ. ID. NO. 28095 | 156-ProAsnProAspGluAlaAlaProAlaAspAsnAlaAla-168 |
| SEQ. ID. NO. 28096 | 174-AlaProAlaAspSerAlaAlaProAlaGluAlaLysAlaGluAspLysGlyAlaAla-192 |
| SEQ. ID. NO. 28097 | 198-ValAspGlyLysLysValPheGlu-205 |
| SEQ. ID. NO. 28098 | 222-IleGlyLysLysAspAspTrpAlaProArgIleLysLysGlyLysGluThrLeuHis-240 |
| SEQ. ID. NO. 28099 | 251-ProAlaLysGlyGlyAsn-256 |
| SEQ. ID. NO. 28100 | 258-GlyLeuSerAspAspGluValLysAla-266 | g132-2
AMPHI Regions - AMPHI

| | |
|---|---|
| SEQ. ID. NO. 28101 | 13-IleIleSerAlaLeuAlaVal-19 |
| SEQ. ID. NO. 28102 | 70-AlaThrCysMetAlaMetVal-76 |
| SEQ. ID. NO. 28103 | 92-IleArgGlnThrGlnGlnAlaProLysProValSerAsnThr-105 |

Antigenic Index - Jameson-Wolf

| | |
|---|---|
| SEQ. ID. NO. 28104 | 26-GlnHisGlyLysGlyAlaAspAla-33 |
| SEQ. ID. NO. 28105 | 38-GlySerGlySerGlySerAla-44 |

TABLE 1-continued

| | |
|---|---|
| SEQ. ID. NO. 28106 | 81-HisThrThrLysHisGlyLeuAspPheSerAsnIleArgGlnThrGlnGlnAlaProLysProValSerAsnThrGluProSerAlaProValProGln GlnGlnLys-116 |

Hydrophilic Regions - Hopp-Woods

| | |
|---|---|
| SEQ. ID. NO. 28107 | 28-GlyLysGlyAlaAspAla-33 |
| SEQ. ID. NO. 28108 | 93-ArgGlnThrGlnGlnAlaProLysProValSerAsnThrGluProSerAla-109 | g134
AMPHI Regions - AMPHI

| | |
|---|---|
| SEQ. ID. NO. 28109 | 39-IleGlnSerAlaGlyThrVal-45 |
| SEQ. ID. NO. 28110 | 47-GlyLysLysThrGly-51 |
| SEQ. ID. NO. 28111 | 56-SerAspTrpMetAspIleGluLysGlnArg-65 |
| SEQ. ID. NO. 28112 | 83-ValAsnLeuLeuAspThrProGlyHis-91 |
| SEQ. ID. NO. 28113 | 97-AspThrTyrArgValLeuThrAlaVal-105 |
| SEQ. ID. NO. 28114 | 114-AlaAlaLysGlyValGlu-119 |
| SEQ. ID. NO. 28115 | 123-IleLysLeuLeuAsnValCysArg-130 |
| SEQ. ID. NO. 28116 | 142-LysTyrAspArgGluVal-147 |
| SEQ. ID. NO. 28117 | 149-AspSerLeuGluLeuLeuAspGluValGluAspIleLeuGln-162 |
| SEQ. ID. NO. 28118 | 176-LysAsnPheLysGlyValTyrHisIleLeu-185 |
| SEQ. ID. NO. 28119 | 201-HisGluPheAspIleIleLysGlyIleAsnAsn-211 |
| SEQ. ID. NO. 28120 | 254-PheGlySerAlaIle-258 |
| SEQ. ID. NO. 28121 | 265-GluIleLeuAsnSerLeuIleAspTrpAlaPro-275 |
| SEQ. ID. NO. 28122 | 322-LysPheGluArgGlyMetLys-328 |
| SEQ. ID. NO. 28123 | 361-AspIleIleGlyIleProAsnHis-368 |
| SEQ. ID. NO. 28124 | 395-LeuPheArgSerValArgIleLys-402 |
| SEQ. ID. NO. 28125 | 404-ProLeuLysIleLysGln-409 |
| SEQ. ID. NO. 28126 | 411-GlnLysGlyLeuGlnGlnLeuGlyGlu-419 |
| SEQ. ID. NO. 28127 | 423-ValGlnValPheLysProMetSer-430 |
| SEQ. ID. NO. 28128 | 449-SerArgLeuAlaAsnGluTyr-455 |
| SEQ. ID. NO. 28129 | 481-AlaGluPheGluLysAlaAsn-487 |
| SEQ. ID. NO. 28130 | 515-ArgTrpProAspIle-519 |

Antigenic Index - Jameson-Wolf

| | |
|---|---|
| SEQ. ID. NO. 28131 | 4-GluIleLeuAspGlnValArgArgArgArgThrPhe-15 |
| SEQ. ID. NO. 28132 | 19-SerHisProAspAlaGlyLysThrThrLeuThr-29 |
| SEQ. ID. NO. 28133 | 43-GlyThrValLysGlyLysLysThrGlyLysPheAlaThr-55 |
| SEQ. ID. NO. 28134 | 57-AspTrpMetAspIleGluLysGlnArgGly-66 |
| SEQ. ID. NO. 28135 | 76-PheAspTyrLysAspHisThrVal-83 |
| SEQ. ID. NO. 28136 | 85-LeuLeuAspThrProGlyHisGlnAspPheSerGluAspThrTyrArg-100 |
| SEQ. ID. NO. 28137 | 113-AspAlaAlaLysGlyValGlu-119 |
| SEQ. ID. NO. 28138 | 129-CysArgLeuArgAspThrPro-135 |
| SEQ. ID. NO. 28139 | 140-MetAsnLysTyrAspArgGluValArgAspSerLeuGluLeuLeuAspGluValGluAsp-159 |
| SEQ. ID. NO. 28140 | 173-GlyMetGlyLysAsnPheLys-179 |
| SEQ. ID. NO. 28141 | 194-AlaGlyGlyGluArgLeuProHis-201 |
| SEQ. ID. NO. 28142 | 207-LysGlyIleAsnAsnProGluLeuGluGlnArgPheProLeu-220 |
| SEQ. ID. NO. 28143 | 223-GlnGlnLeuArgAspGluIleGluLeu-231 |
| SEQ. ID. NO. 28144 | 235-AlaSerAsnGluPheAsnLeu-241 |
| SEQ. ID. NO. 28145 | 274-AlaProAlaProLysProArgAspAlaThrMet-284 |
| SEQ. ID. NO. 28146 | 286-MetValGlyProAspGluProLysPhe-294 |
| SEQ. ID. NO. 28147 | 302-GlnAlaAsnMetAspProLysHisArgAspArgIleAla-314 |
| SEQ. ID. NO. 28148 | 317-ArgValCysSerGlyLysPheGluArgGlyMetLysMetLysHisLeuArgIleAsnArgGluIleAla-339 |
| SEQ. ID. NO. 28149 | 348-SerHisAspArgGluLeuAlaGluGluAlaTyrAla-359 |
| SEQ. ID. NO. 28150 | 365-IleProAsnHisGly-369 |
| SEQ. ID. NO. 28151 | 373-IleGlyAspSerPheSerGluGlyGluGln-382 |
| SEQ. ID. NO. 28152 | 399-ValArgIleLysAsnProLeuLysIleLysGlnLeuGlnLysGlyLeuGlnGlnLeuGlyGluGluGlyAla-422 |
| SEQ. ID. NO. 28153 | 450-ArgLeuAlaAsnGluTyrGlyVal-457 |
| SEQ. ID. NO. 28154 | 459-AlaValPheAspSer-463 |
| SEQ. ID. NO. 28155 | 473-SerCysAspAspLysLysLysLeuAlaGluPheGluLysAlaAsnAla-488 |
| SEQ. ID. NO. 28156 | 503-AlaProAsnArgValAsnLeu-509 |
| SEQ. ID. NO. 28157 | 511-LeuThrGlnGluArgTrpProAspIleVal-520 |
| SEQ. ID. NO. 28158 | 523-GluThrArgGluHisSerVal-529 |

Hydrophilic Regions - Hopp-Woods

| | |
|---|---|
| SEQ. ID. NO. 28159 | 4-GluIleLeuAspGlnValArgArgArgArgThr-14 |
| SEQ. ID. NO. 28160 | 21-ProAspAlaGlyLys-25 |
| SEQ. ID. NO. 28161 | 43-GlyThrValLysGlyLysLysThrGlyLys-52 |
| SEQ. ID. NO. 28162 | 59-MetAspIleGluLysGlnArgGly-66 |
| SEQ. ID. NO. 28163 | 77-AspTyrLysAspHisThr-82 |
| SEQ. ID. NO. 28164 | 92-GlnAspPheSerGluAspThrTyr-99 |
| SEQ. ID. NO. 28165 | 113-AspAlaAlaLysGlyValGlu-119 |
| SEQ. ID. NO. 28166 | 129-CysArgLeuArgAspThrPro-135 |
| SEQ. ID. NO. 28167 | 142-LysTyrAspArgGluValArgAspSerLeuGluLeuLeuAspGluValGluAsp-159 |
| SEQ. ID. NO. 28168 | 194-AlaGlyGlyGluArgLeuProHis-201 |
| SEQ. ID. NO. 28169 | 212-ProGluLeuGluGlnArgPheProLeu-220 |
| SEQ. ID. NO. 28170 | 223-GlnGlnLeuArgAspGluIleGluLeu-231 |
| SEQ. ID. NO. 28171 | 277-ProLysProArgAspAlaThrMet-284 |
| SEQ. ID. NO. 28172 | 287-ValGlyProAspGluProLysPhe-294 |
| SEQ. ID. NO. 28173 | 305-MetAspProLysHisArgAspArgIleAla-314 |
| SEQ. ID. NO. 28174 | 319-CysSerGlyLysPheGluArgGlyMetLysMetLysHisLeuArgIleAsnArgGluIleAla-339 |
| SEQ. ID. NO. 28175 | 348-SerHisAspArgGluLeuAlaGluGluAlaTyrAla-359 |
| SEQ. ID. NO. 28176 | 376-SerPheSerGluGlyGluGln-382 |
| SEQ. ID. NO. 28177 | 399-ValArgIleLysAsnProLeuLysIleLysGlnLeuGln-411 |
| SEQ. ID. NO. 28178 | 417-LeuGlyGluGluGlyAla-422 |
| SEQ. ID. NO. 28179 | 473-SerCysAspAspLysLysLysLeuAlaGluPheGluLysAlaAsnAla-488 |

TABLE 1-continued

| | |
|---|---|
| SEQ. ID. NO. 28180 | 512-ThrGlnGluArgTrpPro-517 |
| SEQ. ID. NO. 28181 | 523-GluThrArgGluHisSerVal-529 |
| g135-2 | |
| AMPHI Regions - AMPHI | |
| SEQ. ID. NO. 28182 | 29-ThrIleThrArgGlnLeuAlaAlaLeu-37 |
| SEQ. ID. NO. 28183 | 85-GluTyrThrAlaAsnLeu-90 |
| SEQ. ID. NO. 28184 | 169-AspIleAspGlyLeuTyrThr-175 |
| SEQ. ID. NO. 28185 | 185-ValArgLeuAspLysIleGluHis-192 |
| SEQ. ID. NO. 28186 | 212-GlyMetLeuThrLysIle-217 |
| SEQ. ID. NO. 28187 | 236-LeuLysProAspSerLeuAlaGluAlaAlaGlu-246 |
| SEQ. ID. NO. 28188 | 284-AlaGluHisAlaLeuSer-289 |
| SEQ. ID. NO. 28189 | 300-IleAlaGlyIleGluGly-305 |
| SEQ. ID. NO. 28190 | 308-SerArgMetAspThrValThrValTyr-316 |
| SEQ. ID. NO. 28191 | 318-LysAlaThrLysGlnPro-323 |
| Antigenic Index - Jameson-Wolf | |
| SEQ. ID. NO. 28192 | 1-MetLysTyrLysArgIleVal-7 |
| SEQ. ID. NO. 28193 | 14-SerIleThrArgSerAspGlySerLeuSerArgGlyLysIleGlnThrIle-30 |
| SEQ. ID. NO. 28194 | 60-GlyPheLysLysArgProValLysIleAlaAspLysGlnAlaSer-74 |
| SEQ. ID. NO. 28195 | 90-LeuSerSerAspGlyIle-95 |
| SEQ. ID. NO. 28196 | 105-AlaAspPheAlaAspLysArgArgTyrGlnAsnAlaGlyGly-118 |
| SEQ. ID. NO. 28197 | 124-LeuGlnArgArgAlaIle-129 |
| SEQ. ID. NO. 28198 | 132-IleAsnGluAsnAspThrValSerValGluGluLeuLysIleGlyAspAsnAspThrLeu-151 |
| SEQ. ID. NO. 28199 | 176-GlyAsnProAsnSerAsnProAspAlaValArgLeuAspLysIleGluHisIleAsn-194 |
| SEQ. ID. NO. 28200 | 202-GlyGlySerGlySerAlaAsnGlyThrGly-211 |
| SEQ. ID. NO. 28201 | 215-ThrLysIleLysAla-219 |
| SEQ. ID. NO. 28202 | 224-AlaGluSerGlyVal-228 |
| SEQ. ID. NO. 28203 | 233-CysSerSerLeuLysProAspSerLeuAlaGluAlaAlaGluHisGlnAlaAspGly-251 |
| SEQ. ID. NO. 28204 | 257-ArgAlaLysGlyLeuArgThrGlnLysGln-266 |
| SEQ. ID. NO. 28205 | 271-TyrSerGluSerArgGlySerValTyrValAspGluGlyAlaGluHisAlaLeuSerGluGlnGlyLysSerLeuLeu-296 |
| SEQ. ID. NO. 28206 | 305-GlyHisPheSerArgMetAspThr-312 |
| SEQ. ID. NO. 28207 | 317-SerLysAlaThrLysGlnProLeuGlyLysGlyArgVal-329 |
| SEQ. ID. NO. 28208 | 335-AlaAlaGluAspLeuLeuLysSerArgLysAlaLys-346 |
| SEQ. ID. NO. 28209 | 350-IleHisArgAspAspTrpIleSer-357 |
| Hydrophilic Regions - Hopp-Woods | |
| SEQ. ID. NO. 28210 | 1-MetLysTyrLysArgIleVal-7 |
| SEQ. ID. NO. 28211 | 14-SerIleThrArgSerAspGlySerLeuSerArgGlyLysIle-27 |
| SEQ. ID. NO. 28212 | 60-GlyPheLysLysArgProValLysIleAlaAspLysGlnAlaSer-74 |
| SEQ. ID. NO. 28213 | 105-AlaAspPheAlaAspLysArgArgTyrGlnAsn-115 |
| SEQ. ID. NO. 28214 | 124-LeuGlnArgArgAlaIle-129 |
| SEQ. ID. NO. 28215 | 133-AsnGluAsnAspThrValSerValGluGluLeuLysIleGlyAspAsnAspThrLeu-151 |
| SEQ. ID. NO. 28216 | 178-ProAsnSerAsnProAspAlaValArgLeuAspLysIleGluHisIleAsn-194 |
| SEQ. ID. NO. 28217 | 215-ThrLysIleLysAla-219 |
| SEQ. ID. NO. 28218 | 236-LeuLysProAspSerLeuAlaGluAlaAlaGluHisGlnAlaAsp-250 |
| SEQ. ID. NO. 28219 | 257-ArgAlaLysGlyLeuArgThrGlnLys-265 |
| SEQ. ID. NO. 28220 | 272-SerGluSerArgGly-276 |
| SEQ. ID. NO. 28221 | 278-ValTyrValAspGluGlyAlaGluHisAlaLeuSerGluGlnGlyLys-293 |
| SEQ. ID. NO. 28222 | 306-HisPheSerArgMetAspThr-312 |
| SEQ. ID. NO. 28223 | 318-LysAlaThrLysGlnProLeuGlyLysGlyArgVal-329 |
| SEQ. ID. NO. 28224 | 335-AlaAlaGluAspLeuLeuLysSerArgLysAlaLys-346 |
| SEQ. ID. NO. 28225 | 351-HisArgAspAspTrp-355 |
| g136 | |
| AMPHI Regions - AMPHI | |
| SEQ. ID. NO. 28226 | 61-AlaValAspValCysGlnArgValArgGlnPheGlyArgLysPheArgGlnLeuAlaPhe-80 |
| SEQ. ID. NO. 28227 | 100-HisHisGlyValLysGlnLeuPheLysArgPheIleIle-112 |
| SEQ. ID. NO. 28228 | 114-GlyPheLysProIleGlyArgHis-121 |
| SEQ. ID. NO. 28229 | 162-ArgHisCysGlnAsn-166 |
| SEQ. ID. NO. 28230 | 184-GlnHisPheGlyGlnPro-189 |
| SEQ. ID. NO. 28231 | 191-GluArgCysGlnPheVal-196 |
| Antigenic Index - Jameson-Wolf | |
| SEQ. ID. NO. 28232 | 1-MetGluIleArgPhe-5 |
| SEQ. ID. NO. 28233 | 52-ArgPheValAspAspArgLeuProVal-60 |
| SEQ. ID. NO. 28234 | 64-ValCysGlnArgValArgGlnPheGlyArgLysPheArg-76 |
| SEQ. ID. NO. 28235 | 83-LeuGlnAlaAspAsn-87 |
| SEQ. ID. NO. 28236 | 113-GlyGlyPheLysProIleGlyArgHisAsnValGln-124 |
| SEQ. ID. NO. 28237 | 153-IleArgHisArgGlyGlyCysPheHisArgHisCysGlnAsnGlnProPheAsp-170 |
| SEQ. ID. NO. 28238 | 173-ThrPheGlyGlyGlyLysLeuArg-180 |
| SEQ. ID. NO. 28239 | 185-HisPheGlyGlnProValGluArg-192 |
| SEQ. ID. NO. 28240 | 198-ProAlaGlnGlnArgArgHisLysThr-206 |
| Hydrophilic Regions - Hopp-Woods | |
| SEQ. ID. NO. 28241 | 1-MetGluIleArgPhe-5 |
| SEQ. ID. NO. 28242 | 52-ArgPheValAspAspArgLeuProVal-60 |
| SEQ. ID. NO. 28243 | 64-ValCysGlnArgValArgGlnPheGlyArgLysPheArg-76 |
| SEQ. ID. NO. 28244 | 199-AlaGlnGlnArgArgHisLysThr-206 |
| g137 | |
| AMPHI Regions - AMPHI | |
| SEQ. ID. NO. 28245 | 24-LeuSerTyrIleLeuGlyPhe-30 |
| SEQ. ID. NO. 28246 | 49-ThrLysGluSerLeu-53 |
| SEQ. ID. NO. 28247 | 55-AspPheLeuThrTrpGly-60 |
| SEQ. ID. NO. 28248 | 78-PheSerAspTyrLeuAlaHisProLeuAspIlePheLysValTrpGluGlyGly-95 |
| SEQ. ID. NO. 28249 | 101-GlyPheLeuGlyValValIle-107 |

TABLE 1-continued

| | |
|---|---|
| SEQ. ID. NO. 28250 | 120-PheLeuLysLeuMetAspThrValAlaProLeuValPro-132 |
| SEQ. ID. NO. 28251 | 139-ArgIleGlyAsnPheIle-144 |
| SEQ. ID. NO. 28252 | 149-TrpGlyArgIleThrAspIleAsnAlaPhe-158 |
| SEQ. ID. NO. 28253 | 178-ProLeuTrpAlaGluTrpLeuGlnGlnTyr-187 |
| SEQ. ID. NO. 28254 | 190-LeuProArgHisProSerGlnLeu-197 |
| SEQ. ID. NO. 28255 | 232-TyrGlyValPheArgPheIleAlaGluPheAlaArgGlnProAspAspTyrLeuGly-250 |

Antigenic Index - Jameson-Wolf

| | |
|---|---|
| SEQ. ID. NO. 28256 | 36-LeuGlyArgArgArgIleAlaGln-43 |
| SEQ. ID. NO. 28257 | 48-PheThrLysGluSerLeuAspAsp-55 |
| SEQ. ID. NO. 28258 | 92-TrpGluGlyGlyMet-96 |
| SEQ. ID. NO. 28259 | 113-SerArgLysHisGlyIle-118 |
| SEQ. ID. NO. 28260 | 136-AlaSerGlyArgIle-140 |
| SEQ. ID. NO. 28261 | 166-AlaHisTyrGluAspAlaGluAlaAlaAla-175 |
| SEQ. ID. NO. 28262 | 191-ProArgHisProSerGlnLeu-197 |
| SEQ. ID. NO. 28263 | 215-SerLysLysProArgProThrGlyGln-223 |
| SEQ. ID. NO. 28264 | 241-PheAlaArgGlnProAspAspTyrLeu-249 |
| SEQ. ID. NO. 28265 | 277-PheGlyMetLysLysGlnHis-283 |

Hydrophilic Regions - Hopp-Woods

| | |
|---|---|
| SEQ. ID. NO. 28266 | 37-GlyArgArgArgIleAla-42 |
| SEQ. ID. NO. 28267 | 48-PheThrLysGluSerLeuAsp-54 |
| SEQ. ID. NO. 28268 | 167-HisTyrGluAspAlaGluAlaAlaAla-175 |
| SEQ. ID. NO. 28269 | 216-LysLysProArgProThrGly-222 |
| SEQ. ID. NO. 28270 | 241-PheAlaArgGlnProAspAspTyr-248 |
| SEQ. ID. NO. 28271 | 278-GlyMetLysLysGlnHis-283 | g138
AMPHI Regions - AMPHI

| | |
|---|---|
| SEQ. ID. NO. 28272 | 21-ProTyrIleArgArgPheSerGlySer-29 |
| SEQ. ID. NO. 28273 | 74-AsnAlaMetLeuGluLysVal-80 |
| SEQ. ID. NO. 28274 | 85-GluPheValGlnGlyMet-90 |
| SEQ. ID. NO. 28275 | 109-ValAsnLysGluIleValSerMetIleAsnThrTyrGly-121 |
| SEQ. ID. NO. 28276 | 152-IleGlyGlnValGlyThrValGluSerIle-161 |
| SEQ. ID. NO. 28277 | 163-ThrGlyLeuValLysGlyLeu-169 |
| SEQ. ID. NO. 28278 | 199-GlyLysLeuAlaGluGluLeu-205 |
| SEQ. ID. NO. 28279 | 213-MetThrAsnIleAlaGlyValMetAspLysThrGlyAsnLeuLeuThrLysLeuThr-231 |
| SEQ. ID. NO. 28280 | 234-ArgIleAspGlyLeu-238 |
| SEQ. ID. NO. 28281 | 247-GlyMetLeuProLysIleAlaSerAlaValGluAlaAlaValAsn-261 |
| SEQ. ID. NO. 28282 | 276-AlaLeuLeuLeuGluIlePheThrAspAla-285 |

Antigenic Index - Jameson-Wolf

| | |
|---|---|
| SEQ. ID. NO. 28283 | 9-AlaAlaAspLysAlaArgIleLeu-16 |
| SEQ. ID. NO. 28284 | 23-IleArgArgPheSerGlySer-29 |
| SEQ. ID. NO. 28285 | 35-TyrGlyGlyAsnAlaMetThr-41 |
| SEQ. ID. NO. 28286 | 43-ProAlaLeuLysGluGlyPheAla-50 |
| SEQ. ID. NO. 28287 | 68-GlyGlyGlyProGln-72 |
| SEQ. ID. NO. 28288 | 76-MetLeuGluLysValGlyLysLysGlyGluPhe-86 |
| SEQ. ID. NO. 28289 | 91-ArgValThrAspLysGluThrMetAsp-99 |
| SEQ. ID. NO. 28290 | 109-ValAsnLysGluIle-113 |
| SEQ. ID. NO. 28291 | 128-SerGlyArgAspAspHisPheIleLysAlaLysLysLeuLeuValAspThrProGluGlnAsnSerValAspIleGlyGln-154 |
| SEQ. ID. NO. 28292 | 159-GluSerIleAspThrGlyLeu-165 |
| SEQ. ID. NO. 28293 | 169-LeuIleGluArgGlyCysIle-175 |
| SEQ. ID. NO. 28294 | 182-GlyValGlyGlyGluLysGlyGluAla-189 |
| SEQ. ID. NO. 28295 | 200-LysLeuAlaGluGluLeuAsnAlaGluLys-209 |
| SEQ. ID. NO. 28296 | 219-ValMetAspLysThrGlyAsnLeuLeuThrLysLeuThrProLysArgIleAspGlyLeuIleAla-240 |
| SEQ. ID. NO. 28297 | 259-AlaValAsnGlyValLys-264 |
| SEQ. ID. NO. 28298 | 269-IleAspGlyArgLeuProAsnAla-276 |
| SEQ. ID. NO. 28299 | 291-IleLeuGlyArgGlyGluAspAla-298 |

Hydrophilic Regions - Hopp-Woods

| | |
|---|---|
| SEQ. ID. NO. 28300 | 9-AlaAlaAspLysAlaArgIleLeu-16 |
| SEQ. ID. NO. 28301 | 43-ProAlaLeuLysGluGlyPheAla-50 |
| SEQ. ID. NO. 28302 | 76-MetLeuGluLysValGlyLysLysGlyGluPhe-86 |
| SEQ. ID. NO. 28303 | 91-ArgValThrAspLysGluThrMetAsp-99 |
| SEQ. ID. NO. 28304 | 109-ValAsnLysGluIle-113 |
| SEQ. ID. NO. 28305 | 128-SerGlyArgAspAspHisPheIleLysAlaLysLysLeuLeuValAspThrProGluGlnAsnSerValAsp-151 |
| SEQ. ID. NO. 28306 | 183-ValGlyGlyGluLysGlyGluAla-189 |
| SEQ. ID. NO. 28307 | 200-LysLeuAlaGluGluLeuAsnAlaGluLys-209 |
| SEQ. ID. NO. 28308 | 219-ValMetAspLysThrGly-224 |
| SEQ. ID. NO. 28309 | 230-LeuThrProLysArgIleAspGlyLeuIle-239 |
| SEQ. ID. NO. 28310 | 269-IleAspGlyArgLeu-273 |
| SEQ. ID. NO. 28311 | 293-GlyArgGlyGluAspAla-298 | g140
AMPHI Regions - AMPHI

| | |
|---|---|
| SEQ. ID. NO. 28312 | 10-TyrLeuAsnSerThr-14 |
| SEQ. ID. NO. 28313 | 32-PhePheLysAsnIleLysThr-38 |
| SEQ. ID. NO. 28314 | 45-SerLeuAspSerValGluLysThrAlaGly-54 |
| SEQ. ID. NO. 28315 | 68-AsnAlaAlaArgThrAlaSer-74 |
| SEQ. ID. NO. 28316 | 108-SerAlaThrProGluThrValGluThrAlaVal-118 |
| SEQ. ID. NO. 28317 | 137-AlaAlaAlaValGlnHisAlaAsnThrAlaAspGlyValArgIlePheAsnSerLeuAlaAlaThr-158 |
| SEQ. ID. NO. 28318 | 175-LeuLysAlaValSerAspGlyLeuAsp-183 |
| SEQ. ID. NO. 28319 | 189-LeuArgValIleAlaGln-194 |
| SEQ. ID. NO. 28320 | 266-IleGlyTyrLeuLysGlyLeuPheSerTyr-275 |
| SEQ. ID. NO. 28321 | 290-GluTyrAlaGluGlySer-295 |

TABLE 1-continued

| | |
|---|---|
| SEQ. ID. NO. 28322 | 303-LeuGlyAlaLeuGly-307 |
| SEQ. ID. NO. 28323 | 352-GlyThrLeuValGlyLeu-357 |
| SEQ. ID. NO. 28324 | 391-GlyGlyPheThrGlyAlaAla-397 |
| SEQ. ID. NO. 28325 | 425-AsnGlyTrpAsnGlyLeuAlaArg-432 |

Antigenic Index - Jameson-Wolf

| | |
|---|---|
| SEQ. ID. NO. 28326 | 1-MetSerAlaArgGlyLysGlyAlaGly-9 |
| SEQ. ID. NO. 28327 | 12-AsnSerThrGlyArgHisVal-18 |
| SEQ. ID. NO. 28328 | 25-LysIleGlyGlnAspTyrSerPhe-32 |
| SEQ. ID. NO. 28329 | 34-LysAsnIleLysThrAspGlyGlyLeu-42 |
| SEQ. ID. NO. 28330 | 47-AspSerValGluLysThrAlaGlySerGluGlyAspThrProSer-61 |
| SEQ. ID. NO. 28331 | 63-TyrValArgArgGlyAsnAlaAlaArgThrAlaSer-74 |
| SEQ. ID. NO. 28332 | 86-HisAlaValGluGlnGlyGlySerAsnLeuGlu-96 |
| SEQ. ID. NO. 28333 | 102-LeuAspAlaSerGluSerSerAlaThrProGluThrValGlu-115 |
| SEQ. ID. NO. 28334 | 117-AlaValAlaAspArgThrAspMetProGlyIleArgLeuArgArgThrThrPhe-134 |
| SEQ. ID. NO. 28335 | 144-AsnThrAlaAspGlyValArg-150 |
| SEQ. ID. NO. 28336 | 160-TyrAlaAspSerAlaAlaAla-166 |
| SEQ. ID. NO. 28337 | 169-AspMetGlnGlyArgArgLeuLysAlaValSerAspGlyLeuAspHisAsnGlyThrGlyLeu-189 |
| SEQ. ID. NO. 28338 | 195-ThrGlnGlnAspGlyGlyThrTrpGluGlnGlyGlyValGluGlyLysMetArgGlySerThr-215 |
| SEQ. ID. NO. 28339 | 221-AlaAlaLysThrGlyGluAsnThrThr-229 |
| SEQ. ID. NO. 28340 | 236-IleGlyArgSerThrTrpSerGluAsnSerAlaAsnAlaLysThrAspSerIle-253 |
| SEQ. ID. NO. 28341 | 259-IleArgHisAspValGlyAsp-265 |
| SEQ. ID. NO. 28342 | 274-SerTyrGlyArgTyrLysAsnSerIleSerArgSerThrGlyAlaAspGluTyrAlaGlu-293 |
| SEQ. ID. NO. 28343 | 315-AlaThrGlyAspLeuThrValGluGlyGlyLeuArgHisAspLeuLeuLys-331 |
| SEQ. ID. NO. 28344 | 333-AspAlaPheAlaGluLysGlySerAlaLeuGlyTrpSerGlyAsnSerLeuThrGluGlyThr-353 |
| SEQ. ID. NO. 28345 | 362-LeuSerGlnProLeuSerAspLysAlaVal-371 |
| SEQ. ID. NO. 28346 | 376-AlaGlyValGluArgAspLeuAsnGlyArgAspTyrAla-388 |
| SEQ. ID. NO. 28347 | 399-AlaThrGlyLysThrGlyAlaArgAsnMetProHisThrArgArgValAla-415 |
| SEQ. ID. NO. 28348 | 421-ValGluPheGlyAsnGlyTrp-427 |
| SEQ. ID. NO. 28349 | 434-SerTyrThrGlySerLysGlnTyrGlyAsnHisSerGly-446 |

Hydrophilic Regions - Hopp-Woods

| | |
|---|---|
| SEQ. ID. NO. 28350 | 1-MetSerAlaArgGlyLysGly-7 |
| SEQ. ID. NO. 28351 | 36-IleLysThrAspGly-40 |
| SEQ. ID. NO. 28352 | 47-AspSerValGluLysThrAlaGlySerGluGlyAspThr-59 |
| SEQ. ID. NO. 28353 | 63-TyrValArgArgGlyAsnAlaAlaArgThrAlaSer-74 |
| SEQ. ID. NO. 28354 | 86-HisAlaValGluGlnGlyGlySerAsnLeu-95 |
| SEQ. ID. NO. 28355 | 102-LeuAspAlaSerGluSerSerAlaThrProGluThrValGlu-115 |
| SEQ. ID. NO. 28356 | 117-AlaValAlaAspArgThrAspMetProGlyIleArgLeuArgArgThrThrPhe-134 |
| SEQ. ID. NO. 28357 | 144-AsnThrAlaAspGly-148 |
| SEQ. ID. NO. 28358 | 169-AspMetGlnGlyArgArgLeuLysAlaValSerAspGlyLeuAspHisAsnGlyThr-187 |
| SEQ. ID. NO. 28359 | 205-GlyGlyValGluGlyLysMetArgGlySerThr-215 |
| SEQ. ID. NO. 28360 | 223-LysThrGlyGluAsnThrThr-229 |
| SEQ. ID. NO. 28361 | 244-AsnSerAlaAsnAlaLysThrAspSer-252 |
| SEQ. ID. NO. 28362 | 259-IleArgHisAspValGlyAsp-265 |
| SEQ. ID. NO. 28363 | 277-ArgTyrLysAsnSerIleSerArgSerThrGlyAlaAspGluTyrAlaGlu-293 |
| SEQ. ID. NO. 28364 | 323-GlyGlyLeuArgHisAspLeuLeuLys-331 |
| SEQ. ID. NO. 28365 | 333-AspAlaPheAlaGluLysGlySer-340 |
| SEQ. ID. NO. 28366 | 364-GlnProLeuSerAspLysAlaVal-371 |
| SEQ. ID. NO. 28367 | 376-AlaGlyValGluArgAspLeuAsnGlyArgAspTyrAla-388 |
| SEQ. ID. NO. 28368 | 399-AlaThrGlyLysThrGlyAlaArgAsnMetProHisThrArgArgValAla-415 | g141
AMPHI Regions - AMPHI

| | |
|---|---|
| SEQ. ID. NO. 28369 | 12-SerSerThrMetArgProIleGlyGluIle-21 |
| SEQ. ID. NO. 28370 | 32-IleGluProTyrGly-36 |
| SEQ. ID. NO. 28371 | 44-ProAlaGluAlaPheLysLeuPro-51 |
| SEQ. ID. NO. 28372 | 80-AlaAspAlaLeuArgHisIle-86 |
| SEQ. ID. NO. 28373 | 131-PheHisAlaIleGlyAla-136 |
| SEQ. ID. NO. 28374 | 139-AsnLeuLeuAlaAlaMetLeuAspAsn-147 |
| SEQ. ID. NO. 28375 | 174-GlnLeuArgAsnIleIleAspGlyMetGlyLysProValAspGlyValMetArgPro-192 |
| SEQ. ID. NO. 28376 | 212-AspIleSerAspLeuLysGluArgPheGly-221 |
| SEQ. ID. NO. 28377 | 244-AlaMetAlaAlaLeuLeuLysAspAlaIleLysProAsnLeu-257 |
| SEQ. ID. NO. 28378 | 259-GlnThrIleGluGlyThrPro-265 |
| SEQ. ID. NO. 28379 | 272-ProPheAlaAsnIleAlaHisGlyCysAsnSerValThrAlaThrArgLeuAlaLysHisLeuAlaAspTyrAla-296 |
| SEQ. ID. NO. 28380 | 330-AlaThrValArgAla-334 |
| SEQ. ID. NO. 28381 | 351-LeuGluAlaLeuAlaLysGlyLeuProAsnLeuLeuHisIleSerAsnLeuLysAsnValPheGly-373 |
| SEQ. ID. NO. 28382 | 406-SerLeuThrGluValTrpGlyLys-413 |
| SEQ. ID. NO. 28383 | 420-AspLeuAlaArgLysValValAsnAlaIleAspAsnGln-432 |
| SEQ. ID. NO. 28384 | 473-IleAlaSerLeuGluLys-478 |
| SEQ. ID. NO. 28385 | 502-LeuGlyCysProGluGly-507 |
| SEQ. ID. NO. 28386 | 525-ValAlaLeuCysGlyAsnMetMetLysMetProGlyLeuProLysValProAlaAla-543 |

Antigenic Index - Jameson-Wolf

| | |
|---|---|
| SEQ. ID. NO. 28387 | 3-PheLysThrAspAlaGluThrAlaGlnSerSerThrMetArgProIleGly-19 |
| SEQ. ID. NO. 28388 | 27-LeuAsnValAspAsnIleGluProTyrGly-36 |
| SEQ. ID. NO. 28389 | 38-TyrLysAlaLysIleAsnProAlaGluAlaPheLysLeuProGlnLysGlnGlyArg-56 |
| SEQ. ID. NO. 28390 | 64-AsnProThrProAlaGlyGluGlyLysThrThr-74 |
| SEQ. ID. NO. 28391 | 81-AspAlaLeuArgHisIleGlyLysAspSerValIleAlaLeuArgGluProSerLeuGlyPro-101 |
| SEQ. ID. NO. 28392 | 105-ValGlyGlyGlyAlaAlaGlyGlyGly-113 |
| SEQ. ID. NO. 28393 | 151-GlnGlyAsnGluLeuAsnIleAspProLysArgValLeuTrp-164 |
| SEQ. ID. NO. 28394 | 166-ArgValValAspMetAsnAspArgGlnLeuArgAsnIleIleAspGlyMetGlyLysProValAspGlyValMetArgProAspGlyPheAspIle-197 |
| SEQ. ID. NO. 28395 | 211-LysAspIleSerAspLeuLysGluArgPheGly-221 |
| SEQ. ID. NO. 28396 | 227-TyrAlaLysAspGlySerProValTyr-235 |

TABLE 1-continued

| | |
|---|---|
| SEQ. ID. NO. 28397 | 237-LysAspLeuLysAla-241 |
| SEQ. ID. NO. 28398 | 251-AspAlaIleLysProAsnLeu-257 |
| SEQ. ID. NO. 28399 | 287-ArgLeuAlaLysHisLeuAla-293 |
| SEQ. ID. NO. 28400 | 306-LeuGlyAlaGluLysPheCysAspIleLysCysArgLeuAlaGlyLeuLysProAspAla-325 |
| SEQ. ID. NO. 28401 | 335-LeuLysTyrAsnGlyGlyValGluArgAlaAsnLeuGlyGluGluAsnLeuGluAlaLeuAla-355 |
| SEQ. ID. NO. 28402 | 383-PheValSerAspSerAspAlaGluLeuAlaMetIleGluLysAlaCysAla-399 |
| SEQ. ID. NO. 28403 | 411-TrpGlyLysGlyGlyAlaGlyGlyAlaAspLeuAlaArgLysValValAsn-427 |
| SEQ. ID. NO. 28404 | 429-IleAspAsnGlnProAsnAsnPhe-436 |
| SEQ. ID. NO. 28405 | 444-LeuGlyIleLysAspLysIleArgAlaIleAla-454 |
| SEQ. ID. NO. 28406 | 458-TyrGlyAlaGluAspValAspPheSerAla-467 |
| SEQ. ID. NO. 28407 | 474-AlaSerLeuGluLysLeuGlyLeuAspLysMetPro-485 |
| SEQ. ID. NO. 28408 | 494-SerLeuSerAspAsnAlaLysLeu-501 |
| SEQ. ID. NO. 28409 | 503-GlyCysProGluGlyPhe-508 |
| SEQ. ID. NO. 28410 | 534-MetProGlyLeuPro-538 |
| SEQ. ID. NO. 28411 | 541-ProAlaAlaGluLysIleAspValAspGluHisGly-552 |
| Hydrophilic Regions - Hopp-Woods | |
| SEQ. ID. NO. 28412 | 3-PheLysThrAspAlaGluThrAlaGln-11 |
| SEQ. ID. NO. 28413 | 38-TyrLysAlaLysIleAsnPro-44 |
| SEQ. ID. NO. 28414 | 46-GluAlaPheLysLeuProGlnLysGlnGlyArg-56 |
| SEQ. ID. NO. 28415 | 67-ProAlaGlyGluGlyLysThr-73 |
| SEQ. ID. NO. 28416 | 81-AspAlaLeuArgHisIleGlyLysAspSerValIleAlaLeuArgGluProSer-98 |
| SEQ. ID. NO. 28417 | 155-LeuAsnIleAspProLysArgValLeuTrp-164 |
| SEQ. ID. NO. 28418 | 166-ArgValValAspMetAsnAspArgGlnLeuArgAsnIleIle-179 |
| SEQ. ID. NO. 28419 | 181-GlyMetGlyLysProValAspGlyValMetArgProAspGlyPhe-195 |
| SEQ. ID. NO. 28420 | 211-LysAspIleSerAspLeuLysGluArgPheGly-221 |
| SEQ. ID. NO. 28421 | 228-AlaLysAspGlySer-232 |
| SEQ. ID. NO. 28422 | 237-LysAspLeuLysAla-241 |
| SEQ. ID. NO. 28423 | 287-ArgLeuAlaLysHisLeuAla-293 |
| SEQ. ID. NO. 28424 | 306-LeuGlyAlaGluLysPheCysAspIleLysCysArgLeuAlaGlyLeuLysProAspAla-325 |
| SEQ. ID. NO. 28425 | 339-GlyGlyValGluArgAlaAsnLeuGlyGluGluAsnLeuGluAlaLeuAla-355 |
| SEQ. ID. NO. 28426 | 383-PheValSerAspSerAspAlaGluLeuAlaMetIleGluLysAlaCysAla-399 |
| SEQ. ID. NO. 28427 | 420-AspLeuAlaArgLysValValAsn-427 |
| SEQ. ID. NO. 28428 | 444-LeuGlyIleLysAspLysIleArgAlaIleAla-454 |
| SEQ. ID. NO. 28429 | 458-TyrGlyAlaGluAspValAspPheSerAla-467 |
| SEQ. ID. NO. 28430 | 474-AlaSerLeuGluLysLeuGlyLeuAspLysMetPro-485 |
| SEQ. ID. NO. 28431 | 541-ProAlaAlaGluLysIleAspValAspGluHisGly-552 |
| g142 | |
| AMPHI Regions - AMPHI | |
| SEQ. ID. NO. 28432 | 26-ArgPheAlaAlaMetProAsnMetValGlyLys-36 |
| SEQ. ID. NO. 28433 | 44-GlyGlnProGlyLysMetPhe-50 |
| SEQ. ID. NO. 28434 | 100-AlaValThrProCysArg-105 |
| SEQ. ID. NO. 28435 | 107-ValCysArgAspAspMetAsn-113 |
| SEQ. ID. NO. 28436 | 118-GlyCysHisArgIleThrGluArgSerLeuLysSerPheLeuGlnIleArgHisPheSerProLeuAsnArg-141 |
| Antigenic Index - Jameson-Wolf | |
| SEQ. ID. NO. 28437 | 37-ProLeuPheGlyArgGlnAlaGlyGlnProGlyLysMet-49 |
| SEQ. ID. NO. 28438 | 60-HisIleAspAlaGluAlaAlaValPheArgGlnAspArgAsnAspSerArgThrPro-78 |
| SEQ. ID. NO. 28439 | 83-HisHisGlyArgArgLeuValGlyAsnArgArgAsnArgArgHisCysAsnAlaValThrProCysArgThrValCysArgAspAspMetAsnAlaCysArgThrGlyCysHisArgIleThrGluArgSerLeuLys-128 |
| SEQ. ID. NO. 28440 | 137-SerProLeuAsnArgProLeuTyrLysAsnAlaAlaHisLysAlaSerProHis-154 |
| Hydrophilic Regions - Hopp-Woods | |
| SEQ. ID. NO. 28441 | 42-GlnAlaGlyGlnPro-46 |
| SEQ. ID. NO. 28442 | 60-HisIleAspAlaGluAlaAlaValPheArgGlnAspArgAsnAspSerArgThr-77 |
| SEQ. ID. NO. 28443 | 84-HisGlyArgArgLeuValGlyAsnArgArgAsnArgArgHisCys-98 |
| SEQ. ID. NO. 28444 | 106-ThrValCysArgAspAspMetAsnAlaCysArg-116 |
| SEQ. ID. NO. 28445 | 121-ArgIleThrGluArgSerLeuLys-128 |
| SEQ. ID. NO. 28446 | 147-AlaAlaHisLysAlaSerPro-153 |
| g144 | |
| AMPHI Regions - AMPHI | |
| SEQ. ID. NO. 28447 | 36-LeuGlyGlyIleValGlnGluPhe-43 |
| SEQ. ID. NO. 28448 | 45-ValLeuAlaAspGlyVal-50 |
| SEQ. ID. NO. 28449 | 58-PheAspAspAlaAlaSer-63 |
| SEQ. ID. NO. 28450 | 71-IleAsnLysGlnIleGlyArgValAlaGlyArg-81 |
| SEQ. ID. NO. 28451 | 144-TyrArgTyrLeuSerArgHis-150 |
| SEQ. ID. NO. 28452 | 170-GlyProAlaArgCysGlySerAlaTyrSerAlaGly-181 |
| SEQ. ID. NO. 28453 | 185-SerGlyArgCysArgLysThrAlaArgLeuAsnGlyPheArgArgProArgSer-202 |
| Antigenic Index - Jameson-Wolf | |
| SEQ. ID. NO. 28454 | 1-MetSerAspThrProAlaThrArgAspPheGlyLeuIleAspGlyArgAla-17 |
| SEQ. ID. NO. 28455 | 23-LeuSerAsnArgArgGlyThr-29 |
| SEQ. ID. NO. 28456 | 47-AlaAspGlyValArgGluAsnPro-54 |
| SEQ. ID. NO. 28457 | 57-SerPheAspAspAlaAlaSerTyrAlaAspAsnProPheGlnIleAsnLysGlnIleGly-76 |
| SEQ. ID. NO. 28458 | 78-ValAlaGlyArgIleArgGlyAlaAla-86 |
| SEQ. ID. NO. 28459 | 88-AspIleAsnGlyArgThrTyrArgValGluAlaAsnGluGlyArgAsnAlaLeuHisGlyGlySerHis-110 |
| SEQ. ID. NO. 28460 | 120-ValAlaAlaAspGlyArgArgLeuSerGlnArg-130 |
| SEQ. ID. NO. 28461 | 136-ProLeuGlyArgGlyArgProAlaTyr-144 |
| SEQ. ID. NO. 28462 | 146-TyrLeuSerArgHisArgAlaArgArgHisGlyValArgProAspAlaAlaHis-163 |
| SEQ. ID. NO. 28463 | 167-AlaGlyArgGlyProAlaArgCysGlySer-176 |
| SEQ. ID. NO. 28464 | 179-SerAlaGlyArgThrTyrSerGlyArgCysArgLysThrAlaArgLeuAsnGlyPheArgArgProArgSerIle-203 |
| Hydrophilic Regions - Hopp-Woods | |
| SEQ. ID. NO. 28465 | 1-MetSerAspThrProAlaThrArgAsp-9 |

TABLE 1-continued

| | |
|---|---|
| SEQ. ID. NO. 28466 | 24-SerAsnArgArgGlyThr-29 |
| SEQ. ID. NO. 28467 | 48-AspGlyValArgGluAsnPro-54 |
| SEQ. ID. NO. 28468 | 57-SerPheAspAspAlaAlaSer-63 |
| SEQ. ID. NO. 28469 | 78-ValAlaGlyArgIleArgGlyAlaAla-86 |
| SEQ. ID. NO. 28470 | 89-IleAsnGlyArgThrTyrArgValGluAlaAsnGluGlyArgAsnAlaLeu-105 |
| SEQ. ID. NO. 28471 | 121-AlaAlaAspGlyArgArgLeuSerGln-129 |
| SEQ. ID. NO. 28472 | 138-GlyArgGlyArgProAla-143 |
| SEQ. ID. NO. 28473 | 148-SerArgHisArgAlaArgArgHisGlyValArgProAspAla-161 |
| SEQ. ID. NO. 28474 | 168-GlyArgGlyProAlaArgCys-174 |
| SEQ. ID. NO. 28475 | 182-ArgThrTyrSerGlyArgCysArgLysThrAlaArg-193 |
| SEQ. ID. NO. 28476 | 195-AsnGlyPheArgArgProArgSerIle-203 | g146
AMPHI Regions - AMPHI

| | |
|---|---|
| SEQ. ID. NO. 28477 | 20-GlnTyrGlyLeuPheAspPheMetProCys-29 |
| SEQ. ID. NO. 28478 | 34-ProLeuAspAsnPheProThrVal-41 |
| SEQ. ID. NO. 28479 | 95-LeuArgAlaCysAlaValIle-101 |
| SEQ. ID. NO. 28480 | 140-AlaArgArgMetArg-144 |
| SEQ. ID. NO. 28481 | 158-ArgHisGlnArgGlyPheAlaArg-165 |

Antigenic Index - Jameson-Wolf

| | |
|---|---|
| SEQ. ID. NO. 28482 | 13-IleAspHisAspLysValGluGln-20 |
| SEQ. ID. NO. 28483 | 29-CysLeuArgGlnProProLeuAspAsn-37 |
| SEQ. ID. NO. 28484 | 41-ValArgProAlaProPheGluAlaArgGlyLysHisValGluArgArgArgGlnAspLysAspThrAspSerPheArgGlnArgValAlaAsnLeuArgArgAlaLeu-76 |
| SEQ. ID. NO. 28485 | 86-AlaCysArgArgGlnArgIleHisAla-94 |
| SEQ. ID. NO. 28486 | 112-SerLeuLeuArgAspLysArgPhe-119 |
| SEQ. ID. NO. 28487 | 138-ArgArgAlaArgArgMetArgHisGlyAsnAla-148 |
| SEQ. ID. NO. 28488 | 155-GlnGlnProArgHisGlnArgGlyPheAla-164 |
| SEQ. ID. NO. 28489 | 166-AlaGlySerGlyArgAsnAspLysAspValAlaPheSerIle-179 |
| SEQ. ID. NO. 28490 | 193-ValSerGlnArgThr-197 |

Hydrophilic Regions - Hopp-Woods

| | |
|---|---|
| SEQ. ID. NO. 28491 | 13-IleAspHisAspLysValGluGln-20 |
| SEQ. ID. NO. 28492 | 44-AlaProPheGluAlaArgGlyLysHisValGluArgArgArgGlnAspLysAspThrAspSerPheArgGlnArgValAlaAsnLeuArgArgAlaLeu-76 |
| SEQ. ID. NO. 28493 | 86-AlaCysArgArgGlnArgIleHisAla-94 |
| SEQ. ID. NO. 28494 | 112-SerLeuLeuArgAspLysArgPhe-119 |
| SEQ. ID. NO. 28495 | 138-ArgArgAlaArgArgMetArgHisGlyAsn-147 |
| SEQ. ID. NO. 28496 | 156-GlnProArgHisGlnArgGlyPheAla-164 |
| SEQ. ID. NO. 28497 | 167-GlySerGlyArgAsnAspLysAspValAla-176 | g148
AMPHI Regions - AMPHI

| | |
|---|---|
| SEQ. ID. NO. 28498 | 25-AlaAspLysIleArgLysIleGluAsnTrpPro-35 |
| SEQ. ID. NO. 28499 | 49-GlnSerAlaGluTyrPheArgLeuLeuValAspLeu-60 |
| SEQ. ID. NO. 28500 | 150-AlaGlyLeuGluLeuIleArgLysLeuGlyGlyGluIle-162 |
| SEQ. ID. NO. 28501 | 165-AlaAlaAlaIleLeuGluPheThrAspLeuGlnGlyGlyLysAsnIleArg-181 |

Antigenic Index - Jameson-Wolf

| | |
|---|---|
| SEQ. ID. NO. 28502 | 4-LysThrSerAsnLeu-8 |
| SEQ. ID. NO. 28503 | 24-LeuAlaAspLysIleArgLysIleGluAsnTrpProGlnLysGly-38 |
| SEQ. ID. NO. 28504 | 66-MetAspGlnLysIleAspIle-72 |
| SEQ. ID. NO. 28505 | 76-LeuAspAlaArgGly-80 |
| SEQ. ID. NO. 28506 | 97-ProIleArgLysLysGlyLysLeuPro-105 |
| SEQ. ID. NO. 28507 | 117-TyrGlyGluAlaAlaVal-122 |
| SEQ. ID. NO. 28508 | 124-IleHisThrAspAlaValLysProGlySerArg-134 |
| SEQ. ID. NO. 28509 | 153-GluLeuIleArgLysLeuGlyGlyGluIleValGlu-164 |
| SEQ. ID. NO. 28510 | 172-ThrAspLeuGlnGlyGlyLysAsnIleArgAlaSerGlyAlaPro-186 |
| SEQ. ID. NO. 28511 | 192-GlnAsnGluGlyCysMetLysGly-199 |

Hydrophilic Regions - Hopp-Woods

| | |
|---|---|
| SEQ. ID. NO. 28512 | 24-LeuAlaAspLysIleArgLysIleGluAsnTrpPro-35 |
| SEQ. ID. NO. 28513 | 66-MetAspGlnLysIleAspIle-72 |
| SEQ. ID. NO. 28514 | 97-ProIleArgLysLysGlyLysLeuPro-105 |
| SEQ. ID. NO. 28515 | 117-TyrGlyGluAlaAlaVal-122 |
| SEQ. ID. NO. 28516 | 124-IleHisThrAspAlaValLysProGlySer-133 |
| SEQ. ID. NO. 28517 | 153-GluLeuIleArgLysLeuGlyGlyGluIleValGlu-164 |
| SEQ. ID. NO. 28518 | 178-LysAsnIleArgAlaSerGly-184 |
| SEQ. ID. NO. 28519 | 195-GlyCysMetLysGly-199 | g149
AMPHI Regions - AMPHI

| | |
|---|---|
| SEQ. ID. NO. 28520 | 72-AsnLeuGlyAspAlaLeuAspGlyValProGlyIle-83 |
| SEQ. ID. NO. 28521 | 101-ThrGlyArgArgIleLysValLeuAsnHisHisGlyGluThrGlyAspMet-117 |
| SEQ. ID. NO. 28522 | 135-GlnValGluIleLeuArgGlyProValThr-144 |
| SEQ. ID. NO. 28523 | 152-ValAlaGlyLeuValAsp-157 |
| SEQ. ID. NO. 28524 | 164-ProGluLysMetProGluAsn-170 |
| SEQ. ID. NO. 28525 | 184-AsnLeuGluLysLeu-188 |
| SEQ. ID. NO. 28526 | 220-TyrArgAsnLeuLysArgLeuProAspSerHis-230 |
| SEQ. ID. NO. 28527 | 345-PheProGlyPheGlu-349 |
| SEQ. ID. NO. 28528 | 366-AlaGlyAspAlaValGluAsnPhePheAsnAsn-376 |
| SEQ. ID. NO. 28529 | 389-ProIleGlyArgLeuLys-394 |
| SEQ. ID. NO. 28530 | 411-AlaIleProGluThrVal-416 |
| SEQ. ID. NO. 28531 | 472-GlnProLeuProAspLeuGlyAla-479 |
| SEQ. ID. NO. 28532 | 565-ArgPheGlyAsnTyrIleTyrAlaGln-573 |
| SEQ. ID. NO. 28533 | 576-AsnAspGlyArgGlyProLysSerIleGluAsp-586 |
| SEQ. ID. NO. 28534 | 627-ArgGlyArgLeuLysAsnLeuProSer-635 |

TABLE 1-continued

| | |
|---|---|
| SEQ. ID. NO. 28535 | 672-LeuThrAspArgIle-676 |
| Antigenic Index - Jameson-Wolf | |
| SEQ. ID. NO. 28536 | 25-HisGluThrGluGln-29 |
| SEQ. ID. NO. 28537 | 40-GlyLysSerArgProArgAlaThrSerGly-49 |
| SEQ. ID. NO. 28538 | 55-ThrAlaSerAspLysIleIleSerGlyAspThrLeuArgGlnLysAla-70 |
| SEQ. ID. NO. 28539 | 97-IleArgGlyGlnThrGlyArgArgIleLysVal-107 |
| SEQ. ID. NO. 28540 | 109-AsnHisHisGlyGluThrGlyAspMetAlaAspPheSerProAspHis-124 |
| SEQ. ID. NO. 28541 | 137-GluIleLeuArgGlyPro-142 |
| SEQ. ID. NO. 28542 | 157-AspValAlaAspGlyLysIleProGluLysMetProGluAsnGlyValSerGlyGluAlaGlyLeu-178 |
| SEQ. ID. NO. 28543 | 180-LeuSerSerGlyAsnLeuGluLysLeuThrSer-190 |
| SEQ. ID. NO. 28544 | 207-GlyLeuTyrArgLysSerGlyAspTyrAlaValProArgTyrArgAsnLeuLysArgLeuProAspSerHisAlaAspSerGlnThrGly-236 |
| SEQ. ID. NO. 28545 | 244-GlyGluLysGlyPhe-248 |
| SEQ. ID. NO. 28546 | 252-AlaTyrSerAspArgArgAspArgTyrGlyLeuProAlaHisSerHisGluTyrAspAspCysHisAla-274 |
| SEQ. ID. NO. 28547 | 281-SerLeuIleAsnLysArgTyrLeu-288 |
| SEQ. ID. NO. 28548 | 295-LeuThrGluGluAspIleAspTyrAspAsnProGlyLeu-307 |
| SEQ. ID. NO. 28549 | 309-CysGlyPheHisAspGlyAspGlyAlaHis-318 |
| SEQ. ID. NO. 28550 | 320-HisThrHisAsnGlyLysProTrpIleAspLeuArgAsnLysArgTyrGluLeuArgAlaGluTrpLysGlnProPheProGly-347 |
| SEQ. ID. NO. 28551 | 354-HisLeuAsnArgAsnAspTyrHisHisAspGluLysAlaGlyAspAlaVal-370 |
| SEQ. ID. NO. 28552 | 374-PheAsnAsnLysThrHisAsnAlaArgIleGluLeuArgHisGlnProIleGlyArgLeuLysGlySerTrp-397 |
| SEQ. ID. NO. 28553 | 402-LeuGlyGlnLysSerSerAla-408 |
| SEQ. ID. NO. 28554 | 413-ProGluThrValGln-417 |
| SEQ. ID. NO. 28555 | 421-LeuIleAspAsnAsnValArg-427 |
| SEQ. ID. NO. 28556 | 437-AlaAsnTrpAspAsnPheThrLeuGluGlyGlyValArgValGluLysGlnLysAlaSerIleArgTyrAspLysAlaLeuIleAspArgGluAsnTyrTyrAsnGlnProLeuProAsp-476 |
| SEQ. ID. NO. 28557 | 506-SerHisGlnGluArgLeuProSerThrGlnGluLeuTyrAlaHisGly-521 |
| SEQ. ID. NO. 28558 | 531-ValGlyAsnLysHisLeuAsnLysGluArgSerAsnAsnIle-544 |
| SEQ. ID. NO. 28559 | 549-GlyTyrGluGlyAspArgTrpGln-556 |
| SEQ. ID. NO. 28560 | 562-TyrArgAsnArgPheGlyAsn-568 |
| SEQ. ID. NO. 28561 | 574-ThrLeuAsnAspGlyArgGlyProLysSerIleGluAspAspSerGluMetLysLeu-592 |
| SEQ. ID. NO. 28562 | 594-ArgTyrAsnGlnSerGlyAlaAspPheTyrGlyAlaGluGly-607 |
| SEQ. ID. NO. 28563 | 609-IleTyrPheLysProThrProArgTyrArgIle-619 |
| SEQ. ID. NO. 28564 | 621-ValSerGlyAspTyrValArgGlyArgLeuLysAsnLeuProSerLeuProGlyArgGluAspProTyrGlyLysArgProPhe-648 |
| SEQ. ID. NO. 28565 | 651-GlnAlaAspGlnAsnAlaProArgIleProAla-661 |
| SEQ. ID. NO. 28566 | 670-ThrSerLeuThrAspArgIleAspAlaAsnLeuAspTyr-682 |
| SEQ. ID. NO. 28567 | 689-AsnLysLeuAlaArgTyrGluThrArgThrProGlyHis-701 |
| SEQ. ID. NO. 28568 | 707-GlyAlaAsnTyrArgArgAsnThrArgTyrGlyGluTrp-719 |
| SEQ. ID. NO. 28569 | 725-AlaAspAsnLeuLeu-729 |
| SEQ. ID. NO. 28570 | 739-PheLeuSerAspThrProGlnMetGlyArgSerPheThrGlyGlyVal-754 |
| Hydrophilic Regions - Hopp-Woods | |
| SEQ. ID. NO. 28571 | 25-HisGluThrGluGln-29 |
| SEQ. ID. NO. 28572 | 40-GlyLysSerArgProArgAlaThr-47 |
| SEQ. ID. NO. 28573 | 55-ThrAlaSerAspLysIleIleSer-62 |
| SEQ. ID. NO. 28574 | 64-AspThrLeuArgGlnLysAla-70 |
| SEQ. ID. NO. 28575 | 100-GlnThrGlyArgArgIleLysVal-107 |
| SEQ. ID. NO. 28576 | 112-GlyGluThrGlyAspMetAlaAspPheSerPro-122 |
| SEQ. ID. NO. 28577 | 157-AspValAlaAspGlyLysIleProGluLysMetProGluAsnGlyValSerGly-174 |
| SEQ. ID. NO. 28578 | 181-SerSerGlyAsnLeuGluLysLeuThr-189 |
| SEQ. ID. NO. 28579 | 207-GlyLeuTyrArgLysSerGlyAsp-214 |
| SEQ. ID. NO. 28580 | 219-ArgTyrArgAsnLeuLysArgLeuProAspSerHisAlaAspSerGlnThr-235 |
| SEQ. ID. NO. 28581 | 253-TyrSerAspArgArgAspArgTyrGly-261 |
| SEQ. ID. NO. 28582 | 267-HisGluTyrAspAspCysHisAla-274 |
| SEQ. ID. NO. 28583 | 295-LeuThrGluGluAspIleAspTyrAspAsn-304 |
| SEQ. ID. NO. 28584 | 312-HisAspGlyAspGlyAlaHis-318 |
| SEQ. ID. NO. 28585 | 330-LeuArgAsnLysArgTyrGluLeuArgAlaGluTrp-341 |
| SEQ. ID. NO. 28586 | 354-HisLeuAsnArgAsnAspTyrHisHisAspGluLysAlaGlyAspAlaVal-370 |
| SEQ. ID. NO. 28587 | 377-LysThrHisAsnAlaArgIleGluLeuArgHis-387 |
| SEQ. ID. NO. 28588 | 391-GlyArgLeuLysGly-395 |
| SEQ. ID. NO. 28589 | 446-GlyGlyValArgValGluLysGlnLysAlaSerIleArgTyrAspLysAlaLeuIleAspArgGluAsnTyr-469 |
| SEQ. ID. NO. 28590 | 506-SerHisGlnGluArgLeuProSer-513 |
| SEQ. ID. NO. 28591 | 535-HisLeuAsnLysGluArgSerAsnAsn-543 |
| SEQ. ID. NO. 28592 | 550-TyrGluGlyAspArgTrp-555 |
| SEQ. ID. NO. 28593 | 562-TyrArgAsnArgPhe-566 |
| SEQ. ID. NO. 28594 | 575-LeuAsnAspGlyArgGlyProLysSerIleGluAspAspSerGluMetLysLeu-592 |
| SEQ. ID. NO. 28595 | 603-TyrGlyAlaGluGly-607 |
| SEQ. ID. NO. 28596 | 613-ProThrProArgTyrArgIle-619 |
| SEQ. ID. NO. 28597 | 624-AspTyrValArgGlyArgLeuLysAsn-632 |
| SEQ. ID. NO. 28598 | 637-ProGlyArgGluAspProTyrGlyLys-645 |
| SEQ. ID. NO. 28599 | 652-AlaAspGlnAsnAlaProArg-658 |
| SEQ. ID. NO. 28600 | 671-SerLeuThrAspArgIleAspAla-678 |
| SEQ. ID. NO. 28601 | 690-LysLeuAlaArgTyrGluThrArgThrProGly-700 |
| SEQ. ID. NO. 28602 | 709-AsnTyrArgArgAsnThrArgTyrGly-717 |
| g150 | |
| AMPHI Regions - AMPHI | |
| SEQ. ID. NO. 28603 | 60-GlyGluIleLeuAspLeuLeu-66 |
| SEQ. ID. NO. 28604 | 87-LeuLeuSerHisPheGlu-92 |
| SEQ. ID. NO. 28605 | 100-PheValLysGlyTyrAla-105 |
| SEQ. ID. NO. 28606 | 132-IleAlaGlyValLeuHisArgPheProAlaLysLeuThrAla-145 |
| SEQ. ID. NO. 28607 | 147-GlnPheAlaGlyLeuLeuArgProLeuAla-156 |
| SEQ. ID. NO. 28608 | 235-GlyValAlaProPheArg-240 |
| SEQ. ID. NO. 28609 | 272-ThrGluTrpGlnGlnPheAlaLys-279 |

TABLE 1-continued

| | |
|---|---|
| SEQ. ID. NO. 28610 | 304-IleArgGluGlnAla-308 |
| SEQ. ID. NO. 28611 | 327-AlaAlaLysMetAlaLysGluValGluAlaAlaLeuLeuAspValIleIleGly-344 |

Antigenic Index - Jameson-Wolf

| | |
|---|---|
| SEQ. ID. NO. 28612 | 2-TerTyrCysLysAlaAspProPhePro-10 |
| SEQ. ID. NO. 28613 | 17-GlnLysIleThrAlaArgGlnSerAspLysAspValArgHisIleGluIleAspLeuSerGlySerAspLeu-40 |
| SEQ. ID. NO. 28614 | 43-LeuProGlyAspAla-47 |
| SEQ. ID. NO. 28615 | 52-PheAspAsnAspProAlaLeuVal-59 |
| SEQ. ID. NO. 28616 | 69-AsnProAlaThrGluIleGlnAlaGlyGlyLysThrLeu-81 |
| SEQ. ID. NO. 28617 | 93-LeuThrGlnAsnThrProAlaPhe-100 |
| SEQ. ID. NO. 28618 | 108-AlaAspAsnAspGluLeuAspArgIleAlaAla-118 |
| SEQ. ID. NO. 28619 | 163-SerSerSerGlnAlaGluAlaGlyAspGluValHis-174 |
| SEQ. ID. NO. 28620 | 181-ArgPheGluHisGluGlyArgAlaArgAlaGlyGlyAlaSerGlyPhePhe-197 |
| SEQ. ID. NO. 28621 | 199-AspArgLeuGluGluAspGlyThrVal-207 |
| SEQ. ID. NO. 28622 | 210-PheAlaGluArgAsnAspGlyPheArgLeuProGluAspSerArgLysPro-226 |
| SEQ. ID. NO. 28623 | 231-GlySerGlyThrGly-235 |
| SEQ. ID. NO. 28624 | 245-GlnArgAlaAlaGluAsnAlaGluGlyArgAsn-255 |
| SEQ. ID. NO. 28625 | 276-GlnPheAlaLysAspGlyPheLeuHisArgTyrAspPheAlaTrpSerArgAspGlnGluGluLysIleTyrVal-300 |
| SEQ. ID. NO. 28626 | 302-AspLysIleArgGluGlnAlaGlu-309 |
| SEQ. ID. NO. 28627 | 326-AspAlaAlaLysMetAlaLysGluValGlu-335 |
| SEQ. ID. NO. 28628 | 345-AlaGlyHisSerAspGluAspGlyAlaGluGlyTyr-356 |
| SEQ. ID. NO. 28629 | 359-MetLeuArgGluGluLysArgTyrGlnArgAspValTyr-371 |

Hydrophilic Regions - Hopp-Woods

| | |
|---|---|
| SEQ. ID. NO. 28630 | 18-LysIleThrAlaArgGlnSerAspLysAspValArgHisIleGluIleAspLeuSerGly-37 |
| SEQ. ID. NO. 28631 | 72-ThrGluIleGlnAlaGlyGlyLys-79 |
| SEQ. ID. NO. 28632 | 108-AlaAspAsnAspGluLeuAspArgIleAlaAla-118 |
| SEQ. ID. NO. 28633 | 165-SerGlnAlaGlyAlaGlyAspGluValHis-174 |
| SEQ. ID. NO. 28634 | 181-ArgPheGluHisGluGlyArgAlaArgAlaGlyGly-192 |
| SEQ. ID. NO. 28635 | 199-AspArgLeuGluGluAspGlyThrVal-207 |
| SEQ. ID. NO. 28636 | 210-PheAlaGluArgAsnAspGlyPheArgLeuProGluAspSerArgLysPro-226 |
| SEQ. ID. NO. 28637 | 246-ArgAlaAlaGluAsnAlaGluGlyArg-254 |
| SEQ. ID. NO. 28638 | 290-TrpSerArgAspGlnGluGluLysIleTyrVal-300 |
| SEQ. ID. NO. 28639 | 302-AspLysIleArgGluGlnAlaGlu-309 |
| SEQ. ID. NO. 28640 | 326-AspAlaAlaLysMetAlaLysGluValGlu-335 |
| SEQ. ID. NO. 28641 | 346-GlyHisSerAspGluAspGlyAlaGluGlyTyr-356 |
| SEQ. ID. NO. 28642 | 359-MetLeuArgGluGluLysArgTyrGlnArgAspValTyr-371 | g151
AMPHI Regions - AMPHI

| | |
|---|---|
| SEQ. ID. NO. 28643 | 6-AsnIleAlaIleIleAla-11 |
| SEQ. ID. NO. 28644 | 22-AspGlnLeuLeuArg-26 |
| SEQ. ID. NO. 28645 | 73-AspThrProGlyHis-77 |
| SEQ. ID. NO. 28646 | 81-GlyGlyGluValGluArgValLeuGlyMetValAspCysVal-94 |
| SEQ. ID. NO. 28647 | 128-LysIleAspLysPro-132 |
| SEQ. ID. NO. 28648 | 144-PheGluLeuPheAspAsnLeuGlyAlaThr-153 |
| SEQ. ID. NO. 28649 | 165-SerGlyLeuSerGlyPheAlaLysLeuGluGluThrAspGlu-178 |
| SEQ. ID. NO. 28650 | 182-MetArgProLeuPheAspThrIleLeuLysTyrThr-193 |
| SEQ. ID. NO. 28651 | 248-GlyArgIleAsnGlnLeuLeuGlyPheLysGlyLeuGluArgVal-262 |
| SEQ. ID. NO. 28652 | 273-ValIleIleSerGlyIleGlu-279 |
| SEQ. ID. NO. 28653 | 330-IleArgAspArgLeuGlnLysGluLeu-338 |
| SEQ. ID. NO. 28654 | 348-AspThrAlaAspAla-352 |
| SEQ. ID. NO. 28655 | 396-CysGluProTyrGluAsnLeuThrValAsp-405 |
| SEQ. ID. NO. 28656 | 457-LeuThrArgGlyValGly-462 |
| SEQ. ID. NO. 28657 | 464-MetSerHisValPheAsp-469 |
| SEQ. ID. NO. 28658 | 537-LysGlyLysLysLeuThrAsnIle-544 |
| SEQ. ID. NO. 28659 | 551-GluAlaValArgLeuThrThr-557 |

Antigenic Index - Jameson-Wolf

| | |
|---|---|
| SEQ. ID. NO. 28660 | 1-MetLysGlnIleArg-5 |
| SEQ. ID. NO. 28661 | 13-ValAspHisGlyLysThrThrLeu-20 |
| SEQ. ID. NO. 28662 | 24-LeuLeuArgGlnSerGlyThrPheArgAlaAsnGlnGlnValAspGluArgValMetAspSerAsnAspLeuGluLysGluArgGlyIle-53 |
| SEQ. ID. NO. 28663 | 59-AsnThrAlaIleAspTyrGluGlyCysHis-68 |
| SEQ. ID. NO. 28664 | 72-ValAspThrProGlyHisAlaAspPheGlyGlyGluValGluArg-86 |
| SEQ. ID. NO. 28665 | 99-AspAlaGlnGluGlyProMetProGlnThrArgPheValThr-112 |
| SEQ. ID. NO. 28666 | 128-LysIleAspLysProSerAlaArgProSerTrp-138 |
| SEQ. ID. NO. 28667 | 151-GlyAlaThrAspGluGlnLeuAsp-158 |
| SEQ. ID. NO. 28668 | 171-AlaLysLeuGluGluThrAspGluSerSerAspMetArgProLeu-185 |
| SEQ. ID. NO. 28669 | 193-ThrProAlaProSerGlySerAlaAspGluProLeu-204 |
| SEQ. ID. NO. 28670 | 211-LeuAspTyrAspAsnTyrThrGly-218 |
| SEQ. ID. NO. 28671 | 226-LeuAsnGlyArgIleLysProGlyGln-234 |
| SEQ. ID. NO. 28672 | 241-HisGluGlnGlnIleAla-246 |
| SEQ. ID. NO. 28673 | 257-LysGlyLeuGluArgValProLeuGluGluAlaGluAlaGlyAsp-271 |
| SEQ. ID. NO. 28674 | 277-GlyIleGluAspIleGly-282 |
| SEQ. ID. NO. 28675 | 287-IleThrValLysAspAsnProLysGlyLeuPro-297 |
| SEQ. ID. NO. 28676 | 300-SerValAspGluProThrLeu-306 |
| SEQ. ID. NO. 28677 | 314-ThrSerProLeuAlaGlyThrGluGlyLysPheValThrSerArgGlnIleArgAspArgLeuGlnLysGluLeuLeu-339 |
| SEQ. ID. NO. 28678 | 344-LeuArgValGluAspThrAlaAspAlaAspValPheArgValSerGlyArgGlyGluLeu-363 |
| SEQ. ID. NO. 28679 | 371-AsnMetArgArgGluGlyTyr-377 |
| SEQ. ID. NO. 28680 | 381-ValGlyLysProArgValValTyrArgAspIleAspGlyGlnLysCysGluProTyrGluAsnLeuThrValAspValProAspAspAsnGlnGly AlaValMetGluGluLeuGlyArgArgArgGlyGluLeuThrAsnMetGluSerAspGlyAsnGlyArgThrArgLeuGluTyr-440 |
| SEQ. ID. NO. 28681 | 467-ValPheAspAspTyrAlaProValLysProAspMetProGlyArgHisAsnGly-484 |
| SEQ. ID. NO. 28682 | 489-GlnGluGlnGlyGlyGlu-493 |
| SEQ. ID. NO. 28683 | 501-AsnLeuGluAspArgGlyArgMetPheValSerProAsnAspLysIleTyr-517 |

TABLE 1-continued

| SEQ. ID. NO. 28684 | 524-IleHisSerArgAspAsnAspLeu-531 |
|---|---|
| SEQ. ID. NO. 28685 | 535-ProLeuLysGlyLysLysLeuThrAsnIleArgAlaSerGlyThrAspGluAlaValArg-554 |
| SEQ. ID. NO. 28686 | 569-PheIleAspAspAspGluLeuValGlu-577 |
| SEQ. ID. NO. 28687 | 579-ThrProGlnSerIleArgLeuArgMet-587 |
| SEQ. ID. NO. 28688 | 591-SerGluLeuGluArgArgArgHisPheLysLysLeuAsp-603 |

Hydrophilic Regions - Hopp-Woods

| SEQ. ID. NO. 28689 | 1-MetLysGlnIleArg-5 |
|---|---|
| SEQ. ID. NO. 28690 | 29-GlyThrPheArgAla-33 |
| SEQ. ID. NO. 28691 | 35-GlnGlnValAspGluArgValMetAspSerAsnAspLeuGluLysGluArgGlyIle-53 |
| SEQ. ID. NO. 28692 | 60-ThrAlaIleAspTyrGluGly-66 |
| SEQ. ID. NO. 28693 | 80-PheGlyGlyGluValGluArg-86 |
| SEQ. ID. NO. 28694 | 99-AspAlaGlnGluGlyProMetPro-106 |
| SEQ. ID. NO. 28695 | 128-LysIleAspLysProSerAla-134 |
| SEQ. ID. NO. 28696 | 151-GlyAlaThrAspGluGlnLeuAsp-158 |
| SEQ. ID. NO. 28697 | 171-AlaLysLeuGluGluThrAspGluSerSerAspMetArgProLeu-185 |
| SEQ. ID. NO. 28698 | 198-GlySerAlaAspGluProLeu-204 |
| SEQ. ID. NO. 28699 | 226-LeuAsnGlyArgIleLysPro-232 |
| SEQ. ID. NO. 28700 | 241-HisGluGlnGlnIleAla-246 |
| SEQ. ID. NO. 28701 | 258-GlyLeuGluArgValProLeuGluGluAlaGluAlaGlyAsp-271 |
| SEQ. ID. NO. 28702 | 277-GlyIleGluAspIleGly-282 |
| SEQ. ID. NO. 28703 | 287-IleThrAspLysAspAsnProLysGly-295 |
| SEQ. ID. NO. 28704 | 300-SerValAspGluProThrLeu-306 |
| SEQ. ID. NO. 28705 | 318-AlaGlyThrGluGlyGlyLysPheValThr-326 |
| SEQ. ID. NO. 28706 | 328-ArgGlnIleArgAspArgLeuGlnLysGluLeuLeu-339 |
| SEQ. ID. NO. 28707 | 344-LeuArgValGluAspThrAlaAspAlaAspValPheArgValSerGlyArgGlyGluLeu-363 |
| SEQ. ID. NO. 28708 | 371-AsnMetArgArgGluGlyTyr-377 |
| SEQ. ID. NO. 28709 | 381-ValGlyLysProArgValValTyrArgAspIleAspGlyGlnLysCysGluProTyrGlu-400 |
| SEQ. ID. NO. 28710 | 405-AspValProAspAspAsnGlnGlyAlaValMetGluGluLeuGlyArgArgArgGlyGluLeuThrAsnMetGluSerAspGlyAsnGlyArgThrArgLeu-438 |
| SEQ. ID. NO. 28711 | 472-AlaProValLysProAspMetProGlyArgHis-482 |
| SEQ. ID. NO. 28712 | 489-GlnGluGlnGlyGlu-493 |
| SEQ. ID. NO. 28713 | 502-LeuGluAspArgGlyArgMet-508 |
| SEQ. ID. NO. 28714 | 512-ProAsnAspLysIleTyr-517 |
| SEQ. ID. NO. 28715 | 525-HisSerArgAspAsnAspLeu-531 |
| SEQ. ID. NO. 28716 | 536-LeuLysGlyLysLysLeuThrAsn-543 |
| SEQ. ID. NO. 28717 | 545-ArgAlaSerGlyThrAspGluAlaValArg-554 |
| SEQ. ID. NO. 28718 | 569-PheIleAspAspAspGluLeuValGlu-577 |
| SEQ. ID. NO. 28719 | 583-IleArgLeuArgMet-587 |
| SEQ. ID. NO. 28720 | 591-SerGluLeuGluArgArgArgHisPheLysLysLeuAsp-603 | g152
AMPHI Regions - AMPHI

| SEQ. ID. NO. 28721 | 10-PheProThrArgLeuPhe-15 |
|---|---|
| SEQ. ID. NO. 28722 | 66-ArgPheSerArgPheValArgGlyTrpAlaGlyIleArgGlyTyrLeuLysAsnGlyIleProGluHisIleGlnProGlyHisAsnProLeu-96 |
| SEQ. ID. NO. 28723 | 103-AlaLeuLeuAlaAla-107 |
| SEQ. ID. NO. 28724 | 130-LeuAsnHisLeuValSerGluHisThrGlySerLeu-141 |
| SEQ. ID. NO. 28725 | 150-PheLysLeuLeuAlaValPheSerAlaValHisIleAlaAlaValAlaAlaTyr-167 |
| SEQ. ID. NO. 28726 | 177-ArgProMetIleThr-181 |

Antigenic Index - Jameson-Wolf

| SEQ. ID. NO. 28727 | 1-MetLysAsnLysThrLysValTrp-8 |
|---|---|
| SEQ. ID. NO. 28728 | 29-SerAlaLysAlaGlyGlyAsp-35 |
| SEQ. ID. NO. 28729 | 61-GlySerAspThrAlaArgPhe-67 |
| SEQ. ID. NO. 28730 | 79-GlyTyrLeuLysAsnGlyIleProGluHisIleGlnProGlyHisAsnProLeu-96 |
| SEQ. ID. NO. 28731 | 119-AlaAsnGluAsnThrPheSerThrAsnGlyTyr-129 |
| SEQ. ID. NO. 28732 | 137-HisThrGlySerLeuIleArg-143 |
| SEQ. ID. NO. 28733 | 169-IlePheLysLysLysAsnLeuVal-176 |
| SEQ. ID. NO. 28734 | 186-IleGluGlyLysThrSerIle-192 |

Hydrophilic Regions - Hopp-Woods

| SEQ. ID. NO. 28735 | 1-MetLysAsnLysThrLysVal-7 |
|---|---|
| SEQ. ID. NO. 28736 | 63-AspThrAlaArgPhe-67 |
| SEQ. ID. NO. 28737 | 169-IlePheLysLysLysAsnLeuVal-176 |
| SEQ. ID. NO. 28738 | 186-IleGluGlyLysThrSerIle-192 | g153
AMPHI Regions - AMPHI

| SEQ. ID. NO. 28739 | 17-AlaAlaSerValLeuSerLeuProGluMetMetArgLeuMetValPhe-32 |
|---|---|
| SEQ. ID. NO. 28740 | 96-ThrLeuValAlaTyrIleLysLeuSerSerValAlaLys-108 |
| SEQ. ID. NO. 28741 | 130-ValSerValProGlnHisTrp-136 |
| SEQ. ID. NO. 28742 | 224-ThrIlePheSerGlyIleAlaTyr-231 |
| SEQ. ID. NO. 28743 | 274-AlaLysLysLeuSerHisLeuTyrArgIleThrGluAlaValGlyArgTrpSerMetIleAspIlePheValIle-298 |

Antigenic Index - Jameson-Wolf

| SEQ. ID. NO. 28744 | 65-IleArgLysGlnAla-69 |
|---|---|
| SEQ. ID. NO. 28745 | 81-ValArgLeuArgGln-85 |
| SEQ. ID. NO. 28746 | 143-ArgLeuThrGlyAsnAsnAla-149 |
| SEQ. ID. NO. 28747 | 151-GlnThrAlaSerGluGlyLysThrCysCysSer-161 |
| SEQ. ID. NO. 28748 | 165-TyrPheArgAspSerAlaGluSerProCysGly-175 |
| SEQ. ID. NO. 28749 | 181-LeuTyrGlyGlyArgProLysProSerLeuSer-190 |
| SEQ. ID. NO. 28750 | 215-SerAsnProAlaAlaThrGlu-221 |
| SEQ. ID. NO. 28751 | 234-AspGluGlyAspArgLeu-239 |
| SEQ. ID. NO. 28752 | 272-AlaGlyAlaLysLysLeu-277 |
| SEQ. ID. NO. 28753 | 339-LeuLeuTrpAspLysArgAlaSerAspGlyIleAla-350 |
| SEQ. ID. NO. 28754 | 352-AsnGluThrGluLysTyrAsp-358 |

TABLE 1-continued

Hydrophilic Regions - Hopp-Woods
SEQ. ID. NO. 28755   81-ValArgLeuArgGln-85
SEQ. ID. NO. 28756   152-ThrAlaSerGluGlyLysThrCysCys-160
SEQ. ID. NO. 28757   168-AspSerAlaGluSerPro-173
SEQ. ID. NO. 28758   182-TyrGlyGlyArgProLysSerLeuSer-190
SEQ. ID. NO. 28759   234-AspGluGlyAspArgLeu-239
SEQ. ID. NO. 28760   273-GlyAlaLysLysLeu-277
SEQ. ID. NO. 28761   339-LeuLeuTrpAspLysArgAlaSerAsp-347
SEQ. ID. NO. 28762   352-AsnGluThrGluLysTyrAsp-358
g154
AMPHI Regions - AMPHI
SEQ. ID. NO. 28763   122-GlyValThrGlyLeuGlyThrLeuLeu-130
SEQ. ID. NO. 28764   152-GlnAspIleProProValThr-158
SEQ. ID. NO. 28765   262-ThrLysAsnSerLysAsnValLysSer-270
SEQ. ID. NO. 28766   298-PheLysGlnSerVal-302
SEQ. ID. NO. 28767   360-SerLysGluHisTrpLysGlnGlnPheGlnThrAlaLeuAsnLysGlyLeuThrAla-378
SEQ. ID. NO. 28768   389-GlyLysMetIleGluLeuAsnAsp-396
SEQ. ID. NO. 28769   429-LysLeuAlaAspLeuLeuAspLysPheAsnAsnLeuPro-441
SEQ. ID. NO. 28770   446-ValAlaGluLeuAsnGly-451
SEQ. ID. NO. 28771   467-LeuSerSerIleAspLysLeuValGlyAsnProGlnThrGlnAsnIleProAsnGluLeuAsnGlnThr-489
SEQ. ID. NO. 28772   506-IleTyrGlyAspValGlnAsnThrLeuGlnSerLeuAspLysThrLeuLysAspValGlnProValIleAsnThrLeuLysGluLys-534
Antigenic Index - Jameson-Wolf
SEQ. ID. NO. 28773   1-MetThrAspAsnSerProProProAsnGlyHisAlaGlnAlaArgValArgLysAsnAsnThr-21
SEQ. ID. NO. 28774   43-LysGluIleArgAsnArgGlyProVal-51
SEQ. ID. NO. 28775   57-AspSerAlaGluGlyIleGluValAsnAsnThr-67
SEQ. ID. NO. 28776   75-AspValGlyArgValThrArgIleLysLeuArgAspAspGlnLysGlyValGlu-92
SEQ. ID. NO. 28777   100-AspValSerGlyLeuIleArgSerAspThrGln-110
SEQ. ID. NO. 28778   114-ValLysProArgIleAspGlnSerGly-122
SEQ. ID. NO. 28779   138-ThrProGlyLysSerGlyGluAlaLysAspValPheGln-150
SEQ. ID. NO. 28780   169-LeuIleGlyLysAsnAspArgIleLeuAsn-178
SEQ. ID. NO. 28781   196-AlaHisPheAspProSerAspGlnSer-204
SEQ. ID. NO. 28782   212-GlnSerProAsnAspLysLeuIle-219
SEQ. ID. NO. 28783   227-LeuGluSerGlyIleAsnIleGluThrThrGlySerGlyIleLysLeuAsnSer-244
SEQ. ID. NO. 28784   256-SerPheAspSerProLysThrLysAsnSerLysAsnValLysSerGluAspSer-273
SEQ. ID. NO. 28785   275-ThrLeuTyrAspSerArgSerGluIleAlaAsnLeuProAspAspArgSerLeu-292
SEQ. ID. NO. 28786   300-GlnSerValArgGlyLeu-305
SEQ. ID. NO. 28787   311-ValGluTyrLysGlyLeuAsnVal-318
SEQ. ID. NO. 28788   325-ProTyrPheAspArgAsnAspSer-332
SEQ. ID. NO. 28789   345-IleArgIleGluProSerArgLeuGluIleAsnAlaAspGluGlnSerLysGluHisTrpLysGlnGlnPhe-368
SEQ. ID. NO. 28790   371-AlaLeuAsnLysGlyLeu-376
SEQ. ID. NO. 28791   386-LeuThrGlyGlyLysMetIleGluLeuAsnAspGlnProSerAlaSerProLysLeuArgPro-406
SEQ. ID. NO. 28792   416-IleAlaThrArgGlyGlyGlyLeuAspAspLeuGlnValLysLeu-430
SEQ. ID. NO. 28793   432-AspLeuLeuAspLysPheAsnAsnLeuProLeuAspLysThrValAla-447
SEQ. ID. NO. 28794   450-AsnGlySerLeuAlaGluLeuLysSerAlaLeuLysSerAlaAsn-464
SEQ. ID. NO. 28795   469-SerIleAspLysLeuValGlyAsnProGlnThrGlnAsnIleProAsnGluLeuAsnGlnThrLeuLysGluLeuArgIle-495
SEQ. ID. NO. 28796   500-ValSerProGlnSer-504
SEQ. ID. NO. 28797   516-SerLeuAspLysThrLeuLysAspValGln-525
SEQ. ID. NO. 28798   530-ThrLeuLysGluLysProAsnAla-537
SEQ. ID. NO. 28799   541-AsnAsnSerSerLysAspProIleProLysGlySerArg-553
Hydrophilic Regions - Hopp-Woods
SEQ. ID. NO. 28800   1-MetThrAspAsnSerProProPro-8
SEQ. ID. NO. 28801   12-AlaGlnAlaArgValArgLysAsnAsn-20
SEQ. ID. NO. 28802   43-LysGluIleArgAsnArgGly-49
SEQ. ID. NO. 28803   57-AspSerAlaGluGlyIleGlu-63
SEQ. ID. NO. 28804   75-AspValGlyArgValThrArgIleLysLeuArgAspAspGlnLysGlyValGlu-92
SEQ. ID. NO. 28805   105-IleArgSerAspThr-109
SEQ. ID. NO. 28806   116-ProArgIleAspGln-120
SEQ. ID. NO. 28807   140-GlyLysSerGlyGluAlaLysAspValPheGln-150
SEQ. ID. NO. 28808   171-GlyLysAsnAspArgIleLeu-177
SEQ. ID. NO. 28809   196-AlaHisPheAspProSerAspGln-203
SEQ. ID. NO. 28810   214-ProAsnAspLysLeuIle-219
SEQ. ID. NO. 28811   258-AspSerProLysThrLysAsnSerLysAsnValLysSerGluAspSer-273
SEQ. ID. NO. 28812   278-AspSerArgSerGluIle-283
SEQ. ID. NO. 28813   285-AsnLeuProAspAspArgSer-291
SEQ. ID. NO. 28814   311-ValGluTyrLysGly-315
SEQ. ID. NO. 28815   328-AspArgAsnAspSer-332
SEQ. ID. NO. 28816   345-IleArgIleGluProSerArgLeuGluIleAsnAlaAspGluGlnSerLysGluHisTrpLys-365
SEQ. ID. NO. 28817   390-LysMetIleGluLeuAsnAspGlnProSerAlaSerProLysLeuArgPro-406
SEQ. ID. NO. 28818   419-ArgGlyGlyGlyLeuAspAspLeuGlnValLysLeu-430
SEQ. ID. NO. 28819   432-AspLeuLeuAspLysPheAsn-438
SEQ. ID. NO. 28820   441-ProLeuAspLysThrValAla-447
SEQ. ID. NO. 28821   454-AlaGluLeuLysSerAlaLeuLysSerAlaAsn-464
SEQ. ID. NO. 28822   469-SerIleAspLysLeuValGly-475
SEQ. ID. NO. 28823   482-IleProAsnGluLeu-486
SEQ. ID. NO. 28824   488-GlnThrLeuLysGluLeuArgIle-495
SEQ. ID. NO. 28825   516-SerLeuAspLysThrLeuLysAspValGln-525
SEQ. ID. NO. 28826   530-ThrLeuLysGluLysProAsn-536
SEQ. ID. NO. 28827   543-SerSerLysAspProIleProLysGlySerArg-553

TABLE 1-continued g155
AMPHI Regions - AMPHI
SEQ. ID. NO. 28828  28-LysLeuGlyPheGlu-32
SEQ. ID. NO. 28829  42-AlaAlaSerLeuAsp-46
SEQ. ID. NO. 28830  105-LeuArgAlaLysLysVal-110
SEQ. ID. NO. 28831  118-ValProArgIleSerArgAlaGlnAlaLeuAspAlaLeuSerSerMetAlaAsnIleSerGlyTyrArgAlaValIleGluAlaAlaAsnAla
                    PheGlyArgPhePheThrGly-155
SEQ. ID. NO. 28832  175-ValAlaGlyLeuAlaAlaIleGlyThrAlaAsnSerLeuGlyAlaValValArgAlaPhe-194
SEQ. ID. NO. 28833  201-AlaGluGlnIleGluSerMetGlyGly-209
SEQ. ID. NO. 28834  225-AspGlyTyrAlaLysValMet-231
SEQ. ID. NO. 28835  262-LysProAlaProLysLeuIleThrLysGluMetValGluSerMetLys-277
SEQ. ID. NO. 28836  294-LeuThrArgProGlyGlu-299
SEQ. ID. NO. 28837  307-ValLysIleIleGlyTyrThrAspMetAlaAsnArgLeuAlaGlyGln-322
SEQ. ID. NO. 28838  329-ThrAsnLeuValAsnLeuThrLysLeuLeuSer-339
SEQ. ID. NO. 28839  403-LysLeuAlaProAlaAlaIle-409
SEQ. ID. NO. 28840  427-AsnHisPheIleVal-431
SEQ. ID. NO. 28841  450-LeuHisThrProLeuMetSerValThrAsnAlaIleSerGlyIleMet-465
SEQ. ID. NO. 28842  468-GlyAlaLeuLeuGln-472
SEQ. ID. NO. 28843  477-AsnGlyPheValSerLeuLeuSerPheValAla-487
SEQ. ID. NO. 28844  493-IleAsnIlePheGlyGly-498
Antigenic Index - Jameson-Wolf
SEQ. ID. NO. 28845  4-GlyIleProArgGluSerLeuSerGlyGluThrArgVal-16
SEQ. ID. NO. 28846  44-SerLeuAspAspAlaAla-49
SEQ. ID. NO. 28847  72-ValAsnAlaProSerGluGlyGluLeuProLeuLeuLysGluGlyGln-87
SEQ. ID. NO. 28848  94-TrpProArgGlnAsnGluAlaLeu-101
SEQ. ID. NO. 28849  105-LeuArgAlaLysLysValAsn-111
SEQ. ID. NO. 28850  117-MetValProArgIleSerArg-123
SEQ. ID. NO. 28851  159-AlaAlaGlyLysValProProAla-166
SEQ. ID. NO. 28852  194-PheAspThrArgLeuGluValAlaGluGlnIleGluSerMetGlyGlyLys-210
SEQ. ID. NO. 28853  216-PheLeuGlnGluSerGlyGlySerGlyAspGlyTyrAla-228
SEQ. ID. NO. 28854  242-LeuPheAlaGluGlnAlaLysGluValAsp-251
SEQ. ID. NO. 28855  259-IleProGlyLysProAlaProLysLeuIleThr-269
SEQ. ID. NO. 28856  271-GluMetValGluSerMetLysSerGlySer-280
SEQ. ID. NO. 28857  289-GlyGlyAsnCysGluLeuThrArgProGlyGluLeuSerVal-302
SEQ. ID. NO. 28858  319-LeuAlaGlyGlnSerSer-324
SEQ. ID. NO. 28859  337-LeuLeuSerProAsnLysAspGlyGluIle-346
SEQ. ID. NO. 28860  348-LeuAspPheGluAspValIle-354
SEQ. ID. NO. 28861  359-ThrValThrArgAspGlyGluIleThrPhePro-369
SEQ. ID. NO. 28862  376-SerAlaArgProGlnGlnThrProSerGluLysAlaAlaProAlaAlaLysProGluProLysPro-397
Hydrophilic Regions - Hopp-Woods
SEQ. ID. NO. 28863  4-GlyIleProArgGluSerLeuSerGlyGluThrArgVal-16
SEQ. ID. NO. 28864  44-SerLeuAspAspAlaAla-49
SEQ. ID. NO. 28865  74-AlaProSerGluGlyGluLeuProLeuLeuLysGluGlyGln-87
SEQ. ID. NO. 28866  96-ArgGlnAsnGluAlaLeu-101
SEQ. ID. NO. 28867  105-LeuArgAlaLysLysValAsn-111
SEQ. ID. NO. 28868  117-MetValProArgIleSerArg-123
SEQ. ID. NO. 28869  194-PheAspThrArgLeuGluValAlaGluGlnIleGluSerMetGly-208
SEQ. ID. NO. 28870  220-SerGlyGlySerGlyAspGlyTyrAla-228
SEQ. ID. NO. 28871  242-LeuPheAlaGluGlnAlaLysGluValAsp-251
SEQ. ID. NO. 28872  260-ProGlyLysProAlaPro-265
SEQ. ID. NO. 28873  271-GluMetValGluSerMetLysSer-278
SEQ. ID. NO. 28874  290-GlyAsnCysGluLeuThrArgProGlyGlu-299
SEQ. ID. NO. 28875  339-SerProAsnLysAspGlyGluIle-346
SEQ. ID. NO. 28876  348-LeuAspPheGluAspValIle-354
SEQ. ID. NO. 28877  359-ThrValThrArgAspGlyGluIle-366
SEQ. ID. NO. 28878  377-AlaArgProGlnGlnThrProSerGluLysAlaAlaProAlaAlaLysProGluProLysPro-397
g156
AMPHI Regions - AMPHI
SEQ. ID. NO. 28879  56-AsnGlyPheGluAlaPheAlaProPhe-64
SEQ. ID. NO. 28880  80-AlaThrValAsnThr-84
Antigenic Index - Jameson-Wolf
SEQ. ID. NO. 28881  21-TyrAlaLysLysAlaGlyGlyPheArgPheLysAspAsnHisAsnProArgGly-38
SEQ. ID. NO. 28882  44-GlnGlyAlaAlaAla-48
SEQ. ID. NO. 28883  51-HisAlaAlaGlnGlnAsnGlyPheGlu-59
SEQ. ID. NO. 28884  73-AlaThrGlyAsnAlaGlyGln-79
SEQ. ID. NO. 28885  103-AspLysAlaAlaLeu-107
Hydrophilic Regions - Hopp-Woods
SEQ. ID. NO. 28886  21-TyrAlaLysLysAlaGlyGlyPheArgPheLysAspAsnHisAsnPro-36
SEQ. ID. NO. 28887  103-AspLysAlaAlaLeu-107
g157
AMPHI Regions - AMPHI
SEQ. ID. NO. 28888  21-GlyArgAspValArgAlaAla-27
SEQ. ID. NO. 28889  29-AlaIleLysIleAsnArgLeuLeuLysArgTyrIleLysArgGly-43
SEQ. ID. NO. 28890  57-ArgLeuGlyGlyPheValArgAlaAlaGln-66
SEQ. ID. NO. 28891  137-LeuGlyGlnAlaGlyGly-142
SEQ. ID. NO. 28892  167-GlnLeuValAspArgLeuProArgGluAla-176
Antigenic Index - Jameson-Wolf
SEQ. ID. NO. 28893  1-MetArgAsnGluGluLysArgAlaLeuArgArgGluLeuArgGlyArgArgSerGlnMetGlyArgAspValArgAla-26
SEQ. ID. NO. 28894  34-ArgLeuLeuLysArgTyrIleLysArgGlyArgLysIle-46
SEQ. ID. NO. 28895  51-ProMetGlyLysGluLeuArg-57

TABLE 1-continued

| | |
|---|---|
| SEQ. ID. NO. 28896 | 64-AlaAlaGlnLysArgGlyAlaLysLeu-72 |
| SEQ. ID. NO. 28897 | 77-IleGluProHisThrArgArgMetTrp-85 |
| SEQ. ID. NO. 28898 | 87-ThrProTyrProGluArgGlyMetGluArgGluArgLysArgGlyArgAlaLysLeu-105 |
| SEQ. ID. NO. 28899 | 110-PheAlaGlyArgLysIleArgVal-117 |
| SEQ. ID. NO. 28900 | 129-GlyIleAspArgGluGlyTyrArgLeuGlyGln-139 |
| SEQ. ID. NO. 28901 | 151-MetLysTyrArgLeuGlnAla-157 |
| SEQ. ID. NO. 28902 | 168-LeuValAspArgLeuProArgGluAlaHisAspLeuProLeu-181 |

Hydrophilic Regions - Hopp-Woods

| | |
|---|---|
| SEQ. ID. NO. 28903 | 1-MetArgAsnGluGluLysArgAlaLeuArgArgGluLeuArgGlyArgArgSerGlnMetGlyArgAspValArgAla-26 |
| SEQ. ID. NO. 28904 | 34-ArgLeuLeuLysArgTyrIleLysArgGlyArgLysIle-46 |
| SEQ. ID. NO. 28905 | 64-AlaAlaGlnLysArgGlyAla-70 |
| SEQ. ID. NO. 28906 | 89-TyrProGluArgGlyMetGluArgGluArgLysArgGlyArgAlaLysLeu-105 |
| SEQ. ID. NO. 28907 | 111-AlaGlyArgLysIleArgVal-117 |
| SEQ. ID. NO. 28908 | 129-GlyIleAspArgGluGlyTyrArg-136 |
| SEQ. ID. NO. 28909 | 151-MetLysTyrArgLeuGlnAla-157 |
| SEQ. ID. NO. 28910 | 168-LeuValAspArgLeuProArgGluAlaHisAspLeuPro-180 | g158
AMPHI Regions - AMPHI

| | |
|---|---|
| SEQ. ID. NO. 28911 | 20-PheSerArgAlaAlaGluGlnLeuGlu-28 |
| SEQ. ID. NO. 28912 | 33-AlaValSerArgIleValLysArgLeuGlu-42 |
| SEQ. ID. NO. 28913 | 46-GlyValAsnLeuLeuAsnArgThrThrArgGlnLeuAsn-58 |
| SEQ. ID. NO. 28914 | 63-GlyAlaGlnTyrPheArgArgAlaGlnArgIleLeuGlnGlu-76 |
| SEQ. ID. NO. 28915 | 85-LeuAlaValHisGluValProGln-92 |
| SEQ. ID. NO. 28916 | 160-PheAspSerHisPheArgValValAlaSerPro-170 |
| SEQ. ID. NO. 28917 | 178-ThrProGlnSerAlaGluAspLeu-185 |
| SEQ. ID. NO. 28918 | 188-HisGlnCysLeuGlyPheThrGluProGlySerLeuAsnThrTrpAlaVal-204 |
| SEQ. ID. NO. 28919 | 287-AspPheLeuValLysGluLeuGlyLysAsnMetAsnArgThrAsnThr-302 |

Antigenic Index - Jameson-Wolf

| | |
|---|---|
| SEQ. ID. NO. 28920 | 1-MetLysThrAsnSerGluGluLeu-8 |
| SEQ. ID. NO. 28921 | 16-GluSerGlySerPheSerArgAlaAlaGluGlnLeuGluMetAlaAsn-31 |
| SEQ. ID. NO. 28922 | 36-ArgIleValLysArgLeuGluGluLysLeuGly-46 |
| SEQ. ID. NO. 28923 | 49-LeuLeuAsnArgThrThrArgGlnLeuAsnLeuThrGluGluGlyAlaGlnTyrPheArgArgAlaGlnArgIleLeuGln-75 |
| SEQ. ID. NO. 28924 | 78-AlaAlaAlaGluThrGluMet-84 |
| SEQ. ID. NO. 28925 | 95-LeuArgValAspSer-99 |
| SEQ. ID. NO. 28926 | 114-LysPheAsnGluArgTyrProHisIleArg-123 |
| SEQ. ID. NO. 28927 | 136-IleGluArgLysValAspIle-142 |
| SEQ. ID. NO. 28928 | 144-LeuArgAlaGlyGluLeuAspAspSerGlyLeuArgAla-156 |
| SEQ. ID. NO. 28929 | 168-AlaSerProGluTyrLeuAla-174 |
| SEQ. ID. NO. 28930 | 176-HisGlyThrProGlnSerAlaGluAspLeuAla-186 |
| SEQ. ID. NO. 28931 | 192-GlyPheThrGluProGlySerLeuAsn-200 |
| SEQ. ID. NO. 28932 | 207-AlaGlnGlyAsnProTyrLysIle-214 |
| SEQ. ID. NO. 28933 | 216-ProHisPheThrAlaSerSerGlyGluIleLeu-226 |
| SEQ. ID. NO. 28934 | 229-LeuCysLeuSerSerCysGly-235 |
| SEQ. ID. NO. 28935 | 243-LeuValAspAsnAspIleThrGluGlyLysLeu-253 |
| SEQ. ID. NO. 28936 | 258-AlaGluGlnThrSerAsnLysThrHisProPhe-268 |
| SEQ. ID. NO. 28937 | 273-TyrSerAspLysAlaValAsnLeu-280 |
| SEQ. ID. NO. 28938 | 292-GluLeuGlyLysAsnMetAsnArgThrAsnThrLys-303 |

Hydrophilic Regions - Hopp-Woods

| | |
|---|---|
| SEQ. ID. NO. 28939 | 1-MetLysThrAsnSerGluGluLeu-8 |
| SEQ. ID. NO. 28940 | 19-SerPheSerArgAlaAlaGluGlnLeuGluMet-29 |
| SEQ. ID. NO. 28941 | 36-ArgIleValLysArgLeuGluGluLysLeuGly-46 |
| SEQ. ID. NO. 28942 | 58-AsnLeuThrGluGluGlyAlaGlnTyrPheArgArgAlaGlnArgIleLeuGln-75 |
| SEQ. ID. NO. 28943 | 78-AlaAlaAlaGluThrGluMet-84 |
| SEQ. ID. NO. 28944 | 95-LeuArgValAspSer-99 |
| SEQ. ID. NO. 28945 | 114-LysPheAsnGluArgTyrPro-120 |
| SEQ. ID. NO. 28946 | 136-IleGluArgLysValAspIle-142 |
| SEQ. ID. NO. 28947 | 144-LeuArgAlaGlyGluLeuAspAspSerGlyLeuArgAla-156 |
| SEQ. ID. NO. 28948 | 180-GlnSerAlaGluAspLeuAla-186 |
| SEQ. ID. NO. 28949 | 246-AsnAspIleThrGluGlyLysLeu-253 |
| SEQ. ID. NO. 28950 | 260-GlnThrSerAsnLysThrHis-266 |
| SEQ. ID. NO. 28951 | 276-LysAlaValAsnLeu-280 |
| SEQ. ID. NO. 28952 | 292-GluLeuGlyLysAsnMetAsnArgThrAsnThrLys-303 | g160
AMPHI Regions - AMPHI

| | |
|---|---|
| SEQ. ID. NO. 28953 | 6-LysLeuValAspLeuAlaGlnLeuThrGly-15 |
| SEQ. ID. NO. 28954 | 27-TrpHisGluThrLeu-31 |
| SEQ. ID. NO. 28955 | 69-GlyLeuGlyHisVal-73 |
| SEQ. ID. NO. 28956 | 97-LysGlnCysGlyAsn-101 |
| SEQ. ID. NO. 28957 | 118-AlaAspLeuMetAsnGlyLeuProGluThr-127 |
| SEQ. ID. NO. 28958 | 154-GlyThrValSerValValAsnAlaLeuProSer-164 |
| SEQ. ID. NO. 28959 | 183-LeuSerGlyValLeuLysGlyTrpGlnAspLysArg-194 |
| SEQ. ID. NO. 28960 | 197-HisLeuIleGlnLysValIleAspLysProGlu-207 |
| SEQ. ID. NO. 28961 | 216-ValAlaAlaAlaAsn-220 |
| SEQ. ID. NO. 28962 | 226-LeuMetArgArgPheLysSer-232 |
| SEQ. ID. NO. 28963 | 239-HisAlaPheValAsnHisIleArg-246 |
| SEQ. ID. NO. 28964 | 276-PheGlyLysAlaPheLys-281 |

Antigenic Index - Jameson-Wolf

| | |
|---|---|
| SEQ. ID. NO. 28965 | 2-AspIleLeuAspLysLeuValAsp-9 |
| SEQ. ID. NO. 28966 | 13-LeuThrGlySerAlaAspVal-19 |
| SEQ. ID. NO. 28967 | 30-ThrLeuGlnArgGluGlyLeu-36 |

TABLE 1-continued

| | |
|---|---|
| SEQ. ID. NO. 28968 | 49-IleAspGlyGluThrSerProArgProValGlyThrGlyAsp-62 |
| SEQ. ID. NO. 28969 | 74-LeuSerHisAspGlyLysTyrGlyGluSerLeuGlnProAspIleArgGlnAsnGlyThrPhe-94 |
| SEQ. ID. NO. 28970 | 98-GlnCysGlyAsnGlyLeu-103 |
| SEQ. ID. NO. 28971 | 112-PheArgTyrAspThrHisAla-118 |
| SEQ. ID. NO. 28972 | 120-LeuMetAsnGlyLeu-124 |
| SEQ. ID. NO. 28973 | 146-LeuGluSerGluLysProLeu-152 |
| SEQ. ID. NO. 28974 | 175-LeuGluGlnAspLysAspValGluLeu-183 |
| SEQ. ID. NO. 28975 | 189-GlyTrpGlnAspLysArgLeuGly-196 |
| SEQ. ID. NO. 28976 | 202-ValIleAspLysProGluAspGluTrpAsnIleAspLysMetVal-216 |
| SEQ. ID. NO. 28977 | 225-GlnLeuMetArgArgPheLysSerGlnVal-234 |
| SEQ. ID. NO. 28978 | 252-LeuLeuLeuLysLysThrProAspSerValLeu-262 |
| SEQ. ID. NO. 28979 | 271-GlnSerGluThrHisPhe-276 |
| SEQ. ID. NO. 28980 | 278-LysAlaPheLysArg-282 |
| SEQ. ID. NO. 28981 | 287-SerProGlyGlnTyrArgLysGluGlyGlyGlnLys-298 |
| Hydrophilic Regions - Hopp-Woods | |
| SEQ. ID. NO. 28982 | 2-AspIleLeuAspLysLeuValAsp-9 |
| SEQ. ID. NO. 28983 | 30-ThrLeuGlnArgGluGlyLeu-36 |
| SEQ. ID. NO. 28984 | 50-AspGlyGluThrSerProArgProValGly-59 |
| SEQ. ID. NO. 28985 | 76-HisAspGlyLysTyrGlyGlu-82 |
| SEQ. ID. NO. 28986 | 84-LeuGlnProAspIleArgGln-90 |
| SEQ. ID. NO. 28987 | 146-LeuGluSerGluLysProLeu-152 |
| SEQ. ID. NO. 28988 | 175-LeuGluGlnAspLysAspValGluLeu-183 |
| SEQ. ID. NO. 28989 | 190-TrpGlnAspLysArgLeuGly-196 |
| SEQ. ID. NO. 28990 | 202-ValIleAspLysProGluAspGluTrpAsnIle-212 |
| SEQ. ID. NO. 28991 | 225-GlnLeuMetArgArgPheLysSer-232 |
| SEQ. ID. NO. 28992 | 255-LysLysThrProAspSerValLeu-262 |
| SEQ. ID. NO. 28993 | 278-LysAlaPheLysArg-282 |
| SEQ. ID. NO. 28994 | 290-GlnTyrArgLysGluGlyGlyGlnLys-298 |
| g163 | |
| AMPHI Regions - AMPHI | |
| SEQ. ID. NO. 28995 | 60-SerGlyLeuGlyAsnIle-65 |
| SEQ. ID. NO. 28996 | 67-LeuGlyArgAspGluAsp-72 |
| SEQ. ID. NO. 28997 | 76-PheGlyPheLeuSerTrpLeuAlaMetLeuPhe-86 |
| SEQ. ID. NO. 28998 | 100-AlaGluProLeuMetHisTyrPheSerAspIle-110 |
| SEQ. ID. NO. 28999 | 170-IleSerGlyArgPheGlyAspAlaIleAspIleMetAlaLeuLeuAlaThrPhePheGlyIleIleThrThr-193 |
| SEQ. ID. NO. 29000 | 227-MetSerLeuAlaValValSerAlaIleSerGlyValGlyLysGlyValLysValLeuSer-246 |
| SEQ. ID. NO. 29001 | 272-AlaPheGlyAspAsnIleGlyAsnTyrLeuGlyAsnLeuValArg-286 |
| SEQ. ID. NO. 29002 | 313-TrpCysSerTrpAlaProPheValGlyLeuPheIleAla-325 |
| SEQ. ID. NO. 29003 | 346-LeuPheGlyValLeuTrpPhe-352 |
| SEQ. ID. NO. 29004 | 367-AlaGlyGlyMetLeuGluLysMetThrSerSer-377 |
| SEQ. ID. NO. 29005 | 380-ThrLeuLeuPheLysPhePheAsnTyrLeuProLeuProGluLeuThrSerIleValSerLeuLeu-401 |
| SEQ. ID. NO. 29006 | 438-TrpValLeuMetSerAla-444 |
| SEQ. ID. NO. 29007 | 454-GlyLeuGlyAsnLeuGlnSerMetThrLeu-463 |
| SEQ. ID. NO. 29008 | 510-ArgLeuValArgIleMetSer-516 |
| SEQ. ID. NO. 29009 | 520-GluGlnAspIleLeuLysPheLeuLysHisThrAla-531 |
| SEQ. ID. NO. 29010 | 535-MetHisGluLeuGlnArgGluLeu-542 |
| SEQ. ID. NO. 29011 | 574-AspPheMetTyrGlyIle-579 |
| SEQ. ID. NO. 29012 | 583-GlyGlnAspValSerAspGlnLeu-590 |
| SEQ. ID. NO. 29013 | 630-AlaAspIleLeuLysAsnTyr-636 |
| Antigenic Index - Jameson-Wolf | |
| SEQ. ID. NO. 29014 | 29-AspArgAlaLysGlu-33 |
| SEQ. ID. NO. 29015 | 65-IleArgLeuGlyArgAspGluAspValPro-74 |
| SEQ. ID. NO. 29016 | 114-AlaProGluHisArgGlnGln-120 |
| SEQ. ID. NO. 29017 | 166-LeuLysGluLysIleSerGlyArgPheGlyAspAlaIleAsp-179 |
| SEQ. ID. NO. 29018 | 200-GlnLeuGlyAlaGlyLeu-205 |
| SEQ. ID. NO. 29019 | 237-GlyValGlyLysGlyValLysVal-244 |
| SEQ. ID. NO. 29020 | 293-AlaTyrGluArgGluHisLysProTrpPhe-302 |
| SEQ. ID. NO. 29021 | 326-ArgIleSerLysGlyArgThrIleArg-334 |
| SEQ. ID. NO. 29022 | 370-MetLeuGluLysMetThrSerSerProGlu-379 |
| SEQ. ID. NO. 29023 | 409-ThrSerAlaAspSerGlyIle-415 |
| SEQ. ID. NO. 29024 | 421-IleThrSerArgAspLysGlyLeuSerAlaProArgTrp-433 |
| SEQ. ID. NO. 29025 | 451-ArgSerGlyGlyLeuGlyAsn-457 |
| SEQ. ID. NO. 29026 | 484-LeuSerAlaAspLysLysTyrPheGluThrArgValAsnProThrSer-499 |
| SEQ. ID. NO. 29027 | 503-ThrGlyGlyLysTrpLysGluArgLeuVal-512 |
| SEQ. ID. NO. 29028 | 516-SerGlnThrGlnGluGlnAspIle-523 |
| SEQ. ID. NO. 29029 | 537-GluLeuGlnArgGluLeuSerGluGluTyrGlyLeu-548 |
| SEQ. ID. NO. 29030 | 550-ValArgValAspLysMetPheHisGlnAspGluProAla-562 |
| SEQ. ID. NO. 29031 | 566-ValIleArgLysGluThrMetArg-573 |
| SEQ. ID. NO. 29032 | 581-SerValGlyGlnAspValSerAspGlnLeuIleAsnAspGlyLysLeuProHisIleArgHisGlnThrThrTyrLysProTyr-608 |
| SEQ. ID. NO. 29033 | 612-PheAspGlyArgValGlyTyr-618 |
| SEQ. ID. NO. 29034 | 622-TyrMetAsnLysAspGluLeuIle-629 |
| SEQ. ID. NO. 29035 | 632-IleLeuLysAsnTyrGlu-637 |
| SEQ. ID. NO. 29036 | 654-GluGlnValGluLeuAlaGlu-660 |
| Hydrophilic Regions - Hopp-Woods | |
| SEQ. ID. NO. 29037 | 29-AspArgAlaLysGlu-33 |
| SEQ. ID. NO. 29038 | 66-ArgLeuGlyArgAspGluAspValPro-74 |
| SEQ. ID. NO. 29039 | 114-AlaProGluHisArgGlnGln-120 |
| SEQ. ID. NO. 29040 | 166-LeuLysGluLysIleSerGlyArgPheGlyAsp-176 |
| SEQ. ID. NO. 29041 | 238-ValGlyLysGlyValLysVal-244 |
| SEQ. ID. NO. 29042 | 293-AlaTyrGluArgGluHisLysPro-300 |

TABLE 1-continued

| | |
|---|---|
| SEQ. ID. NO. 29043 | 327-IleSerLysGlyArgThrIleArg-334 |
| SEQ. ID. NO. 29044 | 370-MetLeuGluLysMetThrSerSerPro-378 |
| SEQ. ID. NO. 29045 | 422-ThrSerArgAspLysGlyLeuSer-429 |
| SEQ. ID. NO. 29046 | 484-LeuSerAlaAspLysLysTyrPheGlu-492 |
| SEQ. ID. NO. 29047 | 506-LysTrpLysGluArgLeuVal-512 |
| SEQ. ID. NO. 29048 | 516-SerGlnThrGlnGluGlnAspIle-523 |
| SEQ. ID. NO. 29049 | 537-GluLeuGlnArgGluLeuSerGluGluTyrGlyLeu-548 |
| SEQ. ID. NO. 29050 | 550-ValArgValAspLysMetPheHisGlnAspGluProAla-562 |
| SEQ. ID. NO. 29051 | 566-ValIleArgLysGluThrMetArg-573 |
| SEQ. ID. NO. 29052 | 581-SerValGlyGlnAspValSerAsp-588 |
| SEQ. ID. NO. 29053 | 590-LeuIleAsnAspGlyLysLeuProHis-598 |
| SEQ. ID. NO. 29054 | 622-TyrMetAsnLysAspGluLeuIle-629 |
| SEQ. ID. NO. 29055 | 654-GluGlnValGluLeuAlaGlu-660 | g164
AMPHI Regions - AMPHI

| | |
|---|---|
| SEQ. ID. NO. 29056 | 12-TyrIleLeuAsnAspCys-17 |
| SEQ. ID. NO. 29057 | 28-LeuSerLysGluLeuAlaGlyLeuLysAla-37 |
| SEQ. ID. NO. 29058 | 62-PhePheGluAsnValArgArgPheProGlu-71 |
| SEQ. ID. NO. 29059 | 75-LeuGlyArgGlnProArgIleAsnAspLeuAlaHis-86 |
| SEQ. ID. NO. 29060 | 104-TyrAlaAsnLeuPheAlaAsnLeuAsnGlyIleGluArgIlePheLys-119 |
| SEQ. ID. NO. 29061 | 179-ValProAlaIleTyrThr-184 |
| SEQ. ID. NO. 29062 | 197-TrpPheAsnArgIle-201 |
| SEQ. ID. NO. 29063 | 226-AlaLysLeuLeuGluGlyTyrGlyLeuSer-235 |
| SEQ. ID. NO. 29064 | 277-GluValGlyGluLeuIle-282 |
| SEQ. ID. NO. 29065 | 289-MetArgGlyTyrLeuAsn-294 |
| SEQ. ID. NO. 29066 | 302-ThrIleValAsnGlyTrpLeuLys-309 |
| SEQ. ID. NO. 29067 | 339-ValTyrProArgGluIleGluGluGlu-347 |
| SEQ. ID. NO. 29068 | 349-HisLysLeuAspAlaValGluAlaAlaAla-358 |
| SEQ. ID. NO. 29069 | 374-PheValGlnLeuLysGlyGlyMet-381 |
| SEQ. ID. NO. 29070 | 387-GluIleArgArgHisLeuArgThrVal-395 |
| SEQ. ID. NO. 29071 | 399-PheLysIleProLysGln-404 |
| SEQ. ID. NO. 29072 | 414-AsnAlaThrGlyLysValLeuLysArgValLeuLysGluGlnPheGluGlyAsn-431 |

Antigenic Index - Jameson-Wolf

| | |
|---|---|
| SEQ. ID. NO. 29073 | 5-LeuLysAsnSerGlu-9 |
| SEQ. ID. NO. 29074 | 15-AsnAspCysLysAla-19 |
| SEQ. ID. NO. 29075 | 27-GlyLeuSerLysGluLeuAlaGly-34 |
| SEQ. ID. NO. 29076 | 37-AlaGlnThrProValGlu-42 |
| SEQ. ID. NO. 29077 | 45-IleTrpThrAspLysSerArgProAlaGlyGluThrAlaGluGly-59 |
| SEQ. ID. NO. 29078 | 65-AsnValArgArgPheProGluLysProAspLeuGlyArgGlnProArgIleAsnAsp-83 |
| SEQ. ID. NO. 29079 | 90-ThrSerGlyThrThrGlyHisProLysGlyAla-100 |
| SEQ. ID. NO. 29080 | 112-AsnGlyIleGluArgIlePheLysIleSerLysArgAspArgPhe-126 |
| SEQ. ID. NO. 29081 | 205-IleSerGlyGlyAlaProLeuAla-212 |
| SEQ. ID. NO. 29082 | 219-PheLysAlaLysPheProArg-225 |
| SEQ. ID. NO. 29083 | 230-GluGlyTyrGlyLeuSerGluAlaSer-238 |
| SEQ. ID. NO. 29084 | 245-ThrProGluArgGlnLysAlaArgSerVal-254 |
| SEQ. ID. NO. 29085 | 258-LeuProGlyLeuGluAlaLysAlaValAspGluGluLeuValGluValProArgGlyGluValGly-279 |
| SEQ. ID. NO. 29086 | 282-IleValArgGlyGlySerValMet-289 |
| SEQ. ID. NO. 29087 | 297-AlaAlaThrAspGluThrIle-303 |
| SEQ. ID. NO. 29088 | 306-GlyTrpLeuLysThrGlyAsp-312 |
| SEQ. ID. NO. 29089 | 315-ThrIleAspGluAspGly-320 |
| SEQ. ID. NO. 29090 | 325-ValAspArgLysLysAspLeuIleIleSerLysGlyGlnAsnValTyrProArgGluIleGluGluGluIleHisLys-350 |
| SEQ. ID. NO. 29091 | 361-GlyValLysAspArgTyrAlaAspGluGluIle-371 |
| SEQ. ID. NO. 29092 | 377-LeuLysGluGlyMetAspLeuGlyGluAspGluIleArgArgHisLeu-392 |
| SEQ. ID. NO. 29093 | 405-IleHisPheLysAspGlyLeuProArgAsnAlaThrGlyLysValLeuLysArgValLeuLysGluGlnPheGluGlyAsnLys-432 |

Hydrophilic Regions - Hopp-Woods

| | |
|---|---|
| SEQ. ID. NO. 29094 | 27-GlyLeuSerLysGluLeuAlaGly-34 |
| SEQ. ID. NO. 29095 | 48-AspLysSerArgProAlaGlyGluThrAlaGluGly-59 |
| SEQ. ID. NO. 29096 | 65-AsnValArgArgPheProGluLysProAspLeuGlyArgGlnProArgIleAsnAsp-83 |
| SEQ. ID. NO. 29097 | 113-GlyIleGluArgIlePheLysIleSerLysArgAspArgPhe-126 |
| SEQ. ID. NO. 29098 | 219-PheLysAlaLysPheProArg-225 |
| SEQ. ID. NO. 29099 | 245-ThrProGluArgGlnLysAlaArgSer-253 |
| SEQ. ID. NO. 29100 | 261-LeuGluAlaLysAlaValAspGluGluLeuValGluValProArgGlyGluValGly-279 |
| SEQ. ID. NO. 29101 | 297-AlaAlaThrAspGluThrIle-303 |
| SEQ. ID. NO. 29102 | 315-ThrIleAspGluAspGly-320 |
| SEQ. ID. NO. 29103 | 325-ValAspArgLysLysAspLeuIleIle-333 |
| SEQ. ID. NO. 29104 | 340-TyrProArgGluIleGluGluGluIleHisLys-350 |
| SEQ. ID. NO. 29105 | 361-GlyValLysAspArgTyrAlaAspGluGluIle-371 |
| SEQ. ID. NO. 29106 | 377-LeuLysGluGlyMetAspLeuGlyGluAspGluIleArgArgHisLeu-392 |
| SEQ. ID. NO. 29107 | 409-AspGlyLeuProArgAsnAlaThr-416 |
| SEQ. ID. NO. 29108 | 418-LysValLeuLysArgValLeuLysGluGlnPheGluGlyAsnLys-432 | g165-1
AMPHI Regions - AMPHI

| | |
|---|---|
| SEQ. ID. NO. 29109 | 17-AlaThrLeuGlyValLeuLeuLysGluLeu-26 |
| SEQ. ID. NO. 29110 | 33-ThrLeuIleGluArgLeuGluAsp-40 |
| SEQ. ID. NO. 29111 | 73-IleAsnProAlaArgAlaLeuAsnIleAla-82 |
| SEQ. ID. NO. 29112 | 90-GlnPheTrpAlaThr-94 |
| SEQ. ID. NO. 29113 | 108-AsnAlaValProHis-112 |
| SEQ. ID. NO. 29114 | 121-HisCysArgTyrLeuGlnLysArg-128 |
| SEQ. ID. NO. 29115 | 130-AspValPheLysThrGlnLysLeuPheGluAsnMet-141 |
| SEQ. ID. NO. 29116 | 182-ArgLeuThrArgGlnMetValLysTyrLeuGlnGly-193 |

TABLE 1-continued

| | |
|---|---|
| SEQ. ID. NO. 29117 | 198-ThrGluPheAsnArgHisValGluAspIleLysArgGlu-210 |
| SEQ. ID. NO. 29118 | 364-LysThrLysGluGlu-368 |
| SEQ. ID. NO. 29119 | 371-AlaSerLeuLeuGluTyrTyrProArgGln-380 |

Antigenic Index - Jameson-Wolf

| | |
|---|---|
| SEQ. ID. NO. 29120 | 1-MetAlaGluAlaThrAsp-6 |
| SEQ. ID. NO. 29121 | 24-LysGluLeuGluProSerTrp-30 |
| SEQ. ID. NO. 29122 | 36-GluArgLeuGluAspValAlaLeuGluSerSerAsnAlaTrpAsnAsnAlaGlyThrGly-55 |
| SEQ. ID. NO. 29123 | 97-AlaGluGlyLysLeuGluAspAsnSer-105 |
| SEQ. ID. NO. 29124 | 117-MetAsnGluAspHisCysArgTyrLeuGlnLysArgTyrAspValPheLysThrGlnLysLeuPheGlu-139 |
| SEQ. ID. NO. 29125 | 141-MetGluPheSerThrAspArgAsnLysIleSerAsp-152 |
| SEQ. ID. NO. 29126 | 157-IleMetArgGlyArgAspGluAsnGlnPro-166 |
| SEQ. ID. NO. 29127 | 169-AlaAsnTyrSerAlaGluGlyThrAspValAspPheGlyArgLeuThrArgGlnMet-187 |
| SEQ. ID. NO. 29128 | 191-LeuGlnGlyLysGlyValLysThrGluPheAsnArgHisValGluAspIleLysArgGluSerAspGly-213 |
| SEQ. ID. NO. 29129 | 219-ThrAlaAspThrArgAsnProAspTrp-227 |
| SEQ. ID. NO. 29130 | 249-GlnLysSerGlyIleProGluGlyLysGlyTyrGlyGly-261 |
| SEQ. ID. NO. 29131 | 269-PheArgAsnSerAsnProGluThrAlaGluGlnHisAsn-281 |
| SEQ. ID. NO. 29132 | 300-LeuAspThrArgAsnValAspGlyLysArgHisLeu-311 |
| SEQ. ID. NO. 29133 | 322-AsnPheLeuLysGlnGlySerPheMet-330 |
| SEQ. ID. NO. 29134 | 361-GluLeuArgLysThrLysGluGluArgPhe-370 |
| SEQ. ID. NO. 29135 | 375-GluTyrTyrProArgGlnThrArgArg-383 |
| SEQ. ID. NO. 29136 | 395-IleXxxTyrAspSerLysLeuArgVal-403 |
| SEQ. ID. NO. 29137 | 410-ValProArgAspAlaArgSerArgIleLeuGluArgArgGlyAlaSerArg-426 |
| SEQ. ID. NO. 29138 | 430-IleSerAlaAspAspThrAlaProSer-438 |

Hydrophilic Regions - Hopp-Woods

| | |
|---|---|
| SEQ. ID. NO. 29139 | 1-MetAlaGluAlaThrAsp-6 |
| SEQ. ID. NO. 29140 | 24-LysGluLeuGluPro-28 |
| SEQ. ID. NO. 29141 | 36-GluArgLeuGluAspValAlaLeuGluSer-45 |
| SEQ. ID. NO. 29142 | 97-AlaGluGlyLysLeuGluAspAsnSer-105 |
| SEQ. ID. NO. 29143 | 117-MetAsnGluAspHisCysArgTyrLeuGlnLysArgTyrAspVal-131 |
| SEQ. ID. NO. 29144 | 141-MetGluPheSerThrAspArgAsnLysIleSerAsp-152 |
| SEQ. ID. NO. 29145 | 158-MetArgGlyArgAspGluAsnGlnPro-166 |
| SEQ. ID. NO. 29146 | 172-SerAlaGluGlyThrAspValAspPhe-180 |
| SEQ. ID. NO. 29147 | 182-ArgLeuThrArgGlnMet-187 |
| SEQ. ID. NO. 29148 | 194-LysGlyValLysThrGluPheAsnArgHisValGluAspIleLysArgGluSerAspGly-213 |
| SEQ. ID. NO. 29149 | 219-ThrAlaAspThrArgAsnProAsp-226 |
| SEQ. ID. NO. 29150 | 252-GlyIleProGluGlyLysGly-258 |
| SEQ. ID. NO. 29151 | 272-SerAsnProGluThrAlaGluGlnHisAsn-281 |
| SEQ. ID. NO. 29152 | 300-LeuAspThrArgAsnValAspGlyLysArg-309 |
| SEQ. ID. NO. 29153 | 361-GluLeuArgLysThrLysGluGluArgPhe-370 |
| SEQ. ID. NO. 29154 | 378-ProArgGlnThrArgArg-383 |
| SEQ. ID. NO. 29155 | 397-TyrAspSerLysLeuArg-402 |
| SEQ. ID. NO. 29156 | 410-ValProArgAspAlaArgSerArgIleLeuGluArgArgGlyAlaSerArg-426 |
| SEQ. ID. NO. 29157 | 431-SerAlaAspAspThrAlaPro-437 | g204
AMPHI Regions - AMPHI

| | |
|---|---|
| SEQ. ID. NO. 29158 | 16-HisIleAlaSerValLeuHisGlyGly-24 |
| SEQ. ID. NO. 29159 | 45-GlnPheAlaAlaValPheGlyAspIleAlaHisGlnPheGly-58 |
| SEQ. ID. NO. 29160 | 89-ValValGlyMetLeuSerGlyGln-96 |
| SEQ. ID. NO. 29161 | 104-GlnAlaPheAsnArgIleThrAspLeuPhePhe-114 |
| SEQ. ID. NO. 29162 | 132-ArgArgIleValAspValPheAsp-139 |
| SEQ. ID. NO. 29163 | 144-PheArgArgAlaLeuCysArgIleLeuArgLeuPheArgArgIlePheGly-160 |
| SEQ. ID. NO. 29164 | 229-ArgAlaPheCysAla-233 |

Antigenic Index - Jameson-Wolf

| | |
|---|---|
| SEQ. ID. NO. 29165 | 4-AlaGluIleLysArgProLeu-10 |
| SEQ. ID. NO. 29166 | 34-LeuGlnGlyGlyMetArgAsnGlnVal-42 |
| SEQ. ID. NO. 29167 | 55-HisGlnPheGlyLys-59 |
| SEQ. ID. NO. 29168 | 68-ArgProAlaArgArgArgValLeu-75 |
| SEQ. ID. NO. 29169 | 82-PheAlaAspAspGlyPheGln-88 |
| SEQ. ID. NO. 29170 | 93-LeuSerGlyGlnProAspGlyValLeu-101 |
| SEQ. ID. NO. 29171 | 125-SerGlnSerGlnThrGlyAsnArgArgIleValAsp-136 |
| SEQ. ID. NO. 29172 | 138-PheAspPheGluAsnArgPheArgArgAlaLeu-148 |
| SEQ. ID. NO. 29173 | 162-AlaAlaGlyGlyLysGlnGlnAla-169 |
| SEQ. ID. NO. 29174 | 172-GlnHisGlyLysArgTyrPhe-178 |
| SEQ. ID. NO. 29175 | 187-SerLysCysArgLeuLysCysArgLeuLysArgGlyArgArgArgPheGlyArgHisTrp-206 |
| SEQ. ID. NO. 29176 | 209-PheAsnGlyArgMetProThrAlaSerArgThrLeuSerAsnAsnSerArgAlaSerLeu-228 |

Hydrophilic Regions - Hopp-Woods

| | |
|---|---|
| SEQ. ID. NO. 29177 | 4-AlaGluIleLysArgProLeu-10 |
| SEQ. ID. NO. 29178 | 68-ArgProAlaArgArgArgValLeu-75 |
| SEQ. ID. NO. 29179 | 83-AlaAspAspGlyPhe-87 |
| SEQ. ID. NO. 29180 | 128-GlnThrGlyAsnArgArgIleValAsp-136 |
| SEQ. ID. NO. 29181 | 138-PheAspPheGluAsnArgPheArgArgAlaLeu-148 |
| SEQ. ID. NO. 29182 | 165-GlyLysGlnGlnAla-169 |
| SEQ. ID. NO. 29183 | 172-GlnHisGlyLysArgTyrPhe-178 |
| SEQ. ID. NO. 29184 | 187-SerLysCysArgLeuLysCysArgLeuLysArgGlyArgArgArgPheGly-203 |
| SEQ. ID. NO. 29185 | 213-MetProThrAlaSerArgThrLeuSerAsnAsnSerArgAlaSerLeu-228 | g205-1
AMPHI Regions - AMPHI

| | |
|---|---|
| SEQ. ID. NO. 29186 | 6-PheAlaValLeuGlyGly-11 |
| SEQ. ID. NO. 29187 | 21-SerGluAsnThrAlaGluGlnProGlnAsnAlaAlaGlnSer-34 |
| SEQ. ID. NO. 29188 | 87-GlyLysHisProAsnAspLeuGluAlaValValGlyLys-99 |

TABLE 1-continued

| | |
|---|---|
| SEQ. ID. NO. 29189 | 119-HisThrLeuPheAlaLysLeuValGlyAsnIleAlaGluAspGlyGlyLys-135 |
| SEQ. ID. NO. 29190 | 147-GlnProTyrGlnAla-151 |

Antigenic Index - Jameson-Wolf

| | |
|---|---|
| SEQ. ID. NO. 29191 | 18-CysGlyLysSerGluAsnThrAlaGluGlnProGlnAsnAlaAlaGlnSerAlaProLysProValPhe-40 |
| SEQ. ID. NO. 29192 | 56-GlyGlnSerSerGluGlyLysThrAsnAspGlyLysLysGlnIle-70 |
| SEQ. ID. NO. 29193 | 73-ProIleLysGlyLeuProGluGlnAsnAla-82 |
| SEQ. ID. NO. 29194 | 85-LeuThrGlyLysHisProAsnAspLeuGluAlaValVal-97 |
| SEQ. ID. NO. 29195 | 99-LysCysMetGluThrAspGlyLysAspAlaProSerGlyTrpAlaGluAsnGly-116 |
| SEQ. ID. NO. 29196 | 129-IleAlaGluAspGlyGlyLysLeuThr-137 |
| SEQ. ID. NO. 29197 | 149-TyrGlnAlaGlyLysSerGlyTyr-156 |
| SEQ. ID. NO. 29198 | 168-IleAspSerGluGlyAlaPhe-174 |

Hydrophilic Regions - Hopp-Woods

| | |
|---|---|
| SEQ. ID. NO. 29199 | 19-GlyLysSerGluAsnThrAlaGluGlnProGln-29 |
| SEQ. ID. NO. 29200 | 57-GlnSerSerGluGlyLysThrAsnAspGlyLysLysGlnIle-70 |
| SEQ. ID. NO. 29201 | 85-LeuThrGlyLysHisProAsnAspLeuGluAlaValVal-97 |
| SEQ. ID. NO. 29202 | 99-LysCysMetGluThrAspGlyLysAspAlaPro-109 |
| SEQ. ID. NO. 29203 | 129-IleAlaGluAspGlyGlyLysLeu-136 |
| SEQ. ID. NO. 29204 | 150-GlnAlaGlyLysSerGly-155 |
| SEQ. ID. NO. 29205 | 168-IleAspSerGluGlyAlaPhe-174 | g206
AMPHI Regions - AMPHI

| | |
|---|---|
| SEQ. ID. NO. 29206 | 32-ProLysGlnThrValArgGlnIleGlnAlaVal-42 |
| SEQ. ID. NO. 29207 | 44-IleSerHisIleGlyArgThrGln-51 |
| SEQ. ID. NO. 29208 | 81-CysSerGlyMetIleGln-86 |
| SEQ. ID. NO. 29209 | 99-ArgThrAlaArgAspMet-104 |
| SEQ. ID. NO. 29210 | 150-SerGlyLysThrIleLysThrGlu-157 |

Antigenic Index - Jameson-Wolf

| | |
|---|---|
| SEQ. ID. NO. 29211 | 2-PheSerProAspLysThrLeu-8 |
| SEQ. ID. NO. 29212 | 21-GlyThrThrSerGlyLysHisArgGlnProLysProLysGlnThrValArg-37 |
| SEQ. ID. NO. 29213 | 48-GlyArgThrGlnGlySerGlnGluLeu-56 |
| SEQ. ID. NO. 29214 | 66-ThrProTyrLysTrpGlyGlySerSerThr-75 |
| SEQ. ID. NO. 29215 | 96-LysLeuProArgThrAlaArgAspMetAlaAlaAlaSerArgLysIleProAspSerArgLeuLysAlaGly-119 |
| SEQ. ID. NO. 29216 | 126-ThrGlyGlyAlaHisArgTyrSer-133 |
| SEQ. ID. NO. 29217 | 146-HisAlaProGlySerGlyLysThrIleLysThrGluLysLeuSer-160 |

Hydrophilic Regions - Hopp-Woods

| | |
|---|---|
| SEQ. ID. NO. 29218 | 23-ThrSerGlyLysHisArgGlnProLysProLysGlnThrVal-36 |
| SEQ. ID. NO. 29219 | 48-GlyArgThrGlnGlySerGln-54 |
| SEQ. ID. NO. 29220 | 96-LysLeuProArgThrAlaArgAspMetAlaAlaAlaSerArgLysIleProAspSerArgLeuLysAlaGly-119 |
| SEQ. ID. NO. 29221 | 149-GlySerGlyLysThrIleLysThrGluLysLeuSer-160 | g211
AMPHI Regions - AMPHI

| | |
|---|---|
| SEQ. ID. NO. 29222 | 18-ValGlyAsnGlyValAspLysPheGlyArgGlyAla-29 |
| SEQ. ID. NO. 29223 | 57-GlnPheGluArgAla-61 |
| SEQ. ID. NO. 29224 | 99-LysGlyPheAspGluIleAsnProAla-107 |
| SEQ. ID. NO. 29225 | 109-AlaLeuAlaGlnValIleGluLeu-116 |
| SEQ. ID. NO. 29226 | 153-AspGlyLysArgHisGlyLysLeuHis-161 |

Antigenic Index - Jameson-Wolf

| | |
|---|---|
| SEQ. ID. NO. 29227 | 8-AsnGlnLeuGlyGlyArgAsnGlyAlaAlaVal-18 |
| SEQ. ID. NO. 29228 | 20-AsnGlyValAspLysPheGlyArgGlyAlaAspAsnGlnValGluPheLeuGlu-37 |
| SEQ. ID. NO. 29229 | 44-GlyAlaSerGlyArgAlaAla-50 |
| SEQ. ID. NO. 29230 | 73-GlyGluAspAspValVal-78 |
| SEQ. ID. NO. 29231 | 99-LysGlyPheAspGluIleAsnPro-106 |
| SEQ. ID. NO. 29232 | 140-CysProArgTyrHisProLysLeuHisAspGlyAsnGlnAspGlyLysArgHisGlyLysLeuHisAspGlyAlaTyr-165 |
| SEQ. ID. NO. 29233 | 169-GlnArgGlnSerAlaGly-174 |

Hydrophilic Regions - Hopp-Woods

| | |
|---|---|
| SEQ. ID. NO. 29234 | 10-LeuGlyGlyArgAsnGlyAla-16 |
| SEQ. ID. NO. 29235 | 21-GlyValAspLysPheGlyArgGlyAlaAspAsnGlnValGluPheLeuGlu-37 |
| SEQ. ID. NO. 29236 | 73-GlyGluAspAspValVal-78 |
| SEQ. ID. NO. 29237 | 100-GlyPheAspGluIleAsn-105 |
| SEQ. ID. NO. 29238 | 143-TyrHisProLysLeuHisAspGlyAsnGlnAspGlyLysArgHisGlyLysLeuHisAsp-162 | g212
AMPHI Regions - AMPHI

| | |
|---|---|
| SEQ. ID. NO. 29239 | 6-TrpAspGlyIleProAspIleArgThr-14 |
| SEQ. ID. NO. 29240 | 16-AspGlnThrIleArgLysHisAlaHis-24 |
| SEQ. ID. NO. 29241 | 40-PheGlnThrAlaGln-44 |
| SEQ. ID. NO. 29242 | 63-CysLeuGlnPheAspSerIleAsnLeuIleGluHisIle-75 |
| SEQ. ID. NO. 29243 | 89-ThrArgArgLeuHisGluHis-95 |
| SEQ. ID. NO. 29244 | 142-AlaSerThrAlaHis-146 |
| SEQ. ID. NO. 29245 | 199-ArgLeuLeuGlyHis-203 |
| SEQ. ID. NO. 29246 | 238-HisAsnHisLeuTyrArgSerIleThrSerAlaGluAlaGluLysIle-253 |
| SEQ. ID. NO. 29247 | 262-TyrAlaGluProLeuCysGlyLeu-269 |
| SEQ. ID. NO. 29248 | 288-SerHisProLeuIleGluLeu-294 |
| SEQ. ID. NO. 29249 | 296-GluAsnThrThrLeu-300 |
| SEQ. ID. NO. 29250 | 397-TrpAsnGluAlaGluGluAla-403 |

Antigenic Index - Jameson-Wolf

| | |
|---|---|
| SEQ. ID. NO. 29251 | 8-GlyIleProAspIleArgThrLeuAspGlnThrIleArgLysHisAlaHisProLeu-26 |
| SEQ. ID. NO. 29252 | 33-ProAspAsnGlnIleProAspPheGlnThrAlaGlnAspAlaSerAspSerGluCysArgLeuLysHisArgLeuAspGln-59 |
| SEQ. ID. NO. 29253 | 85-ProProSerArgThrArgArgLeuHisGlu-94 |
| SEQ. ID. NO. 29254 | 105-AlaIleProGlnThrGluSerLysSerAspLysProTrp-117 |
| SEQ. ID. NO. 29255 | 122-GlnThrSerGluArgLysLysProGluHis-131 |

TABLE 1-continued

| | |
|---|---|
| SEQ. ID. NO. 29256 | 158-LeuGluAlaArgLysAlaAlaGln-165 |
| SEQ. ID. NO. 29257 | 168-SerGlyAsnArgGlnGly-173 |
| SEQ. ID. NO. 29258 | 180-SerProHisAspThrGlyGlnThrGlu-188 |
| SEQ. ID. NO. 29259 | 193-GlyTyrGlyTyrThrLysArgLeuLeu-201 |
| SEQ. ID. NO. 29260 | 205-LeuProAspSerAspThrTrpGlyGlyAsn-214 |
| SEQ. ID. NO. 29261 | 220-AsnTyrSerArgThrGluGlnGlnArgAsnHisGluLeuGlyLeu-234 |
| SEQ. ID. NO. 29262 | 246-ThrSerAlaGluAlaGluLysIleAla-254 |
| SEQ. ID. NO. 29263 | 258-LeuAsnThrProTyrAlaGluProLeu-266 |
| SEQ. ID. NO. 29264 | 303-IleSerHisAspGlyGluLysTrpIle-311 |
| SEQ. ID. NO. 29265 | 328-ThrGlyAlaHisSerProCysLeuPro-336 |
| SEQ. ID. NO. 29266 | 346-ArgGlnIleArgGlyGlnThrGlyLeuThrProSerThrProPheSerGluGlnLeuArg-365 |
| SEQ. ID. NO. 29267 | 376-ProSerTrpHisGly-380 |
| SEQ. ID. NO. 29268 | 391-AsnSerAsnThrGlyTrpAsnGluAlaGluGlnAlaSerAsnArgGlnAla-408 |
| Hydrophilic Regions - Hopp-Woods | |
| SEQ. ID. NO. 29269 | 10-ProAspIleArgThrLeuAspGlnThrIleArgLysHisAla-23 |
| SEQ. ID. NO. 29270 | 44-GlnAspAlaSerAspSerGluCysArgLeuLysHisArgLeuAspGln-59 |
| SEQ. ID. NO. 29271 | 87-SerArgThrArgArgLeuHisGlu-94 |
| SEQ. ID. NO. 29272 | 105-AlaIleProGlnThrGluSerLysSerAspLys-115 |
| SEQ. ID. NO. 29273 | 122-GlnThrSerGluArgLysLysProGluHis-131 |
| SEQ. ID. NO. 29274 | 158-LeuGluAlaArgLysAlaAlaGln-165 |
| SEQ. ID. NO. 29275 | 180-SerProHisAspThrGlyGln-186 |
| SEQ. ID. NO. 29276 | 206-ProAspSerAspThr-210 |
| SEQ. ID. NO. 29277 | 222-SerArgThrGluGlnGlnArgAsnHisGlu-231 |
| SEQ. ID. NO. 29278 | 246-ThrSerAlaGluAlaGluLysIleAla-254 |
| SEQ. ID. NO. 29279 | 304-SerHisAspGlyGluLysTrpIle-311 |
| SEQ. ID. NO. 29280 | 346-ArgGlnIleArgGly-350 |
| SEQ. ID. NO. 29281 | 398-AsnGluAlaGluGluAlaSerAsnArgGlnAla-408 |
| g214-1 | |
| Hydrophilic Regions - Hopp-Woods | |
| SEQ. ID. NO. 29282 | 10-ProAspIleArgThrLeuAspGlnThrIleArgLysHisAla-23 |
| SEQ. ID. NO. 29283 | 44-GlnAspAlaSerAspSerGluCysArgLeuLysHisArgLeuAspGln-59 |
| SEQ. ID. NO. 29284 | 87-SerArgThrArgArgLeuHisGlu-94 |
| SEQ. ID. NO. 29285 | 105-AlaIleProGlnThrGluSerLysSerAspLys-115 |
| SEQ. ID. NO. 29286 | 122-GlnThrSerGluArgLysLysProGluHis-131 |
| SEQ. ID. NO. 29287 | 158-LeuGluAlaArgLysAlaAlaGln-165 |
| SEQ. ID. NO. 29288 | 180-SerProHisAspThrGlyGln-186 |
| SEQ. ID. NO. 29289 | 206-ProAspSerAspThr-210 |
| SEQ. ID. NO. 29290 | 222-SerArgThrGluGlnGlnArgAsnHisGlu-231 |
| SEQ. ID. NO. 29291 | 246-ThrSerAlaGluAlaGluLysIleAla-254 |
| SEQ. ID. NO. 29292 | 304-SerHisAspGlyGluLysTrpIle-311 |
| SEQ. ID. NO. 29293 | 346-ArgGlnIleArgGly-350 |
| SEQ. ID. NO. 29294 | 398-AsnGluAlaGluGluAlaSerAsnArgGlnAla-408 |
| Antigenic Index - Jameson-Wolf | |
| SEQ. ID. NO. 29295 | 23-LeuGlnSerAspSerArgArgProIleGlnIleGluAlaAspGlnGlySerLeuAspGlnAlaAsnGlnSerThrThrPheSerGlyAsn-52 |
| SEQ. ID. NO. 29296 | 71-ArgGlyGlyLysGlyGlyGluSerValArgAlaGluGlySerProValArgPheSerGlnThrLeuAspGlyGlyLysGlyThrValArgGly GlnAlaAsnAsnVal-106 |
| SEQ. ID. NO. 29297 | 119-GlyAsnAlaLysValGlnArgGlyGlyAspValAlaGlu-131 |
| SEQ. ID. NO. 29298 | 138-AsnThrLysThrGluVal-143 |
| SEQ. ID. NO. 29299 | 148-GlySerThrLysSerGlyAlaLysSerAlaSerLysThrGlyArgVal-163 |
| SEQ. ID. NO. 29300 | 169-ProSerSerThrGlnLysThrGlu-176 |
| Hydrophilic Regions - Hopp-Woods | |
| SEQ. ID. NO. 29301 | 25-SerAspSerArgArgProIleGlnIleGluAlaAspGlnGlySerLeuAspGlnAlaAsn-44 |
| SEQ. ID. NO. 29302 | 71-ArgGlyGlyLysGlyGlyGluSerValArgAlaGluGlySerPro-85 |
| SEQ. ID. NO. 29303 | 92-LeuAspGlyGlyLysGlyThrValArgGlyGlnAla-103 |
| SEQ. ID. NO. 29304 | 121-AlaLysValGlnArgGlyGlyAspValAlaGlu-131 |
| SEQ. ID. NO. 29305 | 148-GlySerThrLysSerGlyAlaLysSerAlaSerLysThrGlyArg-162 |
| SEQ. ID. NO. 29306 | 171-SerThrGlnLysThrGlu-176 |
| g215 | |
| AMPHI Regions - AMPHI | |
| SEQ. ID. NO. 29307 | 21-SerLeuSerAlaTrpLeuGlyArgIle-29 |
| SEQ. ID. NO. 29308 | 67-SerAlaLysGlyAlaLysGlnPhe-74 |
| Antigenic Index - Jameson-Wolf | |
| SEQ. ID. NO. 29309 | 3-ValArgTrpArgTyrGly-8 |
| SEQ. ID. NO. 29310 | 28-ArgIleSerGluValGluIleGluGluValArgLeuAsnProAspGluProGlnTyrThrMetAspGlyLeuAspGlyArgArgPheAspGlu GlnGlyTyrLeuLys-63 |
| SEQ. ID. NO. 29311 | 65-HisLeuSerAlaLysGlyAlaLysGlnPheProGluAsnSerAspIleHisPheAspSerProHisLeu-87 |
| SEQ. ID. NO. 29312 | 99-ValGlySerAspGluAlaValTyrHisThrGluAsnLysGlnValLeuPhe-115 |
| SEQ. ID. NO. 29313 | 123-LysThrAlaAspGlyArgArgGlnAlaGlyLysValGluThrGluLysLeuHisValAspThrGluSerGlnTyrAlaGlnThrAspThrProVal-154 |
| SEQ. ID. NO. 29314 | 160-AlaSerHisGlyGlnAlaGlyGly-167 |
| SEQ. ID. NO. 29315 | 170-TyrAsnHisLysThrGly-175 |
| SEQ. ID. NO. 29316 | 179-PheSerSerLysValLys-184 |
| SEQ. ID. NO. 29317 | 187-IleTyrAspThrLysAspMet-193 |
| Hydrophilic Regions - Hopp-Woods | |
| SEQ. ID. NO. 29318 | 29-IleSerGluValGluIleGluGluValArgLeuAsnProAspGluProGlnTyr-46 |
| SEQ. ID. NO. 29319 | 49-AspGlyLeuAspGlyArgArgPheAspGlu-58 |
| SEQ. ID. NO. 29320 | 65-HisLeuSerAlaLysGlyAlaLysGlnPheProGluAsnSerAspIleHisPhe-82 |
| SEQ. ID. NO. 29321 | 99-ValGlySerAspGluAlaValTyr-106 |
| SEQ. ID. NO. 29322 | 108-ThrGluAsnLysGlnValLeu-114 |
| SEQ. ID. NO. 29323 | 123-LysThrAlaAspGlyArgArgGlnAlaGlyLysValGluThrGluLysLeuHisValAspThrGluSerGlnTyrAla-148 |
| SEQ. ID. NO. 29324 | 187-IleTyrAspThrLysAspMet-193 |

TABLE 1-continued g216-2
AMPHI Regions - AMPHI
SEQ. ID. NO. 29325    19-AlaGluGlyLeuArgGluIleAlaAlaGluLeu-29
SEQ. ID. NO. 29326    60-ArgLysMetAlaAla-64
SEQ. ID. NO. 29327    165-LeuGlyAspAlaLeuAlaAlaVal-171
SEQ. ID. NO. 29328    201-ValAlaAspIleMetHis-206
SEQ. ID. NO. 29329    251-GlyAspLeuArgArgLeuPheGlnGluCysAspAsnPheThrGlyLeuSerIle-268
SEQ. ID. NO. 29330    272-MetHisThrHisProLysThrIleSerAla-281
SEQ. ID. NO. 29331    290-LysValMetGlnAlaAsn-295
Antigenic Index - Jameson-Wolf
SEQ. ID. NO. 29332    1-MetAlaGluAsnGluLysTyrLeuAspTrpAlaArg-12
SEQ. ID. NO. 29333    14-ValLeuHisThrGluAlaGluGlyLeuArgGluIleAlaAlaGluLeuAspGlu-31
SEQ. ID. NO. 29334    43-CysLysGlyArgVal-47
SEQ. ID. NO. 29335    51-GlyMetGlyLysSerGlyHisIleGlyArgLysMetAla-63
SEQ. ID. NO. 29336    80-GluAlaAlaHisGlyAspLeu-86
SEQ. ID. NO. 29337    90-ValAspAsnAspVal-94
SEQ. ID. NO. 29338    99-SerAsnSerGlyGluSerAspGluIle-107
SEQ. ID. NO. 29339    113-AlaLeuLysArgLysAspIle-119
SEQ. ID. NO. 29340    125-ThrAlaArgProAspSerThrMetAlaArgHisAlaAsp-137
SEQ. ID. NO. 29341    144-ValSerGlnGluAlaCysProLeu-151
SEQ. ID. NO. 29342    177-ArgAlaPheThrProAspPheAla-185
SEQ. ID. NO. 29343    190-AlaGlySerLeuGlyLys-195
SEQ. ID. NO. 29344    203-AspIleMetHisLysGlyGlyGlyLeuProAla-213
SEQ. ID. NO. 29345    227-MetSerGluLysGlyGlyLeu-232
SEQ. ID. NO. 29346    238-ThrAspGlyGlnGlyCysLeu-244
SEQ. ID. NO. 29347    248-PheThrAspGlyAspLeuArgArgLeuPheGlnGluCysAspAsnPheThr-264
SEQ. ID. NO. 29348    275-HisProLysThrIleSerAlaGluArgLeuAlaThrGluAlaLeuLys-290
Hydrophilic Regions - Hopp-Woods
SEQ. ID. NO. 29349    1-MetAlaGluAsnGluLysTyrLeuAspTrpAlaArg-12
SEQ. ID. NO. 29350    14-ValLeuHisThrGluAlaGluGlyLeuArgGluIleAlaAlaGluLeuAspGlu-31
SEQ. ID. NO. 29351    43-CysLysGlyArgVal-47
SEQ. ID. NO. 29352    56-GlyHisIleGlyArgLysMetAla-63
SEQ. ID. NO. 29353    100-AsnSerGlyGluSerAspGluIle-107
SEQ. ID. NO. 29354    113-AlaLeuLysArgLysAspIle-119
SEQ. ID. NO. 29355    126-AlaArgProAspSerThrMetAlaArgHisAlaAsp-137
SEQ. ID. NO. 29356    144-ValSerGlnGluAla-148
SEQ. ID. NO. 29357    177-ArgAlaPheThrProAspAsp-183
SEQ. ID. NO. 29358    227-MetSerGluLysGlyLeu-232
SEQ. ID. NO. 29359    251-GlyAspLeuArgArgLeuPheGlnGluCysAspAsn-262
SEQ. ID. NO. 29360    277-LysThrIleSerAlaGluArgLeuAlaThrGluAlaLeuLys-290
g218
AMPHI Regions - AMPHI
SEQ. ID. NO. 29361    9-AlaLysValValAsnThrMet-15
SEQ. ID. NO. 29362    23-HisThrMetAspGluIleHisGly-30
SEQ. ID. NO. 29363    78-AlaArgSerTrpTrpArgAsnLeuHisGlyAlaPheGlyThrTrpValSerLeuIleLeu-97
SEQ. ID. NO. 29364    111-TrpGlyGlyLysPheValGlnAlaTrpAsnGlnPhePro-123
SEQ. ID. NO. 29365    176-ThrGluProAsnAsnIle-181
SEQ. ID. NO. 29366    187-PheArgAlaGlyAsnArgPheGlnArgAlaLeuSerVal-199
Antigenic Index - Jameson-Wolf
SEQ. ID. NO. 29367    14-ThrMetProArgAsnGlnGlyTrp-21
SEQ. ID. NO. 29368    26-AspGluIleHisGly-30
SEQ. ID. NO. 29369    62-AlaLysGlnArgGlyIleLys-68
SEQ. ID. NO. 29370    71-LeuLeuProProLysSerArgAlaArgSerTrpTrp-82
SEQ. ID. NO. 29371    86-HisGlyAlaPheGly-90
SEQ. ID. NO. 29372    123-ProAlaGlyLysTrpGlyValGluProAsnProVal-134
SEQ. ID. NO. 29373    143-ValLeuAsnAspGlyLysValLysGlu-151
SEQ. ID. NO. 29374    167-ThrValGlyGluAsnGlyIleAsnProThrGluProAsnAsnIleGlyAsnArgArgProPheArgAlaGlyAsnArgPheGlnArg-195
SEQ. ID. NO. 29375    201-PheAlaGlnArgArgGlyArgGlyMetAspPhe-211
Hydrophilic Regions - Hopp-Woods
SEQ. ID. NO. 29376    26-AspGluIleHisGly-30
SEQ. ID. NO. 29377    64-GlnArgGlyIleLys-68
SEQ. ID. NO. 29378    74-ProLysSerArgAla-78
SEQ. ID. NO. 29379    143-ValLeuAsnAspGlyLysValLysGlu-151
SEQ. ID. NO. 29380    171-AsnGlyIleAsnProThrGluProAsnAsnIleGlyAsnArgArgProPheArgAlaGlyAsnArgPheGlnArg-195
SEQ. ID. NO. 29381    201-PheAlaGlnArgArgGlyArgGlyMetAsp-210
g225-1
AMPHI Regions - AMPHI
SEQ. ID. NO. 29382    23-LeuAlaAspGluLeuThrAsn-29
SEQ. ID. NO. 29383    37-IleLeuArgGlnPhe-41
SEQ. ID. NO. 29384    92-AspLysLeuIleGlySerAlaMetArg-100
SEQ. ID. NO. 29385    122-PheMetGlnHisIlePheLys-128
SEQ. ID. NO. 29386    188-ThrGlyLysAsnIle-192
Antigenic Index - Jameson-Wolf
SEQ. ID. NO. 29387    22-AlaLeuAlaAspGluLeuThr-28
SEQ. ID. NO. 29388    32-SerSerArgGluGlnIleLeu-38
SEQ. ID. NO. 29389    41-PheAlaGluAspGluGlnProVal-48
SEQ. ID. NO. 29390    50-ProValAsnArgAlaProAlaArgArgAlaGlyAsnAlaAspGluLeuIle-66
SEQ. ID. NO. 29391    79-ArgValAsnArgAlaXxxAlaArgArgAlaGlyAsnAlaAspLysLeuIle-95
SEQ. ID. NO. 29392    115-ThrGlyPheAspCysSerGly-121
SEQ. ID. NO. 29393    135-LeuProArgThrSerAlaGluGlnAlaArgMet-145

TABLE 1-continued

| | |
|---|---|
| SEQ. ID. NO. 29394 | 147-AlaProValAlaArgSerGluLeuGlnProGlyAsp-158 |
| SEQ. ID. NO. 29395 | 165-LeuGlyGlySerArgIleSer-171 |
| SEQ. ID. NO. 29396 | 184-HisAlaProArgThrGlyLysAsnIleGlu-193 |
| SEQ. ID. NO. 29397 | 196-SerLeuSerHisLysTyrTrpSerGlyLys-205 |
| SEQ. ID. NO. 29398 | 210-ArgArgValLysLysAsnAspProSerArgPhe-220 |

Hydrophilic Regions - Hopp-Woods

| | |
|---|---|
| SEQ. ID. NO. 29399 | 22-AlaLeuAlaAspGluLeuThr-28 |
| SEQ. ID. NO. 29400 | 32-SerSerArgGluGlnIleLeu-38 |
| SEQ. ID. NO. 29401 | 41-PheAlaGluAspGluGlnPro-47 |
| SEQ. ID. NO. 29402 | 53-ArgAlaProAlaArgArgAlaGlyAsnAlaAspGluLeuIle-66 |
| SEQ. ID. NO. 29403 | 79-ArgValAsnArgAlaXxxAlaArgArgAlaGlyAsnAlaAspLysLeuIle-95 |
| SEQ. ID. NO. 29404 | 137-ArgThrSerAlaGluGlnAlaArgMet-145 |
| SEQ. ID. NO. 29405 | 149-ValAlaArgSerGluLeuGlnPro-156 |
| SEQ. ID. NO. 29406 | 187-ArgThrGlyLysAsnIleGlu-193 |
| SEQ. ID. NO. 29407 | 210-ArgArgValLysLysAsnAspProSerArg-219 | g226
AMPHI Regions - AMPHI

| | |
|---|---|
| SEQ. ID. NO. 29408 | 44-LeuIleAlaTyrLeuLys-49 |
| SEQ. ID. NO. 29409 | 98-GlnLeuAlaGlySerValThrGlyIleValThr-108 |
| SEQ. ID. NO. 29410 | 142-ThrLeuTyrAlaArgValLeuProPro-150 |
| SEQ. ID. NO. 29411 | 165-ThrLeuArgArgPhe-169 |
| SEQ. ID. NO. 29412 | 174-LysLysLeuArgProPheLysProLeuLeuProVal-185 |

Antigenic Index - Jameson-Wolf

| | |
|---|---|
| SEQ. ID. NO. 29413 | 3-GluIleLeuArgGlnProSer-9 |
| SEQ. ID. NO. 29414 | 25-ValArgThrArgThrGlyAsnIle-32 |
| SEQ. ID. NO. 29415 | 67-PheArgLeuLysPro-71 |
| SEQ. ID. NO. 29416 | 81-TyrGlnAsnArgArgLysIle-87 |
| SEQ. ID. NO. 29417 | 117-GlyProAspThrGlnPhe-122 |
| SEQ. ID. NO. 29418 | 124-PheProProArgLeu-128 |
| SEQ. ID. NO. 29419 | 155-ProProLeuLeuProArgLeuGlyProHisThrLeuArgArg-168 |
| SEQ. ID. NO. 29420 | 171-IleLeuProLysLysLeuArgProPheLys-180 |

Hydrophilic Regions - Hopp-Woods

| | |
|---|---|
| SEQ. ID. NO. 29421 | 25-ValArgThrArgThr-29 |
| SEQ. ID. NO. 29422 | 82-GlnAsnArgArgLysIle-87 |
| SEQ. ID. NO. 29423 | 173-ProLysLysLeuArgPro-178 | g227
AMPHI Regions - AMPHI

| | |
|---|---|
| SEQ. ID. NO. 29424 | 36-GlyValLeuPheAlaLeuLeuGlnAla-44 |
| SEQ. ID. NO. 29425 | 51-TrpLeuGlnGlnLeuThrAspAlaLeu-59 |
| SEQ. ID. NO. 29426 | 74-ValIleSerTyrLeuAspLeuIleAlaAspAspTrpPheSer-87 | g230-1
AMPHI Regions - AMPHI

| | |
|---|---|
| SEQ. ID. NO. 29427 | 6-GluLysTyrArgThr-10 |
| SEQ. ID. NO. 29428 | 49-GluHisSerIleAsnAsn-54 |
| SEQ. ID. NO. 29429 | 56-MetGlnAsnGluGln-60 |
| SEQ. ID. NO. 29430 | 69-AspAlaValPheGlnSerLeuLeuGln-77 |
| SEQ. ID. NO. 29431 | 81-LeuLysGlnGlyAlaLys-86 |
| SEQ. ID. NO. 29432 | 96-GlnIleLysGlnMetIle-101 |
| SEQ. ID. NO. 29433 | 115-SerHisAlaLeuLeuSer-120 |
| SEQ. ID. NO. 29434 | 133-PheValGluGluIleArgAspGlnPhe-141 |
| SEQ. ID. NO. 29435 | 144-GlnAsnLeuValSerLeu-149 |
| SEQ. ID. NO. 29436 | 161-AlaGluGlnLeuIleArgLeuThrGlnValAsnArgThrIleArg-175 |
| SEQ. ID. NO. 29437 | 184-PheIleAlaGlnVal-188 |
| SEQ. ID. NO. 29438 | 194-AspLeuGlnLysPheTyrAsn-200 |
| SEQ. ID. NO. 29439 | 234-GluValLysAsnAlaPheGluGluArgValAlaArgLeu-246 |
| SEQ. ID. NO. 29440 | 272-ValAlaAspPheAsnLys-277 |
| SEQ. ID. NO. 29441 | 284-AspAspAlaPheAsnHisProSerSerLeuAlaGluAla-296 |
| SEQ. ID. NO. 29442 | 319-SerGlyMetProGluAsnLeuIleAsnAlaVal-329 |
| SEQ. ID. NO. 29443 | 398-LeuAsnGlyGlyLys-402 |
| SEQ. ID. NO. 29444 | 426-GluAlaTyrAlaGluLeu-431 |
| SEQ. ID. NO. 29445 | 461-ThrProProGluAspIleAlaAla-468 |
| SEQ. ID. NO. 29446 | 488-LeuLeuIleArgTyrPheAsn-494 |

Antigenic Index - Jameson-Wolf

| | |
|---|---|
| SEQ. ID. NO. 29447 | 4-SerIleGluLysTyrArgThrProAla-12 |
| SEQ. ID. NO. 29448 | 32-SerHisProGlyAlaAsp-37 |
| SEQ. ID. NO. 29449 | 42-ValGlyAspGluLysIleSerGluHisSerIle-52 |
| SEQ. ID. NO. 29450 | 56-MetGlnAsnGluGlnAlaAspGlyGlySerProTrpArg-68 |
| SEQ. ID. NO. 29451 | 80-TyrLeuLysGlnGlyAla-85 |
| SEQ. ID. NO. 29452 | 92-ValSerSerGluGlnIleLys-98 |
| SEQ. ID. NO. 29453 | 101-IleValAspAspProAsnPheHisAspAlaAsnGlyLysPhe-114 |
| SEQ. ID. NO. 29454 | 123-LeuSerGlnArgHisMetSerGluAspGlnPheValGluGlnIleArgAsp-139 |
| SEQ. ID. NO. 29455 | 169-GlnValAsnArgThrIleArgSerHisThrPheAsnProAspGluPhe-184 |
| SEQ. ID. NO. 29456 | 189-LysAlaSerGluAlaAspLeu-195 |
| SEQ. ID. NO. 29457 | 199-TyrAsnAlaAsnLysLysAspTyrLeu-207 |
| SEQ. ID. NO. 29458 | 223-AspPheAlaAspLysGlnThrValSerGluThrGluValLysAsnAlaPheGluGluArgValAlaArg-245 |
| SEQ. ID. NO. 29459 | 247-ProAlaHisGluAlaLysProSerPheGluGlnGluLysAlaAlaValGluAsnGluLeuLysMetLysLysAlaValAlaAspPheAsnLys AlaLysGluLysLeuGlyAspAspAlaPheAsnHisProSerSerLeuAlaGluAlaAlaLysAsnSerGlyLeuLysValGluThrGln GluThrTrpLeuSerArgGlnAspAlaGlnMetSerGlyMetProGluAsn-324 |
| SEQ. ID. NO. 29460 | 330-PheSerAspAspValLeuLysLysLysHisAsnSerGlu-342 |
| SEQ. ID. NO. 29461 | 355-ArgAlaLysGluValArgGluGluLysAsnLeuLeu-366 |

TABLE 1-continued

| | |
|---|---|
| SEQ. ID. NO. 29462 | 368-GluGluAlaLysAspAlaValArg-375 |
| SEQ. ID. NO. 29463 | 377-AlaTyrIleArgThrGluAlaAlaLysLeuAlaGluAsnLysAlaLysGluValLeu-395 |
| SEQ. ID. NO. 29464 | 399-AsnGlyGlyLysAlaValAsp-405 |
| SEQ. ID. NO. 29465 | 417-GlnGlnAlaArgGlnSerMetProProGluAlaTyr-428 |
| SEQ. ID. NO. 29466 | 432-LeuLysAlaLysProAlaAsnGlyLysProAla-442 |
| SEQ. ID. NO. 29467 | 459-AlaValThrProProGluAspIleAla-467 |
| SEQ. ID. NO. 29468 | 476-AlaLeuAlaGlnGlnGlnSerAlaAsnThrPhe-486 |
| SEQ. ID. NO. 29469 | 493-PheAsnGlyLysIleLysGlnThrLysGlyAlaGlnSerValAspAsnGlyAspGlyGln-512 |
| Hydrophilic Regions - Hopp-Woods | |
| SEQ. ID. NO. 29470 | 6-GluLysTyrArgThr-10 |
| SEQ. ID. NO. 29471 | 42-ValGlyAspGluLysIleSerGlu-49 |
| SEQ. ID. NO. 29472 | 56-MetGlnAsnGluGlnAlaAspGly-63 |
| SEQ. ID. NO. 29473 | 92-ValSerSerGluGlnIleLys-98 |
| SEQ. ID. NO. 29474 | 101-IleValAspAspProAsnPhe-107 |
| SEQ. ID. NO. 29475 | 110-AlaAsnGlyLysPhe-114 |
| SEQ. ID. NO. 29476 | 126-ArgHisMetSerGluAspGlnPheValGluGluIleArgAsp-139 |
| SEQ. ID. NO. 29477 | 189-LysAlaSerGluAlaAspLeu-195 |
| SEQ. ID. NO. 29478 | 200-AsnAlaAsnLysLysAspTyrLeu-207 |
| SEQ. ID. NO. 29479 | 223-AspPheAlaAspLysGlnThrValSerGluThrGluValLysAsnAlaPheGluGluArgValAlaArg-245 |
| SEQ. ID. NO. 29480 | 247-ProAlaHisGluAlaLysProSerPheGluGlnGluLysAlaAlaValGluAsnGluLeuLysMetLysLysAlaValAlaAspPheAsnLys AlaLysGluLysLeuGlyAspAspAlaPheAsn-288 |
| SEQ. ID. NO. 29481 | 292-SerLeuAlaGluAlaAlaLysAsnSerGlyLeuLysValGluThrGlnGlu-308 |
| SEQ. ID. NO. 29482 | 310-TrpLeuSerArgGlnAspAlaGlnMet-318 |
| SEQ. ID. NO. 29483 | 333-AspValLeuLysLysLysHisAsnSer-341 |
| SEQ. ID. NO. 29484 | 355-ArgAlaLysGluValArgGluGluLysAsnLeuLeu-366 |
| SEQ. ID. NO. 29485 | 368-GluGluAlaLysAspAlaValArg-375 |
| SEQ. ID. NO. 29486 | 377-AlaTyrIleArgThrGluAlaAlaLysLeuAlaGluAsnLysAlaLysGluValLeu-395 |
| SEQ. ID. NO. 29487 | 417-GlnGlnAlaArgGlnSerMetPro-424 |
| SEQ. ID. NO. 29488 | 432-LeuLysAlaLysProAlaAsnGly-439 |
| SEQ. ID. NO. 29489 | 461-ThrProProGluAspIleAla-467 |
| SEQ. ID. NO. 29490 | 496-LysIleLysGlnThrLysGlyAlaGlnSerValAspAsnGlyAspGlyGln-512 |
| g231-1 | |
| AMPHI Regions - AMPHI | |
| SEQ. ID. NO. 29491 | 7-IleAsnArgProTyrGlnLysProAlaGluLeu-17 |
| SEQ. ID. NO. 29492 | 98-ArgIlePheSerPheProGln-104 |
| SEQ. ID. NO. 29493 | 169-TyrAsnGluPheArgThrLeuArgArg-177 |
| SEQ. ID. NO. 29494 | 209-AlaValAspAspValLysGlyIleAlaVal-218 |
| Antigenic Index - Jameson-Wolf | |
| SEQ. ID. NO. 29495 | 1-MetSerLysArgLysSerIleAsnArgProTyrGlnLysProAlaGlu-16 |
| SEQ. ID. NO. 29496 | 18-ProProLeuGlnAsnAsnProProPheTyrArgLysAsnArgArgLeuAsn-34 |
| SEQ. ID. NO. 29497 | 39-AlaAspGlyGlyCysAlaSerProGlnLysCysArgAlaArgGlyPheGln-55 |
| SEQ. ID. NO. 29498 | 90-ProAlaValArgProArgArgLeuArg-98 |
| SEQ. ID. NO. 29499 | 135-MetProArgArgProVal-140 |
| SEQ. ID. NO. 29500 | 167-HisThrTyrAsnGluPheArgThrLeuArgArgArgAlaGlnVal-181 |
| SEQ. ID. NO. 29501 | 196-ValAspIleArgHisProAsn-202 |
| SEQ. ID. NO. 29502 | 209-AlaValAspAspValLysGly-215 |
| Hydrophilic Regions - Hopp-Woods | |
| SEQ. ID. NO. 29503 | 1-MetSerLysArgLysSerIleAsn-8 |
| SEQ. ID. NO. 29504 | 10-ProTyrGlnLysProAlaGlu-16 |
| SEQ. ID. NO. 29505 | 26-PheTyrArgLysAsnArgArg-32 |
| SEQ. ID. NO. 29506 | 45-SerProGlnLysCysArgAlaArgGly-53 |
| SEQ. ID. NO. 29507 | 92-ValArgProArgArgLeuArg-98 |
| SEQ. ID. NO. 29508 | 136-ProArgArgProVal-140 |
| SEQ. ID. NO. 29509 | 173-ArgThrLeuArgArgArgAlaGlnVal-181 |
| SEQ. ID. NO. 29510 | 196-ValAspIleArgHis-200 |
| SEQ. ID. NO. 29511 | 209-AlaValAspAspValLysGly-215 |
| g232 | |
| AMPHI Regions - AMPHI | |
| SEQ. ID. NO. 29512 | 14-AlaIleLeuPheGly-18 |
| SEQ. ID. NO. 29513 | 21-LeuGlyThrAlaVal-25 |
| SEQ. ID. NO. 29514 | 68-ValArgGlyThrLysSerLeuLeuArgGluThrVal-79 |
| SEQ. ID. NO. 29515 | 105-LeuProThrPheThrGln-110 |
| SEQ. ID. NO. 29516 | 151-ValThrValGlyAlaLeuGlySerThrValCys-161 |
| SEQ. ID. NO. 29517 | 173-ArgPheGluGlyLeuAsn-178 |
| SEQ. ID. NO. 29518 | 194-AlaValMetThrLeuIleGlyPhePheGlyGlyPhePheSerValProLeuTyrThrTrpLeu-214 |
| Antigenic Index - Jameson-Wolf | |
| SEQ. ID. NO. 29519 | 54-ValProAlaLysAlaAlaAspThrGlnIle-63 |
| SEQ. ID. NO. 29520 | 69-ArgGlyThrLysSerLeuLeuArgGluThrValArgHisAsnProVal-84 |
| SEQ. ID. NO. 29521 | 112-HisLeuGlyGlyAsnAspAsnVal-119 |
| SEQ. ID. NO. 29522 | 140-LysPheGlyArgGluArgLeu-146 |
| SEQ. ID. NO. 29523 | 170-HisGlyHisArgPheGluGly-176 |
| SEQ. ID. NO. 29524 | 217-AlaSerSerGluThrPheArgAlaArgAla-226 |
| SEQ. ID. NO. 29525 | 274-IleLysArgGluArgArgPheLeu-281 |
| SEQ. ID. NO. 29526 | 285-AlaIleArgLysLysPro-290 |
| Hydrophilic Regions - Hopp-Woods | |
| SEQ. ID. NO. 29527 | 55-ProAlaLysAlaAlaAspThrGlnIle-63 |
| SEQ. ID. NO. 29528 | 69-ArgGlyThrLysSerLeuLeuArgGluThrValArg-80 |
| SEQ. ID. NO. 29529 | 140-LysPheGlyArgGluArgLeu-146 |
| SEQ. ID. NO. 29530 | 172-HisArgPheGluGly-176 |
| SEQ. ID. NO. 29531 | 220-GluThrPheArgAlaArgAla-226 |

TABLE 1-continued

SEQ. ID. NO. 29532    274-IleLysArgGluArgArgPheLeu-281
SEQ. ID. NO. 29533    285-AlaIleArgLysLysPro-290
g233
AMPHI Regions - AMPHI
SEQ. ID. NO. 29534    36-GluHisValLeuGly-40
SEQ. ID. NO. 29535    61-PheAlaAspLysValGlnThr-67
SEQ. ID. NO. 29536    71-GlnValArgValTrpLysAsn-77
SEQ. ID. NO. 29537    88-AsnGlyValAlaLysLeuLeuGluThr-96
SEQ. ID. NO. 29538    119-AlaLeuAlaArgLeuIleGluGlnAlaGlyAsnAla-130
SEQ. ID. NO. 29539    138-ValProValAlaAspThrLeuLysArgAlaGluSer-149
SEQ. ID. NO. 29540    182-GluAsnLeuGlyGlyIleThrAsp-189
Antigenic Index - Jameson-Wolf
SEQ. ID. NO. 29541    1-MetLysArgLysAsnIle-6
SEQ. ID. NO. 29542    17-ArgPheGlyAlaAspLysProLysGlnTyrValGluIleGlySerLysThrValLeu-35
SEQ. ID. NO. 29543    43-GluArgHisGluAlaValAsp-49
SEQ. ID. NO. 29544    56-SerProGluAspThrPheAlaAspLysValGln-66
SEQ. ID. NO. 29545    75-TrpLysAsnGlyGlyGlnThrArgAlaGluThrValArgAsnGlyVal-90
SEQ. ID. NO. 29546    100-AlaGluThrAspAsn-104
SEQ. ID. NO. 29547    109-AspAlaAlaArgCys-113
SEQ. ID. NO. 29548    115-LeuProSerGluAlaLeu-120
SEQ. ID. NO. 29549    123-LeuIleGluGlnAlaGlyAsnAlaAlaGluGlyGly-134
SEQ. ID. NO. 29550    142-AspThrLeuLysArgAlaGluSerGlyGln-151
SEQ. ID. NO. 29551    155-ThrValAspArgSerGlyLeu-161
SEQ. ID. NO. 29552    183-AsnLeuGlyGlyIleThrAspGluAlaSerAlaValGluLysLeuGlyVal-199
SEQ. ID. NO. 29553    206-GlyAspAlaArgAsnLeuLysLeuThrGlnProGlnAspAlaTyr-220
Hydrophilic Regions - Hopp-Woods
SEQ. ID. NO. 29554    1-MetLysArgLysAsnIle-6
SEQ. ID. NO. 29555    18-PheGlyAlaAspLysProLysGlnTyrVal-27
SEQ. ID. NO. 29556    43-GluArgHisGluAlaValAsp-49
SEQ. ID. NO. 29557    56-SerProGluAspThrPheAlaAspLysValGln-66
SEQ. ID. NO. 29558    79-GlyGlnThrArgAlaGluThrValArg-87
SEQ. ID. NO. 29559    100-AlaGluThrAspAsn-104
SEQ. ID. NO. 29560    127-AlaGlyAsnAlaAlaGlu-132
SEQ. ID. NO. 29561    142-AspThrLeuLysArgAlaGluSerGlyGln-151
SEQ. ID. NO. 29562    187-IleThrAspGluAlaSerAlaValGluLysLeuGlyVal-199
SEQ. ID. NO. 29563    206-GlyAspAlaArgAsnLeuLys-212
g234
AMPHI Regions - AMPHI
SEQ. ID. NO. 29564    26-ArgSerLeuGluValAlaLysValAla-34
SEQ. ID. NO. 29565    68-AspArgLeuGlySerGln-73
SEQ. ID. NO. 29566    83-GlnGlnThrAsnArgPheAsnValLeuAsnArgThrAsn-95
SEQ. ID. NO. 29567    121-GlyAspValThrGluPhe-126
SEQ. ID. NO. 29568    205-GluAlaValAspAsnLeuValGlnAlaValAspAsn-216
Antigenic Index - Jameson-Wolf
SEQ. ID. NO. 29569    21-AlaThrGluSerSerArgSerLeuGluValAlaLys-32
SEQ. ID. NO. 29570    51-ThrPheAspAsnArgSerSerPhe-58
SEQ. ID. NO. 29571    62-IlePheSerAspSerGluAspArgLeuGlySerGlnAla-74
SEQ. ID. NO. 29572    83-GlnGlnThrAsnArgPheAsnValLeuAsnArgThrAsn-95
SEQ. ID. NO. 29573    99-LeuLysGlnGluSerGlyIleSerGlyLysAlaGlnAsnLeuLysGlyAlaAspTyr-117
SEQ. ID. NO. 29574    121-GlyAspValThrGluPheGlyArgArgAspValGlyAsp-133
SEQ. ID. NO. 29575    140-LeuGlyArgGlyLysSerGlnIle-147
SEQ. ID. NO. 29576    169-GlnGlyAlaGlyGlu-173
SEQ. ID. NO. 29577    175-AlaLeuSerAsnArgGluIle-181
SEQ. ID. NO. 29578    185-GlyGlyThrSerGlyTyrAspAlaThrLeuAsnGlyLysValLeu-199
SEQ. ID. NO. 29579    214-ValAspAsnGlyAlaTrpGlnSerAsnArg-223
Hydrophilic Regions - Hopp-Woods
SEQ. ID. NO. 29580    21-AlaThrGluSerSerArgSerLeuGluValAlaLys-32
SEQ. ID. NO. 29581    52-PheAspAsnArgSerSerPhe-58
SEQ. ID. NO. 29582    62-IlePheSerAspSerGluAspArgLeuGlySerGlnAla-74
SEQ. ID. NO. 29583    99-LeuLysGlnGluSerGlyIleSerGlyLysAlaGlnAsnLeuLysGly-114
SEQ. ID. NO. 29584    122-AspValThrGluPheGlyArgArgAspValGlyAsp-133
SEQ. ID. NO. 29585    141-GlyArgGlyLysSer-145
SEQ. ID. NO. 29586    176-LeuSerAsnArgGluIle-181
g235
AMPHI Regions - AMPHI
SEQ. ID. NO. 29587    8-LeuAlaAlaValLeuAlaLeu-14
SEQ. ID. NO. 29588    18-GlnValArgLysAlaProAsp-24
SEQ. ID. NO. 29589    88-AsnAlaAlaAspIle-92
SEQ. ID. NO. 29590    95-ValArgProGluLysLeuHisGlnIlePhe-104
SEQ. ID. NO. 29591    120-SerTyrGlnIleLeuAspSerValThrThr-129
SEQ. ID. NO. 29592    165-GlyAlaLeuValGlyAlaValValAsnGlnIleAlaAsnSerLeuThr-180
SEQ. ID. NO. 29593    187-SerLysThrAlaAlaTyrAsnLeuLeu-195
Antigenic Index - Jameson-Wolf
SEQ. ID. NO. 29594    17-CysGlnValArgLysAlaProAspLeuAspTyrThrSerPheLysGluSerLysProAla-36
SEQ. ID. NO. 29595    43-ProLeuAsnGluSerProAspValAsnGlyThr-53
SEQ. ID. NO. 29596    79-GluThrPheLysGluAsnGlyLeu-86
SEQ. ID. NO. 29597    93-HisAlaValArgProGluLysLeu-100
SEQ. ID. NO. 29598    131-SerAlaLysAlaArgLeuValAspSerArgAsnGlyLysGluLeuTrpSerGlySerAlaSerIleArgGluGlySerAsnAsnSerAsnSer-161
SEQ. ID. NO. 29599    178-SerLeuThrAspArgGlyTyrGlnValSerLysThrAla-190
SEQ. ID. NO. 29600    197-ProTyrSerArgAsnGlyIleLeuLysGlyProArgPheValGluGluGlnProLys-215

TABLE 1-continued

Hydrophilic Regions - Hopp-Woods
SEQ. ID. NO. 29601    18-GlnValArgLysAlaProAspLeuAsp-26
SEQ. ID. NO. 29602    29-SerPheLysGluSerLysPro-35
SEQ. ID. NO. 29603    44-LeuAsnGluSerProAspVal-50
SEQ. ID. NO. 29604    79-GluThrPheLysGluAsnGlyLeu-86
SEQ. ID. NO. 29605    93-HisAlaValArgProGluLysLeu-100
SEQ. ID. NO. 29606    131-SerAlaLysAlaArgLeuValAspSerArgAsnGlyLysGluLeuTrp-146
SEQ. ID. NO. 29607    150-AlaSerIleArgGluGlySerAsnAsnSer-159
SEQ. ID. NO. 29608    179-LeuThrAspArgGlyTyrGln-185
SEQ. ID. NO. 29609    207-ProArgPheValGluGluGlnProLys-215
g236
AMPHI Regions - AMPHI
SEQ. ID. NO. 29610    10-IleLeuArgThrAlaPhe-15
SEQ. ID. NO. 29611    107-PheAlaArgPheAlaAspCysArgProPhe-116
SEQ. ID. NO. 29612    146-AspAspValProArgPhePheAlaGlyGlu-155
SEQ. ID. NO. 29613    168-ArgAspValValGlnGlyGlyLeu-175
SEQ. ID. NO. 29614    213-GlyGluValGluGlyIleAlaArgIleValThrAlaCysGlnThrLeuLeuGlnProProArgGlnTyrGln-236
SEQ. ID. NO. 29615    245-IleArgLeuLeuHisGlyIlePheAsnArgIleLysValAla-258
SEQ. ID. NO. 29616    275-PheGlyAsnAlaPheGluAspPhe-282
SEQ. ID. NO. 29617    316-ValAlaAspGlyPheArgHisPheAlaAla-325
Antigenic Index - Jameson-Wolf
SEQ. ID. NO. 29618    43-PheGlyGlyAsnGlyLysPheIleThr-51
SEQ. ID. NO. 29619    58-ArgHisGlnGlnGlyLysAla-64
SEQ. ID. NO. 29620    77-PhePheArgArgGlyAsnPheGlyPheArgLeuGlnGlyArgThrAspSerPhe-94
SEQ. ID. NO. 29621    98-GlnArgLeuAspSerGlyGlyTyr-105
SEQ. ID. NO. 29622    111-AlaAspCysArgProPhe-116
SEQ. ID. NO. 29623    126-ValAspGlyArgGluLeuValProSerMetGluGluAspAla-139
SEQ. ID. NO. 29624    145-AlaAspAspValPro-149
SEQ. ID. NO. 29625    152-PheAlaGlyGluAlaGlnAsnArgCysAsnGlnGluAsnGlnAlaAlaArgAspValValGlnGlyGlyLeu-175
SEQ. ID. NO. 29626    195-ValGluValGluArgAlaGlnValPheArgAlaGluArgAsnAsnValPhe-211
SEQ. ID. NO. 29627    213-GlyGluValGluGlyIleAla-219
SEQ. ID. NO. 29628    230-GlnProProArgGlnTyrGln-236
SEQ. ID. NO. 29629    261-GlyLysGlnGluAlaGlnGly-267
SEQ. ID. NO. 29630    292-IleGlyGlyCysArgProGlnAlaGlnAspValArgAla-304
SEQ. ID. NO. 29631    310-PheLeuArgArgAspAspValAlaAspGly-319
SEQ. ID. NO. 29632    341-CysAlaSerHisGly-345
Hydrophilic Regions - Hopp-Woods
SEQ. ID. NO. 29633    87-LeuGlnGlyArgThrAspSer-93
SEQ. ID. NO. 29634    98-GlnArgLeuAspSer-102
SEQ. ID. NO. 29635    127-AspGlyArgGluLeuValProSerMetGluGluAspAla-139
SEQ. ID. NO. 29636    145-AlaAspAspValPro-149
SEQ. ID. NO. 29637    156-AlaGlnAsnArgCysAsnGlnGluAsnGlnAlaAlaArgAspValVal-171
SEQ. ID. NO. 29638    195-ValGluValGluArgAlaGlnValPheArgAlaGluArgAsnAsn-209
SEQ. ID. NO. 29639    213-GlyGluValGluGlyIleAla-219
SEQ. ID. NO. 29640    261-GlyLysGlnGluAlaGlnGly-267
SEQ. ID. NO. 29641    295-CysArgProGlnAlaGlnAspValArgAla-304
SEQ. ID. NO. 29642    310-PheLeuArgArgAspAspValAlaAspGly-319
g238
AMPHI Regions - AMPHI
SEQ. ID. NO. 29643    103-ValHisSerProPheAsp-108
SEQ. ID. NO. 29644    115-ThrSerAspPheSerGlyGlyVal-122
SEQ. ID. NO. 29645    129-TyrGlnLeuHisArgThrGlySer-136
SEQ. ID. NO. 29646    140-ProAlaAspGlyTyrAspGlyProGlnGlyGlyGlyTyrProGluProGlnGlyAlaArgAspIleTyrSerTyr-164
SEQ. ID. NO. 29647    221-AsnArgMetAspAspIleArgGlyIleValGlnGlyAlaValAsnProPheLeuThrGlyPheGlnGlyVal-244
SEQ. ID. NO. 29648    246-IleGlyAlaIleThrAspSerAlaValSerProValThrAspThrAlaAlaGlnGlnThrLeuGlnGlyIleAsnAspLeuGlyAsn-274
SEQ. ID. NO. 29649    298-IleAsnSerAlaArgGlnTrpAlaAspAla-307
SEQ. ID. NO. 29650    342-AspTrpValLysAsn-346
SEQ. ID. NO. 29651    351-LysProAlaAlaArgHisMetGlnThrVal-360
SEQ. ID. NO. 29652    367-GlyAsnArgProProLysSerIleThrSer-376
SEQ. ID. NO. 29653    383-AlaThrTyrProLysLeuValAsnGlnLeuAsnGluGlnAsnLeu-397
SEQ. ID. NO. 29654    426-GluGluAlaAspArgLeuGlyLysIleTrpVal-436
SEQ. ID. NO. 29655    454-ThrArgGlnTyrArg-458
Antigenic Index - Jameson-Wolf
SEQ. ID. NO. 29656    25-HisAlaAsnGlyLeuAspAlaArgLeuArgAspAspMetGlnAlaLysHisTyrGluProGlyGlyLys-47
SEQ. ID. NO. 29657    53-AsnAlaArgGlySerValLysAsnArgVal-62
SEQ. ID. NO. 29658    80-ThrHisGluArgThrGlyPheGluGly-88
SEQ. ID. NO. 29659    96-PheSerGlyHisGlyHisGluVal-103
SEQ. ID. NO. 29660    105-SerProPheAspAsnHisAspSerLysSerThrSerAspPheSerGlyGlyValAspGlyGly-125
SEQ. ID. NO. 29661    131-LeuHisArgThrGlySerGluIleHisProAlaAspGlyTyrAspGlyProGlnGlyGlyGlyTyrProGluProGlnGlyAlaArgAspIleTyr-162
SEQ. ID. NO. 29662    166-IleLysGlyThrSerThrLysThrLysIle-175
SEQ. ID. NO. 29663    182-ProPheSerAspArgTrpLeuLysGluAsnAlaGlyAla-194
SEQ. ID. NO. 29664    200-SerArgAlaAspGluAlaGly-206
SEQ. ID. NO. 29665    210-TrpGluAsnAspProAspLysAsnTrpArgAlaAsnArgMetAspAspIleArgIle-229
SEQ. ID. NO. 29666    268-GlyIleAsnAspLeuGlyAsnLeuSerProGluAla-279
SEQ. ID. NO. 29667    292-PheAlaValLysAspGlyIleAsnSerAlaArgGlnTrpAlaAspAlaHisProAsnIle-311
SEQ. ID. NO. 29668    328-ValTrpArgGlyLysLysValGluLeuAsnProThrLysTrpAspTrpValLysAsnThrGlyTyrLysLysProAlaAlaArg-355
SEQ. ID. NO. 29669    358-GlnThrValAspGlyGluMetAlaGlyAspAsnProProLysSerIleThrSerGluGlyLysAlaAsn-381
SEQ. ID. NO. 29670    391-GlnLeuAsnGluGlnAsnLeu-397
SEQ. ID. NO. 29671    401-AlaAlaGlnAspProArgLeu-407
SEQ. ID. NO. 29672    411-IleHisGluGlyLysLysAsnPhePro-419

TABLE 1-continued

| | |
|---|---|
| SEQ. ID. NO. 29673 | 423-AlaThrTyrGluGluAlaAspArgLeuGly-432 |
| SEQ. ID. NO. 29674 | 438-GluGlyAlaArgGlnThrSerGlyGlyGlyTrpLeuSerArgAspGlyThrArgGlnTyrArgProProThrGluLysLysSerGln-466 |
| SEQ. ID. NO. 29675 | 480-ThrIleAspSerAsnGluLysArgAsnLysIleLysAsnGly-493 |

Hydrophilic Regions - Hopp-Woods

| | |
|---|---|
| SEQ. ID. NO. 29676 | 29-LeuArgAlaArgLeuArgAspAspMetGlnAlaLysHisTyrGluProGlyGly-46 |
| SEQ. ID. NO. 29677 | 54-AlaArgGlySerValLysAsnArgVal-62 |
| SEQ. ID. NO. 29678 | 80-ThrHisGluArgThrGlyPhe-86 |
| SEQ. ID. NO. 29679 | 107-PheAspAsnHisAspSerLysSerThrSerAspPhe-118 |
| SEQ. ID. NO. 29680 | 133-ArgThrGlySerGluIleHisPro-140 |
| SEQ. ID. NO. 29681 | 142-AspGlyTyrAspGlyProGln-148 |
| SEQ. ID. NO. 29682 | 151-GlyTyrProGluProGlnGlyAlaArgAsp-160 |
| SEQ. ID. NO. 29683 | 168-GlyThrSerThrLysThrLysIle-175 |
| SEQ. ID. NO. 29684 | 186-ArgTrpLeuLysGluAsnAlaGly-193 |
| SEQ. ID. NO. 29685 | 200-SerArgAlaAspGluAlaGly-206 |
| SEQ. ID. NO. 29686 | 212-AsnAspProAspLysAsnTrpArgAlaAsnArgMetAspAspIleArgGly-228 |
| SEQ. ID. NO. 29687 | 296-AspGlyIleAsnSer-300 |
| SEQ. ID. NO. 29688 | 329-TrpArgGlyLysLysValGluLeuAsnProThr-339 |
| SEQ. ID. NO. 29689 | 347-ThrGlyTyrLysLysProAlaAlaArg-355 |
| SEQ. ID. NO. 29690 | 360-ValAspGlyGluMetAlaGlyGlyAsnArgProProLysSerIleThrSerGluGlyLysAlaAsn-381 |
| SEQ. ID. NO. 29691 | 392-LeuAsnGluGlnAsnLeu-397 |
| SEQ. ID. NO. 29692 | 401-AlaAlaGlnAspProArgLeu-407 |
| SEQ. ID. NO. 29693 | 412-HisGluGlyLysLysAsnPhe-418 |
| SEQ. ID. NO. 29694 | 424-ThrTyrGluGluAlaAspArgLeuGly-432 |
| SEQ. ID. NO. 29695 | 438-GluGlyAlaArgGlnThrSer-444 |
| SEQ. ID. NO. 29696 | 449-LeuSerArgAspGlyThrArgGlnTyrArgProProThrGluLysLysSerGln-466 |
| SEQ. ID. NO. 29697 | 482-AspSerAsnGluLysArgAsnLysIleLysAsn-492 | g239
AMPHI Regions - AMPHI

| | |
|---|---|
| SEQ. ID. NO. 29698 | 49-PheArgLeuValGlnSerCys-55 |
| SEQ. ID. NO. 29699 | 72-AsnAlaHisArgLysGln-77 |
| SEQ. ID. NO. 29700 | 123-ProGlyPheAsnAlaLeuProThrIlePhe-132 |
| SEQ. ID. NO. 29701 | 154-GluTyrPheLeuThr-158 |
| SEQ. ID. NO. 29702 | 165-SerSerAsnGluTrp-169 |
| SEQ. ID. NO. 29703 | 221-PheCysAlaThrIleCysAlaSerLeuArg-230 |

Antigenic Index - Jameson-Wolf

| | |
|---|---|
| SEQ. ID. NO. 29704 | 6-GlyIleAlaArgAsnArgArgMetGlu-14 |
| SEQ. ID. NO. 29705 | 19-CysArgArgProAspArgPheVal-26 |
| SEQ. ID. NO. 29706 | 28-ArgGlnThrArgLeuLeu-33 |
| SEQ. ID. NO. 29707 | 53-GlnSerCysGluValGluPro-59 |
| SEQ. ID. NO. 29708 | 66-HisAsnGlyLysSerGlyAsnAlaHisArgLysGlnGlnLysGluIleArg-82 |
| SEQ. ID. NO. 29709 | 84-ValHisCysArgSerAspVal-90 |
| SEQ. ID. NO. 29710 | 100-ProAlaValArgSerAlaThrArgLysThrAla-110 |
| SEQ. ID. NO. 29711 | 132-PheArgGlyGlySerGlyLysSerAlaSer-141 |
| SEQ. ID. NO. 29712 | 147-LeuGlyArgGlySerCysCysGluTyr-155 |
| SEQ. ID. NO. 29713 | 164-ArgSerSerAsnGluTrpLys-170 |
| SEQ. ID. NO. 29714 | 173-ThrAlaLysArgProProSerPheArgArgHisMetThrCysGlyAsnThrAlaProThrSerSerSerSerArgLeuIleLys-200 |
| SEQ. ID. NO. 29715 | 209-ValAlaGlySerCysProArgSerArgValArgThr-220 |
| SEQ. ID. NO. 29716 | 248-TrpArgLeuAsnArgSerSerPro-255 |

Hydrophilic Regions - Hopp-Woods

| | |
|---|---|
| SEQ. ID. NO. 29717 | 6-GlyIleAlaArgAsnArgArgMetGlu-14 |
| SEQ. ID. NO. 29718 | 20-ArgArgProAspArgPheVal-26 |
| SEQ. ID. NO. 29719 | 67-AsnGlyLysSerGlyAsnAlaHisArgLysGlnGlnLysGluIleArg-82 |
| SEQ. ID. NO. 29720 | 102-ValArgSerAlaThrArgLysThrAla-110 |
| SEQ. ID. NO. 29721 | 135-GlySerGlyLysSerAlaSer-141 |
| SEQ. ID. NO. 29722 | 165-SerSerAsnGluTrpLys-170 |
| SEQ. ID. NO. 29723 | 173-ThrAlaLysArgProProSerPheArgArgHisMet-184 |
| SEQ. ID. NO. 29724 | 193-SerSerSerSerArgLeuIleLys-200 |
| SEQ. ID. NO. 29725 | 211-GlySerCysProArgSerArgValArgThr-220 |
| SEQ. ID. NO. 29726 | 251-AsnArgSerSerPro-255 | g240
AMPHI Regions - AMPHI

| | |
|---|---|
| SEQ. ID. NO. 29727 | 19-AlaAspValGlyArgPheLeuHis-26 |
| SEQ. ID. NO. 29728 | 64-IleGlnCysLeuArgAsnHis-70 |
| SEQ. ID. NO. 29729 | 88-AlaProLeuPheAla-92 |
| SEQ. ID. NO. 29730 | 108-GlnGlyGluAspPheProArgAlaGlyIleGlnAsnHis-120 |
| SEQ. ID. NO. 29731 | 164-ValGlnAlaValHisAsn-169 |
| SEQ. ID. NO. 29732 | 178-AsnPheArgAlaValPheAlaIle-185 |
| SEQ. ID. NO. 29733 | 189-PheLysArgLysPheGln-194 |

Antigenic Index - Jameson-Wolf

| | |
|---|---|
| SEQ. ID. NO. 29734 | 10-AlaGluThrArgArgGlnPheAla-17 |
| SEQ. ID. NO. 29735 | 41-AlaHisGlyArgArgSerAspPheIleArg-50 |
| SEQ. ID. NO. 29736 | 68-ArgAsnHisGluArgPheAspCysArgThrArgPheAsp-80 |
| SEQ. ID. NO. 29737 | 102-ValGlyGlyArgIleGlyGlnGlyGluAspPheProArgAlaGlyIleGlnAsnHisHisArgSerGly-124 |
| SEQ. ID. NO. 29738 | 140-GlnGlyLeuAsnProLeuIleGluGlyLysAspAspVal-152 |
| SEQ. ID. NO. 29739 | 189-PheLysArgLysPhe-193 |
| SEQ. ID. NO. 29740 | 202-AsnIleGlyLysSerAspAspValCysLys-211 |

Hydrophilic Regions - Hopp-Woods

| | |
|---|---|
| SEQ. ID. NO. 29741 | 10-AlaGluThrArgArgGlnPheAla-17 |
| SEQ. ID. NO. 29742 | 42-HisGlyArgArgSerAspPheIleArg-50 |
| SEQ. ID. NO. 29743 | 68-ArgAsnHisGluArgPheAspCysArgThrArgPheAsp-80 |

TABLE 1-continued

| | |
|---|---|
| SEQ. ID. NO. 29744 | 106-IleGlyGlnGlyGluAspPheProArg-114 |
| SEQ. ID. NO. 29745 | 146-IleGluGlyLysAspAspVal-152 |
| SEQ. ID. NO. 29746 | 189-PheLysArgLysPhe-193 |
| SEQ. ID. NO. 29747 | 204-GlyLysSerAspAspValCysLys-211 | g241-1
AMPHI Regions - AMPHI

| | |
|---|---|
| SEQ. ID. NO. 29748 | 6-ThrArgAlaAlaAsnProPro-12 |
| SEQ. ID. NO. 29749 | 35-ThrHisThrProHisGluProAlaSerSer-44 |
| SEQ. ID. NO. 29750 | 109-PheLeuIleGlyCysIleAlaHisAlaPheAsnArgSerPheLys-123 |
| SEQ. ID. NO. 29751 | 126-PheHisAlaCysGlnArgMetValAlaVal-135 |
| SEQ. ID. NO. 29752 | 195-HisPheAspArgIleAlaGlyIleLeuThrValIn-206 |
| SEQ. ID. NO. 29753 | 228-GlyPheIleGlnLysLeuIleValGlyIleIleHis-239 |

Antigenic Index - Jameson-Wolf

| | |
|---|---|
| SEQ. ID. NO. 29754 | 1-MetProThrArgProThrArgAlaAlaAsnProProThrPro-14 |
| SEQ. ID. NO. 29755 | 22-TyrCysProArgProProTyrArgProProSerValGlnThrHisThrProHisGluProAlaSerSerThrCysAlaAlaLysSerAla AsnArgArgGluAsnSerHisAsnAlaGlnPro-62 |
| SEQ. ID. NO. 29756 | 68-ProSerAsnLysMetProSerGluThrGluGlnThrLeuPheArgArgHisGlnIleProProSerCysArgGlnSer-93 |
| SEQ. ID. NO. 29757 | 119-AsnArgSerPheLysAla-124 |
| SEQ. ID. NO. 29758 | 147-ThrIleAspAspAsnIleAla-153 |
| SEQ. ID. NO. 29759 | 161-LysHisHisThrAspLeuAspPheAsnArgGluArgAlaArgIlePheAsnThrAspGlnLeu-181 |
| SEQ. ID. NO. 29760 | 188-ArgIleValGlyArgLysArgHisPheAspArg-198 |
| SEQ. ID. NO. 29761 | 209-PheHisGlnArgGluAsnAla-215 |
| SEQ. ID. NO. 29762 | 244-ArgAsnHisGlyIlePheCysAsnSerHis-253 |
| SEQ. ID. NO. 29763 | 255-CysProPheArgAsnSerArgLeuIle-263 |

Hydrophilic Regions - Hopp-Woods

| | |
|---|---|
| SEQ. ID. NO. 29764 | 1-MetProThrArgProThrArgAlaAlaAsn-10 |
| SEQ. ID. NO. 29765 | 37-ThrProHisGluProAlaSer-43 |
| SEQ. ID. NO. 29766 | 46-CysAlaAlaLysSerAlaAsnArgArgGluAsnSerHis-58 |
| SEQ. ID. NO. 29767 | 70-AsnLysMetProSerGluThrGluGlnThrLeuPheArg-82 |
| SEQ. ID. NO. 29768 | 120-ArgSerPheLysAla-124 |
| SEQ. ID. NO. 29769 | 161-LysHisHisThrAspLeuAspPheAsnArgGluArgAlaArgIlePheAsn-177 |
| SEQ. ID. NO. 29770 | 188-ArgIleValGlyArgLysArgHisPheAspArg-198 |
| SEQ. ID. NO. 29771 | 209-PheHisGlnArgGluAsnAla-215 | g242
AMPHI Regions - AMPHI

| | |
|---|---|
| SEQ. ID. NO. 29772 | 25-ValAlaAlaGlnPheValAspPheValGluGln-35 |
| SEQ. ID. NO. 29773 | 46-HisIleLeuGlnAsn-50 |
| SEQ. ID. NO. 29774 | 100-AlaAspGlnThrGln-104 |
| SEQ. ID. NO. 29775 | 122-AsnProPhePheAspPhePheGlnAlaValVal-132 |
| SEQ. ID. NO. 29776 | 137-HisGlnSerGlyPheGlyAspValPhe-145 |
| SEQ. ID. NO. 29777 | 191-PheGlyHisThrArg-195 |
| SEQ. ID. NO. 29778 | 197-PheAspAlaCysLeu-201 |
| SEQ. ID. NO. 29779 | 262-HisProPheAlaAspPheGlyAsnLeuGlnAsnLeuLeuAlaLeu-276 |

Antigenic Index - Jameson-Wolf

| | |
|---|---|
| SEQ. ID. NO. 29780 | 14-PheLysGlnArgAlaGlyGlyIleAla-22 |
| SEQ. ID. NO. 29781 | 33-ValGluGlnGluGlnArgValSer-40 |
| SEQ. ID. NO. 29782 | 54-HisArgAlaAspIleGlyThrAlaValProAla-64 |
| SEQ. ID. NO. 29783 | 73-AlaGlnGlyHisThrAspIlePheProProArgCysPheGlyAspGlyPheAlaGlnArgGlyPheAlaHisAlaArgArgAlaAspGlnThr GlnAsnArgThrPhe-108 |
| SEQ. ID. NO. 29784 | 137-HisGlnSerGlyPhe-141 |
| SEQ. ID. NO. 29785 | 152-LeuProArgGlnSerGluGlnGlyVal-160 |
| SEQ. ID. NO. 29786 | 164-AlaTyrAspGlyGlyPheGlyArgHisArgArgHisHis-176 |
| SEQ. ID. NO. 29787 | 283-MetArgCysAspArgIleGly-289 |

Hydrophilic Regions - Hopp-Woods

| | |
|---|---|
| SEQ. ID. NO. 29788 | 14-PheLysGlnArgAlaGlyGlyIle-21 |
| SEQ. ID. NO. 29789 | 33-ValGluGlnGluGlnArgVal-39 |
| SEQ. ID. NO. 29790 | 54-HisArgAlaAspIle-58 |
| SEQ. ID. NO. 29791 | 95-AlaHisAlaArgArgAlaAspGlnThrGlnAsnArgThrPhe-108 |
| SEQ. ID. NO. 29792 | 154-ArgGlnSerGluGlnGlyVal-160 |
| SEQ. ID. NO. 29793 | 168-GlyPheGlyArgHisArgArgHisHis-176 |
| SEQ. ID. NO. 29794 | 283-MetArgCysAspArgIleGly-289 | g243
AMPHI Regions - AMPHI

| | |
|---|---|
| SEQ. ID. NO. 29795 | 35-MetThrArgLeuAlaArgLysAlaValGlnArgLeuThrAlaSerHisIleGlnArgPheLeu-55 |
| SEQ. ID. NO. 29796 | 80-AspSerSerArgIleThrSerThrIle-88 |

Antigenic Index - Jameson-Wolf

| | |
|---|---|
| SEQ. ID. NO. 29797 | 30-ProSerAsnAlaPro-34 |
| SEQ. ID. NO. 29798 | 37-ArgLeuAlaArgLysAlaValGln-44 |
| SEQ. ID. NO. 29799 | 55-LeuThrGluSerLysThrGlyAlaAsnArgSerSerSerSerCysLysPro-71 |
| SEQ. ID. NO. 29800 | 77-SerAlaSerAspSerSerArgIle-84 |
| SEQ. ID. NO. 29801 | 102-SerThrThrGlyAlaValThrLysSer-110 |

Hydrophilic Regions - Hopp-Woods

| | |
|---|---|
| SEQ. ID. NO. 29802 | 37-ArgLeuAlaArgLysAlaValGln-44 |
| SEQ. ID. NO. 29803 | 55-LeuThrGluSerLysThrGlyAlaAsnArgSerSerSerSerCysLys-70 |
| SEQ. ID. NO. 29804 | 78-AlaSerAspSerSerArgIle-84 | g244-1
AMPHI Regions - AMPHI

| | |
|---|---|
| SEQ. ID. NO. 29805 | 13-IleAlaAlaLeuLeuArg-18 |
| SEQ. ID. NO. 29806 | 24-AsnAlaLeuGlnGluIleAsnGlnIleProGlnThr-36 |
| SEQ. ID. NO. 29807 | 76-ArgLeuHisArgLeu-80 |

TABLE 1-continued

| | |
|---|---|
| SEQ. ID. NO. 29808 | 98-LeuArgGlyIleLysArgLeuLeuGlnLeuIleGlnSerHisLeuHisThrHis-115 |
| SEQ. ID. NO. 29809 | 150-ArgIleGlyAsnPhe-154 |
| SEQ. ID. NO. 29810 | 206-CysLeuAspGlyPheHisArgLeuHis-214 |
| SEQ. ID. NO. 29811 | 217-AsnArgPhePheThr-221 |
| SEQ. ID. NO. 29812 | 249-IleArgThrPheSerArgAsnPheLysGln-258 |

Antigenic Index - Jameson-Wolf

| | |
|---|---|
| SEQ. ID. NO. 29813 | 1-MetProProGluAlaArgProAlaGlySerAspGly-12 |
| SEQ. ID. NO. 29814 | 20-ValTyrThrGlnAsnAla-25 |
| SEQ. ID. NO. 29815 | 35-GlnThrProSerGly-39 |
| SEQ. ID. NO. 29816 | 43-CysHisArgAsnHisSerArgAlaGlnHis-52 |
| SEQ. ID. NO. 29817 | 81-MetAspIleArgIle-85 |
| SEQ. ID. NO. 29818 | 91-PheArgIleAspPheLeuAsp-97 |
| SEQ. ID. NO. 29819 | 99-ArgGlyIleLysArg-103 |
| SEQ. ID. NO. 29820 | 125-IleGlnLysArgHis-129 |
| SEQ. ID. NO. 29821 | 134-LeuAspArgGlnHisPheHisGlyLysLeuLeuSerGlyGluLeuValArg-150 |
| SEQ. ID. NO. 29822 | 178-PheGlnLeuGlyAsnProArgLeu-185 |
| SEQ. ID. NO. 29823 | 191-ArgLeuGlyGlySer-195 |
| SEQ. ID. NO. 29824 | 234-LeuLysThrAsnTrpLysSerLysSerGlyTyrTyrProSerLysIleArgThrPheSerArgAsnPheLysGlnArgGlnGluIleSerHisProProProAsnThrLeuProGlnLysProTyrLysArg-277 |

Hydrophilic Regions - Hopp-Woods

| | |
|---|---|
| SEQ. ID. NO. 29825 | 1-MetProProGluAlaArgProAlaGlySerAspGly-12 |
| SEQ. ID. NO. 29826 | 45-ArgAsnHisSerArgAlaGlnHis-52 |
| SEQ. ID. NO. 29827 | 81-MetAspIleArgIle-85 |
| SEQ. ID. NO. 29828 | 91-PheArgIleAspPheLeuAsp-97 |
| SEQ. ID. NO. 29829 | 99-ArgGlyIleLysArg-103 |
| SEQ. ID. NO. 29830 | 236-ThrAsnTrpLysSerLysSer-242 |
| SEQ. ID. NO. 29831 | 248-LysIleArgThrPheSerArgAsnPheLysGlnArgGlnGluIleSerHis-264 |
| SEQ. ID. NO. 29832 | 273-LysProTyrLysArg-277 | g246
AMPHI Regions - AMPHI

| | |
|---|---|
| SEQ. ID. NO. 29833 | 39-AlaValAsnIleAla-43 |
| SEQ. ID. NO. 29834 | 55-HisValValCysLysArgCysAlaGluValLeuValGluGlnPheAlaAspLeuPhePhe-74 |
| SEQ. ID. NO. 29835 | 83-AspMetGlyArgPhe-87 |
| SEQ. ID. NO. 29836 | 132-PheGlyCysAspAspValValAspAsnLeuAlaGlyPheGlyArgGlyPheArgPro-150 |

Antigenic Index - Jameson-Wolf

| | |
|---|---|
| SEQ. ID. NO. 29837 | 1-MetTyrGlyArgAsnGlySerThrGln-9 |
| SEQ. ID. NO. 29838 | 17-AspGlnThrGlnArgAlaArgPheGlyAsnGlyGluVal-29 |
| SEQ. ID. NO. 29839 | 46-PheAlaGlyGluSerGlyGln-52 |
| SEQ. ID. NO. 29840 | 57-ValCysLysArgCysAla-62 |
| SEQ. ID. NO. 29841 | 78-AspCysGlyHisHisAspMetGlyArg-86 |
| SEQ. ID. NO. 29842 | 92-LeuAspAspLysLeuAla-97 |
| SEQ. ID. NO. 29843 | 133-GlyCysAspAspValValAsp-139 |
| SEQ. ID. NO. 29844 | 143-GlyPheGlyArgGlyPheArgProVal-151 |
| SEQ. ID. NO. 29845 | 165-LeuGlnGlnArgGly-169 |

Hydrophilic Regions - Hopp-Woods

| | |
|---|---|
| SEQ. ID. NO. 29846 | 18-GlnThrGlnArgAlaArgPheGlyAsn-26 |
| SEQ. ID. NO. 29847 | 47-AlaGlyGluSerGly-51 |
| SEQ. ID. NO. 29848 | 57-ValCysLysArgCysAla-62 |
| SEQ. ID. NO. 29849 | 92-LeuAspAspLysLeuAla-97 | g247-1
AMPHI Regions - AMPHI

| | |
|---|---|
| SEQ. ID. NO. 29850 | 34-GlyPheIleGlnArgLeu-39 |
| SEQ. ID. NO. 29851 | 59-ValValSerSerCysSerLysIleAlaLysProGlyLysLysIleSerThrLeuGlnGlu-78 |
| SEQ. ID. NO. 29852 | 105-TyrAlaValGlyArgPheGlyAsn-112 |
| SEQ. ID. NO. 29853 | 164-ArgTyrThrAsnLysPheAspLysSerLys-173 |

Antigenic Index - Jameson-Wolf

| | |
|---|---|
| SEQ. ID. NO. 29854 | 1-ProGlyAlaLysGlnGluAsnProLeuPheSerLeuLysArgSerGlyMetAspLysGlnLeu-21 |
| SEQ. ID. NO. 29855 | 26-GluSerIleAspIleLysTyr-32 |
| SEQ. ID. NO. 29856 | 48-IleAspAspLeuAspAlaSerAla-55 |
| SEQ. ID. NO. 29857 | 62-SerCysSerLysIleAlaLysProGlyLysLysIleSerThrLeuGlnGluAlaLysSer-81 |
| SEQ. ID. NO. 29858 | 85-IleThrAsnAspAspLysGlnAsnGlyAsnIleThrArgGlnLysHis-100 |
| SEQ. ID. NO. 29859 | 109-ArgPheGlyAsnAsnGluGluSerLeu-117 |
| SEQ. ID. NO. 29860 | 120-PheGlnLeuAspAspLysGlyLysTrpGlyAsn-130 |
| SEQ. ID. NO. 29861 | 136-LysLysValLysArgMetAspVal-143 |
| SEQ. ID. NO. 29862 | 149-SerGlyCysProGluAspGluAspAlaGlyLysGluGluLysPheArgTyrThrAsnLysPheAspLysSerLysAsnAlaValThr-177 |
| SEQ. ID. NO. 29863 | 193-IleAlaAlaSerSerAspAsnSer-200 |
| SEQ. ID. NO. 29864 | 210-IleArgGlyGlyAsnValCysAlaAsnArgThrLeu-221 |

Hydrophilic Regions - Hopp-Woods

| | |
|---|---|
| SEQ. ID. NO. 29865 | 1-ProGlyAlaLysGlnGluAsn-7 |
| SEQ. ID. NO. 29866 | 11-SerLeuLysArgSerGlyMetAspLysGlnLeu-21 |
| SEQ. ID. NO. 29867 | 26-GluSerIleAspIleLys-31 |
| SEQ. ID. NO. 29868 | 48-IleAspAspLeuAspAlaSerAla-55 |
| SEQ. ID. NO. 29869 | 64-SerLysIleAlaLysProGlyLysLysIleSerThr-75 |
| SEQ. ID. NO. 29870 | 77-GlnGluAlaLysSer-81 |
| SEQ. ID. NO. 29871 | 86-ThrAsnAspAspLysGlnAsnGlyAsnIleThrArgGlnLysHis-100 |
| SEQ. ID. NO. 29872 | 111-GlyAsnAsnGluGluSerLeu-117 |
| SEQ. ID. NO. 29873 | 121-GlnLeuAspAspLysGlyLysTrpGly-129 |
| SEQ. ID. NO. 29874 | 136-LysLysValLysArgMetAspVal-143 |
| SEQ. ID. NO. 29875 | 151-CysProGluAspGluAspAlaGlyLysGluGluLysPheArgTyr-165 |
| SEQ. ID. NO. 29876 | 167-AsnLysPheAspLysSerLysAsnAlaVal-176 |

TABLE 1-continued

SEQ. ID. NO. 29877    193-IleAlaAlaSerSerAspAsn-199
g248-1
AMPHI Regions - AMPHI
SEQ. ID. NO. 29878    87-SerGluAsnCysGluLysGlyLeu-94
SEQ. ID. NO. 29879    109-GluAlaPheGlyAsn-113
SEQ. ID. NO. 29880    122-ValGluAlaValLysArg-127
SEQ. ID. NO. 29881    153-AlaAlaGlyValSerLysMetProArgTyrIleIleGlu-165
SEQ. ID. NO. 29882    173-GlnAsnValTyrArgValThrAlaLysAlaTrpGlyLysAsn-186
Antigenic Index - Jameson-Wolf
SEQ. ID. NO. 29883    1-MetArgLysGlnAsnThrLeuThr-8
SEQ. ID. NO. 29884    11-ProThrSerAspGlyGlnArgGlySer-19
SEQ. ID. NO. 29885    40-GlnSerTyrAsnThrGluGlnArgIleSerAlaAsnGluSerAspArgLysLeuAla-58
SEQ. ID. NO. 29886    64-AlaAlaLeuArgGluGlyGluPheGln-72
SEQ. ID. NO. 29887    78-TyrAlaAlaAspSerLysValThrPheSerGluAsnCysGluLysGlyLeu-94
SEQ. ID. NO. 29888    101-ArgThrAsnAsnAsnGlySerGluGluAlaPhe-111
SEQ. ID. NO. 29889    118-GlyLysProAlaValGluAlaValLysArgSerCysProAlaLysSerGlyLysAsnSerThr-138
SEQ. ID. NO. 29890    140-LeuCysIleAspAsnLysGlyMetGluTyrAsnLysGlyAlaAlaGlyValSerLysMetProArgTyrIle-163
SEQ. ID. NO. 29891    168-GlyValLysAsnGlyGlnAsnVal-175
SEQ. ID. NO. 29892    182-AlaTrpGlyLysAsnAlaAsnThr-189
SEQ. ID. NO. 29893    197-ValGlyAsnAsnAspGluGln-203
Hydrophilic Regions - Hopp-Woods
SEQ. ID. NO. 29894    1-MetArgLysGlnAsnThr-6
SEQ. ID. NO. 29895    11-ProThrSerAspGlyGlnArgGly-18
SEQ. ID. NO. 29896    42-TyrAsnThrGluGlnArgIleSerAlaAsnGluSerAspArgLysLeuAla-58
SEQ. ID. NO. 29897    64-AlaAlaLeuArgGluGlyGluPheGln-72
SEQ. ID. NO. 29898    78-TyrAlaAlaAspSerLysValThrPhe-86
SEQ. ID. NO. 29899    88-GluAsnCysGluLysGlyLeu-94
SEQ. ID. NO. 29900    101-ArgThrAsnAsnAsnGlySerGluGluAlaPhe-111
SEQ. ID. NO. 29901    120-ProAlaValGluAlaValLysArgSerCysProAlaLysSerGlyLysAsnSerThr-138
SEQ. ID. NO. 29902    140-LeuCysIleAspAsnLysGlyMetGluTyrAsnLys-151
SEQ. ID. NO. 29903    199-AsnAsnAspGluGln-203
g249-1
AMPHI Regions - AMPHI
SEQ. ID. NO. 29904    6-CysLeuArgLeuLys-10
SEQ. ID. NO. 29905    15-GlyMetAlaLeuIleGluValLeuVal-23
SEQ. ID. NO. 29906    42-ThrValAlaSerValArgGluAla-49
SEQ. ID. NO. 29907    53-ThrIleValSerGlnIleThrGlnAsnLeuMetGluGlyMet-66
SEQ. ID. NO. 29908    111-GluGlnLeuLysArgPheSerHisGluLeuLysAsnAlaLeu-124
Antigenic Index - Jameson-Wolf
SEQ. ID. NO. 29909    1-MetLysAsnAsnAspCysLeuArgLeuLysAsnProGlnSerGly-15
SEQ. ID. NO. 29910    44-AlaSerValArgGluAlaGluThr-51
SEQ. ID. NO. 29911    70-ProThrIleAspLeuAspSerAsnLysLysAsnTyr-81
SEQ. ID. NO. 29912    85-MetGlyLysGlnThr-89
SEQ. ID. NO. 29913    93-ValAspGlyGluPhe-97
SEQ. ID. NO. 29914    99-LeuAspAlaGluLysSerLysAlaGlnLeuAlaGluGluGlnLeuLysArgPheSerHisGluLeuLysAsnAlaLeu-124
SEQ. ID. NO. 29915    134-ValCysLysAspSerSerGlyAspAlaProThrLeuSerAspSerGlyAlaPheSerSerAsnCysAspAsnLysAlaAsnGlyAspThrLeu-164
SEQ. ID. NO. 29916    172-AspSerAlaGlyAspSerAspIleSerArgThrAsnLeuGluValSerGlyAspAsn-190
SEQ. ID. NO. 29917    197-AlaArgValGlyGlyArgGlu-203
Hydrophilic Regions - Hopp-Woods
SEQ. ID. NO. 29918    1-MetLysAsnAsnAspCysLeuArgLeuLysAsnProGln-13
SEQ. ID. NO. 29919    44-AlaSerValArgGluAlaGluThr-51
SEQ. ID. NO. 29920    72-IleAspLeuAspSerAsnLysLysAsnTyr-81
SEQ. ID. NO. 29921    99-LeuAspAlaGluLysSerLysAlaGlnLeuAlaGluGluGlnLeuLysArgPheSerHisGluLeuLysAsnAlaLeu-124
SEQ. ID. NO. 29922    134-ValCysLysAspSerSerGlyAspAlaProThrLeuSerAsp-147
SEQ. ID. NO. 29923    154-AsnCysAspAsnLysAlaAsnGly-161
SEQ. ID. NO. 29924    173-SerAlaGlyAspSerAspIleSerArgThrAsnLeu-184
SEQ. ID. NO. 29925    199-ValGlyGlyArgGlu-203
g250
AMPHI Regions - AMPHI
SEQ. ID. NO. 29926    10-GluPheIleArgGlyIleLysGlu-17
SEQ. ID. NO. 29927    54-PheAlaGlyGlySerGlu-59
SEQ. ID. NO. 29928    61-AlaThrValAsnLeuTrpAlaGluPro-69
Antigenic Index - Jameson-Wolf
SEQ. ID. NO. 29929    3-HisThrAlaSerProArgAspGluPheIleArgGlyIleLysGluSerSerPro-20
SEQ. ID. NO. 29930    34-MetGlnGlyGlyGlnLysGlyMetGlyArgLeu-44
SEQ. ID. NO. 29931    54-PheAlaGlyGlySerGlu-59
SEQ. ID. NO. 29932    83-AsnSerArgHisIleLeuMetGlyGlyGly-92
SEQ. ID. NO. 29933    95-HisAlaHisGluArgAsnThrAlaGluLysSerArgAlaArg-108
Hydrophilic Regions - Hopp-Woods
SEQ. ID. NO. 29934    5-AlaSerProArgAspGluPheIleArgGlyIleLysGluSerSer-19
SEQ. ID. NO. 29935    36-GlyGlyGlnLysGlyMetGlyArg-43
SEQ. ID. NO. 29936    95-HisAlaHisGluArgAsnThrAlaGluLysSerArgAlaArg-108
g251
AMPHI Regions - AMPHI
SEQ. ID. NO. 29937    57-ValAlaAspPheGlyGlyIleGluGlyPhe-66
SEQ. ID. NO. 29938    101-ArgThrValGlyGlyThrValArgLeuLeuLysMetIle-113
SEQ. ID. NO. 29939    156-AlaArgThrValPheArgAlaHisLeuArg-165
SEQ. ID. NO. 29940    179-AlaAlaArgValPheAlaValAla-186
SEQ. ID. NO. 29941    200-LeuGlyGlnGluCysArg-205
SEQ. ID. NO. 29942    207-ArgHisIleAlaArgValGluSerLeuLeuArgAlaPheGluTyrAla-222

TABLE 1-continued

```
Antigenic Index - Jameson-Wolf
SEQ. ID. NO. 29943    21-LeuArgGlyArgPheGlnArg-27
SEQ. ID. NO. 29944    48-ValValThrGluValAspAla-54
SEQ. ID. NO. 29945    90-ArgLeuValGlyThr-94
SEQ. ID. NO. 29946    120-ProValValArgGluAlaGlyIle-127
SEQ. ID. NO. 29947    153-ValLysHisAlaArgThrValPhe-160
SEQ. ID. NO. 29948    196-IleLysAsnArgLeuGlyGlnGluCysArgAsnArgHisIleAlaArgValGluSerLeu-215
SEQ. ID. NO. 29949    231-LysThrLysThrArgAlaGluGlnProArgProAla-242
Hydrophilic Regions - Hopp-Woods
SEQ. ID. NO. 29950    23-GlyArgPheGlnArg-27
SEQ. ID. NO. 29951    48-ValValThrGluValAspAla-54
SEQ. ID. NO. 29952    120-ProValValArgGluAlaGlyIle-127
SEQ. ID. NO. 29953    153-ValLysHisAlaArgThrValPhe-160
SEQ. ID. NO. 29954    198-AsnArgLeuGlyGlnGluCysArgAsnArgHisIleAlaArgValGluSerLeu-215
SEQ. ID. NO. 29955    232-ThrLysThrArgAlaGluGlnProArg-240
g254
AMPHI Regions - AMPHI
SEQ. ID. NO. 29956    6-ArgPheAsnThrTyrSerHis-12
SEQ. ID. NO. 29957    32-GlyHisGlyAspGlyTyrArg-38
SEQ. ID. NO. 29958    66-LysLeuLysSerIleLeuLys-72
SEQ. ID. NO. 29959    142-ValLeuAlaValMetLysSerLeuThrAlaSer-152
Antigenic Index - Jameson-Wolf
SEQ. ID. NO. 29960    5-GluArgPheAsnThrTyrSer-11
SEQ. ID. NO. 29961    32-GlyHisGlyAspGlyTyrArg-38
SEQ. ID. NO. 29962    65-GlyLysLeuLysSerIleLeuLysLysThrAspHis-76
SEQ. ID. NO. 29963    94-SerLeuArgAsnGlyProGly-100
SEQ. ID. NO. 29964    120-ThrIleGlyArgLysSerGluLysArgLeuLeu-130
SEQ. ID. NO. 29965    177-AsnAspGluLysIleArgHisGlyHisGly-186
Hydrophilic Regions - Hopp-Woods
SEQ. ID. NO. 29966    65-GlyLysLeuLysSerIleLeuLysLysThrAspHis-76
SEQ. ID. NO. 29967    120-ThrIleGlyArgLysSerGluLysArgLeuLeu-130
SEQ. ID. NO. 29968    177-AsnAspGluLysIleArgHis-183
g255
AMPHI Regions - AMPHI
SEQ. ID. NO. 29969    23-ValLysThrCysAlaAspPheHisAlaPheAspGlyValAspAlaHisHisArg-40
SEQ. ID. NO. 29970    71-GlyIleGlnGlyPheAlaHis-77
Antigenic Index - Jameson-Wolf
SEQ. ID. NO. 29971    33-AspGlyValAspAlaHisHisArgValGlyAspPheGlyIleGluAlaValGluAsnGlyPheAlaGlnThrAspGlyAspValGlyGly-62
SEQ. ID. NO. 29972    67-PheArgAlaAspGlyIleGlnGly-74
SEQ. ID. NO. 29973    91-ValGlyGlyLysLysArgIleLeu-98
SEQ. ID. NO. 29974    115-GlyAsnValGlyGlyAspPheArgAla-123
SEQ. ID. NO. 29975    130-PhePheGlyAsnGlySerGlyGlyAsnAlaGly-140
SEQ. ID. NO. 29976    145-GlyGlyThrProAla-149
SEQ. ID. NO. 29977    168-SerGlyAlaGluGlyGlyGlyAspVal-176
Hydrophilic Regions - Hopp-Woods
SEQ. ID. NO. 29978    33-AspGlyValAspAlaHisHisArgValGlyAspPheGly-45
SEQ. ID. NO. 29979    56-ThrAspGlyAspValGlyGly-62
SEQ. ID. NO. 29980    67-PheArgAlaAspGly-71
SEQ. ID. NO. 29981    92-GlyGlyLysLysArgIleLeu-98
SEQ. ID. NO. 29982    119-GlyAspPheArgAla-123
SEQ. ID. NO. 29983    169-GlyAlaGluGlyGlyGly-174
g256-1
AMPHI Regions - AMPHI
SEQ. ID. NO. 29984    22-AlaLysPheLeuGlnHisPro-28
SEQ. ID. NO. 29985    95-HisPheArgSerCysGlyGlyValAla-103
SEQ. ID. NO. 29986    128-ArgTyrArgGluIleTyrAlaVal-135
SEQ. ID. NO. 29987    143-AlaProAlaLysTyrLeuGlyGluGln-151
SEQ. ID. NO. 29988    179-GlyIleThrArgLeuLeu-184
SEQ. ID. NO. 29989    198-ArgSerLeuGlnGlyPheGlnThrAla-206
SEQ. ID. NO. 29990    208-AlaAlaGlyCysLysThrLeuGlyGluPheAspAspArgPheThrAlaProLeuHisGly-227
SEQ. ID. NO. 29991    234-TyrTyrArgGlnThrSerCysLysProLeuLeuLysHisValAla-248
Antigenic Index - Jameson-Wolf
SEQ. ID. NO. 29992    4-ThrProProAspThrProPhe-10
SEQ. ID. NO. 29993    12-LeuArgAsnGlyAsnAlaAspThrIleAla-21
SEQ. ID. NO. 29994    27-HisProAlaProAlaTyrArgArgGluMetLeuProAspSerThrGlyLysThrLysThrAlaTyr-48
SEQ. ID. NO. 29995    51-SerAlaGlyGlyIleSerProAspAlaPro-60
SEQ. ID. NO. 29996    68-LeuGluGlySerSerArgSerHisTyr-76
SEQ. ID. NO. 29997    84-ValArgAsnArgGlyTrpHis-90
SEQ. ID. NO. 29998    98-SerCysGlyGlyValAlaAsn-104
SEQ. ID. NO. 29999    113-GlyAspThrAlaGlu-117
SEQ. ID. NO. 30000    125-LeuThrAlaArgTyrArgGlu-131
SEQ. ID. NO. 30001    140-GlyGlyAsnAlaProAlaLysTyrLeuGlyGluGlnGlyLysLysAlaLeuPro-157
SEQ. ID. NO. 30002    167-ValAspAlaGluAlaAlaGlySerArgPheAspSerGlyIle-180
SEQ. ID. NO. 30003    193-LeuIleProLysAlaArgSerLeuGln-201
SEQ. ID. NO. 30004    213-ThrLeuGlyGluPheAspAspArgPheThr-222
SEQ. ID. NO. 30005    228-PheAlaAspArgHisAspTyrTyrArgGlnThrSerCysLysProLeuLeu-244
SEQ. ID. NO. 30006    259-AspProPheLeuProProGluAlaLeuProArgAlaAspGluAlaSerGlu-275
SEQ. ID. NO. 30007    283-AlaHisGlyGlyHis-287
SEQ. ID. NO. 30008    292-SerSerThrGlyGlyArgLeu-298
SEQ. ID. NO. 30009    312-AspSerPheArgThrAsnArgArg-319
```

TABLE 1-continued

Hydrophilic Regions - Hopp-Woods
SEQ. ID. NO. 30010    31-AlaTyrArgArgGluMetLeuPro-38
SEQ. ID. NO. 30011    40-SerThrGlyLysThrLysThr-46
SEQ. ID. NO. 30012    69-GluGlySerSerArgSer-74
SEQ. ID. NO. 30013    84-ValArgAsnArgGly-88
SEQ. ID. NO. 30014    125-LeuThrAlaArgTyrArgGlu-131
SEQ. ID. NO. 30015    147-TyrLeuGlyGluGlnGlyLysLysAlaLeuPro-157
SEQ. ID. NO. 30016    167-ValAspAlaGluAlaAlaGlySerArgPheAspSerGlyIle-180
SEQ. ID. NO. 30017    193-LeuIleProLysAlaArgSer-199
SEQ. ID. NO. 30018    213-ThrLeuGlyGluPheAspAspArgPheThr-222
SEQ. ID. NO. 30019    228-PheAlaAspArgHisAspTyrTyrArg-236
SEQ. ID. NO. 30020    266-AlaLeuProArgAlaAspGluAlaSerGlu-275
SEQ. ID. NO. 30021    314-PheArgThrAsnArgArg-319
g257
AMPHI Regions - AMPHI
SEQ. ID. NO. 30022    24-SerPheLeuProAsn-28
SEQ. ID. NO. 30023    73-AspLeuValAsnLysValLeuAlaGluValAlaArgLeuGluLysMetPhe-89
SEQ. ID. NO. 30024    109-SerProProAlaAspPheLeuGluLeuLeuSerLeuAlaAlaIlePheThr-125
Antigenic Index - Jameson-Wolf
SEQ. ID. NO. 30025    1-MetGlyArgHisPheGlyArgArgArgPheLeu-11
SEQ. ID. NO. 30026    32-AlaGlyGlyGluLysArgAsnMetAspLysLysArgAspGluAsn-46
SEQ. ID. NO. 30027    56-GlySerGlyAlaGlu-60
SEQ. ID. NO. 30028    65-GlyValAspAspArgGlnAlaAla-72
SEQ. ID. NO. 30029    83-AlaArgLeuGluLys-87
SEQ. ID. NO. 30030    92-TyrArgGluAspSerLeuIleSerArgLeuAsnArgAspGlyTyrLeuThrSerProProAlaAspPhe-114
Hydrophilic Regions - Hopp-Woods
SEQ. ID. NO. 30031    4-HisPheGlyArgArgArgPheLeu-11
SEQ. ID. NO. 30032    33-GlyGlyGluLysArgAsnMetAspLysLysArgAspGluAsn-46
SEQ. ID. NO. 30033    65-GlyValAspAspArgGlnAlaAla-72
SEQ. ID. NO. 30034    83-AlaArgLeuGluLys-87
SEQ. ID. NO. 30035    92-TyrArgGluAspSerLeuIle-98
SEQ. ID. NO. 30036    100-ArgLeuAsnArgAspGlyTyr-106
g259-1
Antigenic Index - Jameson-Wolf
SEQ. ID. NO. 30037    34-LysAlaTyrThrGluGluLeuProPro-42
SEQ. ID. NO. 30038    62-ValArgSerLysAlaLysAlaGluLysPheTyrArgGluLysMetIleGln-78
SEQ. ID. NO. 30039    93-LeuGluHisLysPro-97
SEQ. ID. NO. 30040    105-LysAsnHisGlyLysGlyMetAlaGluGlnValArgPheLysAla-119
SEQ. ID. NO. 30041    121-ValLeuProAspAspGluAspAlaArgThrIleAla-132
SEQ. ID. NO. 30042    144-GlyThrAspAlaValAlaAlaSerGlyGluThrTyrGlyArgVal-157
Hydrophilic Regions - Hopp-Woods
SEQ. ID. NO. 30043    35-AlaTyrThrGluGluLeuPro-41
SEQ. ID. NO. 30044    62-ValArgSerLysAlaLysAlaGluLysPheTyrArgGluLysMetIleGln-78
SEQ. ID. NO. 30045    93-LeuGluHisLysPro-97
SEQ. ID. NO. 30046    106-AsnHisGlyLysGlyMetAlaGluGlnValArgPheLysAla-119
SEQ. ID. NO. 30047    121-ValLeuProAspAspGluAspAlaArgThrIleAla-132
g260
AMPHI Regions - AMPHI
SEQ. ID. NO. 30048    12-ProPhePheSerLeuPheArgAlaLeuPheGlu-22
SEQ. ID. NO. 30049    53-PheIleAspSerValGlyGlnIleThrAlaArgPhePheGlnAlaPhe-68
SEQ. ID. NO. 30050    151-GlnTyrLeuAlaArgIleAsnGlnValGlyIleValAspLeuIleProValArg-168
SEQ. ID. NO. 30051    177-ThrGlyCysThrGlyIleCysProLysTyrProThrGlyCysArgPro-192
Antigenic Index - Jameson-Wolf
SEQ. ID. NO. 30052    30-GlyAlaHisAspAlaAlaGlu-36
SEQ. ID. NO. 30053    80-ProAlaPheArgAlaArgGluGlnAlaArgArgGlySerGly-93
SEQ. ID. NO. 30054    97-GlyAsnAspLeuArgValLeuHisLysAspAlaValGluValAspIleAspGlyGlyAsnThrVal-118
SEQ. ID. NO. 30055    126-ThrAspPheAspAspGlyAspAla-133
SEQ. ID. NO. 30056    139-AlaGluAlaArgPhe-143
SEQ. ID. NO. 30057    166-ProValArgAlaProGlnGlyGlyThrIle-175
SEQ. ID. NO. 30058    183-CysProLysTyrProThrGlyCysArgProVal-193
Hydrophilic Regions - Hopp-Woods
SEQ. ID. NO. 30059    30-GlyAlaHisAspAlaAlaGlu-36
SEQ. ID. NO. 30060    82-PheArgAlaArgGluGlnAlaArgArgGlySer-92
SEQ. ID. NO. 30061    98-AsnAspLeuArgValLeuHisLysAspAlaValGluValAspIleAspGly-114
SEQ. ID. NO. 30062    126-ThrAspPheAspAspGlyAspAla-133
SEQ. ID. NO. 30063    139-AlaGluAlaArgPhe-143
g261
AMPHI Regions - AMPHI
SEQ. ID. NO. 30064    19-PheThrPheGlnThr-23
SEQ. ID. NO. 30065    32-AspThrAlaArgAlaPheAlaAlaAla-40
SEQ. ID. NO. 30066    50-GlyLeuPheAlaAspVal-55
SEQ. ID. NO. 30067    138-ValHisLysGlyIleGlyAsnAlaValValGlyGlyPheAsp-151
SEQ. ID. NO. 30068    164-GlyValValArgAsnLeu-169
SEQ. ID. NO. 30069    203-GluGlyAspGlyLeuAspValPheAlaProVal-213
SEQ. ID. NO. 30070    217-CysLeuAsnGlnAlaGlyGly-223
Antigenic Index - Jameson-Wolf
SEQ. ID. NO. 30071    13-AlaArgSerAspGly-17
SEQ. ID. NO. 30072    23-ThrPheArgGlnProAla-28
SEQ. ID. NO. 30073    40-AlaAlaAspAspThrLeu-45
SEQ. ID. NO. 30074    62-ValArgGlnArgProArgLeuArgLeu-70

TABLE 1-continued

| | |
|---|---|
| SEQ. ID. NO. 30075 | 74-HisGlnArgArgValAspLeu-80 |
| SEQ. ID. NO. 30076 | 86-ArgGlnIleLysGlyAsnValHisGlyPheAspGluHisAla-99 |
| SEQ. ID. NO. 30077 | 111-AlaHisAlaArgAspAspValProAsp-119 |
| SEQ. ID. NO. 30078 | 122-ProPheGlyLysAsnGlyGlyValLysGlnGluLysArgValThrProVal-138 |
| SEQ. ID. NO. 30079 | 149-GlyPheAspGlyGlyGlyPheAspGlyGlyGly-159 |
| SEQ. ID. NO. 30080 | 183-GlnIleLeuArgAspProLeuCysAla-191 |
| SEQ. ID. NO. 30081 | 201-ValSerGluGlyAspGlyLeuAsp-208 |
| SEQ. ID. NO. 30082 | 219-AsnGlnAlaGlyGlyArgIleLeuThrAlaArgGluAspAspGlnGlyPhe-235 |
| Hydrophilic Regions - Hopp-Woods | |
| SEQ. ID. NO. 30083 | 13-AlaArgSerAspGly-17 |
| SEQ. ID. NO. 30084 | 40-AlaAlaAspAspThrLeu-45 |
| SEQ. ID. NO. 30085 | 62-ValArgGlnArgProArgLeuArgLeu-70 |
| SEQ. ID. NO. 30086 | 74-HisGlnArgArgValAspLeu-80 |
| SEQ. ID. NO. 30087 | 94-GlyPheAspGluHisAla-99 |
| SEQ. ID. NO. 30088 | 112-HisAlaArgAspAspValProAsp-119 |
| SEQ. ID. NO. 30089 | 127-GlyGlyValLysGlnGluLysArgValThrPro-137 |
| SEQ. ID. NO. 30090 | 202-SerGluGlyAspGlyLeu-207 |
| SEQ. ID. NO. 30091 | 226-LeuThrAlaArgGluAspAspGlnGly-234 |
| g263 | |
| AMPHI Regions - AMPHI | |
| SEQ. ID. NO. 30092 | 32-AsnLeuIleGlyValLeuAlaAsnAla-40 |
| SEQ. ID. NO. 30093 | 42-GluAlaLeuAlaPheTyrGlnGluValGlyLysLeuAsnAlaAlaAsnSerLeuThr-60 |
| SEQ. ID. NO. 30094 | 65-GluValIleArgIle-69 |
| SEQ. ID. NO. 30095 | 86-LysLeuAlaThrLeuLysLys-92 |
| SEQ. ID. NO. 30096 | 100-AsnAlaAlaArgAlaLeu-105 |
| SEQ. ID. NO. 30097 | 115-LeuGlyAlaLeuAlaAlaPheThrGln-123 |
| SEQ. ID. NO. 30098 | 137-LeuAsnAlaPheLeuGluAla-143 |
| SEQ. ID. NO. 30099 | 157-ValAlaLeuAlaThrLeuCysAsnTyrAlaAsnAsnLeuAla-170 |
| Antigenic Index - Jameson-Wolf | |
| SEQ. ID. NO. 30100 | 10-GluThrAlaProGluAlaAlaLysProArgValGluAlaValProLysAsnAsnGlyPhe-29 |
| SEQ. ID. NO. 30101 | 62-GlyGluValGluVal-66 |
| SEQ. ID. NO. 30102 | 73-ArgThrAsnGlnCysSer-78 |
| SEQ. ID. NO. 30103 | 97-GlnSerLeuAsnAla-101 |
| SEQ. ID. NO. 30104 | 108-GlyLysSerAspAspAlaLysLeu-115 |
| SEQ. ID. NO. 30105 | 126-MetAlaLysLysGlyAlaValSerAspAspGluLeu-137 |
| SEQ. ID. NO. 30106 | 144-GlyTyrAsnArgGlnGlnAla-150 |
| SEQ. ID. NO. 30107 | 172-ThrGluIleAsnProLysLeu-178 |
| Hydrophilic Regions - Hopp-Woods | |
| SEQ. ID. NO. 30108 | 11-ThrAlaProGluAlaAlaLysProArgValGluAlaValProLys-25 |
| SEQ. ID. NO. 30109 | 62-GlyGluValGluVal-66 |
| SEQ. ID. NO. 30110 | 97-GlnSerLeuAsnAla-101 |
| SEQ. ID. NO. 30111 | 108-GlyLysSerAspAspAlaLysLeu-115 |
| SEQ. ID. NO. 30112 | 126-MetAlaLysLysGlyAlaValSerAspAspGluLeu-137 |
| g264 | |
| AMPHI Regions - AMPHI | |
| SEQ. ID. NO. 30113 | 28-ValValLysProGluLys-33 |
| SEQ. ID. NO. 30114 | 40-ArgSerTyrLysValAlaGluPheThrGlnThrGly-51 |
| SEQ. ID. NO. 30115 | 85-IleProSerHisValArgVal-91 |
| SEQ. ID. NO. 30116 | 113-AsnArgIleIleAspValSer-119 |
| SEQ. ID. NO. 30117 | 172-LeuAsnGlnAlaAlaGlnAsnPhe-179 |
| Antigenic Index - Jameson-Wolf | |
| SEQ. ID. NO. 30118 | 27-AlaValValLysProGluLysLeuHisAlaSerAlaAsnArgSerTyrLys-43 |
| SEQ. ID. NO. 30119 | 48-ThrGlnThrGlyAsnAlaSerTrp-55 |
| SEQ. ID. NO. 30120 | 57-GlyGlyArgPheHisGlyArgLysThrSerGlyGlyAspArgTyrAsp-72 |
| SEQ. ID. NO. 30121 | 91-ValThrAsnThrLysAsnGlyLysSerVal-100 |
| SEQ. ID. NO. 30122 | 103-ArgValAsnAspArgGlyProPheHisGlyAsnArgIleIleAspValSerLysAlaAlaAla-123 |
| SEQ. ID. NO. 30123 | 142-ValProGlyGlnSerAlaProValAlaGluAsnLysAspIlePheIle-157 |
| SEQ. ID. NO. 30124 | 159-LeuLysSerPheGlyThrGluHisGluAla-168 |
| SEQ. ID. NO. 30125 | 181-AlaSerSerSerSerProAsnLeuSerValGluLysArgArgTyrGluTyr-197 |
| SEQ. ID. NO. 30126 | 205-AlaSerGlnGluArgAlaAlaGluAlaGluAlaGlnAla-217 |
| Hydrophilic Regions - Hopp-Woods | |
| SEQ. ID. NO. 30127 | 27-AlaValValLysProGluLysLeuHisAlaSerAlaAsnArgSerTyrLys-43 |
| SEQ. ID. NO. 30128 | 60-PheHisGlyArgLysThrSerGlyGlyAspArgTyrAsp-72 |
| SEQ. ID. NO. 30129 | 92-ThrAsnThrLysAsnGlyLys-98 |
| SEQ. ID. NO. 30130 | 104-ValAsnAspArgGlyProPheHis-111 |
| SEQ. ID. NO. 30131 | 114-ArgIleIleAspValSerLysAlaAlaAla-123 |
| SEQ. ID. NO. 30132 | 148-ProValAlaGluAsnLysAspIlePheIle-157 |
| SEQ. ID. NO. 30133 | 160-LysSerPheGlyThrGluHisGluAla-168 |
| SEQ. ID. NO. 30134 | 188-LeuSerValGluLysArgArgTyrGluTyr-197 |
| SEQ. ID. NO. 30135 | 205-AlaSerGlnGluArgAlaAlaGluAlaGluAlaGlnAla-217 |
| g266 | |
| Antigenic Index - Jameson-Wolf | |
| SEQ. ID. NO. 30136 | 2-GlnPheArgArgHisArgArgArgGlnCysProAsnArgLysProIle-17 |
| SEQ. ID. NO. 30137 | 47-AlaLeuLysArgLysHisPhe-53 |
| SEQ. ID. NO. 30138 | 76-SerArgAlaGlyAla-80 |
| SEQ. ID. NO. 30139 | 110-TrpHisThrArgAsnArgGlu-116 |
| Hydrophilic Regions - Hopp-Woods | |
| SEQ. ID. NO. 30140 | 2-GlnPheArgArgHisArgArgArgGlnCysProAsnArgLysProIle-17 |
| SEQ. ID. NO. 30141 | 47-AlaLeuLysArgLysHisPhe-53 |
| SEQ. ID. NO. 30142 | 76-SerArgAlaGlyAla-80 |

TABLE 1-continued g268-1
AMPHI Regions - AMPHI
SEQ. ID. NO. 30143 42-GluIleLeuValLysLeuValArg-49
SEQ. ID. NO. 30144 57-ValLysThrPheAspAsp-62
SEQ. ID. NO. 30145 77-HisIleArgArgMetValGluArg-84
SEQ. ID. NO. 30146 92-ValArgThrThrGluLysThr-98
SEQ. ID. NO. 30147 129-IleGlyAsnSerHisLys-134
SEQ. ID. NO. 30148 136-ThrProAspPhePheGlnProTyr-143
SEQ. ID. NO. 30149 169-PheAlaGluLeuSerGlnAlaHisAspIleIleHisProLeuSerGluLeuValSerMet-188
SEQ. ID. NO. 30150 191-IleLysGluProLeuAspLys-197
SEQ. ID. NO. 30151 215-AlaArgGluAlaGluGluAlaAla-222
SEQ. ID. NO. 30152 231-GlnGluAlaAlaArgValSerGluTrp-239
SEQ. ID. NO. 30153 249-GluPheGluGlnPheTrpLysGlyLeuProGlnThrValGlnAsn-263
SEQ. ID. NO. 30154 268-SerGlnLysThrTrpLysSerGlyMetAspLys-278
SEQ. ID. NO. 30155 289-GluThrProAsnGlyIleLys-295
Antigenic Index - Jameson-Wolf
SEQ. ID. NO. 30156 1-MetLysLysAsnLeu-5
SEQ. ID. NO. 30157 16-LeuSerGlyCysAspArgLeuGlyIleGlyAsnProPheSerGlyLysGluIleSerCysGlySerGluGluThrLysGluIleLeu-44
SEQ. ID. NO. 30158 47-LeuValArgAspAsnValGluGlyGluThrValLysThrPheAspAspAspAlaPheLysAspGlnAlaPhe-70
SEQ. ID. NO. 30159 77-HisIleArgArgMetValGlu-83
SEQ. ID. NO. 30160 85-LeuGlyIleThrValAspGluValArgThrThrGluLysThrAspThrSerSerLysLeuLysCysGluAlaAlaLeu-110
SEQ. ID. NO. 30161 112-LeuAspValProAspAspValVal-119
SEQ. ID. NO. 30162 127-GlnSerIleGlyAsnSerHisLysLysThrProAspPhePhe-140
SEQ. ID. NO. 30163 143-TyrTyrArgLysGluGlyAlaTyr-150
SEQ. ID. NO. 30164 158-SerValGlnProThrAspAspLysSerLysIle-168
SEQ. ID. NO. 30165 190-LeuIleLysGluProLeuAspLysAlaLysGlnArgAsnGluLysLeuGluAlaAlaGluAlaThrAlaGlnGluAlaArgGluAlaGluGlu
AlaAlaAla-223
SEQ. ID. NO. 30166 226-AlaLeuGlyArgGluGlnGluAlaAlaArgValSerGluTrpGluGluArgTyrLysLeuSerArgSerGluPhe-250
SEQ. ID. NO. 30167 261-ValGlnAsnLysLeuGlnAlaSerGlnLysThrTrpLysSerGlyMetAspLysIleCysAlaAsnAsnAlaLysAlaGluGlyGluThrPro
AsnGlyIleLysValSerGluLeuAlaCysLysThrAlaGluThrGluAlaArgLeuGluGluLeuHisAsnArgLysLysAlaLeuIle-321
SEQ. ID. NO. 30168 323-GluMetValArgGluGluAspLysLysGluLeuProLysArgLeu-337
Hydrophilic Regions - Hopp-Woods
SEQ. ID. NO. 30169 1-MetLysLysAsnLeu-5
SEQ. ID. NO. 30170 18-GlyCysAspArgLeuGly-23
SEQ. ID. NO. 30171 28-PheSerGlyLysGluIleSerCysGlySerGluGluThrLysGluIleLeu-44
SEQ. ID. NO. 30172 47-LeuValArgAspAsnValGluGlyGluThrValLysThrPheAspAspAspAlaPheLysAspGlnAlaPhe-70
SEQ. ID. NO. 30173 77-HisIleArgArgMetValGlu-83
SEQ. ID. NO. 30174 85-LeuGlyIleThrValAspGluValArgThrThrGluLysThrAspThrSerSerLysLeuLysCysGluAlaAlaLeu-110
SEQ. ID. NO. 30175 112-LeuAspValProAspAspValVal-119
SEQ. ID. NO. 30176 131-AsnSerHisLysLysThrProAspPhe-139
SEQ. ID. NO. 30177 143-TyrTyrArgLysGluGly-148
SEQ. ID. NO. 30178 161-ProThrAspAspLysSerLysIle-168
SEQ. ID. NO. 30179 190-LeuIleLysGluProLeuAspLysAlaLysGlnArgAsnGluLysLeuGluAlaAlaGluAlaThrAlaGlnGluAlaArgGluAlaGluGluAla
AlaAla-223
SEQ. ID. NO. 30180 226-AlaLeuGlyArgGluGlnGluAlaAlaArgValSerGluTrpGluGluArgTyrLysLeuSerArgSerGluPhe-250
SEQ. ID. NO. 30181 270-LysThrTrpLysSerGlyMetAspLysIleCys-280
SEQ. ID. NO. 30182 283-AsnAlaLysAlaGluGlyGluThrProAsn-292
SEQ. ID. NO. 30183 294-IleLysValSerGluLeuAlaCysLysThrAlaGluThrGluAlaArgLeuGluGluLeuHisAsnArgLysLysAlaLeuIle-321
SEQ. ID. NO. 30184 323-GluMetValArgGluGluAspLysLysGluLeuProLysArgLeu-337
g269
AMPHI Regions - AMPHI
SEQ. ID. NO. 30185 36-LysProCysAlaSerLeuAspAlaSerSerAla-46
SEQ. ID. NO. 30186 54-TrpAspPheIleArgAsnThrAlaSerPro-63
SEQ. ID. NO. 30187 73-PheLysThrArgAlaLeuGlyArgPheSer-82
Antigenic Index - Jameson-Wolf
SEQ. ID. NO. 30188 28-TrpSerArgSerAlaPheSerCysLysProCysAla-39
SEQ. ID. NO. 30189 58-ArgAsnThrAlaSerProLysVal-65
SEQ. ID. NO. 30190 73-PheLysThrArgAlaLeuGlyArgPheSerAla-83
SEQ. ID. NO. 30191 90-LeuSerAsnArgGlyValLysLysProLeuSerPheLysSerProSerValGlnValAspThrSerAla-112
SEQ. ID. NO. 30192 117-SerLeuArgSerSer-121
Hydrophilic Regions - Hopp-Woods
SEQ. ID. NO. 30193 60-ThrAlaSerProLysVal-65
SEQ. ID. NO. 30194 73-PheLysThrArgAlaLeuGly-79
SEQ. ID. NO. 30195 93-ArgGlyValLysLysProLeuSer-100
g270
AMPHI Regions - AMPHI
SEQ. ID. NO. 30196 13-LeuLeuThrAlaPheAlaAlaPhe-20
SEQ. ID. NO. 30197 41-AspLeuThrGluGlyCys-46
SEQ. ID. NO. 30198 49-ProAspGlySerArg-53
Antigenic Index - Jameson-Wolf
SEQ. ID. NO. 30199 1-MetAsnLysAsnArgLysLeu-7
SEQ. ID. NO. 30200 41-AspLeuThrGluGlyCysThrLeuProAspGlySerArgValArgAlaAlaAlaValSerThrLysLysProPhe-65
SEQ. ID. NO. 30201 71-HisAlaProAlaGlyThrGlu-77
SEQ. ID. NO. 30202 86-LysAsnMetAspMetGlyPhe-92
SEQ. ID. NO. 30203 95-TyrMetPheGluArgGlnProSerGlyThr-104
SEQ. ID. NO. 30204 114-ValCysValGluGlyGlyArgArgAspPheThrAla-124
SEQ. ID. NO. 30205 128-IleGlySerArgThrPhe-133
Hydrophilic Regions - Hopp-Woods
SEQ. ID. NO. 30206 1-MetAsnLysAsnArgLysLeu-7
SEQ. ID. NO. 30207 49-ProAspGlySerArgValArgAla-56

TABLE 1-continued

| | |
|---|---|
| SEQ. ID. NO. 30208 | 60-SerThrLysLysProPhe-65 |
| SEQ. ID. NO. 30209 | 73-ProAlaGlyThrGlu-77 |
| SEQ. ID. NO. 30210 | 96-MetPheGluArgGlnPro-101 |
| SEQ. ID. NO. 30211 | 116-ValGluGlyArgArgAspPheThrAla-124 | g271-2
AMPHI Regions - AMPHI

| | |
|---|---|
| SEQ. ID. NO. 30212 | 6-MetAlaArgIleTrp-10 |
| SEQ. ID. NO. 30213 | 20-SerProCysProAla-24 |
| SEQ. ID. NO. 30214 | 29-ProLysSerProAla-33 |

Antigenic Index - Jameson-Wolf

| | |
|---|---|
| SEQ. ID. NO. 30215 | 2-PheSerSerArgMetAlaArg-8 |
| SEQ. ID. NO. 30216 | 25-LeuThrThrLysProLysSerProAlaLys-34 |
| SEQ. ID. NO. 30217 | 41-ArgSerAsnCysLeu-45 |
| SEQ. ID. NO. 30218 | 61-SerSerThrThrGlyAlaProThrSerArg-70 |
| SEQ. ID. NO. 30219 | 78-SerAlaSerIleAsnLysAspThrArgMetProAlaSerVal-91 |
| SEQ. ID. NO. 30220 | 102-CysCysAlaAsnThrSerLysProProSer-111 |

Hydrophilic Regions - Hopp-Woods

| | |
|---|---|
| SEQ. ID. NO. 30221 | 27-ThrLysProLysSerProAlaLys-34 |
| SEQ. ID. NO. 30222 | 80-SerIleAsnLysAspThrArgMet-87 |
| SEQ. ID. NO. 30223 | 105-AsnThrSerLysProPro-110 | g272-2
AMPHI Regions - AMPHI

| | |
|---|---|
| SEQ. ID. NO. 30224 | 44-IleThrArgIleThrAspGlu-50 |
| SEQ. ID. NO. 30225 | 70-AlaGluGluPheSerSerThrAsn-77 |
| SEQ. ID. NO. 30226 | 106-PheArgAlaIleThrSer-111 |
| SEQ. ID. NO. 30227 | 165-IleIleThrIleGluAspProIleGlu-173 |
| SEQ. ID. NO. 30228 | 194-AsnTrpMetAlaAlaLeuLysAsnThrLeuArgGlnAla-206 |
| SEQ. ID. NO. 30229 | 244-AsnGlnAlaLeuAspArgIleIleAsn-252 |
| SEQ. ID. NO. 30230 | 307-GlyAsnIleHisGluIleLysGluValMetLys-317 |
| SEQ. ID. NO. 30231 | 328-AspGlnHisLeuTyrGln-333 |
| SEQ. ID. NO. 30232 | 343-GlnAspAlaLeuLysAsnAlaAspSer-351 |

Antigenic Index - Jameson-Wolf

| | |
|---|---|
| SEQ. ID. NO. 30233 | 2-PheThrAspGluAsnMetThrAlaLysGluGluLeu-13 |
| SEQ. ID. NO. 30234 | 19-HisMetAsnLysAsnLysGlySerAsp-27 |
| SEQ. ID. NO. 30235 | 38-MetLysLeuAspGlyLysIleThrArgIleThrAspGluProLeuThrAlaGluLysCysMet-58 |
| SEQ. ID. NO. 30236 | 68-LysGlnAlaGluGluPheSerSerThrAsnGlu-78 |
| SEQ. ID. NO. 30237 | 85-LeuProAspThrSerArgPheArgVal-93 |
| SEQ. ID. NO. 30238 | 109-IleThrSerLysIleProLysPheGluSerLeuAsn-120 |
| SEQ. ID. NO. 30239 | 122-ProProAlaLeuLys-126 |
| SEQ. ID. NO. 30240 | 128-ValAlaLeuLysLysArgGly-134 |
| SEQ. ID. NO. 30241 | 142-ThrGlySerGlyLysSerThrSerLeu-150 |
| SEQ. ID. NO. 30242 | 154-IleAspTyrArgAsnGluAsnSerPheGly-163 |
| SEQ. ID. NO. 30243 | 168-IleGluAspProIle-172 |
| SEQ. ID. NO. 30244 | 176-HisGluHisLysAsnCys-181 |
| SEQ. ID. NO. 30245 | 184-ThrGlnArgGluValGlyValAspThrGluAsn-194 |
| SEQ. ID. NO. 30246 | 199-LeuLysAsnThrLeuArgGlnAlaProAsp-208 |
| SEQ. ID. NO. 30247 | 214-GluIleArgAspArgGluThrMet-221 |
| SEQ. ID. NO. 30248 | 241-AsnSerThrAsnGlnAlaLeuAspArg-249 |
| SEQ. ID. NO. 30249 | 254-PheProGluGluArgArgGluGlnLeuLeu-263 |
| SEQ. ID. NO. 30250 | 278-LeuValProArgAspGlyGlyLysGlyArgValAlaAla-290 |
| SEQ. ID. NO. 30251 | 310-HisGluIleLysGluValMetLysLysSerThr-320 |
| SEQ. ID. NO. 30252 | 336-GluLysGlyGlyGluIleSerLeu-342 |
| SEQ. ID. NO. 30253 | 344-AspAlaLeuLysAsnAlaAspSerAlaHisAspLeu-355 |
| SEQ. ID. NO. 30254 | 361-LeuArgSerArgArgAlaGlnSerSerAspProAspLeuGluLeu-375 |

Hydrophilic Regions - Hopp-Woods

| | |
|---|---|
| SEQ. ID. NO. 30255 | 2-PheThrAspGluAsnMetThrAlaLysGluGluLeu-13 |
| SEQ. ID. NO. 30256 | 20-MetAsnLysAsnLysGlySerAsp-27 |
| SEQ. ID. NO. 30257 | 38-MetLysLeuAspGlyLysIleThrArgIleThrAspGluProLeuThrAlaGluLysCysMet-58 |
| SEQ. ID. NO. 30258 | 68-LysGlnAlaGluGluPheSerSer-75 |
| SEQ. ID. NO. 30259 | 87-AspThrSerArgPheArgVal-93 |
| SEQ. ID. NO. 30260 | 112-LysIleProLysPheGluSer-118 |
| SEQ. ID. NO. 30261 | 128-ValAlaLeuLysLysArgGly-134 |
| SEQ. ID. NO. 30262 | 143-GlySerGlyLysSerThrSer-149 |
| SEQ. ID. NO. 30263 | 155-AspTyrArgAsnGluAsnSer-161 |
| SEQ. ID. NO. 30264 | 168-IleGluAspProIle-172 |
| SEQ. ID. NO. 30265 | 176-HisGluHisLysAsn-180 |
| SEQ. ID. NO. 30266 | 184-ThrGlnArgGluValGlyValAspThr-192 |
| SEQ. ID. NO. 30267 | 201-AsnThrLeuArgGlnAlaPro-207 |
| SEQ. ID. NO. 30268 | 214-GluIleArgAspArgGluThrMet-221 |
| SEQ. ID. NO. 30269 | 245-GlnAlaLeuAspArg-249 |
| SEQ. ID. NO. 30270 | 255-ProGluGluArgArgGluGlnLeuLeu-263 |
| SEQ. ID. NO. 30271 | 278-LeuValProArgAspGlyGlyLysGlyArgValAlaAla-290 |
| SEQ. ID. NO. 30272 | 310-HisGluIleLysGluValMetLysLysSerThr-320 |
| SEQ. ID. NO. 30273 | 336-GluLysGlyGlyGluIleSerLeu-342 |
| SEQ. ID. NO. 30274 | 344-AspAlaLeuLysAsnAlaAspSerAlaHisAspLeu-355 |
| SEQ. ID. NO. 30275 | 361-LeuArgSerArgArgAlaGlnSerSerAspProAspLeuGluLeu-375 | g274
AMPHI Regions - AMPHI

| | |
|---|---|
| SEQ. ID. NO. 30276 | 31-TyrLysAspGlyLys-35 |

TABLE 1-continued

SEQ. ID. NO. 30277 111-GluAlaValPheLys-115
Antigenic Index - Jameson-Wolf
SEQ. ID. NO. 30278 25-LeuValThrAspAspTyrTyrLysAspGlyLysHisIleAsp-38
SEQ. ID. NO. 30279 40-GlnLeuHisArgAspGluGluAlaValArgArgHisIle-52
SEQ. ID. NO. 30280 60-ProAspMetAsnAla-64
SEQ. ID. NO. 30281 71-GlyGluPheAspGlyLysGlnPro-78
SEQ. ID. NO. 30282 85-HisProThrArgLysAlaAspAspGlnThrVal-95
SEQ. ID. NO. 30283 99-ProValGlySerAlaGlnAsnGlyArgAlaGluTyr-110
SEQ. ID. NO. 30284 116-ThrLeuProProAlaAsnHis-122
SEQ. ID. NO. 30285 126-ArgValGluAspAlaAlaGly-132
SEQ. ID. NO. 30286 136-ValGluAsnLysTrpIleThrSerGlnGlyAsnAlaValAspLeuThrProMetAspLysLeuPheAsnAsnAlaGlySerLys-163
Hydrophilic Regions - Hopp-Woods
SEQ. ID. NO. 30287 29-AspTyrTyrLysAspGlyLysHisIleAsp-38
SEQ. ID. NO. 30288 40-GlnLeuHisArgAspGluGluAlaValArgArgHisIle-52
SEQ. ID. NO. 30289 72-GluPheAspGlyLysGln-77
SEQ. ID. NO. 30290 86-ProThrArgLysAlaAspAspGlnThrVal-95
SEQ. ID. NO. 30291 104-GlnAsnGlyArgAlaGluTyr-110
SEQ. ID. NO. 30292 126-ArgValGluAspAlaAlaGly-132
SEQ. ID. NO. 30293 151-ThrProMetAspLysLeuPhe-157
g276
AMPHI Regions - AMPHI
SEQ. ID. NO. 30294 19-ArgArgTrpAlaThrMetMet-25
SEQ. ID. NO. 30295 60-SerPheLysMetAlaArg-65
SEQ. ID. NO. 30296 80-ProPheAspProMetGlyTrp-86
SEQ. ID. NO. 30297 115-GlyArgLeuTyrArgThrPheSerAsn-123
SEQ. ID. NO. 30298 164-ThrLysArgGlyArgArgLeuThr-171
SEQ. ID. NO. 30299 207-SerThrSerThrLeuArgLysLeuMetArgProSerThr-219
Antigenic Index - Jameson-Wolf
SEQ. ID. NO. 30300 9-MetMetArgSerAlaAspSerThrVal-17
SEQ. ID. NO. 30301 29-PheSerIleArgArgSerSerAlaCysTrpThrArgArgSerAspSerLeuSer-46
SEQ. ID. NO. 30302 52-SerSerAsnAsnAsnIle-57
SEQ. ID. NO. 30303 67-MetAlaThrArgCysArgCysProProAspLysLeuLeuPro-80
SEQ. ID. NO. 30304 82-AspProMetGlyTrp-86
SEQ. ID. NO. 30305 88-SerProSerGlyAspAlaSerIleArg-96
SEQ. ID. NO. 30306 103-TrpArgAlaAspArgThrSerAlaSerProAlaSerGlyArgLeuTyr-118
SEQ. ID. NO. 30307 121-PheSerAsnArgValSerSerAsnArgAsnThrSerTrpGluThrArgAlaAsnTrpAlaArgArgGlnSerSerLeu-146
SEQ. ID. NO. 30308 158-LeuProAlaAspGlySerThrLysArgGlyArgArgLeuThrThr-172
SEQ. ID. NO. 30309 176-ProLeuProGluArgProThrArgAlaThrArgSerProCysLeu-190
SEQ. ID. NO. 30310 194-LeuLysLeuSerArg-198
SEQ. ID. NO. 30311 200-LeuMetProSerGluArgTyrSerThrSerThrLeuArgLysLeuMetArgProSerThrArgCysGlyAla-223
SEQ. ID. NO. 30312 229-CysSerGlyGlyValSerArgAsnAlaHisThrProSerAlaAlaArgAsn-245
Hydrophilic Regions - Hopp-Woods
SEQ. ID. NO. 30313 29-PheSerIleArgArgSerSer-35
SEQ. ID. NO. 30314 38-TrpThrArgArgSerAspSerLeu-45
SEQ. ID. NO. 30315 67-MetAlaThrArgCysArgCysProProAspLys-77
SEQ. ID. NO. 30316 90-SerGlyAspAlaSerIleArg-96
SEQ. ID. NO. 30317 104-ArgAlaAspArgThrSerAla-110
SEQ. ID. NO. 30318 124-ArgValSerSerAsnArgAsnThrSerTrpGluThr-135
SEQ. ID. NO. 30319 137-AlaAsnTrpAlaArgArgGlnSerSer-145
SEQ. ID. NO. 30320 161-AspGlySerThrLysArgGlyArgArgLeuThrThr-172
SEQ. ID. NO. 30321 176-ProLeuProGluArgProThrArgAlaThrArg-186
SEQ. ID. NO. 30322 194-LeuLysLeuSerArg-198
SEQ. ID. NO. 30323 200-LeuMetProSerGluArgTyrSer-207
SEQ. ID. NO. 30324 210-ThrLeuArgLysLeuMetArgProSerThrArgCys-221
SEQ. ID. NO. 30325 232-GlyValSerArgAsnAlaHis-238
g277-2
AMPHI Regions - AMPHI
SEQ. ID. NO. 30326 39-GlyIleAlaValPheGluValValGlyArgLeuLeuAspPheValLeu-54
SEQ. ID. NO. 30327 72-AsnGluValIleAspValPheHisAlaLeuGln-82
SEQ. ID. NO. 30328 87-AlaPheAspAlaValGlyAsnPheAlaGluTyrGlyArgAlaIleAspThrAlaAspLeuLeuGluIleGlyLysLeuGlyTyrPheHis-116
SEQ. ID. NO. 30329 180-AlaValGlyValValAlaValAla-187
Antigenic Index - Jameson-Wolf
SEQ. ID. NO. 30330 1-MetProArgPheGluAspGlnLeuValGlyArgXxxGlyLysAla-15
SEQ. ID. NO. 30331 68-ArgPheCysProAsnGluVal-74
SEQ. ID. NO. 30332 96-GluTyrGlyArgAlaIleAspThr-103
SEQ. ID. NO. 30333 118-ValGluProAspPheProAlaGlnThrProArgThrGluGlyGly-132
SEQ. ID. NO. 30334 138-PheAspLysAlaAspValVal-144
SEQ. ID. NO. 30335 162-AspIleGlyGlyGlyGlyPheGluGlyAspLeu-172
SEQ. ID. NO. 30336 196-LeuAspValGlyGlyLysProArgLeuGlyAlaGluArgAlaGlnAlaGlyGlyGlyMetGlyCysAlaGlyThrAspPheHis-223
SEQ. ID. NO. 30337 226-GlyLeuAspAspGlyAla-231
SEQ. ID. NO. 30338 237-GluGlyLeuGlnPheGluAspAspLeuLeuGluGlyLysHisGlyLeu-252
Hydrophilic Regions - Hopp-Woods
SEQ. ID. NO. 30339 2-ProArgPheGluAspGlnLeuVal-9
SEQ. ID. NO. 30340 96-GluTyrGlyArgAlaIleAspThr-103
SEQ. ID. NO. 30341 118-ValGluProAspPhe-122
SEQ. ID. NO. 30342 126-ThrProArgThrGluGly-131
SEQ. ID. NO. 30343 138-PheAspLysAlaAspValVal-144
SEQ. ID. NO. 30344 167-GlyPheGluGlyAspLeu-172
SEQ. ID. NO. 30345 198-ValGlyGlyLysProArgLeuGlyAlaGluArgAlaGlnAla-211
SEQ. ID. NO. 30346 226-GlyLeuAspAspGlyAla-231

TABLE 1-continued

SEQ. ID. NO. 30347 239-LeuGlnPheGluAspAspLeuLeuGluGlyLysHisGlyLeu-252
g278-2
AMPHI Regions - AMPHI
SEQ. ID. NO. 30348 20-IleGlyProLeuProSerIleGlyArg-28
SEQ. ID. NO. 30349 42-ThrGlyThrSerLys-46
SEQ. ID. NO. 30350 101-ArgThrIleProSerValThrGluIleThrValProArgValLeuThrSerAlaPhe-119
SEQ. ID. NO. 30351 123-PheSerIleLeuAlaLeuIleArgSerLeuIleSer-134
SEQ. ID. NO. 30352 157-LeuTyrArgGlnIleGlnAsnLeuIleThrHisPheAsnPheTyrAlaAla-173
SEQ. ID. NO. 30353 189-GluThrLeuIleGlnHisLeuArgGlnLeuAlaAsp-200
Antigenic Index - Jameson-Wolf
SEQ. ID. NO. 30354 25-SerIleGlyArgProAsnAlaSerThrThrArgProThrAsnSerArgProThrGlyThrSerLysIleArgPro-49
SEQ. ID. NO. 30355 63-SerProAsnThrThrAlaProThrGluSerArgSerArgPheIleAla-78
SEQ. ID. NO. 30356 80-ProLysValLeuProGlyAsnSerSerIle-89
SEQ. ID. NO. 30357 93-IleAlaSerAspLysProTrpMetArg-101
SEQ. ID. NO. 30358 119-PheThrAspArgPheSer-124
SEQ. ID. NO. 30359 146-ArgHisSerArgValGlnSerThr-153
SEQ. ID. NO. 30360 178-PheAspPheAspArgAspPheGlnLeu-186
SEQ. ID. NO. 30361 209-ThrValAsnAspGlyArgPheAspMetValGlu-219
Hydrophilic Regions - Hopp-Woods
SEQ. ID. NO. 30362 27-GlyArgProAsnAlaSerThrThrArgProThrAsnSerArgProThrGlyThrSerLysIleArgPro-49
SEQ. ID. NO. 30363 68-AlaProThrGluSerArgSerArgPheIleAla-78
SEQ. ID. NO. 30364 93-IleAlaSerAspLysProTrp-99
SEQ. ID. NO. 30365 146-ArgHisSerArgValGln-151
SEQ. ID. NO. 30366 178-PheAspPheAspArgAspPhe-184
SEQ. ID. NO. 30367 211-AsnAspGlyArgPheAspMetValGlu-219
g279
AMPHI Regions - AMPHI
SEQ. ID. NO. 30368 6-GlyCysLeuIleSer-10
SEQ. ID. NO. 30369 58-LeuProAlaIleThrThr-63
Antigenic Index - Jameson-Wolf
SEQ. ID. NO. 30370 28-GlnTrpGluGlyThrAspThrGlySerGlyArgAlaArgLeuAla-42
SEQ. ID. NO. 30371 64-CysProGlyGluLeuLysLeuThr-71
SEQ. ID. NO. 30372 74-ThrThrSerProCysAlaAspSer-81
SEQ. ID. NO. 30373 88-CysSerSerSerLysProLysMet-95
SEQ. ID. NO. 30374 102-ProCysGlyThrAlaAspCysIleSerSerAlaArgArgArgThrSerLeu-118
SEQ. ID. NO. 30375 120-AlaSerAlaLysSerAsnAlaSer-127
SEQ. ID. NO. 30376 148-ProProThrSerLys-152
Hydrophilic Regions - Hopp-Woods
SEQ. ID. NO. 30377 29-TrpGluGlyThrAspThrGlySerGlyArgAlaArgLeuAla-42
SEQ. ID. NO. 30378 66-GlyGluLeuLysLeu-70
SEQ. ID. NO. 30379 89-SerSerSerLysProLysMet-95
SEQ. ID. NO. 30380 110-SerSerAlaArgArgArgThrSerLeu-118
SEQ. ID. NO. 30381 120-AlaSerAlaLysSerAsnAla-126
g280
AMPHI Regions - AMPHI
SEQ. ID. NO. 30382 27-SerPheSerIleLeuGlyAspValAlaLys-36
SEQ. ID. NO. 30383 64-AspIleLysLysIleArgSerAla-71
SEQ. ID. NO. 30384 85-AspIleGlnArgAlaValLys-91
SEQ. ID. NO. 30385 97-TyrAlaGluAlaThrLysGlyIleGlnProLeuLys-108
SEQ. ID. NO. 30386 150-AspTyrAlaGlnAsnValAlaGluThrLeuIleLys-161
SEQ. ID. NO. 30387 237-ValAlaAlaIleIleArgGlnIleLys-245
SEQ. ID. NO. 30388 247-GluGlyIleLysAlaValPheThrGlu-255
SEQ. ID. NO. 30389 258-LysAspThrArgMetValAspArgIleAlaLysGluThr-270
SEQ. ID. NO. 30390 278-LeuTyrSerAspAlaLeuGlyAsnAlaProAlaAspThrTyrIle-292
Antigenic Index - Jameson-Wolf
SEQ. ID. NO. 30391 38-IleGlyGlyGluArgValAla-44
SEQ. ID. NO. 30392 51-AlaAsnGlnAspThrHis-56
SEQ. ID. NO. 30393 61-ThrSerGlyAspIleLysLysIleArgSerAlaLys-72
SEQ. ID. NO. 30394 82-GluAlaAlaAspIleGlnArgAlaValLysGlnSerLysValSerTyrAlaGluAlaThrLysGlyIleGln-105
SEQ. ID. NO. 30395 107-LeuLysAlaGluGluGluGlyGlyHisHisHisAspHisHisHisAspHisAspHisAspHisGluGlyHisHisHisAspHisGlyGlu
TyrAspProHisValTrpAsnAspProValLeu-147
SEQ. ID. NO. 30396 158-ThrLeuIleLysAlaAspProGluGlyLysValTyrTyr-170
SEQ. ID. NO. 30397 180-GlnLeuLysLysLeuHisSerAspAla-188
SEQ. ID. NO. 30398 196-ProAlaAlaLysArgLysValLeuThr-204
SEQ. ID. NO. 30399 212-MetGlyAsnArgTyr-216
SEQ. ID. NO. 30400 224-GlnGlyValSerSerGluAlaGluProSerAlaLysGln-236
SEQ. ID. NO. 30401 242-ArgGlnIleLysArgGluGlyIle-249
SEQ. ID. NO. 30402 255-GluAsnIleLysAspThrArgMetValAspArgIleAlaLysGluThrGlyVal-272
SEQ. ID. NO. 30403 274-ValSerGlyLysLeuTyrSer-280
SEQ. ID. NO. 30404 286-AlaProAlaAspThr-290
SEQ. ID. NO. 30405 295-TyrArgHisAsnVal-299
Hydrophilic Regions - Hopp-Woods
SEQ. ID. NO. 30406 38-IleGlyGlyGluArgValAla-44
SEQ. ID. NO. 30407 63-GlyAspIleLysLysIleArgSerAlaLys-72
SEQ. ID. NO. 30408 82-GluAlaAlaAspIleGlnArgAlaValLysGlnSerLys-94
SEQ. ID. NO. 30409 99-GluAlaThrLysGly-103
SEQ. ID. NO. 30410 107-LeuLysAlaGluGluGluGlyGlyHisHisHisAspHisHisHisAspHisAspHisAspHisGluGlyHisHisHisAspHisGlyGluTyrAsp-138
SEQ. ID. NO. 30411 158-ThrLeuIleLysAlaAspProGluGly-166
SEQ. ID. NO. 30412 180-GlnLeuLysLysLeuHisSerAspAla-188
SEQ. ID. NO. 30413 196-ProAlaAlaLysArgLysValLeuThr-204

TABLE 1-continued

| | |
|---|---|
| SEQ. ID. NO. 30414 | 226-ValSerSerGluAlaGluProSerAlaLysGln-236 |
| SEQ. ID. NO. 30415 | 242-ArgGlnIleLysArgGluGlyIle-249 |
| SEQ. ID. NO. 30416 | 255-GluAsnIleLysAspThrArgMetValAspArgIleAlaLysGluThrGlyVal-272 | g281
AMPHI Regions - AMPHI

| | |
|---|---|
| SEQ. ID. NO. 30417 | 62-AlaAlaGlyMetLeuMetAlaLeuLeuAlaGlyLeuValSerArgPhe-77 |
| SEQ. ID. NO. 30418 | 126-LeuGlnLeuIleAlaAlaValSerGlyLeuThr-136 |
| SEQ. ID. NO. 30419 | 179-LeuValSerGlyPheGlnAlaLeuGlyIleLeu-189 |
| SEQ. ID. NO. 30420 | 216-SerValLeuIleAlaLeuPheCysGlyLeuIleGlyLeu-228 |

Antigenic Index - Jameson-Wolf

| | |
|---|---|
| SEQ. ID. NO. 30421 | 25-ArgArgMetSerLeu-29 |
| SEQ. ID. NO. 30422 | 78-ThrThrLeuLysGluAspAlaAsn-85 |
| SEQ. ID. NO. 30423 | 102-SerLysAsnGlySerSerVal-108 |
| SEQ. ID. NO. 30424 | 158-LysSerValAsnGlyLysGlyGly-165 |
| SEQ. ID. NO. 30425 | 236-IleProSerGlyPro-240 |
| SEQ. ID. NO. 30426 | 256-LeuGlyLysGluGlyGlyIle-262 |
| SEQ. ID. NO. 30427 | 266-TrpPheLysAsnHisArgHisHisThrThr-275 |

Hydrophilic Regions - Hopp-Woods

| | |
|---|---|
| SEQ. ID. NO. 30428 | 25-ArgArgMetSerLeu-29 |
| SEQ. ID. NO. 30429 | 78-ThrThrLeuLysGluAspAlaAsn-85 |
| SEQ. ID. NO. 30430 | 103-LysAsnGlySerSer-107 |
| SEQ. ID. NO. 30431 | 256-LeuGlyLysGluGlyGlyIle-262 |
| SEQ. ID. NO. 30432 | 270-HisArgHisHisThr-274 | g282
AMPHI Regions - AMPHI

| | |
|---|---|
| SEQ. ID. NO. 30433 | 10-LeuIleValAlaLeuLeuValLeuIleAsnProPheSerAlaLeu-24 |
| SEQ. ID. NO. 30434 | 50-ValPheAlaValIleAlaValPheAlaLeuIleGlyGlyAlaLeu-64 |
| SEQ. ID. NO. 30435 | 112-ArgProAlaArgAsn-116 |
| SEQ. ID. NO. 30436 | 176-ValSerArgLeuLeu-180 |
| SEQ. ID. NO. 30437 | 186-ThrIleLeuAsnArgIleMetGlyMet-194 |

Antigenic Index - Jameson-Wolf

| | |
|---|---|
| SEQ. ID. NO. 30438 | 31-ThrAsnGlyHisSerThrLysGluArgArgLysValAlaArg-44 |
| SEQ. ID. NO. 30439 | 92-AsnGlyAsnAspAsnProAlaLysGlnAsnLeuGlyAlaGlnProGluThrGlyGlnAlaArgProAlaArgAsnAlaGly-118 |

Hydrophilic Regions - Hopp-Woods

| | |
|---|---|
| SEQ. ID. NO. 30440 | 34-HisSerThrLysGluArgArgLysValAlaArg-44 |
| SEQ. ID. NO. 30441 | 92-AsnGlyAsnAspAsnProAlaLysGlnAsnLeu-102 |
| SEQ. ID. NO. 30442 | 104-AlaGlnProGluThrGlyGlnAlaArgProAlaArgAsn-116 | g283
AMPHI Regions - AMPHI

| | |
|---|---|
| SEQ. ID. NO. 30443 | 32-GlyGlyAsnSerTyrSerAspValProLysGlnLeuHis-44 |
| SEQ. ID. NO. 30444 | 48-SerGlnIleLeuAsnLeu-53 |

Antigenic Index - Jameson-Wolf

| | |
|---|---|
| SEQ. ID. NO. 30445 | 28-TrpLysAspGlyGlyGlyAsnSerTyrSerAspValProLysGlnLeuHisProAspGlnSerGln-49 |
| SEQ. ID. NO. 30446 | 55-ThrLeuGlnThrLysProAlaValLysProLysProAlaValAspThrAsnAlaAspSerAlaLysGluAsnGluLysAspIleAlaGluLysAsnGlyGlnLeuGluGluGluLysLysLysIleAlaGluThrGluArgGlnAsnLysGluGluAsnCysArgIleSerLysMetAsnLeu-115 |
| SEQ. ID. NO. 30447 | 119-GlyAsnSerAsnAlaLysAsnLysAspAspLeuIleArgLysTyrAsnAsnAlaValAsnLysTyrCysArg-142 |

Hydrophilic Regions - Hopp-Woods

| | |
|---|---|
| SEQ. ID. NO. 30448 | 35-SerTyrSerAspValProLys-41 |
| SEQ. ID. NO. 30449 | 43-LeuHisProAspGlnSerGln-49 |
| SEQ. ID. NO. 30450 | 60-ProAlaValLysProLysProAlaValAspThrAsnAlaAspSerAlaLysGluAsnGluLysAspIleAlaGluLysAsnGlyGlnLeuGluGluGluLysLysLysIleAlaGluThrGluArgGlnAsnLysGluGluAsnCysArgIleSerLysMetAsnLeu-115 |
| SEQ. ID. NO. 30451 | 121-SerAsnAlaLysAsnLysAspAspLeuIleArgLysTyrAsn-134 | g284-2
AMPHI Regions - AMPHI

| | |
|---|---|
| SEQ. ID. NO. 30452 | 43-GluAlaPheAlaGlyPhePheGluThrVal-52 |
| SEQ. ID. NO. 30453 | 61-ThrPheAlaAlaArgPhe-66 |
| SEQ. ID. NO. 30454 | 125-ValAspPheAspValPhe-130 |
| SEQ. ID. NO. 30455 | 154-ValValPheArgLeuPheArgGln-161 |
| SEQ. ID. NO. 30456 | 174-AsnThrAlaCysGlyAsnValGlyGly-182 |
| SEQ. ID. NO. 30457 | 186-PheAlaAlaAlaPhe-190 |
| SEQ. ID. NO. 30458 | 216-PheValGlnPheIleArgAspAspPheGlyHisArg-227 |
| SEQ. ID. NO. 30459 | 277-PheArgValPheGlyGlnPheAlaArgGlnPheAlaAspCysAlaVal-292 |
| SEQ. ID. NO. 30460 | 310-AspGlyPheAspValValAspLys-317 |
| SEQ. ID. NO. 30461 | 342-LeuHisGlnValArgGlnThrAlaArgSerGlyAspAsnGlnIleAspArgPheAlaGln-361 |
| SEQ. ID. NO. 30462 | 381-AlaHisIlePheGly-385 |
| SEQ. ID. NO. 30463 | 387-ArgGlnCysValPhe-391 |
| SEQ. ID. NO. 30464 | 408-ArgAlaPheAlaArgPhePheAlaAlaPheGlyGlnSerLeuGlnSer-423 |

Antigenic Index - Jameson-Wolf

| | |
|---|---|
| SEQ. ID. NO. 30465 | 1-MetProSerGluThrArgAsnArgPhe-9 |
| SEQ. ID. NO. 30466 | 107-HisAlaPheAspGlyGlnPhe-113 |
| SEQ. ID. NO. 30467 | 132-HisPheGlyLysArgAsnArgAsnThrArgAla-142 |
| SEQ. ID. NO. 30468 | 147-GlyAlaProAspAlaVal-152 |
| SEQ. ID. NO. 30469 | 167-ValGlyAsnGlyArgTyrVal-173 |
| SEQ. ID. NO. 30470 | 178-GlyAsnValGlyGlyAsnGlnAsn-185 |
| SEQ. ID. NO. 30471 | 192-GlnIleArgGlnArgAlaVal-198 |
| SEQ. ID. NO. 30472 | 209-AlaValGlyGlyGlu-213 |
| SEQ. ID. NO. 30473 | 219-PheIleArgAspAspPheGlyHisArgPheGlyGlyArgGluAsnHisThr-235 |
| SEQ. ID. NO. 30474 | 292-ValProSerGlyGlyGluGlnXxxSer-300 |
| SEQ. ID. NO. 30475 | 303-ValGlyArgGlyGlyPheHisAspGlyPheAspValValAspLysAlaHis-319 |
| SEQ. ID. NO. 30476 | 346-ArgGlnThrAlaArgSerGlyAspAsnGlnIleAspArgPheAla-360 |

TABLE 1-continued

| | |
|---|---|
| SEQ. ID. NO. 30477 | 362-GlyAlaGlyLeuValAlaGluArgCysAlaAlaAspAspAlaAspGlyAlaGluPro-380 |
| SEQ. ID. NO. 30478 | 393-AspLeuArgArgGlnPheAlaGlyArgCysGlnHisGlnArgAlaArgAla-409 |
| SEQ. ID. NO. 30479 | 419-GlnSerLeuGlnSerArg-424 |
| Hydrophilic Regions - Hopp-Woods | |
| SEQ. ID. NO. 30480 | 1-MetProSerGluThrArgAsnArgPhe-9 |
| SEQ. ID. NO. 30481 | 134-GlyLysArgAsnArgAsnThrArgAla-142 |
| SEQ. ID. NO. 30482 | 193-IleArgGlnArgAlaVal-198 |
| SEQ. ID. NO. 30483 | 220-IleArgAspAspPheGlyHis-226 |
| SEQ. ID. NO. 30484 | 228-PheGlyGlyArgGluAsnHisThr-235 |
| SEQ. ID. NO. 30485 | 294-SerGlyGlyGluGlnXxx-299 |
| SEQ. ID. NO. 30486 | 313-AspValValAspLysAlaHis-319 |
| SEQ. ID. NO. 30487 | 346-ArgGlnThrAlaArgSerGlyAspAsnGlnIleAspArgPheAla-360 |
| SEQ. ID. NO. 30488 | 366-ValAlaGluArgCysAlaAlaAspAspAlaAspGlyAlaGlu-379 |
| SEQ. ID. NO. 30489 | 393-AspLeuArgArgGlnPheAla-399 |
| SEQ. ID. NO. 30490 | 402-CysGlnHisGlnArgAlaArgAla-409 |
| g285-1 | |
| AMPHI Regions - AMPHI | |
| SEQ. ID. NO. 30491 | 15-ValCysPheLeuGly-19 |
| SEQ. ID. NO. 30492 | 34-GlnIleProSerTrp-38 |
| SEQ. ID. NO. 30493 | 50-GlyThrLeuLeuAspGlyPheAsp-57 |
| SEQ. ID. NO. 30494 | 115-GlnGlyLeuProAspSerIleAspLeuPro-124 |
| SEQ. ID. NO. 30495 | 208-HisSerThrAlaArg-212 |
| SEQ. ID. NO. 30496 | 240-HisProPheAlaGluSerLeuAspLysThrLeuGluGluValLeu-254 |
| SEQ. ID. NO. 30497 | 266-ValProSerLeuPro-270 |
| SEQ. ID. NO. 30498 | 280-AlaIleProSerPheSerAsp-286 |
| SEQ. ID. NO. 30499 | 313-GlnValLeuGlyGly-317 |
| SEQ. ID. NO. 30500 | 592-IleGlyLysAlaAlaAspIle-598 |
| SEQ. ID. NO. 30501 | 671-GlyIleAsnArgGluLeuThrArgTrp-679 |
| SEQ. ID. NO. 30502 | 745-LeuHisIleAlaGluLeuHisAsnPhePheLysProProPhe-758 |
| SEQ. ID. NO. 30503 | 836-PheGlyGlyAsnMetAlaAsn-842 |
| SEQ. ID. NO. 30504 | 848-ArgIleThrAlaSerLeu-853 |
| SEQ. ID. NO. 30505 | 855-AspLeuGlyAlaLeu-859 |
| SEQ. ID. NO. 30506 | 868-GlnAsnIleThrGlySer-873 |
| SEQ. ID. NO. 30507 | 955-GlySerIleAlaAsp-959 |
| SEQ. ID. NO. 30508 | 1008-ThrAlaGluLeuSer-1012 |
| SEQ. ID. NO. 30509 | 1061-ValThrGlyMetIleLys-1066 |
| SEQ. ID. NO. 30510 | 1137-GlyAsnValArgGlyValGlyThrValArg-1146 |
| SEQ. ID. NO. 30511 | 1165-ThrValSerPheValGlyProLeuAsn-1173 |
| SEQ. ID. NO. 30512 | 1190-AlaGlyValGluIleLeuGlySerLeuAsn-1199 |
| SEQ. ID. NO. 30513 | 1244-LeuAlaGlyGlnIle-1248 |
| SEQ. ID. NO. 30514 | 1305-ValLysLeuIleTyrArgLeuThrArgAlaIleGlnAlaValAlaArgIleGlySer-1323 |
| SEQ. ID. NO. 30515 | 1335-ArgPheAspArgLeuPheGly-1341 |
| Antigenic Index - Jameson-Wolf | |
| SEQ. ID. NO. 30516 | 43-IleSerSerGlnAsnLeuLysGlyThrLeuLeuAspGlyPheAspGlyAspAsnTrpSerIleGluThrGluGlyAlaAspLeuLysIleSerArg-74 |
| SEQ. ID. NO. 30517 | 80-LysProSerGluLeuMetArgArgSerLeuHis-90 |
| SEQ. ID. NO. 30518 | 104-LysProThrProProLysGluGluArgProProGlnGlyLeuProAspSerIleAsp-122 |
| SEQ. ID. NO. 30519 | 130-AspArgPheGluThrGlyLysIleSerMetGlyLysThrPheAspLysGlnThrValTyr-149 |
| SEQ. ID. NO. 30520 | 157-TyrArgTyrAspArgLysGlyHisArgLeuAspLeuLysAlaAlaAspThrProTrpSerSerSerSerGlySerAla-182 |
| SEQ. ID. NO. 30521 | 185-GlyLeuLysLysProPheAla-191 |
| SEQ. ID. NO. 30522 | 198-ThrLysGlyGlyPheGluGlyGluThrIle-207 |
| SEQ. ID. NO. 30523 | 209-SerThrAlaArgLeuSerGlySerLeuLysAspValArgAla-222 |
| SEQ. ID. NO. 30524 | 224-LeuThrIleAspGlyGlyAsnIleArgLeuSerGlyLysSer-237 |
| SEQ. ID. NO. 30525 | 244-GluSerLeuAspLysThrLeuGlu-251 |
| SEQ. ID. NO. 30526 | 268-SerLeuProAspAla-272 |
| SEQ. ID. NO. 30527 | 292-GlySerLeuAspLeuGluAsnThrLys-300 |
| SEQ. ID. NO. 30528 | 302-GlyPheAlaAspArgAsnGlyIleProVal-311 |
| SEQ. ID. NO. 30529 | 320-IleArgGlnAspGlyThrVal-326 |
| SEQ. ID. NO. 30530 | 337-GlyArgGlyGlyIleArgLeuSerGlyLysIleAspThrGluLysAspIleLeu-354 |
| SEQ. ID. NO. 30531 | 362-SerValGlyAlaGluAspValLeu-369 |
| SEQ. ID. NO. 30532 | 372-AlaPheLysGlyArgLeuAspGlySerIle-381 |
| SEQ. ID. NO. 30533 | 386-ThrThrAlaSerProLysIle-392 |
| SEQ. ID. NO. 30534 | 397-GlyThrGlyThrAlaArgThrAspGlySerLeu-407 |
| SEQ. ID. NO. 30535 | 411-SerAspProAlaAsnGluGlnArgLysLeuVal-421 |
| SEQ. ID. NO. 30536 | 428-SerAlaGlyGluGlySerLeuThr-435 |
| SEQ. ID. NO. 30537 | 442-LeuPheLysArgArgLeuLeuLysLeuAspIleArgSerArgAlaPheAspProSerArgIleAspProGlnPheProAlaGlyAspIleAsnGly-473 |
| SEQ. ID. NO. 30538 | 480-GluLeuAlaLysGluLysPheThrGlyLys-489 |
| SEQ. ID. NO. 30539 | 508-IleValTyrGluSerArgHisLeuProArgAlaAlaVal-520 |
| SEQ. ID. NO. 30540 | 522-LeuArgLeuGlyArgAsnIleValLysThrAspGlyGlyPheGlyLysLysGlyAspArgLeuAsn-543 |
| SEQ. ID. NO. 30541 | 548-AlaProAspLeuSerArgPheGly-555 |
| SEQ. ID. NO. 30542 | 563-AsnValArgGlyHisLeuSerGlyAspLeuAspGlyGlyIleArgThrPheGluThrAspLeuSerGlyThrAlaArg-588 |
| SEQ. ID. NO. 30543 | 594-LysAlaAlaAspIleArgSer-600 |
| SEQ. ID. NO. 30544 | 605-LeuLysGlySerProGlyThrSerArgProMetArgAlaAspIleLysGlyGlyArgLeu-624 |
| SEQ. ID. NO. 30545 | 641-GluGlyThrGlyAla-645 |
| SEQ. ID. NO. 30546 | 647-HisArgIleArgThr-651 |
| SEQ. ID. NO. 30547 | 657-LeuAspGlyLysProPheLysLeuAspLeuAspAlaSerGlyGlyIleAsnArgGluLeuThrArgTrpLysGlySerIle-683 |
| SEQ. ID. NO. 30548 | 696-LeuGlnAsnArgMetThrLeu-702 |
| SEQ. ID. NO. 30549 | 729-SerTrpAspArgLysThrGlyIleSerAlaLysGlyGlyAlaArgGly-744 |
| SEQ. ID. NO. 30550 | 764-LeuAsnGlyAspTrp-768 |
| SEQ. ID. NO. 30551 | 774-HisAsnAlaArgGly-778 |
| SEQ. ID. NO. 30552 | 782-IleSerArgGlnSerGlyAspAlaValLeu-791 |

TABLE 1-continued

| | |
|---|---|
| SEQ. ID. NO. 30553 | 803-SerLeuLysThrArgPheGlnAsnAspArgIleGly-814 |
| SEQ. ID. NO. 30554 | 817-LeuAspGlyGlyAlaArgPheGlyArgIleAsnAla-828 |
| SEQ. ID. NO. 30555 | 844-ProLeuGlyGlyArgIleThr-850 |
| SEQ. ID. NO. 30556 | 880-IleGlyGlyArgValGlySerProSerVal-889 |
| SEQ. ID. NO. 30557 | 893-ValAsnGlySerSerAsnTyrGlyLysIleAsnGly-904 |
| SEQ. ID. NO. 30558 | 908-ValGlyGlnSerArgSerPheAspThrAlaProLeuGlyGlyArg-922 |
| SEQ. ID. NO. 30559 | 928-AlaAspAlaGluAlaPhe-933 |
| SEQ. ID. NO. 30560 | 941-GlnThrValLysGlySerLeu-947 |
| SEQ. ID. NO. 30561 | 956-SerIleAlaAspProHisLeuGlyGly-964 |
| SEQ. ID. NO. 30562 | 966-IleAsnGlyAspLysLeuTyrTyrArgAsnGlnThr-977 |
| SEQ. ID. NO. 30563 | 982-LeuAspAsnGlySerLeuArg-988 |
| SEQ. ID. NO. 30564 | 991-IleAlaGlyArgLysTrpVal-997 |
| SEQ. ID. NO. 30565 | 1001-LeuLysPheArgHisGluGlyThrAlaGluLeuSerGly-1013 |
| SEQ. ID. NO. 30566 | 1015-ValSerMetGluAsnSerValProAspValAspIle-1026 |
| SEQ. ID. NO. 30567 | 1031-AspLysTyrArgIleLeuSerArgProAsnArgArgLeuThr-1044 |
| SEQ. ID. NO. 30568 | 1047-GlyAsnThrArgLeuArgTyrSerProGlnLysGlyIle-1059 |
| SEQ. ID. NO. 30569 | 1065-IleLysThrAspGlnGlyLeuPheGlySerGlnLysSerSerMetProSerValGlyAspAspVal-1086 |
| SEQ. ID. NO. 30570 | 1091-GluValLysLysGluAlaAlaAla-1098 |
| SEQ. ID. NO. 30571 | 1109-AspLeuAsnAspGlyIleArgPhe-1116 |
| SEQ. ID. NO. 30572 | 1134-GlnProGlyGlyAsnValArgGlyValGly-1143 |
| SEQ. ID. NO. 30573 | 1146-ArgValIleLysGlyArgTyrLysAlaTyrGlyGlnAspLeuAspIleThrLysGlyThr-1165 |
| SEQ. ID. NO. 30574 | 1171-ProLeuAsnAspProAsnLeuAsnIleArgAlaGluArgArgLeuSerProValGly-1189 |
| SEQ. ID. NO. 30575 | 1197-SerLeuAsnSerProArgIle-1203 |
| SEQ. ID. NO. 30576 | 1207-AlaAsnGluProMetSerGluLysAspLysLeu-1217 |
| SEQ. ID. NO. 30577 | 1225-AlaGlySerGlySerSerGlyAspAsnAlaAla-1235 |
| SEQ. ID. NO. 30578 | 1246-GlyGlnIleAsnAspArgIleGlyLeu-1254 |
| SEQ. ID. NO. 30579 | 1256-AspAspLeuGlyPheThrSerLysArgSerArgAsnAlaGlnThrGlyGluLeuAsnProAlaGlu-1277 |
| SEQ. ID. NO. 30580 | 1283-GlyLysGlnLeuThrGlyLys-1289 |
| SEQ. ID. NO. 30581 | 1298-IleSerSerAlaGluGlnSerVal-1305 |
| SEQ. ID. NO. 30582 | 1321-IleGlySerArgSerSerGlyGlyGluLeu-1330 |
| SEQ. ID. NO. 30583 | 1335-ArgPheAspArgLeuPheGlySerAspLysLysAspSerAlaGlyAsnGlyLysGlyLys-1354 |
| Hydrophilic Regions - Hopp-Woods | |
| SEQ. ID. NO. 30584 | 56-PheAspGlyAspAsnTrpSerIleGluThrGluGlyAlaAspLeuLysIleSerArg-74 |
| SEQ. ID. NO. 30585 | 83-GluLeuMetArgSerLeuHis-90 |
| SEQ. ID. NO. 30586 | 105-ProThrProProLysGluGluArgProProGlnGlyLeu-117 |
| SEQ. ID. NO. 30587 | 130-AspArgPheGluThrGlyLys-136 |
| SEQ. ID. NO. 30588 | 141-LysThrPheAspLys-145 |
| SEQ. ID. NO. 30589 | 157-TyrArgTyrAspArgLysGlyHisArgLeuAspLeuLysAlaAlaAsp-172 |
| SEQ. ID. NO. 30590 | 200-GlyGlyPheGluGlyGluThrIle-207 |
| SEQ. ID. NO. 30591 | 215-GlySerLeuLysAspValArgAla-222 |
| SEQ. ID. NO. 30592 | 244-GluSerLeuAspLysThrLeuGlu-251 |
| SEQ. ID. NO. 30593 | 292-GlySerLeuAspLeuGluAsnThrLys-300 |
| SEQ. ID. NO. 30594 | 302-GlyPheAlaAspArgAsnGlyIlePro-310 |
| SEQ. ID. NO. 30595 | 320-IleArgGlnAspGly-324 |
| SEQ. ID. NO. 30596 | 343-LeuSerGlyLysIleAspThrGluLysAspIleLeu-354 |
| SEQ. ID. NO. 30597 | 364-GlyAlaGluAspValLeu-369 |
| SEQ. ID. NO. 30598 | 373-PheLysGlyArgLeuAspGly-379 |
| SEQ. ID. NO. 30599 | 400-ThrAlaArgThrAspGly-405 |
| SEQ. ID. NO. 30600 | 411-SerAspProAlaAsnGluGlnArgLysLeuVal-421 |
| SEQ. ID. NO. 30601 | 429-AlaGlyGluGlySerLeu-434 |
| SEQ. ID. NO. 30602 | 442-LeuPheLysAspArgLeuLeuLysLeuAspIleArgSerArgAlaPheAspProSerArgIleAspPro-464 |
| SEQ. ID. NO. 30603 | 480-GluLeuAlaLysGluLysPheThrGly-488 |
| SEQ. ID. NO. 30604 | 508-IleValTyrGluSerArgHisLeuPro-516 |
| SEQ. ID. NO. 30605 | 522-LeuArgLeuGlyArgAsnIleValLysThrArgGlyGlyPheGlyLysLysGlyAspArgLeuAsn-543 |
| SEQ. ID. NO. 30606 | 570-GlyAspLeuAspGlyGlyIleArgThrPheGluThrAspLeuSerGlyThrAla-587 |
| SEQ. ID. NO. 30607 | 594-LysAlaAlaAspIleArgSer-600 |
| SEQ. ID. NO. 30608 | 607-GlySerProGlyThrSerArgProMetArgAlaAspIleLysGlyGlyArg-623 |
| SEQ. ID. NO. 30609 | 647-HisIleArgThr-651 |
| SEQ. ID. NO. 30610 | 657-LeuAspGlyLysProPheLysLeuAspLeuAspAla-668 |
| SEQ. ID. NO. 30611 | 670-GlyGlyIleAsnArgGluLeuThrArgTrpLysGly-681 |
| SEQ. ID. NO. 30612 | 729-SerTrpAspArgLysThrGlyIleSerAlaLysGlyGlyAlaArg-743 |
| SEQ. ID. NO. 30613 | 783-SerArgGlnSerGly-787 |
| SEQ. ID. NO. 30614 | 806-ThrArgPheGlnAsnAspArgIle-813 |
| SEQ. ID. NO. 30615 | 819-GlyGlyAlaArgPheGlyArgIleAsnAla-828 |
| SEQ. ID. NO. 30616 | 928-AlaAspAlaGluAlaPhe-933 |
| SEQ. ID. NO. 30617 | 1001-LeuLysPheArgHisGluGlyThrAlaGluLeu-1011 |
| SEQ. ID. NO. 30618 | 1019-AsnSerValProAspValAspIle-1026 |
| SEQ. ID. NO. 30619 | 1031-AspLysTyrArgIleLeuSerArgProAsnArgArgLeuThr-1044 |
| SEQ. ID. NO. 30620 | 1049-ThrArgLeuArgTyrSerPro-1055 |
| SEQ. ID. NO. 30621 | 1065-IleLysThrAspGln-1069 |
| SEQ. ID. NO. 30622 | 1075-GlnLysSerSerMet-1079 |
| SEQ. ID. NO. 30623 | 1091-GluValLysLysGluAlaAlaAla-1098 |
| SEQ. ID. NO. 30624 | 1109-AspLeuAsnAspGlyIleArg-1115 |
| SEQ. ID. NO. 30625 | 1146-ArgValIleLysGlyArgTyrLysAlaTyrGlyGlnAspLeuAspIleThrLys-1163 |
| SEQ. ID. NO. 30626 | 1179-IleArgAlaGluArgArgLeuSer-1186 |
| SEQ. ID. NO. 30627 | 1209-GluProMetSerGluLysAspLysLeu-1217 |
| SEQ. ID. NO. 30628 | 1225-AlaGlySerGlySerSerGlyAspAsnAlaAla-1235 |
| SEQ. ID. NO. 30629 | 1248-IleAsnAspArgIleGlyLeu-1254 |
| SEQ. ID. NO. 30630 | 1259-GlyPheThrSerLysArgSerArgAsnAlaGlnThrGlyGluLeuAsnPro-1275 |
| SEQ. ID. NO. 30631 | 1300-SerAlaGluGlnSerVal-1305 |

TABLE 1-continued

```
SEQ. ID. NO. 30632    1321-IleGlySerArgSerSerGlyGly-1328
SEQ. ID. NO. 30633    1340-PheGlySerAspLysLysAspSerAlaGlyAsnGlyLysGlyLys-1354
g286-2
AMPHI Regions - AMPHI
SEQ. ID. NO. 30634    69-GluIleLysAspMetVal-74
SEQ. ID. NO. 30635    102-ProAspAsnValLysThr-107
SEQ. ID. NO. 30636    145-ValAlaIleLeuGlyAsp-150
SEQ. ID. NO. 30637    157-LeuAlaGluTyrTyrArgAsnAlaLeuGluAsnTrpGlnGlnProValGlySer-174
SEQ. ID. NO. 30638    199-LeuAlaLysLeuGlyAsn-204
SEQ. ID. NO. 30639    238-ThrGlnArgTyrProGluGlnThrValSerGlyLeuAlaArgPheGlnProGlyThr-256
SEQ. ID. NO. 30640    326-AspTyrTyrAsnLeuPheAsnLys-333
SEQ. ID. NO. 30641    354-IleSerGlnProArg-358
SEQ. ID. NO. 30642    375-ThrThrGlnAsnLeu-379
SEQ. ID. NO. 30643    428-ThrAlaSerTrpLysArgGlnLeuLeu-436
SEQ. ID. NO. 30644    455-ThrLeuGlyThrPheLeu-460
SEQ. ID. NO. 30645    513-GlyAlaSerSerVal-517
SEQ. ID. NO. 30646    555-LeuSerGlyAlaValPheHisAspMetGlyAspAlaAlaAlaAsn-569
SEQ. ID. NO. 30647    584-ArgTrpPheSerProLeu-589
Antigenic Index - Jameson-Wolf
SEQ. ID. NO. 30648    1-MetHisAspThrArgThrMetMet-8
SEQ. ID. NO. 30649    30-AlaAspLeuSerGluAsnLysAla-37
SEQ. ID. NO. 30650    43-PheLysSerLysSerProAspThrGluSerValLysLeuLysProLysPheProVal-61
SEQ. ID. NO. 30651    63-IleAspThrGlnAspSerGluIleLysAspMetValGluGluHisLeu-78
SEQ. ID. NO. 30652    83-GlnGlnGlnGluGluValLeuAspLysGluGlnThr-94
SEQ. ID. NO. 30653    97-LeuAlaGluGluAlaProAspAsnValLysThrMetLeuArgSerLysGlyTyrPheSerSerLysValSerLeuThrGluLysAspGlyAla-127
SEQ. ID. NO. 30654    133-ThrProGlyProArgThrLysIle-140
SEQ. ID. NO. 30655    151-IleLeuSerAspGlyAsnLeuAlaGluTyrTyrArgAsnAlaLeuGluAsnTrpGln-169
SEQ. ID. NO. 30656    172-ValGlySerAspPheAspGlnAspSerTrpGluAsnSerLysThrSerVal-188
SEQ. ID. NO. 30657    192-ValThrArgLysGlyTyrPro-198
SEQ. ID. NO. 30658    201-LysLeuGlyAsnThrArgAlaAlaValAsnProAspThrAlaThrAla-216
SEQ. ID. NO. 30659    223-AspSerGlyArgProIleAla-229
SEQ. ID. NO. 30660    234-GluIleThrGlyThrGlnArgTyrProGluGlnThrVal-246
SEQ. ID. NO. 30661    252-PheGlnProGlyThrProTyrAspLeu-260
SEQ. ID. NO. 30662    270-LeuGluGlnAsnGlyHisTyrSerGly-278
SEQ. ID. NO. 30663    283-AlaAspPheAspArgLeuGlnGlyAspArgValProVal-295
SEQ. ID. NO. 30664    298-SerValThrGluValLysArgHisLysLeuGluThrGlyIleArgLeuAspSerGluTyrGlyLeuGlyGly-321
SEQ. ID. NO. 30665    342-AspMetAspLysTyrGluThr-348
SEQ. ID. NO. 30666    355-SerGlnProArgAsnTyrArgGlyAsnTyrTrp-365
SEQ. ID. NO. 30667    368-AsnValSerTyrAsnArgSerThrThrGlnAsnLeuGluLysArgAlaPheSerGlyGly-387
SEQ. ID. NO. 30668    391-ValArgAspArgAlaGlyIleAspAlaArgLeuGly-402
SEQ. ID. NO. 30669    405-PheLeuAlaGluGlyArgLysIleProGlySerAspValAspLeuGlyAsnSerHis-423
SEQ. ID. NO. 30670    430-SerTrpLysArgGlnLeu-435
SEQ. ID. NO. 30671    441-HisProGluAsnGlyHisTyrLeuAspGlyLysIle-452
SEQ. ID. NO. 30672    468-ThrSerAlaArgAlaGly-473
SEQ. ID. NO. 30673    476-PheThrProGluAsnLysLysLeu-483
SEQ. ID. NO. 30674    496-ValAlaArgAspAsnAlaAspValProSer-505
SEQ. ID. NO. 30675    509-PheArgSerGlyGlyAlaSerSerValArgGlyTyrGluLeuAspSer-524
SEQ. ID. NO. 30676    534-ValLeuProGluArgAlaLeu-540
SEQ. ID. NO. 30677    562-AspMetGlyAspAla-566
SEQ. ID. NO. 30678    568-AlaAsnPheLysArgMetLysLeuLysHisGlySerGlyLeu-581
SEQ. ID. NO. 30679    598-TyrGlyHisSerAspLysLysIleArg-606
Hydrophilic Regions - Hopp-Woods
SEQ. ID. NO. 30680    1-MetHisAspThrArgThrMetMet-8
SEQ. ID. NO. 30681    30-AlaAspLeuSerGluAsnLysAla-37
SEQ. ID. NO. 30682    44-LysSerLysSerProAspThrGluSerValLysLeuLysProLysPheProVal-61
SEQ. ID. NO. 30683    63-IleAspThrGlnAspSerGluIleLysAspMetValGluGluHisLeu-78
SEQ. ID. NO. 30684    84-GlnGlnGluGluValLeuAspLysGluGlnThr-94
SEQ. ID. NO. 30685    97-LeuAlaGluGluAlaProAspAsnValLysThrMetLeuArgSer-111
SEQ. ID. NO. 30686    119-ValSerLeuThrGluLysAspGlyAla-127
SEQ. ID. NO. 30687    134-ProGlyProArgThrLysIle-140
SEQ. ID. NO. 30688    174-SerAspPheAspGlnAspSerTrpGluAsnSerLysThr-186
SEQ. ID. NO. 30689    192-ValThrArgLysGlyTyrPro-198
SEQ. ID. NO. 30690    206-ArgAlaAlaValAsnProAspThrAlaThr-215
SEQ. ID. NO. 30691    239-GlnArgTyrProGlu-243
SEQ. ID. NO. 30692    283-AlaAspPheAspArgLeuGlnGlyAspArgValProVal-295
SEQ. ID. NO. 30693    298-SerValThrGluValLysArgHisLysLeuGluThrGlyIleArgLeuAspSerGluTyr-317
SEQ. ID. NO. 30694    342-AspMetAspLysTyrGluThr-348
SEQ. ID. NO. 30695    373-ArgSerThrThrGlnAsnLeuGluLysArgAlaPhe-384
SEQ. ID. NO. 30696    392-ArgAspArgAlaGlyIleAspAlaArgLeuGly-402
SEQ. ID. NO. 30697    405-PheLeuAlaGluGlyArgLysIleProGlySerAspValAspLeu-419
SEQ. ID. NO. 30698    478-ProGluAsnLysLysLeu-483
SEQ. ID. NO. 30699    496-ValAlaArgAspAsnAlaAspVal-503
SEQ. ID. NO. 30700    518-ArgGlyTyrGluLeuAspSer-524
SEQ. ID. NO. 30701    534-ValLeuProGluArgAlaLeu-540
SEQ. ID. NO. 30702    562-AspMetGlyAspAla-566
SEQ. ID. NO. 30703    568-AlaAsnPheLysArgMetLysLeuLysHis-577
SEQ. ID. NO. 30704    600-HisSerAspLysLysIleArg-606
g287
AMPHI Regions - AMPHI
SEQ. ID. NO. 30705    32-AspThrProSerLysPro-37
```

TABLE 1-continued

| | |
|---|---|
| SEQ. ID. NO. 30706 | 111-MetProGlnAsnAlaAlaGluSerAlaAsnGlnThrGly-123 |
| SEQ. ID. NO. 30707 | 195-LeuSerAspGluGluLysIleLysArgTyrLysLys-206 |
| SEQ. ID. NO. 30708 | 351-LysSerValAspGlyIleIleAspSer-359 |
| SEQ. ID. NO. 30709 | 378-GlyPheLysGlyThrTrpThr-384 |
| SEQ. ID. NO. 30710 | 391-ValSerGlyArgPheTyr-396 |
| Antigenic Index - Jameson-Wolf | |
| SEQ. ID. NO. 30711 | 18-CysGlyGlyGlyGlyGlyGlySerProAspValLysSerAlaAspThrProSerLysProAla-38 |
| SEQ. ID. NO. 30712 | 50-ValLeuProLysGluLysLysAspGluGluAlaAlaGlyGlyAlaProGlnAlaAspThrGlnAspAlaThrAlaGlyGluGlySerGlnAsp-80 |
| SEQ. ID. NO. 30713 | 85-SerAlaGluAsnThrGlyAsnGlyGlyAlaAlaThrThrAspAsnProLysAsnGluAspAlaGlyAlaGlnAsnAspMetProGlnAsnAlaAlaGlu SerAlaAsnGlnThrGlyAsnAsnGlnProAlaGlySerSerAspSerAlaProAlaSerAsnProAlaProAlaAsnGlyGlySerAspPheGlyArg ThrAsnValGly-154 |
| SEQ. ID. NO. 30714 | 160-AspGlyProSerGlnAsn-165 |
| SEQ. ID. NO. 30715 | 169-ThrHisCysLysGlyAspSerCysAsnGlyAspAsnLeuLeuAspGluGluAlaProSerLysSerGluPheGluLysLeuSerAspGluGluLys IleLysArgTyrLysLysAspGluGlnArgGluAsnPhe-213 |
| SEQ. ID. NO. 30716 | 217-ValAlaAspArgValLysLysAspGlyThrAsnLys-228 |
| SEQ. ID. NO. 30717 | 233-TyrThrAspLysProProThrArgSerAlaArgSerArgArgSerLeuPro-249 |
| SEQ. ID. NO. 30718 | 262-ThrLeuIleValAspGlyGluAla-269 |
| SEQ. ID. NO. 30719 | 281-AlaProGluGlyAsnTyrArgTyrLeu-289 |
| SEQ. ID. NO. 30720 | 292-GlyAlaGluLysLeuProGlyGlySerTyr-301 |
| SEQ. ID. NO. 30721 | 305-ValGlnGlyGluProAlaLysGlyGluMet-314 |
| SEQ. ID. NO. 30722 | 329-HisMetGluAsnGlyArgProTyrProSerGlyGlyArgPheAlaAla-344 |
| SEQ. ID. NO. 30723 | 346-ValAspPheGlySerLysSerValAspGlyIleIleAspSerGlyAspAspLeuHisMetGlyThrGlnLysPheLysAlaAlaIleAspGlyAsn GlyPheLysGlyThrTrpThrGluAsnGlyGlyGlyAspValSerGly-393 |
| SEQ. ID. NO. 30724 | 395-PheTyrGlyProAlaGlyGluGluValAlaGlyLysTyrSerTyrArgProThrAspAlaGluLysGlyGlyPhe-419 |
| SEQ. ID. NO. 30725 | 423-AlaGlyLysLysAspArgAsp-429 |
| Hydrophilic Regions - Hopp-Woods | |
| SEQ. ID. NO. 30726 | 22-GlyGlySerProAspValLysSerAlaAspThrProSerLysProAla-38 |
| SEQ. ID. NO. 30727 | 50-ValLeuProLysGluLysLysAspGluGluAlaAlaGly-62 |
| SEQ. ID. NO. 30728 | 65-ProGlnAlaAspThrGlnAspAlaThrAlaGlyGluGlySerGlnAsp-80 |
| SEQ. ID. NO. 30729 | 85-SerAlaGluAsnThrGly-90 |
| SEQ. ID. NO. 30730 | 95-AlaThrThrAspAsnProLysAsnGluAspAlaGlyAlaGlnAsnAspMetProGlnAsnAlaAlaGluSerAlaAsnGln-121 |
| SEQ. ID. NO. 30731 | 126-GlnProAlaGlySerSerAspSerAlaPro-135 |
| SEQ. ID. NO. 30732 | 144-GlyGlySerAspPheGlyArg-150 |
| SEQ. ID. NO. 30733 | 171-CysLysGlyAspSerCysAsnGly-178 |
| SEQ. ID. NO. 30734 | 180-AsnLeuLeuAspGluGluAlaProSerLysSerGluPheGluLysLeuSerAspGluGluLysIleLysArgTyrLysLysAspGluGlnArg GluAsnPhe-213 |
| SEQ. ID. NO. 30735 | 217-ValAlaAspArgValLysLysAspGlyThrAsn-227 |
| SEQ. ID. NO. 30736 | 235-AspLysProProThrArgSerAlaArgSerArgArgSerLeuPro-249 |
| SEQ. ID. NO. 30737 | 263-LeuIleValAspGlyGluAla-269 |
| SEQ. ID. NO. 30738 | 292-GlyAlaGluLysLeuPro-297 |
| SEQ. ID. NO. 30739 | 305-ValGlnGlyGluProAlaLysGlyGluMet-314 |
| SEQ. ID. NO. 30740 | 331-GluAsnGlyArgProTyrProSer-338 |
| SEQ. ID. NO. 30741 | 346-ValAspPheGlySerLysSerValAspGlyIleIleAspSerGlyAspAspLeuHis-364 |
| SEQ. ID. NO. 30742 | 368-GlnLysPheLysAlaAlaIleAsp-375 |
| SEQ. ID. NO. 30743 | 387-GlyGlyGlyAspValSerGly-393 |
| SEQ. ID. NO. 30744 | 399-AlaGlyGluGluValAlaGly-405 |
| SEQ. ID. NO. 30745 | 407-TyrSerTyrArgProThrAspAlaGluLysGlyGly-418 |
| SEQ. ID. NO. 30746 | 423-AlaGlyLysLysAspArgAsp-429 |
| g288 | |
| AMPHI Regions - AMPHI | |
| SEQ. ID. NO. 30747 | 7-ValSerArgValLeu-11 |
| SEQ. ID. NO. 30748 | 54-IleValThrLysCysAla-59 |
| SEQ. ID. NO. 30749 | 61-ArgProTyrArgThrPheSerProLeuProVal-71 |
| SEQ. ID. NO. 30750 | 97-HisSerThrLeuArg-101 |
| SEQ. ID. NO. 30751 | 150-ThrLeuPheGlnAlaGlyPheAsp-157 |
| Antigenic Index - Jameson-Wolf | |
| SEQ. ID. NO. 30752 | 2-HisThrGlyGlnAla-6 |
| SEQ. ID. NO. 30753 | 28-AsnLeuProGluArgSerAlaGlySer-36 |
| SEQ. ID. NO. 30754 | 58-CysAlaValArgProTyrArgThrPheSerPro-68 |
| SEQ. ID. NO. 30755 | 72-LeuProLysGlnProSerAla-78 |
| SEQ. ID. NO. 30756 | 89-LeuProArgProAlaValAsnArgHisSerThrLeuArgSerProAspPheProProArgMet-109 |
| SEQ. ID. NO. 30757 | 113-IleArgGlyAspCysLeuPro-119 |
| SEQ. ID. NO. 30758 | 126-IleIleThrArgAsnAlaLysMetProSerGluThrValGlnValSerAspGlyIleGlnProLys-147 |
| SEQ. ID. NO. 30759 | 155-GlyPheAspGluAlaVal-160 |
| Hydrophilic Regions - Hopp-Woods | |
| SEQ. ID. NO. 30760 | 28-AsnLeuProGluArgSerAla-34 |
| SEQ. ID. NO. 30761 | 58-CysAlaValArgPro-62 |
| SEQ. ID. NO. 30762 | 98-SerThrLeuArgSerProAspPheProPro-107 |
| SEQ. ID. NO. 30763 | 113-IleArgGlyAspCys-117 |
| SEQ. ID. NO. 30764 | 126-IleIleThrArgAsnAlaLysMetProSerGluThrValGlnVal-140 |
| SEQ. ID. NO. 30765 | 155-GlyPheAspGluAlaVal-160 |
| g292-2 | |
| AMPHI Regions - AMPHI | |
| SEQ. ID. NO. 30766 | 7-LysIleLeuThrProPheThrValLeuProLeu-17 |
| SEQ. ID. NO. 30767 | 40-GlyLysSerValAla-44 |
| SEQ. ID. NO. 30768 | 62-ValLeuSerValSerGlu-67 |
| SEQ. ID. NO. 30769 | 69-ProValLysGlyIleTyrGlu-75 |
| SEQ. ID. NO. 30770 | 110-GluArgAlaAlaAspLeu-115 |
| SEQ. ID. NO. 30771 | 124-ProLeuAspLysAlaIleLysGluValArgGly-134 |
| SEQ. ID. NO. 30772 | 150-PheCysLysArgLeuGluHisGluPheGluLysMetThrAspValThr-165 |

TABLE 1-continued

| | |
|---|---|
| SEQ. ID. NO. 30773 | 195-LysAlaTrpThrAspTrpMetArg-202 |
| SEQ. ID. NO. 30774 | 212-IleCysAspAsnProVal-217 |
| Antigenic Index - Jameson-Wolf | |
| SEQ. ID. NO. 30775 | 1-MetLysThrLysLeu-5 |
| SEQ. ID. NO. 30776 | 23-ThrProValSerAsnAlaAsnAlaGluSerAlaValLysAlaGluSerAlaGlyLysSerVal-43 |
| SEQ. ID. NO. 30777 | 47-LeuLysAlaArgLeuGluLysThrTyrSerAlaGlnAspLeuLys-61 |
| SEQ. ID. NO. 30778 | 66-SerGluThrProValLysGlyIle-73 |
| SEQ. ID. NO. 30779 | 85-TyrThrAspAlaGluGlyGlyTyr-92 |
| SEQ. ID. NO. 30780 | 99-IleAsnIleAspThrArgLysAsnLeuThrGluGluArgAlaAlaAspLeuAsnLys-117 |
| SEQ. ID. NO. 30781 | 124-ProLeuAspLysAlaIleLysGluValArgGlyAsnGlyLysLeuLysVal-140 |
| SEQ. ID. NO. 30782 | 142-ValPheSerAspProAspCysProPhe-150 |
| SEQ. ID. NO. 30783 | 152-LysArgLeuGluHisGluPheGluLysMetThrAsp-163 |
| SEQ. ID. NO. 30784 | 177-HisProAspAlaAlaArgLysAla-184 |
| SEQ. ID. NO. 30785 | 189-CysGlnProAspArgAlaLysAla-196 |
| SEQ. ID. NO. 30786 | 200-TrpMetArgLysGlyLysPheProVal-208 |
| SEQ. ID. NO. 30787 | 210-GlySerIleCysAspAsnProValAlaGluThrThrSerLeuGlyGlu-225 |
| SEQ. ID. NO. 30788 | 238-ProAsnGlyArgThrGlnSerGlyTyrSerPro-248 |
| SEQ. ID. NO. 30789 | 250-ProGlnLeuGluGluIleIleArgLysAsnGlnGln-261 |
| Hydrophilic Regions - Hopp-Woods | |
| SEQ. ID. NO. 30790 | 1-MetLysThrLysLeu-5 |
| SEQ. ID. NO. 30791 | 28-AlaAsnAlaGluSerAlaValLysAlaGluSerAlaGlyLysSerVal-43 |
| SEQ. ID. NO. 30792 | 47-LeuLysAlaArgLeuGluLysThrTyrSer-56 |
| SEQ. ID. NO. 30793 | 99-IleAsnIleAspThrArgLysAsnLeuThrGluGluArgAlaAlaAspLeuAsnLys-117 |
| SEQ. ID. NO. 30794 | 124-ProLeuAspLysAlaIleLysGluValArgGlyAsnGlyLysLeuLys-139 |
| SEQ. ID. NO. 30795 | 144-SerAspProAspCysProPhe-150 |
| SEQ. ID. NO. 30796 | 152-LysArgLeuGluHisGluPheGluLysMetThrAsp-163 |
| SEQ. ID. NO. 30797 | 179-AspAlaAlaArgLysAla-184 |
| SEQ. ID. NO. 30798 | 190-GlnProAspArgAlaLysAla-196 |
| SEQ. ID. NO. 30799 | 200-TrpMetArgLysGlyLysPhe-206 |
| SEQ. ID. NO. 30800 | 240-GlyArgThrGlnSer-244 |
| SEQ. ID. NO. 30801 | 250-ProGlnLeuGluGluIleIleArgLysAsnGlnGln-261 |
| g294-2 | |
| AMPHI Regions - AMPHI | |
| SEQ. ID. NO. 30802 | 27-ArgPheProAlaAlaLeuArgArgTyrSer-36 |
| SEQ. ID. NO. 30803 | 45-LysProAlaGlyThr-49 |
| SEQ. ID. NO. 30804 | 51-TrpHisArgValArgArgPheLysSerAsnArgArgThrArgGlyValLysProLeu-69 |
| SEQ. ID. NO. 30805 | 85-AlaTrpThrAlaLeuSerHisAsnIleAlaGluAlaGluAlaGluSerProArgArgCysGlyLysArgTyrAlaAspIleGlyGly-113 |
| SEQ. ID. NO. 30806 | 134-ValAlaHisIleIleHisLeuTyrCys-142 |
| SEQ. ID. NO. 30807 | 165-ValSerArgGluAlaArgArgGluVal-173 |
| SEQ. ID. NO. 30808 | 176-AlaMetSerTyrArg-180 |
| SEQ. ID. NO. 30809 | 212-PheAlaThrSerPheGly-217 |
| SEQ. ID. NO. 30810 | 227-AlaPheSerValLeuAlaHisPhe-234 |
| SEQ. ID. NO. 30811 | 247-ThrValGlyTrpSerLysTyrIleHisAlaVal-257 |
| Antigenic Index - Jameson-Wolf | |
| SEQ. ID. NO. 30812 | 20-AlaValArgThrSerSerAsnArgPhe-28 |
| SEQ. ID. NO. 30813 | 30-AlaAlaLeuArgArgTyrSerArgAlaPheArg-39 |
| SEQ. ID. NO. 30814 | 44-ProLysProAlaGlyThrProTrpHisArgValArgArgPheLysSerAsnArgArgThrArgGlyValLysProLeuLysLysProTyrLeu-74 |
| SEQ. ID. NO. 30815 | 76-ArgGlyAlaGluCysArgCysArgArgAla-85 |
| SEQ. ID. NO. 30816 | 93-IleAlaGluArgAlaArgGluSerProArgArgCysGlyLysArgTyrAlaAspIleGlyGlyAspSerAspThrIleArgIleArgValPheArgLeuGluHisArgMet-129 |
| SEQ. ID. NO. 30817 | 161-HisThrGlyArgValSerArgGluAlaArgArgGluValGluLysAlaMetSer-178 |
| SEQ. ID. NO. 30818 | 240-LysMetAlaArgSer-244 |
| Hydrophilic Regions - Hopp-Woods | |
| SEQ. ID. NO. 30819 | 20-AlaValArgThrSerSerAsnArg-27 |
| SEQ. ID. NO. 30820 | 30-AlaAlaLeuArgArg-34 |
| SEQ. ID. NO. 30821 | 52-HisArgValArgArgPheLysSerAsnArgArgThrArgGlyValLysProLeuLysLys-71 |
| SEQ. ID. NO. 30822 | 76-ArgGlyAlaGluCysArgCysArgArgAla-85 |
| SEQ. ID. NO. 30823 | 93-IleAlaGluArgAlaArgGluSerProArgArgCysGlyLysArgTyrAlaAspIleGlyGlyAspSerAspThrIleArg-119 |
| SEQ. ID. NO. 30824 | 121-ArgValPheArgLeuGluHisArgMet-129 |
| SEQ. ID. NO. 30825 | 164-ArgValSerArgGluAlaArgArgGluValGluLysAlaMetSer-178 |
| g295 | |
| AMPHI Regions - AMPHI | |
| SEQ. ID. NO. 30826 | 79-PheArgGlnProArg-83 |
| SEQ. ID. NO. 30827 | 111-ValGlnArgPhePheArgGlnPro-118 |
| SEQ. ID. NO. 30828 | 131-AlaPheLeuHisGlnIle-136 |
| SEQ. ID. NO. 30829 | 163-ValIleArgLysIleAlaAlaLeu-170 |
| SEQ. ID. NO. 30830 | 176-AsnLeuArgGlyPhePro-181 |
| SEQ. ID. NO. 30831 | 189-HisGlnGlnArgArgIleGlyLysThr-197 |
| SEQ. ID. NO. 30832 | 263-TyrIleIleLysProLeuGluHis-270 |
| Antigenic Index - Jameson-Wolf | |
| SEQ. ID. NO. 30833 | 4-MetAlaArgHisAspGlyGlnGlnGly-12 |
| SEQ. ID. NO. 30834 | 18-LeuProArgArgGlnGln-23 |
| SEQ. ID. NO. 30835 | 36-AlaAlaAlaHisGlyAsnArgProAlaSerAspAlaPhePheLysLeuProArgGlnArgPheHisVal-58 |
| SEQ. ID. NO. 30836 | 73-HisGlyCysArgAlaGlnPheArgGlnProArgArgIleArgLeuArgLeuArgGlnThrAlaArgGlnArgSerGlyCysGlyThrAspGlnAlaAlaAsp-106 |
| SEQ. ID. NO. 30837 | 115-PheArgGlnProArgIleArgGlnLysGlnArgHisThrArgSerProAla-131 |
| SEQ. ID. NO. 30838 | 137-GlyProAspPheGly-141 |
| SEQ. ID. NO. 30839 | 144-GlnAsnAlaGluHisArgAla-150 |
| SEQ. ID. NO. 30840 | 171-ArgIleGlyLysGlnAsnLeuArgGlyPheProSerArgArgGlyHisLeuArgHisGlnGlnArgArgIleGlyLysThrProProGlnLeuAla-202 |
| SEQ. ID. NO. 30841 | 207-GlyGlyThrArgPheSerAspArgAsnGlyValTyrProAsnArgAlaGlyAsnGlyIleArgMetArgLeuAlaGlu-232 |

TABLE 1-continued

| | |
|---|---|
| SEQ. ID. NO. 30842 | 239-ProValCysArgGlyThrSerGly-246 |
| SEQ. ID. NO. 30843 | 253-ProTyrProTyrArgArgLysGlnProGlnTyr-263 |
| SEQ. ID. NO. 30844 | 274-SerCysLysThrAsnAlaValArgThrValArgThrAlaPheArgGlnArgAsnGlnIleSer-294 |

Hydrophilic Regions - Hopp-Woods

| | |
|---|---|
| SEQ. ID. NO. 30845 | 5-AlaArgHisAspGlyGlnGln-11 |
| SEQ. ID. NO. 30846 | 18-LeuProArgArgGlnGln-23 |
| SEQ. ID. NO. 30847 | 36-AlaAlaAlaHisGlyAsnArgProAlaSer-45 |
| SEQ. ID. NO. 30848 | 77-AlaGlnPheArgGlnProArgArgIleArgLeuArgLeuArgGlnThrAlaArgGlnArgSerGlyCysGlyThrAspGlnAlaAla-105 |
| SEQ. ID. NO. 30849 | 118-ProArgIleArgGlnLysGlnArgHisThrArg-128 |
| SEQ. ID. NO. 30850 | 146-AlaGluHisArgAla-150 |
| SEQ. ID. NO. 30851 | 171-ArgIleGlyLysGlnAsnLeu-177 |
| SEQ. ID. NO. 30852 | 180-PheProSerArgArgGlyHisLeuArgHisGlnGlnArgArgIleGlyLysThrProPro-199 |
| SEQ. ID. NO. 30853 | 210-ArgPheSerAspArgAsnGly-216 |
| SEQ. ID. NO. 30854 | 226-IleArgMetArgLeuAlaGlu-232 |
| SEQ. ID. NO. 30855 | 239-ProValCysArgGlyThr-244 |
| SEQ. ID. NO. 30856 | 255-ProTyrArgArgLysGlnPro-261 |
| SEQ. ID. NO. 30857 | 281-ArgThrValArgThrAlaPheArgGlnArgAsnGlnIle-293 | g297
AMPHI Regions - AMPHI

| | |
|---|---|
| SEQ. ID. NO. 30858 | 69-GlnProGlyAspSerLeuAlaAspValLeuAla-79 |
| SEQ. ID. NO. 30859 | 86-AspGluIleAlaArgIleThrGluLysTyr-95 |
| SEQ. ID. NO. 30860 | 157-LeuProThrLeuArg-161 |
| SEQ. ID. NO. 30861 | 199-LeuLysGluGlyAspAla-204 |
| SEQ. ID. NO. 30862 | 272-LeuValTyrThrArgIleSerSer-279 |
| SEQ. ID. NO. 30863 | 333-HisAlaAsnGlyValGluThrLeuTyrAlaHisLeuSerAlaPheSerGln-349 |

Antigenic Index - Jameson-Wolf

| | |
|---|---|
| SEQ. ID. NO. 30864 | 8-AlaLysHisArgLysTyrAla-14 |
| SEQ. ID. NO. 30865 | 31-AlaSerThrGluGlyThrGluArgValArgProGlnArgValGluGlnLysLeuPro-49 |
| SEQ. ID. NO. 30866 | 52-SerTrpGlyGlyAsnGly-57 |
| SEQ. ID. NO. 30867 | 67-AlaValGlnProGlyAspSerLeuAla-75 |
| SEQ. ID. NO. 30868 | 78-LeuAlaArgSerGlyMetAlaArgAspGluIleAlaArgIleThrGluLysTyrGlyGlyGluAlaAspLeuArgHisLeuArgAlaAspGlnSerVal-110 |
| SEQ. ID. NO. 30869 | 115-GlyGlyAspGlySerAlaArgGlu-122 |
| SEQ. ID. NO. 30870 | 127-ThrAspGluAspGlyGluArgAsnLeuValAlaLeuGluLysLysGlyGlyIleTrpArgArgSerAlaSerAspAlaAspMetLysVal-156 |
| SEQ. ID. NO. 30871 | 167-ThrSerAlaArgGlySerLeuAlaArgAlaGluValProValGluIleArgGluSerLeuSer-187 |
| SEQ. ID. NO. 30872 | 194-PheSerLeuAspGlyLeuLysGluGlyAspAlaVal-205 |
| SEQ. ID. NO. 30873 | 228-GluValValLysGlyGlyThrThr-235 |
| SEQ. ID. NO. 30874 | 240-TyrTyrArgSerAspLysGluGlyGlyGlyGlyGlyAsnTyrTyrAspGluAspGlyArgValLeuGlnGluLysGlyGlyPheAsn-268 |
| SEQ. ID. NO. 30875 | 276-ArgIleSerSerProPheGlyTyr-283 |
| SEQ. ID. NO. 30876 | 295-HisThrGlyIleAspTyrAla-301 |
| SEQ. ID. NO. 30877 | 303-ProGlnGlyThrProValArgAlaSerAlaAspGly-314 |
| SEQ. ID. NO. 30878 | 318-PheLysGlyArgLysGlyGlyTyrGly-326 |
| SEQ. ID. NO. 30879 | 333-HisAlaAsnGlyValGlu-338 |
| SEQ. ID. NO. 30880 | 350-AlaGlnGlyAsnValArgGlyGlyGlu-358 |
| SEQ. ID. NO. 30881 | 365-SerThrGlyArgSerThrGlyProHisLeu-374 |
| SEQ. ID. NO. 30882 | 376-TyrGluAlaArgIleAsnGlyGlnProValAsn-386 |
| SEQ. ID. NO. 30883 | 393-ProThrProGluLeuThrGlnAlaAspLysAlaAla-404 |
| SEQ. ID. NO. 30884 | 408-GlnLysGlnLysAlaAspAlaLeu-415 |
| SEQ. ID. NO. 30885 | 426-ValSerGlnSerAsp-430 |

Hydrophilic Regions - Hopp-Woods

| | |
|---|---|
| SEQ. ID. NO. 30886 | 8-AlaLysHisArgLysTyrAla-14 |
| SEQ. ID. NO. 30887 | 33-ThrGluGlyThrGluArgValArgProGlnArgValGluGlnLysLeu-48 |
| SEQ. ID. NO. 30888 | 68-ValGlnProGlyAspSerLeuAla-75 |
| SEQ. ID. NO. 30889 | 82-GlyMetAlaArgAspGluIleAlaArgIleThrGluLysTyrGlyGlyGluAlaAspLeuArgHisLeuArgAlaAspGln-108 |
| SEQ. ID. NO. 30890 | 117-AspGlySerAlaArgGlu-122 |
| SEQ. ID. NO. 30891 | 127-ThrAspGluAspGlyGluArgAsnLeuValAlaLeuGluLysLysGlyGlyIleTrpArgArgSerAlaSerAspAlaAspMetLysVal-156 |
| SEQ. ID. NO. 30892 | 167-ThrSerAlaArgGlySerLeuAlaArgAlaGluValProValGluIleArgGluSerLeu-186 |
| SEQ. ID. NO. 30893 | 194-PheSerLeuAspGlyLeuLysGluGlyAspAlaVal-205 |
| SEQ. ID. NO. 30894 | 242-ArgSerAspLysGluGlyGlyGlyGly-249 |
| SEQ. ID. NO. 30895 | 253-TyrTyrAspGluAspGlyArgValLeuGlnGluLysGlyGlyPhe-267 |
| SEQ. ID. NO. 30896 | 306-ThrProValArgAlaSerAla-312 |
| SEQ. ID. NO. 30897 | 319-LysGlyArgLysGlyGlyTyr-325 |
| SEQ. ID. NO. 30898 | 352-GlyAsnValArgGlyGlyGlu-358 |
| SEQ. ID. NO. 30899 | 366-ThrGlyArgSerThrGly-371 |
| SEQ. ID. NO. 30900 | 378-AlaArgIleAsnGly-382 |
| SEQ. ID. NO. 30901 | 396-GluLeuThrGlnAlaAspLysAlaAla-404 |
| SEQ. ID. NO. 30902 | 408-GlnLysGlnLysAlaAspAlaLeu-415 | g298
AMPHI Regions - AMPHI

| | |
|---|---|
| SEQ. ID. NO. 30903 | 6-SerLeuPheAlaSerIleLeuMetSerAlaLeuIleAla-18 |
| SEQ. ID. NO. 30904 | 26-IleAsnAlaTyrTrpGlnGln-32 |
| SEQ. ID. NO. 30905 | 42-ProLeuAlaAlaTyr-46 |
| SEQ. ID. NO. 30906 | 62-LeuSerAspGlyIleLysThrPhe-69 |
| SEQ. ID. NO. 30907 | 134-ValGlnLysSerLeuLys-139 |
| SEQ. ID. NO. 30908 | 148-AsnLeuSerLysGln-152 |
| SEQ. ID. NO. 30909 | 157-SerTyrProSerPhePheAspTrpProLysThrIleGluGluThrLeuLysLysHisProGlu-177 |
| SEQ. ID. NO. 30910 | 188-AsnAspProTrpAsp-192 |
| SEQ. ID. NO. 30911 | 208-AlaGlnGluTyrLeuLysArgValAspArgIleLeuGlu-220 |
| SEQ. ID. NO. 30912 | 246-MetArgTyrLeuAspLysLeuLeuSerGluHisLeu-257 |
| SEQ. ID. NO. 30913 | 276-ArgTyrThrAspSer-280 |
| SEQ. ID. NO. 30914 | 308-GluLysIleMetGluLys-313 |

TABLE 1-continued

Antigenic Index - Jameson-Wolf
SEQ. ID. NO. 30915  22-SerGlnAsnProIleAsnAlaTyr-29
SEQ. ID. NO. 30916  34-TyrHisArgAsnSerProLeuGluPro-42
SEQ. ID. NO. 30917  47-GlyTrpTrpArgSerGlyAlaAlaLeuGlnGlu-57
SEQ. ID. NO. 30918  70-LeuSerGlyGluThrProProThrAlaGlnAspGlyGlySerAlaAspMetProProGluAlaAlaAlaSerGluAlaAlaProProAlaGlyGlyThr
GluTrpLysGlnGlyThrGlu-109
SEQ. ID. NO. 30919  111-AlaAlaValArgSerGlyAspLysValPhePhe-121
SEQ. ID. NO. 30920  136-LysSerLeuLysGlnGlnTyrGlyIleGluSerAlaAsnLeuSerLysGlnSerThr-154
SEQ. ID. NO. 30921  162-PheAspTrpProLysThrIleGluGluThrLeuLysLysHisProGlu-177
SEQ. ID. NO. 30922  186-GlyProAsnAspProTrp-191
SEQ. ID. NO. 30923  194-ProValGlyLysArgTyrLeu-200
SEQ. ID. NO. 30924  203-AlaSerAspGluTrpAla-208
SEQ. ID. NO. 30925  211-TyrLeuLysArgValAspArgIleLeuGlu-220
SEQ. ID. NO. 30926  238-LysLysValLysLeuAspGlyGlnMetArgTyrLeuAsp-250
SEQ. ID. NO. 30927  252-LeuLeuSerGluHisLeuLysGly-259
SEQ. ID. NO. 30928  269-ThrLeuSerGlyGlyLysGlyArgTyrThrAspSerValAsnValAsnGlyLysProValArgTyrArgSerLysAspGlyIle-296
SEQ. ID. NO. 30929  301-GluGlyGlnLysLeuLeuAla-307
SEQ. ID. NO. 30930  318-ProSerThrGlnProSerSerThrGlnPro-327
Hydrophilic Regions - Hopp-Woods
SEQ. ID. NO. 30931  73-GluThrProProThrAlaGlnAspGlyGlySerAlaAspMetProProGluAlaAlaAlaSerGluAlaAlaPro-97
SEQ. ID. NO. 30932  102-ThrGluTrpLysGlnGlyThrGlu-109
SEQ. ID. NO. 30933  111-AlaAlaValArgSerGlyAsp-117
SEQ. ID. NO. 30934  148-AsnLeuSerLysGlnSerThr-154
SEQ. ID. NO. 30935  166-LysThrIleGluGluThrLeuLysLysHisProGlu-177
SEQ. ID. NO. 30936  211-TyrLeuLysArgValAspArgIleLeuGlu-220
SEQ. ID. NO. 30937  238-LysLysValLysLeuAspGlyGlnMetArgTyrLeuAsp-250
SEQ. ID. NO. 30938  252-LeuLeuSerGluHisLeuLysGly-259
SEQ. ID. NO. 30939  271-SerGlyGlyLysGlyArgTyrThrAsp-279
SEQ. ID. NO. 30940  281-ValAsnValAsnGlyLysProValArgTyrArgSerLysAspGlyIle-296
SEQ. ID. NO. 30941  301-GluGlyGlnLysLeuLeuAla-307
SEQ. ID. NO. 30942  319-SerThrGlnProSerSerThrGlnPro-327
g299
AMPHI Regions - AMPHI
SEQ. ID. NO. 30943  1-MetAsnProLysHisPheIleAlaPheSerAlaLeuPheAlaAlaThrGlnAlaGluAlaLeuProValAlaSerValSerProAspThrValThrValSer
ProSerAlaProTyrThrAspThrAsnGlyLeuLeuThrAspTyrGlyAsnAlaAlaAlaSerProTrpMetLysLysLeuArgSerValAlaGlnGlySerGl
yGluAlaPheArgIleLeuGlnIleGlyAspSerHisThrAlaGlyAspPhePheThrAspAlaLeuArgLysArgLeuGlnLysThrTrpGlyAspGlyGlyI
leGlyTrpValTyrProAlaAsnValLysGlyGlnArgMetAlaAlaValArgHisSerGlyAsnTrpGlnSerPheThrSerArgAsnAsnThrGlyAspPhe
ProLeuGlyGlyIleLeuAlaGlnThrGlySerGlyGlyGlyMetThrLeuThrAlaSerAspGlyLysThrGlyLysGlnArgValSerLeuPheAlaLysPr
oLeuLeuAlaGluGlnThrLeuThrValAsnGlyAsnThrValSerAlaAsnGlyGlyGlyTrpGlnValLeuAspThrGlyAlaAlaLeuProLeuAlaIleG
lnThrGluMetProTrpAspIleGlyPheIleAsnIleGluAsnProAlaGlyGlyIleThrValSerAlaMetGlyIleAsnGlyAlaGlnLeuThrGlnTrp
SerLysTrpArgAlaAspArgMetAsnAspLeuAlaGlnThrGlyAlaAspLeuValIleLeuSerTyrGlyThrAsnGluAlaPheAsnAsnAsnIleAspIl
eAlaAspThrGluGlnLysTrpLeuAspThrValArgGlnIleArgAspSerLeuProAlaAlaGlyIleLeuIleIleGlyAlaProGluSerLeuLysAsnT
hrLeuGlyValCysGlyThrArgProValLeuLeuThrGluValGlnGlnMetGlnArgArgValAlaArgGlnGlyGlnThrMetPheTrpSerTrpGlnAsn
AlaMetGlyGlyIleCysSerMetLysAsnTrpLeuAsnGlnGlyTrpAlaAlaLysAspGlyValHisPheSerAlaGlnGlyTyrArgArgAlaAlaGluMe
tLeuAlaAspSerLeuGluGluLeuValArgAlaAlaAlaIleArgGln-397
Antigenic Index - Jameson-Wolf (SEQ. ID. NO. 30943)
1-MetAsnProLysHisPheIleAlaPheSerAlaLeuPheAlaAlaThrGlnAlaGluAlaLeuProValAlaSe
rValSerProAspThrValThrValSerProSerAlaProTyrThrAspThrAsnGlyLeuLeuThrAspTyrGly
AsnAlaAlaAlaSerProTrpMetLysLysLeuArgSerValAlaGlnGlySerGlyGluAlaPheArgIleLeuG
lnIleGlyAspSerHisThrAlaGlyAspPhePheThrAspAlaLeuArgLysArgLeuGlnLysThrTrpGlyAs
pGlyGlyIleGlyTrpValTyrProAlaAsnValLysGlyGlnArgMetAlaAlaValArgHisSerGlyAsnTrp
GlnSerPheThrSerArgAsnAsnThrGlyAspPheProLeuGlyGlyIleLeuAlaGlnThrGlySerGlyGlyG
lyMetThrLeuThrAlaSerAspGlyLysThrGlyLysGlnArgValSerLeuPheAlaLysProLeuLeuAlaGl
uGlnThrLeuThrValAsnGlyAsnThrValSerAlaAsnGlyGlyGlyTrpGlnValLeuAspThrGlyAlaAla
LeuProLeuAlaIleGlnThrGluMetProTrpAspIleGlyPheIleAsnIleGluAsnProAlaGlyGlyIleT
hrValSerAlaMetGlyIleAsnGlyAlaGlnLeuThrGlnTrpSerLysTrpArgAlaAspArgMetAsnAspLe
uAlaGlnThrGlyAlaAspLeuValIleLeuSerTyrGlyThrAsnGluAlaPheAsnAsnAsnIleAspIleAla
AspThrGluGlnLysTrpLeuAspThrValArgGlnIleArgAspSerLeuProAlaAlaGlyIleLeuIleIleG
lyAlaProGluSerLeuLysAsnThrLeuGlyValCysGlyThrArgProValLeuLeuThrGluValGlnGlnMe
tGlnArgArgValAlaArgGlnGlyGlnThrMetPheTrpSerTrpGlnAsnAlaMetGlyGlyIleCysSerMet
LysAsnTrpLeuAsnGlnGlyTrpAlaAlaLysAspGlyValHisPheSerAlaGlnGlyTyrArgArgAlaAlaG
luMetLeuAlaAspSerLeuGluGluLeuValArgAlaAlaAlaIleArgGln-397
Hydrophilic Regions - Hopp-Woods (SEQ. ID. NO. 30943)
1-MetAsnProLysHisPheIleAlaPheSerAlaLeuPheAlaAlaThrGlnAlaGluAlaLeuProValAlaSe
rValSerProAspThrValThrValSerProSerAlaProTyrThrAspThrAsnGlyLeuLeuThrAspTyrGly
AsnAlaAlaAlaSerProTrpMetLysLysLeuArgSerValAlaGlnGlySerGlyGluAlaPheArgIleLeuG
lnIleGlyAspSerHisThrAlaGlyAspPhePheThrAspAlaLeuArgLysArgLeuGlnLysThrTrpGlyAs
pGlyGlyIleGlyTrpValTyrProAlaAsnValLysGlyGlnArgMetAlaAlaValArgHisSerGlyAsnTrp
GlnSerPheThrSerArgAsnAsnThrGlyAspPheProLeuGlyGlyIleLeuAlaGlnThrGlySerGlyGlyG
lyMetThrLeuThrAlaSerAspGlyLysThrGlyLysGlnArgValSerLeuPheAlaLysProLeuLeuAlaGl
uGlnThrLeuThrValAsnGlyAsnThrValSerAlaAsnGlyGlyGlyTrpGlnValLeuAspThrGlyAlaAla
LeuProLeuAlaIleGlnThrGluMetProTrpAspIleGlyPheIleAsnIleGluAsnProAlaGlyGlyIleT
hrValSerAlaMetGlyIleAsnGlyAlaGlnLeuThrGlnTrpSerLysTrpArgAlaAspArgMetAsnAspLe
uAlaGlnThrGlyAlaAspLeuValIleLeuSerTyrGlyThrAsnGluAlaPheAsnAsnAsnIleAspIleAla
AspThrGluGlnLysTrpLeuAspThrValArgGlnIleArgAspSerLeuProAlaAlaGlyIleLeuIleIleG
lyAlaProGluSerLeuLysAsnThrLeuGlyValCysGlyThrArgProValLeuLeuThrGluValGlnGlnMe
tGlnArgArgValAlaArgGlnGlyGlnThrMetPheTrpSerTrpGlnAsnAlaMetGlyGlyIleCysSerMet
LysAsnTrpLeuAsnGlnGlyTrpAlaAlaLysAspGlyValHisPheSerAlaGlnGlyTyrArgArgAlaAlaG
luMetLeuAlaAspSerLeuGluGluLeuValArgAlaAlaAlaIleArgGln-397

TABLE 1-continued g302
AMPHI Regions - AMPHI
SEQ. ID. NO. 30944  20-SerGlyArgPheLeuArgThrValGluTrpLeuGlyAsnMetLeuProHisPro-37
SEQ. ID. NO. 30945  81-ValValSerLeuLeuAspAlaAspGlyLeuIleLysIleLeuThrHisThrValLysAsnPheThrGlyPheAlaProLeuGlyThrValLeu
ValSerLeu-114
SEQ. ID. NO. 30946  127-SerAlaLeuMetArg-131
SEQ. ID. NO. 30947  171-IlePheHisSerLeuGlyArgHisProLeuAlaGlyLeuAlaAlaAlaPheAlaGlyValSerGly-192
SEQ. ID. NO. 30948  201-GlyThrIleAspProLeuLeuAlaGlyIleThrGlnGlnAla-214
SEQ. ID. NO. 30949  240-IleAlaLeuIleGly-244
SEQ. ID. NO. 30950  271-ArgHisSerAsnGluIle-276
SEQ. ID. NO. 30951  294-LeuSerAlaLeuLeuAlaTrp-300
SEQ. ID. NO. 30952  308-IleLeuArgHisProGluThr-314
SEQ. ID. NO. 30953  341-TyrGlyArgIleThrArgSerLeuArgGly-350
SEQ. ID. NO. 30954  352-ArgGluValValAsnAlaMetAlaGluSerMetSer-363
SEQ. ID. NO. 30955  378-PheValAlaPhePheAsnTrpThrAsnIleGlyGlnTyrIle-391
SEQ. ID. NO. 30956  448-AlaProGlnValIle-452
SEQ. ID. NO. 30957  455-AlaTyrArgIleGlyAspSerValThrAsnIleIleThrProMetMetSerTyrPheGlyLeuIleMetAla-478
SEQ. ID. NO. 30958  505-IleAlaTrpIleAlaLeuPheCysIle-513
Antigenic Index - Jameson-Wolf
SEQ. ID. NO. 30959  8-LysGluLysGlnMetSerGlnThrAspAlaArgArgSerGlyArgPheLeuArg-25
SEQ. ID. NO. 30960  61-SerValProAspProArgProValGlyAlaLysGlyArgAlaAspAspGlyLeu-78
SEQ. ID. NO. 30961  85-LeuAspAlaAspGlyLeu-90
SEQ. ID. NO. 30962  119-IleAlaGluLysSerGly-124
SEQ. ID. NO. 30963  134-LeuThrLysSerProArgLysLeuThr-142
SEQ. ID. NO. 30964  152-LeuSerAsnThrAlaSerGlu-158
SEQ. ID. NO. 30965  175-LeuGlyArgHisProLeu-180
SEQ. ID. NO. 30966  250-LysIleValGluProGlnLeuGlyProTyrGlnSerAspLeuSerGlnGluGluLysAspIleArgHisSerAsnGluIleThrProLeuGluTyrLys-282
SEQ. ID. NO. 30967  304-ProAlaAspGlyIleLeuArgHisProGluThrGlyLeu-316
SEQ. ID. NO. 30968  343-ArgIleThrArgSerLeuArgGlyGluArgGluValVal-355
SEQ. ID. NO. 30969  402-ValGlyLeuGlyGly-406
SEQ. ID. NO. 30970  482-LysTyrLysLysAspAlaGlyVal-489
Hydrophilic Regions - Hopp-Woods
SEQ. ID. NO. 30971  8-LysGluLysGlnMetSerGlnThrAspAlaArgArgSerGlyArgPhe-23
SEQ. ID. NO. 30972  63-ProAspProArgProValGlyAlaLysGlyArgAlaAspAspGlyLeu-78
SEQ. ID. NO. 30973  85-LeuAspAlaAspGlyLeu-90
SEQ. ID. NO. 30974  119-IleAlaGluLysSerGly-124
SEQ. ID. NO. 30975  136-LysSerProArgLysLeu-141
SEQ. ID. NO. 30976  263-LeuSerGlnGluGluLysAspIleArgHisSerAsnGlu-275
SEQ. ID. NO. 30977  307-GlyIleLeuArgHisProGlu-313
SEQ. ID. NO. 30978  344-IleThrArgSerLeuArgGlyGluArgGluValVal-355
SEQ. ID. NO. 30979  482-LysTyrLysLysAspAlaGly-488
g305
AMPHI Regions - AMPHI
SEQ. ID. NO. 30980  10-LeuMetMetGlyLeuValGluGlyPheThrGluPheLeuPro-23
SEQ. ID. NO. 30981  33-PheGlyAsnLeuIleGly-38
SEQ. ID. NO. 30982  66-PheSerAsnValLeuHis-71
SEQ. ID. NO. 30983  93-AlaAlaValMetGly-97
SEQ. ID. NO. 30984  99-LeuPheAspLysGlnIleLysGluTyrLeuPhe-109
SEQ. ID. NO. 30985  141-AspValAspAlaLeuArgProIleAspAla-150
SEQ. ID. NO. 30986  155-ValAlaGlnValPheAla-160
SEQ. ID. NO. 30987  202-AlaTyrAspValLeuLysHisTyrArgPhePheThrLeuHis-215
SEQ. ID. NO. 30988  222-IleGlyPheIleAlaAlaPheValSer-230
SEQ. ID. NO. 30989  235-ValLysAlaLeuLeuLys-240
Antigenic Index - Jameson-Wolf
SEQ. ID. NO. 30990  41-SerAsnHisLysValPhe-46
SEQ. ID. NO. 30991  61-GluTyrArgGlnArgPheSerAsn-68
SEQ. ID. NO. 30992  72-GlyValGlyLysAspArgLysAlaAsn-80
SEQ. ID. NO. 30993  128-ValGluLysArgGlnSerArgAlaGluProLysIleAlaAsp-141
SEQ. ID. NO. 30994  143-AspAlaLeuArgProIleAsp-149
SEQ. ID. NO. 30995  163-ProGlyThrSerArgSerGlySerThr-171
SEQ. ID. NO. 30996  180-IleGluArgLysThrAlaThr-186
SEQ. ID. NO. 30997  241-PheValSerLysLysAsnTyr-247
Hydrophilic Regions - Hopp-Woods
SEQ. ID. NO. 30998  62-TyrArgGlnArgPhe-66
SEQ. ID. NO. 30999  73-ValGlyLysAspArgLysAlaAsn-80
SEQ. ID. NO. 31000  128-ValGluLysArgGlnSerArgAlaGluProLysIleAlaAsp-141
SEQ. ID. NO. 31001  143-AspAlaLeuArgProIleAsp-149
SEQ. ID. NO. 31002  165-ThrSerArgSerGlySer-170
SEQ. ID. NO. 31003  180-IleGluArgLysThrAlaThr-186
SEQ. ID. NO. 31004  242-ValSerLysLysAsn-246
g308-1
AMPHI Regions - AMPHI
SEQ. ID. NO. 31005  6-PheTyrArgIleLeuGlyValAlaAsp-14
SEQ. ID. NO. 31006  27-ThrIleIleAlaGlyLeu-32
SEQ. ID. NO. 31007  64-AlaLeuGluLeuLeuArgAlaGln-71
SEQ. ID. NO. 31008  83-AlaGluMetAlaArgAlaSerGlu-90
SEQ. ID. NO. 31009  101-LeuAlaAspPheValHisProIleGlyAsnIleGlyAlaCys-114
SEQ. ID. NO. 31010  131-SerMetArgThrLeuAlaSerValAlaHisGlyPheGlyAsp-144
SEQ. ID. NO. 31011  172-LeuAlaHisLeuAspAsnMetLysArgValThrGlu-183

TABLE 1-continued

Antigenic Index - Jameson-Wolf
SEQ. ID. NO. 31012    39-TrpGluArgArgMetMetVal-45
SEQ. ID. NO. 31013    68-LeuArgAlaGlnAspValGluThr-75
SEQ. ID. NO. 31014    80-SerLysGlyAlaGluMetAlaArgAlaSerGluThrAspTyrThrLysAspGluVal-98
SEQ. ID. NO. 31015    118-GlyThrPheLysThrAspGlyMet-125
SEQ. ID. NO. 31016    141-GlyPheGlyAspAsnLeuLeu-147
SEQ. ID. NO. 31017    149-ArgAlaAlaAspValValLeuLysGluArgArgArgLeu-161
SEQ. ID. NO. 31018    166-ArgGluThrProLeu-170
SEQ. ID. NO. 31019    176-AspAsnMetLysArgValThrGluMetGly-185
SEQ. ID. NO. 31020    195-MetTyrArgLysProGlnThrAlaAspAspIleVal-206
SEQ. ID. NO. 31021    220-AspThrProAspLeuAlaGlu-226
Hydrophilic Regions - Hopp-Woods
SEQ. ID. NO. 31022    39-TrpGluArgArgMetMetVal-45
SEQ. ID. NO. 31023    68-LeuArgAlaGlnAspValGluThr-75
SEQ. ID. NO. 31024    81-LysGlyAlaGluMetAlaArgAlaSerGluThrAspTyrThrLysAspGluVal-98
SEQ. ID. NO. 31025    120-PheLysThrAspGly-124
SEQ. ID. NO. 31026    149-ArgAlaAlaAspValValLeuLysGluArgArgArgLeu-161
SEQ. ID. NO. 31027    176-AspAsnMetLysArgValThrGlu-183
SEQ. ID. NO. 31028    195-MetTyrArgLysProGlnThrAlaAspAspIleVal-206
g311-1
AMPHI Regions - AMPHI
SEQ. ID. NO. 31029    7-SerHisTrpArgValLeuAlaGluLeuAlaAspGlyLeuProGlnHisValSerGlnLeuAlaArg-28
SEQ. ID. NO. 31030    37-LeuAsnGlyPheTrpGlnGlnMetProAlaHisIleArgGlyLeuLeuArg-53
SEQ. ID. NO. 31031    55-HisAspGlyTyrTrpArgLeuValArgProLeuAlaValPheAspAlaGluGlyLeuArgAspLeuGly-77
SEQ. ID. NO. 31032    124-ArgGlnGlyArgLysTrpSerHisArgLeu-133
SEQ. ID. NO. 31033    155-LeuSerProValAlaAla-160
SEQ. ID. NO. 31034    219-ValGluAsnAlaAlaSerValGlnSerLeuPheGln-230
SEQ. ID. NO. 31035    245-GluThrLeuLeuAlaGluLeuGlyAlaValLeuGluGlnTyrAlaGluGlu-261
SEQ. ID. NO. 31036    265-ProPheLeuAsnGlu-269
SEQ. ID. NO. 31037    291-CysGluGlyThrVal-295
SEQ. ID. NO. 31038    362-ThrValGlySerAlaProTyrArgAspLeuSerProLeu-374
SEQ. ID. NO. 31039    426-TyrArgHisProGluGluHisGlySerAspArgTrpPheAsnAlaLeuGlySer-443
SEQ. ID. NO. 31040    511-AlaValAlaSerGlyMetMetAspAlaValCysGly-522
SEQ. ID. NO. 31041    550-AlaAlaLysValAlaGluAlaLeuProPro-559
SEQ. ID. NO. 31042    576-HisGlyLeuLeuAsnLeu-581
Antigenic Index - Jameson-Wolf
SEQ. ID. NO. 31043    26-LeuAlaArgGluAlaAspMetLysProGlnGln-36
SEQ. ID. NO. 31044    50-GlyLeuLeuArgGlnHisAspGlyTyr-58
SEQ. ID. NO. 31045    71-GluGlyLeuArgAspLeuGlyGluArgSerGlyPheGlnThr-84
SEQ. ID. NO. 31046    86-LeuLysHisGluCysAlaSerSerAsnAspGluIleLeuGlu-99
SEQ. ID. NO. 31047    102-ArgIleAlaProAspLysAlaHisLys-110
SEQ. ID. NO. 31048    116-HisLeuGlnSerLysGlyArgGlyArgGlnGlyArgLysTrpSerHisArgLeuGlyGlu-135
SEQ. ID. NO. 31049    145-PheAspArgProGlnTyrGluLeuGlySer-154
SEQ. ID. NO. 31050    162-AlaCysArgArgAlaLeuGly-168
SEQ. ID. NO. 31051    174-ThrGlnIleLysTrpProAsn-180
SEQ. ID. NO. 31052    182-LeuValValGlyArgAspLysLeuGly-190
SEQ. ID. NO. 31053    196-ThrValArgAlaGlyGlyLysThrVal-204
SEQ. ID. NO. 31054    215-LeuProLysGluValGluAsn-221
SEQ. ID. NO. 31055    231-ThrAlaSerArgArgGlyAsnAlaAsp-239
SEQ. ID. NO. 31056    257-GlnTyrAlaGluGluGlyPhe-263
SEQ. ID. NO. 31057    269-GluTyrGluThrAlaAsnArgAspHisGlyLys-279
SEQ. ID. NO. 31058    283-LeuLeuArgAspGlyGluThrValCysGluGlyThrValLysGlyValAspGlyArgGlyValLeu-304
SEQ. ID. NO. 31059    307-GluThrAlaGluGlyGluGlnThrValValSerGlyGluIleSerLeuArgProAspAsnArgSerValSerValProLysArgProAspSerGluArgPheLeu-341
SEQ. ID. NO. 31060    344-GluGlyGlyAsnSerArgLeuLys-351
SEQ. ID. NO. 31061    364-GlySerAlaProTyrArgAspLeuSerProLeuGly-375
SEQ. ID. NO. 31062    378-TrpAlaGluLysAlaAspGlyAsnValArgIle-388
SEQ. ID. NO. 31063    394-CysGlyGluSerLysLysAlaGlnValLysGluGlnLeuAlaArgLysIleGlu-411
SEQ. ID. NO. 31064    424-AsnHisTyrArgHisProGluGluHisGlySerAspArgTrp-437
SEQ. ID. NO. 31065    440-AlaLeuGlySerArgArgPheSerArgAsnAla-450
SEQ. ID. NO. 31066    464-AlaLeuThrAspAspGlyHisTyrLeuGly-473
SEQ. ID. NO. 31067    483-MetLysGluSerLeuAla-488
SEQ. ID. NO. 31068    492-AlaAsnLeuAsnArgProAlaGlyLysArgTyrPro-503
SEQ. ID. NO. 31069    529-GlyArgLeuLysGluLysAsnGlyAlaGlyLysProVal-541
SEQ. ID. NO. 31070    547-GlyGlyGlyAlaAlaLysValAlaGlu-555
SEQ. ID. NO. 31071    565-AsnThrValArgValAlaAsp-571
SEQ. ID. NO. 31072    584-AlaGluGlyGlyGluSerGluHisAla-592
Hydrophilic Regions - Hopp-Woods
SEQ. ID. NO. 31073    26-LeuAlaArgGluAlaAspMetLysProGlnGln-36
SEQ. ID. NO. 31074    50-GlyLeuLeuArgGlnHis-55
SEQ. ID. NO. 31075    71-GluGlyLeuArgAspLeuGlyGluArgSerGlyPhe-82
SEQ. ID. NO. 31076    86-LeuLysHisGluCysAlaSerSerAsnAspGluIleLeuGlu-99
SEQ. ID. NO. 31077    102-ArgIleAlaProAspLysAlaHisLys-110
SEQ. ID. NO. 31078    118-GlnSerLysGlyArgGlyArgGlnGlyArgLysTrpSerHisArgLeuGlyGlu-135
SEQ. ID. NO. 31079    162-AlaCysArgArgAlaLeu-167
SEQ. ID. NO. 31080    183-ValValGlyArgAspLysLeuGly-190
SEQ. ID. NO. 31081    196-ThrValArgAlaGlyGlyLys-202
SEQ. ID. NO. 31082    217-LysGluValGluAsn-221
SEQ. ID. NO. 31083    232-AlaSerArgArgGlyAsnAlaAsp-239
SEQ. ID. NO. 31084    257-GlnTyrAlaGluGluGlyPhe-263

TABLE 1-continued

| | |
|---|---|
| SEQ. ID. NO. 31085 | 270-TyrGluThrAlaAsnArgAspHisGlyLys-279 |
| SEQ. ID. NO. 31086 | 285-ArgAspGlyGluThrValCys-291 |
| SEQ. ID. NO. 31087 | 293-GlyThrValLysGlyValAspGlyArgGly-302 |
| SEQ. ID. NO. 31088 | 307-GluThrAlaGluGlyGluGlnThrValVal-316 |
| SEQ. ID. NO. 31089 | 320-IleSerLeuArgProAspAsnArgSerValSerValProLysArgProAspSerGluArg-339 |
| SEQ. ID. NO. 31090 | 346-GlyAsnSerArgLeu-350 |
| SEQ. ID. NO. 31091 | 367-ProTyrArgAspLeuSer-372 |
| SEQ. ID. NO. 31092 | 378-TrpAlaGluLysAlaAspGlyAsnVal-386 |
| SEQ. ID. NO. 31093 | 395-GlyGluSerLysLysAlaGlnValLysGluGlnLeuAlaArgLysIleGlu-411 |
| SEQ. ID. NO. 31094 | 424-AsnHisTyrArgHisProGluGluHisGlySer-434 |
| SEQ. ID. NO. 31095 | 442-GlySerArgArgPheSerArg-448 |
| SEQ. ID. NO. 31096 | 464-AlaLeuThrAspAspGlyHis-470 |
| SEQ. ID. NO. 31097 | 483-MetLysGluSerLeuAla-488 |
| SEQ. ID. NO. 31098 | 493-AsnLeuAsnArgProAlaGlyLysArgTyrPro-503 |
| SEQ. ID. NO. 31099 | 529-GlyArgLeuLysGluLysAsnGlyAlaGlyLysProVal-541 |
| SEQ. ID. NO. 31100 | 549-GlyAlaAlaLysValAlaGlu-555 |
| SEQ. ID. NO. 31101 | 565-AsnThrValArgValAlaAsp-571 |
| SEQ. ID. NO. 31102 | 585-GluGlyGlyGluSerGluHisAla-592 |
| g312 | |
| AMPHI Regions - AMPHI | |
| SEQ. ID. NO. 31103 | 6-GlyGluIleLeuGluThrValLysMetValAlaAsp-17 |
| SEQ. ID. NO. 31104 | 44-GlnAsnIleTyrAsnLysIleThrThrValGlyLys-55 |
| SEQ. ID. NO. 31105 | 82-IleAlaGlnIleAlaAlaAlaThr-89 |
| SEQ. ID. NO. 31106 | 96-SerValAlaGlnThrLeuAspLysAlaAlaLys-106 |
| SEQ. ID. NO. 31107 | 109-GlyValSerPheIleGlyGlyPheSerAlaLeuValGln-121 |
| SEQ. ID. NO. 31108 | 133-ArgSerValProGluAlaMetLysThr-141 |
| SEQ. ID. NO. 31109 | 167-GlyGluThrIleLysArgThrAlaGluIle-176 |
| SEQ. ID. NO. 31110 | 182-GlyCysAlaLysIleValValPheCys-190 |
| SEQ. ID. NO. 31111 | 230-SerAspAlaValSerLeuThrGluValAlaGluValValLysLys-244 |
| SEQ. ID. NO. 31112 | 249-IleThrArgValGlyGluLeuIleGlyArgGluAlaSerLys-262 |
| SEQ. ID. NO. 31113 | 281-ValGlyAspSerValAlaArgIleLeuGluGluMetGly-293 |
| SEQ. ID. NO. 31114 | 309-LeuAsnAspAlaVal-313 |
| SEQ. ID. NO. 31115 | 322-SerAlaValGlyGlyLeuSerGly-329 |
| SEQ. ID. NO. 31116 | 349-LeuThrLeuAspLysLeuGluAlaMetThrAla-359 |
| SEQ. ID. NO. 31117 | 374-ThrProAlaHisThrIleSerGlyIleIle-383 |
| SEQ. ID. NO. 31118 | 409-ValGlyAspSerValGluPheGlyGlyLeuLeuGly-420 |
| Antigenic Index - Jameson-Wolf | |
| SEQ. ID. NO. 31119 | 4-GlnSerGlyGluIleLeuGlu-10 |
| SEQ. ID. NO. 31120 | 13-LysMetValAlaAspArgAsnPheAspVal-22 |
| SEQ. ID. NO. 31121 | 35-IleSerThrAspIleAspVal-41 |
| SEQ. ID. NO. 31122 | 52-ThrValGlyLysAspLeuValAla-59 |
| SEQ. ID. NO. 31123 | 64-LeuSerAlaLysTyr-68 |
| SEQ. ID. NO. 31124 | 89-ThrLysAlaAspSerTyrVal-95 |
| SEQ. ID. NO. 31125 | 100-ThrLeuAspLysAlaAlaLys-106 |
| SEQ. ID. NO. 31126 | 121-GlnLysGlyMetSerProSerAspGluValLeu-131 |
| SEQ. ID. NO. 31127 | 134-SerValProGluAlaMetLysThrThrAsp-143 |
| SEQ. ID. NO. 31128 | 152-GlySerThrArgAla-156 |
| SEQ. ID. NO. 31129 | 161-AspAlaValLysLeuAlaGlyGluThrIleLysArgThrAlaGluIleThrProGluGlyPheGly-182 |
| SEQ. ID. NO. 31130 | 192-AlaValGluAspAsnProPhe-198 |
| SEQ. ID. NO. 31131 | 204-HisGlySerGlyGluAspAla-211 |
| SEQ. ID. NO. 31132 | 225-AlaAlaLeuGluAsnSerAspAla-232 |
| SEQ. ID. NO. 31133 | 237-GluValAlaGluValValLys-243 |
| SEQ. ID. NO. 31134 | 251-ArgValGlyGluLeuIleGlyArgGluAlaSerLys-262 |
| SEQ. ID. NO. 31135 | 280-AlaValGlyAspSerValAlaArgIleLeuGlu-290 |
| SEQ. ID. NO. 31136 | 311-AspAlaValLysLysGlyGlyMet-318 |
| SEQ. ID. NO. 31137 | 334-ValSerGluAspGluGlyMet-340 |
| SEQ. ID. NO. 31138 | 352-AspLysLeuGluAla-356 |
| SEQ. ID. NO. 31139 | 370-ValProGlyAspThrProAla-376 |
| SEQ. ID. NO. 31140 | 383-IleAlaAspGluAlaAla-388 |
| SEQ. ID. NO. 31141 | 392-IleAsnSerLysThrThrAla-398 |
| SEQ. ID. NO. 31142 | 405-ThrGlyLysThrValGlyAspSerValGlu-414 |
| SEQ. ID. NO. 31143 | 426-ProAlaLysGluGlySerCys-432 |
| SEQ. ID. NO. 31144 | 435-PheValAsnArgGlyGlyArgIle-442 |
| SEQ. ID. NO. 31145 | 447-GlnSerMetLysAsn-451 |
| Hydrophilic Regions - Hopp-Woods | |
| SEQ. ID. NO. 31146 | 13-LysMetValAlaAspArgAsnPheAspVal-22 |
| SEQ. ID. NO. 31147 | 35-IleSerThrAspIleAspVal-41 |
| SEQ. ID. NO. 31148 | 52-ThrValGlyLysAspLeuValAla-59 |
| SEQ. ID. NO. 31149 | 89-ThrLysAlaAspSer-93 |
| SEQ. ID. NO. 31150 | 100-ThrLeuAspLysAlaAlaLys-106 |
| SEQ. ID. NO. 31151 | 123-GlyMetSerProSerAspValLeu-131 |
| SEQ. ID. NO. 31152 | 134-SerValProGluAlaMetLysThrThrAsp-143 |
| SEQ. ID. NO. 31153 | 161-AspAlaValLysLeuAlaGlyGluThrIleLysArgThrAlaGluIleThrPro-178 |
| SEQ. ID. NO. 31154 | 192-AlaValGluAspAsnPro-197 |
| SEQ. ID. NO. 31155 | 207-GlyGluAlaAspAla-211 |
| SEQ. ID. NO. 31156 | 225-AlaAlaLeuGluAsnSerAspAla-232 |
| SEQ. ID. NO. 31157 | 237-GluValAlaGluValValLys-243 |
| SEQ. ID. NO. 31158 | 251-ArgValGlyGluLeuIleGlyArgGluAlaSerLys-262 |
| SEQ. ID. NO. 31159 | 284-SerValAlaArgIleLeuGlu-290 |
| SEQ. ID. NO. 31160 | 311-AspAlaValLysLysGlyGlyMet-318 |

TABLE 1-continued

| | |
|---|---|
| SEQ. ID. NO. 31161 | 334-ValSerGluAspGluGlyMet-340 |
| SEQ. ID. NO. 31162 | 352-AspLysLeuGluAla-356 |
| SEQ. ID. NO. 31163 | 383-IleAlaAspGluAlaAla-388 |
| SEQ. ID. NO. 31164 | 408-ThrValGlyAspSerValGlu-414 |
| SEQ. ID. NO. 31165 | 426-ProAlaLysGluGlySerCys-432 |
| SEQ. ID. NO. 31166 | 438-ArgGlyGlyArgIle-442 |
| SEQ. ID. NO. 31167 | 447-GlnSerMetLysAsn-451 | g313-2
AMPHI Regions - AMPHI

| | |
|---|---|
| SEQ. ID. NO. 31168 | 27-GlyMetAspAspProArgThrTyrGlySerGly-37 |
| SEQ. ID. NO. 31169 | 41-AlaThrAsnValLeu-45 |
| SEQ. ID. NO. 31170 | 60-AspAlaAlaLysGly-64 |
| SEQ. ID. NO. 31171 | 66-ValAlaValLeuLeuAlaArgValLeuGlnGluPro-77 |
| SEQ. ID. NO. 31172 | 88-ValAlaLeuAlaAlaLeuValGlyHisMetTrpPro-99 |
| SEQ. ID. NO. 31173 | 143-SerLeuAlaAlaLeuValAla-149 |

Antigenic Index - Jameson-Wolf

| | |
|---|---|
| SEQ. ID. NO. 31174 | 26-TyrGlyMetAspAspProArgThrTyrGlySerGlyAsnProGlyAla-41 |
| SEQ. ID. NO. 31175 | 46-ArgSerGlyLysLysLysAlaAla-53 |
| SEQ. ID. NO. 31176 | 73-ValLeuGlnGluProLeuGlyLeuSerAspSerAla-84 |
| SEQ. ID. NO. 31177 | 104-PheLysGlyGlyLysGlyVal-110 |
| SEQ. ID. NO. 31178 | 180-ArgHisLysSerAsn-184 |
| SEQ. ID. NO. 31179 | 189-IleLysGlyLysGluSerLysIleGlyGluLysArg-200 |

Hydrophilic Regions - Hopp-Woods

| | |
|---|---|
| SEQ. ID. NO. 31180 | 26-TyrGlyMetAspAspProArgThrTyrGly-35 |
| SEQ. ID. NO. 31181 | 46-ArgSerGlyLysLysLysAlaAla-53 |
| SEQ. ID. NO. 31182 | 105-LysGlyGlyLysGlyVal-110 |
| SEQ. ID. NO. 31183 | 189-IleLysGlyLysGluSerLysIleGlyGluLysArg-200 | g401
AMPHI Regions - AMPHI

| | |
|---|---|
| SEQ. ID. NO. 31184 | 46-ValLysProTyrAsnAlaLeu-52 |
| SEQ. ID. NO. 31185 | 65-CysTyrAsnCysHisSerGlnMetIleArgProPheArg-77 |
| SEQ. ID. NO. 31186 | 112-ValGlyGlyArgTyrSerAspGluTrpHisArgIle-123 |
| SEQ. ID. NO. 31187 | 157-MetLysAlaLeuArgLysValGlyThr-165 |
| SEQ. ID. NO. 31188 | 172-IleAlaLysAlaProGluAlaLeu-179 |

Antigenic Index - Jameson-Wolf

| | |
|---|---|
| SEQ. ID. NO. 31189 | 5-GlnLeuAlaGluGluLysIle-11 |
| SEQ. ID. NO. 31190 | 38-AlaAlaThrGlnProAlaProGlyValLysProTyrAsn-50 |
| SEQ. ID. NO. 31191 | 55-AlaGlyArgAspIleTyrIleArgGluGlyCysTyrAsnCysHis-69 |
| SEQ. ID. NO. 31192 | 74-ArgProPheArgAlaGluThrGluArgTyrGlyHis-85 |
| SEQ. ID. NO. 31193 | 90-GlyGluSerValTyr-94 |
| SEQ. ID. NO. 31194 | 98-PheGlnTrpGlySerLysArgThrGlyProAspLeuAlaArgValGlyGlyArgTyrSerAspGluTrpHis-121 |
| SEQ. ID. NO. 31195 | 125-LeuLeuAsnProArgAspValValProGluSerAsnMetPro-138 |
| SEQ. ID. NO. 31196 | 146-AsnLysValAspValAspAla-152 |
| SEQ. ID. NO. 31197 | 158-LysAlaLeuArgLysValGlyThrProTyrSerAspGluGluIleAlaLysAlaProGlu-177 |
| SEQ. ID. NO. 31198 | 179-LeuAlaAsnLysSerGluLeuAspAla-187 |

Hydrophilic Regions - Hopp-Woods

| | |
|---|---|
| SEQ. ID. NO. 31199 | 5-GlnLeuAlaGluGluLysIle-11 |
| SEQ. ID. NO. 31200 | 76-PheArgAlaGluThrGluArgTyrGly-84 |
| SEQ. ID. NO. 31201 | 101-GlySerLysArgThrGlyProAspLeuAlaArgValGlyGlyArgTyrSerAspGluTrpHis-121 |
| SEQ. ID. NO. 31202 | 127-AsnProArgAspValValPro-133 |
| SEQ. ID. NO. 31203 | 146-AsnLysValAspValAspAla-152 |
| SEQ. ID. NO. 31204 | 158-LysAlaLeuArgLysValGly-164 |
| SEQ. ID. NO. 31205 | 167-TyrSerAspGluGluIleAlaLysAlaProGlu-177 |
| SEQ. ID. NO. 31206 | 179-LeuAlaAsnLysSerGluLeuAspAla-187 | g402
AMPHI Regions - AMPHI

| | |
|---|---|
| SEQ. ID. NO. 31207 | 13-IleAsnMetLeuSerPheLeuThrGly-21 |
| SEQ. ID. NO. 31208 | 44-GlnAlaPheSerPheIle-49 |
| SEQ. ID. NO. 31209 | 85-AlaGlyIleAlaAspPhe-90 |
| SEQ. ID. NO. 31210 | 100-ThrGlyPheSerGlyPheValHis-107 |
| SEQ. ID. NO. 31211 | 117-AlaValValArgGlyLeu-122 |
| SEQ. ID. NO. 31212 | 136-LysSerGlyArgGln-140 |
| SEQ. ID. NO. 31213 | 146-PheAlaAsnValAlaGly-151 |
| SEQ. ID. NO. 31214 | 218-ValPheGlnAsnIleAlaGlyArgProAsp-227 |
| SEQ. ID. NO. 31215 | 261-AspIlePheAsnSerValAsnGlyIleGlu-270 |
| SEQ. ID. NO. 31216 | 279-LysSerGlyIleArg-283 |
| SEQ. ID. NO. 31217 | 294-SerTrpAlaArgValLeuSerAlaIleProGluMetGln-306 |
| SEQ. ID. NO. 31218 | 344-ArgLysTrpLeuArgArgHisPro-351 |
| SEQ. ID. NO. 31219 | 376-AlaGluPheLeuLysGlnValGlnSerHisLeu-386 |
| SEQ. ID. NO. 31220 | 398-HisSerProHisAlaPheAlaThrAlaValHisSerIlePro-411 |
| SEQ. ID. NO. 31221 | 437-GlnArgLeuSerArgLeu-442 |
| SEQ. ID. NO. 31222 | 460-AlaAlaGlnLysVal-464 |
| SEQ. ID. NO. 31223 | 466-SerArgMetLeuIleArgMet-472 |

Antigenic Index - Jameson-Wolf

| | |
|---|---|
| SEQ. ID. NO. 31224 | 4-ValAsnThrLysProAsnThrSer-11 |
| SEQ. ID. NO. 31225 | 66-ArgIleCysArgSerArgPheValAsp-74 |
| SEQ. ID. NO. 31226 | 130-ValGlyThrAspGlyAsnLysSerGlyArgGlnValSer-142 |
| SEQ. ID. NO. 31227 | 223-AlaGlyArgProAspArgLeuIleGluAsnLysHisGly-235 |
| SEQ. ID. NO. 31228 | 240-TyrHisArgAspGlyAspLysValVal-248 |
| SEQ. ID. NO. 31229 | 264-AsnSerValAsnGlyIleGluArg-271 |

TABLE 1-continued

| | |
|---|---|
| SEQ. ID. NO. 31230 | 277-SerLeuLysSerGlyIleArgArg-284 |
| SEQ. ID. NO. 31231 | 321-IleAlaAspGluProGln-326 |
| SEQ. ID. NO. 31232 | 331-LeuGlnAspLysArgValGluIleValLeuAspAspGlyArgLysTrpLeuArgArgHisProAspGluLysPheAsp-356 |
| SEQ. ID. NO. 31233 | 385-HisLeuThrProAspGly-390 |
| SEQ. ID. NO. 31234 | 429-PheProAsnLysGluLeuLeuLysGlnArgLeuSer-440 |
| SEQ. ID. NO. 31235 | 444-TrpProGluSerGlyArgHisValPheAspSerSerThrVal-457 |
| SEQ. ID. NO. 31236 | 472-MetThrGluProSerAlaGly-478 |
| SEQ. ID. NO. 31237 | 481-ValIleThrAspAspAsnMet-487 |
| SEQ. ID. NO. 31238 | 489-ValGluTyrLysTyrGlyArgGlyIle-497 |
| Hydrophilic Regions - Hopp-Woods | |
| SEQ. ID. NO. 31239 | 4-ValAsnThrLysProAsn-9 |
| SEQ. ID. NO. 31240 | 131-GlyThrAspGlyAsnLysSerGlyArgGlnVal-141 |
| SEQ. ID. NO. 31241 | 223-AlaGlyArgProAspArgLeuIleGluAsnLysHis-234 |
| SEQ. ID. NO. 31242 | 241-HisArgAspGlyAspLysValVal-248 |
| SEQ. ID. NO. 31243 | 278-LeuLysSerGlyIleArg-283 |
| SEQ. ID. NO. 31244 | 321-IleAlaAspGluProGln-326 |
| SEQ. ID. NO. 31245 | 331-LeuGlnAspLysArgValGluIleValLeuAspAspGlyArgLysTrpLeuArgArgHisProAspGluLysPheAsp-356 |
| SEQ. ID. NO. 31246 | 430-ProAsnLysGluLeuLeuLysGlnArgLeuSer-440 |
| SEQ. ID. NO. 31247 | 446-GluSerGlyArgHisValPhe-452 |
| SEQ. ID. NO. 31248 | 472-MetThrGluProSerAlaGly-478 |
| SEQ. ID. NO. 31249 | 481-ValIleThrAspAspAsnMet-487 |
| g501 | |
| AMPHI Regions - AMPHI | |
| SEQ. ID. NO. 31250 | 63-ValGluValLeuGlnGluLeuPheArgGlnTyrArgValAlaArgGlnLeu-79 |
| SEQ. ID. NO. 31251 | 88-ValPheAlaAlaPheGlnAlaValPhePheGlnCysLeuAsnHisCysPheGly-105 |
| SEQ. ID. NO. 31252 | 127-AsnAlaPheGlnGly-131 |
| SEQ. ID. NO. 31253 | 139-ValPheGluAlaLeuGlyAsnIleThrArgArgThrThrGluAla-153 |
| SEQ. ID. NO. 31254 | 183-AspGlyPheThrArgIleAsnArgCysGlyLysArgCysHisAlaPheGlyAspPheIleAsp-203 |
| SEQ. ID. NO. 31255 | 253-AlaPheAlaGlyGlnIle-258 |
| SEQ. ID. NO. 31256 | 307-TyrGlyAsnPheLeuThrValPheGlnGluPheGlyArgIleAlaAlaAlaAsp-324 |
| SEQ. ID. NO. 31257 | 365-GlyAsnGlnTyrValAlaGlyPhe-372 |
| SEQ. ID. NO. 31258 | 492-GlyGluAsnHisPheAspValPheArgThr-501 |
| SEQ. ID. NO. 31259 | 513-PheGluArgGlyPheGluHisIleLysPheValArgValAspArgAlaLeuTyrAspValPheAlaGlnThr-536 |
| Antigenic Index - Jameson-Wolf | |
| SEQ. ID. NO. 31260 | 6-LeuThrAlaAspThrAspIle-12 |
| SEQ. ID. NO. 31261 | 19-GlyGlyAspGlyLysMetGlnHisHisPheAspGly-30 |
| SEQ. ID. NO. 31262 | 46-ValGluAlaGluGlyGln-51 |
| SEQ. ID. NO. 31263 | 56-ValArgAlaAspGlyGluAlaValGluVal-65 |
| SEQ. ID. NO. 31264 | 108-GlnSerAlaAspGluArgAsnHisAspPheAspValGlyGln-121 |
| SEQ. ID. NO. 31265 | 145-AsnIleThrArgArgThrThrGluAlaGlnHis-155 |
| SEQ. ID. NO. 31266 | 179-GlyHisThrAspAspGlyPheThrArgIleAsnArgCysGlyLysArgCysHisAla-197 |
| SEQ. ID. NO. 31267 | 202-IleAspValGluValAspArgGlyCysValThrGlyAspAlaAlaAspAsnPhe-219 |
| SEQ. ID. NO. 31268 | 231-GlnGlnGlyPheArgValAspAlaAspLeuAlaValAspAspLysPheHisThrArgGlnAlaAsp-252 |
| SEQ. ID. NO. 31269 | 258-IleGlyGluAlaGluCysGluPheGly-266 |
| SEQ. ID. NO. 31270 | 270-ValHisHisAspPheAspGlyCys-277 |
| SEQ. ID. NO. 31271 | 283-GlnGlyAspIleGly-287 |
| SEQ. ID. NO. 31272 | 295-GlyIleAspLysAlaGly-300 |
| SEQ. ID. NO. 31273 | 321-AlaAlaAlaAspAspGlyArgAsnThrGlnPheAlaArgAspAspGlyGlyValAla-339 |
| SEQ. ID. NO. 31274 | 345-ValGlyHisAspGlyGlySerThr-352 |
| SEQ. ID. NO. 31275 | 392-LeuThrAspGlyThr-396 |
| SEQ. ID. NO. 31276 | 398-PheAlaGlnAspGly-402 |
| SEQ. ID. NO. 31277 | 421-PheAspGlyPheGly-425 |
| SEQ. ID. NO. 31278 | 442-PheAspIleHisArg-446 |
| SEQ. ID. NO. 31279 | 453-AspGlyGlnArgVal-457 |
| SEQ. ID. NO. 31280 | 479-PheAspValGlyTyr-483 |
| SEQ. ID. NO. 31281 | 502-HisGlyLeuAlaGlnAspGlyGly-509 |
| SEQ. ID. NO. 31282 | 523-ValArgValAspArgAlaLeu-529 |
| SEQ. ID. NO. 31283 | 536-ThrValArgGlyGlyAsnLysAspAspLeuVal-546 |
| SEQ. ID. NO. 31284 | 552-ValGluGlyGluHisHisThr-558 |
| Hydrophilic Regions - Hopp-Woods | |
| SEQ. ID. NO. 31285 | 6-LeuThrAlaAspThr-10 |
| SEQ. ID. NO. 31286 | 19-GlyGlyAspGlyLysMet-24 |
| SEQ. ID. NO. 31287 | 46-ValGluAlaGluGlyGln-51 |
| SEQ. ID. NO. 31288 | 56-ValArgAlaAspGlyGluAlaValGluVal-65 |
| SEQ. ID. NO. 31289 | 108-GlnSerAlaAspGluArgAsnHisAspPheAspVal-119 |
| SEQ. ID. NO. 31290 | 146-IleThrArgArgThrThrGluAlaGlnHis-155 |
| SEQ. ID. NO. 31291 | 179-GlyHisThrAspAspGlyPheThrArgIleAsnArgCysGlyLysArgCysHisAla-197 |
| SEQ. ID. NO. 31292 | 202-IleAspValGluValAspArgGlyCysVal-211 |
| SEQ. ID. NO. 31293 | 214-AspAlaAlaAspAsnPhe-219 |
| SEQ. ID. NO. 31294 | 234-PheArgValAspAlaAspLeuAlaValAspAspLysPheHisThrArgGlnAlaAsp-252 |
| SEQ. ID. NO. 31295 | 258-IleGlyGluAlaGluCysGluPheGly-266 |
| SEQ. ID. NO. 31296 | 270-ValHisHisAspPhe-274 |
| SEQ. ID. NO. 31297 | 295-GlyIleAspLysAlaGly-300 |
| SEQ. ID. NO. 31298 | 321-AlaAlaAlaAspAspGlyArgAsnThrGlnPheAlaArgAspAspGlyGlyVal-338 |
| SEQ. ID. NO. 31299 | 345-ValGlyHisAspGly-349 |
| SEQ. ID. NO. 31300 | 523-ValArgValAspArgAlaLeu-529 |
| SEQ. ID. NO. 31301 | 537-ValArgGlyGlyAsnLysAspAspLeuVal-546 |
| SEQ. ID. NO. 31302 | 552-ValGluGlyGluHisHisThr-558 |

TABLE 1-continued g502-1
AMPHI Regions - AMPHI
SEQ. ID. NO. 31303  6-AsnLeuPheGlnPheLeuAlaValCys-14
SEQ. ID. NO. 31304  26-GlyAlaValAspAlaLeuLysGlnPheAsnAsnAspAlaAspGlyIleSerGlySerPheThrGln-47
SEQ. ID. NO. 31305  98-GlnValThrLysSerSerGlnAsp-105
SEQ. ID. NO. 31306  136-GlyIleAspTyrVal-140
Antigenic Index - Jameson-Wolf
SEQ. ID. NO. 31307  32-LysGlnPheAsnAsnAspAlaAspGlyIleSerGlySer-44
SEQ. ID. NO. 31308  48-ThrValGlnSerLysLysLysThrGlnThrAlaHisGlyThr-61
SEQ. ID. NO. 31309  98-GlnValThrLysSerSerGlnAspGlnAlaIleGlyGlySerPro-112
SEQ. ID. NO. 31310  116-LeuSerAsnLysThrAlaLeuGluSerSerTyrThrLeuLysGluAspGlySerSerAsnGly-136
SEQ. ID. NO. 31311  141-ArgAlaThrProLysArgAsnAsnAlaGly-150
SEQ. ID. NO. 31312  158-PheLysGlyGlyAsn-162
SEQ. ID. NO. 31313  167-GlnLeuLysAspSerPheGlyAsnGlnThr-176
SEQ. ID. NO. 31314  184-AsnThrAsnProGlnLeuSerArgGlyAlaPhe-194
SEQ. ID. NO. 31315  196-PheThrProProLysGlyValAspVal-204
Hydrophilic Regions - Hopp-Woods
SEQ. ID. NO. 31316  34-PheAsnAsnAspAlaAspGlyIle-41
SEQ. ID. NO. 31317  49-ValGlnSerLysLysLysThrGlnThr-57
SEQ. ID. NO. 31318  100-ThrLysSerSerGlnAspGlnAlaIle-108
SEQ. ID. NO. 31319  126-TyrThrLeuLysGluAspGlySerSerAsn-135
SEQ. ID. NO. 31320  141-ArgAlaThrProLysArgAsnAsnAla-149
SEQ. ID. NO. 31321  167-GlnLeuLysAspSerPheGly-173
g503-1
AMPHI Regions - AMPHI
SEQ. ID. NO. 31322  6-TyrArgGluAlaLys-10
SEQ. ID. NO. 31323  95-ThrSerSerThrSerAsnPheAlaArgAlaAlaGluMetArgSerPhe-110
Antigenic Index - Jameson-Wolf
SEQ. ID. NO. 31324  4-SerLeuTyrArgGluAlaLysThr-11
SEQ. ID. NO. 31325  32-ProAlaAsnAspAlaSerGlyArgSerSerAlaValAlaGluGluArgThrAlaThrGluMetSerAlaProSer-56
SEQ. ID. NO. 31326  69-SerAlaSerSerCysSerGlyLysGlyValSer-79
SEQ. ID. NO. 31327  87-LeuProThrArgAlaSerSerGluThrSerSerThrSerAsnPhe-101
SEQ. ID. NO. 31328  103-ArgAlaAlaGluMetArgSerPheArgProLeuCysAlaArgAsnAlaArg-119
Hydrophilic Regions - Hopp-Woods
SEQ. ID. NO. 31329  4-SerLeuTyrArgGluAlaLysThr-11
SEQ. ID. NO. 31330  35-AspAlaSerGlyArgSerSerAlaValAlaGluGluArgThrAlaThrGluMetSerAla-54
SEQ. ID. NO. 31331  73-CysSerGlyLysGlyValSer-79
SEQ. ID. NO. 31332  89-ThrArgAlaSerSerGluThrSerSer-97
SEQ. ID. NO. 31333  103-ArgAlaAlaGluMetArgSerPheArg-111
g505
AMPHI Regions - AMPHI
SEQ. ID. NO. 31334  20-LeuThrAlaLeuLeuLysCysLeuSerLeuLeuSerLeuSerCysLeu-35
SEQ. ID. NO. 31335  37-ThrLeuGlyAsnArg-41
SEQ. ID. NO. 31336  89-ProAlaPhePheLysLysProGluAspIleGluThrMetPheLysAlaValHisGlyTrpGluHisValGlnGlnAlaLeuAsp-116
SEQ. ID. NO. 31337  148-AlaMetTyrLysProProLysIleLysAlaIleAspLysIleMetGlnAlaGly-165
SEQ. ID. NO. 31338  178-IleGlnGlyValLysGlnIleIleLysAlaLeuArg-189
SEQ. ID. NO. 31339  209-GlyValTrpAlaAspPhePheGlyLysPro-218
Antigenic Index - Jameson-Wolf
SEQ. ID. NO. 31340  39-GlyAsnArgLeuGly-43
SEQ. ID. NO. 31341  50-LeuLysGluAspArgAlaArgIle-57
SEQ. ID. NO. 31342  64-AlaGlyLeuAsnProAspThrGlnThrVal-73
SEQ. ID. NO. 31343  79-GluThrAlaLysCysGlyLeu-85
SEQ. ID. NO. 31344  92-PheLysLysProGluAspIleGluThr-100
SEQ. ID. NO. 31345  114-AlaLeuAspLysGlyGluGlyLeu-121
SEQ. ID. NO. 31346  131-TyrAspLeuGlyGlyArgTyrIleSer-139
SEQ. ID. NO. 31347  151-LysProProLysIleLysAlaIleAspLysIleMetGln-163
SEQ. ID. NO. 31348  165-GlyArgValArgGlyLysGlyLysThrAlaProThrGly-177
SEQ. ID. NO. 31349  179-GlnGlyValLysGlnIleIleLys-186
SEQ. ID. NO. 31350  188-LeuArgAlaGlyGlu-192
SEQ. ID. NO. 31351  199-AspHisValProSerProGlnGluGlyGlyGlyVal-210
SEQ. ID. NO. 31352  241-CysGluArgLeuProAspGlyGlnGly-249
SEQ. ID. NO. 31353  257-ValGlnGlyGluLeuAsnGlyAsnLysAlaHisAsp-268
SEQ. ID. NO. 31354  273-AsnArgAsnThrGluTyrTrp-279
SEQ. ID. NO. 31355  292-AsnArgTyrLysThrPro-297
Hydrophilic Regions - Hopp-Woods
SEQ. ID. NO. 31356  50-LeuLysGluAspArgAlaArgIle-57
SEQ. ID. NO. 31357  65-GlyLeuAsnProAspThrGlnThr-72
SEQ. ID. NO. 31358  79-GluThrAlaLysCysGlyLeu-85
SEQ. ID. NO. 31359  92-PheLysLysProGluAspIleGluThr-100
SEQ. ID. NO. 31360  114-AlaLeuAspLysGlyGlu-119
SEQ. ID. NO. 31361  151-LysProProLysIleLysAlaIleAspLysIleMetGln-163
SEQ. ID. NO. 31362  165-GlyArgValArgGlyLysGlyLysThrAla-174
SEQ. ID. NO. 31363  188-LeuArgAlaGlyGlu-192
SEQ. ID. NO. 31364  201-ValProSerProGlnGluGly-207
SEQ. ID. NO. 31365  257-ValGlnGlyGluLeuAsnGlyAsnLysAlaHisAsp-268
g506
AMPHI Regions - AMPHI
SEQ. ID. NO. 31366  6-GluValGlyArgIleAlaHisGlyCysGlyGlyValVal-18
SEQ. ID. NO. 31367  25-ArgValValHisGlnValGluGlnGlyAlaArgLeuAla-37
SEQ. ID. NO. 31368  56-PheGlnArgArgPhe-60

TABLE 1-continued

| | |
|---|---|
| SEQ. ID. NO. 31369 | 99-AlaThrArgThrIleAspGlyAsp-106 |
| SEQ. ID. NO. 31370 | 123-GluGlnThrGlyLeuGln-128 |
| SEQ. ID. NO. 31371 | 138-GlyAsnGluValAlaArgCys-144 |
| SEQ. ID. NO. 31372 | 180-GlnValLysArgMetIleArgHisPhe-188 |
| SEQ. ID. NO. 31373 | 199-ValHisArgProPheArgGluLeuAlaAlaLeuAspGlyPheValGlnVal-215 |
| SEQ. ID. NO. 31374 | 224-GlyAspAspPheCysSerPhePheValGlyGlnValPheAsnProLeuLeu-240 |
| SEQ. ID. NO. 31375 | 249-LysThrPheAlaArgPheValPro-256 |
| SEQ. ID. NO. 31376 | 283-AsnLeuValGlnGlyPhe-288 |
| SEQ. ID. NO. 31377 | 313-PheValGlnValGlyGluPheAlaArgValAlaGlnGluGlu-326 |
| SEQ. ID. NO. 31378 | 372-GlyPhePheAlaAspPheAlaGluAsnPheGlyAlaGlyVal-385 |
| SEQ. ID. NO. 31379 | 408-PheGlyAspAspPheAlaHisGluValGlyGlu-418 |
| SEQ. ID. NO. 31380 | 465-CysSerPheSerGlnValGlyGlnMetGly-474 |
| Antigenic Index - Jameson-Wolf | |
| SEQ. ID. NO. 31381 | 12-HisGlyCysGlyGly-16 |
| SEQ. ID. NO. 31382 | 31-GluGlnGlyAlaArgLeuAla-37 |
| SEQ. ID. NO. 31383 | 54-ValAspPheGlnArgArgPheGlyGluVal-63 |
| SEQ. ID. NO. 31384 | 98-ArgAlaThrArgThrIleAspGlyAspLeuAlaGlu-109 |
| SEQ. ID. NO. 31385 | 131-IleArgAlaArgAlaAspThrGlyAsnGluValAlaArgCysGluGly-146 |
| SEQ. ID. NO. 31386 | 176-ProAsnPheGlyGlnValLysArgMetIle-185 |
| SEQ. ID. NO. 31387 | 195-HisAspLeuAspValHisArgProPheArgGlu-205 |
| SEQ. ID. NO. 31388 | 224-GlyAspAspPheCysSer-229 |
| SEQ. ID. NO. 31389 | 244-MetGluPheHisProLysThrPhe-251 |
| SEQ. ID. NO. 31390 | 259-ValGlyMetArgThrGluAla-265 |
| SEQ. ID. NO. 31391 | 279-HisHisAspGlyAsnLeu-284 |
| SEQ. ID. NO. 31392 | 288-PheGlyGlnGlnArgProGluValProVal-297 |
| SEQ. ID. NO. 31393 | 320-AlaArgValAlaGlnGluGluHisGlyArgValValAla-332 |
| SEQ. ID. NO. 31394 | 344-PheGlnArgLysThrAlaAspVal-351 |
| SEQ. ID. NO. 31395 | 362-CysHisGlyGlyGluThrGlyGlu-369 |
| SEQ. ID. NO. 31396 | 391-CysTyrGlyLysArgThrGluArgAlaArgThr-401 |
| SEQ. ID. NO. 31397 | 408-PheGlyAspAspPheAlaHisGluVal-416 |
| SEQ. ID. NO. 31398 | 428-GlnGlnGlyAlaAlaArgAlaGlyGlyGln-437 |
| SEQ. ID. NO. 31399 | 459-GlyGlySerHisArgSerCysSer-466 |
| SEQ. ID. NO. 31400 | 471-GlyGlnMetGlyGlyLysArgLeuThrValArgPheGlyGlyLysArgIleArgAsnArgPheLeuAspCysAsnLysPheLeuGlu-499 |
| SEQ. ID. NO. 31401 | 508-LysThrMetAspAlaIleIle-514 |
| SEQ. ID. NO. 31402 | 516-GlnAspPheArgTyr-520 |
| Hydrophilic Regions - Hopp-Woods | |
| SEQ. ID. NO. 31403 | 31-GluGlnGlyAlaArgLeuAla-37 |
| SEQ. ID. NO. 31404 | 54-ValAspPheGlnArgArgPheGlyGlu-62 |
| SEQ. ID. NO. 31405 | 98-ArgAlaThrArgThrIleAspGlyAspLeuAlaGlu-109 |
| SEQ. ID. NO. 31406 | 131-IleArgAlaArgAlaAspThrGlyAsnGluValAlaArgCysGluGly-146 |
| SEQ. ID. NO. 31407 | 180-GlnValLysArgMetIle-185 |
| SEQ. ID. NO. 31408 | 195-HisAspLeuAspVal-199 |
| SEQ. ID. NO. 31409 | 201-ArgProPheArgGlu-205 |
| SEQ. ID. NO. 31410 | 244-MetGluPheHisPro-248 |
| SEQ. ID. NO. 31411 | 259-ValGlyMetArgThrGluAla-265 |
| SEQ. ID. NO. 31412 | 289-GlyGlnGlnArgProGluVal-295 |
| SEQ. ID. NO. 31413 | 320-AlaArgValAlaGlnGluGluHisGlyArgValValAla-332 |
| SEQ. ID. NO. 31414 | 344-PheGlnArgLysThrAlaAspVal-351 |
| SEQ. ID. NO. 31415 | 364-GlyGlyGluThrGlyGlu-369 |
| SEQ. ID. NO. 31416 | 393-GlyLysArgThrGluArgAlaArgThr-401 |
| SEQ. ID. NO. 31417 | 412-PheAlaHisGluVal-416 |
| SEQ. ID. NO. 31418 | 429-GlnGlyAlaAlaArgAlaGlyGly-436 |
| SEQ. ID. NO. 31419 | 473-MetGlyGlyLysArgLeuThr-479 |
| SEQ. ID. NO. 31420 | 482-PheGlyGlyLysArgIleArgAsnArgPheLeuAsp-493 |
| SEQ. ID. NO. 31421 | 508-LysThrMetAspAlaIleIle-514 |
| SEQ. ID. NO. 31422 | 516-GlnAspPheArgTyr-520 |
| g513-2 | |
| AMPHI Regions - AMPHI | |
| SEQ. ID. NO. 31423 | 6-ThrGluTrpLeuHisGlyTrpValGlyAlaIleAsnAspProMetTrp-21 |
| SEQ. ID. NO. 31424 | 48-GlyArgSerIleLysGlu-53 |
| SEQ. ID. NO. 31425 | 66-GlyIleThrProPheGlnAlaPheValThrGlyLeuAla-78 |
| SEQ. ID. NO. 31426 | 119-SerSerLeuAlaGlnLeuPheLysValArgAsp-129 |
| SEQ. ID. NO. 31427 | 146-GlyLeuGlyGlnLysTrpLeuGlyVal-154 |
| SEQ. ID. NO. 31428 | 176-IleAlaAspThrVal-180 |
| SEQ. ID. NO. 31429 | 205-GlyGlyIleArgArgIleSerLysAlaAla-214 |
| SEQ. ID. NO. 31430 | 243-ValPheGlyGlnIlePheSer-249 |
| SEQ. ID. NO. 31431 | 259-GlyGlyLeuLeuGlyGlyLeuIle-266 |
| SEQ. ID. NO. 31432 | 288-AlaProAsnAlaAlaAlaAlaAla-295 |
| SEQ. ID. NO. 31433 | 303-GlnGlyMetIleGlnMetLeuGlyValPheValAsp-314 |
| SEQ. ID. NO. 31434 | 332-ProTyrGlyAspLeu-336 |
| SEQ. ID. NO. 31435 | 347-ValSerGlnValGlyGlnTrp-353 |
| SEQ. ID. NO. 31436 | 391-ThrAlaValPheArgMet-396 |
| SEQ. ID. NO. 31437 | 403-TyrPheGlyAlaValAla-408 |
| SEQ. ID. NO. 31438 | 423-IleMetAlaTrpIleAsnLeuValAlaIleLeuLeuLeuSer-436 |
| Antigenic Index - Jameson-Wolf | |
| SEQ. ID. NO. 31439 | 1-MetAsnGluAsnPhe-5 |
| SEQ. ID. NO. 31440 | 48-GlyArgSerIleLysGluMetLeuGlyGlyArgLysGlnGlyAspAspProHisGly-66 |
| SEQ. ID. NO. 31441 | 126-LysValArgAspCysAspAsnHisHisPheArgGlyGlyProAla-140 |
| SEQ. ID. NO. 31442 | 208-ArgArgIleSerLysAlaAlaGlu-215 |
| SEQ. ID. NO. 31443 | 273-GlyIleLysArgGlyLeuTyrSerAsnGluAlaGlyMetGlySerAlaProAsnAla-291 |

TABLE 1-continued

| | |
|---|---|
| SEQ. ID. NO. 31444 | 295-AlaGluValLysHisProValSer-302 |
| SEQ. ID. NO. 31445 | 331-GlnProTyrGlyAspLeuSerGly-338 |
| SEQ. ID. NO. 31446 | 375-AlaTyrAlaGluSerAsnVal-381 |
| SEQ. ID. NO. 31447 | 444-ArgAspTyrThrAlaLysLeuLysMetGlyLysAspProGluPheLysLeuSerGluHisProGlyLeuLysArgArgIleLysSerAspValTrp-475 |

Hydrophilic Regions - Hopp-Woods

| | |
|---|---|
| SEQ. ID. NO. 31448 | 48-GlyArgSerIleLysGluMetLeuGlyGlyArgLysGlnGlyAspAspProHisGly-66 |
| SEQ. ID. NO. 31449 | 126-LysValArgAspCysAspAsnHisHis-134 |
| SEQ. ID. NO. 31450 | 208-ArgArgIleSerLysAlaAlaGlu-215 |
| SEQ. ID. NO. 31451 | 273-GlyIleLysArgGlyLeuTyr-279 |
| SEQ. ID. NO. 31452 | 295-AlaGluValLysHisProVal-301 |
| SEQ. ID. NO. 31453 | 450-LeuLysMetGlyLysAspProGluPheLysLeuSerGlu-462 |
| SEQ. ID. NO. 31454 | 464-ProGlyLeuLysArgArgIleLysSer-472 | g515-1
AMPHI Regions - AMPHI

| | |
|---|---|
| SEQ. ID. NO. 31455 | 8-ArgAlaAlaGlyValAlaArgGlyLeuHisSerGluPheAlaArg-22 |
| SEQ. ID. NO. 31456 | 59-AspValArgPhePheAlaGlnValGluGluIleGlyGlnAspPhePheAlaAspAla-77 |
| SEQ. ID. NO. 31457 | 90-AlaGlyGluCysAlaAspGluValSerAspGlnPro-101 |
| SEQ. ID. NO. 31458 | 122-GluSerAlaGlnSerAlaAlaGlyGlyGlyLeuThrAspGlyPheGly-137 |
| SEQ. ID. NO. 31459 | 176-CysGlyLysThrValGlyVal-182 |
| SEQ. ID. NO. 31460 | 192-LeuHisArgArgAla-196 |
| SEQ. ID. NO. 31461 | 233-ValAlaAspValLeuArg-238 |
| SEQ. ID. NO. 31462 | 251-PheGlyGlyValAlaGlyAspValGlyGlyGlyAlaAspGlyValAlaGlnGlyLeuPheGlyGluVal-273 |
| SEQ. ID. NO. 31463 | 306-HisAlaAspAlaLeuSerGluArgPheAla-315 |
| SEQ. ID. NO. 31464 | 334-AlaAlaGluValGluGluPheGlySerGlyValValGluGln-347 |

Antigenic Index - Jameson-Wolf

| | |
|---|---|
| SEQ. ID. NO. 31465 | 24-ValThrAlaGluGluIleAlaPhe-31 |
| SEQ. ID. NO. 31466 | 38-HisGluAlaArgArgGlyGlyAsnThrPhe-47 |
| SEQ. ID. NO. 31467 | 51-IleAlaAlaAlaGluArgAlaGlyAsp-59 |
| SEQ. ID. NO. 31468 | 67-GluGluIleGlyGln-71 |
| SEQ. ID. NO. 31469 | 77-AlaValAspGlnGluThr-82 |
| SEQ. ID. NO. 31470 | 84-LeuAlaValGluArgAlaAlaGlyGluCysAlaAspGluValSerAspGlnProAlaArgAsnGlyGlyIleGluGluAspGlyValAlaAlaCysArgAspAlaAlaAlaAlaGluSerAlaGln-125 |
| SEQ. ID. NO. 31471 | 128-AlaGlyGlyGlyLeuThrAspGly-135 |
| SEQ. ID. NO. 31472 | 160-GlyGlyAsnAspAlaAlaGlyAlaAsn-167 |
| SEQ. ID. NO. 31473 | 192-LeuHisArgArgAla-196 |
| SEQ. ID. NO. 31474 | 217-AlaAspGlyGlyPheArg-222 |
| SEQ. ID. NO. 31475 | 242-GlyValGlyLysSerGlyAla-248 |
| SEQ. ID. NO. 31476 | 257-AspValGlyGlyGlyAlaAspGlyVal-265 |
| SEQ. ID. NO. 31477 | 284-AspValAsnGlyAsnValGln-290 |
| SEQ. ID. NO. 31478 | 309-AlaLeuSerGluArgPheAla-315 |
| SEQ. ID. NO. 31479 | 318-GlyPheGlyGlyGlyArgAlaArgCys-326 |
| SEQ. ID. NO. 31480 | 328-CysGlnValGluArgAlaAlaAlaGluValGluGluPheGlySerGlyVal-344 |
| SEQ. ID. NO. 31481 | 347-GlnHisAsnAsnLeu-351 |

Hydrophilic Regions - Hopp-Woods

| | |
|---|---|
| SEQ. ID. NO. 31482 | 24-ValThrAlaGluGluIleAlaPhe-31 |
| SEQ. ID. NO. 31483 | 38-HisGluAlaArgArgGlyGlyAsn-45 |
| SEQ. ID. NO. 31484 | 51-IleAlaAlaAlaGluArgAlaGlyAsp-59 |
| SEQ. ID. NO. 31485 | 77-AlaValAspGlnGluThr-82 |
| SEQ. ID. NO. 31486 | 84-LeuAlaValGluArgAlaAlaGlyGluCysAlaAspGluValSerAspGlnProAlaArgAsnGlyGlyIleGluGluAspGlyValAlaAlaCysArgAspAlaAlaAlaAlaGluSerAlaGln-125 |
| SEQ. ID. NO. 31487 | 162-AsnAspAlaAlaGly-166 |
| SEQ. ID. NO. 31488 | 192-LeuHisArgArgAla-196 |
| SEQ. ID. NO. 31489 | 258-ValGlyGlyGlyAlaAspGlyVal-265 |
| SEQ. ID. NO. 31490 | 309-AlaLeuSerGluArgPheAla-315 |
| SEQ. ID. NO. 31491 | 322-GlyArgAlaArgCys-326 |
| SEQ. ID. NO. 31492 | 328-CysGlnValGluArgAlaAlaAlaGluValGluGluPheGly-341 | g519-1
AMPHI Regions - AMPHI

| | |
|---|---|
| SEQ. ID. NO. 31493 | 13-ValPheGlyPheLysSerPhe-19 |
| SEQ. ID. NO. 31494 | 29-ValValGluArgLeuGlyArgPheHisArgAlaLeuThrAlaGly-43 |
| SEQ. ID. NO. 31495 | 105-MetAlaIleThrGlnLeuAlaGlnThrThrLeuArgSerVal-118 |
| SEQ. ID. NO. 31496 | 139-ValSerAlaLeuAspGluAlaAla-146 |
| SEQ. ID. NO. 31497 | 165-GlnGluIleLeuArgAlaMetGln-172 |
| SEQ. ID. NO. 31498 | 192-LysIleGluGlnIle-196 |
| SEQ. ID. NO. 31499 | 221-SerAsnAlaGluLysIleAlaArgIleAsn-230 |
| SEQ. ID. NO. 31500 | 249-AlaIleArgGlnIleAlaAlaAla-256 |
| SEQ. ID. NO. 31501 | 273-GlnTyrValAlaAlaPheAsnAsnLeuAlaLys-283 |
| SEQ. ID. NO. 31502 | 292-AlaAsnValAlaAspIleGlySerLeuIleSerAlaGlyMetLysIleIleAspSerSerLysThrAla-314 |

Antigenic Index - Jameson-Wolf

| | |
|---|---|
| SEQ. ID. NO. 31503 | 31-GluArgLeuGlyArgPheHisArg-38 |
| SEQ. ID. NO. 31504 | 58-HisSerLeuLysGluIleProLeuAspValProSerGln-70 |
| SEQ. ID. NO. 31505 | 72-CysIleThrArgAspAsnThrGlnLeuThrVal-82 |
| SEQ. ID. NO. 31506 | 91-ThrAspProLysLeuAlaSer-97 |
| SEQ. ID. NO. 31507 | 122-MetGluLeuAspLysThrPheGluGluArgAspGluIleAsn-135 |
| SEQ. ID. NO. 31508 | 141-AlaLeuAspGluAlaAlaGly-147 |
| SEQ. ID. NO. 31509 | 154-LeuArgTyrGluIleLysAspLeuValPro-163 |
| SEQ. ID. NO. 31510 | 175-IleThrAlaGluArgGluLysArgAlaArgIleAlaGluSerGluGlyArgLysIleGluGln-195 |
| SEQ. ID. NO. 31511 | 197-AsnLeuAlaSerGlyGlnArgGluAlaGluIleGlnGlnSerGluGlyGluAlaGlnAla-216 |
| SEQ. ID. NO. 31512 | 219-AsnAlaSerAsnAlaGluLysIleAlaArgIleAsnArgAlaLysGlyGluAlaGluSerLeuArgLeu-241 |
| SEQ. ID. NO. 31513 | 245-AlaAsnAlaGluAlaIleArg-251 |

TABLE 1-continued

| | |
|---|---|
| SEQ. ID. NO. 31514 | 258-GlnThrGlnGlyGlyAlaAspAlaValAsn-267 |
| SEQ. ID. NO. 31515 | 281-LeuAlaLysGluSerAsnThr-287 |
| SEQ. ID. NO. 31516 | 303-AlaGlyMetLysIleIleAspSerSerLysThrAlaLys-315 |

Hydrophilic Regions - Hopp-Woods

| | |
|---|---|
| SEQ. ID. NO. 31517 | 31-GluArgLeuGlyArgPheHisArg-38 |
| SEQ. ID. NO. 31518 | 58-HisSerLeuLysGluIleProLeu-65 |
| SEQ. ID. NO. 31519 | 73-IleThrArgAspAsnThr-78 |
| SEQ. ID. NO. 31520 | 91-ThrAspProLysLeu-95 |
| SEQ. ID. NO. 31521 | 122-MetGluLeuAspLysThrPheGluGluArgAspGluIleAsn-135 |
| SEQ. ID. NO. 31522 | 141-AlaLeuAspGluAlaAla-146 |
| SEQ. ID. NO. 31523 | 154-LeuArgTyrGluIleLysAspLeuValPro-163 |
| SEQ. ID. NO. 31524 | 175-IleThrAlaGluArgGluLysArgAlaArgIleAlaGluSerGluGlyArgLysIleGluGln-195 |
| SEQ. ID. NO. 31525 | 200-SerGlyGlnArgGluAlaGluIleGlnGlnSerGluGlyGluAlaGlnAla-216 |
| SEQ. ID. NO. 31526 | 221-SerAsnAlaGluLysIleAlaArgIleAsnArgAlaLysGlyGluAlaGluSerLeuArgLeu-241 |
| SEQ. ID. NO. 31527 | 245-AlaAsnAlaGluAlaIleArg-251 |
| SEQ. ID. NO. 31528 | 281-LeuAlaLysGluSerAsn-286 |
| SEQ. ID. NO. 31529 | 306-LysIleIleAspSerSerLysThrAlaLys-315 | g520-1
AMPHI Regions - AMPHI

| | |
|---|---|
| SEQ. ID. NO. 31530 | 109-AspGlyGlnIleTrpArgAlaPheSerSerLeuLys-120 |

Antigenic Index - Jameson-Wolf

| | |
|---|---|
| SEQ. ID. NO. 31531 | 20-LysProSerArgArgAlaLeu-26 |
| SEQ. ID. NO. 31532 | 47-AlaSerGlyLysIleSerLeuPro-54 |
| SEQ. ID. NO. 31533 | 84-ProProAsnAsnSerThrThrThrSerThrSerLeuArgAlaThrSerSerAsnGlySerLeuThrLysAlaAlaAsp-109 |
| SEQ. ID. NO. 31534 | 122-HisMetAlaGluIleArgIleSerArgProLysArgArgGluIleSerSerAlaLeuSerArgAsnThrAlaAlaAlaPro-148 |
| SEQ. ID. NO. 31535 | 150-ProThrValProLysProLysArgProMet-159 |
| SEQ. ID. NO. 31536 | 166-SerProCysLysProThrGluMet-173 |

Hydrophilic Regions - Hopp-Woods

| | |
|---|---|
| SEQ. ID. NO. 31537 | 20-LysProSerArgArgAlaLeu-26 |
| SEQ. ID. NO. 31538 | 93-ThrSerLeuArgAlaThrSerSer-100 |
| SEQ. ID. NO. 31539 | 103-SerLeuThrLysAlaAlaAsp-109 |
| SEQ. ID. NO. 31540 | 122-HisMetAlaGluIleArgIleSerArgProLysArgArgGluIleSer-137 |
| SEQ. ID. NO. 31541 | 140-LeuSerArgAsnThrAla-145 |
| SEQ. ID. NO. 31542 | 151-ThrValProLysProLysArgProMet-159 |
| SEQ. ID. NO. 31543 | 168-CysLysProThrGluMet-173 | g521
AMPHI Regions - AMPHI

| | |
|---|---|
| SEQ. ID. NO. 31544 | 39-ThrLysProSerLysSerCys-45 |
| SEQ. ID. NO. 31545 | 50-LeuProProIleGly-54 |
| SEQ. ID. NO. 31546 | 86-ValLysThrValSerLysProAlaLysSer-95 |
| SEQ. ID. NO. 31547 | 126-AlaGlnLysMetLeu-130 |
| SEQ. ID. NO. 31548 | 132-GlnAlaArgLeuAlaLysGlyGlyAsn-140 |
| SEQ. ID. NO. 31549 | 146-IleAsnAlaLeuSerAsnValLeuAspArgGlnGlnAsnIle-159 |

Antigenic Index - Jameson-Wolf

| | |
|---|---|
| SEQ. ID. NO. 31550 | 1-MetLysSerLysLeu-5 |
| SEQ. ID. NO. 31551 | 36-ValTyrThrThrLysProSerLysSerCysHisSerThrAspLeuProProIleGlyAsnTyrSerSerGluArgTyrIle-62 |
| SEQ. ID. NO. 31552 | 65-GlnThrProGluProAlaProSerProSerAsnGlyGlyGln-78 |
| SEQ. ID. NO. 31553 | 80-ValLysTyrLysAlaProVal-86 |
| SEQ. ID. NO. 31554 | 88-ThrValSerLysProAlaLysSerAsnThrProProGlnAlaProValAsnAsnSerArgArgSerIleLeuGluAlaGluLeuSerAsn<br>GluArgLysAlaLeuThrGluAlaGlnLysMetLeuSer-131 |
| SEQ. ID. NO. 31555 | 134-ArgLeuAlaLysGlyGlyAsnIleAsnHisGlnLys-145 |
| SEQ. ID. NO. 31556 | 152-ValLeuAspArgGlnGlnAsn-158 |
| SEQ. ID. NO. 31557 | 162-LeuGlnArgGluLeuGlyArg-168 |

Hydrophilic Regions - Hopp-Woods

| | |
|---|---|
| SEQ. ID. NO. 31558 | 1-MetLysSerLysLeu-5 |
| SEQ. ID. NO. 31559 | 40-LysProSerLysSerCysHis-46 |
| SEQ. ID. NO. 31560 | 57-SerSerGluArgTyrIle-62 |
| SEQ. ID. NO. 31561 | 66-ThrProGluProAlaProSerProAsnGly-76 |
| SEQ. ID. NO. 31562 | 80-ValLysTyrLysAlaProVal-86 |
| SEQ. ID. NO. 31563 | 88-ThrValSerLysProAlaLysSerAsnThrPro-98 |
| SEQ. ID. NO. 31564 | 105-AsnAsnSerArgArgSerIleLeuGluAlaGluLeuSerAsnGluArgLysAlaLeuThrGluAlaGlnLysMetLeuSer-131 |
| SEQ. ID. NO. 31565 | 152-ValLeuAspArgGlnGlnAsn-158 |
| SEQ. ID. NO. 31566 | 162-LeuGlnArgGluLeuGlyArg-168 | g522
AMPHI Regions - AMPHI

| | |
|---|---|
| SEQ. ID. NO. 31567 | 57-LysIleValGluSerCysMetLys-64 |
| SEQ. ID. NO. 31568 | 96-MetTrpGluGlnProLeuAspGlyLeuSerGluLysGlnIleSerSerPheGlyLysLeuGlyAlaGlnGluGlnLeuAspLeuLeuGlyGlyAla-127 |

Antigenic Index - Jameson-Wolf

| | |
|---|---|
| SEQ. ID. NO. 31569 | 1-MetThrGluProLysHisGluThrProThrGluGluGlnValAlaAlaArgLysLysAlaLysAlaLysIleArgThr-26 |
| SEQ. ID. NO. 31570 | 48-AlaMetSerLysProGlnAlaLysGlnLysIleValGluSerCysMetLys-64 |
| SEQ. ID. NO. 31571 | 71-LysTrpGlnAsnAspLeuLysAlaArgGlyLeuAspAlaAspAsnThrArgLeu-88 |
| SEQ. ID. NO. 31572 | 103-GlyLeuSerGluLysGlnIleSerSerPheGlyLysLeuGlyAla-117 |
| SEQ. ID. NO. 31573 | 128-AsnAlaPheGluThrArgAspLysGlnCysValAlaAspLeuLysAlaAsp-144 |

Hydrophilic Regions - Hopp-Woods

| | |
|---|---|
| SEQ. ID. NO. 31574 | 1-MetThrGluProLysHisGluThrProThrGluGluGlnValAlaAlaArgLysLysAlaLysAlaLysIleArgThr-26 |
| SEQ. ID. NO. 31575 | 48-AlaMetSerLysProGlnAlaLysGlnLysIleValGluSerCysMet-63 |
| SEQ. ID. NO. 31576 | 72-TrpGlnAsnAspLeuLysAlaArgGlyLeuAspAlaAspAsnThrArgLeu-88 |
| SEQ. ID. NO. 31577 | 103-GlyLeuSerGluLysGlnIle-109 |
| SEQ. ID. NO. 31578 | 130-PheGluThrArgAspLysGlnCysValAlaAspLeuLysAlaAsp-144 |

TABLE 1-continued g525-1
AMPHI Regions - AMPHI
SEQ. ID. NO. 31579  59-GluPheAlaGluPheValAsnSerHisProGln-69
SEQ. ID. NO. 31580  86-LysHisTrpMetLysAsnGly-92
SEQ. ID. NO. 31581  125-ArgLeuProThrIleAspGluTrpGluPhe-134
SEQ. ID. NO. 31582  154-ThrIleLeuAspTrpTyr-159
SEQ. ID. NO. 31583  164-ArgLysGlyLeuHisAspValGly-171
SEQ. ID. NO. 31584  178-TrpGlyValTyrAsp-182
SEQ. ID. NO. 31585  188-TrpGluTrpThrGlu-192
Antigenic Index - Jameson-Wolf
SEQ. ID. NO. 31586  24-ValGlnIleGluGlyGlySerTyrArgProLeuTyrLeuLysLysAspThrGlyLeuIleLys-44
SEQ. ID. NO. 31587  46-LysProPheLysLeuAspLysTyrProValThr-56
SEQ. ID. NO. 31588  67-HisProGlnTrpGlnLysGlyArgIleGlySerLysGlnAlaGlu-81
SEQ. ID. NO. 31589  88-TrpMetLysAsnGlySerArgSerTyrAlaProLysAlaGlyGluLeuLysGlnPro-106
SEQ. ID. NO. 31590  122-GlnGlyLysArgLeuProThrIleAspGluTrpGlu-133
SEQ. ID. NO. 31591  140-AlaThrGlnLysAsnGlySerAsnGluProGlyTyrAsnArgThr-154
SEQ. ID. NO. 31592  159-TyrAlaAspGlyGlyArgLysGlyLeuHisAspValGlyLysAspArgProAsnTyr-177
SEQ. ID. NO. 31593  190-TrpThrGluAspPheAsnSerSerLeuLeuSerSerGlyAsnAla-204
SEQ. ID. NO. 31594  213-AlaSerValGlyAlaSerAspSerSerAsnTyr-223
SEQ. ID. NO. 31595  234-SerLeuGlnSerLysTyr-239
SEQ. ID. NO. 31596  245-GlyPheArgCysAlaSerArg-251
Hydrophilic Regions - Hopp-Woods
SEQ. ID. NO. 31597  35-TyrLeuLysLysAspThrGlyLeuIleLys-44
SEQ. ID. NO. 31598  46-LysProPheLysLeuAspLysTyrPro-54
SEQ. ID. NO. 31599  71-GlnLysGlyArgIleGlySerLysGlnAlaGlu-81
SEQ. ID. NO. 31600  91-AsnGlySerArgSerTyrAla-97
SEQ. ID. NO. 31601  99-LysAlaGlyGluLeuLysGln-105
SEQ. ID. NO. 31602  122-GlnGlyLysArgLeuProThr-128
SEQ. ID. NO. 31603  140-AlaThrGlnLysAsnGlySerAsnGluProGlyTyr-151
SEQ. ID. NO. 31604  162-GlyArgLysGlyLeuHisAspValGlyLysAspArgProAsn-176
SEQ. ID. NO. 31605  216-GlyAlaSerAspSerSerAsn-222
g527
AMPHI Regions - AMPHI
SEQ. ID. NO. 31606  7-PhePheGlnProValGln-12
SEQ. ID. NO. 31607  29-AspAlaAlaGluLeuValGluLeuPheAlaLeuPhePro-41
SEQ. ID. NO. 31608  73-GlyLysGlyIleGluArgGlnValAspAsnIleAlaAspValTyrGlyPhe-89
Antigenic Index - Jameson-Wolf
SEQ. ID. NO. 31609  19-GlyArgSerAlaValGlyMetGlyGlySerAspAlaAlaGlu-32
SEQ. ID. NO. 31610  52-GlnLysProArgLeuGlyCysArg-59
SEQ. ID. NO. 31611  71-PheMetGlyLysGlyIleGluArgGlnValAspAsnIleAla-84
SEQ. ID. NO. 31612  107-LeuLeuArgLysGlyThrGlyLeuGluLysThrCysArgProLysProPheValGlnProHisGlyGlyArg-130
Hydrophilic Regions - Hopp-Woods
SEQ. ID. NO. 31613  26-GlyGlySerAspAlaAlaGlu-32
SEQ. ID. NO. 31614  53-LysProArgLeuGlyCys-58
SEQ. ID. NO. 31615  71-PheMetGlyLysGlyIleGluArgGlnValAspAsnIleAla-84
SEQ. ID. NO. 31616  107-LeuLeuArgLysGlyThrGlyLeuGluLysThrCysArgProLysPro-122
g528
AMPHI Regions - AMPHI
SEQ. ID. NO. 31617  23-ArgLeuAlaGlyTrpTyrGluCysSerSerLeuSerGlyTrpCysLysProArgLysProAlaAlaIle-45
SEQ. ID. NO. 31618  69-AsnArgSerValArg-73
SEQ. ID. NO. 31619  87-ArgLysIleGlyLysPhe-92
SEQ. ID. NO. 31620  106-ProLeuValGluArgPheLys-112
Antigenic Index - Jameson-Wolf
SEQ. ID. NO. 31621  29-GluCysSerSerLeuSerGlyTrpCysLysProArgLysProAlaAla-44
SEQ. ID. NO. 31622  49-AspIleGlyGlyGluSerProLeuSerLeuGluAspTyrGluIleProLeuSerLeuAspGlyAsnArgSerValArgAlaAsnGluTyrGluSerAla
GlnLysSerTyrPhe-85
SEQ. ID. NO. 31623  88-LysIleGlyLysPheGluAlaCysGlyLeuAspTrpArgThrArgAspGlyLysProLeuValGluArgPheLysGlnGluGlyPheAspCysLeu
GluLysGlnGlyLeuArgArgAsnGlyLeuSerGluArgValArgTrp-135
Hydrophilic Regions - Hopp-Woods
SEQ. ID. NO. 31624  37-CysLysProArgLysProAlaAla-44
SEQ. ID. NO. 31625  54-SerProLeuSerLeuGluAspTyrGluIleProLeu-65
SEQ. ID. NO. 31626  67-AspGlyAsnArgSerValArgAlaAsnGluTyrGluSerAlaGln-81
SEQ. ID. NO. 31627  88-LysIleGlyLysPheGluAlaCys-95
SEQ. ID. NO. 31628  99-TrpArgThrArgAspGlyLysProLeuValGluArgPheLysGlnGluGlyPheAspCysLeuGluLysGlnGlyLeuArgArgAsnGlyLeuSerGlu
ArgValArgTrp-135
g531
AMPHI Regions - AMPHI
SEQ. ID. NO. 31629  64-LeuAlaAspTyrMetAla-69
SEQ. ID. NO. 31630  90-GlySerIleIleGlyIlePhePheSerLeuProGlyLeuIleLeuGly-105
SEQ. ID. NO. 31631  108-IleGlyAlaAlaAlaGly-113
SEQ. ID. NO. 31632  132-LeuLeuGlyLeuValVal-137
Antigenic Index - Jameson-Wolf
SEQ. ID. NO. 31633  77-ThrGlyAlaGlyLysLeuAlaVal-84
SEQ. ID. NO. 31634  114-GluLeuIleAspArgArgAsnMet-121
Hydrophilic Regions - Hopp-Woods
SEQ. ID. NO. 31635  114-GluLeuIleAspArgArgAsnMet-121
g532-2
AMPHI Regions - AMPHI
SEQ. ID. NO. 31636  6-LysLysGlnAlaAsp-10
SEQ. ID. NO. 31637  27-AlaLeuLeuSerAlaValThrHisLeuLeuAlaIlePheValProMetIleThr-44

TABLE 1-continued

| SEQ. ID. NO. | Sequence |
|---|---|
| SEQ. ID. NO. 31638 | 76-TyrLeuGlnValAsnArgPheGlySerVal-85 |
| SEQ. ID. NO. 31639 | 122-SerThrLeuLeuGlyValSerPhe-129 |
| SEQ. ID. NO. 31640 | 147-LysValIleThrProThrVal-153 |
| SEQ. ID. NO. 31641 | 184-ThrPheGlySerMetGluAsnLeuGly-192 |
| SEQ. ID. NO. 31642 | 206-CysMetLysAsnPro-210 |
| SEQ. ID. NO. 31643 | 224-GlyTyrIleValAlaLeu-229 |
| SEQ. ID. NO. 31644 | 236-PheSerAlaLeuGlnAsnLeuPro-243 |
| SEQ. ID. NO. 31645 | 271-LeuGlyValPheGluAlaValGlyAspLeuThrAla-282 |
| SEQ. ID. NO. 31646 | 297-ThrLysArgLeuArgGlyGlyVal-304 |
| SEQ. ID. NO. 31647 | 307-AspGlyLeuValSerValIleAlaThrAlaLeuGly-318 |
| SEQ. ID. NO. 31648 | 338-AlaSerArgHisValGlyLysTyr-345 |
| SEQ. ID. NO. 31649 | 361-ArgAlaPheThrThrIleProSerProVal-370 |

Antigenic Index - Jameson-Wolf

| SEQ. ID. NO. | Sequence |
|---|---|
| SEQ. ID. NO. 31650 | 3-GluThrMetLysLysGlnAlaAspSerProAspLeu-14 |
| SEQ. ID. NO. 31651 | 16-TyrGlyLeuGluAspArgProProPhe-24 |
| SEQ. ID. NO. 31652 | 80-AsnArgPheGlySer-84 |
| SEQ. ID. NO. 31653 | 94-XxxXxxXxxXxxSerSer-99 |
| SEQ. ID. NO. 31654 | 108-AlaGlyMetLysGluGlyGlyLeuSerGluGlyAla-119 |
| SEQ. ID. NO. 31655 | 177-PheGlyAlaLysAlaAspGlyThrPheGlySer-187 |
| SEQ. ID. NO. 31656 | 207-MetLysAsnProLeuLeuArg-213 |
| SEQ. ID. NO. 31657 | 286-ValSerAspGlnProIleGluGlyGluGluTyrThrLysArgLeuArgGlyGlyValLeu-305 |
| SEQ. ID. NO. 31658 | 394-GlyIleArgArgArgGluAlaVal-401 |
| SEQ. ID. NO. 31659 | 431-IleSerGlyGlyGly-435 |
| SEQ. ID. NO. 31660 | 445-LeuProGluAspLysThrGluAlaAlaValLysPheAspThrAspHisLeuGluHis-463 |

Hydrophilic Regions - Hopp-Woods

| SEQ. ID. NO. | Sequence |
|---|---|
| SEQ. ID. NO. 31661 | 3-GluThrMetLysLysGlnAlaAspSerProAsp-13 |
| SEQ. ID. NO. 31662 | 18-LeuGluAspArgProProPhe-24 |
| SEQ. ID. NO. 31663 | 109-GlyMetLysGluGlyGlyLeuSer-116 |
| SEQ. ID. NO. 31664 | 179-AlaLysAlaAspGly-183 |
| SEQ. ID. NO. 31665 | 289-GlnProIleGluGlyGluGluTyrThrLysArgLeuArgGly-302 |
| SEQ. ID. NO. 31666 | 394-GlyIleArgArgArgGluAlaVal-401 |
| SEQ. ID. NO. 31667 | 445-LeuProGluAspLysThrGluAlaAlaValLysPheAspThrAspHisLeuGluHis-463 | g537
AMPHI Regions - AMPHI

| SEQ. ID. NO. | Sequence |
|---|---|
| SEQ. ID. NO. 31668 | 38-GlnIleArgAspGlyGlyAspAlaLeuHisTyrLeuAsnArgIle-52 |
| SEQ. ID. NO. 31669 | 86-HisGlyGluHisHis-90 |
| SEQ. ID. NO. 31670 | 109-GlyTyrLeuTyrAsnGlyValHisGlu-117 |
| SEQ. ID. NO. 31671 | 138-ArgGlnValAspAlaLeuMetSerAlaIleTyr-148 |
| SEQ. ID. NO. 31672 | 180-AsnGlySerPheGluArg-185 |
| SEQ. ID. NO. 31673 | 190-GlyArgArgGlnProGluAlaGlyArgLysTyrTyrArgAsnAlaCys-205 |
| SEQ. ID. NO. 31674 | 281-ArgProValArgValLeuThrAlaGly-289 |
| SEQ. ID. NO. 31675 | 315-TyrThrAlaValPheAspTyrValArgAsnGly-325 |
| SEQ. ID. NO. 31676 | 374-ThrArgTyrThrTyr-378 |

Antigenic Index - Jameson-Wolf

| SEQ. ID. NO. | Sequence |
|---|---|
| SEQ. ID. NO. 31677 | 21-ThrGlnAsnGlnSerLeuProAlaGly-29 |
| SEQ. ID. NO. 31678 | 32-ValTyrProSerAlaProGlnIleArgAspGlyGlyAspAla-45 |
| SEQ. ID. NO. 31679 | 69-AsnSerAlaArgArgHisAlaArg-76 |
| SEQ. ID. NO. 31680 | 80-LeuAsnProGluAspGlyHisGlyGluHisHisProAspAsnProHis-95 |
| SEQ. ID. NO. 31681 | 99-GlnLysLeuThrGluArgThrArgLeu-107 |
| SEQ. ID. NO. 31682 | 115-ValHisGluAsnIleSerThrGluGluGluAlaAlaGluSerSerAspSerAspIleArgThrGlnGlnArgGlnValAsp-141 |
| SEQ. ID. NO. 31683 | 152-SerLeuLeuAspArgHisThrAspGluAlaGly-162 |
| SEQ. ID. NO. 31684 | 165-PheValArgGluAsnGlyLysThr-172 |
| SEQ. ID. NO. 31685 | 178-GlnGlyAsnGlySerPheGluArgAlaCysAlaLysGlyArgArgGlnProGluAlaGlyArgLysTyrTyrArgAsnAlaCysHisAsnGly-208 |
| SEQ. ID. NO. 31686 | 238-TyrGlyGluArgProAspProValProGluTyrGluIleThrGlyAsnProAlaSer-256 |
| SEQ. ID. NO. 31687 | 258-AspPheSerGluAlaAlaGly-264 |
| SEQ. ID. NO. 31688 | 266-IleAlaMetLysSer-270 |
| SEQ. ID. NO. 31689 | 274-TyrGlnGlyLysAsnGluIleArgPro-282 |
| SEQ. ID. NO. 31690 | 287-ThrAlaGlyAsnAspProAsnGlyArgLeuThr-297 |
| SEQ. ID. NO. 31691 | 321-TyrValArgAsnGlyArgHisAlaGln-329 |
| SEQ. ID. NO. 31692 | 334-PheArgThrArgLysProAspTyrProTyr-343 |
| SEQ. ID. NO. 31693 | 345-GluValAsnGlyGlyGluThrLeuAlaValArgLysGlyGluLys-359 |
| SEQ. ID. NO. 31694 | 364-TrpArgGlyArgTrpCysLeu-370 |
| SEQ. ID. NO. 31695 | 380-ArgGlnPheGlyAsnSer-385 |
| SEQ. ID. NO. 31696 | 389-LeuArgHisGluAlaGlyGly-395 |
| SEQ. ID. NO. 31697 | 402-GlyMetAlaGlySerArgIleArgLeuThrProGluAspSerProGluArgGly-419 |

Hydrophilic Regions - Hopp-Woods

| SEQ. ID. NO. | Sequence |
|---|---|
| SEQ. ID. NO. 31698 | 37-ProGlnIleArgAspGlyGlyAsp-44 |
| SEQ. ID. NO. 31699 | 69-AsnSerAlaArgArgHisAlaArg-76 |
| SEQ. ID. NO. 31700 | 81-AsnProGluAspGlyHisGlyGluHisHisProAsp-92 |
| SEQ. ID. NO. 31701 | 100-LysLeuThrGluArgThrArgLeu-107 |
| SEQ. ID. NO. 31702 | 119-IleSerThrGluGluGluAlaAlaGluSerSerAspSerAspIleArgThrGlnGlnArgGlnValAsp-141 |
| SEQ. ID. NO. 31703 | 152-SerLeuLeuAspArgHisThrAspGluAlaGly-162 |
| SEQ. ID. NO. 31704 | 165-PheValArgGluAsnGlyLys-171 |
| SEQ. ID. NO. 31705 | 181-GlySerPheGluArgAlaCysAlaLysGlyArgArgGlnProGluAlaGlyArgLysTyrTyrArg-202 |
| SEQ. ID. NO. 31706 | 240-GluArgProAspProValProGluTyrGluIle-250 |
| SEQ. ID. NO. 31707 | 258-AspPheSerGluAlaAlaGly-264 |
| SEQ. ID. NO. 31708 | 266-IleAlaMetLysSer-270 |
| SEQ. ID. NO. 31709 | 275-GlnGlyLysAsnGluIleArgPro-282 |
| SEQ. ID. NO. 31710 | 289-GlyAsnAspProAsnGlyArgLeuThr-297 |
| SEQ. ID. NO. 31711 | 323-ArgAsnGlyArgHisAlaGln-329 |

TABLE 1-continued

| | |
|---|---|
| SEQ. ID. NO. 31712 | 334-PheArgThrArgLysProAsp-340 |
| SEQ. ID. NO. 31713 | 352-LeuAlaValArgLysGlyGluLys-359 |
| SEQ. ID. NO. 31714 | 389-LeuArgHisGluAla-393 |
| SEQ. ID. NO. 31715 | 406-SerArgIleArgLeuThrProGluAspSerProGluArgGly-419 | g538
AMPHI Regions - AMPHI

| | |
|---|---|
| SEQ. ID. NO. 31716 | 41-ThrAlaLeuAlaGluAlaValGluLeuValLysAlaAlaGly-54 |
| SEQ. ID. NO. 31717 | 78-LysAlaAlaGluLeuSerGluAlaValAla-87 |
| SEQ. ID. NO. 31718 | 104-GlnGluArgAsnLeuGluLysIleLeuGlnCysArgValLeuAspArgVal-120 |
| SEQ. ID. NO. 31719 | 144-GlnLeuSerHisLeuAlaGlyArgLeuIleArgGlyTyrGlyHisLeuGln-160 |
| SEQ. ID. NO. 31720 | 187-IleAsnAlaLeuLysLysGlnLeuAla-195 |
| SEQ. ID. NO. 31721 | 211-GlyArgIleLysThrPheAlaLeuValGlyTyrThrAsn-223 |
| SEQ. ID. NO. 31722 | 230-PheAsnArgLeuThrLys-235 |
| SEQ. ID. NO. 31723 | 270-GlyPheValSerAspLeuProHisLysLeuIleSerAlaPheSerAlaThrLeuGlu-288 |
| SEQ. ID. NO. 31724 | 306-AsnSerGlyGlnGlnIleGluAspValGluAsnValLeuGlnGluIleHis-322 |
| SEQ. ID. NO. 31725 | 364-GluAsnThrGlyIleAspAlaLeuArgGluAlaIleAlaGluTyrCysAla-380 |

Antigenic Index - Jameson-Wolf

| | |
|---|---|
| SEQ. ID. NO. 31726 | 1-SerGlyArgThrGlyArgAsnSerAlaThrGlnAlaGlnProGluArgVal-17 |
| SEQ. ID. NO. 31727 | 24-LeuAspLysAspAspThrGlySerAsnAlaAlaArg-35 |
| SEQ. ID. NO. 31728 | 47-ValGluLeuValLys-51 |
| SEQ. ID. NO. 31729 | 53-AlaGlyGlyAspSerValArgValGluThrAlaLysArgAspArgProHisThr-70 |
| SEQ. ID. NO. 31730 | 76-ThrGlyLysAlaAlaGluLeuSerGlu-84 |
| SEQ. ID. NO. 31731 | 99-GluLeuThrProThrGlnGluArgAsnLeuGluLys-110 |
| SEQ. ID. NO. 31732 | 128-AlaArgArgAlaArgThrGlnGluGlyArgLeuGlnVal-140 |
| SEQ. ID. NO. 31733 | 160-GlnSerGlnArgGlyGlyIleGlyMetLysGlyProGlyGluThrLysLeuGluThrAspArgArgLeuThrAla-184 |
| SEQ. ID. NO. 31734 | 188-AsnAlaLeuLysLysGlnLeuAlaAsnLeuLysLysGlnArgAlaLeuArgArgLysSerArgGluSerGlyArgIleLysThr-215 |
| SEQ. ID. NO. 31735 | 223-AsnValGlyLysSerSerLeu-229 |
| SEQ. ID. NO. 31736 | 232-ArgLeuThrLysSerGlyIleTyrAla-240 |
| SEQ. ID. NO. 31737 | 286-ThrLeuGluGluThrValGln-292 |
| SEQ. ID. NO. 31738 | 302-AlaAlaAlaArgAsnSerGlyGlnGlnIleGluAspValGluAsnValLeu-318 |
| SEQ. ID. NO. 31739 | 332-TyrAsnLysThrAspLeuLeuProSerGluGluGlnAsnThrGlyIle-347 |
| SEQ. ID. NO. 31740 | 364-GluAsnThrGlyIleAspAlaLeuArgGluAlaIle-375 |
| SEQ. ID. NO. 31741 | 380-AlaAlaAlaProAsnThrAspGluThrGluMetPro-391 |

Hydrophilic Regions - Hopp-Woods

| | |
|---|---|
| SEQ. ID. NO. 31742 | 1-SerGlyArgThrGlyArgAsnSerAla-9 |
| SEQ. ID. NO. 31743 | 12-AlaGlnProGluArg-16 |
| SEQ. ID. NO. 31744 | 24-LeuAspLysAspAspThrGlySerAsnAlaAlaArg-35 |
| SEQ. ID. NO. 31745 | 47-ValGluLeuValLys-51 |
| SEQ. ID. NO. 31746 | 53-AlaGlyGlyAspSerValArgValGluThrAlaLysArgAspArgProHis-69 |
| SEQ. ID. NO. 31747 | 77-GlyLysAlaAlaGluLeuSerGlu-84 |
| SEQ. ID. NO. 31748 | 100-LeuThrProThrGlnGluArgAsnLeuGluLys-110 |
| SEQ. ID. NO. 31749 | 128-AlaArgArgAlaArgThrGlnGluGlyArgLeuGlnVal-140 |
| SEQ. ID. NO. 31750 | 160-GlnSerGlnArgGlyGlyIle-166 |
| SEQ. ID. NO. 31751 | 170-GlyProGlyGluThrLysLeuGluThrAspArgArgLeuThrAla-184 |
| SEQ. ID. NO. 31752 | 188-AsnAlaLeuLysLysGlnLeuAlaAsnLeuLysLysGlnArgAlaLeuArgArgLysSerArgGluSerGlyArgIleLys-214 |
| SEQ. ID. NO. 31753 | 286-ThrLeuGluGluThrValGln-292 |
| SEQ. ID. NO. 31754 | 302-AlaAlaAlaArgAsnSerGlyGlnGlnIleGluAspValGluAsnValLeu-318 |
| SEQ. ID. NO. 31755 | 336-AspLeuLeuProSerGluGluGlnAsn-344 |
| SEQ. ID. NO. 31756 | 369-AspAlaLeuArgGluAlaIle-375 |
| SEQ. ID. NO. 31757 | 383-ProAsnThrAspGluThrGluMetPro-391 | g538
AMPHI Regions - AMPHI

| | |
|---|---|
| SEQ. ID. NO. 31758 | 41-ThrAlaLeuAlaGluAlaValGluLeuValLysAlaAlaGly-54 |
| SEQ. ID. NO. 31759 | 78-LysAlaAlaGluLeuSerGluAlaValAla-87 |
| SEQ. ID. NO. 31760 | 104-GlnGluArgAsnLeuGluLysIleLeuGlnCysArgValLeuAspArgVal-120 |
| SEQ. ID. NO. 31761 | 144-GlnLeuSerHisLeuAlaGlyArgLeuIleArgGlyTyrGlyHisLeuGln-160 |
| SEQ. ID. NO. 31762 | 187-IleAsnAlaLeuLysLysGlnLeuAla-195 |
| SEQ. ID. NO. 31763 | 211-GlyArgIleLysThrPheAlaLeuValGlyTyrThrAsn-223 |
| SEQ. ID. NO. 31764 | 230-PheAsnArgLeuThrLys-235 |
| SEQ. ID. NO. 31765 | 270-GlyPheValSerAspLeuProHisLysLeuIleSerAlaPheSerAlaThrLeuGlu-288 |
| SEQ. ID. NO. 31766 | 306-AsnSerGlyGlnGlnIleGluAspValGluAsnValLeuGlnGluIleHis-322 |
| SEQ. ID. NO. 31767 | 364-GluAsnThrGlyIleAspAlaLeuArgGluAlaIleAlaGluTyrCysAla-380 |

Antigenic Index - Jameson-Wolf

| | |
|---|---|
| SEQ. ID. NO. 31768 | 1-SerGlyArgThrGlyArgAsnSerAlaThrGlnAlaGlnProGluArgVal-17 |
| SEQ. ID. NO. 31769 | 24-LeuAspLysAspAspThrGlySerAsnAlaAlaArg-35 |
| SEQ. ID. NO. 31770 | 47-ValGluLeuValLys-51 |
| SEQ. ID. NO. 31771 | 53-AlaGlyGlyAspSerValArgValGluThrAlaLysArgAspArgProHisThr-70 |
| SEQ. ID. NO. 31772 | 76-ThrGlyLysAlaAlaGluLeuSerGlu-84 |
| SEQ. ID. NO. 31773 | 99-GluLeuThrProThrGlnGluArgAsnLeuGluLys-110 |
| SEQ. ID. NO. 31774 | 128-AlaArgArgAlaArgThrGlnGluGlyArgLeuGlnVal-140 |
| SEQ. ID. NO. 31775 | 160-GlnSerGlnArgGlyGlyIleGlyMetLysGlyProGlyGluThrLysLeuGluThrAspArgArgLeuThrAla-184 |
| SEQ. ID. NO. 31776 | 188-AsnAlaLeuLysLysGlnLeuAlaAsnLeuLysLysGlnArgAlaLeuArgArgLysSerArgGluSerGlyArgIleLysThr-215 |
| SEQ. ID. NO. 31777 | 223-AsnValGlyLysSerSerLeu-229 |
| SEQ. ID. NO. 31778 | 232-ArgLeuThrLysSerGlyIleTyrAla-240 |
| SEQ. ID. NO. 31779 | 286-ThrLeuGluGluThrValGln-292 |
| SEQ. ID. NO. 31780 | 302-AlaAlaAlaArgAsnSerGlyGlnGlnIleGluAspValGluAsnValLeu-318 |
| SEQ. ID. NO. 31781 | 332-TyrAsnLysThrAspLeuLeuProSerGluGluGlnAsnThrGlyIle-347 |
| SEQ. ID. NO. 31782 | 364-GluAsnThrGlyIleAspAlaLeuArgGluAlaIle-375 |
| SEQ. ID. NO. 31783 | 380-AlaAlaAlaProAsnThrAspGluThrGluMetPro-391 |

TABLE 1-continued

Hydrophilic Regions - Hopp-Woods
SEQ. ID. NO. 31784  1-SerGlyArgThrGlyArgAsnSerAla-9
SEQ. ID. NO. 31785  12-AlaGlnProGluArg-16
SEQ. ID. NO. 31786  24-LeuAspLysAspAspThrGlySerAsnAlaAlaArg-35
SEQ. ID. NO. 31787  47-ValGluLeuValLys-51
SEQ. ID. NO. 31788  53-AlaGlyGlyAspSerValArgValGluThrAlaLysArgAspArgProHis-69
SEQ. ID. NO. 31789  77-GlyLysAlaAlaGluLeuSerGlu-84
SEQ. ID. NO. 31790  100-LeuThrProThrGlnGluArgAsnLeuGluLys-110
SEQ. ID. NO. 31791  128-AlaArgArgAlaArgThrGlnGluGlyArgLeuGlnVal-140
SEQ. ID. NO. 31792  160-GlnSerGlnArgGlyGlyIle-166
SEQ. ID. NO. 31793  170-GlyProGlyGluThrLysLeuGluThrAspArgArgLeuThrAla-184
SEQ. ID. NO. 31794  188-AsnAlaLeuLysLysGlnLeuAlaAsnLeuLysLysGlnArgAlaLeuArgArgLysSerArgGluSerGlyArgIleLys-214
SEQ. ID. NO. 31795  286-ThrLeuGluGluThrValGln-292
SEQ. ID. NO. 31796  302-AlaAlaAlaArgAsnSerGlyGlnGlnIleGluAspValGluAsnValLeu-318
SEQ. ID. NO. 31797  336-AspLeuLeuProSerGluGluGlnAsn-344
SEQ. ID. NO. 31798  369-AspAlaLeuArgGluAlaIle-375
SEQ. ID. NO. 31799  383-ProAsnThrAspGluThrGluMetPro-391
g539
AMPHI Regions - AMPHI
SEQ. ID. NO. 31800  18-ArgGlnArgGluHisHisArgLeuHisHisThr-28
SEQ. ID. NO. 31801  44-LeuValGlyGlyPheAspPheLeuArgValIleGlyCysGlyGly-58
SEQ. ID. NO. 31802  108-AlaGlyGlyAlaGlyAsnAlaAla-115
SEQ. ID. NO. 31803  123-ArgAlaIleMetGlyPhe-128
SEQ. ID. NO. 31804  142-AspLeuValGluAspPheLeu-148
SEQ. ID. NO. 31805  172-AspAlaLeuCysAspCysLeuThr-179
SEQ. ID. NO. 31806  197-GlnValPheGlyAsnValGln-203
SEQ. ID. NO. 31807  220-PheGlyAlaAlaAlaGlnTyr-226
SEQ. ID. NO. 31808  328-GlyArgSerLeuThrAsnPro-334
SEQ. ID. NO. 31809  354-ValSerArgValAlaLysSerTrpSerPheAla-364
SEQ. ID. NO. 31810  366-MetProAspLeuValSerArgLeu-373
Antigenic Index - Jameson-Wolf
SEQ. ID. NO. 31811  1-MetGluAspLeuGlnGluIleGly-8
SEQ. ID. NO. 31812  15-LysValGlyArgGlnArgGluHisHisArg-24
SEQ. ID. NO. 31813  26-HisHisThrGlnSerGlyAsnGlyLysAlaAspAsp-37
SEQ. ID. NO. 31814  63-ProAspPheGlnGlnAsnValGlyGluAlaAsp-73
SEQ. ID. NO. 31815  77-ValProAspAspAlaAlaAla-83
SEQ. ID. NO. 31816  88-IleGluValAspAlaAspAspAlaValCys-97
SEQ. ID. NO. 31817  102-LeuPheAspGlnProAspAlaGlyGlyAlaGlyAsnAlaAlaGluHis-117
SEQ. ID. NO. 31818  169-GlyIleAspAspAlaLeuCys-175
SEQ. ID. NO. 31819  229-MetAlaSerArgSerAlaSer-235
SEQ. ID. NO. 31820  242-ThrGluMetArgThr-246
SEQ. ID. NO. 31821  261-CysSerSerAspGlySerArgSer-268
SEQ. ID. NO. 31822  304-ThrThrCysSerSerThrSer-310
SEQ. ID. NO. 31823  313-ThrValSerSerLysValAlaGluLysAlaGluIle-324
SEQ. ID. NO. 31824  326-LeuCysGlyArgSerLeuThrAsnProThrVal-336
SEQ. ID. NO. 31825  348-TyrSerArgArgAlaValVal-354
SEQ. ID. NO. 31826  356-ArgValAlaLysSer-360
SEQ. ID. NO. 31827  369-LeuValSerArgLeuAsnArgLeuAspLeu-378
Hydrophilic Regions - Hopp-Woods
SEQ. ID. NO. 31828  1-MetGluAspLeuGlnGluIleGly-8
SEQ. ID. NO. 31829  15-LysValGlyArgGlnArgGluHisHisArg-24
SEQ. ID. NO. 31830  31-GlyAsnGlyLysAlaAspAsp-37
SEQ. ID. NO. 31831  69-ValGlyGluAlaAsp-73
SEQ. ID. NO. 31832  78-ProAspAspAlaAlaAla-83
SEQ. ID. NO. 31833  88-IleGluValAspAlaAspAspAlaValCys-97
SEQ. ID. NO. 31834  102-LeuPheAspGlnProAspAlaGlyGly-110
SEQ. ID. NO. 31835  113-AsnAlaAlaGluHis-117
SEQ. ID. NO. 31836  169-GlyIleAspAspAlaLeu-174
SEQ. ID. NO. 31837  230-AlaSerArgSerAla-234
SEQ. ID. NO. 31838  242-ThrGluMetArgThr-246
SEQ. ID. NO. 31839  263-SerAspGlySerArg-267
SEQ. ID. NO. 31840  317-LysValAlaGluLysAlaGluIle-324
SEQ. ID. NO. 31841  348-TyrSerArgArgAlaValVal-354
SEQ. ID. NO. 31842  369-LeuValSerArgLeuAsnArgLeuAspLeu-378
g542
AMPHI Regions - AMPHI
SEQ. ID. NO. 31843  6-ArgIleArgArgCysSerVal-12
Antigenic Index - Jameson-Wolf
SEQ. ID. NO. 31844  1-MetProLysTrpSerArgIleArgArgCysSerVal-12
SEQ. ID. NO. 31845  29-ProProSerAsnAla-33
SEQ. ID. NO. 31846  37-ValArgLeuLysSerSerAspGlyIleAlaSer-47
SEQ. ID. NO. 31847  56-GlySerMetProSerGluThrValSerHisLysSerAspSerSerArgAsnThrSerAlaSerArgArgAsnValSerProLysCysProPheGly-87
SEQ. ID. NO. 31848  90-CysArgGlnAspAlaAlaLysProArgArgPheGlyGlyLys-103
SEQ. ID. NO. 31849  107-LeuThrGlySerArg-111
Hydrophilic Regions - Hopp-Woods
SEQ. ID. NO. 31850  5-SerArgIleArgArgCysSer-11
SEQ. ID. NO. 31851  37-ValArgLeuLysSerSerAspGlyIleAla-46
SEQ. ID. NO. 31852  58-MetProSerGluThrValSerHisLysSerAspSerSerArgAsnThrSerAlaSerArgArgAsnValSerPro-82
SEQ. ID. NO. 31853  90-CysArgGlnAspAlaAlaLysProArgArgPheGlyGly-102

TABLE 1-continued g544-2
AMPHI Regions - AMPHI
SEQ. ID. NO. 31854    55-PheTrpPheProSerCysProGlyCysValSerGluMetProLysValThrLysThrAlaAsnAspTyrLys-78
SEQ. ID. NO. 31855    85-LeuAlaValAlaGlnProIleAspProIleGluSerValArgGlnTyrVal-101
SEQ. ID. NO. 31856    116-LysAlaValGlyGlnAlaPhe-122
Antigenic Index - Jameson-Wolf
SEQ. ID. NO. 31857    1-MetLysLysIleLeu-5
SEQ. ID. NO. 31858    22-IleProAspSerLysThrAlaPro-29
SEQ. ID. NO. 31859    35-AspLeuHisGlyLysThrValSerAsnAlaAspLeuGlnGly-48
SEQ. ID. NO. 31860    59-SerCysProGlyCys-63
SEQ. ID. NO. 31861    66-GluMetProLysValThrLysThrAlaAsnAspTyrLysAsnLysAspPhe-82
SEQ. ID. NO. 31862    90-ProIleAspProIleGluSerValArgGlnTyrValLysAspTyrGly-105
SEQ. ID. NO. 31863    113-AspAlaAspLysAlaVal-118
SEQ. ID. NO. 31864    133-IleGlyLysLysGlyGluIleLeu-140
SEQ. ID. NO. 31865    144-ValGlyGluProAspPheGlyLysLeuTyrGlnGluIleAspThr-158
Hydrophilic Regions - Hopp-Woods
SEQ. ID. NO. 31866    1-MetLysLysIleLeu-5
SEQ. ID. NO. 31867    23-ProAspSerLysThr-27
SEQ. ID. NO. 31868    66-GluMetProLysValThrLysThrAlaAsnAspTyrLysAsnLysAspPhe-82
SEQ. ID. NO. 31869    92-AspProIleGluSerValArgGlnTyrValLys-102
SEQ. ID. NO. 31870    113-AspAlaAspLysAlaVal-118
SEQ. ID. NO. 31871    133-IleGlyLysLysGlyGluIle-139
g547
AMPHI Regions - AMPHI
SEQ. ID. NO. 31872    7-PheAsnLysThrValAlaSerPheAlaGlnIleValGluThrPheAspVal-23
SEQ. ID. NO. 31873    62-AsnArgSerPheLys-66
SEQ. ID. NO. 31874    120-GluLeuLeuThrIleLeuValLys-127
Antigenic Index - Jameson-Wolf
SEQ. ID. NO. 31875    3-ValAspAsnGlyPheAsnLysThrVal-11
SEQ. ID. NO. 31876    35-GlnMetLysGlnArgCysGly-41
SEQ. ID. NO. 31877    56-CysGlyPheGluIleProAsnArgSerPheLysGlu-67
SEQ. ID. NO. 31878    76-LeuSerGluArgPheArgThrAsnAlaGluValGluMet-88
SEQ. ID. NO. 31879    128-AsnLeuSerProAsnGlyLysLysArgPhe-137
Hydrophilic Regions - Hopp-Woods
SEQ. ID. NO. 31880    36-MetLysGlnArgCys-40
SEQ. ID. NO. 31881    60-IleProAsnArgSerPheLysGlu-67
SEQ. ID. NO. 31882    76-LeuSerGluArgPheArgThrAsnAlaGluValGluMet-88
SEQ. ID. NO. 31883    129-LeuSerProAsnGlyLysLysArgPhe-137
g548
AMPHI Regions - AMPHI
SEQ. ID. NO. 31884    7-SerPheLeuValLeuAlaAlaLeuAlaAlaCysLys-22
SEQ. ID. NO. 31885    31-AlaAlaSerSerSer-35
SEQ. ID. NO. 31886    41-AlaGluAsnAlaAlaLysPro-47
SEQ. ID. NO. 31887    89-PheThrHisCysProAspValCysProThr-98
SEQ. ID. NO. 31888    103-TyrSerAspThrLeuLysGlnLeuGlyGlyGln-113
SEQ. ID. NO. 31889    132-GluIleIleGlyLysTyrAlaLys-139
Antigenic Index - Jameson-Wolf
SEQ. ID. NO. 31890    22-LysProGlnAspAsnSerAla-28
SEQ. ID. NO. 31891    33-SerSerSerAlaSer-37
SEQ. ID. NO. 31892    39-ProAlaAlaGluAsnAlaAlaLysProGlnThrArgGlyThrAspMetArgLysGluAspIleGlyGlyAspPheThrLeuThrAspGlyGluGly
                      LysProPheSer-74
SEQ. ID. NO. 31893    76-SerAspLeuLysGly-80
SEQ. ID. NO. 31894    93-ProAspValCysPro-97
SEQ. ID. NO. 31895    104-SerAspThrLeuLysGlnLeuGlyGlyGlnAlaLysAspValLys-118
SEQ. ID. NO. 31896    124-IleAspProGluArgAspThrProGluIleIleGlyLysTyrAlaLysGlnPheAsnProAspPhe-145
SEQ. ID. NO. 31897    150-AlaThrGlyGlyGln-154
SEQ. ID. NO. 31898    169-LysIleAsnGlnLysAspAspSerGluAsnTyrLeu-180
SEQ. ID. NO. 31899    189-LeuIleAspLysAsnGlyGlu-195
SEQ. ID. NO. 31900    200-SerProTyrGlySerGluProGluThrIleAlaAlaAspVal-213
Hydrophilic Regions - Hopp-Woods
SEQ. ID. NO. 31901    22-LysProGlnAspAsnSerAla-28
SEQ. ID. NO. 31902    39-ProAlaAlaGluAsnAlaAlaLysProGlnThrArgGlyThrAspMetArgLysGluAspIleGlyGly-61
SEQ. ID. NO. 31903    64-ThrLeuThrAspGlyGluGlyLysPro-72
SEQ. ID. NO. 31904    76-SerAspLeuLysGly-80
SEQ. ID. NO. 31905    111-GlyGlyGlnAlaLysAspValLys-118
SEQ. ID. NO. 31906    124-IleAspProGluArgAspThrProGluIleIle-134
SEQ. ID. NO. 31907    170-IleAsnGlnLysAspAspSerGluAsnTyrLeu-180
SEQ. ID. NO. 31908    191-AspLysAsnGlyGlu-195
SEQ. ID. NO. 31909    203-GlySerGluProGluThrIleAlaAlaAspVal-213
g553
AMPHI Regions - AMPHI
SEQ. ID. NO. 31910    31-LeuAlaAlaValAlaGlyPheTyrGlyPheTyrThrAspLeu-44
SEQ. ID. NO. 31911    59-AsnLeuAlaAspIleValArgPheAlaAspAsp-69
SEQ. ID. NO. 31912    83-GluLeuGlySerLeu-87
SEQ. ID. NO. 31913    99-HisPheValValLeu-103
SEQ. ID. NO. 31914    162-GlyIleSerGlyLeuGlyArgThrLeuPhe-171
SEQ. ID. NO. 31915    173-LeuLeuAlaLeuAlaAlaAlaMetGluValPheAlaPheLeu-186
SEQ. ID. NO. 31916    232-HisAspIleTyrSerLeuProProPro-240
Antigenic Index - Jameson-Wolf
SEQ. ID. NO. 31917    11-LeuThrLysLysLeu-15

TABLE 1-continued

| | |
|---|---|
| SEQ. ID. NO. 31918 | 45-ArgAlaLeuArgSerLysTyr-51 |
| SEQ. ID. NO. 31919 | 55-LeuLysGlyGluAsnLeuAlaAsp-62 |
| SEQ. ID. NO. 31920 | 75-ArgAlaLeuArgLeuAspLeuAspGluLeuGlySer-86 |
| SEQ. ID. NO. 31921 | 106-ValSerSerAspGly-110 |
| SEQ. ID. NO. 31922 | 115-AspProAlaSerGlyArgArgLysValLysThrGluGluIleSerArgLysPheThr-133 |
| SEQ. ID. NO. 31923 | 140-TrpProAsnThrArgPheGluAlaGlyGluGluLysGlnGluIleArg-155 |
| SEQ. ID. NO. 31924 | 163-IleSerGlyLeuGly-167 |
| SEQ. ID. NO. 31925 | 192-LysIleGlyArgGlyGluSer-198 |
| SEQ. ID. NO. 31926 | 202-IleGlyArgSerGlyCysGlyLysSerThrLeu-212 |
| SEQ. ID. NO. 31927 | 216-LeuSerGlyAsnLeuProProGluSerGlyLysVal-227 |
| SEQ. ID. NO. 31928 | 245-PheGluCysAspGlyGlnGlyArgThr-253 |
| SEQ. ID. NO. 31929 | 258-GlyLeuAsnLeuAsnArg-263 |
| Hydrophilic Regions - Hopp-Woods | |
| SEQ. ID. NO. 31930 | 11-LeuThrLysLysLeu-15 |
| SEQ. ID. NO. 31931 | 45-ArgAlaLeuArgSer-49 |
| SEQ. ID. NO. 31932 | 55-LeuLysGlyGluAsnLeuAlaAsp-62 |
| SEQ. ID. NO. 31933 | 75-ArgAlaLeuArgLeuAspLeuAspGluLeuGlySer-86 |
| SEQ. ID. NO. 31934 | 106-ValSerSerAspGly-110 |
| SEQ. ID. NO. 31935 | 116-ProAlaSerGlyArgArgLysValLysThrGluGluIleSerArgLysPheThr-133 |
| SEQ. ID. NO. 31936 | 144-ArgPheGluAlaGlyGluGluLysGlnGluIleArg-155 |
| SEQ. ID. NO. 31937 | 192-LysIleGlyArgGlyGluSer-198 |
| SEQ. ID. NO. 31938 | 205-SerGlyCysGlyLys-209 |
| SEQ. ID. NO. 31939 | 220-LeuProProGluSerGlyLys-226 |
| SEQ. ID. NO. 31940 | 245-PheGluCysAspGlyGlnGly-251 |
| g554 | |
| AMPHI Regions - AMPHI | |
| SEQ. ID. NO. 31941 | 35-AlaProThrLeuGlnThrProGluThrLeu-44 |
| SEQ. ID. NO. 31942 | 71-AlaAlaLeuThrGlnLeuMet-77 |
| SEQ. ID. NO. 31943 | 110-ArgMetPheValArgProGlyAspThrVal-119 |
| SEQ. ID. NO. 31944 | 124-LeuLeuLysGlyMetIleAla-130 |
| SEQ. ID. NO. 31945 | 141-AlaAspArgLeuGlyAsnGlySerIleGluAsnPheValGlnGlnMetAsnLysGlu-159 |
| SEQ. ID. NO. 31946 | 193-GluAlaLeuMetArgAspPheProGluTyrTyrProLeuPheSer-207 |
| SEQ. ID. NO. 31947 | 280-ArgAlaLeuGlnAlaPheAspThrPro-288 |
| SEQ. ID. NO. 31948 | 296-ThrValAlaGlnIle-300 |
| SEQ. ID. NO. 31949 | 331-GluGlnIleLeuGluThrIleGlnProIleProAla-342 |
| Antigenic Index - Jameson-Wolf | |
| SEQ. ID. NO. 31950 | 24-SerProAlaProAsnArgProThr-31 |
| SEQ. ID. NO. 31951 | 37-ThrLeuGlnThrProGluThr-43 |
| SEQ. ID. NO. 31952 | 53-LeuGlnSerArgGlnThrLeuSerAlaLysAsnThrAsnThrProValGlu-69 |
| SEQ. ID. NO. 31953 | 84-LysAsnMetLysSerGlyAsnIleGlnSerGluGluAsnLeuLysIleProGlu-101 |
| SEQ. ID. NO. 31954 | 104-TrpAlaSerGluGlySerArgMetPheValArgProGlyAspThrValSerThrAspLysLeuLeu-125 |
| SEQ. ID. NO. 31955 | 142-AspArgLeuGlyAsnGlySerIleGluAsnPhe-152 |
| SEQ. ID. NO. 31956 | 156-MetAsnLysGluAlaArgArgLeuGlyMetLysAsnThrValPheLysAsnProThrGlyLeuGlyArgGluGlyGlnValSerThrAlaLysAspLeuSerLeu-190 |
| SEQ. ID. NO. 31957 | 194-AlaLeuMetArgAspPheProGluTyrTyr-203 |
| SEQ. ID. NO. 31958 | 214-GluAsnIleGluGlnAsnAsnArgAsnIleLeu-224 |
| SEQ. ID. NO. 31959 | 226-TyrArgAspAsnAsnValAsnGlyLeuLysAlaGlyHisThrGluSerGlyGlyTyr-244 |
| SEQ. ID. NO. 31960 | 250-TyrSerGlyAsnGlyArgHis-256 |
| SEQ. ID. NO. 31961 | 262-LeuGlySerGluSerAlaGluThrArgAlaSerAspAsnSerLysLeuLeuAsn-279 |
| SEQ. ID. NO. 31962 | 286-AspThrProLysIleTyrProLysGlyLysThr-296 |
| SEQ. ID. NO. 31963 | 302-IleSerGlyGlySerLysLysThrValArg-311 |
| SEQ. ID. NO. 31964 | 323-ProHisLysGluAlaLysMetAlaGluGlnIleLeu-334 |
| SEQ. ID. NO. 31965 | 342-AlaProValLysLysGlyGlnIleLeuGlyLysIleLysIleArgGlnAsnGlyHisThrIleAlaGluLysGluIleValAla-369 |
| SEQ. ID. NO. 31966 | 371-GluAsnValGluLysArgSerArgTrpGlnArgLeu-382 |
| Hydrophilic Regions - Hopp-Woods | |
| SEQ. ID. NO. 31967 | 26-AlaProAsnArgProThr-31 |
| SEQ. ID. NO. 31968 | 57-GlnThrLeuSerAlaLysAsnThrAsnThrProValGlu-69 |
| SEQ. ID. NO. 31969 | 85-AsnMetLysSerGlyAsnIleGlnSerGluGluAsnLeuLysIleProGlu-101 |
| SEQ. ID. NO. 31970 | 107-GluGlySerArgMetPheValArgProGlyAspThrValSerThrAspLysLeuLeu-125 |
| SEQ. ID. NO. 31971 | 156-MetAsnLysGluAlaArgArgLeuGlyMet-165 |
| SEQ. ID. NO. 31972 | 174-ThrGlyLeuGlyArgGluGlyGlnValSerThrAlaLysAspLeuSerLeu-190 |
| SEQ. ID. NO. 31973 | 214-GluAsnIleGluGlnAsnAsnArg-221 |
| SEQ. ID. NO. 31974 | 227-ArgAspAsnAsnValAsn-232 |
| SEQ. ID. NO. 31975 | 237-GlyHisThrGluSerGly-242 |
| SEQ. ID. NO. 31976 | 264-SerGluSerAlaGluThrArgAlaSerAspAsnSerLysLeuLeuAsn279 |
| SEQ. ID. NO. 31977 | 289-LysIleTyrProLysGlyLysThr-296 |
| SEQ. ID. NO. 31978 | 304-GlyGlySerLysLysThrValArg-311 |
| SEQ. ID. NO. 31979 | 323-ProHisLysGluAlaLysMetAlaGluGlnIleLeu-334 |
| SEQ. ID. NO. 31980 | 343-ProValLysLysGlyGlnIle-349 |
| SEQ. ID. NO. 31981 | 353-IleLysIleArgGlnAsnGly-359 |
| SEQ. ID. NO. 31982 | 362-IleAlaGluLysGluIleValAla-369 |
| SEQ. ID. NO. 31983 | 371-GluAsnValGluLysArgSerArgTrp-379 |
| g556 | |
| AMPHI Regions - AMPHI | |
| SEQ. ID. NO. 31984 | 61-IleGluArgLeuLys-65 |
| Antigenic Index - Jameson-Wolf | |
| SEQ. ID. NO. 31985 | 1-MetAspAsnLysThrLysLeuArgLeu-9 |
| SEQ. ID. NO. 31986 | 52-ThrSerArgArgGlnGlnArgGlnPheIleGluArgLeuLysLysPheAspIleAspProGluLysGlyArgIleAsnGluAlaAsnLeuArgArgMetTyrHisSerGlyGlyGlnHisGlnLysAspAla-95 |
| SEQ. ID. NO. 31987 | 102-SerGlnLysCysSerValAspGluAlaHisAlaMetPheLysLysArgProThrArgGlnGluIleAsn-124 |

TABLE 1-continued

| | |
|---|---|
| SEQ. ID. NO. 31988 | 127-AlaAlaLysGlnSerArgGlyGlnLysArgProHisArg-139 |

Hydrophilic Regions - Hopp-Woods

| | |
|---|---|
| SEQ. ID. NO. 31989 | 1-MetAspAsnLysThrLysLeuArgLeu-9 |
| SEQ. ID. NO. 31990 | 53-SerArgArgGlnGlnArgGlnPheIleGluArgLeuLysLysPheAspIleAspProGluLysGlyArgIleAsnGluAlaAsnLeuArgArgMetTyr-85 |
| SEQ. ID. NO. 31991 | 90-GlnHisGlnLysAspAla-95 |
| SEQ. ID. NO. 31992 | 105-CysSerValAspGluAlaHisAlaMetPheLysLysArgProThrArgGlnGluIleAsn-124 |
| SEQ. ID. NO. 31993 | 127-AlaAlaLysGlnSerArgGlyGlnLysArgProHisArg-139 | g557
AMPHI Regions - AMPHI

| | |
|---|---|
| SEQ. ID. NO. 31994 | 22-GlyAlaAspGlyIle-26 |
| SEQ. ID. NO. 31995 | 55-SerGlyArgValAspAspAlaAla-62 |
| SEQ. ID. NO. 31996 | 113-ThrValSerValArgArgIleLeuAspTyrAlaAsp-124 |
| SEQ. ID. NO. 31997 | 142-ArgGlnAspValAlaGluGlnIle-149 |

Antigenic Index - Jameson-Wolf

| | |
|---|---|
| SEQ. ID. NO. 31998 | 20-LeuLysGlyAlaAspGlyIleSerProProLeuThrTyrArgSerTrpHisIleGluGlyGlyGlnAlaLeu-43 |
| SEQ. ID. NO. 31999 | 54-AlaSerGlyArgValAspAspAlaAlaGly-63 |
| SEQ. ID. NO. 32000 | 68-LeuArgIleAspSerValSerGlnAsnLysGluThrTyrThr-81 |
| SEQ. ID. NO. 32001 | 100-GlnValLeuLysArgGlyGluProValGlyLysProMet-112 |
| SEQ. ID. NO. 32002 | 118-ArgIleLeuAspTyrAlaAspAsnGluIleLeuGlyLysGlnGluGluGluGluThrLeu-137 |
| SEQ. ID. NO. 32003 | 141-MetArgGlnAspValAlaGluGlnIleValArg-151 |

Hydrophilic Regions - Hopp-Woods

| | |
|---|---|
| SEQ. ID. NO. 32004 | 21-LysGlyAlaAspGlyIle-26 |
| SEQ. ID. NO. 32005 | 56-GlyArgValAspAspAlaAlaGly-63 |
| SEQ. ID. NO. 32006 | 68-LeuArgIleAspSerValSerGlnAsnLysGluThrTyrThr-81 |
| SEQ. ID. NO. 32007 | 100-GlnValLeuLysArgGlyGluProValGly-109 |
| SEQ. ID. NO. 32008 | 126-GluIleLeuGlyLysGlnGluGluGluGluThrLeu-137 |
| SEQ. ID. NO. 32009 | 141-MetArgGlnAspValAlaGluGlnIleValArg-151 | g560
AMPHI Regions - AMPHI

| | |
|---|---|
| SEQ. ID. NO. 32010 | 30-PheArgAspGlyAlaHisLysMetAlaArgValTrpValGly-43 |
| SEQ. ID. NO. 32011 | 167-ArgMetAlaLysMetPhe-172 |
| SEQ. ID. NO. 32012 | 192-PheLeuLysTyrProGlyGlu-198 |
| SEQ. ID. NO. 32013 | 216-GluLeuMetGluLysCysGluHisLeuIleGlu-226 |

Antigenic Index - Jameson-Wolf

| | |
|---|---|
| SEQ. ID. NO. 32014 | 29-ProPheArgAspGlyAlaHisLysMet-37 |
| SEQ. ID. NO. 32015 | 63-GluHisIleProAspArgProSer-70 |
| SEQ. ID. NO. 32016 | 75-LysHisGlnSerGlyTrpGlu-81 |
| SEQ. ID. NO. 32017 | 95-ValAlaLysArgGluLeuPhe-101 |
| SEQ. ID. NO. 32018 | 116-IleGlyIleAspArgAsnAsnArgArgGluAlaAsnGluGlnLeuIle-131 |
| SEQ. ID. NO. 32019 | 134-GlyLeuAlaArgLysAsnGluGlyTyr-142 |
| SEQ. ID. NO. 32020 | 148-ProGluGlyThrArgLeuAlaProGlyLysArgGlyLysTyrLysLeuGlyGly-165 |
| SEQ. ID. NO. 32021 | 182-AsnAlaSerGlyGluPheTrpProLysAsnSerPheLeuLysTyrProGlyIle-199 |
| SEQ. ID. NO. 32022 | 209-HisAlaSerGlySerGluAlaGluLeuMetGluLysCysGluHisLeuIle-225 |
| SEQ. ID. NO. 32023 | 242-MetProSerGluThr-246 |

Hydrophilic Regions - Hopp-Woods

| | |
|---|---|
| SEQ. ID. NO. 32024 | 29-ProPheArgAspGlyAlaHisLysMet-37 |
| SEQ. ID. NO. 32025 | 64-HisIleProAspArgProSer-70 |
| SEQ. ID. NO. 32026 | 95-ValAlaLysArgGluLeuPhe-101 |
| SEQ. ID. NO. 32027 | 116-IleGlyIleAspArgAsnAsnArgArgGluAlaAsnGluGlnLeuIle-131 |
| SEQ. ID. NO. 32028 | 134-GlyLeuAlaArgLysAsnGlu-140 |
| SEQ. ID. NO. 32029 | 149-GluGlyThrArgLeuAlaProGlyLysArgGlyLysTyrLysLeuGlyGly-165 |
| SEQ. ID. NO. 32030 | 211-SerGlySerGluAlaGluLeuMetGluLysCysGluHisLeuIle-225 |
| SEQ. ID. NO. 32031 | 242-MetProSerGluThr-246 | g561-2
AMPHI Regions - AMPHI

| | |
|---|---|
| SEQ. ID. NO. 32032 | 6-ArgPheSerAspGly-10 |
| SEQ. ID. NO. 32033 | 22-GlyLeuTrpValGlyLeuAlaAla-29 |
| SEQ. ID. NO. 32034 | 46-AlaSerValIleGluGluAlaGlyAsn-54 |
| SEQ. ID. NO. 32035 | 74-GlnIleAspAsnGlnIleAlaGluPheGluLysSerLeuLysArgIleSerGlnSerAsp-93 |
| SEQ. ID. NO. 32036 | 128-AlaTyrArgProThrGlnIle-135 |
| SEQ. ID. NO. 32037 | 188-ValIleArgProLeuGlnAlaLeuArgGluGlyAlaGluArgIleGly-203 |
| SEQ. ID. NO. 32038 | 219-PheLysGlnValGlyArgCysPheAsnGln-228 |
| SEQ. ID. NO. 32039 | 237-TyrAspAspLeuGluGlyGln-243 |
| SEQ. ID. NO. 32040 | 247-GlnThrHisAsnLeuGluLysGln-254 |
| SEQ. ID. NO. 32041 | 263-ArgThrThrArgAspLeuHisGlnSerTyr-272 |
| SEQ. ID. NO. 32042 | 276-GlnAlaAlaGluGluPheLeuAsnHisIleLeuPro-287 |
| SEQ. ID. NO. 32043 | 358-GlnThrLeuIleArgGlnLeuGly-365 |
| SEQ. ID. NO. 32044 | 391-GlnGlyLeuHisAspSerIleAlaGlnAlaLeuThr-402 |
| SEQ. ID. NO. 32045 | 433-GlyValGlnGluCysTyrGluAspValArgGluLeu-444 |
| SEQ. ID. NO. 32046 | 455-LysGluPheProGluAlaValAlaAspLeuPheAlaArgPhe-468 |
| SEQ. ID. NO. 32047 | 503-LeuSerAsnIleArgLysHisAlaArg-511 |
| SEQ. ID. NO. 32048 | 539-ThrGluLysIleGlyGluProThr-546 |

Antigenic Index - Jameson-Wolf

| | |
|---|---|
| SEQ. ID. NO. 32049 | 4-ProThrArgPheSerAspGlyIlePro-12 |
| SEQ. ID. NO. 32050 | 48-ValIleGluGluAlaGlyAsn-54 |
| SEQ. ID. NO. 32051 | 66-AlaGlyGluGlySerProArgAlaGlnIleAspAsnGlnIleAlaGluPheGluLysSerLeuLysArgIleSerGlnSerAspAlaIleHis-96 |
| SEQ. ID. NO. 32052 | 99-IleProSerAspAsnProLeuAla-106 |
| SEQ. ID. NO. 32053 | 124-ProProLeuGlnAlaTyrArgArgProThrGlnIleGluLeu-137 |
| SEQ. ID. NO. 32054 | 152-GluAsnAlaGlyGluLysAsnThrTrpTrp-161 |

TABLE 1-continued

| | |
|---|---|
| SEQ. ID. NO. 32055 | 193-GlnAlaLeuArgGluGlyAlaGluArgIleGlyGlnArgHisPheAspIleProValProGluAspGlyThrProGluPheLysGlnValGlyArgCysPheAsn-227 |
| SEQ. ID. NO. 32056 | 235-ThrLeuTyrAspAspLeuGluGlyGlnValAlaGluGlnThrHisAsnLeuGluLysGlnAsnArgAsnLeu-258 |
| SEQ. ID. NO. 32057 | 263-ArgThrThrArgAspLeuHisGlnSerTyrThrProArgGlnAlaAlaGluGluPhe-281 |
| SEQ. ID. NO. 32058 | 291-AlaGlnSerGlyAsn-295 |
| SEQ. ID. NO. 32059 | 297-CysLeuGluAsnGlySerAspThrAspIle-306 |
| SEQ. ID. NO. 32060 | 310-ThrAlaGluHisGlyLysLysProProLeuGluLysTyrHisAspGluThrPhe-327 |
| SEQ. ID. NO. 32061 | 331-TyrGlnAsnGluLysLeuGly-337 |
| SEQ. ID. NO. 32062 | 342-GlyPheSerAspGlyThrSerLeuThrGlyAspAspArgThrLeu-356 |
| SEQ. ID. NO. 32063 | 370-GlyAlaLysGlnGluGluGluLysArgLeu-379 |
| SEQ. ID. NO. 32064 | 383-LeuGlnGluArgAsnLeu-388 |
| SEQ. ID. NO. 32065 | 393-LeuHisAspSerIle-397 |
| SEQ. ID. NO. 32066 | 414-AlaPheAlaGluAsnLysArgGluGluAlaAlaGlu-425 |
| SEQ. ID. NO. 32067 | 433-GlyValGlnGluCysTyrGluAspValArgGlu-443 |
| SEQ. ID. NO. 32068 | 449-ArgThrLysIleSerAsnLysGluPheProGluAlaVal-461 |
| SEQ. ID. NO. 32069 | 480-TrpGluAsnGlySer-484 |
| SEQ. ID. NO. 32070 | 487-ProThrGlnAspGluGlnLeu-493 |
| SEQ. ID. NO. 32071 | 502-SerLeuSerAsnIleArgLysHisAlaArg-511 |
| SEQ. ID. NO. 32072 | 520-SerGluTyrGlyGlyArgPhe-526 |
| SEQ. ID. NO. 32073 | 530-IleGlnAspAsnGlyGlnGlyPheAspThrGluLysIleGlyGluProThrGlySerHis-549 |
| SEQ. ID. NO. 32074 | 555-MetGlnGluArgAlaLysArgIleArgAla-564 |
| SEQ. ID. NO. 32075 | 566-LeuGluIleArgSerGlnAlaGlnGlnGlyThr-576 |
| SEQ. ID. NO. 32076 | 581-ThrGlyAlaProLysGluSerLeuPro-589 |
| Hydrophilic Regions - Hopp-Woods | |
| SEQ. ID. NO. 32077 | 48-ValIleGluGluAlaGlyAsn-54 |
| SEQ. ID. NO. 32078 | 68-GluGlySerProArgAlaGlnIle-75 |
| SEQ. ID. NO. 32079 | 78-GlnIleAlaGluPheGluLysSerLeuLysArgIleSerGln-91 |
| SEQ. ID. NO. 32080 | 128-AlaTyrArgArgProThrGln-134 |
| SEQ. ID. NO. 32081 | 152-GluAsnAlaGlyGluLys-157 |
| SEQ. ID. NO. 32082 | 193-GlnAlaLeuArgGluGlyAlaGluArgIleGlyGlnArgHisPhe-207 |
| SEQ. ID. NO. 32083 | 210-ProValProGluAspGlyThrProGluPheLysGlnValGly-223 |
| SEQ. ID. NO. 32084 | 235-ThrLeuTyrAspAspLeuGluGlyGlnValAlaGluGlnThrHisAsnLeuGluLysGlnAsnArg-256 |
| SEQ. ID. NO. 32085 | 264-ThrThrArgAspLeuHis-269 |
| SEQ. ID. NO. 32086 | 276-GlnAlaAlaGluGluPhe-281 |
| SEQ. ID. NO. 32087 | 300-AsnGlySerAspThrAspIle-306 |
| SEQ. ID. NO. 32088 | 312-GluHisGlyLysLysProProLeuGluLysTyrHisAspGluThrPhe-327 |
| SEQ. ID. NO. 32089 | 331-TyrGlnAsnGluLysLeuGly-337 |
| SEQ. ID. NO. 32090 | 347-ThrSerLeuThrGlyAspAspArgThrLeu-356 |
| SEQ. ID. NO. 32091 | 370-GlyAlaLysGlnGluGluGluLysArgLeu-379 |
| SEQ. ID. NO. 32092 | 383-LeuGlnGluArgAsnLeu-388 |
| SEQ. ID. NO. 32093 | 414-AlaPheAlaGluAsnLysArgGluGluAlaAlaGlu-425 |
| SEQ. ID. NO. 32094 | 436-GluCysTyrGluAspValArgGlu-443 |
| SEQ. ID. NO. 32095 | 450-ThrLysIleSerAsnLysGluPheProGluAlaVal-461 |
| SEQ. ID. NO. 32096 | 488-ThrGlnAspGluGlnLeu-493 |
| SEQ. ID. NO. 32097 | 502-SerLeuSerAsnIleArgLysHisAlaArg-511 |
| SEQ. ID. NO. 32098 | 532-AspAsnGlyGlnGlyPheAspThrGluLysIleGlyGluProThrGly-547 |
| SEQ. ID. NO. 32099 | 555-MetGlnGluArgAlaLysArgIleArgAla-564 |
| SEQ. ID. NO. 32100 | 566-LeuGluIleArgSerGlnAlaGln-573 |
| SEQ. ID. NO. 32101 | 582-GlyAlaProLysGluSerLeuPro-589 |
| g562 | |
| AMPHI Regions - AMPHI | |
| SEQ. ID. NO. 32102 | 48-TrpSerLeuValSerAlaTrpMetValValIle-58 |
| SEQ. ID. NO. 32103 | 84-LeuGluThrThrValMetSerAlaValArgThrLeu-95 |
| SEQ. ID. NO. 32104 | 97-PheThrProTyrThrThrValAlaSerThrSer-107 |
| SEQ. ID. NO. 32105 | 116-ThrPhePheAlaProLeuSerArgTrp-124 |
| SEQ. ID. NO. 32106 | 133-AsnAlaProValHisSerMetThrLysSerThrProSerSerPheHis-148 |
| SEQ. ID. NO. 32107 | 184-ValSerAsnLeuValArgTrpAlaLeu-192 |
| Antigenic Index - Jameson-Wolf | |
| SEQ. ID. NO. 32108 | 9-PheAsnSerGlyLysThrLysPro-16 |
| SEQ. ID. NO. 32109 | 32-ProLeuArgAlaArgArgArgSerLeuTrpArg-42 |
| SEQ. ID. NO. 32110 | 72-AlaThrGlyGluArgGlnLeuVal-79 |
| SEQ. ID. NO. 32111 | 105-SerThrSerSerProProGlyAlaGluMet-114 |
| SEQ. ID. NO. 32112 | 139-MetThrLysSerThrProSerSerPheHisGlySerSerAla-152 |
| SEQ. ID. NO. 32113 | 154-LeuArgValGluLysLysGlyIleLeuSerProLeuThr-166 |
| SEQ. ID. NO. 32114 | 168-ArgLeuProProSerTrpAspThrSerAlaSerLysArgProCysThr-183 |
| Hydrophilic Regions - Hopp-Woods | |
| SEQ. ID. NO. 32115 | 11-SerGlyLysThrLysPro-16 |
| SEQ. ID. NO. 32116 | 33-LeuArgAlaArgArgArgSerLeuTrp-41 |
| SEQ. ID. NO. 32117 | 72-AlaThrGlyGluArgGlnLeuVal-79 |
| SEQ. ID. NO. 32118 | 110-ProGlyAlaGluMet-114 |
| SEQ. ID. NO. 32119 | 140-ThrLysSerThrPro-144 |
| SEQ. ID. NO. 32120 | 154-LeuArgValGluLysLysGlyIle-161 |
| SEQ. ID. NO. 32121 | 176-SerAlaSerLysArgProCysThr-183 |
| 563g | |
| AMPHI Regions - AMPHI | |
| SEQ. ID. NO. 32122 | 24-ThrLysArgGluGlyLysSerCys-31 |
| SEQ. ID. NO. 32123 | 115-AsnGlnTyrAlaGlnPhe-120 |
| SEQ. ID. NO. 32124 | 159-ValAsnGlnIleAsnSerSerHisProSerGlnLeuAsnGlyTyrIleGlu-175 |
| SEQ. ID. NO. 32125 | 292-AlaAlaAsnValGlnAspMetAsnAsnThrAla-302 |
| SEQ. ID. NO. 32126 | 332-IleGlnAsnThrGlyLysLeuLeuSerAlaGly-342 |

TABLE 1-continued

| | |
|---|---|
| SEQ. ID. NO. 32127 | 457-AspAsnAlaValGlnGly-462 |
| SEQ. ID. NO. 32128 | 495-GlnMetAsnAsnIleGlyThr-501 |
| SEQ. ID. NO. 32129 | 571-AlaGlnArgIleHisAsnAlaGly-578 |
| SEQ. ID. NO. 32130 | 594-LeuHisAsnThrAsnGlu-599 |
| SEQ. ID. NO. 32131 | 616-TyrGluAlaPheGlyArg-621 |
| SEQ. ID. NO. 32132 | 642-SerAspHisLeuArgThrProAspGlyValAlaHisGluAsnTrp-656 |
| SEQ. ID. NO. 32133 | 673-ThrAlaProAlaLysIle-678 |
| SEQ. ID. NO. 32134 | 729-GlyLysLeuHisAsnTyrTrpArg-736 |
| SEQ. ID. NO. 32135 | 756-GluGluIleThrArg-760 |
| SEQ. ID. NO. 32136 | 771-SerHisSerLysAlaLeu-776 |
| SEQ. ID. NO. 32137 | 809-ProAsnSerPheThrProLeuPro-816 |
| SEQ. ID. NO. 32138 | 861-LeuHisLysArgLeuGlyAspGlyTyr-869 |
| SEQ. ID. NO. 32139 | 877-GluGlnIleAlaGluLeuThrGlyHisArgArgLeuAspGlyTyrGlnAsn-893 |
| SEQ. ID. NO. 32140 | 899-LysAlaLeuMetAsp-903 |
| SEQ. ID. NO. 32141 | 1002-ThrLeuAspAsnIleGlyGly-1008 |
| SEQ. ID. NO. 32142 | 1019-AlaThrGlnAspIleAsnAsnIleGlyGlyIleLeu-1030 |
| SEQ. ID. NO. 32143 | 1051-LysSerSerGlnAsn-1055 |
| SEQ. ID. NO. 32144 | 1106-GlnAlaGlyArgAspIle-1111 |
| SEQ. ID. NO. 32145 | 1135-GlySerThrAsnGluValGlySerSer-1143 |
| SEQ. ID. NO. 32146 | 1191-ValAspAspAlaSerLysHisThrGlyArg-1200 |
| SEQ. ID. NO. 32147 | 1215-SerHisHisGluThr-1219 |
| SEQ. ID. NO. 32148 | 1254-GlnAlaGlyAsnHisVal-1259 |
| SEQ. ID. NO. 32149 | 1269-GlnSerGluThrTyrHisGln-1275 |
| SEQ. ID. NO. 32150 | 1326-TyrGluGlnThrGly-1330 |
| SEQ. ID. NO. 32151 | 1388-SerThrGlnSerSerLysGlnVal-1395 |
| SEQ. ID. NO. 32152 | 1416-TyrGlnThrGlyLysGlyAlaGlnAsnLeuAlaAsnGlyThrThrAsn-1431 |
| SEQ. ID. NO. 32153 | 1508-GluGlnSerAsnThrGluArgSerGln-1516 |
| SEQ. ID. NO. 32154 | 1542-GlyGlyAsnValGlyLysGlyTyr-1549 |
| SEQ. ID. NO. 32155 | 1692-SerAspIleGlnAsnTyrSerGln-1699 |
| SEQ. ID. NO. 32156 | 1718-LeuGlyGlnGlyAlaLys-1723 |
| SEQ. ID. NO. 32157 | 1761-IleAsnThrProLysAsnIle-1767 |
| SEQ. ID. NO. 32158 | 1796-ThrAspThrAlaGluArgHisSerGlySerLeuLysAsn-1808 |
| SEQ. ID. NO. 32159 | 1825-ValSerGlnAspPheSerLysAsnValGln-1834 |
| SEQ. ID. NO. 32160 | 1893-IleLeuAsnMetLeuAlaSerGlyLeuAlaGluProThr-1905 |
| SEQ. ID. NO. 32161 | 1925-GlyGlnHisPheLysAspLeuAlaGly-1933 |
| SEQ. ID. NO. 32162 | 1968-ProAlaGlyAlaLeu-1972 |
| SEQ. ID. NO. 32163 | 2006-SerAlaIleThrArgMetLeuGlyThrAla-2015 |
| SEQ. ID. NO. 32164 | 2032-PheGlnThrAlaSerAspPheAlaSerSerPheSerTyrProIleAsn-2047 |
| Antigenic Index - Jameson-Wolf | |
| SEQ. ID. NO. 32165 | 1-MetAsnLysThrLeu-5 |
| SEQ. ID. NO. 32166 | 9-IlePheAsnArgLysArgGlyAlaVal-17 |
| SEQ. ID. NO. 32167 | 22-GluThrThrLysArgGluGlyLysSerCysAlaAspSerGlySerGlySer-38 |
| SEQ. ID. NO. 32168 | 48-ProThrHisSerLys-52 |
| SEQ. ID. NO. 32169 | 78-IleIleThrAspLysAlaAlaProLysThrGlnGln-89 |
| SEQ. ID. NO. 32170 | 122-ValGlyAsnArgGlyAlaIleLeuAsnAsnSerArgSerAsnThrGlnThr-138 |
| SEQ. ID. NO. 32171 | 147-AsnProTrpLeuThrArgGlyGluAlaArgVal-157 |
| SEQ. ID. NO. 32172 | 162-IleAsnSerSerHisProSerGlnLeuAsnGly-172 |
| SEQ. ID. NO. 32173 | 174-IleGluValGlyGlyArgArgAlaGluVal-183 |
| SEQ. ID. NO. 32174 | 200-AsnAlaSerArgAlaThrLeu-206 |
| SEQ. ID. NO. 32175 | 208-ThrGlyGlnProGlnTyrGlnAlaGlyAspPheSerGlyPheLysIleArgGlnGlyAsnAla-228 |
| SEQ. ID. NO. 32176 | 234-GlyLeuAspAlaArgAspThrAspPhe-242 |
| SEQ. ID. NO. 32177 | 261-AlaGlyIleArgAsnGlnGlyGlnLeu-269 |
| SEQ. ID. NO. 32178 | 279-AspAlaAsnGlyArgLeuValAsn-286 |
| SEQ. ID. NO. 32179 | 296-GlnAspMetAsnAsnThrAlaGluHisLysValAsnIleArg-309 |
| SEQ. ID. NO. 32180 | 311-GlnAlaPheGluAsnSerGlyThrAlaVal-320 |
| SEQ. ID. NO. 32181 | 322-GlnGlnGlyThrGlnIleHis-328 |
| SEQ. ID. NO. 32182 | 330-GlnSerIleGlnAsnThrGlyLysLeu-338 |
| SEQ. ID. NO. 32183 | 340-SerAlaGlyThrGluAspLeuAlaVal-348 |
| SEQ. ID. NO. 32184 | 351-SerLeuAsnAsnGlnAsnGlyGluIleAlaThrAsn-362 |
| SEQ. ID. NO. 32185 | 366-IleIleHisAspGlyGlnGlnSer-373 |
| SEQ. ID. NO. 32186 | 379-AsnThrAsnGlyThrIleGlnSerGlyArgAspValAlaIle-392 |
| SEQ. ID. NO. 32187 | 395-LysSerLeuSerAsnAsnGlyThrLeuAlaAlaAspAsnLysLeuAspIleAlaLeu-413 |
| SEQ. ID. NO. 32188 | 415-AspAspPheTyrValGluArgLysIleValAlaGlyAsnGluLeu-429 |
| SEQ. ID. NO. 32189 | 431-LeuSerThrArgGlySerLeuLysAsnSerHisThr-442 |
| SEQ. ID. NO. 32190 | 444-GlnAlaGlyLysArgIleArgIleLysAlaAsnAsnLeuAspAsn-458 |
| SEQ. ID. NO. 32191 | 463-AsnIleGlnSerGlyGlyThrThrAspIleGlyThrGlnHisAsnLeuThrAsnArgGlyLeuIleAspGlyGlnGlnThrLysIleGln-492 |
| SEQ. ID. NO. 32192 | 513-AlaThrArgLeuAspAsnGlnAspGluAsnGlyThrGly-525 |
| SEQ. ID. NO. 32193 | 529-AlaAlaArgGluAsnLeu-534 |
| SEQ. ID. NO. 32194 | 540-GlnLeuAsnAsnArgGluAsnSerLeu-548 |
| SEQ. ID. NO. 32195 | 559-GlyAlaLeuAspThrAsnAspGlnAlaThrGlyLysAlaGlnArgIleHisAsnAlaGlyAla-579 |
| SEQ. ID. NO. 32196 | 583-AlaAlaGlyLysMetArgLeuGlyValGluLysLeuHisAsnThrAsnGluHisLeuLys-602 |
| SEQ. ID. NO. 32197 | 607-GluThrGlyArgGluArgIleValAsp-615 |
| SEQ. ID. NO. 32198 | 623-GluLeuLeuArgGluGlyThrGlnHis-631 |
| SEQ. ID. NO. 32199 | 638-TyrAsnAsnGluSerAspHisLeuArgThrProAspGlyValAlaHis-653 |
| SEQ. ID. NO. 32200 | 657-HisLysTyrAspTyrGluValThrGlnGluThrGlnVal-670 |
| SEQ. ID. NO. 32201 | 680-AlaGlySerAspLeuIleIleAspSerLysAlaValPheAsnSerAspSerArgIle-698 |
| SEQ. ID. NO. 32202 | 707-GlnThrGluLysAspGlyLeuHisAsnGluGlnThrPheGlyGluLysLysValPheSerGluAsnGlyLysLeuHisAsn-733 |
| SEQ. ID. NO. 32203 | 735-TrpArgAlaArgArgLysGlyHisAspGluThrGlyHisArgGluGlnAsnTyrThrLeuProGluGluIleThrArgAspIleSerLeu-764 |
| SEQ. ID. NO. 32204 | 770-GluSerHisSerLysAlaLeuSerArgHisAlaProSerGlnGlyThrGluLeuProGlnSerAsnArgAspAsnIleArgThrAlaLysSerAsnGlyIle-803 |

TABLE 1-continued

| | |
|---|---|
| SEQ. ID. NO. 32205 | 825-ProAlaAsnLysGlyTyrLeuValGluThrAspProArgPheAlaAsn-840 |
| SEQ. ID. NO. 32206 | 854-LeuLysLeuAspProAsnAsnLeuHisLysArgLeuGlyAspGlyTyrTyrGluGlnArgLeuIleAsn-876 |
| SEQ. ID. NO. 32207 | 883-ThrGlyHisArgArgLeuAlaGlyTyrGlnAsnAspGluGluGlnPheLysAlaLeuMetAspAsnGlyAlaThrAlaAlaArgSerMetAsn-913 |
| SEQ. ID. NO. 32208 | 922-AlaGluGlnAlaAla-926 |
| SEQ. ID. NO. 32209 | 938-LysGluValLysLeuProAspGlyGlyThr-947 |
| SEQ. ID. NO. 32210 | 959-ValLysAsnGlyGlyIleAspGlyLysGly-968 |
| SEQ. ID. NO. 32211 | 982-GlySerLeuLysAsnSerGlyThrIleAlaGlyArgAsnAla-995 |
| SEQ. ID. NO. 32212 | 999-AsnThrAspThrLeuAspAsnIleGlyGly-1008 |
| SEQ. ID. NO. 32213 | 1010-IleHisAlaGlnLysSerAlaVal-1017 |
| SEQ. ID. NO. 32214 | 1040-AlaGlyAsnAsnIleAsnAsnGlnSerThrAlaLysSerSerGlnAsnAlaGlnGlySer-1059 |
| SEQ. ID. NO. 32215 | 1072-ThrGlyLysGluLysGlyVal-1078 |
| SEQ. ID. NO. 32216 | 1083-AlaGlyLysAspIleAsnIle-1089 |
| SEQ. ID. NO. 32217 | 1094-IleSerAsnGlnSerAspGlnGlyGlnThrArgLeuGlnAlaGlyArgAspIleAsnLeuAspThrValGlnThrGlyLysTyrGlnGluIle HisPheAspAlaAspAsnHisThrIleArgGlySerThrAsnGluValGlySerSerIleGlnThrLysGlyAspVal-1150 |
| SEQ. ID. NO. 32218 | 1155-GlyAsnAsnLeuAsnAlaLysAlaAlaGluValGlySerAlaLysGlyThr-1171 |
| SEQ. ID. NO. 32219 | 1175-TyrAlaLysAsnAspIleThrIle-1182 |
| SEQ. ID. NO. 32220 | 1190-GlnValAspAspAlaSerLysHisThrGlyArgSerGlyGlyGlyAsnLys-1206 |
| SEQ. ID. NO. 32221 | 1208-ValIleThrAspLysAlaGlnSerHisHisGluThrAlaGlnSerSerThrPheGluGlyLysGln-1229 |
| SEQ. ID. NO. 32222 | 1233-GlnAlaGlyAsnAspAlaAsn-1239 |
| SEQ. ID. NO. 32223 | 1245-ValIleSerAspAsnGlyThrArgIleGlnAla-1255 |
| SEQ. ID. NO. 32224 | 1262-GlyThrThrGlnThrGlnSerGlnSerGluThrTyrHisGlnThrGlnLysSerGlyLeu-1281 |
| SEQ. ID. NO. 32225 | 1291-GlySerLysThrAsnThrGlnGluAsnGlnSerGlnSerAsnGluHisThrGlySerThrValGlySerLeuLysGlyAspThrThrIle-1320 |
| SEQ. ID. NO. 32226 | 1324-LysHisTyrGluGlnThrGlySerAsnValSerSerProGluGlyAsnAsnLeu-1341 |
| SEQ. ID. NO. 32227 | 1354-AsnGlnLeuAsnSerLysThrThrGlnThrTyrGluGlnLysGlyLeu-1369 |
| SEQ. ID. NO. 32228 | 1379-ArgPheGlyThrThrSerAspCysArgSerThrGlnSerSerLysGlnValGlyGlnSerLysAsnAspArgValAsnAla-1405 |
| SEQ. ID. NO. 32229 | 1415-AlaTyrGlnThrGlyLysGlyAlaGlnAsnLeuAlaAsnGlyThrThrAsnAlaLys-1433 |
| SEQ. ID. NO. 32230 | 1441-TyrGlyGluGlnGlnAsnArgGlnThrThrGln-1451 |
| SEQ. ID. NO. 32231 | 1460-SerGlnIleGlnAlaGlyGlyLysThr-1468 |
| SEQ. ID. NO. 32232 | 1470-LeuTyrCysArgArgCysGlyGluGlnSerAsn-1480 |
| SEQ. ID. NO. 32233 | 1487-GlyValSerGlyArgAlaGlyThr-1494 |
| SEQ. ID. NO. 32234 | 1496-LeuIleAlaAspLysGlnIle-1502 |
| SEQ. ID. NO. 32235 | 1506-SerAlaGluGlnSerAsnThrGluArgSerGlnAsnLysSerAlaGlyTrpAsn-1523 |
| SEQ. ID. NO. 32236 | 1543-GlyAsnValGlyLysGlyTyrGlyTyrGlyAspSerValThrHisArgHisSerHisIleGlyAspLysGlySerGln-1568 |
| SEQ. ID. NO. 32237 | 1572-GlnSerGlyGlyAspThrIleIle-1579 |
| SEQ. ID. NO. 32238 | 1582-AlaGlnValArgGlyLysGlyValGlnValAsnAlaLysAsn-1595 |
| SEQ. ID. NO. 32239 | 1600-SerValGlnAspArgGluThrTyrGlnSerLysGlnGlnAsnAlaGlyAla-1616 |
| SEQ. ID. NO. 32240 | 1626-AlaSerGlyAspTyrSerGlnSerLysIleArgAlaAspHis-1639 |
| SEQ. ID. NO. 32241 | 1641-SerValThrGluGlnSerGlyIleTyrAlaGlyGluAspGlyTyrGln-1656 |
| SEQ. ID. NO. 32242 | 1660-GlyAsnHisThrGlyLeuLysGlyGlyIle-1669 |
| SEQ. ID. NO. 32243 | 1673-SerGlnSerAlaLysAspLysGlyLysAsnArgPheSerThrGlyThrLeuAlaGlySerAspIleGlnAsnTyrSerGlnTyrGluGlyLys SerPheGly-1706 |
| SEQ. ID. NO. 32244 | 1713-ValSerGlyLysThrLeuGlyGlnGlyAlaLysAsnLysProGlnAspLysHisLeu-1731 |
| SEQ. ID. NO. 32245 | 1734-IleAlaAspLysAsnGlyAlaSerSer-1742 |
| SEQ. ID. NO. 32246 | 1745-GlyTyrGlySerAspSerAspSerGlnAsnSerSerIleThrLysSerGlyIleAsnThrProLysAsnIleGlnIleThrAspGluAlaAlaGln-1775 |
| SEQ. ID. NO. 32247 | 1778-LeuThrGlyLysIleAlaAlaGlnThrLysAlaAspIleAspThrAsnValThrThrAspThrAlaGluArgHisSerGlySerLeuLysAsn IlePheAspLysAspArgValGlnSerGluLeuAspLeuGlnArgThrValSerGlnAspPheSerLysAsnValGlnGlnThrAsnThrGluIle-1840 |
| SEQ. ID. NO. 32248 | 1842-GlnHisLeuAspLysLeuLysAlaAspLysGluAlaAlaGluThrAlaAla-1858 |
| SEQ. ID. NO. 32249 | 1863-AlaAsnGlyAspMetGluThrAlaLysArgLysAlaHisGluAlaGlnAspAlaAlaAlaLysAlaAspAsnTrpGlnGln-1889 |
| SEQ. ID. NO. 32250 | 1899-SerGlyLeuAlaGluProThrGlnSerGly-1908 |
| SEQ. ID. NO. 32251 | 1915-ThrAlaSerProAspValSer-1921 |
| SEQ. ID. NO. 32252 | 1927-HisPheLysAspLeuAlaGlyGlnAsnAlaAsnGlyLysLeuThrAlaSerGlnGluThr-1946 |
| SEQ. ID. NO. 32253 | 1963-XxxGlyAsnAsnAlaPro-1968 |
| SEQ. ID. NO. 32254 | 1973-GlyAlaGlyGlySerGluAlaAla-1980 |
| SEQ. ID. NO. 32255 | 1988-LeuTyrGlyLysGlyAspGlyGlySerLeuAsnAlaGluGluLysGluThrVal-2005 |
| SEQ. ID. NO. 32256 | 2017-GlyAlaAlaGluGlyAsnSerSerAlaAspAla-2027 |
| SEQ. ID. NO. 32257 | 2034-ThrAlaSerAspPheAlaSerSerPheSerTyr-2044 |
| Hydrophilic Regions - Hopp-Woods | |
| SEQ. ID. NO. 32258 | 10-PheAsnArgLysArgGlyAla-16 |
| SEQ. ID. NO. 32259 | 22-GluThrThrLysArgGluGlyLysSerCysAlaAspSerGlySer-36 |
| SEQ. ID. NO. 32260 | 78-IleIleThrAspLysAlaAlaProLysThrGlnGln-89 |
| SEQ. ID. NO. 32261 | 131-AsnSerArgSerAsnThr-136 |
| SEQ. ID. NO. 32262 | 153-GlyGluAlaArgVal-157 |
| SEQ. ID. NO. 32263 | 176-ValGlyGlyArgArgAlaGluVal-183 |
| SEQ. ID. NO. 32264 | 235-LeuAspAlaArgAspThrAspPhe-242 |
| SEQ. ID. NO. 32265 | 261-AlaGlyIleArgAsn-265 |
| SEQ. ID. NO. 32266 | 296-GlnAspMetAsnAsnThrAlaGluHisLysValAsnIle-308 |
| SEQ. ID. NO. 32267 | 311-GlnAlaPheGluAsnSerGly-317 |
| SEQ. ID. NO. 32268 | 342-GlyThrGluAspLeuAla-347 |
| SEQ. ID. NO. 32269 | 355-GlnAsnGlyGluIleAlaThr-361 |
| SEQ. ID. NO. 32270 | 385-GlnSerGlyArgAspValAlaIle-392 |
| SEQ. ID. NO. 32271 | 403-LeuAlaAlaAspAsnLysLeuAspIleAlaLeu-413 |
| SEQ. ID. NO. 32272 | 417-PheTyrValGluArgLysIleValAla-425 |
| SEQ. ID. NO. 32273 | 435-GlySerLeuLysAsn-439 |
| SEQ. ID. NO. 32274 | 444-GlnAlaGlyLysArgIleArgIleLysAlaAsnAsnLeu-456 |
| SEQ. ID. NO. 32275 | 468-GlyThrThrAspIleGlyThr-474 |
| SEQ. ID. NO. 32276 | 487-GlnGlnThrLysIleGln-492 |
| SEQ. ID. NO. 32277 | 514-ThrArgLeuAspAsnGlnAspGluAsnGlyThr-524 |
| SEQ. ID. NO. 32278 | 529-AlaAlaArgGluAsnLeu-534 |
| SEQ. ID. NO. 32279 | 540-GlnLeuAsnAsnArgGluAsnSer-547 |
| SEQ. ID. NO. 32280 | 561-LeuAspThrAsnAspGlnAlaThrGlyLysAlaGlnArgIleHis-575 |

TABLE 1-continued

| | |
|---|---|
| SEQ. ID. NO. 32281 | 583-AlaAlaGlyLysMetArgLeuGlyValGluLysLeuHisAsnThrAsnGluHisLeuLys-602 |
| SEQ. ID. NO. 32282 | 607-GluThrGlyArgGluArgIleValAsp-615 |
| SEQ. ID. NO. 32283 | 623-GluLeuLeuArgGluGlyThrGlnHis-631 |
| SEQ. ID. NO. 32284 | 640-AsnGluSerAspHisLeuArgThrProAspGlyValAla-652 |
| SEQ. ID. NO. 32285 | 659-TyrAspTyrGluLysValThrGln-666 |
| SEQ. ID. NO. 32286 | 684-LeuIleIleAspSerLysAla-690 |
| SEQ. ID. NO. 32287 | 694-SerAspSerArgIle-698 |
| SEQ. ID. NO. 32288 | 707-GlnThrGluLysAspGlyLeuHisAsn-715 |
| SEQ. ID. NO. 32289 | 717-GlnThrPheGlyGluLysLysValPheSerGluAsnGlyLys-730 |
| SEQ. ID. NO. 32290 | 736-ArgAlaArgArgLysGlyHisAspGluThrGlyHisArgGluGlnAsn-751 |
| SEQ. ID. NO. 32291 | 756-GluGluIleThrArgAspIleSer-763 |
| SEQ. ID. NO. 32292 | 771-SerHisSerLysAlaLeuSerArgHisAlaPro-781 |
| SEQ. ID. NO. 32293 | 783-GlnGlyThrGluLeuProGlnSerAsnArgAspAsnIleArgThrAlaLysSerAsnGly-802 |
| SEQ. ID. NO. 32294 | 830-TyrLeuValGluThrAspProArgPheAlaAsn-840 |
| SEQ. ID. NO. 32295 | 854-LeuLysLeuAspPro-858 |
| SEQ. ID. NO. 32296 | 860-AsnLeuHisLysArgLeuGly-866 |
| SEQ. ID. NO. 32297 | 883-ThrGlyHisArgArgLeuAspGlyTyrGlnAsnAspGluGluGlnPheLysAlaLeuMet-902 |
| SEQ. ID. NO. 32298 | 905-GlyAlaThrAlaAlaArg-910 |
| SEQ. ID. NO. 32299 | 922-AlaGluGlnAlaAla-926 |
| SEQ. ID. NO. 32300 | 938-LysGluValLysLeuProAspGlyGlyThr-947 |
| SEQ. ID. NO. 32301 | 959-ValLysAsnGlyGlyIleAspGlyLysGly-968 |
| SEQ. ID. NO. 32302 | 982-GlySerLeuLysAsn-986 |
| SEQ. ID. NO. 32303 | 1010-IleHisAlaGlnLysSerAlaVal-1017 |
| SEQ. ID. NO. 32304 | 1048-SerThrAlaLysSerSerGlnAsnAlaGlnGly-1058 |
| SEQ. ID. NO. 32305 | 1073-GlyLysGluLysGlyVal-1078 |
| SEQ. ID. NO. 32306 | 1083-AlaGlyLysAspIleAsn-1088 |
| SEQ. ID. NO. 32307 | 1096-AsnGlnSerAspGlnGlyGlnThrArgLeuGlnAlaGlyArgAspIleAsnLeu-1113 |
| SEQ. ID. NO. 32308 | 1125-HisPheAspAlaAspAsnHisThrIleArgGlySerThrAsnGluValGlySer-1142 |
| SEQ. ID. NO. 32309 | 1144-IleGlnThrLysGlyAspVal-1150 |
| SEQ. ID. NO. 32310 | 1158-LeuAsnAlaLysAlaAlaGluValGlySerAlaLysGly-1170 |
| SEQ. ID. NO. 32311 | 1176-AlaLysAsnAspIle-1180 |
| SEQ. ID. NO. 32312 | 1190-GlnValAspAspAlaSerLysHisThrGlyArgSerGlyGlyGly-1204 |
| SEQ. ID. NO. 32313 | 1208-ValIleThrAspLysAlaGlnSerHisHisGluThrAlaGln-1221 |
| SEQ. ID. NO. 32314 | 1223-SerThrPheGluGlyLysGln-1229 |
| SEQ. ID. NO. 32315 | 1249-AsnGlyThrArgIleGlnAla-1255 |
| SEQ. ID. NO. 32316 | 1267-GlnSerGlnSerGluThr-1272 |
| SEQ. ID. NO. 32317 | 1276-ThrGlnLysSerGlyLeu-1281 |
| SEQ. ID. NO. 32318 | 1292-SerLysThrAsnThrGlnGluAsnGlnSerGlnSerAsnGluHisThrGly-1308 |
| SEQ. ID. NO. 32319 | 1314-LeuLysGlyAspThr-1318 |
| SEQ. ID. NO. 32320 | 1324-LysHisTyrGluGlnThrGly-1330 |
| SEQ. ID. NO. 32321 | 1334-SerSerProGluGly-1338 |
| SEQ. ID. NO. 32322 | 1356-LeuAsnSerLysThrThrGln-1362 |
| SEQ. ID. NO. 32323 | 1364-TyrGluGlnLysGly-1368 |
| SEQ. ID. NO. 32324 | 1384-SerAspCysArgSerThrGlnSerSerLysGlnValGlyGlnSerLysAsnAspArgValAsn-1404 |
| SEQ. ID. NO. 32325 | 1417-GlnThrGlyLysGlyAlaGln-1423 |
| SEQ. ID. NO. 32326 | 1443-GluGlnGlnAsnArgGlnThrThr-1450 |
| SEQ. ID. NO. 32327 | 1474-ArgCysGlyGluGlnSerAsn-1480 |
| SEQ. ID. NO. 32328 | 1488-ValSerGlyArgAlaGly-1493 |
| SEQ. ID. NO. 32329 | 1497-IleAlaAspLysGlnIle-1502 |
| SEQ. ID. NO. 32330 | 1506-SerAlaGluGlnSerAsnThrGluArgSerGlnAsnLys-1518 |
| SEQ. ID. NO. 32331 | 1560-SerHisIleGlyAspLysGlySer-1567 |
| SEQ. ID. NO. 32332 | 1582-AlaGlnValArgGlyLysGlyVal-1589 |
| SEQ. ID. NO. 32333 | 1600-SerValGlnAspArgGluThrTyrGlnSerLysGlnGlnAsn-1613 |
| SEQ. ID. NO. 32334 | 1628-GlyAspTyrSerGlnSerLysIleArgAlaAspHis-1639 |
| SEQ. ID. NO. 32335 | 1650-AlaGlyGluAspGlyTyrGln-1656 |
| SEQ. ID. NO. 32336 | 1674-GlnSerAlaLysAspLysGlyLysAsnArgPheSer-1685 |
| SEQ. ID. NO. 32337 | 1700-TyrGluGlyLysSer-1704 |
| SEQ. ID. NO. 32338 | 1717-ThrLeuGlyGlnGlyAlaLysAsnLysProGlnAspLysHisLeu-1731 |
| SEQ. ID. NO. 32339 | 1734-IleAlaAspLysAsnGlyAla-1740 |
| SEQ. ID. NO. 32340 | 1748-SerAspSerAspSerGlnSerSerIleThr-1757 |
| SEQ. ID. NO. 32341 | 1768-GlnIleThrAspGluAlaAlaGln-1775 |
| SEQ. ID. NO. 32342 | 1786-ThrLysAlaAspIleAspThr-1792 |
| SEQ. ID. NO. 32343 | 1794-ValThrThrAspThrAlaArgHisSerGlySerLeu-1806 |
| SEQ. ID. NO. 32344 | 1808-AsnIlePheAspLysAspArgValGlnSerGluLeuAspLeuGlnArgThrValSer-1826 |
| SEQ. ID. NO. 32345 | 1836-ThrAsnThrGluIle-1840 |
| SEQ. ID. NO. 32346 | 1842-GlnHisLeuAspLysLeuLysAlaAspLysGluAlaAlaGluThrAlaAla-1858 |
| SEQ. ID. NO. 32347 | 1865-GlyAspMetGluThrAlaLysArgLysAlaHisGluAlaGlnAspAlaAlaAlaLysAlaAspAsn-1886 |
| SEQ. ID. NO. 32348 | 1901-LeuAlaGluProThrGln-1906 |
| SEQ. ID. NO. 32349 | 1927-HisPheLysAspLeuAlaGly-1933 |
| SEQ. ID. NO. 32350 | 1936-AlaAsnGlyLysLeuThrAlaSerGlnGluThr-1946 |
| SEQ. ID. NO. 32351 | 1975-GlyGlySerGluAlaAla-1980 |
| SEQ. ID. NO. 32352 | 1991-LysGlyAspGlyGlySerLeuAsnAlaGluGluLysGluThrVal-2005 |
| SEQ. ID. NO. 32353 | 2017-GlyAlaAlaGluGlyAsnSerSerAla-2025 | g565-2
AMPHI Regions - AMPHI

| | |
|---|---|
| SEQ. ID. NO. 32354 | 50-AlaThrCysThrArgAlaMetSerLysSer-59 |
| SEQ. ID. NO. 32355 | 66-SerSerTrpAlaArg-70 |
| SEQ. ID. NO. 32356 | 103-AspPheMetSerGlnLeuAspLeuThr-111 |
| SEQ. ID. NO. 32357 | 139-CysSerAsnSerGlyGluThrIleSerSerCysProAlaMetAlaSerIleThrLysProAsn-159 |
| SEQ. ID. NO. 32358 | 184-AlaAsnThrThrAsnAlaPheAsnThr-192 |

TABLE 1-continued

Antigenic Index - Jameson-Wolf
SEQ. ID. NO. 32359   1-MetAspSerThrLeuSerLysThrCys-9
SEQ. ID. NO. 32360   23-PheAlaArgProArgProAlaAlaSerAsnThrSerLeu-35
SEQ. ID. NO. 32361   37-PheAlaSerProAsnAspThrGlySer-45
SEQ. ID. NO. 32362   55-AlaMetSerLysSerSerAlaLysTyrGly-64
SEQ. ID. NO. 32363   67-SerTrpAlaArgThrArgProThrValCysProProLeuProLysProThrIle-84
SEQ. ID. NO. 32364   86-ThrXxxSerAspLeu-90
SEQ. ID. NO. 32365   97-MetLeuCysArgSerSerAspPheMetSer-106
SEQ. ID. NO. 32366   109-AspLeuThrLysArgProThrSerAlaSerLeuProProLysArgLysGlyAlaIle-127
SEQ. ID. NO. 32367   129-IleAspSerArgThrAlaAla-135
SEQ. ID. NO. 32368   139-CysSerAsnSerGlyGluThrIleSer-147
SEQ. ID. NO. 32369   155-IleThrLysProAsnSerProProCysAlaArgTyr-166
SEQ. ID. NO. 32370   170-LeuArgLeuSerProThrGlu-176
SEQ. ID. NO. 32371   194-SerIleAlaAsnSerIleAsnThrCysArgGlnProPro-206
Hydrophilic Regions - Hopp-Woods
SEQ. ID. NO. 32372   24-AlaArgProArgProAlaAla-30
SEQ. ID. NO. 32373   39-SerProAsnAspThrGlySer-45
SEQ. ID. NO. 32374   55-AlaMetSerLysSerSerAla-61
SEQ. ID. NO. 32375   69-AlaArgThrArgPro-73
SEQ. ID. NO. 32376   100-ArgSerSerAspPhe-104
SEQ. ID. NO. 32377   109-AspLeuThrLysArgProThrSer-116
SEQ. ID. NO. 32378   119-LeuProProLysArgLysGlyAlaIle-127
SEQ. ID. NO. 32379   129-IleAspSerArgThr-133
SEQ. ID. NO. 32380   141-AsnSerGlyGluThrIleSer-147
SEQ. ID. NO. 32381   156-ThrLysProAsnSer-160
g566
AMPHI Regions - AMPHI
SEQ. ID. NO. 32382   52-GlyPheValGlyAspPheHisAlaPhe-60
Antigenic Index - Jameson-Wolf
SEQ. ID. NO. 32383   36-ProAsnCysGlyAlaAspGlyThrGlyGlyLysGlyHisAla-49
SEQ. ID. NO. 32384   61-AlaValGlyGlyGluGluGlyGlyVal-69
SEQ. ID. NO. 32385   77-AlaAspGlyGlyLysAlaAspGlyGlyArgIleAlaArg-89
SEQ. ID. NO. 32386   105-AlaAlaGluArgAlaGlyAspAspPheAla-114
Hydrophilic Regions - Hopp-Woods
SEQ. ID. NO. 32387   39-GlyAlaAspGlyThrGlyGlyLysGlyHisAla-49
SEQ. ID. NO. 32388   63-GlyGlyGluGluGlyGlyVal-69
SEQ. ID. NO. 32389   78-AspGlyGlyLysAlaAspGlyGlyArgIleAlaArg-89
SEQ. ID. NO. 32390   105-AlaAlaGluArgAlaGlyAspAspPheAla-114
g567
AMPHI Regions - AMPHI
SEQ. ID. NO. 32391   54-GluLeuValGlnGluIleAlaArgGluVal-63
SEQ. ID. NO. 32392   68-AlaLeuLysAlaVal-72
SEQ. ID. NO. 32393   110-TyrAlaLeuGluGlyIleSerAspLeuIleAlaThrValArgLysIleArgGln-127
SEQ. ID. NO. 32394   136-ThrGlyIleValArg-140
SEQ. ID. NO. 32395   151-AlaGluValSerGluGlnLeuArgSerHisPheGlyAspLeuLeu-165
SEQ. ID. NO. 32396   170-IleProArgAsnIleArgLeuAla-177
Antigenic Index - Jameson-Wolf
SEQ. ID. NO. 32397   1-MetArgArgArgAlaAlaAlaSerThrArgArgValCysSerProAlaPhe-17
SEQ. ID. NO. 32398   24-MetArgThrCysSerArgArgArgTyrAlaAlaLysArgAlaAspThr-39
SEQ. ID. NO. 32399   51-AlaGluIleGluLeu-55
SEQ. ID. NO. 32400   57-GlnGluIleAlaArgGluValArgLeuLysAsnAlaLeu-69
SEQ. ID. NO. 32401   71-AlaValAlaGluAspTyrAsp-77
SEQ. ID. NO. 32402   83-CysProProSerLeu-87
SEQ. ID. NO. 32403   123-ArgLysIleArgGlnAlaValAsnProAspLeuAspIle-135
SEQ. ID. NO. 32404   141-ThrMetTyrAspSerArgSerArgLeuValAlaAlaGluValSerGluGlnLeuArgSerHisPheGlyAspLeu-164
SEQ. ID. NO. 32405   169-AlaIleProArgAsnIleArgLeuAlaGluAlaProSerHisGly-183
SEQ. ID. NO. 32406   191-AlaGlnAlaLysGlyAlaLys-197
SEQ. ID. NO. 32407   204-AspGluLeuAlaAlaArgValSerGlyLys-213
Hydrophilic Regions - Hopp-Woods
SEQ. ID. NO. 32408   1-MetArgArgArgAlaAlaAlaSerThrArgArgValCys-13
SEQ. ID. NO. 32409   26-ThrCysSerArgArgArgTyrAlaAlaLysArgAlaAspThr-39
SEQ. ID. NO. 32410   51-AlaGluIleGluLeu-55
SEQ. ID. NO. 32411   57-GlnGluIleAlaArgGluValArgLeuLysAsnAlaLeu-69
SEQ. ID. NO. 32412   71-AlaValAlaGluAspTyrAsp-77
SEQ. ID. NO. 32413   123-ArgLysIleArgGln-127
SEQ. ID. NO. 32414   131-ProAspLeuAspIle-135
SEQ. ID. NO. 32415   142-MetTyrAspSerArgSerArgLeuValAlaAlaGluValSerGluGlnLeuArg-158
SEQ. ID. NO. 32416   172-ArgAsnIleArgLeuAlaGlu-178
SEQ. ID. NO. 32417   191-AlaGlnAlaLysGlyAlaLys-197
SEQ. ID. NO. 32418   204-AspGluLeuAlaAla-208
g568-2
AMPHI Regions - AMPHI
SEQ. ID. NO. 32419   32-AsnIlePheArgArgIle-37
SEQ. ID. NO. 32420   49-LysAlaCysLysAsn-53
SEQ. ID. NO. 32421   71-GluLysAlaAsnThrValArgTyr-78
SEQ. ID. NO. 32422   82-SerLeuAlaGlnCysPheThr-88
SEQ. ID. NO. 32423   112-ArgProLeuProSerIleIleThrAla-120
SEQ. ID. NO. 32424   154-ProXxxAspLeuAsn-158
SEQ. ID. NO. 32425   177-LeuValGlyGlnPheLeuAsnArgLeuPhe-186
SEQ. ID. NO. 32426   200-GluGluPhePheAspValValVal-207

TABLE 1-continued

| | |
|---|---|
| SEQ. ID. NO. 32427 | 227-AspPheAsnGlnValPheAlaAlaPheLeu-236 |
| SEQ. ID. NO. 32428 | 241-HisArgHisAlaAspGlnIleAlaAspSerCysArgValGlnSerGln-256 |

Antigenic Index - Jameson-Wolf

| | |
|---|---|
| SEQ. ID. NO. 32429 | 12-LysAlaSerAlaSerSerIlePro-19 |
| SEQ. ID. NO. 32430 | 21-ArgIleCysArgLeuLysArgSerArgLeuProAsnIlePhe-34 |
| SEQ. ID. NO. 32431 | 39-PheSerCysArgArgArgThrCysPheCysLysAlaCysLysAsnSerProIleArgAsnGluThrSerSerSerGlyArgArgGlnPheSerVal GluLysAlaAsnThr-75 |
| SEQ. ID. NO. 32432 | 91-SerAsnAlaSerLysProArgLeu-98 |
| SEQ. ID. NO. 32433 | 102-IleArgGlyArgLysArgPhePheAla-110 |
| SEQ. ID. NO. 32434 | 141-PheArgGlySerAlaPheLysCysArgLeuAsnAlaAlaProXxxAspLeuAsnArg-159 |
| SEQ. ID. NO. 32435 | 166-GlySerGlnAsnLeu-170 |
| SEQ. ID. NO. 32436 | 213-ValAlaAspArgAspAlaSer-219 |
| SEQ. ID. NO. 32437 | 237-GlyGlnHisGlyHisArgHisAlaAspGlnIleAlaAspSerCysArgValGlnSerGln-256 |

Hydrophilic Regions - Hopp-Woods

| | |
|---|---|
| SEQ. ID. NO. 32438 | 21-ArgIleCysArgLeuLysArgSerArgLeu-30 |
| SEQ. ID. NO. 32439 | 41-CysArgArgArgThrCysPhe-47 |
| SEQ. ID. NO. 32440 | 49-LysAlaCysLysAsnSerProIleArgAsnGluThrSerSerSerGlyArgArgGlnPheSerValGluLysAlaAsnThr-75 |
| SEQ. ID. NO. 32441 | 93-AlaSerLysProArgLeu-98 |
| SEQ. ID. NO. 32442 | 102-IleArgGlyArgLysArgPhePheAla-110 |
| SEQ. ID. NO. 32443 | 144-SerAlaPheLysCysArgLeu-150 |
| SEQ. ID. NO. 32444 | 152-AlaAlaProXxxAspLeuAsnArg-159 |
| SEQ. ID. NO. 32445 | 213-ValAlaAspArgAspAlaSer-219 |
| SEQ. ID. NO. 32446 | 239-HisGlyHisArgHisAlaAspGlnIleAlaAspSerCysArgVal-253 | g569-2
AMPHI Regions - AMPHI

| | |
|---|---|
| SEQ. ID. NO. 32447 | 29-AlaAlaPheCysGlyLeuIleAlaLeuThrAlaLeuTrpGluTyrAlaArgMetAlaGlyLeuCysLys-51 |
| SEQ. ID. NO. 32448 | 86-PheTrpLeuAlaValMetPro-92 |
| SEQ. ID. NO. 32449 | 161-IleAlaArgAlaIleSerProGlyLysSerTrpGluGlyAlaIle-175 |
| SEQ. ID. NO. 32450 | 203-ThrValLeuIleGlyLeu-208 |
| SEQ. ID. NO. 32451 | 210-LeuThrValValSerValCysGlyAspLeuLeuGluSerTrpLeuLys-225 |

Antigenic Index - Jameson-Wolf

| | |
|---|---|
| SEQ. ID. NO. 32452 | 50-CysLysThrGluThrAsnHis-56 |
| SEQ. ID. NO. 32453 | 98-LysTrpArgLeuAsnGlyGlyTrp-105 |
| SEQ. ID. NO. 32454 | 124-SerLeuArgProHisProAspAspAlaLeu-133 |
| SEQ. ID. NO. 32455 | 154-LysAlaLeuGlyLysHisLysIleAlaArg-163 |
| SEQ. ID. NO. 32456 | 165-IleSerProGlyLysSerTrpGlu-172 |
| SEQ. ID. NO. 32457 | 227-AlaAlaGlyIleLysAspSerSerAsnLeuLeuProGlyHis-240 |
| SEQ. ID. NO. 32458 | 242-GlyValPheAspArgThrAspSer-249 |

Hydrophilic Regions - Hopp-Woods

| | |
|---|---|
| SEQ. ID. NO. 32459 | 50-CysLysThrGluThr-54 |
| SEQ. ID. NO. 32460 | 127-ProHisProAspAspAlaLeu-133 |
| SEQ. ID. NO. 32461 | 155-AlaLeuGlyLysHisLysIleAlaArg-163 |
| SEQ. ID. NO. 32462 | 227-AlaAlaGlyIleLysAspSerSerAsn-235 |
| SEQ. ID. NO. 32463 | 243-ValPheAspArgThrAspSer-249 | g570
AMPHI Regions - AMPHI

| | |
|---|---|
| SEQ. ID. NO. 32464 | 6-ArgAlaPheAlaAlaAlaLeuIleGlyLeu-15 |
| SEQ. ID. NO. 32465 | 22-HisAlaAspThrPheGlnLysIleGlyPheIleAsn-33 |
| SEQ. ID. NO. 32466 | 43-GlnAlaArgAsnIleGlnLysThrLeuAspGly-53 |
| SEQ. ID. NO. 32467 | 60-AspGluLeuGlnLysLeuGln-66 |
| SEQ. ID. NO. 32468 | 81-LeuLysAspAlaLysLys-86 |
| SEQ. ID. NO. 32469 | 91-GluLysTrpArgGlyLeuValGluAlaPheArg-101 |
| SEQ. ID. NO. 32470 | 122-LeuGlnGlnAsnAlaAsnArgValIleValLysIle-133 |

Antigenic Index - Jameson-Wolf

| | |
|---|---|
| SEQ. ID. NO. 32471 | 33-AsnThrGluArgIleTyrLeuGluSerLysGlnAlaArgAsnIleGlnLysThrLeuAspGlyGluPheSerAlaArgGlnAspGluLeuGln LysLeuGlnArgGluGlyLeuAspLeuGluArgGlnLeuAlaGlyGlyLysLeuLysAspAlaLysLysAlaGlnAlaGluGluLysTrpArgGly-95 |
| SEQ. ID. NO. 32472 | 99-AlaPheArgLysLysGlnAlaGlnPheGluGluAspTyrAsnLeuArgArgAsnGluGluPheAla-120 |
| SEQ. ID. NO. 32473 | 123-GlnGlnAsnAlaAsnArgVal-129 |
| SEQ. ID. NO. 32474 | 133-IleAlaLysGlnGluGlyTyrAspValIle-142 |
| SEQ. ID. NO. 32475 | 150-AsnThrGlnTyrAspValThrAspSerValIleLysGluMetAsnAlaArg-166 |

Hydrophilic Regions - Hopp-Woods

| | |
|---|---|
| SEQ. ID. NO. 32476 | 37-IleTyrLeuGluSerLysGlnAlaArgAsnIleGlnLysThrLeuAspGlyGluPheSerAlaArgGlnAspGluLeuGlnLysLeuGlnArg GluGlyLeuAspLeuGluArgGlnLeuAla-77 |
| SEQ. ID. NO. 32477 | 79-GlyLysLeuLysAspAlaLysLysAlaGlnAlaGluGluLysTrpArgGly-95 |
| SEQ. ID. NO. 32478 | 99-AlaPheArgLysLysGlnAlaGlnPheGluGluAspTyrAsnLeuArgArgAsnGluGluPheAla-120 |
| SEQ. ID. NO. 32479 | 133-IleAlaLysGlnGluGlyTyr-139 |
| SEQ. ID. NO. 32480 | 154-AspValThrAspSerValIleLysGluMetAsnAlaArg-166 | g571
AMPHI Regions - AMPHI

| | |
|---|---|
| SEQ. ID. NO. 32481 | 10-ValValThrValPheGlyGlyGlyIleGlySerAlaVal-22 |
| SEQ. ID. NO. 32482 | 58-AlaAlaValAlaAspPhePheAlaVal-66 |
| SEQ. ID. NO. 32483 | 89-ValGluValPheLysGlu-94 |

Antigenic Index - Jameson-Wolf

| | |
|---|---|
| SEQ. ID. NO. 32484 | 30-LysGlnAlaGlnAlaAspGly-36 |
| SEQ. ID. NO. 32485 | 40-PheArgThrGlyHisArgGluGluGlnLeuGlyGlyAspVal-53 |
| SEQ. ID. NO. 32486 | 72-ArgAlaGluArgAlaAla-77 |
| SEQ. ID. NO. 32487 | 91-ValPheLysGluGlyAspPhe-97 |
| SEQ. ID. NO. 32488 | 105-ArgAsnAlaAspPheAlaAlaGluHisArgGluGlyPheAla-119 |

Hydrophilic Regions - Hopp-Woods

| | |
|---|---|
| SEQ. ID. NO. 32489 | 30-LysGlnAlaGlnAlaAsp-35 |

TABLE 1-continued

| | |
|---|---|
| SEQ. ID. NO. 32490 | 42-ThrGlyHisArgGluGluGlnLeuGly-50 |
| SEQ. ID. NO. 32491 | 72-ArgAlaGluArgAlaAla-77 |
| SEQ. ID. NO. 32492 | 91-ValPheLysGluGlyAspPhe-97 |
| SEQ. ID. NO. 32493 | 105-ArgAsnAlaAspPheAlaAlaGluHisGlnArgGluGlyPheAla-119 | g572
AMPHI Regions - AMPHI

| | |
|---|---|
| SEQ. ID. NO. 32494 | 10-LeuProSerAlaLeuAla-15 |
| SEQ. ID. NO. 32495 | 61-GlnValLeuProArgAspTyrThrAspArgLeuAsn-72 |
| SEQ. ID. NO. 32496 | 94-SerThrPheAspSerIleThrPro-101 |
| SEQ. ID. NO. 32497 | 154-IleHisSerMetValArg-159 |
| SEQ. ID. NO. 32498 | 183-GlyLeuProGluArgIleAspSerGly-191 |
| SEQ. ID. NO. 32499 | 200-LeuSerAlaLeuThr-204 |

Antigenic Index - Jameson-Wolf

| | |
|---|---|
| SEQ. ID. NO. 32500 | 18-GlnLysGlyLysThr-22 |
| SEQ. ID. NO. 32501 | 26-AlaAsnLysGluThrLeu-31 |
| SEQ. ID. NO. 32502 | 41-ThrAlaArgAlaAsnGly-46 |
| SEQ. ID. NO. 32503 | 51-ProValAspSerGluHis-56 |
| SEQ. ID. NO. 32504 | 63-LeuProArgAspTyrThrAspArgLeuAsnGluHisGlyIleAsp-77 |
| SEQ. ID. NO. 32505 | 97-AspSerIleThrProGluGlnAlaValLysHisProAsnTrpArgMetGlyArgLysIleSerValAspSer-120 |
| SEQ. ID. NO. 32506 | 122-ThrMetAlaAsnLysGlyLeuGluLeu-130 |
| SEQ. ID. NO. 32507 | 138-AsnCysProProAspLysLeuGluVal-146 |
| SEQ. ID. NO. 32508 | 158-ValArgTyrArgAspGlySerVal-165 |
| SEQ. ID. NO. 32509 | 170-GlyAsnProAspMetArgThr-176 |
| SEQ. ID. NO. 32510 | 184-LeuProGluArgIleAspSerGlyValGlyLysLeuAsp-196 |
| SEQ. ID. NO. 32511 | 205-PheGlnLysProAspPheGlyArg-212 |
| SEQ. ID. NO. 32512 | 224-AsnAlaGlyGlyAla-228 |

Hydrophilic Regions - Hopp-Woods

| | |
|---|---|
| SEQ. ID. NO. 32513 | 27-AsnLysGluThrLeu-31 |
| SEQ. ID. NO. 32514 | 41-ThrAlaArgAlaAsnGly-46 |
| SEQ. ID. NO. 32515 | 52-ValAspSerGluHis-56 |
| SEQ. ID. NO. 32516 | 66-AspTyrThrAspArgLeuAsnGluHisGlyIle-76 |
| SEQ. ID. NO. 32517 | 111-ArgMetGlyArgLysIleSerVal-118 |
| SEQ. ID. NO. 32518 | 126-LysGlyLeuGluLeu-130 |
| SEQ. ID. NO. 32519 | 140-ProProAspLysLeuGlu-145 |
| SEQ. ID. NO. 32520 | 158-ValArgTyrArgAspGlySer-164 |
| SEQ. ID. NO. 32521 | 170-GlyAsnProAspMetArgThr-176 |
| SEQ. ID. NO. 32522 | 184-LeuProGluArgIleAspSerGlyValGlyLysLeuAsp-196 |
| SEQ. ID. NO. 32523 | 206-GlnLysProAspPheGly-211 | g574
AMPHI Regions - AMPHI

| | |
|---|---|
| SEQ. ID. NO. 32524 | 6-ProAsnSerLeuLysLys-11 |
| SEQ. ID. NO. 32525 | 47-LeuLysGlnAlaLysSerIleProSerGlyPheTyrLysSerLeuAspAlaLeuValAspArgAsnSerGlyArgAlaAlaArgGluLeuAlaGluValValAsp-81 |
| SEQ. ID. NO. 32526 | 94-GlyLysLeuTyrArgGln-99 |
| SEQ. ID. NO. 32527 | 113-MetLeuAspSerProAspThr-119 |
| SEQ. ID. NO. 32528 | 175-GluLysAlaValGlu-179 |
| SEQ. ID. NO. 32529 | 218-AsnValGlyLysAlaLeuGluAlaAsnLysLysCys-229 |
| SEQ. ID. NO. 32530 | 246-PheProAlaAlaValGluAlaTyrAlaAlaIleGlu-257 |
| SEQ. ID. NO. 32531 | 266-MetValGlyGluLysLeuTyrGluAlaTyrAla-276 |
| SEQ. ID. NO. 32532 | 281-ProGluGluGlyLeuAsnArgLeuThrGlyTyrMetGlnThrPheProGluLeuAspLeu-300 |
| SEQ. ID. NO. 32533 | 332-AsnGlyValTyrArg-336 |
| SEQ. ID. NO. 32534 | 357-ArgSerValIleGlyArgGlnLeuGlnArgSer-367 |

Antigenic Index - Jameson-Wolf

| | |
|---|---|
| SEQ. ID. NO. 32535 | 7-AsnSerLeuLysLysAlaAspMetAspAsn-16 |
| SEQ. ID. NO. 32536 | 45-ThrValLeuLysGlnAlaLysSerIleProSerGlyPheTyrLysSerLeuAspAlaLeuValAspArgAsnSerGlyArgAlaAlaArgGluLeuAlaGluValValAspGlyArgProGlnSerTyrAsp-88 |
| SEQ. ID. NO. 32537 | 96-LeuTyrArgGlnArgGlyGluAsnAspLysAlaIleAsnIleHisArgThrMetLeuAspSerProAspThrValGlyGluLysArgAlaArgVal-127 |
| SEQ. ID. NO. 32538 | 135-TyrGlnSerAlaGlyLeuValAspArgAlaGlu-145 |
| SEQ. ID. NO. 32539 | 151-LeuGlnAspGlyGluMetAlaArgGluAlaArgGln-162 |
| SEQ. ID. NO. 32540 | 168-TyrGlnGlnAspArgAspTrpGluLysAlaValGlu-179 |
| SEQ. ID. NO. 32541 | 185-SerHisAspGluGlnThrTyr-191 |
| SEQ. ID. NO. 32542 | 210-SerAsnPheAspAlaAlaArg-216 |
| SEQ. ID. NO. 32543 | 221-LysAlaLeuGluAlaAsnLysLysCysThrArg-231 |
| SEQ. ID. NO. 32544 | 238-AspIleGluHisArgGlnGlyAsn-245 |
| SEQ. ID. NO. 32545 | 277-AlaGlnGlyLysProGluGluGlyLeuAsnArgLeuThrGlyTyr-291 |
| SEQ. ID. NO. 32546 | 309-LeuLeuLeuLysGlyGluLysGluAlaAla-318 |
| SEQ. ID. NO. 32547 | 323-GluLeuValArgArgLysProAspLeuAsnGly-333 |
| SEQ. ID. NO. 32548 | 341-LysLeuSerAspLeuAspProAlaTrpLysAlaAspAlaAspMetMetArg-357 |
| SEQ. ID. NO. 32549 | 368-ValMetTyrArgCysArgAsnCysHisPheLys-378 |
| SEQ. ID. NO. 32550 | 386-CysProAlaCysAsnLysTrpGlnThrPheThrProAsnLysIleGluVal-402 |

Hydrophilic Regions - Hopp-Woods

| | |
|---|---|
| SEQ. ID. NO. 32551 | 7-AsnSerLeuLysLysAlaAspMetAspAsn-16 |
| SEQ. ID. NO. 32552 | 45-ThrValLeuLysGlnAlaLysSerIle-53 |
| SEQ. ID. NO. 32553 | 62-AspAlaLeuValAspArgAsnSerGlyArgAlaAlaArgGluLeuAlaGluValValAspGlyArgProGlnSer-86 |
| SEQ. ID. NO. 32554 | 96-LeuTyrArgGlnArgGlyGluAsnAspLysAlaIleAsn-108 |
| SEQ. ID. NO. 32555 | 112-ThrMetLeuAspSerProAspThrValGlyGluLysArgAlaArgVal-127 |
| SEQ. ID. NO. 32556 | 140-LeuValAspArgAlaGlu-145 |
| SEQ. ID. NO. 32557 | 152-GlnAspGlyGluMetAlaArgGluAlaArgGln-162 |
| SEQ. ID. NO. 32558 | 169-GlnGlnAspArgAspTrpGluLysAlaValGlu-179 |
| SEQ. ID. NO. 32559 | 185-SerHisAspGluGlnThrTyr-191 |

TABLE 1-continued

| | |
|---|---|
| SEQ. ID. NO. 32560 | 211-AsnPheAspAlaAlaArg-216 |
| SEQ. ID. NO. 32561 | 221-LysAlaLeuGluAlaAsnLysLysCysThrArg-231 |
| SEQ. ID. NO. 32562 | 238-AspIleGluHisArgGlnGlyAsn-245 |
| SEQ. ID. NO. 32563 | 279-GlyLysProGluGluGlyLeuAsn-286 |
| SEQ. ID. NO. 32564 | 309-LeuLeuLeuLysGlyGluLysGluAlaAla-318 |
| SEQ. ID. NO. 32565 | 323-GluLeuValArgArgLysProAspLeu-331 |
| SEQ. ID. NO. 32566 | 341-LysLeuSerAspLeuAspPro-347 |
| SEQ. ID. NO. 32567 | 349-TrpLysAlaAspAlaAspMetMetArg-357 |
| SEQ. ID. NO. 32568 | 368-ValMetTyrArgCysArgAsnCysHis-376 |
| SEQ. ID. NO. 32569 | 398-AsnLysIleGluVal-402 |
| g575 | |
| AMPHI Regions - AMPHI | |
| SEQ. ID. NO. 32570 | 31-ProValArgGlnValArg-36 |
| SEQ. ID. NO. 32571 | 93-TrpArgSerValAlaGluAlaGlyValSer-102 |
| SEQ. ID. NO. 32572 | 104-ThrAlaGlyLeuGlySerGlyArgThrAlaGlyPheSerAlaPheAlaSerGlyAla-122 |
| SEQ. ID. NO. 32573 | 124-ThrPheAlaSerGlyPheSerThrGly-132 |
| SEQ. ID. NO. 32574 | 149-GlySerAspGlyMetAspAlaValSerAlaLeu-159 |
| Antigenic Index - Jameson-Wolf | |
| SEQ. ID. NO. 32575 | 3-CysLeuArgArgGlnAlaAlaArgCysThrAsnArgArgThrAspArgGlnThrVal-21 |
| SEQ. ID. NO. 32576 | 27-LeuArgGlnLysProValArgGlnValArgGlnArgValArgArg-41 |
| SEQ. ID. NO. 32577 | 49-GlnGlnValArgLysArgCysTyrArgPheArgArgSerAlaCysArgTrpGlnLysArgArgLeuLeuGlyGlyAlaAspSerAlaAlaVal-79 |
| SEQ. ID. NO. 32578 | 89-ThrGlyProGlyTrp-93 |
| SEQ. ID. NO. 32579 | 100-GlyValSerAspThrAlaGlyLeuGlySerGlyArgThrAla-113 |
| SEQ. ID. NO. 32580 | 129-PheSerThrGlyPheSerThr-135 |
| SEQ. ID. NO. 32581 | 147-LeuAspGlySerAspGlyMetAsp-154 |
| Hydrophilic Regions - Hopp-Woods | |
| SEQ. ID. NO. 32582 | 3-CysLeuArgArgGlnAlaAlaArgCysThrAsnArgArgThrAspArgGlnThrVal-21 |
| SEQ. ID. NO. 32583 | 27-LeuArgGlnLysProValArgGlnValArgGlnArgValArgArg-41 |
| SEQ. ID. NO. 32584 | 50-GlnValArgLysArgCysTyrArgPheArgArgSerAlaCysArgTrpGlnLysArgArgLeuLeuGly-72 |
| SEQ. ID. NO. 32585 | 74-AlaAspSerAlaAlaVal-79 |
| SEQ. ID. NO. 32586 | 148-AspGlySerAspGlyMetAsp-154 |
| g576-1 | |
| AMPHI Regions - AMPHI | |
| SEQ. ID. NO. 32587 | 31-AlaSerGluProAlaAlaAla-37 |
| SEQ. ID. NO. 32588 | 46-SerIleGlySerThr-50 |
| SEQ. ID. NO. 32589 | 63-GlyArgSerLeuLysGlnMetLys-70 |
| SEQ. ID. NO. 32590 | 82-ThrAspAlaMetGln-86 |
| SEQ. ID. NO. 32591 | 102-GlnGluValMetMetLysPheLeuGlnGluGlnGlnAlaLysAlaValGluLysHis-120 |
| SEQ. ID. NO. 32592 | 140-AlaLysAspGlyValLysThrThr-147 |
| SEQ. ID. NO. 32593 | 200-GlnValIleProGlyTrpThrGluGlyValArgLeuLeuLysGluGly-215 |
| Antigenic Index - Jameson-Wolf | |
| SEQ. ID. NO. 32594 | 20-AlaCysGlyLysLysGluAlaAlaPro-28 |
| SEQ. ID. NO. 32595 | 30-SerAlaSerGluProAlaAla-36 |
| SEQ. ID. NO. 32596 | 40-AlaGlnGlyAspThrSerSerIleGlySerThrMetGlnGln-53 |
| SEQ. ID. NO. 32597 | 61-AspIleGlyArgSerLeuLysGlnMetLysGluGlnGlyAlaGluIleAspLeu-78 |
| SEQ. ID. NO. 32598 | 89-TyrAspGlyLysGluIleLysMetThrGluGluGlnAlaGln-102 |
| SEQ. ID. NO. 32599 | 109-LeuGlnGluGlnGlnAlaLysAlaValGluLysHisLysAlaAspAlaLysAlaAsnLysGluLysGlyGluAlaPheLeuLysGluAsnAlaAlaLysAspGlyValLysThrThrAlaSerGlyLeu-151 |
| SEQ. ID. NO. 32600 | 154-LysIleThrLysGlnGlyGluGlyLysGlnProThrLysAspAspIleVal-170 |
| SEQ. ID. NO. 32601 | 173-GluTyrGluGlyArgLeuIleAsp-180 |
| SEQ. ID. NO. 32602 | 183-ValPheAspSerSerLysAlaAsnGlyGlyPro-193 |
| SEQ. ID. NO. 32603 | 203-ProGlyTrpThrGlu-207 |
| SEQ. ID. NO. 32604 | 209-ValArgLeuLeuLysGluGlyGlyGlu-217 |
| SEQ. ID. NO. 32605 | 224-SerAsnLeuAlaTyrArgGluGlnGlyAlaGlyGluLysIleGlyPro-239 |
| SEQ. ID. NO. 32606 | 253-GlyAlaProGluAsnAlaProAlaLysGlnProAspGlnValAspIleLysLysValAsn-272 |
| Hydrophilic Regions - Hopp-Woods | |
| SEQ. ID. NO. 32607 | 21-CysGlyLysLysGluAlaAlaPro-28 |
| SEQ. ID. NO. 32608 | 30-SerAlaSerGluProAlaAla-36 |
| SEQ. ID. NO. 32609 | 40-AlaGlnGlyAspThrSerSer-46 |
| SEQ. ID. NO. 32610 | 61-AspIleGlyArgSerLeuLysGlnMetLysGluGlnGlyAlaGluIleAspLeu-78 |
| SEQ. ID. NO. 32611 | 89-TyrAspGlyLysGluIleLysMetThrGluGluGlnAlaGln-102 |
| SEQ. ID. NO. 32612 | 112-GlnGlnAlaLysAlaValGluLysHisLysAlaAspAlaLysAlaAsnLysGluLysGlyGluAlaPheLeuLysGluAsnAlaAlaLysAspGlyValLysThrThrAla-148 |
| SEQ. ID. NO. 32613 | 155-IleThrLysGlnGlyGluGlyLysGlnProThrLysAspAspIleVal-170 |
| SEQ. ID. NO. 32614 | 173-GluTyrGluGlyArgLeuIleAsp-180 |
| SEQ. ID. NO. 32615 | 185-AspSerSerLysAlaAsnGly-191 |
| SEQ. ID. NO. 32616 | 209-ValArgLeuLeuLysGluGlyGlyGlu-217 |
| SEQ. ID. NO. 32617 | 227-AlaTyrArgGluGlnGlyAlaGlyGluLysIleGlyPro-239 |
| SEQ. ID. NO. 32618 | 253-GlyAlaProGluAsnAlaProAlaLysGlnProAspGlnValAspIleLysLysValAsn-272 |
| g577 | |
| AMPHI Regions - AMPHI | |
| SEQ. ID. NO. 32619 | 8-GlyLysIleValGlyAsnArgIleLeuArgMetProSerGluHis-22 |
| SEQ. ID. NO. 32620 | 26-PheTyrProLysProCysLysSerPheLysLeuThr-37 |
| SEQ. ID. NO. 32621 | 62-ThrValIleLysIleIle-67 |
| SEQ. ID. NO. 32622 | 104-AlaPheValValGlyIle-109 |
| SEQ. ID. NO. 32623 | 112-GlyMetPheAlaLeuPheGlyArg-119 |
| Antigenic Index - Jameson-Wolf | |
| SEQ. ID. NO. 32624 | 1-MetGluArgSerGlyVal-6 |
| SEQ. ID. NO. 32625 | 14-ArgIleLeuArgMetProSerGluHis-22 |
| SEQ. ID. NO. 32626 | 28-ProLysProCysLysSerPheLysLeu-36 |

TABLE 1-continued

SEQ. ID. NO. 32627  43-ValArgSerCysProCys-48
SEQ. ID. NO. 32628  121-LeuSerLeuArgGlyGluAsnSerArgLeuArgAlaGluValLysLysSerAlaArgLeuSerGlyGlnLysLeuThrAla-147
SEQ. ID. NO. 32629  152-AsnAlaAlaGluSerAlaLysGlnPro-160
Hydrophilic Regions - Hopp-Woods
SEQ. ID. NO. 32630  1-MetGluArgSerGlyVal-6
SEQ. ID. NO. 32631  14-ArgIleLeuArgMetProSerGluHis-22
SEQ. ID. NO. 32632  29-LysProCysLysSerPheLys-35
SEQ. ID. NO. 32633  121-LeuSerLeuArgGlyGluAsnSerArgLeuArgAlaGluValLysLysSerAlaArgLeuSerGly-142
SEQ. ID. NO. 32634  152-AsnAlaAlaGluSerAlaLysGlnPro-160
g578
AMPHI Regions - AMPHI
SEQ. ID. NO. 32635  10-PheAlaAspPhePheLysAspPheAlaProGlnPheGlyGlyPheGlnAsn-26
SEQ. ID. NO. 32636  34-AspPhePheAlaAlaPheLeuGlyGlyLeuGlyGlyHisValGlyAsp-49
SEQ. ID. NO. 32637  58-PheHisGlyValValAlaPhe-64
SEQ. ID. NO. 32638  71-AsnThrAspAlaAlaArgPhe-77
Antigenic Index - Jameson-Wolf
SEQ. ID. NO. 32639  13-PhePheLysAspPheAlaProGlnPheGlyGly-23
SEQ. ID. NO. 32640  43-LeuGluGlyHisValGlyAspAlaAla-51
SEQ. ID. NO. 32641  71-AsnThrAspAlaAlaArgPheAla-78
SEQ. ID. NO. 32642  88-HisAsnGlnAsnIleGlnThrGlyAsnAspPheArgLeuGluArgGlyGlyValGly-106
Hydrophilic Regions - Hopp-Woods
SEQ. ID. NO. 32643  73-AspAlaAlaArgPheAla-78
SEQ. ID. NO. 32644  96-AsnAspPheArgLeuGluArgGlyGlyVal-105
g579
AMPHI Regions - AMPHI
SEQ. ID. NO. 32645  6-PheAspPheLeuHisLeuIleSerValSerGlyTrpGlyHisLeuAlaGlu-22
SEQ. ID. NO. 32646  49-ValAlaValMetArg-53
SEQ. ID. NO. 32647  66-IleSerPheLeuCysAsn-71
SEQ. ID. NO. 32648  115-LeuSerAsnPheAla-119
SEQ. ID. NO. 32649  129-ProPheLysValGlyAspPheIleArgValGlyGlyPheGluGlyTyrValArgGluIleLys-149
SEQ. ID. NO. 32650  206-LeuLysAlaAlaAlaGlu-211
SEQ. ID. NO. 32651  258-GlnValValGluAsnLeuArg-264
Antigenic Index - Jameson-Wolf
SEQ. ID. NO. 32652  110-SerLeuLysAspGlnLeuSer-116
SEQ. ID. NO. 32653  128-ArgProPheLysVal-132
SEQ. ID. NO. 32654  136-IleArgValGlyGlyPheGluGlyTyrValArgGluIleLysMet-150
SEQ. ID. NO. 32655  154-SerLeuArgThrThrAspAsnGluGluValValLeu-165
SEQ. ID. NO. 32656  175-IleValAsnArgSerSerLeuProLeu-183
SEQ. ID. NO. 32657  198-LeuLysValAlaLysGluAlaValLeu-206
SEQ. ID. NO. 32658  216-ValGlnAsnGluGluArgGlnPro-223
SEQ. ID. NO. 32659  231-GlyAspAsnAlaIle-235
SEQ. ID. NO. 32660  244-AsnGluAlaAspArgTrpThrLeu-251
SEQ. ID. NO. 32661  253-CysAspLeuAsnGluGlnValValGluAsnLeuArgLysValAsn-267
SEQ. ID. NO. 32662  271-ProPheProGlnArgAspIleHis-278
Hydrophilic Regions - Hopp-Woods
SEQ. ID. NO. 32663  110-SerLeuLysAspGlnLeu-115
SEQ. ID. NO. 32664  144-TyrValArgGluIleLysMet-150
SEQ. ID. NO. 32665  155-LeuArgThrThrAspAsnGluGluValVal-164
SEQ. ID. NO. 32666  198-LeuLysValAlaLysGluAlaValLeu-206
SEQ. ID. NO. 32667  216-ValGlnAsnGluGluArgGlnPro-223
SEQ. ID. NO. 32668  244-AsnGluAlaAspArgTrp-249
SEQ. ID. NO. 32669  254-AspLeuAsnGluGlnValValGluAsnLeuArgLysValAsn-267
SEQ. ID. NO. 32670  273-ProGlnArgAspIleHis-278
g580
AMPHI Regions - AMPHI
SEQ. ID. NO. 32671  47-ProValSerAlaSerLys-52
SEQ. ID. NO. 32672  54-SerLeuValLysProLeuSerGlnProLeuAla-64
Antigenic Index - Jameson-Wolf
SEQ. ID. NO. 32673  1-MetAspSerProLysValGlyCysGly-9
SEQ. ID. NO. 32674  48-ValSerAlaSerLys-52
SEQ. ID. NO. 32675  66-AlaArgProGluAlaAlaHis-72
SEQ. ID. NO. 32676  81-ArgProAspAlaLeuAlaAspAsnSerValSerProThrHisAlaThrSerGlyGluVal-100
Hydrophilic Regions - Hopp-Woods
SEQ. ID. NO. 32677  1-MetAspSerProLysVal-6
SEQ. ID. NO. 32678  66-AlaArgProGluAlaAlaHis-72
SEQ. ID. NO. 32679  81-ArgProAspAlaLeuAla-86
SEQ. ID. NO. 32680  96-ThrSerGlyGluVal-100
g581
AMPHI Regions - AMPHI
SEQ. ID. NO. 32681  43-SerHisPheIleSerLeu-48
SEQ. ID. NO. 32682  56-ArgGluCysPheValGlyPhe-62
SEQ. ID. NO. 32683  76-AlaThrAlaPheGlyArgIleAsnGln-84
SEQ. ID. NO. 32684  90-GlnIleHisGlyPheLeuThrThrPheAlaGlyArgValAlaAsnProThrHisCysGlnSerGlnThr-112
Antigenic Index - Jameson-Wolf
SEQ. ID. NO. 32685  8-GlyGlnThrGlyIleGluGlnAsnThrPheCysArgArgGlyPheThrArgIleAspMetGlyGlyAsnThrAspVal-33
SEQ. ID. NO. 32686  35-ValGlnAlaAspArgGlyLeuThrSer-43
SEQ. ID. NO. 32687  49-SerLysLeuGluThrGluValArgGluCysPhe-59
SEQ. ID. NO. 32688  79-PheGlyArgIleAsnGln-84
SEQ. ID. NO. 32689  98-PheAlaGlyArgValAlaAsnProThrHisCysGlnSerGlnThrAla-113

TABLE 1-continued

Hydrophilic Regions - Hopp-Woods
SEQ. ID. NO. 32690    35-ValGlnAlaAspArgGlyLeu-41
SEQ. ID. NO. 32691    49-SerLysLeuGluThrGluValArgGlu-57
g582
AMPHI Regions - AMPHI
SEQ. ID. NO. 32692    27-ThrAspAsnValThrArgLeuAla-34
SEQ. ID. NO. 32693    65-ValArgSerSerLeu-69
SEQ. ID. NO. 32694    91-GlyGluThrAlaAspIleTyrThrProLeuSer-101
SEQ. ID. NO. 32695    139-SerSerProThrArg-143
SEQ. ID. NO. 32696    169-IleAlaGluAsnLeuPhe-174
SEQ. ID. NO. 32697    246-SerArgSerTrpAsnArgIleTyrAlaMet-255
SEQ. ID. NO. 32698    263-LeuThrValIleProArgValTrpValArgAlaPheAspGlnSer-277
SEQ. ID. NO. 32699    286-IleAlaAspTyrMetGlyTyr-292
SEQ. ID. NO. 32700    334-LeuLysGlyValValArgGlyPheHisGlyTyrGlyGlu-346
Antigenic Index - Jameson-Wolf
SEQ. ID. NO. 32701    26-LeuThrAspAsnValThr-31
SEQ. ID. NO. 32702    34-AlaCysTyrAspArg-38
SEQ. ID. NO. 32703    44-LeuProSerSerAlaGlyGlnGluGlyGlnGluSerLysAla-57
SEQ. ID. NO. 32704    63-GluThrValArgSerSerLeuAspLysGlyGluAla-74
SEQ. ID. NO. 32705    77-ValValGluLysGlyGlyAspAlaLeuProAlaAspSerAlaGlyGluThrAlaAsp-95
SEQ. ID. NO. 32706    105-AspLeuAspLysAsnAspLeuArgGly-113
SEQ. ID. NO. 32707    115-LeuGlyValArgGluHisAsnProMetTyr-124
SEQ. ID. NO. 32708    130-TyrAsnAsnSerProAsnTyrAlaProSerSerProThrArgGlyThrThrValGlnGluLysPheGlyGlnGlnLysArgAlaGluThrLysLeu-161
SEQ. ID. NO. 32709    165-PheLysSerLysIleAla-170
SEQ. ID. NO. 32710    173-LeuPheLysThrArgAla-178
SEQ. ID. NO. 32711    183-GlyTyrThrGlnArgSerAspTrpGlnIleTyrAsnGlnGlyArgLysSerAlaProPheArgAsnThrAspTyrLysPro-209
SEQ. ID. NO. 32712    216-ProValLysAlaAspLeuProPheGlyGlyArgLeuArgMet-229
SEQ. ID. NO. 32713    237-GlnSerAsnGlyGlnSerArgProGluSerArgSerTrpAsn-250
SEQ. ID. NO. 32714    273-AlaPheAspGlnSerGlyAspLysAsnAspAsnProAspIleAlaAsp-288
SEQ. ID. NO. 32715    291-GlyTyrGlyAspValLysLeuGlnTyrArgLeuAsnAspArgGlnAsnVal-307
SEQ. ID. NO. 32716    312-ArgTyrAsnProLysThrGlyTyr-319
SEQ. ID. NO. 32717    330-IleLysGlyLysLeuLysGlyValVal-338
SEQ. ID. NO. 32718    342-HisGlyTyrGlyGluSerLeuIleAspTyrAsnHisLysGlnAsnGly-357
SEQ. ID. NO. 32719    365-AsnAspTrpAspGlyIle-370
Hydrophilic Regions - Hopp-Woods
SEQ. ID. NO. 32720    48-AlaGlyGlnGluGlyGlnGluSerLysAla-57
SEQ. ID. NO. 32721    63-GluThrValArgSerSerLeuAspLysGlyGluAla-74
SEQ. ID. NO. 32722    79-GluLysGlyGlyAspAlaLeuPro-86
SEQ. ID. NO. 32723    88-AspSerAlaGlyGluThrAlaAsp-95
SEQ. ID. NO. 32724    105-AspLeuAspLysAsnAspLeuArgGly-113
SEQ. ID. NO. 32725    115-LeuGlyValArgGluHisAsn-121
SEQ. ID. NO. 32726    140-SerProThrArgGlyThrThrValGlnGluLysPheGlyGlnGlnLysArgAlaGluThrLysLeu-161
SEQ. ID. NO. 32727    165-PheLysSerLysIleAla-170
SEQ. ID. NO. 32728    173-LeuPheLysThrArgAla-178
SEQ. ID. NO. 32729    195-GlnGlyArgLysSerAlaProPheArgAsnThrAspTyrLysPro-209
SEQ. ID. NO. 32730    225-GlyArgLeuArgMet-229
SEQ. ID. NO. 32731    239-AsnGlyGlnSerArgProGluSerArgSerTrp-249
SEQ. ID. NO. 32732    274-PheAspGlnSerGlyAspLysAsnAspAsnProAspIleAlaAsp-288
SEQ. ID. NO. 32733    293-GlyAspValLysLeu-297
SEQ. ID. NO. 32734    299-TyrArgLeuAsnAspArgGlnAsn-306
SEQ. ID. NO. 32735    332-GlyLysLeuLysGlyValVal-338
SEQ. ID. NO. 32736    352-AsnHisLysGlnAsn-356
g583
AMPHI Regions - AMPHI
SEQ. ID. NO. 32737    11-HisLeuAlaPheCysAlaPheCysGlyIle-20
SEQ. ID. NO. 32738    28-ArgLeuHisAsnArgMetTyrAsnAlaAlaAlaAlaArg-40
SEQ. ID. NO. 32739    58-ValThrAspAlaGln-62
SEQ. ID. NO. 32740    66-SerLysAsnGlyAspLysGlnIle-73
SEQ. ID. NO. 32741    75-AspThrHisProGlnPro-80
SEQ. ID. NO. 32742    117-GlyTyrAlaGlyTyrCysAspGln-124
SEQ. ID. NO. 32743    141-AsnGlyGlyAsnHisThrAsp-147
SEQ. ID. NO. 32744    162-GlyTyrGlyGlnCysGlnAsnGlnGlyAla-171
Antigenic Index - Jameson-Wolf
SEQ. ID. NO. 32745    24-ThrAlaGlyAsnArgLeuHisAsnArgMetTyr-34
SEQ. ID. NO. 32746    41-GlyIleGlyArgGlyAsnGlySerGlnGlnGlnPheGlyLysSerGluThrValThrAspAlaGlnArgPheSerSerLysAsnGlyAspLysGln
                      IleSerAspThrHisProGlnProCysPheGluGlnThrAlaArgAsnHisAsnCysAspGlyAsnGlnProAsnGlnArgIleGlyGluArgThrGlnArg
                      IleAlaHisArgArgAlaArgPhe-114
SEQ. ID. NO. 32747    117-GlyTyrAlaGlyTyrCysAspGlnProAspGlyAsnAsnArgGlnArgAlaGlnArgHisAsnLeuAlaAspAsnGlyGlyAsnHisThrAspLys
                      HisSerGlnGlnArgProSerLeuArgLeuAspProValGlyTyrGlyGlnCysGlnAsnGlnGlyAlaGlnTyrCysGlyAsnGlyGluGlyTyrArg
                      Phe-182
SEQ. ID. NO. 32748    190-AspLeuArgLysLysAspArgProGluLysSerGluLys-202
Hydrophilic Regions - Hopp-Woods
SEQ. ID. NO. 32749    27-AsnArgLeuHisAsn-31
SEQ. ID. NO. 32750    41-GlyIleGlyArgGlyAsnGlySer-48
SEQ. ID. NO. 32751    51-GlnPheGlyLysSerGluThrValThrAspAlaGlnArgPheSerSerLysAsnGlyAspLysGlnIleSerAspThrHisPro-78
SEQ. ID. NO. 32752    84-GlnThrAlaArgAsnHisAsnCysAspGlyAsnGlnProAsnGlnArgIleGlyGluArgThrGlnArgIleAlaHisArgArgAlaArgPhe-114
SEQ. ID. NO. 32753    123-AspGlnProAspGlyAsnAsnArgGlnArgAlaGlnArgHisAsnLeuAlaAspAsnGlyGlyAsnHisThrAspLysHisSerGlnGlnArgPro
                      SerLeuArgLeuAspPro-160
SEQ. ID. NO. 32754    178-GluGlyTyrArgPhe-182
SEQ. ID. NO. 32755    190-AspLeuArgLysLysAspArgProGluLysSerGluLys-202

TABLE 1-continued g584
AMPHI Regions - AMPHI
SEQ. ID. NO. 32756    28-GluPheSerGluSerAlaGly-34
SEQ. ID. NO. 32757    60-AlaGluPheValLysLysPheAsnAsnPheThrArgLys-72
SEQ. ID. NO. 32758    116-PheAspAlaLeuAsnArgPheIleAlaAspVal-126
SEQ. ID. NO. 32759    148-IleAspGlnValSerLysAsp-154
SEQ. ID. NO. 32760    166-LeuAlaGlyValLeuGly-171
Antigenic Index - Jameson-Wolf
SEQ. ID. NO. 32761    37-ValAlaGlnAspThrMetSer-43
SEQ. ID. NO. 32762    50-AlaGluGlyArgAspLysAsnAlaVal-58
SEQ. ID. NO. 32763    61-GluPheValLysLysPheAsnAsnPheThrArgLysSerLysAsnGlySerPheLysThrGluLeuValSerArgSerAlaMetProArgTyrGlnTyr
                      ThrAsnGlyArgArgIleGlnThrGlyTrpGluGluArgAlaGluPheLysAlaGluGlyArgAspPheAspAla-118
SEQ. ID. NO. 32764    126-ValGlnThrAspAlaSerLeuGluAspThrAspPheSerValSerArgGluArgArgAsnGluValIleAspGlnValSerLysAspAlaValLeu-157
SEQ. ID. NO. 32765    159-PheLysAlaArgAlaGluLysLeuAla-167
SEQ. ID. NO. 32766    189-IleAlaGlyAspGlyAlaValArgAlaLysMetLeuArg-201
SEQ. ID. NO. 32767    210-AsnMetLysGlyThrAspSerAlaAlaProGlyValGluGluIleSer-225
Hydrophilic Regions - Hopp-Woods
SEQ. ID. NO. 32768    50-AlaGluGlyArgAspLysAsnAlaVal-58
SEQ. ID. NO. 32769    67-AsnAsnPheThrArgLysSerLysAsnGlySerPheLysThrGluLeuValSer-84
SEQ. ID. NO. 32770    95-AsnGlyArgArgIleGlnThrGlyTrpGluGluArgAlaGluPheLysAlaGluGlyArgAspPheAspAla-118
SEQ. ID. NO. 32771    130-AlaSerLeuGluAspThrAspPheSerValSerArgGluArgArgAsnGluValIleAspGlnValSerLysAspAlaValLeu-157
SEQ. ID. NO. 32772    159-PheLysAlaArgAlaGluLysLeuAla-167
SEQ. ID. NO. 32773    193-GlyAlaValArgAlaLysMetLeuArg-201
SEQ. ID. NO. 32774    210-AsnMetLysGlyThrAspSerAlaAlaProGlyValGluGluIleSer-225
g585
AMPHI Regions - AMPHI
SEQ. ID. NO. 32775    6-ArgIlePheAlaThrPheCysAlaValIleValCys-17
SEQ. ID. NO. 32776    46-ThrThrLeuMetGlySerIleIleSer-54
SEQ. ID. NO. 32777    65-ArgGluIleLeuThrGluTrpLys-72
SEQ. ID. NO. 32778    93-AsnArgTyrIleAsp-97
SEQ. ID. NO. 32779    136-AspAsnHisGlnAlaGlnArg-142
SEQ. ID. NO. 32780    153-ProLeuAlaProIleTrp-158
SEQ. ID. NO. 32781    178-LeuAlaGlyAsnIleAlaLysProIleArgIleLeuGlyAsnGlyMetAspArgValAlaGluArgGlu-200
Antigenic Index - Jameson-Wolf
SEQ. ID. NO. 32782    36-AsnGlnPheAsnGlnArgArgThrIleGlu-45
SEQ. ID. NO. 32783    56-PheLysThrArgGlyAspAsnGlyAlaArgGluIleLeuThrGluTrpLysAsnSerProValSer-77
SEQ. ID. NO. 32784    84-GlnGlyAspGluLysLysAspIleLeu-92
SEQ. ID. NO. 32785    99-TyrThrIleGluArgAlaArgLeu-106
SEQ. ID. NO. 32786    119-IleGluTyrAspArgPheGlyGlu-126
SEQ. ID. NO. 32787    134-GlyTrpAspAsnHisGlnAlaGlnArgLeuProSerPro-146
SEQ. ID. NO. 32788    189-LeuGlyAsnGlyMetAspArgValAlaGluArgGluLeuGluAspArgValCysGlnGlnValArgAspArgAspGluLeuAlaAsp-218
SEQ. ID. NO. 32789    225-ThrMetValGluLysLeuGlu-231
Hydrophilic Regions - Hopp-Woods
SEQ. ID. NO. 32790    37-GlnPheAsnGlnArgArgThrIleGlu-45
SEQ. ID. NO. 32791    56-PheLysThrArgGlyAspAsnGlyAlaArgGluIleLeuThr-69
SEQ. ID. NO. 32792    84-GlnGlyAspGluLysLysAspIleLeu-92
SEQ. ID. NO. 32793    100-ThrIleGluArgAlaArgLeu-106
SEQ. ID. NO. 32794    119-IleGluTyrAspArgPheGlyGlu-126
SEQ. ID. NO. 32795    139-GlnAlaGlnArgLeu-143
SEQ. ID. NO. 32796    192-GlyMetAspArgValAlaGluArgGluLeuGluAspArgValCysGlnGlnValArgAspArgAspGluLeuAlaAsp-218
SEQ. ID. NO. 32797    225-ThrMetValGluLysLeuGlu-231
g586
AMPHI Regions - AMPHI
SEQ. ID. NO. 32798    12-AspAsnPheLysTyrPheTrpLysThr-20
SEQ. ID. NO. 32799    30-IleLeuAlaAlaLeuGly-35
SEQ. ID. NO. 32800    56-ValLeuAlaAsnIleValGluLysAlaGlnAsnLysAlaPro-69
SEQ. ID. NO. 32801    80-LeuGlnGlnSerTyrProHisSerIleSer-89
SEQ. ID. NO. 32802    177-SerGlnGluAlaLeuLysAsnTyrGlyGlnAlaLeuGluLysMetProGlnAspSerValGlyArg-198
Antigenic Index - Jameson-Wolf
SEQ. ID. NO. 32803    4-HisLeuGluGluGlnGlnGluLeuAspAsn-13
SEQ. ID. NO. 32804    43-GlnAsnArgAlaAlaSerGlnAsnGlnGluAla-53
SEQ. ID. NO. 32805    60-IleValGluLysAlaGlnAsnLysAlaProGlnSerGluIleAsnAlaGluLeuSerLysLeuGlnGln-82
SEQ. ID. NO. 32806    100-ThrGluPheAspAlaGlnArgTyrAspValAlaGluGly-112
SEQ. ID. NO. 32807    118-LeuSerAsnGlnLysAspSerLeu-125
SEQ. ID. NO. 32808    140-GlnGlnLysLysTyrAspAla-146
SEQ. ID. NO. 32809    153-ThrProValGluAlaAspPhe-159
SEQ. ID. NO. 32810    164-MetGluThrLysGlyAspVal-170
SEQ. ID. NO. 32811    172-AlaAlaGlnGluLysSerGlnGluAlaLeuLysAsnTyrGlyGlnAlaLeuGluLysMetProGlnAspSerValGlyArgGluLeuLeu-201
SEQ. ID. NO. 32812    204-LysLeuAspSerLeuLys-209
Hydrophilic Regions - Hopp-Woods
SEQ. ID. NO. 32813    4-HisLeuGluGluGlnGlnGluLeuAspAsn-13
SEQ. ID. NO. 32814    45-ArgAlaAlaSerGlnAsnGlnGluAla-53
SEQ. ID. NO. 32815    60-IleValGluLysAlaGlnAsnLysAlaProGlnSerGluIleAsnAlaGluLeuSerLysLeu-80
SEQ. ID. NO. 32816    100-ThrGluPheAspAlaGlnArgTyrAspValAlaGluGly-112
SEQ. ID. NO. 32817    120-AsnGlnLysAspSerLeu-125
SEQ. ID. NO. 32818    140-GlnGlnLysLysTyrAspAla-146
SEQ. ID. NO. 32819    153-ThrProValGluAlaAspPhe-159
SEQ. ID. NO. 32820    164-MetGluThrLysGlyAspVal-170
SEQ. ID. NO. 32821    172-AlaAlaGlnGluLysSerGlnGluAlaLeuLys-182
SEQ. ID. NO. 32822    187-AlaLeuGluLysMetProGlnAspSerValGlyArgGluLeuLeu-201

TABLE 1-continued

SEQ. ID. NO. 32823 204-LysLeuAspSerLeuLys-209
g587
AMPHI Regions - AMPHI
SEQ. ID. NO. 32824 6-LeuProAlaLeuProAlaIleLeuProLeuSerAla-17
SEQ. ID. NO. 32825 122-LysArgMetSerAspIleSerAlaGlyIleSerHis-133
Antigenic Index - Jameson-Wolf
SEQ. ID. NO. 32826 27-AspIleMetThrAspLysGlyLysTrpLysLeuGluThr-39
SEQ. ID. NO. 32827 45-AsnSerGluAsnSerArgAla-51
SEQ. ID. NO. 32828 71-ThrGluIleGlnGluAsnGlySerAsnThr-80
SEQ. ID. NO. 32829 95-GlyAsnThrAspIleTyrGlySerGlySer-104
SEQ. ID. NO. 32830 108-HisGluGluArgLysLeuAspGlyAsnGlyLysThrArgAsnLysArgMetSerAspIle-127
SEQ. ID. NO. 32831 135-PheLeuLysAspGlyLysAsnProAla-143
SEQ. ID. NO. 32832 151-ThrValTyrGluLysSerArgAsnLysAlaSerLeuIleLysLysArgGlyLeuCys-169
Hydrophilic Regions - Hopp-Woods
SEQ. ID. NO. 32833 27-AspIleMetThrAspLysGlyLysTrpLysLeu-37
SEQ. ID. NO. 32834 47-GluAsnSerArgAla-51
SEQ. ID. NO. 32835 72-GluIleGlnGluAsnGlySerAsn-79
SEQ. ID. NO. 32836 108-HisGluGluArgLysLeuAspGlyAsnGlyLysThrArgAsnLysArgMetSerAspIle-127
SEQ. ID. NO. 32837 135-PheLeuLysAspGlyLysAsn-141
SEQ. ID. NO. 32838 151-ThrValTyrGluLysSerArgAsnLysAlaSerLeuIleLysLysArgGlyLeu-168
g588
AMPHI Regions - AMPHI
SEQ. ID. NO. 32839 55-ArgGlyTyrThrGlySer-60
Antigenic Index - Jameson-Wolf
SEQ. ID. NO. 32840 24-SerProTyrGlnGluThrGlyCysThrTyrGluGlyGlyIleGlyLysAspGlyLeuProSerGlyLysGlyIleTrpArgCysArgAspGly
 ArgGlyTyrThrGlySerPheLysAsnGlyLysPheAspGlyGlnGly-70
SEQ. ID. NO. 32841 85-PheAsnSerAspSerThrLysPheArgAsn-94
SEQ. ID. NO. 32842 105-LeuAlaHisGlyArgPheAlaAlaSerGlnAsnGlyGluThr-118
SEQ. ID. NO. 32843 124-MetArgThrArgHisAsp-129
Hydrophilic Regions - Hopp-Woods
SEQ. ID. NO. 32844 36-GlyIleGlyLysAspGlyLeuProSer-44
SEQ. ID. NO. 32845 49-TrpArgCysArgAspGlyArgGlyTyr-57
SEQ. ID. NO. 32846 61-PheLysAsnGlyLysPheAspGly-68
SEQ. ID. NO. 32847 85-PheAsnSerAspSerThrLysPheArgAsn-94
SEQ. ID. NO. 32848 124-MetArgThrArgHisAsp-129
g589
AMPHI Regions - AMPHI
SEQ. ID. NO. 32849 18-AlaSerArgIleGluLysValLeu-25
SEQ. ID. NO. 32850 54-ValAlaAspIleAlaLysIleIleGluLys-63
SEQ. ID. NO. 32851 103-MetValGlyMetMet-107
SEQ. ID. NO. 32852 127-ValLeuAlaSerIleValGlnLeuTrpLeuAla-137
SEQ. ID. NO. 32853 155-MetAspValLeuValThrIle-161
SEQ. ID. NO. 32854 198-PheValSerLeuGlyLysPheLeuGluHisArg-208
SEQ. ID. NO. 32855 230-ValGlnArgAsnGlyGlu-235
SEQ. ID. NO. 32856 245-GlnIleGlyAspLeuIleArg-251
SEQ. ID. NO. 32857 315-LeuGlyAspMetMetAsnAlaLeuSerGluAlaGln-326
SEQ. ID. NO. 32858 330-AlaProIleAlaArgValAlaAspLys-338
SEQ. ID. NO. 32859 396-MetGlyLysAlaVal-400
SEQ. ID. NO. 32860 471-IleValSerAlaAlaGln-476
SEQ. ID. NO. 32861 482-IleProAlaAlaGln-486
SEQ. ID. NO. 32862 502-GlyValGlyLeuValLys-507
SEQ. ID. NO. 32863 539-LysProIleGlyAlaPheAlaLeuSerAspAlaLeuLys-551
SEQ. ID. NO. 32864 553-AspThrAlaGluAlaIleGlyArgLeu-561
SEQ. ID. NO. 32865 591-AlaPheGlyAsnMetSerProCysAspLysAlaAlaGluValGlnLysLeuLysAlaAla-610
SEQ. ID. NO. 32866 617-ValGlyAspGlyIleAsnAspAlaPro-625
SEQ. ID. NO. 32867 640-AlaAspValAlaGluHisThr-646
SEQ. ID. NO. 32868 653-GlnHisSerValAsnGlnLeu-659
SEQ. ID. NO. 32869 680-AlaPhePheTyrAsnIleLeu-686
Antigenic Index - Jameson-Wolf
SEQ. ID. NO. 32870 1-MetGlnGlnLysIleArgPhe-7
SEQ. ID. NO. 32871 17-CysAlaSerArgIleGluLysValLeuAsnLysLysAspPheValGluSer-33
SEQ. ID. NO. 32872 39-AlaSerGluGluAlaGlnValThrPheAspGlySerLysThrSerVal-54
SEQ. ID. NO. 32873 59-LysIleIleGluLysThrGlyTyrGlyAlaLysGluLysThrGluAspThrLeuProGlnProGluAlaGluHis-83
SEQ. ID. NO. 32874 114-ThrArgHisAspTrp-118
SEQ. ID. NO. 32875 148-IleLysGlyGlyLeu-152
SEQ. ID. NO. 32876 205-LeuGluHisArgThrLysLysSerSerLeuAsn-215
SEQ. ID. NO. 32877 228-ValAsnValGlnArgAsnGlyGluTrpLysGlnLeuProIleAspGln-243
SEQ. ID. NO. 32878 248-AspLeuIleArgThrAsnHisGlyGluArgIleAlaAla-260
SEQ. ID. NO. 32879 262-GlyIleIleGluSerGlySerGlyTrpAlaAspGluSerHisLeuThrGlyGluSerAsnProGluGluLysLysAlaGlyGly-289
SEQ. ID. NO. 32880 298-ThrGluGlySerVal-302
SEQ. ID. NO. 32881 323-SerGluAlaGlnGlySerLysAlaProIle-332
SEQ. ID. NO. 32882 334-ArgValAlaAspLysAlaAlaAla-340
SEQ. ID. NO. 32883 361-IleLysGlyAspTrp-365
SEQ. ID. NO. 32884 396-MetGlyLysAlaValLys-401
SEQ. ID. NO. 32885 409-AlaAlaAlaMetGluGluAlaAlaHis-417
SEQ. ID. NO. 32886 422-ValLeuAspLysThrGlyThrLeuThrGluGlyArgProGlnVal-436
SEQ. ID. NO. 32887 443-ProAspSerGlyPheAspGluAspAlaLeu-452
SEQ. ID. NO. 32888 459-ValGluGlnAsnAla-463
SEQ. ID. NO. 32889 498-AlaGluValGluGly-502
SEQ. ID. NO. 32890 507-LysSerGlyLysAlaGluPheAla-514

TABLE 1-continued

| | |
|---|---|
| SEQ. ID. NO. 32891 | 520-LysPheSerAspGlyVal-525 |
| SEQ. ID. NO. 32892 | 535-SerValAsnGlyLysProIle-541 |
| SEQ. ID. NO. 32893 | 548-AspAlaLeuLysAlaAspThrAlaGluAlaIleGlyArgLeuLysLysHisAsnIle-566 |
| SEQ. ID. NO. 32894 | 572-SerGlyAspAsnGlnSerThrVal-579 |
| SEQ. ID. NO. 32895 | 596-SerProCysAspLysAlaAlaGluValGlnLysLeuLysAlaAlaGly-611 |
| SEQ. ID. NO. 32896 | 617-ValGlyAspGlyIleAsnAspAla-624 |
| SEQ. ID. NO. 32897 | 636-MetLysGlyGlyAlaAspValAlaGlu-644 |

Hydrophilic Regions - Hopp-Woods

| | |
|---|---|
| SEQ. ID. NO. 32898 | 1-MetGlnGlnLysIleArgPhe-7 |
| SEQ. ID. NO. 32899 | 19-SerArgIleGluLysValLeuAsnLysLysAspPheValGlu-32 |
| SEQ. ID. NO. 32900 | 39-AlaSerGluGluAlaGlnVal-45 |
| SEQ. ID. NO. 32901 | 48-AspGlySerLysThrSerVal-54 |
| SEQ. ID. NO. 32902 | 64-ThrGlyTyrGlyAlaLysGluLysThrGluAspThrLeuProGlnProGluAlaGluHis-83 |
| SEQ. ID. NO. 32903 | 205-LeuGluHisArgThrLysLysSerSerLeu-214 |
| SEQ. ID. NO. 32904 | 229-AsnValGlnArgAsnGlyGluTrpLys-237 |
| SEQ. ID. NO. 32905 | 253-AsnHisGlyGluArgIleAlaAla-260 |
| SEQ. ID. NO. 32906 | 262-GlyIleIleGluSer-266 |
| SEQ. ID. NO. 32907 | 270-TrpAlaAspGluSerHisLeuThrGlyGluSerAsnProGluGluLysLysAlaGlyGly-289 |
| SEQ. ID. NO. 32908 | 323-SerGluAlaGlnGlySerLysAlaProIle-332 |
| SEQ. ID. NO. 32909 | 334-ArgValAlaAspLysAlaAla-340 |
| SEQ. ID. NO. 32910 | 409-AlaAlaAlaMetGluGluAlaAlaHis-417 |
| SEQ. ID. NO. 32911 | 422-ValLeuAspLysThrGlyThrLeuThrGluGlyArgProGln-435 |
| SEQ. ID. NO. 32912 | 445-SerGlyPheAspGluAspAlaLeu-452 |
| SEQ. ID. NO. 32913 | 459-ValGluGlnAsnAla-463 |
| SEQ. ID. NO. 32914 | 498-AlaGluValGluGly-502 |
| SEQ. ID. NO. 32915 | 507-LysSerGlyLysAlaGluPheAla-514 |
| SEQ. ID. NO. 32916 | 548-AspAlaLeuLysAlaAspThrAlaGluAlaIleGlyArgLeuLysLysHisAsnIle-566 |
| SEQ. ID. NO. 32917 | 573-GlyAspAsnGlnSer-577 |
| SEQ. ID. NO. 32918 | 596-SerProCysAspLysAlaAlaGluValGlnLysLeuLysAlaAlaGly-611 |
| SEQ. ID. NO. 32919 | 638-GlyGlyAlaAspValAlaGlu-644 | g590
AMPHI Regions - AMPHI

| | |
|---|---|
| SEQ. ID. NO. 32920 | 90-ValThrLeuValAsnHisIleThrHis-98 |
| SEQ. ID. NO. 32921 | 100-ProPheAlaGlyGlyPhe-105 |
| SEQ. ID. NO. 32922 | 123-LysValLeuGluArgPhePhe-129 |
| SEQ. ID. NO. 32923 | 132-GlnValProValSerLeu-137 |
| SEQ. ID. NO. 32924 | 177-TyrGlnLysGlyPheLysSerTyrArgAsnSer-187 |
| SEQ. ID. NO. 32925 | 213-GluThrSerAspGlyIleAsnProLeu-221 |
| SEQ. ID. NO. 32926 | 248-AsnGluLeuValAsnLeuVal-254 |
| SEQ. ID. NO. 32927 | 331-LysArgLysPheAla-335 |
| SEQ. ID. NO. 32928 | 420-LysMetLeuGluAsp-424 |
| SEQ. ID. NO. 32929 | 450-AspIleAsnGluThrLeuArgLeuMet-458 |
| SEQ. ID. NO. 32930 | 460-AspSerThrValGln-464 |

Antigenic Index - Jameson-Wolf

| | |
|---|---|
| SEQ. ID. NO. 32931 | 1-MetLysLysProLeu-5 |
| SEQ. ID. NO. 32932 | 26-LysAlaGluGluSerLeuThrGlnGlnGlnLysIleLeuGlnLysThrGly-42 |
| SEQ. ID. NO. 32933 | 48-SerHisGlnTyrAspArgGlyTrpPheThrSerThrGluThrThrValIleArgLeuLysProGluLeu-70 |
| SEQ. ID. NO. 32934 | 75-GlnLysTyrLeuProAspAsnLeuLys-83 |
| SEQ. ID. NO. 32935 | 111-IleGluThrGluPheLysTyrAlaProGluThrGluLysValLeuGlu-126 |
| SEQ. ID. NO. 32936 | 128-PhePheGlyLysGlnVal-133 |
| SEQ. ID. NO. 32937 | 144-AsnGlySerGlyLysMetGluVal-151 |
| SEQ. ID. NO. 32938 | 157-AspTyrGluGluLeuSerGly-163 |
| SEQ. ID. NO. 32939 | 179-LysGlyPheLysSerTyrArgAsnSerTyrAspAlaProLeu-192 |
| SEQ. ID. NO. 32940 | 196-LysLeuAlaAspLysGlyAspAlaAlaPheGlu-206 |
| SEQ. ID. NO. 32941 | 208-AlaHisPheAspSerGluThrSerAspGlyIleAsn-219 |
| SEQ. ID. NO. 32942 | 233-PheSerLeuGluTrpLysGluGlyValAspTyr-243 |
| SEQ. ID. NO. 32943 | 264-AsnProAsnGlySerIleAlaProSerLysIleGluValGly-277 |
| SEQ. ID. NO. 32944 | 281-PheSerThrLysThrGlyGluSerGlyAla-290 |
| SEQ. ID. NO. 32945 | 292-IleAspSerGluGlyArgPheArgPhe-300 |
| SEQ. ID. NO. 32946 | 304-ValTyrGlyAspGluLysTyrGlyPro-312 |
| SEQ. ID. NO. 32947 | 329-ValLeuLysArgLysPheAla-335 |
| SEQ. ID. NO. 32948 | 338-SerAlaLysLysMetThrGluGluGlnIleArgAsnAspLeu-351 |
| SEQ. ID. NO. 32949 | 355-ValLysGlyAspAlaSerGly-361 |
| SEQ. ID. NO. 32950 | 378-LeuProGlnGlyLysIleAspValGlyGly-387 |
| SEQ. ID. NO. 32951 | 393-GlyMetLysLysGluAspLeuAsnGln-401 |
| SEQ. ID. NO. 32952 | 406-LeuLysLysThrGluAlaAsnIle-413 |
| SEQ. ID. NO. 32953 | 437-AsnAlaGluAspGluAlaGluAlaArgAlaSerIle-448 |
| SEQ. ID. NO. 32954 | 450-AspIleAsnGluThrLeu-455 |
| SEQ. ID. NO. 32955 | 466-MetAlaArgGluLysTyrLeu-472 |
| SEQ. ID. NO. 32956 | 485-LeuLysAsnAsnAlaLeuLysLeuAsnGlyLysThrLeuGlnAsnGluProAspProAspPheAspGluGlyAspMetValSerGlyGlnProHis-516 |

Hydrophilic Regions - Hopp-Woods

| | |
|---|---|
| SEQ. ID. NO. 32957 | 1-MetLysLysProLeu-5 |
| SEQ. ID. NO. 32958 | 26-LysAlaGluGluSerLeuThrGln-33 |
| SEQ. ID. NO. 32959 | 62-ThrValIleArgLeuLysProGluLeu-70 |
| SEQ. ID. NO. 32960 | 77-TyrLeuProAspAsnLeu-82 |
| SEQ. ID. NO. 32961 | 111-IleGluThrGluPheLysTyrAlaProGluThrGluLysValLeuGlu-126 |
| SEQ. ID. NO. 32962 | 147-GlyLysMetGluVal-151 |
| SEQ. ID. NO. 32963 | 157-AspTyrGluGluLeuSerGly-163 |
| SEQ. ID. NO. 32964 | 180-GlyPheLysSerTyrArgAsnSerTyr-188 |
| SEQ. ID. NO. 32965 | 196-LysLeuAlaAspLysGlyAspAlaAlaPheGlu-206 |

TABLE 1-continued

| | |
|---|---|
| SEQ. ID. NO. 32966 | 208-AlaHisPheAspSerGluThrSerAspGly-217 |
| SEQ. ID. NO. 32967 | 233-PheSerLeuGluTrpLysGluGlyValAspTyr-243 |
| SEQ. ID. NO. 32968 | 272-SerLysIleGluValGly-277 |
| SEQ. ID. NO. 32969 | 292-IleAspSerGluGlyArgPheArgPhe-300 |
| SEQ. ID. NO. 32970 | 304-ValTyrGlyAspGluLysTyrGlyPro-312 |
| SEQ. ID. NO. 32971 | 329-ValLeuLysArgLysPheAla-335 |
| SEQ. ID. NO. 32972 | 338-SerAlaLysLysMetThrGluGluGlnIleArgAsnAspLeu-351 |
| SEQ. ID. NO. 32973 | 355-ValLysGlyAspAla-359 |
| SEQ. ID. NO. 32974 | 381-GlyLysIleAspValGlyGly-387 |
| SEQ. ID. NO. 32975 | 393-GlyMetLysLysGluAspLeuAsn-400 |
| SEQ. ID. NO. 32976 | 406-LeuLysLysThrGluAlaAsnIle-413 |
| SEQ. ID. NO. 32977 | 437-AsnAlaGluAspGluAlaGluAlaArgAlaSerIle-448 |
| SEQ. ID. NO. 32978 | 450-AspIleAsnGluThrLeu-455 |
| SEQ. ID. NO. 32979 | 466-MetAlaArgGluLysTyrLeu-472 |
| SEQ. ID. NO. 32980 | 496-ThrLeuGlnAsnGluProAspProAspPheAspGluGlyAspMetValSer-512 | g591
AMPHI Regions - AMPHI

| | |
|---|---|
| SEQ. ID. NO. 32981 | 6-AlaPheIlePheAla-10 |
| SEQ. ID. NO. 32982 | 17-LeuHisGluPheGlyHisTyrIleValAla-26 |
| SEQ. ID. NO. 32983 | 61-LeuGlyGlyTyrValLysMetValAsp-69 |
| SEQ. ID. NO. 32984 | 143-GlyAspLysIleGlnSerValAsnGlyValSerValGln-155 |
| SEQ. ID. NO. 32985 | 181-SerGlyAlaGlnThrValArgThrIleAspAlaAlaGlyThrProGluAlaGlyLysIleAlaLys-202 |
| SEQ. ID. NO. 32986 | 218-AlaGlyGlyValGluLys-223 |
| SEQ. ID. NO. 32987 | 234-ProGlyAspArgLeu-238 |
| SEQ. ID. NO. 32988 | 245-ProIleAlaSerTrpGlnGluTrpAlaAsnLeuThrArg-257 |
| SEQ. ID. NO. 32989 | 304-AlaTrpAspAlaGlnIleArg-310 |
| SEQ. ID. NO. 32990 | 313-TyrArgProSerValValArgAlaPheGly-322 |
| SEQ. ID. NO. 32991 | 324-GlyTrpGluLysThrValSerHis-331 |
| SEQ. ID. NO. 32992 | 335-ThrLeuLysPhePheGlyLysLeuIle-343 |
| SEQ. ID. NO. 32993 | 351-HisIleSerGlyProLeuThrIleAla-359 |
| SEQ. ID. NO. 32994 | 373-TyrLeuGluPheLeuAlaLeu-379 |

Antigenic Index - Jameson-Wolf

| | |
|---|---|
| SEQ. ID. NO. 32995 | 44-PhePheThrArgLysArgGlyAspThrGlu-53 |
| SEQ. ID. NO. 32996 | 68-ValAspThrArgGluGlyGluValSerGluAlaAspLeu-80 |
| SEQ. ID. NO. 32997 | 84-PheAspLysGlnHisProAlaLysArg-92 |
| SEQ. ID. NO. 32998 | 128-ThrValGluProAspThrValAla-135 |
| SEQ. ID. NO. 32999 | 139-GlyPheGlnSerGlyAspLysIleGlnSer-148 |
| SEQ. ID. NO. 33000 | 156-AspTrpSerSerAlaGlnThr-162 |
| SEQ. ID. NO. 33001 | 187-ArgThrIleAspAlaAlaGlyThrProGluAlaGlyLysIleAlaLysAsnGlnGly-205 |
| SEQ. ID. NO. 33002 | 219-GlyGlyValGluLysGlySerProAlaGluLysAlaGlyLeuLysProGlyAspArgLeuThrAlaAlaAspGlyLysProIle-246 |
| SEQ. ID. NO. 33003 | 254-AsnLeuThrArgGlnSerProGlyLysLysIle-264 |
| SEQ. ID. NO. 33004 | 268-TyrGluArgAlaGlyGlnThrHisThrAlaAspIleArgProAspThrValGluGlnProAspHisThrLeu-291 |
| SEQ. ID. NO. 33005 | 295-ValGlyLeuArgProGlnProAspArgAlaTrp-305 |
| SEQ. ID. NO. 33006 | 307-AlaGlnIleArgArgSerTyrArgProSerVal-317 |
| SEQ. ID. NO. 33007 | 327-LysThrValSerHisSer-332 |
| SEQ. ID. NO. 33008 | 343-IleSerGlyAsnAla-347 |
| SEQ. ID. NO. 33009 | 362-AlaGlyGlnSerAla-366 |
| SEQ. ID. NO. 33010 | 408-IleArgGlyLysProLeuGlyGluArgValGln-418 |

Hydrophilic Regions - Hopp-Woods

| | |
|---|---|
| SEQ. ID. NO. 33011 | 44-PhePheThrArgLysArgGlyAspThr-52 |
| SEQ. ID. NO. 33012 | 68-ValAspThrArgGluGlyGluValSerGluAlaAspLeu-80 |
| SEQ. ID. NO. 33013 | 84-PheAspLysGlnHisProAlaLysArg-92 |
| SEQ. ID. NO. 33014 | 129-ValGluProAspThrValAla-135 |
| SEQ. ID. NO. 33015 | 139-GlyPheGlnSerGlyAspLysIleGlnSer-148 |
| SEQ. ID. NO. 33016 | 193-GlyThrProGluAlaGlyLysIleAlaLys-202 |
| SEQ. ID. NO. 33017 | 220-GlyValGluLysGlySerProAlaGluLysAlaGlyLeuLysProGlyAspArgLeuThrAlaAlaAspGlyLysPro-245 |
| SEQ. ID. NO. 33018 | 256-ThrArgGlnSerProGlyLysLysIle-264 |
| SEQ. ID. NO. 33019 | 268-TyrGluArgAlaGlyGln-273 |
| SEQ. ID. NO. 33020 | 277-AlaAspIleArgProAspThrValGluGlnProAsp-288 |
| SEQ. ID. NO. 33021 | 299-ProGlnProAspArgAlaTrp-305 |
| SEQ. ID. NO. 33022 | 308-GlnIleArgArgSerTyrArg-314 |
| SEQ. ID. NO. 33023 | 362-AlaGlyGlnSerAla-366 |
| SEQ. ID. NO. 33024 | 411-LysProLeuGlyGluArgValGln-418 | g592
AMPHI Regions - AMPHI

| | |
|---|---|
| SEQ. ID. NO. 33025 | 6-PheGlyGlnIlePheSer-11 |
| SEQ. ID. NO. 33026 | 21-GlyGlyLeuLeuGlyGlyLeuIle-28 |
| SEQ. ID. NO. 33027 | 50-AlaProAsnAlaAlaAlaAlaAla-57 |
| SEQ. ID. NO. 33028 | 65-GlnGlyMetIleGlnMetLeuGlyValPheValAsp-76 |
| SEQ. ID. NO. 33029 | 94-ProTyrGlyAspLeu-98 |
| SEQ. ID. NO. 33030 | 109-ValSerGlnValGlyGlnTrp-115 |
| SEQ. ID. NO. 33031 | 153-ThrAlaValPheArgMet-158 |
| SEQ. ID. NO. 33032 | 165-TyrPheGlyAlaValAla-170 |
| SEQ. ID. NO. 33033 | 185-IleMetAlaTrpIleAsnLeuValAlaIleLeuLeuLeuSer-198 |

Antigenic Index - Jameson-Wolf

| | |
|---|---|
| SEQ. ID. NO. 33034 | 35-GlyIleLysArgGlyLeuTyrSerAsnGluAlaGlyMetGlySerAlaProAsnAla-53 |
| SEQ. ID. NO. 33035 | 57-AlaGluValLysHisProValSer-64 |
| SEQ. ID. NO. 33036 | 93-GlnProTyrGlyAspLeuSerGly-100 |
| SEQ. ID. NO. 33037 | 137-AlaTyrAlaGluSerAsnVal-143 |
| SEQ. ID. NO. 33038 | 206-ArgAspTyrThrAlaLysLeuLysMetGlyLysAspProGluPheLysLeuSerGluHisProGlyLeuLysArgArgIleLysSerAspValTrp-237 |

TABLE 1-continued

Hydrophilic Regions - Hopp-Woods
SEQ. ID. NO. 33039   35-GlyIleLysArgGlyLeuTyr-41
SEQ. ID. NO. 33040   57-AlaGluValLysHisProVal-63
SEQ. ID. NO. 33041   212-LeuLysMetGlyLysAspProGluPheLysLeuSerGlu-224
SEQ. ID. NO. 33042   226-ProGlyLeuLysArgArgIleLysSer-234
g593
AMPHI Regions - AMPHI
SEQ. ID. NO. 33043   6-GlyLeuCysLysCysPheGlyGly-13
SEQ. ID. NO. 33044   41-SerThrLeuLeuAsnMetIleAlaGlyIleValArg-52
SEQ. ID. NO. 33045   87-HisMetSerAlaLeuGlu-92
SEQ. ID. NO. 33046   113-LeuSerAlaLeuAlaGlu-118
SEQ. ID. NO. 33047   125-AlaHisArgLysProGluLysLeuSerGlyGlyGlu-136
SEQ. ID. NO. 33048   159-PheSerSerLeuAsp-163
SEQ. ID. NO. 33049   165-HisLeuArgAspArgLeuArgArgMet-173
SEQ. ID. NO. 33050   217-GluThrLeuIleGlnThrProAlaGlyValGlnValAlaArgLeuMetGlyLeu-234
SEQ. ID. NO. 33051   259-LeuLeuSerLeuValArgLeuProAspSerLeuArg-270
SEQ. ID. NO. 33052   290-HisThrAspGlyIle-294
Antigenic Index - Jameson-Wolf
SEQ. ID. NO. 33053   10-CysPheGlyGlyLysThrValAla-17
SEQ. ID. NO. 33054   24-ValGlyArgGlyLysIle-29
SEQ. ID. NO. 33055   33-LeuGlyArgSerGlyCysGlyLysSerThr-42
SEQ. ID. NO. 33056   50-IleValArgProAspGlyGlyGluIleArgLeuAsnGlyGluAsnIleThr-66
SEQ. ID. NO. 33057   69-ProProGluLysArgArgIle-75
SEQ. ID. NO. 33058   99-LysMetGlnLysMetProLysAlaGluAlaGluArgLeuAla-112
SEQ. ID. NO. 33059   119-ValGlyLeuGluAsnGluAlaHisArgLysProGluLysLeuSerGlyGlyGluLysGlnArgLeuAlaLeu-142
SEQ. ID. NO. 33060   157-GluSerPheSerSerLeu-162
SEQ. ID. NO. 33061   164-ThrHisLeuArgAspArgLeuArgArgMetThrAlaGluArgIleArgLysGlyGlyIle-183
SEQ. ID. NO. 33062   190-HisSerProGluGluAlaCysThrAlaAlaAspGluIleAlaVal-204
SEQ. ID. NO. 33063   206-HisGluGlyLysIleLeuGlnCysGlyThrProGluThrLeu-219
SEQ. ID. NO. 33064   233-GlyLeuProAsnThrAspAspArgHisIleProGlnAsnAla-247
SEQ. ID. NO. 33065   250-LeuAspAsnHisGlyThrGluCysArg-258
SEQ. ID. NO. 33066   264-ArgLeuProAspSerLeuArgLeu-271
SEQ. ID. NO. 33067   275-HisProGluHisGlyGlu-280
SEQ. ID. NO. 33068   289-GlnHisThrAspGlyIleSerGlyAsnGly-298
SEQ. ID. NO. 33069   300-ValArgIleArgValAspGluGlyArgIleValArgPheArg-313
Hydrophilic Regions - Hopp-Woods
SEQ. ID. NO. 33070   25-GlyArgGlyLysIle-29
SEQ. ID. NO. 33071   36-SerGlyCysGlyLys-40
SEQ. ID. NO. 33072   51-ValArgProAspGlyGlyGluIleArgLeuAsnGly-62
SEQ. ID. NO. 33073   69-ProProGluLysArgArgIle-75
SEQ. ID. NO. 33074   99-LysMetGlnLysMetProLysAlaGluAlaGluArgLeuAla-112
SEQ. ID. NO. 33075   119-ValGlyLeuGluAsnGluAlaHisArgLysProGluLysLeuSerGlyGlyGluLysGlnArgLeuAlaLeu-142
SEQ. ID. NO. 33076   164-ThrHisLeuArgAspArgLeuArgArgMetThrAlaGluArgIleArgLysGlyGly-182
SEQ. ID. NO. 33077   191-SerProGluGluAlaCysThrAlaAlaAspGluIleAlaVal-204
SEQ. ID. NO. 33078   206-HisGluGlyLysIle-210
SEQ. ID. NO. 33079   236-AsnThrAspAspAspArgHisIlePro-244
SEQ. ID. NO. 33080   253-HisGlyThrGluCysArg-258
SEQ. ID. NO. 33081   264-ArgLeuProAspSerLeuArg-270
SEQ. ID. NO. 33082   275-HisProGluHisGlyGlu-280
SEQ. ID. NO. 33083   289-GlnHisThrAspGlyIleSer-295
SEQ. ID. NO. 33084   300-ValArgIleArgValAspGluGlyArgIleValArgPheArg-313
g594
AMPHI Regions - AMPHI
SEQ. ID. NO. 33085   21-SerIleLeuArgLeu-25
SEQ. ID. NO. 33086   108-AlaGlyArgLysCysGlnGluThrAlaAlaAla-118
SEQ. ID. NO. 33087   138-AlaIleLysHisCysAsnPheThr-145
Antigenic Index - Jameson-Wolf
SEQ. ID. NO. 33088   1-MetGlyAlaAspThrAspGlyAspLysAspValArgLeuAsnArgThr-16
SEQ. ID. NO. 33089   51-ValGluHisProAsnArgPhe-57
SEQ. ID. NO. 33090   75-HisLeuAspGlySerThrGlyGly-82
SEQ. ID. NO. 33091   86-PheArgArgGluLysThrGlyHisLysArgArgCysHisThrGlnCys-101
SEQ. ID. NO. 33092   103-HisSerAlaArgAlaAlaGlyArgLysCysGlnGluThr-115
SEQ. ID. NO. 33093   137-ArgAlaIleLysHisCysAsn-143
Hydrophilic Regions - Hopp-Woods
SEQ. ID. NO. 33094   1-MetGlyAlaAspThrAspGlyAspLysAspValArgLeuAsnArg-15
SEQ. ID. NO. 33095   86-PheArgArgGluLysThrGlyHisLysArgArgCysHis-98
SEQ. ID. NO. 33096   105-AlaArgAlaAlaGlyArgLysCysGlnGluThr-115
g595
AMPHI Regions - AMPHI
SEQ. ID. NO. 33097   20-CysGlnProProGluAla-25
SEQ. ID. NO. 33098   98-GlyLeuSerAspLysMetAsnArg-105
SEQ. ID. NO. 33099   140-AlaAspLeuGluLysLeuProGlnProLeuAlaAspTyrLys-153
SEQ. ID. NO. 33100   157-GlnGlyGluValLys-161
SEQ. ID. NO. 33101   170-PheThrGluAlaValLysAlaGlyAspIleGluLysAlaLys-183
SEQ. ID. NO. 33102   196-IleGluProIleAlaGluLeuPheSerGluLeuAspProValIleAspAlaCysGluAspAspPheLysAspGly-220
SEQ. ID. NO. 33103   224-AlaGlyPheThrGlyPheHisArg-231
SEQ. ID. NO. 33104   247-GluThrAlaAlaLeuMetThrAspValGluAlaLeuGlnLysGluIleAsp-264
SEQ. ID. NO. 33105   274-ValGlyGlyAlaSerGluLeuIleGlu-282
SEQ. ID. NO. 33106   311-SerLysLysIleValAspLeuPheArgProLeu-321
SEQ. ID. NO. 33107   337-PheLysGlnValAsnGluIleLeuAlaLys-346

TABLE 1-continued

| | |
|---|---|
| SEQ. ID. NO. 33108 | 351-AspGlyPheGluThrTyrAspLysLeuSerGluAlaAsp-363 |
| SEQ. ID. NO. 33109 | 369-AlaProIleAsnAlaLeuAlaGluAspLeuAlaGlnLeuArgGlyIleLeuGlyLeu-387 |
| Antigenic Index - Jameson-Wolf | |
| SEQ. ID. NO. 33110 | 1-MetArgLysPheAsn-5 |
| SEQ. ID. NO. 33111 | 21-GlnProProGluAlaGluLysAlaAlaPro-30 |
| SEQ. ID. NO. 33112 | 32-AlaSerGlyGluThrGlnSerAlaAsnGluGlyGlySer-44 |
| SEQ. ID. NO. 33113 | 50-AsnAspAsnAlaCysGluProMetAsnLeu-59 |
| SEQ. ID. NO. 33114 | 70-IleLysAsnAsnSerGlyArgLysLeuGluTrpGluIle-82 |
| SEQ. ID. NO. 33115 | 87-MetValValAspGluArgGluAsnIleAla-96 |
| SEQ. ID. NO. 33116 | 98-GlyLeuSerAspLysMetAsnArgAsnLeuLeuProGlyGluTyrGluMet-114 |
| SEQ. ID. NO. 33117 | 120-ThrAsnProArgGlyLysLeuValVal-128 |
| SEQ. ID. NO. 33118 | 130-AspSerGlyPheLysAspThrAlaAsnGluAlaAspLeuGluLysLeuPro-146 |
| SEQ. ID. NO. 33119 | 158-GlyGluValLysGluLeuAlaAlaLysThrLysThrPheThrGluAlaValLysAlaGlyAspIleGluLysAlaLysSer-184 |
| SEQ. ID. NO. 33120 | 191-ValHisTyrGluArgIleGluProIle-199 |
| SEQ. ID. NO. 33121 | 204-SerGluLeuAspProValIleAspAlaCysGluAspAspPheLysAspGlyAlaLysAspAlaGly-225 |
| SEQ. ID. NO. 33122 | 238-ValGluLysAspValSerGlyValLysGluThrAlaAla-250 |
| SEQ. ID. NO. 33123 | 252-LeuMetThrAspValGluAlaLeuGlnLysGluIleAsp-264 |
| SEQ. ID. NO. 33124 | 269-ProProGlyLysValValGlyGlyAla-277 |
| SEQ. ID. NO. 33125 | 279-GluLeuIleGluGluAlaAlaGlySerLysIleSerGlyGluGluAspArgTyrSerHisThrAspLeuSerAspPheGlnAlaAsnAlaAspGlySerLysLysIleValAsp-316 |
| SEQ. ID. NO. 33126 | 322-IleGluAlaLysAsnLysAlaLeuLeuGluLysThrAspThrAsnPheLysGlnValAsn-341 |
| SEQ. ID. NO. 33127 | 345-AlaLysTyrArgThrLysAspGlyPheGluThrTyrAspLysLeuSerGluAlaAspArgLysAlaLeu-367 |
| SEQ. ID. NO. 33128 | 374-LeuAlaGluAspLeuAlaGln-380 |
| Hydrophilic Regions - Hopp-Woods | |
| SEQ. ID. NO. 33129 | 1-MetArgLysPheAsn-5 |
| SEQ. ID. NO. 33130 | 21-GlnProProGluAlaGluLysAlaAlaPro-30 |
| SEQ. ID. NO. 33131 | 32-AlaSerGlyGluThrGlnSerAlaAsnGluGlyGlySer-44 |
| SEQ. ID. NO. 33132 | 72-AsnAsnSerGlyArgLysLeuGluTrpGluIle-82 |
| SEQ. ID. NO. 33133 | 87-MetValValAspGluArgGluAsnIle-95 |
| SEQ. ID. NO. 33134 | 99-LeuSerAspLysMetAsnArg-105 |
| SEQ. ID. NO. 33135 | 110-GlyGluTyrGluMet-114 |
| SEQ. ID. NO. 33136 | 122-ProArgGlyLysLeuValVal-128 |
| SEQ. ID. NO. 33137 | 131-SerGlyPheLysAspThrAlaAsnGluAlaAspLeuGluLysLeuPro-146 |
| SEQ. ID. NO. 33138 | 158-GlyGluValLysGluLeuAlaAlaLysThrLysThrPheThrGluAlaValLysAlaGlyAspIleGluLysAlaLysSer-184 |
| SEQ. ID. NO. 33139 | 191-ValHisTyrGluArgIleGluProIle-199 |
| SEQ. ID. NO. 33140 | 204-SerGluLeuAspProValIleAspAlaCysGluAspAspPheLysAspGlyAlaLysAspAlaGly-225 |
| SEQ. ID. NO. 33141 | 238-ValGluLysAspValSerGlyValLysGluThrAlaAla-250 |
| SEQ. ID. NO. 33142 | 252-LeuMetThrAspValGluAlaLeuGlnLysGluIleAsp-264 |
| SEQ. ID. NO. 33143 | 279-GluLeuIleGluGluAlaAlaGlySerLysIleSerGlyGluGluAspArgTyrSerHis-298 |
| SEQ. ID. NO. 33144 | 308-AlaAspGlySerLysLysIleValAsp-316 |
| SEQ. ID. NO. 33145 | 322-IleGluAlaLysAsnLysAlaLeuLeuGluLysThrAspThrAsnPhe-337 |
| SEQ. ID. NO. 33146 | 347-TyrArgThrLysAspGlyPheGluThrTyrAspLysLeuSerGluAlaAspArgLysAlaLeu-367 |
| SEQ. ID. NO. 33147 | 374-LeuAlaGluAspLeuAlaGln-380 |
| g596-2 | |
| AMPHI Regions - AMPHI | |
| SEQ. ID. NO. 33148 | 9-MetLeuArgValSerLysValVal-16 |
| SEQ. ID. NO. 33149 | 50-LeuArgIleMetAlaGlyValAspLys-58 |
| SEQ. ID. NO. 33150 | 87-ValArgGluGluValGluSerGlyLeuGlyGluValAlaAlaAlaGlnLysArgLeuGluGluValTyrAlaGluTyr-112 |
| SEQ. ID. NO. 33151 | 192-ProThrAsnHisLeuAsp-197 |
| SEQ. ID. NO. 33152 | 202-GluTrpLeuGluGluGlnPheLeuValArgPheProGly-213 |
| SEQ. ID. NO. 33153 | 296-ArgPheGluGluMetSerAsnTyr-303 |
| SEQ. ID. NO. 33154 | 322-LeuGlyAsnGluValIleGluPheValAsnValSerLysSerPhe-336 |
| SEQ. ID. NO. 33155 | 366-SerThrLeuPheLysMet-371 |
| SEQ. ID. NO. 33156 | 409-AspAsnIleAlaGlu-413 |
| SEQ. ID. NO. 33157 | 440-AspGlnSerLysIleAlaArgGlnLeuSerGly-450 |
| SEQ. ID. NO. 33158 | 483-LeuArgAlaLeuGluAspAlaLeuLeuGluPheAla-494 |
| Antigenic Index - Jameson-Wolf | |
| SEQ. ID. NO. 33159 | 16-ValProProGlnLysThrIleIleLysAspIleSer-27 |
| SEQ. ID. NO. 33160 | 41-LeuAsnGlyThrGlyLysSerThrVal-49 |
| SEQ. ID. NO. 33161 | 54-AlaGlyValAspLysGluPheGluGlyGluAla-64 |
| SEQ. ID. NO. 33162 | 75-LeuProGlnGluProGluLeuAspProGluLysThrValArgGluGluValGluSerGlyLeu-95 |
| SEQ. ID. NO. 33163 | 99-AlaAlaAlaGlnLysArgLeuGluGluValTyr-109 |
| SEQ. ID. NO. 33164 | 112-TyrAlaAsnProAspAlaPheAspAlaLeuAlaGluGluGlnGlyArgLeuGlu-130 |
| SEQ. ID. NO. 33165 | 136-GlySerSerThrGlyGlyGlyAlaGluHisGluLeuGluIleAlaAlaAspAlaLeuArgLeuProAspTrpAspAlaLysIle-163 |
| SEQ. ID. NO. 33166 | 165-AsnLeuSerGlyGlyGluLysArgArgValAla-175 |
| SEQ. ID. NO. 33167 | 181-LeuSerLysProAspMet-186 |
| SEQ. ID. NO. 33168 | 190-AspGluProThrAsnHisLeuAspAlaGluSer-200 |
| SEQ. ID. NO. 33169 | 219-ThrHisAspArgTyrPhe-224 |
| SEQ. ID. NO. 33170 | 233-LeuGluLeuAspArgGlyHisGlyIle-241 |
| SEQ. ID. NO. 33171 | 243-TrpLysGlyAsnTyrSerSer-249 |
| SEQ. ID. NO. 33172 | 251-LeuGluGlnLysGluLysArgLeuGluGluAsnGluAlaLysSerGluAlaAlaArgValLysAlaMetLysGlnGluLeuGluTrpValArgGlnAsnAlaLysGlyArgGlnAlaLysProLysAlaArgLeuAlaArgPheGluGluMetSerAsnTyrGluTyrGlnLysArgAsnGluThrGlnGlu-313 |
| SEQ. ID. NO. 33173 | 319-AlaGluArgLeuGlyAsnGluVal-326 |
| SEQ. ID. NO. 33174 | 333-SerLysSerPheGlyAspLysValLeu-341 |
| SEQ. ID. NO. 33175 | 360-ProAsnGlyAlaGlyLysSerThrLeu-368 |
| SEQ. ID. NO. 33176 | 373-AlaGlyLysGluGlnProAspSerGlyGluValLysIle-385 |
| SEQ. ID. NO. 33177 | 395-AspGlnSerArgGluGlyLeuGlnAsnAspLysThrValPhe-408 |
| SEQ. ID. NO. 33178 | 411-IleAlaGluGlyArgAspIleLeu-418 |
| SEQ. ID. NO. 33179 | 425-IleProAlaArgGlnTyrLeuGlyArgPheAsnPheLysGlySerAspGlnSerLysIleAlaArgGlnLeuSerGlyGlyGluArgGlyArgLeuHisLeu-458 |

TABLE 1-continued

| | |
|---|---|
| SEQ. ID. NO. 33180 | 471-LeuAspGluProSerAsnAspLeuAspValGluThrLeuArgAlaLeuGlu-487 |
| SEQ. ID. NO. 33181 | 501-SerHisAspArgTrpPhe-506 |
| SEQ. ID. NO. 33182 | 516-AlaCysGluGlyAspSerLysTrp-523 |
| SEQ. ID. NO. 33183 | 527-AspGlyAsnTyrGlnGluTyrGluAlaAspLysLysArgArgLeuGlyLysGluGlyAlaLysProLysArgIleLysTyrLysProValThrArg-558 |
| Hydrophilic Regions - Hopp-Woods | |
| SEQ. ID. NO. 33184 | 54-AlaGlyValAspLysGluPheGluGlyGluAla-64 |
| SEQ. ID. NO. 33185 | 77-GlnGluProGluLeuAspProGluLysThrValArgGluGluValGluSerGlyLeu-95 |
| SEQ. ID. NO. 33186 | 99-AlaAlaAlaGlnLysArgLeuGluGluValTyr-109 |
| SEQ. ID. NO. 33187 | 113-AlaAsnProAspAlaAspPheAspAlaLeuAlaGluGluGlnGlyArgLeuGlu-130 |
| SEQ. ID. NO. 33188 | 141-GlyGlyAlaGluHisGluLeuGluIleAlaAlaAspAlaLeuArg-155 |
| SEQ. ID. NO. 33189 | 157-ProAspTrpAspAlaLysIle-163 |
| SEQ. ID. NO. 33190 | 167-SerGlyGlyGluLysArgArgValAla-175 |
| SEQ. ID. NO. 33191 | 181-LeuSerLysProAsp-185 |
| SEQ. ID. NO. 33192 | 190-AspGluProThrAsnHisLeuAspAlaGluSer-200 |
| SEQ. ID. NO. 33193 | 233-LeuGluLeuAspArgGlyHis-239 |
| SEQ. ID. NO. 33194 | 251-LeuGluGlnLysGluLysArgLeuGluAsnGluAlaLysSerGluAlaAlaArgValLysAlaMetLysGlnGluLeuGluTrp-278 |
| SEQ. ID. NO. 33195 | 280-ArgGlnAsnAlaLysGlyArgGlnAlaLysProLysAlaArgLeuAlaArgPheGluGluMetSerAsn-302 |
| SEQ. ID. NO. 33196 | 304-GluTyrGlnLysArgAsnGluThrGln-312 |
| SEQ. ID. NO. 33197 | 319-AlaGluArgLeuGlyAsnGluVal-326 |
| SEQ. ID. NO. 33198 | 373-AlaGlyLysGluGlnProAspSerGlyGluValLysIle-385 |
| SEQ. ID. NO. 33199 | 395-AspGlnSerArgGluGlyLeuGlnAsnAspLysThrValPhe-408 |
| SEQ. ID. NO. 33200 | 411-IleAlaGluGlyArgAspIleLeu-418 |
| SEQ. ID. NO. 33201 | 435-AsnPheLysGlySerAspGlnSerLysIleAlaArg-446 |
| SEQ. ID. NO. 33202 | 448-LeuSerGlyGlyGluArgGlyArgLeuHisLeu-458 |
| SEQ. ID. NO. 33203 | 472-AspGluProSerAsnAspLeuAspValGluThrLeuArgAlaLeuGlu-487 |
| SEQ. ID. NO. 33204 | 517-CysGluGlyAspSer-521 |
| SEQ. ID. NO. 33205 | 529-AsnTyrGlnGluTyrGluAlaAspLysLysArgArgLeuGlyLysGluGlyAlaLysProLysArgIleLysTyr-553 |
| g597 | |
| AMPHI Regions - AMPHI | |
| SEQ. ID. NO. 33206 | 6-SerAsnSerLeuLysGlnLeuGlnGlu-14 |
| SEQ. ID. NO. 33207 | 45-TrpAspLysPheGlnLysLeu-51 |
| SEQ. ID. NO. 33208 | 68-GlnIleSerArgPheValSerGly-75 |
| SEQ. ID. NO. 33209 | 101-LeuArgTyrThrArgTyrValAsnAla-109 |
| SEQ. ID. NO. 33210 | 111-AsnArgGluValValLysAspLeuGluLysGlnGln-122 |
| SEQ. ID. NO. 33211 | 132-IleAsnAsnGluLeuAlaArgLeuLysLys-141 |
| SEQ. ID. NO. 33212 | 144-AlaAsnValGlnSerLeu-149 |
| SEQ. ID. NO. 33213 | 157-AspAlaAlaGluGlnThrGlu-163 |
| SEQ. ID. NO. 33214 | 170-LysIleSerLysAspAlaArg-176 |
| SEQ. ID. NO. 33215 | 189-AsnLysLeuLeuSer-193 |
| SEQ. ID. NO. 33216 | 253-ProSerValMetGlyIleGlySerAlaAspGlyPheSerArgMetGlnGlyArgLeuLysLysProValAspGlyValProThrGly-281 |
| SEQ. ID. NO. 33217 | 302-ProAlaThrValGluSerIleAla-309 |
| SEQ. ID. NO. 33218 | 314-SerTyrAlaAspGluLeuAspGlyTyrGlyLysVal-325 |
| SEQ. ID. NO. 33219 | 336-SerIleTyrAlaGlyLeuSerGluIleSerAlaGlyLys-348 |
| Antigenic Index - Jameson-Wolf | |
| SEQ. ID. NO. 33220 | 7-AsnSerLeuLysGlnLeuGlnGluGluArgIleArgGlnGluArgIleArgGlnGluArgIleArgGlnAlaArgGlyAsnLeu-34 |
| SEQ. ID. NO. 33221 | 36-SerValAsnArgLysGlnArgGluAlaTrpAspLysPheGlnLysLeuAsnThrGluLeuAsnArgLeuLysThrGluValAlaAla-64 |
| SEQ. ID. NO. 33222 | 74-SerGlyAsnTyrLysAsnSerArgProAsnAla-84 |
| SEQ. ID. NO. 33223 | 91-AsnAlaGluProGlyGlnLysAsnArgPhe-100 |
| SEQ. ID. NO. 33224 | 107-ValAsnAlaSerAsnArgGluValValLysAspLeuGluLysGlnGlnLys-123 |
| SEQ. ID. NO. 33225 | 128-GlnGluGlnLysIleAsnAsnGluLeuAlaArgLeuLysLysIleGln-143 |
| SEQ. ID. NO. 33226 | 149-LeuLeuLysLysGlnGlyValThrAspAlaAlaGluGlnThrGluSerArgArgGlnAsnAlaLysIleSerLysAspAlaArgLysLeuLeuGlu<br>GlnLysGlyAsnGluGlnGlnLeu-188 |
| SEQ. ID. NO. 33227 | 191-LeuLeuSerAsnLeuGluLysLysLysAlaGluHisArgIleGlnAspAlaGluAlaLysArgLysLeuAlaGluAlaLysLeuAlaAlaAlaGlu<br>LysAlaArgLysGluAlaAlaGlnGlnLysAlaGluAlaArgArgAlaGluMetSerAsnLeuThrAlaGluAspArgAsnIleGlnAla<br>ProSer-254 |
| SEQ. ID. NO. 33228 | 259-GlySerAlaAspGlyPheSerArgMetGlnGlyArgLeuLysLysProValAspGlyValProThr-280 |
| SEQ. ID. NO. 33229 | 284-GlyGlnAsnArgSerGlyGlyAspVal-292 |
| SEQ. ID. NO. 33230 | 314-SerTyrAlaAspGluLeuAspGlyTyrGly-323 |
| SEQ. ID. NO. 33231 | 329-AspHisGlyGluAsnTyr-334 |
| SEQ. ID. NO. 33232 | 343-GluIleSerAlaGlyLysGlyTyrThr-351 |
| SEQ. ID. NO. 33233 | 354-AlaGlySerLysIleGlyThrSerGlySerLeuProAspGlyGluGluGlyLeu-371 |
| SEQ. ID. NO. 33234 | 375-IleArgTyrArgGlyGlnValLeuAsnProSerGlyTrp-387 |
| Hydrophilic Regions - Hopp-Woods | |
| SEQ. ID. NO. 33235 | 7-AsnSerLeuLysGlnLeuGlnGluGluArgIleArgGlnGluArgIleArgGlnGluArgIleArgGlnAlaArgGlyAsn-33 |
| SEQ. ID. NO. 33236 | 37-ValAsnArgLysGlnArgGluAlaTrpAspLysPheGlnLysLeuAsnThrGluLeuAsnArgLeuLysThrGluValAlaAla-64 |
| SEQ. ID. NO. 33237 | 77-TyrLysAsnSerArgProAsn-83 |
| SEQ. ID. NO. 33238 | 91-AsnAlaGluProGlyGlnLysAsnArgPhe-100 |
| SEQ. ID. NO. 33239 | 110-SerAsnArgGluValValLysAspLeuGluLysGlnGlnLys-123 |
| SEQ. ID. NO. 33240 | 128-GlnGluGlnLysIleAsnAsnGluLeuAlaArgLeuLysLysIleGln-143 |
| SEQ. ID. NO. 33241 | 149-LeuLeuLysLysGlnGlyValThrAspAlaAlaGluGlnThrGluSerArgArgGlnAsnAlaLysIleSerLysAspAlaArgLysLeuLeuGlu<br>GlnLysGlyAsnGluGlnGlnLeu-188 |
| SEQ. ID. NO. 33242 | 193-SerAsnLeuGluLysLysLysAlaGluHisArgIleGlnAspAlaGluAlaLysArgLysLeuAlaGluAlaLysLeuAlaAlaAlaGluLysAla<br>ArgLysGluAlaAlaGlnGlnLysAlaGluAlaArgArgAlaGluMet-240 |
| SEQ. ID. NO. 33243 | 244-ThrAlaGluAspArgAsnIleGln-251 |
| SEQ. ID. NO. 33244 | 267-MetGlnGlyArgLeuLysLysProValAsp-276 |
| SEQ. ID. NO. 33245 | 286-AsnArgSerGlyGlyAspVal-292 |
| SEQ. ID. NO. 33246 | 315-TyrAlaAspGluLeuAspGlyTyrGly-323 |
| SEQ. ID. NO. 33247 | 356-SerLysIleGlyThr-360 |
| SEQ. ID. NO. 33248 | 363-SerLeuProAspGlyGluGluGlyLeu-371 |

TABLE 1-continued g601
AMPHI Regions - AMPHI
SEQ. ID. NO. 33249    7-LeuValAspGluIleAspValProAsnIleGlyArg-18
SEQ. ID. NO. 33250    26-AlaGlyIleProThrValPhe-32
SEQ. ID. NO. 33251    42-GlyLysGluLeuGlnAspAspIleAsnAsnAspAlaAlaAlaLeuGluLysPheGluThrIleArgAlaTyrGlyAlaLeu-68
SEQ. ID. NO. 33252    70-MetGlyLeuIleSerAspValSerGlu-78
SEQ. ID. NO. 33253    100-SerSerGlyLysThrValAsn-106
SEQ. ID. NO. 33254    137-AlaValLeuGlyThrLeuValAsnLeuAlaAla-147
SEQ. ID. NO. 33255    167-GlyAlaAlaAlaGlu-171
Antigenic Index - Jameson-Wolf
SEQ. ID. NO. 33256    3-ProThrGlyAsnLeuValAspGluIleAspValProAsnIleGlyArgLeuLys-20
SEQ. ID. NO. 33257    39-GlyTyrThrGlyLysGluLeuGlnAspAspIleAsnAsnAspAlaAlaAlaLeuGluLysPheGluThr-61
SEQ. ID. NO. 33258    75-AspValSerGluAlaAlaAlaArgAlaArgThrProLysProAlaPhe-90
SEQ. ID. NO. 33259    97-TyrThrAlaSerSerGlyLysThrValAsn-106
SEQ. ID. NO. 33260    108-AlaAspIleAspLeuProVal-114
SEQ. ID. NO. 33261    147-AlaGlyGlyGlyThrArgLysGluValArgPheGlyHisProSerGlyThrLeuArg-165
SEQ. ID. NO. 33262    170-AlaGluCysGlnAspGlyGln-176
SEQ. ID. NO. 33263    183-ValMetSerArgSerAlaArgValIle-191
SEQ. ID. NO. 33264    196-ValArgValProAspAspCysPhe-203
Hydrophilic Regions - Hopp-Woods
SEQ. ID. NO. 33265    7-LeuValAspGluIleAspVal-13
SEQ. ID. NO. 33266    40-TyrThrGlyLysGluLeuGlnAspAspIleAsnAsnAspAlaAlaAlaLeuGluLysPheGluThr-61
SEQ. ID. NO. 33267    75-AspValSerGluAlaAlaAlaArgAlaArgThrProLys-87
SEQ. ID. NO. 33268    99-AlaSerSerGlyLysThrValAsn-106
SEQ. ID. NO. 33269    108-AlaAspIleAspLeuProVal-114
SEQ. ID. NO. 33270    149-GlyGlyThrArgLysGluValArgPhe-157
SEQ. ID. NO. 33271    170-AlaGluCysGlnAsp-174
SEQ. ID. NO. 33272    186-ArgSerAlaArgValIle-191
SEQ. ID. NO. 33273    198-ValProAspAspCysPhe-203
g602
AMPHI Regions - AMPHI
SEQ. ID. NO. 33274    54-ArgGlnValAlaGlnIle-59
SEQ. ID. NO. 33275    61-AlaGlyLeuHisValCysAsnGlyVal-69
Antigenic Index - Jameson-Wolf
SEQ. ID. NO. 33276    5-GlnCysAspLysAlaArgHisMetArgPro-14
SEQ. ID. NO. 33277    17-LeuGlyGlyGlnIleAsnArgHisArgGlnAlaSerAsnArgGlyLeuCys-33
SEQ. ID. NO. 33278    35-PheGlyGlyPheGlnGlyAsnArgGluAlaGln-45
SEQ. ID. NO. 33279    51-LeuIleAspArgGlnVal-56
SEQ. ID. NO. 33280    88-GlyArgGlnMetProSerGluLysThrLeu-97
SEQ. ID. NO. 33281    103-GlnMetArgAspTyr-107
Hydrophilic Regions - Hopp-Woods
SEQ. ID. NO. 33282    5-GlnCysAspLysAlaArgHisMet-12
SEQ. ID. NO. 33283    21-IleAsnArgHisArgGlnAlaSerAsnArgGly-31
SEQ. ID. NO. 33284    39-GlnGlyAsnArgGluAlaGln-45
SEQ. ID. NO. 33285    51-LeuIleAspArgGlnVal-56
SEQ. ID. NO. 33286    91-MetProSerGluLysThrLeu-97
g603
AMPHI Regions - AMPHI
SEQ. ID. NO. 33287    119-MetLeuLeuAsnGluLeuGluLys-126
SEQ. ID. NO. 33288    131-AspArgIleLysAlaIleGlyArgArgIleAlaHisGlyGlyGluLysTyr-147
SEQ. ID. NO. 33289    157-ValLeuAspGluLeuLysAlaCysIlePro-166
SEQ. ID. NO. 33290    171-HisAsnProAlaAsnIleSerGlyIleLeuAla-181
SEQ. ID. NO. 33291    185-HisPheProGlyLeuProAsnValGly-193
SEQ. ID. NO. 33292    198-SerPheHisGlnThrMetPro-204
SEQ. ID. NO. 33293    211-AlaValProArgGluLeu-216
SEQ. ID. NO. 33294    238-GluAlaAlaArgIleLeuGlyLysProLeuGluAspIleArgMetIleIleAlaHis-256
SEQ. ID. NO. 33295    259-AsnGlyAlaSerIleThrAlaValLysAsnGlyLysSerVal-272
SEQ. ID. NO. 33296    279-ThrProIleGluGly-283
SEQ. ID. NO. 33297    298-TyrSerTyrProThr-302
SEQ. ID. NO. 33298    323-ProGlyIleSerGluLeuProAsnAspCysArgThr-334
SEQ. ID. NO. 33299    356-ArgLeuAlaLysTyrIleAlaSerMetAla-365
SEQ. ID. NO. 33300    392-ValSerTyrLeuAsp-396
Antigenic Index - Jameson-Wolf
SEQ. ID. NO. 33301    1-MetAspSerArgLeuArgGlyAsnAspAlaArgLysTyrGly-14
SEQ. ID. NO. 33302    17-PheAlaGlnArgGlyArgLeuLysHisThrProProAsnAlaHisProPheSerAspGlyProAlaProLysLysGlnProGlnThrThrArgArg
                      AsnIleMetSer-52
SEQ. ID. NO. 33303    64-SerSerLeuLysGlyAlaValIleAspArgLysSerGlySer-77
SEQ. ID. NO. 33304    83-LeuGlyGluArgLeuThrThrProGluAla-92
SEQ. ID. NO. 33305    95-ThrPheAsnLysAspGlyAsnLysArgGlnValProLeuSerGlyArgAsnCysHis-113
SEQ. ID. NO. 33306    123-GluLeuGluLysHisGlyLeuHisAspArgIleLysAlaIleGlyArgArgIleAlaHisGlyGlyGluLysTyrHisGlu-149
SEQ. ID. NO. 33307    151-ValLeuIleAspGlnAspValLeuAspGluLeuLysAla-163
SEQ. ID. NO. 33308    202-ThrMetProGluArgAlaTyr-208
SEQ. ID. NO. 33309    214-ArgGluLeuArgLysLysTyrAlaPheArgArgTyrGlyPheHisGlyThrGlyMet-232
SEQ. ID. NO. 33310    238-GluAlaAlaArgIleLeuGlyLysProLeuGluAspIleArg-251
SEQ. ID. NO. 33311    257-LeuGlyAsnGlyAla-261
SEQ. ID. NO. 33312    264-ThrAlaValLysAsnGlyLysSerValAspThrGlyMet-276
SEQ. ID. NO. 33313    288-ThrArgCysGlyAspThrAspProGlyVal-297
SEQ. ID. NO. 33314    310-AlaGlnValAspGluMetLeuAsnGluLysSerGlyPheProGlyIleSerGluLeuProAsnAspCysArgThrLeuGluIleAlaAlaAspGlu
                      GlyArgGluGlyAlaArgLeu-348
SEQ. ID. NO. 33315    379-GlyIleGlyGluAsnSerArgAsnIleArgAlaLysThr-391

TABLE 1-continued

| | |
|---|---|
| SEQ. ID. NO. 33316 | 402-IleAspThrLysAlaAsnMetGluLysArgTyrGlyAsnSerGlyIle-417 |
| SEQ. ID. NO. 33317 | 419-SerProThrAspSerSerPro-425 |
| SEQ. ID. NO. 33318 | 431-ProThrAsnGluGluLeu-436 |
| Hydrophilic Regions - Hopp-Woods | |
| SEQ. ID. NO. 33319 | 1-MetAspSerArgLeuArgGlyAsnAspAlaArgLysTyrGly-14 |
| SEQ. ID. NO. 33320 | 17-PheAlaGlnArgGlyArgLeuLysHisThrPro-27 |
| SEQ. ID. NO. 33321 | 34-SerAspGlyProAlaProLysLysGlnProGlnThrThrArgArgAsnIleMet-51 |
| SEQ. ID. NO. 33322 | 69-AlaValIleAspArgLysSerGly-76 |
| SEQ. ID. NO. 33323 | 83-LeuGlyGluArgLeuThrThr-89 |
| SEQ. ID. NO. 33324 | 96-PheAsnLysAspGlyAsnLysArgGlnValProLeuSerGlyArgAsnCysHis-113 |
| SEQ. ID. NO. 33325 | 123-GluLeuGluLysHisGlyLeuHisAspArgIleLysAlaIleGlyArgArgIleAlaHisGlyGlyGluLysTyrHisGlu-149 |
| SEQ. ID. NO. 33326 | 156-AspValLeuAspGluLeuLysAla-163 |
| SEQ. ID. NO. 33327 | 203-MetProGluArgAlaTyr-208 |
| SEQ. ID. NO. 33328 | 214-ArgGluLeuArgLysLysTyrAlaPhe-222 |
| SEQ. ID. NO. 33329 | 238-GluAlaAlaArgIleLeuGlyLysProLeuGluAspIleArg-251 |
| SEQ. ID. NO. 33330 | 267-LysAsnGlyLysSerValAspThr-274 |
| SEQ. ID. NO. 33331 | 289-ArgCysGlyAspThrAspPro-295 |
| SEQ. ID. NO. 33332 | 310-AlaGlnValAspGluMetLeuAsnGluLysSerGly-321 |
| SEQ. ID. NO. 33333 | 328-LeuProAsnAspCysArgThrLeuGluIleAlaAlaAspGluGlyArgGluGlyAlaArgLeu-348 |
| SEQ. ID. NO. 33334 | 380-IleGlyGluAsnSerArgAsnIleArgAlaLysThr-391 |
| SEQ. ID. NO. 33335 | 402-IleAspThrLysAlaAsnMetGluLysArgTyrGly-413 |
| SEQ. ID. NO. 33336 | 432-ThrAsnGluGluLeu-436 |
| g604 | |
| AMPHI Regions - AMPHI | |
| SEQ. ID. NO. 33337 | 35-SerValValGlnPheAla-40 |
| SEQ. ID. NO. 33338 | 49-IleAspValGlyGlyValTyrGly-56 |
| SEQ. ID. NO. 33339 | 98-AspGlyPheLysPhePheGln-104 |
| SEQ. ID. NO. 33340 | 111-AspValValLeuGlnLeuPheAlaArgValAlaGlnValGlyGlyValGlnGluAsn-129 |
| SEQ. ID. NO. 33341 | 146-ArgHisIleAsnPheValAspGlnIleAlaGlyTrpGlu-158 |
| Antigenic Index - Jameson-Wolf | |
| SEQ. ID. NO. 33342 | 10-SerAlaAlaCysGlyLysValAspGlnArgThrGluHisGlyGlyGlyAspGlyAspArgGlyAspAlaHis-33 |
| SEQ. ID. NO. 33343 | 44-GlyAlaTyrArgGlnIleAspVal-51 |
| SEQ. ID. NO. 33344 | 65-GlyGlyGlyArgAspGluGlyGlyPheArgArgAlaArgAlaGlyGlyGlyPhe-82 |
| SEQ. ID. NO. 33345 | 95-IleCysAlaAspGly-99 |
| SEQ. ID. NO. 33346 | 101-LysPhePheGlnArgGlyGlyIle-108 |
| SEQ. ID. NO. 33347 | 125-GlyValGlnGluAsnGlyArgAsnAlaArgValAspGluArgGlyPheGln-141 |
| Hydrophilic Regions - Hopp-Woods | |
| SEQ. ID. NO. 33348 | 14-GlyLysValAspGlnArgThrGluHisGlyGlyGlyAspGlyAspArgGlyAspAlaHis-33 |
| SEQ. ID. NO. 33349 | 66-GlyGlyArgAspGluGlyGlyPheArgArgAlaArgAla-78 |
| SEQ. ID. NO. 33350 | 125-GlyValGlnGluAsnGlyArgAsnAlaArgValAspGluArgGlyPhe-140 |
| g605 | |
| AMPHI Regions - AMPHI | |
| SEQ. ID. NO. 33351 | 13-ArgGlnIleTrpLysIleAlaAsp-20 |
| SEQ. ID. NO. 33352 | 38-ThrLeuPheTyrArgPheIleSerGluAsnPheThrAspTyrMetGln-53 |
| SEQ. ID. NO. 33353 | 107-LysLeuLysGluIlePheThrAlaIle-115 |
| SEQ. ID. NO. 33354 | 126-GlnGlyIleLysGlyLeuPheAspAspPheAsp-136 |
| SEQ. ID. NO. 33355 | 141-ArgLeuGlySerThr-145 |
| SEQ. ID. NO. 33356 | 155-AlaValLeuLysGlyValAlaGluLeu-163 |
| SEQ. ID. NO. 33357 | 178-AspAlaTyrGluTyrLeuIleSerAsn-186 |
| SEQ. ID. NO. 33358 | 188-AlaAlaAsnAlaGlyLys-193 |
| SEQ. ID. NO. 33359 | 204-ValSerLysLeuIleAlaArg-210 |
| SEQ. ID. NO. 33360 | 217-GluLysValAsnLysIleTyrAspPro-225 |
| SEQ. ID. NO. 33361 | 240-PheAspGluHisIle-244 |
| SEQ. ID. NO. 33362 | 291-AspSerLysProPheAspAlaValValSerAsn-301 |
| SEQ. ID. NO. 33363 | 341-HisAlaLeuAsnTyr-345 |
| SEQ. ID. NO. 33364 | 355-ValSerPheProGly-359 |
| SEQ. ID. NO. 33365 | 433-GluHisIleAlaGluIleValLysLeuPheAla-443 |
| SEQ. ID. NO. 33366 | 452-AlaGlnAsnAlaAlaGlnGlnThr-459 |
| SEQ. ID. NO. 33367 | 478-ThrArgGluValIleAspIle-484 |
| SEQ. ID. NO. 33368 | 489-AlaGluIleSerGluThrValAlaLysIleGluArgLeuArgArgGluIleAspGluValIleAlaGluIleGlu-513 |
| Antigenic Index - Jameson-Wolf | |
| SEQ. ID. NO. 33369 | 5-MetGlnGlnArgAlaGlnLeu-11 |
| SEQ. ID. NO. 33370 | 18-IleAlaAspGluValArgGlyAlaValAspGlyTrpAsp-30 |
| SEQ. ID. NO. 33371 | 44-IleSerGluAsnPheThrAspTyrMetGlnAlaGlyAspSerSerIleAsp-60 |
| SEQ. ID. NO. 33372 | 63-AlaMetProAspSer-67 |
| SEQ. ID. NO. 33373 | 71-ProGluIleLysAspAspAlaValLysVal-80 |
| SEQ. ID. NO. 33374 | 98-AlaHisGlnAsnGluGluLeuAsnThrLysLeuLysGlu-110 |
| SEQ. ID. NO. 33375 | 116-GluSerSerAlaSerGlyTyrProSerGluGlnGlyIleLysGlyLeuPheAspAspPheAspThrThrSerSerArgLeu-142 |
| SEQ. ID. NO. 33376 | 146-ValAlaAspLysAsnLysArgLeu-153 |
| SEQ. ID. NO. 33377 | 164-AspPheGlyAsnPheGluAspHisArgIle-173 |
| SEQ. ID. NO. 33378 | 190-AsnAlaGlyLysSerValGlyGlyPhePheThr-200 |
| SEQ. ID. NO. 33379 | 215-GlyGlnGluLysValAsnLysIleTyrAspProAlaCysGlySerGlySer-231 |
| SEQ. ID. NO. 33380 | 235-GlnAlaLysLysGlnPheAsp-241 |
| SEQ. ID. NO. 33381 | 253-GluIleAsnHisThrThrTyrAsn-260 |
| SEQ. ID. NO. 33382 | 280-LeuGlyAspThrLeuThrAsnProLysLeuLysAspSerLysProPheAspAla-297 |
| SEQ. ID. NO. 33383 | 309-IleGlySerAspAspProThrLeuIleAsnAspAspArgPheAlaPro-324 |
| SEQ. ID. NO. 33384 | 330-ProLysSerLysAlaAsp-335 |
| SEQ. ID. NO. 33385 | 345-TyrLeuSerGlyArgGlyArgAlaAla-353 |
| SEQ. ID. NO. 33386 | 362-TyrArgGlyGlyAlaGluGlnLysIleArg-371 |
| SEQ. ID. NO. 33387 | 403-LeuSerLysHisLysAspAsnThrAsp-411 |

TABLE 1-continued

| | |
|---|---|
| SEQ. ID. NO. 33388 | 419-GlyPhePheLysLysGluThrAsnAsnAsnValLeuThrGluGluHisIle-435 |
| SEQ. ID. NO. 33389 | 442-PheAlaAspLysAlaAspVal-448 |
| SEQ. ID. NO. 33390 | 458-GlnThrValLysAspAsnGlyTyr-465 |
| SEQ. ID. NO. 33391 | 473-ValGluAlaGluAspThrArgGluValIleAsp-483 |
| SEQ. ID. NO. 33392 | 490-GluIleSerGluThrValAlaLysIleGluArgLeuArgArgGluIleAspGluValIleAlaGluIleGluThr-514 |

Hydrophilic Regions - Hopp-Woods

| | |
|---|---|
| SEQ. ID. NO. 33393 | 18-IleAlaAspGluValArgGlyAlaValAsp-27 |
| SEQ. ID. NO. 33394 | 55-GlyAspSerSerIle-59 |
| SEQ. ID. NO. 33395 | 71-ProGluIleLysAspAspAlaValLysVal-80 |
| SEQ. ID. NO. 33396 | 98-AlaHisGlnAsnGluGluLeuAsnThrLysLeuLysGlu-110 |
| SEQ. ID. NO. 33397 | 131-LeuPheAspAspPheAspThrThrSerSerArgLeu-142 |
| SEQ. ID. NO. 33398 | 146-ValAlaAspLysAsnLysArgLeu-153 |
| SEQ. ID. NO. 33399 | 167-AsnPheGluAspHisArgIle-173 |
| SEQ. ID. NO. 33400 | 191-AlaGlyLysSerGlyGly-196 |
| SEQ. ID. NO. 33401 | 215-GlyGlnGluLysValAsnLysIleTyrAsp-224 |
| SEQ. ID. NO. 33402 | 235-GlnAlaLysLysGlnPheAsp-241 |
| SEQ. ID. NO. 33403 | 287-ProLysLeuLysAspSerLysProPhe-295 |
| SEQ. ID. NO. 33404 | 310-GlySerAspAspProThrLeuIleAsnAspAspArgPheAla-323 |
| SEQ. ID. NO. 33405 | 330-ProLysSerLysAlaAsp-335 |
| SEQ. ID. NO. 33406 | 348-GlyArgGlyArgAla-352 |
| SEQ. ID. NO. 33407 | 364-GlyGlyAlaGluGlnLysIleArg-371 |
| SEQ. ID. NO. 33408 | 404-SerLysHisLysAspAsnThrAsp-411 |
| SEQ. ID. NO. 33409 | 419-GlyPhePheLysLysGluThrAsn-426 |
| SEQ. ID. NO. 33410 | 430-LeuThrGluGluHisIle-435 |
| SEQ. ID. NO. 33411 | 442-PheAlaAspLysAlaAspVal-448 |
| SEQ. ID. NO. 33412 | 458-GlnThrValLysAspAsnGly-464 |
| SEQ. ID. NO. 33413 | 473-ValGluAlaGluAspThrArgGluValIleAsp-483 |
| SEQ. ID. NO. 33414 | 490-GluIleSerGluThrValAlaLysIleGluArgLeuArgArgGluIleAspGluValIleAlaGluIleGluThr-514 | g606
AMPHI Regions - AMPHI

| | |
|---|---|
| SEQ. ID. NO. 33415 | 72-LeuLeuAspHisMetThrArgAspGlu-80 |
| SEQ. ID. NO. 33416 | 90-AlaHisValGlyAsnGlyAsp-96 |
| SEQ. ID. NO. 33417 | 100-LeuThrLeuIleGlnGlyValValAsnThrPhe-110 |
| SEQ. ID. NO. 33418 | 116-ArgIleIleAlaAsn-120 |
| SEQ. ID. NO. 33419 | 139-SerMetValPheGlnIleLeuPheGlyPheLeuAlaSerLeuIleVal-154 |
| SEQ. ID. NO. 33420 | 171-LysLeuValGlyAlaProLysMetIleSerAlaLeuGlnArg-184 |
| SEQ. ID. NO. 33421 | 191-AspLeuProGluGluMetAsnAla-198 |

Antigenic Index - Jameson-Wolf

| | |
|---|---|
| SEQ. ID. NO. 33422 | 13-GluValIleAspThrProArgThrGluGluGluAla-24 |
| SEQ. ID. NO. 33423 | 31-GluAlaGlnAlaArgGlnTrpAsnLeuLysThrProGlu-43 |
| SEQ. ID. NO. 33424 | 48-HisSerProGluProAsnAla-54 |
| SEQ. ID. NO. 33425 | 57-ThrGlyAlaSerArgAsnSerSer-64 |
| SEQ. ID. NO. 33426 | 75-HisMetThrArgAspGluValGluAla-83 |
| SEQ. ID. NO. 33427 | 92-ValGlyAsnGlyAsp-96 |
| SEQ. ID. NO. 33428 | 122-IleAlaArgAsnAsnAspGlySerGlnSerGlnGlyThr-134 |
| SEQ. ID. NO. 33429 | 159-ArgGlnArgGluTyrArgAlaAspAlaGlyAla-169 |
| SEQ. ID. NO. 33430 | 182-LeuGlnArgLeuLysGlyAsnProValAspLeuProGluGluMetAsn-197 |
| SEQ. ID. NO. 33431 | 203-GlyAspThrArgAspSerLeuLeuSerThrHisProSerLeuAspAsnArgIleAlaArgLeuLysSer-225 |

Hydrophilic Regions - Hopp-Woods

| | |
|---|---|
| SEQ. ID. NO. 33432 | 13-GluValIleAspThrProArgThrGluGluGluAla-24 |
| SEQ. ID. NO. 33433 | 59-AlaSerArgAsnSer-63 |
| SEQ. ID. NO. 33434 | 75-HisMetThrArgAspGluValGluAla-83 |
| SEQ. ID. NO. 33435 | 124-ArgAsnAsnAspGlySerGlnSer-131 |
| SEQ. ID. NO. 33436 | 159-ArgGlnArgGluTyrArgAlaAspAlaGlyAla-169 |
| SEQ. ID. NO. 33437 | 183-GlnArgLeuLysGlyAsnPro-189 |
| SEQ. ID. NO. 33438 | 191-AspLeuProGluGluMetAsn-197 |
| SEQ. ID. NO. 33439 | 203-GlyAspThrArgAspSerLeu-209 |
| SEQ. ID. NO. 33440 | 214-ProSerLeuAspAsnArgIleAlaArgLeuLysSer-225 | g607
AMPHI Regions - AMPHI

| | |
|---|---|
| SEQ. ID. NO. 33441 | 15-LysGluIleArgLeuLeuThrAlaLeuAlaLeu-25 |
| SEQ. ID. NO. 33442 | 70-PheMetGlyIleMetAlaAlaLeuAsnProMetIleAlaGln-83 |
| SEQ. ID. NO. 33443 | 90-ThrGlyValAlaGlyGlu-95 |
| SEQ. ID. NO. 33444 | 104-GlyLeuIleLeuGlyIlePheGlyMetIleLeuMetTrpAlaAlaIleThrProPheArgAsnTrpLeuThrLeuSerAspTyrValGluGlyThrMet-136 |
| SEQ. ID. NO. 33445 | 151-MetValHisArgAlaLeuHisAlaTyrAlaSerSer-162 |
| SEQ. ID. NO. 33446 | 226-PhePheArgProPheGly-231 |
| SEQ. ID. NO. 33447 | 244-PheLysGlnIleTrpLysIleGlyAla-252 |
| SEQ. ID. NO. 33448 | 320-AlaArgTyrIleSerGlyValSerLeu-328 |
| SEQ. ID. NO. 33449 | 337-IleThrValLeuSerLeuVal-343 |
| SEQ. ID. NO. 33450 | 348-ProLeuAlaSerMetTyr-353 |
| SEQ. ID. NO. 33451 | 373-PheGlnProAlaAspPheThrGlnCysIleAlaSerTyrAla-386 |
| SEQ. ID. NO. 33452 | 424-TyrGlyPheTrpThrAlaLeuIleAla-432 |

Antigenic Index - Jameson-Wolf

| | |
|---|---|
| SEQ. ID. NO. 33453 | 4-AspLeuAspArgPheSer-9 |
| SEQ. ID. NO. 33454 | 47-GlyAlaGlyLysGluAspLeuAla-54 |
| SEQ. ID. NO. 33455 | 86-GlyAlaGlyLysThrGlyGluAlaGlyGluThrGlyArgGln-99 |
| SEQ. ID. NO. 33456 | 121-ProPheArgAsnTrp-125 |
| SEQ. ID. NO. 33457 | 128-LeuSerAspTyrValGluGlyThr-135 |
| SEQ. ID. NO. 33458 | 160-AlaSerSerLeuAsnArgProArgLeu-168 |
| SEQ. ID. NO. 33459 | 222-AlaLysGluLysPhePheArg-228 |

TABLE 1-continued

| | |
|---|---|
| SEQ. ID. NO. 33460 | 234-AlaLysPheGlyLysProAspTrp-241 |
| SEQ. ID. NO. 33461 | 311-SerLeuGlyArgArgGluPheSerArgAlaArgTyrIleSer-324 |
| SEQ. ID. NO. 33462 | 348-ProLeuAlaSerMetTyrAsnAspAspProAla-358 |
| SEQ. ID. NO. 33463 | 388-ArgGlyTyrLysValThrLys-394 |
| SEQ. ID. NO. 33464 | 452-LeuValLysSerHisLysAlaVal-459 |
| Hydrophilic Regions - Hopp-Woods | |
| SEQ. ID. NO. 33465 | 47-GlyAlaGlyLysGluAspLeuAla-54 |
| SEQ. ID. NO. 33466 | 89-LysThrGlyGluAlaGlyGluThrGlyArg-98 |
| SEQ. ID. NO. 33467 | 163-LeuAsnArgProArg-167 |
| SEQ. ID. NO. 33468 | 222-AlaLysGluLysPhePhe-227 |
| SEQ. ID. NO. 33469 | 312-LeuGlyArgArgGluPheSerArg-319 |
| SEQ. ID. NO. 33470 | 353-TyrAsnAspAspProAla-358 |
| SEQ. ID. NO. 33471 | 390-TyrLysValThrLys-394 |
| SEQ. ID. NO. 33472 | 452-LeuValLysSerHisLysAlaVal-459 |
| g608 | |
| AMPHI Regions - AMPHI | |
| SEQ. ID. NO. 33473 | 66-AlaIleArgLysIleLeuGln-72 |
| SEQ. ID. NO. 33474 | 93-ValLeuSerLeuLeu-97 |
| SEQ. ID. NO. 33475 | 103-ArgAlaSerAspGluLeuAlaArgIlePheGlyThr-114 |
| SEQ. ID. NO. 33476 | 124-AspIleGlyHisGlyIleLysGlnIleGlyArgAsnIleAlaGluGlnIleGlyGlyPheSerArgGluProGluSerAlaAsnThrGlyAsnGlu AlaLeuAlaAspCysLeuAspGluIleSerArgLeuArgAspGlyValGluArgLeuAsnGluArgLeuAspArgLeu-181 |
| Antigenic Index - Jameson-Wolf | |
| SEQ. ID. NO. 33477 | 13-LeuGlnSerProAspSerArgSerGluLeuThr-23 |
| SEQ. ID. NO. 33478 | 39-LeuAlaGlyArgIleThrGluAspGlyLeuLeuSerAlaGlyAsnGlyPheAlaAspThrGluIleThrPheArgAsnSerAlaIleArgLysIle LeuGlnGlyGlyGluProGlyAlaGlyAspIleArgLeuGluGly-85 |
| SEQ. ID. NO. 33479 | 98-GlySerLeuArgSerArgAlaSerAspGluLeuAla-109 |
| SEQ. ID. NO. 33480 | 116-AlaGlyIleGlySerArgAlaThrAspIle-125 |
| SEQ. ID. NO. 33481 | 130-LysGlnIleGlyArgAsnIleAla-137 |
| SEQ. ID. NO. 33482 | 140-IleGlyGlyPheSerArgGluProGluSerAlaAsnThrGlyAsnGluAlaLeuAlaAspCysLeuAspGluIleSerArgLeuArgAspGlyVal GluArgLeuAsnGluArgLeuAspArgLeuGluArgAspIleTrp-186 |
| Hydrophilic Regions - Hopp-Woods | |
| SEQ. ID. NO. 33483 | 15-SerProAspSerArgSerGluLeu-22 |
| SEQ. ID. NO. 33484 | 39-LeuAlaGlyArgIleThrGluAspGlyLeu-48 |
| SEQ. ID. NO. 33485 | 56-AlaAspThrGluIleThrPhe-62 |
| SEQ. ID. NO. 33486 | 65-SerAlaIleArgLysIleLeuGln-72 |
| SEQ. ID. NO. 33487 | 74-GlyGluProGlyAlaGlyAspIleArgLeuGluGly-85 |
| SEQ. ID. NO. 33488 | 100-LeuArgSerArgAlaSerAspGluLeuAla-109 |
| SEQ. ID. NO. 33489 | 118-IleGlySerArgAlaThrAsp-124 |
| SEQ. ID. NO. 33490 | 143-PheSerArgGluProGluSerAlaAsnThrGlyAsnGluAlaLeuAlaAspCysLeuAspGluIleSerArgLeuArgAspGlyValGluArgLeu AsnGluArgLeuAspArgLeuGluArgAspIleTrp-186 |
| g609 | |
| AMPHI Regions - AMPHI | |
| SEQ. ID. NO. 33491 | 15-ThrLeuAspAlaPheVal-20 |
| SEQ. ID. NO. 33492 | 30-HisHisIlePheHisGluPheArgValPheValGlyLeuPhe-43 |
| SEQ. ID. NO. 33493 | 52-PheGluGlnAlaValGlu-57 |
| SEQ. ID. NO. 33494 | 67-IleAspAsnPheLeu-71 |
| SEQ. ID. NO. 33495 | 114-ValAlaValCysProVal-119 |
| Antigenic Index - Jameson-Wolf | |
| SEQ. ID. NO. 33496 | 10-AlaLeuAspAspGluThrLeu-16 |
| SEQ. ID. NO. 33497 | 20-ValGlyAsnGlnArgSerSerAspIleAla-29 |
| SEQ. ID. NO. 33498 | 71-LeuAspThrAspPheGlyIleGlySerGlnAlaAspGlyAsnValArg-86 |
| SEQ. ID. NO. 33499 | 99-GlyThrArgAlaLysArgGlyTyrGlyAsnHisAspLeu-111 |
| SEQ. ID. NO. 33500 | 124-ArgGluAlaAspIle-128 |
| Hydrophilic Regions - Hopp-Woods | |
| SEQ. ID. NO. 33501 | 10-AlaLeuAspAspGluThrLeu-16 |
| SEQ. ID. NO. 33502 | 23-GlnArgSerSerAspIle-28 |
| SEQ. ID. NO. 33503 | 79-SerGlnAlaAspGlyAsnVal-85 |
| SEQ. ID. NO. 33504 | 100-ThrArgAlaLysArgGlyTyrGly-107 |
| SEQ. ID. NO. 33505 | 124-ArgGluAlaAspIle-128 |
| g610 | |
| AMPHI Regions - AMPHI | |
| SEQ. ID. NO. 33506 | 6-MetGlnPheProTyrArg-11 |
| SEQ. ID. NO. 33507 | 18-MetArgArgMetArgArg-23 |
| SEQ. ID. NO. 33508 | 97-ThrGlyArgAlaGlnGluAlaTyr-104 |
| SEQ. ID. NO. 33509 | 111-ProSerThrValArgAlaLeuArgGluArg-120 |
| SEQ. ID. NO. 33510 | 187-IleArgGluAlaLeuGlu-192 |
| SEQ. ID. NO. 33511 | 208-TyrAlaSerAlaPheTyrGlyProPheArgAsp-218 |
| SEQ. ID. NO. 33512 | 223-SerGlyAsnLeuGlyLysAlaAsp-230 |
| SEQ. ID. NO. 33513 | 268-LeuAspValValArgArgValLysAspGlu-277 |
| SEQ. ID. NO. 33514 | 296-AlaAlaValAlaAsn-300 |
| Antigenic Index - Jameson-Wolf | |
| SEQ. ID. NO. 33515 | 11-ArgAsnValProAlaSerArgMetArgArgMetArgArgAspAspPheSerArgArgLeuMetArg-32 |
| SEQ. ID. NO. 33516 | 34-HisMetLeuThrAlaAspAsp-40 |
| SEQ. ID. NO. 33517 | 50-GlyAlaAlaArgGluGluAspValProSerMetProGlyValLysArgGlnSerLeuAsp-69 |
| SEQ. ID. NO. 33518 | 75-AlaGluGluAlaValLys-80 |
| SEQ. ID. NO. 33519 | 93-ThrAlaAsnLysThrGlyArgAlaGlnGluAlaTyrAsnProGluGlyLeuVal-110 |
| SEQ. ID. NO. 33520 | 115-ArgAlaLeuArgGluArgPhePro-122 |
| SEQ. ID. NO. 33521 | 139-GlyGlnAspGlyLeuThrAspGluAsnGlyTyrValMetAsnAspGluThrVal-156 |
| SEQ. ID. NO. 33522 | 175-AlaProSerAspMetMetAspGlyArgIleGlyAlaIleArgGluAlaLeuGluAspAlaGlyHis-196 |
| SEQ. ID. NO. 33523 | 215-ProPheArgAspAlaValGlySerSerGlyAsnLeuGlyLysAlaAspLysLysThrTyrGlnMetAspProAlaAsnThrAspGluAlaLeuHis-246 |

TABLE 1-continued

| | |
|---|---|
| SEQ. ID. NO. 33524 | 250-LeuAspIleGlnGluGlyAlaAsp-257 |
| SEQ. ID. NO. 33525 | 270-ValValArgArgValLysAspGluPheGlyVal-280 |
| SEQ. ID. NO. 33526 | 302-TrpLeuAspGlyGlyLysValVal-309 |
| SEQ. ID. NO. 33527 | 317-LysArgAlaGlyAlaAspGly-323 |
| SEQ. ID. NO. 33528 | 331-GluAlaAlaLysMetLeuLysArg-338 |

Hydrophilic Regions - Hopp-Woods

| | |
|---|---|
| SEQ. ID. NO. 33529 | 14-ProAlaSerArgMetArgArgMetArgArgAspAspPheSerArgArgLeuMetArg-32 |
| SEQ. ID. NO. 33530 | 34-HisMetLeuThrAla-38 |
| SEQ. ID. NO. 33531 | 50-GlyAlaAlaArgGluGluAspValProSer-59 |
| SEQ. ID. NO. 33532 | 61-ProGlyValLysArgGlnSerLeuAsp-69 |
| SEQ. ID. NO. 33533 | 75-AlaGluGluAlaValLys-80 |
| SEQ. ID. NO. 33534 | 95-AsnLysThrGlyArgAlaGlnGluAlaTyrAsn-105 |
| SEQ. ID. NO. 33535 | 115-ArgAlaLeuArgGluArgPhePro-122 |
| SEQ. ID. NO. 33536 | 141-AspGlyLeuThrAspGluAsnGly-148 |
| SEQ. ID. NO. 33537 | 151-MetAsnAspGluThrVal-156 |
| SEQ. ID. NO. 33538 | 178-AspMetMetAspGlyArgIleGlyAlaIleArgGluAlaLeuGluAspAlaGly-195 |
| SEQ. ID. NO. 33539 | 216-PheArgAspAlaValGly-221 |
| SEQ. ID. NO. 33540 | 225-AsnLeuGlyLysAlaAspLysLysThrTyrGln-235 |
| SEQ. ID. NO. 33541 | 238-ProAlaAsnThrAspGluAlaLeuHis-246 |
| SEQ. ID. NO. 33542 | 250-LeuAspIleGlnGluGlyAlaAsp-257 |
| SEQ. ID. NO. 33543 | 270-ValValArgArgValLysAspGluPheGly-279 |
| SEQ. ID. NO. 33544 | 317-LysArgAlaGlyAla-321 |
| SEQ. ID. NO. 33545 | 331-GluAlaAlaLysMetLeuLysArg-338 | g611
AMPHI Regions - AMPHI

| | |
|---|---|
| SEQ. ID. NO. 33546 | 15-CysArgLeuPheGlyLysLeuSerLeu-23 |
| SEQ. ID. NO. 33547 | 26-ArgLeuLeuProGlyLeuCysArgGly-34 |
| SEQ. ID. NO. 33548 | 48-ArgSerValArgArgValIle-54 |
| SEQ. ID. NO. 33549 | 63-GlnValValAlaVal-67 |
| SEQ. ID. NO. 33550 | 104-ValPheIleGluAspPheVal-110 |
| SEQ. ID. NO. 33551 | 130-GlyPheLeuGlyAsnValLeuArgThr-138 |

Antigenic Index - Jameson-Wolf

| | |
|---|---|
| SEQ. ID. NO. 33552 | 1-MetProSerGluAsnGlyMetGlyLysArgGlnLeuAla-13 |
| SEQ. ID. NO. 33553 | 29-ProGlyLeuCysArgGlyGlyValCysArgGlyArgCys-41 |
| SEQ. ID. NO. 33554 | 45-PheProSerArgSerValArgArgValIlePheArgArgValArgIle-60 |
| SEQ. ID. NO. 33555 | 119-AsnProAlaAspPheArgVal-125 |
| SEQ. ID. NO. 33556 | 142-AlaProGlnGluAsp-146 |

Hydrophilic Regions - Hopp-Woods

| | |
|---|---|
| SEQ. ID. NO. 33557 | 1-MetProSerGluAsnGlyMetGlyLysArgGlnLeuAla-13 |
| SEQ. ID. NO. 33558 | 35-GlyValCysArgGlyArgCys-41 |
| SEQ. ID. NO. 33559 | 53-ValIlePheArgArgValArgIle-60 |
| SEQ. ID. NO. 33560 | 121-AlaAspPheArgVal-125 | g612
AMPHI Regions - AMPHI

| | |
|---|---|
| SEQ. ID. NO. 33561 | 6-AsnIleAlaLysLysLeuAlaGlyVal-14 |
| SEQ. ID. NO. 33562 | 57-LysAlaValGluLysCysAlaGluAsnValLeu-67 |
| SEQ. ID. NO. 33563 | 80-ValGlyAspPheProAsn-85 |

Antigenic Index - Jameson-Wolf

| | |
|---|---|
| SEQ. ID. NO. 33564 | 7-IleAlaLysLysLeuAlaGlyValAsp-15 |
| SEQ. ID. NO. 33565 | 17-IleAlaPheAspPheAspGly-23 |
| SEQ. ID. NO. 33566 | 27-AspPheGlyArgAspAspAlaValArgHisSerGlyVal-39 |
| SEQ. ID. NO. 33567 | 57-LysAlaValGluLysCysAlaGlu-64 |
| SEQ. ID. NO. 33568 | 98-HisHisArgAsnProTyrIleLysLeuAsnLysSerLysSerProAspIlePheArg-116 |
| SEQ. ID. NO. 33569 | 119-PheTyrGlyHisSerAsn-124 |

Hydrophilic Regions - Hopp-Woods

| | |
|---|---|
| SEQ. ID. NO. 33570 | 7-IleAlaLysLysLeuAlaGlyValAsp-15 |
| SEQ. ID. NO. 33571 | 28-PheGlyArgAspAspAlaValArg-35 |
| SEQ. ID. NO. 33572 | 57-LysAlaValGluLysCysAlaGlu-64 |
| SEQ. ID. NO. 33573 | 105-LysLeuAsnLysSerLysSerProAspIlePhe-115 | g613
AMPHI Regions - AMPHI

| | |
|---|---|
| SEQ. ID. NO. 33574 | 95-MetProArgMetArgSerProSerSerLeuMetSerProAla-108 |
| SEQ. ID. NO. 33575 | 140-SerSerValMetArgProAla-146 |
| SEQ. ID. NO. 33576 | 166-GluArgLeuSerGlyLeuCysArgIle-174 |
| SEQ. ID. NO. 33577 | 184-AspIlePheSerAspTrpGly-190 |

Antigenic Index - Jameson-Wolf

| | |
|---|---|
| SEQ. ID. NO. 33578 | 1-MetSerArgSerSerLeuSerArgArgSerLeuArgArgSerThrProSerArg-18 |
| SEQ. ID. NO. 33579 | 23-SerSerArgGlnSerAlaArgAla-30 |
| SEQ. ID. NO. 33580 | 36-AlaAspSerGlySerArgGluAsnProProIleCysSer-48 |
| SEQ. ID. NO. 33581 | 73-ProLysIleArgAlaAsnSerSerAspAlaArgGluArgArgLeuProSerArgAspSerThrAla-94 |
| SEQ. ID. NO. 33582 | 96-ProArgMetArgSerProSerSerLeu-104 |
| SEQ. ID. NO. 33583 | 107-ProAlaProGlySerProPro-113 |
| SEQ. ID. NO. 33584 | 130-AlaLysProPheProAlaGluSerLysProSerSerValMetArgProAlaSer-147 |
| SEQ. ID. NO. 33585 | 159-ProAlaLysGluValSerSerGluArgLeuSerGlyLeuCysArgIleArgArg-176 |
| SEQ. ID. NO. 33586 | 178-MetMetGlyArgArgAlaAspIlePheSerAspTrpGlyGlyGluCys-193 |

Hydrophilic Regions - Hopp-Woods

| | |
|---|---|
| SEQ. ID. NO. 33587 | 1-MetSerArgSerSerLeuSerArgArgSerLeuArgArgSerThrProSer-17 |
| SEQ. ID. NO. 33588 | 24-SerArgGlnSerAlaArgAla-30 |
| SEQ. ID. NO. 33589 | 38-SerGlySerArgGluAsnProPro-45 |
| SEQ. ID. NO. 33590 | 73-ProLysIleArgAlaAsnSerSerAspAlaArgGluArgArgLeuProSerArgAspSerThrAla-94 |

TABLE 1-continued

| | |
|---|---|
| SEQ. ID. NO. 33591 | 96-ProArgMetArgSerProSer-102 |
| SEQ. ID. NO. 33592 | 133-PheProAlaGluSerLysProSerSerValMetArg-144 |
| SEQ. ID. NO. 33593 | 159-ProAlaLysGluValSerSerGluArgLeuSerGly-170 |
| SEQ. ID. NO. 33594 | 172-CysArgIleArgArg-176 |
| SEQ. ID. NO. 33595 | 178-MetMetGlyArgArgAlaAspIle-185 |
| g614 | |
| AMPHI Regions - AMPHI | |
| SEQ. ID. NO. 33596 | 20-SerGlnPheIleArgGlnValAsnAsnGly-29 |
| SEQ. ID. NO. 33597 | 65-AsnLeuIleGlnThrLeuLeuAsn-72 |
| SEQ. ID. NO. 33598 | 90-AlaLeuPheTyrSerLeuLeuProValLeu-99 |
| SEQ. ID. NO. 33599 | 144-ValAlaGlyCysAspGluAlaLysGluGluValGlnGluIleValAspTyrLeuLysAlaProAsnArgTyrGlnSerLeu-170 |
| SEQ. ID. NO. 33600 | 210-AspPheValGluMetPheVal-216 |
| SEQ. ID. NO. 33601 | 222-ArgValArgAspMetPheGluGln-229 |
| SEQ. ID. NO. 33602 | 242-GluIleAspAlaValGlyArg-248 |
| SEQ. ID. NO. 33603 | 295-ProAlaLeuGlnArgProGlyArgPheAsp-304 |
| SEQ. ID. NO. 33604 | 333-SerValAspLeuLeuSerLeuAla-340 |
| SEQ. ID. NO. 33605 | 349-AlaLeuAspLeuAlaLysLeuVal-355 |
| Antigenic Index - Jameson-Wolf | |
| SEQ. ID. NO. 33606 | 7-LeuAspGlyLysLysGluAspAsnGlyGlnIleGlu-18 |
| SEQ. ID. NO. 33607 | 25-GlnValAsnAsnGlyGluValSerGly-33 |
| SEQ. ID. NO. 33608 | 45-LeuIleLysGlyGluArgThrAspLysSerThrPhe-56 |
| SEQ. ID. NO. 33609 | 59-AsnAlaProLeuAspAspAsnLeu-66 |
| SEQ. ID. NO. 33610 | 70-LeuLeuAsnLysAsnValArgValLysValThrProGluGluLysProSerAla-87 |
| SEQ. ID. NO. 33611 | 112-GlnAlaGlyGlyGlyGlyLysGlyGly-120 |
| SEQ. ID. NO. 33612 | 123-SerPheGlyLysSerArgAlaArgLeuLeuAspLysAspAlaAsnLys-138 |
| SEQ. ID. NO. 33613 | 145-AlaGlyCysAspGluAlaLysGluGluValGlnGlu-156 |
| SEQ. ID. NO. 33614 | 161-LeuLysAlaProAsnArgTyrGlnSerLeuGlyGlyArgValProArgGly-177 |
| SEQ. ID. NO. 33615 | 182-GlySerProGlyThrGlyLysThrLeuLeu-191 |
| SEQ. ID. NO. 33616 | 207-SerGlySerAspPhe-211 |
| SEQ. ID. NO. 33617 | 219-GlyAlaSerArgValArgAspMetPheGluGlnAlaLysLysAsnAla-234 |
| SEQ. ID. NO. 33618 | 241-AspGluIleAspAlaValGlyArgGlnArgGlyAlaGlyLeuGlyGlyGlyAsnAspGluArgGluGlnThrLeu-265 |
| SEQ. ID. NO. 33619 | 272-MetAspGlyPheGluSerAsnGln-279 |
| SEQ. ID. NO. 33620 | 287-ThrAsnArgProAspValLeuAspProAlaLeuGlnArgProGlyArgPheAspArg-305 |
| SEQ. ID. NO. 33621 | 311-LeuProAspIleArgGlyArgGluGlnXxx-320 |
| SEQ. ID. NO. 33622 | 323-ValHisSerLysLysValProLeuAspGluSerValAsp-335 |
| SEQ. ID. NO. 33623 | 341-ArgGlyThrProGlyPheSerGly-348 |
| SEQ. ID. NO. 33624 | 362-AlaGlyArgArgAsnLysValLysValAspGlnSerAspLeuLysThrProLysThrLysSer-382 |
| Hydrophilic Regions - Hopp-Woods | |
| SEQ. ID. NO. 33625 | 7-LeuAspGlyLysLysGluAspAsnGlyGln-16 |
| SEQ. ID. NO. 33626 | 26-ValAsnAsnGlyGluValSer-32 |
| SEQ. ID. NO. 33627 | 46-IleLysGlyGluArgThrAspLysSerThr-55 |
| SEQ. ID. NO. 33628 | 61-ProLeuAspAspAsnLeu-66 |
| SEQ. ID. NO. 33629 | 73-LysAsnValArgValLysValThrProGluGluLysProSerAla-87 |
| SEQ. ID. NO. 33630 | 115-GlyGlyGlyLysGlyGly-120 |
| SEQ. ID. NO. 33631 | 125-GlyLysSerArgAlaArgLeuLeuAspLysAspAlaAsnLys-138 |
| SEQ. ID. NO. 33632 | 145-AlaGlyCysAspGluAlaLysGluGluValGlnGlu-156 |
| SEQ. ID. NO. 33633 | 162-LysAlaProAsnArg-166 |
| SEQ. ID. NO. 33634 | 171-GlyGlyArgValProArg-176 |
| SEQ. ID. NO. 33635 | 221-SerArgValArgAspMetPheGluGlnAlaLysLysAsnAla-234 |
| SEQ. ID. NO. 33636 | 241-AspGluIleAspAlaValGlyArgGlnArgGlyAlaGly-253 |
| SEQ. ID. NO. 33637 | 256-GlyGlyAsnAspGluArgGluGlnThr-264 |
| SEQ. ID. NO. 33638 | 273-AspGlyPheGluSer-277 |
| SEQ. ID. NO. 33639 | 287-ThrAsnArgProAspValLeuAsp-294 |
| SEQ. ID. NO. 33640 | 296-AlaLeuGlnArgProGlyArgPheAspArg-305 |
| SEQ. ID. NO. 33641 | 312-ProAspIleArgGlyArgGluGlnXxx-320 |
| SEQ. ID. NO. 33642 | 324-HisSerLysLysValProLeuAspGluSerValAsp-335 |
| SEQ. ID. NO. 33643 | 362-AlaGlyArgArgAsnLysValLysValAspGlnSerAspLeuLysThrProLysThrLys-381 |
| g616 | |
| AMPHI Regions - AMPHI | |
| SEQ. ID. NO. 33644 | 6-LysMetValValGlyLeu-11 |
| SEQ. ID. NO. 33645 | 13-AsnProGlyLysGluTyrGlu-19 |
| SEQ. ID. NO. 33646 | 48-PheGlyGluValAlaArgAla-54 |
| SEQ. ID. NO. 33647 | 77-ValAlaAlaLeuAlaGlnPheTyrLys-85 |
| SEQ. ID. NO. 33648 | 115-GlyHisAsnGlyLeuLysAspIle-122 |
| SEQ. ID. NO. 33649 | 152-LeuAsnLysProSerAla-157 |
| SEQ. ID. NO. 33650 | 177-HisHisPheArgGlnMetGlyArg-184 |
| SEQ. ID. NO. 33651 | 203-ThrAlaPheSerArgPheProTyr-210 |
| SEQ. ID. NO. 33652 | 267-AlaProValGlnAsnLeuProAsnValAla-276 |
| SEQ. ID. NO. 33653 | 299-GlyGlyIleTyrSerLeuLeuPhe-306 |
| SEQ. ID. NO. 33654 | 319-PheAspLysAlaAla-323 |
| SEQ. ID. NO. 33655 | 363-GluCysAlaGlnAlaTrp-368 |
| SEQ. ID. NO. 33656 | 374-ThrGlySerLeuGlyAspValLeuAlaAspLeuThr-385 |
| Antigenic Index - Jameson-Wolf | |
| SEQ. ID. NO. 33657 | 11-LeuGlyAsnProGlyLysGluTyrGluGlnThrArgHisAsnAlaGlyPhe-27 |
| SEQ. ID. NO. 33658 | 39-AlaSerPheLysGluGluLysLysPhePhe-48 |
| SEQ. ID. NO. 33659 | 55-AlaLeuProAspGly-59 |
| SEQ. ID. NO. 33660 | 70-MetAsnArgSerGlyGlnAla-76 |
| SEQ. ID. NO. 33661 | 86-IleLysProGluGlu-90 |
| SEQ. ID. NO. 33662 | 96-AspGluLeuAspIleProCysGlyArgIleLysPhe-107 |
| SEQ. ID. NO. 33663 | 109-LeuGlyGlyGlyAsnGlyGlyHisAsnGlyLeuLysAspIleGlnAla-124 |

TABLE 1-continued

| | |
|---|---|
| SEQ. ID. NO. 33664 | 138-IleGlyHisProGlyAspArgAsnLeu-146 |
| SEQ. ID. NO. 33665 | 152-LeuAsnLysProSerAlaGluAlaProProAlaAsnArgArgCysArgArgGlnIleProAlaGlyArgThrArgHisHisPheArgGlnMetGly ArgGlyAsnAlaLeu-188 |
| SEQ. ID. NO. 33666 | 197-ArgLeuLysProPheGlnThrAla-204 |
| SEQ. ID. NO. 33667 | 209-ProTyrProAsnSerHisGluArgThrGlnAla-219 |
| SEQ. ID. NO. 33668 | 221-TyrProAsnGlyIleHisProArgHisArgArgAsnProArgPheProAla-237 |
| SEQ. ID. NO. 33669 | 239-ArgMetGlnHisArgArgSerThrValArgArgArgSerGlyThrMetAlaArgHisThrCysArgThrArgArgGlnIle-265 |
| SEQ. ID. NO. 33670 | 275-ValAlaGlyArgGlyGlyGlyMetLysLeuProArgAsnArgPhe-289 |
| SEQ. ID. NO. 33671 | 308-AlaAlaAspThrAlaProProPro-315 |
| SEQ. ID. NO. 33672 | 317-ProHisPheAspLysAlaAla-323 |
| SEQ. ID. NO. 33673 | 338-AlaPheLysThrGlyLysLeuProIlePro-347 |
| SEQ. ID. NO. 33674 | 371-AlaThrArgThrGlySerLeuGly-378 |
| SEQ. ID. NO. 33675 | 394-AlaArgSerAlaCysArgProAsp-401 |
| Hydrophilic Regions - Hopp-Woods | |
| SEQ. ID. NO. 33676 | 13-AsnProGlyLysGluTyrGluGlnThrArgHis-23 |
| SEQ. ID. NO. 33677 | 39-AlaSerPheLysGluGluLysLysPhePhe-48 |
| SEQ. ID. NO. 33678 | 86-IleLysProGluGlu-90 |
| SEQ. ID. NO. 33679 | 96-AspGluLeuAspIleProCysGlyArgIleLysPhe-107 |
| SEQ. ID. NO. 33680 | 117-AsnGlyLeuLysAspIleGlnAla-124 |
| SEQ. ID. NO. 33681 | 140-HisProGlyAspArgAsnLeu-146 |
| SEQ. ID. NO. 33682 | 155-ProSerAlaGluAlaProProAlaAsnArgArgCysArgArgGlnIleProAlaGlyArgThrArgHisHisPhe-179 |
| SEQ. ID. NO. 33683 | 212-AsnSerHisGluArgThrGln-218 |
| SEQ. ID. NO. 33684 | 225-IleHisProArgHisArgArgAsnProArg-234 |
| SEQ. ID. NO. 33685 | 240-MetGlnHisArgArgSerThrValArgArgArgSerGlyThrMet-254 |
| SEQ. ID. NO. 33686 | 257-HisThrCysArgThrArgArgGlnIle-265 |
| SEQ. ID. NO. 33687 | 276-AlaGlyArgGlyGlyGly-281 |
| SEQ. ID. NO. 33688 | 283-LysLeuProArgAsnArgPhe-289 |
| SEQ. ID. NO. 33689 | 308-AlaAlaAspThrAla-312 |
| SEQ. ID. NO. 33690 | 318-HisPheAspLysAlaAla-323 |
| SEQ. ID. NO. 33691 | 338-AlaPheLysThrGlyLys-343 |
| SEQ. ID. NO. 33692 | 396-SerAlaCysArgProAsp-401 |
| g619 | |
| AMPHI Regions - AMPHI | |
| SEQ. ID. NO. 33693 | 50-LysLeuAlaAlaLeuLeu-55 |
| SEQ. ID. NO. 33694 | 66-GlnLeuPheGlnThrLeuThrAsn-73 |
| SEQ. ID. NO. 33695 | 146-GlyValIlePheGlyIleLeuPheArgSerLeuSerSerLeuLeuSerArg-162 |
| SEQ. ID. NO. 33696 | 165-AspProGluGluPhe-169 |
| SEQ. ID. NO. 33697 | 175-AsnMetPheAlaGlyPheAsn-181 |
| SEQ. ID. NO. 33698 | 246-AlaValValGlyProValSerPhePheGlyLeuLeuAlaAlaSerLeuAlaAsnHisPheSer-266 |
| SEQ. ID. NO. 33699 | 303-LeuSerValValValGluPhe-309 |
| Antigenic Index - Jameson-Wolf | |
| SEQ. ID. NO. 33700 | 1-MetProSerGluLysAsnIle-7 |
| SEQ. ID. NO. 33701 | 12-GlySerSerArgProLeuArg-18 |
| SEQ. ID. NO. 33702 | 35-AsnValLysGlyAspTrpAsp-41 |
| SEQ. ID. NO. 33703 | 132-IleArgGlnGlyGlyArgAspLeuPro-140 |
| SEQ. ID. NO. 33704 | 163-MetIleAspProGluGluPheThr-170 |
| SEQ. ID. NO. 33705 | 182-ThrValArgSerGluLeu-187 |
| SEQ. ID. NO. 33706 | 205-GluArgTyrArgSerAspValHisLeuLeuGlyArgAspGlnAlaVal-220 |
| SEQ. ID. NO. 33707 | 265-PheSerProSerValArgHisSerVal-273 |
| Hydrophilic Regions - Hopp-Woods | |
| SEQ. ID. NO. 33708 | 1-MetProSerGluLysAsnIle-7 |
| SEQ. ID. NO. 33709 | 13-SerSerArgProLeu-17 |
| SEQ. ID. NO. 33710 | 134-GlnGlyGlyArgAspLeuPro-140 |
| SEQ. ID. NO. 33711 | 163-MetIleAspProGluGluPheThr-170 |
| SEQ. ID. NO. 33712 | 183-ValArgSerGluLeu-187 |
| SEQ. ID. NO. 33713 | 205-GluArgTyrArgSerAspVal-211 |
| SEQ. ID. NO. 33714 | 213-LeuLeuGlyArgAspGlnAla-219 |
| SEQ. ID. NO. 33715 | 269-ValArgHisSerVal-273 |
| g620 | |
| AMPHI Regions - AMPHI | |
| SEQ. ID. NO. 33716 | 8-IleValAlaValPheAlaLeuSerAla-16 |
| SEQ. ID. NO. 33717 | 31-IleSerAspArgSerVal-36 |
| SEQ. ID. NO. 33718 | 69-ValLysGlnMetPheGlyTyrThrLysLeuProGluGluProLysGlyIleArgValIleTyrValThrAspMetGlyAsnValThrAspTrpThr-100 |
| SEQ. ID. NO. 33719 | 139-GlnAlaGluLysPhe-143 |
| Antigenic Index - Jameson-Wolf | |
| SEQ. ID. NO. 33720 | 16-AlaCysArgGlnAlaGluGluAlaProProProLeuProArgGlnIleSerAspArgSerValGlyHisTyrCysSerMetAsnLeuThrGluHis AsnGlyProLysAla-52 |
| SEQ. ID. NO. 33721 | 56-LeuAsnGlyLysProAspGlnProVal-64 |
| SEQ. ID. NO. 33722 | 75-TyrThrLysLeuProGluGluProLysGlyIle-85 |
| SEQ. ID. NO. 33723 | 92-AspMetGlyAsnValThrAspTrpThrAsnProAsnAlaAspThrGluTrpIleAspAlaLysLys-113 |
| SEQ. ID. NO. 33724 | 125-GlyMetGlyAlaGluAspAlaLeuProPheGlyAsnLysGluGlnAlaGluLysPheAlaLysAspLysGlyGlyLysValValGly-153 |
| SEQ. ID. NO. 33725 | 155-AspAspMetProAsp-159 |
| Hydrophilic Regions - Hopp-Woods | |
| SEQ. ID. NO. 33726 | 18-ArgGlnAlaGluGluAlaProProProLeu-27 |
| SEQ. ID. NO. 33727 | 30-GlnIleSerAspArgSerVal-36 |
| SEQ. ID. NO. 33728 | 46-GluHisAsnGlyProLys-51 |
| SEQ. ID. NO. 33729 | 58-GlyLysProAspGln-62 |
| SEQ. ID. NO. 33730 | 77-LysLeuProGluGluProLysGlyIle-85 |
| SEQ. ID. NO. 33731 | 103-AsnAlaAspThrGluTrpIleAspAlaLysLys-113 |
| SEQ. ID. NO. 33732 | 127-GlyAlaGluAspAlaLeu-132 |

TABLE 1-continued

| | |
|---|---|
| SEQ. ID. NO. 33733 | 135-GlyAsnLysGluGlnAlaGluLysPheAlaLysAspLysGlyGlyLys-150 |
| SEQ. ID. NO. 33734 | 155-AspAspMetProAsp-159 |
| g622 | |
| AMPHI Regions - AMPHI | |
| SEQ. ID. NO. 33735 | 28-LeuProGluAlaValArgAsnLeuAlaArg-37 |
| SEQ. ID. NO. 33736 | 62-GluGluIleIleArgTrpLeuAlaAsp-70 |
| SEQ. ID. NO. 33737 | 112-IleLeuGlyGlnIleLysAspAlaValArgAlaAlaGlnGlu-125 |
| SEQ. ID. NO. 33738 | 132-LysLeuAsnAlaLeuPheGlnLys-139 |
| SEQ. ID. NO. 33739 | 142-SerValAlaLysGluVal-147 |
| SEQ. ID. NO. 33740 | 169-GluGlnIlePheProAspIleGlyAsp-177 |
| SEQ. ID. NO. 33741 | 187-GluMetIleGluLeuValAla-193 |
| SEQ. ID. NO. 33742 | 214-AlaGlnGluLeuCysAspLys-220 |
| SEQ. ID. NO. 33743 | 232-AspLeuProAlaIleLeuHis-238 |
| SEQ. ID. NO. 33744 | 288-AspLeuAsnAspAla-292 |
| SEQ. ID. NO. 33745 | 297-ValAspAspMetValAsnIleValGlnSerGly-307 |
| SEQ. ID. NO. 33746 | 324-GluLysValAlaGluPheValArgGlnGln-333 |
| SEQ. ID. NO. 33747 | 345-LeuArgAspGluGlyGluLys-351 |
| SEQ. ID. NO. 33748 | 354-LysGlnValLeuGluAsnAlaMetLysGlnLeuAlaLys-366 |
| SEQ. ID. NO. 33749 | 372-GluValLeuGluArgLeuSerValGlnLeuThr-382 |
| SEQ. ID. NO. 33750 | 384-LysLeuLeuHisSerProThrGlnThrLeuAsnLysAlaGlyGlu-398 |
| Antigenic Index - Jameson-Wolf | |
| SEQ. ID. NO. 33751 | 16-SerIleArgGluLysLeuAla-22 |
| SEQ. ID. NO. 33752 | 30-GluAlaValArgAsnLeuAlaArgSerAsnAlaAla-41 |
| SEQ. ID. NO. 33753 | 49-ThrCysAsnArgThrGlu-54 |
| SEQ. ID. NO. 33754 | 57-CysValGlyAspSerGluIleIle-65 |
| SEQ. ID. NO. 33755 | 75-ProIleGluGluIleArgProTyr-82 |
| SEQ. ID. NO. 33756 | 87-AspMetGlnGluThrValArgHis-94 |
| SEQ. ID. NO. 33757 | 115-GlnIleLysAspAlaValArgAlaAlaGlnGluGlnGluSerMetGlyAla-131 |
| SEQ. ID. NO. 33758 | 142-SerValAlaLysGluValArgThrAspThrAlaValGlyGluAsnSerVal-158 |
| SEQ. ID. NO. 33759 | 174-AspIleGlyAspLeuAsn-179 |
| SEQ. ID. NO. 33760 | 199-LysAsnProArgLeu-203 |
| SEQ. ID. NO. 33761 | 210-ThrLeuAlaArgAlaGlnGluLeuCysAspLysLeuGlyValAsnAlaGlu-226 |
| SEQ. ID. NO. 33762 | 257-GlyMetValGluArgAlaLeuLysGlnArgGlnSer-268 |
| SEQ. ID. NO. 33763 | 277-AlaValProArgAspIleGluAlaGluValGlyAspLeuAsnAsp-291 |
| SEQ. ID. NO. 33764 | 305-GlnSerGlyLysGluAlaArgGlnLysAlaAlaAlaAla-317 |
| SEQ. ID. NO. 33765 | 321-LeuValSerGluLysValAlaGluPheValArgGlnGlnGlnGlyArgGlnSerVal-339 |
| SEQ. ID. NO. 33766 | 343-LysAlaLeuArgAspGluGlyGluLysAlaArgLysGlnValLeu-357 |
| SEQ. ID. NO. 33767 | 368-AlaThrAlaGluGluValLeuGlu-375 |
| SEQ. ID. NO. 33768 | 381-LeuThrAsnLysLeuLeuHisSerProThrGlnThrLeuAsnLysAlaGlyGluGluAspLysAspLeuVal-404 |
| Hydrophilic Regions - Hopp-Woods | |
| SEQ. ID. NO. 33769 | 16-SerIleArgGluLysLeuAla-22 |
| SEQ. ID. NO. 33770 | 30-GluAlaValArgAsnLeuAlaArgSerAsnAlaAla-41 |
| SEQ. ID. NO. 33771 | 59-GlyAspSerGluGluIleIle-65 |
| SEQ. ID. NO. 33772 | 75-ProIleGluGluIleArg-80 |
| SEQ. ID. NO. 33773 | 87-AspMetGlnGluThrValArgHis-94 |
| SEQ. ID. NO. 33774 | 115-GlnIleLysAspAlaValArgAlaAlaAlaGlnGluGlnGluSerMetGly-130 |
| SEQ. ID. NO. 33775 | 142-SerValAlaLysGluValArgThrAspThrAlaValGly-154 |
| SEQ. ID. NO. 33776 | 210-ThrLeuAlaArgAlaGlnGluLeuCysAsp-219 |
| SEQ. ID. NO. 33777 | 257-GlyMetValGluArgAlaLeuLysGlnArgGlnSer-268 |
| SEQ. ID. NO. 33778 | 277-AlaValProArgAspIleGluAlaGluValGlyAspLeuAsn-290 |
| SEQ. ID. NO. 33779 | 305-GlnSerGlyLysGluAlaArgGlnLysAlaAlaAlaAla-317 |
| SEQ. ID. NO. 33780 | 321-LeuValSerGluLysValAlaGluPheValArg-331 |
| SEQ. ID. NO. 33781 | 333-GlnGlnGlyArgGlnSer-338 |
| SEQ. ID. NO. 33782 | 343-LysAlaLeuArgAspGluGlyGluLysAlaArgLysGlnValLeu-357 |
| SEQ. ID. NO. 33783 | 368-AlaThrAlaGluGluValLeuGlu-375 |
| SEQ. ID. NO. 33784 | 392-ThrLeuAsnLysAlaGlyGluGluAspLysAspLeuVal-404 |
| g624 | |
| AMPHI Regions - AMPHI | |
| SEQ. ID. NO. 33785 | 17-GlyIleIleGlyIlePheLeuPro-24 |
| SEQ. ID. NO. 33786 | 45-ArgPheHisArgTrpLeuHis-51 |
| SEQ. ID. NO. 33787 | 58-ProMetValHisAsn-62 |
| SEQ. ID. NO. 33788 | 102-SerSerValPheCys-106 |
| Antigenic Index - Jameson-Wolf | |
| SEQ. ID. NO. 33789 | 41-LysAlaSerProArgPheHisArgTrp-49 |
| SEQ. ID. NO. 33790 | 51-HisArgHisArgTyrPheGlyProMet-59 |
| SEQ. ID. NO. 33791 | 63-TrpGluGlnAsnGlyAlaValProArgLysAlaLys-74 |
| SEQ. ID. NO. 33792 | 114-TrpHisArgProGluSer-119 |
| Hydrophilic Regions - Hopp-Woods | |
| SEQ. ID. NO. 33793 | 67-GlyAlaValProArgLysAlaLys-74 |
| SEQ. ID. NO. 33794 | 115-HisArgProGluSer-119 |
| g625 | |
| AMPHI Regions - AMPHI | |
| SEQ. ID. NO. 33795 | 14-ThrArgArgValArgSerTrpLeuAla-22 |
| SEQ. ID. NO. 33796 | 24-SerSerGlyArgIleIleSerIleAlaAla-33 |
| SEQ. ID. NO. 33797 | 64-LysMetProProGluMetValTyrArgAla-73 |
| SEQ. ID. NO. 33798 | 78-MetLysGlyIleTyrSer-83 |
| Antigenic Index - Jameson-Wolf | |
| SEQ. ID. NO. 33799 | 5-ArgLysMetLysLysMetThrMetCysThrArgArgValArg-18 |
| SEQ. ID. NO. 33800 | 57-ProPheLysSerProGlnThrLysMetProPro-67 |
| SEQ. ID. NO. 33801 | 73-AlaSerSerSerArgMetLysGly-80 |

TABLE 1-continued

| | |
|---|---|
| SEQ. ID. NO. 33802 | 96-AspAlaProLysThrLysLeuAsnGlyMetArgLysSerAsnValGln-111 |

Hydrophilic Regions - Hopp-Woods
| | |
|---|---|
| SEQ. ID. NO. 33803 | 5-ArgLysMetLysLysMetThrMetCysThrArgArgValArg-18 |
| SEQ. ID. NO. 33804 | 60-SerProGlnThrLysMetProPro-67 |
| SEQ. ID. NO. 33805 | 74-SerSerSerArgMetLysGly-80 |
| SEQ. ID. NO. 33806 | 96-AspAlaProLysThrLysLeuAsnGlyMetArgLysSerAsnValGln-111 | g627
AMPHI Regions - AMPHI
| | |
|---|---|
| SEQ. ID. NO. 33807 | 21-LeuGlnAsnLeuVal-25 |
| SEQ. ID. NO. 33808 | 56-IleAlaGluValGlyLysLeuPheLeuGlyIlePheIleThrIlePheProValLeuSerIleLeuLysAlaGlyGluAlaGlyAlaLeuGlyGlyValValSerLeuValHisAspThrAlaGlyHisPro-99 |
| SEQ. ID. NO. 33809 | 109-GlyIleLeuSerAlaPheLeuAspAsnAla-118 |
| SEQ. ID. NO. 33810 | 153-PheMetGlyAlaLeuThrTyrIleGlyAsnAlaProAsnPheMetValLys-169 |
| SEQ. ID. NO. 33811 | 180-ProThrPhePheArgTyr-185 |

Antigenic Index - Jameson-Wolf
| | |
|---|---|
| SEQ. ID. NO. 33812 | 3-GlyLeuTrpLysProGluHisProGlyPhe-12 |
| SEQ. ID. NO. 33813 | 41-ThrProLysGlnValArgAlaGlyAsnGluPheAsnPhe-53 |
| SEQ. ID. NO. 33814 | 94-AspThrAlaGlyHis-98 |
| SEQ. ID. NO. 33815 | 128-AlaGlyGlyAspAla-132 |
| SEQ. ID. NO. 33816 | 170-AlaIleAlaGluGlnArgGlyValPro-178 |

Hydrophilic Regions - Hopp-Woods
| | |
|---|---|
| SEQ. ID. NO. 33817 | 5-TrpLysProGluHisProGly-11 |
| SEQ. ID. NO. 33818 | 43-LysGlnValArgAlaGlyAsn-49 |
| SEQ. ID. NO. 33819 | 170-AlaIleAlaGluGlnArgGlyVal-177 | g628
AMPHI Regions - AMPHI
| | |
|---|---|
| SEQ. ID. NO. 33820 | 10-CysGlyProProAsnSerCysValSerIleLeuAlaAlaPhe-23 |
| SEQ. ID. NO. 33821 | 25-AspGlyThrSerAlaProAlaAla-32 |
| SEQ. ID. NO. 33822 | 34-HisThrTrpIleLeuArgSer-40 |

Antigenic Index - Jameson-Wolf
| | |
|---|---|
| SEQ. ID. NO. 33823 | 6-LysProAlaGlyCysGlyProProAsnSer-15 |
| SEQ. ID. NO. 33824 | 23-PheSerAspGlyThrSerAla-29 |
| SEQ. ID. NO. 33825 | 40-SerValArgArgLeuAsnThrAsnArgProArgLeuLysSerSerAla-55 |
| SEQ. ID. NO. 33826 | 77-MetAlaAsnGlySerAlaSerThr-84 |
| SEQ. ID. NO. 33827 | 91-GlyArgValArgSerAlaValHisLysProAspIleArgLeuArgArg-106 |
| SEQ. ID. NO. 33828 | 115-SerAlaSerGlyThr-119 |

Hydrophilic Regions - Hopp-Woods
| | |
|---|---|
| SEQ. ID. NO. 33829 | 40-SerValArgArgLeuAsnThrAsnArgProArgLeuLysSerSerAla-55 |
| SEQ. ID. NO. 33830 | 91-GlyArgValArgSerAlaValHisLysProAspIleArgLeuArgArg-106 | g629
AMPHI Regions - AMPHI
| | |
|---|---|
| SEQ. ID. NO. 33831 | 32-ArgTrpSerAspValPheSer-38 |
| SEQ. ID. NO. 33832 | 48-IleSerArgLeuProArgThrPhe-55 |
| SEQ. ID. NO. 33833 | 116-ValAlaAlaLeuIleGlyMetLeu-123 |
| SEQ. ID. NO. 33834 | 145-XxxIlePheGlyGlyValValGluAlaValAlaThrPhe-157 |
| SEQ. ID. NO. 33835 | 164-MetLeuGlnMetLeuGlyValTrpGlnGlnGlyAsp-175 |
| SEQ. ID. NO. 33836 | 206-IleLeuGlyLeuGlyGlu-211 |
| SEQ. ID. NO. 33837 | 253-ValProAsnIleValSerArgLeuMetGlyAspArgLeuArgGlnSer-268 |
| SEQ. ID. NO. 33838 | 285-IleIleGlyArgMet-289 |
| SEQ. ID. NO. 33839 | 300-ThrValPheGlyValLeu-305 |

Antigenic Index - Jameson-Wolf
| | |
|---|---|
| SEQ. ID. NO. 33840 | 38-SerLeuSerAspSerGln-43 |
| SEQ. ID. NO. 33841 | 50-ArgLeuProArgThr-54 |
| SEQ. ID. NO. 33842 | 77-AsnArgPheValGluProSerMetAlaGlyAlaGlyGln-89 |
| SEQ. ID. NO. 33843 | 130-ArgArgLeuProProThrAla-136 |
| SEQ. ID. NO. 33844 | 260-LeuMetGlyAspArgLeuArgGlnSer-268 |

Hydrophilic Regions - Hopp-Woods
| | |
|---|---|
| SEQ. ID. NO. 33845 | 260-LeuMetGlyAspArgLeuArgGln-267 | g630
AMPHI Regions - AMPHI
| | |
|---|---|
| SEQ. ID. NO. 33846 | 30-ProAspLeuLeuGlnGln-35 |
| SEQ. ID. NO. 33847 | 81-GlyGlyPheTrpGluValLeuPheAla-89 |
| SEQ. ID. NO. 33848 | 135-PheGlyGlyThrGlyLysAsnPhe-142 |
| SEQ. ID. NO. 33849 | 169-AlaValAspGlyTyrSerGlyAlaThrAlaLeuAlaGlnTrp-182 |
| SEQ. ID. NO. 33850 | 187-AlaAspGlyLeuLysAsnAlaVal-194 |
| SEQ. ID. NO. 33851 | 203-AspAlaPheIleGlyLysLeuProGlySerIleGlyGluValSer-217 |
| SEQ. ID. NO. 33852 | 230-PheAlaArgIleAlaSerTrpArgIleIleAlaGlyValMet-243 |
| SEQ. ID. NO. 33853 | 247-IleAlaMetSerSerLeuIleAsnPhe-255 |

Antigenic Index - Jameson-Wolf
| | |
|---|---|
| SEQ. ID. NO. 33854 | 37-IleAlaHisAspGlyAsnTyr-43 |
| SEQ. ID. NO. 33855 | 53-MetSerProGluAla-57 |
| SEQ. ID. NO. 33856 | 90-SerValArgLysHisGluIleAsnGlu-98 |
| SEQ. ID. NO. 33857 | 133-GluValPheGlyGlyThrGlyLysAsnPheMet-143 |
| SEQ. ID. NO. 33858 | 157-TyrProAlaAsnLeuSerGlyAspAla-165 |
| SEQ. ID. NO. 33859 | 186-GlyAlaAspGlyLeuLys-191 |
| SEQ. ID. NO. 33860 | 209-LeuProGlySerIleGly-214 |
| SEQ. ID. NO. 33861 | 257-GlySerAspThrLysAla-262 |
| SEQ. ID. NO. 33862 | 271-GlyThrTrpTrpLysAspAspTyrHisSerLeu-281 |

Hydrophilic Regions - Hopp-Woods
| | |
|---|---|
| SEQ. ID. NO. 33863 | 90-SerValArgLysHisGluIleAsn-97 |

TABLE 1-continued

SEQ. ID. NO. 33864   258-SerAspThrLysAla-262
g638
AMPHI Regions - AMPHI
SEQ. ID. NO. 33865   17-LeuAlaArgPheValAspAsnIle-24
SEQ. ID. NO. 33866   30-IleValAspIleValGlu-35
SEQ. ID. NO. 33867   46-AspIleValGluHisPheGluProPheGlyLys-56
SEQ. ID. NO. 33868   108-ProPheGlyAsnValValAlaAsp-115
SEQ. ID. NO. 33869   118-ArgAlaGlyArgValPro-123
SEQ. ID. NO. 33870   148-ArgIleGlyArgThrMetLysValTyrAlaGluArgIleIle-161
SEQ. ID. NO. 33871   198-GluArgTyrValArgArgValTyrGly-206
SEQ. ID. NO. 33872   212-LeuValProPheAspGlyCysGlyThrValGlyArg-223
SEQ. ID. NO. 33873   242-SerGlnPheAspArgIleAlaArgProGlyAlaGlyLysAsnPheGlyLysValValLeuArgGlyAsnVal-265
SEQ. ID. NO. 33874   304-TrpProAsnLysIleLysHisHis-311
Antigenic Index - Jameson-Wolf
SEQ. ID. NO. 33875   13-GlyLysAsnAlaLeu-17
SEQ. ID. NO. 33876   43-AlaAspGlyAspIle-47
SEQ. ID. NO. 33877   52-GluProPheGlyLys-56
SEQ. ID. NO. 33878   81-ValAspGlyGluThrGlnVal-87
SEQ. ID. NO. 33879   99-AlaGlyIleGlyLysAsnAlaVal-106
SEQ. ID. NO. 33880   113-ValAlaAspAspLeuArgAlaGlyArgValProAsnGlyAsn-126
SEQ. ID. NO. 33881   148-ArgIleGlyArgThrMet-153
SEQ. ID. NO. 33882   169-GlnGlyAlaArgGlyGlyPhe-175
SEQ. ID. NO. 33883   188-HisThrGlyThrGlyAsnGlyGlnValAlaGluArgTyrValArg-202
SEQ. ID. NO. 33884   216-AspGlyCysGlyThrValGlyArgProPheAsnArgAsnArgPheValAsp-232
SEQ. ID. NO. 33885   240-AlaGlySerGlnPheAspArgIleAlaArgProGlyAlaGlyLysAsnPheGly-257
SEQ. ID. NO. 33886   260-ValLeuArgGlyAsnValAspAspGlyCysArgCysArgLeuLysAsnAlaAlaGlyGlyLysTyrGlnHis-283
SEQ. ID. NO. 33887   285-LeuGlnProTyrThrGluArgGlyCys-293
SEQ. ID. NO. 33888   304-TrpProAsnLysIleLysHisHisSerAsn-313
SEQ. ID. NO. 33889   319-AlaLysProProGluThrValArg-326
Hydrophilic Regions - Hopp-Woods
SEQ. ID. NO. 33890   43-AlaAspGlyAspIle-47
SEQ. ID. NO. 33891   81-ValAspGlyGluThrGlnVal-87
SEQ. ID. NO. 33892   113-ValAlaAspAspLeuArgAlaGlyArgValProAsn-124
SEQ. ID. NO. 33893   148-ArgIleGlyArgThrMet-153
SEQ. ID. NO. 33894   195-GlnValAlaGluArgTyrValArg-202
SEQ. ID. NO. 33895   243-GlnPheAspArgIleAlaArgProGlyAlaGlyLysAsnPheGly-257
SEQ. ID. NO. 33896   263-GlyAsnValAspAspGlyCysArgCysArgLeuLysAsnAlaAla-277
SEQ. ID. NO. 33897   288-TyrThrGluArgGlyCys-293
SEQ. ID. NO. 33898   320-LysProProGluThrValArg-326
g639-1
AMPHI Regions - AMPHI
SEQ. ID. NO. 33899   95-TyrLysAsnAsnArg-99
SEQ. ID. NO. 33900   137-LeuLysValPheAspAsnIle-143
SEQ. ID. NO. 33901   156-ValAsnTyrSerAspIleHisAspAsnIleIleAsnLysAla-169
SEQ. ID. NO. 33902   268-AlaProValSerArg-272
SEQ. ID. NO. 33903   289-GlnPheProAlaValLeuProGly-296
Antigenic Index - Jameson-Wolf
SEQ. ID. NO. 33904   25-AsnIlePheAspAsnSerPhe-31
SEQ. ID. NO. 33905   41-AlaMetValArgGluAsnLysIleValGly-50
SEQ. ID. NO. 33906   52-AlaThrLeuArgValAsnGluArgGlyAsnGly-62
SEQ. ID. NO. 33907   75-GlyAsnAspIleSerLysGlyArgAspGlyIlePheSerAsnThrSerThrHisAsnThrTyrLysAsnAsnArgPheSerAsp-102
SEQ. ID. NO. 33908   111-TyrThrAsnAspSerGluValSerGly-119
SEQ. ID. NO. 33909   135-GluArgLeuLysVal-139
SEQ. ID. NO. 33910   145-ValGlySerArgAspGlyIle-151
SEQ. ID. NO. 33911   159-SerAspIleHisAspAsnIleIleAsnLysAlaGlyLys-171
SEQ. ID. NO. 33912   178-AlaAsnTyrAspLysLeuSerAlaAsnHis-187
SEQ. ID. NO. 33913   202-GluGlyThrSerLeuHisAspAsnSer-210
SEQ. ID. NO. 33914   212-IleAsnAsnGlySerGlnValLysTyrValSer-222
SEQ. ID. NO. 33915   227-AspTrpSerGluGlyGlyHisGlyAsnTyrTrpSerAspAsnSerProPhe-243
SEQ. ID. NO. 33916   245-LeuAsnGlyAspGlyPheGlyAspSerAlaTyrArgProAspGlyIleIle-261
SEQ. ID. NO. 33917   296-GlyGlyValValAspSerLysProLeuMetLysProTyrAlaProLysIleGlnThr-314
SEQ. ID. NO. 33918   317-GlnAlaMetLysAspGluLeuLeuLysGluAlaGluThrArgGlnSerGluArgGlyArgAlaGluAsnGlySerLeuAsn-343
Hydrophilic Regions - Hopp-Woods
SEQ. ID. NO. 33919   41-AlaMetValArgGluAsnLysIleValGly-50
SEQ. ID. NO. 33920   52-AlaThrLeuArgValAsnGluArgGlyAsn-61
SEQ. ID. NO. 33921   77-AspIleSerLysGlyArgAspGlyIle-85
SEQ. ID. NO. 33922   95-TyrLysAsnAsnArgPheSerAsp-102
SEQ. ID. NO. 33923   113-AsnAspSerGluValSerGly-119
SEQ. ID. NO. 33924   135-GluArgLeuLysVal-139
SEQ. ID. NO. 33925   146-GlySerArgAspGlyIle-151
SEQ. ID. NO. 33926   179-AsnTyrAspLysLeuSer-184
SEQ. ID. NO. 33927   253-SerAlaTyrArgProAspGlyIleIle-261
SEQ. ID. NO. 33928   298-ValValAspSerLysProLeuMet-305
SEQ. ID. NO. 33929   317-GlnAlaMetLysAspGluLeuLeuLysGluAlaGluThrArgGlnSerGluArgGlyArgAlaGluAsnGlySer-341
g640
AMPHI Regions - AMPHI
SEQ. ID. NO. 33930   6-SerIleLeuLysSerIleGly-12
SEQ. ID. NO. 33931   22-SerIleArgArgMetSer-27
SEQ. ID. NO. 33932   47-LeuProAlaTyrAlaGluArgLeuProAspPheLeuAlaLysIleGlnPro-63
SEQ. ID. NO. 33933   72-ArgTyrGlyLysPro-76

TABLE 1-continued

| | |
|---|---|
| SEQ. ID. NO. 33934 | 109-SerLysProIleAspThrLeuMetAla-117 |
| SEQ. ID. NO. 33935 | 127-AlaLysLeuValAspHisHis-133 |
| SEQ. ID. NO. 33936 | 145-ArgValAspLysPheIleAsp-151 |
| SEQ. ID. NO. 33937 | 155-GlyLeuAsnPheIleLysAsnProProThr-164 |
| SEQ. ID. NO. 33938 | 187-IleGlnArgSerTyrLysValIle-194 |
| SEQ. ID. NO. 33939 | 209-AlaSerAlaSerAsp-213 |
| SEQ. ID. NO. 33940 | 224-ArgProArgArgMetAlaAsnProAsp-232 |
| SEQ. ID. NO. 33941 | 255-LeuAspGlnIleAsnLysLeuPheGluLysGly-265 |
| SEQ. ID. NO. 33942 | 267-LysAlaGlyValAlaAspHisAlaGluGlnGly-277 |
| SEQ. ID. NO. 33943 | 281-AspThrPheIleAspLeuTyrVal-288 |
| SEQ. ID. NO. 33944 | 346-MetIleGlnGlyGluAsnSerPhe-353 |
| SEQ. ID. NO. 33945 | 359-GlnHisGluArgValValGluLeuSerAlaAlaAspAlaProArg-373 |
| Antigenic Index - Jameson-Wolf | |
| SEQ. ID. NO. 33946 | 24-ArgArgMetSerAlaPheArgAlaArgIle-33 |
| SEQ. ID. NO. 33947 | 50-TyrAlaGluArgLeuProAspPhe-57 |
| SEQ. ID. NO. 33948 | 59-AlaLysIleGlnProSerGluIlePheProGlyAlaAspArgTyrGlyLysProGluGlyLysProMetVal-82 |
| SEQ. ID. NO. 33949 | 84-ArgValTyrLysGlyAspGluGlnLeu-92 |
| SEQ. ID. NO. 33950 | 101-AlaValAsnThrArgGlyTyrSerSerLysProIleAsp-113 |
| SEQ. ID. NO. 33951 | 128-LysLeuValAspHisHisGlu-134 |
| SEQ. ID. NO. 33952 | 142-ProGlnSerArgValAspLysPheIleAsp-151 |
| SEQ. ID. NO. 33953 | 159-IleLysAsnProProThrProSerValAlaProGlyAsp-171 |
| SEQ. ID. NO. 33954 | 184-AsnAspSerIleGlnArgSerTyrLys-192 |
| SEQ. ID. NO. 33955 | 196-AsnGlnTyrArgLeuGlySerAspLysAlaLeuGln-207 |
| SEQ. ID. NO. 33956 | 209-AlaSerAlaSerAspValArgGluAlaAlaProAlaSerGluThrArgProArgArgMetAlaAsnProAspLysGlnAspIle-236 |
| SEQ. ID. NO. 33957 | 241-GluLeuLeuLysGlnLysAla-247 |
| SEQ. ID. NO. 33958 | 257-GlnIleAsnLysLeuPheGluLysGlyGlyLysAlaGlyVal-270 |
| SEQ. ID. NO. 33959 | 272-AspHisAlaGluGlnGlyAspProAspAspThrPheIle-284 |
| SEQ. ID. NO. 33960 | 294-ProSerIleGlyLysSerLeuLeuGlyGluAspGlyTrp-306 |
| SEQ. ID. NO. 33961 | 309-LeuGlnLysArgLeuLysProGlyGln-317 |
| SEQ. ID. NO. 33962 | 322-ValAlaGlyGlyGluGlyArgTyrSerTrpLysGlySerGlyTyrValArg-337 |
| SEQ. ID. NO. 33963 | 342-AspArgIleGluMetIleGlnGlyGluAsnSerPheArgPheThrAspAlaGlnHisGluArgValValGlu-365 |
| SEQ. ID. NO. 33964 | 367-SerAlaAlaAspAlaProArgPheLysGlu-376 |
| SEQ. ID. NO. 33965 | 382-IleProGluGlyValAla-387 |
| SEQ. ID. NO. 33966 | 389-AspGlyAlaGluProTrpArg-395 |
| Hydrophilic Regions - Hopp-Woods | |
| SEQ. ID. NO. 33967 | 24-ArgArgMetSerAlaPheArgAlaArgIle-33 |
| SEQ. ID. NO. 33968 | 50-TyrAlaGluArgLeuPro-55 |
| SEQ. ID. NO. 33969 | 68-ProGlyAlaAspArgTyrGlyLysProGluGlyLysProMetVal-82 |
| SEQ. ID. NO. 33970 | 85-ValTyrLysGlyAspGluGlnLeu-92 |
| SEQ. ID. NO. 33971 | 128-LysLeuValAspHisHisGlu-134 |
| SEQ. ID. NO. 33972 | 143-GlnSerArgValAspLysPheIleAsp-151 |
| SEQ. ID. NO. 33973 | 186-SerIleGlnArgSerTyrLys-192 |
| SEQ. ID. NO. 33974 | 200-LeuGlySerAspLysAlaLeuGln-207 |
| SEQ. ID. NO. 33975 | 210-SerAlaSerAspValArgGluAlaAlaProAlaSerGluThrArgProArgArgMetAlaAsnProAspLysGlnAsp-235 |
| SEQ. ID. NO. 33976 | 241-GluLeuLeuLysGlnLysAla-247 |
| SEQ. ID. NO. 33977 | 257-GlnIleAsnLysLeuPheGluLysGlyGlyLysAlaGlyVal-270 |
| SEQ. ID. NO. 33978 | 272-AspHisAlaGluGlnGlyAspProAspAspThrPhe-283 |
| SEQ. ID. NO. 33979 | 309-LeuGlnLysArgLeuLysProGlyGln-317 |
| SEQ. ID. NO. 33980 | 324-GlyGluGlyArgTyrSerTrp-330 |
| SEQ. ID. NO. 33981 | 342-AspArgIleGluMetIleGlnGly-349 |
| SEQ. ID. NO. 33982 | 351-AsnSerPheArgPheThrAspAlaGlnHisGluArgValValGlu-365 |
| SEQ. ID. NO. 33983 | 367-SerAlaAlaAspAlaProArgPheLysGlu-376 |
| g642 | |
| AMPHI Regions - AMPHI | |
| SEQ. ID. NO. 33984 | 22-LysSerAlaCysArg-26 |
| SEQ. ID. NO. 33985 | 28-IleCysProLeuSerAlaIleSerAlaVal-37 |
| SEQ. ID. NO. 33986 | 63-SerGlyAspAspPhe-67 |
| SEQ. ID. NO. 33987 | 139-IleLysHisIleValArgAlaPhe-146 |
| SEQ. ID. NO. 33988 | 157-AspIleAlaGlyTrpValSerAlaPheLysThrLeuArgAlaGlnGluPheLeuGlnHisLeuArgGlyGlyVal-181 |
| SEQ. ID. NO. 33989 | 184-PheArgGlyGluGly-188 |
| SEQ. ID. NO. 33990 | 190-AspAspValArgLeu-194 |
| SEQ. ID. NO. 33991 | 209-AlaAspValAlaValLysAspPheGlyAsnLeuMetAlaAlaLeuAsp-224 |
| SEQ. ID. NO. 33992 | 241-ValGlnValValLysAspValPheHisAsnAlaValArgHisAlaAspGlnLeuGln-259 |
| SEQ. ID. NO. 33993 | 293-ValAspGlyValThrAspGlyAla-300 |
| SEQ. ID. NO. 33994 | 319-GlnValAspAspPheGlyGluPheAlaValPhe-329 |
| SEQ. ID. NO. 33995 | 348-PheArgGlyValAspVal-353 |
| SEQ. ID. NO. 33996 | 403-GluLeuLeuGlnArg-407 |
| SEQ. ID. NO. 33997 | 410-HisGlnArgAlaPheAspAlaGlyThr-418 |
| Antigenic Index - Jameson-Wolf | |
| SEQ. ID. NO. 33998 | 1-MetArgTyrProPro-5 |
| SEQ. ID. NO. 33999 | 16-CysLeuLeuArgArgProLysSerAlaCysArgArgIleCysPro-30 |
| SEQ. ID. NO. 34000 | 45-ValGlnGlnGluGlyCysGly-51 |
| SEQ. ID. NO. 34001 | 58-TyrGluAspLysLysSerGlyAspAspPheAlaAspGluAspPheLeu-73 |
| SEQ. ID. NO. 34002 | 75-GlyAlaGlyValGly-79 |
| SEQ. ID. NO. 34003 | 98-GlyAsnGlyGlyLysAlaAspIle-105 |
| SEQ. ID. NO. 34004 | 126-PheGlyGlyGlyAlaAspGluLeu-133 |
| SEQ. ID. NO. 34005 | 146-PheLysAsnArgGluGlyAlaAspIleAspGlyAspIle-158 |
| SEQ. ID. NO. 34006 | 166-LysThrLeuArgAla-170 |
| SEQ. ID. NO. 34007 | 184-PheArgGlyGluGlyPheAspAspValArgLeu-194 |
| SEQ. ID. NO. 34008 | 198-MetGlyAspGlyArgAspGlyArgAsnGlyMet-208 |

TABLE 1-continued

| | |
|---|---|
| SEQ. ID. NO. 34009 | 230-IleAspGluSerAspIleValAla-237 |
| SEQ. ID. NO. 34010 | 253-ArgHisAlaAspGlnLeuGlnAlaAlaAlaAspLysAspValLeuGluArgAlaGlnThrGlySerValAlaProGlyGlu-279 |
| SEQ. ID. NO. 34011 | 281-HisHisGlyGlyCysArg-286 |
| SEQ. ID. NO. 34012 | 288-PheGlyIleAspAlaValAspGlyValThrAspGly-299 |
| SEQ. ID. NO. 34013 | 313-CysPheGlyAspGluGlnGlnValAspAspPheGly-324 |
| SEQ. ID. NO. 34014 | 332-PheGlyGlyAsnGluGluGluValAla-340 |
| SEQ. ID. NO. 34015 | 369-CysAsnArgArgAlaGlyGlyPhe-376 |
| SEQ. ID. NO. 34016 | 412-ArgAlaPheAspAlaGlyThrGlnArgAsnGly-422 |
| SEQ. ID. NO. 34017 | 425-ValMetProArgAsnPro-430 |
| Hydrophilic Regions - Hopp-Woods | |
| SEQ. ID. NO. 34018 | 16-CysLeuLeuArgArgProLysSerAlaCysArgArgIleCys-29 |
| SEQ. ID. NO. 34019 | 58-TyrGluAspLysLysSerGlyAspAspPheAlaAspGluAspPheLeu-73 |
| SEQ. ID. NO. 34020 | 99-AsnGlyGlyLysAlaAspIle-105 |
| SEQ. ID. NO. 34021 | 129-GlyAlaAspGluLeu-133 |
| SEQ. ID. NO. 34022 | 146-PheLysAsnArgGluGlyAlaAspIleAspGlyAspIle-158 |
| SEQ. ID. NO. 34023 | 166-LysThrLeuArgAla-170 |
| SEQ. ID. NO. 34024 | 187-GluGlyPheAspAspValArgLeu-194 |
| SEQ. ID. NO. 34025 | 199-GlyAspGlyArgAspGlyArgAsnGlyMet-208 |
| SEQ. ID. NO. 34026 | 230-IleAspGluSerAspIleValAla-237 |
| SEQ. ID. NO. 34027 | 253-ArgHisAlaAspGlnLeuGlnAlaAlaAlaAspLysAspValLeuGluArgAlaGlnThr-272 |
| SEQ. ID. NO. 34028 | 292-AlaValAspGlyValThrAspGly-299 |
| SEQ. ID. NO. 34029 | 313-CysPheGlyAspGluGlnGlnValAspAspPheGly-324 |
| SEQ. ID. NO. 34030 | 334-GlyAsnGluGluGluValAla-340 |
| SEQ. ID. NO. 34031 | 369-CysAsnArgArgAlaGly-374 |
| SEQ. ID. NO. 34032 | 417-GlyThrGlnArgAsnGly-422 |
| g644 | |
| AMPHI Regions - AMPHI | |
| SEQ. ID. NO. 34033 | 26-GlyArgArgPheAspArgPro-32 |
| SEQ. ID. NO. 34034 | 55-MetAspThrAlaAlaPheLeuLysHisIleGluSerAlaPheProArgIlePheSerAspGlyIleAspLeuMetArgTyrLeu-82 |
| SEQ. ID. NO. 34035 | 111-GlnPheGluIleGlnGluValLeuArgIleAlaGly-122 |
| SEQ. ID. NO. 34036 | 141-GlnProLeuGlnGluPheGlyGly-148 |
| SEQ. ID. NO. 34037 | 181-ArgGluMetGlnSerCysTyrGluTyr-189 |
| SEQ. ID. NO. 34038 | 202-TyrTrpGlnGlyAsn-206 |
| SEQ. ID. NO. 34039 | 224-LeuAlaLysValIleAspLeuLeu-231 |
| SEQ. ID. NO. 34040 | 267-ValMetLysLeuSerArg-272 |
| SEQ. ID. NO. 34041 | 278-LeuArgAlaPheGlnAsn-283 |
| SEQ. ID. NO. 34042 | 295-MetThrHisGlyIleMetGluTyrIleLeuAspAsnLeuAsnArgTyrValArgAsn-313 |
| SEQ. ID. NO. 34043 | 333-GluIleLeuTyrArgTyrValCysHis-341 |
| SEQ. ID. NO. 34044 | 343-ValSerProValAlaProValAlaHis-351 |
| SEQ. ID. NO. 34045 | 356-AlaAsnIleValLysThrLeuAla-363 |
| SEQ. ID. NO. 34046 | 372-GlnMetLeuGlnLys-376 |
| SEQ. ID. NO. 34047 | 399-PheThrIlePheGluGlyProAsn-406 |
| SEQ. ID. NO. 34048 | 408-MetLeuTyrAlaGluIleTyrAspGlnPheValArgAla-420 |
| SEQ. ID. NO. 34049 | 456-LeuProGluAspIleArgSerPhe-463 |
| SEQ. ID. NO. 34050 | 481-GlyLysIleIleAlaArgLeu-487 |
| Antigenic Index - Jameson-Wolf | |
| SEQ. ID. NO. 34051 | 1-MetProSerGluArgProAlaAspCysCys-10 |
| SEQ. ID. NO. 34052 | 22-ThrLeuAsnCysGlyArgArgPheAspArgProProIleAsnGlyAsnArgGlnArgLysProMetIleHisThrGluProSerAlaGlnProSerThrMetAsp-56 |
| SEQ. ID. NO. 34053 | 70-ArgIlePheSerAspGlyIleAspLeu-78 |
| SEQ. ID. NO. 34054 | 82-LeuProGluAspLysTrpLeu-88 |
| SEQ. ID. NO. 34055 | 100-LeuAspLysLysHisGlyGlyArgLysGlySerGln-111 |
| SEQ. ID. NO. 34056 | 160-PheLysGlyGluSerArgArgLeuGlyValThrGluProGluThrSerGly-176 |
| SEQ. ID. NO. 34057 | 178-AlaIleAlaArgGluMetGlnSerCysTyrGluTyrThrAspGluGlnThr-194 |
| SEQ. ID. NO. 34058 | 202-TyrTrpGlnGlyAsnSerGlnSerAspPhe-211 |
| SEQ. ID. NO. 34059 | 216-AlaLysGluArgLysAsnGlyLysLeuAlaLys-226 |
| SEQ. ID. NO. 34060 | 235-LysThrTyrIleArg-239 |
| SEQ. ID. NO. 34061 | 241-GluThrLeuAlaSerGluGlyLeuArg-249 |
| SEQ. ID. NO. 34062 | 254-AlaValAsnArgIleAspAlaGluMet-262 |
| SEQ. ID. NO. 34063 | 269-LysLeuSerArgGlyAspAlaAlaGly-277 |
| SEQ. ID. NO. 34064 | 306-AsnLeuAsnArgTyrValArgAsnIleArgPheValAspTyrGluArgArgGluIleGlnArgArgHisGlnVal-331 |
| SEQ. ID. NO. 34065 | 381-LysGlyPheGluArgGlyHisProAlaGly-390 |
| SEQ. ID. NO. 34066 | 403-GluGlyProAsnAspMetLeu-409 |
| SEQ. ID. NO. 34067 | 420-AlaThrAlaGluGluLysGluAlaGlyIleLysLeuAspLysAsnGlnThr-436 |
| SEQ. ID. NO. 34068 | 441-ValGlnThrAspValArg-446 |
| SEQ. ID. NO. 34069 | 449-AlaValAlaArgAspTyrAlaLeu-456 |
| SEQ. ID. NO. 34070 | 458-GluAspIleArgSerPheLeu-464 |
| SEQ. ID. NO. 34071 | 492-GlnGluGluHisGluAspThrThr-499 |
| SEQ. ID. NO. 34072 | 505-AspIleArgLysAspIleLeuAspCysArgTyrCysGly-517 |
| Hydrophilic Regions - Hopp-Woods | |
| SEQ. ID. NO. 34073 | 1-MetProSerGluArgProAlaAsp-8 |
| SEQ. ID. NO. 34074 | 25-CysGlyArgArgPheAspArgProProIleAsnGlyAsnArgGlnArgLysProMetIle-44 |
| SEQ. ID. NO. 34075 | 72-PheSerAspGlyIleAsp-77 |
| SEQ. ID. NO. 34076 | 82-LeuProGluAspLysTrpLeu-88 |
| SEQ. ID. NO. 34077 | 100-LeuAspLysLysHisGlyGlyArgLysGlySerGln-111 |
| SEQ. ID. NO. 34078 | 160-PheLysGlyGluSerArgArgLeuGlyValThrGluProGluThrSerGly-176 |
| SEQ. ID. NO. 34079 | 178-AlaIleAlaArgGluMetGlnSer-185 |
| SEQ. ID. NO. 34080 | 188-GluTyrThrAspGluGlnThr-194 |
| SEQ. ID. NO. 34081 | 216-AlaLysGluArgLysAsnGlyLysLeuAlaLys-226 |
| SEQ. ID. NO. 34082 | 254-AlaValAsnArgIleAspAlaGluMet-262 |

| | |
|---|---|
| SEQ. ID. NO. 34083 | 269-LysLeuSerArgGlyAspAlaAlaGly-277 |
| SEQ. ID. NO. 34084 | 306-AsnLeuAsnArgTyrValArgAsnAspIleArgPheValAspTyrGluArgArgGluIleGlnArgArgHisGlnVal-331 |
| SEQ. ID. NO. 34085 | 381-LysGlyPheGluArgGlyHisPro-388 |
| SEQ. ID. NO. 34086 | 420-AlaThrAlaGluGluLysGluAlaGlyIleLysLeuAspLysAsnGlnThr-436 |
| SEQ. ID. NO. 34087 | 441-ValGlnThrAspValArg-446 |
| SEQ. ID. NO. 34088 | 458-GluAspIleArgSerPheLeu-464 |
| SEQ. ID. NO. 34089 | 492-GlnGluGluHisGluAspThrThr-499 |
| SEQ. ID. NO. 34090 | 505-AspIleArgLysAspIleLeuAsp-512 | g645
AMPHI Regions - AMPHI

| | |
|---|---|
| SEQ. ID. NO. 34091 | 87-ArgThrLeuProSerLeuAsnGlyLeuThrLys-97 |
| SEQ. ID. NO. 34092 | 149-ArgThrProLysArgCysSerSerSerIle-158 |
| SEQ. ID. NO. 34093 | 162-ProLysPheLeuAsnPheMetSerSerCysThrAsnLeuCys-175 |
| SEQ. ID. NO. 34094 | 211-SerAlaLysArgSer-215 |
| SEQ. ID. NO. 34095 | 250-SerValLeuProLysProThrSerProHisThrSerArg-262 |

Antigenic Index - Jameson-Wolf

| | |
|---|---|
| SEQ. ID. NO. 34096 | 24-AsnLeuCysCysLysLysSerArgMetThrCysSerSerSerArgSerArgSerCysProCys-44 |
| SEQ. ID. NO. 34097 | 47-ProIleArgAlaSerGlySerArgValSerSerArgSerArgIle-61 |
| SEQ. ID. NO. 34098 | 68-SerLeuCysArgLysAsnThrCysProProArgLeuSerSerArgAsnThrAlaSerArgThrLeuProSer-91 |
| SEQ. ID. NO. 34099 | 99-PheThrAlaArgArgArgLeuGly-106 |
| SEQ. ID. NO. 34100 | 110-IleSerGluLysSerArgArgProSerSerAlaMetLeuArg-123 |
| SEQ. ID. NO. 34101 | 137-ThrLeuAlaArgArgArgLeuSerCysSerPheCysArgThrProLysArgCysSerSer-156 |
| SEQ. ID. NO. 34102 | 158-IleIleAsnLysProLysPheLeuAsn-166 |
| SEQ. ID. NO. 34103 | 168-MetSerSerCysThrAsn-173 |
| SEQ. ID. NO. 34104 | 199-LeuLysArgGluArgLeuAla-205 |
| SEQ. ID. NO. 34105 | 208-ThrGlyLysSerAlaLysArgSerAlaLys-217 |
| SEQ. ID. NO. 34106 | 222-CysSerThrArgSerValValGlyAla-230 |
| SEQ. ID. NO. 34107 | 243-AsnAlaAlaArgArgAlaThr-249 |
| SEQ. ID. NO. 34108 | 251-ValLeuProLysProThrSerProHisThrSerArg-262 |

Hydrophilic Regions - Hopp-Woods

| | |
|---|---|
| SEQ. ID. NO. 34109 | 26-CysCysLysLysSerArgMetThrCysSerSerSerArgSerArgSerCysPro-43 |
| SEQ. ID. NO. 34110 | 48-IleArgAlaSerGlySerArgValSerSerArgSerArgIle-61 |
| SEQ. ID. NO. 34111 | 69-LeuCysArgLysAsnThrCysProProArgLeuSerSerArgAsnThrAlaSerArgThr-88 |
| SEQ. ID. NO. 34112 | 99-PheThrAlaArgArgArgLeuGly-106 |
| SEQ. ID. NO. 34113 | 110-IleSerGluLysSerArgArgProSer-118 |
| SEQ. ID. NO. 34114 | 137-ThrLeuAlaArgArgArgLeuSer-144 |
| SEQ. ID. NO. 34115 | 149-ArgThrProLysArgCysSer-155 |
| SEQ. ID. NO. 34116 | 158-IleIleAsnLysProLys-163 |
| SEQ. ID. NO. 34117 | 199-LeuLysArgGluArgLeuAla-205 |
| SEQ. ID. NO. 34118 | 210-LysSerAlaLysArgSerAlaLys-217 |
| SEQ. ID. NO. 34119 | 243-AsnAlaAlaArgArgAlaThr-249 | g647
AMPHI Regions - AMPHI

| | |
|---|---|
| SEQ. ID. NO. 34120 | 38-GlyLysValCysArgCysPheGluGlnVal-47 |
| SEQ. ID. NO. 34121 | 69-ThrValPheArgGlnIleValGlyValVal-78 |

Antigenic Index - Jameson-Wolf

| | |
|---|---|
| SEQ. ID. NO. 34122 | 26-GlyLeuValLysGluArgAlaArg-33 |
| SEQ. ID. NO. 34123 | 39-LysValCysArgCysPhe-44 |
| SEQ. ID. NO. 34124 | 54-GlyThrValGlyGlnThrGluArgGlyThr-63 |
| SEQ. ID. NO. 34125 | 78-ValAspAspThrAspAlaGluArgThrAlaValHisSerArgGlyThrArgGlyPhe-96 |

Hydrophilic Regions - Hopp-Woods

| | |
|---|---|
| SEQ. ID. NO. 34126 | 26-GlyLeuValLysGluArgAlaArg-33 |
| SEQ. ID. NO. 34127 | 40-ValCysArgCysPhe-44 |
| SEQ. ID. NO. 34128 | 56-ValGlyGlnThrGluArgGlyThr-63 |
| SEQ. ID. NO. 34129 | 78-ValAspAspThrAspAlaGluArgThrAlaValHisSerArgGlyThrArgGly-95 | g648
AMPHI Regions - AMPHI

| | |
|---|---|
| SEQ. ID. NO. 34130 | 7-ArgIleGluArgAlaValArg-13 |
| SEQ. ID. NO. 34131 | 15-AlaValIleAspValLeuAsn-21 |
| SEQ. ID. NO. 34132 | 94-AlaValAspLeuHisAlaIleIleLysLeuAlaAspThr-106 |
| SEQ. ID. NO. 34133 | 127-GlnGlyValGluGlnGly-132 |
| SEQ. ID. NO. 34134 | 148-ArgLeuLysHisLeuLysGluGlyAsnAla-157 |
| SEQ. ID. NO. 34135 | 182-AlaArgAlaLeuGlyAsnValPheHis-190 |
| SEQ. ID. NO. 34136 | 194-GlySerGlyIleAspGlyIleGlnThrIleValAlaPheAsnGlnHisThr-210 |

Antigenic Index - Jameson-Wolf

| | |
|---|---|
| SEQ. ID. NO. 34137 | 1-MetAsnArgArgAsnAlaArgIleGluArgAlaValArg-13 |
| SEQ. ID. NO. 34138 | 24-AlaProGlyProGly-28 |
| SEQ. ID. NO. 34139 | 30-LeuLeuHisGlnArgGlyLysGlnValGlySerArgAsnAspThrLeuAla-46 |
| SEQ. ID. NO. 34140 | 65-GlyLysLysArgPheValGlnProArgAsnLeuValGlyArgLysGlnArgAsn-82 |
| SEQ. ID. NO. 34141 | 123-PheAsnMetProGlnGlyValGluGlnGlyCysArg-134 |
| SEQ. ID. NO. 34142 | 141-LeuArgThrArgPheAspArgArgLeuLysHisLeuLysGluGlyAsnAla-157 |
| SEQ. ID. NO. 34143 | 170-ValGlnProAlaAspThrSerGlyIleAspAlaAspAlaArgAla-184 |
| SEQ. ID. NO. 34144 | 191-AsnArgAlaGlySerGlyIleAspGly-199 |

Hydrophilic Regions - Hopp-Woods

| | |
|---|---|
| SEQ. ID. NO. 34145 | 1-MetAsnArgArgAsnAlaArgIleGluArgAlaValArg-13 |
| SEQ. ID. NO. 34146 | 33-GlnArgGlyLysGlnValGlySerArgAsnAspThr-44 |
| SEQ. ID. NO. 34147 | 65-GlyLysLysArgPheValGln-71 |
| SEQ. ID. NO. 34148 | 74-AsnLeuValGlyArgLysGlnArgAsn-82 |
| SEQ. ID. NO. 34149 | 127-GlnGlyValGluGlnGlyCysArg-134 |
| SEQ. ID. NO. 34150 | 141-LeuArgThrArgPheAspArgArgLeuLysHisLeuLysGluGlyAsnAla-157 |

TABLE 1-continued

| | |
|---|---|
| SEQ. ID. NO. 34151 | 172-ProAlaAspThrSerGlyIleAspAlaAspAlaArgAla-184 | g649
AMPHI Regions - AMPHI

| | |
|---|---|
| SEQ. ID. NO. 34152 | 6-LeuSerAlaIleLeuGlyLeuVal-13 |
| SEQ. ID. NO. 34153 | 24-ProAlaHisArgHisThrLysHisIleSerLysAla-35 |
| SEQ. ID. NO. 34154 | 57-SerGlnGlyAsnVal-61 |
| SEQ. ID. NO. 34155 | 63-GluLeuArgGluAsnLys-68 |
| SEQ. ID. NO. 34156 | 71-ArgLysAlaPheArgThrLeuPro-78 |

Antigenic Index - Jameson-Wolf

| | |
|---|---|
| SEQ. ID. NO. 34157 | 20-GlyThrSerGluProAlaHisArgHisThrLysHisIleSerLysAlaAsnLys-37 |
| SEQ. ID. NO. 34158 | 40-LeuHisProGluCysArgLysTyrLeuGluArgArgAlaAla-53 |
| SEQ. ID. NO. 34159 | 56-ArgSerGlnGlyAsnValGlnGluLeuArgGluAsnLysLysAlaArgLysAlaPheArg-75 |
| SEQ. ID. NO. 34160 | 80-AlaGluGlnLysIleGlnCys-86 |
| SEQ. ID. NO. 34161 | 92-AlaPheAspAspPheAspGlyGlyArgPheArgArg-103 |

Hydrophilic Regions - Hopp-Woods

| | |
|---|---|
| SEQ. ID. NO. 34162 | 20-GlyThrSerGluProAlaHisArgHisThrLysHisIleSerLysAlaAsnLys-37 |
| SEQ. ID. NO. 34163 | 42-ProGluCysArgLysTyrLeuGluArgArgAlaAla-53 |
| SEQ. ID. NO. 34164 | 59-GlyAsnValGlnGluLeuArgGluAsnLysLysAlaArgLysAlaPheArg-75 |
| SEQ. ID. NO. 34165 | 80-AlaGluGlnLysIleGlnCys-86 |
| SEQ. ID. NO. 34166 | 92-AlaPheAspAspPheAspGlyGlyArgPheArgArg-103 | g650
AMPHI Regions - AMPHI

| | |
|---|---|
| SEQ. ID. NO. 34167 | 15-SerValCysProGly-19 |
| SEQ. ID. NO. 34168 | 57-LeuTrpAspGluLeuArgGlnGly-64 |
| SEQ. ID. NO. 34169 | 72-ProGluLeuValArgArgHisGlu-79 |
| SEQ. ID. NO. 34170 | 89-PheAspArgValValAsn-94 |
| SEQ. ID. NO. 34171 | 137-SerGlyLeuTrpGln-141 |
| SEQ. ID. NO. 34172 | 173-AsnTyrLeuGlnTyrLeuTyrGlyLeuPheGlyAspTrpPro-186 |
| SEQ. ID. NO. 34173 | 198-AsnValGlyArgAlaValAsnArgAlaArg-207 |
| SEQ. ID. NO. 34174 | 218-LeuArgMetProAsnGluThr-224 |
| SEQ. ID. NO. 34175 | 260-ValGluProGlyArgProLeu-266 |
| SEQ. ID. NO. 34176 | 269-GluAlaIleAlaArgLeuAlaGlyIleThrGlnSer-280 |
| SEQ. ID. NO. 34177 | 314-SerAsnTyrLeuAsnAlaAlaProAsp-322 |
| SEQ. ID. NO. 34178 | 341-IleSerThrAlaThrGlyMet-347 |
| SEQ. ID. NO. 34179 | 349-IleAlaAspIleLysArgLeuAsnAsnLeu-358 |
| SEQ. ID. NO. 34180 | 433-ValArgThrGlyThrArgSer-439 |

Antigenic Index - Jameson-Wolf

| | |
|---|---|
| SEQ. ID. NO. 34181 | 1-MetSerLysLeuLys-5 |
| SEQ. ID. NO. 34182 | 24-GlnAsnThrSerSerHis-29 |
| SEQ. ID. NO. 34183 | 38-LeuAsnSerSerIleLeuAspLeuProProThrLysGlnTyrPhe-52 |
| SEQ. ID. NO. 34184 | 54-SerGlySerLeuTrpAspGluLeuArgGlnGlyPheArgMetGlyGluValAsnProGluLeuValArgArgHisGluSerLysPheIleAla-84 |
| SEQ. ID. NO. 34185 | 87-SerTyrPheAspArgValValAsnArgSerArgPro-98 |
| SEQ. ID. NO. 34186 | 105-AsnGluValLysLysArgAsnMetProAla-114 |
| SEQ. ID. NO. 34187 | 128-ThrLysAlaLysSerHisValGlyAlaSerGly-138 |
| SEQ. ID. NO. 34188 | 145-AlaThrGlyArgHisTyrGlyLeuGluLysThrProValTyrAspGlyArgHisAspVal-164 |
| SEQ. ID. NO. 34189 | 192-TyrAsnTrpGlyGluGlyAsnValGlyArgAlaValAsnArgAlaArgAspGlnGlyLeuGluProThrTyrGluAsnLeuArgMetProAsnGluThrArgAsnTyrVal-228 |
| SEQ. ID. NO. 34190 | 247-AsnIleSerAspIleAspAsnLysProTyr-256 |
| SEQ. ID. NO. 34191 | 259-AlaValGluProGlyArgProLeuAspAsnGluAlaIleAla-272 |
| SEQ. ID. NO. 34192 | 294-PheIleProLysAsnLysArgLysLeu-302 |
| SEQ. ID. NO. 34193 | 318-AsnAlaAlaProAspSer-323 |
| SEQ. ID. NO. 34194 | 332-ProAlaAlaLysThrSerLeuSerAspIleSerThr-343 |
| SEQ. ID. NO. 34195 | 350-AlaAspIleLysArgLeuAsnAsnLeuAsnGly-360 |
| SEQ. ID. NO. 34196 | 370-LeuValAlaLysAsnGlyLysThrLeu-378 |
| SEQ. ID. NO. 34197 | 388-IleAspIleAspAsnThrProAspThrTyrArgSerAsnMetProAla-403 |
| SEQ. ID. NO. 34198 | 431-GluThrValArgThrGlyThrArgSerProCysProHisTyrArgThrArgProCysAspSerArgSerAlaThrSerAsnArgLysThrAspCysHisAla-464 |

Hydrophilic Regions - Hopp-Woods

| | |
|---|---|
| SEQ. ID. NO. 34199 | 1-MetSerLysLeuLys-5 |
| SEQ. ID. NO. 34200 | 59-AspGluLeuArgGlnGlyPheArgMetGlyGluValAsnProGluLeuValArgArgHisGluSerLysPheIleAla-84 |
| SEQ. ID. NO. 34201 | 92-ValValAsnArgSerArgPro-98 |
| SEQ. ID. NO. 34202 | 105-AsnGluValLysLysArgAsnMetProAla-114 |
| SEQ. ID. NO. 34203 | 128-ThrLysAlaLysSerHisVal-134 |
| SEQ. ID. NO. 34204 | 150-TyrGlyLeuGluLysThrProValTyrAspGlyArgHisAspVal-164 |
| SEQ. ID. NO. 34205 | 202-AlaValAsnArgAlaArgAspGlnGlyLeu-211 |
| SEQ. ID. NO. 34206 | 213-ProThrTyrGluAsnLeuArgMetProAsnGluThrArgAsnTyrVal-228 |
| SEQ. ID. NO. 34207 | 249-SerAspIleAspAsn-253 |
| SEQ. ID. NO. 34208 | 261-GluProGlyArgProLeuAspAsnGluAlaIleAla-272 |
| SEQ. ID. NO. 34209 | 296-ProLysAsnLysArgLysLeu-302 |
| SEQ. ID. NO. 34210 | 334-AlaLysThrSerLeu-338 |
| SEQ. ID. NO. 34211 | 350-AlaAspIleLysArgLeuAsn-356 |
| SEQ. ID. NO. 34212 | 373-LysAsnGlyLysThr-377 |
| SEQ. ID. NO. 34213 | 389-AspIleAspAsnThrProAspThrTyrArg-398 |
| SEQ. ID. NO. 34214 | 431-GluThrValArgThrGlyThrArgSerPro-440 |
| SEQ. ID. NO. 34215 | 444-TyrArgThrArgProCysAspSerArgSerAlaThrSerAsnArgLysThrAspCys-462 | g652-1
AMPHI Regions - AMPHI

| | |
|---|---|
| SEQ. ID. NO. 34216 | 6-AspIlePheAlaArg-10 |
| SEQ. ID. NO. 34217 | 52-ArgAspGlyAspLys-56 |
| SEQ. ID. NO. 34218 | 62-LysGlyValLeuLysAlaValGluHisValAsnAsnGlnIleAlaGlnAla-78 |

TABLE 1-continued

| | |
|---|---|
| SEQ. ID. NO. 34219 | 130-LeuTyrArgTyrLeuGlyGlyAlaGlyPro-139 |
| SEQ. ID. NO. 34220 | 149-ValIleAsnGlyGly-153 |
| SEQ. ID. NO. 34221 | 173-LysSerPheArgGluAlaLeuArgCys-181 |
| SEQ. ID. NO. 34222 | 184-GluIlePheHisAlaLeuLysLys-191 |
| SEQ. ID. NO. 34223 | 266-AlaGluPheAlaGluTyrLeuGluGlyLeuValAsn-277 |
| SEQ. ID. NO. 34224 | 299-LeuThrGluLysLeu-303 |
| SEQ. ID. NO. 34225 | 323-AlaGluGlyIleGluLysGlyVal-330 |
| SEQ. ID. NO. 34226 | 338-ValAsnGlnIleGlyThrLeuSerGluThrLeuLysAlaValAspLeuAlaLysCysAsnArgTyrAlaSer-361 |
| SEQ. ID. NO. 34227 | 377-AspLeuAlaValAla-381 |
| SEQ. ID. NO. 34228 | 391-SerLeuSerArgSerAspArgMetAlaLysTyrAsnGlnLeuLeuArgIleGluGlu-409 |
| Antigenic Index - Jameson-Wolf | |
| SEQ. ID. NO. 34229 | 11-GluIleLeuAspSerArgGlyAsnProThrValGlu-22 |
| SEQ. ID. NO. 34230 | 36-AlaValProSerGlyAlaSerThrGlyGlnLysGluAlaLeuGluLeuArgAspGlyAspLysSerArgTyrSerGlyLysGlyValLeuLysAlaVal GluHisValAsn-72 |
| SEQ. ID. NO. 34231 | 83-AspAlaAsnGluGlnSerTyr-89 |
| SEQ. ID. NO. 34232 | 97-LeuAspGlyThrGluAsnLysGlyAsnLeuGly-107 |
| SEQ. ID. NO. 34233 | 121-AlaAlaAlaGluAspSerGlyLeuPro-129 |
| SEQ. ID. NO. 34234 | 135-GlyGlyAlaGlyProMet-140 |
| SEQ. ID. NO. 34235 | 151-AsnGlyGlyGluHisAlaAsnAsnSer-159 |
| SEQ. ID. NO. 34236 | 173-LysSerPheArgGluAlaLeuArgCysGlyAla-183 |
| SEQ. ID. NO. 34237 | 190-LysLysLeuCysAspSerLysGlyPheProThrThrValGlyAspGluGlyGlyPhe-208 |
| SEQ. ID. NO. 34238 | 211-AsnLeuAsnSerHisLysGluAlaLeu-219 |
| SEQ. ID. NO. 34239 | 243-CysAlaSerSerGluPheTyrLysAspGlyLysTyrHisLeuGluAlaGluGlyArgSerTyrThrAsn-265 |
| SEQ. ID. NO. 34240 | 283-SerIleGluAspGlyMetAspGluAsnAspTrpGluGly-295 |
| SEQ. ID. NO. 34241 | 299-LeuThrGluLysLeuGlyLysLysValGlnLeuValGlyAspAspLeu-314 |
| SEQ. ID. NO. 34242 | 318-AsnProLysIleLeuAlaGluGlyIleGluLysGlyVal-330 |
| SEQ. ID. NO. 34243 | 352-AspLeuAlaLysCysAsnArgTyr-359 |
| SEQ. ID. NO. 34244 | 363-MetSerHisArgSerGlyGluThrGluAspSerThrIle-375 |
| SEQ. ID. NO. 34245 | 388-LysThrGlySerLeuSerArgSerAspArgMetAlaLys-400 |
| SEQ. ID. NO. 34246 | 405-LeuArgIleGluGluGluLeuAlaGlu-413 |
| Hydrophilic Regions - Hopp-Woods | |
| SEQ. ID. NO. 34247 | 11-GluIleLeuAspSerArgGlyAsnProThrValGlu-22 |
| SEQ. ID. NO. 34248 | 43-ThrGlyGlnLysGluAlaLeuGluLeuArgAspGlyAspLysSerArgTyrSerGly-61 |
| SEQ. ID. NO. 34249 | 63-GlyValLeuLysAlaValGlu-69 |
| SEQ. ID. NO. 34250 | 97-LeuAspGlyThrGluAsnLysGlyAsnLeu-106 |
| SEQ. ID. NO. 34251 | 121-AlaAlaAlaGluAspSerGly-127 |
| SEQ. ID. NO. 34252 | 153-GlyGluHisAlaAsn-157 |
| SEQ. ID. NO. 34253 | 173-LysSerPheArgGluAlaLeuArgCysGlyAla-183 |
| SEQ. ID. NO. 34254 | 190-LysLysLeuCysAspSerLysGly-197 |
| SEQ. ID. NO. 34255 | 202-ValGlyAspGluGlyGlyPhe-208 |
| SEQ. ID. NO. 34256 | 213-AsnSerHisLysGluAlaLeu-219 |
| SEQ. ID. NO. 34257 | 247-GluPheTyrLysAspGlyLysTyrHisLeuGluAlaGluGlyArgSerTyrThr-264 |
| SEQ. ID. NO. 34258 | 283-SerIleGluAspGlyMetAspGluAsnAspTrpGluGly-295 |
| SEQ. ID. NO. 34259 | 299-LeuThrGluLysLeuGlyLysLysValGlnLeuValGly-311 |
| SEQ. ID. NO. 34260 | 321-IleLeuAlaGluGlyIleGluLysGlyVal-330 |
| SEQ. ID. NO. 34261 | 352-AspLeuAlaLysCysAsnArg-358 |
| SEQ. ID. NO. 34262 | 364-SerHisArgSerGlyGluThrGluAspSerThrIle-375 |
| SEQ. ID. NO. 34263 | 391-SerLeuSerArgSerAspArgMetAlaLys-400 |
| SEQ. ID. NO. 34264 | 405-LeuArgIleGluGluGluLeuAlaGlu-413 |
| g653 | |
| AMPHI Regions - AMPHI | |
| SEQ. ID. NO. 34265 | 60-ThrMetArgLysProArgLeuThr-67 |
| SEQ. ID. NO. 34266 | 75-AlaLeuIlePheThrCysPheAla-82 |
| SEQ. ID. NO. 34267 | 96-ThrAlaLeuAlaAlaIleThrCysIle-104 |
| SEQ. ID. NO. 34268 | 111-LeuGlyLysMetGluGluPheSer-118 |
| Antigenic Index - Jameson-Wolf | |
| SEQ. ID. NO. 34269 | 4-GluProMetArgMetProGlu-10 |
| SEQ. ID. NO. 34270 | 14-GlyPheSerGlySer-18 |
| SEQ. ID. NO. 34271 | 45-GlyCysArgSerThrArgLysThr-52 |
| SEQ. ID. NO. 34272 | 56-ValArgProGluThrMetArgLysProArgLeuThrAsnSerSerAla-71 |
| SEQ. ID. NO. 34273 | 86-AsnSerGlyCysAsnAla-91 |
| SEQ. ID. NO. 34274 | 103-CysIleAsnGlyProProCysArgLeuGlyLysMetGluGlu-116 |
| SEQ. ID. NO. 34275 | 125-SerArgHisLysIleThrProProArgGlyProArgArgVal-138 |
| SEQ. ID. NO. 34276 | 145-ThrLysSerGlnAsnGlyThrGly-152 |
| SEQ. ID. NO. 34277 | 156-SerProProAlaThrSerProAla-163 |
| Hydrophilic Regions - Hopp-Woods | |
| SEQ. ID. NO. 34278 | 4-GluProMetArgMetProGlu-10 |
| SEQ. ID. NO. 34279 | 47-ArgSerThrArgLysThr-52 |
| SEQ. ID. NO. 34280 | 57-ArgProGluThrMetArgLysProArgLeuThrAsn-68 |
| SEQ. ID. NO. 34281 | 107-ProProCysArgLeuGlyLysMetGluGlu-116 |
| SEQ. ID. NO. 34282 | 126-ArgHisLysIleThrProProArgGlyProArg-136 |
| g656 | |
| AMPHI Regions - AMPHI | |
| SEQ. ID. NO. 34283 | 6-GlySerIleSerSerMetIleSerIleAlaArgThrPheGlyAlaProGlu-22 |
| SEQ. ID. NO. 34284 | 42-LysGlnProSerThr-46 |
| SEQ. ID. NO. 34285 | 92-LeuAlaSerLeuAsnLysSerCys-99 |
| Antigenic Index - Jameson-Wolf | |
| SEQ. ID. NO. 34286 | 4-PheSerGlySerIle-8 |
| SEQ. ID. NO. 34287 | 19-GlyAlaProGluSerValProAlaGlyLysValAlaAla-31 |
| SEQ. ID. NO. 34288 | 40-SerPheLysGlnProSerThrLeuGlu-48 |

TABLE 1-continued

| | |
|---|---|
| SEQ. ID. NO. 34289 | 74-ArgProThrSerLeuArgProLysSerIle-83 |
| SEQ. ID. NO. 34290 | 94-SerLeuAsnLysSerCysSerLeuAlaArgSerSerAlaGlyValLeuProArgArgArgValProAla-116 |
| SEQ. ID. NO. 34291 | 120-ThrMetThrSerSerArgSerArgArgThrArgIleSerGlyGluGluProThrMetTrpLysSerProLysSer-144 |
| Hydrophilic Regions - Hopp-Woods | |
| SEQ. ID. NO. 34292 | 76-ThrSerLeuArgProLysSer-82 |
| SEQ. ID. NO. 34293 | 99-CysSerLeuAlaArgSerSer-105 |
| SEQ. ID. NO. 34294 | 109-LeuProArgArgArgValProAla-116 |
| SEQ. ID. NO. 34295 | 121-MetThrSerSerArgSerArgArgThrArgIleSerGlyGluGluProThrMet-138 |
| SEQ. ID. NO. 34296 | 140-LysSerProLysSer-144 |
| g657 | |
| AMPHI Regions - AMPHI | |
| SEQ. ID. NO. 34297 | 20-LeuGlyArgMetPheAla-25 |
| SEQ. ID. NO. 34298 | 65-AspGluLeuAlaLysCysAlaAla-72 |
| SEQ. ID. NO. 34299 | 83-AspAlaMetArgSerLeuAlaLysHisThrAsn-93 |
| SEQ. ID. NO. 34300 | 128-CysLysAlaGluAspIleThrGluAlaSer-137 |
| SEQ. ID. NO. 34301 | 139-GlnPheLeuProGlyIleLeuLysThr-147 |
| SEQ. ID. NO. 34302 | 161-LysThrLeuAspGluLeuLysAlaAla-169 |
| SEQ. ID. NO. 34303 | 178-CysValLeuGluLysMetValAsp-185 |
| SEQ. ID. NO. 34304 | 205-PheAspProAlaGluAsnIle-211 |
| SEQ. ID. NO. 34305 | 232-GlnGlnAlaArgGlnThrAlaGlnArgLeuAlaAspGluLeuAspTyrValGlyValLeu-251 |
| Antigenic Index - Jameson-Wolf | |
| SEQ. ID. NO. 34306 | 37-ValLeuAspProAspProAsnAlaPro-45 |
| SEQ. ID. NO. 34307 | 57-ProPheAspAspArgAlaAlaLeuAspGluLeuAlaLys-69 |
| SEQ. ID. NO. 34308 | 75-ThrGluPheGluAsnValAsnAlaAspAlaMetArgSerLeuAlaLysHisThrAsnValSerProSerGlyAspCysVal-101 |
| SEQ. ID. NO. 34309 | 104-AlaGlnAsnArgIleGlnLysAlaTrpIle-114 |
| SEQ. ID. NO. 34310 | 128-CysLysAlaGluAspIleThrGluAla-136 |
| SEQ. ID. NO. 34311 | 150-LeuGlyTyrAspGlyLysGlyGlnIleArgValLysThrLeuAspGluLeuLysAlaAlaPhe-170 |
| SEQ. ID. NO. 34312 | 182-LysMetValAspLeuArgGlyGluIle-190 |
| SEQ. ID. NO. 34313 | 196-ArgLeuAsnAspGluAsnValGln-203 |
| SEQ. ID. NO. 34314 | 205-PheAspProAlaGluAsnIleHisGluAsnGly-215 |
| SEQ. ID. NO. 34315 | 230-ValGlnGlnGlnAlaArgGlnThrAlaGlnArgLeuAlaAspGluLeuAsp-246 |
| SEQ. ID. NO. 34316 | 268-GluThrAlaProArgThrHisAsnSerGlyHisHis-279 |
| SEQ. ID. NO. 34317 | 288-GlnPheGlnGlnGln-292 |
| SEQ. ID. NO. 34318 | 300-ProProAlaAspThrLysLeuLeuSer-308 |
| SEQ. ID. NO. 34319 | 319-ValTrpGlnGluAspGlyGlyGluProAspTrp-329 |
| SEQ. ID. NO. 34320 | 332-LeuGlnSerArgProAsnAla-338 |
| SEQ. ID. NO. 34321 | 344-GlyLysLysThrAlaGlnLysGlyArgLysMetGly-355 |
| SEQ. ID. NO. 34322 | 361-ThrThrAspSerAspThrAlaPheGlnGluAlaLysLysLeuHis-375 |
| Hydrophilic Regions - Hopp-Woods | |
| SEQ. ID. NO. 34323 | 37-ValLeuAspProAspProAsnAlaPro-45 |
| SEQ. ID. NO. 34324 | 57-ProPheAspAspArgAlaAlaLeuAspGluLeuAlaLys-69 |
| SEQ. ID. NO. 34325 | 75-ThrGluPheGluAsnValAsn-81 |
| SEQ. ID. NO. 34326 | 83-AspAlaMetArgSerLeuAlaLys-90 |
| SEQ. ID. NO. 34327 | 128-CysLysAlaGluAspIleThrGluAla-136 |
| SEQ. ID. NO. 34328 | 152-TyrAspGlyLysGlyGlnIleArgValLysThrLeuAspGluLeuLysAlaAlaPhe-170 |
| SEQ. ID. NO. 34329 | 182-LysMetValAspLeuArgGlyGluIle-190 |
| SEQ. ID. NO. 34330 | 196-ArgLeuAsnAspGluAsnValGln-203 |
| SEQ. ID. NO. 34331 | 206-AspProAlaGluAsnIleHis-212 |
| SEQ. ID. NO. 34332 | 230-ValGlnGlnGlnAlaArgGlnThrAlaGlnArgLeuAlaAspGluLeuAsp-246 |
| SEQ. ID. NO. 34333 | 269-ThrAlaProArgThrHisAsn-275 |
| SEQ. ID. NO. 34334 | 301-ProAlaAspThrLysLeu-306 |
| SEQ. ID. NO. 34335 | 320-TrpGlnGluAspGlyGlyGluProAsp-328 |
| SEQ. ID. NO. 34336 | 344-GlyLysLysThrAlaGlnLysGlyArgLysMetGly-355 |
| SEQ. ID. NO. 34337 | 362-ThrAspSerAspThrAlaPheGlnGluAlaLysLysLeuHis-375 |
| g658 | |
| AMPHI Regions - AMPHI | |
| SEQ. ID. NO. 34338 | 28-ArgGlnTyrAlaAspIleIleGlnPheValArgGlnAlaLeuArgArgLeuProArgLeuLeuLeu-49 |
| SEQ. ID. NO. 34339 | 68-ValAspValPheGlyGlyValGluGly-76 |
| SEQ. ID. NO. 34340 | 93-AlaGlnValHisHisPhePheGlnAsnAlaIleHisAla-105 |
| SEQ. ID. NO. 34341 | 139-GlnLysLeuArgAlaCysPheSerAsnValPheGly-150 |
| SEQ. ID. NO. 34342 | 155-LeuIleArgArgGlyLeuGln-161 |
| Antigenic Index - Jameson-Wolf | |
| SEQ. ID. NO. 34343 | 6-ValArgAlaArgGlyGlyPheIleAsp-14 |
| SEQ. ID. NO. 34344 | 21-AlaAspAsnLysHisPhe-26 |
| SEQ. ID. NO. 34345 | 40-AlaLeuArgArgLeuPro-45 |
| SEQ. ID. NO. 34346 | 53-ThrGlnProArgGlyAspAspGlyIleSerGlnAspAlaVal-66 |
| SEQ. ID. NO. 34347 | 86-TyrAspHisGlyAsn-90 |
| SEQ. ID. NO. 34348 | 107-ValPheGlyLysArgGlyPheGluPhe-115 |
| SEQ. ID. NO. 34349 | 130-GlnArgSerArgPheGlnAspAlaGlyGlnLysLeuArgAla-143 |
| SEQ. ID. NO. 34350 | 154-ArgLeuIleArgArgGlyLeuGln-161 |
| SEQ. ID. NO. 34351 | 193-ArgAlaHisArgValGly-198 |
| SEQ. ID. NO. 34352 | 202-PheLysPheGlyArgAsnArgArgAla-210 |
| SEQ. ID. NO. 34353 | 216-GlnArgGlyProValValLysArgArgAlaGln-226 |
| SEQ. ID. NO. 34354 | 230-GlyLysPheArgArgArgArgIleArgValGlyIleGluAsnGly-244 |
| SEQ. ID. NO. 34355 | 251-PheSerGlyAsnGlyLysHisSerAla-259 |
| Hydrophilic Regions - Hopp-Woods | |
| SEQ. ID. NO. 34356 | 6-ValArgAlaArgGlyGlyPheIle-13 |
| SEQ. ID. NO. 34357 | 21-AlaAspAsnLysHisPhe-26 |
| SEQ. ID. NO. 34358 | 40-AlaLeuArgArgLeuPro-45 |
| SEQ. ID. NO. 34359 | 53-ThrGlnProArgGlyAspAspGlyIleSer-62 |

| | |
|---|---|
| SEQ. ID. NO. 34360 | 130-GlnArgSerArgPheGlnAspAlaGlyGlnLysLeuArgAla-143 |
| SEQ. ID. NO. 34361 | 154-ArgLeuIleArgArgGlyLeu-160 |
| SEQ. ID. NO. 34362 | 193-ArgAlaHisArgValGly-198 |
| SEQ. ID. NO. 34363 | 205-GlyArgAsnArgArgAla-210 |
| SEQ. ID. NO. 34364 | 210-ProValValLysArgArgAlaGln-226 |
| SEQ. ID. NO. 34365 | 230-GlyLysPheArgArgArgArgIleArgValGlyIle-241 |
| SEQ. ID. NO. 34366 | 253-GlyAsnGlyLysHisSerAla-259 |
| g661 | |
| AMPHI Regions - AMPHI | |
| SEQ. ID. NO. 34367 | 19-GlyIleAlaAspLysProPheArgArgLeuCysArgAlaPheGlyAla-34 |
| SEQ. ID. NO. 34368 | 48-LeuArgAsnThrGlyLysThrLeu-55 |
| SEQ. ID. NO. 34369 | 76-ProGluGlnMetAlaAsp-81 |
| SEQ. ID. NO. 34370 | 122-AlaAlaIleLeuGluAlaValValLys-130 |
| SEQ. ID. NO. 34371 | 152-ProAlaValAlaLysIleAlaGlu-159 |
| SEQ. ID. NO. 34372 | 222-HisAspArgAlaArg-226 |
| SEQ. ID. NO. 34373 | 237-PheGluAlaLeuCysArg-242 |
| SEQ. ID. NO. 34374 | 246-PheThrAlaCysLeuGluPhe-252 |
| Antigenic Index - Jameson-Wolf | |
| SEQ. ID. NO. 34375 | 20-IleAlaAspLysProPheArgArgLeuCysArg-30 |
| SEQ. ID. NO. 34376 | 45-AspProThrLeuArgAsnThrGlyLysThrLeuHisArgSerAspPheAlaAspGluGlyGly-65 |
| SEQ. ID. NO. 34377 | 72-AlaGlySerAspProGluGlnMetAlaAspAlaAlaArg-84 |
| SEQ. ID. NO. 34378 | 97-AsnMetGlyCysProAlaLysLysValCys-106 |
| SEQ. ID. NO. 34379 | 115-MetGlnAspGluProLeu-120 |
| SEQ. ID. NO. 34380 | 143-GlyTrpHisAspAspAspGlnAsnLeu-151 |
| SEQ. ID. NO. 34381 | 156-LysIleAlaGluAspCysGly-162 |
| SEQ. ID. NO. 34382 | 169-ProArgAlaArgAla-173 |
| SEQ. ID. NO. 34383 | 175-AlaAsnValGlnArgArgGlyAlaLeuArgThrHisArgArgAspGlnLysProSerGluHisProGlyLeuGlyGlnArgArgHisHisPheAla AlaLysSerArgArgArgProGlnThrAsnArgArgArgArgHisHisAspArgAlaArgArgAlaArgGln-230 |
| SEQ. ID. NO. 34384 | 241-CysArgThrArgArgPhe-246 |
| SEQ. ID. NO. 34385 | 253-GlyArgMetGlnSerArgHisPheGluProHisProArgHisAlaArg-268 |
| SEQ. ID. NO. 34386 | 271-TrpXxxAspArgArgCysAlaHisArgThrGlnThrHisArgLeuValHisArgArgAsnAlaArgArgArgThrGlyAlaAla-298 |
| Hydrophilic Regions - Hopp-Woods | |
| SEQ. ID. NO. 34387 | 20-IleAlaAspLysProPheArgArgLeuCysArg-30 |
| SEQ. ID. NO. 34388 | 46-ProThrLeuArgAsnThrGlyLysThrLeuHisArgSerAspPheAlaAspGluGlyGly-65 |
| SEQ. ID. NO. 34389 | 73-GlySerAspProGluGlnMetAlaAspAlaAlaArg-84 |
| SEQ. ID. NO. 34390 | 100-CysProAlaLysLysValCys-106 |
| SEQ. ID. NO. 34391 | 115-MetGlnAspGluProLeu-120 |
| SEQ. ID. NO. 34392 | 144-TrpHisAspAspAspGlnAsn-150 |
| SEQ. ID. NO. 34393 | 156-LysIleAlaGluAspCysGly-162 |
| SEQ. ID. NO. 34394 | 169-ProArgAlaArgAla-173 |
| SEQ. ID. NO. 34395 | 175-AlaAsnValGlnArgArgGlyAlaLeuArgThrHisArgArgAspGlnLysProSerGluHisProGlyLeuGlyGlnArgArgHisHisPhe-205 |
| SEQ. ID. NO. 34396 | 207-AlaLysSerArgArgArgProGlnThrAsnArgArgArgArgHisHisAspArgAlaArgArgAlaArgGln-230 |
| SEQ. ID. NO. 34397 | 241-CysArgThrArgArgPhe-246 |
| SEQ. ID. NO. 34398 | 253-GlyArgMetGlnSerArgHisPheGluProHisProArgHisAla-267 |
| SEQ. ID. NO. 34399 | 271-TrpXxxAspArgArgCysAlaHisArgThrGlnThr-282 |
| SEQ. ID. NO. 34400 | 285-LeuValHisArgArgAsnAlaArgArgArgThrGlyAla-297 |
| g663 | |
| AMPHI Regions - AMPHI | |
| SEQ. ID. NO. 34401 | 19-ProPheAlaLeuLeuHisLysIleAlaGlyLeuIleGlySerLeuAlaTyr-35 |
| SEQ. ID. NO. 34402 | 66-LysGlnHisPheLysHisMetAlaLysLeu-75 |
| SEQ. ID. NO. 34403 | 86-SerAlaLysCysLeuLysSerLeuValArg-95 |
| SEQ. ID. NO. 34404 | 168-GluGlyLeuArgAlaLeuValLysGlnPheArgLys-179 |
| SEQ. ID. NO. 34405 | 209-ThrIleThrGlyLeuSerArgIleAlaAlaLeuAlaAsn-221 |
| SEQ. ID. NO. 34406 | 243-ProAlaTrpLysSer-247 |
| SEQ. ID. NO. 34407 | 258-GlnArgMetAsnArgPheIleGluGluArgValArgGluHis-271 |
| Antigenic Index - Jameson-Wolf | |
| SEQ. ID. NO. 34408 | 38-ValLysProArgArgArgIleGlyGlu-46 |
| SEQ. ID. NO. 34409 | 54-ProGluTrpAspGluGluLysArgLysThrValLeu-65 |
| SEQ. ID. NO. 34410 | 87-AlaLysCysLeuLysSer-92 |
| SEQ. ID. NO. 34411 | 94-ValArgTyrArgAsnLysHisTyrLeuAsp-103 |
| SEQ. ID. NO. 34412 | 105-AlaLeuAlaAlaGlyGluLys-111 |
| SEQ. ID. NO. 34413 | 139-TyrSerHisGlnLysAsnLysIleLeuAsp-148 |
| SEQ. ID. NO. 34414 | 150-GlnIleLeuLysGlyArgAsnArgTyr-158 |
| SEQ. ID. NO. 34415 | 166-ArgThrGluGlyLeuArgAlaLeu-173 |
| SEQ. ID. NO. 34416 | 175-LysGlnPheArgLysSerSerAla-182 |
| SEQ. ID. NO. 34417 | 188-ProAspGlnAspPheGlyArgAsnAsnSer-197 |
| SEQ. ID. NO. 34418 | 229-ProValArgGluAlaAspAsnThrVal-237 |
| SEQ. ID. NO. 34419 | 243-ProAlaTrpLysSerPheProSerGluAspAlaGlnAlaAspAlaGlnArgMetAsnArgPheIleGluGluArgValArgGluHisProGlu-273 |
| SEQ. ID. NO. 34420 | 280-LysArgPheLysThrArgProGluGlySerProAspPheTyr-293 |
| Hydrophilic Regions - Hopp-Woods | |
| SEQ. ID. NO. 34421 | 39-LysProArgArgArgIleGlyGlu-46 |
| SEQ. ID. NO. 34422 | 54-ProGluTrpAspGluGluLysArgLysThrValLeu-65 |
| SEQ. ID. NO. 34423 | 88-LysCysLeuLysSer-92 |
| SEQ. ID. NO. 34424 | 94-ValArgTyrArgAsn-98 |
| SEQ. ID. NO. 34425 | 105-AlaLeuAlaAlaGlyGluLys-111 |
| SEQ. ID. NO. 34426 | 142-GlnLysAsnLysIleLeuAsp-148 |
| SEQ. ID. NO. 34427 | 150-GlnIleLeuLysGlyArgAsnArgTyr-158 |
| SEQ. ID. NO. 34428 | 166-ArgThrGluGlyLeuArgAlaLeu-173 |
| SEQ. ID. NO. 34429 | 176-GlnPheArgLysSerSer-181 |
| SEQ. ID. NO. 34430 | 190-GlnAspPheGlyArg-194 |

TABLE 1-continued

| | |
|---|---|
| SEQ. ID. NO. 34431 | 229-ProValArgGluAlaAspAsn-235 |
| SEQ. ID. NO. 34432 | 248-PheProSerGluAspAlaGlnAlaAspAlaGlnArgMetAsnArgPheIleGluGluArgValArgGluHisProGlu-273 |
| SEQ. ID. NO. 34433 | 280-LysArgPheLysThrArgProGluGlySerPro-290 | g664
AMPHI Regions - AMPHI

| | |
|---|---|
| SEQ. ID. NO. 34434 | 28-AlaHisArgMetGly-32 |
| SEQ. ID. NO. 34435 | 47-AlaAspValLeuAspAlaAlaHisGlyAlaAlaGly-58 |
| SEQ. ID. NO. 34436 | 90-ProValValGluIle-94 |
| SEQ. ID. NO. 34437 | 158-LeuHisArgValPheSerThrIleProArg-167 |

Antigenic Index - Jameson-Wolf

| | |
|---|---|
| SEQ. ID. NO. 34438 | 26-AspGlyAlaHisArgMetGlyGlyArgAla-35 |
| SEQ. ID. NO. 34439 | 73-PheLeuGlnArgLysLeuGluPro-80 |
| SEQ. ID. NO. 34440 | 113-AlaValGlyGluAspGluLeuGlyVal-121 |
| SEQ. ID. NO. 34441 | 138-TyrGlyAspAspHisGluAsn-144 |
| SEQ. ID. NO. 34442 | 163-SerThrIleProArgGlnSerArgProTrp-172 |
| SEQ. ID. NO. 34443 | 175-ProLeuArgTrpCysLysThrArgPhe-183 |

Hydrophilic Regions - Hopp-Woods

| | |
|---|---|
| SEQ. ID. NO. 34444 | 27-GlyAlaHisArgMetGlyGly-33 |
| SEQ. ID. NO. 34445 | 74-LeuGlnArgLysLeuGluPro-80 |
| SEQ. ID. NO. 34446 | 113-AlaValGlyGluAspGluLeuGlyVal-121 |
| SEQ. ID. NO. 34447 | 138-TyrGlyAspAspHisGluAsn-144 |
| SEQ. ID. NO. 34448 | 166-ProArgGlnSerArg-170 | g665-1
AMPHI Regions - AMPHI

| | |
|---|---|
| SEQ. ID. NO. 34449 | 6-ArgTyrLeuLysAspTyrGln-12 |
| SEQ. ID. NO. 34450 | 115-GlnCysGluProGluGlyPheArgLysIleThr-125 |
| SEQ. ID. NO. 34451 | 132-AspValMetSerLysPheThrThrThr-140 |
| SEQ. ID. NO. 34452 | 167-ArgHisTrpValLysTrpGluAspProPhe-176 |
| SEQ. ID. NO. 34453 | 225-SerLeuLysAsnAlaMetLys-231 |
| SEQ. ID. NO. 34454 | 286-GlyIleGluSerValVal-291 |
| SEQ. ID. NO. 34455 | 294-GluTyrPheHisAsnTrpThr-300 |
| SEQ. ID. NO. 34456 | 307-ArgAspTrpPheGlnLeuSerLeu-314 |
| SEQ. ID. NO. 34457 | 329-AspArgAlaGlyArgAlaValArgArgIleGluAsnIleArgLeuLeuArgGln-346 |
| SEQ. ID. NO. 34458 | 358-HisProValArgProValSerTyrGluGluMetAsnAsnPheTyrThr-373 |
| SEQ. ID. NO. 34459 | 380-GlyAlaGluValValArgMetTyrHisThrLeu-390 |
| SEQ. ID. NO. 34460 | 396-PheGlnLysGlyMetLys-401 |
| SEQ. ID. NO. 34461 | 517-GluGlyValThrGluAlaValValProSerLeuLeuArgGlyPheSerAlaProVal-535 |
| SEQ. ID. NO. 34462 | 559-CysTrpGluAlaAla-563 |
| SEQ. ID. NO. 34463 | 575-LeuAlaAlaLeuSerAspGlyIle-582 |
| SEQ. ID. NO. 34464 | 589-LysLeuLeuAlaAlaValGlu-595 |
| SEQ. ID. NO. 34465 | 603-LeuAspAsnAlaPheLysAlaLeu-610 |
| SEQ. ID. NO. 34466 | 622-AspGlyThrGluAsnIleAspProLeu-630 |
| SEQ. ID. NO. 34467 | 642-ThrLeuAlaValArg-646 |
| SEQ. ID. NO. 34468 | 648-LeuProLysTrpHisGluLeuAspArg-656 |
| SEQ. ID. NO. 34469 | 674-AspTrpArgThrLeuArgAsnValCysArgAla-684 |
| SEQ. ID. NO. 34470 | 696-ThrValAlaGluLysTyrGlyGluMetAlaGlnAsnMet-708 |
| SEQ. ID. NO. 34471 | 712-TrpGlyIleLeuSer-716 |
| SEQ. ID. NO. 34472 | 730-LeuAlaGlnPheAlaAspLysPheSer-738 |
| SEQ. ID. NO. 34473 | 758-AspThrLeuGlnGlnValGlnThrAla-766 |
| SEQ. ID. NO. 34474 | 782-SerLeuIleGlySerPheSerArgAsnVal-791 |
| SEQ. ID. NO. 34475 | 822-ArgLeuValGlnAlaPheAsnLeuCysAsnLysLeu-833 |

Antigenic Index - Jameson-Wolf

| | |
|---|---|
| SEQ. ID. NO. 34476 | 1-MetSerLysThrValArgTyrLeuLysAspTyrGlnThrProAla-15 |
| SEQ. ID. NO. 34477 | 32-ThrValValLysSerArgLeuThrValGluProGlnArgAlaGlyGlu-47 |
| SEQ. ID. NO. 34478 | 49-LeuValLeuAspGlySerAla-55 |
| SEQ. ID. NO. 34479 | 79-AlaAspValProSerGluArgPheThrVal-88 |
| SEQ. ID. NO. 34480 | 90-ValGluThrGluIleLeuProAlaGluAsnLysSerLeu-102 |
| SEQ. ID. NO. 34481 | 115-GlnCysGluProGluGlyPheArgLys-123 |
| SEQ. ID. NO. 34482 | 128-IleAspArgProAspValMetSer-135 |
| SEQ. ID. NO. 34483 | 142-ValAlaAspLysLysArgTyrPro-149 |
| SEQ. ID. NO. 34484 | 153-SerAsnGlyAsnLysIleAspGlyGlyGluPheSerAspGlyArgHisTrpValLysTrpGluAspProPheAlaLysProSer-180 |
| SEQ. ID. NO. 34485 | 191-AlaValThrGluAspArgPheThrThrMetSerGlyArgAsnValLysIle-207 |
| SEQ. ID. NO. 34486 | 211-ThrThrGluAlaAspLysProLysVal-219 |
| SEQ. ID. NO. 34487 | 230-MetLysTrpAspGluThrArgPhe-237 |
| SEQ. ID. NO. 34488 | 255-AsnMetGlyAlaMetGluAsnLysGlyLeu-264 |
| SEQ. ID. NO. 34489 | 275-AspSerArgThrAlaThrAspThrAspPheGluGlyIleGlu-288 |
| SEQ. ID. NO. 34490 | 295-TyrPheHisAsnTrpThrGlyAsnArgValThrCysArgAspTrp-309 |
| SEQ. ID. NO. 34491 | 313-SerLeuLysGluGly-317 |
| SEQ. ID. NO. 34492 | 322-ArgAspGlnGluPheSerGlyAspArgAlaGlyAlaValArgArgIleGluAsn-340 |
| SEQ. ID. NO. 34493 | 342-ArgLeuLeuArgGlnAsnGlnPheProGluAspAlaGlyProThrAlaisProValArgProValSerTyrGluGluMetAsn-369 |
| SEQ. ID. NO. 34494 | 376-ValTyrGluLysGlyAlaGluVal-383 |
| SEQ. ID. NO. 34495 | 394-GluGlyPheGlnLysGlyMet-400 |
| SEQ. ID. NO. 34496 | 404-PheGlnArgHisAspGlyGlnAlaValThrCysAspAspPheArgAlaAlaMet-421 |
| SEQ. ID. NO. 34497 | 437-SerGlnAlaGlyThrPro-442 |
| SEQ. ID. NO. 34498 | 444-LeuGluAlaGluGlyArgLeuLysAsnAsnVal-454 |
| SEQ. ID. NO. 34499 | 459-IleLysGlnThrValProProThrProAspMetAlaAspLysGlnPro-474 |
| SEQ. ID. NO. 34500 | 483-LeuLeuAsnArgAsnGlyGluAlaVal-491 |
| SEQ. ID. NO. 34501 | 494-AspTyrGlnGlyLysArgAlaThrGlu-502 |
| SEQ. ID. NO. 34502 | 508-ThrGluAlaGluGln-512 |
| SEQ. ID. NO. 34503 | 538-AsnTyrProTyrSerAspAspAspLeu-546 |

TABLE 1-continued

| | |
|---|---|
| SEQ. ID. NO. 34504 | 552-HisAspSerAspAla-556 |
| SEQ. ID. NO. 34505 | 578-LeuSerAspGlyIleGlyLeuProLysHisGluLysLeu-590 |
| SEQ. ID. NO. 34506 | 594-ValGluLysValIleSerAspAspLeuLeu-603 |
| SEQ. ID. NO. 34507 | 614-ValProSerGluAlaGluLeuTrpAspGlyThrGluAsnIleAspProLeuArg-631 |
| SEQ. ID. NO. 34508 | 633-HisGlnAlaArgGluAlaLeu-639 |
| SEQ. ID. NO. 34509 | 652-HisGluLeuAspArgGlnAlaAlaLysGlnGluAsnGlnSerTyrGluTyrSerProGluThrAlaAsp-674 |
| SEQ. ID. NO. 34510 | 676-ArgThrLeuArgAsnValCys-682 |
| SEQ. ID. NO. 34511 | 689-AlaAspProAlaHis-693 |
| SEQ. ID. NO. 34512 | 696-ThrValAlaGluLysTyrGlyGlu-703 |
| SEQ. ID. NO. 34513 | 718-ValAsnGlyAsnGluSerAspThrArgAsnCys-728 |
| SEQ. ID. NO. 34514 | 733-PheAlaAspLysPheSerAspAspAlaLeuVal-743 |
| SEQ. ID. NO. 34515 | 752-GlySerSerArgArgSerAspThrLeuGln-761 |
| SEQ. ID. NO. 34516 | 768-GlnHisProLysPheSerLeuGluAsnProAsnLysAlaArgSer-782 |
| SEQ. ID. NO. 34517 | 785-GlySerPheSerArgAsnValPro-792 |
| SEQ. ID. NO. 34518 | 796-AlaGlnAspGlySerGlyTyrArgPheIleAla-806 |
| SEQ. ID. NO. 34519 | 808-LysValIleGluIleAspArgPheAsnProGlnVal-819 |
| SEQ. ID. NO. 34520 | 831-AsnLysLeuGluProHisArgLysAsnLeuValLysGlnGluLeuGlnCys-847 |
| SEQ. ID. NO. 34521 | 849-ArgAlaGlnGluGlyLeuSerLysAspValGlyGluIleVal-862 |
| Hydrophilic Regions - Hopp-Woods | |
| SEQ. ID. NO. 34522 | 1-MetSerLysThrValArgTyrLeuLys-9 |
| SEQ. ID. NO. 34523 | 32-ThrValValLysSerArgLeuThrValGluProGlnArgAlaGlyGlu-47 |
| SEQ. ID. NO. 34524 | 81-ValProSerGluArgPheThrVal-88 |
| SEQ. ID. NO. 34525 | 90-ValGluThrGluIleLeuProAlaGluAsnLysSer-101 |
| SEQ. ID. NO. 34526 | 116-CysGluProGluGlyPheArg-122 |
| SEQ. ID. NO. 34527 | 129-AspArgProAspValMetSer-135 |
| SEQ. ID. NO. 34528 | 142-ValAlaAspLysLysArgTyr-148 |
| SEQ. ID. NO. 34529 | 154-AsnGlyAsnLysIleAspGlyGlyGluPheSerAsp-165 |
| SEQ. ID. NO. 34530 | 170-ValLysTrpGluAspProPheAla-177 |
| SEQ. ID. NO. 34531 | 191-AlaValThrGluAspArgPheThr-198 |
| SEQ. ID. NO. 34532 | 201-SerGlyArgAsnValLys-206 |
| SEQ. ID. NO. 34533 | 213-GluAlaAspLysProLysVal-219 |
| SEQ. ID. NO. 34534 | 230-MetLysTrpAspGluThrArgPhe-237 |
| SEQ. ID. NO. 34535 | 258-AlaMetGluAsnLysGly-263 |
| SEQ. ID. NO. 34536 | 275-AspSerArgThrAlaThrAspThrAspPheGluGlyIleGlu-288 |
| SEQ. ID. NO. 34537 | 313-SerLeuLysGluGly-317 |
| SEQ. ID. NO. 34538 | 322-ArgAspGlnGluPheSerGlyAspArgAlaGlyArgAlaValArgArgIleGluAsn-340 |
| SEQ. ID. NO. 34539 | 348-GlnPheProGluAspAlaGlyPro-355 |
| SEQ. ID. NO. 34540 | 363-ValSerTyrGluGluMetAsn-369 |
| SEQ. ID. NO. 34541 | 376-ValTyrGluLysGlyAlaGluVal-383 |
| SEQ. ID. NO. 34542 | 394-GluGlyPheGlnLysGlyMet-400 |
| SEQ. ID. NO. 34543 | 406-ArgHisAspGlyGln-410 |
| SEQ. ID. NO. 34544 | 413-ThrCysAspAspPheArgAlaAlaMet-421 |
| SEQ. ID. NO. 34545 | 444-LeuGluAlaGluGlyArgLeuLysAsnAsnVal-454 |
| SEQ. ID. NO. 34546 | 467-ProAspMetAlaAspLysGlnPro-474 |
| SEQ. ID. NO. 34547 | 495-TyrGlnGlyLysArgAlaThrGlu-502 |
| SEQ. ID. NO. 34548 | 508-ThrGluAlaGluGln-512 |
| SEQ. ID. NO. 34549 | 541-TyrSerAspAspAspLeu-546 |
| SEQ. ID. NO. 34550 | 552-HisAspSerAspAla-556 |
| SEQ. ID. NO. 34551 | 585-ProLysHisGluLysLeu-590 |
| SEQ. ID. NO. 34552 | 594-ValGluLysValIleSer-599 |
| SEQ. ID. NO. 34553 | 616-SerGluAlaGluLeu-620 |
| SEQ. ID. NO. 34554 | 622-AspGlyThrGluAsnIleAspPro-629 |
| SEQ. ID. NO. 34555 | 633-HisGlnAlaArgGluAlaLeu-639 |
| SEQ. ID. NO. 34556 | 652-HisGluLeuAspArgGlnAlaAlaLysGlnGluAsnGlnSer-665 |
| SEQ. ID. NO. 34557 | 668-TyrSerProGluThrAlaAsp-674 |
| SEQ. ID. NO. 34558 | 689-AlaAspProAlaHis-693 |
| SEQ. ID. NO. 34559 | 696-ThrValAlaGluLysTyrGlyGlu-703 |
| SEQ. ID. NO. 34560 | 719-AsnGlyAsnGluSerAspThrArgAsn-727 |
| SEQ. ID. NO. 34561 | 733-PheAlaAspLysPheSerAspAspAlaLeuVal-743 |
| SEQ. ID. NO. 34562 | 753-SerSerArgArgSerAspThrLeu-760 |
| SEQ. ID. NO. 34563 | 776-AsnProAsnLysAlaArgSer-782 |
| SEQ. ID. NO. 34564 | 797-GlnAspGlySerGly-801 |
| SEQ. ID. NO. 34565 | 808-LysValIleGluIleAspArgPheAsn-816 |
| SEQ. ID. NO. 34566 | 831-AsnLysLeuGluProHisArgLysAsnLeuValLysGlnGluLeuGlnCys-847 |
| SEQ. ID. NO. 34567 | 849-ArgAlaGlnGluGlyLeuSerLysAspValGlyGluIleVal-862 |
| g666 | |
| AMPHI Regions - AMPHI | |
| SEQ. ID. NO. 34568 | 24-AlaLeuIleMetSerMetVal-30 |
| SEQ. ID. NO. 34569 | 57-HisThrProGluHisValThrGly-64 |
| SEQ. ID. NO. 34570 | 89-GlyTyrAspIleLeuLysGlnGlyGlySer-98 |
| SEQ. ID. NO. 34571 | 162-LeuLysPheMetGluAlaValVal-169 |
| Antigenic Index - Jameson-Wolf | |
| SEQ. ID. NO. 34572 | 6-TyrGlnSerAsnSerGlyGluGlyValLeu-15 |
| SEQ. ID. NO. 34573 | 40-AsnGlnGlyLysValAsnThr-46 |
| SEQ. ID. NO. 34574 | 55-AspAlaHisThrProGluHis-61 |
| SEQ. ID. NO. 34575 | 63-ThrGlyLeuThrGluGlnLysGln-70 |
| SEQ. ID. NO. 34576 | 80-SerAlaAsnProLeuAla-85 |
| SEQ. ID. NO. 34577 | 92-IleLeuLysGlnGlyGlySerAlaAla-100 |
| SEQ. ID. NO. 34578 | 114-GluProGlnSerSerGlyLeuGlyGly-122 |
| SEQ. ID. NO. 34579 | 130-AspAsnThrAlaLysThr-135 |

TABLE 1-continued

SEQ. ID. NO. 34580   137-ThrThrPheAspGlyArgGluThrAlaPro-146
SEQ. ID. NO. 34581   154-PheLeuAspLysAspGlyXxxProLeuLys-163
Hydrophilic Regions - Hopp-Woods
SEQ. ID. NO. 34582   40-AsnGlnGlyLysValAsnThr-46
SEQ. ID. NO. 34583   66-ThrGluGlnLysGln-70
SEQ. ID. NO. 34584   96-GlyGlySerAlaAla-100
SEQ. ID. NO. 34585   139-PheAspGlyArgGluThrAlaPro-146
SEQ. ID. NO. 34586   154-PheLeuAspLysAspGlyXxxPro-161
g667
AMPHI Regions - AMPHI
SEQ. ID. NO. 34587   46-PheAlaIleIleAlaAsp-51
SEQ. ID. NO. 34588   56-AlaArgValGluArgPheProHisPheAlaAla-66
SEQ. ID. NO. 34589   71-LeuAlaArgLysAlaAlaGlnPhe-78
SEQ. ID. NO. 34590   115-IleAlaAlaValAlaGluIle-121
SEQ. ID. NO. 34591   153-AlaAspGlnLeuArgArgMetPhePheAsnGlnPheGluLysLeuGlyAsnHisAsp-171
SEQ. ID. NO. 34592   202-GluValValLeuHisLysIleAlaAlaGlyLeu-212
Antigenic Index - Jameson-Wolf
SEQ. ID. NO. 34593   7-LeuGlyGlyGluIleValSerAspProCysAspPhe-18
SEQ. ID. NO. 34594   25-ValGluSerAlaAlaAspGlnThrGluThrGln-35
SEQ. ID. NO. 34595   56-AlaArgValGluArg-60
SEQ. ID. NO. 34596   71-LeuAlaArgLysAlaAlaGln-77
SEQ. ID. NO. 34597   84-ArgHisIleArgProArgLeuValLysArgGluGlnIle-96
SEQ. ID. NO. 34598   152-ProAlaAspGlnLeuArg-157
SEQ. ID. NO. 34599   165-GluLysLeuGlyAsnHisAspPhe-172
SEQ. ID. NO. 34600   192-HisThrAlaGlyAsnArgHisAsnLeu-200
SEQ. ID. NO. 34601   225-ValIleArgGlnGlyArgArgGlnValIleGlnArgThrAspThrLeu-240
SEQ. ID. NO. 34602   248-IleGluSerGlnAsnArgIleHisGlySerThrLeuHisSerLysThrAspLeu-265
Hydrophilic Regions - Hopp-Woods
SEQ. ID. NO. 34603   11-IleValSerAspProCysAsp-17
SEQ. ID. NO. 34604   25-ValGluSerAlaAlaAspGlnThrGluThrGln-35
SEQ. ID. NO. 34605   56-AlaArgValGluArg-60
SEQ. ID. NO. 34606   71-LeuAlaArgLysAlaAlaGln-77
SEQ. ID. NO. 34607   84-ArgHisIleArgProArgLeuValLysArgGluGlnIle-96
SEQ. ID. NO. 34608   165-GluLysLeuGlyAsn-169
SEQ. ID. NO. 34609   227-ArgGlnGlyArgArgGlnValIleGlnArgThrAspThr-239
SEQ. ID. NO. 34610   250-SerGlnAsnArgIleHis-255
SEQ. ID. NO. 34611   259-LeuHisSerLysThrAspLeu-265
g669
AMPHI Regions - AMPHI
SEQ. ID. NO. 34612   24-LysLeuHisArgAlaPhe-29
SEQ. ID. NO. 34613   59-GlnIlePheArgHisValGlnSer-66
SEQ. ID. NO. 34614   79-LysProProAsnThrAla-84
Antigenic Index - Jameson-Wolf
SEQ. ID. NO. 34615   1-MetArgArgIleValLysLysHisGlnProValAsnAla-13
SEQ. ID. NO. 34616   33-GlyArgLysArgProHisHisHisAspArgSerLeuArgArgGlnHisGlyIleGluGlyMetGlyPhe-55
SEQ. ID. NO. 34617   64-ValGlnSerSerAsnArgGlnSerGlyArgGlnProValCysThrLysProProAsnThrAlaSer-85
SEQ. ID. NO. 34618   100-AlaAspIleLysArgIleLeu-106
Hydrophilic Regions - Hopp-Woods
SEQ. ID. NO. 34619   1-MetArgArgIleValLysLysHisGlnPro-10
SEQ. ID. NO. 34620   33-GlyArgLysArgProHisHisHisAspArgSerLeuArgArgGlnHisGly-49
SEQ. ID. NO. 34621   65-GlnSerSerAsnArgGlnSerGlyArgGlnProValCysThrLysProProAsn-82
SEQ. ID. NO. 34622   100-AlaAspIleLysArgIleLeu-106
g670
AMPHI Regions - AMPHI
SEQ. ID. NO. 34623   10-ArgSerCysPheGly-14
SEQ. ID. NO. 34624   16-ValLysAsnAlaSerGlyValSer-23
SEQ. ID. NO. 34625   34-IleThrArgSerAla-38
SEQ. ID. NO. 34626   126-PheSerAlaCysSerAlaPheCysProLeu-135
Antigenic Index - Jameson-Wolf
SEQ. ID. NO. 34627   4-CysArgAsnCysLeuAlaArgSerCys-12
SEQ. ID. NO. 34628   18-AsnAlaSerGlyValSerSerSerArgIleCysProLeuSer-31
SEQ. ID. NO. 34629   33-LysIleThrArgSerAlaThrSerArgAlaAsnProIle-45
SEQ. ID. NO. 34630   65-AsnThrSerProThrIleSerGlySerSerAlaGluValGlySerSerAsnSerIleThrArgGlySerIleAlaSerProArgAlaIleAla-95
SEQ. ID. NO. 34631   100-TrpProProGluSerTrpGluGlyLysAla-109
SEQ. ID. NO. 34632   114-AlaSerProThrArgSerLysSerSer-122
SEQ. ID. NO. 34633   128-AlaCysSerAlaPhe-132
SEQ. ID. NO. 34634   146-AsnThrValArgCysGly-151
Hydrophilic Regions - Hopp-Woods
SEQ. ID. NO. 34635   33-LysIleThrArgSerAlaThrSerArgAlaAsn-43
SEQ. ID. NO. 34636   73-SerSerAlaGluValGlySer-79
SEQ. ID. NO. 34637   116-ProThrArgSerLysSer-121
g671
AMPHI Regions - AMPHI
SEQ. ID. NO. 34638   11-PheAsnAlaProAsn-15
SEQ. ID. NO. 34639   72-LysGlyAlaAlaLys-76
SEQ. ID. NO. 34640   119-ArgLeuPheIleArgTyr-124
Antigenic Index - Jameson-Wolf
SEQ. ID. NO. 34641   9-ThrProPheAsnAlaProAsnThrProProLysMetArgLeuAlaLysProArgProThrAlaGluThrAlaProValSerSerGluArg-38
SEQ. ID. NO. 34642   45-GlnAlaMetThrAsnArgGluMetAsnAspArgAlaAsnAlaAsnArgArgGlyTrpAsnGluAlaLysAlaArgSerAlaLysGlyAlaAla-75
SEQ. ID. NO. 34643   77-SerLeuAlaLysLysLysGluThrThr-85

TABLE 1-continued

| SEQ. ID. NO. 34644 | 110-AlaGluAlaArgArgSerAlaMet-117 |

Hydrophilic Regions - Hopp-Woods

| SEQ. ID. NO. 34645 | 16-ThrProProLysMetArgLeuAlaLysProArgProThrAlaGlu-30 |
| SEQ. ID. NO. 34646 | 32-AlaProValSerSerGluArg-38 |
| SEQ. ID. NO. 34647 | 47-MetThrAsnArgGluMetAsnAspArgAlaAsnAlaAsnArgArgGlyTrpAsnGluAlaLysAlaArgSerAlaLysGlyAlaAla-75 |
| SEQ. ID. NO. 34648 | 77-SerLeuAlaLysLysLysGluThrThr-85 |
| SEQ. ID. NO. 34649 | 110-AlaGluAlaArgArgSerAlaMet-117 | g672

AMPHI Regions - AMPHI

| SEQ. ID. NO. 34650 | 38-ArgAlaIleAspIleIleLysAlaGlnLys-47 |
| SEQ. ID. NO. 34651 | 50-AlaAlaLeuProProPheValSerValVal-59 |
| SEQ. ID. NO. 34652 | 67-AlaGlnAsnIleArgArgIleLeuAlaGluValPro-78 |
| SEQ. ID. NO. 34653 | 91-AlaPheCysArgGlnPheAspArgProTyr-100 |
| SEQ. ID. NO. 34654 | 105-ArgValGlnThrAlaSerAspIle-112 |
| SEQ. ID. NO. 34655 | 115-AlaAlaThrArgPheProAsn-121 |
| SEQ. ID. NO. 34656 | 131-HisProSerGluTyrGly-136 |
| SEQ. ID. NO. 34657 | 163-ProGluAsnValGlyGluAlaValArg-171 |
| SEQ. ID. NO. 34658 | 173-ThrGlyAlaGluAla-177 |

Antigenic Index - Jameson-Wolf

| SEQ. ID. NO. 34659 | 1-MetArgLysIleArgThrLysIleCysGlyIleThrThrProGluAspAlaLeu-18 |
| SEQ. ID. NO. 34660 | 34-ProGlnSerProArgAlaIleAspIleIleLysAlaGlnLys-47 |
| SEQ. ID. NO. 34661 | 65-GluSerAlaGlnAsnIleArgArgIleLeuAla-75 |
| SEQ. ID. NO. 34662 | 84-PheHisGlyAspGluAspAspAlaPhe-92 |
| SEQ. ID. NO. 34663 | 95-GlnPheAspArgProTyrIle-101 |
| SEQ. ID. NO. 34664 | 107-GlnThrAlaSerAspIleArgAsnAlaAla-116 |
| SEQ. ID. NO. 34665 | 130-TyrHisProSerGluTyrGlyGlyThrGlyHisArgPheAsp-143 |
| SEQ. ID. NO. 34666 | 149-GluTyrSerGlyLysPro-154 |
| SEQ. ID. NO. 34667 | 159-GlyGlyLeuThrProGluAsnValGlyGluAlaValArg-171 |
| SEQ. ID. NO. 34668 | 176-GluAlaValAspValSerGlyGlyValGluAlaSerLysGlyLysLysAspProAlaLys-195 |
| SEQ. ID. NO. 34669 | 202-ThrAlaAsnArgLeuSerArg-208 |

Hydrophilic Regions - Hopp-Woods

| SEQ. ID. NO. 34670 | 1-MetArgLysIleArgThrLysIle-8 |
| SEQ. ID. NO. 34671 | 13-ThrProGluAspAlaLeu-18 |
| SEQ. ID. NO. 34672 | 36-SerProArgAlaIleAsp-41 |
| SEQ. ID. NO. 34673 | 43-IleLysAlaGlnLys-47 |
| SEQ. ID. NO. 34674 | 66-SerAlaGlnAsnIleArgArgIleLeuAla-75 |
| SEQ. ID. NO. 34675 | 85-HisGlyAspGluAspAspAlaPhe-92 |
| SEQ. ID. NO. 34676 | 110-SerAspIleArgAsnAlaAla-116 |
| SEQ. ID. NO. 34677 | 165-AsnValGlyGluAlaValArg-171 |
| SEQ. ID. NO. 34678 | 184-ValGluAlaSerLysGlyLysLysAspProAlaLys-195 |
| SEQ. ID. NO. 34679 | 204-AsnArgLeuSerArg-208 | g673

AMPHI Regions - AMPHI

| SEQ. ID. NO. 34680 | 84-LeuAsnAspArgLeuAsnGlnAsnValThrGluAlaLeuGlyGlyValAspVal-101 |
| SEQ. ID. NO. 34681 | 110-ArgLeuThrAspAla-114 |
| SEQ. ID. NO. 34682 | 117-ValValLeuLysGlnLeuProLys-124 |
| SEQ. ID. NO. 34683 | 172-ArgIleAlaAsnLeuLeuGluLeuLeuLysProTyrLeu-184 |
| SEQ. ID. NO. 34684 | 212-LysLeuPheArgTyrLeuGlyGluGlu-220 |
| SEQ. ID. NO. 34685 | 232-PheGluGluGlyAspGly-237 |
| SEQ. ID. NO. 34686 | 261-GlyGluArgLeuLysLysIleSerThr-269 |
| SEQ. ID. NO. 34687 | 286-LysValTrpValLysValLys-292 |

Antigenic Index - Jameson-Wolf

| SEQ. ID. NO. 34688 | 7-LeuAlaGlyGluArgAlaAlaGlyGlyTyrArg-17 |
| SEQ. ID. NO. 34689 | 24-ValGlyArgProAsnValGlyLysSerThr-33 |
| SEQ. ID. NO. 34690 | 44-SerIleThrSerLysLysAlaGlnThrThrArgAsnArgValThr-58 |
| SEQ. ID. NO. 34691 | 61-TyrThrAspAspThrAla-66 |
| SEQ. ID. NO. 34692 | 73-ThrProGlyPheGlnThrAspHisArgAsnAlaLeuAsnAspArgLeuAsnGlnAsnValThrGlu-94 |
| SEQ. ID. NO. 34693 | 109-MetArgLeuThrAspAlaAspArgValVal-118 |
| SEQ. ID. NO. 34694 | 121-GlnLeuProLysHisThr-126 |
| SEQ. ID. NO. 34695 | 134-LysIleAspLysAspLysAlaLysAspArgTyrAla-145 |
| SEQ. ID. NO. 34696 | 153-ValArgAlaGluPhe-157 |
| SEQ. ID. NO. 34697 | 180-LeuLysProTyrLeuProGluSerVal-188 |
| SEQ. ID. NO. 34698 | 190-MetTyrProGluAspMetValThrAspLysSerAlaArg-202 |
| SEQ. ID. NO. 34699 | 208-IleValArgGluLysLeuPhe-214 |
| SEQ. ID. NO. 34700 | 217-LeuGlyGluGluLeuPro-222 |
| SEQ. ID. NO. 34701 | 227-ValGluValGluGlnPheGluGluGlyAspGlyLeuAsn-239 |
| SEQ. ID. NO. 34702 | 247-ValAspLysGluSerGlnLys-253 |
| SEQ. ID. NO. 34703 | 258-GlyLysGlyGlyGluArgLeuLysLysIleSerThrGluAlaArgLeuAspMetGluLysLeuPheAspAsnLysVal-283 |
| SEQ. ID. NO. 34704 | 291-ValLysSerGlyTrpAlaAspAspIleArgPheLeuArg-303 |

Hydrophilic Regions - Hopp-Woods

| SEQ. ID. NO. 34705 | 7-LeuAlaGlyGluArgAlaAlaGly-14 |
| SEQ. ID. NO. 34706 | 45-IleThrSerLysLysAlaGlnThrThrArgAsnArgVal-57 |
| SEQ. ID. NO. 34707 | 61-TyrThrAspAspThrAla-66 |
| SEQ. ID. NO. 34708 | 78-ThrAspHisArgAsnAlaLeuAsnAspArgLeuAsn-89 |
| SEQ. ID. NO. 34709 | 109-MetArgLeuThrAspAlaAspArgValVal-118 |
| SEQ. ID. NO. 34710 | 134-LysIleAspLysAspLysAlaLysAspArgTyrAla-145 |
| SEQ. ID. NO. 34711 | 153-ValArgAlaGluPhe-157 |
| SEQ. ID. NO. 34712 | 194-AspMetValThrAspLysSerAlaArg-202 |
| SEQ. ID. NO. 34713 | 208-IleValArgGluLysLeuPhe-214 |
| SEQ. ID. NO. 34714 | 217-LeuGlyGluGluLeuPro-222 |

TABLE 1-continued

| | |
|---|---|
| SEQ. ID. NO. 34715 | 227-ValGluValGluGlnPheGluGluGlyAspGlyLeuAsn-239 |
| SEQ. ID. NO. 34716 | 247-ValAspLysGluSerGlnLys-253 |
| SEQ. ID. NO. 34717 | 259-LysGlyGlyGluArgLeuLysLysIleSerThrGluAlaArgLeuAspMetGluLysLeuPheAsp-280 |
| SEQ. ID. NO. 34718 | 293-SerGlyTrpAlaAspAspIleArgPheLeuArg-303 | g674
AMPHI Regions - AMPHI

| | |
|---|---|
| SEQ. ID. NO. 34719 | 16-ValTyrGlnSerLeuIle-21 |
| SEQ. ID. NO. 34720 | 24-ThrAlaAlaProGluIleAlaLysAsnIleArgGluMetSerAspPheAlaLysAlaAspGluGluLeu-46 |
| SEQ. ID. NO. 34721 | 58-AlaAlaAspTyrIleGlnLysIleArg-66 |
| SEQ. ID. NO. 34722 | 86-ThrAlaCysHisGluLeuSerAlaMetProGluThr-97 |
| SEQ. ID. NO. 34723 | 107-IleGluValThrLysThrPheGlyGlyThrAspGlyHisLysPheValAsnGlyIleLeuAspLysLeuAla-130 |

Antigenic Index - Jameson-Wolf

| | |
|---|---|
| SEQ. ID. NO. 34724 | 1-MetLysThrAlaArgArgArgSerArgGluLeuAla-12 |
| SEQ. ID. NO. 34725 | 28-GluIleAlaLysAsnIleArgGluMetSerAspPheAlaLysAlaAspGluGluLeuPhe-47 |
| SEQ. ID. NO. 34726 | 54-ThrGlnThrAsnAla-58 |
| SEQ. ID. NO. 34727 | 61-TyrIleGlnLysIleArgProLeuLeuAspArgAspGluLysAspLeuAsnProIleGluArg-81 |
| SEQ. ID. NO. 34728 | 93-AlaMetProGluThrProTyr-99 |
| SEQ. ID. NO. 34729 | 105-GluAlaIleGluValThrLysThrPheGlyGlyThrAspGlyHisLysPhe-121 |
| SEQ. ID. NO. 34730 | 129-LeuAlaAlaGlnIleArgProAspGluProLysArgArg-141 |

Hydrophilic Regions - Hopp-Woods

| | |
|---|---|
| SEQ. ID. NO. 34731 | 1-MetLysThrAlaArgArgArgSerArgGluLeuAla-12 |
| SEQ. ID. NO. 34732 | 28-GluIleAlaLysAsnIleArgGluMetSerAspPheAlaLysAlaAspGluGluLeuPhe-47 |
| SEQ. ID. NO. 34733 | 63-GlnLysIleArgProLeuLeuAspArgAspGluLysAspLeuAsnProIleGluArg-81 |
| SEQ. ID. NO. 34734 | 105-GluAlaIleGluVal-109 |
| SEQ. ID. NO. 34735 | 133-IleArgProAspGluProLysArgArg-141 | g675
AMPHI Regions - AMPHI

| | |
|---|---|
| SEQ. ID. NO. 34736 | 21-ArgPheThrAsnGluIleGlySerGlnMetLeuLysValCysCysArgThrLeuGlnGluLeuGly-42 |
| SEQ. ID. NO. 34737 | 74-AlaLeuIleAlaIle-78 |
| SEQ. ID. NO. 34738 | 123-GlnAlaIleGluArgIleGlyGluLysAlaSerAsp-134 |
| SEQ. ID. NO. 34739 | 141-GluCysAlaAsnLeuValAsnLeuLeuLeuGlu-151 |

Antigenic Index - Jameson-Wolf

| | |
|---|---|
| SEQ. ID. NO. 34740 | 6-ProAsnLeuAspGlyLysHisLeuArg-14 |
| SEQ. ID. NO. 34741 | 42-GlyValAlaAspGluAsnIle-48 |
| SEQ. ID. NO. 34742 | 68-SerSerGluLysPheAsp-73 |
| SEQ. ID. NO. 34743 | 82-IleArgGlyGluThrTyr-87 |
| SEQ. ID. NO. 34744 | 93-AlaAsnGluSerGlyAlaGlyIle-100 |
| SEQ. ID. NO. 34745 | 118-ThrGluAsnAspAlaGlnAlaIleGluArgIleGlyGluLysAlaSerAspAlaAlaLysValAlaVal-140 |
| SEQ. ID. NO. 34746 | 152-GluGlnPheGluAspGluGlu-158 |

Hydrophilic Regions - Hopp-Woods

| | |
|---|---|
| SEQ. ID. NO. 34747 | 8-LeuAspGlyLysHisLeuArg-14 |
| SEQ. ID. NO. 34748 | 42-GlyValAlaAspGluAsnIle-48 |
| SEQ. ID. NO. 34749 | 68-SerSerGluLysPheAsp-73 |
| SEQ. ID. NO. 34750 | 82-IleArgGlyGluThrTyr-87 |
| SEQ. ID. NO. 34751 | 95-GluSerGlyAlaGly-99 |
| SEQ. ID. NO. 34752 | 118-ThrGluAsnAspAlaGlnAlaIleGluArgIleGlyGluLysAlaSerAspAlaAlaLysValAlaVal-140 |
| SEQ. ID. NO. 34753 | 152-GluGlnPheGluAspGluGlu-158 | g677
AMPHI Regions - AMPHI

| | |
|---|---|
| SEQ. ID. NO. 34754 | 19-ThrValArgLeuCysArgPheArgArg-27 |
| SEQ. ID. NO. 34755 | 45-LeuThrAlaPheArgArgValGlnAsnHisPheValAlaPheAlaArgPheAsnGlnAlaThrArgGlnArgArg-69 |
| SEQ. ID. NO. 34756 | 79-IleAspPheIleAspAlaAsp-85 |
| SEQ. ID. NO. 34757 | 87-PheAspGlyLeuLeuAla-92 |
| SEQ. ID. NO. 34758 | 155-CysArgProValAspAspLeuAspAsp-163 |
| SEQ. ID. NO. 34759 | 166-AlaPhePheIleAspGlnLeuIleLysLeuValPheGlnCys-179 |

Antigenic Index - Jameson-Wolf

| | |
|---|---|
| SEQ. ID. NO. 34760 | 23-CysArgPheArgArgHisSerArgSerValAsp-33 |
| SEQ. ID. NO. 34761 | 35-AspValPheAspArgLysAspPheAsnPhe-44 |
| SEQ. ID. NO. 34762 | 63-GlnAlaThrArgGlnArgArgAsnProArgAsnPheVal-75 |
| SEQ. ID. NO. 34763 | 82-IleAspAlaAspAspPheAspGly-89 |
| SEQ. ID. NO. 34764 | 97-GlnGlnThrAspGlyArgAlaGluLys-105 |
| SEQ. ID. NO. 34765 | 115-GlyIleAspAspAspGlySerLeu-122 |
| SEQ. ID. NO. 34766 | 125-PheGlyGlnGluThrAspAlaAlaVal-133 |
| SEQ. ID. NO. 34767 | 156-ArgProValAspAspLeuAspAspPheGly-165 |
| SEQ. ID. NO. 34768 | 181-ProSerGlyGlyArgAsn-186 |

Hydrophilic Regions - Hopp-Woods

| | |
|---|---|
| SEQ. ID. NO. 34769 | 23-CysArgPheArgArgHisSerArgSerValAsp-33 |
| SEQ. ID. NO. 34770 | 35-AspValPheAspArgLysAspPhe-42 |
| SEQ. ID. NO. 34771 | 63-GlnAlaThrArgGlnArgArgAsnProArg-72 |
| SEQ. ID. NO. 34772 | 82-IleAspAlaAspAspPheAsp-88 |
| SEQ. ID. NO. 34773 | 97-GlnGlnThrAspGlyArgAlaGluLys-105 |
| SEQ. ID. NO. 34774 | 115-GlyIleAspAspAspGlySer-121 |
| SEQ. ID. NO. 34775 | 126-GlyGlnGluThrAspAlaAlaVal-133 |
| SEQ. ID. NO. 34776 | 156-ArgProValAspAspLeuAspAsp-163 | g678
AMPHI Regions - AMPHI

| | |
|---|---|
| SEQ. ID. NO. 34777 | 24-MetArgGlyValIle-28 |
| SEQ. ID. NO. 34778 | 47-PheAlaAlaProPhe-51 |
| SEQ. ID. NO. 34779 | 80-IleGlnLysMetLeuArgSerLeuLeuThrGlyAla-91 |
| SEQ. ID. NO. 34780 | 102-ArgIleLeuGlyGlyValPheGlyAlaLeu-111 |

TABLE 1-continued

SEQ. ID. NO. 34781	130-ProAspThrGluGlu-134
Antigenic Index - Jameson-Wolf
SEQ. ID. NO. 34782	125-SerLysThrAspLeuProAspThrGluGluTrpGlnGlnSerTyr-139
SEQ. ID. NO. 34783	153-AsnHisThrAspAsnAlaProGluSerLeuAspAspAsp-165
Hydrophilic Regions - Hopp-Woods
SEQ. ID. NO. 34784	125-SerLysThrAspLeuProAspThrGluGluTrpGln-136
SEQ. ID. NO. 34785	155-ThrAspAsnAlaProGluSerLeuAspAspAsp-165
g681
AMPHI Regions - AMPHI
SEQ. ID. NO. 34786	12-PheSerGluGluAlaLysPheIleSerAlaMet-22
SEQ. ID. NO. 34787	110-CysAlaValPheGlyLysLeuProArg-118
SEQ. ID. NO. 34788	123-LeuGlyLysGlnCysGly-128
SEQ. ID. NO. 34789	137-ValGlyGluAlaAspAspAla-143
SEQ. ID. NO. 34790	146-ValGlyValValGlyValPheVal-153
SEQ. ID. NO. 34791	202-LysCysValHisCysGlyAsnThr-209
SEQ. ID. NO. 34792	212-GlyGlyLysLeuAlaAspPheThrThrIleProAla-223
SEQ. ID. NO. 34793	235-CysAlaProPheAlaAlaLeuArgCysPheCysIlePheGlyValTrpLysArgIleArgAlaValPheCysGlyArg-260
Antigenic Index - Jameson-Wolf
SEQ. ID. NO. 34794	11-AsnPheSerGluGluAlaLysPhe-18
SEQ. ID. NO. 34795	39-AlaThrProAsnSerTrpArgValArgGlnGln-49
SEQ. ID. NO. 34796	59-LeuValLysArgAlaCys-64
SEQ. ID. NO. 34797	67-ProMetArgArgCysLeuProSerArgLeu-76
SEQ. ID. NO. 34798	91-SerGluCysArgLeuLys-96
SEQ. ID. NO. 34799	122-GlyLeuGlyLysGlnCysGlyGlyPhe-130
SEQ. ID. NO. 34800	134-PheGlyAspValGlyGluAlaAspAspAlaGluVal-145
SEQ. ID. NO. 34801	157-AlaAlaGluGluThrPro-162
SEQ. ID. NO. 34802	173-AlaValLysGluAlaAspGly-179
SEQ. ID. NO. 34803	185-AspGlyValGlyGlyAspAlaAlaValGluCysArgGlyLysCysLeuCys-201
SEQ. ID. NO. 34804	209-ThrLeuGlyGlyGlyLysLeuAlaAsp-217
SEQ. ID. NO. 34805	224-LeuSerAlaAspGlyGlyGly-230
SEQ. ID. NO. 34806	257-PheCysGlyArgArg-261
Hydrophilic Regions - Hopp-Woods
SEQ. ID. NO. 34807	11-AsnPheSerGluGluAlaLysPhe-18
SEQ. ID. NO. 34808	44-TrpArgValArgGln-48
SEQ. ID. NO. 34809	59-LeuValLysArgAlaCys-64
SEQ. ID. NO. 34810	67-ProMetArgArgCysLeuPro-73
SEQ. ID. NO. 34811	91-SerGluCysArgLeuLys-96
SEQ. ID. NO. 34812	136-AspValGlyGluAlaAspAspAlaGluVal-145
SEQ. ID. NO. 34813	157-AlaAlaGluGluThrPro-162
SEQ. ID. NO. 34814	173-AlaValLysGluAlaAspGly-179
SEQ. ID. NO. 34815	191-AlaAlaValGluCysArgGlyLysCysLeu-200
SEQ. ID. NO. 34816	257-PheCysGlyArgArg-261
g682
AMPHI Regions - AMPHI
SEQ. ID. NO. 34817	33-ArgLeuArgLysCysGlyArgIleLeuSerGlyIleCysGluProPhe-48
SEQ. ID. NO. 34818	75-IleLysMetProSerGluPro-81
SEQ. ID. NO. 34819	91-AlaGlyPheIleArgPhePro-97
Antigenic Index - Jameson-Wolf
SEQ. ID. NO. 34820	9-ProTyrGlyGluArgArgLysAsnTrpAsp-18
SEQ. ID. NO. 34821	29-LeuSerProThrArgLeuArgLysCysGlyArg-39
SEQ. ID. NO. 34822	70-CysValAsnAspGluIleLysMetProSerGluProAspTrp-83
SEQ. ID. NO. 34823	95-ArgPheProThrAspArgProIleLeu-103
SEQ. ID. NO. 34824	112-IleSerProArgThrGlyPheArgTyrProThrArgSerLeuProLysSerLysLysAlaTyrGly-133
Hydrophilic Regions - Hopp-Woods
SEQ. ID. NO. 34825	11-GlyGluArgArgLysAsnTrpAsp-18
SEQ. ID. NO. 34826	30-SerProThrArgLeuArgLysCysGlyArg-39
SEQ. ID. NO. 34827	72-AsnAspGluIleLysMetProSerGluProAspTrp-83
SEQ. ID. NO. 34828	97-ProThrAspArgProIleLeu-103
SEQ. ID. NO. 34829	124-SerLeuProLysSerLysLysAlaTyrGly-133
g683
AMPHI Regions - AMPHI
SEQ. ID. NO. 34830	26-ThrProAspLysSerAlaArgTrpGluAsnIleGlyThrIleSerAsn-41
SEQ. ID. NO. 34831	75-ArgPheAlaAsnThrPro-80
SEQ. ID. NO. 34832	101-SerSerLeuGlnLeuPhe-106
SEQ. ID. NO. 34833	124-ArgProMetSerIleLeuSerGly-131
Antigenic Index - Jameson-Wolf
SEQ. ID. NO. 34834	24-CysSerThrProAspLysSerAlaArgTrpGluAsn-35
SEQ. ID. NO. 34835	37-GlyThrIleSerAsnGly-42
SEQ. ID. NO. 34836	48-IleAsnLysAspSerValArgLysAsnGlyAsn-58
SEQ. ID. NO. 34837	63-GlnAspLysLysValValThrAsnLeuLysGlnGluArgPheAlaAsnThrProAlaTyr-82
SEQ. ID. NO. 34838	93-CysAsnAsnLysThrTyrArgLeu-100
SEQ. ID. NO. 34839	106-PheAspThrLysAsnThrGluIleSerThrGlnAsnTyrThrAlaSerSerLeuArgPro-125
SEQ. ID. NO. 34840	131-GlyThrLeuThrGluLysGlnTyrGlu-139
SEQ. ID. NO. 34841	141-ValCysGlyLysLysLeu-146
Hydrophilic Regions - Hopp-Woods
SEQ. ID. NO. 34842	25-SerThrProAspLysSerAlaArgTrpGluAsn-35
SEQ. ID. NO. 34843	48-IleAsnLysAspSerValArgLysAsnGly-57
SEQ. ID. NO. 34844	63-GlnAspLysLysValValThr-69
SEQ. ID. NO. 34845	71-LeuLysGlnGluArgPheAla-77
SEQ. ID. NO. 34846	107-AspThrLysAsnThrGluIleSer-114

TABLE 1-continued

| | |
|---|---|
| SEQ. ID. NO. 34847 | 133-LeuThrGluLysGlnTyrGlu-139 |
| SEQ. ID. NO. 34848 | 141-ValCysGlyLysLysLeu-146 | g684
AMPHI Regions - AMPHI

| | |
|---|---|
| SEQ. ID. NO. 34849 | 13-AlaAlaCysGlyThrValGln-19 |
| SEQ. ID. NO. 34850 | 47-LeuAlaGluProLeu-51 |
| SEQ. ID. NO. 34851 | 73-TrpAlaAspThrLeuAspAspMetLeuGluAlaAlaLeuSerAsnAlaPheAsnArgLeuAspSerThrArg-96 |
| SEQ. ID. NO. 34852 | 110-TrpThrValTyrIleAspAlaPheGlnGlySerTyr-121 |
| SEQ. ID. NO. 34853 | 154-AlaMetThrAlaAlaLeuGluGlnGlyLeuLysGlnAlaAlaGlnGlnMetVal-171 |

Antigenic Index - Jameson-Wolf

| | |
|---|---|
| SEQ. ID. NO. 34854 | 26-LeuProAspSerArgTyrIleArgProAlaThrGlnGlyGlyGluThrAlaValGluValArgLeuAlaGluProLeuLysArgGlyGlyLeu-56 |
| SEQ. ID. NO. 34855 | 60-ThrAspProTyrArgIleAsnThrAlaGln-69 |
| SEQ. ID. NO. 34856 | 76-ThrLeuAspAspMetLeuGlu-82 |
| SEQ. ID. NO. 34857 | 90-AsnArgLeuAspSerThrArgThrPhe-98 |
| SEQ. ID. NO. 34858 | 101-AlaSerArgSerGlySerThrAspLys-109 |
| SEQ. ID. NO. 34859 | 117-PheGlnGlySerTyrThrGlyLysThrLeu-126 |
| SEQ. ID. NO. 34860 | 133-LeuProAspGlyThrAsnArgProPheHisIleGluThrGluGlnGlnGlyAspGlyTyrAla-153 |
| SEQ. ID. NO. 34861 | 161-GlnGlyLeuLysGlnAlaAla-167 |

Hydrophilic Regions - Hopp-Woods

| | |
|---|---|
| SEQ. ID. NO. 34862 | 27-ProAspSerArgTyrIleArg-33 |
| SEQ. ID. NO. 34863 | 35-AlaThrGlnGlyGlyGluThrAlaValGluValArgLeuAlaGluProLeuLysArgGlyGly-55 |
| SEQ. ID. NO. 34864 | 76-ThrLeuAspAspMetLeuGlu-82 |
| SEQ. ID. NO. 34865 | 90-AsnArgLeuAspSerThrArg-96 |
| SEQ. ID. NO. 34866 | 102-SerArgSerGlySerThrAspLys-109 |
| SEQ. ID. NO. 34867 | 141-PheHisIleGluThrGluGlnGlnGlyAsp-150 |
| SEQ. ID. NO. 34868 | 161-GlnGlyLeuLysGlnAlaAla-167 | g685
AMPHI Regions - AMPHI

| | |
|---|---|
| SEQ. ID. NO. 34869 | 7-AsnPheAlaPheCysGlyValVal-14 |
| SEQ. ID. NO. 34870 | 44-CysAlaValLeuPro-48 |
| SEQ. ID. NO. 34871 | 61-ValSerAlaAlaSerGln-66 |
| SEQ. ID. NO. 34872 | 98-TrpAlaAlaLeuAspThrLeuThrGluPro-107 |
| SEQ. ID. NO. 34873 | 141-CysGluSerLeuHisArgHis-147 |
| SEQ. ID. NO. 34874 | 158-GlyAlaGluAlaTyrGluGlnLeuAlaLysAsn-168 |
| SEQ. ID. NO. 34875 | 186-GluLysGlnMetGluThrLeuSerArgIlePheGly-197 |
| SEQ. ID. NO. 34876 | 300-AlaValGluValLeu-304 |
| SEQ. ID. NO. 34877 | 340-AlaAlaGluGlnLeuLysAlaAla-347 |

Antigenic Index - Jameson-Wolf

| | |
|---|---|
| SEQ. ID. NO. 34878 | 20-LeuAsnAsnLysHisSerTyrSerTyrAlaLysGluProHisThrValLysProArgPhe-39 |
| SEQ. ID. NO. 34879 | 51-CysSerProGluProAlaAlaGluLysThrValSer-62 |
| SEQ. ID. NO. 34880 | 78-ProThrAlaArgGlyAspAlaValValProLysAsnProGluArgValAla-94 |
| SEQ. ID. NO. 34881 | 103-ThrLeuThrGluProGlyVal-109 |
| SEQ. ID. NO. 34882 | 126-AlaPheAspLysAlaAla-131 |
| SEQ. ID. NO. 34883 | 137-PheGluProAspCysGluSerLeuHisArgHisAsnPro-149 |
| SEQ. ID. NO. 34884 | 155-GlyGlyProGlyAlaGluAlaTyrGluGlnLeuAlaLysAsnAlaThr-170 |
| SEQ. ID. NO. 34885 | 174-LeuThrValAspAsnGlyAsnIleArgThrSerGlyGluLysGlnMetGluThrLeu-192 |
| SEQ. ID. NO. 34886 | 195-IlePheGlyLysGluAlaArgValAlaGlu-204 |
| SEQ. ID. NO. 34887 | 213-PheAlaGlnLysArgGluAlaAlaLysGlyLysGlyArgGlyLeu-227 |
| SEQ. ID. NO. 34888 | 231-ValThrGlyAsnLysValSerAlaPheGlyThrGlnSerArgLeu-245 |
| SEQ. ID. NO. 34889 | 251-GlyAspIleGlyLeuProProValAspGluSerLeuArgAsnGluGlyHisGlyGln-269 |
| SEQ. ID. NO. 34890 | 275-TyrIleLysGluLysAsnProGlyTrp-283 |
| SEQ. ID. NO. 34891 | 289-ArgThrAlaAlaIleGlyGlnGluGlyProAla-299 |
| SEQ. ID. NO. 34892 | 313-AsnAlaTrpLysArgLysGln-319 |
| SEQ. ID. NO. 34893 | 342-GluGlnLeuLysAlaAlaPheGluLysAlaGluProValAla-355 |

Hydrophilic Regions - Hopp-Woods

| | |
|---|---|
| SEQ. ID. NO. 34894 | 28-TyrAlaLysGluProHisThrValLys-36 |
| SEQ. ID. NO. 34895 | 51-CysSerProGluProAlaAlaGluLysThrValSer-62 |
| SEQ. ID. NO. 34896 | 79-ThrAlaArgGlyAspAlaValVal-86 |
| SEQ. ID. NO. 34897 | 88-LysAsnProGluArgValAla-94 |
| SEQ. ID. NO. 34898 | 126-AlaPheAspLysAlaAla-131 |
| SEQ. ID. NO. 34899 | 137-PheGluProAspCysGluSerLeuHisArgHis-147 |
| SEQ. ID. NO. 34900 | 160-GluAlaTyrGluGlnLeuAlaLys-167 |
| SEQ. ID. NO. 34901 | 179-GlyAsnIleArgThrSerGlyGluLysGlnMetGluThrLeu-192 |
| SEQ. ID. NO. 34902 | 195-IlePheGlyLysGluAlaArgValAlaGlu-204 |
| SEQ. ID. NO. 34903 | 213-PheAlaGlnLysArgGluAlaAlaLysGlyLysGlyArgGly-226 |
| SEQ. ID. NO. 34904 | 257-ProValAspGluSerLeuArgAsnGluGlyHisGly-268 |
| SEQ. ID. NO. 34905 | 275-TyrIleLysGluLysAsnPro-281 |
| SEQ. ID. NO. 34906 | 294-GlyGlnGluGlyProAla-299 |
| SEQ. ID. NO. 34907 | 314-AlaTrpLysArgLysGln-319 |
| SEQ. ID. NO. 34908 | 342-GluGlnLeuLysAlaAlaPheGluLysAlaGluProValAla-355 | g686
AMPHI Regions - AMPHI

| | |
|---|---|
| SEQ. ID. NO. 34909 | 10-AspValPheAspAspIleCysSerAlaValGluGlyPheGlyGlyIleAlaArgSerValGlnLeu-31 |
| SEQ. ID. NO. 34910 | 50-SerAlaGlyIleValGluThrValGlyLysProLeu-61 |
| SEQ. ID. NO. 34911 | 70-ValGluAlaAspIle-74 |
| SEQ. ID. NO. 34912 | 86-IleProArgAlaPheGlySerGlyIleAlaAlaAlaLeu-98 |

Antigenic Index - Jameson-Wolf

| | |
|---|---|
| SEQ. ID. NO. 34913 | 1-TerTerAsnPheSerCysArgAlaAspAspValPheAsp-13 |
| SEQ. ID. NO. 34914 | 46-LeuArgGlnHisSerAlaGlyIle-53 |
| SEQ. ID. NO. 34915 | 56-ThrValGlyLysProLeuSerGlyAla-64 |

TABLE 1-continued

| | |
|---|---|
| SEQ. ID. NO. 34916 | 70-ValGluAlaAspIle-74 |
| SEQ. ID. NO. 34917 | 115-AspAlaValLysAlaGluSerValAsnGlyThrThrGly-127 |

Hydrophilic Regions - Hopp-Woods

| | |
|---|---|
| SEQ. ID. NO. 34918 | 6-CysArgAlaAspAspValPheAsp-13 |
| SEQ. ID. NO. 34919 | 70-ValGluAlaAspIle-74 |
| SEQ. ID. NO. 34920 | 115-AspAlaValLysAlaGluSerValAsn-123 | g687
AMPHI Regions - AMPHI

| | |
|---|---|
| SEQ. ID. NO. 34921 | 13-AlaAlaLeuPheAlaLeu-18 |
| SEQ. ID. NO. 34922 | 66-LysValGluValLeuGluPhePheGlyTyrPheCysPro-78 |
| SEQ. ID. NO. 34923 | 80-CysAlaArgLeuGluPro-85 |
| SEQ. ID. NO. 34924 | 87-LeuSerLysHisAlaLysSerPhe-94 |
| SEQ. ID. NO. 34925 | 114-LeuAlaArgLeuAlaAlaAla-120 |
| SEQ. ID. NO. 34926 | 137-PheAspAlaMetVal-141 |
| SEQ. ID. NO. 34927 | 150-ProGluValLeuLysLysTrpLeu-157 |
| SEQ. ID. NO. 34928 | 174-SerProGluSerGln-178 |
| SEQ. ID. NO. 34929 | 182-GlyLysMetGlnGluLeuThrGluThrPhe-191 |

Antigenic Index - Jameson-Wolf

| | |
|---|---|
| SEQ. ID. NO. 34930 | 1-MetLysSerArgHis-5 |
| SEQ. ID. NO. 34931 | 21-CysAspSerLysValGlnThrSerValProAlaAspSerAlaPro-35 |
| SEQ. ID. NO. 34932 | 45-GlyLeuValGluGlyGlnAsnTyr-52 |
| SEQ. ID. NO. 34933 | 58-ProIleProGlnGlnGlnAlaGlyLysValGluVal-69 |
| SEQ. ID. NO. 34934 | 77-CysProHisCysAlaArgLeuGluProValLeu-87 |
| SEQ. ID. NO. 34935 | 89-LysHisAlaLysSerPheLysAspAspMetTyrLeu-100 |
| SEQ. ID. NO. 34936 | 124-AlaAlaAlaGluSerLysAspValAlaAsn-133 |
| SEQ. ID. NO. 34937 | 143-GlnLysIleLysLeuGlnGluProGluValLeuLys-154 |
| SEQ. ID. NO. 34938 | 161-ThrAlaPheAspGlyLysLysVal-168 |
| SEQ. ID. NO. 34939 | 173-GluSerProGluSerGlnAlaArgAlaGlyLysMetGlnGluLeuThrGlu-189 |
| SEQ. ID. NO. 34940 | 191-PheGlnIleAspGlyThrPro-197 |
| SEQ. ID. NO. 34941 | 201-ValGlyGlyLysTyrLysValGluPheAlaAsp-211 |
| SEQ. ID. NO. 34942 | 213-GluSerGlyMetAsnThr-218 |
| SEQ. ID. NO. 34943 | 222-LeuAlaAspLysValArgGluGluGlnLysAlaAlaGln-234 |

Hydrophilic Regions - Hopp-Woods

| | |
|---|---|
| SEQ. ID. NO. 34944 | 1-MetLysSerArgHis-5 |
| SEQ. ID. NO. 34945 | 21-CysAspSerLysValGlnThr-27 |
| SEQ. ID. NO. 34946 | 29-ValProAlaAspSerAlaPro-35 |
| SEQ. ID. NO. 34947 | 63-GlnAlaGlyLysValGluVal-69 |
| SEQ. ID. NO. 34948 | 81-AlaArgLeuGluProValLeu-87 |
| SEQ. ID. NO. 34949 | 89-LysHisAlaLysSerPheLysAspAspMetTyrLeu-100 |
| SEQ. ID. NO. 34950 | 124-AlaAlaAlaGluSerLysAspValAla-132 |
| SEQ. ID. NO. 34951 | 143-GlnLysIleLysLeuGlnGluProGluValLeuLys-154 |
| SEQ. ID. NO. 34952 | 161-ThrAlaPheAspGlyLysLysVal-168 |
| SEQ. ID. NO. 34953 | 173-GluSerProGluSerGlnAlaArgAlaGlyLysMetGlnGluLeuThrGlu-189 |
| SEQ. ID. NO. 34954 | 203-GlyLysTyrLysValGluPheAlaAsp-211 |
| SEQ. ID. NO. 34955 | 222-LeuAlaAspLysValArgGluGluGlnLysAlaAlaGln-234 | g688
AMPHI Regions - AMPHI

| | |
|---|---|
| SEQ. ID. NO. 34956 | 22-LeuSerAlaLeuPheSerLeu-28 |
| SEQ. ID. NO. 34957 | 119-GlyAspAlaLeuGlnAsnAlaAla-126 |

Antigenic Index - Jameson-Wolf

| | |
|---|---|
| SEQ. ID. NO. 34958 | 5-SerArgPheAlaGlnLysGlySerProValAsnLys-16 |
| SEQ. ID. NO. 34959 | 31-CysSerValGluArg-35 |
| SEQ. ID. NO. 34960 | 46-IleIleGlnGlyAsnGluLeuGluProArgAla-56 |
| SEQ. ID. NO. 34961 | 61-ArgProGlyMetThrLysAspGln-68 |
| SEQ. ID. NO. 34962 | 81-AlaPheHisThrAspArgTrpAspTyr-89 |
| SEQ. ID. NO. 34963 | 91-PheAsnThrSerArgAsnGlyIleIleLysGluArgSerAsnLeu-105 |
| SEQ. ID. NO. 34964 | 115-ValArgThrGluGlyAspAlaLeuGlnAsnAlaAlaGluAlaLeuArgAlaLysGlnAsnAlaAspLysGln-138 |

Hydrophilic Regions - Hopp-Woods

| | |
|---|---|
| SEQ. ID. NO. 34965 | 7-PheAlaGlnLysGlySerProVal-14 |
| SEQ. ID. NO. 34966 | 50-AsnGluLeuGluProArgAla-56 |
| SEQ. ID. NO. 34967 | 63-GlyMetThrLysAspGln-68 |
| SEQ. ID. NO. 34968 | 97-GlyIleIleLysGluArgSerAsn-104 |
| SEQ. ID. NO. 34969 | 115-ValArgThrGluGlyAspAlaLeuGlnAsnAlaAlaGluAlaLeuArgAlaLysGlnAsnAlaAspLysGln-138 | g689
AMPHI Regions - AMPHI

| | |
|---|---|
| SEQ. ID. NO. 34970 | 16-ValLeuMetAlaValLeuValAlaLeu-24 |
| SEQ. ID. NO. 34971 | 33-LeuProAlaIleProGluMetAlaGln-41 |
| SEQ. ID. NO. 34972 | 49-ArgIleGluSerLeu-53 |
| SEQ. ID. NO. 34973 | 62-PheGlyGlnValAlaGlyGly-68 |
| SEQ. ID. NO. 34974 | 73-IleLysGlyArgLys-77 |
| SEQ. ID. NO. 34975 | 103-LeuLeuAsnLeuArgAlaValGlnAlaPhe-112 |
| SEQ. ID. NO. 34976 | 138-PheAlaLeuIleGlyIleIleLeu-145 |
| SEQ. ID. NO. 34977 | 152-AlaProMetValGlyAlaLeuLeuGlnGlyLeuGlyGlyTrpArgAlaIlePheVal-170 |
| SEQ. ID. NO. 34978 | 177-ProValLeuProGlyLeuValGlnTyrPhe-186 |
| SEQ. ID. NO. 34979 | 195-LysIleGlyArgAspVal-200 |
| SEQ. ID. NO. 34980 | 207-ArgPheLysArgValLeu-212 |
| SEQ. ID. NO. 34981 | 227-SerPheGlySerMetPheAla-233 |
| SEQ. ID. NO. 34982 | 288-GlyIleValValGln-292 |
| SEQ. ID. NO. 34983 | 347-AlaAsnAlaValSerGlyValPheArgSerLeuIle-358 |

TABLE 1-continued

Antigenic Index - Jameson-Wolf
SEQ. ID. NO. 34984    1-TerTerSerProProLeuProProMetSerGlyLys-12
SEQ. ID. NO. 34985    46-AspIleHisArgIleGluSer-52
SEQ. ID. NO. 34986    71-SerAspIleLysGlyArgLysProVal-79
SEQ. ID. NO. 34987    98-SerSerThrGluGln-102
SEQ. ID. NO. 34988    124-MetValArgAspTyrTyrSerGlyArgLysAlaAla-135
SEQ. ID. NO. 34989    189-AsnProAlaValGlyGlyLysIleGlyArgAspVal-200
SEQ. ID. NO. 34990    207-ArgPheLysArgValLeuLysThrArgAla-216
SEQ. ID. NO. 34991    275-LeuLysThrGlyAlaHisProGlnSer-283
SEQ. ID. NO. 34992    340-PheLysGluGluGlyGlySerAla-347
SEQ. ID. NO. 34993    390-LysAlaTrpLysGluAsnGluLysLysArgIleLeu-401
Hydrophilic Regions - Hopp-Woods
SEQ. ID. NO. 34994    46-AspIleHisArgIleGluSer-52
SEQ. ID. NO. 34995    71-SerAspIleLysGlyArgLysProVal-79
SEQ. ID. NO. 34996    128-TyrTyrSerGlyArgLysAlaAla-135
SEQ. ID. NO. 34997    195-LysIleGlyArgAspVal-200
SEQ. ID. NO. 34998    207-ArgPheLysArgValLeuLysThrArgAla-216
SEQ. ID. NO. 34999    340-PheLysGluGluGlyGlySer-346
SEQ. ID. NO. 35000    390-LysAlaTrpLysGluAsnGluLysLysArgIleLeu-401
g690
AMPHI Regions - AMPHI
SEQ. ID. NO. 35001    38-SerSerAlaSerSer-42
SEQ. ID. NO. 35002    54-SerAlaProAspAsnValLysGlnAla-62
SEQ. ID. NO. 35003    73-HisProAlaAlaGlyIleGlyAspLeuIleGlnGlnIleAlaGluHisIle-89
SEQ. ID. NO. 35004    112-GlyTyrAspAsnIleGlnArgLeu-119
SEQ. ID. NO. 35005    146-ThrArgThrIleSerArgGlnAlaGlnAspAla-156
SEQ. ID. NO. 35006    185-ProLysArgAlaArgTyrPhe-191
SEQ. ID. NO. 35007    209-GlyAsnPheGlnTyrIleGlyGlnLeuProGlyTyrLeuLysMetHisGlyGluMet-227
Antigenic Index - Jameson-Wolf
SEQ. ID. NO. 35008    1-MetLysAsnLysThrSerSerLeu-8
SEQ. ID. NO. 35009    20-ArgSerProSerLysGluAspLysThrLysGluAsnGlyAla-33
SEQ. ID. NO. 35010    37-SerSerSerAlaSerSerAlaSerSerGlnThrAspLeuGlnPro-51
SEQ. ID. NO. 35011    54-SerAlaProAspAsnValLysGlnAlaGluSerAlaProLeuAsnCysThrGly-71
SEQ. ID. NO. 35012    86-AlaGluHisIleAspSerAspCys-93
SEQ. ID. NO. 35013    100-AsnGluLeuGluThrArgPhe-106
SEQ. ID. NO. 35014    108-LeuProGlyGlyGlyTyrAspAsnIleGln-117
SEQ. ID. NO. 35015    122-ProAspIleArgProGluAspProAspTyrHisGln-133
SEQ. ID. NO. 35016    140-GluAspLeuArgTyrGlyThrArgThrIleSerArgGlnAlaGln-154
SEQ. ID. NO. 35017    156-AlaIleMetGluGlnGluArgArgLeuArgGluAlaThr-168
SEQ. ID. NO. 35018    173-GlnGlySerGlnLysThrArgGlyGlnGlyGluGluProLysArgAlaArgTyr-190
SEQ. ID. NO. 35019    199-TyrLeuAsnArgHisAsnAsnGlyLeuGlyGlyAsn-210
SEQ. ID. NO. 35020    223-MetHisGlyGluMetLeuGluAsnGlnSerLeu-233
SEQ. ID. NO. 35021    235-ArgLeuSerAsnArgGluArgAsnProAspLysProPheLeu-248
SEQ. ID. NO. 35022    251-HisPheAspGluAsnGlyLysIleThr-259
SEQ. ID. NO. 35023    263-ValTyrGluLysAsnIle-268
Hydrophilic Regions - Hopp-Woods
SEQ. ID. NO. 35024    1-MetLysAsnLysThrSer-6
SEQ. ID. NO. 35025    20-ArgSerProSerLysGluAspLysThrLysGluAsnGlyAla-33
SEQ. ID. NO. 35026    39-SerAlaSerSerAlaSerSerGlnThrAspLeu-49
SEQ. ID. NO. 35027    54-SerAlaProAspAsnValLysGlnAlaGluSerAlaPro-66
SEQ. ID. NO. 35028    87-GluHisIleAspSer-91
SEQ. ID. NO. 35029    100-AsnGluLeuGluThr-104
SEQ. ID. NO. 35030    124-IleArgProGluAspProAspTyrHisGln-133
SEQ. ID. NO. 35031    140-GluAspLeuArgTyrGlyThr-146
SEQ. ID. NO. 35032    148-ThrIleSerArgGlnAlaGln-154
SEQ. ID. NO. 35033    156-AlaIleMetGluGlnGluArgArgLeuArgGluAlaThr-168
SEQ. ID. NO. 35034    174-GlySerGlnLysThrArgGlyGlnGlyGluGluProLysArgAlaArgTyr-190
SEQ. ID. NO. 35035    223-MetHisGlyGluMetLeuGlu-229
SEQ. ID. NO. 35036    236-LeuSerAsnArgGluArgAsnProAspLysProPhe-247
SEQ. ID. NO. 35037    251-HisPheAspGluAsnGlyLysIleThr-259
g691
AMPHI Regions - AMPHI
SEQ. ID. NO. 35038    11-LysProAlaAlaSer-15
SEQ. ID. NO. 35039    55-HisAsnGluLeuArgLysIleArgAla-63
SEQ. ID. NO. 35040    101-AlaArgAspTyrVal-105
Antigenic Index - Jameson-Wolf
SEQ. ID. NO. 35041    7-CysArgPheAlaLys-11
SEQ. ID. NO. 35042    35-ProProAsnAspPheGlnProAsnCysAspIleArgArgLeuGlyLeuThrGlnGlyGlnHisAsnGluLeuArgLysIleArgAla-63
SEQ. ID. NO. 35043    67-MetAlaGlyAspArgAlaArgLeuLysValMetHis-78
SEQ. ID. NO. 35044    80-GluHisSerArgArgArgSerVal-87
SEQ. ID. NO. 35045    91-IleSerSerAspValPheAsnArgAsnGluAlaArgAspTyrValGluSerArgTyrHisSerSerMet-113
SEQ. ID. NO. 35046    115-PheAlaValAspGluLeuGluIle-122
SEQ. ID. NO. 35047    131-ThrProGlnGlnGlnGln-136
SEQ. ID. NO. 35048    140-SerSerCysLeuLys-144
Hydrophilic Regions - Hopp-Woods
SEQ. ID. NO. 35049    43-CysAspIleArgArgLeuGly-49
SEQ. ID. NO. 35050    54-GlnHisAsnGluLeuArgLysIleArgAla-63
SEQ. ID. NO. 35051    67-MetAlaGlyAspArgAlaArgLeuLysValMetHis-78
SEQ. ID. NO. 35052    80-GluHisSerArgArgArgSerVal-87
SEQ. ID. NO. 35053    95-ValPheAsnArgAsnGluAlaArgAspTyrValGlu-106

TABLE 1-continued

| | |
|---|---|
| SEQ. ID. NO. 35054 | 115-PheAlaValAspGluLeuGluIle-122 | g692
AMPHI Regions - AMPHI

| | |
|---|---|
| SEQ. ID. NO. 35055 | 9-SerGluSerIleArgArgIleTrpArgAsnGlyArgGlu-21 |
| SEQ. ID. NO. 35056 | 58-PheValAlaLeuGluAla-63 |
| SEQ. ID. NO. 35057 | 77-LeuGlyTyrValPheLysProLeuAlaValPheVal-88 |
| SEQ. ID. NO. 35058 | 106-GlnGlyPheGlyGlnLeuHis-112 |
| SEQ. ID. NO. 35059 | 143-PheAspValPheGlnValPheArgAsp-151 |
| SEQ. ID. NO. 35060 | 179-CysGluValGlyArgValValGlyArgGlyTyrGlyAlaAlaValPheAspPhePheGlnArgPheGlnPhe-202 |
| SEQ. ID. NO. 35061 | 205-IleGlnSerGlnArgArgGlyArgHisLeuGluGlyPheGlyAsp-219 |
| SEQ. ID. NO. 35062 | 254-ValGlyLysPheAspGlnPheAspGlyVal-263 |
| SEQ. ID. NO. 35063 | 275-PheAspHisIleAlaGluVal-281 |
| SEQ. ID. NO. 35064 | 302-GlyGlyArgGlyCys-306 |

Antigenic Index - Jameson-Wolf

| | |
|---|---|
| SEQ. ID. NO. 35065 | 4-ThrArgCysArgCysSerGluSerIleArgArgIleTrpArgAsnGlyArgGluTrpArgIleLysGlyGlnLysCysArgLeuAsnThrAspAlaValGln-37 |
| SEQ. ID. NO. 35066 | 89-GlyGlyPheAspGlyArgProValAspIleGlyLysAlaArgLeuLeuGlu-105 |
| SEQ. ID. NO. 35067 | 120-AlaValAspAspGlyLysIle-126 |
| SEQ. ID. NO. 35068 | 136-CysGlyPheLysLeuAspAspPheAspVal-145 |
| SEQ. ID. NO. 35069 | 150-ArgAspValGlyPheGlyCysGlyGlnArgIle-160 |
| SEQ. ID. NO. 35070 | 177-GlyAlaCysGluValGlyArgValValGlyArgGlyTyr-189 |
| SEQ. ID. NO. 35071 | 204-ArgIleGlnSerGlnArgArgGlyArgHisLeuGluGlyPheGlyAsp-219 |
| SEQ. ID. NO. 35072 | 236-GluAspValAspVal-240 |
| SEQ. ID. NO. 35073 | 256-LysPheAspGlnPheAspGlyVal-263 |
| SEQ. ID. NO. 35074 | 282-AlaHisGlyArgAlaGluAspAspPhePhePhe-292 |
| SEQ. ID. NO. 35075 | 296-ValIleGlyArgArgGlyGlyGlyArgGlyCysGlyArg-308 |
| SEQ. ID. NO. 35076 | 316-GlyCysGluAspGluArgGluCysGlyGlyGlyLysGlyPheGluGlu-331 |

Hydrophilic Regions - Hopp-Woods

| | |
|---|---|
| SEQ. ID. NO. 35077 | 4-ThrArgCysArgCysSerGluSerIleArgArgIleTrpArgAsnGlyArgGluTrpArgIleLysGlyGlnLysCysArgLeuAsnThr-33 |
| SEQ. ID. NO. 35078 | 91-PheAspGlyArgProValAspIleGlyLysAlaArgLeuLeuGlu-105 |
| SEQ. ID. NO. 35079 | 120-AlaValAspAspGlyLysIle-126 |
| SEQ. ID. NO. 35080 | 139-LysLeuAspAspPheAsp-144 |
| SEQ. ID. NO. 35081 | 179-CysGluValGlyArgValValGly-186 |
| SEQ. ID. NO. 35082 | 206-GlnSerGlnArgArgGlyArgHisLeuGluGlyPheGly-218 |
| SEQ. ID. NO. 35083 | 236-GluAspValAspVal-240 |
| SEQ. ID. NO. 35084 | 282-AlaHisGlyArgAlaGluAspAspPhePhePhe-292 |
| SEQ. ID. NO. 35085 | 296-ValIleGlyArgArgGlyGlyGlyArgGlyCysGly-307 |
| SEQ. ID. NO. 35086 | 316-GlyCysGluAspGluArgGluCysGlyGly-325 |
| SEQ. ID. NO. 35087 | 327-LysGlyPheGluGlu-331 | g694
AMPHI Regions - AMPHI

| | |
|---|---|
| SEQ. ID. NO. 35088 | 13-LeuThrProAlaSerThr-18 |
| SEQ. ID. NO. 35089 | 69-ArgGlyArgAlaCysArg-74 |
| SEQ. ID. NO. 35090 | 88-GlnValGlyArgValVal-93 |
| SEQ. ID. NO. 35091 | 103-CysArgHisPheAlaGln-108 |
| SEQ. ID. NO. 35092 | 110-ValAlaValGlyArgIleGly-116 |
| SEQ. ID. NO. 35093 | 139-ArgArgIleAlaAspValPheLeuVal-147 |
| SEQ. ID. NO. 35094 | 149-IleAlaAspIleGlyGlu-154 |
| SEQ. ID. NO. 35095 | 171-ArgGlyLeuAlaAspIleGlyGluPheValGlyValSerAsp-184 |
| SEQ. ID. NO. 35096 | 194-PheAspGlnLysHisPheAlaArgCys-202 |
| SEQ. ID. NO. 35097 | 238-HisGlnArgAlaSerArgIleLys-245 |
| SEQ. ID. NO. 35098 | 270-ArgAlaArgArgHisPheArgGlnValPheAsp-280 |
| SEQ. ID. NO. 35099 | 298-AspPheValAlaHisIle-303 |
| SEQ. ID. NO. 35100 | 327-AlaAlaArgIleGlyLysAspAsp-334 |

Antigenic Index - Jameson-Wolf

| | |
|---|---|
| SEQ. ID. NO. 35101 | 34-GlyGlnAspGluHisAspAla-40 |
| SEQ. ID. NO. 35102 | 45-ProProPheAlaHisGlyPhe-51 |
| SEQ. ID. NO. 35103 | 53-ProProSerAlaTyrGlyCysGln-60 |
| SEQ. ID. NO. 35104 | 63-ProHisGlnHisPheGlyArgGlyArgAlaCysArgTyr-75 |
| SEQ. ID. NO. 35105 | 82-PheLysProArgAla-86 |
| SEQ. ID. NO. 35106 | 97-ArgIleAspSerAlaArgCysArgHis-105 |
| SEQ. ID. NO. 35107 | 113-GlyArgIleGlyArgThrAspHisAsnHisAsp-123 |
| SEQ. ID. NO. 35108 | 130-LeuPheAspGlyGlyLeuProValGlyArgArgIleAla-142 |
| SEQ. ID. NO. 35109 | 150-AlaAspIleGlyGluThrArgValGlnArgGlyAspAsp-162 |
| SEQ. ID. NO. 35110 | 167-IleAspArgGluArgGlyLeuAlaAsp-175 |
| SEQ. ID. NO. 35111 | 189-HisIleSerAspArgPheAspGlnLysHisPheAla-200 |
| SEQ. ID. NO. 35112 | 202-CysLysLeuProHisArgAlaPheAsp-210 |
| SEQ. ID. NO. 35113 | 214-ProLeuMetProAspHisAspAspPheThr-223 |
| SEQ. ID. NO. 35114 | 237-ArgHisGlnArgAlaSerArgIleLysTyrProGluThrAlaLeu-251 |
| SEQ. ID. NO. 35115 | 265-ArgIleAsnGlnCysArgAlaArgArgHisPhe-275 |
| SEQ. ID. NO. 35116 | 278-ValPheAspLysHisArg-283 |
| SEQ. ID. NO. 35117 | 303-IleAsnArgArgAlaGluPhe-309 |
| SEQ. ID. NO. 35118 | 313-ThrPheAspAsnThrAspCysProIleHisThrGlyAlaGluAlaAlaArgIleGlyLysAspAspGlyPheSer-337 |
| SEQ. ID. NO. 35119 | 344-ProCysSerAspGly-348 |
| SEQ. ID. NO. 35120 | 356-LeuCysAspGlyArgTyrCysGlnAlaProProThrProHisArgArgArg-372 |

Hydrophilic Regions - Hopp-Woods

| | |
|---|---|
| SEQ. ID. NO. 35121 | 34-GlyGlnAspGluHisAspAla-40 |
| SEQ. ID. NO. 35122 | 68-GlyArgGlyArgAlaCysArg-74 |
| SEQ. ID. NO. 35123 | 82-PheLysProArgAla-86 |
| SEQ. ID. NO. 35124 | 97-ArgIleAspSerAlaArgCysArgHis-105 |

TABLE 1-continued

| | |
|---|---|
| SEQ. ID. NO. 35125 | 114-ArgIleGlyArgThrAspHisAsnHis-122 |
| SEQ. ID. NO. 35126 | 137-ValGlyArgArgIleAla-142 |
| SEQ. ID. NO. 35127 | 150-AlaAspIleGlyGluThrArgValGlnArgGlyAspAsp-162 |
| SEQ. ID. NO. 35128 | 167-IleAspArgGluArgGlyLeuAlaAsp-175 |
| SEQ. ID. NO. 35129 | 189-HisIleSerAspArgPheAspGlnLysHisPheAla-200 |
| SEQ. ID. NO. 35130 | 202-CysLysLeuProHisArgAlaPhe-209 |
| SEQ. ID. NO. 35131 | 217-ProAspHisAspAsp-221 |
| SEQ. ID. NO. 35132 | 237-ArgHisGlnArgAlaSerArgIleLysTyrProGluThrAlaLeu-251 |
| SEQ. ID. NO. 35133 | 267-AsnGlnCysArgAlaArgArgHisPhe-275 |
| SEQ. ID. NO. 35134 | 278-ValPheAspLysHisArg-283 |
| SEQ. ID. NO. 35135 | 303-IleAsnArgArgAlaGluPhe-309 |
| SEQ. ID. NO. 35136 | 314-PheAspAsnThrAsp-318 |
| SEQ. ID. NO. 35137 | 325-AlaGluAlaAlaArgIleGlyLysAspAspGlyPheSer-337 |
| SEQ. ID. NO. 35138 | 367-ThrProHisArgArgArg-372 |
| g695 | |
| AMPHI Regions - AMPHI | |
| SEQ. ID. NO. 35139 | 34-GlnAsnSerGlnArg-38 |
| SEQ. ID. NO. 35140 | 41-SerLysProAlaGluArgTyrAlaAspCysProHis-52 |
| SEQ. ID. NO. 35141 | 83-AlaSerCysAlaSerValLeu-89 |
| SEQ. ID. NO. 35142 | 128-ValArgLeuSerAsnGluVal-134 |
| SEQ. ID. NO. 35143 | 157-ValGlnLysLeuAsp-161 |
| SEQ. ID. NO. 35144 | 182-ValGluThrAlaGlnAsnLeuTyrAsnGlnAlaLeuLysHisTyrGlnAsnGly-199 |
| SEQ. ID. NO. 35145 | 237-CysGluSerValIleGluIle-243 |
| SEQ. ID. NO. 35146 | 247-TyrAlaAsnArgPheLysAspSer-254 |
| SEQ. ID. NO. 35147 | 277-AlaArgAlaThrTrpArgSerLeuIleGlnThrTyrProGly-290 |
| Antigenic Index - Jameson-Wolf | |
| SEQ. ID. NO. 35148 | 1-LeuProGlnThrArgProAlaArgArgHisHisArgHisArgGlnTyrPheValGluArgLysGlyAspAlaArgSerGlyPhe-28 |
| SEQ. ID. NO. 35149 | 32-GlnCysGlnAsnSerGlnArgPheGlnSerLysProAlaGluArgTyrAlaAspCysProHisHisProAlaArgArgArgArgPheAspProAla SerGluLysIleMetLysThrLys-71 |
| SEQ. ID. NO. 35150 | 90-ProValProGluGlySerArgThrGluMetProThrGlnGluAsnAlaSerAspGlyIleProTyr-111 |
| SEQ. ID. NO. 35151 | 116-LeuGlnAspArgLeuAspTyrLeuGlu-124 |
| SEQ. ID. NO. 35152 | 126-LysIleValArgLeuSerAsnGluValGluMetLeuAsnGlyLysValLysAlaLeuGluHisThrLysIleHisProSerGlyArgThrTyrVal GlnLysLeuAspAspArgLysLeuLysGlu-167 |
| SEQ. ID. NO. 35153 | 169-TyrLeuAsnThrGluGlyGlySerAla-177 |
| SEQ. ID. NO. 35154 | 192-AlaLeuLysHisTyrGlnAsnGlyArg-200 |
| SEQ. ID. NO. 35155 | 208-LeuLysGlyAlaAspGlyGlyAspGlyGlySerIleAlaGln-221 |
| SEQ. ID. NO. 35156 | 229-GlnSerArgAlaArgMetGlyAsnCys-237 |
| SEQ. ID. NO. 35157 | 243-IleGlyGlyArgTyrAlaAsnArgPheLysAspSerProThrAla-257 |
| SEQ. ID. NO. 35158 | 265-GlyGluCysGlnTyr-269 |
| SEQ. ID. NO. 35159 | 271-LeuGlnGlnLysAspIleAla-277 |
| SEQ. ID. NO. 35160 | 288-TyrProGlySerProAlaAlaLysArgAlaAlaAlaAlaValArgLysArg-304 |
| Hydrophilic Regions - Hopp-Woods | |
| SEQ. ID. NO. 35161 | 2-ProGlnThrArgProAlaArgArgHisHisArgHisArg-14 |
| SEQ. ID. NO. 35162 | 17-PheValGluArgLysGlyAspAlaArgSer-26 |
| SEQ. ID. NO. 35163 | 35-AsnSerGlnArgPheGlnSerLysProAlaGluArgTyrAlaAsp-49 |
| SEQ. ID. NO. 35164 | 51-ProHisHisProAlaArgArgArgArgPheAspProAlaSerGluLysIleMetLysThrLys-71 |
| SEQ. ID. NO. 35165 | 92-ProGluGlySerArgThrGluMetProThrGlnGluAsnAlaSerAsp-107 |
| SEQ. ID. NO. 35166 | 116-LeuGlnAspArgLeuAspTyrLeuGlu-124 |
| SEQ. ID. NO. 35167 | 126-LysIleValArgLeuSerAsnGluValGluMetLeuAsnGlyLysValLysAlaLeuGluHisThrLysIleHisProSerGly-153 |
| SEQ. ID. NO. 35168 | 156-TyrValGlnLysLeuAspAspArgLysLeuLysGlu-167 |
| SEQ. ID. NO. 35169 | 209-LysGlyAlaAspGlyGlyAspGlyGlySerIleAlaGln-221 |
| SEQ. ID. NO. 35170 | 230-SerArgAlaArgMetGlyAsn-236 |
| SEQ. ID. NO. 35171 | 247-TyrAlaAsnArgPheLysAspSerProThrAla-257 |
| SEQ. ID. NO. 35172 | 265-GlyGluCysGlnTyr-269 |
| SEQ. ID. NO. 35173 | 271-LeuGlnGlnLysAspIleAla-277 |
| SEQ. ID. NO. 35174 | 292-ProAlaAlaLysArgAlaAlaAlaAlaValArgLysArg-304 |
| g700 | |
| AMPHI Regions - AMPHI | |
| SEQ. ID. NO. 35175 | 6-ThrLeuPheSerValLeuValProMetPheAlaGlyPhePheIleArgValProLys-24 |
| SEQ. ID. NO. 35176 | 51-ArgValGluAspLeuGlySerArg-58 |
| SEQ. ID. NO. 35177 | 80-AlaLeuAlaValLeuGlyLysLeu-87 |
| SEQ. ID. NO. 35178 | 189-GlyValSerTrpThrLysGlyLeu-196 |
| SEQ. ID. NO. 35179 | 204-TrpTyrSerLeuSerGlyLeuVal-211 |
| SEQ. ID. NO. 35180 | 216-TyrGlyAlaValTrp-220 |
| SEQ. ID. NO. 35181 | 228-AspLeuAlaArgGluLeu-233 |
| SEQ. ID. NO. 35182 | 268-GlyAlaGlyGlyLeu-272 |
| Antigenic Index - Jameson-Wolf | |
| SEQ. ID. NO. 35183 | 21-ArgValProLysProTyrLeuProAlaSerAspLysVal-33 |
| SEQ. ID. NO. 35184 | 50-SerArgValGluAspLeuGlySerArgLeuGlyAsp-61 |
| SEQ. ID. NO. 35185 | 88-SerProTrpArgIleGlyGlyLysGlyLysGlyVal-99 |
| SEQ. ID. NO. 35186 | 103-ValSerGlySerValArg-108 |
| SEQ. ID. NO. 35187 | 118-ValSerGlyLysLeuMet-123 |
| SEQ. ID. NO. 35188 | 128-MetProSerGluAsnAlaGlyMet-135 |
| SEQ. ID. NO. 35189 | 149-LeuLysSerSerGlyValSerLeu-156 |
| SEQ. ID. NO. 35190 | 160-LeuLeuAsnArgArgGlyIleArgLeu-168 |
| SEQ. ID. NO. 35191 | 245-ArgPheProAspAla-249 |
| SEQ. ID. NO. 35192 | 268-GlyAlaGlyGlyLeu-272 |
| Hydrophilic Regions - Hopp-Woods | |
| SEQ. ID. NO. 35193 | 29-AlaSerAspLysVal-33 |
| SEQ. ID. NO. 35194 | 50-SerArgValGluAspLeuGlySerArgLeuGlyAsp-61 |

TABLE 1-continued

| | |
|---|---|
| SEQ. ID. NO. 35195 | 92-IleGlyGlyLysGlyLysGlyVal-99 |
| SEQ. ID. NO. 35196 | 149-LeuLysSerSerGlyValSer-155 |
| SEQ. ID. NO. 35197 | 160-LeuLeuAsnArgArgGlyIleArg-167 | g701
AMPHI Regions - AMPHI
| | |
|---|---|
| SEQ. ID. NO. 35198 | 6-PheGlnValAlaGly-10 |
| SEQ. ID. NO. 35199 | 30-CysLeuGluThrSer-34 |
| SEQ. ID. NO. 35200 | 45-ProAsnSerPheAlaGlyPheLysArgPheSerSerIle-57 |
| SEQ. ID. NO. 35201 | 79-GlyProAlaProAlaMet-84 |
| SEQ. ID. NO. 35202 | 111-ArgAlaIleSerSerLeu-116 |

Antigenic Index - Jameson-Wolf
| | |
|---|---|
| SEQ. ID. NO. 35203 | 17-AlaGlnSerThrProSerSerProThrMet-26 |
| SEQ. ID. NO. 35204 | 29-ThrCysLeuGluThrSerProGluAlaGly-38 |
| SEQ. ID. NO. 35205 | 52-LysArgPheSerSer-56 |
| SEQ. ID. NO. 35206 | 72-AsnLysAlaAspIleProThrGlyProAla-81 |
| SEQ. ID. NO. 35207 | 104-GlyLysAlaSerLeuAsnSerArgAla-112 |
| SEQ. ID. NO. 35208 | 119-SerCysGlyGlyThrArgLeu-125 |

Hydrophilic Regions - Hopp-Woods
| | |
|---|---|
| SEQ. ID. NO. 35209 | 72-AsnLysAlaAspIleProThr-78 | g702
AMPHI Regions - AMPHI
| | |
|---|---|
| SEQ. ID. NO. 35210 | 51-CysSerGlyLeuValThrValProAla-59 |
| SEQ. ID. NO. 35211 | 74-AlaSerSerProThrGlyValArgLysValIle-84 |

Antigenic Index - Jameson-Wolf
| | |
|---|---|
| SEQ. ID. NO. 35212 | 1-MetProCysSerLysAlaSerTrp-8 |
| SEQ. ID. NO. 35213 | 10-SerProGlyValAla-14 |
| SEQ. ID. NO. 35214 | 27-AlaLeuAlaArgAspSerCysLysProGlyLeu-37 |
| SEQ. ID. NO. 35215 | 41-ThrAlaProAlaSerSer-46 |
| SEQ. ID. NO. 35216 | 69-AlaIleArgArgMetAlaSerSerProThrGlyValArgLysValIleSer-85 |
| SEQ. ID. NO. 35217 | 88-GlyMetProProSerThrArgAlaArgAspLysSerThrAla-101 |
| SEQ. ID. NO. 35218 | 118-ArgIleSerArgGlyValSer-124 |

Hydrophilic Regions - Hopp-Woods
| | |
|---|---|
| SEQ. ID. NO. 35219 | 27-AlaLeuAlaArgAspSerCysLys-34 |
| SEQ. ID. NO. 35220 | 69-AlaIleArgArgMetAlaSer-75 |
| SEQ. ID. NO. 35221 | 78-ThrGlyValArgLysValIleSer-85 |
| SEQ. ID. NO. 35222 | 91-ProSerThrArgAlaArgAspLysSerThrAla-101 |
| SEQ. ID. NO. 35223 | 118-ArgIleSerArgGlyValSer-124 | g703
AMPHI Regions - AMPHI
| | |
|---|---|
| SEQ. ID. NO. 35224 | 21-GlnThrLeuAlaThrValAsnGly-28 |
| SEQ. ID. NO. 35225 | 64-GluValValAsnThrValValAlaGlnGlu-73 |
| SEQ. ID. NO. 35226 | 79-LeuAspArgSerAlaGlu-84 |
| SEQ. ID. NO. 35227 | 136-GlnGluValLysAlaValTyrAspAsnIleSerGlyPheTyrLysGly-151 |
| SEQ. ID. NO. 35228 | 181-PheAspAlaValLeu-185 |
| SEQ. ID. NO. 35229 | 204-ValProLeuLysAspLeuGluGlnGlyValProProLeuTyrGlnAlaIleLysAspLeuLysLys-225 |
| SEQ. ID. NO. 35230 | 252-ValProSerPheAsp-256 |
| SEQ. ID. NO. 35231 | 270-ArgIleAspArgAlaValCys-276 |

Antigenic Index - Jameson-Wolf
| | |
|---|---|
| SEQ. ID. NO. 35232 | 1-MetLysAlaLysIle-5 |
| SEQ. ID. NO. 35233 | 26-ValAsnGlyGlnLysIleAspSerSerVal-35 |
| SEQ. ID. NO. 35234 | 43-PheArgAlaGluAsnSerArgAlaGluAspThrProGlnLeuArg-57 |
| SEQ. ID. NO. 35235 | 72-GlnGluValLysArgLeuLysLeuAspArgSerAlaGluPheLysAspAlaLeuAlaLysLeuArgAlaGluAlaLysLysSerGlyAspAspLys LysProSerPheLysThr-109 |
| SEQ. ID. NO. 35236 | 129-LysThrGlnProValSerGluGlnGluValLysAlaValTyr-142 |
| SEQ. ID. NO. 35237 | 144-AsnIleSerGlyPheTyrLysGlyThrGlnGluValGlnLeu-157 |
| SEQ. ID. NO. 35238 | 160-IleLeuThrAspLysGluGluAsnAlaLysLysAlaValAlaAspLeuLysAlaLysLysGlyPhe-181 |
| SEQ. ID. NO. 35239 | 188-TyrSerLeuAsnAspArgThrLysArgThrGlyAlaProAspGlyTyrValPro-205 |
| SEQ. ID. NO. 35240 | 207-LysAspLeuGluGlnGlyValProPro-215 |
| SEQ. ID. NO. 35241 | 221-LysAspLeuLysLysGlyGluPheThrAlaThrProLeuLysAsnGlyAspPhe-238 |
| SEQ. ID. NO. 35242 | 243-TyrValAsnAspSerArgGluValLysValProSerPheAspGluMetLysGly-260 |
| SEQ. ID. NO. 35243 | 266-LeuGlnAlaGluArgIleAspArgAlaVal-275 |
| SEQ. ID. NO. 35244 | 282-AlaAsnIleLysProAlaLys-288 |

Hydrophilic Regions - Hopp-Woods
| | |
|---|---|
| SEQ. ID. NO. 35245 | 1-MetLysAlaLysIle-5 |
| SEQ. ID. NO. 35246 | 29-GlnLysIleAspSerSerVal-35 |
| SEQ. ID. NO. 35247 | 43-PheArgAlaGluAsnSerArgAlaGluAspThrProGlnLeuArg-57 |
| SEQ. ID. NO. 35248 | 72-GlnGluValLysArgLeuLysLeuAspArgSerAlaGluPheLysAspAlaLeuAlaLysLeuArgAlaGluAlaLysLysSerGlyAspAspLysLys ProSerPhe-107 |
| SEQ. ID. NO. 35249 | 131-GlnProValSerGluGlnGluValLysAlaValTyr-142 |
| SEQ. ID. NO. 35250 | 160-IleLeuThrAspLysGluGluAsnAlaLysLysAlaValAlaAspLeuLysAlaLysLysGlyPhe-181 |
| SEQ. ID. NO. 35251 | 189-SerLeuAsnAspArgThrLysArgThrGlyAla-199 |
| SEQ. ID. NO. 35252 | 207-LysAspLeuGluGln-211 |
| SEQ. ID. NO. 35253 | 221-LysAspLeuLysLysGlyGluPhe-228 |
| SEQ. ID. NO. 35254 | 245-AsnAspSerArgGluValLysValProSerPheAspGluMetLysGly-260 |
| SEQ. ID. NO. 35255 | 266-LeuGlnAlaGluArgIleAspArgAlaVal-275 |
| SEQ. ID. NO. 35256 | 282-AlaAsnIleLysProAlaLys-288 | g704
AMPHI Regions - AMPHI
| | |
|---|---|
| SEQ. ID. NO. 35257 | 36-AlaValAlaGlnSerIleIleAspSerGlyLeuGly-47 |
| SEQ. ID. NO. 35258 | 65-GlnGluIleLeuAspGlnIleArgLeuTyrAspLeuProGluValGlnSerAspPheValGluThrHis-87 |

TABLE 1-continued

| | |
|---|---|
| SEQ. ID. NO. 35259 | 184-LeuGlyMetMetGln-188 |
| SEQ. ID. NO. 35260 | 208-LeuGlnIleLeuHisTrpGlyGlyPheLeuMetValLeuPro-221 |
| SEQ. ID. NO. 35261 | 232-GlnGlyAlaLeuArgAspLeuLys-239 |
| SEQ. ID. NO. 35262 | 252-AlaIleIleMetThrPheIleAlaGlyIleTyrSer-263 |
| SEQ. ID. NO. 35263 | 289-PheMetGluHisIleAlaArg-295 |
| SEQ. ID. NO. 35264 | 298-AlaGlyAspAlaAlaGluArgLeuValLysLeuIleProAlaPheCysHisArgMetProGlyTyrProAlaValGlnAsp-324 |
| SEQ. ID. NO. 35265 | 326-ArgGluSerAlaValVal-331 |
| SEQ. ID. NO. 35266 | 400-GlyGlyThrArgLeuSerHisIleValArgLeuLeuAspArgAlaLeuAla-416 |
| SEQ. ID. NO. 35267 | 423-GluLeuAlaGluGlnTyr-428 |
| SEQ. ID. NO. 35268 | 499-AlaIleGluThrLeuSerGln-505 |
| SEQ. ID. NO. 35269 | 527-IleGluLeuLeuGlySerMet-533 |
| SEQ. ID. NO. 35270 | 574-GlnArgLeuAsnArgIleGlyGluGlyValGly-584 |
| SEQ. ID. NO. 35271 | 639-LeuLysAspSerAlaAlaGluAlaValArgGlnLeuAla-651 |
| SEQ. ID. NO. 35272 | 670-GluThrAlaArgAlaLeuGlyIle-677 |
| SEQ. ID. NO. 35273 | 691-GluTyrValGluAlaLeuGlnLysGlu-699 |
| SEQ. ID. NO. 35274 | 744-AspLeuArgThrValAlaHisLeuLeuAsp-753 |
| SEQ. ID. NO. 35275 | 780-AlaValLeuGlyTyrValGlnProTrpIleAlaAla-791 |
| SEQ. ID. NO. 35276 | 799-LeuAlaValLeuGly-803 |
| Antigenic Index - Jameson-Wolf | |
| SEQ. ID. NO. 35277 | 1-MetLysLysThrCys-5 |
| SEQ. ID. NO. 35278 | 9-GlyLeuAspValProGluAsn-15 |
| SEQ. ID. NO. 35279 | 20-ValArgTyrGluGlyGluAspArgGluThrCysCysValGly-33 |
| SEQ. ID. NO. 35280 | 42-IleAspSerGlyLeuGlySerTyrTyrLysArgArgThrAlaAspAlaLysLysThrGluLeuProProGlnGluIleLeuAsp-69 |
| SEQ. ID. NO. 35281 | 77-ProGluValGlnSerAspPheValGluThrHisAsnGlyThrHis-91 |
| SEQ. ID. NO. 35282 | 112-GlnLeuLeuArgThrAspGlyIleVal-120 |
| SEQ. ID. NO. 35283 | 124-LeuAsnTyrSerThrHisArgCys-131 |
| SEQ. ID. NO. 35284 | 133-ValValTrpAspAspGlyLysIleArgLeu-142 |
| SEQ. ID. NO. 35285 | 149-IleArgGlnThrGlyTyr-154 |
| SEQ. ID. NO. 35286 | 158-ProTyrAspAlaGlnLysIleGluAlaAlaAsnGlnLysGluArgLysGlnTyr-175 |
| SEQ. ID. NO. 35287 | 199-TyrGlyGlyAspIleGluProAspPhe-207 |
| SEQ. ID. NO. 35288 | 234-AlaLeuArgAspLeuLysAsnArgArgAlaGlyMetAspThrPro-248 |
| SEQ. ID. NO. 35289 | 293-IleAlaArgArgLysAlaGlyAspAlaAlaGluArgLeuVal-306 |
| SEQ. ID. NO. 35290 | 315-ArgMetProGlyTyr-319 |
| SEQ. ID. NO. 35291 | 323-GlnAspValArgGluSerAlaVal-330 |
| SEQ. ID. NO. 35292 | 342-LysProGlyGluThrIleProValAspGlyThrVal-353 |
| SEQ. ID. NO. 35293 | 355-GluGlyAsnSerAlaValAsnGluSer-363 |
| SEQ. ID. NO. 35294 | 365-LeuThrGlyGluSer-369 |
| SEQ. ID. NO. 35295 | 374-LysMetProSerGluLysValThrAla-382 |
| SEQ. ID. NO. 35296 | 393-IleArgThrAspArgThrGlyGlyGlyThrArg-403 |
| SEQ. ID. NO. 35297 | 414-AlaLeuAlaGlnLysProArgThrAlaGluLeuAlaGlu-426 |
| SEQ. ID. NO. 35298 | 486-ThrLeuAlaArgGluGlyIle-492 |
| SEQ. ID. NO. 35299 | 495-GlyGlyLysGlnAlaIle-500 |
| SEQ. ID. NO. 35300 | 510-IlePheAspLysThrGlyThrLeuThrGlnGlyAsnProAlaValArgArgIleGluLeu-529 |
| SEQ. ID. NO. 35301 | 544-SerLeuGluGlnGlnSerGluHisProLeu-553 |
| SEQ. ID. NO. 35302 | 561-ArgIleSerGlyGlySerValPro-568 |
| SEQ. ID. NO. 35303 | 571-GlnValGlyGlnArgLeuAsnArgIleGlyGluGlyVal-583 |
| SEQ. ID. NO. 35304 | 589-ValAsnGlyGluThr-593 |
| SEQ. ID. NO. 35305 | 605-AlaGluIleSerGlyLysGluProGlnThrGluGlyGlyGlySer-619 |
| SEQ. ID. NO. 35306 | 635-LeuGlnAspProLeuLysAspSerAlaAlaGluAlaValArg-648 |
| SEQ. ID. NO. 35307 | 650-LeuAlaGlyLysAsnLeu-655 |
| SEQ. ID. NO. 35308 | 659-IleLeuSerGlyAspArgGluGluAlaValAlaGluThrAlaArg-673 |
| SEQ. ID. NO. 35309 | 684-AlaMetProGluAspLysLeuGluTyr-692 |
| SEQ. ID. NO. 35310 | 694-GluAlaLeuGlnLysGluGlyLysLys-702 |
| SEQ. ID. NO. 35311 | 707-GlyAspGlyIleAsnAspAla-713 |
| SEQ. ID. NO. 35312 | 727-GlyGlyThrAspIleAlaArgAspGlyAlaAsp-737 |
| SEQ. ID. NO. 35313 | 743-GluAspLeuArgThr-747 |
| SEQ. ID. NO. 35314 | 753-AspGlnAlaArgArgThrArgHisIleIle-762 |
| SEQ. ID. NO. 35315 | 807-ArgLeuHisLysArgGlyGluMetProSerGluGln-818 |
| Hydrophilic Regions - Hopp-Woods | |
| SEQ. ID. NO. 35316 | 1-MetLysLysThrCys-5 |
| SEQ. ID. NO. 35317 | 22-TyrGluGlyGluAspArgGluThrCys-30 |
| SEQ. ID. NO. 35318 | 50-TyrLysArgArgThrAlaAspAlaLysLysThrGluLeuProPro-64 |
| SEQ. ID. NO. 35319 | 77-ProGluValGlnSerAspPheValGlu-85 |
| SEQ. ID. NO. 35320 | 87-HisAsnGlyThrHis-91 |
| SEQ. ID. NO. 35321 | 112-GlnLeuLeuArgThrAspGlyIleVal-120 |
| SEQ. ID. NO. 35322 | 133-ValValTrpAspAspGlyLysIleArgLeu-142 |
| SEQ. ID. NO. 35323 | 160-AspAlaGlnLysIleGluAlaAlaAsnGlnLysGluArgLysGlnTyr-175 |
| SEQ. ID. NO. 35324 | 201-GlyAspIleGluProAspPhe-207 |
| SEQ. ID. NO. 35325 | 234-AlaLeuArgAspLeuLysAsnArgArgAlaGlyMet-245 |
| SEQ. ID. NO. 35326 | 293-IleAlaArgArgLysAlaGlyAspAlaAlaGluArgLeuVal-306 |
| SEQ. ID. NO. 35327 | 323-GlnAspValArgGluSerAlaVal-330 |
| SEQ. ID. NO. 35328 | 375-MetProSerGluLysValThr-381 |
| SEQ. ID. NO. 35329 | 393-IleArgThrAspArgThrGlyGlyGlyThrArg-403 |
| SEQ. ID. NO. 35330 | 414-AlaLeuAlaGlnLysProArgThrAlaGluLeuAlaGlu-426 |
| SEQ. ID. NO. 35331 | 486-ThrLeuAlaArgGluGlyIle-492 |
| SEQ. ID. NO. 35332 | 522-ProAlaValArgArgIleGluLeu-529 |
| SEQ. ID. NO. 35333 | 545-LeuGluGlnGlnSerGluHisProLeu-553 |
| SEQ. ID. NO. 35334 | 574-GlnArgLeuAsnArgIleGlyGlu-581 |
| SEQ. ID. NO. 35335 | 607-IleSerGlyLysGluProGlnThrGluGlyGlyGly-618 |
| SEQ. ID. NO. 35336 | 637-AspProLeuLysAspSerAlaAlaGluAlaValArg-648 |

TABLE 1-continued

| | |
|---|---|
| SEQ. ID. NO. 35337 | 661-SerGlyAspArgGluGluAlaValAlaGluThrAlaArg-673 |
| SEQ. ID. NO. 35338 | 684-AlaMetProGluAspLysLeuGluTyr-692 |
| SEQ. ID. NO. 35339 | 694-GluAlaLeuGlnLysGluGlyLysLys-702 |
| SEQ. ID. NO. 35340 | 730-AspIleAlaArgAspGlyAlaAsp-737 |
| SEQ. ID. NO. 35341 | 743-GluAspLeuArgThr-747 |
| SEQ. ID. NO. 35342 | 753-AspGlnAlaArgArgThrArgHisIleIle-762 |
| SEQ. ID. NO. 35343 | 807-ArgLeuHisLysArgGlyGluMetProSerGluGln-818 | g705
AMPHI Regions - AMPHI

| | |
|---|---|
| SEQ. ID. NO. 35344 | 67-LysCysLeuLeuLysLeu-72 |
| SEQ. ID. NO. 35345 | 104-AsnProIleProAla-108 |
| SEQ. ID. NO. 35346 | 147-TyrMetGlnThrPheArgArgIleValAlaProGln-158 |
| SEQ. ID. NO. 35347 | 169-AsnGluPheIleGlyLeuPheLysAsn-177 |
| SEQ. ID. NO. 35348 | 183-ValValThrValThrGluLeuPheArgValAlaGln-194 |
| SEQ. ID. NO. 35349 | 196-ThrAlaAsnArgThr-200 |

Antigenic Index - Jameson-Wolf

| | |
|---|---|
| SEQ. ID. NO. 35350 | 13-ThrGluThrArgAlaAspMet-19 |
| SEQ. ID. NO. 35351 | 132-ValProLysGlyGlnTrpGlu-138 |
| SEQ. ID. NO. 35352 | 165-ProProLeuSerAsnGlu-170 |
| SEQ. ID. NO. 35353 | 193-AlaGlnGluThrAlaAsnArgThrTyrAsp-202 |
| SEQ. ID. NO. 35354 | 226-AlaArgLeuGluLysArgPheAspArgTyrValAla-237 |

Hydrophilic Regions - Hopp-Woods

| | |
|---|---|
| SEQ. ID. NO. 35355 | 13-ThrGluThrArgAlaAspMet-19 |
| SEQ. ID. NO. 35356 | 193-AlaGlnGluThrAlaAsnArgThr-200 |
| SEQ. ID. NO. 35357 | 226-AlaArgLeuGluLysArgPheAspArgTyrValAla-237 | g706
AMPHI Regions - AMPHI

| | |
|---|---|
| SEQ. ID. NO. 35358 | 11-GlyArgTrpLeuAsnSerTyr-17 |
| SEQ. ID. NO. 35359 | 24-ArgLeuIleHisAlaValArg-30 |
| SEQ. ID. NO. 35360 | 39-ThrAlaLeuAlaArgLeuLeuHis-46 |
| SEQ. ID. NO. 35361 | 70-IleTyrSerAsnAlaValGluArgMetLeuGlyThrValIleGly-84 |
| SEQ. ID. NO. 35362 | 111-ThrAlaSerAlaLeuAlaGlyTrpAlaAla-120 |
| SEQ. ID. NO. 35363 | 153-ArgAlaMetAsnValLeu-158 |
| SEQ. ID. NO. 35364 | 183-LeuAlaAspAsnLeuAlaAspCysSerLysMetIleAlaGluIleSerAsnGlyArg-201 |
| SEQ. ID. NO. 35365 | 241-SerMetMetGluAlaMetGlnHisAlaHisArgLysIleVal-254 |
| SEQ. ID. NO. 35366 | 318-AlaLeuAlaGluHisLeuHis-324 |

Antigenic Index - Jameson-Wolf

| | |
|---|---|
| SEQ. ID. NO. 35367 | 1-MetAsnSerSerGlnArgLysArgLeuSerGlyArgTrpLeuAsnSerTyrGluArgTyrArgHisArgArgLeu-25 |
| SEQ. ID. NO. 35368 | 30-ArgLeuGlyGlyThr-34 |
| SEQ. ID. NO. 35369 | 71-TyrSerAsnAlaValGluArgMetLeu-79 |
| SEQ. ID. NO. 35370 | 97-HisTyrPheHisGlyAsnLeu-103 |
| SEQ. ID. NO. 35371 | 122-GlyLysAsnGlyTyrVal-127 |
| SEQ. ID. NO. 35372 | 140-GlyAspAsnGlySerGluTrpLeuAsp-148 |
| SEQ. ID. NO. 35373 | 186-AsnLeuAlaAspCysSerLysMetIleAlaGluIleSerAsnGlyArgArgMetThrArgGluArgLeuGluGlnAsnMetValLysMetArgGlnIleAsn-219 |
| SEQ. ID. NO. 35374 | 221-ArgMetValLysSerArgSerHisLeuAlaAlaThrSerGlyGluSerArgIleSerProSerMet-242 |
| SEQ. ID. NO. 35375 | 249-AlaHisArgLysIleValAsn-255 |
| SEQ. ID. NO. 35376 | 266-LysLeuGlnSerProLysLeuAsnGlySerGluIleArgLeuLeuAsp-281 |
| SEQ. ID. NO. 35377 | 289-ThrAspLeuGlnGln-293 |
| SEQ. ID. NO. 35378 | 300-GlyArgHisAlaArgArgIleArgIleAspThrAlaIleAsnProGluLeuGluAlaLeuAla-320 |
| SEQ. ID. NO. 35379 | 334-SerThrAsnMetArgGlnGluIle-341 |
| SEQ. ID. NO. 35380 | 349-GlnArgThrArgArgLysTrpLeuAspAlaHisGluArgGlnHisLeu-364 |
| SEQ. ID. NO. 35381 | 367-SerLeuLeuGluThrArgGluHisGly-375 |

Hydrophilic Regions - Hopp-Woods

| | |
|---|---|
| SEQ. ID. NO. 35382 | 3-SerSerGlnArgLysArgLeuSer-10 |
| SEQ. ID. NO. 35383 | 17-TyrGluArgTyrArgHisArgArgLeu-25 |
| SEQ. ID. NO. 35384 | 74-AlaValGluArgMetLeu-79 |
| SEQ. ID. NO. 35385 | 142-AsnGlySerGluTrpLeu-147 |
| SEQ. ID. NO. 35386 | 186-AsnLeuAlaAspCysSerLysMetIleAla-195 |
| SEQ. ID. NO. 35387 | 198-SerAsnGlyArgArgMetThrArgGluArgLeuGluGlnAsnMetValLysMetArgGlnIleAsn-219 |
| SEQ. ID. NO. 35388 | 221-ArgMetValLysSerArgSerHis-228 |
| SEQ. ID. NO. 35389 | 232-ThrSerGlyGluSerArgIleSer-239 |
| SEQ. ID. NO. 35390 | 249-AlaHisArgLysIleValAsn-255 |
| SEQ. ID. NO. 35391 | 266-LysLeuGlnSerProLysLeuAsnGlySerGluIleArgLeuLeuAsp-281 |
| SEQ. ID. NO. 35392 | 301-ArgHisAlaArgArgIleArgIle-308 |
| SEQ. ID. NO. 35393 | 314-ProGluLeuGluAlaLeuAla-320 |
| SEQ. ID. NO. 35394 | 336-AsnMetArgGlnGluIle-341 |
| SEQ. ID. NO. 35395 | 349-GlnArgThrArgArgLysTrpLeuAspAlaHisGluArgGlnHisLeu-364 |
| SEQ. ID. NO. 35396 | 367-SerLeuLeuGluThrArgGluHisGly-375 | g707
AMPHI Regions - AMPHI

| | |
|---|---|
| SEQ. ID. NO. 35397 | 36-GlyIleGluLysMetAlaThrGln-43 |
| SEQ. ID. NO. 35398 | 91-HisAlaGlyAspIleAsnGlnIleMetSerLeu-101 |
| SEQ. ID. NO. 35399 | 116-IleLeuAlaAlaPro-120 |
| SEQ. ID. NO. 35400 | 134-ProGlyTyrLeuArgSerIleArgIle-142 |
| SEQ. ID. NO. 35401 | 168-AspLeuLeuAsnLeuArgAsp-174 |
| SEQ. ID. NO. 35402 | 182-LeuLysCysLeuPro-186 |
| SEQ. ID. NO. 35403 | 208-ValGlnTrpArgArgLeuLeuPro-215 |
| SEQ. ID. NO. 35404 | 248-SerAspMetPheTyr-252 |
| SEQ. ID. NO. 35405 | 256-GlyArgSerIleGlyGly-261 |

TABLE 1-continued

| | |
|---|---|
| SEQ. ID. NO. 35406 | 301-ArgTyrHisGlnAlaValSerGlyLeuSerGluValTyrAsp-314 |
| SEQ. ID. NO. 35407 | 368-TrpLeuAlaGluLeuSerHis-374 |
| SEQ. ID. NO. 35408 | 393-ThrGlyMetLysAspAlaLeuArgAlaProGluGluAlaPheGlyGluGly-409 |
| SEQ. ID. NO. 35409 | 440-HisAlaGlnTrpAsnLys-445 |
| SEQ. ID. NO. 35410 | 542-LeuLysLysProGluTyrPhe-548 |

Antigenic Index - Jameson-Wolf

| | |
|---|---|
| SEQ. ID. NO. 35411 | 1-GluAlaValSerGlnGlnGlnAspIleLeuGlnArgGlnArgGluLysGlnLeuArgGluGlnMetGlnProGluGlnAspValArgLeuAspGlyThrAspThrGlyIleGluLysMetAla-41 |
| SEQ. ID. NO. 35412 | 44-ValGlyGlyAlaAsnSerAspGluAlaSerProCys-55 |
| SEQ. ID. NO. 35413 | 62-GluLeuValGlyGluGluAlaAlaLys-70 |
| SEQ. ID. NO. 35414 | 120-ProGlnAspLeuAsnSerGlyLysLeu-128 |
| SEQ. ID. NO. 35415 | 140-IleArgIleAspArgSerAsnAspAspGlnThrHis-151 |
| SEQ. ID. NO. 35416 | 160-AsnLysPheProThrArgSerAsnAspLeuLeuAsn-171 |
| SEQ. ID. NO. 35417 | 173-ArgAspLeuGluGlnGlyLeuGluAsn-181 |
| SEQ. ID. NO. 35418 | 188-AlaGluAlaAspLeu-192 |
| SEQ. ID. NO. 35419 | 196-ProValGluArgGluProAsnGlnSerAsp-205 |
| SEQ. ID. NO. 35420 | 221-GlyMetAspAsnSerGlySerGluAlaThrGlyLysTyrGlnGly-235 |
| SEQ. ID. NO. 35421 | 241-AlaAspAsnProPheGlyLeu-247 |
| SEQ. ID. NO. 35422 | 255-TyrGlyArgSerIleGlyGlyThrProAspGluGluAsnPheAspGlyHisArgLysGluGlyGlySerAsn-278 |
| SEQ. ID. NO. 35423 | 297-HisAsnGlyTyrArg-301 |
| SEQ. ID. NO. 35424 | 311-GluValTyrAspTyrAsnGlyLysSerTyrAsnThrAspPheGlyPhe-326 |
| SEQ. ID. NO. 35425 | 330-LeuTyrArgAspAlaLysArgLysThrTyrLeu-340 |
| SEQ. ID. NO. 35426 | 345-TrpThrArgGluThrLysSerTyrIleAspAspAlaGluLeuThrValGlnArgArgLysThrThr-366 |
| SEQ. ID. NO. 35427 | 372-LeuSerHisLysGlyTyrIleGlyArgSerThrAlaAspPheLysLeuLysTyrLysHisGlyThrGlyMetLysAspAlaLeuArgAlaProGluGluAlaPheGlyGluGlyThrArgArg-412 |
| SEQ. ID. NO. 35428 | 419-SerAlaAspValAsnThrPro-425 |
| SEQ. ID. NO. 35429 | 442-GlnTrpAsnLysThrProLeuThrSerGlnAspLysLeuAla-455 |
| SEQ. ID. NO. 35430 | 460-HisThrValArgGlyPheAspGlyGluMetSerLeuProAlaGluArgGlyTrpTyrTrpArgAsnAspLeuSerTrpGlnPheLysProGlyHis-491 |
| SEQ. ID. NO. 35431 | 503-SerGlyGlnSerAlaLys-508 |
| SEQ. ID. NO. 35432 | 540-ArgAlaLeuLysLysProGluTyrPheGlnThrLysLysTrpValThr-555 |

Hydrophilic Regions - Hopp-Woods

| | |
|---|---|
| SEQ. ID. NO. 35433 | 1-GluAlaValSerGlnGlnGlnAspIleLeuGlnArgGlnArgGluLysGlnLeuArgGluGlnMetGlnProGluGlnAspValArgLeuAspGlyThrAspThrGlyIleGluLysMetAla-41 |
| SEQ. ID. NO. 35434 | 47-AlaAsnSerAspGluAlaSer-53 |
| SEQ. ID. NO. 35435 | 62-GluLeuValGlyGluGluAlaAlaLys-70 |
| SEQ. ID. NO. 35436 | 121-GlnAspLeuAsnSerGlyLys-127 |
| SEQ. ID. NO. 35437 | 140-IleArgIleAspArgSerAsnAspAspGlnThrHis-151 |
| SEQ. ID. NO. 35438 | 162-PheProThrArgSerAsnAsp-168 |
| SEQ. ID. NO. 35439 | 173-ArgAspLeuGluGlnGlyLeuGluAsn-181 |
| SEQ. ID. NO. 35440 | 188-AlaGluAlaAspLeu-192 |
| SEQ. ID. NO. 35441 | 196-ProValGluArgGluProAsnGlnSer-204 |
| SEQ. ID. NO. 35442 | 222-MetAspAsnSerGlySerGluAlaThrGlyLysTyr-233 |
| SEQ. ID. NO. 35443 | 259-IleGlyGlyThrProAspGluGluAsnPheAspGlyHisArgLysGluGlyGlySer-277 |
| SEQ. ID. NO. 35444 | 313-TyrAspTyrAsnGly-317 |
| SEQ. ID. NO. 35445 | 330-LeuTyrArgAspAlaLysArgLysThrTyrLeu-340 |
| SEQ. ID. NO. 35446 | 345-TrpThrArgGluThrLysSerTyrIleAspAspAlaGluLeuThrValGlnArgArgLysThrThr-366 |
| SEQ. ID. NO. 35447 | 381-SerThrAlaAspPheLysLeuLysTyrLysHis-391 |
| SEQ. ID. NO. 35448 | 393-ThrGlyMetLysAspAlaLeuArgAlaProGluGluAlaPheGly-40 |
| SEQ. ID. NO. 35449 | 447-ProLeuThrSerGlnAspLysLeuAla-455 |
| SEQ. ID. NO. 35450 | 463-ArgGlyPheAspGlyGluMet-469 |
| SEQ. ID. NO. 35451 | 540-ArgAlaLeuLysLysProGluTyrPheGln-549 | g708
AMPHI Regions - AMPHI

| | |
|---|---|
| SEQ. ID. NO. 35452 | 26-ProSerArgAlaGluLysAlaAsnGlnValSerAsnIle-38 |
| SEQ. ID. NO. 35453 | 56-ThrAlaSerIleGluAspAlaLeuLysSerAsnPro-67 |
| SEQ. ID. NO. 35454 | 79-IleTyrGlnTyrLeuLys-84 |
| SEQ. ID. NO. 35455 | 89-AlaGlnGluSerPhe-93 |
| SEQ. ID. NO. 35456 | 119-AsnArgProAlaGluSerMetAla-126 |
| SEQ. ID. NO. 35457 | 128-PheAspLysAlaLeu-132 |
| SEQ. ID. NO. 35458 | 142-IleAlaAsnLeuAsnLys-147 |
| SEQ. ID. NO. 35459 | 176-ProAlaPheLysGluLeuAlaArg-183 |
| SEQ. ID. NO. 35460 | 221-LysAlaLeuGlyAsnValGlnAla-228 |

Antigenic Index - Jameson-Wolf

| | |
|---|---|
| SEQ. ID. NO. 35461 | 2-ProPheLysProSerLysArgIleSer-10 |
| SEQ. ID. NO. 35462 | 19-AlaCysSerThrSerTyrArgProSerArgAlaGluLysAlaAsnGln-34 |
| SEQ. ID. NO. 35463 | 46-TyrMetArgGlyGlnAspTyrArgGlnAlaThrAlaSerIleGluAspAlaLeuLysSerAsnProLysAsnGluLeu-71 |
| SEQ. ID. NO. 35464 | 84-LysValAsnAspLysAlaGlnGluSerPheArg-94 |
| SEQ. ID. NO. 35465 | 97-LeuSerIleLysProAspSerAlaGluIleAsnAsnAsnTyrGlyTrp-112 |
| SEQ. ID. NO. 35466 | 115-CysGlyArgLeuAsnArgProAlaGlu-123 |
| SEQ. ID. NO. 35467 | 131-AlaLeuAlaAspProThrTyrProThr-139 |
| SEQ. ID. NO. 35468 | 145-LeuAsnLysGlyIleCysSerAlaLysGlnGlyGln-156 |
| SEQ. ID. NO. 35469 | 176-ProAlaPheLysGluLeuAlaArgThrLysMet-186 |
| SEQ. ID. NO. 35470 | 191-LeuGlyAspAlaAspTyrTyrPheLysLysTyrGlnSerArgValGluValLeuGlnAlaAspAspLeu-213 |
| SEQ. ID. NO. 35471 | 240-PheProTyrSerGluGluLeuGln-247 |

Hydrophilic Regions - Hopp-Woods

| | |
|---|---|
| SEQ. ID. NO. 35472 | 4-LysProSerLysArgIle-9 |
| SEQ. ID. NO. 35473 | 24-TyrArgProSerArgAlaGluLysAlaAsnGln-34 |
| SEQ. ID. NO. 35474 | 46-TyrMetArgGlyGlnAspTyrArgGln-54 |
| SEQ. ID. NO. 35475 | 56-ThrAlaSerIleGluAspAlaLeuLysSerAsnProLysAsnGlu-70 |
| SEQ. ID. NO. 35476 | 84-LysValAsnAspLysAlaGlnGluSerPheArg-94 |

TABLE 1-continued

| | |
|---|---|
| SEQ. ID. NO. 35477 | 99-IleLysProAspSerAlaGluIle-106 |
| SEQ. ID. NO. 35478 | 117-ArgLeuAsnArgProAlaGlu-123 |
| SEQ. ID. NO. 35479 | 149-IleCysSerAlaLysGlnGly-155 |
| SEQ. ID. NO. 35480 | 177-AlaPheLysGluLeuAlaArgThrLysMet-186 |
| SEQ. ID. NO. 35481 | 201-TyrGlnSerArgValGluValLeuGlnAlaAspAspLeu-213 | g709
AMPHI Regions - AMPHI

| | |
|---|---|
| SEQ. ID. NO. 35482 | 6-SerLeuLeuAspMetProArgGlyGlu-14 |
| SEQ. ID. NO. 35483 | 18-ValValValAlaLeuIleAlaAlaMetGly-27 |
| SEQ. ID. NO. 35484 | 37-ProHisMetSerIleIleAlaAlaIleValValLeu-48 |
| SEQ. ID. NO. 35485 | 54-AlaArgGlyLeuLysTyr-59 |
| SEQ. ID. NO. 35486 | 67-IleGlyAlaLeuAsnGlnGlyMet-74 |
| SEQ. ID. NO. 35487 | 115-SerAlaPheAlaLeuCysSerVal-122 |
| SEQ. ID. NO. 35488 | 130-SerLeuThrAlaCysAla-135 |
| SEQ. ID. NO. 35489 | 171-ProLeuSerAspThr-175 |
| SEQ. ID. NO. 35490 | 185-IleAspLeuPheGluHisIleLysAsnMetMetTyrThrThr-198 |
| SEQ. ID. NO. 35491 | 221-LeuAsnSerValGluSerPheArg-228 |
| SEQ. ID. NO. 35492 | 245-PheAlaLeuLeuValValLeu-251 |
| SEQ. ID. NO. 35493 | 261-AlaMetLeuPheThrValIleAlaAlaValAlaValThrTyr-274 |
| SEQ. ID. NO. 35494 | 278-ThrProAspLeuArgGlnLeuGlyAlaTrpPhe-288 |
| SEQ. ID. NO. 35495 | 298-AlaPheLysAspIleAlaLysLeuIleSerArgGlyGly-310 |
| SEQ. ID. NO. 35496 | 334-LeuGlyValIleProSerLeuLeuGluAlaValArgThrPheLeuThr-349 |
| SEQ. ID. NO. 35497 | 382-ThrPheLysProVal-386 |
| SEQ. ID. NO. 35498 | 396-AsnLeuSerArgThrLeuGluAspAlaGlyThrValIleAsnProLeuValProTrpSerValCysGlyValPheIleSerHis-423 |

Antigenic Index - Jameson-Wolf

| | |
|---|---|
| SEQ. ID. NO. 35499 | 8-LeuAspMetProArgGlyGluAla-15 |
| SEQ. ID. NO. 35500 | 55-ArgGlyLeuLysTyrAsnAspMetGln-63 |
| SEQ. ID. NO. 35501 | 165-PheGlyAspLysMetSerProLeuSerAspThrThrGly-177 |
| SEQ. ID. NO. 35502 | 222-AsnSerValGluSerPheArgSerGlnLeuGlu-232 |
| SEQ. ID. NO. 35503 | 277-SerThrProAspLeuArgGln-283 |
| SEQ. ID. NO. 35504 | 290-GlyGlyTyrLysLeuGluGlyGluAlaPheLysAspIleAlaLysLeuIleSerArgGlyGlyLeuGlu-312 |
| SEQ. ID. NO. 35505 | 349-ThrAsnAlaGlyArgAlaThr-355 |
| SEQ. ID. NO. 35506 | 378-LeuSerGlyGluThrPheLysProValTyrAspLysLeuGly-391 |
| SEQ. ID. NO. 35507 | 396-AsnLeuSerArgThrLeuGluAspAlaGlyThr-406 |

Hydrophilic Regions - Hopp-Woods

| | |
|---|---|
| SEQ. ID. NO. 35508 | 8-LeuAspMetProArgGlyGluAla-15 |
| SEQ. ID. NO. 35509 | 57-LeuLysTyrAsnAsp-61 |
| SEQ. ID. NO. 35510 | 167-AspLysMetSerProLeuSerAsp-174 |
| SEQ. ID. NO. 35511 | 225-GluSerPheArgSerGlnLeuGlu-232 |
| SEQ. ID. NO. 35512 | 279-ProAspLeuArgGln-283 |
| SEQ. ID. NO. 35513 | 293-LysLeuGluGlyGluAlaPheLysAspIleAlaLysLeuIleSer-307 |
| SEQ. ID. NO. 35514 | 399-ArgThrLeuGluAspAlaGly-405 | g716
AMPHI Regions - AMPHI

| | |
|---|---|
| SEQ. ID. NO. 35515 | 33-GlyValGlnLysSerAlaGlnGly-40 |
| SEQ. ID. NO. 35516 | 81-AlaThrValLysLysAlaHisLysHisThrLysAla-92 |

Antigenic Index - Jameson-Wolf

| | |
|---|---|
| SEQ. ID. NO. 35517 | 1-MetAsnLysAsnIle-5 |
| SEQ. ID. NO. 35518 | 26-LysProAlaSerAsnAlaThrGlyValGlnLysSerAlaGlnGlySerCysGlyAlaSerLysSerAlaGluGlySerCysGlyAlaSerLysSerAlaGluGlySerCysGly-63 |
| SEQ. ID. NO. 35519 | 65-AlaAlaSerLysAlaGlyGluGlyLysCysGlyGluGlyLysCysGlyAlaThrValLysLysAlaHisLysHisThrLysAlaSerLysAlaLysAlaLysSerAlaGluGlyLysCysGlyGluGlyLysCysGlySerLys-112 |

Hydrophilic Regions - Hopp-Woods

| | |
|---|---|
| SEQ. ID. NO. 35520 | 33-GlyValGlnLysSerAlaGln-39 |
| SEQ. ID. NO. 35521 | 43-GlyAlaSerLysSerAlaGluGlySerCysGlyAlaSerLysSerAlaGluGlySerCys-62 |
| SEQ. ID. NO. 35522 | 65-AlaAlaSerLysAlaGlyGluGlyLysCysGlyGluGlyLysCys-79 |
| SEQ. ID. NO. 35523 | 81-AlaThrValLysLysAlaHisLysHisThrLysAlaSerLysAlaLysAlaLysSerAlaGluGlyLysCysGlyGluGlyLysCysGlySerLys-112 | g717
AMPHI Regions - AMPHI

| | |
|---|---|
| SEQ. ID. NO. 35524 | 87-AlaAlaIleAlaAla-91 |
| SEQ. ID. NO. 35525 | 174-ThrAlaValTyrAlaLeuAlaAsn-181 |
| SEQ. ID. NO. 35526 | 209-LeuHisArgGlyLeu-213 |
| SEQ. ID. NO. 35527 | 223-SerLeuAlaTyrTrp-227 |
| SEQ. ID. NO. 35528 | 241-AlaGlyLeuGluGlnLeuGly-247 |
| SEQ. ID. NO. 35529 | 263-GlnSerIlePheSerThrValTrpThrProTyrIlePheArgAlaIleGluGlu-280 |
| SEQ. ID. NO. 35530 | 305-ThrGlyIlePheSerProLeuAlaSer-313 |
| SEQ. ID. NO. 35531 | 347-LeuAsnValValArgLysThr-353 |
| SEQ. ID. NO. 35532 | 358-LeuAlaThrLeuGlyAlaLeuAla-365 |
| SEQ. ID. NO. 35533 | 401-SerSerCysArgLeuTrpGlnProLeuLysArgLeu-412 |
| SEQ. ID. NO. 35534 | 430-CysPheGlyThrPro-434 |
| SEQ. ID. NO. 35535 | 442-GlyValTrpAlaAlaTyrLeuAlaGly-450 |
| SEQ. ID. NO. 35536 | 457-LysAsnLeuHisLysLeuPheHisTyr-465 |

Antigenic Index - Jameson-Wolf

| | |
|---|---|
| SEQ. ID. NO. 35537 | 1-MetAspThrLysGlu-5 |
| SEQ. ID. NO. 35538 | 32-ProAlaAspAspIleGlyArg-38 |
| SEQ. ID. NO. 35539 | 69-AlaAspLysAspThrLeu-74 |
| SEQ. ID. NO. 35540 | 95-SerArgProSerLeuProSerGluIle-103 |
| SEQ. ID. NO. 35541 | 135-MetGluGlyArgAla-139 |
| SEQ. ID. NO. 35542 | 192-AsnArgCysArgLeuLysAlaValArgArgAlaProPheSer-205 |
| SEQ. ID. NO. 35543 | 231-SerAlaAspArgLeuPheLeu-237 |

TABLE 1-continued

| | |
|---|---|
| SEQ. ID. NO. 35544 | 277-AlaIleGluGluAsnAlaThrProAlaArgLeu-287 |
| SEQ. ID. NO. 35545 | 289-AlaThrAlaGluSer-293 |
| SEQ. ID. NO. 35546 | 317-ProGluAsnTyrAla-321 |
| SEQ. ID. NO. 35547 | 349-ValValArgLysThrArgProIleAla-357 |
| SEQ. ID. NO. 35548 | 376-ProSerGlyGlyThrArgGlyAla-383 |
| SEQ. ID. NO. 35549 | 398-LysThrGluSerSerCysArgLeu-405 |
| SEQ. ID. NO. 35550 | 453-LeuArgHisArgLysAsnLeu-459 |
| Hydrophilic Regions - Hopp-Woods | |
| SEQ. ID. NO. 35551 | 1-MetAspThrLysGlu-5 |
| SEQ. ID. NO. 35552 | 69-AlaAspLysAspThrLeu-74 |
| SEQ. ID. NO. 35553 | 135-MetGluGlyArgAla-139 |
| SEQ. ID. NO. 35554 | 192-AsnArgCysArgLeuLysAlaValArgArgAlaPro-203 |
| SEQ. ID. NO. 35555 | 277-AlaIleGluGluAsnAlaThrProAlaArgLeu-287 |
| SEQ. ID. NO. 35556 | 289-AlaThrAlaGluSer-293 |
| SEQ. ID. NO. 35557 | 349-ValValArgLysThrArgPro-355 |
| SEQ. ID. NO. 35558 | 378-GlyGlyThrArgGly-382 |
| SEQ. ID. NO. 35559 | 399-ThrGluSerSerCys-403 |
| SEQ. ID. NO. 35560 | 453-LeuArgHisArgLysAsnLeu-459 |
| g728 | |
| AMPHI Regions - AMPHI | |
| SEQ. ID. NO. 35561 | 11-SerPhePheAlaLeuValPheAla-18 |
| SEQ. ID. NO. 35562 | 39-AlaThrGluValProGluAsnPro-46 |
| SEQ. ID. NO. 35563 | 48-AlaPheValAlaLysLeuAlaArgLeuPheArgAsnAla-60 |
| SEQ. ID. NO. 35564 | 74-GluGluSerLeuAlaGlyAlaValAspAsp-83 |
| SEQ. ID. NO. 35565 | 167-HisGlyGluAsnTyrGluThr-173 |
| SEQ. ID. NO. 35566 | 198-GluAspValTyrGluHisCysLeuGlyCysTyrGlnMet-210 |
| SEQ. ID. NO. 35567 | 218-TyrArgAspValAlaAsn-223 |
| SEQ. ID. NO. 35568 | 235-SerAsnArgIleAlaSer-240 |
| SEQ. ID. NO. 35569 | 251-MetArgGluLeuMetProArg-257 |
| SEQ. ID. NO. 35570 | 355-GluLysGluValSerArgTyrAlaGluAlaAlaAlaArg-367 |
| Antigenic Index - Jameson-Wolf | |
| SEQ. ID. NO. 35571 | 29-IleAsnProArgTrp-33 |
| SEQ. ID. NO. 35572 | 35-LeuSerAspThrAlaThrGluValProGluAsnProAsnAla-48 |
| SEQ. ID. NO. 35573 | 57-PheArgAsnAlaAspArgAla-63 |
| SEQ. ID. NO. 35574 | 67-ValLysGluSerMetArgThrGluGluSerLeu-77 |
| SEQ. ID. NO. 35575 | 80-AlaValAspAspGlyProLeuGlnSerGluLysAspTyr-92 |
| SEQ. ID. NO. 35576 | 98-ArgLeuSerArgLeuLysGluLysAlaLys-107 |
| SEQ. ID. NO. 35577 | 112-ThrGluGlnGluHisGlyGlu-118 |
| SEQ. ID. NO. 35578 | 125-TyrIleGlyGluGlyGly-130 |
| SEQ. ID. NO. 35579 | 136-LeuSerGlnArgSerProGluAlaPheVal-145 |
| SEQ. ID. NO. 35580 | 149-TyrLeuTyrArgAsnAspArgProPheSer-158 |
| SEQ. ID. NO. 35581 | 166-AlaHisGlyGluAsnTyrGluThrThrGlyGluTyrArgVal-179 |
| SEQ. ID. NO. 35582 | 182-GlnProAspGlySerVal-187 |
| SEQ. ID. NO. 35583 | 190-AlaAlaGlyArgGlyLysIleGlyGluAspValTyr-201 |
| SEQ. ID. NO. 35584 | 217-LysTyrArgAspValAlaAsnAspGluGlnLysValTrpAspPheArgGluGluSerAsnArgIleAlaSerAspSerArgAspTyrVal-246 |
| SEQ. ID. NO. 35585 | 250-AsnMetArgGluLeuMetProArgGlyMetLysAlaAsnSer-263 |
| SEQ. ID. NO. 35586 | 267-GlyTyrAspAlaAspGlyLeuProGlnLys-276 |
| SEQ. ID. NO. 35587 | 280-SerPheAspAsnGlyLysLysArgGlnSerPheGluTyrTyrLeuLysAsnGlyAsn-298 |
| SEQ. ID. NO. 35588 | 309-LeuLysAlaAspGlyValThr-315 |
| SEQ. ID. NO. 35589 | 329-LeuAspGlyGlyArgIleIleArgGluGluLysGlnGlyAspArgLeuProAspPhe-347 |
| SEQ. ID. NO. 35590 | 349-LeuAsnLeuGluAspLeuGluLysGluValSerArgTyrAlaGluAlaAlaAlaArgArgSerGlyGlyArgArgGlyLeuSerHis-377 |
| Hydrophilic Regions - Hopp-Woods | |
| SEQ. ID. NO. 35591 | 38-ThrAlaThrGluValProGluAsnPro-46 |
| SEQ. ID. NO. 35592 | 57-PheArgAsnAlaAspArgAla-63 |
| SEQ. ID. NO. 35593 | 67-ValLysGluSerMetArgThrGluGluSerLeu-77 |
| SEQ. ID. NO. 35594 | 80-AlaValAspAspGlyProLeuGlnSerGluLysAspTyr-92 |
| SEQ. ID. NO. 35595 | 98-ArgLeuSerArgLeuLysGluLysAlaLys-107 |
| SEQ. ID. NO. 35596 | 112-ThrGluGlnGluHisGlyGlu-118 |
| SEQ. ID. NO. 35597 | 136-LeuSerGlnArgSerProGlu-142 |
| SEQ. ID. NO. 35598 | 151-TyrArgAsnAspArgProPhe-157 |
| SEQ. ID. NO. 35599 | 169-GluAsnTyrGluThrThrGlyGluTyr-177 |
| SEQ. ID. NO. 35600 | 190-AlaAlaGlyArgGlyLysIleGlyGluAspValTyr-201 |
| SEQ. ID. NO. 35601 | 217-LysTyrArgAspValAlaAsnAspGluGlnLysValTrpAspPheArgGluGluSerAsnArgIleAlaSerAspSerArgAsp-244 |
| SEQ. ID. NO. 35602 | 250-AsnMetArgGluLeuMetProArgGlyMetLys-260 |
| SEQ. ID. NO. 35603 | 268-TyrAspAlaAspGlyLeuPro-274 |
| SEQ. ID. NO. 35604 | 282-AspAsnGlyLysLysArgGlnSer-289 |
| SEQ. ID. NO. 35605 | 309-LeuLysAlaAspGlyValThr-315 |
| SEQ. ID. NO. 35606 | 331-GlyGlyArgIleIleArgGluGluLysGlnGlyAspArgLeuPro-345 |
| SEQ. ID. NO. 35607 | 349-LeuAsnLeuGluAspLeuGluLysGluValSerArgTyrAlaGluAlaAlaAlaArgArgSerGlyGlyArgArgGlyLeuSer-376 |
| g729 | |
| AMPHI Regions - AMPHI | |
| SEQ. ID. NO. 35608 | 21-CysThrMetIleProGlnTyr-27 |
| SEQ. ID. NO. 35609 | 55-HisAspTyrPheAla-59 |
| SEQ. ID. NO. 35610 | 61-ProArgLeuGlnLysLeuIleAspIle-69 |
| SEQ. ID. NO. 35611 | 149-GlnGlyTyrPheAla-153 |
| SEQ. ID. NO. 35612 | 242-LeuAlaThrLeuIleAsn-247 |
| SEQ. ID. NO. 35613 | 250-IleProGluAspLeuProAla-256 |
| SEQ. ID. NO. 35614 | 268-LysLeuProAlaGlyLeu-273 |
| SEQ. ID. NO. 35615 | 321-GluLeuGlyGlyLeuProPheLysSerGly-329 |
| SEQ. ID. NO. 35616 | 371-ValGlnSerAlaPheGlnAspValAlaAsnAla-381 |

TABLE 1-continued

| SEQ. ID. NO. 35617 | 388-LeuAspLysAlaTyrAspAlaLeuSerLysGlnSerArg-400 |
| SEQ. ID. NO. 35618 | 419-GlyAlaLeuAspLeuLeuAspAlaGlu-427 |
| SEQ. ID. NO. 35619 | 442-LeuThrArgAlaGluAsnLeuAlaAspLeuTyrLysAlaLeuAspGlyGlyLeu-459 |

Antigenic Index - Jameson-Wolf

| SEQ. ID. NO. 35620 | 25-ProGlnTyrGluGlnProLysValGluVal-34 |
| SEQ. ID. NO. 35621 | 36-GluThrPheGlnAsnAspThrSerValSerSer-46 |
| SEQ. ID. NO. 35622 | 53-GlyTrpHisAspTyrPheAlaAspProArgLeuGlnLys-65 |
| SEQ. ID. NO. 35623 | 70-AlaLeuGluArgAsnThrSerLeuArgThr-79 |
| SEQ. ID. NO. 35624 | 85-GluIleTyrArgLysGlnTyrMetIleGluArgAsnAsnLeuLeuPro-100 |
| SEQ. ID. NO. 35625 | 106-AlaAsnGlySerArgGlnGlySerLeuSerGlyGlyAsnValSerSerSerTyrAsn-124 |
| SEQ. ID. NO. 35626 | 138-GlyArgValArgSerAsnSerGluAlaAla-147 |
| SEQ. ID. NO. 35627 | 156-AlaAsnArgAspAlaAla-161 |
| SEQ. ID. NO. 35628 | 173-TyrPheAsnGluArgTyrAlaGluLysAlaMet-183 |
| SEQ. ID. NO. 35629 | 188-ArgValLeuLysThrArgGluGluThrTyrLysLeuSerGluLeuArgTyr-204 |
| SEQ. ID. NO. 35630 | 215-ArgGlnGlnGluAlaLeuIleGluSerAlaLysAlaAspTyr-228 |
| SEQ. ID. NO. 35631 | 232-AlaArgSerArgGluGlnAlaArgAsn-240 |
| SEQ. ID. NO. 35632 | 247-AsnArgProIleProGluAspLeuProAla-256 |
| SEQ. ID. NO. 35633 | 277-ValLeuLeuAspArgProAspIleArgAlaAlaGluHisAlaLeuLysGlnAlaAsnAla-296 |
| SEQ. ID. NO. 35634 | 310-ArgLeuThrGlySerValGlyThrGlySer-319 |
| SEQ. ID. NO. 35635 | 326-PheLysSerGlyThr-330 |
| SEQ. ID. NO. 35636 | 347-GlyThrAsnLysAlaAsnLeuAspValAlaLysLeuArgGlnGln-361 |
| SEQ. ID. NO. 35637 | 383-AlaAlaArgGluGlnLeuAspLysAlaTyrAspAlaLeuSerLysGlnSerArgAlaSerLysGluAlaLeuArg-407 |
| SEQ. ID. NO. 35638 | 411-LeuArgTyrLysHisGlyValSer-418 |
| SEQ. ID. NO. 35639 | 424-LeuAspAlaGluArgIleSerTyrSerAlaGluGly-435 |
| SEQ. ID. NO. 35640 | 442-LeuThrArgAlaGluAsnLeu-448 |
| SEQ. ID. NO. 35641 | 455-LeuAspGlyGlyLeuLysArgAspThrGlnThrGlyLys-467 |

Hydrophilic Regions - Hopp-Woods

| SEQ. ID. NO. 35642 | 28-GluGlnProLysValGluVal-34 |
| SEQ. ID. NO. 35643 | 42-ThrSerValSerSer-46 |
| SEQ. ID. NO. 35644 | 61-ProArgLeuGlnLys-65 |
| SEQ. ID. NO. 35645 | 70-AlaLeuGluArgAsnThrSerLeu-77 |
| SEQ. ID. NO. 35646 | 91-TyrMetIleGluArgAsnAsn-97 |
| SEQ. ID. NO. 35647 | 107-AsnGlySerArgGlnGlySer-113 |
| SEQ. ID. NO. 35648 | 138-GlyArgValArgSerAsnSerGluAlaAla-147 |
| SEQ. ID. NO. 35649 | 156-AlaAsnArgAspAlaAla-161 |
| SEQ. ID. NO. 35650 | 177-ArgTyrAlaGluLysAlaMet-183 |
| SEQ. ID. NO. 35651 | 188-ArgValLeuLysThrArgGluGluThrTyrLys-198 |
| SEQ. ID. NO. 35652 | 200-SerGluLeuArgTyr-204 |
| SEQ. ID. NO. 35653 | 215-ArgGlnGlnGluAlaLeuIleGluSerAlaLysAlaAspTyr-228 |
| SEQ. ID. NO. 35654 | 232-AlaArgSerArgGluGlnAlaArgAsn-240 |
| SEQ. ID. NO. 35655 | 249-ProIleProGluAspLeuPro-255 |
| SEQ. ID. NO. 35656 | 277-ValLeuLeuAspArgProAspIleArgAlaAlaGluHisAlaLeuLysGlnAlaAsn-295 |
| SEQ. ID. NO. 35657 | 350-LysAlaAsnLeuAspValAlaLysLeuArgGln-360 |
| SEQ. ID. NO. 35658 | 383-AlaAlaArgGluGlnLeuAspLysAlaTyrAspAlaLeuSerLysGlnSerArgAlaSerLysGluAlaLeuArg-407 |
| SEQ. ID. NO. 35659 | 424-LeuAspAlaGluArgIleSerTyr-431 |
| SEQ. ID. NO. 35660 | 442-LeuThrArgAlaGluAsnLeu-448 |
| SEQ. ID. NO. 35661 | 455-LeuAspGlyGlyLeuLysArgAspThrGlnThrGlyLys-467 | g730

AMPHI Regions - AMPHI

| SEQ. ID. NO. 35662 | 6-ArgLeuThrAsnLeuLeuAlaAlaCysAla-15 |
| SEQ. ID. NO. 35663 | 26-LeuAlaAlaAspLeu-30 |
| SEQ. ID. NO. 35664 | 67-LysIleAsnValIleGlnAspTyrThrHisGln-77 |
| SEQ. ID. NO. 35665 | 111-AsnHisAlaAlaAsp-115 |
| SEQ. ID. NO. 35666 | 141-HisProAlaAspAlaTyrAspGlyProLysGlyGlyAsnTyrProLysProThr-158 |
| SEQ. ID. NO. 35667 | 187-GlnArgIlePheAspAsnTyrAsnAsnLeuGlySerAsnPheSerAspArgAlaAspGlu-206 |
| SEQ. ID. NO. 35668 | 214-HisAsnAlaLysLeu-218 |
| SEQ. ID. NO. 35669 | 220-ArgTrpGlyAsnSerMetGluPheValAsnGlyValAla-232 |
| SEQ. ID. NO. 35670 | 234-GlyAlaLeuAsnProPheIleSer-241 |
| SEQ. ID. NO. 35671 | 262-AlaAlaMetArgAsnIleAla-268 |
| SEQ. ID. NO. 35672 | 277-AlaAlaIleGlyGlyLeuGlySerAla-285 |
| SEQ. ID. NO. 35673 | 288-PheGluLysAsnThrArgGluAlaValAspArgTrpIleGlnGlu-302 |
| SEQ. ID. NO. 35674 | 305-AsnAlaAlaGluThrValGluAlaLeuValAsnValLeuProPheAlaLysValLysAsnLeuThrLysAlaAlaLysPro-331 |
| SEQ. ID. NO. 35675 | 353-LeuValLysThrAlaAspGlyTyrLysAlaIleAlaHisIleGlnAla-368 |
| SEQ. ID. NO. 35676 | 390-ArgTyrGlyAsnProTyr-395 |
| SEQ. ID. NO. 35677 | 403-ValSerAspGlyIle-407 |
| SEQ. ID. NO. 35678 | 434-LysAlaGlySerArgLeuLeuSerGluSer-443 |
| SEQ. ID. NO. 35679 | 458-ProLeuLysAlaTyr-462 |
| SEQ. ID. NO. 35680 | 510-AspSerHisArgSerValGlyAspSerAsnArgValValArgGluGlyLys-526 |
| SEQ. ID. NO. 35681 | 553-GlnValThrGlnPheLys-558 |

Antigenic Index - Jameson-Wolf

| SEQ. ID. NO. 35682 | 2-LysProLeuArgArgLeuThr-8 |
| SEQ. ID. NO. 35683 | 35-PheIleThrAspAsnThrGlnArgGlnHisTyrGluProGlyGlyLys-50 |
| SEQ. ID. NO. 35684 | 55-GlyAspProArgGlySerValSerAspArgThrGlyLysIleAsnVal-70 |
| SEQ. ID. NO. 35685 | 99-SerGlyHisGlyHisGluGluHisAlaProPheAsp-110 |
| SEQ. ID. NO. 35686 | 112-HisAlaAlaAspSerAlaSerGluGluLysGlyAsnValAspAspGlyPhe-128 |
| SEQ. ID. NO. 35687 | 133-LeuAsnTrpGluGlyHisGluHisHisProAlaAspAlaTyrAspGlyProLysGlyGlyAsnTyrProLysProThrGlyAlaArgAspGluTyrThrTyrHisVal-168 |
| SEQ. ID. NO. 35688 | 170-GlyThrAlaArgSerIleLysLeuAsnProThrAspThrArgSerIleArgGlnArgIle-189 |
| SEQ. ID. NO. 35689 | 191-AspAsnTyrAsnAsnLeuGlySerAsnPheSerAspArgAlaAspGluAlaAsnArgLysMetPheGluHisAsnAlaLysLeuAspArgTrpGlyAsnSer-224 |

TABLE 1-continued

| | |
|---|---|
| SEQ. ID. NO. 35690 | 257-TyrAlaIleAspLysAlaAlaMet-264 |
| SEQ. ID. NO. 35691 | 271-ProAlaGluGlyLysPhe-276 |
| SEQ. ID. NO. 35692 | 287-GlyPheGluLysAsnThrArgGluAlaValAsp-297 |
| SEQ. ID. NO. 35693 | 299-TrpIleGlnGluAsnProAsnAlaAlaGluThrValGlu-311 |
| SEQ. ID. NO. 35694 | 323-LysAsnLeuThrLysAlaAlaLysProGlyLysAlaAlaValSerGlyAspPheSerLysSerTyr-344 |
| SEQ. ID. NO. 35695 | 355-LysThrAlaAspGlyTyrLys-361 |
| SEQ. ID. NO. 35696 | 367-GlnAlaGlyAspArgValLeuSerLysAspGluAlaSerGlyGluThrGlyTyrLysProValThrAlaArgTyrGlyAsnProTyrGlnGlu-397 |
| SEQ. ID. NO. 35697 | 403-ValSerAspGlyIleGlyAsnSer-410 |
| SEQ. ID. NO. 35698 | 422-TyrSerAspGlyLysTrpIleLysAlaGluAspLeuLysAlaGlySerArgLeuLeuSerGluSerGlyLysThrGlnThr-448 |
| SEQ. ID. NO. 35699 | 453-ValValLysProLysProLeuLys-460 |
| SEQ. ID. NO. 35700 | 474-ValLysGlyAsnGlnAlaGluThrGlu-482 |
| SEQ. ID. NO. 35701 | 487-HisAsnAspCysProProLysProLysProThrAsnHisAlaGlnGlnArgLysGluGluAlaLysAsnAspSerHisArgSerValGlyAspSerAsn ArgValValArgGluGlyLysGlnTyrLeuAspSerAspThrGlyAsn-535 |
| SEQ. ID. NO. 35702 | 538-TyrValLysGlyAspLysVal-544 |
| SEQ. ID. NO. 35703 | 547-LeuThrProAspGlyArgGlnValThrGlnPheLysAsnSerLysAlaAsnThrSerLysArgValLysAsnGlyLysTrpThrProLys-576 |
| Hydrophilic Regions - Hopp-Woods | |
| SEQ. ID. NO. 35704 | 2-LysProLeuArgArgLeuThr-8 |
| SEQ. ID. NO. 35705 | 39-AsnThrGlnArgGlnHisTyrGluProGlyGly-49 |
| SEQ. ID. NO. 35706 | 55-GlyAspProArgGlySerValSerAspArgThrGlyLys-67 |
| SEQ. ID. NO. 35707 | 102-GlyHisGluGluHisAlaPro-108 |
| SEQ. ID. NO. 35708 | 112-HisAlaAlaAspSerAlaSerGluGluLysGlyAsnValAspAspGly-127 |
| SEQ. ID. NO. 35709 | 135-TrpGluGlyHisGluHisHisPro-142 |
| SEQ. ID. NO. 35710 | 144-AspAlaTyrAspGlyProLysGlyGlyAsnTyrProLys-156 |
| SEQ. ID. NO. 35711 | 158-ThrGlyAlaArgAspGluTyr-164 |
| SEQ. ID. NO. 35712 | 170-GlyThrAlaArgSerIleLys-176 |
| SEQ. ID. NO. 35713 | 178-AsnProThrAspThrArgSerIleArgGlnArgIle-189 |
| SEQ. ID. NO. 35714 | 200-PheSerAspArgAlaAspGluAlaAsnArgLysMetPheGluHisAsnIaLysLeuAspArgTrpGlyAsn-223 |
| SEQ. ID. NO. 35715 | 257-TyrAlaIleAspLysAlaAlaMet-264 |
| SEQ. ID. NO. 35716 | 271-ProAlaGluGlyLysPhe-276 |
| SEQ. ID. NO. 35717 | 287-GlyPheGluLysAsnThrArgGluAlaValAsp-297 |
| SEQ. ID. NO. 35718 | 303-AsnProAsnAlaAlaGluThrValGlu-311 |
| SEQ. ID. NO. 35719 | 323-LysAsnLeuThrLysAlaAlaLysProGlyLysAlaAlaVal-336 |
| SEQ. ID. NO. 35720 | 355-LysThrAlaAspGlyTyrLys-361 |
| SEQ. ID. NO. 35721 | 368-AlaGlyAspArgValLeuSerLysAspGluAlaSerGlyGluThrGlyTyr-384 |
| SEQ. ID. NO. 35722 | 403-ValSerAspGlyIleGly-408 |
| SEQ. ID. NO. 35723 | 426-LysTrpIleLysAlaGluAspLeuLysAlaGlySer-437 |
| SEQ. ID. NO. 35724 | 439-LeuLeuSerGluSerGlyLysThrGlnThr-448 |
| SEQ. ID. NO. 35725 | 453-ValValLysProLysProLeuLys-460 |
| SEQ. ID. NO. 35726 | 477-AsnGlnAlaGluThrGlu-482 |
| SEQ. ID. NO. 35727 | 489-AspCysProProLysProLysProThrAsn-498 |
| SEQ. ID. NO. 35728 | 500-AlaGlnAsnArgLysGluGluAlaLysAsnAspSerHisArgSerValGlyAspSerAsnArgValValArgGluGlyLysGlnTyrLeuAspSer AspThrGly-534 |
| SEQ. ID. NO. 35729 | 539-ValLysGlyAspLys-543 |
| SEQ. ID. NO. 35730 | 549-ProAspGlyArgGln-553 |
| SEQ. ID. NO. 35731 | 558-LysAsnSerLysAlaAsnThrSerLysArgValLysAsnGlyLysTrpThrPro-575 |
| g731 | |
| AMPHI Regions - AMPHI | |
| SEQ. ID. NO. 35732 | 17-AlaCysAlaValProGluAlaTyrAspGlyGly-27 |
| SEQ. ID. NO. 35733 | 40-GlyProAspAspPheArgAlaPheSerCys-49 |
| Antigenic Index - Jameson-Wolf | |
| SEQ. ID. NO. 35734 | 22-GluAlaTyrAspGlyGlyGlyArgGlyTyr-31 |
| SEQ. ID. NO. 35735 | 33-ProProValGlnAsnGlnAlaGlyProAspAspPheArgAla-46 |
| SEQ. ID. NO. 35736 | 48-SerCysGluAsnGlyLeu-53 |
| SEQ. ID. NO. 35737 | 55-ValArgValArgAsnLeuAspGlyGlyLysIleAlaLeuArgLeuAspGlyArgArgAlaValLeuSerSerAspValAlaAlaSerGlyGluArgTyr ThrAla-89 |
| SEQ. ID. NO. 35738 | 92-GlyLeuPheGlyAsnGlyThrGluTrpHisGlnLysGlyGlyGluAla-107 |
| SEQ. ID. NO. 35739 | 113-AspAlaTyrGlyAsnSerValGluThrSerCysArgAlaArg-126 |
| Hydrophilic Regions - Hopp-Woods | |
| SEQ. ID. NO. 35740 | 22-GluAlaTyrAspGlyGlyGly-28 |
| SEQ. ID. NO. 35741 | 39-AlaGlyProAspAspPheArg-45 |
| SEQ. ID. NO. 35742 | 55-ValArgValArgAsnLeuAspGlyGlyLysIleAlaLeuArgLeuAspGlyArgArgAlaValLeu-76 |
| SEQ. ID. NO. 35743 | 80-ValAlaAlaSerGlyGluArgTyrThrAla-89 |
| SEQ. ID. NO. 35744 | 100-TrpHisGlnLysGlyGlyGlu-106 |
| SEQ. ID. NO. 35745 | 119-ValGluThrSerCysArgAlaArg-126 |
| g732 | |
| AMPHI Regions - AMPHI | |
| SEQ. ID. NO. 35746 | 14-LeuGlyAlaIleSer-18 |
| SEQ. ID. NO. 35747 | 43-ValGlnSerIleArgThrMetAlaGluValTyrGly-54 |
| SEQ. ID. NO. 35748 | 66-AspAlaAspLeuPheGluGlyAlaMetLysGlyMetVal-78 |
| SEQ. ID. NO. 35749 | 95-GluIleLysGluSerThrSerGly-102 |
| SEQ. ID. NO. 35750 | 115-AspGlyPheValLysValValSerProIleGluAsp-126 |
| SEQ. ID. NO. 35751 | 155-GluAlaValLysLysMet-160 |
| SEQ. ID. NO. 35752 | 183-ValAsnLeuThrArg-187 |
| SEQ. ID. NO. 35753 | 214-GluArgThrValGluSerValAsnThrAlaAlaLys-225 |
| SEQ. ID. NO. 35754 | 283-LysAlaValProGluAspTyrValTyr-291 |
| SEQ. ID. NO. 35755 | 293-MetGlyGlyAspProLeuAlaGlyIleProAlaGluLeu-305 |
| SEQ. ID. NO. 35756 | 322-SerGluIleValAlaGly-327 |
| SEQ. ID. NO. 35757 | 400-LeuValGlyHisIleGlyAsn-406 |
| SEQ. ID. NO. 35758 | 446-ArgArgIleProAsnProAlaLysAsp-454 |
| SEQ. ID. NO. 35759 | 459-LysAlaLeuAspLeuValLysSerProGluGlnTrpGlnLysSerLeu-474 |

TABLE 1-continued

Antigenic Index - Jameson-Wolf
SEQ. ID. NO. 35760    30-AlaAlaGluLysAspGlyArgAspAsnGluVal-40
SEQ. ID. NO. 35761    59-AsnTyrTyrHisAspLysProAspAlaAspLeuPhe-70
SEQ. ID. NO. 35762    82-AspProHisSerGluTyrMetAspLysLysGlyTyrAlaGluIleLysGluSerThrSerGlyGluPheGlyGly-106
SEQ. ID. NO. 35763    111-IleGlyGlnGluAspGlyPhe-117
SEQ. ID. NO. 35764    122-SerProIleGluAspThrProAlaGluArgAlaGluValLysSerGlyAspPhe-139
SEQ. ID. NO. 35765    144-AspAsnValSerThrArgGlyMetThr-152
SEQ. ID. NO. 35766    155-GluAlaValLysLysMetArgGlyLysProGlyThrLysIle-168
SEQ. ID. NO. 35767    172-LeuSerArgLysAsnAlaAspLysProIle-181
SEQ. ID. NO. 35768    199-LeuIleGluProAspTyrGlyTyr-206
SEQ. ID. NO. 35769    211-GlnPheGlnGluArgThrValGlu-218
SEQ. ID. NO. 35770    221-AsnThrAlaAlaLysGluLeuValLysGluAsnLysGlyLysProLeuLys-237
SEQ. ID. NO. 35771    242-AspLeuArgAspAspProGlyLeu-250
SEQ. ID. NO. 35772    269-ValSerThrLysGlyArgAspGlyLysAspGlyMetVal-281
SEQ. ID. NO. 35773    284-AlaValProGluAspTyr-289
SEQ. ID. NO. 35774    293-MetGlyGlyAspPro-297
SEQ. ID. NO. 35775    303-AlaGluLeuLysThr-307
SEQ. ID. NO. 35776    316-SerGlySerAlaSerAla-321
SEQ. ID. NO. 35777    330-GlnAspHisLysArgAlaVal-336
SEQ. ID. NO. 35778    340-ThrGlnSerPheGlyLysGlySerVal-348
SEQ. ID. NO. 35779    354-LeuSerAsnGlySer-358
SEQ. ID. NO. 35780    368-TyrThrProAsnAspArgSerIleGln-376
SEQ. ID. NO. 35781    384-ValGluValLysAspLysGluArgThrPheGluSerArgGluAlaAspLeu-400
SEQ. ID. NO. 35782    405-GlyAsnProLeuGlyGlyGluAspValAsnSerGlu-416
SEQ. ID. NO. 35783    421-ProLeuGluLysAspAlaAspLysProAlaAlaGluLysGlyLysLysLysLysAspGluAspLeuSerSerArgArgIleProAsnProAla
                      LysAspAspGlnLeuArgLysAlaLeuAspLeuValLysSerProGluGlnTrpGlnLys-472
SEQ. ID. NO. 35784    477-AlaAlaLysLysProValSerAsnLysAspLysLysAspLysLys-491
Hydrophilic Regions - Hopp-Woods
SEQ. ID. NO. 35785    30-AlaAlaGluLysAspGlyArgAspAsnGluVal-40
SEQ. ID. NO. 35786    60-TyrTyrHisAspLysProAspAlaAspLeuPhe-70
SEQ. ID. NO. 35787    82-AspProHisSerGluTyrMetAspLysLysGlyTyrAlaGluIleLysGluSerThrSerGlyGlu-103
SEQ. ID. NO. 35788    111-IleGlyGlnGluAspGlyPhe-117
SEQ. ID. NO. 35789    122-SerProIleGluAspThrProAlaGluArgAlaGluValLysSerGlyAspPhe-139
SEQ. ID. NO. 35790    144-AspAsnValSerThr-148
SEQ. ID. NO. 35791    155-GluAlaValLysLysMetArgGlyLysProGlyThr-166
SEQ. ID. NO. 35792    172-LeuSerArgLysAsnAlaAspLysProIle-181
SEQ. ID. NO. 35793    211-GlnPheGlnGluArgThrValGlu-218
SEQ. ID. NO. 35794    221-AsnThrAlaAlaLysGluLeuValLysGluAsnLysGlyLysProLeuLys-237
SEQ. ID. NO. 35795    242-AspLeuArgAspAspProGly-248
SEQ. ID. NO. 35796    271-ThrLysGlyArgAspGlyLysAspGlyMetVal-281
SEQ. ID. NO. 35797    303-AlaGluLeuLysThr-307
SEQ. ID. NO. 35798    330-GlnAspHisLysArgAlaVal-336
SEQ. ID. NO. 35799    370-ProAsnAspArgSerIleGln-376
SEQ. ID. NO. 35800    384-ValGluValLysAspLysGluArgThrPheGluSerArgGluAlaAspLeu-400
SEQ. ID. NO. 35801    408-LeuGlyGlyGluAspValAsnSer-415
SEQ. ID. NO. 35802    421-ProLeuGluLysAspAlaAspLysProAlaAlaGluLysGlyLysLysLysLysAspGluAspLeuSerSerArgArgIleProAsnProAla
                      LysAspAspGlnLeuArgLysAlaLeuAspLeuValLysSerProGluGlnTrpGln-471
SEQ. ID. NO. 35803    477-AlaAlaLysLysProValSerAsnLysAspLysLysAspLysLys-491
g733
AMPHI Regions - AMPHI
SEQ. ID. NO. 35804    6-ThrLeuGlyArgLeuSer-11
SEQ. ID. NO. 35805    16-ValLeuAlaLeuThrAla-21
SEQ. ID. NO. 35806    33-TyrGlyGlyTyrProAspThrValTyrGluGly-43
SEQ. ID. NO. 35807    53-LysGlnThrGluLysMetGluLysTyrPheAlaGluAlaAlaAsn-67
SEQ. ID. NO. 35808    92-GlyAlaPheArgGlnPheGluGlu-99
Antigenic Index - Jameson-Wolf
SEQ. ID. NO. 35809    2-MetAsnProLysThrLeuGly-8
SEQ. ID. NO. 35810    23-AlaGlyGlyGlyHisLys-28
SEQ. ID. NO. 35811    32-TyrTyrGlyGlyTyrProAspThrValTyrGluGlyLeuLysAsnAspAspThrSerLeuGlyLysGlnThrGluLysMetGluLysTyrPhe-62
SEQ. ID. NO. 35812    65-AlaAlaAsnLysLysMetAsnAlaAlaProGlyAla-76
SEQ. ID. NO. 35813    84-LeuSerArgSerGlyAspLysGluGlyAlaPheArgGlnPheGluGluGluLysArgLeuPheProGlu-106
SEQ. ID. NO. 35814    115-MetLysThrGlyLysGlyGlyLysArg-123
Hydrophilic Regions - Hopp-Woods
SEQ. ID. NO. 35815    40-ValTyrGluGlyLeuLysAsnAspAspThrSerLeuGlyLysGlnThrGluLysMetGluLysTyrPhe-62
SEQ. ID. NO. 35816    65-AlaAlaAsnLysLysMetAsnAla-72
SEQ. ID. NO. 35817    86-ArgSerGlyAspLysGluGlyAlaPheArgGlnPheGluGluGluLysArgLeuPhePro-105
SEQ. ID. NO. 35818    115-MetLysThrGlyLysGlyGlyLysArg-123
g734
AMPHI Regions - AMPHI
SEQ. ID. NO. 35819    26-TyrLeuAlaValTrpGlnAsnProGlnAspAlaAsnAspValLeuGlnVal-42
SEQ. ID. NO. 35820    53-GluAlaPheAlaGluLeuGluAlaPheCysLys-63
SEQ. ID. NO. 35821    77-ThrGlyCysArgSerValValSer-84
SEQ. ID. NO. 35822    92-LeuAlaTyrProLysAlaLeuGlyAlaMetArg-102
SEQ. ID. NO. 35823    113-ArgPheThrSerVal-117
SEQ. ID. NO. 35824    121-AlaLeuAsnGlnCysIleLysLys-128
Antigenic Index - Jameson-Wolf
SEQ. ID. NO. 35825    31-GlnAsnProGlnAspAlaAsnAspValLeuGln-41
SEQ. ID. NO. 35826    43-LysThrThrLysGluAspSerAlaLysSerGluAlaPheAlaGlu-57
SEQ. ID. NO. 35827    60-AlaPheCysLysGlyGlnAspThr-67
SEQ. ID. NO. 35828    71-IleAlaGluAspGluProThrGlyCysArgSer-81

TABLE 1-continued

| | |
|---|---|
| SEQ. ID. NO. 35829 | 101-MetArgValGluAsn-105 |
| SEQ. ID. NO. 35830 | 111-SerProArgPheThrSer-116 |
| SEQ. ID. NO. 35831 | 125-CysIleLysLysTyrGlyAlaGlnGly-133 |
| SEQ. ID. NO. 35832 | 145-SerSerTyrTyrGly-149 |

Hydrophilic Regions - Hopp-Woods

| | |
|---|---|
| SEQ. ID. NO. 35833 | 34-GlnAspAlaAsnAsp-38 |
| SEQ. ID. NO. 35834 | 43-LysThrThrLysGluAspSerAlaLysSerGluAlaPheAlaGlu-57 |
| SEQ. ID. NO. 35835 | 60-AlaPheCysLysGlyGlnAspThr-67 |
| SEQ. ID. NO. 35836 | 71-IleAlaGluAspGluProThrGlyCys-79 |
| SEQ. ID. NO. 35837 | 101-MetArgValGluAsn-105 |
| SEQ. ID. NO. 35838 | 125-CysIleLysLysTyrGlyAla-131 | g736
AMPHI Regions - AMPHI

| | |
|---|---|
| SEQ. ID. NO. 35839 | 13-GlyLeuIleGlnSerPheGlySer-20 |
| SEQ. ID. NO. 35840 | 50-GlyValLeuSerVal-54 |
| SEQ. ID. NO. 35841 | 61-GlyLeuPheValGly-65 |
| SEQ. ID. NO. 35842 | 70-LeuGlnGlyTyrThrGlnLeuSerLysPheLysSerAlaAspIle-84 |
| SEQ. ID. NO. 35843 | 93-LeuLeuArgGluLeuGlyProVal-100 |
| SEQ. ID. NO. 35844 | 120-LeuMetLysThrThrGlyGlnLeuGluAlaMetAsnValMet-133 |
| SEQ. ID. NO. 35845 | 135-ValAsnProValAlaArgValVal-142 |
| SEQ. ID. NO. 35846 | 144-ProArgPheTrpAlaGlyValPheSerMetPro-154 |
| SEQ. ID. NO. 35847 | 156-LeuAlaSerIlePheAsnValAlaGlyIlePheGlyAla-168 |
| SEQ. ID. NO. 35848 | 196-AspValIleAsnGlyLeu-201 |
| SEQ. ID. NO. 35849 | 230-LeuArgAlaSerThrArgThr-236 |

Antigenic Index - Jameson-Wolf

| | |
|---|---|
| SEQ. ID. NO. 35850 | 30-AlaLysSerGlyThrAlaPheAlaArgProArgLeuSerVal-43 |
| SEQ. ID. NO. 35851 | 77-SerLysPheLysSer-81 |
| SEQ. ID. NO. 35852 | 93-LeuLeuArgGluLeuGly-98 |
| SEQ. ID. NO. 35853 | 109-SerAlaGlyGlyAlaMetThrSer-116 |
| SEQ. ID. NO. 35854 | 186-GlnMetGlnAsnAsn-190 |
| SEQ. ID. NO. 35855 | 224-ProThrSerGluGlyIleLeuArgAlaSerThr-234 |

Hydrophilic Regions - Hopp-Woods

| | |
|---|---|
| SEQ. ID. NO. 35856 | 37-AlaArgProArgLeuSerVal-43 |
| SEQ. ID. NO. 35857 | 77-SerLysPheLysSer-81 |
| SEQ. ID. NO. 35858 | 93-LeuLeuArgGluLeuGly-98 | g737
AMPHI Regions - AMPHI

| | |
|---|---|
| SEQ. ID. NO. 35859 | 56-AlaAlaTrpAlaArgValGlyGly-63 |

Antigenic Index - Jameson-Wolf

| | |
|---|---|
| SEQ. ID. NO. 35860 | 24-AlaHisHisAspGlyHisGlyAspAspAspHisGlyHis-36 |
| SEQ. ID. NO. 35861 | 38-AlaHisGlnHisGlyLysGlnAspLysIleIleSer-49 |
| SEQ. ID. NO. 35862 | 51-AlaGlnAlaGluLysAlaAla-57 |
| SEQ. ID. NO. 35863 | 60-ArgValGlyGlyLysIleThrAspIleAspLeuGluHisAspAspGlyArgProHisTyrAspValGluIleValLysAsnGlyGlnGluTyr-90 |
| SEQ. ID. NO. 35864 | 94-ValAspAlaArgThrGlyArgValIleSerSerArgArgAspAsp-108 |

Hydrophilic Regions - Hopp-Woods

| | |
|---|---|
| SEQ. ID. NO. 35865 | 27-AspGlyHisGlyAspAspAspHisGlyHis-36 |
| SEQ. ID. NO. 35866 | 40-GlnHisGlyLysGlnAspLysIleIleSer-49 |
| SEQ. ID. NO. 35867 | 51-AlaGlnAlaGluLysAlaAla-57 |
| SEQ. ID. NO. 35868 | 61-ValGlyGlyLysIleThrAspIleAspLeuGluHisAspAspGlyArgProHisTyr-79 |
| SEQ. ID. NO. 35869 | 82-GluIleValLysAsnGlyGlnGluTyr-90 |
| SEQ. ID. NO. 35870 | 94-ValAspAlaArgThrGlyArg-100 |
| SEQ. ID. NO. 35871 | 102-IleSerSerArgArgAspAsp-108 | g738
AMPHI Regions - AMPHI

| | |
|---|---|
| SEQ. ID. NO. 35872 | 91-LeuMetAsnLeuIleTyrProGlyMetAsnAspIleAla-103 |
| SEQ. ID. NO. 35873 | 139-IleGlySerLeuLeuGlnSerCysIle-147 |
| SEQ. ID. NO. 35874 | 201-LysIleProAlaAlaLeu-206 |
| SEQ. ID. NO. 35875 | 228-ThrTyrIleAlaAlaIleAlaLeuIle-236 |
| SEQ. ID. NO. 35876 | 271-AlaIleLeuGluThrPheThrGlyIle-279 |
| SEQ. ID. NO. 35877 | 285-ValGluArgValAlaAsnGlyGlyPheThrAspLeuProArgGlnSer-300 |
| SEQ. ID. NO. 35878 | 304-LysAlaLeuAlaAlaPheGlnSer-311 |
| SEQ. ID. NO. 35879 | 316-GlyHisGlyTrpAsnSerPheAla-323 |
| SEQ. ID. NO. 35880 | 338-AspAsnPheLeuSerThrLeuPheThr-346 |
| SEQ. ID. NO. 35881 | 353-LeuGlnLeuLeuAlaGlu-358 |
| SEQ. ID. NO. 35882 | 371-LeuLeuThrGlyIleAlaGlyLeuLeuLysArg-381 |
| SEQ. ID. NO. 35883 | 398-MetCysHisSerMetLeu-403 |
| SEQ. ID. NO. 35884 | 461-ArgLeuValAsnSerPheSerPro-468 |
| SEQ. ID. NO. 35885 | 472-AspSerAlaLysThrLeuAsnArgLys-480 |
| SEQ. ID. NO. 35886 | 482-AsnGluLeuArgTyrIleSer-488 |
| SEQ. ID. NO. 35887 | 507-LeuProGluTyrProGluThr-513 |
| SEQ. ID. NO. 35888 | 549-AlaLysGlnTrpMetArgAlaThr-556 |
| SEQ. ID. NO. 35889 | 567-TyrAlaAspGluIleArgLysLeuProVal-576 |
| SEQ. ID. NO. 35890 | 579-ProLeuLeuProGluLeuLeuLysAspCysLysAlaPheAlaAlaAlaPro-595 |

Antigenic Index - Jameson-Wolf

| | |
|---|---|
| SEQ. ID. NO. 35891 | 5-ThrThrValSerGlyAlaArgProAlaAla-14 |
| SEQ. ID. NO. 35892 | 37-ArgLeuLysProSerProAspPheTyr-45 |
| SEQ. ID. NO. 35893 | 62-AlaGlyLysLysLeuPheAsp-68 |
| SEQ. ID. NO. 35894 | 124-TyrGlyGlnGluArgIle-129 |
| SEQ. ID. NO. 35895 | 167-HisArgGlyGlnGly-171 |
| SEQ. ID. NO. 35896 | 176-IleGlyGlnArgAsnAsnLeuGly-183 |

TABLE 1-continued

| | |
|---|---|
| SEQ. ID. NO. 35897 | 196-LeuAsnGlyGlnArgLysIlePro-203 |
| SEQ. ID. NO. 35898 | 242-PheArgSerAspLysSerAsnArgArgThrMet-252 |
| SEQ. ID. NO. 35899 | 283-ThrAlaValGluArgValAlaAsnGlyGlyPheThrAspLeuProArgGlnSerGluTrpAsn-303 |
| SEQ. ID. NO. 35900 | 316-GlyHisGlyTrpAsnSerPheAla-323 |
| SEQ. ID. NO. 35901 | 335-ThrIleHisAspAsnPhe-340 |
| SEQ. ID. NO. 35902 | 378-LeuLeuLysArgSerLeuThrProAlaSer-387 |
| SEQ. ID. NO. 35903 | 424-ProAlaGluAlaSerAspGlyIleAlaPheLysLysAlaAla-437 |
| SEQ. ID. NO. 35904 | 467-SerProAlaAlaAspAspSerAlaLysThrLeuAsnArgLysIleAsnGlu-483 |
| SEQ. ID. NO. 35905 | 508-ProGluTyrProGluThrGlnThrTrpAlaGlu-518 |
| SEQ. ID. NO. 35906 | 525-LeuLysTyrArgProTyrSerAla-532 |
| SEQ. ID. NO. 35907 | 542-ArgGlnGlyLysValAlaGluAlaLysGlnTrpMet-553 |
| SEQ. ID. NO. 35908 | 555-AlaThrGlnSerTyr-559 |
| SEQ. ID. NO. 35909 | 566-ArgTyrAlaAspGluIleArgLys-573 |
| SEQ. ID. NO. 35910 | 584-LeuLeuLysAspCysLysAla-590 |
| SEQ. ID. NO. 35911 | 595-ProGlyHisProGluThrLysProCysLys-604 |
| Hydrophilic Regions - Hopp-Woods | |
| SEQ. ID. NO. 35912 | 5-ThrThrValSerGlyAlaArgProAlaAla-14 |
| SEQ. ID. NO. 35913 | 38-LeuLysProSerPro-42 |
| SEQ. ID. NO. 35914 | 62-AlaGlyLysLysLeuPheAsp-68 |
| SEQ. ID. NO. 35915 | 125-GlyGlnGluArgIle-129 |
| SEQ. ID. NO. 35916 | 177-GlyGlnArgAsnAsn-181 |
| SEQ. ID. NO. 35917 | 198-GlyGlnArgLysIlePro-203 |
| SEQ. ID. NO. 35918 | 243-ArgSerAspLysSerAsnArgArgThrMet-252 |
| SEQ. ID. NO. 35919 | 283-ThrAlaValGluArgValAla-289 |
| SEQ. ID. NO. 35920 | 295-AspLeuProArgGlnSerGluTrpAsn-303 |
| SEQ. ID. NO. 35921 | 378-LeuLeuLysArgSerLeuThr-384 |
| SEQ. ID. NO. 35922 | 425-AlaGluAlaSerAsp-429 |
| SEQ. ID. NO. 35923 | 431-IleAlaPheLysLysAlaAla-437 |
| SEQ. ID. NO. 35924 | 468-ProAlaAlaAspAspSerAlaLysThrLeuAsnArgLysIleAsnGlu-483 |
| SEQ. ID. NO. 35925 | 542-ArgGlnGlyLysValAlaGluAlaLysGlnTrpMet-553 |
| SEQ. ID. NO. 35926 | 566-ArgTyrAlaAspGluIleArgLys-573 |
| SEQ. ID. NO. 35927 | 584-LeuLeuLysAspCysLysAla-590 |
| SEQ. ID. NO. 35928 | 596-GlyHisProGluThrLysProCysLys-604 |
| g739 | |
| AMPHI Regions - AMPHI | |
| SEQ. ID. NO. 35929 | 6-AsnLysProPheArgLeu-11 |
| SEQ. ID. NO. 35930 | 53-HisThrAspSerPro-57 |
| SEQ. ID. NO. 35931 | 88-GlnProAspGlyThrGlu-93 |
| SEQ. ID. NO. 35932 | 116-AspAlaAlaArgAlaAlaAspSerLeuThrGlyThr-127 |
| SEQ. ID. NO. 35933 | 131-AlaGluAsnThrLeu-135 |
| Antigenic Index - Jameson-Wolf | |
| SEQ. ID. NO. 35934 | 1-MetAlaLysLysProAsnLysProPheArgLeuThrPro-13 |
| SEQ. ID. NO. 35935 | 39-PheAsnProAsnGlyAspLysThrLeuGlnThrGluProGlnHisThrAspSerProArgGluThrGluPhe-62 |
| SEQ. ID. NO. 35936 | 64-LeuProAsnGlyAlaValGlyGlnAspAlaAlaGlnProGluHisHisHis-80 |
| SEQ. ID. NO. 35937 | 82-AlaSerSerGluProAlaGlnProAspGlyThrGluGluSerGlySerGlyLeuProSerProAlaAlaProLysLysAsnArgValLysProArgProSerAspAlaAlaArgAlaAlaAspSerLeuThrGlyThrGlyThrGlnAlaGluAsnThrLeuLysGluThrProVal-140 |
| SEQ. ID. NO. 35938 | 142-ProThrAsnAlaProHisProGluProArgLysGluThrProGluLysGlnAlaGlnProLysGluThrProLysGluLysGluThrProLysGluAsnHisThrLysProAspThrProLysAsnThrProAlaLysProHisLysGluIleLeu-193 |
| Hydrophilic Regions - Hopp-Woods | |
| SEQ. ID. NO. 35939 | 1-MetAlaLysLysProAsnLysProPheArgLeu-11 |
| SEQ. ID. NO. 35940 | 41-ProAsnGlyAspLysThrLeuGlnThrGluProGlnHisThrAspSerProArgGluThrGlu-61 |
| SEQ. ID. NO. 35941 | 69-ValGlyGlnAspAlaAlaGlnProGluHisHisHis-80 |
| SEQ. ID. NO. 35942 | 82-AlaSerSerGluProAlaGlnProAspGlyThrGluGluSerGlySer-97 |
| SEQ. ID. NO. 35943 | 103-AlaAlaProLysLysAsnArgValLysProArgProSerAspAlaAlaArgAlaAlaAspSerLeuThr-125 |
| SEQ. ID. NO. 35944 | 129-ThrGlnAlaGluAsnThrLeuLysGluThrPro-139 |
| SEQ. ID. NO. 35945 | 146-ProHisProGluProArgLysGluThrProGluLysGlnAlaGlnProLysGluThrProLysGluLysGluThrProLysGluAsnHisThrLysProAspThrProLysAsnThrProAlaLysProHisLysGluIleLeu-193 |
| g740 | |
| AMPHI Regions - AMPHI | |
| SEQ. ID. NO. 35946 | 6-LeuValArgTrpLeuAlaVal-12 |
| SEQ. ID. NO. 35947 | 57-IleLysHisHisLeu-61 |
| Antigenic Index - Jameson-Wolf | |
| SEQ. ID. NO. 35948 | 25-AlaAsnProProGluAspLysProGln-33 |
| SEQ. ID. NO. 35949 | 57-IleLysHisHisLeu-61 |
| SEQ. ID. NO. 35950 | 63-GlnGlyPheAspLeuLysArgGlnThr-71 |
| Hydrophilic Regions - Hopp-Woods | |
| SEQ. ID. NO. 35951 | 27-ProProGluAspLysProGln-33 |
| SEQ. ID. NO. 35952 | 57-IleLysHisHisLeu-61 |
| SEQ. ID. NO. 35953 | 63-GlnGlyPheAspLeuLysArgGlnThr-71 |
| g741 | |
| AMPHI Regions - AMPHI | |
| SEQ. ID. NO. 35954 | 35-GlyThrGlyLeuAlaAspAlaLeuThrAla-44 |
| SEQ. ID. NO. 35955 | 74-GlyAlaGluLysThrPheLysAlaGly-82 |
| SEQ. ID. NO. 35956 | 138-LysIleAsnAsnProAspLysIleAspSerLeuIle-149 |
| SEQ. ID. NO. 35957 | 164-ThrAlaPheAsnGlnLeuProAsp-171 |
| SEQ. ID. NO. 35958 | 205-IleGluHisLeuLys-209 |
| Antigenic Index - Jameson-Wolf | |
| SEQ. ID. NO. 35959 | 1-ValAsnArgThrThrPhe-6 |
| SEQ. ID. NO. 35960 | 12-ThrAlaGlyProAspSerAspArgLeuGlnGlnArgArgGlyGlyGlyGlyGlyVal-30 |
| SEQ. ID. NO. 35961 | 46-LeuAspHisLysAspLysGlyLeuLys-54 |

TABLE 1-continued

| | |
|---|---|
| SEQ. ID. NO. 35962 | 61-SerIleProGlnAsnGly-66 |
| SEQ. ID. NO. 35963 | 73-GlnGlyAlaGluLysThrPheLysAlaGlyGlyLysAspAsnSerLeuAsnThrGlyLysLeuLysAsnAspLysIleSerArg-100 |
| SEQ. ID. NO. 35964 | 107-IleGluValAspGlyGln-112 |
| SEQ. ID. NO. 35965 | 123-IleTyrLysGlnAspHisSerAla-130 |
| SEQ. ID. NO. 35966 | 135-ArgIleGluLysIleAsnAsnProAspLysIleAspSer-147 |
| SEQ. ID. NO. 35967 | 149-IleAsnGlnArgSer-153 |
| SEQ. ID. NO. 35968 | 157-SerAspLeuGlyGlyGluHisThr-164 |
| SEQ. ID. NO. 35969 | 168-GlnLeuProAspGlyLysAlaGluTyrHisGly-178 |
| SEQ. ID. NO. 35970 | 180-AlaPheSerSerAspAspAlaAspGlyLysLeu-190 |
| SEQ. ID. NO. 35971 | 196-PheAlaAlaLysGlnGlyHisGlyLysIleGluHisLeuLysThrProGluGlnAsnVal-215 |
| SEQ. ID. NO. 35972 | 218-AlaSerAlaGluLeuLysAlaAspGluLysSerHis-229 |
| SEQ. ID. NO. 35973 | 234-GlyAspThrArgTyrGlyGlyGluGluLysGlyThrTyrArg-247 |
| SEQ. ID. NO. 35974 | 251-PheGlyAspArgAlaGlnGluIleAlaGly-260 |
| SEQ. ID. NO. 35975 | 265-LysIleGlyGluLysValHisGlu-272 |
| SEQ. ID. NO. 35976 | 274-GlyIleAlaAspLysGln-279 |
| Hydrophilic Regions - Hopp-Woods | |
| SEQ. ID. NO. 35977 | 13-AlaGlyProAspSerAspArgLeuGlnGlnArgArgGlyGlyGly-27 |
| SEQ. ID. NO. 35978 | 46-LeuAspHisLysAspLysGlyLeuLys-54 |
| SEQ. ID. NO. 35979 | 73-GlnGlyAlaGluLysThrPheLysAlaGlyGlyLysAspAsnSerLeuAsn-89 |
| SEQ. ID. NO. 35980 | 91-GlyLysLeuLysAsnAspLysIleSerArg-100 |
| SEQ. ID. NO. 35981 | 107-IleGluValAspGly-111 |
| SEQ. ID. NO. 35982 | 135-ArgIleGluLysIleAsnAsnProAspLysIleAspSer-147 |
| SEQ. ID. NO. 35983 | 170-ProAspGlyLysAlaGluTyrHisGly-178 |
| SEQ. ID. NO. 35984 | 180-AlaPheSerSerAspAspAlaAspGlyLysLeu-190 |
| SEQ. ID. NO. 35985 | 200-GlnGlyHisGlyLysIleGluHisLeuLysThrProGluGlnAsnVal-215 |
| SEQ. ID. NO. 35986 | 218-AlaSerAlaGluLeuLysAlaAspGluLysSerHis-229 |
| SEQ. ID. NO. 35987 | 236-ThrArgTyrGlyGlyGluGluLysGlyThrTyr-246 |
| SEQ. ID. NO. 35988 | 252-GlyAspArgAlaGlnGluIleAlaGly-260 |
| SEQ. ID. NO. 35989 | 265-LysIleGlyGluLysValHisGlu-272 |
| SEQ. ID. NO. 35990 | 274-GlyIleAlaAspLysGln-279 |
| g746 | |
| AMPHI Regions - AMPHI | |
| SEQ. ID. NO. 35991 | 83-ThrAlaAlaAspLysProGlnAsp-90 |
| SEQ. ID. NO. 35992 | 105-SerGluProGluAsn-109 |
| SEQ. ID. NO. 35993 | 126-IleLysGlyLeuGluGluSerGluLysLeuGlnGlnAlaGlu-139 |
| SEQ. ID. NO. 35994 | 154-GluLysValSerAlaThr-159 |
| SEQ. ID. NO. 35995 | 164-AspThrValAlaValGlu-169 |
| SEQ. ID. NO. 35996 | 171-ProLysArgThrAlaGluPro-177 |
| SEQ. ID. NO. 35997 | 181-LysAlaGluArgThr-185 |
| SEQ. ID. NO. 35998 | 195-ThrLysThrAlaGluLysValAlaAspLysProLys-206 |
| SEQ. ID. NO. 35999 | 221-SerAlaValLysGluAlaLysLysAlaAspLysAlaGluGly-234 |
| SEQ. ID. NO. 36000 | 249-GluThrAlaGlnLysThrLysSerAlaAspLysThrLysThrAlaGluLysGluLysSerGlyLysAla-271 |
| SEQ. ID. NO. 36001 | 301-SerThrIleThrGluIleMetThr-308 |
| SEQ. ID. NO. 36002 | 321-TyrLysAsnAlaArgAspAlaGluArgAspLeu-331 |
| Antigenic Index - Jameson-Wolf | |
| SEQ. ID. NO. 36003 | 1-MetSerGluAsnLysGlnAsnGlu-8 |
| SEQ. ID. NO. 36004 | 14-GluGlnLeuLysArgArgAsnArgArgArgLeuValThr-26 |
| SEQ. ID. NO. 36005 | 42-LeuSerSerAspProAlaAspSerAsnProAlaProGlnAlaGlyGluThrGlyAlaThrGluSerGlnThrAlaAsnThrAlaGln-70 |
| SEQ. ID. NO. 36006 | 76-SerAlaAlaGluAsnGlyGluThrAlaAlaAspLysProGlnAspLeuAlaGlyGluAspLysProSerAlaAlaAspSerGluIleSerGluPro GluAsnVal-110 |
| SEQ. ID. NO. 36007 | 118-AsnAspArgLeuGluAspSerAsnIleLysGlyLeuGluGluSerGluLysLeuGlnGlnAlaGluThrAlaLysThrGluProLysGlnAlaLys GlnArgAlaAlaGluLysValSerAlaThrAlaAspSerThrAspThrValAlaValGluLysProLysArgThrAlaGluPro LysProGlnLysAlaGluArgThrAlaGluAlaLysProLysAlaLysGluThrLysThrAlaGluLysValAlaAspLysPro LysThrAlaAlaGluLysThrLysProAspThrAlaLysSerAspSerAlaValLysGluAlaLysLysAlaAspLysAlaGlu GlyLysLysThrAlaGluLysAspArgSerAspGlyLysLysHisGluThrAlaGlnLysThrAspLysAlaAspLysThrLys ThrAlaGluLysGluLysSerGlyLysAlaGlyLysLysAlaAla-276 |
| SEQ. ID. NO. 36008 | 280-GlyTyrAlaGluLysGluArgAlaLeuSerLeuGlnArgLysMetLysAlaAlaGlyIle-299 |
| SEQ. ID. NO. 36009 | 306-IleMetThrAspAsnGlyLysValTyrArgValLysSerSerAsnTyrLysAsnAlaArgAspAlaGluArgAspLeuAsnLysLeuArgVal-336 |
| Hydrophilic Regions - Hopp-Woods | |
| SEQ. ID. NO. 36010 | 1-MetSerGluAsnLysGlnAsnGlu-8 |
| SEQ. ID. NO. 36011 | 14-GluGlnLeuLysArgArgAsnArgArgArgLeuVal-25 |
| SEQ. ID. NO. 36012 | 42-LeuSerSerAspProAlaAspSerAsnPro-51 |
| SEQ. ID. NO. 36013 | 54-GlnAlaGlyGluThrGlyAlaThrGluSerGlnThr-65 |
| SEQ. ID. NO. 36014 | 76-SerAlaAlaGluAsnGlyGluThrAlaAlaAspLysProGlnAspLeuAlaGlyGluAspLysProSerAlaAlaAspSerGluIleSerGluPro GluAsnVal-110 |
| SEQ. ID. NO. 36015 | 119-AspArgLeuGluAspSerAsnIleLysGlyLeuGluGluSerGluLysLeuGlnGlnAlaGluThrAlaLysThrGluProLysGlnAlaLysGln ArgAlaAlaGluLysValSerAlaThrAlaAspSerThrAsp-164 |
| SEQ. ID. NO. 36016 | 166-ValAlaValGluLysProLysArgThrAlaGluProLysProGlnLysAlaGluArgThrAlaGluAlaLysProLysAlaLysGluThrLysThr AlaGluLysValAlaAspLysProLysThrAlaAlaGluLysThrLysProAspThrAlaLysSerAspSerAlaValLysGluAla LysLysAlaAspLysAlaGluGlyLysLysThrAlaGluLysAspArgSerAspGlyLysLysHisGluThrAlaGlnLysThrAsp LysAlaAspLysThrLysThrAlaGluLysGluLysSerGlyLysAlaGlyLysLysAlaAla-276 |
| SEQ. ID. NO. 36017 | 281-TyrAlaGluLysGluArgAlaLeuSerLeuGlnArgLysMetLysAlaAlaGlyIle-299 |
| SEQ. ID. NO. 36018 | 306-IleMetThrAspAsnGlyLysValTyrArgValLysSerSerAsnTyrLysAsnAlaArgAspAlaGluArgAspLeuAsnLysLeuArgVal-336 |
| g748 | |
| AMPHI Regions - AMPHI | |
| SEQ. ID. NO. 36019 | 22-GlyAlaIleGlyAlaIleGlyGly-29 |
| SEQ. ID. NO. 36020 | 37-GlyGluThrAlaGluArgThrAlaGluSerGlnHis-48 |
| SEQ. ID. NO. 36021 | 82-SerAlaLysGlnLeuGluAsnLeuPheArgThrLeu-93 |
| SEQ. ID. NO. 36022 | 155-LeuGlnGluMetArgAspPheProAsnAspLysLeuGlnLysSerTrp-170 |
| SEQ. ID. NO. 36023 | 188-GlnThrAlaLeuArgAspIleIleLysHisThr-198 |

TABLE 1-continued

| | |
|---|---|
| SEQ. ID. NO. 36024 | 250-GlyValAlaAlaAsnSer-255 |
| SEQ. ID. NO. 36025 | 257-AspGluProGluTrp-261 |
| SEQ. ID. NO. 36026 | 268-GlnAlaValArgLeuIleArgArgPheValGluPheTrpAspArg-282 |
| SEQ. ID. NO. 36027 | 310-GlnProAspPheAlaLysAspProGlu-318 |
| SEQ. ID. NO. 36028 | 330-LeuAlaAsnProArgAspProGlu-337 |
| SEQ. ID. NO. 36029 | 390-LeuGluGluTyrIleSerProPhe-397 |

Antigenic Index - Jameson-Wolf

| | |
|---|---|
| SEQ. ID. NO. 36030 | 1-MetSerGlnAsnGlnProAlaGlnProThrLysArgAsnLeuPhe-15 |
| SEQ. ID. NO. 36031 | 30-TyrPheGlyGlyLysLysGlnGlyGluThrAlaGluArgThrAlaGluSerGlnHisSerProGlnAla-52 |
| SEQ. ID. NO. 36032 | 80-AlaGlnSerAlaLysGlnLeuGluAsn-88 |
| SEQ. ID. NO. 36033 | 101-ThrGlnGlyGlyGluTyrGlnAspGlyAspAspLysLeuProSerAlaGlySerGly-119 |
| SEQ. ID. NO. 36034 | 125-PheAsnProAspGlyLeuThr-131 |
| SEQ. ID. NO. 36035 | 139-SerLeuPheAspGlyArgPheGlyLeuLysAspLysLysThrValHis-154 |
| SEQ. ID. NO. 36036 | 156-GlnGluMetArgAspPheProAsnAspLysLeuGlnLysSerTrpCysAspGlyAspLeuSer-176 |
| SEQ. ID. NO. 36037 | 183-ThrProGluThrCys-187 |
| SEQ. ID. NO. 36038 | 208-IleAspGlyTrpGlnProLysSerGluProGlyAlaMetAla-221 |
| SEQ. ID. NO. 36039 | 226-LeuGlyPheArgAspGlyThrGlyAsnProLysValSerAspProLysThrAlaAspGlu-245 |
| SEQ. ID. NO. 36040 | 255-SerLeuAspGluProGluTrpAlaLysAsnGlySerTyrGlnAla-269 |
| SEQ. ID. NO. 36041 | 271-ArgLeuIleArgArgPhe-276 |
| SEQ. ID. NO. 36042 | 279-PheTrpAspArgThrProLeuGlnGluGlnThrAspIlePheGlyArgArgLysTyrSerGlyAlaProMetAspGlyLysLysGluAlaAspGln ProAspPheAlaLysAspProGluGlyAspIleThrProLysAspSerHisMetArgLeuAlaAsnProArgAspProGluPheLeuLys-340 |
| SEQ. ID. NO. 36043 | 348-AlaTyrSerTyrSerArgGlyProAlaSerSerGlyGlnLeu-361 |
| SEQ. ID. NO. 36044 | 385-LeuAsnGlyGluProLeuGluGluTyr-393 |
| SEQ. ID. NO. 36045 | 407-GlyValGlyLysGlyGlyPhe-413 |

Hydrophilic Regions - Hopp-Woods

| | |
|---|---|
| SEQ. ID. NO. 36046 | 8-GlnProThrLysArgAsnLeuPhe-15 |
| SEQ. ID. NO. 36047 | 32-GlyGlyLysLysGlnGlyGluThrAlaGluArgThrAlaGluSerGlnHis-48 |
| SEQ. ID. NO. 36048 | 80-AlaGlnSerAlaLysGlnLeuGluAsn-88 |
| SEQ. ID. NO. 36049 | 104-GlyGluTyrGlnAspGlyAspAspLysLeuProSer-115 |
| SEQ. ID. NO. 36050 | 145-PheGlyLeuLysAspLysLysThrValHis-154 |
| SEQ. ID. NO. 36051 | 156-GlnGluMetArgAspPheProAsnAspLysLeuGlnLysSerTrpCysAspGlyAspLeu-175 |
| SEQ. ID. NO. 36052 | 211-TrpGlnProLysSerGluProGlyAlaMetAla-221 |
| SEQ. ID. NO. 36053 | 229-ArgAspGlyThrGlyAsnProLysValSerAspProLysThrAlaAsp-244 |
| SEQ. ID. NO. 36054 | 255-SerLeuAspGluProGluTrpAlaLys-263 |
| SEQ. ID. NO. 36055 | 271-ArgLeuIleArgArgPhe-276 |
| SEQ. ID. NO. 36056 | 283-ThrProLeuGlnGluGlnThrAspIlePheGlyArgArgLysTyrSer-298 |
| SEQ. ID. NO. 36057 | 301-ProMetAspGlyLysLysGluAlaAspGlnProAspPheAlaLysAspProGluGlyAspIleThrProLysAspSerHisMet-328 |
| SEQ. ID. NO. 36058 | 331-AlaAsnProArgAspProGluPheLeuLys-340 |
| SEQ. ID. NO. 36059 | 353-ArgGlyProAlaSer-357 |
| SEQ. ID. NO. 36060 | 388-GluProLeuGluGluTyr-393 | g749
AMPHI Regions - AMPHI

| | |
|---|---|
| SEQ. ID. NO. 36061 | 1-MetArgLysPheAsnLeuThrAlaLeuSerValMetLeuAlaLeuGlyLeuThrAlaCysGlnProProGluAlaGluLysAlaAlaProAlaAlaSerGlyGluThrGlnSerAlaAsnGluGlyGlySerValGlyIleAlaValAsnAspAsnAlaCysGluProMetAsnLeuThrValProSerGlyGlnValValPheAsnIleLysAsnAsnSerGlyArgLysLeuGluTrpGluIleLeuLysGlyValMetValValAspGluArgGluAsnIleAlaProGlyLeuSerAspLysMetThrValThrLeuLeuProGlyGluTyrGluMetThrCysGlyLeuLeuThrAsnProArgGlyLysLeuValValAlaAspSerGlyPheLysAspThrAlaAsnGluAlaAspLeuGluLysLeuProGlnProLeuAlaAspTyrLysAlaTyrValGlnGlyGluValLysGluLeuAlaAlaLysThrLysThrPheThrGluAlaValLysAlaGlyAspIleGluLysAlaLysSerLeuPheAlaAlaThrArgValHisTyrGluArgIleGluProIleAlaGluLeuPheSerGluLeuAspProValIleAspAlaCysGluAspAspPheLysAspGlyAlaLysAspAlaGlyPheThrGlyPheHisArgIleGluHisAlaLeuTrpValGluLysAspValSerGlyValLysGluThrAlaAlaLysLeuMetThrAspValGluAlaLeuGlnLysGluIleAspAlaLeuAlaPheProProGlyLysValValGlyGlyAlaSerGluLeuIleGluGluAlaAlaGlySerLysSerIleSerGlyGluGluAspArgTyrSerHisThrAspLeuSerAspPheGlnAlaAsnAlaAspGlySerLysLysIleValAspLeuPheArgProLeuIleGluAlaLysAsnLysAlaLeuLeuGluLysThrAspThrAsnPheLysGlnValAsnGluIleLeuAlaLysTyrArgThrLysAspGlyPheGluThrTyrAspLysLeuSerGluAlaAspArgLysAlaLeuGlnAlaProIleAsnAlaLeuAlaGluAspLeuAlaGlnLeuArgGlyIleLeuGlyLeuLys-388 |

Antigenic Index - Jameson-Wolf (SEQ. ID. NO. 36061)
1-MetArgLysPheAsnLeuThrAlaLeuSerValMetLeuAlaLeuGlyLeuThrAlaCysGlnProProGluAl
aGluLysAlaAlaProAlaAlaSerGlyGluThrGlnSerAlaAsnGluGlyGlySerValGlyIleAlaValAsn
AspAsnAlaCysGluProMetAsnLeuThrValProSerGlyGlnValValPheAsnIleLysAsnAsnSerGlyA
rgLysLeuGluTrpGluIleLeuLysGlyValMetValValAspGluArgGluAsnIleAlaProGlyLeuSerAs
pLysMetThrValThrLeuLeuProGlyGluTyrGluMetThrCysGlyLeuLeuThrAsnProArgGlyLysLeu
ValValAlaAspSerGlyPheLysAspThrAlaAsnGluAlaAspLeuGluLysLeuProGlnProLeuAlaAspT
yrLysAlaTyrValGlnGlyGluValLysGluLeuAlaAlaLysThrLysThrPheThrGluAlaValLysAlaGl
yAspIleGluLysAlaLysSerLeuPheAlaAlaThrArgValHisTyrGluArgIleGluProIleAlaGluLeu
PheSerGluLeuAspProValIleAspAlaCysGluAspAspPheLysAspGlyAlaLysAspAlaGlyPheThrG
lyPheHisArgIleGluHisAlaLeuTrpValGluLysAspValSerGlyValLysGluThrAlaAlaLysLeuMe
tThrAspValGluAlaLeuGlnLysGluIleAspAlaLeuAlaPheProProGlyLysValValGlyGlyAlaSer
GluLeuIleGluGluAlaAlaGlySerLysSerIleSerGlyGluGluAspArgTyrSerHisThrAspLeuSerAspP
heGlnAlaAsnAlaAspGlySerLysLysIleValAspLeuPheArgProLeuIleGluAlaLysAsnLysAlaLe
uLeuGluLysThrAspThrAsnPheLysGlnValAsnGluIleLeuAlaLysTyrArgThrLysAspGlyPheGlu
ThrTyrAspLysLeuSerGluAlaAspArgLysAlaLeuGlnAlaProIleAsnAlaLeuAlaGluAspLeuAlaG
lnLeuArgGlyIleLeuGlyLeuLys-388

Hydrophilic Regions - Hopp-Woods (SEQ. ID. NO. 36061)
1-MetArgLysPheAsnLeuThrAlaLeuSerValMetLeuAlaLeuGlyLeuThrAlaCysGlnProProGluAl
aGluLysAlaAlaProAlaAlaSerGlyGluThrGlnSerAlaAsnGluGlyGlySerValGlyIleAlaValAsn
AspAsnAlaCysGluProMetAsnLeuThrValProSerGlyGlnValValPheAsnIleLysAsnAsnSerGlyA
rgLysLeuGluTrpGluIleLeuLysGlyValMetValValAspGluArgGluAsnIleAlaProGlyLeuSerAs
pLysMetThrValThrLeuLeuProGlyGluTyrGluMetThrCysGlyLeuLeuThrAsnProArgGlyLysLeu
ValValAlaAspSerGlyPheLysAspThrAlaAsnGluAlaAspLeuGluLysLeuProGlnProLeuAlaAspT
yrLysAlaTyrValGlnGlyGluValLysGluLeuAlaAlaLysThrLysThrPheThrGluAlaValLysAlaGl
yAspIleGluLysAlaLysSerLeuPheAlaAlaThrArgValHisTyrGluArgIleGluProIleAlaGluLeu TABLE 1-continued PheSerGluLeuAspProValIleAspAlaCysGluAspAspPheLysAspGlyAlaLysAspAlaGlyPheThrG
lyPheHisArgIleGluHisAlaLeuTrpValGluLysAspValSerGlyValLysGluThrAlaAlaLysLeuMe
tThrAspValGluAlaLeuGlnLysGluIleAspAlaLeuAlaPheProProGlyLysValValGlyGlyAlaSer
GluLeuIleGluGluAlaAlaGlySerLysIleSerGlyGluGluAspArgTyrSerHisThrAspLeuSerAspP
heGlnAlaAsnAlaAspGlySerLysLysIleValAspLeuPheArgProLeuIleGluAlaLysAsnLysAlaLe
uLeuGluLysThrAspThrAsnPheLysGlnValAsnGluIleLeuAlaLysTyrArgThrLysAspGlyPheGlu
ThrTyrAspLysLeuSerGluAlaAspArgLysAlaLeuGlnAlaProIleAsnAlaLeuAlaGluAspLeuAlaG
lnLeuArgGlyIleLeuGlyLeuLys-388
g750
AMPHI Regions - AMPHI
SEQ. ID. NO. 36062    1-ValLysProArgPheTyrTrpAlaAlaCysAlaValLeuProAlaAlaCy
sSerProGluProAlaAlaGluLysThrValSerAlaAlaSerGlnAlaAlaSerThrProValAlaThrLeuThrValProThrAlaArgGlyAspAlaValV
alProLysAsnProGluArgValAlaValTyrAspTrpAlaAlaLeuAspThrLeuThrGluProGlyValAsnValGlyAlaThrThrAlaProValArgVal
AspTyrLeuGlnProAlaPheAspLysAlaAlaThrValGlyThrLeuPheGluProAspCysGluSerLeuHisArgHisAsnProGlnPheValIleThrGl
yGlyProGlyAlaGluAlaTyrGluGlnLeuAlaLysAsnAlaThrThrIleAspLeuThrValAspAsnGlyAsnIleArgThrSerGlyGluLysGlnMetG
luThrLeuSerArgIlePheGlyLysGluAlaArgValAlaGluLeuAsnAlaGlnIleAspAlaLeuPheAlaGlnLysArgGluAlaAlaLysGlyLysGly
ArgGlyLeuValLeuSerValThrGlyAsnLysValSerAlaPheGlyThrGlnSerArgLeuAlaSerTrpIleHisGlyAspIleGlyLeuProProValAs
pGluSerLeuArgAsnGluGlyHisGlyGlnProValSerPheGluTyrIleLysGluLysAsnProGlyTrpIlePheIleIleAspArgThrAlaAlaIleG
lyGlnGluGlyProAlaAlaValGluValLeuAspAsnAlaLeuValCysGlyThrAsnAlaTrpLysArgLysGlnIleIleValMetProAlaAlaAsnTyr
IleValAlaGlyGlyAlaArgGlnLeuIleGlnAlaAlaGluGlnLeuLysAlaAlaPheGluLysAlaGluProValAlaAlaGln-323
Antigenic Index - Jameson-Wolf (SEQ. ID. NO. 36062)
1-ValLysProArgPheTyrTrpAlaAlaCysAlaValLeuProAlaAlaCysSerProGluProAlaAlaGluLy
sThrValSerAlaAlaSerGlnAlaAlaSerThrProValAlaThrLeuThrValProThrAlaArgGlyAspAla
ValValProLysAsnProGluArgValAlaValTyrAspTrpAlaAlaLeuAspThrLeuThrGluProGlyValA
snValGlyAlaThrThrAlaProValArgValAspTyrLeuGlnProAlaPheAspLysAlaAlaThrValGlyTh
rLeuPheGluProAspCysGluSerLeuHisArgHisAsnProGlnPheValIleThrGlyGlyProGlyAlaGlu
AlaTyrGluGlnLeuAlaLysAsnAlaThrThrIleAspLeuThrValAspAsnGlyAsnIleArgThrSerGlyG
luLysGlnMetGluThrLeuSerArgIlePheGlyLysGluAlaArgValAlaGluLeuAsnAlaGlnIleAspAl
aLeuPheAlaGlnLysArgGluAlaAlaLysGlyLysGlyArgGlyLeuValLeuSerValThrGlyAsnLysVal
SerAlaPheGlyThrGlnSerArgLeuAlaSerTrpIleHisGlyAspIleGlyLeuProProValAspGluSerL
euArgAsnGluGlyHisGlyGlnProValSerPheGluTyrIleLysGluLysAsnProGlyTrpIlePheIleIl
eAspArgThrAlaAlaIleGlyGlnGluGlyProAlaAlaValGluValLeuAspAsnAlaLeuValCysGlyThr
AsnAlaTrpLysArgLysGlnIleIleValMetProAlaAlaAsnTyrIleValAlaGlyGlyAlaArgGlnLeuI
leGlnAlaAlaGluGlnLeuLysAlaAlaPheGluLysAlaGluProValAlaAlaGln-323
Hydrophilic Regions - Hopp-Woods (SEQ. ID. NO. 36062)
1-ValLysProArgPheTyrTrpAlaAlaCysAlaValLeuProAlaAlaCysSerProGluProAlaAlaGluLy
sThrValSerAlaAlaSerGlnAlaAlaSerThrProValAlaThrLeuThrValProThrAlaArgGlyAspAla
ValValProLysAsnProGluArgValAlaValTyrAspTrpAlaAlaLeuAspThrLeuThrGluProGlyValA
snValGlyAlaThrThrAlaProValArgValAspTyrLeuGlnProAlaPheAspLysAlaAlaThrValGlyTh
rLeuPheGluProAspCysGluSerLeuHisArgHisAsnProGlnPheValIleThrGlyGlyProGlyAlaGlu
AlaTyrGluGlnLeuAlaLysAsnAlaThrThrIleAspLeuThrValAspAsnGlyAsnIleArgThrSerGlyG
luLysGlnMetGluThrLeuSerArgIlePheGlyLysGluAlaArgValAlaGluLeuAsnAlaGlnIleAspAl
aLeuPheAlaGlnLysArgGluAlaAlaLysGlyLysGlyArgGlyLeuValLeuSerValThrGlyAsnLysVal
SerAlaPheGlyThrGlnSerArgLeuAlaSerTrpIleHisGlyAspIleGlyLeuProProValAspGluSerL
euArgAsnGluGlyHisGlyGlnProValSerPheGluTyrIleLysGluLysAsnProGlyTrpIlePheIleIl
eAspArgThrAlaAlaIleGlyGlnGluGlyProAlaAlaValGluValLeuAspAsnAlaLeuValCysGlyThr
AsnAlaTrpLysArgLysGlnIleIleValMetProAlaAlaAsnTyrIleValAlaGlyGlyAlaArgGlnLeuI
leGlnAlaAlaGluGlnLeuLysAlaAlaPheGluLysAlaGluProValAlaAlaGln-323
g760
AMPHI Regions - AMPHI
SEQ. ID. NO. 36063    1-AsnAsnArgAsnThrArgTyrAlaAlaLeuGlyLysArgValMetGluGl
yValGluThrGluIleSerGlyAlaIleThrProLysTrpGlnIleHisAlaGlyTyrSerTyrLeuHisSerGlnIleLysThrAlaAlaAsnProArgAspA
spGlyIlePheLeuLeuValProLysHisSerAlaAsnLeuTrpThrThrTyrGlnValThrProGlyLeuThrValGlyGlyGlyValAsnAlaMetSerGly
IleThrSerSerAlaGlyMetHisAlaGlyGlyTyrAlaThrPheAspAlaMetAlaAlaTyrArgPheThrProLysLeuLysLeuGlnIleAsnAlaAspAs
nIlePheAsnArgHisTyrTyrAlaArgValGlyGlyThrAsnThrPheAsnIleProGlySerGluArgSerLeuThrAlaAsnLeuArgTyrSerPhe-154
Antigenic Index - Jameson-Wolf (SEQ. ID. NO. 36063)
1-AsnAsnArgAsnThrArgTyrAlaAlaLeuGlyLysArgValMetGluGlyValGluThrGluIleSerGlyAl
aIleThrProLysTrpGlnIleHisAlaGlyTyrSerTyrLeuHisSerGlnIleLysThrAlaAlaAsnProArg
AspAspGlyIlePheLeuLeuValProLysHisSerAlaAsnLeuTrpThrThrTyrGlnValThrProGlyLeuT
hrValGlyGlyGlyValAsnAlaMetSerGlyIleThrSerSerAlaGlyMetHisAlaGlyGlyTyrAlaThrPh
eAspAlaMetAlaAlaTyrArgPheThrProLysLeuLysLeuGlnIleAsnAlaAspAsnIlePheAsnArgHis
TyrTyrAlaArgValGlyGlyThrAsnThrPheAsnIleProGlySerGluArgSerLeuThrAlaAsnLeuArgT
yrSerPhe-154
Hydrophilic Regions - Hopp-Woods (SEQ. ID. NO. 36063)
1-AsnAsnArgAsnThrArgTyrAlaAlaLeuGlyLysArgValMetGluGlyValGluThrGluIleSerGlyAl
aIleThrProLysTrpGlnIleHisAlaGlyTyrSerTyrLeuHisSerGlnIleLysThrAlaAlaAsnProArg
AspAspGlyIlePheLeuLeuValProLysHisSerAlaAsnLeuTrpThrThrTyrGlnValThrProGlyLeuT
hrValGlyGlyGlyValAsnAlaMetSerGlyIleThrSerSerAlaGlyMetHisAlaGlyGlyTyrAlaThrPh
eAspAlaMetAlaAlaTyrArgPheThrProLysLeuLysLeuGlnIleAsnAlaAspAsnIlePheAsnArgHis
TyrTyrAlaArgValGlyGlyThrAsnThrPheAsnIleProGlySerGluArgSerLeuThrAlaAsnLeuArgT
yrSerPhe-154
g767
AMPHI Regions - AMPHI
SEQ. ID. NO. 36064    41-GlyLysIleGluValLeuGluPhePheGlyTyrPheCysVal-54
SEQ. ID. NO. 36065    89-GlyLeuAlaArgMetAlaAlaAlaValLys-98
SEQ. ID. NO. 36066    140-LysLysLeuMetArgAlaTyrAspSerProGlu-150
SEQ. ID. NO. 36067    160-LysLeuThrGluGlnTyr-165
SEQ. ID. NO. 36068    187-PheAspGlyGlyValHisThrIleLysGluLeuValAla-199
Antigenic Index - Jameson-Wolf
SEQ. ID. NO. 36069    23-ThrGluGlyGluAspTyrLeuVal-30

TABLE 1-continued

SEQ. ID. NO. 36070   32-AspLysProIleProGlnGluGlnProGlyLysIleGluVal-45
SEQ. ID. NO. 36071   66-LeuGlyLysAlaLeuProSerAspThrTyrLeuArg-77
SEQ. ID. NO. 36072   99-LeuSerGlyLeuLysTyrGlnAla-106
SEQ. ID. NO. 36073   115-TyrGluGlnLysIleArgLeuGluAsnArgAlaValAla-127
SEQ. ID. NO. 36074   132-LeuSerGlnLysGlyPheAspGlyLysLysLeuMetArgAlaTyrAspSerProGluAla-151
SEQ. ID. NO. 36075   157-LysMetGlnLysLeuThrGluGlnTyrGlyIleAspSerThrPro-171
SEQ. ID. NO. 36076   175-ValGlyGlyLysTyrArgVal-181
SEQ. ID. NO. 36077   183-PheAsnAsnGlyPheAspGlyGly-190
SEQ. ID. NO. 36078   197-LeuValAlaLysValArgGluGluArgLysArgGlnThrProAlaValGlnLys-214
Hydrophilic Regions - Hopp-Woods
SEQ. ID. NO. 36079   23-ThrGluGlyGluAsp-27
SEQ. ID. NO. 36080   33-LysProIleProGlnGluGlnProGlyLysIleGluVal-45
SEQ. ID. NO. 36081   115-TyrGluGlnLysIleArgLeuGluAsnArgAlaValAla-127
SEQ. ID. NO. 36082   135-LysGlyPheAspGlyLysLysLeuMetArgAlaTyrAspSerProGluAla-151
SEQ. ID. NO. 36083   157-LysMetGlnLysLeuThrGlu-163
SEQ. ID. NO. 36084   197-LeuValAlaLysValArgGluGluArgLysArgGlnThrProAlaValGlnLys-214
g768
AMPHI Regions - AMPHI
SEQ. ID. NO. 36085   1-MetAsnIleLysGlnLeuIleThrAlaAlaLeuIleAlaSerAlaAlaPh
                     eAlaThrGlnAlaAlaProGlnLysProValSerAlaAlaGlnThrAlaGlnHisSerAlaValTrpIleAspValArgSerGluGlnGluPheSerGluGlyH
                     isLeuHisAsnAlaValAsnIleProValAspGlnIleValArgArgIleTyrGluAlaAlaProAspLysAspThrProValAsnLeuTyrCysArgSerGly
                     ArgArgAlaGluAlaAlaLeuGlnGluLeuLysLysAlaGlyTyrThrAsnValAlaAsnHisGlyGlyTyrGluAspLeuLeuLysLysGlyMetLys-119
Antigenic Index - Jameson-Wolf (SEQ. ID. NO. 36085)
1-MetAsnIleLysGlnLeuIleThrAlaAlaLeuIleAlaSerAlaAlaPheAlaThrGlnAlaAlaProGlnLy
sProValSerAlaAlaGlnThrAlaGlnHisSerAlaValTrpIleAspValArgSerGluGlnGluPheSerGlu
GlyHisLeuHisAsnAlaValAsnIleProValAspGlnIleValArgArgIleTyrGluAlaAlaProAspLysA
spThrProValAsnLeuTyrCysArgSerGlyArgArgAlaGluAlaAlaLeuGlnGluLeuLysLysAlaGlyTy
rThrAsnValAlaAsnHisGlyGlyTyrGluAspLeuLeuLysLysGlyMetLys-119
Hydrophilic Regions - Hopp-Woods (SEQ. ID. NO. 36085)
1-MetAsnIleLysGlnLeuIleThrAlaAlaLeuIleAlaSerAlaAlaPheAlaThrGlnAlaAlaProGlnLy
sProValSerAlaAlaGlnThrAlaGlnHisSerAlaValTrpIleAspValArgSerGluGlnGluPheSerGlu
GlyHisLeuHisAsnAlaValAsnIleProValAspGlnIleValArgArgIleTyrGluAlaAlaProAspLysA
spThrProValAsnLeuTyrCysArgSerGlyArgArgAlaGluAlaAlaLeuGlnGluLeuLysLysAlaGlyTy
rThrAsnValAlaAsnHisGlyGlyTyrGluAspLeuLeuLysLysGlyMetLys-119
g769
AMPHI Regions - AMPHI
SEQ. ID. NO. 36086   1-LeuIleMetValIlePheTyrPheTyrPheCysGlyLysThrPheMetPr
                     oAlaArgAsnArgTrpMetLeuLeuProLeuLeuAlaSerAlaAlaTyrAlaGluGluThrProCysGluProAspLeuArgSerArgProGluPheArgLeuH
                     isGluAlaGluValLysProIleAspArgGluLysValProGlyGlnValArgGluLysGlyLysValLeuGlnValAspGlyGluThrLeuLeuLysAsnPro
                     GluLeuLeuSerArgAlaMetTyrSerAlaValValSerAsnAsnIleAlaGlyIleArgValIleLeuProIleTyrLeuGlnGlnAlaArgGlnAspLysMe
                     tLeuAlaLeuTyrAlaGlnGlyIleLeuAlaGlnAlaGluGlyArgValLysGluAlaValSerHisTyrArgGluLeuIleAlaAlaGlnProAspAlaProA
                     laValArgMetArgLeuAlaAlaAlaLeuPheGluAspArgGlnAsnGluAlaAlaAlaAspGlnPheAspArgLeuLysThrGluAspLeuProProGlnLeu
                     MetGluGlnValGluLeuTyrArgLysAlaLeuArgGluArgAspAlaTrpLysValAsnGlyGlyPheSerValThrArgGluHisAsnIleAsnGlnAlaPr
                     oLysGlnGlnGlnTyrGlyAsnTrpThrPheProLysGlnValAspGlyThrAlaValAsnTyrArgPheGlyAlaGluLysLysTrpSerLeuLysAsnGlyT
                     rpTyrThrThrAlaGlyGlyAspValSerGlyArgValTyrProGlyAsnLysLysPheAsnAspMetThrAlaGlyValSerGlyGlyIleGlyPheAlaAsp
                     ArgArgLysAspValGlyLeuAlaValPheHisGluArgArgThrTyrGlyAsnAspAlaTyrSerTyrAlaAsnGlyAlaArgLeuTyrPheAsnArgTrpGl
                     nThrProArgTrpGlnThrLeuSerSerAlaGluTrpGlyArgLeuLysAsnThrArgArgAlaArgSerAspAsnThrHisLeuGlnIleSerAsnSerLeuV
                     alPheTyrArgAsnAlaArgGlnTyrTrpThrGlyGlyLeuAspPheTyrArgGluArgAsnProAlaAspArgGlyAspAsnPheAsnArgTyrGlyLeuArg
                     PheAlaTrpGlyGlnGluTrpGlyGlySerGlyLeuSerSerLeuPheArgLeuGlyValAlaLysArgHisTyrGluLysProGlyPhePheSerSerPheLy
                     sGlyGluArgArgArgAspLysGluSerAspThrSerLeuSerLeuTrpHisArgAlaLeuHisPheLysGlyIleThrProArgLeuThrLeuSerHisArgG
                     luThrTrpSerAsnAspValPheAsnGluTyrGluLysAsnArgAlaPheValGluPheAsnLysThrPhe-491
Antigenic Index - Jameson-Wolf (SEQ. ID. NO. 36086)
1-LeuIleMetValIlePheTyrPheTyrPheCysGlyLysThrPheMetProAlaArgAsnArgTrpMetLeuLe
uProLeuLeuAlaSerAlaAlaTyrAlaGluGluThrProCysGluProAspLeuArgSerArgProGluPheArg
LeuHisGluAlaGluValLysProIleAspArgGluLysValProGlyGlnValArgGluLysGlyLysValLeuG
lnValAspGlyGluThrLeuLeuLysAsnProGluLeuLeuSerArgAlaMetTyrSerAlaValValSerAsnAs
nIleAlaGlyIleArgValIleLeuProIleTyrLeuGlnGlnAlaArgGlnAspLysMetLeuAlaLeuTyrAla
GlnGlyIleLeuAlaGlnAlaGluGlyArgValLysGluAlaValSerHisTyrArgGluLeuIleAlaAlaGlnP
roAspAlaProAlaValArgMetArgLeuAlaAlaAlaLeuPheGluAspArgGlnAsnGluAlaAlaAlaAspGl
nPheAspArgLeuLysThrGluAspLeuProProGlnLeuMetGluGlnValGluLeuTyrArgLysAlaLeuArg
GluArgAspAlaTrpLysValAsnGlyGlyPheSerValThrArgGluHisAsnIleAsnGlnAlaProLysGlnG
lnGlnTyrGlyAsnTrpThrPheProLysGlnValAspGlyThrAlaValAsnTyrArgPheGlyAlaGluLysLy
sTrpSerLeuLysAsnGlyTrpTyrThrThrAlaGlyGlyAspValSerGlyArgValTyrProGlyAsnLysLys
PheAsnAspMetThrAlaGlyValSerGlyGlyIleGlyPheAlaAspArgArgLysAspValGlyLeuAlaValP
heHisGluArgArgThrTyrGlyAsnAspAlaTyrSerTyrAlaAsnGlyAlaArgLeuTyrPheAsnArgTrpGl
nThrProArgTrpGlnThrLeuSerSerAlaGluTrpGlyArgLeuLysAsnThrArgArgAlaArgSerAspAsn
ThrHisLeuGlnIleSerAsnSerLeuValPheTyrArgAsnAlaArgGlnTyrTrpThrGlyGlyLeuAspPheT
yrArgGluArgAsnProAlaAspArgGlyAspAsnPheAsnArgTyrGlyLeuArgPheAlaTrpGlyGlnGluTr
pGlyGlySerGlyLeuSerSerLeuPheArgLeuGlyValAlaLysArgHisTyrGluLysProGlyPhePheSer
SerPheLysGlyGluArgArgArgAspLysGluSerAspThrSerLeuSerLeuTrpHisArgAlaLeuHisPheL
ysGlyIleThrProArgLeuThrLeuSerHisArgGluThrTrpSerAsnAspValPheAsnGluTyrGluLysAs
nArgAlaPheValGluPheAsnLysThrPhe-491
Hydrophilic Regions - Hopp-Woods (SEQ. ID. NO. 36086)
1-LeuIleMetValIlePheTyrPheTyrPheCysGlyLysThrPheMetProAlaArgAsnArgTrpMetLeuLe
uProLeuLeuAlaSerAlaAlaTyrAlaGluGluThrProCysGluProAspLeuArgSerArgProGluPheArg
LeuHisGluAlaGluValLysProIleAspArgGluLysValProGlyGlnValArgGluLysGlyLysValLeuG
lnValAspGlyGluThrLeuLeuLysAsnProGluLeuLeuSerArgAlaMetTyrSerAlaValValSerAsnAs
nIleAlaGlyIleArgValIleLeuProIleTyrLeuGlnGlnAlaArgGlnAspLysMetLeuAlaLeuTyrAla
GlnGlyIleLeuAlaGlnAlaGluGlyArgValLysGluAlaValSerHisTyrArgGluLeuIleAlaAlaGlnP
roAspAlaProAlaValArgMetArgLeuAlaAlaAlaLeuPheGluAspArgGlnAsnGluAlaAlaAlaAspGl TABLE 1-continued nPheAspArgLeuLysThrGluAspLeuProProGlnLeuMetGluGlnValGluLeuTyrArgLysAlaLeuArg
GluArgAspAlaTrpLysValAsnGlyGlyPheSerValThrArgGluHisAsnIleAsnGlnAlaProLysGlnG
lnGlnTyrGlyAsnTrpThrPheProLysGlnValAspGlyThrAlaValAsnTyrArgPheGlyAlaGluLysLy
sTrpSerLeuLysAsnGlyTrpTyrThrThrAlaGlyGlyAspValSerGlyArgValTyrProGlyAsnLysLys
PheAsnAspMetThrAlaGlyValSerGlyGlyIleGlyPheAlaAspArgArgLysAspValGlyLeuAlaValP
heHisGluArgArgThrTyrGlyAsnAspAlaTyrSerTyrAlaAsnGlyAlaArgLeuTyrPheAsnArgTrpGl
nThrProArgTrpGlnThrLeuSerSerAlaGluTrpGlyArgLeuLysAsnThrArgArgAlaArgSerAspAsn
ThrHisLeuGlnIleSerAsnSerLeuValPheTyrArgAsnAlaArgGlnTyrTrpThrGlyGlyLeuAspPheT
yrArgGluArgAsnProAlaAspArgGlyAspAsnPheAsnArgTyrGlyLeuArgPheAlaTrpGlyGlnGluTr
pGlyGlySerGlyLeuSerSerLeuPheArgLeuGlyValAlaLysArgHisTyrGluLysProGlyPhePheSer
SerPheLysGlyGluArgArgArgAspLysGluSerAspThrSerLeuSerLeuTrpHisArgAlaLeuHisPheL
ysGlyIleThrProArgLeuThrLeuSerHisArgGluThrTrpSerAsnAspValPheAsnGluTyrGluLysAs
nArgAlaPheValGluPheAsnLysThrPhe-491
g770
AMPHI Regions - AMPHI
SEQ. ID. NO. 36087    1-MetAsnArgLeuLeuLeuLeuSerAlaAlaValLeuProThrAlaCysGl
                     ySerGlyGluThrAspLysIleGlyArgAlaSerThrValPheAsnMetLeuGlyLysAsnAspArgIleGluValGluGlyPheAspAspProAspValGlnG
                     lyValAlaCysTyrIleSerTyrAlaLysLysGlyGlyLeuLysGluMetValAsnLeuGluGluAspAlaSerAspAlaSerValSerCysValGlnThrAla
                     SerSerIleSerPheAspGluThrAlaValArgLysProLysGluValPheLysArgGlyThrGlyPheAlaPheLysSerArgGlnIleValArgTyrTyrAs
                     pProLysArgLysAlaPheAlaTyrLeuValTyrSerAspLysIleValGlnGlySerProLysAsnSerLeuSerAlaValSerCysPheGlySerGlyIleP
                     roGlnThrAspGlyValGlnAlaAspThrSerGlyLysLeuLeuAlaGlyAlaCysIleIleSerAsnProIleLysAsnProAspLysArg-186
Antigenic Index - Jameson-Wolf (SEQ. ID. NO. 36087)
1-MetAsnArgLeuLeuLeuLeuSerAlaAlaValLeuProThrAlaCysGlySerGlyGluThrAspLysIleGl
yArgAlaSerThrValPheAsnMetLeuGlyLysAsnAspArgIleGluValGluGlyPheAspAspProAspVal
GlnGlyValAlaCysTyrIleSerTyrAlaLysLysGlyGlyLeuLysGluMetValAsnLeuGluGluAspAlaS
erAspAlaSerValSerCysValGlnThrAlaSerSerIleSerPheAspGluThrAlaValArgLysProLysGl
uValPheLysArgGlyThrGlyPheAlaPheLysSerArgGlnIleValArgTyrTyrAspProLysArgLysAla
PheAlaTyrLeuValTyrSerAspLysIleValGlnGlySerProLysAsnSerLeuSerAlaValSerCysPheG
lySerGlyIleProGlnThrAspGlyValGlnAlaAspThrSerGlyLysLeuLeuAlaGlyAlaCysIleIleSe
rAsnProIleLysAsnProAspLysArg-186
Hydrophilic Regions - Hopp-Woods (SEQ. ID. NO. 36087)
1-MetAsnArgLeuLeuLeuLeuSerAlaAlaValLeuProThrAlaCysGlySerGlyGluThrAspLysIleGl
yArgAlaSerThrValPheAsnMetLeuGlyLysAsnAspArgIleGluValGluGlyPheAspAspProAspVal
GlnGlyValAlaCysTyrIleSerTyrAlaLysLysGlyGlyLeuLysGluMetValAsnLeuGluGluAspAlaS
erAspAlaSerValSerCysValGlnThrAlaSerSerIleSerPheAspGluThrAlaValArgLysProLysGl
uValPheLysArgGlyThrGlyPheAlaPheLysSerArgGlnIleValArgTyrTyrAspProLysArgLysAla
PheAlaTyrLeuValTyrSerAspLysIleValGlnGlySerProLysAsnSerLeuSerAlaValSerCysPheG
lySerGlyIleProGlnThrAspGlyValGlnAlaAspThrSerGlyLysLeuLeuAlaGlyAlaCysIleIleSe
rAsnProIleLysAsnProAspLysArg-186
g771
AMPHI Regions - AMPHI
SEQ. ID. NO. 36088    49-SerIleAlaHisThr-53
SEQ. ID. NO. 36089    133-IleGlnAspLeuPheAspGlyAla-140
SEQ. ID. NO. 36090    312-GlyIleAlaAsnIleGlyAsn-318
SEQ. ID. NO. 36091    358-LeuGlnAspThrValAspArgLeuPro-366
SEQ. ID. NO. 36092    369-ArgPheIleSerArgLeuAspGlySer-377
SEQ. ID. NO. 36093    391-AsnGlyThrPheAsp-395
SEQ. ID. NO. 36094    427-TyrLeuAspGluPheArg-432
SEQ. ID. NO. 36095    437-LysIlePheProAspIleLeuGlyArgLeuSerGly-448
SEQ. ID. NO. 36096    523-LeuGlnAspLeuPheGlyPheHis-530
SEQ. ID. NO. 36097    581-GlyLeuSerGlyLys-585
SEQ. ID. NO. 36098    601-IleSerAspGlyIleSerArgHisIleAspThr-611
Antigenic Index - Jameson-Wolf
SEQ. ID. NO. 36099    37-PheThrProGluAsnIleArgSerArgLeuGlnGln-48
SEQ. ID. NO. 36100    52-HisThrHisArgLysIleSerPhe-59
SEQ. ID. NO. 36101    61-AlaAspIleArgArgArgLeuLeuProArgProThrVal-73
SEQ. ID. NO. 36102    79-ThrIleThrGluProAspGlyGlyArg-87
SEQ. ID. NO. 36103    90-ValSerValLysGluThrLysIle-97
SEQ. ID. NO. 36104    104-LeuTrpSerAspArgIleGlnVal-111
SEQ. ID. NO. 36105    122-AlaLeuThrArgArgAsnGlyAlaTrp-131
SEQ. ID. NO. 36106    135-AspLeuPheAspGlyAlaLysHisSerAlaSerValAsn-147
SEQ. ID. NO. 36107    150-IleValGluAsnSerThrValArg-157
SEQ. ID. NO. 36108    174-LeuGlnSerProAspSerSerGlyGlnGlnPheGluSerSerGly-188
SEQ. ID. NO. 36109    197-ValProTrpLysSerArgGlyLeuPhe-205
SEQ. ID. NO. 36110    208-AspGlyIleGlyThrProGluIleSerPro-217
SEQ. ID. NO. 36111    222-AlaSerThrSerLeuAspGlyHisGly-230
SEQ. ID. NO. 36112    235-ThrThrGlySerProSerValArgPheAsnAlaGlyGlyAlaAsp-249
SEQ. ID. NO. 36113    255-LeuArgAlaAspThrSerPhe-261
SEQ. ID. NO. 36114    275-LeuLysAsnAsnSerIleLysThrGlyThrVal-285
SEQ. ID. NO. 36115    291-AlaGlyGlyGluTyrAlaArgTrpAspGlySerPheLysLeuAspLysAlaAsnLeu-309
SEQ. ID. NO. 36116    317-GlyAsnAlaGluIleSerGlySerPheLysThrProArgLeuGln-331
SEQ. ID. NO. 36117    342-TrpSerArgAspAsnGlyLeuAspAlaProArg-352
SEQ. ID. NO. 36118    360-AspThrValAspArgLeuProGlnProArgPheIleSerArgLeuAspGlySerLeu-378
SEQ. ID. NO. 36119    389-GluLeuAsnGlyThrPheAspArgGlnProVal-399
SEQ. ID. NO. 36120    404-LysTyrThrArgGluGlyAlaProHisLeu-413
SEQ. ID. NO. 36121    429-AspGluPheArgGlnGlnAsnGlyLysIle-438
SEQ. ID. NO. 36122    443-LeuGlyArgLeuSerGlyAsnValGluAla-452
SEQ. ID. NO. 36123    464-LeuGlnLeuAspAspMetGlu-470
SEQ. ID. NO. 36124    473-LeuHisAlaAspLysAspHisIleAla-481
SEQ. ID. NO. 36125    483-SerArgPheLysSerGlyLeuTyrGlyGlyHisThrGluGlyGlyIle-498

TABLE 1-continued

| | |
|---|---|
| SEQ. ID. NO. 36126 | 502-AsnThrArgProAlaThrTyrArgLeuGlnGlnAsnAlaSerAsn-516 |
| SEQ. ID. NO. 36127 | 531-SerPheSerGlyAsnGlyAspAlaVal-539 |
| SEQ. ID. NO. 36128 | 543-ThrAlaSerGlyGluAsnArgLysGlnLeuIleArgSerLeuGlnGlySerLeu-560 |
| SEQ. ID. NO. 36129 | 564-IleSerAsnGlyAla-568 |
| SEQ. ID. NO. 36130 | 573-AspMetAspSerIleLeuLysAsnGlyLeuSerGlyLysIleSerGly-588 |
| SEQ. ID. NO. 36131 | 597-LeuAsnSerGluIleSerAspGlyIleSerArgHisIleAsp-610 |
| SEQ. ID. NO. 36132 | 623-AsnGlyTyrThrAsnLeuAspThrGlnGluLeuSerGlu-635 |
| SEQ. ID. NO. 36133 | 642-AlaValHisProLysAsnLysProIlePro-651 |
| SEQ. ID. NO. 36134 | 656-GlyThrValAspLysProSerIleThrValAspTyrGlyArgLeuThrGlyGlyIleAsnSerArgLysGluLysGlnLysIleLeuGlu-685 |
| SEQ. ID. NO. 36135 | 695-LeuLysProLysGluPro-700 |

Hydrophilic Regions - Hopp-Woods

| | |
|---|---|
| SEQ. ID. NO. 36136 | 40-GluAsnIleArgSerArgLeuGln-47 |
| SEQ. ID. NO. 36137 | 53-ThrHisArgLysIleSerPhe-59 |
| SEQ. ID. NO. 36138 | 61-AlaAspIleArgArgArgLeuLeuPro-69 |
| SEQ. ID. NO. 36139 | 81-ThrGluProAspGlyGlyArg-87 |
| SEQ. ID. NO. 36140 | 90-ValSerValLysGluThrLysIle-97 |
| SEQ. ID. NO. 36141 | 122-AlaLeuThrArgAspArgAsnGly-129 |
| SEQ. ID. NO. 36142 | 135-AspLeuPheAspGlyAlaLysHisSerAlaSer-145 |
| SEQ. ID. NO. 36143 | 175-GlnSerProAspSerSerGlyGlnGlnPheGlu-185 |
| SEQ. ID. NO. 36144 | 255-LeuArgAlaAspThrSerPhe-261 |
| SEQ. ID. NO. 36145 | 302-PheLysLeuAspLysAlaAsnLeu-309 |
| SEQ. ID. NO. 36146 | 325-PheLysThrProArgLeu-330 |
| SEQ. ID. NO. 36147 | 344-ArgAspAsnGlyLeuAspAlaProArg-352 |
| SEQ. ID. NO. 36148 | 360-AspThrValAspArgLeuProGln-367 |
| SEQ. ID. NO. 36149 | 370-PheIleSerArgLeuAspGly-376 |
| SEQ. ID. NO. 36150 | 392-GlyThrPheAspArgGlnProVal-399 |
| SEQ. ID. NO. 36151 | 404-LysTyrThrArgGluGlyAlaPro-411 |
| SEQ. ID. NO. 36152 | 429-AspGluPheArgGlnGlnAsn-435 |
| SEQ. ID. NO. 36153 | 465-GlnLeuAspAspMetGlu-470 |
| SEQ. ID. NO. 36154 | 473-LeuHisAlaAspLysAspHisIleAla-481 |
| SEQ. ID. NO. 36155 | 544-AlaSerGlyGluAsnArgLysGlnLeuIle-553 |
| SEQ. ID. NO. 36156 | 600-GluIleSerAspGlyIleSerArgHisIleAsp-610 |
| SEQ. ID. NO. 36157 | 629-AspThrGlnGluLeuSerGlu-635 |
| SEQ. ID. NO. 36158 | 643-ValHisProLysAsnLysProIlePro-651 |
| SEQ. ID. NO. 36159 | 656-GlyThrValAspLysProSerIle-663 |
| SEQ. ID. NO. 36160 | 674-IleAsnSerArgLysGluLysGlnLysIleLeuGlu-685 |
| SEQ. ID. NO. 36161 | 696-LysProLysGluPro-700 | g772
AMPHI Regions - AMPHI

| | |
|---|---|
| SEQ. ID. NO. 36162 | 1-ValPheGlyThrValLeuArgThrAspAlaAspCysLeuGlnIleIleVa
lValGlyLysPhePheGlnValValAlaTyrGlyPheAlaAlaLeuAlaGluGlyGluPheHisGlnPheGlyGluMetIleGluIleValArgLeuAlaAspT
hrValPheHisArgAsnHisAlaHisHisCysGlyIleAspPheArgArgGlyIleGluArgPheGlyArgHisValAsnGlnGlnLeuHisIleGluLysIle
LeuGlnHisHisThrGlnAlaThrValValValAlaPheArgArgGlyAsnHisAlaLeuAspHisPhePheLeuGlnHisLysValHisIleGlyAspIleVa
lArgHisLeuArgGlnPheGluGlnLysArgArgGlyAspValIleArgGlnValAlaAspAspPheLeuPheAlaAspAlaValGluIleLysLeuGlnHisV
alAlaPheValAsnHisGlnPheIleArgLysArgGlnArgPheGlnThrAlaTyrAspValAlaValAspPheAspAsnValGlnAlaValGlnLeuPheArg
GlnArgPheGlyAsnCysArgGlnThrArgAlaAspPheAsnHisAspIleIleArgLeuArgAlaHisGlyValAspAsnIleAlaAspAsnProArgValLe
uGlnLysIleLeuProGluThrLeuAlaGlyPheValPhePheHisArgValSerSerSerValGluThrProProPheArgAlaAlaGlySerAspSerValT
rpAlaGlyArgAsnProPheGlnIleArgThrThrHisArgAlaValLeuTyrValSerSerCysValLeuGluHisLysCysValTyrSerIleArgLeuMet
SerAlaLeu-297 |

Antigenic Index - Jameson-Wolf (SEQ. ID. NO. 36162)
1-ValPheGlyThrValLeuArgThrAspAlaAspCysLeuGlnIleIleValValGlyLysPhePheGlnValVa
lAlaTyrGlyPheAlaAlaLeuAlaGluGlyGluPheHisGlnPheGlyGluMetIleGluIleValArgLeuAla
AspThrValPheHisArgAsnHisAlaHisHisCysGlyIleAspPheArgArgGlyIleGluArgPheGlyArgH
isValAsnGlnGlnLeuHisIleGluLysIleLeuGlnHisHisThrGlnAlaThrValValValAlaPheArgAr
gGlyAsnHisAlaLeuAspHisPhePheLeuGlnHisLysValHisIleGlyAspIleValArgHisLeuArgGln
PheGluGlnLysArgArgGlyAspValIleArgGlnValAlaAspAspPheLeuPheAlaAspAlaValGluIleL
ysLeuGlnHisValAlaPheValAsnHisGlnPheIleArgLysArgGlnArgPheGlnThrAlaTyrAspValAl
aValAspPheAspAsnValGlnAlaValGlnLeuPheArgGlnArgPheGlyAsnCysArgGlnThrArgAlaAsp
PheAsnHisAspIleIleArgLeuArgAlaHisGlyValAspAsnIleAlaAspAsnProArgValLeuGlnLysI
leLeuProGluThrLeuAlaGlyPheValPhePheHisArgValSerSerSerValGluThrProProPheArgAl
aAlaGlySerAspSerValTrpAlaGlyArgAsnProPheGlnIleArgThrThrHisArgAlaValLeuTyrVal
SerSerCysValLeuGluHisLysCysValTyrSerIleArgLeuMetSerAlaLeu-297
Hydrophilic Regions - Hopp-Woods (SEQ. ID. NO. 36162)
1-ValPheGlyThrValLeuArgThrAspAlaAspCysLeuGlnIleIleValValGlyLysPhePheGlnValVa
lAlaTyrGlyPheAlaAlaLeuAlaGluGlyGluPheHisGlnPheGlyGluMetIleGluIleValArgLeuAla
AspThrValPheHisArgAsnHisAlaHisHisCysGlyIleAspPheArgArgGlyIleGluArgPheGlyArgH
isValAsnGlnGlnLeuHisIleGluLysIleLeuGlnHisHisThrGlnAlaThrValValValAlaPheArgAr
gGlyAsnHisAlaLeuAspHisPhePheLeuGlnHisLysValHisIleGlyAspIleValArgHisLeuArgGln
PheGluGlnLysArgArgGlyAspValIleArgGlnValAlaAspAspPheLeuPheAlaAspAlaValGluIleL
ysLeuGlnHisValAlaPheValAsnHisGlnPheIleArgLysArgGlnArgPheGlnThrAlaTyrAspValAl
aValAspPheAspAsnValGlnAlaValGlnLeuPheArgGlnArgPheGlyAsnCysArgGlnThrArgAlaAsp
PheAsnHisAspIleIleArgLeuArgAlaHisGlyValAspAsnIleAlaAspAsnProArgValLeuGlnLysI
leLeuProGluThrLeuAlaGlyPheValPhePheHisArgValSerSerSerValGluThrProProPheArgAl
aAlaGlySerAspSerValTrpAlaGlyArgAsnProPheGlnIleArgThrThrHisArgAlaValLeuTyrVal
SerSerCysValLeuGluHisLysCysValTyrSerIleArgLeuMetSerAlaLeu-297
g774
AMPHI Regions - AMPHI

| | |
|---|---|
| SEQ. ID. NO. 36163 | 16-AlaSerCysAlaSerValLeu-22 |
| SEQ. ID. NO. 36164 | 61-ValArgLeuSerAsnGluVal-67 |
| SEQ. ID. NO. 36165 | 90-ValGlnLysLeuAsp-94 |

TABLE 1-continued

| | |
|---|---|
| SEQ. ID. NO. 36166 | 115-ValGluThrAlaGlnAsnLeuTyrAsnGlnAlaLeuLysHisTyrGlnAsnGly-132 |
| SEQ. ID. NO. 36167 | 170-CysGluSerValIleGluIle-176 |
| SEQ. ID. NO. 36168 | 180-TyrAlaAsnArgPheLysAspSer-187 |
| SEQ. ID. NO. 36169 | 210-AlaArgAlaThrTrpArgSerLeuIleGlnThrTyrProGly-223 |
| Antigenic Index - Jameson-Wolf | |
| SEQ. ID. NO. 36170 | 23-ProValProGluGlySerArgThrGluMetProThrGlnGluAsnAlaSerAspGlyIlePro-43 |
| SEQ. ID. NO. 36171 | 49-LeuGlnAspArgLeuAspTyrLeuGlu-57 |
| SEQ. ID. NO. 36172 | 59-LysIleValArgLeuSerAsnGluValGluMetLeuAsnGlyLysValLysAlaLeuGluHisThrLysIleHisProSerGlyArgThrTyrVal GlnLysLeuAspAspArgLysLeuLysGlu-100 |
| SEQ. ID. NO. 36173 | 102-TyrLeuAsnThrGluGlyGlySerAla-110 |
| SEQ. ID. NO. 36174 | 125-AlaLeuLysHisTyrGlnAsnGlyArgPhe-134 |
| SEQ. ID. NO. 36175 | 142-LysGlyAlaAspGlyGlyAspGlyGlySerIleAlaGln-154 |
| SEQ. ID. NO. 36176 | 162-GlnSerArgAlaArgMetGlyAsnCys-170 |
| SEQ. ID. NO. 36177 | 176-IleGlyGlyArgTyrAlaAsnArgPheLysAspSerProThrAla-190 |
| SEQ. ID. NO. 36178 | 198-GlyGluCysGlnTyr-202 |
| SEQ. ID. NO. 36179 | 204-LeuGlnGlnLysAspIleAla-210 |
| SEQ. ID. NO. 36180 | 221-TyrProGlySerProAlaAlaLysArgAlaAlaAlaAlaValArgLysArg-237 |
| Hydrophilic Regions - Hopp-Woods | |
| SEQ. ID. NO. 36181 | 25-ProGluGlySerArgThrGluMetProThrGlnGluAsnAlaSerAsp-40 |
| SEQ. ID. NO. 36182 | 49-LeuGlnAspArgLeuAspTyrLeuGlu-57 |
| SEQ. ID. NO. 36183 | 59-LysIleValArgLeuSerAsnGluValGluMetLeuAsnGlyLysValLysAlaLeuGluHisThrLysIleHisProSerGly-86 |
| SEQ. ID. NO. 36184 | 89-TyrValGlnLysLeuAspAspArgLysLeuLysGlu-100 |
| SEQ. ID. NO. 36185 | 142-LysGlyAlaAspGlyGlyAspGlyGlySerIleAlaGln-154 |
| SEQ. ID. NO. 36186 | 163-SerArgAlaArgMetGlyAsn-169 |
| SEQ. ID. NO. 36187 | 180-TyrAlaAsnArgPheLysAspSerProThrAla-190 |
| SEQ. ID. NO. 36188 | 198-GlyGluCysGlnTyr-202 |
| SEQ. ID. NO. 36189 | 204-LeuGlnGlnLysAspIleAla-210 |
| SEQ. ID. NO. 36190 | 225-ProAlaAlaLysArgAlaAlaAlaAlaValArgLysArg-237 |
| g900-2 | |
| AMPHI Regions - AMPHI | |
| SEQ. ID. NO. 36191 | 6-LeuGluAsnGlyThrHisSer-12 |
| SEQ. ID. NO. 36192 | 19-GluArgThrTyrProGluProCysHisGluCysLysTerTerLeuArgArgIle-36 |
| SEQ. ID. NO. 36193 | 43-AlaPheAlaGlnPheCys-48 |
| SEQ. ID. NO. 36194 | 68-ValGlyLysHisLeuArgLysPheArgArgPheArgArgArgGly-82 |
| SEQ. ID. NO. 36195 | 94-ValGlyLeuPheArgLeuAlaArgLeuPheHisValGlyAsnAspPheValAspArgPheLeuGlyPhePhe-117 |
| SEQ. ID. NO. 36196 | 130-PheGlyHisPheAlaSer-135 |
| SEQ. ID. NO. 36197 | 153-GlyGluGluPheLeuGluThrValValGluAlaAlaGlyAsnValAlaArgHisPheAspValLeuAspLeu-176 |
| SEQ. ID. NO. 36198 | 193-SerHisGlnAsnArgIle-198 |
| SEQ. ID. NO. 36199 | 230-HisGlnThrLeuGlyGlyAspAlaGly-238 |
| SEQ. ID. NO. 36200 | 242-ValGlnLeuHisHisPheGly-248 |
| SEQ. ID. NO. 36201 | 265-GlyLysProSerGlyGlyAsnGlyLeuGlyGlyLeuValAsn-278 |
| SEQ. ID. NO. 36202 | 311-AspGlyAlaAspValValAlaGlnMet-319 |
| Antigenic Index - Jameson-Wolf | |
| SEQ. ID. NO. 36203 | 1-GlyTerProGluProLeuGluAsnGlyThrHisSerGlyProThrGluMetAsxGluArgThrTyrProGluProCysHisGluCysLysTerTer LeuArgArgIleArgGlyGlnCys-40 |
| SEQ. ID. NO. 36204 | 50-PheGlyValAspPheArgArgArgLysPhePhe-60 |
| SEQ. ID. NO. 36205 | 70-LysHisLeuArgLysPheArgArgPheArgArgArgGlyGluGlyPheIle-86 |
| SEQ. ID. NO. 36206 | 88-PheLysGlnArgAla-92 |
| SEQ. ID. NO. 36207 | 105-ValGlyAsnAspPheValAsp-111 |
| SEQ. ID. NO. 36208 | 120-PheProLysArgAsnGlyIleAla-127 |
| SEQ. ID. NO. 36209 | 135-SerValGlnThrAspGlnGluPhe-142 |
| SEQ. ID. NO. 36210 | 150-PheGlyGlnGlyGluGluPheLeu-157 |
| SEQ. ID. NO. 36211 | 163-AlaAlaGlyAsnVal-167 |
| SEQ. ID. NO. 36212 | 177-ValAlaProAspGlyAspPheValGly-185 |
| SEQ. ID. NO. 36213 | 189-GlnAsnValGlySerHisGlnAsnArgIleThrGluGlnThrHisPhe-204 |
| SEQ. ID. NO. 36214 | 233-LeuGlyGlyAspAlaGlyGlnAsnPro-241 |
| SEQ. ID. NO. 36215 | 261-ValGluSerAlaGlyLysProSerGlyGlyAsnGly-272 |
| SEQ. ID. NO. 36216 | 289-ValValIleGlyGluGluGluGluGlyPhe-298 |
| SEQ. ID. NO. 36217 | 302-ValLeuArgArgAlaAspGlyGlyAlaAspGlyAlaAsp-314 |
| SEQ. ID. NO. 36218 | 319-MetArgGlyAlaGlyGlyGlyTyrAlaGly-328 |
| SEQ. ID. NO. 36219 | 343-MetProSerGluArgGluLysMetArgArg-352 |
| SEQ. ID. NO. 36220 | 361-ProAlaAspAsnArg-365 |
| Hydrophilic Regions - Hopp-Woods | |
| SEQ. ID. NO. 36221 | 1-GlyTerProGluProLeuGluAsnGlyThrHisSerGlyProThrGluMetAsxGluArgThrTyrPro-23 |
| SEQ. ID. NO. 36222 | 25-ProCysHisGluCysLysTerTerLeuArgArgIleArgGly-38 |
| SEQ. ID. NO. 36223 | 53-AspPheArgArgArgLysPhePhe-60 |
| SEQ. ID. NO. 36224 | 70-LysHisLeuArgLysPheArgArgPheArgArgArgGlyGluGly-84 |
| SEQ. ID. NO. 36225 | 121-ProLysArgAsnGly-125 |
| SEQ. ID. NO. 36226 | 137-GlnThrAspGlnGluPhe-142 |
| SEQ. ID. NO. 36227 | 152-GlnGlyGluGluPheLeu-157 |
| SEQ. ID. NO. 36228 | 177-ValAlaProAspGlyAspPheValGly-185 |
| SEQ. ID. NO. 36229 | 194-HisGlnAsnArgIleThrGlu-200 |
| SEQ. ID. NO. 36230 | 233-LeuGlyGlyAspAlaGlyGln-239 |
| SEQ. ID. NO. 36231 | 263-SerAlaGlyLysProSerGly-269 |
| SEQ. ID. NO. 36232 | 289-ValValIleGlyGluGluGluGluGlyPhe-298 |
| SEQ. ID. NO. 36233 | 302-ValLeuArgArgAlaAspGlyGlyAlaAspGlyAlaAsp-314 |
| SEQ. ID. NO. 36234 | 343-MetProSerGluArgGluLysMetArgArg-352 |
| g902 | |
| AMPHI Regions - AMPHI | |
| SEQ. ID. NO. 36235 | 56-AlaValGlyHisPheAlaAspValProAla-65 |

TABLE 1-continued

| | |
|---|---|
| SEQ. ID. NO. 36236 | 77-LeuThrIleLysArgValHisGly-84 |
| SEQ. ID. NO. 36237 | 128-AspAlaValGlyGlyGly-133 |
| SEQ. ID. NO. 36238 | 190-PheGlyAspPheGlyAsp-195 |
| SEQ. ID. NO. 36239 | 216-AlaArgArgLeuAsp-220 |
| SEQ. ID. NO. 36240 | 241-AspValAlaHisPheLeuGlyGlyAla-249 |
| SEQ. ID. NO. 36241 | 266-ArgArgIleArgHisLeuPheGlyVal-274 |
| SEQ. ID. NO. 36242 | 288-GlyLysIleThrAlaValGlnGlyPheSer-297 |
| SEQ. ID. NO. 36243 | 318-ArgProThrGluAlaAlaGluGlyPhe-326 |
| SEQ. ID. NO. 36244 | 334-ArgLysCysAspGlyValValAspLysIleThrAlaAspVal-347 |

Antigenic Index - Jameson-Wolf

| | |
|---|---|
| SEQ. ID. NO. 36245 | 1-MetProSerGluProGluArgArgHisGlyAsnThrAla-13 |
| SEQ. ID. NO. 36246 | 26-PheSerGlyLysProPheLysIleThrGly-35 |
| SEQ. ID. NO. 36247 | 38-ValValLeuArgArgArgIleValGln-46 |
| SEQ. ID. NO. 36248 | 72-AlaHisThrAspGlyLeuThrIleLysArgValHisGly-84 |
| SEQ. ID. NO. 36249 | 89-GlnAsnGlyGlySer-93 |
| SEQ. ID. NO. 36250 | 97-GlnThrGlnGlyArgArgXxxAsn-104 |
| SEQ. ID. NO. 36251 | 113-IleAlaGluLysProArgProAlaLeu-121 |
| SEQ. ID. NO. 36252 | 134-LeuPheGluAspGlyGlyGlyPheLeuArgArgSerAspValAlaValAspProGlyArgAspValGln-156 |
| SEQ. ID. NO. 36253 | 175-ArgAlaArgAlaProValAsnGlyLysGlyGlyAsn-186 |
| SEQ. ID. NO. 36254 | 192-AspPheGlyAspGlyGlyGln-198 |
| SEQ. ID. NO. 36255 | 210-PheGluGlyAsnGlyTyrAlaArgArgLeuAspHisArgLeuGlnAsnGlyGlyAsnGlnArgLeu-231 |
| SEQ. ID. NO. 36256 | 252-IleAspValAspAspLeuArgProGluSerAspValValThrArgArgIleArg-269 |
| SEQ. ID. NO. 36257 | 277-GlyAsnLeuHisGlyAsnAspAla-284 |
| SEQ. ID. NO. 36258 | 296-PheSerGlyIleProGluArgArgIleAla-305 |
| SEQ. ID. NO. 36259 | 310-AlaHisArgProThrCysAlaLysArgProThrGluAlaAlaGlu-324 |
| SEQ. ID. NO. 36260 | 330-AlaArgHisArgArgLysCysAspGlyValValAspLysIleThrAla-345 |
| SEQ. ID. NO. 36261 | 347-ValHisAsnGlyProAlaPheGlnLysSerAla-357 |

Hydrophilic Regions - Hopp-Woods

| | |
|---|---|
| SEQ. ID. NO. 36262 | 1-MetProSerGluProGluArgArgHisGlyAsn-11 |
| SEQ. ID. NO. 36263 | 29-LysProPheLysIleThrGly-35 |
| SEQ. ID. NO. 36264 | 38-ValValLeuArgArgArgIleValGln-46 |
| SEQ. ID. NO. 36265 | 77-LeuThrIleLysArgValHisGly-84 |
| SEQ. ID. NO. 36266 | 99-GlnGlyArgArgXxxAsn-104 |
| SEQ. ID. NO. 36267 | 113-IleAlaGluLysProArgProAlaLeu-121 |
| SEQ. ID. NO. 36268 | 134-LeuPheGluAspGlyGlyGlyPheLeuArgArgSerAspValAlaValAspProGlyArgAspValGln-156 |
| SEQ. ID. NO. 36269 | 175-ArgAlaArgAlaProValAsnGlyLysGlyGlyAsn-186 |
| SEQ. ID. NO. 36270 | 214-GlyTyrAlaArgArgLeuAspHisArgLeuGlnAsn-225 |
| SEQ. ID. NO. 36271 | 252-IleAspValAspAspLeuArgProGluSerAspValValThrArgArgIleArg-269 |
| SEQ. ID. NO. 36272 | 299-IleProGluArgArgIleAla-305 |
| SEQ. ID. NO. 36273 | 313-ProThrCysAlaLysArgProThrGluAlaAlaGlu-324 |
| SEQ. ID. NO. 36274 | 330-AlaArgHisArgArgLysCysAspGlyValValAspLysIleThrAla-345 | g904
AMPHI Regions - AMPHI

| | |
|---|---|
| SEQ. ID. NO. 36275 | 1-MetMetGlnHisAsnArgPhePheAlaValGlyAlaGlyGlyAspAspGlyAspArgArgAlaAlaAspPhePheAsnProPheGlnIleCysPheGlyIleGlyArgGlnCysValValAlaPheHisAlaAspSerArgPheAlaProAlaGlyHisGlyPheValAsnArgPheAlaGlyPheHisArgIleArgThrAlaArgGlnAspValGlyPheAlaAlaAlaTrpGlnPheValAlaAspAlaAspIleAspGlyPheAsnAlaValHisTyrIleGluPheGlyAsnAlaHisThrGlyAsnAlaValAspLeuAspGlyAlaPheGlnGlyGlyGlyIleLysProAlaAlaAlaAlaArgAlaAlaAlaAlaGlyTyrArgThrGluPheValSerAlaLeuArgGlnThrCysAlaTyrPheValGluGlnPheGlyArgGluArgAlaArgThrAspAlaArgGlyIleGlyPheAspAspAlaGlnAsnIleIleGlnHisLeuArgThrTyrAlaArgAlaCysArgSerArgAlaGlyGluThrValGlyArgGlyAsnGluGlyValSerAlaValValAspValGlnGlnArgThrLeuArgAlaPheLysGlnGlnPhePheAlaValPhePheValPheValGlnHisAlaGlyHisValGlyAsnHisArgArgAsnAlaArgArgAspPhePheAspAsnArgHisHisValPheArgPheAsnArgSerGlyValMetGlnValLeuGluLeuAspValValIleGlyLysAspGlyIleGlnPhePheThrGlnPhePheArgMetGlnGlnIleGlyGlyAlaAsnGlyAlaAlaCysHisPheValPheValGlyArgAlaAspAlaAlaAlaGlyArgAlaAspPheAlaPheAlaAlaArgCysPheAlaGlyLeuValGluArgAspValValArgGlnAspGlnArgAlaGlyArgArgAspPheGlnThrAlaPheAspValPheHisAlaCysArgValGlnLeuValAspPheAlaGlnGlnGlyPheGlyGlyAsnAspAsnAlaArgThrAspGluAlaIleGlnSerPheValGlnAspThrAlaArgAsnGlnAlaGlnAsnGlyPhePheAlaAlaAspAspGlnGlyMetAlaArgIleValAlaAlaLeuGluAlaHisAspAlaAlaGlyPhePheArgGlnProValAsnAspPheThrPheThrLeuValAlaProLeuCysAlaAspTyrTyrAsnIlePheSerHisSerHisIleThrTyrArgTyr-436 |

Antigenic Index - Jameson-Wolf (SEQ. ID. NO. 36275)
1-MetMetGlnHisAsnArgPhePheAlaValGlyAlaGlyGlyAspAspGlyAspArgArgAlaAlaAspPhePheAsnProPheGlnIleCysPheGlyIleGlyArgGlnCysValValAlaPheHisAlaAspSerArgPheAlaProAlaGlyHisGlyPheValAsnArgPheAlaGlyPheHisArgIleArgThrAlaArgGlnAspValGlyPheAlaAlaAlaAlaTrpGlnPheValAlaAspAlaAspIleAspGlyPheAsnAlaValHisTyrIleGluPheGlyAsnAlaHisThrGlyAsnAlaValAspLeuAspGlyAlaPheGlnGlyGlyGlyIleLysProAlaAlaAlaAlaArgAlaAlaGlyTyrArgThrGluPheValSerAlaLeuArgGlnThrCysAlaTyrPheValGluGlnPheGlyArgGluArgAlaArgThrAspAlaArgGlyIleGlyPheAspAspAlaGlnAsnIleIleGlnHisLeuArgThrTyrAlaArgAlaCysArgSerArgAlaGlyGluThrValGlyArgGlyAsnGluGlyValSerAlaValValAspValGlnGlnArgThrLeuArgAlaPheLysGlnGlnPhePheAlaValPhePheValPheValGlnHisAlaGlyHisValGlyAsnHisArgArgAsnAlaArgArgAspPhePheAspAsnArgHisHisValPheArgPheAsnArgSerGlyValMetGlnValLeuGluLeuAspValValIleGlyLysAspGlyIleGlnPhePheThrGlnPhePheArgMetGlnGlnIleGlyGlyAlaAsnGlyAlaAlaCysHisPheValPheValGlyArgAlaAspAlaAlaAlaGlyArgAlaAspPheAlaPheAlaAlaAlaArgCysPheAlaGlyLeuValGluArgAspValValArgGlnAspGlnArgAlaGlyArgArgAspPheGlnThrAlaPheAspValPheHisAlaCysArgValGlnLeuValAspPheAlaGlnGlnGlyPheGlyGlyAsnAspAsnAlaArgThrAspGluAlaIleGlnSerPheValGlnAspThrAlaArgAsnGlnAlaGlnAsnGlyPhePheAlaAlaAspAspGlnGlyMetAlaArgIleValAlaAlaLeuGluAlaHisAspAlaAlaGlyPhePheArgGlnProValAsnAspPheThrPheThrLeuValAlaProLeuCysAlaAspTyrTyrAsnIlePheSerHisSerHisIleThrTyrArgTyr-436

Hydrophilic Regions - Hopp-Woods (SEQ. ID. NO. 36275)
1-MetMetGlnHisAsnArgPhePheAlaValGlyAlaGlyGlyAspAspGlyAspArgArgAlaAlaAspPhePheAsnProPheGlnIleCysPheGlyIleGlyArgGlnCysValValAlaPheHisAlaAspSerArgPheAlaProAlaGlyHisGlyPheValAsnArgPheAlaGlyPheHisArgIleArgThrAlaArgGlnAspValGlyPheAlaA TABLE 1-continued laAlaTrpGlnPheValAlaAspAlaAspIleAspGlyPheAsnAlaValHisTyrIleGluPheGlyAsnAlaHi
sThrGlyAsnAlaValAspLeuAspGlyAlaPheGlnGlyGlyGlyIleLysProAlaAlaAlaAlaArgAlaAla
GlyTyrArgThrGluPheValSerAlaLeuArgGlnThrCysAlaTyrPheValGluGlnPheGlyArgGluArgA
laArgThrAspAlaArgGlyIleGlyPheAspAspAlaGlnAsnIleIleGlnHisLeuArgThrTyrAlaArgAl
aCysArgSerArgAlaGlyGluThrValGlyArgGlyAsnGluGlyValSerAlaValValAspValGlnGlnArg
ThrLeuArgAlaPheLysGlnGlnPhePheAlaValPheValPhePheValGlnHisAlaGlyHisValGlyAsnH
isArgArgAsnAlaArgArgAspPhePheAspAsnArgHisHisValPheArgPheAsnArgSerGlyValMetGl
nValLeuGluLeuAspValValIleGlyLysAspGlyIleGlnPhePheThrGlnPhePheArgMetGlnGlnIle
GlyGlyAlaAsnGlyAlaAlaCysHisPheValPheValGlyArgAlaAspAlaAlaAlaGlyArgAlaAspPheA
laPheAlaAlaArgCysPheAlaGlyLeuValGluArgAspValValArgGlnAspGlnArgAlaGlyArgArgAs
pPheGlnThrAlaPheAspValPheHisAlaCysArgValGlnLeuValAspPheAlaGlnGlnGlyPheGlyGly
AsnAspAsnAlaArgThrAspGluAlaIleGlnSerPheValGlnAspThrAlaArgAsnGlnAlaGlnAsnGlyP
hePheAlaAlaAspAspGlnGlyMetAlaArgIleValAlaAlaLeuGluAlaHisAspAlaAlaGlyPhePheAr
gGlnProValAsnAspPheThrPheThrLeuValAlaProLeuCysAlaAspTyrTyrAsnIlePheSerHisSer
HisIleThrTyrArgTyr-436
g907-2
AMPHI Regions - AMPHI
SEQ. ID. NO. 36276  6-LeuGluAsnGlyThrHisSer-12
SEQ. ID. NO. 36277  19-GluArgThrTyrProGluProCysHisGluCysLysTerTerMetLysLysProThrAspThrLeuPro-41
SEQ. ID. NO. 36278  74-AspAspValAlaSerValMetArgSer-82
SEQ. ID. NO. 36279  98-LysGluGlyGluArgTrpLeuSerAlaMetSer-108
SEQ. ID. NO. 36280  110-ArgLeuAlaArgPheValPro-116
SEQ. ID. NO. 36281  161-GlyAlaArgGlyLeu-165
SEQ. ID. NO. 36282  174-AsnTyrIleGlyLysProAlaHis-181
SEQ. ID. NO. 36283  197-LeuArgHisTyrArgAsnLeuGluLysGlyAspIleValArgAlaLeuAlaArgPheAsnGly-217
Antigenic Index - Jameson-Wolf
SEQ. ID. NO. 36284  1-GlyTerProGluProLeuGluAsnGlyThrHisSerGluProThrGluMetAsxGluArgThrTyrProGluProCysHisGluCysLysTer
    TerMetLysLysProThrAspThrLeuPro-41
SEQ. ID. NO. 36285  44-LeuGlnArgArgArgLeuLeu-50
SEQ. ID. NO. 36286  65-GlyAlaGlnArgGluGluThrLeuAlaAspAspValAlaSer-78
SEQ. ID. NO. 36287  83-SerValGlySerValAsnProProArgLeuValPheAspAsnProLysGluGlyGluArgTrp-103
SEQ. ID. NO. 36288  113-ArgPheValProAspGluGlyGluArgArgArgLeu-124
SEQ. ID. NO. 36289  129-GlnTyrGluSerSerArgAlaGlyLeu-137
SEQ. ID. NO. 36290  147-GluValGluSerAlaPhe-152
SEQ. ID. NO. 36291  174-AsnTyrIleGlyLysProAlaHisAsn-182
SEQ. ID. NO. 36292 187-ArgThrAsnLeuArgTyrGly-193
SEQ. ID. NO. 36293 200-TyrArgAsnLeuGluLysGlyAspIleVal-209
SEQ. ID. NO. 36294 216-AsnGlySerLeuGlySerAsnLysTyrProAsnAla-227
SEQ. ID. NO. 36295 232-TrpArgAsnArgTrpGlnTrp-238

Hydrophilic Regions - Hopp-Woods

SEQ. ID. NO. 36296 1-GlyTerProGluProLeuGluAsnGlyThrHisSerGluProThrGluMe
tAsxGluArgThrTyrPro-23
SEQ. ID. NO. 36297 25-ProCysHisGluCysLysTerTerMetLysLysProThrAsp-38
SEQ. ID. NO. 36298 44-LeuGlnArgArgArgLeuLeu-50
SEQ. ID. NO. 36299 65-GlyAlaGlnArgGluGluThrLeuAlaAspAspValAlaSer-78
SEQ. ID. NO. 36300 92-LeuValPheAspAsnProLysGluGlyGluArgTrp-103
SEQ. ID. NO. 36301 115-ValProAspGluGlyGluArgArgArgLeu-124
SEQ. ID. NO. 36302 131-GluSerSerArgAlaGlyLeu-137
SEQ. ID. NO. 36303 147-GluValGluSerAlaPhe-152
SEQ. ID. NO. 36304 201-ArgAsnLeuGluLysGlyAspIleVal-209 g908

AMPHI Regions - AMPHI

SEQ. ID. NO. 36305 24-ThrAlaAlaGluLeu-28
SEQ. ID. NO. 36306 125-ThrAspCysTyrArgSerTyrAspValLeuAspValSerGluPheSerHisPheSer-143

Antigenic Index - Jameson-Wolf

SEQ. ID. NO. 36307 1-LysSerArgLeuSerArgTyrLysGlnAsnLysLeu-12
SEQ. ID. NO. 36308 30-GlyIleAsnLysAsnThrAla-36
SEQ. ID. NO. 36309 49-GlnAsnGlyProHis-53
SEQ. ID. NO. 36310 57-PheAspGlyGluValGluAlaAspGluSerTyrPheGlyGlyGlnArgLysGlyLysArgGlyArgGlyAlaAlaGlyLys-83
SEQ. ID. NO. 36311 89-LeuLeuLysArgAsnGlyLysVal-96
SEQ. ID. NO. 36312 113-IleArgGluGlnValLysProAspSerIleVal-123
SEQ. ID. NO. 36313 125-ThrAspCysTyrArgSerTyrAsp-132
SEQ. ID. NO. 36314 159-ArgThrThrLysProTyr-164

Hydrophilic Regions - Hopp-Woods

SEQ. ID. NO. 36315 1-LysSerArgLeuSerArgTyrLysGlnAsnLys-11
SEQ. ID. NO. 36316 57-PheAspGlyGluValGluAlaAspGluSerTyr-67
SEQ. ID. NO. 36317 70-GlyGlnArgLysGlyLysArgGlyArgGlyAlaAlaGly-82
SEQ. ID. NO. 36318 90-LeuLysArgAsnGlyLys-95
SEQ. ID. NO. 36319 113-IleArgGluGlnValLysProAspSer-121 g909

AMPHI Regions - AMPHI

SEQ. ID. NO. 36320 24-GlnAspGlySerGly-28

Antigenic Index - Jameson-Wolf

SEQ. ID. NO. 36321 22-ThrTyrGlnAspGlySerGlyLysThrAlaValArgAlaLysCysSerThrGlyThrPro-41
SEQ. ID. NO. 36322 45-GlnAspGlyArgGlySerLysLysValAspCysAspGluTyrGlyGlyGluArgArgAlaValLeuArgAsnGlnLysArgGlyLysProAlaThr
ArgArgAlaAlaThr-81
SEQ. ID. NO. 36323 83-GlyLysProSerPheArgAlaArgAspGlyGlyGlyArgValAsnArgAlaGluThrGlyGluGlyLysArgSerAlaArg-109

Hydrophilic Regions - Hopp-Woods

SEQ. ID. NO. 36324 23-TyrGlnAspGlySerGlyLysThrAlaValArgAlaLysCysSerThr-38

TABLE 1-continued

| | |
|---|---|
| SEQ. ID. NO. 36325 | 46-AspGlyArgGlySerLysLysValAspCysAspGluTyrGlyGlyGluArgArgAlaValLeuArgAsnGlnLysArgGlyLysProAlaThrArgArgAlaAlaThr-81 |
| SEQ. ID. NO. 36326 | 85-ProSerPheArgAlaArgAspGlyGlyGlyArgValAsnArgAlaGluThrGlyGluGlyLysArgSerAlaArg-109 | g910
AMPHI Regions - AMPHI

| | |
|---|---|
| SEQ. ID. NO. 36327 | 22-SerAlaGluArgGlnIle-27 |
| SEQ. ID. NO. 36328 | 39-LysAlaValLysMetLeuGlu-45 |
| SEQ. ID. NO. 36329 | 69-AlaTyrLysAspGlyArg-74 |

Antigenic Index - Jameson-Wolf

| | |
|---|---|
| SEQ. ID. NO. 36330 | 19-AlaGlyAspSerAlaGluArgGlnIleTyrGlyAspProHisPheGluGlnAsnArgThrLysAlaValLysMetLeuGluGlnArgGlyTyrGln-50 |
| SEQ. ID. NO. 36331 | 53-AspValAspAlaAspAspTyrTrpGlyLysProValLeuGlu-66 |
| SEQ. ID. NO. 36332 | 68-GluAlaTyrLysAspGlyArgGluTyrAsp-77 |
| SEQ. ID. NO. 36333 | 83-ProAspLeuLysIleIleLysGluGlnLeuAspArg-94 |

Hydrophilic Regions - Hopp-Woods

| | |
|---|---|
| SEQ. ID. NO. 36334 | 21-AspSerAlaGluArgGlnIleTyr-28 |
| SEQ. ID. NO. 36335 | 31-ProHisPheGluGlnAsnArgThrLysAlaValLysMetLeuGluGlnArgGly-48 |
| SEQ. ID. NO. 36336 | 53-AspValAspAlaAspAspTyrTrp-60 |
| SEQ. ID. NO. 36337 | 68-GluAlaTyrLysAspGlyArgGluTyrAsp-77 |
| SEQ. ID. NO. 36338 | 86-LysIleIleLysGluGlnLeuAspArg-94 | g911
AMPHI Regions - AMPHI

| | |
|---|---|
| SEQ. ID. NO. 36339 | 6-LeuGluPheTrpValGlyLeuPhe-13 |
| SEQ. ID. NO. 36340 | 43-ValTyrAlaAspPheGlyAspIleGly-51 |
| SEQ. ID. NO. 36341 | 97-ValSerAlaGlnIle-101 |
| SEQ. ID. NO. 36342 | 118-GlyAspThrGluAsnLeuAla-124 |
| SEQ. ID. NO. 36343 | 140-AsnLeuIleGlyLysPheMetThrSerPhe-149 |

Antigenic Index - Jameson-Wolf

| | |
|---|---|
| SEQ. ID. NO. 36344 | 1-MetLysLysAsnIle-5 |
| SEQ. ID. NO. 36345 | 35-GlyGlySerAspLysThrTyr-41 |
| SEQ. ID. NO. 36346 | 48-GlyAspIleGlyGlyLeuLysValAsnAlaProValLys-60 |
| SEQ. ID. NO. 36347 | 74-LeuAspProLysSerTyrGlnAlaArgValArgLeuAspLeuAspGlyLysTyrGlnPheSerSerAspVal-97 |
| SEQ. ID. NO. 36348 | 103-ThrSerGlyLeuLeuGly-108 |
| SEQ. ID. NO. 36349 | 115-GlnGlnGlyGlyAspThrGluAsn-122 |
| SEQ. ID. NO. 36350 | 149-PheAlaGluLysAsnAlaGluGlyGlyAsnAlaGluLysAlaAlaGlu-164 |

Hydrophilic Regions - Hopp-Woods

| | |
|---|---|
| SEQ. ID. NO. 36351 | 1-MetLysLysAsnIle-5 |
| SEQ. ID. NO. 36352 | 36-GlySerAspLysThr-40 |
| SEQ. ID. NO. 36353 | 74-LeuAspProLysSerTyrGlnAlaArgValArgLeuAspLeuAspGly-89 |
| SEQ. ID. NO. 36354 | 116-GlnGlyGlyAspThrGluAsn-122 |
| SEQ. ID. NO. 36355 | 149-PheAlaGluLysAsnAlaGluGlyGlyAsnAlaGluLysAlaAlaGlu-164 | g912
AMPHI Regions - AMPHI

| | |
|---|---|
| SEQ. ID. NO. 36356 | 23-SerProAlaAspAlaValGlyGlnIle-31 |
| SEQ. ID. NO. 36357 | 63-AspPheGlnArgMetThrAlaLeuAlaValGlyAsnProTrpArgThrAlaSerAspAlaGlnLys-84 |
| SEQ. ID. NO. 36358 | 89-LysGluPheGlnThrLeu-94 |
| SEQ. ID. NO. 36359 | 169-TyrArgAsnGlnPheGlyGluIleIleLysAlaLysGlyIleAspGlyLeuIleAla-187 |

Antigenic Index - Jameson-Wolf

| | |
|---|---|
| SEQ. ID. NO. 36360 | 1-ValLysLysSerSer-5 |
| SEQ. ID. NO. 36361 | 23-SerProAlaAspAla-27 |
| SEQ. ID. NO. 36362 | 31-IleArgGlnAsnAlaThrGln-37 |
| SEQ. ID. NO. 36363 | 42-LeuLysSerGlyAspAlaAlaSerAlaArgProLysAlaGluAla-56 |
| SEQ. ID. NO. 36364 | 74-AsnProTrpArgThrAlaSerAspAlaGlnLysGlnAlaLeuAlaLysGluPhe-91 |
| SEQ. ID. NO. 36365 | 104-LeuLysPheLysAsn-108 |
| SEQ. ID. NO. 36366 | 112-AsnValLysAspAsnProIleValAsnLysGlyGlyLysGluIleValVal-128 |
| SEQ. ID. NO. 36367 | 134-IleProGlyGlnLysProValAsnMet-142 |
| SEQ. ID. NO. 36368 | 146-ThrTyrGlnSerGlyGlyLysTyrArgThr-155 |
| SEQ. ID. NO. 36369 | 169-TyrArgAsnGlnPhe-173 |
| SEQ. ID. NO. 36370 | 177-IleLysAlaLysGlyIleAsp-183 |
| SEQ. ID. NO. 36371 | 189-LeuLysAlaLysAsnGlyGlyLys-196 |

Hydrophilic Regions - Hopp-Woods

| | |
|---|---|
| SEQ. ID. NO. 36372 | 1-ValLysLysSerSer-5 |
| SEQ. ID. NO. 36373 | 31-IleArgGlnAsnAla-35 |
| SEQ. ID. NO. 36374 | 43-LysSerGlyAspAlaAlaSerAlaArgProLysAlaGluAla-56 |
| SEQ. ID. NO. 36375 | 78-ThrAlaSerAspAlaGlnLysGlnAlaLeuAlaLysGluPhe-91 |
| SEQ. ID. NO. 36376 | 104-LeuLysPheLysAsn-108 |
| SEQ. ID. NO. 36377 | 112-AsnValLysAspAsnProIleVal-119 |
| SEQ. ID. NO. 36378 | 121-LysGlyGlyLysGluIleValVal-128 |
| SEQ. ID. NO. 36379 | 177-IleLysAlaLysGlyIleAsp-183 |
| SEQ. ID. NO. 36380 | 189-LeuLysAlaLysAsnGlyGlyLys-196 | g913
AMPHI Regions - AMPHI

| | |
|---|---|
| SEQ. ID. NO. 36381 | 22-GluThrArgProAlaAspProTyrGluGlyTyrAsnArgAlaValSerLysPheAsnAspGlnAla-43 |
| SEQ. ID. NO. 36382 | 53-ArgGlyTyrArgLysValThrProLys-61 |
| SEQ. ID. NO. 36383 | 66-GlyValSerAsnPhePheAsnAsnLeuArgLysAspValValSer-79 |
| SEQ. ID. NO. 36384 | 107-LeuGlyGlyLeuIleLeuAspIleAlaGly-115 |
| SEQ. ID. NO. 36385 | 151-ValArgAspAlaLeuGlyThrGlyIleThrSerValTyr-163 |
| SEQ. ID. NO. 36386 | 193-AspLeuThrAspSerLeuAspGluAlaAla-202 |
| SEQ. ID. NO. 36387 | 240-LeuValGluSerAla-244 |
| SEQ. ID. NO. 36388 | 259-SerGluThrGlnAla-263 |

TABLE 1-continued

Antigenic Index - Jameson-Wolf
SEQ. ID. NO. 36389  1-MetLysLysThrAla-5
SEQ. ID. NO. 36390  21-AlaGluThrArgProAlaAspProTyrGluGlyTyrAsnArgAlaValSerLysPheAsnAspGlnAlaAspArgTyr-46
SEQ. ID. NO. 36391  51-AlaAlaArgGlyTyrArgLysValThrProLysProValArgAla-65
SEQ. ID. NO. 36392  87-LeuAspIleLysArgAlaSerGluAspLeuVal-97
SEQ. ID. NO. 36393  117-GlyGlyValProAspAsnLysAsnThrLeuGlyAsp-128
SEQ. ID. NO. 36394  132-SerTrpGlyTrpLysAsnSerAsn-139
SEQ. ID. NO. 36395  149-SerThrValArgAspAlaLeu-155
SEQ. ID. NO. 36396  163-TyrProProLysAsn-167
SEQ. ID. NO. 36397  173-ProAlaGlyArgTrpGly-178
SEQ. ID. NO. 36398  186-SerThrArgGluGlyLeuLeuAspLeuThrAspSerLeuAspGluAlaAlaIleAspLysTyrSerTyrThrArgAspLeuTyrMet-214
SEQ. ID. NO. 36399  216-ValArgAlaArgGlnThrGlyAlaThrProAlaGluGlyThrGluAspAsnIleAspIleAspGluLeuValGluSerAlaGluThrGly
                    AlaAla-249
SEQ. ID. NO. 36400  252-AlaValHisGluAspSerValSerGluThrGlnAlaGluAlaAlaGlyGluAlaGluThrGlnProGlyThrGlnPro-277
Hydrophilic Regions - Hopp-Woods
SEQ. ID. NO. 36401  1-MetLysLysThrAla-5
SEQ. ID. NO. 36402  21-AlaGluThrArgProAlaAspProTyrGluGlyTyrAsn-33
SEQ. ID. NO. 36403  35-AlaValSerLysPheAsnAspGlnAlaAsp-44
SEQ. ID. NO. 36404  53-ArgGlyTyrArgLysValThrProLysProValArg-64
SEQ. ID. NO. 36405  87-LeuAspIleLysArgAlaSerGluAspLeuVal-97
SEQ. ID. NO. 36406  118-GlyValProAspAsnLysAsnThrLeu-126
SEQ. ID. NO. 36407  150-ThrValAspAlaLeu-155
SEQ. ID. NO. 36408  186-SerThrArgGluGlyLeuLeuAspLeuThrAspSerLeuAspGluAlaAlaIleAsp-204
SEQ. ID. NO. 36409  216-ValArgAlaArgGlnThrGly-222
SEQ. ID. NO. 36410  224-ThrProAlaGluGlyThrGluAspAsnIleAspIleAspGluLeuValGluSerAlaGluThrGlyAlaAla-249
SEQ. ID. NO. 36411  252-AlaValHisGluAspSerValSerGluThrGlnAlaGluAlaAlaGlyGluAlaGluThrGlnPro-273
g914-2
AMPHI Regions - AMPHI
SEQ. ID. NO. 36412  6-LeuGlyIleLeuThrAlaCysAlaAlaMet-15
SEQ. ID. NO. 36413  17-AlaPheAlaAspArgIleSerAspLeu-25
SEQ. ID. NO. 36414  65-PheGlnLysThrPheGlu-70
SEQ. ID. NO. 36415  81-GlnLysValArgGlnAlaCys-87
Antigenic Index - Jameson-Wolf
SEQ. ID. NO. 36416  18-PheAlaAspArgIleSerAspLeuGluAlaArgLeuAlaGlnLeuGluHisArgValAlaValLeuGluSerGlyGlyAsnThrValLys-47
SEQ. ID. NO. 36417  50-LeuPheGlySerAsnSer-55
SEQ. ID. NO. 36418  64-ProPheGlnLysThrPheGluAlaSerAspArgAsnGluGlyValAlaArgGlnLysValArgGlnAlaCysAsnArgGluThrSerAla-93
SEQ. ID. NO. 36419  96-CysGlyAspGluAlaIleArgCysArgLysPheAsp-107
Hydrophilic Regions - Hopp-Woods
SEQ. ID. NO. 36420  18-PheAlaAspArgIleSerAspLeuGluAlaArgLeuAlaGlnLeuGluHisArgValAlaVal-38
SEQ. ID. NO. 36421  67-LysThrPheGluAlaSerAspArgAsnGluGlyValAlaArgGlnLysValArgGlnAlaCysAsnArgGluThrSer-92
SEQ. ID. NO. 36422  96-CysGlyAspGluAlaIleArgCysArgLysPheAsp-107
g915
AMPHI Regions - AMPHI
SEQ. ID. NO. 36423  8-IleValAlaValPheAlaLeuSerAla-16
SEQ. ID. NO. 36424  31-IleSerAspArgSerVal-36
SEQ. ID. NO. 36425  69-ValLysGlnMetPheGlyTyrThrLysLeuProGluGluProLysGlyIleArgValIleTyrValThrAspMetGlyAsnValThrAspTrpThr-100
SEQ. ID. NO. 36426  139-GlnAlaGluLysPhe-143
Antigenic Index - Jameson-Wolf
SEQ. ID. NO. 36427  16-AlaCysArgGlnAlaGluGluAlaProProProLeuProArgGlnIleSerAspArgSerValGlyHisTyrCysSerMetAsnLeuThrGluHis
                    AsnGlyProLysAla-52
SEQ. ID. NO. 36428  56-LeuAsnGlyLysProAspGlnProVal-64
SEQ. ID. NO. 36429  75-TyrThrLysLeuProGluGluProLysGlyIle-85
SEQ. ID. NO. 36430  92-AspMetGlyAsnValThrAspTrpThrAsnProAsnAlaAspThrGluTrpIleAspAlaLysLys-113
SEQ. ID. NO. 36431  125-GlyMetGlyAlaGluAspAlaLeuProPheGlyAsnLysGluGlnAlaGluLysPheAlaLysAspLysGlyGlyLysValValGly-153
SEQ. ID. NO. 36432  155-AspAspMetProAsp-159
Hydrophilic Regions - Hopp-Woods
SEQ. ID. NO. 36433  18-ArgGlnAlaGluGluAlaProProProLeu-27
SEQ. ID. NO. 36434  30-GlnIleSerAspArgSerVal-36
SEQ. ID. NO. 36435  46-GluHisAsnGlyProLys-51
SEQ. ID. NO. 36436  58-GlyLysProAspGln-62
SEQ. ID. NO. 36437  77-LysLeuProGluGluProLysGlyIle-85
SEQ. ID. NO. 36438  103-AsnAlaAspThrGluTrpIleAspAlaLysLys-113
SEQ. ID. NO. 36439  127-GlyAlaGluAspAlaLeu-132
SEQ. ID. NO. 36440  135-GlyAsnLysGluGlnAlaGluLysPheAlaLysAspLysGlyGlyLys-150
SEQ. ID. NO. 36441  155-AspAspMetProAsp-159
g917
AMPHI Regions - AMPHI
SEQ. ID. NO. 36442  6-ProLeuAlaValLeuThrAlaLeuLeuLeu-15
SEQ. ID. NO. 36443  35-GlnAsnValLeuLysIleTyrAsnTrpSerGluTyrValAspProGluThrValAlaAsp-54
SEQ. ID. NO. 36444  99-IleLysAlaGlyAlaTyrGlnLysIleAspLysSer-110
SEQ. ID. NO. 36445  124-ArgLeuMetAspGlyValAsp-130
SEQ. ID. NO. 36446  152-ArgValLysLysAlaLeu-157
SEQ. ID. NO. 36447  188-AspSerAlaAlaGlu-192
SEQ. ID. NO. 36448  206-AsnSerSerAsnThrGluAspIleArgGluAlaThr-217
SEQ. ID. NO. 36449  292-AlaLysAsnValAlaAsnAlaHisLysTyrIleAsnAspPheLeuAsp-307
SEQ. ID. NO. 36450  325-LysProAlaArgAspLeuMetGluAsp-333
Antigenic Index - Jameson-Wolf
SEQ. ID. NO. 36451  18-CysGlyGlySerAspLysProProAlaGluLysProAlaProAlaGluAsnGlnAsnVal-37
SEQ. ID. NO. 36452  44-SerGluTyrValAspProGluThrValAlaAspPheGluLysLysAsnGlyIleLysValThr-64
SEQ. ID. NO. 36453  68-TyrAspSerAspGluThrLeuGluSerLysValLeuThrGlyLysSerGlyTyrAsp-86

TABLE 1-continued

| | |
|---|---|
| SEQ. ID. NO. 36454 | 102-GlyAlaTyrGlnLysIleAspLysSerMetIleProAsnTyrLysHisLeuAsnProGluMetMetArgLeuMetAspGlyValAspProAsp HisGluTyr-135 |
| SEQ. ID. NO. 36455 | 149-AsnThrGluArgValLysLysAlaLeuGlyThrAspLysLeuProAspAsnGln-166 |
| SEQ. ID. NO. 36456 | 171-PheAsnProGluTyr-175 |
| SEQ. ID. NO. 36457 | 179-LeuLysGlnCysGly-183 |
| SEQ. ID. NO. 36458 | 201-LeuGlyLysAsnProAsnSerSerAsnThrGluAspIleArgGluAlaThrAlaLeuLeuLysLysAsnArgProAsnIleLysArgPheThrSer SerGlyPheIle-236 |
| SEQ. ID. NO. 36459 | 238-AspLeuAlaArgGlyAspThr-244 |
| SEQ. ID. NO. 36460 | 255-AsnIleAlaLysArgArgAlaGluGluAlaGlyGlyLysGluLysIleArgValMetMetProLysGluGlyValGly-280 |
| SEQ. ID. NO. 36461 | 287-ValIleProLysAspAlaLysAsnValAlaAsn-297 |
| SEQ. ID. NO. 36462 | 305-PheLeuAspProGluValSerAlaLysAsnGlyAsn-316 |
| SEQ. ID. NO. 36463 | 320-TyrAlaProSerSerLysProAlaArgAspLeuMetGluAspGluPheLysAsnAspAsnThrIlePheProSerGlyGluAspLeuLysAsn-350 |
| SEQ. ID. NO. 36464 | 368-GlnTrpGlnAspValLysAlaGlyLys-376 |
| Hydrophilic Regions - Hopp-Woods | |
| SEQ. ID. NO. 36465 | 19-GlyGlySerAspLysProProAlaGluLysProAlaProAlaGluAsn-34 |
| SEQ. ID. NO. 36466 | 47-ValAspProGluThrValAlaAspPheGluLysLysAsnGlyIle-61 |
| SEQ. ID. NO. 36467 | 68-TyrAspSerAspGluThrLeuGluSerLysValLeuThr-80 |
| SEQ. ID. NO. 36468 | 105-GlnLysIleAspLysSerMet-111 |
| SEQ. ID. NO. 36469 | 121-GluMetMetArgLeuMetAspGlyValAspProAspHisGluTyr-135 |
| SEQ. ID. NO. 36470 | 149-AsnThrGluArgValLysLysAlaLeuGlyThrAspLysLeuProAspAsnGln-166 |
| SEQ. ID. NO. 36471 | 204-AsnProAsnSerSerAsnThrGluAspIleArgGluAlaThrAlaLeuLeuLysLysAsnArgProAsnIleLysArgPheThr-231 |
| SEQ. ID. NO. 36472 | 238-AspLeuAlaArgGlyAspThr-244 |
| SEQ. ID. NO. 36473 | 255-AsnIleAlaLysArgArgAlaGluGluAlaGlyGlyLysGluLysIleArgValMetMetProLysGluGly-278 |
| SEQ. ID. NO. 36474 | 290-LysAspAlaLysAsnValAlaAsn-297 |
| SEQ. ID. NO. 36475 | 305-PheLeuAspProGluValSerAlaLysAsn-314 |
| SEQ. ID. NO. 36476 | 322-ProSerSerLysProAlaArgAspLeuMetGluAspGluPheLysAsnAspAsn-339 |
| SEQ. ID. NO. 36477 | 344-SerGlyGluAspLeuLysAsn-350 |
| SEQ. ID. NO. 36478 | 370-GlnAspValLysAlaGlyLys-376 |
| g919 | |
| AMPHI Regions - AMPHI | |
| SEQ. ID. NO. 36479 | 8-SerAlaLeuTyrGlyIleAlaAlaAlaIleLeu-18 |
| SEQ. ID. NO. 36480 | 24-ArgSerIleGlnThrPheProGln-31 |
| SEQ. ID. NO. 36481 | 37-IleAsnGlyProAspArgProAlaGlyIleProAspProAlaGly-51 |
| SEQ. ID. NO. 36482 | 76-AspPheAlaLysSerLeuGln-82 |
| SEQ. ID. NO. 36483 | 98-GlnAspValCysAlaGlnAlaPheGlnThrProVal-109 |
| SEQ. ID. NO. 36484 | 118-PheGluArgTyrPheThr-123 |
| SEQ. ID. NO. 36485 | 133-LeuAlaGlyThrValThrGlyTyrGlu-142 |
| SEQ. ID. NO. 36486 | 161-GlyIleProAspAspPheIleSerValPro-170 |
| SEQ. ID. NO. 36487 | 176-ArgGlyGlyLysAsnLeuValArgIleArgGln-186 |
| SEQ. ID. NO. 36488 | 191-SerGlyThrIleAspAsnAlaGlyGlyThr-200 |
| SEQ. ID. NO. 36489 | 308-GlnGlyIleLysAlaTyrMetArgGlnAsnProGlnArgLeuAlaGluValLeu-325 |
| SEQ. ID. NO. 36490 | 348-AlaLeuGlyThrProLeuMetGlyGluTyrAlaGlyAlaIle-361 |
| SEQ. ID. NO. 36491 | 382-ArgLysAlaLeuAsnArg-387 |
| Antigenic Index - Jameson-Wolf | |
| SEQ. ID. NO. 36492 | 1-MetLysLysHisLeuLeu-6 |
| SEQ. ID. NO. 36493 | 21-CysGlnSerArgSerIleGln-27 |
| SEQ. ID. NO. 36494 | 30-ProGlnProAspThr-34 |
| SEQ. ID. NO. 36495 | 36-ValIleAsnGlyProAspArgProAlaGlyIleProAspProAlaGly-51 |
| SEQ. ID. NO. 36496 | 76-AspPheAlaLysSerLeuGln-82 |
| SEQ. ID. NO. 36497 | 87-GlyCysAlaAsnLeuLysAsnArgGlnGlyTrpGln-98 |
| SEQ. ID. NO. 36498 | 113-GlnAlaLysArgPhePhe-118 |
| SEQ. ID. NO. 36499 | 121-TyrPheThrProTrp-125 |
| SEQ. ID. NO. 36500 | 143-ProValLeuLysGlyAspGlyArgArgThrGluArgAlaArg-156 |
| SEQ. ID. NO. 36501 | 161-GlyIleProAspAspPheIle-167 |
| SEQ. ID. NO. 36502 | 173-AlaGlyLeuArgGlyGlyLysAsnLeuValArgIleArgGlnThrGlyLysAsnSerGlyThrIleAspAsnAlaGlyGlyThrHis-201 |
| SEQ. ID. NO. 36503 | 215-ThrAlaIleLysGlyArgPheGluGlySerArgPheLeuProTyrHisThrArgAsnGlnIleAsnGlyGlyAlaLeuAspGlyLysAlaPro-245 |
| SEQ. ID. NO. 36504 | 250-AlaGluAspProValGlu-255 |
| SEQ. ID. NO. 36505 | 262-GlnGlySerGlyArgLeuLysThrProSerGlyLysTyrIleArg-276 |
| SEQ. ID. NO. 36506 | 278-GlyTyrAlaAspLysAsnGluHisPro-286 |
| SEQ. ID. NO. 36507 | 293-TyrMetAlaAspLysGlyTyrLeuLysLeuGlyGln-304 |
| SEQ. ID. NO. 36508 | 312-AlaTyrMetArgGlnAsnProGlnArgLeuAlaGlu-323 |
| SEQ. ID. NO. 36509 | 326-GlyGlnAsnProSer-330 |
| SEQ. ID. NO. 36510 | 337-LeuAlaGlySerGlyAsnGluGlyProVal-346 |
| SEQ. ID. NO. 36511 | 359-GlyAlaIleAspArgHisTyr-365 |
| SEQ. ID. NO. 36512 | 379-ProValThrArgLysAlaLeuAsn-386 |
| SEQ. ID. NO. 36513 | 393-AspThrGlySerAlaIleLysGlyAlaValArg-403 |
| SEQ. ID. NO. 36514 | 409-GlyTyrGlyAspGluAlaGlyGluLeuAlaGlyLysGlnLysThrThr-424 |
| SEQ. ID. NO. 36515 | 431-LeuProAsnGlyMetLysProGluTyrArgPro-441 |
| Hydrophilic Regions - Hopp-Woods | |
| SEQ. ID. NO. 36516 | 1-MetLysLysHisLeuLeu-6 |
| SEQ. ID. NO. 36517 | 38-AsnGlyProAspArgProAlaGlyIleProAspProAlaGly-51 |
| SEQ. ID. NO. 36518 | 90-AsnLeuLysAsnArgGlnGlyTrp-97 |
| SEQ. ID. NO. 36519 | 144-ValLeuLysGlyAspGlyArgArgThrGluArgAlaArg-156 |
| SEQ. ID. NO. 36520 | 175-LeuArgGlyGlyLysAsnLeuValArgIleArgGlnThrGlyLysAsnSerGlyThrIleAspAsnAlaGly-198 |
| SEQ. ID. NO. 36521 | 215-ThrAlaIleLysGlyArgPheGluGly-223 |
| SEQ. ID. NO. 36522 | 239-AlaLeuAspGlyLysAla-244 |
| SEQ. ID. NO. 36523 | 250-AlaGluAspProVal-254 |
| SEQ. ID. NO. 36524 | 265-GlyArgLeuLysThrProSer-271 |
| SEQ. ID. NO. 36525 | 279-TyrAlaAspLysAsnGluHis-285 |
| SEQ. ID. NO. 36526 | 317-AsnProGlnArgLeuAlaGlu-323 |

TABLE 1-continued

| | |
|---|---|
| SEQ. ID. NO. 36527 | 337-LeuAlaGlySerGlyAsnGluGlyPro-345 |
| SEQ. ID. NO. 36528 | 380-ValThrArgLysAlaLeuAsn-386 |
| SEQ. ID. NO. 36529 | 393-AspThrGlySerAlaIle-398 |
| SEQ. ID. NO. 36530 | 412-AspGluAlaGlyGluLeuAlaGlyLysGlnLysThr-423 |
| SEQ. ID. NO. 36531 | 434-GlyMetLysProGluTyrArgPro-441 | g920-2
AMPHI Regions - AMPHI

| | |
|---|---|
| SEQ. ID. NO. 36532 | 43-GlyGluPheProGluLeuGluProIleAla-52 |
| SEQ. ID. NO. 36533 | 117-GlyIleLysGluMetProAsp-123 |
| SEQ. ID. NO. 36534 | 135-LysAsnIleValAsnVal-140 |
| SEQ. ID. NO. 36535 | 163-LeuAspAsnProAlaAsn-168 |
| SEQ. ID. NO. 36536 | 190-ThrValThrAlaThrPheAspGlyPheAspThrSerAspArgSerLys-205 |
| SEQ. ID. NO. 36537 | 212-GlnAlaPheSerAspSerThr-218 |

Antigenic Index - Jameson-Wolf

| | |
|---|---|
| SEQ. ID. NO. 36538 | 40-LeuGlyTyrGlyGluPheProGlu-47 |
| SEQ. ID. NO. 36539 | 49-GluProIleAlaLysAspArgLeu-56 |
| SEQ. ID. NO. 36540 | 66-ValThrGluLysGlyLysGluAsnMetIle-75 |
| SEQ. ID. NO. 36541 | 77-ArgGlyThrTyrAsnTyrGlnTyrArgSerAsnArgProValLysAspGlySerTyr-95 |
| SEQ. ID. NO. 36542 | 104-ThrPheTrpSerLysAsnLysAlaGlyTrp-113 |
| SEQ. ID. NO. 36543 | 116-AlaGlyIleLysGluMetProAspAlaSerTyrCysGluGlnThrArgMetPheGlyLysAsnIleValAsnValGlyHisGluSerAlaAspThr-147 |
| SEQ. ID. NO. 36544 | 152-LysProValGlyGlnAsnLeuGlu-159 |
| SEQ. ID. NO. 36545 | 162-ProLeuAspAsnProAla-167 |
| SEQ. ID. NO. 36546 | 173-GluArgPheLysVal-177 |
| SEQ. ID. NO. 36547 | 181-PheArgGlyGluProLeuProAsnAla-189 |
| SEQ. ID. NO. 36548 | 194-ThrPheAspGlyPheAspThrSerAspArgSerLysThrHisLysThrGluAla-211 |
| SEQ. ID. NO. 36549 | 213-AlaPheSerAspSerThrAspAspLysGlyGluValAsp-225 |
| SEQ. ID. NO. 36550 | 237-AsnValGluHisLysThrAspPheProAspGlnSerValCysGlnLysGlnAlaAsnTyrSer-257 |

Hydrophilic Regions - Hopp-Woods

| | |
|---|---|
| SEQ. ID. NO. 36551 | 49-GluProIleAlaLysAspArgLeu-56 |
| SEQ. ID. NO. 36552 | 66-ValThrGluLysGlyLysGluAsnMetIle-75 |
| SEQ. ID. NO. 36553 | 85-ArgSerAsnArgProValLysAspGlySer-94 |
| SEQ. ID. NO. 36554 | 107-SerLysAsnLysAlaGlyTrp-113 |
| SEQ. ID. NO. 36555 | 116-AlaGlyIleLysGluMetProAsp-123 |
| SEQ. ID. NO. 36556 | 128-GluGlnThrArgMetPheGly-134 |
| SEQ. ID. NO. 36557 | 142-HisGluSerAlaAsp-146 |
| SEQ. ID. NO. 36558 | 173-GluArgPheLysVal-177 |
| SEQ. ID. NO. 36559 | 196-AspGlyPheAspThrSerAspArgSerLysThrHisLysThrGluAla-211 |
| SEQ. ID. NO. 36560 | 213-AlaPheSerAspSerThrAspAspLysGlyGluValAsp-225 |
| SEQ. ID. NO. 36561 | 237-AsnValGluHisLysThrAspPheProAsp-246 |
| SEQ. ID. NO. 36562 | 248-SerValCysGlnLys-252 | g921
AMPHI Regions - AMPHI

| | |
|---|---|
| SEQ. ID. NO. 36563 | 12-AlaValLeuSerGlyCysGlnSerIleTyrValProThrLeuThrGluIleProValAsn-31 |
| SEQ. ID. NO. 36564 | 33-IleAsnThrValLysThr-38 |
| SEQ. ID. NO. 36565 | 51-HisTrpAlaAspValAlaLysIleSerAspGlu-61 |
| SEQ. ID. NO. 36566 | 72-GlyLysMetThrLysValGlnAlaAlaGlnTyrLeuAsnAsnPheArgLys-88 |
| SEQ. ID. NO. 36567 | 98-AspSerMetTyrGluIleTyrLeuArg-106 |
| SEQ. ID. NO. 36568 | 126-GluAsnAlaLeuArgGlyTrpGlnGlnArgTrp-136 |

Antigenic Index - Jameson-Wolf

| | |
|---|---|
| SEQ. ID. NO. 36569 | 36-ValLysThrGluAlaProAlaLysGlyPheArg-46 |
| SEQ. ID. NO. 36570 | 56-AlaLysIleSerAspGluAlaThrArg-64 |
| SEQ. ID. NO. 36571 | 72-GlyLysMetThrLys-76 |
| SEQ. ID. NO. 36572 | 84-AsnAsnPheArgLysArgLeuValGlyArgAsnAlaValAspAspSerMet-100 |
| SEQ. ID. NO. 36573 | 107-SerAlaValAspSerGlnArgGlyGluIleAsnThrGluGlnSerLysLeuTyr-124 |
| SEQ. ID. NO. 36574 | 128-AlaLeuArgGlyTrpGlnGlnArgTrpLysAsnMetAspAlaLysProAspAsnProAla-147 |

Hydrophilic Regions - Hopp-Woods

| | |
|---|---|
| SEQ. ID. NO. 36575 | 36-ValLysThrGluAlaProAlaLysGlyPheArg-46 |
| SEQ. ID. NO. 36576 | 56-AlaLysIleSerAspGluAlaThrArg-64 |
| SEQ. ID. NO. 36577 | 86-PheArgLysArgLeuValGly-92 |
| SEQ. ID. NO. 36578 | 94-AsnAlaValAspAspSerMet-100 |
| SEQ. ID. NO. 36579 | 107-SerAlaValAspSerGlnArgGlyGluIleAsnThrGluGlnSerLysLeuTyr-124 |
| SEQ. ID. NO. 36580 | 136-TrpLysAsnMetAspAlaLysProAspAsn-145 | g922
AMPHI Regions - AMPHI

| | |
|---|---|
| SEQ. ID. NO. 36581 | 16-LeuSerAlaCysThrAla-21 |
| SEQ. ID. NO. 36582 | 28-ArgAlaAsnGluAlaGlnAlaPro-35 |
| SEQ. ID. NO. 36583 | 66-ValArgArgPheValAspAsp-72 |
| SEQ. ID. NO. 36584 | 82-AlaGluTrpGlnAspPhePheAspLys-90 |
| SEQ. ID. NO. 36585 | 98-ValLysIleMetHis-102 |
| SEQ. ID. NO. 36586 | 138-AspAspValAlaGln-142 |
| SEQ. ID. NO. 36587 | 166-GlySerPheArgValAlaAspAlaLeu-174 |
| SEQ. ID. NO. 36588 | 190-LysGluLeuValGluLeuLeuLysLeuAla-199 |
| SEQ. ID. NO. 36589 | 216-AlaMetGlyMetPro-220 |
| SEQ. ID. NO. 36590 | 239-HisArgAspIleTrpGlyAsnValGlyAspValAlaAlaSerValAlaAsnTyrMetLysGlnHis-260 |
| SEQ. ID. NO. 36591 | 292-ArgThrValAlaAspAlaLeuLysAlaTyr-300 |
| SEQ. ID. NO. 36592 | 329-TyrLeuGlyLeuAsnAsnPheTyrThr-337 |

Antigenic Index - Jameson-Wolf

| | |
|---|---|
| SEQ. ID. NO. 36593 | 1-MetGluLysArgLysIleLeu-7 |
| SEQ. ID. NO. 36594 | 22-MetGluAlaArgThrProArgAlaAsnGluAlaGlnAlaProArgAlaAspGluMetLysLysGluSerArgProAlaPhe-48 |
| SEQ. ID. NO. 36595 | 55-ValSerAspSerGlyPhe-60 |

TABLE 1-continued

| | |
|---|---|
| SEQ. ID. NO. 36596 | 64-AlaAsnValArgArgPheValAspAspGluValGlyLysGlyAspPheSerGln-81 |
| SEQ. ID. NO. 36597 | 101-MetHisArgProSerThrSerArgPro-109 |
| SEQ. ID. NO. 36598 | 114-ArgThrGlyAsnSerGlyArgAlaLysPheHisGly-125 |
| SEQ. ID. NO. 36599 | 127-ArgArgPheTyrAlaGluAsnArgAlaValIleAspAspValAlaGlnLysTyrGlyVal-146 |
| SEQ. ID. NO. 36600 | 157-IleGluThrAsnTyrGlyLysAsnThrGlySer-167 |
| SEQ. ID. NO. 36601 | 180-AspTyrProArgArgAlaGlyPhePhe-188 |
| SEQ. ID. NO. 36602 | 197-LysLeuAlaLysGluGluGlyGlyAsp-205 |
| SEQ. ID. NO. 36603 | 223-MetProSerSerTyrArgLysTrpAlaValAspTyrAspGlyAspGlyHisArgAspIle-242 |
| SEQ. ID. NO. 36604 | 260-HisGlyTrpArgThrGlyLysMet-268 |
| SEQ. ID. NO. 36605 | 275-AlaProGlyAlaAsp-279 |
| SEQ. ID. NO. 36606 | 284-IleGlyGluLysThrAlaLeu-290 |
| SEQ. ID. NO. 36607 | 304-ProGlyGluThrLeuAlaAspAspGluLysAlaVal-315 |
| SEQ. ID. NO. 36608 | 320-GluThrAlaProGly-324 |
| SEQ. ID. NO. 36609 | 351-ValArgAspIleAlaAsnSerLeuGlyGlyProGlyLeu-363 |
| Hydrophilic Regions - Hopp-Woods | |
| SEQ. ID. NO. 36610 | 1-MetGluLysArgLysIleLeu-7 |
| SEQ. ID. NO. 36611 | 22-MetGluAlaArgThrProArgAlaAsnGluAlaGlnAlaProArgAlaAspGluMetLysLysGluSerArgProAlaPhe-48 |
| SEQ. ID. NO. 36612 | 64-AlaAsnValArgArgPheValAspAspGluValGlyLysGlyAspPheSerGln-81 |
| SEQ. ID. NO. 36613 | 116-GlyAsnSerGlyArgAlaLysPheHisGly-125 |
| SEQ. ID. NO. 36614 | 127-ArgArgPheTyrAlaGluAsnArgAlaValIleAspAspValAlaGln-142 |
| SEQ. ID. NO. 36615 | 160-AsnTyrGlyLysAsnThrGly-166 |
| SEQ. ID. NO. 36616 | 181-TyrProArgArgAlaGlyPhePhe-188 |
| SEQ. ID. NO. 36617 | 197-LysLeuAlaLysGluGluGlyGlyAsp-205 |
| SEQ. ID. NO. 36618 | 234-TyrAspGlyAspGlyHisArgAspIle-242 |
| SEQ. ID. NO. 36619 | 284-IleGlyGluLysThrAlaLeu-290 |
| SEQ. ID. NO. 36620 | 307-ThrLeuAlaAspAspGluLysAlaVal-315 |
| SEQ. ID. NO. 36621 | 351-ValArgAspIleAla-355 |
| g923-2 | |
| AMPHI Regions - AMPHI | |
| SEQ. ID. NO. 36622 | 9-ProMetAlaCysAlaAlaPheLeu-16 |
| SEQ. ID. NO. 36623 | 26-LeuGlyAlaCysTyrAlaIleLeuSerLeuTyrAla-37 |
| SEQ. ID. NO. 36624 | 63-ProAlaLeuPheGlyGlyTrpThrGly-71 |
| Antigenic Index - Jameson-Wolf | |
| SEQ. ID. NO. 36625 | 43-IleAspLysArgArgAlaValArgGlyLysArgArgIleProGluHisArgLeu-60 |
| SEQ. ID. NO. 36626 | 77-ArgMetPheArgHisLysThrAlaLysLysArgPhe-88 |
| Hydrophilic Regions - Hopp-Woods | |
| SEQ. ID. NO. 36627 | 43-IleAspLysArgArgAlaValArgGlyLysArgArgIleProGluHisArgLeu-60 |
| SEQ. ID. NO. 36628 | 77-ArgMetPheArgHisLysThrAlaLysLysArgPhe-88 |
| g925-1 | |
| AMPHI Regions - AMPHI | |
| SEQ. ID. NO. 36629 | 115-LysCysGlyGlnThrAlaGln-121 |
| SEQ. ID. NO. 36630 | 154-PheAspGluLeuGlu-158 |
| Antigenic Index - Jameson-Wolf | |
| SEQ. ID. NO. 36631 | 16-GlyCysGlyLysAspAlaGlyGlyTyrGluGlyTyrTrpArgGluLysSerAspLysLysGluGlyValIleAlaValLysLysLysGlyAsnTyrPhe-48 |
| SEQ. ID. NO. 36632 | 56-ThrGlyLysGluGluSerLeuLeuLeuSerGluLysAspGlyAla-70 |
| SEQ. ID. NO. 36633 | 74-AsnThrGlyIleGly-78 |
| SEQ. ID. NO. 36634 | 80-IleProIleLysLeuSerAspAspGlyLysGluLeuTyrValGluArgArgArgTyrValLysThrAspAlaAlaMetLysAspLysIleIleAlaHisGlnLysLysCysGlyGlnThr-119 |
| SEQ. ID. NO. 36635 | 124-LeuAspAlaArgAsnAlaLeuProSerAsnGlnThrTyrGlnGlnArgGlnAlaAla-142 |
| SEQ. ID. NO. 36636 | 144-GluGlnLeuLysArgArgPheGluAlaGluPheAspGluLeuGluLysGluIleLysCysAsnGlyLysProThr-168 |
| Hydrophilic Regions - Hopp-Woods | |
| SEQ. ID. NO. 36637 | 17-CysGlyLysAspAlaGlyGly-23 |
| SEQ. ID. NO. 36638 | 27-TyrTrpArgGluLysSerAspLysLysGluGlyValIleAlaValLysLysLysGly-45 |
| SEQ. ID. NO. 36639 | 56-ThrGlyLysGluGluSerLeuLeuLeuSerGluLysAspGlyAla-70 |
| SEQ. ID. NO. 36640 | 80-IleProIleLysLeuSerAspAspGlyLysGluLeuTyrValGluArgArgArgTyrValLysThrAspAlaAlaMetLysAspLysIleIleAlaHisGlnLysLysCysGlyGln-118 |
| SEQ. ID. NO. 36641 | 124-LeuAspAlaArgAsnAlaLeu-130 |
| SEQ. ID. NO. 36642 | 136-TyrGlnGlnArgGlnAlaAla-142 |
| SEQ. ID. NO. 36643 | 144-GluGlnLeuLysArgArgPheGluAlaGluPheAspGluLeuGluLysGluIleLysCysAsnGlyLys-166 |
| g926 | |
| AMPHI Regions - AMPHI | |
| SEQ. ID. NO. 36644 | 29-ProSerGluHisIleSerSerPhe-36 |
| SEQ. ID. NO. 36645 | 72-LeuGlySerThrLeuGlyGln-78 |
| SEQ. ID. NO. 36646 | 98-AlaGluGlyThrGluAspLeuSerArgGln-107 |
| Antigenic Index - Jameson-Wolf | |
| SEQ. ID. NO. 36647 | 19-LeuProGlnAsnAsnGluAsnLeuTrpGlnProSerGluHisIleSer-34 |
| SEQ. ID. NO. 36648 | 37-AlaAlaGluGlyArgLeuAlaValLysAlaGluGlyLysGlySerTyrAla-53 |
| SEQ. ID. NO. 36649 | 70-ThrProLeuGlySer-74 |
| SEQ. ID. NO. 36650 | 79-LeuCysGlnAspArgAspGlyAlaLeu-87 |
| SEQ. ID. NO. 36651 | 89-ValAspGlyLysGlyAsnValTyr-96 |
| SEQ. ID. NO. 36652 | 98-AlaGluGlyThrGluAspLeuSerArgGln-107 |
| SEQ. ID. NO. 36653 | 123-GluGlyArgArgValAlaGlyAlaProTyrArgIleArgSerAspGlyIleLeu-140 |
| SEQ. ID. NO. 36654 | 143-TyrGlyTrpThrIleGlyGlnAsnCysArgGlnTrpGly-155 |
| SEQ. ID. NO. 36655 | 157-SerProAsnValAlaThrGlu-163 |
| Hydrophilic Regions - Hopp-Woods | |
| SEQ. ID. NO. 36656 | 37-AlaAlaGluGlyArgLeuAlaValLysAlaGluGlyLysGlySer-51 |
| SEQ. ID. NO. 36657 | 80-CysGlnAspArgAspGlyAlaLeu-87 |
| SEQ. ID. NO. 36658 | 89-ValAspGlyLysGly-93 |
| SEQ. ID. NO. 36659 | 99-GluGlyThrGluAspLeuSerArg-106 |

TABLE 1-continued

```
SEQ. ID. NO. 36660    123-GluGlyArgArgValAla-128
SEQ. ID. NO. 36661    132-TyrArgIleArgSerAspGlyIleLeu-140
g927
AMPHI Regions - AMPHI
SEQ. ID. NO. 36662    13-LeuLeuThrAlaCys-17
SEQ. ID. NO. 36663    48-SerTyrAspValThrArgTyrPheTyrLysGlu-58
SEQ. ID. NO. 36664    120-LysGlyTrpGlnGlnAlaLeuPro-127
SEQ. ID. NO. 36665    145-AsnProLysGlnIleArgAspTrpAsnAspLeuAlaLysAspGly-159
SEQ. ID. NO. 36666    195-LysLeuValAlaSerIleLeu-201
Antigenic Index - Jameson-Wolf
SEQ. ID. NO. 36667    17-CysSerProAlaAlaAspSerAsnHisProSerGlyGlnAsnAlaProAlaAsnThrGluSerAspGlyLysAsnIle-42
SEQ. ID. NO. 36668    65-GlyThrTyrGlnSerGluHisProGlyThrSer-75
SEQ. ID. NO. 36669    81-SerHisGlyGlyPheSer-86
SEQ. ID. NO. 36670    104-AsnGlnSerSerAspIleAspLeuLeuGluLysXxxGlyLeuVal-118
SEQ. ID. NO. 36671    126-LeuProAspHisAlaAlaProTyrThr-134
SEQ. ID. NO. 36672    142-ArgLysAsnAsnProLysGlnIleArgAspTrpAsnAspLeuAlaLysAspGlyVal-160
SEQ. ID. NO. 36673    165-AlaLysThrSerGlyAsnGlyArg-172
SEQ. ID. NO. 36674    183-LeuLysAlaAsnAsnGlyAsnGluGlnGluAlaGlnLys-195
SEQ. ID. NO. 36675    201-LeuLysAsnThrProValPheGluAsnGlyGlyArgXxxProProProProSerHisAsnAlaThrSer-224
SEQ. ID. NO. 36676    229-SerLeuLeuLysThrLysProThrThrSerAlaLysAsn-241
Hydrophilic Regions - Hopp-Woods
SEQ. ID. NO. 36677    19-ProAlaAlaAspSerAsnHisProSer-27
SEQ. ID. NO. 36678    33-AlaAsnThrGluSerAspGlyLysAsn-41
SEQ. ID. NO. 36679    68-GlnSerGluHisProGly-73
SEQ. ID. NO. 36680    105-GlnSerSerAspIleAspLeuLeuGluLysXxxGlyLeuVal-118
SEQ. ID. NO. 36681    142-ArgLysAsnAsnProLysGlnIleArgAspTrpAsnAspLeuAlaLysAspGlyVal-160
SEQ. ID. NO. 36682    167-ThrSerGlyAsnGly-171
SEQ. ID. NO. 36683    185-AlaAsnAsnGlyAsnGluGlnGluAlaGlnLys-195
SEQ. ID. NO. 36684    209-AsnGlyGlyArgXxxProProPro-216
SEQ. ID. NO. 36685    231-LeuLysThrLysProThrThrSerAlaLysAsn-241
g929
AMPHI Regions - AMPHI
SEQ. ID. NO. 36686    25-ValProAspGlyValLys-30
SEQ. ID. NO. 36687    34-TrpThrLeuLeuAlaMetPheValGlyValIleAlaAlaIleIleGly-49
SEQ. ID. NO. 36688    53-ProLeuGlyAlaLeuSer-58
SEQ. ID. NO. 36689    76-GlyAlaAlaMetSerAspAlaLeuSerAlaPhe-86
SEQ. ID. NO. 36690    155-HisProIleMetGlnSerIleAlaGlySerTyrGlySerAsnProAlaLys-171
SEQ. ID. NO. 36691    180-TyrLeuAlaLeuVal-184
SEQ. ID. NO. 36692    187-HisSerAsnProIle-191
SEQ. ID. NO. 36693    204-ProLeuIleValAsnLeuIleAlaGluAsnLeuGly-215
SEQ. ID. NO. 36694    233-GlyValIleAlaPhePhe-238
SEQ. ID. NO. 36695    265-ArgLeuSerGluMetGlyLys-271
SEQ. ID. NO. 36696    280-AlaValIlePheGlyIle-285
SEQ. ID. NO. 36697    355-LeuGlyLeuIleLysTrpPheSerGlyValLeuAlaGluSerValGlyGlyLeu-372
SEQ. ID. NO. 36698    398-ThrAlaHisIleThrAlaMetPheGlyAlaPheLeuAla-410
SEQ. ID. NO. 36699    452-TyrThrThrMetGlyGluTrpTrp-459
SEQ. ID. NO. 36700    469-AsnPheLeuIlePheSerValIleGlySerIleTrpTrpLysValLeuGlyTyr-486
Antigenic Index - Jameson-Wolf
SEQ. ID. NO. 36701    25-ValProAspGlyValLysProGln-32
SEQ. ID. NO. 36702    71-ThrAlaAspLysProGlyAlaAlaMet-79
SEQ. ID. NO. 36703    122-GlyArgLysThrLeuGlyIle-128
SEQ. ID. NO. 36704    143-ThrProSerAsnThrAlaArgGlyGlyGly-152
SEQ. ID. NO. 36705    163-GlySerTyrGlySerAsnProAlaLysGlyThrGluGlyLysMetGlyLys-179
SEQ. ID. NO. 36706    187-HisSerAsnProIleSer-192
SEQ. ID. NO. 36707    213-AsnLeuGlySerSerPhe-218
SEQ. ID. NO. 36708    248-TyrProProGluIleLysGluThrProAsn-257
SEQ. ID. NO. 36709    261-PheAlaLysAspArgLeuSerGluMetGlyLysMetSerAlaAspGluIle-277
SEQ. ID. NO. 36710    328-AspValLeuLysGluLysSerAlaTrp-336
Hydrophilic Regions - Hopp-Woods
SEQ. ID. NO. 36711    71-ThrAlaAspLysProGlyAlaAlaMet-79
SEQ. ID. NO. 36712    146-AsnThrAlaArgGly-150
SEQ. ID. NO. 36713    168-AsnProAlaLysGlyThrGluGlyLysMetGlyLys-179
SEQ. ID. NO. 36714    250-ProGluIleLysGluThrProAsn-257
SEQ. ID. NO. 36715    261-PheAlaLysAspArgLeuSerGluMetGlyLysMetSerAlaAspGluIle-277
SEQ. ID. NO. 36716    328-AspValLeuLysGluLysSerAlaTrp-336
g930-1
AMPHI Regions - AMPHI
SEQ. ID. NO. 36717    6-AlaGlyAspIleAsnGlnIleMetSerLeu-15
SEQ. ID. NO. 36718    30-IleLeuAlaAlaPro-34
SEQ. ID. NO. 36719    48-ProGlyTyrLeuArgSerIleArgIle-56
SEQ. ID. NO. 36720    82-AspLeuLeuAsnLeuArgAsp-88
SEQ. ID. NO. 36721    96-LeuLysCysLeuPro-100
SEQ. ID. NO. 36722    163-SerAspMetPheTyr-167
SEQ. ID. NO. 36723    171-GlyArgSerIleGlyGly-176
SEQ. ID. NO. 36724    216-ArgTyrHisGlnAlaValSerGlyLeuSerGluValTyrAsp-229
SEQ. ID. NO. 36725    283-TrpLeuAlaGluLeuSerHis-289
SEQ. ID. NO. 36726    308-ThrGlyMetLysAspAlaLeuArgAlaProGluGluAlaPheGlyGluGly-324
SEQ. ID. NO. 36727    355-HisAlaGlnTrpAsnLys-360
SEQ. ID. NO. 36728    457-LeuLysLysProGluTyrPhe-463
```

TABLE 1-continued

Antigenic Index - Jameson-Wolf
SEQ. ID. NO. 36729  1-GlyLysCysLeuHisAlaGlyAsp-8
SEQ. ID. NO. 36730  34-ProGlnAspLeuAsnSerGlyLysLeu-42
SEQ. ID. NO. 36731  54-IleArgIleAspArgSerAsnAspAspGlnThrHisAlaGlyArgIleAla-70
SEQ. ID. NO. 36732  74-AsnLysPheProThrArgSerAsnAspLeuLeuAsn-85
SEQ. ID. NO. 36733  87-ArgAspLeuGluGlnGlyLeuGluAsn-95
SEQ. ID. NO. 36734  102-AlaGluAlaAspLeu-106
SEQ. ID. NO. 36735  110-ProValGluArgGluProAsnGlnSerAsp-119
SEQ. ID. NO. 36736  136-GlyMetAspAsnSerGlySerGluAlaThrGlyLysTyrGlnGly-150
SEQ. ID. NO. 36737  156-AlaAspAsnProPheGlyLeu-162
SEQ. ID. NO. 36738  170-TyrGlyArgSerIleGlyGlyThrProAspGluGluAsnPheAspGlyHisArgLysGluGlyGlySerAsn-193
SEQ. ID. NO. 36739  212-HisAsnGlyTyrArg-216
SEQ. ID. NO. 36740  226-GluValTyrAspTyrAsnGlyLysSerTyrAsnThrAspPheGlyPhe-241
SEQ. ID. NO. 36741  245-LeuTyrArgAspAlaLysArgLysThrTyrLeu-255
SEQ. ID. NO. 36742  260-TrpThrArgGluThrLysSerTyrIleAspAspAlaGluLeuThrValGlnArgArgLysThrThr-281
SEQ. ID. NO. 36743  287-LeuSerHisLysGlyTyrIleGlyArgSerThrAlaAspPheLysLeuLysTyrLysHisGlyThrGlyMetLysAspAlaLeuArgAlaPro
                    GluGluAlaPheGlyGluGlyThrSerArg-327
SEQ. ID. NO. 36744  334-SerAlaAspValAsnThrPro-340
SEQ. ID. NO. 36745  357-GlnTrpAsnLysThrProLeuThrSerGlnAspLysLeuAla-370
SEQ. ID. NO. 36746  375-HisThrValArgGlyPheAspGlyGluMetSerLeuProAlaGluArgGlyTrpTyrTrpArgAsnAspLeuSerTrpGlnPheLysProGlyHis-406
SEQ. ID. NO. 36747  418-SerGlyGlnSerAlaLys-423
SEQ. ID. NO. 36748  455-ArgAlaLeuLysLysProGluTyrPheGlnThrLysLysTrpValThr-470
Hydrophilic Regions - Hopp-Woods
SEQ. ID. NO. 36749  35-GlnAspLeuAsnSerGlyLys-41
SEQ. ID. NO. 36750  54-IleArgIleAspArgSerAsnAspAspGlnThrHisAla-66
SEQ. ID. NO. 36751  76-PheProThrArgSerAsnAsp-82
SEQ. ID. NO. 36752  87-ArgAspLeuGluGlnGlyLeuGluAsn-95
SEQ. ID. NO. 36753  102-AlaGluAlaAspLeu-106
SEQ. ID. NO. 36754  110-ProValGluArgGluProAsnGlnSer-118
SEQ. ID. NO. 36755  137-MetAspAsnSerGlySerGluAlaThrGlyLysTyr-148
SEQ. ID. NO. 36756  174-IleGlyGlyThrProAspGluGluAsnPheAspGlyHisArgLysGluGlyGlySer-192
SEQ. ID. NO. 36757  228-TyrAspTyrAsnGly-232
SEQ. ID. NO. 36758  245-LeuTyrArgAspAlaLysArgLysThrTyrLeu-255
SEQ. ID. NO. 36759  260-TrpThrArgGluThrLysSerTyrIleAspAspAlaGluLeuThrValGlnArgArgLysThrThr-281
SEQ. ID. NO. 36760  296-SerThrAlaAspPheLysLeuLysTyrLysHis-306
SEQ. ID. NO. 36761  308-ThrGlyMetLysAspAlaLeuArgAlaProGluGluAlaPheGly-322
SEQ. ID. NO. 36762  362-ProLeuThrSerGlnAspLysLeuAla-370
SEQ. ID. NO. 36763  378-ArgGlyPheAspGlyGluMet-384
SEQ. ID. NO. 36764  455-ArgAlaLeuLysLysProGluTyrPheGln-464
g931
AMPHI Regions - AMPHI
SEQ. ID. NO. 36765  43-LysAlaSerLysThrValAlaAsnPheValArgTyrAlaArgLys-57
SEQ. ID. NO. 36766  67-ArgValIleGlyGly-71
SEQ. ID. NO. 36767  81-GluAspLeuValGlnLysAlaThrAspLysAla-91
SEQ. ID. NO. 36768  93-AlaAsnGluSerGlyAsnGlyLeuLysAsnThrValGly-105
SEQ. ID. NO. 36769  142-ThrValPheGlyArgValGluSerGlyMetAspThrValSerLysIleAlaArgValLysThrAlaThrArgGlyPhe-167
Antigenic Index - Jameson-Wolf
SEQ. ID. NO. 36770  1-MetLysProLysPhe-5
SEQ. ID. NO. 36771  30-ThrAspMetGlyAsn-34
SEQ. ID. NO. 36772  38-ValLeuAspGluSerLysAlaSerLysThr-47
SEQ. ID. NO. 36773  54-TyrAlaArgLysGlyPheTyrAspAsn-62
SEQ. ID. NO. 36774  75-GlnGlyAspGlyLeuThrGluAspLeuValGlnLysAlaThrAspLysAlaValAlaAsnGluSerGlyAsnGlyLeuLysAsnThrVal-104
SEQ. ID. NO. 36775  113-AlaAlaProAspSerAla-118
SEQ. ID. NO. 36776  127-AlaAspAsnGlySerLeuAspTyrLysAsnGlyGlnTyrGly-140
SEQ. ID. NO. 36777  145-GlyArgValGluSerGlyMetAspThrValSerLysIleAlaArgValLysThrAlaThrArgGlyPhe-167
SEQ. ID. NO. 36778  176-ValLysIleArgArg-180
Hydrophilic Regions - Hopp-Woods
SEQ. ID. NO. 36779  1-MetLysProLysPhe-5
SEQ. ID. NO. 36780  30-ThrAspMetGlyAsn-34
SEQ. ID. NO. 36781  38-ValLeuAspGluSerLysAlaSerLysThr-47
SEQ. ID. NO. 36782  78-GlyLeuThrGluAspLeuValGlnLysAlaThrAspLysAlaValAlaAsnGluSerGlyAsnGlyLeu-100
SEQ. ID. NO. 36783  113-AlaAlaProAspSerAla-118
SEQ. ID. NO. 36784  130-GlySerLeuAspTyrLysAsn-136
SEQ. ID. NO. 36785  145-GlyArgValGluSerGlyMetAspThrValSerLysIleAlaArgValLysThrAlaThr-164
SEQ. ID. NO. 36786  176-ValLysIleArgArg-180
g933
AMPHI Regions - AMPHI
SEQ. ID. NO. 36787  26-ProAsnIleProAlaLeuPheProLysHisProPheAspProPheGluAsnIleAsnAsnSerLysLys-48
SEQ. ID. NO. 36788  63-GlyPheAlaArgGly-67
SEQ. ID. NO. 36789  78-GluLysProLeuArgGlnTyrPheLysAspCysValAsnThr-91
SEQ. ID. NO. 36790  101-IleSerSerPheGlyAsn-106
SEQ. ID. NO. 36791  135-ValGlyAsnTyrIleGluTrpLeu-142
SEQ. ID. NO. 36792  145-ThrLeuAsnLysLeuThrGlyTrpGlnGluHisLeuTyrAlaGlyLeuAspProPheHisTyrIleGluVal-168
SEQ. ID. NO. 36793  264-AlaLeuAspAsnLeuLysHisLeuAspGlyHisGlnIleValLysValAsn-280
SEQ. ID. NO. 36794  309-GlyPhePheThrLys-313
SEQ. ID. NO. 36795  356-TrpLeuArgValIleAspGlyHisSerAsn-365
SEQ. ID. NO. 36796  374-ProValGluGlyTyrArgLysGly-381
SEQ. ID. NO. 36797  431-AlaGlyValTyrAlaThrTrpHis-438
SEQ. ID. NO. 36798  447-AlaTyrValAspSerTrpMetGlnTyrGln-456
SEQ. ID. NO. 36799  474-LysGlyIleThrAlaSer-479

TABLE 1-continued

| | |
|---|---|
| SEQ. ID. NO. 36800 | 483-GlyTyrAsnAlaLeuLeuAla-489 |
| SEQ. ID. NO. 36801 | 555-GlnProPheValAlaVal-560 |
| SEQ. ID. NO. 36802 | 606-PheAsnArgGlnThrSer-611 |
| Antigenic Index - Jameson-Wolf | |
| SEQ. ID. NO. 36803 | 1-LysLysLeuArgAspArgAsnSerGluTyrTrpLysGluGluThrTyrHisIleLysSerAsnGlyArgThrTyrPro-26 |
| SEQ. ID. NO. 36804 | 33-ProLysHisProPheAspProPheGluAsnIleAsnAsnSerLysLysIleSerPheTyrAspLysGluTyrThrGluAspTyr-60 |
| SEQ. ID. NO. 36805 | 68-PheGlyValGluLysArgAsnGlyGluGluGluLysProLeuArg-82 |
| SEQ. ID. NO. 36806 | 88-CysValAsnThrGluAsnSerAsnAsnAspAsnCysLysIleSerSer-103 |
| SEQ. ID. NO. 36807 | 112-IleLysSerAspIle-116 |
| SEQ. ID. NO. 36808 | 122-GlnIleLysAsnSerHisIleAsnSerGluIle-132 |
| SEQ. ID. NO. 36809 | 144-ProThrLeuAsnLysLeuThrGlyTrpGlnGlu-154 |
| SEQ. ID. NO. 36810 | 167-GluValThrAspAsnSerHis-173 |
| SEQ. ID. NO. 36811 | 189-SerLeuTrpLysProArgTrpAsnSerAsnIle-199 |
| SEQ. ID. NO. 36812 | 205-LysAsnAlaGluIleArgPheAsnThrLysAsnGluSerLeuLeuValLysGluAspTyrAlaGlyGlyAlaArgPhe-230 |
| SEQ. ID. NO. 36813 | 234-TyrAspLeuLysAspLysValProGlu-242 |
| SEQ. ID. NO. 36814 | 248-PheGluLysAsnIleThrGlyThrSer-256 |
| SEQ. ID. NO. 36815 | 263-LysAlaLeuAspAsnLeuLysHisLeuAspGlyHisGlnIleValLysValAsnAspThrAlaAspLysAspAlaPheArgLeuSerSerLysTyrArgLys-296 |
| SEQ. ID. NO. 36816 | 303-LeuGlnGlnArgProGluGlyPhe-310 |
| SEQ. ID. NO. 36817 | 313-LysValGlnGluArgAspAspIle-320 |
| SEQ. ID. NO. 36818 | 337-ArgLeuAsnAspLysAsnSerAspIlePheAspArgThrLeuProArgLysGlyLeu-355 |
| SEQ. ID. NO. 36819 | 360-IleAspGlyHisSerAsnGlnTrpValGlnGlyLysThrAlaProValGluGlyTyrArgLysGlyVal-382 |
| SEQ. ID. NO. 36820 | 392-GlnAsnGluSerAsnGlnLeu-398 |
| SEQ. ID. NO. 36821 | 403-MetGlyGlyGlnAlaGluGlnArgSerThrPheArgAsnProAspThrAspAsnLeuThr-422 |
| SEQ. ID. NO. 36822 | 424-GlyAsnValLysGly-428 |
| SEQ. ID. NO. 36823 | 440-LeuGlnAspLysGlnThrGlyAlaTyr-448 |
| SEQ. ID. NO. 36824 | 456-GlnArgPheArgHisArgIleAsnThrGluTyrAlaThrGluArgPheThrSerLysGlyIle-476 |
| SEQ. ID. NO. 36825 | 491-HisPheThrLysLysGlyAsnSerLeu-499 |
| SEQ. ID. NO. 36826 | 514-ValAsnGlyLysPheSerAspSerGluAsnAla-524 |
| SEQ. ID. NO. 36827 | 529-LeuGlySerArgGlnLeuGlnSerArgValGlyVal-540 |
| SEQ. ID. NO. 36828 | 567-LysProPheGlyValGluIleAspGlyAspArgArgValIleAsnAsnLysThrValIleGluThr-588 |
| SEQ. ID. NO. 36829 | 594-AlaLysIleLysSer-598 |
| SEQ. ID. NO. 36830 | 605-SerPheAsnArgGlnThrSerLysHisHisHisAlaLys-617 |
| Hydrophilic Regions - Hopp-Woods | |
| SEQ. ID. NO. 36831 | 1-LysLysLeuArgAspArgAsnSerGluTyrTrpLysGluGluThrTyrHis-17 |
| SEQ. ID. NO. 36832 | 20-SerAsnGlyArgThr-24 |
| SEQ. ID. NO. 36833 | 35-HisProPheAspPro-39 |
| SEQ. ID. NO. 36834 | 44-AsnAsnSerLysLysIleSerPheTyrAspLysGluTyrThrGlu-58 |
| SEQ. ID. NO. 36835 | 68-PheGlyValGluLysArgAsnGlyGluGluGluLysProLeu-81 |
| SEQ. ID. NO. 36836 | 88-CysValAsnThrGluAsnSerAsnAsnAspAsnCysLys-100 |
| SEQ. ID. NO. 36837 | 205-LysAsnAlaGluIleArgPheAsnThrLysAsnGluSerLeuLeuValLysGluAspTyrAlaGly-226 |
| SEQ. ID. NO. 36838 | 234-TyrAspLeuLysAspLysValProGlu-242 |
| SEQ. ID. NO. 36839 | 250-LysAsnIleThrGly-254 |
| SEQ. ID. NO. 36840 | 263-LysAlaLeuAspAsnLeuLysHisLeuAsp-272 |
| SEQ. ID. NO. 36841 | 278-LysValAsnAspThrAlaAspLysAspAlaPheArgLeuSerSerLysTyrArgLys-296 |
| SEQ. ID. NO. 36842 | 304-GlnGlnArgProGluGlyPhe-310 |
| SEQ. ID. NO. 36843 | 314-ValGlnGluArgAspAspIle-320 |
| SEQ. ID. NO. 36844 | 338-LeuAsnAspLysAsnSerAspIlePheAsp-347 |
| SEQ. ID. NO. 36845 | 376-GluGlyTyrArgLysGlyVal-382 |
| SEQ. ID. NO. 36846 | 393-AsnGluSerAsnGln-397 |
| SEQ. ID. NO. 36847 | 406-GlnAlaGluGlnArgSerThrPheArgAsnProAspThrAspAsnLeuThr-422 |
| SEQ. ID. NO. 36848 | 440-LeuGlnAspLysGlnThr-445 |
| SEQ. ID. NO. 36849 | 456-GlnArgPheArgHisArgIleAsnThr-464 |
| SEQ. ID. NO. 36850 | 491-HisPheThrLysLysGlyAsnSer-498 |
| SEQ. ID. NO. 36851 | 517-LysPheSerAspSerGluAsnAla-524 |
| SEQ. ID. NO. 36852 | 532-ArgGlnLeuGlnSer-536 |
| SEQ. ID. NO. 36853 | 569-PheGlyValGluIleAspGlyAspArgArgValIleAsn-581 |
| SEQ. ID. NO. 36854 | 594-AlaLysIleLysSer-598 |
| SEQ. ID. NO. 36855 | 606-PheAsnArgGlnThrSerLysHisHisHisAlaLys-617 |
| g933 | |
| AMPHI Regions - AMPHI | |
| SEQ. ID. NO. 36856 | 26-ProAsnIleProAlaLeuPheProLysHisProPheAspProPheGluAsnIleAsnAsnSerLysLys-48 |
| SEQ. ID. NO. 36857 | 63-GlyPheAlaArgGly-67 |
| SEQ. ID. NO. 36858 | 78-GluLysProLeuArgGlnTyrPheLysAspCysValAsnThr-91 |
| SEQ. ID. NO. 36859 | 101-IleSerSerPheGlyAsn-106 |
| SEQ. ID. NO. 36860 | 135-ValGlyAsnTyrIleGluTrpLeu-142 |
| SEQ. ID. NO. 36861 | 145-ThrLeuAsnLysLeuThrGlyTrpGlnGluHisLeuTyrAlaGlyLeuAspProPheHisTyrIleGluVal-168 |
| SEQ. ID. NO. 36862 | 264-AlaLeuAspAsnLeuLysHisLeuAspGlyHisGlnIleValLysValAsn-280 |
| SEQ. ID. NO. 36863 | 309-GlyPhePheThrLys-313 |
| SEQ. ID. NO. 36864 | 356-TrpLeuArgValIleAspGlyHisSerAsn-365 |
| SEQ. ID. NO. 36865 | 374-ProValGluGlyTyrArgLysGly-381 |
| SEQ. ID. NO. 36866 | 431-AlaGlyValTyrAlaThrTrpHis-438 |
| SEQ. ID. NO. 36867 | 447-AlaTyrValAspSerTrpMetGlnTyrGln-456 |
| SEQ. ID. NO. 36868 | 474-LysGlyIleThrAlaSer-479 |
| SEQ. ID. NO. 36869 | 483-GlyTyrAsnAlaLeuLeuAla-489 |
| SEQ. ID. NO. 36870 | 555-GlnProPheValAlaVal-560 |
| SEQ. ID. NO. 36871 | 606-PheAsnArgGlnThrSer-611 |
| Antigenic Index - Jameson-Wolf | |
| SEQ. ID. NO. 36872 | 1-LysLysLeuArgAspArgAsnSerGluTyrTrpLysGluGluThrTyrHisIleLysSerAsnGlyArgThrTyrPro-26 |
| SEQ. ID. NO. 36873 | 33-ProLysHisProPheAspProPheGluAsnIleAsnAsnSerLysLysIleSerPheTyrAspLysGluTyrThrGluAspTyr-60 |

TABLE 1-continued

| | |
|---|---|
| SEQ. ID. NO. 36874 | 68-PheGlyValGluLysArgAsnGlyGluGluGluLysProLeuArg-82 |
| SEQ. ID. NO. 36875 | 88-CysValAsnThrGluAsnSerAsnAsnAspAsnCysLysIleSerSer-103 |
| SEQ. ID. NO. 36876 | 112-IleLysSerAspIle-116 |
| SEQ. ID. NO. 36877 | 122-GlnIleLysAsnSerHisIleAsnSerGluIle-132 |
| SEQ. ID. NO. 36878 | 144-ProThrLeuAsnLysLeuThrGlyTrpGlnGlu-154 |
| SEQ. ID. NO. 36879 | 167-GluValThrAspAsnSerHis-173 |
| SEQ. ID. NO. 36880 | 189-SerLeuTrpLysProArgTrpAsnSerAsnIle-199 |
| SEQ. ID. NO. 36881 | 205-LysAsnAlaGluIleArgPheAsnThrLysAsnGluSerLeuLeuValLysGluAspTyrAlaGlyGlyAlaArgPhe-230 |
| SEQ. ID. NO. 36882 | 234-TyrAspLeuLysAspLysValProGlu-242 |
| SEQ. ID. NO. 36883 | 248-PheGluLysAsnIleThrGlyThrSer-256 |
| SEQ. ID. NO. 36884 | 263-LysAlaLeuAspAsnLeuLysHisLeuAspGlyHisGlnIleValLysValAsnAspThrAlaAspLysAspAlaPheArgLeuSerSerLysTyrArgLys-296 |
| SEQ. ID. NO. 36885 | 303-LeuGlnGlnArgProGluGlyPhe-310 |
| SEQ. ID. NO. 36886 | 313-LysValGlnGluArgAspAspIle-320 |
| SEQ. ID. NO. 36887 | 337-ArgLeuAsnAspLysAsnSerAspIlePheArgThrLeuProArgLysGlyLeu-355 |
| SEQ. ID. NO. 36888 | 360-IleAspGlyHisSerAsnGlnTrpValGlnGlyLysThrAlaProValGluGlyTyrArgLysGlyVal-382 |
| SEQ. ID. NO. 36889 | 392-GlnAsnGluSerAsnGlnLeu-398 |
| SEQ. ID. NO. 36890 | 403-MetGlyGlyGlnAlaGluGlnArgSerThrPheArgAsnProAspThrAspAsnLeuThr-422 |
| SEQ. ID. NO. 36891 | 424-GlyAsnValLysGly-428 |
| SEQ. ID. NO. 36892 | 440-LeuGlnAspLysGlnThrGlyAlaTyr-448 |
| SEQ. ID. NO. 36893 | 456-GlnArgPheArgHisArgIleAsnThrGluTyrAlaThrGluArgPheThrSerLysGlyIle-476 |
| SEQ. ID. NO. 36894 | 491-HisPheThrLysLysGlyAsnSerLeu-499 |
| SEQ. ID. NO. 36895 | 514-ValAsnGlyLysPheSerAspSerGluAsnAla-524 |
| SEQ. ID. NO. 36896 | 529-LeuGlySerArgGlnLeuGlnSerArgValGlyVal-540 |
| SEQ. ID. NO. 36897 | 567-LysProPheGlyValGluIleAspGlyAspArgArgValIleAsnAsnLysThrValIleGluThr-588 |
| SEQ. ID. NO. 36898 | 594-AlaLysIleLysSer-598 |
| SEQ. ID. NO. 36899 | 605-SerPheAsnArgGlnThrSerLysHisHisHisAlaLys-617 |
| Hydrophilic Regions - Hopp-Woods | |
| SEQ. ID. NO. 36900 | 1-LysLysLeuArgAspArgAsnSerGluTyrTrpLysGluGluThrTyrHis-17 |
| SEQ. ID. NO. 36901 | 20-SerAsnGlyArgThr-24 |
| SEQ. ID. NO. 36902 | 35-HisProPheAspPro-39 |
| SEQ. ID. NO. 36903 | 44-AsnAsnSerLysLysIleSerPheTyrAspLysGluTyrThrGlu-58 |
| SEQ. ID. NO. 36904 | 68-PheGlyValGluLysArgAsnGlyGluGluGluLysProLeu-81 |
| SEQ. ID. NO. 36905 | 88-CysValAsnThrGluAsnSerAsnAsnAspAsnCysLys-100 |
| SEQ. ID. NO. 36906 | 205-LysAsnAlaGluIleArgPheAsnThrLysAsnGluSerLeuLeuValLysGluAspTyrAlaGly-226 |
| SEQ. ID. NO. 36907 | 234-TyrAspLeuLysAspLysValProGlu-242 |
| SEQ. ID. NO. 36908 | 250-LysAsnIleThrGly-254 |
| SEQ. ID. NO. 36909 | 263-LysAlaLeuAspAsnLeuLysHisLeuAsp-272 |
| SEQ. ID. NO. 36910 | 278-LysValAsnAspThrAlaAspLysAspAlaPheArgLeuSerSerLysTyrArgLys-296 |
| SEQ. ID. NO. 36911 | 304-GlnGlnArgProGluGlyPhe-310 |
| SEQ. ID. NO. 36912 | 314-ValGlnGluArgAspAspIle-320 |
| SEQ. ID. NO. 36913 | 338-LeuAsnAspLysAsnSerAspIlePheAsp-347 |
| SEQ. ID. NO. 36914 | 376-GluGlyTyrArgLysGlyVal-382 |
| SEQ. ID. NO. 36915 | 393-AsnGluSerAsnGln-397 |
| SEQ. ID. NO. 36916 | 406-GlnAlaGluGlnArgSerThrPheArgAsnProAspThrAspAsnLeuThr-422 |
| SEQ. ID. NO. 36917 | 440-LeuGlnAspLysGlnThr-445 |
| SEQ. ID. NO. 36918 | 456-GlnArgPheArgHisArgIleAsnThr-464 |
| SEQ. ID. NO. 36919 | 491-HisPheThrLysLysGlyAsnSer-498 |
| SEQ. ID. NO. 36920 | 517-LysPheSerAspSerGluAsnAla-524 |
| SEQ. ID. NO. 36921 | 532-ArgGlnLeuGlnSer-536 |
| SEQ. ID. NO. 36922 | 569-PheGlyValGluIleAspGlyAspArgArgValIleAsn-581 |
| SEQ. ID. NO. 36923 | 594-AlaLysIleLysSer-598 |
| SEQ. ID. NO. 36924 | 606-PheAsnArgGlnThrSerLysHisHisHisAlaLys-617 |
| g936-1 | |
| AMPHI Regions - AMPHI | |
| SEQ. ID. NO. 36925 | 10-ThrLeuIleAlaAla-14 |
| SEQ. ID. NO. 36926 | 19-AlaLeuGlyGlyCysPheSerAlaVal-27 |
| SEQ. ID. NO. 36927 | 100-GlnPheValGlyGlnIle-105 |
| SEQ. ID. NO. 36928 | 112-AlaGluGlyValTyrAsnTyrIleThrValAlaSerLeuProArgThrAlaGlyAspIleAlaGlyAsp-134 |
| Antigenic Index - Jameson-Wolf | |
| SEQ. ID. NO. 36929 | 1-MetLysProLysProHisThrVal-8 |
| SEQ. ID. NO. 36930 | 37-SerValIleAspArgArgThrThrGlyAlaGlnThrAspAspAsnValMet-53 |
| SEQ. ID. NO. 36931 | 56-ArgIleGluThrThrAlaArgSerTyrLeuArgGlnAsnAsnGlnThrLysGlyTyr-74 |
| SEQ. ID. NO. 36932 | 94-AlaThrGluGlyGluLysGlnPhe-101 |
| SEQ. ID. NO. 36933 | 106-AlaArgSerGluGlnAlaAla-112 |
| SEQ. ID. NO. 36934 | 124-LeuProArgThrAlaGlyAspIleAlaGlyAspThrTrpAsnThrSerLysValArgAla-143 |
| SEQ. ID. NO. 36935 | 149-SerProAlaThrGlnAlaArgValLys-157 |
| SEQ. ID. NO. 36936 | 172-ThrProGluGluGlnAlaGlnIleThr-180 |
| Hydrophilic Regions - Hopp-Woods | |
| SEQ. ID. NO. 36937 | 1-MetLysProLysProHisThr-7 |
| SEQ. ID. NO. 36938 | 37-SerValIleAspArgArgThrThrGlyAlaGlnThrAspAspAsnValMet-53 |
| SEQ. ID. NO. 36939 | 56-ArgIleGluThrThrAla-61 |
| SEQ. ID. NO. 36940 | 68-AsnAsnGlnThrLysGlyTyr-74 |
| SEQ. ID. NO. 36941 | 94-AlaThrGluGlyGluLysGlnPhe-101 |
| SEQ. ID. NO. 36942 | 106-AlaArgSerGluGlnAlaAla-112 |
| SEQ. ID. NO. 36943 | 125-ProArgThrAlaGly-129 |
| SEQ. ID. NO. 36944 | 152-ThrGlnAlaArgValLys-157 |
| SEQ. ID. NO. 36945 | 172-ThrProGluGluGlnAlaGlnIle-179 | g937
AMPHI Regions - AMPHI
SEQ. ID. NO. 36946    121-LysArgMetSerAspIleSerAlaGlyIleSerHis-132
SEQ. ID. NO. 36947    231-LysGlnProAspArgIleAsp-237
Antigenic Index - Jameson-Wolf
SEQ. ID. NO. 36948    18-ThrAspLeuProLeuAsnIle-24
SEQ. ID. NO. 36949    26-AspIleMetThrAspLysGlyLysTrpLysLeuGluThr-38
SEQ. ID. NO. 36950    43-LeuAsnSerGluAsnSerArgAlaAlaLeu-52
SEQ. ID. NO. 36951    69-ProThrGluIleGlnGluAsnGlySerAsnThrAsp-80
SEQ. ID. NO. 36952    94-GlyAsnThrAspIleTyrGlySerGlySer-103
SEQ. ID. NO. 36953    107-HisGluGluArgLysLeuAspGlyAsnGlyLysThrArgAsnLysArgMetSerAspIle-126
SEQ. ID. NO. 36954    134-PheLeuLysAspGlyLysAsnProAla-142
SEQ. ID. NO. 36955    150-ThrValTyrGluLysSerArgAsnLysAlaSerSerGlyLys-163
SEQ. ID. NO. 36956    186-TyrArgIleAsnGlySerLysThrLeuSerAspAspValLysTyrLysAlaGly-203
SEQ. ID. NO. 36957    216-AlaAsnAspArgIleSerLeuThrGlyGly-225
SEQ. ID. NO. 36958    230-GlyLysGlnProAspArgIleAspGlyLysLysGluSerAlaArgAsnThrSerThr-248
SEQ. ID. NO. 36959    272-ValSerGlyGlnSerSerSerGluLeuLysLeu-282
Hydrophilic Regions - Hopp-Woods
SEQ. ID. NO. 36960    26-AspIleMetThrAspLysGlyLysTrpLysLeu-36
SEQ. ID. NO. 36961    46-GluAsnSerArgAlaAlaLeu-52
SEQ. ID. NO. 36962    71-GluIleGlnGluAsnGlySerAsnThr-79
SEQ. ID. NO. 36963    107-HisGluGluArgLysLeuAspGlyAsnGlyLysThrArgAsnLysArgMetSerAspIle-126
SEQ. ID. NO. 36964    134-PheLeuLysAspGlyLysAsn-140
SEQ. ID. NO. 36965    150-ThrValTyrGluLysSerArgAsnLysAlaSerSerGly-162
SEQ. ID. NO. 36966    192-LysThrLeuSerAspAspValLysTyrLysAla-202
SEQ. ID. NO. 36967    216-AlaAsnAspArgIleSer-221
SEQ. ID. NO. 36968    231-LysGlnProAspArgIleAspGlyLysLysGluSerAlaArgAsn-245
SEQ. ID. NO. 36969    276-SerSerSerGluLeuLysLeu-282
g950
AMPHI Regions - AMPHI
SEQ. ID. NO. 36970    33-GlyValGlnLysSerAlaGlnGly-40
SEQ. ID. NO. 36971    81-AlaThrValLysLysAlaHisLysHisThrLysAla-92
Antigenic Index - Jameson-Wolf
SEQ. ID. NO. 36972    1-MetAsnLysAsnIle-5
SEQ. ID. NO. 36973    26-LysProAlaSerAsnAlaThrGlyValGlnLysSerAlaGlnGlySerCysGlyAlaSerLysSerAlaGluGlySerCysGlyAlaSerLysSer
                       AlaGluGlySerCysGly-63
SEQ. ID. NO. 36974    65-AlaAlaSerLysAlaGlyGluGlyLysCysGlyGluGlyLysCysGlyAlaThrValLysLysAlaHisLysHisThrLysAlaSerLysAlaLys
                       AlaLysSerAlaGluGlyLysCysGlyGluGlyLysCysGlySerLys-112
Hydrophilic Regions - Hopp-Woods
SEQ. ID. NO. 36975    33-GlyValGlnLysSerAlaGln-39
SEQ. ID. NO. 36976    43-GlyAlaSerLysSerAlaGluGlySerCysGlyAlaSerLysSerAlaGluGlySerCys-62
SEQ. ID. NO. 36977    65-AlaAlaSerLysAlaGlyGluGlyLysCysGlyGluGlyLysCys-79
SEQ. ID. NO. 36978    81-AlaThrValLysLysAlaHisLysHisThrLysAlaSerLysAlaLysAlaLysSerAlaGluGlyLysCysGlyGluGlyLysCysGlySerLys-112
g951
AMPHI Regions - AMPHI
SEQ. ID. NO. 36979    9-ThrIleLeuSerValLeuAlaAla-16
SEQ. ID. NO. 36980    32-GluLeuProLysGluValGlyLysValLeuArgLysHisArgArgTyr-47
SEQ. ID. NO. 36981    62-ValGlyGluArgValAsnArgValPhe-70
SEQ. ID. NO. 36982    127-TrpArgGlnIleGluProIleProGlyGlu-136
SEQ. ID. NO. 36983    145-ArgAsnValLeuArgGluGlyGlyAsnGlnHisLeuAspGlyLeuGluGluValLeuAla-164
SEQ. ID. NO. 36984    189-AlaGlnLysAlaSerLysAlaValArgArg-198
SEQ. ID. NO. 36985    204-GluHisLeuProGluAlaAla-210
SEQ. ID. NO. 36986    227-IleGluAlaLeuGlnArgLeuAlaLysLeu-236
SEQ. ID. NO. 36987    254-LysTyrProGluIleLeuAspGlyPhePheGlu-264
SEQ. ID. NO. 36988    278-MetGluIleMetAsnLeuValSerLeuArgLysProAspAspAla-292
SEQ. ID. NO. 36989    325-ValIleAspGlyTyrAlaGluLys-332
SEQ. ID. NO. 36990    362-ValArgGlnTrpLeuLys-367
SEQ. ID. NO. 36991    395-AlaLeuArgGlnIleGlyArgValArgLysLeuProGluGlnGln-409
SEQ. ID. NO. 36992    416-AspAsnLeuSerLysIle-421
SEQ. ID. NO. 36993    423-MetLeuAlaLeuSer-427
SEQ. ID. NO. 36994    441-AsnIleIleAlaLysLeuSerAlaAlaGlySerThrGluProLeuAlaGlu-457
SEQ. ID. NO. 36995    474-LysMetIleAlaAspLeuGluThr-481
SEQ. ID. NO. 36996    495-AsnLeuGlyTyrSer-499
SEQ. ID. NO. 36997    503-AspSerLysArgLeu-507
SEQ. ID. NO. 36998    563-HisLeuGlyGluVal-567
SEQ. ID. NO. 36999    579-AspValTrpThrGlnAla-584
SEQ. ID. NO. 37000    592-LysIleTrpArgGluThrLeuLys-599
Antigenic Index - Jameson-Wolf
SEQ. ID. NO. 37001    29-AlaAspValGluLeuProLysGluValGlyLysValLeuArgLysHisArgArgTyrSerGluGluGluIleLysAsnGluArgAlaArgLeu-59
SEQ. ID. NO. 37002    61-AlaValGlyGluArgValAsnArg-68
SEQ. ID. NO. 37003    77-ThrAlaLeuGlnLysGlyGlnAla-84
SEQ. ID. NO. 37004    96-GluArgThrLysSerProGluValAlaGluArgAlaLeuGlu-109
SEQ. ID. NO. 37005    126-LysTrpArgGlnIleGluProIleProGlyGluAlaGlnLysArgAlaGlyTrp-143
SEQ. ID. NO. 37006    147-ValLeuArgGluGlyGlyAsnGlnHisLeuAspGlyLeuGluGluValLeuAlaGlnSerAspAspValGlnLysArgArgIle-174
SEQ. ID. NO. 37007    187-GlyValAlaGlnLysAlaSerLysAlaValArgArgAlaAlaLeuLys-202
SEQ. ID. NO. 37008    219-GlnGlyArgGluLysGluLysAlaIleGluAlaAlaGlnArgLeuAlaLysLeuAspThrGluIleLeuPro-242
SEQ. ID. NO. 37009    250-LeuThrAlaArgLysTyrProGluIleLeuAspGlyPhePheGluGlnThrAspThrGlnAsn-270
SEQ. ID. NO. 37010    285-SerLeuArgLysProAspAspAlaTyrAla-294
SEQ. ID. NO. 37011    301-GluHisAsnProAsnAlaAsn-307
SEQ. ID. NO. 37012    317-AlaAsnArgLysGluGlyAlaSer-324

TABLE 1-continued

| | |
|---|---|
| SEQ. ID. NO. 37013 | 326-IleAspGlyTyrAlaGluLysAlaTyrGlyArgGlyThrGlyGluGlnArgGlyArgAla-345 |
| SEQ. ID. NO. 37014 | 354-AlaAspArgArgAspTyrAlaLys-361 |
| SEQ. ID. NO. 37015 | 364-GlnTrpLeuLysLysValSerAlaPro-372 |
| SEQ. ID. NO. 37016 | 375-LeuPheAspLysGlyVal-380 |
| SEQ. ID. NO. 37017 | 387-AlaGluLeuAspGlyGlyArgAlaAlaLeu-396 |
| SEQ. ID. NO. 37018 | 398-GlnIleGlyArgValArgLysLeuProGluGlnGlnGlyArgTyrPheThr-414 |
| SEQ. ID. NO. 37019 | 428-LysLeuProAspLysArgGluAlaLeu-436 |
| SEQ. ID. NO. 37020 | 447-SerAlaAlaGlySerThrGluProLeuAla-456 |
| SEQ. ID. NO. 37021 | 467-GluGlnPheGlyLysArgGlyLysMetIleAlaAspLeuGluThr-481 |
| SEQ. ID. NO. 37022 | 485-LeuThrProAspAsn-489 |
| SEQ. ID. NO. 37023 | 501-LeuSerAspSerLysArgLeuAspGluGlyPhe-511 |
| SEQ. ID. NO. 37024 | 519-GlnIleAsnProAspAspThrAlaValAsnAspSerIle-531 |
| SEQ. ID. NO. 37025 | 537-LeuLysGlyAspAlaGluSerAla-544 |
| SEQ. ID. NO. 37026 | 549-ArgTyrSerPheGluAsnAspProGluProGluVal-560 |
| SEQ. ID. NO. 37027 | 572-GlyGluArgAspGlnAla-577 |
| SEQ. ID. NO. 37028 | 585-AlaHisLeuArgGlyAspLysLysIleTrpArgGluThrLeuLysArgTyrGly-602 |
| SEQ. ID. NO. 37029 | 604-AlaLeuProGluProSerArgLysProArgLys-614 |
| Hydrophilic Regions - Hopp-Woods | |
| SEQ. ID. NO. 37030 | 29-AlaAspValGluLeuProLysGluValGlyLysValLeuArgLysHisArgArgTyrSerGluGluGluIleLysAsnGluArgAlaArgLeu-59 |
| SEQ. ID. NO. 37031 | 61-AlaValGlyGluArgValAsnArg-68 |
| SEQ. ID. NO. 37032 | 77-ThrAlaLeuGlnLysGlyGlnAla-84 |
| SEQ. ID. NO. 37033 | 96-GluArgThrLysSerProGluValAlaGluArgAlaLeuGlu-109 |
| SEQ. ID. NO. 37034 | 133-IleProGlyGluAlaGlnLysArgAlaGlyTrp-143 |
| SEQ. ID. NO. 37035 | 147-ValLeuArgGluGlyGlyAsnGlnHis-155 |
| SEQ. ID. NO. 37036 | 157-AspGlyLeuGluGluValLeuAlaGlnSerAspAspValGlnLysArgArgIle-174 |
| SEQ. ID. NO. 37037 | 188-ValAlaGlnLysAlaSerLysAlaValArgArgAlaAlaLeuLys-202 |
| SEQ. ID. NO. 37038 | 219-GlnGlyArgGluLysGluLysAlaIleGluAlaLeuGlnArgLeuAlaLysLeuAspThrGluIle-240 |
| SEQ. ID. NO. 37039 | 250-LeuThrAlaArgLysTyrProGluIle-258 |
| SEQ. ID. NO. 37040 | 263-PheGluGlnThrAspThrGlnAsn-270 |
| SEQ. ID. NO. 37041 | 285-SerLeuArgLysProAspAspAlaTyrAla-294 |
| SEQ. ID. NO. 37042 | 317-AlaAsnArgLysGluGlyAlaSer-324 |
| SEQ. ID. NO. 37043 | 329-TyrAlaGluLysAlaTyrGly-335 |
| SEQ. ID. NO. 37044 | 337-GlyThrGlyGluGlnArgGlyArgAla-345 |
| SEQ. ID. NO. 37045 | 354-AlaAspArgArgAspTyrAlaLys-361 |
| SEQ. ID. NO. 37046 | 387-AlaGluLeuAspGlyGlyArgAlaAlaLeu-396 |
| SEQ. ID. NO. 37047 | 398-GlnIleGlyArgValArgLysLeuProGluGlnGlnGly-410 |
| SEQ. ID. NO. 37048 | 428-LysLeuProAspLysArgGluAlaLeu-436 |
| SEQ. ID. NO. 37049 | 450-GlySerThrGluProLeuAla-456 |
| SEQ. ID. NO. 37050 | 469-PheGlyLysArgGlyLysMetIleAlaAspLeuGluThr-481 |
| SEQ. ID. NO. 37051 | 485-LeuThrProAspAsn-489 |
| SEQ. ID. NO. 37052 | 502-SerAspSerLysArgLeuAspGlu-509 |
| SEQ. ID. NO. 37053 | 521-AsnProAspAspThrAlaVal-527 |
| SEQ. ID. NO. 37054 | 539-GlyAspAlaGluSer-543 |
| SEQ. ID. NO. 37055 | 552-PheGluAsnAspProGluProGluVal-560 |
| SEQ. ID. NO. 37056 | 572-GlyGluArgAspGlnAla-577 |
| SEQ. ID. NO. 37057 | 587-LeuArgGlyAspLysLysIleTrpArgGluThrLeuLys-599 |
| SEQ. ID. NO. 37058 | 607-GluProSerArgLysProArgLys-614 |
| g952 | |
| AMPHI Regions - AMPHI | |
| SEQ. ID. NO. 37059 | 47-SerValAlaThrLeuLeuAsn-53 |
| SEQ. ID. NO. 37060 | 66-LeuGluLysLeuGlyLysGluGlnMetArgAla-76 |
| SEQ. ID. NO. 37061 | 78-PheGluAspMetArgArgIle-84 |
| SEQ. ID. NO. 37062 | 100-GluGlnLeuAlaGlnLeu-105 |
| SEQ. ID. NO. 37063 | 122-SerValLeuArgGlyVal-127 |
| SEQ. ID. NO. 37064 | 147-AlaGlnPheLeuGluAla-152 |
| Antigenic Index - Jameson-Wolf | |
| SEQ. ID. NO. 37065 | 24-GlnSerTrpLysAlaArgArgAspPheAsnIleValLysGlnAspLeuAspPheSerCys-43 |
| SEQ. ID. NO. 37066 | 59-LysLeuThrGluGluGluValLeuGluLysLeuLeuGlyLysGluGlnMetArgAlaSerPheGluAspMetArgArgIleMetPro-86 |
| SEQ. ID. NO. 37067 | 88-LeuGlyPheGluAlaLysGlyTyr-95 |
| SEQ. ID. NO. 37068 | 113-LeuLysTyrArgLysAspAspHisPheSer-122 |
| SEQ. ID. NO. 37069 | 125-ArgGlyValAspGlyAsnThr-131 |
| SEQ. ID. NO. 37070 | 135-AlaAspProSerProGlyHis-141 |
| SEQ. ID. NO. 37071 | 153-TrpGlnThrArgGluGlyAsnLeuAlaGly-162 |
| SEQ. ID. NO. 37072 | 168-ValProLysLysAlaGluAlaIleSer-176 |
| SEQ. ID. NO. 37073 | 183-HisHisProLysArgGlnThrGlu-190 |
| Hydrophilic Regions - Hopp-Woods | |
| SEQ. ID. NO. 37074 | 25-SerTrpLysAlaArgArgAspPheAsnIleValLysGlnAspLeuAspPhe-41 |
| SEQ. ID. NO. 37075 | 59-LysLeuThrGluGluGluValLeuGluLysLeuLeuGlyLysGluGlnMetArgAlaSerPheGluAspMetArgArgIleMetPro-86 |
| SEQ. ID. NO. 37076 | 88-LeuGlyPheGluAlaLysGly-94 |
| SEQ. ID. NO. 37077 | 114-LysTyrArgLysAspAspHisPheSer-122 |
| SEQ. ID. NO. 37078 | 153-TrpGlnThrArgGluGlyAsnLeu-160 |
| SEQ. ID. NO. 37079 | 168-ValProLysLysAlaGluAlaIleSer-176 |
| SEQ. ID. NO. 37080 | 184-HisProLysArgGlnThrGlu-190 |
| g953 | |
| AMPHI Regions - AMPHI | |
| SEQ. ID. NO. 37081 | 38-AsnThrSerThrAsnValGlyGlyPheTyrGlyLeuThr-50 |
| SEQ. ID. NO. 37082 | 79-ProPheThrGlyHis-83 |
| SEQ. ID. NO. 37083 | 85-LysSerAlaAspIlePheAspAlaAlaGln-94 |
| SEQ. ID. NO. 37084 | 150-GlyAspPheSerThrThr-155 |

TABLE 1-continued

Antigenic Index - Jameson-Wolf
SEQ. ID. NO. 37085    21-TyrLysValAspGluTyrHisAla-28
SEQ. ID. NO. 37086    37-PheAsnThrSerThrAsnVal-43
SEQ. ID. NO. 37087    53-ValGluPheAspGlnAlaLysArgAspGlyLysIleAspIle-66
SEQ. ID. NO. 37088    74-GlnSerGlySerGlnPro-79
SEQ. ID. NO. 37089    94-GlnTyrProAspIleArgPheValSer-102
SEQ. ID. NO. 37090    104-LysPheAsnPheAsnGlyLysLysLeuValSer-114
SEQ. ID. NO. 37091    121-MetArgGlyLysThrAlaProValLysLeuLysAlaGluLys-134
SEQ. ID. NO. 37092    136-AsnCysTyrGlnSerProMetAlaGluThrGluValCysGlyGlyAspPheSerThrThrIleAspArgThrLysTrpGlyValAsp-164
SEQ. ID. NO. 37093    170-GlyMetThrLysAsnValArgIle-177
SEQ. ID. NO. 37094    179-IleGlnIleGluAlaAlaLysGln-186
Hydrophilic Regions - Hopp-Woods
SEQ. ID. NO. 37095    21-TyrLysValAspGluTyrHisAla-28
SEQ. ID. NO. 37096    53-ValGluPheAspGlnAlaLysArgAspGlyLysIleAspIle-66
SEQ. ID. NO. 37097    107-PheAsnGlyLysLysLeuValSer-114
SEQ. ID. NO. 37098    121-MetArgGlyLysThrAlaProValLysLeuLysAlaGluLys-134
SEQ. ID. NO. 37099    142-MetAlaGluThrGluValCysGly-149
SEQ. ID. NO. 37100    154-ThrThrIleAspArgThrLysTrp-161
SEQ. ID. NO. 37101    173-LysAsnValArgIle-177
SEQ. ID. NO. 37102    179-IleGlnIleGluAlaAlaLysGln-186
g957-2
AMPHI Regions - AMPHI
SEQ. ID. NO. 37103    11-SerPhePheAlaLeuValPheAla-18
SEQ. ID. NO. 37104    39-AlaThrGluValProGluAsnPro-46
SEQ. ID. NO. 37105    48-AlaPheValAlaLysLeuAlaArgLeuPheArgAsnAla-60
SEQ. ID. NO. 37106    74-GluGluSerLeuAlaGlyAlaValAspAsp-83
SEQ. ID. NO. 37107    167-HisGlyGluAsnTyrGluThr-173
SEQ. ID. NO. 37108    198-GluAspValTyrGluHisCysLeuGlyCysTyrGlnMet-210
SEQ. ID. NO. 37109    218-TyrArgAspValAlaAsn-223
SEQ. ID. NO. 37110    235-SerAsnArgIleAlaSer-240
SEQ. ID. NO. 37111    251-MetArgGluLeuMetProArg-257
SEQ. ID. NO. 37112    355-GluLysGluValSerArgTyrAlaGluAlaAlaAlaArg-367
Antigenic Index - Jameson-Wolf
SEQ. ID. NO. 37113    29-IleAsnProArgTrp-33
SEQ. ID. NO. 37114    35-LeuSerAspThrAlaThrGluValProGluAsnProAsnAla-48
SEQ. ID. NO. 37115    57-PheArgAsnAlaAspArgAla-63
SEQ. ID. NO. 37116    67-ValLysGluSerMetArgThrGluGluSerLeu-77
SEQ. ID. NO. 37117    80-AlaValAspAspGlyProLeuGlnSerGluLysAspTyr-92
SEQ. ID. NO. 37118    98-ArgLeuSerArgLeuLysGluLysAlaLys-107
SEQ. ID. NO. 37119    112-ThrGluGlnGluHisGlyGlu-118
SEQ. ID. NO. 37120    125-TyrIleGlyGluGlyGly-130
SEQ. ID. NO. 37121    136-LeuSerGlnArgSerProGluAlaPheVal-145
SEQ. ID. NO. 37122    149-TyrLeuTyrArgAsnAspArgProPheSer-158
SEQ. ID. NO. 37123    166-AlaHisGlyGluAsnTyrGluThrThrGlyGluTyrArgVal-179
SEQ. ID. NO. 37124    182-GlnProAspGlySerVal-187
SEQ. ID. NO. 37125    190-AlaAlaGlyArgGlyLysIleGlyGluAspValTyr-201
SEQ. ID. NO. 37126    217-LysTyrArgAspValAlaAsnAspGluGlnLysValTrpAspPheArg
                      GluGluSerAsnArgIleAlaSerAspSerArgAspTyrVal-246
SEQ. ID. NO. 37127    250-AsnMetArgGluLeuMetProArgGlyMetLysAlaAsnSer-263
SEQ. ID. NO. 37128    267-GlyTyrAspAlaAspGlyLeuProGlnLys-276
SEQ. ID. NO. 37129    280-SerPheAspAsnGlyLysLysArgGlnSerPheGluTyrTyrLeuLysAsnGlyAsn-298
SEQ. ID. NO. 37130    309-LeuLysAlaAspGlyValThr-315
SEQ. ID. NO. 37131    329-LeuAspGlyGlyArgIleIleArgGluGluLysGlnGlyAspArgLeuProAspPhe-347
SEQ. ID. NO. 37132    349-LeuAsnLeuGluAspLeuGluLysGluValSerArgTyrAlaGluAlaAlaAlaArgArgSerGlyGlyArgArgGlyLeuSerHis-377
Hydrophilic Regions - Hopp-Woods
SEQ. ID. NO. 37133    38-ThrAlaThrGluValProGluAsnPro-46
SEQ. ID. NO. 37134    57-PheArgAsnAlaAspArgAla-63
SEQ. ID. NO. 37135    67-ValLysGluSerMetArgThrGluGluSerLeu-77
SEQ. ID. NO. 37136    80-AlaValAspAspGlyProLeuGlnSerGluLysAspTyr-92
SEQ. ID. NO. 37137    98-ArgLeuSerArgLeuLysGluLysAlaLys-107
SEQ. ID. NO. 37138    112-ThrGluGlnGluHisGlyGlu-118
SEQ. ID. NO. 37139    136-LeuSerGlnArgSerProGlu-142
SEQ. ID. NO. 37140    151-TyrArgAsnAspArgProPhe-157
SEQ. ID. NO. 37141    169-GluAsnTyrGluThrThrGlyGluTyr-177
SEQ. ID. NO. 37142    190-AlaAlaGlyArgGlyLysIleGlyGluAspValTyr-201
SEQ. ID. NO. 37143    217-LysTyrArgAspValAlaAsnAspGluGlnLysValTrpAspPheArgGluGluSerAsnArgIleAlaSerAspSerArgAsp-244
SEQ. ID. NO. 37144    250-AsnMetArgGluLeuMetProArgGlyMetLys-260
SEQ. ID. NO. 37145    268-TyrAspAlaAspGlyLeuPro-274
SEQ. ID. NO. 37146    282-AspAsnGlyLysLysArgGlnSer-289
SEQ. ID. NO. 37147    309-LeuLysAlaAspGlyValThr-315
SEQ. ID. NO. 37148    331-GlyGlyArgIleIleArgGluGluLysGlnGlyAspArgLeuPro-345
SEQ. ID. NO. 37149    349-LeuAsnLeuGluAspLeuGluLysGluValSerArgTyrAlaGluAlaAlaAlaArgArgSerGlyGlyArgArgGlyLeuSer-376
g958
AMPHIRegions - AMPHI
SEQ. ID. NO. 37150    39-GlyGlyAlaGlnGlyAlaSerGluSerAlaGln-49
SEQ. ID. NO. 37151    85-ProGluAspTyrThrArgIleValAlaAsp-94
SEQ. ID. NO. 37152    175-GlyArgArgLeuGlnSerValSerArgThrAlaGluMetLeuGly-189
SEQ. ID. NO. 37153    342-IleSerAspThrLeuGln-347
SEQ. ID. NO. 37154    400-GlnLysTyrGlnThrLeuAlaAsn-407
SEQ. ID. NO. 37155    426-TrpHisLysAsnAlaGly-431

TABLE 1-continued

| | |
|---|---|
| SEQ. ID. NO. 37156 | 489-GlyGlyLysAlaSerArgSerValGlyArgValLeuProValVal-503 |
| SEQ. ID. NO. 37157 | 526-IleGluProArgLeu-530 |
| SEQ. ID. NO. 37158 | 540-GlnAsnAspLeuProAsnPheAsp-547 |
| SEQ. ID. NO. 37159 | 571-AsnAlaAlaAsnSerLeuSerThrAlaValGlnSer-582 |
| | 615-ValGlyLysAsnPro-619 |
| SEQ. ID. NO. 37160 | 692-AspLysLeuSerGln-696 |
| SEQ. ID. NO. 37161 | 722-LysLysProIleGlu-726 |
| | 768-AspLeuSerSerVal-GlyArgAsnPro-776 |
| Antigenic Index - Jameson-Wolf | |
| SEQ. ID. NO. 37162 | 19-GlyThrHisCysAla-23 |
| SEQ. ID. NO. 37163 | 27-ValAlaAlaGluGluAlaAspGlyArgValAlaGluGlyGlyAlaGlnGlyAlaSerGluSerAlaGlnAlaSer-51 |
| SEQ. ID. NO. 37164 | 62-CysSerAsnGluSerGlySerProGluArgThrGluAlaAlaValGlnGlySerGlyGluAlaSerValProGluAspTyrThrArgIleValAla AspArgMetGluGlyGlnSerLysValLysValArgAlaGluGly-108 |
| SEQ. ID. NO. 37165 | 110-ValIleIleGluArgAspGlyAlaValLeu-119 |
| SEQ. ID. NO. 37166 | 122-AspTrpAlaAspTyrAspGlnSerGlyAsp-131 |
| SEQ. ID. NO. 37167 | 134-ThrValGlyAspArgPheAlaLeuGlnGlnAspGlyThrLeuIleArgGlyGluThrLeu-153 |
| SEQ. ID. NO. 37168 | 157-LeuAspGlnGlnThrGlyGluAlaHisAsnValArgMetGluThrGluGlnGlyGlyArgArgLeuGlnSerValSerArgThrAlaGluMetLeu GlyGluGlyArgTyrLysLeuThrGluThrGlnPheAsnThrCysSerAlaGlyAspAlaGlyTrp-210 |
| SEQ. ID. NO. 37169 | 215-AlaSerValGluAlaAspArgGlyLysGlyIleGly-226 |
| SEQ. ID. NO. 37170 | 248-PheProLeuAspGlyAsnArgLysSerGlyLeu-258 |
| SEQ. ID. NO. 37171 | 264-SerAlaGlySerAspGlyVal-270 |
| SEQ. ID. NO. 37172 | 291-GlyIleIleGlyGluArgGlyAlaThrPheAspGlyGlnIleArgTyrLeuArgProAspTyrSerGlyGlnThrAsp-316 |
| SEQ. ID. NO. 37173 | 320-LeuProHisAspLysLysSerGlyArgAsnAsnArgTyrGlnAla-334 |
| SEQ. ID. NO. 37174 | 336-TrpGlnHisArgHisAspIleSerAspThrLeu-346 |
| SEQ. ID. NO. 37175 | 351-AspPheAsnGlnValSerAspSerGlyTyrTyrArgAspPheTyrGlyGlyGluGluIleAlaGlyAsnValAsnLeuAsnArgArgValTrp-381 |
| SEQ. ID. NO. 37176 | 383-AspTyrGlyGlyArgAlaAlaGlyGlySerLeuAsn-394 |
| SEQ. ID. NO. 37177 | 400-GlnLysTyrGlnThr-404 |
| SEQ. ID. NO. 37178 | 406-AlaAsnGlnSerGlyTyrLysAspGluProTyr-416 |
| SEQ. ID. NO. 37179 | 420-ProArgLeuSerAlaAspTrpHisLysAsnAlaGlyArgAlaGlnIle-435 |
| SEQ. ID. NO. 37180 | 443-ArgPheSerHisAspGlyArgGlnAspGlySerArg-454 |
| SEQ. ID. NO. 37181 | 465-PheSerAsnSerTrpGly-470 |
| SEQ. ID. NO. 37182 | 473-ArgProLysLeuGlyLeu-478 |
| SEQ. ID. NO. 37183 | 487-SerPheGlyGlyLysAlaSerArgSerValGlyArg-498 |
| SEQ. ID. NO. 37184 | 506-AspGlyGlyThrThrPheGluArgAsnThrArgLeuPheGlyGlyGly-521 |
| SEQ. ID. NO. 37185 | 537-AlaLysSerGlnAsnAspLeuProAsnPheAspSerSerGluSerSerPheGly-554 |
| SEQ. ID. NO. 37186 | 559-PheArgGluAsnLeuTyrTyrGlyAsnAspArgIleAsnAla-572 |
| SEQ. ID. NO. 37187 | 583-ArgIleLeuAspGlyAlaThrGlyGluGluArgPheArgAlaGlyIleGlyGlnLysPheTyrPheLysAspAspAlaValMetLeuAspGlySerValG lyLysAsnProArgSerArgSerAspTrp-625 |
| SEQ. ID. NO. 37188 | 630-SerGlyGlyIleGlyGly-635 |
| SEQ. ID. NO. 37189 | 641-SerSerIleHisTyrAsnGlnAsnAspLysArgAlaGluHis-654 |
| SEQ. ID. NO. 37190 | 659-AlaGlyTyrArgProAlaProGlyLysValLeuAsnAlaArgTyrLysTyrGlyArgAsnGluLysIle-681 |
| SEQ. ID. NO. 37191 | 692-AspLysLeuSerGln-696 |
| SEQ. ID. NO. 37192 | 717-TyrGlyPheGluAlaLysLysProIleGlu-726 |
| SEQ. ID. NO. 37193 | 731-AlaGluTyrLysSerSerCysGlyCysTrp-740 |
| SEQ. ID. NO. 37194 | 750-ValThrGlyGluAsnThrTyrLysAsn-758 |
| SEQ. ID. NO. 37195 | 765-GlnLeuLysAspLeuSerSerValGlyArgAsnProAlaGlyArgMetAspVal-782 |
| SEQ. ID. NO. 37196 | 792-SerLeuSerAlaGlyArgAsnLysArgPro-801 |
| Hydrophilic Regions - Hopp-Woods | |
| SEQ. ID. NO. 37197 | 27-ValAlaAlaGluGluAlaAspGlyArgValAlaGluGlyGlyAla-41 |
| SEQ. ID. NO. 37198 | 43-GlyAlaSerGluSerAlaGlnAlaSer-51 |
| SEQ. ID. NO. 37199 | 64-AsnGluSerGlySerProGluArgThrGluAlaAlaVal-76 |
| SEQ. ID. NO. 37200 | 78-GlySerGlyGluAlaSerValProGluAspTyrThr-89 |
| SEQ. ID. NO. 37201 | 92-ValAlaAspArgMetGluGlyGlnSerLysValLysValArgAlaGluGly-108 |
| SEQ. ID. NO. 37202 | 110-ValIleIleGluArgAspGlyAla-117 |
| SEQ. ID. NO. 37203 | 124-AlaAspTyrAspGlnSerGlyAsp-131 |
| SEQ. ID. NO. 37204 | 146-ThrLeuIleArgGlyGluThr-152 |
| SEQ. ID. NO. 37205 | 159-GlnGlnThrGlyGluAlaHisAsnValArgMetGluThrGluGlnGlyGlyArgArgLeuGlnSerValSerArgThrAlaGluMetLeuGlyGlu GlyArgTyrLysLeuThrGlu-197 |
| SEQ. ID. NO. 37206 | 215-AlaSerValGluAlaAspArgGlyLysGly-224 |
| SEQ. ID. NO. 37207 | 249-ProLeuAspGlyAsnArgLysSerGly-257 |
| SEQ. ID. NO. 37208 | 265-AlaGlySerAspGlyVal-270 |
| SEQ. ID. NO. 37209 | 293-IleGlyGluArgGlyAlaThr-299 |
| SEQ. ID. NO. 37210 | 304-IleArgTyrLeuArg-308 |
| SEQ. ID. NO. 37211 | 322-HisAspLysLysSerGlyArgAsnAsnArgTyrGlnAla-334 |
| SEQ. ID. NO. 37212 | 336-TrpGlnHisArgHisAspIleSerAsp-344 |
| SEQ. ID. NO. 37213 | 409-SerGlyTyrLysAspGluProTyr-416 |
| SEQ. ID. NO. 37214 | 422-LeuSerAlaAspTrpHisLysAsnAlaGlyArgAla-433 |
| SEQ. ID. NO. 37215 | 444-PheSerHisAspGlyArgGlnAspGlySerArg-454 |
| SEQ. ID. NO. 37216 | 488-PheGlyGlyLysAlaSerArgSerValGly-497 |
| SEQ. ID. NO. 37217 | 509-ThrThrPheGluArgAsnThrArg-516 |
| SEQ. ID. NO. 37218 | 538-LysSerGlnAsnAsp-542 |
| SEQ. ID. NO. 37219 | 547-AspSerSerGluSer-551 |
| SEQ. ID. NO. 37220 | 568-AspArgIleAsnAla-572 |
| SEQ. ID. NO. 37221 | 588-AlaThrGlyGluGluArgPheArgAla-596 |
| SEQ. ID. NO. 37222 | 603-TyrPheLysAspAspAlaValMet-610 |
| SEQ. ID. NO. 37223 | 614-SerValGlyLysAsnProArgSerArgSerAsp-624 |
| SEQ. ID. NO. 37224 | 647-GlnAsnAspLysArgAlaGluHis-654 |
| SEQ. ID. NO. 37225 | 673-TyrLysTyrGlyArgAsnGluLysIle-681 |
| SEQ. ID. NO. 37226 | 719-PheGluAlaLysLysProIleGlu-726 |

TABLE 1-continued

| | |
|---|---|
| SEQ. ID. NO. 37227 | 731-AlaGluTyrLysSer-735 |
| SEQ. ID. NO. 37228 | 765-GlnLeuLysAspLeuSerSerValGlyArgAsnProAlaGlyArgMetAspVal-782 |
| SEQ. ID. NO. 37229 | 794-SerAlaGlyArgAsnLysArgPro-801 | g959
AMPHI Regions - AMPHI

| | |
|---|---|
| SEQ. ID. NO. 37230 | 56-AlaAlaTrpAlaArgValGlyGly-63 |

Antigenic Index - Jameson-Wolf

| | |
|---|---|
| SEQ. ID. NO. 37231 | 24-AlaHisHisAspGlyHisGlyAspAspHisGlyHis-36 |
| SEQ. ID. NO. 37232 | 38-AlaHisGlnHisGlyLysGlnAspLysIleIleSer-49 |
| SEQ. ID. NO. 37233 | 51-AlaGlnAlaGluLysAlaAla-57 |
| SEQ. ID. NO. 37234 | 60-ArgValGlyGlyLysIleThrAspIleAspLeuGluHisAspAspGlyArgProHisTyrAspValGluIleValLysAsnGlyGlnGluTyr-90 |
| SEQ. ID. NO. 37235 | 94-ValAspAlaArgThrGlyArgValIleSerSerArgArgAspAsp-108 |

Hydrophilic Regions - Hopp-Woods

| | |
|---|---|
| SEQ. ID. NO. 37236 | 27-AspGlyHisGlyAspAspAspHisGlyHis-36 |
| SEQ. ID. NO. 37237 | 40-GlnHisGlyLysGlnAspLysIleIleSer-49 |
| SEQ. ID. NO. 37238 | 51-AlaGlnAlaGluLysAlaAla-57 |
| SEQ. ID. NO. 37239 | 61-ValGlyGlyLysIleThrAspIleAspLeuGluHisAspAspGlyArgProHisTyr-79 |
| SEQ. ID. NO. 37240 | 82-GluIleValLysAsnGlyGlnGluTyr-90 |
| SEQ. ID. NO. 37241 | 94-ValAspAlaArgThrGlyArg-100 |
| SEQ. ID. NO. 37242 | 102-IleSerSerArgArgAspAsp-108 | g973
AMPHI Regions - AMPHI

| | |
|---|---|
| SEQ. ID. NO. 37243 | 12-GluArgLeuIleAlaArgLeuAlaArgGluProAspSerAlaGluAspValLeuAsnLeuLeuArgGlnAla-35 |
| SEQ. ID. NO. 37244 | 44-AspThrLeuThrArgLeuGluLysValLeuAspPhe-55 |
| SEQ. ID. NO. 37245 | 77-AspSerIleGluArgIleThrAlaTyr-85 |
| SEQ. ID. NO. 37246 | 112-AspLeuLeuLysTyrMet-117 |
| SEQ. ID. NO. 37247 | 143-AlaLeuLeuLysGluPheArgGluGln-151 |
| SEQ. ID. NO. 37248 | 171-PheGluAspIleIleGluGlnIleValGlyAspIleGluAsp-184 |
| SEQ. ID. NO. 37249 | 190-GluSerAlaAspAspIleHisSerVal-198 |
| SEQ. ID. NO. 37250 | 208-AlaThrGluIleGluAspIleAsnAlaPhe-217 |
| SEQ. ID. NO. 37251 | 235-IleGlnGluLeuGly-239 |

Antigenic Index - Jameson-Wolf

| | |
|---|---|
| SEQ. ID. NO. 37252 | 1-MetAspGlyAlaGlnProLysThrAsnPhe-10 |
| SEQ. ID. NO. 37253 | 18-LeuAlaArgGluProAspSerAlaGluAspVal-28 |
| SEQ. ID. NO. 37254 | 34-GlnAlaHisGluGlnGluValPheAspAlaAspThrLeuThrArgLeuGluLysValLeuAsp-54 |
| SEQ. ID. NO. 37255 | 56-AlaGluLeuGluValArgAspAlaMetIleThrArgSerArgMetAsnValLeuLysGluAsnAspSerIleGluArg-81 |
| SEQ. ID. NO. 37256 | 96-ValIleGlyGluAspLysAspGluVal-104 |
| SEQ. ID. NO. 37257 | 118-PheAsnProGluGlnPheHis-124 |
| SEQ. ID. NO. 37258 | 136-ProGluGlyLysSer-140 |
| SEQ. ID. NO. 37259 | 146-LysGluPheArgGluGlnArgAsnHis-154 |
| SEQ. ID. NO. 37260 | 159-IleAspGluTyrGlyGlyThrSerGly-167 |
| SEQ. ID. NO. 37261 | 178-IleValGlyAspIleGluAspGluPheAspGluAspGluSerAlaAspAspIleHis-196 |
| SEQ. ID. NO. 37262 | 199-SerAlaGluArgTrpArg-204 |
| SEQ. ID. NO. 37263 | 209-ThrGluIleGluAsp-213 |
| SEQ. ID. NO. 37264 | 219-GlyThrGluTyrGlySerGluGluAlaAspThr-229 |
| SEQ. ID. NO. 37265 | 239-GlyHisLeuProValArgGlyGluLysValLeu-249 |
| SEQ. ID. NO. 37266 | 258-AlaArgAlaAspAsnArgArgLeuHis-266 |

Hydrophilic Regions - Hopp-Woods

| | |
|---|---|
| SEQ. ID. NO. 37267 | 1-MetAspGlyAlaGlnProLys-7 |
| SEQ. ID. NO. 37268 | 18-LeuAlaArgGluProAspSerAlaGluAspVal-28 |
| SEQ. ID. NO. 37269 | 34-GlnAlaHisGluGlnGluValPheAsp-42 |
| SEQ. ID. NO. 37270 | 44-AspThrLeuThrArgLeuGluLysValLeuAsp-54 |
| SEQ. ID. NO. 37271 | 56-AlaGluLeuGluValArgAspAlaMetIleThrArgSerArgMetAsnValLeuLysGluAsnAspSerIleGluArg-81 |
| SEQ. ID. NO. 37272 | 96-ValIleGlyGluAspLysAspGluVal-104 |
| SEQ. ID. NO. 37273 | 136-ProGluGlyLysSer-140 |
| SEQ. ID. NO. 37274 | 146-LysGluPheArgGluGlnArgAsn-153 |
| SEQ. ID. NO. 37275 | 178-IleValGlyAspIleGluAspGluPheAspGluAspGluSerAlaAspAspIleHis-196 |
| SEQ. ID. NO. 37276 | 199-SerAlaGluArgTrpArg-204 |
| SEQ. ID. NO. 37277 | 209-ThrGluIleGluAsp-213 |
| SEQ. ID. NO. 37278 | 222-TyrGlySerGluGluAlaAspThr-229 |
| SEQ. ID. NO. 37279 | 243-ValArgGlyGluLysValLeu-249 |
| SEQ. ID. NO. 37280 | 258-AlaArgAlaAspAsnArgArgLeuHis-266 | g981
AMPHI Regions - AMPHI

| | |
|---|---|
| SEQ. ID. NO. 37281 | 32-AsnProGlyLysValTyrArgValAlaSer-41 |
| SEQ. ID. NO. 37282 | 46-AlaProPheGluSerLeuAsp-52 |
| SEQ. ID. NO. 37283 | 66-AsnAlaMetAlaLys-70 |
| SEQ. ID. NO. 37284 | 132-LysValSerSerSerGluAspLeuLysLysMetAsnLysValGly-146 |
| SEQ. ID. NO. 37285 | 167-LysIleAlaArgPheGlu-172 |
| SEQ. ID. NO. 37286 | 181-LeuGluAsnGlyGlyLeuAspSerValVal-190 |
| SEQ. ID. NO. 37287 | 197-AlaAsnTyrValLysAsnAsnPro-204 |
| SEQ. ID. NO. 37288 | 207-GlyMetAspPheValThrLeuPro-214 |
| SEQ. ID. NO. 37289 | 233-ValLysMetLeuAsnAspAlaLeuGluLysValArgGluSerGlyGluTyr-249 |

Antigenic Index - Jameson-Wolf

| | |
|---|---|
| SEQ. ID. NO. 37290 | 19-CysGlyGlyGlnGlyLysAspAlaAlaAla-28 |
| SEQ. ID. NO. 37291 | 30-AlaAlaAsnProGlyLysValTyrArg-38 |
| SEQ. ID. NO. 37292 | 49-GluSerLeuAspSerLysGlyAsnValGluGlyPheAsp-61 |
| SEQ. ID. NO. 37293 | 76-IleGluPheLysHisGlnProTrpAspSer-85 |
| SEQ. ID. NO. 37294 | 90-LeuAsnAsnGlyAspAlaAspVal-97 |
| SEQ. ID. NO. 37295 | 104-IleThrAspAspArgLysGlnSerMetAspPheSerAspProTyrPhe-119 |

TABLE 1-continued

| | |
|---|---|
| SEQ. ID. NO. 37296 | 127-ValProLysGlyLysLysValSerSerSerGluAspLeuLysLysMetAsnLysValGly-146 |
| SEQ. ID. NO. 37297 | 149-ThrGlyHisThrGlyAspPheSerVal-157 |
| SEQ. ID. NO. 37298 | 159-LysLeuLeuGlyAsnAspAsnProLysIleAlaArg-170 |
| SEQ. ID. NO. 37299 | 179-LysGluLeuGluAsnGlyGlyLeuAspSerValValSerAspSerAla-194 |
| SEQ. ID. NO. 37300 | 201-LysAsnAsnProAlaLysGlyMetAspPhe-210 |
| SEQ. ID. NO. 37301 | 214-ProAspPheThrThr-218 |
| SEQ. ID. NO. 37302 | 225-ValArgLysGlyAspGluAlaThrVal-233 |
| SEQ. ID. NO. 37303 | 235-MetLeuAsnAspAlaLeuGluLysValArgGluSerGlyGluTyrAspLysIleTyr-253 |
| SEQ. ID. NO. 37304 | 257-PheAlaLysGluGlyGlyGlnAlaAlaLys-266 |
| SEQ. ID. NO. 37305 | 21-GlyGlnGlyLysAspAlaAlaAla-28 |
| SEQ. ID. NO. 37306 | 49-GluSerLeuAspSerLysGlyAsnValGluGlyPheAsp-61 |
| SEQ. ID. NO. 37307 | 91-AsnAsnGlyAspAlaAspVal-97 |
| SEQ. ID. NO. 37308 | 104-IleThrAspArgLysGlnSerMetAspPheSer-115 |
| SEQ. ID. NO. 37309 | 128-ProLysGlyLysLysValSerSerSerGluAspLeuLysLysMetAsnLys-144 |
| SEQ. ID. NO. 37310 | 164-AspAsnProLysIleAlaArg-170 |
| SEQ. ID. NO. 37311 | 179-LysGluLeuGluAsnGlyGlyLeu-186 |
| SEQ. ID. NO. 37312 | 203-AsnProAlaLysGlyMetAsp-209 |
| SEQ. ID. NO. 37313 | 225-ValArgLysGlyAspGluAlaThrVal-233 |
| SEQ. ID. NO. 37314 | 235-MetLeuAsnAspAlaLeuGluLysValArgGluSerGlyGluTyrAspLysIleTyr-253 |
| SEQ. ID. NO. 37315 | 257-PheAlaLysGluGlyGlyGlnAlaAlaLys-266 |
| g982 | |
| AMPHI Regions - AMPHI | |
| SEQ. ID. NO. 37316 | 10-ArgPheLeuGlnLysMetValAsnGlyValAsnIleLeuProAlaAlaAspTrp-27 |
| SEQ. ID. NO. 37317 | 70-AlaGlnMetValLysGluValAlaSerLysThr-80 |
| SEQ. ID. NO. 37318 | 99-ValAlaGluGlyMetLysTyr-105 |
| SEQ. ID. NO. 37319 | 114-AspLeuLysArgGlyIleAspLysAlaValAlaAlaLeuValGluGluLeuLysAsnIleAlaLysProCysAspThrSerLysGluIleAlaGln ValGlySer-148 |
| SEQ. ID. NO. 37320 | 159-AlaIleIleAlaGluAlaMetGluLysValGly-169 |
| SEQ. ID. NO. 37321 | 184-AsnGluLeuAspValValGluGlyMet-192 |
| SEQ. ID. NO. 37322 | 208-GluLysGlnIleAlaGlyLeuAsp-215 |
| SEQ. ID. NO. 37323 | 226-IleSerAsnIleArgAspLeuLeuProValLeuGluGlnValAlaLysAla-242 |
| SEQ. ID. NO. 37324 | 264-AsnAsnIleArgGlyIleLeuLysThrValAla-274 |
| SEQ. ID. NO. 37325 | 312-ThrLeuAspAspLeuGlyGlnThrLysArg-321 |
| SEQ. ID. NO. 37326 | 330-ThrValIleAspGlyPheGlyAspAlaAla-339 |
| SEQ. ID. NO. 37327 | 366-GluArgValAlaLysLeuAlaGlyGlyVal-375 |
| SEQ. ID. NO. 37328 | 425-LeuGluAsnLeuHisThr-430 |
| SEQ. ID. NO. 37329 | 443-LeuArgAlaValGluSerProLeuArgGlnIleValAlaAsnAla-457 |
| SEQ. ID. NO. 37330 | 483-GluTyrGlyAspMetIleGlyMet-490 |
| SEQ. ID. NO. 37331 | 499-ThrArgSerAlaLeu-503 |
| Antigenic Index - Jameson-Wolf | |
| SEQ. ID. NO. 37332 | 1-AlaSerGlnAsnLeuArgPheAspAsnArgPheLeu-12 |
| SEQ. ID. NO. 37333 | 31-GlyAlaLysGlyArgAsnValValVal-39 |
| SEQ. ID. NO. 37334 | 42-AlaPheGlyGlyProHisIleThrLysAspGlyValThrValAlaLysGluIleGluLeuLysAspLysPheGluAsnMetGly-69 |
| SEQ. ID. NO. 37335 | 72-MetValLysGluValAlaSerLysThrAsnAspValAlaGlyAspGlyThrThr-89 |
| SEQ. ID. NO. 37336 | 111-AsnProThrAspLeuLysArgGlyIleAspLysAlaVal-123 |
| SEQ. ID. NO. 37337 | 128-GluGluLeuLysAsnIleAlaLysProCysAspThrSerLysGluIleAla-144 |
| SEQ. ID. NO. 37338 | 149-IleSerAlaAsnSerAspGluGlnVal-157 |
| SEQ. ID. NO. 37339 | 163-GluAlaMetGluLysValGlyLysGluGlyValIleThrValGluAspGlyLysSerLeuGluAsnGluLeuAspVal-188 |
| SEQ. ID. NO. 37340 | 192-MetGlnPheAspArgGlyTyr-198 |
| SEQ. ID. NO. 37341 | 206-AspAlaGluLysGlnIleAla-212 |
| SEQ. ID. NO. 37342 | 222-PheAspLysLysIleSerAsnIleArgAsp-231 |
| SEQ. ID. NO. 37343 | 238-GlnValAlaLysAlaSerArg-244 |
| SEQ. ID. NO. 37344 | 251-GluAspValGluGlyGluAla-257 |
| SEQ. ID. NO. 37345 | 265-AsnIleArgGlyIleLeu-270 |
| SEQ. ID. NO. 37346 | 277-AlaProGlyPheGlyAspArgArgLysAlaMetLeu-288 |
| SEQ. ID. NO. 37347 | 300-IleSerGluGluValGlyLeuSerLeuGluLysAlaThrLeuAspAspLeuGlyGlnThrLysArgIleGluLeuGlyGluGluAsnThrThr-330 |
| SEQ. ID. NO. 37348 | 333-AspGlyPheGlyAspAlaAlaGlnIleGluAlaArgValAlaGluIleArgGlnGlnIleGluThrAlaThrSerAspTyrAspLysGluLysLeu GlnGluArgValAlaLysLeuAlaGly-373 |
| SEQ. ID. NO. 37349 | 384-ThrGluValGluMetLysGluLysLysAspArgValGluAspAlaLeuHis-400 |
| SEQ. ID. NO. 37350 | 404-AlaAlaValGluGluGlyVal-410 |
| SEQ. ID. NO. 37351 | 420-ArgAlaArgAlaAlaLeu-425 |
| SEQ. ID. NO. 37352 | 428-LeuHisThrGlyAsnAlaAspGlnAspAlaGlyVal-439 |
| SEQ. ID. NO. 37353 | 445-AlaValGluSerProLeuArg-451 |
| SEQ. ID. NO. 37354 | 456-AsnAlaGlyGlyGluProSerVal-463 |
| SEQ. ID. NO. 37355 | 468-ValLeuGluGlyLysGlyAsnTyrGlyTyr-477 |
| SEQ. ID. NO. 37356 | 479-AlaGlySerGlyGluTyrGlyAsp-486 |
| SEQ. ID. NO. 37357 | 494-AspProAlaLysValThrArgSerAlaLeu-503 |
| SEQ. ID. NO. 37358 | 522-GluIleProGluGluLysProAlaValProAspMetGlyGly-535 |
| Hydrophilic Regions - Hopp-Woods | |
| SEQ. ID. NO. 37359 | 5-LeuArgPheAspAsn-9 |
| SEQ. ID. NO. 37360 | 32-AlaLysGlyArgAsnValValVal-39 |
| SEQ. ID. NO. 37361 | 47-HisIleThrLysAspGlyValThrValAlaLysGluIleGluLeuLysAspLysPheGluAsn-67 |
| SEQ. ID. NO. 37362 | 72-MetValLysGluValAlaSerLysThrAsnAspValAlaGlyAspGlyThrThr-89 |
| SEQ. ID. NO. 37363 | 113-ThrAspLeuLysArgGlyIleAspLysAlaVal-123 |
| SEQ. ID. NO. 37364 | 128-GluGluLeuLysAsnIleAlaLysProCysAspThrSerLysGluIleAla-144 |
| SEQ. ID. NO. 37365 | 151-AlaAsnSerAspGluGlnVal-157 |
| SEQ. ID. NO. 37366 | 163-GluAlaMetGluLysValGlyLysGluGlyValIleThrValGluAspGlyLysSerLeuGluAsnGluLeuAspVal-188 |
| SEQ. ID. NO. 37367 | 206-AspAlaGluLysGlnIleAla-212 |
| SEQ. ID. NO. 37368 | 222-PheAspLysLysIleSerAsnIleArgAsp-231 |
| SEQ. ID. NO. 37369 | 238-GlnValAlaLysAlaSerArg-244 |

TABLE 1-continued

| | |
|---|---|
| SEQ. ID. NO. 37370 | 251-GluAspValGluGlyGluAla-257 |
| SEQ. ID. NO. 37371 | 279-GlyPheGlyAspArgArgLysAlaMetLeu-288 |
| SEQ. ID. NO. 37372 | 300-IleSerGluGluValGlyLeuSerLeuGluLysAlaThrLeuAspAspLeuGlyGlnThrLysArgIleGluIleGlyGluGluAsnThrThr-330 |
| SEQ. ID. NO. 37373 | 339-AlaGlnIleGluAlaArgValAlaGluIleArgGlnGlnIleGluThrAlaThrSerAspTyrAspLysGluLysLeuGlnGluArgValAlaLys-370 |
| SEQ. ID. NO. 37374 | 384-ThrGluValGluMetLysGluLysLysAspArgValGluAspAlaLeuHis-400 |
| SEQ. ID. NO. 37375 | 404-AlaAlaValGluGluGlyVal-410 |
| SEQ. ID. NO. 37376 | 420-ArgAlaArgAlaAlaLeu-425 |
| SEQ. ID. NO. 37377 | 431-GlyAsnAlaAspGlnAspAla-437 |
| SEQ. ID. NO. 37378 | 445-AlaValGluSerProLeu-450 |
| SEQ. ID. NO. 37379 | 457-AlaGlyGlyGluPro-461 |
| SEQ. ID. NO. 37380 | 468-ValLeuGluGlyLysGly-473 |
| SEQ. ID. NO. 37381 | 480-GlySerGlyGluTyrGlyAsp-486 |
| SEQ. ID. NO. 37382 | 494-AspProAlaLysValThrArg-500 |
| SEQ. ID. NO. 37383 | 522-GluIleProGluGluLysProAlaVal-530 |
| g986 | |
| AMPHI Regions - AMPHI | |
| SEQ. ID. NO. 37384 | 6-GlnTyrPheAlaLeuAlaAlaLeuCysAlaAlaLeuLeuAla-19 |
| SEQ. ID. NO. 37385 | 21-CysGluLysAlaGly-25 |
| SEQ. ID. NO. 37386 | 36-SerPheValGluArgIleGluHis-43 |
| SEQ. ID. NO. 37387 | 55-ProAspPheAlaGlnLeuValGln-62 |
| SEQ. ID. NO. 37388 | 97-AspProPheTyrGluPhePheLysArgLeuValProAsnMetProGluIleProGln-115 |
| SEQ. ID. NO. 37389 | 145-AlaGlyMetGlySerIle-150 |
| SEQ. ID. NO. 37390 | 162-AlaLysLeuIleGlySerAspVal-169 |
| SEQ. ID. NO. 37391 | 189-IleGlyAsnProLysAsnLeuLysProGly-198 |
| SEQ. ID. NO. 37392 | 200-TrpValAlaAlaIleGly-205 |
| SEQ. ID. NO. 37393 | 287-AlaGluGlnLeuLysAsnThrGlyLysVal-296 |
| SEQ. ID. NO. 37394 | 393-AlaAlaGluHisThrGly-398 |
| SEQ. ID. NO. 37395 | 471-ArgLysAlaMetAspLysAla-477 |
| Antigenic Index - Jameson-Wolf | |
| SEQ. ID. NO. 37396 | 20-GlyCysGluLysAlaGlySer-26 |
| SEQ. ID. NO. 37397 | 29-GlyAlaAspLysLysGluAlaSerPheValGluArgIleGluHisThrLysAspAspGlySerVal-50 |
| SEQ. ID. NO. 37398 | 61-ValGlnSerGluGlyProAla-67 |
| SEQ. ID. NO. 37399 | 75-ProAlaProArgThrGlnAsnGlySerGlyAsnAlaGluThrAspSerAspProLeuAlaAspSerAspProPhe-99 |
| SEQ. ID. NO. 37400 | 104-LysArgLeuValProAsnMetProGluIleProGlnGluGluAlaAspAspGlyGlyLeu-123 |
| SEQ. ID. NO. 37401 | 154-LeuAsnAspLysArgGluTyrThr-161 |
| SEQ. ID. NO. 37402 | 165-IleGlySerAspValGlnSerAspValAla-174 |
| SEQ. ID. NO. 37403 | 179-AspAlaThrGluGluLeuPro-185 |
| SEQ. ID. NO. 37404 | 189-IleGlyAsnProLysAsnLeuLysProGlyGlu-199 |
| SEQ. ID. NO. 37405 | 208-PheGlyPheAspAsnSerVal-214 |
| SEQ. ID. NO. 37406 | 219-ValSerAlaLysGlyArgSerLeuProAsnGluSerTyr-231 |
| SEQ. ID. NO. 37407 | 242-AsnProGlyAsnSerGlyGlyPro-249 |
| SEQ. ID. NO. 37408 | 265-TyrSerArgSerGlyGly-270 |
| SEQ. ID. NO. 37409 | 288-GluGlnLeuLysAsnThrGlyLysValGlnArgGlyGlnLeu-301 |
| SEQ. ID. NO. 37410 | 316-PheGlyLeuAspLysAlaSerGly-323 |
| SEQ. ID. NO. 37411 | 330-LeuProGlySerProAlaGluArgAlaGlyLeuGlnAlaGlyAsp-344 |
| SEQ. ID. NO. 37412 | 349-LeuAspGlyGlyGluIleArgSerSerGlyAspLeu-360 |
| SEQ. ID. NO. 37413 | 368-ThrProGlyLysGluValSer-374 |
| SEQ. ID. NO. 37414 | 378-TrpArgLysGlyGluGluIleThrIle-386 |
| SEQ. ID. NO. 37415 | 394-AlaGluHisThrGlyAlaSerSerLysThrAspGluAlaProTyrThrGluGlnGlnSerGlyThrPhe-416 |
| SEQ. ID. NO. 37416 | 427-ThrHisThrAspSerSerGlyLysHis-435 |
| SEQ. ID. NO. 37417 | 440-ArgValSerAspAlaAlaGluArgAlaGlyLeuArgArgGlyAspGluIleLeu-457 |
| SEQ. ID. NO. 37418 | 463-ProValAsnAspGluAlaGlyPheArgLysAlaMetAspLysAlaGlyLysAsnVal-481 |
| SEQ. ID. NO. 37419 | 486-MetArgArgGlyAsnThr-491 |
| Hydrophilic Regions - Hopp-Woods | |
| SEQ. ID. NO. 37420 | 20-GlyCysGluLysAlaGly-25 |
| SEQ. ID. NO. 37421 | 29-GlyAlaAspLysLysGluAlaSerPheValGluArgIleGluHisThrLysAspAspGlySer-49 |
| SEQ. ID. NO. 37422 | 75-ProAlaProArgThrGlnAsnGlySerGlyAsnAlaGluThrAspSerAspProLeuAlaAspSerAspPro-98 |
| SEQ. ID. NO. 37423 | 111-ProGluIleProGlnGluGluAlaAspAspGlyGly-122 |
| SEQ. ID. NO. 37424 | 154-LeuAsnAspLysArgGluTyrThr-161 |
| SEQ. ID. NO. 37425 | 179-AspAlaThrGluGluLeuPro-185 |
| SEQ. ID. NO. 37426 | 193-LysAsnLeuLysPro-197 |
| SEQ. ID. NO. 37427 | 221-AlaLysGlyArgSerLeuPro-227 |
| SEQ. ID. NO. 37428 | 288-GluGlnLeuLysAsnThrGlyLysValGlnArgGlyGln-300 |
| SEQ. ID. NO. 37429 | 317-GlyLeuAspLysAlaSer-322 |
| SEQ. ID. NO. 37430 | 333-SerProAlaGluArgAlaGlyLeuGln-341 |
| SEQ. ID. NO. 37431 | 350-AspGlyGlyGluIleArgSerSerGlyAsp-359 |
| SEQ. ID. NO. 37432 | 368-ThrProGlyLysGluValSer-374 |
| SEQ. ID. NO. 37433 | 379-ArgLysGlyGluGluIleThrIle-386 |
| SEQ. ID. NO. 37434 | 394-AlaGluHisThrGlyAlaSerSerLysThrAspGluAlaProTyrThrGluGlnGlnSer-413 |
| SEQ. ID. NO. 37435 | 428-HisThrAspSerSerGly-433 |
| SEQ. ID. NO. 37436 | 440-ArgValSerAspAlaAlaGluArgAlaGlyLeuArgArgGlyAspGluIleLeu-457 |
| SEQ. ID. NO. 37437 | 463-ProValAsnAspGluAlaGlyPheArgLysAlaMetAspLysAlaGlyLys-479 |
| g987 | |
| AMPHI Regions - AMPHI | |
| SEQ. ID. NO. 37438 | 17-CysSerSerTrpLeu-21 |
| SEQ. ID. NO. 37439 | 65-ProHisGluAlaPhe-69 |
| SEQ. ID. NO. 37440 | 121-AsnThrArgGly-124 |
| SEQ. ID. NO. 37441 | 135-HisProAsnIleValArgLeuPheAsnProPheValLeuArgLysTrpArgAlaLeuGlyTyrLeuThrAspPheProArgLeuAsnArg-164 |
| SEQ. ID. NO. 37442 | 186-GlyAspGluTyrPheLysVal-192 |
| SEQ. ID. NO. 37443 | 201-LeuAspIleLeuAlaThr-206 |

TABLE 1-continued

| | |
|---|---|
| SEQ. ID. NO. 37444 | 210-ValGlyGluValSerHisAspPheAspArgTyrTrpAla-222 |
| SEQ. ID. NO. 37445 | 229-AlaThrArgIleIleArgSerGly-236 |
| SEQ. ID. NO. 37446 | 238-IleGlyLysGlyLeuGlnAla-244 |
| SEQ. ID. NO. 37447 | 288-SerAspSerProAlaLysGlyLeuAspArg-297 |
| SEQ. ID. NO. 37448 | 306-GlyArgLeuGlnAspAlaLeuLysGlnPro-315 |
| SEQ. ID. NO. 37449 | 332-GlyThrAspAlaLeuAlaLysLeuValGlnAsp-342 |
| SEQ. ID. NO. 37450 | 354-GlnAlaThrAspValAlaAla-360 |
| SEQ. ID. NO. 37451 | 442-LysIleAlaGluGlnMetGluArgThrLeuAlaAspThrThrPro-456 |
| SEQ. ID. NO. 37452 | 485-ProGluAlaLysLeuTrpLysArgIleAlaAlaLysIleLeuSerLeuLeuProIleGluGlyLeu-506 |
| Antigenic Index - Jameson-Wolf | |
| SEQ. ID. NO. 37453 | 1-MetLysThrArgSer-5 |
| SEQ. ID. NO. 37454 | 23-ProLeuGluGluArgThrGluSerArgHisPheAsnThrSerLysProValLeu-40 |
| SEQ. ID. NO. 37455 | 49-HisThrProHisAsnAsnGlyLeuSer-57 |
| SEQ. ID. NO. 37456 | 77-GluSerAlaGluHisSerLeu-83 |
| SEQ. ID. NO. 37457 | 90-TrpArgAsnAspIleSerGlyArgLeu-98 |
| SEQ. ID. NO. 37458 | 107-AlaGluArgGlyValArg-112 |
| SEQ. ID. NO. 37459 | 115-LeuLeuLeuAspAspAsnAsnThrArgGlyLeuAsp-126 |
| SEQ. ID. NO. 37460 | 134-SerHisProAsnIle-138 |
| SEQ. ID. NO. 37461 | 158-AspPheProArgLeuAsnArgArgMetHisAsnLysSerPheThrAlaAspAsnArgAla-177 |
| SEQ. ID. NO. 37462 | 181-GlyGlyArgAsnIleGlyAspGluTyrPheLysValGlyGluAspThrVal-197 |
| SEQ. ID. NO. 37463 | 213-ValSerHisAspPheAspArgTyrTrp-221 |
| SEQ. ID. NO. 37464 | 224-HisSerAlaHisAsn-228 |
| SEQ. ID. NO. 37465 | 231-ArgIleIleArgSerGlyAsnIleGlyLysGlyLeu-242 |
| SEQ. ID. NO. 37466 | 246-GlyTyrAsnAspGluThrSerArg-253 |
| SEQ. ID. NO. 37467 | 258-ArgTyrArgGluThrValGlu-264 |
| SEQ. ID. NO. 37468 | 266-SerProLeuTyrGln-270 |
| SEQ. ID. NO. 37469 | 272-IleGlnThrGlyArgIleAsp-278 |
| SEQ. ID. NO. 37470 | 286-LeuIleSerAspSerProAlaLysGlyLeuAspArgAspArgArgLysProProIle-304 |
| SEQ. ID. NO. 37471 | 307-ArgLeuGlnAspAlaLeuLysGlnProGluLysSer-318 |
| SEQ. ID. NO. 37472 | 327-ValProThrLysSerGlyThrAspAlaLeu-336 |
| SEQ. ID. NO. 37473 | 339-LeuValGlnAspGlyIleAsp-345 |
| SEQ. ID. NO. 37474 | 366-ValLysTyrArgLysProLeuLeu-373 |
| SEQ. ID. NO. 37475 | 390-AlaThrLysAspLysGlyLeuThrGlySerSerVal-401 |
| SEQ. ID. NO. 37476 | 411-ValAspGlyLysArgIlePhe-417 |
| SEQ. ID. NO. 37477 | 421-PheAsnLeuAspProArgSerAlaArgLeuAsnThr-432 |
| SEQ. ID. NO. 37478 | 439-GluSerProLysIleAlaGluGlnMetGluArgThrLeuAlaAspThrThrProGluTyrAlaTyr-460 |
| SEQ. ID. NO. 37479 | 462-ValThrLeuAspLysHisAsnArgLeuGlnTrpHisAspProAlaThrArgLysThrTyrProAsnGluProGluAlaLysLeuTrpLys-491 |
| Hydrophilic Regions - Hopp-Woods | |
| SEQ. ID. NO. 37480 | 1-MetLysThrArgSer-5 |
| SEQ. ID. NO. 37481 | 24-LeuGluGluArgThrGluSerArgHisPheAsnThr-35 |
| SEQ. ID. NO. 37482 | 77-GluSerAlaGluHisSerLeu-83 |
| SEQ. ID. NO. 37483 | 107-AlaGluArgGlyValArg-112 |
| SEQ. ID. NO. 37484 | 115-LeuLeuLeuAspAspAsnAsnThrArgGlyLeuAsp-126 |
| SEQ. ID. NO. 37485 | 160-ProArgLeuAsnArgArgMetHisAsn-168 |
| SEQ. ID. NO. 37486 | 171-PheThrAlaAspAsnArgAla-177 |
| SEQ. ID. NO. 37487 | 188-GluTyrPheLysValGlyGluAspThrVal-197 |
| SEQ. ID. NO. 37488 | 213-ValSerHisAspPheAspArg-219 |
| SEQ. ID. NO. 37489 | 247-TyrAsnAspGluThrSerArg-253 |
| SEQ. ID. NO. 37490 | 258-ArgTyrArgGluThrValGlu-264 |
| SEQ. ID. NO. 37491 | 273-GlnThrGlyArgIleAsp-278 |
| SEQ. ID. NO. 37492 | 290-SerProAlaLysGlyLeuAspArgAspArgArgLysProProIle-304 |
| SEQ. ID. NO. 37493 | 307-ArgLeuGlnAspAlaLeuLysGlnProGluLysSer-318 |
| SEQ. ID. NO. 37494 | 330-LysSerGlyThrAspAlaLeu-336 |
| SEQ. ID. NO. 37495 | 339-LeuValGlnAspGlyIleAsp-345 |
| SEQ. ID. NO. 37496 | 366-ValLysTyrArgLysProLeuLeu-373 |
| SEQ. ID. NO. 37497 | 390-AlaThrLysAspLysGlyLeuThr-397 |
| SEQ. ID. NO. 37498 | 423-LeuAspProArgSerAlaArgLeuAsnThr-432 |
| SEQ. ID. NO. 37499 | 439-GluSerProLysIleAlaGluGlnMetGluArgThrLeuAla-452 |
| SEQ. ID. NO. 37500 | 463-ThrLeuAspLysHisAsnArg-469 |
| SEQ. ID. NO. 37501 | 475-ProAlaThrArgLysThrTyrProAsnGluProGluAlaLysLeuTrpLys-491 |
| g988 | |
| AMPHI Regions - AMPHI | |
| SEQ. ID. NO. 37502 | 45-SerLysIleGluSerLeuAlaArg-52 |
| SEQ. ID. NO. 37503 | 125-GlnMetArgGlyVal-129 |
| SEQ. ID. NO. 37504 | 154-AspIleValGluArgAlaGlnSerLysVal-163 |
| SEQ. ID. NO. 37505 | 221-AlaLysIleIleGluValLeuGlyAspTyrAlaAsp-232 |
| SEQ. ID. NO. 37506 | 248-HisArgPheSerGluAlaCysAlaLysSerAlaLysLysIleProAspHisValArgLys-267 |
| SEQ. ID. NO. 37507 | 288-ThrAlaArgAspPheAspAsp-294 |
| SEQ. ID. NO. 37508 | 299-GluLysValGlyArgAsnTyr-305 |
| SEQ. ID. NO. 37509 | 310-AlaIleAlaAspValSerHisTyrValArgProAspAsp-322 |
| SEQ. ID. NO. 37510 | 348-AsnLeuSerAsnGly-352 |
| SEQ. ID. NO. 37511 | 396-AsnGlnValTrpLysTrpLeuSerAspGlyIleGlyAsnProHisLys-411 |
| SEQ. ID. NO. 37512 | 413-GlnIleAspThrLeuTyrLysLeuPheLysIleLeuGlnLys-426 |
| SEQ. ID. NO. 37513 | 494-LeuGlyProThrProGluLysLeuAlaThrLeu-504 |
| SEQ. ID. NO. 37514 | 524-LysAspTyrAlaAlaLeuAlaGlyGlnPheLys-534 |
| SEQ. ID. NO. 37515 | 544-ValMetMetLeuArgSerMetGlnGlnAla-553 |
| SEQ. ID. NO. 37516 | 555-TyrGluProHisCys-559 |
| SEQ. ID. NO. 37517 | 569-AlaTyrAlaHisPheThrSerProIleArgArgTyrProAspLeuThrValHisArgAlaIleLysAlaVal-592 |
| SEQ. ID. NO. 37518 | 618-AlaAspAspAlaGlyArgAspValGluAsnTrpLeuLys-630 |

TABLE 1-continued

| | |
|---|---|
| SEQ. ID. NO. 37519 | 641-IlePheGluGlyLysIleSerArgGly-649 |
| SEQ. ID. NO. 37520 | 653-PheGlyIlePheValThrLeu-659 |
| SEQ. ID. NO. 37521 | 667-LeuValHisIleSerAspLeuGlyGlu-675 |
| Antigenic Index - Jameson-Wolf | |
| SEQ. ID. NO. 37522 | 1-MetAsnLysAsnIleLys-6 |
| SEQ. ID. NO. 37523 | 8-LeuAsnLeuArgGluLysAspProPheLeuSerArgGluLysGlnArgTyrGluHisProLeuProSerArgGluTrpIle-34 |
| SEQ. ID. NO. 37524 | 37-LeuLeuGluArgLysGlyValProSerLysIleGluSerLeuAlaArgGluLeuSerIleThrGluAspGluTyrValPhePheGluArgArgLeuLysAlaMetAlaArgAspGlyGln-76 |
| SEQ. ID. NO. 37525 | 79-IleAsnArgArgGlyAlaVal-85 |
| SEQ. ID. NO. 37526 | 87-AlaAlaAspLysLeuAspLeuValLysCysArgValGluAlaHisLysAspGlyPhe-105 |
| SEQ. ID. NO. 37527 | 113-ProMetAspGluGlyAsp-118 |
| SEQ. ID. NO. 37528 | 124-ArgGlnMetArgGlyValMetHisGlyAspThrValThr-136 |
| SEQ. ID. NO. 37529 | 138-ArgProAlaGlyMetAspArgArgGlyArgArgGluGlyThrPhe-152 |
| SEQ. ID. NO. 37530 | 154-AspIleValGluArgAlaGlnSerLysValVal-164 |
| SEQ. ID. NO. 37531 | 168-TyrMetAspArgGlyValAla-174 |
| SEQ. ID. NO. 37532 | 176-LeuGluProGluAspLysArgLeuAsnGlnSerIle-187 |
| SEQ. ID. NO. 37533 | 189-LeuGluProAspGlyValAlaArgPheLysProGluSerGlyGln-203 |
| SEQ. ID. NO. 37534 | 210-GluValTyrProGluGlnAsnArgProAlaVal-220 |
| SEQ. ID. NO. 37535 | 227-LeuGlyAspTyrAlaAspSerGlyMetGluIle-237 |
| SEQ. ID. NO. 37536 | 239-IleAlaValArgLysHisHisLeuProHisArgPheSerGluAlaCysAlaLysSerAlaLysLysIleProAspHisValArgLysSerAspLeuLysGlyArgValAspLeuCys-277 |
| SEQ. ID. NO. 37537 | 283-ThrIleAspGlyGluThrAlaArgAspPheAspAsp-294 |
| SEQ. ID. NO. 37538 | 299-GluLysValGlyArgAsnTyrArg-306 |
| SEQ. ID. NO. 37539 | 316-HisTyrValArgProAspAspAlaIleAspAlaAspAlaGlnGluArgSerThrSerValTyrPheProArgArgMetIleProMetLeuProGluAsnLeuSerAsnGlyIleCysSerLeuAsnProAspValGluArgLeu-363 |
| SEQ. ID. NO. 37540 | 374-AlaGlyAsnIleLysGluTyrArgPhe-382 |
| SEQ. ID. NO. 37541 | 393-LeuThrTyrAsnGln-397 |
| SEQ. ID. NO. 37542 | 402-LeuSerAspGlyIleGlyAsnProHisLysAlaGlnIle-414 |
| SEQ. ID. NO. 37543 | 424-LeuGlnLysLysArgLeuAlaArgGlyAlaValGluPheGluSerValGlu-440 |
| SEQ. ID. NO. 37544 | 443-MetIlePheAspAspAsnGlyLysIleGluLys-453 |
| SEQ. ID. NO. 37545 | 458-ValArgAsnAspAlaHisLysLeuIleGlu-467 |
| SEQ. ID. NO. 37546 | 482-LeuLysAsnLysHisThrAla-488 |
| SEQ. ID. NO. 37547 | 493-HisLeuGlyProThrProGluLysLeuAlaThrLeuArgGluGlnLeu-508 |
| SEQ. ID. NO. 37548 | 516-GlyGlyGlyAspAsnProSerProLysAspTyrAlaAla-528 |
| SEQ. ID. NO. 37549 | 531-GluGlnPheLysGlyArgProAspAlaGluLeu-541 |
| SEQ. ID. NO. 37550 | 555-TyrGluProHisCysGluGlyHis-562 |
| SEQ. ID. NO. 37551 | 575-SerProIleArgArgTyrProAspLeuThrVal-585 |
| SEQ. ID. NO. 37552 | 592-ValLeuAsnArgLysThrTyrThrProAsnLysSerTrp-604 |
| SEQ. ID. NO. 37553 | 613-PheCysGluArgArgAlaAspAspAlaGlyArgAspValGluAsn-627 |
| SEQ. ID. NO. 37554 | 633-TyrMetArgAspLysValGlyGluIlePheGluGlyLysIleSerArgGlyValAla-651 |
| SEQ. ID. NO. 37555 | 671-SerAspLeuGlyGluAspTyrPheAsnPheArgPro-682 |
| SEQ. ID. NO. 37556 | 684-IleMetAlaIleGluGlyGluArgSerGlyIleArgPheAsnMetGlyAspArgValAlaValArgValAlaArgAlaAspLeuAspAspGlyLysIle-716 |
| SEQ. ID. NO. 37557 | 724-GluSerGlyArgArgArgLysValLysLeu-733 |
| SEQ. ID. NO. 37558 | 735-AlaSerAlaLysProAlaGlyAlaAlaGlyLysGlyLysSerLysThrThrAlaGluLysLysThrAlaArgCysGlyLysValArgGlyArgGlyValProAla-769 |
| SEQ. ID. NO. 37559 | 771-AlaGluSerGlyLysLysAlaLysLysProValProIleLysValLysLysArgLysGlyLysSer-792 |
| Hydrophilic Regions - Hopp-Woods | |
| SEQ. ID. NO. 37560 | 1-MetAsnLysAsnIleLys-6 |
| SEQ. ID. NO. 37561 | 8-LeuAsnLeuArgGluLysAspProPheLeuSerArgGluLysGlnArgTyrGluHis-26 |
| SEQ. ID. NO. 37562 | 37-LeuLeuGluArgLysGlyValProSerLysIleGluSerLeuAlaArgGluLeuSerIleThrGluAspGluTyrValPhePheGluArgArgLeuLysAlaMetAlaArgAspGlyGln-76 |
| SEQ. ID. NO. 37563 | 79-IleAsnArgArgGlyAla-84 |
| SEQ. ID. NO. 37564 | 87-AlaAlaAspLysLeuAspLeuValLysCysArgValGluAlaHisLysAspGlyPhe-105 |
| SEQ. ID. NO. 37565 | 113-ProMetAspGluGlyAsp-118 |
| SEQ. ID. NO. 37566 | 140-AlaGlyMetAspArgArgGlyArgArgGluGlyThr-151 |
| SEQ. ID. NO. 37567 | 155-IleValGluArgAlaGlnSerLysValVal-164 |
| SEQ. ID. NO. 37568 | 176-LeuGluProGluAspLysArgLeuAsn-184 |
| SEQ. ID. NO. 37569 | 189-LeuGluProAspGlyValAlaArgPheLysProGluSerGly-202 |
| SEQ. ID. NO. 37570 | 210-GluValTyrProGluGlnAsnArgProAlaVal-220 |
| SEQ. ID. NO. 37571 | 230-TyrAlaAspSerGlyMetGluIle-237 |
| SEQ. ID. NO. 37572 | 239-IleAlaValArgLysHisHisLeu-246 |
| SEQ. ID. NO. 37573 | 249-ArgPheSerGluAlaCysAlaLysSerAlaLysLysIleProAspHisValArgLysSerAspLeuLysGlyArgValAspLeu-276 |
| SEQ. ID. NO. 37574 | 284-IleAspGlyGluThrAlaArgAspPheAspAsp-294 |
| SEQ. ID. NO. 37575 | 299-GluLysValGlyArgAsnTyr-305 |
| SEQ. ID. NO. 37576 | 318-ValArgProAspAspAlaIleAspAlaAspAlaGlnGluArgSerThr-333 |
| SEQ. ID. NO. 37577 | 358-ProAspValGluArg-362 |
| SEQ. ID. NO. 37578 | 376-AsnIleLysGluTyrArg-381 |
| SEQ. ID. NO. 37579 | 406-IleGlyAsnProHisLysAlaGlnIle-414 |
| SEQ. ID. NO. 37580 | 424-LeuGlnLysLysArgLeuAlaArgGlyAlaValGluPheGluSerValGlu-440 |
| SEQ. ID. NO. 37581 | 443-MetIlePheAspAspAsnGlyLysIleGluLys-453 |
| SEQ. ID. NO. 37582 | 458-ValArgAsnAspAlaHisLysLeuIleGlu-467 |
| SEQ. ID. NO. 37583 | 496-ProThrProGluLysLeuAlaThrLeuArgGluGlnLeu-508 |
| SEQ. ID. NO. 37584 | 517-GlyGlyAspAsnProSerProLysAspTyrAlaAla-528 |
| SEQ. ID. NO. 37585 | 531-GluGlnPheLysGlyArgProAspAlaGluLeu-541 |
| SEQ. ID. NO. 37586 | 576-ProIleArgArgTyrProAsp-582 |
| SEQ. ID. NO. 37587 | 592-ValLeuAsnArgLysThrTyrThrPro-600 |
| SEQ. ID. NO. 37588 | 613-PheCysGluArgArgAlaAspAspAlaGlyArgAspValGluAsn-627 |
| SEQ. ID. NO. 37589 | 633-TyrMetArgAspLysValGlyGluIlePheGluGlyLysIleSerArg-648 |

TABLE 1-continued

| | |
|---|---|
| SEQ. ID. NO. 37590 | 684-IleMetAlaIleGluGlyGluArgSerGlyIle-694 |
| SEQ. ID. NO. 37591 | 697-AsnMetGlyAspArgValAlaValArgValAlaArgAlaAspLeuAspAspGlyLysIle-716 |
| SEQ. ID. NO. 37592 | 724-GluSerGlyArgArgArgLysValLysLeu-733 |
| SEQ. ID. NO. 37593 | 735-AlaSerAlaLysProAlaGlyAlaAlaGlyLysGlyLysSerLysThrThrAlaGluLysLysThrAlaArgCysGlyLysValArgGlyArgGly-766 |
| SEQ. ID. NO. 37594 | 771-AlaGluSerGlyLysLysAlaLysLysProValProIleLysValLysLysArgLysGlyLysSer-792 | g989
AMPHI Regions - AMPHI

| | |
|---|---|
| SEQ. ID. NO. 37595 | 36-AlaGlnSerThrAlaAsnAlaAla-43 |
| SEQ. ID. NO. 37596 | 53-AlaGlyLeuThrLysLeu-58 |
| SEQ. ID. NO. 37597 | 80-SerAlaThrAspPhe-84 |
| SEQ. ID. NO. 37598 | 104-ProHisIleTyrGlyAla-109 |
| SEQ. ID. NO. 37599 | 178-GluLeuArgLysTyrAlaAspGlyIle-186 |
| SEQ. ID. NO. 37600 | 195-AlaThrProSerAsnProThr-201 |
| SEQ. ID. NO. 37601 | 287-ValThrProGluSer-291 |
| SEQ. ID. NO. 37602 | 293-SerValHisGlyMetTyrLysValSer-301 |
| SEQ. ID. NO. 37603 | 312-TrpThrArgHisSerArg-317 |
| SEQ. ID. NO. 37604 | 357-SerTyrGlnIleSerGluPro-363 |
| SEQ. ID. NO. 37605 | 439-SerCysAlaArgPheLysAsnHisAlaAsp-448 |

Antigenic Index - Jameson-Wolf

| | |
|---|---|
| SEQ. ID. NO. 37606 | 41-AsnAlaAlaAspAlaSer-46 |
| SEQ. ID. NO. 37607 | 52-ProAlaGlyLeuThrLysLeuAspSerSerGlnIle-63 |
| SEQ. ID. NO. 37608 | 76-TyrGluAlaAspSerAlaThrAspPheThr-85 |
| SEQ. ID. NO. 37609 | 89-ValGlnGlySerLysAsnGlyLysIleThrLysThrThr-101 |
| SEQ. ID. NO. 37610 | 111-LysValAsnAspAsnLeuThr-117 |
| SEQ. ID. NO. 37611 | 127-GlySerAlaThrGluTyrGluLysAspSerValLeu-138 |
| SEQ. ID. NO. 37612 | 141-AsnIleAsnLysLeuGly-146 |
| SEQ. ID. NO. 37613 | 159-LysLeuAsnGluArgHisSerPheGly-167 |
| SEQ. ID. NO. 37614 | 174-HisAsnSerAlaGluLeuArgLysTyrAlaAspGlyIleProLysLysAlaGln-191 |
| SEQ. ID. NO. 37615 | 196-ThrProSerAsnPro-200 |
| SEQ. ID. NO. 37616 | 206-IleLysAlaAspGlyHisAlaAspValLysGlySerAspTrpGly-220 |
| SEQ. ID. NO. 37617 | 230-AspIleAsnAspArgAlaArgValGlyValAsnTyrArgSerLysValSerHisThrLeuLysGlyAspAlaGluTrpAlaAla-257 |
| SEQ. ID. NO. 37618 | 259-GlyAlaAlaAlaLysGlnGlnTrpAsnAspAsnMet-270 |
| SEQ. ID. NO. 37619 | 278-AlaAsnGluLysAlaSerVal-284 |
| SEQ. ID. NO. 37620 | 287-ValThrProGluSer-291 |
| SEQ. ID. NO. 37621 | 298-TyrLysValSerAspLysAlaAspLeu-306 |
| SEQ. ID. NO. 37622 | 313-ThrArgHisSerArgPheAsnLys-320 |
| SEQ. ID. NO. 37623 | 323-LeuPhePheGluLysGluLysAsnIleAlaAsnGlyLysLysSerAspArgThrThrIleThrProAsnTrpArgAsnThrTyrLys-351 |
| SEQ. ID. NO. 37624 | 353-GlyLeuGlyGlySerTyrGlnIleSerGlu-362 |
| SEQ. ID. NO. 37625 | 372-PheAspLysProProValArgAsnAlaAspTyrArgMetAsnSerLeuProAspGlyAsnArg-392 |
| SEQ. ID. NO. 37626 | 402-HisIleGlyLysAsnHisVal-408 |
| SEQ. ID. NO. 37627 | 419-AsnAspThrSerTyrArgThrAlaLysAlaSerGlyAsnAspValAspSerLysGlyAlaSerCysAlaArgPheLysAsnHisAla-447 |

Hydrophilic Regions - Hopp-Woods

| | |
|---|---|
| SEQ. ID. NO. 37628 | 56-ThrLysLeuAspSerSerGln-62 |
| SEQ. ID. NO. 37629 | 76-TyrGluAlaAspSerAlaThr-82 |
| SEQ. ID. NO. 37630 | 90-GlnGlySerLysAsnGlyLysIleThrLys-99 |
| SEQ. ID. NO. 37631 | 130-ThrGluTyrGluLysAspSerValLeu-138 |
| SEQ. ID. NO. 37632 | 159-LysLeuAsnGluArgHisSer-165 |
| SEQ. ID. NO. 37633 | 175-AsnSerAlaGluLeuArgLysTyrAlaAspGlyIleProLysLysAlaGln-191 |
| SEQ. ID. NO. 37634 | 206-IleLysAlaAspGlyHisAlaAspValLysGlySerAsp-218 |
| SEQ. ID. NO. 37635 | 231-IleAsnAspArgAlaArgVal-237 |
| SEQ. ID. NO. 37636 | 241-TyrArgSerLysVal-245 |
| SEQ. ID. NO. 37637 | 249-LeuLysGlyAspAlaGluTrpAlaAla-257 |
| SEQ. ID. NO. 37638 | 278-AlaAsnGluLysAlaSerVal-284 |
| SEQ. ID. NO. 37639 | 299-LysValSerAspLysAlaAspLeu-306 |
| SEQ. ID. NO. 37640 | 316-SerArgPheAsnLys-320 |
| SEQ. ID. NO. 37641 | 323-LeuPhePheGluLysGluLysAsnIleAlaAsnGlyLysLysSerAspArgThrThrIle-342 |
| SEQ. ID. NO. 37642 | 372-PheAspLysProProValArgAsnAlaAspTyrArgMet-384 |
| SEQ. ID. NO. 37643 | 386-SerLeuProAspGlyAsn-391 |
| SEQ. ID. NO. 37644 | 421-ThrSerTyrArgThrAlaLysAlaSerGlyAsnAspValAspSerLysGlyAlaSer-439 |
| SEQ. ID. NO. 37645 | 441-AlaArgPheLysAsnHisAla-447 | g992
AMPHI Regions - AMPHI

| | |
|---|---|
| SEQ. ID. NO. 37646 | 6-ArgHisLeuLysAsnMetGlnIleLysLysIleMetLysTrp-19 |
| SEQ. ID. NO. 37647 | 24-LeuSerLeuLeuGlyAlaLeuGlyTyr-32 |
| SEQ. ID. NO. 37648 | 45-AlaValLeuAspValLeuGlyThr-52 |
| SEQ. ID. NO. 37649 | 72-HisSerTyrThrGlyThrValSerLysValTyr-82 |
| SEQ. ID. NO. 37650 | 140-TyrGlnArgGluValAlaGlnVal-147 |
| SEQ. ID. NO. 37651 | 158-GlnValGlnAspGly-162 |
| SEQ. ID. NO. 37652 | 179-AspPheAlaAspTyr-183 |

Antigenic Index - Jameson-Wolf

| | |
|---|---|
| SEQ. ID. NO. 37653 | 1-MetPheArgArgHisArgHisLeuLys-9 |
| SEQ. ID. NO. 37654 | 33-ThrGlyTyrAspSerGluAlaValArg-41 |
| SEQ. ID. NO. 37655 | 51-GlyThrAlaGlyAspValGlyPhe-58 |
| SEQ. ID. NO. 37656 | 60-AlaProValArgArgArgAlaSerAlaLysSerGlyHisSerTyr-74 |
| SEQ. ID. NO. 37657 | 79-SerLysValTyrAspGlyAspThr-86 |
| SEQ. ID. NO. 37658 | 90-IleAspGlyAspGlyAlaLysHisLysIle-99 |
| SEQ. ID. NO. 37659 | 105-AspAlaProGluMetLysGlnAlaTyrGlyThrArgSerArgAspAsnLeuArgAlaAlaAlaGluGlyArgLysValSer-131 |
| SEQ. ID. NO. 37660 | 134-ValPheGluThrAspArgTyrGlnArgGluValAla-145 |
| SEQ. ID. NO. 37661 | 148-SerAlaGlyLysThrAspLeu-154 |
| SEQ. ID. NO. 37662 | 168-LysSerTyrAlaLysGluGlnGlnAspLysAlaAspPhe-180 |

TABLE 1-continued

| | |
|---|---|
| SEQ. ID. NO. 37663 | 187-GlnIleGlnAlaGluArgGluArgLysGlyLeuTrpLysAlaLysAsnProGlnAlaPro-206 |
| SEQ. ID. NO. 37664 | 208-AlaTyrArgArgAlaGlyArgSerGlyGlyGlyAsnLysAspTrpMetAspSerValGlyGlu-228 |
| Hydrophilic Regions - Hopp-Woods | |
| SEQ. ID. NO. 37665 | 1-MetPheArgArgHisArgHisLeuLys-9 |
| SEQ. ID. NO. 37666 | 35-TyrAspSerGluAlaValArg-41 |
| SEQ. ID. NO. 37667 | 60-AlaProValArgArgArgAlaSerAlaLysSerGlyHis-72 |
| SEQ. ID. NO. 37668 | 80-LysValTyrAspGlyAspThr-86 |
| SEQ. ID. NO. 37669 | 90-IleAspGlyAspGlyAlaLysHisLysIle-99 |
| SEQ. ID. NO. 37670 | 105-AspAlaProGluMetLysGln-111 |
| SEQ. ID. NO. 37671 | 113-TyrGlyThrArgSerArgAspAsnLeuArgAlaAlaAlaGluGlyArgLysValSer-131 |
| SEQ. ID. NO. 37672 | 134-ValPheGluThrAspArgTyrGlnArgGluValAla-145 |
| SEQ. ID. NO. 37673 | 148-SerAlaGlyLysThrAspLeu-154 |
| SEQ. ID. NO. 37674 | 169-SerTyrAlaLysGluGlnGlnAspLysAlaAspPhe-180 |
| SEQ. ID. NO. 37675 | 187-GlnIleGlnAlaGluArgGluArgLysGlyLeuTrpLysAlaLysAsnPro-203 |
| SEQ. ID. NO. 37676 | 211-ArgAlaGlyArgSerGlyGlyGlyAsnLysAspTrpMetAspSerVal-226 |
| g993 | |
| AMPHI Regions - AMPHI | |
| SEQ. ID. NO. 37677 | 6-GlySerPheGlnGlyProLeuAspLeuLeuLeu-16 |
| SEQ. ID. NO. 37678 | 35-ThrGlyGlnTyrLeuHisTyrIleAlaGlnMet-45 |
| SEQ. ID. NO. 37679 | 105-GlyLeuAspAlaLeuProArgAla-112 |
| SEQ. ID. NO. 37680 | 133-GluValTyrIleAlaAspLeuMetGlnAlaTrpLeuGly-145 |
| SEQ. ID. NO. 37681 | 152-HisThrArgSerHisGluValIle-159 |
| SEQ. ID. NO. 37682 | 169-MetThrAlaIleLeuArgArgLeuAsnGluHisGlyIleCysArgPheHisAlaLeuPheAsn-189 |
| SEQ. ID. NO. 37683 | 198-IleValAsnPheIleAlaLeuLeu-205 |
| Antigenic Index - Jameson-Wolf | |
| SEQ. ID. NO. 37684 | 7-SerPheGlnGlyProLeu-12 |
| SEQ. ID. NO. 37685 | 20-ArgLysGlnAsnIleAsp-25 |
| SEQ. ID. NO. 37686 | 70-LeuLeuLeuProArgThrGluAlaValGluAspGluGluAlaAspProArgAlaGluLeuValArg-91 |
| SEQ. ID. NO. 37687 | 108-AlaLeuProArgAlaGlyArgAspPhe-116 |
| SEQ. ID. NO. 37688 | 125-IleAlaAlaGluThrLysLeuPro-132 |
| SEQ. ID. NO. 37689 | 148-SerArgAlaLysHisThrArgSerHisGluValIleGln-160 |
| SEQ. ID. NO. 37690 | 174-ArgArgLeuAsnGluHisGlyIle-181 |
| SEQ. ID. NO. 37691 | 189-AsnProGluGlnGly-193 |
| SEQ. ID. NO. 37692 | 207-LeuAlaLysGluGlyLeu-212 |
| SEQ. ID. NO. 37693 | 216-ValGlnGluAspGlyPheGlyGluIleArgIle-226 |
| SEQ. ID. NO. 37694 | 228-LeuAsnHisGluGlyAlaHisSerAspGlyIlePheGlyThrArgGlyGlyArgAspValPhe-248 |
| Hydrophilic Regions - Hopp-Woods | |
| SEQ. ID. NO. 37695 | 20-ArgLysGlnAsnIleAsp-25 |
| SEQ. ID. NO. 37696 | 70-LeuLeuLeuProArgThrGluAlaValGluAspGluGluAlaAspProArgAlaGluLeuValArg-91 |
| SEQ. ID. NO. 37697 | 108-AlaLeuProArgAlaGlyArg-114 |
| SEQ. ID. NO. 37698 | 125-IleAlaAlaGluThrLysLeuPro-132 |
| SEQ. ID. NO. 37699 | 148-SerArgAlaLysHisThrArgSerHisGluValIleGln-160 |
| SEQ. ID. NO. 37700 | 174-ArgArgLeuAsnGlu-178 |
| SEQ. ID. NO. 37701 | 207-LeuAlaLysGluGlyLeu-212 |
| SEQ. ID. NO. 37702 | 216-ValGlnGluAspGlyPheGly-222 |
| SEQ. ID. NO. 37703 | 242-ArgGlyGlyArgAspValPhe-248 |
| g996 | |
| AMPHI Regions - AMPHI | |
| SEQ. ID. NO. 37704 | 21-LysSerAlaArgThrHisAlaLysIlePro-30 |
| SEQ. ID. NO. 37705 | 50-ProGlyGluSerTyrProAlaGlnLeuGlnLysLeuThrGlyTrpAsn-65 |
| SEQ. ID. NO. 37706 | 75-ThrSerAlaGlnAlaLeuSerArgLeuProAla-85 |
| SEQ. ID. NO. 37707 | 104-LeuArgLysValProGluGlu-110 |
| SEQ. ID. NO. 37708 | 115-AsnIleAlaLysIleIleGluThrValGlnLys-125 |
| SEQ. ID. NO. 37709 | 140-LeuGlyAlaLeuPheGlyHisLeuSerAsp-149 |
| SEQ. ID. NO. 37710 | 167-GlyAlaTrpAlaGlu-171 |
| SEQ. ID. NO. 37711 | 186-AsnGlyLysGlyTyrArgLysPheAlaGluAsnLeuAsnGlnPheLeuArgLysHisGlyPhe-206 |
| Antigenic Index - Jameson-Wolf | |
| SEQ. ID. NO. 37712 | 1-MetAsnArgArgThrPhe-6 |
| SEQ. ID. NO. 37713 | 18-CysGlyArgLysSerAlaArgThrHisAlaLysIleProGluGlySerThr-34 |
| SEQ. ID. NO. 37714 | 46-TyrGlyAlaAsnProGlyGluSerTyrPro-55 |
| SEQ. ID. NO. 37715 | 69-GlyGlyValSerGlyAspThrSerAla-77 |
| SEQ. ID. NO. 37716 | 87-LeuAlaArgLysProLys-92 |
| SEQ. ID. NO. 37717 | 99-GlyGlyAsnAspPheLeuArgLysValProGluGluGlnThrArgAlaAsnIle-116 |
| SEQ. ID. NO. 37718 | 121-GluThrValGlnLysGluAsnIle-128 |
| SEQ. ID. NO. 37719 | 148-SerAspHisProLeuTyrGluAspLeuSerGluGluTyrGly-161 |
| SEQ. ID. NO. 37720 | 174-GlyAsnAsnAsnLeu-LysSerAspGlnIleHisAlaAsnGlyLysGlyTyrArgLysPheAlaGluAsnLeuAsnGlnPheLeuArgLysHisGlyPheArg-207 |
| Hydrophilic Regions - Hopp-Woods | |
| SEQ. ID. NO. 37721 | 18-CysGlyArgLysSerAlaArgThrHisAlaLysIleProGlu-31 |
| SEQ. ID. NO. 37722 | 49-AsnProGlyGluSerTyr-54 |
| SEQ. ID. NO. 37723 | 71-ValSerGlyAspThrSerAla-77 |
| SEQ. ID. NO. 37724 | 87-LeuAlaArgLysProLys-92 |
| SEQ. ID. NO. 37725 | 102-AspPheLeuArgLysValProGluGluGlnThrArgAlaAsnIle-116 |
| SEQ. ID. NO. 37726 | 121-GluThrValGlnLysGluAsnIle-128 |
| SEQ. ID. NO. 37727 | 154-GluAspLeuSerGluGluTyrGly-161 |
| SEQ. ID. NO. 37728 | 177-AsnLeuLysSerAspGlnIleHisAlaAsn-186 |
| SEQ. ID. NO. 37729 | 188-LysGlyTyrArgLysPheAlaGlu-195 |
| g997 | |
| AMPHI Regions - AMPHI | |
| SEQ. ID. NO. 37730 | 18-TrpAlaGlyLeuSerAlaAlaVal-25 |

TABLE 1-continued

| SEQ. ID. NO. 37731 | 70-TyrArgGlyValLeuArgLeuMetLysThrIleGly-81 |
| --- | --- |
| SEQ. ID. NO. 37732 | 107-ProLeuProAlaProLeuHisIle-114 |
| SEQ. ID. NO. 37733 | 123-ArgValProSerAlaPheLysAlaLysLeuLeuAlaAspMetSerAspLeuGlnLysSerAlaArgLeuGly-146 |
| SEQ. ID. NO. 37734 | 164-AlaAlaValMetGlnPheTrpGlnProLeuValTrpGly-176 |
| SEQ. ID. NO. 37735 | 189-ValLeuCysAsnValLeuSerAsp-196 |
| SEQ. ID. NO. 37736 | 222-AlaLeuAlaGluLeuGlnArg-228 |
| SEQ. ID. NO. 37737 | 241-ArgLeuAsnThrLeuPro-246 |
| SEQ. ID. NO. 37738 | 275-GluGlyThrProGluHisValGlnThrAla-284 |
| SEQ. ID. NO. 37739 | 300-TyrAlaGluProValArgLeuProAlaProLeuThrGlyIleAlaAspGly-316 |
| Antigenic Index - Jameson-Wolf | |
| SEQ. ID. NO. 37740 | 3-AsnThrProHisProArgProLysIle-11 |
| SEQ. ID. NO. 37741 | 37-GluAlaGlyArgGlnAlaGlyGlyArgAlaArgThrLeuAlaGlyAsnThrAspGlyPheGly-57 |
| SEQ. ID. NO. 37742 | 78-LysThrIleGlySerAspProArgAlaAla-87 |
| SEQ. ID. NO. 37743 | 122-ArgArgValProSerAlaPheLys-129 |
| SEQ. ID. NO. 37744 | 132-LeuLeuAlaAspMetSerAspLeuGlnLysSerAlaArgLeuGlyGlnProAspThrThr-151 |
| SEQ. ID. NO. 37745 | 156-LeuLysGlnArgAsnValProArg-163 |
| SEQ. ID. NO. 37746 | 180-ThrProLeuGluThrAlaSer-186 |
| SEQ. ID. NO. 37747 | 197-GlyValLeuThrLysLysSerGlySerAspTyrLeuLeuProLysGlnAspLeu-214 |
| SEQ. ID. NO. 37748 | 225-GluLeuGlnArgLeuGlyAlaAspIleArgLeuGluThrArgValCysArg-241 |
| SEQ. ID. NO. 37749 | 243-AsnThrLeuProAspGlyLysVal-250 |
| SEQ. ID. NO. 37750 | 273-LeuProGluGlyThrProGluHisVal-281 |
| SEQ. ID. NO. 37751 | 324-ProGlyGlnAlaProAspCysProGlnAsnGluValSer-336 |
| SEQ. ID. NO. 37752 | 341-ValSerAspArgValGlyAlaPheAlaAsnArgTerTerTerTer-355 |
| Hydrophilic Regions - Hopp-Woods | |
| SEQ. ID. NO. 37753 | 5-ProHisProArgProLysIle-11 |
| SEQ. ID. NO. 37754 | 37-GluAlaGlyArgGlnAlaGlyGlyArgAlaArgThrLeuAlaGlyAsn-52 |
| SEQ. ID. NO. 37755 | 80-IleGlySerAspProArgAlaAla-87 |
| SEQ. ID. NO. 37756 | 122-ArgArgValProSer-126 |
| SEQ. ID. NO. 37757 | 132-LeuLeuAlaAspMetSerAspLeuGlnLysSerAlaArgLeuGlyGlnProAspThrThr-151 |
| SEQ. ID. NO. 37758 | 198-ValLeuThrLysLysSerGlySer-205 |
| SEQ. ID. NO. 37759 | 208-LeuLeuProLysGlnAspLeu-214 |
| SEQ. ID. NO. 37760 | 225-GluLeuGlnArgLeuGlyAlaAspIleArgLeuGluThrArgValCysArg-241 |
| SEQ. ID. NO. 37761 | 246-ProAspGlyLysVal-250 |
| SEQ. ID. NO. 37762 | 276-GlyThrProGluHisVal-281 |
| SEQ. ID. NO. 37763 | 326-GlnAlaProAspCysProGlnAsnGluVal-335 |
| SEQ. ID. NO. 37764 | 341-ValSerAspArgValGly-346 |

It will be understood that the invention is described above by way of example only and modifications may be made whilst remaining within the scope and spirit of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08734812B1). An electronic copy of the "Sequence Listing" will also be available from the USPTO upon request and payment of the fee set forth in 37 CFR 1.19(b)(3).

The invention claimed is:

1. An isolated polypeptide having the amino acid sequence of SEQ ID NO: 11076, with the proviso that the polypeptide does not comprise the full length protein sequence of SEQ ID NO: 41369.

2. The isolated polypeptide of claim 1, further comprising a pharmaceutically acceptable carrier.

3. A purified polypeptide having the amino acid sequence of SEQ ID NO: 11076, with the proviso that the polypeptide does not comprise the full length protein sequence of SEQ ID NO: 41369.

4. The purified polypeptide of claim 3 further comprising a pharmaceutically acceptable carrier.

5. The isolated polypeptide of claim 1, wherein the polypeptide has a length of 100 amino acids or less.

6. The purified polypeptide of claim 3, wherein the polypeptide has a length of 100 amino acids or less.

7. The isolated polypeptide of claim 1, wherein the amino acid sequence of SEQ ID NO: 11076 is an antigenic fragment of the full length protein sequence of SEQ ID NO: 41369.

8. The purified polypeptide of claim 3, wherein the amino acid sequence of SEQ ID NO: 11076 is an antigenic fragment of the full length protein sequence of SEQ ID NO: 41369.

9. A composition comprising the isolated polypeptide of claim 1 and an aluminum salt.

10. The composition of claim 9, further comprising a pharmaceutically acceptable carrier.

11. The composition of claim 9, wherein the polypeptide has a length of 100 amino acids or less.

12. The composition of claim 9, wherein the amino acid sequence of SEQ ID NO: 11076 is an antigenic fragment of the full length protein sequence of SEQ ID NO: 41369.

13. A composition comprising the purified polypeptide of claim 3 and an aluminum salt.

14. The composition of claim 13, further comprising a pharmaceutically acceptable carrier.

15. The composition of claim 13, wherein the polypeptide has a length of 100 amino acids or less.

16. The composition of claim 13, wherein the amino acid sequence of SEQ ID NO: 11076 is an antigenic fragment of the full length protein sequence of SEQ ID NO: 41369.

\* \* \* \* \*